US007649015B2

(12) United States Patent
Arimili et al.

(10) Patent No.: US 7,649,015 B2
(45) Date of Patent: Jan. 19, 2010

(54) CELLULAR ACCUMULATION OF PHOSPHONATE ANALOGS OF HIV PROTEASE INHIBITOR COMPOUNDS

(75) Inventors: Murty N. Arimili, Oakridge, NC (US); Xiaowu Chen, San Mateo, CA (US); Maria Fardis, San Carlos, CA (US); Gong-Xin He, Fremont, CA (US); Haolun Jin, Foster City, CA (US); Choung U. Kim, San Carlos, CA (US); William A. Lee, Los Altos, CA (US); Kuei-Ying Lin, Fremont, CA (US); Hongtao Liu, Foster City, CA (US); Richard L. Mackman, Millbrae, CA (US); Michael L. Mitchell, Foster City, CA (US); Hyung-Jung Pyun, Fremont, CA (US); Mark Sparacino, Morgan Hill, CA (US); Sundaramoorthi Swaminathan, Burlingame, CA (US); Jianying Wang, Foster City, CA (US); Matthew A. Williams, San Mateo, CA (US); Lianhong Xu, San Mateo, CA (US); Zheng-Yu Yang, Foster City, CA (US); Richard H. Yu, San Francisco, CA (US); Jiancun Zhang, Oakland, CA (US); Lijun Zhang, Foster City, CA (US)

(73) Assignee: Gilead Sciences, Inc., Palo Alto, CA (US)

( * ) Notice: Subject to any disclaimer, the term of this patent is extended or adjusted under 35 U.S.C. 154(b) by 751 days.

(21) Appl. No.: 10/423,496

(22) Filed: Apr. 25, 2003

(65) Prior Publication Data

US 2005/0209197 A1 Sep. 22, 2005

Related U.S. Application Data

(60) Provisional application No. 60/375,622, filed on Apr. 26, 2002, provisional application No. 60/375,779, filed on Apr. 26, 2002, provisional application No. 60/375,834, filed on Apr. 26, 2002, provisional application No. 60/375,665, filed on Apr. 26, 2002.

(51) Int. Cl.
*A61K 31/343* (2006.01)
*C07F 9/28* (2006.01)

(52) U.S. Cl. ...................................... 514/470; 549/220

(58) Field of Classification Search ................. 549/218, 549/464, 465, 220; 514/470
See application file for complete search history.

(56) References Cited

U.S. PATENT DOCUMENTS

| | | | | |
|---|---|---|---|---|
| 5,413,996 | A | 5/1995 | Bodor | |
| 5,585,397 | A | 12/1996 | Tung et al. | |
| 5,670,497 | A | 9/1997 | Bold et al. | |
| 5,750,343 | A | 5/1998 | Maag et al. | |
| 5,750,493 | A | 5/1998 | Schinazi et al. | |
| 5,811,422 | A | 9/1998 | Lam et al. | |
| 5,874,577 | A | 2/1999 | Chen et al. | |
| 5,914,332 | A | 6/1999 | Chen et al. | |
| 6,072,053 | A | 6/2000 | Vince et al. | |
| 6,312,662 | B1 | 11/2001 | Robinson et al. | |
| 6,716,825 | B2 * | 4/2004 | Hostetler et al. | 514/52 |
| 6,767,900 | B2 | 7/2004 | Ubasawa et al. | |
| 2001/0031773 | A1 | 10/2001 | Camden | |
| 2003/0109498 | A1 | 6/2003 | Yuasa et al. | |

FOREIGN PATENT DOCUMENTS

| | | |
|---|---|---|
| EP | 0 267 050 | 5/1988 |
| EP | 0 441 192 | 1/1991 |
| EP | 0 465 297 | 1/1992 |
| EP | 0 531 597 | 3/1993 |
| EP | 0 632 048 | 1/1995 |
| EP | 0 786 455 | 7/1997 |
| EP | 0 852 233 | 7/1998 |
| EP | 0 919 562 | 6/1999 |
| EP | 1 295 879 | 3/2003 |
| WO | WO 88/06158 | 8/1988 |
| WO | WO 91/19721 | 12/1991 |
| WO | WO 92/00988 | 1/1992 |
| WO | WO 92/18520 | 10/1992 |
| WO | WO 93/12123 | 6/1993 |

(Continued)

OTHER PUBLICATIONS

Abdel-Meguid, Sherin S. et al., Inhibition.of Human Immunodeficiency Virus-1 Protease by a $C_2$-Symmetric Phosphinate, Synthesis and Crystallographic Analysis, *Biochemistry*, 1993, 1543-1572, vol. 32, No. 31.

(Continued)

*Primary Examiner*—Taofiq A Solola
(74) *Attorney, Agent, or Firm*—Max D. Hensley; Cynthia H. Zhang; Gilead Sciences, Inc.

(57) ABSTRACT

Phosphonate substituted compounds with HIV protease inhibitory properties having use as therapeutics and for other industrial purposes are disclosed. The compositions inhibit HIV protease activity and/or are useful therapeutically for the treatment of AIDS and other antiviral infections, as well as in assays for the detection of HIV protease.

11 Claims, 5 Drawing Sheets

FOREIGN PATENT DOCUMENTS

| | | |
|---|---|---|
| WO | WO 93/24510 | 12/1993 |
| WO | WO 96/14314 | 5/1996 |
| WO | WO 96/40156 | 12/1996 |
| WO | WO 98/04569 | 2/1998 |
| WO | WO 98/11906 | 3/1998 |
| WO | WO 99/33815 | 7/1999 |
| WO | WO 99/62921 | 12/1999 |
| WO | WO 00/04033 | * 1/2000 |
| WO | WO 01/13957 | 3/2001 |
| WO | WO 01/17982 | 3/2001 |
| WO | WO 01/19320 | 3/2001 |
| WO | WO 01/46204 | 6/2001 |
| WO | WO 01/64693 | 9/2001 |
| WO | WO 01/96329 | 12/2001 |
| WO | WO 02/03997 | 1/2002 |
| WO | WO 02/06292 | 1/2002 |
| WO | WO 02/008241 | 1/2002 |
| WO | WO 02/08241 | 1/2002 |
| WO | WO 02/14344 | 2/2002 |
| WO | WO 02/057425 | 7/2002 |
| WO | WO 02/100415 | 12/2002 |
| WO | WO 03/028737 | 4/2003 |
| WO | WO 03/050129 | 6/2003 |
| WO | WO 03/059255 | 7/2003 |
| WO | WO 03/064383 | 8/2003 |
| WO | WO 03/066005 | 8/2003 |
| WO | WO 03/080078 | 10/2003 |
| WO | WO 03/090690 | 11/2003 |
| WO | WO 2004/096234 | 11/2004 |
| WO | WO 2005/011709 | 2/2005 |

OTHER PUBLICATIONS

Allen, Lee F. et al., CI-1040 (PDI84352), a Targeted Signal Transduction Inhibitor of MEK (MAPKK), *Seminars in Oncology*, Oct. 2003, pp. 105-116, vol. 30, No. 5, Elsevier Inc.

Bantia, Shanta et al., Purine nucleoside phosphorylase inhibitor BCX-1777 (Immucillin-H)—a novel potent and orally active immunosuppressive agent, *International Immunopharmacology*, 2001, pp. 1199-1210, Elsevier Science B.V.

Beauchamp, Lilia M., et al., Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase, *Journal of Medicinal Chemistry*, 1996, pp. 949-956, American Chemical Society.

Bohani D. W. et al., A-420983: a potent, orally active inhibitor of Ick with efficacy in a model of transplant rejection, *Bioorganic & Medicinal Chemistry Letters*, 2004, vol. 14.

Bzowska, Agnieszka et al., Purine nucleoside phosphorylases: properties, functions, and clinical aspects, *Pharmacology & Therapeutics*, 2000, pp. 349-425, vol. 88, Elsevier Science Inc.

Chapman, H. et al., Practical Synthesis, Separation, and Stereochemical Assignment of the PMPA Pro-Drug GS-7340, Nucleosides, Nucleotides & Nucleic Acids, 2001, pp. 621-628, vol. 20, Nos. 4-7, Marcel Dekker, Inc.

Clark, Jeremy L. et al., Mycophenolic Acid Analogues as Potential Agents Against West Nile Virus Infection.

Conklyn, Maryrose et al., The JAK3 inhibitor CP-690550 selectively reduces NK and CD8+ cell numbers in cynomolgus monkey blood following chronic oral dosing, *Journal of Leukocyte Biology*, Dec. 2004, pp. 1-8, vol. 76, The Society for Leukocyte Biology.

De Clereq, E., Highlights in the Development of New Antiviral Agents, *Mini Reviews in Medicinal Chemistry*, 2002, 163-175, vol. 2, No. 2., Bentham Science Publishers, Ltd.

De Clercq, Erik, New Developments in Anti-HIV Chemotherapy, *Current Medicinal Chemistry*, 2001, 1543-1572, vol. 8, No. 13, Bentham Science Publishers Ltd.

Dvorakova, Hana et al., Synthesis of 2'-Aminomethyl Derivatives of N-(2-(Phosphonomethoxy)ethyl) Nucleotide Analogues as Potential Antiviral Agents, *J. Med. Chem.*, 1996, 3263-3268. vol. 38, No. 17.

Evans, Gary B., Exploring Structure—Activity Relationships of Transition State Analogues of Human Purine Nucleoside Phosphorylase, *J. Med. Chem.*, 2003, 3412-3423, vol. 46, No. 15, American Chemical Society.

Gumina, Giuseppe et al., Advances in antiviral agents for hepatitis B virus, *Antiviral Chemistry & Chemotherapy*, 2001, 93-112, vol. 12, Suppl. 1, International Medical Press.

Gobec, S. at al., Phosphonate inhibitors of antiget 85C, a crucial enzyme involved in the biosynthesis of the mycobacterium tuberculosis cell wall, *Bioorganic and Medicinal Chemistry Letters*, 2004, vol. 14.

Hegedus, Louis S. et al., Synthesis of 4'-Methyl and 4'-cyano Carbocyclic 2',3'-Didehydro Nucleoside Analogues via 1,4-Addition to Substituted Cyclopentenones, *J. Org. Chem.*, 2004, 8492-8495, vol. 69, No. 24, American Chemical Society.

Herczegh P., et al., Osteoadsorptive bisphosphonate derivatives of fluoroquinolone antibacterials, *J. Med. Chem.*, 2002, vol. 45.

Hirabayashi, Hideki et al., Bone-Specific Drug Delivery Systems, *Clinical Pharacokinetics*, 2003, 1319-1330, vol. 42, No. 15.

Holy A. et al., *Synthesis, Cllect. Czech. Chem. Commun.*, 1989, vol. 54, pp. 2190-2210.

Jain, Jugnu et al., Characterization of Pharmacological Efficacy of VX-148, a New, Potent Immunosuppressive Inosine 5'-Monophosphate Dehydrogenase Inhibitor, *Journal of Pharmacology and Experimental Therapeutics*, 2002, 1272-1277, vol. 302, No. 3, The American Society for Pharmacology and Experimental Therapeutics.

Karpenko, Inna L. et al., Synthesis and Antitherpetic Activity of Acyclovir Phosphonates, Nucleosides, Nucleotides & Nucleic Acids, 2003, 319-328, vol. 22, No. 3, Marcel Dekker, Inc.

Kato, Keisuke et al., Stereoselective synthesis of 4' -.alpha.-alkycicarbovir derivatives based on an asymmetric synthesis or chemo-enzymatic procedure, *Chemical & Pharmaceutical Bulletin*, 1999, 1256-1264, vol. 49, No. 9, Pharmaceutical Society of Japan.

Kato, Keisuke et al., Enantio- and diastereoselective syntheis of 4'-α-substituted carbocyclic nucleosides, Tetrahedron: *Asymmetry*, 1998, 911-914, vol. 9, Elsevier Science Ltd.

Kilpatrick, J. Michael, Intravenous and oral pharmacokinetic study of BCX-1777, a novel purine nucleoside phosphorylase transition-state inhibitor, In vivo effects on blood 2'- deoxyguanosine in primates, *International Immunopharmacology*, 2003, 541-548, vol. 3, Elsevier Science B.V.

Kim, Choung Un et al, Regiospecific and Highly Stereoselective Electrophilic Addition to Furanoid Glycals: Synthesis of Phosphonate Nucleotide Analogues with Potent Activity against HIV, J. Org. Chem., 1991, 2642-2647, vol. 56, No. 8, American Chemical Society.

Kinsky, Stephen C. et al., Inhibition of cell proliferation by putative metabolites and non-degradable analogs of methotrexate-.gama.-dimyristoylphosphatidylethanolamine, *Biochimica et Biphysica Acta*, 19878, 211-218, vol. 917, No. 2., Elsevier Science Publishers B. V.

Kinsky, Stephen C. at al., Effect of liposomes sentitized with methotrexate-γ-dimyristoylphosphatidylethanolamine on cells that are resistant to methotrexate, *Biochimica et Biophysica Acta*, 1986, 129-135, vol. 885, Elsevier Science Publishers B.V.

Kinsky, Stephen C. et al., Circumvention of the methotrexate transport system by methotrexate-phosphatidylethanolamine derivatives effect of fatty acid chain length, *Biochimica et Biophysica Acta*, 1987, 96-103, vol. 921, Elsevier Science Publishers B.V.

Ko, Ok Hyun et al., Efficient synthesis of novel carbocyclic nucleosides via sequential Claisen rearrangement and ring-closing metathesis, *Tetrahedron Letters*, 2002, 6399-6402, vol. 43, Elsevier Science Ltd.

Lewandowicz, Andrzej et al., Achieving the Ultimate Physiological Goal in Transition State Analogue Inhibitors for Purine Nucleoside Phosphorylase, *The Journal of Biological Chemistry*, 2003, 31465-31468, vol. 278, No. 34, The American Society for Biochemistry and Molecular Biology, Inc.

Menendez-Arias, Luis et al., Targeting HIV: antiretroviral therapy and development of drug resistance, *TRENDS in Pharmacological Sciences*, 2002, 381-388, vol. 23, No. 8, Elsevier Science Ltd.

Ono-Nita, Suzane Kioko et al., Novel Nucleoside Analogue MCC-478 (LY582563) Is Effective against Wild-Type or Lamivudine-Resistant Hepatitis B Virus, *Antimicrobial Agents and Chemotherapy*, 2002, 2602-2605, vol. 46, No. 8, American Society for Microbiology.

Pankiewicz, Krzysztof W., Novel Mycophenolic Adenine Bis(phosphonate) Analogues As Potential Differentiation Agents against Human Leukemia, *J. Med. Chem.*, 2002 703-712, vol. 45, No. 3, American Chemical Society.

Parang, Keykavous et al., Novel Approaches for Designing 5'-O-Ester Prodrugs of 3'-Azido-2', 3'-dideoxythymidine (AZT), *Current Medicinal Chemistry*, 2000, 995-1039, vol. 7, No. 10, Bentham Science Publishers Ltd.

Prashad, Mahavir at al., An Efficient and Large-Scale Enantioselective Synthesis of PNP405: A Purine Nucleoside Phosphorylase Inhibitor, *J. Org. Chem.*, 2002, 6612-6617, vol. 67, No. 19, American Chemical Society.

Ray, Adrian S. et al., Role of Purine Nucleoside Phosphorylase in Interactions between 2', 3'-Dideoxyinosine and Allopurinal, Ganciclovir, or Tenofovir, Antimicrobial Agents and Chemotherapy, 2004, 1089-1095, vol. 48, No. 4, American Society for Microbiology.

Reed, Leff et al., Antidiabetic PPARγ Ligands: An update on Compounds in development, *Curr. Med. Chem.—Imun., Endoc. & Metab. Agents*, 2002, 33-47, vol. 2, No. 1, Bentham Science Publishers Ltd.

Roberts, Stanley M., Development of the route to the new anti-AIDS drug abacavir: A highlight of academic/industry laison, *IDrugs*, 1998, 896-899, vol. 1, No. 8, Current Drugs Ltd.

Rosowsky, Andre et al., Methotrexate Analogues-27, *Biochemical Pharmacology*, 1986, 3327-3333, vol. 35, No. 19, Pergamon Journals Ltd.

Rosowsky, Andre et al., Methotrexate Analogues, 32, Chain Extension, α-Carboxyl Replacement by Sulfonate and Phosphonate: Effect on Enzyme Binding and Cell-Growth Inhibition, *J. Med. Chem.*, 1988, 1326-1331, vol. 31, No. 7, American Chemical Society.

Schultz, C., Prodrugs of biologically active phosphate esters, *Bioorganic & Medicinal Chemistry*, 2003, 885-898, vol. 11, Elsevier Science Ltd., GB.

Sekiya, Kouichi et al., 2-Amino-6-arylthio-9-[2-(phosphonomethoxy) ethyl) purine Bis(2,2,2-trifluoroethyl) Esters as Novel HBV-Specific Antiviral Reagents, Journal of Medicinal Chemistry, 2002, 3138-3142, vol. 45, No. 14, American Chemical Society.

Shi, Wuxian et al., *Plasmodium falciparum* Purine Nucleoside Phosphorylase, The Journal of Biological Chemistry, 2004, 18103-18106, vol. 279, No. 18, The American Society of Biochemistry and Molecular Biology, Inc.

Sintchak, Michael D. et al., The structure of inosine 5'-monophosphate dehydrogenase and the design of novel inhibitors, Immunopharmachology, 2000, 163-184, vol. 47, Elsevier.

Srinivas, Ranga V. et al., Metabolism and In Vitro Antiretroviral Activities of Bis(Pivaloyloxymethyl) Prodrugs of Acyclic Nucleoside Phosphonates, Antimicrobial Agents and Chemotherapy, 1993, 2247-2250, vol. 37, No. 10, American Society for Microbiology.

Sturtz, Georges et al., Su rune nouvelle approche de pharmacomodulation du methotrexate: synthese d'analogues gem-diphosphoniques d'amethopterine et de la N-10 deaza amethopterine, Medicinal Chemistry, C. R. Acad. Sci. Paris, 1990, vol. 10, No. 2, 739-742, Academie des Sciences.

Sturtz, Georges et al., Analogues phosphonoglutamiques d'amethopterine (methotrexate), Eur. J. Med. Chem—Chim. Ther., 1984, 267-273, vol. 19, No. 3.

Sturtz, G. et al., Synthesis of gem-bisphosphonic methotrexate conjugates and their biological response towards Walker's osteosarcoma, *Eur. J. Med. Chem.*, 1993, 899-903, vol. 28, Elsevier.

Sturtz, G. et al., A study of the delivery-targeting concept applied to antineoplasic drugs active on human osteosarcoma, I. Synthesis and biological activity in nude mice carrying human osteosarcoma xenografts of gem-bisphosphonic methotrexate analogues, Eur J. Med. Chem., 1992, 825-833, vol. 27, No. 8, Elsevier.

Vielhaber, Bernd, Bericht vom 3rd International Workshop on Salvage Therapy for HIV- Infection, *Deutsche Aids-Hilfe e. V. FaxReport zu HIV und AIDS*, 2000, 12-14.

Waegell W. et al. A420983, a novel, small molecule inhibitor of LCK prevents allograft rejection, Transplantation Proceedings, 2002, 1411-1417, vol. 34.

Wroblewski, Andrzej et al., Synthesis of (1R,2S)- and (1S,2S)-3-(4-carbamoyl-1,2,3-triazol-1-yl)-1,2-dihydroxypropylphosphonates, Tetrahedron: Asymmetry, 2004, 1457-1464, vol. 15, Elsevier.

Jose M. Gatell, "From Amprenavir to GW433908", XP-001120503, J. HIV Ther. Nov. 2001 6(4) 96-99.

Yoshimura et al. "New HIV-1 Protease Inhibitors in Development," Nippon Rinsho vol. 60. No. 4. Apr. 2002 pp, 780-783.

* cited by examiner

CELLULAR ACCUMULATION OF PHOSPHONATE ANALOGS OF HIV PROTEASE INHIBITOR COMPOUNDS

This non-provisional application claims the benefit of Provisional Applications 60/375,622, filed Apr. 26, 2002; Provisional Application No. 60/375,779 filed Apr. 26, 2002; Provisional Application No. 60/375,834, filed Apr. 26, 2002, and Provisional Application No. 60/375,665 filed Apr. 26, 2002, all of which are incorporated herein by reference. Additionally, applications Ser. No. 10/424,186 filed Apr. 28, 2003 now US 2004-0121316 and Ser. No. 10/424,130, filed Apr. 28, 2003 now U.S. Pat. No. 7,462,608 are also incorporated herein by reference in their entirety.

FIELD OF THE INVENTION

The invention relates generally to compounds with antiviral activity and more specifically with anti-HIV protease properties.

BACKGROUND OF THE INVENTION

AIDS is a major public health problem worldwide. Although drugs targeting HIV viruses are in wide use and have shown effectiveness, toxicity and development of resistant strains have limited their usefulness. Assay methods capable of determining the presence, absence or amounts of HIV viruses are of practical utility in the search for inhibitors as well as for diagnosing the presence of HIV.

Human immunodeficiency virus (HIV) infection and related disease is a major public health problem worldwide. The retrovirus human immunodeficiency virus type 1 (HIV-1), a member of the primate lentivirus family (DeClercq E (1994) *Annals of the New York Academy of Sciences,* 724: 438-456; Barre-Sinoussi F (1996) *Lancet,* 348:31-35), is generally accepted to be the causative agent of acquired immunodeficiency syndrome (AIDS) Tarrago etal *FASEB Journal* 1994, 8:497-503). AIDS is the result of repeated replication of HIV-1 and a decrease in immune capacity, most prominently a fall in the number of CD4+ lymphocytes. The mature virus has a single stranded RNA genome that encodes 15 proteins (Frankel etal (1998) *Annual Review of Biochemistry,* 67:1-25; Katz etal (1994) *Annual Review of Biochemistry,* 63:133-173), including three key enzymes: (i) protease (Prt) (von der Helm K (1996) *Biological Chemistry,* 377:765-774); (ii) reverse transcriptase (RT) (Hottiger etal (1996) *Biological Chemistry Hoppe-Seyler,* 377:97-120), an enzyme unique to retroviruses; and (iii) integrase (Asante etal (1999) *Advances in Virus Research* 52:351-369; Wlodawer A (1999) *Advances in Virus Research* 52:335-350; Esposito etal (1999) *Advances in Virus Research* 52:319-333). Protease is responsible for processing the viral precursor polyproteins, integrase is responsible for the integration of the double stranded DNA form of the viral genome into host DNA and RT is the key enzyme in the replication of the viral genome. In viral replication, RT acts as both an RNA- and a DNA-dependent DNA polymerase, to convert the single stranded RNA genome into double stranded DNA. Since virally encoded Reverse Transcriptase (RT) mediates specific reactions during the natural reproduction of the virus, inhibition of HIV RT is an important therapeutic target for treatment of HIV infection and related disease.

Sequence analysis of the complete genomes from several infective and non-infective HIV-isolates has shed considerable light on the make-up of the virus and the types of molecules that are essential for its replication and maturation to an infective species. The HIV protease is essential for the processing of the viral gag and gag-pol polypeptides into mature virion proteins. L. Ratner, et al., Nature, 313:277-284 (1985); L. H. Pearl and W. R. Taylor, Nature, 329:351 (1987). HIV exhibits the same gag/pol/env organization seen in other retroviruses. L. Ratner, et al., above; S. Wain-Hobson, et al., Cell, 40:9-17 (1985); R. Sanchez-Pescador, et al., Science, 227:484-492 (1985); and M. A. Muesing, et al., Nature, 313: 450-458 (1985).

A therapeutic target in AIDS involves inhibition of the viral protease (or proteinase) that is essential for processing HIV-fusion polypeptide precursors. In HIV and several other retroviruses, the proteolytic maturation of the gag and gag/pol fusion polypeptides (a process indispensable for generation of infective viral particles) has been shown to be mediated by a protease that is, itself, encoded by the pol region of the viral genome. Y. Yoshinaka, et al., Proc. Natl. Acad. Sci. USA, 82:1618-1622 (1985); Y. Yoshinaka, et al., J. Virol., 55:870-873 (1985); Y. Yoshinaka, et al., J. Virol., 57:826-832 (1986); and K. von der Helm, Proc. Natl. Acad. Sci., USA, 74:911-915 (1977). Inhibition of the protease has been shown to inhibit the processing of the HIV p55 in mammalian cell and HIV replication in T lymphocytes. T. J. McQuade, et al., Science, 247:454 (1990).

Drugs approved in the United States for AIDS therapy include nucleoside inhibitors of RT (Smith et al (1994) *Clinical Investigator,* 17:226-243), protease inhibitors and non-nucleoside RT inhibitors (NNRTI), (Johnson et al (2000) *Advances in Internal Medicine,* 45 (1-40; Porche D J (1999) *Nursing Clinics of North America,* 34:95-112).

The protease (or proteinase), consisting of only 99 amino acids, is among the smallest enzymes known, and its demonstrated homology to aspartyl proteases such as pepsin and renin (L. H. Pearl and W. R. Taylor, Nature, 329:351-354 (1987); and I. Katoh, et al., Nature, 329:654-656 (1987)), led to inferences regarding the three-dimensional structure and mechanism of the enzyme (L. H. Pearl and W. R. Taylor, above) that have since been borne out experimentally. Active HIV protease has been expressed in bacteria (see, e.g., P. L. Darke, et al., J. Biol. Chem., 264:2307-2312 (1989)) and chemically synthesized (J. Schneider and S. B. Kent, Cell, 54:363-368 (1988); and R. F. Nutt, et al., Proc. Natl. Acad. Sci., USA, 85:7129-7133 (1988)). Site directed mutagenesis (P. L. Darke, et al., above); and N. E. Kohl, et al., Proc. Natl. Acad. Sci., USA, 85:4686-4690 (1988)) and pepstatin inhibition (P. L. Darke, et al., J. Biol. Chem., 264:2307-2312 (1989); S. Seelmeier, et al., Proc. Natl. Acad. Sci., USA, 85:6612-6616 (1988); C.-Z. Giam and I. Borsos, J. Biol. Chem., 263:14617-14720 (1988); and J. Hansen, et al., EMBO J., 7:1785-1791 (1988)) have provided evidence for HIV protease's mechanistic function as an aspartyl protease. A study has demonstrated that the protease cleaves at the sites expected in peptides modeled after the regions actually cleaved by the enzyme in the gag and pol precursor proteins during viral maturation. P. L. Darke, et al., Biochem. Biophys. Res. Communs., 156:297-303 (1988). X-ray crystallographic analysis of the HIV-protease (M. A. Navia, et al., Nature, 337:615-620 (1989)) and a related retroviral enzyme from Rous sarcoma virus (M. Miller, et al., Nature, 337:576-579 (1989)) reveal an active site in the protease dimer that is identical to that seen in other aspartyl proteases, thus supporting the supposition (L. H. Pearl and W. R. Taylor, above) that the HIV enzyme is active as a dimer. See also Joseph A. Martin, "Recent Advances in the Design of HIV Proteinase Inhibitors," Antiviral Research, 17 (1992) 265-278.

Inhibitors of HIV protease are useful to limit the establishment and progression of infection by therapeutic administration as well as in diagnostic assays for HIV. Protease inhibitor drugs approved by the FDA include:

saquinavir (Invirase®, Fortovase®, Hoffman-La Roche, EP-00432695 and EP-00432694)

ritonavir (Norvir®, Abbott Laboratories)

indinavir (Crixivan®, Merck & Co.)

nelfinavir (Viracept®, Pfizer)

amprenavir (Agenerase®, GlaxoSmithKline, Vertex Pharmaceuticals)

lopinavir/ritonavir (Kaletra®, Abbott Laboratories)

Experimental protease inhibitor drugs include:

fosamprenavir (GlaxoSmithKline, Vertex Pharmaceuticals)

tipranavir (Boehringer Ingelheim)

atazanavir (Bristol-Myers Squibb).

There is a need for anti-HIV therapeutic agents, i.e. drugs having improved antiviral and pharmacokinetic properties with enhanced activity against development of HIV resistance, improved oral bioavailability, greater potency and extended effective half-life in vivo. New HIV protease inhibitors (PI) should be active against mutant HIV strains, have distinct resistance profiles, fewer side effects, less complicated dosing schedules, and orally active. In particular, there is a need for a less onerous dosage regimen, such as one pill, once per day. Although drugs targeting HIV protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001).

Combination therapy of PI and RT inhibitors has proven to be highly effective in suppressing viral replication to unquantifiable levels for a sustained period of time. Also, combination therapy with RT and protease inhibitors have shown synergistic effects in suppressing HIV replication. Unfortunately, many patients currently fail combination therapy due to the development of drug resistance, non-compliance with complicated dosing regimens, pharmacokinetic interactions, toxicity, and lack of potency. Therefore, there is a need for new HIV protease inhibitors that are synergistic in combination with other HIV inhibitors.

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g. to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the cellular and tissue barriers, e.g. blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells. Intracellular targeting may be achieved by methods and compositions which allow accumulation or retention of biologically active agents inside cells.

SUMMARY OF THE INVENTION

The present invention provides novel compounds with HIV protease activity, i.e. novel human retroviral protease inhibitors. Therefore, the compounds of the invention may inhibit retroviral proteases and thus inhibit the replication of the virus. They are useful for treating human patients infected with a human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases. The present invention includes novel phosphonate HIV protease inhibitor (PI) compounds and phosphonate analogs of known approved and experimental protease inhibitors. The compounds of the invention optionally provide cellular accumulation as set forth below.

The present invention relates generally to the accumulation or retention of therapeutic compounds inside cells. The invention is more particularly related to attaining high concentrations of phosphonate-containing molecules in HIV infected cells. Intracellular targeting may be achieved by methods and compositions which allow accumulation or retention of biologically active agents inside cells. Such effective targeting may be applicable to a variety of therapeutic formulations and procedures.

Compositions of the invention include new PI compounds having at least one phosphonate group. The invention includes all known approved and experimental protease inhibitors with at least one phosphonate group.

In one aspect, the invention includes compounds having Formulas I, II, III, IV, V, VI, VII and VIIIa-d:

I

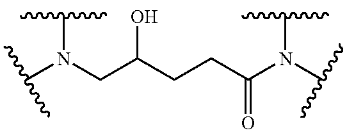

II

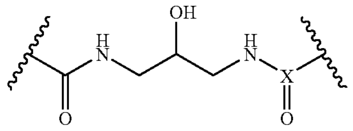

X = C, SO

III

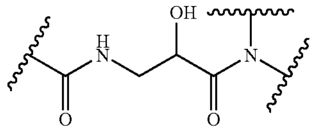

IV

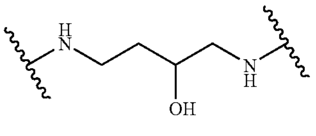

-continued

V

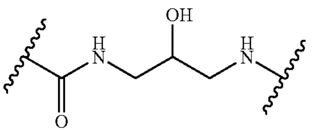

VI

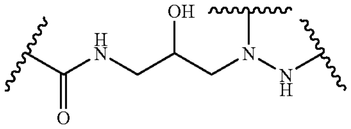

VII

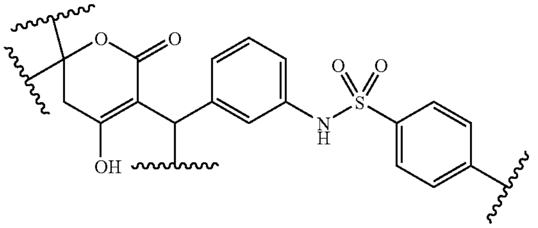

VIIIa

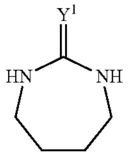

VIIIb

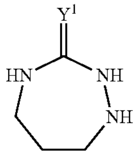

VIIIc

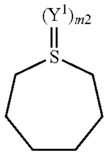

and

VIIId

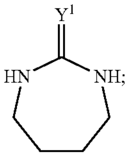

where a wavy line indicates the other structural moieties of the compounds.

Formulas I-VIII are substituted with one or more covalently attached groups, including at least one phosphonate group. Formulas I-VIII are "scaffolds", i.e. substructures which are common to the specific compounds encompassed therein.

Another aspect of the invention provides a pharmaceutical combination comprising an effective amount of a compound selected from Formulas I-VIII and a second compound having anti-HIV properties.

Another aspect of the invention provides a method for the treatment or prevention of the symptoms or effects of an HIV infection in an infected animal which comprises administering to, i.e. treating, said animal with a pharmaceutical combination comprising an effective amount of a compound selected from Formulas I-VIII and a second compound having anti-HIV properties.

The invention provides a pharmaceutical composition comprising an effective amount of a compound selected from Formulas I-VIII, or a pharmaceutically acceptable salt thereof, in combination with a pharmaceutically acceptable diluent or carrier.

This invention pertains to a method of increasing cellular accumulation and retention of drug compounds, thus improving their therapeutic and diagnostic value.

The invention also provides a method of inhibiting HIV, comprising administering to a mammal infected with HIV (HIV positive) an amount of a compound of Formulas I-VIII, effective to inhibit the growth of said HIV infected cells.

The invention also provides a compound selected from Formulas I-VIII for use in medical therapy (preferably for use in treating cancer, e.g. solid tumors), as well as the use of a compound of Formulas I-VIII for the manufacture of a medicament useful for the treatment of cancer, e.g. solid tumors.

The invention also provides processes and novel intermediates disclosed herein which are useful for preparing compounds of the invention. Some of the compounds of Formulas I-VIII are useful to prepare other compounds of Formulas I-VIII.

In another aspect of the invention, the activity of HIV protease is inhibited by a method comprising the step of treating a sample suspected of containing HIV virus with a compound or composition of the invention.

Another aspect of the invention provides a method for inhibiting the activity of HIV protease comprising the step of contacting a sample suspected of containing HIV virus with a composition of the invention.

In other aspects, novel methods for synthesis analysis, separation, isolation, purification, characterization, and testing of the compounds of this invention are provided.

DETAILED DESCRIPTION OF EXEMPLARY EMBODIMENTS

Figure 1:
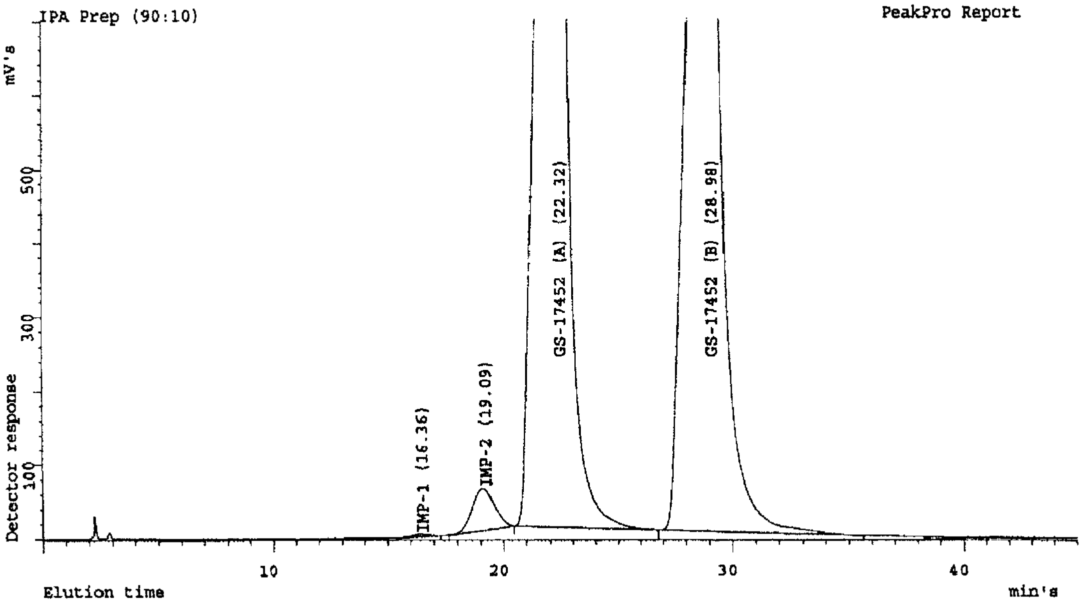
FIG. 1 shows resolution of compound 14 diastereomers by HPLC on an analytical Ailtech Econosil column.

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. These substituents may be part of a prodrug moiety. As defined herein, "phosphonate" and "phosphonate group" include molecules with phosphonic acid, phosphonic monoester, phosphonic diester, phosphonamidate, phosphondiamidate and phosphonthioate functional groups.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Pharmaceutically acceptable prodrug" refers to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

Exemplary prodrug moieties include the hydrolytically sensitive or labile acyloxymethyl esters $—CH_2OC(=O)R^9$ and acyloxymethyl carbonates $—CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al (1983) *J. Pharm. Sci.* 72: 324; also U.S. Pat. Nos. 4,816,570, 4,968,788, 5,663,159 and 5,792,756. In certain compounds of the invention, a prodrug moiety is part of a phosphonate group. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) $—CH_2OC(=O)C(CH_3)_3$. An exemplary acyloxymethyl carbonate prodrug moiety is pivaloyloxymethylcarbonate (POC) $—CH_2OC(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert et al (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans. I* 2345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al (1993) *Antiviral Res.,* 22: 155-174; Benzaria et al (1996) *J. Med. Chem.* 39: 4958). Cyclic phosphonate esters have also been described as prodrugs of phosphorus-containing compounds (Erion et al, U.S. Pat. No. 6,312,662).

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-b y ($—CH(CH_3)C(CH_3)_3$.

"Alkenyl" is $C_2$-$C_{18}$ hydrocarbon containing normal, secondary, tertiary or cyclic carbon atoms with at least one site of unsaturation, i.e. a carbon-carbon, $Sp^2$ double bond. Examples include, but are not limited to: ethylene or vinyl ($—CH{=}CH_2$), allyl ($—CH_2CH{=}CH_2$), cyclopentenyl ($—C_5H_7$), and 5-hexenyl ($—CH_2\ CH_2CH_2CH_2CH{=}CH_2$)

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic ($—C{\equiv}CH$) and propargyl ($—CH_2C{\equiv}CH$), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene ($—CH_2—$) 1,2-ethyl ($—CH_2CH_2—$), 1,3-propyl ($—CH_2CH_2CH_2—$), 1,4-butyl ($—CH_2CH_2CH_2CH_2—$), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene ($—CH{=}CH—$).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene ($—C{\equiv}C—$), propargyl ($—CH_2C{\equiv}C—$), and 4-pentynyl ($—CH_2CH_2CH_2C{\equiv}CH—$).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the arylmoiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O—, —OR, —SR, $—S^-$, $—NR_2$, $—NR_3$, =NR, $—CX_3$, —CN, —OCN, —SCN, —N=C=O, —NCS, —NO, $—NO_2$, $=N_2$, $—N_3$, NC(=O)R, —C(=O)R, —C(=O)NRR $—S(=O)_2O^-$, $—S(=O)_2OH$, $—S(=O)_2R$, $—OS(=O)_2OR$, $—S(=O)_2NR$, —S(=O)R, $—OP(=O)O_2RR$, $—P(=O)O_2RR$, $—P(=O)(O^-)_2$, $—P(=O)(OH)_2$, —C(=O)R, —C(=O)X, —C(S)R, —C(O)OR, $—C(O)O^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc. (*1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

One embodiment of the bis-tetrahydrofuranyl group is:

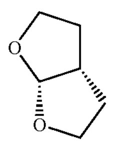

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated, unsaturated or aromatic ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" means a chemical moiety comprising a covalent bond or a chain of atoms that covalently attaches a phosphonate group to a drug. Linkers include portions of substituents $A^1$ and $A^3$ enumerated in Formula I, or substituents $A_1$ and $A_3$ enumerated in Formula II, which include moieties such as: repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

HIV Protease Inhibitor Compounds

The compounds of the invention include those with HIV protease inhibitory activity. In particular, the compounds include HIV protease inhibitors. The compounds of the inventions bear a phosphonate group, which may be a prodrug moiety.

In various embodiments of the invention one identifies compounds that may fall within the generic scope of the documents cited under the definition of the terms ILPPI (Indinavir-like phosphonate protease inhibitors, Formula I); AMLPPI (Amprenavir-like phosphonate protease inhibitors, Formula II); KNILPPI (KNI-like phosphonate protease inhibitors, Formula III); RLPPI (Ritonavir-like phosphonate protease inhibitors, Formula IV); LLPPI (Lopinavir-like phosphonate protease inhibitors, Formula IV); NLPPI (Nelfinavir-like phosphonate protease inhibitors, Formula V); SLPPI (Saquinavir-like phosphonate protease inhibitors, Formula V); ATLPPI (Atanzavir-like phosphonate protease inhibitors, Formula VI); TLPPI (Tipranavir-like phosphonate protease inhibitors, Formula VII); and CCLPPI (Cyclic carbonyl-like phosphonate protease inhibitors, Formula VIIIa-d) all of which comprise a phosphonate group, e.g. a phosphonate diester, phosphonamidate-ester prodrug, or a phosphondiamidate-ester (Jiang et al, US 2002/0173490 A1).

Whenever a compound described herein is substituted with more than one of the same designated group, e.g., "$R^1$" or "$R^{6a}$", then it will be understood that the groups may be the same or different, i.e., each group is independently selected. Wavy lines indicate the site of covalent bond attachments to the adjoining groups, moieties, or atoms.

Compounds of the invention are set forth in the schemes, examples, descriptions and claims below and include the invention includes compounds having Formulas I, II, III, IV, V, VI, VII and VIIIa-d:

I

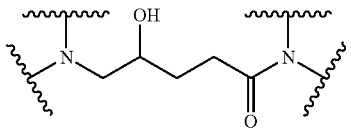

II

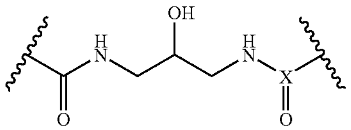

X = C, SO

III

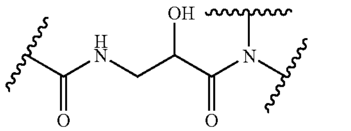

IV

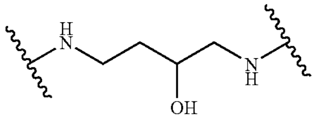

V

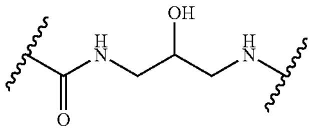

VI

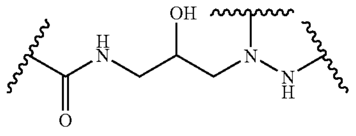

VII

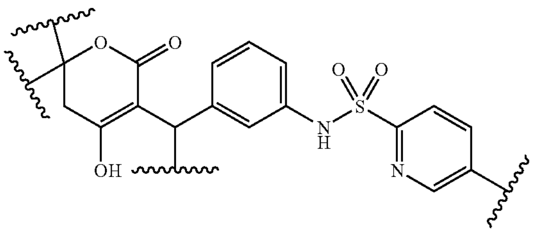

-continued

VIIIa

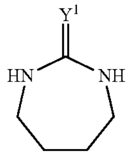

VIIIb

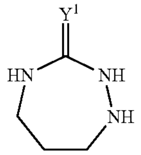

VIIIc

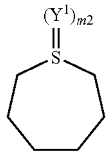

and

VIIId

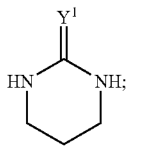

where a wavy line indicates the other structural moieties of the compounds.

Formula I compounds have a 3-hydroxy-5-amino-pentamide core. Formula II compounds have a 2-hydroxy-1,3-amino-propylamide or 2-hydroxy-1,3-amino-propylaminosulfone core. Formula III compounds have a 2-hydroxy-3-amino-propylamide core. Formula IV compounds have a 2-hydroxy-4-amino-butylamine core. Formula V compounds have a acylated 1,3-diaminopropane core. Formula VI compounds have a 2-hydroxy-3-diaza-propylamide core. Formula VII compounds have a sulfonamide 5,6-dihydro-4-hydroxy-2-pyrone core. Formula VIIIa-d compounds have a six or seven-membered ring, and a cyclic carbonyl, sulfhydryl, sulfoxide or sulfone core, where Y, is oxygen, sulfur, or substituted nitrogen and m2 is 0, 1 or 2.

Formulas I, II, III, IV, V, VI, VII and VIIIa-d are substituted with one or more covalently attached groups, including at least one phosphonate group. Formulas I, II, III, IV, V, VI, VII and VIIIa-d are substituted with one or more covalently attached $A^0$ groups, including simultaneous substitutions at any or all $A^0$. $A^0$ is $A^1$, $A^2$ or $W^3$. Compounds of Formulas I, II, III, IV, V, VI, VII and VIIIa-d include at least one $A^1$.

$A^1$ is:

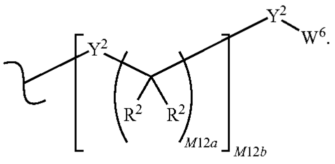

-continued $A^2$ is:

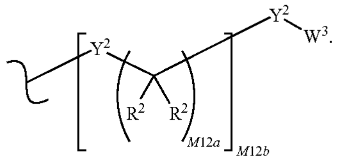

$A^3$ is:

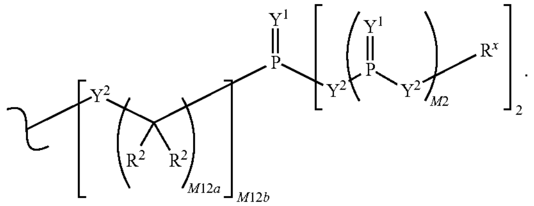

$Y^1$ is independently O, S, $N(R^x)$, $N(O)(R^x)$, $N(OR^x)$, $N(O)(OR^X)$, or $N(N(R^x)(R^x))$.

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$.

$R^x$ is independently H, $W^3$, a protecting group, or the formula:

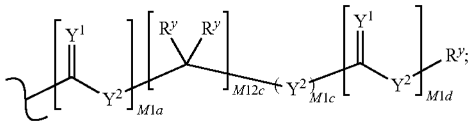

wherein:

M1a, M1c, and M1d are independently 0 or 1;

M12c is 0, 1, 2, 3, 4, 5, 6, 7, 8, 9, 10, 1 or 12; and $R^y$ is independently H, $W^3$, $R^2$ or a protecting group.

Alternatively, $R^x$ is a group of the formula:

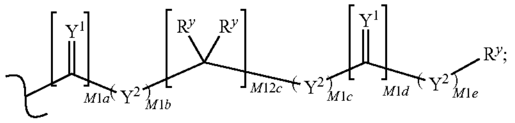

wherein:

m1a, m1b, m1c, m1d and m/e are independently 0 or 1;

m12c is 0, 1, 2, 3, 4, 5, 6, 7, 8, 9, 10, 11 or 12;

$R^y$ is H, $W^3$, $R^2$ or a protecting group;

provided that:

if m1a, m12c, and mid are 0, then m1b, m1c and m/e are 0;

if m1a and m12c are 0 and m1d is not 0, then m1b and m1c are 0;

if m1a and mid are 0 and m12c is not 0, then m1b and at least one of m1c and m/e are 0;

if m1a is 0 and m12c and m1d are not 0, then m1b is 0;

if m12c and mid are 0 and m1a is not 0, then at least two of m1b, m1c and m/e are 0;

if m12c is 0 and m1a and m1d are not 0, then at least one of m1b and m1c are 0; and if mid is 0 and m1a and m12c are not 0, then at least one of m1c and mile are 0.

$R^1$ is independently H or alkyl of 1 to 18 carbon atoms.

$R^2$ is independently H, $R^3$ or $R^4$ wherein each $R^4$ is independently substituted with 0 to 3 $R^3$ groups. Alternatively, taken together at a carbon atom, two $R^2$ groups form a ring, i.e. a spiro carbon. The ring may be, for example, cyclopropyl, cyclobutyl, cyclopentyl, or cyclohexyl. The ring may be substituted with 0 to 3 $R^3$ groups.

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$.

$R^{3a}$ is F, Cl, Br, I, —CN, $N_3$ or $—NO_2$.

$R^{3b}$ is $Y^1$.

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y)OR^x$, $—OC(Y^1)(N(R^x)(R^x))$, $—SC(Y)R^x$, $—SC(Y^1)OR^x$, $—SC(Y^1)(N(R^x)(R^x))$, $N(R^x)C(Y^1)R^x$, $—N(R^x)C(Y^1)OR^x$, or $—N(R^x)C(Y^1)(N(R^x)(R^x))$.

$R^{3d}$ is $—C(Y^1)R^x$, $—C(Y^1)OR^x$ or $—C(Y^1)(N(R^x)(R^x))$.

$R^4$ is an alkyl of 1 to 18 carbon atoms, alkenyl of 2 to 18 carbon atoms, or alkynyl of 2 to 18 carbon atoms.

$R^5$ is $R^4$ wherein each $R^4$ is substituted with 0 to 3 $R^3$ groups.

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups.

$W^3$ is $W^4$ or $W^5$.

$W^4$ is $R^5$, $—C(Y^1)R^5$, $—C(Y^1)W^5$, $—SO_2R^5$, or $—SO_2W^5$.

$W^5$ is carbocycle or heterocycle wherein $W^5$ is independently substituted with 0 to 3 $R^2$ groups.

$W^{3a}$ is $W^{4a}$ or $W^{5a}$.

$W^{4a}$ is $R^{5a}$, $—C(Y^1)R^{5a}$, $—C(Y^1)W^{5a}$, $—SO_2R^{5a}$, or $—SO_2W^{5a}$.

$W^{5a}$ is a multivalent substituted carbocycle or heterocycle wherein $W^{5a}$ is independently substituted with 0 to 3 $R^2$ groups.

$W^6$ is $W^3$ independently substituted with 1, 2, or 3 $A^3$ groups.

M2 is 0, 1 or 2;

M12a is 1, 2, 3, 4, 5, 6, 7, 8, 9, 10, 11 or 12; and

M12b is 0, 1, 2, 3, 4, 5, 6, 7, 8, 9, 10, 11 or 12.

$W^5$ and $W^{5a}$ carbocycles and $W^5$ and $W^{5a}$ heterocycles may be independently substituted with 0 to 3 $R^2$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ or $W^{5a}$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ and $W^{5a}$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ and $W^{5a}$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ and $W^{5a}$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

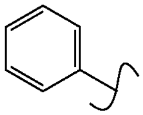,
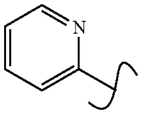,
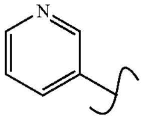,
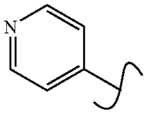,
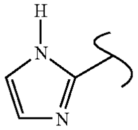,
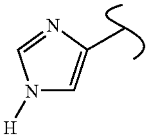,
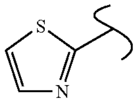,
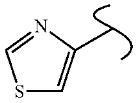, and
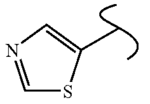.

$W^5$ and $W^{5a}$ carbocycles and heterocycles may be independently substituted with 0 to 3 $R^2$ groups, as defined above. For example, substituted $W^5$ carbocycles include:

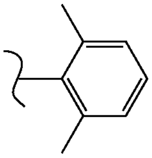
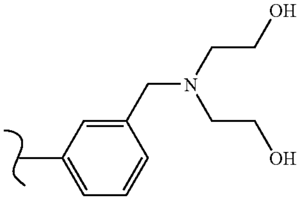
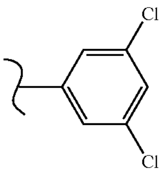
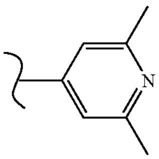
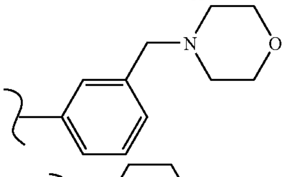
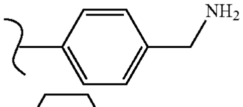
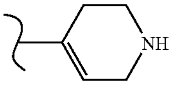
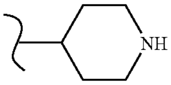
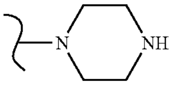
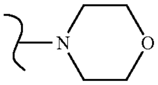

-continued

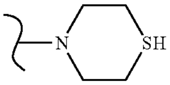
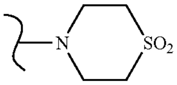

Examples of substituted phenyl carbocycles include:

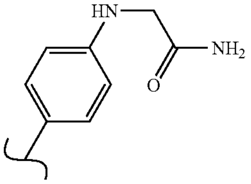
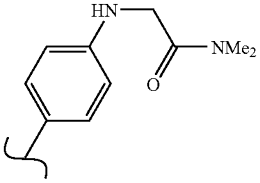
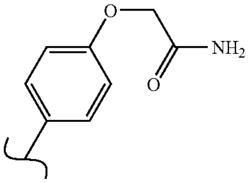
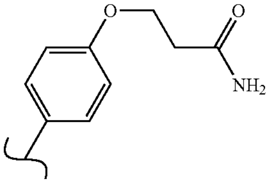
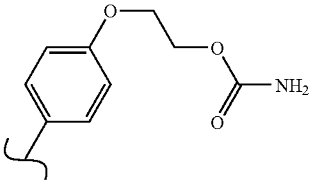
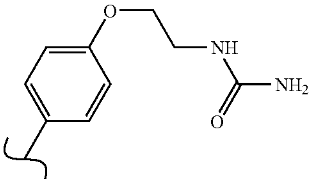

Embodiments of $A^1$ include:

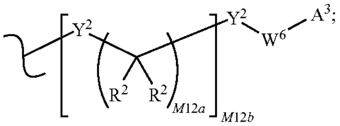

and where one or more $Y^2$ are a bond, such as:

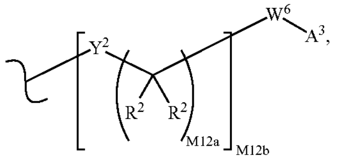

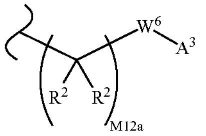

, and

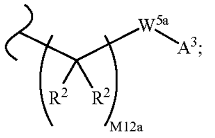

where $W^{5a}$ is a carbocycle or a heterocycle and $W^{5a}$ is independently substituted with 0 or 1 $R^2$ groups.

Embodiments of $A^1$ also include:

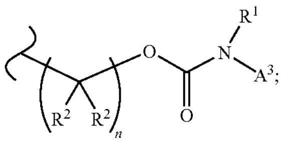

where n is an integer from 1 to 18.

Embodiments of $A^3$ include where M2 is 0, such as:

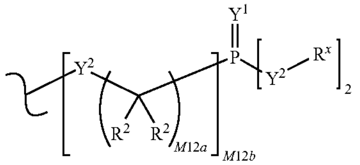

and where M12b is 1, $Y^1$ is oxygen, and $Y^{2b}$ is oxygen (O) or nitrogen ($N(R^x)$) such as:

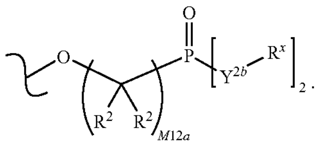

An embodiment of $A^3$ includes:

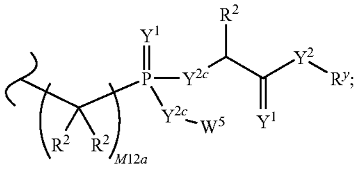

where $Y^{2c}$ is O, $N(R^y)$ or S. For example, $R^1$ may be H and n may be 1.

Another embodiment of $A^3$ includes:

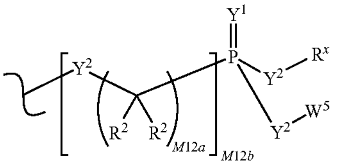

where $W^5$ is a carbocycle such as phenyl or substituted phenyl. Such embodiments include:

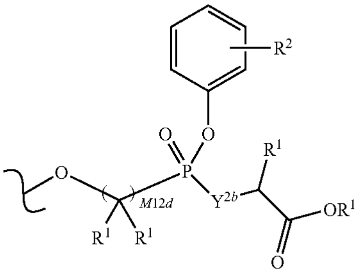

where $Y^{2b}$ is O or $N(R^x)$; M12d is 1, 2, 3, 4, 5, 6, 7 or 8; and the phenyl carbocycle is substituted with 0 to 3 $R^2$ groups. Such embodiments of $A^3$ include phenyl phosphonamidate amino acid, e.g. alanate esters and phenyl phosphonate-lactate esters:

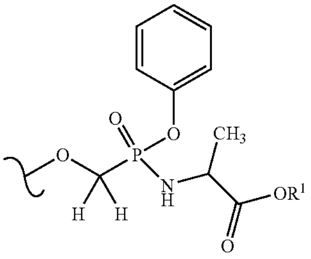

and

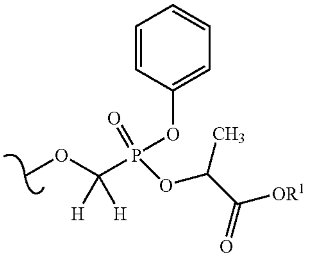

.

The chiral carbon of the amino acid and lactate moieties may be either the R or S configuration or the racemic mixture.

Embodiments of $R^x$ include esters, carbamates, carbonates, thioesters, amides, thioamides, and urea groups:

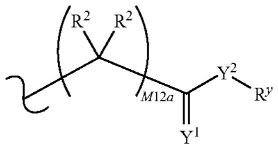

and

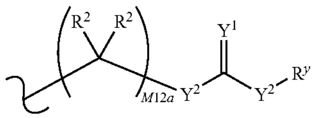

.

Embodiments of $A^2$ include where $W^3$ is $W^5$, such as:

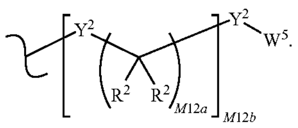

Alternatively, $A^2$ is phenyl, substituted phenyl, benzyl, substituted benzyl, pyridyl or substituted pyridyl.

Exemplary embodiments of Formula I compounds include, but are not limited to, structures:

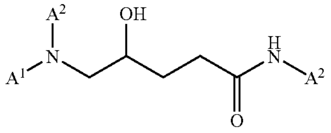

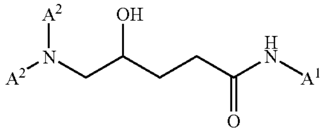

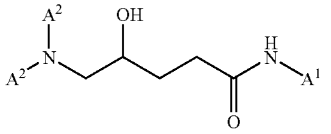

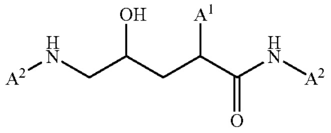

where $A^1$ denotes a covalent attachment site of a phosphonate group.

Exemplary embodiments of Formula II compounds include, but are not limited to, structures:

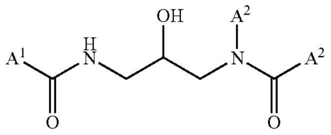

-continued

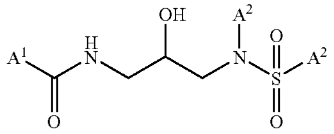

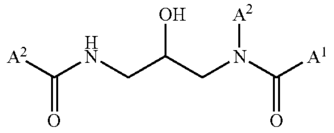

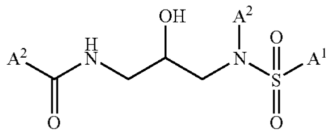

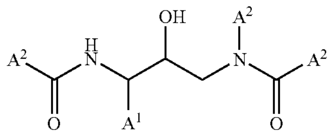

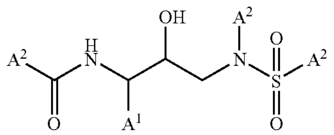

where $A^1$ denotes a covalent attachment site of a phosphonate group.

Exemplary embodiments of Formula III compounds include, but are not limited to, structures:

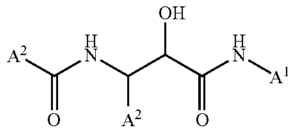

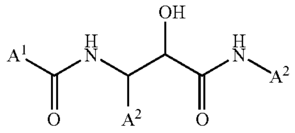

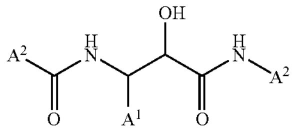

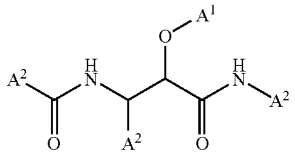

where $A^1$ denotes a covalent attachment site of a phosphonate group.

Exemplary embodiments of Formula IV compounds include, but are not limited to, structures:

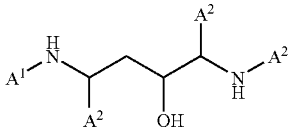

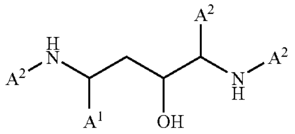

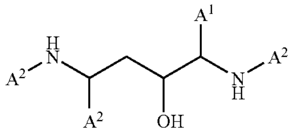

where A[1] denotes a covalent attachment site of a phosphonate group.

Exemplary embodiments of Formula V compounds include, but are not limited to, structures:

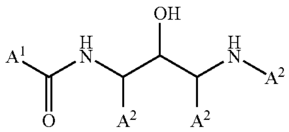

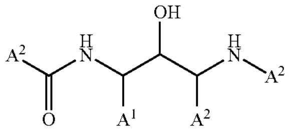

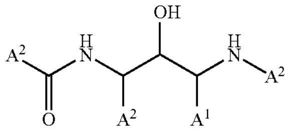

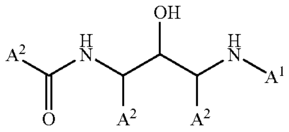

and

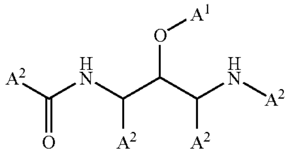

where A[1] denotes a covalent attachment site of a phosphonate group.

Exemplary embodiments of Formula VI compounds include, but are not limited to, structures:

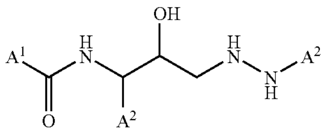

-continued

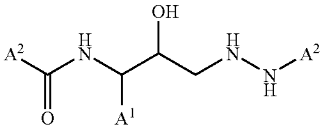

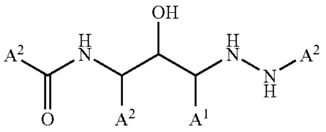

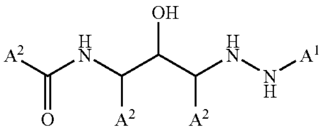

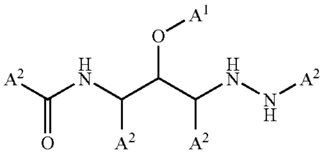

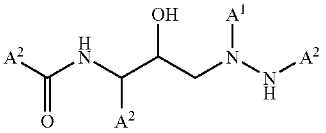

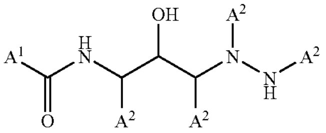

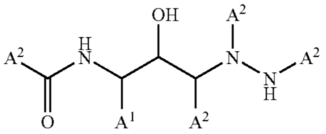

where A[1] denotes a covalent attachment site of a phosphonate group.

Exemplary embodiments of Formula VII compounds include, but are not limited to, structures:

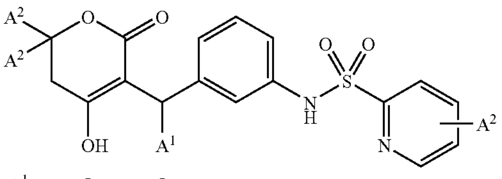

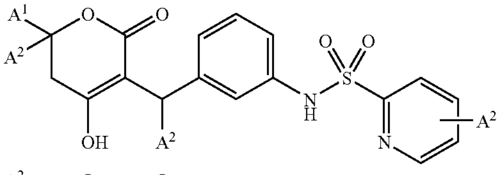

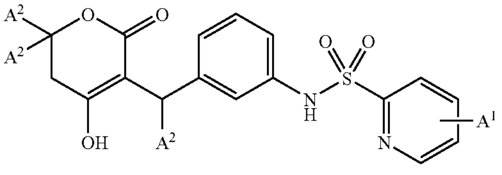

-continued

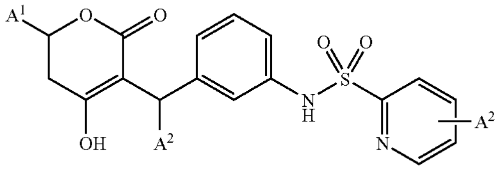

where $A^1$ denotes a covalent attachment site of a phosphonate group.

Exemplary embodiments of Formula VIIIa compounds include structures:

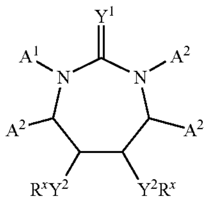

and

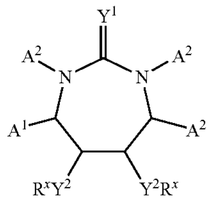

Exemplary embodiments of Formula VIIIb compounds include structures:

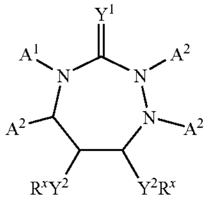

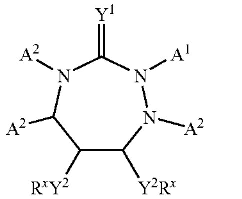

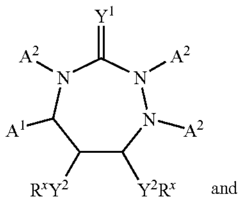

and

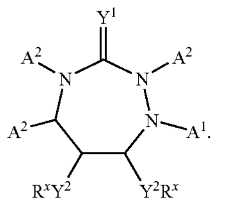

Exemplary embodiments of Formula VIIIc compounds include structures:

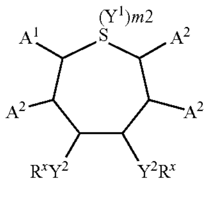

and

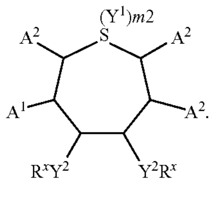

Exemplary embodiments of Formula VIIId compounds include structures:

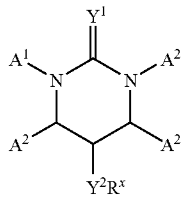

and

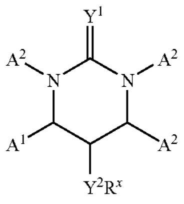

where $A^1$ denotes a covalent attachment site of a phosphonate group.

A Cellular Accumulation Embodiment

Another embodiment of the invention is directed toward an HIV protease inhibitor compound capable of accumulating in human PBMCs. Accumulation in human PBMCs is described in the examples herein. Typically, the compounds of this embodiment further comprise a phosponate or phosphonate prodrug. More typically, the phosphonate or phosphonate prodrug has the structure $A^3$ as described herein. Each of the preferred embodiments of $A^3$ described herein is a preferred embodiment of $A^3$ in the present embodiment.

Optionally, the compounds of this embodiment demonstrate improved intracellular half-life of the compounds or intracellular metabolites of the compounds in human PBMCs when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In a preferred embodiment, the intracellular half-life of a metabolite of the compound in human PBMCs is improved when compared to an analog of the compound not having the phosphonate or phosphonate prodrug. In such embodiments, the metabolite is typically generated intracellularly, more typically, it is generated within human PBMCs. Still more typically, the metabolite is a product of the cleavage of a phosphonate prodrug within human PBMCs. More typically yet, the phosphonate prodrug is cleaved to form a metabolite having at least one negative charge at physiological pH. Most typically, the phosphonate prodrug is enzymatically cleaved within human PBMCs to form a phosphonate having at least one active hydrogen atom of the form P—OH.

Not withstanding other disclosure herein which describes the role or presents of phosphonates in the compounds of the invention, in another embodiment of the invention $A^3$ is $A^{3a}$ which is of the formula:

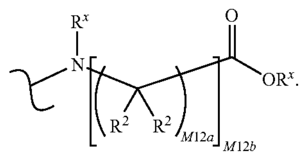

In this embodiment of the invention, any $A^3$ group may be $A^{3a}$.

In another aspect of the invention, $A^3$ is of the formula:

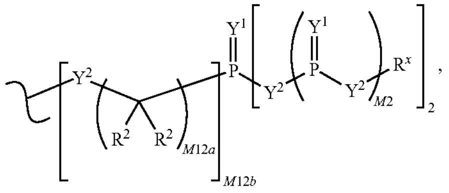

M12a is other than 0 and at least one phosphonate group present in the compound is not bonded directly to $W^3$. More typically, the phosphonate is not bonded directly to $W^5$. In such an embodiment, the phosphorous atom of the phosphonate is not bonded directly to a carbon atom of a ring.

In another aspect of the invention an Amprenavir like phosphonate protease inhibitor, as described above in the description and below in the claims, contains an $A^3$ group of the formula:

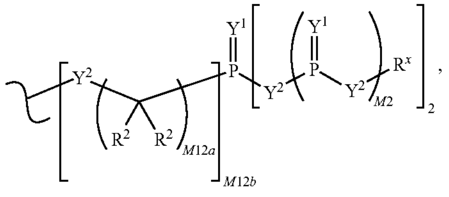

M12a is other than 0 and at least one phosphonate group present in the compound is not bonded directly to $W^3$. More typically, the phosphonate is not bonded directly to $W^5$. In such an embodiment, the phosphorous atom of the phosphonate is not bonded directly to a carbon atom of a ring.

One embodiment of Amprenavir like phosphonate protease inhibitors as described above in the description and below in the claims excludes compounds of the formulas:

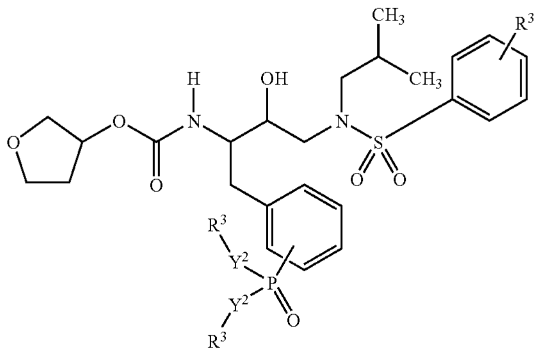

or

-continued

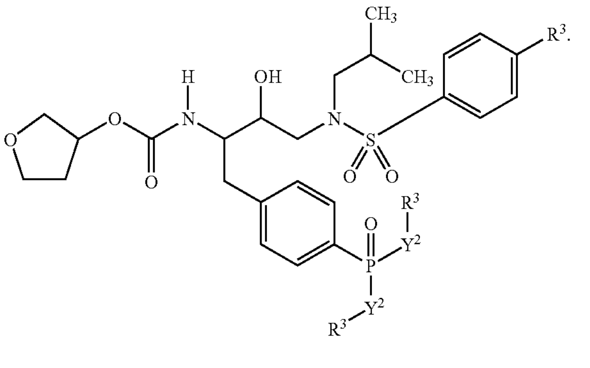

In another aspect of the invention, $A^3$ is of the formula:

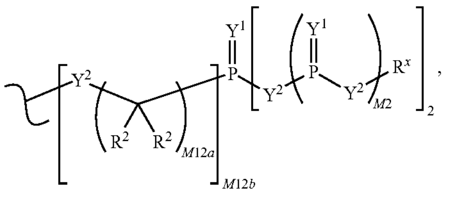

M12a is 0 and at least one phosphonate group present in the compound is bonded directly to $W^3$. More typically, the phosphonate is bonded directly to $W^5$. In such an embodiment, the phosphorous atom of the phosphonate is bonded directly to a carbon atom of a ring.

In another aspect of the invention an Amprenavir like phosphonate protease inhibitor, as described above in the description and below in the claims, contains an $A^3$ group of the formula:

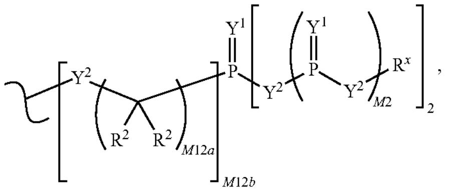

M12a is 0 and at least one phosphonate group present in the compound is bonded directly to $W^3$. More typically, the phosphonate is bonded directly to $W^5$. In such an embodiment, the phosphorous atom of the phosphonate is bonded directly to a carbon atom of a ring.

One embodiment of Amprenavir like phosphonate protease inhibitors as described above in the description and below in the claims is directed to compounds of the formulas:

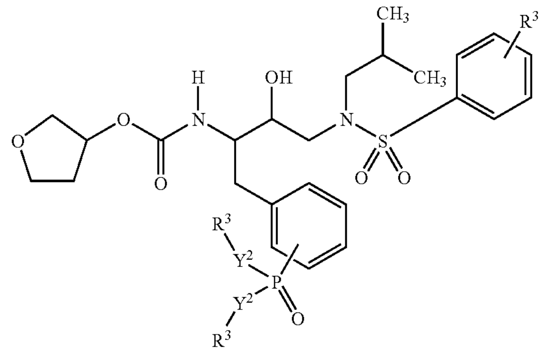

or

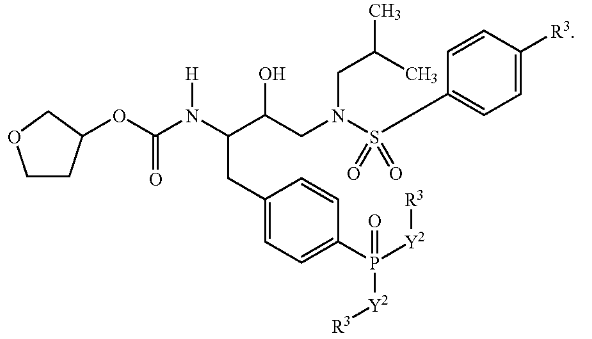

Exemplary Enumerated Compounds.

By way of example and not limitation, embodiments of the invention are named below in tabular format (Table 100). These embodiments are of the general formula "MBF":

MBF

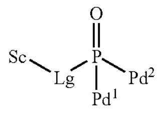

Each embodiment of MBF is depicted as a substituted nucleus (Sc) in which the nucleus is designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug ($Pd^1$ and $Pd^2$) substituents, again by letter or number designation, respectively.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups ($Pd^1$ and $Pd^2$) from Table 20.1-20.36. In graphical tabular form, each embodiment of Table 100 appears as a name having the syntax:

$Sc.Lg.Pd^1.Pd^2$

Thus, ignoring stereochemistry, structure 10, Scheme 2, Scheme Section A, is represented by 12.AH.247.247.

12.AH.247.247

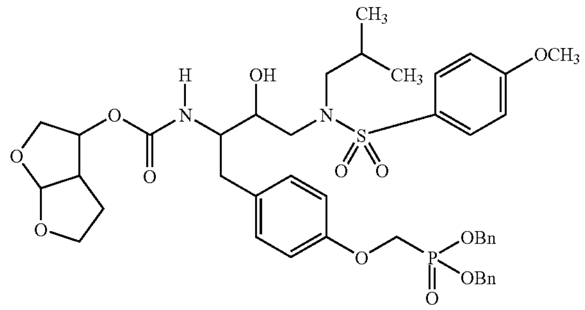

Each Sc group is shown having a tilda ("~"). The tilda is the point of covalent attachment of Sc to Lg. $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the tilda symbol ("~"). Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1

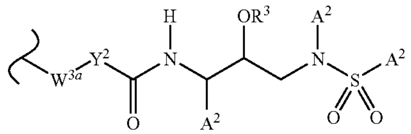

1

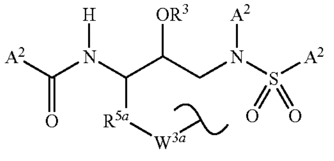

2

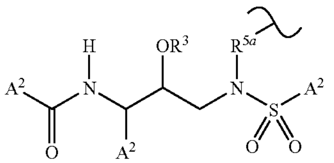

3

TABLE 1.1-continued
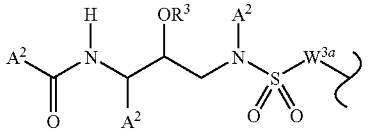
4
TABLE 1.2
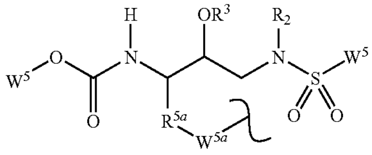
5
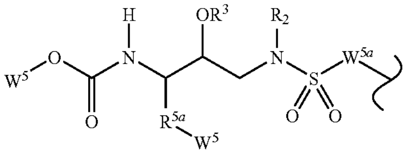
6
TABLE 1.3
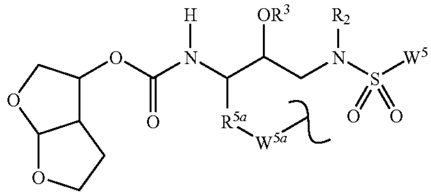
7
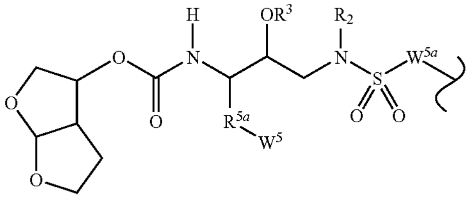
8
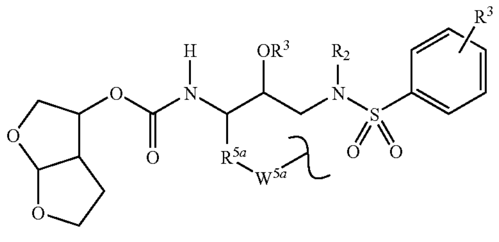
9
TABLE 1.3-continued
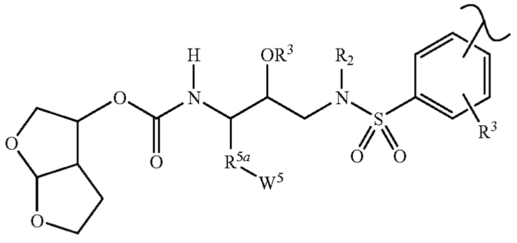
10
TABLE 1.4
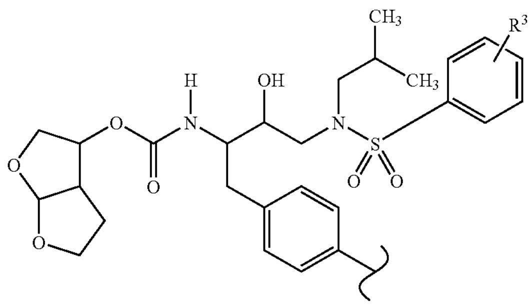
11
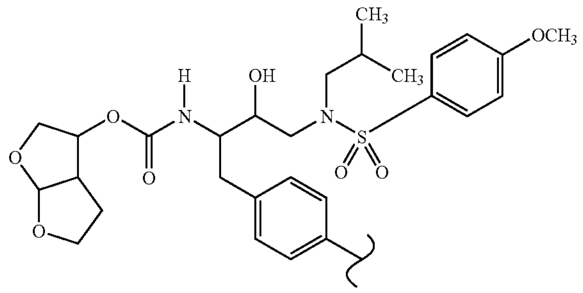
12
TABLE 1.5
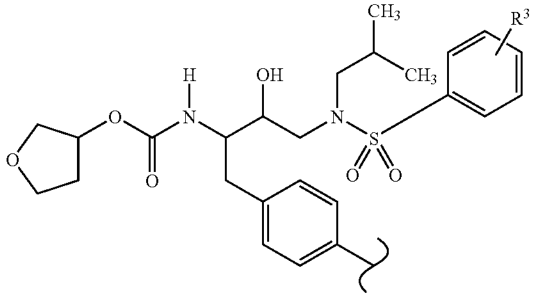
13

TABLE 1.5-continued
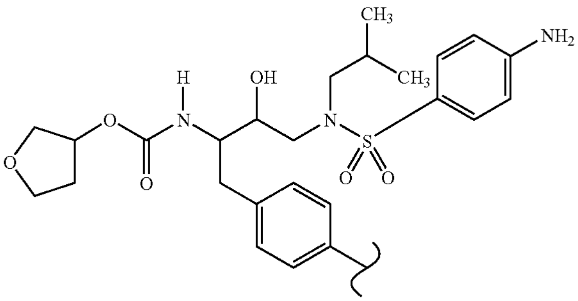
14
TABLE 10.1
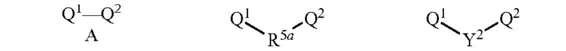
A B C
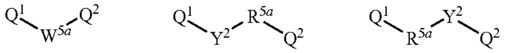
D E F
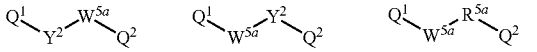
G H I
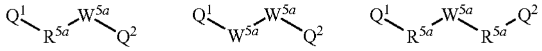
J K L
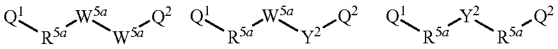
M N O
TABLE 10.2
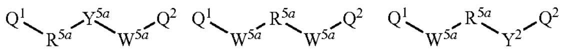
P Q R
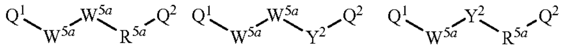
S T U
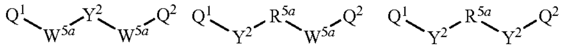
V W X
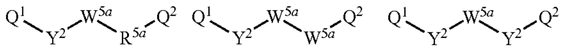
Y Z AA
TABLE 10.3
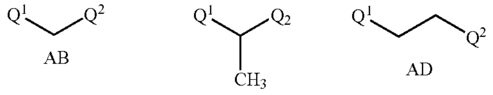
AB AC AD
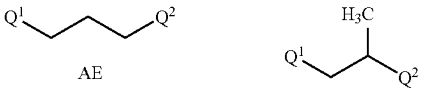
AE AF
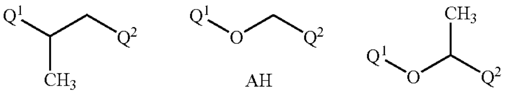
AG AH AI
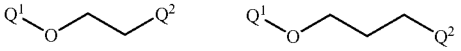
AJ AK
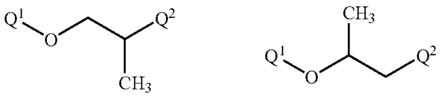
AL AM
TABLE 10.4
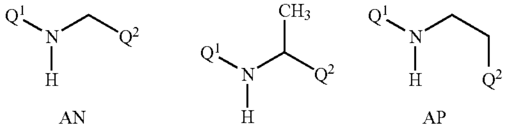
AN AO AP
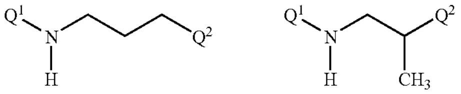
AQ AR
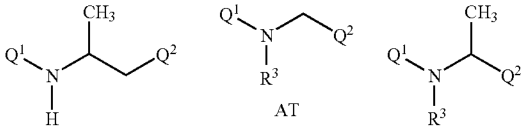
AS AT AU
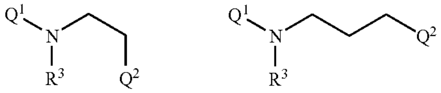
AV AW
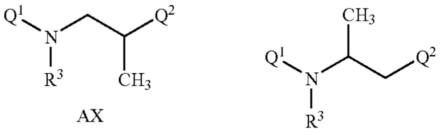
AX AY TABLE 10.5
| | |
|---|---|
| 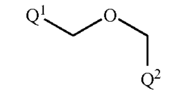 AZ | 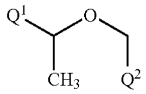 BA |
| 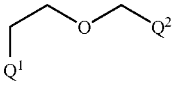 BB | 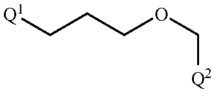 BC |
| 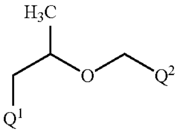 BD | 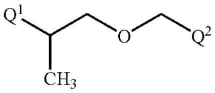 BE |
| 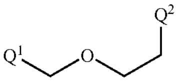 BF | 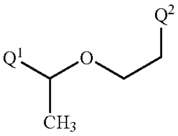 BG |
| 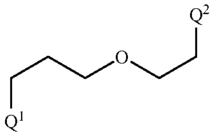 BH | 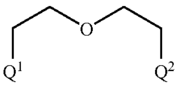 BI |
| 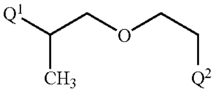 BJ1 | 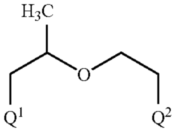 BJ2 |
TABLE 10.6
| | |
|---|---|
| 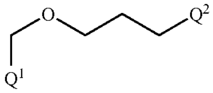 BK | 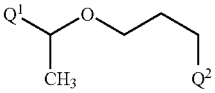 BL |
| 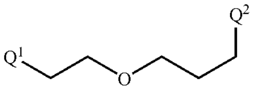 BM | 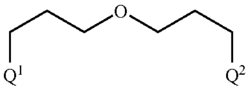 BN |
| 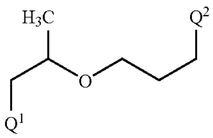 BO | 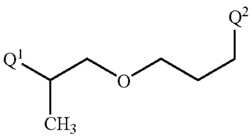 BP |
TABLE 10.7
| | |
|---|---|
| 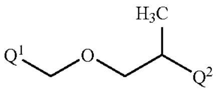 BQ | 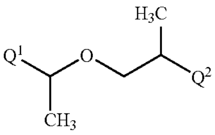 BR |
| 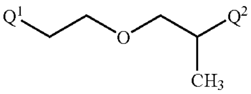 BS | 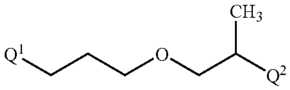 BT |
| 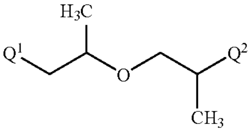 BU | 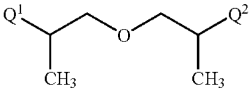 BV |
TABLE 10.8
| | |
|---|---|
| 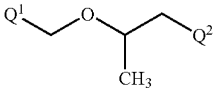 BW | 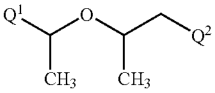 BX |
| 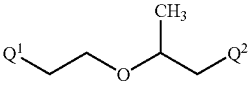 BY | 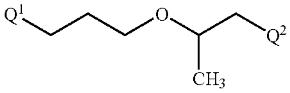 BZ |
| 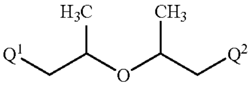 CA | 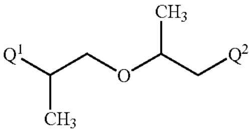 CB |
TABLE 10.9
| | |
|---|---|
| 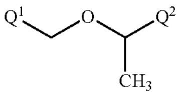 CC | 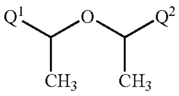 CD |
| 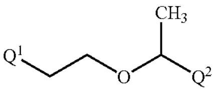 CE | 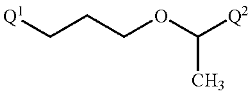 CF |

TABLE 10.9-continued
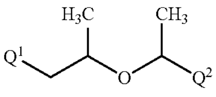
CG
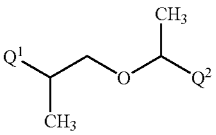
CH
TABLE 10.10
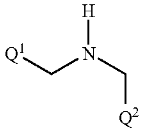
CI
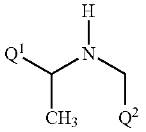
CJ
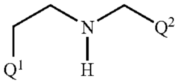
CK
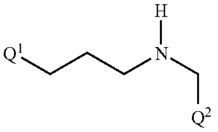
CL
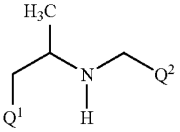
CM
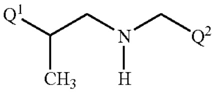
CN
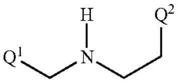
CO
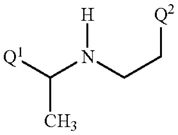
CP
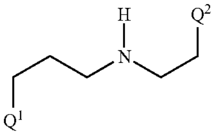
CQ
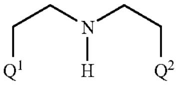
CR
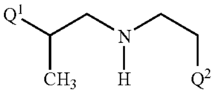
CS
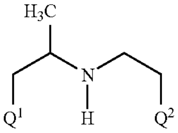
CT
TABLE 10.11
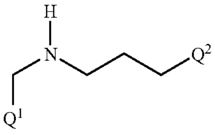
CU
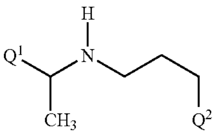
CV
TABLE 10.11-continued
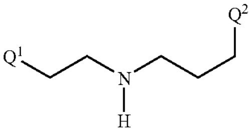
CW
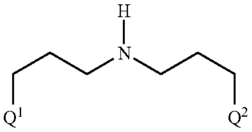
CX
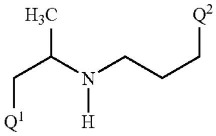
CY
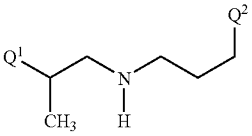
CZ
TABLE 10.12
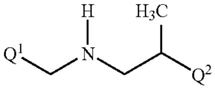
DA
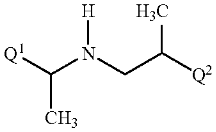
DB
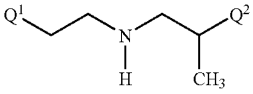
DC
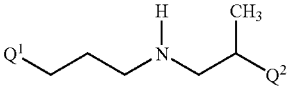
DD
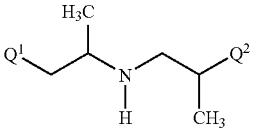
DE
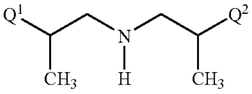
DF
TABLE 10.13
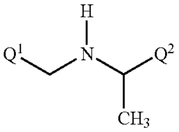
DG
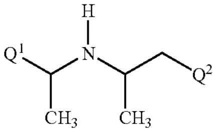
DH
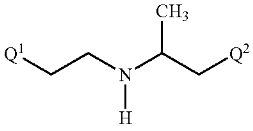
DI
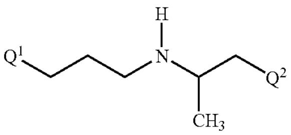
DJ
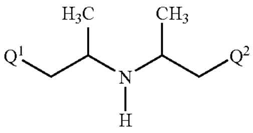
DK
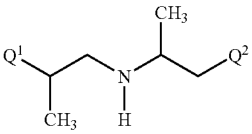
DL TABLE 10.14
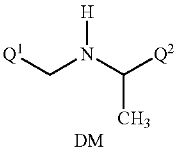
DM
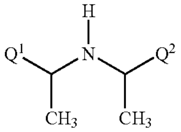
DN
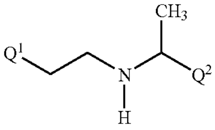
DO
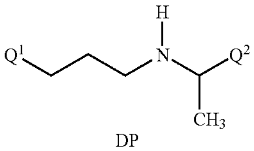
DP
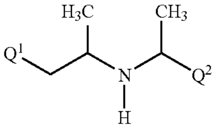
DQ
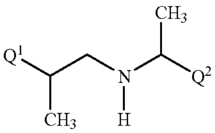
DR
TABLE 10.15
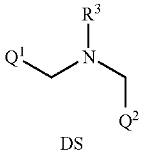
DS
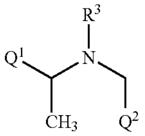
DT
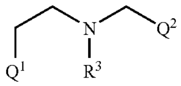
DU
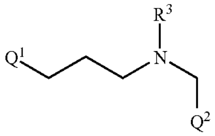
DV
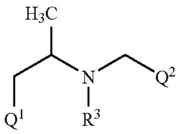
DW
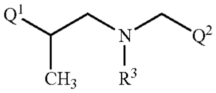
DX
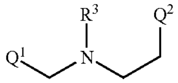
DY
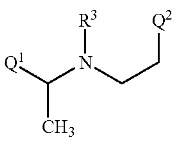
DZ
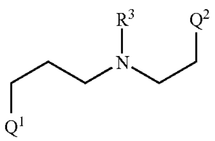
EA
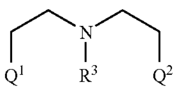
EB
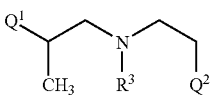
EC
TABLE 10.15-continued
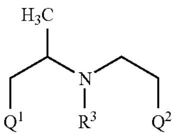
ED
TABLE 10.16
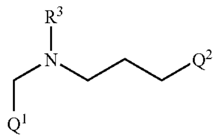
EE
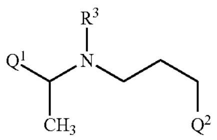
EF
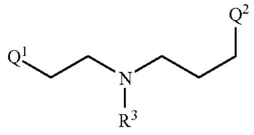
EG
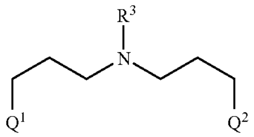
EH
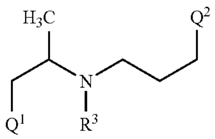
EI
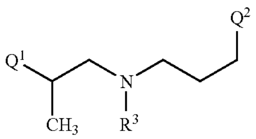
EJ
TABLE 10.17
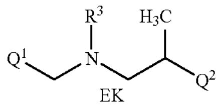
EK
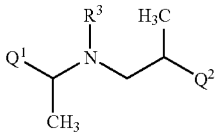
EL
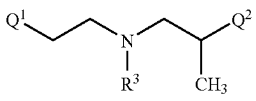
EM
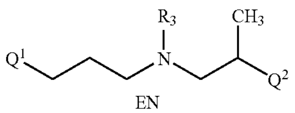
EN
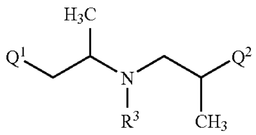
EO
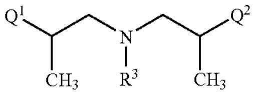
EP TABLE 10.18
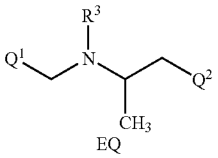
EQ
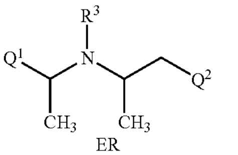
ER
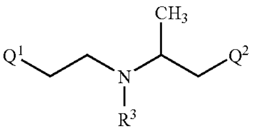
ES
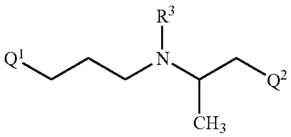
ET
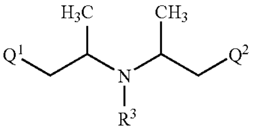
EU
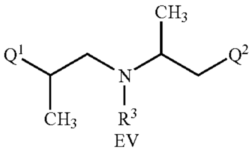
EV
TABLE 10.19
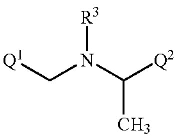
EW
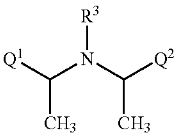
EX
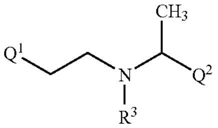
EY
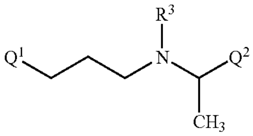
EZ
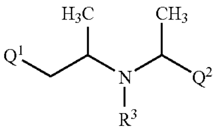
FA
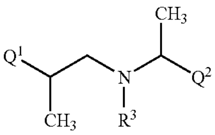
FB
TABLE 20.1
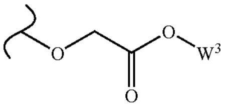
1
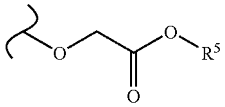
2
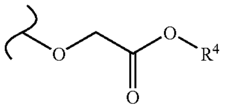
3
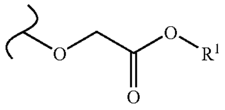
4
TABLE 20.1-continued
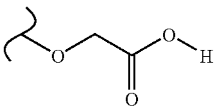
5
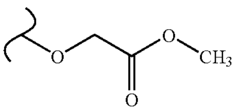
6
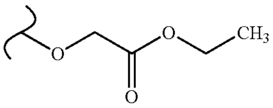
7
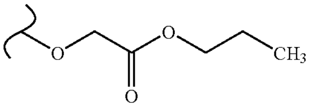
8
TABLE 20.2
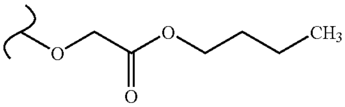
9
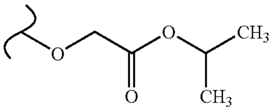
10
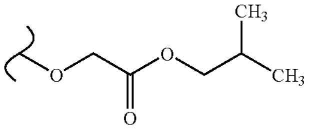
11
TABLE 20.3
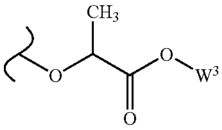
12
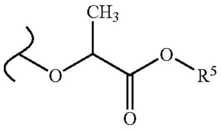
13
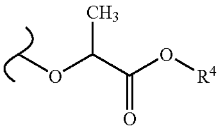
14
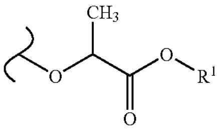
15

TABLE 20.3-continued
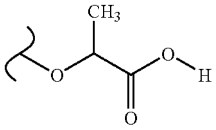
16
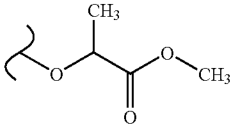
17
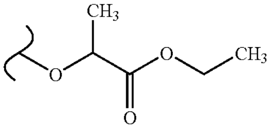
18
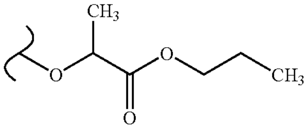
19
TABLE 20.4
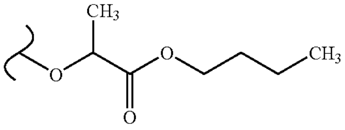
20
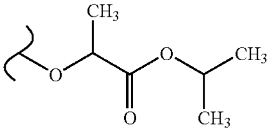
21
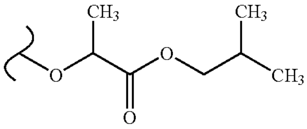
22
TABLE 20.5
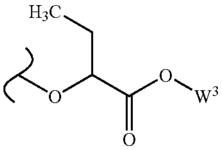
23
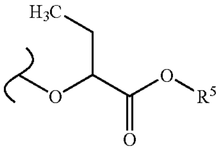
24
TABLE 20.5-continued
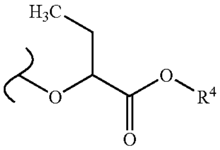
25
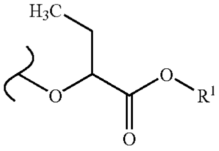
26
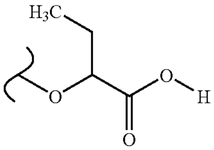
27
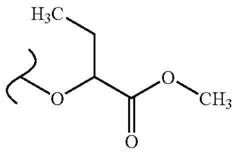
28
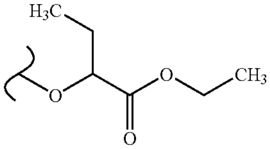
29
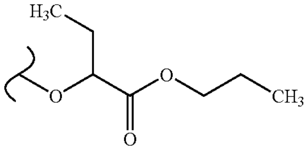
30
TABLE 20.6
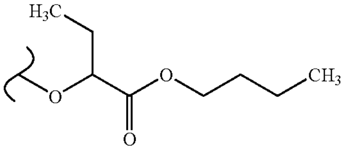
31
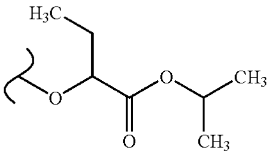
32
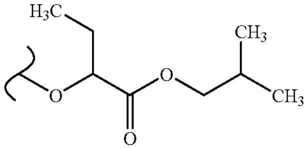
33

TABLE 20.7
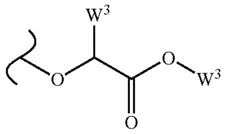
34
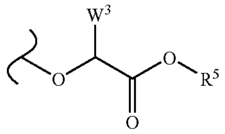
35
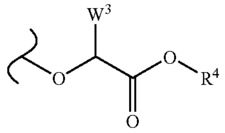
36
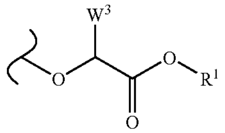
37
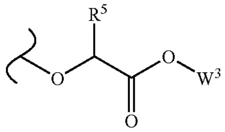
38
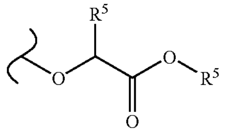
39
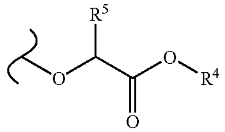
40
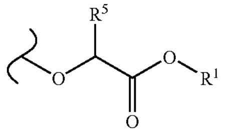
41
TABLE 20.8
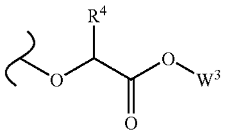
42
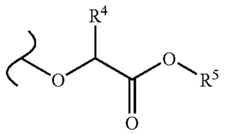
43
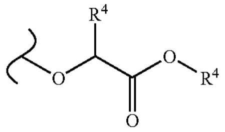
44
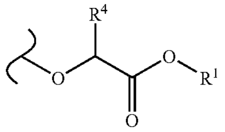
45
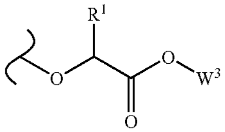
46
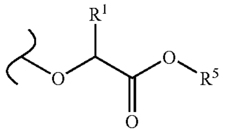
47
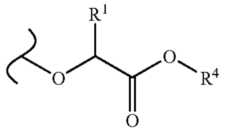
48
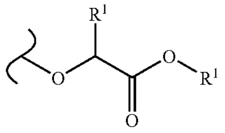
49
TABLE 20.9
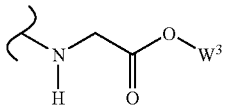
50
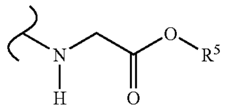
51
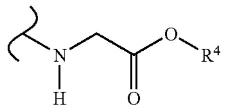
52
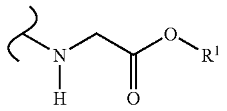
53
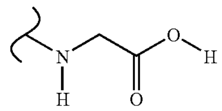
54
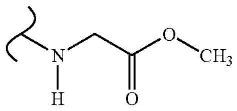
55
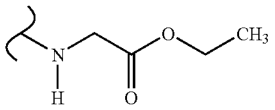
56
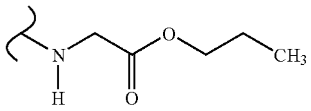
57
TABLE 20.10
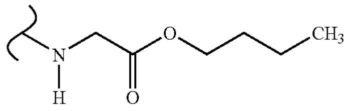
58
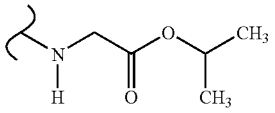
59
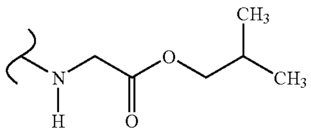
60

TABLE 20.11
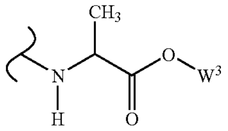
61
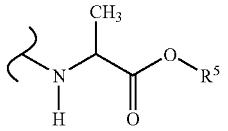
62
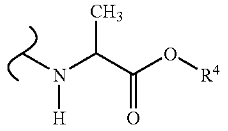
63
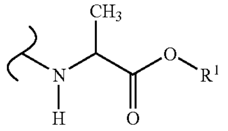
64
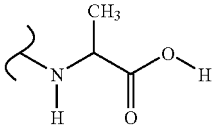
65
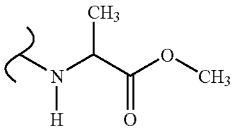
66
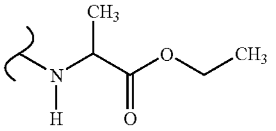
67
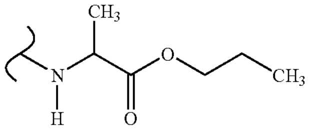
68
TABLE 20.12
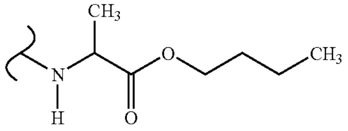
69
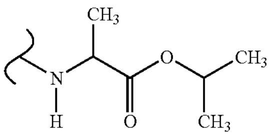
70
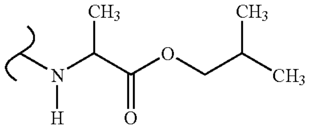
71
TABLE 20.13
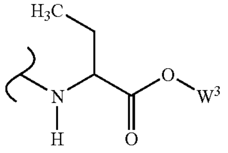
72
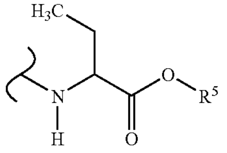
73
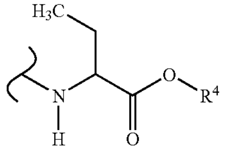
74
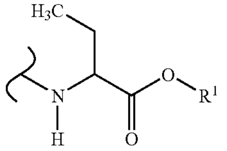
75
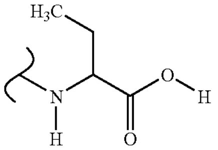
76
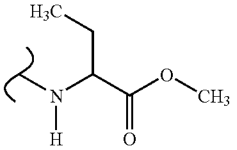
77
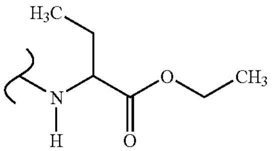
78
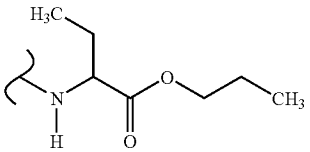
79
TABLE 20.14
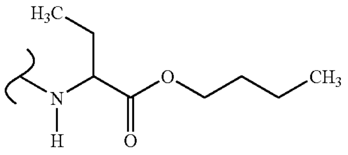
80
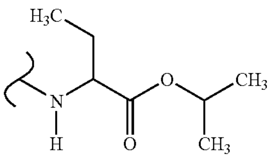
81

TABLE 20.14-continued
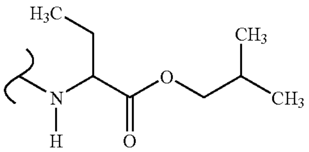
82
TABLE 20.15
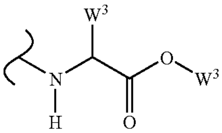
83
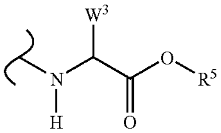
84
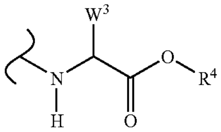
85
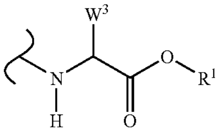
86
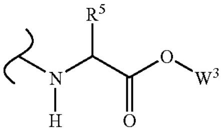
87
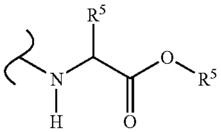
88
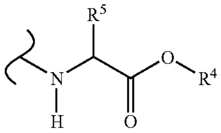
89
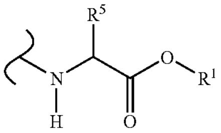
90
TABLE 20.16
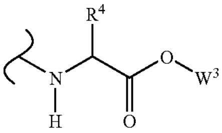
91
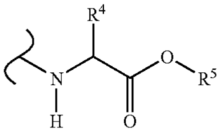
92
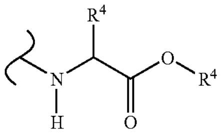
93
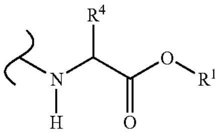
94
TABLE 20.16-continued
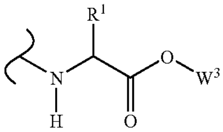
95
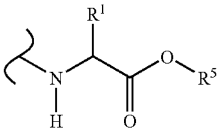
96
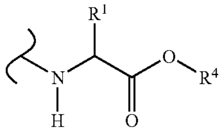
97
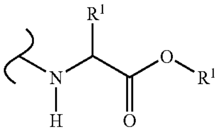
98
TABLE 20.17
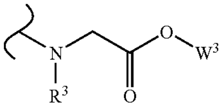
99
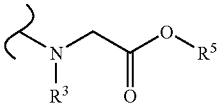
100
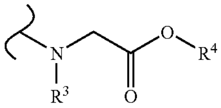
101
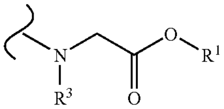
102
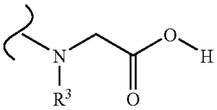
103
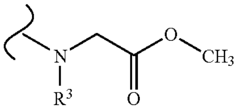
104
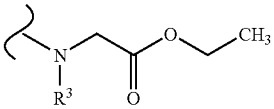
105
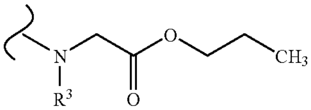
106
TABLE 20.18
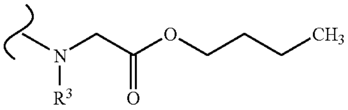
107
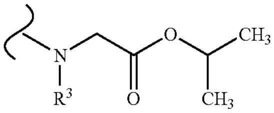
108

TABLE 20.18-continued
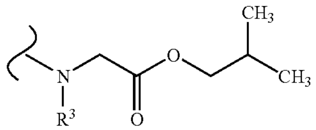
109
TABLE 20.19
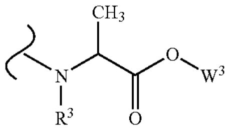
110
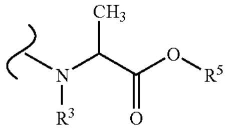
111
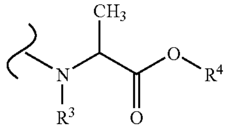
112
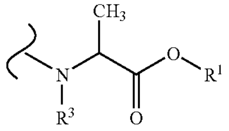
113
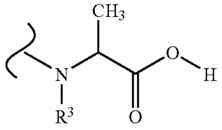
114
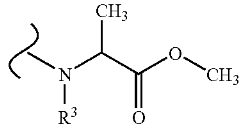
115
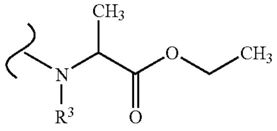
116
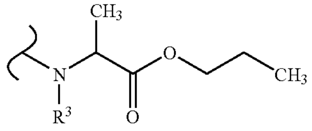
117
TABLE 20.20
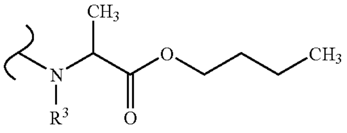
118
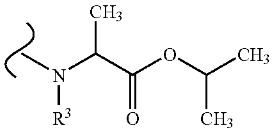
119
TABLE 20.20-continued
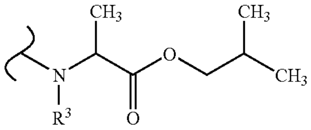
120
TABLE 20.21
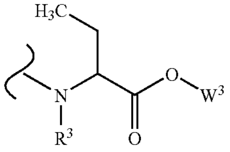
121
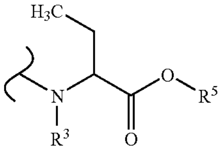
122
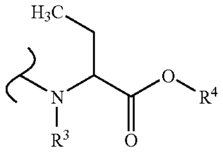
123
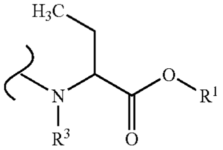
124
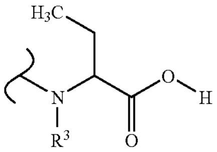
125
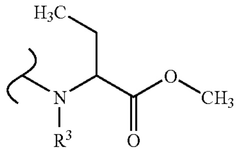
126
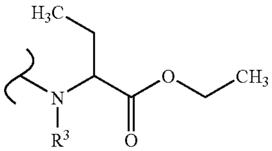
127
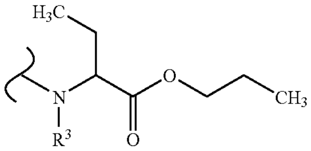
128
TABLE 20.22
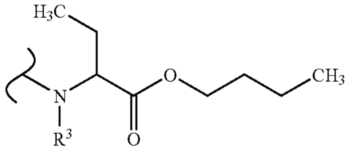
129

TABLE 20.22-continued
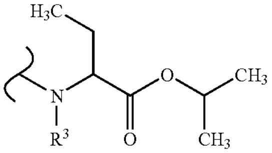
130
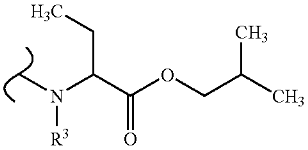
131
TABLE 20.23
| | |
|---|---|
| 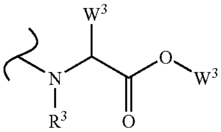 132 | 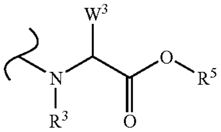 133 |
| 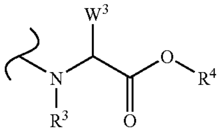 134 | 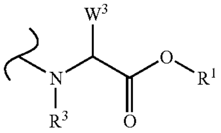 135 |
| 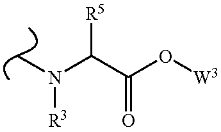 136 | 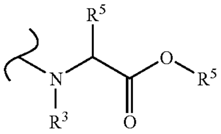 137 |
| 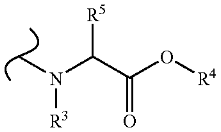 138 | 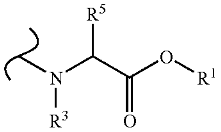 139 |
TABLE 20.24
| | |
|---|---|
| 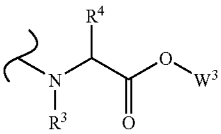 140 | 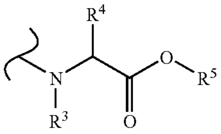 141 |
| 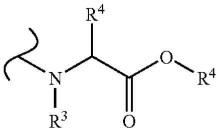 142 | 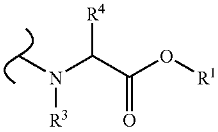 143 |
| 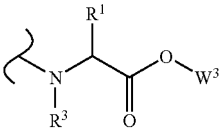 144 | 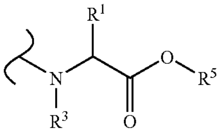 145 |
| 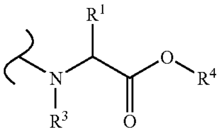 146 | 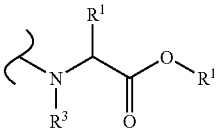 147 |
TABLE 20.25
| | | |
|---|---|---|
| 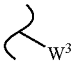 148 | 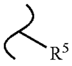 149 | 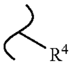 150 |
| 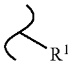 151 | 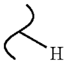 152 | 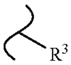 153 |
| 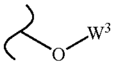 154 | 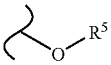 155 | 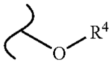 156 |
| 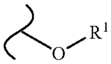 157 | 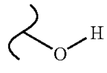 158 | 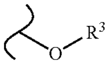 159 |
TABLE 20.26
| | | |
|---|---|---|
| 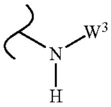 160 | 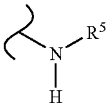 161 | 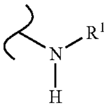 162 |
| 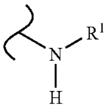 163 | 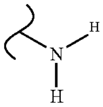 164 | 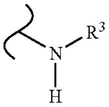 165 |
| 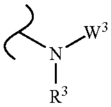 166 | 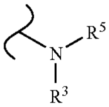 167 | 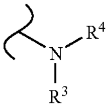 168 |

TABLE 20.26-continued
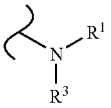
169
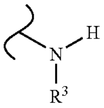
170
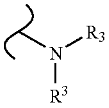
171
TABLE 20.27
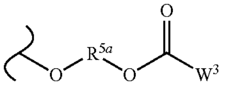
172
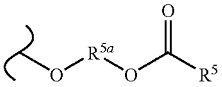
173
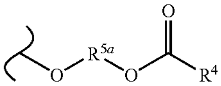
174
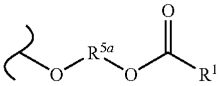
175
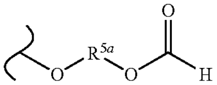
176
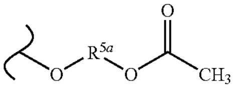
177
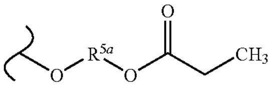
178
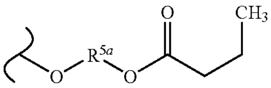
179
TABLE 20.28
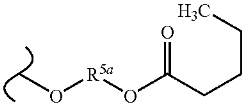
180
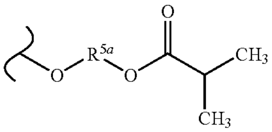
181
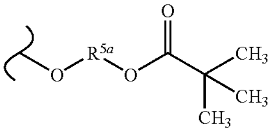
182
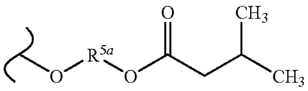
183
TABLE 20.28-continued
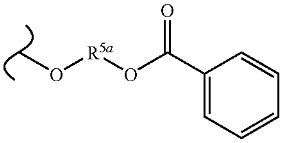
184
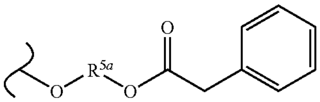
185
TABLE 20.29
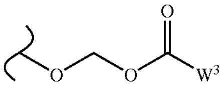
186
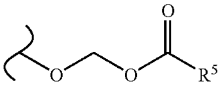
187
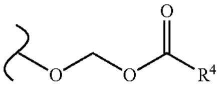
188
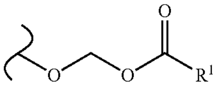
189
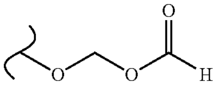
190
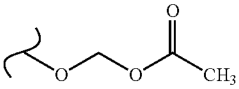
191
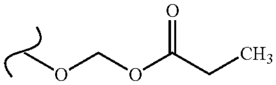
192
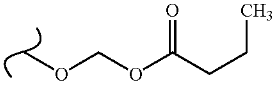
193
TABLE 20.30
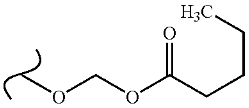
194
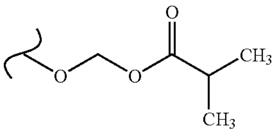
195
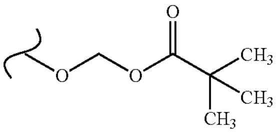
196

TABLE 20.30-continued
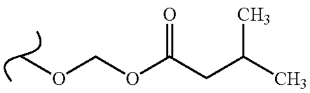
197
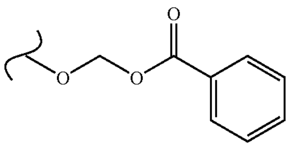
198
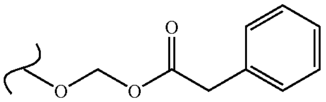
199
TABLE 20.31
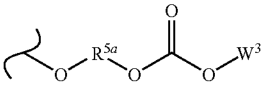
200
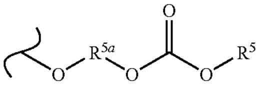
201
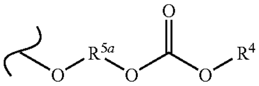
202
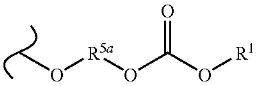
203
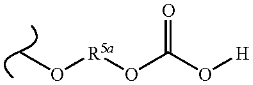
204
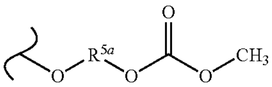
205
TABLE 20.31-continued
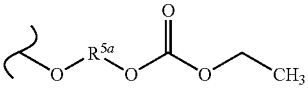
206
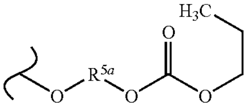
207
TABLE 20.32
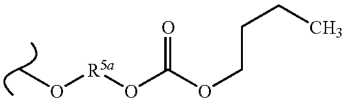
208
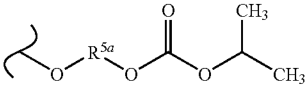
209
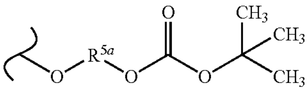
210
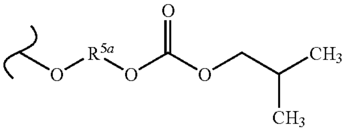
211
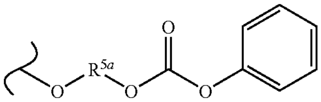
212
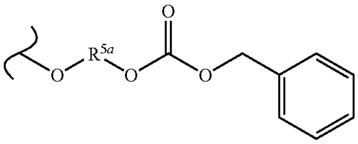
213
TABLE 20.33
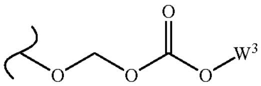
214

TABLE 20.33-continued
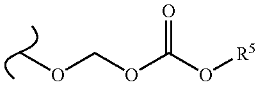
215
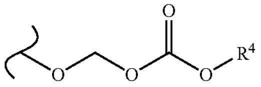
216
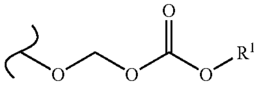
217
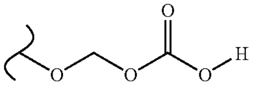
218
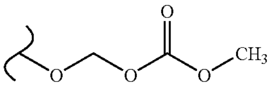
219
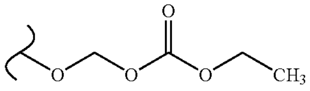
220
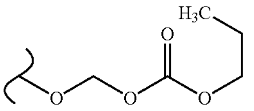
221
TABLE 20.34
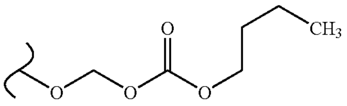
222
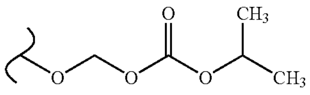
223
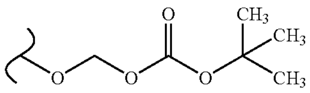
224
TABLE 20.34-continued
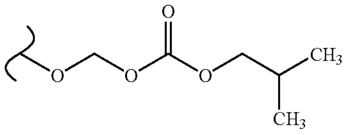
225
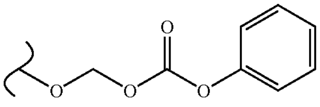
226
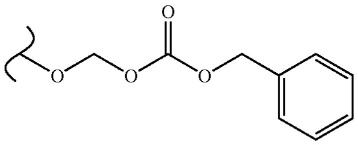
227
TABLE 20.35
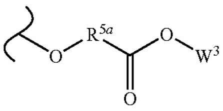
228
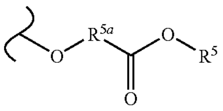
229
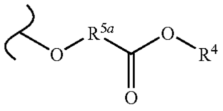
230
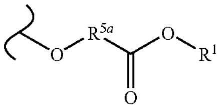
231
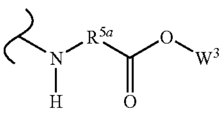
232
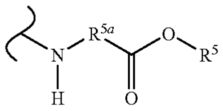
233
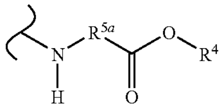
234
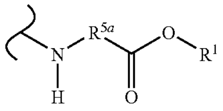
235
TABLE 20.36
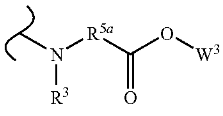
236
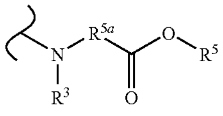
237

TABLE 20.36-continued

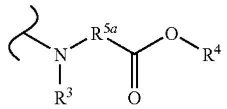

238

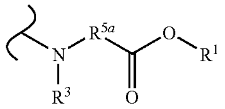

239

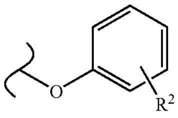

240

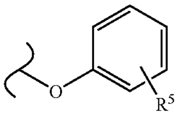

241

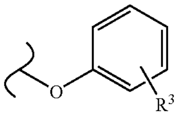

242

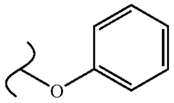

243

TABLE 20.36-continued

TABLE 20.37

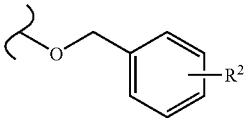

244

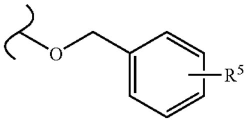

245

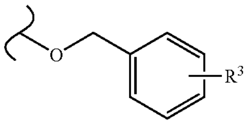

246

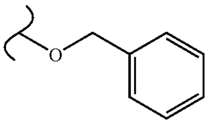

247

TABLE 100

Prodrugs of 1.B

1.B.228.228; 1.B.228.229; 1.B.228.230; 1.B.228.231; 1.B.228.236; 1.B.228.237; 1.B.228.238; 1.B.228.239; 1.B.228.154; 1.B.228.157; 1.B.228.166; 1.B.228.169; 1.B.228.172; 1.B.228.175; 1.B.228.240; 1.B.228.244; 1.B.229.228; 1.B.229.229; 1.B.229.230; 1.B.229.231; 1.B.229.236; 1.B.229.237; 1.B.229.238; 1.B.229.239; 1.B.229.154; 1.B.229.157; 1.B.229.166; 1.B.229.169; 1.B.229.172; 1.B.229.175; 1.B.229.240; 1.B.229.244; 1.B.230.228; 1.B.230.229; 1.B.230.230; 1.B.230.231; 1.B.230.236; 1.B.230.237; 1.B.230.238; 1.B.230.239; 1.B.230.154; 1.B.230.157; 1.B.230.166; 1.B.230.169; 1.B.230.172; 1.B.230.175; 1.B.230.240; 1.B.230.244; 1.B.231.228; 1.B.231.229; 1.B.231.230; 1.B.231.231; 1.B.231.236; 1.B.231.237; 1.B.231.238; 1.B.231.239; 1.B.231.154; 1.B.231.157; 1.B.231.166; 1.B.231.169; 1.B.231.172; 1.B.231.175; 1.B.231.240; 1.B.231.244; 1.B.236.228; 1.B.236.229; 1.B.236.230; 1.B.236.231; 1.B.236.236; 1.B.236.237; 1.B.236.238; 1.B.236.239; 1.B.236.154; 1.B.236.157; 1.B.236.166; 1.B.236.169; 1.B.236.172; 1.B.236.175; 1.B.236.240; 1.B.236.244; 1.B.237.228; 1.B.237.229; 1.B.237.230; 1.B.237.231; 1.B.237.236; 1.B.237.237; 1.B.237.238; 1.B.237.239; 1.B.237.154; 1.B.237.157; 1.B.237.166; 1.B.237.169; 1.B.237.172; 1.B.237.175; 1.B.237.240; 1.B.237.244; 1.B.238.228; 1.B.238.229; 1.B.238.230; 1.B.238.231; 1.B.238.236; 1.B.238.237; 1.B.238.238; 1.B.238.239; 1.B.238.154; 1.B.238.157; 1.B.238.166; 1.B.238.169; 1.B.238.172; 1.B.238.175; 1.B.238.240; 1.B.238.244; 1.B.239.228; 1.B.239.229; 1.B.239.230; 1.B.239.231; 1.B.239.236; 1.B.239.237; 1.B.239.238; 1.B.239.239; 1.B.239.154; 1.B.239.157; 1.B.239.166; 1.B.239.169; 1.B.239.172; 1.B.239.175; 1.B.239.240; 1.B.239.244; 1.B.154.228; 1.B.154.229; 1.B.154.230; 1.B.154.231; 1.B.154.236; 1.B.154.237; 1.B.154.238; 1.B.154.239; 1.B.154.154; 1.B.154.157; 1.B.154.166; 1.B.154.169; 1.B.154.172; 1.B.154.175; 1.B.154.240; 1.B.154.244; 1.B.157.228; 1.B.157.229; 1.B.157.230; 1.B.157.231; 1.B.157.236; 1.B.157.237; 1.B.157.238; 1.B.157.239; 1.B.157.154; 1.B.157.157; 1.B.157.166; 1.B.157.169; 1.B.157.172; 1.B.157.175; 1.B.157.240; 1.B.157.244; 1.B.166.228; 1.B.166.229; 1.B.166.230; 1.B.166.231; 1.B.166.236; 1.B.166.237; 1.B.166.238; 1.B.166.239; 1.B.166.154; 1.B.166.157; 1.B.166.166; 1.B.166.169; 1.B.166.172; 1.B.166.175; 1.B.166.240; 1.B.166.244; 1.B.169.228; 1.B.169.229; 1.B.169.230; 1.B.169.231; 1.B.169.236; 1.B.169.237; 1.B.169.238; 1.B.169.239; 1.B.169.154; 1.B.169.157; 1.B.169.166; 1.B.169.169; 1.B.169.172; 1.B.169.175; 1.B.169.240; 1.B.169.244; 1.B.172.228; 1.B.172.229; 1.B.172.230; 1.B.172.231; 1.B.172.236; 1.B.172.237; 1.B.172.238; 1.B.172.239; 1.B.172.154; 1.B.172.157; 1.B.172.166; 1.B.172.169; 1.B.172.172; 1.B.172.175; 1.B.172.240; 1.B.172.244; 1.B.175.228; 1.B.175.229; 1.B.175.230; 1.B.175.231; 1.B.175.236; 1.B.175.237; 1.B.175.238; 1.B.175.239; 1.B.175.154; 1.B.175.157; 1.B.175.166; 1.B.175.169; 1.B.175.172; 1.B.175.175; 1.B.175.240; 1.B.175.244; 1.B.240.228; 1.B.240.229; 1.B.240.230; 1.B.240.231; 1.B.240.236; 1.B.240.237; 1.B.240.238; 1.B.240.239; 1.B.240.154; 1.B.240.157; 1.B.240.166; 1.B.240.169; 1.B.240.172; 1.B.240.175; 1.B.240.240; 1.B.240.244; 1.B.244.228; 1.B.244.229; 1.B.244.230; 1.B.244.231; 1.B.244.236; 1.B.244.237; 1.B.244.238; 1.B.244.239; 1.B.244.154; 1.B.244.157; 1.B.244.166; 1.B.244.169; 1.B.244.172; 1.B.244.175; 1.B.244.240; 1.B.244.244;

Prodrugs of 1.D

1.D.228.228; 1.D.228.229; 1.D.228.230; 1.D.228.231; 1.D.228.236; 1.D.228.237; 1.D.228.238; 1.D.228.239; 1.D.228.154; 1.D.228.157; 1.D.228.166; 1.D.228.169; 1.D.228.172; 1.D.228.175; 1.D.228.240; 1.D.228.244; 1.D.229.228; 1.D.229.229; 1.D.229.230; 1.D.229.231; 1.D.229.236; 1.D.229.237; 1.D.229.238; 1.D.229.239; 1.D.229.154; 1.D.229.157; 1.D.229.166; 1.D.229.169; 1.D.229.172; 1.D.229.175; 1.D.229.240; 1.D.229.244; 1.D.230.228; 1.D.230.229; 1.D.230.230; 1.D.230.231; 1.D.230.236; 1.D.230.237; 1.D.230.238; 1.D.230.239; 1.D.230.154; 1.D.230.157; 1.D.230.166; 1.D.230.169; 1.D.230.172; 1.D.230.175; 1.D.230.240; 1.D.230.244; 1.D.231.228; 1.D.231.229; 1.D.231.230; 1.D.231.231; 1.D.231.236; 1.D.231.237;

TABLE 100-continued

1.D.231.238; 1.D.231.239; 1.D.231.154; 1.D.231.157; 1.D.231.166; 1.D.231.169;
1.D.231.172; 1.D.231.175; 1.D.231.240; 1.D.231.244; 1.D.236.228; 1.D.236.229;
1.D.236.230; 1.D.236.231; 1.D.236.236; 1.D.236.237; 1.D.236.238; 1.D.236.239;
1.D.236.154; 1.D.236.157; 1.D.236.166; 1.D.236.169; 1.D.236.172; 1.D.236.175;
1.D.236.240; 1.D.236.244; 1.D.237.228; 1.D.237.229; 1.D.237.230; 1.D.237.231;
1.D.237.236; 1.D.237.237; 1.D.237.238; 1.D.237.239; 1.D.237.154; 1.D.237.157;
1.D.237.166; 1.D.237.169; 1.D.237.172; 1.D.237.175; 1.D.237.240; 1.D.237.244;
1.D.238.228; 1.D.238.229; 1.D.238.230; 1.D.238.231; 1.D.238.236; 1.D.238.237;
1.D.238.238; 1.D.238.239; 1.D.238.154; 1.D.238.157; 1.D.238.166; 1.D.238.169;
1.D.238.172; 1.D.238.175; 1.D.238.240; 1.D.238.244; 1.D.239.228; 1.D.239.229;
1.D.239.230; 1.D.239.231; 1.D.239.236; 1.D.239.237; 1.D.239.238; 1.D.239.239;
1.D.239.154; 1.D.239.157; 1.D.239.166; 1.D.239.169; 1.D.239.172; 1.D.239.175;
1.D.239.240; 1.D.239.244; 1.D.154.228; 1.D.154.229; 1.D.154.230; 1.D.154.231;
1.D.154.236; 1.D.154.237; 1.D.154.238; 1.D.154.239; 1.D.154.154; 1.D.154.157;
1.D.154.166; 1.D.154.169; 1.D.154.172; 1.D.154.175; 1.D.154.240; 1.D.154.244;
1.D.157.228; 1.D.157.229; 1.D.157.230; 1.D.157.231; 1.D.157.236; 1.D.157.237;
1.D.157.238; 1.D.157.239; 1.D.157.154; 1.D.157.157; 1.D.157.166; 1.D.157.169;
1.D.157.172; 1.D.157.175; 1.D.157.240; 1.D.157.244; 1.D.166.228; 1.D.166.229;
1.D.166.230; 1.D.166.231; 1.D.166.236; 1.D.166.237; 1.D.166.238; 1.D.166.239;
1.D.166.154; 1.D.166.157; 1.D.166.166; 1.D.166.169; 1.D.166.172; 1.D.166.175;
1.D.166.240; 1.D.166.244; 1.D.169.228; 1.D.169.229; 1.D.169.230; 1.D.169.231;
1.D.169.236; 1.D.169.237; 1.D.169.238; 1.D.169.239; 1.D.169.154; 1.D.169.157;
1.D.169.166; 1.D.169.169; 1.D.169.172; 1.D.169.175; 1.D.169.240; 1.D.169.244;
1.D.172.228; 1.D.172.229; 1.D.172.230; 1.D.172.231; 1.D.172.236; 1.D.172.237;
1.D.172.238; 1.D.172.239; 1.D.172.154; 1.D.172.157; 1.D.172.166; 1.D.172.169;
1.D.172.172; 1.D.172.175; 1.D.172.240; 1.D.172.244; 1.D.175.228; 1.D.175.229;
1.D.175.230; 1.D.175.231; 1.D.175.236; 1.D.175.237; 1.D.175.238; 1.D.175.239;
1.D.175.154; 1.D.175.157; 1.D.175.166; 1.D.175.169; 1.D.175.172; 1.D.175.175;
1.D.175.240; 1.D.175.244; 1.D.240.228; 1.D.240.229; 1.D.240.230; 1.D.240.231;
1.D.240.236; 1.D.240.237; 1.D.240.238; 1.D.240.239; 1.D.240.154; 1.D.240.157;
1.D.240.166; 1.D.240.169; 1.D.240.172; 1.D.240.175; 1.D.240.240; 1.D.240.244;
1.D.244.228; 1.D.244.229; 1.D.244.230; 1.D.244.231; 1.D.244.236; 1.D.244.237;
1.D.244.238; 1.D.244.239; 1.D.244.154; 1.D.244.157; 1.D.244.166; 1.D.244.169;
1.D.244.172; 1.D.244.175; 1.D.244.240; 1.D.244.244;

Prodrugs of 1.E

1.E.228.228; 1.E.228.229; 1.E.228.230; 1.E.228.231; 1.E.228.236; 1.E.228.237;
1.E.228.238; 1.E.228.239; 1.E.228.154; 1.E.228.157; 1.E.228.166; 1.E.228.169; 1.E.228.172;
1.E.228.175; 1.E.228.240; 1.E.228.244; 1.E.229.228; 1.E.229.229; 1.E.229.230; 1.E.229.231;
1.E.229.236; 1.E.229.237; 1.E.229.238; 1.E.229.239; 1.E.229.154; 1.E.229.157; 1.E.229.166;
1.E.229.169; 1.E.229.172; 1.E.229.175; 1.E.229.240; 1.E.229.244; 1.E.230.228; 1.E.230.229;
1.E.230.230; 1.E.230.231; 1.E.230.236; 1.E.230.237; 1.E.230.238; 1.E.230.239; 1.E.230.154;
1.E.230.157; 1.E.230.166; 1.E.230.169; 1.E.230.172; 1.E.230.175; 1.E.230.240; 1.E.230.244;
1.E.231.228; 1.E.231.229; 1.E.231.230; 1.E.231.231; 1.E.231.236; 1.E.231.237; 1.E.231.238;
1.E.231.239; 1.E.231.154; 1.E.231.157; 1.E.231.166; 1.E.231.169; 1.E.231.172; 1.E.231.175;
1.E.231.240; 1.E.231.244; 1.E.236.228; 1.E.236.229; 1.E.236.230; 1.E.236.231; 1.E.236.236;
1.E.236.237; 1.E.236.238; 1.E.236.239; 1.E.236.154; 1.E.236.157; 1.E.236.166; 1.E.236.169;
1.E.236.172; 1.E.236.175; 1.E.236.240; 1.E.236.244; 1.E.237.228; 1.E.237.229; 1.E.237.230;
1.E.237.231; 1.E.237.236; 1.E.237.237; 1.E.237.238; 1.E.237.239; 1.E.237.154; 1.E.237.157;
1.E.237.166; 1.E.237.169; 1.E.237.172; 1.E.237.175; 1.E.237.240; 1.E.237.244; 1.E.238.228;
1.E.238.229; 1.E.238.230; 1.E.238.231; 1.E.238.236; 1.E.238.237; 1.E.238.238; 1.E.238.239;
1.E.238.154; 1.E.238.157; 1.E.238.166; 1.E.238.169; 1.E.238.172; 1.E.238.175; 1.E.238.240;
1.E.238.244; 1.E.239.228; 1.E.239.229; 1.E.239.230; 1.E.239.231; 1.E.239.236; 1.E.239.237;
1.E.239.238; 1.E.239.239; 1.E.239.154; 1.E.239.157; 1.E.239.166; 1.E.239.169; 1.E.239.172;
1.E.239.175; 1.E.239.240; 1.E.239.244; 1.E.154.228; 1.E.154.229; 1.E.154.230; 1.E.154.231;
1.E.154.236; 1.E.154.237; 1.E.154.238; 1.E.154.239; 1.E.154.154; 1.E.154.157; 1.E.154.166;
1.E.154.169; 1.E.154.172; 1.E.154.175; 1.E.154.240; 1.E.154.244; 1.E.157.228; 1.E.157.229;
1.E.157.230; 1.E.157.231; 1.E.157.236; 1.E.157.237; 1.E.157.238; 1.E.157.239; 1.E.157.154;
1.E.157.157; 1.E.157.166; 1.E.157.169; 1.E.157.172; 1.E.157.175; 1.E.157.240; 1.E.157.244;
1.E.166.228; 1.E.166.229; 1.E.166.230; 1.E.166.231; 1.E.166.236; 1.E.166.237; 1.E.166.238;
1.E.166.239; 1.E.166.154; 1.E.166.157; 1.E.166.166; 1.E.166.169; 1.E.166.172; 1.E.166.175;
1.E.166.240; 1.E.166.244; 1.E.169.228; 1.E.169.229; 1.E.169.230; 1.E.169.231; 1.E.169.236;
1.E.169.237; 1.E.169.238; 1.E.169.239; 1.E.169.154; 1.E.169.157; 1.E.169.166; 1.E.169.169;
1.E.169.172; 1.E.169.175; 1.E.169.240; 1.E.169.244; 1.E.172.228; 1.E.172.229; 1.E.172.230;
1.E.172.231; 1.E.172.236; 1.E.172.237; 1.E.172.238; 1.E.172.239; 1.E.172.154; 1.E.172.157;
1.E.172.166; 1.E.172.169; 1.E.172.172; 1.E.172.175; 1.E.172.240; 1.E.172.244; 1.E.175.228;
1.E.175.229; 1.E.175.230; 1.E.175.231; 1.E.175.236; 1.E.175.237; 1.E.175.238; 1.E.175.239;
1.E.175.154; 1.E.175.157; 1.E.175.166; 1.E.175.169; 1.E.175.172; 1.E.175.175; 1.E.175.240;
1.E.175.244; 1.E.240.228; 1.E.240.229; 1.E.240.230; 1.E.240.231; 1.E.240.236; 1.E.240.237;
1.E.240.238; 1.E.240.239; 1.E.240.154; 1.E.240.157; 1.E.240.166; 1.E.240.169; 1.E.240.172;
1.E.240.175; 1.E.240.240; 1.E.240.244; 1.E.244.228; 1.E.244.229; 1.E.244.230; 1.E.244.231;
1.E.244.236; 1.E.244.237; 1.E.244.238; 1.E.244.239; 1.E.244.154; 1.E.244.157; 1.E.244.166;
1.E.244.169; 1.E.244.172; 1.E.244.175; 1.E.244.240; 1.E.244.244;

Prodrugs of 1.G

1.G.228.228; 1.G.228.229; 1.G.228.230; 1.G.228.231; 1.G.228.236; 1.G.228.237;
1.G.228.238; 1.G.228.239; 1.G.228.154; 1.G.228.157; 1.G.228.166; 1.G.228.169;
1.G.228.172; 1.G.228.175; 1.G.228.240; 1.G.228.244; 1.G.229.228; 1.G.229.229;
1.G.229.230; 1.G.229.231; 1.G.229.236; 1.G.229.237; 1.G.229.238; 1.G.229.239;

TABLE 100-continued

1.G.229.154; 1.G.229.157; 1.G.229.166; 1.G.229.169; 1.G.229.172; 1.G.229.175;
1.G.229.240; 1.G.229.244; 1.G.230.228; 1.G.230.229; 1.G.230.230; 1.G.230.231;
1.G.230.236; 1.G.230.237; 1.G.230.238; 1.G.230.239; 1.G.230.154; 1.G.230.157;
1.G.230.166; 1.G.230.169; 1.G.230.172; 1.G.230.175; 1.G.230.240; 1.G.230.244;
1.G.231.228; 1.G.231.229; 1.G.231.230; 1.G.231.231; 1.G.231.236; 1.G.231.237;
1.G.231.238; 1.G.231.239; 1.G.231.154; 1.G.231.157; 1.G.231.166; 1.G.231.169;
1.G.231.172; 1.G.231.175; 1.G.231.240; 1.G.231.244; 1.G.236.228; 1.G.236.229;
1.G.236.230; 1.G.236.231; 1.G.236.236; 1.G.236.237; 1.G.236.238; 1.G.236.239;
1.G.236.154; 1.G.236.157; 1.G.236.166; 1.G.236.169; 1.G.236.172; 1.G.236.175;
1.G.236.240; 1.G.236.244; 1.G.237.228; 1.G.237.229; 1.G.237.230; 1.G.237.231;
1.G.237.236; 1.G.237.237; 1.G.237.238; 1.G.237.239; 1.G.237.154; 1.G.237.157;
1.G.237.166; 1.G.237.169; 1.G.237.172; 1.G.237.175; 1.G.237.240; 1.G.237.244;
1.G.238.228; 1.G.238.229; 1.G.238.230; 1.G.238.231; 1.G.238.236; 1.G.238.237;
1.G.238.238; 1.G.238.239; 1.G.238.154; 1.G.238.157; 1.G.238.166; 1.G.238.169;
1.G.238.172; 1.G.238.175; 1.G.238.240; 1.G.238.244; 1.G.239.228; 1.G.239.229;
1.G.239.230; 1.G.239.231; 1.G.239.236; 1.G.239.237; 1.G.239.238; 1.G.239.239;
1.G.239.154; 1.G.239.157; 1.G.239.166; 1.G.239.169; 1.G.239.172; 1.G.239.175;
1.G.239.240; 1.G.239.244; 1.G.154.228; 1.G.154.229; 1.G.154.230; 1.G.154.231;
1.G.154.236; 1.G.154.237; 1.G.154.238; 1.G.154.239; 1.G.154.154; 1.G.154.157;
1.G.154.166; 1.G.154.169; 1.G.154.172; 1.G.154.175; 1.G.154.240; 1.G.154.244;
1.G.157.228; 1.G.157.229; 1.G.157.230; 1.G.157.231; 1.G.157.236; 1.G.157.237;
1.G.157.238; 1.G.157.239; 1.G.157.154; 1.G.157.157; 1.G.157.166; 1.G.157.169;
1.G.157.172; 1.G.157.175; 1.G.157.240; 1.G.157.244; 1.G.166.228; 1.G.166.229;
1.G.166.230; 1.G.166.231; 1.G.166.236; 1.G.166.237; 1.G.166.238; 1.G.166.239;
1.G.166.154; 1.G.166.157; 1.G.166.166; 1.G.166.169; 1.G.166.172; 1.G.166.175;
1.G.166.240; 1.G.166.244; 1.G.169.228; 1.G.169.229; 1.G.169.230; 1.G.169.231;
1.G.169.236; 1.G.169.237; 1.G.169.238; 1.G.169.239; 1.G.169.154; 1.G.169.157;
1.G.169.166; 1.G.169.169; 1.G.169.172; 1.G.169.175; 1.G.169.240; 1.G.169.244;
1.G.172.228; 1.G.172.229; 1.G.172.230; 1.G.172.231; 1.G.172.236; 1.G.172.237;
1.G.172.238; 1.G.172.239; 1.G.172.154; 1.G.172.157; 1.G.172.166; 1.G.172.169;
1.G.172.172; 1.G.172.175; 1.G.172.240; 1.G.172.244; 1.G.175.228; 1.G.175.229;
1.G.175.230; 1.G.175.231; 1.G.175.236; 1.G.175.237; 1.G.175.238; 1.G.175.239;
1.G.175.154; 1.G.175.157; 1.G.175.166; 1.G.175.169; 1.G.175.172; 1.G.175.175;
1.G.175.240; 1.G.175.244; 1.G.240.228; 1.G.240.229; 1.G.240.230; 1.G.240.231;
1.G.240.236; 1.G.240.237; 1.G.240.238; 1.G.240.239; 1.G.240.154; 1.G.240.157;
1.G.240.166; 1.G.240.169; 1.G.240.172; 1.G.240.175; 1.G.240.240; 1.G.240.244;
1.G.244.228; 1.G.244.229; 1.G.244.230; 1.G.244.231; 1.G.244.236; 1.G.244.237;
1.G.244.238; 1.G.244.239; 1.G.244.154; 1.G.244.157; 1.G.244.166; 1.G.244.169;
1.G.244.172; 1.G.244.175; 1.G.244.240; 1.G.244.244;

Prodrugs of 1.I

1.I.228.228; 1.I.228.229; 1.I.228.230; 1.I.228.231; 1.I.228.236; 1.I.228.237; 1.I.228.238;
1.I.228.239; 1.I.228.154; 1.I.228.157; 1.I.228.166; 1.I.228.169; 1.I.228.172; 1.I.228.175;
1.I.228.240; 1.I.228.244; 1.I.229.228; 1.I.229.229; 1.I.229.230; 1.I.229.231; 1.I.229.236;
1.I.229.237; 1.I.229.238; 1.I.229.239; 1.I.229.154; 1.I.229.157; 1.I.229.166; 1.I.229.169;
1.I.229.172; 1.I.229.175; 1.I.229.240; 1.I.229.244; 1.I.230.228; 1.I.230.229; 1.I.230.230;
1.I.230.231; 1.I.230.236; 1.I.230.237; 1.I.230.238; 1.I.230.239; 1.I.230.154; 1.I.230.157;
1.I.230.166; 1.I.230.169; 1.I.230.172; 1.I.230.175; 1.I.230.240; 1.I.230.244; 1.I.231.228;
1.I.231.229; 1.I.231.230; 1.I.231.231; 1.I.231.236; 1.I.231.237; 1.I.231.238; 1.I.231.239;
1.I.231.154; 1.I.231.157; 1.I.231.166; 1.I.231.169; 1.I.231.172; 1.I.231.175; 1.I.231.240;
1.I.231.244; 1.I.236.228; 1.I.236.229; 1.I.236.230; 1.I.236.231; 1.I.236.236; 1.I.236.237;
1.I.236.238; 1.I.236.239; 1.I.236.154; 1.I.236.157; 1.I.236.166; 1.I.236.169; 1.I.236.172;
1.I.236.175; 1.I.236.240; 1.I.236.244; 1.I.237.228; 1.I.237.229; 1.I.237.230; 1.I.237.231;
1.I.237.236; 1.I.237.237; 1.I.237.238; 1.I.237.239; 1.I.237.154; 1.I.237.157; 1.I.237.166;
1.I.237.169; 1.I.237.172; 1.I.237.175; 1.I.237.240; 1.I.237.244; 1.I.238.228; 1.I.238.229;
1.I.238.230; 1.I.238.231; 1.I.238.236; 1.I.238.237; 1.I.238.238; 1.I.238.239; 1.I.238.154;
1.I.238.157; 1.I.238.166; 1.I.238.169; 1.I.238.172; 1.I.238.175; 1.I.238.240; 1.I.238.244;
1.I.239.228; 1.I.239.229; 1.I.239.230; 1.I.239.231; 1.I.239.236; 1.I.239.237; 1.I.239.238;
1.I.239.239; 1.I.239.154; 1.I.239.157; 1.I.239.166; 1.I.239.169; 1.I.239.172; 1.I.239.175;
1.I.239.240; 1.I.239.244; 1.I.154.228; 1.I.154.229; 1.I.154.230; 1.I.154.231; 1.I.154.236;
1.I.154.237; 1.I.154.238; 1.I.154.239; 1.I.154.154; 1.I.154.157; 1.I.154.166; 1.I.154.169;
1.I.154.172; 1.I.154.175; 1.I.154.240; 1.I.154.244; 1.I.157.228; 1.I.157.229; 1.I.157.230;
1.I.157.231; 1.I.157.236; 1.I.157.237; 1.I.157.238; 1.I.157.239; 1.I.157.154; 1.I.157.157;
1.I.157.166; 1.I.157.169; 1.I.157.172; 1.I.157.175; 1.I.157.240; 1.I.157.244; 1.I.166.228;
1.I.166.229; 1.I.166.230; 1.I.166.231; 1.I.166.236; 1.I.166.237; 1.I.166.238; 1.I.166.239;
1.I.166.154; 1.I.166.157; 1.I.166.166; 1.I.166.169; 1.I.166.172; 1.I.166.175; 1.I.166.240;
1.I.166.244; 1.I.169.228; 1.I.169.229; 1.I.169.230; 1.I.169.231; 1.I.169.236; 1.I.169.237;
1.I.169.238; 1.I.169.239; 1.I.169.154; 1.I.169.157; 1.I.169.166; 1.I.169.169; 1.I.169.172;
1.I.169.175; 1.I.169.240; 1.I.169.244; 1.I.172.228; 1.I.172.229; 1.I.172.230; 1.I.172.231;
1.I.172.236; 1.I.172.237; 1.I.172.238; 1.I.172.239; 1.I.172.154; 1.I.172.157; 1.I.172.166;
1.I.172.169; 1.I.172.172; 1.I.172.175; 1.I.172.240; 1.I.172.244; 1.I.175.228; 1.I.175.229;
1.I.175.230; 1.I.175.231; 1.I.175.236; 1.I.175.237; 1.I.175.238; 1.I.175.239; 1.I.175.154;
1.I.175.157; 1.I.175.166; 1.I.175.169; 1.I.175.172; 1.I.175.175; 1.I.175.240; 1.I.175.244;
1.I.240.228; 1.I.240.229; 1.I.240.230; 1.I.240.231; 1.I.240.236; 1.I.240.237; 1.I.240.238;
1.I.240.239; 1.I.240.154; 1.I.240.157; 1.I.240.166; 1.I.240.169; 1.I.240.172; 1.I.240.175;
1.I.240.240; 1.I.240.244; 1.I.244.228; 1.I.244.229; 1.I.244.230; 1.I.244.231; 1.I.244.236;
1.I.244.237; 1.I.244.238; 1.I.244.239; 1.I.244.154; 1.I.244.157; 1.I.244.166; 1.I.244.169;
1.I.244.172; 1.I.244.175; 1.I.244.240; 1.I.244.244;

TABLE 100-continued

Prodrugs of 1.J

1.J.228.228; 1.J.228.229; 1.J.228.230; 1.J.228.231; 1.J.228.236; 1.J.228.237; 1.J.228.238; 1.J.228.239; 1.J.228.154; 1.J.228.157; 1.J.228.166; 1.J.228.169; 1.J.228.172; 1.J.228.175; 1.J.228.240; 1.J.228.244; 1.J.229.228; 1.J.229.229; 1.J.229.230; 1.J.229.231; 1.J.229.236; 1.J.229.237; 1.J.229.238; 1.J.229.239; 1.J.229.154; 1.J.229.157; 1.J.229.166; 1.J.229.169; 1.J.229.172; 1.J.229.175; 1.J.229.240; 1.J.229.244; 1.J.230.228; 1.J.230.229; 1.J.230.230; 1.J.230.231; 1.J.230.236; 1.J.230.237; 1.J.230.238; 1.J.230.239; 1.J.230.154; 1.J.230.157; 1.J.230.166; 1.J.230.169; 1.J.230.172; 1.J.230.175; 1.J.230.240; 1.J.230.244; 1.J.231.228; 1.J.231.229; 1.J.231.230; 1.J.231.231; 1.J.231.236; 1.J.231.237; 1.J.231.238; 1.J.231.239; 1.J.231.154; 1.J.231.157; 1.J.231.166; 1.J.231.169; 1.J.231.172; 1.J.231.175; 1.J.231.240; 1.J.231.244; 1.J.236.228; 1.J.236.229; 1.J.236.230; 1.J.236.231; 1.J.236.236; 1.J.236.237; 1.J.236.238; 1.J.236.239; 1.J.236.154; 1.J.236.157; 1.J.236.166; 1.J.236.169; 1.J.236.172; 1.J.236.175; 1.J.236.240; 1.J.236.244; 1.J.237.228; 1.J.237.229; 1.J.237.230; 1.J.237.231; 1.J.237.236; 1.J.237.237; 1.J.237.238; 1.J.237.239; 1.J.237.154; 1.J.237.157; 1.J.237.166; 1.J.237.169; 1.J.237.172; 1.J.237.175; 1.J.237.240; 1.J.237.244; 1.J.238.228; 1.J.238.229; 1.J.238.230; 1.J.238.231; 1.J.238.236; 1.J.238.237; 1.J.238.238; 1.J.238.239; 1.J.238.154; 1.J.238.157; 1.J.238.166; 1.J.238.169; 1.J.238.172; 1.J.238.175; 1.J.238.240; 1.J.238.244; 1.J.239.228; 1.J.239.229; 1.J.239.230; 1.J.239.231; 1.J.239.236; 1.J.239.237; 1.J.239.238; 1.J.239.239; 1.J.239.154; 1.J.239.157; 1.J.239.166; 1.J.239.169; 1.J.239.172; 1.J.239.175; 1.J.239.240; 1.J.239.244; 1.J.154.228; 1.J.154.229; 1.J.154.230; 1.J.154.231; 1.J.154.236; 1.J.154.237; 1.J.154.238; 1.J.154.239; 1.J.154.154; 1.J.154.157; 1.J.154.166; 1.J.154.169; 1.J.154.172; 1.J.154.175; 1.J.154.240; 1.J.154.244; 1.J.157.228; 1.J.157.229; 1.J.157.230; 1.J.157.231; 1.J.157.236; 1.J.157.237; 1.J.157.238; 1.J.157.239; 1.J.157.154; 1.J.157.157; 1.J.157.166; 1.J.157.169; 1.J.157.172; 1.J.157.175; 1.J.157.240; 1.J.157.244; 1.J.166.228; 1.J.166.229; 1.J.166.230; 1.J.166.231; 1.J.166.236; 1.J.166.237; 1.J.166.238; 1.J.166.239; 1.J.166.154; 1.J.166.157; 1.J.166.166; 1.J.166.169; 1.J.166.172; 1.J.166.175; 1.J.166.240; 1.J.166.244; 1.J.169.228; 1.J.169.229; 1.J.169.230; 1.J.169.231; 1.J.169.236; 1.J.169.237; 1.J.169.238; 1.J.169.239; 1.J.169.154; 1.J.169.157; 1.J.169.166; 1.J.169.169; 1.J.169.172; 1.J.169.175; 1.J.169.240; 1.J.169.244; 1.J.172.228; 1.J.172.229; 1.J.172.230; 1.J.172.231; 1.J.172.236; 1.J.172.237; 1.J.172.238; 1.J.172.239; 1.J.172.154; 1.J.172.157; 1.J.172.166; 1.J.172.169; 1.J.172.172; 1.J.172.175; 1.J.172.240; 1.J.172.244; 1.J.175.228; 1.J.175.229; 1.J.175.230; 1.J.175.231; 1.J.175.236; 1.J.175.237; 1.J.175.238; 1.J.175.239; 1.J.175.154; 1.J.175.157; 1.J.175.166; 1.J.175.169; 1.J.175.172; 1.J.175.175; 1.J.175.240; 1.J.175.244; 1.J.240.228; 1.J.240.229; 1.J.240.230; 1.J.240.231; 1.J.240.236; 1.J.240.237; 1.J.240.238; 1.J.240.239; 1.J.240.154; 1.J.240.157; 1.J.240.166; 1.J.240.169; 1.J.240.172; 1.J.240.175; 1.J.240.240; 1.J.240.244; 1.J.244.228; 1.J.244.229; 1.J.244.230; 1.J.244.231; 1.J.244.236; 1.J.244.237; 1.J.244.238; 1.J.244.239; 1.J.244.154; 1.J.244.157; 1.J.244.166; 1.J.244.169; 1.J.244.172; 1.J.244.175; 1.J.244.240; 1.J.244.244;

Prodrugs of 1.L

1.L.228.228; 1.L.228.229; 1.L.228.230; 1.L.228.231; 1.L.228.236; 1.L.228.237; 1.L.228.238; 1.L.228.239; 1.L.228.154; 1.L.228.157; 1.L.228.166; 1.L.228.169; 1.L.228.172; 1.L.228.175; 1.L.228.240; 1.L.228.244; 1.L.229.228; 1.L.229.229; 1.L.229.230; 1.L.229.231; 1.L.229.236; 1.L.229.237; 1.L.229.238; 1.L.229.239; 1.L.229.154; 1.L.229.157; 1.L.229.166; 1.L.229.169; 1.L.229.172; 1.L.229.175; 1.L.229.240; 1.L.229.244; 1.L.230.228; 1.L.230.229; 1.L.230.230; 1.L.230.231; 1.L.230.236; 1.L.230.237; 1.L.230.238; 1.L.230.239; 1.L.230.154; 1.L.230.157; 1.L.230.166; 1.L.230.169; 1.L.230.172; 1.L.230.175; 1.L.230.240; 1.L.230.244; 1.L.231.228; 1.L.231.229; 1.L.231.230; 1.L.231.231; 1.L.231.236; 1.L.231.237; 1.L.231.238; 1.L.231.239; 1.L.231.154; 1.L.231.157; 1.L.231.166; 1.L.231.169; 1.L.231.172; 1.L.231.175; 1.L.231.240; 1.L.231.244; 1.L.236.228; 1.L.236.229; 1.L.236.230; 1.L.236.231; 1.L.236.236; 1.L.236.237; 1.L.236.238; 1.L.236.239; 1.L.236.154; 1.L.236.157; 1.L.236.166; 1.L.236.169; 1.L.236.172; 1.L.236.175; 1.L.236.240; 1.L.236.244; 1.L.237.228; 1.L.237.229; 1.L.237.230; 1.L.237.231; 1.L.237.236; 1.L.237.237; 1.L.237.238; 1.L.237.239; 1.L.237.154; 1.L.237.157; 1.L.237.166; 1.L.237.169; 1.L.237.172; 1.L.237.175; 1.L.237.240; 1.L.237.244; 1.L.238.228; 1.L.238.229; 1.L.238.230; 1.L.238.231; 1.L.238.236; 1.L.238.237; 1.L.238.238; 1.L.238.239; 1.L.238.154; 1.L.238.157; 1.L.238.166; 1.L.238.169; 1.L.238.172; 1.L.238.175; 1.L.238.240; 1.L.238.244; 1.L.239.228; 1.L.239.229; 1.L.239.230; 1.L.239.231; 1.L.239.236; 1.L.239.237; 1.L.239.238; 1.L.239.239; 1.L.239.154; 1.L.239.157; 1.L.239.166; 1.L.239.169; 1.L.239.172; 1.L.239.175; 1.L.239.240; 1.L.239.244; 1.L.154.228; 1.L.154.229; 1.L.154.230; 1.L.154.231; 1.L.154.236; 1.L.154.237; 1.L.154.238; 1.L.154.239; 1.L.154.154; 1.L.154.157; 1.L.154.166; 1.L.154.169; 1.L.154.172; 1.L.154.175; 1.L.154.240; 1.L.154.244; 1.L.157.228; 1.L.157.229; 1.L.157.230; 1.L.157.231; 1.L.157.236; 1.L.157.237; 1.L.157.238; 1.L.157.239; 1.L.157.154; 1.L.157.157; 1.L.157.166; 1.L.157.169; 1.L.157.172; 1.L.157.175; 1.L.157.240; 1.L.157.244; 1.L.166.228; 1.L.166.229; 1.L.166.230; 1.L.166.231; 1.L.166.236; 1.L.166.237; 1.L.166.238; 1.L.166.239; 1.L.166.154; 1.L.166.157; 1.L.166.166; 1.L.166.169; 1.L.166.172; 1.L.166.175; 1.L.166.240; 1.L.166.244; 1.L.169.228; 1.L.169.229; 1.L.169.230; 1.L.169.231; 1.L.169.236; 1.L.169.237; 1.L.169.238; 1.L.169.239; 1.L.169.154; 1.L.169.157; 1.L.169.166; 1.L.169.169; 1.L.169.172; 1.L.169.175; 1.L.169.240; 1.L.169.244; 1.L.172.228; 1.L.172.229; 1.L.172.230; 1.L.172.231; 1.L.172.236; 1.L.172.237; 1.L.172.238; 1.L.172.239; 1.L.172.154; 1.L.172.157; 1.L.172.166; 1.L.172.169; 1.L.172.172; 1.L.172.175; 1.L.172.240; 1.L.172.244; 1.L.175.228; 1.L.175.229; 1.L.175.230; 1.L.175.231; 1.L.175.236; 1.L.175.237; 1.L.175.238; 1.L.175.239; 1.L.175.154; 1.L.175.157; 1.L.175.166; 1.L.175.169; 1.L.175.172; 1.L.175.175; 1.L.175.240; 1.L.175.244; 1.L.240.228; 1.L.240.229; 1.L.240.230; 1.L.240.231; 1.L.240.236; 1.L.240.237; 1.L.240.238; 1.L.240.239; 1.L.240.154; 1.L.240.157; 1.L.240.166; 1.L.240.169; 1.L.240.172; 1.L.240.175; 1.L.240.240; 1.L.240.244; 1.L.244.228; 1.L.244.229; 1.L.244.230; 1.L.244.231; 1.L.244.236; 1.L.244.237; 1.L.244.238; 1.L.244.239; 1.L.244.154; 1.L.244.157; 1.L.244.166; 1.L.244.169; 1.L.244.172; 1.L.244.175; 1.L.244.240; 1.L.244.244;

TABLE 100-continued

Prodrugs of 1.O

1.O.228.228; 1.O.228.229; 1.O.228.230; 1.O.228.231; 1.O.228.236; 1.O.228.237;
1.O.228.238; 1.O.228.239; 1.O.228.154; 1.O.228.157; 1.O.228.166; 1.O.228.169;
1.O.228.172; 1.O.228.175; 1.O.228.240; 1.O.228.244; 1.O.229.228; 1.O.229.229;
1.O.229.230; 1.O.229.231; 1.O.229.236; 1.O.229.237; 1.O.229.238; 1.O.229.239;
1.O.229.154; 1.O.229.157; 1.O.229.166; 1.O.229.169; 1.O.229.172; 1.O.229.175;
1.O.229.240; 1.O.229.244; 1.O.230.228; 1.O.230.229; 1.O.230.230; 1.O.230.231;
1.O.230.236; 1.O.230.237; 1.O.230.238; 1.O.230.239; 1.O.230.154; 1.O.230.157;
1.O.230.166; 1.O.230.169; 1.O.230.172; 1.O.230.175; 1.O.230.240; 1.O.230.244;
1.O.231.228; 1.O.231.229; 1.O.231.230; 1.O.231.231; 1.O.231.236; 1.O.231.237;
1.O.231.238; 1.O.231.239; 1.O.231.154; 1.O.231.157; 1.O.231.166; 1.O.231.169;
1.O.231.172; 1.O.231.175; 1.O.231.240; 1.O.231.244; 1.O.236.228; 1.O.236.229;
1.O.236.230; 1.O.236.231; 1.O.236.236; 1.O.236.237; 1.O.236.238; 1.O.236.239;
1.O.236.154; 1.O.236.157; 1.O.236.166; 1.O.236.169; 1.O.236.172; 1.O.236.175;
1.O.236.240; 1.O.236.244; 1.O.237.228; 1.O.237.229; 1.O.237.230; 1.O.237.231;
1.O.237.236; 1.O.237.237; 1.O.237.238; 1.O.237.239; 1.O.237.154; 1.O.237.157;
1.O.237.166; 1.O.237.169; 1.O.237.172; 1.O.237.175; 1.O.237.240; 1.O.237.244;
1.O.238.228; 1.O.238.229; 1.O.238.230; 1.O.238.231; 1.O.238.236; 1.O.238.237;
1.O.238.238; 1.O.238.239; 1.O.238.154; 1.O.238.157; 1.O.238.166; 1.O.238.169;
1.O.238.172; 1.O.238.175; 1.O.238.240; 1.O.238.244; 1.O.239.228; 1.O.239.229;
1.O.239.230; 1.O.239.231; 1.O.239.236; 1.O.239.237; 1.O.239.238; 1.O.239.239;
1.O.239.154; 1.O.239.157; 1.O.239.166; 1.O.239.169; 1.O.239.172; 1.O.239.175;
1.O.239.240; 1.O.239.244; 1.O.154.228; 1.O.154.229; 1.O.154.230; 1.O.154.231;
1.O.154.236; 1.O.154.237; 1.O.154.238; 1.O.154.239; 1.O.154.154; 1.O.154.157;
1.O.154.166; 1.O.154.169; 1.O.154.172; 1.O.154.175; 1.O.154.240; 1.O.154.244;
1.O.157.228; 1.O.157.229; 1.O.157.230; 1.O.157.231; 1.O.157.236; 1.O.157.237;
1.O.157.238; 1.O.157.239; 1.O.157.154; 1.O.157.157; 1.O.157.166; 1.O.157.169;
1.O.157.172; 1.O.157.175; 1.O.157.240; 1.O.157.244; 1.O.166.228; 1.O.166.229;
1.O.166.230; 1.O.166.231; 1.O.166.236; 1.O.166.237; 1.O.166.238; 1.O.166.239;
1.O.166.154; 1.O.166.157; 1.O.166.166; 1.O.166.169; 1.O.166.172; 1.O.166.175;
1.O.166.240; 1.O.166.244; 1.O.169.228; 1.O.169.229; 1.O.169.230; 1.O.169.231;
1.O.169.236; 1.O.169.237; 1.O.169.238; 1.O.169.239; 1.O.169.154; 1.O.169.157;
1.O.169.166; 1.O.169.169; 1.O.169.172; 1.O.169.175; 1.O.169.240; 1.O.169.244;
1.O.172.228; 1.O.172.229; 1.O.172.230; 1.O.172.231; 1.O.172.236; 1.O.172.237;
1.O.172.238; 1.O.172.239; 1.O.172.154; 1.O.172.157; 1.O.172.166; 1.O.172.169;
1.O.172.172; 1.O.172.175; 1.O.172.240; 1.O.172.244; 1.O.175.228; 1.O.175.229;
1.O.175.230; 1.O.175.231; 1.O.175.236; 1.O.175.237; 1.O.175.238; 1.O.175.239;
1.O.175.154; 1.O.175.157; 1.O.175.166; 1.O.175.169; 1.O.175.172; 1.O.175.175;
1.O.175.240; 1.O.175.244; 1.O.240.228; 1.O.240.229; 1.O.240.230; 1.O.240.231;
1.O.240.236; 1.O.240.237; 1.O.240.238; 1.O.240.239; 1.O.240.154; 1.O.240.157;
1.O.240.166; 1.O.240.169; 1.O.240.172; 1.O.240.175; 1.O.240.240; 1.O.240.244;
1.O.244.228; 1.O.244.229; 1.O.244.230; 1.O.244.231; 1.O.244.236; 1.O.244.237;
1.O.244.238; 1.O.244.239; 1.O.244.154; 1.O.244.157; 1.O.244.166; 1.O.244.169;
1.O.244.172; 1.O.244.175; 1.O.244.240; 1.O.244.244;

Prodrugs of 1.P

1.P.228.228; 1.P.228.229; 1.P.228.230; 1.P.228.231; 1.P.228.236; 1.P.228.237;
1.P.228.238; 1.P.228.239; 1.P.228.154; 1.P.228.157; 1.P.228.166; 1.P.228.169; 1.P.228.172;
1.P.228.175; 1.P.228.240; 1.P.228.244; 1.P.229.228; 1.P.229.229; 1.P.229.230; 1.P.229.231;
1.P.229.236; 1.P.229.237; 1.P.229.238; 1.P.229.239; 1.P.229.154; 1.P.229.157; 1.P.229.166;
1.P.229.169; 1.P.229.172; 1.P.229.175; 1.P.229.240; 1.P.229.244; 1.P.230.228; 1.P.230.229;
1.P.230.230; 1.P.230.231; 1.P.230.236; 1.P.230.237; 1.P.230.238; 1.P.230.239; 1.P.230.154;
1.P.230.157; 1.P.230.166; 1.P.230.169; 1.P.230.172; 1.P.230.175; 1.P.230.240; 1.P.230.244;
1.P.231.228; 1.P.231.229; 1.P.231.230; 1.P.231.231; 1.P.231.236; 1.P.231.237; 1.P.231.238;
1.P.231.239; 1.P.231.154; 1.P.231.157; 1.P.231.166; 1.P.231.169; 1.P.231.172; 1.P.231.175;
1.P.231.240; 1.P.231.244; 1.P.236.228; 1.P.236.229; 1.P.236.230; 1.P.236.231; 1.P.236.236;
1.P.236.237; 1.P.236.238; 1.P.236.239; 1.P.236.154; 1.P.236.157; 1.P.236.166; 1.P.236.169;
1.P.236.172; 1.P.236.175; 1.P.236.240; 1.P.236.244; 1.P.237.228; 1.P.237.229; 1.P.237.230;
1.P.237.231; 1.P.237.236; 1.P.237.237; 1.P.237.238; 1.P.237.239; 1.P.237.154; 1.P.237.157;
1.P.237.166; 1.P.237.169; 1.P.237.172; 1.P.237.175; 1.P.237.240; 1.P.237.244; 1.P.238.228;
1.P.238.229; 1.P.238.230; 1.P.238.231; 1.P.238.236; 1.P.238.237; 1.P.238.238; 1.P.238.239;
1.P.238.154; 1.P.238.157; 1.P.238.166; 1.P.238.169; 1.P.238.172; 1.P.238.175; 1.P.238.240;
1.P.238.244; 1.P.239.228; 1.P.239.229; 1.P.239.230; 1.P.239.231; 1.P.239.236; 1.P.239.237;
1.P.239.238; 1.P.239.239; 1.P.239.154; 1.P.239.157; 1.P.239.166; 1.P.239.169; 1.P.239.172;
1.P.239.175; 1.P.239.240; 1.P.239.244; 1.P.154.228; 1.P.154.229; 1.P.154.230; 1.P.154.231;
1.P.154.236; 1.P.154.237; 1.P.154.238; 1.P.154.239; 1.P.154.154; 1.P.154.157; 1.P.154.166;
1.P.154.169; 1.P.154.172; 1.P.154.175; 1.P.154.240; 1.P.154.244; 1.P.157.228; 1.P.157.229;
1.P.157.230; 1.P.157.231; 1.P.157.236; 1.P.157.237; 1.P.157.238; 1.P.157.239; 1.P.157.154;
1.P.157.157; 1.P.157.166; 1.P.157.169; 1.P.157.172; 1.P.157.175; 1.P.157.240; 1.P.157.244;
1.P.166.228; 1.P.166.229; 1.P.166.230; 1.P.166.231; 1.P.166.236; 1.P.166.237; 1.P.166.238;
1.P.166.239; 1.P.166.154; 1.P.166.157; 1.P.166.166; 1.P.166.169; 1.P.166.172; 1.P.166.175;
1.P.166.240; 1.P.166.244; 1.P.169.228; 1.P.169.229; 1.P.169.230; 1.P.169.231; 1.P.169.236;
1.P.169.237; 1.P.169.238; 1.P.169.239; 1.P.169.154; 1.P.169.157; 1.P.169.166; 1.P.169.169;
1.P.169.172; 1.P.169.175; 1.P.169.240; 1.P.169.244; 1.P.172.228; 1.P.172.229; 1.P.172.230;
1.P.172.231; 1.P.172.236; 1.P.172.237; 1.P.172.238; 1.P.172.239; 1.P.172.154; 1.P.172.157;
1.P.172.166; 1.P.172.169; 1.P.172.172; 1.P.172.175; 1.P.172.240; 1.P.172.244; 1.P.175.228;
1.P.175.229; 1.P.175.230; 1.P.175.231; 1.P.175.236; 1.P.175.237; 1.P.175.238; 1.P.175.239;
1.P.175.154; 1.P.175.157; 1.P.175.166; 1.P.175.169; 1.P.175.172; 1.P.175.175; 1.P.175.240;

TABLE 100-continued

1.P.175.244; 1.P.240.228; 1.P.240.229; 1.P.240.230; 1.P.240.231; 1.P.240.236; 1.P.240.237;
1.P.240.238; 1.P.240.239; 1.P.240.154; 1.P.240.157; 1.P.240.166; 1.P.240.169; 1.P.240.172;
1.P.240.175; 1.P.240.240; 1.P.240.244; 1.P.244.228; 1.P.244.229; 1.P.244.230; 1.P.244.231;
1.P.244.236; 1.P.244.237; 1.P.244.238; 1.P.244.239; 1.P.244.154; 1.P.244.157; 1.P.244.166;
1.P.244.169; 1.P.244.172; 1.P.244.175; 1.P.244.240; 1.P.244.244;

Prodrugs of 1.U

1.U.228.228; 1.U.228.229; 1.U.228.230; 1.U.228.231; 1.U.228.236; 1.U.228.237;
1.U.228.238; 1.U.228.239; 1.U.228.154; 1.U.228.157; 1.U.228.166; 1.U.228.169;
1.U.228.172; 1.U.228.175; 1.U.228.240; 1.U.228.244; 1.U.229.228; 1.U.229.229;
1.U.229.230; 1.U.229.231; 1.U.229.236; 1.U.229.237; 1.U.229.238; 1.U.229.239;
1.U.229.154; 1.U.229.157; 1.U.229.166; 1.U.229.169; 1.U.229.172; 1.U.229.175;
1.U.229.240; 1.U.229.244; 1.U.230.228; 1.U.230.229; 1.U.230.230; 1.U.230.231;
1.U.230.236; 1.U.230.237; 1.U.230.238; 1.U.230.239; 1.U.230.154; 1.U.230.157;
1.U.230.166; 1.U.230.169; 1.U.230.172; 1.U.230.175; 1.U.230.240; 1.U.230.244;
1.U.231.228; 1.U.231.229; 1.U.231.230; 1.U.231.231; 1.U.231.236; 1.U.231.237;
1.U.231.238; 1.U.231.239; 1.U.231.154; 1.U.231.157; 1.U.231.166; 1.U.231.169;
1.U.231.172; 1.U.231.175; 1.U.231.240; 1.U.231.244; 1.U.236.228; 1.U.236.229;
1.U.236.230; 1.U.236.231; 1.U.236.236; 1.U.236.237; 1.U.236.238; 1.U.236.239;
1.U.236.154; 1.U.236.157; 1.U.236.166; 1.U.236.169; 1.U.236.172; 1.U.236.175;
1.U.236.240; 1.U.236.244; 1.U.237.228; 1.U.237.229; 1.U.237.230; 1.U.237.231;
1.U.237.236; 1.U.237.237; 1.U.237.238; 1.U.237.239; 1.U.237.154; 1.U.237.157;
1.U.237.166; 1.U.237.169; 1.U.237.172; 1.U.237.175; 1.U.237.240; 1.U.237.244;
1.U.238.228; 1.U.238.229; 1.U.238.230; 1.U.238.231; 1.U.238.236; 1.U.238.237;
1.U.238.238; 1.U.238.239; 1.U.238.154; 1.U.238.157; 1.U.238.166; 1.U.238.169;
1.U.238.172; 1.U.238.175; 1.U.238.240; 1.U.238.244; 1.U.239.228; 1.U.239.229;
1.U.239.230; 1.U.239.231; 1.U.239.236; 1.U.239.237; 1.U.239.238; 1.U.239.239;
1.U.239.154; 1.U.239.157; 1.U.239.166; 1.U.239.169; 1.U.239.172; 1.U.239.175;
1.U.239.240; 1.U.239.244; 1.U.154.228; 1.U.154.229; 1.U.154.230; 1.U.154.231;
1.U.154.236; 1.U.154.237; 1.U.154.238; 1.U.154.239; 1.U.154.154; 1.U.154.157;
1.U.154.166; 1.U.154.169; 1.U.154.172; 1.U.154.175; 1.U.154.240; 1.U.154.244;
1.U.157.228; 1.U.157.229; 1.U.157.230; 1.U.157.231; 1.U.157.236; 1.U.157.237;
1.U.157.238; 1.U.157.239; 1.U.157.154; 1.U.157.157; 1.U.157.166; 1.U.157.169;
1.U.157.172; 1.U.157.175; 1.U.157.240; 1.U.157.244; 1.U.166.228; 1.U.166.229;
1.U.166.230; 1.U.166.231; 1.U.166.236; 1.U.166.237; 1.U.166.238; 1.U.166.239;
1.U.166.154; 1.U.166.157; 1.U.166.166; 1.U.166.169; 1.U.166.172; 1.U.166.175;
1.U.166.240; 1.U.166.244; 1.U.169.228; 1.U.169.229; 1.U.169.230; 1.U.169.231;
1.U.169.236; 1.U.169.237; 1.U.169.238; 1.U.169.239; 1.U.169.154; 1.U.169.157;
1.U.169.166; 1.U.169.169; 1.U.169.172; 1.U.169.175; 1.U.169.240; 1.U.169.244;
1.U.172.228; 1.U.172.229; 1.U.172.230; 1.U.172.231; 1.U.172.236; 1.U.172.237;
1.U.172.238; 1.U.172.239; 1.U.172.154; 1.U.172.157; 1.U.172.166; 1.U.172.169;
1.U.172.172; 1.U.172.175; 1.U.172.240; 1.U.172.244; 1.U.175.228; 1.U.175.229;
1.U.175.230; 1.U.175.231; 1.U.175.236; 1.U.175.237; 1.U.175.238; 1.U.175.239;
1.U.175.154; 1.U.175.157; 1.U.175.166; 1.U.175.169; 1.U.175.172; 1.U.175.175;
1.U.175.240; 1.U.175.244; 1.U.240.228; 1.U.240.229; 1.U.240.230; 1.U.240.231;
1.U.240.236; 1.U.240.237; 1.U.240.238; 1.U.240.239; 1.U.240.154; 1.U.240.157;
1.U.240.166; 1.U.240.169; 1.U.240.172; 1.U.240.175; 1.U.240.240; 1.U.240.244;
1.U.244.228; 1.U.244.229; 1.U.244.230; 1.U.244.231; 1.U.244.236; 1.U.244.237;
1.U.244.238; 1.U.244.239; 1.U.244.154; 1.U.244.157; 1.U.244.166; 1.U.244.169;
1.U.244.172; 1.U.244.175; 1.U.244.240; 1.U.244.244;

Prodrugs of 1.W

1.W.228.228; 1.W.228.229; 1.W.228.230; 1.W.228.231; 1.W.228.236; 1.W.228.237;
1.W.228.238; 1.W.228.239; 1.W.228.154; 1.W.228.157; 1.W.228.166; 1.W.228.169;
1.W.228.172; 1.W.228.175; 1.W.228.240; 1.W.228.244; 1.W.229.228; 1.W.229.229;
1.W.229.230; 1.W.229.231; 1.W.229.236; 1.W.229.237; 1.W.229.238; 1.W.229.239;
1.W.229.154; 1.W.229.157; 1.W.229.166; 1.W.229.169; 1.W.229.172; 1.W.229.175;
1.W.229.240; 1.W.229.244; 1.W.230.228; 1.W.230.229; 1.W.230.230; 1.W.230.231;
1.W.230.236; 1.W.230.237; 1.W.230.238; 1.W.230.239; 1.W.230.154; 1.W.230.157;
1.W.230.166; 1.W.230.169; 1.W.230.172; 1.W.230.175; 1.W.230.240; 1.W.230.244;
1.W.231.228; 1.W.231.229; 1.W.231.230; 1.W.231.231; 1.W.231.236; 1.W.231.237;
1.W.231.238; 1.W.231.239; 1.W.231.154; 1.W.231.157; 1.W.231.166; 1.W.231.169;
1.W.231.172; 1.W.231.175; 1.W.231.240; 1.W.231.244; 1.W.236.228; 1.W.236.229;
1.W.236.230; 1.W.236.231; 1.W.236.236; 1.W.236.237; 1.W.236.238; 1.W.236.239;
1.W.236.154; 1.W.236.157; 1.W.236.166; 1.W.236.169; 1.W.236.172; 1.W.236.175;
1.W.236.240; 1.W.236.244; 1.W.237.228; 1.W.237.229; 1.W.237.230; 1.W.237.231;
1.W.237.236; 1.W.237.237; 1.W.237.238; 1.W.237.239; 1.W.237.154; 1.W.237.157;
1.W.237.166; 1.W.237.169; 1.W.237.172; 1.W.237.175; 1.W.237.240; 1.W.237.244;
1.W.238.228; 1.W.238.229; 1.W.238.230; 1.W.238.231; 1.W.238.236; 1.W.238.237;
1.W.238.238; 1.W.238.239; 1.W.238.154; 1.W.238.157; 1.W.238.166; 1.W.238.169;
1.W.238.172; 1.W.238.175; 1.W.238.240; 1.W.238.244; 1.W.239.228; 1.W.239.229;
1.W.239.230; 1.W.239.231; 1.W.239.236; 1.W.239.237; 1.W.239.238; 1.W.239.239;
1.W.239.154; 1.W.239.157; 1.W.239.166; 1.W.239.169; 1.W.239.172; 1.W.239.175;
1.W.239.240; 1.W.239.244; 1.W.154.228; 1.W.154.229; 1.W.154.230; 1.W.154.231;
1.W.154.236; 1.W.154.237; 1.W.154.238; 1.W.154.239; 1.W.154.154; 1.W.154.157;
1.W.154.166; 1.W.154.169; 1.W.154.172; 1.W.154.175; 1.W.154.240; 1.W.154.244;
1.W.157.228; 1.W.157.229; 1.W.157.230; 1.W.157.231; 1.W.157.236; 1.W.157.237;
1.W.157.238; 1.W.157.239; 1.W.157.154; 1.W.157.157; 1.W.157.166; 1.W.157.169;
1.W.157.172; 1.W.157.175; 1.W.157.240; 1.W.157.244; 1.W.166.228; 1.W.166.229;

TABLE 100-continued

1.W.166.230; 1.W.166.231; 1.W.166.236; 1.W.166.237; 1.W.166.238; 1.W.166.239;
1.W.166.154; 1.W.166.157; 1.W.166.166; 1.W.166.169; 1.W.166.172; 1.W.166.175;
1.W.166.240; 1.W.166.244; 1.W.169.228; 1.W.169.229; 1.W.169.230; 1.W.169.231;
1.W.169.236; 1.W.169.237; 1.W.169.238; 1.W.169.239; 1.W.169.154; 1.W.169.157;
1.W.169.166; 1.W.169.169; 1.W.169.172; 1.W.169.175; 1.W.169.240; 1.W.169.244;
1.W.172.228; 1.W.172.229; 1.W.172.230; 1.W.172.231; 1.W.172.236; 1.W.172.237;
1.W.172.238; 1.W.172.239; 1.W.172.154; 1.W.172.157; 1.W.172.166; 1.W.172.169;
1.W.172.172; 1.W.172.175; 1.W.172.240; 1.W.172.244; 1.W.175.228; 1.W.175.229;
1.W.175.230; 1.W.175.231; 1.W.175.236; 1.W.175.237; 1.W.175.238; 1.W.175.239;
1.W.175.154; 1.W.175.157; 1.W.175.166; 1.W.175.169; 1.W.175.172; 1.W.175.175;
1.W.175.240; 1.W.175.244; 1.W.240.228; 1.W.240.229; 1.W.240.230; 1.W.240.231;
1.W.240.236; 1.W.240.237; 1.W.240.238; 1.W.240.239; 1.W.240.154; 1.W.240.157;
1.W.240.166; 1.W.240.169; 1.W.240.172; 1.W.240.175; 1.W.240.240; 1.W.240.244;
1.W.244.228; 1.W.244.229; 1.W.244.230; 1.W.244.231; 1.W.244.236; 1.W.244.237;
1.W.244.238; 1.W.244.239; 1.W.244.154; 1.W.244.157; 1.W.244.166; 1.W.244.169;
1.W.244.172; 1.W.244.175; 1.W.244.240; 1.W.244.244;

Prodrugs of 1.Y

1.Y.228.228; 1.Y.228.229; 1.Y.228.230; 1.Y.228.231; 1.Y.228.236; 1.Y.228.237;
1.Y.228.238; 1.Y.228.239; 1.Y.228.154; 1.Y.228.157; 1.Y.228.166; 1.Y.228.169;
1.Y.228.172; 1.Y.228.175; 1.Y.228.240; 1.Y.228.244; 1.Y.229.228; 1.Y.229.229;
1.Y.229.230; 1.Y.229.231; 1.Y.229.236; 1.Y.229.237; 1.Y.229.238; 1.Y.229.239;
1.Y.229.154; 1.Y.229.157; 1.Y.229.166; 1.Y.229.169; 1.Y.229.172; 1.Y.229.175;
1.Y.229.240; 1.Y.229.244; 1.Y.230.228; 1.Y.230.229; 1.Y.230.230; 1.Y.230.231;
1.Y.230.236; 1.Y.230.237; 1.Y.230.238; 1.Y.230.239; 1.Y.230.154; 1.Y.230.157;
1.Y.230.166; 1.Y.230.169; 1.Y.230.172; 1.Y.230.175; 1.Y.230.240; 1.Y.230.244;
1.Y.231.228; 1.Y.231.229; 1.Y.231.230; 1.Y.231.231; 1.Y.231.236; 1.Y.231.237;
1.Y.231.238; 1.Y.231.239; 1.Y.231.154; 1.Y.231.157; 1.Y.231.166; 1.Y.231.169;
1.Y.231.172; 1.Y.231.175; 1.Y.231.240; 1.Y.231.244; 1.Y.236.228; 1.Y.236.229;
1.Y.236.230; 1.Y.236.231; 1.Y.236.236; 1.Y.236.237; 1.Y.236.238; 1.Y.236.239;
1.Y.236.154; 1.Y.236.157; 1.Y.236.166; 1.Y.236.169; 1.Y.236.172; 1.Y.236.175;
1.Y.236.240; 1.Y.236.244; 1.Y.237.228; 1.Y.237.229; 1.Y.237.230; 1.Y.237.231;
1.Y.237.236; 1.Y.237.237; 1.Y.237.238; 1.Y.237.239; 1.Y.237.154; 1.Y.237.157;
1.Y.237.166; 1.Y.237.169; 1.Y.237.172; 1.Y.237.175; 1.Y.237.240; 1.Y.237.244;
1.Y.238.228; 1.Y.238.229; 1.Y.238.230; 1.Y.238.231; 1.Y.238.236; 1.Y.238.237;
1.Y.238.238; 1.Y.238.239; 1.Y.238.154; 1.Y.238.157; 1.Y.238.166; 1.Y.238.169;
1.Y.238.172; 1.Y.238.175; 1.Y.238.240; 1.Y.238.244; 1.Y.239.228; 1.Y.239.229;
1.Y.239.230; 1.Y.239.231; 1.Y.239.236; 1.Y.239.237; 1.Y.239.238; 1.Y.239.239;
1.Y.239.154; 1.Y.239.157; 1.Y.239.166; 1.Y.239.169; 1.Y.239.172; 1.Y.239.175;
1.Y.239.240; 1.Y.239.244; 1.Y.154.228; 1.Y.154.229; 1.Y.154.230; 1.Y.154.231;
1.Y.154.236; 1.Y.154.237; 1.Y.154.238; 1.Y.154.239; 1.Y.154.154; 1.Y.154.157;
1.Y.154.166; 1.Y.154.169; 1.Y.154.172; 1.Y.154.175; 1.Y.154.240; 1.Y.154.244;
1.Y.157.228; 1.Y.157.229; 1.Y.157.230; 1.Y.157.231; 1.Y.157.236; 1.Y.157.237;
1.Y.157.238; 1.Y.157.239; 1.Y.157.154; 1.Y.157.157; 1.Y.157.166; 1.Y.157.169;
1.Y.157.172; 1.Y.157.175; 1.Y.157.240; 1.Y.157.244; 1.Y.166.228; 1.Y.166.229;
1.Y.166.230; 1.Y.166.231; 1.Y.166.236; 1.Y.166.237; 1.Y.166.238; 1.Y.166.239;
1.Y.166.154; 1.Y.166.157; 1.Y.166.166; 1.Y.166.169; 1.Y.166.172; 1.Y.166.175;
1.Y.166.240; 1.Y.166.244; 1.Y.169.228; 1.Y.169.229; 1.Y.169.230; 1.Y.169.231;
1.Y.169.236; 1.Y.169.237; 1.Y.169.238; 1.Y.169.239; 1.Y.169.154; 1.Y.169.157;
1.Y.169.166; 1.Y.169.169; 1.Y.169.172; 1.Y.169.175; 1.Y.169.240; 1.Y.169.244;
1.Y.172.228; 1.Y.172.229; 1.Y.172.230; 1.Y.172.231; 1.Y.172.236; 1.Y.172.237;
1.Y.172.238; 1.Y.172.239; 1.Y.172.154; 1.Y.172.157; 1.Y.172.166; 1.Y.172.169;
1.Y.172.172; 1.Y.172.175; 1.Y.172.240; 1.Y.172.244; 1.Y.175.228; 1.Y.175.229;
1.Y.175.230; 1.Y.175.231; 1.Y.175.236; 1.Y.175.237; 1.Y.175.238; 1.Y.175.239;
1.Y.175.154; 1.Y.175.157; 1.Y.175.166; 1.Y.175.169; 1.Y.175.172; 1.Y.175.175;
1.Y.175.240; 1.Y.175.244; 1.Y.240.228; 1.Y.240.229; 1.Y.240.230; 1.Y.240.231;
1.Y.240.236; 1.Y.240.237; 1.Y.240.238; 1.Y.240.239; 1.Y.240.154; 1.Y.240.157;
1.Y.240.166; 1.Y.240.169; 1.Y.240.172; 1.Y.240.175; 1.Y.240.240; 1.Y.240.244;
1.Y.244.228; 1.Y.244.229; 1.Y.244.230; 1.Y.244.231; 1.Y.244.236; 1.Y.244.237;
1.Y.244.238; 1.Y.244.239; 1.Y.244.154; 1.Y.244.157; 1.Y.244.166; 1.Y.244.169;
1.Y.244.172; 1.Y.244.175; 1.Y.244.240; 1.Y.244.244;

Prodrugs of 2.B

2.B.228.228; 2.B.228.229; 2.B.228.230; 2.B.228.231; 2.B.228.236; 2.B.228.237;
2.B.228.238; 2.B.228.239; 2.B.228.154; 2.B.228.157; 2.B.228.166; 2.B.228.169; 2.B.228.172;
2.B.228.175; 2.B.228.240; 2.B.228.244; 2.B.229.228; 2.B.229.229; 2.B.229.230; 2.B.229.231;
2.B.229.236; 2.B.229.237; 2.B.229.238; 2.B.229.239; 2.B.229.154; 2.B.229.157; 2.B.229.166;
2.B.229.169; 2.B.229.172; 2.B.229.175; 2.B.229.240; 2.B.229.244; 2.B.230.228; 2.B.230.229;
2.B.230.230; 2.B.230.231; 2.B.230.236; 2.B.230.237; 2.B.230.238; 2.B.230.239; 2.B.230.154;
2.B.230.157; 2.B.230.166; 2.B.230.169; 2.B.230.172; 2.B.230.175; 2.B.230.240; 2.B.230.244;
2.B.231.228; 2.B.231.229; 2.B.231.230; 2.B.231.231; 2.B.231.236; 2.B.231.237; 2.B.231.238;
2.B.231.239; 2.B.231.154; 2.B.231.157; 2.B.231.166; 2.B.231.169; 2.B.231.172; 2.B.231.175;
2.B.231.240; 2.B.231.244; 2.B.236.228; 2.B.236.229; 2.B.236.230; 2.B.236.231; 2.B.236.236;
2.B.236.237; 2.B.236.238; 2.B.236.239; 2.B.236.154; 2.B.236.157; 2.B.236.166; 2.B.236.169;
2.B.236.172; 2.B.236.175; 2.B.236.240; 2.B.236.244; 2.B.237.228; 2.B.237.229; 2.B.237.230;
2.B.237.231; 2.B.237.236; 2.B.237.237; 2.B.237.238; 2.B.237.239; 2.B.237.154; 2.B.237.157;
2.B.237.166; 2.B.237.169; 2.B.237.172; 2.B.237.175; 2.B.237.240; 2.B.237.244; 2.B.238.228;
2.B.238.229; 2.B.238.230; 2.B.238.231; 2.B.238.236; 2.B.238.237; 2.B.238.238; 2.B.238.239;
2.B.238.154; 2.B.238.157; 2.B.238.166; 2.B.238.169; 2.B.238.172; 2.B.238.175; 2.B.238.240;

TABLE 100-continued

2.B.238.244; 2.B.239.228; 2.B.239.229; 2.B.239.230; 2.B.239.231; 2.B.239.236; 2.B.239.237;
2.B.239.238; 2.B.239.239; 2.B.239.154; 2.B.239.157; 2.B.239.166; 2.B.239.169; 2.B.239.172;
2.B.239.175; 2.B.239.240; 2.B.239.244; 2.B.154.228; 2.B.154.229; 2.B.154.230; 2.B.154.231;
2.B.154.236; 2.B.154.237; 2.B.154.238; 2.B.154.239; 2.B.154.154; 2.B.154.157; 2.B.154.166;
2.B.154.169; 2.B.154.172; 2.B.154.175; 2.B.154.240; 2.B.154.244; 2.B.157.228; 2.B.157.229;
2.B.157.230; 2.B.157.231; 2.B.157.236; 2.B.157.237; 2.B.157.238; 2.B.157.239; 2.B.157.154;
2.B.157.157; 2.B.157.166; 2.B.157.169; 2.B.157.172; 2.B.157.175; 2.B.157.240; 2.B.157.244;
2.B.166.228; 2.B.166.229; 2.B.166.230; 2.B.166.231; 2.B.166.236; 2.B.166.237; 2.B.166.238;
2.B.166.239; 2.B.166.154; 2.B.166.157; 2.B.166.166; 2.B.166.169; 2.B.166.172; 2.B.166.175;
2.B.166.240; 2.B.166.244; 2.B.169.228; 2.B.169.229; 2.B.169.230; 2.B.169.231; 2.B.169.236;
2.B.169.237; 2.B.169.238; 2.B.169.239; 2.B.169.154; 2.B.169.157; 2.B.169.166; 2.B.169.169;
2.B.169.172; 2.B.169.175; 2.B.169.240; 2.B.169.244; 2.B.172.228; 2.B.172.229; 2.B.172.230;
2.B.172.231; 2.B.172.236; 2.B.172.237; 2.B.172.238; 2.B.172.239; 2.B.172.154; 2.B.172.157;
2.B.172.166; 2.B.172.169; 2.B.172.172; 2.B.172.175; 2.B.172.240; 2.B.172.244; 2.B.175.228;
2.B.175.229; 2.B.175.230; 2.B.175.231; 2.B.175.236; 2.B.175.237; 2.B.175.238; 2.B.175.239;
2.B.175.154; 2.B.175.157; 2.B.175.166; 2.B.175.169; 2.B.175.172; 2.B.175.175; 2.B.175.240;
2.B.175.244; 2.B.240.228; 2.B.240.229; 2.B.240.230; 2.B.240.231; 2.B.240.236; 2.B.240.237;
2.B.240.238; 2.B.240.239; 2.B.240.154; 2.B.240.157; 2.B.240.166; 2.B.240.169; 2.B.240.172;
2.B.240.175; 2.B.240.240; 2.B.240.244; 2.B.244.228; 2.B.244.229; 2.B.244.230; 2.B.244.231;
2.B.244.236; 2.B.244.237; 2.B.244.238; 2.B.244.239; 2.B.244.154; 2.B.244.157; 2.B.244.166;
2.B.244.169; 2.B.244.172; 2.B.244.175; 2.B.244.240; 2.B.244.244;

Prodrugs of 2.D

2.D.228.228; 2.D.228.229; 2.D.228.230; 2.D.228.231; 2.D.228.236; 2.D.228.237;
2.D.228.238; 2.D.228.239; 2.D.228.154; 2.D.228.157; 2.D.228.166; 2.D.228.169;
2.D.228.172; 2.D.228.175; 2.D.228.240; 2.D.228.244; 2.D.229.228; 2.D.229.229;
2.D.229.230; 2.D.229.231; 2.D.229.236; 2.D.229.237; 2.D.229.238; 2.D.229.239;
2.D.229.154; 2.D.229.157; 2.D.229.166; 2.D.229.169; 2.D.229.172; 2.D.229.175;
2.D.229.240; 2.D.229.244; 2.D.230.228; 2.D.230.229; 2.D.230.230; 2.D.230.231;
2.D.230.236; 2.D.230.237; 2.D.230.238; 2.D.230.239; 2.D.230.154; 2.D.230.157;
2.D.230.166; 2.D.230.169; 2.D.230.172; 2.D.230.175; 2.D.230.240; 2.D.230.244;
2.D.231.228; 2.D.231.229; 2.D.231.230; 2.D.231.231; 2.D.231.236; 2.D.231.237;
2.D.231.238; 2.D.231.239; 2.D.231.154; 2.D.231.157; 2.D.231.166; 2.D.231.169;
2.D.231.172; 2.D.231.175; 2.D.231.240; 2.D.231.244; 2.D.236.228; 2.D.236.229;
2.D.236.230; 2.D.236.231; 2.D.236.236; 2.D.236.237; 2.D.236.238; 2.D.236.239;
2.D.236.154; 2.D.236.157; 2.D.236.166; 2.D.236.169; 2.D.236.172; 2.D.236.175;
2.D.236.240; 2.D.236.244; 2.D.237.228; 2.D.237.229; 2.D.237.230; 2.D.237.231;
2.D.237.236; 2.D.237.237; 2.D.237.238; 2.D.237.239; 2.D.237.154; 2.D.237.157;
2.D.237.166; 2.D.237.169; 2.D.237.172; 2.D.237.175; 2.D.237.240; 2.D.237.244;
2.D.238.228; 2.D.238.229; 2.D.238.230; 2.D.238.231; 2.D.238.236; 2.D.238.237;
2.D.238.238; 2.D.238.239; 2.D.238.154; 2.D.238.157; 2.D.238.166; 2.D.238.169;
2.D.238.172; 2.D.238.175; 2.D.238.240; 2.D.238.244; 2.D.239.228; 2.D.239.229;
2.D.239.230; 2.D.239.231; 2.D.239.236; 2.D.239.237; 2.D.239.238; 2.D.239.239;
2.D.239.154; 2.D.239.157; 2.D.239.166; 2.D.239.169; 2.D.239.172; 2.D.239.175;
2.D.239.240; 2.D.239.244; 2.D.154.228; 2.D.154.229; 2.D.154.230; 2.D.154.231;
2.D.154.236; 2.D.154.237; 2.D.154.238; 2.D.154.239; 2.D.154.154; 2.D.154.157;
2.D.154.166; 2.D.154.169; 2.D.154.172; 2.D.154.175; 2.D.154.240; 2.D.154.244;
2.D.157.228; 2.D.157.229; 2.D.157.230; 2.D.157.231; 2.D.157.236; 2.D.157.237;
2.D.157.238; 2.D.157.239; 2.D.157.154; 2.D.157.157; 2.D.157.166; 2.D.157.169;
2.D.157.172; 2.D.157.175; 2.D.157.240; 2.D.157.244; 2.D.166.228; 2.D.166.229;
2.D.166.230; 2.D.166.231; 2.D.166.236; 2.D.166.237; 2.D.166.238; 2.D.166.239;
2.D.166.154; 2.D.166.157; 2.D.166.166; 2.D.166.169; 2.D.166.172; 2.D.166.175;
2.D.166.240; 2.D.166.244; 2.D.169.228; 2.D.169.229; 2.D.169.230; 2.D.169.231;
2.D.169.236; 2.D.169.237; 2.D.169.238; 2.D.169.239; 2.D.169.154; 2.D.169.157;
2.D.169.166; 2.D.169.169; 2.D.169.172; 2.D.169.175; 2.D.169.240; 2.D.169.244;
2.D.172.228; 2.D.172.229; 2.D.172.230; 2.D.172.231; 2.D.172.236; 2.D.172.237;
2.D.172.238; 2.D.172.239; 2.D.172.154; 2.D.172.157; 2.D.172.166; 2.D.172.169;
2.D.172.172; 2.D.172.175; 2.D.172.240; 2.D.172.244; 2.D.175.228; 2.D.175.229;
2.D.175.230; 2.D.175.231; 2.D.175.236; 2.D.175.237; 2.D.175.238; 2.D.175.239;
2.D.175.154; 2.D.175.157; 2.D.175.166; 2.D.175.169; 2.D.175.172; 2.D.175.175;
2.D.175.240; 2.D.175.244; 2.D.240.228; 2.D.240.229; 2.D.240.230; 2.D.240.231;
2.D.240.236; 2.D.240.237; 2.D.240.238; 2.D.240.239; 2.D.240.154; 2.D.240.157;
2.D.240.166; 2.D.240.169; 2.D.240.172; 2.D.240.175; 2.D.240.240; 2.D.240.244;
2.D.244.228; 2.D.244.229; 2.D.244.230; 2.D.244.231; 2.D.244.236; 2.D.244.237;
2.D.244.238; 2.D.244.239; 2.D.244.154; 2.D.244.157; 2.D.244.166; 2.D.244.169;
2.D.244.172; 2.D.244.175; 2.D.244.240; 2.D.244.244;

Prodrugs of 2.E

2.E.228.228; 2.E.228.229; 2.E.228.230; 2.E.228.231; 2.E.228.236; 2.E.228.237;
2.E.228.238; 2.E.228.239; 2.E.228.154; 2.E.228.157; 2.E.228.166; 2.E.228.169; 2.E.228.172;
2.E.228.175; 2.E.228.240; 2.E.228.244; 2.E.229.228; 2.E.229.229; 2.E.229.230; 2.E.229.231;
2.E.229.236; 2.E.229.237; 2.E.229.238; 2.E.229.239; 2.E.229.154; 2.E.229.157; 2.E.229.166;
2.E.229.169; 2.E.229.172; 2.E.229.175; 2.E.229.240; 2.E.229.244; 2.E.230.228; 2.E.230.229;
2.E.230.230; 2.E.230.231; 2.E.230.236; 2.E.230.237; 2.E.230.238; 2.E.230.239; 2.E.230.154;
2.E.230.157; 2.E.230.166; 2.E.230.169; 2.E.230.172; 2.E.230.175; 2.E.230.240; 2.E.230.244;
2.E.231.228; 2.E.231.229; 2.E.231.230; 2.E.231.231; 2.E.231.236; 2.E.231.237; 2.E.231.238;
2.E.231.239; 2.E.231.154; 2.E.231.157; 2.E.231.166; 2.E.231.169; 2.E.231.172; 2.E.231.175;
2.E.231.240; 2.E.231.244; 2.E.236.228; 2.E.236.229; 2.E.236.230; 2.E.236.231; 2.E.236.236;
2.E.236.237; 2.E.236.238; 2.E.236.239; 2.E.236.154; 2.E.236.157; 2.E.236.166; 2.E.236.169;

TABLE 100-continued

2.E.236.172; 2.E.236.175; 2.E.236.240; 2.E.236.244; 2.E.237.228; 2.E.237.229; 2.E.237.230;
2.E.237.231; 2.E.237.236; 2.E.237.237; 2.E.237.238; 2.E.237.239; 2.E.237.154; 2.E.237.157;
2.E.237.166; 2.E.237.169; 2.E.237.172; 2.E.237.175; 2.E.237.240; 2.E.237.244; 2.E.238.228;
2.E.238.229; 2.E.238.230; 2.E.238.231; 2.E.238.236; 2.E.238.237; 2.E.238.238; 2.E.238.239;
2.E.238.154; 2.E.238.157; 2.E.238.166; 2.E.238.169; 2.E.238.172; 2.E.238.175; 2.E.238.240;
2.E.238.244; 2.E.239.228; 2.E.239.229; 2.E.239.230; 2.E.239.231; 2.E.239.236; 2.E.239.237;
2.E.239.238; 2.E.239.239; 2.E.239.154; 2.E.239.157; 2.E.239.166; 2.E.239.169; 2.E.239.172;
2.E.239.175; 2.E.239.240; 2.E.239.244; 2.E.154.228; 2.E.154.229; 2.E.154.230; 2.E.154.231;
2.E.154.236; 2.E.154.237; 2.E.154.238; 2.E.154.239; 2.E.154.154; 2.E.154.157; 2.E.154.166;
2.E.154.169; 2.E.154.172; 2.E.154.175; 2.E.154.240; 2.E.154.244; 2.E.157.228; 2.E.157.229;
2.E.157.230; 2.E.157.231; 2.E.157.236; 2.E.157.237; 2.E.157.238; 2.E.157.239; 2.E.157.154;
2.E.157.157; 2.E.157.166; 2.E.157.169; 2.E.157.172; 2.E.157.175; 2.E.157.240; 2.E.157.244;
2.E.166.228; 2.E.166.229; 2.E.166.230; 2.E.166.231; 2.E.166.236; 2.E.166.237; 2.E.166.238;
2.E.166.239; 2.E.166.154; 2.E.166.157; 2.E.166.166; 2.E.166.169; 2.E.166.172; 2.E.166.175;
2.E.166.240; 2.E.166.244; 2.E.169.228; 2.E.169.229; 2.E.169.230; 2.E.169.231; 2.E.169.236;
2.E.169.237; 2.E.169.238; 2.E.169.239; 2.E.169.154; 2.E.169.157; 2.E.169.166; 2.E.169.169;
2.E.169.172; 2.E.169.175; 2.E.169.240; 2.E.169.244; 2.E.172.228; 2.E.172.229; 2.E.172.230;
2.E.172.231; 2.E.172.236; 2.E.172.237; 2.E.172.238; 2.E.172.239; 2.E.172.154; 2.E.172.157;
2.E.172.166; 2.E.172.169; 2.E.172.172; 2.E.172.175; 2.E.172.240; 2.E.172.244; 2.E.175.228;
2.E.175.229; 2.E.175.230; 2.E.175.231; 2.E.175.236; 2.E.175.237; 2.E.175.238; 2.E.175.239;
2.E.175.154; 2.E.175.157; 2.E.175.166; 2.E.175.169; 2.E.175.172; 2.E.175.175; 2.E.175.240;
2.E.175.244; 2.E.240.228; 2.E.240.229; 2.E.240.230; 2.E.240.231; 2.E.240.236; 2.E.240.237;
2.E.240.238; 2.E.240.239; 2.E.240.154; 2.E.240.157; 2.E.240.166; 2.E.240.169; 2.E.240.172;
2.E.240.175; 2.E.240.240; 2.E.240.244; 2.E.244.228; 2.E.244.229; 2.E.244.230; 2.E.244.231;
2.E.244.236; 2.E.244.237; 2.E.244.238; 2.E.244.239; 2.E.244.154; 2.E.244.157; 2.E.244.166;
2.E.244.169; 2.E.244.172; 2.E.244.175; 2.E.244.240; 2.E.244.244;

Prodrugs of 2.G

2.G.228.228; 2.G.228.229; 2.G.228.230; 2.G.228.231; 2.G.228.236; 2.G.228.237;
2.G.228.238; 2.G.228.239; 2.G.228.154; 2.G.228.157; 2.G.228.166; 2.G.228.169;
2.G.228.172; 2.G.228.175; 2.G.228.240; 2.G.228.244; 2.G.229.228; 2.G.229.229;
2.G.229.230; 2.G.229.231; 2.G.229.236; 2.G.229.237; 2.G.229.238; 2.G.229.239;
2.G.229.154; 2.G.229.157; 2.G.229.166; 2.G.229.169; 2.G.229.172; 2.G.229.175;
2.G.229.240; 2.G.229.244; 2.G.230.228; 2.G.230.229; 2.G.230.230; 2.G.230.231;
2.G.230.236; 2.G.230.237; 2.G.230.238; 2.G.230.239; 2.G.230.154; 2.G.230.157;
2.G.230.166; 2.G.230.169; 2.G.230.172; 2.G.230.175; 2.G.230.240; 2.G.230.244;
2.G.231.228; 2.G.231.229; 2.G.231.230; 2.G.231.231; 2.G.231.236; 2.G.231.237;
2.G.231.238; 2.G.231.239; 2.G.231.154; 2.G.231.157; 2.G.231.166; 2.G.231.169;
2.G.231.172; 2.G.231.175; 2.G.231.240; 2.G.231.244; 2.G.236.228; 2.G.236.229;
2.G.236.230; 2.G.236.231; 2.G.236.236; 2.G.236.237; 2.G.236.238; 2.G.236.239;
2.G.236.154; 2.G.236.157; 2.G.236.166; 2.G.236.169; 2.G.236.172; 2.G.236.175;
2.G.236.240; 2.G.236.244; 2.G.237.228; 2.G.237.229; 2.G.237.230; 2.G.237.231;
2.G.237.236; 2.G.237.237; 2.G.237.238; 2.G.237.239; 2.G.237.154; 2.G.237.157;
2.G.237.166; 2.G.237.169; 2.G.237.172; 2.G.237.175; 2.G.237.240; 2.G.237.244;
2.G.238.228; 2.G.238.229; 2.G.238.230; 2.G.238.231; 2.G.238.236; 2.G.238.237;
2.G.238.238; 2.G.238.239; 2.G.238.154; 2.G.238.157; 2.G.238.166; 2.G.238.169;
2.G.238.172; 2.G.238.175; 2.G.238.240; 2.G.238.244; 2.G.239.228; 2.G.239.229;
2.G.239.230; 2.G.239.231; 2.G.239.236; 2.G.239.237; 2.G.239.238; 2.G.239.239;
2.G.239.154; 2.G.239.157; 2.G.239.166; 2.G.239.169; 2.G.239.172; 2.G.239.175;
2.G.239.240; 2.G.239.244; 2.G.154.228; 2.G.154.229; 2.G.154.230; 2.G.154.231;
2.G.154.236; 2.G.154.237; 2.G.154.238; 2.G.154.239; 2.G.154.154; 2.G.154.157;
2.G.154.166; 2.G.154.169; 2.G.154.172; 2.G.154.175; 2.G.154.240; 2.G.154.244;
2.G.157.228; 2.G.157.229; 2.G.157.230; 2.G.157.231; 2.G.157.236; 2.G.157.237;
2.G.157.238; 2.G.157.239; 2.G.157.154; 2.G.157.157; 2.G.157.166; 2.G.157.169;
2.G.157.172; 2.G.157.175; 2.G.157.240; 2.G.157.244; 2.G.166.228; 2.G.166.229;
2.G.166.230; 2.G.166.231; 2.G.166.236; 2.G.166.237; 2.G.166.238; 2.G.166.239;
2.G.166.154; 2.G.166.157; 2.G.166.166; 2.G.166.169; 2.G.166.172; 2.G.166.175;
2.G.166.240; 2.G.166.244; 2.G.169.228; 2.G.169.229; 2.G.169.230; 2.G.169.231;
2.G.169.236; 2.G.169.237; 2.G.169.238; 2.G.169.239; 2.G.169.154; 2.G.169.157;
2.G.169.166; 2.G.169.169; 2.G.169.172; 2.G.169.175; 2.G.169.240; 2.G.169.244;
2.G.172.228; 2.G.172.229; 2.G.172.230; 2.G.172.231; 2.G.172.236; 2.G.172.237;
2.G.172.238; 2.G.172.239; 2.G.172.154; 2.G.172.157; 2.G.172.166; 2.G.172.169;
2.G.172.172; 2.G.172.175; 2.G.172.240; 2.G.172.244; 2.G.175.228; 2.G.175.229;
2.G.175.230; 2.G.175.231; 2.G.175.236; 2.G.175.237; 2.G.175.238; 2.G.175.239;
2.G.175.154; 2.G.175.157; 2.G.175.166; 2.G.175.169; 2.G.175.172; 2.G.175.175;
2.G.175.240; 2.G.175.244; 2.G.240.228; 2.G.240.229; 2.G.240.230; 2.G.240.231;
2.G.240.236; 2.G.240.237; 2.G.240.238; 2.G.240.239; 2.G.240.154; 2.G.240.157;
2.G.240.166; 2.G.240.169; 2.G.240.172; 2.G.240.175; 2.G.240.240; 2.G.240.244;
2.G.244.228; 2.G.244.229; 2.G.244.230; 2.G.244.231; 2.G.244.236; 2.G.244.237;
2.G.244.238; 2.G.244.239; 2.G.244.154; 2.G.244.157; 2.G.244.166; 2.G.244.169;
2.G.244.172; 2.G.244.175; 2.G.244.240; 2.G.244.244;

Prodrugs of 2.I

2.I.228.228; 2.I.228.229; 2.I.228.230; 2.I.228.231; 2.I.228.236; 2.I.228.237; 2.I.228.238;
2.I.228.239; 2.I.228.154; 2.I.228.157; 2.I.228.166; 2.I.228.169; 2.I.228.172; 2.I.228.175;
2.I.228.240; 2.I.228.244; 2.I.229.228; 2.I.229.229; 2.I.229.230; 2.I.229.231; 2.I.229.236;
2.I.229.237; 2.I.229.238; 2.I.229.239; 2.I.229.154; 2.I.229.157; 2.I.229.166; 2.I.229.169;
2.I.229.172; 2.I.229.175; 2.I.229.240; 2.I.229.244; 2.I.230.228; 2.I.230.229; 2.I.230.230;
2.I.230.231; 2.I.230.236; 2.I.230.237; 2.I.230.238; 2.I.230.239; 2.I.230.154; 2.I.230.157;

TABLE 100-continued

2.I.230.166; 2.I.230.169; 2.I.230.172; 2.I.230.175; 2.I.230.240; 2.I.230.244; 2.I.231.228; 2.I.231.229; 2.I.231.230; 2.I.231.231; 2.I.231.236; 2.I.231.237; 2.I.231.238; 2.I.231.239; 2.I.231.154; 2.I.231.157; 2.I.231.166; 2.I.231.169; 2.I.231.172; 2.I.231.175; 2.I.231.240; 2.I.231.244; 2.I.236.228; 2.I.236.229; 2.I.236.230; 2.I.236.231; 2.I.236.236; 2.I.236.237; 2.I.236.238; 2.I.236.239; 2.I.236.154; 2.I.236.157; 2.I.236.166; 2.I.236.169; 2.I.236.172; 2.I.236.175; 2.I.236.240; 2.I.236.244; 2.I.237.228; 2.I.237.229; 2.I.237.230; 2.I.237.231; 2.I.237.236; 2.I.237.237; 2.I.237.238; 2.I.237.239; 2.I.237.154; 2.I.237.157; 2.I.237.166; 2.I.237.169; 2.I.237.172; 2.I.237.175; 2.I.237.240; 2.I.237.244; 2.I.238.228; 2.I.238.229; 2.I.238.230; 2.I.238.231; 2.I.238.236; 2.I.238.237; 2.I.238.238; 2.I.238.239; 2.I.238.154; 2.I.238.157; 2.I.238.166; 2.I.238.169; 2.I.238.172; 2.I.238.175; 2.I.238.240; 2.I.238.244; 2.I.239.228; 2.I.239.229; 2.I.239.230; 2.I.239.231; 2.I.239.236; 2.I.239.237; 2.I.239.238; 2.I.239.239; 2.I.239.154; 2.I.239.157; 2.I.239.166; 2.I.239.169; 2.I.239.172; 2.I.239.175; 2.I.239.240; 2.I.239.244; 2.I.154.228; 2.I.154.229; 2.I.154.230; 2.I.154.231; 2.I.154.236; 2.I.154.237; 2.I.154.238; 2.I.154.239; 2.I.154.154; 2.I.154.157; 2.I.154.166; 2.I.154.169; 2.I.154.172; 2.I.154.175; 2.I.154.240; 2.I.154.244; 2.I.157.228; 2.I.157.229; 2.I.157.230; 2.I.157.231; 2.I.157.236; 2.I.157.237; 2.I.157.238; 2.I.157.239; 2.I.157.154; 2.I.157.157; 2.I.157.166; 2.I.157.169; 2.I.157.172; 2.I.157.175; 2.I.157.240; 2.I.157.244; 2.I.166.228; 2.I.166.229; 2.I.166.230; 2.I.166.231; 2.I.166.236; 2.I.166.237; 2.I.166.238; 2.I.166.239; 2.I.166.154; 2.I.166.157; 2.I.166.166; 2.I.166.169; 2.I.166.172; 2.I.166.175; 2.I.166.240; 2.I.166.244; 2.I.169.228; 2.I.169.229; 2.I.169.230; 2.I.169.231; 2.I.169.236; 2.I.169.237; 2.I.169.238; 2.I.169.239; 2.I.169.154; 2.I.169.157; 2.I.169.166; 2.I.169.169; 2.I.169.172; 2.I.169.175; 2.I.169.240; 2.I.169.244; 2.I.172.228; 2.I.172.229; 2.I.172.230; 2.I.172.231; 2.I.172.236; 2.I.172.237; 2.I.172.238; 2.I.172.239; 2.I.172.154; 2.I.172.157; 2.I.172.166; 2.I.172.169; 2.I.172.172; 2.I.172.175; 2.I.172.240; 2.I.172.244; 2.I.175.228; 2.I.175.229; 2.I.175.230; 2.I.175.231; 2.I.175.236; 2.I.175.237; 2.I.175.238; 2.I.175.239; 2.I.175.154; 2.I.175.157; 2.I.175.166; 2.I.175.169; 2.I.175.172; 2.I.175.175; 2.I.175.240; 2.I.175.244; 2.I.240.228; 2.I.240.229; 2.I.240.230; 2.I.240.231; 2.I.240.236; 2.I.240.237; 2.I.240.238; 2.I.240.239; 2.I.240.154; 2.I.240.157; 2.I.240.166; 2.I.240.169; 2.I.240.172; 2.I.240.175; 2.I.240.240; 2.I.240.244; 2.I.244.228; 2.I.244.229; 2.I.244.230; 2.I.244.231; 2.I.244.236; 2.I.244.237; 2.I.244.238; 2.I.244.239; 2.I.244.154; 2.I.244.157; 2.I.244.166; 2.I.244.169; 2.I.244.172; 2.I.244.175; 2.I.244.240; 2.I.244.244;

Prodrugs of 2.J

2.J.228.228; 2.J.228.229; 2.J.228.230; 2.J.228.231; 2.J.228.236; 2.J.228.237; 2.J.228.238; 2.J.228.239; 2.J.228.154; 2.J.228.157; 2.J.228.166; 2.J.228.169; 2.J.228.172; 2.J.228.175; 2.J.228.240; 2.J.228.244; 2.J.229.228; 2.J.229.229; 2.J.229.230; 2.J.229.231; 2.J.229.236; 2.J.229.237; 2.J.229.238; 2.J.229.239; 2.J.229.154; 2.J.229.157; 2.J.229.166; 2.J.229.169; 2.J.229.172; 2.J.229.175; 2.J.229.240; 2.J.229.244; 2.J.230.228; 2.J.230.229; 2.J.230.230; 2.J.230.231; 2.J.230.236; 2.J.230.237; 2.J.230.238; 2.J.230.239; 2.J.230.154; 2.J.230.157; 2.J.230.166; 2.J.230.169; 2.J.230.172; 2.J.230.175; 2.J.230.240; 2.J.230.244; 2.J.231.228; 2.J.231.229; 2.J.231.230; 2.J.231.231; 2.J.231.236; 2.J.231.237; 2.J.231.238; 2.J.231.239; 2.J.231.154; 2.J.231.157; 2.J.231.166; 2.J.231.169; 2.J.231.172; 2.J.231.175; 2.J.231.240; 2.J.231.244; 2.J.236.228; 2.J.236.229; 2.J.236.230; 2.J.236.231; 2.J.236.236; 2.J.236.237; 2.J.236.238; 2.J.236.239; 2.J.236.154; 2.J.236.157; 2.J.236.166; 2.J.236.169; 2.J.236.172; 2.J.236.175; 2.J.236.240; 2.J.236.244; 2.J.237.228; 2.J.237.229; 2.J.237.230; 2.J.237.231; 2.J.237.236; 2.J.237.237; 2.J.237.238; 2.J.237.239; 2.J.237.154; 2.J.237.157; 2.J.237.166; 2.J.237.169; 2.J.237.172; 2.J.237.175; 2.J.237.240; 2.J.237.244; 2.J.238.228; 2.J.238.229; 2.J.238.230; 2.J.238.231; 2.J.238.236; 2.J.238.237; 2.J.238.238; 2.J.238.239; 2.J.238.154; 2.J.238.157; 2.J.238.166; 2.J.238.169; 2.J.238.172; 2.J.238.175; 2.J.238.240; 2.J.238.244; 2.J.239.228; 2.J.239.229; 2.J.239.230; 2.J.239.231; 2.J.239.236; 2.J.239.237; 2.J.239.238; 2.J.239.239; 2.J.239.154; 2.J.239.157; 2.J.239.166; 2.J.239.169; 2.J.239.172; 2.J.239.175; 2.J.239.240; 2.J.239.244; 2.J.154.228; 2.J.154.229; 2.J.154.230; 2.J.154.231; 2.J.154.236; 2.J.154.237; 2.J.154.238; 2.J.154.239; 2.J.154.154; 2.J.154.157; 2.J.154.166; 2.J.154.169; 2.J.154.172; 2.J.154.175; 2.J.154.240; 2.J.154.244; 2.J.157.228; 2.J.157.229; 2.J.157.230; 2.J.157.231; 2.J.157.236; 2.J.157.237; 2.J.157.238; 2.J.157.239; 2.J.157.154; 2.J.157.157; 2.J.157.166; 2.J.157.169; 2.J.157.172; 2.J.157.175; 2.J.157.240; 2.J.157.244; 2.J.166.228; 2.J.166.229; 2.J.166.230; 2.J.166.231; 2.J.166.236; 2.J.166.237; 2.J.166.238; 2.J.166.239; 2.J.166.154; 2.J.166.157; 2.J.166.166; 2.J.166.169; 2.J.166.172; 2.J.166.175; 2.J.166.240; 2.J.166.244; 2.J.169.228; 2.J.169.229; 2.J.169.230; 2.I.169.231; 2.J.169.236; 2.J.169.237; 2.J.169.238; 2.J.169.239; 2.J.169.154; 2.J.169.157; 2.J.169.166; 2.J.169.169; 2.J.169.172; 2.J.169.175; 2.J.169.240; 2.J.169.244; 2.J.172.228; 2.J.172.229; 2.J.172.230; 2.J.172.231; 2.J.172.236; 2.J.172.237; 2.J.172.238; 2.J.172.239; 2.J.172.154; 2.J.172.157; 2.J.172.166; 2.J.172.169; 2.J.172.172; 2.J.172.175; 2.J.172.240; 2.J.172.244; 2.J.175.228; 2.J.175.229; 2.J.175.230; 2.J.175.231; 2.J.175.236; 2.J.175.237; 2.J.175.238; 2.J.175.239; 2.J.175.154; 2.J.175.157; 2.J.175.166; 2.J.175.169; 2.J.175.172; 2.J.175.175; 2.J.175.240; 2.J.175.244; 2.J.240.228; 2.J.240.229; 2.J.240.230; 2.J.240.231; 2.J.240.236; 2.J.240.237; 2.J.240.238; 2.J.240.239; 2.J.240.154; 2.J.240.157; 2.J.240.166; 2.J.240.169; 2.J.240.172; 2.J.240.175; 2.J.240.240; 2.J.240.244; 2.J.244.228; 2.J.244.229; 2.J.244.230; 2.J.244.231; 2.J.244.236; 2.J.244.237; 2.J.244.238; 2.J.244.239; 2.J.244.154; 2.J.244.157; 2.J.244.166; 2.J.244.169; 2.J.244.172; 2.J.244.175; 2.J.244.240; 2.J.244.244;

Prodrugs of 2.L

2.L.228.228; 2.L.228.229; 2.L.228.230; 2.L.228.231; 2.L.228.236; 2.L.228.237; 2.L.228.238; 2.L.228.239; 2.L.228.154; 2.L.228.157; 2.L.228.166; 2.L.228.169; 2.L.228.172; 2.L.228.175; 2.L.228.240; 2.L.228.244; 2.L.229.228; 2.L.229.229; 2.L.229.230; 2.L.229.231; 2.L.229.236; 2.L.229.237; 2.L.229.238; 2.L.229.239; 2.L.229.154; 2.L.229.157; 2.L.229.166; 2.L.229.169; 2.L.229.172; 2.L.229.175; 2.L.229.240; 2.L.229.244; 2.L.230.228; 2.L.230.229; 2.L.230.230; 2.L.230.231; 2.L.230.236; 2.L.230.237; 2.L.230.238; 2.L.230.239; 2.L.230.154; 2.L.230.157; 2.L.230.166; 2.L.230.169; 2.L.230.172; 2.L.230.175; 2.L.230.240; 2.L.230.244;

TABLE 100-continued

2.L.231.228; 2.L.231.229; 2.L.231.230; 2.L.231.231; 2.L.231.236; 2.L.231.237; 2.L.231.238;
2.L.231.239; 2.L.231.154; 2.L.231.157; 2.L.231.166; 2.L.231.169; 2.L.231.172; 2.L.231.175;
2.L.231.240; 2.L.231.244; 2.L.236.228; 2.L.236.229; 2.L.236.230; 2.L.236.231; 2.L.236.236;
2.L.236.237; 2.L.236.238; 2.L.236.239; 2.L.236.154; 2.L.236.157; 2.L.236.166; 2.L.236.169;
2.L.236.172; 2.L.236.175; 2.L.236.240; 2.L.236.244; 2.L.237.228; 2.L.237.229; 2.L.237.230;
2.L.237.231; 2.L.237.236; 2.L.237.237; 2.L.237.238; 2.L.237.239; 2.L.237.154; 2.L.237.157;
2.L.237.166; 2.L.237.169; 2.L.237.172; 2.L.237.175; 2.L.237.240; 2.L.237.244; 2.L.238.228;
2.L.238.229; 2.L.238.230; 2.L.238.231; 2.L.238.236; 2.L.238.237; 2.L.238.238; 2.L.238.239;
2.L.238.154; 2.L.238.157; 2.L.238.166; 2.L.238.169; 2.L.238.172; 2.L.238.175; 2.L.238.240;
2.L.238.244; 2.L.239.228; 2.L.239.229; 2.L.239.230; 2.L.239.231; 2.L.239.236; 2.L.239.237;
2.L.239.238; 2.L.239.239; 2.L.239.154; 2.L.239.157; 2.L.239.166; 2.L.239.169; 2.L.239.172;
2.L.239.175; 2.L.239.240; 2.L.239.244; 2.L.154.228; 2.L.154.229; 2.L.154.230; 2.L.154.231;
2.L.154.236; 2.L.154.237; 2.L.154.238; 2.L.154.239; 2.L.154.154; 2.L.154.157; 2.L.154.166;
2.L.154.169; 2.L.154.172; 2.L.154.175; 2.L.154.240; 2.L.154.244; 2.L.157.228; 2.L.157.229;
2.L.157.230; 2.L.157.231; 2.L.157.236; 2.L.157.237; 2.L.157.238; 2.L.157.239; 2.L.157.154;
2.L.157.157; 2.L.157.166; 2.L.157.169; 2.L.157.172; 2.L.157.175; 2.L.157.240; 2.L.157.244;
2.L.166.228; 2.L.166.229; 2.L.166.230; 2.L.166.231; 2.L.166.236; 2.L.166.237; 2.L.166.238;
2.L.166.239; 2.L.166.154; 2.L.166.157; 2.L.166.166; 2.L.166.169; 2.L.166.172; 2.L.166.175;
2.L.166.240; 2.L.166.244; 2.L.169.228; 2.L.169.229; 2.L.169.230; 2.L.169.231; 2.L.169.236;
2.L.169.237; 2.L.169.238; 2.L.169.239; 2.L.169.154; 2.L.169.157; 2.L.169.166; 2.L.169.169;
2.L.169.172; 2.L.169.175; 2.L.169.240; 2.L.169.244; 2.L.172.228; 2.L.172.229; 2.L.172.230;
2.L.172.231; 2.L.172.236; 2.L.172.237; 2.L.172.238; 2.L.172.239; 2.L.172.154; 2.L.172.157;
2.L.172.166; 2.L.172.169; 2.L.172.172; 2.L.172.175; 2.L.172.240; 2.L.172.244; 2.L.175.228;
2.L.175.229; 2.L.175.230; 2.L.175.231; 2.L.175.236; 2.L.175.237; 2.L.175.238; 2.L.175.239;
2.L.175.154; 2.L.175.157; 2.L.175.166; 2.L.175.169; 2.L.175.172; 2.L.175.175; 2.L.175.240;
2.L.175.244; 2.L.240.228; 2.L.240.229; 2.L.240.230; 2.L.240.231; 2.L.240.236; 2.L.240.237;
2.L.240.238; 2.L.240.239; 2.L.240.154; 2.L.240.157; 2.L.240.166; 2.L.240.169; 2.L.240.172;
2.L.240.175; 2.L.240.240; 2.L.240.244; 2.L.244.228; 2.L.244.229; 2.L.244.230; 2.L.244.231;
2.L.244.236; 2.L.244.237; 2.L.244.238; 2.L.244.239; 2.L.244.154; 2.L.244.157; 2.L.244.166;
2.L.244.169; 2.L.244.172; 2.L.244.175; 2.L.244.240; 2.L.244.244;

Prodrugs of 2.O

2.O.228.228; 2.O.228.229; 2.O.228.230; 2.O.228.231; 2.O.228.236; 2.O.228.237;
2.O.228.238; 2.O.228.239; 2.O.228.154; 2.O.228.157; 2.O.228.166; 2.O.228.169;
2.O.228.172; 2.O.228.175; 2.O.228.240; 2.O.228.244; 2.O.229.228; 2.O.229.229;
2.O.229.230; 2.O.229.231; 2.O.229.236; 2.O.229.237; 2.O.229.238; 2.O.229.239;
2.O.229.154; 2.O.229.157; 2.O.229.166; 2.O.229.169; 2.O.229.172; 2.O.229.175;
2.O.229.240; 2.O.229.244; 2.O.230.228; 2.O.230.229; 2.O.230.230; 2.O.230.231;
2.O.230.236; 2.O.230.237; 2.O.230.238; 2.O.230.239; 2.O.230.154; 2.O.230.157;
2.O.230.166; 2.O.230.169; 2.O.230.172; 2.O.230.175; 2.O.230.240; 2.O.230.244;
2.O.231.228; 2.O.231.229; 2.O.231.230; 2.O.231.231; 2.O.231.236; 2.O.231.237;
2.O.231.238; 2.O.231.239; 2.O.231.154; 2.O.231.157; 2.O.231.166; 2.O.231.169;
2.O.231.172; 2.O.231.175; 2.O.231.240; 2.O.231.244; 2.O.236.228; 2.O.236.229;
2.O.236.230; 2.O.236.231; 2.O.236.236; 2.O.236.237; 2.O.236.238; 2.O.236.239;
2.O.236.154; 2.O.236.157; 2.O.236.166; 2.O.236.169; 2.O.236.172; 2.O.236.175;
2.O.236.240; 2.O.236.244; 2.O.237.228; 2.O.237.229; 2.O.237.230; 2.O.237.231;
2.O.237.236; 2.O.237.237; 2.O.237.238; 2.O.237.239; 2.O.237.154; 2.O.237.157;
2.O.237.166; 2.O.237.169; 2.O.237.172; 2.O.237.175; 2.O.237.240; 2.O.237.244;
2.O.238.228; 2.O.238.229; 2.O.238.230; 2.O.238.231; 2.O.238.236; 2.O.238.237;
2.O.238.238; 2.O.238.239; 2.O.238.154; 2.O.238.157; 2.O.238.166; 2.O.238.169;
2.O.238.172; 2.O.238.175; 2.O.238.240; 2.O.238.244; 2.O.239.228; 2.O.239.229;
2.O.239.230; 2.O.239.231; 2.O.239.236; 2.O.239.237; 2.O.239.238; 2.O.239.239;
2.O.239.154; 2.O.239.157; 2.O.239.166; 2.O.239.169; 2.O.239.172; 2.O.239.175;
2.O.239.240; 2.O.239.244; 2.O.154.228; 2.O.154.229; 2.O.154.230; 2.O.154.231;
2.O.154.236; 2.O.154.237; 2.O.154.238; 2.O.154.239; 2.O.154.154; 2.O.154.157;
2.O.154.166; 2.O.154.169; 2.O.154.172; 2.O.154.175; 2.O.154.240; 2.O.154.244;
2.O.157.228; 2.O.157.229; 2.O.157.230; 2.O.157.231; 2.O.157.236; 2.O.157.237;
2.O.157.238; 2.O.157.239; 2.O.157.154; 2.O.157.157; 2.O.157.166; 2.O.157.169;
2.O.157.172; 2.O.157.175; 2.O.157.240; 2.O.157.244; 2.O.166.228; 2.O.166.229;
2.O.166.230; 2.O.166.231; 2.O.166.236; 2.O.166.237; 2.O.166.238; 2.O.166.239;
2.O.166.154; 2.O.166.157; 2.O.166.166; 2.O.166.169; 2.O.166.172; 2.O.166.175;
2.O.166.240; 2.O.166.244; 2.O.169.228; 2.O.169.229; 2.O.169.230; 2.O.169.231;
2.O.169.236; 2.O.169.237; 2.O.169.238; 2.O.169.239; 2.O.169.154; 2.O.169.157;
2.O.169.166; 2.O.169.169; 2.O.169.172; 2.O.169.175; 2.O.169.240; 2.O.169.244;
2.O.172.228; 2.O.172.229; 2.O.172.230; 2.O.172.231; 2.O.172.236; 2.O.172.237;
2.O.172.238; 2.O.172.239; 2.O.172.154; 2.O.172.157; 2.O.172.166; 2.O.172.169;
2.O.172.172; 2.O.172.175; 2.O.172.240; 2.O.172.244; 2.O.175.228; 2.O.175.229;
2.O.175.230; 2.O.175.231; 2.O.175.236; 2.O.175.237; 2.O.175.238; 2.O.175.239;
2.O.175.154; 2.O.175.157; 2.O.175.166; 2.O.175.169; 2.O.175.172; 2.O.175.175;
2.O.175.240; 2.O.175.244; 2.O.240.228; 2.O.240.229; 2.O.240.230; 2.O.240.231;
2.O.240.236; 2.O.240.237; 2.O.240.238; 2.O.240.239; 2.O.240.154; 2.O.240.157;
2.O.240.166; 2.O.240.169; 2.O.240.172; 2.O.240.175; 2.O.240.240; 2.O.240.244;
2.O.244.228; 2.O.244.229; 2.O.244.230; 2.O.244.231; 2.O.244.236; 2.O.244.237;
2.O.244.238; 2.O.244.239; 2.O.244.154; 2.O.244.157; 2.O.244.166; 2.O.244.169;
2.O.244.172; 2.O.244.175; 2.O.244.240; 2.O.244.244;

Prodrugs of 2.P

2.P.228.228; 2.P.228.229; 2.P.228.230; 2.P.228.231; 2.P.228.236; 2.P.228.237;
2.P.228.238; 2.P.228.239; 2.P.228.154; 2.P.228.157; 2.P.228.166; 2.P.228.169; 2.P.228.172;

TABLE 100-continued

2.P.228.175; 2.P.228.240; 2.P.228.244; 2.P.229.228; 2.P.229.229; 2.P.229.230; 2.P.229.231;
2.P.229.236; 2.P.229.237; 2.P.229.238; 2.P.229.239; 2.P.229.154; 2.P.229.157; 2.P.229.166;
2.P.229.169; 2.P.229.172; 2.P.229.175; 2.P.229.240; 2.P.229.244; 2.P.230.228; 2.P.230.229;
2.P.230.230; 2.P.230.231; 2.P.230.236; 2.P.230.237; 2.P.230.238; 2.P.230.239; 2.P.230.154;
2.P.230.157; 2.P.230.166; 2.P.230.169; 2.P.230.172; 2.P.230.175; 2.P.230.240; 2.P.230.244;
2.P.231.228; 2.P.231.229; 2.P.231.230; 2.P.231.231; 2.P.231.236; 2.P.231.237; 2.P.231.238;
2.P.231.239; 2.P.231.154; 2.P.231.157; 2.P.231.166; 2.P.231.169; 2.P.231.172; 2.P.231.175;
2.P.231.240; 2.P.231.244; 2.P.236.228; 2.P.236.229; 2.P.236.230; 2.P.236.231; 2.P.236.236;
2.P.236.237; 2.P.236.238; 2.P.236.239; 2.P.236.154; 2.P.236.157; 2.P.236.166; 2.P.236.169;
2.P.236.172; 2.P.236.175; 2.P.236.240; 2.P.236.244; 2.P.237.228; 2.P.237.229; 2.P.237.230;
2.P.237.231; 2.P.237.236; 2.P.237.237; 2.P.237.238; 2.P.237.239; 2.P.237.154; 2.P.237.157;
2.P.237.166; 2.P.237.169; 2.P.237.172; 2.P.237.175; 2.P.237.240; 2.P.237.244; 2.P.238.228;
2.P.238.229; 2.P.238.230; 2.P.238.231; 2.P.238.236; 2.P.238.237; 2.P.238.238; 2.P.238.239;
2.P.238.154; 2.P.238.157; 2.P.238.166; 2.P.238.169; 2.P.238.172; 2.P.238.175; 2.P.238.240;
2.P.238.244; 2.P.239.228; 2.P.239.229; 2.P.239.230; 2.P.239.231; 2.P.239.236; 2.P.239.237;
2.P.239.238; 2.P.239.239; 2.P.239.154; 2.P.239.157; 2.P.239.166; 2.P.239.169; 2.P.239.172;
2.P.239.175; 2.P.239.240; 2.P.239.244; 2.P.154.228; 2.P.154.229; 2.P.154.230; 2.P.154.231;
2.P.154.236; 2.P.154.237; 2.P.154.238; 2.P.154.239; 2.P.154.154; 2.P.154.157; 2.P.154.166;
2.P.154.169; 2.P.154.172; 2.P.154.175; 2.P.154.240; 2.P.154.244; 2.P.157.228; 2.P.157.229;
2.P.157.230; 2.P.157.231; 2.P.157.236; 2.P.157.237; 2.P.157.238; 2.P.157.239; 2.P.157.154;
2.P.157.157; 2.P.157.166; 2.P.157.169; 2.P.157.172; 2.P.157.175; 2.P.157.240; 2.P.157.244;
2.P.166.228; 2.P.166.229; 2.P.166.230; 2.P.166.231; 2.P.166.236; 2.P.166.237; 2.P.166.238;
2.P.166.239; 2.P.166.154; 2.P.166.157; 2.P.166.166; 2.P.166.169; 2.P.166.172; 2.P.166.175;
2.P.166.240; 2.P.166.244; 2.P.169.228; 2.P.169.229; 2.P.169.230; 2.P.169.231; 2.P.169.236;
2.P.169.237; 2.P.169.238; 2.P.169.239; 2.P.169.154; 2.P.169.157; 2.P.169.166; 2.P.169.169;
2.P.169.172; 2.P.169.175; 2.P.169.240; 2.P.169.244; 2.P.172.228; 2.P.172.229; 2.P.172.230;
2.P.172.231; 2.P.172.236; 2.P.172.237; 2.P.172.238; 2.P.172.239; 2.P.172.154; 2.P.172.157;
2.P.172.166; 2.P.172.169; 2.P.172.172; 2.P.172.175; 2.P.172.240; 2.P.172.244; 2.P.175.228;
2.P.175.229; 2.P.175.230; 2.P.175.231; 2.P.175.236; 2.P.175.237; 2.P.175.238; 2.P.175.239;
2.P.175.154; 2.P.175.157; 2.P.175.166; 2.P.175.169; 2.P.175.172; 2.P.175.175; 2.P.175.240;
2.P.175.244; 2.P.240.228; 2.P.240.229; 2.P.240.230; 2.P.240.231; 2.P.240.236; 2.P.240.237;
2.P.240.238; 2.P.240.239; 2.P.240.154; 2.P.240.157; 2.P.240.166; 2.P.240.169; 2.P.240.172;
2.P.240.175; 2.P.240.240; 2.P.240.244; 2.P.244.228; 2.P.244.229; 2.P.244.230; 2.P.244.231;
2.P.244.236; 2.P.244.237; 2.P.244.238; 2.P.244.239; 2.P.244.154; 2.P.244.157; 2.P.244.166;
2.P.244.169; 2.P.244.172; 2.P.244.175; 2.P.244.240; 2.P.244.244;

Prodrugs of 2.U

2.U.228.228; 2.U.228.229; 2.U.228.230; 2.U.228.231; 2.U.228.236; 2.U.228.237;
2.U.228.238; 2.U.228.239; 2.U.228.154; 2.U.228.157; 2.U.228.166; 2.U.228.169;
2.U.228.172; 2.U.228.175; 2.U.228.240; 2.U.228.244; 2.U.229.228; 2.U.229.229;
2.U.229.230; 2.U.229.231; 2.U.229.236; 2.U.229.237; 2.U.229.238; 2.U.229.239;
2.U.229.154; 2.U.229.157; 2.U.229.166; 2.U.229.169; 2.U.229.172; 2.U.229.175;
2.U.229.240; 2.U.229.244; 2.U.230.228; 2.U.230.229; 2.U.230.230; 2.U.230.231;
2.U.230.236; 2.U.230.237; 2.U.230.238; 2.U.230.239; 2.U.230.154; 2.U.230.157;
2.U.230.166; 2.U.230.169; 2.U.230.172; 2.U.230.175; 2.U.230.240; 2.U.230.244;
2.U.231.228; 2.U.231.229; 2.U.231.230; 2.U.231.231; 2.U.231.236; 2.U.231.237;
2.U.231.238; 2.U.231.239; 2.U.231.154; 2.U.231.157; 2.U.231.166; 2.U.231.169;
2.U.231.172; 2.U.231.175; 2.U.231.240; 2.U.231.244; 2.U.236.228; 2.U.236.229;
2.U.236.230; 2.U.236.231; 2.U.236.236; 2.U.236.237; 2.U.236.238; 2.U.236.239;
2.U.236.154; 2.U.236.157; 2.U.236.166; 2.U.236.169; 2.U.236.172; 2.U.236.175;
2.U.236.240; 2.U.236.244; 2.U.237.228; 2.U.237.229; 2.U.237.230; 2.U.237.231;
2.U.237.236; 2.U.237.237; 2.U.237.238; 2.U.237.239; 2.U.237.154; 2.U.237.157;
2.U.237.166; 2.U.237.169; 2.U.237.172; 2.U.237.175; 2.U.237.240; 2.U.237.244;
2.U.238.228; 2.U.238.229; 2.U.238.230; 2.U.238.231; 2.U.238.236; 2.U.238.237;
2.U.238.238; 2.U.238.239; 2.U.238.154; 2.U.238.157; 2.U.238.166; 2.U.238.169;
2.U.238.172; 2.U.238.175; 2.U.238.240; 2.U.238.244; 2.U.239.228; 2.U.239.229;
2.U.239.230; 2.U.239.231; 2.U.239.236; 2.U.239.237; 2.U.239.238; 2.U.239.239;
2.U.239.154; 2.U.239.157; 2.U.239.166; 2.U.239.169; 2.U.239.172; 2.U.239.175;
2.U.239.240; 2.U.239.244; 2.U.154.228; 2.U.154.229; 2.U.154.230; 2.U.154.231;
2.U.154.236; 2.U.154.237; 2.U.154.238; 2.U.154.239; 2.U.154.154; 2.U.154.157;
2.U.154.166; 2.U.154.169; 2.U.154.172; 2.U.154.175; 2.U.154.240; 2.U.154.244;
2.U.157.228; 2.U.157.229; 2.U.157.230; 2.U.157.231; 2.U.157.236; 2.U.157.237;
2.U.157.238; 2.U.157.239; 2.U.157.154; 2.U.157.157; 2.U.157.166; 2.U.157.169;
2.U.157.172; 2.U.157.175; 2.U.157.240; 2.U.157.244; 2.U.166.228; 2.U.166.229;
2.U.166.230; 2.U.166.231; 2.U.166.236; 2.U.166.237; 2.U.166.238; 2.U.166.239;
2.U.166.154; 2.U.166.157; 2.U.166.166; 2.U.166.169; 2.U.166.172; 2.U.166.175;
2.U.166.240; 2.U.166.244; 2.U.169.228; 2.U.169.229; 2.U.169.230; 2.U.169.231;
2.U.169.236; 2.U.169.237; 2.U.169.238; 2.U.169.239; 2.U.169.154; 2.U.169.157;
2.U.169.166; 2.U.169.169; 2.U.169.172; 2.U.169.175; 2.U.169.240; 2.U.169.244;
2.U.172.228; 2.U.172.229; 2.U.172.230; 2.U.172.231; 2.U.172.236; 2.U.172.237;
2.U.172.238; 2.U.172.239; 2.U.172.154; 2.U.172.157; 2.U.172.166; 2.U.172.169;
2.U.172.172; 2.U.172.175; 2.U.172.240; 2.U.172.244; 2.U.175.228; 2.U.175.229;
2.U.175.230; 2.U.175.231; 2.U.175.236; 2.U.175.237; 2.U.175.238; 2.U.175.239;
2.U.175.154; 2.U.175.157; 2.U.175.166; 2.U.175.169; 2.U.175.172; 2.U.175.175;
2.U.175.240; 2.U.175.244; 2.U.240.228; 2.U.240.229; 2.U.240.230; 2.U.240.231;
2.U.240.236; 2.U.240.237; 2.U.240.238; 2.U.240.239; 2.U.240.154; 2.U.240.157;
2.U.240.166; 2.U.240.169; 2.U.240.172; 2.U.240.175; 2.U.240.240; 2.U.240.244;
2.U.244.228; 2.U.244.229; 2.U.244.230; 2.U.244.231; 2.U.244.236; 2.U.244.237;

TABLE 100-continued

2.U.244.238; 2.U.244.239; 2.U.244.154; 2.U.244.157; 2.U.244.166; 2.U.244.169;
2.U.244.172; 2.U.244.175; 2.U.244.240; 2.U.244.244;

Prodrugs of 2.W

2.W.228.228; 2.W.228.229; 2.W.228.230; 2.W.228.231; 2.W.228.236; 2.W.228.237;
2.W.228.238; 2.W.228.239; 2.W.228.154; 2.W.228.157; 2.W.228.166; 2.W.228.169;
2.W.228.172; 2.W.228.175; 2.W.228.240; 2.W.228.244; 2.W.229.228; 2.W.229.229;
2.W.229.230; 2.W.229.231; 2.W.229.236; 2.W.229.237; 2.W.229.238; 2.W.229.239;
2.W.229.154; 2.W.229.157; 2.W.229.166; 2.W.229.169; 2.W.229.172; 2.W.229.175;
2.W.229.240; 2.W.229.244; 2.W.230.228; 2.W.230.229; 2.W.230.230; 2.W.230.231;
2.W.230.236; 2.W.230.237; 2.W.230.238; 2.W.230.239; 2.W.230.154; 2.W.230.157;
2.W.230.166; 2.W.230.169; 2.W.230.172; 2.W.230.175; 2.W.230.240; 2.W.230.244;
2.W.231.228; 2.W.231.229; 2.W.231.230; 2.W.231.231; 2.W.231.236; 2.W.231.237;
2.W.231.238; 2.W.231.239; 2.W.231.154; 2.W.231.157; 2.W.231.166; 2.W.231.169;
2.W.231.172; 2.W.231.175; 2.W.231.240; 2.W.231.244; 2.W.236.228; 2.W.236.229;
2.W.236.230; 2.W.236.231; 2.W.236.236; 2.W.236.237; 2.W.236.238; 2.W.236.239;
2.W.236.154; 2.W.236.157; 2.W.236.166; 2.W.236.169; 2.W.236.172; 2.W.236.175;
2.W.236.240; 2.W.236.244; 2.W.237.228; 2.W.237.229; 2.W.237.230; 2.W.237.231;
2.W.237.236; 2.W.237.237; 2.W.237.238; 2.W.237.239; 2.W.237.154; 2.W.237.157;
2.W.237.166; 2.W.237.169; 2.W.237.172; 2.W.237.175; 2.W.237.240; 2.W.237.244;
2.W.238.228; 2.W.238.229; 2.W.238.230; 2.W.238.231; 2.W.238.236; 2.W.238.237;
2.W.238.238; 2.W.238.239; 2.W.238.154; 2.W.238.157; 2.W.238.166; 2.W.238.169;
2.W.238.172; 2.W.238.175; 2.W.238.240; 2.W.238.244; 2.W.239.228; 2.W.239.229;
2.W.239.230; 2.W.239.231; 2.W.239.236; 2.W.239.237; 2.W.239.238; 2.W.239.239;
2.W.239.154; 2.W.239.157; 2.W.239.166; 2.W.239.169; 2.W.239.172; 2.W.239.175;
2.W.239.240; 2.W.239.244; 2.W.154.228; 2.W.154.229; 2.W.154.230; 2.W.154.231;
2.W.154.236; 2.W.154.237; 2.W.154.238; 2.W.154.239; 2.W.154.154; 2.W.154.157;
2.W.154.166; 2.W.154.169; 2.W.154.172; 2.W.154.175; 2.W.154.240; 2.W.154.244;
2.W.157.228; 2.W.157.229; 2.W.157.230; 2.W.157.231; 2.W.157.236; 2.W.157.237;
2.W.157.238; 2.W.157.239; 2.W.157.154; 2.W.157.157; 2.W.157.166; 2.W.157.169;
2.W.157.172; 2.W.157.175; 2.W.157.240; 2.W.157.244; 2.W.166.228; 2.W.166.229;
2.W.166.230; 2.W.166.231; 2.W.166.236; 2.W.166.237; 2.W.166.238; 2.W.166.239;
2.W.166.154; 2.W.166.157; 2.W.166.166; 2.W.166.169; 2.W.166.172; 2.W.166.175;
2.W.166.240; 2.W.166.244; 2.W.169.228; 2.W.169.229; 2.W.169.230; 2.W.169.231;
2.W.169.236; 2.W.169.237; 2.W.169.238; 2.W.169.239; 2.W.169.154; 2.W.169.157;
2.W.169.166; 2.W.169.169; 2.W.169.172; 2.W.169.175; 2.W.169.240; 2.W.169.244;
2.W.172.228; 2.W.172.229; 2.W.172.230; 2.W.172.231; 2.W.172.236; 2.W.172.237;
2.W.172.238; 2.W.172.239; 2.W.172.154; 2.W.172.157; 2.W.172.166; 2.W.172.169;
2.W.172.172; 2.W.172.175; 2.W.172.240; 2.W.172.244; 2.W.175.228; 2.W.175.229;
2.W.175.230; 2.W.175.231; 2.W.175.236; 2.W.175.237; 2.W.175.238; 2.W.175.239;
2.W.175.154; 2.W.175.157; 2.W.175.166; 2.W.175.169; 2.W.175.172; 2.W.175.175;
2.W.175.240; 2.W.175.244; 2.W.240.228; 2.W.240.229; 2.W.240.230; 2.W.240.231;
2.W.240.236; 2.W.240.237; 2.W.240.238; 2.W.240.239; 2.W.240.154; 2.W.240.157;
2.W.240.166; 2.W.240.169; 2.W.240.172; 2.W.240.175; 2.W.240.240; 2.W.240.244;
2.W.244.228; 2.W.244.229; 2.W.244.230; 2.W.244.231; 2.W.244.236; 2.W.244.237;
2.W.244.238; 2.W.244.239; 2.W.244.154; 2.W.244.157; 2.W.244.166; 2.W.244.169;
2.W.244.172; 2.W.244.175; 2.W.244.240; 2.W.244.244;

Prodrugs of 2.Y

2.Y.228.228; 2.Y.228.229; 2.Y.228.230; 2.Y.228.231; 2.Y.228.236; 2.Y.228.237;
2.Y.228.238; 2.Y.228.239; 2.Y.228.154; 2.Y.228.157; 2.Y.228.166; 2.Y.228.169;
2.Y.228.172; 2.Y.228.175; 2.Y.228.240; 2.Y.228.244; 2.Y.229.228; 2.Y.229.229;
2.Y.229.230; 2.Y.229.231; 2.Y.229.236; 2.Y.229.237; 2.Y.229.238; 2.Y.229.239;
2.Y.229.154; 2.Y.229.157; 2.Y.229.166; 2.Y.229.169; 2.Y.229.172; 2.Y.229.175;
2.Y.229.240; 2.Y.229.244; 2.Y.230.228; 2.Y.230.229; 2.Y.230.230; 2.Y.230.231;
2.Y.230.236; 2.Y.230.237; 2.Y.230.238; 2.Y.230.239; 2.Y.230.154; 2.Y.230.157;
2.Y.230.166; 2.Y.230.169; 2.Y.230.172; 2.Y.230.175; 2.Y.230.240; 2.Y.230.244;
2.Y.231.228; 2.Y.231.229; 2.Y.231.230; 2.Y.231.231; 2.Y.231.236; 2.Y.231.237;
2.Y.231.238; 2.Y.231.239; 2.Y.231.154; 2.Y.231.157; 2.Y.231.166; 2.Y.231.169;
2.Y.231.172; 2.Y.231.175; 2.Y.231.240; 2.Y.231.244; 2.Y.236.228; 2.Y.236.229;
2.Y.236.230; 2.Y.236.231; 2.Y.236.236; 2.Y.236.237; 2.Y.236.238; 2.Y.236.239;
2.Y.236.154; 2.Y.236.157; 2.Y.236.166; 2.Y.236.169; 2.Y.236.172; 2.Y.236.175;
2.Y.236.240; 2.Y.236.244; 2.Y.237.228; 2.Y.237.229; 2.Y.237.230; 2.Y.237.231;
2.Y.237.236; 2.Y.237.237; 2.Y.237.238; 2.Y.237.239; 2.Y.237.154; 2.Y.237.157;
2.Y.237.166; 2.Y.237.169; 2.Y.237.172; 2.Y.237.175; 2.Y.237.240; 2.Y.237.244;
2.Y.238.228; 2.Y.238.229; 2.Y.238.230; 2.Y.238.231; 2.Y.238.236; 2.Y.238.237;
2.Y.238.238; 2.Y.238.239; 2.Y.238.154; 2.Y.238.157; 2.Y.238.166; 2.Y.238.169;
2.Y.238.172; 2.Y.238.175; 2.Y.238.240; 2.Y.238.244; 2.Y.239.228; 2.Y.239.229;
2.Y.239.230; 2.Y.239.231; 2.Y.239.236; 2.Y.239.237; 2.Y.239.238; 2.Y.239.239;
2.Y.239.154; 2.Y.239.157; 2.Y.239.166; 2.Y.239.169; 2.Y.239.172; 2.Y.239.175;
2.Y.239.240; 2.Y.239.244; 2.Y.154.228; 2.Y.154.229; 2.Y.154.230; 2.Y.154.231;
2.Y.154.236; 2.Y.154.237; 2.Y.154.238; 2.Y.154.239; 2.Y.154.154; 2.Y.154.157;
2.Y.154.166; 2.Y.154.169; 2.Y.154.172; 2.Y.154.175; 2.Y.154.240; 2.Y.154.244;
2.Y.157.228; 2.Y.157.229; 2.Y.157.230; 2.Y.157.231; 2.Y.157.236; 2.Y.157.237;
2.Y.157.238; 2.Y.157.239; 2.Y.157.154; 2.Y.157.157; 2.Y.157.166; 2.Y.157.169;
2.Y.157.172; 2.Y.157.175; 2.Y.157.240; 2.Y.157.244; 2.Y.166.228; 2.Y.166.229;
2.Y.166.230; 2.Y.166.231; 2.Y.166.236; 2.Y.166.237; 2.Y.166.238; 2.Y.166.239;
2.Y.166.154; 2.Y.166.157; 2.Y.166.166; 2.Y.166.169; 2.Y.166.172; 2.Y.166.175;
2.Y.166.240; 2.Y.166.244; 2.Y.169.228; 2.Y.169.229; 2.Y.169.230; 2.Y.169.231;

TABLE 100-continued

2.Y.169.236; 2.Y.169.237; 2.Y.169.238; 2.Y.169.239; 2.Y.169.154; 2.Y.169.157; 2.Y.169.166; 2.Y.169.169; 2.Y.169.172; 2.Y.169.175; 2.Y.169.240; 2.Y.169.244; 2.Y.172.228; 2.Y.172.229; 2.Y.172.230; 2.Y.172.231; 2.Y.172.236; 2.Y.172.237; 2.Y.172.238; 2.Y.172.239; 2.Y.172.154; 2.Y.172.157; 2.Y.172.166; 2.Y.172.169; 2.Y.172.172; 2.Y.172.175; 2.Y.172.240; 2.Y.172.244; 2.Y.175.228; 2.Y.175.229; 2.Y.175.230; 2.Y.175.231; 2.Y.175.236; 2.Y.175.237; 2.Y.175.238; 2.Y.175.239; 2.Y.175.154; 2.Y.175.157; 2.Y.175.166; 2.Y.175.169; 2.Y.175.172; 2.Y.175.175; 2.Y.175.240; 2.Y.175.244; 2.Y.240.228; 2.Y.240.229; 2.Y.240.230; 2.Y.240.231; 2.Y.240.236; 2.Y.240.237; 2.Y.240.238; 2.Y.240.239; 2.Y.240.154; 2.Y.240.157; 2.Y.240.166; 2.Y.240.169; 2.Y.240.172; 2.Y.240.175; 2.Y.240.240; 2.Y.240.244; 2.Y.244.228; 2.Y.244.229; 2.Y.244.230; 2.Y.244.231; 2.Y.244.236; 2.Y.244.237; 2.Y.244.238; 2.Y.244.239; 2.Y.244.154; 2.Y.244.157; 2.Y.244.166; 2.Y.244.169; 2.Y.244.172; 2.Y.244.175; 2.Y.244.240; 2.Y.244.244;

Prodrugs of 3.B

3.B.228.228; 3.B.228.229; 3.B.228.230; 3.B.228.231; 3.B.228.236; 3.B.228.237; 3.B.228.238; 3.B.228.239; 3.B.228.154; 3.B.228.157; 3.B.228.166; 3.B.228.169; 3.B.228.172; 3.B.228.175; 3.B.228.240; 3.B.228.244; 3.B.229.228; 3.B.229.229; 3.B.229.230; 3.B.229.231; 3.B.229.236; 3.B.229.237; 3.B.229.238; 3.B.229.239; 3.B.229.154; 3.B.229.157; 3.B.229.166; 3.B.229.169; 3.B.229.172; 3.B.229.175; 3.B.229.240; 3.B.229.244; 3.B.230.228; 3.B.230.229; 3.B.230.230; 3.B.230.231; 3.B.230.236; 3.B.230.237; 3.B.230.238; 3.B.230.239; 3.B.230.154; 3.B.230.157; 3.B.230.166; 3.B.230.169; 3.B.230.172; 3.B.230.175; 3.B.230.240; 3.B.230.244; 3.B.231.228; 3.B.231.229; 3.B.231.230; 3.B.231.231; 3.B.231.236; 3.B.231.237; 3.B.231.238; 3.B.231.239; 3.B.231.154; 3.B.231.157; 3.B.231.166; 3.B.231.169; 3.B.231.172; 3.B.231.175; 3.B.231.240; 3.B.231.244; 3.B.236.228; 3.B.236.229; 3.B.236.230; 3.B.236.231; 3.B.236.236; 3.B.236.237; 3.B.236.238; 3.B.236.239; 3.B.236.154; 3.B.236.157; 3.B.236.166; 3.B.236.169; 3.B.236.172; 3.B.236.175; 3.B.236.240; 3.B.236.244; 3.B.237.228; 3.B.237.229; 3.B.237.230; 3.B.237.231; 3.B.237.236; 3.B.237.237; 3.B.237.238; 3.B.237.239; 3.B.237.154; 3.B.237.157; 3.B.237.166; 3.B.237.169; 3.B.237.172; 3.B.237.175; 3.B.237.240; 3.B.237.244; 3.B.238.228; 3.B.238.229; 3.B.238.230; 3.B.238.231; 3.B.238.236; 3.B.238.237; 3.B.238.238; 3.B.238.239; 3.B.238.154; 3.B.238.157; 3.B.238.166; 3.B.238.169; 3.B.238.172; 3.B.238.175; 3.B.238.240; 3.B.238.244; 3.B.239.228; 3.B.239.229; 3.B.239.230; 3.B.239.231; 3.B.239.236; 3.B.239.237; 3.B.239.238; 3.B.239.239; 3.B.239.154; 3.B.239.157; 3.B.239.166; 3.B.239.169; 3.B.239.172; 3.B.239.175; 3.B.239.240; 3.B.239.244; 3.B.154.228; 3.B.154.229; 3.B.154.230; 3.B.154.231; 3.B.154.236; 3.B.154.237; 3.B.154.238; 3.B.154.239; 3.B.154.154; 3.B.154.157; 3.B.154.166; 3.B.154.169; 3.B.154.172; 3.B.154.175; 3.B.154.240; 3.B.154.244; 3.B.157.228; 3.B.157.229; 3.B.157.230; 3.B.157.231; 3.B.157.236; 3.B.157.237; 3.B.157.238; 3.B.157.239; 3.B.157.154; 3.B.157.157; 3.B.157.166; 3.B.157.169; 3.B.157.172; 3.B.157.175; 3.B.157.240; 3.B.157.244; 3.B.166.228; 3.B.166.229; 3.B.166.230; 3.B.166.231; 3.B.166.236; 3.B.166.237; 3.B.166.238; 3.B.166.239; 3.B.166.154; 3.B.166.157; 3.B.166.166; 3.B.166.169; 3.B.166.172; 3.B.166.175; 3.B.166.240; 3.B.166.244; 3.B.169.228; 3.B.169.229; 3.B.169.230; 3.B.169.231; 3.B.169.236; 3.B.169.237; 3.B.169.238; 3.B.169.239; 3.B.169.154; 3.B.169.157; 3.B.169.166; 3.B.169.169; 3.B.169.172; 3.B.169.175; 3.B.169.240; 3.B.169.244; 3.B.172.228; 3.B.172.229; 3.B.172.230; 3.B.172.231; 3.B.172.236; 3.B.172.237; 3.B.172.238; 3.B.172.239; 3.B.172.154; 3.B.172.157; 3.B.172.166; 3.B.172.169; 3.B.172.172; 3.B.172.175; 3.B.172.240; 3.B.172.244; 3.B.175.228; 3.B.175.229; 3.B.175.230; 3.B.175.231; 3.B.175.236; 3.B.175.237; 3.B.175.238; 3.B.175.239; 3.B.175.154; 3.B.175.157; 3.B.175.166; 3.B.175.169; 3.B.175.172; 3.B.175.175; 3.B.175.240; 3.B.175.244; 3.B.240.228; 3.B.240.229; 3.B.240.230; 3.B.240.231; 3.B.240.236; 3.B.240.237; 3.B.240.238; 3.B.240.239; 3.B.240.154; 3.B.240.157; 3.B.240.166; 3.B.240.169; 3.B.240.172; 3.B.240.175; 3.B.240.240; 3.B.240.244; 3.B.244.228; 3.B.244.229; 3.B.244.230; 3.B.244.231; 3.B.244.236; 3.B.244.237; 3.B.244.238; 3.B.244.239; 3.B.244.154; 3.B.244.157; 3.B.244.166; 3.B.244.169; 3.B.244.172; 3.B.244.175; 3.B.244.240; 3.B.244.244;

Prodrugs of 3.D

3.D.228.228; 3.D.228.229; 3.D.228.230; 3.D.228.231; 3.D.228.236; 3.D.228.237; 3.D.228.238; 3.D.228.239; 3.D.228.154; 3.D.228.157; 3.D.228.166; 3.D.228.169; 3.D.228.172; 3.D.228.175; 3.D.228.240; 3.D.228.244; 3.D.229.228; 3.D.229.229; 3.D.229.230; 3.D.229.231; 3.D.229.236; 3.D.229.237; 3.D.229.238; 3.D.229.239; 3.D.229.154; 3.D.229.157; 3.D.229.166; 3.D.229.169; 3.D.229.172; 3.D.229.175; 3.D.229.240; 3.D.229.244; 3.D.230.228; 3.D.230.229; 3.D.230.230; 3.D.230.231; 3.D.230.236; 3.D.230.237; 3.D.230.238; 3.D.230.239; 3.D.230.154; 3.D.230.157; 3.D.230.166; 3.D.230.169; 3.D.230.172; 3.D.230.175; 3.D.230.240; 3.D.230.244; 3.D.231.228; 3.D.231.229; 3.D.231.230; 3.D.231.231; 3.D.231.236; 3.D.231.237; 3.D.231.238; 3.D.231.239; 3.D.231.154; 3.D.231.157; 3.D.231.166; 3.D.231.169; 3.D.231.172; 3.D.231.175; 3.D.231.240; 3.D.231.244; 3.D.236.228; 3.D.236.229; 3.D.236.230; 3.D.236.231; 3.D.236.236; 3.D.236.237; 3.D.236.238; 3.D.236.239; 3.D.236.154; 3.D.236.157; 3.D.236.166; 3.D.236.169; 3.D.236.172; 3.D.236.175; 3.D.236.240; 3.D.236.244; 3.D.237.228; 3.D.237.229; 3.D.237.230; 3.D.237.231; 3.D.237.236; 3.D.237.237; 3.D.237.238; 3.D.237.239; 3.D.237.154; 3.D.237.157; 3.D.237.166; 3.D.237.169; 3.D.237.172; 3.D.237.175; 3.D.237.240; 3.D.237.244; 3.D.238.228; 3.D.238.229; 3.D.238.230; 3.D.238.231; 3.D.238.236; 3.D.238.237; 3.D.238.238; 3.D.238.239; 3.D.238.154; 3.D.238.157; 3.D.238.166; 3.D.238.169; 3.D.238.172; 3.D.238.175; 3.D.238.240; 3.D.238.244; 3.D.239.228; 3.D.239.229; 3.D.239.230; 3.D.239.231; 3.D.239.236; 3.D.239.237; 3.D.239.238; 3.D.239.239; 3.D.239.154; 3.D.239.157; 3.D.239.166; 3.D.239.169; 3.D.239.172; 3.D.239.175; 3.D.239.240; 3.D.239.244; 3.D.154.228; 3.D.154.229; 3.D.154.230; 3.D.154.231; 3.D.154.236; 3.D.154.237; 3.D.154.238; 3.D.154.239; 3.D.154.154; 3.D.154.157; 3.D.154.166; 3.D.154.169; 3.D.154.172; 3.D.154.175; 3.D.154.240; 3.D.154.244; 3.D.157.228; 3.D.157.229; 3.D.157.230; 3.D.157.231; 3.D.157.236; 3.D.157.237;

TABLE 100-continued

| |
|---|
| 3.D.157.238; 3.D.157.239; 3.D.157.154; 3.D.157.157; 3.D.157.166; 3.D.157.169; 3.D.157.172; 3.D.157.175; 3.D.157.240; 3.D.157.244; 3.D.166.228; 3.D.166.229; 3.D.166.230; 3.D.166.231; 3.D.166.236; 3.D.166.237; 3.D.166.238; 3.D.166.239; 3.D.166.154; 3.D.166.157; 3.D.166.166; 3.D.166.169; 3.D.166.172; 3.D.166.175; 3.D.166.240; 3.D.166.244; 3.D.169.228; 3.D.169.229; 3.D.169.230; 3.D.169.231; 3.D.169.236; 3.D.169.237; 3.D.169.238; 3.D.169.239; 3.D.169.154; 3.D.169.157; 3.D.169.166; 3.D.169.169; 3.D.169.172; 3.D.169.175; 3.D.169.240; 3.D.169.244; 3.D.172.228; 3.D.172.229; 3.D.172.230; 3.D.172.231; 3.D.172.236; 3.D.172.237; 3.D.172.238; 3.D.172.239; 3.D.172.154; 3.D.172.157; 3.D.172.166; 3.D.172.169; 3.D.172.172; 3.D.172.175; 3.D.172.240; 3.D.172.244; 3.D.175.228; 3.D.175.229; 3.D.175.230; 3.D.175.231; 3.D.175.236; 3.D.175.237; 3.D.175.238; 3.D.175.239; 3.D.175.154; 3.D.175.157; 3.D.175.166; 3.D.175.169; 3.D.175.172; 3.D.175.175; 3.D.175.240; 3.D.175.244; 3.D.240.228; 3.D.240.229; 3.D.240.230; 3.D.240.231; 3.D.240.236; 3.D.240.237; 3.D.240.238; 3.D.240.239; 3.D.240.154; 3.D.240.157; 3.D.240.166; 3.D.240.169; 3.D.240.172; 3.D.240.175; 3.D.240.240; 3.D.240.244; 3.D.244.228; 3.D.244.229; 3.D.244.230; 3.D.244.231; 3.D.244.236; 3.D.244.237; 3.D.244.238; 3.D.244.239; 3.D.244.154; 3.D.244.157; 3.D.244.166; 3.D.244.169; 3.D.244.172; 3.D.244.175; 3.D.244.240; 3.D.244.244; |
| Prodrugs of 3.E |
| 3.E.228.228; 3.E.228.229; 3.E.228.230; 3.E.228.231; 3.E.228.236; 3.E.228.237; 3.E.228.238; 3.E.228.239; 3.E.228.154; 3.E.228.157; 3.E.228.166; 3.E.228.169; 3.E.228.172; 3.E.228.175; 3.E.228.240; 3.E.228.244; 3.E.229.228; 3.E.229.229; 3.E.229.230; 3.E.229.231; 3.E.229.236; 3.E.229.237; 3.E.229.238; 3.E.229.239; 3.E.229.154; 3.E.229.157; 3.E.229.166; 3.E.229.169; 3.E.229.172; 3.E.229.175; 3.E.229.240; 3.E.229.244; 3.E.230.228; 3.E.230.229; 3.E.230.230; 3.E.230.231; 3.E.230.236; 3.E.230.237; 3.E.230.238; 3.E.230.239; 3.E.230.154; 3.E.230.157; 3.E.230.166; 3.E.230.169; 3.E.230.172; 3.E.230.175; 3.E.230.240; 3.E.230.244; 3.E.231.228; 3.E.231.229; 3.E.231.230; 3.E.231.231; 3.E.231.236; 3.E.231.237; 3.E.231.238; 3.E.231.239; 3.E.231.154; 3.E.231.157; 3.E.231.166; 3.E.231.169; 3.E.231.172; 3.E.231.175; 3.E.231.240; 3.E.231.244; 3.E.236.228; 3.E.236.229; 3.E.236.230; 3.E.236.231; 3.E.236.236; 3.E.236.237; 3.E.236.238; 3.E.236.239; 3.E.236.154; 3.E.236.157; 3.E.236.166; 3.E.236.169; 3.E.236.172; 3.E.236.175; 3.E.236.240; 3.E.236.244; 3.E.237.228; 3.E.237.229; 3.E.237.230; 3.E.237.231; 3.E.237.236; 3.E.237.237; 3.E.237.238; 3.E.237.239; 3.E.237.154; 3.E.237.157; 3.E.237.166; 3.E.237.169; 3.E.237.172; 3.E.237.175; 3.E.237.240; 3.E.237.244; 3.E.238.228; 3.E.238.229; 3.E.238.230; 3.E.238.231; 3.E.238.236; 3.E.238.237; 3.E.238.238; 3.E.238.239; 3.E.238.154; 3.E.238.157; 3.E.238.166; 3.E.238.169; 3.E.238.172; 3.E.238.175; 3.E.238.240; 3.E.238.244; 3.E.239.228; 3.E.239.229; 3.E.239.230; 3.E.239.231; 3.E.239.236; 3.E.239.237; 3.E.239.238; 3.E.239.239; 3.E.239.154; 3.E.239.157; 3.E.239.166; 3.E.239.169; 3.E.239.172; 3.E.239.175; 3.E.239.240; 3.E.239.244; 3.E.154.228; 3.E.154.229; 3.E.154.230; 3.E.154.231; 3.E.154.236; 3.E.154.237; 3.E.154.238; 3.E.154.239; 3.E.154.154; 3.E.154.157; 3.E.154.166; 3.E.154.169; 3.E.154.172; 3.E.154.175; 3.E.154.240; 3.E.154.244; 3.E.157.228; 3.E.157.229; 3.E.157.230; 3.E.157.231; 3.E.157.236; 3.E.157.237; 3.E.157.238; 3.E.157.239; 3.E.157.154; 3.E.157.157; 3.E.157.166; 3.E.157.169; 3.E.157.172; 3.E.157.175; 3.E.157.240; 3.E.157.244; 3.E.166.228; 3.E.166.229; 3.E.166.230; 3.E.166.231; 3.E.166.236; 3.E.166.237; 3.E.166.238; 3.E.166.239; 3.E.166.154; 3.E.166.157; 3.E.166.166; 3.E.166.169; 3.E.166.172; 3.E.166.175; 3.E.166.240; 3.E.166.244; 3.E.169.228; 3.E.169.229; 3.E.169.230; 3.E.169.231; 3.E.169.236; 3.E.169.237; 3.E.169.238; 3.E.169.239; 3.E.169.154; 3.E.169.157; 3.E.169.166; 3.E.169.169; 3.E.169.172; 3.E.169.175; 3.E.169.240; 3.E.169.244; 3.E.172.228; 3.E.172.229; 3.E.172.230; 3.E.172.231; 3.E.172.236; 3.E.172.237; 3.E.172.238; 3.E.172.239; 3.E.172.154; 3.E.172.157; 3.E.172.166; 3.E.172.169; 3.E.172.172; 3.E.172.175; 3.E.172.240; 3.E.172.244; 3.E.175.228; 3.E.175.229; 3.E.175.230; 3.E.175.231; 3.E.175.236; 3.E.175.237; 3.E.175.238; 3.E.175.239; 3.E.175.154; 3.E.175.157; 3.E.175.166; 3.E.175.169; 3.E.175.172; 3.E.175.175; 3.E.175.240; 3.E.175.244; 3.E.240.228; 3.E.240.229; 3.E.240.230; 3.E.240.231; 3.E.240.236; 3.E.240.237; 3.E.240.238; 3.E.240.239; 3.E.240.154; 3.E.240.157; 3.E.240.166; 3.E.240.169; 3.E.240.172; 3.E.240.175; 3.E.240.240; 3.E.240.244; 3.E.244.228; 3.E.244.229; 3.E.244.230; 3.E.244.231; 3.E.244.236; 3.E.244.237; 3.E.244.238; 3.E.244.239; 3.E.244.154; 3.E.244.157; 3.E.244.166; 3.E.244.169; 3.E.244.172; 3.E.244.175; 3.E.244.240; 3.E.244.244; |
| Prodrugs of 3.G |
| 3.G.228.228; 3.G.228.229; 3.G.228.230; 3.G.228.231; 3.G.228.236; 3.G.228.237; 3.G.228.238; 3.G.228.239; 3.G.228.154; 3.G.228.157; 3.G.228.166; 3.G.228.169; 3.G.228.172; 3.G.228.175; 3.G.228.240; 3.G.228.244; 3.G.229.228; 3.G.229.229; 3.G.229.230; 3.G.229.231; 3.G.229.236; 3.G.229.237; 3.G.229.238; 3.G.229.239; 3.G.229.154; 3.G.229.157; 3.G.229.166; 3.G.229.169; 3.G.229.172; 3.G.229.175; 3.G.229.240; 3.G.229.244; 3.G.230.228; 3.G.230.229; 3.G.230.230; 3.G.230.231; 3.G.230.236; 3.G.230.237; 3.G.230.238; 3.G.230.239; 3.G.230.154; 3.G.230.157; 3.G.230.166; 3.G.230.169; 3.G.230.172; 3.G.230.175; 3.G.230.240; 3.G.230.244; 3.G.231.228; 3.G.231.229; 3.G.231.230; 3.G.231.231; 3.G.231.236; 3.G.231.237; 3.G.231.238; 3.G.231.239; 3.G.231.154; 3.G.231.157; 3.G.231.166; 3.G.231.169; 3.G.231.172; 3.G.231.175; 3.G.231.240; 3.G.231.244; 3.G.236.228; 3.G.236.229; 3.G.236.230; 3.G.236.231; 3.G.236.236; 3.G.236.237; 3.G.236.238; 3.G.236.239; 3.G.236.154; 3.G.236.157; 3.G.236.166; 3.G.236.169; 3.G.236.172; 3.G.236.175; 3.G.236.240; 3.G.236.244; 3.G.237.228; 3.G.237.229; 3.G.237.230; 3.G.237.231; 3.G.237.236; 3.G.237.237; 3.G.237.238; 3.G.237.239; 3.G.237.154; 3.G.237.157; 3.G.237.166; 3.G.237.169; 3.G.237.172; 3.G.237.175; 3.G.237.240; 3.G.237.244; 3.G.238.228; 3.G.238.229; 3.G.238.230; 3.G.238.231; 3.G.238.236; 3.G.238.237; 3.G.238.238; 3.G.238.239; 3.G.238.154; 3.G.238.157; 3.G.238.166; 3.G.238.169; 3.G.238.172; 3.G.238.175; 3.G.238.240; 3.G.238.244; 3.G.239.228; 3.G.239.229; 3.G.239.230; 3.G.239.231; 3.G.239.236; 3.G.239.237; 3.G.239.238; 3.G.239.239; |

TABLE 100-continued

3.G.239.154; 3.G.239.157; 3.G.239.166; 3.G.239.169; 3.G.239.172; 3.G.239.175; 3.G.239.240; 3.G.239.244; 3.G.154.228; 3.G.154.229; 3.G.154.230; 3.G.154.231; 3.G.154.236; 3.G.154.237; 3.G.154.238; 3.G.154.239; 3.G.154.154; 3.G.154.157; 3.G.154.166; 3.G.154.169; 3.G.154.172; 3.G.154.175; 3.G.154.240; 3.G.154.244; 3.G.157.228; 3.G.157.229; 3.G.157.230; 3.G.157.231; 3.G.157.236; 3.G.157.237; 3.G.157.238; 3.G.157.239; 3.G.157.154; 3.G.157.157; 3.G.157.166; 3.G.157.169; 3.G.157.172; 3.G.157.175; 3.G.157.240; 3.G.157.244; 3.G.166.228; 3.G.166.229; 3.G.166.230; 3.G.166.231; 3.G.166.236; 3.G.166.237; 3.G.166.238; 3.G.166.239; 3.G.166.154; 3.G.166.157; 3.G.166.166; 3.G.166.169; 3.G.166.172; 3.G.166.175; 3.G.166.240; 3.G.166.244; 3.G.169.228; 3.G.169.229; 3.G.169.230; 3.G.169.231; 3.G.169.236; 3.G.169.237; 3.G.169.238; 3.G.169.239; 3.G.169.154; 3.G.169.157; 3.G.169.166; 3.G.169.169; 3.G.169.172; 3.G.169.175; 3.G.169.240; 3.G.169.244; 3.G.172.228; 3.G.172.229; 3.G.172.230; 3.G.172.231; 3.G.172.236; 3.G.172.237; 3.G.172.238; 3.G.172.239; 3.G.172.154; 3.G.172.157; 3.G.172.166; 3.G.172.169; 3.G.172.172; 3.G.172.175; 3.G.172.240; 3.G.172.244; 3.G.175.228; 3.G.175.229; 3.G.175.230; 3.G.175.231; 3.G.175.236; 3.G.175.237; 3.G.175.238; 3.G.175.239; 3.G.175.154; 3.G.175.157; 3.G.175.166; 3.G.175.169; 3.G.175.172; 3.G.175.175; 3.G.175.240; 3.G.175.244; 3.G.240.228; 3.G.240.229; 3.G.240.230; 3.G.240.231; 3.G.240.236; 3.G.240.237; 3.G.240.238; 3.G.240.239; 3.G.240.154; 3.G.240.157; 3.G.240.166; 3.G.240.169; 3.G.240.172; 3.G.240.175; 3.G.240.240; 3.G.240.244; 3.G.244.228; 3.G.244.229; 3.G.244.230; 3.G.244.231; 3.G.244.236; 3.G.244.237; 3.G.244.238; 3.G.244.239; 3.G.244.154; 3.G.244.157; 3.G.244.166; 3.G.244.169; 3.G.244.172; 3.G.244.175; 3.G.244.240; 3.G.244.244;

Prodrugs of 3.I

3.I.228.228; 3.I.228.229; 3.I.228.230; 3.I.228.231; 3.I.228.236; 3.I.228.237; 3.I.228.238; 3.I.228.239; 3.I.228.154; 3.I.228.157; 3.I.228.166; 3.I.228.169; 3.I.228.172; 3.I.228.175; 3.I.228.240; 3.I.228.244; 3.I.229.228; 3.I.229.229; 3.I.229.230; 3.I.229.231; 3.I.229.236; 3.I.229.237; 3.I.229.238; 3.I.229.239; 3.I.229.154; 3.I.229.157; 3.I.229.166; 3.I.229.169; 3.I.229.172; 3.I.229.175; 3.I.229.240; 3.I.229.244; 3.I.230.228; 3.I.230.229; 3.I.230.230; 3.I.230.231; 3.I.230.236; 3.I.230.237; 3.I.230.238; 3.I.230.239; 3.I.230.154; 3.I.230.157; 3.I.230.166; 3.I.230.169; 3.I.230.172; 3.I.230.175; 3.I.230.240; 3.I.230.244; 3.I.231.228; 3.I.231.229; 3.I.231.230; 3.I.231.231; 3.I.231.236; 3.I.231.237; 3.I.231.238; 3.I.231.239; 3.I.231.154; 3.I.231.157; 3.I.231.166; 3.I.231.169; 3.I.231.172; 3.I.231.175; 3.I.231.240; 3.I.231.244; 3.I.236.228; 3.I.236.229; 3.I.236.230; 3.I.236.231; 3.I.236.236; 3.I.236.237; 3.I.236.238; 3.I.236.239; 3.I.236.154; 3.I.236.157; 3.I.236.166; 3.I.236.169; 3.I.236.172; 3.I.236.175; 3.I.236.240; 3.I.236.244; 3.I.237.228; 3.I.237.229; 3.I.237.230; 3.I.237.231; 3.I.237.236; 3.I.237.237; 3.I.237.238; 3.I.237.239; 3.I.237.154; 3.I.237.157; 3.I.237.166; 3.I.237.169; 3.I.237.172; 3.I.237.175; 3.I.237.240; 3.I.237.244; 3.I.238.228; 3.I.238.229; 3.I.238.230; 3.I.238.231; 3.I.238.236; 3.I.238.237; 3.I.238.238; 3.I.238.239; 3.I.238.154; 3.I.238.157; 3.I.238.166; 3.I.238.169; 3.I.238.172; 3.I.238.175; 3.I.238.240; 3.I.238.244; 3.I.239.228; 3.I.239.229; 3.I.239.230; 3.I.239.231; 3.I.239.236; 3.I.239.237; 3.I.239.238; 3.I.239.239; 3.I.239.154; 3.I.239.157; 3.I.239.166; 3.I.239.169; 3.I.239.172; 3.I.239.175; 3.I.239.240; 3.I.239.244; 3.I.154.228; 3.I.154.229; 3.I.154.230; 3.I.154.231; 3.I.154.236; 3.I.154.237; 3.I.154.238; 3.I.154.239; 3.I.154.154; 3.I.154.157; 3.I.154.166; 3.I.154.169; 3.I.154.172; 3.I.154.175; 3.I.154.240; 3.I.154.244; 3.I.157.228; 3.I.157.229; 3.I.157.230; 3.I.157.231; 3.I.157.236; 3.I.157.237; 3.I.157.238; 3.I.157.239; 3.I.157.154; 3.I.157.157; 3.I.157.166; 3.I.157.169; 3.I.157.172; 3.I.157.175; 3.I.157.240; 3.I.157.244; 3.I.166.228; 3.I.166.229; 3.I.166.230; 3.I.166.231; 3.I.166.236; 3.I.166.237; 3.I.166.238; 3.I.166.239; 3.I.166.154; 3.I.166.157; 3.I.166.166; 3.I.166.169; 3.I.166.172; 3.I.166.175; 3.I.166.240; 3.I.166.244; 3.I.169.228; 3.I.169.229; 3.I.169.230; 3.I.169.231; 3.I.169.236; 3.I.169.237; 3.I.169.238; 3.I.169.239; 3.I.169.154; 3.I.169.157; 3.I.169.166; 3.I.169.169; 3.I.169.172; 3.I.169.175; 3.I.169.240; 3.I.169.244; 3.I.172.228; 3.I.172.229; 3.I.172.230; 3.I.172.231; 3.I.172.236; 3.I.172.237; 3.I.172.238; 3.I.172.239; 3.I.172.154; 3.I.172.157; 3.I.172.166; 3.I.172.169; 3.I.172.172; 3.I.172.175; 3.I.172.240; 3.I.172.244; 3.I.175.228; 3.I.175.229; 3.I.175.230; 3.I.175.231; 3.I.175.236; 3.I.175.237; 3.I.175.238; 3.I.175.239; 3.I.175.154; 3.I.175.157; 3.I.175.166; 3.I.175.169; 3.I.175.172; 3.I.175.175; 3.I.175.240; 3.I.175.244; 3.I.240.228; 3.I.240.229; 3.I.240.230; 3.I.240.231; 3.I.240.236; 3.I.240.237; 3.I.240.238; 3.I.240.239; 3.I.240.154; 3.I.240.157; 3.I.240.166; 3.I.240.169; 3.I.240.172; 3.I.240.175; 3.I.240.240; 3.I.240.244; 3.I.244.228; 3.I.244.229; 3.I.244.230; 3.I.244.231; 3.I.244.236; 3.I.244.237; 3.I.244.238; 3.I.244.239; 3.I.244.154; 3.I.244.157; 3.I.244.166; 3.I.244.169; 3.I.244.172; 3.I.244.175; 3.I.244.240; 3.I.244.244;

Prodrugs of 3.J

3.J.228.228; 3.J.228.229; 3.J.228.230; 3.J.228.231; 3.J.228.236; 3.J.228.237; 3.J.228.238; 3.J.228.239; 3.J.228.154; 3.J.228.157; 3.J.228.166; 3.J.228.169; 3.J.228.172; 3.J.228.175; 3.J.228.240; 3.J.228.244; 3.J.229.228; 3.J.229.229; 3.J.229.230; 3.J.229.231; 3.J.229.236; 3.J.229.237; 3.J.229.238; 3.J.229.239; 3.J.229.154; 3.J.229.157; 3.J.229.166; 3.J.229.169; 3.J.229.172; 3.J.229.175; 3.J.229.240; 3.J.229.244; 3.J.230.228; 3.J.230.229; 3.J.230.230; 3.J.230.231; 3.J.230.236; 3.J.230.237; 3.J.230.238; 3.J.230.239; 3.J.230.154; 3.J.230.157; 3.J.230.166; 3.J.230.169; 3.J.230.172; 3.J.230.175; 3.J.230.240; 3.J.230.244; 3.J.231.228; 3.J.231.229; 3.J.231.230; 3.J.231.231; 3.J.231.236; 3.J.231.237; 3.J.231.238; 3.J.231.239; 3.J.231.154; 3.J.231.157; 3.J.231.166; 3.J.231.169; 3.J.231.172; 3.J.231.175; 3.J.231.240; 3.J.231.244; 3.J.236.228; 3.J.236.229; 3.J.236.230; 3.J.236.231; 3.J.236.236; 3.J.236.237; 3.J.236.238; 3.J.236.239; 3.J.236.154; 3.J.236.157; 3.J.236.166; 3.J.236.169; 3.J.236.172; 3.J.236.175; 3.J.236.240; 3.J.236.244; 3.J.237.228; 3.J.237.229; 3.J.237.230; 3.J.237.231; 3.J.237.236; 3.J.237.237; 3.J.237.238; 3.J.237.239; 3.J.237.154; 3.J.237.157; 3.J.237.166; 3.J.237.169; 3.J.237.172; 3.J.237.175; 3.J.237.240; 3.J.237.244; 3.J.238.228; 3.J.238.229; 3.J.238.230; 3.J.238.231; 3.J.238.236; 3.J.238.237; 3.J.238.238; 3.J.238.239; 3.J.238.154;

TABLE 100-continued

3.J.238.157; 3.J.238.166; 3.J.238.169; 3.J.238.172; 3.J.238.175; 3.J.238.240; 3.J.238.244;
3.J.239.228; 3.J.239.229; 3.J.239.230; 3.J.239.231; 3.J.239.236; 3.J.239.237; 3.J.239.238;
3.J.239.239; 3.J.239.154; 3.J.239.157; 3.J.239.166; 3.J.239.169; 3.J.239.172; 3.J.239.175;
3.J.239.240; 3.J.239.244; 3.J.154.228; 3.J.154.229; 3.J.154.230; 3.J.154.231; 3.J.154.236;
3.J.154.237; 3.J.154.238; 3.J.154.239; 3.J.154.154; 3.J.154.157; 3.J.154.166; 3.J.154.169;
3.J.154.172; 3.J.154.175; 3.J.154.240; 3.J.154.244; 3.J.157.228; 3.J.157.229; 3.J.157.230;
3.J.157.231; 3.J.157.236; 3.J.157.237; 3.J.157.238; 3.J.157.239; 3.J.157.154; 3.J.157.157;
3.J.157.166; 3.J.157.169; 3.J.157.172; 3.J.157.175; 3.J.157.240; 3.J.157.244; 3.J.166.228;
3.J.166.229; 3.J.166.230; 3.J.166.231; 3.J.166.236; 3.J.166.237; 3.J.166.238; 3.J.166.239;
3.J.166.154; 3.J.166.157; 3.J.166.166; 3.J.166.169; 3.J.166.172; 3.J.166.175; 3.J.166.240;
3.J.166.244; 3.J.169.228; 3.J.169.229; 3.J.169.230; 3.J.169.231; 3.J.169.236; 3.J.169.237;
3.J.169.238; 3.J.169.239; 3.J.169.154; 3.J.169.157; 3.J.169.166; 3.J.169.169; 3.J.169.172;
3.J.169.175; 3.J.169.240; 3.J.169.244; 3.J.172.228; 3.J.172.229; 3.J.172.230; 3.J.172.231;
3.J.172.236; 3.J.172.237; 3.J.172.238; 3.J.172.239; 3.J.172.154; 3.J.172.157; 3.J.172.166;
3.J.172.169; 3.J.172.172; 3.J.172.175; 3.J.172.240; 3.J.172.244; 3.J.175.228; 3.J.175.229;
3.J.175.230; 3.J.175.231; 3.J.175.236; 3.J.175.237; 3.J.175.238; 3.J.175.239; 3.J.175.154;
3.J.175.157; 3.J.175.166; 3.J.175.169; 3.J.175.172; 3.J.175.175; 3.J.175.240; 3.J.175.244;
3.J.240.228; 3.J.240.229; 3.J.240.230; 3.J.240.231; 3.J.240.236; 3.J.240.237; 3.J.240.238;
3.J.240.239; 3.J.240.154; 3.J.240.157; 3.J.240.166; 3.J.240.169; 3.J.240.172; 3.J.240.175;
3.J.240.240; 3.J.240.244; 3.J.244.228; 3.J.244.229; 3.J.244.230; 3.J.244.231; 3.J.244.236;
3.J.244.237; 3.J.244.238; 3.J.244.239; 3.J.244.154; 3.J.244.157; 3.J.244.166; 3.J.244.169;
3.J.244.172; 3.J.244.175; 3.J.244.240; 3.J.244.244;

Prodrugs of 3.L

3.L.228.228; 3.L.228.229; 3.L.228.230; 3.L.228.231; 3.L.228.236; 3.L.228.237;
3.L.228.238; 3.L.228.239; 3.L.228.154; 3.L.228.157; 3.L.228.166; 3.L.228.169; 3.L.228.172;
3.L.228.175; 3.L.228.240; 3.L.228.244; 3.L.229.228; 3.L.229.229; 3.L.229.230; 3.L.229.231;
3.L.229.236; 3.L.229.237; 3.L.229.238; 3.L.229.239; 3.L.229.154; 3.L.229.157; 3.L.229.166;
3.L.229.169; 3.L.229.172; 3.L.229.175; 3.L.229.240; 3.L.229.244; 3.L.230.228; 3.L.230.229;
3.L.230.230; 3.L.230.231; 3.L.230.236; 3.L.230.237; 3.L.230.238; 3.L.230.239; 3.L.230.154;
3.L.230.157; 3.L.230.166; 3.L.230.169; 3.L.230.172; 3.L.230.175; 3.L.230.240; 3.L.230.244;
3.L.231.228; 3.L.231.229; 3.L.231.230; 3.L.231.231; 3.L.231.236; 3.L.231.237; 3.L.231.238;
3.L.231.239; 3.L.231.154; 3.L.231.157; 3.L.231.166; 3.L.231.169; 3.L.231.172; 3.L.231.175;
3.L.231.240; 3.L.231.244; 3.L.236.228; 3.L.236.229; 3.L.236.230; 3.L.236.231; 3.L.236.236;
3.L.236.237; 3.L.236.238; 3.L.236.239; 3.L.236.154; 3.L.236.157; 3.L.236.166; 3.L.236.169;
3.L.236.172; 3.L.236.175; 3.L.236.240; 3.L.236.244; 3.L.237.228; 3.L.237.229; 3.L.237.230;
3.L.237.231; 3.L.237.236; 3.L.237.237; 3.L.237.238; 3.L.237.239; 3.L.237.154; 3.L.237.157;
3.L.237.166; 3.L.237.169; 3.L.237.172; 3.L.237.175; 3.L.237.240; 3.L.237.244; 3.L.238.228;
3.L.238.229; 3.L.238.230; 3.L.238.231; 3.L.238.236; 3.L.238.237; 3.L.238.238; 3.L.238.239;
3.L.238.154; 3.L.238.157; 3.L.238.166; 3.L.238.169; 3.L.238.172; 3.L.238.175; 3.L.238.240;
3.L.238.244; 3.L.239.228; 3.L.239.229; 3.L.239.230; 3.L.239.231; 3.L.239.236; 3.L.239.237;
3.L.239.238; 3.L.239.239; 3.L.239.154; 3.L.239.157; 3.L.239.166; 3.L.239.169; 3.L.239.172;
3.L.239.175; 3.L.239.240; 3.L.239.244; 3.L.154.228; 3.L.154.229; 3.L.154.230; 3.L.154.231;
3.L.154.236; 3.L.154.237; 3.L.154.238; 3.L.154.239; 3.L.154.154; 3.L.154.157; 3.L.154.166;
3.L.154.169; 3.L.154.172; 3.L.154.175; 3.L.154.240; 3.L.154.244; 3.L.157.228; 3.L.157.229;
3.L.157.230; 3.L.157.231; 3.L.157.236; 3.L.157.237; 3.L.157.238; 3.L.157.239; 3.L.157.154;
3.L.157.157; 3.L.157.166; 3.L.157.169; 3.L.157.172; 3.L.157.175; 3.L.157.240; 3.L.157.244;
3.L.166.228; 3.L.166.229; 3.L.166.230; 3.L.166.231; 3.L.166.236; 3.L.166.237; 3.L.166.238;
3.L.166.239; 3.L.166.154; 3.L.166.157; 3.L.166.166; 3.L.166.169; 3.L.166.172; 3.L.166.175;
3.L.166.240; 3.L.166.244; 3.L.169.228; 3.L.169.229; 3.L.169.230; 3.L.169.231; 3.L.169.236;
3.L.169.237; 3.L.169.238; 3.L.169.239; 3.L.169.154; 3.L.169.157; 3.L.169.166; 3.L.169.169;
3.L.169.172; 3.L.169.175; 3.L.169.240; 3.L.169.244; 3.L.172.228; 3.L.172.229; 3.L.172.230;
3.L.172.231; 3.L.172.236; 3.L.172.237; 3.L.172.238; 3.L.172.239; 3.L.172.154; 3.L.172.157;
3.L.172.166; 3.L.172.169; 3.L.172.172; 3.L.172.175; 3.L.172.240; 3.L.172.244; 3.L.175.228;
3.L.175.229; 3.L.175.230; 3.L.175.231; 3.L.175.236; 3.L.175.237; 3.L.175.238; 3.L.175.239;
3.L.175.154; 3.L.175.157; 3.L.175.166; 3.L.175.169; 3.L.175.172; 3.L.175.175; 3.L.175.240;
3.L.175.244; 3.L.240.228; 3.L.240.229; 3.L.240.230; 3.L.240.231; 3.L.240.236; 3.L.240.237;
3.L.240.238; 3.L.240.239; 3.L.240.154; 3.L.240.157; 3.L.240.166; 3.L.240.169; 3.L.240.172;
3.L.240.175; 3.L.240.240; 3.L.240.244; 3.L.244.228; 3.L.244.229; 3.L.244.230; 3.L.244.231;
3.L.244.236; 3.L.244.237; 3.L.244.238; 3.L.244.239; 3.L.244.154; 3.L.244.157; 3.L.244.166;
3.L.244.169; 3.L.244.172; 3.L.244.175; 3.L.244.240; 3.L.244.244;

Prodrugs of 3.O

3.O.228.228; 3.O.228.229; 3.O.228.230; 3.O.228.231; 3.O.228.236; 3.O.228.237;
3.O.228.238; 3.O.228.239; 3.O.228.154; 3.O.228.157; 3.O.228.166; 3.O.228.169;
3.O.228.172; 3.O.228.175; 3.O.228.240; 3.O.228.244; 3.O.229.228; 3.O.229.229;
3.O.229.230; 3.O.229.231; 3.O.229.236; 3.O.229.237; 3.O.229.238; 3.O.229.239;
3.O.229.154; 3.O.229.157; 3.O.229.166; 3.O.229.169; 3.O.229.172; 3.O.229.175;
3.O.229.240; 3.O.229.244; 3.O.230.228; 3.O.230.229; 3.O.230.230; 3.O.230.231;
3.O.230.236; 3.O.230.237; 3.O.230.238; 3.O.230.239; 3.O.230.154; 3.O.230.157;
3.O.230.166; 3.O.230.169; 3.O.230.172; 3.O.230.175; 3.O.230.240; 3.O.230.244;
3.O.231.228; 3.O.231.229; 3.O.231.230; 3.O.231.231; 3.O.231.236; 3.O.231.237;
3.O.231.238; 3.O.231.239; 3.O.231.154; 3.O.231.157; 3.O.231.166; 3.O.231.169;
3.O.231.172; 3.O.231.175; 3.O.231.240; 3.O.231.244; 3.O.236.228; 3.O.236.229;
3.O.236.230; 3.O.236.231; 3.O.236.236; 3.O.236.237; 3.O.236.238; 3.O.236.239;
3.O.236.154; 3.O.236.157; 3.O.236.166; 3.O.236.169; 3.O.236.172; 3.O.236.175;
3.O.236.240; 3.O.236.244; 3.O.237.228; 3.O.237.229; 3.O.237.230; 3.O.237.231;
3.O.237.236; 3.O.237.237; 3.O.237.238; 3.O.237.239; 3.O.237.154; 3.O.237.157;
3.O.237.166; 3.O.237.169; 3.O.237.172; 3.O.237.175; 3.O.237.240; 3.O.237.244;

TABLE 100-continued

3.O.238.228; 3.O.238.229; 3.O.238.230; 3.O.238.231; 3.O.238.236; 3.O.238.237;
3.O.238.238; 3.O.238.239; 3.O.238.154; 3.O.238.157; 3.O.238.166; 3.O.238.169;
3.O.238.172; 3.O.238.175; 3.O.238.240; 3.O.238.244; 3.O.239.228; 3.O.239.229;
3.O.239.230; 3.O.239.231; 3.O.239.236; 3.O.239.237; 3.O.239.238; 3.O.239.239;
3.O.239.154; 3.O.239.157; 3.O.239.166; 3.O.239.169; 3.O.239.172; 3.O.239.175;
3.O.239.240; 3.O.239.244; 3.O.154.228; 3.O.154.229; 3.O.154.230; 3.O.154.231;
3.O.154.236; 3.O.154.237; 3.O.154.238; 3.O.154.239; 3.O.154.154; 3.O.154.157;
3.O.154.166; 3.O.154.169; 3.O.154.172; 3.O.154.175; 3.O.154.240; 3.O.154.244;
3.O.157.228; 3.O.157.229; 3.O.157.230; 3.O.157.231; 3.O.157.236; 3.O.157.237;
3.O.157.238; 3.O.157.239; 3.O.157.154; 3.O.157.157; 3.O.157.166; 3.O.157.169;
3.O.157.172; 3.O.157.175; 3.O.157.240; 3.O.157.244; 3.O.166.228; 3.O.166.229;
3.O.166.230; 3.O.166.231; 3.O.166.236; 3.O.166.237; 3.O.166.238; 3.O.166.239;
3.O.166.154; 3.O.166.157; 3.O.166.166; 3.O.166.169; 3.O.166.172; 3.O.166.175;
3.O.166.240; 3.O.166.244; 3.O.169.228; 3.O.169.229; 3.O.169.230; 3.O.169.231;
3.O.169.236; 3.O.169.237; 3.O.169.238; 3.O.169.239; 3.O.169.154; 3.O.169.157;
3.O.169.166; 3.O.169.169; 3.O.169.172; 3.O.169.175; 3.O.169.240; 3.O.169.244;
3.O.172.228; 3.O.172.229; 3.O.172.230; 3.O.172.231; 3.O.172.236; 3.O.172.237;
3.O.172.238; 3.O.172.239; 3.O.172.154; 3.O.172.157; 3.O.172.166; 3.O.172.169;
3.O.172.172; 3.O.172.175; 3.O.172.240; 3.O.172.244; 3.O.175.228; 3.O.175.229;
3.O.175.230; 3.O.175.231; 3.O.175.236; 3.O.175.237; 3.O.175.238; 3.O.175.239;
3.O.175.154; 3.O.175.157; 3.O.175.166; 3.O.175.169; 3.O.175.172; 3.O.175.175;
3.O.175.240; 3.O.175.244; 3.O.240.228; 3.O.240.229; 3.O.240.230; 3.O.240.231;
3.O.240.236; 3.O.240.237; 3.O.240.238; 3.O.240.239; 3.O.240.154; 3.O.240.157;
3.O.240.166; 3.O.240.169; 3.O.240.172; 3.O.240.175; 3.O.240.240; 3.O.240.244;
3.O.244.228; 3.O.244.229; 3.O.244.230; 3.O.244.231; 3.O.244.236; 3.O.244.237;
3.O.244.238; 3.O.244.239; 3.O.244.154; 3.O.244.157; 3.O.244.166; 3.O.244.169;
3.O.244.172; 3.O.244.175; 3.O.244.240; 3.O.244.244;

Prodrugs of 3.P

3.P.228.228; 3.P.228.229; 3.P.228.230; 3.P.228.231; 3.P.228.236; 3.P.228.237;
3.P.228.238; 3.P.228.239; 3.P.228.154; 3.P.228.157; 3.P.228.166; 3.P.228.169; 3.P.228.172;
3.P.228.175; 3.P.228.240; 3.P.228.244; 3.P.229.228; 3.P.229.229; 3.P.229.230; 3.P.229.231;
3.P.229.236; 3.P.229.237; 3.P.229.238; 3.P.229.239; 3.P.229.154; 3.P.229.157; 3.P.229.166;
3.P.229.169; 3.P.229.172; 3.P.229.175; 3.P.229.240; 3.P.229.244; 3.P.230.228; 3.P.230.229;
3.P.230.230; 3.P.230.231; 3.P.230.236; 3.P.230.237; 3.P.230.238; 3.P.230.239; 3.P.230.154;
3.P.230.157; 3.P.230.166; 3.P.230.169; 3.P.230.172; 3.P.230.175; 3.P.230.240; 3.P.230.244;
3.P.231.228; 3.P.231.229; 3.P.231.230; 3.P.231.231; 3.P.231.236; 3.P.231.237; 3.P.231.238;
3.P.231.239; 3.P.231.154; 3.P.231.157; 3.P.231.166; 3.P.231.169; 3.P.231.172; 3.P.231.175;
3.P.231.240; 3.P.231.244; 3.P.236.228; 3.P.236.229; 3.P.236.230; 3.P.236.231; 3.P.236.236;
3.P.236.237; 3.P.236.238; 3.P.236.239; 3.P.236.154; 3.P.236.157; 3.P.236.166; 3.P.236.169;
3.P.236.172; 3.P.236.175; 3.P.236.240; 3.P.236.244; 3.P.237.228; 3.P.237.229; 3.P.237.230;
3.P.237.231; 3.P.237.236; 3.P.237.237; 3.P.237.238; 3.P.237.239; 3.P.237.154; 3.P.237.157;
3.P.237.166; 3.P.237.169; 3.P.237.172; 3.P.237.175; 3.P.237.240; 3.P.237.244; 3.P.238.228;
3.P.238.229; 3.P.238.230; 3.P.238.231; 3.P.238.236; 3.P.238.237; 3.P.238.238; 3.P.238.239;
3.P.238.154; 3.P.238.157; 3.P.238.166; 3.P.238.169; 3.P.238.172; 3.P.238.175; 3.P.238.240;
3.P.238.244; 3.P.239.228; 3.P.239.229; 3.P.239.230; 3.P.239.231; 3.P.239.236; 3.P.239.237;
3.P.239.238; 3.P.239.239; 3.P.239.154; 3.P.239.157; 3.P.239.166; 3.P.239.169; 3.P.239.172;
3.P.239.175; 3.P.239.240; 3.P.239.244; 3.P.154.228; 3.P.154.229; 3.P.154.230; 3.P.154.231;
3.P.154.236; 3.P.154.237; 3.P.154.238; 3.P.154.239; 3.P.154.154; 3.P.154.157; 3.P.154.166;
3.P.154.169; 3.P.154.172; 3.P.154.175; 3.P.154.240; 3.P.154.244; 3.P.157.228; 3.P.157.229;
3.P.157.230; 3.P.157.231; 3.P.157.236; 3.P.157.237; 3.P.157.238; 3.P.157.239; 3.P.157.154;
3.P.157.157; 3.P.157.166; 3.P.157.169; 3.P.157.172; 3.P.157.175; 3.P.157.240; 3.P.157.244;
3.P.166.228; 3.P.166.229; 3.P.166.230; 3.P.166.231; 3.P.166.236; 3.P.166.237; 3.P.166.238;
3.P.166.239; 3.P.166.154; 3.P.166.157; 3.P.166.166; 3.P.166.169; 3.P.166.172; 3.P.166.175;
3.P.166.240; 3.P.166.244; 3.P.169.228; 3.P.169.229; 3.P.169.230; 3.P.169.231; 3.P.169.236;
3.P.169.237; 3.P.169.238; 3.P.169.239; 3.P.169.154; 3.P.169.157; 3.P.169.166; 3.P.169.169;
3.P.169.172; 3.P.169.175; 3.P.169.240; 3.P.169.244; 3.P.172.228; 3.P.172.229; 3.P.172.230;
3.P.172.231; 3.P.172.236; 3.P.172.237; 3.P.172.238; 3.P.172.239; 3.P.172.154; 3.P.172.157;
3.P.172.166; 3.P.172.169; 3.P.172.172; 3.P.172.175; 3.P.172.240; 3.P.172.244; 3.P.175.228;
3.P.175.229; 3.P.175.230; 3.P.175.231; 3.P.175.236; 3.P.175.237; 3.P.175.238; 3.P.175.239;
3.P.175.154; 3.P.175.157; 3.P.175.166; 3.P.175.169; 3.P.175.172; 3.P.175.175; 3.P.175.240;
3.P.175.244; 3.P.240.228; 3.P.240.229; 3.P.240.230; 3.P.240.231; 3.P.240.236; 3.P.240.237;
3.P.240.238; 3.P.240.239; 3.P.240.154; 3.P.240.157; 3.P.240.166; 3.P.240.169; 3.P.240.172;
3.P.240.175; 3.P.240.240; 3.P.240.244; 3.P.244.228; 3.P.244.229; 3.P.244.230; 3.P.244.231;
3.P.244.236; 3.P.244.237; 3.P.244.238; 3.P.244.239; 3.P.244.154; 3.P.244.157; 3.P.244.166;
3.P.244.169; 3.P.244.172; 3.P.244.175; 3.P.244.240; 3.P.244.244;

Prodrugs of 3.U

3.U.228.228; 3.U.228.229; 3.U.228.230; 3.U.228.231; 3.U.228.236; 3.U.228.237;
3.U.228.238; 3.U.228.239; 3.U.228.154; 3.U.228.157; 3.U.228.166; 3.U.228.169;
3.U.228.172; 3.U.228.175; 3.U.228.240; 3.U.228.244; 3.U.229.228; 3.U.229.229;
3.U.229.230; 3.U.229.231; 3.U.229.236; 3.U.229.237; 3.U.229.238; 3.U.229.239;
3.U.229.154; 3.U.229.157; 3.U.229.166; 3.U.229.169; 3.U.229.172; 3.U.229.175;
3.U.229.240; 3.U.229.244; 3.U.230.228; 3.U.230.229; 3.U.230.230; 3.U.230.231;
3.U.230.236; 3.U.230.237; 3.U.230.238; 3.U.230.239; 3.U.230.154; 3.U.230.157;
3.U.230.166; 3.U.230.169; 3.U.230.172; 3.U.230.175; 3.U.230.240; 3.U.230.244;
3.U.231.228; 3.U.231.229; 3.U.231.230; 3.U.231.231; 3.U.231.236; 3.U.231.237;
3.U.231.238; 3.U.231.239; 3.U.231.154; 3.U.231.157; 3.U.231.166; 3.U.231.169;
3.U.231.172; 3.U.231.175; 3.U.231.240; 3.U.231.244; 3.U.236.228; 3.U.236.229;

TABLE 100-continued

3.U.236.230; 3.U.236.231; 3.U.236.236; 3.U.236.237; 3.U.236.238; 3.U.236.239;
3.U.236.154; 3.U.236.157; 3.U.236.166; 3.U.236.169; 3.U.236.172; 3.U.236.175;
3.U.236.240; 3.U.236.244; 3.U.237.228; 3.U.237.229; 3.U.237.230; 3.U.237.231;
3.U.237.236; 3.U.237.237; 3.U.237.238; 3.U.237.239; 3.U.237.154; 3.U.237.157;
3.U.237.166; 3.U.237.169; 3.U.237.172; 3.U.237.175; 3.U.237.240; 3.U.237.244;
3.U.238.228; 3.U.238.229; 3.U.238.230; 3.U.238.231; 3.U.238.236; 3.U.238.237;
3.U.238.238; 3.U.238.239; 3.U.238.154; 3.U.238.157; 3.U.238.166; 3.U.238.169;
3.U.238.172; 3.U.238.175; 3.U.238.240; 3.U.238.244; 3.U.239.228; 3.U.239.229;
3.U.239.230; 3.U.239.231; 3.U.239.236; 3.U.239.237; 3.U.239.238; 3.U.239.239;
3.U.239.154; 3.U.239.157; 3.U.239.166; 3.U.239.169; 3.U.239.172; 3.U.239.175;
3.U.239.240; 3.U.239.244; 3.U.154.228; 3.U.154.229; 3.U.154.230; 3.U.154.231;
3.U.154.236; 3.U.154.237; 3.U.154.238; 3.U.154.239; 3.U.154.154; 3.U.154.157;
3.U.154.166; 3.U.154.169; 3.U.154.172; 3.U.154.175; 3.U.154.240; 3.U.154.244;
3.U.157.228; 3.U.157.229; 3.U.157.230; 3.U.157.231; 3.U.157.236; 3.U.157.237;
3.U.157.238; 3.U.157.239; 3.U.157.154; 3.U.157.157; 3.U.157.166; 3.U.157.169;
3.U.157.172; 3.U.157.175; 3.U.157.240; 3.U.157.244; 3.U.166.228; 3.U.166.229;
3.U.166.230; 3.U.166.231; 3.U.166.236; 3.U.166.237; 3.U.166.238; 3.U.166.239;
3.U.166.154; 3.U.166.157; 3.U.166.166; 3.U.166.169; 3.U.166.172; 3.U.166.175;
3.U.166.240; 3.U.166.244; 3.U.169.228; 3.U.169.229; 3.U.169.230; 3.U.169.231;
3.U.169.236; 3.U.169.237; 3.U.169.238; 3.U.169.239; 3.U.169.154; 3.U.169.157;
3.U.169.166; 3.U.169.169; 3.U.169.172; 3.U.169.175; 3.U.169.240; 3.U.169.244;
3.U.172.228; 3.U.172.229; 3.U.172.230; 3.U.172.231; 3.U.172.236; 3.U.172.237;
3.U.172.238; 3.U.172.239; 3.U.172.154; 3.U.172.157; 3.U.172.166; 3.U.172.169;
3.U.172.172; 3.U.172.175; 3.U.172.240; 3.U.172.244; 3.U.175.228; 3.U.175.229;
3.U.175.230; 3.U.175.231; 3.U.175.236; 3.U.175.237; 3.U.175.238; 3.U.175.239;
3.U.175.154; 3.U.175.157; 3.U.175.166; 3.U.175.169; 3.U.175.172; 3.U.175.175;
3.U.175.240; 3.U.175.244; 3.U.240.228; 3.U.240.229; 3.U.240.230; 3.U.240.231;
3.U.240.236; 3.U.240.237; 3.U.240.238; 3.U.240.239; 3.U.240.154; 3.U.240.157;
3.U.240.166; 3.U.240.169; 3.U.240.172; 3.U.240.175; 3.U.240.240; 3.U.240.244;
3.U.244.228; 3.U.244.229; 3.U.244.230; 3.U.244.231; 3.U.244.236; 3.U.244.237;
3.U.244.238; 3.U.244.239; 3.U.244.154; 3.U.244.157; 3.U.244.166; 3.U.244.169;
3.U.244.172; 3.U.244.175; 3.U.244.240; 3.U.244.244;

Prodrugs of 3.W

3.W.228.228; 3.W.228.229; 3.W.228.230; 3.W.228.231; 3.W.228.236; 3.W.228.237;
3.W.228.238; 3.W.228.239; 3.W.228.154; 3.W.228.157; 3.W.228.166; 3.W.228.169;
3.W.228.172; 3.W.228.175; 3.W.228.240; 3.W.228.244; 3.W.229.228; 3.W.229.229;
3.W.229.230; 3.W.229.231; 3.W.229.236; 3.W.229.237; 3.W.229.238; 3.W.229.239;
3.W.229.154; 3.W.229.157; 3.W.229.166; 3.W.229.169; 3.W.229.172; 3.W.229.175;
3.W.229.240; 3.W.229.244; 3.W.230.228; 3.W.230.229; 3.W.230.230; 3.W.230.231;
3.W.230.236; 3.W.230.237; 3.W.230.238; 3.W.230.239; 3.W.230.154; 3.W.230.157;
3.W.230.166; 3.W.230.169; 3.W.230.172; 3.W.230.175; 3.W.230.240; 3.W.230.244;
3.W.231.228; 3.W.231.229; 3.W.231.230; 3.W.231.231; 3.W.231.236; 3.W.231.237;
3.W.231.238; 3.W.231.239; 3.W.231.154; 3.W.231.157; 3.W.231.166; 3.W.231.169;
3.W.231.172; 3.W.231.175; 3.W.231.240; 3.W.231.244; 3.W.236.228; 3.W.236.229;
3.W.236.230; 3.W.236.231; 3.W.236.236; 3.W.236.237; 3.W.236.238; 3.W.236.239;
3.W.236.154; 3.W.236.157; 3.W.236.166; 3.W.236.169; 3.W.236.172; 3.W.236.175;
3.W.236.240; 3.W.236.244; 3.W.237.228; 3.W.237.229; 3.W.237.230; 3.W.237.231;
3.W.237.236; 3.W.237.237; 3.W.237.238; 3.W.237.239; 3.W.237.154; 3.W.237.157;
3.W.237.166; 3.W.237.169; 3.W.237.172; 3.W.237.175; 3.W.237.240; 3.W.237.244;
3.W.238.228; 3.W.238.229; 3.W.238.230; 3.W.238.231; 3.W.238.236; 3.W.238.237;
3.W.238.238; 3.W.238.239; 3.W.238.154; 3.W.238.157; 3.W.238.166; 3.W.238.169;
3.W.238.172; 3.W.238.175; 3.W.238.240; 3.W.238.244; 3.W.239.228; 3.W.239.229;
3.W.239.230; 3.W.239.231; 3.W.239.236; 3.W.239.237; 3.W.239.238; 3.W.239.239;
3.W.239.154; 3.W.239.157; 3.W.239.166; 3.W.239.169; 3.W.239.172; 3.W.239.175;
3.W.239.240; 3.W.239.244; 3.W.154.228; 3.W.154.229; 3.W.154.230; 3.W.154.231;
3.W.154.236; 3.W.154.237; 3.W.154.238; 3.W.154.239; 3.W.154.154; 3.W.154.157;
3.W.154.166; 3.W.154.169; 3.W.154.172; 3.W.154.175; 3.W.154.240; 3.W.154.244;
3.W.157.228; 3.W.157.229; 3.W.157.230; 3.W.157.231; 3.W.157.236; 3.W.157.237;
3.W.157.238; 3.W.157.239; 3.W.157.154; 3.W.157.157; 3.W.157.166; 3.W.157.169;
3.W.157.172; 3.W.157.175; 3.W.157.240; 3.W.157.244; 3.W.166.228; 3.W.166.229;
3.W.166.230; 3.W.166.231; 3.W.166.236; 3.W.166.237; 3.W.166.238; 3.W.166.239;
3.W.166.154; 3.W.166.157; 3.W.166.166; 3.W.166.169; 3.W.166.172; 3.W.166.175;
3.W.166.240; 3.W.166.244; 3.W.169.228; 3.W.169.229; 3.W.169.230; 3.W.169.231;
3.W.169.236; 3.W.169.237; 3.W.169.238; 3.W.169.239; 3.W.169.154; 3.W.169.157;
3.W.169.166; 3.W.169.169; 3.W.169.172; 3.W.169.175; 3.W.169.240; 3.W.169.244;
3.W.172.228; 3.W.172.229; 3.W.172.230; 3.W.172.231; 3.W.172.236; 3.W.172.237;
3.W.172.238; 3.W.172.239; 3.W.172.154; 3.W.172.157; 3.W.172.166; 3.W.172.169;
3.W.172.172; 3.W.172.175; 3.W.172.240; 3.W.172.244; 3.W.175.228; 3.W.175.229;
3.W.175.230; 3.W.175.231; 3.W.175.236; 3.W.175.237; 3.W.175.238; 3.W.175.239;
3.W.175.154; 3.W.175.157; 3.W.175.166; 3.W.175.169; 3.W.175.172; 3.W.175.175;
3.W.175.240; 3.W.175.244; 3.W.240.228; 3.W.240.229; 3.W.240.230; 3.W.240.231;
3.W.240.236; 3.W.240.237; 3.W.240.238; 3.W.240.239; 3.W.240.154; 3.W.240.157;
3.W.240.166; 3.W.240.169; 3.W.240.172; 3.W.240.175; 3.W.240.240; 3.W.240.244;
3.W.244.228; 3.W.244.229; 3.W.244.230; 3.W.244.231; 3.W.244.236; 3.W.244.237;
3.W.244.238; 3.W.244.239; 3.W.244.154; 3.W.244.157; 3.W.244.166; 3.W.244.169;
3.W.244.172; 3.W.244.175; 3.W.244.240; 3.W.244.244;

TABLE 100-continued

Prodrugs of 3.Y

3.Y.228.228; 3.Y.228.229; 3.Y.228.230; 3.Y.228.231; 3.Y.228.236; 3.Y.228.237; 3.Y.228.238; 3.Y.228.239; 3.Y.228.154; 3.Y.228.157; 3.Y.228.166; 3.Y.228.169; 3.Y.228.172; 3.Y.228.175; 3.Y.228.240; 3.Y.228.244; 3.Y.229.228; 3.Y.229.229; 3.Y.229.230; 3.Y.229.231; 3.Y.229.236; 3.Y.229.237; 3.Y.229.238; 3.Y.229.239; 3.Y.229.154; 3.Y.229.157; 3.Y.229.166; 3.Y.229.169; 3.Y.229.172; 3.Y.229.175; 3.Y.229.240; 3.Y.229.244; 3.Y.230.228; 3.Y.230.229; 3.Y.230.230; 3.Y.230.231; 3.Y.230.236; 3.Y.230.237; 3.Y.230.238; 3.Y.230.239; 3.Y.230.154; 3.Y.230.157; 3.Y.230.166; 3.Y.230.169; 3.Y.230.172; 3.Y.230.175; 3.Y.230.240; 3.Y.230.244; 3.Y.231.228; 3.Y.231.229; 3.Y.231.230; 3.Y.231.231; 3.Y.231.236; 3.Y.231.237; 3.Y.231.238; 3.Y.231.239; 3.Y.231.154; 3.Y.231.157; 3.Y.231.166; 3.Y.231.169; 3.Y.231.172; 3.Y.231.175; 3.Y.231.240; 3.Y.231.244; 3.Y.236.228; 3.Y.236.229; 3.Y.236.230; 3.Y.236.231; 3.Y.236.236; 3.Y.236.237; 3.Y.236.238; 3.Y.236.239; 3.Y.236.154; 3.Y.236.157; 3.Y.236.166; 3.Y.236.169; 3.Y.236.172; 3.Y.236.175; 3.Y.236.240; 3.Y.236.244; 3.Y.237.228; 3.Y.237.229; 3.Y.237.230; 3.Y.237.231; 3.Y.237.236; 3.Y.237.237; 3.Y.237.238; 3.Y.237.239; 3.Y.237.154; 3.Y.237.157; 3.Y.237.166; 3.Y.237.169; 3.Y.237.172; 3.Y.237.175; 3.Y.237.240; 3.Y.237.244; 3.Y.238.228; 3.Y.238.229; 3.Y.238.230; 3.Y.238.231; 3.Y.238.236; 3.Y.238.237; 3.Y.238.238; 3.Y.238.239; 3.Y.238.154; 3.Y.238.157; 3.Y.238.166; 3.Y.238.169; 3.Y.238.172; 3.Y.238.175; 3.Y.238.240; 3.Y.238.244; 3.Y.239.228; 3.Y.239.229; 3.Y.239.230; 3.Y.239.231; 3.Y.239.236; 3.Y.239.237; 3.Y.239.238; 3.Y.239.239; 3.Y.239.154; 3.Y.239.157; 3.Y.239.166; 3.Y.239.169; 3.Y.239.172; 3.Y.239.175; 3.Y.239.240; 3.Y.239.244; 3.Y.154.228; 3.Y.154.229; 3.Y.154.230; 3.Y.154.231; 3.Y.154.236; 3.Y.154.237; 3.Y.154.238; 3.Y.154.239; 3.Y.154.154; 3.Y.154.157; 3.Y.154.166; 3.Y.154.169; 3.Y.154.172; 3.Y.154.175; 3.Y.154.240; 3.Y.154.244; 3.Y.157.228; 3.Y.157.229; 3.Y.157.230; 3.Y.157.231; 3.Y.157.236; 3.Y.157.237; 3.Y.157.238; 3.Y.157.239; 3.Y.157.154; 3.Y.157.157; 3.Y.157.166; 3.Y.157.169; 3.Y.157.172; 3.Y.157.175; 3.Y.157.240; 3.Y.157.244; 3.Y.166.228; 3.Y.166.229; 3.Y.166.230; 3.Y.166.231; 3.Y.166.236; 3.Y.166.237; 3.Y.166.238; 3.Y.166.239; 3.Y.166.154; 3.Y.166.157; 3.Y.166.166; 3.Y.166.169; 3.Y.166.172; 3.Y.166.175; 3.Y.166.240; 3.Y.166.244; 3.Y.169.228; 3.Y.169.229; 3.Y.169.230; 3.Y.169.231; 3.Y.169.236; 3.Y.169.237; 3.Y.169.238; 3.Y.169.239; 3.Y.169.154; 3.Y.169.157; 3.Y.169.166; 3.Y.169.169; 3.Y.169.172; 3.Y.169.175; 3.Y.169.240; 3.Y.169.244; 3.Y.172.228; 3.Y.172.229; 3.Y.172.230; 3.Y.172.231; 3.Y.172.236; 3.Y.172.237; 3.Y.172.238; 3.Y.172.239; 3.Y.172.154; 3.Y.172.157; 3.Y.172.166; 3.Y.172.169; 3.Y.172.172; 3.Y.172.175; 3.Y.172.240; 3.Y.172.244; 3.Y.175.228; 3.Y.175.229; 3.Y.175.230; 3.Y.175.231; 3.Y.175.236; 3.Y.175.237; 3.Y.175.238; 3.Y.175.239; 3.Y.175.154; 3.Y.175.157; 3.Y.175.166; 3.Y.175.169; 3.Y.175.172; 3.Y.175.175; 3.Y.175.240; 3.Y.175.244; 3.Y.240.228; 3.Y.240.229; 3.Y.240.230; 3.Y.240.231; 3.Y.240.236; 3.Y.240.237; 3.Y.240.238; 3.Y.240.239; 3.Y.240.154; 3.Y.240.157; 3.Y.240.166; 3.Y.240.169; 3.Y.240.172; 3.Y.240.175; 3.Y.240.240; 3.Y.240.244; 3.Y.244.228; 3.Y.244.229; 3.Y.244.230; 3.Y.244.231; 3.Y.244.236; 3.Y.244.237; 3.Y.244.238; 3.Y.244.239; 3.Y.244.154; 3.Y.244.157; 3.Y.244.166; 3.Y.244.169; 3.Y.244.172; 3.Y.244.175; 3.Y.244.240; 3.Y.244.244;

Prodrugs of 4.B

4.B.228.228; 4.B.228.229; 4.B.228.230; 4.B.228.231; 4.B.228.236; 4.B.228.237; 4.B.228.238; 4.B.228.239; 4.B.228.154; 4.B.228.157; 4.B.228.166; 4.B.228.169; 4.B.228.172; 4.B.228.175; 4.B.228.240; 4.B.228.244; 4.B.229.228; 4.B.229.229; 4.B.229.230; 4.B.229.231; 4.B.229.236; 4.B.229.237; 4.B.229.238; 4.B.229.239; 4.B.229.154; 4.B.229.157; 4.B.229.166; 4.B.229.169; 4.B.229.172; 4.B.229.175; 4.B.229.240; 4.B.229.244; 4.B.230.228; 4.B.230.229; 4.B.230.230; 4.B.230.231; 4.B.230.236; 4.B.230.237; 4.B.230.238; 4.B.230.239; 4.B.230.154; 4.B.230.157; 4.B.230.166; 4.B.230.169; 4.B.230.172; 4.B.230.175; 4.B.230.240; 4.B.230.244; 4.B.231.228; 4.B.231.229; 4.B.231.230; 4.B.231.231; 4.B.231.236; 4.B.231.237; 4.B.231.238; 4.B.231.239; 4.B.231.154; 4.B.231.157; 4.B.231.166; 4.B.231.169; 4.B.231.172; 4.B.231.175; 4.B.231.240; 4.B.231.244; 4.B.236.228; 4.B.236.229; 4.B.236.230; 4.B.236.231; 4.B.236.236; 4.B.236.237; 4.B.236.238; 4.B.236.239; 4.B.236.154; 4.B.236.157; 4.B.236.166; 4.B.236.169; 4.B.236.172; 4.B.236.175; 4.B.236.240; 4.B.236.244; 4.B.237.228; 4.B.237.229; 4.B.237.230; 4.B.237.231; 4.B.237.236; 4.B.237.237; 4.B.237.238; 4.B.237.239; 4.B.237.154; 4.B.237.157; 4.B.237.166; 4.B.237.169; 4.B.237.172; 4.B.237.175; 4.B.237.240; 4.B.237.244; 4.B.238.228; 4.B.238.229; 4.B.238.230; 4.B.238.231; 4.B.238.236; 4.B.238.237; 4.B.238.238; 4.B.238.239; 4.B.238.154; 4.B.238.157; 4.B.238.166; 4.B.238.169; 4.B.238.172; 4.B.238.175; 4.B.238.240; 4.B.238.244; 4.B.239.228; 4.B.239.229; 4.B.239.230; 4.B.239.231; 4.B.239.236; 4.B.239.237; 4.B.239.238; 4.B.239.239; 4.B.239.154; 4.B.239.157; 4.B.239.166; 4.B.239.169; 4.B.239.172; 4.B.239.175; 4.B.239.240; 4.B.239.244; 4.B.154.228; 4.B.154.229; 4.B.154.230; 4.B.154.231; 4.B.154.236; 4.B.154.237; 4.B.154.238; 4.B.154.239; 4.B.154.154; 4.B.154.157; 4.B.154.166; 4.B.154.169; 4.B.154.172; 4.B.154.175; 4.B.154.240; 4.B.154.244; 4.B.157.228; 4.B.157.229; 4.B.157.230; 4.B.157.231; 4.B.157.236; 4.B.157.237; 4.B.157.238; 4.B.157.239; 4.B.157.154; 4.B.157.157; 4.B.157.166; 4.B.157.169; 4.B.157.172; 4.B.157.175; 4.B.157.240; 4.B.157.244; 4.B.166.228; 4.B.166.229; 4.B.166.230; 4.B.166.231; 4.B.166.236; 4.B.166.237; 4.B.166.238; 4.B.166.239; 4.B.166.154; 4.B.166.157; 4.B.166.166; 4.B.166.169; 4.B.166.172; 4.B.166.175; 4.B.166.240; 4.B.166.244; 4.B.169.228; 4.B.169.229; 4.B.169.230; 4.B.169.231; 4.B.169.236; 4.B.169.237; 4.B.169.238; 4.B.169.239; 4.B.169.154; 4.B.169.157; 4.B.169.166; 4.B.169.169; 4.B.169.172; 4.B.169.175; 4.B.169.240; 4.B.169.244; 4.B.172.228; 4.B.172.229; 4.B.172.230; 4.B.172.231; 4.B.172.236; 4.B.172.237; 4.B.172.238; 4.B.172.239; 4.B.172.154; 4.B.172.157; 4.B.172.166; 4.B.172.169; 4.B.172.172; 4.B.172.175; 4.B.172.240; 4.B.172.244; 4.B.175.228; 4.B.175.229; 4.B.175.230; 4.B.175.231; 4.B.175.236; 4.B.175.237; 4.B.175.238; 4.B.175.239; 4.B.175.154; 4.B.175.157; 4.B.175.166; 4.B.175.169; 4.B.175.172; 4.B.175.175; 4.B.175.240;

TABLE 100-continued

4.B.175.244; 4.B.240.228; 4.B.240.229; 4.B.240.230; 4.B.240.231; 4.B.240.236; 4.B.240.237;
4.B.240.238; 4.B.240.239; 4.B.240.154; 4.B.240.157; 4.B.240.166; 4.B.240.169; 4.B.240.172;
4.B.240.175; 4.B.240.240; 4.B.240.244; 4.B.244.228; 4.B.244.229; 4.B.244.230; 4.B.244.231;
4.B.244.236; 4.B.244.237; 4.B.244.238; 4.B.244.239; 4.B.244.154; 4.B.244.157; 4.B.244.166;
4.B.244.169; 4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236; 4.D.228.237;
4.D.228.238; 4.D.228.239; 4.D.228.154; 4.D.228.157; 4.D.228.166; 4.D.228.169;
4.D.228.172; 4.D.228.175; 4.D.228.240; 4.D.228.244; 4.D.229.228; 4.D.229.229;
4.D.229.230; 4.D.229.231; 4.D.229.236; 4.D.229.237; 4.D.229.238; 4.D.229.239;
4.D.229.154; 4.D.229.157; 4.D.229.166; 4.D.229.169; 4.D.229.172; 4.D.229.175;
4.D.229.240; 4.D.229.244; 4.D.230.228; 4.D.230.229; 4.D.230.230; 4.D.230.231;
4.D.230.236; 4.D.230.237; 4.D.230.238; 4.D.230.239; 4.D.230.154; 4.D.230.157;
4.D.230.166; 4.D.230.169; 4.D.230.172; 4.D.230.175; 4.D.230.240; 4.D.230.244;
4.D.231.228; 4.D.231.229; 4.D.231.230; 4.D.231.231; 4.D.231.236; 4.D.231.237;
4.D.231.238; 4.D.231.239; 4.D.231.154; 4.D.231.157; 4.D.231.166; 4.D.231.169;
4.D.231.172; 4.D.231.175; 4.D.231.240; 4.D.231.244; 4.D.236.228; 4.D.236.229;
4.D.236.230; 4.D.236.231; 4.D.236.236; 4.D.236.237; 4.D.236.238; 4.D.236.239;
4.D.236.154; 4.D.236.157; 4.D.236.166; 4.D.236.169; 4.D.236.172; 4.D.236.175;
4.D.236.240; 4.D.236.244; 4.D.237.228; 4.D.237.229; 4.D.237.230; 4.D.237.231;
4.D.237.236; 4.D.237.237; 4.D.237.238; 4.D.237.239; 4.D.237.154; 4.D.237.157;
4.D.237.166; 4.D.237.169; 4.D.237.172; 4.D.237.175; 4.D.237.240; 4.D.237.244;
4.D.238.228; 4.D.238.229; 4.D.238.230; 4.D.238.231; 4.D.238.236; 4.D.238.237;
4.D.238.238; 4.D.238.239; 4.D.238.154; 4.D.238.157; 4.D.238.166; 4.D.238.169;
4.D.238.172; 4.D.238.175; 4.D.238.240; 4.D.238.244; 4.D.239.228; 4.D.239.229;
4.D.239.230; 4.D.239.231; 4.D.239.236; 4.D.239.237; 4.D.239.238; 4.D.239.239;
4.D.239.154; 4.D.239.157; 4.D.239.166; 4.D.239.169; 4.D.239.172; 4.D.239.175;
4.D.239.240; 4.D.239.244; 4.D.154.228; 4.D.154.229; 4.D.154.230; 4.D.154.231;
4.D.154.236; 4.D.154.237; 4.D.154.238; 4.D.154.239; 4.D.154.154; 4.D.154.157;
4.D.154.166; 4.D.154.169; 4.D.154.172; 4.D.154.175; 4.D.154.240; 4.D.154.244;
4.D.157.228; 4.D.157.229; 4.D.157.230; 4.D.157.231; 4.D.157.236; 4.D.157.237;
4.D.157.238; 4.D.157.239; 4.D.157.154; 4.D.157.157; 4.D.157.166; 4.D.157.169;
4.D.157.172; 4.D.157.175; 4.D.157.240; 4.D.157.244; 4.D.166.228; 4.D.166.229;
4.D.166.230; 4.D.166.231; 4.D.166.236; 4.D.166.237; 4.D.166.238; 4.D.166.239;
4.D.166.154; 4.D.166.157; 4.D.166.166; 4.D.166.169; 4.D.166.172; 4.D.166.175;
4.D.166.240; 4.D.166.244; 4.D.169.228; 4.D.169.229; 4.D.169.230; 4.D.169.231;
4.D.169.236; 4.D.169.237; 4.D.169.238; 4.D.169.239; 4.D.169.154; 4.D.169.157;
4.D.169.166; 4.D.169.169; 4.D.169.172; 4.D.169.175; 4.D.169.240; 4.D.169.244;
4.D.172.228; 4.D.172.229; 4.D.172.230; 4.D.172.231; 4.D.172.236; 4.D.172.237;
4.D.172.238; 4.D.172.239; 4.D.172.154; 4.D.172.157; 4.D.172.166; 4.D.172.169;
4.D.172.172; 4.D.172.175; 4.D.172.240; 4.D.172.244; 4.D.175.228; 4.D.175.229;
4.D.175.230; 4.D.175.231; 4.D.175.236; 4.D.175.237; 4.D.175.238; 4.D.175.239;
4.D.175.154; 4.D.175.157; 4.D.175.166; 4.D.175.169; 4.D.175.172; 4.D.175.175;
4.D.175.240; 4.D.175.244; 4.D.240.228; 4.D.240.229; 4.D.240.230; 4.D.240.231;
4.D.240.236; 4.D.240.237; 4.D.240.238; 4.D.240.239; 4.D.240.154; 4.D.240.157;
4.D.240.166; 4.D.240.169; 4.D.240.172; 4.D.240.175; 4.D.240.240; 4.D.240.244;
4.D.244.228; 4.D.244.229; 4.D.244.230; 4.D.244.231; 4.D.244.236; 4.D.244.237;
4.D.244.238; 4.D.244.239; 4.D.244.154; 4.D.244.157; 4.D.244.166; 4.D.244.169;
4.D.244.172; 4.D.244.175; 4.D.244.240; 4.D.244.244;

Prodrugs of 4.E

4.E.228.228; 4.E.228.229; 4.E.228.230; 4.E.228.231; 4.E.228.236; 4.E.228.237;
4.E.228.238; 4.E.228.239; 4.E.228.154; 4.E.228.157; 4.E.228.166; 4.E.228.169; 4.E.228.172;
4.E.228.175; 4.E.228.240; 4.E.228.244; 4.E.229.228; 4.E.229.229; 4.E.229.230; 4.E.229.231;
4.E.229.236; 4.E.229.237; 4.E.229.238; 4.E.229.239; 4.E.229.154; 4.E.229.157; 4.E.229.166;
4.E.229.169; 4.E.229.172; 4.E.229.175; 4.E.229.240; 4.E.229.244; 4.E.230.228; 4.E.230.229;
4.E.230.230; 4.E.230.231; 4.E.230.236; 4.E.230.237; 4.E.230.238; 4.E.230.239; 4.E.230.154;
4.E.230.157; 4.E.230.166; 4.E.230.169; 4.E.230.172; 4.E.230.175; 4.E.230.240; 4.E.230.244;
4.E.231.228; 4.E.231.229; 4.E.231.230; 4.E.231.231; 4.E.231.236; 4.E.231.237; 4.E.231.238;
4.E.231.239; 4.E.231.154; 4.E.231.157; 4.E.231.166; 4.E.231.169; 4.E.231.172; 4.E.231.175;
4.E.231.240; 4.E.231.244; 4.E.236.228; 4.E.236.229; 4.E.236.230; 4.E.236.231; 4.E.236.236;
4.E.236.237; 4.E.236.238; 4.E.236.239; 4.E.236.154; 4.E.236.157; 4.E.236.166; 4.E.236.169;
4.E.236.172; 4.E.236.175; 4.E.236.240; 4.E.236.244; 4.E.237.228; 4.E.237.229; 4.E.237.230;
4.E.237.231; 4.E.237.236; 4.E.237.237; 4.E.237.238; 4.E.237.239; 4.E.237.154; 4.E.237.157;
4.E.237.166; 4.E.237.169; 4.E.237.172; 4.E.237.175; 4.E.237.240; 4.E.237.244; 4.E.238.228;
4.E.238.229; 4.E.238.230; 4.E.238.231; 4.E.238.236; 4.E.238.237; 4.E.238.238; 4.E.238.239;
4.E.238.154; 4.E.238.157; 4.E.238.166; 4.E.238.169; 4.E.238.172; 4.E.238.175; 4.E.238.240;
4.E.238.244; 4.E.239.228; 4.E.239.229; 4.E.239.230; 4.E.239.231; 4.E.239.236; 4.E.239.237;
4.E.239.238; 4.E.239.239; 4.E.239.154; 4.E.239.157; 4.E.239.166; 4.E.239.169; 4.E.239.172;
4.E.239.175; 4.E.239.240; 4.E.239.244; 4.E.154.228; 4.E.154.229; 4.E.154.230; 4.E.154.231;
4.E.154.236; 4.E.154.237; 4.E.154.238; 4.E.154.239; 4.E.154.154; 4.E.154.157; 4.E.154.166;
4.E.154.169; 4.E.154.172; 4.E.154.175; 4.E.154.240; 4.E.154.244; 4.E.157.228; 4.E.157.229;
4.E.157.230; 4.E.157.231; 4.E.157.236; 4.E.157.237; 4.E.157.238; 4.E.157.239; 4.E.157.154;
4.E.157.157; 4.E.157.166; 4.E.157.169; 4.E.157.172; 4.E.157.175; 4.E.157.240; 4.E.157.244;
4.E.166.228; 4.E.166.229; 4.E.166.230; 4.E.166.231; 4.E.166.236; 4.E.166.237; 4.E.166.238;
4.E.166.239; 4.E.166.154; 4.E.166.157; 4.E.166.166; 4.E.166.169; 4.E.166.172; 4.E.166.175;
4.E.166.240; 4.E.166.244; 4.E.169.228; 4.E.169.229; 4.E.169.230; 4.E.169.231; 4.E.169.236;
4.E.169.237; 4.E.169.238; 4.E.169.239; 4.E.169.154; 4.E.169.157; 4.E.169.166; 4.E.169.169;

TABLE 100-continued

4.E.169.172; 4.E.169.175; 4.E.169.240; 4.E.169.244; 4.E.172.228; 4.E.172.229; 4.E.172.230; 4.E.172.231; 4.E.172.236; 4.E.172.237; 4.E.172.238; 4.E.172.239; 4.E.172.154; 4.E.172.157; 4.E.172.166; 4.E.172.169; 4.E.172.172; 4.E.172.175; 4.E.172.240; 4.E.172.244; 4.E.175.228; 4.E.175.229; 4.E.175.230; 4.E.175.231; 4.E.175.236; 4.E.175.237; 4.E.175.238; 4.E.175.239; 4.E.175.154; 4.E.175.157; 4.E.175.166; 4.E.175.169; 4.E.175.172; 4.E.175.175; 4.E.175.240; 4.E.175.244; 4.E.240.228; 4.E.240.229; 4.E.240.230; 4.E.240.231; 4.E.240.236; 4.E.240.237; 4.E.240.238; 4.E.240.239; 4.E.240.154; 4.E.240.157; 4.E.240.166; 4.E.240.169; 4.E.240.172; 4.E.240.175; 4.E.240.240; 4.E.240.244; 4.E.244.228; 4.E.244.229; 4.E.244.230; 4.E.244.231; 4.E.244.236; 4.E.244.237; 4.E.244.238; 4.E.244.239; 4.E.244.154; 4.E.244.157; 4.E.244.166; 4.E.244.169; 4.E.244.172; 4.E.244.175; 4.E.244.240; 4.E.244.244;

Prodrugs of 4.G

4.G.228.228; 4.G.228.229; 4.G.228.230; 4.G.228.231; 4.G.228.236; 4.G.228.237; 4.G.228.238; 4.G.228.239; 4.G.228.154; 4.G.228.157; 4.G.228.166; 4.G.228.169; 4.G.228.172; 4.G.228.175; 4.G.228.240; 4.G.228.244; 4.G.229.228; 4.G.229.229; 4.G.229.230; 4.G.229.231; 4.G.229.236; 4.G.229.237; 4.G.229.238; 4.G.229.239; 4.G.229.154; 4.G.229.157; 4.G.229.166; 4.G.229.169; 4.G.229.172; 4.G.229.175; 4.G.229.240; 4.G.229.244; 4.G.230.228; 4.G.230.229; 4.G.230.230; 4.G.230.231; 4.G.230.236; 4.G.230.237; 4.G.230.238; 4.G.230.239; 4.G.230.154; 4.G.230.157; 4.G.230.166; 4.G.230.169; 4.G.230.172; 4.G.230.175; 4.G.230.240; 4.G.230.244; 4.G.231.228; 4.G.231.229; 4.G.231.230; 4.G.231.231; 4.G.231.236; 4.G.231.237; 4.G.231.238; 4.G.231.239; 4.G.231.154; 4.G.231.157; 4.G.231.166; 4.G.231.169; 4.G.231.172; 4.G.231.175; 4.G.231.240; 4.G.231.244; 4.G.236.228; 4.G.236.229; 4.G.236.230; 4.G.236.231; 4.G.236.236; 4.G.236.237; 4.G.236.238; 4.G.236.239; 4.G.236.154; 4.G.236.157; 4.G.236.166; 4.G.236.169; 4.G.236.172; 4.G.236.175; 4.G.236.240; 4.G.236.244; 4.G.237.228; 4.G.237.229; 4.G.237.230; 4.G.237.231; 4.G.237.236; 4.G.237.237; 4.G.237.238; 4.G.237.239; 4.G.237.154; 4.G.237.157; 4.G.237.166; 4.G.237.169; 4.G.237.172; 4.G.237.175; 4.G.237.240; 4.G.237.244; 4.G.238.228; 4.G.238.229; 4.G.238.230; 4.G.238.231; 4.G.238.236; 4.G.238.237; 4.G.238.238; 4.G.238.239; 4.G.238.154; 4.G.238.157; 4.G.238.166; 4.G.238.169; 4.G.238.172; 4.G.238.175; 4.G.238.240; 4.G.238.244; 4.G.239.228; 4.G.239.229; 4.G.239.230; 4.G.239.231; 4.G.239.236; 4.G.239.237; 4.G.239.238; 4.G.239.239; 4.G.239.154; 4.G.239.157; 4.G.239.166; 4.G.239.169; 4.G.239.172; 4.G.239.175; 4.G.239.240; 4.G.239.244; 4.G.154.228; 4.G.154.229; 4.G.154.230; 4.G.154.231; 4.G.154.236; 4.G.154.237; 4.G.154.238; 4.G.154.239; 4.G.154.154; 4.G.154.157; 4.G.154.166; 4.G.154.169; 4.G.154.172; 4.G.154.175; 4.G.154.240; 4.G.154.244; 4.G.157.228; 4.G.157.229; 4.G.157.230; 4.G.157.231; 4.G.157.236; 4.G.157.237; 4.G.157.238; 4.G.157.239; 4.G.157.154; 4.G.157.157; 4.G.157.166; 4.G.157.169; 4.G.157.172; 4.G.157.175; 4.G.157.240; 4.G.157.244; 4.G.166.228; 4.G.166.229; 4.G.166.230; 4.G.166.231; 4.G.166.236; 4.G.166.237; 4.G.166.238; 4.G.166.239; 4.G.166.154; 4.G.166.157; 4.G.166.166; 4.G.166.169; 4.G.166.172; 4.G.166.175; 4.G.166.240; 4.G.166.244; 4.G.169.228; 4.G.169.229; 4.G.169.230; 4.G.169.231; 4.G.169.236; 4.G.169.237; 4.G.169.238; 4.G.169.239; 4.G.169.154; 4.G.169.157; 4.G.169.166; 4.G.169.169; 4.G.169.172; 4.G.169.175; 4.G.169.240; 4.G.169.244; 4.G.172.228; 4.G.172.229; 4.G.172.230; 4.G.172.231; 4.G.172.236; 4.G.172.237; 4.G.172.238; 4.G.172.239; 4.G.172.154; 4.G.172.157; 4.G.172.166; 4.G.172.169; 4.G.172.172; 4.G.172.175; 4.G.172.240; 4.G.172.244; 4.G.175.228; 4.G.175.229; 4.G.175.230; 4.G.175.231; 4.G.175.236; 4.G.175.237; 4.G.175.238; 4.G.175.239; 4.G.175.154; 4.G.175.157; 4.G.175.166; 4.G.175.169; 4.G.175.172; 4.G.175.175; 4.G.175.240; 4.G.175.244; 4.G.240.228; 4.G.240.229; 4.G.240.230; 4.G.240.231; 4.G.240.236; 4.G.240.237; 4.G.240.238; 4.G.240.239; 4.G.240.154; 4.G.240.157; 4.G.240.166; 4.G.240.169; 4.G.240.172; 4.G.240.175; 4.G.240.240; 4.G.240.244; 4.G.244.228; 4.G.244.229; 4.G.244.230; 4.G.244.231; 4.G.244.236; 4.G.244.237; 4.G.244.238; 4.G.244.239; 4.G.244.154; 4.G.244.157; 4.G.244.166; 4.G.244.169; 4.G.244.172; 4.G.244.175; 4.G.244.240; 4.G.244.244;

Prodrugs of 4.I

4.I.228.228; 4.I.228.229; 4.I.228.230; 4.I.228.231; 4.I.228.236; 4.I.228.237; 4.I.228.238; 4.I.228.239; 4.I.228.154; 4.I.228.157; 4.I.228.166; 4.I.228.169; 4.I.228.172; 4.I.228.175; 4.I.228.240; 4.I.228.244; 4.I.229.228; 4.I.229.229; 4.I.229.230; 4.I.229.231; 4.I.229.236; 4.I.229.237; 4.I.229.238; 4.I.229.239; 4.I.229.154; 4.I.229.157; 4.I.229.166; 4.I.229.169; 4.I.229.172; 4.I.229.175; 4.I.229.240; 4.I.229.244; 4.I.230.228; 4.I.230.229; 4.I.230.230; 4.I.230.231; 4.I.230.236; 4.I.230.237; 4.I.230.238; 4.I.230.239; 4.I.230.154; 4.I.230.157; 4.I.230.166; 4.I.230.169; 4.I.230.172; 4.I.230.175; 4.I.230.240; 4.I.230.244; 4.I.231.228; 4.I.231.229; 4.I.231.230; 4.I.231.231; 4.I.231.236; 4.I.231.237; 4.I.231.238; 4.I.231.239; 4.I.231.154; 4.I.231.157; 4.I.231.166; 4.I.231.169; 4.I.231.172; 4.I.231.175; 4.I.231.240; 4.I.231.244; 4.I.236.228; 4.I.236.229; 4.I.236.230; 4.I.236.231; 4.I.236.236; 4.I.236.237; 4.I.236.238; 4.I.236.239; 4.I.236.154; 4.I.236.157; 4.I.236.166; 4.I.236.169; 4.I.236.172; 4.I.236.175; 4.I.236.240; 4.I.236.244; 4.I.237.228; 4.I.237.229; 4.I.237.230; 4.I.237.231; 4.I.237.236; 4.I.237.237; 4.I.237.238; 4.I.237.239; 4.I.237.154; 4.I.237.157; 4.I.237.166; 4.I.237.169; 4.I.237.172; 4.I.237.175; 4.I.237.240; 4.I.237.244; 4.I.238.228; 4.I.238.229; 4.I.238.230; 4.I.238.231; 4.I.238.236; 4.I.238.237; 4.I.238.238; 4.I.238.239; 4.I.238.154; 4.I.238.157; 4.I.238.166; 4.I.238.169; 4.I.238.172; 4.I.238.175; 4.I.238.240; 4.I.238.244; 4.I.239.228; 4.I.239.229; 4.I.239.230; 4.I.239.231; 4.I.239.236; 4.I.239.237; 4.I.239.238; 4.I.239.239; 4.I.239.154; 4.I.239.157; 4.I.239.166; 4.I.239.169; 4.I.239.172; 4.I.239.175; 4.I.239.240; 4.I.239.244; 4.I.154.228; 4.I.154.229; 4.I.154.230; 4.I.154.231; 4.I.154.236; 4.I.154.237; 4.I.154.238; 4.I.154.239; 4.I.154.154; 4.I.154.157; 4.I.154.166; 4.I.154.169; 4.I.154.172; 4.I.154.175; 4.I.154.240; 4.I.154.244; 4.I.157.228; 4.I.157.229; 4.I.157.230; 4.I.157.231; 4.I.157.236; 4.I.157.237; 4.I.157.238; 4.I.157.239; 4.I.157.154; 4.I.157.157;

TABLE 100-continued

4.I.157.166; 4.I.157.169; 4.I.157.172; 4.I.157.175; 4.I.157.240; 4.I.157.244; 4.I.166.228; 4.I.166.229; 4.I.166.230; 4.I.166.231; 4.I.166.236; 4.I.166.237; 4.I.166.238; 4.I.166.239; 4.I.166.154; 4.I.166.157; 4.I.166.166; 4.I.166.169; 4.I.166.172; 4.I.166.175; 4.I.166.240; 4.I.166.244; 4.I.169.228; 4.I.169.229; 4.I.169.230; 4.I.169.231; 4.I.169.236; 4.I.169.237; 4.I.169.238; 4.I.169.239; 4.I.169.154; 4.I.169.157; 4.I.169.166; 4.I.169.169; 4.I.169.172; 4.I.169.175; 4.I.169.240; 4.I.169.244; 4.I.172.228; 4.I.172.229; 4.I.172.230; 4.I.172.231; 4.I.172.236; 4.I.172.237; 4.I.172.238; 4.I.172.239; 4.I.172.154; 4.I.172.157; 4.I.172.166; 4.I.172.169; 4.I.172.172; 4.I.172.175; 4.I.172.240; 4.I.172.244; 4.I.175.228; 4.I.175.229; 4.I.175.230; 4.I.175.231; 4.I.175.236; 4.I.175.237; 4.I.175.238; 4.I.175.239; 4.I.175.154; 4.I.175.157; 4.I.175.166; 4.I.175.169; 4.I.175.172; 4.I.175.175; 4.I.175.240; 4.I.175.244; 4.I.240.228; 4.I.240.229; 4.I.240.230; 4.I.240.231; 4.I.240.236; 4.I.240.237; 4.I.240.238; 4.I.240.239; 4.I.240.154; 4.I.240.157; 4.I.240.166; 4.I.240.169; 4.I.240.172; 4.I.240.175; 4.I.240.240; 4.I.240.244; 4.I.244.228; 4.I.244.229; 4.I.244.230; 4.I.244.231; 4.I.244.236; 4.I.244.237; 4.I.244.238; 4.I.244.239; 4.I.244.154; 4.I.244.157; 4.I.244.166; 4.I.244.169; 4.I.244.172; 4.I.244.175; 4.I.244.240; 4.I.244.244;

Prodrugs of 4.J

4.J.228.228; 4.J.228.229; 4.J.228.230; 4.J.228.231; 4.J.228.236; 4.J.228.237; 4.J.228.238; 4.J.228.239; 4.J.228.154; 4.J.228.157; 4.J.228.166; 4.J.228.169; 4.J.228.172; 4.J.228.175; 4.J.228.240; 4.J.228.244; 4.J.229.228; 4.J.229.229; 4.J.229.230; 4.J.229.231; 4.J.229.236; 4.J.229.237; 4.J.229.238; 4.J.229.239; 4.J.229.154; 4.J.229.157; 4.J.229.166; 4.J.229.169; 4.J.229.172; 4.J.229.175; 4.J.229.240; 4.J.229.244; 4.J.230.228; 4.J.230.229; 4.J.230.230; 4.J.230.231; 4.J.230.236; 4.J.230.237; 4.J.230.238; 4.J.230.239; 4.J.230.154; 4.J.230.157; 4.J.230.166; 4.J.230.169; 4.J.230.172; 4.J.230.175; 4.J.230.240; 4.J.230.244; 4.J.231.228; 4.J.231.229; 4.J.231.230; 4.J.231.231; 4.J.231.236; 4.J.231.237; 4.J.231.238; 4.J.231.239; 4.J.231.154; 4.J.231.157; 4.J.231.166; 4.J.231.169; 4.J.231.172; 4.J.231.175; 4.J.231.240; 4.J.231.244; 4.J.236.228; 4.J.236.229; 4.J.236.230; 4.J.236.231; 4.J.236.236; 4.J.236.237; 4.J.236.238; 4.J.236.239; 4.J.236.154; 4.J.236.157; 4.J.236.166; 4.J.236.169; 4.J.236.172; 4.J.236.175; 4.J.236.240; 4.J.236.244; 4.J.237.228; 4.J.237.229; 4.J.237.230; 4.J.237.231; 4.J.237.236; 4.J.237.237; 4.J.237.238; 4.J.237.239; 4.J.237.154; 4.J.237.157; 4.J.237.166; 4.J.237.169; 4.J.237.172; 4.J.237.175; 4.J.237.240; 4.J.237.244; 4.J.238.228; 4.J.238.229; 4.J.238.230; 4.J.238.231; 4.J.238.236; 4.J.238.237; 4.J.238.238; 4.J.238.239; 4.J.238.154; 4.J.238.157; 4.J.238.166; 4.J.238.169; 4.J.238.172; 4.J.238.175; 4.J.238.240; 4.J.238.244; 4.J.239.228; 4.J.239.229; 4.J.239.230; 4.J.239.231; 4.J.239.236; 4.J.239.237; 4.J.239.238; 4.J.239.239; 4.J.239.154; 4.J.239.157; 4.J.239.166; 4.J.239.169; 4.J.239.172; 4.J.239.175; 4.J.239.240; 4.J.239.244; 4.J.154.228; 4.J.154.229; 4.J.154.230; 4.J.154.231; 4.J.154.236; 4.J.154.237; 4.J.154.238; 4.J.154.239; 4.J.154.154; 4.J.154.157; 4.J.154.166; 4.J.154.169; 4.J.154.172; 4.J.154.175; 4.J.154.240; 4.J.154.244; 4.J.157.228; 4.J.157.229; 4.J.157.230; 4.J.157.231; 4.J.157.236; 4.J.157.237; 4.J.157.238; 4.J.157.239; 4.J.157.154; 4.J.157.157; 4.J.157.166; 4.J.157.169; 4.J.157.172; 4.J.157.175; 4.J.157.240; 4.J.157.244; 4.J.166.228; 4.J.166.229; 4.J.166.230; 4.J.166.231; 4.J.166.236; 4.J.166.237; 4.J.166.238; 4.J.166.239; 4.J.166.154; 4.J.166.157; 4.J.166.166; 4.J.166.169; 4.J.166.172; 4.J.166.175; 4.J.166.240; 4.J.166.244; 4.J.169.228; 4.J.169.229; 4.J.169.230; 4.J.169.231; 4.J.169.236; 4.J.169.237; 4.J.169.238; 4.J.169.239; 4.J.169.154; 4.J.169.157; 4.J.169.166; 4.J.169.169; 4.J.169.172; 4.J.169.175; 4.J.169.240; 4.J.169.244; 4.J.172.228; 4.J.172.229; 4.J.172.230; 4.J.172.231; 4.J.172.236; 4.J.172.237; 4.J.172.238; 4.J.172.239; 4.J.172.154; 4.J.172.157; 4.J.172.166; 4.J.172.169; 4.J.172.172; 4.J.172.175; 4.J.172.240; 4.J.172.244; 4.J.175.228; 4.J.175.229; 4.J.175.230; 4.J.175.231; 4.J.175.236; 4.J.175.237; 4.J.175.238; 4.J.175.239; 4.J.175.154; 4.J.175.157; 4.J.175.166; 4.J.175.169; 4.J.175.172; 4.J.175.175; 4.J.175.240; 4.J.175.244; 4.J.240.228; 4.J.240.229; 4.J.240.230; 4.J.240.231; 4.J.240.236; 4.J.240.237; 4.J.240.238; 4.J.240.239; 4.J.240.154; 4.J.240.157; 4.J.240.166; 4.J.240.169; 4.J.240.172; 4.J.240.175; 4.J.240.240; 4.J.240.244; 4.J.244.228; 4.J.244.229; 4.J.244.230; 4.J.244.231; 4.J.244.236; 4.J.244.237; 4.J.244.238; 4.J.244.239; 4.J.244.154; 4.J.244.157; 4.J.244.166; 4.J.244.169; 4.J.244.172; 4.J.244.175; 4.J.244.240; 4.J.244.244;

Prodrugs of 4.L

4.L.228.228; 4.L.228.229; 4.L.228.230; 4.L.228.231; 4.L.228.236; 4.L.228.237; 4.L.228.238; 4.L.228.239; 4.L.228.154; 4.L.228.157; 4.L.228.166; 4.L.228.169; 4.L.228.172; 4.L.228.175; 4.L.228.240; 4.L.228.244; 4.L.229.228; 4.L.229.229; 4.L.229.230; 4.L.229.231; 4.L.229.236; 4.L.229.237; 4.L.229.238; 4.L.229.239; 4.L.229.154; 4.L.229.157; 4.L.229.166; 4.L.229.169; 4.L.229.172; 4.L.229.175; 4.L.229.240; 4.L.229.244; 4.L.230.228; 4.L.230.229; 4.L.230.230; 4.L.230.231; 4.L.230.236; 4.L.230.237; 4.L.230.238; 4.L.230.239; 4.L.230.154; 4.L.230.157; 4.L.230.166; 4.L.230.169; 4.L.230.172; 4.L.230.175; 4.L.230.240; 4.L.230.244; 4.L.231.228; 4.L.231.229; 4.L.231.230; 4.L.231.231; 4.L.231.236; 4.L.231.237; 4.L.231.238; 4.L.231.239; 4.L.231.154; 4.L.231.157; 4.L.231.166; 4.L.231.169; 4.L.231.172; 4.L.231.175; 4.L.231.240; 4.L.231.244; 4.L.236.228; 4.L.236.229; 4.L.236.230; 4.L.236.231; 4.L.236.236; 4.L.236.237; 4.L.236.238; 4.L.236.239; 4.L.236.154; 4.L.236.157; 4.L.236.166; 4.L.236.169; 4.L.236.172; 4.L.236.175; 4.L.236.240; 4.L.236.244; 4.L.237.228; 4.L.237.229; 4.L.237.230; 4.L.237.231; 4.L.237.236; 4.L.237.237; 4.L.237.238; 4.L.237.239; 4.L.237.154; 4.L.237.157; 4.L.237.166; 4.L.237.169; 4.L.237.172; 4.L.237.175; 4.L.237.240; 4.L.237.244; 4.L.238.228; 4.L.238.229; 4.L.238.230; 4.L.238.231; 4.L.238.236; 4.L.238.237; 4.L.238.238; 4.L.238.239; 4.L.238.154; 4.L.238.157; 4.L.238.166; 4.L.238.169; 4.L.238.172; 4.L.238.175; 4.L.238.240; 4.L.238.244; 4.L.239.228; 4.L.239.229; 4.L.239.230; 4.L.239.231; 4.L.239.236; 4.L.239.237; 4.L.239.238; 4.L.239.239; 4.L.239.154; 4.L.239.157; 4.L.239.166; 4.L.239.169; 4.L.239.172; 4.L.239.175; 4.L.239.240; 4.L.239.244; 4.L.154.228; 4.L.154.229; 4.L.154.230; 4.L.154.231; 4.L.154.236; 4.L.154.237; 4.L.154.238; 4.L.154.239; 4.L.154.154; 4.L.154.157; 4.L.154.166; 4.L.154.169; 4.L.154.172; 4.L.154.175; 4.L.154.240; 4.L.154.244; 4.L.157.228; 4.L.157.229; 4.L.157.230; 4.L.157.231; 4.L.157.236; 4.L.157.237; 4.L.157.238; 4.L.157.239; 4.L.157.154; 4.L.157.157; 4.L.157.166; 4.L.157.169; 4.L.157.172; 4.L.157.175; 4.L.157.240; 4.L.157.244;

TABLE 100-continued

4.L.166.228; 4.L.166.229; 4.L.166.230; 4.L.166.231; 4.L.166.236; 4.L.166.237; 4.L.166.238;
4.L.166.239; 4.L.166.154; 4.L.166.157; 4.L.166.166; 4.L.166.169; 4.L.166.172; 4.L.166.175;
4.L.166.240; 4.L.166.244; 4.L.169.228; 4.L.169.229; 4.L.169.230; 4.L.169.231; 4.L.169.236;
4.L.169.237; 4.L.169.238; 4.L.169.239; 4.L.169.154; 4.L.169.157; 4.L.169.166; 4.L.169.169;
4.L.169.172; 4.L.169.175; 4.L.169.240; 4.L.169.244; 4.L.172.228; 4.L.172.229; 4.L.172.230;
4.L.172.231; 4.L.172.236; 4.L.172.237; 4.L.172.238; 4.L.172.239; 4.L.172.154; 4.L.172.157;
4.L.172.166; 4.L.172.169; 4.L.172.172; 4.L.172.175; 4.L.172.240; 4.L.172.244; 4.L.175.228;
4.L.175.229; 4.L.175.230; 4.L.175.231; 4.L.175.236; 4.L.175.237; 4.L.175.238; 4.L.175.239;
4.L.175.154; 4.L.175.157; 4.L.175.166; 4.L.175.169; 4.L.175.172; 4.L.175.175; 4.L.175.240;
4.L.175.244; 4.L.240.228; 4.L.240.229; 4.L.240.230; 4.L.240.231; 4.L.240.236; 4.L.240.237;
4.L.240.238; 4.L.240.239; 4.L.240.154; 4.L.240.157; 4.L.240.166; 4.L.240.169; 4.L.240.172;
4.L.240.175; 4.L.240.240; 4.L.240.244; 4.L.244.228; 4.L.244.229; 4.L.244.230; 4.L.244.231;
4.L.244.236; 4.L.244.237; 4.L.244.238; 4.L.244.239; 4.L.244.154; 4.L.244.157; 4.L.244.166;
4.L.244.169; 4.L.244.172; 4.L.244.175; 4.L.244.240; 4.L.244.244;

Prodrugs of 4.O

4.O.228.228; 4.O.228.229; 4.O.228.230; 4.O.228.231; 4.O.228.236; 4.O.228.237;
4.O.228.238; 4.O.228.239; 4.O.228.154; 4.O.228.157; 4.O.228.166; 4.O.228.169;
4.O.228.172; 4.O.228.175; 4.O.228.240; 4.O.228.244; 4.O.229.228; 4.O.229.229;
4.O.229.230; 4.O.229.231; 4.O.229.236; 4.O.229.237; 4.O.229.238; 4.O.229.239;
4.O.229.154; 4.O.229.157; 4.O.229.166; 4.O.229.169; 4.O.229.172; 4.O.229.175;
4.O.229.240; 4.O.229.244; 4.O.230.228; 4.O.230.229; 4.O.230.230; 4.O.230.231;
4.O.230.236; 4.O.230.237; 4.O.230.238; 4.O.230.239; 4.O.230.154; 4.O.230.157;
4.O.230.166; 4.O.230.169; 4.O.230.172; 4.O.230.175; 4.O.230.240; 4.O.230.244;
4.O.231.228; 4.O.231.229; 4.O.231.230; 4.O.231.231; 4.O.231.236; 4.O.231.237;
4.O.231.238; 4.O.231.239; 4.O.231.154; 4.O.231.157; 4.O.231.166; 4.O.231.169;
4.O.231.172; 4.O.231.175; 4.O.231.240; 4.O.231.244; 4.O.236.228; 4.O.236.229;
4.O.236.230; 4.O.236.231; 4.O.236.236; 4.O.236.237; 4.O.236.238; 4.O.236.239;
4.O.236.154; 4.O.236.157; 4.O.236.166; 4.O.236.169; 4.O.236.172; 4.O.236.175;
4.O.236.240; 4.O.236.244; 4.O.237.228; 4.O.237.229; 4.O.237.230; 4.O.237.231;
4.O.237.236; 4.O.237.237; 4.O.237.238; 4.O.237.239; 4.O.237.154; 4.O.237.157;
4.O.237.166; 4.O.237.169; 4.O.237.172; 4.O.237.175; 4.O.237.240; 4.O.237.244;
4.O.238.228; 4.O.238.229; 4.O.238.230; 4.O.238.231; 4.O.238.236; 4.O.238.237;
4.O.238.238; 4.O.238.239; 4.O.238.154; 4.O.238.157; 4.O.238.166; 4.O.238.169;
4.O.238.172; 4.O.238.175; 4.O.238.240; 4.O.238.244; 4.O.239.228; 4.O.239.229;
4.O.239.230; 4.O.239.231; 4.O.239.236; 4.O.239.237; 4.O.239.238; 4.O.239.239;
4.O.239.154; 4.O.239.157; 4.O.239.166; 4.O.239.169; 4.O.239.172; 4.O.239.175;
4.O.239.240; 4.O.239.244; 4.O.154.228; 4.O.154.229; 4.O.154.230; 4.O.154.231;
4.O.154.236; 4.O.154.237; 4.O.154.238; 4.O.154.239; 4.O.154.154; 4.O.154.157;
4.O.154.166; 4.O.154.169; 4.O.154.172; 4.O.154.175; 4.O.154.240; 4.O.154.244;
4.O.157.228; 4.O.157.229; 4.O.157.230; 4.O.157.231; 4.O.157.236; 4.O.157.237;
4.O.157.238; 4.O.157.239; 4.O.157.154; 4.O.157.157; 4.O.157.166; 4.O.157.169;
4.O.157.172; 4.O.157.175; 4.O.157.240; 4.O.157.244; 4.O.166.228; 4.O.166.229;
4.O.166.230; 4.O.166.231; 4.O.166.236; 4.O.166.237; 4.O.166.238; 4.O.166.239;
4.O.166.154; 4.O.166.157; 4.O.166.166; 4.O.166.169; 4.O.166.172; 4.O.166.175;
4.O.166.240; 4.O.166.244; 4.O.169.228; 4.O.169.229; 4.O.169.230; 4.O.169.231;
4.O.169.236; 4.O.169.237; 4.O.169.238; 4.O.169.239; 4.O.169.154; 4.O.169.157;
4.O.169.166; 4.O.169.169; 4.O.169.172; 4.O.169.175; 4.O.169.240; 4.O.169.244;
4.O.172.228; 4.O.172.229; 4.O.172.230; 4.O.172.231; 4.O.172.236; 4.O.172.237;
4.O.172.238; 4.O.172.239; 4.O.172.154; 4.O.172.157; 4.O.172.166; 4.O.172.169;
4.O.172.172; 4.O.172.175; 4.O.172.240; 4.O.172.244; 4.O.175.228; 4.O.175.229;
4.O.175.230; 4.O.175.231; 4.O.175.236; 4.O.175.237; 4.O.175.238; 4.O.175.239;
4.O.175.154; 4.O.175.157; 4.O.175.166; 4.O.175.169; 4.O.175.172; 4.O.175.175;
4.O.175.240; 4.O.175.244; 4.O.240.228; 4.O.240.229; 4.O.240.230; 4.O.240.231;
4.O.240.236; 4.O.240.237; 4.O.240.238; 4.O.240.239; 4.O.240.154; 4.O.240.157;
4.O.240.166; 4.O.240.169; 4.O.240.172; 4.O.240.175; 4.O.240.240; 4.O.240.244;
4.O.244.228; 4.O.244.229; 4.O.244.230; 4.O.244.231; 4.O.244.236; 4.O.244.237;
4.O.244.238; 4.O.244.239; 4.O.244.154; 4.O.244.157; 4.O.244.166; 4.O.244.169;
4.O.244.172; 4.O.244.175; 4.O.244.240; 4.O.244.244;

Prodrugs of 4.P

4.P.228.228; 4.P.228.229; 4.P.228.230; 4.P.228.231; 4.P.228.236; 4.P.228.237;
4.P.228.238; 4.P.228.239; 4.P.228.154; 4.P.228.157; 4.P.228.166; 4.P.228.169; 4.P.228.172;
4.P.228.175; 4.P.228.240; 4.P.228.244; 4.P.229.228; 4.P.229.229; 4.P.229.230; 4.P.229.231;
4.P.229.236; 4.P.229.237; 4.P.229.238; 4.P.229.239; 4.P.229.154; 4.P.229.157; 4.P.229.166;
4.P.229.169; 4.P.229.172; 4.P.229.175; 4.P.229.240; 4.P.229.244; 4.P.230.228; 4.P.230.229;
4.P.230.230; 4.P.230.231; 4.P.230.236; 4.P.230.237; 4.P.230.238; 4.P.230.239; 4.P.230.154;
4.P.230.157; 4.P.230.166; 4.P.230.169; 4.P.230.172; 4.P.230.175; 4.P.230.240; 4.P.230.244;
4.P.231.228; 4.P.231.229; 4.P.231.230; 4.P.231.231; 4.P.231.236; 4.P.231.237; 4.P.231.238;
4.P.231.239; 4.P.231.154; 4.P.231.157; 4.P.231.166; 4.P.231.169; 4.P.231.172; 4.P.231.175;
4.P.231.240; 4.P.231.244; 4.P.236.228; 4.P.236.229; 4.P.236.230; 4.P.236.231; 4.P.236.236;
4.P.236.237; 4.P.236.238; 4.P.236.239; 4.P.236.154; 4.P.236.157; 4.P.236.166; 4.P.236.169;
4.P.236.172; 4.P.236.175; 4.P.236.240; 4.P.236.244; 4.P.237.228; 4.P.237.229; 4.P.237.230;
4.P.237.231; 4.P.237.236; 4.P.237.237; 4.P.237.238; 4.P.237.239; 4.P.237.154; 4.P.237.157;
4.P.237.166; 4.P.237.169; 4.P.237.172; 4.P.237.175; 4.P.237.240; 4.P.237.244; 4.P.238.228;
4.P.238.229; 4.P.238.230; 4.P.238.231; 4.P.238.236; 4.P.238.237; 4.P.238.238; 4.P.238.239;
4.P.238.154; 4.P.238.157; 4.P.238.166; 4.P.238.169; 4.P.238.172; 4.P.238.175; 4.P.238.240;
4.P.238.244; 4.P.239.228; 4.P.239.229; 4.P.239.230; 4.P.239.231; 4.P.239.236; 4.P.239.237;
4.P.239.238; 4.P.239.239; 4.P.239.154; 4.P.239.157; 4.P.239.166; 4.P.239.169; 4.P.239.172;

TABLE 100-continued

4.P.239.175; 4.P.239.240; 4.P.239.244; 4.P.154.228; 4.P.154.229; 4.P.154.230; 4.P.154.231; 4.P.154.236; 4.P.154.237; 4.P.154.238; 4.P.154.239; 4.P.154.154; 4.P.154.157; 4.P.154.166; 4.P.154.169; 4.P.154.172; 4.P.154.175; 4.P.154.240; 4.P.154.244; 4.P.157.228; 4.P.157.229; 4.P.157.230; 4.P.157.231; 4.P.157.236; 4.P.157.237; 4.P.157.238; 4.P.157.239; 4.P.157.154; 4.P.157.157; 4.P.157.166; 4.P.157.169; 4.P.157.172; 4.P.157.175; 4.P.157.240; 4.P.157.244; 4.P.166.228; 4.P.166.229; 4.P.166.230; 4.P.166.231; 4.P.166.236; 4.P.166.237; 4.P.166.238; 4.P.166.239; 4.P.166.154; 4.P.166.157; 4.P.166.166; 4.P.166.169; 4.P.166.172; 4.P.166.175; 4.P.166.240; 4.P.166.244; 4.P.169.228; 4.P.169.229; 4.P.169.230; 4.P.169.231; 4.P.169.236; 4.P.169.237; 4.P.169.238; 4.P.169.239; 4.P.169.154; 4.P.169.157; 4.P.169.166; 4.P.169.169; 4.P.169.172; 4.P.169.175; 4.P.169.240; 4.P.169.244; 4.P.172.228; 4.P.172.229; 4.P.172.230; 4.P.172.231; 4.P.172.236; 4.P.172.237; 4.P.172.238; 4.P.172.239; 4.P.172.154; 4.P.172.157; 4.P.172.166; 4.P.172.169; 4.P.172.172; 4.P.172.175; 4.P.172.240; 4.P.172.244; 4.P.175.228; 4.P.175.229; 4.P.175.230; 4.P.175.231; 4.P.175.236; 4.P.175.237; 4.P.175.238; 4.P.175.239; 4.P.175.154; 4.P.175.157; 4.P.175.166; 4.P.175.169; 4.P.175.172; 4.P.175.175; 4.P.175.240; 4.P.175.244; 4.P.240.228; 4.P.240.229; 4.P.240.230; 4.P.240.231; 4.P.240.236; 4.P.240.237; 4.P.240.238; 4.P.240.239; 4.P.240.154; 4.P.240.157; 4.P.240.166; 4.P.240.169; 4.P.240.172; 4.P.240.175; 4.P.240.240; 4.P.240.244; 4.P.244.228; 4.P.244.229; 4.P.244.230; 4.P.244.231; 4.P.244.236; 4.P.244.237; 4.P.244.238; 4.P.244.239; 4.P.244.154; 4.P.244.157; 4.P.244.166; 4.P.244.169; 4.P.244.172; 4.P.244.175; 4.P.244.240; 4.P.244.244;

Prodrugs of 4.U

4.U.228.228; 4.U.228.229; 4.U.228.230; 4.U.228.231; 4.U.228.236; 4.U.228.237; 4.U.228.238; 4.U.228.239; 4.U.228.154; 4.U.228.157; 4.U.228.166; 4.U.228.169; 4.U.228.172; 4.U.228.175; 4.U.228.240; 4.U.228.244; 4.U.229.228; 4.U.229.229; 4.U.229.230; 4.U.229.231; 4.U.229.236; 4.U.229.237; 4.U.229.238; 4.U.229.239; 4.U.229.154; 4.U.229.157; 4.U.229.166; 4.U.229.169; 4.U.229.172; 4.U.229.175; 4.U.229.240; 4.U.229.244; 4.U.230.228; 4.U.230.229; 4.U.230.230; 4.U.230.231; 4.U.230.236; 4.U.230.237; 4.U.230.238; 4.U.230.239; 4.U.230.154; 4.U.230.157; 4.U.230.166; 4.U.230.169; 4.U.230.172; 4.U.230.175; 4.U.230.240; 4.U.230.244; 4.U.231.228; 4.U.231.229; 4.U.231.230; 4.U.231.231; 4.U.231.236; 4.U.231.237; 4.U.231.238; 4.U.231.239; 4.U.231.154; 4.U.231.157; 4.U.231.166; 4.U.231.169; 4.U.231.172; 4.U.231.175; 4.U.231.240; 4.U.231.244; 4.U.236.228; 4.U.236.229; 4.U.236.230; 4.U.236.231; 4.U.236.236; 4.U.236.237; 4.U.236.238; 4.U.236.239; 4.U.236.154; 4.U.236.157; 4.U.236.166; 4.U.236.169; 4.U.236.172; 4.U.236.175; 4.U.236.240; 4.U.236.244; 4.U.237.228; 4.U.237.229; 4.U.237.230; 4.U.237.231; 4.U.237.236; 4.U.237.237; 4.U.237.238; 4.U.237.239; 4.U.237.154; 4.U.237.157; 4.U.237.166; 4.U.237.169; 4.U.237.172; 4.U.237.175; 4.U.237.240; 4.U.237.244; 4.U.238.228; 4.U.238.229; 4.U.238.230; 4.U.238.231; 4.U.238.236; 4.U.238.237; 4.U.238.238; 4.U.238.239; 4.U.238.154; 4.U.238.157; 4.U.238.166; 4.U.238.169; 4.U.238.172; 4.U.238.175; 4.U.238.240; 4.U.238.244; 4.U.239.228; 4.U.239.229; 4.U.239.230; 4.U.239.231; 4.U.239.236; 4.U.239.237; 4.U.239.238; 4.U.239.239; 4.U.239.154; 4.U.239.157; 4.U.239.166; 4.U.239.169; 4.U.239.172; 4.U.239.175; 4.U.239.240; 4.U.239.244; 4.U.154.228; 4.U.154.229; 4.U.154.230; 4.U.154.231; 4.U.154.236; 4.U.154.237; 4.U.154.238; 4.U.154.239; 4.U.154.154; 4.U.154.157; 4.U.154.166; 4.U.154.169; 4.U.154.172; 4.U.154.175; 4.U.154.240; 4.U.154.244; 4.U.157.228; 4.U.157.229; 4.U.157.230; 4.U.157.231; 4.U.157.236; 4.U.157.237; 4.U.157.238; 4.U.157.239; 4.U.157.154; 4.U.157.157; 4.U.157.166; 4.U.157.169; 4.U.157.172; 4.U.157.175; 4.U.157.240; 4.U.157.244; 4.U.166.228; 4.U.166.229; 4.U.166.230; 4.U.166.231; 4.U.166.236; 4.U.166.237; 4.U.166.238; 4.U.166.239; 4.U.166.154; 4.U.166.157; 4.U.166.166; 4.U.166.169; 4.U.166.172; 4.U.166.175; 4.U.166.240; 4.U.166.244; 4.U.169.228; 4.U.169.229; 4.U.169.230; 4.U.169.231; 4.U.169.236; 4.U.169.237; 4.U.169.238; 4.U.169.239; 4.U.169.154; 4.U.169.157; 4.U.169.166; 4.U.169.169; 4.U.169.172; 4.U.169.175; 4.U.169.240; 4.U.169.244; 4.U.172.228; 4.U.172.229; 4.U.172.230; 4.U.172.231; 4.U.172.236; 4.U.172.237; 4.U.172.238; 4.U.172.239; 4.U.172.154; 4.U.172.157; 4.U.172.166; 4.U.172.169; 4.U.172.172; 4.U.172.175; 4.U.172.240; 4.U.172.244; 4.U.175.228; 4.U.175.229; 4.U.175.230; 4.U.175.231; 4.U.175.236; 4.U.175.237; 4.U.175.238; 4.U.175.239; 4.U.175.154; 4.U.175.157; 4.U.175.166; 4.U.175.169; 4.U.175.172; 4.U.175.175; 4.U.175.240; 4.U.175.244; 4.U.240.228; 4.U.240.229; 4.U.240.230; 4.U.240.231; 4.U.240.236; 4.U.240.237; 4.U.240.238; 4.U.240.239; 4.U.240.154; 4.U.240.157; 4.U.240.166; 4.U.240.169; 4.U.240.172; 4.U.240.175; 4.U.240.240; 4.U.240.244; 4.U.244.228; 4.U.244.229; 4.U.244.230; 4.U.244.231; 4.U.244.236; 4.U.244.237; 4.U.244.238; 4.U.244.239; 4.U.244.154; 4.U.244.157; 4.U.244.166; 4.U.244.169; 4.U.244.172; 4.U.244.175; 4.U.244.240; 4.U.244.244;

Prodrugs of 4.W

4.W.228.228; 4.W.228.229; 4.W.228.230; 4.W.228.231; 4.W.228.236; 4.W.228.237; 4.W.228.238; 4.W.228.239; 4.W.228.154; 4.W.228.157; 4.W.228.166; 4.W.228.169; 4.W.228.172; 4.W.228.175; 4.W.228.240; 4.W.228.244; 4.W.229.228; 4.W.229.229; 4.W.229.230; 4.W.229.231; 4.W.229.236; 4.W.229.237; 4.W.229.238; 4.W.229.239; 4.W.229.154; 4.W.229.157; 4.W.229.166; 4.W.229.169; 4.W.229.172; 4.W.229.175; 4.W.229.240; 4.W.229.244; 4.W.230.228; 4.W.230.229; 4.W.230.230; 4.W.230.231; 4.W.230.236; 4.W.230.237; 4.W.230.238; 4.W.230.239; 4.W.230.154; 4.W.230.157; 4.W.230.166; 4.W.230.169; 4.W.230.172; 4.W.230.175; 4.W.230.240; 4.W.230.244; 4.W.231.228; 4.W.231.229; 4.W.231.230; 4.W.231.231; 4.W.231.236; 4.W.231.237; 4.W.231.238; 4.W.231.239; 4.W.231.154; 4.W.231.157; 4.W.231.166; 4.W.231.169; 4.W.231.172; 4.W.231.175; 4.W.231.240; 4.W.231.244; 4.W.236.228; 4.W.236.229; 4.W.236.230; 4.W.236.231; 4.W.236.236; 4.W.236.237; 4.W.236.238; 4.W.236.239; 4.W.236.154; 4.W.236.157; 4.W.236.166; 4.W.236.169; 4.W.236.172; 4.W.236.175;

TABLE 100-continued

4.W.236.240; 4.W.236.244; 4.W.237.228; 4.W.237.229; 4.W.237.230; 4.W.237.231; 4.W.237.236; 4.W.237.237; 4.W.237.238; 4.W.237.239; 4.W.237.154; 4.W.237.157; 4.W.237.166; 4.W.237.169; 4.W.237.172; 4.W.237.175; 4.W.237.240; 4.W.237.244; 4.W.238.228; 4.W.238.229; 4.W.238.230; 4.W.238.231; 4.W.238.236; 4.W.238.237; 4.W.238.238; 4.W.238.239; 4.W.238.154; 4.W.238.157; 4.W.238.166; 4.W.238.169; 4.W.238.172; 4.W.238.175; 4.W.238.240; 4.W.238.244; 4.W.239.228; 4.W.239.229; 4.W.239.230; 4.W.239.231; 4.W.239.236; 4.W.239.237; 4.W.239.238; 4.W.239.239; 4.W.239.154; 4.W.239.157; 4.W.239.166; 4.W.239.169; 4.W.239.172; 4.W.239.175; 4.W.239.240; 4.W.239.244; 4.W.154.228; 4.W.154.229; 4.W.154.230; 4.W.154.231; 4.W.154.236; 4.W.154.237; 4.W.154.238; 4.W.154.239; 4.W.154.154; 4.W.154.157; 4.W.154.166; 4.W.154.169; 4.W.154.172; 4.W.154.175; 4.W.154.240; 4.W.154.244; 4.W.157.228; 4.W.157.229; 4.W.157.230; 4.W.157.231; 4.W.157.236; 4.W.157.237; 4.W.157.238; 4.W.157.239; 4.W.157.154; 4.W.157.157; 4.W.157.166; 4.W.157.169; 4.W.157.172; 4.W.157.175; 4.W.157.240; 4.W.157.244; 4.W.166.228; 4.W.166.229; 4.W.166.230; 4.W.166.231; 4.W.166.236; 4.W.166.237; 4.W.166.238; 4.W.166.239; 4.W.166.154; 4.W.166.157; 4.W.166.166; 4.W.166.169; 4.W.166.172; 4.W.166.175; 4.W.166.240; 4.W.166.244; 4.W.169.228; 4.W.169.229; 4.W.169.230; 4.W.169.231; 4.W.169.236; 4.W.169.237; 4.W.169.238; 4.W.169.239; 4.W.169.154; 4.W.169.157; 4.W.169.166; 4.W.169.169; 4.W.169.172; 4.W.169.175; 4.W.169.240; 4.W.169.244; 4.W.172.228; 4.W.172.229; 4.W.172.230; 4.W.172.231; 4.W.172.236; 4.W.172.237; 4.W.172.238; 4.W.172.239; 4.W.172.154; 4.W.172.157; 4.W.172.166; 4.W.172.169; 4.W.172.172; 4.W.172.175; 4.W.172.240; 4.W.172.244; 4.W.175.228; 4.W.175.229; 4.W.175.230; 4.W.175.231; 4.W.175.236; 4.W.175.237; 4.W.175.238; 4.W.175.239; 4.W.175.154; 4.W.175.157; 4.W.175.166; 4.W.175.169; 4.W.175.172; 4.W.175.175; 4.W.175.240; 4.W.175.244; 4.W.240.228; 4.W.240.229; 4.W.240.230; 4.W.240.231; 4.W.240.236; 4.W.240.237; 4.W.240.238; 4.W.240.239; 4.W.240.154; 4.W.240.157; 4.W.240.166; 4.W.240.169; 4.W.240.172; 4.W.240.175; 4.W.240.240; 4.W.240.244; 4.W.244.228; 4.W.244.229; 4.W.244.230; 4.W.244.231; 4.W.244.236; 4.W.244.237; 4.W.244.238; 4.W.244.239; 4.W.244.154; 4.W.244.157; 4.W.244.166; 4.W.244.169; 4.W.244.172; 4.W.244.175; 4.W.244.240; 4.W.244.244;

Prodrugs of 4.Y

4.Y.228.228; 4.Y.228.229; 4.Y.228.230; 4.Y.228.231; 4.Y.228.236; 4.Y.228.237; 4.Y.228.238; 4.Y.228.239; 4.Y.228.154; 4.Y.228.157; 4.Y.228.166; 4.Y.228.169; 4.Y.228.172; 4.Y.228.175; 4.Y.228.240; 4.Y.228.244; 4.Y.229.228; 4.Y.229.229; 4.Y.229.230; 4.Y.229.231; 4.Y.229.236; 4.Y.229.237; 4.Y.229.238; 4.Y.229.239; 4.Y.229.154; 4.Y.229.157; 4.Y.229.166; 4.Y.229.169; 4.Y.229.172; 4.Y.229.175; 4.Y.229.240; 4.Y.229.244; 4.Y.230.228; 4.Y.230.229; 4.Y.230.230; 4.Y.230.231; 4.Y.230.236; 4.Y.230.237; 4.Y.230.238; 4.Y.230.239; 4.Y.230.154; 4.Y.230.157; 4.Y.230.166; 4.Y.230.169; 4.Y.230.172; 4.Y.230.175; 4.Y.230.240; 4.Y.230.244; 4.Y.231.228; 4.Y.231.229; 4.Y.231.230; 4.Y.231.231; 4.Y.231.236; 4.Y.231.237; 4.Y.231.238; 4.Y.231.239; 4.Y.231.154; 4.Y.231.157; 4.Y.231.166; 4.Y.231.169; 4.Y.231.172; 4.Y.231.175; 4.Y.231.240; 4.Y.231.244; 4.Y.236.228; 4.Y.236.229; 4.Y.236.230; 4.Y.236.231; 4.Y.236.236; 4.Y.236.237; 4.Y.236.238; 4.Y.236.239; 4.Y.236.154; 4.Y.236.157; 4.Y.236.166; 4.Y.236.169; 4.Y.236.172; 4.Y.236.175; 4.Y.236.240; 4.Y.236.244; 4.Y.237.228; 4.Y.237.229; 4.Y.237.230; 4.Y.237.231; 4.Y.237.236; 4.Y.237.237; 4.Y.237.238; 4.Y.237.239; 4.Y.237.154; 4.Y.237.157; 4.Y.237.166; 4.Y.237.169; 4.Y.237.172; 4.Y.237.175; 4.Y.237.240; 4.Y.237.244; 4.Y.238.228; 4.Y.238.229; 4.Y.238.230; 4.Y.238.231; 4.Y.238.236; 4.Y.238.237; 4.Y.238.238; 4.Y.238.239; 4.Y.238.154; 4.Y.238.157; 4.Y.238.166; 4.Y.238.169; 4.Y.238.172; 4.Y.238.175; 4.Y.238.240; 4.Y.238.244; 4.Y.239.228; 4.Y.239.229; 4.Y.239.230; 4.Y.239.231; 4.Y.239.236; 4.Y.239.237; 4.Y.239.238; 4.Y.239.239; 4.Y.239.154; 4.Y.239.157; 4.Y.239.166; 4.Y.239.169; 4.Y.239.172; 4.Y.239.175; 4.Y.239.240; 4.Y.239.244; 4.Y.154.228; 4.Y.154.229; 4.Y.154.230; 4.Y.154.231; 4.Y.154.236; 4.Y.154.237; 4.Y.154.238; 4.Y.154.239; 4.Y.154.154; 4.Y.154.157; 4.Y.154.166; 4.Y.154.169; 4.Y.154.172; 4.Y.154.175; 4.Y.154.240; 4.Y.154.244; 4.Y.157.228; 4.Y.157.229; 4.Y.157.230; 4.Y.157.231; 4.Y.157.236; 4.Y.157.237; 4.Y.157.238; 4.Y.157.239; 4.Y.157.154; 4.Y.157.157; 4.Y.157.166; 4.Y.157.169; 4.Y.157.172; 4.Y.157.175; 4.Y.157.240; 4.Y.157.244; 4.Y.166.228; 4.Y.166.229; 4.Y.166.230; 4.Y.166.231; 4.Y.166.236; 4.Y.166.237; 4.Y.166.238; 4.Y.166.239; 4.Y.166.154; 4.Y.166.157; 4.Y.166.166; 4.Y.166.169; 4.Y.166.172; 4.Y.166.175; 4.Y.166.240; 4.Y.166.244; 4.Y.169.228; 4.Y.169.229; 4.Y.169.230; 4.Y.169.231; 4.Y.169.236; 4.Y.169.237; 4.Y.169.238; 4.Y.169.239; 4.Y.169.154; 4.Y.169.157; 4.Y.169.166; 4.Y.169.169; 4.Y.169.172; 4.Y.169.175; 4.Y.169.240; 4.Y.169.244; 4.Y.172.228; 4.Y.172.229; 4.Y.172.230; 4.Y.172.231; 4.Y.172.236; 4.Y.172.237; 4.Y.172.238; 4.Y.172.239; 4.Y.172.154; 4.Y.172.157; 4.Y.172.166; 4.Y.172.169; 4.Y.172.172; 4.Y.172.175; 4.Y.172.240; 4.Y.172.244; 4.Y.175.228; 4.Y.175.229; 4.Y.175.230; 4.Y.175.231; 4.Y.175.236; 4.Y.175.237; 4.Y.175.238; 4.Y.175.239; 4.Y.175.154; 4.Y.175.157; 4.Y.175.166; 4.Y.175.169; 4.Y.175.172; 4.Y.175.175; 4.Y.175.240; 4.Y.175.244; 4.Y.240.228; 4.Y.240.229; 4.Y.240.230; 4.Y.240.231; 4.Y.240.236; 4.Y.240.237; 4.Y.240.238; 4.Y.240.239; 4.Y.240.154; 4.Y.240.157; 4.Y.240.166; 4.Y.240.169; 4.Y.240.172; 4.Y.240.175; 4.Y.240.240; 4.Y.240.244; 4.Y.244.228; 4.Y.244.229; 4.Y.244.230; 4.Y.244.231; 4.Y.244.236; 4.Y.244.237; 4.Y.244.238; 4.Y.244.239; 4.Y.244.154; 4.Y.244.157; 4.Y.244.166; 4.Y.244.169; 4.Y.244.172; 4.Y.244.175; 4.Y.244.240; 4.Y.244.244;

Prodrugs of 5.B

5.B.228.228; 5.B.228.229; 5.B.228.230; 5.B.228.231; 5.B.228.236; 5.B.228.237; 5.B.228.238; 5.B.228.239; 5.B.228.154; 5.B.228.157; 5.B.228.166; 5.B.228.169; 5.B.228.172;

TABLE 100-continued

5.B.228.175; 5.B.228.240; 5.B.228.244; 5.B.229.228; 5.B.229.229; 5.B.229.230; 5.B.229.231; 5.B.229.236; 5.B.229.237; 5.B.229.238; 5.B.229.239; 5.B.229.154; 5.B.229.157; 5.B.229.166; 5.B.229.169; 5.B.229.172; 5.B.229.175; 5.B.229.240; 5.B.229.244; 5.B.230.228; 5.B.230.229; 5.B.230.230; 5.B.230.231; 5.B.230.236; 5.B.230.237; 5.B.230.238; 5.B.230.239; 5.B.230.154; 5.B.230.157; 5.B.230.166; 5.B.230.169; 5.B.230.172; 5.B.230.175; 5.B.230.240; 5.B.230.244; 5.B.231.228; 5.B.231.229; 5.B.231.230; 5.B.231.231; 5.B.231.236; 5.B.231.237; 5.B.231.238; 5.B.231.239; 5.B.231.154; 5.B.231.157; 5.B.231.166; 5.B.231.169; 5.B.231.172; 5.B.231.175; 5.B.231.240; 5.B.231.244; 5.B.236.228; 5.B.236.229; 5.B.236.230; 5.B.236.231; 5.B.236.236; 5.B.236.237; 5.B.236.238; 5.B.236.239; 5.B.236.154; 5.B.236.157; 5.B.236.166; 5.B.236.169; 5.B.236.172; 5.B.236.175; 5.B.236.240; 5.B.236.244; 5.B.237.228; 5.B.237.229; 5.B.237.230; 5.B.237.231; 5.B.237.236; 5.B.237.237; 5.B.237.238; 5.B.237.239; 5.B.237.154; 5.B.237.157; 5.B.237.166; 5.B.237.169; 5.B.237.172; 5.B.237.175; 5.B.237.240; 5.B.237.244; 5.B.238.228; 5.B.238.229; 5.B.238.230; 5.B.238.231; 5.B.238.236; 5.B.238.237; 5.B.238.238; 5.B.238.239; 5.B.238.154; 5.B.238.157; 5.B.238.166; 5.B.238.169; 5.B.238.172; 5.B.238.175; 5.B.238.240; 5.B.238.244; 5.B.239.228; 5.B.239.229; 5.B.239.230; 5.B.239.231; 5.B.239.236; 5.B.239.237; 5.B.239.238; 5.B.239.239; 5.B.239.154; 5.B.239.157; 5.B.239.166; 5.B.239.169; 5.B.239.172; 5.B.239.175; 5.B.239.240; 5.B.239.244; 5.B.154.228; 5.B.154.229; 5.B.154.230; 5.B.154.231; 5.B.154.236; 5.B.154.237; 5.B.154.238; 5.B.154.239; 5.B.154.154; 5.B.154.157; 5.B.154.166; 5.B.154.169; 5.B.154.172; 5.B.154.175; 5.B.154.240; 5.B.154.244; 5.B.157.228; 5.B.157.229; 5.B.157.230; 5.B.157.231; 5.B.157.236; 5.B.157.237; 5.B.157.238; 5.B.157.239; 5.B.157.154; 5.B.157.157; 5.B.157.166; 5.B.157.169; 5.B.157.172; 5.B.157.175; 5.B.157.240; 5.B.157.244; 5.B.166.228; 5.B.166.229; 5.B.166.230; 5.B.166.231; 5.B.166.236; 5.B.166.237; 5.B.166.238; 5.B.166.239; 5.B.166.154; 5.B.166.157; 5.B.166.166; 5.B.166.169; 5.B.166.172; 5.B.166.175; 5.B.166.240; 5.B.166.244; 5.B.169.228; 5.B.169.229; 5.B.169.230; 5.B.169.231; 5.B.169.236; 5.B.169.237; 5.B.169.238; 5.B.169.239; 5.B.169.154; 5.B.169.157; 5.B.169.166; 5.B.169.169; 5.B.169.172; 5.B.169.175; 5.B.169.240; 5.B.169.244; 5.B.172.228; 5.B.172.229; 5.B.172.230; 5.B.172.231; 5.B.172.236; 5.B.172.237; 5.B.172.238; 5.B.172.239; 5.B.172.154; 5.B.172.157; 5.B.172.166; 5.B.172.169; 5.B.172.172; 5.B.172.175; 5.B.172.240; 5.B.172.244; 5.B.175.228; 5.B.175.229; 5.B.175.230; 5.B.175.231; 5.B.175.236; 5.B.175.237; 5.B.175.238; 5.B.175.239; 5.B.175.154; 5.B.175.157; 5.B.175.166; 5.B.175.169; 5.B.175.172; 5.B.175.175; 5.B.175.240; 5.B.175.244; 5.B.240.228; 5.B.240.229; 5.B.240.230; 5.B.240.231; 5.B.240.236; 5.B.240.237; 5.B.240.238; 5.B.240.239; 5.B.240.154; 5.B.240.157; 5.B.240.166; 5.B.240.169; 5.B.240.172; 5.B.240.175; 5.B.240.240; 5.B.240.244; 5.B.244.228; 5.B.244.229; 5.B.244.230; 5.B.244.231; 5.B.244.236; 5.B.244.237; 5.B.244.238; 5.B.244.239; 5.B.244.154; 5.B.244.157; 5.B.244.166; 5.B.244.169; 5.B.244.172; 5.B.244.175; 5.B.244.240; 5.B.244.244;

Prodrugs of 5.D

5.D.228.228; 5.D.228.229; 5.D.228.230; 5.D.228.231; 5.D.228.236; 5.D.228.237; 5.D.228.238; 5.D.228.239; 5.D.228.154; 5.D.228.157; 5.D.228.166; 5.D.228.169; 5.D.228.172; 5.D.228.175; 5.D.228.240; 5.D.228.244; 5.D.229.228; 5.D.229.229; 5.D.229.230; 5.D.229.231; 5.D.229.236; 5.D.229.237; 5.D.229.238; 5.D.229.239; 5.D.229.154; 5.D.229.157; 5.D.229.166; 5.D.229.169; 5.D.229.172; 5.D.229.175; 5.D.229.240; 5.D.229.244; 5.D.230.228; 5.D.230.229; 5.D.230.230; 5.D.230.231; 5.D.230.236; 5.D.230.237; 5.D.230.238; 5.D.230.239; 5.D.230.154; 5.D.230.157; 5.D.230.166; 5.D.230.169; 5.D.230.172; 5.D.230.175; 5.D.230.240; 5.D.230.244; 5.D.231.228; 5.D.231.229; 5.D.231.230; 5.D.231.231; 5.D.231.236; 5.D.231.237; 5.D.231.238; 5.D.231.239; 5.D.231.154; 5.D.231.157; 5.D.231.166; 5.D.231.169; 5.D.231.172; 5.D.231.175; 5.D.231.240; 5.D.231.244; 5.D.236.228; 5.D.236.229; 5.D.236.230; 5.D.236.231; 5.D.236.236; 5.D.236.237; 5.D.236.238; 5.D.236.239; 5.D.236.154; 5.D.236.157; 5.D.236.166; 5.D.236.169; 5.D.236.172; 5.D.236.175; 5.D.236.240; 5.D.236.244; 5.D.237.228; 5.D.237.229; 5.D.237.230; 5.D.237.231; 5.D.237.236; 5.D.237.237; 5.D.237.238; 5.D.237.239; 5.D.237.154; 5.D.237.157; 5.D.237.166; 5.D.237.169; 5.D.237.172; 5.D.237.175; 5.D.237.240; 5.D.237.244; 5.D.238.228; 5.D.238.229; 5.D.238.230; 5.D.238.231; 5.D.238.236; 5.D.238.237; 5.D.238.238; 5.D.238.239; 5.D.238.154; 5.D.238.157; 5.D.238.166; 5.D.238.169; 5.D.238.172; 5.D.238.175; 5.D.238.240; 5.D.238.244; 5.D.239.228; 5.D.239.229; 5.D.239.230; 5.D.239.231; 5.D.239.236; 5.D.239.237; 5.D.239.238; 5.D.239.239; 5.D.239.154; 5.D.239.157; 5.D.239.166; 5.D.239.169; 5.D.239.172; 5.D.239.175; 5.D.239.240; 5.D.239.244; 5.D.154.228; 5.D.154.229; 5.D.154.230; 5.D.154.231; 5.D.154.236; 5.D.154.237; 5.D.154.238; 5.D.154.239; 5.D.154.154; 5.D.154.157; 5.D.154.166; 5.D.154.169; 5.D.154.172; 5.D.154.175; 5.D.154.240; 5.D.154.244; 5.D.157.228; 5.D.157.229; 5.D.157.230; 5.D.157.231; 5.D.157.236; 5.D.157.237; 5.D.157.238; 5.D.157.239; 5.D.157.154; 5.D.157.157; 5.D.157.166; 5.D.157.169; 5.D.157.172; 5.D.157.175; 5.D.157.240; 5.D.157.244; 5.D.166.228; 5.D.166.229; 5.D.166.230; 5.D.166.231; 5.D.166.236; 5.D.166.237; 5.D.166.238; 5.D.166.239; 5.D.166.154; 5.D.166.157; 5.D.166.166; 5.D.166.169; 5.D.166.172; 5.D.166.175; 5.D.166.240; 5.D.166.244; 5.D.169.228; 5.D.169.229; 5.D.169.230; 5.D.169.231; 5.D.169.236; 5.D.169.237; 5.D.169.238; 5.D.169.239; 5.D.169.154; 5.D.169.157; 5.D.169.166; 5.D.169.169; 5.D.169.172; 5.D.169.175; 5.D.169.240; 5.D.169.244; 5.D.172.228; 5.D.172.229; 5.D.172.230; 5.D.172.231; 5.D.172.236; 5.D.172.237; 5.D.172.238; 5.D.172.239; 5.D.172.154; 5.D.172.157; 5.D.172.166; 5.D.172.169; 5.D.172.172; 5.D.172.175; 5.D.172.240; 5.D.172.244; 5.D.175.228; 5.D.175.229; 5.D.175.230; 5.D.175.231; 5.D.175.236; 5.D.175.237; 5.D.175.238; 5.D.175.239; 5.D.175.154; 5.D.175.157; 5.D.175.166; 5.D.175.169; 5.D.175.172; 5.D.175.175; 5.D.175.240; 5.D.175.244; 5.D.240.228; 5.D.240.229; 5.D.240.230; 5.D.240.231; 5.D.240.236; 5.D.240.237; 5.D.240.238; 5.D.240.239; 5.D.240.154; 5.D.240.157; 5.D.240.166; 5.D.240.169; 5.D.240.172; 5.D.240.175; 5.D.240.240; 5.D.240.244; 5.D.244.228; 5.D.244.229; 5.D.244.230; 5.D.244.231; 5.D.244.236; 5.D.244.237;

TABLE 100-continued

5.D.244.238; 5.D.244.239; 5.D.244.154; 5.D.244.157; 5.D.244.166; 5.D.244.169; 5.D.244.172; 5.D.244.175; 5.D.244.240; 5.D.244.244;

Prodrugs of 5.E

5.E.228.228; 5.E.228.229; 5.E.228.230; 5.E.228.231; 5.E.228.236; 5.E.228.237; 5.E.228.238; 5.E.228.239; 5.E.228.154; 5.E.228.157; 5.E.228.166; 5.E.228.169; 5.E.228.172; 5.E.228.175; 5.E.228.240; 5.E.228.244; 5.E.229.228; 5.E.229.229; 5.E.229.230; 5.E.229.231; 5.E.229.236; 5.E.229.237; 5.E.229.238; 5.E.229.239; 5.E.229.154; 5.E.229.157; 5.E.229.166; 5.E.229.169; 5.E.229.172; 5.E.229.175; 5.E.229.240; 5.E.229.244; 5.E.230.228; 5.E.230.229; 5.E.230.230; 5.E.230.231; 5.E.230.236; 5.E.230.237; 5.E.230.238; 5.E.230.239; 5.E.230.154; 5.E.230.157; 5.E.230.166; 5.E.230.169; 5.E.230.172; 5.E.230.175; 5.E.230.240; 5.E.230.244; 5.E.231.228; 5.E.231.229; 5.E.231.230; 5.E.231.231; 5.E.231.236; 5.E.231.237; 5.E.231.238; 5.E.231.239; 5.E.231.154; 5.E.231.157; 5.E.231.166; 5.E.231.169; 5.E.231.172; 5.E.231.175; 5.E.231.240; 5.E.231.244; 5.E.236.228; 5.E.236.229; 5.E.236.230; 5.E.236.231; 5.E.236.236; 5.E.236.237; 5.E.236.238; 5.E.236.239; 5.E.236.154; 5.E.236.157; 5.E.236.166; 5.E.236.169; 5.E.236.172; 5.E.236.175; 5.E.236.240; 5.E.236.244; 5.E.237.228; 5.E.237.229; 5.E.237.230; 5.E.237.231; 5.E.237.236; 5.E.237.237; 5.E.237.238; 5.E.237.239; 5.E.237.154; 5.E.237.157; 5.E.237.166; 5.E.237.169; 5.E.237.172; 5.E.237.175; 5.E.237.240; 5.E.237.244; 5.E.238.228; 5.E.238.229; 5.E.238.230; 5.E.238.231; 5.E.238.236; 5.E.238.237; 5.E.238.238; 5.E.238.239; 5.E.238.154; 5.E.238.157; 5.E.238.166; 5.E.238.169; 5.E.238.172; 5.E.238.175; 5.E.238.240; 5.E.238.244; 5.E.239.228; 5.E.239.229; 5.E.239.230; 5.E.239.231; 5.E.239.236; 5.E.239.237; 5.E.239.238; 5.E.239.239; 5.E.239.154; 5.E.239.157; 5.E.239.166; 5.E.239.169; 5.E.239.172; 5.E.239.175; 5.E.239.240; 5.E.239.244; 5.E.154.228; 5.E.154.229; 5.E.154.230; 5.E.154.231; 5.E.154.236; 5.E.154.237; 5.E.154.238; 5.E.154.239; 5.E.154.154; 5.E.154.157; 5.E.154.166; 5.E.154.169; 5.E.154.172; 5.E.154.175; 5.E.154.240; 5.E.154.244; 5.E.157.228; 5.E.157.229; 5.E.157.230; 5.E.157.231; 5.E.157.236; 5.E.157.237; 5.E.157.238; 5.E.157.239; 5.E.157.154; 5.E.157.157; 5.E.157.166; 5.E.157.169; 5.E.157.172; 5.E.157.175; 5.E.157.240; 5.E.157.244; 5.E.166.228; 5.E.166.229; 5.E.166.230; 5.E.166.231; 5.E.166.236; 5.E.166.237; 5.E.166.238; 5.E.166.239; 5.E.166.154; 5.E.166.157; 5.E.166.166; 5.E.166.169; 5.E.166.172; 5.E.166.175; 5.E.166.240; 5.E.166.244; 5.E.169.228; 5.E.169.229; 5.E.169.230; 5.E.169.231; 5.E.169.236; 5.E.169.237; 5.E.169.238; 5.E.169.239; 5.E.169.154; 5.E.169.157; 5.E.169.166; 5.E.169.169; 5.E.169.172; 5.E.169.175; 5.E.169.240; 5.E.169.244; 5.E.172.228; 5.E.172.229; 5.E.172.230; 5.E.172.231; 5.E.172.236; 5.E.172.237; 5.E.172.238; 5.E.172.239; 5.E.172.154; 5.E.172.157; 5.E.172.166; 5.E.172.169; 5.E.172.172; 5.E.172.175; 5.E.172.240; 5.E.172.244; 5.E.175.228; 5.E.175.229; 5.E.175.230; 5.E.175.231; 5.E.175.236; 5.E.175.237; 5.E.175.238; 5.E.175.239; 5.E.175.154; 5.E.175.157; 5.E.175.166; 5.E.175.169; 5.E.175.172; 5.E.175.175; 5.E.175.240; 5.E.175.244; 5.E.240.228; 5.E.240.229; 5.E.240.230; 5.E.240.231; 5.E.240.236; 5.E.240.237; 5.E.240.238; 5.E.240.239; 5.E.240.154; 5.E.240.157; 5.E.240.166; 5.E.240.169; 5.E.240.172; 5.E.240.175; 5.E.240.240; 5.E.240.244; 5.E.244.228; 5.E.244.229; 5.E.244.230; 5.E.244.231; 5.E.244.236; 5.E.244.237; 5.E.244.238; 5.E.244.239; 5.E.244.154; 5.E.244.157; 5.E.244.166; 5.E.244.169; 5.E.244.172; 5.E.244.175; 5.E.244.240; 5.E.244.244;

Prodrugs of 5.G

5.G.228.228; 5.G.228.229; 5.G.228.230; 5.G.228.231; 5.G.228.236; 5.G.228.237; 5.G.228.238; 5.G.228.239; 5.G.228.154; 5.G.228.157; 5.G.228.166; 5.G.228.169; 5.G.228.172; 5.G.228.175; 5.G.228.240; 5.G.228.244; 5.G.229.228; 5.G.229.229; 5.G.229.230; 5.G.229.231; 5.G.229.236; 5.G.229.237; 5.G.229.238; 5.G.229.239; 5.G.229.154; 5.G.229.157; 5.G.229.166; 5.G.229.169; 5.G.229.172; 5.G.229.175; 5.G.229.240; 5.G.229.244; 5.G.230.228; 5.G.230.229; 5.G.230.230; 5.G.230.231; 5.G.230.236; 5.G.230.237; 5.G.230.238; 5.G.230.239; 5.G.230.154; 5.G.230.157; 5.G.230.166; 5.G.230.169; 5.G.230.172; 5.G.230.175; 5.G.230.240; 5.G.230.244; 5.G.231.228; 5.G.231.229; 5.G.231.230; 5.G.231.231; 5.G.231.236; 5.G.231.237; 5.G.231.238; 5.G.231.239; 5.G.231.154; 5.G.231.157; 5.G.231.166; 5.G.231.169; 5.G.231.172; 5.G.231.175; 5.G.231.240; 5.G.231.244; 5.G.236.228; 5.G.236.229; 5.G.236.230; 5.G.236.231; 5.G.236.236; 5.G.236.237; 5.G.236.238; 5.G.236.239; 5.G.236.154; 5.G.236.157; 5.G.236.166; 5.G.236.169; 5.G.236.172; 5.G.236.175; 5.G.236.240; 5.G.236.244; 5.G.237.228; 5.G.237.229; 5.G.237.230; 5.G.237.231; 5.G.237.236; 5.G.237.237; 5.G.237.238; 5.G.237.239; 5.G.237.154; 5.G.237.157; 5.G.237.166; 5.G.237.169; 5.G.237.172; 5.G.237.175; 5.G.237.240; 5.G.237.244; 5.G.238.228; 5.G.238.229; 5.G.238.230; 5.G.238.231; 5.G.238.236; 5.G.238.237; 5.G.238.238; 5.G.238.239; 5.G.238.154; 5.G.238.157; 5.G.238.166; 5.G.238.169; 5.G.238.172; 5.G.238.175; 5.G.238.240; 5.G.238.244; 5.G.239.228; 5.G.239.229; 5.G.239.230; 5.G.239.231; 5.G.239.236; 5.G.239.237; 5.G.239.238; 5.G.239.239; 5.G.239.154; 5.G.239.157; 5.G.239.166; 5.G.239.169; 5.G.239.172; 5.G.239.175; 5.G.239.240; 5.G.239.244; 5.G.154.228; 5.G.154.229; 5.G.154.230; 5.G.154.231; 5.G.154.236; 5.G.154.237; 5.G.154.238; 5.G.154.239; 5.G.154.154; 5.G.154.157; 5.G.154.166; 5.G.154.169; 5.G.154.172; 5.G.154.175; 5.G.154.240; 5.G.154.244; 5.G.157.228; 5.G.157.229; 5.G.157.230; 5.G.157.231; 5.G.157.236; 5.G.157.237; 5.G.157.238; 5.G.157.239; 5.G.157.154; 5.G.157.157; 5.G.157.166; 5.G.157.169; 5.G.157.172; 5.G.157.175; 5.G.157.240; 5.G.157.244; 5.G.166.228; 5.G.166.229; 5.G.166.230; 5.G.166.231; 5.G.166.236; 5.G.166.237; 5.G.166.238; 5.G.166.239; 5.G.166.154; 5.G.166.157; 5.G.166.166; 5.G.166.169; 5.G.166.172; 5.G.166.175; 5.G.166.240; 5.G.166.244; 5.G.169.228; 5.G.169.229; 5.G.169.230; 5.G.169.231; 5.G.169.236; 5.G.169.237; 5.G.169.238; 5.G.169.239; 5.G.169.154; 5.G.169.157; 5.G.169.166; 5.G.169.169; 5.G.169.172; 5.G.169.175; 5.G.169.240; 5.G.169.244; 5.G.172.228; 5.G.172.229; 5.G.172.230; 5.G.172.231; 5.G.172.236; 5.G.172.237; 5.G.172.238; 5.G.172.239; 5.G.172.154; 5.G.172.157; 5.G.172.166; 5.G.172.169; 5.G.172.172; 5.G.172.175; 5.G.172.240; 5.G.172.244; 5.G.175.228; 5.G.175.229; 5.G.175.230; 5.G.175.231; 5.G.175.236; 5.G.175.237; 5.G.175.238; 5.G.175.239;

TABLE 100-continued

5.G.175.154; 5.G.175.157; 5.G.175.166; 5.G.175.169; 5.G.175.172; 5.G.175.175;
5.G.175.240; 5.G.175.244; 5.G.240.228; 5.G.240.229; 5.G.240.230; 5.G.240.231;
5.G.240.236; 5.G.240.237; 5.G.240.238; 5.G.240.239; 5.G.240.154; 5.G.240.157;
5.G.240.166; 5.G.240.169; 5.G.240.172; 5.G.240.175; 5.G.240.240; 5.G.240.244;
5.G.244.228; 5.G.244.229; 5.G.244.230; 5.G.244.231; 5.G.244.236; 5.G.244.237;
5.G.244.238; 5.G.244.239; 5.G.244.154; 5.G.244.157; 5.G.244.166; 5.G.244.169;
5.G.244.172; 5.G.244.175; 5.G.244.240; 5.G.244.244;

Prodrugs of 5.I

5.I.228.228; 5.I.228.229; 5.I.228.230; 5.I.228.231; 5.I.228.236; 5.I.228.237; 5.I.228.238;
5.I.228.239; 5.I.228.154; 5.I.228.157; 5.I.228.166; 5.I.228.169; 5.I.228.172; 5.I.228.175;
5.I.228.240; 5.I.228.244; 5.I.229.228; 5.I.229.229; 5.I.229.230; 5.I.229.231; 5.I.229.236;
5.I.229.237; 5.I.229.238; 5.I.229.239; 5.I.229.154; 5.I.229.157; 5.I.229.166; 5.I.229.169;
5.I.229.172; 5.I.229.175; 5.I.229.240; 5.I.229.244; 5.I.230.228; 5.I.230.229; 5.I.230.230;
5.I.230.231; 5.I.230.236; 5.I.230.237; 5.I.230.238; 5.I.230.239; 5.I.230.154; 5.I.230.157;
5.I.230.166; 5.I.230.169; 5.I.230.172; 5.I.230.175; 5.I.230.240; 5.I.230.244; 5.I.231.228;
5.I.231.229; 5.I.231.230; 5.I.231.231; 5.I.231.236; 5.I.231.237; 5.I.231.238; 5.I.231.239;
5.I.231.154; 5.I.231.157; 5.I.231.166; 5.I.231.169; 5.I.231.172; 5.I.231.175; 5.I.231.240;
5.I.231.244; 5.I.236.228; 5.I.236.229; 5.I.236.230; 5.I.236.231; 5.I.236.236; 5.I.236.237;
5.I.236.238; 5.I.236.239; 5.I.236.154; 5.I.236.157; 5.I.236.166; 5.I.236.169; 5.I.236.172;
5.I.236.175; 5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157; 5.I.237.166;
5.I.237.169; 5.I.237.172; 5.I.237.175; 5.I.237.240; 5.I.237.244; 5.I.238.228; 5.I.238.229;
5.I.238.230; 5.I.238.231; 5.I.238.236; 5.I.238.237; 5.I.238.238; 5.I.238.239; 5.I.238.154;
5.I.238.157; 5.I.238.166; 5.I.238.169; 5.I.238.172; 5.I.238.175; 5.I.238.240; 5.I.238.244;
5.I.239.228; 5.I.239.229; 5.I.239.230; 5.I.239.231; 5.I.239.236; 5.I.239.237; 5.I.239.238;
5.I.239.239; 5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231; 5.I.154.236;
5.I.154.237; 5.I.154.238; 5.I.154.239; 5.I.154.154; 5.I.154.157; 5.I.154.166; 5.I.154.169;
5.I.154.172; 5.I.154.175; 5.I.154.240; 5.I.154.244; 5.I.157.228; 5.I.157.229; 5.I.157.230;
5.I.157.231; 5.I.157.236; 5.I.157.237; 5.I.157.238; 5.I.157.239; 5.I.157.154; 5.I.157.157;
5.I.157.166; 5.I.157.169; 5.I.157.172; 5.I.157.175; 5.I.157.240; 5.I.157.244; 5.I.166.228;
5.I.166.229; 5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175; 5.I.166.240;
5.I.166.244; 5.I.169.228; 5.I.169.229; 5.I.169.230; 5.I.169.231; 5.I.169.236; 5.I.169.237;
5.I.169.238; 5.I.169.239; 5.I.169.154; 5.I.169.157; 5.I.169.166; 5.I.169.169; 5.I.169.172;
5.I.169.175; 5.I.169.240; 5.I.169.244; 5.I.172.228; 5.I.172.229; 5.I.172.230; 5.I.172.231;
5.I.172.236; 5.I.172.237; 5.I.172.238; 5.I.172.239; 5.I.172.154; 5.I.172.157; 5.I.172.166;
5.I.172.169; 5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239; 5.I.175.154;
5.I.175.157; 5.I.175.166; 5.I.175.169; 5.I.175.172; 5.I.175.175; 5.I.175.240; 5.I.175.244;
5.I.240.228; 5.I.240.229; 5.I.240.230; 5.I.240.231; 5.I.240.236; 5.I.240.237; 5.I.240.238;
5.I.240.239; 5.I.240.154; 5.I.240.157; 5.I.240.166; 5.I.240.169; 5.I.240.172; 5.I.240.175;
5.I.240.240; 5.I.240.244; 5.I.244.228; 5.I.244.229; 5.I.244.230; 5.I.244.231; 5.I.244.236;
5.I.244.237; 5.I.244.238; 5.I.244.239; 5.I.244.154; 5.I.244.157; 5.I.244.166; 5.I.244.169;
5.I.244.172; 5.I.244.175; 5.I.244.240; 5.I.244.244;

Prodrugs of 5.J

5.J.228.228; 5.J.228.229; 5.J.228.230; 5.J.228.231; 5.J.228.236; 5.J.228.237; 5.J.228.238;
5.J.228.239; 5.J.228.154; 5.J.228.157; 5.J.228.166; 5.J.228.169; 5.J.228.172; 5.J.228.175;
5.J.228.240; 5.J.228.244; 5.J.229.228; 5.J.229.229; 5.J.229.230; 5.J.229.231; 5.J.229.236;
5.J.229.237; 5.J.229.238; 5.J.229.239; 5.J.229.154; 5.J.229.157; 5.J.229.166; 5.J.229.169;
5.J.229.172; 5.J.229.175; 5.J.229.240; 5.J.229.244; 5.J.230.228; 5.J.230.229; 5.J.230.230;
5.J.230.231; 5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244; 5.J.231.228;
5.J.231.229; 5.J.231.230; 5.J.231.231; 5.J.231.236; 5.J.231.237; 5.J.231.238; 5.J.231.239;
5.J.231.154; 5.J.231.157; 5.J.231.166; 5.J.231.169; 5.J.231.172; 5.J.231.175; 5.J.231.240;
5.J.231.244; 5.J.236.228; 5.J.236.229; 5.J.236.230; 5.J.236.231; 5.J.236.236; 5.J.236.237;
5.J.236.238; 5.J.236.239; 5.J.236.154; 5.J.236.157; 5.J.236.166; 5.J.236.169; 5.J.236.172;
5.J.236.175; 5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157; 5.J.237.166;
5.J.237.169; 5.J.237.172; 5.J.237.175; 5.J.237.240; 5.J.237.244; 5.J.238.228; 5.J.238.229;
5.J.238.230; 5.J.238.231; 5.J.238.236; 5.J.238.237; 5.J.238.238; 5.J.238.239; 5.J.238.154;
5.J.238.157; 5.J.238.166; 5.J.238.169; 5.J.238.172; 5.J.238.175; 5.J.238.240; 5.J.238.244;
5.J.239.228; 5.J.239.229; 5.J.239.230; 5.J.239.231; 5.J.239.236; 5.J.239.237; 5.J.239.238;
5.J.239.239; 5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231; 5.J.154.236;
5.J.154.237; 5.J.154.238; 5.J.154.239; 5.J.154.154; 5.J.154.157; 5.J.154.166; 5.J.154.169;
5.J.154.172; 5.J.154.175; 5.J.154.240; 5.J.154.244; 5.J.157.228; 5.J.157.229; 5.J.157.230;
5.J.157.231; 5.J.157.236; 5.J.157.237; 5.J.157.238; 5.J.157.239; 5.J.157.154; 5.J.157.157;
5.J.157.166; 5.J.157.169; 5.J.157.172; 5.J.157.175; 5.J.157.240; 5.J.157.244; 5.J.166.228;
5.J.166.229; 5.J.166.230; 5.J.166.231; 5.J.166.236; 5.J.166.237; 5.J.166.238; 5.J.166.239;
5.J.166.154; 5.J.166.157; 5.J.166.166; 5.J.166.169; 5.J.166.172; 5.J.166.175; 5.J.166.240;
5.J.166.244; 5.J.169.228; 5.J.169.229; 5.J.169.230; 5.J.169.231; 5.J.169.236; 5.J.169.237;
5.J.169.238; 5.J.169.239; 5.J.169.154; 5.J.169.157; 5.J.169.166; 5.J.169.169; 5.J.169.172;
5.J.169.175; 5.J.169.240; 5.J.169.244; 5.J.172.228; 5.J.172.229; 5.J.172.230; 5.J.172.231;
5.J.172.236; 5.J.172.237; 5.J.172.238; 5.J.172.239; 5.J.172.154; 5.J.172.157; 5.J.172.166;
5.J.172.169; 5.J.172.172; 5.J.172.175; 5.J.172.240; 5.J.172.244; 5.J.175.228; 5.J.175.229;
5.J.175.230; 5.J.175.231; 5.J.175.236; 5.J.175.237; 5.J.175.238; 5.J.175.239; 5.J.175.154;

TABLE 100-continued

5.J.175.157; 5.J.175.166; 5.J.175.169; 5.J.175.172; 5.J.175.175; 5.J.175.240; 5.J.175.244; 5.J.240.228; 5.J.240.229; 5.J.240.230; 5.J.240.231; 5.J.240.236; 5.J.240.237; 5.J.240.238; 5.J.240.239; 5.J.240.154; 5.J.240.157; 5.J.240.166; 5.J.240.169; 5.J.240.172; 5.J.240.175; 5.J.240.240; 5.J.240.244; 5.J.244.228; 5.J.244.229; 5.J.244.230; 5.J.244.231; 5.J.244.236; 5.J.244.237; 5.J.244.238; 5.J.244.239; 5.J.244.154; 5.J.244.157; 5.J.244.166; 5.J.244.169; 5.J.244.172; 5.J.244.175; 5.J.244.240; 5.J.244.244;

Prodrugs of 5.L

5.L.228.228; 5.L.228.229; 5.L.228.230; 5.L.228.231; 5.L.228.236; 5.L.228.237; 5.L.228.238; 5.L.228.239; 5.L.228.154; 5.L.228.157; 5.L.228.166; 5.L.228.169; 5.L.228.172; 5.L.228.175; 5.L.228.240; 5.L.228.244; 5.L.229.228; 5.L.229.229; 5.L.229.230; 5.L.229.231; 5.L.229.236; 5.L.229.237; 5.L.229.238; 5.L.229.239; 5.L.229.154; 5.L.229.157; 5.L.229.166; 5.L.229.169; 5.L.229.172; 5.L.229.175; 5.L.229.240; 5.L.229.244; 5.L.230.228; 5.L.230.229; 5.L.230.230; 5.L.230.231; 5.L.230.236; 5.L.230.237; 5.L.230.238; 5.L.230.239; 5.L.230.154; 5.L.230.157; 5.L.230.166; 5.L.230.169; 5.L.230.172; 5.L.230.175; 5.L.230.240; 5.L.230.244; 5.L.231.228; 5.L.231.229; 5.L.231.230; 5.L.231.231; 5.L.231.236; 5.L.231.237; 5.L.231.238; 5.L.231.239; 5.L.231.154; 5.L.231.157; 5.L.231.166; 5.L.231.169; 5.L.231.172; 5.L.231.175; 5.L.231.240; 5.L.231.244; 5.L.236.228; 5.L.236.229; 5.L.236.230; 5.L.236.231; 5.L.236.236; 5.L.236.237; 5.L.236.238; 5.L.236.239; 5.L.236.154; 5.L.236.157; 5.L.236.166; 5.L.236.169; 5.L.236.172; 5.L.236.175; 5.L.236.240; 5.L.236.244; 5.L.237.228; 5.L.237.229; 5.L.237.230; 5.L.237.231; 5.L.237.236; 5.L.237.237; 5.L.237.238; 5.L.237.239; 5.L.237.154; 5.L.237.157; 5.L.237.166; 5.L.237.169; 5.L.237.172; 5.L.237.175; 5.L.237.240; 5.L.237.244; 5.L.238.228; 5.L.238.229; 5.L.238.230; 5.L.238.231; 5.L.238.236; 5.L.238.237; 5.L.238.238; 5.L.238.239; 5.L.238.154; 5.L.238.157; 5.L.238.166; 5.L.238.169; 5.L.238.172; 5.L.238.175; 5.L.238.240; 5.L.238.244; 5.L.239.228; 5.L.239.229; 5.L.239.230; 5.L.239.231; 5.L.239.236; 5.L.239.237; 5.L.239.238; 5.L.239.239; 5.L.239.154; 5.L.239.157; 5.L.239.166; 5.L.239.169; 5.L.239.172; 5.L.239.175; 5.L.239.240; 5.L.239.244; 5.L.154.228; 5.L.154.229; 5.L.154.230; 5.L.154.231; 5.L.154.236; 5.L.154.237; 5.L.154.238; 5.L.154.239; 5.L.154.154; 5.L.154.157; 5.L.154.166; 5.L.154.169; 5.L.154.172; 5.L.154.175; 5.L.154.240; 5.L.154.244; 5.L.157.228; 5.L.157.229; 5.L.157.230; 5.L.157.231; 5.L.157.236; 5.L.157.237; 5.L.157.238; 5.L.157.239; 5.L.157.154; 5.L.157.157; 5.L.157.166; 5.L.157.169; 5.L.157.172; 5.L.157.175; 5.L.157.240; 5.L.157.244; 5.L.166.228; 5.L.166.229; 5.L.166.230; 5.L.166.231; 5.L.166.236; 5.L.166.237; 5.L.166.238; 5.L.166.239; 5.L.166.154; 5.L.166.157; 5.L.166.166; 5.L.166.169; 5.L.166.172; 5.L.166.175; 5.L.166.240; 5.L.166.244; 5.L.169.228; 5.L.169.229; 5.L.169.230; 5.L.169.231; 5.L.169.236; 5.L.169.237; 5.L.169.238; 5.L.169.239; 5.L.169.154; 5.L.169.157; 5.L.169.166; 5.L.169.169; 5.L.169.172; 5.L.169.175; 5.L.169.240; 5.L.169.244; 5.L.172.228; 5.L.172.229; 5.L.172.230; 5.L.172.231; 5.L.172.236; 5.L.172.237; 5.L.172.238; 5.L.172.239; 5.L.172.154; 5.L.172.157; 5.L.172.166; 5.L.172.169; 5.L.172.172; 5.L.172.175; 5.L.172.240; 5.L.172.244; 5.L.175.228; 5.L.175.229; 5.L.175.230; 5.L.175.231; 5.L.175.236; 5.L.175.237; 5.L.175.238; 5.L.175.239; 5.L.175.154; 5.L.175.157; 5.L.175.166; 5.L.175.169; 5.L.175.172; 5.L.175.175; 5.L.175.240; 5.L.175.244; 5.L.240.228; 5.L.240.229; 5.L.240.230; 5.L.240.231; 5.L.240.236; 5.L.240.237; 5.L.240.238; 5.L.240.239; 5.L.240.154; 5.L.240.157; 5.L.240.166; 5.L.240.169; 5.L.240.172; 5.L.240.175; 5.L.240.240; 5.L.240.244; 5.L.244.228; 5.L.244.229; 5.L.244.230; 5.L.244.231; 5.L.244.236; 5.L.244.237; 5.L.244.238; 5.L.244.239; 5.L.244.154; 5.L.244.157; 5.L.244.166; 5.L.244.169; 5.L.244.172; 5.L.244.175; 5.L.244.240; 5.L.244.244;

Prodrugs of 5.O

5.O.228.228; 5.O.228.229; 5.O.228.230; 5.O.228.231; 5.O.228.236; 5.O.228.237; 5.O.228.238; 5.O.228.239; 5.O.228.154; 5.O.228.157; 5.O.228.166; 5.O.228.169; 5.O.228.172; 5.O.228.175; 5.O.228.240; 5.O.228.244; 5.O.229.228; 5.O.229.229; 5.O.229.230; 5.O.229.231; 5.O.229.236; 5.O.229.237; 5.O.229.238; 5.O.229.239; 5.O.229.154; 5.O.229.157; 5.O.229.166; 5.O.229.169; 5.O.229.172; 5.O.229.175; 5.O.229.240; 5.O.229.244; 5.O.230.228; 5.O.230.229; 5.O.230.230; 5.O.230.231; 5.O.230.236; 5.O.230.237; 5.O.230.238; 5.O.230.239; 5.O.230.154; 5.O.230.157; 5.O.230.166; 5.O.230.169; 5.O.230.172; 5.O.230.175; 5.O.230.240; 5.O.230.244; 5.O.231.228; 5.O.231.229; 5.O.231.230; 5.O.231.231; 5.O.231.236; 5.O.231.237; 5.O.231.238; 5.O.231.239; 5.O.231.154; 5.O.231.157; 5.O.231.166; 5.O.231.169; 5.O.231.172; 5.O.231.175; 5.O.231.240; 5.O.231.244; 5.O.236.228; 5.O.236.229; 5.O.236.230; 5.O.236.231; 5.O.236.236; 5.O.236.237; 5.O.236.238; 5.O.236.239; 5.O.236.154; 5.O.236.157; 5.O.236.166; 5.O.236.169; 5.O.236.172; 5.O.236.175; 5.O.236.240; 5.O.236.244; 5.O.237.228; 5.O.237.229; 5.O.237.230; 5.O.237.231; 5.O.237.236; 5.O.237.237; 5.O.237.238; 5.O.237.239; 5.O.237.154; 5.O.237.157; 5.O.237.166; 5.O.237.169; 5.O.237.172; 5.O.237.175; 5.O.237.240; 5.O.237.244; 5.O.238.228; 5.O.238.229; 5.O.238.230; 5.O.238.231; 5.O.238.236; 5.O.238.237; 5.O.238.238; 5.O.238.239; 5.O.238.154; 5.O.238.157; 5.O.238.166; 5.O.238.169; 5.O.238.172; 5.O.238.175; 5.O.238.240; 5.O.238.244; 5.O.239.228; 5.O.239.229; 5.O.239.230; 5.O.239.231; 5.O.239.236; 5.O.239.237; 5.O.239.238; 5.O.239.239; 5.O.239.154; 5.O.239.157; 5.O.239.166; 5.O.239.169; 5.O.239.172; 5.O.239.175; 5.O.239.240; 5.O.239.244; 5.O.154.228; 5.O.154.229; 5.O.154.230; 5.O.154.231; 5.O.154.236; 5.O.154.237; 5.O.154.238; 5.O.154.239; 5.O.154.154; 5.O.154.157; 5.O.154.166; 5.O.154.169; 5.O.154.172; 5.O.154.175; 5.O.154.240; 5.O.154.244; 5.O.157.228; 5.O.157.229; 5.O.157.230; 5.O.157.231; 5.O.157.236; 5.O.157.237; 5.O.157.238; 5.O.157.239; 5.O.157.154; 5.O.157.157; 5.O.157.166; 5.O.157.169; 5.O.157.172; 5.O.157.175; 5.O.157.240; 5.O.157.244; 5.O.166.228; 5.O.166.229; 5.O.166.230; 5.O.166.231; 5.O.166.236; 5.O.166.237; 5.O.166.238; 5.O.166.239; 5.O.166.154; 5.O.166.157; 5.O.166.166; 5.O.166.169; 5.O.166.172; 5.O.166.175; 5.O.166.240; 5.O.166.244; 5.O.169.228; 5.O.169.229; 5.O.169.230; 5.O.169.231; 5.O.169.236; 5.O.169.237; 5.O.169.238; 5.O.169.239; 5.O.169.154; 5.O.169.157; 5.O.169.166; 5.O.169.169; 5.O.169.172; 5.O.169.175; 5.O.169.240; 5.O.169.244;

TABLE 100-continued

5.O.172.228; 5.O.172.229; 5.O.172.230; 5.O.172.231; 5.O.172.236; 5.O.172.237; 5.O.172.238; 5.O.172.239; 5.O.172.154; 5.O.172.157; 5.O.172.166; 5.O.172.169; 5.O.172.172; 5.O.172.175; 5.O.172.240; 5.O.172.244; 5.O.175.228; 5.O.175.229; 5.O.175.230; 5.O.175.231; 5.O.175.236; 5.O.175.237; 5.O.175.238; 5.O.175.239; 5.O.175.154; 5.O.175.157; 5.O.175.166; 5.O.175.169; 5.O.175.172; 5.O.175.175; 5.O.175.240; 5.O.175.244; 5.O.240.228; 5.O.240.229; 5.O.240.230; 5.O.240.231; 5.O.240.236; 5.O.240.237; 5.O.240.238; 5.O.240.239; 5.O.240.154; 5.O.240.157; 5.O.240.166; 5.O.240.169; 5.O.240.172; 5.O.240.175; 5.O.240.240; 5.O.240.244; 5.O.244.228; 5.O.244.229; 5.O.244.230; 5.O.244.231; 5.O.244.236; 5.O.244.237; 5.O.244.238; 5.O.244.239; 5.O.244.154; 5.O.244.157; 5.O.244.166; 5.O.244.169; 5.O.244.172; 5.O.244.175; 5.O.244.240; 5.O.244.244;

Prodrugs of 5.P

5.P.228.228; 5.P.228.229; 5.P.228.230; 5.P.228.231; 5.P.228.236; 5.P.228.237; 5.P.228.238; 5.P.228.239; 5.P.228.154; 5.P.228.157; 5.P.228.166; 5.P.228.169; 5.P.228.172; 5.P.228.175; 5.P.228.240; 5.P.228.244; 5.P.229.228; 5.P.229.229; 5.P.229.230; 5.P.229.231; 5.P.229.236; 5.P.229.237; 5.P.229.238; 5.P.229.239; 5.P.229.154; 5.P.229.157; 5.P.229.166; 5.P.229.169; 5.P.229.172; 5.P.229.175; 5.P.229.240; 5.P.229.244; 5.P.230.228; 5.P.230.229; 5.P.230.230; 5.P.230.231; 5.P.230.236; 5.P.230.237; 5.P.230.238; 5.P.230.239; 5.P.230.154; 5.P.230.157; 5.P.230.166; 5.P.230.169; 5.P.230.172; 5.P.230.175; 5.P.230.240; 5.P.230.244; 5.P.231.228; 5.P.231.229; 5.P.231.230; 5.P.231.231; 5.P.231.236; 5.P.231.237; 5.P.231.238; 5.P.231.239; 5.P.231.154; 5.P.231.157; 5.P.231.166; 5.P.231.169; 5.P.231.172; 5.P.231.175; 5.P.231.240; 5.P.231.244; 5.P.236.228; 5.P.236.229; 5.P.236.230; 5.P.236.231; 5.P.236.236; 5.P.236.237; 5.P.236.238; 5.P.236.239; 5.P.236.154; 5.P.236.157; 5.P.236.166; 5.P.236.169; 5.P.236.172; 5.P.236.175; 5.P.236.240; 5.P.236.244; 5.P.237.228; 5.P.237.229; 5.P.237.230; 5.P.237.231; 5.P.237.236; 5.P.237.237; 5.P.237.238; 5.P.237.239; 5.P.237.154; 5.P.237.157; 5.P.237.166; 5.P.237.169; 5.P.237.172; 5.P.237.175; 5.P.237.240; 5.P.237.244; 5.P.238.228; 5.P.238.229; 5.P.238.230; 5.P.238.231; 5.P.238.236; 5.P.238.237; 5.P.238.238; 5.P.238.239; 5.P.238.154; 5.P.238.157; 5.P.238.166; 5.P.238.169; 5.P.238.172; 5.P.238.175; 5.P.238.240; 5.P.238.244; 5.P.239.228; 5.P.239.229; 5.P.239.230; 5.P.239.231; 5.P.239.236; 5.P.239.237; 5.P.239.238; 5.P.239.239; 5.P.239.154; 5.P.239.157; 5.P.239.166; 5.P.239.169; 5.P.239.172; 5.P.239.175; 5.P.239.240; 5.P.239.244; 5.P.154.228; 5.P.154.229; 5.P.154.230; 5.P.154.231; 5.P.154.236; 5.P.154.237; 5.P.154.238; 5.P.154.239; 5.P.154.154; 5.P.154.157; 5.P.154.166; 5.P.154.169; 5.P.154.172; 5.P.154.175; 5.P.154.240; 5.P.154.244; 5.P.157.228; 5.P.157.229; 5.P.157.230; 5.P.157.231; 5.P.157.236; 5.P.157.237; 5.P.157.238; 5.P.157.239; 5.P.157.154; 5.P.157.157; 5.P.157.166; 5.P.157.169; 5.P.157.172; 5.P.157.175; 5.P.157.240; 5.P.157.244; 5.P.166.228; 5.P.166.229; 5.P.166.230; 5.P.166.231; 5.P.166.236; 5.P.166.237; 5.P.166.238; 5.P.166.239; 5.P.166.154; 5.P.166.157; 5.P.166.166; 5.P.166.169; 5.P.166.172; 5.P.166.175; 5.P.166.240; 5.P.166.244; 5.P.169.228; 5.P.169.229; 5.P.169.230; 5.P.169.231; 5.P.169.236; 5.P.169.237; 5.P.169.238; 5.P.169.239; 5.P.169.154; 5.P.169.157; 5.P.169.166; 5.P.169.169; 5.P.169.172; 5.P.169.175; 5.P.169.240; 5.P.169.244; 5.P.172.228; 5.P.172.229; 5.P.172.230; 5.P.172.231; 5.P.172.236; 5.P.172.237; 5.P.172.238; 5.P.172.239; 5.P.172.154; 5.P.172.157; 5.P.172.166; 5.P.172.169; 5.P.172.172; 5.P.172.175; 5.P.172.240; 5.P.172.244; 5.P.175.228; 5.P.175.229; 5.P.175.230; 5.P.175.231; 5.P.175.236; 5.P.175.237; 5.P.175.238; 5.P.175.239; 5.P.175.154; 5.P.175.157; 5.P.175.166; 5.P.175.169; 5.P.175.172; 5.P.175.175; 5.P.175.240; 5.P.175.244; 5.P.240.228; 5.P.240.229; 5.P.240.230; 5.P.240.231; 5.P.240.236; 5.P.240.237; 5.P.240.238; 5.P.240.239; 5.P.240.154; 5.P.240.157; 5.P.240.166; 5.P.240.169; 5.P.240.172; 5.P.240.175; 5.P.240.240; 5.P.240.244; 5.P.244.228; 5.P.244.229; 5.P.244.230; 5.P.244.231; 5.P.244.236; 5.P.244.237; 5.P.244.238; 5.P.244.239; 5.P.244.154; 5.P.244.157; 5.P.244.166; 5.P.244.169; 5.P.244.172; 5.P.244.175; 5.P.244.240; 5.P.244.244;

Prodrugs of 5.U

5.U.228.228; 5.U.228.229; 5.U.228.230; 5.U.228.231; 5.U.228.236; 5.U.228.237; 5.U.228.238; 5.U.228.239; 5.U.228.154; 5.U.228.157; 5.U.228.166; 5.U.228.169; 5.U.228.172; 5.U.228.175; 5.U.228.240; 5.U.228.244; 5.U.229.228; 5.U.229.229; 5.U.229.230; 5.U.229.231; 5.U.229.236; 5.U.229.237; 5.U.229.238; 5.U.229.239; 5.U.229.154; 5.U.229.157; 5.U.229.166; 5.U.229.169; 5.U.229.172; 5.U.229.175; 5.U.229.240; 5.U.229.244; 5.U.230.228; 5.U.230.229; 5.U.230.230; 5.U.230.231; 5.U.230.236; 5.U.230.237; 5.U.230.238; 5.U.230.239; 5.U.230.154; 5.U.230.157; 5.U.230.166; 5.U.230.169; 5.U.230.172; 5.U.230.175; 5.U.230.240; 5.U.230.244; 5.U.231.228; 5.U.231.229; 5.U.231.230; 5.U.231.231; 5.U.231.236; 5.U.231.237; 5.U.231.238; 5.U.231.239; 5.U.231.154; 5.U.231.157; 5.U.231.166; 5.U.231.169; 5.U.231.172; 5.U.231.175; 5.U.231.240; 5.U.231.244; 5.U.236.228; 5.U.236.229; 5.U.236.230; 5.U.236.231; 5.U.236.236; 5.U.236.237; 5.U.236.238; 5.U.236.239; 5.U.236.154; 5.U.236.157; 5.U.236.166; 5.U.236.169; 5.U.236.172; 5.U.236.175; 5.U.236.240; 5.U.236.244; 5.U.237.228; 5.U.237.229; 5.U.237.230; 5.U.237.231; 5.U.237.236; 5.U.237.237; 5.U.237.238; 5.U.237.239; 5.U.237.154; 5.U.237.157; 5.U.237.166; 5.U.237.169; 5.U.237.172; 5.U.237.175; 5.U.237.240; 5.U.237.244; 5.U.238.228; 5.U.238.229; 5.U.238.230; 5.U.238.231; 5.U.238.236; 5.U.238.237; 5.U.238.238; 5.U.238.239; 5.U.238.154; 5.U.238.157; 5.U.238.166; 5.U.238.169; 5.U.238.172; 5.U.238.175; 5.U.238.240; 5.U.238.244; 5.U.239.228; 5.U.239.229; 5.U.239.230; 5.U.239.231; 5.U.239.236; 5.U.239.237; 5.U.239.238; 5.U.239.239; 5.U.239.154; 5.U.239.157; 5.U.239.166; 5.U.239.169; 5.U.239.172; 5.U.239.175; 5.U.239.240; 5.U.239.244; 5.U.154.228; 5.U.154.229; 5.U.154.230; 5.U.154.231; 5.U.154.236; 5.U.154.237; 5.U.154.238; 5.U.154.239; 5.U.154.154; 5.U.154.157; 5.U.154.166; 5.U.154.169; 5.U.154.172; 5.U.154.175; 5.U.154.240; 5.U.154.244; 5.U.157.228; 5.U.157.229; 5.U.157.230; 5.U.157.231; 5.U.157.236; 5.U.157.237; 5.U.157.238; 5.U.157.239; 5.U.157.154; 5.U.157.157; 5.U.157.166; 5.U.157.169; 5.U.157.172; 5.U.157.175; 5.U.157.240; 5.U.157.244; 5.U.166.228; 5.U.166.229;

TABLE 100-continued

5.U.166.230; 5.U.166.231; 5.U.166.236; 5.U.166.237; 5.U.166.238; 5.U.166.239; 5.U.166.154; 5.U.166.157; 5.U.166.166; 5.U.166.169; 5.U.166.172; 5.U.166.175; 5.U.166.240; 5.U.166.244; 5.U.169.228; 5.U.169.229; 5.U.169.230; 5.U.169.231; 5.U.169.236; 5.U.169.237; 5.U.169.238; 5.U.169.239; 5.U.169.154; 5.U.169.157; 5.U.169.166; 5.U.169.169; 5.U.169.172; 5.U.169.175; 5.U.169.240; 5.U.169.244; 5.U.172.228; 5.U.172.229; 5.U.172.230; 5.U.172.231; 5.U.172.236; 5.U.172.237; 5.U.172.238; 5.U.172.239; 5.U.172.154; 5.U.172.157; 5.U.172.166; 5.U.172.169; 5.U.172.172; 5.U.172.175; 5.U.172.240; 5.U.172.244; 5.U.175.228; 5.U.175.229; 5.U.175.230; 5.U.175.231; 5.U.175.236; 5.U.175.237; 5.U.175.238; 5.U.175.239; 5.U.175.154; 5.U.175.157; 5.U.175.166; 5.U.175.169; 5.U.175.172; 5.U.175.175; 5.U.175.240; 5.U.175.244; 5.U.240.228; 5.U.240.229; 5.U.240.230; 5.U.240.231; 5.U.240.236; 5.U.240.237; 5.U.240.238; 5.U.240.239; 5.U.240.154; 5.U.240.157; 5.U.240.166; 5.U.240.169; 5.U.240.172; 5.U.240.175; 5.U.240.240; 5.U.240.244; 5.U.244.228; 5.U.244.229; 5.U.244.230; 5.U.244.231; 5.U.244.236; 5.U.244.237; 5.U.244.238; 5.U.244.239; 5.U.244.154; 5.U.244.157; 5.U.244.166; 5.U.244.169; 5.U.244.172; 5.U.244.175; 5.U.244.240; 5.U.244.244;

Prodrugs of 5.W

5.W.228.228; 5.W.228.229; 5.W.228.230; 5.W.228.231; 5.W.228.236; 5.W.228.237; 5.W.228.238; 5.W.228.239; 5.W.228.154; 5.W.228.157; 5.W.228.166; 5.W.228.169; 5.W.228.172; 5.W.228.175; 5.W.228.240; 5.W.228.244; 5.W.229.228; 5.W.229.229; 5.W.229.230; 5.W.229.231; 5.W.229.236; 5.W.229.237; 5.W.229.238; 5.W.229.239; 5.W.229.154; 5.W.229.157; 5.W.229.166; 5.W.229.169; 5.W.229.172; 5.W.229.175; 5.W.229.240; 5.W.229.244; 5.W.230.228; 5.W.230.229; 5.W.230.230; 5.W.230.231; 5.W.230.236; 5.W.230.237; 5.W.230.238; 5.W.230.239; 5.W.230.154; 5.W.230.157; 5.W.230.166; 5.W.230.169; 5.W.230.172; 5.W.230.175; 5.W.230.240; 5.W.230.244; 5.W.231.228; 5.W.231.229; 5.W.231.230; 5.W.231.231; 5.W.231.236; 5.W.231.237; 5.W.231.238; 5.W.231.239; 5.W.231.154; 5.W.231.157; 5.W.231.166; 5.W.231.169; 5.W.231.172; 5.W.231.175; 5.W.231.240; 5.W.231.244; 5.W.236.228; 5.W.236.229; 5.W.236.230; 5.W.236.231; 5.W.236.236; 5.W.236.237; 5.W.236.238; 5.W.236.239; 5.W.236.154; 5.W.236.157; 5.W.236.166; 5.W.236.169; 5.W.236.172; 5.W.236.175; 5.W.236.240; 5.W.236.244; 5.W.237.228; 5.W.237.229; 5.W.237.230; 5.W.237.231; 5.W.237.236; 5.W.237.237; 5.W.237.238; 5.W.237.239; 5.W.237.154; 5.W.237.157; 5.W.237.166; 5.W.237.169; 5.W.237.172; 5.W.237.175; 5.W.237.240; 5.W.237.244; 5.W.238.228; 5.W.238.229; 5.W.238.230; 5.W.238.231; 5.W.238.236; 5.W.238.237; 5.W.238.238; 5.W.238.239; 5.W.238.154; 5.W.238.157; 5.W.238.166; 5.W.238.169; 5.W.238.172; 5.W.238.175; 5.W.238.240; 5.W.238.244; 5.W.239.228; 5.W.239.229; 5.W.239.230; 5.W.239.231; 5.W.239.236; 5.W.239.237; 5.W.239.238; 5.W.239.239; 5.W.239.154; 5.W.239.157; 5.W.239.166; 5.W.239.169; 5.W.239.172; 5.W.239.175; 5.W.239.240; 5.W.239.244; 5.W.154.228; 5.W.154.229; 5.W.154.230; 5.W.154.231; 5.W.154.236; 5.W.154.237; 5.W.154.238; 5.W.154.239; 5.W.154.154; 5.W.154.157; 5.W.154.166; 5.W.154.169; 5.W.154.172; 5.W.154.175; 5.W.154.240; 5.W.154.244; 5.W.157.228; 5.W.157.229; 5.W.157.230; 5.W.157.231; 5.W.157.236; 5.W.157.237; 5.W.157.238; 5.W.157.239; 5.W.157.154; 5.W.157.157; 5.W.157.166; 5.W.157.169; 5.W.157.172; 5.W.157.175; 5.W.157.240; 5.W.157.244; 5.W.166.228; 5.W.166.229; 5.W.166.230; 5.W.166.231; 5.W.166.236; 5.W.166.237; 5.W.166.238; 5.W.166.239; 5.W.166.154; 5.W.166.157; 5.W.166.166; 5.W.166.169; 5.W.166.172; 5.W.166.175; 5.W.166.240; 5.W.166.244; 5.W.169.228; 5.W.169.229; 5.W.169.230; 5.W.169.231; 5.W.169.236; 5.W.169.237; 5.W.169.238; 5.W.169.239; 5.W.169.154; 5.W.169.157; 5.W.169.166; 5.W.169.169; 5.W.169.172; 5.W.169.175; 5.W.169.240; 5.W.169.244; 5.W.172.228; 5.W.172.229; 5.W.172.230; 5.W.172.231; 5.W.172.236; 5.W.172.237; 5.W.172.238; 5.W.172.239; 5.W.172.154; 5.W.172.157; 5.W.172.166; 5.W.172.169; 5.W.172.172; 5.W.172.175; 5.W.172.240; 5.W.172.244; 5.W.175.228; 5.W.175.229; 5.W.175.230; 5.W.175.231; 5.W.175.236; 5.W.175.237; 5.W.175.238; 5.W.175.239; 5.W.175.154; 5.W.175.157; 5.W.175.166; 5.W.175.169; 5.W.175.172; 5.W.175.175; 5.W.175.240; 5.W.175.244; 5.W.240.228; 5.W.240.229; 5.W.240.230; 5.W.240.231; 5.W.240.236; 5.W.240.237; 5.W.240.238; 5.W.240.239; 5.W.240.154; 5.W.240.157; 5.W.240.166; 5.W.240.169; 5.W.240.172; 5.W.240.175; 5.W.240.240; 5.W.240.244; 5.W.244.228; 5.W.244.229; 5.W.244.230; 5.W.244.231; 5.W.244.236; 5.W.244.237; 5.W.244.238; 5.W.244.239; 5.W.244.154; 5.W.244.157; 5.W.244.166; 5.W.244.169; 5.W.244.172; 5.W.244.175; 5.W.244.240; 5.W.244.244;

Prodrugs of 5.Y

5.Y.228.228; 5.Y.228.229; 5.Y.228.230; 5.Y.228.231; 5.Y.228.236; 5.Y.228.237; 5.Y.228.238; 5.Y.228.239; 5.Y.228.154; 5.Y.228.157; 5.Y.228.166; 5.Y.228.169; 5.Y.228.172; 5.Y.228.175; 5.Y.228.240; 5.Y.228.244; 5.Y.229.228; 5.Y.229.229; 5.Y.229.230; 5.Y.229.231; 5.Y.229.236; 5.Y.229.237; 5.Y.229.238; 5.Y.229.239; 5.Y.229.154; 5.Y.229.157; 5.Y.229.166; 5.Y.229.169; 5.Y.229.172; 5.Y.229.175; 5.Y.229.240; 5.Y.229.244; 5.Y.230.228; 5.Y.230.229; 5.Y.230.230; 5.Y.230.231; 5.Y.230.236; 5.Y.230.237; 5.Y.230.238; 5.Y.230.239; 5.Y.230.154; 5.Y.230.157; 5.Y.230.166; 5.Y.230.169; 5.Y.230.172; 5.Y.230.175; 5.Y.230.240; 5.Y.230.244; 5.Y.231.228; 5.Y.231.229; 5.Y.231.230; 5.Y.231.231; 5.Y.231.236; 5.Y.231.237; 5.Y.231.238; 5.Y.231.239; 5.Y.231.154; 5.Y.231.157; 5.Y.231.166; 5.Y.231.169; 5.Y.231.172; 5.Y.231.175; 5.Y.231.240; 5.Y.231.244; 5.Y.236.228; 5.Y.236.229; 5.Y.236.230; 5.Y.236.231; 5.Y.236.236; 5.Y.236.237; 5.Y.236.238; 5.Y.236.239; 5.Y.236.154; 5.Y.236.157; 5.Y.236.166; 5.Y.236.169; 5.Y.236.172; 5.Y.236.175; 5.Y.236.240; 5.Y.236.244; 5.Y.237.228; 5.Y.237.229; 5.Y.237.230; 5.Y.237.231; 5.Y.237.236; 5.Y.237.237; 5.Y.237.238; 5.Y.237.239; 5.Y.237.154; 5.Y.237.157; 5.Y.237.166; 5.Y.237.169; 5.Y.237.172; 5.Y.237.175; 5.Y.237.240; 5.Y.237.244;

TABLE 100-continued

5.Y.238.228; 5.Y.238.229; 5.Y.238.230; 5.Y.238.231; 5.Y.238.236; 5.Y.238.237; 5.Y.238.238; 5.Y.238.239; 5.Y.238.154; 5.Y.238.157; 5.Y.238.166; 5.Y.238.169; 5.Y.238.172; 5.Y.238.175; 5.Y.238.240; 5.Y.238.244; 5.Y.239.228; 5.Y.239.229; 5.Y.239.230; 5.Y.239.231; 5.Y.239.236; 5.Y.239.237; 5.Y.239.238; 5.Y.239.239; 5.Y.239.154; 5.Y.239.157; 5.Y.239.166; 5.Y.239.169; 5.Y.239.172; 5.Y.239.175; 5.Y.239.240; 5.Y.239.244; 5.Y.154.228; 5.Y.154.229; 5.Y.154.230; 5.Y.154.231; 5.Y.154.236; 5.Y.154.237; 5.Y.154.238; 5.Y.154.239; 5.Y.154.154; 5.Y.154.157; 5.Y.154.166; 5.Y.154.169; 5.Y.154.172; 5.Y.154.175; 5.Y.154.240; 5.Y.154.244; 5.Y.157.228; 5.Y.157.229; 5.Y.157.230; 5.Y.157.231; 5.Y.157.236; 5.Y.157.237; 5.Y.157.238; 5.Y.157.239; 5.Y.157.154; 5.Y.157.157; 5.Y.157.166; 5.Y.157.169; 5.Y.157.172; 5.Y.157.175; 5.Y.157.240; 5.Y.157.244; 5.Y.166.228; 5.Y.166.229; 5.Y.166.230; 5.Y.166.231; 5.Y.166.236; 5.Y.166.237; 5.Y.166.238; 5.Y.166.239; 5.Y.166.154; 5.Y.166.157; 5.Y.166.166; 5.Y.166.169; 5.Y.166.172; 5.Y.166.175; 5.Y.166.240; 5.Y.166.244; 5.Y.169.228; 5.Y.169.229; 5.Y.169.230; 5.Y.169.231; 5.Y.169.236; 5.Y.169.237; 5.Y.169.238; 5.Y.169.239; 5.Y.169.154; 5.Y.169.157; 5.Y.169.166; 5.Y.169.169; 5.Y.169.172; 5.Y.169.175; 5.Y.169.240; 5.Y.169.244; 5.Y.172.228; 5.Y.172.229; 5.Y.172.230; 5.Y.172.231; 5.Y.172.236; 5.Y.172.237; 5.Y.172.238; 5.Y.172.239; 5.Y.172.154; 5.Y.172.157; 5.Y.172.166; 5.Y.172.169; 5.Y.172.172; 5.Y.172.175; 5.Y.172.240; 5.Y.172.244; 5.Y.175.228; 5.Y.175.229; 5.Y.175.230; 5.Y.175.231; 5.Y.175.236; 5.Y.175.237; 5.Y.175.238; 5.Y.175.239; 5.Y.175.154; 5.Y.175.157; 5.Y.175.166; 5.Y.175.169; 5.Y.175.172; 5.Y.175.175; 5.Y.175.240; 5.Y.175.244; 5.Y.240.228; 5.Y.240.229; 5.Y.240.230; 5.Y.240.231; 5.Y.240.236; 5.Y.240.237; 5.Y.240.238; 5.Y.240.239; 5.Y.240.154; 5.Y.240.157; 5.Y.240.166; 5.Y.240.169; 5.Y.240.172; 5.Y.240.175; 5.Y.240.240; 5.Y.240.244; 5.Y.244.228; 5.Y.244.229; 5.Y.244.230; 5.Y.244.231; 5.Y.244.236; 5.Y.244.237; 5.Y.244.238; 5.Y.244.239; 5.Y.244.154; 5.Y.244.157; 5.Y.244.166; 5.Y.244.169; 5.Y.244.172; 5.Y.244.175; 5.Y.244.240; 5.Y.244.244;

Prodrugs of 6.B

6.B.228.228; 6.B.228.229; 6.B.228.230; 6.B.228.231; 6.B.228.236; 6.B.228.237; 6.B.228.238; 6.B.228.239; 6.B.228.154; 6.B.228.157; 6.B.228.166; 6.B.228.169; 6.B.228.172; 6.B.228.175; 6.B.228.240; 6.B.228.244; 6.B.229.228; 6.B.229.229; 6.B.229.230; 6.B.229.231; 6.B.229.236; 6.B.229.237; 6.B.229.238; 6.B.229.239; 6.B.229.154; 6.B.229.157; 6.B.229.166; 6.B.229.169; 6.B.229.172; 6.B.229.175; 6.B.229.240; 6.B.229.244; 6.B.230.228; 6.B.230.229; 6.B.230.230; 6.B.230.231; 6.B.230.236; 6.B.230.237; 6.B.230.238; 6.B.230.239; 6.B.230.154; 6.B.230.157; 6.B.230.166; 6.B.230.169; 6.B.230.172; 6.B.230.175; 6.B.230.240; 6.B.230.244; 6.B.231.228; 6.B.231.229; 6.B.231.230; 6.B.231.231; 6.B.231.236; 6.B.231.237; 6.B.231.238; 6.B.231.239; 6.B.231.154; 6.B.231.157; 6.B.231.166; 6.B.231.169; 6.B.231.172; 6.B.231.175; 6.B.231.240; 6.B.231.244; 6.B.236.228; 6.B.236.229; 6.B.236.230; 6.B.236.231; 6.B.236.236; 6.B.236.237; 6.B.236.238; 6.B.236.239; 6.B.236.154; 6.B.236.157; 6.B.236.166; 6.B.236.169; 6.B.236.172; 6.B.236.175; 6.B.236.240; 6.B.236.244; 6.B.237.228; 6.B.237.229; 6.B.237.230; 6.B.237.231; 6.B.237.236; 6.B.237.237; 6.B.237.238; 6.B.237.239; 6.B.237.154; 6.B.237.157; 6.B.237.166; 6.B.237.169; 6.B.237.172; 6.B.237.175; 6.B.237.240; 6.B.237.244; 6.B.238.228; 6.B.238.229; 6.B.238.230; 6.B.238.231; 6.B.238.236; 6.B.238.237; 6.B.238.238; 6.B.238.239; 6.B.238.154; 6.B.238.157; 6.B.238.166; 6.B.238.169; 6.B.238.172; 6.B.238.175; 6.B.238.240; 6.B.238.244; 6.B.239.228; 6.B.239.229; 6.B.239.230; 6.B.239.231; 6.B.239.236; 6.B.239.237; 6.B.239.238; 6.B.239.239; 6.B.239.154; 6.B.239.157; 6.B.239.166; 6.B.239.169; 6.B.239.172; 6.B.239.175; 6.B.239.240; 6.B.239.244; 6.B.154.228; 6.B.154.229; 6.B.154.230; 6.B.154.231; 6.B.154.236; 6.B.154.237; 6.B.154.238; 6.B.154.239; 6.B.154.154; 6.B.154.157; 6.B.154.166; 6.B.154.169; 6.B.154.172; 6.B.154.175; 6.B.154.240; 6.B.154.244; 6.B.157.228; 6.B.157.229; 6.B.157.230; 6.B.157.231; 6.B.157.236; 6.B.157.237; 6.B.157.238; 6.B.157.239; 6.B.157.154; 6.B.157.157; 6.B.157.166; 6.B.157.169; 6.B.157.172; 6.B.157.175; 6.B.157.240; 6.B.157.244; 6.B.166.228; 6.B.166.229; 6.B.166.230; 6.B.166.231; 6.B.166.236; 6.B.166.237; 6.B.166.238; 6.B.166.239; 6.B.166.154; 6.B.166.157; 6.B.166.166; 6.B.166.169; 6.B.166.172; 6.B.166.175; 6.B.166.240; 6.B.166.244; 6.B.169.228; 6.B.169.229; 6.B.169.230; 6.B.169.231; 6.B.169.236; 6.B.169.237; 6.B.169.238; 6.B.169.239; 6.B.169.154; 6.B.169.157; 6.B.169.166; 6.B.169.169; 6.B.169.172; 6.B.169.175; 6.B.169.240; 6.B.169.244; 6.B.172.228; 6.B.172.229; 6.B.172.230; 6.B.172.231; 6.B.172.236; 6.B.172.237; 6.B.172.238; 6.B.172.239; 6.B.172.154; 6.B.172.157; 6.B.172.166; 6.B.172.169; 6.B.172.172; 6.B.172.175; 6.B.172.240; 6.B.172.244; 6.B.175.228; 6.B.175.229; 6.B.175.230; 6.B.175.231; 6.B.175.236; 6.B.175.237; 6.B.175.238; 6.B.175.239; 6.B.175.154; 6.B.175.157; 6.B.175.166; 6.B.175.169; 6.B.175.172; 6.B.175.175; 6.B.175.240; 6.B.175.244; 6.B.240.228; 6.B.240.229; 6.B.240.230; 6.B.240.231; 6.B.240.236; 6.B.240.237; 6.B.240.238; 6.B.240.239; 6.B.240.154; 6.B.240.157; 6.B.240.166; 6.B.240.169; 6.B.240.172; 6.B.240.175; 6.B.240.240; 6.B.240.244; 6.B.244.228; 6.B.244.229; 6.B.244.230; 6.B.244.231; 6.B.244.236; 6.B.244.237; 6.B.244.238; 6.B.244.239; 6.B.244.154; 6.B.244.157; 6.B.244.166; 6.B.244.169; 6.B.244.172; 6.B.244.175; 6.B.244.240; 6.B.244.244;

Prodrugs of 6.D

6.D.228.228; 6.D.228.229; 6.D.228.230; 6.D.228.231; 6.D.228.236; 6.D.228.237; 6.D.228.238; 6.D.228.239; 6.D.228.154; 6.D.228.157; 6.D.228.166; 6.D.228.169; 6.D.228.172; 6.D.228.175; 6.D.228.240; 6.D.228.244; 6.D.229.228; 6.D.229.229; 6.D.229.230; 6.D.229.231; 6.D.229.236; 6.D.229.237; 6.D.229.238; 6.D.229.239; 6.D.229.154; 6.D.229.157; 6.D.229.166; 6.D.229.169; 6.D.229.172; 6.D.229.175; 6.D.229.240; 6.D.229.244; 6.D.230.228; 6.D.230.229; 6.D.230.230; 6.D.230.231; 6.D.230.236; 6.D.230.237; 6.D.230.238; 6.D.230.239; 6.D.230.154; 6.D.230.157; 6.D.230.166; 6.D.230.169; 6.D.230.172; 6.D.230.175; 6.D.230.240; 6.D.230.244; 6.D.231.228; 6.D.231.229; 6.D.231.230; 6.D.231.231; 6.D.231.236; 6.D.231.237; 6.D.231.238; 6.D.231.239; 6.D.231.154; 6.D.231.157; 6.D.231.166; 6.D.231.169; 6.D.231.172; 6.D.231.175; 6.D.231.240; 6.D.231.244; 6.D.236.228; 6.D.236.229;

TABLE 100-continued

6.D.236.230; 6.D.236.231; 6.D.236.236; 6.D.236.237; 6.D.236.238; 6.D.236.239; 6.D.236.154; 6.D.236.157; 6.D.236.166; 6.D.236.169; 6.D.236.172; 6.D.236.175; 6.D.236.240; 6.D.236.244; 6.D.237.228; 6.D.237.229; 6.D.237.230; 6.D.237.231; 6.D.237.236; 6.D.237.237; 6.D.237.238; 6.D.237.239; 6.D.237.154; 6.D.237.157; 6.D.237.166; 6.D.237.169; 6.D.237.172; 6.D.237.175; 6.D.237.240; 6.D.237.244; 6.D.238.228; 6.D.238.229; 6.D.238.230; 6.D.238.231; 6.D.238.236; 6.D.238.237; 6.D.238.238; 6.D.238.239; 6.D.238.154; 6.D.238.157; 6.D.238.166; 6.D.238.169; 6.D.238.172; 6.D.238.175; 6.D.238.240; 6.D.238.244; 6.D.239.228; 6.D.239.229; 6.D.239.230; 6.D.239.231; 6.D.239.236; 6.D.239.237; 6.D.239.238; 6.D.239.239; 6.D.239.154; 6.D.239.157; 6.D.239.166; 6.D.239.169; 6.D.239.172; 6.D.239.175; 6.D.239.240; 6.D.239.244; 6.D.154.228; 6.D.154.229; 6.D.154.230; 6.D.154.231; 6.D.154.236; 6.D.154.237; 6.D.154.238; 6.D.154.239; 6.D.154.154; 6.D.154.157; 6.D.154.166; 6.D.154.169; 6.D.154.172; 6.D.154.175; 6.D.154.240; 6.D.154.244; 6.D.157.228; 6.D.157.229; 6.D.157.230; 6.D.157.231; 6.D.157.236; 6.D.157.237; 6.D.157.238; 6.D.157.239; 6.D.157.154; 6.D.157.157; 6.D.157.166; 6.D.157.169; 6.D.157.172; 6.D.157.175; 6.D.157.240; 6.D.157.244; 6.D.166.228; 6.D.166.229; 6.D.166.230; 6.D.166.231; 6.D.166.236; 6.D.166.237; 6.D.166.238; 6.D.166.239; 6.D.166.154; 6.D.166.157; 6.D.166.166; 6.D.166.169; 6.D.166.172; 6.D.166.175; 6.D.166.240; 6.D.166.244; 6.D.169.228; 6.D.169.229; 6.D.169.230; 6.D.169.231; 6.D.169.236; 6.D.169.237; 6.D.169.238; 6.D.169.239; 6.D.169.154; 6.D.169.157; 6.D.169.166; 6.D.169.169; 6.D.169.172; 6.D.169.175; 6.D.169.240; 6.D.169.244; 6.D.172.228; 6.D.172.229; 6.D.172.230; 6.D.172.231; 6.D.172.236; 6.D.172.237; 6.D.172.238; 6.D.172.239; 6.D.172.154; 6.D.172.157; 6.D.172.166; 6.D.172.169; 6.D.172.172; 6.D.172.175; 6.D.172.240; 6.D.172.244; 6.D.175.228; 6.D.175.229; 6.D.175.230; 6.D.175.231; 6.D.175.236; 6.D.175.237; 6.D.175.238; 6.D.175.239; 6.D.175.154; 6.D.175.157; 6.D.175.166; 6.D.175.169; 6.D.175.172; 6.D.175.175; 6.D.175.240; 6.D.175.244; 6.D.240.228; 6.D.240.229; 6.D.240.230; 6.D.240.231; 6.D.240.236; 6.D.240.237; 6.D.240.238; 6.D.240.239; 6.D.240.154; 6.D.240.157; 6.D.240.166; 6.D.240.169; 6.D.240.172; 6.D.240.175; 6.D.240.240; 6.D.240.244; 6.D.244.228; 6.D.244.229; 6.D.244.230; 6.D.244.231; 6.D.244.236; 6.D.244.237; 6.D.244.238; 6.D.244.239; 6.D.244.154; 6.D.244.157; 6.D.244.166; 6.D.244.169; 6.D.244.172; 6.D.244.175; 6.D.244.240; 6.D.244.244;

Prodrugs of 6.E

6.E.228.228; 6.E.228.229; 6.E.228.230; 6.E.228.231; 6.E.228.236; 6.E.228.237; 6.E.228.238; 6.E.228.239; 6.E.228.154; 6.E.228.157; 6.E.228.166; 6.E.228.169; 6.E.228.172; 6.E.228.175; 6.E.228.240; 6.E.228.244; 6.E.229.228; 6.E.229.229; 6.E.229.230; 6.E.229.231; 6.E.229.236; 6.E.229.237; 6.E.229.238; 6.E.229.239; 6.E.229.154; 6.E.229.157; 6.E.229.166; 6.E.229.169; 6.E.229.172; 6.E.229.175; 6.E.229.240; 6.E.229.244; 6.E.230.228; 6.E.230.229; 6.E.230.230; 6.E.230.231; 6.E.230.236; 6.E.230.237; 6.E.230.238; 6.E.230.239; 6.E.230.154; 6.E.230.157; 6.E.230.166; 6.E.230.169; 6.E.230.172; 6.E.230.175; 6.E.230.240; 6.E.230.244; 6.E.231.228; 6.E.231.229; 6.E.231.230; 6.E.231.231; 6.E.231.236; 6.E.231.237; 6.E.231.238; 6.E.231.239; 6.E.231.154; 6.E.231.157; 6.E.231.166; 6.E.231.169; 6.E.231.172; 6.E.231.175; 6.E.231.240; 6.E.231.244; 6.E.236.228; 6.E.236.229; 6.E.236.230; 6.E.236.231; 6.E.236.236; 6.E.236.237; 6.E.236.238; 6.E.236.239; 6.E.236.154; 6.E.236.157; 6.E.236.166; 6.E.236.169; 6.E.236.172; 6.E.236.175; 6.E.236.240; 6.E.236.244; 6.E.237.228; 6.E.237.229; 6.E.237.230; 6.E.237.231; 6.E.237.236; 6.E.237.237; 6.E.237.238; 6.E.237.239; 6.E.237.154; 6.E.237.157; 6.E.237.166; 6.E.237.169; 6.E.237.172; 6.E.237.175; 6.E.237.240; 6.E.237.244; 6.E.238.228; 6.E.238.229; 6.E.238.230; 6.E.238.231; 6.E.238.236; 6.E.238.237; 6.E.238.238; 6.E.238.239; 6.E.238.154; 6.E.238.157; 6.E.238.166; 6.E.238.169; 6.E.238.172; 6.E.238.175; 6.E.238.240; 6.E.238.244; 6.E.239.228; 6.E.239.229; 6.E.239.230; 6.E.239.231; 6.E.239.236; 6.E.239.237; 6.E.239.238; 6.E.239.239; 6.E.239.154; 6.E.239.157; 6.E.239.166; 6.E.239.169; 6.E.239.172; 6.E.239.175; 6.E.239.240; 6.E.239.244; 6.E.154.228; 6.E.154.229; 6.E.154.230; 6.E.154.231; 6.E.154.236; 6.E.154.237; 6.E.154.238; 6.E.154.239; 6.E.154.154; 6.E.154.157; 6.E.154.166; 6.E.154.169; 6.E.154.172; 6.E.154.175; 6.E.154.240; 6.E.154.244; 6.E.157.228; 6.E.157.229; 6.E.157.230; 6.E.157.231; 6.E.157.236; 6.E.157.237; 6.E.157.238; 6.E.157.239; 6.E.157.154; 6.E.157.157; 6.E.157.166; 6.E.157.169; 6.E.157.172; 6.E.157.175; 6.E.157.240; 6.E.157.244; 6.E.166.228; 6.E.166.229; 6.E.166.230; 6.E.166.231; 6.E.166.236; 6.E.166.237; 6.E.166.238; 6.E.166.239; 6.E.166.154; 6.E.166.157; 6.E.166.166; 6.E.166.169; 6.E.166.172; 6.E.166.175; 6.E.166.240; 6.E.166.244; 6.E.169.228; 6.E.169.229; 6.E.169.230; 6.E.169.231; 6.E.169.236; 6.E.169.237; 6.E.169.238; 6.E.169.239; 6.E.169.154; 6.E.169.157; 6.E.169.166; 6.E.169.169; 6.E.169.172; 6.E.169.175; 6.E.169.240; 6.E.169.244; 6.E.172.228; 6.E.172.229; 6.E.172.230; 6.E.172.231; 6.E.172.236; 6.E.172.237; 6.E.172.238; 6.E.172.239; 6.E.172.154; 6.E.172.157; 6.E.172.166; 6.E.172.169; 6.E.172.172; 6.E.172.175; 6.E.172.240; 6.E.172.244; 6.E.175.228; 6.E.175.229; 6.E.175.230; 6.E.175.231; 6.E.175.236; 6.E.175.237; 6.E.175.238; 6.E.175.239; 6.E.175.154; 6.E.175.157; 6.E.175.166; 6.E.175.169; 6.E.175.172; 6.E.175.175; 6.E.175.240; 6.E.175.244; 6.E.240.228; 6.E.240.229; 6.E.240.230; 6.E.240.231; 6.E.240.236; 6.E.240.237; 6.E.240.238; 6.E.240.239; 6.E.240.154; 6.E.240.157; 6.E.240.166; 6.E.240.169; 6.E.240.172; 6.E.240.175; 6.E.240.240; 6.E.240.244; 6.E.244.228; 6.E.244.229; 6.E.244.230; 6.E.244.231; 6.E.244.236; 6.E.244.237; 6.E.244.238; 6.E.244.239; 6.E.244.154; 6.E.244.157; 6.E.244.166; 6.E.244.169; 6.E.244.172; 6.E.244.175; 6.E.244.240; 6.E.244.244;

Prodrugs of 6.G

6.G.228.228; 6.G.228.229; 6.G.228.230; 6.G.228.231; 6.G.228.236; 6.G.228.237; 6.G.228.238; 6.G.228.239; 6.G.228.154; 6.G.228.157; 6.G.228.166; 6.G.228.169; 6.G.228.172; 6.G.228.175; 6.G.228.240; 6.G.228.244; 6.G.229.228; 6.G.229.229; 6.G.229.230; 6.G.229.231; 6.G.229.236; 6.G.229.237; 6.G.229.238; 6.G.229.239; 6.G.229.154; 6.G.229.157; 6.G.229.166; 6.G.229.169; 6.G.229.172; 6.G.229.175; 6.G.229.240; 6.G.229.244; 6.G.230.228; 6.G.230.229; 6.G.230.230; 6.G.230.231;

TABLE 100-continued

6.G.230.236; 6.G.230.237; 6.G.230.238; 6.G.230.239; 6.G.230.154; 6.G.230.157; 6.G.230.166; 6.G.230.169; 6.G.230.172; 6.G.230.175; 6.G.230.240; 6.G.230.244; 6.G.231.228; 6.G.231.229; 6.G.231.230; 6.G.231.231; 6.G.231.236; 6.G.231.237; 6.G.231.238; 6.G.231.239; 6.G.231.154; 6.G.231.157; 6.G.231.166; 6.G.231.169; 6.G.231.172; 6.G.231.175; 6.G.231.240; 6.G.231.244; 6.G.236.228; 6.G.236.229; 6.G.236.230; 6.G.236.231; 6.G.236.236; 6.G.236.237; 6.G.236.238; 6.G.236.239; 6.G.236.154; 6.G.236.157; 6.G.236.166; 6.G.236.169; 6.G.236.172; 6.G.236.175; 6.G.236.240; 6.G.236.244; 6.G.237.228; 6.G.237.229; 6.G.237.230; 6.G.237.231; 6.G.237.236; 6.G.237.237; 6.G.237.238; 6.G.237.239; 6.G.237.154; 6.G.237.157; 6.G.237.166; 6.G.237.169; 6.G.237.172; 6.G.237.175; 6.G.237.240; 6.G.237.244; 6.G.238.228; 6.G.238.229; 6.G.238.230; 6.G.238.231; 6.G.238.236; 6.G.238.237; 6.G.238.238; 6.G.238.239; 6.G.238.154; 6.G.238.157; 6.G.238.166; 6.G.238.169; 6.G.238.172; 6.G.238.175; 6.G.238.240; 6.G.238.244; 6.G.239.228; 6.G.239.229; 6.G.239.230; 6.G.239.231; 6.G.239.236; 6.G.239.237; 6.G.239.238; 6.G.239.239; 6.G.239.154; 6.G.239.157; 6.G.239.166; 6.G.239.169; 6.G.239.172; 6.G.239.175; 6.G.239.240; 6.G.239.244; 6.G.154.228; 6.G.154.229; 6.G.154.230; 6.G.154.231; 6.G.154.236; 6.G.154.237; 6.G.154.238; 6.G.154.239; 6.G.154.154; 6.G.154.157; 6.G.154.166; 6.G.154.169; 6.G.154.172; 6.G.154.175; 6.G.154.240; 6.G.154.244; 6.G.157.228; 6.G.157.229; 6.G.157.230; 6.G.157.231; 6.G.157.236; 6.G.157.237; 6.G.157.238; 6.G.157.239; 6.G.157.154; 6.G.157.157; 6.G.157.166; 6.G.157.169; 6.G.157.172; 6.G.157.175; 6.G.157.240; 6.G.157.244; 6.G.166.228; 6.G.166.229; 6.G.166.230; 6.G.166.231; 6.G.166.236; 6.G.166.237; 6.G.166.238; 6.G.166.239; 6.G.166.154; 6.G.166.157; 6.G.166.166; 6.G.166.169; 6.G.166.172; 6.G.166.175; 6.G.166.240; 6.G.166.244; 6.G.169.228; 6.G.169.229; 6.G.169.230; 6.G.169.231; 6.G.169.236; 6.G.169.237; 6.G.169.238; 6.G.169.239; 6.G.169.154; 6.G.169.157; 6.G.169.166; 6.G.169.169; 6.G.169.172; 6.G.169.175; 6.G.169.240; 6.G.169.244; 6.G.172.228; 6.G.172.229; 6.G.172.230; 6.G.172.231; 6.G.172.236; 6.G.172.237; 6.G.172.238; 6.G.172.239; 6.G.172.154; 6.G.172.157; 6.G.172.166; 6.G.172.169; 6.G.172.172; 6.G.172.175; 6.G.172.240; 6.G.172.244; 6.G.175.228; 6.G.175.229; 6.G.175.230; 6.G.175.231; 6.G.175.236; 6.G.175.237; 6.G.175.238; 6.G.175.239; 6.G.175.154; 6.G.175.157; 6.G.175.166; 6.G.175.169; 6.G.175.172; 6.G.175.175; 6.G.175.240; 6.G.175.244; 6.G.240.228; 6.G.240.229; 6.G.240.230; 6.G.240.231; 6.G.240.236; 6.G.240.237; 6.G.240.238; 6.G.240.239; 6.G.240.154; 6.G.240.157; 6.G.240.166; 6.G.240.169; 6.G.240.172; 6.G.240.175; 6.G.240.240; 6.G.240.244; 6.G.244.228; 6.G.244.229; 6.G.244.230; 6.G.244.231; 6.G.244.236; 6.G.244.237; 6.G.244.238; 6.G.244.239; 6.G.244.154; 6.G.244.157; 6.G.244.166; 6.G.244.169; 6.G.244.172; 6.G.244.175; 6.G.244.240; 6.G.244.244;

Prodrugs of 6.I

6.I.228.228; 6.I.228.229; 6.I.228.230; 6.I.228.231; 6.I.228.236; 6.I.228.237; 6.I.228.238; 6.I.228.239; 6.I.228.154; 6.I.228.157; 6.I.228.166; 6.I.228.169; 6.I.228.172; 6.I.228.175; 6.I.228.240; 6.I.228.244; 6.I.229.228; 6.I.229.229; 6.I.229.230; 6.I.229.231; 6.I.229.236; 6.I.229.237; 6.I.229.238; 6.I.229.239; 6.I.229.154; 6.I.229.157; 6.I.229.166; 6.I.229.169; 6.I.229.172; 6.I.229.175; 6.I.229.240; 6.I.229.244; 6.I.230.228; 6.I.230.229; 6.I.230.230; 6.I.230.231; 6.I.230.236; 6.I.230.237; 6.I.230.238; 6.I.230.239; 6.I.230.154; 6.I.230.157; 6.I.230.166; 6.I.230.169; 6.I.230.172; 6.I.230.175; 6.I.230.240; 6.I.230.244; 6.I.231.228; 6.I.231.229; 6.I.231.230; 6.I.231.231; 6.I.231.236; 6.I.231.237; 6.I.231.238; 6.I.231.239; 6.I.231.154; 6.I.231.157; 6.I.231.166; 6.I.231.169; 6.I.231.172; 6.I.231.175; 6.I.231.240; 6.I.231.244; 6.I.236.228; 6.I.236.229; 6.I.236.230; 6.I.236.231; 6.I.236.236; 6.I.236.237; 6.I.236.238; 6.I.236.239; 6.I.236.154; 6.I.236.157; 6.I.236.166; 6.I.236.169; 6.I.236.172; 6.I.236.175; 6.I.236.240; 6.I.236.244; 6.I.237.228; 6.I.237.229; 6.I.237.230; 6.I.237.231; 6.I.237.236; 6.I.237.237; 6.I.237.238; 6.I.237.239; 6.I.237.154; 6.I.237.157; 6.I.237.166; 6.I.237.169; 6.I.237.172; 6.I.237.175; 6.I.237.240; 6.I.237.244; 6.I.238.228; 6.I.238.229; 6.I.238.230; 6.I.238.231; 6.I.238.236; 6.I.238.237; 6.I.238.238; 6.I.238.239; 6.I.238.154; 6.I.238.157; 6.I.238.166; 6.I.238.169; 6.I.238.172; 6.I.238.175; 6.I.238.240; 6.I.238.244; 6.I.239.228; 6.I.239.229; 6.I.239.230; 6.I.239.231; 6.I.239.236; 6.I.239.237; 6.I.239.238; 6.I.239.239; 6.I.239.154; 6.I.239.157; 6.I.239.166; 6.I.239.169; 6.I.239.172; 6.I.239.175; 6.I.239.240; 6.I.239.244; 6.I.154.228; 6.I.154.229; 6.I.154.230; 6.I.154.231; 6.I.154.236; 6.I.154.237; 6.I.154.238; 6.I.154.239; 6.I.154.154; 6.I.154.157; 6.I.154.166; 6.I.154.169; 6.I.154.172; 6.I.154.175; 6.I.154.240; 6.I.154.244; 6.I.157.228; 6.I.157.229; 6.I.157.230; 6.I.157.231; 6.I.157.236; 6.I.157.237; 6.I.157.238; 6.I.157.239; 6.I.157.154; 6.I.157.157; 6.I.157.166; 6.I.157.169; 6.I.157.172; 6.I.157.175; 6.I.157.240; 6.I.157.244; 6.I.166.228; 6.I.166.229; 6.I.166.230; 6.I.166.231; 6.I.166.236; 6.I.166.237; 6.I.166.238; 6.I.166.239; 6.I.166.154; 6.I.166.157; 6.I.166.166; 6.I.166.169; 6.I.166.172; 6.I.166.175; 6.I.166.240; 6.I.166.244; 6.I.169.228; 6.I.169.229; 6.I.169.230; 6.I.169.231; 6.I.169.236; 6.I.169.237; 6.I.169.238; 6.I.169.239; 6.I.169.154; 6.I.169.157; 6.I.169.166; 6.I.169.169; 6.I.169.172; 6.I.169.175; 6.I.169.240; 6.I.169.244; 6.I.172.228; 6.I.172.229; 6.I.172.230; 6.I.172.231; 6.I.172.236; 6.I.172.237; 6.I.172.238; 6.I.172.239; 6.I.172.154; 6.I.172.157; 6.I.172.166; 6.I.172.169; 6.I.172.172; 6.I.172.175; 6.I.172.240; 6.I.172.244; 6.I.175.228; 6.I.175.229; 6.I.175.230; 6.I.175.231; 6.I.175.236; 6.I.175.237; 6.I.175.238; 6.I.175.239; 6.I.175.154; 6.I.175.157; 6.I.175.166; 6.I.175.169; 6.I.175.172; 6.I.175.175; 6.I.175.240; 6.I.175.244; 6.I.240.228; 6.I.240.229; 6.I.240.230; 6.I.240.231; 6.I.240.236; 6.I.240.237; 6.I.240.238; 6.I.240.239; 6.I.240.154; 6.I.240.157; 6.I.240.166; 6.I.240.169; 6.I.240.172; 6.I.240.175; 6.I.240.240; 6.I.240.244; 6.I.244.228; 6.I.244.229; 6.I.244.230; 6.I.244.231; 6.I.244.236; 6.I.244.237; 6.I.244.238; 6.I.244.239; 6.I.244.154; 6.I.244.157; 6.I.244.166; 6.I.244.169; 6.I.244.172; 6.I.244.175; 6.I.244.240; 6.I.244.244;

TABLE 100-continued

Prodrugs of 6.J

6.J.228.228; 6.J.228.229; 6.J.228.230; 6.J.228.231; 6.J.228.236; 6.J.228.237; 6.J.228.238; 6.J.228.239; 6.J.228.154; 6.J.228.157; 6.J.228.166; 6.J.228.169; 6.J.228.172; 6.J.228.175; 6.J.228.240; 6.J.228.244; 6.J.229.228; 6.J.229.229; 6.J.229.230; 6.J.229.231; 6.J.229.236; 6.J.229.237; 6.J.229.238; 6.J.229.239; 6.J.229.154; 6.J.229.157; 6.J.229.166; 6.J.229.169; 6.J.229.172; 6.J.229.175; 6.J.229.240; 6.J.229.244; 6.J.230.228; 6.J.230.229; 6.J.230.230; 6.J.230.231; 6.J.230.236; 6.J.230.237; 6.J.230.238; 6.J.230.239; 6.J.230.154; 6.J.230.157; 6.J.230.166; 6.J.230.169; 6.J.230.172; 6.J.230.175; 6.J.230.240; 6.J.230.244; 6.J.231.228; 6.J.231.229; 6.J.231.230; 6.J.231.231; 6.J.231.236; 6.J.231.237; 6.J.231.238; 6.J.231.239; 6.J.231.154; 6.J.231.157; 6.J.231.166; 6.J.231.169; 6.J.231.172; 6.J.231.175; 6.J.231.240; 6.J.231.244; 6.J.236.228; 6.J.236.229; 6.J.236.230; 6.J.236.231; 6.J.236.236; 6.J.236.237; 6.J.236.238; 6.J.236.239; 6.J.236.154; 6.J.236.157; 6.J.236.166; 6.J.236.169; 6.J.236.172; 6.J.236.175; 6.J.236.240; 6.J.236.244; 6.J.237.228; 6.J.237.229; 6.J.237.230; 6.J.237.231; 6.J.237.236; 6.J.237.237; 6.J.237.238; 6.J.237.239; 6.J.237.154; 6.J.237.157; 6.J.237.166; 6.J.237.169; 6.J.237.172; 6.J.237.175; 6.J.237.240; 6.J.237.244; 6.J.238.228; 6.J.238.229; 6.J.238.230; 6.J.238.231; 6.J.238.236; 6.J.238.237; 6.J.238.238; 6.J.238.239; 6.J.238.154; 6.J.238.157; 6.J.238.166; 6.J.238.169; 6.J.238.172; 6.J.238.175; 6.J.238.240; 6.J.238.244; 6.J.239.228; 6.J.239.229; 6.J.239.230; 6.J.239.231; 6.J.239.236; 6.J.239.237; 6.J.239.238; 6.J.239.239; 6.J.239.154; 6.J.239.157; 6.J.239.166; 6.J.239.169; 6.J.239.172; 6.J.239.175; 6.J.239.240; 6.J.239.244; 6.J.154.228; 6.J.154.229; 6.J.154.230; 6.J.154.231; 6.J.154.236; 6.J.154.237; 6.J.154.238; 6.J.154.239; 6.J.154.154; 6.J.154.157; 6.J.154.166; 6.J.154.169; 6.J.154.172; 6.J.154.175; 6.J.154.240; 6.J.154.244; 6.J.157.228; 6.J.157.229; 6.J.157.230; 6.J.157.231; 6.J.157.236; 6.J.157.237; 6.J.157.238; 6.J.157.239; 6.J.157.154; 6.J.157.157; 6.J.157.166; 6.J.157.169; 6.J.157.172; 6.J.157.175; 6.J.157.240; 6.J.157.244; 6.J.166.228; 6.J.166.229; 6.J.166.230; 6.J.166.231; 6.J.166.236; 6.J.166.237; 6.J.166.238; 6.J.166.239; 6.J.166.154; 6.J.166.157; 6.J.166.166; 6.J.166.169; 6.J.166.172; 6.J.166.175; 6.J.166.240; 6.J.166.244; 6.J.169.228; 6.J.169.229; 6.J.169.230; 6.J.169.231; 6.J.169.236; 6.J.169.237; 6.J.169.238; 6.J.169.239; 6.J.169.154; 6.J.169.157; 6.J.169.166; 6.J.169.169; 6.J.169.172; 6.J.169.175; 6.J.169.240; 6.J.169.244; 6.J.172.228; 6.J.172.229; 6.J.172.230; 6.J.172.231; 6.J.172.236; 6.J.172.237; 6.J.172.238; 6.J.172.239; 6.J.172.154; 6.J.172.157; 6.J.172.166; 6.J.172.169; 6.J.172.172; 6.J.172.175; 6.J.172.240; 6.J.172.244; 6.J.175.228; 6.J.175.229; 6.J.175.230; 6.J.175.231; 6.J.175.236; 6.J.175.237; 6.J.175.238; 6.J.175.239; 6.J.175.154; 6.J.175.157; 6.J.175.166; 6.J.175.169; 6.J.175.172; 6.J.175.175; 6.J.175.240; 6.J.175.244; 6.J.240.228; 6.J.240.229; 6.J.240.230; 6.J.240.231; 6.J.240.236; 6.J.240.237; 6.J.240.238; 6.J.240.239; 6.J.240.154; 6.J.240.157; 6.J.240.166; 6.J.240.169; 6.J.240.172; 6.J.240.175; 6.J.240.240; 6.J.240.244; 6.J.244.228; 6.J.244.229; 6.J.244.230; 6.J.244.231; 6.J.244.236; 6.J.244.237; 6.J.244.238; 6.J.244.239; 6.J.244.154; 6.J.244.157; 6.J.244.166; 6.J.244.169; 6.J.244.172; 6.J.244.175; 6.J.244.240; 6.J.244.244;

Prodrugs of 6.L

6.L.228.228; 6.L.228.229; 6.L.228.230; 6.L.228.231; 6.L.228.236; 6.L.228.237; 6.L.228.238; 6.L.228.239; 6.L.228.154; 6.L.228.157; 6.L.228.166; 6.L.228.169; 6.L.228.172; 6.L.228.175; 6.L.228.240; 6.L.228.244; 6.L.229.228; 6.L.229.229; 6.L.229.230; 6.L.229.231; 6.L.229.236; 6.L.229.237; 6.L.229.238; 6.L.229.239; 6.L.229.154; 6.L.229.157; 6.L.229.166; 6.L.229.169; 6.L.229.172; 6.L.229.175; 6.L.229.240; 6.L.229.244; 6.L.230.228; 6.L.230.229; 6.L.230.230; 6.L.230.231; 6.L.230.236; 6.L.230.237; 6.L.230.238; 6.L.230.239; 6.L.230.154; 6.L.230.157; 6.L.230.166; 6.L.230.169; 6.L.230.172; 6.L.230.175; 6.L.230.240; 6.L.230.244; 6.L.231.228; 6.L.231.229; 6.L.231.230; 6.L.231.231; 6.L.231.236; 6.L.231.237; 6.L.231.238; 6.L.231.239; 6.L.231.154; 6.L.231.157; 6.L.231.166; 6.L.231.169; 6.L.231.172; 6.L.231.175; 6.L.231.240; 6.L.231.244; 6.L.236.228; 6.L.236.229; 6.L.236.230; 6.L.236.231; 6.L.236.236; 6.L.236.237; 6.L.236.238; 6.L.236.239; 6.L.236.154; 6.L.236.157; 6.L.236.166; 6.L.236.169; 6.L.236.172; 6.L.236.175; 6.L.236.240; 6.L.236.244; 6.L.237.228; 6.L.237.229; 6.L.237.230; 6.L.237.231; 6.L.237.236; 6.L.237.237; 6.L.237.238; 6.L.237.239; 6.L.237.154; 6.L.237.157; 6.L.237.166; 6.L.237.169; 6.L.237.172; 6.L.237.175; 6.L.237.240; 6.L.237.244; 6.L.238.228; 6.L.238.229; 6.L.238.230; 6.L.238.231; 6.L.238.236; 6.L.238.237; 6.L.238.238; 6.L.238.239; 6.L.238.154; 6.L.238.157; 6.L.238.166; 6.L.238.169; 6.L.238.172; 6.L.238.175; 6.L.238.240; 6.L.238.244; 6.L.239.228; 6.L.239.229; 6.L.239.230; 6.L.239.231; 6.L.239.236; 6.L.239.237; 6.L.239.238; 6.L.239.239; 6.L.239.154; 6.L.239.157; 6.L.239.166; 6.L.239.169; 6.L.239.172; 6.L.239.175; 6.L.239.240; 6.L.239.244; 6.L.154.228; 6.L.154.229; 6.L.154.230; 6.L.154.231; 6.L.154.236; 6.L.154.237; 6.L.154.238; 6.L.154.239; 6.L.154.154; 6.L.154.157; 6.L.154.166; 6.L.154.169; 6.L.154.172; 6.L.154.175; 6.L.154.240; 6.L.154.244; 6.L.157.228; 6.L.157.229; 6.L.157.230; 6.L.157.231; 6.L.157.236; 6.L.157.237; 6.L.157.238; 6.L.157.239; 6.L.157.154; 6.L.157.157; 6.L.157.166; 6.L.157.169; 6.L.157.172; 6.L.157.175; 6.L.157.240; 6.L.157.244; 6.L.166.228; 6.L.166.229; 6.L.166.230; 6.L.166.231; 6.L.166.236; 6.L.166.237; 6.L.166.238; 6.L.166.239; 6.L.166.154; 6.L.166.157; 6.L.166.166; 6.L.166.169; 6.L.166.172; 6.L.166.175; 6.L.166.240; 6.L.166.244; 6.L.169.228; 6.L.169.229; 6.L.169.230; 6.L.169.231; 6.L.169.236; 6.L.169.237; 6.L.169.238; 6.L.169.239; 6.L.169.154; 6.L.169.157; 6.L.169.166; 6.L.169.169; 6.L.169.172; 6.L.169.175; 6.L.169.240; 6.L.169.244; 6.L.172.228; 6.L.172.229; 6.L.172.230; 6.L.172.231; 6.L.172.236; 6.L.172.237; 6.L.172.238; 6.L.172.239; 6.L.172.154; 6.L.172.157; 6.L.172.166; 6.L.172.169; 6.L.172.172; 6.L.172.175; 6.L.172.240; 6.L.172.244; 6.L.175.228; 6.L.175.229; 6.L.175.230; 6.L.175.231; 6.L.175.236; 6.L.175.237; 6.L.175.238; 6.L.175.239; 6.L.175.154; 6.L.175.157; 6.L.175.166; 6.L.175.169; 6.L.175.172; 6.L.175.175; 6.L.175.240; 6.L.175.244; 6.L.240.228; 6.L.240.229; 6.L.240.230; 6.L.240.231; 6.L.240.236; 6.L.240.237; 6.L.240.238; 6.L.240.239; 6.L.240.154; 6.L.240.157; 6.L.240.166; 6.L.240.169; 6.L.240.172; 6.L.240.175; 6.L.240.240; 6.L.240.244; 6.L.244.228; 6.L.244.229; 6.L.244.230; 6.L.244.231; 6.L.244.236; 6.L.244.237; 6.L.244.238; 6.L.244.239; 6.L.244.154; 6.L.244.157; 6.L.244.166; 6.L.244.169; 6.L.244.172; 6.L.244.175; 6.L.244.240; 6.L.244.244;

TABLE 100-continued

Prodrugs of 6.O

6.O.228.228; 6.O.228.229; 6.O.228.230; 6.O.228.231; 6.O.228.236; 6.O.228.237;
6.O.228.238; 6.O.228.239; 6.O.228.154; 6.O.228.157; 6.O.228.166; 6.O.228.169;
6.O.228.172; 6.O.228.175; 6.O.228.240; 6.O.228.244; 6.O.229.228; 6.O.229.229;
6.O.229.230; 6.O.229.231; 6.O.229.236; 6.O.229.237; 6.O.229.238; 6.O.229.239;
6.O.229.154; 6.O.229.157; 6.O.229.166; 6.O.229.169; 6.O.229.172; 6.O.229.175;
6.O.229.240; 6.O.229.244; 6.O.230.228; 6.O.230.229; 6.O.230.230; 6.O.230.231;
6.O.230.236; 6.O.230.237; 6.O.230.238; 6.O.230.239; 6.O.230.154; 6.O.230.157;
6.O.230.166; 6.O.230.169; 6.O.230.172; 6.O.230.175; 6.O.230.240; 6.O.230.244;
6.O.231.228; 6.O.231.229; 6.O.231.230; 6.O.231.231; 6.O.231.236; 6.O.231.237;
6.O.231.238; 6.O.231.239; 6.O.231.154; 6.O.231.157; 6.O.231.166; 6.O.231.169;
6.O.231.172; 6.O.231.175; 6.O.231.240; 6.O.231.244; 6.O.236.228; 6.O.236.229;
6.O.236.230; 6.O.236.231; 6.O.236.236; 6.O.236.237; 6.O.236.238; 6.O.236.239;
6.O.236.154; 6.O.236.157; 6.O.236.166; 6.O.236.169; 6.O.236.172; 6.O.236.175;
6.O.236.240; 6.O.236.244; 6.O.237.228; 6.O.237.229; 6.O.237.230; 6.O.237.231;
6.O.237.236; 6.O.237.237; 6.O.237.238; 6.O.237.239; 6.O.237.154; 6.O.237.157;
6.O.237.166; 6.O.237.169; 6.O.237.172; 6.O.237.175; 6.O.237.240; 6.O.237.244;
6.O.238.228; 6.O.238.229; 6.O.238.230; 6.O.238.231; 6.O.238.236; 6.O.238.237;
6.O.238.238; 6.O.238.239; 6.O.238.154; 6.O.238.157; 6.O.238.166; 6.O.238.169;
6.O.238.172; 6.O.238.175; 6.O.238.240; 6.O.238.244; 6.O.239.228; 6.O.239.229;
6.O.239.230; 6.O.239.231; 6.O.239.236; 6.O.239.237; 6.O.239.238; 6.O.239.239;
6.O.239.154; 6.O.239.157; 6.O.239.166; 6.O.239.169; 6.O.239.172; 6.O.239.175;
6.O.239.240; 6.O.239.244; 6.O.154.228; 6.O.154.229; 6.O.154.230; 6.O.154.231;
6.O.154.236; 6.O.154.237; 6.O.154.238; 6.O.154.239; 6.O.154.154; 6.O.154.157;
6.O.154.166; 6.O.154.169; 6.O.154.172; 6.O.154.175; 6.O.154.240; 6.O.154.244;
6.O.157.228; 6.O.157.229; 6.O.157.230; 6.O.157.231; 6.O.157.236; 6.O.157.237;
6.O.157.238; 6.O.157.239; 6.O.157.154; 6.O.157.157; 6.O.157.166; 6.O.157.169;
6.O.157.172; 6.O.157.175; 6.O.157.240; 6.O.157.244; 6.O.166.228; 6.O.166.229;
6.O.166.230; 6.O.166.231; 6.O.166.236; 6.O.166.237; 6.O.166.238; 6.O.166.239;
6.O.166.154; 6.O.166.157; 6.O.166.166; 6.O.166.169; 6.O.166.172; 6.O.166.175;
6.O.166.240; 6.O.166.244; 6.O.169.228; 6.O.169.229; 6.O.169.230; 6.O.169.231;
6.O.169.236; 6.O.169.237; 6.O.169.238; 6.O.169.239; 6.O.169.154; 6.O.169.157;
6.O.169.166; 6.O.169.169; 6.O.169.172; 6.O.169.175; 6.O.169.240; 6.O.169.244;
6.O.172.228; 6.O.172.229; 6.O.172.230; 6.O.172.231; 6.O.172.236; 6.O.172.237;
6.O.172.238; 6.O.172.239; 6.O.172.154; 6.O.172.157; 6.O.172.166; 6.O.172.169;
6.O.172.172; 6.O.172.175; 6.O.172.240; 6.O.172.244; 6.O.175.228; 6.O.175.229;
6.O.175.230; 6.O.175.231; 6.O.175.236; 6.O.175.237; 6.O.175.238; 6.O.175.239;
6.O.175.154; 6.O.175.157; 6.O.175.166; 6.O.175.169; 6.O.175.172; 6.O.175.175;
6.O.175.240; 6.O.175.244; 6.O.240.228; 6.O.240.229; 6.O.240.230; 6.O.240.231;
6.O.240.236; 6.O.240.237; 6.O.240.238; 6.O.240.239; 6.O.240.154; 6.O.240.157;
6.O.240.166; 6.O.240.169; 6.O.240.172; 6.O.240.175; 6.O.240.240; 6.O.240.244;
6.O.244.228; 6.O.244.229; 6.O.244.230; 6.O.244.231; 6.O.244.236; 6.O.244.237;
6.O.244.238; 6.O.244.239; 6.O.244.154; 6.O.244.157; 6.O.244.166; 6.O.244.169;
6.O.244.172; 6.O.244.175; 6.O.244.240; 6.O.244.244;

Prodrugs of 6.P

6.P.228.228; 6.P.228.229; 6.P.228.230; 6.P.228.231; 6.P.228.236; 6.P.228.237;
6.P.228.238; 6.P.228.239; 6.P.228.154; 6.P.228.157; 6.P.228.166; 6.P.228.169; 6.P.228.172;
6.P.228.175; 6.P.228.240; 6.P.228.244; 6.P.229.228; 6.P.229.229; 6.P.229.230; 6.P.229.231;
6.P.229.236; 6.P.229.237; 6.P.229.238; 6.P.229.239; 6.P.229.154; 6.P.229.157; 6.P.229.166;
6.P.229.169; 6.P.229.172; 6.P.229.175; 6.P.229.240; 6.P.229.244; 6.P.230.228; 6.P.230.229;
6.P.230.230; 6.P.230.231; 6.P.230.236; 6.P.230.237; 6.P.230.238; 6.P.230.239; 6.P.230.154;
6.P.230.157; 6.P.230.166; 6.P.230.169; 6.P.230.172; 6.P.230.175; 6.P.230.240; 6.P.230.244;
6.P.231.228; 6.P.231.229; 6.P.231.230; 6.P.231.231; 6.P.231.236; 6.P.231.237; 6.P.231.238;
6.P.231.239; 6.P.231.154; 6.P.231.157; 6.P.231.166; 6.P.231.169; 6.P.231.172; 6.P.231.175;
6.P.231.240; 6.P.231.244; 6.P.236.228; 6.P.236.229; 6.P.236.230; 6.P.236.231; 6.P.236.236;
6.P.236.237; 6.P.236.238; 6.P.236.239; 6.P.236.154; 6.P.236.157; 6.P.236.166; 6.P.236.169;
6.P.236.172; 6.P.236.175; 6.P.236.240; 6.P.236.244; 6.P.237.228; 6.P.237.229; 6.P.237.230;
6.P.237.231; 6.P.237.236; 6.P.237.237; 6.P.237.238; 6.P.237.239; 6.P.237.154; 6.P.237.157;
6.P.237.166; 6.P.237.169; 6.P.237.172; 6.P.237.175; 6.P.237.240; 6.P.237.244; 6.P.238.228;
6.P.238.229; 6.P.238.230; 6.P.238.231; 6.P.238.236; 6.P.238.237; 6.P.238.238; 6.P.238.239;
6.P.238.154; 6.P.238.157; 6.P.238.166; 6.P.238.169; 6.P.238.172; 6.P.238.175; 6.P.238.240;
6.P.238.244; 6.P.239.228; 6.P.239.229; 6.P.239.230; 6.P.239.231; 6.P.239.236; 6.P.239.237;
6.P.239.238; 6.P.239.239; 6.P.239.154; 6.P.239.157; 6.P.239.166; 6.P.239.169; 6.P.239.172;
6.P.239.175; 6.P.239.240; 6.P.239.244; 6.P.154.228; 6.P.154.229; 6.P.154.230; 6.P.154.231;
6.P.154.236; 6.P.154.237; 6.P.154.238; 6.P.154.239; 6.P.154.154; 6.P.154.157; 6.P.154.166;
6.P.154.169; 6.P.154.172; 6.P.154.175; 6.P.154.240; 6.P.154.244; 6.P.157.228; 6.P.157.229;
6.P.157.230; 6.P.157.231; 6.P.157.236; 6.P.157.237; 6.P.157.238; 6.P.157.239; 6.P.157.154;
6.P.157.157; 6.P.157.166; 6.P.157.169; 6.P.157.172; 6.P.157.175; 6.P.157.240; 6.P.157.244;
6.P.166.228; 6.P.166.229; 6.P.166.230; 6.P.166.231; 6.P.166.236; 6.P.166.237; 6.P.166.238;
6.P.166.239; 6.P.166.154; 6.P.166.157; 6.P.166.166; 6.P.166.169; 6.P.166.172; 6.P.166.175;
6.P.166.240; 6.P.166.244; 6.P.169.228; 6.P.169.229; 6.P.169.230; 6.P.169.231; 6.P.169.236;
6.P.169.237; 6.P.169.238; 6.P.169.239; 6.P.169.154; 6.P.169.157; 6.P.169.166; 6.P.169.169;
6.P.169.172; 6.P.169.175; 6.P.169.240; 6.P.169.244; 6.P.172.228; 6.P.172.229; 6.P.172.230;
6.P.172.231; 6.P.172.236; 6.P.172.237; 6.P.172.238; 6.P.172.239; 6.P.172.154; 6.P.172.157;
6.P.172.166; 6.P.172.169; 6.P.172.172; 6.P.172.175; 6.P.172.240; 6.P.172.244; 6.P.175.228;
6.P.175.229; 6.P.175.230; 6.P.175.231; 6.P.175.236; 6.P.175.237; 6.P.175.238; 6.P.175.239;
6.P.175.154; 6.P.175.157; 6.P.175.166; 6.P.175.169; 6.P.175.172; 6.P.175.175; 6.P.175.240;

TABLE 100-continued

6.P.175.244; 6.P.240.228; 6.P.240.229; 6.P.240.230; 6.P.240.231; 6.P.240.236; 6.P.240.237;
6.P.240.238; 6.P.240.239; 6.P.240.154; 6.P.240.157; 6.P.240.166; 6.P.240.169; 6.P.240.172;
6.P.240.175; 6.P.240.240; 6.P.240.244; 6.P.244.228; 6.P.244.229; 6.P.244.230; 6.P.244.231;
6.P.244.236; 6.P.244.237; 6.P.244.238; 6.P.244.239; 6.P.244.154; 6.P.244.157; 6.P.244.166;
6.P.244.169; 6.P.244.172; 6.P.244.175; 6.P.244.240; 6.P.244.244;

Prodrugs of 6.U

6.U.228.228; 6.U.228.229; 6.U.228.230; 6.U.228.231; 6.U.228.236; 6.U.228.237;
6.U.228.238; 6.U.228.239; 6.U.228.154; 6.U.228.157; 6.U.228.166; 6.U.228.169;
6.U.228.172; 6.U.228.175; 6.U.228.240; 6.U.228.244; 6.U.229.228; 6.U.229.229;
6.U.229.230; 6.U.229.231; 6.U.229.236; 6.U.229.237; 6.U.229.238; 6.U.229.239;
6.U.229.154; 6.U.229.157; 6.U.229.166; 6.U.229.169; 6.U.229.172; 6.U.229.175;
6.U.229.240; 6.U.229.244; 6.U.230.228; 6.U.230.229; 6.U.230.230; 6.U.230.231;
6.U.230.236; 6.U.230.237; 6.U.230.238; 6.U.230.239; 6.U.230.154; 6.U.230.157;
6.U.230.166; 6.U.230.169; 6.U.230.172; 6.U.230.175; 6.U.230.240; 6.U.230.244;
6.U.231.228; 6.U.231.229; 6.U.231.230; 6.U.231.231; 6.U.231.236; 6.U.231.237;
6.U.231.238; 6.U.231.239; 6.U.231.154; 6.U.231.157; 6.U.231.166; 6.U.231.169;
6.U.231.172; 6.U.231.175; 6.U.231.240; 6.U.231.244; 6.U.236.228; 6.U.236.229;
6.U.236.230; 6.U.236.231; 6.U.236.236; 6.U.236.237; 6.U.236.238; 6.U.236.239;
6.U.236.154; 6.U.236.157; 6.U.236.166; 6.U.236.169; 6.U.236.172; 6.U.236.175;
6.U.236.240; 6.U.236.244; 6.U.237.228; 6.U.237.229; 6.U.237.230; 6.U.237.231;
6.U.237.236; 6.U.237.237; 6.U.237.238; 6.U.237.239; 6.U.237.154; 6.U.237.157;
6.U.237.166; 6.U.237.169; 6.U.237.172; 6.U.237.175; 6.U.237.240; 6.U.237.244;
6.U.238.228; 6.U.238.229; 6.U.238.230; 6.U.238.231; 6.U.238.236; 6.U.238.237;
6.U.238.238; 6.U.238.239; 6.U.238.154; 6.U.238.157; 6.U.238.166; 6.U.238.169;
6.U.238.172; 6.U.238.175; 6.U.238.240; 6.U.238.244; 6.U.239.228; 6.U.239.229;
6.U.239.230; 6.U.239.231; 6.U.239.236; 6.U.239.237; 6.U.239.238; 6.U.239.239;
6.U.239.154; 6.U.239.157; 6.U.239.166; 6.U.239.169; 6.U.239.172; 6.U.239.175;
6.U.239.240; 6.U.239.244; 6.U.154.228; 6.U.154.229; 6.U.154.230; 6.U.154.231;
6.U.154.236; 6.U.154.237; 6.U.154.238; 6.U.154.239; 6.U.154.154; 6.U.154.157;
6.U.154.166; 6.U.154.169; 6.U.154.172; 6.U.154.175; 6.U.154.240; 6.U.154.244;
6.U.157.228; 6.U.157.229; 6.U.157.230; 6.U.157.231; 6.U.157.236; 6.U.157.237;
6.U.157.238; 6.U.157.239; 6.U.157.154; 6.U.157.157; 6.U.157.166; 6.U.157.169;
6.U.157.172; 6.U.157.175; 6.U.157.240; 6.U.157.244; 6.U.166.228; 6.U.166.229;
6.U.166.230; 6.U.166.231; 6.U.166.236; 6.U.166.237; 6.U.166.238; 6.U.166.239;
6.U.166.154; 6.U.166.157; 6.U.166.166; 6.U.166.169; 6.U.166.172; 6.U.166.175;
6.U.166.240; 6.U.166.244; 6.U.169.228; 6.U.169.229; 6.U.169.230; 6.U.169.231;
6.U.169.236; 6.U.169.237; 6.U.169.238; 6.U.169.239; 6.U.169.154; 6.U.169.157;
6.U.169.166; 6.U.169.169; 6.U.169.172; 6.U.169.175; 6.U.169.240; 6.U.169.244;
6.U.172.228; 6.U.172.229; 6.U.172.230; 6.U.172.231; 6.U.172.236; 6.U.172.237;
6.U.172.238; 6.U.172.239; 6.U.172.154; 6.U.172.157; 6.U.172.166; 6.U.172.169;
6.U.172.172; 6.U.172.175; 6.U.172.240; 6.U.172.244; 6.U.175.228; 6.U.175.229;
6.U.175.230; 6.U.175.231; 6.U.175.236; 6.U.175.237; 6.U.175.238; 6.U.175.239;
6.U.175.154; 6.U.175.157; 6.U.175.166; 6.U.175.169; 6.U.175.172; 6.U.175.175;
6.U.175.240; 6.U.175.244; 6.U.240.228; 6.U.240.229; 6.U.240.230; 6.U.240.231;
6.U.240.236; 6.U.240.237; 6.U.240.238; 6.U.240.239; 6.U.240.154; 6.U.240.157;
6.U.240.166; 6.U.240.169; 6.U.240.172; 6.U.240.175; 6.U.240.240; 6.U.240.244;
6.U.244.228; 6.U.244.229; 6.U.244.230; 6.U.244.231; 6.U.244.236; 6.U.244.237;
6.U.244.238; 6.U.244.239; 6.U.244.154; 6.U.244.157; 6.U.244.166; 6.U.244.169;
6.U.244.172; 6.U.244.175; 6.U.244.240; 6.U.244.244;

Prodrugs of 6.W

6.W.228.228; 6.W.228.229; 6.W.228.230; 6.W.228.231; 6.W.228.236; 6.W.228.237;
6.W.228.238; 6.W.228.239; 6.W.228.154; 6.W.228.157; 6.W.228.166; 6.W.228.169;
6.W.228.172; 6.W.228.175; 6.W.228.240; 6.W.228.244; 6.W.229.228; 6.W.229.229;
6.W.229.230; 6.W.229.231; 6.W.229.236; 6.W.229.237; 6.W.229.238; 6.W.229.239;
6.W.229.154; 6.W.229.157; 6.W.229.166; 6.W.229.169; 6.W.229.172; 6.W.229.175;
6.W.229.240; 6.W.229.244; 6.W.230.228; 6.W.230.229; 6.W.230.230; 6.W.230.231;
6.W.230.236; 6.W.230.237; 6.W.230.238; 6.W.230.239; 6.W.230.154; 6.W.230.157;
6.W.230.166; 6.W.230.169; 6.W.230.172; 6.W.230.175; 6.W.230.240; 6.W.230.244;
6.W.231.228; 6.W.231.229; 6.W.231.230; 6.W.231.231; 6.W.231.236; 6.W.231.237;
6.W.231.238; 6.W.231.239; 6.W.231.154; 6.W.231.157; 6.W.231.166; 6.W.231.169;
6.W.231.172; 6.W.231.175; 6.W.231.240; 6.W.231.244; 6.W.236.228; 6.W.236.229;
6.W.236.230; 6.W.236.231; 6.W.236.236; 6.W.236.237; 6.W.236.238; 6.W.236.239;
6.W.236.154; 6.W.236.157; 6.W.236.166; 6.W.236.169; 6.W.236.172; 6.W.236.175;
6.W.236.240; 6.W.236.244; 6.W.237.228; 6.W.237.229; 6.W.237.230; 6.W.237.231;
6.W.237.236; 6.W.237.237; 6.W.237.238; 6.W.237.239; 6.W.237.154; 6.W.237.157;
6.W.237.166; 6.W.237.169; 6.W.237.172; 6.W.237.175; 6.W.237.240; 6.W.237.244;
6.W.238.228; 6.W.238.229; 6.W.238.230; 6.W.238.231; 6.W.238.236; 6.W.238.237;
6.W.238.238; 6.W.238.239; 6.W.238.154; 6.W.238.157; 6.W.238.166; 6.W.238.169;
6.W.238.172; 6.W.238.175; 6.W.238.240; 6.W.238.244; 6.W.239.228; 6.W.239.229;
6.W.239.230; 6.W.239.231; 6.W.239.236; 6.W.239.237; 6.W.239.238; 6.W.239.239;
6.W.239.154; 6.W.239.157; 6.W.239.166; 6.W.239.169; 6.W.239.172; 6.W.239.175;
6.W.239.240; 6.W.239.244; 6.W.154.228; 6.W.154.229; 6.W.154.230; 6.W.154.231;
6.W.154.236; 6.W.154.237; 6.W.154.238; 6.W.154.239; 6.W.154.154; 6.W.154.157;
6.W.154.166; 6.W.154.169; 6.W.154.172; 6.W.154.175; 6.W.154.240; 6.W.154.244;
6.W.157.228; 6.W.157.229; 6.W.157.230; 6.W.157.231; 6.W.157.236; 6.W.157.237;
6.W.157.238; 6.W.157.239; 6.W.157.154; 6.W.157.157; 6.W.157.166; 6.W.157.169;
6.W.157.172; 6.W.157.175; 6.W.157.240; 6.W.157.244; 6.W.166.228; 6.W.166.229;

TABLE 100-continued

6.W.166.230; 6.W.166.231; 6.W.166.236; 6.W.166.237; 6.W.166.238; 6.W.166.239; 6.W.166.154; 6.W.166.157; 6.W.166.166; 6.W.166.169; 6.W.166.172; 6.W.166.175; 6.W.166.240; 6.W.166.244; 6.W.169.228; 6.W.169.229; 6.W.169.230; 6.W.169.231; 6.W.169.236; 6.W.169.237; 6.W.169.238; 6.W.169.239; 6.W.169.154; 6.W.169.157; 6.W.169.166; 6.W.169.169; 6.W.169.172; 6.W.169.175; 6.W.169.240; 6.W.169.244; 6.W.172.228; 6.W.172.229; 6.W.172.230; 6.W.172.231; 6.W.172.236; 6.W.172.237; 6.W.172.238; 6.W.172.239; 6.W.172.154; 6.W.172.157; 6.W.172.166; 6.W.172.169; 6.W.172.172; 6.W.172.175; 6.W.172.240; 6.W.172.244; 6.W.175.228; 6.W.175.229; 6.W.175.230; 6.W.175.231; 6.W.175.236; 6.W.175.237; 6.W.175.238; 6.W.175.239; 6.W.175.154; 6.W.175.157; 6.W.175.166; 6.W.175.169; 6.W.175.172; 6.W.175.175; 6.W.175.240; 6.W.175.244; 6.W.240.228; 6.W.240.229; 6.W.240.230; 6.W.240.231; 6.W.240.236; 6.W.240.237; 6.W.240.238; 6.W.240.239; 6.W.240.154; 6.W.240.157; 6.W.240.166; 6.W.240.169; 6.W.240.172; 6.W.240.175; 6.W.240.240; 6.W.240.244; 6.W.244.228; 6.W.244.229; 6.W.244.230; 6.W.244.231; 6.W.244.236; 6.W.244.237; 6.W.244.238; 6.W.244.239; 6.W.244.154; 6.W.244.157; 6.W.244.166; 6.W.244.169; 6.W.244.172; 6.W.244.175; 6.W.244.240; 6.W.244.244;

Prodrugs of 6.Y

6.Y.228.228; 6.Y.228.229; 6.Y.228.230; 6.Y.228.231; 6.Y.228.236; 6.Y.228.237; 6.Y.228.238; 6.Y.228.239; 6.Y.228.154; 6.Y.228.157; 6.Y.228.166; 6.Y.228.169; 6.Y.228.172; 6.Y.228.175; 6.Y.228.240; 6.Y.228.244; 6.Y.229.228; 6.Y.229.229; 6.Y.229.230; 6.Y.229.231; 6.Y.229.236; 6.Y.229.237; 6.Y.229.238; 6.Y.229.239; 6.Y.229.154; 6.Y.229.157; 6.Y.229.166; 6.Y.229.169; 6.Y.229.172; 6.Y.229.175; 6.Y.229.240; 6.Y.229.244; 6.Y.230.228; 6.Y.230.229; 6.Y.230.230; 6.Y.230.231; 6.Y.230.236; 6.Y.230.237; 6.Y.230.238; 6.Y.230.239; 6.Y.230.154; 6.Y.230.157; 6.Y.230.166; 6.Y.230.169; 6.Y.230.172; 6.Y.230.175; 6.Y.230.240; 6.Y.230.244; 6.Y.231.228; 6.Y.231.229; 6.Y.231.230; 6.Y.231.231; 6.Y.231.236; 6.Y.231.237; 6.Y.231.238; 6.Y.231.239; 6.Y.231.154; 6.Y.231.157; 6.Y.231.166; 6.Y.231.169; 6.Y.231.172; 6.Y.231.175; 6.Y.231.240; 6.Y.231.244; 6.Y.236.228; 6.Y.236.229; 6.Y.236.230; 6.Y.236.231; 6.Y.236.236; 6.Y.236.237; 6.Y.236.238; 6.Y.236.239; 6.Y.236.154; 6.Y.236.157; 6.Y.236.166; 6.Y.236.169; 6.Y.236.172; 6.Y.236.175; 6.Y.236.240; 6.Y.236.244; 6.Y.237.228; 6.Y.237.229; 6.Y.237.230; 6.Y.237.231; 6.Y.237.236; 6.Y.237.237; 6.Y.237.238; 6.Y.237.239; 6.Y.237.154; 6.Y.237.157; 6.Y.237.166; 6.Y.237.169; 6.Y.237.172; 6.Y.237.175; 6.Y.237.240; 6.Y.237.244; 6.Y.238.228; 6.Y.238.229; 6.Y.238.230; 6.Y.238.231; 6.Y.238.236; 6.Y.238.237; 6.Y.238.238; 6.Y.238.239; 6.Y.238.154; 6.Y.238.157; 6.Y.238.166; 6.Y.238.169; 6.Y.238.172; 6.Y.238.175; 6.Y.238.240; 6.Y.238.244; 6.Y.239.228; 6.Y.239.229; 6.Y.239.230; 6.Y.239.231; 6.Y.239.236; 6.Y.239.237; 6.Y.239.238; 6.Y.239.239; 6.Y.239.154; 6.Y.239.157; 6.Y.239.166; 6.Y.239.169; 6.Y.239.172; 6.Y.239.175; 6.Y.239.240; 6.Y.239.244; 6.Y.154.228; 6.Y.154.229; 6.Y.154.230; 6.Y.154.231; 6.Y.154.236; 6.Y.154.237; 6.Y.154.238; 6.Y.154.239; 6.Y.154.154; 6.Y.154.157; 6.Y.154.166; 6.Y.154.169; 6.Y.154.172; 6.Y.154.175; 6.Y.154.240; 6.Y.154.244; 6.Y.157.228; 6.Y.157.229; 6.Y.157.230; 6.Y.157.231; 6.Y.157.236; 6.Y.157.237; 6.Y.157.238; 6.Y.157.239; 6.Y.157.154; 6.Y.157.157; 6.Y.157.166; 6.Y.157.169; 6.Y.157.172; 6.Y.157.175; 6.Y.157.240; 6.Y.157.244; 6.Y.166.228; 6.Y.166.229; 6.Y.166.230; 6.Y.166.231; 6.Y.166.236; 6.Y.166.237; 6.Y.166.238; 6.Y.166.239; 6.Y.166.154; 6.Y.166.157; 6.Y.166.166; 6.Y.166.169; 6.Y.166.172; 6.Y.166.175; 6.Y.166.240; 6.Y.166.244; 6.Y.169.228; 6.Y.169.229; 6.Y.169.230; 6.Y.169.231; 6.Y.169.236; 6.Y.169.237; 6.Y.169.238; 6.Y.169.239; 6.Y.169.154; 6.Y.169.157; 6.Y.169.166; 6.Y.169.169; 6.Y.169.172; 6.Y.169.175; 6.Y.169.240; 6.Y.169.244; 6.Y.172.228; 6.Y.172.229; 6.Y.172.230; 6.Y.172.231; 6.Y.172.236; 6.Y.172.237; 6.Y.172.238; 6.Y.172.239; 6.Y.172.154; 6.Y.172.157; 6.Y.172.166; 6.Y.172.169; 6.Y.172.172; 6.Y.172.175; 6.Y.172.240; 6.Y.172.244; 6.Y.175.228; 6.Y.175.229; 6.Y.175.230; 6.Y.175.231; 6.Y.175.236; 6.Y.175.237; 6.Y.175.238; 6.Y.175.239; 6.Y.175.154; 6.Y.175.157; 6.Y.175.166; 6.Y.175.169; 6.Y.175.172; 6.Y.175.175; 6.Y.175.240; 6.Y.175.244; 6.Y.240.228; 6.Y.240.229; 6.Y.240.230; 6.Y.240.231; 6.Y.240.236; 6.Y.240.237; 6.Y.240.238; 6.Y.240.239; 6.Y.240.154; 6.Y.240.157; 6.Y.240.166; 6.Y.240.169; 6.Y.240.172; 6.Y.240.175; 6.Y.240.240; 6.Y.240.244; 6.Y.244.228; 6.Y.244.229; 6.Y.244.230; 6.Y.244.231; 6.Y.244.236; 6.Y.244.237; 6.Y.244.238; 6.Y.244.239; 6.Y.244.154; 6.Y.244.157; 6.Y.244.166; 6.Y.244.169; 6.Y.244.172; 6.Y.244.175; 6.Y.244.240; 6.Y.244.244;

Prodrugs of 7.AH

7.AH.4.157; 7.AH.4.158; 7.AH.4.196; 7.AH.4.223; 7.AH.4.240; 7.AH.4.244; 7.AH.4.243; 7.AH.4.247; 7.AH.5.157; 7.AH.5.158; 7.AH.5.196; 7.AH.5.223; 7.AH.5.240; 7.AH.5.244; 7.AH.5.243; 7.AH.5.247; 7.AH.7.157; 7.AH.7.158; 7.AH.7.196; 7.AH.7.223; 7.AH.7.240; 7.AH.7.244; 7.AH.7.243; 7.AH.7.247; 7.AH.15.157; 7.AH.15.158; 7.AH.15.196; 7.AH.15.223; 7.AH.15.240; 7.AH.15.244; 7.AH.15.243; 7.AH.15.247; 7.AH.16.157; 7.AH.16.158; 7.AH.16.196; 7.AH.16.223; 7.AH.16.240; 7.AH.16.244; 7.AH.16.243; 7.AH.16.247; 7.AH.18.157; 7.AH.18.158; 7.AH.18.196; 7.AH.18.223; 7.AH.18.240; 7.AH.18.244; 7.AH.18.243; 7.AH.18.247; 7.AH.26.157; 7.AH.26.158; 7.AH.26.196; 7.AH.26.223; 7.AH.26.240; 7.AH.26.244; 7.AH.26.243; 7.AH.26.247; 7.AH.27.157; 7.AH.27.158; 7.AH.27.196; 7.AH.27.223; 7.AH.27.240; 7.AH.27.244; 7.AH.27.243; 7.AH.27.247; 7.AH.29.157; 7.AH.29.158; 7.AH.29.196; 7.AH.29.223; 7.AH.29.240; 7.AH.29.244; 7.AH.29.243; 7.AH.29.247; 7.AH.54.157; 7.AH.54.158; 7.AH.54.196; 7.AH.54.223; 7.AH.54.240; 7.AH.54.244; 7.AH.54.243; 7.AH.54.247; 7.AH.55.157; 7.AH.55.158; 7.AH.55.196; 7.AH.55.223; 7.AH.55.240; 7.AH.55.244; 7.AH.55.243; 7.AH.55.247; 7.AH.56.157; 7.AH.56.158; 7.AH.56.196; 7.AH.56.223; 7.AH.56.240; 7.AH.56.244; 7.AH.56.243; 7.AH.56.247; 7.AH.157.157; 7.AH.157.158; 7.AH.157.196;

TABLE 100-continued

7.AH.157.223; 7.AH.157.240; 7.AH.157.244; 7.AH.157.243; 7.AH.157.247; 7.AH.196.157; 7.AH.196.158; 7.AH.196.196; 7.AH.196.223; 7.AH.196.240; 7.AH.196.244; 7.AH.196.243; 7.AH.196.247; 7.AH.223.157; 7.AH.223.158; 7.AH.223.196; 7.AH.223.223; 7.AH.223.240; 7.AH.223.244; 7.AH.223.243; 7.AH.223.247; 7.AH.240.157; 7.AH.240.158; 7.AH.240.196; 7.AH.240.223; 7.AH.240.240; 7.AH.240.244; 7.AH.240.243; 7.AH.240.247; 7.AH.244.157; 7.AH.244.158; 7.AH.244.196; 7.AH.244.223; 7.AH.244.240; 7.AH.244.244; 7.AH.244.243; 7.AH.244.247; 7.AH.247.157; 7.AH.247.158; 7.AH.247.196; 7.AH.247.223; 7.AH.247.240; 7.AH.247.244; 7.AH.247.243; 7.AH.247.247;

Prodrugs of 7.AJ

7.AJ.4.157; 7.AJ.4.158; 7.AJ.4.196; 7.AJ.4.223; 7.AJ.4.240; 7.AJ.4.244; 7.AJ.4.243; 7.AJ.4.247; 7.AJ.5.157; 7.AJ.5.158; 7.AJ.5.196; 7.AJ.5.223; 7.AJ.5.240; 7.AJ.5.244; 7.AJ.5.243; 7.AJ.5.247; 7.AJ.7.157; 7.AJ.7.158; 7.AJ.7.196; 7.AJ.7.223; 7.AJ.7.240; 7.AJ.7.244; 7.AJ.7.243; 7.AJ.7.247; 7.AJ.15.157; 7.AJ.15.158; 7.AJ.15.196; 7.AJ.15.223; 7.AJ.15.240; 7.AJ.15.244; 7.AJ.15.243; 7.AJ.15.247; 7.AJ.16.157; 7.AJ.16.158; 7.AJ.16.196; 7.AJ.16.223; 7.AJ.16.240; 7.AJ.16.244; 7.AJ.16.243; 7.AJ.16.247; 7.AJ.18.157; 7.AJ.18.158; 7.AJ.18.196; 7.AJ.18.223; 7.AJ.18.240; 7.AJ.18.244; 7.AJ.18.243; 7.AJ.18.247; 7.AJ.26.157; 7.AJ.26.158; 7.AJ.26.196; 7.AJ.26.223; 7.AJ.26.240; 7.AJ.26.244; 7.AJ.26.243; 7.AJ.26.247; 7.AJ.27.157; 7.AJ.27.158; 7.AJ.27.196; 7.AJ.27.223; 7.AJ.27.240; 7.AJ.27.244; 7.AJ.27.243; 7.AJ.27.247; 7.AJ.29.157; 7.AJ.29.158; 7.AJ.29.196; 7.AJ.29.223; 7.AJ.29.240; 7.AJ.29.244; 7.AJ.29.243; 7.AJ.29.247; 7.AJ.54.157; 7.AJ.54.158; 7.AJ.54.196; 7.AJ.54.223; 7.AJ.54.240; 7.AJ.54.244; 7.AJ.54.243; 7.AJ.54.247; 7.AJ.55.157; 7.AJ.55.158; 7.AJ.55.196; 7.AJ.55.223; 7.AJ.55.240; 7.AJ.55.244; 7.AJ.55.243; 7.AJ.55.247; 7.AJ.56.157; 7.AJ.56.158; 7.AJ.56.196; 7.AJ.56.223; 7.AJ.56.240; 7.AJ.56.244; 7.AJ.56.243; 7.AJ.56.247; 7.AJ.157.157; 7.AJ.157.158; 7.AJ.157.196; 7.AJ.157.223; 7.AJ.157.240; 7.AJ.157.244; 7.AJ.157.243; 7.AJ.157.247; 7.AJ.196.157; 7.AJ.196.158; 7.AJ.196.196; 7.AJ.196.223; 7.AJ.196.240; 7.AJ.196.244; 7.AJ.196.243; 7.AJ.196.247; 7.AJ.223.157; 7.AJ.223.158; 7.AJ.223.196; 7.AJ.223.223; 7.AJ.223.240; 7.AJ.223.244; 7.AJ.223.243; 7.AJ.223.247; 7.AJ.240.157; 7.AJ.240.158; 7.AJ.240.196; 7.AJ.240.223; 7.AJ.240.240; 7.AJ.240.244; 7.AJ.240.243; 7.AJ.240.247; 7.AJ.244.157; 7.AJ.244.158; 7.AJ.244.196; 7.AJ.244.223; 7.AJ.244.240; 7.AJ.244.244; 7.AJ.244.243; 7.AJ.244.247; 7.AJ.247.157; 7.AJ.247.158; 7.AJ.247.196; 7.AJ.247.223; 7.AJ.247.240; 7.AJ.247.244; 7.AJ.247.243; 7.AJ.247.247;

Prodrugs of 7.AN

7.AN.4.157; 7.AN.4.158; 7.AN.4.196; 7.AN.4.223; 7.AN.4.240; 7.AN.4.244; 7.AN.4.243; 7.AN.4.247; 7.AN.5.157; 7.AN.5.158; 7.AN.5.196; 7.AN.5.223; 7.AN.5.240; 7.AN.5.244; 7.AN.5.243; 7.AN.5.247; 7.AN.7.157; 7.AN.7.158; 7.AN.7.196; 7.AN.7.223; 7.AN.7.240; 7.AN.7.244; 7.AN.7.243; 7.AN.7.247; 7.AN.15.157; 7.AN.15.158; 7.AN.15.196; 7.AN.15.223; 7.AN.15.240; 7.AN.15.244; 7.AN.15.243; 7.AN.15.247; 7.AN.16.157; 7.AN.16.158; 7.AN.16.196; 7.AN.16.223; 7.AN.16.240; 7.AN.16.244; 7.AN.16.243; 7.AN.16.247; 7.AN.18.157; 7.AN.18.158; 7.AN.18.196; 7.AN.18.223; 7.AN.18.240; 7.AN.18.244; 7.AN.18.243; 7.AN.18.247; 7.AN.26.157; 7.AN.26.158; 7.AN.26.196; 7.AN.26.223; 7.AN.26.240; 7.AN.26.244; 7.AN.26.243; 7.AN.26.247; 7.AN.27.157; 7.AN.27.158; 7.AN.27.196; 7.AN.27.223; 7.AN.27.240; 7.AN.27.244; 7.AN.27.243; 7.AN.27.247; 7.AN.29.157; 7.AN.29.158; 7.AN.29.196; 7.AN.29.223; 7.AN.29.240; 7.AN.29.244; 7.AN.29.243; 7.AN.29.247; 7.AN.54.157; 7.AN.54.158; 7.AN.54.196; 7.AN.54.223; 7.AN.54.240; 7.AN.54.244; 7.AN.54.243; 7.AN.54.247; 7.AN.55.157; 7.AN.55.158; 7.AN.55.196; 7.AN.55.223; 7.AN.55.240; 7.AN.55.244; 7.AN.55.243; 7.AN.55.247; 7.AN.56.157; 7.AN.56.158; 7.AN.56.196; 7.AN.56.223; 7.AN.56.240; 7.AN.56.244; 7.AN.56.243; 7.AN.56.247; 7.AN.157.157; 7.AN.157.158; 7.AN.157.196; 7.AN.157.223; 7.AN.157.240; 7.AN.157.244; 7.AN.157.243; 7.AN.157.247; 7.AN.196.157; 7.AN.196.158; 7.AN.196.196; 7.AN.196.223; 7.AN.196.240; 7.AN.196.244; 7.AN.196.243; 7.AN.196.247; 7.AN.223.157; 7.AN.223.158; 7.AN.223.196; 7.AN.223.223; 7.AN.223.240; 7.AN.223.244; 7.AN.223.243; 7.AN.223.247; 7.AN.240.157; 7.AN.240.158; 7.AN.240.196; 7.AN.240.223; 7.AN.240.240; 7.AN.240.244; 7.AN.240.243; 7.AN.240.247; 7.AN.244.157; 7.AN.244.158; 7.AN.244.196; 7.AN.244.223; 7.AN.244.240; 7.AN.244.244; 7.AN.244.243; 7.AN.244.247; 7.AN.247.157; 7.AN.247.158; 7.AN.247.196; 7.AN.247.223; 7.AN.247.240; 7.AN.247.244; 7.AN.247.243; 7.AN.247.247;

Prodrugs of 7.AP

7.AP.4.157; 7.AP.4.158; 7.AP.4.196; 7.AP.4.223; 7.AP.4.240; 7.AP.4.244; 7.AP.4.243; 7.AP.4.247; 7.AP.5.157; 7.AP.5.158; 7.AP.5.196; 7.AP.5.223; 7.AP.5.240; 7.AP.5.244; 7.AP.5.243; 7.AP.5.247; 7.AP.7.157; 7.AP.7.158; 7.AP.7.196; 7.AP.7.223; 7.AP.7.240; 7.AP.7.244; 7.AP.7.243; 7.AP.7.247; 7.AP.15.157; 7.AP.15.158; 7.AP.15.196; 7.AP.15.223; 7.AP.15.240; 7.AP.15.244; 7.AP.15.243; 7.AP.15.247; 7.AP.16.157; 7.AP.16.158; 7.AP.16.196; 7.AP.16.223; 7.AP.16.240; 7.AP.16.244; 7.AP.16.243; 7.AP.16.247; 7.AP.18.157; 7.AP.18.158; 7.AP.18.196; 7.AP.18.223; 7.AP.18.240; 7.AP.18.244; 7.AP.18.243; 7.AP.18.247; 7.AP.26.157; 7.AP.26.158; 7.AP.26.196; 7.AP.26.223; 7.AP.26.240; 7.AP.26.244; 7.AP.26.243; 7.AP.26.247; 7.AP.27.157; 7.AP.27.158; 7.AP.27.196; 7.AP.27.223; 7.AP.27.240; 7.AP.27.244; 7.AP.27.243; 7.AP.27.247; 7.AP.29.157; 7.AP.29.158; 7.AP.29.196; 7.AP.29.223; 7.AP.29.240; 7.AP.29.244; 7.AP.29.243; 7.AP.29.247; 7.AP.54.157; 7.AP.54.158; 7.AP.54.196; 7.AP.54.223; 7.AP.54.240; 7.AP.54.244; 7.AP.54.243; 7.AP.54.247; 7.AP.55.157; 7.AP.55.158; 7.AP.55.196; 7.AP.55.223; 7.AP.55.240; 7.AP.55.244; 7.AP.55.243; 7.AP.55.247; 7.AP.56.157; 7.AP.56.158; 7.AP.56.196; 7.AP.56.223; 7.AP.56.240; 7.AP.56.244; 7.AP.56.243; 7.AP.56.247; 7.AP.157.157; 7.AP.157.158; 7.AP.157.196; 7.AP.157.223; 7.AP.157.240; 7.AP.157.244; 7.AP.157.243; 7.AP.157.247; 7.AP.196.157; 7.AP.196.158; 7.AP.196.196; 7.AP.196.223; 7.AP.196.240; 7.AP.196.244; 7.AP.196.243; 7.AP.196.247; 7.AP.223.157; 7.AP.223.158; 7.AP.223.196; 7.AP.223.223; 7.AP.223.240; 7.AP.223.244;

TABLE 100-continued

7.AP.223.243; 7.AP.223.247; 7.AP.240.157; 7.AP.240.158; 7.AP.240.196; 7.AP.240.223; 7.AP.240.240; 7.AP.240.244; 7.AP.240.243; 7.AP.240.247; 7.AP.244.157; 7.AP.244.158; 7.AP.244.196; 7.AP.244.223; 7.AP.244.240; 7.AP.244.244; 7.AP.244.243; 7.AP.244.247; 7.AP.247.157; 7.AP.247.158; 7.AP.247.196; 7.AP.247.223; 7.AP.247.240; 7.AP.247.244; 7.AP.247.243; 7.AP.247.247;

Prodrugs of 7.AZ

7.AZ.4.157; 7.AZ.4.158; 7.AZ.4.196; 7.AZ.4.223; 7.AZ.4.240; 7.AZ.4.244; 7.AZ.4.243; 7.AZ.4.247; 7.AZ.5.157; 7.AZ.5.158; 7.AZ.5.196; 7.AZ.5.223; 7.AZ.5.240; 7.AZ.5.244; 7.AZ.5.243; 7.AZ.5.247; 7.AZ.7.157; 7.AZ.7.158; 7.AZ.7.196; 7.AZ.7.223; 7.AZ.7.240; 7.AZ.7.244; 7.AZ.7.243; 7.AZ.7.247; 7.AZ.15.157; 7.AZ.15.158; 7.AZ.15.196; 7.AZ.15.223; 7.AZ.15.240; 7.AZ.15.244; 7.AZ.15.243; 7.AZ.15.247; 7.AZ.16.157; 7.AZ.16.158; 7.AZ.16.196; 7.AZ.16.223; 7.AZ.16.240; 7.AZ.16.244; 7.AZ.16.243; 7.AZ.16.247; 7.AZ.18.157; 7.AZ.18.158; 7.AZ.18.196; 7.AZ.18.223; 7.AZ.18.240; 7.AZ.18.244; 7.AZ.18.243; 7.AZ.18.247; 7.AZ.26.157; 7.AZ.26.158; 7.AZ.26.196; 7.AZ.26.223; 7.AZ.26.240; 7.AZ.26.244; 7.AZ.26.243; 7.AZ.26.247; 7.AZ.27.157; 7.AZ.27.158; 7.AZ.27.196; 7.AZ.27.223; 7.AZ.27.240; 7.AZ.27.244; 7.AZ.27.243; 7.AZ.27.247; 7.AZ.29.157; 7.AZ.29.158; 7.AZ.29.196; 7.AZ.29.223; 7.AZ.29.240; 7.AZ.29.244; 7.AZ.29.243; 7.AZ.29.247; 7.AZ.54.157; 7.AZ.54.158; 7.AZ.54.196; 7.AZ.54.223; 7.AZ.54.240; 7.AZ.54.244; 7.AZ.54.243; 7.AZ.54.247; 7.AZ.55.157; 7.AZ.55.158; 7.AZ.55.196; 7.AZ.55.223; 7.AZ.55.240; 7.AZ.55.244; 7.AZ.55.243; 7.AZ.55.247; 7.AZ.56.157; 7.AZ.56.158; 7.AZ.56.196; 7.AZ.56.223; 7.AZ.56.240; 7.AZ.56.244; 7.AZ.56.243; 7.AZ.56.247; 7.AZ.157.157; 7.AZ.157.158; 7.AZ.157.196; 7.AZ.157.223; 7.AZ.157.240; 7.AZ.157.244; 7.AZ.157.243; 7.AZ.157.247; 7.AZ.196.157; 7.AZ.196.158; 7.AZ.196.196; 7.AZ.196.223; 7.AZ.196.240; 7.AZ.196.244; 7.AZ.196.243; 7.AZ.196.247; 7.AZ.223.157; 7.AZ.223.158; 7.AZ.223.196; 7.AZ.223.223; 7.AZ.223.240; 7.AZ.223.244; 7.AZ.223.243; 7.AZ.223.247; 7.AZ.240.157; 7.AZ.240.158; 7.AZ.240.196; 7.AZ.240.223; 7.AZ.240.240; 7.AZ.240.244; 7.AZ.240.243; 7.AZ.240.247; 7.AZ.244.157; 7.AZ.244.158; 7.AZ.244.196; 7.AZ.244.223; 7.AZ.244.240; 7.AZ.244.244; 7.AZ.244.243; 7.AZ.244.247; 7.AZ.247.157; 7.AZ.247.158; 7.AZ.247.196; 7.AZ.247.223; 7.AZ.247.240; 7.AZ.247.244; 7.AZ.247.243; 7.AZ.247.247;

Prodrugs of 7.BF

7.BF.4.157; 7.BF.4.158; 7.BF.4.196; 7.BF.4.223; 7.BF.4.240; 7.BF.4.244; 7.BF.4.243; 7.BF.4.247; 7.BF.5.157; 7.BF.5.158; 7.BF.5.196; 7.BF.5.223; 7.BF.5.240; 7.BF.5.244; 7.BF.5.243; 7.BF.5.247; 7.BF.7.157; 7.BF.7.158; 7.BF.7.196; 7.BF.7.223; 7.BF.7.240; 7.BF.7.244; 7.BF.7.243; 7.BF.7.247; 7.BF.15.157; 7.BF.15.158; 7.BF.15.196; 7.BF.15.223; 7.BF.15.240; 7.BF.15.244; 7.BF.15.243; 7.BF.15.247; 7.BF.16.157; 7.BF.16.158; 7.BF.16.196; 7.BF.16.223; 7.BF.16.240; 7.BF.16.244; 7.BF.16.243; 7.BF.16.247; 7.BF.18.157; 7.BF.18.158; 7.BF.18.196; 7.BF.18.223; 7.BF.18.240; 7.BF.18.244; 7.BF.18.243; 7.BF.18.247; 7.BF.26.157; 7.BF.26.158; 7.BF.26.196; 7.BF.26.223; 7.BF.26.240; 7.BF.26.244; 7.BF.26.243; 7.BF.26.247; 7.BF.27.157; 7.BF.27.158; 7.BF.27.196; 7.BF.27.223; 7.BF.27.240; 7.BF.27.244; 7.BF.27.243; 7.BF.27.247; 7.BF.29.157; 7.BF.29.158; 7.BF.29.196; 7.BF.29.223; 7.BF.29.240; 7.BF.29.244; 7.BF.29.243; 7.BF.29.247; 7.BF.54.157; 7.BF.54.158; 7.BF.54.196; 7.BF.54.223; 7.BF.54.240; 7.BF.54.244; 7.BF.54.243; 7.BF.54.247; 7.BF.55.157; 7.BF.55.158; 7.BF.55.196; 7.BF.55.223; 7.BF.55.240; 7.BF.55.244; 7.BF.55.243; 7.BF.55.247; 7.BF.56.157; 7.BF.56.158; 7.BF.56.196; 7.BF.56.223; 7.BF.56.240; 7.BF.56.244; 7.BF.56.243; 7.BF.56.247; 7.BF.157.157; 7.BF.157.158; 7.BF.157.196; 7.BF.157.223; 7.BF.157.240; 7.BF.157.244; 7.BF.157.243; 7.BF.157.247; 7.BF.196.157; 7.BF.196.158; 7.BF.196.196; 7.BF.196.223; 7.BF.196.240; 7.BF.196.244; 7.BF.196.243; 7.BF.196.247; 7.BF.223.157; 7.BF.223.158; 7.BF.223.196; 7.BF.223.223; 7.BF.223.240; 7.BF.223.244; 7.BF.223.243; 7.BF.223.247; 7.BF.240.157; 7.BF.240.158; 7.BF.240.196; 7.BF.240.223; 7.BF.240.240; 7.BF.240.244; 7.BF.240.243; 7.BF.240.247; 7.BF.244.157; 7.BF.244.158; 7.BF.244.196; 7.BF.244.223; 7.BF.244.240; 7.BF.244.244; 7.BF.244.243; 7.BF.244.247; 7.BF.247.157; 7.BF.247.158; 7.BF.247.196; 7.BF.247.223; 7.BF.247.240; 7.BF.247.244; 7.BF.247.243; 7.BF.247.247;

Prodrugs of 7.CI

7.CI.4.157; 7.CI.4.158; 7.CI.4.196; 7.CI.4.223; 7.CI.4.240; 7.CI.4.244; 7.CI.4.243; 7.CI.4.247; 7.CI.5.157; 7.CI.5.158; 7.CI.5.196; 7.CI.5.223; 7.CI.5.240; 7.CI.5.244; 7.CI.5.243; 7.CI.5.247; 7.CI.7.157; 7.CI.7.158; 7.CI.7.196; 7.CI.7.223; 7.CI.7.240; 7.CI.7.244; 7.CI.7.243; 7.CI.7.247; 7.CI.15.157; 7.CI.15.158; 7.CI.15.196; 7.CI.15.223; 7.CI.15.240; 7.CI.15.244; 7.CI.15.243; 7.CI.15.247; 7.CI.16.157; 7.CI.16.158; 7.CI.16.196; 7.CI.16.223; 7.CI.16.240; 7.CI.16.244; 7.CI.16.243; 7.CI.16.247; 7.CI.18.157; 7.CI.18.158; 7.CI.18.196; 7.CI.18.223; 7.CI.18.240; 7.CI.18.244; 7.CI.18.243; 7.CI.18.247; 7.CI.26.157; 7.CI.26.158; 7.CI.26.196; 7.CI.26.223; 7.CI.26.240; 7.CI.26.244; 7.CI.26.243; 7.CI.26.247; 7.CI.27.157; 7.CI.27.158; 7.CI.27.196; 7.CI.27.223; 7.CI.27.240; 7.CI.27.244; 7.CI.27.243; 7.CI.27.247; 7.CI.29.157; 7.CI.29.158; 7.CI.29.196; 7.CI.29.223; 7.CI.29.240; 7.CI.29.244; 7.CI.29.243; 7.CI.29.247; 7.CI.54.157; 7.CI.54.158; 7.CI.54.196; 7.CI.54.223; 7.CI.54.240; 7.CI.54.244; 7.CI.54.243; 7.CI.54.247; 7.CI.55.157; 7.CI.55.158; 7.CI.55.196; 7.CI.55.223; 7.CI.55.240; 7.CI.55.244; 7.CI.55.243; 7.CI.55.247; 7.CI.56.157; 7.CI.56.158; 7.CI.56.196; 7.CI.56.223; 7.CI.56.240; 7.CI.56.244; 7.CI.56.243; 7.CI.56.247; 7.CI.157.157; 7.CI.157.158; 7.CI.157.196; 7.CI.157.223; 7.CI.157.240; 7.CI.157.244; 7.CI.157.243; 7.CI.157.247; 7.CI.196.157; 7.CI.196.158; 7.CI.196.196; 7.CI.196.223; 7.CI.196.240; 7.CI.196.244; 7.CI.196.243; 7.CI.196.247; 7.CI.223.157; 7.CI.223.158; 7.CI.223.196; 7.CI.223.223; 7.CI.223.240; 7.CI.223.244; 7.CI.223.243; 7.CI.223.247; 7.CI.240.157; 7.CI.240.158; 7.CI.240.196; 7.CI.240.223; 7.CI.240.240; 7.CI.240.244; 7.CI.240.243; 7.CI.240.247; 7.CI.244.157; 7.CI.244.158; 7.CI.244.196; 7.CI.244.223; 7.CI.244.240;

TABLE 100-continued

7.CI.244.244; 7.CI.244.243; 7.CI.244.247; 7.CI.247.157; 7.CI.247.158; 7.CI.247.196; 7.CI.247.223; 7.CI.247.240; 7.CI.247.244; 7.CI.247.243; 7.CI.247.247;

Prodrugs of 7.CO

7.CO.4.157; 7.CO.4.158; 7.CO.4.196; 7.CO.4.223; 7.CO.4.240; 7.CO.4.244; 7.CO.4.243; 7.CO.4.247; 7.CO.5.157; 7.CO.5.158; 7.CO.5.196; 7.CO.5.223; 7.CO.5.240; 7.CO.5.244; 7.CO.5.243; 7.CO.5.247; 7.CO.7.157; 7.CO.7.158; 7.CO.7.196; 7.CO.7.223; 7.CO.7.240; 7.CO.7.244; 7.CO.7.243; 7.CO.7.247; 7.CO.15.157; 7.CO.15.158; 7.CO.15.196; 7.CO.15.223; 7.CO.15.240; 7.CO.15.244; 7.CO.15.243; 7.CO.15.247; 7.CO.16.157; 7.CO.16.158; 7.CO.16.196; 7.CO.16.223; 7.CO.16.240; 7.CO.16.244; 7.CO.16.243; 7.CO.16.247; 7.CO.18.157; 7.CO.18.158; 7.CO.18.196; 7.CO.18.223; 7.CO.18.240; 7.CO.18.244; 7.CO.18.243; 7.CO.18.247; 7.CO.26.157; 7.CO.26.158; 7.CO.26.196; 7.CO.26.223; 7.CO.26.240; 7.CO.26.244; 7.CO.26.243; 7.CO.26.247; 7.CO.27.157; 7.CO.27.158; 7.CO.27.196; 7.CO.27.223; 7.CO.27.240; 7.CO.27.244; 7.CO.27.243; 7.CO.27.247; 7.CO.29.157; 7.CO.29.158; 7.CO.29.196; 7.CO.29.223; 7.CO.29.240; 7.CO.29.244; 7.CO.29.243; 7.CO.29.247; 7.CO.54.157; 7.CO.54.158; 7.CO.54.196; 7.CO.54.223; 7.CO.54.240; 7.CO.54.244; 7.CO.54.243; 7.CO.54.247; 7.CO.55.157; 7.CO.55.158; 7.CO.55.196; 7.CO.55.223; 7.CO.55.240; 7.CO.55.244; 7.CO.55.243; 7.CO.55.247; 7.CO.56.157; 7.CO.56.158; 7.CO.56.196; 7.CO.56.223; 7.CO.56.240; 7.CO.56.244; 7.CO.56.243; 7.CO.56.247; 7.CO.157.157; 7.CO.157.158; 7.CO.157.196; 7.CO.157.223; 7.CO.157.240; 7.CO.157.244; 7.CO.157.243; 7.CO.157.247; 7.CO.196.157; 7.CO.196.158; 7.CO.196.196; 7.CO.196.223; 7.CO.196.240; 7.CO.196.244; 7.CO.196.243; 7.CO.196.247; 7.CO.223.157; 7.CO.223.158; 7.CO.223.196; 7.CO.223.223; 7.CO.223.240; 7.CO.223.244; 7.CO.223.243; 7.CO.223.247; 7.CO.240.157; 7.CO.240.158; 7.CO.240.196; 7.CO.240.223; 7.CO.240.240; 7.CO.240.244; 7.CO.240.243; 7.CO.240.247; 7.CO.244.157; 7.CO.244.158; 7.CO.244.196; 7.CO.244.223; 7.CO.244.240; 7.CO.244.244; 7.CO.244.243; 7.CO.244.247; 7.CO.4.157; 7.CO.4.158; 7.CO.4.196; 7.CO.4.223; 7.CO.4.240; 7.CO.4.244; 7.CO.4.243; 7.CO.4.247;

Prodrugs of 8.AH

8.AH.4.157; 8.AH.4.158; 8.AH.4.196; 8.AH.4.223; 8.AH.4.240; 8.AH.4.244; 8.AH.4.243; 8.AH.4.247; 8.AH.5.157; 8.AH.5.158; 8.AH.5.196; 8.AH.5.223; 8.AH.5.240; 8.AH.5.244; 8.AH.5.243; 8.AH.5.247; 8.AH.7.157; 8.AH.7.158; 8.AH.7.196; 8.AH.7.223; 8.AH.7.240; 8.AH.7.244; 8.AH.7.243; 8.AH.7.247; 8.AH.15.157; 8.AH.15.158; 8.AH.15.196; 8.AH.15.223; 8.AH.15.240; 8.AH.15.244; 8.AH.15.243; 8.AH.15.247; 8.AH.16.157; 8.AH.16.158; 8.AH.16.196; 8.AH.16.223; 8.AH.16.240; 8.AH.16.244; 8.AH.16.243; 8.AH.16.247; 8.AH.18.157; 8.AH.18.158; 8.AH.18.196; 8.AH.18.223; 8.AH.18.240; 8.AH.18.244; 8.AH.18.243; 8.AH.18.247; 8.AH.26.157; 8.AH.26.158; 8.AH.26.196; 8.AH.26.223; 8.AH.26.240; 8.AH.26.244; 8.AH.26.243; 8.AH.26.247; 8.AH.27.157; 8.AH.27.158; 8.AH.27.196; 8.AH.27.223; 8.AH.27.240; 8.AH.27.244; 8.AH.27.243; 8.AH.27.247; 8.AH.29.157; 8.AH.29.158; 8.AH.29.196; 8.AH.29.223; 8.AH.29.240; 8.AH.29.244; 8.AH.29.243; 8.AH.29.247; 8.AH.54.157; 8.AH.54.158; 8.AH.54.196; 8.AH.54.223; 8.AH.54.240; 8.AH.54.244; 8.AH.54.243; 8.AH.54.247; 8.AH.55.157; 8.AH.55.158; 8.AH.55.196; 8.AH.55.223; 8.AH.55.240; 8.AH.55.244; 8.AH.55.243; 8.AH.55.247; 8.AH.56.157; 8.AH.56.158; 8.AH.56.196; 8.AH.56.223; 8.AH.56.240; 8.AH.56.244; 8.AH.56.243; 8.AH.56.247; 8.AH.157.157; 8.AH.157.158; 8.AH.157.196; 8.AH.157.223; 8.AH.157.240; 8.AH.157.244; 8.AH.157.243; 8.AH.157.247; 8.AH.196.157; 8.AH.196.158; 8.AH.196.196; 8.AH.196.223; 8.AH.196.240; 8.AH.196.244; 8.AH.196.243; 8.AH.196.247; 8.AH.223.157; 8.AH.223.158; 8.AH.223.196; 8.AH.223.223; 8.AH.223.240; 8.AH.223.244; 8.AH.223.243; 8.AH.223.247; 8.AH.240.157; 8.AH.240.158; 8.AH.240.196; 8.AH.240.223; 8.AH.240.240; 8.AH.240.244; 8.AH.240.243; 8.AH.240.247; 8.AH.244.157; 8.AH.244.158; 8.AH.244.196; 8.AH.244.223; 8.AH.244.240; 8.AH.244.244; 8.AH.244.243; 8.AH.244.247; 8.AH.247.157; 8.AH.247.158; 8.AH.247.196; 8.AH.247.223; 8.AH.247.240; 8.AH.247.244; 8.AH.247.243; 8.AH.247.247;

Prodrugs of 8.AJ

8.AJ.4.157; 8.AJ.4.158; 8.AJ.4.196; 8.AJ.4.223; 8.AJ.4.240; 8.AJ.4.244; 8.AJ.4.243; 8.AJ.4.247; 8.AJ.5.157; 8.AJ.5.158; 8.AJ.5.196; 8.AJ.5.223; 8.AJ.5.240; 8.AJ.5.244; 8.AJ.5.243; 8.AJ.5.247; 8.AJ.7.157; 8.AJ.7.158; 8.AJ.7.196; 8.AJ.7.223; 8.AJ.7.240; 8.AJ.7.244; 8.AJ.7.243; 8.AJ.7.247; 8.AJ.15.157; 8.AJ.15.158; 8.AJ.15.196; 8.AJ.15.223; 8.AJ.15.240; 8.AJ.15.244; 8.AJ.15.243; 8.AJ.15.247; 8.AJ.16.157; 8.AJ.16.158; 8.AJ.16.196; 8.AJ.16.223; 8.AJ.16.240; 8.AJ.16.244; 8.AJ.16.243; 8.AJ.16.247; 8.AJ.18.157; 8.AJ.18.158; 8.AJ.18.196; 8.AJ.18.223; 8.AJ.18.240; 8.AJ.18.244; 8.AJ.18.243; 8.AJ.18.247; 8.AJ.26.157; 8.AJ.26.158; 8.AJ.26.196; 8.AJ.26.223; 8.AJ.26.240; 8.AJ.26.244; 8.AJ.26.243; 8.AJ.26.247; 8.AJ.27.157; 8.AJ.27.158; 8.AJ.27.196; 8.AJ.27.223; 8.AJ.27.240; 8.AJ.27.244; 8.AJ.27.243; 8.AJ.27.247; 8.AJ.29.157; 8.AJ.29.158; 8.AJ.29.196; 8.AJ.29.223; 8.AJ.29.240; 8.AJ.29.244; 8.AJ.29.243; 8.AJ.29.247; 8.AJ.54.157; 8.AJ.54.158; 8.AJ.54.196; 8.AJ.54.223; 8.AJ.54.240; 8.AJ.54.244; 8.AJ.54.243; 8.AJ.54.247; 8.AJ.55.157; 8.AJ.55.158; 8.AJ.55.196; 8.AJ.55.223; 8.AJ.55.240; 8.AJ.55.244; 8.AJ.55.243; 8.AJ.55.247; 8.AJ.56.157; 8.AJ.56.158; 8.AJ.56.196; 8.AJ.56.223; 8.AJ.56.240; 8.AJ.56.244; 8.AJ.56.243; 8.AJ.56.247; 8.AJ.157.157; 8.AJ.157.158; 8.AJ.157.196; 8.AJ.157.223; 8.AJ.157.240; 8.AJ.157.244; 8.AJ.157.243; 8.AJ.157.247; 8.AJ.196.157; 8.AJ.196.158; 8.AJ.196.196; 8.AJ.196.223; 8.AJ.196.240; 8.AJ.196.244; 8.AJ.196.243; 8.AJ.196.247; 8.AJ.223.157; 8.AJ.223.158; 8.AJ.223.196; 8.AJ.223.223; 8.AJ.223.240; 8.AJ.223.244; 8.AJ.223.243; 8.AJ.223.247; 8.AJ.240.157; 8.AJ.240.158; 8.AJ.240.196; 8.AJ.240.223; 8.AJ.240.240; 8.AJ.240.244; 8.AJ.240.243; 8.AJ.240.247; 8.AJ.244.157; 8.AJ.244.158; 8.AJ.244.196; 8.AJ.244.223; 8.AJ.244.240; 8.AJ.244.244; 8.AJ.244.243; 8.AJ.244.247; 8.AJ.247.157; 8.AJ.247.158; 8.AJ.247.196; 8.AJ.247.223; 8.AJ.247.240; 8.AJ.247.244; 8.AJ.247.243; 8.AJ.247.247;

TABLE 100-continued

Prodrugs of 8.AN

8.AN.4.157; 8.AN.4.158; 8.AN.4.196; 8.AN.4.223; 8.AN.4.240; 8.AN.4.244; 8.AN.4.243; 8.AN.4.247; 8.AN.5.157; 8.AN.5.158; 8.AN.5.196; 8.AN.5.223; 8.AN.5.240; 8.AN.5.244; 8.AN.5.243; 8.AN.5.247; 8.AN.7.157; 8.AN.7.158; 8.AN.7.196; 8.AN.7.223; 8.AN.7.240; 8.AN.7.244; 8.AN.7.243; 8.AN.7.247; 8.AN.15.157; 8.AN.15.158; 8.AN.15.196; 8.AN.15.223; 8.AN.15.240; 8.AN.15.244; 8.AN.15.243; 8.AN.15.247; 8.AN.16.157; 8.AN.16.158; 8.AN.16.196; 8.AN.16.223; 8.AN.16.240; 8.AN.16.244; 8.AN.16.243; 8.AN.16.247; 8.AN.18.157; 8.AN.18.158; 8.AN.18.196; 8.AN.18.223; 8.AN.18.240; 8.AN.18.244; 8.AN.18.243; 8.AN.18.247; 8.AN.26.157; 8.AN.26.158; 8.AN.26.196; 8.AN.26.223; 8.AN.26.240; 8.AN.26.244; 8.AN.26.243; 8.AN.26.247; 8.AN.27.157; 8.AN.27.158; 8.AN.27.196; 8.AN.27.223; 8.AN.27.240; 8.AN.27.244; 8.AN.27.243; 8.AN.27.247; 8.AN.29.157; 8.AN.29.158; 8.AN.29.196; 8.AN.29.223; 8.AN.29.240; 8.AN.29.244; 8.AN.29.243; 8.AN.29.247; 8.AN.54.157; 8.AN.54.158; 8.AN.54.196; 8.AN.54.223; 8.AN.54.240; 8.AN.54.244; 8.AN.54.243; 8.AN.54.247; 8.AN.55.157; 8.AN.55.158; 8.AN.55.196; 8.AN.55.223; 8.AN.55.240; 8.AN.55.244; 8.AN.55.243; 8.AN.55.247; 8.AN.56.157; 8.AN.56.158; 8.AN.56.196; 8.AN.56.223; 8.AN.56.240; 8.AN.56.244; 8.AN.56.243; 8.AN.56.247; 8.AN.157.157; 8.AN.157.158; 8.AN.157.196; 8.AN.157.223; 8.AN.157.240; 8.AN.157.244; 8.AN.157.243; 8.AN.157.247; 8.AN.196.157; 8.AN.196.158; 8.AN.196.196; 8.AN.196.223; 8.AN.196.240; 8.AN.196.244; 8.AN.196.243; 8.AN.196.247; 8.AN.223.157; 8.AN.223.158; 8.AN.223.196; 8.AN.223.223; 8.AN.223.240; 8.AN.223.244; 8.AN.223.243; 8.AN.223.247; 8.AN.240.157; 8.AN.240.158; 8.AN.240.196; 8.AN.240.223; 8.AN.240.240; 8.AN.240.244; 8.AN.240.243; 8.AN.240.247; 8.AN.244.157; 8.AN.244.158; 8.AN.244.196; 8.AN.244.223; 8.AN.244.240; 8.AN.244.244; 8.AN.244.243; 8.AN.244.247; 8.AN.247.157; 8.AN.247.158; 8.AN.247.196; 8.AN.247.223; 8.AN.247.240; 8.AN.247.244; 8.AN.247.243; 8.AN.247.247;

Prodrugs of 8.AP

8.AP.4.157; 8.AP.4.158; 8.AP.4.196; 8.AP.4.223; 8.AP.4.240; 8.AP.4.244; 8.AP.4.243; 8.AP.4.247; 8.AP.5.157; 8.AP.5.158; 8.AP.5.196; 8.AP.5.223; 8.AP.5.240; 8.AP.5.244; 8.AP.5.243; 8.AP.5.247; 8.AP.7.157; 8.AP.7.158; 8.AP.7.196; 8.AP.7.223; 8.AP.7.240; 8.AP.7.244; 8.AP.7.243; 8.AP.7.247; 8.AP.15.157; 8.AP.15.158; 8.AP.15.196; 8.AP.15.223; 8.AP.15.240; 8.AP.15.244; 8.AP.15.243; 8.AP.15.247; 8.AP.16.157; 8.AP.16.158; 8.AP.16.196; 8.AP.16.223; 8.AP.16.240; 8.AP.16.244; 8.AP.16.243; 8.AP.16.247; 8.AP.18.157; 8.AP.18.158; 8.AP.18.196; 8.AP.18.223; 8.AP.18.240; 8.AP.18.244; 8.AP.18.243; 8.AP.18.247; 8.AP.26.157; 8.AP.26.158; 8.AP.26.196; 8.AP.26.223; 8.AP.26.240; 8.AP.26.244; 8.AP.26.243; 8.AP.26.247; 8.AP.27.157; 8.AP.27.158; 8.AP.27.196; 8.AP.27.223; 8.AP.27.240; 8.AP.27.244; 8.AP.27.243; 8.AP.27.247; 8.AP.29.157; 8.AP.29.158; 8.AP.29.196; 8.AP.29.223; 8.AP.29.240; 8.AP.29.244; 8.AP.29.243; 8.AP.29.247; 8.AP.54.157; 8.AP.54.158; 8.AP.54.196; 8.AP.54.223; 8.AP.54.240; 8.AP.54.244; 8.AP.54.243; 8.AP.54.247; 8.AP.55.157; 8.AP.55.158; 8.AP.55.196; 8.AP.55.223; 8.AP.55.240; 8.AP.55.244; 8.AP.55.243; 8.AP.55.247; 8.AP.56.157; 8.AP.56.158; 8.AP.56.196; 8.AP.56.223; 8.AP.56.240; 8.AP.56.244; 8.AP.56.243; 8.AP.56.247; 8.AP.157.157; 8.AP.157.158; 8.AP.157.196; 8.AP.157.223; 8.AP.157.240; 8.AP.157.244; 8.AP.157.243; 8.AP.157.247; 8.AP.196.157; 8.AP.196.158; 8.AP.196.196; 8.AP.196.223; 8.AP.196.240; 8.AP.196.244; 8.AP.196.243; 8.AP.196.247; 8.AP.223.157; 8.AP.223.158; 8.AP.223.196; 8.AP.223.223; 8.AP.223.240; 8.AP.223.244; 8.AP.223.243; 8.AP.223.247; 8.AP.240.157; 8.AP.240.158; 8.AP.240.196; 8.AP.240.223; 8.AP.240.240; 8.AP.240.244; 8.AP.240.243; 8.AP.240.247; 8.AP.244.157; 8.AP.244.158; 8.AP.244.196; 8.AP.244.223; 8.AP.244.240; 8.AP.244.244; 8.AP.244.243; 8.AP.244.247; 8.AP.247.157; 8.AP.247.158; 8.AP.247.196; 8.AP.247.223; 8.AP.247.240; 8.AP.247.244; 8.AP.247.243; 8.AP.247.247;

Prodrugs of 8.AZ

8.AZ.4.157; 8.AZ.4.158; 8.AZ.4.196; 8.AZ.4.223; 8.AZ.4.240; 8.AZ.4.244; 8.AZ.4.243; 8.AZ.4.247; 8.AZ.5.157; 8.AZ.5.158; 8.AZ.5.196; 8.AZ.5.223; 8.AZ.5.240; 8.AZ.5.244; 8.AZ.5.243; 8.AZ.5.247; 8.AZ.7.157; 8.AZ.7.158; 8.AZ.7.196; 8.AZ.7.223; 8.AZ.7.240; 8.AZ.7.244; 8.AZ.7.243; 8.AZ.7.247; 8.AZ.15.157; 8.AZ.15.158; 8.AZ.15.196; 8.AZ.15.223; 8.AZ.15.240; 8.AZ.15.244; 8.AZ.15.243; 8.AZ.15.247; 8.AZ.16.157; 8.AZ.16.158; 8.AZ.16.196; 8.AZ.16.223; 8.AZ.16.240; 8.AZ.16.244; 8.AZ.16.243; 8.AZ.16.247; 8.AZ.18.157; 8.AZ.18.158; 8.AZ.18.196; 8.AZ.18.223; 8.AZ.18.240; 8.AZ.18.244; 8.AZ.18.243; 8.AZ.18.247; 8.AZ.26.157; 8.AZ.26.158; 8.AZ.26.196; 8.AZ.26.223; 8.AZ.26.240; 8.AZ.26.244; 8.AZ.26.243; 8.AZ.26.247; 8.AZ.27.157; 8.AZ.27.158; 8.AZ.27.196; 8.AZ.27.223; 8.AZ.27.240; 8.AZ.27.244; 8.AZ.27.243; 8.AZ.27.247; 8.AZ.29.157; 8.AZ.29.158; 8.AZ.29.196; 8.AZ.29.223; 8.AZ.29.240; 8.AZ.29.244; 8.AZ.29.243; 8.AZ.29.247; 8.AZ.54.157; 8.AZ.54.158; 8.AZ.54.196; 8.AZ.54.223; 8.AZ.54.240; 8.AZ.54.244; 8.AZ.54.243; 8.AZ.54.247; 8.AZ.55.157; 8.AZ.55.158; 8.AZ.55.196; 8.AZ.55.223; 8.AZ.55.240; 8.AZ.55.244; 8.AZ.55.243; 8.AZ.55.247; 8.AZ.56.157; 8.AZ.56.158; 8.AZ.56.196; 8.AZ.56.223; 8.AZ.56.240; 8.AZ.56.244; 8.AZ.56.243; 8.AZ.56.247; 8.AZ.157.157; 8.AZ.157.158; 8.AZ.157.196; 8.AZ.157.223; 8.AZ.157.240; 8.AZ.157.244; 8.AZ.157.243; 8.AZ.157.247; 8.AZ.196.157; 8.AZ.196.158; 8.AZ.196.196; 8.AZ.196.223; 8.AZ.196.240; 8.AZ.196.244; 8.AZ.196.243; 8.AZ.196.247; 8.AZ.223.157; 8.AZ.223.158; 8.AZ.223.196; 8.AZ.223.223; 8.AZ.223.240; 8.AZ.223.244; 8.AZ.223.243; 8.AZ.223.247; 8.AZ.240.157; 8.AZ.240.158; 8.AZ.240.196; 8.AZ.240.223; 8.AZ.240.240; 8.AZ.240.244; 8.AZ.240.243; 8.AZ.240.247; 8.AZ.244.157; 8.AZ.244.158; 8.AZ.244.196; 8.AZ.244.223; 8.AZ.244.240; 8.AZ.244.244; 8.AZ.244.243; 8.AZ.244.247; 8.AZ.247.157; 8.AZ.247.158; 8.AZ.247.196; 8.AZ.247.223; 8.AZ.247.240; 8.AZ.247.244; 8.AZ.247.243; 8.AZ.247.247;

TABLE 100-continued

Prodrugs of 8.BF

8.BF.4.157; 8.BF.4.158; 8.BF.4.196; 8.BF.4.223; 8.BF.4.240; 8.BF.4.244; 8.BF.4.243; 8.BF.4.247; 8.BF.5.157; 8.BF.5.158; 8.BF.5.196; 8.BF.5.223; 8.BF.5.240; 8.BF.5.244; 8.BF.5.243; 8.BF.5.247; 8.BF.7.157; 8.BF.7.158; 8.BF.7.196; 8.BF.7.223; 8.BF.7.240; 8.BF.7.244; 8.BF.7.243; 8.BF.7.247; 8.BF.15.157; 8.BF.15.158; 8.BF.15.196; 8.BF.15.223; 8.BF.15.240; 8.BF.15.244; 8.BF.15.243; 8.BF.15.247; 8.BF.16.157; 8.BF.16.158; 8.BF.16.196; 8.BF.16.223; 8.BF.16.240; 8.BF.16.244; 8.BF.16.243; 8.BF.16.247; 8.BF.18.157; 8.BF.18.158; 8.BF.18.196; 8.BF.18.223; 8.BF.18.240; 8.BF.18.244; 8.BF.18.243; 8.BF.18.247; 8.BF.26.157; 8.BF.26.158; 8.BF.26.196; 8.BF.26.223; 8.BF.26.240; 8.BF.26.244; 8.BF.26.243; 8.BF.26.247; 8.BF.27.157; 8.BF.27.158; 8.BF.27.196; 8.BF.27.223; 8.BF.27.240; 8.BF.27.244; 8.BF.27.243; 8.BF.27.247; 8.BF.29.157; 8.BF.29.158; 8.BF.29.196; 8.BF.29.223; 8.BF.29.240; 8.BF.29.244; 8.BF.29.243; 8.BF.29.247; 8.BF.54.157; 8.BF.54.158; 8.BF.54.196; 8.BF.54.223; 8.BF.54.240; 8.BF.54.244; 8.BF.54.243; 8.BF.54.247; 8.BF.55.157; 8.BF.55.158; 8.BF.55.196; 8.BF.55.223; 8.BF.55.240; 8.BF.55.244; 8.BF.55.243; 8.BF.55.247; 8.BF.56.157; 8.BF.56.158; 8.BF.56.196; 8.BF.56.223; 8.BF.56.240; 8.BF.56.244; 8.BF.56.243; 8.BF.56.247; 8.BF.157.157; 8.BF.157.158; 8.BF.157.196; 8.BF.157.223; 8.BF.157.240; 8.BF.157.244; 8.BF.157.243; 8.BF.157.247; 8.BF.196.157; 8.BF.196.158; 8.BF.196.196; 8.BF.196.223; 8.BF.196.240; 8.BF.196.244; 8.BF.196.243; 8.BF.196.247; 8.BF.223.157; 8.BF.223.158; 8.BF.223.196; 8.BF.223.223; 8.BF.223.240; 8.BF.223.244; 8.BF.223.243; 8.BF.223.247; 8.BF.240.157; 8.BF.240.158; 8.BF.240.196; 8.BF.240.223; 8.BF.240.240; 8.BF.240.244; 8.BF.240.243; 8.BF.240.247; 8.BF.244.157; 8.BF.244.158; 8.BF.244.196; 8.BF.244.223; 8.BF.244.240; 8.BF.244.244; 8.BF.244.243; 8.BF.244.247; 8.BF.247.157; 8.BF.247.158; 8.BF.247.196; 8.BF.247.223; 8.BF.247.240; 8.BF.247.244; 8.BF.247.243; 8.BF.247.247;

Prodrugs of 8.CI

8.CI.4.157; 8.CI.4.158; 8.CI.4.196; 8.CI.4.223; 8.CI.4.240; 8.CI.4.244; 8.CI.4.243; 8.CI.4.247; 8.CI.5.157; 8.CI.5.158; 8.CI.5.196; 8.CI.5.223; 8.CI.5.240; 8.CI.5.244; 8.CI.5.243; 8.CI.5.247; 8.CI.7.157; 8.CI.7.158; 8.CI.7.196; 8.CI.7.223; 8.CI.7.240; 8.CI.7.244; 8.CI.7.243; 8.CI.7.247; 8.CI.15.157; 8.CI.15.158; 8.CI.15.196; 8.CI.15.223; 8.CI.15.240; 8.CI.15.244; 8.CI.15.243; 8.CI.15.247; 8.CI.16.157; 8.CI.16.158; 8.CI.16.196; 8.CI.16.223; 8.CI.16.240; 8.CI.16.244; 8.CI.16.243; 8.CI.16.247; 8.CI.18.157; 8.CI.18.158; 8.CI.18.196; 8.CI.18.223; 8.CI.18.240; 8.CI.18.244; 8.CI.18.243; 8.CI.18.247; 8.CI.26.157; 8.CI.26.158; 8.CI.26.196; 8.CI.26.223; 8.CI.26.240; 8.CI.26.244; 8.CI.26.243; 8.CI.26.247; 8.CI.27.157; 8.CI.27.158; 8.CI.27.196; 8.CI.27.223; 8.CI.27.240; 8.CI.27.244; 8.CI.27.243; 8.CI.27.247; 8.CI.29.157; 8.CI.29.158; 8.CI.29.196; 8.CI.29.223; 8.CI.29.240; 8.CI.29.244; 8.CI.29.243; 8.CI.29.247; 8.CI.54.157; 8.CI.54.158; 8.CI.54.196; 8.CI.54.223; 8.CI.54.240; 8.CI.54.244; 8.CI.54.243; 8.CI.54.247; 8.CI.55.157; 8.CI.55.158; 8.CI.55.196; 8.CI.55.223; 8.CI.55.240; 8.CI.55.244; 8.CI.55.243; 8.CI.55.247; 8.CI.56.157; 8.CI.56.158; 8.CI.56.196; 8.CI.56.223; 8.CI.56.240; 8.CI.56.244; 8.CI.56.243; 8.CI.56.247; 8.CI.157.157; 8.CI.157.158; 8.CI.157.196; 8.CI.157.223; 8.CI.157.240; 8.CI.157.244; 8.CI.157.243; 8.CI.157.247; 8.CI.196.157; 8.CI.196.158; 8.CI.196.196; 8.CI.196.223; 8.CI.196.240; 8.CI.196.244; 8.CI.196.243; 8.CI.196.247; 8.CI.223.157; 8.CI.223.158; 8.CI.223.196; 8.CI.223.223; 8.CI.223.240; 8.CI.223.244; 8.CI.223.243; 8.CI.223.247; 8.CI.240.157; 8.CI.240.158; 8.CI.240.196; 8.CI.240.223; 8.CI.240.240; 8.CI.240.244; 8.CI.240.243; 8.CI.240.247; 8.CI.244.157; 8.CI.244.158; 8.CI.244.196; 8.CI.244.223; 8.CI.244.240; 8.CI.244.244; 8.CI.244.243; 8.CI.244.247; 8.CI.247.157; 8.CI.247.158; 8.CI.247.196; 8.CI.247.223; 8.CI.247.240; 8.CI.247.244; 8.CI.247.243; 8.CI.247.247;

Prodrugs of 8.CO

8.CO.4.157; 8.CO.4.158; 8.CO.4.196; 8.CO.4.223; 8.CO.4.240; 8.CO.4.244; 8.CO.4.243; 8.CO.4.247; 8.CO.5.157; 8.CO.5.158; 8.CO.5.196; 8.CO.5.223; 8.CO.5.240; 8.CO.5.244; 8.CO.5.243; 8.CO.5.247; 8.CO.7.157; 8.CO.7.158; 8.CO.7.196; 8.CO.7.223; 8.CO.7.240; 8.CO.7.244; 8.CO.7.243; 8.CO.7.247; 8.CO.15.157; 8.CO.15.158; 8.CO.15.196; 8.CO.15.223; 8.CO.15.240; 8.CO.15.244; 8.CO.15.243; 8.CO.15.247; 8.CO.16.157; 8.CO.16.158; 8.CO.16.196; 8.CO.16.223; 8.CO.16.240; 8.CO.16.244; 8.CO.16.243; 8.CO.16.247; 8.CO.18.157; 8.CO.18.158; 8.CO.18.196; 8.CO.18.223; 8.CO.18.240; 8.CO.18.244; 8.CO.18.243; 8.CO.18.247; 8.CO.26.157; 8.CO.26.158; 8.CO.26.196; 8.CO.26.223; 8.CO.26.240; 8.CO.26.244; 8.CO.26.243; 8.CO.26.247; 8.CO.27.157; 8.CO.27.158; 8.CO.27.196; 8.CO.27.223; 8.CO.27.240; 8.CO.27.244; 8.CO.27.243; 8.CO.27.247; 8.CO.29.157; 8.CO.29.158; 8.CO.29.196; 8.CO.29.223; 8.CO.29.240; 8.CO.29.244; 8.CO.29.243; 8.CO.29.247; 8.CO.54.157; 8.CO.54.158; 8.CO.54.196; 8.CO.54.223; 8.CO.54.240; 8.CO.54.244; 8.CO.54.243; 8.CO.54.247; 8.CO.55.157; 8.CO.55.158; 8.CO.55.196; 8.CO.55.223; 8.CO.55.240; 8.CO.55.244; 8.CO.55.243; 8.CO.55.247; 8.CO.56.157; 8.CO.56.158; 8.CO.56.196; 8.CO.56.223; 8.CO.56.240; 8.CO.56.244; 8.CO.56.243; 8.CO.56.247; 8.CO.157.157; 8.CO.157.158; 8.CO.157.196; 8.CO.157.223; 8.CO.157.240; 8.CO.157.244; 8.CO.157.243; 8.CO.157.247; 8.CO.196.157; 8.CO.196.158; 8.CO.196.196; 8.CO.196.223; 8.CO.196.240; 8.CO.196.244; 8.CO.196.243; 8.CO.196.247; 8.CO.223.157; 8.CO.223.158; 8.CO.223.196; 8.CO.223.223; 8.CO.223.240; 8.CO.223.244; 8.CO.223.243; 8.CO.223.247; 8.CO.240.157; 8.CO.240.158; 8.CO.240.196; 8.CO.240.223; 8.CO.240.240; 8.CO.240.244; 8.CO.240.243; 8.CO.240.247; 8.CO.244.157; 8.CO.244.158; 8.CO.244.196; 8.CO.244.223; 8.CO.244.240; 8.CO.244.244; 8.CO.244.243; 8.CO.244.247; 8.CO.247.157; 8.CO.247.158; 8.CO.247.196; 8.CO.247.223; 8.CO.247.240; 8.CO.247.244; 8.CO.247.243; 8.CO.247.247;

TABLE 100-continued

Prodrugs of 9.AH

9.AH.4.157; 9.AH.4.158; 9.AH.4.196; 9.AH.4.223; 9.AH.4.240; 9.AH.4.244; 9.AH.4.243; 9.AH.4.247; 9.AH.5.157; 9.AH.5.158; 9.AH.5.196; 9.AH.5.223; 9.AH.5.240; 9.AH.5.244; 9.AH.5.243; 9.AH.5.247; 9.AH.7.157; 9.AH.7.158; 9.AH.7.196; 9.AH.7.223; 9.AH.7.240; 9.AH.7.244; 9.AH.7.243; 9.AH.7.247; 9.AH.15.157; 9.AH.15.158; 9.AH.15.196; 9.AH.15.223; 9.AH.15.240; 9.AH.15.244; 9.AH.15.243; 9.AH.15.247; 9.AH.16.157; 9.AH.16.158; 9.AH.16.196; 9.AH.16.223; 9.AH.16.240; 9.AH.16.244; 9.AH.16.243; 9.AH.16.247; 9.AH.18.157; 9.AH.18.158; 9.AH.18.196; 9.AH.18.223; 9.AH.18.240; 9.AH.18.244; 9.AH.18.243; 9.AH.18.247; 9.AH.26.157; 9.AH.26.158; 9.AH.26.196; 9.AH.26.223; 9.AH.26.240; 9.AH.26.244; 9.AH.26.243; 9.AH.26.247; 9.AH.27.157; 9.AH.27.158; 9.AH.27.196; 9.AH.27.223; 9.AH.27.240; 9.AH.27.244; 9.AH.27.243; 9.AH.27.247; 9.AH.29.157; 9.AH.29.158; 9.AH.29.196; 9.AH.29.223; 9.AH.29.240; 9.AH.29.244; 9.AH.29.243; 9.AH.29.247; 9.AH.54.157; 9.AH.54.158; 9.AH.54.196; 9.AH.54.223; 9.AH.54.240; 9.AH.54.244; 9.AH.54.243; 9.AH.54.247; 9.AH.55.157; 9.AH.55.158; 9.AH.55.196; 9.AH.55.223; 9.AH.55.240; 9.AH.55.244; 9.AH.55.243; 9.AH.55.247; 9.AH.56.157; 9.AH.56.158; 9.AH.56.196; 9.AH.56.223; 9.AH.56.240; 9.AH.56.244; 9.AH.56.243; 9.AH.56.247; 9.AH.157.157; 9.AH.157.158; 9.AH.157.196; 9.AH.157.223; 9.AH.157.240; 9.AH.157.244; 9.AH.157.243; 9.AH.157.247; 9.AH.196.157; 9.AH.196.158; 9.AH.196.196; 9.AH.196.223; 9.AH.196.240; 9.AH.196.244; 9.AH.196.243; 9.AH.196.247; 9.AH.223.157; 9.AH.223.158; 9.AH.223.196; 9.AH.223.223; 9.AH.223.240; 9.AH.223.244; 9.AH.223.243; 9.AH.223.247; 9.AH.240.157; 9.AH.240.158; 9.AH.240.196; 9.AH.240.223; 9.AH.240.240; 9.AH.240.244; 9.AH.240.243; 9.AH.240.247; 9.AH.244.157; 9.AH.244.158; 9.AH.244.196; 9.AH.244.223; 9.AH.244.240; 9.AH.244.244; 9.AH.244.243; 9.AH.244.247; 9.AH.247.157; 9.AH.247.158; 9.AH.247.196; 9.AH.247.223; 9.AH.247.240; 9.AH.247.244; 9.AH.247.243; 9.AH.247.247;

Prodrugs of 9.AJ

9.AJ.4.157; 9.AJ.4.158; 9.AJ.4.196; 9.AJ.4.223; 9.AJ.4.240; 9.AJ.4.244; 9.AJ.4.243; 9.AJ.4.247; 9.AJ.5.157; 9.AJ.5.158; 9.AJ.5.196; 9.AJ.5.223; 9.AJ.5.240; 9.AJ.5.244; 9.AJ.5.243; 9.AJ.5.247; 9.AJ.7.157; 9.AJ.7.158; 9.AJ.7.196; 9.AJ.7.223; 9.AJ.7.240; 9.AJ.7.244; 9.AJ.7.243; 9.AJ.7.247; 9.AJ.15.157; 9.AJ.15.158; 9.AJ.15.196; 9.AJ.15.223; 9.AJ.15.240; 9.AJ.15.244; 9.AJ.15.243; 9.AJ.15.247; 9.AJ.16.157; 9.AJ.16.158; 9.AJ.16.196; 9.AJ.16.223; 9.AJ.16.240; 9.AJ.16.244; 9.AJ.16.243; 9.AJ.16.247; 9.AJ.18.157; 9.AJ.18.158; 9.AJ.18.196; 9.AJ.18.223; 9.AJ.18.240; 9.AJ.18.244; 9.AJ.18.243; 9.AJ.18.247; 9.AJ.26.157; 9.AJ.26.158; 9.AJ.26.196; 9.AJ.26.223; 9.AJ.26.240; 9.AJ.26.244; 9.AJ.26.243; 9.AJ.26.247; 9.AJ.27.157; 9.AJ.27.158; 9.AJ.27.196; 9.AJ.27.223; 9.AJ.27.240; 9.AJ.27.244; 9.AJ.27.243; 9.AJ.27.247; 9.AJ.29.157; 9.AJ.29.158; 9.AJ.29.196; 9.AJ.29.223; 9.AJ.29.240; 9.AJ.29.244; 9.AJ.29.243; 9.AJ.29.247; 9.AJ.54.157; 9.AJ.54.158; 9.AJ.54.196; 9.AJ.54.223; 9.AJ.54.240; 9.AJ.54.244; 9.AJ.54.243; 9.AJ.54.247; 9.AJ.55.157; 9.AJ.55.158; 9.AJ.55.196; 9.AJ.55.223; 9.AJ.55.240; 9.AJ.55.244; 9.AJ.55.243; 9.AJ.55.247; 9.AJ.56.157; 9.AJ.56.158; 9.AJ.56.196; 9.AJ.56.223; 9.AJ.56.240; 9.AJ.56.244; 9.AJ.56.243; 9.AJ.56.247; 9.AJ.157.157; 9.AJ.157.158; 9.AJ.157.196; 9.AJ.157.223; 9.AJ.157.240; 9.AJ.157.244; 9.AJ.157.243; 9.AJ.157.247; 9.AJ.196.157; 9.AJ.196.158; 9.AJ.196.196; 9.AJ.196.223; 9.AJ.196.240; 9.AJ.196.244; 9.AJ.196.243; 9.AJ.196.247; 9.AJ.223.157; 9.AJ.223.158; 9.AJ.223.196; 9.AJ.223.223; 9.AJ.223.240; 9.AJ.223.244; 9.AJ.223.243; 9.AJ.223.247; 9.AJ.240.157; 9.AJ.240.158; 9.AJ.240.196; 9.AJ.240.223; 9.AJ.240.240; 9.AJ.240.244; 9.AJ.240.243; 9.AJ.240.247; 9.AJ.244.157; 9.AJ.244.158; 9.AJ.244.196; 9.AJ.244.223; 9.AJ.244.240; 9.AJ.244.244; 9.AJ.244.243; 9.AJ.244.247; 9.AJ.247.157; 9.AJ.247.158; 9.AJ.247.196; 9.AJ.247.223; 9.AJ.247.240; 9.AJ.247.244; 9.AJ.247.243; 9.AJ.247.247;

Prodrugs of 9.AN

9.AN.4.157; 9.AN.4.158; 9.AN.4.196; 9.AN.4.223; 9.AN.4.240; 9.AN.4.244; 9.AN.4.243; 9.AN.4.247; 9.AN.5.157; 9.AN.5.158; 9.AN.5.196; 9.AN.5.223; 9.AN.5.240; 9.AN.5.244; 9.AN.5.243; 9.AN.5.247; 9.AN.7.157; 9.AN.7.158; 9.AN.7.196; 9.AN.7.223; 9.AN.7.240; 9.AN.7.244; 9.AN.7.243; 9.AN.7.247; 9.AN.15.157; 9.AN.15.158; 9.AN.15.196; 9.AN.15.223; 9.AN.15.240; 9.AN.15.244; 9.AN.15.243; 9.AN.15.247; 9.AN.16.157; 9.AN.16.158; 9.AN.16.196; 9.AN.16.223; 9.AN.16.240; 9.AN.16.244; 9.AN.16.243; 9.AN.16.247; 9.AN.18.157; 9.AN.18.158; 9.AN.18.196; 9.AN.18.223; 9.AN.18.240; 9.AN.18.244; 9.AN.18.243; 9.AN.18.247; 9.AN.26.157; 9.AN.26.158; 9.AN.26.196; 9.AN.26.223; 9.AN.26.240; 9.AN.26.244; 9.AN.26.243; 9.AN.26.247; 9.AN.27.157; 9.AN.27.158; 9.AN.27.196; 9.AN.27.223; 9.AN.27.240; 9.AN.27.244; 9.AN.27.243; 9.AN.27.247; 9.AN.29.157; 9.AN.29.158; 9.AN.29.196; 9.AN.29.223; 9.AN.29.240; 9.AN.29.244; 9.AN.29.243; 9.AN.29.247; 9.AN.54.157; 9.AN.54.158; 9.AN.54.196; 9.AN.54.223; 9.AN.54.240; 9.AN.54.244; 9.AN.54.243; 9.AN.54.247; 9.AN.55.157; 9.AN.55.158; 9.AN.55.196; 9.AN.55.223; 9.AN.55.240; 9.AN.55.244; 9.AN.55.243; 9.AN.55.247; 9.AN.56.157; 9.AN.56.158; 9.AN.56.196; 9.AN.56.223; 9.AN.56.240; 9.AN.56.244; 9.AN.56.243; 9.AN.56.247; 9.AN.157.157; 9.AN.157.158; 9.AN.157.196; 9.AN.157.223; 9.AN.157.240; 9.AN.157.244; 9.AN.157.243; 9.AN.157.247; 9.AN.196.157; 9.AN.196.158; 9.AN.196.196; 9.AN.196.223; 9.AN.196.240; 9.AN.196.244; 9.AN.196.243; 9.AN.196.247; 9.AN.223.157; 9.AN.223.158; 9.AN.223.196; 9.AN.223.223; 9.AN.223.240; 9.AN.223.244; 9.AN.223.243; 9.AN.223.247; 9.AN.240.157; 9.AN.240.158; 9.AN.240.196; 9.AN.240.223; 9.AN.240.240; 9.AN.240.244; 9.AN.240.243; 9.AN.240.247; 9.AN.244.157; 9.AN.244.158; 9.AN.244.196; 9.AN.244.223; 9.AN.244.240; 9.AN.244.244; 9.AN.244.243; 9.AN.244.247; 9.AN.247.157; 9.AN.247.158; 9.AN.247.196; 9.AN.247.223; 9.AN.247.240; 9.AN.247.244; 9.AN.247.243; 9.AN.247.247;

TABLE 100-continued

Prodrugs of 9.AP

9.AP.4.157; 9.AP.4.158; 9.AP.4.196; 9.AP.4.223; 9.AP.4.240; 9.AP.4.244; 9.AP.4.243; 9.AP.4.247; 9.AP.5.157; 9.AP.5.158; 9.AP.5.196; 9.AP.5.223; 9.AP.5.240; 9.AP.5.244; 9.AP.5.243; 9.AP.5.247; 9.AP.7.157; 9.AP.7.158; 9.AP.7.196; 9.AP.7.223; 9.AP.7.240; 9.AP.7.244; 9.AP.7.243; 9.AP.7.247; 9.AP.15.157; 9.AP.15.158; 9.AP.15.196; 9.AP.15.223; 9.AP.15.240; 9.AP.15.244; 9.AP.15.243; 9.AP.15.247; 9.AP.16.157; 9.AP.16.158; 9.AP.16.196; 9.AP.16.223; 9.AP.16.240; 9.AP.16.244; 9.AP.16.243; 9.AP.16.247; 9.AP.18.157; 9.AP.18.158; 9.AP.18.196; 9.AP.18.223; 9.AP.18.240; 9.AP.18.244; 9.AP.18.243; 9.AP.18.247; 9.AP.26.157; 9.AP.26.158; 9.AP.26.196; 9.AP.26.223; 9.AP.26.240; 9.AP.26.244; 9.AP.26.243; 9.AP.26.247; 9.AP.27.157; 9.AP.27.158; 9.AP.27.196; 9.AP.27.223; 9.AP.27.240; 9.AP.27.244; 9.AP.27.243; 9.AP.27.247; 9.AP.29.157; 9.AP.29.158; 9.AP.29.196; 9.AP.29.223; 9.AP.29.240; 9.AP.29.244; 9.AP.29.243; 9.AP.29.247; 9.AP.54.157; 9.AP.54.158; 9.AP.54.196; 9.AP.54.223; 9.AP.54.240; 9.AP.54.244; 9.AP.54.243; 9.AP.54.247; 9.AP.55.157; 9.AP.55.158; 9.AP.55.196; 9.AP.55.223; 9.AP.55.240; 9.AP.55.244; 9.AP.55.243; 9.AP.55.247; 9.AP.56.157; 9.AP.56.158; 9.AP.56.196; 9.AP.56.223; 9.AP.56.240; 9.AP.56.244; 9.AP.56.243; 9.AP.56.247; 9.AP.157.157; 9.AP.157.158; 9.AP.157.196; 9.AP.157.223; 9.AP.157.240; 9.AP.157.244; 9.AP.157.243; 9.AP.157.247; 9.AP.196.157; 9.AP.196.158; 9.AP.196.196; 9.AP.196.223; 9.AP.196.240; 9.AP.196.244; 9.AP.196.243; 9.AP.196.247; 9.AP.223.157; 9.AP.223.158; 9.AP.223.196; 9.AP.223.223; 9.AP.223.240; 9.AP.223.244; 9.AP.223.243; 9.AP.223.247; 9.AP.240.157; 9.AP.240.158; 9.AP.240.196; 9.AP.240.223; 9.AP.240.240; 9.AP.240.244; 9.AP.240.243; 9.AP.240.247; 9.AP.244.157; 9.AP.244.158; 9.AP.244.196; 9.AP.244.223; 9.AP.244.240; 9.AP.244.244; 9.AP.244.243; 9.AP.244.247; 9.AP.247.157; 9.AP.247.158; 9.AP.247.196; 9.AP.247.223; 9.AP.247.240; 9.AP.247.244; 9.AP.247.243; 9.AP.247.247;

Prodrugs of 9.AZ

9.AZ.4.157; 9.AZ.4.158; 9.AZ.4.196; 9.AZ.4.223; 9.AZ.4.240; 9.AZ.4.244; 9.AZ.4.243; 9.AZ.4.247; 9.AZ.5.157; 9.AZ.5.158; 9.AZ.5.196; 9.AZ.5.223; 9.AZ.5.240; 9.AZ.5.244; 9.AZ.5.243; 9.AZ.5.247; 9.AZ.7.157; 9.AZ.7.158; 9.AZ.7.196; 9.AZ.7.223; 9.AZ.7.240; 9.AZ.7.244; 9.AZ.7.243; 9.AZ.7.247; 9.AZ.15.157; 9.AZ.15.158; 9.AZ.15.196; 9.AZ.15.223; 9.AZ.15.240; 9.AZ.15.244; 9.AZ.15.243; 9.AZ.15.247; 9.AZ.16.157; 9.AZ.16.158; 9.AZ.16.196; 9.AZ.16.223; 9.AZ.16.240; 9.AZ.16.244; 9.AZ.16.243; 9.AZ.16.247; 9.AZ.18.157; 9.AZ.18.158; 9.AZ.18.196; 9.AZ.18.223; 9.AZ.18.240; 9.AZ.18.244; 9.AZ.18.243; 9.AZ.18.247; 9.AZ.26.157; 9.AZ.26.158; 9.AZ.26.196; 9.AZ.26.223; 9.AZ.26.240; 9.AZ.26.244; 9.AZ.26.243; 9.AZ.26.247; 9.AZ.27.157; 9.AZ.27.158; 9.AZ.27.196; 9.AZ.27.223; 9.AZ.27.240; 9.AZ.27.244; 9.AZ.27.243; 9.AZ.27.247; 9.AZ.29.157; 9.AZ.29.158; 9.AZ.29.196; 9.AZ.29.223; 9.AZ.29.240; 9.AZ.29.244; 9.AZ.29.243; 9.AZ.29.247; 9.AZ.54.157; 9.AZ.54.158; 9.AZ.54.196; 9.AZ.54.223; 9.AZ.54.240; 9.AZ.54.244; 9.AZ.54.243; 9.AZ.54.247; 9.AZ.55.157; 9.AZ.55.158; 9.AZ.55.196; 9.AZ.55.223; 9.AZ.55.240; 9.AZ.55.244; 9.AZ.55.243; 9.AZ.55.247; 9.AZ.56.157; 9.AZ.56.158; 9.AZ.56.196; 9.AZ.56.223; 9.AZ.56.240; 9.AZ.56.244; 9.AZ.56.243; 9.AZ.56.247; 9.AZ.157.157; 9.AZ.157.158; 9.AZ.157.196; 9.AZ.157.223; 9.AZ.157.240; 9.AZ.157.244; 9.AZ.157.243; 9.AZ.157.247; 9.AZ.196.157; 9.AZ.196.158; 9.AZ.196.196; 9.AZ.196.223; 9.AZ.196.240; 9.AZ.196.244; 9.AZ.196.243; 9.AZ.196.247; 9.AZ.223.157; 9.AZ.223.158; 9.AZ.223.196; 9.AZ.223.223; 9.AZ.223.240; 9.AZ.223.244; 9.AZ.223.243; 9.AZ.223.247; 9.AZ.240.157; 9.AZ.240.158; 9.AZ.240.196; 9.AZ.240.223; 9.AZ.240.240; 9.AZ.240.244; 9.AZ.240.243; 9.AZ.240.247; 9.AZ.244.157; 9.AZ.244.158; 9.AZ.244.196; 9.AZ.244.223; 9.AZ.244.240; 9.AZ.244.244; 9.AZ.244.243; 9.AZ.244.247; 9.AZ.247.157; 9.AZ.247.158; 9.AZ.247.196; 9.AZ.247.223; 9.AZ.247.240; 9.AZ.247.244; 9.AZ.247.243; 9.AZ.247.247;

Prodrugs of 9.BF

9.BF.4.157; 9.BF.4.158; 9.BF.4.196; 9.BF.4.223; 9.BF.4.240; 9.BF.4.244; 9.BF.4.243; 9.BF.4.247; 9.BF.5.157; 9.BF.5.158; 9.BF.5.196; 9.BF.5.223; 9.BF.5.240; 9.BF.5.244; 9.BF.5.243; 9.BF.5.247; 9.BF.7.157; 9.BF.7.158; 9.BF.7.196; 9.BF.7.223; 9.BF.7.240; 9.BF.7.244; 9.BF.7.243; 9.BF.7.247; 9.BF.15.157; 9.BF.15.158; 9.BF.15.196; 9.BF.15.223; 9.BF.15.240; 9.BF.15.244; 9.BF.15.243; 9.BF.15.247; 9.BF.16.157; 9.BF.16.158; 9.BF.16.196; 9.BF.16.223; 9.BF.16.240; 9.BF.16.244; 9.BF.16.243; 9.BF.16.247; 9.BF.18.157; 9.BF.18.158; 9.BF.18.196; 9.BF.18.223; 9.BF.18.240; 9.BF.18.244; 9.BF.18.243; 9.BF.18.247; 9.BF.26.157; 9.BF.26.158; 9.BF.26.196; 9.BF.26.223; 9.BF.26.240; 9.BF.26.244; 9.BF.26.243; 9.BF.26.247; 9.BF.27.157; 9.BF.27.158; 9.BF.27.196; 9.BF.27.223; 9.BF.27.240; 9.BF.27.244; 9.BF.27.243; 9.BF.27.247; 9.BF.29.157; 9.BF.29.158; 9.BF.29.196; 9.BF.29.223; 9.BF.29.240; 9.BF.29.244; 9.BF.29.243; 9.BF.29.247; 9.BF.54.157; 9.BF.54.158; 9.BF.54.196; 9.BF.54.223; 9.BF.54.240; 9.BF.54.244; 9.BF.54.243; 9.BF.54.247; 9.BF.55.157; 9.BF.55.158; 9.BF.55.196; 9.BF.55.223; 9.BF.55.240; 9.BF.55.244; 9.BF.55.243; 9.BF.55.247; 9.BF.56.157; 9.BF.56.158; 9.BF.56.196; 9.BF.56.223; 9.BF.56.240; 9.BF.56.244; 9.BF.56.243; 9.BF.56.247; 9.BF.157.157; 9.BF.157.158; 9.BF.157.196; 9.BF.157.223; 9.BF.157.240; 9.BF.157.244; 9.BF.157.243; 9.BF.157.247; 9.BF.196.157; 9.BF.196.158; 9.BF.196.196; 9.BF.196.223; 9.BF.196.240; 9.BF.196.244; 9.BF.196.243; 9.BF.196.247; 9.BF.223.157; 9.BF.223.158; 9.BF.223.196; 9.BF.223.223; 9.BF.223.240; 9.BF.223.244; 9.BF.223.243; 9.BF.223.247; 9.BF.240.157; 9.BF.240.158; 9.BF.240.196; 9.BF.240.223; 9.BF.240.240; 9.BF.240.244; 9.BF.240.243; 9.BF.240.247; 9.BF.244.157; 9.BF.244.158; 9.BF.244.196; 9.BF.244.223; 9.BF.244.240; 9.BF.244.244; 9.BF.244.243; 9.BF.244.247; 9.BF.247.157; 9.BF.247.158; 9.BF.247.196; 9.BF.247.223; 9.BF.247.240; 9.BF.247.244; 9.BF.247.243; 9.BF.247.247;

TABLE 100-continued

Prodrugs of 9.CI

9.CI.4.157; 9.CI.4.158; 9.CI.4.196; 9.CI.4.223; 9.CI.4.240; 9.CI.4.244; 9.CI.4.243; 9.CI.4.247; 9.CI.5.157; 9.CI.5.158; 9.CI.5.196; 9.CI.5.223; 9.CI.5.240; 9.CI.5.244; 9.CI.5.243; 9.CI.5.247; 9.CI.7.157; 9.CI.7.158; 9.CI.7.196; 9.CI.7.223; 9.CI.7.240; 9.CI.7.244; 9.CI.7.243; 9.CI.7.247; 9.CI.15.157; 9.CI.15.158; 9.CI.15.196; 9.CI.15.223; 9.CI.15.240; 9.CI.15.244; 9.CI.15.243; 9.CI.15.247; 9.CI.16.157; 9.CI.16.158; 9.CI.16.196; 9.CI.16.223; 9.CI.16.240; 9.CI.16.244; 9.CI.16.243; 9.CI.16.247; 9.CI.18.157; 9.CI.18.158; 9.CI.18.196; 9.CI.18.223; 9.CI.18.240; 9.CI.18.244; 9.CI.18.243; 9.CI.18.247; 9.CI.26.157; 9.CI.26.158; 9.CI.26.196; 9.CI.26.223; 9.CI.26.240; 9.CI.26.244; 9.CI.26.243; 9.CI.26.247; 9.CI.27.157; 9.CI.27.158; 9.CI.27.196; 9.CI.27.223; 9.CI.27.240; 9.CI.27.244; 9.CI.27.243; 9.CI.27.247; 9.CI.29.157; 9.CI.29.158; 9.CI.29.196; 9.CI.29.223; 9.CI.29.240; 9.CI.29.244; 9.CI.29.243; 9.CI.29.247; 9.CI.54.157; 9.CI.54.158; 9.CI.54.196; 9.CI.54.223; 9.CI.54.240; 9.CI.54.244; 9.CI.54.243; 9.CI.54.247; 9.CI.55.157; 9.CI.55.158; 9.CI.55.196; 9.CI.55.223; 9.CI.55.240; 9.CI.55.244; 9.CI.55.243; 9.CI.55.247; 9.CI.56.157; 9.CI.56.158; 9.CI.56.196; 9.CI.56.223; 9.CI.56.240; 9.CI.56.244; 9.CI.56.243; 9.CI.56.247; 9.CI.157.157; 9.CI.157.158; 9.CI.157.196; 9.CI.157.223; 9.CI.157.240; 9.CI.157.244; 9.CI.157.243; 9.CI.157.247; 9.CI.196.157; 9.CI.196.158; 9.CI.196.196; 9.CI.196.223; 9.CI.196.240; 9.CI.196.244; 9.CI.196.243; 9.CI.196.247; 9.CI.223.157; 9.CI.223.158; 9.CI.223.196; 9.CI.223.223; 9.CI.223.240; 9.CI.223.244; 9.CI.223.243; 9.CI.223.247; 9.CI.240.157; 9.CI.240.158; 9.CI.240.196; 9.CI.240.223; 9.CI.240.240; 9.CI.240.244; 9.CI.240.243; 9.CI.240.247; 9.CI.244.157; 9.CI.244.158; 9.CI.244.196; 9.CI.244.223; 9.CI.244.240; 9.CI.244.244; 9.CI.244.243; 9.CI.244.247; 9.CI.247.157; 9.CI.247.158; 9.CI.247.196; 9.CI.247.223; 9.CI.247.240; 9.CI.247.244; 9.CI.247.243; 9.CI.247.247;

Prodrugs of 9.CO

9.CO.4.157; 9.CO.4.158; 9.CO.4.196; 9.CO.4.223; 9.CO.4.240; 9.CO.4.244; 9.CO.4.243; 9.CO.4.247; 9.CO.5.157; 9.CO.5.158; 9.CO.5.196; 9.CO.5.223; 9.CO.5.240; 9.CO.5.244; 9.CO.5.243; 9.CO.5.247; 9.CO.7.157; 9.CO.7.158; 9.CO.7.196; 9.CO.7.223; 9.CO.7.240; 9.CO.7.244; 9.CO.7.243; 9.CO.7.247; 9.CO.15.157; 9.CO.15.158; 9.CO.15.196; 9.CO.15.223; 9.CO.15.240; 9.CO.15.244; 9.CO.15.243; 9.CO.15.247; 9.CO.16.157; 9.CO.16.158; 9.CO.16.196; 9.CO.16.223; 9.CO.16.240; 9.CO.16.244; 9.CO.16.243; 9.CO.16.247; 9.CO.18.157; 9.CO.18.158; 9.CO.18.196; 9.CO.18.223; 9.CO.18.240; 9.CO.18.244; 9.CO.18.243; 9.CO.18.247; 9.CO.26.157; 9.CO.26.158; 9.CO.26.196; 9.CO.26.223; 9.CO.26.240; 9.CO.26.244; 9.CO.26.243; 9.CO.26.247; 9.CO.27.157; 9.CO.27.158; 9.CO.27.196; 9.CO.27.223; 9.CO.27.240; 9.CO.27.244; 9.CO.27.243; 9.CO.27.247; 9.CO.29.157; 9.CO.29.158; 9.CO.29.196; 9.CO.29.223; 9.CO.29.240; 9.CO.29.244; 9.CO.29.243; 9.CO.29.247; 9.CO.54.157; 9.CO.54.158; 9.CO.54.196; 9.CO.54.223; 9.CO.54.240; 9.CO.54.244; 9.CO.54.243; 9.CO.54.247; 9.CO.55.157; 9.CO.55.158; 9.CO.55.196; 9.CO.55.223; 9.CO.55.240; 9.CO.55.244; 9.CO.55.243; 9.CO.55.247; 9.CO.56.157; 9.CO.56.158; 9.CO.56.196; 9.CO.56.223; 9.CO.56.240; 9.CO.56.244; 9.CO.56.243; 9.CO.56.247; 9.CO.157.157; 9.CO.157.158; 9.CO.157.196; 9.CO.157.223; 9.CO.157.240; 9.CO.157.244; 9.CO.157.243; 9.CO.157.247; 9.CO.196.157; 9.CO.196.158; 9.CO.196.196; 9.CO.196.223; 9.CO.196.240; 9.CO.196.244; 9.CO.196.243; 9.CO.196.247; 9.CO.223.157; 9.CO.223.158; 9.CO.223.196; 9.CO.223.223; 9.CO.223.240; 9.CO.223.244; 9.CO.223.243; 9.CO.223.247; 9.CO.240.157; 9.CO.240.158; 9.CO.240.196; 9.CO.240.223; 9.CO.240.240; 9.CO.240.244; 9.CO.240.243; 9.CO.240.247; 9.CO.244.157; 9.CO.244.158; 9.CO.244.196; 9.CO.244.223; 9.CO.244.240; 9.CO.244.244; 9.CO.244.243; 9.CO.244.247; 9.CO.247.157; 9.CO.247.158; 9.CO.247.196; 9.CO.247.223; 9.CO.247.240; 9.CO.247.244; 9.CO.247.243; 9.CO.247.247;

Prodrugs of 10.AH

10.AH.4.157; 10.AH.4.158; 10.AH.4.196; 10.AH.4.223; 10.AH.4.240; 10.AH.4.244; 10.AH.4.243; 10.AH.4.247; 10.AH.5.157; 10.AH.5.158; 10.AH.5.196; 10.AH.5.223; 10.AH.5.240; 10.AH.5.244; 10.AH.5.243; 10.AH.5.247; 10.AH.7.157; 10.AH.7.158; 10.AH.7.196; 10.AH.7.223; 10.AH.7.240; 10.AH.7.244; 10.AH.7.243; 10.AH.7.247; 10.AH.15.157; 10.AH.15.158; 10.AH.15.196; 10.AH.15.223; 10.AH.15.240; 10.AH.15.244; 10.AH.15.243; 10.AH.15.247; 10.AH.16.157; 10.AH.16.158; 10.AH.16.196; 10.AH.16.223; 10.AH.16.240; 10.AH.16.244; 10.AH.16.243; 10.AH.16.247; 10.AH.18.157; 10.AH.18.158; 10.AH.18.196; 10.AH.18.223; 10.AH.18.240; 10.AH.18.244; 10.AH.18.243; 10.AH.18.247; 10.AH.26.157; 10.AH.26.158; 10.AH.26.196; 10.AH.26.223; 10.AH.26.240; 10.AH.26.244; 10.AH.26.243; 10.AH.26.247; 10.AH.27.157; 10.AH.27.158; 10.AH.27.196; 10.AH.27.223; 10.AH.27.240; 10.AH.27.244; 10.AH.27.243; 10.AH.27.247; 10.AH.29.157; 10.AH.29.158; 10.AH.29.196; 10.AH.29.223; 10.AH.29.240; 10.AH.29.244; 10.AH.29.243; 10.AH.29.247; 10.AH.54.157; 10.AH.54.158; 10.AH.54.196; 10.AH.54.223; 10.AH.54.240; 10.AH.54.244; 10.AH.54.243; 10.AH.54.247; 10.AH.55.157; 10.AH.55.158; 10.AH.55.196; 10.AH.55.223; 10.AH.55.240; 10.AH.55.244; 10.AH.55.243; 10.AH.55.247; 10.AH.56.157; 10.AH.56.158; 10.AH.56.196; 10.AH.56.223; 10.AH.56.240; 10.AH.56.244; 10.AH.56.243; 10.AH.56.247; 10.AH.157.157; 10.AH.157.158; 10.AH.157.196; 10.AH.157.223; 10.AH.157.240; 10.AH.157.244; 10.AH.157.243; 10.AH.157.247; 10.AH.196.157; 10.AH.196.158; 10.AH.196.196; 10.AH.196.223; 10.AH.196.240; 10.AH.196.244; 10.AH.196.243; 10.AH.196.247; 10.AH.223.157; 10.AH.223.158; 10.AH.223.196; 10.AH.223.223; 10.AH.223.240; 10.AH.223.244; 10.AH.223.243; 10.AH.223.247; 10.AH.240.157; 10.AH.240.158; 10.AH.240.196; 10.AH.240.223; 10.AH.240.240; 10.AH.240.244; 10.AH.240.243; 10.AH.240.247; 10.AH.244.157; 10.AH.244.158; 10.AH.244.196; 10.AH.244.223; 10.AH.244.240; 10.AH.244.244; 10.AH.244.243; 10.AH.244.247; 10.AH.247.157; 10.AH.247.158; 10.AH.247.196; 10.AH.247.223; 10.AH.247.240; 10.AH.247.244; 10.AH.247.243; 10.AH.247.247;

TABLE 100-continued

Prodrugs of 10.AJ

10.AJ.4.157; 10.AJ.4.158; 10.AJ.4.196; 10.AJ.4.223; 10.AJ.4.240; 10.AJ.4.244; 10.AJ.4.243; 10.AJ.4.247; 10.AJ.5.157; 10.AJ.5.158; 10.AJ.5.196; 10.AJ.5.223; 10.AJ.5.240; 10.AJ.5.244; 10.AJ.5.243; 10.AJ.5.247; 10.AJ.7.157; 10.AJ.7.158; 10.AJ.7.196; 10.AJ.7.223; 10.AJ.7.240; 10.AJ.7.244; 10.AJ.7.243; 10.AJ.7.247; 10.AJ.15.157; 10.AJ.15.158; 10.AJ.15.196; 10.AJ.15.223; 10.AJ.15.240; 10.AJ.15.244; 10.AJ.15.243; 10.AJ.15.247; 10.AJ.16.157; 10.AJ.16.158; 10.AJ.16.196; 10.AJ.16.223; 10.AJ.16.240; 10.AJ.16.244; 10.AJ.16.243; 10.AJ.16.247; 10.AJ.18.157; 10.AJ.18.158; 10.AJ.18.196; 10.AJ.18.223; 10.AJ.18.240; 10.AJ.18.244; 10.AJ.18.243; 10.AJ.18.247; 10.AJ.26.157; 10.AJ.26.158; 10.AJ.26.196; 10.AJ.26.223; 10.AJ.26.240; 10.AJ.26.244; 10.AJ.26.243; 10.AJ.26.247; 10.AJ.27.157; 10.AJ.27.158; 10.AJ.27.196; 10.AJ.27.223; 10.AJ.27.240; 10.AJ.27.244; 10.AJ.27.243; 10.AJ.27.247; 10.AJ.29.157; 10.AJ.29.158; 10.AJ.29.196; 10.AJ.29.223; 10.AJ.29.240; 10.AJ.29.244; 10.AJ.29.243; 10.AJ.29.247; 10.AJ.54.157; 10.AJ.54.158; 10.AJ.54.196; 10.AJ.54.223; 10.AJ.54.240; 10.AJ.54.244; 10.AJ.54.243; 10.AJ.54.247; 10.AJ.55.157; 10.AJ.55.158; 10.AJ.55.196; 10.AJ.55.223; 10.AJ.55.240; 10.AJ.55.244; 10.AJ.55.243; 10.AJ.55.247; 10.AJ.56.157; 10.AJ.56.158; 10.AJ.56.196; 10.AJ.56.223; 10.AJ.56.240; 10.AJ.56.244; 10.AJ.56.243; 10.AJ.56.247; 10.AJ.157.157; 10.AJ.157.158; 10.AJ.157.196; 10.AJ.157.223; 10.AJ.157.240; 10.AJ.157.244; 10.AJ.157.243; 10.AJ.157.247; 10.AJ.196.157; 10.AJ.196.158; 10.AJ.196.196; 10.AJ.196.223; 10.AJ.196.240; 10.AJ.196.244; 10.AJ.196.243; 10.AJ.196.247; 10.AJ.223.157; 10.AJ.223.158; 10.AJ.223.196; 10.AJ.223.223; 10.AJ.223.240; 10.AJ.223.244; 10.AJ.223.243; 10.AJ.223.247; 10.AJ.240.157; 10.AJ.240.158; 10.AJ.240.196; 10.AJ.240.223; 10.AJ.240.240; 10.AJ.240.244; 10.AJ.240.243; 10.AJ.240.247; 10.AJ.244.157; 10.AJ.244.158; 10.AJ.244.196; 10.AJ.244.223; 10.AJ.244.240; 10.AJ.244.244; 10.AJ.244.243; 10.AJ.244.247; 10.AJ.247.157; 10.AJ.247.158; 10.AJ.247.196; 10.AJ.247.223; 10.AJ.247.240; 10.AJ.247.244; 10.AJ.247.243; 10.AJ.247.247;

Prodrugs of 10.AN

10.AN.4.157; 10.AN.4.158; 10.AN.4.196; 10.AN.4.223; 10.AN.4.240; 10.AN.4.244; 10.AN.4.243; 10.AN.4.247; 10.AN.5.157; 10.AN.5.158; 10.AN.5.196; 10.AN.5.223; 10.AN.5.240; 10.AN.5.244; 10.AN.5.243; 10.AN.5.247; 10.AN.7.157; 10.AN.7.158; 10.AN.7.196; 10.AN.7.223; 10.AN.7.240; 10.AN.7.244; 10.AN.7.243; 10.AN.7.247; 10.AN.15.157; 10.AN.15.158; 10.AN.15.196; 10.AN.15.223; 10.AN.15.240; 10.AN.15.244; 10.AN.15.243; 10.AN.15.247; 10.AN.16.157; 10.AN.16.158; 10.AN.16.196; 10.AN.16.223; 10.AN.16.240; 10.AN.16.244; 10.AN.16.243; 10.AN.16.247; 10.AN.18.157; 10.AN.18.158; 10.AN.18.196; 10.AN.18.223; 10.AN.18.240; 10.AN.18.244; 10.AN.18.243; 10.AN.18.247; 10.AN.26.157; 10.AN.26.158; 10.AN.26.196; 10.AN.26.223; 10.AN.26.240; 10.AN.26.244; 10.AN.26.243; 10.AN.26.247; 10.AN.27.157; 10.AN.27.158; 10.AN.27.196; 10.AN.27.223; 10.AN.27.240; 10.AN.27.244; 10.AN.27.243; 10.AN.27.247; 10.AN.29.157; 10.AN.29.158; 10.AN.29.196; 10.AN.29.223; 10.AN.29.240; 10.AN.29.244; 10.AN.29.243; 10.AN.29.247; 10.AN.54.157; 10.AN.54.158; 10.AN.54.196; 10.AN.54.223; 10.AN.54.240; 10.AN.54.244; 10.AN.54.243; 10.AN.54.247; 10.AN.55.157; 10.AN.55.158; 10.AN.55.196; 10.AN.55.223; 10.AN.55.240; 10.AN.55.244; 10.AN.55.243; 10.AN.55.247; 10.AN.56.157; 10.AN.56.158; 10.AN.56.196; 10.AN.56.223; 10.AN.56.240; 10.AN.56.244; 10.AN.56.243; 10.AN.56.247; 10.AN.157.157; 10.AN.157.158; 10.AN.157.196; 10.AN.157.223; 10.AN.157.240; 10.AN.157.244; 10.AN.157.243; 10.AN.157.247; 10.AN.196.157; 10.AN.196.158; 10.AN.196.196; 10.AN.196.223; 10.AN.196.240; 10.AN.196.244; 10.AN.196.243; 10.AN.196.247; 10.AN.223.157; 10.AN.223.158; 10.AN.223.196; 10.AN.223.223; 10.AN.223.240; 10.AN.223.244; 10.AN.223.243; 10.AN.223.247; 10.AN.240.157; 10.AN.240.158; 10.AN.240.196; 10.AN.240.223; 10.AN.240.240; 10.AN.240.244; 10.AN.240.243; 10.AN.240.247; 10.AN.244.157; 10.AN.244.158; 10.AN.244.196; 10.AN.244.223; 10.AN.244.240; 10.AN.244.244; 10.AN.244.243; 10.AN.244.247; 10.AN.247.157; 10.AN.247.158; 10.AN.247.196; 10.AN.247.223; 10.AN.247.240; 10.AN.247.244; 10.AN.247.243; 10.AN.247.247;

Prodrugs of 10.AP

10.AP.4.157; 10.AP.4.158; 10.AP.4.196; 10.AP.4.223; 10.AP.4.240; 10.AP.4.244; 10.AP.4.243; 10.AP.4.247; 10.AP.5.157; 10.AP.5.158; 10.AP.5.196; 10.AP.5.223; 10.AP.5.240; 10.AP.5.244; 10.AP.5.243; 10.AP.5.247; 10.AP.7.157; 10.AP.7.158; 10.AP.7.196; 10.AP.7.223; 10.AP.7.240; 10.AP.7.244; 10.AP.7.243; 10.AP.7.247; 10.AP.15.157; 10.AP.15.158; 10.AP.15.196; 10.AP.15.223; 10.AP.15.240; 10.AP.15.244; 10.AP.15.243; 10.AP.15.247; 10.AP.16.157; 10.AP.16.158; 10.AP.16.196; 10.AP.16.223; 10.AP.16.240; 10.AP.16.244; 10.AP.16.243; 10.AP.16.247; 10.AP.18.157; 10.AP.18.158; 10.AP.18.196; 10.AP.18.223; 10.AP.18.240; 10.AP.18.244; 10.AP.18.243; 10.AP.18.247; 10.AP.26.157; 10.AP.26.158; 10.AP.26.196; 10.AP.26.223; 10.AP.26.240; 10.AP.26.244; 10.AP.26.243; 10.AP.26.247; 10.AP.27.157; 10.AP.27.158; 10.AP.27.196; 10.AP.27.223; 10.AP.27.240; 10.AP.27.244; 10.AP.27.243; 10.AP.27.247; 10.AP.29.157; 10.AP.29.158; 10.AP.29.196; 10.AP.29.223; 10.AP.29.240; 10.AP.29.244; 10.AP.29.243; 10.AP.29.247; 10.AP.54.157; 10.AP.54.158; 10.AP.54.196; 10.AP.54.223; 10.AP.54.240; 10.AP.54.244; 10.AP.54.243; 10.AP.54.247; 10.AP.55.157; 10.AP.55.158; 10.AP.55.196; 10.AP.55.223; 10.AP.55.240; 10.AP.55.244; 10.AP.55.243; 10.AP.55.247; 10.AP.56.157; 10.AP.56.158; 10.AP.56.196; 10.AP.56.223; 10.AP.56.240; 10.AP.56.244; 10.AP.56.243; 10.AP.56.247; 10.AP.157.157; 10.AP.157.158; 10.AP.157.196; 10.AP.157.223; 10.AP.157.240; 10.AP.157.244; 10.AP.157.243; 10.AP.157.247; 10.AP.196.157; 10.AP.196.158; 10.AP.196.196; 10.AP.196.223; 10.AP.196.240; 10.AP.196.244; 10.AP.196.243; 10.AP.196.247; 10.AP.223.157; 10.AP.223.158; 10.AP.223.196; 10.AP.223.223; 10.AP.223.240; 10.AP.223.244; 10.AP.223.243; 10.AP.223.247; 10.AP.240.157;

TABLE 100-continued

10.AP.240.158; 10.AP.240.196; 10.AP.240.223; 10.AP.240.240; 10.AP.240.244; 10.AP.240.243; 10.AP.240.247; 10.AP.244.157; 10.AP.244.158; 10.AP.244.196; 10.AP.244.223; 10.AP.244.240; 10.AP.244.244; 10.AP.244.243; 10.AP.244.247; 10.AP.247.157; 10.AP.247.158; 10.AP.247.196; 10.AP.247.223; 10.AP.247.240; 10.AP.247.244; 10.AP.247.243; 10.AP.247.247;

Prodrugs of 10.AZ

10.AZ.4.157; 10.AZ.4.158; 10.AZ.4.196; 10.AZ.4.223; 10.AZ.4.240; 10.AZ.4.244; 10.AZ.4.243; 10.AZ.4.247; 10.AZ.5.157; 10.AZ.5.158; 10.AZ.5.196; 10.AZ.5.223; 10.AZ.5.240; 10.AZ.5.244; 10.AZ.5.243; 10.AZ.5.247; 10.AZ.7.157; 10.AZ.7.158; 10.AZ.7.196; 10.AZ.7.223; 10.AZ.7.240; 10.AZ.7.244; 10.AZ.7.243; 10.AZ.7.247; 10.AZ.15.157; 10.AZ.15.158; 10.AZ.15.196; 10.AZ.15.223; 10.AZ.15.240; 10.AZ.15.244; 10.AZ.15.243; 10.AZ.15.247; 10.AZ.16.157; 10.AZ.16.158; 10.AZ.16.196; 10.AZ.16.223; 10.AZ.16.240; 10.AZ.16.244; 10.AZ.16.243; 10.AZ.16.247; 10.AZ.18.157; 10.AZ.18.158; 10.AZ.18.196; 10.AZ.18.223; 10.AZ.18.240; 10.AZ.18.244; 10.AZ.18.243; 10.AZ.18.247; 10.AZ.26.157; 10.AZ.26.158; 10.AZ.26.196; 10.AZ.26.223; 10.AZ.26.240; 10.AZ.26.244; 10.AZ.26.243; 10.AZ.26.247; 10.AZ.27.157; 10.AZ.27.158; 10.AZ.27.196; 10.AZ.27.223; 10.AZ.27.240; 10.AZ.27.244; 10.AZ.27.243; 10.AZ.27.247; 10.AZ.29.157; 10.AZ.29.158; 10.AZ.29.196; 10.AZ.29.223; 10.AZ.29.240; 10.AZ.29.244; 10.AZ.29.243; 10.AZ.29.247; 10.AZ.54.157; 10.AZ.54.158; 10.AZ.54.196; 10.AZ.54.223; 10.AZ.54.240; 10.AZ.54.244; 10.AZ.54.243; 10.AZ.54.247; 10.AZ.55.157; 10.AZ.55.158; 10.AZ.55.196; 10.AZ.55.223; 10.AZ.55.240; 10.AZ.55.244; 10.AZ.55.243; 10.AZ.55.247; 10.AZ.56.157; 10.AZ.56.158; 10.AZ.56.196; 10.AZ.56.223; 10.AZ.56.240; 10.AZ.56.244; 10.AZ.56.243; 10.AZ.56.247; 10.AZ.157.157; 10.AZ.157.158; 10.AZ.157.196; 10.AZ.157.223; 10.AZ.157.240; 10.AZ.157.244; 10.AZ.157.243; 10.AZ.157.247; 10.AZ.196.157; 10.AZ.196.158; 10.AZ.196.196; 10.AZ.196.223; 10.AZ.196.240; 10.AZ.196.244; 10.AZ.196.243; 10.AZ.196.247; 10.AZ.223.157; 10.AZ.223.158; 10.AZ.223.196; 10.AZ.223.223; 10.AZ.223.240; 10.AZ.223.244; 10.AZ.223.243; 10.AZ.223.247; 10.AZ.240.157; 10.AZ.240.158; 10.AZ.240.196; 10.AZ.240.223; 10.AZ.240.240; 10.AZ.240.244; 10.AZ.240.243; 10.AZ.240.247; 10.AZ.244.157; 10.AZ.244.158; 10.AZ.244.196; 10.AZ.244.223; 10.AZ.244.240; 10.AZ.244.244; 10.AZ.244.243; 10.AZ.244.247; 10.AZ.247.157; 10.AZ.247.158; 10.AZ.247.196; 10.AZ.247.223; 10.AZ.247.240; 10.AZ.247.244; 10.AZ.247.243; 10.AZ.247.247;

Prodrugs of 10.BF

10.BF.4.157; 10.BF.4.158; 10.BF.4.196; 10.BF.4.223; 10.BF.4.240; 10.BF.4.244; 10.BF.4.243; 10.BF.4.247; 10.BF.5.157; 10.BF.5.158; 10.BF.5.196; 10.BF.5.223; 10.BF.5.240; 10.BF.5.244; 10.BF.5.243; 10.BF.5.247; 10.BF.7.157; 10.BF.7.158; 10.BF.7.196; 10.BF.7.223; 10.BF.7.240; 10.BF.7.244; 10.BF.7.243; 10.BF.7.247; 10.BF.15.157; 10.BF.15.158; 10.BF.15.196; 10.BF.15.223; 10.BF.15.240; 10.BF.15.244; 10.BF.15.243; 10.BF.15.247; 10.BF.16.157; 10.BF.16.158; 10.BF.16.196; 10.BF.16.223; 10.BF.16.240; 10.BF.16.244; 10.BF.16.243; 10.BF.16.247; 10.BF.18.157; 10.BF.18.158; 10.BF.18.196; 10.BF.18.223; 10.BF.18.240; 10.BF.18.244; 10.BF.18.243; 10.BF.18.247; 10.BF.26.157; 10.BF.26.158; 10.BF.26.196; 10.BF.26.223; 10.BF.26.240; 10.BF.26.244; 10.BF.26.243; 10.BF.26.247; 10.BF.27.157; 10.BF.27.158; 10.BF.27.196; 10.BF.27.223; 10.BF.27.240; 10.BF.27.244; 10.BF.27.243; 10.BF.27.247; 10.BF.29.157; 10.BF.29.158; 10.BF.29.196; 10.BF.29.223; 10.BF.29.240; 10.BF.29.244; 10.BF.29.243; 10.BF.29.247; 10.BF.54.157; 10.BF.54.158; 10.BF.54.196; 10.BF.54.223; 10.BF.54.240; 10.BF.54.244; 10.BF.54.243; 10.BF.54.247; 10.BF.55.157; 10.BF.55.158; 10.BF.55.196; 10.BF.55.223; 10.BF.55.240; 10.BF.55.244; 10.BF.55.243; 10.BF.55.247; 10.BF.56.157; 10.BF.56.158; 10.BF.56.196; 10.BF.56.223; 10.BF.56.240; 10.BF.56.244; 10.BF.56.243; 10.BF.56.247; 10.BF.157.157; 10.BF.157.158; 10.BF.157.196; 10.BF.157.223; 10.BF.157.240; 10.BF.157.244; 10.BF.157.243; 10.BF.157.247; 10.BF.196.157; 10.BF.196.158; 10.BF.196.196; 10.BF.196.223; 10.BF.196.240; 10.BF.196.244; 10.BF.196.243; 10.BF.196.247; 10.BF.223.157; 10.BF.223.158; 10.BF.223.196; 10.BF.223.223; 10.BF.223.240; 10.BF.223.244; 10.BF.223.243; 10.BF.223.247; 10.BF.240.157; 10.BF.240.158; 10.BF.240.196; 10.BF.240.223; 10.BF.240.240; 10.BF.240.244; 10.BF.240.243; 10.BF.240.247; 10.BF.244.157; 10.BF.244.158; 10.BF.244.196; 10.BF.244.223; 10.BF.244.240; 10.BF.244.244; 10.BF.244.243; 10.BF.244.247; 10.BF.247.157; 10.BF.247.158; 10.BF.247.196; 10.BF.247.223; 10.BF.247.240; 10.BF.247.244; 10.BF.247.243; 10.BF.247.247;

Prodrugs of 10.CI

10.CI.4.157; 10.CI.4.158; 10.CI.4.196; 10.CI.4.223; 10.CI.4.240; 10.CI.4.244; 10.CI.4.243; 10.CI.4.247; 10.CI.5.157; 10.CI.5.158; 10.CI.5.196; 10.CI.5.223; 10.CI.5.240; 10.CI.5.244; 10.CI.5.243; 10.CI.5.247; 10.CI.7.157; 10.CI.7.158; 10.CI.7.196; 10.CI.7.223; 10.CI.7.240; 10.CI.7.244; 10.CI.7.243; 10.CI.7.247; 10.CI.15.157; 10.CI.15.158; 10.CI.15.196; 10.CI.15.223; 10.CI.15.240; 10.CI.15.244; 10.CI.15.243; 10.CI.15.247; 10.CI.16.157; 10.CI.16.158; 10.CI.16.196; 10.CI.16.223; 10.CI.16.240; 10.CI.16.244; 10.CI.16.243; 10.CI.16.247; 10.CI.18.157; 10.CI.18.158; 10.CI.18.196; 10.CI.18.223; 10.CI.18.240; 10.CI.18.244; 10.CI.18.243; 10.CI.18.247; 10.CI.26.157; 10.CI.26.158; 10.CI.26.196; 10.CI.26.223; 10.CI.26.240; 10.CI.26.244; 10.CI.26.243; 10.CI.26.247; 10.CI.27.157; 10.CI.27.158; 10.CI.27.196; 10.CI.27.223; 10.CI.27.240; 10.CI.27.244; 10.CI.27.243; 10.CI.27.247; 10.CI.29.157; 10.CI.29.158; 10.CI.29.196; 10.CI.29.223; 10.CI.29.240; 10.CI.29.244; 10.CI.29.243; 10.CI.29.247; 10.CI.54.157; 10.CI.54.158; 10.CI.54.196; 10.CI.54.223; 10.CI.54.240; 10.CI.54.244; 10.CI.54.243; 10.CI.54.247; 10.CI.55.157; 10.CI.55.158; 10.CI.55.196; 10.CI.55.223; 10.CI.55.240; 10.CI.55.244; 10.CI.55.243; 10.CI.55.247; 10.CI.56.157; 10.CI.56.158; 10.CI.56.196; 10.CI.56.223; 10.CI.56.240; 10.CI.56.244; 10.CI.56.243; 10.CI.56.247; 10.CI.157.157; 10.CI.157.158;

TABLE 100-continued

10.CI.157.196; 10.CI.157.223; 10.CI.157.240; 10.CI.157.244; 10.CI.157.243; 10.CI.157.247; 10.CI.196.157; 10.CI.196.158; 10.CI.196.196; 10.CI.196.223; 10.CI.196.240; 10.CI.196.244; 10.CI.196.243; 10.CI.196.247; 10.CI.223.157; 10.CI.223.158; 10.CI.223.196; 10.CI.223.223; 10.CI.223.240; 10.CI.223.244; 10.CI.223.243; 10.CI.223.247; 10.CI.240.157; 10.CI.240.158; 10.CI.240.196; 10.CI.240.223; 10.CI.240.240; 10.CI.240.244; 10.CI.240.243; 10.CI.240.247; 10.CI.244.157; 10.CI.244.158; 10.CI.244.196; 10.CI.244.223; 10.CI.244.240; 10.CI.244.244; 10.CI.244.243; 10.CI.244.247; 10.CI.247.157; 10.CI.247.158; 10.CI.247.196; 10.CI.247.223; 10.CI.247.240; 10.CI.247.244; 10.CI.247.243; 10.CI.247.247;

Prodrugs of 10.CO

10.CO.4.157; 10.CO.4.158; 10.CO.4.196; 10.CO.4.223; 10.CO.4.240; 10.CO.4.244; 10.CO.4.243; 10.CO.4.247; 10.CO.5.157; 10.CO.5.158; 10.CO.5.196; 10.CO.5.223; 10.CO.5.240; 10.CO.5.244; 10.CO.5.243; 10.CO.5.247; 10.CO.7.157; 10.CO.7.158; 10.CO.7.196; 10.CO.7.223; 10.CO.7.240; 10.CO.7.244; 10.CO.7.243; 10.CO.7.247; 10.CO.15.157; 10.CO.15.158; 10.CO.15.196; 10.CO.15.223; 10.CO.15.240; 10.CO.15.244; 10.CO.15.243; 10.CO.15.247; 10.CO.16.157; 10.CO.16.158; 10.CO.16.196; 10.CO.16.223; 10.CO.16.240; 10.CO.16.244; 10.CO.16.243; 10.CO.16.247; 10.CO.18.157; 10.CO.18.158; 10.CO.18.196; 10.CO.18.223; 10.CO.18.240; 10.CO.18.244; 10.CO.18.243; 10.CO.18.247; 10.CO.26.157; 10.CO.26.158; 10.CO.26.196; 10.CO.26.223; 10.CO.26.240; 10.CO.26.244; 10.CO.26.243; 10.CO.26.247; 10.CO.27.157; 10.CO.27.158; 10.CO.27.196; 10.CO.27.223; 10.CO.27.240; 10.CO.27.244; 10.CO.27.243; 10.CO.27.247; 10.CO.29.157; 10.CO.29.158; 10.CO.29.196; 10.CO.29.223; 10.CO.29.240; 10.CO.29.244; 10.CO.29.243; 10.CO.29.247; 10.CO.54.157; 10.CO.54.158; 10.CO.54.196; 10.CO.54.223; 10.CO.54.240; 10.CO.54.244; 10.CO.54.243; 10.CO.54.247; 10.CO.55.157; 10.CO.55.158; 10.CO.55.196; 10.CO.55.223; 10.CO.55.240; 10.CO.55.244; 10.CO.55.243; 10.CO.55.247; 10.CO.56.157; 10.CO.56.158; 10.CO.56.196; 10.CO.56.223; 10.CO.56.240; 10.CO.56.244; 10.CO.56.243; 10.CO.56.247; 10.CO.157.157; 10.CO.157.158; 10.CO.157.196; 10.CO.157.223; 10.CO.157.240; 10.CO.157.244; 10.CO.157.243; 10.CO.157.247; 10.CO.196.157; 10.CO.196.158; 10.CO.196.196; 10.CO.196.223; 10.CO.196.240; 10.CO.196.244; 10.CO.196.243; 10.CO.196.247; 10.CO.223.157; 10.CO.223.158; 10.CO.223.196; 10.CO.223.223; 10.CO.223.240; 10.CO.223.244; 10.CO.223.243; 10.CO.223.247; 10.CO.240.157; 10.CO.240.158; 10.CO.240.196; 10.CO.240.223; 10.CO.240.240; 10.CO.240.244; 10.CO.240.243; 10.CO.240.247; 10.CO.244.157; 10.CO.244.158; 10.CO.244.196; 10.CO.244.223; 10.CO.244.240; 10.CO.244.244; 10.CO.244.243; 10.CO.244.247; 10.CO.247.157; 10.CO.247.158; 10.CO.247.196; 10.CO.247.223; 10.CO.247.240; 10.CO.247.244; 10.CO.247.243; 10.CO.247.247;

Prodrugs of 11.AH

11.AH.4.157; 11.AH.4.158; 11.AH.4.196; 11.AH.4.223; 11.AH.4.240; 11.AH.4.244; 11.AH.4.243; 11.AH.4.247; 11.AH.5.157; 11.AH.5.158; 11.AH.5.196; 11.AH.5.223; 11.AH.5.240; 11.AH.5.244; 11.AH.5.243; 11.AH.5.247; 11.AH.7.157; 11.AH.7.158; 11.AH.7.196; 11.AH.7.223; 11.AH.7.240; 11.AH.7.244; 11.AH.7.243; 11.AH.7.247; 11.AH.15.157; 11.AH.15.158; 11.AH.15.196; 11.AH.15.223; 11.AH.15.240; 11.AH.15.244; 11.AH.15.243; 11.AH.15.247; 11.AH.16.157; 11.AH.16.158; 11.AH.16.196; 11.AH.16.223; 11.AH.16.240; 11.AH.16.244; 11.AH.16.243; 11.AH.16.247; 11.AH.18.157; 11.AH.18.158; 11.AH.18.196; 11.AH.18.223; 11.AH.18.240; 11.AH.18.244; 11.AH.18.243; 11.AH.18.247; 11.AH.26.157; 11.AH.26.158; 11.AH.26.196; 11.AH.26.223; 11.AH.26.240; 11.AH.26.244; 11.AH.26.243; 11.AH.26.247; 11.AH.27.157; 11.AH.27.158; 11.AH.27.196; 11.AH.27.223; 11.AH.27.240; 11.AH.27.244; 11.AH.27.243; 11.AH.27.247; 11.AH.29.157; 11.AH.29.158; 11.AH.29.196; 11.AH.29.223; 11.AH.29.240; 11.AH.29.244; 11.AH.29.243; 11.AH.29.247; 11.AH.54.157; 11.AH.54.158; 11.AH.54.196; 11.AH.54.223; 11.AH.54.240; 11.AH.54.244; 11.AH.54.243; 11.AH.54.247; 11.AH.55.157; 11.AH.55.158; 11.AH.55.196; 11.AH.55.223; 11.AH.55.240; 11.AH.55.244; 11.AH.55.243; 11.AH.55.247; 11.AH.56.157; 11.AH.56.158; 11.AH.56.196; 11.AH.56.223; 11.AH.56.240; 11.AH.56.244; 11.AH.56.243; 11.AH.56.247; 11.AH.157.157; 11.AH.157.158; 11.AH.157.196; 11.AH.157.223; 11.AH.157.240; 11.AH.157.244; 11.AH.157.243; 11.AH.157.247; 11.AH.196.157; 11.AH.196.158; 11.AH.196.196; 11.AH.196.223; 11.AH.196.240; 11.AH.196.244; 11.AH.196.243; 11.AH.196.247; 11.AH.223.157; 11.AH.223.158; 11.AH.223.196; 11.AH.223.223; 11.AH.223.240; 11.AH.223.244; 11.AH.223.243; 11.AH.223.247; 11.AH.240.157; 11.AH.240.158; 11.AH.240.196; 11.AH.240.223; 11.AH.240.240; 11.AH.240.244; 11.AH.240.243; 11.AH.240.247; 11.AH.244.157; 11.AH.244.158; 11.AH.244.196; 11.AH.244.223; 11.AH.244.240; 11.AH.244.244; 11.AH.244.243; 11.AH.244.247; 11.AH.247.157; 11.AH.247.158; 11.AH.247.196; 11.AH.247.223; 11.AH.247.240; 11.AH.247.244; 11.AH.247.243; 11.AH.247.247;

Prodrugs of 11.AJ

11.AJ.4.157; 11.AJ.4.158; 11.AJ.4.196; 11.AJ.4.223; 11.AJ.4.240; 11.AJ.4.244; 11.AJ.4.243; 11.AJ.4.247; 11.AJ.5.157; 11.AJ.5.158; 11.AJ.5.196; 11.AJ.5.223; 11.AJ.5.240; 11.AJ.5.244; 11.AJ.5.243; 11.AJ.5.247; 11.AJ.7.157; 11.AJ.7.158; 11.AJ.7.196; 11.AJ.7.223; 11.AJ.7.240; 11.AJ.7.244; 11.AJ.7.243; 11.AJ.7.247; 11.AJ.15.157; 11.AJ.15.158; 11.AJ.15.196; 11.AJ.15.223; 11.AJ.15.240; 11.AJ.15.244; 11.AJ.15.243; 11.AJ.15.247; 11.AJ.16.157; 11.AJ.16.158; 11.AJ.16.196; 11.AJ.16.223; 11.AJ.16.240; 11.AJ.16.244; 11.AJ.16.243; 11.AJ.16.247; 11.AJ.18.157; 11.AJ.18.158; 11.AJ.18.196; 11.AJ.18.223; 11.AJ.18.240; 11.AJ.18.244; 11.AJ.18.243; 11.AJ.18.247; 11.AJ.26.157; 11.AJ.26.158; 11.AJ.26.196; 11.AJ.26.223; 11.AJ.26.240; 11.AJ.26.244; 11.AJ.26.243; 11.AJ.26.247; 11.AJ.27.157; 11.AJ.27.158; 11.AJ.27.196; 11.AJ.27.223; 11.AJ.27.240; 11.AJ.27.244; 11.AJ.27.243; 11.AJ.27.247; 11.AJ.29.157; 11.AJ.29.158; 11.AJ.29.196; 11.AJ.29.223; 11.AJ.29.240; 11.AJ.29.244; 11.AJ.29.243; 11.AJ.29.247; 11.AJ.54.157; 11.AJ.54.158; 11.AJ.54.196; 11.AJ.54.223; 11.AJ.54.240; 11.AJ.54.244; 11.AJ.54.243; 11.AJ.54.247;

TABLE 100-continued

11.AJ.55.157; 11.AJ.55.158; 11.AJ.55.196; 11.AJ.55.223; 11.AJ.55.240; 11.AJ.55.244; 11.AJ.55.243; 11.AJ.55.247; 11.AJ.56.157; 11.AJ.56.158; 11.AJ.56.196; 11.AJ.56.223; 11.AJ.56.240; 11.AJ.56.244; 11.AJ.56.243; 11.AJ.56.247; 11.AJ.157.157; 11.AJ.157.158; 11.AJ.157.196; 11.AJ.157.223; 11.AJ.157.240; 11.AJ.157.244; 11.AJ.157.243; 11.AJ.157.247; 11.AJ.196.157; 11.AJ.196.158; 11.AJ.196.196; 11.AJ.196.223; 11.AJ.196.240; 11.AJ.196.244; 11.AJ.196.243; 11.AJ.196.247; 11.AJ.223.157; 11.AJ.223.158; 11.AJ.223.196; 11.AJ.223.223; 11.AJ.223.240; 11.AJ.223.244; 11.AJ.223.243; 11.AJ.223.247; 11.AJ.240.157; 11.AJ.240.158; 11.AJ.240.196; 11.AJ.240.223; 11.AJ.240.240; 11.AJ.240.244; 11.AJ.240.243; 11.AJ.240.247; 11.AJ.244.157; 11.AJ.244.158; 11.AJ.244.196; 11.AJ.244.223; 11.AJ.244.240; 11.AJ.244.244; 11.AJ.244.243; 11.AJ.244.247; 11.AJ.247.157; 11.AJ.247.158; 11.AJ.247.196; 11.AJ.247.223; 11.AJ.247.240; 11.AJ.247.244; 11.AJ.247.243; 11.AJ.247.247;

Prodrugs of 11.AN

11.AN.4.157; 11.AN.4.158; 11.AN.4.196; 11.AN.4.223; 11.AN.4.240; 11.AN.4.244; 11.AN.4.243; 11.AN.4.247; 11.AN.5.157; 11.AN.5.158; 11.AN.5.196; 11.AN.5.223; 11.AN.5.240; 11.AN.5.244; 11.AN.5.243; 11.AN.5.247; 11.AN.7.157; 11.AN.7.158; 11.AN.7.196; 11.AN.7.223; 11.AN.7.240; 11.AN.7.244; 11.AN.7.243; 11.AN.7.247; 11.AN.15.157; 11.AN.15.158; 11.AN.15.196; 11.AN.15.223; 11.AN.15.240; 11.AN.15.244; 11.AN.15.243; 11.AN.15.247; 11.AN.16.157; 11.AN.16.158; 11.AN.16.196; 11.AN.16.223; 11.AN.16.240; 11.AN.16.244; 11.AN.16.243; 11.AN.16.247; 11.AN.18.157; 11.AN.18.158; 11.AN.18.196; 11.AN.18.223; 11.AN.18.240; 11.AN.18.244; 11.AN.18.243; 11.AN.18.247; 11.AN.26.157; 11.AN.26.158; 11.AN.26.196; 11.AN.26.223; 11.AN.26.240; 11.AN.26.244; 11.AN.26.243; 11.AN.26.247; 11.AN.27.157; 11.AN.27.158; 11.AN.27.196; 11.AN.27.223; 11.AN.27.240; 11.AN.27.244; 11.AN.27.243; 11.AN.27.247; 11.AN.29.157; 11.AN.29.158; 11.AN.29.196; 11.AN.29.223; 11.AN.29.240; 11.AN.29.244; 11.AN.29.243; 11.AN.29.247; 11.AN.54.157; 11.AN.54.158; 11.AN.54.196; 11.AN.54.223; 11.AN.54.240; 11.AN.54.244; 11.AN.54.243; 11.AN.54.247; 11.AN.55.157; 11.AN.55.158; 11.AN.55.196; 11.AN.55.223; 11.AN.55.240; 11.AN.55.244; 11.AN.55.243; 11.AN.55.247; 11.AN.56.157; 11.AN.56.158; 11.AN.56.196; 11.AN.56.223; 11.AN.56.240; 11.AN.56.244; 11.AN.56.243; 11.AN.56.247; 11.AN.157.157; 11.AN.157.158; 11.AN.157.196; 11.AN.157.223; 11.AN.157.240; 11.AN.157.244; 11.AN.157.243; 11.AN.157.247; 11.AN.196.157; 11.AN.196.158; 11.AN.196.196; 11.AN.196.223; 11.AN.196.240; 11.AN.196.244; 11.AN.196.243; 11.AN.196.247; 11.AN.223.157; 11.AN.223.158; 11.AN.223.196; 11.AN.223.223; 11.AN.223.240; 11.AN.223.244; 11.AN.223.243; 11.AN.223.247; 11.AN.240.157; 11.AN.240.158; 11.AN.240.196; 11.AN.240.223; 11.AN.240.240; 11.AN.240.244; 11.AN.240.243; 11.AN.240.247; 11.AN.244.157; 11.AN.244.158; 11.AN.244.196; 11.AN.244.223; 11.AN.244.240; 11.AN.244.244; 11.AN.244.243; 11.AN.244.247; 11.AN.247.157; 11.AN.247.158; 11.AN.247.196; 11.AN.247.223; 11.AN.247.240; 11.AN.247.244; 11.AN.247.243; 11.AN.247.247;

Prodrugs of 11.AP

11.AP.4.157; 11.AP.4.158; 11.AP.4.196; 11.AP.4.223; 11.AP.4.240; 11.AP.4.244; 11.AP.4.243; 11.AP.4.247; 11.AP.5.157; 11.AP.5.158; 11.AP.5.196; 11.AP.5.223; 11.AP.5.240; 11.AP.5.244; 11.AP.5.243; 11.AP.5.247; 11.AP.7.157; 11.AP.7.158; 11.AP.7.196; 11.AP.7.223; 11.AP.7.240; 11.AP.7.244; 11.AP.7.243; 11.AP.7.247; 11.AP.15.157; 11.AP.15.158; 11.AP.15.196; 11.AP.15.223; 11.AP.15.240; 11.AP.15.244; 11.AP.15.243; 11.AP.15.247; 11.AP.16.157; 11.AP.16.158; 11.AP.16.196; 11.AP.16.223; 11.AP.16.240; 11.AP.16.244; 11.AP.16.243; 11.AP.16.247; 11.AP.18.157; 11.AP.18.158; 11.AP.18.196; 11.AP.18.223; 11.AP.18.240; 11.AP.18.244; 11.AP.18.243; 11.AP.18.247; 11.AP.26.157; 11.AP.26.158; 11.AP.26.196; 11.AP.26.223; 11.AP.26.240; 11.AP.26.244; 11.AP.26.243; 11.AP.26.247; 11.AP.27.157; 11.AP.27.158; 11.AP.27.196; 11.AP.27.223; 11.AP.27.240; 11.AP.27.244; 11.AP.27.243; 11.AP.27.247; 11.AP.29.157; 11.AP.29.158; 11.AP.29.196; 11.AP.29.223; 11.AP.29.240; 11.AP.29.244; 11.AP.29.243; 11.AP.29.247; 11.AP.54.157; 11.AP.54.158; 11.AP.54.196; 11.AP.54.223; 11.AP.54.240; 11.AR.54.244; 11.AP.54.243; 11.AP.54.247; 11.AP.55.157; 11.AP.55.158; 11.AP.55.196; 11.AP.55.223; 11.AP.55.240; 11.AP.55.244; 11.AP.55.243; 11.AP.55.247; 11.AP.56.157; 11.AP.56.158; 11.AP.56.196; 11.AP.56.223; 11.AP.56.240; 11.AP.56.244; 11.AP.56.243; 11.AP.56.247; 11.AP.157.157; 11.AP.157.158; 11.AP.157.196; 11.AP.157.223; 11.AP.157.240; 11.AP.157.244; 11.AP.157.243; 11.AP.157.247; 11.AP.196.157; 11.AP.196.158; 11.AP.196.196; 11.AP.196.223; 11.AP.196.240; 11.AP.196.244; 11.AP.196.243; 11.AP.196.247; 11.AP.223.157; 11.AP.223.158; 11.AP.223.196; 11.AP.223.223; 11.AP.223.240; 11.AP.223.244; 11.AP.223.243; 11.AP.223.247; 11.AP.240.157; 11.AP.240.158; 11.AP.240.196; 11.AP.240.223; 11.AP.240.240; 11.AP.240.244; 11.AP.240.243; 11.AP.240.247; 11.AP.244.157; 11.AP.244.158; 11.AP.244.196; 11.AP.244.223; 11.AP.244.240; 11.AP.244.244; 11.AP.244.243; 11.AP.244.247; 11.AP.247.157; 11.AP.247.158; 11.AP.247.196; 11.AP.247.223; 11.AP.247.240; 11.AP.247.244; 11.AP.247.243; 11.AP.247.247;

Prodrugs of 11.AZ

11.AZ.4.157; 11.AZ.4.158; 11.AZ.4.196; 11.AZ.4.223; 11.AZ.4.240; 11.AZ.4.244; 11.AZ.4.243; 11.AZ.4.247; 11.AZ.5.157; 11.AZ.5.158; 11.AZ.5.196; 11.AZ.5.223; 11.AZ.5.240; 11.AZ.5.244; 11.AZ.5.243; 11.AZ.5.247; 11.AZ.7.157; 11.AZ.7.158; 11.AZ.7.196; 11.AZ.7.223; 11.AZ.7.240; 11.AZ.7.244; 11.AZ.7.243; 11.AZ.7.247; 11.AZ.15.157; 11.AZ.15.158; 11.AZ.15.196; 11.AZ.15.223; 11.AZ.15.240; 11.AZ.15.244; 11.AZ.15.243; 11.AZ.15.247; 11.AZ.16.157; 11.AZ.16.158; 11.AZ.16.196; 11.AZ.16.223; 11.AZ.16.240; 11.AZ.16.244; 11.AZ.16.243; 11.AZ.16.247; 11.AZ.18.157; 11.AZ.18.158; 11.AZ.18.196; 11.AZ.18.223; 11.AZ.18.240; 11.AZ.18.244; 11.AZ.18.243; 11.AZ.18.247;

TABLE 100-continued

11.AZ.26.157; 11.AZ.26.158; 11.AZ.26.196; 11.AZ.26.223; 11.AZ.26.240; 11.AZ.26.244; 11.AZ.26.243; 11.AZ.26.247; 11.AZ.27.157; 11.AZ.27.158; 11.AZ.27.196; 11.AZ.27.223; 11.AZ.27.240; 11.AZ.27.244; 11.AZ.27.243; 11.AZ.27.247; 11.AZ.29.157; 11.AZ.29.158; 11.AZ.29.196; 11.AZ.29.223; 11.AZ.29.240; 11.AZ.29.244; 11.AZ.29.243; 11.AZ.29.247; 11.AZ.54.157; 11.AZ.54.158; 11.AZ.54.196; 11.AZ.54.223; 11.AZ.54.240; 11.AZ.54.244; 11.AZ.54.243; 11.AZ.54.247; 11.AZ.55.157; 11.AZ.55.158; 11.AZ.55.196; 11.AZ.55.223; 11.AZ.55.240; 11.AZ.55.244; 11.AZ.55.243; 11.AZ.55.247; 11.AZ.56.157; 11.AZ.56.158; 11.AZ.56.196; 11.AZ.56.223; 11.AZ.56.240; 11.AZ.56.244; 11.AZ.56.243; 11.AZ.56.247; 11.AZ.157.157; 11.AZ.157.158; 11.AZ.157.196; 11.AZ.157.223; 11.AZ.157.240; 11.AZ.157.244; 11.AZ.157.243; 11.AZ.157.247; 11.AZ.196.157; 11.AZ.196.158; 11.AZ.196.196; 11.AZ.196.223; 11.AZ.196.240; 11.AZ.196.244; 11.AZ.196.243; 11.AZ.196.247; 11.AZ.223.157; 11.AZ.223.158; 11.AZ.223.196; 11.AZ.223.223; 11.AZ.223.240; 11.AZ.223.244; 11.AZ.223.243; 11.AZ.223.247; 11.AZ.240.157; 11.AZ.240.158; 11.AZ.240.196; 11.AZ.240.223; 11.AZ.240.240; 11.AZ.240.244; 11.AZ.240.243; 11.AZ.240.247; 11.AZ.244.157; 11.AZ.244.158; 11.AZ.244.196; 11.AZ.244.223; 11.AZ.244.240; 11.AZ.244.244; 11.AZ.244.243; 11.AZ.244.247; 11.AZ.247.157; 11.AZ.247.158; 11.AZ.247.196; 11.AZ.247.223; 11.AZ.247.240; 11.AZ.247.244; 11.AZ.247.243; 11.AZ.247.247;

Prodrugs of 11.BF

11.BF.4.157; 11.BF.4.158; 11.BF.4.196; 11.BF.4.223; 11.BF.4.240; 11.BF.4.244; 11.BF.4.243; 11.BF.4.247; 11.BF.5.157; 11.BF.5.158; 11.BF.5.196; 11.BF.5.223; 11.BF.5.240; 11.BF.5.244; 11.BF.5.243; 11.BF.5.247; 11.BF.7.157; 11.BF.7.158; 11.BF.7.196; 11.BF.7.223; 11.BF.7.240; 11.BF.7.244; 11.BF.7.243; 11.BF.7.247; 11.BF.15.157; 11.BF.15.158; 11.BF.15.196; 11.BF.15.223; 11.BF.15.240; 11.BF.15.244; 11.BF.15.243; 11.BF.15.247; 11.BF.16.157; 11.BF.16.158; 11.BF.16.196; 11.BF.16.223; 11.BF.16.240; 11.BF.16.244; 11.BF.16.243; 11.BF.16.247; 11.BF.18.157; 11.BF.18.158; 11.BF.18.196; 11.BF.18.223; 11.BF.18.240; 11.BF.18.244; 11.BF.18.243; 11.BF.18.247; 11.BF.26.157; 11.BF.26.158; 11.BF.26.196; 11.BF.26.223; 11.BF.26.240; 11.BF.26.244; 11.BF.26.243; 11.BF.26.247; 11.BF.27.157; 11.BF.27.158; 11.BF.27.196; 11.BF.27.223; 11.BF.27.240; 11.BF.27.244; 11.BF.27.243; 11.BF.27.247; 11.BF.29.157; 11.BF.29.158; 11.BF.29.196; 11.BF.29.223; 11.BF.29.240; 11.BF.29.244; 11.BF.29.243; 11.BF.29.247; 11.BF.54.157; 11.BF.54.158; 11.BF.54.196; 11.BF.54.223; 11.BF.54.240; 11.BF.54.244; 11.BF.54.243; 11.BF.54.247; 11.BF.55.157; 11.BF.55.158; 11.BF.55.196; 11.BF.55.223; 11.BF.55.240; 11.BF.55.244; 11.BF.55.243; 11.BF.55.247; 11.BF.56.157; 11.BF.56.158; 11.BF.56.196; 11.BF.56.223; 11.BF.56.240; 11.BF.56.244; 11.BF.56.243; 11.BF.56.247; 11.BF.157.157; 11.BF.157.158; 11.BF.157.196; 11.BF.157.223; 11.BF.157.240; 11.BF.157.244; 11.BF.157.243; 11.BF.157.247; 11.BF.196.157; 11.BF.196.158; 11.BF.196.196; 11.BF.196.223; 11.BF.196.240; 11.BF.196.244; 11.BF.196.243; 11.BF.196.247; 11.BF.223.157; 11.BF.223.158; 11.BF.223.196; 11.BF.223.223; 11.BF.223.240; 11.BF.223.244; 11.BF.223.243; 11.BF.223.247; 11.BF.240.157; 11.BF.240.158; 11.BF.240.196; 11.BF.240.223; 11.BF.240.240; 11.BF.240.244; 11.BF.240.243; 11.BF.240.247; 11.BF.244.157; 11.BF.244.158; 11.BF.244.196; 11.BF.244.223; 11.BF.244.240; 11.BF.244.244; 11.BF.244.243; 11.BF.244.247; 11.BF.247.157; 11.BF.247.158; 11.BF.247.196; 11.BF.247.223; 11.BF.247.240; 11.BF.247.244; 11.BF.247.243; 11.BF.247.247;

Prodrugs of 11.CI

11.CI.4.157; 11.CI.4.158; 11.CI.4.196; 11.CI.4.223; 11.CI.4.240; 11.CI.4.244; 11.CI.4.243; 11.CI.4.247; 11.CI.5.157; 11.CI.5.158; 11.CI.5.196; 11.CI.5.223; 11.CI.5.240; 11.CI.5.244; 11.CI.5.243; 11.CI.5.247; 11.CI.7.157; 11.CI.7.158; 11.CI.7.196; 11.CI.7.223; 11.CI.7.240; 11.CI.7.244; 11.CI.7.243; 11.CI.7.247; 11.CI.15.157; 11.CI.15.158; 11.CI.15.196; 11.CI.15.223; 11.CI.15.240; 11.CI.15.244; 11.CI.15.243; 11.CI.15.247; 11.CI.16.157; 11.CI.16.158; 11.CI.16.196; 11.CI.16.223; 11.CI.16.240; 11.CI.16.244; 11.CI.16.243; 11.CI.16.247; 11.CI.18.157; 11.CI.18.158; 11.CI.18.196; 11.CI.18.223; 11.CI.18.240; 11.CI.18.244; 11.CI.18.243; 11.CI.18.247; 11.CI.26.157; 11.CI.26.158; 11.CI.26.196; 11.CI.26.223; 11.CI.26.240; 11.CI.26.244; 11.CI.26.243; 11.CI.26.247; 11.CI.27.157; 11.CI.27.158; 11.CI.27.196; 11.CI.27.223; 11.CI.27.240; 11.CI.27.244; 11.CI.27.243; 11.CI.27.247; 11.CI.29.157; 11.CI.29.158; 11.CI.29.196; 11.CI.29.223; 11.CI.29.240; 11.CI.29.244; 11.CI.29.243; 11.CI.29.247; 11.CI.54.157; 11.CI.54.158; 11.CI.54.196; 11.CI.54.223; 11.CI.54.240; 11.CI.54.244; 11.CI.54.243; 11.CI.54.247; 11.CI.55.157; 11.CI.55.158; 11.CI.55.196; 11.CI.55.223; 11.CI.55.240; 11.CI.55.244; 11.CI.55.243; 11.CI.55.247; 11.CI.56.157; 11.CI.56.158; 11.CI.56.196; 11.CI.56.223; 11.CI.56.240; 11.CI.56.244; 11.CI.56.243; 11.CI.56.247; 11.CI.157.157; 11.CI.157.158; 11.CI.157.196; 11.CI.157.223; 11.CI.157.240; 11.CI.157.244; 11.CI.157.243; 11.CI.157.247; 11.CI.196.157; 11.CI.196.158; 11.CI.196.196; 11.CI.196.223; 11.CI.196.240; 11.CI.196.244; 11.CI.196.243; 11.CI.196.247; 11.CI.223.157; 11.CI.223.158; 11.CI.223.196; 11.CI.223.223; 11.CI.223.240; 11.CI.223.244; 11.CI.223.243; 11.CI.223.247; 11.CI.240.157; 11.CI.240.158; 11.CI.240.196; 11.CI.240.223; 11.CI.240.240; 11.CI.240.244; 11.CI.240.243; 11.CI.240.247; 11.CI.244.157; 11.CI.244.158; 11.CI.244.196; 11.CI.244.223; 11.CI.244.240; 11.CI.244.244; 11.CI.244.243; 11.CI.244.247; 11.CI.247.157; 11.CI.247.158; 11.CI.247.196; 11.CI.247.223; 11.CI.247.240; 11.CI.247.244; 11.CI.247.243; 11.CI.247.247;

Prodrugs of 11.CO

11.CO.4.157; 11.CO.4.158; 11.CO.4.196; 11.CO.4.223; 11.CO.4.240; 11.CO.4.244; 11.CO.4.243; 11.CO.4.247; 11.CO.5.157; 11.CO.5.158; 11.CO.5.196; 11.CO.5.223; 11.CO.5.240; 11.CO.5.244; 11.CO.5.243; 11.CO.5.247; 11.CO.7.157; 11.CO.7.158; 11.CO.7.196; 11.CO.7.223; 11.CO.7.240; 11.CO.7.244; 11.CO.7.243; 11.CO.7.247; 11.CO.15.157; 11.CO.15.158; 11.CO.15.196; 11.CO.15.223; 11.CO.15.240; 11.CO.15.244;

TABLE 100-continued

11.CO.15.243; 11.CO.15.247; 11.CO.16.157; 11.CO.16.158; 11.CO.16.196; 11.CO.16.223; 11.CO.16.240; 11.CO.16.244; 11.CO.16.243; 11.CO.16.247; 11.CO.18.157; 11.CO.18.158; 11.CO.18.196; 11.CO.18.223; 11.CO.18.240; 11.CO.18.244; 11.CO.18.243; 11.CO.18.247; 11.CO.26.157; 11.CO.26.158; 11.CO.26.196; 11.CO.26.223; 11.CO.26.240; 11.CO.26.244; 11.CO.26.243; 11.CO.26.247; 11.CO.27.157; 11.CO.27.158; 11.CO.27.196; 11.CO.27.223; 11.CO.27.240; 11.CO.27.244; 11.CO.27.243; 11.CO.27.247; 11.CO.29.157; 11.CO.29.158; 11.CO.29.196; 11.CO.29.223; 11.CO.29.240; 11.CO.29.244; 11.CO.29.243; 11.CO.29.247; 11.CO.54.157; 11.CO.54.158; 11.CO.54.196; 11.CO.54.223; 11.CO.54.240; 11.CO.54.244; 11.CO.54.243; 11.CO.54.247; 11.CO.55.157; 11.CO.55.158; 11.CO.55.196; 11.CO.55.223; 11.CO.55.240; 11.CO.55.244; 11.CO.55.243; 11.CO.55.247; 11.CO.56.157; 11.CO.56.158; 11.CO.56.196; 11.CO.56.223; 11.CO.56.240; 11.CO.56.244; 11.CO.56.243; 11.CO.56.247; 11.CO.157.157; 11.CO.157.158; 11.CO.157.196; 11.CO.157.223; 11.CO.157.240; 11.CO.157.244; 11.CO.157.243; 11.CO.157.247; 11.CO.196.157; 11.CO.196.158; 11.CO.196.196; 11.CO.196.223; 11.CO.196.240; 11.CO.196.244; 11.CO.196.243; 11.CO.196.247; 11.CO.223.157; 11.CO.223.158; 11.CO.223.196; 11.CO.223.223; 11.CO.223.240; 11.CO.223.244; 11.CO.223.243; 11.CO.223.247; 11.CO.240.157; 11.CO.240.158; 11.CO.240.196; 11.CO.240.223; 11.CO.240.240; 11.CO.240.244; 11.CO.240.243; 11.CO.240.247; 11.CO.244.157; 11.CO.244.158; 11.CO.244.196; 11.CO.244.223; 11.CO.244.240; 11.CO.244.244; 11.CO.244.243; 11.CO.244.247; 11.CO.247.157; 11.CO.247.158; 11.CO.247.196; 11.CO.247.223; 11.CO.247.240; 11.CO.247.244; 11.CO.247.243; 11.CO.247.247;

Prodrugs of 12.AH

12.AH.4.157; 12.AH.4.158; 12.AH.4.196; 12.AH.4.223; 12.AH.4.240; 12.AH.4.244; 12.AH.4.243; 12.AH.4.247; 12.AH.5.157; 12.AH.5.158; 12.AH.5.196; 12.AH.5.223; 12.AH.5.240; 12.AH.5.244; 12.AH.5.243; 12.AH.5.247; 12.AH.7.157; 12.AH.7.158; 12.AH.7.196; 12.AH.7.223; 12.AH.7.240; 12.AH.7.244; 12.AH.7.243; 12.AH.7.247; 12.AH.15.157; 12.AH.15.158; 12.AH.15.196; 12.AH.15.223; 12.AH.15.240; 12.AH.15.244; 12.AH.15.243; 12.AH.15.247; 12.AH.16.157; 12.AH.16.158; 12.AH.16.196; 12.AH.16.223; 12.AH.16.240; 12.AH.16.244; 12.AH.16.243; 12.AH.16.247; 12.AH.18.157; 12.AH.18.158; 12.AH.18.196; 12.AH.18.223; 12.AH.18.240; 12.AH.18.244; 12.AH.18.243; 12.AH.18.247; 12.AH.26.157; 12.AH.26.158; 12.AH.26.196; 12.AH.26.223; 12.AH.26.240; 12.AH.26.244; 12.AH.26.243; 12.AH.26.247; 12.AH.27.157; 12.AH.27.158; 12.AH.27.196; 12.AH.27.223; 12.AH.27.240; 12.AH.27.244; 12.AH.27.243; 12.AH.27.247; 12.AH.29.157; 12.AH.29.158; 12.AH.29.196; 12.AH.29.223; 12.AH.29.240; 12.AH.29.244; 12.AH.29.243; 12.AH.29.247; 12.AH.54.157; 12.AH.54.158; 12.AH.54.196; 12.AH.54.223; 12.AH.54.240; 12.AH.54.244; 12.AH.54.243; 12.AH.54.247; 12.AH.55.157; 12.AH.55.158; 12.AH.55.196; 12.AH.55.223; 12.AH.55.240; 12.AH.55.244; 12.AH.55.243; 12.AH.55.247; 12.AH.56.157; 12.AH.56.158; 12.AH.56.196; 12.AH.56.223; 12.AH.56.240; 12.AH.56.244; 12.AH.56.243; 12.AH.56.247; 12.AH.157.157; 12.AH.157.158; 12.AH.157.196; 12.AH.157.223; 12.AH.157.240; 12.AH.157.244; 12.AH.157.243; 12.AH.157.247; 12.AH.196.157; 12.AH.196.158; 12.AH.196.196; 12.AH.196.223; 12.AH.196.240; 12.AH.196.244; 12.AH.196.243; 12.AH.196.247; 12.AH.223.157; 12.AH.223.158; 12.AH.223.196; 12.AH.223.223; 12.AH.223.240; 12.AH.223.244; 12.AH.223.243; 12.AH.223.247; 12.AH.240.157; 12.AH.240.158; 12.AH.240.196; 12.AH.240.223; 12.AH.240.240; 12.AH.240.244; 12.AH.240.243; 12.AH.240.247; 12.AH.244.157; 12.AH.244.158; 12.AH.244.196; 12.AH.244.223; 12.AH.244.240; 12.AH.244.244; 12.AH.244.243; 12.AH.244.247; 12.AH.247.157; 12.AH.247.158; 12.AH.247.196; 12.AH.247.223; 12.AH.247.240; 12.AH.247.244; 12.AH.247.243; 12.AH.247.247;

Prodrugs of 12.AJ

12.AJ.4.157; 12.AJ.4.158; 12.AJ.4.196; 12.AJ.4.223; 12.AJ.4.240; 12.AJ.4.244; 12.AJ.4.243; 12.AJ.4.247; 12.AJ.5.157; 12.AJ.5.158; 12.AJ.5.196; 12.AJ.5.223; 12.AJ.5.240; 12.AJ.5.244; 12.AJ.5.243; 12.AJ.5.247; 12.AJ.7.157; 12.AJ.7.158; 12.AJ.7.196; 12.AJ.7.223; 12.AJ.7.240; 12.AJ.7.244; 12.AJ.7.243; 12.AJ.7.247; 12.AJ.15.157; 12.AJ.15.158; 12.AJ.15.196; 12.AJ.15.223; 12.AJ.15.240; 12.AJ.15.244; 12.AJ.15.243; 12.AJ.15.247; 12.AJ.16.157; 12.AJ.16.158; 12.AJ.16.196; 12.AJ.16.223; 12.AJ.16.240; 12.AJ.16.244; 12.AJ.16.243; 12.AJ.16.247; 12.AJ.18.157; 12.AJ.18.158; 12.AJ.18.196; 12.AJ.18.223; 12.AJ.18.240; 12.AJ.18.244; 12.AJ.18.243; 12.AJ.18.247; 12.AJ.26.157; 12.AJ.26.158; 12.AJ.26.196; 12.AJ.26.223; 12.AJ.26.240; 12.AJ.26.244; 12.AJ.26.243; 12.AJ.26.247; 12.AJ.27.157; 12.AJ.27.158; 12.AJ.27.196; 12.AJ.27.223; 12.AJ.27.240; 12.AJ.27.244; 12.AJ.27.243; 12.AJ.27.247; 12.AJ.29.157; 12.AJ.29.158; 12.AJ.29.196; 12.AJ.29.223; 12.AJ.29.240; 12.AJ.29.244; 12.AJ.29.243; 12.AJ.29.247; 12.AJ.54.157; 12.AJ.54.158; 12.AJ.54.196; 12.AJ.54.223; 12.AJ.54.240; 12.AJ.54.244; 12.AJ.54.243; 12.AJ.54.247; 12.AJ.55.157; 12.AJ.55.158; 12.AJ.55.196; 12.AJ.55.223; 12.AJ.55.240; 12.AJ.55.244; 12.AJ.55.243; 12.AJ.55.247; 12.AJ.56.157; 12.AJ.56.158; 12.AJ.56.196; 12.AJ.56.223; 12.AJ.56.240; 12.AJ.56.244; 12.AJ.56.243; 12.AJ.56.247; 12.AJ.157.157; 12.AJ.157.158; 12.AJ.157.196; 12.AJ.157.223; 12.AJ.157.240; 12.AJ.157.244; 12.AJ.157.243; 12.AJ.157.247; 12.AJ.196.157; 12.AJ.196.158; 12.AJ.196.196; 12.AJ.196.223; 12.AJ.196.240; 12.AJ.196.244; 12.AJ.196.243; 12.AJ.196.247; 12.AJ.223.157; 12.AJ.223.158; 12.AJ.223.196; 12.AJ.223.223; 12.AJ.223.240; 12.AJ.223.244; 12.AJ.223.243; 12.AJ.223.247; 12.AJ.240.157; 12.AJ.240.158; 12.AJ.240.196; 12.AJ.240.223; 12.AJ.240.240; 12.AJ.240.244; 12.AJ.240.243; 12.AJ.240.247; 12.AJ.244.157; 12.AJ.244.158; 12.AJ.244.196; 12.AJ.244.223; 12.AJ.244.240; 12.AJ.244.244; 12.AJ.244.243; 12.AJ.244.247; 12.AJ.247.157; 12.AJ.247.158; 12.AJ.247.196; 12.AJ.247.223; 12.AJ.247.240; 12.AJ.247.244; 12.AJ.247.243; 12.AJ.247.247;

TABLE 100-continued

Prodrugs of 12.AN

12.AN.4.157; 12.AN.4.158; 12.AN.4.196; 12.AN.4.223; 12.AN.4.240; 12.AN.4.244; 12.AN.4.243; 12.AN.4.247; 12.AN.5.157; 12.AN.5.158; 12.AN.5.196; 12.AN.5.223; 12.AN.5.240; 12.AN.5.244; 12.AN.5.243; 12.AN.5.247; 12.AN.7.157; 12.AN.7.158; 12.AN.7.196; 12.AN.7.223; 12.AN.7.240; 12.AN.7.244; 12.AN.7.243; 12.AN.7.247; 12.AN.15.157; 12.AN.15.158; 12.AN.15.196; 12.AN.15.223; 12.AN.15.240; 12.AN.15.244; 12.AN.15.243; 12.AN.15.247; 12.AN.16.157; 12.AN.16.158; 12.AN.16.196; 12.AN.16.223; 12.AN.16.240; 12.AN.16.244; 12.AN.16.243; 12.AN.16.247; 12.AN.18.157; 12.AN.18.158; 12.AN.18.196; 12.AN.18.223; 12.AN.18.240; 12.AN.18.244; 12.AN.18.243; 12.AN.18.247; 12.AN.26.157; 12.AN.26.158; 12.AN.26.196; 12.AN.26.223; 12.AN.26.240; 12.AN.26.244; 12.AN.26.243; 12.AN.26.247; 12.AN.27.157; 12.AN.27.158; 12.AN.27.196; 12.AN.27.223; 12.AN.27.240; 12.AN.27.244; 12.AN.27.243; 12.AN.27.247; 12.AN.29.157; 12.AN.29.158; 12.AN.29.196; 12.AN.29.223; 12.AN.29.240; 12.AN.29.244; 12.AN.29.243; 12.AN.29.247; 12.AN.54.157; 12.AN.54.158; 12.AN.54.196; 12.AN.54.223; 12.AN.54.240; 12.AN.54.244; 12.AN.54.243; 12.AN.54.247; 12.AN.55.157; 12.AN.55.158; 12.AN.55.196; 12.AN.55.223; 12.AN.55.240; 12.AN.55.244; 12.AN.55.243; 12.AN.55.247; 12.AN.56.157; 12.AN.56.158; 12.AN.56.196; 12.AN.56.223; 12.AN.56.240; 12.AN.56.244; 12.AN.56.243; 12.AN.56.247; 12.AN.157.157; 12.AN.157.158; 12.AN.157.196; 12.AN.157.223; 12.AN.157.240; 12.AN.157.244; 12.AN.157.243; 12.AN.157.247; 12.AN.196.157; 12.AN.196.158; 12.AN.196.196; 12.AN.196.223; 12.AN.196.240; 12.AN.196.244; 12.AN.196.243; 12.AN.196.247; 12.AN.223.157; 12.AN.223.158; 12.AN.223.196; 12.AN.223.223; 12.AN.223.240; 12.AN.223.244; 12.AN.223.243; 12.AN.223.247; 12.AN.240.157; 12.AN.240.158; 12.AN.240.196; 12.AN.240.223; 12.AN.240.240; 12.AN.240.244; 12.AN.240.243; 12.AN.240.247; 12.AN.244.157; 12.AN.244.158; 12.AN.244.196; 12.AN.244.223; 12.AN.244.240; 12.AN.244.244; 12.AN.244.243; 12.AN.244.247; 12.AN.247.157; 12.AN.247.158; 12.AN.247.196; 12.AN.247.223; 12.AN.247.240; 12.AN.247.244; 12.AN.247.243; 12.AN.247.247;

Prodrugs of 12.AP

12.AP.4.157; 12.AP.4.158; 12.AP.4.196; 12.AP.4.223; 12.AP.4.240; 12.AP.4.244; 12.AP.4.243; 12.AP.4.247; 12.AP.5.157; 12.AP.5.158; 12.AP.5.196; 12.AP.5.223; 12.AP.5.240; 12.AP.5.244; 12.AP.5.243; 12.AP.5.247; 12.AP.7.157; 12.AP.7.158; 12.AP.7.196; 12.AP.7.223; 12.AP.7.240; 12.AP.7.244; 12.AP.7.243; 12.AP.7.247; 12.AP.15.157; 12.AP.15.158; 12.AP.15.196; 12.AP.15.223; 12.AP.15.240; 12.AP.15.244; 12.AP.15.243; 12.AP.15.247; 12.AP.16.157; 12.AP.16.158; 12.AP.16.196; 12.AP.16.223; 12.AP.16.240; 12.AP.16.244; 12.AP.16.243; 12.AP.16.247; 12.AP.18.157; 12.AP.18.158; 12.AP.18.196; 12.AP.18.223; 12.AP.18.240; 12.AP.18.244; 12.AP.18.243; 12.AP.18.247; 12.AP.26.157; 12.AP.26.158; 12.AP.26.196; 12.AP.26.223; 12.AP.26.240; 12.AP.26.244; 12.AP.26.243; 12.AP.26.247; 12.AP.27.157; 12.AP.27.158; 12.AP.27.196; 12.AP.27.223; 12.AP.27.240; 12.AP.27.244; 12.AP.27.243; 12.AP.27.247; 12.AP.29.157; 12.AP.29.158; 12.AP.29.196; 12.AP.29.223; 12.AP.29.240; 12.AP.29.244; 12.AP.29.243; 12.AP.29.247; 12.AP.54.157; 12.AP.54.158; 12.AP.54.196; 12.AP.54.223; 12.AP.54.240; 12.AP.54.244; 12.AP.54.243; 12.AP.54.247; 12.AP.55.157; 12.AP.55.158; 12.AP.55.196; 12.AP.55.223; 12.AP.55.240; 12.AP.55.244; 12.AP.55.243; 12.AP.55.247; 12.AP.56.157; 12.AP.56.158; 12.AP.56.196; 12.AP.56.223; 12.AP.56.240; 12.AP.56.244; 12.AP.56.243; 12.AP.56.247; 12.AP.157.157; 12.AP.157.158; 12.AP.157.196; 12.AP.157.223; 12.AP.157.240; 12.AP.157.244; 12.AP.157.243; 12.AP.157.247; 12.AP.196.157; 12.AP.196.158; 12.AP.196.196; 12.AP.196.223; 12.AP.196.240; 12.AP.196.244; 12.AP.196.243; 12.AP.196.247; 12.AP.223.157; 12.AP.223.158; 12.AP.223.196; 12.AP.223.223; 12.AP.223.240; 12.AP.223.244; 12.AP.223.243; 12.AP.223.247; 12.AP.240.157; 12.AP.240.158; 12.AP.240.196; 12.AP.240.223; 12.AP.240.240; 12.AP.240.244; 12.AP.240.243; 12.AP.240.247; 12.AP.244.157; 12.AP.244.158; 12.AP.244.196; 12.AP.244.223; 12.AP.244.240; 12.AP.244.244; 12.AP.244.243; 12.AP.244.247; 12.AP.247.157; 12.AP.247.158; 12.AP.247.196; 12.AP.247.223; 12.AP.247.240; 12.AP.247.244; 12.AP.247.243; 12.AP.247.247;

Prodrugs of 12.AZ

12.AZ.4.157; 12.AZ.4.158; 12.AZ.4.196; 12.AZ.4.223; 12.AZ.4.240; 12.AZ.4.244; 12.AZ.4.243; 12.AZ.4.247; 12.AZ.5.157; 12.AZ.5.158; 12.AZ.5.196; 12.AZ.5.223; 12.AZ.5.240; 12.AZ.5.244; 12.AZ.5.243; 12.AZ.5.247; 12.AZ.7.157; 12.AZ.7.158; 12.AZ.7.196; 12.AZ.7.223; 12.AZ.7.240; 12.AZ.7.244; 12.AZ.7.243; 12.AZ.7.247; 12.AZ.15.157; 12.AZ.15.158; 12.AZ.15.196; 12.AZ.15.223; 12.AZ.15.240; 12.AZ.15.244; 12.AZ.15.243; 12.AZ.15.247; 12.AZ.16.157; 12.AZ.16.158; 12.AZ.16.196; 12.AZ.16.223; 12.AZ.16.240; 12.AZ.16.244; 12.AZ.16.243; 12.AZ.16.247; 12.AZ.18.157; 12.AZ.18.158; 12.AZ.18.196; 12.AZ.18.223; 12.AZ.18.240; 12.AZ.18.244; 12.AZ.18.243; 12.AZ.18.247; 12.AZ.26.157; 12.AZ.26.158; 12.AZ.26.196; 12.AZ.26.223; 12.AZ.26.240; 12.AZ.26.244; 12.AZ.26.243; 12.AZ.26.247; 12.AZ.27.157; 12.AZ.27.158; 12.AZ.27.196; 12.AZ.27.223; 12.AZ.27.240; 12.AZ.27.244; 12.AZ.27.243; 12.AZ.27.247; 12.AZ.29.157; 12.AZ.29.158; 12.AZ.29.196; 12.AZ.29.223; 12.AZ.29.240; 12.AZ.29.244; 12.AZ.29.243; 12.AZ.29.247; 12.AZ.54.157; 12.AZ.54.158; 12.AZ.54.196; 12.AZ.54.223; 12.AZ.54.240; 12.AZ.54.244; 12.AZ.54.243; 12.AZ.54.247; 12.AZ.55.157; 12.AZ.55.158; 12.AZ.55.196; 12.AZ.55.223; 12.AZ.55.240; 12.AZ.55.244; 12.AZ.55.243; 12.AZ.55.247; 12.AZ.56.157; 12.AZ.56.158; 12.AZ.56.196; 12.AZ.56.223; 12.AZ.56.240; 12.AZ.56.244; 12.AZ.56.243; 12.AZ.56.247; 12.AZ.157.157; 12.AZ.157.158; 12.AZ.157.196; 12.AZ.157.223; 12.AZ.157.240; 12.AZ.157.244; 12.AZ.157.243; 12.AZ.157.247; 12.AZ.196.157; 12.AZ.196.158; 12.AZ.196.196; 12.AZ.196.223; 12.AZ.196.240; 12.AZ.196.244; 12.AZ.196.243; 12.AZ.196.247; 12.AZ.223.157; 12.AZ.223.158; 12.AZ.223.196; 12.AZ.223.223; 12.AZ.223.240; 12.AZ.223.244; 12.AZ.223.243; 12.AZ.223.247; 12.AZ.240.157;

TABLE 100-continued

12.AZ.240.158; 12.AZ.240.196; 12.AZ.240.223; 12.AZ.240.240; 12.AZ.240.244; 12.AZ.240.243; 12.AZ.240.247; 12.AZ.244.157; 12.AZ.244.158; 12.AZ.244.196; 12.AZ.244.223; 12.AZ.244.240; 12.AZ.244.244; 12.AZ.244.243; 12.AZ.244.247; 12.AZ.247.157; 12.AZ.247.158; 12.AZ.247.196; 12.AZ.247.223; 12.AZ.247.240; 12.AZ.247.244; 12.AZ.247.243; 12.AZ.247.247;

Prodrugs of 12.BF

12.BF.4.157; 12.BF.4.158; 12.BF.4.196; 12.BF.4.223; 12.BF.4.240; 12.BF.4.244; 12.BF.4.243; 12.BF.4.247; 12.BF.5.157; 12.BF.5.158; 12.BF.5.196; 12.BF.5.223; 12.BF.5.240; 12.BF.5.244; 12.BF.5.243; 12.BF.5.247; 12.BF.7.157; 12.BF.7.158; 12.BF.7.196; 12.BF.7.223; 12.BF.7.240; 12.BF.7.244; 12.BF.7.243; 12.BF.7.247; 12.BF.15.157; 12.BF.15.158; 12.BF.15.196; 12.BF.15.223; 12.BF.15.240; 12.BF.15.244; 12.BF.15.243; 12.BF.15.247; 12.BF.16.157; 12.BF.16.158; 12.BF.16.196; 12.BF.16.223; 12.BF.16.240; 12.BF.16.244; 12.BF.16.243; 12.BF.16.247; 12.BF.18.157; 12.BF.18.158; 12.BF.18.196; 12.BF.18.223; 12.BF.18.240; 12.BF.18.244; 12.BF.18.243; 12.BF.18.247; 12.BF.26.157; 12.BF.26.158; 12.BF.26.196; 12.BF.26.223; 12.BF.26.240; 12.BF.26.244; 12.BF.26.243; 12.BF.26.247; 12.BF.27.157; 12.BF.27.158; 12.BF.27.196; 12.BF.27.223; 12.BF.27.240; 12.BF.27.244; 12.BF.27.243; 12.BF.27.247; 12.BF.29.157; 12.BF.29.158; 12.BF.29.196; 12.BF.29.223; 12.BF.29.240; 12.BF.29.244; 12.BF.29.243; 12.BF.29.247; 12.BF.54.157; 12.BF.54.158; 12.BF.54.196; 12.BF.54.223; 12.BF.54.240; 12.BF.54.244; 12.BF.54.243; 12.BF.54.247; 12.BF.55.157; 12.BF.55.158; 12.BF.55.196; 12.BF.55.223; 12.BF.55.240; 12.BF.55.244; 12.BF.55.243; 12.BF.55.247; 12.BF.56.157; 12.BF.56.158; 12.BF.56.196; 12.BF.56.223; 12.BF.56.240; 12.BF.56.244; 12.BF.56.243; 12.BF.56.247; 12.BF.157.157; 12.BF.157.158; 12.BF.157.196; 12.BF.157.223; 12.BF.157.240; 12.BF.157.244; 12.BF.157.243; 12.BF.157.247; 12.BF.196.157; 12.BF.196.158; 12.BF.196.196; 12.BF.196.223; 12.BF.196.240; 12.BF.196.244; 12.BF.196.243; 12.BF.196.247; 12.BF.223.157; 12.BF.223.158; 12.BF.223.196; 12.BF.223.223; 12.BF.223.240; 12.BF.223.244; 12.BF.223.243; 12.BF.223.247; 12.BF.240.157; 12.BF.240.158; 12.BF.240.196; 12.BF.240.223; 12.BF.240.240; 12.BF.240.244; 12.BF.240.243; 12.BF.240.247; 12.BF.244.157; 12.BF.244.158; 12.BF.244.196; 12.BF.244.223; 12.BF.244.240; 12.BF.244.244; 12.BF.244.243; 12.BF.244.247; 12.BF.247.157; 12.BF.247.158; 12.BF.247.196; 12.BF.247.223; 12.BF.247.240; 12.BF.247.244; 12.BF.247.243; 12.BF.247.247;

Prodrugs of 12.CI

12.CI.4.157; 12.CI.4.158; 12.CI.4.196; 12.CI.4.223; 12.CI.4.240; 12.CI.4.244; 12.CI.4.243; 12.CI.4.247; 12.CI.5.157; 12.CI.5.158; 12.CI.5.196; 12.CI.5.223; 12.CI.5.240; 12.CI.5.244; 12.CI.5.243; 12.CI.5.247; 12.CI.7.157; 12.CI.7.158; 12.CI.7.196; 12.CI.7.223; 12.CI.7.240; 12.CI.7.244; 12.CI.7.243; 12.CI.7.247; 12.CI.15.157; 12.CI.15.158; 12.CI.15.196; 12.CI.15.223; 12.CI.15.240; 12.CI.15.244; 12.CI.15.243; 12.CI.15.247; 12.CI.16.157; 12.CI.16.158; 12.CI.16.196; 12.CI.16.223; 12.CI.16.240; 12.CI.16.244; 12.CI.16.243; 12.CI.16.247; 12.CI.18.157; 12.CI.18.158; 12.CI.18.196; 12.CI.18.223; 12.CI.18.240; 12.CI.18.244; 12.CI.18.243; 12.CI.18.247; 12.CI.26.157; 12.CI.26.158; 12.CI.26.196; 12.CI.26.223; 12.CI.26.240; 12.CI.26.244; 12.CI.26.243; 12.CI.26.247; 12.CI.27.157; 12.CI.27.158; 12.CI.27.196; 12.CI.27.223; 12.CI.27.240; 12.CI.27.244; 12.CI.27.243; 12.CI.27.247; 12.CI.29.157; 12.CI.29.158; 12.CI.29.196; 12.CI.29.223; 12.CI.29.240; 12.CI.29.244; 12.CI.29.243; 12.CI.29.247; 12.CI.54.157; 12.CI.54.158; 12.CI.54.196; 12.CI.54.223; 12.CI.54.240; 12.CI.54.244; 12.CI.54.243; 12.CI.54.247; 12.CI.55.157; 12.CI.55.158; 12.CI.55.196; 12.CI.55.223; 12.CI.55.240; 12.CI.55.244; 12.CI.55.243; 12.CI.55.247; 12.CI.56.157; 12.CI.56.158; 12.CI.56.196; 12.CI.56.223; 12.CI.56.240; 12.CI.56.244; 12.CI.56.243; 12.CI.56.247; 12.CI.157.157; 12.CI.157.158; 12.CI.157.196; 12.CI.157.223; 12.CI.157.240; 12.CI.157.244; 12.CI.157.243; 12.CI.157.247; 12.CI.196.157; 12.CI.196.158; 12.CI.196.196; 12.CI.196.223; 12.CI.196.240; 12.CI.196.244; 12.CI.196.243; 12.CI.196.247; 12.CI.223.157; 12.CI.223.158; 12.CI.223.196; 12.CI.223.223; 12.CI.223.240; 12.CI.223.244; 12.CI.223.243; 12.CI.223.247; 12.CI.240.157; 12.CI.240.158; 12.CI.240.196; 12.CI.240.223; 12.CI.240.240; 12.CI.240.244; 12.CI.240.243; 12.CI.240.247; 12.CI.244.157; 12.CI.244.158; 12.CI.244.196; 12.CI.244.223; 12.CI.244.240; 12.CI.244.244; 12.CI.244.243; 12.CI.244.247; 12.CI.247.157; 12.CI.247.158; 12.CI.247.196; 12.CI.247.223; 12.CI.247.240; 12.CI.247.244; 12.CI.247.243; 12.CI.247.247;

Prodrugs of 12.CO

12.CO.4.157; 12.CO.4.158; 12.CO.4.196; 12.CO.4.223; 12.CO.4.240; 12.CO.4.244; 12.CO.4.243; 12.CO.4.247; 12.CO.5.157; 12.CO.5.158; 12.CO.5.196; 12.CO.5.223; 12.CO.5.240; 12.CO.5.244; 12.CO.5.243; 12.CO.5.247; 12.CO.7.157; 12.CO.7.158; 12.CO.7.196; 12.CO.7.223; 12.CO.7.240; 12.CO.7.244; 12.CO.7.243; 12.CO.7.247; 12.CO.15.157; 12.CO.15.158; 12.CO.15.196; 12.CO.15.223; 12.CO.15.240; 12.CO.15.244; 12.CO.15.243; 12.CO.15.247; 12.CO.16.157; 12.CO.16.158; 12.CO.16.196; 12.CO.16.223; 12.CO.16.240; 12.CO.16.244; 12.CO.16.243; 12.CO.16.247; 12.CO.18.157; 12.CO.18.158; 12.CO.18.196; 12.CO.18.223; 12.CO.18.240; 12.CO.18.244; 12.CO.18.243; 12.CO.18.247; 12.CO.26.157; 12.CO.26.158; 12.CO.26.196; 12.CO.26.223; 12.CO.26.240; 12.CO.26.244; 12.CO.26.243; 12.CO.26.247; 12.CO.27.157; 12.CO.27.158; 12.CO.27.196; 12.CO.27.223; 12.CO.27.240; 12.CO.27.244; 12.CO.27.243; 12.CO.27.247; 12.CO.29.157; 12.CO.29.158; 12.CO.29.196; 12.CO.29.223; 12.CO.29.240; 12.CO.29.244; 12.CO.29.243; 12.CO.29.247; 12.CO.54.157; 12.CO.54.158; 12.CO.54.196; 12.CO.54.223; 12.CO.54.240; 12.CO.54.244; 12.CO.54.243; 12.CO.54.247; 12.CO.55.157; 12.CO.55.158; 12.CO.55.196; 12.CO.55.223; 12.CO.55.240; 12.CO.55.244; 12.CO.55.243; 12.CO.55.247; 12.CO.56.157; 12.CO.56.158; 12.CO.56.196; 12.CO.56.223; 12.CO.56.240; 12.CO.56.244; 12.CO.56.243; 12.CO.56.247; 12.CO.157.157; 12.CO.157.158; 12.CO.157.196; 12.CO.157.223; 12.CO.157.240; 12.CO.157.244; 12.CO.157.243; 12.CO.157.247; 12.CO.196.157; 12.CO.196.158;

TABLE 100-continued

12.CO.196.196; 12.CO.196.223; 12.CO.196.240; 12.CO.196.244; 12.CO.196.243; 12.CO.196.247; 12.CO.223.157; 12.CO.223.158; 12.CO.223.196; 12.CO.223.223; 12.CO.223.240; 12.CO.223.244; 12.CO.223.243; 12.CO.223.247; 12.CO.240.157; 12.CO.240.158; 12.CO.240.196; 12.CO.240.223; 12.CO.240.240; 12.CO.240.244; 12.CO.240.243; 12.CO.240.247; 12.CO.244.157; 12.CO.244.158; 12.CO.244.196; 12.CO.244.223; 12.CO.244.240; 12.CO.244.244; 12.CO.244.243; 12.CO.244.247; 12.CO.247.157; 12.CO.247.158; 12.CO.247.196; 12.CO.247.223; 12.CO.247.240; 12.CO.247.244; 12.CO.247.243; 12.CO.247.247.

Prodrugs of 13.B

13.B.228.228; 13.B.228.229; 13.B.228.230; 13.B.228.231; 13.B.228.236; 13.B.228.237; 13.B.228.238; 13.B.228.239; 13.B.228.154; 13.B.228.157; 13.B.228.166; 13.B.228.169; 13.B.228.172; 13.B.228.175; 13.B.228.240; 13.B.228.244; 13.B.229.228; 13.B.229.229; 13.B.229.230; 13.B.229.231; 13.B.229.236; 13.B.229.237; 13.B.229.238; 13.B.229.239; 13.B.229.154; 13.B.229.157; 13.B.229.166; 13.B.229.169; 13.B.229.172; 13.B.229.175; 13.B.229.240; 13.B.229.244; 13.B.230.228; 13.B.230.229; 13.B.230.230; 13.B.230.231; 13.B.230.236; 13.B.230.237; 13.B.230.238; 13.B.230.239; 13.B.230.154; 13.B.230.157; 13.B.230.166; 13.B.230.169; 13.B.230.172; 13.B.230.175; 13.B.230.240; 13.B.230.244; 13.B.231.228; 13.B.231.229; 13.B.231.230; 13.B.231.231; 13.B.231.236; 13.B.231.237; 13.B.231.238; 13.B.231.239; 13.B.231.154; 13.B.231.157; 13.B.231.166; 13.B.231.169; 13.B.231.172; 13.B.231.175; 13.B.231.240; 13.B.231.244; 13.B.236.228; 13.B.236.229; 13.B.236.230; 13.B.236.231; 13.B.236.236; 13.B.236.237; 13.B.236.238; 13.B.236.239; 13.B.236.154; 13.B.236.157; 13.B.236.166; 13.B.236.169; 13.B.236.172; 13.B.236.175; 13.B.236.240; 13.B.236.244; 13.B.237.228; 13.B.237.229; 13.B.237.230; 13.B.237.231; 13.B.237.236; 13.B.237.237; 13.B.237.238; 13.B.237.239; 13.B.237.154; 13.B.237.157; 13.B.237.166; 13.B.237.169; 13.B.237.172; 13.B.237.175; 13.B.237.240; 13.B.237.244; 13.B.238.228; 13.B.238.229; 13.B.238.230; 13.B.238.231; 13.B.238.236; 13.B.238.237; 13.B.238.238; 13.B.238.239; 13.B.238.154; 13.B.238.157; 13.B.238.166; 13.B.238.169; 13.B.238.172; 13.B.238.175; 13.B.238.240; 13.B.238.244; 13.B.239.228; 13.B.239.229; 13.B.239.230; 13.B.239.231; 13.B.239.236; 13.B.239.237; 13.B.239.238; 13.B.239.239; 13.B.239.154; 13.B.239.157; 13.B.239.166; 13.B.239.169; 13.B.239.172; 13.B.239.175; 13.B.239.240; 13.B.239.244; 13.B.154.228; 13.B.154.229; 13.B.154.230; 13.B.154.231; 13.B.154.236; 13.B.154.237; 13.B.154.238; 13.B.154.239; 13.B.154.154; 13.B.154.157; 13.B.154.166; 13.B.154.169; 13.B.154.172; 13.B.154.175; 13.B.154.240; 13.B.154.244; 13.B.157.228; 13.B.157.229; 13.B.157.230; 13.B.157.231; 13.B.157.236; 13.B.157.237; 13.B.157.238; 13.B.157.239; 13.B.157.154; 13.B.157.157; 13.B.157.166; 13.B.157.169; 13.B.157.172; 13.B.157.175; 13.B.157.240; 13.B.157.244; 13.B.166.228; 13.B.166.229; 13.B.166.230; 13.B.166.231; 13.B.166.236; 13.B.166.237; 13.B.166.238; 13.B.166.239; 13.B.166.154; 13.B.166.157; 13.B.166.166; 13.B.166.169; 13.B.166.172; 13.B.166.175; 13.B.166.240; 13.B.166.244; 13.B.169.228; 13.B.169.229; 13.B.169.230; 13.B.169.231; 13.B.169.236; 13.B.169.237; 13.B.169.238; 13.B.169.239; 13.B.169.154; 13.B.169.157; 13.B.169.166; 13.B.169.169; 13.B.169.172; 13.B.169.175; 13.B.169.240; 13.B.169.244; 13.B.172.228; 13.B.172.229; 13.B.172.230; 13.B.172.231; 13.B.172.236; 13.B.172.237; 13.B.172.238; 13.B.172.239; 13.B.172.154; 13.B.172.157; 13.B.172.166; 13.B.172.169; 13.B.172.172; 13.B.172.175; 13.B.172.240; 13.B.172.244; 13.B.175.228; 13.B.175.229; 13.B.175.230; 13.B.175.231; 13.B.175.236; 13.B.175.237; 13.B.175.238; 13.B.175.239; 13.B.175.154; 13.B.175.157; 13.B.175.166; 13.B.175.169; 13.B.175.172; 13.B.175.175; 13.B.175.240; 13.B.175.244; 13.B.240.228; 13.B.240.229; 13.B.240.230; 13.B.240.231; 13.B.240.236; 13.B.240.237; 13.B.240.238; 13.B.240.239; 13.B.240.154; 13.B.240.157; 13.B.240.166; 13.B.240.169; 13.B.240.172; 13.B.240.175; 13.B.240.240; 13.B.240.244; 13.B.244.228; 13.B.244.229; 13.B.244.230; 13.B.244.231; 13.B.244.236; 13.B.244.237; 13.B.244.238; 13.B.244.239; 13.B.244.154; 13.B.244.157; 13.B.244.166; 13.B.244.169; 13.B.244.172; 13.B.244.175; 13.B.244.240; 13.B.244.244;

Prodrugs of 13.D

13.D.228.228; 13.D.228.229; 13.D.228.230; 13.D.228.231; 13.D.228.236; 13.D.228.237; 13.D.228.238; 13.D.228.239; 13.D.228.154; 13.D.228.157; 13.D.228.166; 13.D.228.169; 13.D.228.172; 13.D.228.175; 13.D.228.240; 13.D.228.244; 13.D.229.228; 13.D.229.229; 13.D.229.230; 13.D.229.231; 13.D.229.236; 13.D.229.237; 13.D.229.238; 13.D.229.239; 13.D.229.154; 13.D.229.157; 13.D.229.166; 13.D.229.169; 13.D.229.172; 13.D.229.175; 13.D.229.240; 13.D.229.244; 13.D.230.228; 13.D.230.229; 13.D.230.230; 13.D.230.231; 13.D.230.236; 13.D.230.237; 13.D.230.238; 13.D.230.239; 13.D.230.154; 13.D.230.157; 13.D.230.166; 13.D.230.169; 13.D.230.172; 13.D.230.175; 13.D.230.240; 13.D.230.244; 13.D.231.228; 13.D.231.229; 13.D.231.230; 13.D.231.231; 13.D.231.236; 13.D.231.237; 13.D.231.238; 13.D.231.239; 13.D.231.154; 13.D.231.157; 13.D.231.166; 13.D.231.169; 13.D.231.172; 13.D.231.175; 13.D.231.240; 13.D.231.244; 13.D.236.228; 13.D.236.229; 13.D.236.230; 13.D.236.231; 13.D.236.236; 13.D.236.237; 13.D.236.238; 13.D.236.239; 13.D.236.154; 13.D.236.157; 13.D.236.166; 13.D.236.169; 13.D.236.172; 13.D.236.175; 13.D.236.240; 13.D.236.244; 13.D.237.228; 13.D.237.229; 13.D.237.230; 13.D.237.231; 13.D.237.236; 13.D.237.237; 13.D.237.238; 13.D.237.239; 13.D.237.154; 13.D.237.157; 13.D.237.166; 13.D.237.169; 13.D.237.172; 13.D.237.175; 13.D.237.240; 13.D.237.244; 13.D.238.228; 13.D.238.229; 13.D.238.230; 13.D.238.231; 13.D.238.236; 13.D.238.237; 13.D.238.238; 13.D.238.239; 13.D.238.154; 13.D.238.157; 13.D.238.166; 13.D.238.169; 13.D.238.172; 13.D.238.175; 13.D.238.240; 13.D.238.244; 13.D.239.228; 13.D.239.229; 13.D.239.230; 13.D.239.231; 13.D.239.236; 13.D.239.237; 13.D.239.238; 13.D.239.239; 13.D.239.154; 13.D.239.157; 13.D.239.166; 13.D.239.169; 13.D.239.172; 13.D.239.175; 13.D.239.240; 13.D.239.244; 13.D.154.228; 13.D.154.229; 13.D.154.230; 13.D.154.231; 13.D.154.236; 13.D.154.237; 13.D.154.238; 13.D.154.239; 13.D.154.154; 13.D.154.157; 13.D.154.166; 13.D.154.169; 13.D.154.172; 13.D.154.175; 13.D.154.240; 13.D.154.244;

TABLE 100-continued

13.D.157.228; 13.D.157.229; 13.D.157.230; 13.D.157.231; 13.D.157.236; 13.D.157.237;
13.D.157.238; 13.D.157.239; 13.D.157.154; 13.D.157.157; 13.D.157.166; 13.D.157.169;
13.D.157.172; 13.D.157.175; 13.D.157.240; 13.D.157.244; 13.D.166.228; 13.D.166.229;
13.D.166.230; 13.D.166.231; 13.D.166.236; 13.D.166.237; 13.D.166.238; 13.D.166.239;
13.D.166.154; 13.D.166.157; 13.D.166.166; 13.D.166.169; 13.D.166.172; 13.D.166.175;
13.D.166.240; 13.D.166.244; 13.D.169.228; 13.D.169.229; 13.D.169.230; 13.D.169.231;
13.D.169.236; 13.D.169.237; 13.D.169.238; 13.D.169.239; 13.D.169.154; 13.D.169.157;
13.D.169.166; 13.D.169.169; 13.D.169.172; 13.D.169.175; 13.D.169.240; 13.D.169.244;
13.D.172.228; 13.D.172.229; 13.D.172.230; 13.D.172.231; 13.D.172.236; 13.D.172.237;
13.D.172.238; 13.D.172.239; 13.D.172.154; 13.D.172.157; 13.D.172.166; 13.D.172.169;
13.D.172.172; 13.D.172.175; 13.D.172.240; 13.D.172.244; 13.D.175.228; 13.D.175.229;
13.D.175.230; 13.D.175.231; 13.D.175.236; 13.D.175.237; 13.D.175.238; 13.D.175.239;
13.D.175.154; 13.D.175.157; 13.D.175.166; 13.D.175.169; 13.D.175.172; 13.D.175.175;
13.D.175.240; 13.D.175.244; 13.D.240.228; 13.D.240.229; 13.D.240.230; 13.D.240.231;
13.D.240.236; 13.D.240.237; 13.D.240.238; 13.D.240.239; 13.D.240.154; 13.D.240.157;
13.D.240.166; 13.D.240.169; 13.D.240.172; 13.D.240.175; 13.D.240.240; 13.D.240.244;
13.D.244.228; 13.D.244.229; 13.D.244.230; 13.D.244.231; 13.D.244.236; 13.D.244.237;
13.D.244.238; 13.D.244.239; 13.D.244.154; 13.D.244.157; 13.D.244.166; 13.D.244.169;
13.D.244.172; 13.D.244.175; 13.D.244.240; 13.D.244.244;

Prodrugs of 13.E

13.E.228.228; 13.E.228.229; 13.E.228.230; 13.E.228.231; 13.E.228.236; 13.E.228.237;
13.E.228.238; 13.E.228.239; 13.E.228.154; 13.E.228.157; 13.E.228.166; 13.E.228.169;
13.E.228.172; 13.E.228.175; 13.E.228.240; 13.E.228.244; 13.E.229.228; 13.E.229.229;
13.E.229.230; 13.E.229.231; 13.E.229.236; 13.E.229.237; 13.E.229.238; 13.E.229.239;
13.E.229.154; 13.E.229.157; 13.E.229.166; 13.E.229.169; 13.E.229.172; 13.E.229.175;
13.E.229.240; 13.E.229.244; 13.E.230.228; 13.E.230.229; 13.E.230.230; 13.E.230.231;
13.E.230.236; 13.E.230.237; 13.E.230.238; 13.E.230.239; 13.E.230.154; 13.E.230.157;
13.E.230.166; 13.E.230.169; 13.E.230.172; 13.E.230.175; 13.E.230.240; 13.E.230.244;
13.E.231.228; 13.E.231.229; 13.E.231.230; 13.E.231.231; 13.E.231.236; 13.E.231.237;
13.E.231.238; 13.E.231.239; 13.E.231.154; 13.E.231.157; 13.E.231.166; 13.E.231.169;
13.E.231.172; 13.E.231.175; 13.E.231.240; 13.E.231.244; 13.E.236.228; 13.E.236.229;
13.E.236.230; 13.E.236.231; 13.E.236.236; 13.E.236.237; 13.E.236.238; 13.E.236.239;
13.E.236.154; 13.E.236.157; 13.E.236.166; 13.E.236.169; 13.E.236.172; 13.E.236.175;
13.E.236.240; 13.E.236.244; 13.E.237.228; 13.E.237.229; 13.E.237.230; 13.E.237.231;
13.E.237.236; 13.E.237.237; 13.E.237.238; 13.E.237.239; 13.E.237.154; 13.E.237.157;
13.E.237.166; 13.E.237.169; 13.E.237.172; 13.E.237.175; 13.E.237.240; 13.E.237.244;
13.E.238.228; 13.E.238.229; 13.E.238.230; 13.E.238.231; 13.E.238.236; 13.E.238.237;
13.E.238.238; 13.E.238.239; 13.E.238.154; 13.E.238.157; 13.E.238.166; 13.E.238.169;
13.E.238.172; 13.E.238.175; 13.E.238.240; 13.E.238.244; 13.E.239.228; 13.E.239.229;
13.E.239.230; 13.E.239.231; 13.E.239.236; 13.E.239.237; 13.E.239.238; 13.E.239.239;
13.E.239.154; 13.E.239.157; 13.E.239.166; 13.E.239.169; 13.E.239.172; 13.E.239.175;
13.E.239.240; 13.E.239.244; 13.E.154.228; 13.E.154.229; 13.E.154.230; 13.E.154.231;
13.E.154.236; 13.E.154.237; 13.E.154.238; 13.E.154.239; 13.E.154.154; 13.E.154.157;
13.E.154.166; 13.E.154.169; 13.E.154.172; 13.E.154.175; 13.E.154.240; 13.E.154.244;
13.E.157.228; 13.E.157.229; 13.E.157.230; 13.E.157.231; 13.E.157.236; 13.E.157.237;
13.E.157.238; 13.E.157.239; 13.E.157.154; 13.E.157.157; 13.E.157.166; 13.E.157.169;
13.E.157.172; 13.E.157.175; 13.E.157.240; 13.E.157.244; 13.E.166.228; 13.E.166.229;
13.E.166.230; 13.E.166.231; 13.E.166.236; 13.E.166.237; 13.E.166.238; 13.E.166.239;
13.E.166.154; 13.E.166.157; 13.E.166.166; 13.E.166.169; 13.E.166.172; 13.E.166.175;
13.E.166.240; 13.E.166.244; 13.E.169.228; 13.E.169.229; 13.E.169.230; 13.E.169.231;
13.E.169.236; 13.E.169.237; 13.E.169.238; 13.E.169.239; 13.E.169.154; 13.E.169.157;
13.E.169.166; 13.E.169.169; 13.E.169.172; 13.E.169.175; 13.E.169.240; 13.E.169.244;
13.E.172.228; 13.E.172.229; 13.E.172.230; 13.E.172.231; 13.E.172.236; 13.E.172.237;
13.E.172.238; 13.E.172.239; 13.E.172.154; 13.E.172.157; 13.E.172.166; 13.E.172.169;
13.E.172.172; 13.E.172.175; 13.E.172.240; 13.E.172.244; 13.E.175.228; 13.E.175.229;
13.E.175.230; 13.E.175.231; 13.E.175.236; 13.E.175.237; 13.E.175.238; 13.E.175.239;
13.E.175.154; 13.E.175.157; 13.E.175.166; 13.E.175.169; 13.E.175.172; 13.E.175.175;
13.E.175.240; 13.E.175.244; 13.E.240.228; 13.E.240.229; 13.E.240.230; 13.E.240.231;
13.E.240.236; 13.E.240.237; 13.E.240.238; 13.E.240.239; 13.E.240.154; 13.E.240.157;
13.E.240.166; 13.E.240.169; 13.E.240.172; 13.E.240.175; 13.E.240.240; 13.E.240.244;
13.E.244.228; 13.E.244.229; 13.E.244.230; 13.E.244.231; 13.E.244.236; 13.E.244.237;
13.E.244.238; 13.E.244.239; 13.E.244.154; 13.E.244.157; 13.E.244.166; 13.E.244.169;
13.E.244.172; 13.E.244.175; 13.E.244.240; 13.E.244.244;

Prodrugs of 13.G

13.G.228.228; 13.G.228.229; 13.G.228.230; 13.G.228.231; 13.G.228.236; 13.G.228.237;
13.G.228.238; 13.G.228.239; 13.G.228.154; 13.G.228.157; 13.G.228.166; 13.G.228.169;
13.G.228.172; 13.G.228.175; 13.G.228.240; 13.G.228.244; 13.G.229.228; 13.G.229.229;
13.G.229.230; 13.G.229.231; 13.G.229.236; 13.G.229.237; 13.G.229.238; 13.G.229.239;
13.G.229.154; 13.G.229.157; 13.G.229.166; 13.G.229.169; 13.G.229.172; 13.G.229.175;
13.G.229.240; 13.G.229.244; 13.G.230.228; 13.G.230.229; 13.G.230.230; 13.G.230.231;
13.G.230.236; 13.G.230.237; 13.G.230.238; 13.G.230.239; 13.G.230.154; 13.G.230.157;
13.G.230.166; 13.G.230.169; 13.G.230.172; 13.G.230.175; 13.G.230.240; 13.G.230.244;
13.G.231.228; 13.G.231.229; 13.G.231.230; 13.G.231.231; 13.G.231.236; 13.G.231.237;
13.G.231.238; 13.G.231.239; 13.G.231.154; 13.G.231.157; 13.G.231.166; 13.G.231.169;
13.G.231.172; 13.G.231.175; 13.G.231.240; 13.G.231.244; 13.G.236.228; 13.G.236.229;
13.G.236.230; 13.G.236.231; 13.G.236.236; 13.G.236.237; 13.G.236.238; 13.G.236.239;
13.G.236.154; 13.G.236.157; 13.G.236.166; 13.G.236.169; 13.G.236.172; 13.G.236.175;

TABLE 100-continued

13.G.236.240; 13.G.236.244; 13.G.237.228; 13.G.237.229; 13.G.237.230; 13.G.237.231;
13.G.237.236; 13.G.237.237; 13.G.237.238; 13.G.237.239; 13.G.237.154; 13.G.237.157;
13.G.237.166; 13.G.237.169; 13.G.237.172; 13.G.237.175; 13.G.237.240; 13.G.237.244;
13.G.238.228; 13.G.238.229; 13.G.238.230; 13.G.238.231; 13.G.238.236; 13.G.238.237;
13.G.238.238; 13.G.238.239; 13.G.238.154; 13.G.238.157; 13.G.238.166; 13.G.238.169;
13.G.238.172; 13.G.238.175; 13.G.238.240; 13.G.238.244; 13.G.239.228; 13.G.239.229;
13.G.239.230; 13.G.239.231; 13.G.239.236; 13.G.239.237; 13.G.239.238; 13.G.239.239;
13.G.239.154; 13.G.239.157; 13.G.239.166; 13.G.239.169; 13.G.239.172; 13.G.239.175;
13.G.239.240; 13.G.239.244; 13.G.154.228; 13.G.154.229; 13.G.154.230; 13.G.154.231;
13.G.154.236; 13.G.154.237; 13.G.154.238; 13.G.154.239; 13.G.154.154; 13.G.154.157;
13.G.154.166; 13.G.154.169; 13.G.154.172; 13.G.154.175; 13.G.154.240; 13.G.154.244;
13.G.157.228; 13.G.157.229; 13.G.157.230; 13.G.157.231; 13.G.157.236; 13.G.157.237;
13.G.157.238; 13.G.157.239; 13.G.157.154; 13.G.157.157; 13.G.157.166; 13.G.157.169;
13.G.157.172; 13.G.157.175; 13.G.157.240; 13.G.157.244; 13.G.166.228; 13.G.166.229;
13.G.166.230; 13.G.166.231; 13.G.166.236; 13.G.166.237; 13.G.166.238; 13.G.166.239;
13.G.166.154; 13.G.166.157; 13.G.166.166; 13.G.166.169; 13.G.166.172; 13.G.166.175;
13.G.166.240; 13.G.166.244; 13.G.169.228; 13.G.169.229; 13.G.169.230; 13.G.169.231;
13.G.169.236; 13.G.169.237; 13.G.169.238; 13.G.169.239; 13.G.169.154; 13.G.169.157;
13.G.169.166; 13.G.169.169; 13.G.169.172; 13.G.169.175; 13.G.169.240; 13.G.169.244;
13.G.172.228; 13.G.172.229; 13.G.172.230; 13.G.172.231; 13.G.172.236; 13.G.172.237;
13.G.172.238; 13.G.172.239; 13.G.172.154; 13.G.172.157; 13.G.172.166; 13.G.172.169;
13.G.172.172; 13.G.172.175; 13.G.172.240; 13.G.172.244; 13.G.175.228; 13.G.175.229;
13.G.175.230; 13.G.175.231; 13.G.175.236; 13.G.175.237; 13.G.175.238; 13.G.175.239;
13.G.175.154; 13.G.175.157; 13.G.175.166; 13.G.175.169; 13.G.175.172; 13.G.175.175;
13.G.175.240; 13.G.175.244; 13.G.240.228; 13.G.240.229; 13.G.240.230; 13.G.240.231;
13.G.240.236; 13.G.240.237; 13.G.240.238; 13.G.240.239; 13.G.240.154; 13.G.240.157;
13.G.240.166; 13.G.240.169; 13.G.240.172; 13.G.240.175; 13.G.240.240; 13.G.240.244;
13.G.244.228; 13.G.244.229; 13.G.244.230; 13.G.244.231; 13.G.244.236; 13.G.244.237;
13.G.244.238; 13.G.244.239; 13.G.244.154; 13.G.244.157; 13.G.244.166; 13.G.244.169;
13.G.244.172; 13.G.244.175; 13.G.244.240; 13.G.244.244;

Prodrugs of 13.I

13.I.228.228; 13.I.228.229; 13.I.228.230; 13.I.228.231; 13.I.228.236; 13.I.228.237;
13.I.228.238; 13.I.228.239; 13.I.228.154; 13.I.228.157; 13.I.228.166; 13.I.228.169;
13.I.228.172; 13.I.228.175; 13.I.228.240; 13.I.228.244; 13.I.229.228; 13.I.229.229;
13.I.229.230; 13.I.229.231; 13.I.229.236; 13.I.229.237; 13.I.229.238; 13.I.229.239;
13.I.229.154; 13.I.229.157; 13.I.229.166; 13.I.229.169; 13.I.229.172; 13.I.229.175;
13.I.229.240; 13.I.229.244; 13.I.230.228; 13.I.230.229; 13.I.230.230; 13.I.230.231;
13.I.230.236; 13.I.230.237; 13.I.230.238; 13.I.230.239; 13.I.230.154; 13.I.230.157;
13.I.230.166; 13.I.230.169; 13.I.230.172; 13.I.230.175; 13.I.230.240; 13.I.230.244;
13.I.231.228; 13.I.231.229; 13.I.231.230; 13.I.231.231; 13.I.231.236; 13.I.231.237;
13.I.231.238; 13.I.231.239; 13.I.231.154; 13.I.231.157; 13.I.231.166; 13.I.231.169;
13.I.231.172; 13.I.231.175; 13.I.231.240; 13.I.231.244; 13.I.236.228; 13.I.236.229;
13.I.236.230; 13.I.236.231; 13.I.236.236; 13.I.236.237; 13.I.236.238; 13.I.236.239;
13.I.236.154; 13.I.236.157; 13.I.236.166; 13.I.236.169; 13.I.236.172; 13.I.236.175;
13.I.236.240; 13.I.236.244; 13.I.237.228; 13.I.237.229; 13.I.237.230; 13.I.237.231;
13.I.237.236; 13.I.237.237; 13.I.237.238; 13.I.237.239; 13.I.237.154; 13.I.237.157;
13.I.237.166; 13.I.237.169; 13.I.237.172; 13.I.237.175; 13.I.237.240; 13.I.237.244;
13.I.238.228; 13.I.238.229; 13.I.238.230; 13.I.238.231; 13.I.238.236; 13.I.238.237;
13.I.238.238; 13.I.238.239; 13.I.238.154; 13.I.238.157; 13.I.238.166; 13.I.238.169;
13.I.238.172; 13.I.238.175; 13.I.238.240; 13.I.238.244; 13.I.239.228; 13.I.239.229;
13.I.239.230; 13.I.239.231; 13.I.239.236; 13.I.239.237; 13.I.239.238; 13.I.239.239;
13.I.239.154; 13.I.239.157; 13.I.239.166; 13.I.239.169; 13.I.239.172; 13.I.239.175;
13.I.239.240; 13.I.239.244; 13.I.154.228; 13.I.154.229; 13.I.154.230; 13.I.154.231;
13.I.154.236; 13.I.154.237; 13.I.154.238; 13.I.154.239; 13.I.154.154; 13.I.154.157;
13.I.154.166; 13.I.154.169; 13.I.154.172; 13.I.154.175; 13.I.154.240; 13.I.154.244;
13.I.157.228; 13.I.157.229; 13.I.157.230; 13.I.157.231; 13.I.157.236; 13.I.157.237;
13.I.157.238; 13.I.157.239; 13.I.157.154; 13.I.157.157; 13.I.157.166; 13.I.157.169;
13.I.157.172; 13.I.157.175; 13.I.157.240; 13.I.157.244; 13.I.166.228; 13.I.166.229;
13.I.166.230; 13.I.166.231; 13.I.166.236; 13.I.166.237; 13.I.166.238; 13.I.166.239;
13.I.166.154; 13.I.166.157; 13.I.166.166; 13.I.166.169; 13.I.166.172; 13.I.166.175;
13.I.166.240; 13.I.166.244; 13.I.169.228; 13.I.169.229; 13.I.169.230; 13.I.169.231;
13.I.169.236; 13.I.169.237; 13.I.169.238; 13.I.169.239; 13.I.169.154; 13.I.169.157;
13.I.169.166; 13.I.169.169; 13.I.169.172; 13.I.169.175; 13.I.169.240; 13.I.169.244;
13.I.172.228; 13.I.172.229; 13.I.172.230; 13.I.172.231; 13.I.172.236; 13.I.172.237;
13.I.172.238; 13.I.172.239; 13.I.172.154; 13.I.172.157; 13.I.172.166; 13.I.172.169;
13.I.172.172; 13.I.172.175; 13.I.172.240; 13.I.172.244; 13.I.175.228; 13.I.175.229;
13.I.175.230; 13.I.175.231; 13.I.175.236; 13.I.175.237; 13.I.175.238; 13.I.175.239;
13.I.175.154; 13.I.175.157; 13.I.175.166; 13.I.175.169; 13.I.175.172; 13.I.175.175;
13.I.175.240; 13.I.175.244; 13.I.240.228; 13.I.240.229; 13.I.240.230; 13.I.240.231;
13.I.240.236; 13.I.240.237; 13.I.240.238; 13.I.240.239; 13.I.240.154; 13.I.240.157;
13.I.240.166; 13.I.240.169; 13.I.240.172; 13.I.240.175; 13.I.240.240; 13.I.240.244;
13.I.244.228; 13.I.244.229; 13.I.244.230; 13.I.244.231; 13.I.244.236; 13.I.244.237;
13.I.244.238; 13.I.244.239; 13.I.244.154; 13.I.244.157; 13.I.244.166; 13.I.244.169;
13.I.244.172; 13.I.244.175; 13.I.244.240; 13.I.244.244;

Prodrugs of 13.J

13.J.228.228; 13.J.228.229; 13.J.228.230; 13.J.228.231; 13.J.228.236; 13.J.228.237;
13.J.228.238; 13.J.228.239; 13.J.228.154; 13.J.228.157; 13.J.228.166; 13.J.228.169;

TABLE 100-continued

13.J.228.172; 13.J.228.175; 13.J.228.240; 13.J.228.244; 13.J.229.228; 13.J.229.229;
13.J.229.230; 13.J.229.231; 13.J.229.236; 13.J.229.237; 13.J.229.238; 13.J.229.239;
13.J.229.154; 13.J.229.157; 13.J.229.166; 13.J.229.169; 13.J.229.172; 13.J.229.175;
13.J.229.240; 13.J.229.244; 13.J.230.228; 13.J.230.229; 13.J.230.230; 13.J.230.231;
13.J.230.236; 13.J.230.237; 13.J.230.238; 13.J.230.239; 13.J.230.154; 13.J.230.157;
13.J.230.166; 13.J.230.169; 13.J.230.172; 13.J.230.175; 13.J.230.240; 13.J.230.244;
13.J.231.228; 13.J.231.229; 13.J.231.230; 13.J.231.231; 13.J.231.236; 13.J.231.237;
13.J.231.238; 13.J.231.239; 13.J.231.154; 13.J.231.157; 13.J.231.166; 13.J.231.169;
13.J.231.172; 13.J.231.175; 13.J.231.240; 13.J.231.244; 13.J.236.228; 13.J.236.229;
13.J.236.230; 13.J.236.231; 13.J.236.236; 13.J.236.237; 13.J.236.238; 13.J.236.239;
13.J.236.154; 13.J.236.157; 13.J.236.166; 13.J.236.169; 13.J.236.172; 13.J.236.175;
13.J.236.240; 13.J.236.244; 13.J.237.228; 13.J.237.229; 13.J.237.230; 13.J.237.231;
13.J.237.236; 13.J.237.237; 13.J.237.238; 13.J.237.239; 13.J.237.154; 13.J.237.157;
13.J.237.166; 13.J.237.169; 13.J.237.172; 13.J.237.175; 13.J.237.240; 13.J.237.244;
13.J.238.228; 13.J.238.229; 13.J.238.230; 13.J.238.231; 13.J.238.236; 13.J.238.237;
13.J.238.238; 13.J.238.239; 13.J.238.154; 13.J.238.157; 13.J.238.166; 13.J.238.169;
13.J.238.172; 13.J.238.175; 13.J.238.240; 13.J.238.244; 13.J.239.228; 13.J.239.229;
13.J.239.230; 13.J.239.231; 13.J.239.236; 13.J.239.237; 13.J.239.238; 13.J.239.239;
13.J.239.154; 13.J.239.157; 13.J.239.166; 13.J.239.169; 13.J.239.172; 13.J.239.175;
13.J.239.240; 13.J.239.244; 13.J.154.228; 13.J.154.229; 13.J.154.230; 13.J.154.231;
13.J.154.236; 13.J.154.237; 13.J.154.238; 13.J.154.239; 13.J.154.154; 13.J.154.157;
13.J.154.166; 13.J.154.169; 13.J.154.172; 13.J.154.175; 13.J.154.240; 13.J.154.244;
13.J.157.228; 13.J.157.229; 13.J.157.230; 13.J.157.231; 13.J.157.236; 13.J.157.237;
13.J.157.238; 13.J.157.239; 13.J.157.154; 13.J.157.157; 13.J.157.166; 13.J.157.169;
13.J.157.172; 13.J.157.175; 13.J.157.240; 13.J.157.244; 13.J.166.228; 13.J.166.229;
13.J.166.230; 13.J.166.231; 13.J.166.236; 13.J.166.237; 13.J.166.238; 13.J.166.239;
13.J.166.154; 13.J.166.157; 13.J.166.166; 13.J.166.169; 13.J.166.172; 13.J.166.175;
13.J.166.240; 13.J.166.244; 13.J.169.228; 13.J.169.229; 13.J.169.230; 13.J.169.231;
13.J.169.236; 13.J.169.237; 13.J.169.238; 13.J.169.239; 13.J.169.154; 13.J.169.157;
13.J.169.166; 13.J.169.169; 13.J.169.172; 13.J.169.175; 13.J.169.240; 13.J.169.244;
13.J.172.228; 13.J.172.229; 13.J.172.230; 13.J.172.231; 13.J.172.236; 13.J.172.237;
13.J.172.238; 13.J.172.239; 13.J.172.154; 13.J.172.157; 13.J.172.166; 13.J.172.169;
13.J.172.172; 13.J.172.175; 13.J.172.240; 13.J.172.244; 13.J.175.228; 13.J.175.229;
13.J.175.230; 13.J.175.231; 13.J.175.236; 13.J.175.237; 13.J.175.238; 13.J.175.239;
13.J.175.154; 13.J.175.157; 13.J.175.166; 13.J.175.169; 13.J.175.172; 13.J.175.175;
13.J.175.240; 13.J.175.244; 13.J.240.228; 13.J.240.229; 13.J.240.230; 13.J.240.231;
13.J.240.236; 13.J.240.237; 13.J.240.238; 13.J.240.239; 13.J.240.154; 13.J.240.157;
13.J.240.166; 13.J.240.169; 13.J.240.172; 13.J.240.175; 13.J.240.240; 13.J.240.244;
13.J.244.228; 13.J.244.229; 13.J.244.230; 13.J.244.231; 13.J.244.236; 13.J.244.237;
13.J.244.238; 13.J.244.239; 13.J.244.154; 13.J.244.157; 13.J.244.166; 13.J.244.169;
13.J.244.172; 13.J.244.175; 13.J.244.240; 13.J.244.244;

Prodrugs of 13.L

13.L.228.228; 13.L.228.229; 13.L.228.230; 13.L.228.231; 13.L.228.236; 13.L.228.237;
13.L.228.238; 13.L.228.239; 13.L.228.154; 13.L.228.157; 13.L.228.166; 13.L.228.169;
13.L.228.172; 13.L.228.175; 13.L.228.240; 13.L.228.244; 13.L.229.228; 13.L.229.229;
13.L.229.230; 13.L.229.231; 13.L.229.236; 13.L.229.237; 13.L.229.238; 13.L.229.239;
13.L.229.154; 13.L.229.157; 13.L.229.166; 13.L.229.169; 13.L.229.172; 13.L.229.175;
13.L.229.240; 13.L.229.244; 13.L.230.228; 13.L.230.229; 13.L.230.230; 13.L.230.231;
13.L.230.236; 13.L.230.237; 13.L.230.238; 13.L.230.239; 13.L.230.154; 13.L.230.157;
13.L.230.166; 13.L.230.169; 13.L.230.172; 13.L.230.175; 13.L.230.240; 13.L.230.244;
13.L.231.228; 13.L.231.229; 13.L.231.230; 13.L.231.231; 13.L.231.236; 13.L.231.237;
13.L.231.238; 13.L.231.239; 13.L.231.154; 13.L.231.157; 13.L.231.166; 13.L.231.169;
13.L.231.172; 13.L.231.175; 13.L.231.240; 13.L.231.244; 13.L.236.228; 13.L.236.229;
13.L.236.230; 13.L.236.231; 13.L.236.236; 13.L.236.237; 13.L.236.238; 13.L.236.239;
13.L.236.154; 13.L.236.157; 13.L.236.166; 13.L.236.169; 13.L.236.172; 13.L.236.175;
13.L.236.240; 13.L.236.244; 13.L.237.228; 13.L.237.229; 13.L.237.230; 13.L.237.231;
13.L.237.236; 13.L.237.237; 13.L.237.238; 13.L.237.239; 13.L.237.154; 13.L.237.157;
13.L.237.166; 13.L.237.169; 13.L.237.172; 13.L.237.175; 13.L.237.240; 13.L.237.244;
13.L.238.228; 13.L.238.229; 13.L.238.230; 13.L.238.231; 13.L.238.236; 13.L.238.237;
13.L.238.238; 13.L.238.239; 13.L.238.154; 13.L.238.157; 13.L.238.166; 13.L.238.169;
13.L.238.172; 13.L.238.175; 13.L.238.240; 13.L.238.244; 13.L.239.228; 13.L.239.229;
13.L.239.230; 13.L.239.231; 13.L.239.236; 13.L.239.237; 13.L.239.238; 13.L.239.239;
13.L.239.154; 13.L.239.157; 13.L.239.166; 13.L.239.169; 13.L.239.172; 13.L.239.175;
13.L.239.240; 13.L.239.244; 13.L.154.228; 13.L.154.229; 13.L.154.230; 13.L.154.231;
13.L.154.236; 13.L.154.237; 13.L.154.238; 13.L.154.239; 13.L.154.154; 13.L.154.157;
13.L.154.166; 13.L.154.169; 13.L.154.172; 13.L.154.175; 13.L.154.240; 13.L.154.244;
13.L.157.228; 13.L.157.229; 13.L.157.230; 13.L.157.231; 13.L.157.236; 13.L.157.237;
13.L.157.238; 13.L.157.239; 13.L.157.154; 13.L.157.157; 13.L.157.166; 13.L.157.169;
13.L.157.172; 13.L.157.175; 13.L.157.240; 13.L.157.244; 13.L.166.228; 13.L.166.229;
13.L.166.230; 13.L.166.231; 13.L.166.236; 13.L.166.237; 13.L.166.238; 13.L.166.239;
13.L.166.154; 13.L.166.157; 13.L.166.166; 13.L.166.169; 13.L.166.172; 13.L.166.175;
13.L.166.240; 13.L.166.244; 13.L.169.228; 13.L.169.229; 13.L.169.230; 13.L.169.231;
13.L.169.236; 13.L.169.237; 13.L.169.238; 13.L.169.239; 13.L.169.154; 13.L.169.157;
13.L.169.166; 13.L.169.169; 13.L.169.172; 13.L.169.175; 13.L.169.240; 13.L.169.244;
13.L.172.228; 13.L.172.229; 13.L.172.230; 13.L.172.231; 13.L.172.236; 13.L.172.237;
13.L.172.238; 13.L.172.239; 13.L.172.154; 13.L.172.157; 13.L.172.166; 13.L.172.169;
13.L.172.172; 13.L.172.175; 13.L.172.240; 13.L.172.244; 13.L.175.228; 13.L.175.229;
13.L.175.230; 13.L.175.231; 13.L.175.236; 13.L.175.237; 13.L.175.238; 13.L.175.239;

TABLE 100-continued

13.L.175.154; 13.L.175.157; 13.L.175.166; 13.L.175.169; 13.L.175.172; 13.L.175.175; 13.L.175.240; 13.L.175.244; 13.L.240.228; 13.L.240.229; 13.L.240.230; 13.L.240.231; 13.L.240.236; 13.L.240.237; 13.L.240.238; 13.L.240.239; 13.L.240.154; 13.L.240.157; 13.L.240.166; 13.L.240.169; 13.L.240.172; 13.L.240.175; 13.L.240.240; 13.L.240.244; 13.L.244.228; 13.L.244.229; 13.L.244.230; 13.L.244.231; 13.L.244.236; 13.L.244.237; 13.L.244.238; 13.L.244.239; 13.L.244.154; 13.L.244.157; 13.L.244.166; 13.L.244.169; 13.L.244.172; 13.L.244.175; 13.L.244.240; 13.L.244.244;

Prodrugs of 13.O

13.O.228.228; 13.O.228.229; 13.O.228.230; 13.O.228.231; 13.O.228.236; 13.O.228.237; 13.O.228.238; 13.O.228.239; 13.O.228.154; 13.O.228.157; 13.O.228.166; 13.O.228.169; 13.O.228.172; 13.O.228.175; 13.O.228.240; 13.O.228.244; 13.O.229.228; 13.O.229.229; 13.O.229.230; 13.O.229.231; 13.O.229.236; 13.O.229.237; 13.O.229.238; 13.O.229.239; 13.O.229.154; 13.O.229.157; 13.O.229.166; 13.O.229.169; 13.O.229.172; 13.O.229.175; 13.O.229.240; 13.O.229.244; 13.O.230.228; 13.O.230.229; 13.O.230.230; 13.O.230.231; 13.O.230.236; 13.O.230.237; 13.O.230.238; 13.O.230.239; 13.O.230.154; 13.O.230.157; 13.O.230.166; 13.O.230.169; 13.O.230.172; 13.O.230.175; 13.O.230.240; 13.O.230.244; 13.O.231.228; 13.O.231.229; 13.O.231.230; 13.O.231.231; 13.O.231.236; 13.O.231.237; 13.O.231.238; 13.O.231.239; 13.O.231.154; 13.O.231.157; 13.O.231.166; 13.O.231.169; 13.O.231.172; 13.O.231.175; 13.O.231.240; 13.O.231.244; 13.O.236.228; 13.O.236.229; 13.O.236.230; 13.O.236.231; 13.O.236.236; 13.O.236.237; 13.O.236.238; 13.O.236.239; 13.O.236.154; 13.O.236.157; 13.O.236.166; 13.O.236.169; 13.O.236.172; 13.O.236.175; 13.O.236.240; 13.O.236.244; 13.O.237.228; 13.O.237.229; 13.O.237.230; 13.O.237.231; 13.O.237.236; 13.O.237.237; 13.O.237.238; 13.O.237.239; 13.O.237.154; 13.O.237.157; 13.O.237.166; 13.O.237.169; 13.O.237.172; 13.O.237.175; 13.O.237.240; 13.O.237.244; 13.O.238.228; 13.O.238.229; 13.O.238.230; 13.O.238.231; 13.O.238.236; 13.O.238.237; 13.O.238.238; 13.O.238.239; 13.O.238.154; 13.O.238.157; 13.O.238.166; 13.O.238.169; 13.O.238.172; 13.O.238.175; 13.O.238.240; 13.O.238.244; 13.O.239.228; 13.O.239.229; 13.O.239.230; 13.O.239.231; 13.O.239.236; 13.O.239.237; 13.O.239.238; 13.O.239.239; 13.O.239.154; 13.O.239.157; 13.O.239.166; 13.O.239.169; 13.O.239.172; 13.O.239.175; 13.O.239.240; 13.O.239.244; 13.O.154.228; 13.O.154.229; 13.O.154.230; 13.O.154.231; 13.O.154.236; 13.O.154.237; 13.O.154.238; 13.O.154.239; 13.O.154.154; 13.O.154.157; 13.O.154.166; 13.O.154.169; 13.O.154.172; 13.O.154.175; 13.O.154.240; 13.O.154.244; 13.O.157.228; 13.O.157.229; 13.O.157.230; 13.O.157.231; 13.O.157.236; 13.O.157.237; 13.O.157.238; 13.O.157.239; 13.O.157.154; 13.O.157.157; 13.O.157.166; 13.O.157.169; 13.O.157.172; 13.O.157.175; 13.O.157.240; 13.O.157.244; 13.O.166.228; 13.O.166.229; 13.O.166.230; 13.O.166.231; 13.O.166.236; 13.O.166.237; 13.O.166.238; 13.O.166.239; 13.O.166.154; 13.O.166.157; 13.O.166.166; 13.O.166.169; 13.O.166.172; 13.O.166.175; 13.O.166.240; 13.O.166.244; 13.O.169.228; 13.O.169.229; 13.O.169.230; 13.O.169.231; 13.O.169.236; 13.O.169.237; 13.O.169.238; 13.O.169.239; 13.O.169.154; 13.O.169.157; 13.O.169.166; 13.O.169.169; 13.O.169.172; 13.O.169.175; 13.O.169.240; 13.O.169.244; 13.O.172.228; 13.O.172.229; 13.O.172.230; 13.O.172.231; 13.O.172.236; 13.O.172.237; 13.O.172.238; 13.O.172.239; 13.O.172.154; 13.O.172.157; 13.O.172.166; 13.O.172.169; 13.O.172.172; 13.O.172.175; 13.O.172.240; 13.O.172.244; 13.O.175.228; 13.O.175.229; 13.O.175.230; 13.O.175.231; 13.O.175.236; 13.O.175.237; 13.O.175.238; 13.O.175.239; 13.O.175.154; 13.O.175.157; 13.O.175.166; 13.O.175.169; 13.O.175.172; 13.O.175.175; 13.O.175.240; 13.O.175.244; 13.O.240.228; 13.O.240.229; 13.O.240.230; 13.O.240.231; 13.O.240.236; 13.O.240.237; 13.O.240.238; 13.O.240.239; 13.O.240.154; 13.O.240.157; 13.O.240.166; 13.O.240.169; 13.O.240.172; 13.O.240.175; 13.O.240.240; 13.O.240.244; 13.O.244.228; 13.O.244.229; 13.O.244.230; 13.O.244.231; 13.O.244.236; 13.O.244.237; 13.O.244.238; 13.O.244.239; 13.O.244.154; 13.O.244.157; 13.O.244.166; 13.O.244.169; 13.O.244.172; 13.O.244.175; 13.O.244.240; 13.O.244.244;

Prodrugs of 13.P

13.P.228.228; 13.P.228.229; 13.P.228.230; 13.P.228.231; 13.P.228.236; 13.P.228.237; 13.P.228.238; 13.P.228.239; 13.P.228.154; 13.P.228.157; 13.P.228.166; 13.P.228.169; 13.P.228.172; 13.P.228.175; 13.P.228.240; 13.P.228.244; 13.P.229.228; 13.P.229.229; 13.P.229.230; 13.P.229.231; 13.P.229.236; 13.P.229.237; 13.P.229.238; 13.P.229.239; 13.P.229.154; 13.P.229.157; 13.P.229.166; 13.P.229.169; 13.P.229.172; 13.P.229.175; 13.P.229.240; 13.P.229.244; 13.P.230.228; 13.P.230.229; 13.P.230.230; 13.P.230.231; 13.P.230.236; 13.P.230.237; 13.P.230.238; 13.P.230.239; 13.P.230.154; 13.P.230.157; 13.P.230.166; 13.P.230.169; 13.P.230.172; 13.P.230.175; 13.P.230.240; 13.P.230.244; 13.P.231.228; 13.P.231.229; 13.P.231.230; 13.P.231.231; 13.P.231.236; 13.P.231.237; 13.P.231.238; 13.P.231.239; 13.P.231.154; 13.P.231.157; 13.P.231.166; 13.P.231.169; 13.P.231.172; 13.P.231.175; 13.P.231.240; 13.P.231.244; 13.P.236.228; 13.P.236.229; 13.P.236.230; 13.P.236.231; 13.P.236.236; 13.P.236.237; 13.P.236.238; 13.P.236.239; 13.P.236.154; 13.P.236.157; 13.P.236.166; 13.P.236.169; 13.P.236.172; 13.P.236.175; 13.P.236.240; 13.P.236.244; 13.P.237.228; 13.P.237.229; 13.P.237.230; 13.P.237.231; 13.P.237.236; 13.P.237.237; 13.P.237.238; 13.P.237.239; 13.P.237.154; 13.P.237.157; 13.P.237.166; 13.P.237.169; 13.P.237.172; 13.P.237.175; 13.P.237.240; 13.P.237.244; 13.P.238.228; 13.P.238.229; 13.P.238.230; 13.P.238.231; 13.P.238.236; 13.P.238.237; 13.P.238.238; 13.P.238.239; 13.P.238.154; 13.P.238.157; 13.P.238.166; 13.P.238.169; 13.P.238.172; 13.P.238.175; 13.P.238.240; 13.P.238.244; 13.P.239.228; 13.P.239.229; 13.P.239.230; 13.P.239.231; 13.P.239.236; 13.P.239.237; 13.P.239.238; 13.P.239.239; 13.P.239.154; 13.P.239.157; 13.P.239.166; 13.P.239.169; 13.P.239.172; 13.P.239.175; 13.P.239.240; 13.P.239.244; 13.P.154.228; 13.P.154.229; 13.P.154.230; 13.P.154.231; 13.P.154.236; 13.P.154.237; 13.P.154.238; 13.P.154.239; 13.P.154.154; 13.P.154.157; 13.P.154.166; 13.P.154.169; 13.P.154.172; 13.P.154.175; 13.P.154.240; 13.P.154.244; 13.P.157.228; 13.P.157.229; 13.P.157.230; 13.P.157.231; 13.P.157.236; 13.P.157.237;

TABLE 100-continued

13.P.157.238; 13.P.157.239; 13.P.157.154; 13.P.157.157; 13.P.157.166; 13.P.157.169;
13.P.157.172; 13.P.157.175; 13.P.157.240; 13.P.157.244; 13.P.166.228; 13.P.166.229;
13.P.166.230; 13.P.166.231; 13.P.166.236; 13.P.166.237; 13.P.166.238; 13.P.166.239;
13.P.166.154; 13.P.166.157; 13.P.166.166; 13.P.166.169; 13.P.166.172; 13.P.166.175;
13.P.166.240; 13.P.166.244; 13.P.169.228; 13.P.169.229; 13.P.169.230; 13.P.169.231;
13.P.169.236; 13.P.169.237; 13.P.169.238; 13.P.169.239; 13.P.169.154; 13.P.169.157;
13.P.169.166; 13.P.169.169; 13.P.169.172; 13.P.169.175; 13.P.169.240; 13.P.169.244;
13.P.172.228; 13.P.172.229; 13.P.172.230; 13.P.172.231; 13.P.172.236; 13.P.172.237;
13.P.172.238; 13.P.172.239; 13.P.172.154; 13.P.172.157; 13.P.172.166; 13.P.172.169;
13.P.172.172; 13.P.172.175; 13.P.172.240; 13.P.172.244; 13.P.175.228; 13.P.175.229;
13.P.175.230; 13.P.175.231; 13.P.175.236; 13.P.175.237; 13.P.175.238; 13.P.175.239;
13.P.175.154; 13.P.175.157; 13.P.175.166; 13.P.175.169; 13.P.175.172; 13.P.175.175;
13.P.175.240; 13.P.175.244; 13.P.240.228; 13.P.240.229; 13.P.240.230; 13.P.240.231;
13.P.240.236; 13.P.240.237; 13.P.240.238; 13.P.240.239; 13.P.240.154; 13.P.240.157;
13.P.240.166; 13.P.240.169; 13.P.240.172; 13.P.240.175; 13.P.240.240; 13.P.240.244;
13.P.244.228; 13.P.244.229; 13.P.244.230; 13.P.244.231; 13.P.244.236; 13.P.244.237;
13.P.244.238; 13.P.244.239; 13.P.244.154; 13.P.244.157; 13.P.244.166; 13.P.244.169;
13.P.244.172; 13.P.244.175; 13.P.244.240; 13.P.244.244;

Prodrugs of 13.U

13.U.228.228; 13.U.228.229; 13.U.228.230; 13.U.228.231; 13.U.228.236; 13.U.228.237;
13.U.228.238; 13.U.228.239; 13.U.228.154; 13.U.228.157; 13.U.228.166; 13.U.228.169;
13.U.228.172; 13.U.228.175; 13.U.228.240; 13.U.228.244; 13.U.229.228; 13.U.229.229;
13.U.229.230; 13.U.229.231; 13.U.229.236; 13.U.229.237; 13.U.229.238; 13.U.229.239;
13.U.229.154; 13.U.229.157; 13.U.229.166; 13.U.229.169; 13.U.229.172; 13.U.229.175;
13.U.229.240; 13.U.229.244; 13.U.230.228; 13.U.230.229; 13.U.230.230; 13.U.230.231;
13.U.230.236; 13.U.230.237; 13.U.230.238; 13.U.230.239; 13.U.230.154; 13.U.230.157;
13.U.230.166; 13.U.230.169; 13.U.230.172; 13.U.230.175; 13.U.230.240; 13.U.230.244;
13.U.231.228; 13.U.231.229; 13.U.231.230; 13.U.231.231; 13.U.231.236; 13.U.231.237;
13.U.231.238; 13.U.231.239; 13.U.231.154; 13.U.231.157; 13.U.231.166; 13.U.231.169;
13.U.231.172; 13.U.231.175; 13.U.231.240; 13.U.231.244; 13.U.236.228; 13.U.236.229;
13.U.236.230; 13.U.236.231; 13.U.236.236; 13.U.236.237; 13.U.236.238; 13.U.236.239;
13.U.236.154; 13.U.236.157; 13.U.236.166; 13.U.236.169; 13.U.236.172; 13.U.236.175;
13.U.236.240; 13.U.236.244; 13.U.237.228; 13.U.237.229; 13.U.237.230; 13.U.237.231;
13.U.237.236; 13.U.237.237; 13.U.237.238; 13.U.237.239; 13.U.237.154; 13.U.237.157;
13.U.237.166; 13.U.237.169; 13.U.237.172; 13.U.237.175; 13.U.237.240; 13.U.237.244;
13.U.238.228; 13.U.238.229; 13.U.238.230; 13.U.238.231; 13.U.238.236; 13.U.238.237;
13.U.238.238; 13.U.238.239; 13.U.238.154; 13.U.238.157; 13.U.238.166; 13.U.238.169;
13.U.238.172; 13.U.238.175; 13.U.238.240; 13.U.238.244; 13.U.239.228; 13.U.239.229;
13.U.239.230; 13.U.239.231; 13.U.239.236; 13.U.239.237; 13.U.239.238; 13.U.239.239;
13.U.239.154; 13.U.239.157; 13.U.239.166; 13.U.239.169; 13.U.239.172; 13.U.239.175;
13.U.239.240; 13.U.239.244; 13.U.154.228; 13.U.154.229; 13.U.154.230; 13.U.154.231;
13.U.154.236; 13.U.154.237; 13.U.154.238; 13.U.154.239; 13.U.154.154; 13.U.154.157;
13.U.154.166; 13.U.154.169; 13.U.154.172; 13.U.154.175; 13.U.154.240; 13.U.154.244;
13.U.157.228; 13.U.157.229; 13.U.157.230; 13.U.157.231; 13.U.157.236; 13.U.157.237;
13.U.157.238; 13.U.157.239; 13.U.157.154; 13.U.157.157; 13.U.157.166; 13.U.157.169;
13.U.157.172; 13.U.157.175; 13.U.157.240; 13.U.157.244; 13.U.166.228; 13.U.166.229;
13.U.166.230; 13.U.166.231; 13.U.166.236; 13.U.166.237; 13.U.166.238; 13.U.166.239;
13.U.166.154; 13.U.166.157; 13.U.166.166; 13.U.166.169; 13.U.166.172; 13.U.166.175;
13.U.166.240; 13.U.166.244; 13.U.169.228; 13.U.169.229; 13.U.169.230; 13.U.169.231;
13.U.169.236; 13.U.169.237; 13.U.169.238; 13.U.169.239; 13.U.169.154; 13.U.169.157;
13.U.169.166; 13.U.169.169; 13.U.169.172; 13.U.169.175; 13.U.169.240; 13.U.169.244;
13.U.172.228; 13.U.172.229; 13.U.172.230; 13.U.172.231; 13.U.172.236; 13.U.172.237;
13.U.172.238; 13.U.172.239; 13.U.172.154; 13.U.172.157; 13.U.172.166; 13.U.172.169;
13.U.172.172; 13.U.172.175; 13.U.172.240; 13.U.172.244; 13.U.175.228; 13.U.175.229;
13.U.175.230; 13.U.175.231; 13.U.175.236; 13.U.175.237; 13.U.175.238; 13.U.175.239;
13.U.175.154; 13.U.175.157; 13.U.175.166; 13.U.175.169; 13.U.175.172; 13.U.175.175;
13.U.175.240; 13.U.175.244; 13.U.240.228; 13.U.240.229; 13.U.240.230; 13.U.240.231;
13.U.240.236; 13.U.240.237; 13.U.240.238; 13.U.240.239; 13.U.240.154; 13.U.240.157;
13.U.240.166; 13.U.240.169; 13.U.240.172; 13.U.240.175; 13.U.240.240; 13.U.240.244;
13.U.244.228; 13.U.244.229; 13.U.244.230; 13.U.244.231; 13.U.244.236; 13.U.244.237;
13.U.244.238; 13.U.244.239; 13.U.244.154; 13.U.244.157; 13.U.244.166; 13.U.244.169;
13.U.244.172; 13.U.244.175; 13.U.244.240; 13.U.244.244;

Prodrugs of 13.W

13.W.228.228; 13.W.228.229; 13.W.228.230; 13.W.228.231; 13.W.228.236;
13.W.228.237; 13.W.228.238; 13.W.228.239; 13.W.228.154; 13.W.228.157; 13.W.228.166;
13.W.228.169; 13.W.228.172; 13.W.228.175; 13.W.228.240; 13.W.228.244; 13.W.229.228;
13.W.229.229; 13.W.229.230; 13.W.229.231; 13.W.229.236; 13.W.229.237; 13.W.229.238;
13.W.229.239; 13.W.229.154; 13.W.229.157; 13.W.229.166; 13.W.229.169; 13.W.229.172;
13.W.229.175; 13.W.229.240; 13.W.229.244; 13.W.230.228; 13.W.230.229; 13.W.230.230;
13.W.230.231; 13.W.230.236; 13.W.230.237; 13.W.230.238; 13.W.230.239; 13.W.230.154;
13.W.230.157; 13.W.230.166; 13.W.230.169; 13.W.230.172; 13.W.230.175; 13.W.230.240;
13.W.230.244; 13.W.231.228; 13.W.231.229; 13.W.231.230; 13.W.231.231; 13.W.231.236;
13.W.231.237; 13.W.231.238; 13.W.231.239; 13.W.231.154; 13.W.231.157; 13.W.231.166;
13.W.231.169; 13.W.231.172; 13.W.231.175; 13.W.231.240; 13.W.231.244; 13.W.236.228;
13.W.236.229; 13.W.236.230; 13.W.236.231; 13.W.236.236; 13.W.236.237; 13.W.236.238;
13.W.236.239; 13.W.236.154; 13.W.236.157; 13.W.236.166; 13.W.236.169; 13.W.236.172;
13.W.236.175; 13.W.236.240; 13.W.236.244; 13.W.237.228; 13.W.237.229; 13.W.237.230;

TABLE 100-continued

13.W.237.231; 13.W.237.236; 13.W.237.237; 13.W.237.238; 13.W.237.239; 13.W.237.154; 13.W.237.157; 13.W.237.166; 13.W.237.169; 13.W.237.172; 13.W.237.175; 13.W.237.240; 13.W.237.244; 13.W.238.228; 13.W.238.229; 13.W.238.230; 13.W.238.231; 13.W.238.236; 13.W.238.237; 13.W.238.238; 13.W.238.239; 13.W.238.154; 13.W.238.157; 13.W.238.166; 13.W.238.169; 13.W.238.172; 13.W.238.175; 13.W.238.240; 13.W.238.244; 13.W.239.228; 13.W.239.229; 13.W.239.230; 13.W.239.231; 13.W.239.236; 13.W.239.237; 13.W.239.238; 13.W.239.239; 13.W.239.154; 13.W.239.157; 13.W.239.166; 13.W.239.169; 13.W.239.172; 13.W.239.175; 13.W.239.240; 13.W.239.244; 13.W.154.228; 13.W.154.229; 13.W.154.230; 13.W.154.231; 13.W.154.236; 13.W.154.237; 13.W.154.238; 13.W.154.239; 13.W.154.154; 13.W.154.157; 13.W.154.166; 13.W.154.169; 13.W.154.172; 13.W.154.175; 13.W.154.240; 13.W.154.244; 13.W.157.228; 13.W.157.229; 13.W.157.230; 13.W.157.231; 13.W.157.236; 13.W.157.237; 13.W.157.238; 13.W.157.239; 13.W.157.154; 13.W.157.157; 13.W.157.166; 13.W.157.169; 13.W.157.172; 13.W.157.175; 13.W.157.240; 13.W.157.244; 13.W.166.228; 13.W.166.229; 13.W.166.230; 13.W.166.231; 13.W.166.236; 13.W.166.237; 13.W.166.238; 13.W.166.239; 13.W.166.154; 13.W.166.157; 13.W.166.166; 13.W.166.169; 13.W.166.172; 13.W.166.175; 13.W.166.240; 13.W.166.244; 13.W.169.228; 13.W.169.229; 13.W.169.230; 13.W.169.231; 13.W.169.236; 13.W.169.237; 13.W.169.238; 13.W.169.239; 13.W.169.154; 13.W.169.157; 13.W.169.166; 13.W.169.169; 13.W.169.172; 13.W.169.175; 13.W.169.240; 13.W.169.244; 13.W.172.228; 13.W.172.229; 13.W.172.230; 13.W.172.231; 13.W.172.236; 13.W.172.237; 13.W.172.238; 13.W.172.239; 13.W.172.154; 13.W.172.157; 13.W.172.166; 13.W.172.169; 13.W.172.172; 13.W.172.175; 13.W.172.240; 13.W.172.244; 13.W.175.228; 13.W.175.229; 13.W.175.230; 13.W.175.231; 13.W.175.236; 13.W.175.237; 13.W.175.238; 13.W.175.239; 13.W.175.154; 13.W.175.157; 13.W.175.166; 13.W.175.169; 13.W.175.172; 13.W.175.175; 13.W.175.240; 13.W.175.244; 13.W.240.228; 13.W.240.229; 13.W.240.230; 13.W.240.231; 13.W.240.236; 13.W.240.237; 13.W.240.238; 13.W.240.239; 13.W.240.154; 13.W.240.157; 13.W.240.166; 13.W.240.169; 13.W.240.172; 13.W.240.175; 13.W.240.240; 13.W.240.244; 13.W.244.228; 13.W.244.229; 13.W.244.230; 13.W.244.231; 13.W.244.236; 13.W.244.237; 13.W.244.238; 13.W.244.239; 13.W.244.154; 13.W.244.157; 13.W.244.166; 13.W.244.169; 13.W.244.172; 13.W.244.175; 13.W.244.240; 13.W.244.244;

Prodrugs of 13.Y

13.Y.228.228; 13.Y.228.229; 13.Y.228.230; 13.Y.228.231; 13.Y.228.236; 13.Y.228.237; 13.Y.228.238; 13.Y.228.239; 13.Y.228.154; 13.Y.228.157; 13.Y.228.166; 13.Y.228.169; 13.Y.228.172; 13.Y.228.175; 13.Y.228.240; 13.Y.228.244; 13.Y.229.228; 13.Y.229.229; 13.Y.229.230; 13.Y.229.231; 13.Y.229.236; 13.Y.229.237; 13.Y.229.238; 13.Y.229.239; 13.Y.229.154; 13.Y.229.157; 13.Y.229.166; 13.Y.229.169; 13.Y.229.172; 13.Y.229.175; 13.Y.229.240; 13.Y.229.244; 13.Y.230.228; 13.Y.230.229; 13.Y.230.230; 13.Y.230.231; 13.Y.230.236; 13.Y.230.237; 13.Y.230.238; 13.Y.230.239; 13.Y.230.154; 13.Y.230.157; 13.Y.230.166; 13.Y.230.169; 13.Y.230.172; 13.Y.230.175; 13.Y.230.240; 13.Y.230.244; 13.Y.231.228; 13.Y.231.229; 13.Y.231.230; 13.Y.231.231; 13.Y.231.236; 13.Y.231.237; 13.Y.231.238; 13.Y.231.239; 13.Y.231.154; 13.Y.231.157; 13.Y.231.166; 13.Y.231.169; 13.Y.231.172; 13.Y.231.175; 13.Y.231.240; 13.Y.231.244; 13.Y.236.228; 13.Y.236.229; 13.Y.236.230; 13.Y.236.231; 13.Y.236.236; 13.Y.236.237; 13.Y.236.238; 13.Y.236.239; 13.Y.236.154; 13.Y.236.157; 13.Y.236.166; 13.Y.236.169; 13.Y.236.172; 13.Y.236.175; 13.Y.236.240; 13.Y.236.244; 13.Y.237.228; 13.Y.237.229; 13.Y.237.230; 13.Y.237.231; 13.Y.237.236; 13.Y.237.237; 13.Y.237.238; 13.Y.237.239; 13.Y.237.154; 13.Y.237.157; 13.Y.237.166; 13.Y.237.169; 13.Y.237.172; 13.Y.237.175; 13.Y.237.240; 13.Y.237.244; 13.Y.238.228; 13.Y.238.229; 13.Y.238.230; 13.Y.238.231; 13.Y.238.236; 13.Y.238.237; 13.Y.238.238; 13.Y.238.239; 13.Y.238.154; 13.Y.238.157; 13.Y.238.166; 13.Y.238.169; 13.Y.238.172; 13.Y.238.175; 13.Y.238.240; 13.Y.238.244; 13.Y.239.228; 13.Y.239.229; 13.Y.239.230; 13.Y.239.231; 13.Y.239.236; 13.Y.239.237; 13.Y.239.238; 13.Y.239.239; 13.Y.239.154; 13.Y.239.157; 13.Y.239.166; 13.Y.239.169; 13.Y.239.172; 13.Y.239.175; 13.Y.239.240; 13.Y.239.244; 13.Y.154.228; 13.Y.154.229; 13.Y.154.230; 13.Y.154.231; 13.Y.154.236; 13.Y.154.237; 13.Y.154.238; 13.Y.154.239; 13.Y.154.154; 13.Y.154.157; 13.Y.154.166; 13.Y.154.169; 13.Y.154.172; 13.Y.154.175; 13.Y.154.240; 13.Y.154.244; 13.Y.157.228; 13.Y.157.229; 13.Y.157.230; 13.Y.157.231; 13.Y.157.236; 13.Y.157.237; 13.Y.157.238; 13.Y.157.239; 13.Y.157.154; 13.Y.157.157; 13.Y.157.166; 13.Y.157.169; 13.Y.157.172; 13.Y.157.175; 13.Y.157.240; 13.Y.157.244; 13.Y.166.228; 13.Y.166.229; 13.Y.166.230; 13.Y.166.231; 13.Y.166.236; 13.Y.166.237; 13.Y.166.238; 13.Y.166.239; 13.Y.166.154; 13.Y.166.157; 13.Y.166.166; 13.Y.166.169; 13.Y.166.172; 13.Y.166.175; 13.Y.166.240; 13.Y.166.244; 13.Y.169.228; 13.Y.169.229; 13.Y.169.230; 13.Y.169.231; 13.Y.169.236; 13.Y.169.237; 13.Y.169.238; 13.Y.169.239; 13.Y.169.154; 13.Y.169.157; 13.Y.169.166; 13.Y.169.169; 13.Y.169.172; 13.Y.169.175; 13.Y.169.240; 13.Y.169.244; 13.Y.172.228; 13.Y.172.229; 13.Y.172.230; 13.Y.172.231; 13.Y.172.236; 13.Y.172.237; 13.Y.172.238; 13.Y.172.239; 13.Y.172.154; 13.Y.172.157; 13.Y.172.166; 13.Y.172.169; 13.Y.172.172; 13.Y.172.175; 13.Y.172.240; 13.Y.172.244; 13.Y.175.228; 13.Y.175.229; 13.Y.175.230; 13.Y.175.231; 13.Y.175.236; 13.Y.175.237; 13.Y.175.238; 13.Y.175.239; 13.Y.175.154; 13.Y.175.157; 13.Y.175.166; 13.Y.175.169; 13.Y.175.172; 13.Y.175.175; 13.Y.175.240; 13.Y.175.244; 13.Y.240.228; 13.Y.240.229; 13.Y.240.230; 13.Y.240.231; 13.Y.240.236; 13.Y.240.237; 13.Y.240.238; 13.Y.240.239; 13.Y.240.154; 13.Y.240.157; 13.Y.240.166; 13.Y.240.169; 13.Y.240.172; 13.Y.240.175; 13.Y.240.240; 13.Y.240.244; 13.Y.244.228; 13.Y.244.229; 13.Y.244.230; 13.Y.244.231; 13.Y.244.236; 13.Y.244.237; 13.Y.244.238; 13.Y.244.239; 13.Y.244.154; 13.Y.244.157; 13.Y.244.166; 13.Y.244.169; 13.Y.244.172; 13.Y.244.175; 13.Y.244.240; 13.Y.244.244;

Prodrugs of 14.AH

14.AH.4.157; 14.AH.4.158; 14.AH.4.196; 14.AH.4.223; 14.AH.4.240; 14.AH.4.244; 14.AH.4.243; 14.AH.4.247; 14.AH.5.157; 14.AH.5.158; 14.AH.5.196; 14.AH.5.223; 14.AH.5.240; 14.AH.5.244; 14.AH.5.243; 14.AH.5.247; 14.AH.7.157; 14.AH.7.158;

TABLE 100-continued

14.AH.7.196; 14.AH.7.223; 14.AH.7.240; 14.AH.7.244; 14.AH.7.243; 14.AH.7.247;
14.AH.15.157; 14.AH.15.158; 14.AH.15.196; 14.AH.15.223; 14.AH.15.240; 14.AH.15.244;
14.AH.15.243; 14.AH.15.247; 14.AH.16.157; 14.AH.16.158; 14.AH.16.196; 14.AH.16.223;
14.AH.16.240; 14.AH.16.244; 14.AH.16.243; 14.AH.16.247; 14.AH.18.157; 14.AH.18.158;
14.AH.18.196; 14.AH.18.223; 14.AH.18.240; 14.AH.18.244; 14.AH.18.243; 14.AH.18.247;
14.AH.26.157; 14.AH.26.158; 14.AH.26.196; 14.AH.26.223; 14.AH.26.240; 14.AH.26.244;
14.AH.26.243; 14.AH.26.247; 14.AH.27.157; 14.AH.27.158; 14.AH.27.196; 14.AH.27.223;
14.AH.27.240; 14.AH.27.244; 14.AH.27.243; 14.AH.27.247; 14.AH.29.157; 14.AH.29.158;
14.AH.29.196; 14.AH.29.223; 14.AH.29.240; 14.AH.29.244; 14.AH.29.243; 14.AH.29.247;
14.AH.54.157; 14.AH.54.158; 14.AH.54.196; 14.AH.54.223; 14.AH.54.240; 14.AH.54.244;
14.AH.54.243; 14.AH.54.247; 14.AH.55.157; 14.AH.55.158; 14.AH.55.196; 14.AH.55.223;
14.AH.55.240; 14.AH.55.244; 14.AH.55.243; 14.AH.55.247; 14.AH.56.157; 14.AH.56.158;
14.AH.56.196; 14.AH.56.223; 14.AH.56.240; 14.AH.56.244; 14.AH.56.243; 14.AH.56.247;
14.AH.157.157; 14.AH.157.158; 14.AH.157.196; 14.AH.157.223; 14.AH.157.240;
14.AH.157.244; 14.AH.157.243; 14.AH.157.247; 14.AH.196.157; 14.AH.196.158;
14.AH.196.196; 14.AH.196.223; 14.AH.196.240; 14.AH.196.244; 14.AH.196.243;
14.AH.196.247; 14.AH.223.157; 14.AH.223.158; 14.AH.223.196; 14.AH.223.223;
14.AH.223.240; 14.AH.223.244; 14.AH.223.243; 14.AH.223.247; 14.AH.240.157;
14.AH.240.158; 14.AH.240.196; 14.AH.240.223; 14.AH.240.240; 14.AH.240.244;
14.AH.240.243; 14.AH.240.247; 14.AH.244.157; 14.AH.244.158; 14.AH.244.196;
14.AH.244.223; 14.AH.244.240; 14.AH.244.244; 14.AH.244.243; 14.AH.244.247;
14.AH.247.157; 14.AH.247.158; 14.AH.247.196; 14.AH.247.223; 14.AH.247.240;
14.AH.247.244; 14.AH.247.243; 14.AH.247.247;

Prodrugs of 14.AJ

14.AJ.4.157; 14.AJ.4.158; 14.AJ.4.196; 14.AJ.4.223; 14.AJ.4.240; 14.AJ.4.244;
14.AJ.4.243; 14.AJ.4.247; 14.AJ.5.157; 14.AJ.5.158; 14.AJ.5.196; 14.AJ.5.223; 14.AJ.5.240;
14.AJ.5.244; 14.AJ.5.243; 14.AJ.5.247; 14.AJ.7.157; 14.AJ.7.158; 14.AJ.7.196; 14.AJ.7.223;
14.AJ.7.240; 14.AJ.7.244; 14.AJ.7.243; 14.AJ.7.247; 14.AJ.15.157; 14.AJ.15.158;
14.AJ.15.196; 14.AJ.15.223; 14.AJ.15.240; 14.AJ.15.244; 14.AJ.15.243; 14.AJ.15.247;
14.AJ.16.157; 14.AJ.16.158; 14.AJ.16.196; 14.AJ.16.223; 14.AJ.16.240; 14.AJ.16.244;
14.AJ.16.243; 14.AJ.16.247; 14.AJ.18.157; 14.AJ.18.158; 14.AJ.18.196; 14.AJ.18.223;
14.AJ.18.240; 14.AJ.18.244; 14.AJ.18.243; 14.AJ.18.247; 14.AJ.26.157; 14.AJ.26.158;
14.AJ.26.196; 14.AJ.26.223; 14.AJ.26.240; 14.AJ.26.244; 14.AJ.26.243; 14.AJ.26.247;
14.AJ.27.157; 14.AJ.27.158; 14.AJ.27.196; 14.AJ.27.223; 14.AJ.27.240; 14.AJ.27.244;
14.AJ.27.243; 14.AJ.27.247; 14.AJ.29.157; 14.AJ.29.158; 14.AJ.29.196; 14.AJ.29.223;
14.AJ.29.240; 14.AJ.29.244; 14.AJ.29.243; 14.AJ.29.247; 14.AJ.54.157; 14.AJ.54.158;
14.AJ.54.196; 14.AJ.54.223; 14.AJ.54.240; 14.AJ.54.244; 14.AJ.54.243; 14.AJ.54.247;
14.AJ.55.157; 14.AJ.55.158; 14.AJ.55.196; 14.AJ.55.223; 14.AJ.55.240; 14.AJ.55.244;
14.AJ.55.243; 14.AJ.55.247; 14.AJ.56.157; 14.AJ.56.158; 14.AJ.56.196; 14.AJ.56.223;
14.AJ.56.240; 14.AJ.56.244; 14.AJ.56.243; 14.AJ.56.247; 14.AJ.157.157; 14.AJ.157.158;
14.AJ.157.196; 14.AJ.157.223; 14.AJ.157.240; 14.AJ.157.244; 14.AJ.157.243;
14.AJ.157.247; 14.AJ.196.157; 14.AJ.196.158; 14.AJ.196.196; 14.AJ.196.223;
14.AJ.196.240; 14.AJ.196.244; 14.AJ.196.243; 14.AJ.196.247; 14.AJ.223.157;
14.AJ.223.158; 14.AJ.223.196; 14.AJ.223.223; 14.AJ.223.240; 14.AJ.223.244;
14.AJ.223.243; 14.AJ.223.247; 14.AJ.240.157; 14.AJ.240.158; 14.AJ.240.196;
14.AJ.240.223; 14.AJ.240.240; 14.AJ.240.244; 14.AJ.240.243; 14.AJ.240.247;
14.AJ.244.157; 14.AJ.244.158; 14.AJ.244.196; 14.AJ.244.223; 14.AJ.244.240;
14.AJ.244.244; 14.AJ.244.243; 14.AJ.244.247; 14.AJ.247.157; 14.AJ.247.158;
14.AJ.247.196; 14.AJ.247.223; 14.AJ.247.240; 14.AJ.247.244; 14.AJ.247.243;
14.AJ.247.247;

Prodrugs of 14.AN

14.AN.4.157; 14.AN.4.158; 14.AN.4.196; 14.AN.4.223; 14.AN.4.240; 14.AN.4.244;
14.AN.4.243; 14.AN.4.247; 14.AN.5.157; 14.AN.5.158; 14.AN.5.196; 14.AN.5.223;
14.AN.5.240; 14.AN.5.244; 14.AN.5.243; 14.AN.5.247; 14.AN.7.157; 14.AN.7.158;
14.AN.7.196; 14.AN.7.223; 14.AN.7.240; 14.AN.7.244; 14.AN.7.243; 14.AN.7.247;
14.AN.15.157; 14.AN.15.158; 14.AN.15.196; 14.AN.15.223; 14.AN.15.240; 14.AN.15.244;
14.AN.15.243; 14.AN.15.247; 14.AN.16.157; 14.AN.16.158; 14.AN.16.196; 14.AN.16.223;
14.AN.16.240; 14.AN.16.244; 14.AN.16.243; 14.AN.16.247; 14.AN.18.157; 14.AN.18.158;
14.AN.18.196; 14.AN.18.223; 14.AN.18.240; 14.AN.18.244; 14.AN.18.243; 14.AN.18.247;
14.AN.26.157; 14.AN.26.158; 14.AN.26.196; 14.AN.26.223; 14.AN.26.240; 14.AN.26.244;
14.AN.26.243; 14.AN.26.247; 14.AN.27.157; 14.AN.27.158; 14.AN.27.196; 14.AN.27.223;
14.AN.27.240; 14.AN.27.244; 14.AN.27.243; 14.AN.27.247; 14.AN.29.157; 14.AN.29.158;
14.AN.29.196; 14.AN.29.223; 14.AN.29.240; 14.AN.29.244; 14.AN.29.243; 14.AN.29.247;
14.AN.54.157; 14.AN.54.158; 14.AN.54.196; 14.AN.54.223; 14.AN.54.240; 14.AN.54.244;
14.AN.54.243; 14.AN.54.247; 14.AN.55.157; 14.AN.55.158; 14.AN.55.196; 14.AN.55.223;
14.AN.55.240; 14.AN.55.244; 14.AN.55.243; 14.AN.55.247; 14.AN.56.157; 14.AN.56.158;
14.AN.56.196; 14.AN.56.223; 14.AN.56.240; 14.AN.56.244; 14.AN.56.243; 14.AN.56.247;
14.AN.157.157; 14.AN.157.158; 14.AN.157.196; 14.AN.157.223; 14.AN.157.240;
14.AN.157.244; 14.AN.157.243; 14.AN.157.247; 14.AN.196.157; 14.AN.196.158;
14.AN.196.196; 14.AN.196.223; 14.AN.196.240; 14.AN.196.244; 14.AN.196.243;
14.AN.196.247; 14.AN.223.157; 14.AN.223.158; 14.AN.223.196; 14.AN.223.223;
14.AN.223.240; 14.AN.223.244; 14.AN.223.243; 14.AN.223.247; 14.AN.240.157;
14.AN.240.158; 14.AN.240.196; 14.AN.240.223; 14.AN.240.240; 14.AN.240.244;
14.AN.240.243; 14.AN.240.247; 14.AN.244.157; 14.AN.244.158; 14.AN.244.196;
14.AN.244.223; 14.AN.244.240; 14.AN.244.244; 14.AN.244.243; 14.AN.244.247;
14.AN.247.157; 14.AN.247.158; 14.AN.247.196; 14.AN.247.223; 14.AN.247.240;
14.AN.247.244; 14.AN.247.243; 14.AN.247.247;

TABLE 100-continued

Prodrugs of 14.AP

14.AP.4.157; 14.AP.4.158; 14.AP.4.196; 14.AP.4.223; 14.AP.4.240; 14.AP.4.244; 14.AP.4.243; 14.AP.4.247; 14.AP.5.157; 14.AP.5.158; 14.AP.5.196; 14.AP.5.223; 14.AP.5.240; 14.AP.5.244; 14.AP.5.243; 14.AP.5.247; 14.AP.7.157; 14.AP.7.158; 14.AP.7.196; 14.AP.7.223; 14.AP.7.240; 14.AP.7.244; 14.AP.7.243; 14.AP.7.247; 14.AP.15.157; 14.AP.15.158; 14.AP.15.196; 14.AP.15.223; 14.AP.15.240; 14.AP.15.244; 14.AP.15.243; 14.AP.15.247; 14.AP.16.157; 14.AP.16.158; 14.AP.16.196; 14.AP.16.223; 14.AP.16.240; 14.AP.16.244; 14.AP.16.243; 14.AP.16.247; 14.AP.18.157; 14.AP.18.158; 14.AP.18.196; 14.AP.18.223; 14.AP.18.240; 14.AP.18.244; 14.AP.18.243; 14.AP.18.247; 14.AP.26.157; 14.AP.26.158; 14.AP.26.196; 14.AP.26.223; 14.AP.26.240; 14.AP.26.244; 14.AP.26.243; 14.AP.26.247; 14.AP.27.157; 14.AP.27.158; 14.AP.27.196; 14.AP.27.223; 14.AP.27.240; 14.AP.27.244; 14.AP.27.243; 14.AP.27.247; 14.AP.29.157; 14.AP.29.158; 14.AP.29.196; 14.AP.29.223; 14.AP.29.240; 14.AP.29.244; 14.AP.29.243; 14.AP.29.247; 14.AP.54.157; 14.AP.54.158; 14.AP.54.196; 14.AP.54.223; 14.AP.54.240; 14.AP.54.244; 14.AP.54.243; 14.AP.54.247; 14.AP.55.157; 14.AP.55.158; 14.AP.55.196; 14.AP.55.223; 14.AP.55.240; 14.AP.55.244; 14.AP.55.243; 14.AP.55.247; 14.AP.56.157; 14.AP.56.158; 14.AP.56.196; 14.AP.56.223; 14.AP.56.240; 14.AP.56.244; 14.AP.56.243; 14.AP.56.247; 14.AP.157.157; 14.AP.157.158; 14.AP.157.196; 14.AP.157.223; 14.AP.157.240; 14.AP.157.244; 14.AP.157.243; 14.AP.157.247; 14.AP.196.157; 14.AP.196.158; 14.AP.196.196; 14.AP.196.223; 14.AP.196.240; 14.AP.196.244; 14.AP.196.243; 14.AP.196.247; 14.AP.223.157; 14.AP.223.158; 14.AP.223.196; 14.AP.223.223; 14.AP.223.240; 14.AP.223.244; 14.AP.223.243; 14.AP.223.247; 14.AP.240.157; 14.AP.240.158; 14.AP.240.196; 14.AP.240.223; 14.AP.240.240; 14.AP.240.244; 14.AP.240.243; 14.AP.240.247; 14.AP.244.157; 14.AP.244.158; 14.AP.244.196; 14.AP.244.223; 14.AP.244.240; 14.AP.244.244; 14.AP.244.243; 14.AP.244.247; 14.AP.247.157; 14.AP.247.158; 14.AP.247.196; 14.AP.247.223; 14.AP.247.240; 14.AP.247.244; 14.AP.247.243; 14.AP.247.247;

Prodrugs of 14.AZ

14.AZ.4.157; 14.AZ.4.158; 14.AZ.4.196; 14.AZ.4.223; 14.AZ.4.240; 14.AZ.4.244; 14.AZ.4.243; 14.AZ.4.247; 14.AZ.5.157; 14.AZ.5.158; 14.AZ.5.196; 14.AZ.5.223; 14.AZ.5.240; 14.AZ.5.244; 14.AZ.5.243; 14.AZ.5.247; 14.AZ.7.157; 14.AZ.7.158; 14.AZ.7.196; 14.AZ.7.223; 14.AZ.7.240; 14.AZ.7.244; 14.AZ.7.243; 14.AZ.7.247; 14.AZ.15.157; 14.AZ.15.158; 14.AZ.15.196; 14.AZ.15.223; 14.AZ.15.240; 14.AZ.15.244; 14.AZ.15.243; 14.AZ.15.247; 14.AZ.16.157; 14.AZ.16.158; 14.AZ.16.196; 14.AZ.16.223; 14.AZ.16.240; 14.AZ.16.244; 14.AZ.16.243; 14.AZ.16.247; 14.AZ.18.157; 14.AZ.18.158; 14.AZ.18.196; 14.AZ.18.223; 14.AZ.18.240; 14.AZ.18.244; 14.AZ.18.243; 14.AZ.18.247; 14.AZ.26.157; 14.AZ.26.158; 14.AZ.26.196; 14.AZ.26.223; 14.AZ.26.240; 14.AZ.26.244; 14.AZ.26.243; 14.AZ.26.247; 14.AZ.27.157; 14.AZ.27.158; 14.AZ.27.196; 14.AZ.27.223; 14.AZ.27.240; 14.AZ.27.244; 14.AZ.27.243; 14.AZ.27.247; 14.AZ.29.157; 14.AZ.29.158; 14.AZ.29.196; 14.AZ.29.223; 14.AZ.29.240; 14.AZ.29.244; 14.AZ.29.243; 14.AZ.29.247; 14.AZ.54.157; 14.AZ.54.158; 14.AZ.54.196; 14.AZ.54.223; 14.AZ.54.240; 14.AZ.54.244; 14.AZ.54.243; 14.AZ.54.247; 14.AZ.55.157; 14.AZ.55.158; 14.AZ.55.196; 14.AZ.55.223; 14.AZ.55.240; 14.AZ.55.244; 14.AZ.55.243; 14.AZ.55.247; 14.AZ.56.157; 14.AZ.56.158; 14.AZ.56.196; 14.AZ.56.223; 14.AZ.56.240; 14.AZ.56.244; 14.AZ.56.243; 14.AZ.56.247; 14.AZ.157.157; 14.AZ.157.158; 14.AZ.157.196; 14.AZ.157.223; 14.AZ.157.240; 14.AZ.157.244; 14.AZ.157.243; 14.AZ.157.247; 14.AZ.196.157; 14.AZ.196.158; 14.AZ.196.196; 14.AZ.196.223; 14.AZ.196.240; 14.AZ.196.244; 14.AZ.196.243; 14.AZ.196.247; 14.AZ.223.157; 14.AZ.223.158; 14.AZ.223.196; 14.AZ.223.223; 14.AZ.223.240; 14.AZ.223.244; 14.AZ.223.243; 14.AZ.223.247; 14.AZ.240.157; 14.AZ.240.158; 14.AZ.240.196; 14.AZ.240.223; 14.AZ.240.240; 14.AZ.240.244; 14.AZ.240.243; 14.AZ.240.247; 14.AZ.244.157; 14.AZ.244.158; 14.AZ.244.196; 14.AZ.244.223; 14.AZ.244.240; 14.AZ.244.244; 14.AZ.244.243; 14.AZ.244.247; 14.AZ.247.157; 14.AZ.247.158; 14.AZ.247.196; 14.AZ.247.223; 14.AZ.247.240; 14.AZ.247.244; 14.AZ.247.243; 14.AZ.247.247;

Prodrugs of 14.BF

14.BF.4.157; 14.BF.4.158; 14.BF.4.196; 14.BF.4.223; 14.BF.4.240; 14.BF.4.244; 14.BF.4.243; 14.BF.4.247; 14.BF.5.157; 14.BF.5.158; 14.BF.5.196; 14.BF.5.223; 14.BF.5.240; 14.BF.5.244; 14.BF.5.243; 14.BF.5.247; 14.BF.7.157; 14.BF.7.158; 14.BF.7.196; 14.BF.7.223; 14.BF.7.240; 14.BF.7.244; 14.BF.7.243; 14.BF.7.247; 14.BF.15.157; 14.BF.15.158; 14.BF.15.196; 14.BF.15.223; 14.BF.15.240; 14.BF.15.244; 14.BF.15.243; 14.BF.15.247; 14.BF.16.157; 14.BF.16.158; 14.BF.16.196; 14.BF.16.223; 14.BF.16.240; 14.BF.16.244; 14.BF.16.243; 14.BF.16.247; 14.BF.18.157; 14.BF.18.158; 14.BF.18.196; 14.BF.18.223; 14.BF.18.240; 14.BF.18.244; 14.BF.18.243; 14.BF.18.247; 14.BF.26.157; 14.BF.26.158; 14.BF.26.196; 14.BF.26.223; 14.BF.26.240; 14.BF.26.244; 14.BF.26.243; 14.BF.26.247; 14.BF.27.157; 14.BF.27.158; 14.BF.27.196; 14.BF.27.223; 14.BF.27.240; 14.BF.27.244; 14.BF.27.243; 14.BF.27.247; 14.BF.29.157; 14.BF.29.158; 14.BF.29.196; 14.BF.29.223; 14.BF.29.240; 14.BF.29.244; 14.BF.29.243; 14.BF.29.247; 14.BF.54.157; 14.BF.54.158; 14.BF.54.196; 14.BF.54.223; 14.BF.54.240; 14.BF.54.244; 14.BF.54.243; 14.BF.54.247; 14.BF.55.157; 14.BF.55.158; 14.BF.55.196; 14.BF.55.223; 14.BF.55.240; 14.BF.55.244; 14.BF.55.243; 14.BF.55.247; 14.BF.56.157; 14.BF.56.158; 14.BF.56.196; 14.BF.56.223; 14.BF.56.240; 14.BF.56.244; 14.BF.56.243; 14.BF.56.247; 14.BF.157.157; 14.BF.157.158; 14.BF.157.196; 14.BF.157.223; 14.BF.157.240; 14.BF.157.244; 14.BF.157.243; 14.BF.157.247; 14.BF.196.157; 14.BF.196.158; 14.BF.196.196; 14.BF.196.223; 14.BF.196.240; 14.BF.196.244; 14.BF.196.243; 14.BF.196.247; 14.BF.223.157; 14.BF.223.158; 14.BF.223.196; 14.BF.223.223; 14.BF.223.240; 14.BF.223.244; 14.BF.223.243; 14.BF.223.247; 14.BF.240.157;

TABLE 100-continued

| |
|---|
| 14.BF.240.158; 14.BF.240.196; 14.BF.240.223; 14.BF.240.240; 14.BF.240.244; 14.BF.240.243; 14.BF.240.247; 14.BF.244.157; 14.BF.244.158; 14.BF.244.196; 14.BF.244.223; 14.BF.244.240; 14.BF.244.244; 14.BF.244.243; 14.BF.244.247; 14.BF.247.157; 14.BF.247.158; 14.BF.247.196; 14.BF.247.223; 14.BF.247.240; 14.BF.247.244; 14.BF.247.243; 14.BF.247.247; |
| Prodrugs of 14.CI |
| 14.CI.4.157; 14.CI.4.158; 14.CI.4.196; 14.CI.4.223; 14.CI.4.240; 14.CI.4.244; 14.CI.4.243; 14.CI.4.247; 14.CI.5.157; 14.CI.5.158; 14.CI.5.196; 14.CI.5.223; 14.CI.5.240; 14.CI.5.244; 14.CI.5.243; 14.CI.5.247; 14.CI.7.157; 14.CI.7.158; 14.CI.7.196; 14.CI.7.223; 14.CI.7.240; 14.CI.7.244; 14.CI.7.243; 14.CI.7.247; 14.CI.15.157; 14.CI.15.158; 14.CI.15.196; 14.CI.15.223; 14.CI.15.240; 14.CI.15.244; 14.CI.15.243; 14.CI.15.247; 14.CI.16.157; 14.CI.16.158; 14.CI.16.196; 14.CI.16.223; 14.CI.16.240; 14.CI.16.244; 14.CI.16.243; 14.CI.16.247; 14.CI.18.157; 14.CI.18.158; 14.CI.18.196; 14.CI.18.223; 14.CI.18.240; 14.CI.18.244; 14.CI.18.243; 14.CI.18.247; 14.CI.26.157; 14.CI.26.158; 14.CI.26.196; 14.CI.26.223; 14.CI.26.240; 14.CI.26.244; 14.CI.26.243; 14.CI.26.247; 14.CI.27.157; 14.CI.27.158; 14.CI.27.196; 14.CI.27.223; 14.CI.27.240; 14.CI.27.244; 14.CI.27.243; 14.CI.27.247; 14.CI.29.157; 14.CI.29.158; 14.CI.29.196; 14.CI.29.223; 14.CI.29.240; 14.CI.29.244; 14.CI.29.243; 14.CI.29.247; 14.CI.54.157; 14.CI.54.158; 14.CI.54.196; 14.CI.54.223; 14.CI.54.240; 14.CI.54.244; 14.CI.54.243; 14.CI.54.247; 14.CI.55.157; 14.CI.55.158; 14.CI.55.196; 14.CI.55.223; 14.CI.55.240; 14.CI.55.244; 14.CI.55.243; 14.CI.55.247; 14.CI.56.157; 14.CI.56.158; 14.CI.56.196; 14.CI.56.223; 14.CI.56.240; 14.CI.56.244; 14.CI.56.243; 14.CI.56.247; 14.CI.157.157; 14.CI.157.158; 14.CI.157.196; 14.CI.157.223; 14.CI.157.240; 14.CI.157.244; 14.CI.157.243; 14.CI.157.247; 14.CI.196.157; 14.CI.196.158; 14.CI.196.196; 14.CI.196.223; 14.CI.196.240; 14.CI.196.244; 14.CI.196.243; 14.CI.196.247; 14.CI.223.157; 14.CI.223.158; 14.CI.223.196; 14.CI.223.223; 14.CI.223.240; 14.CI.223.244; 14.CI.223.243; 14.CI.223.247; 14.CI.240.157; 14.CI.240.158; 14.CI.240.196; 14.CI.240.223; 14.CI.240.240; 14.CI.240.244; 14.CI.240.243; 14.CI.240.247; 14.CI.244.157; 14.CI.244.158; 14.CI.244.196; 14.CI.244.223; 14.CI.244.240; 14.CI.244.244; 14.CI.244.243; 14.CI.244.247; 14.CI.247.157; 14.CI.247.158; 14.CI.247.196; 14.CI.247.223; 14.CI.247.240; 14.CI.247.244; 14.CI.247.243; 14.CI.247.247; |
| Prodrugs of 14.CO |
| 14.CO.4.157; 14.CO.4.158; 14.CO.4.196; 14.CO.4.223; 14.CO.4.240; 14.CO.4.244; 14.CO.4.243; 14.CO.4.247; 14.CO.5.157; 14.CO.5.158; 14.CO.5.196; 14.CO.5.223; 14.CO.5.240; 14.CO.5.244; 14.CO.5.243; 14.CO.5.247; 14.CO.7.157; 14.CO.7.158; 14.CO.7.196; 14.CO.7.223; 14.CO.7.240; 14.CO.7.244; 14.CO.7.243; 14.CO.7.247; 14.CO.15.157; 14.CO.15.158; 14.CO.15.196; 14.CO.15.223; 14.CO.15.240; 14.CO.15.244; 14.CO.15.243; 14.CO.15.247; 14.CO.16.157; 14.CO.16.158; 14.CO.16.196; 14.CO.16.223; 14.CO.16.240; 14.CO.16.244; 14.CO.16.243; 14.CO.16.247; 14.CO.18.157; 14.CO.18.158; 14.CO.18.196; 14.CO.18.223; 14.CO.18.240; 14.CO.18.244; 14.CO.18.243; 14.CO.18.247; 14.CO.26.157; 14.CO.26.158; 14.CO.26.196; 14.CO.26.223; 14.CO.26.240; 14.CO.26.244; 14.CO.26.243; 14.CO.26.247; 14.CO.27.157; 14.CO.27.158; 14.CO.27.196; 14.CO.27.223; 14.CO.27.240; 14.CO.27.244; 14.CO.27.243; 14.CO.27.247; 14.CO.29.157; 14.CO.29.158; 14.CO.29.196; 14.CO.29.223; 14.CO.29.240; 14.CO.29.244; 14.CO.29.243; 14.CO.29.247; 14.CO.54.157; 14.CO.54.158; 14.CO.54.196; 14.CO.54.223; 14.CO.54.240; 14.CO.54.244; 14.CO.54.243; 14.CO.54.247; 14.CO.55.157; 14.CO.55.158; 14.CO.55.196; 14.CO.55.223; 14.CO.55.240; 14.CO.55.244; 14.CO.55.243; 14.CO.55.247; 14.CO.56.157; 14.CO.56.158; 14.CO.56.196; 14.CO.56.223; 14.CO.56.240; 14.CO.56.244; 14.CO.56.243; 14.CO.56.247; 14.CO.157.157; 14.CO.157.158; 14.CO.157.196; 14.CO.157.223; 14.CO.157.240; 14.CO.157.244; 14.CO.157.243; 14.CO.157.247; 14.CO.196.157; 14.CO.196.158; 14.CO.196.196; 14.CO.196.223; 14.CO.196.240; 14.CO.196.244; 14.CO.196.243; 14.CO.196.247; 14.CO.223.157; 14.CO.223.158; 14.CO.223.196; 14.CO.223.223; 14.CO.223.240; 14.CO.223.244; 14.CO.223.243; 14.CO.223.247; 14.CO.240.157; 14.CO.240.158; 14.CO.240.196; 14.CO.240.223; 14.CO.240.240; 14.CO.240.244; 14.CO.240.243; 14.CO.240.247; 14.CO.244.157; 14.CO.244.158; 14.CO.244.196; 14.CO.244.223; 14.CO.244.240; 14.CO.244.244; 14.CO.244.243; 14.CO.244.247; 14.CO.4.157; 14.CO.4.158; 14.CO.4.196; 14.CO.4.223; 14.CO.4.240; 14.CO.4.244; 14.CO.4.243; 14.CO.4.247; |

Recursive Substituents

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $W^3$ will occur 0 to 8 times, $R^y$ will occur 0 to 6 times and $R^3$ will occur 0 to 10 times in a given embodiment. Even more typically, $W^3$ will occur 0 to 6 times, $R^y$ will occur 0 to 4 times and $R^3$ will occur 0 to 8 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Protecting Groups

In the context of the present invention, embodiments of protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PRT" will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect functional groups such as carboxyl, hydroxyl or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are embodiments of "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may not be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary embodiment of a phosphonate ester-forming group is the phenyl carbocycle in substructure $A_3$ having the formula:

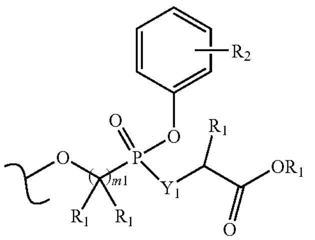

wherein m1 is 1, 2, 3, 4, 5, 6, 7 or 8, and the phenyl carbocycle is substituted with 0 to 3 $R_2$ groups. Also, in this embodiment, where $Y_1$ is O, a lactate ester is formed. Alternatively, where $Y_1$ is $N(R_2)$, $N(OR_2)$ or $N(N(R_2)_2$, then phosphonamidate esters result. $R_1$ may be H or $C_1$-$C_{12}$ alkyl. The corollary exemplary substructure $A^3$ is included in the invention with $Y^1$, $R^1$ and $R^2$ substituents.

In its ester-forming role, a protecting group typically is bound to any acidic group such as, by way of example and not limitation, a —$CO_2H$ or —C(S)OH group, thereby resulting in —$CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R^1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3 and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-, 3- and 4-acetylphenyl, 1,8-dihydroxynaphthyl ($—C_{10}H_6—OH$) and aryloxy ethyl [$C_6$-$C_9$ aryl (including phenoxy ethyl)], 2,2'-dihydroxybiphenyl, 2-, 3- and 4-N,N-dialkylaminophenol, $—C_6H_4CH_2—N(CH_3)_2$, trimethoxybenzyl, triethoxybenzyl, 2-alkyl pyridinyl ($C_{1-4}$ alkyl);

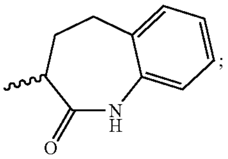

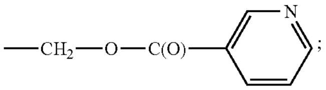

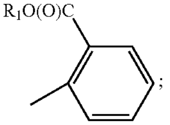

$C_4$-$C_8$ esters of 2-carboxyphenyl; and $C_1$-$C_4$ alkylene-$C_3$-$C_6$ aryl (including benzyl, $—CH_2$-pyrrolyl, $—CH_2$-thienyl, $—CH_2$-imidazolyl, $CH_2$-oxazolyl, $—CH_2$-isoxazolyl, $—CH_2$-thiazolyl, $—CH_2$-isothiazolyl, $—CH_2$-pyrazolyl, $—CH_2$-pyridinyl and $—CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including $—CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including $—CH_2—CH_2—O—CH_3$ (methoxy ethyl)]; alkyl substituted by any of the groups set forth above for aryl, in particular OH or by 1 to 3 halo atoms (including $—CH_3$, $—CH(CH_3)_2$, $—C(CH_3)_3$, $—CH_2CH_3$, $—(CH_2)_2CH_3$, $—(CH_2)_3CH_3$, $—(CH_2)_4CH_3$, $—(CH_2)_5CH_3$, $CH_2CH_2F$, $—CH_2CH_2Cl$, $—CH_2CF_3$, and $—CH_2CCl_3$);

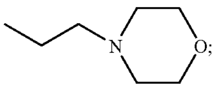

—N-2-propylmorpholino, 2,3-dihydro-6-hydroxyindene, sesamol, catechol monoester, $—CH_2—C(O)N(R^1)_2$, $—CH_2—S(O)(R^1)$, $—CH_2—S(O)_2(R^1)$, $—CH_2—CH(OC(O)CH_2R^1)—CH_2(OC(O)CH_2R^1)$, cholesteryl, enolpyruvate ($HOOC—C(=CH_2)—$), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671;

cyclic carbonates such as (5-$R_d$-2-oxo-1,3-dioxolen-4-yl) methyl esters (Sakamoto et al., *Chem. Pharm. Bull.* (1984) 32(6)2241-2248) where $R^d$ is $R_1$, $R_4$ or aryl; and

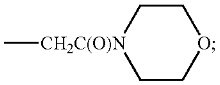

The hydroxyl groups of the compounds of this invention optionally are substituted with one of groups III, IV or V disclosed in WO 94/21604, or with isopropyl.

As further embodiments, Table A lists examples of protecting group ester moieties that for example can be bonded via oxygen to $—C(O)O—$ and $—P(O)(O—)_2$ groups. Several amidates also are shown, which are bound directly to $—C(O)—$ or $—P(O)_2$. Esters of structures 1-5,8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| 1. | $—CH_2—C(O)—N(R_1)_2$* |
| 2. | $—CH_2—S(O)(R_1)$ |
| 3. | $—CH_2—S(O)_2(R_1)$ |
| 4. | $—CH_2—O—C(O)—CH_2—C_6H_5$ |
| 5. | 3-cholesteryl |
| 6. | 3-pyridyl |
| 7. | N-ethylmorpholino |
| 8. | $—CH_2—O—C(O)—C_6H_5$ |
| 9. | $—CH_2—O—C(O)—CH_2CH_3$ |
| 10. | $—CH_2—O—C(O)—C(CH_3)_3$ |
| 11. | $—CH_2—CCl_3$ |
| 12. | $—C_6H_5$ |
| 13. | $—NH—CH_2—C(O)O—CH_2CH_3$ |
| 14. | $—N(CH_3)—CH_2—C(O)O—CH_2CH_3$ |
| 15. | $—NHR_1$ |
| 16. | $—CH_2—O—C(O)—C_{10}H_{15}$ |
| 17. | $—CH_2—O—C(O)—CH(CH_3)_2$ |
| 18. | $—CH_2—C$#$H(OC(O)CH_2R_1)—CH_2—(OC(O)CH_2R_1)$* |
| 19. | 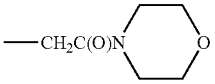 |
| 20. | 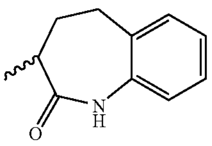 |
| 21. | 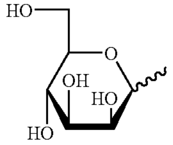 |

TABLE A-continued

| | |
|---|---|
| 22. | 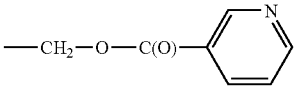 |
| 23. | 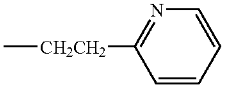 |
| 24. | 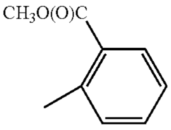 |
| 25. | 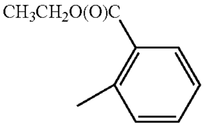 |
| 26. | 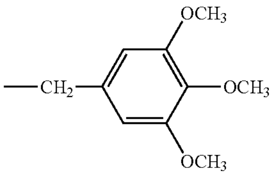 |

#-chiral center is (R), (S) or racemate.

Other esters that are suitable for use herein are described in EP 632048.

Protecting groups also includes "double ester" forming profunctionalities such as $—CH_2OC(O)OCH_3$,

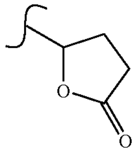

$—CH_2SCOCH_3$, $—CH_2OCON(CH_3)_2$, or alkyl- or aryl-acyloxyalkyl groups of the structure $—CH(R^1$ or $W^5)O((CO)R^{37})$ or $—CH(R^1$ or $W^5)((CO)OR^{38})$ (linked to oxygen of the acidic group) wherein $R^{37}$ and $R^{38}$ are alkyl, aryl, or alkylaryl groups (see U.S. Pat. No. 4,968,788). Frequently $R^{37}$ and $R^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including $—CH(CH_2CH_2OCH_3)OC(O)C(CH_3)_3$,

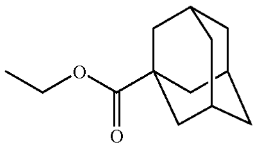

;

$—CH_2OC(O)C_{10}H_{15}$, $—CH_2OC(O)C(CH_3)_3$, $—CH(CH_2OCH_3)OC(O)C(CH_3)_3$, $—CH(CH(CH_3)_2)OC(O)C(CH_3)_3$, $—CH_2OC(O)CH_2CH(CH_3)_2$, $—CH_2OC(O)C_6H_{11}$, $—CH_2OC(O)C_6H_5$, $—CH_2OC(O)C_{10}H_{15}$, $—CH_2OC(O)CH_2CH_3$, $—CH_2OC(O)CH(CH_3)_2$, $—CH_2OC(O)C(CH_3)_3$ and $—CH_2OC(O)CH_2C_6H_5$.

For prodrug purposes, the ester typically chosen is one heretofore used for antibiotic drugs, in particular the cyclic carbonates, double esters, or the phthalidyl, aryl or alkyl esters.

In some embodiments the protected acidic group is an ester of the acidic group and is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under $R^{31}$ or $R^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

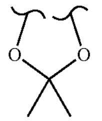

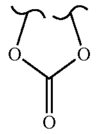

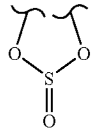

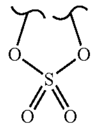

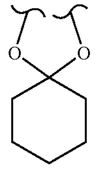

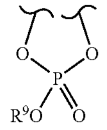

TABLE B-continued

| |
|---|
| 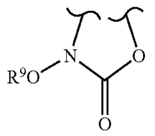 |
| 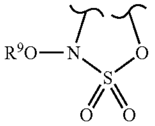 |
| 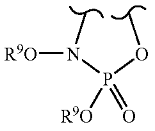 |
| 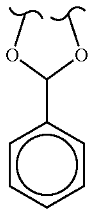 |

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

Protected amino groups include carbamates, amides and amidines, e.g. —NHC(O)OR$^1$, —NHC(O)R$^1$ or —N═CR$^1$N(R$^1$)$_2$. Another protecting group, also useful as a prodrug for amino or —NH(R$^5$), is:

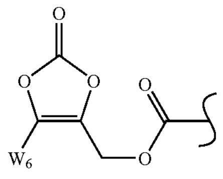

See for example Alexander, J. et al (1996) *J. Med. Chem.* 39:480-486.

Amino Acid and Polypeptide Protecting Group and Conjugates

An amino acid or polypeptide protecting group of a compound of the invention has the structure R$^{15}$NHCH(R$^{16}$)C(O)—, where R$^{15}$ is H, an amino acid or polypeptide residue, or R$^5$, and R$^{16}$ is defined below.

R$^{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. R$^{16}$ also is taken together with the amino acid α-N to form a proline residue (R$^{16}$═—$CH_2$)$_3$—). However, R$^{16}$ is generally the side group of a naturally-occurring amino acid such as H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —CH(OH)—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—C($NH_2$)—$NH_2$. R$^{16}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —$NHSO_2R$, NHC(O)R, —$N(R)_2$, $NH_2$ or —NH(R)(H), whereby for example a carboxylic acid is reacted, i.e. coupled, with the amine to form an amide, as in C(O)$NR_2$. A phosphonic acid may be reacted with the amine to form a phosphonamidate, as in —P(O)(OR)($NR_2$).

Amino acids have the structure R$^{17}$C(O)CH(R$^{16}$)NH—, where R$^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono-or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at R$^3$ of substituents A$^1$, A$^2$ or A$^3$ in Formula I, or substituted at $R_3$ of substituents $A_1$, $A_2$ or $A_3$ in Formula II. These conjugates are generally produced by forming an amide bond between a carboxyl group of the amino acid (or C-terminal amino acid of a polypeptide for example). Alternatively, conjugates are formed between R$^3$ (Formula I) or $R_3$ (Formula II) and an amino group of an amino acid or polypeptide. Generally, only one of any site in the scaffold drug-like compound is amidated with an amino acid as described herein, although it is within the scope of this invention to introduce amino acids at more than one permitted site. Usually, a carboxyl group of R$^3$ is amidated with an amino acid. In general, the α-amino or α-carboxyl group of the amino acid or the terminal amino or carboxyl group of a polypeptide are bonded to the scaffold, parental functionalities. Carboxyl or amino groups in the amino acid side chains generally may be used to form the amide bonds with the parental compound or these groups may need to be protected during synthesis of the conjugates as described further below.

With respect to the carboxyl-containing side chains of amino acids or polypeptides it will be understood that the carboxyl group optionally will be blocked, e.g. by R$^1$, esterified with R$^5$ or amidated. Similarly, the amino side chains R$^{16}$ optionally will be blocked with R$^1$ or substituted with R$^5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used.

In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β, γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, βaminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α, α'-diaminosuccinic acid, α, α'-diaminoglutaric acid, α, α'-diaminoadipic acid, α, α'-diaminopimelic acid, α, α'-diamino-β-hydroxypimelic acid, α, α'-diaminosuberic acid, α, α'-diaminoazelaic acid, and α, α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ϵ-hydroxycaproic acid, isovaline, α-methylglutamic acid, α-aminoisobutyric acid, α-aminodiethylacetic acid, α-aminodiisopropylacetic acid, α-aminodi-n-propylacetic acid, αaminodiisobutylacetic acid, α-aminodi-n-butylacetic acid, α-aminoethylisopropylacetic acid, α-amino-n-propylacetic acid, α-aminodiisoamyacetic acid, α-methylaspartic acid, αmethylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ϵ-hydroxy acids such as homoserine, δ-hydroxynorvaline, γ-hydroxynorvaline, and ϵ-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, p-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may be immunogenic in an animal typically used to raise antibodies, e.g., rabbit, mouse, horse, or rat. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases, which digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In certain embodiments, a phosphonate group substituted with an amino acid or peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, A, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CT, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, EN, ED, FC, FE, FQ, FG, FH, FH, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$-pro-$X^5$— (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978. Transport competent peptides can thus be used to enhance bioavailability of the amidate compounds. Di- or tripeptides having one or more amino acids in the D configuration may be compatible with peptide transport. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Phosphonate Analogs of known Experimental or Approved Protease Inhibitor Drugs

The known experimental or approved protease inhibitor drugs which can be derivatized in accord with the present invention must contain at least one functional group capable of linking, i.e. bonding to the phosphorus atom in the phosphonate moiety. The phosphonate derivatives of Formulas I-VIII may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in Formulas I-VIII thus affords an unstable intermediate which releases a negatively charged "locked in" intermediate.

After passage inside a cell, intracellular enzymatic cleavage or modification of the phosphonate prodrug compound may result in an intracellular accumulation of the cleaved or modified compound by a "trapping" mechanism. The cleaved or modified compound may then be "locked-in" the cell, i.e. accumulate in the cell by a significant change in charge, polarity, or other physical property change which decreases the rate at which the cleaved or modified compound can exit the cell, relative to the rate at which it entered as the phosphonate prodrug. Other mechanisms by which a therapeutic effect is achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

In selected instances in which the drug is of the nucleoside type, such as is the case of zidovudine and numerous other antiretroviral agents, it is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be converted, via the derivatives of this invention, to the active phosphorylated species.

From the foregoing, it will be apparent that many structurally different known approved and experimental HIV protease inhibitor drugs can be derivatized in accord with the present invention. Numerous such drugs are specifically mentioned herein. However, it should be understood that the discussion of drug families and their specific members for derivatization according to this invention is not intended to be exhaustive, but merely illustrative.

As another example, when the selected drug contains multiple reactive hydroxyl functions, a mixture of intermediates and final products may again be obtained. In the unusual case in which all hydroxy groups are approximately equally reactive, there is not expected to be a single, predominant product, as each mono-substituted product will be obtained in approximate by equal amounts, while a lesser amount of multiply-substituted product will also result. Generally speaking, however, one of the hydroxyl groups will be more susceptible to substitution than the other(s), e.g. a primary hydroxyl will be more reactive than a secondary hydroxyl, an unhindered hydroxyl will be more reactive than a hindered one. Consequently, the major product will be a mono-substituted one in which the most reactive hydroxyl has been derivatized while other mono-substituted and multiply-substituted products may be obtained as minor products.

Formula I compounds having a 3-hydroxy-5-amino-pentamide core include Indinavir-like phosphonate protease inhibitors (ILPPI). Compounds of the invention include phosphonate analogs of other known PI compounds with a 3-hydroxy-5-amino-pentamide core which have been identified as CGP-49689, CGP-53437, CGP-57813 (Novartis); L-689502, L-693549, L-748496, L-754394, MK-944a, Iddb63, Iddb88

(Merck); Lasinavir (Bristol-Myers Squibb); U-81749 (PNU/Pfizer); SB-203386, SKF-108922 (SmithKline Beecham).

I

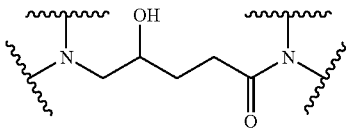

Formula II compounds having a 2-hydroxy-1,3-amino-propylamide or 2-hydroxy-1,3-amino-propylaminosulfone core include Amprenavir-like phosphonate protease inhibitors (AMLPPI). Compounds of the invention include phosphonate analogs of other known PI compounds with a 2-hydroxy-3-amido-propylamide or 2-hydroxy-3-amido-propylaminosulfone core which have been identified as Droxinavir, Telinavir, Iddb51 (Searle); Ph4556 (WO 95/29922; Ph5145 (WO 96/31527; DPC-681, DPC-684 (DuPont); VB-11328 (Vertex); TMC-114 (Tibotech/Johnson & Johnson). Formula II compounds also include phosphonate analogs of fosamprenavir where the 2-hydroxy is phosphorylated, i.e. having a or 2-phosphate-1,3-amino-propylaminosulfone core (U.S. Pat. No. 6,436,989).

II

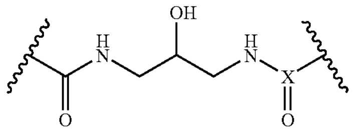

X = C, SO

The embodiments of the invention also include the following phosphonate analogs of Formula II, represented as Formulas IIa-Ig:

IIa

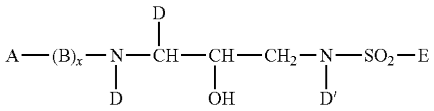

described as "(I)" in: WO 94/05639 (published Mar. 17, 1994) at page 4, line 15, to page 6, line 27, page 15, line 21, to page 17, line 33, and Claim 1; U.S. Pat. No. 5,585,397 (issued 17 Dec. 1996) at col. 2, line 45, to col. 3, line 53, and col. 8, line 1, to col. 9, line 12; U.S. Pat. No. 5,783,701 (issued Jul. 21, 1998) at col. 2, line 43, to col. 3, line 64, col. 8, line 13, to col. 9, line 33, and Claim 1; U.S. Pat. No. 5,856,353 (issued Jan. 5, 1999) at col. 2, line 45, to col. 3, line 65, col. 8, line 14, to col. 9, line 37, and Claim 1; U.S. Pat. No. 5,977,137 (issued Nov. 2, 1999) at col. 2, line 43, to col. 3, line 65, col. 8, line 15, to col. 9, line 38, and Claim 1; and U.S. Pat. No. 6,004,957 (issued Dec. 21, 1999) at col. 2, line 47, to col. 4, line 3, col. 8, line 18, to col. 9, line 41, and Claim 1 therein.

IIb

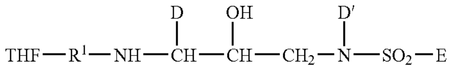

described as "(1)" in: WO 96/33184 (published Oct. 24, 1996) at page 4, line 19, to page 6, line 5, page 17, line 11, to page 19, line 31, and Claim 1; and U.S. Pat. No. 5,723,490 (issued Mar. 3, 1998) at col. 2, line 49, to col. 3, line 39, col. 8, line 66, to col. 10, line 36, and Claim 1.

IIc

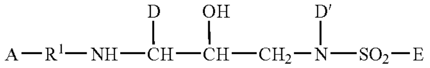

described as "(I)" in: WO 96/33187 (published Oct. 24, 1996) at page 4, line 23, to page 6, line 18, page 18, line 8, to page 21, line 18, and Claims 1 and 6; U.S. Pat. No. 5,691,372 (issued Nov. 24, 1997) at col. 2, line 43, to col. 3, line 47, col. 9, line 21, to col. 11, line 5, and Claims 1 and 5; and U.S. Pat. No. 5,990,155 (issued Nov. 23, 1999) at col. 2, line 46, to col. 3, line 55, col. 9, line 25, to col. 11, line 13, and Claims 1 and 3.

IId

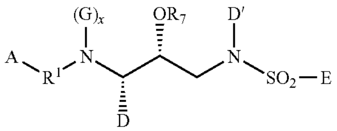

described as "(I)" in: WO 99/33793 (published Jul. 8, 1999) at page 4, line 1, to page 7, line 29, page 17, line 1, to page 20, line 33, and Claim 1.

IIe

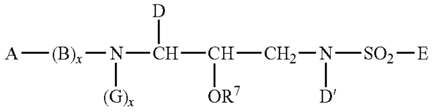

described as "(I)" in: WO 99/33815 (published Jul. 8, 1999) at page 4, line 1, to page 7, line 19, page 12, line 18, to page 16, line 7, and Claim 1; and WO 99/65870 (published Dec. 23, 1999) at page 4, line 7, to page 8, line 4, page 12, line 7, to page 16, line 4, and Claim 1.

IIf

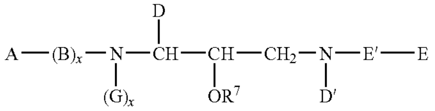

described as "(1)" in: WO 00/47551 (published Aug. 17, 2000) at page 4, line 10, to page 8, line 29, page 13, line 14, to page 17, line 32, and Claim 1.

IIg

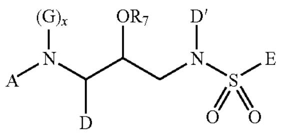

described as "(I)" in: WO 00/76961 (published Dec. 21, 2000) at page 5, line 1, to page 10, line 24, page 14, line 28, to page 20, line 21, and Claim 1.

IIh

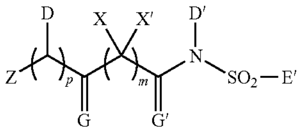

described as "(I)" in: WO 99/33792 (published Jul. 8, 1999) at page 4, line 5, to page 7, line 35, page 17, line 10, to page 21, line 6, and Claim 1; WO 95/24385 (published Sep. 14, 1995) at page 4, line 24, to page 7, line 14, page 16, line 20, to page 19, line 8, and Claims 1 and 29; and U.S. Pat. No. 6,127,372 (issued Oct. 3, 2000) at col. 2, line 58, to col. 4, line 28, col. 8, line 66, to col. 10, line 37, and Claim 1.

Formula III compounds having a 2-hydroxy-3-amino-propylamide core include KNI-like phosphonate protease inhibitors (KNILPPI). Compounds of the invention include phosphonate analogs of other known PI compounds with a 2-hydroxy-3-amido-propylamide or 2-hydroxy-3-amido-propylaminosulfone core which have been identified as KNI-764 (JE-2147, AG1776); KNI-102, KNI-227, KNI-241, KNI-272, KNI-413, KNI-549, KNI-577, KNI-727, JE-2178 (Japan Energy); Ph3939 (EP 587311); R-87366, Iddb134 (Sankyo); VLE-776 (Scripps Institute).

III

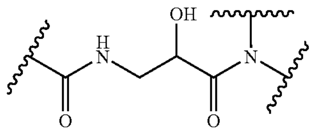

Formula IV compounds having a 2-hydroxy-4-amino-butylamine core include Ritonavir-like phosphonate protease inhibitors (RLPPI) and Lopinavir-like phosphonate protease inhibitors (LLPPI). Compounds of the invention include phosphonate analogs of other known PI compounds with a 2-hydroxy-4-amino-butylamine core which have been identified as A-76928, A-80735, A-80987 (Abbott Laboratories).

IV

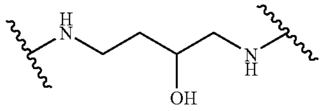

Formula V compounds having an acylated 1,3-diaminopropane core include Saquinavir-like phosphonate protease inhibitors (SLPPI) and Nelfinavir-like phosphonate protease inhibitors (NLPPI). Compounds of the invention include phosphonate analogs of other known PI compounds with an acylated 1,3-diaminopropane core which have been identified as Ro-33-2910, Ro-33-4649 (Hofman La Roche); BMS-182193, BMS-186318, BMS-187071 (Bristol-Myers Squibb); JG-365 (Univ. of Wisconsin); L-704325, L-738872, L-739594, L-743770 (Merck & Co.); LB-71206 (LG Chemical Ltd.); LY-296242, LY-314163, LY-316683, LY-326620 (Eli Lilly Co.), Palinavir (BioMega/B1); Ph5640, Ph6090 (WO 97/21100).

V

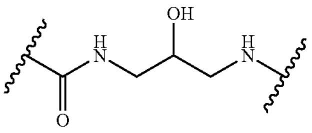

Formula VI compounds having a 2-hydroxy-3-diaza-propylamide core include Atazanavir-like phosphonate protease inhibitors (ATLPPI). Compounds of the invention include phosphonate analogs of other known PI compounds with a 2-hydroxy-3-diaza-propylamide core which have been identified as CGP-56603, CGP-53820, CGP-70726 (Novartis), ABT-538 (Abbott Laboratories), and DG-35 (National Cancer Institute).

VI

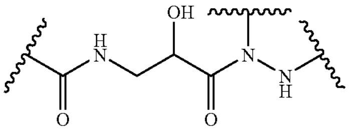

Formula VII compounds having sulfonamide 5,6-dihydro-4-hydroxy-2-pyrone core include Tipranavir-like phosphonate protease inhibitors (TLPPI).

VII

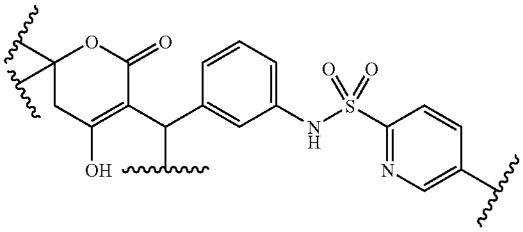

Formula VIII compounds have a six or seven-membered ring, cyclic carbonyl, sulfone, or sulfonyl core, where $Y^1$ is oxygen, sulfur, or substituted nitrogen and M2 is 1 or 2. The invention includes Cyclic carbonyl-like phosphonate protease inhibitor compounds (CCLPPI), e.g. Formula VIIIa-d.

VIIIa

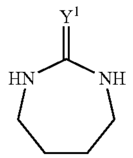

VIIIb

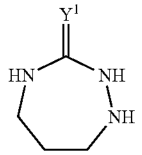

VIIIc

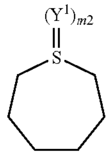

and

VIIId

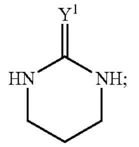

Cyclic carbonyl protease inhibitors without a phosphonate group are described in U.S. Pat. Nos. RE37,781; 6,503,898; 5,880,295; 5,811,422; 5,610,294; 5,559,252; and 5,506,355, as well as patent applications and granted patents which are equivalents of, or related by priority claims thereto. CCLPPI compounds also include phosphonate analogs of:

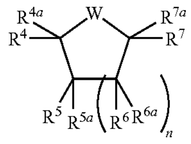

described as "(I)" in WO 94/19329 (published Sep. 1, 1994) at page 4, line 23, to page 21, line 16 and Claim 1. Also contemplated are patent applications and granted patents which are equivalents of or related by priority claims to WO 94/19329.

Stereoisomers

The compounds of the invention, exemplified by Formula I and II, may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt may be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HIV Protease

Another aspect of the invention relates to methods of inhibiting the activity of HIV protease comprising the step of treating a sample suspected of containing HIV with a composition of the invention.

Compositions of the invention may act as inhibitors of HIV protease, as intermediates for such inhibitors or have other utilities as described below. The inhibitors will bind to locations on the surface or in a cavity of HIV protease having a geometry unique to HIV protease. Compositions binding HIV protease may bind with varying degrees of reversibility. Those compounds binding substantially irreversibly are ideal candidates for use in this method of the invention. Once labeled, the substantially irreversibly binding compositions are useful as probes for the detection of HIV protease. Accordingly, the invention relates to methods of detecting HIV protease in a sample suspected of containing HIV protease comprising the steps of: treating a sample suspected of containing HIV protease with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HIV protease include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HIV protease, frequently a pathogenic organism such as HIV. Samples can be contained in any medium including water and organic solvent-water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HIV protease after application of the composition can be observed by any method including direct and indirect methods of detecting HIV protease activity. Quantitative, qualitative, and semiquantitative methods of determining HIV protease activity are all contemplated. Typically one of the screening methods described above are applied, however, any other method such as observation of the physiological properties of a living organism are also applicable.

Organisms that contain HIV protease include the HIV virus. The compounds of this invention are useful in the treatment or prophylaxis of HIV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HIV protease Inhibitors.

Compositions of the invention are screened for inhibitory activity against HIV protease by any of the conventional techniques for evaluating enzyme activity. Within the context of the invention, typically compositions are first screened for inhibition of HIV protease in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. Such combinations are selected based on the condition to be treated, cross-reactivities of ingredients and pharmaco-properties of the combination. For example, when treating viral infections the compositions of the invention may be combined with other antivirals such as other protease inhibitors, nucleoside reverse transcriptase inhibitors, non-nucleoside reverse transcriptase inhibitors or HIV integrase inhibitors.

It is possible to combine any compound of the invention with one or more other active ingredients in a unitary dosage form for simultaneous or sequential administration to an HIV infected patient. The combination therapy may be administered as a simultaneous or sequential regimen. When administered sequentially, the combination may be administered in two or more administrations. Second and third active ingredients in the combination may have anti-HIV activity. Exemplary active ingredients to be administered in combination with compounds of the invention are protease inhibitors, nucleoside reverse transcriptase inhibitors, non-nucleoside reverse transcriptase inhibitors, and HIV integrase inhibitors.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HIV protease inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but may be substantially hydrolyzed to the parental drug in the digestive lumen, liver or other metabolic organ, or within cells in general.

Exemplary Methods of Making the Compounds of the Invention.

The invention provides many methods of making the compositions of the invention. The compositions are prepared by any of the applicable techniques of organic synthesis. Many such techniques are well known in the art, such as those elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

Dialkyl phosphonates may be prepared according to the methods of: Quast et al (1974) Synthesis 490; Stowell et al (1990) *Tetrahedron Lett.* 3261; U.S. Pat. No. 5,663,159.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) J. *Chem. Soc. Perkin Trans. I,* 1577). Chlorophosphonate species may also be generated in situ from corresponding cyclic phosphites (Silverburg, et al., (1996) *Tetrahedron Lett.,* 37:771774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron Lett.,* 29:5763-66). Caution: fluorophosphonate compounds may be highly toxic!

Phosphonate prodrugs of the present invention may also be prepared from the precursor free acid by Mitsunobu reactions (Mitsunobu, (1981) *Synthesis,* 1; Campbell, (1992) *J. Org. Chem.,* 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.,* 2:145; Ohashi, et al, (1988) *Tetrahedron Lett.,* 29:1189), and benzotriazolyloxytris-(dimethylamino)phosphonium salts (Campagne, et al, (1993) *Tetrahedron Lett.,* 34:6743).

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis, et al, (1987) *J. Am. Chem. Soc.* 109:2831; Lu, et al, (1987) *Synthesis,* 726). In another method, aryl phosphonate esters are prepared from aryl phosphates under anionic rearrangement conditions (Melvin (1981) Tetrahedron Lett. 22:3375; Casteel, et al, (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The carbamoyl group may be formed by reaction of a hydroxy group according to the methods known in the art, including the teachings of Ellis, US 2002/0103378 A1 and Hajima, U.S. Pat. No. 6,018,049.

SCHEMES AND EXAMPLES

A number of exemplary methods for the preparation of the compositions of the invention are provided below. These methods are intended to illustrate the nature of such preparations are not intended to limit the scope of applicable methods.

General aspects of these exemplary methods are described below and in the Examples. Each of the products of the following processes is optionally separated, isolated, and/or purified prior to its use in subsequent processes.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes above and in the examples (hereafter "exemplary schemes") leads to various analogs of the specific exemplary materials produce. The above cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.,* 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

EXAMPLES GENERAL SECTION

The following Examples refer to the Schemes.

Some Examples have been performed multiple times. In repeated Examples, reaction conditions such as time, temperature, concentration and the like, and yields were within normal experimental ranges. In repeated Examples where significant modifications were made, these have been noted where the results varied significantly from those described. In Examples where different starting materials were used, these are noted. When the repeated Examples refer to a "corresponding" analog of a compound, such as a "corresponding ethyl ester", this intends that an otherwise present group, in this case typically a methyl ester, is taken to be the same group modified as indicated.

In a number of the following schemes, the term "etc" appears as a substituent on chemical structures and as a term within the schemes. When used in the charts, the term is defined for each chart. When the term "etc" appears in a scheme and is not a substituent on a chemical structure, it means "and the like".

Saquinavir-like Phosphonate Protease Inhibitors (SLPPI)

Preparation of the Intermediate Phosphonate Esters.

The structures of the intermediate phosphonate esters 1 to 6, and the structures for the component groups $R^1$, $R^4$ and $R^7$ of this invention are shown in Chart 1.

The structures of the $R^2NHCH(R^3)CONHR^4$ and $R^5XCH_2$ components are shown in Charts 2 and 2a, and the structures of the $R^6COOH$ components are shown in Charts 3a, 3b and 3c. Specific stereoisomers of some of the structures are shown in Charts 1, 2 and 3; however, all stereoisomers are utilized in the syntheses of the compounds 1 to 6. Subsequent chemical modifications to the compounds 1 to 6, as described herein, permit the synthesis of the final compounds of this invention.

The intermediate compounds 1 to 6 incorporate a phosphonate moiety $(R^1O)_2P(O)$ connected to the nucleus by means of a variable linking group, designated as "link" in the attached structures. Charts 4 and 5 illustrate examples of the linking groups present in the structures 1-5, and in which "etc" refers to the scaffold, e.g., saquinavir.

CHART 1

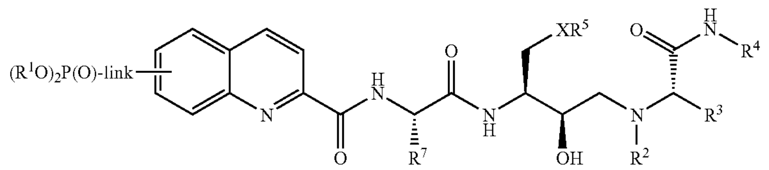

1

CHART 1-continued
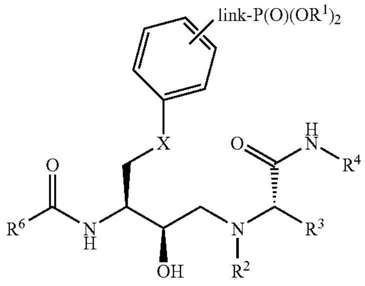
2
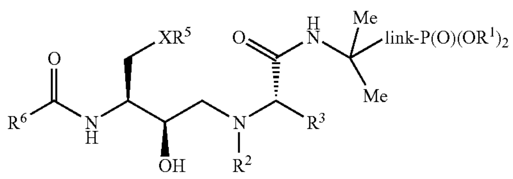
3
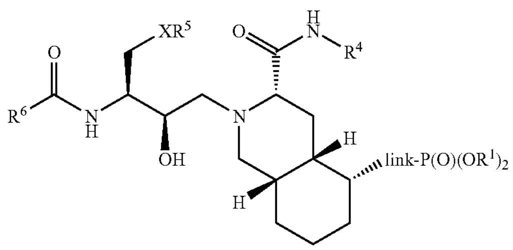
4
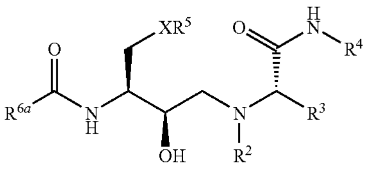
5
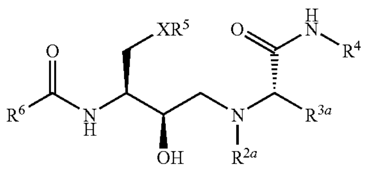
6
$R^{6a}$ = phosphonate-containing $R^6$
$^{2a}$, $R^{3a}$ = phosphonate-containing $R^2$ or $R^3$
$R^1$ = H, alkyl, haloalkyl, alkenyl, aralkyl, aryl
$R^4$ = $CH(CH_3)_3$; $CH_2CF_3$; $CH_2C_6H_4(CH_3)$-2
$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
X = S, direct bond CHART 2
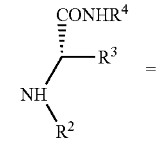
1.2
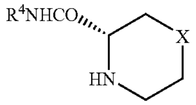
A1
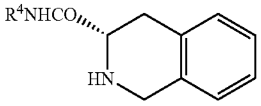
A2
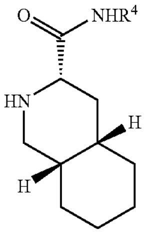
A3
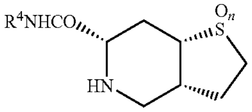
A4
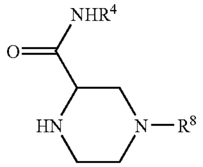
A5
$R^8$ =
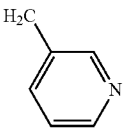
A6
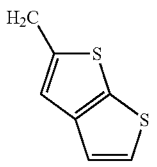
A7
CHART 2-continued
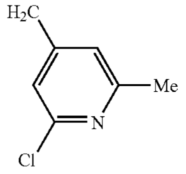
A8
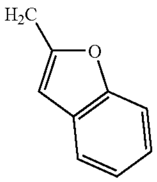
A9
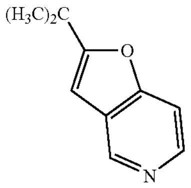
A10
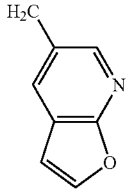
A11
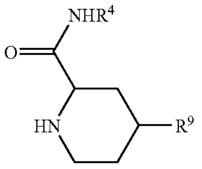
A12
$R^9$ = $OCH_2Ph$
S-3-pyridyl
S-4-pyridyl
$OCH_2$-4-pyridyl
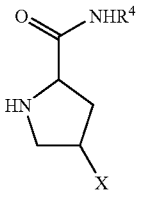
A13
X = Cl, OMe CHART 2-continued
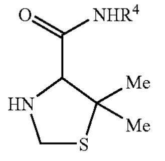
A14
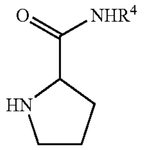
A15
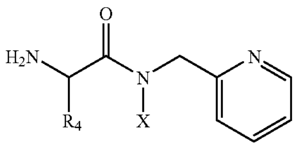
X = H or Me
A16
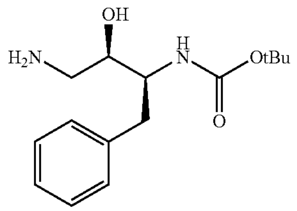
A17
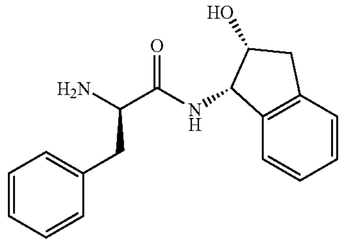
A18
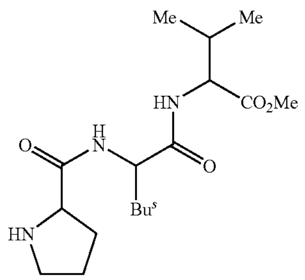
A19
CHART 2-continued
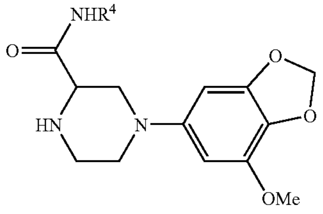
A20
CHART 2a
$R^5CH_2X$ =
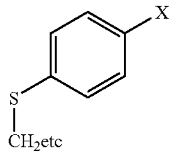
21
X = H, F
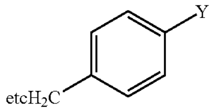
22
Y = H, $OC_2H_5$, $OCH_2C_6H_5$
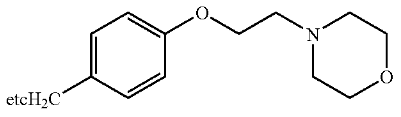
23
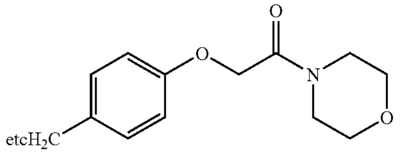
24
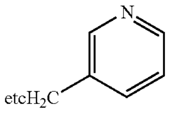
25
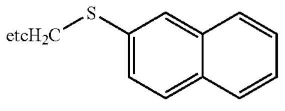
26

CHART 3a
Structures of the $R^6COOH$ components
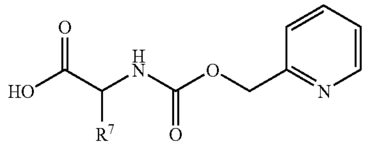
C1
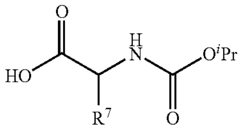
C2
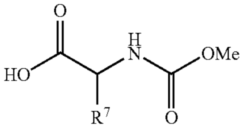
C3
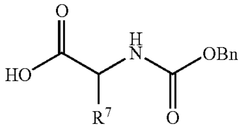
C4
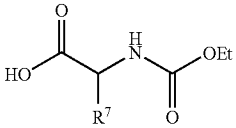
C5
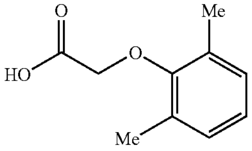
C6
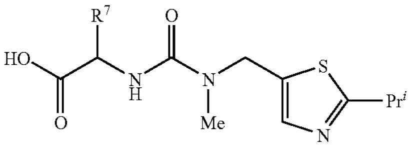
C7
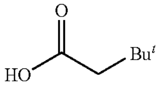
C8
CHART 3a-continued
Structures of the $R^6COOH$ components
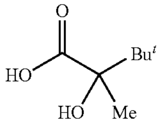
C9
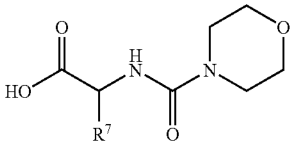
C10
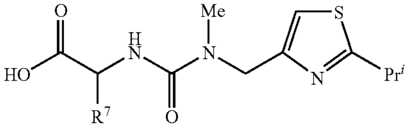
C11
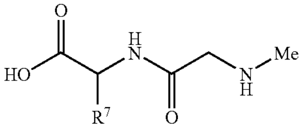
C12
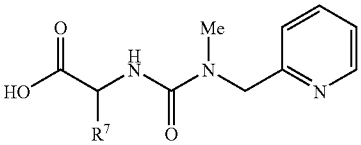
C13
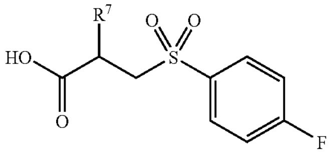
C14
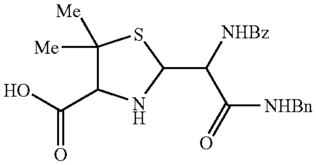
C15
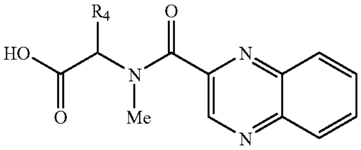
C16

CHART 3a-continued
Structures of the $R^6COOH$ components
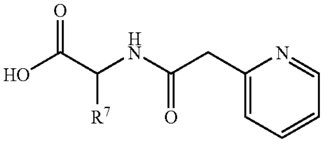
C17
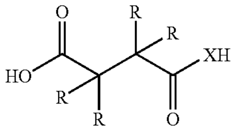
X = O, NH
R = H, alkyl
C18
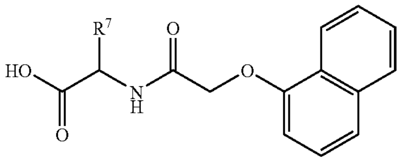
C19
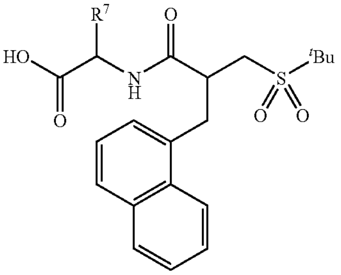
C20
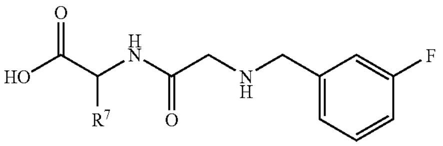
C21
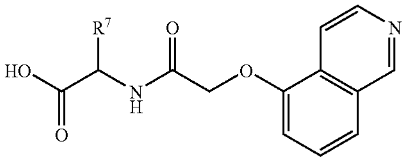
C22
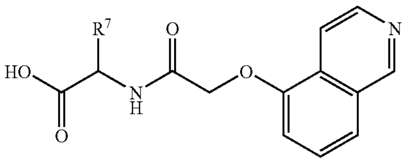
CHART 3a-continued
Structures of the $R^6COOH$ components
C23
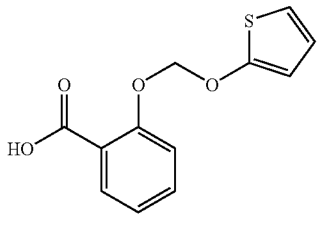
C24
$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 3b
Structures of the $R^6COOH$ components
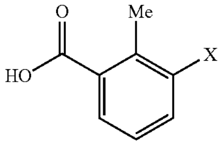
C25
X = OH, $NH_2$
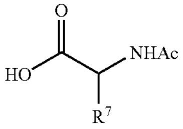
C26
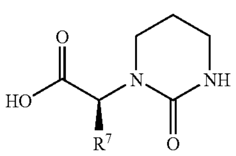
C27
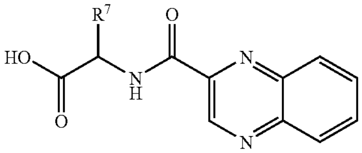
C28
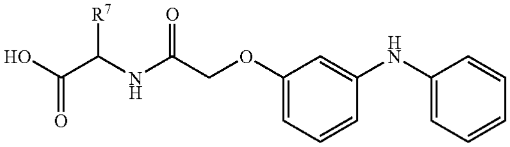
C29
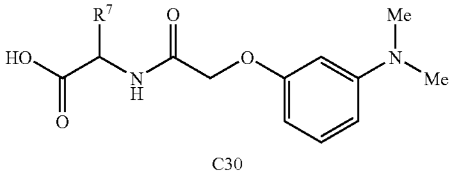
C30

CHART 3b-continued
Structures of the $R^6COOH$ components
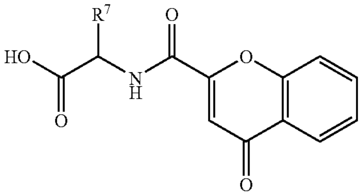
C31
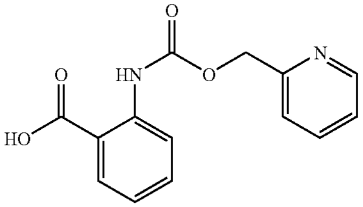
C32
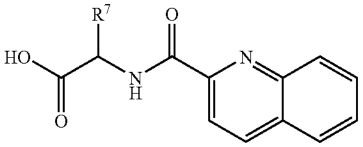
C33
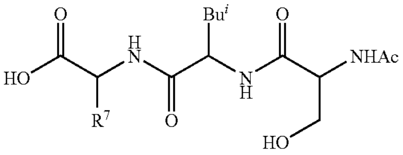
C34
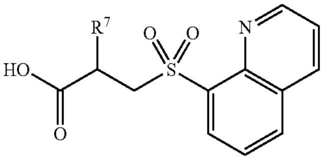
C35
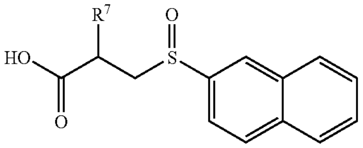
C36
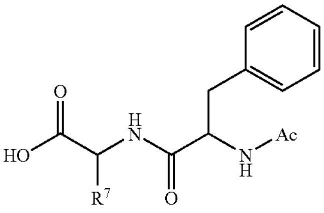
C37
CHART 3b-continued
Structures of the $R^6COOH$ components
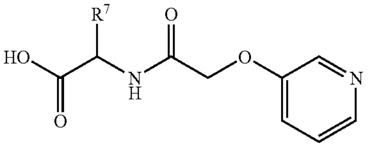
C38
$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 3c
Structures of the $R^6COOH$ components
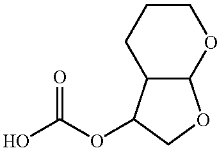
C38
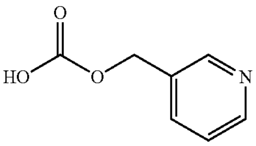
C39
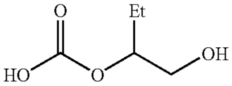
C40
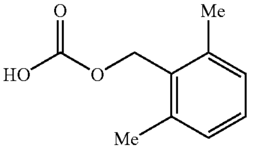
C41
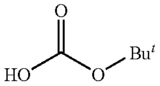
C42
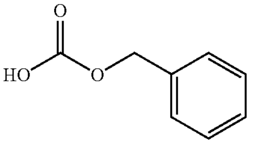
C43
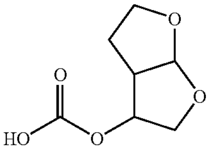
C44
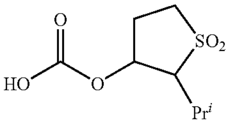
C45
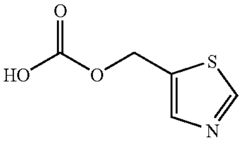
C46
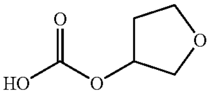
C47
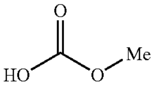
C48
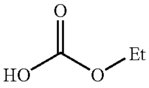
C49

CHART 4
Examples of the linking group between the scaffold and the phosphonate moiety.
| link | examples |
| --- | --- |
| direct bond | 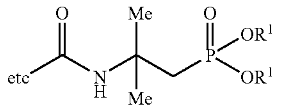 38 |
| | 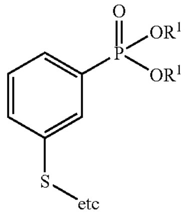 39 |
| | 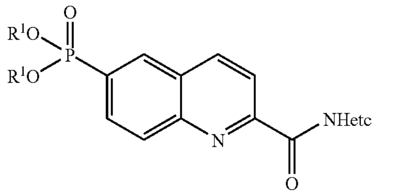 40 |
| single carbon | 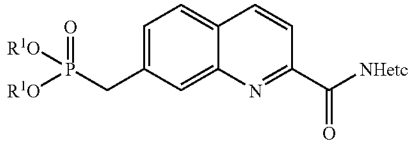 41 |
| | 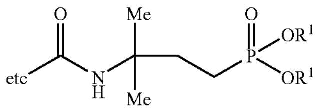 42 |
| | 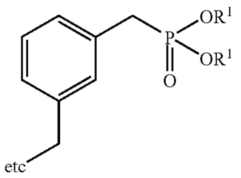 43 |
| multiple carbon | 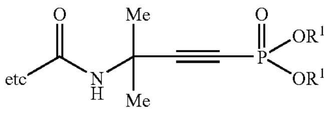 44 |
| | 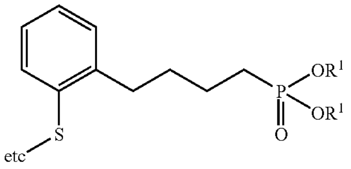 45 |
CHART 4-continued
Examples of the linking group between the scaffold and the phosphonate moiety.
| link | examples |
| --- | --- |
| | 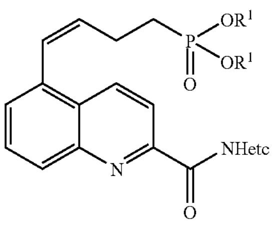 46 |
| hetero atoms | 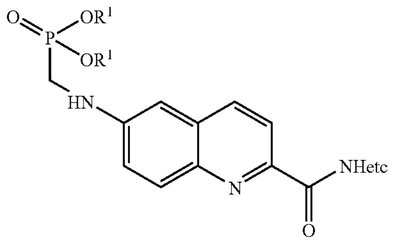 47 |
| | 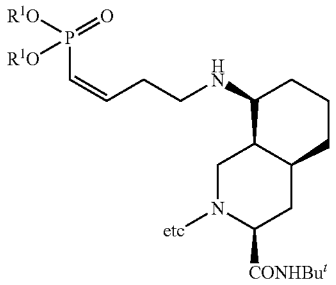 48 |
| | 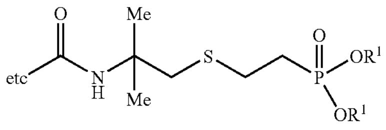 49 |
| | 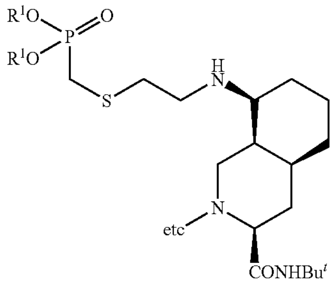 50 |

CHART 4-continued

Examples of the linking group between the scaffold and the phosphonate moiety.

| link | examples |
|---|---|
| | 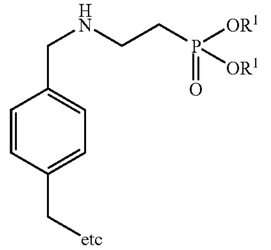 51 |
| | 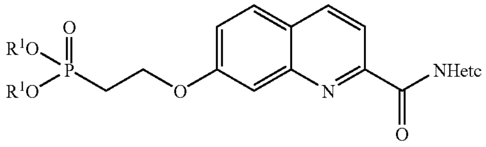 52 |

CHART 5

Examples of the linking group between the scaffold and the phosphonate moiety.

| link | examples |
|---|---|
| aryl, heteroaryl | 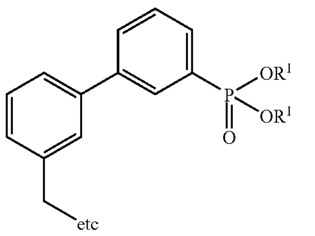 53 |
| | 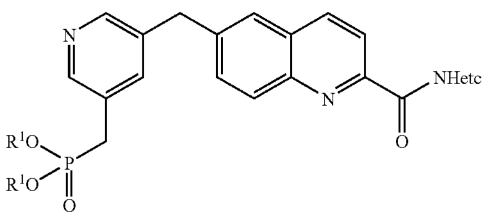 55 |
| cycloalkyl | 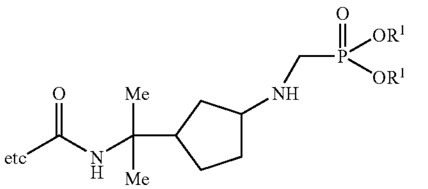 56 |
| | 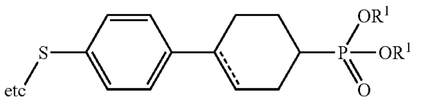 57 |

CHART 5-continued

Examples of the linking group between the scaffold and the phosphonate moiety.

| link | examples |
|---|---|
| cyclized | 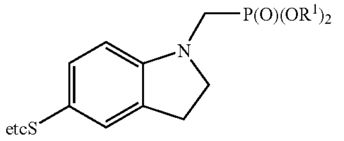 58 |
| | 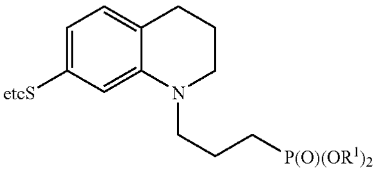 59 |

Schemes 1-69 illustrate the syntheses of the intermediate phosphonate compounds of this invention, 1-4, and of the intermediate compounds necessary for their synthesis. The preparation of the phosphonate esters 5 and 6, in which the phosphonate moiety is incorporated into the groups $R^6COOH$ and $R^2NHCH(R^3)CONHR^4$, are also described below.

Protection of the Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990. Reactive substituents which may be protected are shown in the accompanying schemes as, for example, [OH], [SH].

Preparation of the Phosphonate Intermediates 1.

Scheme 1 illustrates one method for the preparation of the phosphonate esters 1.6 in which X is a direct bond. In this procedure, an amine $R^2NHCH(R^3)CONHR^4$ 1.2 is reacted with an epoxide 1.1 to afford the aminoalcohol 1.3. The preparation of the epoxide 1.1 is described below, (Scheme 2) The preparation of aminoalcohols by reaction between an amine and an epoxide is described, for example, in Advanced Organic Chemistry, by J. March, McGraw Hill, 1968, p 334. In a typical procedure, equimolar amounts of the reactants are combined in a polar solvent such as an alcohol or dimethylformamide and the like, at from ambient to about 100°, for from 1 to 24 hours, to afford the product 1.3. The carbobenzyloxy protecting group is then removed. The removal of carbobenzyloxy protecting groups is described, for example, in Protective Groups in Organic Synthesis, by T. W. Greene and P. G. M Wuts, Wiley, Second Edition 1990, p 335. The reaction can be effected by means of catalytic hydrogenation in the presence of hydrogen or a hydrogen donor, by reaction with a Lewis acid such as aluminum chloride or boron tribromide, or by basic hydrolysis, for example employing barium hydroxide in an aqueous organic solvent mixture. Preferably, the protected amine 1.3 is converted into the free amine 1.4 by means of hydrogenation over 10% palladium on carbon catalyst in ethanol, as described in U.S. Pat. No. 5,196,438. The amine product 1.4 is then reacted with a carboxylic acid 1.5 to afford the amide 1.6. The coupling reaction of amines 1.4 and a carboxylic acid 1.5 can be effected under a variety of conditions, for example as described in Comprehensive Organic Transformations, by R. C. Larock, VCH, 1989, p. 972ff. The carboxylic acid can be activated by conversion to an imidazolide, mixed anhydride or active ester such as, for example, the ester with hydroxybenztriazole or N-hydroxysuccimirde. Alternatively, the reactants can be combined in the presence of a carbodiimide, such as, for example, dicyclohexylcarbodiimide or diisopropylcarbodiimide, to afford the amide product 1.6. Preferably, equimolar amounts of the amine and the carboxylic acid are reacted in tetrahydrofuran at ca. −10°, in the presence of dicyclohexylcarbodiimide, as described in U.S. Pat. No. 5,196,438, to afford the amide 1.6. The carboxylic acid 1.5 employed in the above reaction is obtained by means of the reaction between the substituted quinoline-2-carboxylic acid 1.7, in which the substituent A is either the group link-$P(O)(OR^1)_2$ or a precursor group thereto, such as [OH], [SH], Br, as described below, and an aminoacid 1.8. The reaction is performed under similar conditions to those described above for the preparation of the amide 1.6. Preferably, the quinoline carboxylic acid 1.7 is reacted with N-hydroxy succinimide and a carbodiimide to afford the hydroxysuccinimide ester, which is then reacted with the aminoacid 1.8 in dimethylformamide at ambient temperature for 2-4 days, as described in U.S. Pat. No. 5,196,438, to afford the amide product 1.5. The preparation of the substituted quinoline carboxylic acids 1.7 is described below, Schemes 24-27.

Scheme 2 illustrates the preparation of the epoxides 1.1 used above in Scheme 1. The preparation of the epoxide 1.1 in which $R^{10}$ is H is described in J. Med. Chem., 1997, 40, 3979. Analogs in which $R^{10}$ is one of the substituents defined in Chart 2 are prepared as shown in Scheme 2. A substituted phenylalanine 2.1 is first converted into the benzyloxycarbonyl derivative 2.2. The preparation of benzyloxycarbonyl amines is described in Protective Groups in Organic Synthesis, by T. W. Greene and P. G. M Wuts, Wiley, Second Edition 1990, p. 335. The aminoacid 2.1 is reacted with benzyl chloroformate or dibenzyl carbonate in the presence of a suitable base such as sodium carbonate or triethylamine, to afford the protected amine product 2.2. The conversion of the carboxylic acid 2.2 into the epoxide 1.1 for example using the sequence of reactions which is described in J. Med. Chem., 1994, 37, 1758, is then effected. The carboxylic acid is first converted into an activated derivative such as the acid chloride 2.3, in which X is Cl, for example by treatment with oxalyl chloride, or into a mixed carbonate, for example by treatment with isobutyl chloroformate, and the activated derivative thus obtained is reacted with ethereal diazomethane, to afford the diazoketone 2.4. The reaction is performed by the addition of a solution of the activated carboxylic acid derivative to an ethereal solution of three or more molar equivalents of diazomethane at 0° C. The diazoketone is converted into the chloroketone 2.5 by reaction with anhydrous hydrogen chloride, in a suitable solvent such as diethyl ether, as described in J. Med. Chem., 1997, 40, 3979. The latter compound is then reduced, for example by the use of an equimolar amount of sodium borohydride in an ethereal solvent such as tetrahydrofuran at 0° C., to produce a mixture of chlorohydrins from which the desired 2S, 3S diastereomer 2.6 is separated by chromatography. The chlorohydrin 2.6 is then converted into the epoxide 1.1 by treatment with a base such as an alkali metal hydroxide in an alcoholic solvent, for example as described in J. Med. Chem., 1997, 40, 3979. Preferably, the compound 2.6 is reacted with ethanolic potassium hydroxide at ambient temperature to afford the epoxide 1.1.

Scheme 3 illustrates the preparation of the amine reactant $R^2NHCH(R^3)CONHR^4$ (1.2) employed above (Scheme 1). In this procedure, the carboxylic acid $R^2NHCH(R^3)COOH$ 3.1 is first converted into the N-protected analog 3.2, for example by reaction with benzyloxychloroformate and triethylamine in tetrahydrofuran. The carboxyl group is then activated, for example by conversion to the acid chloride or a mixed anhydride, or by reaction with isobutyl chloroformate, as described in Chimia, 50, 532, 1996 and in Synthesis, 1972, 453, and the activated derivative is then reacted with the amine $R^4NH_2$ to produce the amide 3.4. Deprotection, for example as described above, then affords the free amine 1.2.

Scheme 4 depicts an alternative method for the preparation of the compounds 1 in which X is a direct bond. In this procedure, a hydroxymethyl-substituted oxazolidinone 4.1 is converted into an activated derivative 4.2 which is then reacted with the amine $R^2NHCH(R^3)CONHR^4$ (1.2) to afford the amide 4.3. The preparation of the hydroxymethyl-substituted oxazolidinone 4.1 is described below, (Scheme 5) The hydroxyl group can be converted into a bromo derivative, for example by reaction with triphenylphosphine and carbon tetrabromide, as described in J. Am. Chem. Soc., 92, 2139, 1970, or a methanesulfonyloxy derivative, by reaction with methanesulfonyl chloride and a base, or, preferably, into the 4-nitrobenzenesulfonyloxy derivative 4.2, by reaction in a solvent such as ethyl acetate or tetrahydrofuran, with 4-nitrobenzenesulfonyl chloride and a base such as triethylamine or N-methylmorpholine, as described in WO 9607642. The nosylate product 4.2 is then reacted with the amine component 1.2 to afford the displacement product 4.3. Equimolar amounts of the reactants are combined in an inert solvent such as dimethylformamide, acetonitrile or acetone, optionally in the presence of an organic or inorganic base such as triethylamine or sodium carbonate, at from about 0° C. to 100° C. to afford the amine product 4.3. Preferably, the reaction is performed in methyl isobutyl ketone at 80° C., in the presence of sodium carbonate, as described in WO 9607642. The oxazolidinone group present in the product 4.3 is then hydrolyzed to afford the hydroxyamine 4.4. The hydrolysis reaction is effected in the presence of aqueous solution of a base such as an alkali metal hydroxide, optionally in the presence of an organic co-solvent. Preferably, the oxazolidinone compound 4.3 is reacted with aqueous ethanolic sodium hydroxide at reflux temperature, as described in WO 9607642, to afford the amine 4.4. This product is then reacted with the carboxylic acid or activated derivative thereof, 1.5, the preparation of which is described above, to afford the product 1.6. The amide-forming reaction is conducted under the same conditions as described above, (Scheme 1)

Scheme 5 depicts the preparation of the hydroxymethyl oxazolidinones 4.1, which are utilized in the preparation of the phosphonate esters 1, as described above in Scheme 4. In this procedure, phenylalanine, or a substituted derivative thereof, 2.1, in which $R^{10}$ is as defined in Chart 2, is converted into the phthalimido derivative 5.1. The conversion of amines into phthalimido derivatives is described, for example, in Protective Groups in Organic Synthesis, by T. W. Greene and P. G. M Wuts, Wiley, Second Edition 1990, p. 358. The amine is reacted with phthalic anhydride, 2-carboethoxybenzoyl chloride or N-carboethoxyphthalimide, optionally in the presence of a base such as triethylamine or sodium carbonate, to afford the protected amine 5.1. Preferably, the aminoacid is reacted with phthalic anhydride in toluene at reflux, to yield the phthalimido product. The carboxylic acid is then transformed into an activated derivative such as the acid chloride 5.2, in which X is Cl. The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of a tertiary amide such as dimethylformamide. Preferably, the carboxylic acid is transformed into the acid chloride by reaction with oxalyl chloride and a catalytic amount of dimethylformamide, in toluene solution at ambient temperature, as described in WO 9607642. The acid chloride 5.2, X=Cl, is then converted into the aldehyde 5.3 by means of a reduction reaction. This procedure is described, for example, in Comprehensive Organic Transformations, by R. C. Larock, VCH, 1989, p. 620. The transformation can be effected by means of catalytic hydrogenation, a procedure which is referred to as the Rosenmund reaction, or by chemical reduction employing, for example, sodium borohydride, lithium aluminum tri-tertiarybutoxy hydride or triethylsilane. Preferably, the acid chloride 5.2 X=Cl, is hydrogenated in toluene solution over a 5% palladium on carbon catalyst, in the presence of butylene oxide, as described in WO 9607642, to afford the aldehyde 5.3. The aldehyde 5.3 is then transformed into the cyanohydrin derivative 5.4. The conversion of aldehydes into cyanohydrins is described in Protective Groups in Organic Synthesis, by T. W. Greene and P. G. M Wuts, Wiley, Second Edition 1990, p. 211. For example, the aldehyde 5.3 is converted into the cyanohydrin 5.4 by reaction with trimethylsilyl cyanide in an inert solvent such as dichloromethane, followed by treatment with an organic acid such as citric acid, as described in WO 9607642, or by alternative methods described therein. The cyanohydrin is then subjected to acidic hydrolysis, to effect conversion of the cyano group into the corresponding carboxy group, with concomitant hydrolysis of the phthalimido substituent to afford the aminoacid 5.5 The hydrolysis reactions are effected by the use of aqueous mineral acid. For example, the substrate 5.4 is reacted with aqueous hydrochloric acid at reflux, as described in WO 9607642, to afford the carboxylic acid product 5.5. The aminoacid is then converted into a carbamate, for example the ethyl carbamate 5.6. The conversion of amines into carbamates is described in Protective Groups in Organic Synthesis, by T. W. Greene and P. G. M Wuts, Wiley, Second Edition 1990, p. 317. The amine is reacted with a chloroformate, for example ethyl chloroformate, in the presence of a base such as potassium carbonate, to afford the carbamate 5.6. For example, the aminoacid 5.5 is reacted, in aqueous solution, with ethyl chloroformate and sufficient aqueous sodium hydroxide to maintain a neutral pH, as described in WO 9607642, to afford the carbamate 5.6. The latter compound is then transformed into the oxazolidinone 5.7, for example by treatment with aqueous sodium hydroxide at ambient temperature, as described in WP 9607642. The resultant carboxylic acid is transformed into the methyl ester 5.8 by means of a conventional esterification reaction. The conversion of carboxylic acids into esters is described for example, in Comprehensive Organic Transformations, by R. C. Larock, VCH, 1989, p. 966. The conversion can be effected by means of an acid-catalyzed reaction between the carboxylic acid and an alcohol, or by means of a base-catalyzed reaction between the carboxylic acid and an alkyl halide, for example an alkyl bromide. For example, the carboxylic acid 5.7 is converted into the methyl ester 5.8 by treatment with methanol at reflux temperature, in the presence of a catalytic amount of sulfuric acid, as described in WO 9607642. The carbomethoxyl group present in the compound 5.8 is then reduced to yield the corresponding carbinol 4.1. The reduction of carboxylic esters to the carbinols is described in Comprehensive Organic Transformations, by R. C. Larock, VCH, 1989, p. 550. The transformation can be effected by the use of reducing agents such as borane-dimethylsulfide, lithium borohydride, diisobutyl aluminum hydride, lithium aluminum hydride and the like. For example, the ester 5.8 is reduced to the carbinol 4.1 by reaction with sodium borohydride in ethanol at ambient temperature, as described in WO 9607642.

Scheme 1

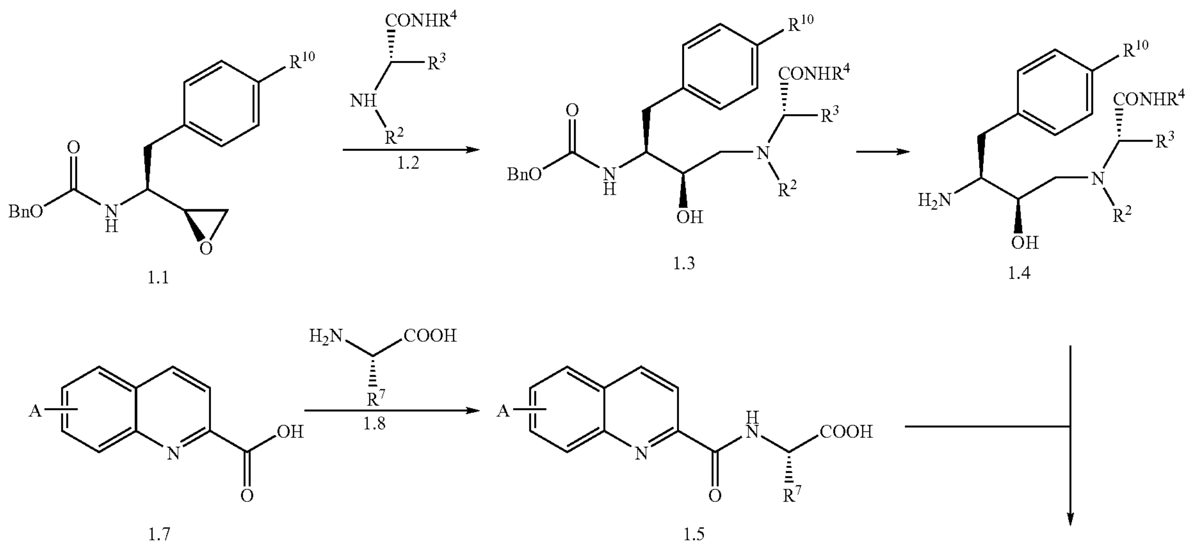

-continued
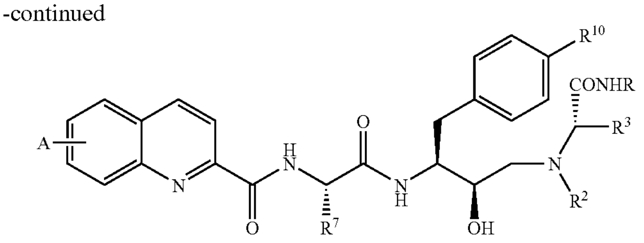
1.6
$R^{10}$ = H, $OC_2H_5$, $OCH_2C_6H_5$, $OCH_2CH_2$morpholino, $OCH_2CO$morpholino
A = [OH], [SH], [$NH_2$], Br etc or link-P(O)$(OR^1)_2$
Scheme 2
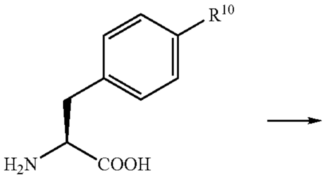
2.1
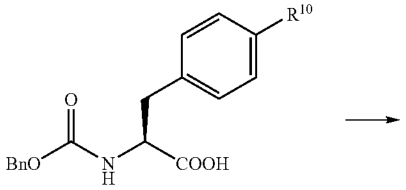
2.2
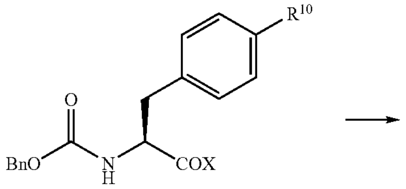
2.3
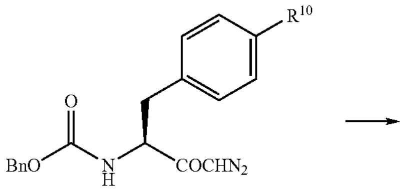
2.4
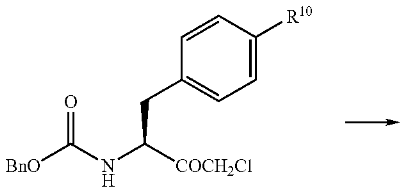
2.5
-continued
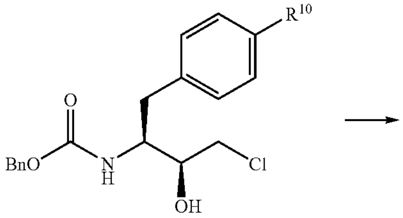
2.6
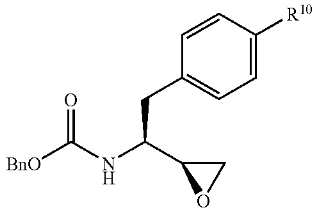
1.1
Scheme 3
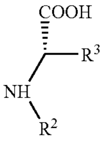
3.1
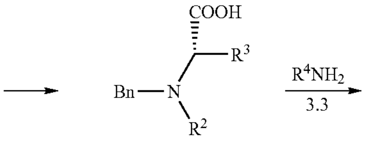
3.2
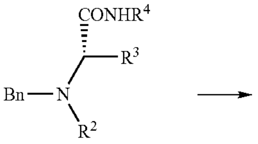
3.4
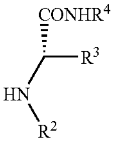
1.2

Scheme 4
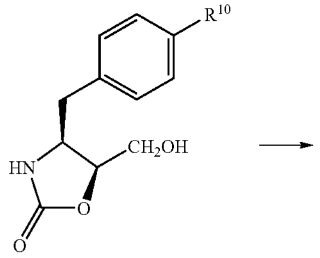
4.1
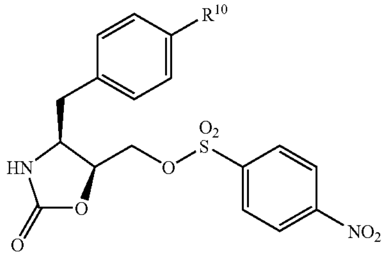
4.2
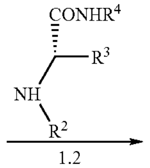
1.2
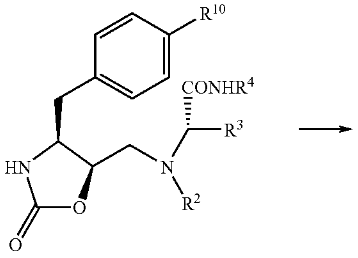
4.3
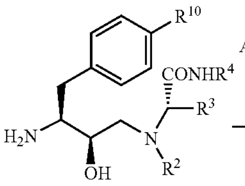
4.4
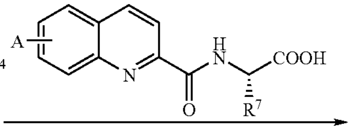
1.5
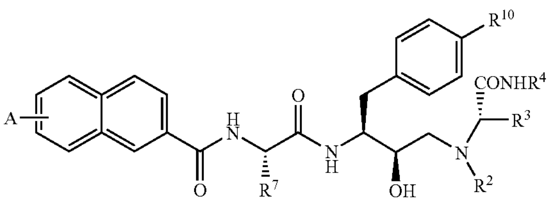
1.6
Scheme 5
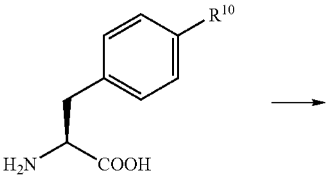
2.1
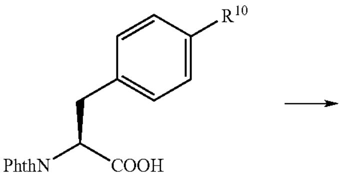
5.1
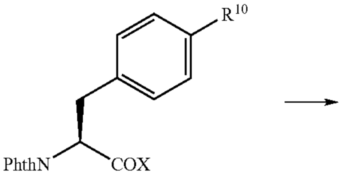
5.2
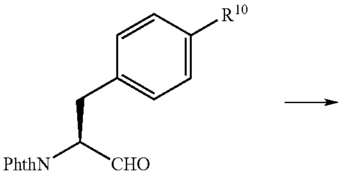
5.3
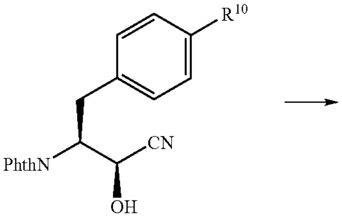
5.4
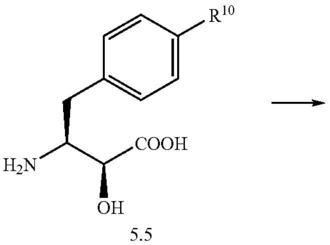
5.5
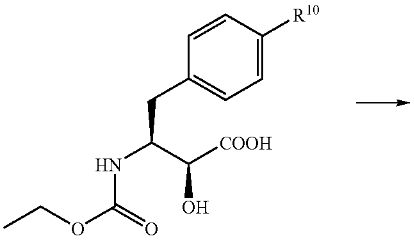
5.6

-continued

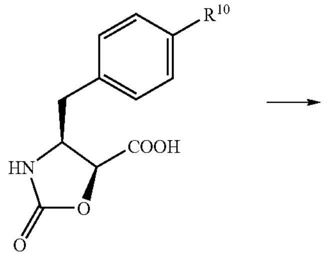

5.7

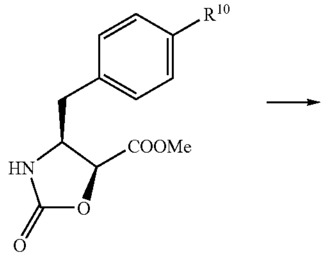

5.8

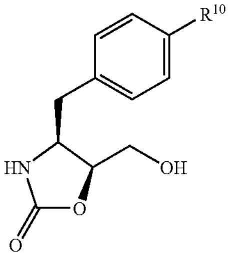

5.9

The procedures illustrated in Schemes 1 and 4 depict the preparation of the compounds 1.6 in which X is a direct bond, and in which the substituent A is either the group link-P(O)$(OR^1)_2$ or a precursor thereto, such as [OH], [SH] Br, as described below. Scheme 6 illustrates the conversion of compounds 1.6 in which A is a precursor to the group link-P(O)$(OR^1)_2$ into the compounds 1. Procedures for the conversion of the substituent A into the group link-P(O)$(OR^1)_2$ are illustrated below, (Schemes 24-69). In the procedures illustrated above, Schemes 1, 4 and in the procedures illustrated below (Schemes 24-69) for the preparation of the phosphonate esters 2-6, compounds in which the group A is a precursor to the group link-P(O)$(OR^1)_2$ may be converted into compounds in which A is link-P(O)$(OR^1)_2$ at any appropriate stage in the reaction sequence, or, as shown in Scheme 6, at the end of the sequence. The selection of an appropriate stage to effect the conversion of the group A into the group link-P(O)$(OR^1)_2$ is made after consideration of the nature of the reactions involved in the conversion, and the stability of the various components of the substrate to those conditions.

Scheme 7

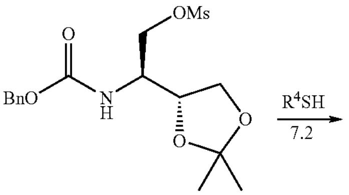

7.1

Scheme 6

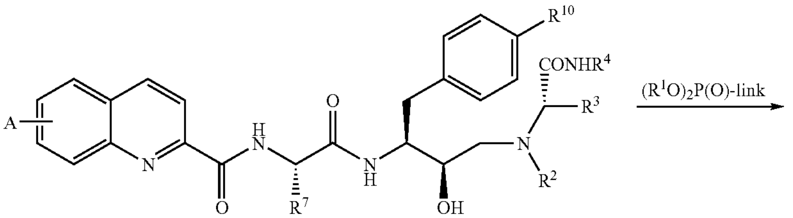

1.6

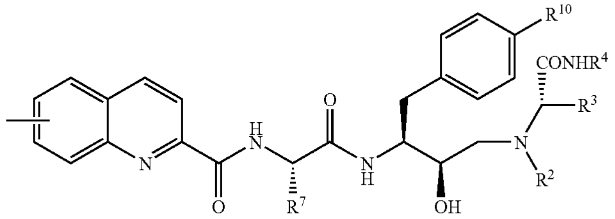

1

-continued
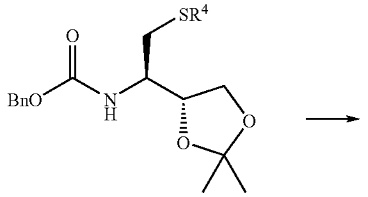
7.3
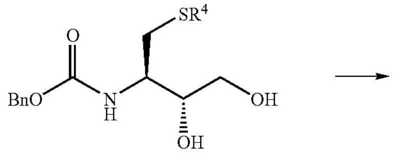
7.4
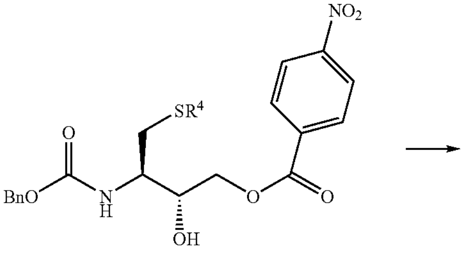
7.5
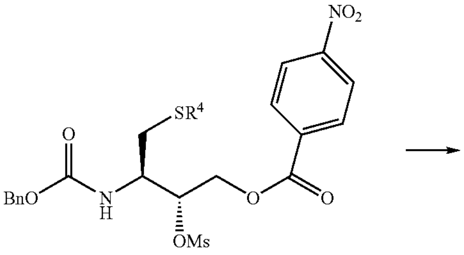
7.6
-continued
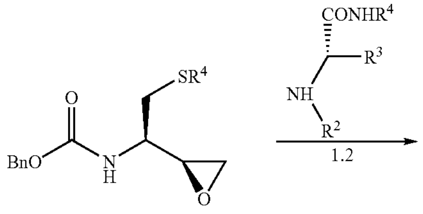
7.7
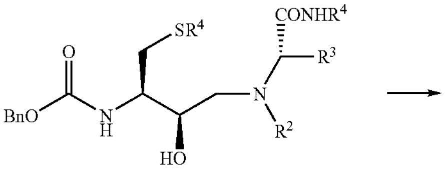
7.8
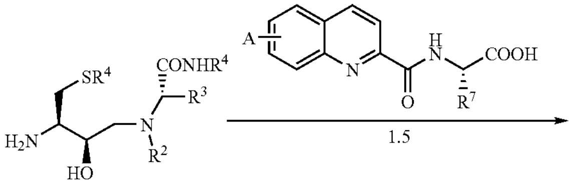
7.9
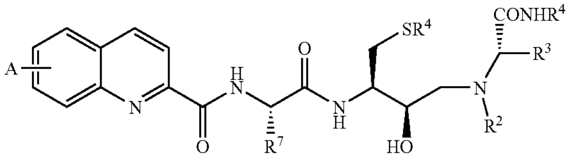
7.10
$R^4SH = C_6H_5SH$, $4\text{-}FC_6H_5SH$, 2-naphthyl-SH
Scheme 8
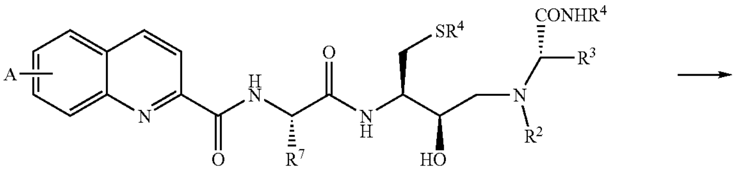
7.10
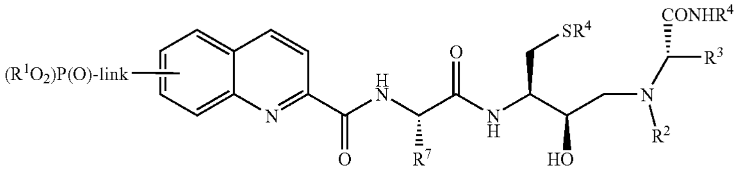
1

Scheme 7 illustrates the preparation of the compounds 1 in which the substituent X is S, and in which the group A is either the group link-P(O)($OR^1$)$_2$ or a precursor thereto, such as [OH], [SH] Br, as described below.

In this sequence, methanesulfonic acid 2-benzoyloxycarbonylamino-2-(2,2-dimethyl-[1,3]dioxolan-4-yl)-ethyl ester, 7.1, prepared as described in J. Org. Chem, 2000, 65, 1623, is reacted with a thiol $R^4$SH 7.2, as defined above, to afford the thioether 7.3.

The reaction is conducted in a suitable solvent such as, for example, pyridine, DMF and the like, in the presence of an inorganic or organic base, at from 0° C. to 80° C., for from 1-12 hours, to afford the thioether 7.3. Preferably the mesylate 7.1 is reacted with an equimolar amount of the thiol $R^4$SH, in a mixture of a water-immiscible organic solvent such as toluene, and water, in the presence of a phase-transfer catalyst such as, for example, tetrabutyl ammonium bromide, and an inorganic base such as sodium hydroxide, at about 50° C., to give the product 7.3. The 1,3-dioxolane protecting group present in the compound 7.3 is then removed by acid catalyzed hydrolysis or by exchange with a reactive carbonyl compound to afford the diol 7.4. Methods for conversion of 1,3-dioxolanes to the corresponding diols are described in Protective Groups in Organic Synthesis, by T. W. Greene and P. G. M Wuts, Second Edition 1990, p. 191. For example, the 1,3-dioxolane compound 7.3 is hydrolyzed by reaction with a catalytic amount of an acid in an aqueous organic solvent mixture. Preferably, the 1,3-dioxolane 7.3 is dissolved in aqueous methanol containing hydrochloric acid, and heated at ca. 50° C., to yield the product 7.4.

The primary hydroxyl group of the diol 7.4 is then selectively acylated by reaction with an electron-withdrawing acyl halide such as, for example, pentafluorobenzoyl chloride or mono- or di-nitrobenzoyl chlorides. The reaction is conducted in an inert solvent such as dichloromethane and the like, in the presence of an inorganic or organic base.

Preferably, equimolar amounts of the diol 7.4 and 4-nitrobenzoyl chloride are reacted in a solvent such as ethyl acetate, in the presence of a tertiary organic base such as 2-picoline, at ambient temperature, to afford the hydroxy ester 7.5. The hydroxy ester is next reacted with a sulfonyl chloride such as methanesulfonyl chloride, 4-toluenesulfonyl chloride and the like, in the presence of a base, in an aprotic polar solvent at low temperature, to afford the corresponding sulfonyl ester 7.6. Preferably, equimolar amounts of the carbinol 7.5 and methanesulfonyl chloride are reacted together in ethyl acetate containing triethylamine, at about 10° C., to yield the mesylate 7.6. The compound 7.6 is then subjected to a hydrolysis-cyclization reaction to afford the oxirane 7.7. The mesylate or analogous leaving group present in 7.6 is displaced by hydroxide ion, and the carbinol thus produced, without isolation, spontaneously transforms into the oxirane 7.7 with elimination of 4-nitrobenzoate. To effect this transformation, the sulfonyl ester 7.6 is reacted with an alkali metal hydroxide or tetraalkylammonium hydroxide in an aqueous organic solvent. Preferably, the mesylate 7.6 is reacted with potassium hydroxide in aqueous dioxan at ambient temperature for about 1 hour, to afford the oxirane 7.7.

The oxirane compound 7.7 is then subjected to regiospecific ring-opening reaction by treatment with a secondary amine 1.2, to give the aminoalcohol 7.8. The amine and the oxirane are reacted in a protic organic solvent, optionally in the additional presence of water, at 0° C. to 100° C., and in the presence of an inorganic base, for 1 to 12 hours, to give the product 7.8. Preferably, equimolar amounts of the reactants 7.7 and 1.2 are reacted in aqueous methanol at about 60° C. in the presence of potassium carbonate, for about 6 hours, to afford the aminoalcohol 7.8. The carbobenzyloxy (cbz) protecting group in the product 7.8 is removed to afford the free amine 7.9. Methods for removal of cbz groups are described, for example, in Protective Groups in Organic Synthesis, by T. W. Greene and P. G. M Wuts, Second Edition, p. 335. The methods include catalytic hydrogenation and acidic or basic hydrolysis.

For example, the cbz-protected amine 7.8 is reacted with an alkali metal or alkaline earth hydroxide in an aqueous organic or alcoholic solvent, to yield the free amine 7.9. Preferably, the cbz group is removed by the reaction of 7.8 with potassium hydroxide in an alcohol such as isopropanol at ca. 60° C. to afford the amine 7.9. The amine 7.9 so obtained is next acylated with a carboxylic acid or activated derivative 1.5, using the conditions described above for the conversion of the amine 1.4 into the amide 1.6 (Scheme 1), to yield the final amide product 7.10.

The procedures illustrated in Scheme 7 depict the preparation of the compounds 1 in which X is S, and in which the substituent A is either the group link-P(O)($OR^1$)$_2$ or a precursor thereto, such as [OH], [SH] Br, as described below. Scheme 8 illustrates the conversion of compounds 7.10 in which A is a precursor to the group link-P(O)($OR^1$)$_2$ into the compounds 1. Procedures for the conversion of the substituent A into the group link-P(O)($OR^1$)$_2$ are illustrated below, (Schemes 24-69).

The reactions illustrated in Schemes 1-7 illustrate the preparation of the compounds 1 in which A is either the group link-P(O)($OR^1$)$_2$ or a precursor thereto, such as, for example, optionally protected OH, SH, NH, as described below. Scheme 8 depicts the conversion of the compounds 1 in which A is OH, SH, NH, as described below, into the compounds 1 in which A is the group link-P(O)($OR^1$)$_2$. Procedures for the conversion of the group A into the group link-P(O))($OR^1$)$_2$ are described below, (Schemes 24-69).

In this and succeeding examples, the nature of the phosphonate ester group can be varied, either before or after incorporation into the scaffold, by means of chemical transformations. The transformations, and the methods by which they are accomplished, are described below, (Scheme 54)

Preparation of the Phosphonate Intermediates 2.

Scheme 9 depicts the one method for the preparation of the compounds 2 in which X is a direct bond, and in which the substituent A is either the group link-P(O)($OR^1$)$_2$ or a precursor thereto, such as [OH], [SH] Br, as described below. In this procedure, the hydroxymethyl oxazolidinone 9.1, the preparation of which is described below, is converted into an activated derivative, for example the 4-nitrobenzenesulfonate 9.2. The conditions for this transformation are the same as those described above (Scheme 4) for the conversion of the carbinol 4.1 into the nosylate 4.2. The activated ester 9.2 is then reacted with the amine 1.2, under the same conditions as described above for the preparation of the amine 4.3 to afford the oxazolidinone amine 9.3. The oxazolidinone group is then hydrolyzed by treatment with aqueous alcoholic base, to produce the primary amine 4.4. For example, the oxazolidinone 9.3 is reacted with aqueous ethanolic sodium hydroxide at reflux temperature, as described in WO 9607642, to afford the amine product 9.4. The latter compound is then coupled with the carboxylic acid 9.6, to afford the amide 9.5. The conditions for the coupling reaction are the same as those described above for the preparation of the amide 1.6.

The phosphonate esters 2-6 which incorporate the group $R^6$CO derived formally from the carboxylic acids depicted in Chart 2c contain a carbamate group. Various methods for the preparation of carbamates are described below, (Scheme 55)

Scheme 10 illustrates an alternative method for the preparation of the compounds 2 in which X is a direct bond, and in which the substituent A is either the group link-$P(O)(OR^1)_2$ or a precursor thereto, such as [OH], [SH] Br, as described below. In this procedure, the oxirane 10.1, the preparation of which is described below, is reacted with the amine 1.2 to afford the aminoalcohol 10.2. The reaction is conducted under the same conditions as are described above for the preparation of the aminoalcohol 1.3. (Scheme 1) The benzyloxycarbonyl protecting group is then removed from the product 10.2 to afford the free amine 10.3. The conditions for the debenzylation reaction are the same as those described above for the debenzylation of the compound 1.3. The amine 10.3 is then coupled with the carboxylic acid 9.6 to produce the amide 9.5, employing the same conditions as are described above (Scheme 9).

The procedures illustrated in Schemes 9 and 10 depict the preparation of the compounds 9.5 in which the substituent A is either the group link-$P(O)(OR^1)_2$ or a precursor thereto, such as [OH], [SH] Br, as described below. Scheme 11 illustrates the conversion of compounds 9.5 in which A is a precursor to the group link-$P(O)(OR^1)_2$ into the compounds 2. Procedures for the conversion of the substituent A into the group link-$P(O)(OR^1)_2$ are illustrated below, (Schemes 24-69).

Schemes 12 and 13 depict the preparation of compounds 2 in which X is sulfur. As shown in Scheme 12, a substituted thiophenol 12.2, in which the substituent A is either the group link-$P(O)(OR^1)_2$ or a precursor thereto, such as [OH], [SH] Br, as described below, is reacted with methanesulfonic acid 2-benzyloxycarbonylamino-2-(2,2-dimethyl-[1,3]dioxolan-4-yl)-ethyl ester 12.1, the preparation of which is described in J. Org. Chem, 2000, 65, 1623, to afford the displacement product 12.3. The conditions for the reaction are the same as described above for the preparation of the thioether 7.3. Methods for the preparation of the substituted thiophenol 12.2 are described below, Schemes 35-44. The thioether product 12.3 is then transformed, using the series of reactions described above, Scheme 7, for the conversion of the thioether 7.3 into the amine 7.9. The conditions employed for this series of reactions are the same as those described above, (Scheme 7). The amine 12.4 is then reacted with the carboxylic acid or activated derivative thereof, 9.6 to afford the amide 12.5. The conditions for the reaction are the same as those described above for the preparation of the amide 9.5.

The procedures illustrated in Scheme 12 depict the preparation of the compounds 12.5 in which the substituent A is either the group link-$P(O)(OR^1)_2$ or a precursor thereto, such as [OH], [SH] Br, as described below. Scheme 13 illustrates the conversion of compounds 12.5 in which A is a precursor to the group link-$P(O)(OR^1)_2$ into the compounds 2. Procedures for the conversion of the substituent A into the group link-$P(O)(OR^1)_2$ are illustrated below, (Schemes 24-69).

Scheme 9

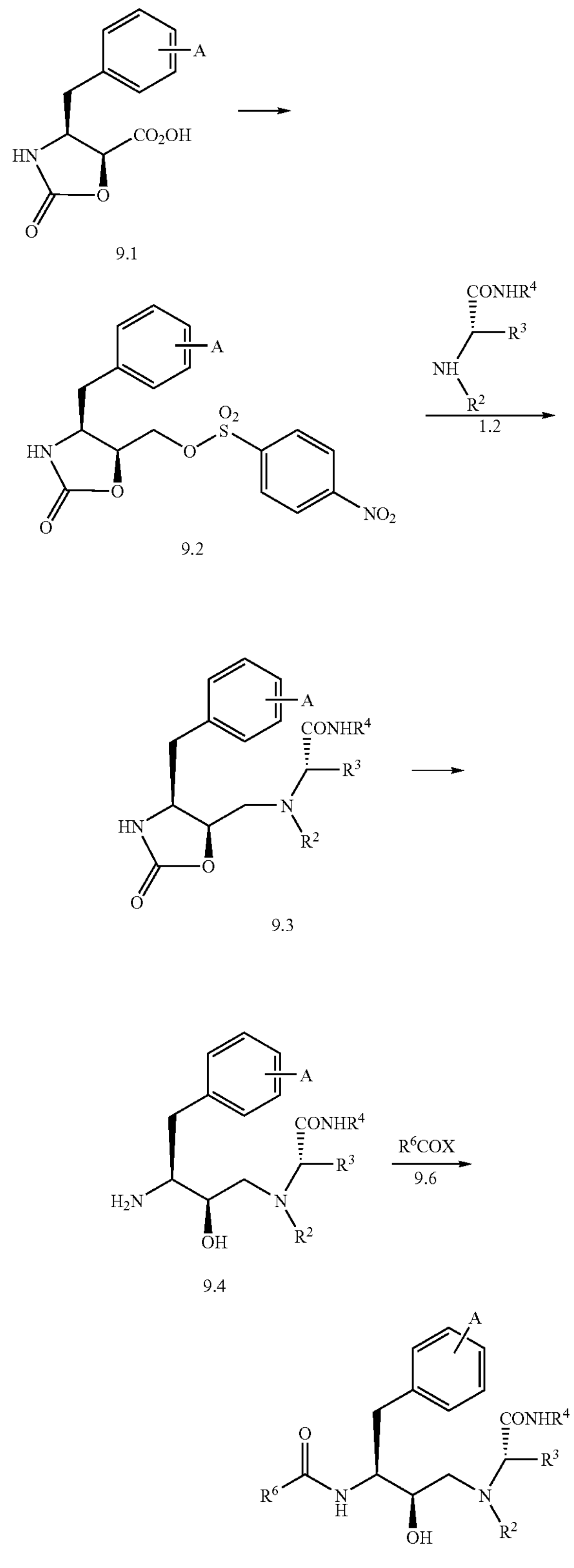

9.1

9.2

9.3

9.4

9.5

Scheme 10
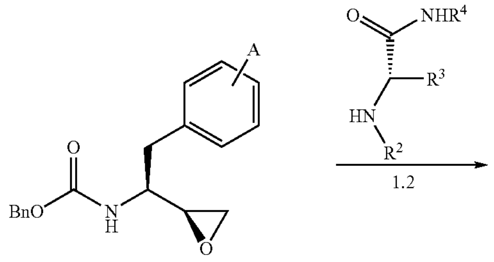
10.1
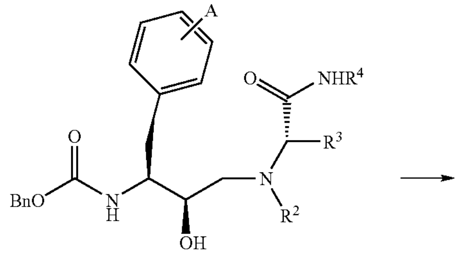
10.2
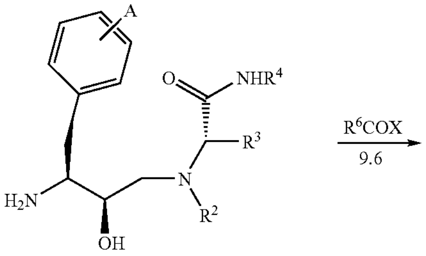
10.3
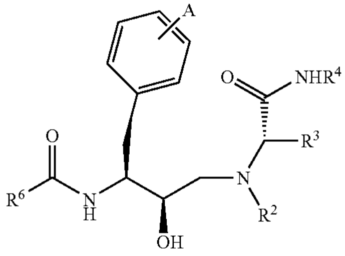
9.5
Scheme 11
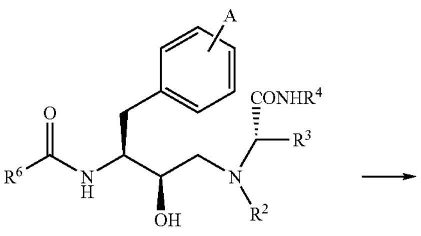
9.5
-continued
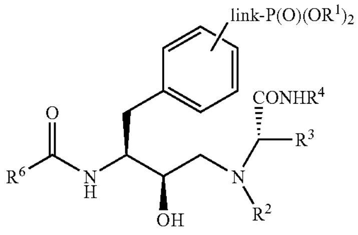
1
Scheme 12
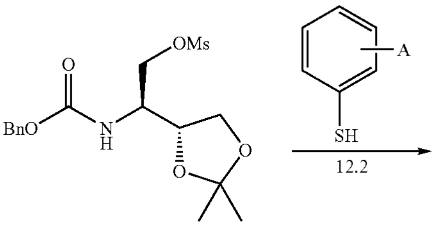
12.1
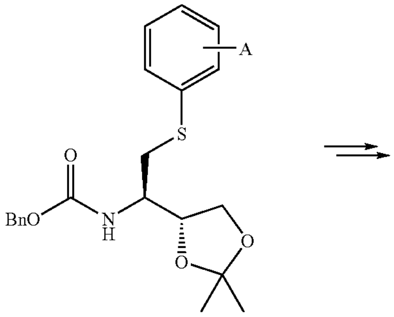
12.3
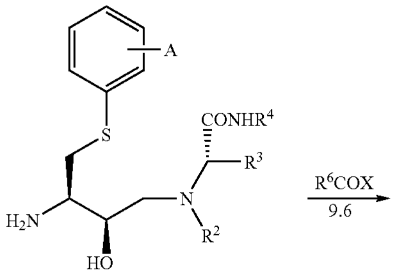
12.4
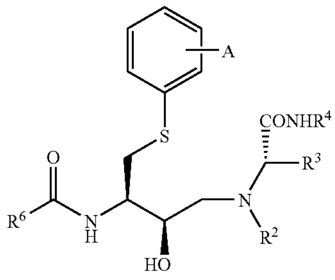
12.5

Scheme 13

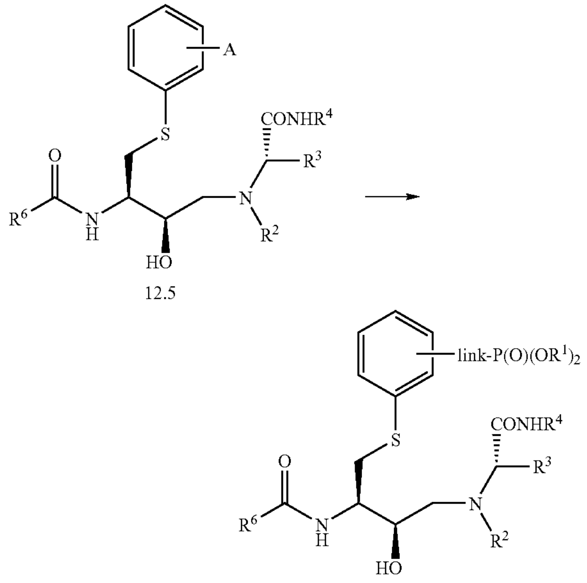

12.5

2

Preparation of the Phosphonate Intermediates 3.

Schemes 14-16 depict the preparation of the phosphonate esters 3 in which X is a direct bond. As shown in Scheme 14, the oxirane 1.1, the preparation of which is described above, is reacted with the amine 14.1 in which the substituent A is either the group link-P(O)(OR$^1$)$_2$ or a precursor thereto, such as [OH], [SH] Br, as described below, to yield the hydroxyamine 14.2. The conditions for the reaction are the same as described above for the preparation of the amine 1.3. Methods for the preparation of the amine 14.1 are described below, Schemes 45-48. The hydroxyamine product 14.2 is then deprotected to afford the free amine 14.3. The conditions for the debenzylation reaction are the same as those described above for the preparation of the amine 1.4. (Scheme 1). The amine 14.3 is then coupled with the carboxylic acid or activated derivative thereof, 9.6, to afford the amide 14.4, using the conditions described above for the preparation of the amide 12.5.

Scheme 15 illustrates an alternative method for the preparation of the phosphonate esters 14.4. In this reaction sequence, the 4-nitrobenzenesulfonate 4.2, the preparation of which is described above, (Scheme 4), is reacted with the amine 14.1, in which the substituent A is either the group link-P(O)(OR$^1$)$_2$ or a precursor thereto, such as [OH], [SH] Br, as described below, to yield the amine 15.1. The reaction is conducted under the same conditions as described above for the preparation of the amide 4.3. The oxazolidine moiety present in the product is then removed, using the procedure described above for the conversion of the oxazolidine 4.3 into the hydroxyamine 4.4, to afford the hydroxyamine 15.2. The latter compound is then coupled, as described above, with the carboxylic acid or activated derivative thereof, 9.6, to afford the amide 14.4.

The procedures illustrated in Schemes 14 and 15 depict the preparation of the compounds 14.4 in which the substituent A is either the group link-P(O)(OR$^1$)$_2$ or a precursor thereto, such as [OH], [SH] Br, as described below. Scheme 16 illustrates the conversion of compounds 14.4 in which A is a precursor to the group link-P(O)(OR$^1$)$_2$ into the compounds 3. Procedures for the conversion of the substituent A into the group link-P(O)(OR$^1$)$_2$ are illustrated below, (Schemes 24-69).

Schemes 17 and 18 illustrates the preparation of the phosphonate esters 3 in which X is sulfur. As shown in Scheme 17, the oxirane 7.7, the preparation of which is described above, (Scheme 7) is reacted with the amine 14.1. The conditions for the ring-opening reaction are the same as those described above for the preparation of the aminoalcohol 7.8, (Scheme 7). The benzyloxycarbonyl protecting group is then removed to produce the free amine 17.2. The conditions for the deprotection reaction are the same as those described above for the conversion of the protected amine 7.8 to the amine 7.9 (Scheme 7) The amine product 17.2 is then coupled with the carboxylic acid or activated derivative thereof, 9.6, using the same conditions as described above, to afford the amide 17.3.

The procedures illustrated in Scheme 17 depict the preparation of the compound 17.3 in which the substituent A is either the group link-P(O)(OR$^1$)$_2$ or a precursor thereto, such as [OH], [SH] Br, as described below. Scheme 18 illustrates the conversion of compounds 17.3 in which A is a precursor to the group link-P(O)(OR$^1$)$_2$ into the compounds 3. Procedures for the conversion of the substituent A into the group link-P(O)(OR$^1$)$_2$ are illustrated below, (Schemes 24-69).

Scheme 14

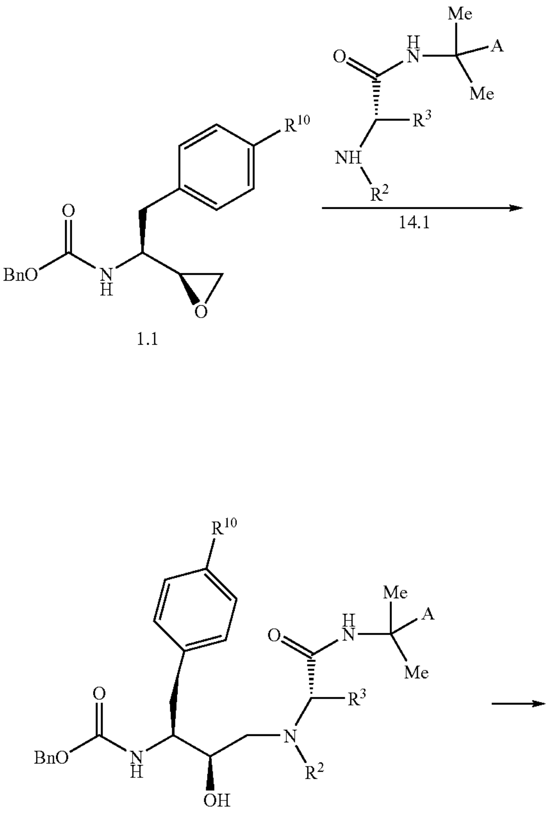

1.1

14.1

14.2

-continued
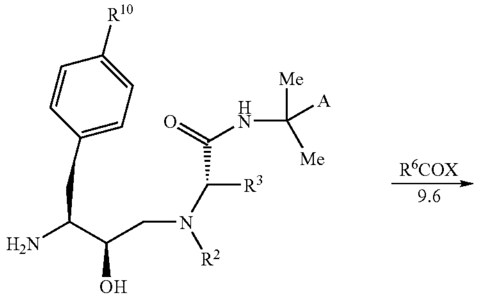
14.3
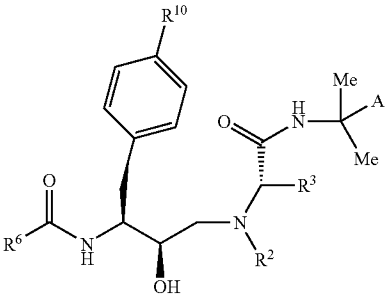
14.4
-continued
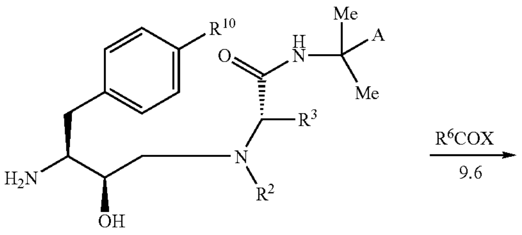
15.2
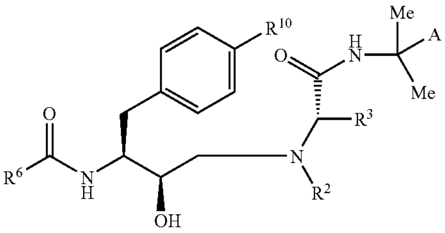
14.4
Scheme 15
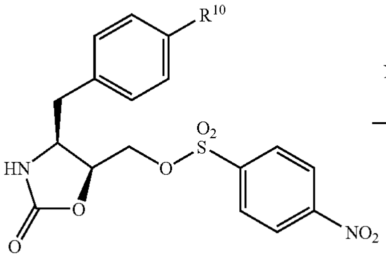
4.2
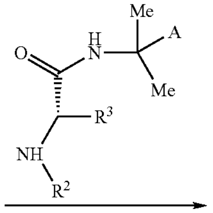
14.1
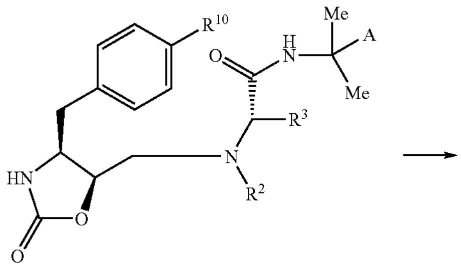
15.1
Scheme 16
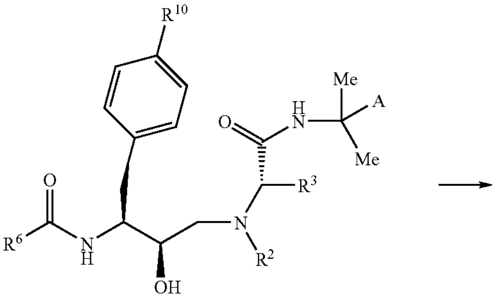
14.4
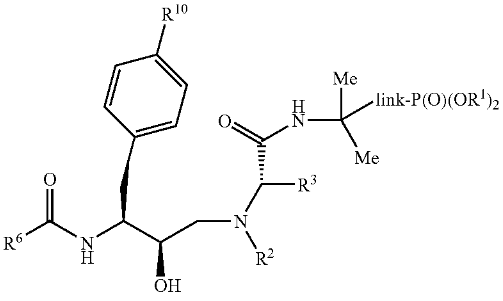
3

Scheme 17

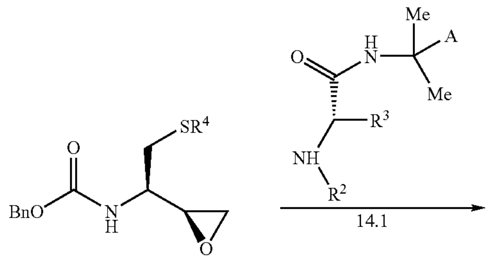

7.7

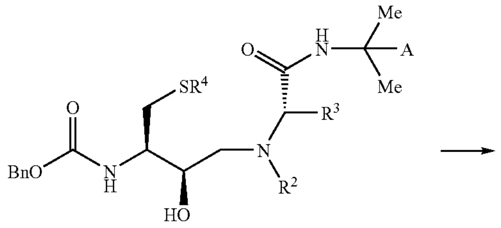

17.1

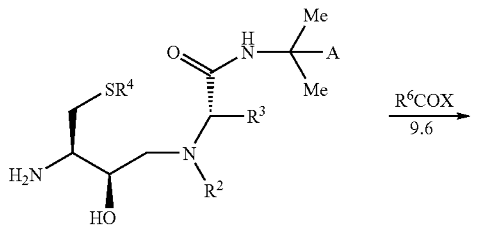

17.2

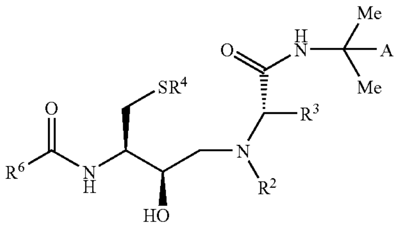

17.3

Scheme 18

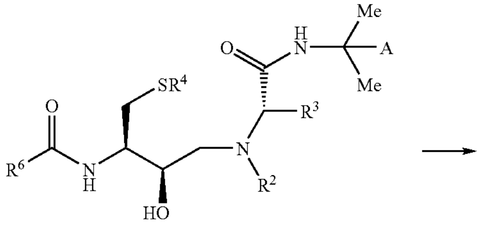

17.3

-continued

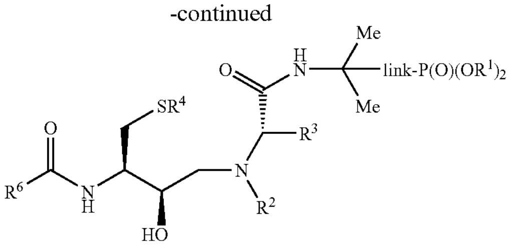

3

Preparation of the Phosphonate Intermediates 4.

Scheme 19 illustrates one method for the preparation of the phosphonate esters 4 in which X is a direct bond. In this reaction sequence, the oxirane 1.1, the preparation of which is described above (Scheme 2) is reacted with the decahydroisoquinoline amine 19.1, in which the substituent A is either the group link-$P(O)(OR^1)_2$ or a precursor thereto, such as [OH], [SH] Br, as described below, to afford the aminoalcohol product 19.2. The conditions for the ring-opening reaction are the same as those described above for the preparation of the aminoalcohol 1.3. The preparation of the decahydroisoquinoline derivatives 19.1 is described below, (Schemes 48a-52). The cbz protecting group is then removed to yield the free amine 19.3, using the same conditions as described above for the preparation of the amine 1.4, (Scheme 1). The amine 19.3 is then coupled with the carboxylic acid or activated derivative thereof, 9.6, using the same conditions as described above, to afford the amide 19.4.

Scheme 20 illustrates an alternative method for the preparation of the phosphonate intermediates 19.4. In this procedure, the 4-nitrobenzenesulfonyl ester 4.2, the preparation of which is described above, (Scheme 4) is reacted with the decahydroisoquinoline derivative 20.1, in which the substituent A is either the group link-$P(O)(OR^1)_2$ or a precursor thereto, such as [OH], [SH] Br, as described below. The reaction conditions for the displacement reaction are the same as those described above for the preparation of the amine 4.3, (Scheme 4). The oxazolidinone moiety present in the product 20.2 is then hydrolyzed, using the procedures described above (Scheme 4) to afford the free amine 20.3. This compound is then coupled with the carboxylic acid or activated derivative thereof, 9.6, using the same conditions as are described above, to afford the amide product 19.4.

The procedures illustrated in Schemes 19 and 20 depict the preparation of the compounds 19.4 in which the substituent A is either the group link-$P(O)(OR^1)_2$ or a precursor thereto, such as [OH], [SH] Br, as described below. Scheme 21 illustrates the conversion of compounds 19.4 in which A is a precursor to the group link-$P(O)(OR^1)_2$ into the compounds 4. Procedures for the conversion of the substituent A into the group link-$P(O)(OR^1)_2$ are illustrated below, (Schemes 24-69).

Schemes 22 and 23 depict the preparation of the phosphonate esters 4 in which X is sulfur. As shown in Scheme 22, the oxirane 7.7, prepared as described above (Scheme 7) is reacted with the decahydroisoquinoline derivative 19.1, in which the substituent A is either the group link-$P(O)(OR^1)_2$ or a precursor thereto, such as [OH], [SH] Br, as described below. The reaction is conducted under the same conditions as described above for the preparation of the amine 7.8, (Scheme 7), to produce the hydroxyamine 22.1. The cbz protecting group present in the product 22.1 is then removed, using the same procedures as described above (Scheme 7) to afford the free amine 22.2. This material is then coupled with the carboxylic acid or activated derivative thereof, 9.6 to yield the amide 22.3. The coupling reaction is preformed under the same conditions as previously described.

The procedures illustrated in Scheme 22 depict the preparation of the compounds 22.3 in which the substituent A is either the group link-P(O)(OR[1])$_2$ or a precursor thereto, such as [OH], [SH] Br, as described below. Scheme 23 illustrates the conversion of compounds 22.3 in which A is a precursor to the group link-P(O)(OR[1])$_2$ into the compounds 4. Procedures for the conversion of the substituent A into the group link-P(O)(OR[1])$_2$ are illustrated below, (Schemes 24-69).

Scheme 19

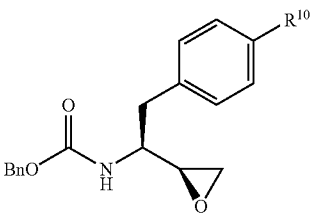

1.1

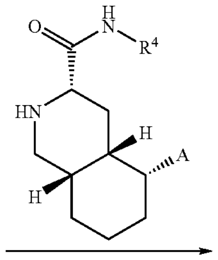

19.1

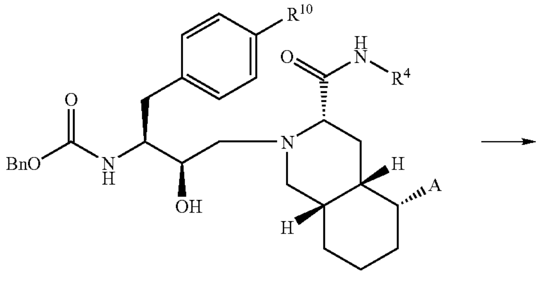

19.2

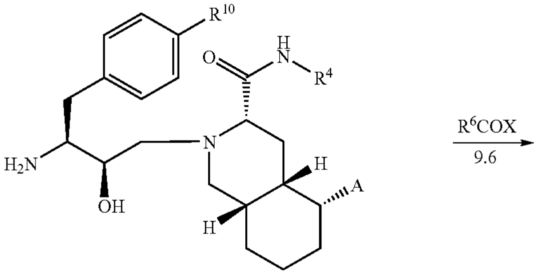

19.3

-continued

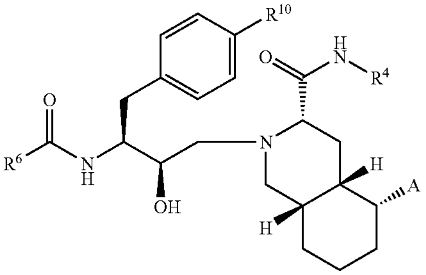

19.4

Scheme 20

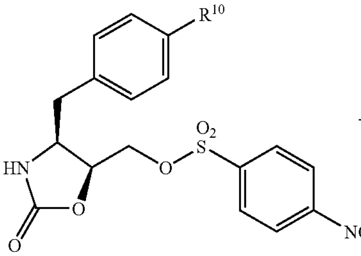

4.2

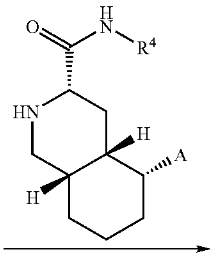

20.1

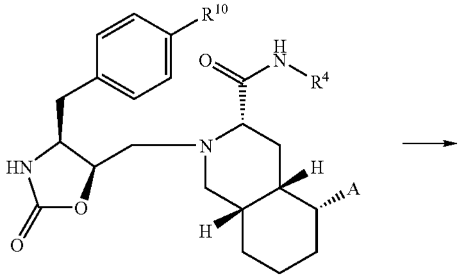

20.2

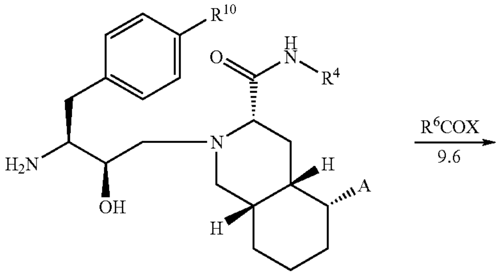

20.3

-continued
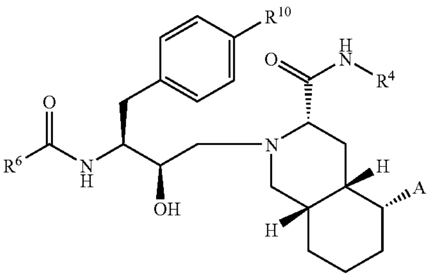
19.4
Scheme 21
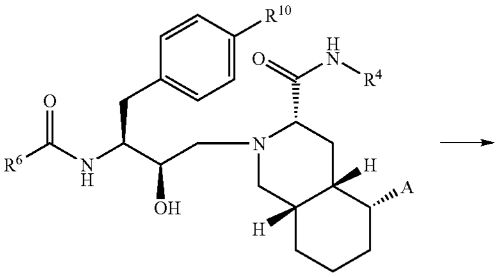
19.4
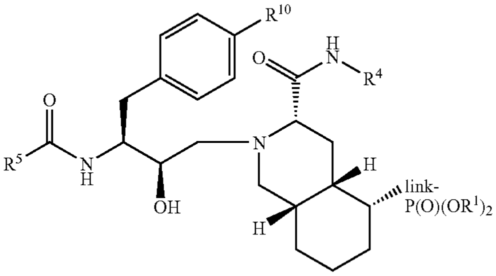
4
Scheme 22
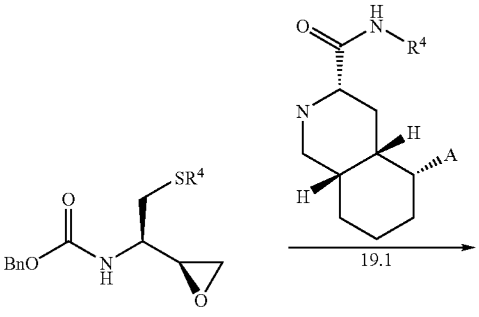
7.7
-continued
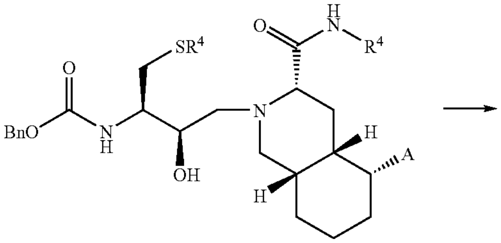
22.1
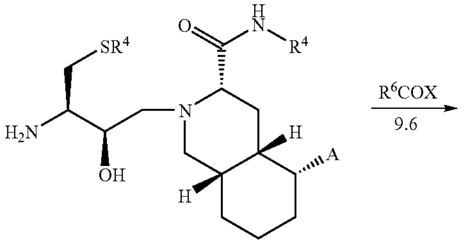
22.2
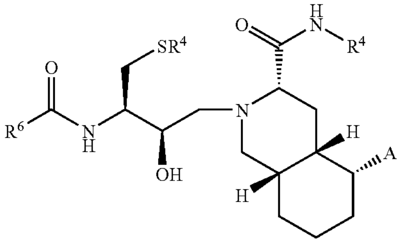
22.3
Scheme 23
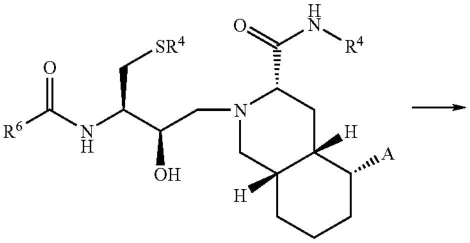
22.3
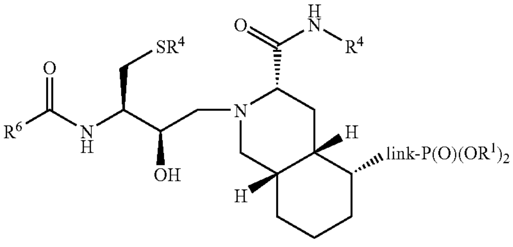
4

Scheme 24

Method

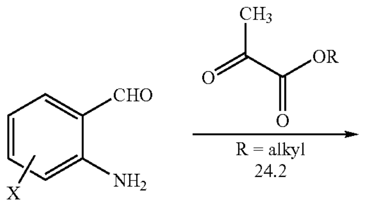

24.1

X = OH, SH, $NH_2$, Br

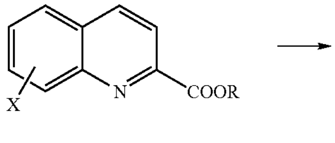

24.3

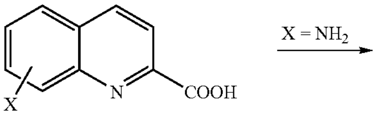

24.4

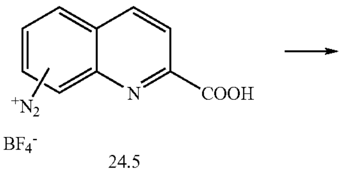

24.5

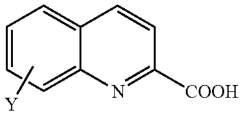

Y = OH, SH, Br 24.6

Example

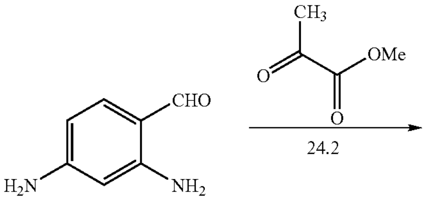

24.7

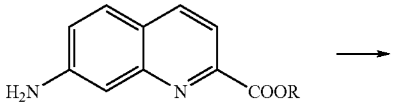

24.8

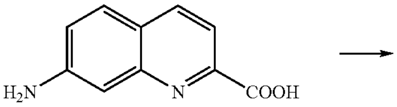

24.9

-continued

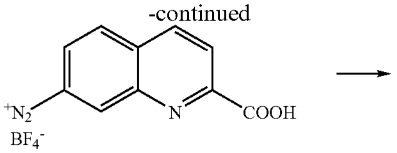

24.10

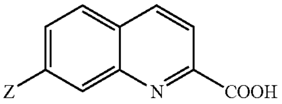

Z = OH, SH, Br 24.11

Preparation of Quinoline 2-carboxylic Acids 1.7 Incorporating Phosphonate Moieties or Precursors Thereto.

The reaction sequence depicted in Scheme 1 requires the use of a quinoline-2-carboxylic acid reactant 1.7 in which the substituent A is either the group link-$P(O)(OR^1)_2$ or a precursor thereto, such as [OH], [SH] Br.

A number of suitably substituted quinoline-2-carboxylic acids are available commercially or are described in the chemical literature. For example, the preparations of 6-hydroxy, 6-amino and 6-bromoquinoline-2-carboxylic acids are described respectively in DE 3004370, J. Het. Chem., 1989, 26, 929 and J. Labelled Comp. Radiopharm., 1998, 41, 1103, and the preparation of 7-aminoquinoline-2-carboxylic acid is described in J. Am. Chem. Soc., 1987, 109, 620. Suitably substituted quinoline-2-carboxylic acids can also be prepared by procedures known to those skilled in the art. The synthesis of variously substituted quinolines is described, for example, in Chemistry of Heterocyclic Compounds, Vol. 32, G. Jones, ed., Wiley, 1977, p. 93ff. Quinoline-2-carboxylic acids can be prepared by means of the Friedlander reaction, which is described in Chemistry of Heterocyclic Compounds, Vol. 4, R. C. Elderfield, ed., Wiley, 1952, p. 204.

Scheme 24 illustrates the preparation of quinoline-2-carboxylic acids by means of the Friedlander reaction, and further transformations of the products obtained. In this reaction sequence, a substituted 2-aminobenzaldehyde 24.1 is reacted with an alkyl pyruvate ester 24.2, in the presence of an organic or inorganic base, to afford the substituted quinoline-2-carboxylic ester 24.3. Hydrolysis of the ester, for example by the use of aqueous base, then afford the corresponding carboxylic acid 24.4. The carboxylic acid product 24.4 in which X is $NH_2$ can be further transformed into the corresponding compounds 24.6 in which Z is OH, SH or Br. The latter transformations are effected by means of a diazotization reaction. The conversion of aromatic amines into the corresponding phenols and bromides by means of a diazotization reaction is described respectively in Synthetic Organic Chemistry, R. B. Wagner, H. D. Zook, Wiley, 1953, pages 167 and 94; the conversion of amines into the corresponding thiols is described in Sulfur Lett., 2000, 24, 123. The amine is first converted into the diazonium salt by reaction with nitrous acid. The diazonium salt, preferably the diazonium tetrafluoborate, is then heated in aqueous solution, for example as described in Organic Functional Group Preparations, by S. R. Sandler and W. Karo, Academic Press, 1968, p. 83, to afford the corresponding phenol 24.6, X=OH. Alternatively, the diazonium salt is reacted in aqueous solution with cuprous bromide and lithium bromide, as described in Organic Functional Group Preparations, by S. R. Sandler and W. Karo, Academic Press, 1968, p. 138, to yield the corresponding bromo compound, 24.6, Y=Br. Alternatively, the diazonium tetrafluoborate is reacted in acetonitrile solution with a sulfhydryl ion exchange resin, as described in Sulfur Lett., 200, 24, 123, to afford the thiol 24.6, Y=SH. Optionally, the diazotization reactions described above can be performed on the carboxylic esters 24.3 instead of the carboxylic acids 24.5.

For example, 2,4-diaminobenzaldehyde 24.7 (Apin Chemicals) is reacted with one molar equivalent of methylpyruvate 24.2 in methanol, in the presence if a base such as piperidine, to afford methyl-7-aminoquinoline-2-carboxylate 24.8. Basic hydrolysis of the product, employing one molar equivalent of lithium hydroxide in aqueous methanol, then yields the carboxylic acid 24.9. The amino-substituted carboxylic acid is then converted into the diazonium tetrafluoborate 24.10 by reaction with sodium nitrite and tetrafluoboric acid. The diazonium salt is heated in aqueous solution to afford the 7-hydroxyquinoline-2-carboxylic acid, 24.11, Z=OH. Alternatively, the diazonium tetrafluoborate is heated in aqueous organic solution with one molar equivalent of cuprous bromide and lithium bromide, to afford 7-bromoquinoline-2-carboxylic acid 24.11, X=Br. Alternatively, the diazonium tetrafluoborate 24.10 is reacted in acetonitrile solution with the sulfhydryl form of an ion exchange resin, as described in Sulfur Lett., 2000, 24, 123, to prepare 7-mercaptoquinoline-2-carboxylic acid 24.11, Z=SH.

Using the above procedures, but employing, in place of 2,4-diaminobenzaldehyde 24.7, different aminobenzaldehydes 24.1, the corresponding amino, hydroxy, bromo or mercapto-substituted quinoline-2-carboxylic acids 24.6 are obtained. The variously substituted quinoline carboxylic acids and esters can then be transformed, as described below, (Schemes 25-27) into phosphonate-containing derivatives.

Scheme 25 depicts the preparation of quinoline-2-carboxylic acids incorporating a phosphonate moiety attached to the quinoline ring by means of an oxygen or a sulfur atom. In this procedure, an amino-substituted quinoline-2-carboxylate ester 25.1 is transformed, via a diazotization procedure as described above (Scheme 24) into the corresponding phenol or thiol 25.2. The latter compound is then reacted with a dialkyl hydroxymethylphosphonate 25.3, under the conditions of the Mitsonobu reaction, to afford the phosphonate ester 25.4. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the thioether products 25.5. Basic hydrolysis of the ester group, for example employing one molar equivalent of lithium hydroxide in aqueous methanol, then yields the carboxylic acid 25.6.

For example, methyl 6-amino-2-quinoline carboxylate 25.7, prepared as described in J. Het. Chem., 1989, 26, 929, is converted, by means of the diazotization procedure described above, into methyl 6-mercaptoquinoline-2-carboxylate 25.8. This material is reacted with a dialkyl hydroxymethylphosphonate 25.9 (Aldrich) in the presence of diethyl azodicarboxylate and triphenylphosphine in tetrahydrofuran solution, to afford the thioether 25.10. Basic hydrolysis then afford the carboxylic acid 25.11.

Using the above procedures, but employing, in place of methyl 6-amino-2-quinoline carboxylate 25.7, different aminoquinoline carboxylic esters 25.1, and/or different dialkyl hydroxymethylphosphonates 25.9 the corresponding phosphnoate ester products 25.3 are obtained.

Scheme 26 illustrates the preparation of quinoline-2-carboxylic acids incorporating phosphonate esters attached to the quinoline ring by means of a saturated or unsaturated carbon chain. In this reaction sequence, a bromo-substituted quinoline carboxylic ester 26.1 is coupled, by means of a palladium-catalyzed Heck reaction, with a dialkyl alkenylphosphonate 26.2. The coupling of aryl halides with olefins by means of the Heck reaction is described, for example, in Advanced Organic Chemistry, by F. A. Carey and R. J. Sundberg, Plenum, 2001, p. 503ff. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Thus, Heck coupling of the bromo compound 26.1 and the olefin 26.2 affords the olefinic ester 26.3. Hydrolysis, for example by reaction with lithium hydroxide in aqueous methanol, or by treatment with porcine liver esterase, then yields the carboxylic acid 26.4. Optionally, the unsaturated carboxylic acid 26.4 can be reduced to afford the saturated analog 26.5. The reduction reaction can be effected chemically, for example by the use of diimide or diborane, as described in Comprehensive Organic Transformations, by R. C. Larock, VCH, 1989, p. 5. For example, methyl 7-bromoquinoline-2-carboxylate, 26.6, prepared as described in J. Labelled Comp. Radiopharm., 1998, 41, 1103, is reacted in dimethylformamide at 60° C. with a dialkyl vinylphosphonate 26.7 (Aldrich) in the presence of 2 mol % of tetrakis(triphenylphosphine)palladium and triethylamine, to afford the coupled product 26.8.

The product is then reacted with lithium hydroxide in aqueous tetrahydrofuran to produce the carboxylic acid 26.9. The latter compound is reacted with diimide, prepared by basic hydrolysis of diethyl azodicarboxylate, as described in Angew. Chem. Int. Ed., 4, 271, 1965, to yield the saturated product 26.10.

Using the above procedures, but employing, in place of methyl 6-bromo-2-quinolinecarboxylate 26.6, different bromoquinoline carboxylic esters 26.1, and/or different dialkyl alkenylphosphonates 26.2, the corresponding phosphonate ester products 26.4 and 26.5 are obtained.

Scheme 27 depicts the preparation of quinoline-2-carboxylic acids 27.5 in which the phosphonate group is attached by means of a nitrogen atom and an alkylene chain. In this reaction sequence, a methyl aminoquinoline-2-carboxylate 27.1 is reacted with a phosphonate aldehyde 27.2 under reductive amination conditions, to afford the aminoalkyl product 27.3. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p. 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The ester product 27.4 is then hydrolyzed to yield the free carboxylic acid 27.5.

For example, methyl 7-aminoquinoline-2-carboxylate 27.6, prepared as described in J. Amer. Chem. Soc., 1987, 109, 620, is reacted with a dialkyl formylmethylphosphonate 27.7 (Aurora) in methanol solution in the presence of sodium borohydride, to afford the alkylated product 27.8. The ester is then hydrolyzed, as described above, to yield the carboxylic acid 27.9. Using the above procedures, but employing, in place of the formylmethyl phosphonate 27.2, different formylalkyl phosphonates, and/or different aminoquinolines 27.1, the corresponding products 27.5 are obtained.
Scheme 25
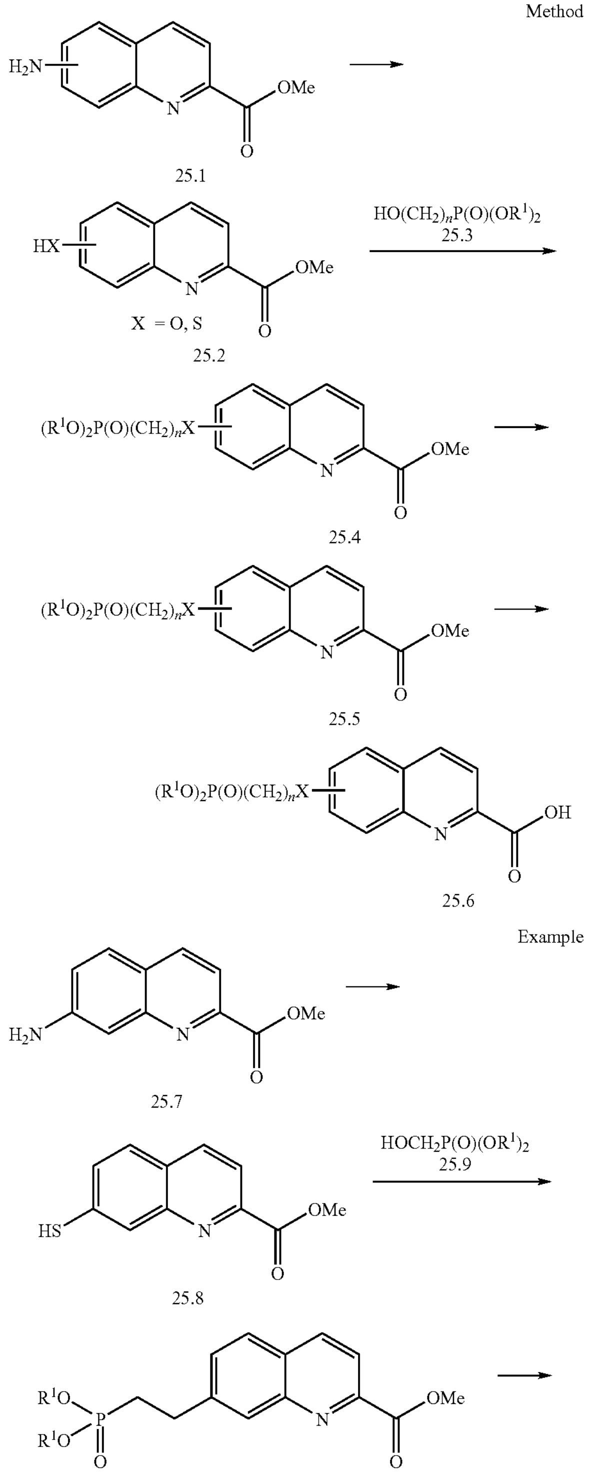
25.1
25.2
25.4
25.5
25.6
25.7
25.8
25.10
-continued
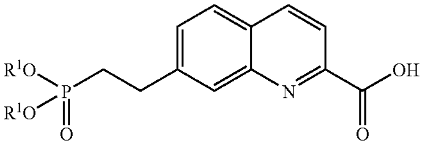
25.11
Scheme 26
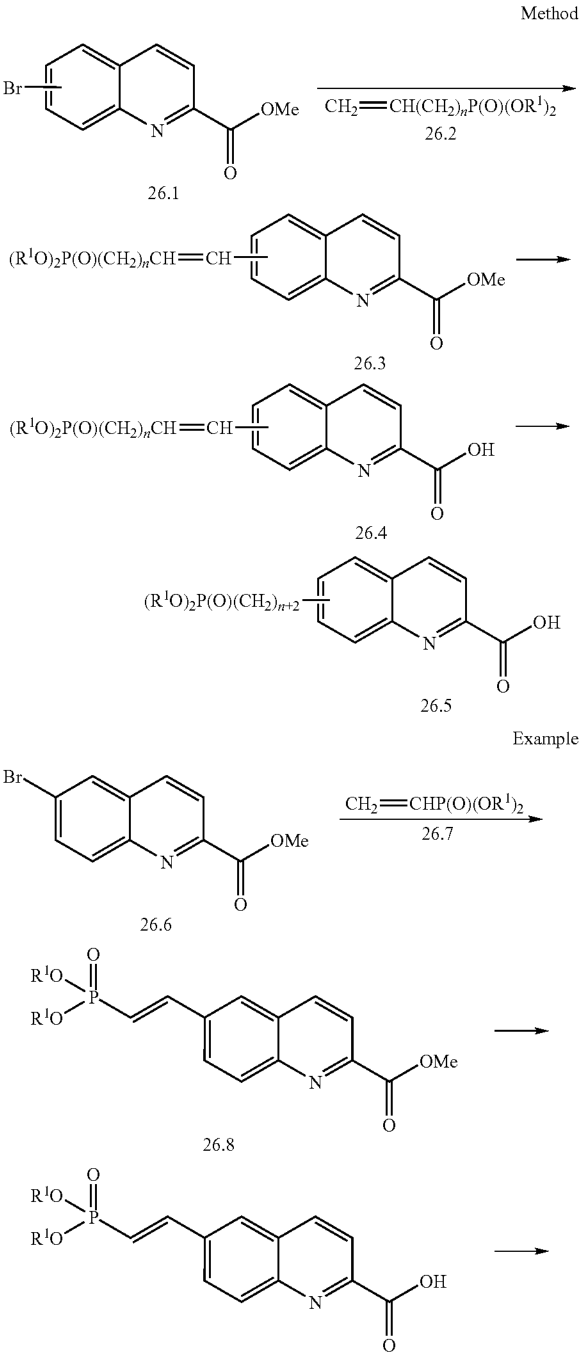
26.1
26.3
26.4
26.5
26.6
26.8
26.9

-continued
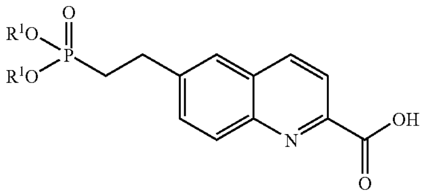
26.10
Scheme 27
Method
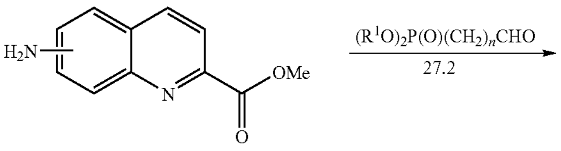
27.1
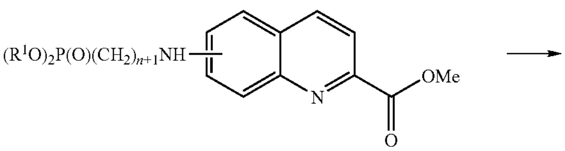
27.3
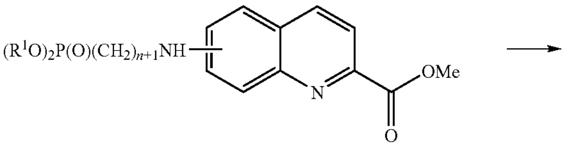
27.4
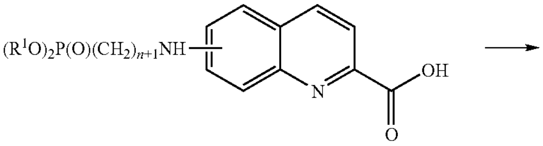
27.5
Example
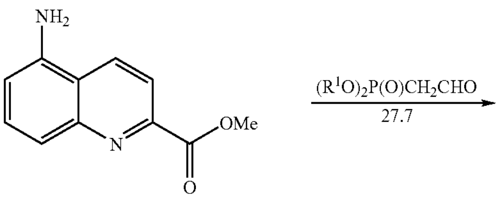
27.6
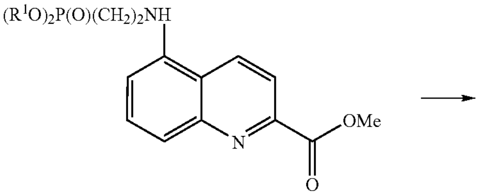
27.8
-continued
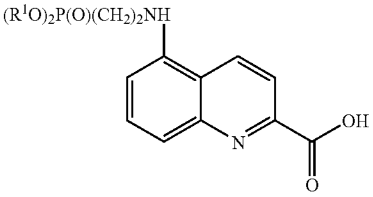
27.9
Scheme 28
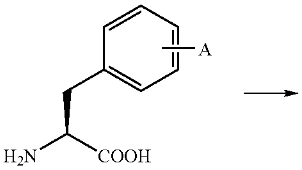
28.1
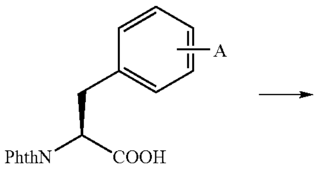
28.2
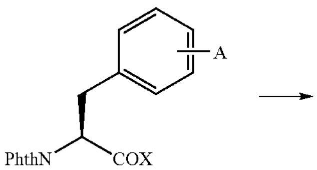
28.3
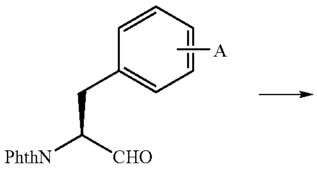
28.4
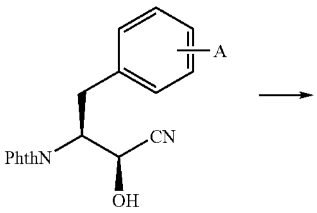
28.5
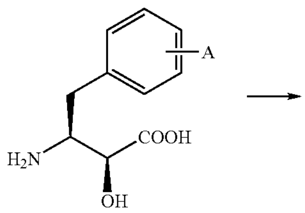
28.6

-continued

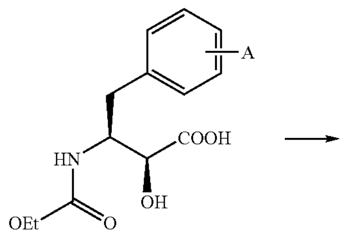

28.7

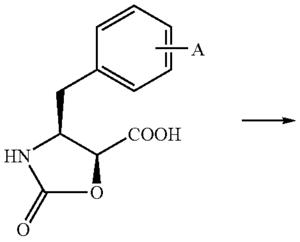

28.8

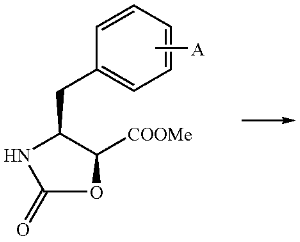

28.9

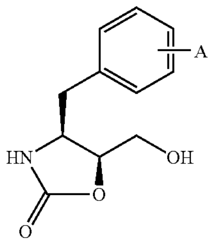

9.1

-continued

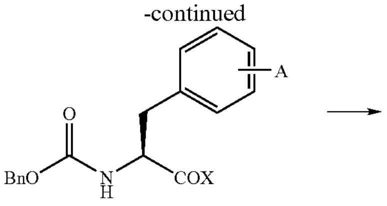

29.3

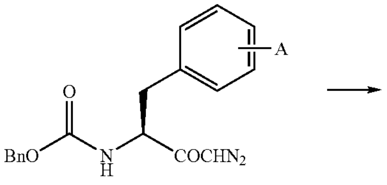

29.4

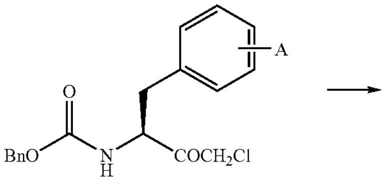

29.5

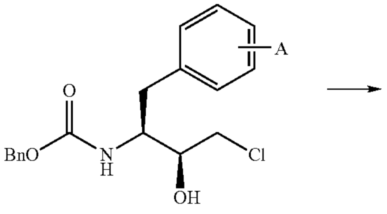

29.6

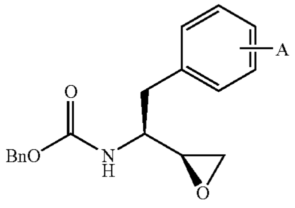

10.1

Scheme 29

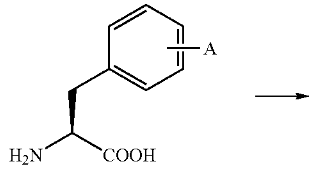

29.1

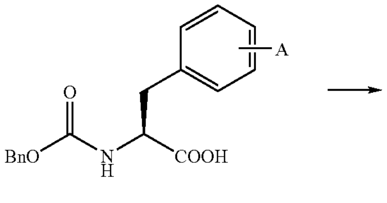

29.2

Preparation of Phenylalanine Derivatives 9.1 and 10.1 Incorporating Phosphonate Moieties or Precursors Thereto.

Scheme 28 illustrates the preparation of the hydroxymethyl oxazolidine derivative 9.1, in which the substituent A is either the group link-P(O)$(OR^1)_2$ or a precursor thereto, such as [OH], [SH] Br. In this reaction sequence, the substituted phenylalanine 28.1, in which A is as defined above, is transformed, via the intermediates 28.2-28.9, into the hydroxymethyl product 9.1. The reaction conditions for each step in the sequence are the same as those described above for the corresponding step shown in Scheme 5. The conversion of the substituent A into the group link-P(O)$(OR^1)_2$ may be effected at any convenient step in the reaction sequence, or after the reactant 9.1 has been incorporated into the intermediates 9.5 (Scheme 9). Specific examples of the preparation of the hydroxymethyl oxazolidinone reactant 9.1 are shown below, (Schemes 30-31).

Scheme 29 illustrates the preparation of the oxirane intermediate 10.1, in which the substituent A is either the group link-$P(O)(OR^1)_2$ or a precursor thereto, such as [OH], [SH] Br. In this reaction sequence, the substituted phenylalanine 29.1, in which A is as defined above, is transformed, via the intermediates 29.2-29.6, into the oxirane 10.1. The reaction conditions for each step in the sequence are the same as those described above for the corresponding step shown in Scheme 2. The conversion of the substituent A into the group link-$P(O)(OR^1)_2$ may be effected at any convenient step in the reaction sequence, or after the reactant 10.1 has been incorporated into the intermediates 9.5 (Scheme 10). Specific examples of the preparation of the oxiranes reactant 10.1 are shown below, (Schemes 32-34).

Scheme 30 depicts the preparation of hydroxymethyloxazolidinones 30.9 in which the phosphonate ester moiety is attached directly to the phenyl ring. In this procedure, a bromo-substituted phenylalanine 30.1 is converted, using the series of reactions illustrated in Scheme 28, into the bromophenyloxazolidinone 30.2. The bromophenyl compound is then coupled, in the presence of a palladium (0) catalyst, with a dialkyl phosphite 30.3, to afford the phosphonate product 30.4. The reaction between aryl bromide and dialkyl phosphites to yield aryl phosphonates is described in Synthesis, 56, 1981, and in J. Med. Chem., 1992, 35, 1371.

The reaction is conducted in an inert solvent such as toluene or xylene, at about 100° C., in the presence of a palladium (0) catalyst such as tetrakis(triphenylphosphine)palladium and a tertiary organic base such as triethylamine. The carbomethoxy substituent in the resultant phosphonate ester 30.4 is then reduced with sodium borohydride to the corresponding hydroxymethyl derivative 30.5, using the procedure described above (Scheme 28) For example, 3-bromophenylalanine 30.6, prepared as described in Pept. Res., 1990, 3, 176, is converted, using the sequence of reactions shown in Scheme 28, into 4-(3-bromo-benzyl)-2-oxo-oxazolidine-5-carboxylic acid methyl ester 30.7. This compound is then coupled with a dialkyl phosphite 30.3, in toluene solution at reflux, in the presence of a catalytic amount of tetrakis(triphenylphosphine)palladium(0) and triethylamine, to afford the phosphonate ester 30.8. The carbomethoxy substituent is then reduced with sodium borohydride, as described above, to afford the hydroxymethyl product 30.9.

Using the above procedures, but employing, in place of 3-bromophenylalanine 30.6 different bromophenylalanines 30.1 and/or different dialkyl phosphites 30.3, the corresponding products 30.5 are obtained.

Scheme 31 illustrates the preparation of phosphonate-containing hydroxymethyl oxazolidinones 31.9 and 31.12 in which the phosphonate group is attached by means of a heteroatom and a carbon chain. In this sequence of reactions, a hydroxy or thio-substituted phenylalanine 31.1 is converted into the benzyl ester 31.2 by means of a conventional acid catalyzed esterification reaction. The hydroxyl or mercapto group is then protected. The protection of phenyl hydroxyl and thiol groups are described, respectively, in Protective Groups in Organic Synthesis, by T. W. Greene and P. G. M Wuts, Wiley, Second Edition 1990, p. 10, and p. 277. For example, hydroxyl and thiol substituents can be protected as trialkylsilyloxy groups. Trialkylsilyl groups are introduced by the reaction of the phenol or thiophenol with a chlorotrialkylsilane and a base such as imidazole, for example as described in Protective Groups in Organic Synthesis, by T. W. Greene and P. G. M Wuts, Wiley, Second Edition 1990, p. 10, p. 68-86. Alternatively, thiol substituents can be protected by conversion to tert-butyl or adamantyl thioethers, or 4-methoxybenzyl thioethers, prepared by the reaction between the thiol and 4-methoxybenzyl chloride in the presence of ammonium hydroxide, as described in Bull. Chem. Soc. Jpn., 37, 433, 1974. The protected ester 31.3 is then reacted with phthalic anhydride, as described above (Scheme 28) to afford the phthalimide 31.4. The benzyl ester is then removed, for example by catalytic hydrogenation or by treatment with aqueous base, to afford the carboxylic acid 31.5. This compound is transformed, by means of the series of reactions shown in Scheme 28, into the carbomethoxy oxazolidinone 31.6, using in each step the same conditions as are described above (Scheme 28). The protected OH or SH group is then deprotected. Deprotection of phenols and thiophenols is described in Protective Groups in Organic Synthesis, by T. W. Greene and P. G. M Wuts, Wiley, Second Edition 1990, p. For example, trialkylsilyl ethers or thioethers can be deprotected by treatment with a tetraalkylammonium fluoride in an inert solvent such as tetrahydrofuran, as described in J. Am Chem. Soc., 94, 6190, 1972. Tert-butyl or adamantyl thioethers can be converted into the corresponding thiols by treatment with mercuric trifluoroacetate in aqueous acetic acid at ambient temperatures, as described in Chem. Pharm. Bull., 26, 1576, 1978. The resultant phenol or thiol 31.7 is then reacted with a hydroxyalkyl phosphonate 31.20 under the conditions of the Mitsonobu reaction, as described above (Scheme 25), to afford the ether or thioether 31.8. The latter compound is then reduced with sodium borohydride, as described above (Scheme 28) to afford the hydroxymethyl analog 31.9.

Alternatively, the phenol or thiophenol 31.7 is reacted with a dialkyl bromoalkyl phosphonate 31.10 to afford the alkylation product 31.11. The alkylation reaction is preformed in a polar organic solvent such as dimethylformamide, acetonitrile and the like, optionally in the presence of potassium iodide, and in the presence of an inorganic base such as potassium or cesium carbonate, or an organic base such as diazabicyclononene or dimethylaminopyridine. The ether or thioether product is then reduced with sodium borohydride to afford the hydroxymethyl compound 31.12.

For example, 3-hydroxyphenylalanine 31.13 (Fluka) is converted in to the benzyl ester 31.14 by means of a conventional acid-catalyzed esterification reaction. The ester is then reacted with tert-butylchlorodimethylsilane and imidazole in dimethylformamide, to afford the silyl ether 31.15. The protected ether is then reacted with phthalic anhydride, as described above (Scheme 28) to yield the phthalimido-protected compound 31.16. Basic hydrolysis, for example by reaction with lithium hydroxide in aqueous methanol, then affords the carboxylic acid 31.17. This compound is then transformed, by means of the series of reactions shown in Scheme 28, into the carbomethoxy-substituted oxazolidinone 31.18. The silyl protecting group is then removed by treatment with tetrabutylammonium fluoride in tetrahydrofuran at ambient temperature, to produce the phenol 31.19. The latter compound is reacted with a dialkyl hydroxymethyl phosphonate 31.20 diethylazodicarboxylate and triphenylphosphine, by means of the Mitsonobu reaction, as described above (Scheme 25) to yield the phenolic ether 31.21. The carbomethoxy group is then reduced by reaction with sodium borohydride, as described above, to afford the carbinol 31.22.

Using the above procedures, but employing, in place of 3-hydroxyphenylalanine 31.13, different hydroxy or mercapto-substituted phenylalanines 31.1, and/or different dialkyl hydroxyalkyl phosphonates 31.20, the corresponding products 31.9 are obtained. As a further example of the methods illustrated in Scheme 31, 4-mercaptophenylalanine 31.23, prepared as described in J. Amer. Chem. Soc., 1997, 119, 7173, is converted into the benzyl ester 31.24 by means of a conventional acid-catalyzed esterification reaction. The mercapto group is then protected by conversion to the S-adamantyl group, by reaction with 1-adamantanol and trifluoroacetic acid at ambient temperature as described in Chem. Pharm. Bull., 26, 1576, 1978. The amino group is then converted into the phthalimido group as described above, and the ester moiety is hydrolyzed with aqueous base to afford the carboxylic acid 31.27. The latter compound is then transformed, by means of the series of reactions shown in Scheme 28, into the carbomethoxy oxazolidinone 31.28. The adamantyl protecting group is then removed by treatment of the thioether 31.28 with mercuric acetate in trifluoroacetic acid at 0° C., as described in Chem. Pharm. Bull., 26, 1576, 1978, to produce the thiol 31.29. The thiol is then reacted with one molar equivalent of a dialkyl bromoethylphosphonate 31.30, (Aldrich) and cesium carbonate in dimethylformamide at 70° C., to afford the thioether product 31.31. The carbomethoxy group is then reduced with sodium borohydride, as described above, to prepare the carbinol 31.32.

Using the above procedures, but employing, in place of 4-mercaptophenylalanine 31.23, different hydroxy or mercapto-substituted phenylalanines 31.10, and/or different dialkyl bromoalkyl phosphonates 31.10, the corresponding products 31.12 are obtained.

Scheme 32 illustrates the preparation of phenylalanine derivatives 32.3 in which the phosphonate group is attached directly to the phenyl ring. In this procedure, a bromo-substituted phenylalanine 32.1 is converted, by means of the series of reactions shown in Scheme 29 into the oxirane 32.2. This compound is then coupled with a dialkyl phosphite 30.3, in the presence of a palladium(0) catalyst and an organic base, to afford the phosphonate oxirane 32.3. The coupling reaction is performed under the same conditions previously described, (Scheme 30).

For example, 3-bromophenylalanine 32.4, prepared as described in Pept. Res., 1990, 3, 176, is converted, as described above, into the oxirane 32.5. This compound is reacted, in toluene solution at reflux temperature, with a dialkyl phosphonate 30.3, in the presence of tetrakis(triphenylphosphine)palladium(0) and triethylamine to afford the phosphonate ester 32.6.

Using the above procedures, but employing, in place of 4-bromophenylalanine 32.4, different bromo-substituted phenylalanines 32.1, and/or different dialkyl phosphites 30.3, the corresponding products 32.3 are obtained.

Scheme 33 depicts the preparation of compounds 33.4 in which the phosphonate group is attached to the phenyl ring by means of a styrene moiety. In this reaction sequence, a vinyl-substituted phenylalanine 33.1 is converted, by means of the series of reactions shown in Scheme 29, into the oxirane 33.2. This compound is then coupled with a dialkyl bromophenylphosphonate 33.3, employing the conditions of the Heck reaction, as described above (Scheme 26) to afford the coupled product 33.4.

For example, 4-vinylphenylalanine 33.5, prepared as described in EP 206460, is converted, as described above, into the oxirane 33.6. This compound is then coupled with a dialkyl 4-bromophenylphosphonate 33.7, prepared as described in J. Chem. Soc. Perkin Trans., 1977, 2, 789, using tetrakis(triphenylphosphine)palladium(0) as catalyst, to yield the phosphonate ester 33.8.

Using the above procedures, but employing, in place of 4-vinylphenylalanine 33.5, different vinyl-substituted phenylalanines 33.1, and/or different dialkyl bromophenylphosphonates 33.3, the corresponding products 33.4 are obtained.

Scheme 34 depicts the preparation of phosphonate-substituted phenylalanine derivatives in which the phosphonate moiety is attached by means of an alkylene chain incorporating a heteroatom. In this procedure, a hydroxymethyl-substituted phenylalanine 34.1 is converted into the cbz protected methyl ester 34.2, using the procedures described above (Scheme 29). The product 34.2 is then converted into a halomethyl-substituted compound 34.3. For example, the carbinol 34.2 is treated with triphenylphosphine and carbon tetrabromide, as described in J. Amer. Chem. Soc., 108, 1035, 1986 to afford the product 34.3 in which Z is Br. The bromo compound is then reacted with a dialkyl terminally hetero-substituted alkylphosphonate 34.4. The reaction is accomplished in the presence of a base, the nature of which depends on the nature of the substituent X. For example, if X is SH, $NH_2$ or NHalkyl, an inorganic base such as cesium carbonate, or an organic base such as diazabicyclononene or dimethylaminopyridine, can be employed. If X is OH, a strong base such as lithium hexamethyldisilylazide or the like can be employed. The condensation reaction affords the phosphonate-substituted ester 34.5, which is hydrolyzed to afford the carboxylic acid 34.6. The latter compound is then, by means of the sequence of reactions shown in Scheme 29, is transformed into the epoxide 34.7.

For example, the protected 4-hydroxymethyl-substituted phenylalanine derivative 34.9, obtained from the 4-hydroxymethyl phenylalanine 34.8, the preparation of which is described in Syn. Comm., 1998, 28, 4279, is converted into the bromo derivative 34.10, as described above. The product is then reacted with a dialkyl 2-aminoethyl phosphonate 34.11, the preparation of which is described in J. Org. Chem., 2000, 65, 676, in the presence of cesium carbonate in dimethylformamide at ambient temperature, to afford the amine product 34.12. The latter compound is then converted, using the sequence of reactions shown in Scheme 29, into the epoxide 34.14.

Using the above procedures, but employing different carbinols 34.1 in place of the carbinol 34.8, and/or different phosphonates 34.4, the corresponding products 34.7 are obtained.

Scheme 30

Method

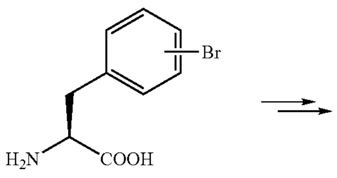

30.1

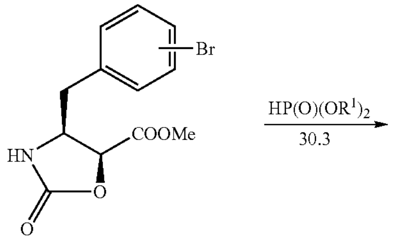

30.2

-continued
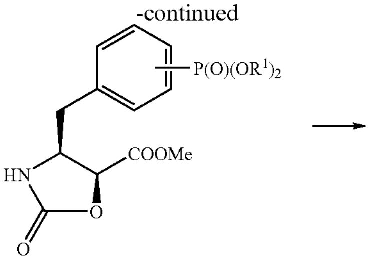
30.4
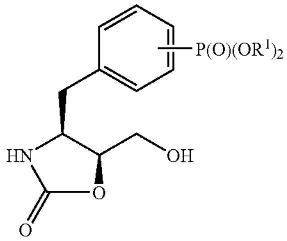
30.5
Example
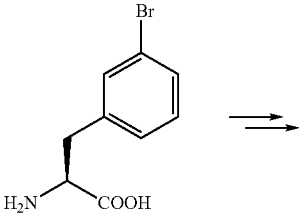
30.6
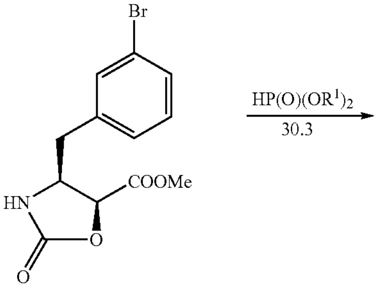
30.7
-continued
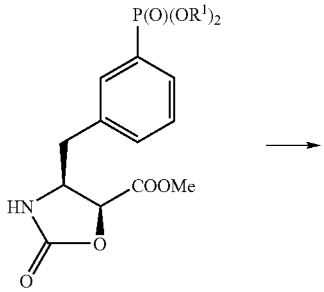
30.8
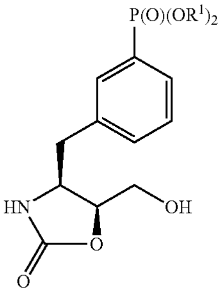
30.9
Scheme 31
Method
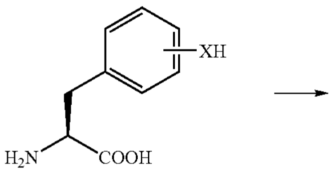
X = O, S
31.1
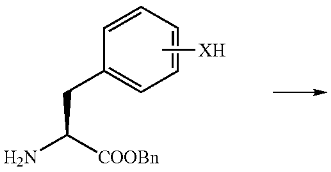
31.2
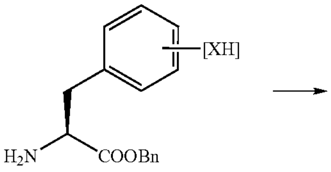
31.3

-continued
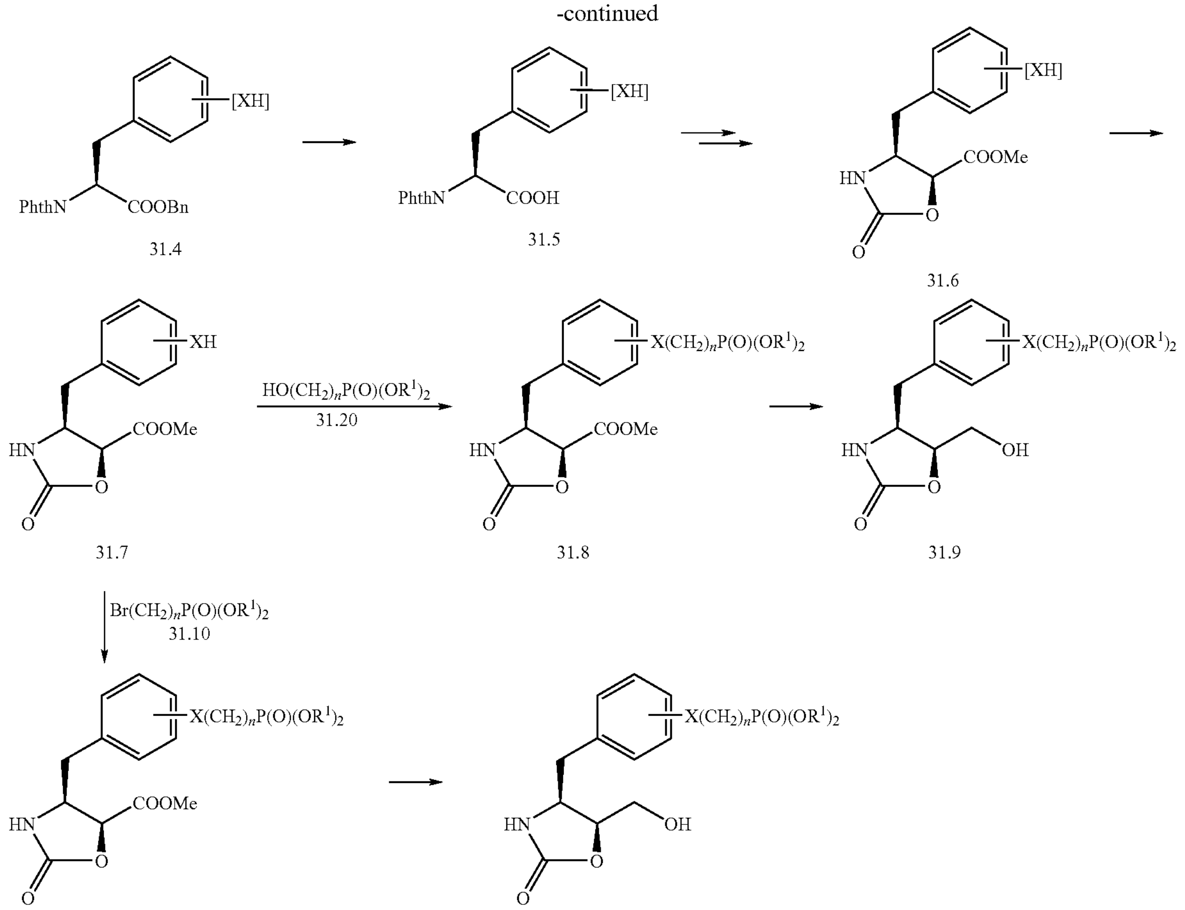
31.4, 31.5, 31.6, 31.7, 31.8, 31.9, 31.11, 31.12
Scheme 31
Example 1
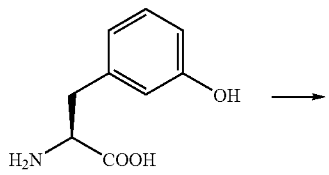
31.13
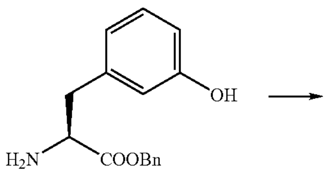
31.14
-continued
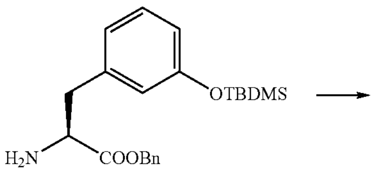
31.15
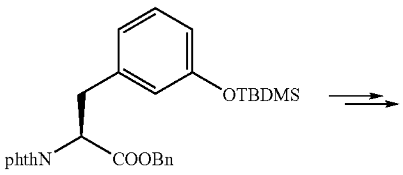
31.16 phth = phthalimido
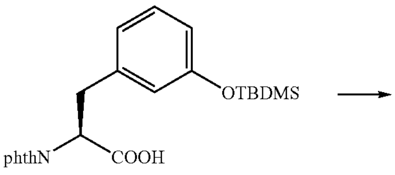
31.17

-continued
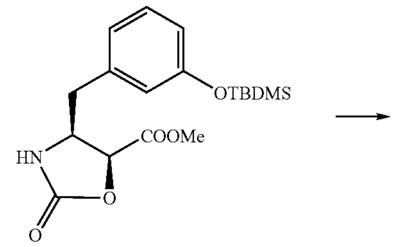
31.18
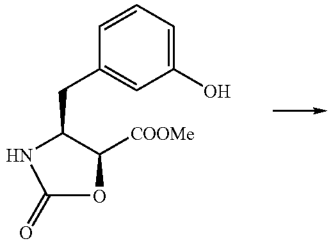
$HOCH_2P(O)(OR^1)_2$
31.20
31.19
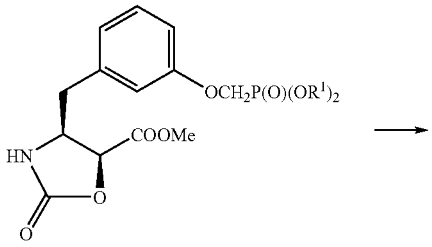
31.21
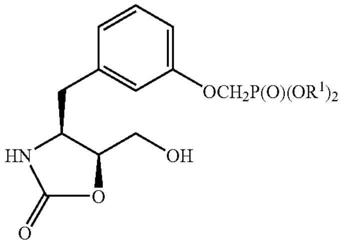
31.22
Example 2
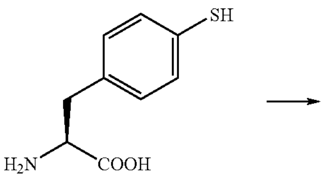
31.23
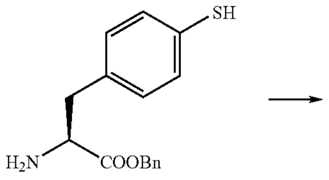
31.24
-continued
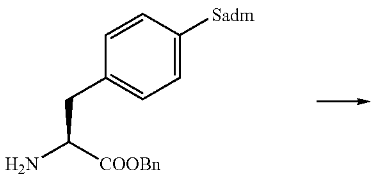
31.25
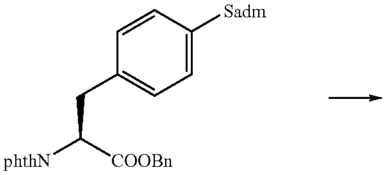
31.26
adm = adamanthyl
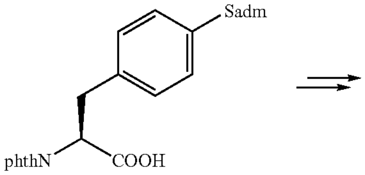
31.27
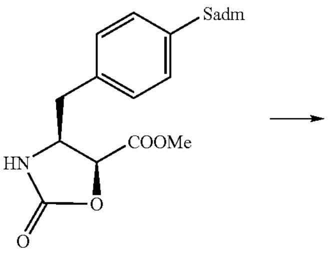
31.28
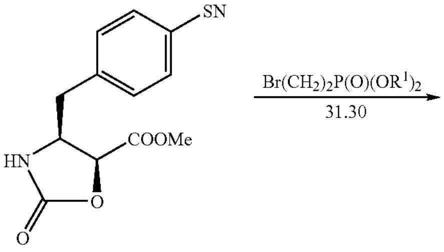
31.29
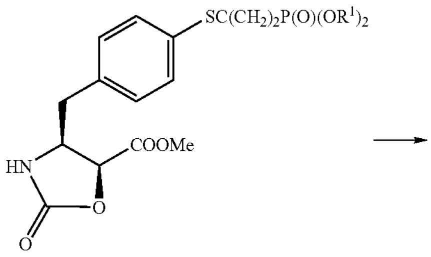
31.31

-continued
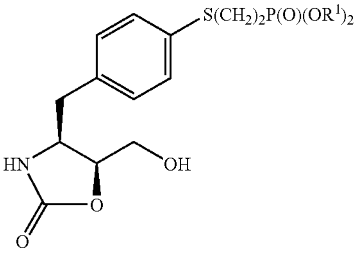
31.32
Scheme 32
Method
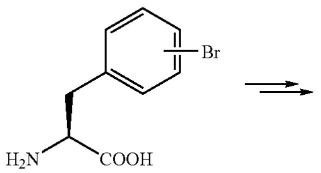
32.1
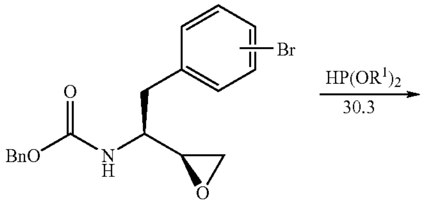
32.2
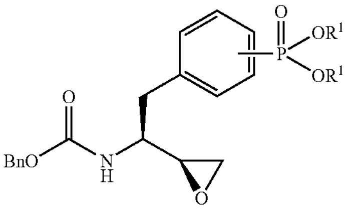
32.3
Example
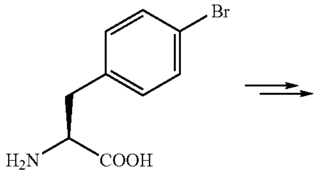
32.4
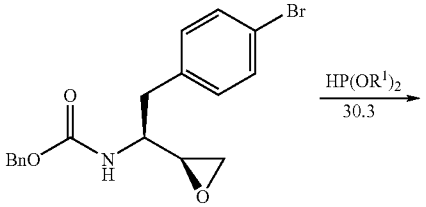
32.5
-continued
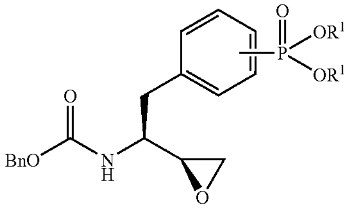
32.6
Scheme 33
Method
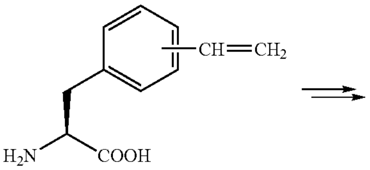
33.1
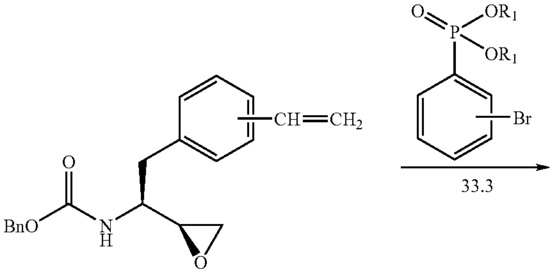
33.3
33.2
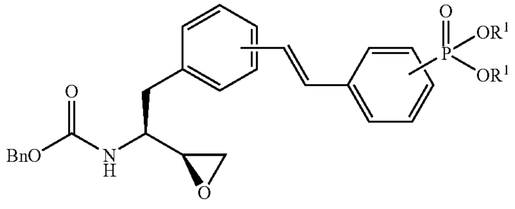
33.4
Example
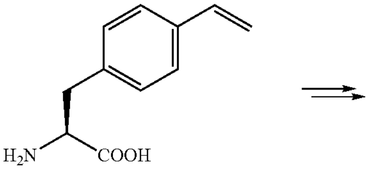
33.5

-continued
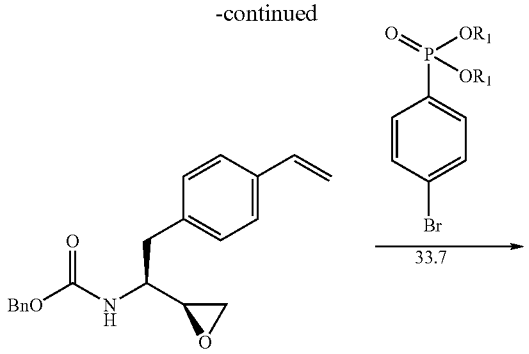
33.6
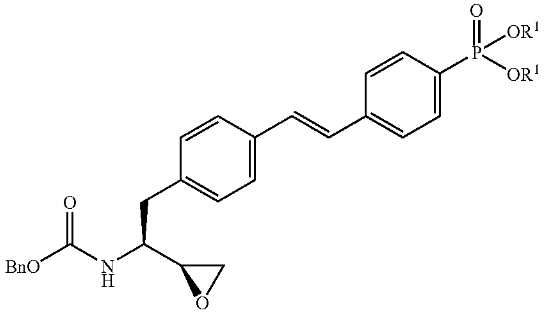
33.8
Scheme 34
Method
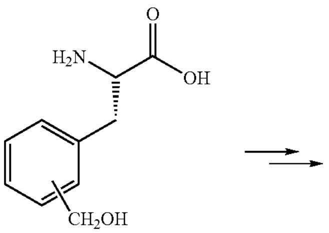
34.1
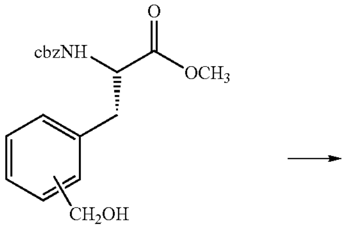
34.2
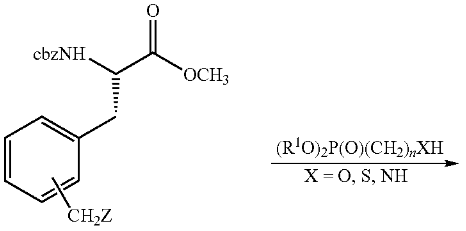
Z = Cl, Br
34.3
34.4
-continued
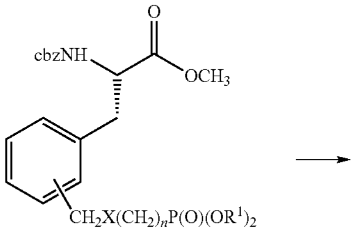
34.5
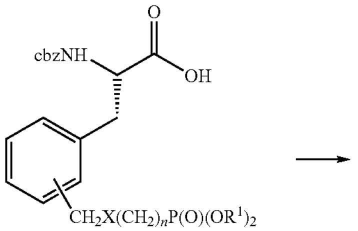
34.6
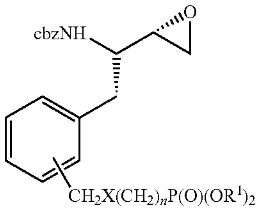
34.7
Example
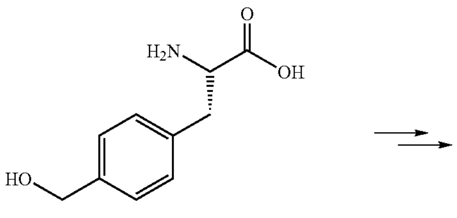
34.8
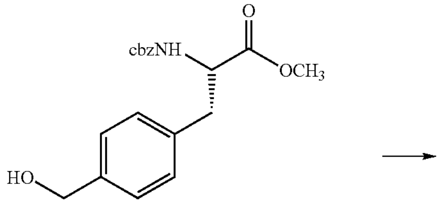
34.9
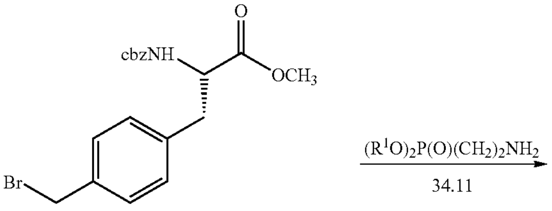
34.10

-continued

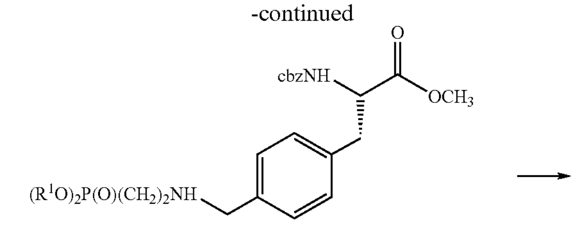

34.12

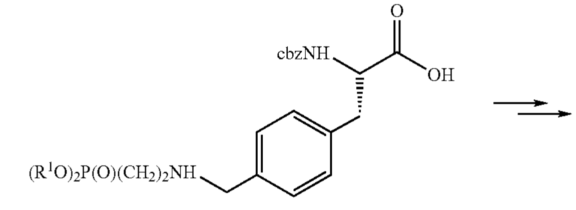

34.13

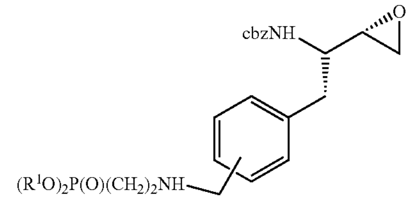

34.14

Preparation of Thiophenols 12.2 Incorporating Phosphonate Groups.

Scheme 35 illustrates the preparation of thiophenols in which a phosphonate moiety is attached directly to the aromatic ring. In this procedure, a halo-substituted thiophenol 35.1 is subjected to a suitable protection procedure. The protection of thiophenols is described, for example, in Protective Groups in Organic Synthesis, by T. W. Greene and P. G. M Wuts, Wiley, Second Edition 1990, p 277ff. The protected compound 35.2 is then coupled, under the influence of a transition metal catalyst, with a dialkyl phosphite 30.3, to afford the product 35.3. The product is then deprotected to afford the free thiophenol 35.4. Suitable protecting groups for this procedure include alkyl groups such as triphenylmethyl and the like. Palladium (0) catalysts are employed, and the reaction is conducted in an inert solvent such as benzene, toluene and the like, as described in J. Med. Chem., 35, 1371, 1992. Preferably, the 3-bromothiophenol 35.5 is protected by conversion to the 9-fluorenylmethyl derivative 35.6, as described in Protective Groups in Organic Synthesis, by T. W. Greene and P. G. M. Wuts, Wiley, 1991, pp. 284, and the product is reacted in toluene with a dialkyl phosphite in the presence of tetrakis(triphenylphosphine)palladium (0) and triethylamine, to yield the product 35.7. Deprotection, for example by treatment with aqueous ammonia in the presence of an organic co-solvent, as described in J. Chem. Soc. Chem. Comm. 1501, 1986, then gives the thiol 35.8.

Using the above procedures, but employing, in place of the bromo compound 35.5, different bromo compounds 35.2, and/or different phosphonates 30.3, there are obtained the corresponding thiols 35.4.

Scheme 36 illustrates an alternative method for obtaining thiophenols with a directly attached phosphonate group. In this procedure, a suitably protected halo-substituted thiophenol 36.2 is metallated, for example by reaction with magnesium or by transmetallation with an alkyllithium reagent, to afford the metallated derivative 36.3. The latter compound is reacted with a halodialkyl phosphate 36.4, followed by deprotection as described previously, to afford the product 36.5.

For example, 4-bromothiophenol 36.7 is converted into the S-triphenylmethyl (trityl) derivative 36.8, as described in Protective Groups in Organic Synthesis, by T. W. Greene and P. G. M. Wuts, Wiley, 1991, pp. 287. The product is converted into the lithium derivative 36.9 by reaction with butyllithium in an ethereal solvent at low temperature, and the resulting lithio compound is reacted with a dialkyl chlorodiethyl phosphite 36.10 to afford the phosphonate 36.11. Removal of the trityl group, for example by treatment with dilute hydrochloric acid in acetic acid, as described in J. Org. Chem., 31, 1-118, 1966, then affords the thiol 36.12. Using the above procedures, but employing, in place of the bromo compound 36.7, different halo compounds 36.2, and/or different halo dialkyl phosphites 36.4, there are obtained the corresponding thiols 36.6.

Scheme 37 illustrates the preparation of phosphonate-substituted thiophenols in which the phosphonate group is attached by means of a one-carbon link. In this procedure, a suitably protected methyl-substituted thiophenol 37.1 is subjected to free-radical bromination to afford a bromomethyl product 37.1a. This compound is reacted with a sodium dialkyl phosphite 37.2 or a trialkyl phosphite, to give the displacement or rearrangement product 37.3, which upon deprotection affords the thiophenols 37.4.

For example, 2-methylthiophenol 37.5 is protected by conversion to the benzoyl derivative 37.6, as described in Protective Groups in Organic Synthesis, by T. W. Greene and P. G. M. Wuts, Wiley, 1991, pp. 298. The product is reacted with N-bromosuccinimide in ethyl acetate to yield the bromomethyl product 37.7. This material is reacted with a sodium dialkyl phosphite 37.2, as described in J. Med. Chem., 35, 1371, 1992, to afford the product 37.8. Alternatively, the bromomethyl compound 37.7 can be converted into the phosphonate 37.8 by means of the Arbuzov reaction, for example as described in Handb. Organophosphorus Chem., 1992, 115. In this procedure, the bromomethyl compound 37.7 is heated with a trialkyl phosphate $P(OR^1)_3$ at ca. 100° C. to produce the phosphonate 37.8. Deprotection of 37.8, for example by treatment with aqueous ammonia, as described in J. Amer. Chem. Soc., 85, 1337, 1963, then affords the thiol 37.9.

Using the above procedures, but employing, in place of the bromomethyl compound 37.7, different bromomethyl compounds 37.2, there are obtained the corresponding thiols 37.4.

Scheme 38 illustrates the preparation of thiophenols bearing a phosphonate group linked to the phenyl nucleus by oxygen or sulfur. In this procedure, a suitably protected hydroxy or thio-substituted thiophenol 38.1 is reacted with a dialkyl hydroxyalkylphosphonate 38.2 under the conditions of the Mitsonobu reaction, for example as described in Org. React., 1992, 42, 335, to afford the coupled product 38.3. Deprotection then yields the O- or S-linked products 38.4.

For example, the substrate 3-hydroxythiophenol, 38.5, is converted into the monotrityl ether 38.6, by reaction with one equivalent of trityl chloride, as described above. This compound is reacted with diethyl azodicarboxylate, triphenyl phosphine and a dialkyl 1-hydroxymethyl phosphonate 38.7 in benzene, as described in Synthesis, 4, 327, 1998, to afford the ether compound 38.8. Removal of the trityl protecting group, as described above, then affords the thiophenol 38.9.

Using the above procedures, but employing, in place of the phenol 38.5, different phenols or thiophenols 38.1, and/or different phosphonates 38.2, there are obtained the corresponding thiols 38.4.

Scheme 39 illustrates the preparation of thiophenols 39.4 bearing a phosphonate group linked to the phenyl nucleus by oxygen, sulfur or nitrogen. In this procedure, a suitably protected O, S or N-substituted thiophenol 39.1 is reacted with an activated ester, for example the trifluoromethanesulfonate 39.2, of a dialkyl hydroxyalkyl phosphonate, to afford the coupled product 39.3. Deprotection then affords the thiol 39.4.

For example, 4-methylaminothiophenol 39.5, is reacted with one equivalent of acetyl chloride, as described in Protective Groups in Organic Synthesis, by T. W. Greene and P. G. M. Wuts, Wiley, 1991, pp. 298, to afford the product 39.6. This material is then reacted with, for example, a dialkyl trifluoromethanesulfonylmethyl phosphonate 39.7, the preparation of which is described in Tet. Lett., 1986, 27, 1477, to afford the displacement product 39.8. Preferably, equimolar amounts of the phosphonate 39.7 and the amine 39.6 are reacted together in an aprotic solvent such as dichloromethane, in the presence of a base such as 2,6-lutidine, at ambient temperatures, to afford the phosphonate product 39.8. Deprotection, for example by treatment with dilute aqueous sodium hydroxide for two minutes, as described in J. Amer. Chem. Soc., 85, 1337, 1963, then affords the thiophenol 39.9.

Using the above procedures, but employing, in place of the thioamine 39.5, different phenols, thiophenols or amines 39.1, and/or different phosphonates 39.2, there are obtained the corresponding products 39.4.

Scheme 40 illustrates the preparation of phosphonate esters linked to a thiophenol nucleus by means of a heteroatom and a multiple-carbon chain, employing a nucleophilic displacement reaction on a dialkyl bromoalkyl phosphonate 40.2. In this procedure, a suitably protected hydroxy, thio or amino substituted thiophenol 40.1 is reacted with a dialkyl bromoalkyl phosphonate 40.2 to afford the product 40.3. Deprotection then affords the free thiophenol 40.4.

For example, 3-hydroxythiophenol 40.5 is converted into the S-trityl compound 40.6, as described above. This compound is then reacted with, for example, a dialkyl 4-bromobutyl phosphonate 40.7, the synthesis of which is described in Synthesis, 1994, 9, 909. The reaction is conducted in a dipolar aprotic solvent, for example dimethylformamide, in the presence of a base such as potassium carbonate, and optionally in the presence of a catalytic amount of potassium iodide, at about 50° C. to yield the ether product 40.8. Deprotection, as described above, then affords the thiol 40.9.

Using the above procedures, but employing, in place of the phenol 40.5, different phenols, thiophenols or amines 40.1, and/or different phosphonates 40.2, there are obtained the corresponding products 40.4.

Scheme 41 depicts the preparation of phosphonate esters linked to a thiophenol nucleus by means of unsaturated and saturated carbon chains. The carbon chain linkage is formed by means of a palladium catalyzed Heck reaction, in which an olefinic phosphonate 41.2 is coupled with an aromatic bromo compound 41.1. Deprotection, or hydrogenation of the double bond followed by deprotection, affords respectively the unsaturated phosphonate 41.4, or the saturated analog 41.6.

For example, 3-bromothiophenol is converted into the S—Fm derivative 41.7, as described above, and this compound is reacted with diethyl 1-butenyl phosphonate 41.8, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 100° C. to afford the coupled product 41.9. Deprotection, as described above, then affords the thiol 41.10. Optionally, the initially formed unsaturated phosphonate 41.9 can be subjected to catalytic hydrogenation, using, for example, palladium on carbon as catalyst, to yield the saturated product 41.11, which upon deprotection affords the thiol 41.12.

Using the above procedures, but employing, in place of the bromo compound 41.7, different bromo compounds 41.1, and/or different phosphonates 41.2, there are obtained the corresponding products 41.4 and 41.6

Scheme 42 illustrates the preparation of an aryl-linked phosphonate ester 42.4 by means of a palladium(0) or palladium(II) catalyzed coupling reaction between a bromobenzene and a phenylboronic acid, as described in Comprehensive Organic Transformations, by R. C. Larock, VCH, 1989, p. 57. The sulfur-substituted phenylboronic acid 42.1 is obtained by means of a metallation-boronation sequence applied to a protected bromo-substituted thiophenol, for example as described in J. Org. Chem., 49, 5237, 1984. A coupling reaction then affords the diaryl product 42.3 which is deprotected to yield the thiol 42.4.

For example, protection of 4-bromothiophenol by reaction with tert-butylchlorodimethylsilane, in the presence of a base such as Imidazole, as described in Protective Groups in Organic Synthesis, by T. W. Greene and P. G. M. Wuts, Wiley, 1991, p. 297, followed by metallation with butyllithium and boronation, as described in J. Organomet. Chem., 1999, 581, 82, affords the boronate 42.5. This material is reacted with diethyl 4-bromophenylphosphonate 42.6, the preparation of which is described in J. Chem. Soc., Perkin Trans., 1977, 2, 789, in the presence of tetrakis(triphenylphosphine)palladium (0) and an inorganic base such as sodium carbonate, to afford the coupled product 42.7. Deprotection, for example by the use of tetrabutylammonium fluoride in anhydrous tetrahydrofuran, then yields the thiol 42.8.

Using the above procedures, but employing, in place of the boronate 42.5, different boronates 42.1, and/or different phosphonates 42.2, there are obtained the corresponding products 42.4.

Scheme 43 depicts the preparation of dialkyl phosphonates in which the phosphonate moiety is linked to the thiophenyl group by means of a chain which incorporates an aromatic or heteroaromatic ring. In this procedure, a suitably protected O, S or N-substituted thiophenol 43.1 is reacted with a dialkyl bromomethyl-substituted aryl or heteroarylphosphonate 43.2, prepared, for example, by means of an Arbuzov reaction between equimolar amounts of a bis(bromo-methyl) substituted aromatic compound and a trialkyl phosphite. The reaction product 43.3 is then deprotected to afford the thiol 43.4. For example, 1,4-dimercaptobenzene is converted into the monobenzoyl ester 43.5 by reaction with one molar equivalent of benzoyl chloride, in the presence of a base such as pyridine. The monoprotected thiol 43.5 is then reacted with, for example diethyl 4-(bromomethyl)phenylphosphonate, 43.6, the preparation of which is described in Tetrahedron, 1998, 54, 9341. The reaction is conducted in a solvent such as dimethylformamide, in the presence of a base such as potassium carbonate, at about 50° C. The thioether product 43.7 thus obtained is deprotected, as described above, to afford the thiol 43.8.

Using the above procedures, but employing, in place of the thiophenol 43.5, different phenols, thiophenols or amines 43.1, and/or different phosphonates 43.2, there are obtained the corresponding products 43.4.

Scheme 44 illustrates the preparation of phosphonate-containing thiophenols in which the attached phosphonate chain forms a ring with the thiophenol moiety.

In this procedure, a suitably protected thiophenol 44.1, for example an indoline (in which X—Y is $(CH_2)_2$), an indole (X—Y is CH═CH) or a tetrahydroquinoline (X—Y is $(CH_2)_3$) is reacted with a dialkyl trifluoromethanesulfonyloxymethyl phosphonate 44.2, in the presence of an organic or inorganic base, in a polar aprotic solvent such as, for example, dimethylformamide, to afford the phosphonate ester 44.3. Deprotection, as described above, then affords the thiol 44.4. The preparation of thio-substituted indolines is described in EP 209751. Thio-substituted indoles, indolines and tetrahydroquinolines can also be obtained from the corresponding hydroxy-substituted compounds, for example by thermal rearrangement of the dimethylthiocarbamoyl esters, as described in J. Org. Chem., 31, 3980, 1966. The preparation of hydroxy-substituted indoles is described in Syn., 1994, 10, 1018; preparation of hydroxy-substituted indolines is described in Tet. Lett., 1986, 27, 4565, and the preparation of hydroxy-substituted tetrahydroquinolines is described in J. Het. Chem., 1991, 28, 1517, and in J. Med. Chem., 1979, 22, 599. Thio-substituted indoles, indolines and tetrahydroquinolines can also be obtained from the corresponding amino and bromo compounds, respectively by diazotization, as described in Sulfur Letters, 2000, 24, 123, or by reaction of the derived organolithium or magnesium derivative with sulfur, as described in Comprehensive Organic Functional Group Preparations, A. R. Katritzky et al, eds, Pergamon, 1995, Vol. 2, p 707. For example, 2,3-dihydro-1H-indole-5-thiol, 44.5, the preparation of which is described in EP 209751, is converted into the benzoyl ester 44.6, as described above, and the ester is then reacted with the triflate 44.7, using the conditions described above for the preparation of 39.8, (Scheme 39, to yield the phosphonate 44.8. Deprotection, for example by reaction with dilute aqueous ammonia, as described above, then affords the thiol 44.9.

Using the above procedures, but employing, in place of the thiol 44.5, different thiols 44.1, and/or different triflates 44.2, there are obtained the corresponding products 44.4.

Scheme 35

Method

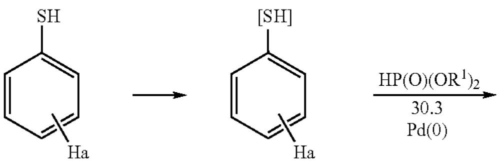

35.1 35.2

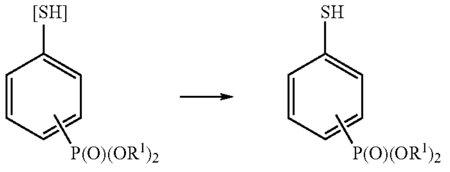

35.3 35.4

-continued

Example

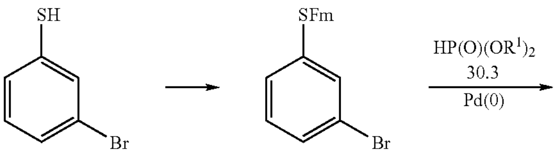

35.5 35.6

Fm = 9-fluorenylmethyl

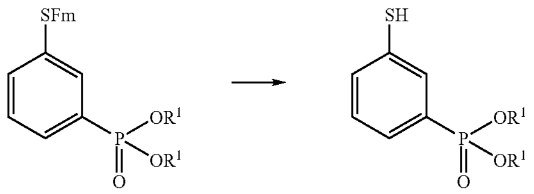

35.7 35.8

Scheme 36

Method

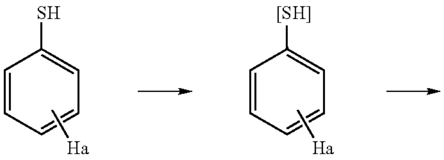

36.1 36.2

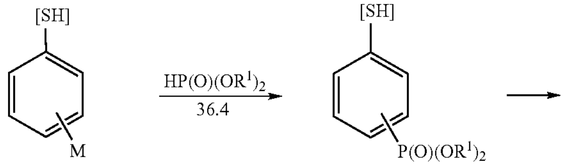

36.3 36.5

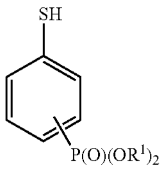

36.6

Example

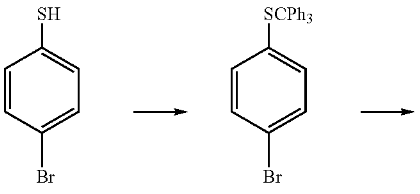

36.7 36.8

-continued
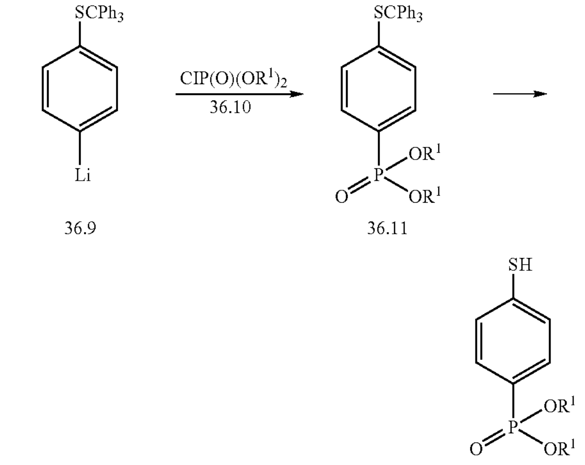
36.9
36.11
36.12
Scheme 37
Method
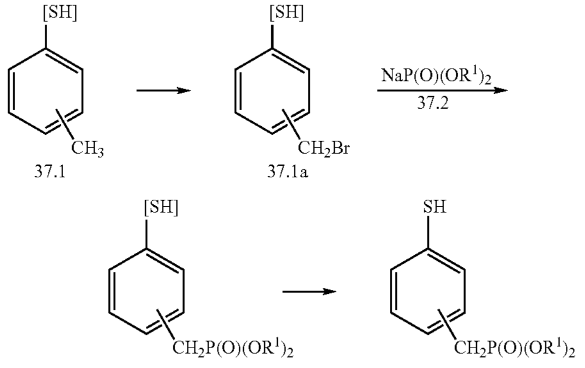
37.1
37.1a
37.3
37.4
Example
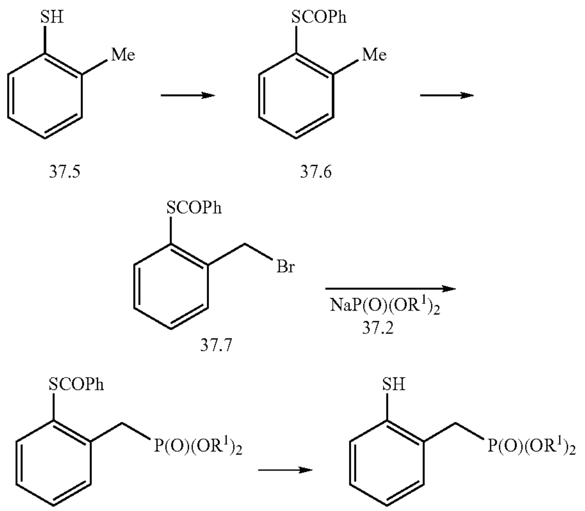
37.5
37.6
37.7
37.8
37.9
Scheme 38
Method
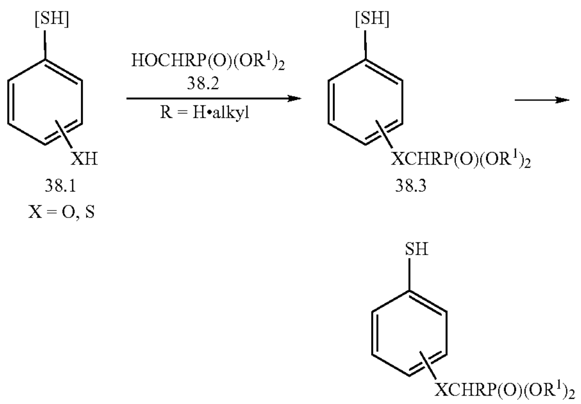
38.1
X = O, S
38.3
38.4
X = O, S
Example
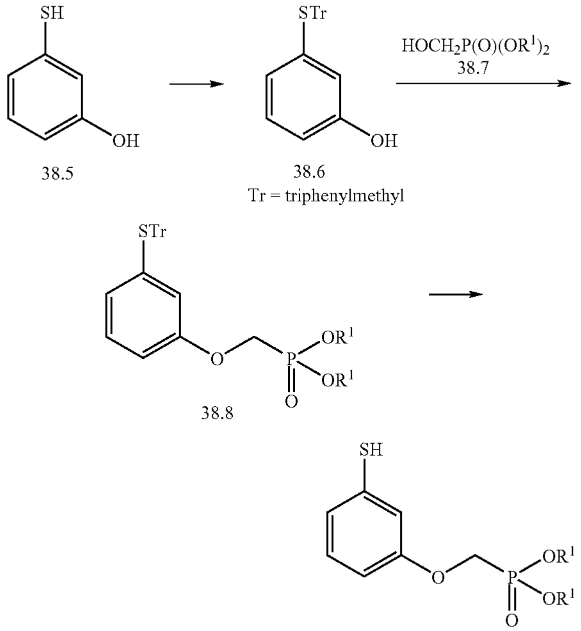
38.5
38.6
Tr = triphenylmethyl
38.8
38.9
Scheme 39
Method
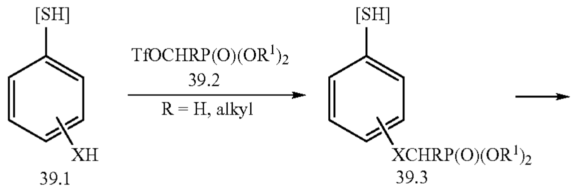
39.1
X = O, S, NH, Nalkyl
39.3

-continued
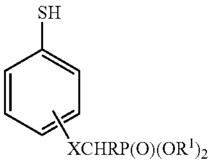
39.4
Example
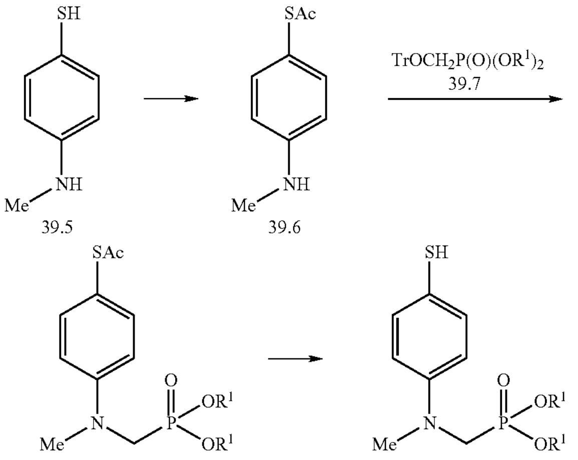
39.5 39.6 39.8 39.9
-continued
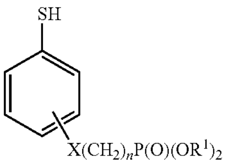
40.4
Example
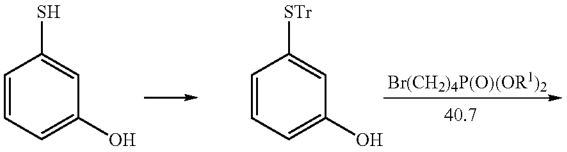
40.5 40.6
Tr = triphenylmethyl
Scheme 40
Method
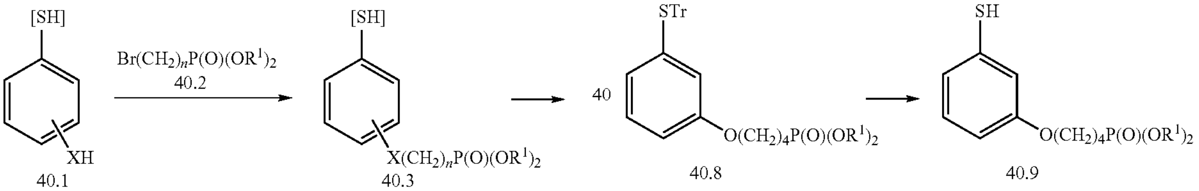
40.1 40.3 40.8 40.9
X = O, S, NH, Nalkyl
Scheme 41
Method
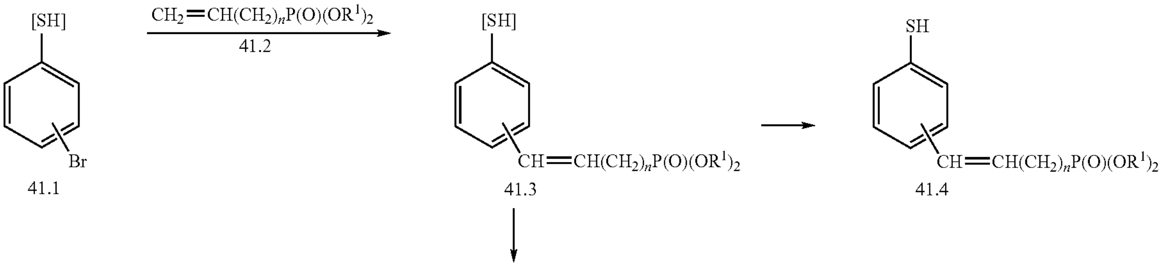
41.1 41.3 41.4

-continued
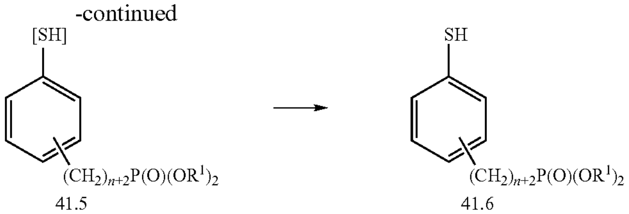
41.5 41.6
Example
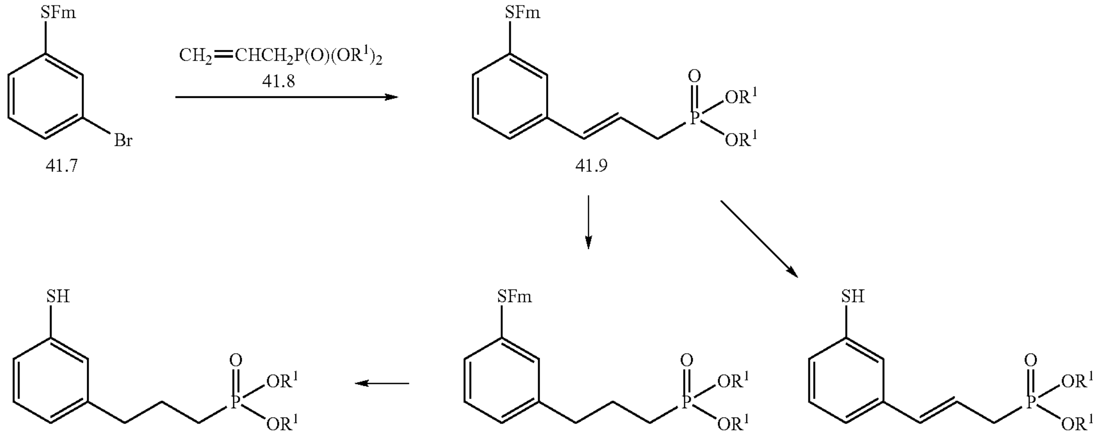
41.7 41.9 41.12 41.11 41.10
Scheme 42
Method
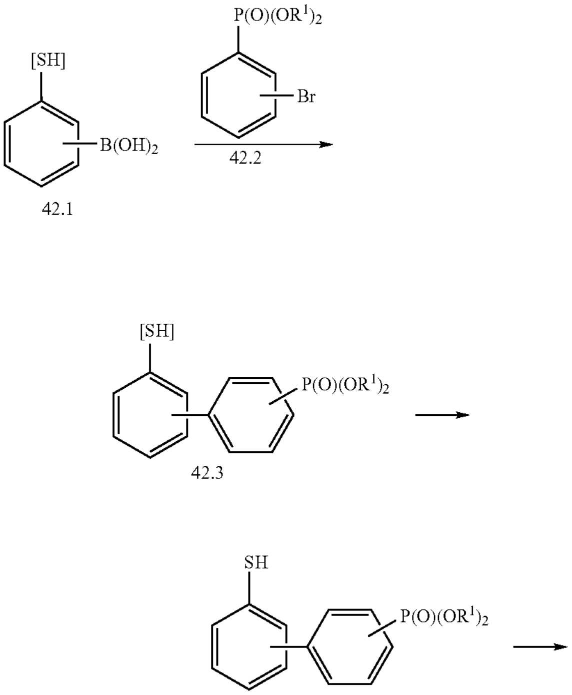
42.1 42.2 42.3 42.4
-continued
Example
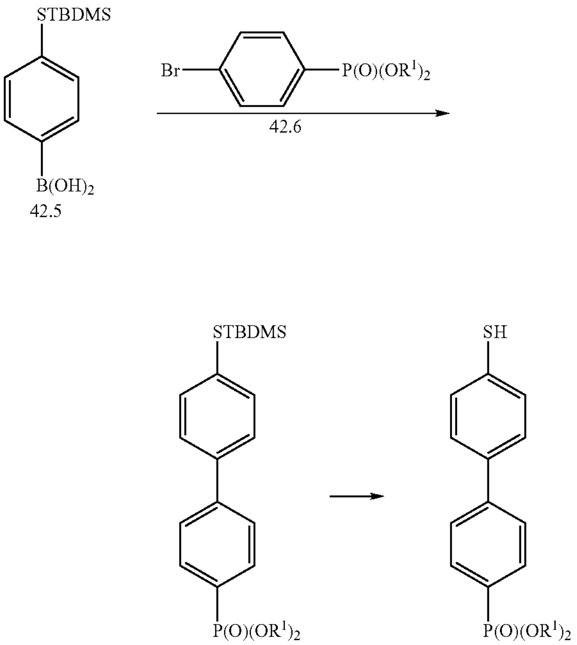
42.5 42.6 42.7 42.8

Scheme 43

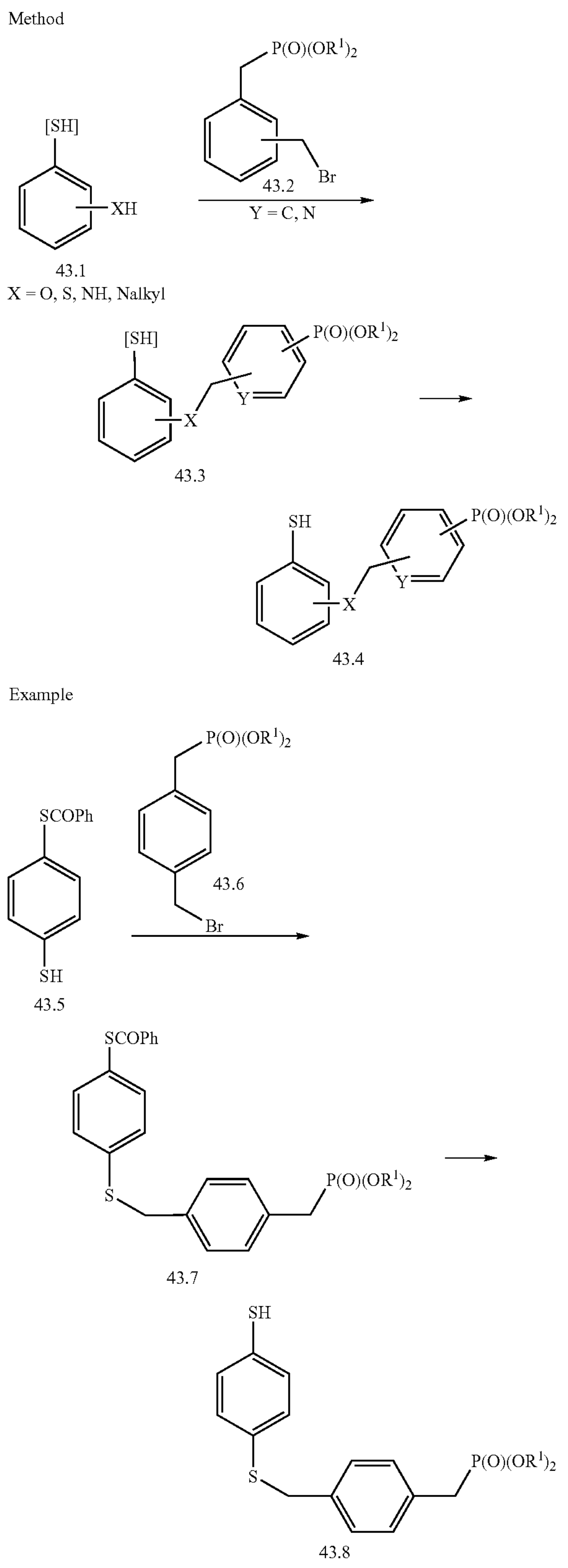

Scheme 44

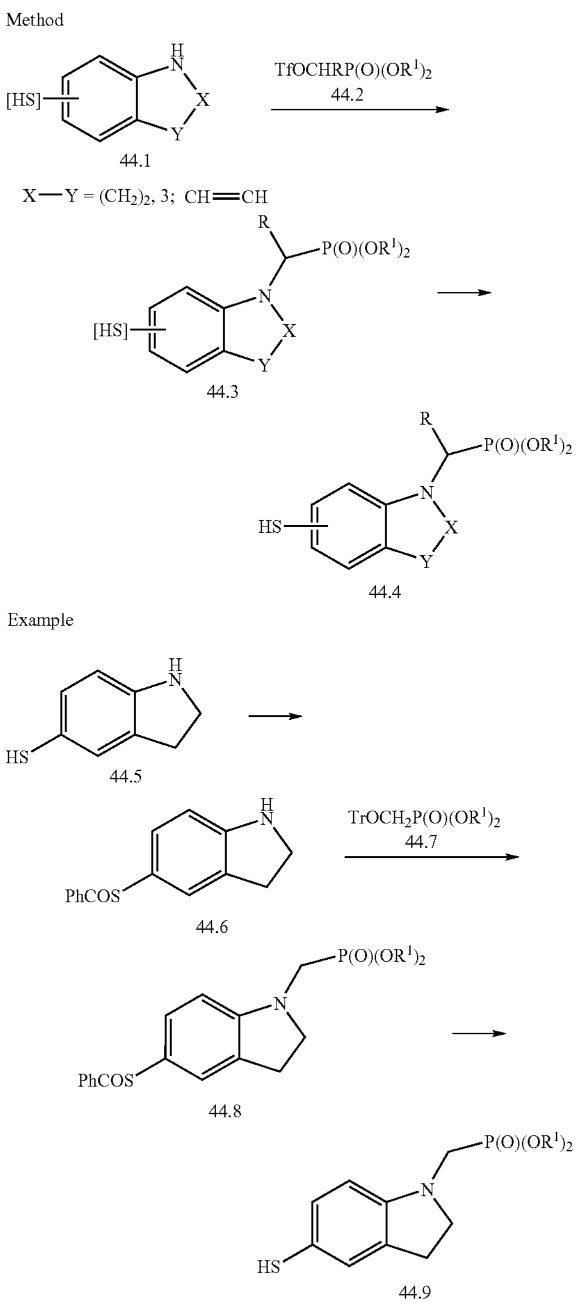

Preparation of Tert-butylamine Derivatives Incorporating Phosphonate Groups.

Scheme 45 describes the preparation of tert-butylamines in which the phosphonate moiety is directly attached to the tert-butyl group. A suitably protected 2.2-dimethyl-2-amino-ethyl bromide 45.1 is reacted with a trialkyl phosphite 45.2, under the conditions of the Arbuzov reaction, as described above, to afford the phosphonate 45.3, which is then deprotected as described previously to give 45.4

For example, the cbz derivative of 2,2-dimethyl-2-amino-ethyl bromide 45.6, is heated with a trialkyl phosphite at ca 150° C. to afford the product 45.7. Deprotection, as previously described, then affords the free amine 45.8.

Using the above procedures, but employing different trisubstituted phosphites, there are obtained the corresponding amines 45.4.

Scheme 46 illustrates the preparation of phosphonate esters attached to the tert butylamine by means of a heteroatom and a carbon chain. An optionally protected alcohol or thiol 46.1 is reacted with a bromoalkylphosphonate 46.2, to afford the displacement product 46.3. Deprotection, if needed, then yields the amine 46.4.

For example, the cbz derivative of 2-amino-2,2-dimethylethanol 46.5 is reacted with a dialkyl 4-bromobutyl phosphonate 46.6, prepared as described in Synthesis, 1994, 9, 909, in dimethylformamide containing potassium carbonate and potassium iodide, at ca 60° C. to afford the phosphonate 46.7 Deprotection then affords the free amine 46.8.

Using the above procedures, but employing different alcohols or thiols 46.1, and/or different bromoalkylphosphonates 46.2, there are obtained the corresponding products 46.4.

Scheme 47 describes the preparation of carbon-linked phosphonate tert butylamine derivatives, in which the carbon chain can be unsaturated or saturated.

In the procedure, a terminal acetylenic derivative of tert-butylamine 47.1 is reacted, under basic conditions, with a dialkyl chlorophosphite 47.2, as described above in the preparation of 36.5, (Scheme 36). The coupled product 47.3 is deprotected to afford the amine 47.4. Partial or complete catalytic hydrogenation of this compound affords the olefinic and saturated products 47.5 and 47.6 respectively.

For example, 2-amino-2-methylprop-1-yne 47.7, the preparation of which is described in WO 9320804, is converted into the N-phthalimido derivative 47.8, by reaction with phthalic anhydride, as described in Protective Groups in Organic Synthesis, by T. W. Greene and P. G. M. Wuts, Wiley, 1991, pp. 358. This compound is reacted with lithium diisopropylamide in tetrahydrofuran at −78° C. The resultant anion is then reacted with a dialkyl chlorophosphite 47.2 to afford the phosphonate 47.9. Deprotection, for example by treatment with hydrazine, as described in J. Org. Chem., 43, 2320, 1978, then affords the free amine 47.10. Partial catalytic hydrogenation, for example using Lindlar catalyst, as described in Reagents for Organic Synthesis, by L. F. Fieser and M. Fieser, Volume 1, p 566, produces the olefinic phosphonate 47.11, and conventional catalytic hydrogenation, as described in Organic Functional Group Preparations, by S. R. Sandler and W. Karo, Academic Press, 1968, p3. for example using 5% palladium on carbon as catalyst, affords the saturated phosphonate 47.12. Using the above procedures, but employing different acetylenic amines 47.1, and/or different dialkyl halophosphites, there are obtained the corresponding products 47.4, 47.5 and 47.6.

Scheme 48 illustrates the preparation of a tert butylamine phosphonate in which the phosphonate moiety is attached by means of a cyclic amine.

In this method, an aminoethyl-substituted cyclic amine 48.1 is reacted with a limited amount of a bromoalkyl phosphonate 48.2, using, for example, the conditions described above for the preparation of 40.3, (Scheme 40) to afford the displacement product 48.3.

For example, 3-(1-amino-1-methyl)ethylpyrrolidine 48.4, the preparation of which is described in Chem. Pharm. Bull., 1994, 42, 1442, is reacted with a dialkyl 4-bromobutyl phosphonate 48.5, prepared as described in Synthesis, 1994, 9, 909, to afford the displacement product 48.6.

Using the above procedures, but employing different cyclic amines 48.1, and/or different bromoalkylphosphonates 48.2, there are obtained the corresponding products 48.3.

Scheme 45

Method

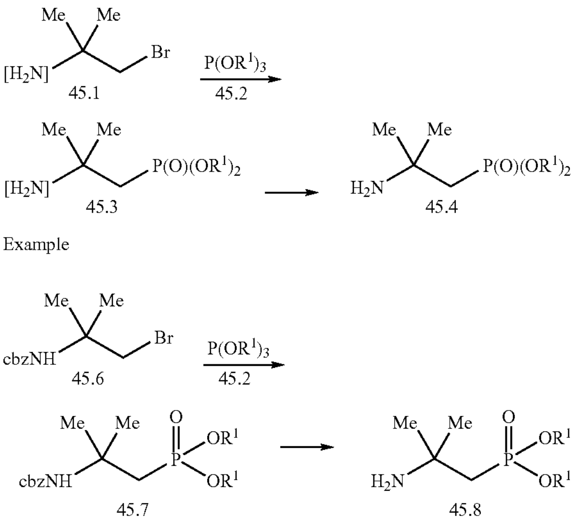

45.1 45.2 45.3 45.4

Example 45.6 45.2 45.7 45.8

Scheme 46

Method

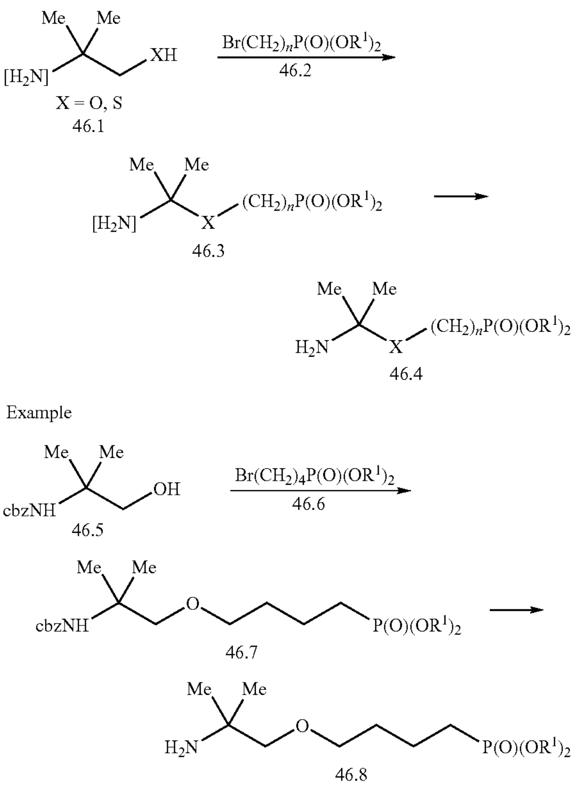

X = O, S 46.1 46.2 46.3 46.4

Example 46.5 46.6 46.7 46.8

Scheme 47

Method

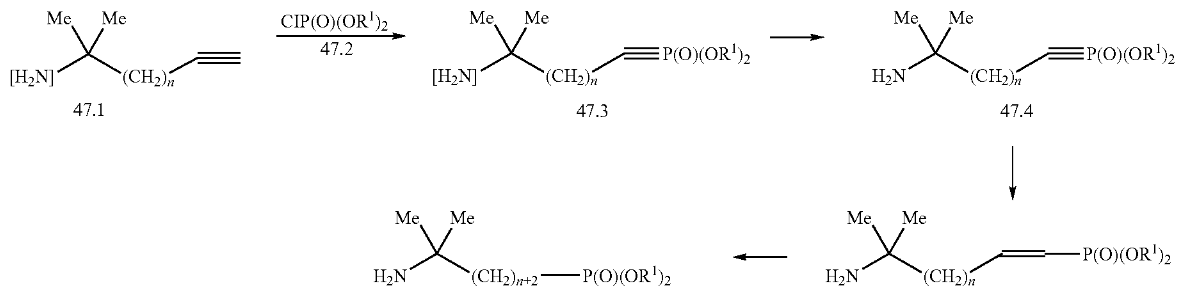

47.1 47.3 47.4 47.5 47.6

Example

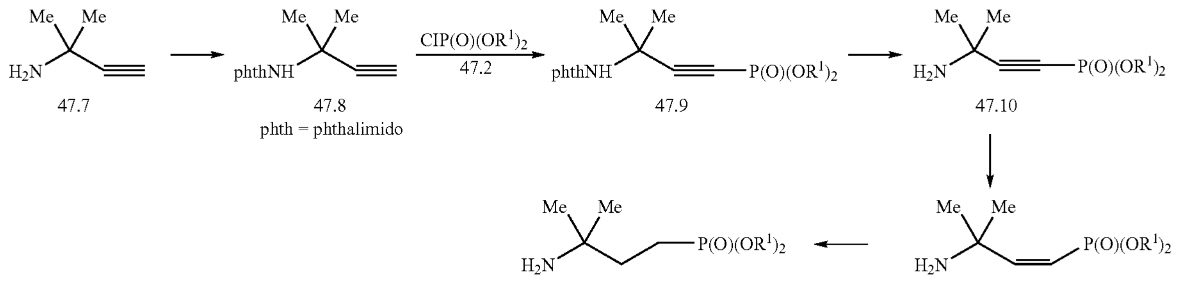

47.7 47.8 47.9 47.10 47.11 47.12 phth = phthalimido

Scheme 48

Method

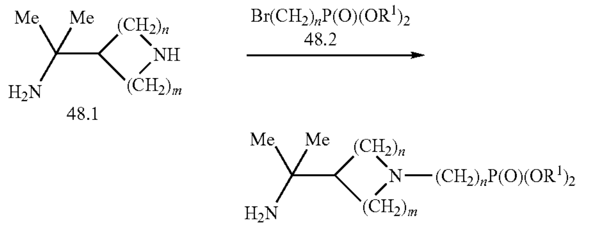

48.1 48.3

Example

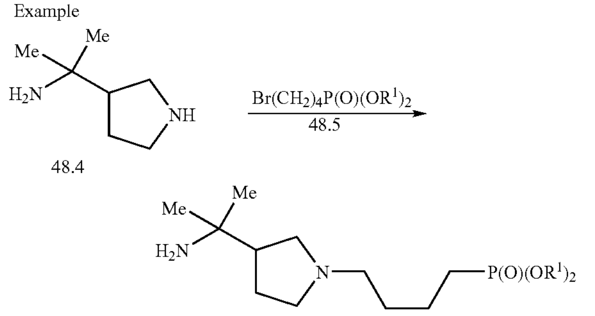

48.4 48.6

Preparation of Decahydroquinolines with Phosphonate Moieties at the 6-position.

Scheme 48a illustrates methods for the synthesis of intermediates for the preparation of decahydroquinolines with phosphonate moieties at the 6-position. Two methods for the preparation of the intermediate 48a.4 are shown.

In the first route, 2-hydroxy-6-methylphenylalanine 48a.1, the preparation of which is described in J. Med. Chem., 1969, 12, 1028, is converted into the protected derivative 48a.2. For example, the carboxylic acid is first transformed into the benzyl ester, and the product is reacted with acetic anhydride in the presence of an organic base such as, for example, pyridine, to afford the product 48a.2, in which R is benzyl. This compound is reacted with a brominating agent, for example N-bromosuccinimide, to effect benzylic bromination and yield the product 48a.3. The reaction is conducted in an aprotic solvent such as, for example, ethyl acetate or carbon tetrachloride, at reflux. The brominated compound 48a.3 is then treated with acid, for example dilute hydrochloric acid, to effect hydrolysis and cyclization to afford the tetrahydroisoquinoline 48a.4, in which R is benzyl.

Alternatively, the tetrahydroisoquinoline 48a.4 can be obtained from 2-hydroxyphenylalanine 48a.5, the preparation of which is described in Can. J. Bioch., 1971, 49, 877. This compound is subjected to the conditions of the Pictet-Spengler reaction, for example as described in Chem. Rev., 1995, 95, 1797.

Typically, the substrate 48a.5 is reacted with aqueous formaldehyde, or an equivalent such as paraformaldehyde or dimethoxymethane, in the presence of hydrochloric acid, for example as described in J. Med. Chem., 1986, 29, 784, to afford the tetrahydroisoquinoline product 48a.4, in which R is H. Catalytic hydrogenation of the latter compound, using, for example, platinum as catalyst, as described in J. Amer. Chem.

Soc., 69, 1250, 1947, or using rhodium on alumina as catalyst, as described in J. Med. Chem., 1995, 38, 4446, then gives the hydroxy-substituted decahydroisoquinoline 48a.6. The reduction can also be performed electrochemically, as described in Trans SAEST 1984, 19, 189.

For example, the tetrahydroisoquinoline 48a.4 is subjected to hydrogenation in an alcoholic solvent, in the presence of a dilute mineral acid such as hydrochloric acid, and 5% rhodium on alumina as catalyst. The hydrogenation pressure is ca. 750 psi, and the reaction is conducted at ca 50° C., to afford the decahydroisoquinoline 48a.6.

Protection of the carboxyl and NH groups present in 48a.6 for example by conversion of the carboxylic acid into the trichloroethyl ester, as described in Protective Groups in Organic Synthesis, by T. W. Greene and P. G. M. Wuts, Wiley, 1991, p. 240, and conversion of the NH into the N-cbz group, as described above, followed by oxidation, using, for example, pyridinium chlorochromate and the like, as described in Reagents for Organic Synthesis, by L. F. Fieser and M. Fieser, Volume 6, p. 498, affords the protected ketone 48a.9, in which R is trichloroethyl and $R_1$ is cbz. Reduction of the ketone, for example by the use of sodium borohydride, as described in J. Amer. Chem. Soc., 88, 2811, 1966, or lithium tri-tertiary butyl aluminum hydride, as described in J. Amer. Chem. Soc., 80, 5372, 1958, then affords the alcohol 48a.10.

For example, the ketone is reduced by treatment with sodium borohydride in an alcoholic solvent such as isopropanol, at ambient temperature, to afford the alcohol 48a.10.

The alcohol 48a.6 can be converted into the thiol 48a.13 and the amine 48a.14, by means of displacement reactions with suitable nucleophiles, with inversion of stereochemistry. For example, the alcohol 48a.6 can be converted into an activated ester such as the trifluoromethanesulfonyl ester or the methanesulfonate ester 48a.7, by treatment with methanesulfonyl chloride and a base. The mesylate 48a.7 is then treated with a sulfur nucleophile, for example potassium thioacetate, as described in Tet. Lett., 1992, 4099, or sodium thiophosphate, as described in Acta Chem. Scand., 1960, 1980, to effect displacement of the mesylate, followed by mild basic hydrolysis, for example by treatment with aqueous ammonia, to afford the thiol 48a.13.

For example, the mesylate 48a.7 is reacted with one molar equivalent of sodium thioacetate in a polar aprotic solvent such as, for example, dimethylformamide, at ambient temperature, to afford the thioacetate 48a.12, in which R is $COCH_3$. The product then treated with, a mild base such as, for example, aqueous ammonia, in the presence of an organic co-solvent such as ethanol, at ambient temperature, to afford the thiol 48a.13.

The mesylate 48a.7 can be treated with a nitrogen nucleophile, for example sodium phthalimide or sodium bis(trimethylsilyl)amide, as described in Comprehensive Organic Transformations, by R. C. Larock, p. 399, followed by deprotection as described previously, to afford the amine 48a.14.

For example, the mesylate 48a.7 is reacted, as described in Angew. Chem. Int. Ed., 7, 919, 1968, with one molar equivalent of potassium phthalimide, in a dipolar aprotic solvent, such as, for example, dimethylformamide, at ambient temperature, to afford the displacement product 48a.8, in which $NR^aR^b$ is phthalimido. Removal of the phthalimido group, for example by treatment with an alcoholic solution of hydrazine at ambient temperature, as described in J. Org. Chem., 38, 3034, 1973, then yields the amine 48a.14.

The application of the procedures described above for the conversion of the β-carbinol 48a.6 to the x-thiol 48a.13 and the α-amine 48a.14 can also be applied to the α-carbinol 48a.10, so as to afford the β-thiol and β-amine, 48a.11.

Scheme 49 illustrates the preparation of compounds in which the phosphonate moiety is attached to the decahydroisoquinoline by means of a heteroatom and a carbon chain. In this procedure, an alcohol, thiol or amine 49.1 is reacted with a bromoalkyl phosphonate 49.2, under the conditions described above for the preparation of the phosphonate 40.3 (Scheme 40), to afford the displacement product 49.3. Removal of the ester group, followed by conversion of the acid to the $R^4$NH amide and N-deprotection, as described below, (Scheme 53) then yields the amine 49.8.

For example, the compound 49.5, in which the carboxylic acid group is protected as the trichloroethyl ester, as described in Protective Groups in Organic Synthesis, by T. W. Greene and P. G. M. Wuts, Wiley, 1991, p. 240, and the amine is protected as the cbz group, is reacted with a dialkyl 3-bromopropylphosphonate, 49.6, the preparation of which is described in J. Amer. Chem. Soc., 2000, 122, 1554 to afford the displacement product 49.7. Deprotection of the ester group, followed by conversion of the acid to the $R^4$NH amide and N-deprotection, as described below, (Scheme 53) then yields the amine 49.8.

Using the above procedures, but employing, in place of the α-thiol 49.5, the alcohols, thiols or amines 48a.6, 48a.10, 48a.11, 48a.13, 48a.14, of either α- or β-orientation, there are obtained the corresponding products 49.4, in which the orientation of the side chain is the same as that of the O, N or S precursors.

Scheme 50 illustrates the preparation of phosphonates linked to the decahydroisoquinoline moiety by means of a nitrogen atom and a carbon chain. The compounds are prepared by means of a reductive amination procedure, for example as described in Comprehensive Organic Transformations, by R. C. Larock, p. 421.

In this procedure, the amines 48a.14 or 48a.11 are reacted with a phosphonate aldehyde 50.1, in the presence of a reducing agent, to afford the alkylated amine 50.2. Deprotection of the ester group, followed by conversion of the acid to the $R^4$NH amide and N-deprotection, as described below, (Scheme 53) then yields the amine 50.3.

For example, the protected amino compound 48a.14 is reacted with a dialkyl formylphosphonate 50.4, the preparation of which is described in U.S. Pat. No. 3,784,590, in the presence of sodium cyanoborohydride, and a polar organic solvent such as ethanolic acetic acid, as described in Org. Prep. Proc. Int., 11, 201, 1979, to give the amine phosphonate 50.5. Deprotection of the ester group, followed by conversion of the acid to the $R^4$NH amide and N-deprotection, as described below, (Scheme 53) then yields the amine 50.6.

Using the above procedures, but employing, instead of the α-amine 48a.14, the β isomer, 48a.11 and/or different aldehydes 50.1, there are obtained the corresponding products 50.3, in which the orientation of the side chain is the same as that of the amine precursor.

Scheme 51 depicts the preparation of a decahydroisoquinoline phosphonate in which the phosphonate moiety is linked by means of a sulfur atom and a carbon chain.

In this procedure, a thiol phosphonate 51.2 is reacted with a mesylate 51.1, to effect displacement of the mesylate group with inversion of stereochemistry, to afford the thioether product 51.3. Deprotection of the ester group, followed by conversion of the acid to the tert. butyl amide and N-deprotection, as described below, (Scheme 53) then yields the amine 51.4. For example, the protected mesylate 51.5 is reacted with an equimolar amount of a dialkyl 2-mercaptoethyl phosphonate 51.6, the preparation of which is described in Aust. J. Chem., 43, 1123, 1990. The reaction is conducted in a polar organic solvent such as ethanol, in the presence of a base such as, for example, potassium carbonate, at ambient temperature, to afford the thio ether phosphonate 51.7. Deprotection of the ester group, followed by conversion of the acid to the tert. butyl amide and N-deprotection, as described below, (Scheme 53) then yields the amine 51.8

Using the above procedures, but employing, instead of the phosphonate 51.6, different phosphonates 51.2, there are obtained the corresponding products 51.4.

Scheme 52 illustrates the preparation of decahydroisoquinoline phosphonates 52.4 in which the phosphonate group is linked by means of an aromatic or heteroaromatic ring. The compounds are prepared by means of a displacement reaction between hydroxy, thio or amino substituted substrates 52.1 and a bromomethyl substituted phosphonate 52.2. The reaction is performed in an aprotic solvent in the presence of a base of suitable strength, depending on the nature of the reactant 52.1. If X is S or NH, a weak organic or inorganic base such as triethylamine or potassium carbonate can be employed. If X is O, a strong base such as sodium hydride or lithium hexamethyldisilylazide is required. The displacement reaction affords the ether, thioether or amine compounds 52.3. Deprotection of the ester group, followed by conversion of the acid to the $R^4NH$ amide and N-deprotection, as described below, (Scheme 53) then yields the amine 52.4.

For example, the protected alcohol 52.5 is reacted at ambient temperature with a dialkyl 3-bromomethyl phenylmethylphosphonate 52.6, the preparation of which is described above, (Scheme 43). The reaction is conducted in a dipolar aprotic solvent such as, for example, dioxan or dimethylformamide. The solution of the carbinol is treated with one equivalent of a strong base, such as, for example, lithium hexamethyldisilylazide, and to the resultant mixture is added one molar equivalent of the bromomethyl phosphonate 52.6, to afford the product 52.7. Deprotection of the ester group, followed by conversion of the acid to the $R^4NH$ amide and N-deprotection, as described below, (Scheme 53) then yields the amine 52.8. Using the above procedures, but employing, instead of the β-carbinol 52.5, different carbinols, thiols or amines 52.1, of either α- or β-orientation, and/or different phosphonates 52.2, in place of the phosphonate 52.6, there are obtained the corresponding products 52.4 in which the orientation of the side-chain is the same as that of the starting material 52.1.

Schemes 49-52 illustrate the preparation of decahydroisoquinoline esters incorporating a phosphonate group linked to the decahydroisoquinoline nucleus.

Scheme 53 illustrates the conversion of the latter group of compounds 53.1 (in which the group B is link-$P(O)(OR^1)_2$ or optionally protected precursor substituents thereto, such as, for example, OH, SH, $NH_2$) to the corresponding $R^4NH$ amides 53.5.

As shown in Scheme 53, the ester compounds 53.1 are deprotected to form the corresponding carboxylic acids 53.2. The methods employed for the deprotection are chosen based on the nature of the protecting group R, the nature of the N-protecting group $R^2$, and the nature of the substituent at the 6-position. For example, if R is trichloroethyl, the ester group is removed by treatment with zinc in acetic acid, as described in J. Amer. Chem. Soc., 88, 852, 1966.

Conversion of the carboxylic acid 53.2 to the $R^4NH$ amide 53.4 is then accomplished by reaction of the carboxylic acid, or an activated derivative thereof, with the amine $R^4NH_2$ 53.3 to afford the amide 53.4, using the conditions described above for the preparation of the amide 1.6. Deprotection of the $NR^2$ group, as described above, then affords the free amine 53.5.

Scheme 48a.
Intermediates for the preparation of phosphonate-containing decahydroisoquinolines.

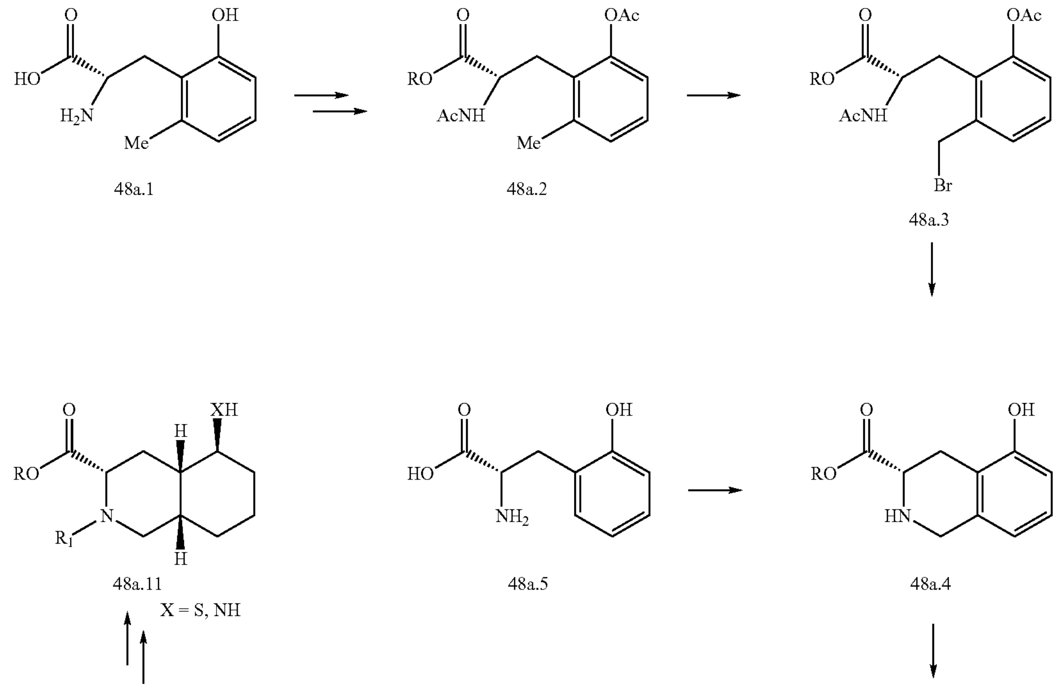

48a.1 48a.2 48a.3 48a.11 X = S, NH 48a.5 48a.4

-continued
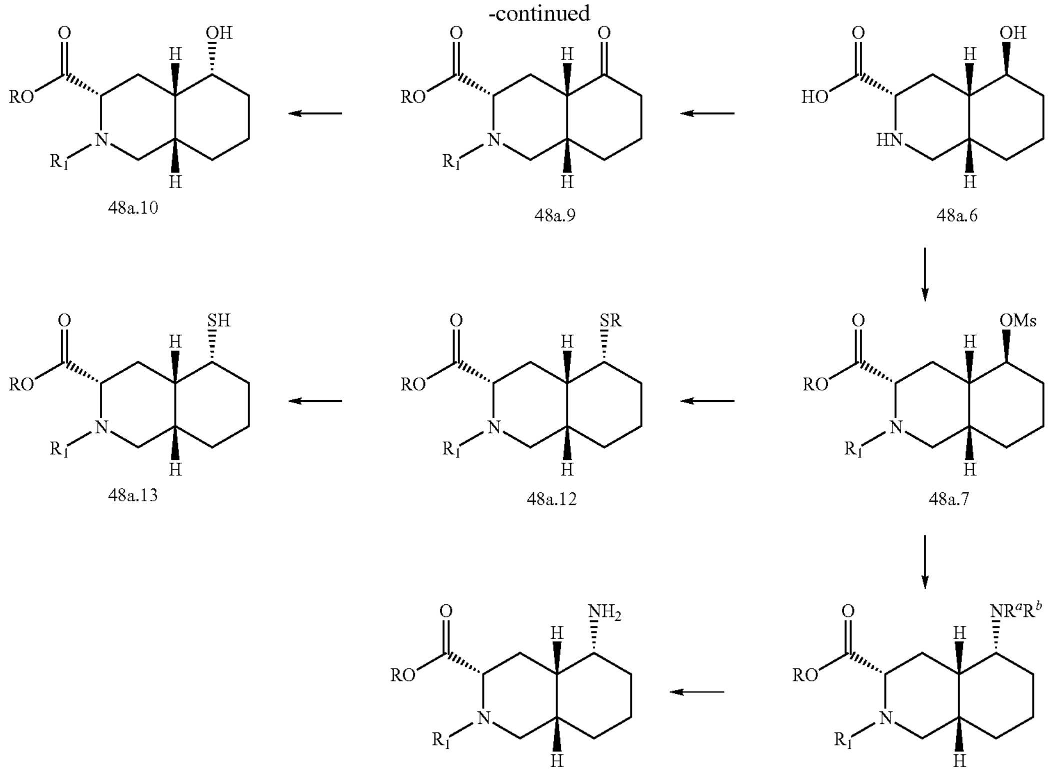
48a.10 48a.9 48a.6
48a.13 48a.12 48a.7
48a.14 48a.8
Scheme 49
Method
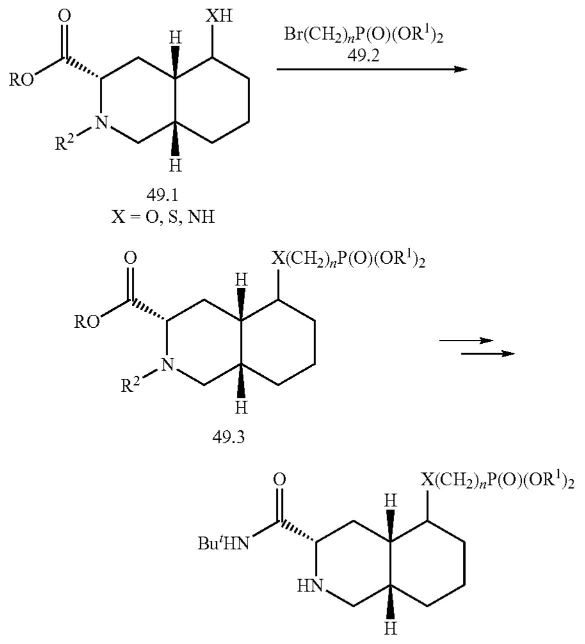
49.1
X = O, S, NH
49.3
49.4
Example
-continued
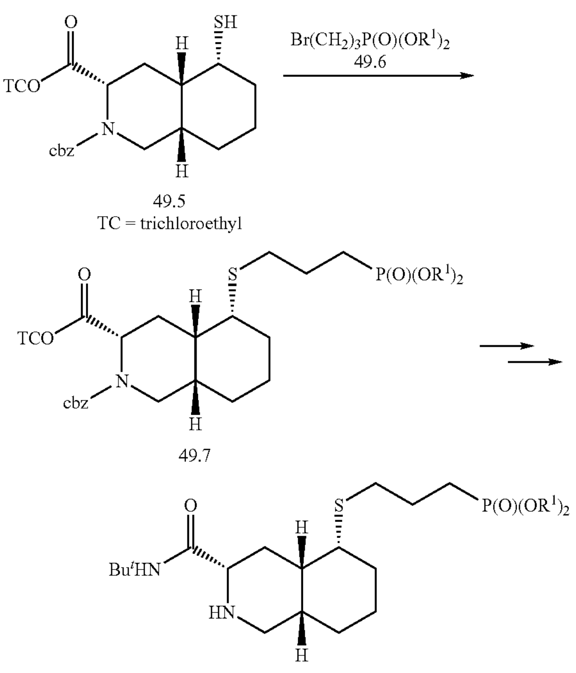
49.5
TC = trichloroethyl
49.7
49.8

Scheme 50
Method
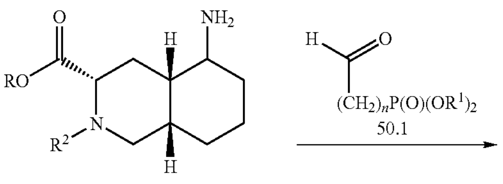
48a.11/14
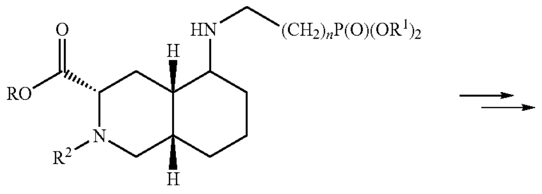
50.2
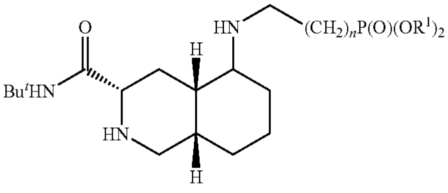
50.3
Example
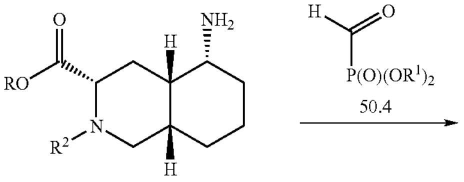
48a.14
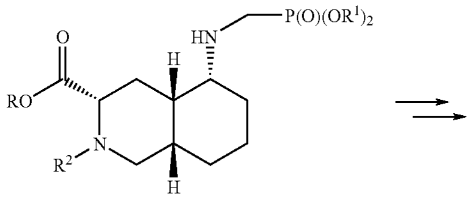
50.5
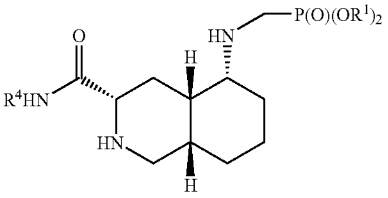
50.6
Scheme 51
Method
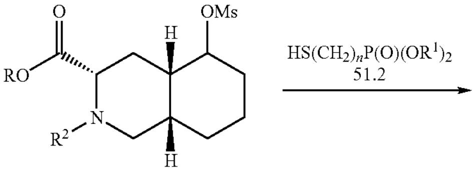
51.1
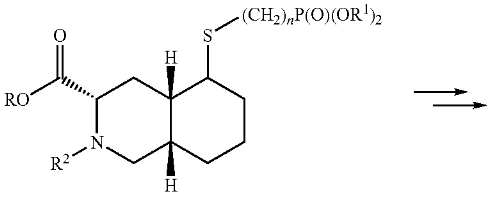
51.3
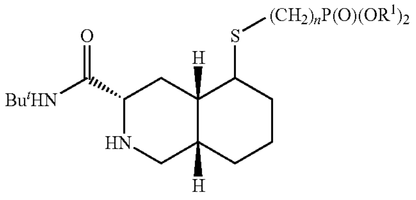
51.4
Example
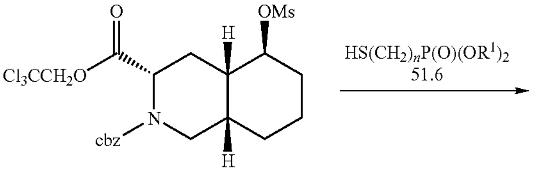
51.5
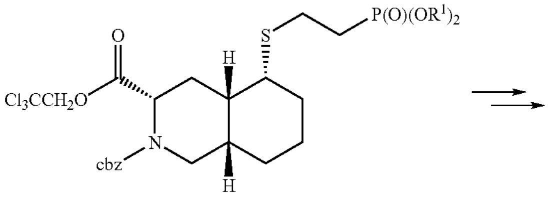
51.7
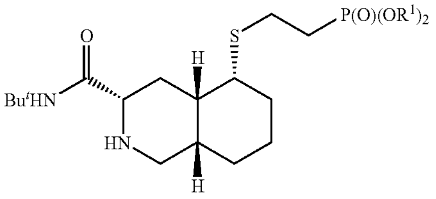
51.8

Scheme 52
Method
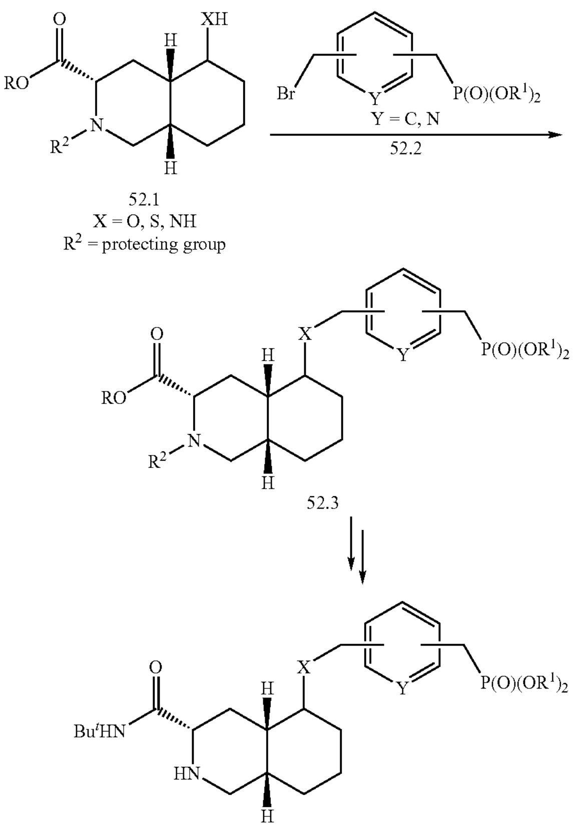
52.1
X = O, S, NH
$R^2$ = protecting group
52.3
52.4
Example
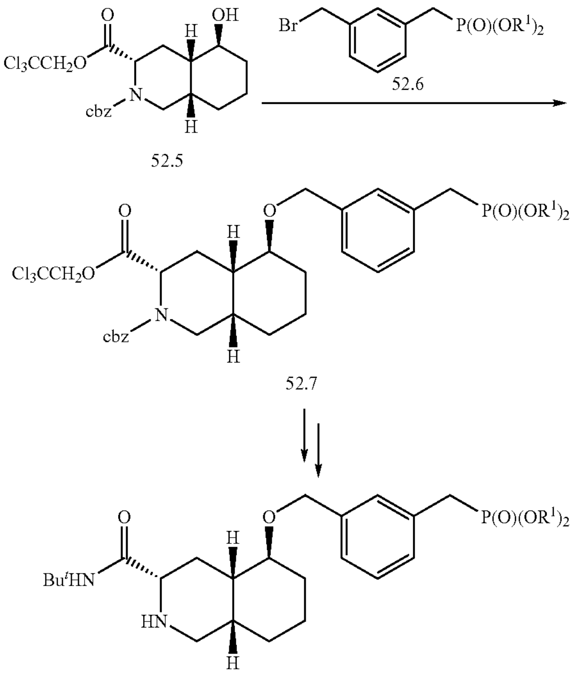
52.5
52.7
52.8
Scheme 53
Method
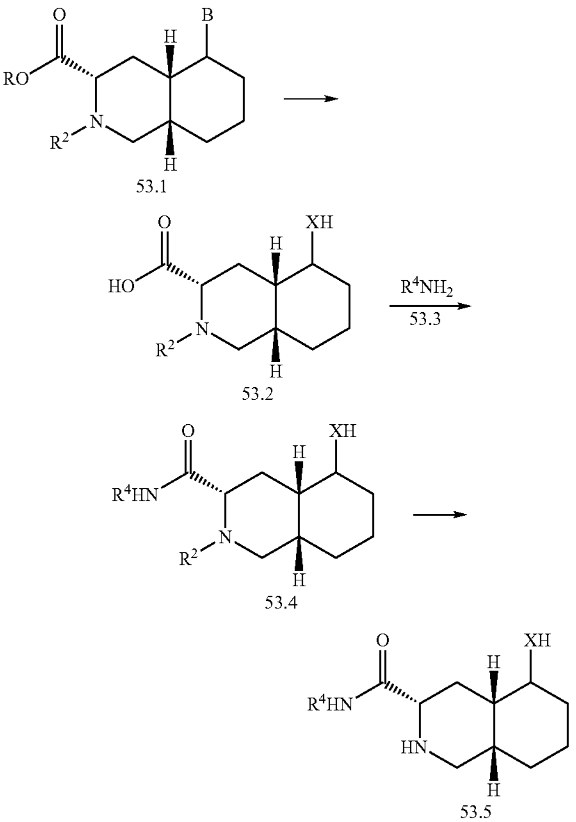
53.1
53.2
53.4
53.5
Scheme 54
Method
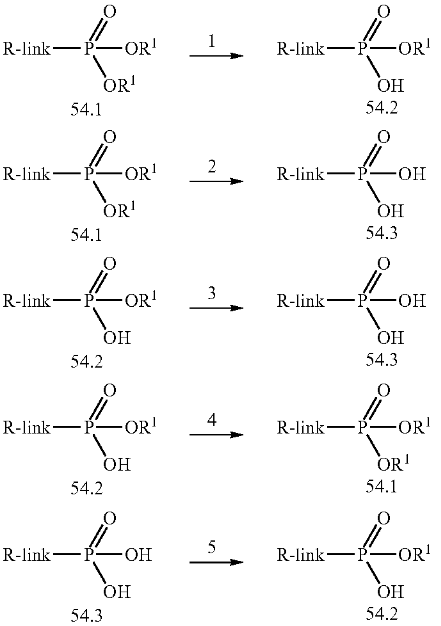
54.1 54.2
54.1 54.3
54.2 54.3
54.2 54.1
54.3 54.2

-continued

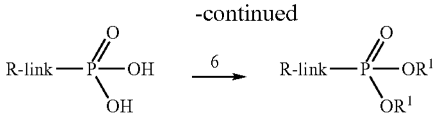

54.3

54.1

Interconversions of the Phosphonates R-link-P(O)($OR^1$)$_2$, R-link-P(O)($OR^1$)(OH) and R-link-P(O)($OH$)$_2$.

Schemes 1-69 described the preparations of phosphonate esters of the general structure R-link-P(O)($OR^1$)$_2$, in which the groups $R^1$, the structures of which are defined in Chart 1, may be the same or different. The $R^1$ groups attached to a phosphonate esters 1-6, or to precursors thereto, may be changed using established chemical transformations. The interconversions reactions of phosphonates are illustrated in Scheme 54. The group R in Scheme 54 represents the substructure to which the substituent link-P(O)($OR^1$)$_2$ is attached, either in the compounds 1-6 or in precursors thereto. The $R^1$ group may be changed, using the procedures described below, either in the precursor compounds, or in the esters 1-6. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 54.1 into the corresponding phosphonate monoester 54.2 (Scheme 54, Reaction 1) can be accomplished by a number of methods. For example, the ester 54.1 in which $R^1$ is an aralkyl group such as benzyl, can be converted into the monoester compound 54.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110° C. The conversion of the diester 54.1 in which $R^1$ is an aryl group such as phenyl, or an alkenyl group such as allyl, into the monoester 54.2 can be effected by treatment of the ester 54.1 with a base such as aqueous sodium hydroxide in acetonitrile or lithium hydroxide in aqueous tetrahydrofuran.

Phosphonate diesters 54.1 in which one of the groups $R^1$ is aralkyl, such as benzyl, and the other is alkyl, can be converted into the monoesters 54.2 in which $R^1$ is alkyl by hydrogenation, for example using a palladium on carbon catalyst. Phosphonate diesters in which both of the groups $R^1$ are alkenyl, such as allyl, can be converted into the monoester 54.2 in which $R^1$ is alkenyl, by treatment with chlorotris (triphenylphosphine)rhodium (Wilkison's catalyst) in aqueous ethanol at reflux, optionally in the presence of diazabicyclooctane, for example by using the procedure described in J. Org. Chem., 38 3224 1973 for the cleavage of allyl carboxylates.

The conversion of a phosphonate diester 54.1 or a phosphonate monoester 54.2 into the corresponding phosphonic acid 54.3 (Scheme 54, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 54.2 in which $R^1$ is aralkyl such as benzyl, can be converted into the corresponding phosphonic acid 54.3 by hydrogenation over a palladium catalyst, or by treatment with hydrogen chloride in an ethereal solvent such as dioxan. A phosphonate monoester 54.2 in which $R^1$ is alkenyl such as, for example, allyl, can be converted into the phosphonic acid 54.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 54.1 in which $R^1$ is benzyl is described in J. Org. Chem., 24, 434, 1959. Platinum-catalyzed hydrogenolysis of phosphonate esters 54.1 in which $R^1$ is phenyl is described in J. Amer. Chem. Soc., 78, 2336, 1956.

The conversion of a phosphonate monoester 54.2 into a phosphonate diester 54.1 (Scheme 54, Reaction 4) in which the newly introduced $R^1$ group is alkyl, aralkyl, haloalkyl such as chloroethyl, or aralkyl can be effected by a number of reactions in which the substrate 54.2 is reacted with a hydroxy compound $R^1OH$, in the presence of a coupling agent. Suitable coupling agents are those employed for the preparation of carboxylate esters, and include a carbodiimide such as dicyclohexylcarbodilmide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 54.2 to the diester 54.1 can be effected by the use of the Mitsonobu reaction, as described above (Scheme 25). The substrate is reacted with the hydroxy compound $R^1OH$, in the presence of diethyl azodicarboxylate and a triarylphosphine such as triphenyl phosphine. Alternatively, the phosphonate monoester 54.2 can be transformed into the phosphonate diester 54.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 54.2 is transformed into the chloro analog RP(O)($OR^1$)Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product RP(O)($OR^1$)Cl is then reacted with the hydroxy compound $R^1OH$, in the presence of a base such as triethylamine, to afford the phosphonate diester 54.1.

A phosphonic acid R-link-P(O)($OH$)$_2$ can be transformed into a phosphonate monoester RP(O)($OR^1$)(OH) (Scheme 54, Reaction 5) by means of the methods described above of for the preparation of the phosphonate diester R-link-P(O)($OR^1$)$_2$ 54.1, except that only one molar proportion of the component $R^1OH$ or $R^1Br$ is employed.

A phosphonic acid R-link-P(O)($OH$)$_2$ 54.3 can be transformed into a phosphonate diester R-link-P(O)($OR^1$)$_2$ 54.1 (Scheme 54, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids 54.3 can be transformed into phosphonic esters 54.1 in which $R^1$ is aryl, by means of a coupling reaction employing, for example, dicyclohexylcarbodiimide in pyridine at ca 70° C. Alternatively, phosphonic acids 54.3 can be transformed into phosphonic esters 54.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 54.1.

Scheme 55

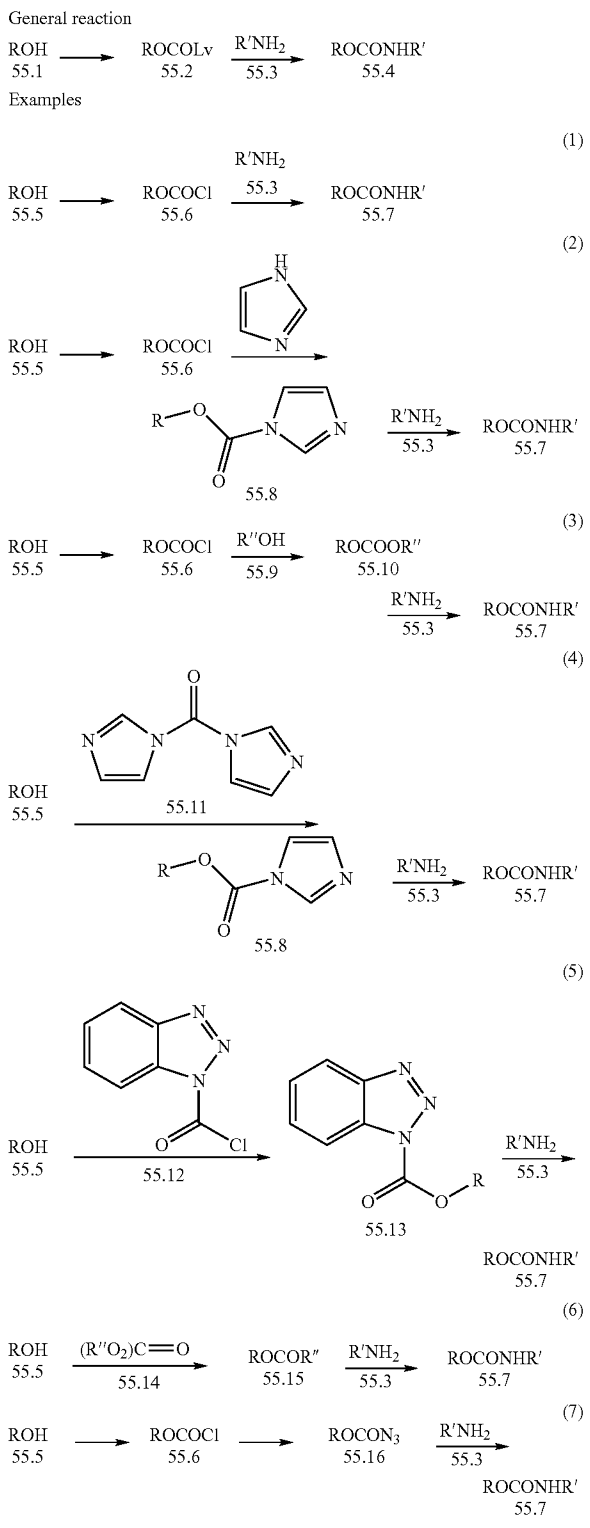

-continued

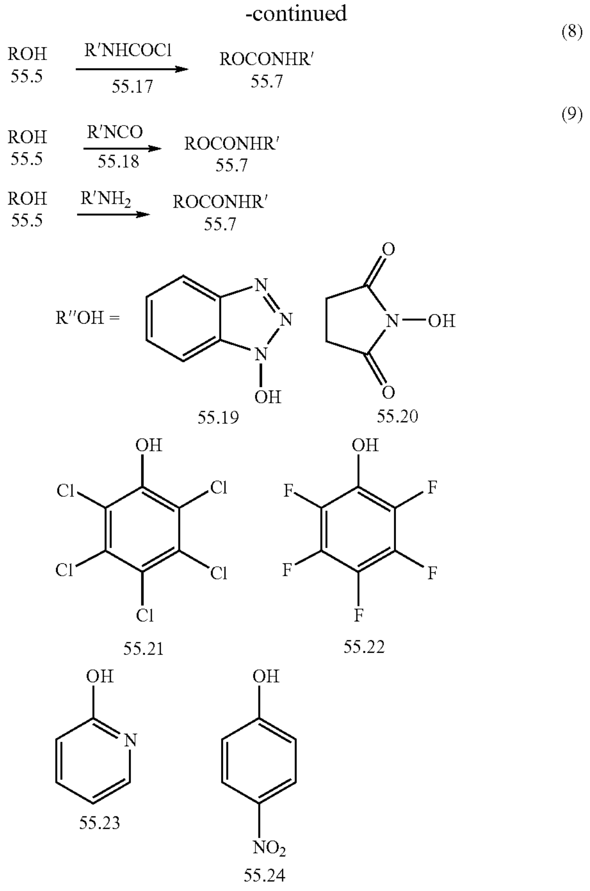

Preparation of the Phosphonate Esters 1-6 Incorporating Carbamate Moieties.

The phosphonate esters 1-6 in which the $R^6CO$ group is formally derived from the carboxylic acid synthons C39-C49 as shown in Chart 2c, contain a carbamate moiety. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 55 illustrates various methods by which the carbamate linkage can be synthesized. As shown in Scheme 55, in the general reaction generating carbamates, a carbinol 55.1 is converted into the activated derivative 55.2 in which Lv is a leaving group such as halo, imidazolyl, benztriazolyl and the like, as described below. The activated derivative 55.2 is then reacted with an amine 55.3, to afford the carbamate product 55.4. Examples 1-7 in Scheme 55 depict methods by which the general reaction can be effected. Examples 8-10 illustrate alternative methods for the preparation of carbamates.

Scheme 55, Example 1 illustrates the preparation of carbamates employing a chloroformyl derivative of the carbinol 55.5. In this procedure, the carbinol 55.5 is reacted with phosgene, in an inert solvent such as toluene, at about 0° C., as described in Org. Syn. Coil. Vol. 3, 167, 1965, or with an equivalent reagent such as trichloromethoxy chloroformate, as described in Org. Syn. Coll. Vol. 6, 715, 1988, to afford the chloroformate 55.6. The latter compound is then reacted with the amine component 55.3, in the presence of an organic or inorganic base, to afford the carbamate 55.7. For example, the chloroformyl compound 55.6 is reacted with the amine 55.3 in a water-miscible solvent such as tetrahydrofuran, in the presence of aqueous sodium hydroxide, as described in Org. Syn. Coil. Vol. 3, 167, 1965, to yield the carbamate 55.7. Alternatively, the reaction is preformed in dichloromethane in the presence of an organic base such as diisopropylethylamine or dimethylaminopyridine.

Scheme 55, Example 2 depicts the reaction of the chloroformate compound 55.6 with imidazole, 55.7, to produce the imidazolide 55.8. The imidazolide product is then reacted with the amine 55.3 to yield the carbamate 55.7. The preparation of the imidazolide is performed in an aprotic solvent such as dichloromethane at 0° C., and the preparation of the carbamate is conducted in a similar solvent at ambient temperature, optionally in the presence of a base such as dimethylaminopyridine, as described in J. Med. Chem., 1989, 32, 357. Scheme 55 Example 3, depicts the reaction of the chloroformate 55.6 with an activated hydroxyl compound R"OH, to yield the mixed carbonate ester 55.10. The reaction is conducted in an inert organic solvent such as ether or dichloromethane, in the presence of a base such as dicyclohexylamine or triethylamine. The hydroxyl component R"OH is selected from the group of compounds 55.19-55.24 shown in Scheme 55, and similar compounds. For example, if the component R"OH is hydroxybenztriazole 55.19, N-hydroxysuccinimide 55.20, or pentachlorophenol, 55.21, the mixed carbonate 55.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 55.22 or 2-hydroxypyridine 55.23 can be performed in an ethereal solvent in the presence of triethylamine, as described in Syn., 1986, 303, and Chem. Ber. 118, 468, 1985.

Scheme 55 Example 4 illustrates the preparation of carbamates in which an alkyloxycarbonylimidazole 55.8 is employed. In this procedure, a carbinol 55.5 is reacted with an equimolar amount of carbonyl diimidazole 55.11 to prepare the intermediate 55.8. The reaction is conducted in an aprotic organic solvent such as dichloromethane or tetrahydrofuran. The acyloxyimidazole 55.8 is then reacted with an equimolar amount of the amine R'$NH_2$ to afford the carbamate 55.7. The reaction is performed in an aprotic organic solvent such as dichloromethane, as described in Tet. Lett., 42, 2001, 5227, to afford the carbamate 55.7.

Scheme 55, Example 5 illustrates the preparation of carbamates by means of an intermediate alkoxycarbonylbenztriazole 55.13. In this procedure, a carbinol ROH is reacted at ambient temperature with an equimolar amount of benztriazole carbonyl chloride 55.12, to afford the alkoxycarbonyl product 55.13. The reaction is performed in an organic solvent such as benzene or toluene, in the presence of a tertiary organic amine such as triethylamine, as described in Syn., 1977, 704. This product is then reacted with the amine R'$NH_2$ to afford the carbamate 55.7. The reaction is conducted in toluene or ethanol, at from ambient temperature to about 80° C. as described in Syn., 1977, 704.

Scheme 55, Example 6 illustrates the preparation of carbamates in which a carbonate $(R''O)_2CO$, 55.14, is reacted with a carbinol 55.5 to afford the intermediate alkyloxycarbonyl intermediate 55.15. The latter reagent is then reacted with the amine R'$NH_2$ to afford the carbamate 55.7. The procedure in which the reagent 55.15 is derived from hydroxybenztriazole 55.19 is described in Synthesis, 1993, 908; the procedure in which the reagent 55.15 is derived from N-hydroxysuccinimide 55.20 is described in Tet. Lett., 1992, 2781; the procedure in which the reagent 55.15 is derived from 2-hydroxypyridine 55.23 is described in Tet. Lett., 1991, 4251; the procedure in which the reagent 55.15 is derived from 4-nitrophenol 55.24 is described in Syn. 1993, 103. The reaction between equimolar amounts of the carbinol ROH and the carbonate 55.14 is conducted in an inert organic solvent at ambient temperature.

Scheme 55, Example 7 illustrates the preparation of carbamates from alkoxycarbonyl azides 55.16. in this procedure, an alkyl chloroformate 55.6 is reacted with an azide, for example sodium azide, to afford the alkoxycarbonyl azide 55.16. The latter compound is then reacted with an equimolar amount of the amine R'$NH_2$ to afford the carbamate 55.7. The reaction is conducted at ambient temperature in a polar aprotic solvent such as dimethylsulfoxide, for example as described in Syn., 1982, 404.

Scheme 55, Example 8 illustrates the preparation of carbamates by means of the reaction between a carbinol ROH and the chloroformyl derivative of an amine. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 55.7. Scheme 55, Example 9 illustrates the preparation of carbamates by means of the reaction between a carbinol ROH and an isocyanate 55.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 55.7.

Scheme 55, Example 10 illustrates the preparation of carbamates by means of the reaction between a carbinol ROH and an amine R'$NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 55.7.

Preparation of Phosphonate Intermediates 5 and 6 with Phosphonate Moieties Incorporated into the Group $R^6COOH$ and $R^2NHCH(R^3)CONHR^4$.

The chemical transformations described in Schemes 1-55 illustrate the preparation of compounds 1-4 in which the phosphonate ester moiety is attached to the quinoline-2-carboxylate substructure, (Schemes 1-8), the phenylalanine or thiophenol moiety (Schemes 913), the tert-butylamine moiety (Schemes 14-18) and the decahydroisoquinoline moiety (Schemes 19-22).

The various chemical methods employed herein (Schemes 25-69) for the preparation of phosphonate groups can, with appropriate modifications known to those skilled in the art, be applied to the introduction of phosphonate ester groups into the compounds $R^6COOH$, as defined in Charts 3a, 3b and 3c, and into the compounds $R^2NHCH(R^3)CONHR^4$ as defined in Chart 2. For example, Schemes 56-61 illustrate the preparation of phosphonate-containing analogs of the phenoxyacetic acid C8 (Chart 3a), Schemes 62-65 illustrate the preparation of phosphonate-containing analogs of the carboxylic acid C4, Schemes 66-69 illustrate the preparation of phosphonate-containing analogs of the amine A12 (Chart 2), and Schemes 7075 illustrate the preparation of phosphonate-containing analogs of the carboxylic acid C38. The resultant phosphonate-containing analogs $R^{6a}COOH$ and $R^{2a}NHCH(R^{3a})CONHR^4$ can then, using the procedures described above, be employed in the preparation of the compounds 5 and 6. The procedures required for the introduction of the phosphonate-containing analogs $R^{6a}COOH$ and $R^{2a}NHCH(R^{3a})CONHR^4$ are the same as those described above for the introduction of the $R^6CO$ and $R^2NHCH(R^3)CONHR^4$ moieties.

Preparation of Dimethylphenoxyacetic Acids Incorporating Phosphonate Moieties.

Scheme 56 illustrates two alternative methods by means of which 2,6-dimethylphenoxyacetic acids bearing phosphonate moieties may be prepared. The phosphonate group may be introduced into the 2,6-dimethylphenol moiety, followed by attachment of the acetic acid group, or the phosphonate group may be introduced into a preformed 2,6-dimethylphenoxyacetic acid intermediate. In the first sequence, a substituted 2,6-dimethylphenol 56.1, in which the substituent B is a precursor to the group link-$P(O)(OR^1)_2$, and in which the phenolic hydroxyl may or may not be protected, depending on the reactions to be performed, is converted into a phosphonate-containing compound 56.2. Methods for the conversion of the substituent B into the group link-$P(O)(OR^1)_2$ are described in Schemes 25-69.

The protected phenolic hydroxyl group present in the phosphonate-containing product 56.2 is then deprotected, using methods described below, to afford the phenol 56.3. The phenolic product 56.3 is then transformed into the corresponding phenoxyacetic acid 56.4, in a two step procedure. In the first step, the phenol 56.3 is reacted with an ester of bromoacetic acid 56.5, in which R is an alkyl group or a protecting group. Methods for the protection of carboxylic acids are described in Protective Groups in Organic Synthesis, by T. W. Greene and P. G. M Wuts, Wiley, Second Edition 1990, p. 224ff. The alkylation of phenols to afford phenolic ethers is described, for example, in Comprehensive Organic Transformations, by R. C. Larock, VCH, 1989, p. 446ff. Typically, the phenol and the alkylating agent are reacted together in the presence of an organic or inorganic base, such as, for example, diazabicyclononene, (DBN) or potassium carbonate, in a polar organic solvent such as, for example, dimethylformamide or acetonitrile.

Preferably, equimolar amounts of the phenol 56.3 and ethyl bromoacetate are reacted together in the presence of cesium carbonate, in dioxan at reflux temperature, for example as described in U.S. Pat. No. 5,914,332, to afford the ester 56.6.

The thus-obtained ester 56.6 is then hydrolyzed to afford the carboxylic acid 56.4. The methods used for this reaction depend on the nature of the group R. If R is an alkyl group such as methyl, hydrolysis can be effected by treatment of the ester with aqueous or aqueous alcoholic base, or by use of an esterase enzyme such as porcine liver esterase. If R is a protecting group, methods for hydrolysis are described in Protective Groups in Organic Synthesis, by T. W. Greene and P. G. M Wuts, Wiley, Second Edition 1990, p. 224ff. Preferably, the ester product 56.6 which R is ethyl is hydrolyzed to the carboxylic acid 56.4 by reaction with lithium hydroxide in aqueous methanol at ambient temperature, as described in U.S. Pat. No. 5,914,332.

Alternatively, an appropriately substituted 2,6-dimethylphenol 56.7, in which the substituent B is a precursor to the group link-$P(O)(OR^1)_2$, is transformed into the corresponding phenoxyacetic ester 56.8. The conditions employed for the alkylation reaction are similar to those described above for the conversion of the phenol 56.3 into the ester 56.6.

The phenolic ester 56.8 is then converted, by transformation of the group B into the group link-$P(O)(OR^1)_2$ followed by ester hydrolysis, into the carboxylic acid 56.4. The group B which is present in the ester 56.4 may be transformed into the group link-$P(O)(OR^1)_2$ either before or after hydrolysis of the ester moiety into the carboxylic acid group, depending on the nature of the chemical transformations required.

Schemes 56-61 illustrate the preparation of 2,6-dimethylphenoxyacetic acids incorporating phosphonate ester groups. The procedures shown can also be applied to the preparation of phenoxyacetic esters acids 56.8, with, if appropriate, modifications made according to the knowledge of one skilled in the art.

Scheme 57 illustrates the preparation of 2,6-dimethylphenoxyacetic acids incorporating a phosphonate ester which is attached to the phenolic group by means of a carbon chain incorporating a nitrogen atom. The compounds 57.4 are obtained by means of a reductive alkylation reaction between a 2,6-dimethylphenol aldehyde 57.1 and an aminoalkyl phosphonate ester 57.2. The preparation of amines by means of reductive amination procedures is described, for example, in Comprehensive Organic Transformations, by R. C. Larock, VCH, p. 421. In this procedure, the amine component 57.2 and the aldehyde component 57.1 are reacted together in the presence of a reducing agent such as, for example, borane, sodium cyanoborohydride or diisobutylaluminum hydride, to yield the amine product 57.3. The amination product 57.3 is then converted into the phenoxyacetic acid compound 57.4, using the alkylation and ester hydrolysis procedures described above, (Scheme 56) For example, equimolar amounts of 4-hydroxy-3,5-dimethylbenzaldehyde 57.5 (Aldrich) and a dialkyl aminoethyl phosphonate 57.6, the preparation of which is described in J. Org. Chem., 2000, 65, 676, are reacted together in the presence of sodium cyanoborohydride and acetic acid, as described, for example, in J. Amer. Chem. Soc., 91, 3996, 1969, to afford the amine product 57.3. The product is then converted into the acetic acid 57.8, as described above. Using the above procedures, but employing, in place of the aldehyde 57.5, different aldehydes 57.1, and/or different aminoalkyl phosphonates 57.2, the corresponding products 57.4 are obtained.

In this and succeeding examples, the nature of the phosphonate ester group can be varied, either before or after incorporation into the scaffold, by means of chemical transformations. The transformations, and the methods by which they are accomplished, are described above (Scheme 54)

Scheme 58 depicts the preparation of 2,6-dimethylphenols incorporating a phosphonate group linked to the phenyl ring by means of a saturated or unsaturated alkylene chain. In this procedure, an optionally protected bromo-substituted 2,6-dimethylphenol 58.1 is coupled, by means of a palladium-catalyzed Heck reaction, with a dialkyl alkenyl phosphonate 58.2. The coupling of aryl bromides with olefins by means of the Heck reaction is described, for example, in Advanced Organic Chemistry, by F. A. Carey and R. J. Sundberg, Plenum, 2001, p. 503. The aryl bromide and the olefin are coupled in a polar solvent such as dimethylformamide or dioxan, in the presence of a palladium(0) or palladium (2) catalyst. Following the coupling reaction, the product 58.3 is converted, using the procedures described above, (Scheme 56) into the corresponding phenoxyacetic acid 58.4. Alternatively, the olefinic product 58.3 is reduced to afford the saturated 2,6-dimethylphenol derivative 58.5. Methods for the reduction of carbon-carbon double bonds are described, for example, in Comprehensive Organic Transformations, by R. C. Larock, VCH, 1989, p. 6. The methods include catalytic reduction, or chemical reduction employing, for example, diborane or diimide. Following the reduction reaction, the product 58.5 is converted, as described above, (Scheme 56) into the corresponding phenoxyacetic acid 58.6.

For example, 3-bromo-2,6-dimethylphenol 58.7, prepared as described in Can. J. Chem., 1983, 61, 1045, is converted into the tert-butyldimethylsilyl ether 58.8, by reaction with chloro-tert-butyldimethylsilane, and a base such as imidazole, as described in Protective Groups in Organic Synthesis, by T. W. Greene and P. G. M Wuts, Wiley, Second Edition 1990 p. 77. The product 58.8 is reacted with an equimolar amount of a dialkyl allyl phosphonate 58.9, for example diethyl allylphosphonate (Aldrich) in the presence of ca. 3 mol % of bis(triphenylphosphine)palladium(II) chloride, in dimethylformamide at ca. 60° C., to produce the coupled product 58.10. The silyl group is removed, for example by the treatment of the ether 58.10 with a solution of tetrabutylammonium fluoride in tetrahydrofuran, as described in J. Am. Chem., Soc., 94, 6190, 1972, to afford the phenol 58.11. This compound is converted, employing the procedures described above, (Scheme 56) into the corresponding phenoxyacetic acid 58.12. Alternatively, the unsaturated compound 58.11 is reduced, for example by catalytic hydrogenation employing 5% palladium on carbon as catalyst, in an alcoholic solvent such as methanol, as described, for example, in Hydrogenation Methods, by R. N. Rylander, Academic Press, 1985, Ch. 2, to afford the saturated analog 58.13. This compound is converted, employing the procedures described above, (Scheme 56) into the corresponding phenoxyacetic acid 58.14.

Using the above procedures, but employing, in place of 3-bromo-2,6-dimethylphenol 58.7, different bromophenols 58.1, and/or different dialkyl alkenyl phosphonates 58.2, the corresponding products 58.4 and 58.6 are obtained.

Scheme 59 illustrates the preparation of phosphonate-containing 2,6-dimethylphenoxyacetic acids 59.1 in which the phosphonate group is attached to the 2,6-dimethylphenoxy moiety by means of a carbocyclic ring. In this procedure, a bromo-substituted 2,6-dimethylphenol 59.2 is converted, using the procedures illustrated in Scheme 56, into the corresponding 2,6-dimethylphenoxyacetic ester 59.3. The latter compound is then reacted, by means of a palladium-catalyzed Heck reaction, with a cycloalkenone 59.4, in which n is 1 or 2. The coupling reaction is conducted under the same conditions as those described above for the preparation of 58.3 (Scheme 58). The product 59.5 is then reduced catalytically, as described above for the reduction of 58.3, (Scheme 58), to afford the substituted cycloalkanone 59.6. The ketone is then subjected to a reductive amination procedure, by reaction with a dialkyl 2-aminoethylphosphonate 59.7 and sodium triacetoxyborohydride, as described in J. Org. Chem., 61, 3849, 1996, to yield the amine phosphonate 59.8. The reductive amination reaction is conducted under the same conditions as those described above for the preparation of the amine 57.3 (Scheme 57). The resultant ester 59.8 is then hydrolyzed, as described above, to afford the phenoxyacetic acid 59.1.

For example, 4-bromo-2,6-dimethylphenol 59.9 (Aldrich) is converted, as described above, into the phenoxy ester 59.10. The latter compound is then coupled, in dimethylformamide solution at ca. 60° C., with cyclohexenone 59.11, in the presence of tetrakis(triphenylphosphine)palladium(0) and triethylamine, to yield the cyclohexenone 59.12.

The enone is then reduced to the saturated ketone 59.13, by means of catalytic hydrogenation employing 5% palladium on carbon as catalyst. The saturated ketone is then reacted with an equimolar amount of a dialkyl aminoethylphosphonate 59.14, prepared as described in J. Org. Chem., 2000, 65, 676, in the presence of sodium cyanoborohydride, to yield the amine 59.15. Hydrolysis, employing lithium hydroxide in aqueous methanol at ambient temperature, then yields the acetic acid 59.16.

Using the above procedures, but employing, in place of 4-bromo-2,6-dimethylphenol 59.9, different bromo-substituted 2,6-dimethylphenols 59.2, and/or different cycloalkenones 59.4, and/or different dialkyl aminoalkylphosphonates 59.7, the corresponding products 59.1 are obtained.

Scheme 60 illustrates the preparation of 2,6-dimethylphenoxyacetic acids incorporating a phosphonate group attached to the phenyl ring by means of a heteroatom and an alkylene chain. The compounds are obtained by means of alkylation reactions in which an optionally protected hydroxy, thio or amino-substituted 2,6-dimethylphenol 60.1 is reacted, in the presence of a base such as, for example, potassium carbonate, and optionally in the presence of a catalytic amount of an iodide such as potassium iodide, with a dialkyl bromoalkyl phosphonate 60.2. The reaction is conducted in a polar organic solvent such as dimethylformamide or acetonitrile at from ambient temperature to about 80° C. The product of the alkylation reaction, 60.3 is then converted, as described above (Scheme 56) into the phenoxyacetic acid 60.4.

For example, 2,6-dimethyl-4-mercaptophenol 60.5, prepared as described in EP 482342, is reacted in dimethylformamide at ca. 60° C. with an equimolar amount of a dialkyl bromobutyl phosphonate 60.6, the preparation of which is described in Synthesis, 1994, 9, 909, in the presence of ca. 5 molar equivalents of potassium carbonate, to afford the thioether product 60.7. This compound is converted, employing the procedures described above, (Scheme 56) into the corresponding phenoxyacetic acid 60.8.

Using the above procedures, but employing, in place of 2,6-dimethyl-4-mercaptophenol 60.5, different hydroxy, thio or aminophenols 60.1, and/or different dialkyl bromoalkyl phosphonates 60.2, the corresponding products 60.4 are obtained.

Scheme 61 illustrates the preparation of 2,6-dimethylphenoxyacetic acids incorporating a phosphonate ester group attached by means of an aromatic or heteroaromatic group. In this procedure, an optionally protected hydroxy, mercapto or amino-substituted 2.6-dimethylphenol 61.1 is reacted, under basic conditions, with a bis(halomethyl)aryl or heteroaryl compound 61.2. Equimolar amounts of the phenol and the halomethyl compound are reacted in a polar organic solvent such as dimethylformamide or acetonitrile, in the presence of a base such as potassium or cesium carbonate, or dimethylaminopyridine, to afford the ether, thioether or amino product 61.3. The product 61.3 is then converted, using the procedures described above, (Scheme 56) into the phenoxyacetic ester 61.4. The latter compound is then subjected to an Arbuzov reaction by reaction with a trialkylphosphite 61.5 at ca. 100° C. to afford the phosphonate ester 61.6. The preparation of phosphonates by means of the Arbuzov reaction is described, for example, in Handb. Organophosphorus Chem., 1992, 115. The resultant product 61.6 is then converted into the acetic acid 61.7 by hydrolysis of the ester moiety, using the procedures described above, (Scheme 56).

For example, 4-hydroxy-2,6-dimethylphenol 61.8 (Aldrich) is reacted with one molar equivalent of 3,5-bis(chloromethyl)pyridine, the preparation of which is described in Eur. J. Inorg. Chem., 1998, 2, 163, to afford the ether 61.10. The reaction is conducted in acetonitrile at ambient temperature in the presence of five molar equivalents of potassium carbonate. The product 61.10 is then reacted with ethyl bromoacetate, using the procedures described above, (Scheme 56) to afford the phenoxyacetic ester 61.11. This product is heated at 100° C. for 3 hours with three molar equivalents of triethyl phosphite 61.12, to afford the phosphonate ester 61.13. Hydrolysis of the acetic ester moiety, as described above, for example by reaction with lithium hydroxide in aqueous ethanol, then affords the phenoxyacetic acid 61.14.

Using the above procedures, but employing, in place of the bis(chloromethyl) pyridine 61.9, different bis(halomethyl) aromatic or heteroaromatic compounds 61.2, and/or different hydroxy, mercapto or amino-substituted 2,6-dimethylphenols 61.1 and/or different trialkyl phosphites 61.5, the corresponding products 61.7 are obtained.

Scheme 56
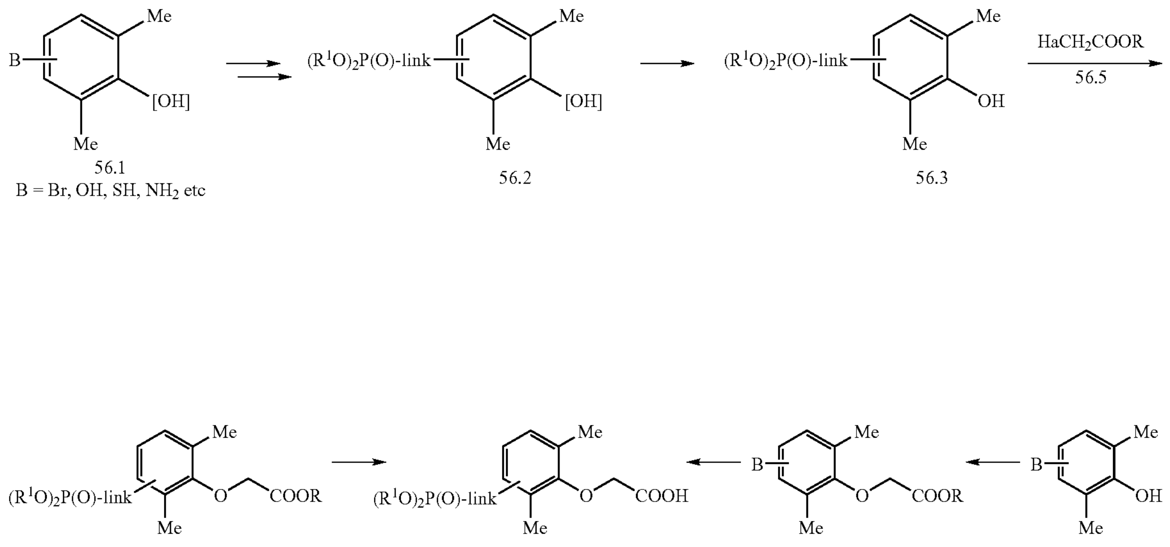
56.1 56.2 56.3 56.6 56.4 56.8 56.7
Scheme 57
Method
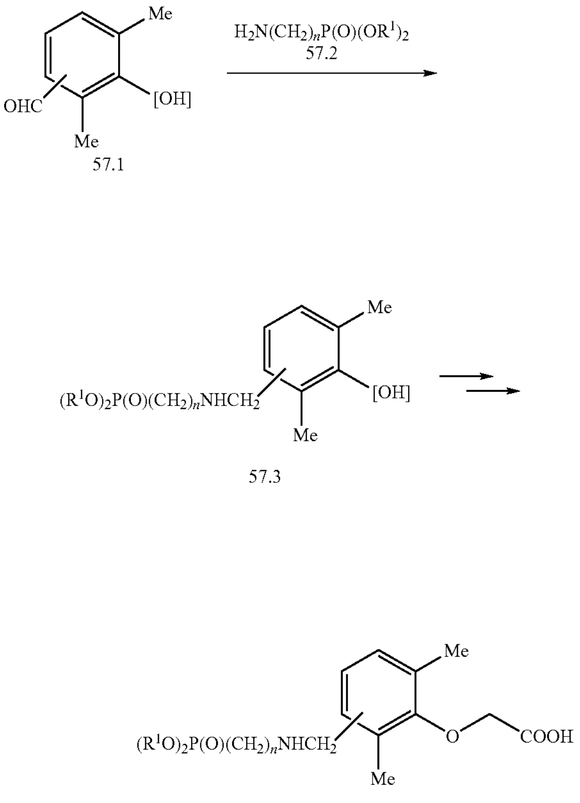
57.1 57.3 57.4
-continued
Example
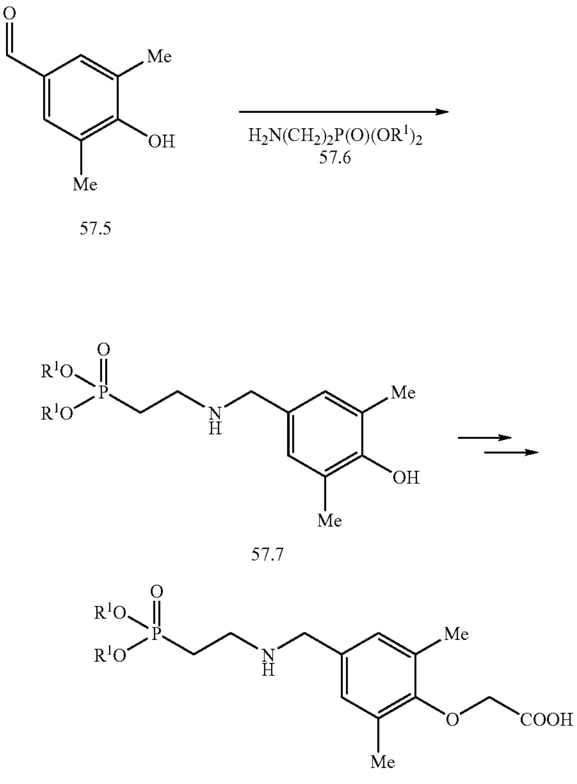
57.5 57.7 57.8

Scheme 58
Method
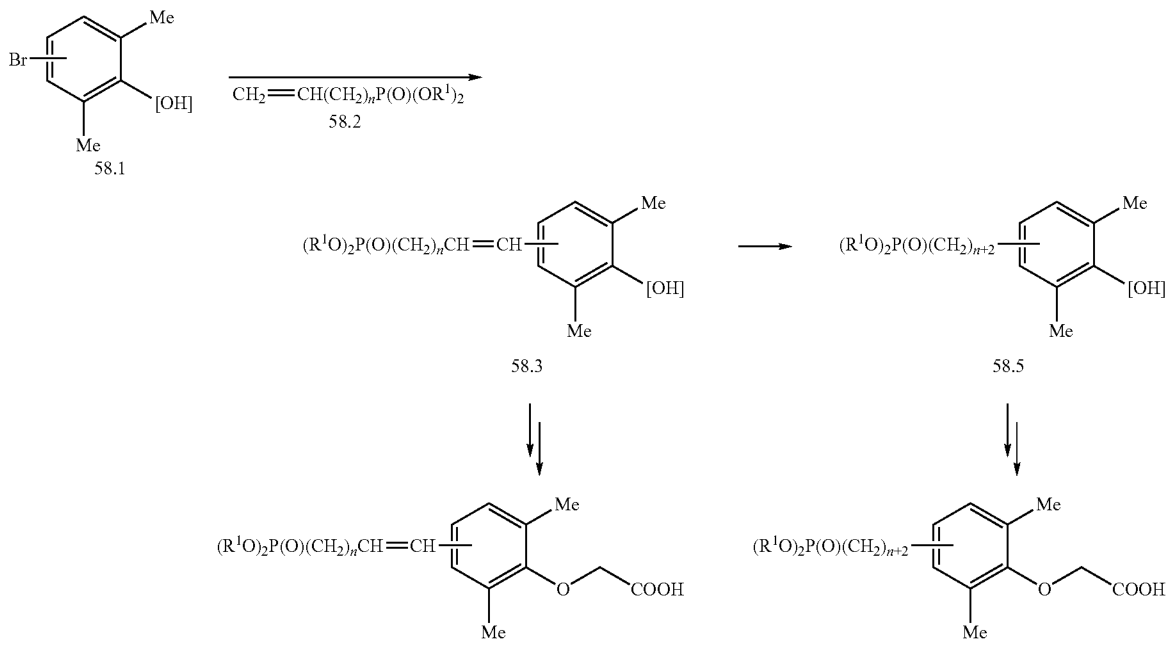
58.1, 58.3, 58.5, 58.4, 58.6
Example
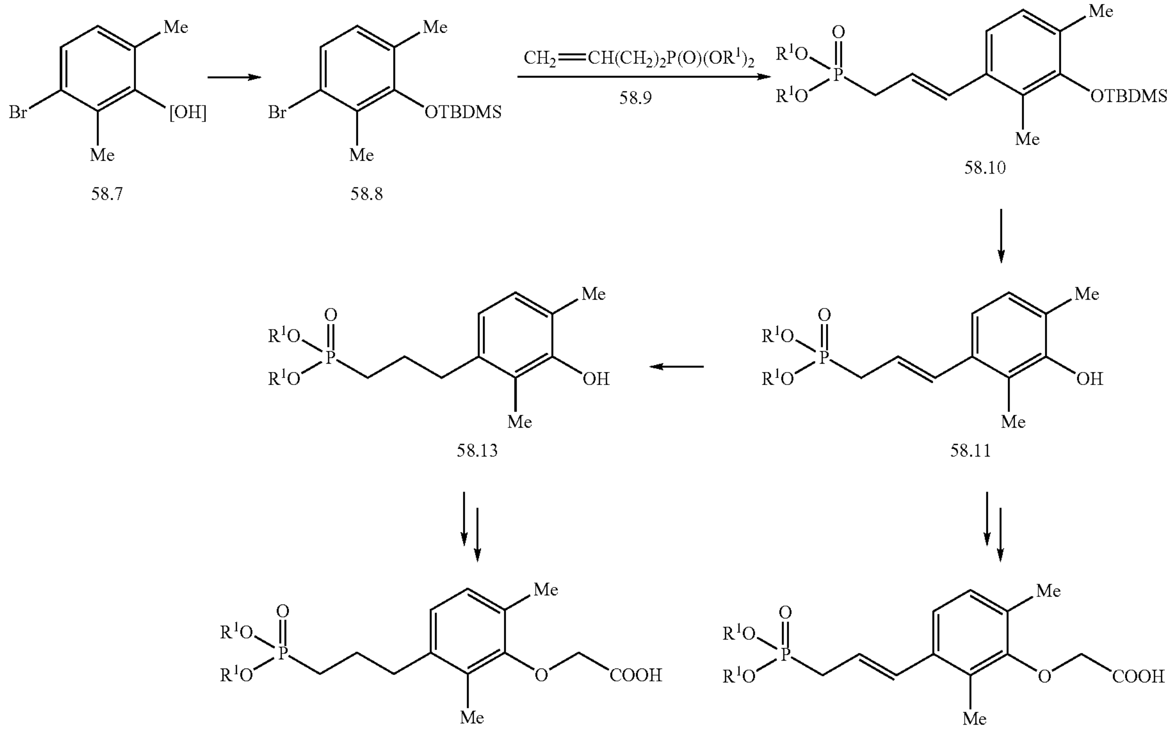
58.7, 58.8, 58.10, 58.11, 58.13, 58.12, 58.14

Scheme 59
Method
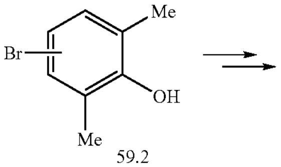
59.2
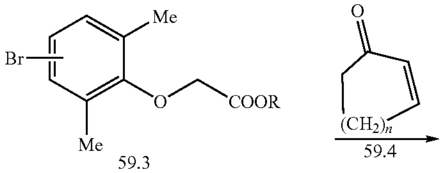
59.3 59.4
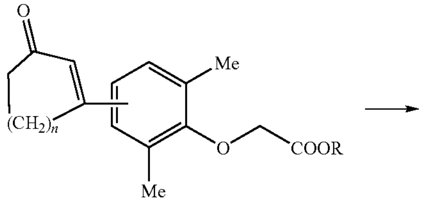
59.5
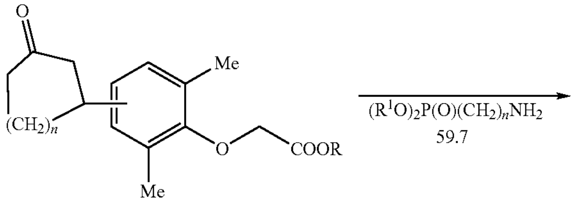
59.6 59.7
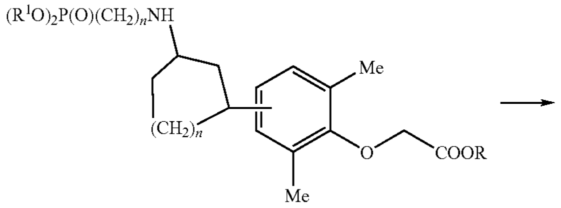
59.8
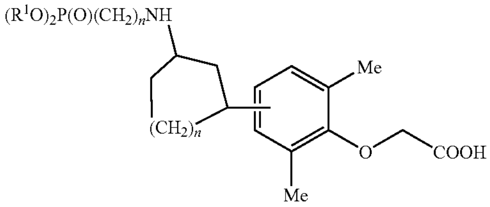
59.1
Example
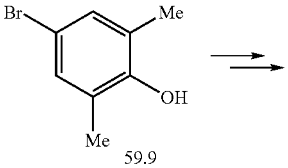
59.9
-continued
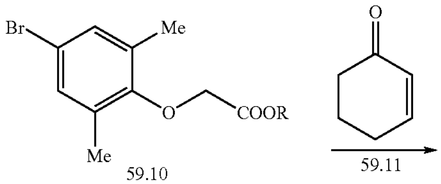
59.10 59.11
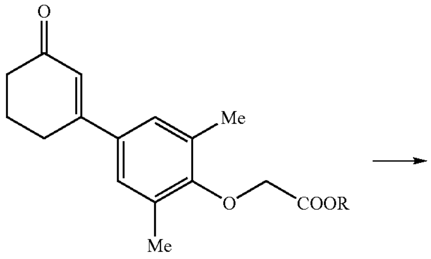
59.12
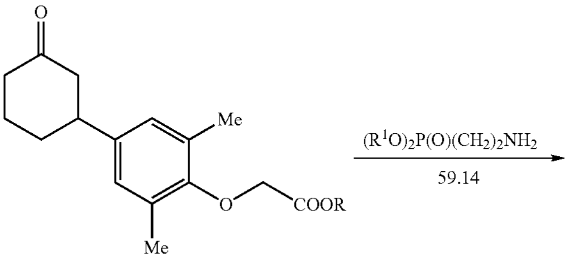
59.13 59.14
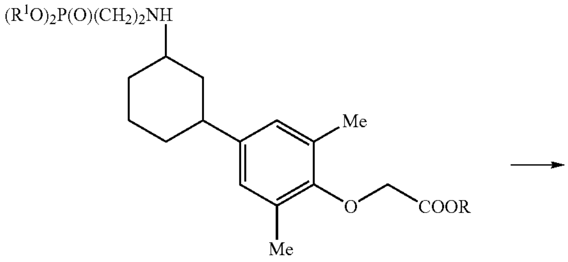
59.15
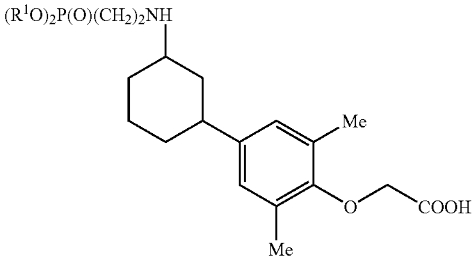
59.16

Scheme 60
Method
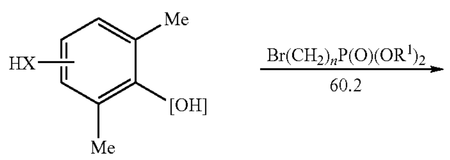
X = O, S, NH, Nalkyl
60.1
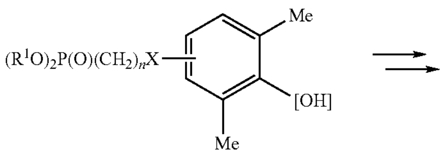
60.3
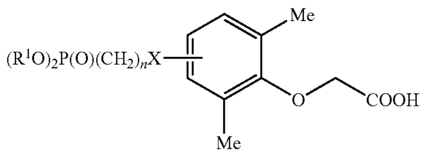
60.4
Example
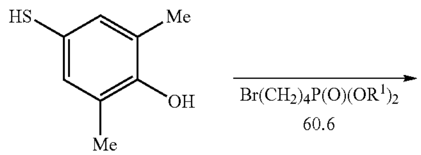
60.5
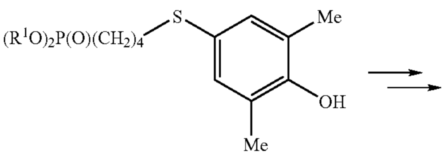
60.7
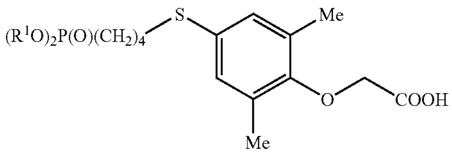
60.8
Scheme 61
Method
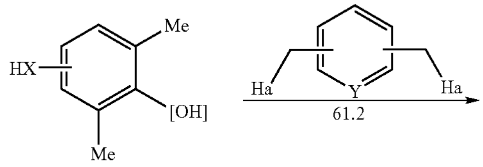
X = O, S, NH, Nalkyl
Y = CH, N
61.1
-continued
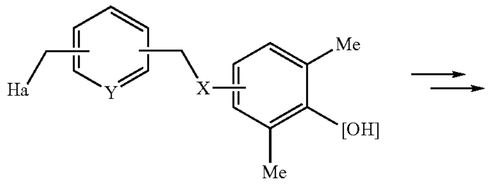
61.3
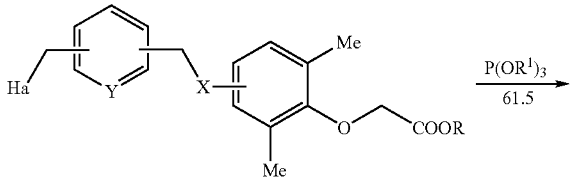
61.4
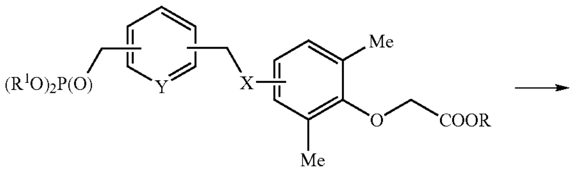
61.6
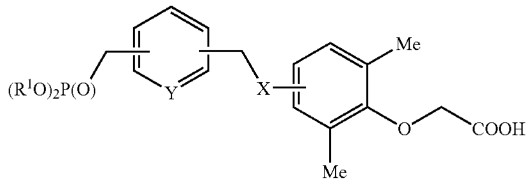
61.7
Example
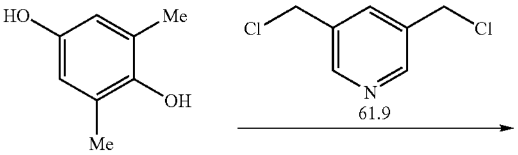
61.8
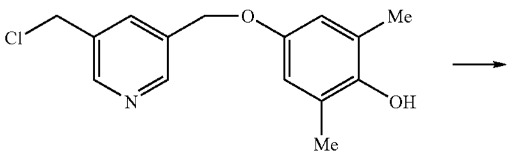
61.10
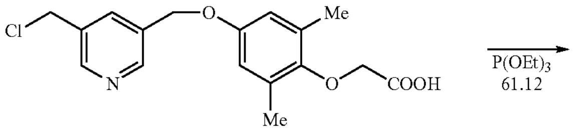
61.11
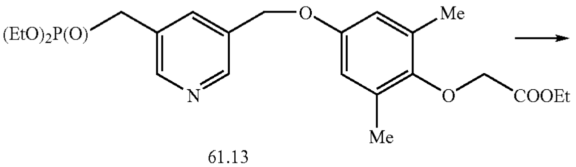
61.13

-continued

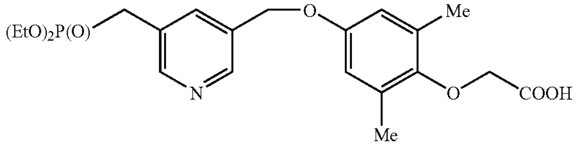

61.14

Preparation of Benzyl Carbamate Compounds Incorporating Phosphonate Groups.

Scheme 62 depicts the preparation of phosphonate-containing analogs of the benzyl carbamate aminoacid derivative C4 in which the phosphonate moiety is either directly attached to the phenyl ring or attached by means of an alkylene chain. In this procedure, a dialkyl hydroxymethylphenyl alkylphosphonate 62.1 is converted into an activated derivative 62.2, in which Lv is a leaving group, as described above (Scheme 55). The product is then reacted with a suitably protected aminoacid 62.3, to afford the carbamate product 62.4. The reaction is conducted under the conditions described above for the preparation of carbamates (Scheme 55). The protecting group on the carboxylic acid group in the product 62.4 is then removed to afford the free carboxylic acid 62.5. Methods for the protection and deprotection of carboxylic acids are described, for example, in Protective Groups in Organic Synthesis, by T. W. Greene and P. G. M Wuts, Wiley, Second Edition 1990, p. 224ff.

For example, as shown in Scheme 62, Example 1, a dialkyl 4-hydroxymethylphenyl phosphonate 62.6, prepared as described in U.S. Pat. No. 5,569,664, is reacted with phosgene, or an equivalent thereof, as described above (Scheme 55), to afford the chloroformyl product 62.7. This compound is then reacted in an inert solvent such as dichloromethane or tetrahydrofuran, with the tert. butyl aminoacid ester 62.3, in the presence of a base such as triethylamine, to yield the carbamate product 62.8. The conversion of acids into tert. butyl esters is described in Protective Groups in Organic Synthesis, by T. W. Greene and P. G. M Wuts, Wiley, Second Edition 1990, p. 245ff. The ester can be prepared by the reaction of the carboxylic acid with isobutylene and an acid catalyst, or by conventional esterification procedures employing tert. butanol. The tert. butyl protecting group is then removed from the product 62.8, for example by reaction with trifluoroacetic acid at ambient temperature for about one hour, to afford the carboxylic acid 62.9.

As a further example, Scheme 62, Example 2 shows the conversion of a dialkyl 4hydroxymethyl benzyl phosphonate 62.10, prepared as described in J. Am. Chem. Soc., 1996, 118, 5881, into the hydroxybenztriazole derivative 62.11. The reaction is performed as described above (Scheme 55). The activated derivative is then reacted with the aminoacid derivative 62.3, as described above, to afford the carbamate 62.12. deprotection, as previously described, then affords the carboxylic acid 62.13.

Using the above procedures, but employing, in place of the phosphonates 62.6 and 62.10, different phosphonates 62.1, and/or different aminoacid derivatives 62.3, the corresponding products 62.5 are obtained.

Scheme 63 depicts the preparation of phosphonate-containing analogs of the benzyl carbamate aminoacid derivative C4 in which the phosphonate moiety is attached to the phenyl ring by means of a saturated or unsaturated alkylene chain. In this procedure, a bromo-substituted benzyl alcohol 63.1 is subjected to a palladium catalyzed Heck reaction, as described above, (Scheme 26) with a dialkyl alkenyl phosphonate 63.2, to afford the olefinic product 63.3. The product is then converted into the activated derivative 63.4, which is then reacted with aminoacid derivative 62.3, as described above, to afford, after deprotection of the carboxyl group, the carbamate product 63.5. Optionally, the olefinic coupling product can be reduced to the saturated analog 63.6. The reduction reaction can be effected chemically, for example by the use of diimide or diborane, as described in Comprehensive Organic Transformations, by R. C. Larock, VCH, 1989, p. 5. The product 63.6 is then converted, as described above, into the carbamate derivative 63.8.

For example, 3-bromobenzyl alcohol 63.9 is coupled in acetonitrile solution, with a dialkyl allylphosphonate 63.10 (Aldrich), in the presence of palladium acetate, triethylamine and tri-o-tolylphosphine, as described in Synthesis, 1983, 556, to afford the product 63.11. This material is then reacted with carbonyl diimidazole, as described above, (Scheme 55) to afford the imidazolide 63.12. The product is then coupled with the aminoacid derivative 62.3, to afford after deprotection, the product 63.13. Alternatively, the unsaturated phosphonate 63.11 is reduced, for example by reaction with diborane in tetrahydrofuran at ambient temperature, as described in Comprehensive Organic Transformations, by R. C. Larock, VCH, 1989, p. 5., to afford the saturated analog 63.14. The latter compound is then transformed, as described above, into the carbamate aminoacid derivative 63.15.

Using the above procedures, but employing, in place of the 3-bromobenzyl alcohol 63.9, different bromobenzyl alcohols 63.1, and/or different alkenyl phosphonates 63.2, and/or different amino acid derivatives, the corresponding products 63.5 and 63.8 are obtained.

Scheme 64 depicts the preparation of phosphonate-containing analogs of the benzyl carbamate aminoacid derivative C4 in which the phosphonate moiety is attached to the phenyl ring by means of an amino-containing alkylene chain. In this procedure, a formyl-substituted benzyl alcohol 64.1 is converted, using the procedures described above is Schemes 55 and 63, into the aminoacid carbamate derivative 64.2. The product is then subjected to a reductive amination reaction with a dialkyl aminoalkyl phosphonate 64.3, to afford the phosphonate product 64.4. Reductive amination of carbonyl compounds is described above (Scheme 27). For example, 3-formyl benzyl alcohol 64.5 is converted into the carbamate derivative 64.6. The product is then reacted in ethanol solution at ambient temperature with a dialkyl aminoethyl phosphonate 64.7, the preparation of which is described in J. Org. Chem., 2000, 65, 676, in the presence of sodium cyanoborohydride, to yield the phosphonate product 64.8. Using the above procedures, but employing, in place of the 3-formylbenzyl alcohol 64.5, different formylbenzyl alcohols 64.1, and/or different aminoalkyl phosphonates 64.3, the corresponding products 64.4 are obtained.

Scheme 65 depicts the preparation of phosphonate-containing analogs of the benzyl carbamate aminoacid derivative C4 in which the phosphonate moiety is attached to the phenyl ring by means of an O, S or N-alkyl-containing alkylene chain. In this procedure, a chloromethyl-substituted benzyl alcohol 65.1 is reacted with a dialkyl hydroxy, mercapto or alkylaminoalkyl phosphonate 65.2. The alkylation reaction is conducted between equimolar amounts of the reactants in a polar organic solvent such as dimethylformamide or acetonitrile, in the presence of an inorganic or organic base, such as diisopropylethylamine, dimethylaminopyridine, potassium carbonate and the like. The alkylated product 65.3 is then converted, as previously described, into the carbamate aminoacid derivative 65.4.

For example, 4-chloromethylbenzyl alcohol 65.5, (Aldrich) is reacted at ca. 60° C. in acetonitrile solution with a dialkyl hydroxypropyl phosphonate 65.6, the preparation of which is described in Zh. Obschei. Khin., 1974, 44, 1834, in the presence of dimethylaminopyridine, to afford the ether product 65.7. The product is then converted, as previously described, into the carbamate derivative 65.8.

Using the above procedures, but employing, in place of 4-(chloromethyl)benzyl alcohol 65.5, different chloromethyl benzyl alcohols 65.1, and/or different hydroxy, mercapto or alkylamino phosphonates 65.2, the corresponding products 65.4 are obtained.

Scheme 62

Method

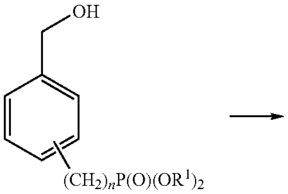

62.1

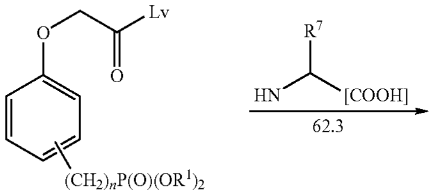

62.2

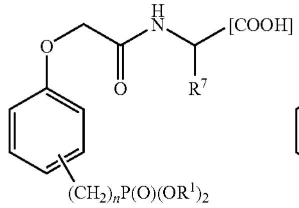

62.4

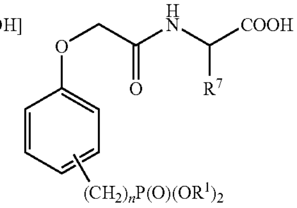

62.5

Example 1

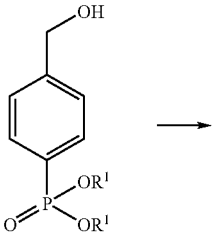

62.6

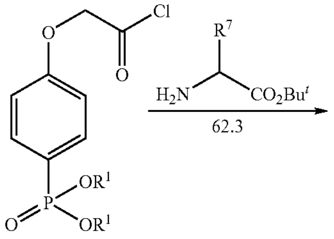

62.7

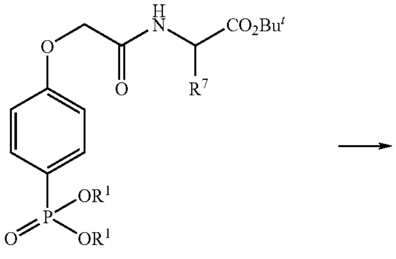

62.8

-continued

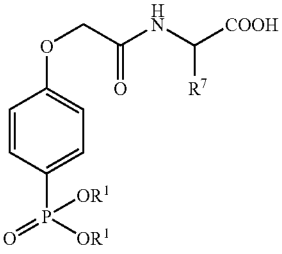

62.9

Example 2

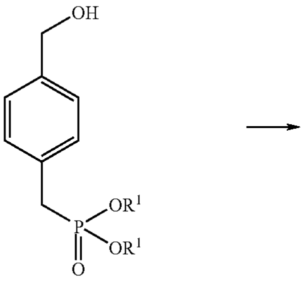

62.10

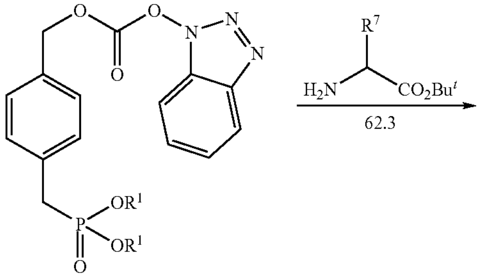

62.11

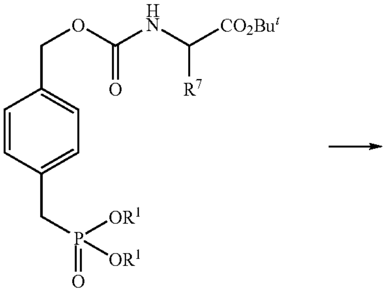

62.12

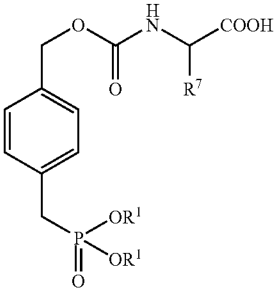

62.13

Scheme 63
Method
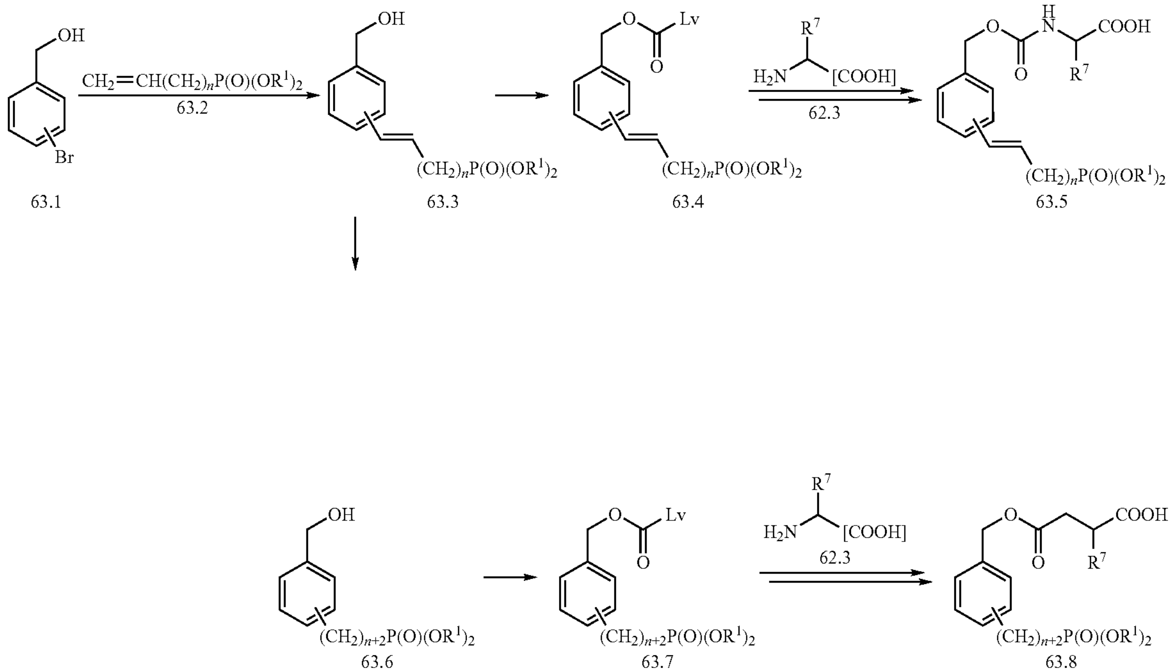
63.1 63.3 63.4 63.5
63.6 63.7 63.8
Example
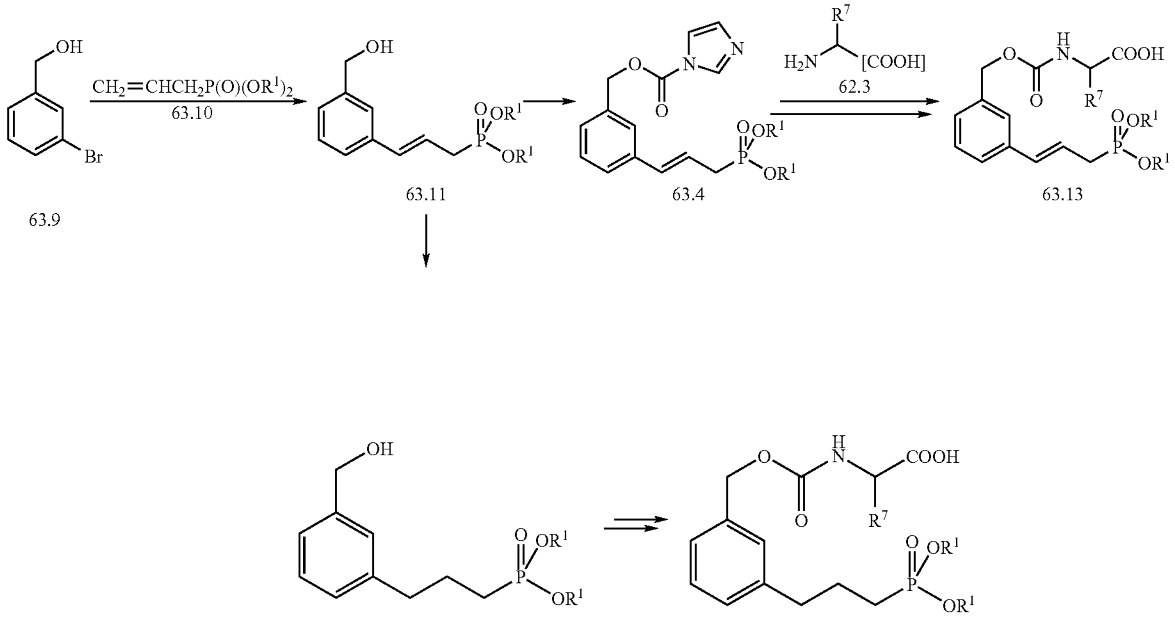
63.9 63.11 63.4 63.13
63.14 63.15

Scheme 64

Method

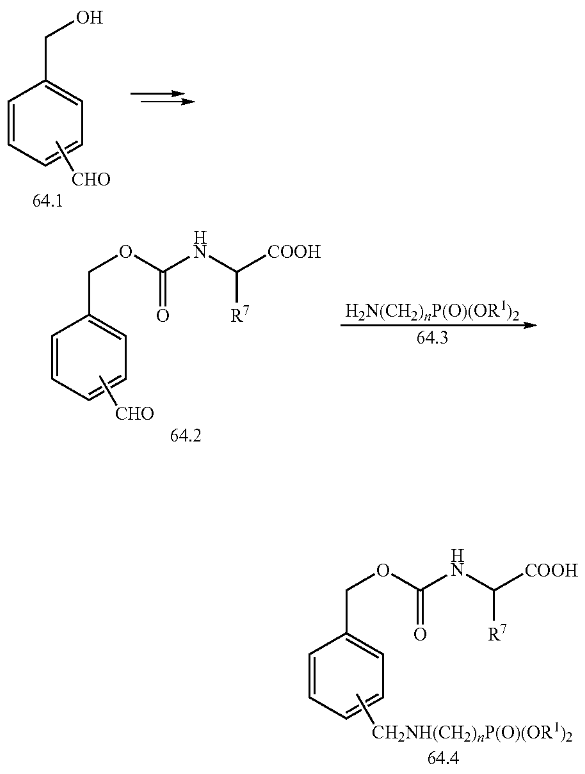

Example

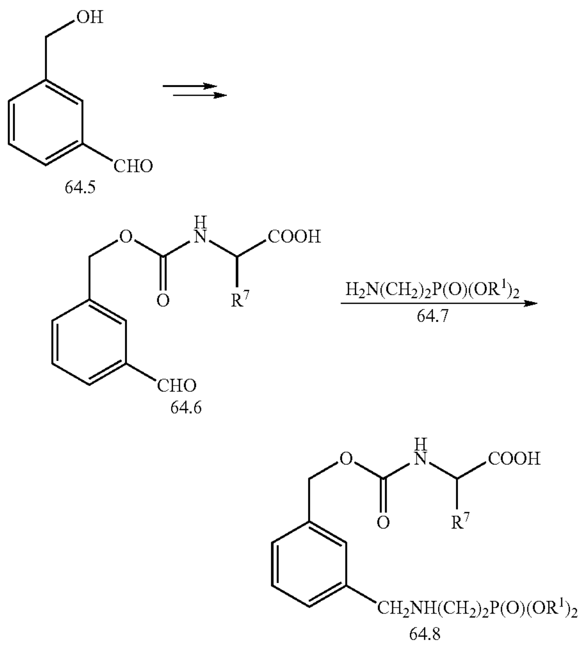

Scheme 65

Method

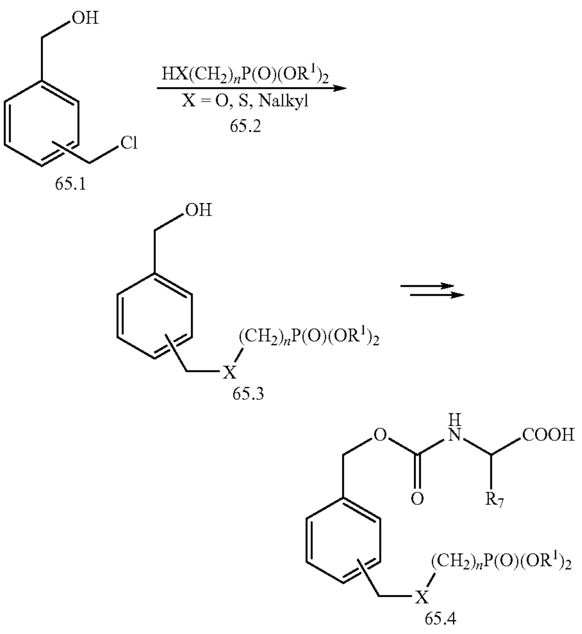

Example

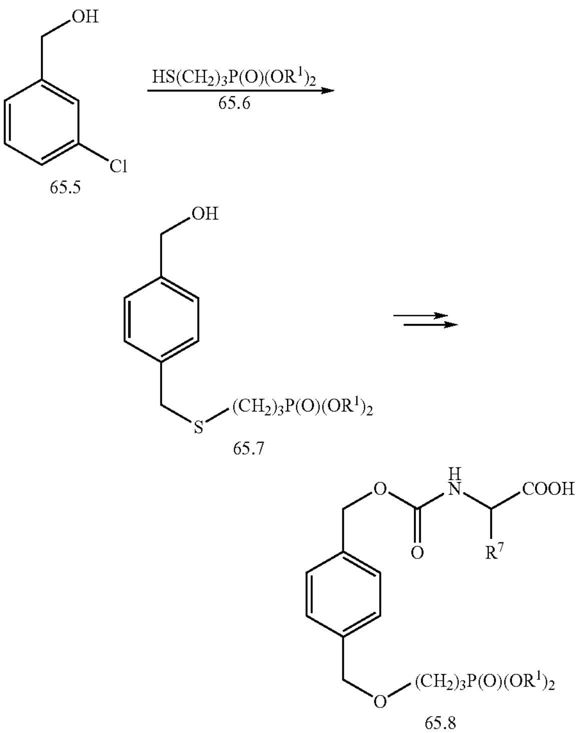

Preparation of Pyridinyloxymethyl Piperidine Derivatives Incorporating Phosphonate Groups.

Scheme 66 illustrates the preparation of phosphonate-containing analogs of the amine A12 in which the phosphonate moiety is attached to the pyridine ring by means of a heteroatom and an alkylene chain. In this procedure, 2-bromo-4-hydroxymethylpyridine, the preparation of which is described in Chem. Pharm. Bull., 1990, 38, 2446, is subjected to a nucleophilic displacement reaction with a dialkyl hydroxy, thio or aminoalkyl-substituted alkyl phosphonate 66.2. The preparation of pyridine ethers, thioethers and amines by means of displacement reactions of 2-bromopyridines by alcohols, thiols and amines is described, for example, in Heterocyclic Compounds, Volume 3, R. A. Abramovitch, ed., Wiley, 1975, p. 597, 191, and 41 respectively. Equimolar amounts of the reactants are combined in a polar solvent such as dimethylformamide at ca 100° C. in the presence of a base such as potassium carbonate. The displacement product 66.3 is then converted into the activated derivative 66.4, in which Lv is a leaving group such as halo, methanesulfonyloxy, p-toluenesulfonyloxy and the like. The conversion of alcohols into chlorides and bromides is described, for example, in Comprehensive Organic Transformations, by R. C. Larock, VCH, 1989, p. 354ff and p. 356ff. For example, benzyl alcohols can be transformed into the chloro compounds, in which Ha is chloro, by reaction with triphenylphosphine and N-chlorosuccinimide, as described in J. Am. Chem. Soc., 106, 3286, 1984. Benzyl alcohols can be transformed into bromo compounds by reaction with carbon tetrabromide and triphenylphosphine, as described in J. Am. Chem. Soc., 92, 2139, 1970. Alcohols can be converted into sulfonate esters by treatment with the alkyl or aryl sulfonyl chloride and a base, in a solvent such as dichloromethane or pyridine. Preferably, the carbinol 66.3 is converted into the corresponding chloro compound, 66.4, in which Lv is Cl, as described above. The product is then reacted with the piperidinol derivative 66.5. The preparation of the compounds 66.5 is described in U.S. Pat. No. 5,614,533, and in J. Org. Chem., 1997, 62, 3440. The piperidinol derivative 66.5 is treated in dimethylformamide with a strong base such as sodium hydride, and the alkylating agent 66.4 is then added. The reaction proceeds to afford the ether product 66.6, and the BOC protecting group is then removed to yield the free amine compound 66.7. The removal of BOC protecting groups is described, for example, in Protective Groups in Organic Synthesis, by T. W. Greene and P. G. M Wuts, Wiley, Second Edition 1990, p. 328. The deprotection can be effected by treatment of the BOC compound with anhydrous acids, for example, hydrogen chloride or trifluoroacetic acid, or by reaction with trimethylsilyl iodide or aluminum chloride. Preferably, the BOC group is removed by treatment of the substrate 66.6 with hydrochloric acid, as described in J. Org. Chem., 1997, 62, 3440.

For example, 2-bromo-4-hydroxymethylpyridine 66.1 the preparation of which is described in Chem. Pharm. Bull., 1990, 38, 2446, is reacted in dimethylformamide solution at ca 80° C. with an equimolar amount of a dialkyl mercaptoethyl phosphonate 66.8, prepared as described in Zh. Obschei. Khim., 1973, 43, 2364, and potassium carbonate, to yield the thioether product 66.9. The product is then reacted with one molar equivalent of methanesulfonyl chloride in pyridine at 0° C., to produce the mesylate compound 66.10. This material is reacted with the piperidinol reagent 66.5, using the conditions described above, to afford the ether 66.11. The BOC protecting group is then removed as previously described, to afford the amine product 66.12.

Using the above procedures, but employing, in place of the mercaptoethyl phosphonate 66.8, different hydroxy, mercapto or alkylamino phosphonates 66.2, the corresponding products 66.7 are obtained.

Scheme 67 illustrates the preparation of phosphonate-containing analogs of the amine A12 in which the phosphonate moiety is directly attached to the pyridine ring. In this procedure, a bromo-substituted 4-hydroxymethylpyridine 67.1 is coupled, in the presence of a palladium catalyst, with a dialkyl phosphite 67.2. The reaction between aryl bromides and dialkyl phosphites to yield aryl phosphonates is described in Synthesis, 56, 1981, and in J. Med. Chem., 1992, 35, 1371. The reaction is conducted in an inert solvent such as toluene or xylene, at about 100° C., in the presence of a palladium(0) catalyst such as tetrakis(triphenylphosphine)palladium and a tertiary organic base such as triethylamine. The thus-obtained pyridylphosphonate 67.3 is then converted, as described above (Scheme 66) into an activated derivative 67.4, and the latter compound is transformed as described above into the amine 67.5.

For example, 3-bromo-4-hydroxymethylpyridine 67.5, prepared as described in Bioorg. Med. Chem. Lett., 1992, 2, 1619, is reacted with a dialkyl phosphite 67.2, as described above, to prepare the phosphonate 67.7. The product is then transformed into the chloro derivative by reaction with triphenylphosphine and N-chlorosuccinimide, and the product is converted, as described above (Scheme 66) into the amine 67.9.

Using the above procedures, but employing, in place of the 3-bromopyridine derivative 67.6, different bromopyridines 67.1, and/or different phosphites, the corresponding products 67.5 are obtained.

Scheme 68 illustrates the preparation of phosphonate-containing analogs of the amine A12 in which the phosphonate moiety is attached to the pyridine ring by means of an amine group and an alkyl chain. In this procedure, an amino-substituted 4-hydroxymethylpyridine 68.1 is subjected to a reductive amination reaction with a dialkyl formylalkyl phosphonate 68.2. The preparation of amines by means of reductive amination procedures is described, for example, in Comprehensive Organic Transformations, by R. C. Larock, VCH, p. 421, and in Advanced Organic Chemistry, Part B, by F. A. Carey and R. J. Sundberg, Plenum, 2001, p. 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The amine product 68.3 is then converted, as described above, into the piperidine derivative 68.5.

For example, 2-amino-4-hydroymethylpyridine 68.6, prepared as described in Aust. J. Chem., 1993, 46, 9897, is reacted in ethanol solution with a dialkyl formylmethylphosphonate 68.7, prepared as described in Zh. Obschei. Khim., 1987, 57, 2793, in the presence of sodium cyanoborohydride, to yield the amine product 68.8. This material is then transformed into the chloro derivative 68.9 by reaction with hydrogen chloride in ether. The chloro product is then transformed, as described above, into the piperidine derivative 68.10.

Using the above procedures, but employing, in place of the 2-aminopyridine derivative 68.6, different aminopyridines 68.1, and/or different formylalkyl phosphonates 68.2 the corresponding products 68.5 are obtained.

Scheme 69 illustrates the preparation of phosphonate-containing analogs of the amine A12 in which the phosphonate moiety is attached to the pyridine ring by means of a saturated or unsaturated alkyl chain. In this procedure, a bromo-substituted 4-hydroxymethylpyridine 69.1 is coupled, by means of a palladium-catalyzed Heck reaction, with a dialkyl alkenyl phosphonate 69.2. The coupling of aryl bromides and olefins is described above (Scheme 26). The product is then converted, as described above, into the piperidine derivative 69.5.

Optionally, the latter compound can be reduced, for example as described above in Scheme 26, to afford the saturated analog 69.6.

For example, 3-bromo-4-hydroxymethylpyridine 69.7, prepared as described in Bioorg. Med. Chem. Lett., 1992, 2, 1619, is coupled with a dialkyl vinylphosphonate 69.8, prepared as described in Synthesis, 1983, 556, to yield the olefinic product 69.9. The product is reacted with one molar equivalent of p-toluenesulfonyl chloride in pyridine at ambient temperature to afford the tosylate 69.10. The latter compound is then transformed, as previously described, into the piperidine derivative 69.11. Optionally, the latter compound is reduced, for example by reaction with diimide, to yield the saturated analog 69.12.

Using the above procedures, but employing, in place of the 3-bromopyridine derivative 69.7, different bromopyridines 69.1, and/or different alkenyl phosphonates 69.2 the corresponding products 69.5 and 69.6 are obtained.

Scheme 66

Method

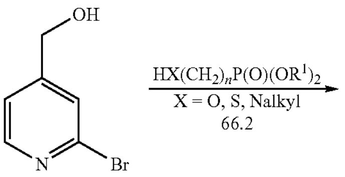

66.1

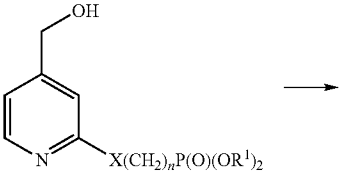

66.3

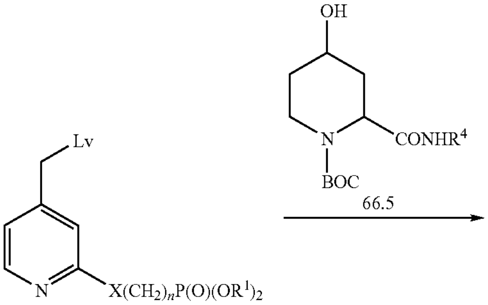

66.4

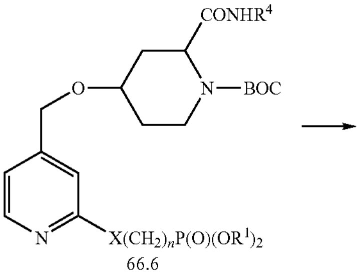

66.6

-continued

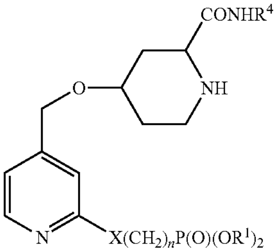

66.7

Example

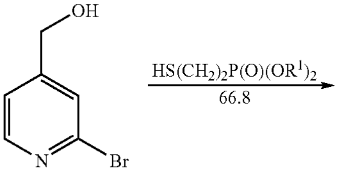

66.1

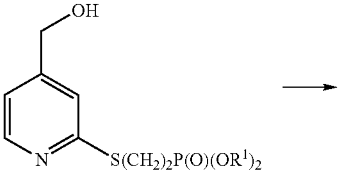

66.9

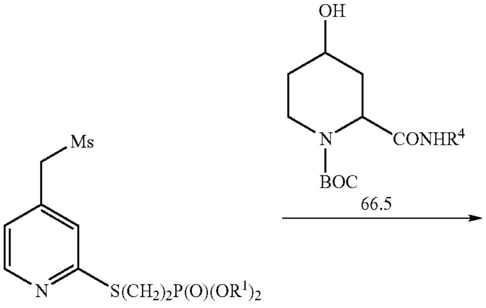

66.10

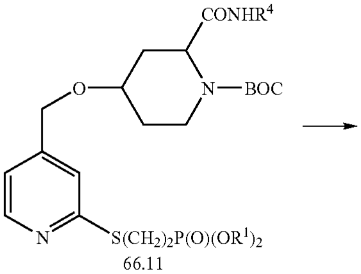

66.11

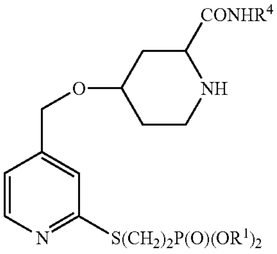

66.12

Scheme 67
Method
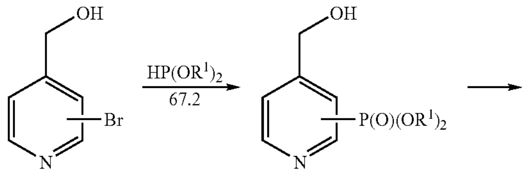
67.1 67.3
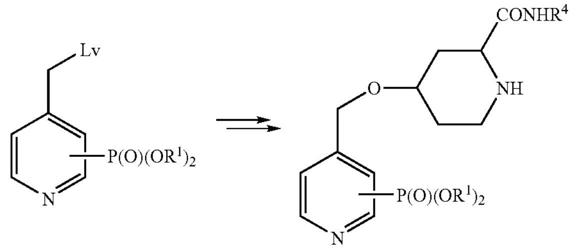
67.4 67.5
Example
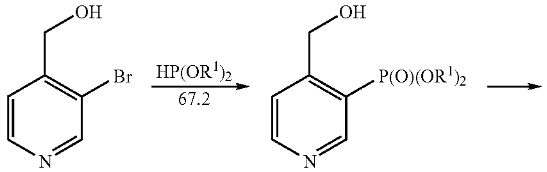
67.6 67.7
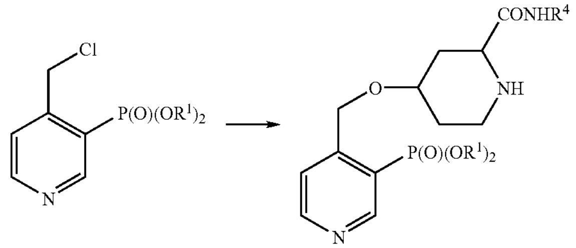
67.8 67.9
Scheme 68
Method
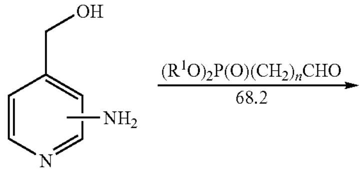
68.1
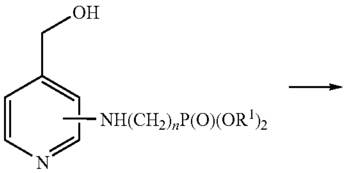
68.3
-continued
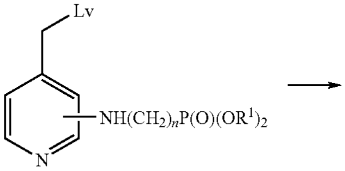
68.4
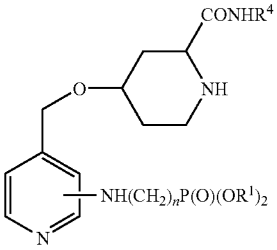
68.5
Example
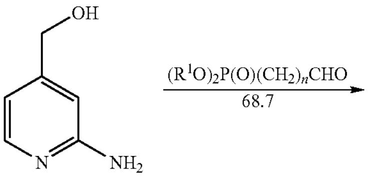
68.6
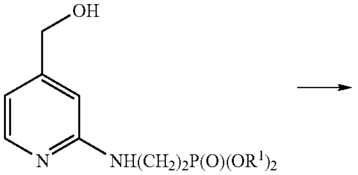
68.8
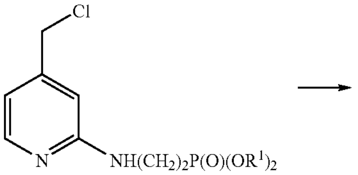
68.9
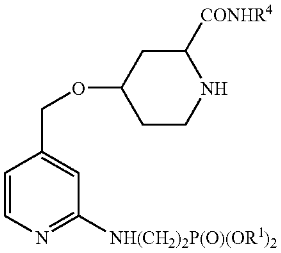
68.10

Scheme 69

Method

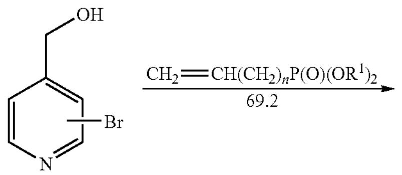

69.1

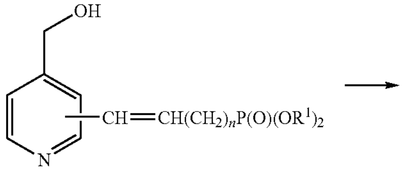

69.3

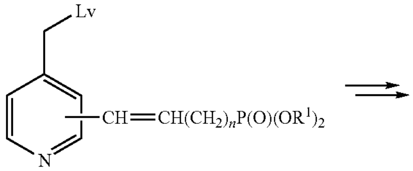

69.4

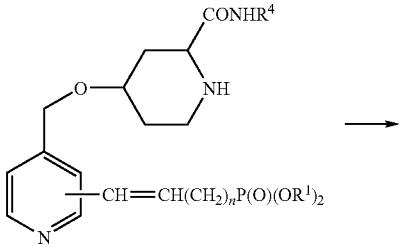

69.5

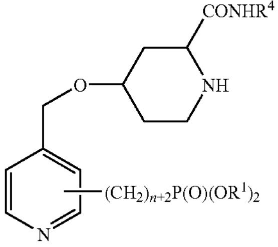

69.6

Example

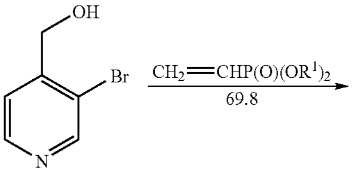

69.7

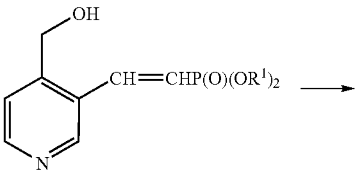

69.9

-continued

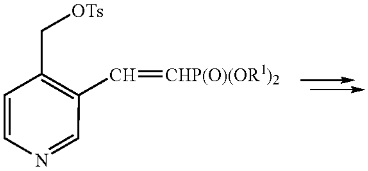

69.10

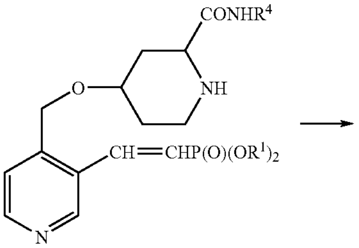

69.11

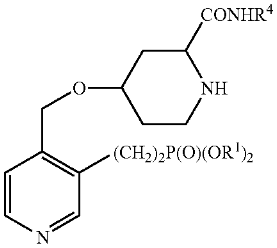

69.12

General Applicability of Methods for Introduction of Phosphonate Substituents.

The procedures described herein for the introduction of phosphonate moieties are, with appropriate modifications, transferable to different chemical substrates. For example, the methods described above for the introduction of phosphonate groups into the quinoline-2carboxylic moiety (Schemes 24-27), can, with appropriate modifications known to those skilled in the art, be applied to the introduction of phosphonate groups into the phenylalanine, thiophenol, tert-butylamine and decahydroisoquinoline moieties. Similarly, the methods described above for the introduction of phosphonate groups into the phenylalanine moiety (Schemes 28-34), the thiophenol moiety (Schemes 35-44) the tert-butylamine moiety (Schemes 45-48), decahydroisoquinoline moiety (Schemes 48a-52), dimethylphenoxyacetic acids (Schemes 56-61), benzyl carbamates (Schemes 62-65) and pyridines (Schemes 66-69) can, with appropriate modifications known to those skilled in the art, be applied to the introduction of phosphonate groups into the quinoline-2-carboxylic acid component.

Preparation of (Pyridin-3-yloxy)-acetic Acids Incorporating Phosphonate Moieties.

Scheme 70 illustrates two alternative methods by means of which (pyridin-3-yloxy)-acetic acids bearing phosphonate moieties may be prepared. The phosphonate group may be introduced into the pyridyl moiety, followed by attachment of the acetic acid group, or the phosphonate group may be introduced into a preformed (Pyridin-3-yloxy)-acetic acid intermediate. In the first sequence, a substituted 3-hydroxypyridine 70.1, in which the substituent B is a precursor to the group link-$P(O)(OR^1)_2$, and in which the aryl hydroxyl may or may not be protected, depending on the reactions to be performed, is converted into a phosphonate-containing compound 70.2. Methods for the conversion of the substituent B into the group link-$P(O)(OR^1)_2$ are described in Schemes 25-75.

The protected aryl hydroxyl group present in the phosphonate-containing product 70.2 is then deprotected, using methods described below, to afford the phenol 70.3.

The product 70.3 is then transformed into the corresponding (pyridin-3-yloxy)acetic acid 70.4, in a two step procedure. In the first step, the phenol 70.3 is reacted with an ester of bromoacetic acid 70.9, in which R is an alkyl group or a protecting group. Methods for the protection of carboxylic acids are described in Protective Groups in Organic Synthesis, by T. W. Greene and P. G. M Wuts, Wiley, Second Edition 1990, p. 224ff. The alkylation of aryl hydroxyl groups to afford aryl ethers is described, for example, in Comprehensive Organic Transformations, by R. C. Larock, VCH, 1989, p. 446ff. Typically, the aryl reagent and the alkylating agent are reacted together in the presence of an organic or inorganic base, such as, for example, diazabicyclononene, (DBN) or potassium carbonate, in a polar organic solvent such as, for example, dimethylformamide or acetonitrile.

Preferably, equimolar amounts of the phenol 70.3 and ethyl bromoacetate are reacted together in the presence of cesium carbonate, in dioxan at reflux temperature, for example as described in U.S. Pat. No. 5,914,332, to afford the ester 70.4.

The thus-obtained ester 70.4 is then hydrolyzed to afford the carboxylic acid 70.5. The methods used for this reaction depend on the nature of the group R. If R is an alkyl group such as methyl, hydrolysis can be effected by treatment of the ester with aqueous or aqueous alcoholic base, or by use of an esterase enzyme such as porcine liver esterase. If R is a protecting group, methods for hydrolysis are described in Protective Groups in Organic Synthesis, by T. W. Greene and P. G. M Wuts, Wiley, Second Edition 1990, p. 224ff. Preferably, the ester product 70.4 which R is ethyl is hydrolyzed to the carboxylic acid 70.5 by reaction with lithium hydroxide in aqueous methanol at ambient temperature, as described in U.S. Pat. No. 5,914,332.

Alternatively, an appropriately substituted 3-hydroxypyridine 70.6, in which the substituent B is a precursor to the group link-$P(O)(OR^1)_2$, is transformed into the corresponding acetic acid ester 70.7. The conditions employed for the alkylation reaction are similar to those described above for the conversion of the phenol 70.3 into the ester 70.4.

The acetic acid ester 70.7 is then converted into the carboxylic acid 70.5 using the 2 step procedure shown above, involving transformation of the group B into the group link-$P(O)(OR^1)_2$ followed by ester hydrolysis of the acetic acid ester. The group B which is present in the ester 70.7 may be transformed into the group link-$P(O)(OR^1)_2$ either before or after hydrolysis of the ester moiety into the carboxylic acid group, depending on the nature of the chemical transformations required.

Schemes 70-75 illustrate the preparation of (Pyridin-3-yloxy)-acetic acids incorporating phosphonate ester groups. The procedures shown can also be applied to the preparation of acetic esters acids 70.7, with, if appropriate, modifications made according to the knowledge of one skilled in the art.

Scheme 71 depicts the preparation of (pyridin-3-yloxy) acetic acids incorporating a phosphonate group linked to the pyridyl ring by means of a saturated or unsaturated alkylene chain. In this procedure, an optionally protected halo-substituted 3-hydroxypyridine 71.1 is coupled, by means of a palladium-catalyzed Heck reaction, with a dialkyl alkenyl phosphonate 71.2. The coupling of aryl bromides with olefins by means of the Heck reaction is described, for example, in Advanced Organic Chemistry, by F. A. Carey and R. J. Sundberg, Plenum, 2001, p. 503. The aryl halide and the olefin are coupled in a polar solvent such as dimethylformamide or dioxan, in the presence of a palladium(0) or palladium (2) catalyst. Following the coupling reaction, the product 71.3 is converted, using the procedures described above, (Scheme 70) into the corresponding (pyridin-3-yloxy)acetic acid 71.4. Alternatively, the olefinic product 71.3 is reduced to afford the saturated derivative 71.5. Methods for the reduction of carbon-carbon double bonds are described, for example, in Comprehensive Organic Transformations, by R. C. Larock, VCH, 1989, p. 6. The methods include catalytic reduction, or chemical reduction employing, for example, diborane or diimide. Following the reduction reaction, the product 71.5 is converted, as described above, (Scheme 70) into the corresponding (pyridin-3-yloxy)acetic acid 71.6.

For example, 2-iodo-5-hydroxy pyridine 71.7, prepared as described in J. Org. Chem., 1990, 55, 18, p. 5287, is converted into the tert-butyldimethylsilyl ether 71.8, by reaction with chloro-tert-butyldimethylsilane, and a base such as imidazole, as described in Protective Groups in Organic Synthesis, by T. W. Greene and P. G. M Wuts, Wiley, Second Edition 1990 p. 77. The product 71.8 is reacted with an equimolar amount of a dialkyl allyl phosphonate 71.9, for example diethyl allylphosphonate (Aldrich) in the presence of ca. 3 mol % of bis(triphenylphosphine)palladium(II) chloride, in dimethylformamide at ca. 60° C., to produce the coupled product 71.10. Alternatively see J. Med. Chem. 1999, 42, 4, p. 669 for alternative conditions for this reaction. The silyl group is removed, for example by the treatment of the ether 71.10 with a solution of tetrabutylammonium fluoride in tetrahydrofuran, as described in J. Am. Chem., Soc., 94, 6190, 1972, to afford the phenol 71.11. This compound is converted, employing the procedures described above, (Scheme 70) into the corresponding (pyridin-3yloxy) acetic acid 71.12. Alternatively, the unsaturated compound 71.11 is reduced, for example by catalytic hydrogenation employing 5% palladium on carbon as catalyst, in an alcoholic solvent such as methanol, as described, for example, in Hydrogenation Methods, by R. N. Rylander, Academic Press, 1985, Ch. 2, to afford the saturated analog 71.13. This compound is converted, employing the procedures described above, (Scheme 70) into the corresponding (pyridin-3-yloxy)acetic acid 71.14.

Using the above procedures, but employing, in place of 2-iodo-5-hydroxy pyridine 71.7, different iodo or bromohydroxypyridines 71.1, and/or different dialkyl alkenyl phosphonates 71.2, the corresponding products 71.4 and 71.6 are obtained.

In this and succeeding examples, the nature of the phosphonate ester group can be varied, either before or after incorporation into the scaffold, by means of chemical transformations. The transformations, and the methods by which they are accomplished, are described above (Scheme 54).

Scheme 72 illustrates the preparation of phosphonate-containing analogs of (pyridin-3-yloxy) acetic acids in which the phosphonate moiety is attached to the pyridine ring by means of a heteroatom and an alkyl chain. In this procedure, a suitably protected 2-halo-5-hydroxypyridine, (see Scheme 71) is subjected to a nucleophilic displacement reaction with a dialkyl hydroxy, thio or aminoalkyl-substituted alkyl phosphonate 72.2. The preparation of pyridine ethers, thioethers and amines by means of displacement reactions of 2bromopyridines, by alcohols, thiols and amines is described, for example, in Heterocyclic Compounds, Volume 3, R. A. Abramovitch, ed., Wiley, 1975, p. 597, 191, and 41 respectively. Equimolar amounts of the reactants are combined in a polar solvent such as dimethylformamide at ca 100° C. in the presence of a base such as potassium carbonate. The displacement product 72.3 is then converted into the hydroxyl derivative 72.4 and then into the (pyridin-3-yloxy)acetic acid phosphonate ester 72.5 using the procedures described above (Scheme 70).

For example, 2-iodo-5-hydroxypyridine 71.7 (Scheme 71) is treated with benzyl bromide in the presence of base such as potassium carbonate as described in Protective Groups in Organic Synthesis, by T. W. Greene and P. G. M Wuts, Wiley, Third Edition 1999, p. 266 to give 72.6. The benzyl ether 72.6 is reacted in dimethylformamide solution at ca 80° C. with an equimolar amount of a dialkyl mercaptoethyl phosphonate 72.7, prepared as described in Zh. Obschei. Khim., 1973, 43, 2364, and potassium carbonate, to yield the thioether product 72.8. The benzyl group is then removed by catalytic hydrogenation employing 5% palladium on carbon as catalyst, in an alcoholic solvent such as methanol, as described, for example, in Protective Groups in Organic Synthesis, by T. W. Greene and P. G. M Wuts, Wiley, Third Edition 1999 p. 266ff., to afford the hydroxyl compound 72.9. The product 72.9 is then converted into the (pyridin-3-yloxy)acetic acid phosphonate ester 72.10 using the procedures described above (Scheme 70).

Using the above procedures, but employing, in place of the mercaptoethyl phosphonate 72.7, different hydroxy, mercapto or alkylamino phosphonates 72.2, and/or in place of the pyridine 71.7 different halo pyridines 71.1, the corresponding products 72.5 are obtained.

Scheme 73 illustrates the preparation of phosphonate-containing analogs of (pyridin-3-yloxy) acetic acids in which the phosphonate moiety is directly attached to the pyridine ring. In this procedure, a suitably protected 2-bromo-5-hydroxypyridine 73.1 is coupled, in the presence of a palladium catalyst, with a dialkyl phosphite 73.2. The reaction between aryl bromides and dialkyl phosphites to yield aryl phosphonates is described in Synthesis, 70, 1981, and in J. Med. Chem., 1992, 35, 1371. The reaction is conducted in an inert solvent such as toluene or xylene, at about 100° C., in the presence of a palladium(0) catalyst such as tetrakis(triphenylphosphine) palladium and a tertiary organic base such as triethylamine. The thus-obtained pyridylphosphonate 73.3 is then converted, as described above (Scheme 72) into the (pyridin-3-yloxy)acetic acid phosphonate ester 73.5.

For example, 3-bromo-5-hydroxypyridine 73.6 (Synchem-OHG) is treated with benzyl bromide in the presence of base such as potassium carbonate as described in Protective Groups in Organic Synthesis, by T. W. Greene and P. G. M Wuts, Wiley, Third Edition 1999, p. 266 to give 73.7. The product 73.7 is then treated with a dialkylphosphite 73.2 as described above to give the phosphonate 73.8. Employing the conditions described above (Scheme 72) 73.8 is converted in several steps to the (pyridin-3-yloxy)acetic acid phosphonate ester 73.10. Using the above procedures, but employing, in place of the 3-bromopyridine derivative 73.6, different bromopyridines 73.1, and/or different phosphites, the corresponding products 73.5 are obtained.

Scheme 74 illustrates the preparation of (pyridin-3-yloxy) acetic acids incorporating a phosphonate group attached to the pyridyl ring by means of a heteroatom and an alkylene chain. The compounds are obtained by means of alkylation reactions in which an hydroxy, thio or amino-substituted 3-hydroxy pyridine 74.1, protected at the 3-hydroxyl position is reacted, in the presence of a base such as, for example, potassium carbonate, and optionally in the presence of a catalytic amount of an iodide such as potassium iodide, with a dialkyl bromoalkyl phosphonate 74.6. The reaction is conducted in a polar organic solvent such as dimethylformamide or acetonitrile at from ambient temperature to about 80° C. The product of the alkylation reaction, 74.2 is then converted, as described above for converting 72.3 to 72.5 (Scheme 72) into the acid 74.5.

Alternatively, the protected pyridine 74.7 is converted to the acetic acid ester derivative 74.8 using the procedures described above in Scheme 70. The acetic acid ester 74.8, is then deprotected following the procedures described in Protective Groups in Organic Synthesis, by T. W. Greene and P. G. M Wuts, Wiley, Third Edition 1999, ch 3,6, and 7, and the product treated with a dialkyl bromoalkyl phosphonate 74.6 to give 74.4. The ester 74.4 is converted to the acid 74.5 using the procedures described above (Scheme 70).

For example, 3-benzyloxy, 5-hydroxy pyridine 74.10, prepared as described Bioorg and Med. Chem. Lett. 1998, p. 2797, is converted to the ester 74.11 by treatment with ethylbromoacetate as described above (Scheme 70). The benzyl group is removed, for example by catalytic hydrogenation employing 5% palladium on carbon as catalyst, in an alcoholic solvent such as methanol, as described, for example, in Hydrogenation Methods, by R. N. Rylander, Academic Press, 1985, Ch. 2, to afford the hydroxy pyridine 74.12. The product 74.12 is reacted in dimethylformamide at ca. 60° C. with an equimolar amount of a dialkyl bromobutyl phosphonate 74.14, the preparation of which is described in Synthesis, 1994, 9, 909, in the presence of ca. 5 molar equivalents of potassium carbonate, to afford the phosphonate ether product 74.13. This compound is converted, employing the procedures described above, (Scheme 70) into the corresponding acid 74.15.

Using the above procedures, but employing, in place of the pyridine 74.10, different hydroxy, thio or aminophenols 74.1, and/or different dialkyl bromoalkyl phosphonates 74.6, the corresponding products 74.5 are obtained.

Scheme 75 illustrates the preparation of (Pyridin-3-yloxy)-acetic acids incorporating a phosphonate ester which is attached to the pyridyl group by means of a carbon chain incorporating a nitrogen atom. The compounds 75.4 are obtained by means of a reductive alkylation reaction between hydroxyl protected 3-hydroxypyridyl aldehyde 75.1 and an aminoalkyl phosphonate ester 75.2. The preparation of amines by means of reductive amination procedures is described, for example, in Comprehensive Organic Transformations, by R. C. Larock, VCH, p. 421. In this procedure, the amine component 75.2 and the aldehyde component 75.1 are reacted together in the presence of a reducing agent such as, for example, borane, sodium cyanoborohydride or diisobutylaluminum hydride, to yield the amine product 75.3. The amination product 75.3 is then deprotected according to procedures described in Protective Groups in Organic Synthesis, by T. W. Greene and P. G. M Wuts, Wiley, Third Edition 1999, ch3, and subsequently converted into the (pyridin-3-yloxy) acetic acid compound 75.4, using the alkylation and ester hydrolysis procedures described above (Scheme 70).

For example, the ester 75.5 (TCI-US) is reacted with benzyl bromide in the presence of base such as potassium carbonate as described in Protective Groups in Organic Synthesis, by T. W. Greene and P. G. M Wuts, Wiley, Third Edition 1999, p. 266 to give 75.6. The benzyl ether 75.6 is then converted to the aldehyde 75.7 by reaction with DIBAL (see Comprehensive Organic Transformations, by R. C. Larock, $2^{nd}$ Edition, 1999, p. 1267. for examples). Equimolar amounts of aldehyde 75.7, and a dialkyl amino ethyl phosphonate 75.8, the preparation of which is described in J. Org. Chem., 2000, 65, 676, are reacted together in the presence of sodium cyanoborohydride and acetic acid, as described, for example, in J. Amer. Chem. Soc., 91, 3996, 1969, to afford the amine product 75.9. The benzyl group is then removed by catalytic hydrogenation employing 5% palladium on carbon as catalyst, in an alcoholic solvent such as methanol, as described, for example, in Hydrogenation Methods, by R. N. Rylander, Academic Press, 1985, Ch. 2, to afford the hydroxyl compound 75.10. The product 75.10 is then converted into the acetic acid 75.11, as described above (Scheme 70). Using the above procedures, but employing, in place of the aldehyde 75.7, different aldehydes 75.1, and/or different aminoalkyl phosphonates 75.2, the corresponding products 75.4 are obtained.

Scheme 70

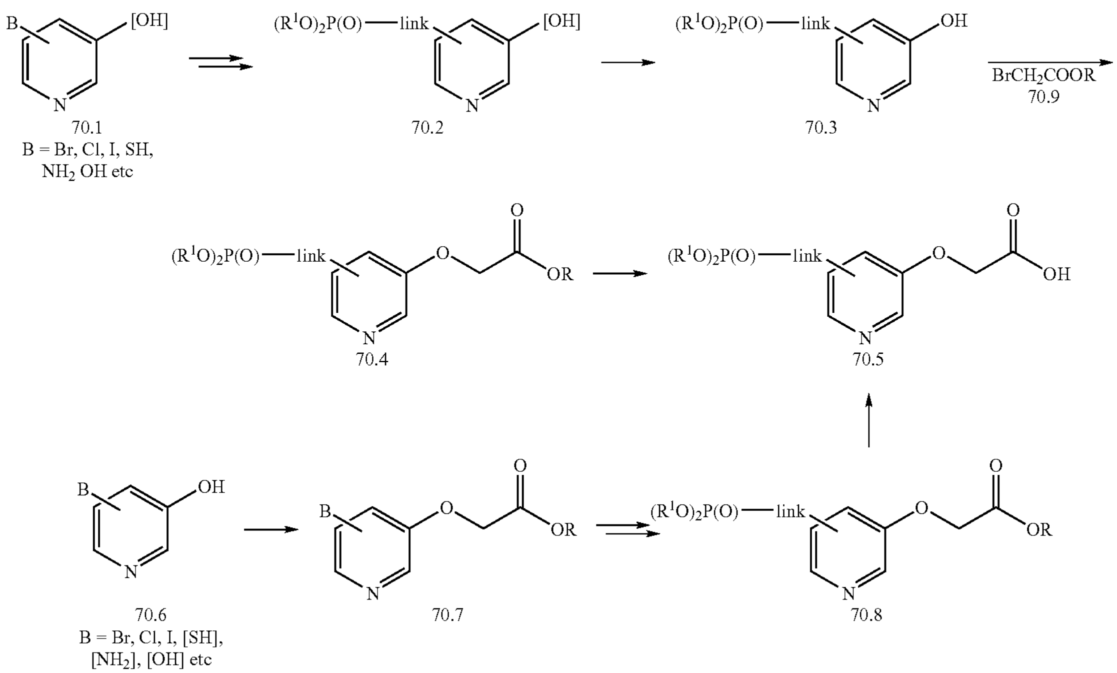

Scheme 71

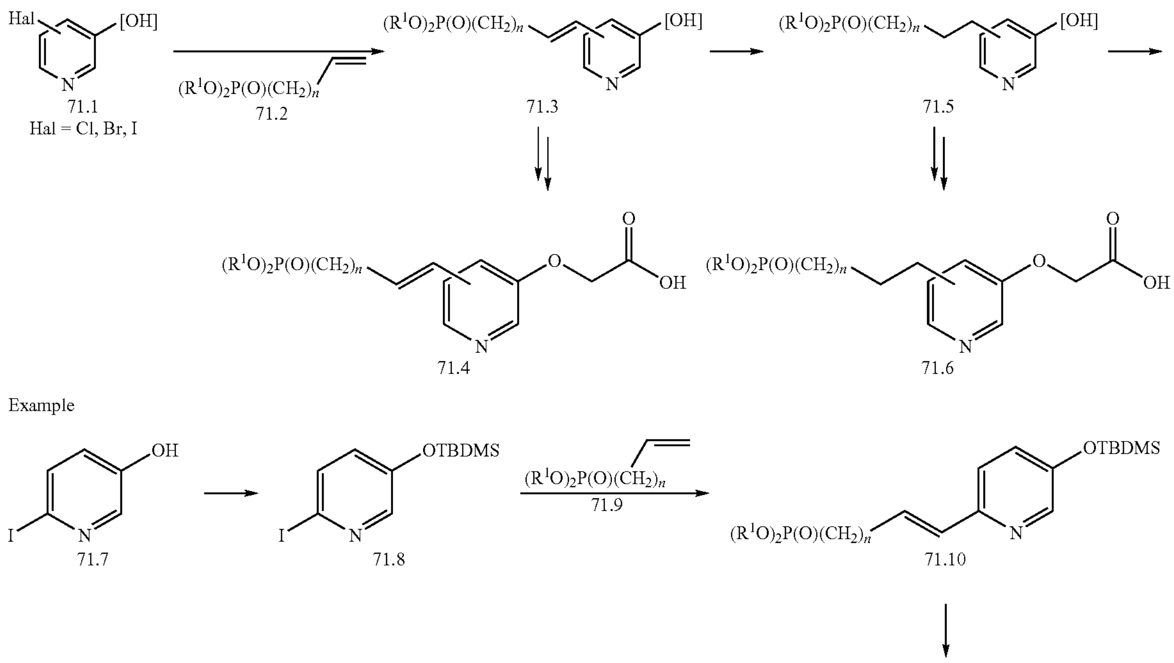

-continued
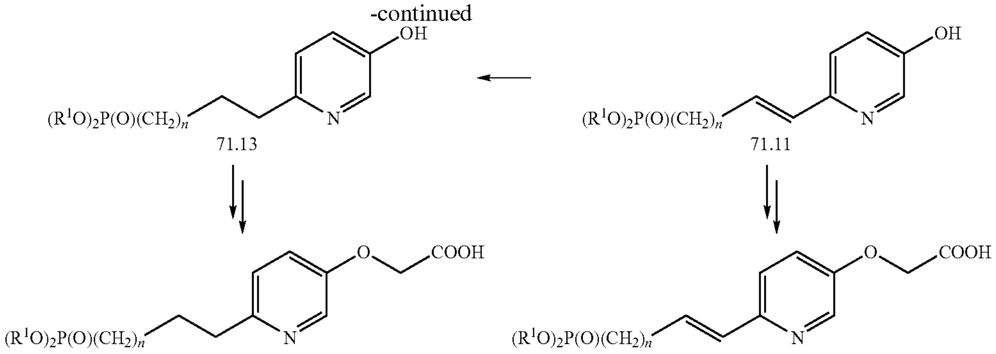
71.13 71.11 71.14 71.12
Scheme 72
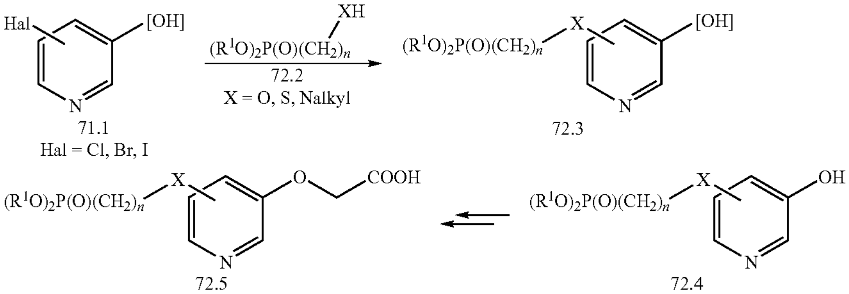
71.1
Hal = Cl, Br, I
72.3 72.5 72.4
Example
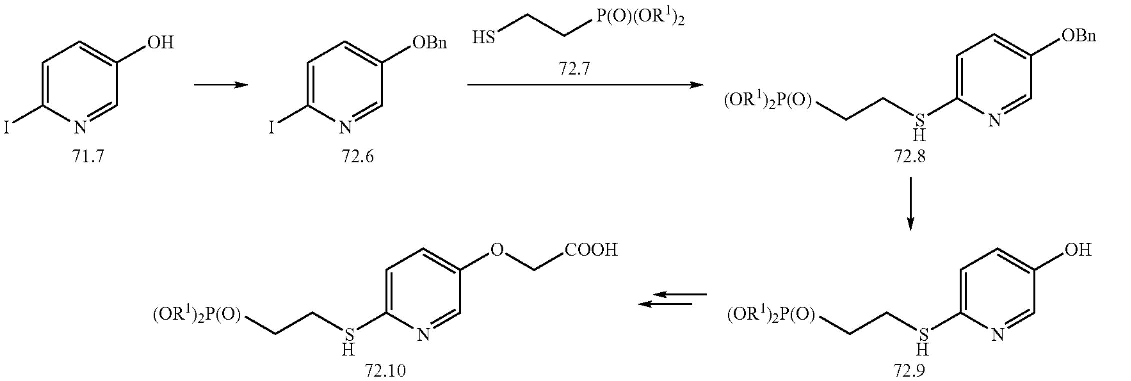
71.7 72.6 72.8 72.10 72.9
Scheme 73
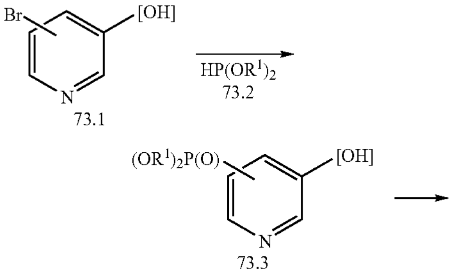
73.1 73.3
-continued
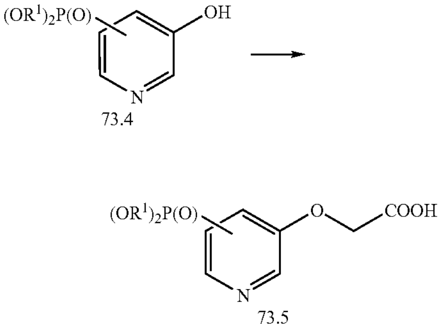
73.4 73.5

-continued
Example
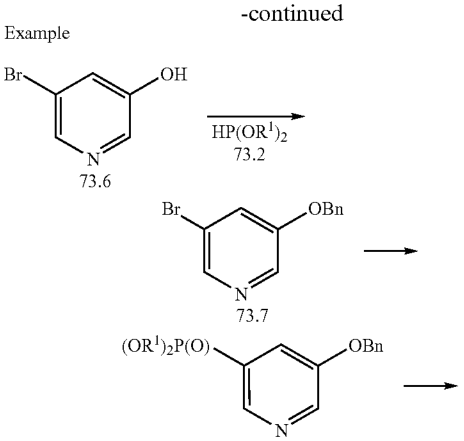
73.6
73.7
73.8
-continued
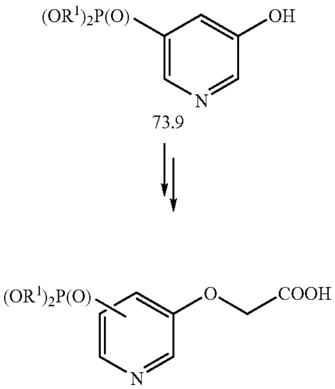
73.9
73.10
Scheme 74
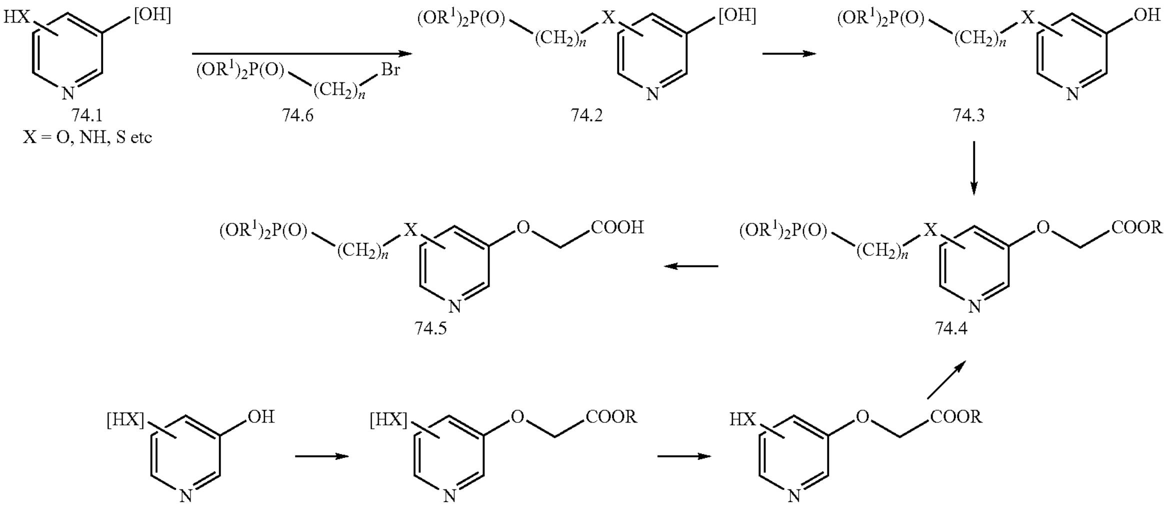
74.1
74.2
74.3
74.4
74.5
74.7
74.8
74.9
Example
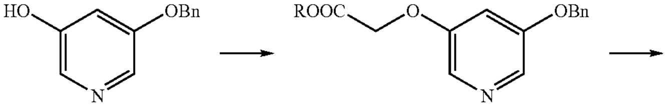
74.10
74.11
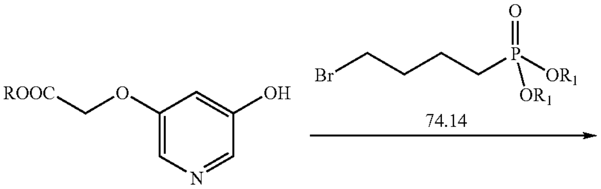
74.12
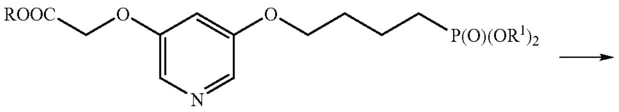
74.13

-continued

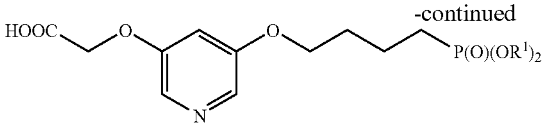

74.15

Scheme 75

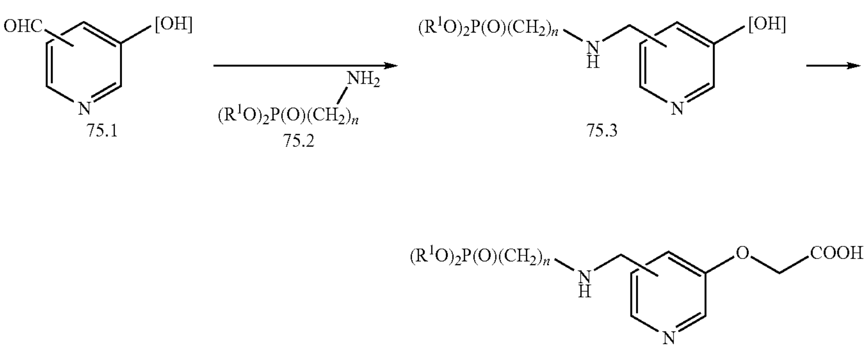

75.1 75.2 75.3 75.4

Example

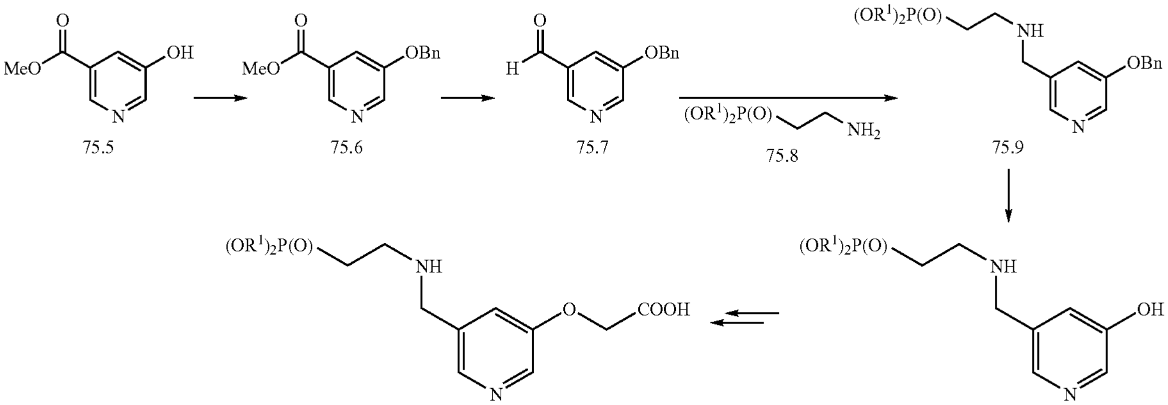

75.5 75.6 75.7 75.8 75.9 75.10 75.11

Ritonavir-like Phosphonate Protease Inhibitors (RLPPI)

Chemistry for Ritonavir Analogs.

Preparation of the Intermediate Phosphonate Esters.

The structures of the intermediate phosphonate esters 1 to 7, and the structures for the component groups $R^1$ of this invention are shown in Chart 1. The structures of the components $R^2COOH$, $R^3COOH$ and $R^4$ are shown in Charts 2a, 2b and 2c. Specific stereoisomers of some of the structures are shown in Charts 1 and 2; however, all stereoisomers are utilized in the syntheses of the compounds 1 to 7. Subsequent chemical modifications to the compounds 1 to 7, as described herein, permit the synthesis of the final compounds of this invention.

The intermediate compounds 1 to 7 incorporate a phosphonate moiety connected to the nucleus by means of a variable linking group, designated as "link" in the attached structures. Charts 3 and 4 illustrate examples of the linking groups present in the structures 1-7, and in which "etc" refers to the scaffold, e.g., ritonavir.

Schemes 1-28 illustrate the syntheses of the intermediate phosphonate compounds of this invention, 1-5, and of the intermediate compounds necessary for their synthesis. The preparation of the compounds 6 and 7, in which the phosphonate moiety is attached to the $R^2COOH$ or $R^3COOH$ group, is also described below.

CHART 1
Structures of the intermediate phosphonate esters 1-7
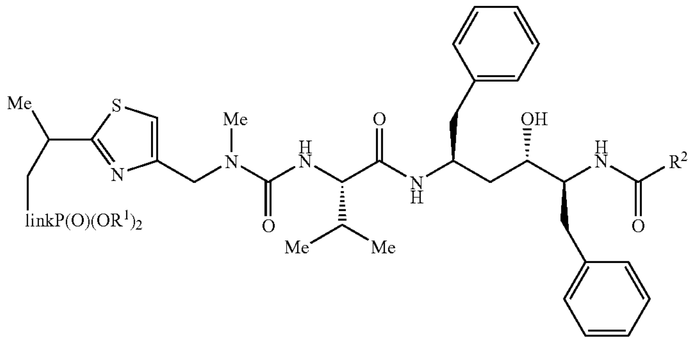
1
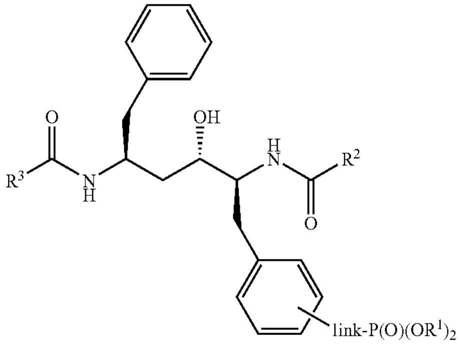
2
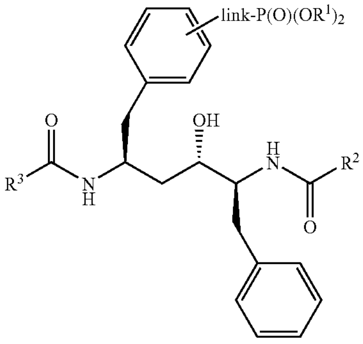
3
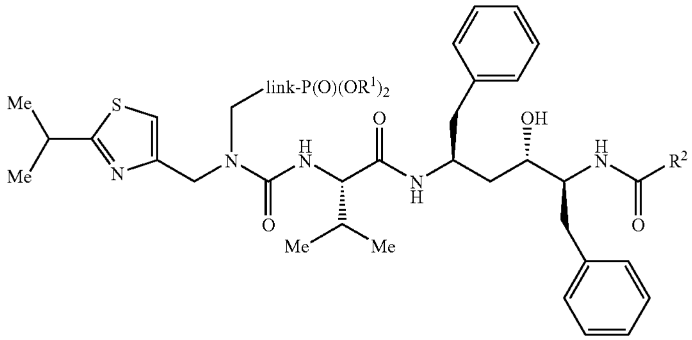
4

CHART 1-continued
Structures of the intermediate phosphonate esters 1-7
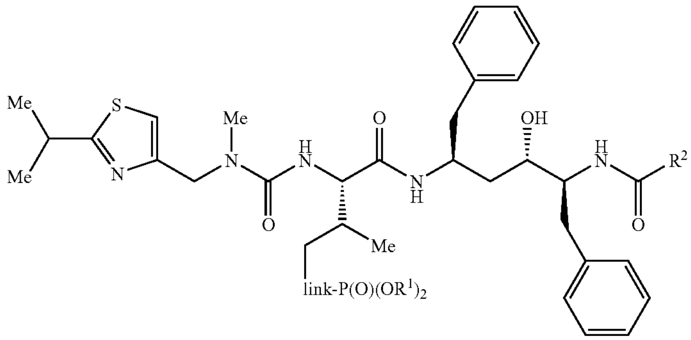
5
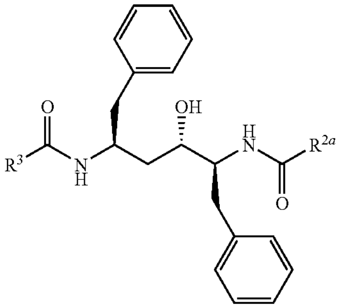
6
$R^{2a}$ = phosphonate-containing $R^2$ group
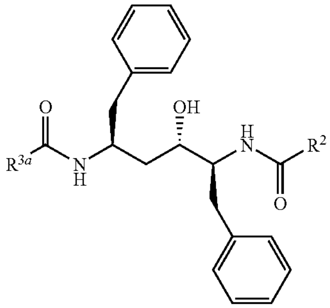
7
$R^{3a}$ = phosphonate-containing $R^3$ group
$R^1$ = H, alkyl, alkenyl, aralkyl, aryl.
CHART 2a
Structures of the $R^2COOH$ and $R^3COOH$ components
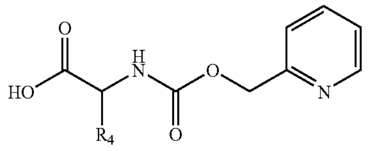
8
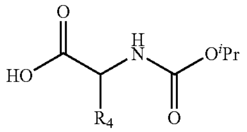
9
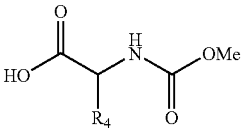
10
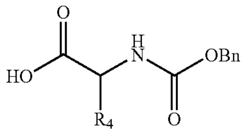
11
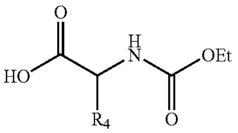
12
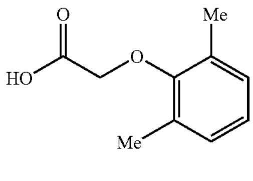
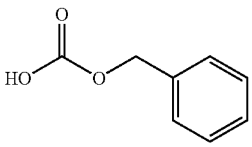
CHART 2a-continued
Structures of the $R^2COOH$ and $R^3COOH$ components
13
14
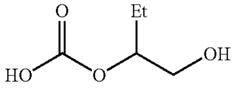
15
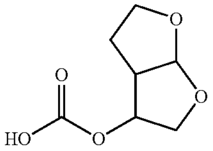
16
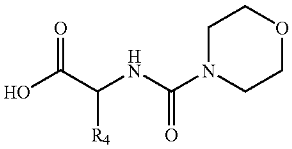
17
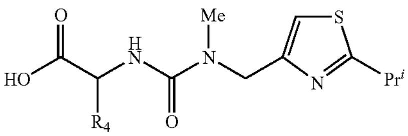
18

CHART 2a-continued
Structures of the $R^2COOH$ and $R^3COOH$ components
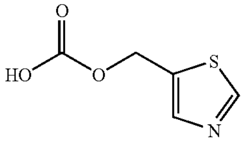
19
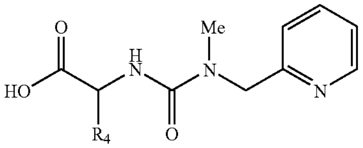
20
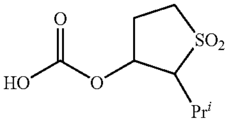
21
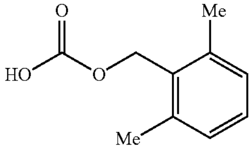
22
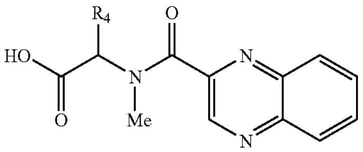
23
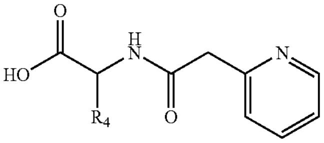
24
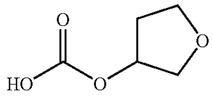
25
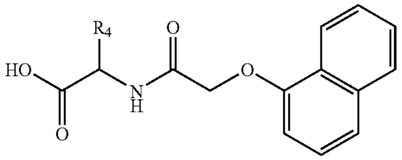
26
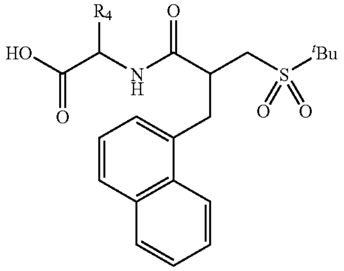
27
CHART 2a-continued
Structures of the $R^2COOH$ and $R^3COOH$ components
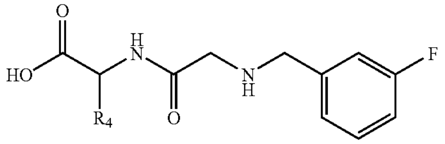
28
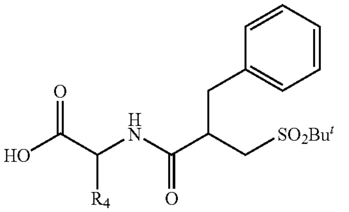
29
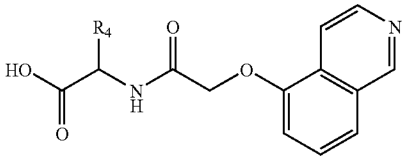
30
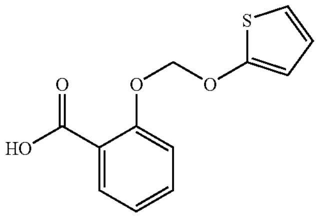
31
$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 2b
Structures of the $R^2COOH$ and $R^3COOH$ components
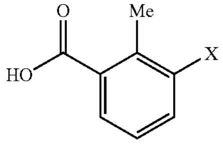
32
X = OH, $NH_2$
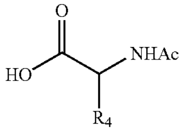
33
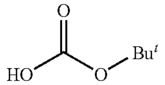
34
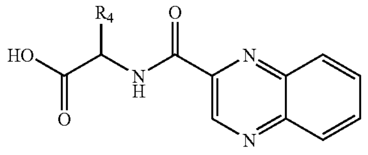
35

CHART 2b-continued
Structures of the $R^2COOH$ and $R^3COOH$ components
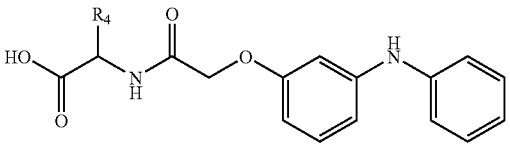
36
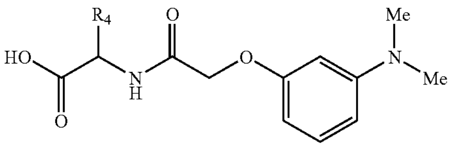
37
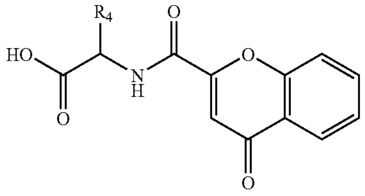
38
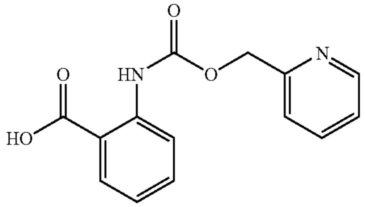
39
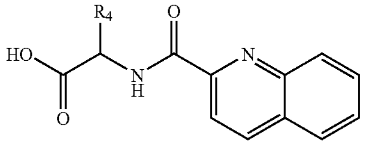
40
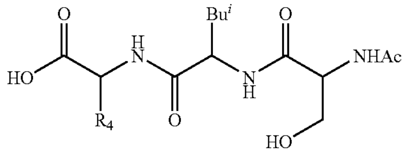
41
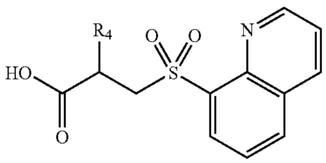
42
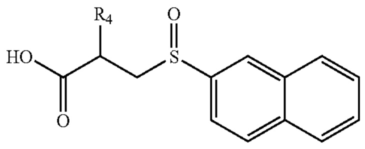
43
CHART 2b-continued
Structures of the $R^2COOH$ and $R^3COOH$ components
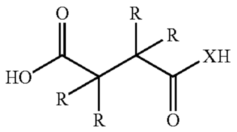
44
X = O, NH
R = H, alkyl
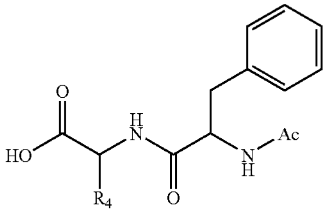
45
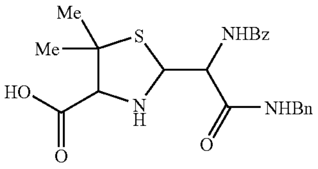
46
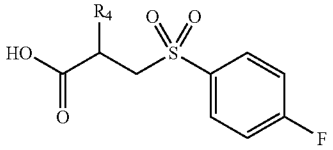
47
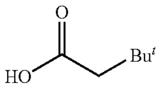
48
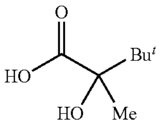
49
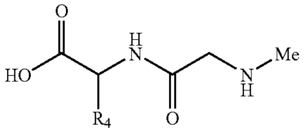
50
$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 2c
Structures of the $R^2COOH$ and $R^3COOH$ components
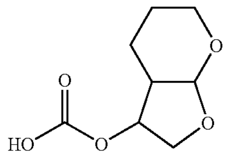
51
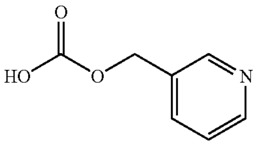
52

CHART 2c-continued

| Structures of the $R^2COOH$ and $R^3COOH$ components |
|---|
| 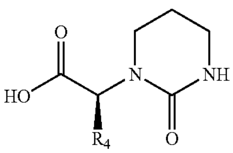<br>53 |
| 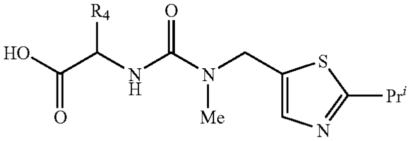<br>54 |

$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$

CHART 3

Examples of the linking group between the scaffold and the phosphonate moiety.

| link | examples |
|---|---|
| direct bond | 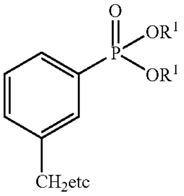<br>63 |
| | 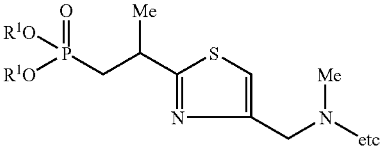<br>64 |
| | 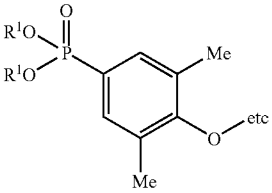<br>65 |
| | 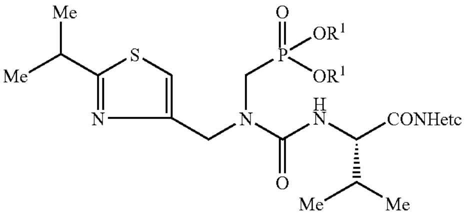<br>66 |

CHART 3-continued

Examples of the linking group between the scaffold and the phosphonate moiety.

| link | examples |
|---|---|
| | 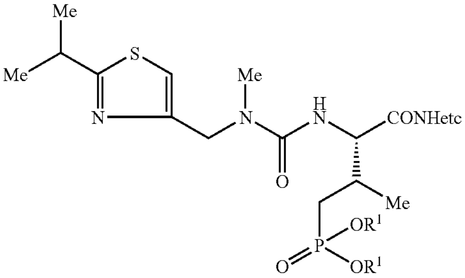<br>67 |
| single carbon | 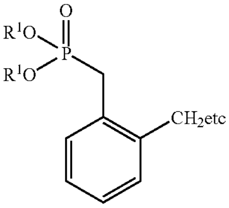<br>68 |
| | 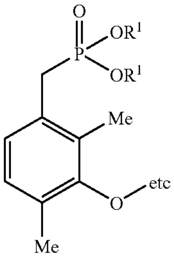<br>69 |
| | 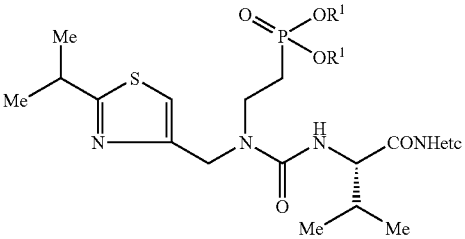<br>70 |
| multiple carbon | 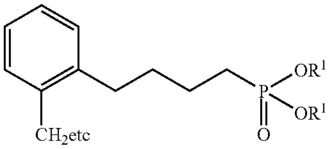<br>71 |
| | 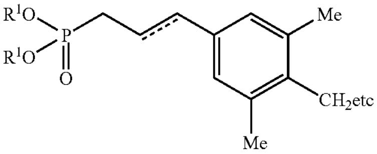<br>72 |

CHART 3-continued

Examples of the linking group between the scaffold and the phosphonate moiety.

| link | examples |
| --- | --- |
| | 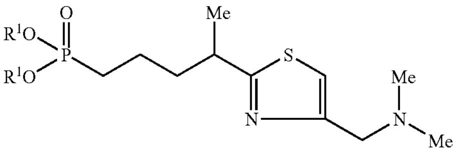 73 |
| hetero atoms | 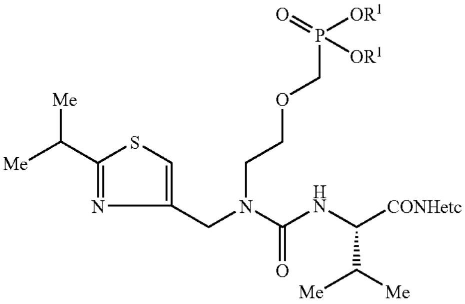 74 |
| | 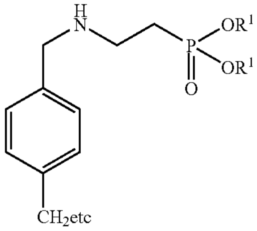 75 |
| | 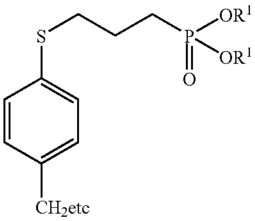 76 |

CHART 4

Examples of the linking group between the scaffold and the phosphonate moiety.

| link | examples |
| --- | --- |
| aryl, heteroaryl | 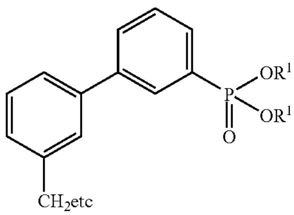 77 |

CHART 4-continued

Examples of the linking group between the scaffold and the phosphonate moiety.

| link | examples |
| --- | --- |
| | 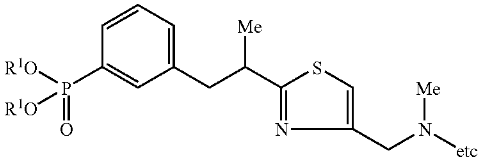 78 |
| | 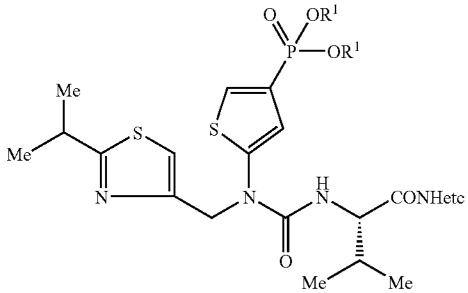 79 |
| cycloalkyl | 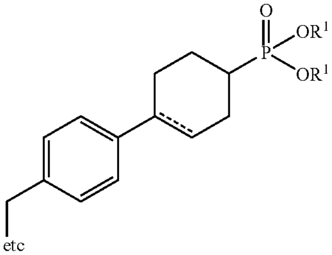 80 |
| | 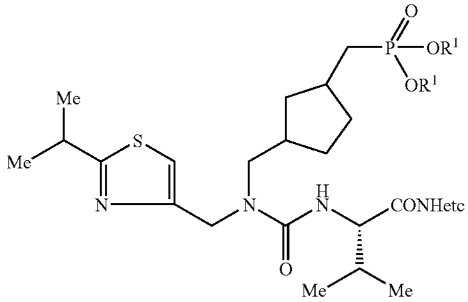 81 |
| cyclized | 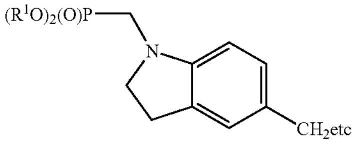 82 |

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W.

Greene and P. G. M Wuts, Wiley, Second Edition 1990. Reactive substituents which may be protected are shown in the accompanying schemes as, for example, [OH], [SH].

Preparation of the Phosphonate Intermediates 1.

Two methods for the preparation of the phosphonate intermediate compounds 1, in which the phosphonate moiety is attached to the isopropyl group of the carboxylic acid reactant 1.5, are shown in Schemes 1 and 2. The selection of the route to be employed for a given compound is made after consideration of the substituents which are present, and their stability under the reaction conditions required.

As shown in Scheme 1,5-amino-2-dibenzylamino-1,6-diphenyl-hexan-3-ol, 1.1, the preparation of which is described in Org. Process Res. Dev., 1994, 3, 94, is reacted with a carboxylic acid $R^2COOH$ 1.2, or an activated derivative thereof, to produce the amide 1.3. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of hydroxybenztriazole, in a non-protic solvent such as, for example, pyridine, dimethylformamide or dichloromethane, to afford the amide.

Alternatively, the carboxylic acid may first be converted into an activated derivative such as the acid chloride, anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane.

Preferably, the carboxylic acid 1.2 is converted into the acid chloride, and the latter compound is reacted with an equimolar amount of the amine 1.1, in an aprotic solvent such as, for example, tetrahydrofuran, at ambient temperature. The reaction is conducted in the presence of an organic base such as triethylamine, so as to afford the amide 1.3.

The N,N-dibenzylamino amide product 1.3 is then transformed into the free amine compound 1.4 by means of a debenzylation procedure. The deprotection of N-benzyl amines is described, for example, in Protective Groups in Organic Synthesis, by T. W. Greene and P. G. M Wuts, Wiley, Second Edition 1990, p 365. The transformation can be effected under reductive conditions, for example by the use of hydrogen or a hydrogen donor, in the presence of a palladium catalyst, or by treatment of the N-benzyl amine with sodium in liquid ammonia, or under oxidative conditions, for example by treatment with 3-chloroperoxybenzoic acid and ferrous chloride.

Preferably, the N,N-dibenzyl compound 1.3 is converted into the amine 1.4 by means of hydrogen transfer catalytic hydrogenolysis, for example by treatment with methanolic ammonium formate and 5% palladium on carbon catalyst, at ca. 75° C. for ca. 6 hours, for example as described in U.S. Pat. No. 5,914,332.

The thus-obtained amine 1.4 is then transformed into the amide 1.6 by reaction with the carboxylic acid 1.5, or an activated derivative thereof, in which the substituent A is either the group link-$P(O)(OR^1)_2$ or a precursor thereto. Preparations of the carboxylic acids 1.5 are described below, Schemes 13-15. The amide-forming reaction is conducted under similar conditions to those described above for the preparation of the amide 1.3.

Preferably, the carboxylic acid is converted into the acid chloride, and the acid chloride is reacted with the amine 1.4 in a solvent mixture composed of an organic solvent such as ethyl acetate, and water, in the presence of a base such as sodium bicarbonate, for example as described in Org. Process Res. Dev., 2000, 4, 264, to afford the amide product 1.6. Scheme 2 illustrates an alternative method for the preparation of the phosphonate-containing diamides 1. In this procedure, 2-phenyl-1-[4-phenyl-2-(1-vinyl-propenyl)[1,3,2]oxazaborinan-6-yl]-ethylamine 2.1, the preparation of which is described in WO 9414436, is reacted with the carboxylic acid $R^2COOH$ 1.2, or an activated derivative thereof, to afford the amide product 2.2. The reaction is effected employing the same conditions as were described above for the preparation of the amide 1.3. Preferably, equimolar amounts of the acid chloride derived from the carboxylic acid 1.2 is reacted with the amine 2.1 in a polar aprotic solvent such as tetrahydrofuran or dimethylformamide, at from ambient temperature to about −60° C., in the presence of an organic or inorganic base, to produce the amide 2.2. The product is then reacted with the carboxylic acid 1.5, or an activated derivative thereof, to afford the amide 1.6. The amide-forming reaction is conducted under similar conditions to those described above for the preparation of the amide 1.3. Preferably, the acid 1.5 and the amine 2.2 are reacted in the presence of hydroxybenztriazole, and N-ethyl-N'-dimethylaminopropyl carbodiimide, in tetrahydrofuran at ambient temperature, as described in U.S. Pat. No. 5,484,801, to yield the amide 1.6.

The reactions illustrated in Schemes 1 and 2 illustrate the preparation of the compounds 1.6 in which A is either the group link-$P(O)(OR^1)_2$ or a precursor thereto, such as, for example, optionally protected OH, SH, NH, as described below. Scheme 3 depicts the conversion of the compounds 1.6 in which A is OH, SH, NH, as described below, into the compounds 1 in which A is the group link-$P(O)(OR^1)_2$. Procedures for the conversion of the group A into the group link-$P(O))(OR^1)_2$ are described below, (Schemes 16-26).

In this and succeeding examples, the nature of the phosphonate ester group can be varied, either before or after incorporation into the scaffold, by means of chemical transformations. The transformations, and the methods by which they are accomplished, are described below, (Scheme 27)

Scheme 1
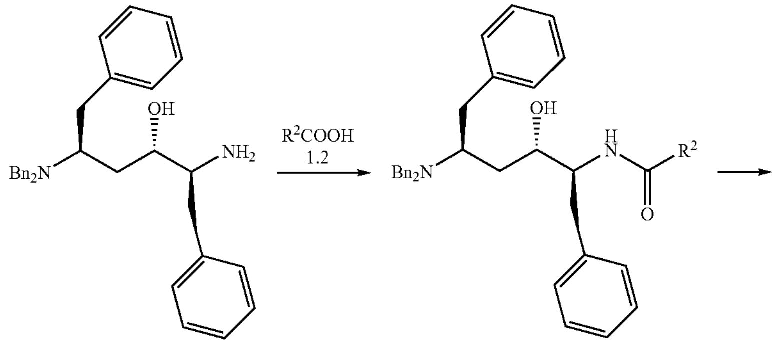
1.1 1.3
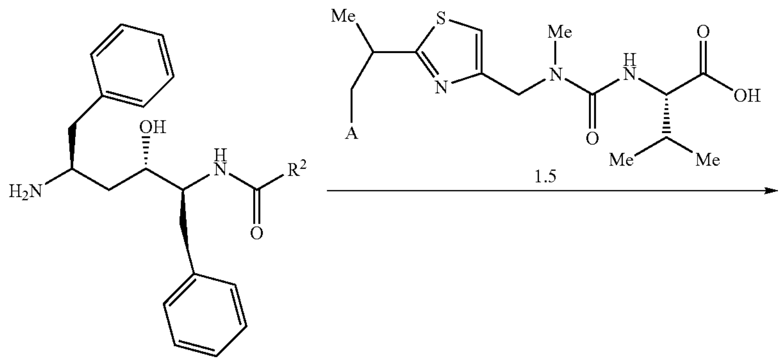
1.4
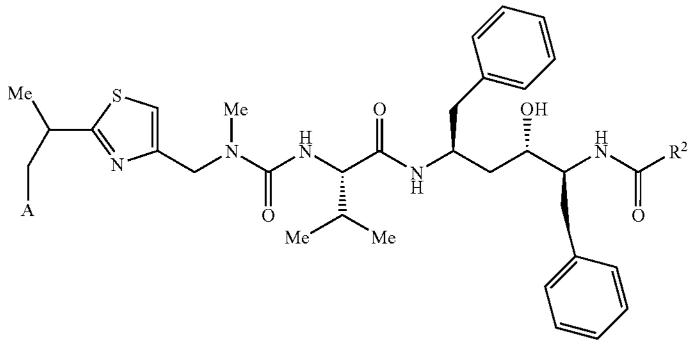
1.6

Scheme 2
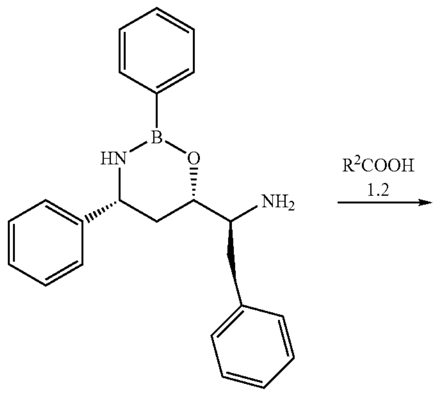
2.1
-continued
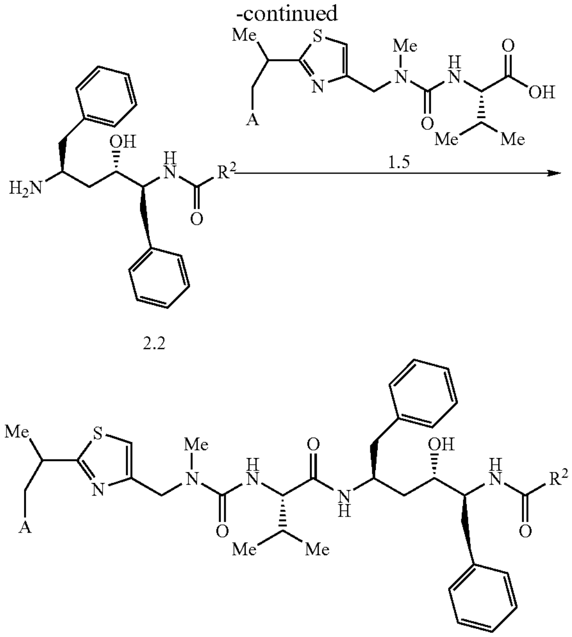
2.2
1.6
Scheme 3
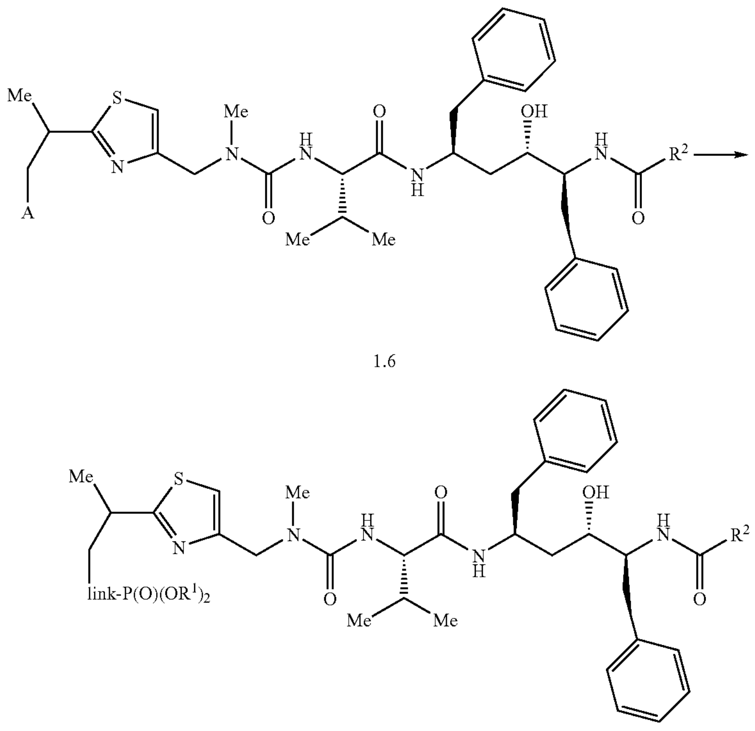
1.6
1

Preparation of the Phosphonate Intermediates 2.

Two methods for the preparation of the phosphonate intermediate compounds 2 are shown in Schemes 4 and 5. The selection of the route to be employed for a given compound is made after consideration of the substituents which are present, and their stability under the reaction conditions required.

As depicted in Scheme 4, the tribenzylated phenylalanine derivative 4.1, in which the substituent A is either the group link-$P(O)(OR^1)_2$ or a precursor thereto, as described below, is reacted with the anion 4.2 derived from acetonitrile, to afford the ketonitrile 4.3. Preparations of the tribenzylated phenylalanine derivatives 4.1 are described below, Schemes 16-18.

The anion of acetonitrile is prepared by the treatment of acetonitrile with a strong base, such as, for example, lithium hexamethyldisilylazide or sodium hydride, in an inert organic solvent such as tetrahydrofuran or dimethoxyethane, as described, for example, in U.S. Pat. No. 5,491,253. The solution of the acetonitrile anion 4.2, in an aprotic solvent such as tetrahydrofuran, dimethoxyethane and the like, is then added to a solution of the ester 4.1 at low temperature, to afford the coupled product 4.3.

Preferably, a solution of ca. two molar equivalent of acetonitrile, prepared by the addition of ca. two molar equivalent of sodium amide to a solution of acetonitrile in tetrahydrofuran at −40° C., is added to a solution of one molar equivalent of the ester 4.1 in tetrahydrofuran at −40° C., as described in J. Org. Chem., 1994, 59, 4040, to produce the ketonitrile 4.3. The above-described ketonitrile compound 4.3 is then reacted with an organometallic benzyl reagent 4.4, such as a benzyl Grignard reagent or benzyllithium, to afford the ketoenamine 4.5. The reaction is conducted in an inert aprotic organic solvent such as diethyl ether, tetrahydrofuran or the like, at from −80° C. to ambient temperature.

Preferably, the ketonitrile 4.3 is reacted with three molar equivalents of benzylmagnesium chloride in tetrahydrofuran at ambient temperature, to produce, after quenching by treatment with an organic carboxylic acid such as citric acid, as described in J. Org. Chem., 1994, 59, 4040, the ketoenamine 4.5.

The ketoenamine 4.5 is then reduced, in two stages, via the ketoamine 4.6, to produce the amino alcohol 4.7. The transformation of the ketoenamine 4.5 to the aminoalcohol 4.7 can be effected in one step, or in two steps, with or without isolation of the intermediate ketoamine 4.6, as described in U.S. Pat. No. 5,491,253.

For example, the ketoenamine 4.5 is reduced with a boron-containing reducing agent such as sodium borohydride, sodium cyanoborohydride and the like, in the presence of an acid such as methanesulfonic acid, as described in J. Org. Chem., 1994, 59, 4040, to afford the ketoamine 4.6. The reaction is performed in an ethereal solvent such as, for example, tetrahydrofuran or methyl tert-butyl ether. The latter compound is then reduced with sodium borohydride-trifluoroacetic acid, as described in U.S. Pat. No. 5,491,253, to afford the aminoalcohol 4.7. Alternatively, the ketoenamine 4.5 can be reduced to the aminoalcohol 4.7 without isolation of the intermediate ketoamine 4.6. In this procedure, described in U.S. Pat. No. 5,491,253, the ketoenamine 4.5 is reacted with sodium borohydride-methanesulfonic acid, in an ethereal solvent such as dimethoxyethane and the like. The reaction mixture is then treated with a quenching agent such as triethanolamine, and the procedure is continued by the addition of sodium borohydride and a solvent such as dimethyl formamide or dimethylacetamide or the like, to afford the aminoalcohol 4.7.

The aminoalcohol 4.7 is converted into the amide 4.9 by reaction with the acid $R^3COOH$ 4.8, or an activated derivative thereof, to produce the amide 4.9. This reaction is conducted under similar conditions to those described above for the preparation of the amides 1.3 and 1.6. The dibenzylated amide product 4.9 is deprotected to afford the free amine 4.10. The conditions for the debenzylation reaction are the same as those described above for the deprotection of the dibenzyl amine 1.3 to yield the amine 1.4, (Scheme 1).

The amine 4.10 is then reacted with the carboxylic acid $R^2COOH$ 1.2, or an activated derivative thereof, to produce the amide 4.11. This reaction is conducted under similar conditions to those described above for the preparation of the amides 1.3 and 1.6.

Alternatively, the amide 4.11 can be prepared by means of the sequence of reactions illustrated in Scheme 5.

In this sequence, the tribenzylated amino acid derivative 4.1 is converted, by means of the reaction sequence shown in Scheme 4 into the dibenzylated amine 4.7. This compound is then converted into a protected derivative, for example the tert-butoxycarbonyl (BOC) derivative 5.1. Methods for the conversion of amines into the BOC derivative are described in Protective Groups in Organic Synthesis, by T. W. Greene and P. G. M Wuts, Wiley, Second Edition 1990, p. 327. For example, the amine can be reacted with di-tert-butoxycarbonylanhydride (BOC anhydride) and a base, or with 2-(tert-butoxycarbonyloxyimino)-2-phenylacetonitrile (BOC—ON), and the like.

Preferably, the amine is reacted with ca. 1.5 molar equivalents of BOC anhydride and excess potassium carbonate, in methyl tert-butyl ether, at ambient temperature, for example as described in U.S. Pat. No. 5,914,3332, to yield the BOC-protected product 5.1.

The N-benzyl protecting groups are then removed from the amide product 5.1 to afford the free amine 5.2. The conditions for this transformation are similar to those described above for the preparation of the amine 1.4, (Scheme 1).

Preferably, the N,N-dibenzyl compound 5.1 is converted into the amine 5.2 by means of hydrogen transfer catalytic hydrogenolysis, for example by treatment with methanolic ammonium formate and 5% palladium on carbon catalyst, at ca. 75° C. for ca. 6 hours, for example as described in U.S. Pat. No. 5,914,332.

The amine compound 5.2 is then reacted with the carboxylic acid $R^2COOH$ 1.2, or an activated derivative thereof, to produce the amide 5.3. This reaction is conducted under similar conditions to those described above for the preparation of the amides 1.3 and 1.6, to afford the amide product 5.3.

The latter compound is then converted into the amine 5.4 by removal of the BOC protecting group. The removal of BOC protecting groups is described, for example, in Protective Groups in Organic Synthesis, by T. W. Greene and P. G. M Wuts, Wiley, Second Edition 1990, p. 328. The deprotection can be effected by treatment of the BOC compound with anhydrous acids, for example, hydrogen chloride or trifluoroacetic acid, or by reaction with trimethylsilyl iodide or aluminum chloride.

Preferably, the BOC group is removed by treatment of the substrate 5.3 with trifluoroacetic acid in dichloromethane at ambient temperature, for example as described in U.S. Pat. No. 5,914,232, to afford the free amine product 5.4.

The free amine thus obtained is then reacted with the carboxylic acid $R^3COOH$ 4.8, or an activated derivative thereof, to produce the amide 4.11. This reaction is conducted under similar conditions to those described above for the preparation of the amides 1.3 and 1.6.

The reactions shown in Schemes 4 and 5 illustrate the preparation of the compounds 4.11 in which A is either the group link-$P(O)(OR^1)_2$ or a precursor thereto, such as, for example, optionally protected OH, SH, NH, as described below. Scheme 6 depicts the conversion of the compounds 4.11 in which A is OH, SH, NH, as described below, into the compounds 2. Procedures for the conversion of the group A into the group link-$P(O))(OR^1)_2$ are described below, (Schemes 16-26).

Scheme 4

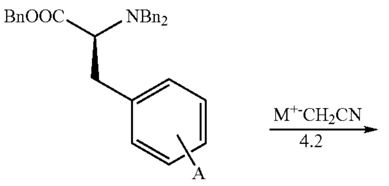

4.1

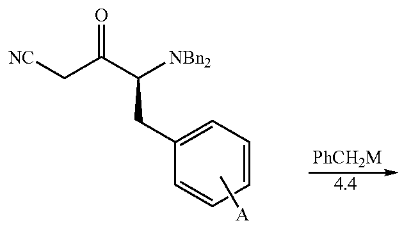

4.3

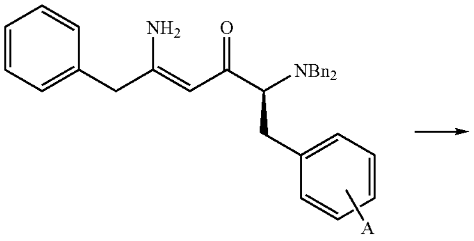

4.5

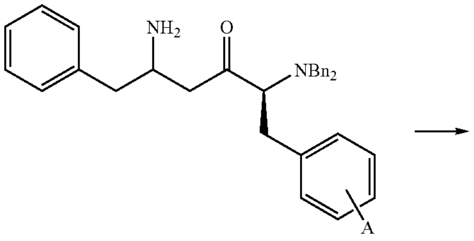

4.6

-continued

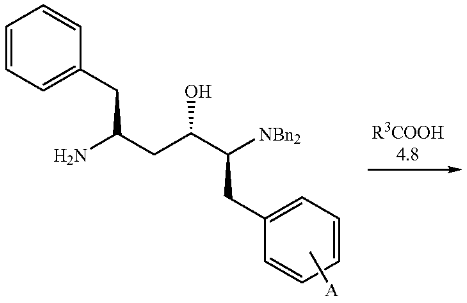

4.7

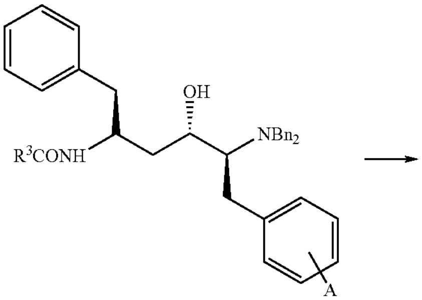

4.9

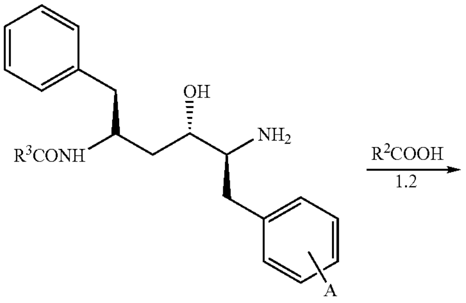

4.10

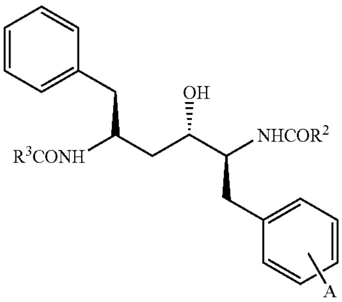

4.11

Scheme 5

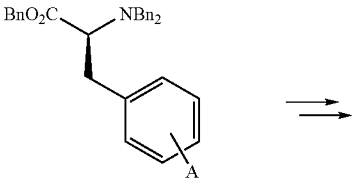

4.1

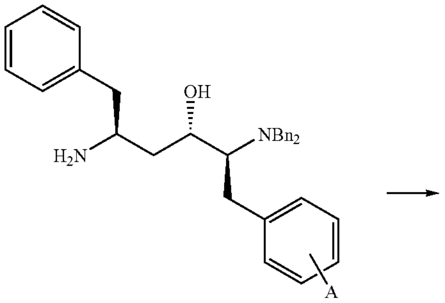

4.7

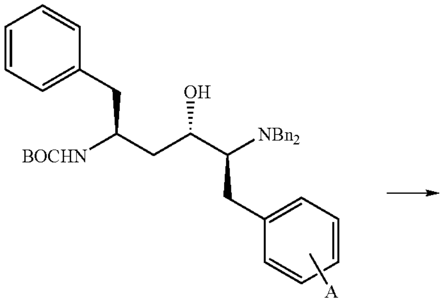

5.1

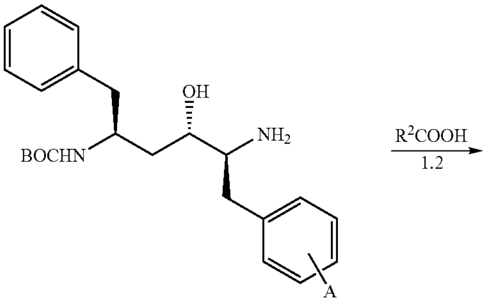

5.2

-continued

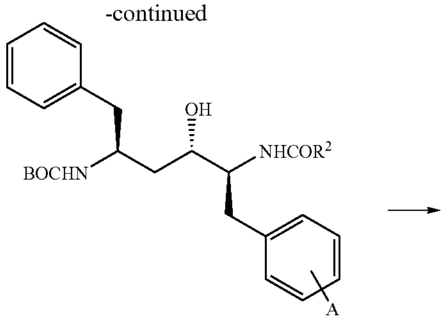

5.3

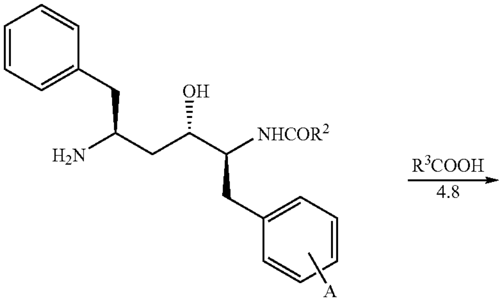

5.4

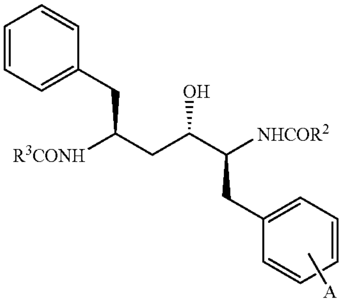

4.11

Preparation of the Phosphonate Intermediates 3.

The phosphonate ester intermediate compounds 3 can be prepared by two alternative methods, illustrated in Schemes 7 and 8. The selection of the route to be employed for a given compound is made after consideration of the substituents which are present, and their stability under the reaction conditions required.

As shown in Scheme 7,4-dibenzylamino-3-oxo-5-phenylpentanenitrile 7.1, the preparation of which is described in J. Org. Chem., 1994, 59, 4040, is reacted with a substituted benzylmagnesium halide reagent 7.2, in which the group B is a substituent, protected if appropriate, which can be converted, during or after the sequence of reactions shown in Scheme 7, into the moiety link-P(O)($OR^1$)$_2$. Examples of the substituent B are Br, [OH], [SH], [$NH_2$] and the like; procedures for the transformation of these groups into the phosphonate moiety are shown below in Schemes 16-26. The conditions for the reaction between the benzylmagnesium halide and the ketonitrile are similar to those described above for the preparation of the ketoenamine 4.5 (Scheme 4).

Preferably, the ketonitrile 7.1 is reacted with three molar equivalents of the substituted benzylmagnesium chloride 7.2 in tetrahydrofuran at ambient temperature, to produce, after quenching by treatment with an organic carboxylic acid such as citric acid, as described in J. Org. Chem., 1994, 59, 4040, the ketoenamine 7.3.

The thus-obtained ketoenamine 7.3 is then transformed, via the intermediate compounds 7.4, 7.5, 7.6, and 7.7 into the diacylated carbinol 7.8. The conditions for each step in the conversion of the ketoenamine 7.3 to the diacylated carbinol 7.8 are the same as those described above (Scheme 4) for the transformation of the ketoenamine 4.5 into the diacylated carbinol 4.11.

The diacylated carbinol 7.8 is then converted into the phosphonate ester 3, using procedures illustrated below in Schemes 16-26.

Alternatively, the phosphonate esters 3 can be obtained by means of the reactions illustrated in Scheme 8. In this procedure, the amine 7.5, the preparation of which is described above, (Scheme 7) is converted into the BOC derivative 8.1. The conditions for the introduction of the BOC group are similar to those described above for the protection of the amine 5.1, (Scheme 5).

Preferably, the amine is reacted with ca. 1.5 molar equivalents of BOC anhydride and excess potassium carbonate, in methyl tert-butyl ether, at ambient temperature, for example as described in U.S. Pat. No. 5,914,332, to yield the BOC-protected product 8.1.

The BOC-protected amine 8.1 is then converted, via the intermediates 8.2, 8.3 and 8.4 into the diacylated carbinol 8.5. The reaction conditions for this sequence of reactions are similar to those described above for the transformation of the BOC-protected amine 5.1 into the diacylated carbinol 5.4 (Scheme 5).

The diacylated carbinol 8.5 is then converted into the phosphonate ester 3, using procedures illustrated below in Schemes 16-26.

Scheme 6

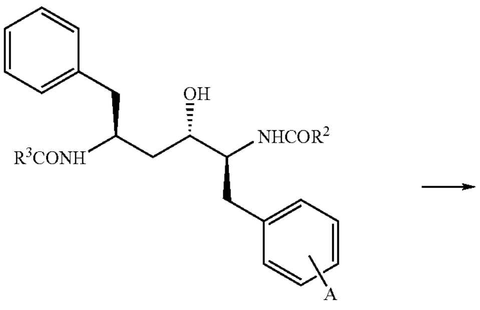

4.11

-continued

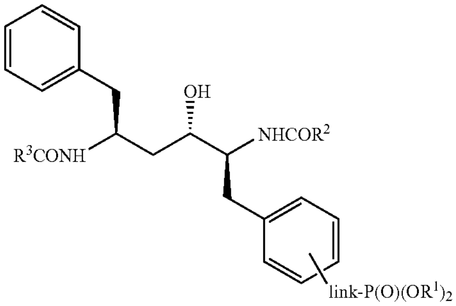

2

Scheme 7

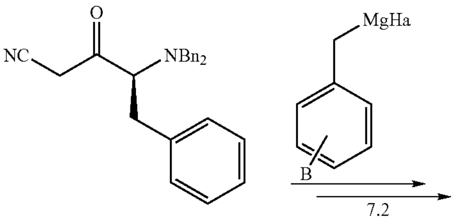

7.2

7.1

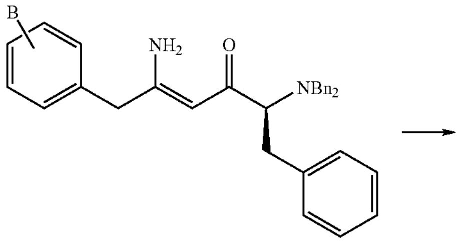

B = Br, [OH], [SH], [$NH_2$] etc 7.3

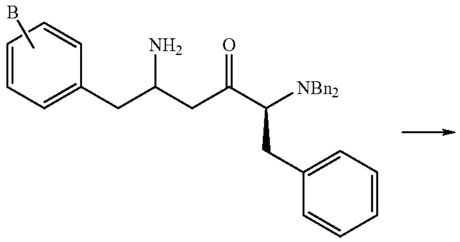

7.4

-continued
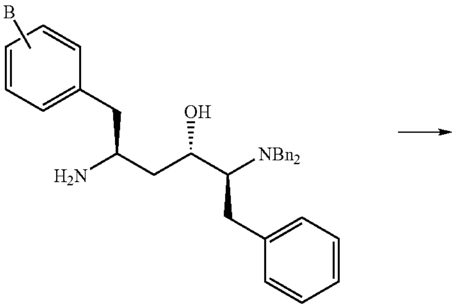
7.5
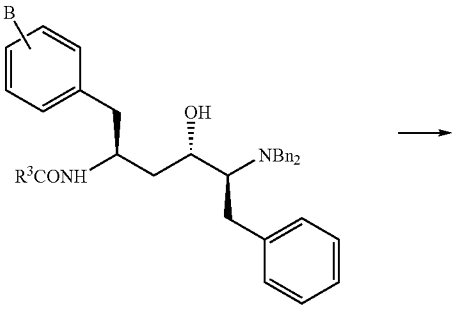
7.6
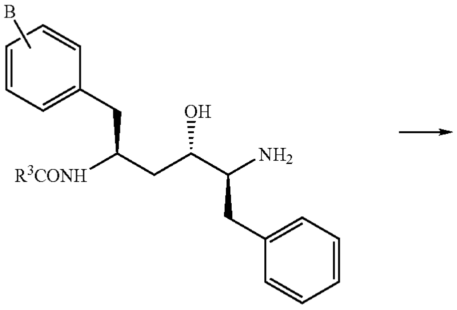
7.7
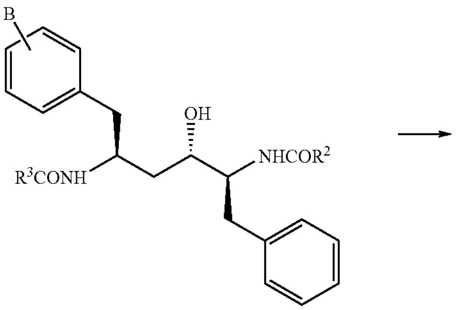
7.8
-continued
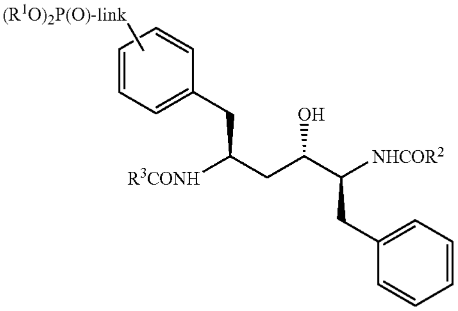
3
Scheme 8
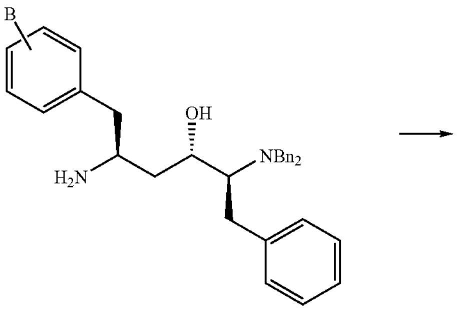
7.5
B = [OH], [SH], [$NH_2$] etc
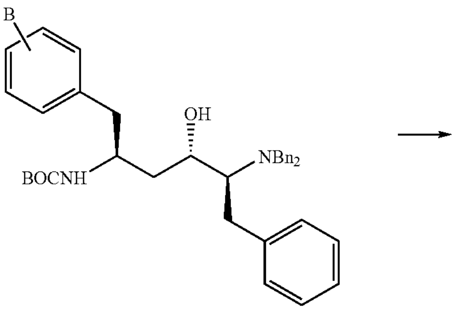
8.1
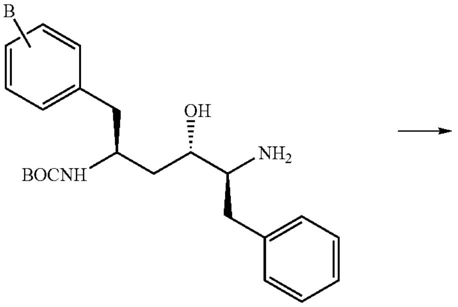
8.2

-continued

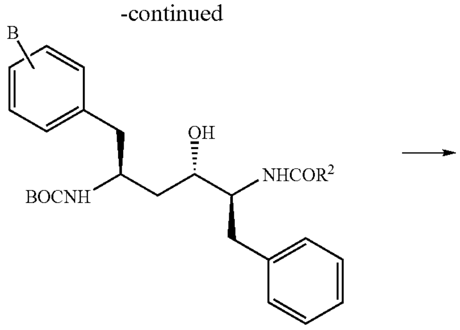

8.3

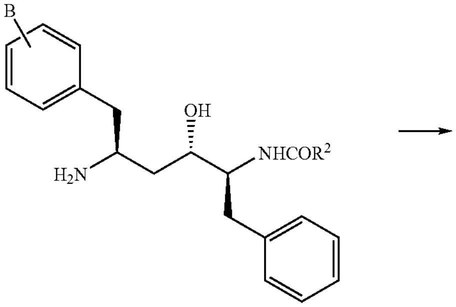

8.4

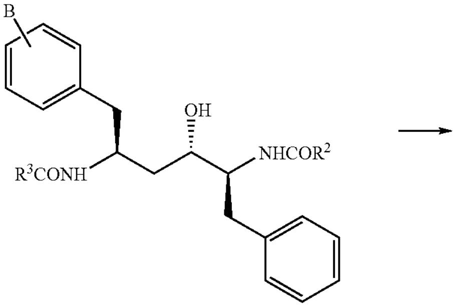

8.5

-continued

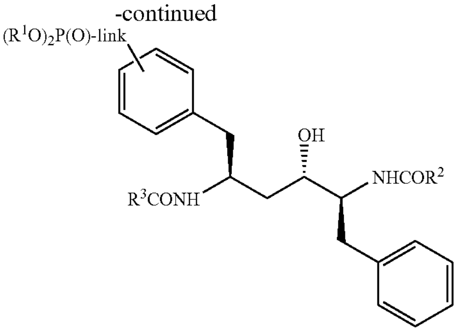

3

Preparation of the Phosphonate Intermediates 4.

Scheme 9 illustrates the preparation of the intermediate phosphonate esters 9.2 in which the substituent A, which is the phosphonate ester moiety or a precursor group thereto, is attached to one of the urea nitrogen atoms in the carboxylic acid reactant 9.1. The preparation of the carboxylic acid reactant 9.1 is described below, Schemes 24-25. In this procedure, the amine 1.4, prepared as described in Scheme 1, is reacted with the carboxylic acid 9.1, to afford the amide 9.2. The reaction between the amine 1.4 and the carboxylic acid 9.1, or an activated derivative thereof, is conducted under the same general conditions as those described above for the preparation of the amide 1.6 (Scheme 1). Preferably, the reactants are combined in the presence of hydroxybenztriazole and a carbodiimide, as described in U.S. Pat. No. 5,484,801, to yield the amide product 9.2.

The procedure shown in Scheme 9 describes the preparation of the compounds 9.2 in which the substituent A is either the group link-$P(O)(OR^1)_2$ or a precursor group thereto, such as [OH], [SH, [NH], as described below. Scheme 10 depicts the conversion of compounds 9.2 in which A is [OH], [SH, [NH], into the compounds 4, in which the group A has been transformed into the group link-$P(O)(OR^1)_2$ The methods for accomplishing this transformation are described below, Schemes 16-26.

Scheme 9

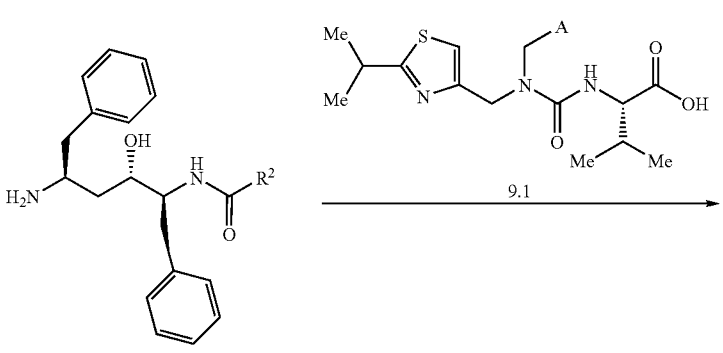

1.4

-continued

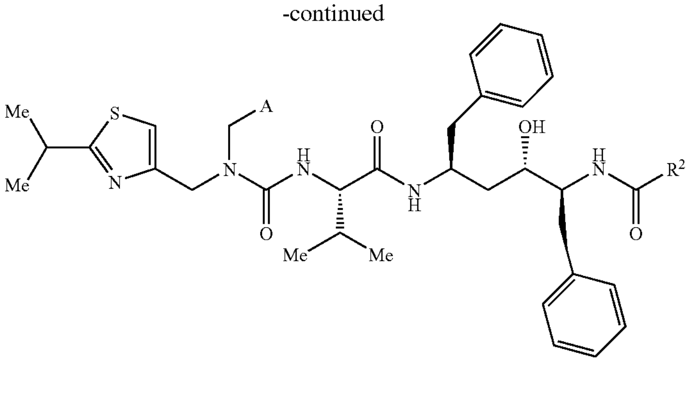

9.2

Scheme 10

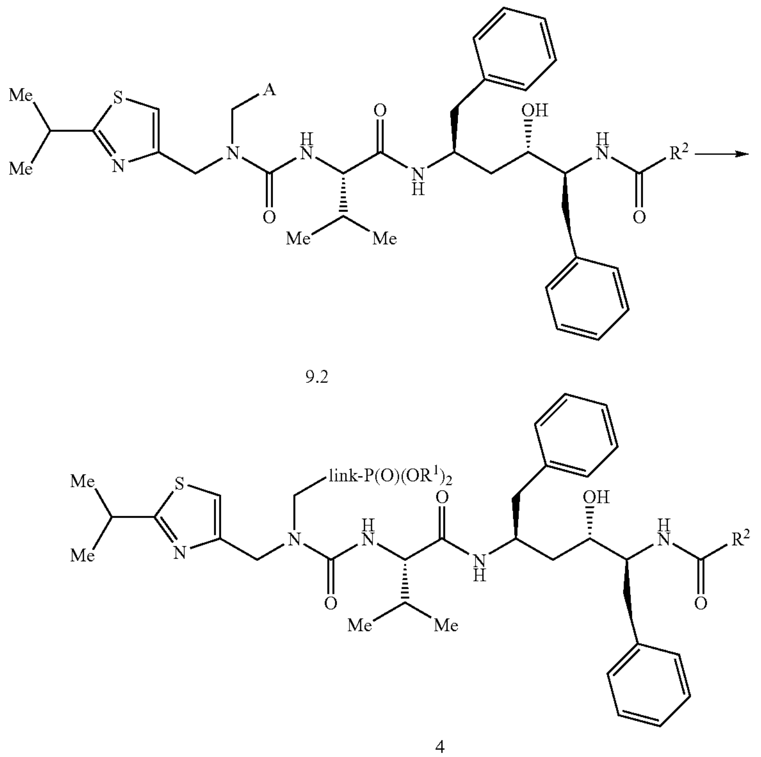

9.2

4

Preparation of the Phosphonate Intermediates 5.

Scheme 11 illustrates the preparation of the intermediate phosphonate esters 11.2 in which the substituent A, which is the phosphonate ester moiety or a precursor group thereto, is attached to the valine moiety in the carboxylic acid reactant 11.1. The preparation of the carboxylic acid reactant 11.1 is described below, Scheme 26. The reaction between the amine 1.4 and the carboxylic acid 11.1, or an activated derivative thereof, is conducted under the same general conditions as those described above for the preparation of the amide 1.3 (Scheme 1). Preferably, the reactants are combined in the presence of hydroxybenztriazole and a carbodiimide, as described in U.S. Pat. No. 5,484,801, to yield the amide product 11.2. The procedure shown in Scheme 11 describes the preparation of the compounds 11.2 in which the substituent A is either the group link-$P(O)(OR^1)_2$ or a precursor group thereto, such as [OH], [SH, [NH] Ha, as described below. Scheme 12 depicts the conversion of compounds 11.2 in which A is [OH], [SH, [NH] Br, into the compounds 5, in which the group A has been transformed into the group link-$P(O)(OR^1)_2$. The methods for accomplishing this transformation are described below, Schemes 16-26.

Scheme 11
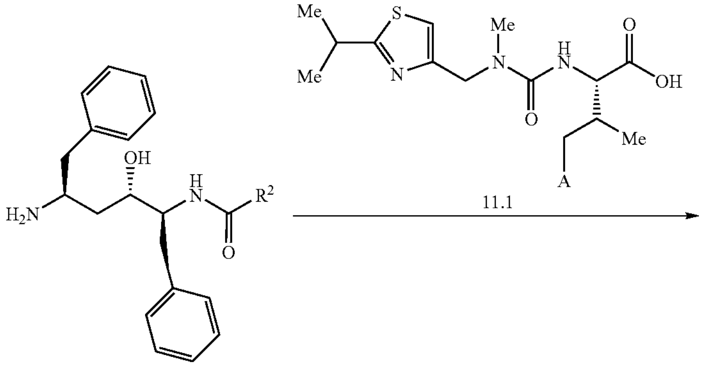
1.4
11.1
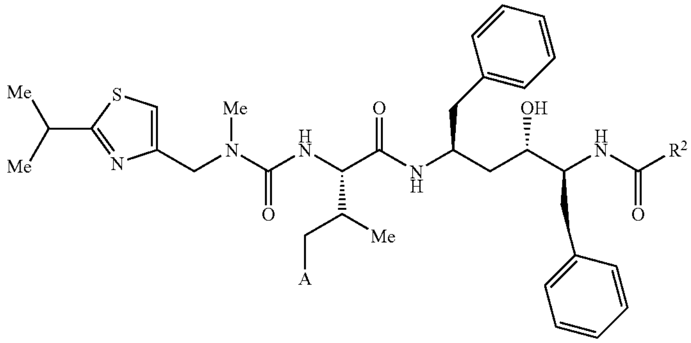
11.2
Scheme 12
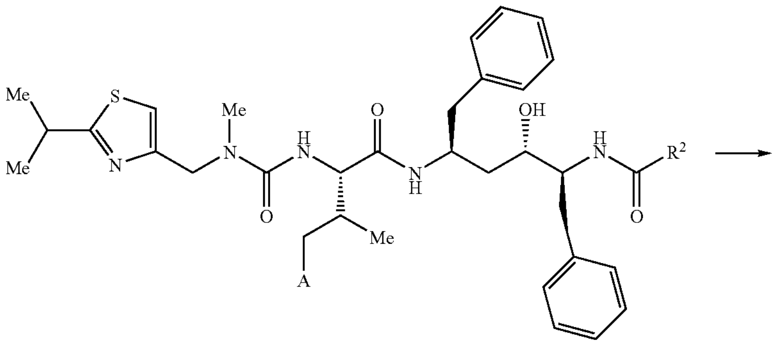
11.2

-continued

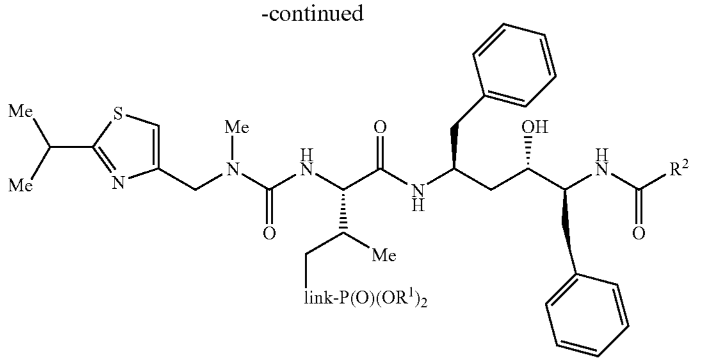

5

Preparation of Carboxylic Acids 1.5, with a Phosphonate Moiety Attached to the Isopropyl Group.

Scheme 13 illustrates the preparation of carboxylic acid reactants 1.5, in which a substituent A, attached to the isopropyl group, is either the group link-P(O)(OR$^1$)$_2$ or a precursor group thereto, such as [OH], [SH, [NH] Br. During the series of reaction shown in Scheme 13, the group A may, at an appropriate stage, be converted into the group link-P(O)(OR$^1$)$_2$, according to the knowledge of one skilled in the art. Alternatively, the carboxylic acid 1.5, in which A is link-P(O)(OR$^1$)$_2$, may be incorporated into the diamide compounds 1.6, as described above, (Schemes 1 and 2) before effecting the transformation of the group A into the group link-P(O)(OR$^1$)$_2$.

As shown in Scheme 13, a substituted derivative of isobutyramide 13.1 is converted into the corresponding thioamide 13.2. The conversion of amides into thioamides is described in Synthetic Organic Chemistry, by R. B. Wagner and H. D. Zook, Wiley, 1953, p. 827. The amide is reacted with a sulfur-containing reagent such as phosphorus pentasulfide or Lawessson's reagent, as described in Reagents for Organic Synthesis, by L. F. Fieser and M. Fieser, Wiley, Vol. 13, p. 38, to yield the thioamide 13.2. Preferably, the amide 13.1 is reacted with phosphorus pentasulfide in ether solution, at ambient temperature, as described in U.S. Pat. No. 5,484,801, to afford the amide 13.2. The latter compound is then reacted with 1,3-dichloroacetone 13.3 to produce the substituted thiazole 13.4. The preparation of thiazoles by the reaction between a thioamide and a chloroketone is described, for example, in Heterocyclic Chemistry, by T. A. Gilchrist, Longman, 1997, p. 321. Preferably, equimolar amounts of the reactants are combined in acetone solution at reflux temperature, in the presence of magnesium sulfate, as described in U.S. Pat. No. 5,484,801, to produce the thiazole product 13.4. The chloromethyl thiazole 13.4 is then reacted with methylamine to afford the substituted methylamine 13.6. The preparation of amines by the reaction of amines with alkyl halides is described, for example, in Comprehensive Organic Transformations, by R. C. Larock, VCH, 1989, p. 397. Typically, the components are reacted together in a polar solvent such as an alkanol or dimethylformamide and the like. Preferably, the chloro compound 13.4 is reacted with excess aqueous methylamine at ambient temperature, as described in U.S. Pat. No. 5,484,801, to afford the amine product 13.6. The amine is then converted into the urea derivative 13.8 by reaction with an activated derivative of the valine carbamic acid 13.7, in which X is a leaving group such as alkanoyloxy or 4-nitrophenoxy. The preparation of ureas by the reaction between carbamic acid derivatives and amines is described in Chem. Rev., 57, 47, 1957. Suitable carbaric acid derivatives are prepared by the reaction between an amine and an alkyl or aryl chloroformate, for example as described in WO 9312326. Preferably, the reaction is performed using carbamic acid derivative 13.7, in which X is 4-nitrophenoxy, and the amine 13.8; the reaction is conducted at about 0° C. in an inert solvent such as dichloromethane, in the presence of an organic base such as dimethylaminopyridine or N-methylmorpholine, as described in U.S. Pat. No. 5,484,801, to yield the urea product 13.8. The ester group present in the urea product 13.8 is then hydrolyzed to afford the corresponding carboxylic acid 1.5. Hydrolysis methods for converting esters into carboxylic acids are described, for example, in Comprehensive Organic Transformations, by R. C. Larock, VCH, 1989, p. 981. The methods include the use of enzymes such as pig liver esterase, and chemical methods such as the use of alkali metal hydroxides in aqueous organic solvent mixtures. Preferably, the methyl ester is hydrolyzed by treatment with lithium hydroxide in aqueous dioxan, as described in U.S. Pat. No. 5,848,801, to yield the carboxylic acid 1.5. Scheme 14 illustrates the preparation of the carboxylic acids 9.1 in which the group A, attached to the amine moiety, is either the group link-P(O)(OR$^1$)$_2$ or a precursor group thereto, such as [OH], [SH, [NH] Br. During the series of reaction shown in Scheme 14, the group A may, at an appropriate stage, be converted into the group link-P(O)(OR$^1$)$_2$, according to the knowledge of one skilled in the art. Alternatively, the carboxylic acid 9.1, in which A is link-P(O)(OR$^1$)$_2$, may be incorporated into the diamide compounds 9.2, as described above, (Scheme 9) before effecting the transformation of the group A into the group link-P(O)(OR$^1$)$_2$. As shown in Scheme 14, 4-chloromethyl-2-isopropyl-thiazole 14.1, prepared as described in WO 9414436, is reacted with an amine 14.2, in which A is as described above, to afford the amine 13.6. The conditions for the alkylation reaction are the same as those described above for the preparation of the amine 13.6. The product is then transformed, via the intermediate ester 14.4, into the carboxylic acid 9.1. The conditions for the reactions required to transform the amine 14.3 into the carboxylic acid 9.1 are the same as those described above (Scheme 13) for the analogous chemical steps.

Scheme 15 illustrates the preparation of the carboxylic acids 11.1 in which the group A, attached to the valine moiety, is either the group link-P(O)(OR$^1$)$_2$ or a precursor group thereto, such as [OH], [SH, [NH] Br. During the series of reaction shown in Scheme 15, the group A may, at an appropriate stage, be converted into the group link-P(O)(OR[1])$_2$, according to the knowledge of one skilled in the art. Alternatively, the carboxylic acid 11.1, in which A is link-P(O)(OR[1])$_2$ may be incorporated into the diamide compounds 11.2, as described above, (Scheme 11) before effecting the transformation of the group A into the group link-P(O)(OR[1])$_2$.

As shown in Scheme 15, (2-isopropyl-thiazol-4-ylmethyl)-methyl-amine, 15.1, prepared as described in WO 9414436, is reacted with a substituted valine derivative 15.2, in which the group A is as defined above. Methods for the preparation of the valine derivatives 15.2 are described below, Scheme 26. The resultant ester 15.3 is then hydrolyzed, as described above, to afford the carboxylic acid 11.1

-continued

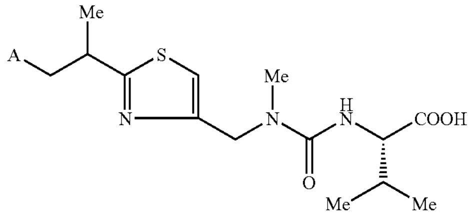

1.5

Scheme 13

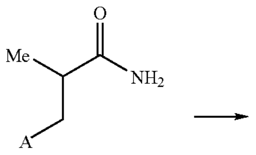

13.1

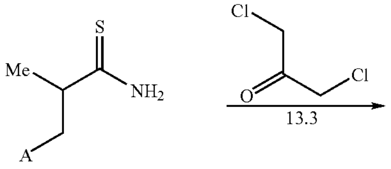

13.2

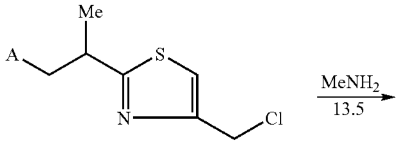

13.4

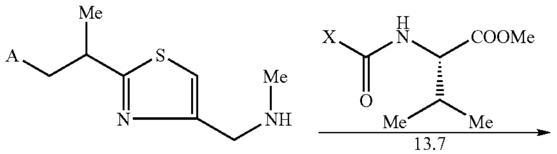

13.6

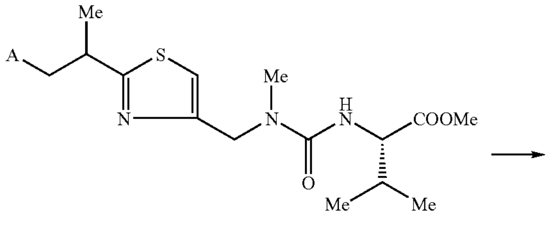

13.8

Scheme 14

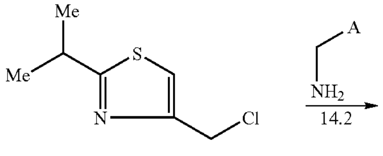

14.1

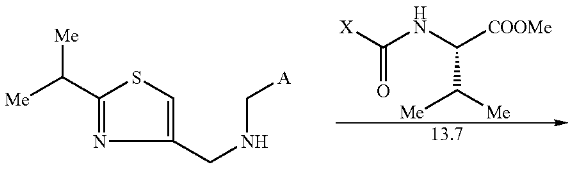

14.3

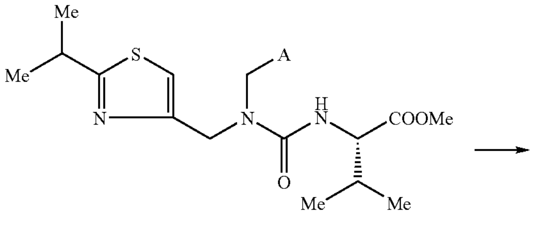

14.4

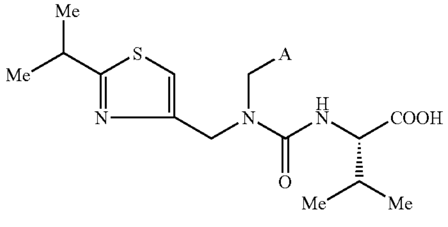

9.1

Scheme 15

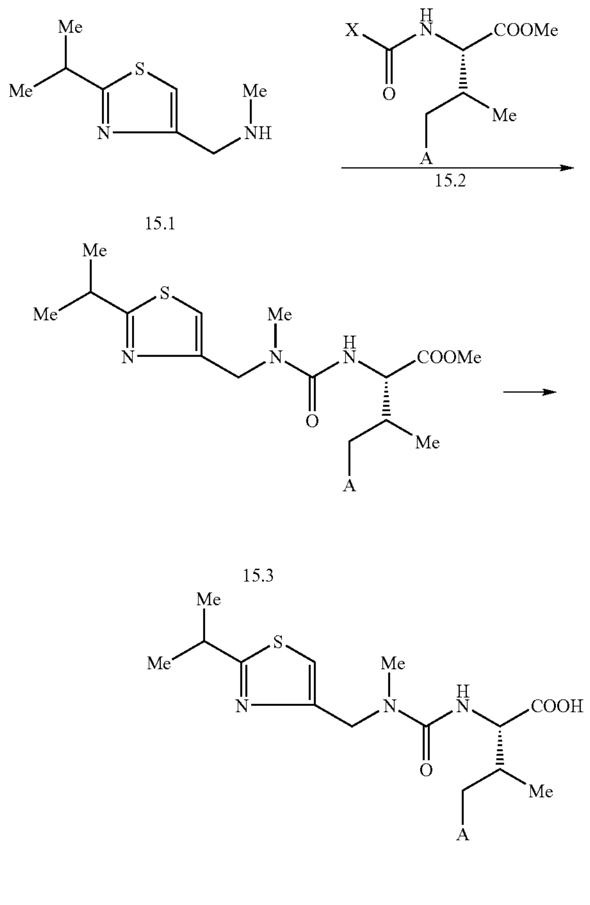

15.1

15.2

15.3

11.1

Preparation of Phenylalanine Derivatives 4.1 Incorporating Phosphonate Moieties.

Scheme 16 illustrates the preparation of phenylalanine derivatives incorporating phosphonate moieties attached to the phenyl ring by means of a heteroatom and an alkylene chain. The compounds are obtained by means of alkylation or condensation reactions of hydroxy or mercapto-substituted phenylalanine derivatives 16.1.

In this procedure, a hydroxy or mercapto-substituted phenylalanine is converted into the benzyl ester 16.2. The conversion of carboxylic acids into esters is described for example, in Comprehensive Organic Transformations, by R. C. Larock, VCH, 1989, p. 966. The conversion can be effected by means of an acid-catalyzed reaction between the carboxylic acid and benzyl alcohol, or by means of a base-catalyzed reaction between the carboxylic acid and a benzyl halide, for example benzyl chloride. The hydroxyl or mercapto substituent present in the benzyl ester 16.2 is then protected. Protection methods for phenols and thiols are described respectively, for example, in Protective Groups in Organic Synthesis, by T. W. Greene and P. G. M Wuts, Wiley, Second Edition 1990, p. 10, p 277. For example, suitable protecting groups for phenols and thiophenols include tert-butyldimethylsilyl or tert-butyldiphenylsilyl. Thiophenols may also be protected as S-adamantyl groups, as described in Protective Groups in Organic Synthesis, by T. W. Greene and P. G. M Wuts, Wiley, Second Edition 1990, p. 289. The protected hydroxy- or mercapto ester 16.3 is then reacted with a benzyl or substituted benzyl halide and a base, for example as described in U.S. Pat. No. 5,491,253, to afford the N,N-dibenzyl product 16.4. For example, the amine 16.3 is reacted at ca. 90° C. with two molar equivalents of benzyl chloride in aqueous ethanol containing potassium carbonate, to afford the tribenzylated product 16.4, as described in U.S. Pat. No. 5,491,253. The protecting group present on the O or S substituent is then removed. Removal of 6 or S protecting groups is described in Protective Groups in Organic Synthesis, by T. W. Greene and P. G. M Wuts, Wiley, Second Edition 1990, p. 10, p. 277. For example, silyl protecting groups are removed by treatment with tetrabutylammonium fluoride and the like, in a solvent such as tetrahydrofuran at ambient temperature, as described in J. Am. Chem. Soc., 94, 6190, 1972. S-Adamantyl groups can be removed by treatment with mercuric trifluoroacetate in acetic acid, as described in Chem. Pharm. Bull., 26, 1576, 1978.

The resultant phenol or thiophenol 16.5 is then reacted under various conditions to provide protected phenylalanine derivatives 16.9, 16.10 or 16.11, incorporating phosphonate moieties attached by means of a heteroatom and an alkylene chain.

In this step, the phenol or thiophenol 16.5 is reacted with a dialkyl bromoalkyl phosphonate 16.6 to afford the product 16.9. The alkylation reaction between 16.5 and 16.6 is effected in the presence of an organic or inorganic base, such as, for example, diazabicyclononene, cesium carbonate or potassium carbonate, The reaction is performed at from ambient temperature to ca. 80° C., in a polar organic solvent such as dimethylformamide or acetonitrile, to afford the ether or thioether product 16.9.

For example, as illustrated in Scheme 16, Example 1, a hydroxy-substituted phenylalanine derivative such as tyrosine, 16.12 is converted, as described above, into the benzyl ester 16.13.

The latter compound is then reacted with one molar equivalent of chloro tert-butyldimethylsilane, in the presence of a base such as imidazole, as described in J. Am. Chem. Soc., 94, 6190, 1972, to afford the silyl ether 16.14. This compound is then converted, as described above, into the tribenzylated derivative 16.15. The silyl protecting group is removed by treatment of 16.15 with a tetrahydrofuran solution of tetrabutyl ammonium fluoride at ambient temperature, as described in J. Am. Chem. Soc., 94, 6190, 1972, to afford the phenol 16.16. The latter compound is then reacted in dimethylformamide at ca. 60° C., with one molar equivalent of a dialkyl 3-bromopropyl phosphonate 16.17 (Aldrich), in the presence of cesium carbonate, to afford the alkylated product 16.18.

Using the above procedures, but employing, in place of the hydroxy-substituted phenylalanine derivative 16.12, different hydroxy or thio-substituted phenylalanine derivatives 16.1, and/or different bromoalkyl phosphonates 16.6, the corresponding ether or thioether products 16.9 are obtained.

Alternatively, the hydroxy or mercapto-substituted tribenzylated phenylalanine derivative 16.5 is reacted with a dialkyl hydroxymethyl phosphonate 16.7 under the conditions of the Mitsonobu reaction, to afford the ether or thioether compounds 16.10. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the ether or thioether products 16.10.

For example, as shown in Scheme 16, Example 2,3-mercaptophenylalanine 16.19, prepared as described in WO 0036136, is converted, as described above, into the benzyl ester 16.20. The resultant ester is then reacted in tetrahydrofuran solution with one molar equivalent of 4-methoxybenzyl chloride in the presence of ammonium hydroxide, as described in Bull. Chem. Soc. Jpn., 37, 433, 1974, to afford the 4-methoxybenzyl thioether 16.21. This compound is then converted, as described above for the preparation of the compound 16.4, into the tribenzyl derivative 16.22. The 4-methoxybenzyl group is then removed by the reaction of the thioether 16.22 with mercuric trifluoroacetate and anisole in trifluoroacetic acid, as described in J. Org. Chem., 52, 4420, 1987, to afford the thiol 16.23. The latter compound is reacted, under the conditions of the Mitsonobu reaction, with diethyl hydroxymethyl phosphonate 16.7, diethylazodicarboxylate and triphenylphosphine, for example as described in Synthesis, 4, 327, 1998, to yield the thioether product 16.24.

Using the above procedures, but employing, in place of the mercapto-substituted phenylalanine derivative 16.19, different hydroxy or mercapto-substituted phenylalanines 16.1, and/or different dialkylhydroxymethyl phosphonates 16.7, the corresponding products 16.10 are obtained.

Alternatively, the hydroxy or mercapto-substituted tribenzylated phenylalanine derivative 16.5 is reacted with an activated derivative of a dialkyl hydroxymethylphosphonate 16.8 in which Lv is a leaving group. The components are reacted together in a polar aprotic solvent such as, for example, dimethylformamide or dioxan, in the presence of an organic or inorganic base such as triethylamine or cesium carbonate, to afford the ether or thioether products 16.11.

For example, as illustrated in Scheme 16, Example 3,3-hydroxyphenylalanine 16.25 (Fluka) is converted, using the procedures described above, into the tribenzylated compound 16.26. The latter compound is reacted, in dimethylformamide at ca. 50° C., in the presence of potassium carbonate, with diethyl trifluoromethanesulfonyloxymethylphosphonate 16.27, prepared as described in Tet. Lett., 1986, 27, 1477, to afford the ether product 16.28.

Using the above procedures, but employing, in place of the hydroxy-substituted phenylalanine derivative 16.25, different hydroxy or mercapto-substituted phenylalanines 16.1, and/or different dialkyl trifluoromethanesulfonyloxymethylphosphonates 16.8, the corresponding products 16.11 are obtained.

Scheme 17 illustrates the preparation of phenylalanine derivatives incorporating phosphonate moieties attached to the phenyl ring by means of an alkylene chain incorporating a nitrogen atom. The compounds are obtained by means of a reductive alkylation reaction between a formyl-substituted tribenzylated phenylalanine derivative 17.3 and a dialkyl aminoalkylphosphonate 17.4.

In this procedure, a hydroxymethyl-substituted phenylalanine 17.1 is converted into the tribenzylated derivative 17.2 by reaction with three equivalents of a benzyl halide, for example, benzyl chloride, in the presence of an organic or inorganic base such as diazabicyclononene or potassium carbonate. The reaction is conducted in a polar solvent optionally in the additional presence of water. For example, the aminoacid 17.1 is reacted with three equivalents of benzyl chloride in aqueous ethanol containing potassium carbonate, as described in U.S. Pat. No. 5,491,253, to afford the product 17.2. The latter compound is then oxidized to afford the corresponding aldehyde 17.3. The conversion of alcohols to aldehydes is described, for example, in Comprehensive Organic Transformations, by R. C. Larock, VCH, 1989, p. 604ff. Typically, the alcohol is reacted with an oxidizing agent such as pyridinium chlorochromate, silver carbonate, or dimethyl sulfoxide/acetic anhydride, to afford the aldehyde product 17.3. For example, the carbinol 17.2 is reacted with phosgene, dimethyl sulfoxide and triethylamine, as described in J. Org. Chem., 43, 2480, 1978, to yield the aldehyde 17.3. This compound is reacted with a dialkyl aminoalkylphosphonate 17.4 in the presence of a suitable reducing agent to afford the amine product 17.5. The preparation of amines by means of reductive amination procedures is described, for example, in Comprehensive Organic Transformations, by R. C. Larock, VCH, p. 421, and in Advanced Organic Chemistry, Part B, by F. A. Carey and R. J. Sundberg, Plenum, 2001, p. 269. In this procedure, the amine component and the aldehyde or ketone component are reacted together in the presence of a reducing agent such as, for example, borane, sodium cyanoborohydride, sodium triacetoxyborohydride or diisobutylalumninum hydride, optionally in the presence of a Lewis acid, such as titanium tetraisopropoxide, as described in J. Org. Chem., 55, 2552, 1990.

For example, 3-(hydroxymethyl)-phenylalanine 17.6, prepared as described in Acta Chem. Scand. Ser. B, 1977, B31, 109, is converted, as described above, into the formylated derivative 17.7. This compound is then reacted with a dialkyl aminoethylphosphonate 17.8, prepared as described in J. Org. Chem., 200, 65, 676, in the presence of sodium cyanoborohydride, to produce the alkylated product 17.9.

Using the above procedures, but employing, in place of 3-(hydroxymethyl)-phenylalanine 17.6, different hydroxymethyl phenylalanines 17.1, and/or different aminoalkyl phosphonates 17.4, the corresponding products 17.5 are obtained.

Scheme 18 depicts the preparation of phenylalanine derivatives in which a phosphonate moiety is attached directly to the phenyl ring. In this procedure, a bromo-substituted phenylalanine 18.1 is converted, as described above, (Scheme 17) into the tribenzylated derivative 18.2. The product is then coupled, in the presence of a palladium(0) catalyst, with a dialkyl phosphite 18.3 to produce the phosphonate ester 18.4. The preparation of arylphosphonates by means of a coupling reaction between aryl bromides and dialkyl phosphites is described in J. Med. Chem., 35, 1371, 1992.

For example, 3-bromophenylalanine 18.5, prepared as described in Pept. Res., 1990, 3, 176, is converted, as described above, (Scheme 17) into the tribenzylated compound 18.6. This compound is then reacted, in toluene solution at reflux, with diethyl phosphite 18.7, triethylamine and tetrakis(triphenylphosphine)palladium(0), as described in J. Med. Chem., 35, 1371, 1992, to afford the phosphonate product 18.8.

Using the above procedures, but employing, in place of 3-bromophenylalanine 18.5, different bromophenylalanines b18.1, and/or different dialkylphosphites 18.3, the corresponding products 18.4 are obtained.

Scheme 16
Method
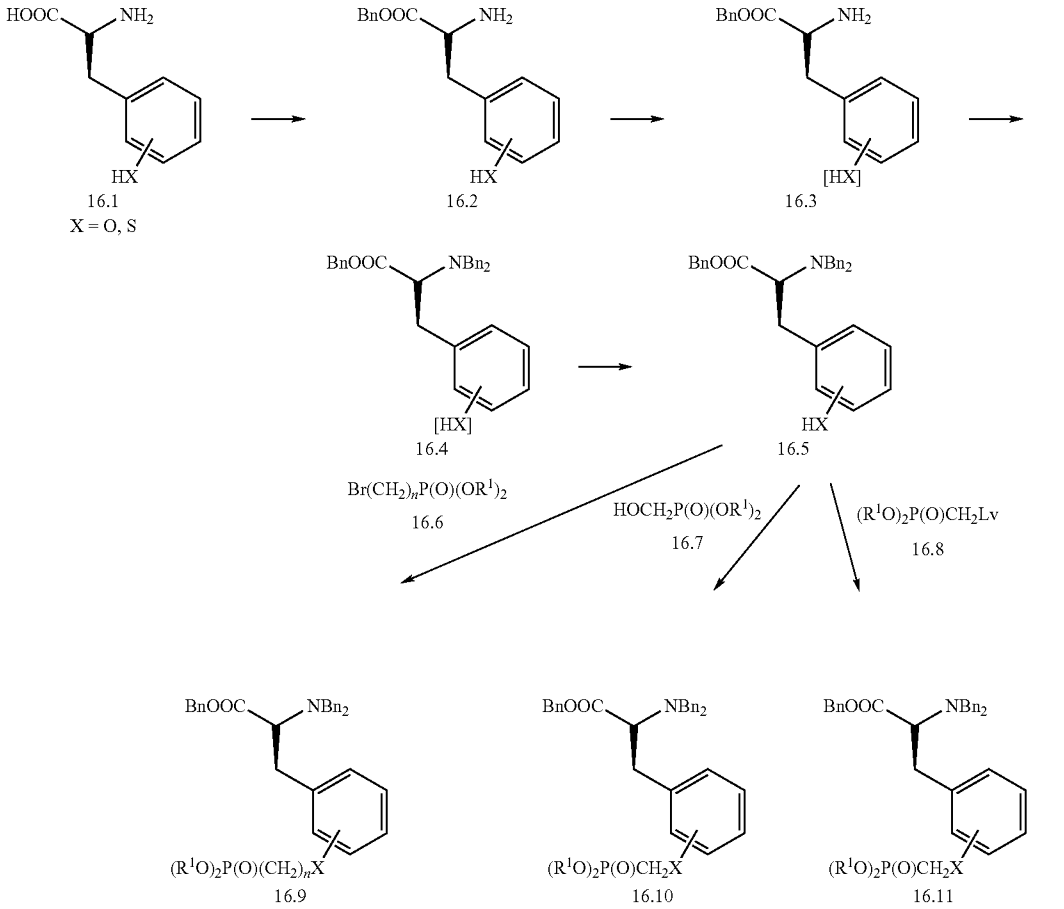
Example 1
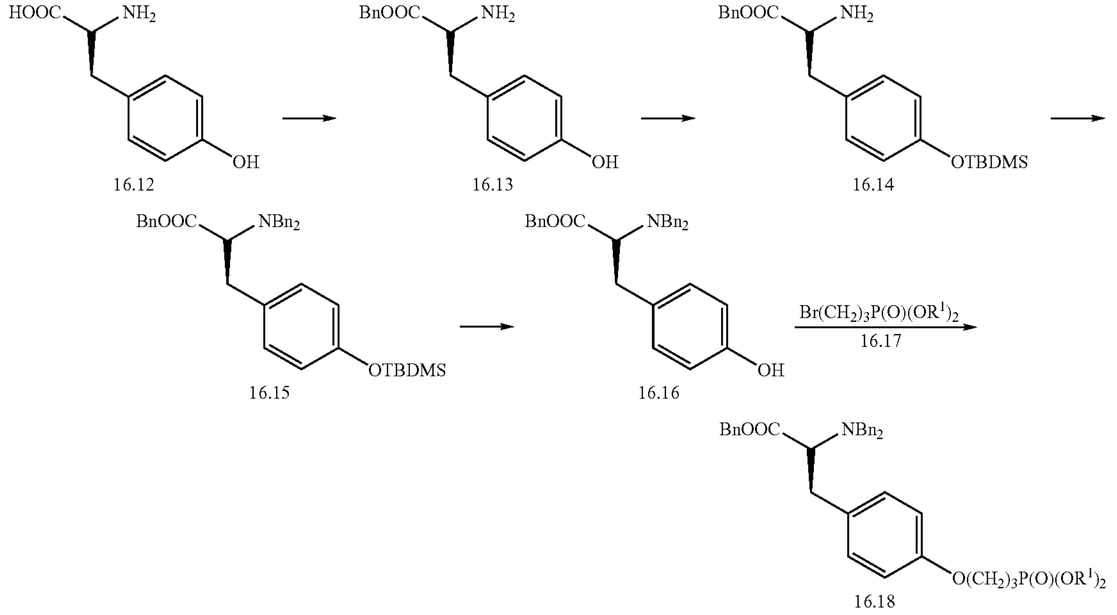

-continued
Example 2
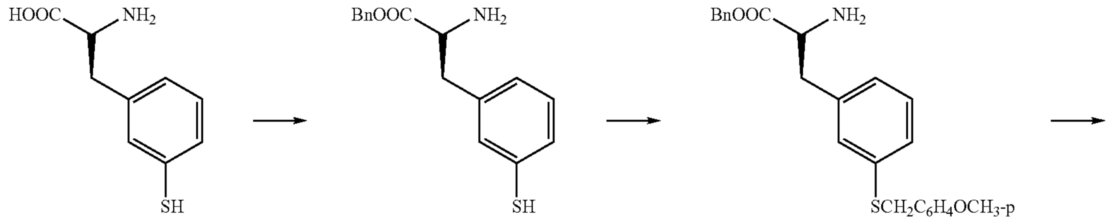
16.19 16.20 16.21
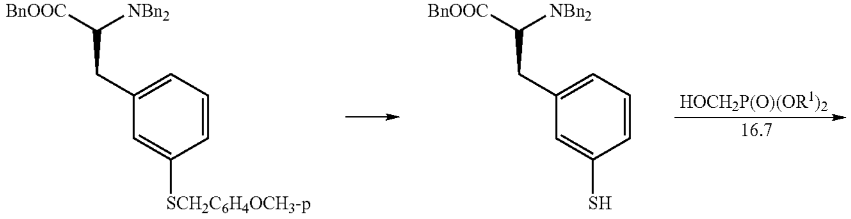
16.22 16.23
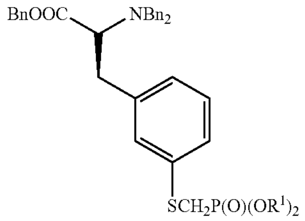
16.24
Example 3
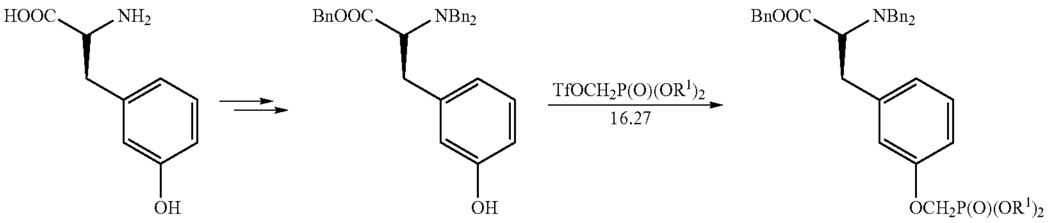
16.25 16.26 16.28
Scheme 17
Method
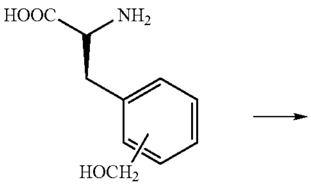
17.1
-continued
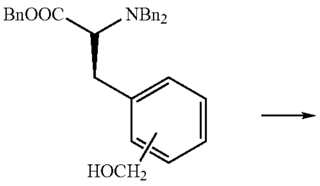
17.2
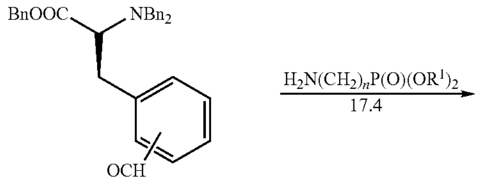
17.3

-continued

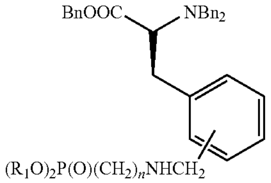

17.5

Example

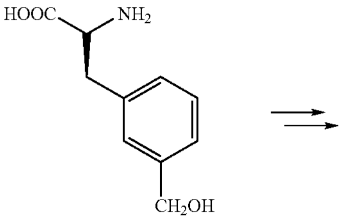

17.6

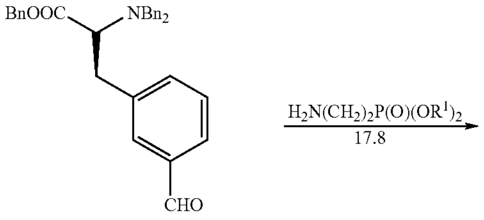

17.7

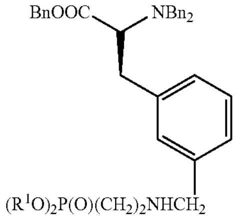

17.9

Scheme 18

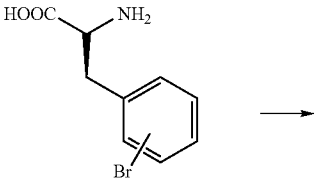

18.1

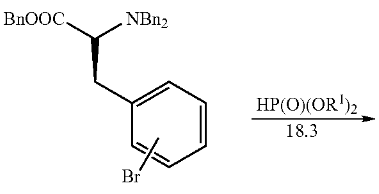

18.2

-continued

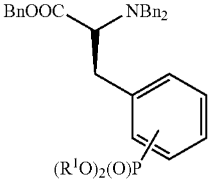

18.4

Example

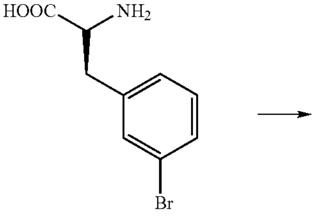

18.5

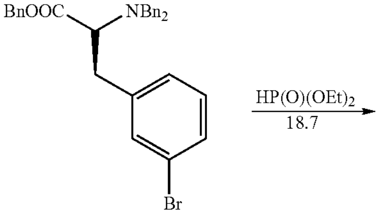

18.6

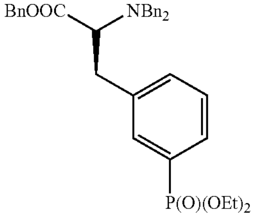

18.8

Preparation of Phosphonate Esters with Structure 3.

Scheme 19 illustrates the preparation of compounds 3 in which the phosphonate ester moiety is attached directly to the phenyl ring. In this procedure, the ketonitrile 7.1, prepared as described in J. Org. Chem., 1994, 59, 4080, is reacted with a bromobenzylmagnesium halide reagent 19.1. The resultant ketoenamine 19.2 is then converted into the diacylated bromophenyl carbinol 19.3. The conditions required for the conversion of the ketoenamine 19.2 into the carbinol 19.3 are similar to those described above (Scheme 4) for the conversion of the ketoenamine 4.5 into the carbinol 4.12. The product 19.3 is then reacted with a dialkyl phosphite 18.3, in the presence of a palladium (0) catalyst, to yield the phosphonate ester 19.4. The conditions for the coupling reaction are the same as those described above (Scheme 18) for the preparation of the phosphonate ester 18.4.

For example, the ketonitrile 7.1 is reacted, in tetrahydrofuran solution at −40° C., with three molar equivalents of 4-bromobenzylmagnesium bromide 19.5, the preparation of which is described in Tetrahedron, 2000, 56, 10067, to afford the ketoenamine 19.6. The latter compound is then converted into the bromophenyl carbinol 19.7, using the sequence of reactions described above (Scheme 4) for the conversion of the ketoenamine 4.5 into the carbinol 4.12. The resultant bromo compound 19.7 is then reacted with diethyl phosphite 18.3 and triethylamine, in toluene solution at reflux, in the presence of tetrakis(triphenylphosphine)palladium(0), as described in J. Med. Chem., 35, 1371, 1992, to afford the phosphonate product 19.8.

Using the above procedures, but employing, in place of 4-bromobenzylmagnesium bromide 19.5, different bromobenzylmagnesium halides 19.1 and/or different dialkyl phosphites 18.3, there are obtained the corresponding phosphonate esters 19.4.

Scheme 20 illustrates the preparation of compounds 3 in which the phosphonate ester moiety is attached to the nucleus by means of a phenyl ring. In this procedure, a bromophenyl-substituted benzylmagnesium bromide 20.1, prepared from the corresponding bromomethyl compound by reaction with magnesium, is reacted with the ketonitrile 7.1. The conditions for this transformation are the same as those described above (Scheme 4). The product of the Grignard addition reaction is then transformed, using the sequence of reactions described above, (Scheme 4) into the diacylated carbinol 20.2. The latter compound is then coupled, in the presence of a palladium(0) catalyst, with a dialkyl phosphite 18.3, to afford the phenylphosphonate 20.3. The procedure for the coupling reaction is the same as those described above for the preparation of the phosphonate 19.8.

For example, 4-(4-bromophenyl)benzyl bromide, prepared as described in DE 2262340, is reacted with magnesium to afford 4-(4-bromophenyl)benzylmagnesium bromine 20.4. This product is then reacted with the ketonitrile 7.1, as described above, to yield, after the sequence of reactions shown in Scheme 4, the diacylated carbinol 20.5. The latter compounds then reacted, as described above, (Scheme 18) with a dialkyl phosphite 18.3, to afford the phenylphosphonate 20.6.

Using the above procedures, but employing, in place of 4-(4-bromophenyl)benzyl bromide 20.4, different bromophenylbenzyl bromides 20.1, and/or different dialkyl phosphites 18.3, the corresponding products 20.3 are obtained.

Scheme 21 depicts the preparation of phosphonate esters 3 in which the phosphonate group is attached by means of a heteroatom and a methylene group. In this procedure, a hetero-substituted benzyl alcohol 21.1 is protected, affording the derivative 21.2. The protection of phenyl hydroxyl, thiol and amino groups are described, respectively, in Protective Groups in Organic Synthesis, by T. W. Greene and P. G. M Wuts, Wiley, Second Edition 1990, p. 10, p. 277, 309. For example, hydroxyl and thiol substituents can be protected as trialkylsilyloxy groups. Trialkylsilyl groups are introduced by the reaction of the phenol or thiophenol with a chlorotrialkylsilane, for example as described in Protective Groups in Organic Synthesis, by T. W. Greene and P. G. M Wuts, Wiley, Second Edition 1990, p. 10, p. 68-86. Alternatively, thiol substituents can be protected by conversion to tert-butyl or adamantyl thioethers, as described in Protective Groups in Organic Synthesis, by T. W. Greene and P. G. M Wuts, Wiley, Second Edition 1990, p. 289. Amino groups can be protected, for example by dibenzylation. The conversion of amines into dibenzylamines, for example by treatment with benzyl bromide in a polar solvent such as acetonitrile or aqueous ethanol, in the presence of a base such as triethylamine or sodium carbonate, is described in Protective Groups in Organic Synthesis, by T. W. Greene and P. G. M Wuts, Wiley, Second Edition 1990, p. 36[4]. The resultant protected benzyl alcohol 21.1 is converted into a halo derivative 21.2, in which Ha is chloro or bromo.

The conversion of alcohols into chlorides and bromides is described, for example, in Comprehensive Organic Transformations, by R. C. Larock, VCH, 1989, p. 354ff and p. 356ff. For example, benzyl alcohols 21.2 can be transformed into the chloro compounds 21.3, in which Ha is chloro, by reaction with triphenylphosphine and N-chlorosuccinimide, as described in J. Am. Chem. Soc., 106, 3286, 1984. Benzyl alcohols can be transformed into bromo compounds by reaction with carbon tetrabromide and triphenylphosphine, as described in J. Am. Chem. Soc., 92, 2139, 1970. The resultant protected benzyl halide 21.3 is then converted into the corresponding benzylmagnesium halide 21.4 by reaction with magnesium metal in an ethereal solvent, or by a Grignard exchange reaction treatment with an alkyl magnesium halide. The resultant substituted benzylinagnesium halide 21.4 is then converted, using the sequence of reactions described above (Scheme 4) for the preparation of the diacylated carbinol 4.11, into the carbinol 21.5 in which the substituent XH is suitably protected.

The protecting group is then removed to afford the phenol, thiophenol or amine 21.6. Deprotection of phenols, thiophenols and amines is described respectively in Protective Groups in Organic Synthesis, by T. W. Greene and P. G. M Wuts, Wiley, Second Edition 1990. For example, trialkylsilyl ethers or thioethers can be deprotected by treatment with a tetraalkylammonium fluoride in an inert solvent such as tetrahydrofuran, as described in J. Am Chem. Soc., 94, 6190, 1972. Tert-butyl or adamantyl thioethers can be converted into the corresponding thiols by treatment with mercuric trifluoroacetate in aqueous acetic acid at ambient temperatures, as described in Chem. Pharm. Bull., 26, 1576, 1978. N,N-dibenzyl amines can be converted into the unprotected amines by catalytic reduction in the presence of a palladium catalyst, as described above (Scheme 1). The resultant phenol, thiophenol or amine 21.6 is then converted into the phosphonate ester 21.7 by reaction with an activated derivative of a dialkyl hydroxymethyl phosphonate 16.27, in which Lv is a leaving group. The reaction is conducted under the same conditions as described above for the conversion of 16.5 to 16.11 (Scheme 16).

For example, 3-hydroxybenzyl alcohol 21.8 (Aldrich) is reacted with chlorotriisopropylsilane and imidazole in dimethylformamide, as described in Tet. Lett., 2865, 1964, to afford the silyl ether 21.9. This compound is reacted with carbon tetrabromide and triphenylphosphine in dichloromethane, as described in J. Am. Chem. Soc., 109, 2738, 1987, to afford the brominated product 21.10. This material is reacted with magnesium in ether to afford the Grignard reagent 21.11, which is then subjected to the series of reaction shown in Scheme 4 to afford the carbinol 21.12. The triisopropylsilyl protecting group is then removed by treatment of the ether 21.12 with tetrabutylammonium fluoride in tetrahydrofuran, as described in J. Org. Chem., 51, 4941, 1986. The resultant phenol 21.13 is then reacted with a dialkyl trifluoromethanesulfonyloxymethylphosphonate 16.27, prepared as described in Tet. Lett., 1986, 27, 1477, in dimethylformamide solution at 60° C. in the presence of cesium carbonate, to afford the phosphonate product 21.14.

Using the above procedures, but employing, in place of 3-hydroxybenzyl alcohol 21.8, different hydroxy, mercapto or amino-substituted benzyl alcohols 21.1, and/or different dialkyl trifluoromethanesulfonyloxymethyl phosphonates 16.27, the corresponding products 21.7 are obtained.

Scheme 19
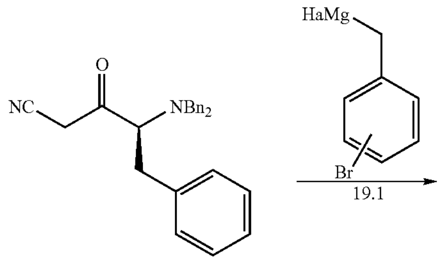
7.1
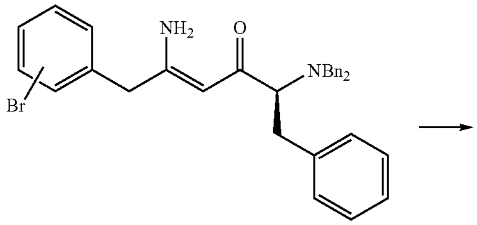
19.2
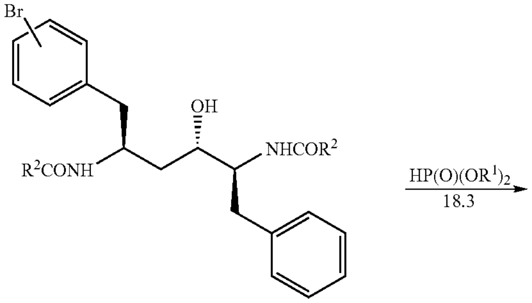
19.3
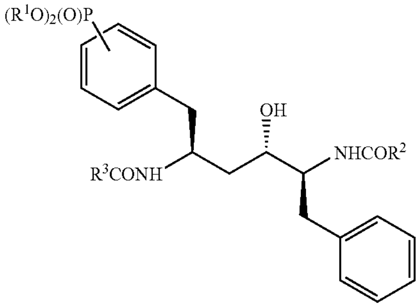
19.4
Example
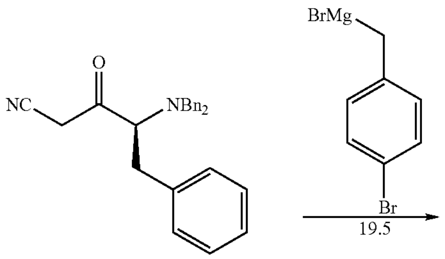
7.1
-continued
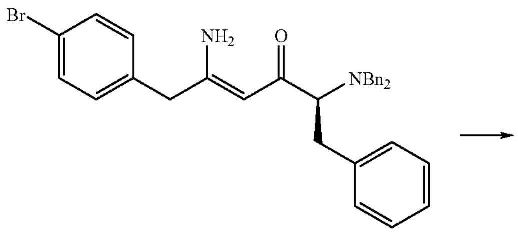
19.6
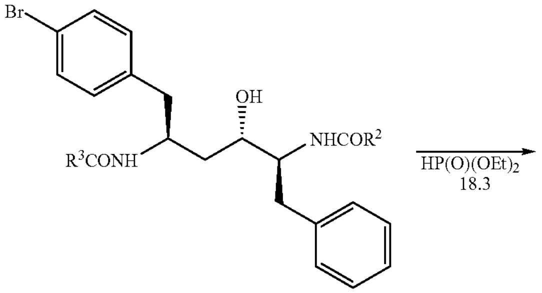
19.7
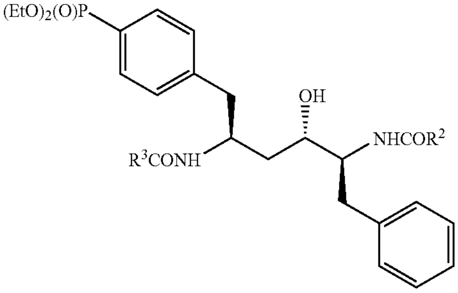
19.8
Scheme 20
Method
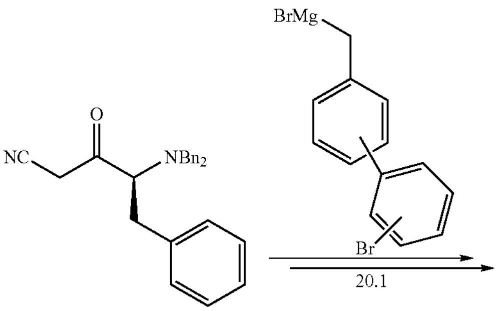
7.1

-continued
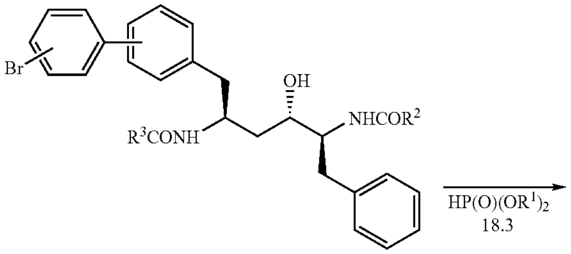
20.2
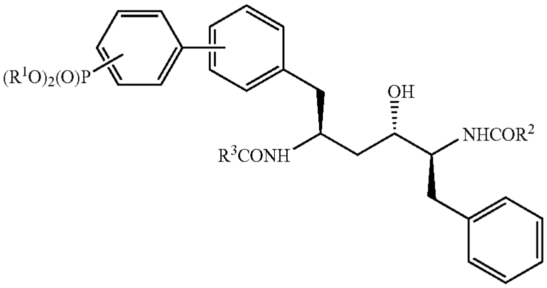
20.3
Example
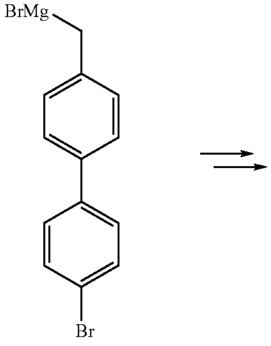
20.4
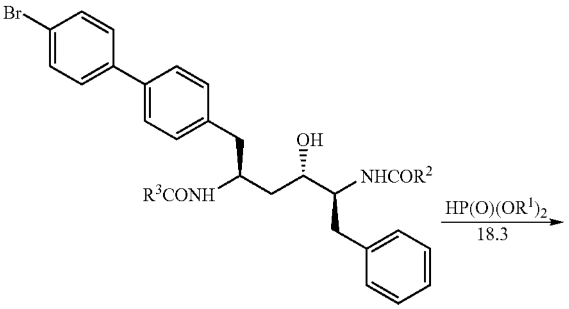
20.5
-continued
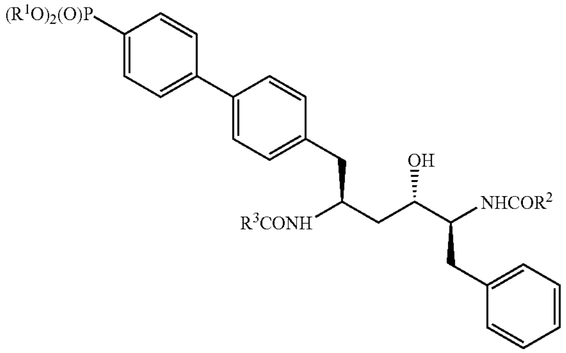
20.6
Scheme 21
Method
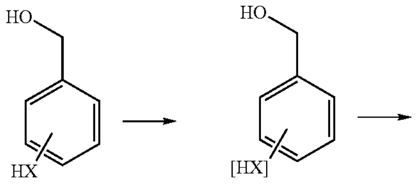
21.1
X = O, S, NH
21.2
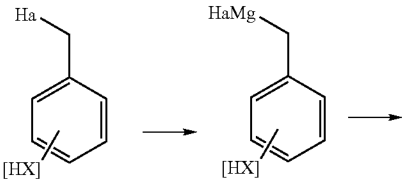
21.3
21.4
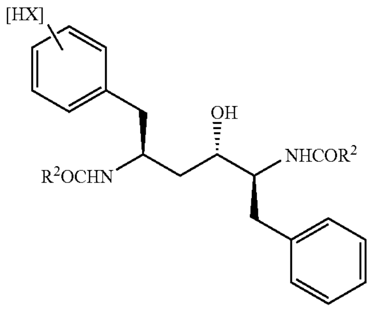
21.5

-continued

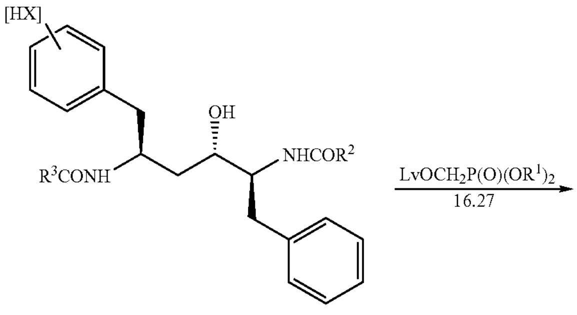

21.6

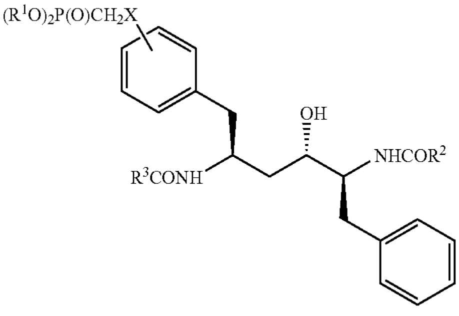

21.7

-continued

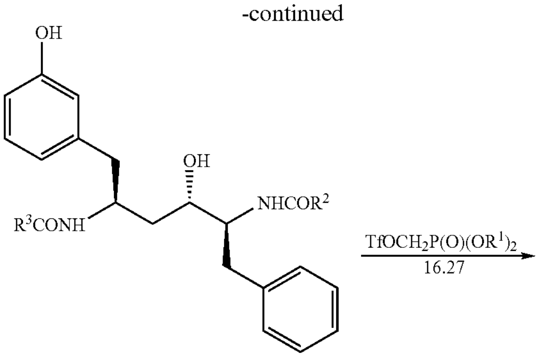

21.13

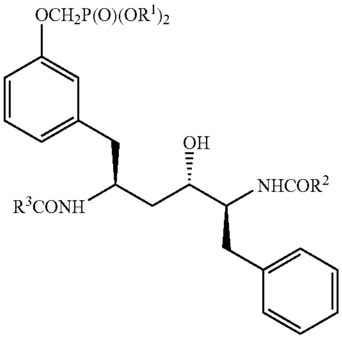

21.14

Example

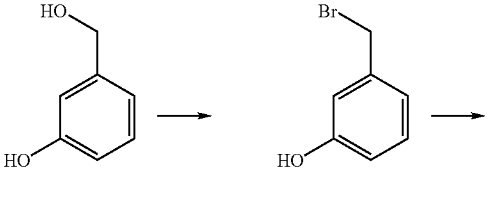

21.8

21.9

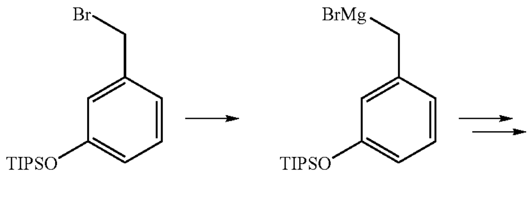

21.10

21.11

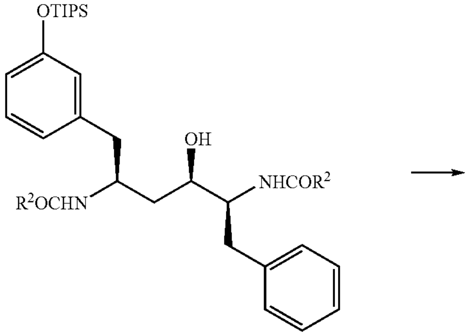

21.12

Preparation of Phosphonate-containing Carboxylic Acids 1.5.

Scheme 22 illustrates methods for the preparation of carboxylic acids 1.5, in which A is Br, and methods for the conversion of the bromo substituent into various phosphonate-containing substituents.

In this procedure, 3-bromo-2-methylpropanamide 22.1 is substituted for the isobutyramide derivative 13.1 in the reaction sequence illustrated in Scheme 13, so as to afford 2-{3-[2-(2bromo-1-methyl-ethyl)-thiazol-4-ylmethyl]-3-methyl-ureido}-3-methyl-butyric acid methyl ester, 22.2. The conditions required for the various reactions are the same as those described above (Scheme 13). The bromo-substituted ester 22.2 is then subjected to various transformations so as to introduce phosphonate-containing substituents. For example, the ester 22.2 is reacted with a trialkyl phosphate 22.3 in an Arbuzov reaction, to afford the phosphonate ester 22.4. The preparation of phosphonates by means of the Arbuzov reaction is described, for example, in Handb. Organophosphorus Chem., 1992, 115. The reaction is performed by heating the substrate at 100° C. to 150° C. with an excess of the trialkyl phosphite. The methyl ester group in the phosphonate product 22.4 is then hydrolyzed, using the procedures described above, (Scheme 13) to prepare the carboxylic acid 22.5.

For example, as shown in Scheme 22, Example 1, the bromo compound 22.2 is heated at 120° C. with a ten molar excess of tribenzyl phosphite 22.6 to afford the benzylphosphonate 22.7. Hydrolysis of the methyl ester, as described above, then yields 2-(3-{2-[2-(bis-benzyloxy-phosphoryl)-1-methyl-ethyl]-thiazol-4-ylmethyl}-3-methyl-ureido)-3-methyl-butyric acid 22.8.

Alternatively, the bromoester 22.2 is oxidized to the corresponding aldehyde 22.9. Methods for the oxidation of bromo compounds to the corresponding aldehyde are described, for example, in Comprehensive Organic Transformations, by R.

C. Larock, VCH, 1989 p. 599. The transformation can be effected by reaction of the aldehyde with dimethyl sulfoxide, optionally in the presence of a silver salt, as described in Chem. Rev., 67, 247, 1967. Alternatively, the bromo compound is reacted with trimethylamine oxide, as described in Ber., 94, 1360, 1961, to prepare 3-methyl-2-{3-methyl-3-[2-(1-methyl-2-oxo-ethyl)-thiazol-4ylmethyl]-ureido}-butyric acid methyl ester 22.9. The aldehyde is then reacted with a dialkyl aminoalkyl phosphonate 22.10 in a reductive amination reaction to afford the aminophosphonate 22.11. The conditions for the reductive amination reaction are the same as those described above for the preparation of the aminophosphonate 17.5, (Scheme 17). The methyl ester group present in the product 22.11 is then hydrolyzed, as described above, to yield the carboxylic acid 22.12.

For example, as shown in Scheme 22, Example 2, the bromo compound 22.2 is heated at 80° C. in dimethylsulfoxide solution, in the presence of one molar equivalent of silver tetrafluoborate and triethylamine, as described in J. Chem. Soc., Chem. Comm., 1338, 1970, to afford the aldehyde 22.9. Reductive amination of the product, in the presence of a dialkyl aminoethyl phosphonate 22.13, the preparation of which is described in J. Org. Chem., 2000, 65, 676 and sodium triacetoxy borohydride, then affords the amino phosphonate 22.14. Hydrolysis of the methyl ester, as described above, then afford the carboxylic acid 22.15.

Alternatively, the bromo compound 22.2 is reacted with a dialkyl thioalkyl phosphonate 22.16 to effect displacement of the bromo substituent to afford the thioether 22.17. The preparation of thioethers by the reaction of bromo compounds with thiols is described, for example, in Synthetic Organic Chemistry, R. B. Wagner, H. D. Zook, Wiley, 1953, p. 787. The reactants are combined in the presence of a suitable base, such as sodium hydroxide, dimethylaminopyridine, potassium carbonate and the like, in a polar organic solvent such as dimethylformamide or ethanol, to afford the thioether 22.17. The product is then subjected to hydrolysis, as described above, to afford the carboxylic acid 22.18.

For example, as shown in Scheme 22, Example 3, the bromo compound 22.2 is reacted with a dialkyl thioethylphosphonate 22.19, the preparation of which is described in Aust. J. Chem., 43, 1123, 1990, and dimethylaminopyridine, in dimethylformamide solution at ambient temperature, to yield the thioether 22.20. Hydrolysis of the methyl ester group, as described above, then afford the carboxylic acid 22.21.

Scheme 23 illustrates the preparation of carboxylic acids 23.7 in which the phosphonate moiety is attached to the isopropyl group by means of a phenyl ring and a heteroatom. In this procedure, the hydroxy or mercapto substituent on a phenylbutanamide 23.1 is protected. Methods for the protection of hydroxyl and thiol groups are described above (Scheme 21). The protected amide 23.2 is then subjected to the series of reactions illustrated in Scheme 13, so as to afford the O- or S-protected ester 23.3. The protecting group is then removed. Methods for the deprotection of phenols and thiophenols are described above (Scheme 16).

The resultant phenol or thiophenol 23.4 is then reacted with a dialkyl bromoalkyl phosphonate 23.5, to afford the ether or thioether compounds 23.6. Conditions for the alkylation of phenols and thiophenols are described above (Scheme 16). The ester groups present in the product 23.6 is then hydrolyzed, as described above, to afford the corresponding carboxylic acid 23.7.

For example, 3-(4-hydroxyphenyl)butyric acid 23.8, prepared as described in J. Med. Chem., 1992, 35, 548, is converted into the acid chloride by reaction with thionyl chloride. The acid chloride is then reacted with excess aqueous ethanolic ammonia to afford the amide 23.9. This compound is converted into the tert. butyldimethylsilyl derivative 23.10 by treatment with tert-butylchlorodimethylsilane and imidazole in dichloromethane. The resultant amide 23.10 is then subjected to the series of reactions shown in Scheme 13, so as to yield the ester 23.11. Desilylation, by treatment with tetrabutylammonium fluoride in tetrahydrofuran, then affords the phenol 23.12. This compound is reacted with a dialkyl bromoethyl phosphonate 23.13 (Aldrich) and potassium carbonate, in dimethylformamide at 80° C., to produce the ether 23.14. Hydrolysis of the ester group, by treatment with aqueous methanolic lithium hydroxide, then affords the carboxylic acid 23.15.

Using the above procedures, but employing, in place of the amide 23.9, different hydroxy- or thio-substituted amides 23.23.1, and/or different bromoalkylphosphonates 23.5, the corresponding products 23.7 are obtained.

Scheme 24 and 25 describes the preparation of carboxylic acids 9.1 in which the phosphonate moiety is attached to the amine component. In this procedure, the chloromethylthiazole 14.1, is reacted with a dialkyl aminoalkyl phosphonate 24.1 to produce the substituted amine 24.2. The preparation of amines by reacting amines with alkyl halides is described, for example, in Comprehensive Organic Transformations, by R. C. Larock, VCH, 1989, p. 397. Typically, the components are reacted together in a polar solvent such as an alkanol or dimethylformamide and the like, to yield the substituted amine 24.2. The latter compound is then converted into the carboxylic acid 24.3, by means of the series of reactions shown in Scheme 14.

For example, the chloromethyl thiazole 14.1 is reacted at 50° C. in acetonitrile solution containing potassium carbonate, with one molar equivalent of a dialkyl aminomethyl phosphonate 24.4, prepared as described in Bioorg. Chem., 2001, 29, 77, to afford the substituted amine 24.5. The product is then converted, using the reactions shown in Scheme 14, into the carboxylic acid 24.6.

Using the above procedures, but employing, in place of the dialkyl aminoethyl phosphonate 24.4, different dialkyl aminoalkyl phosphonates 24.1, the corresponding products 24.3 are obtained.

Scheme 25 illustrates the preparation of carboxylic acids 9.1 in which the phosphonate moiety is attached to the amine component by means of a saturated or unsaturated alkyl chain and a phenyl ring. In this procedure, the chloromethylthiazole 14.1 is reacted with allylamine 25.1, using the procedures described above (Scheme 24) to afford allyl-(2-isopropyl-thiazol-4ylmethyl)-amine 25.2. The ester amine is then converted, by means of the series of reactions shown in Scheme 14, into 2-[3-allyl-3-(2-isopropyl-thiazol-4-ylmethyl)-ureido]-3-methyl-butyric acid methyl ester 25.3. This material is coupled with a dialkyl bromo-substituted phenylphosphonate 25.4, under the conditions of the palladium-catalyzed Heck reaction, to afford the coupled product 25.5. The coupling of aryl halides with olefins by means of the Heck reaction is described, for example, in Advanced Organic Chemistry, by F. A. Carey and R. J. Sundberg, Plenum, 2001, p. 503ff. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Hydrolysis of the methyl ester, as described above, then yields the carboxylic acid 25.6.

Optionally, the double bond present in the product 25.6 is reduced to afford the dihydro analog 25.7. The double bond is reduced in the presence of a palladium catalyst, such as, for example, 5% palladium on carbon, in a solvent such as methanol or ethanol, to afford the product 25.7.

For example, the allyl-substituted urea 25.3 is reacted with a dialkyl 4-bromophenyl phosphonate 25.8, prepared as described in J. Chem. Soc., Perkin Trans., 1977, 2, 789 in the presence of tetrakis(triphenylphosphine)palladium (0) and triethylamine, to afford the phosphonate ester 25.9. Ester hydrolysis, as described above, then affords the carboxylic acid 25.10. Hydrogenation, as described above, then affords the saturated analog 25.11.

Using the above procedures, but employing, in place of the 4-bromophenyl phosphonate 25.8, different bromophenyl phosphonates 25.4, the corresponding products 25.6 and 25.7 are obtained.

Scheme 26 illustrates the preparation of carboxylic acids 11.1 in which the phosphonate moiety is attached to the valine substructure. In this procedure, 2-amino-4-bromo-3-methyl-butyric acid methyl ester 26.1, prepared as described in U.S. Pat. No. 5,346,898, is reacted with a chloroformate, for example 4-nitrophenyl chloroformate, to prepare the activated derivative 26.2 in which X is a leaving group. For example, the aminoester 26.1 is reacted with 4-nitrophenyl-chloroformate in dichloromethane at 0° C., as described in U.S. Pat. No. 5,484,801, to afford the product 26.2 in which X is 4-nitrophenoxy. The latter compound is reacted with (2 isopropyl-thiazol-4-ylmethyl)-methyl-amine 26.3, prepared as described in U.S. Pat. No. 5,484,801, in the presence of a base such as triethylamine or dimethylaminopyridine, in an inert solvent such as dichloromethane or tetrahydrofuran, to afford 4-bromo-2-[3-(2-isopropyl-thiazol-4ylmethyl)-3-methyl-ureido]-3-methyl-butyric acid methyl ester 26.4. The bromo compound 26.4 is then oxidized to afford the aldehyde 26.5. The oxidation of bromo compounds to afford the corresponding aldehydes is described above (Scheme 22). In a typical procedure, the bromo compound is heated at 80° C. in dimethylsulfoxide solution, optionally in the presence of silver salt such as silver perchlorate or silver tetrafluoborate, as described in J. Am. Chem. Soc., 81, 4113, 1959, to afford 2-[3-(2-isopropyl-thiazol-4-ylmethyl)-3-methylureido]-3-methyl-4-oxo-butyric acid methyl ester 26.5. The aldehyde is then subjected to a reductive amination procedure, in the presence of a dialkyl aminoalkyl phosphonate 26.6, to afford the amine product 26.7. The preparation of amines by means of reductive alkylation reactions is described above (Scheme 22). Equimolar amounts of the aldehyde 26.5 and the amine 26.6 are reacted in the presence of a boron-containing reducing agent such as, for example, sodium triacetoxyborohydride, to yield the amine 26.7. The methyl ester is then hydrolyzed, as described above, to yield the carboxylic acid 26.8.

For example, 2-[3-(2-isopropyl-thiazol-4-ylmethyl)-3-methyl-ureido]-3-methyl-4-oxo-butyric acid methyl ester 26.5 is reacted with a dialkyl aminoethylphosphonate 26.9 and sodium cyanoborohydride, to afford the amine product 26.10. The methyl ester is then hydrolyzed, as described above to yield the carboxylic acid 26.11.

Using the above procedures, but employing, in place of the dialkyl aminoethylphosphonate 26.9, different aminoalkyl phosphonates 26.6, the corresponding products 26.8 are obtained. Alternatively, the bromo-substituted methyl ester 26.4 is then reacted with a dialkyl mercaptoalkyl phosphonate 26.12 to afford the thioether 26.13. The preparation of thioethers by the reaction of bromo compounds with thiols is described, for example, in Synthetic Organic Chemistry, R. B. Wagner, H. D. Zook, Wiley, 1953, p. 787. The reactants are combined in the presence of a suitable base, such as sodium hydroxide, dimethylamino pyridine, potassium or cesium carbonate and the like, in a polar organic solvent such as dimethylformamide or ethanol, to afford the thioether 26.13. The methyl ester is then hydrolyzed, as described above to yield the carboxylic acid 26.14.

For example, the bromo compound 26.4 is reacted with a dialkyl mercaptoethyl phosphonate 26.15, the preparation of which is described in Aust. J. Chem., 43, 1123, 1990, in dimethylformamide solution, in the presence of cesium carbonate, to produce the thio ether product 26.16. The methyl ester is then hydrolyzed, as described above, to yield the carboxylic acid 26.17.

Using the above procedures, but employing, in place of the dialkyl mercaptoethyl phosphonate 26.15, different mercaptoalkyl phosphonates 26.12, the corresponding products 26.14 are obtained.

Scheme 22

Method

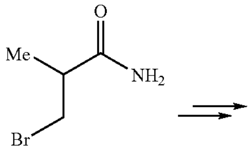

22.1

-continued
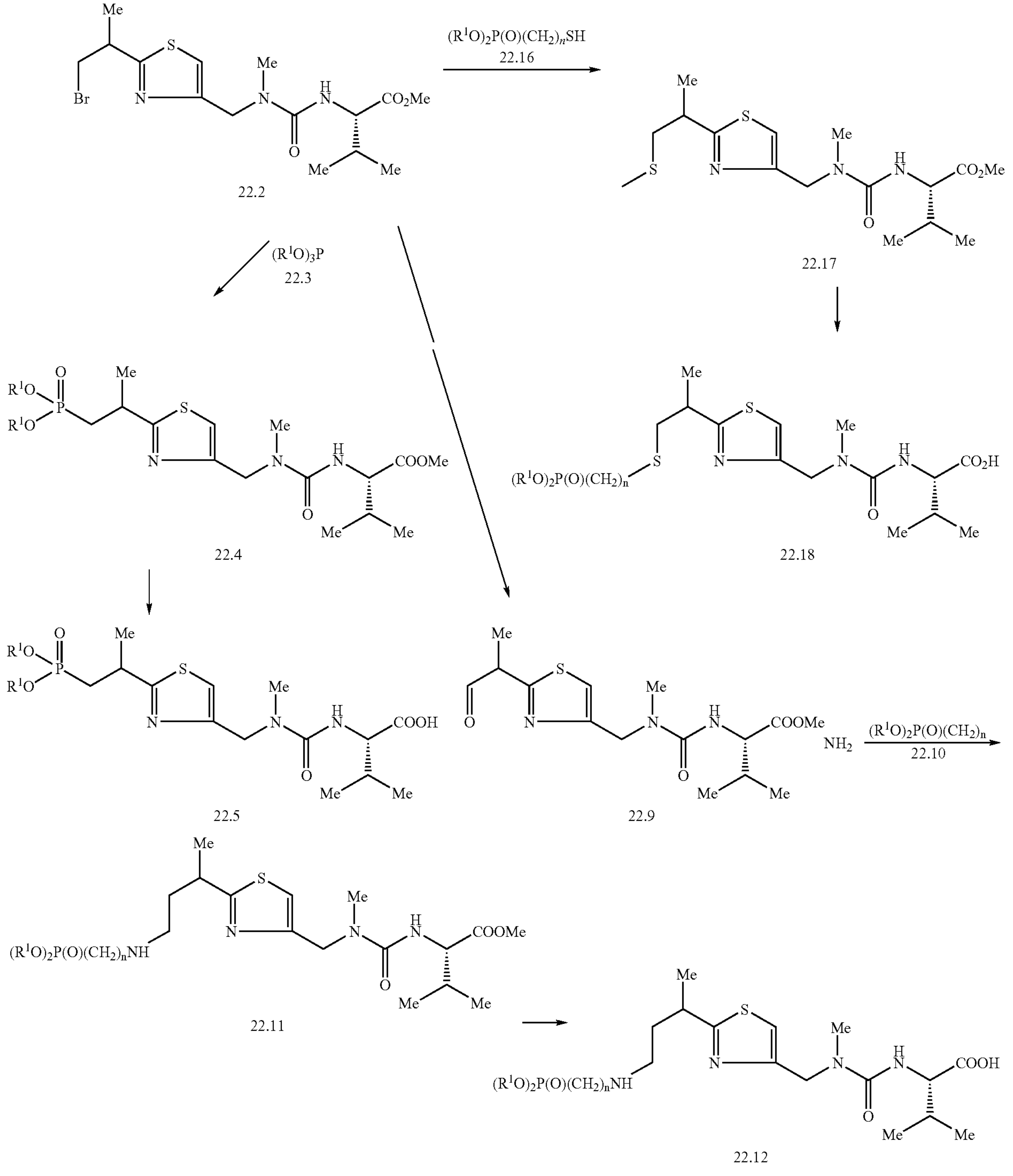
22.2 22.17 22.4 22.18 22.5 22.9 22.11 22.12
Example 1
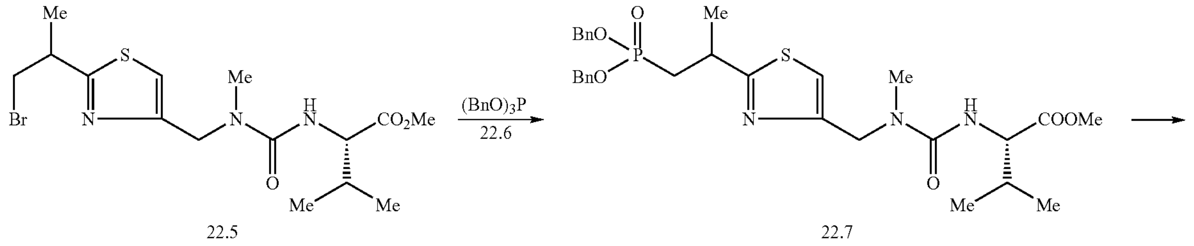
22.5 22.7

-continued
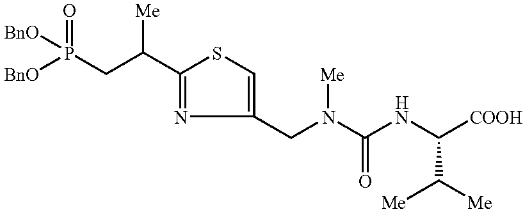
22.8
Example 2
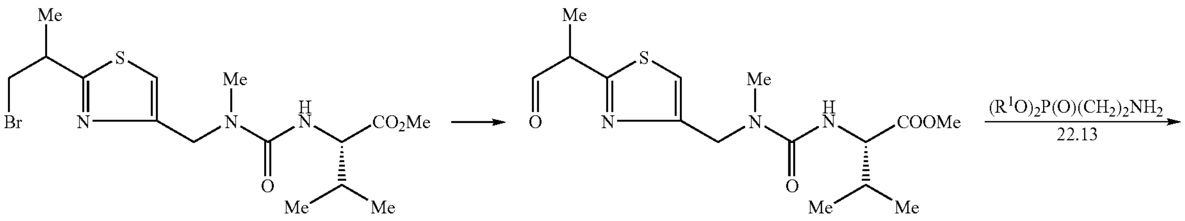
22.2 22.9
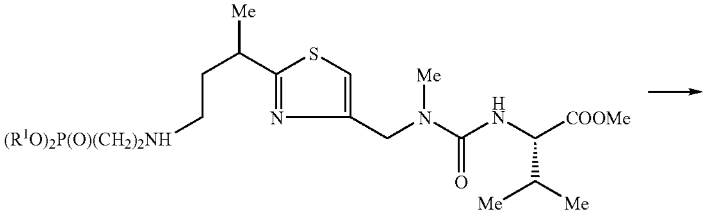
22.14
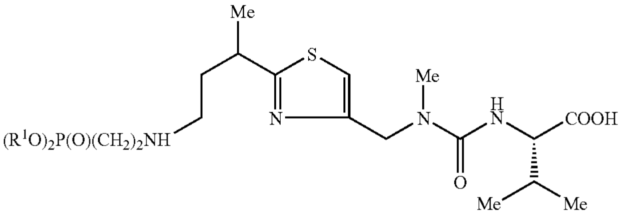
22.15
Example 3
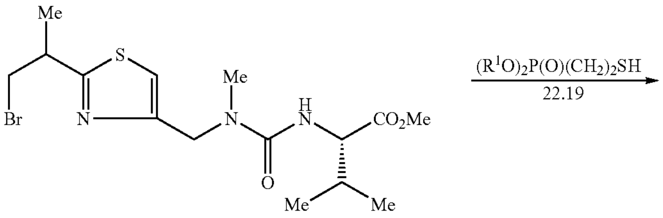
22.2
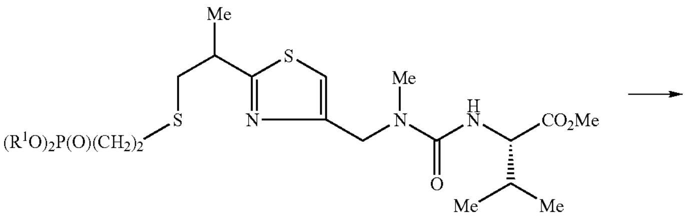
22.20

-continued
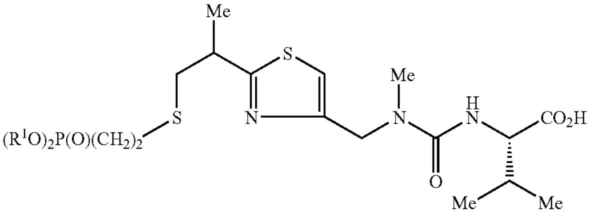
22.21
Scheme 23
Method
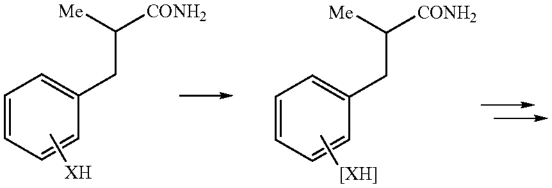
X = O, S
23.1
23.2
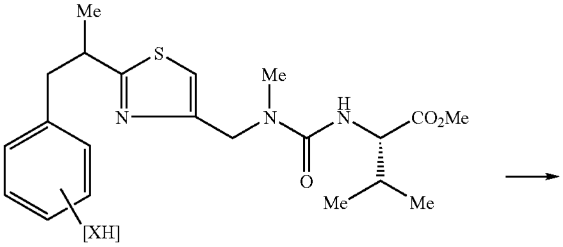
23.3
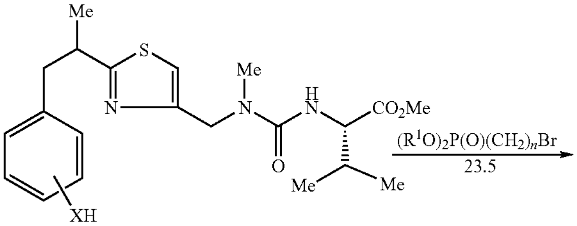
23.4
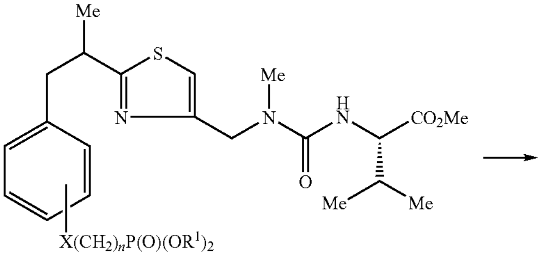
23.6
-continued
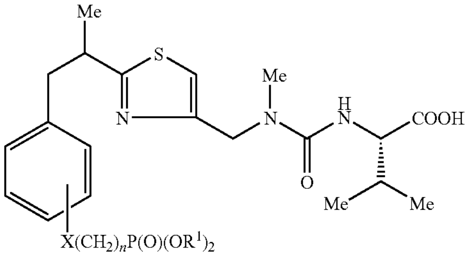
23.7
Example
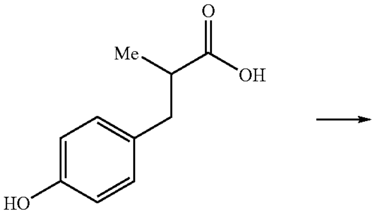
23.8
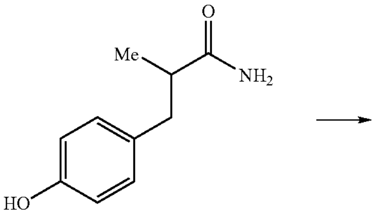
23.9
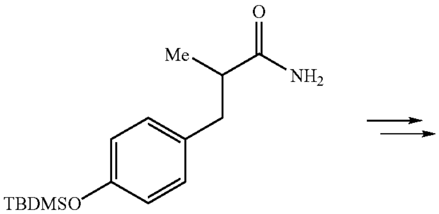
23.10

-continued
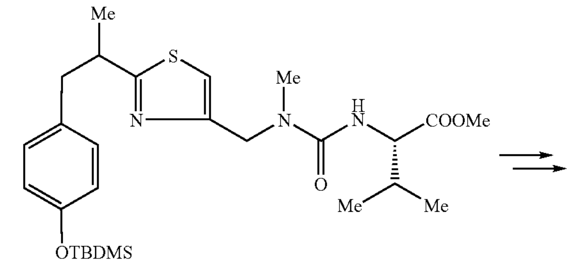
23.11
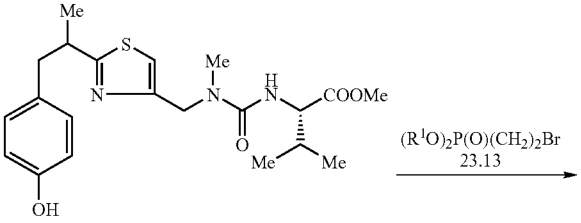
23.12
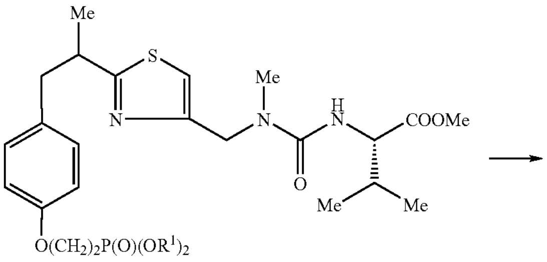
23.14
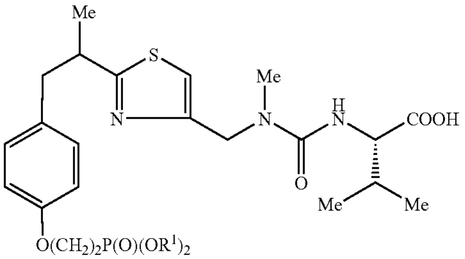
23.15
Scheme 24
Method
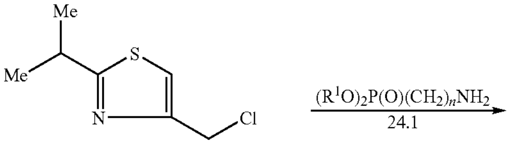
14.1
-continued
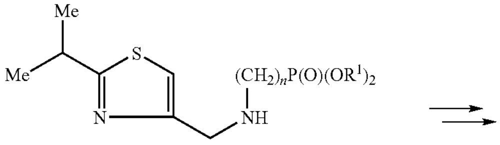
24.2
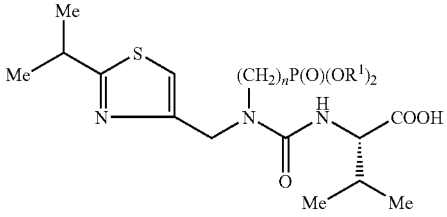
24.3
Example
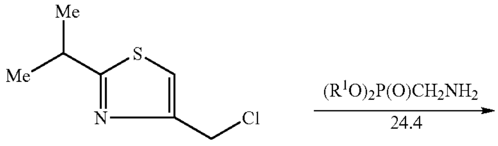
14.1
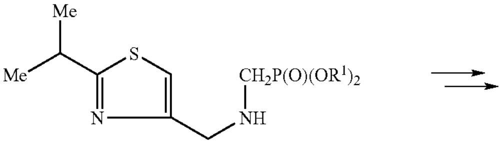
24.5
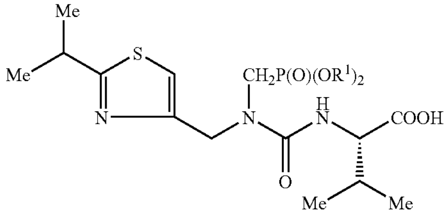
24.6
Scheme 25
Method
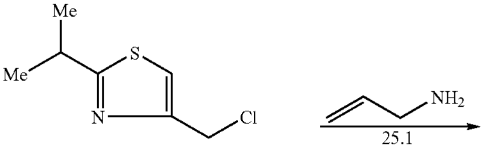
14.1
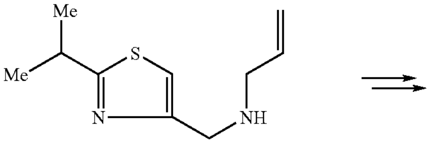
25.2

-continued
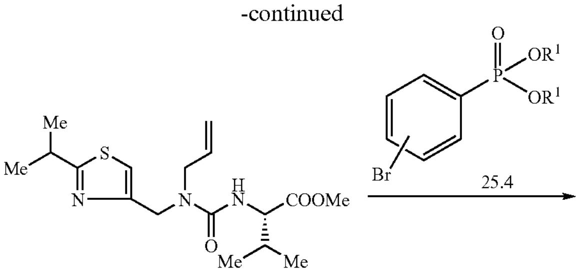
25.3
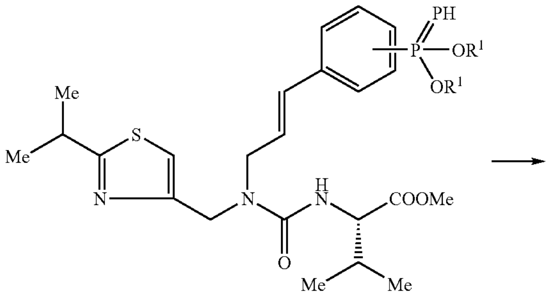
25.5
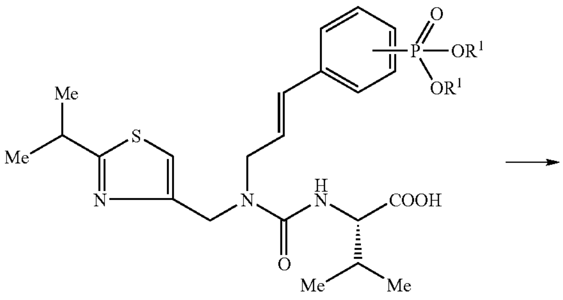
25.6
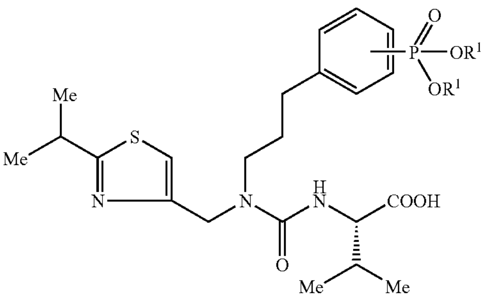
25.7
-continued
Example
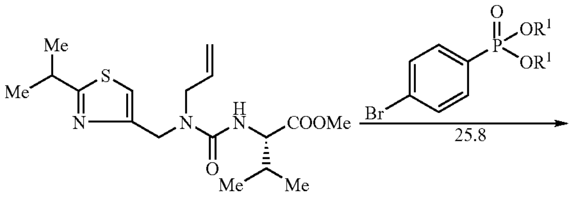
25.3
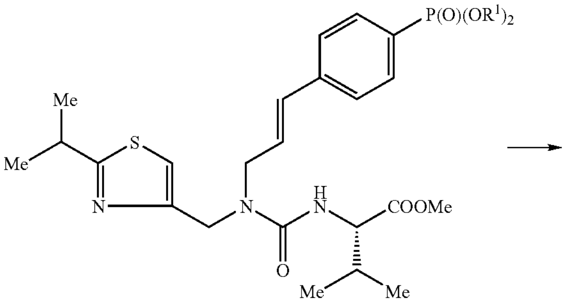
25.9
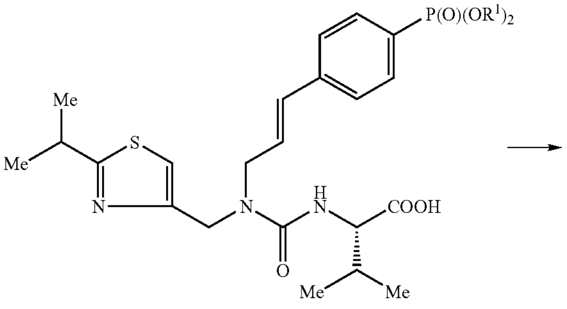
25.10
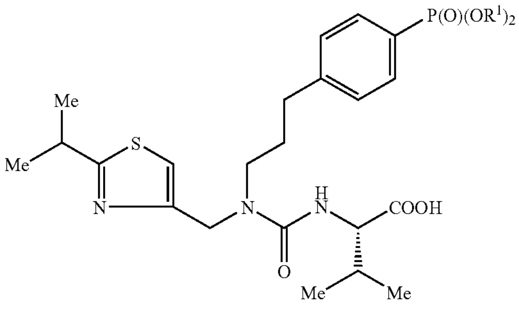
25.11

Scheme 26
Method
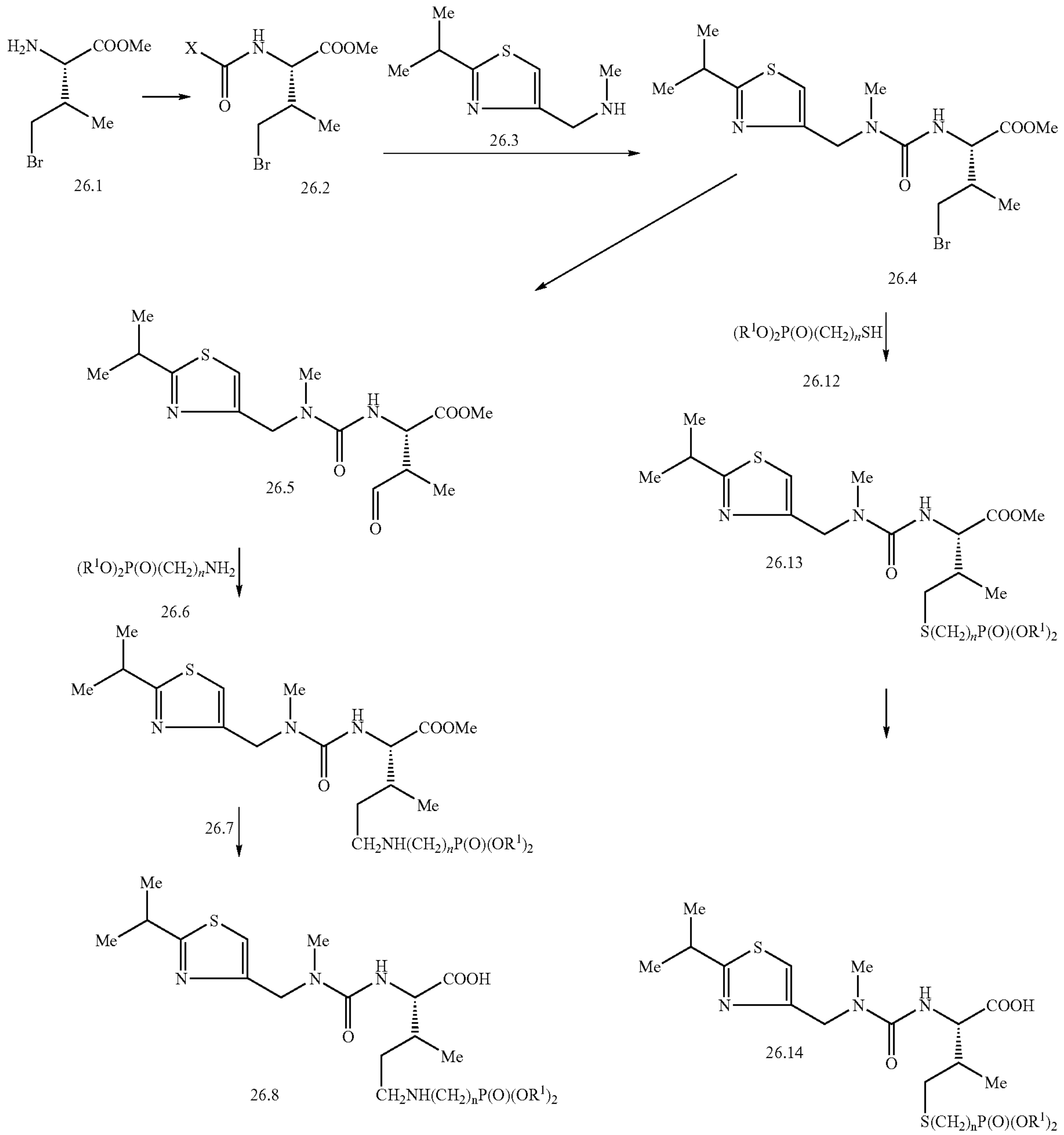
Example 1
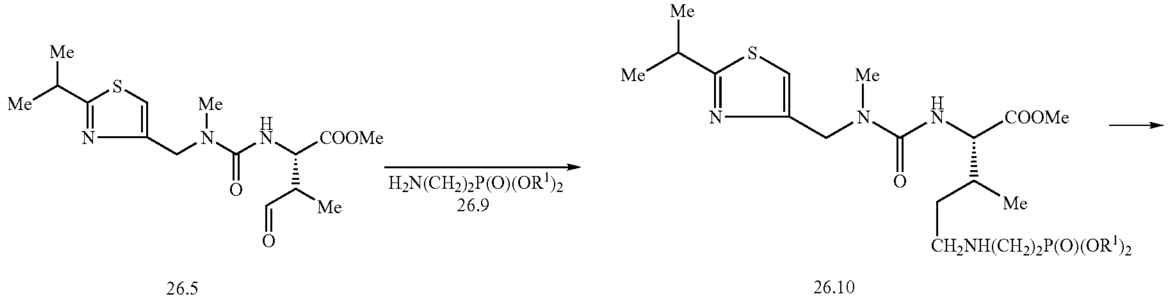

-continued

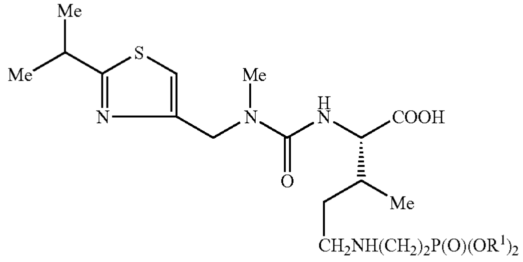

26.11

Interconversions of the Phosphonates R-link-P(O)($OR^1$)$_2$, R-link-P(O)($OR^1$)(OH) and R-link-P(O)(OH)$_2$.

Schemes 1-26 described the preparations of phosphonate esters of the general structure R-link-P(O)($OR^1$)$_2$, in which the groups $R^1$, the structures of which are defined in Chart 1, may be the same or different. The $R^1$ groups attached to a phosphonate esters 1-7, or to precursors thereto, may be changed using established chemical transformations. The interconversions reactions of phosphonates are illustrated in Scheme 27. The group R in Scheme 27 represents the substructure to which the substituent link-P(O)($OR^1$)$_2$ is attached, either in the compounds 1-7 or in precursors thereto. The $R^1$ group may be changed, using the procedures described below, either in the precursor compounds, or in the esters 1-7. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 27.1 into the corresponding phosphonate monoester 27.2 (Scheme 27, Reaction 1) can be accomplished by a number of methods. For example, the ester 27.1 in which $R^1$ is an aralkyl group such as benzyl, can be converted into the monoester compound 27.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110° C. The conversion of the diester 27.1 in which $R^1$ is an aryl group such as phenyl, or an alkenyl group such as allyl, into the monoester 27.2 can be effected by treatment of the ester 27.1 with a base such as aqueous sodium hydroxide in acetonitrile or lithium hydroxide in aqueous tetrahydrofuran.

Phosphonate diesters 27.1 in which one of the groups $R^1$ is aralkyl, such as benzyl, and the other is alkyl, can be converted into the monoesters 27.2 in which $R^1$ is alkyl by hydrogenation, for example using a palladium on carbon catalyst. Phosphonate diesters in which both of the groups $R^1$ are alkenyl, such as allyl, can be converted into the monoester 27.2 in which $R^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in J. Org. Chem., 38 3224 1973 for the cleavage of allyl carboxylates.

The conversion of a phosphonate diester 27.1 or a phosphonate monoester 27.2 into the corresponding phosphonic acid 27.3 (Scheme 27, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 27.2 in which $R^1$ is aralkyl such as benzyl, can be converted into the corresponding phosphonic acid 27.3 by hydrogenation over a palladium catalyst, or by treatment with hydrogen chloride in an ethereal solvent such as dioxan. A phosphonate monoester 27.2 in which $R^1$ is alkenyl such as, for example, allyl, can be converted into the phosphonic acid 27.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 27.1 in which $R^1$ is benzyl is described in J. Org. Chem., 24, 434, 1959. Platinum-catalyzed hydrogenolysis of phosphonate esters 27.1 in which $R^1$ is phenyl is described in J. Amer. Chem. Soc., 78, 2336, 1956.

The conversion of a phosphonate monoester 27.2 into a phosphonate diester 27.1 (Scheme 27, Reaction 4) in which the newly introduced $R^1$ group is alkyl, aralkyl, haloalkyl such as chloroethyl, or aralkyl can be effected by a number of reactions in which the substrate 27.2 is reacted with a hydroxy compound $R^1$OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 27.2 to the diester 27.1 can be effected by the use of the Mitsonobu reaction, as described above (Scheme 16). The substrate is reacted with the hydroxy compound $R^1$OH, in the presence of diethyl azodicarboxylate and a triarylphosphine such as triphenyl phosphine. Alternatively, the phosphonate monoester 27.2 can be transformed into the phosphonate diester 27.1, in which the introduced $R^1$ group is alkenyl or aralkyl, by reaction of the monoester with the halide $R^1$Br, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 27.2 is transformed into the chloro analog RP(O)

$(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester 27.1.

A phosphonic acid R-link-$P(O)(OH)_2$ can be transformed into a phosphonate monoester $RP(O)(OR^1)(OH)$ (Scheme 27, Reaction 5) by means of the methods described above of for the preparation of the phosphonate diester R-link-$P(O)(OR^1)_2$ 27.1, except that only one molar proportion of the component $R^1OH$ or $R^1Br$ is employed.

A phosphonic acid R-link-$P(O)(OH)_2$ 27.3 can be transformed into a phosphonate diester R-link-$P(O)(OR^1)_2$ 27.1 (Scheme 27, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine.

Alternatively, phosphonic acids 27.3 can be transformed into phosphonic esters 27.1 in which $R^1$ is aryl, by means of a coupling reaction employing, for example, dicyclohexylcarbodiimide in pyridine at ca 70° C. Alternatively, phosphonic acids 27.3 can be transformed into phosphonic esters 27.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 27.1.

Scheme 26

Example 2

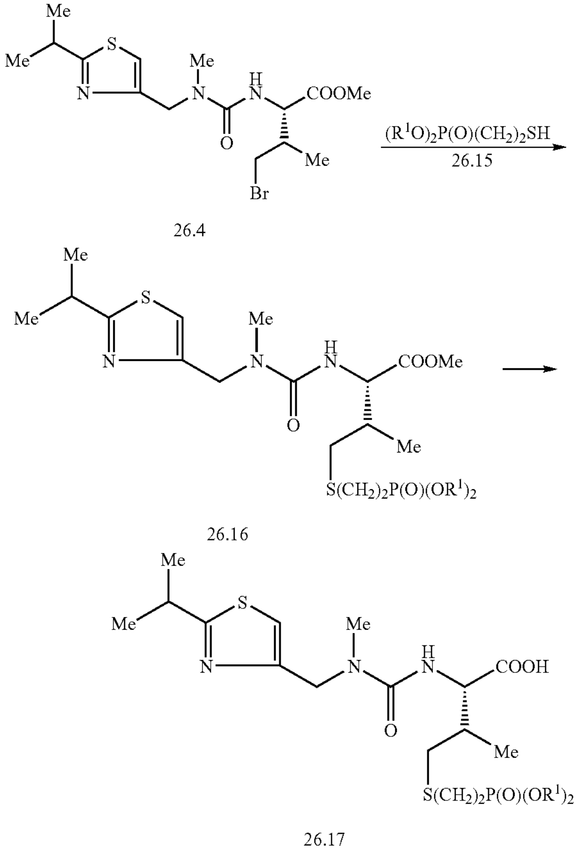

Scheme 27

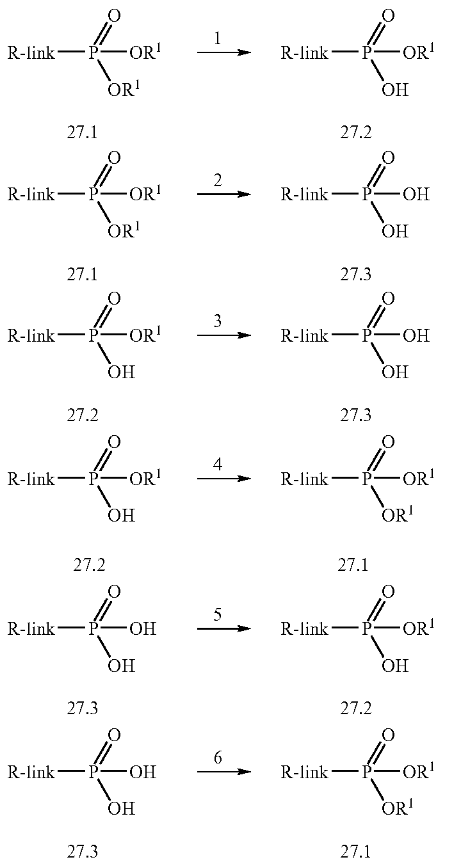

General Applicability of Methods for Introduction of Phosphonate Substituents.

The procedures described above for the conversion of various functional groups into phosphonate moieties are of general application. For example, the methods described above for the introduction of phosphonate groups into the phenylalanine moiety, can, with appropriate modifications known to those skilled in the art, be applied to the introduction of phosphonate groups into the thiazole compounds 1.5, 9.1 and 11.1, and for the preparation of the phosphonate esters 3. Similarly, the methods described above for the introduction of phosphonate groups into the thiazole compounds 1.5, 9.1 and 11.1 can, with appropriate modifications known to those skilled in the art, be applied to the introduction of phosphonate groups into the phenylalanine intermediates 4.1 and for the preparation of the compounds 3.

Phosphonate Esters 1-7 Incorporating Carbamate Moieties.

The phosphonate esters 1-7 in which the $R^2CO$ or $R^3CO$ groups are formally derived from the carboxylic acid synthons 14-16, 19, 21, 22, 25, 34, 51 or 52 as shown in Charts 2a, 2b, and 2c, contain a carbamate moiety. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 28 illustrates various methods by which the carbamate linkage can be synthesized. As shown in Scheme 28, in the general reaction generating carbamates, a carbinol 28.1 is converted into the activated derivative 28.2 in which Lv is a leaving group such as halo, imidazolyl, benztriazolyl and the like, as described below. The activated derivative 28.2 is then reacted with an amine 28.3, to afford the carbamate product 28.4. Examples 1-7 in Scheme 28 depict methods by which the general reaction can be effected. Examples 8-10 illustrate alternative methods for the preparation of carbamates.

Scheme 28, Example 1 illustrates the preparation of carbamates employing a chloroformyl derivative of the carbinol 28.5. In this procedure, the carbinol 28.5 is reacted with phosgene, in an inert solvent such as toluene, at about 0° C., as described in Org. Syn. Coil. Vol. 3, 167, 1965, or with an equivalent reagent such as trichloromethoxy chloroformate, as described in Org. Syn. Coil. Vol. 6, 715, 1988, to afford the chloroformate 28.6. The latter compound is then reacted with the amine component 28.3, in the presence of an organic or inorganic base, to afford the carbamate 28.7. cFor example, the chloroformyl compound 28.6 is reacted with the amine 28.3 in a water-miscible solvent such as tetrahydrofuran, in the presence of aqueous sodium hydroxide, as described in Org. Syn. Coll. Vol. 3, 167, 1965, to yield the carbamate 28.7. cAlternatively, the reaction is preformed in dichloromethane in the presence of an organic base such as diisopropylethylamine or dimethylaminopyridine.

Scheme 28, Example 2 depicts the reaction of the chloroformate compound 28.6 with imidazole, 28.7, to produce the imidazolide 28.8. The imidazolide product is then reacted with the amine 28.3 to yield the carbamate 28.7. The preparation of the imidazolide is performed in an aprotic solvent such as dichloromethane at 0° C., and the preparation of the carbamate is conducted in a similar solvent at ambient temperature, optionally in the presence of a base such as dimethylaminopyridine, as described in J. Med. Chem., 1989, 32, 357.

Scheme 28 Example 3, depicts the reaction of the chloroformate 28.6 with an activated hydroxyl compound R"OH, to yield the mixed carbonate ester 28.10. The reaction is conducted in an inert organic solvent such as ether or dichloromethane, in the presence of a base such as dicyclohexylamine or triethylamine. The hydroxyl component R"OH is selected from the group of compounds 28.19-28.24 shown in Scheme 28, and similar compounds. For example, if the component R"OH is hydroxybenztriazole 28.19, N-hydroxysuccinimide 28.20, or pentachlorophenol, 28.21, the mixed carbonate 28.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 28.22 or 2-hydroxypyridine 28.23 can be performed in an ethereal solvent in the presence of triethylamine, as described in Syn., 1986, 303, and Chem. Ber. 118, 468, 1985.

Scheme 28 Example 4 illustrates the preparation of carbamates in which an alkyloxycarbonylimidazole 28.8 is employed. In this procedure, a carbinol 28.5 is reacted with an equimolar amount of carbonyl diimidazole 28.11 to prepare the intermediate 28.8. The reaction is conducted in an aprotic organic solvent such as dichloromethane or tetrahydrofuran. The acyloxyimidazole 28.8 is then reacted with an equimolar amount of the amine $R'NH_2$ to afford the carbamate 28.7. The reaction is performed in an aprotic organic solvent such as dichloromethane, as described in Tet. Lett., 42, 2001, 5227, to afford the carbamate 28.7.

Scheme 28, Example 5 illustrates the preparation of carbamates by means of an intermediate alkoxycarbonylbenztriazole 28.13. In this procedure, a carbinol ROH is reacted at ambient temperature with an equimolar amount of benztriazole carbonyl chloride 28.12, to afford the alkoxycarbonyl product 28.13. The reaction is performed in an organic solvent such as benzene or toluene, in the presence of a tertiary organic amine such as triethylamine, as described in Syn., 1977, 704. This product is then reacted with the amine $R'NH_2$ to afford the carbamate 28.7. The reaction is conducted in toluene or ethanol, at from ambient temperature to about 80° C. as described in Syn., 1977, 704.

Scheme 28, Example 6 illustrates the preparation of carbamates in which a carbonate $(R''O)_2CO$, 28.14, is reacted with a carbinol 28.5 to afford the intermediate alkyloxycarbonyl intermediate 28.15. The latter reagent is then reacted with the amine $R'NH_2$ to afford the carbamate 28.7. The procedure in which the reagent 28.15 is derived from hydroxybenztriazole 28.19 is described in Synthesis, 1993, 908; the procedure in which the reagent 28.15 is derived from N-hydroxysuccimmide 28.20 is described in Tet. Lett., 1992, 2781; the procedure in which the reagent 28.15 is derived from 2-hydroxypyridine 28.23 is described in Tet. Lett., 1991, 4251; the procedure in which the reagent 28.15 is derived from 4-nitrophenol 28.24 is described in Syn. 1993, 103. The reaction between equimolar amounts of the carbinol ROH and the carbonate 28.14 is conducted in an inert organic solvent at ambient temperature.

Scheme 28, Example 7 illustrates the preparation of carbamates from alkoxycarbonyl azides 28.16. in this procedure, an alkyl chloroformate 28.6 is reacted with an azide, for example sodium azide, to afford the alkoxycarbonyl azide 28.16. The latter compound is then reacted with an equimolar amount of the amine $R'NH_2$ to afford the carbamate 28.7. The reaction is conducted at ambient temperature in a polar aprotic solvent such as dimethylsulfoxide, for example as described in Syn., 1982, 404.

Scheme 28, Example 8 illustrates the preparation of carbamates by means of the reaction between a carbinol ROH and the chloroformyl derivative of an amine. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 28.7.

Scheme 28, Example 9 illustrates the preparation of carbamates by means of the reaction between a carbinol ROH and an isocyanate 28.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 28.7.

Scheme 28, Example 10 illustrates the preparation of carbamates by means of the reaction between a carbinol ROH and an amine $R'NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 28.7.

Scheme 28

General reaction

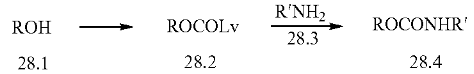

28.1 28.2 28.4

-continued

Examples

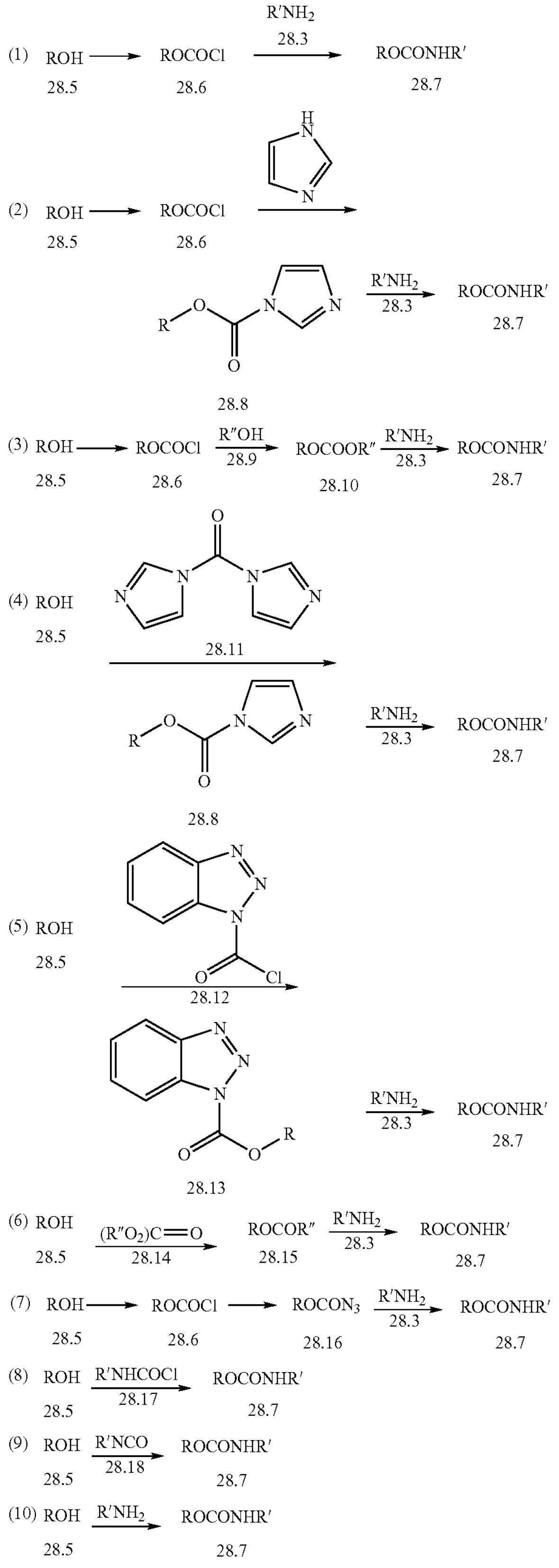

-continued

R″OH =

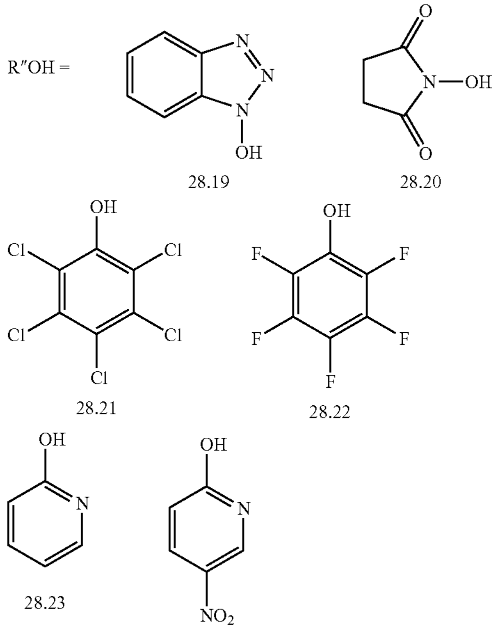

28.19 28.20 28.21 28.22 28.23 28.24

Preparation of Phosphonate Intermediates 6 and 7 with Phosphonate Moieties Incorporated into the Group $R^2COOH$ and $R^3COOH$.

The chemical transformations described in Schemes 1-28 illustrate the preparation of compounds 1-5 in which the phosphonate ester moiety is attached to the thiazole substructure, (Schemes 1-3,9-10, and 11-12), the phenylalanine moiety (Schemes 4-6), and the benzyl moiety (Schemes 7-8).

The various chemical methods employed for the preparation of phosphonate groups can, with appropriate modifications known to those skilled in the art, be applied to the introduction of phosphonate ester groups into the compounds $R^2COOH$ and $R^3COOH$, as defined in Charts 2a, 2b and 2c. The resultant phosphonate-containing analogs, designated as $R^{2a}COOH$ and $R^{3a}COOH$ can then, using the procedures described above, be employed in the preparation of the compounds 6 and 7. The procedures required for the introduction of the phosphonate-containing analogs $R^{2a}COOH$ and $R^{3a}COOH$ are the same as those described above (Schemes 4, 5, and 28) for the introduction of the $R^2CO$ and $R^3CO$ moieties.

Indinavir-like Phosphonate Protease Inhibitors (ILPPI)

Preparation of the Intermediate Phosphonate Esters 1-24.

The structures of the intermediate phosphonate esters 1 to 22 and the structures of the component groups $R^1$, $R^4$, $R^8$, $R^9$, $R^{11}$, X and X' of this invention are shown in Charts 1-3. The structures of the $R^2R^3NH$ components are shown in Chart 4; the structures of the amines components $R^7NHCH(R^6)CONHR^4$ are shown as the structures A1-A16 in Chart 4. The structures of the $R^5XCH_2$ groups are shown in Chart 5, and those of the $R^{10}CO$ components are illustrated in Chart 6. The structures of the $R^7NHCH(R^6)COOH$ components are shown in Chart 10.

Specific stereoisomers of some of the structures are shown in Charts 1-10; however, all stereoisomers are utilized in the syntheses of the compounds 1 to 24. Subsequent chemical modifications to the compounds 1 to 24, as described herein, permit the synthesis of the final compounds of this invention.

The intermediate compounds 1 to 24 incorporate a phosphonate moiety $(R^{10})_2P(O)$ connected to the nucleus by means of a variable linking group, designated as "link" in the attached structures. Charts 7, 8 and 9 illustrate examples of the linking groups present in the structures 1-24.

Schemes 1-207 illustrate the syntheses of the intermediate phosphonate compounds of this invention, 1-22, and of the intermediate compounds necessary for their synthesis. The preparation of the phosphonate esters 23 and 24, in which a phosphonate moiety is incorporated into one of the groups $R^2$, $R^3$, $R^5$, $R^{10}$ or $R^{11}$ is also described below. In compounds 2, 6, 23 and 24 where two groups are the same Chart 4 it is noted that these groups may be independent or identical.

CHART 1

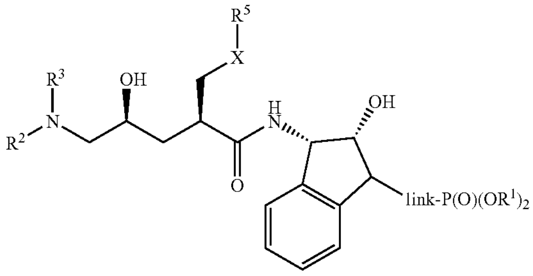

1

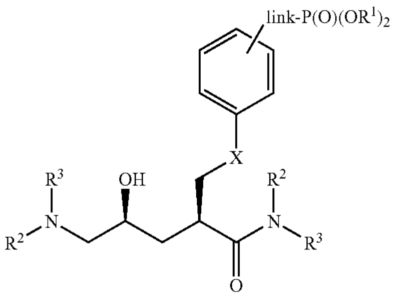

2

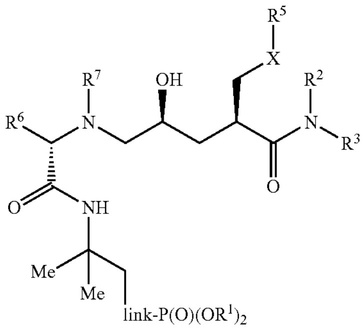

3

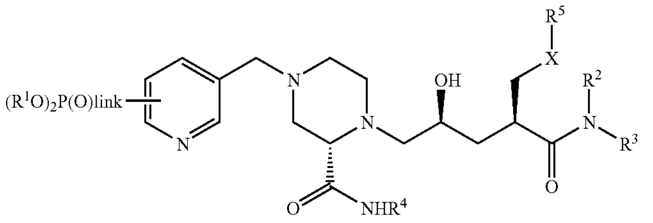

4

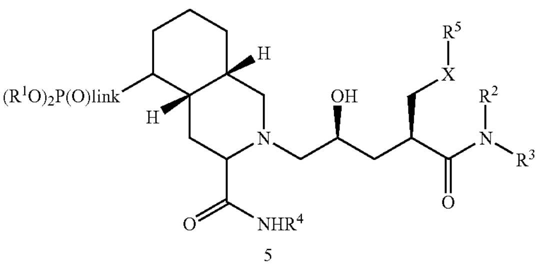

5

CHART 1-continued
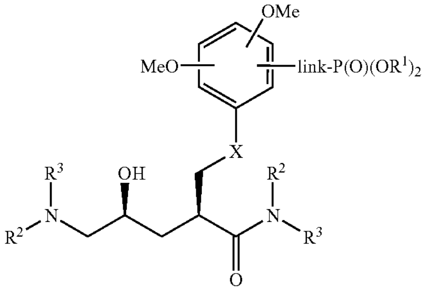
6
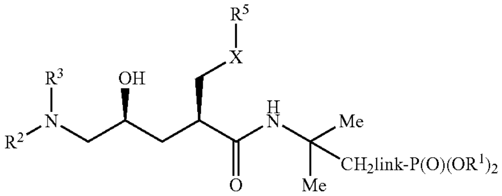
7
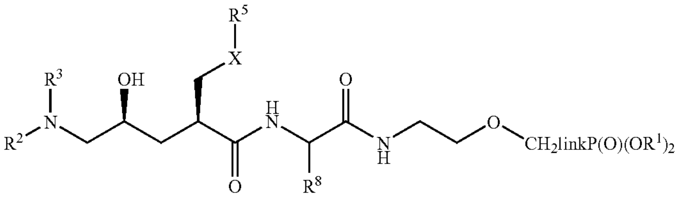
8
$R^1$ = H, alkyl, haloalkyl, alkenyl, aralkyl, aryl
$R^4$ = $CH(CH_3)_3$; $CH_2CF_3$; $CH_2C_6H_4(CH_3)$-2; $CH_2C_6H_3(CH_3)_2$ 2,6
CHART 2
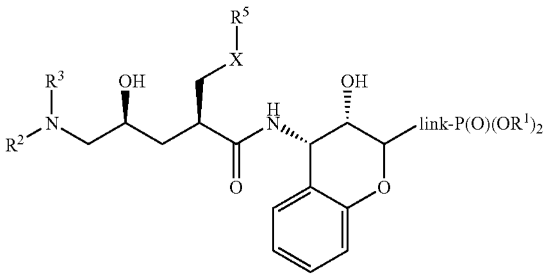
9
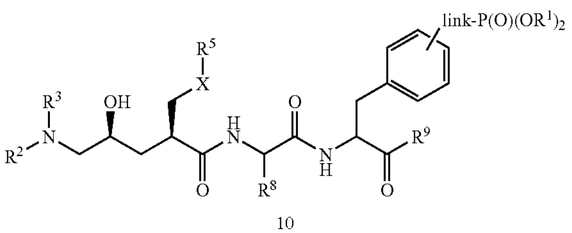
10
CHART 2-continued
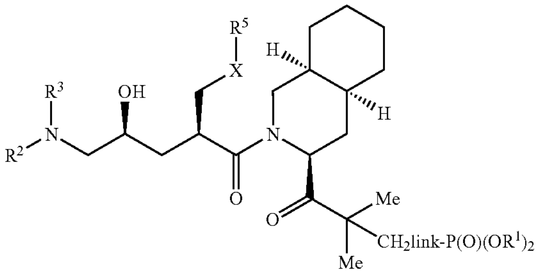
11
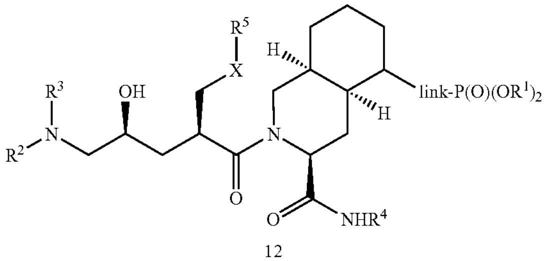
12

CHART 2-continued
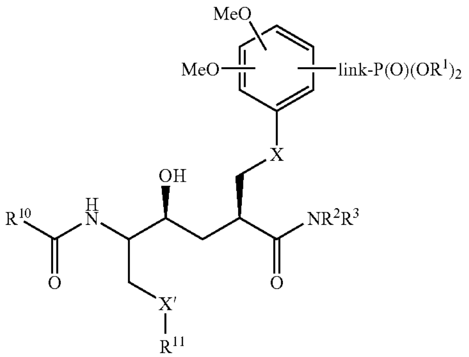
13
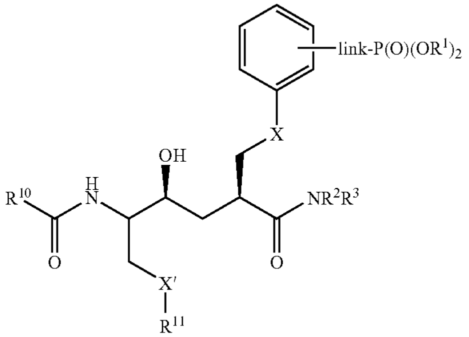
14
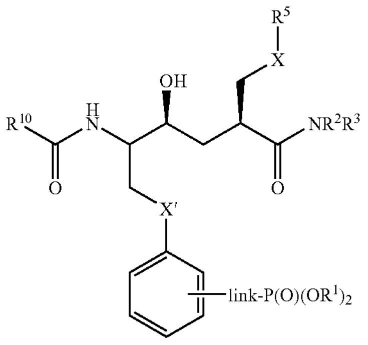
CHART 2-continued
15
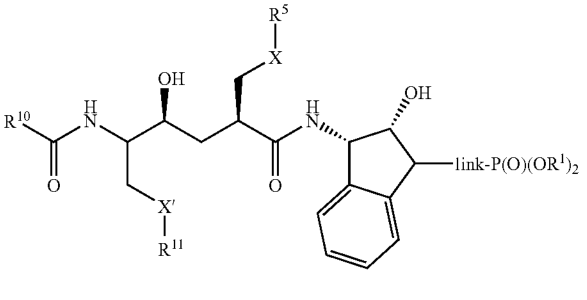
16
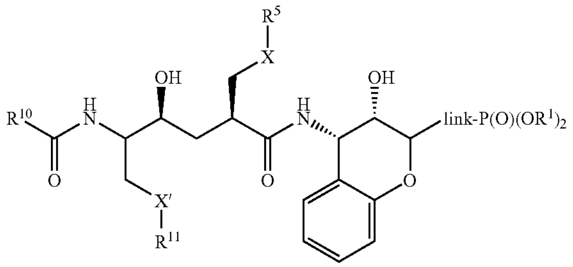
17
$R^{11}$ = phenyl, alkyl
$R^1$ = H, alkyl, haloalkyl, alkenyl, aralkyl, aryl
$R^4$ = $CH(CH_3)_3$; $CH_2CF_3$; $CH_2C_6H_4(CH_3)$-2; $CH_2C_6H_3(CH_3)_2$ 2,6
$R^9$ = morpholino or methoxy
CHART 3
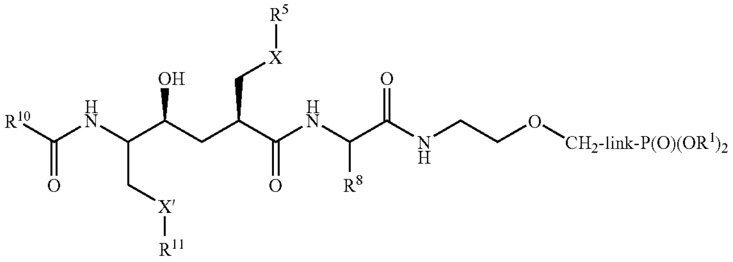
18

CHART 3-continued
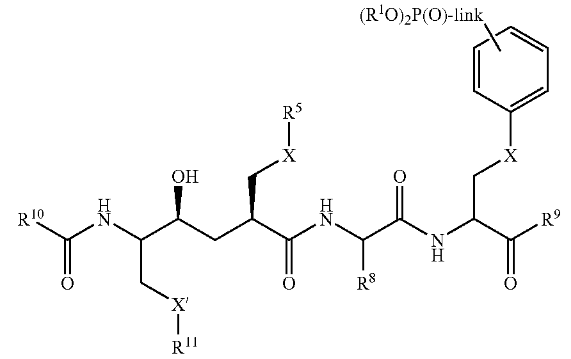
19
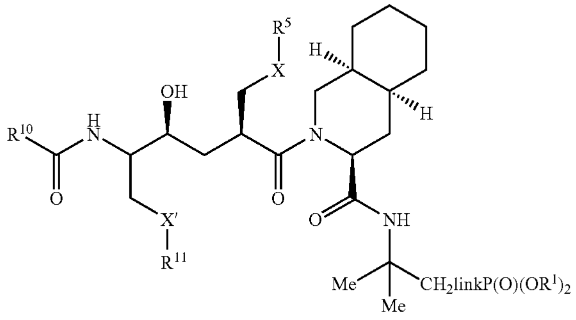
20
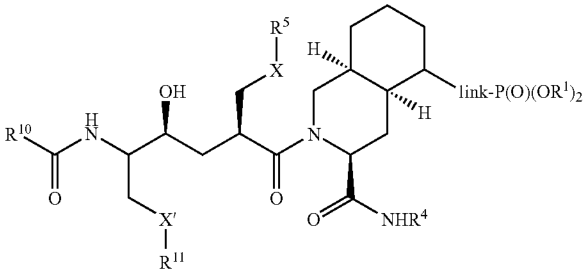
21
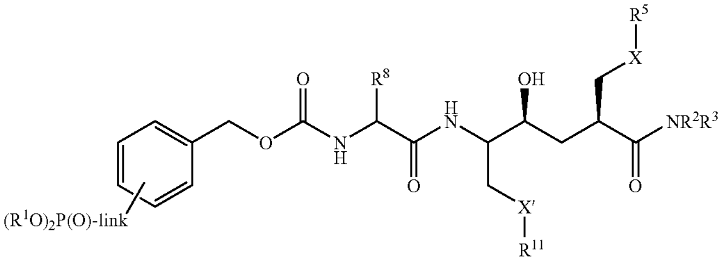
22

CHART 3-continued

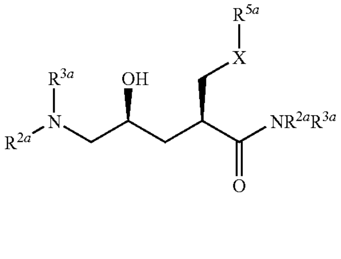

23

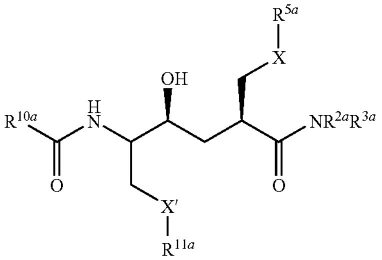

24

$R^{xa}$ = phosphonate containing $R^x$ $R^1$ = H, alkyl, haloalkyl, alkenyl, aralkyl, aryl
$R^4$ = $C(CH_3)3$; $CH_2CF_3$; $CH_2C_6H_4(CH_3)$-2; $CH_2C_6H_3(CH_3)_2$ 2,6
$R^8$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
$R^9$ = morpholino; alkoxy.
$R^{11}$ = phenyl, alkyl
X, X' = S, direct bond

CHART 4

Structures of the $R^2R^3NH$ components

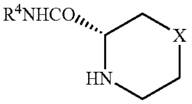

X = NH, $CH_2$

A1

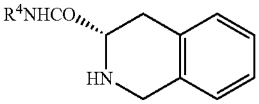

A2

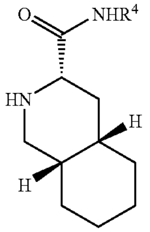

A3

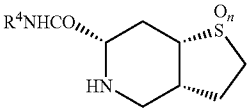

n = 0, 2

A4

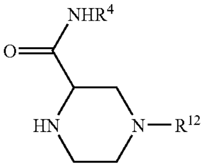

A5

$R^{12}$ =

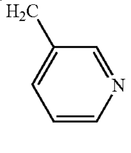

A6

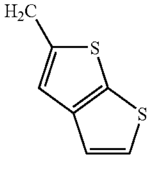

A7

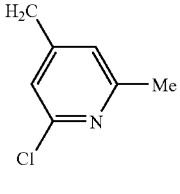

A8

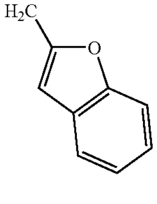

A9

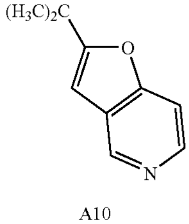

A10

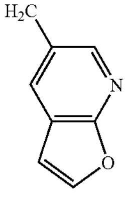

A11

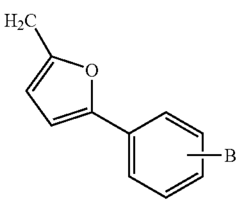

B = F or Cl

A10a

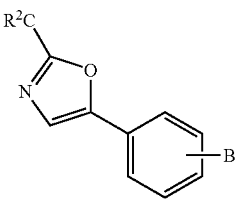

B = F or Cl
R — Me

A10b

CHART 4-continued
Structures of the $R^2R^3NH$ components
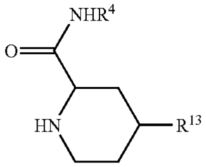
$R^{13}$ = $OCH_2Ph$
S-3-pyridyl
S-4-pyridyl
$OCH_2$-4-pyridyl
A12
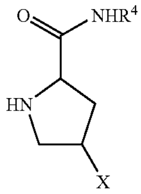
X = Cl, OMe
A13
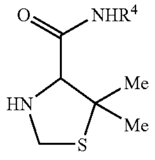
A14
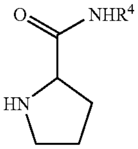
A15
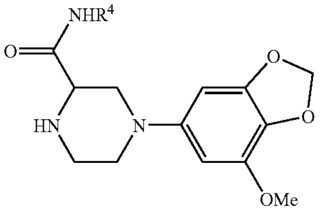
A16
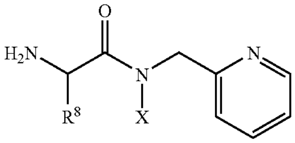
X = H or Me
A17
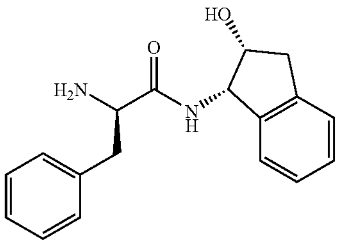
A18
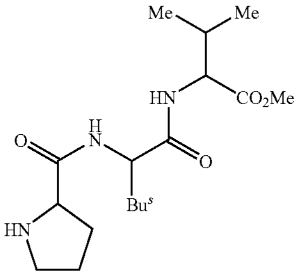
A19
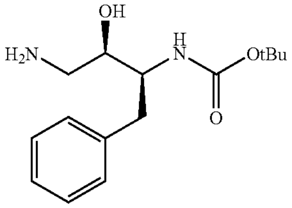
A20
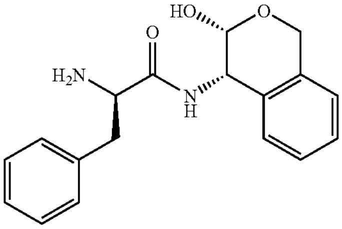
A21
CHART 5
Structures of the $R^5XCH_2$ groups.
$R^5SCH_2$ = S-alkyl
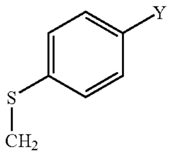
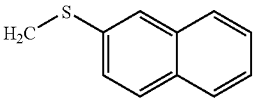
24 25 26
Y = H, F
CHART 5-continued
Structures of the $R^5XCH_2$ groups.
$R^5CH_2$ = alkyl
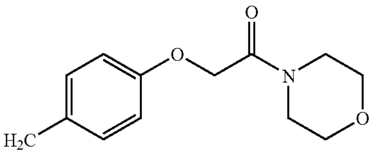
27 28
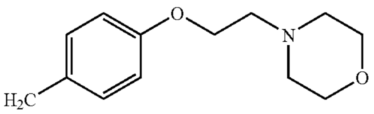
29

CHART 5-continued
Structures of the $R^5XCH_2$ groups.
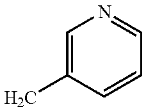
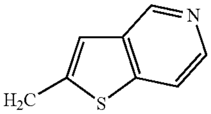
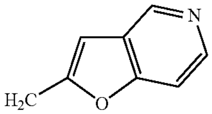
30 30a 30b
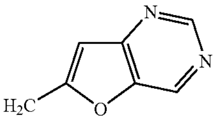
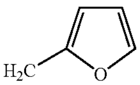
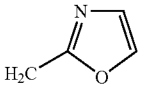
30c 30d 30e
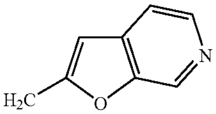
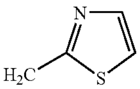
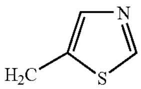
30f 30g 30h
CHART 5-continued
Structures of the $R^5XCH_2$ groups.
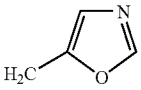
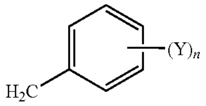
30i 31
Y = H, $OC_2H_5$, $OCH_2O_6H_5$, MeO, $(MeO)_2$, $(MeO)_3$, $CH_2CH_2OH$, OH, Ha, CN, Ph, $OCH_2O$, $OCH_2Ph$
CHART 6
Structures of the $R^{10}CO$ components
$R^{10}CO$ = alkyl OCO
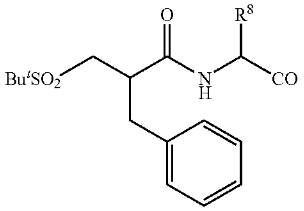
32 33
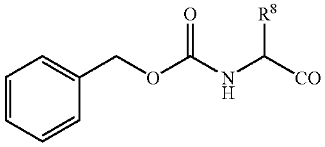
34
CHART 7
Examples of linking groups
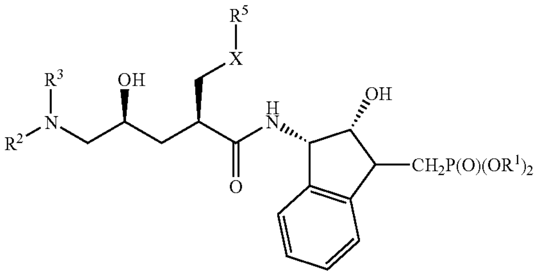
L1
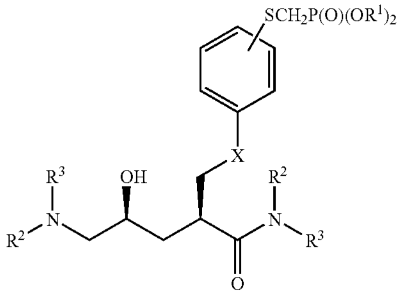
L2

CHART 7-continued
| Examples of linking groups |
| --- |
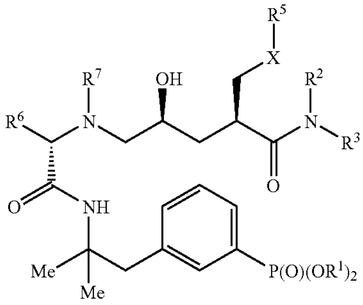
L3
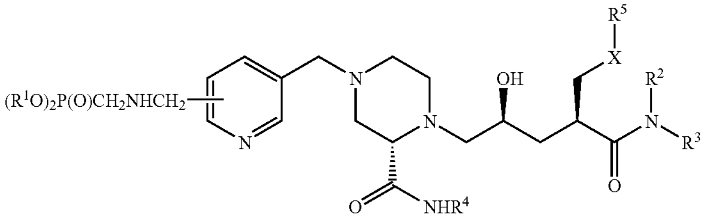
L4
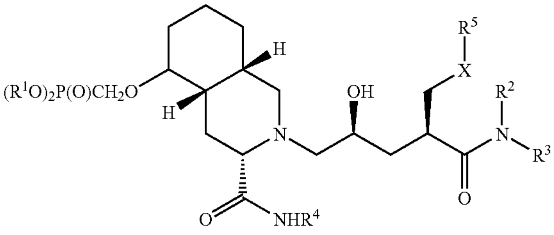
L5
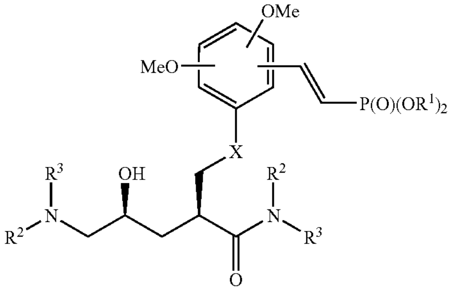
L6
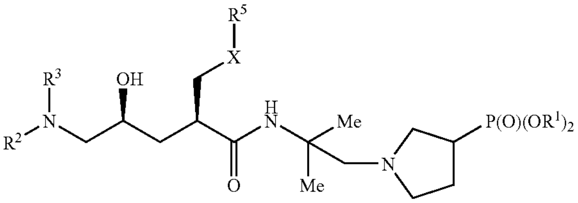
L7

CHART 7-continued
Examples of linking groups
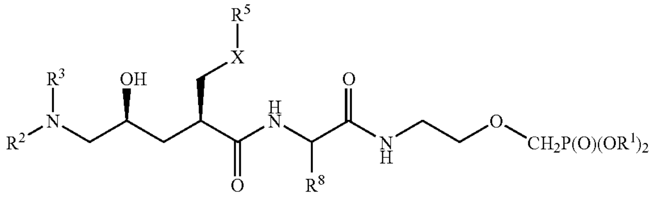
L8
CHART 8
Examples of linking groups
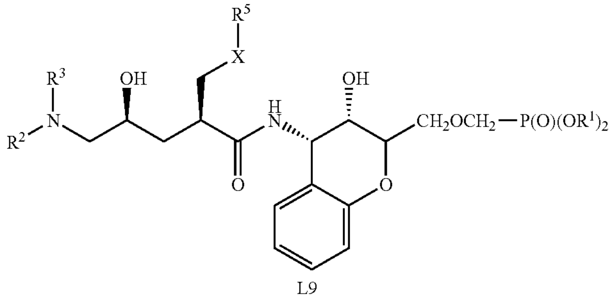
L9
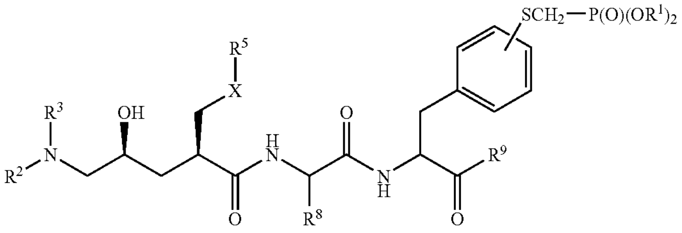
L10
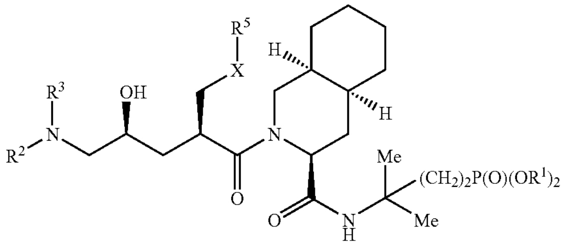
L11
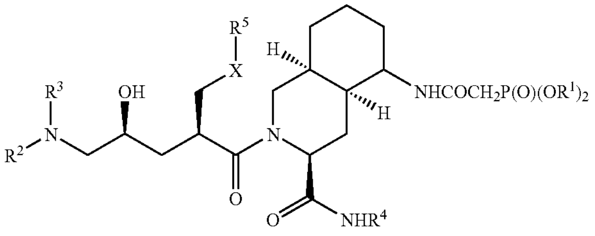
L12

CHART 8-continued
Examples of linking groups
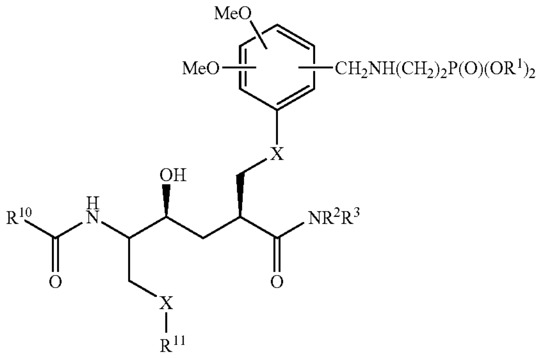
L13
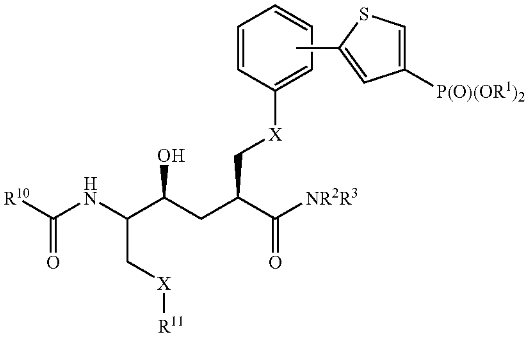
L14
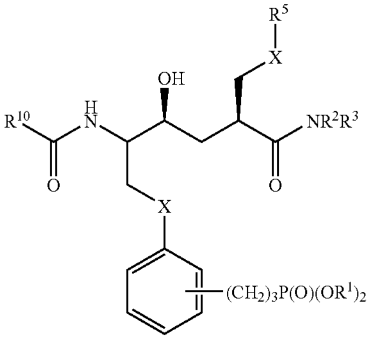
L15
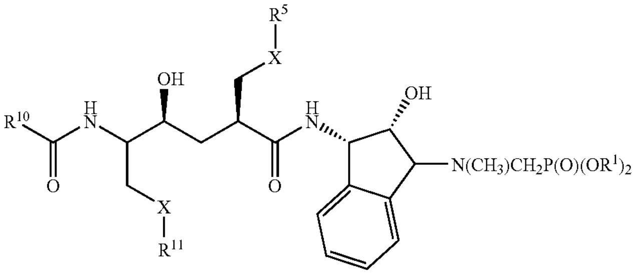
L16
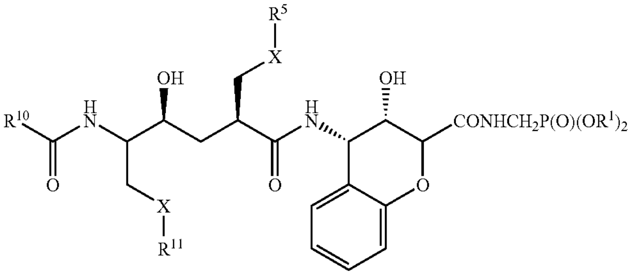
L17

CHART 9
Examples of linking groups
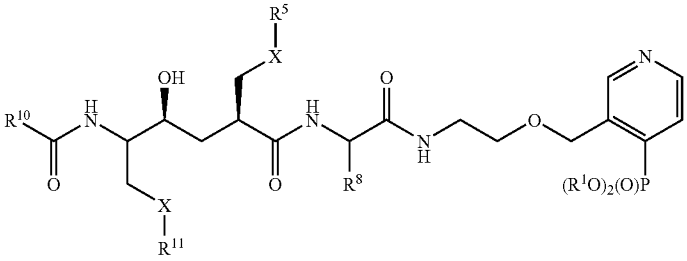
L18
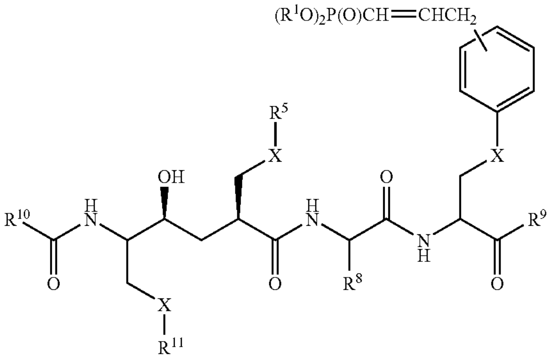
L19
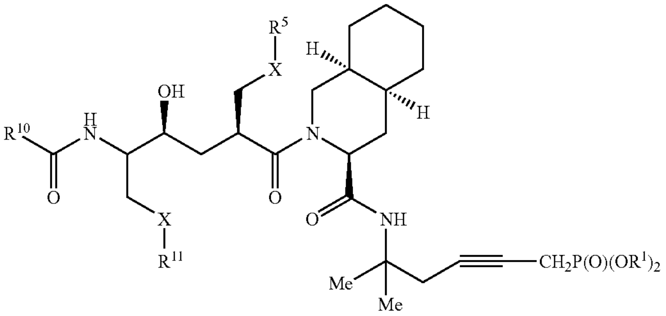
L20
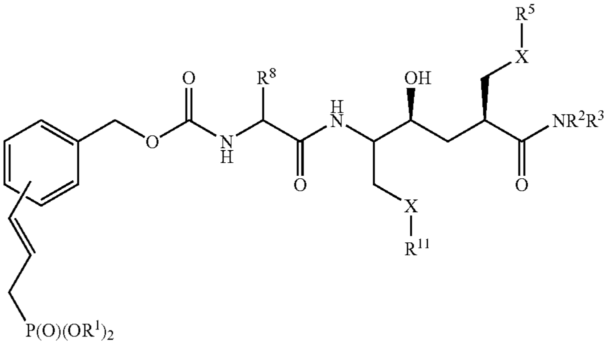
L21
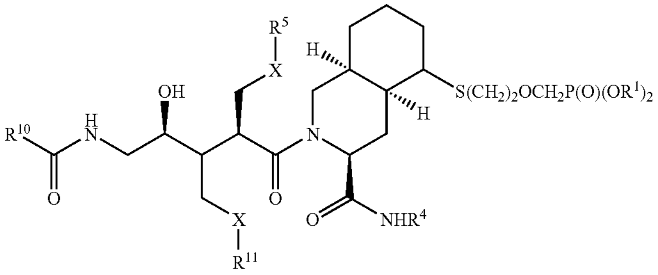
L22

Chart 10. Structures of the $R^7NHCH(R^6)COOH$ components
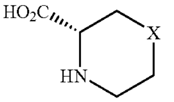
X = NH, $CH_2$
C1
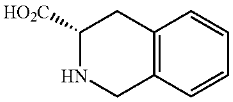
C2
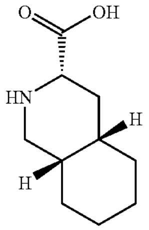
C3
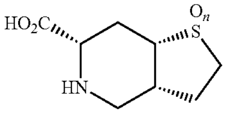
n = 0,2
C4
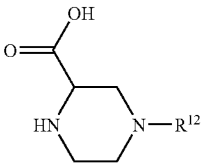
C5
$R^{12}$ =
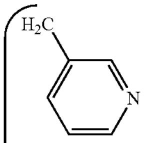
C6
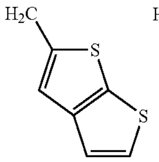
C7
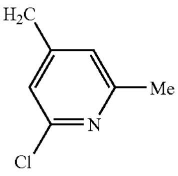
C8
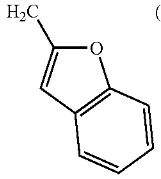
C9
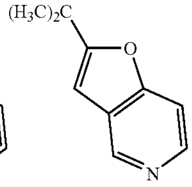
C10
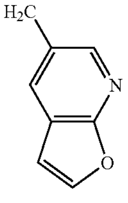
C11
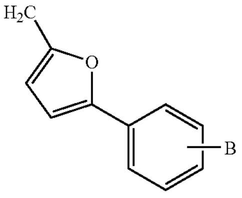
B = F or Cl
C10a
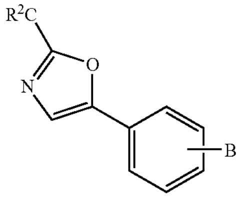
B = F or Cl
R-Me
C10b
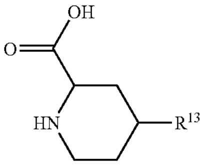
$R^{13}$ = $OCH_2Ph$
S-3-pyridyl
S-4-pyridyl
$OCH_2$-4-pyridyl
C12
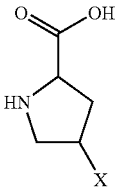
X = Cl, OMe
C13
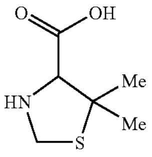
C14
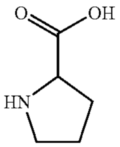
C15
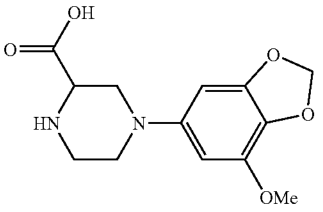
C16

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990. Reactive substituents which may be protected are shown in the accompanying schemes as, for example, [OH], [SH].

Preparation of the Phosphonate Ester Intermediates 1 in which X is a Direct Bond.

The intermediate phosphonate esters 1, in which the group A is attached to the aminoindanol moiety, are prepared as shown in Schemes 1 and 2.

In this procedure, the propionic acid 1.1, or an activated derivative thereof, is reacted with an aminoindanol derivative 1.2, in which the substituent A is either the group link-P(O)$(OR^1)_2$ or a precursor such as [OH], [SH], [NH], Br, to afford the amide 1.3. The preparation of the aminoindanol derivatives 1.2 is described in Schemes 133-137.

The preparation of amides from carboxylic acids and derivatives is described, for example, in Organic Functional Group Preparations, by S. R. Sandler and W. Karo, Academic Press, 1968, p. 274. The carboxylic acid is reacted with the amine in the presence of an activating agent, such as, for example, dicyclohexylcarbodiimide or diisopropylcarbodiimide, optionally in the presence of, for example, hydroxybenztriazole, in a non-protic solvent such as, for example, pyridine, DMF or dichloromethane, to afford the amide.

Alternatively, the carboxylic acid may first be converted into an activated derivative such as the acid chloride or anhydride, and then reacted with the amine, in the presence of an organic base such as, for example, pyridine, to afford the amide.

The conversion of a carboxylic acid into the corresponding acid chloride is effected by treatment of the carboxylic acid with a reagent such as, for example, thionyl chloride or oxalyl chloride in an inert organic solvent such as dichloromethane.

Preferably, the carboxylic acid 1.1 is reacted with an equimolar amount of the amine 1.2 in the presence of dicyclohexylcarbodiimide and hydroxybenztriazole, in an aprotic solvent such as, for example, tetrahydrofuran, at about ambient temperature, so as to afford the amide product 1.3. The amide is then reacted with 2-(S)glycidyl tosylate 1.4, or an equivalent thereof, such as, for example, 2-(S) glycidyl p-nitrobenzenesulfonate, as described in Tet Lett., 35, 673, 1994. To effect the reaction, the amide 1.3 is first converted into the α-anion, by treatment with a strong base, such as, for example, sodium hydride, potassium tert. butoxide and the like. The anion is then reacted with the epoxide 1.4, or an equivalent, as described above, in an inert solvent such as, for example, dimethylformamide, dioxan and the like. The reaction is conducted at a temperature of from 0° C. to −1001C to yield the alkylated product 1.5. Preferably, equimolar amounts of the amide 1.3 and the epoxide 1.4 are dissolved in tetrahydrofuran at about −50° C., and a slight excess of lithium hexamethyldisilylazide is added, as described in WO 9612492 and Tet. Lett., 35, 673, 1994. The temperature is raised to about −25° C. to effect stereoselective alkylation and conversion to the epoxide 1.5. The thus-obtained epoxide 1.5 is then subjected to a regiospecific ring-opening reaction with the amine 1.6 to yield the hydroxyamine 1.7. The preparation of hydroxyamines by the reaction between an amine and an epoxide is described, for example, in Organic Functional Group Preparations, by S. R. Sandler and W. Karo, Academic Press, 1968, p. 357. The amine and the epoxide are reacted together in a polar organic solvent such as, for example, dimethylformamide or an alcohol, to effect the ring-opening reaction.

Preferably, equimolar amounts of the amine 1.6 and the epoxide 1.5 are heated in isopropanol at reflux for about 24 hours, to prepare the hydroxyamine product 1.7, for example as described in WO 9628439 and Tet. Lett., 35, 673, 1994.

The hydroxyamine product 1.7 is then deprotected to remove the acetonide group and produce the compound 1.8 in which A is either the group link-P(O)$(OR^1)_2$ or a precursor such as [OH], [SH], [NH], Br. Acetonide protecting groups are removed by treatment with an acid, for example acetic acid or dilute hydrochloric acid, optionally in the presence of water and a water-miscible organic solvent such as, for example, tetrahydrofuran or an alcohol.

Preferably, the acetonide protecting group is removed by treatment of the acetonide 1.7 with 6N hydrochloric acid in isopropanol at ambient temperature, as described in WO 9612492, to afford the indanol 1.8.

The reactions shown in Scheme 1 illustrate the preparation of the compounds 1.8 in which A is either the group link-P(O)$(OR^1)_2$ or a precursor such as [OH], [SH], [NH], Br. Scheme 2 depicts the conversion of the compounds 1.8 in which A is [OH], [SH], [NH], Br, into the compounds 1 in which A is the group link-P(O)$(OR^1)_2$. In this procedure, the compounds 1.7 are converted, using the procedures described below, Schemes 133-197, into the compounds 2.1. Deprotection, by removal of the acetonide protecting group, as described above, then affords the intermediate phosphonate esters 1 in which X is a direct bond.

In the preceding and following schemes, the conversion of various substituents into the group link-P(O)$(OR^1)_2$ can be effected at any convenient stage of the synthetic sequence, or in the final step. The selection of an appropriate step for the introduction of the phosphonate substituent is made after consideration of the chemical procedures required, and the stability of the substrates to those procedures. It may be necessary to protect reactive groups, for example hydroxyl, during the introduction of the group link-P(O)$(OR^1)_2$.

In the preceding and succeeding examples, the nature of the phosphonate ester group can be varied, either before or after incorporation into the scaffold, by means of chemical transformations. The transformations, and the methods by which they are accomplished, are described below (Scheme 199).

Scheme 1

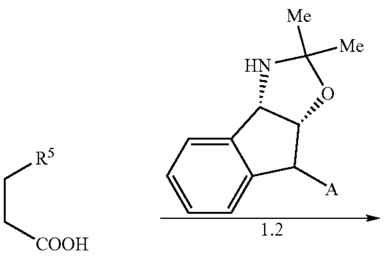

1.1

1.2

-continued

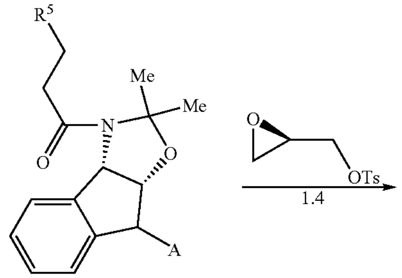

1.3

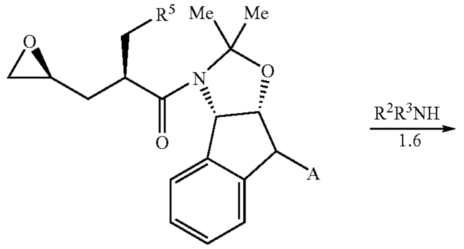

1.5

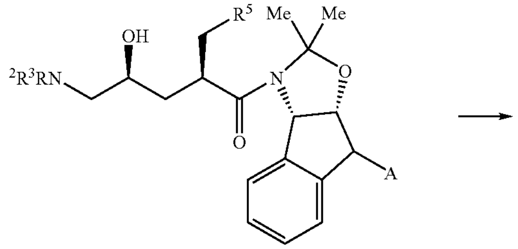

1.7

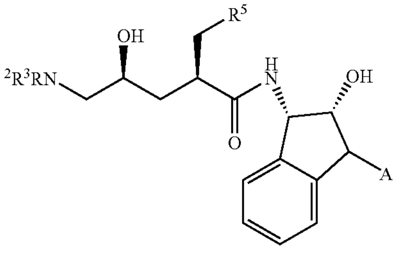

1.8

Scheme 2

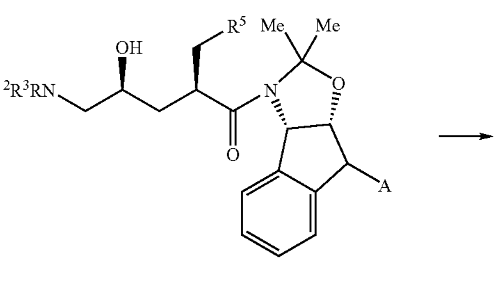

1.7

-continued

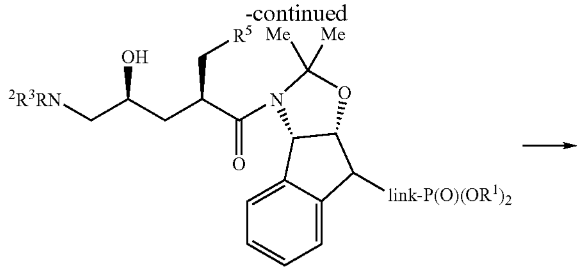

2.1

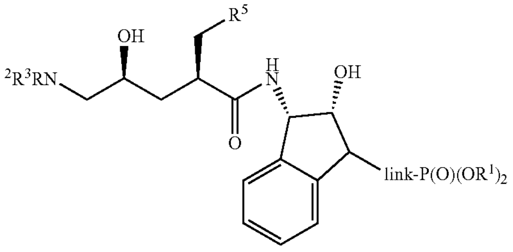

1

Preparation of the Phosphonate Ester Intermediates 1 in which X is Sulfur.

Schemes 3 and 4 illustrate the preparation of the phosphonate esters 1 in which X is sulfur. As shown in Scheme 3, methyl 2-allyl-3-hydroxypropionate 3.1, prepared as described in Tet. Lett., 1973, 2429, is converted into the benzyl ether 3.2. The conversion of alcohols into benzyl ethers is described in Protective Groups in Organic Synthesis, by T. W. Greene and P. G. M Wuts, Wiley, Second Edition 1990, p. 47. The reaction is effected by treatment of the carbinol with a benzyl halide, in the presence of a base such as potassium hydroxide, silver oxide, sodium hydride and the like, in an organic or aqueous organic solvent, optionally in the presence of a phase transfer catalyst. Preferably, the carbinol 3.1 is reacted with benzyl bromide and silver oxide in dimethylformamide at ambient temperature for 48 hours, to afford the product 3.2. The benzyl ether is then subjected to an epoxidation reaction to produce the epoxide 3.3. The conversion of olefins into epoxides is described in Comprehensive Organic Transformations, by R. C. Larock, VCH, 1989, p. 456. The reaction is performed by the use of a peracid such as peracetic acid, m-chloroperbenzoic acid or monoperphthalic acid, optionally in the presence of a base such as potassium carbonate or sodium bicarbonate, or by the use of tert. butyl hydroperoxide, optionally in the presence of a chiral auxiliary such as diethyl tartrate. Preferably, equimolar amounts of the olefin and m-chloroperbenzoic acid are reacted in dichloromethane in the presence of sodium bicarbonate, as described in Tet. Lett., 849, 1965, to afford the epoxide 3.3. This compound is then reacted with the amine 1.6 to yield the hydroxyamine 3.4. The reaction is performed as described above for the preparation of the hydroxyamine 1.7. The hydroxyl substituent is then protected by conversion to the silyl ether 3.5, in which OTBD is tert. butyldimethylsilyloxy. The preparation of silyl ethers is described in Protective Groups in Organic Synthesis, by T. W. Greene and P. G. M Wuts, Wiley, Second Edition 1990, p. 77. The reaction is effected by treatment of the carbinol with tert. butylchlorodimethylsilane and a base such as imidazole, dimethylaminopyridine or 2,6-lutidine, in an organic solvent such as dichloromethane or dimethylformamide. Preferably, equimolar amounts of the carbinol, tert. butylchlorodimethylsilane and imidazole are reacted in dimethylformamide at ambient temperature to give the silyl ether 3.5. The benzyl ether is then removed to afford the carbinol 3.6. The removal of benzyl protecting groups is described in Protective Groups in Organic Synthesis, by T. W. Greene and P. G. M Wuts, Wiley, Second Edition 1990, p. 49. The conversion is effected by means of catalytic hydrogenation over a palladium catalyst, with hydrogen or a hydrogen transfer agent, or by electrolytic reduction, by treatment with trimethylsilyl iodide, or by the use of a Lewis acid such as boron trifluoride or stannic chloride, or by oxidation with ferric chloride or ruthenium dioxide. Preferably, the benzyl ether is removed by reaction of the substrate with 5% palladium on carbon catalyst and ammonium formate in refluxing methanol, as described in Synthesis, 76, 1985. The resultant carbinol 3.6 is then converted into the mesylate ester 3.7 by reaction with one molar equivalent of methanesulfonyl chloride or anhydride, in an organic solvent such as dichloromethane, and in the presence of a base such as dimethylaminopyridine or diisopropylethylamine. The product 3.7 is then reacted with the thiol $R^5SH$, to prepare the thioether 3.9. The preparation of thioethers by alkylation of thiols is described in Synthetic Organic Chemistry, by R. B. Wagner, H. D. Zook, Wiley, 1953, p. 787. The reaction is effected by treatment of the thiol with a base such as sodium hydroxide, potassium carbonate or diazabicyclononene, in a solvent such as ethanol or dioxan, in the presence of the mesylate 3.7, to afford the product 3.9. The methyl ester moiety present in the latter compound is then hydrolyzed to give the carboxylic acid 3.10. The transformation is effected hydrolytically, for example by the use of an alkali metal hydroxide in an aqueous organic solvent, or enzymically, for example by the use of porcine liver esterase, as described in J. Am. Chem. Soc., 104, 7294, 1982. Preferably, the ester group is hydrolyzed by treatment of the ester 3.9 with one molar equivalent of lithium hydroxide in aqueous methanol at ambient temperature, to give the carboxylic acid 3.10. The latter compound is then reacted, as described above, with the aminoindanol acetonide 1.3 to give the amide 3.11. Removal of the acetonide group, as described above, with concomitant desilylation, then affords the hydroxyamide 3.12.

The reactions shown in Scheme 3 illustrate the preparation of the compounds 3.12 in which A is either the group link-P$(O)(OR^1)_2$ or a precursor such as [OH], [SH], [NH], Br. Scheme 4 depicts the conversion of the compounds 3.11 in which A is [OH], [SH], [NH], Br, into the phosphonate esters 1 in which X is sulfur. In this procedure, the compounds 3.11 are converted, using the procedures described below, Schemes 133-197, into the compounds 4.1. Deprotection, by removal of the acetonide protecting group, as described above, then affords the intermediate phosphonate esters 1 in which X is sulfur.

Scheme 3

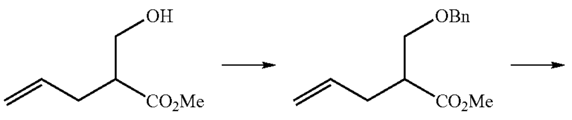

3.1 3.2

-continued

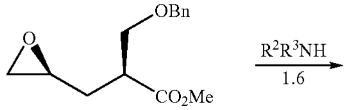

3.3

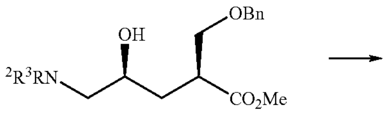

3.4

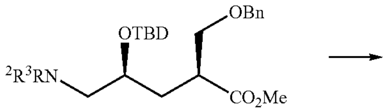

3.5

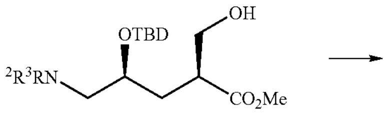

3.6

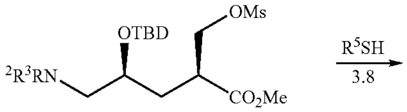

3.7

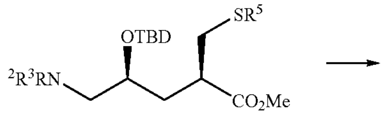

3.9

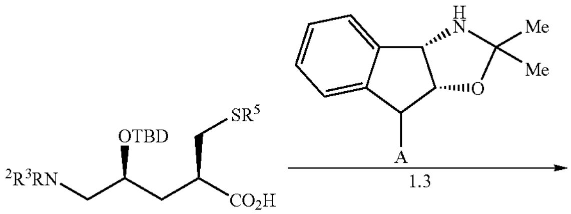

3.10

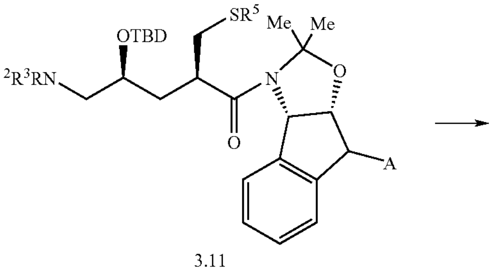

3.11

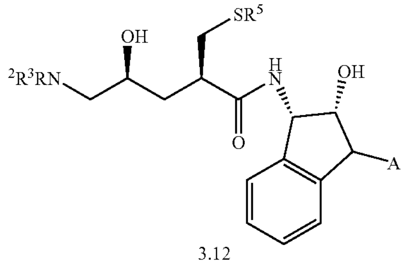

3.12

Scheme 4

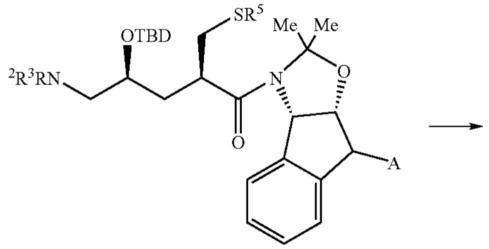

3.11

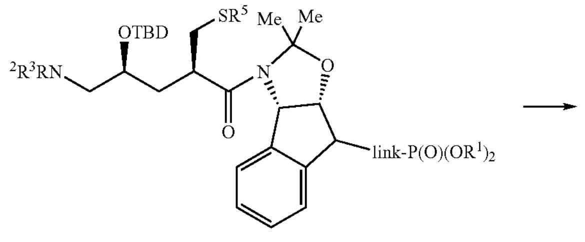

4.1

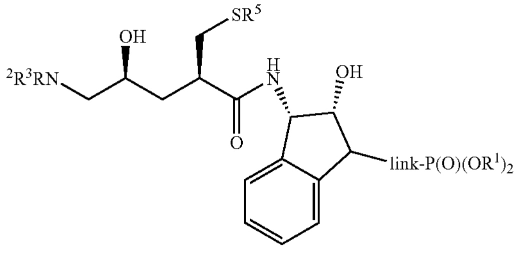

1

Preparation of the Phosphonate Ester Intermediates 2 in which X is a Direct Bond.

Schemes 5 and 6 illustrate the preparation of the phosphonate esters 2 in which X is a direct bond. As shown in Scheme 5, the substituted phenyl propionic ester 5.1, in which the substituent A is either the group link-P(O)($OR^1$)$_2$ or a precursor such as [OH], [SH], [NH], Br, is reacted with the glycidyl tosylate 1.4 to afford the alkylated product 5.2. The preparation of the phenylpropionic esters 5.1 is described below, (Schemes 138-143). The reaction is performed as described above for the preparation of the oxirane 1.5. The product 5.2 is then reacted with the amine $R^2R^3NH$ (1.6) to yield the hydroxyamine 5.3. The reaction is performed as described above for the preparation of the hydroxyamine 1.7. The secondary hydroxy group is then protected, for example by conversion to the tert. butyldimethyl silyl ether 5.4, using the conditions described above for the preparation of the silyl ether 3.5. The methyl ester is then hydrolyzed to produce the carboxylic acid 5.5, using the conditions described above for the hydrolysis of the methyl ester 3.9. The carboxylic acid is then coupled with the amine 1.6 to give the amide 5.6. The reaction is effected under the conditions described above for the preparation of the amide 1.3. The product is desilylated, for example by treatment with 1M tetrabutyl ammonium fluoride in tetrahydrofuran, as described in J. Am. Chem. Soc., 94, 6190, 1972, to give the carbinol 5.7.

The reactions shown in Scheme 5 illustrate the preparation of the compounds 5.7 in which the substituent A is either the group link-P(O)($OR^1$)$_2$ or a precursor such as [OH], [SH], [NH], Br, as described herein. Scheme 6 depicts the conversion of the compounds 5.7 in which A is [OH], [SH], [NH], Br, into the phosphonate esters 2 in which X is a direct bond. In this procedure, the compounds 5.7 are converted, using the procedures described below, Schemes 133-197, into the compounds 2.

Scheme 5

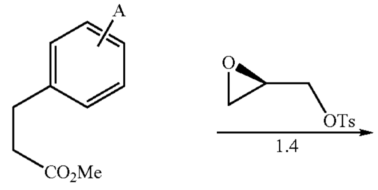

5.1

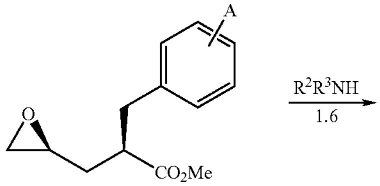

5.2

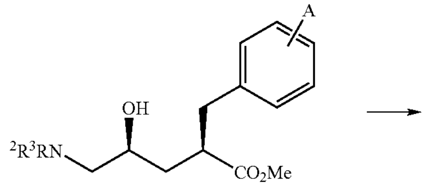

5.3

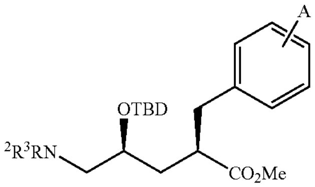

5.4

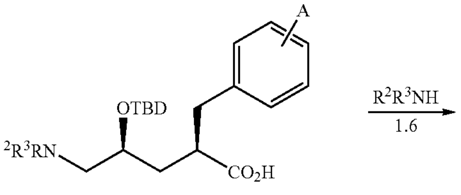

5.5

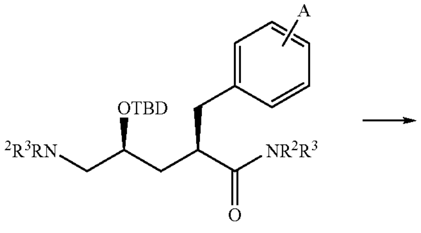

5.6

-continued

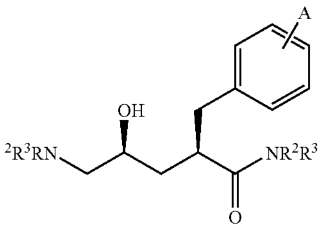

5.7

Scheme 6

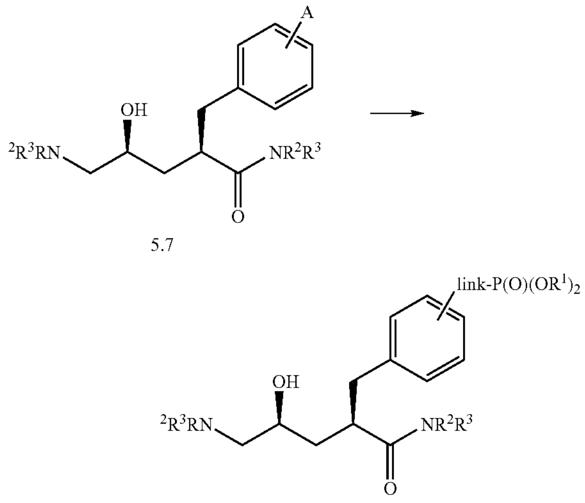

5.7

2

Scheme 7

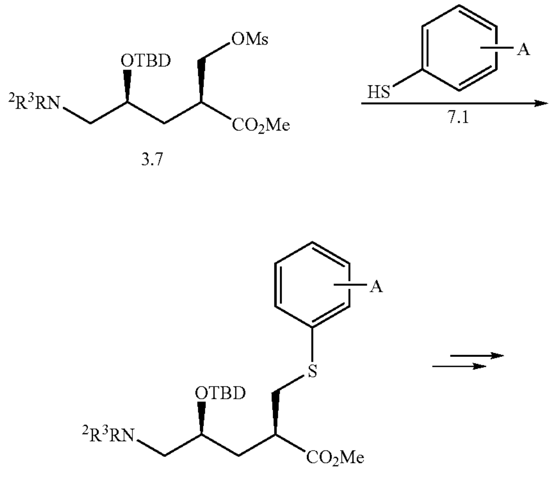

3.7

7.1

7.2

-continued

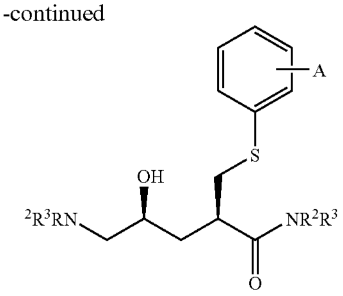

7.3

Scheme 8

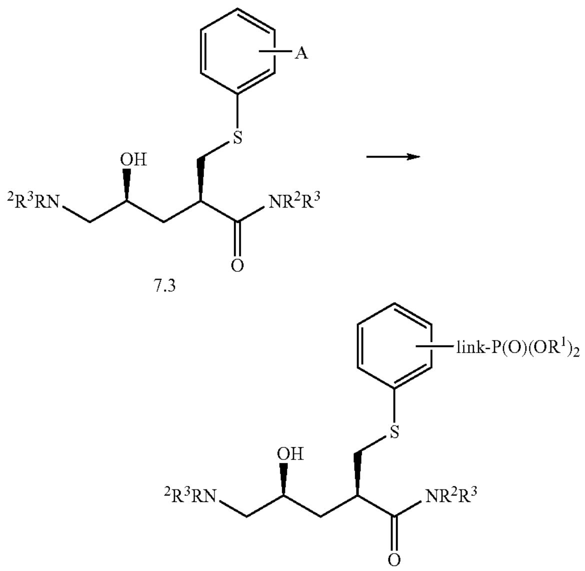

7.3

2

Preparation of the Phosphonate Ester Intermediates 2 in which X is Sulfur.

Schemes 7 and 8 illustrate the preparation of the phosphonate esters 2 in which X is sulfur. As shown in Scheme 7, the mesylate 3.7 is reacted with the thiophenol 7.1, in which the substituent A is either the group link-P(O)(OR$^1$)$_2$ or a precursor such as [OH], [SH], [NH], Br, to afford the thioether 7.2. The reaction is performed under the same conditions as described above for the preparation of the thioether 3.9. The preparation of the thiophenols 7.2 is described in Schemes 144-153. The product 7.2 is then transformed, using the sequence of reactions described above for the conversion of the ester 5.4 into the aminoamide 5.7, into the aminoamide 7.3.

The reactions shown in Scheme 7 illustrate the preparation of the compounds 7.3 in which the substituent A is either the group link-P(O)(OR$^1$)$_2$ or a precursor such as [OH], [SH], [NH], Br. Scheme 8 depicts the conversion of the compounds 7.3 in which A is [OH], [SH], [NH], Br, into the phosphonate esters 2 in which X is sulfur. In this procedure, the compounds 7.3 are converted, using the procedures described below, Schemes 133-197, into the compounds 2.

Preparation of the Phosphonate Ester Intermediates 3 in which X is a Direct Bond.

Schemes 9 and 10 illustrate the preparation of the phosphonate esters 3 in which X is a direct bond. As shown in Scheme 9, the methyl ester 9.1 is reacted, as described above, (Scheme 1) with the epoxide 1.4 to afford the alkylated ester 9.2. The product is then reacted with the amine 9.3, in which the substituent A is either the group link-$P(O)(OR^1)_2$ or a precursor, to yield the hydroxyamine 9.4. The preparation of the tert. butylamine derivatives 9.3 is described below, (Schemes 154-158). The hydroxyamine is then transformed, using the sequence of reactions described above for the conversion of the aminoester 5.3 into the aminoamide 5.7, into the aminoamide 9.5.

The reactions shown in Scheme 9 illustrate the preparation of the compounds 9.5 in which the substituent A is either the group link-$P(O)(OR^1)_2$ or a precursor such as [OH], [SH], [NH], Br. Scheme 10 depicts the conversion of the compounds 9.5 in which A is [OH], [SH], [NH], Br, into the phosphonate esters 3 in which X is a direct bond. In this procedure, the compounds 9.5 are converted, using the procedures described below, Schemes 133-197, into the compounds 3.

Preparation of the Phosphonate Ester Intermediates 3 in which X is Sulfur.

Schemes 11 and 12 illustrate the preparation of the phosphonate esters 3 in which X is sulfur. As shown in Scheme 11, the benzyl-protected oxirane 3.3 is reacted, as described above, with the substituted tert. butylamine 9.3 to afford the hydroxyamine 11.1. The product is then converted, using the sequence of reactions shown in Scheme 5 for the conversion of the hydroxyamine 5.3 into the aminoamide 5.7, into the aminoamide 11.2.

The reactions shown in Scheme 11 illustrate the preparation of the compounds 11.2 in which the substituent A is either the group link-$P(O)(OR^1)_2$ or a precursor such as [OH], [SH], [NH], Br. Scheme 12 depicts the conversion of the compounds 11.2 in which A is [OH], [SH], [NH], Br, into the phosphonate esters 3 in which X is sulfur. In this procedure, the compounds 11.2 are converted, using the procedures described below, Schemes 133-197, into the compounds 3.

Scheme 9

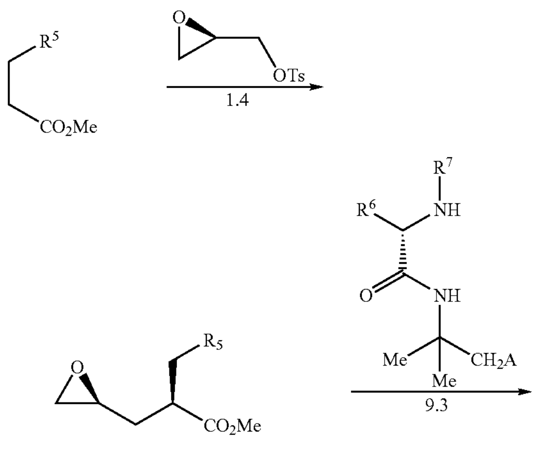

9.2

-continued

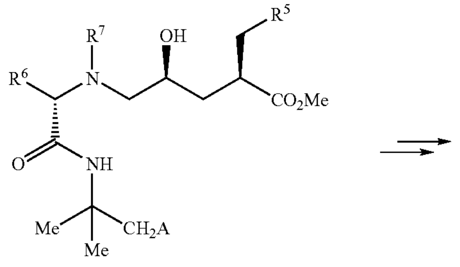

9.4

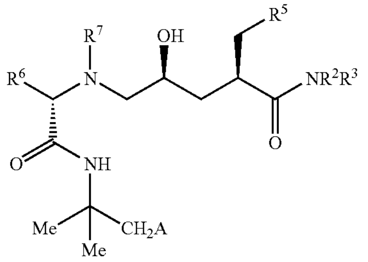

9.5

Scheme 10

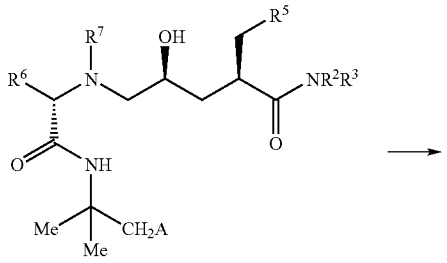

9.5

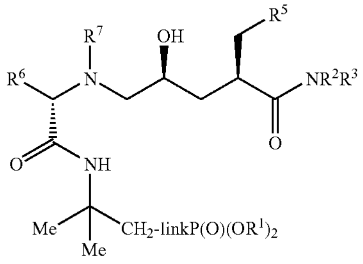

3

Scheme 11

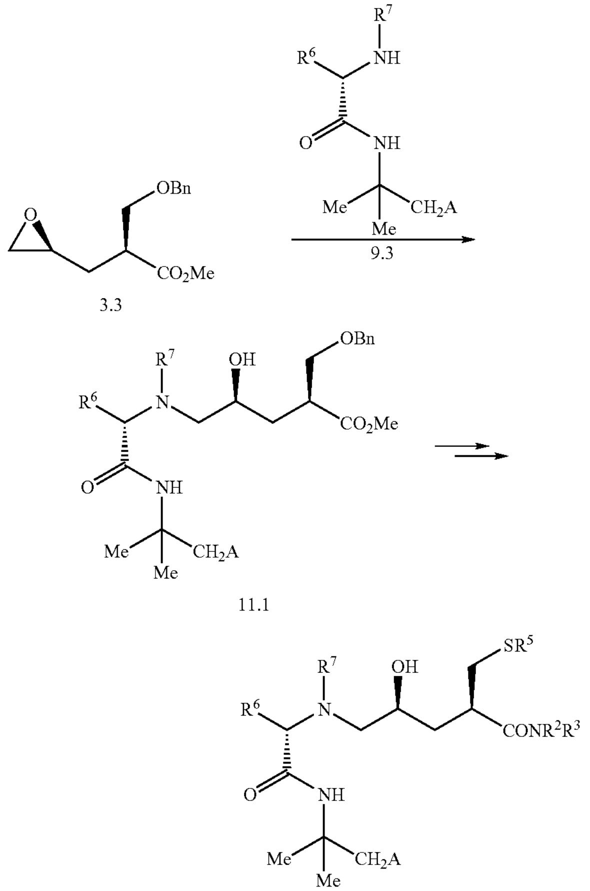
3.3

9.3

11.1

11.2

Scheme 12

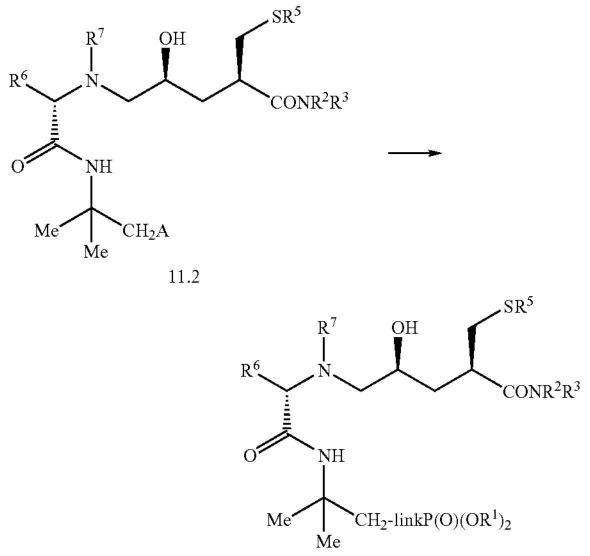
11.2

3

Preparation of the Phosphonate Ester Intermediates 4 in which X is a Direct Bond.

Schemes 13 and 14 illustrate the preparation of the phosphonate esters 4 in which X is a direct bond. As shown in Scheme 13, the oxirane 9.2 is reacted, as described in Scheme 1, with the pyridyl piperazine derivative 13.1 to produce the hydroxyamine 13.2. The preparation of the pyridyl piperazine derivatives 13.1 is described in Schemes 159-164. The product is then transformed, as described previously, (Scheme 5) into the amide 13.3.

The reactions shown in Scheme 13 illustrate the preparation of the compounds 13.3 in which the substituent A is either the group link-$P(O)(OR^1)_2$ or a precursor such as [OH], [SH], [NH], Br. Scheme 12 depicts the conversion of the compounds 13.3 in which A is [OH], [SH], [NH], Br, into the phosphonate esters 4 in which X is a direct bond. In this procedure, the compounds 13.3 are converted, using the procedures described below, Schemes 133-197, into the compounds 4.

Preparation of the Phosphonate Ester Intermediates 4 in which X is Sulfur.

Schemes 15 and 16 illustrate the preparation of the phosphonate esters 4 in which X is sulfur. As shown in Scheme 15, the benzyl-protected oxirane 3.3 is reacted, as described above, with the pyridyl piperazine derivative 13.1 to afford the hydroxyamine 15.1. The product is then converted, as described above (Scheme 5) into the aminoamide 15.2.

The reactions shown in Scheme 15 illustrate the preparation of the compounds 15.2 in which the substituent A is either the group link-$P(O)(OR^1)_2$ or a precursor such as [OH], [SH], [NH], Br. Scheme 16 depicts the conversion of the compounds 15.2 in which A is [OH], [SH], [NH], Br, into the phosphonate esters 4 in which X is sulfur. In this procedure, the compounds 15.2 are converted, using the procedures described below, Schemes 133-197, into the compounds 4.

Preparation of the Phosphonate Ester Intermediates 5 in which X is a Direct Bond.

Schemes 17 and 18 illustrate the preparation of the phosphonate esters 5 in which X is a direct bond. As shown in Scheme 17, the oxirane 9.2 is reacted, as described in Scheme 1, with the decahydroisoquinoline derivative 17.1 to produce the hydroxyamine 17.2. The preparation of the decahydroisoquinoline derivatives 17.1 is described in Schemes 192-197. The product is then transformed, as described previously, (Scheme 3) into the amide 17.3.

The reactions shown in Scheme 17 illustrate the preparation of the compounds 17.3 in which the substituent A is either the group link-$P(O)(OR^1)_2$ or a precursor such as [OH], [SH], [NH], Br. Scheme 18 depicts the conversion of the compounds 17.3 in which A is [OH], [SH], [NH], Br, into the phosphonate esters 5 in which X is a direct bond. In this procedure, the compounds 17.3 are converted, using the procedures described below, Schemes 133-197, into the compounds 5.

Preparation of the Phosphonate Ester Intermediates 5 in which X is Sulfur.

Schemes 19 and 20 illustrate the preparation of the phosphonate esters 5 in which X is sulfur. As shown in Scheme 19, the benzyl-protected oxirane 3.3 is reacted, as described above, with the decahydroisoquinoline derivative 17.1 to afford the hydroxyamine 19.1. The product is then converted, as described above (Scheme 5) into the aminoamide 19.2.

The reactions shown in Scheme 19 illustrate the preparation of the compounds 19.2 in which the substituent A is either the group link-$P(O)(OR^1)_2$ or a precursor such as [OH],

[SH], [NH], Br. Scheme 20 depicts the conversion of the compounds 19.2 in which A is [OH], [SH], [NH], Br, into the phosphonate esters 5 in which X is sulfur. In this procedure, the compounds 19.2 are converted, using the procedures described below, Schemes 133-197, into the compounds 5.
Scheme 13
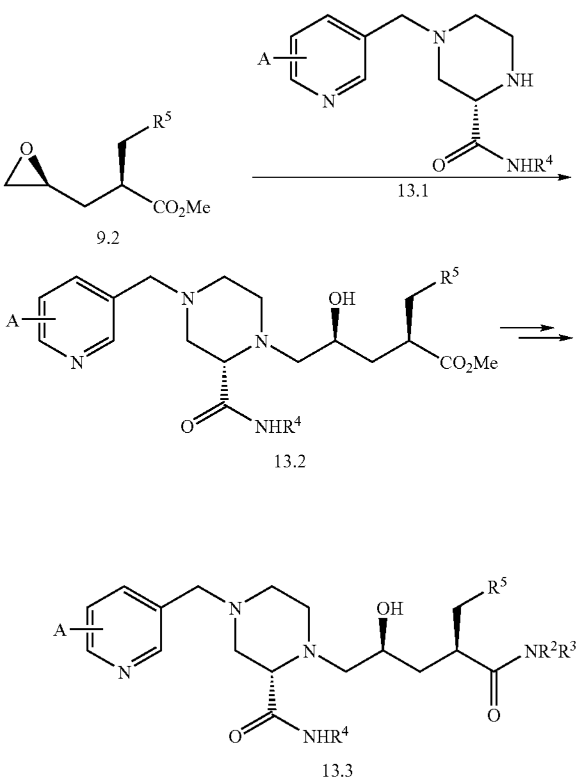
9.2
13.1
13.2
13.3
Scheme 14
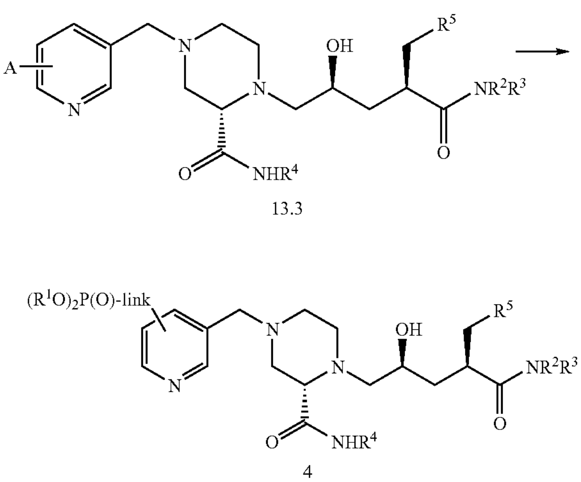
13.3
4
Scheme 15
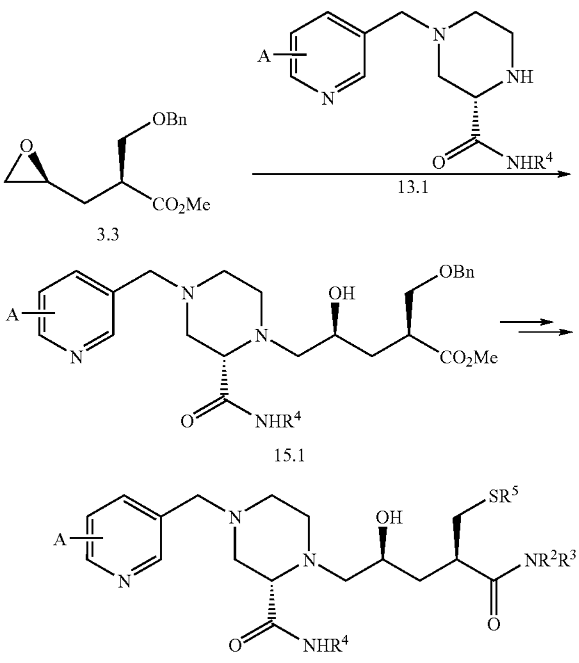
3.3
13.1
15.1
15.2
Scheme 16
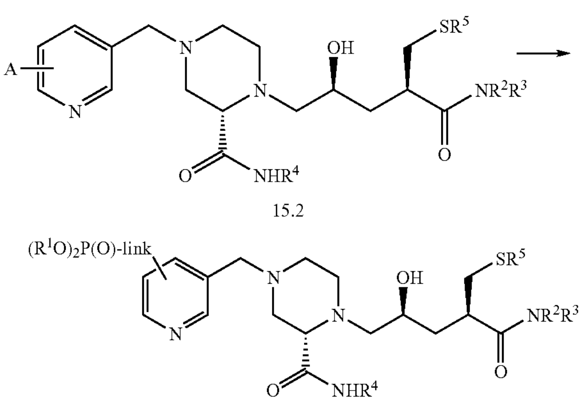
15.2
4
Scheme 17
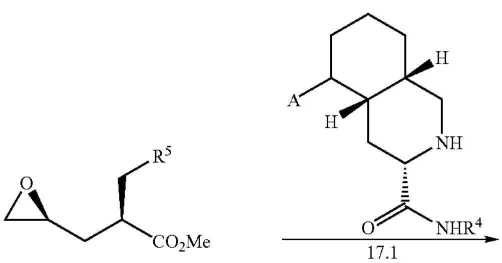
9.2
17.1

-continued

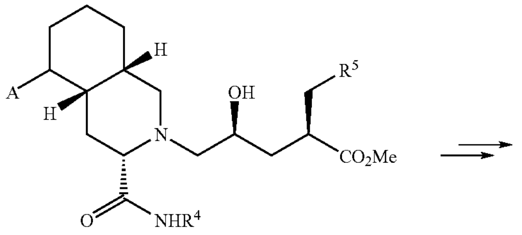

17.2

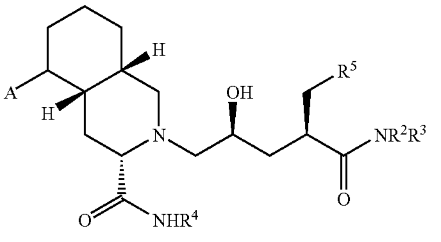

17.3

Scheme 18

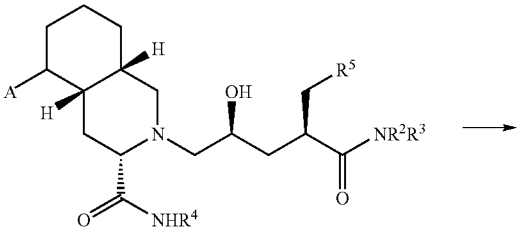

17.3

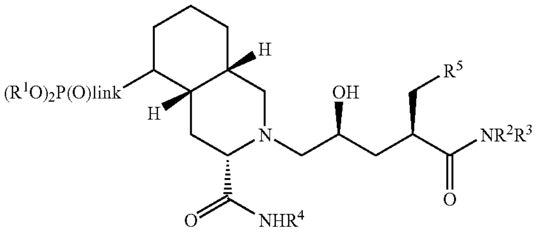

5

Scheme 19

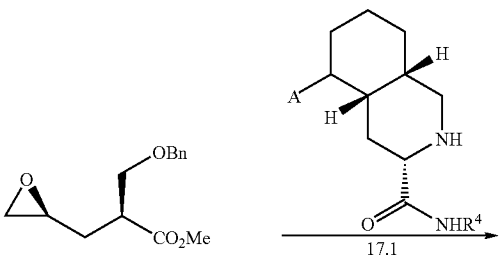

17.1

3.3

-continued

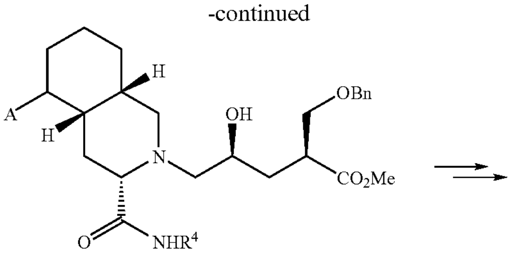

19.1

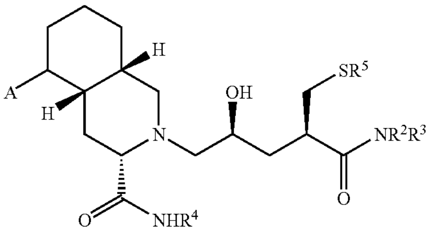

19.2

Scheme 20

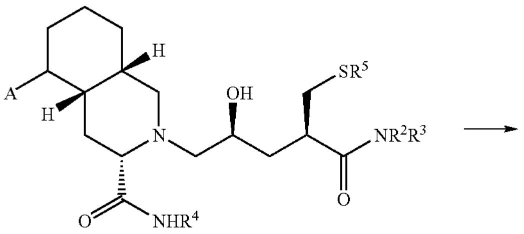

19.2

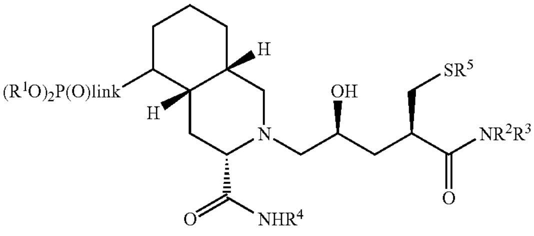

5

Preparation of the Phosphonate Ester Intermediates 6 in which X is a Direct Bond.

Schemes 21 and 22 illustrate the preparation of the phosphonate esters 6 in which X is a direct bond. As shown in Scheme 21, the glycidyl tosylate 1.4 is reacted, as described in Scheme 5, with the anion of the dimethoxyphenyl propionic ester 21.1 to afford the alkylated product 21.2. The preparation of the dimethoxyphenyl propionic ester derivatives 21.1 is described in Scheme 186. The product is then transformed, as described previously, (Scheme 5) into the amide 21.3.

The reactions shown in Scheme 21 illustrate the preparation of the compounds 21.3 in which the substituent A is either the group link-P(O)$(OR^1)_2$ or a precursor such as [OH], [SH], [NH], Br. Scheme 22 depicts the conversion of the compounds 21.3 in which A is [OH], [SH], [NH], Br, into the phosphonate esters 6 in which X is a direct bond. In this procedure, the compounds 21.3 are converted, using the procedures described below, Schemes 133-197, into the compounds 6.

Preparation of the Phosphonate Ester Intermediates 6 in which X is Sulfur.

Schemes 23 and 24 illustrate the preparation of the phosphonate esters 6 in which X is sulfur. As shown in Scheme 23, the mesylate 3.7 is reacted, as described in Scheme 3, with the dimethoxyphenyl mercaptan 23.1 to yield the thioether 23.2. The preparation of the substituted thiols 23.1 is described below in Schemes 170-173. The product is then converted, as described above (Scheme 5) into the aminoamide 23.3.

The reactions shown in Scheme 23 illustrate the preparation of the compounds 23.3 in which the substituent A is either the group link-$P(O)(OR^1)_2$ or a precursor such as [OH], [SH], [NH], Br. Scheme 24 depicts the conversion of the compounds 23.3 in which A is [OH], [SH], [NH], Br, into the phosphonate esters 6 in which X is sulfur. In this procedure, the compounds 23.3 are converted, using the procedures described below, Schemes 133-197, into the compounds 6.

Preparation of the Phosphonate Ester Intermediates 7 in which X is a Direct Bond.

Schemes 25 and 26 illustrate the preparation of the phosphonate esters 7 in which X is a direct bond. As shown in Scheme 25, the oxirane 9.2 is reacted, as described above (Scheme 1) with the amine 1.6 to afford the hydroxyamine 25.1. The product is then converted into the silyl ether 25.2, using the procedures described in Scheme 3. The methyl ester is then hydrolyzed to give the carboxylic acid 25.3, and this compound is then coupled with the tert. butylamine derivative 25.4, using the procedures described in Scheme 1, to yield the amide 25.5. The preparation of the tert. butylamine derivatives 25.4 is described in Schemes 154-157. Desilylation then produces the hydroxyamide 25.6.

The reactions shown in Scheme 25 illustrate the preparation of the compounds 25.6 in which the substituent A is either the group link-$P(O)(OR^1)_2$ or a precursor such as [OH], [SH], [NH], Br. Scheme 26 depicts the conversion of the compounds 25.6 in which A is [OH], [SH], [NH], Br, into the phosphonate esters 7 in which X is a direct bond. In this procedure, the compounds 25.6 are converted, using the procedures described below, Schemes 133-197, into the compounds 7.

Preparation of the Phosphonate Ester Intermediates 7 in which X is Sulfur.

Schemes 27 and 28 illustrate the preparation of the phosphonate esters 7 in which X is sulfur. As shown in Scheme 27, the carboxylic acid 3.10 is coupled, as described in Scheme 3, with the tert. butylamine derivative 25.4 to yield the amide product 27.1. The product is then desilylated, as described above, to afford the amide 27.2.

The reactions shown in Scheme 27 illustrate the preparation of the compounds 27.2 in which the substituent A is either the group link-$P(O)(OR^1)_2$ or a precursor such as [OH], [SH], [NH], Br. Scheme 28 depicts the conversion of the compounds 27.2 in which A is [OH], [SH], [NH], Br, into the phosphonate esters 7 in which X is sulfur. In this procedure, the compounds 27.2 are converted, using the procedures described below, Schemes 133-197, into the compounds 7.

Preparation of the Phosphonate Ester Intermediates 8 in which X is a Direct Bond.

Schemes 29 and 30 illustrate the preparation of the phosphonate esters 8 in which X is a direct bond. As shown in Scheme 29, the silylated carboxylic acid 25.3 is coupled, as described above, (Scheme 1) with the amine 29.1 to afford the amide 29.2 which upon desilylation produces the hydroxyamide 29.3. The preparation of the ethanolamine derivatives 29.1 is described in Schemes 174-178.

The reactions shown in Scheme 29 illustrate the preparation of the compounds 29.3 in which the substituent A is either the group link-$P(O)(OR^1)_2$ or a precursor such as [OH], [SH], [NH], Br. Scheme 30 depicts the conversion of the compounds 29.3 in which A is [OH], [SH], [NH], Br, into the phosphonate esters 8 in which X is a direct bond. In this procedure, the compounds 29.3 are converted, using the procedures described below, Schemes 133-197, into the compounds 8.

Preparation of the Phosphonate Ester Intermediates 8 in which X is Sulfur.

Schemes 31 and 32 illustrate the preparation of the phosphonate esters 8 in which X is sulfur. As shown in Scheme 31, the carboxylic acid 3.10 is coupled, as described previously, with the ethanolamine derivative 29.1 to yield the amide; the product is then desilylated, as described above, to afford the hydroxyamide 31.1.

The reactions shown in Scheme 31 illustrate the preparation of the compounds 31.1 in which the substituent A is either the group link-$P(O)(OR^1)_2$ or a precursor such as [OH], [SH], [NH], Br. Scheme 32 depicts the conversion of the compounds 31.1 in which A is [OH], [SH], [NH], Br, into the phosphonate esters 8 in which X is sulfur. In this procedure, the compounds 31.1 are converted, using the procedures described below, Schemes 133-197, into the compounds 8.

Preparation of the Phosphonate Ester Intermediates 9 in which X is a Direct Bond.

Schemes 33 and 34 illustrate the preparation of the phosphonate esters 9 in which X is a direct bond. As shown in Scheme 33, the silylated carboxylic acid 25.3 is coupled, as described above, (Scheme 1) with the chroman amine 33.1 to afford the corresponding amide, which upon desilylation produces the hydroxyamide 33.2. The preparation of the chroman amines 33.1 is described in Schemes 179-181a.

The reactions shown in Scheme 33 illustrate the preparation of the compounds 33.2 in which the substituent A is either the group link-$P(O)(OR^1)_2$ or a precursor such as [OH], [SH], [NH], Br. Scheme 34 depicts the conversion of the compounds 33.2 in which A is [OH], [SH], [NH], Br, into the phosphonate esters 9 in which X is a direct bond. In this procedure, the compounds 33.2 are converted, using the procedures described below, Schemes 133-197, into the compounds 9.

Scheme 21

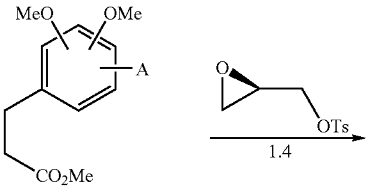

21.1

-continued
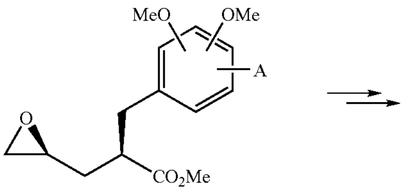
21.2
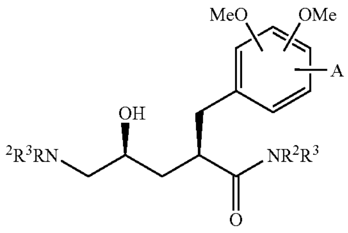
21.3
Scheme 22
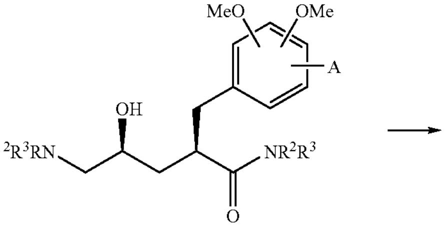
21.3
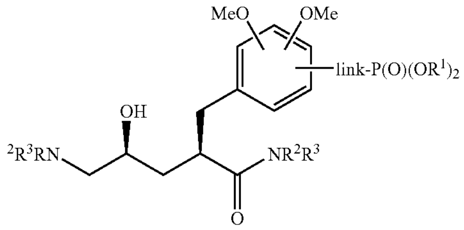
6
Scheme 23
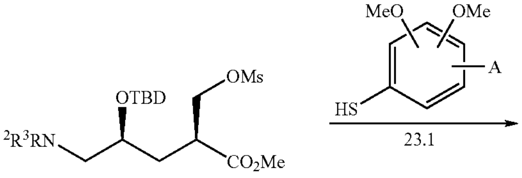
3.7
-continued
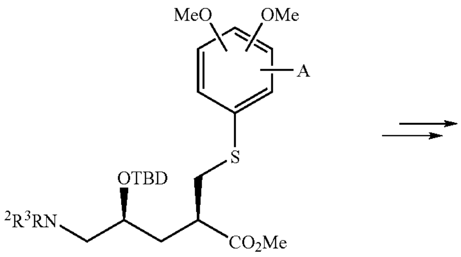
23.2
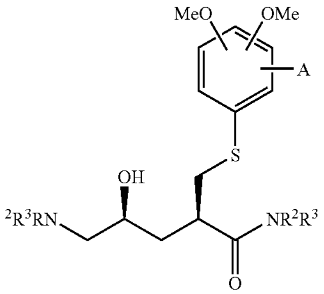
23.3
Scheme 24
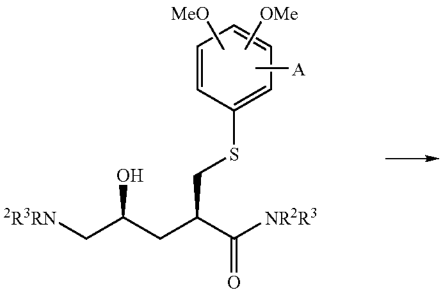
23.3
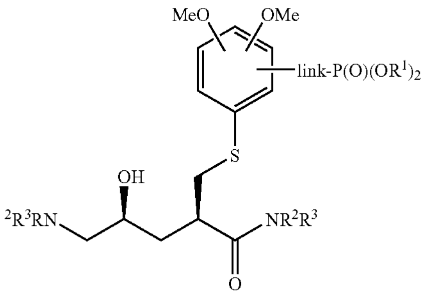
6
Scheme 25
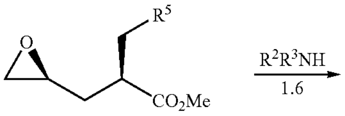
9.2

-continued
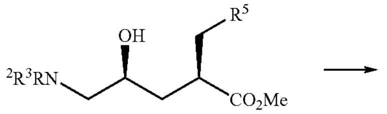
25.1
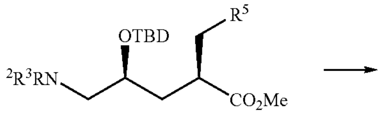
25.2
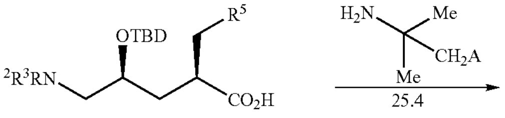
25.3
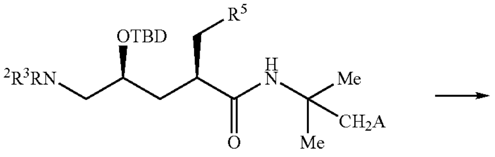
25.5
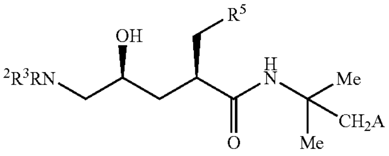
25.6
Scheme 26
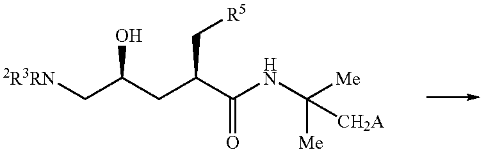
25.6
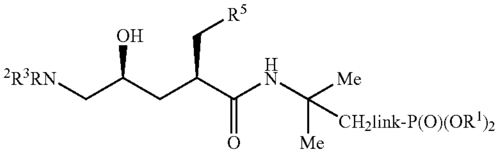
7
Scheme 27
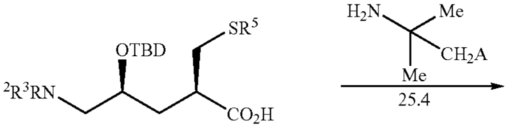
3.10
-continued
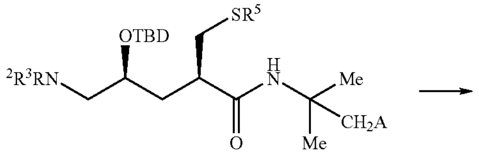
27.1
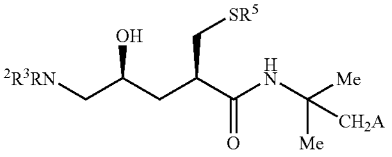
27.2
Scheme 28
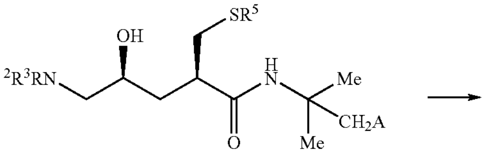
27.2
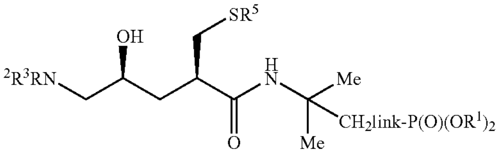
7
Scheme 29
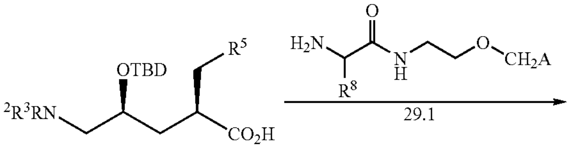
25.3
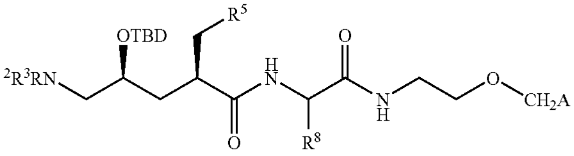
29.2
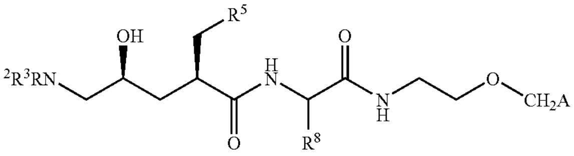
29.3

Scheme 30

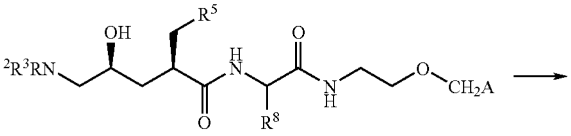

29.3

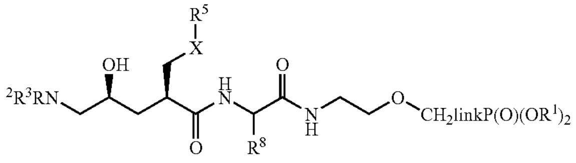

8

Scheme 31

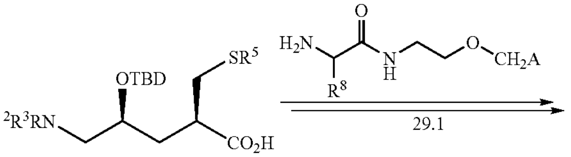

29.1

3.10

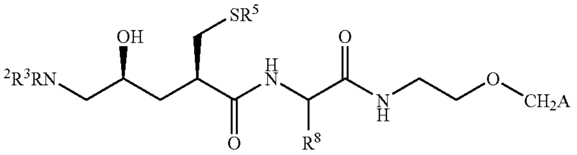

31.1

Scheme 32

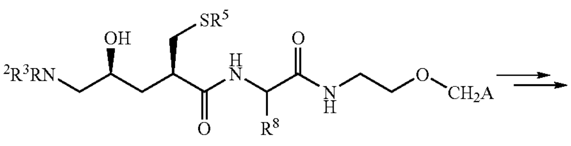

31.1

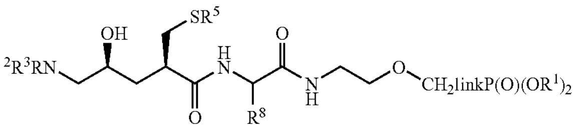

8

Scheme 33

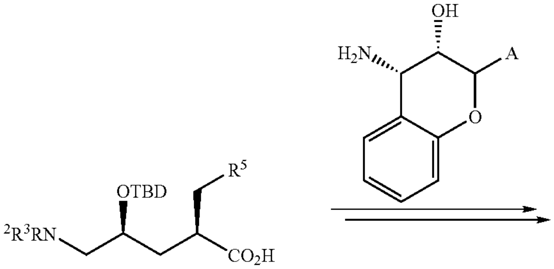

25.3

33.1

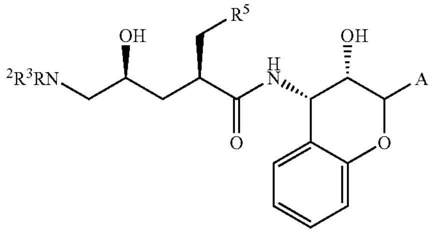

33.2

Scheme 34

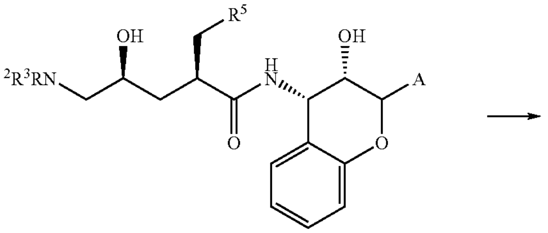

33.2

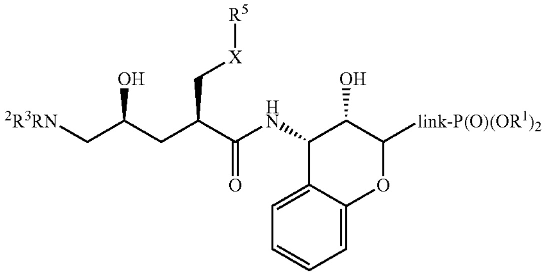

9

Preparation of the Phosphonate Ester Intermediates 9 in which X is Sulfur.

Schemes 35 and 36 illustrate the preparation of the phosphonate esters 9 in which X is sulfur. As shown in Scheme 35, the carboxylic acid 3.10 is coupled, as described previously, with the chroman amine 33.1 to yield the amide; the product is then desilylated, as described above, to afford the amide 35.1.

The reactions shown in Scheme 35 illustrate the preparation of the compounds 35.1 in which the substituent A is either the group link-P(O)$(OR^1)_2$ or a precursor such as [OH], [SH], [NH], Br. Scheme 36 depicts the conversion of the compounds 35.1 in which A is [OH], [SH], [NH], Br, into the phosphonate esters 9 in which X is sulfur. In this procedure, the compounds 35.1 are converted, using the procedures described below, Schemes 133-197, into the compounds 9.

Preparation of the Phosphonate Ester Intermediates 10 in which X is a Direct Bond.

Schemes 37 and 38 illustrate the preparation of the phosphonate esters 10 in which X is a direct bond. As shown in Scheme 37, the silylated carboxylic acid 25.3 is coupled, as described above, (Scheme 1) with the phenylalanine derivative 37.1 to afford the corresponding amide, which upon desilylation produces the hydroxyamide 37.2. The preparation of the phenylalanine derivatives 37.1 is described in Schemes 182-185.

The reactions shown in Scheme 37 illustrate the preparation of the compounds 37.2 in which the substituent A is either the group link-P(O)(OR$^1$)$_2$ or a precursor such as [OH], [SH], [NH], Br. Scheme 38 depicts the conversion of the compounds 37.2 in which A is [OH], [SH], [NH], Br, into the phosphonate esters 10 in which X is a direct bond. In this procedure, the compounds 37.2 are converted, using the procedures described below, Schemes 133-197, into the compounds 10.

Preparation of the Phosphonate Ester Intermediates 10 in which X is Sulfur.

Schemes 39 and 40 illustrate the preparation of the phosphonate esters 10 in which X is sulfur. As shown in Scheme 39, the carboxylic acid 3.10 is coupled, as described previously, with the phenylalanine derivative 37.1 to yield the corresponding amide; the product is then desilylated, as described above, to afford the amide 39.1.

The reactions shown in Scheme 39 illustrate the preparation of the compounds 39.1 in which the substituent A is either the group link-P(O)(OR$^1$)$_2$ or a precursor such as [OH], [SH], [NH], Br. Scheme 40 depicts the conversion of the compounds 39.1 in which A is [OH], [SH], [NH], Br, into the phosphonate esters 10 in which X is sulfur. In this procedure, the compounds 39.1 are converted, using the procedures described below, Schemes 133-197, into the compounds 10.

Preparation of the Phosphonate Ester Intermediates 11 in which X is a Direct Bond.

Schemes 41 and 42 illustrate the preparation of the phosphonate esters 11 in which X is a direct bond. As shown in Scheme 41, the silylated carboxylic acid 25.3 is coupled, as described above, (Scheme 1) with the decahydroisoquinoline carboxamide 41.1, prepared as described in Scheme 158, to afford the corresponding amide, which upon desilylation produces the hydroxyamide 41.2.

The reactions shown in Scheme 41 illustrate the preparation of the compounds 41.2 in which the substituent A is either the group link-P(O)(OR$^1$)$_2$ or a precursor such as [OH], [SH], [NH], Br. Scheme 42 depicts the conversion of the compounds 41.2 in which A is [OH], [SH], [NH], Br, into the phosphonate esters 11 in which X is a direct bond. In this procedure, the compounds 41.2 are converted, using the procedures described below, Schemes 133-197, into the compound Preparation of the Phosphonate Ester Intermediates 11 in which X is Sulfur.

Schemes 43 and 44 illustrate the preparation of the phosphonate esters 11 in which X is sulfur. As shown in Scheme 43, the carboxylic acid 3.10 is coupled, as described previously, with the decahydroisoquinoline carboxamide 41.1 to yield the corresponding amide; the product is then desilylated, as described above, to afford the amide 43.1.

The reactions shown in Scheme 43 illustrate the preparation of the compounds 43.1 in which the substituent A is either the group link-P(O)(OR$^1$)$_2$ or a precursor such as [OH], [SH], [NH], Br. Scheme 44 depicts the conversion of the compounds 43.1 in which A is [OH], [SH], [NH], Br, into the phosphonate esters 11 in which X is sulfur. In this procedure, the compounds 43.1 are converted, using the procedures described below, Schemes 133-197, into the compounds 11.

Scheme 35

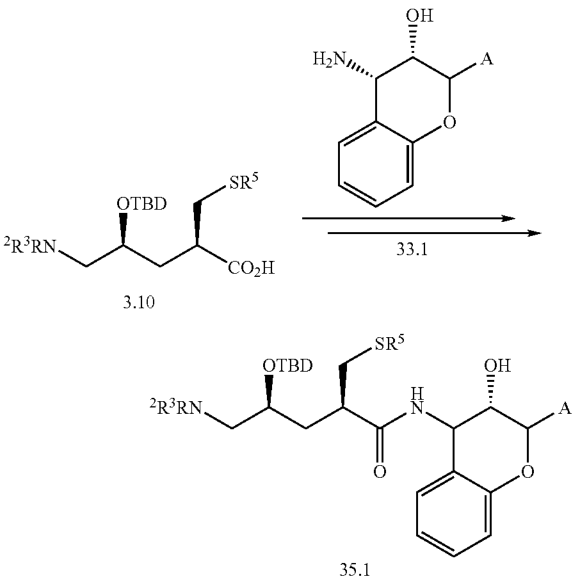

3.10

33.1

35.1

Scheme 36

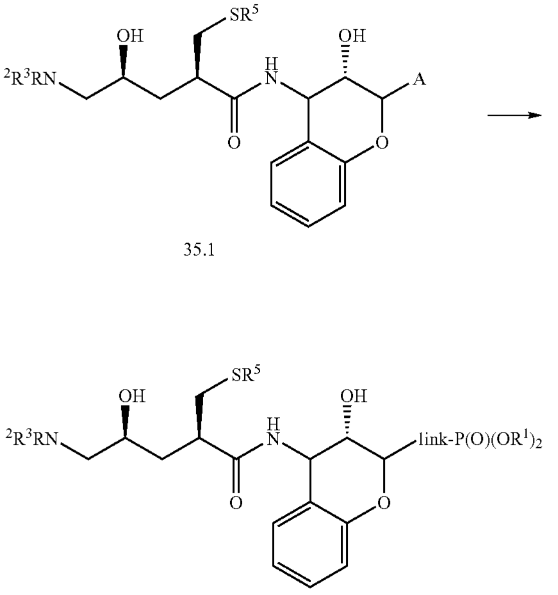

35.1

9

Scheme 37
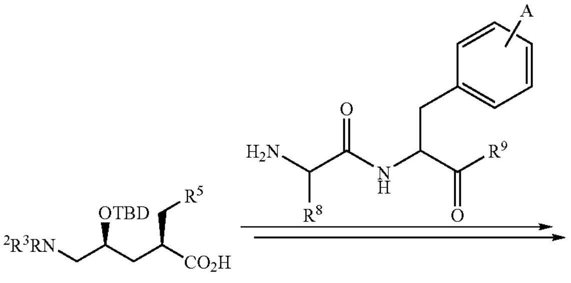
25.3 37.1
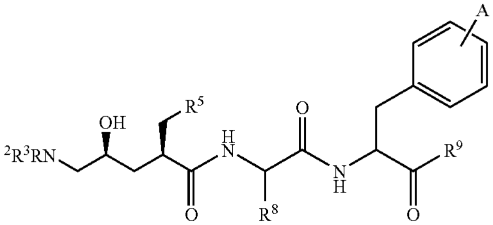
37.2
Scheme 38
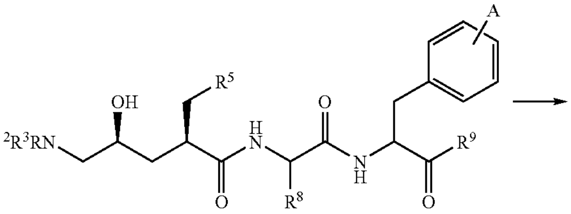
37.2
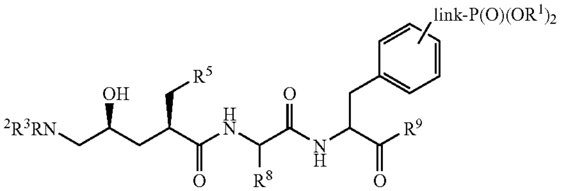
10
Scheme 39
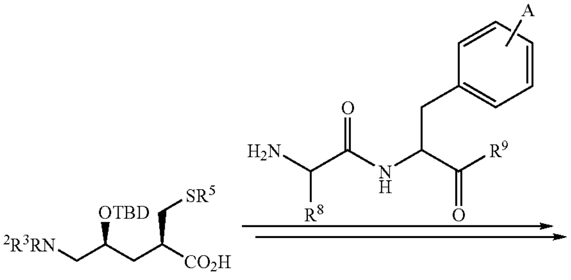
3.10 37.1
-continued
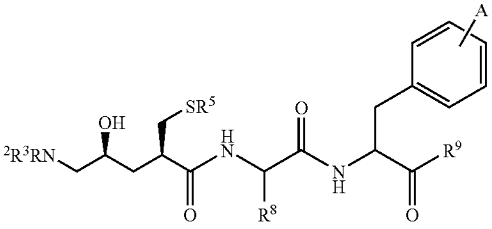
39.1
Scheme 40
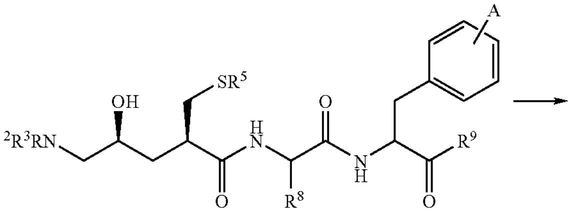
39.1
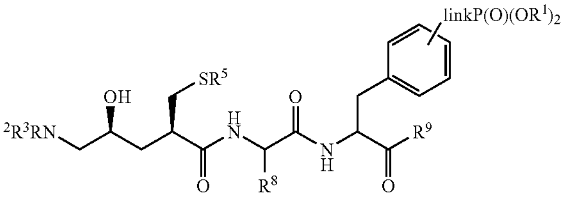
10
Scheme 41
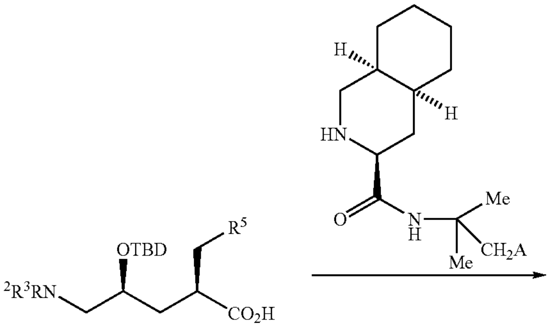
25.3 41.1

-continued

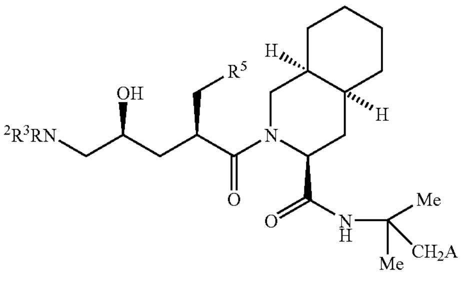

41.2

Scheme 42

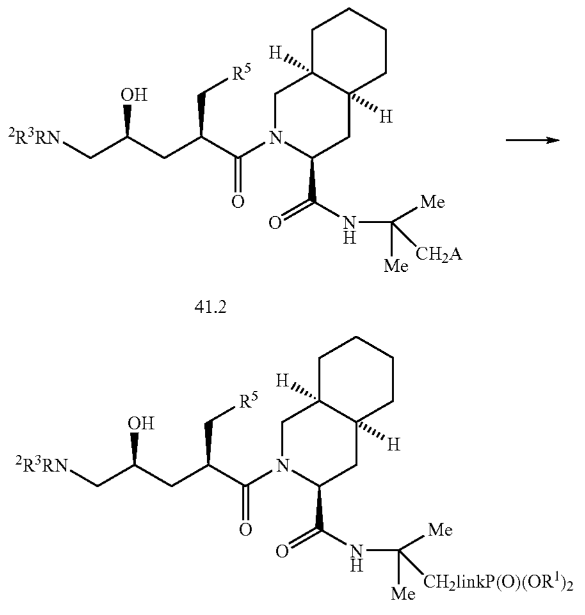

41.2

11

Scheme 43

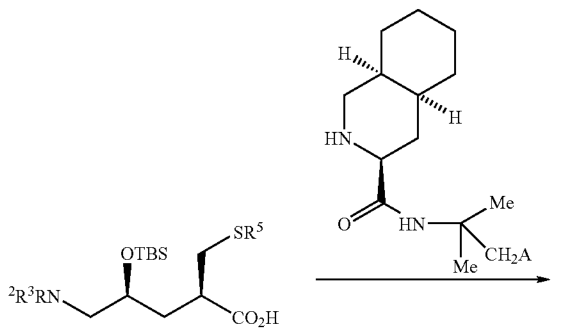

3.10

41.1

-continued

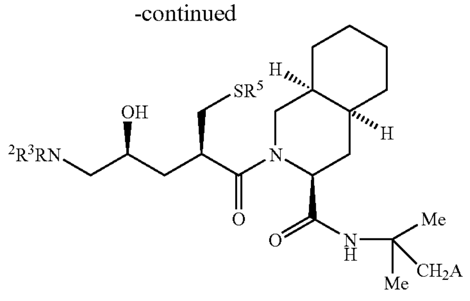

43.1

Scheme 44

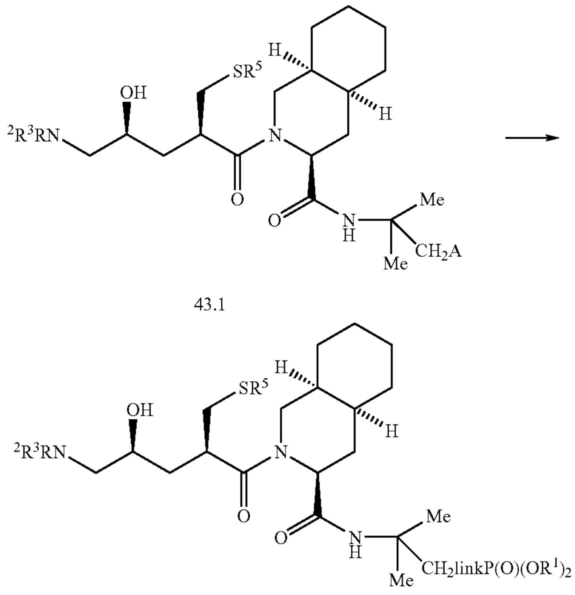

43.1

11

Preparation of the Phosphonate Ester Intermediates 12 in which X is a Direct Bond.

Schemes 45 and 46 illustrate the preparation of the phosphonate esters 12 in which X is a direct bond. As shown in Scheme 45, the silylated carboxylic acid 25.3 is coupled, as described above, (Scheme 1) with the decahydroisoquinoline derivative 45.1 to afford the corresponding amide, which upon desilylation produces the hydroxyamide 45.2. The preparation of the decahydroisoquinoline derivatives 45.1 is described in Schemes 192-197.

The reactions shown in Scheme 45 illustrate the preparation of the compounds 45.2 in which the substituent A is either the group link-P(O)($OR^1$)$_2$ or a precursor such as [OH], [SH], [NH], Br. Scheme 46 depicts the conversion of the compounds 45.2 in which A is [OH], [SH], [NH], Br, into the phosphonate esters 12 in which X is a direct bond. In this procedure, the compounds 45.2 are converted, using the procedures described below, Schemes 133-197, into the compounds 12.

Preparation of the Phosphonate Ester Intermediates 12 in which X is Sulfur.

Schemes 47 and 48 illustrate the preparation of the phosphonate esters 12 in which X is sulfur. As shown in Scheme 47, the carboxylic acid 3.10 is coupled, as described previously, with the decahydroisoquinoline derivative 45.1 to yield the corresponding amide; the product is then desilylated, as described above, to afford the amide 47.1.

The reactions shown in Scheme 47 illustrate the preparation of the compounds 47.1 in which the substituent A is either the group link-$P(O)(OR^1)_2$ or a precursor such as [OH], [SH], [NH], Br. Scheme 48 depicts the conversion of the compounds 47.1 in which A is [OH], [SH], [NH], Br, into the phosphonate esters 12 in which X is sulfur. In this procedure, the compounds 47.1 are converted, using the procedures described below, Schemes 133-197, into the compounds 12.

Preparation of the Phosphonate Ester Intermediates 13 in which X and X' are Direct Bonds.

Schemes 49 and 50 illustrate the preparation of the phosphonate esters 12 in which X and X' are direct bonds. As shown in Scheme 49, a BOC-protected aminoacid 49.1 is converted into the corresponding aldehyde 49.2. A number of methods are known for the conversion of carboxylic acids and derivatives into the corresponding aldehydes, for example as described in Comprehensive Organic Transformations, by R. C. Larock, VCH, 1989, p. 619-627. The conversion is effected by direct reduction of the carboxylic acid, for example employing diisobutyl aluminum hydride, as described in J. Gen. Chem. USSR., 34, 1021, 1964, or alkyl borane reagents, for example as described in J. Org. Chem., 37, 2942, 1972. Alternatively, the carboxylic acid is converted into an amide, such as the N-methoxy N-methyl amide, and the latter compound is reduced with lithium aluminum hydride, for example as described in J. Med. Chem., 1994, 37, 2918, to afford the aldehyde. Alternatively, the carboxylic acid is reduced to the corresponding carbinol which is then oxidized to the aldehyde. The reduction of carboxylic acids to carbinols is described, for example, in Comprehensive Organic Transformations, by R. C. Larock, VCH, 1989, p. 548ff. The reduction reaction is performed by the use of reducing agents such as borane, as described in J. Am. Chem. Soc., 92, 1637, 1970, or by lithium aluminum hydride, as described in Org. Reac., 6, 649, 1951. The resultant carbinol is then converted into the aldehyde by means of an oxidation reaction. The oxidation of a carbinol to the corresponding aldehyde is described, for example, in Comprehensive Organic Transformations, by R. C. Larock, VCH, 1989, p. 604ff. The conversion is effected by the use of oxidizing agents such as pyridinium chlorochromate, as described in J.Org. Chem., 50, 262, 1985, or silver carbonate, as described in Compt. Rend. Ser. C., 267, 900, 1968, or dimethyl sulfoxide/acetic anhydride, as described in J. Am. Chem. Soc., 87, 4214, 1965. Preferably, the procedure described in EP 708085 is employed. The carboxylic acid 49.1 is first reacted with equimolar amounts of isobutyl chloroformate and triethylamine in tetrahydrofuran, to afford a mixed anhydride which is then reduced by treatment with sodium borohydride in aqueous tetrahydrofuran at ambient temperature to afford the carbinol 49.2.

The carbinol is then oxidized to the aldehyde 49.3 by reaction with oxalyl chloride and dimethylsulfoxide in dichloromethane at −60° C., as described in EP708085. To transform the aldehyde into the hydroxyester 49.5, ethyl 3-iodopropionate 49.4 is reacted first with a zinc-copper couple, prepared as described in Org. Syn. Coll. Vol. 5, 855, 1973, and the product is then reacted with trichlorotitanium isopropoxide, as described in EP 708085. The resultant reagent is then treated with the aldehyde 49.3 in dichloromethane at −20° C. to yield the hydroxyester 49.5. The hydroxyester is then cyclized to the lactone 49.6 by treatment with acetic acid in toluene at 100° C., as described in EP 708085. A number of alternative preparations of the lactone 49.6 are known, for example as described in J. Org. Chem., 1985, 50, 4615, J. Org. Chem., 1995, 60, 7927 and J. Org. Chem., 1991, 56, 6500. The lactone 49.6 is then reacted with a substituted benzyl iodide 49.7 to afford the alkylated product 49.8.

The preparation of the benzyl halides 49.7 is described below, (Schemes 165-169). The alkylation reaction is performed in an aprotic organic solvent such as dimethylformamide or tetrahydrofuran, in the presence of a strong base such as sodium hydride or lithium hexamethyl disilylazide. Preferably, the lactone is first reacted with lithium bis(trimethylsilyl)amide in a mixture of tetrahydrofuran and 1,3-dimethyltetrahydropyrimidinone, and then ethyl 3-iodopropioinate is added, as described in EP 708085, to prepare the alkylated lactone 49.8. The lactone is then converted into the corresponding hydroxyacid 49.9 by alkaline hydrolysis, for example by treatment with lithium hydroxide in aqueous dimethoxyethane, as described in EP 708085. The hydroxyacid is then converted into the tert. butyldimethylsilyl ether 49.10, by reaction with excess chloro tert. butyldimethylsilane and imidazole in dimethylformamide, followed by alkaline hydrolysis, employing potassium carbonate in aqueous methanolic tetrahydrofuran, as described in EP 708085, to yield the silyl ether 49.10. The carboxylic acid is then coupled, as described above (Scheme 5) with the amine $R^2R^3NH$ to afford the amide product 49.11. The BOC protecting group is then removed to give the free amine 49.12. The removal of BOC protecting groups is described, for example, in Protective Groups in Organic Synthesis, by T. W. Greene and P. G. M Wuts, Wiley, Second Edition 1990, p. 328. The deprotection can be effected by treatment of the BOC compound with anhydrous acids, for example, hydrogen chloride or trifluoroacetic acid, or by reaction with trimethylsilyl iodide or aluminum chloride. Preferably, the BOC protecting group is removed by treatment of the substrate with 3M hydrogen chloride in ethyl acetate, as described in J. Org. Chem., 43, 2285, 1978, a procedure which also removes the silyl protecting group to afford the hydroxy amine 49.12. The latter compound is then coupled with the carboxylic acid $R^{10}COOH$, or a functional equivalent thereof, to give the amide or carbamate product 49.13. The preparation of amides by the reaction between amines and amides is described above (Scheme 1). Compounds in which the group $R^{10}$ is alkoxy are carbamates; the preparation of carbamates is described below (Scheme 198)

The reactions shown in Scheme 49 illustrate the preparation of the compounds 49.13 in which the substituent A is either the group link-$P(O)(OR^1)_2$ or a precursor such as [OH], [SH], [NH], Br. Scheme 50 depicts the conversion of the compounds 49.13 in which A is [OH], [SH], [NH], Br, into the phosphonate esters 13 in which X and X' are direct bonds. In this procedure, the compounds 49.13 are converted, using the procedures described below, Schemes 133-197, into the compounds 13.

Preparation of the Phosphonate Ester Intermediates 13 in which X is a Direct Bond and X' is Sulfur.

Schemes 51 and 52 illustrate the preparation of the phosphonate esters 13 in which X is a direct bond and X' is sulfur. In this procedure, BOC serine methyl ester mesylate, 51.1, the preparation of which is described in Synlett., 1997, 169, is reacted with the thiol 51.2, employing the conditions described in Scheme 3, to prepare the thioether 51.3. The methyl ester group is then transformed into the corresponding aldehyde 51.4. The reduction of esters to aldehydes is described, for example, in Comprehensive Organic Transformations, by R. C. Larock, VCH, 1989, p. 621. The conversion is effected by treatment with diisobutyl aluminum hydride, sodium aluminum hydride, lithium tri-tertiary butoxy aluminum hydride and the like. Preferably, the ester 51.3 is reduced to the aldehyde 51.4 by reaction with the stoichiometric amount of diisobutyl aluminum hydride in toluene at −80° C., as described in Syn., 617, 1975. The aldehyde is then transformed into the diamide 51.5, using the sequence of reactions and reaction conditions described above (Scheme 49) for the conversion of the aldehyde 49.3 into the diamide 49.13.

The reactions shown in Scheme 51 illustrate the preparation of the compounds 51.5 in which the substituent A is either the group link-$P(O)(OR^1)_2$ or a precursor such as [OH], [SH], [NH], Br. Scheme 52 depicts the conversion of the compounds 51.5 in which A is [OH], [SH], [NH], Br, into the phosphonate esters 13 in which X is a direct bond and X' is sulfur. In this procedure, the compounds 51.5 are converted, using the procedures described below, Schemes 133-197, into the compounds 13.

Preparation of the Phosphonate Ester Intermediates 13 in which X and X' are Sulfur.

Schemes 53, 54 and 55 illustrate the preparation of the phosphonate esters 13 in which X and X' are sulfur. As shown in Scheme 53, the aldehyde 51.4 is reacted with the dianion of N-methylmethacrylamide 53.1 to form the hydroxyamide 53.2. The dianion is generated by treatment of N-methylmethacrylamide with two equivalents of an alkyllithium, for example n-butyllithium, in an organic solvent such as tetrahydrofuran or dimethoxyethane, as described in J. Org. Chem., 1986, 51, 3921. The dianion is then reacted with the aldehyde in the presence of chlorotitanium triisopropoxide, to afford the olefinic amide 53.2. The product is cyclized to produce the methylene lactone 53.3 by heating in an inert solvent such as xylene, at reflux temperature, as described in J. Org. Chem., 1986, 51, 3921. The methylene lactone is then reacted with the thiol 53.4 to yield the thioether 53.5. The preparation of the thiols 53.4 is described below, (Schemes 170-173). The addition of thiols to methylene lactones analogous to the compound 53.3 is described in J. Org. Chem., 1986, 51, 3921. Equimolar amounts of the reactants are combined in an alcoholic solvent such as methanol at about 600C, in the presence of a tertiary base such as triethylamine, to give the addition product 53.5. The latter compound is then subjected to basic hydrolysis, for example by reaction with lithium hydroxide, as described above, (Scheme 49) to produce the hydroxyacid 53.6. The product is silylated, as described in Scheme 49, to give the silylated carbinol 53.7, and the product is then converted, as described in Scheme 49, into the diamide 53.8.

Scheme 54 illustrates an alternative method for the preparation of the diamides 53.8. In this procedure, the anion of the lactone 54.1, obtained as an intermediate in the conversion of the aldehyde 51.4 into the diamide 51.5, (Scheme 51) is reacted with formaldehyde or a functional equivalent thereof, to afford the hydroxymethyl compound 54.2. The generation of the anion of lactones analogous to 54.1, and alkylation thereof, is described above in Scheme 49.

Preferably, the anion is prepared by reaction of the lactone, in a solvent mixture composed of tetrahydrofuran and 1,3-dimethyltetrahydropyrimidinone, with lithium bis(trimethylsilyl)amide, as described in EP 708085, and formaldehyde, generated by pyrolysis of paraformaldehyde, is then introduced in an inert gas stream. The hydroxymethyl product is then converted into the corresponding mesylate 54.3, by reaction with methanesulfonyl chloride in dichloromethane containing a tertiary base such as triethylamine or dimethylaminopyridine, and the mesylate is then reacted with the thiol reagent 53.4, using the procedure described above for the preparation of the thioether 51.3, to yield the thioether 53.5. The product is then transformed, as described above, into the diamide 53.8.

The reactions shown in Schemes 53 and 54 illustrate the preparation of the compounds 53.8 in which the substituent A is either the group link-$P(O)(OR^1)_2$ or a precursor such as [OH], [SH], [NH], Br. Scheme 55 depicts the conversion of the compounds 53.8 in which A is [OH], [SH], [NH], Br, into the phosphonate esters 13 in which X and X' are sulfur. In this procedure, the compounds 53.8 are converted, using the procedures described below, Schemes 133-197, into the compounds 13.

Scheme 45

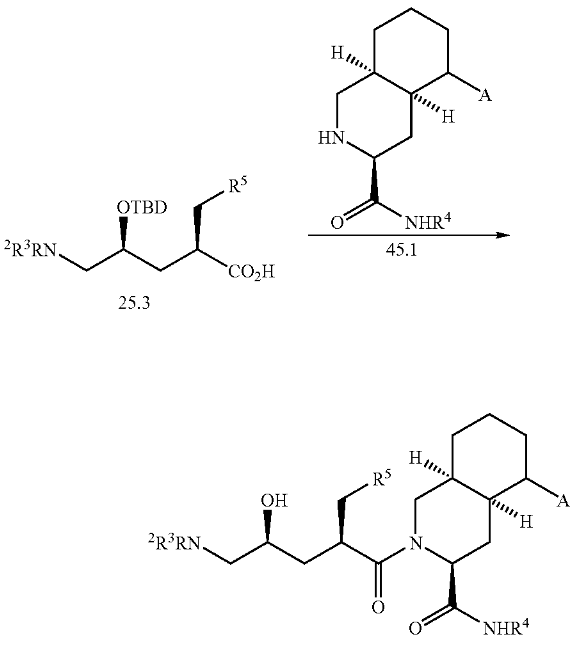

25.3

45.1

45.2

Scheme 46

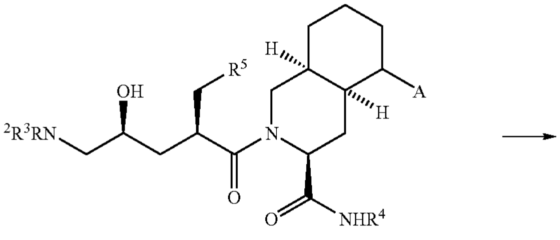

45.2

-continued
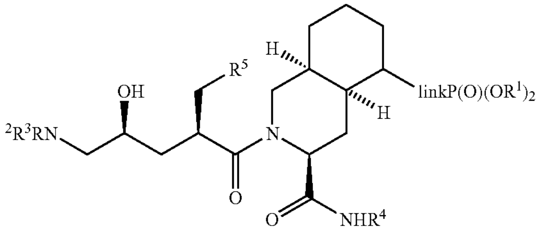
12
Scheme 47
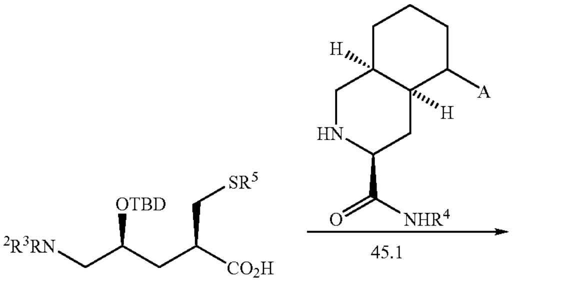
3.10
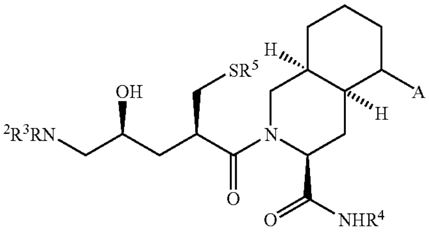
47.1
Scheme 48
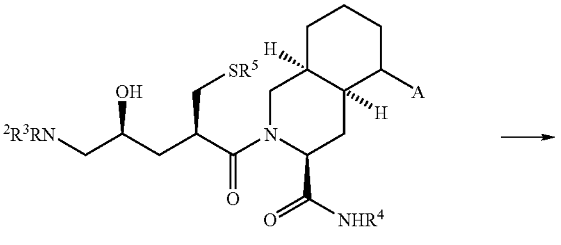
47.1
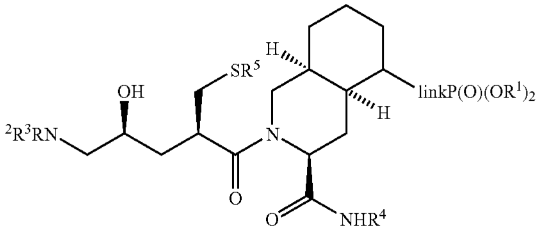
12
Scheme 49
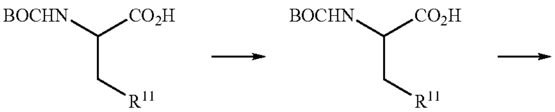
49.1 49.2
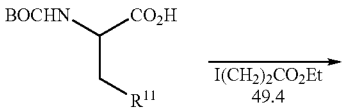
49.3
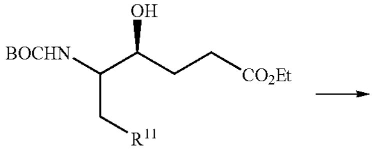
49.5
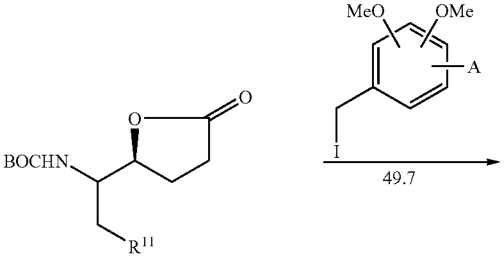
49.6
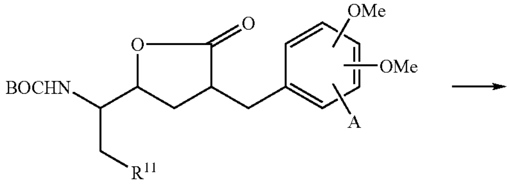
49.8
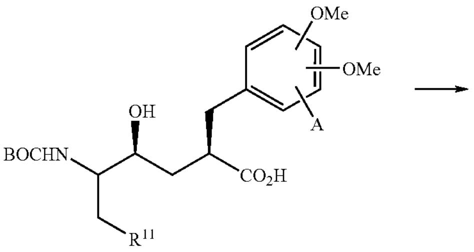
49.9
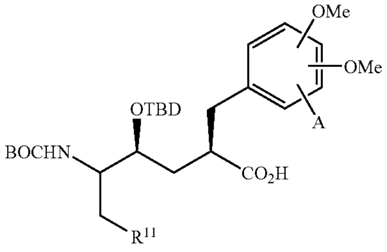
49.10

-continued
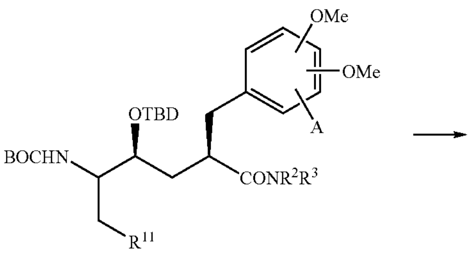
49.11
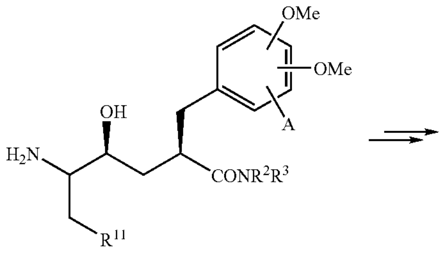
49.12
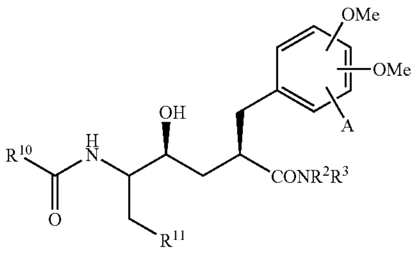
49.13
Scheme 50
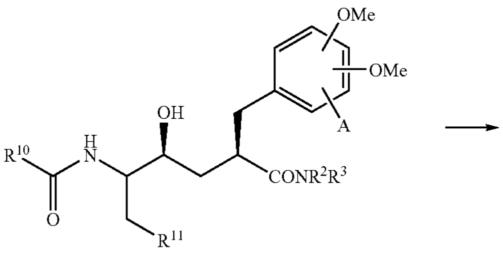
49.13
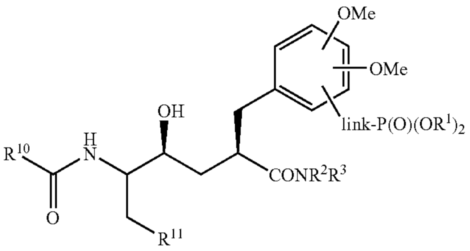
13
Scheme 51
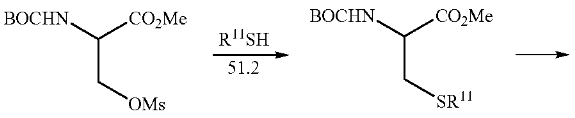
51.1 51.3
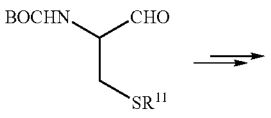
51.4
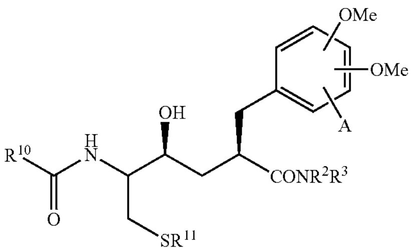
51.5
Scheme 52
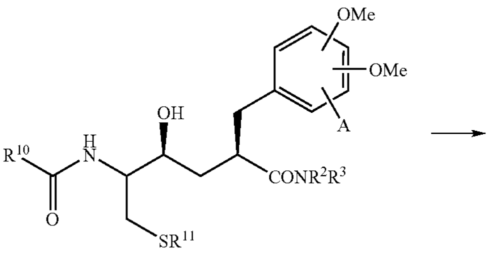
51.5
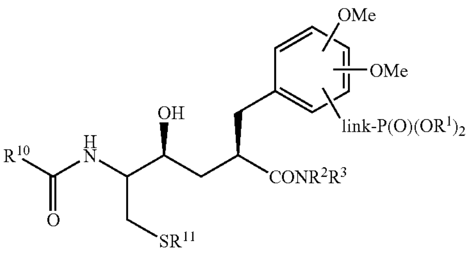
13
Scheme 53
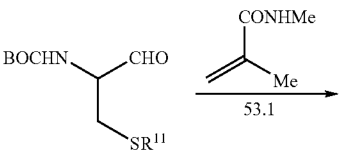
51.4

-continued
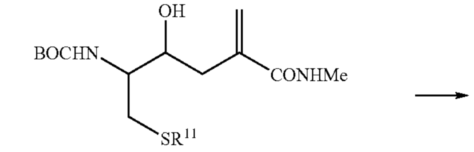
53.2
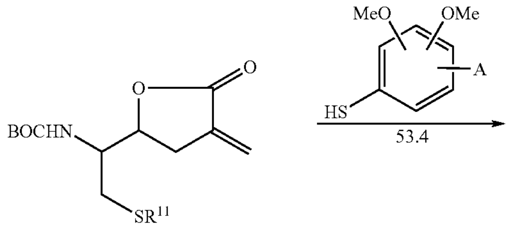
53.3
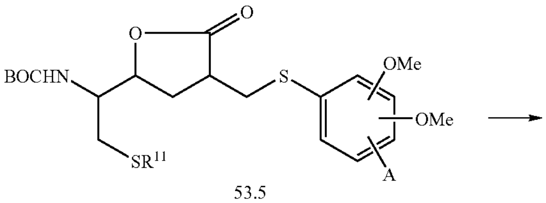
53.5
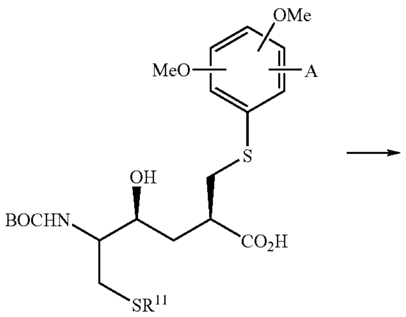
53.6
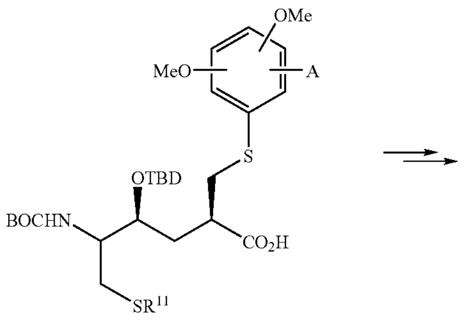
53.7
-continued
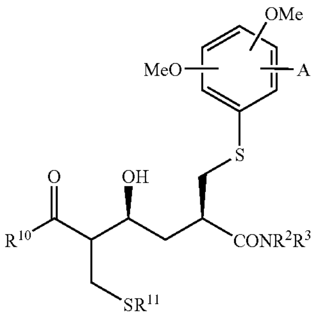
53.8
Scheme 54
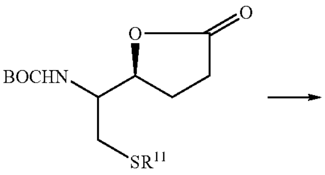
54.1
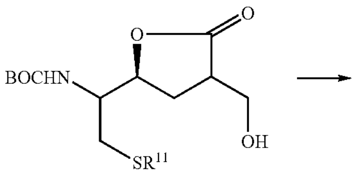
54.2
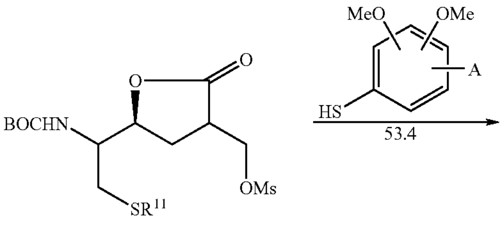
54.3
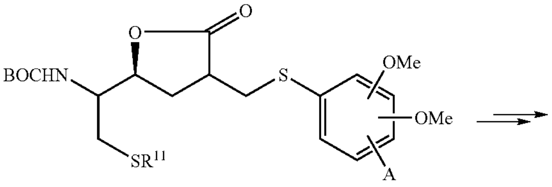
53.5

-continued

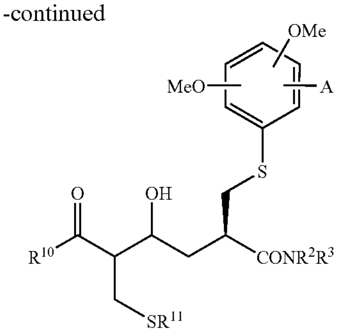

53.8

Scheme 55

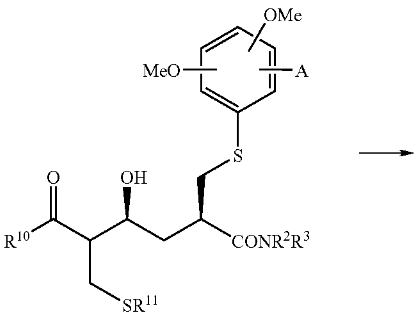

53.8

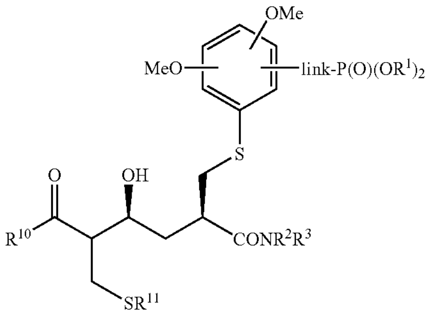

13

Preparation of the Phosphonate Ester Intermediates 13 in which X is Sulfur and X' is a Direct Bond.

Schemes 56 and 57 illustrate the preparation of the phosphonate esters 13 in which X is sulfur and X' is a direct bond. In this procedure, the BOC-protected aldehyde 49.3 is converted, as described in Scheme 53, into the methylene lactone 56.1. The lactone is then reacted with the thiol 53.4 and a base, as described in Scheme 53, to yield the thioether 56.2. The thioether is then transformed, as described in Scheme 53, into the diamide 56.3.

The reactions shown in Scheme 56 illustrate the preparation of the compounds 56.3 in which the substituent A is either the group link-$P(O)(OR^1)_2$ or a precursor such as [OH], [SH], [NH], Br. Scheme 57 depicts the conversion of the compounds 56.3 in which A is [OH], [SH], [NH], Br, into the phosphonate esters 13 in which X is sulfur and X'is a direct bond. In this procedure, the compounds 56.3 are converted, using the procedures described below, Schemes 133-197, into the compounds 13.

Preparation of the Phosphonate Ester Intermediates 14 in which X and X' are Direct Bonds.

Schemes 58 and 59 illustrate the preparation of the phosphonate esters 14 in which X and X' are direct bonds. In this procedure, the lactone 49.6 is reacted, as described in Scheme 49, with a substituted benzyl iodide 58.1, to produce the alkylated compound 58.2. The preparation of the benzyl iodides 58.1 is described in Schemes 187-191. The product is then transformed, as described in Scheme 49, into the diamide 58.3.

The reactions shown in Scheme 58 illustrate the preparation of the compounds 58.3 in which the substituent A is either the group link-$P(O)(OR^1)_2$ or a precursor such as [OH], [SH], [NH], Br. Scheme 59 depicts the conversion of the compounds 58.3 in which A is [OH], [SH], [NH], Br, into the phosphonate esters 14 in which X and X' are direct bonds. In this procedure, the compounds 58.3 are converted, using the procedures described below, Schemes 133-197, into the compounds 14.

Preparation of the Phosphonate Ester Intermediates 14 in which X is a Direct Bond and X' is Sulfur.

Schemes 60 and 61 illustrate the preparation of the phosphonate esters 14 in which X is a direct bond and X' is sulfur. In this procedure, the lactone 54.1 is reacted, as described in Scheme 49, with a substituted benzyl iodide 58.1, to produce the alkylated compound 60.1. The product is then transformed, as described in Scheme 49, into the diamide 60.2.

The reactions shown in Scheme 60 illustrate the preparation of the compounds 60.2 in which the substituent A is either the group link-$P(O)(OR^1)_2$ or a precursor such as [OH], [SH], [NH], Br. Scheme 61 depicts the conversion of the compounds 60.2 in which A is [OH], [SH], [NH], Br, into the phosphonate esters 14 in which X is a direct bond and X' is sulfur. In this procedure, the compounds 60.2 are converted, using the procedures described below, Schemes 133-197, into the compounds 14.

Preparation of the Phosphonate Ester Intermediates 14 in which X and X' are Sulfur.

Schemes 62, 63 and 64 illustrate the preparation of the phosphonate esters 14 in which X and X' are sulfur. As shown in Scherme 62, the methylene lactone 53.3 is reacted, as described in Scheme 53, with a substituted thiophenol 62.1 to produce the addition product 62.2. The preparation of the substituted thiophenols 62.1 is described below, (Schemes 144-153). The product is then transformed, as described in Scheme 53, into the diamide 62.3.

Scheme 63 illustrates an alternative method for the preparation of the diamide 62.3. In this procedure, the mesylate 54.3 is reacted, as described in Scheme 54, with the thiol 62.1 to afford the alkylation product 63.1. The product is then transformed, as described in Scheme 53, into the diamide 62.3.

The reactions shown in Schemes 62 and 63 illustrate the preparation of the compounds 62.3 in which the substituent A is either the group link-$P(O)(OR^1)_2$ or a precursor such as [OH], [SH], [NH], Br. Scheme 64 depicts the conversion of the compounds 62.3 in which A is [OH], [SH], [NH], Br, into the phosphonate esters 14 in which X and X' are sulfur. In this procedure, the compounds 62.3 are converted, using the procedures described below, Schemes 133-197, into the compounds 14.

Preparation of the Phosphonate Ester Intermediates 14 in which X is Sulfur and X' is a Direct Bond.

Schemes 65 and 66 illustrate the preparation of the phosphonate esters 14 in which X is sulfur and X' is a direct bond.

In this procedure, the methylene lactone 56.1 is reacted, as described in Scheme 53, with a substituted thiophenol 62.1, to produce the thioether 65.1. The product is then transformed, as described in Scheme 53, into the diamide 65.2.

The reactions shown in Scheme 65 illustrate the preparation of the compounds 65.2 in which the substituent A is either the group link-P(O)($OR^1$)$_2$ or a precursor such as [OH], [SH], [NH], Br. Scheme 66 depicts the conversion of the compounds 65.2 in which A is [OH], [SH], [NH], Br, into the phosphonate esters 14 in which X is sulfur and X' is a direct bond. In this procedure, the compounds 65.2 are converted, using the procedures described below, Schemes 133-197, into the compounds 14.

Preparation of the Phosphonate Ester Intermediates 15 in which X and X' are Direct Bonds.

Schemes 67 and 68 illustrate the preparation of the phosphonate esters 15 in which X and X' are direct bonds. In this procedure, the BOC-protected phenylalanine derivative 67.1 is converted into the corresponding aldehyde 67.2, using the procedures described above (Scheme 49). The preparation of the phenylalanine derivatives 67.1 is described below, (Schemes 182-184). The aldehyde is then converted, using the procedures described in Scheme 49, into the lactone 67.3. The latter compound is then alkylated, as described in Scheme 49, with the reagent $R^5CH_2I$, (67.4), to afford the alkylated product 67.5. This compound is then converted, as described in Scheme 49, into the diamide 67.6.

The reactions shown in Scheme 67 illustrate the preparation of the compounds 67.6 in which the substituent A is either the group link-P(O)($OR^1$)$_2$ or a precursor such as [OH], [SH], [NH], Br. Scheme 68 depicts the conversion of the compounds 67.6 in which A is [OH], [SH], [NH], Br, into the phosphonate esters 15 in which X and X' are direct bonds. In this procedure, the compounds 67.6 are converted, using the procedures described below, Schemes 133-197, into the compounds 15.

Scheme 56

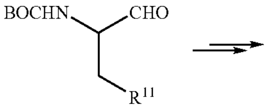

49.3

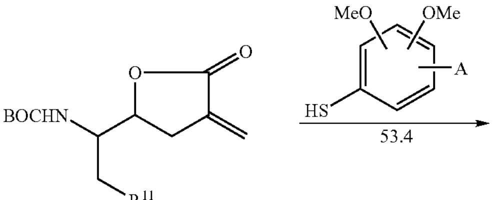

56.1

53.4

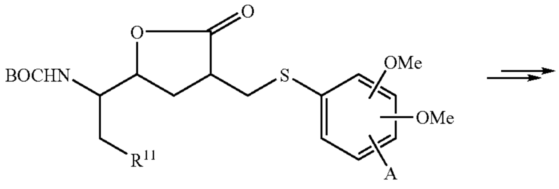

56.2

-continued

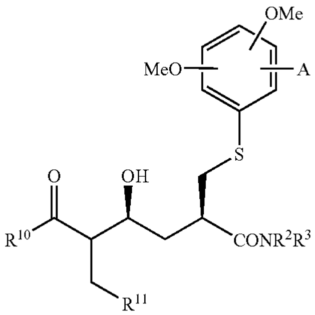

56.3

Scheme 57

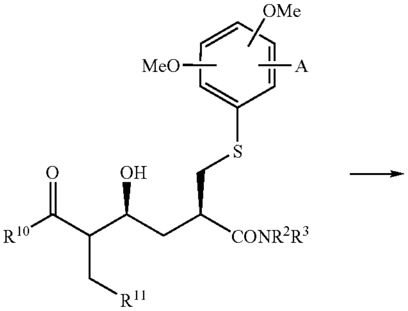

56.3

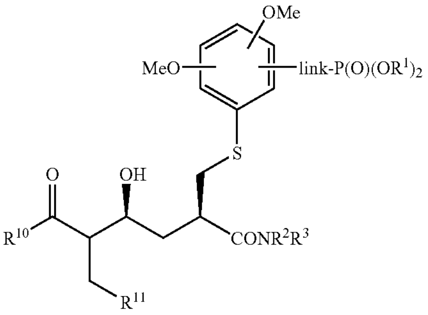

13

Scheme 58

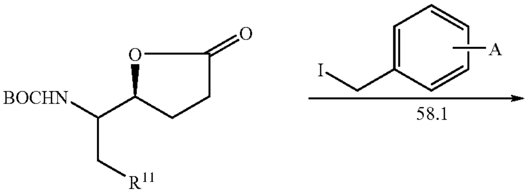

49.6

58.1

-continued
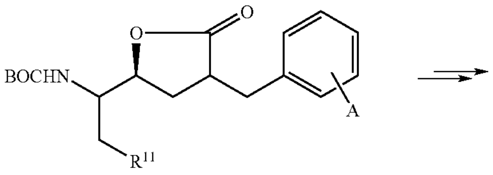
58.2
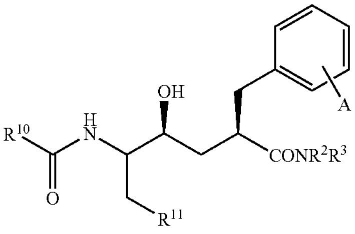
58.3
Scheme 59
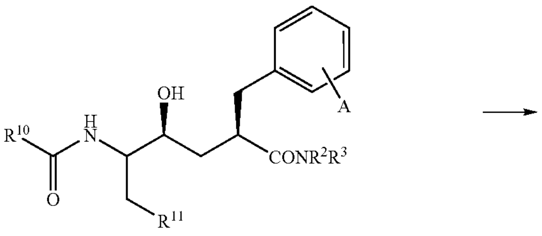
58.3
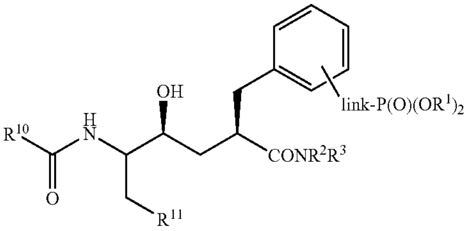
14
Scheme 60
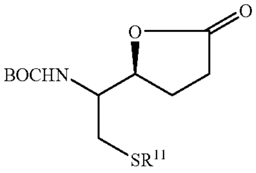
54.1
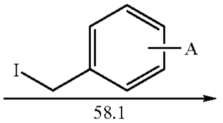
58.1
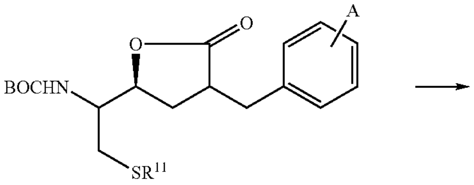
60.1
-continued
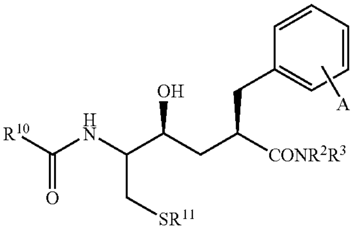
60.2
Scheme 61
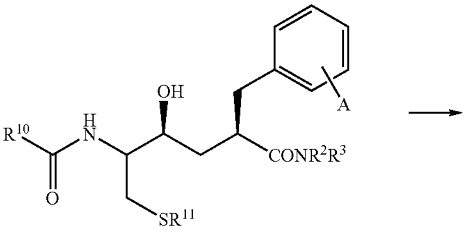
60.2
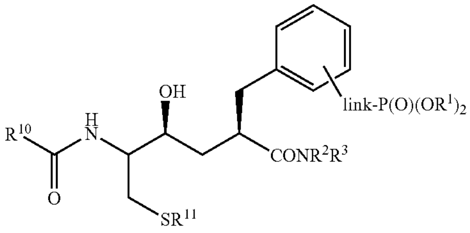
14
Scheme 62
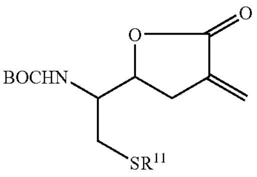
53.3
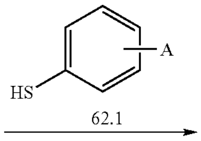
62.1
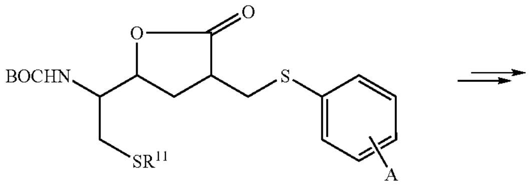
62.2

-continued
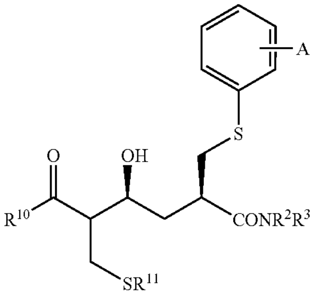
62.3
Scheme 63
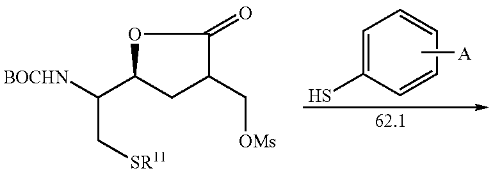
54.3
62.1
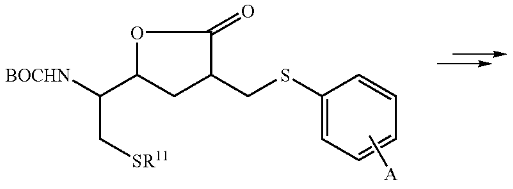
63.1
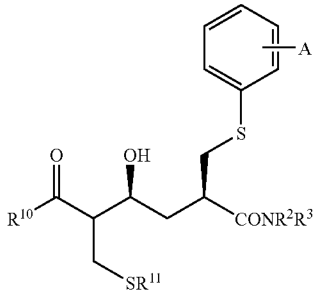
62.3
Scheme 64
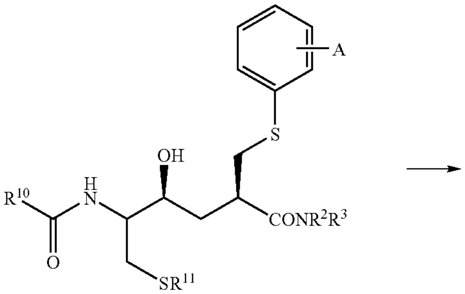
62.3
-continued
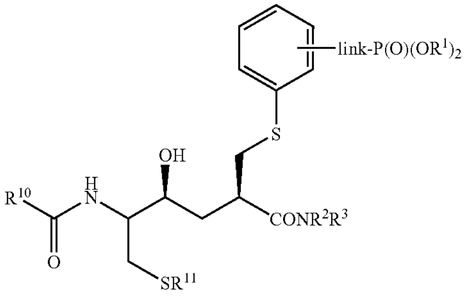
14
Scheme 65
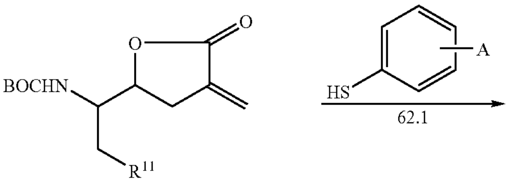
56.1
62.1
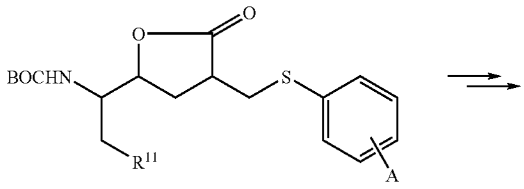
65.1
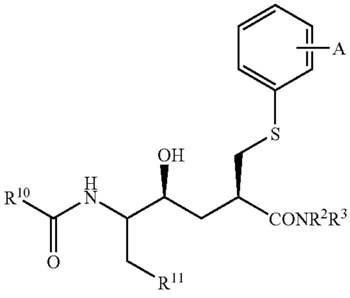
65.2
Scheme 66
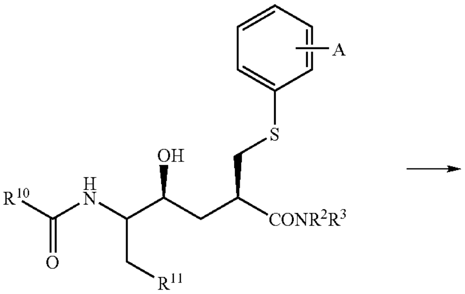
65.2

-continued

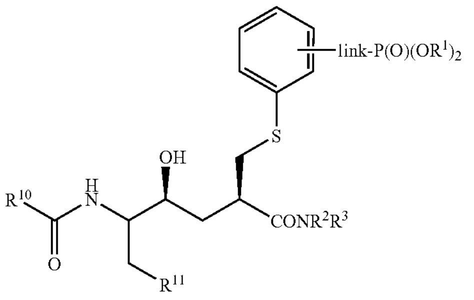

14

Scheme 67

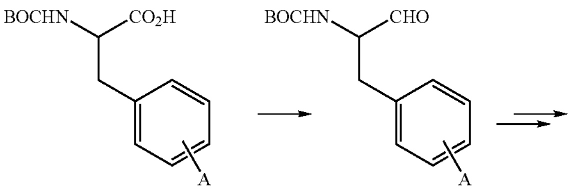

67.1 67.2

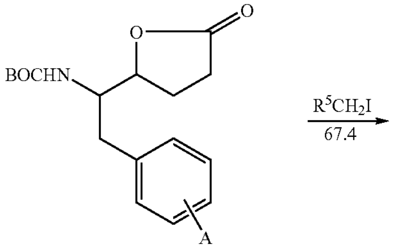

67.3

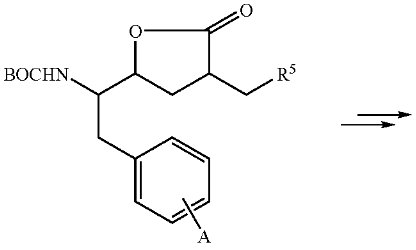

67.5

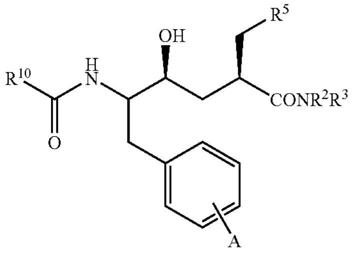

67.6

Scheme 68

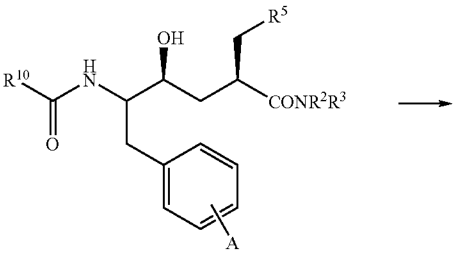

67.6

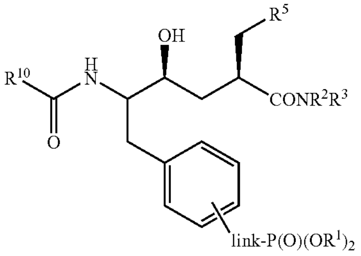

15

Preparation of the Phosphonate Ester Intermediates 15 in which X is a Direct Bond and X' is Sulfur.

Schemes 69 and 70 illustrate the preparation of the phosphonate esters 15 in which X is a direct bond and X' is sulfur. In this procedure, the mesylate 51.1 is reacted, as described in Scheme 51, with the thiophenol derivative 69.1. The preparation of the thiophenol derivatives 69.1 is described below, Schemes 144-153. The product is then converted, as described in Scheme 51, into the corresponding aldehyde 69.3, and the latter compound is then transformed, as described in Scheme 49, into the lactone 69.4. The lactone is then alkylated, as described in Scheme 49, with the reagent $R^5CH_2I$, (67.4), to afford the alkylated product 69.5. This compound is then converted, as described in Scheme 49, into the diamide 69.6.

The reactions shown in Scheme 69 illustrate the preparation of the compounds 69.6 in which the substituent A is either the group link-$P(O)(OR^1)_2$ or a precursor such as [OH], [SH], [NH], Br. Scheme 70 depicts the conversion of the compounds 69.6 in which A is [OH], [SH], [NH], Br, into the phosphonate esters 15 in which X is a direct bond and X' is sulfur. In this procedure, the compounds 69.6 are converted, using the procedures described below, Schemes 133-197, into the compounds 15.

Preparation of the Phosphonate Ester Intermediates 15 in which X and X' are Sulfur.

Schemes 71, 72 and 73 illustrate the preparation of the phosphonate esters 15 in which X and X' are sulfur. As shown in Scheme 71, the aldehyde 69.3 is converted, as described in Scheme 53, into the methylene lactone 71.1. The lactone is then reacted, as described in Scheme 53, with the thiol reagent 71.2 to yield the thioether product 71.3. The product is then transformed, as described in Scheme 53, into the diamide 71.4.

Scheme 72 illustrates an alternative method for the preparation of the diamide 71.4. In this procedure, the lactone 69.4 is reacted, as described in Scheme 54, with formaldehyde or a formaldehyde equivalent, to afford the hydroxymethyl product 72.1. The product is then transformed, by mesylation followed by reaction of the mesylate with the thiol reagent 71.2, using the procedures described in Scheme 53, into the thioether 71.3. The latter compound is then converted, as described in Scheme 53, into the diamide 71.4.

The reactions shown in Schemes 71 and 72 illustrate the preparation of the compounds 71.4 in which the substituent A is either the group link-$P(O)(OR^1)_2$ or a precursor such as [OH], [SH], [NH], Br. Scheme 73 depicts the conversion of the compounds 71.4 in which A is [OH], [SH], [NH], Br, into the phosphonate esters 15 in which X and X' are sulfur. In this procedure, the compounds 71.4 are converted, using the procedures described below, Schemes 133-197, into the compounds 15.

Preparation of the Phosphonate Ester Intermediates 15 in which X is Sulfur and X' is a Direct Bond.

Schemes 74 and 75 illustrate the preparation of the phosphonate esters 15 in which X is sulfur and X' is a direct bond. In this procedure, the aldehyde 67.2 is converted, as described in Scheme 53, into the methylene lactone 74.1. The lactone is then reacted, as described in Scheme 53, with the thiol 71.2 to afford the thioether 74.2. This compound is then converted, as described in Scheme 53, into the diamide 74.3.

The reactions shown in Schemes 74 illustrate the preparation of the compounds 74.3 in which the substituent A is either the group link-$P(O)(OR^1)_2$ or a precursor such as [OH], [SH], [NH], Br. Scheme 75 depicts the conversion of the compounds 74.3 in which A is [OH], [SH], [NH], Br, into the phosphonate esters 15 in which X is sulfur and X' is a direct bond. In this procedure, the compounds 74.3 are converted, using the procedures described below, Schemes 133-197, into the compounds 15.

Preparation of the Phosphonate Ester Intermediates 16 in which X and X' are Direct Bonds.

Schemes 76 and 77 illustrate the preparation of the phosphonate esters 16 in which X and X' are direct bonds. In this procedure, the lactone 49.6 is reacted, as described in Scheme 49, with the iodo compound 67.4 to yield the alkylated lactone 76.1. The lactone is then converted, as described in Scheme 49, into the carboxylic acid 76.2. The carboxylic acid is then coupled, as described in Scheme 1, with the aminoindanol derivative 1.2 to afford the amide 76.3. The latter compound is then converted, as described in Scheme 49, into the diamide 76.4.

The reactions shown in Scheme 76 illustrate the preparation of the compounds 76.4 in which the substituent A is either the group link-$P(O)(OR^1)_2$ or a precursor such as [OH], [SH], [NH], Br. Scheme 77 depicts the conversion of the compounds 76.4 in which A is [OH], [SH], [NH], Br, into the phosphonate esters 16 in which X and X' are direct bonds. In this procedure, the compounds 76.4 are converted, using the procedures described below, Schemes 133-197, into the compounds 16.

Preparation of the Phosphonate Ester Intermediates 16 in which X is a Direct Bond and X' is Sulfur.

Schemes 78 and 79 illustrate the preparation of the phosphonate esters 16 in which X is a direct bond and X' is sulfur. In this procedure, the lactone 54.1 is reacted, as described in Scheme 49, with the iodo compound 67.4, to produce the alkylated compound 78.1. This material is then transformed, as described in Scheme 49, into the carboxylic acid 78.2, which is then transformed, as described in Scheme 76, into the diamide 78.3.

The reactions shown in Scheme 78 illustrate the preparation of the compounds 78.3 in which the substituent A is either the group link-$P(O)(OR^1)_2$ or a precursor such as [OH], [SH], [NH], Br. Scheme 79 depicts the conversion of the compounds 78.3 in which A is [OH], [SH], [NH], Br, into the phosphonate esters 16 in which X is a direct bond and X' is sulfur. In this procedure, the compounds 78.3 are converted, using the procedures described below, Schemes 133-197, into the compounds 16.

Preparation of the Phosphonate Ester Intermediates 16 in which X and X' are Sulfur.

Schemes 80, 81 and 82 illustrate the preparation of the phosphonate esters 15 in which X and X' are sulfur. As shown in Scheme 80, the methylene lactone 53.3 is reacted with the thiol 71.2 to produce the thioether 80.1. The compound is then transformed, as described in Scheme 49, into the silyl-protected carboxylic acid 80.2. This material is then converted, as described in Scheme 76, into the diamide 80.3.

Scheme 81 illustrates an alternative method for the preparation of the compounds 80.2. In this procedure, the mesylate 54.3 is reacted, as described in Scheme 54, with the thiol 71.2, to prepare the thioether 80.1. The product is then transformed, as described in Scheme 54, into the diamide 80.3.

The reactions shown in Schemes 80 and 81 illustrate the preparation of the compounds 80.3 in which the substituent A is either the group link-$P(O)(OR^1)_2$ or a precursor such as [OH], [SH], [NH], Br. Scheme 82 depicts the conversion of the compounds 80.3 in which A is [OH], [SH], [NH], Br, into the phosphonate esters 16 in which X and X' are sulfur. In this procedure, the compounds 80.3 are converted, using the procedures described below, Schemes 133-197, into the compounds 16.

Preparation of the Phosphonate Ester Intermediates 16 in which X is Sulfur and X' is a Direct Bond.

Schemes 83 and 84 illustrate the preparation of the phosphonate esters 16 in which X is sulfur and X' is a direct bond. In this procedure, the methylene lactone 53.3 is reacted, as described in Scheme 53, with the thiol 71.2 to yield the thioether 83.1. The product is then converted, as described in Scheme 76, into the diamide 83.2.

The reactions shown in Scheme 83 illustrate the preparation of the compounds 83.2 in which the substituent A is either the group link-$P(O)(OR^1)_2$ or a precursor such as [OH], [SH], [NH], Br. Scheme 84 depicts the conversion of the compounds 83.2 in which A is [OH], [SH], [NH], Br, into the phosphonate esters 16 in which X is sulfur and X' is a direct bond. In this procedure, the compounds 83.2 are converted, using the procedures described below, Schemes 133-197, into the compounds 16.

Scheme 69

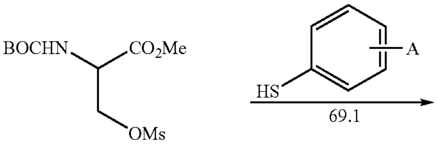

51.1

69.1

-continued
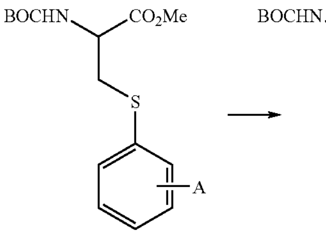
69.2
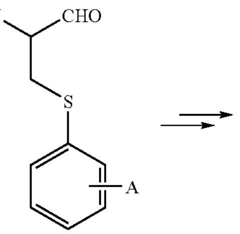
69.3
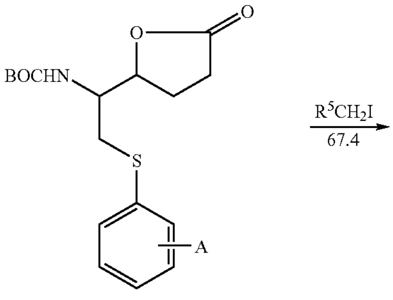
69.4
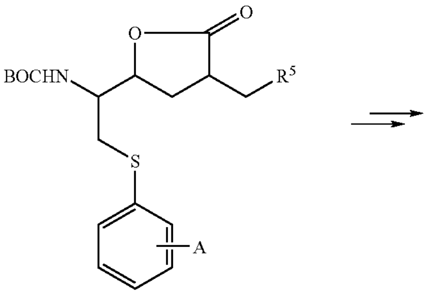
69.5
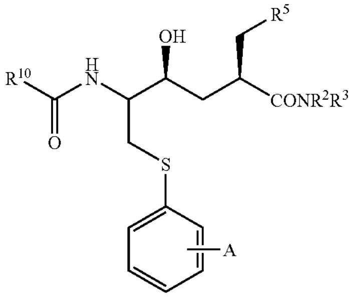
69.6
Scheme 70
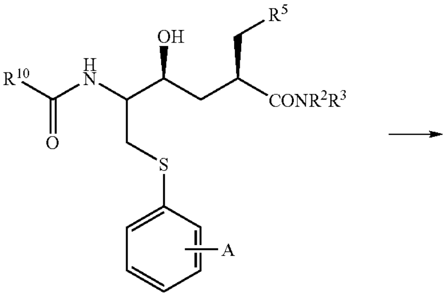
69.6
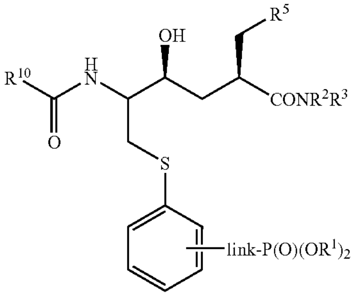
15
Scheme 71
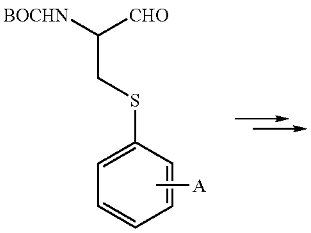
69.3
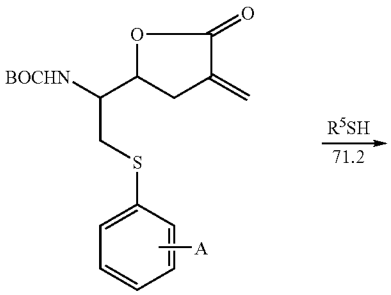
71.1

-continued
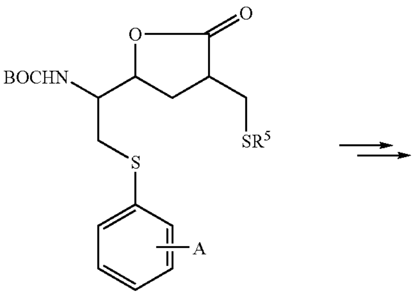
71.3
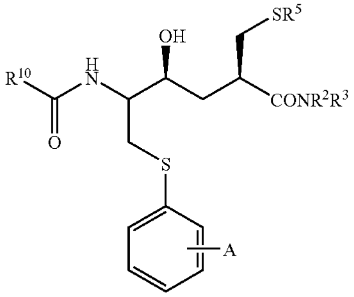
71.4
-continued
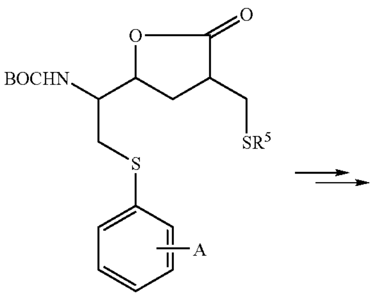
71.3
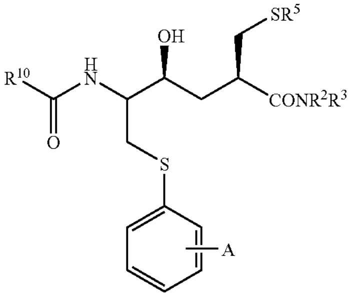
71.4
Scheme 72
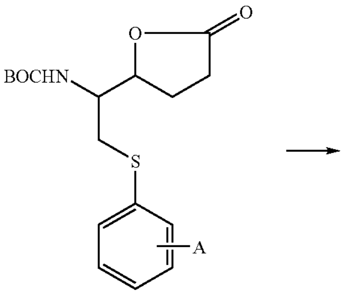
69.4
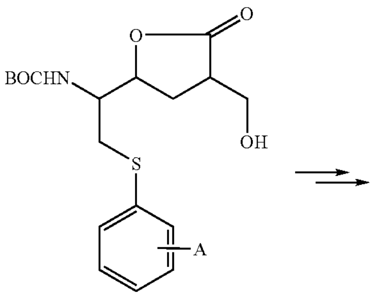
72.1
Scheme 73
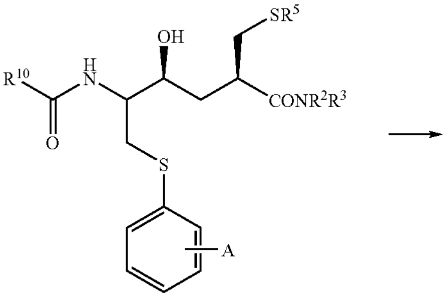
71.4
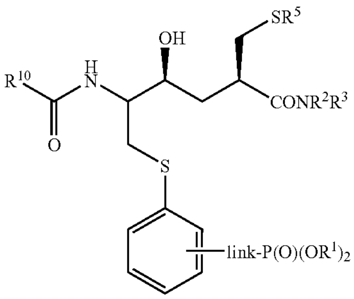
15

Scheme 74
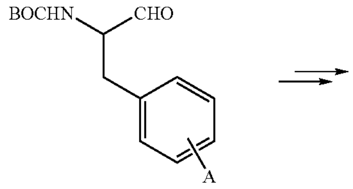
67.2
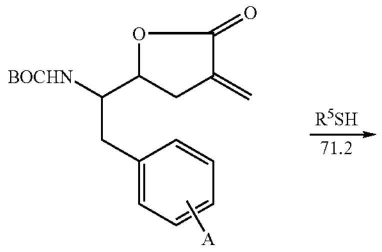
74.1
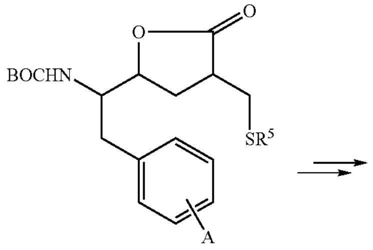
74.2
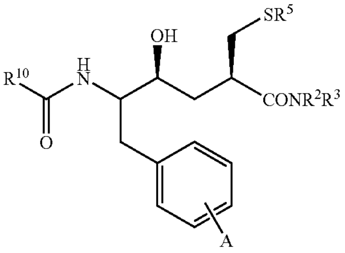
74.3
Scheme 75
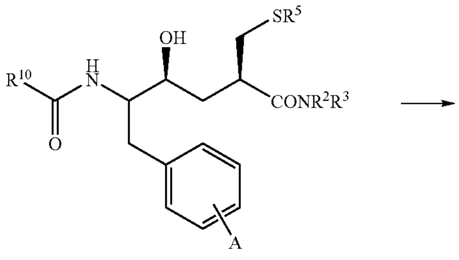
74.3
-continued
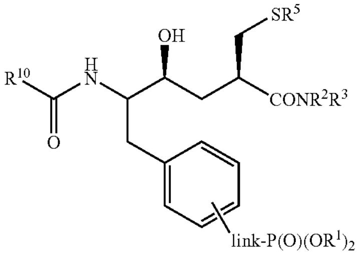
15
Scheme 76
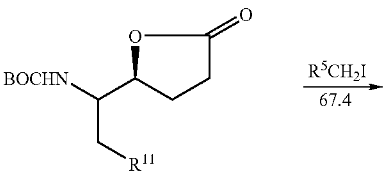
49.6
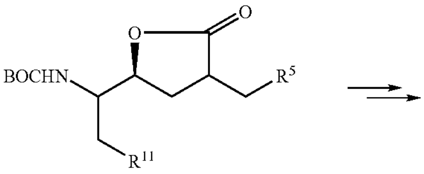
76.1
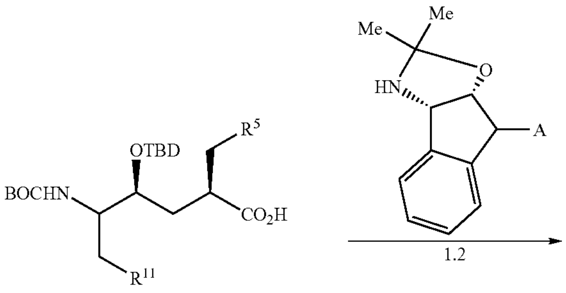
76.2
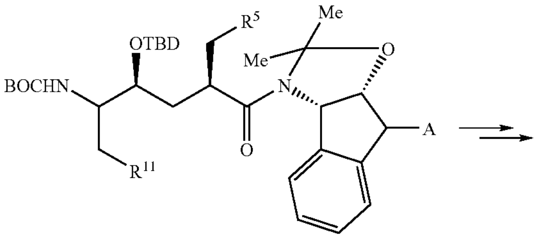
76.3
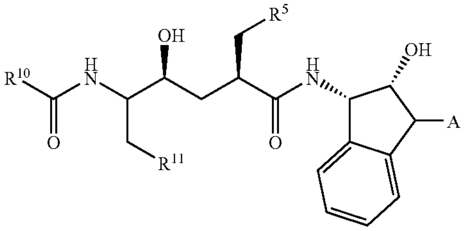
76.4

Scheme 77
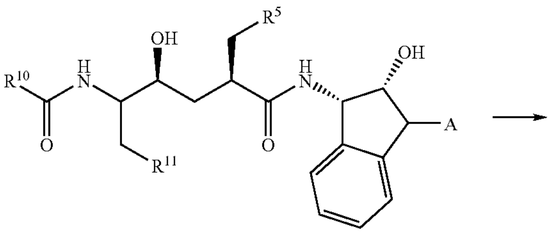
76.4
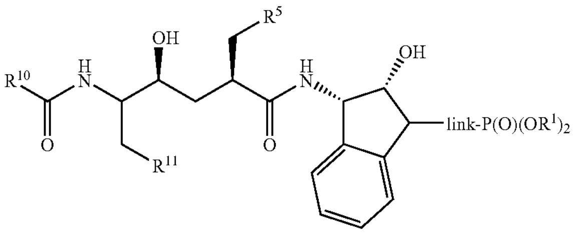
16
Scheme 78
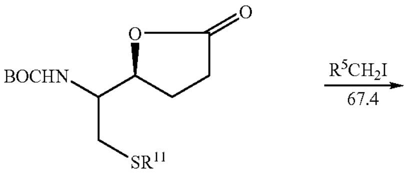
54.1
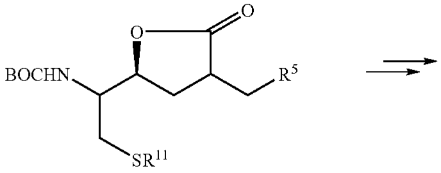
78.1
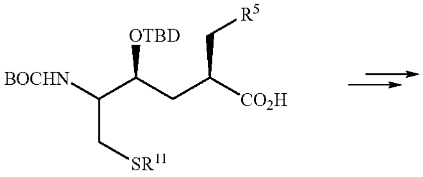
78.2
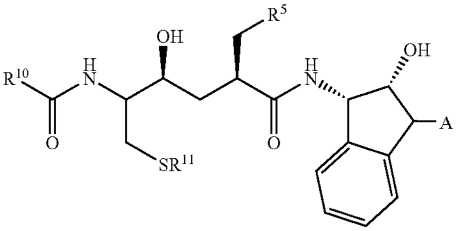
78.3
Scheme 79
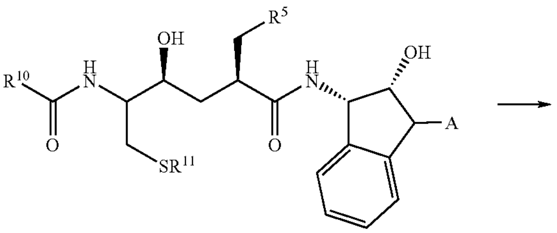
78.3
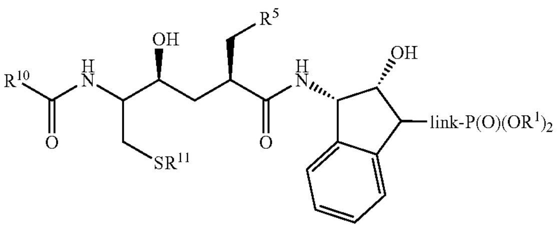
16
Scheme 80
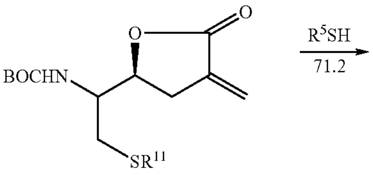
53.3
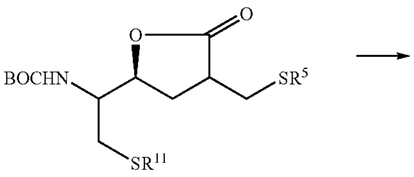
80.1
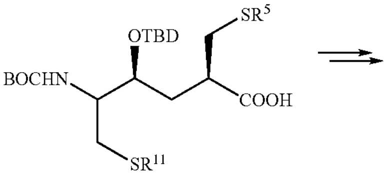
80.2
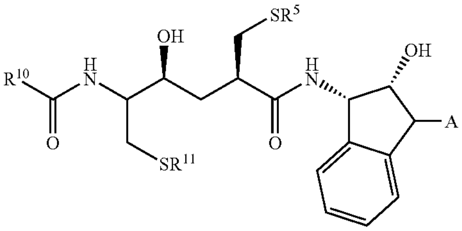
80.3

Scheme 81

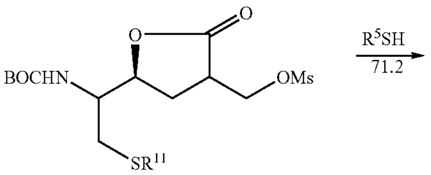

54.3

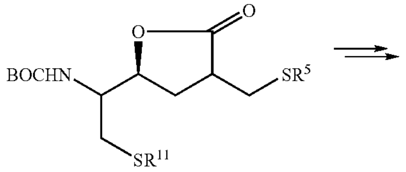

80.1

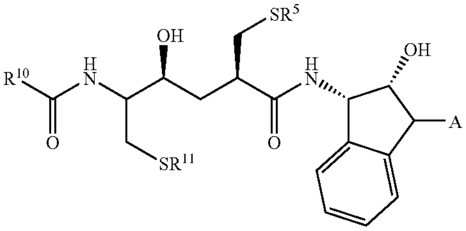

80.3

Scheme 82

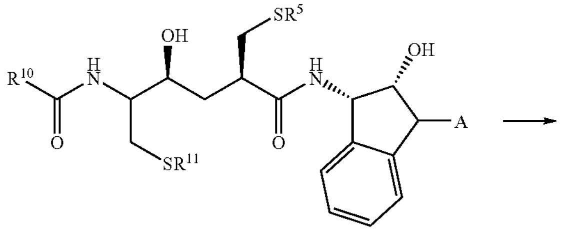

80.3

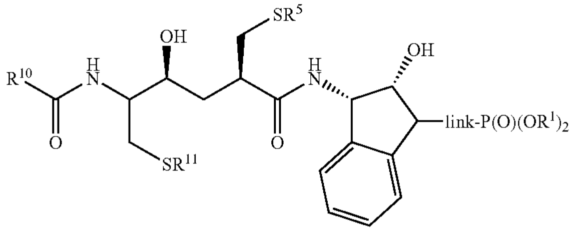

16

Scheme 83

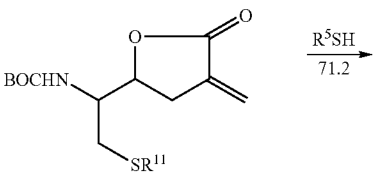

53.3

-continued

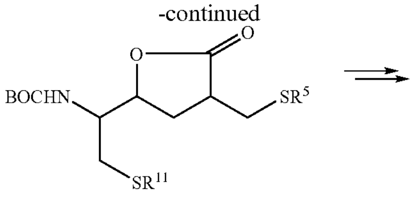

83.1

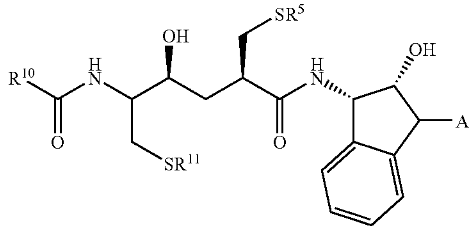

83.2

Scheme 84

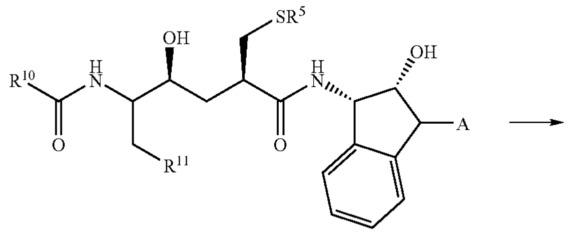

83.2

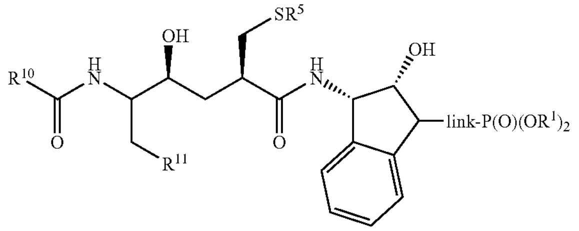

16

Preparation of the Phosphonate Ester Intermediates 17 in which X and X' are Direct Bonds.

Schemes 85 and 86 illustrate the preparation of the phosphonate esters 17 in which X and X' are direct bonds. In this procedure, the carboxylic acid 76.2 is coupled, as described in Scheme 1, with the aminochroman derivative 33.1 to afford the amide 85.1. The product is then converted, as described in Scheme 49, into the diamide 85.2.

The reactions shown in Scheme 85 illustrate the preparation of the compounds 85.2 in which the substituent A is either the group link-P(O)$(OR^1)_2$ or a precursor such as [OH], [SH], [NH], Br. Scheme 86 depicts the conversion of the compounds 85.2 in which A is [OH], [SH], [NH], Br, into the phosphonate esters 17 in which X and X' are direct bonds. In this procedure, the compounds 85.2 are converted, using the procedures described below, Schemes 133-197, into the compounds 17.

Preparation of the Phosphonate Ester Intermediates 17 in which X is a Direct Bond and X' is Sulfur.

Schemes 87 and 88 illustrate the preparation of the phosphonate esters 17 in which X is a direct bond and X' is sulfur.

In this procedure, the carboxylic acid 78.2 is coupled with the amine 33.1 to afford the amide 87.1. The product is then converted, as described in Scheme 49, into the diamide 87.2.

The reactions shown in Scheme 87 illustrate the preparation of the compounds 87.2 in which the substituent A is either the group link-$P(O)(OR^1)_2$ or a precursor such as [OH], [SH], [NH], Br. Scheme 88 depicts the conversion of the compounds 87.2 in which A is [OH], [SH], [NH], Br, into the phosphonate esters 17 in which X is a direct bond and X' is sulfur. In this procedure, the compounds 87.2 are converted, using the procedures described below, Schemes 133-197, into the compounds 17.

Preparation of the Phosphonate Ester Intermediates 17 in which X and X' are Sulfur.

Schemes 89 and 90 illustrate the preparation of the phosphonate esters 17 in which X and X' are sulfur. As shown in Scheme 89, the carboxylic acid 80.2 is coupled, as described in Scheme 1, with the chroman amine 33.1 to give the amide 89.1. The product is then transformed, as described in Scheme 49, into the diamide 89.2.

The reactions shown in Scheme 89 illustrate the preparation of the compounds 89.2 in which the substituent A is either the group link-$P(O)(OR^1)_2$ or a precursor such as [OH], [SH], [NH], Br. Scheme 90 depicts the conversion of the compounds 89.2 in which A is [OH], [SH], [NH], Br, into the phosphonate esters 17 in which X and X' are sulfur. In this procedure, the compounds 89.2 are converted, using the procedures described below, Schemes 133-197, into the compounds 17.

Preparation of the Phosphonate Ester Intermediates 17 in which X is Sulfur and X' is a Direct Bond.

Schemes 91 and 92 illustrate the preparation of the phosphonate esters 17 in which X is sulfur and X' is a direct bond. In this procedure, the carboxylic acid 91.1, which is an intermediate compound in the conversion of the lactone 83.1 into the diamide 83.2, (Scheme 83), is coupled, as described in Scheme 1, with the chroman amine 33.1 to afford the amide 91.2. The product is then converted, as described in Scheme 49, into the diamide 91.3.

The reactions shown in Scheme 91 illustrate the preparation of the compounds 91.3 in which the substituent A is either the group link-$P(O)(OR^1)_2$ or a precursor such as [OH], [SH], [NH], Br. Scheme 92 depicts the conversion of the compounds 91.3 in which A is [OH], [SH], [NH], Br, into the phosphonate esters 17 in which X is sulfur and X' is a direct bond. In this procedure, the compounds 91.3 are converted, using the procedures described below, Schemes 133-197, into the compounds 17.

Preparation of the phosphonate ester intermediates 18 in which X and X' are direct bonds.

Schemes 93 and 94 illustrate the preparation of the phosphonate esters 18 in which X and X' are direct bonds. In this procedure, the carboxylic acid 76.2 is coupled, as described in Scheme 1, with the ethanolamine derivative 29.1 to afford the amide 93.1. The product is then converted, as described in Scheme 49, into the diamide 93.2.

The reactions shown in Scheme 93 illustrate the preparation of the compounds 93.2 in which the substituent A is either the group link-$P(O)(OR^1)_2$ or a precursor such as [OH], [SH], [NH], Br. Scheme 94 depicts the conversion of the compounds 93.2 in which A is [OH], [SH], [NH], Br, into the phosphonate esters 18 in which X and X' are direct bonds. In this procedure, the compounds 93.2 are converted, using the procedures described below, Schemes 133-197, into the compounds 18.

Preparation of the Phosphonate Ester Intermediates 18 in which X and X' are Sulfur.

Scheme 85

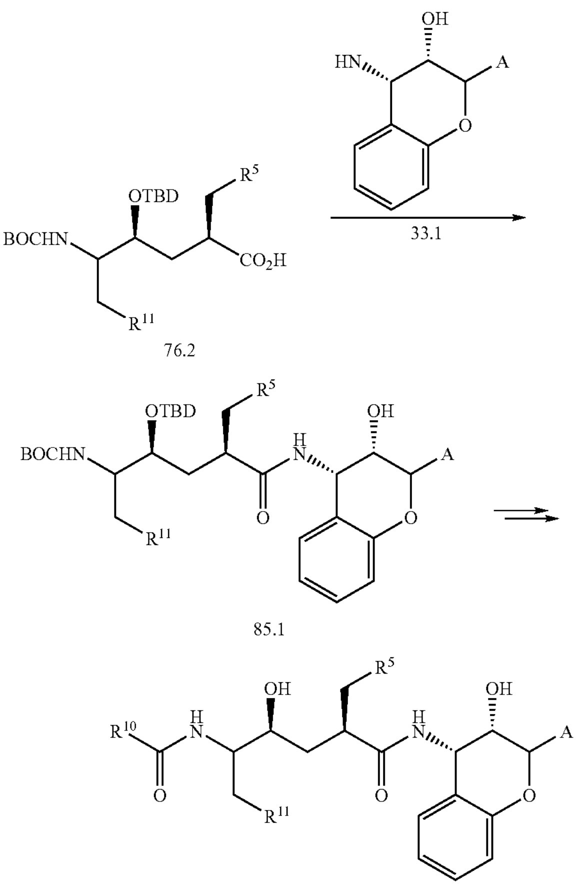

76.2

85.1

85.2

Scheme 86

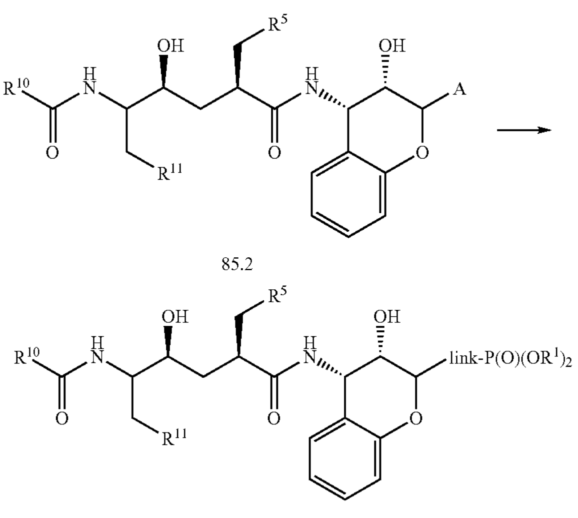

85.2

17

Scheme 87
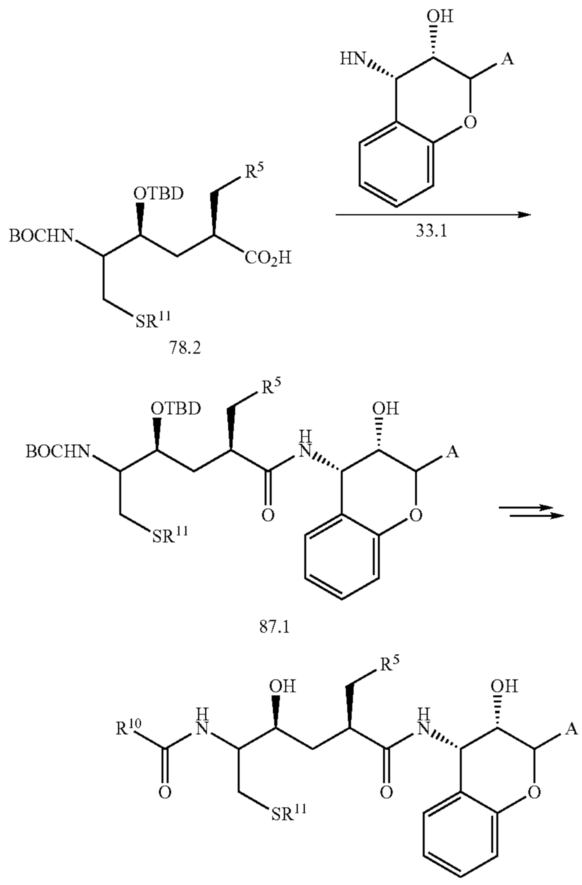
78.2
87.1
87.2
Scheme 88
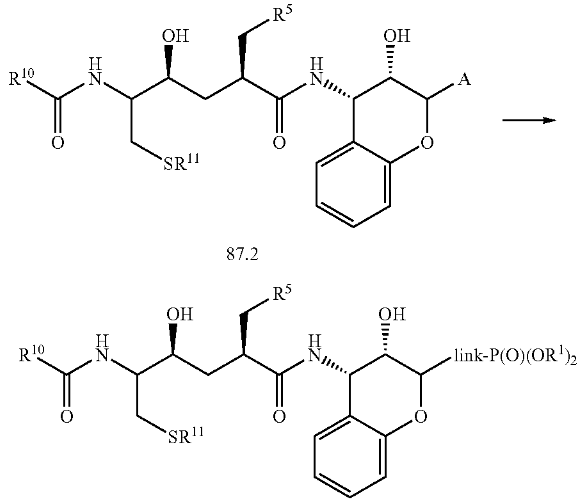
87.2
17
Scheme 89
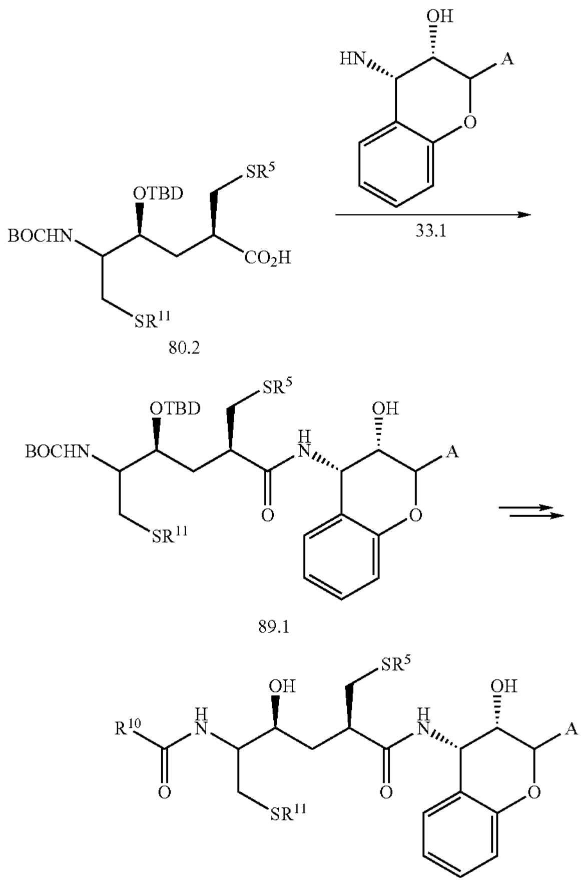
80.2
89.1
89.2
Scheme 90
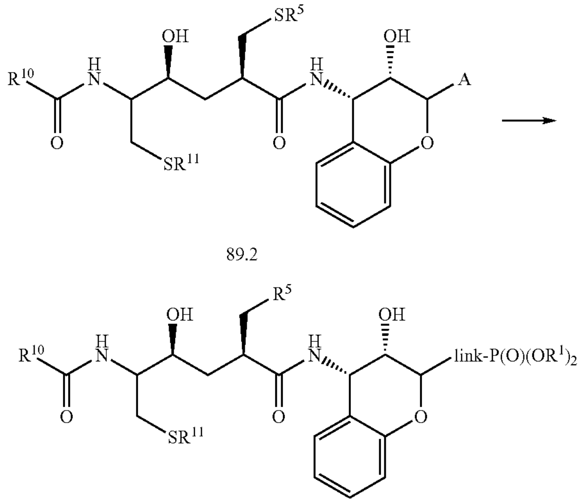
89.2
17

Scheme 91
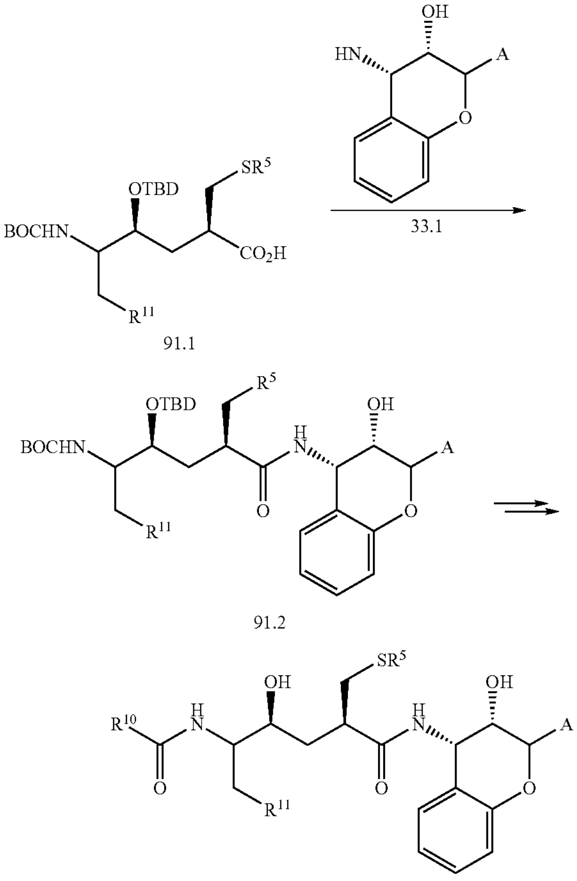
91.1
91.2
91.3
Scheme 92
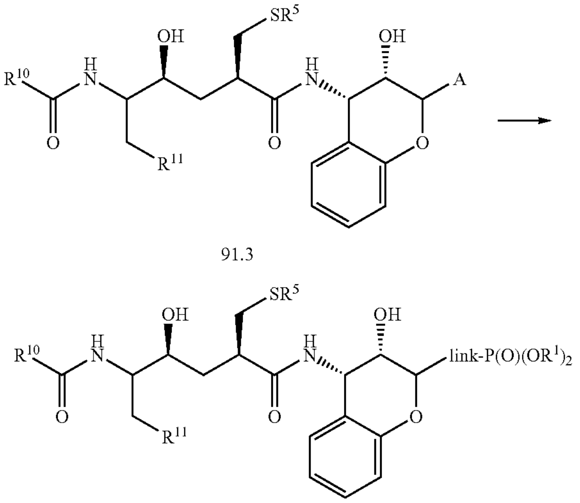
91.3
17
Scheme 93
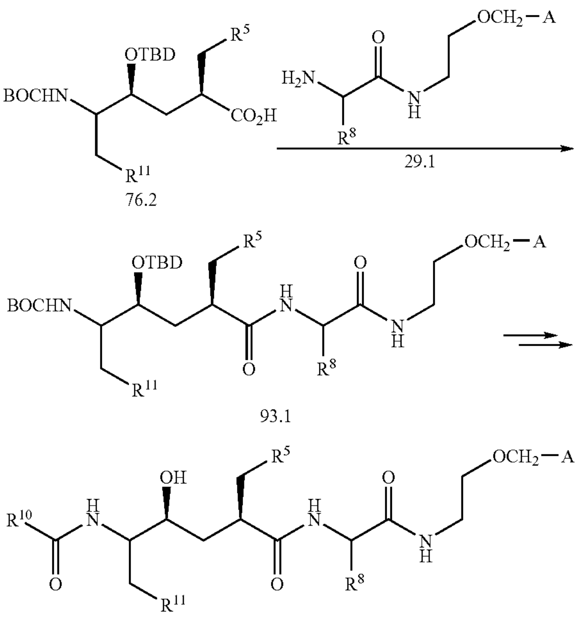
76.2
93.1
93.2
Scheme 94
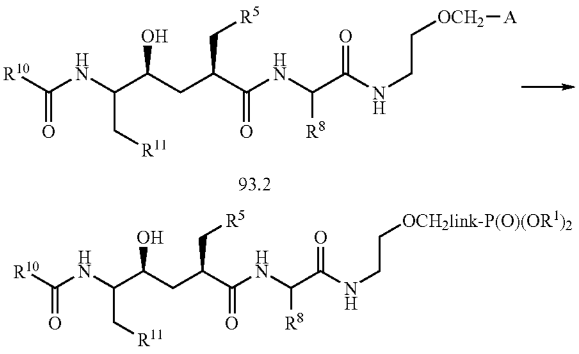
93.2
18
Scheme 95
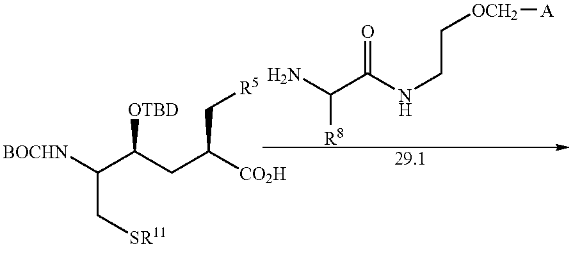
78.2

-continued

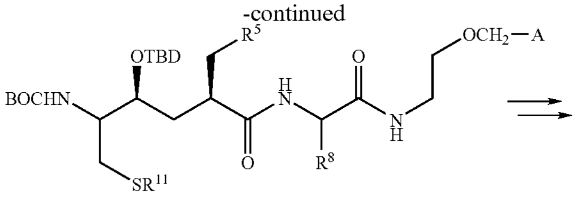

95.1

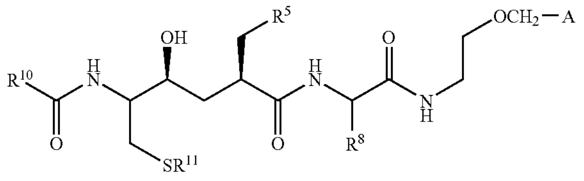

95.2

Scheme 96

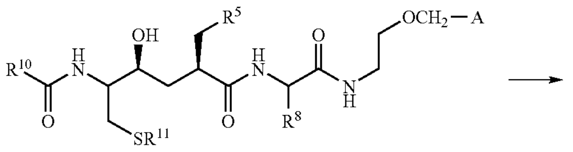

95.2

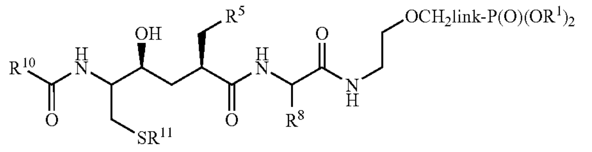

18

Schemes 97 and 98 illustrate the preparation of the phosphonate esters 18 in which X and X' are sulfur. As shown in Scheme 97, the carboxylic acid 80.2 is coupled, as described in Scheme 1, with the ethanolamine derivative 29.1 to give the amide 97.1. The product is then transformed, as described in Scheme 49, into the diamide 97.2.

The reactions shown in Scheme 97 illustrate the preparation of the compounds 97.2 in which the substituent A is either the group link-$P(O)(OR^1)_2$ or a precursor such as [OH], [SH], [NH], Br. Scheme 98 depicts the conversion of the compounds 97.2 in which A is [OH], [SH], [NH], Br, into the phosphonate esters 18 in which X and X' are sulfur. In this procedure, the compounds 97.2 are converted, using the procedures described below, Schemes 133-197, into the compounds 18.

Preparation of the Phosphonate Ester Intermediates 18 in which X is Sulfur and X' is a Direct Bond.

Schemes 99 and 100 illustrate the preparation of the phosphonate esters 18 in which X is sulfur and X' is a direct bond. In this procedure, the carboxylic acid 91.1 is coupled, as described in Scheme 1, with the ethanolamine derivative 29.1 to afford the amide 99.1. The product is then converted, as described in Scheme 49, into the diamide 99.2.

The reactions shown in Scheme 99 illustrate the preparation of the compounds 99.2 in which the substituent A is either the group link-$P(O)(OR^1)_2$ or a precursor such as [OH], [SH], [NH], Br. Scheme 100 depicts the conversion of the compounds 99.2 in which A is [OH], [SH], [NH], Br, into the phosphonate esters 18 in which X is sulfur and X' is a direct bond. In this procedure, the compounds 99.2 are converted, using the procedures described below, Schemes 133-197, into the compounds 18.

Preparation of the Phosphonate Ester Intermediates 19 in which X and X' are Direct Bonds.

Schemes 101 and 102 illustrate the preparation of the phosphonate esters 19 in which X and X' are direct bonds. In this procedure, the carboxylic acid 76.2 is coupled, as described in Scheme 1, with the phenylalanine derivative 37.1 to afford the amide 101.1. The product is then converted, as described in Scheme 49, into the diamide 101.2.

The reactions shown in Scheme 101 illustrate the preparation of the compounds 101.2 in which the substituent A is either the group link-$P(O)(OR^1)_2$ or a precursor such as [OH], [SH], [NH], Br. Scheme 102 depicts the conversion of the compounds 101.2 in which A is [OH], [SH], [NH], Br, into the phosphonate esters 19 in which X and X' are direct bonds. In this procedure, the compounds 101.2 are converted, using the procedures described below, Schemes 133-197, into the compounds 19.

Preparation of the Phosphonate Ester Intermediates 19 in which X is a Direct Bond and X' is Sulfur.

Schemes 103 and 104 illustrate the preparation of the phosphonate esters 19 in which X is a direct bond and X' is sulfur. In this procedure, the carboxylic acid 78.2 is coupled, as described in Scheme 1, with the amine 37.1 to afford the amide 103.1. The product is then converted, as described in Scheme 49, into the diamide 103.2.

The reactions shown in Scheme 103 illustrate the preparation of the compounds 103.2 in which the substituent A is either the group link-$P(O)(OR^1)_2$ or a precursor such as [OH], [SH], [NH], Br. Scheme 104 depicts the conversion of the compounds 103.2 in which A is [OH], [SH], [NH], Br, into the phosphonate esters 19 in which X is a direct bond and X' is sulfur. In this procedure, the compounds 103.2 are converted, using the procedures described below, Schemes 133-197, into the compounds 19.

Preparation of the Phosphonate Ester Intermediates 19 in which X and X' are Sulfur.

Schemes 105 and 106 illustrate the preparation of the phosphonate esters 19 in which X and X' are sulfur. As shown in Scheme 105, the carboxylic acid 80.2 is coupled, as described in Scheme 1, with the phenylalanine derivative 37.1 to give the amide 105.1. The product is then transformed, as described in Scheme 49, into the diamide 105.2.

The reactions shown in Scheme 105 illustrate the preparation of the compounds 105.2 in which the substituent A is either the group link-$P(O)(OR^1)_2$ or a precursor such as [OH], [SH], [NH], Br. Scheme 106 depicts the conversion of the compounds 105.2 in which A is [OH], [SH], [NH], Br, into the phosphonate esters 19 in which X and X' are sulfur. In this procedure, the compounds 105.2 are converted, using the procedures described below, Schemes 133-197, into the compounds 19.

Scheme 97
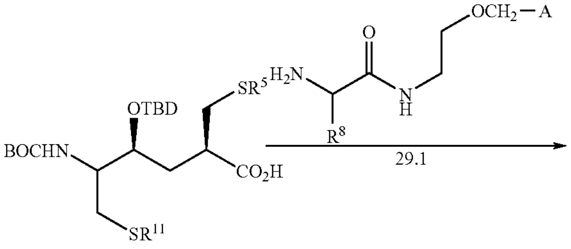
80.2
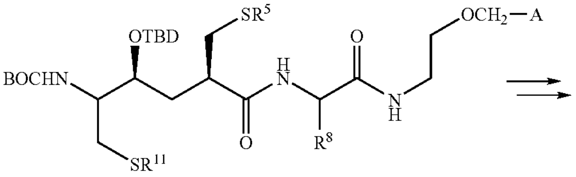
97.1
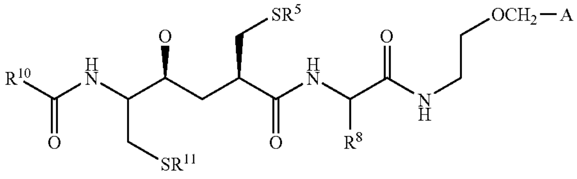
97.2
Scheme 98
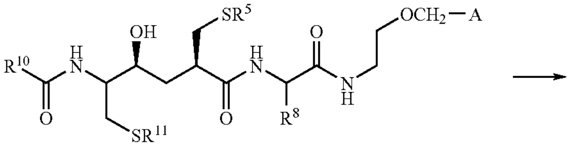
97.2
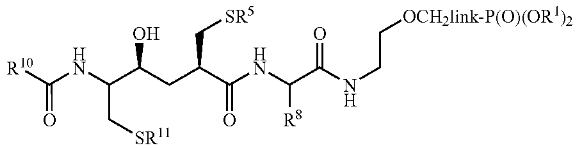
18
Scheme 99
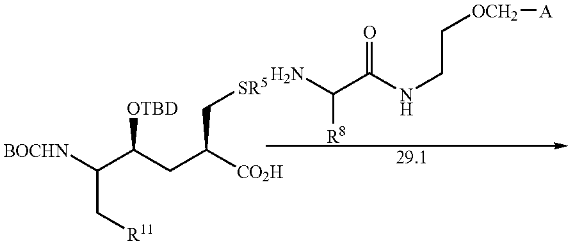
91.1
-continued
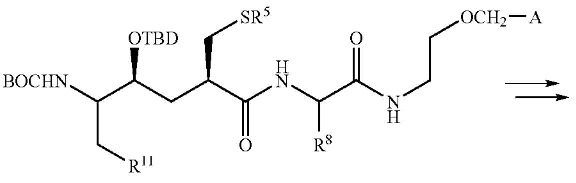
99.1
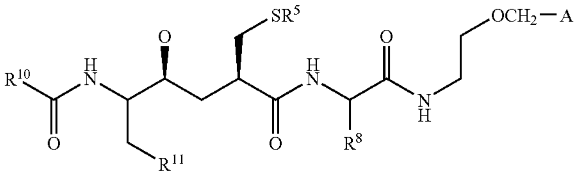
99.2
Scheme 100
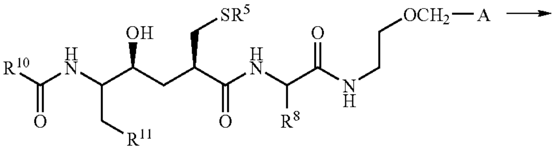
99.2
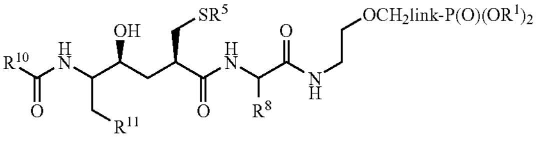
18
Scheme 101
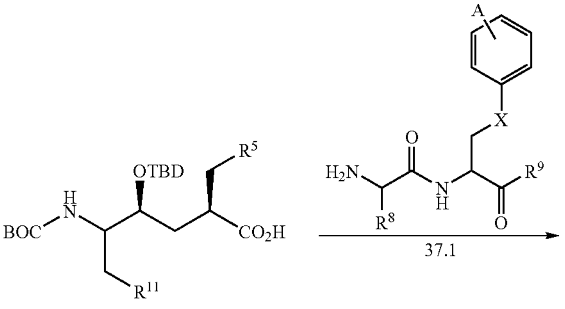
76.2

-continued
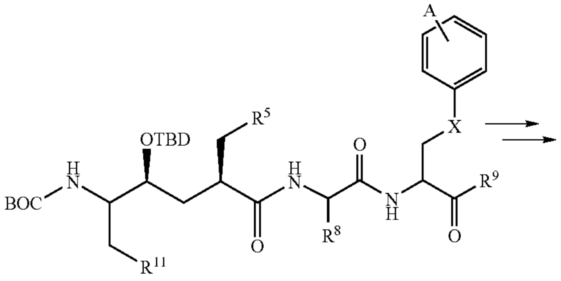
101.1
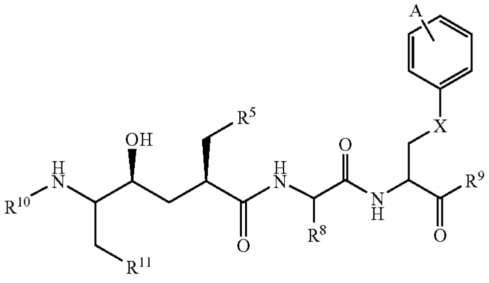
101.2
Scheme 102
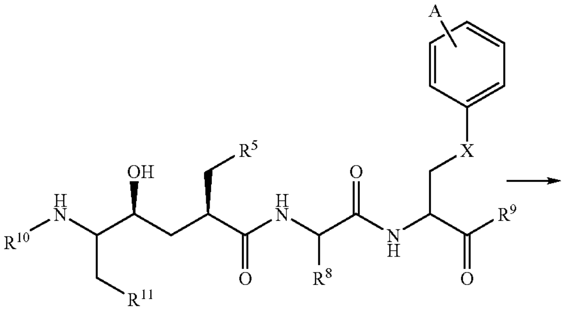
101.2
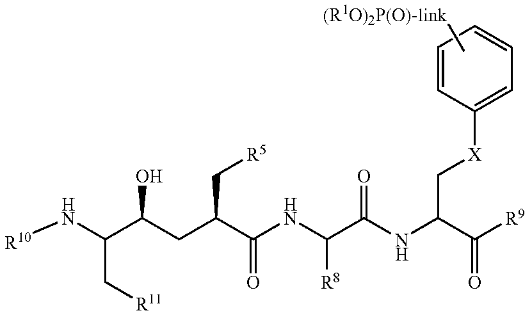
19
Scheme 103
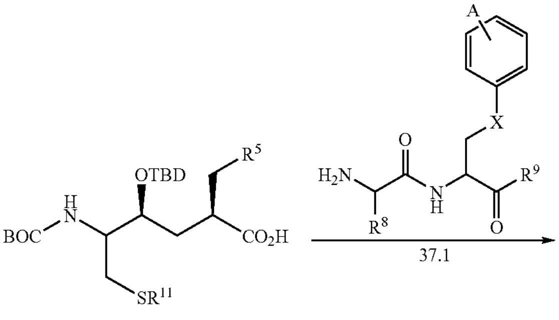
78.2
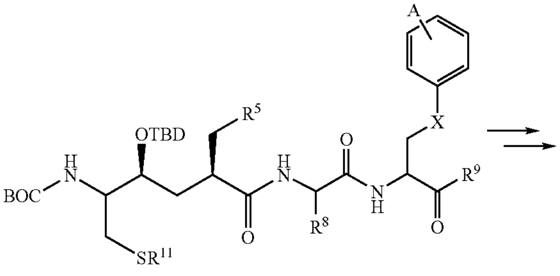
103.1
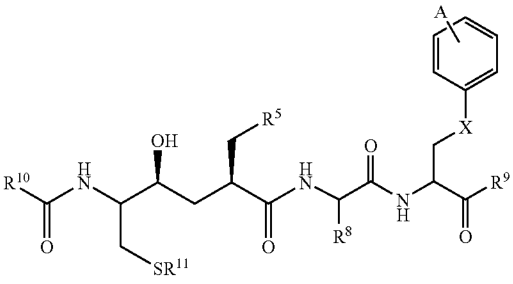
103.2
Scheme 104
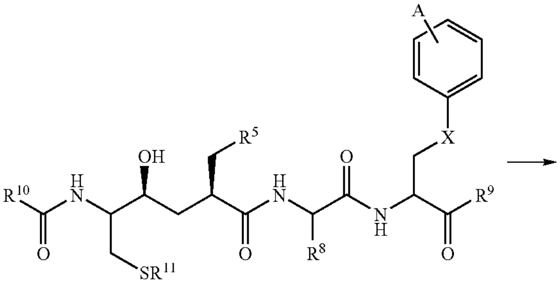
103.2

-continued

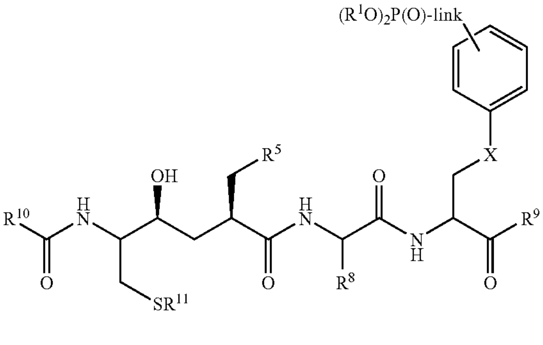

19

Scheme 105

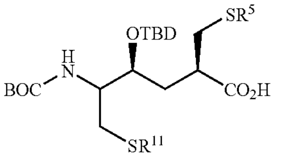

80.2

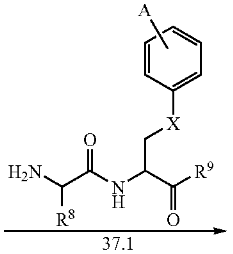

37.1

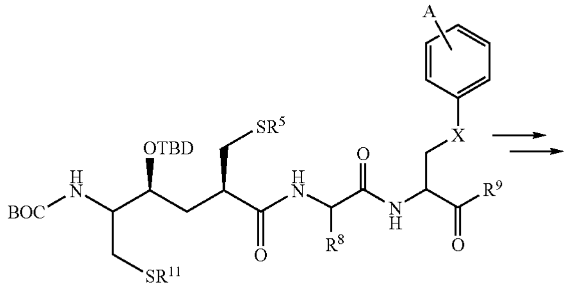

105.1

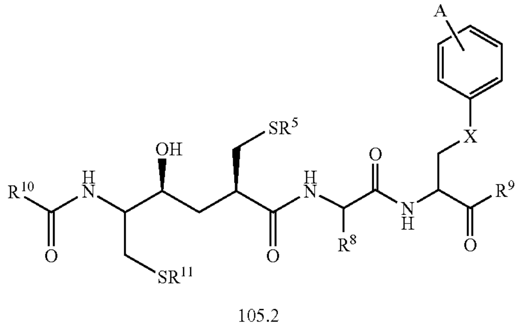

105.2

Scheme 106

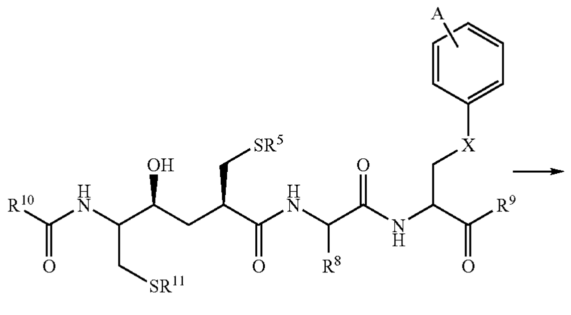

105.2

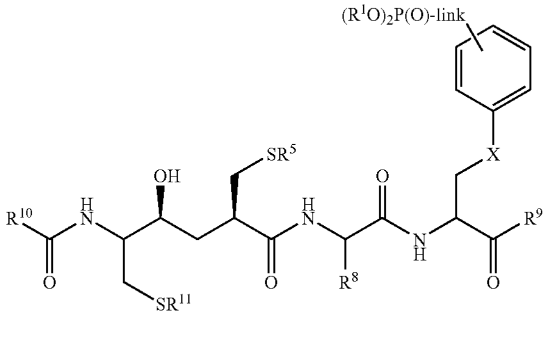

19

Preparation of the Phosphonate Ester Intermediates 19 in which X is Sulfur and X' is a Direct Bond.

Schemes 107 and 108 illustrate the preparation of the phosphonate esters 19 in which X is sulfur and X' is a direct bond. In this procedure, the carboxylic acid 91.1 is coupled, as described in Scheme 1, with the phenylalanine derivative 37.1 to afford the amide 107.1. The product is then converted, as described in Scheme 49, into the diamide 107.2.

The reactions shown in Scheme 107 illustrate the preparation of the compounds 107.2 in which the substituent A is either the group link-P(O)(OR$^1$)$_2$ or a precursor such as [OH], [SH], [NH], Br. Scheme 108 depicts the conversion of the compounds 107.2 in which A is [OH], [SH], [NH], Br, into the phosphonate esters 19 in which X is sulfur and X' is a direct bond. In this procedure, the compounds 107.2 are converted, using the procedures described below, Schemes 133-197, into the compounds 19.

Preparation of the Phosphonate Ester Intermediates 20 in which X and X' are Direct Bonds.

Schemes 109 and 110 illustrate the preparation of the phosphonate esters 20 in which X and X' are direct bonds. In this procedure, the carboxylic acid 76.2 is coupled, as described in Scheme 1, with the tert. butylamine derivative 41.1 to afford the amide 109.1. The product is then converted, as described in Scheme 49, into the diamide 109.2.

The reactions shown in Scheme 109 illustrate the preparation of the compounds 109.2 in which the substituent A is either the group link-P(O)(OR$^1$)$_2$ or a precursor such as [OH], [SH], [NH], Br. Scheme 110 depicts the conversion of the compounds 109.2 in which A is [OH], [SH], [NH], Br, into the phosphonate esters 20 in which X and X' are direct bonds. In this procedure, the compounds 109.2 are converted, using the procedures described below, Schemes 133-197, into the compounds 20.

Preparation of the Phosphonate Ester Intermediates 20 in which X is a Direct Bond and X' is Sulfur.

Schemes 111 and 112 illustrate the preparation of the phosphonate esters 20 in which X is a direct bond and X' is sulfur. In this procedure, the carboxylic acid 78.2 is coupled, as described in Scheme 1, with the amine 41.1 to afford the amide 111.1. The product is then converted, as described in Scheme 49, into the diamide 111.2.

The reactions shown in Scheme 111 illustrate the preparation of the compounds 111.2 in which the substituent A is either the group link-P(O)$(OR^1)_2$ or a precursor such as [OH], [SH], [NH], Br. Scheme 112 depicts the conversion of the compounds 111.2 in which A is [OH], [SH], [NH], Br, into the phosphonate esters 20 in which X is a direct bond and X' is sulfur. In this procedure, the compounds 111.2 are converted, using the procedures described below, Schemes 133-197, into the compounds 20.

Preparation of the Phosphonate Ester Intermediates 20 in which X and X' are Sulfur.

Schemes 113 and 114 illustrate the preparation of the phosphonate esters 20 in which X and X' are sulfur. As shown in Scheme 113, the carboxylic acid 80.2 is coupled, as described in Scheme 1, with the tert. butylamine derivative 41.1 to give the amide 113.1. The product is then transformed, as described in Scheme 49, into the diamide 113.2.

The reactions shown in Scheme 113 illustrate the preparation of the compounds 113.2 in which the substituent A is either the group link-P(O)$(OR^1)_2$ or a precursor such as [OH], [SH], [NH], Br. Scheme 114 depicts the conversion of the compounds 113.2 in which A is [OH], [SH], [NH], Br, into the phosphonate esters 20 in which X and X' are sulfur. In this procedure, the compounds 113.2 are converted, using the procedures described below, Schemes 133-197, into the compounds 20.

Preparation of the Phosphonate Ester Intermediates 20 in which X is Sulfur and X' is a Direct Bond.

Schemes 115 and 116 illustrate the preparation of the phosphonate esters 20 in which X is sulfur and X' is a direct bond. In this procedure, the carboxylic acid 91.1 is coupled, as described in Scheme 1, with the tert. butylamine derivative 41.1 to afford the amide 115.1.

The product is then converted, as described in Scheme 49, into the diamide 115.2. The reactions shown in Scheme 115 illustrate the preparation of the compounds 115.2 in which the substituent A is either the group link-P(O)$(OR^1)_2$ or a precursor such as [OH], [SH], [NH], Br. Scheme 116 depicts the conversion of the compounds 115.2 in which A is [OH], [SH], [NH], Br, into the phosphonate esters 20 in which X is sulfur and X' is a direct bond. In this procedure, the compounds 115.2 are converted, using the procedures described below, Schemes 133-197, into the compounds 20.

Preparation of the Phosphonate Ester Intermediates 21 in which X and X' are Direct Bonds.

Schemes 117 and 118 illustrate the preparation of the phosphonate esters 21 in which X and X' are direct bonds. In this procedure, the carboxylic acid 76.2 is coupled, as described in Scheme 1, with the decahydroisoquinoline derivative 45.1 to afford the amide 117.1. The product is then converted, as described in Scheme 49, into the diamide 117.2.

The reactions shown in Scheme 117 illustrate the preparation of the compounds 117.2 in which the substituent A is either the group link-P(O)$(OR^1)_2$ or a precursor such as [OH], [SH], [NH], Br. Scheme 118 depicts the conversion of the compounds 117.2 in which A is [OH], [SH], [NH], Br, into the phosphonate esters 21 in which X and X' are direct bonds. In this procedure, the compounds 117.2 are converted, using the procedures described below, Schemes 133-197, into the compounds 21.

Preparation of the Phosphonate Ester Intermediates 21 in which X is a Direct Bond and X' is Sulfur.

Schemes 119 and 120 illustrate the preparation of the phosphonate esters 21 in which X is a direct bond and X' is sulfur. In this procedure, the carboxylic acid 78.2 is coupled, as described in Scheme 1, with the amine 45.1 to afford the amide 119.1. The product is then converted, as described in Scheme 49, into the diamide 119.2.

The reactions shown in Scheme 119 illustrate the preparation of the compounds 119.2 in which the substituent A is either the group link-P(O)$(OR^1)_2$ or a precursor such as [OH], [SH], [NH], Br. Scheme 120 depicts the conversion of the compounds 119.2 in which A is [OH], [SH], [NH], Br, into the phosphonate esters 21 in which X is a direct bond and X' is sulfur. In this procedure, the compounds 119.2 are converted, using the procedures described below, Schemes 133-197, into the compounds 21.

Scheme 107

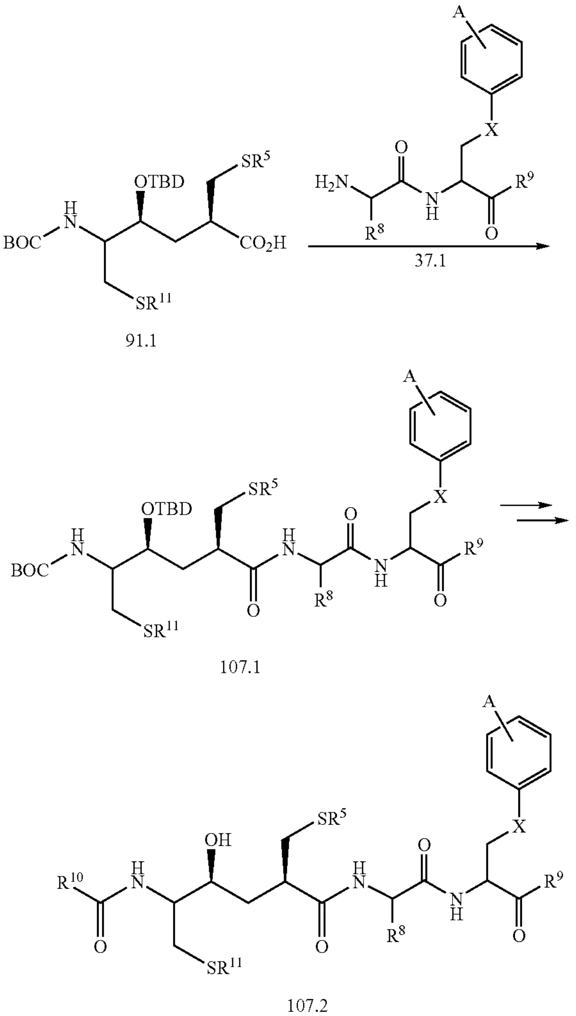

91.1

107.1

107.2

Scheme 108
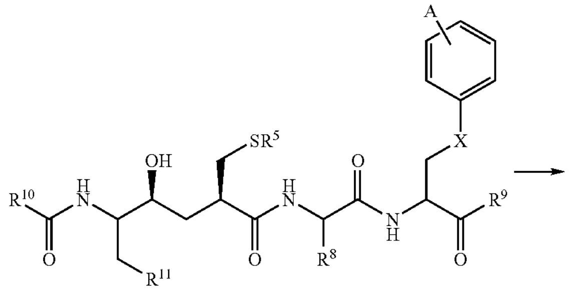
107.2
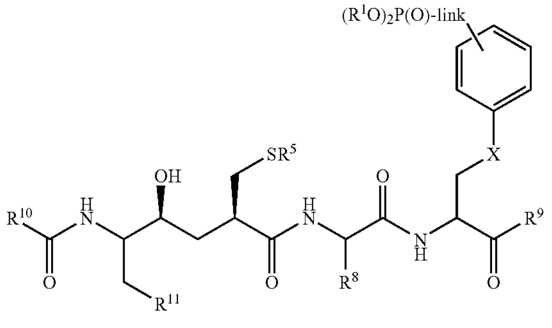
19
Scheme 109
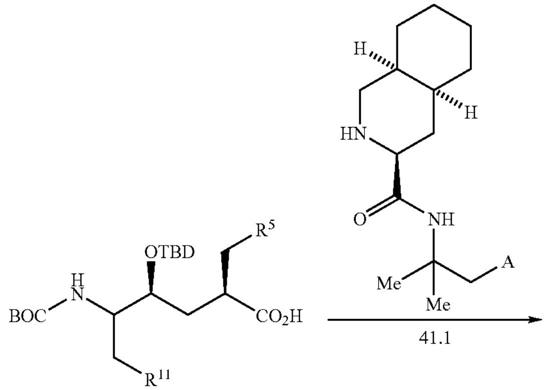
76.2
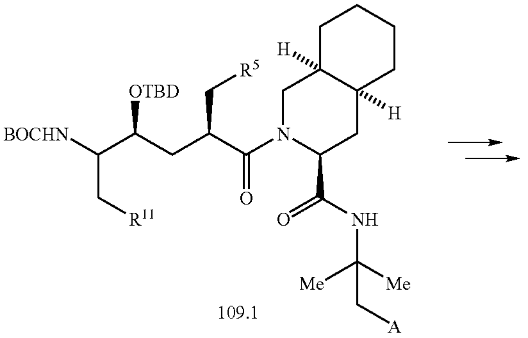
109.1
-continued
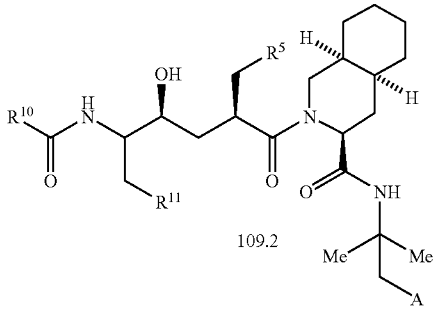
109.2
Scheme 110
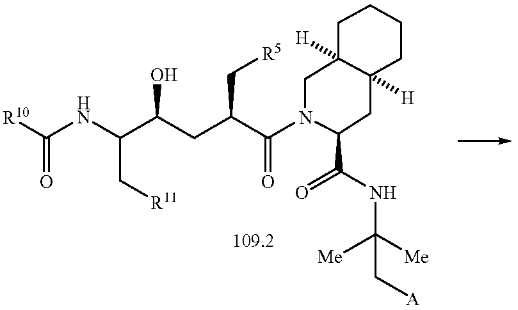
109.2
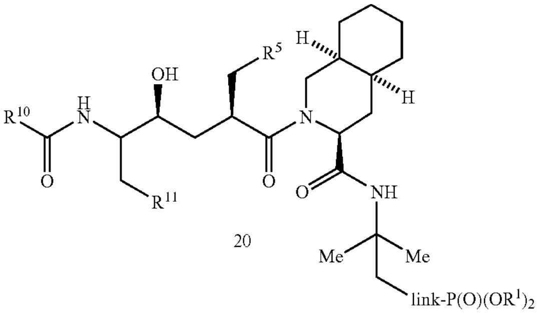
20
Scheme 111
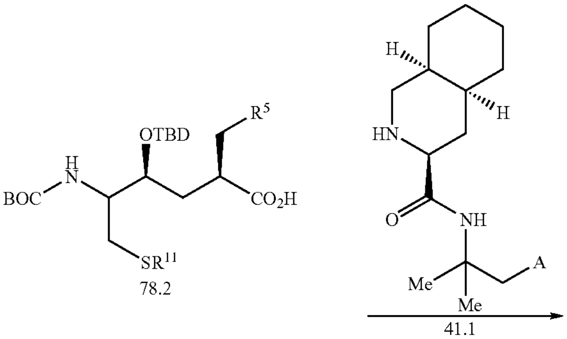
78.2

-continued
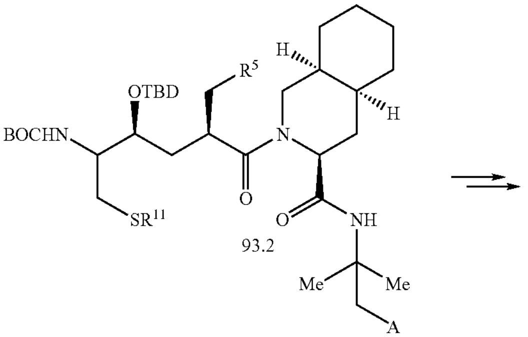
93.2
111.1
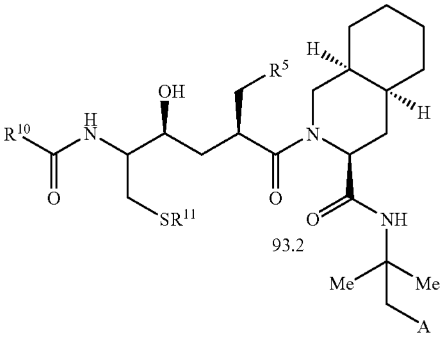
93.2
111.2
Scheme 112
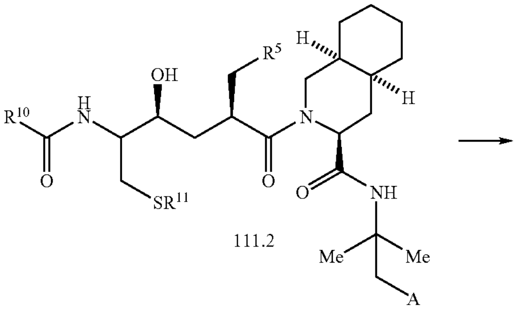
111.2
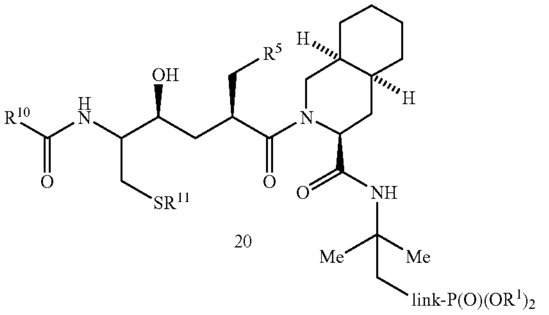
20
Scheme 113
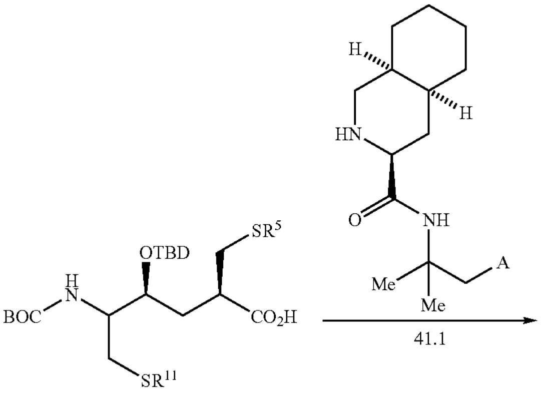
41.1
80.2
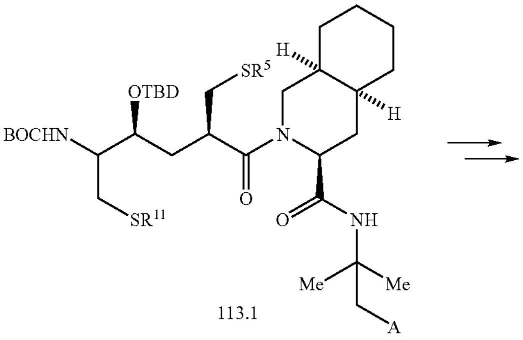
113.1
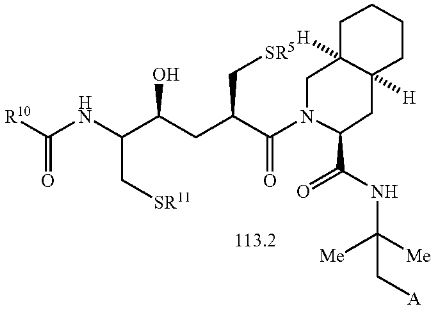
113.2
Scheme 114
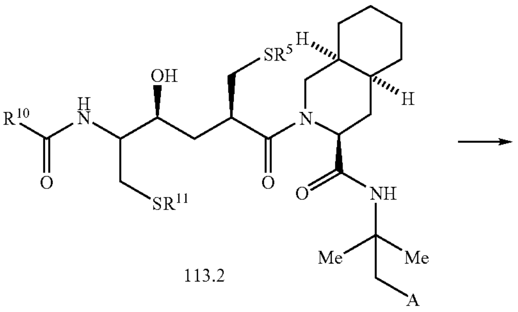
113.2

-continued
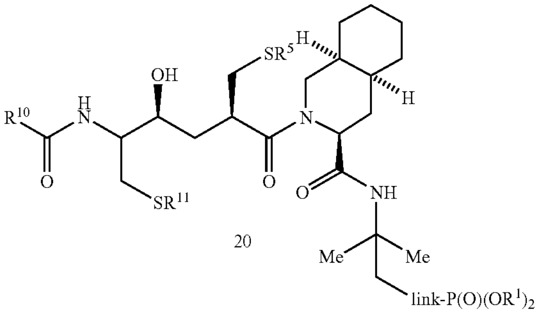
20
Scheme 115
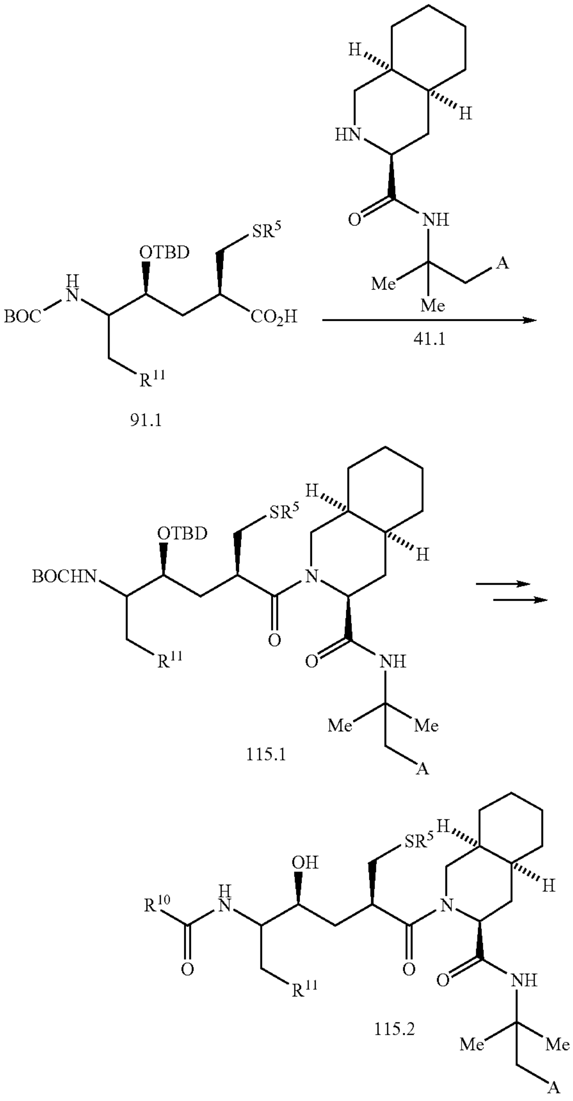
91.1
41.1
115.1
115.2
Scheme 116
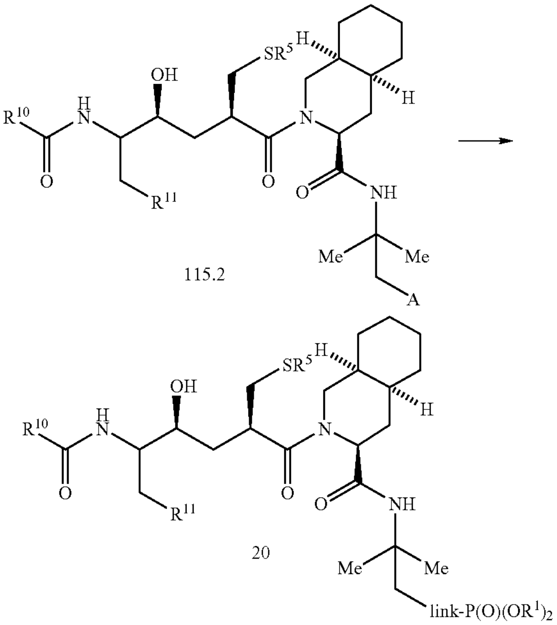
115.2
20
Scheme 117
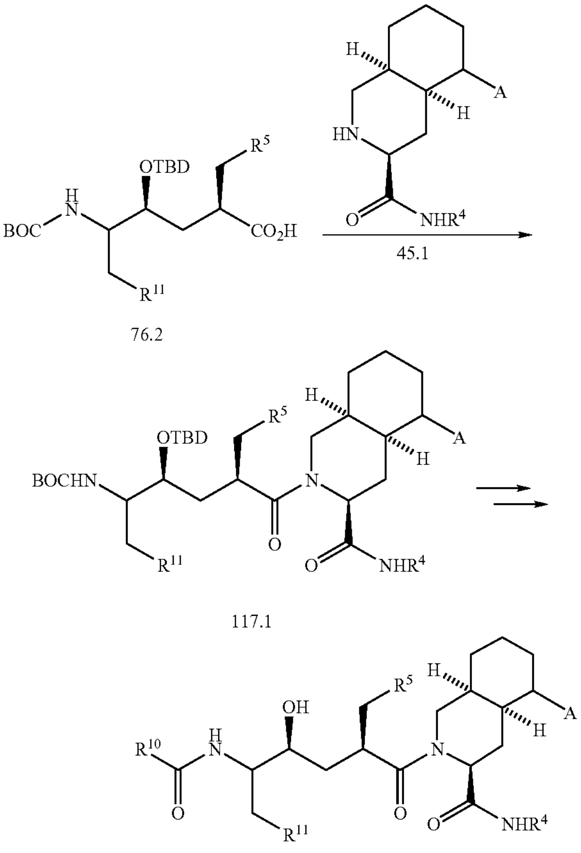
76.2
45.1
117.1
117.2

Scheme 118

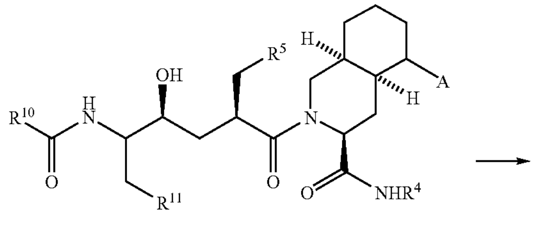

117.2

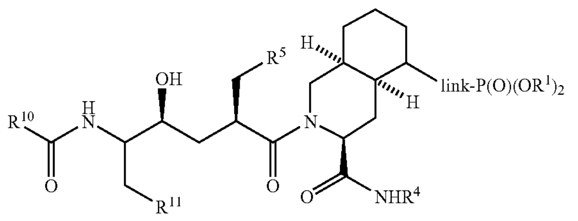

21

Scheme 119

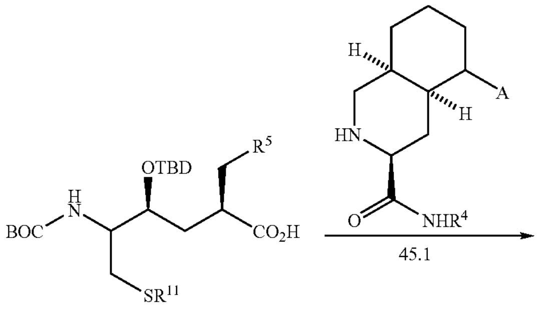

78.2

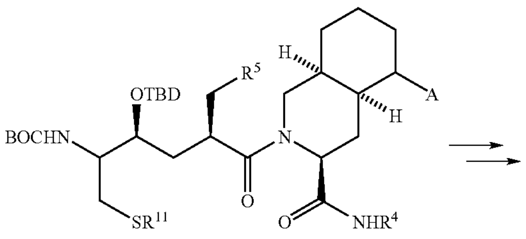

119.1

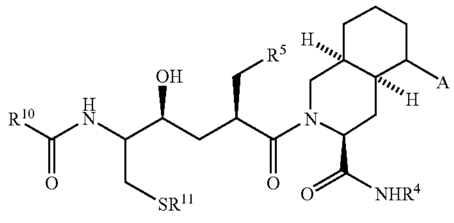

119.2

Scheme 120

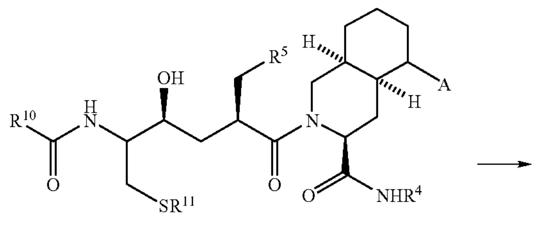

119.2

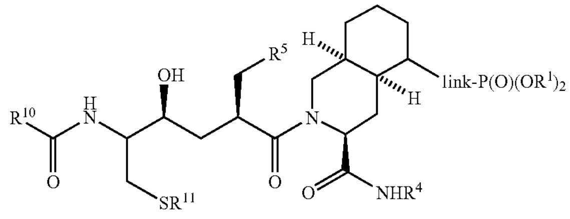

21

Preparation of the Phosphonate Ester Intermediates 21 in which X and X' are Sulfur.

Schemes 121 and 122 illustrate the preparation of the phosphonate esters 21 in which X and X' are sulfur. As shown in Scheme 121, the carboxylic acid 80.2 is coupled with the amine 45.1 to give the amide 121.1. The product is then transformed, as described in Scheme 49, into the diamide 121.2.

The reactions shown in Scheme 121 illustrate the preparation of the compounds 121.2 in which the substituent A is either the group link-$P(O)(OR^1)_2$ or a precursor such as [OH], [SH], [NH], Br. Scheme 122 depicts the conversion of the compounds 121.2 in which A is [OH], [SH], [NH], Br, into the phosphonate esters 21 in which X and X' are sulfur. In this procedure, the compounds 121.2 are converted, using the procedures described below, Schemes 133-197, into the compounds 21.

Preparation of the Phosphonate Ester Intermediates 21 in which X is Sulfur and X' is a Direct Bond.

Schemes 123 and 124 illustrate the preparation of the phosphonate esters 21 in which X is sulfur and X' is a direct bond. In this procedure, the carboxylic acid 91.1 is coupled, as described in Scheme 1, with the amine 45.1 to afford the amide 123.1. The product is then converted, as described in Scheme 49, into the diamide 123.2.

The reactions shown in Schemes 123 illustrate the preparation of the compounds 123.2 in which the substituent A is either the group link-$P(O)(OR^1)_2$ or a precursor such as [OH], [SH], [NH], Br. Scheme 124 depicts the conversion of the compounds 123.2 in which A is [OH], [SH], [NH], Br, into the phosphonate esters 21 in which X is sulfur and X' is a direct bond. In this procedure, the compounds 123.2 are converted, using the procedures described below, Schemes 133-197, into the compounds 21.

Preparation of the Phosphonate Ester Intermediates 22 in which X and X' are Direct Bonds.

Schemes 125 and 126 illustrate the preparation of the phosphonate esters 22 in which X and X' are direct bonds. In this procedure, the carboxylic acid 76.2 is coupled, as described in Scheme 5 with the amine 1.6, to afford the amide 125.1. The BOC protecting group is then removed, as described in Scheme 49, to yield the amine 125.2. The latter compound is then coupled with the carboxylic acid 125.3 to produce the amide 125.4. The preparation of the carboxylic acid reactant 125.3 is described in Scheme 191.

The reactions shown in Scheme 125 illustrate the preparation of the compounds 125.4 in which the substituent A is either the group link-$P(O)(OR^1)_2$ or a precursor such as [OH], [SH], [NH], Br. Scheme 126 depicts the conversion of the compounds 125.4 in which A is [OH], [SH], [NH], Br, into the phosphonate esters 22 in which X and X' are direct bonds. In this procedure, the compounds 125.4 are converted, using the procedures described below, Schemes 133-197, into the compounds 22

Preparation of the Phosphonate Ester Intermediates 22 in which X is a Direct Bond and X' is Sulfur.

Schemes 127 and 128 illustrate the preparation of the phosphonate esters 22 in which X is a direct bond and X' is sulfur. In this procedure, the carboxylic acid 78.2 is coupled, as described in Scheme 5 with the amine 1.6, to afford the amide 127.1. The BOC protecting group is then removed, as described in Scheme 49, to yield the amine 127.2. The latter compound is then coupled, as described in Scheme 1, with the carboxylic acid 125.3 to produce the amide 127.3.

The reactions shown in Scheme 127 illustrate the preparation of the compounds 127.3 in which the substituent A is either the group link-$P(O)(OR^1)_2$ or a precursor such as [OH], [SH], [NH], Br. Scheme 128 depicts the conversion of the compounds 127.3 in which A is [OH], [SH], [NH], Br, into the phosphonate esters 22, in which X is a direct bond and X' is sulfur. In this procedure, the compounds 127.3 are converted, using the procedures described below, Schemes 133-197, into the compounds 22.

Preparation of the Phosphonate Ester Intermediates 22 in which X and X' are Sulfur.

Schemes 129 and 130 illustrate the preparation of the phosphonate esters 22 in which X and X' are sulfur. As shown in Scheme 129, the carboxylic acid 80.2 is coupled, as described in Scheme 5, with the amine 1.6, to afford the amide 129.1. The BOC protecting group is then removed, as described in Scheme 49, to yield the amine 129.2. The latter compound is then coupled, as described in Scheme 1, with the carboxylic acid 125.3 to produce the amide 129.3.

The reactions shown in Scheme 129 illustrate the preparation of the compounds 129.3 in which the substituent A is either the group link-$P(O)(OR^1)_2$ or a precursor such as [OH], [SH], [NH], Br. Scheme 130 depicts the conversion of the compounds 129.3 in which A is [OH], [SH], [NH], Br, into the phosphonate esters 22, in which X and X' are sulfur. In this procedure, the compounds 129.3 are converted, using the procedures described below, Schemes 133-197, into the compounds 22.

Preparation of the Phosphonate Ester Intermediates 22 in which X is Sulfur and X' is a Direct Bond.

Schemes 131 and 132 illustrate the preparation of the phosphonate esters 22 in which X is sulfur and X' is a direct bond. In this procedure, the carboxylic acid 91.1 is coupled, as described in Scheme 5, with the amine 1.6, to afford the amide 131.1. The BOC protecting group is then removed, as described in Scheme 49, to yield the amine 131.2. The latter compound is then coupled, as described in Scheme 1, with the carboxylic acid 125.3 to produce the amide 131.3.

The reactions shown in Scheme 131 illustrate the preparation of the compounds 131.3 in which the substituent A is either the group link-$P(O)(OR^1)_2$ or a precursor such as [OH], [SH], [NH], Br. Scheme 132 depicts the conversion of the compounds 131.3 in which A is [OH], [SH], [NH], Br, into the phosphonate esters 22 in which X is sulfur and X' is a direct bond. In this procedure, the compounds 131.3 are converted, using the procedures described below, Schemes 133-197, into the compounds 22.

Scheme 125

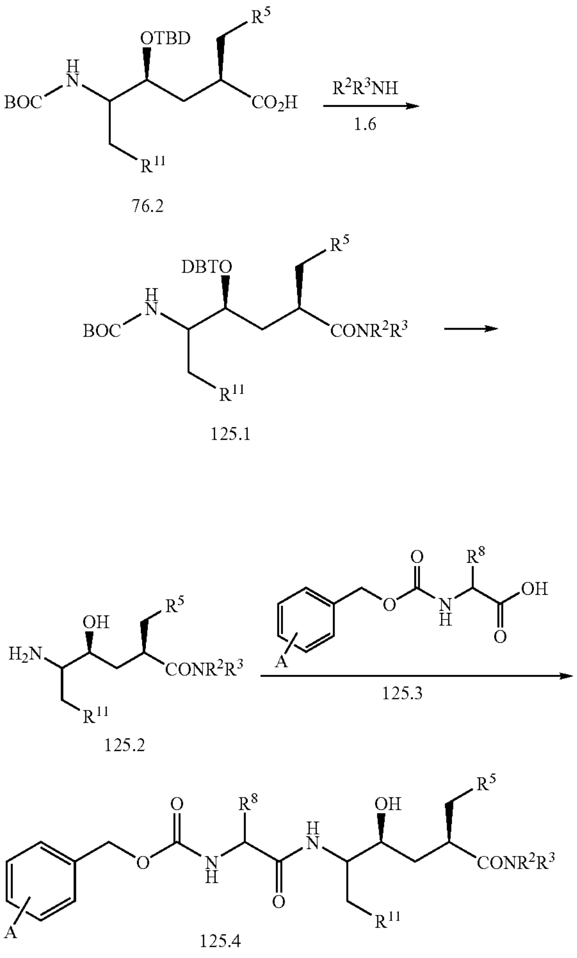

76.2
125.1
125.2
125.4

Scheme 126

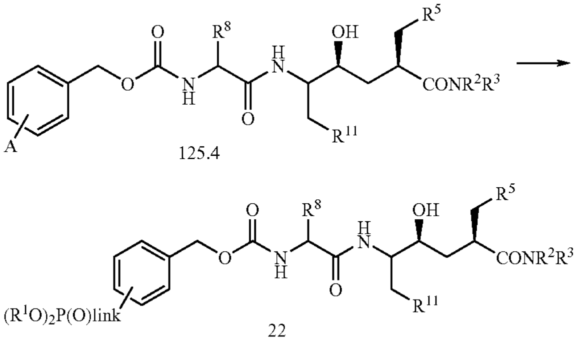
125.4
22

Scheme 127
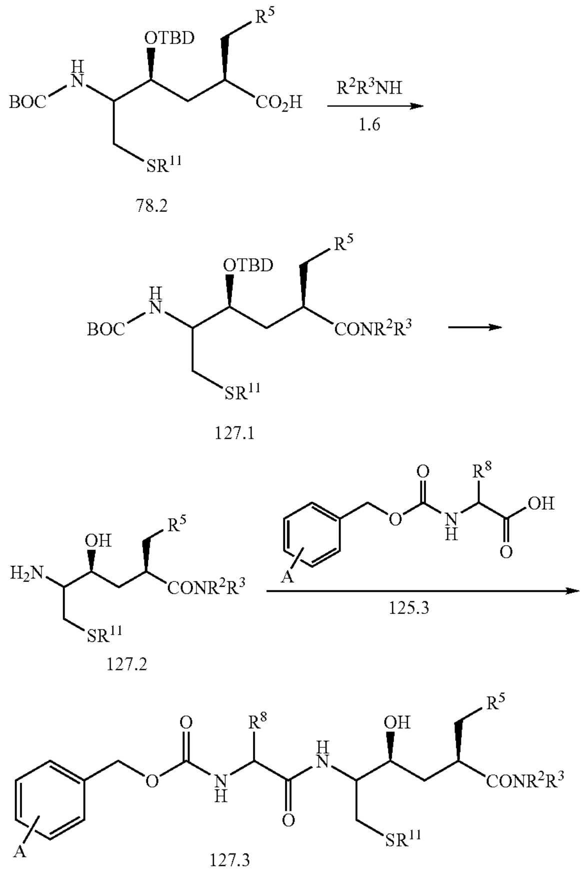
Scheme 128
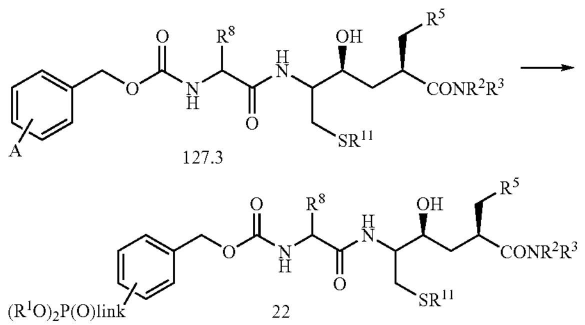
Scheme 129
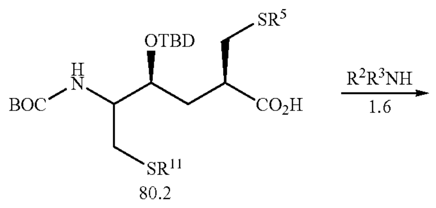
-continued
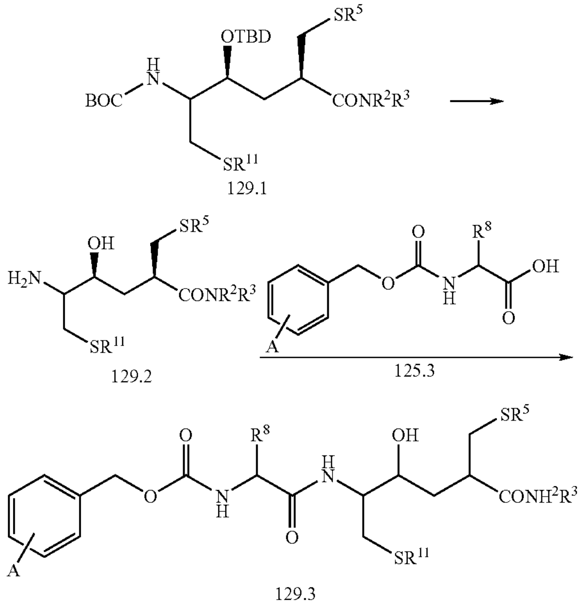
Scheme 130
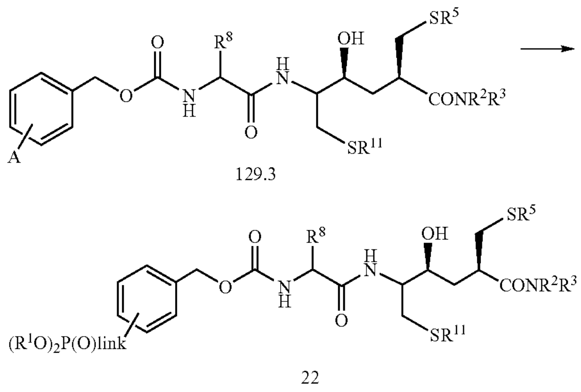
Scheme 131
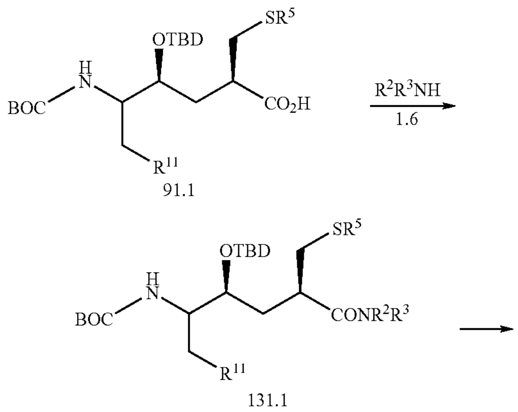

-continued

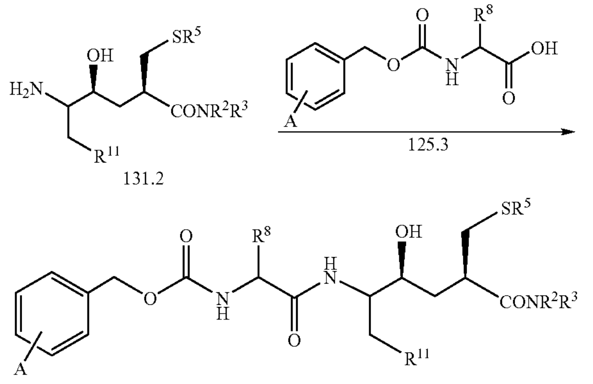

131.2

125.3

131.3

Scheme 132

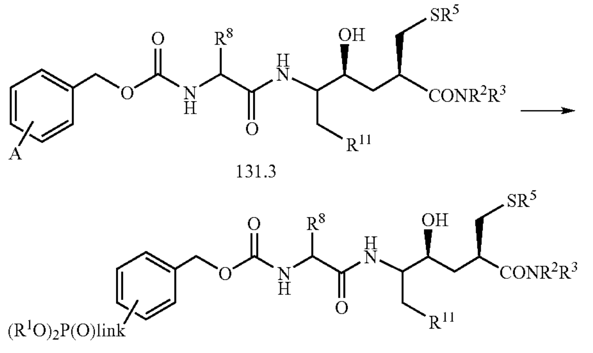

131.3

22

Preparation of Aminoindanol Derivatives 1.2 Incorporating Phosphonate Moieties.

Scheme 133 illustrates the preparation of variously substituted derivatives of 3-amino-indan-1,2-diol, the preparation of which is described in J. Med. Chem., 1991, 34, 1228. The alcohols, thiols, amines and bromo compounds shown in Scheme 133 can then be transformed into phosphonate-containing reactants 1.2, as described below, (Schemes 134-137). The reactants 1.2 are employed in the preparation of the phosphonate esters 1 and 16.

In order to effect changes to the 1-substituent, the starting material 133.1 is transformed into the protected compound 133.2. For example, the aminoalcohol 133.1 is treated with 2-methoxypropene in the presence of an acid catalyst, such as p-toluenesulfonic acid, in a solvent such as tetrahydrofuran, as described in WO9628439, to afford the acetonide-protected product 133.2.

The amino group present in 133.2 is protected to afford the intermediate 133.3, in which $R^{12}$ is a protecting group, stable to the subsequent reactions. For example, $R^{12}$ can be carbobenzyloxy (cbz), tert-butoxycarbonyl (BOC) and the like, as described in Protective Groups in Organic Synthesis, by T. W. Greene and P. G. M Wuts, Wiley, Second Edition 1990, p. 309.

The free hydroxyl group present in the N-protected acetonide 133.3 is then converted into a suitable leaving group, such as, for example, trifluoromethylsulfonyloxy, p-toluenesulfonyloxy or, preferably, methanesulfonyloxy.

This transformation is effected by treatment of 133.3 with a slight molar excess of the corresponding acid chloride or anhydride, in the presence of an organic base.

For example, treatment of 133.3 with methanesulfonyl chloride and pyridine in dichloromethane at ambient temperature affords the mesylate 133.4.

The α-mesylate group in the product 133.4 is then subjected to displacement reactions with nitrogen, sulfur or oxygen nucleophiles, to effect introduction of the various heteroatoms with inversion of stereochemistry.

For example, the mesylate 133.4 is reacted with a nitrogen nucleophile such as potassium phthalimide or sodium bis (trimethylsilyl)amide, as described in Comprehensive Organic Transformations, by R. C. Larock, VCH, p. 399, to afford the amine 133.9.

Preferably, the mesylate 133.4 is reacted, as described in Angew. Chem. Int. Ed., 7, 919, 1968, with one molar equivalent of potassium phthalimide, in a dipolar aprotic solvent, such as, for example, dimethylformamide, at ambient temperature, to afford the displacement product 133.5, in which $NR^aR^b$ is phthalimido. Removal of the phthalimido group, for example by treatment with an alcoholic solution of hydrazine at ambient temperature, as described in J. Org. Chem., 38, 3034, 1973, then yields the β-amine 133.9.

The mesylate 133.4 is treated with a sulfur nucleophile, for example potassium thioacetate, as described in Tet. Lett., 1992, 4099, or sodium thiophosphate, as described in Acta Chem. Scand., 1960, 1980, to effect displacement of the mesylate group, followed by mild basic hydrolysis, for example by treatment with aqueous sodium bicarbonate or aqueous ammonia, to afford the β-thiol 133.12.

Preferably, the mesylate 133.4 is reacted with one molar equivalent of potassium thioacetate in a polar aprotic solvent such as, for example, dimethylformamide, at ambient temperature, to afford the thioacetate 133.8. The product then treated with a mild base such as, for example, aqueous ammonia, in the presence of an organic co-solvent such as ethanol, at ambient temperature, to afford the β-thiol 133.12.

The mesylate 133.4 is transformed into the β-carbinol 133.7, by treatment with an oxygen nucleophile. Conversion of sulfonate esters and related compounds to the corresponding carbinols is described, for example, in Comprehensive Organic Transformations, by R. C. Larock, VCH, p. 481. For example, the mesylate can be reacted with potassium superoxide, in the presence of a crown ether such as 18-crown-6, as described in Tet. Lett., 3183, 1975, to afford the β-carbinol 133.7.

The carbinol 133.3 is also transformed into the β-bromo compound 133.6. Methods for the conversion of carbinols to bromo compounds are described, for example, in Comprehensive Organic Transformations, by R. C. Larock, VCH, p. 356.

For example, the α-carbinol 133.3 is reacted with hexabromoethane and triphenylphosphine, in an aprotic solvent such as ethyl acetate, as described in Syn., 139, 1983, to afford the β-bromo compound 133.6.

Using the above described procedures for the conversion of the α-carbinol 133.3 into the β-oriented amine 133.9, thiol 133.12 and bromo compound 133.6, the β-carbinol 133.7 is transformed into the α-oriented amine or thiol 133.11 or the bromo compound 133.10.

Schemes 134-137 illustrate the preparation of aminoindanol derivatives incorporating the group link-$P(O)(OR^1)_2$, derived from the intermediates whose syntheses are described above (Scheme 133).

Scheme 134 depicts the preparation of phosphonate esters linked to the aminoindanol nucleus by means of a carbon chain and a heteroatom O, S or N. In this procedure, the hetero-substituted indanol 134.1 is reacted with a bromoalkylphosphonate 134.2, in the presence of a suitable base. The base required for this transformation depends on the nature of the heteroatom X. For example, if X is N or S, an excess of an inorganic base such as, for example, potassium carbonate, in the presence of an organic solvent such as dimethylformamide, is suitable. The reaction proceeds at from ambient temperature to about 80° C. to afford the displacement products 134.3. If X is 0, an equimolar amount of a strong base, such as, for example, lithium hexamethyldisilylazide and the like, is employed, in the presence of a solvent such as tetrahydrofuran. Deprotection, by removal of the group $R^{12}$, then affords the amine 134.4.

For example, the β-thiol 133.12 is reacted with an equimolar amount of dialkyl 4-bromobutyl phosphonate 134.5, the preparation of which is described in Synthesis, 1999, 9, 909, in dimethylformamide containing excess potassium carbonate, at ca 60° C. to afford the thioether phosphonate product 134.6. Deprotection then affords the amine 134.7.

Using the above procedures, but employing, in place of the thiol 133.12, different carbinols, thiols or amines 134.1, and/or different bromoalkylphosphonates 134.2, the corresponding products 134.4 are obtained.

Scheme 135 illustrates the preparation of aminoindanol derivatives in which the phosphonate ester group is attached by means of a nitrogen atom and a carbon chain. In this method, the aminoindanol 135.1 is reacted with a formyl-substituted phosphonate ester, utilizing a reductive amination procedure. The preparation of amines by means of reductive amination procedures is described, for example, in Comprehensive Organic Transformations, by R. C. Larock, VCH, p. 421. In this procedure, the amine component 135.1 and the aldehyde component 135.2 are reacted together in the presence of a reducing agent such as, for example, borane, sodium cyanoborohydride or diisobutylaluminum hydride, to yield the amine product 135.3. Deprotection, by removal of the $R^{12}$ group, then affords the amine 135.4.

For example, equimolar amounts of the amine 133.11 and a dialkylformylphosphonate 135.5, prepared as described in U.S. Pat. No. 3,784,590, are reacted together in the presence of sodium cyanoborohydride and acetic acid, as described, for example, in J. Am. Chem. Soc., 91, 3996, 1969, to afford the product 135.6 which is then deprotected to produce the amine 135.7. Using the above procedures, but employing, in place of the α-amine 133.11, the β-amine 133.9, and/or different formyl-substituted phosphonates 135.2, the corresponding products 135.4 are obtained.

Scheme 136 depicts the preparation of aminoindanol phosphonates in which the phosphonate moiety is attached to the nucleus by means of a heteroatom and one carbon. In this procedure, a carbinol, thiol or amine 136.1 is reacted with a dialkyl trifluoromethylsulfonyloxy phosphonate 136.2, in the presence of a suitable base, to afford the alkylation product 136.3. Deprotection of the product 136.3 then yields the amine 136.4. The base required for this reaction between 136.1 and 136.2 depends on the nature of the heteroatom X. For example, if X is N or S, an excess of inorganic base such as, for example, potassium carbonate, cesium carbonate or the like, in the presence of an organic solvent such as dimethylformamide, is suitable. The reaction proceeds at from ambient temperature to about 80° to afford the displacement products 136.3. If X is O, an equimolar amount of a strong base, such as, for example, lithium hexamethyldisilylazide, sodium hydride or the like, is employed, in the presence of a solvent such as tetrahydrofuran.

For example, the α-carbinol 133.3 is reacted with one equivalent of lithium hexamethyl disilylazide in tetrahydrofuran, followed by addition of an equimolar amount of a dialkyl trifluoromethylsulfonyloxymethyl phosphonate 136.5, the preparation of which is described in Tet. Lett., 1986, 27, 1497, to afford the ether product 136.6. Deprotection, by removal of the $R^{12}$ group, then affords the amine 136.7.

Using the above procedures, but employing, in place of the α-carbinol 133.3, different carbinols, thiols or amines 136.1, and/or different dialkyl trifluoromethylsulfonyloxymethyl phosphonates 136.2, the corresponding products 136.4 are obtained.

Scheme 137 illustrates the preparation of aminoindanol phosphonate esters in which the phosphonate group is attached directly to the aminoindanol nucleus.

In this procedure, the bromoindanol derivative 137.1 is reacted with a sodium dialkyl phosphite, in a suitable aprotic polar solvent such as dimethyl formamide or N-methylpyrrolidinone. Displacement of the bromo substituent occurs to yield the phosphonate 137.3. Deprotection, by removal of the $R^{12}$ group, then affords the amine 137.4. For example, equimolar amounts of the α-bromo compound 133.10 and the dialkyl sodium phosphite 137.2, are dissolved in dimethylformamide and the mixture is heated at ca. 60° C., as described in J. Med. Chem., 35, 1371, 1992, to afford the β-phosphonate 137.5. Alternatively, the phosphonate compound 137.5 is obtained by means of an Arbuzov reaction between the bromo compound 133.10 and a trialkyl phosphite $P(OR^1)_3$. In this procedure, as described in Handb. Organophosphorus Chem., 1992, 115, the reactants are heated together at ca. 100° C. to afford the product 137.5. Deprotection of the latter compound affords the amine 137.6.

Using the above procedures, but employing, in place of the Q-bromo compound 133.10, the β-bromo compound 133.6, and/or different phosphites 137.2, the corresponding phosphonates 137.4 are obtained.

Preparation of Phenylpropionic Acid Intermediates 5.1 Incorporating Phosphonate Moieties.

Phenylpropionic acid derivatives incorporating the substituent link-$P(O)(OR^1)_2$ are prepared by the reactions illustrated in Schemes 139-143, using as starting materials variously substituted phenylpropionic acids. The phenylpropionic acid derivatives 5.1 are employed in the preparation of the phosphonate esters 2 in which X is a direct bond.

A number of the substituted phenylpropionic acids required for the reactions shown in Schemes 139-143 are commercially available; in addition, the syntheses of variously substituted phenylpropionic acids have been reported. For those substituted phenylpropionic acids which are not commercially available, and whose syntheses have not been reported, a number of well-established synthetic routes are available. Representative methods for the synthesis of substituted phenylpropionic acids from commercially available starting materials are shown in Scheme 138.

For example, variously substituted benzaldehydes 138.1 are subjected to a Wittig reaction with carboethoxymethylenetriphenylphosphorane 138.2, as described in Ylid Chemistry, by A. W. Johnson, Academic Press, 1966, p. 132, to afford the corresponding cinnamate esters 138.3. Equimolar amounts of the reactants 138.1 and 138.2 are heated in an inert solvent such as dioxan or dimethylformamide, at ca 50° C., to afford the product 138.3. Reduction of the double bond in the product 138.3 then afford the saturated ester 138.6, (X=H) which upon hydrolysis yields the phenylpropionic acid intermediate 138.10.

Methods for the reduction of carbon-carbon double bonds are described, for example, in Comprehensive Organic Transformations, by R. C. Larock, VCH, p. 6. Typical of the available reduction methods are catalytic hydrogenation, for example using palladium catalysts, as described in Hydrogenation Methods, by P. N. Rylander, Academic Press, New York, 1985, hydroboration-protonolysis, as described in J. Am. Chem. Soc., 81, 4108, 1959, or diimide reduction, as described in J. Org. Chem., 52, 4665, 1987. The choice of a particular reduction method is made by one skilled in the art, depending on the nature of the substituent groups attached to the cinnamnic acid ester 138.3.

Alternatively, the cinnamic esters 138.3 are obtained by means of a palladium-catalyzed Heck reaction between an appropriately substituted bromobenzene 138.5 and ethyl acrylate 138.4. In this procedure, a substituted bromobenzene 138.5 is reacted with ethyl acrylate in the presence of a palladium (II) catalyst, as described in J. Med. Chem., 35, 1371, 1992, to afford the cinnamate ester 138.3. Equimolar amounts of the reactants 138.4 and 138.5 are dissolved in a polar aprotic solvent such as dimethylformamide or tetrahydrofuran, at a temperature of about 60° C., in the presence or ca. 3 mol % of, for example, bis(triphenylphosphine)palladium (II) chloride and triethylamine, to afford the product 138.3.

Alternatively, the substituted phenylpropionic acid intermediates are obtained from the correspondingly substituted methylbenzenes 138.7. In this procedure, the methylbenzene 138.7 is subjected to free-radical bromination, for example by reaction with an equimolar amount of N-bromosuccinimide, as described in Chem. Rev., 63, 21, 1963, to afford the bromomethyl derivative 138.8. The latter compound is then reacted with a salt of an ester of malonic acid, for example the sodium salt of diethyl malonate 138.9, as described in Synthetic Organic Chemistry, R. B. Wagner, H. D. Zook, Wiley, 1953, p. 489, to afford the displacement product 138.6, (X=COOEt). The latter compound is subjected to hydrolysis and decarboxylation, for example by treatment with aqueous alkali or dilute aqueous acid, to afford the phenylpropionic acid 138.10.

Scheme 139 illustrates the preparation of phosphonate-containing phenylpropionic acids in which the phosphonate moiety is attached to the phenyl ring by means of an aromatic group. In this procedure, the carboxyl group of a bromo-substituted phenylpropionic acid 139.1 is protected. Methods for the protection of carboxylic acids are described, for example, in Protective Groups in Organic Synthesis, by T. W. Greene and P. G. M Wuts, Wiley, Second Edition 1990, p. 224. The product 139.2 is then subjected to halogen-methyl exchange, for example by reaction with an alkyllithium, to afford the product 139.3 in which M is Li. The latter compound is subjected to palladium (II) or palladium (0) catalyzed coupling, as described in Comprehensive Organic Transformations, by R. C. Larock, VCH, 1989, p. 57. Compound 139.3 is first converted into the boronic acid 139.4, by reaction with a trialkyl borate, and the boronic acid product is coupled with a dialkyl bromophenylphosphonate 139.5 to yield the product 139.6. Deprotection then affords the intermediate phosphonate-substituted phenylpropionic acid 139.7.

For example, 4-bromophenylpropionic acid 139.8, prepared as described in U.S. Pat. No. 4,032,533, is converted into the acid chloride, by treatment with thionyl chloride, oxalyl chloride and the like. The acid chloride is then reacted with 3-methyl-3-oxetanemethanol 139.9 (Aldrich), in the presence of a tertiary organic base such as pyridine, in a solvent such as dichloromethane, to afford the ester 139.10. This product is then rearranged by treatment with boron trifluoride etherate in dichloromethane, at about −15° C. as described in Protective Groups in Organic Synthesis, by T. W. Greene and P. G. M Wuts, Wiley, Second Edition 1990, p. 268, to yield the orthoester 139.11, known as an OBO ester. The latter product is then reacted with one molar equivalent of n-butyllithium, in a solvent such as ether, at about −80° C., to afford the lithio derivative, which is reacted with a trialkyl borate, as described in J. Organomet. Chem., 1999, 581, 82, to yield the boronate 139.12. This material is coupled, in the presence of a catalytic amount of tetrakis(triphenylphosphine)palladium(0), and an inorganic base such as sodium carbonate, with a dialkyl 4-bromophenylphosphonate 139.13, prepared as described in J. Chem. Soc., Perkin Trans., 1977, 2, 789, to give the coupled product 139.14. Deprotection, for example by treatment with aqueous pyridine p-toluenesulfonate, as described in Can. J. Chem., 61, 712, 1983, then affords the carboxylic acid 139.15.

Using the above procedures, but employing, in place of the 4-bromophenylpropionic acid 139.8, different bromophenylpropionic acids 139.1, and/or different dialkyl bromophenyl phosphonates 139.5, the corresponding products 139.7 are obtained.

Scheme 140 depicts the preparation of phenylpropionic acids in which a phosphonate ester is attached to the phenyl ring by means of a heteroatom. In this procedure, a suitably protected hydroxy, thio or amino-substituted phenyl propionic acid 140.1 is reacted with a derivative of a hydroxymethyl dialkylphosphonate 140.2, in which Lv is a leaving group such as methanesulfonyloxy and the like. The reaction is conducted in a polar aprotic solvent, in the presence of an organic or inorganic base, to afford the displacement product 140.3. Deprotection then affords the carboxylic acid 140.4.

For example, trichloroethyl 3-hydroxyphenylpropionic acid 140.5, prepared by reaction of 3hydroxyphenylpropionic acid (Fluka) with trichloroethanol and dicyclohexylcarbodiimide, as described in J. Am. Chem. Soc., 88, 852, 1966, is reacted with a dialkyl trifluoromethanesulfonyloxymethyl phosphonate 140.6, prepared as described in Tet. Lett., 1986, 27, 1477, to afford the ether product 140.7. Equimolar amounts of the reactants are combined in a polar solvent such as dimethylformamide, in the presence of a base such as potassium carbonate, at about 50° C., to afford the product 140.7. Removal of the trichloroethyl ester group, for example by treatment with zinc in acetic acid at 0° C., as described in J. Am. Chem. Soc., 88, 852, 1966, then yields the carboxylic acid 140.8.

Using the above procedures, but employing, in place of the phenol 140.5, different phenols, thiols or amines 140.1, and/or different phosphonates 140.2, the corresponding products 140.4 are obtained.

Scheme 141 illustrates the preparation of phenylpropionic acids in which a phosphonate moiety is attached by means of a chain incorporating a heteroatom. In this procedure, a carboxyl protected halomethyl substituted phenylpropionic acid 141.1 is reacted with a dialkyl hydroxy, thio or amino-substituted alkylphosphonate 141.2. The reaction is performed in the presence of a base, in a polar aprotic solvent such as dioxan or N-methylpyrrolidinone. The base employed in the reaction depends on the nature of the reactant 141.2. For example, if X is O, a strong base such as, for example, lithium hexamethyldisilylazide or potassium tert. butoxide is employed. If X is S, NH or N-alkyl, an inorganic base such as cesium carbonate and the like is employed.

For example, 4-bromomethyl phenylpropionic acid, prepared as described in U.S. Pat. No. 4,032,533, is converted into the methoxymethyl ester 141.5, by reaction with methoxymethyl chloride and triethylamine in dimethylformamide, as described in J. Chem. Soc, 2127, 1965. Equimolar amounts of the ester 141.5 and a dialkyl 2-aminoethyl phosphonate 141.6, prepared as described in J. Org. Chem., 2000, 65, 676, are reacted in dimethylformamide at ca 80° C., in the presence of potassium carbonate, to afford the displacement product 141.7. Deprotection, for example by treatment with trimethylsilyl bromide and a trace of methanol, as described in Aldrichimica Acta, 11, 23, 1978, then yields the carboxylic acid 141.8.

Using the above procedures, but employing, in place of the amine 141.6, different amines, alcohols or thiols 141.2 and/or different halomethyl-substituted phenylpropionic acids 141.1, the corresponding products 141.4 are obtained.

Scheme 142 illustrates the preparation of phosphonate esters attached to the phenyl ring by means of an oxygen or sulfur link, by means of a Mitsonobu reaction. In this procedure, a protected hydroxy- or thio-substituted phenylpropionic acid 142.1 is reacted with a dialkyl hydroxyalkyl phosphonate 142.2. The condensation reaction between 142.1 and 142.2 is effected in the presence of a triaryl phosphine and diethyl azodicarboxylate, as described in Org. React., 1992, 42, 335. The product 142.3 is then deprotected to afford the carboxylic acid 142.4.

For example, 3-mercaptophenylpropionic acid (Apin Chemicals) is converted into the tert. butyl ester 142.5, by treatment with carbonyl diimidazole, tert. butanol and diazabicycloundecene, as described in Synthesis, 833, 1982. The ester is reacted with a dialkyl hydroxymethylphosphonate 142.6, prepared as described in Synthesis, 4, 327, 1998, in the presence of triphenyl phosphine, triethylamine and diethyl azodicarboxylate, to afford the thioether 142.7. The tert. butyl group is removed by treatment with formic acid at ambient temperature, as described in J. Org. Chem., 42, 3972, 1977, to yield the carboxylic acid 142.8. Using the above procedures, but employing, in place of the thiol 142.5, different phenols or thiols 142.1 and/or different hydroxyalkyl phosphonates 142.2, the corresponding products 142.4 are obtained.

Scheme 143 depicts the preparation of phenylpropionic acids linked to a phosphonate ester by means of an aromatic or heteroaromatic ring. The products 143.3 are obtained by means of an alkylation reaction in which a bromomethyl aryl or heteroaryl phosphonate 143.1 is reacted with a carboxyl-protected hydroxy, thio or amino-substituted phenylpropionic acid 140.1. The reaction is conducted in the presence of a base, the nature of which is determined by the substituent X in the reactant 140.1. For example, if X is O, a strong base such as lithium hexamethyldisilylazide or sodium hydride is employed. If X is S or N, an organic or inorganic base, such as diisopropylethylamine or cesium carbonate is employed. The alkylated product 143.2 is then deprotected to afford the carboxylic acid 143.3.

For example, 3-(4-aminophenyl)propionic acid (Aldrich) is reacted with tert. butyl chlorodimethylsilane and imidazole in dimethylformamide, as described in Protective Groups in Organic Synthesis, by T. W. Greene and P. G. M Wuts, Wiley, Second Edition 1990, p. 262, to afford the silyl ester 143.4. This compound is reacted with a an equimolar amount of a dialkyl 4-bromomethylbenzylphosphonate 143.5, prepared as described in Tet. Lett., 1998, 54, 9341, in the presence of cesium carbonate in dimethylformamide at ambient temperature, to afford the product 143.6. The silyl ester is removed by treatment with tetrabutylammonium fluoride in tetrahydrofuran at ambient temperature, as described in J. Am. Chem. Soc., 94, 6190, 1972, to give the carboxylic acid 143.7.

Using the above procedures, but employing, in place of the amino compound 143.4, different phenols, mercaptans or amines 140.1, and/or different halomethyl phosphonates 143.1, the corresponding products 143.3 are obtained.

Scheme 133

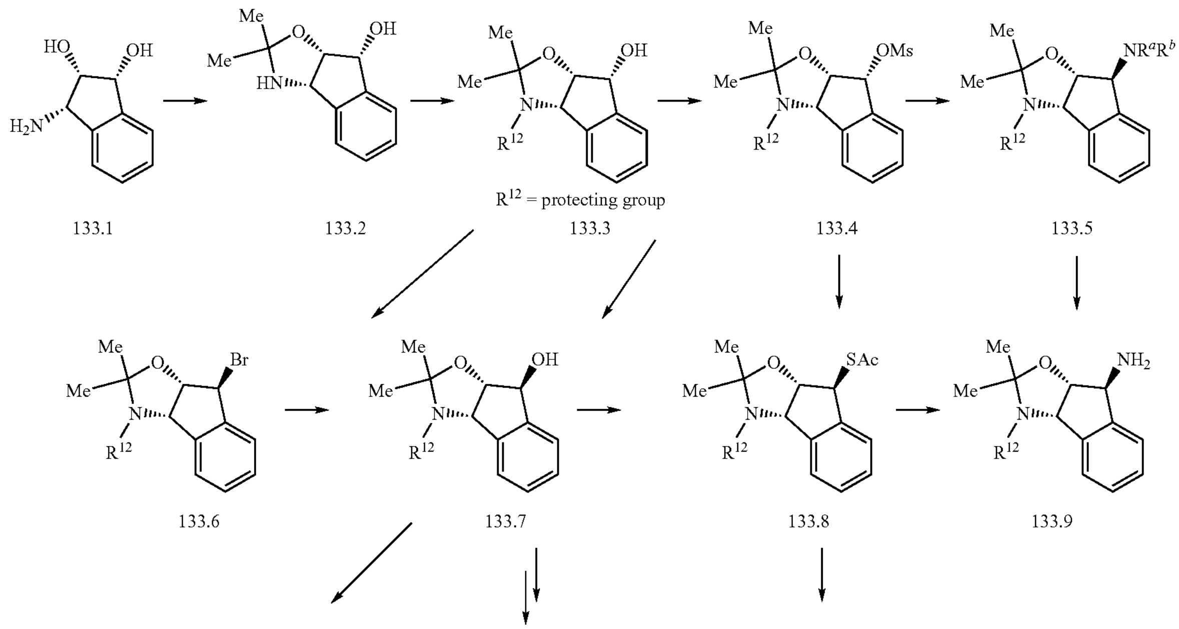

133.1 133.2 133.3 133.4 133.5 133.6 133.7 133.8 133.9

-continued
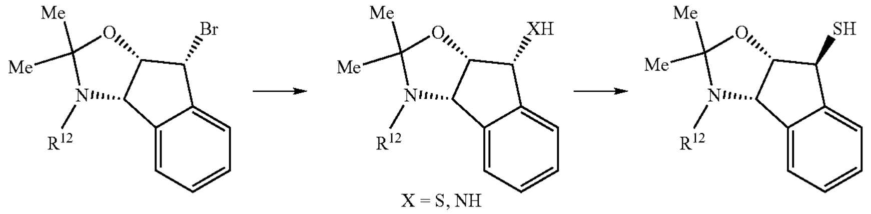
X = S, NH
133.10 133.11 133.12
Scheme 134
Method
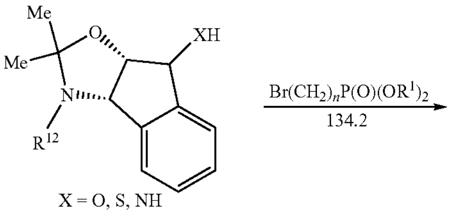
X = O, S, NH
134.1
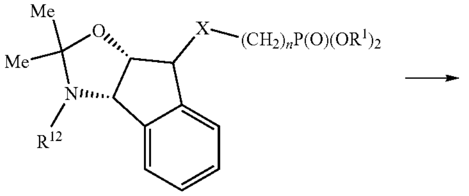
134.3
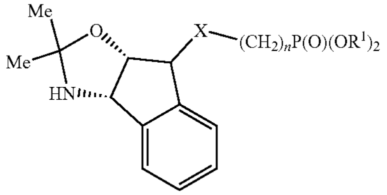
134.4
Example
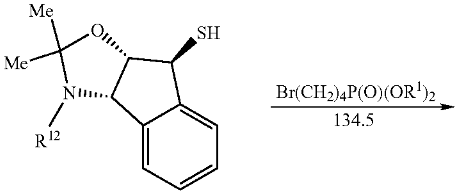
133.12
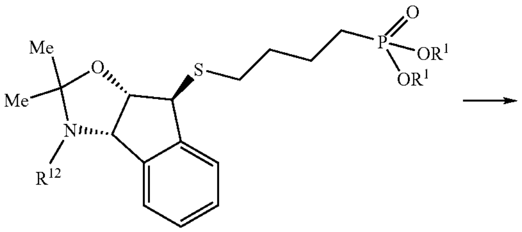
134.6
-continued
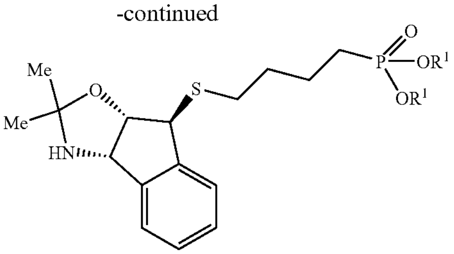
134.7
Scheme 135
Method
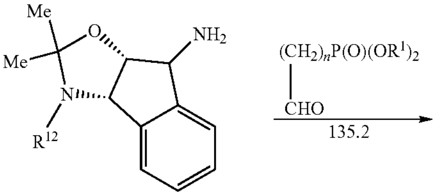
135.1
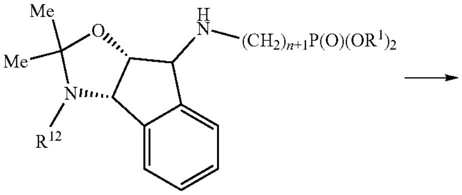
135.3
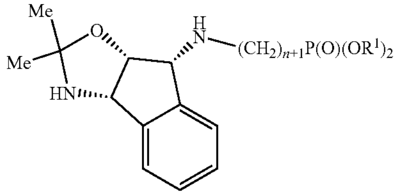
135.4
Example
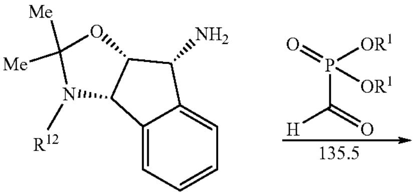
133.11

-continued
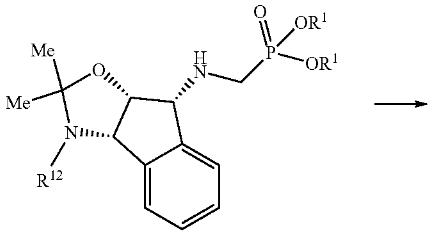
135.6
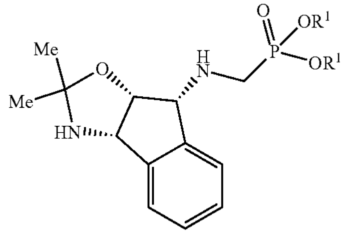
135.7
Scheme 136
Method
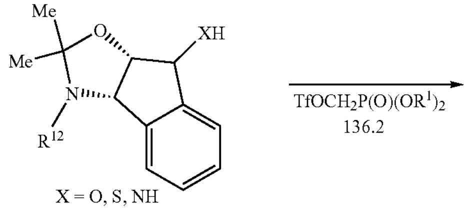
X = O, S, NH
136.1
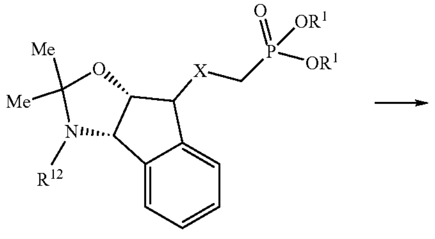
136.3
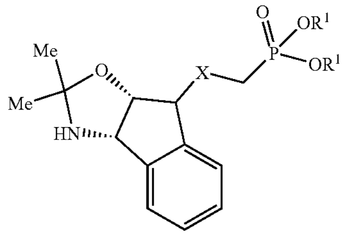
136.4
Example
-continued
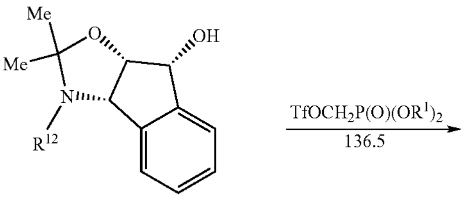
133.3
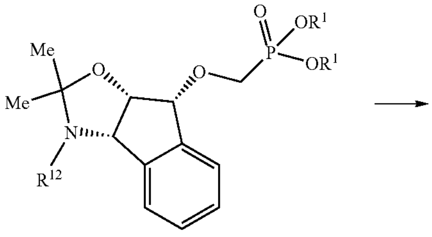
136.6
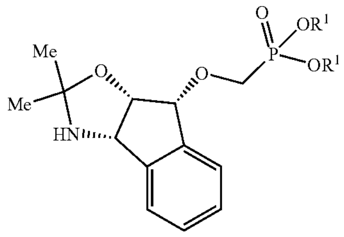
136.7
Scheme 137
Method
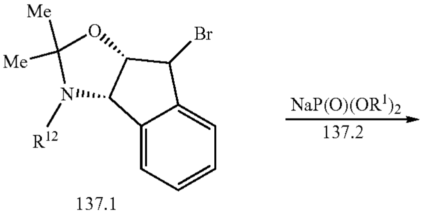
137.1
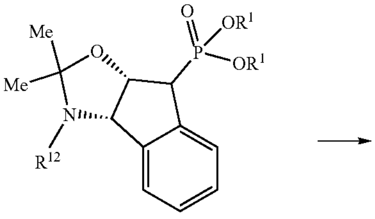
137.3
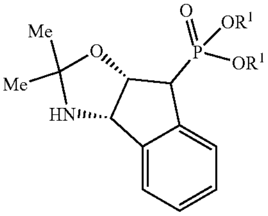
137.4
Example -continued
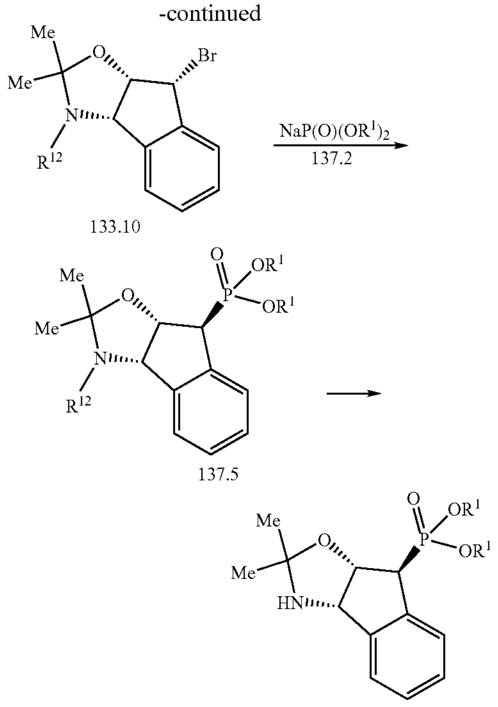
133.10
137.5
137.6
Scheme 139
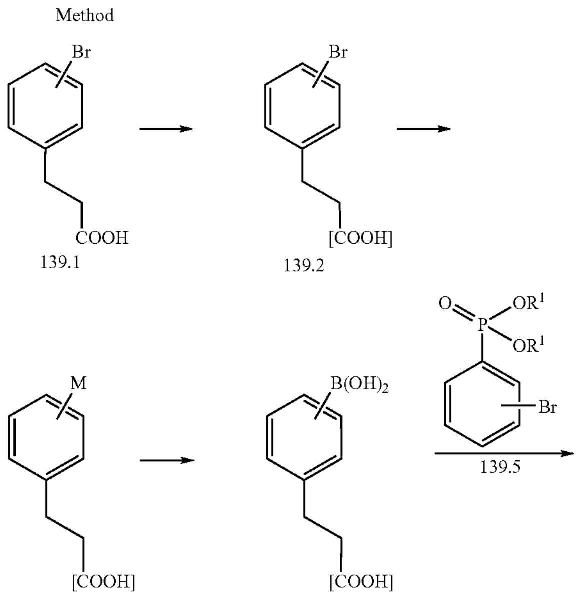
139.1
139.2
139.3
139.4
Scheme 138
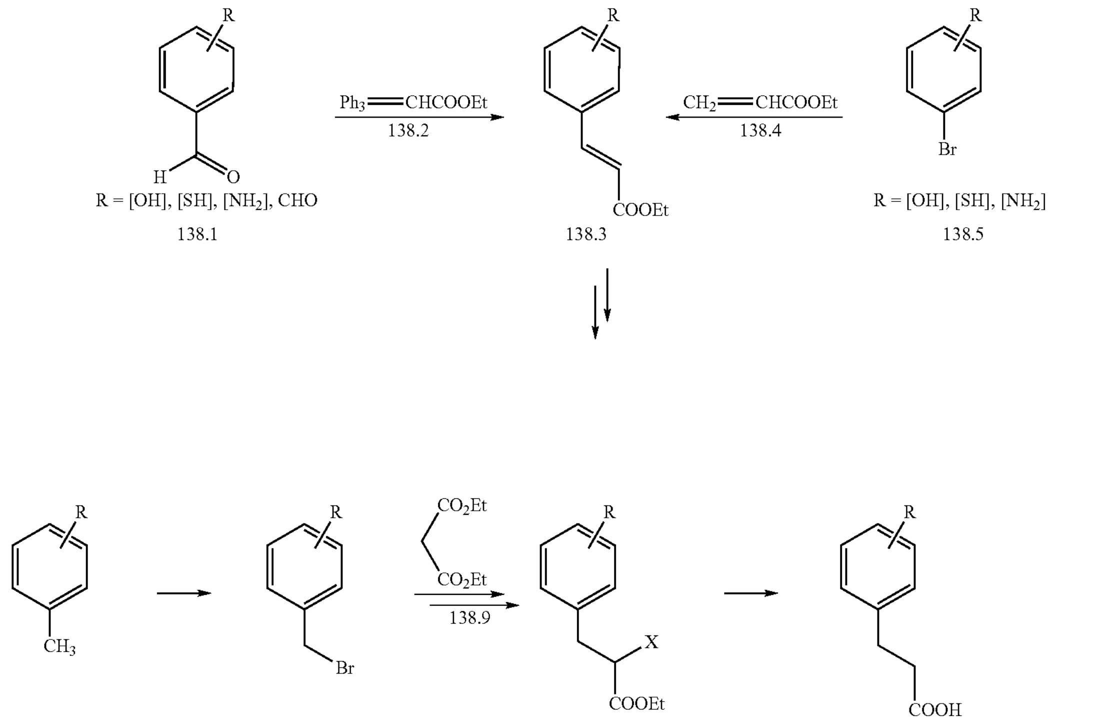
R = [OH], [SH], [$NH_2$], CHO
138.1
138.3
R = [OH], [SH], [$NH_2$]
138.5
R = [OH], [SH], [$NH_2$],
138.7
[NH]alkyl, $CH_2$Ha
138.8
X = COOEt or H
138.6
R = [OH], [SH], [$NH_2$] [NH]alkyl, $CH_2$Ha
138.10

-continued
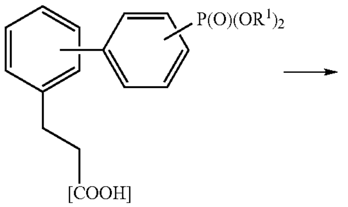
139.6
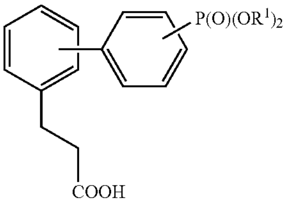
139.7
Example
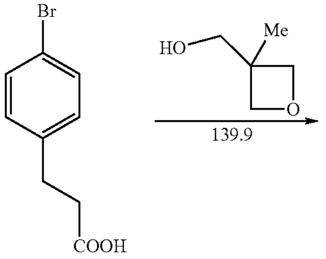
139.8
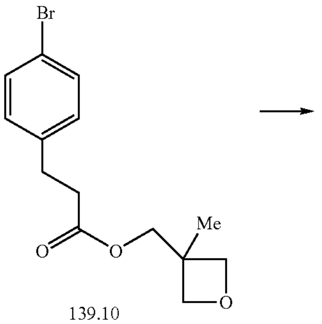
139.10
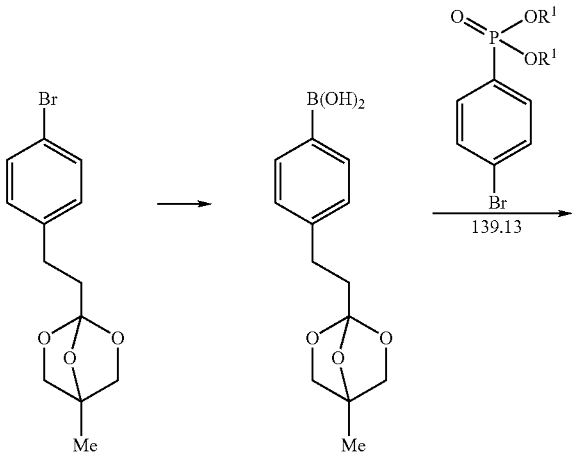
139.11 139.12
-continued
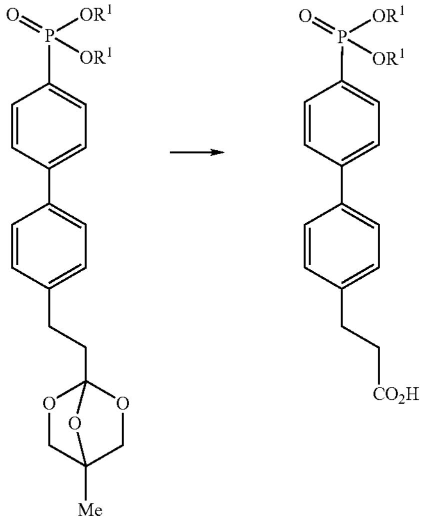
139.14 139.15
Scheme 140
Method
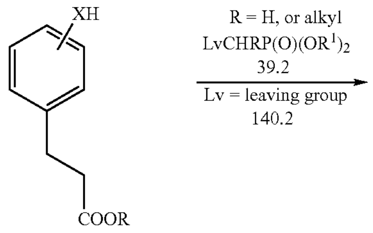
X = O, S, NH, Nalkyl
140.1
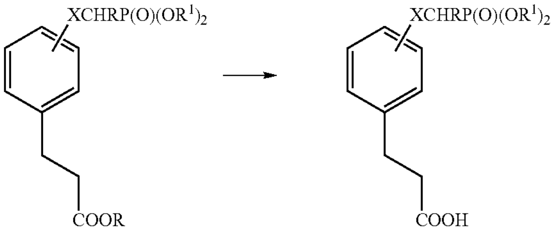
140.3 140.4
Example
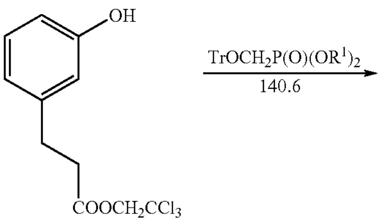
140.5

-continued
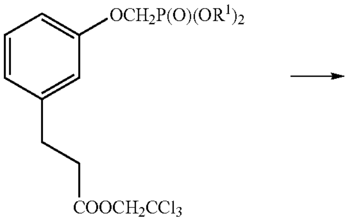
140.7
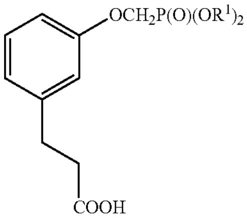
140.8
Scheme 141
Method
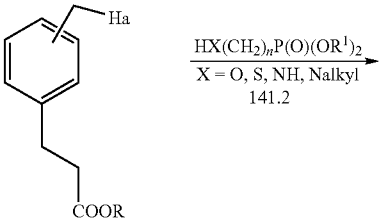
141.1
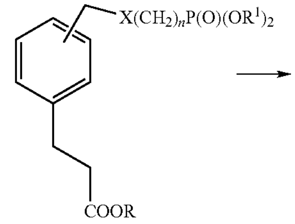
141.3
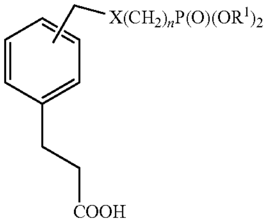
141.4
Example
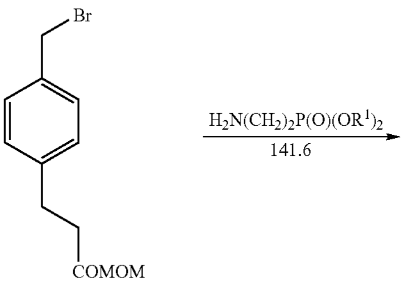
MOM = $OCH_2OCH_3$
141.5
-continued
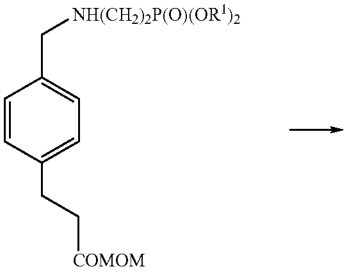
141.7
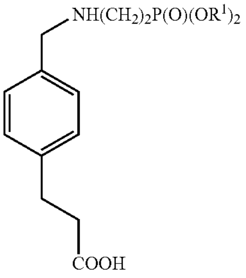
141.8
Scheme 142
Method
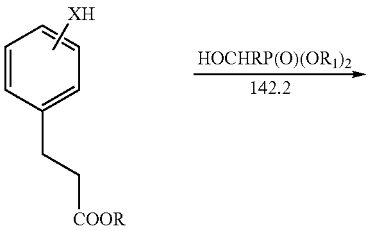
X = O, S
142.1
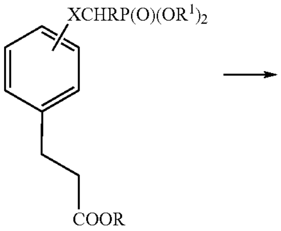
142.3
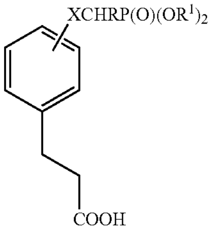
142.4
Example
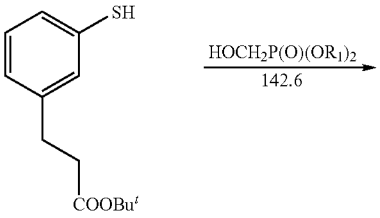
142.5

-continued

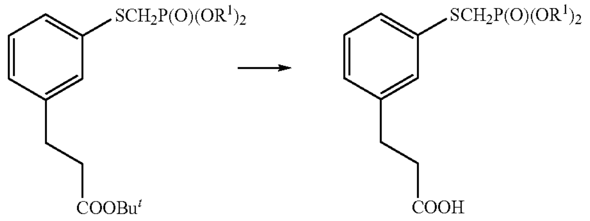

142.7 142.8

Scheme 143

Method

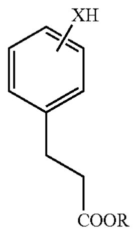

X = O, S, NH, Nalkyl 140.1

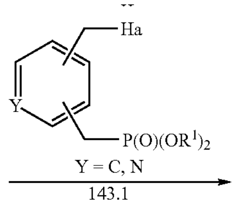

143.1

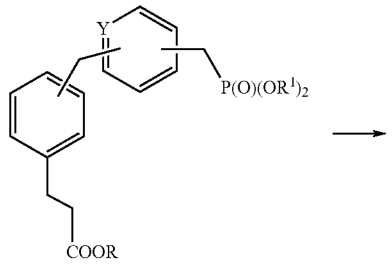

143.2

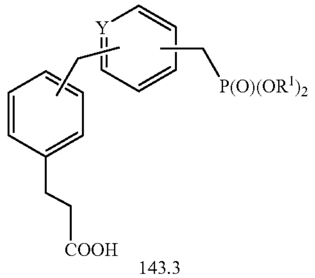

143.3

Example

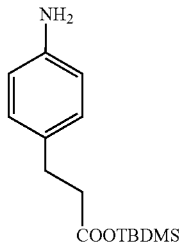

143.4

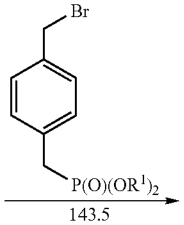

143.5

-continued

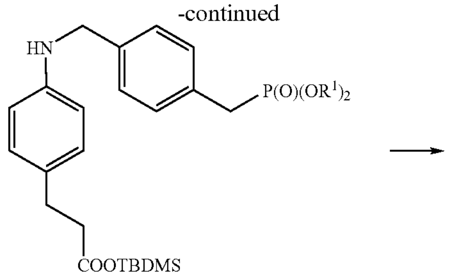

143.6

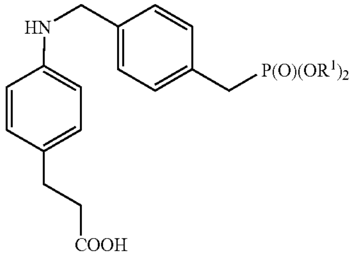

143.7

Preparation of the Phosphonate-containing Thiophenol Derivatives 7.1.

Schemes 144-153 describe the preparation of phosphonate-containing thiophenol derivatives 7.1 which are employed in the preparation of the phosphonate ester intermediates 2, 14 and 19 in which X is sulfur, and of the intermediate 15 in which X' is sulfur.

Scheme 144 depicts the preparation of thiophenol derivatives in which the phosphonate moiety is attached directly to the phenyl ring. In this procedure, a halo-substituted thiophenol 144.1 is protected to afford the product 144.2. The protection and deprotection of thiophenols is described in Protective Groups in Organic Synthesis, by T. W. Greene and P. G. M Wuts, Wiley, Second Edition 1990, p. 277. For example, thiol substituents are protected as trialkylsilyloxy groups. Trialkylsilyl groups are introduced by the reaction of the thiophenol with a chlorotrialkylsilane and a base such as imidazole. Alternatively, thiol substituents are protected by conversion to tert-butyl or adamantyl thioethers, or 4-methoxybenzyl thioethers, prepared by the reaction between the thiol and 4-methoxybenzyl chloride in the presence of ammonium hydroxide, as described in Bull. Chem. Soc. Jpn., 37, 433, 1974. The product is then coupled, in the presence of a palladium catalyst, with a dialkyl phosphite 144.3, to afford the phosphonate ester 144.4. The preparation of arylphosphonates by the coupling of aryl halides with dialkyl phosphites is described in J. Med. Chem., 35, 1371, 1992. The thiol protecting group is then removed, as described above, to afford the thiol 144.5.

For example, 3-bromothiophenol 144.6 is converted into the 9-fluorenylmethyl (Fm) derivative 144.7 by reaction with 9-fluorenylmethyl chloride and diisopropylethylamine in dimethylformamide, as described in Int. J. Pept. Protein Res., 20, 434, 1982. The product is then reacted with a dialkyl phosphite 144.3 to afford the phosphonate ester 144.8. The preparation of arylphosphonates by means of a coupling reaction between aryl bromides and dialkyl phosphites is described in J. Med. Chem., 35, 1371, 1992. The compound 144.7 is reacted, in toluene solution at reflux, with a dialkyl phosphite 144.3, triethylamine and tetrakis(triphenylphosphine)palladium(0), as described in J. Med. Chem., 35, 1371, 1992, to afford the phosphonate product 144.8. The Fm protecting group is then removed by treatment of the product with piperidine in dimethylformamide at ambient temperature, as described in J. Chem. Soc., Chem. Comm., 1501, 1986, to give the thiol 144.9.

Using the above procedures, but employing, in place of 3-bromothiophenol 144.6, different thiophenols 144.1, and/or different dialkyl phosphites 144.3, the corresponding products 144.5 are obtained.

Scheme 145 illustrates an alternative method for obtaining thiophenols with a directly attached phosphonate group. In this procedure, a suitably protected halo-substituted thiophenol 145.2 is metallated, for example by reaction with magnesium or by transmetallation with an alkyllithium reagent, to afford the metallated derivative 145.3. The latter compound is reacted with a halodialkyl phosphite 145.4 to afford the product 145.5; deprotection then affords the thiophenol 145.6

For example, 4-bromothiophenol 145.7 is converted into the S-triphenylmethyl (trityl) derivative 145.8, as described in Protective Groups in Organic Synthesis, by T. W. Greene and P. G. M. Wuts, Wiley, 1991, p. 287. The product is converted into the lithium derivative 145.9 by reaction with butyllithium in an ethereal solvent at low temperature, and the resulting lithio compound is reacted with a dialkyl chlorophosphite 145.10 to afford the phosphonate 145.11. Removal of the trityl group, for example by treatment with dilute hydrochloric acid in acetic acid, as described in J. Org. Chem., 31, 1118, 1966, then affords the thiol 145.12. Using the above procedures, but employing, in place of the bromo compound 145.7, different halo compounds 145.1, and/or different halo dialkyl phosphites 145.4, there are obtained the corresponding thiols 145.6.

Scheme 146 illustrates the preparation of phosphonate-substituted thiophenols in which the phosphonate group is attached by means of a one-carbon link. In this procedure, a suitably protected methyl-substituted thiophenol 146.1 is subjected to free-radical bromination to afford a bromomethyl product 146.2. This compound is reacted with a sodium dialkyl phosphite 146.3 or a trialkyl phosphite, to give the displacement or rearrangement product 146.4, which upon deprotection affords the thiophenol 146.5.

For example, 2-methylthiophenol 146.5 is protected by conversion to the benzoyl derivative 146.7, as described in Protective Groups in Organic Synthesis, by T. W. Greene and P. G. M. Wuts, Wiley, 1991, p. 298. The product is reacted with N-bromosuccinimide in ethyl acetate to yield the bromomethyl product 146.8. This material is reacted with a sodium dialkyl phosphite 146.3, as described in J. Med. Chem., 35, 1371, 1992, to afford the product 146.9.

Alternatively, the bromomethyl compound 146.8 is converted into the phosphonate 146.9 by means of the Arbuzov reaction, for example as described in Handb. Organophosphorus Chem., 1992, 115. In this procedure, the bromomethyl compound 146.8 is heated with a trialkyl phosphate $P(OR^1)_3$ at ca. 100° C. to produce the phosphonate 146.9. Deprotection of the phosphonate 146.9, for example by treatment with aqueous ammonia, as described in J. Am. Chem. Soc., 85, 1337, 1963, then affords the thiol 146.10.

Using the above procedures, but employing, in place of the bromomethyl compound 146.8, different bromomethyl compounds 146.2, there are obtained the corresponding thiols 146.5.

Scheme 147 illustrates the preparation of thiophenols bearing a phosphonate group linked to the phenyl nucleus by oxygen or sulfur. In this procedure, a suitably protected hydroxy or thio-substituted thiophenol 147.1 is reacted with a dialkyl hydroxyalkylphosphonate 147.2 under the conditions of the Mitsonobu reaction, for example as described in Org. React., 1992, 42, 335, to afford the coupled product 147.3. Deprotection then yields the O- or S-linked products 147.4.

For example, 3-hydroxythiophenol, 147.5, is converted into the monotrityl ether 147.6, by reaction with one equivalent of trityl chloride, as described above. This compound is reacted with diethyl azodicarboxylate, triphenyl phosphine and a dialkyl 1-hydroxymethyl phosphonate 147.7 in benzene, as described in Synthesis, 4, 327, 1998, to afford the ether compound 147.8. Removal of the trityl protecting group, as described above, then affords the thiophenol 147.9. Using the above procedures, but employing, in place of the phenol 147.5, different phenols or thiophenols 147.1, there are obtained the corresponding thiols 147.4.

Scheme 148 illustrates the preparation of thiophenols 148.4 bearing a phosphonate group linked to the phenyl nucleus by oxygen, sulfur or nitrogen. In this procedure, a suitably protected O, S or N-substituted thiophenol 148.1 is reacted with an activated ester, for example the trifluoromethanesulfonate 148.2, of a dialkyl hydroxyalkyl phosphonate, to afford the coupled product 148.3. Deprotection then affords the thiol 148.4.

For example, 4-methylaminothiophenol 148.5 is reacted in dichloromethane solution with one equivalent of acetyl chloride and a base such as pyridine, as described in Protective Groups in Organic Synthesis, by T. W. Greene and P. G. M. Wuts, Wiley, 1991, p. 298, to afford the S-acetyl product 148.6. This material is then reacted with a dialkyl trifluoromethanesulfonyloxymethyl phosphonate 148.7, the preparation of which is described in Tet. Lett., 1986, 27, 1477, to afford the displacement product 148.8. Preferably, equimolar amounts of the phosphonate 148.7 and the amine 148.6 are reacted together in an aprotic solvent such as dichloromethane, in the presence of a base such as 2,6-lutidine, at ambient temperatures, to afford the phosphonate product 148.8. Deprotection, for example by treatment with dilute aqueous sodium hydroxide for two minutes, as described in J. Am. Chem. Soc., 85, 1337, 1963, then affords the thiophenol 148.9.

Using the above procedures, but employing, in place of the thioamine 148.5, different phenols, thiophenols or amines 148.1, and/or different phosphonates 148.2, there are obtained the corresponding products 148.4.

Scheme 149 illustrates the preparation of phosphonate esters linked to a thiophenol nucleus by means of a heteroatom and a multiple-carbon chain, employing a nucleophilic displacement reaction on a dialkyl bromoalkyl phosphonate 149.2. In this procedure, a suitably protected hydroxy, thio or amino substituted thiophenol 149.1 is reacted with a dialkyl bromoalkyl phosphonate 149.2 to afford the product 149.3. Deprotection then affords the free thiophenol 149.4.

For example, 3-hydroxythiophenol 149.5 is converted into the S-trityl compound 149.6, as described above. This compound is then reacted with a dialkyl 4-bromobutyl phosphonate 149.7, the synthesis of which is described in Synthesis, 1994, 9, 909. The reaction is conducted in a dipolar aprotic solvent, for example dimethylformamide, in the presence of a base such as potassium carbonate, and optionally in the presence of a catalytic amount of potassium iodide, at about 50° C. to yield the ether product 149.8. Deprotection, as described above, then affords the thiol-149.9.

Using the above procedures, but employing, in place of the phenol 149.5, different phenols, thiophenols or amines 149.1, and/or different phosphonates 149.2, there are obtained the corresponding products 149.4.

Scheme 150 depicts the preparation of phosphonate esters linked to a thiophenol nucleus by means of unsaturated and saturated carbon chains. The carbon chain linkage is formed by means of a palladium catalyzed Heck reaction, in which an olefinic phosphonate 150.2 is coupled with an aromatic bromo compound 150.1. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or a palladium(II) catalyst such as palladium(II) acetate, and optionally in the presence of a base such as triethylamine or potassium carbonate, to afford the coupled product 150.3. Deprotection, or hydrogenation of the double bond followed by deprotection, affords respectively the unsaturated phosphonate 150.4, or the saturated analog 150.6.

For example, 3-bromothiophenol is converted into the S—Fm derivative 150.7, as described above, and this compound is reacted with a dialkyl 1-butenyl phosphonate 150.8, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 100° C. to afford the coupled product 150.9. Deprotection, as described above, then affords the thiol 150.10. Optionally, the initially formed unsaturated phosphonate 150.9 is subjected to catalytic or chemical reduction, for example using diimide, as described in Scheme 138, to yield the saturated product 150.11, which upon deprotection affords the thiol 150.12.

Using the above procedures, but employing, in place of the bromo compound 150.7, different bromo compounds 150.1, and/or different phosphonates 150.2, there are obtained the corresponding products 150.4 and 150.6

Scheme 151 illustrates the preparation of an aryl-linked phosphonate ester 151.4 by means of a palladium(0) or palladium(II) catalyzed coupling reaction between a bromobenzene and a phenylboronic acid, as described in Comprehensive Organic Transformations, by R. C. Larock, VCH, 1989, p. 57. The sulfur-substituted phenylboronic acid 151.1 is obtained by means of a metallation-boronation sequence applied to a protected bromo-substituted thiophenol, for example as described in J. Org. Chem., 49, 5237, 1984. A coupling reaction then affords the diaryl product 151.3 which is deprotected to yield the thiol 151.4.

For example, protection of 4-bromothiophenol by reaction with tert-butylchlorodimethylsilane, in the presence of a base such as imidazole, as described in Protective Groups in Organic Synthesis, by T. W. Greene and P. G. M. Wuts, Wiley, 1991, p. 297, followed by metallation with butyllithium and boronation, as described in J. Organomet. Chem., 1999, 581, 82, affords the boronate 151.5. This material is reacted with a dialkyl 4-bromophenylphosphonate 151.6, the preparation of which is described in J. Chem. Soc., Perkin Trans., 1977, 2, 789, in the presence of tetrakis(triphenylphosphine)palladium (0) and an inorganic base such as sodium carbonate, to afford the coupled product 151.7. Deprotection, for example by the use of tetrabutylammonium fluoride in anhydrous tetrahydrofuran, then yields the thiol 151.8. Using the above procedures, but employing, in place of the boronate 151.5, different boronates 151.1, and/or different phosphonates 151.2, there are obtained the corresponding products 151.4.

Scheme 152 depicts the preparation of dialkyl phosphonates in which the phosphonate moiety is linked to the thiophenyl group by means of a chain which incorporates an aromatic or heteroaromatic ring. In this procedure, a suitably protected O, S or N-substituted thiophenol 152.1 is reacted with a dialkyl bromomethyl-substituted aryl or heteroarylphosphonate 152.2, prepared, for example, by means of an Arbuzov reaction between equimolar amounts of a bis(bromo-methyl) substituted aromatic compound and a trialkyl phosphite. The reaction product 152.3 is then deprotected to afford the thiol 152.4.

For example, 1,4-dimercaptobenzene is converted into the monobenzoyl ester 152.5 by reaction with one molar equivalent of benzoyl chloride, in the presence of a base such as pyridine. The monoprotected thiol 152.5 is then reacted with a dialkyl 4-(bromomethyl)phenylphosphonate, 152.6, the preparation of which is described in Tetrahedron, 1998, 54, 9341. The reaction is conducted in a solvent such as dimethylformamide, in the presence of a base such as potassium carbonate, at about 50° C. The thioether product 152.7 thus obtained is deprotected, as described above, to afford the thiol 152.8.

Using the above procedures, but employing, in place of the thiophenol 152.5, different phenols, thiophenols or amines 152.1, and/or different phosphonates 152.2, there are obtained the corresponding products 152.4.

Scheme 153 illustrates the preparation of phosphonate-containing thiophenols in which the attached phosphonate chain forms a ring with the thiophenol moiety.

In this procedure, a suitably protected thiophenol 153.1, for example an indoline (in which X—Y is $(CH_2)_2$), an indole (X—Y is CH═CH) or a tetrahydroquinoline (X—Y is $(CH_2)_3$) is reacted with a dialkyl trifluoromethanesulfonyloxymethyl phosphonate 153.2, in the presence of an organic or inorganic base, in a polar aprotic solvent such as, for example, dimethylformamide, to afford the phosphonate ester 153.3. Deprotection, as described above, then affords the thiol 153.4. The preparation of thio-substituted indolines is described in EP 209751. Thio-substituted indoles, indolines and tetrahydroquinolines are also obtained from the corresponding hydroxy-substituted compounds, for example by thermal rearrangement of the dimethylthiocarbamoyl esters, as described in J. Org. Chem., 31, 3980, 1966. The preparation of hydroxy-substituted indoles is described in Syn., 1994, 10, 1018; preparation of hydroxy-substituted indolines is described in Tet. Lett., 1986, 27, 4565, and the preparation of hydroxy-substituted tetrahydroquinolines is described in J. Het. Chem., 1991, 28, 1517, and in J. Med. Chem., 1979, 22, 599. Thio-substituted indoles, indolines and tetrahydroquinolines are also obtained from the corresponding amino and bromo compounds, respectively by diazotization, as described in Sulfur Letters, 2000, 24, 123, or by reaction of the derived organolithium or magnesium derivative with sulfur, as described in Comprehensive Organic Functional Group Preparations, A. R. Katritzky et al, eds, Pergamon, 1995, Vol. 2, p. 707. For example, 2,3-dihydro-1H-indole-5-thiol, 153.5, the preparation of which is described in EP 209751, is converted into the benzoyl ester 153.6, as described above, and the ester is then reacted with the trifluoromethanesulfonate 153.7, using the conditions described above for the preparation of the phosphonate 148.8, (Scheme 148), to yield the phosphonate 153.8. Deprotection, for example by reaction with dilute aqueous ammonia, as described above, then affords the thiol 153.9.

Using the above procedures, but employing, in place of the thiol 153.5, different thiols 153.1, and/or different triflates 153.2, there are obtained the corresponding products 153.4.

Scheme 144
Method
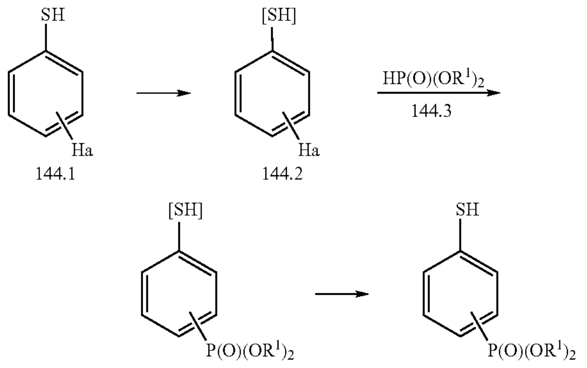
144.1 144.2 144.4 144.5
Example
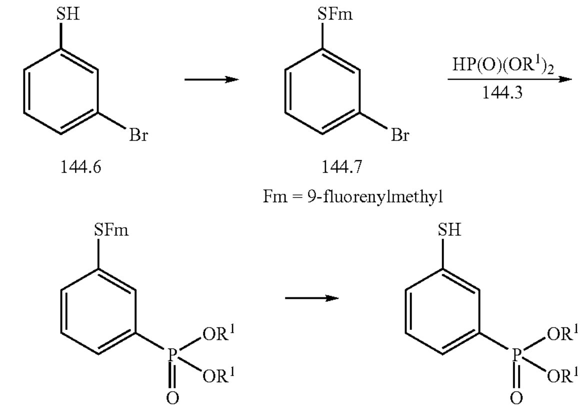
144.6 144.7
Fm = 9-fluorenylmethyl
144.8 144.9
Scheme 145
Method
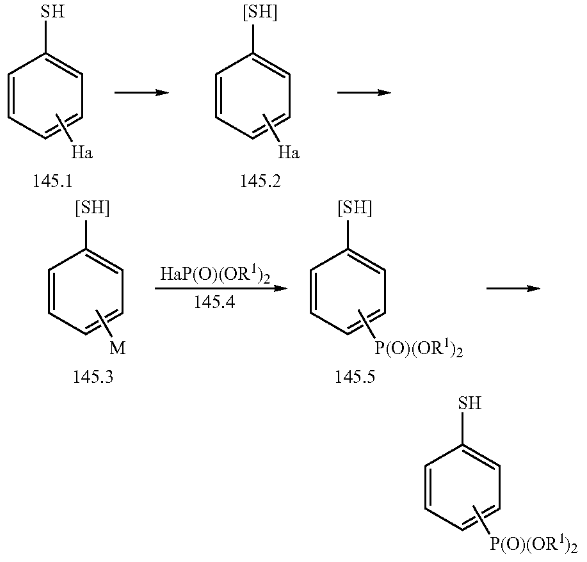
145.1 145.2 145.3 145.5 145.6
-continued
Example
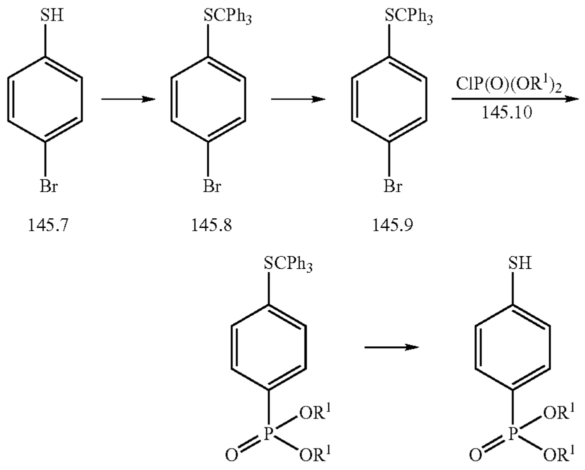
145.7 145.8 145.9 145.11 145.12
Scheme 146
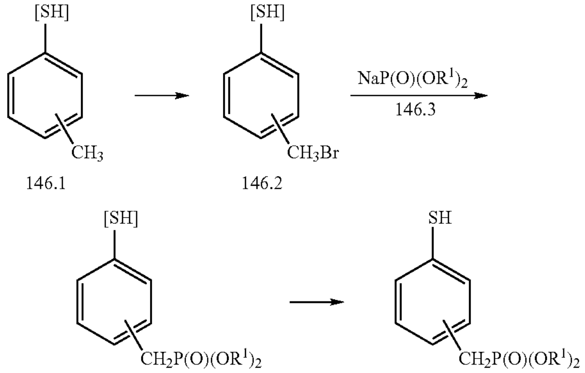
146.1 146.2 146.4 146.5
Example
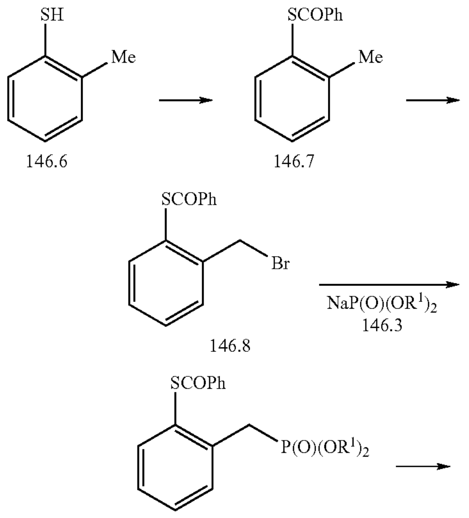
146.6 146.7 146.8 146.9

-continued
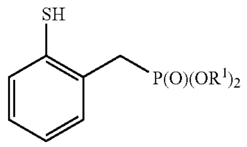
146.10
Scheme 147
Method
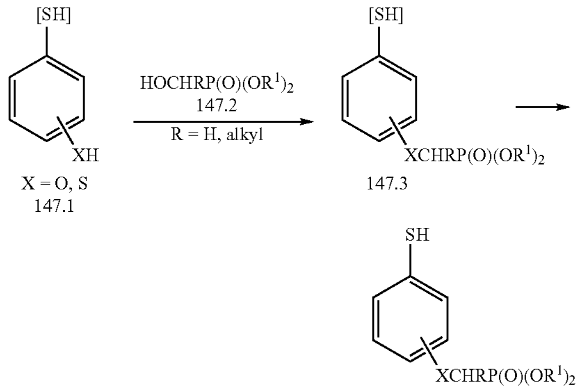
X = O, S
147.1
147.3
147.4
Example
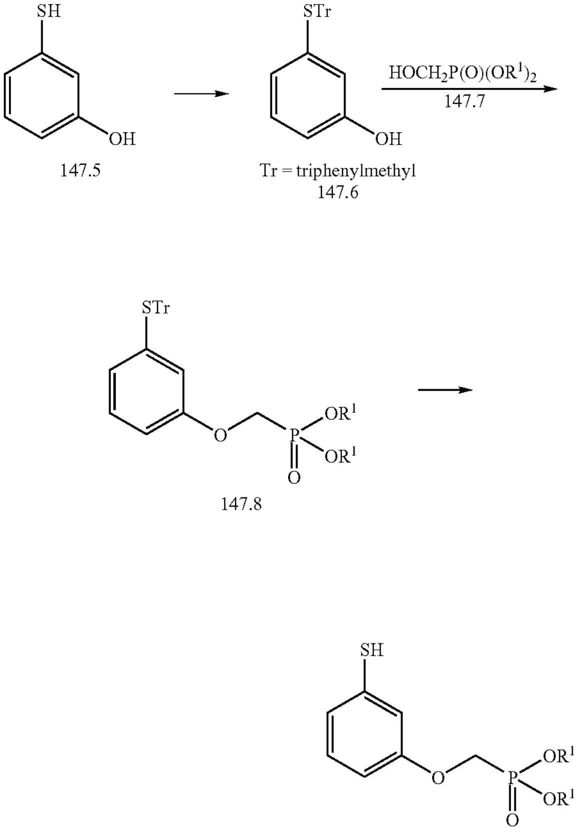
147.5
Tr = triphenylmethyl
147.6
147.8
147.9
Scheme 148
Method
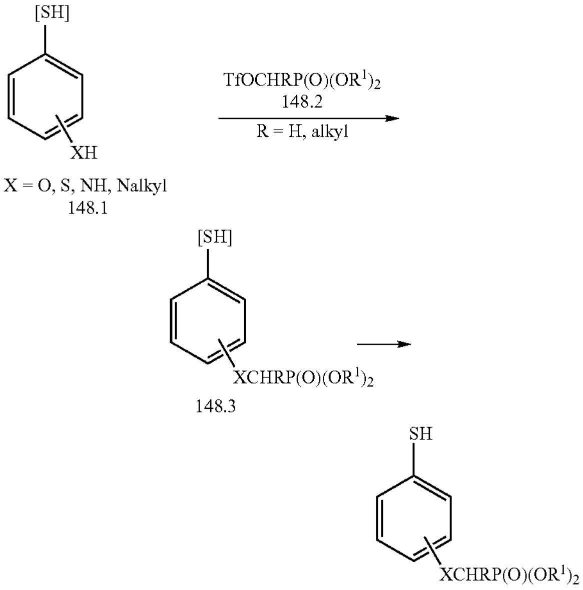
X = O, S, NH, Nalkyl
148.1
148.3
148.4
Example
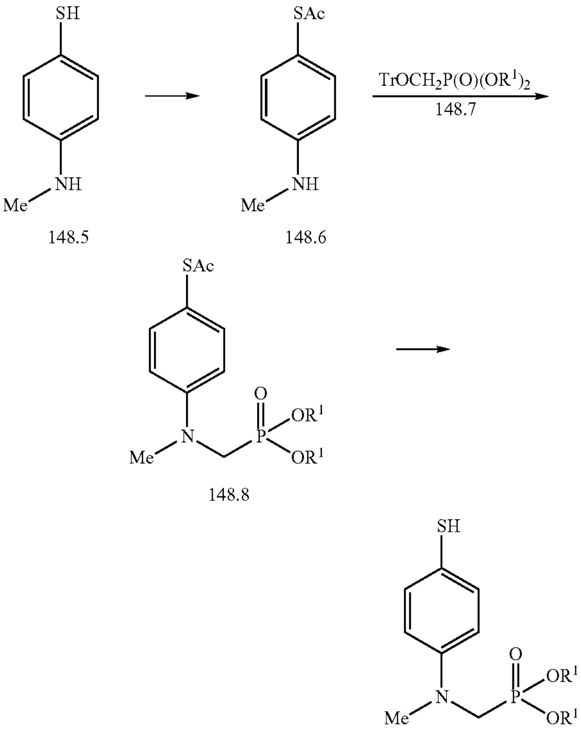
148.5
148.6
148.8
148.9

Scheme 149
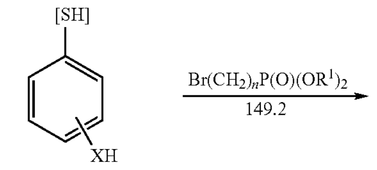
X = O, S, NH, Nalkyl
149.1
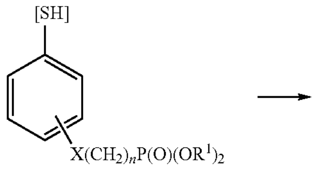
149.3
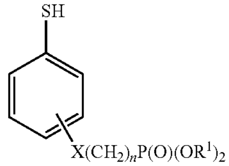
149.4
Example
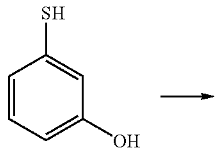
149.5
-continued
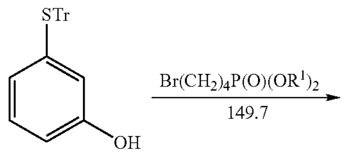
Tr = triphenylmethyl
149.6
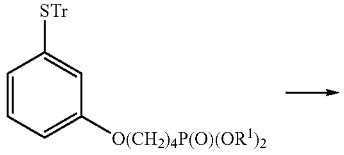
149.8
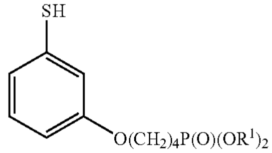
149.9
Scheme 150
Method
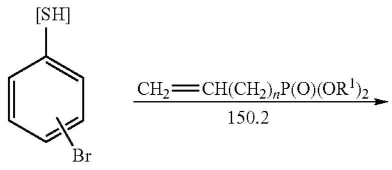
150.1
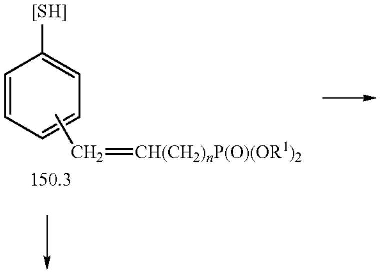
150.3
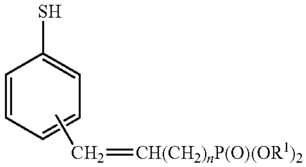
150.4
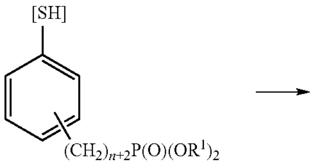
150.5
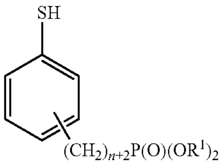
150.6
Example -continued
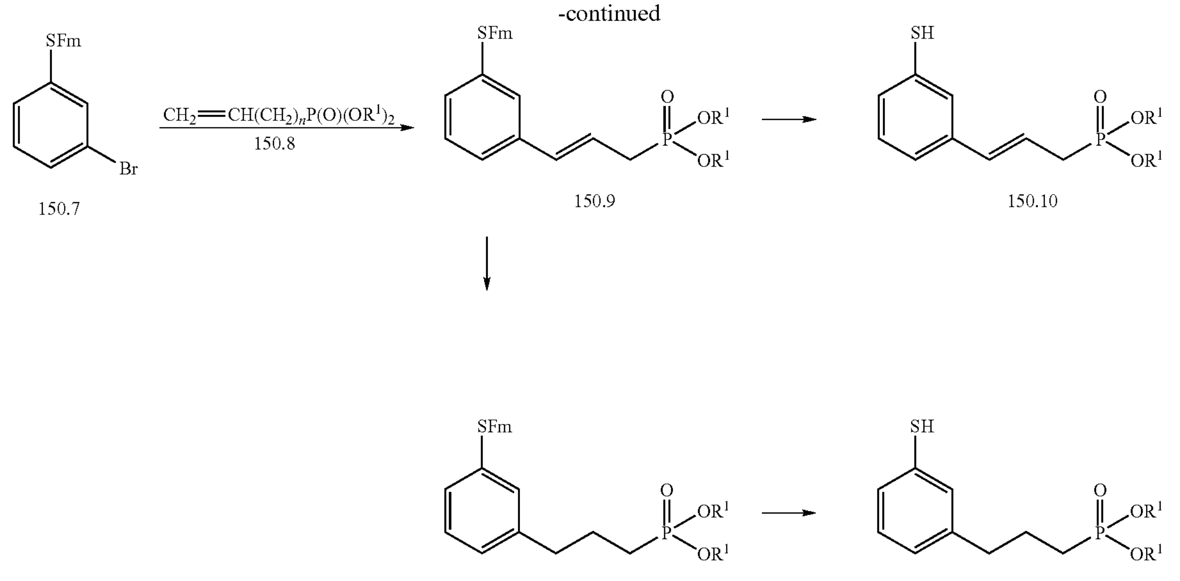
150.7 150.9 150.10
150.11 150.12
Scheme 151
Method
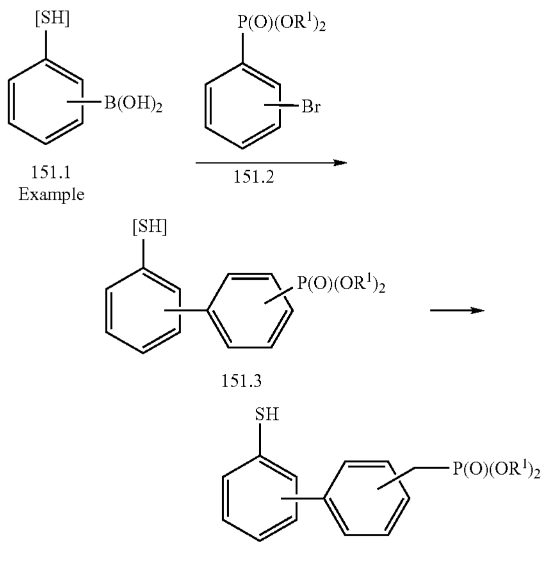
151.1
Example
151.3
152.4
Example
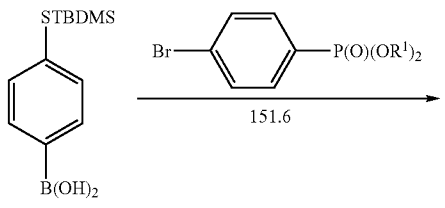
151.5
-continued
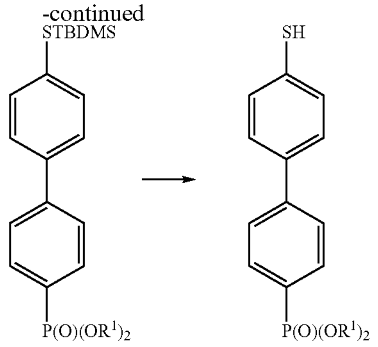
151.7 151.8
Scheme 152
Method
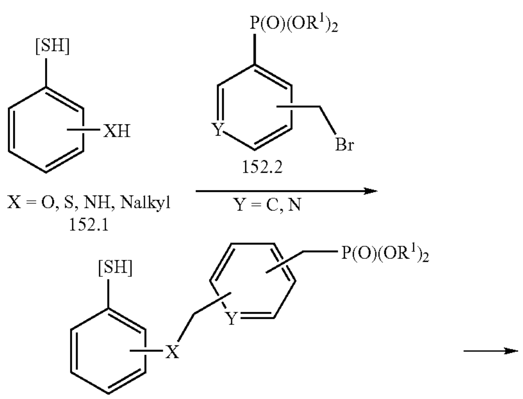
X = O, S, NH, Nalkyl
152.1
152.2
152.3

-continued

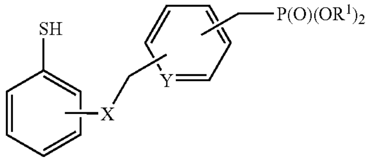

152.4

Example

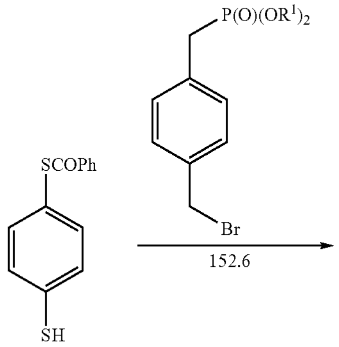

152.5

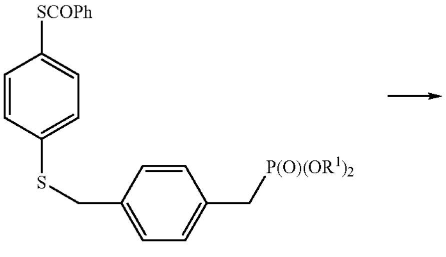

152.7

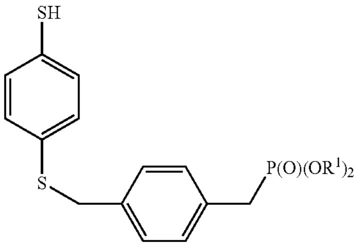

152.8

Scheme 153

Method

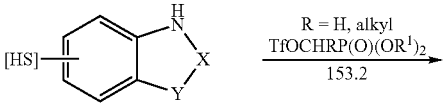

153.1

X—Y = $(CH_2)_{2,3}$; CH═CH

-continued

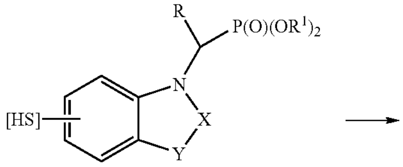

153.3

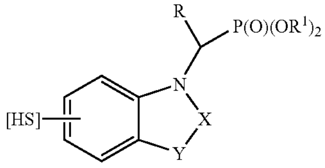

153.4

Example

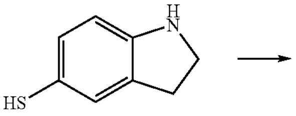

153.5

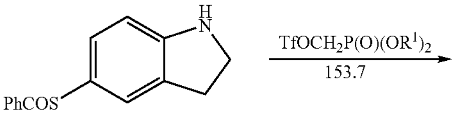

153.6

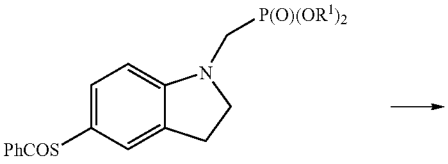

153.8

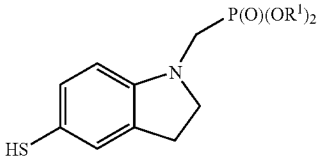

153.9

Preparation of Tert-Butylamine Derivatives 9.3 and 25.4 Incorporating Phosphonate Groups.

Schemes 154-158 illustrate the preparation of the tert. butylamine derivatives 9.3 and 25.4 in which the substituent A is either the group link $P(O)(OR^1)_2$ or a precursor, such as [OH], [SH], Br, which are employed in the preparation of the intermediate phosphonate esters 3, 7, 11 and 20.

Scheme 154 describes the preparation of tert-butylamines in which the phosphonate moiety is directly attached to the tert-butyl group. A suitably protected 2.2-dimethyl-2-amino-ethyl bromide 154.1 is reacted with a trialkyl phosphite 154.2, under the conditions of the Arbuzov reaction, as described in Scheme 137, to afford the phosphonate 154.3, which is then deprotected to give the amine 154.4.

For example, the cbz derivative of 2,2-dimethyl-2-amino-ethyl bromide 154.6, is heated with a trialkyl phosphite at ca 150° C. to afford the product 154.7. Deprotection then affords the free amine 154.8. The removal of carbobenzyloxy substituents to afford the corresponding amines is described in Protective Groups in Organic Synthesis, by T. W. Greene and P. G. M Wuts, Wiley, Second Edition 1990, p. 335. The conversion is effected by the use of catalytic hydrogenation, in the presence of hydrogen or a hydrogen donor and a palladium catalyst.

Alternatively, the cbz group is removed by treatment of the substrate with triethylsilane, triethylamine and a catalytic amount of palladium (II) chloride, as described in Chem. Ber., 94, 821, 1961, or by the use of trimethylsilyl iodide in acetonitrile at ambient temperature, as described in J. Chem. Soc., Perkin Trans. I, 1277, 1988. The cbz group is also removed by treatment with Lewis acid such as boron tribromide, as described in J. Org. Chem., 39, 1247, 1974, or aluminum chloride, as described in Tet. Lett., 2793, 1979.

Using the above procedures, but employing different trialkyl phosphites, there are obtained the corresponding amines 154.4.

Scheme 155 illustrates the preparation of phosphonate esters attached to the tert butylamine by means of a heteroatom and a carbon chain. A protected alcohol or thiol 155.1 is reacted with a dialkyl bromoalkylphosphonate 155.2, to afford the displacement product 155.3. Deprotection, if needed, then yields the amine 155.4.

For example, the cbz derivative of 2-amino-2,2-dimethylethanol 155.5 is reacted with a dialkyl 4-bromobutyl phosphonate 155.6, prepared as described in Synthesis, 1994, 9, 909, in dimethylformamide containing potassium carbonate and a catalytic amount of potassium iodide, at ca 60° to afford the phosphonate 155.7 Deprotection, by hydrogenation over a palladium catalyst, then affords the free amine 155.8.

Using the above procedures, but employing different alcohols or thiols 155.1, and/or different bromoalkylphosphonates 155.2, there are obtained the corresponding ether and thioether products 155.4.

Scheme 156 describes the preparation of carbon-linked tert. butylamine phosphonate derivatives, in which the carbon chain is unsaturated or saturated.

In the procedure, a terminal acetylenic derivative of tert-butylamine 156.1 is reacted, under basic conditions, with a dialkyl chlorophosphite 156.2, to afford the acetylenic phosphonate 156.3. The coupled product 156.3 is deprotected to afford the amine 156.4. Partial or complete catalytic hydrogenation of this compound affords the olefinic and saturated products 156.5 and 156.6 respectively.

For example, 2-amino-2-methylprop-1-yne 156.7, the preparation of which is described in WO 9320804, is converted into the N-phthalimido derivative 156.8, by reaction with phthalic anhydride, as described in Protective Groups in Organic Synthesis, by T. W. Greene and P. G. M. Wuts, Wiley, 1991, pp. 358. This compound is reacted with lithium diisopropylamide in tetrahydrofuran at −78° C. The resultant anion is then reacted with a dialkyl chlorophosphite 156.2 to afford the phosphonate 156.9. Deprotection, for example by treatment with hydrazine, as described in J. Org. Chem., 43, 2320, 1978, then affords the free amine 156.10. Partial catalytic hydrogenation, for example using Lindlar catalyst, as described in Reagents for Organic Synthesis, by L. F. Fieser and M. Fieser, Volume 1, p. 566, produces the olefrnic phosphonate 156.11, and conventional catalytic hydrogenation, as described in Organic Functional Group Preparations, by S. R. Sandler and W. Karo, Academic Press, 1968, p. 3. for example using 5% palladium on carbon as catalyst, affords the saturated phosphonate 156.12. Using the above procedures, but employing different acetylenic amines 156.1, and/or different dialkyl halophosphites, there are obtained the corresponding products 156.4, 156.5 and 156.6.

Scheme 157 illustrates the preparation of a tert butylamine phosphonate in which the phosphonate moiety is attached by means of a cyclic amine.

In this method, an aminopropyl-substituted cyclic amine 157.1 is reacted with a limited amount of a bromoalkyl phosphonate 157.2, using, for example, the conditions described above (Scheme 149) to afford the displacement product 157.3.

For example, 3-(1-amino-1-methyl)ethylpyrrolidine 157.4, the preparation of which is described in Chem. Pharm. Bull., 1994, 42, 1442, is reacted with one molar equivalent of a dialkyl 4-bromobutyl phosphonate 157.5, prepared as described in Synthesis, 1994, 9, 909, to afford the displacement product 157.6.

Using the above procedures, but employing, in place of 3-(1-amino-1-methyl)ethylpyrrolidine 157.4, different cyclic amines 157.1, and/or different bromoalkylphosphonates 157.2, there are obtained the corresponding products 157.3.

Scheme 158 illustrates the preparation of the amides 9.3 which are employed in the preparation of the phosphonate esters 3. In this procedure, the carboxylic acids 158.1, the structures of which are illustrated in Chart 10, compounds C1-C16, are converted into the BOC-protected derivatives 155.8. Methods for the conversion of amines into the BOC derivative are described in Protective Groups in Organic Synthesis, by T. W. Greene and P. G. M Wuts, Wiley, Second Edition 1990, p. 327. For example, the amine is reacted with di-tert-butoxycarbonylanhydride (BOC anhydride) and a base, or with 2-(tert-butoxycarbonyloxyimino)-2-phenylacetonitrile (BOC-ON), and the like. The carboxylic acid 158.2 is then coupled, as described in Scheme 1, with the tert. butylamine derivatives 25.4, or precursors thereto, the preparation of which is described in Schemes 154-157, to afford the amide 158.3. The BOC group is then removed to yield the amine 9.3. The removal of BOC protecting groups is described, for example, in Protective Groups in Organic Synthesis, by T. W. Greene and P. G. M Wuts, Wiley, Second Edition 1990, p. 328. The deprotection is effected by treatment of the BOC compound with anhydrous acids, for example, hydrogen chloride or trifluoroacetic acid, or by reaction with trimethylsilyl iodide or aluminum chloride.

Preparation of Pyridine Intermediates 13.1 Incorporating Phosphonate Substituents.

Schemes 159-163, described the preparation of chloromethyl or formyl pyridine derivatives incorporating phosphonate moieties. Scheme 164 illustrates the conversion of the above compounds into the piperazine derivatives 13.1 which are employed in the preparation of the phosphonate esters 4.

Scheme 159 illustrates the preparation of chloromethyl-substituted pyridines in which a phosphonate moiety is directly attached to the pyridine ring.

In this procedure, a halo-substituted methylpyridine 159.1 is reacted with a dialkyl phosphite 159.2, to afford the phosphonate product 159.3. The coupling reaction is conducted in the presence of a palladium (0) catalyst, for example as described in J. Med. Chem., 35, 1371, 1992. The product 159.3 is then converted into the chloromethyl derivative 159.4 by means of a chlorination reaction. The chlorination of benzylic methyl groups is described in Comprehensive Organic Transformations, by R. C. Larock, VCH, 1989, p. 313. A variety of free-radical chlorinating agents are employed.

For example, 3-bromo-5-methylpyridine, 159.5 (ChemPacific) is reacted with an equimolar amount of a dialkyl sodium phosphite, 13.2 in the presence of tetrakis(triphenylphosphine)palladium(0) and triethylamine, in toluene at reflux, to yield the phosphonate 159.6. The latter compound is then chlorinated, for example by the use of one molar equivalent of phenyliodonium dichloride, as described in J. Org. Chem., 29, 3692, 1964, to prepare the chloromethyl compound 159.7.

Using the above procedures, but employing, in place of the bromomethylpyridine 159.5, different halomethylpyridines 159.1, and/or different dialkyl phosphites 159.2 the corresponding products 159.4 are obtained.

Scheme 160 depicts the preparation of chloromethylpyridines incorporating a phosphonate group attached to the pyridine ring by means of a carbon link. In this procedure, a bis(chloromethyl)pyridine 160.1 is reacted with a sodium dialkyl phosphite 146.3, employing, for example, procedures described in J. Med. Chem., 35, 1371, 1992, to afford the displacement product 160.2.

For example, 3,5-bis(chloromethyl)pyridine 160.3, the preparation of which is described in Eur. J. Inorg. Chem., 1998, 2, 163, is reacted with one molar equivalent of a dialkyl sodium phosphite 146.3 in tetrahydrofuran, at ambient temperature, to afford the product 160.4.

Using the above procedures, but employing, in place of the bis(chloromethyl) compound 160.3, different bis(chloromethyl) pyridines 160.1, and/or different dialkyl sodium phosphites 146.3 the corresponding products 160.2 are obtained.

Scheme 161 illustrates the preparation of pyridine aldehydes incorporating a phosphonate group linked to the pyridine nucleus by means of a saturated or unsaturated carbon chain. In this procedure, a suitably protected halo-substituted pyridine carboxaldehyde 161.1 is coupled, by means of a palladium-catalyzed Heck reaction, as described in Scheme 150, with a dialkyl alkenyl phosphonate 161.2. Methods for the protection of aldehydes are described in Protective Groups in Organic Synthesis, by T. W. Greene and P. G. M. Wuts, Wiley, 1991, p. 175. The protected aldehyde 161.1 is reacted with an olefinic phosphonate 161.2, in the presence of a palladium (0) catalyst, to afford the coupled product 161.3. Deprotection of the aldehyde group then affords the product 161.6. Alternatively, the unsaturated compound 161.3 is reduced to afford the saturated analog 161.5, which upon deprotection yields the saturated analog 161.7. Methods for the reduction of carbon-carbon double bonds are described, for example, in Comprehensive Organic Transformations, by R. C. Larock, VCH, 1989, p. 6. The methods include catalytic reduction, and chemical reduction, the latter for example employing diborane or diimide.

For example, 5-bromopyridine-3-carboxaldehyde 161.8 (ChemPacific) is converted into the dimethyl acetal, by reaction with methanolic ammonium chloride, as described in J. Org. Chem., 26, 1156, 1961. The acetal 161.9 is then reacted with a dialkyl butenyl phosphonate 161.10, the preparation of which is described in J. Med. Chem., 1996, 39, 949, in the presence of bis(triphenylphosphine)palladium(II) chloride, as described in J. Med. Chem., 1992, 35, 1371, to afford the coupled product 161.11. Deprotection, for example by treatment with formic acid in pentane, as described in Synthesis, 651, 1983, yields the free aldehyde 161.13.

The product is reduced, for example by reaction with diimide, as described in J. Org. Chem., 30, 3965, 1965, to afford the saturated product 161.12.

Using the above procedures, but employing, in place of the aldehyde 161.8, different aldehydes 161.1, and/or different phosphonates 161.2, the corresponding products 161.6 and 161.7 are obtained.

Scheme 162 illustrates the preparation of pyridine aldehydes incorporating a phosphonate group linked to the pyridine by a heteroatom and a carbon chain. In this procedure, a 2- or 4-halo-substituted pyridine aldehyde 162.1 is reacted with a dialkyl hydroxy- or thio-alkylphosphonate 162.2. The preparation of alkoxypyridines by the reaction of alkoxides with halopyridines is described, for example, in J. Am. Chem. Soc., 82, 4414, 1960. The preparation of pyridine thioethers by reaction of halopyridines with thiols is described, for example, in Chemistry of Heterocyclic Compounds, Pyridine and its derivatives, E. Klingsberg, Ed, part 4, p. 358. The alcohols and thiols are transformed into metal salts, for example sodium or potassium salts, and then reacted with the halopyridine substrates at elevated temperatures, optionally in the presence of copper powder catalyst, to afford the ether or thioether products 162.3.

For example, a tetrahydrofuran solution of 2-bromo-pyridine-5-aldehyde 162.4, prepared as described in Tet. Lett., 2001, 42, 4841, is heated at reflux with an equimolar amount of a dialkyl 2-mercaptoethylphophonate 162.5, the preparation of which is described in Aust. J. Chem., 43, 1123, 1990, in the presence of sodium carbonate, to afford the thioether product 162.6.

Using the above procedures, but employing, in place of the haloaldehyde 162.4, different haloaldehydes 162.1, and/or different hydroxy or thio-alkyl phosphonates 162.2, the corresponding products 162.3 are obtained.

Scheme 163 depicts the preparation of pyridine aldehydes 163.3 in which the phosphonate group is attached to the pyridine nucleus by means of a chain incorporating a nitrogen atom. In this procedure, a pyridine dicarboxaldehyde 163.1 is reacted with a dialkyl aminoalkyl phosphonate 163.2, in the presence of a reducing agent, so as to effect a reductive amination reaction, yielding the product 163.3. The preparation of amines by means of reductive amination of aldehydes is described, for example, in Advanced Organic Chemistry, F. A. Carey, R. J. Sundberg, Plenum, 2001, part B, p. 269. The reactants are combined in an inert solvent such as an alcohol or ether, and treated with a reducing agent such as, for example, sodium cyanoborohydride or sodium triacetoxy borohydride, so as to yield the amine product 163.3.

For example, equimolar amounts of pyridine 3,5-dicarboxaldehyde 163.4, prepared as described in Tet. Lett., 1994, 35, 6191, and a dialkyl 2-aminoethyl phosphonate 163.5 prepared as described in J. Org. Chem., 2000, 65, 676, are reacted with sodium cyanoborohydride in isopropanol containing acetic acid, at ambient temperature, so as to produce the amine product 163.6

Using the above procedures, but employing, in place of the dicarboxaldehyde 163.4, different dicarboxaldehydes 163.1, and/or different aminoalkyl phosphonates 163.2, the corresponding products 163.3 are obtained.

Scheme 164 illustrates the incorporation of the formyl or chloromethylpyridines, the syntheses of which are described above, into the piperazine reagent 13.1. Compounds 164.2 in which Z is chloromethyl are reacted with the mono-protected piperazine derivatives 164.1, the preparation of which are described in WO 9711698, to afford the alkylated product 164.3. The preparation of amines by means of alkylation reactions is described, for example, in Comprehensive Organic Transformations, by R. C. Larock, VCH, p. 397. Equimolar amounts of the reactants 164.1 and the halomethylpyridine compound 164.2, are combined in a organic solvent such as an alcohol or dimethylformamide, in the presence of a base such as triethylamine or potassium carbonate, to give the alkylated products 164.3. The alkylation of a piperazine derivative by a 3-chloromethylpyridine is described in WO9628439. Alternatively, the amine 164.1 is reacted with the aldehyde 164.2 to afford the product 164.3 in a reductive alkylation reaction. The preparation of amines by means of reductive amination procedures is described in Scheme 163. In this procedure, the amine component and the aldehyde component are reacted together in the presence of a reducing agent such as, for example, borane, sodium cyanoborohydride or diisobutylaluminum hydride, optionally in the presence of a Lewis acid, such as titanium tetraisopropoxide, as described in J. Org. Chem., 55, 2552, 1990. The reductive alkylation reaction between 3-pyridinecarboxaldehyde and a substituted piperazine is described in WO9628439. Deprotection of the product 164.3 then yields the free amine 13.1.

Scheme 154

Method

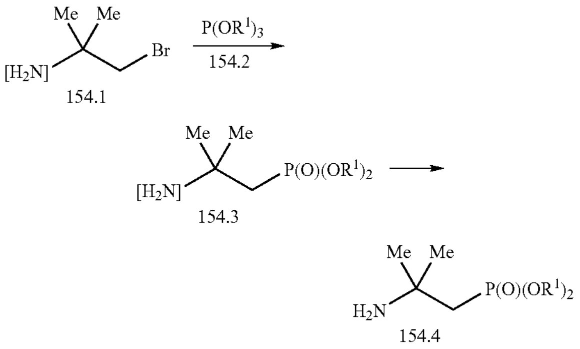

154.1 154.3 154.4

Example

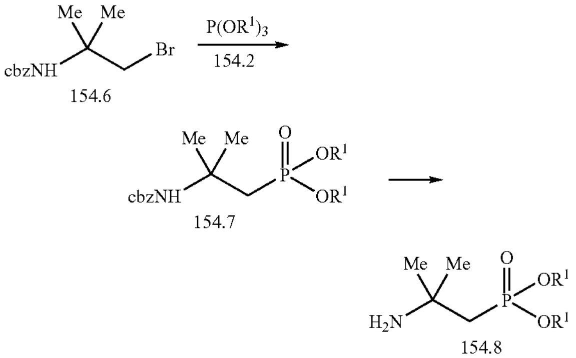

154.6 154.7 154.8

Scheme 155

Method

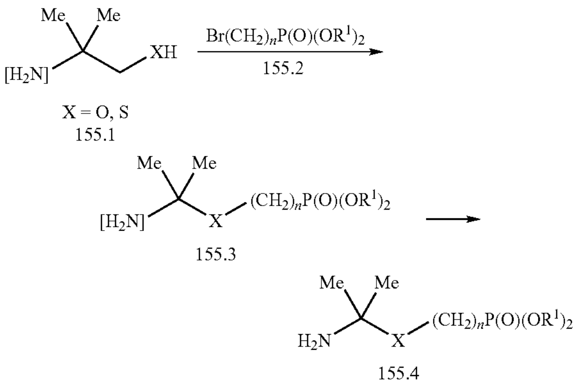

X = O, S
155.1 155.3 155.4

Example

-continued

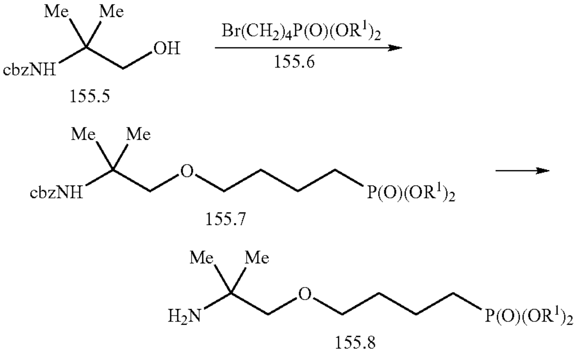

155.5 155.7 155.8

Scheme 156

Method

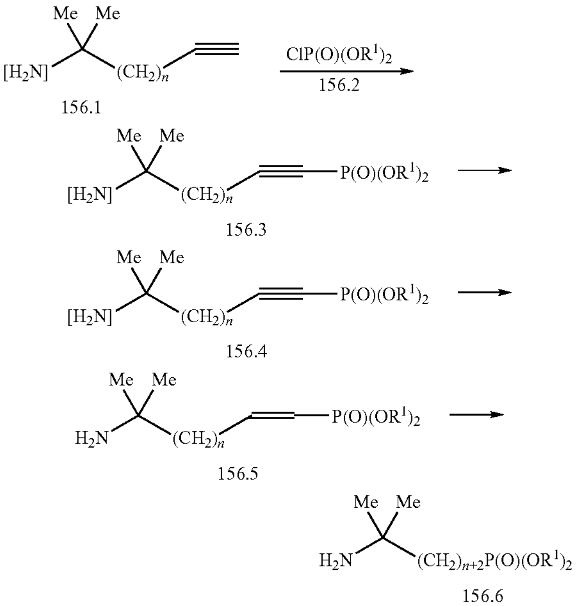

156.1 156.3 156.4 156.5 156.6

Example

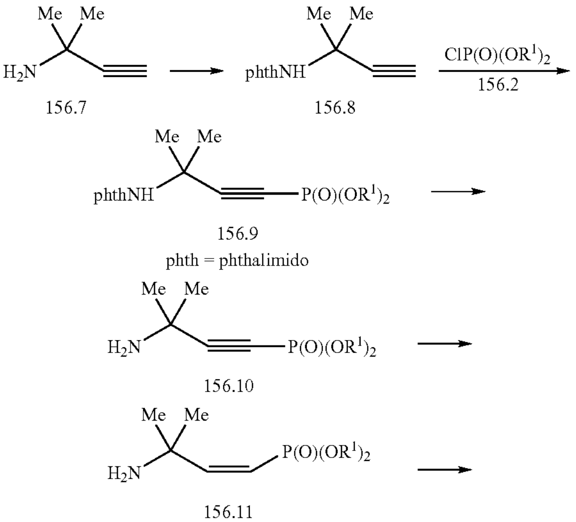

156.7 156.8 156.9 phth = phthalimido 156.10 156.11

-continued
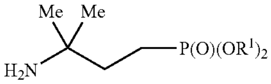
156.12
Scheme 157
Method
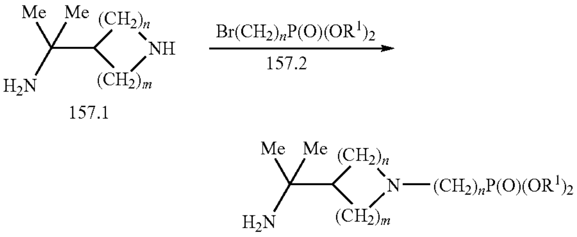
157.1
157.3
Example
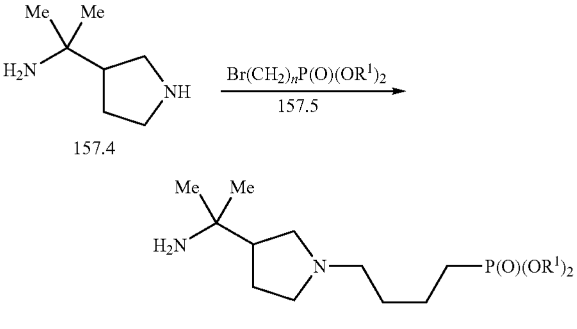
157.4
157.6
Scheme 158
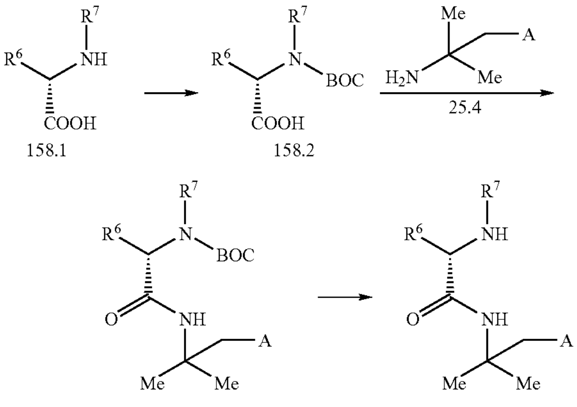
158.1
158.2
158.3
9.3
Scheme 159
Method
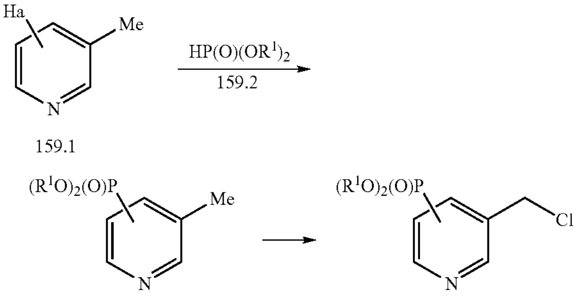
159.1
159.3
159.4
Example
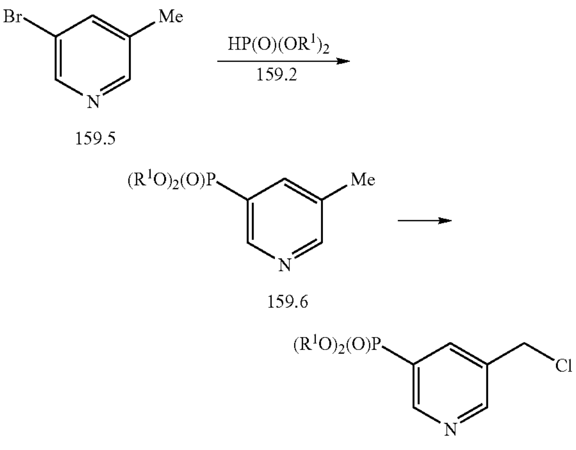
159.5
159.6
159.7
Scheme 160
Method
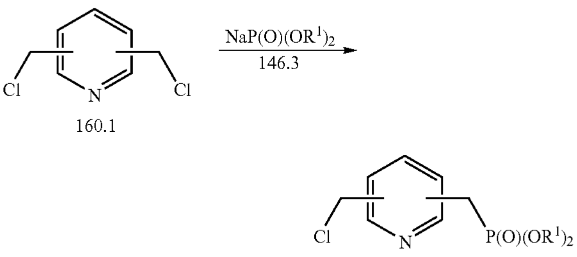
160.1
160.2
Example
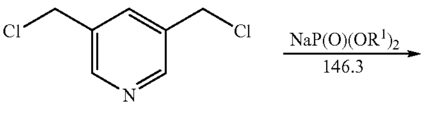
160.3

-continued
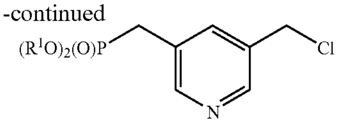
160.4
-continued
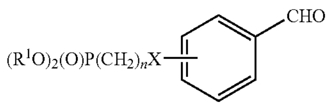
162.3
Scheme 161
Method
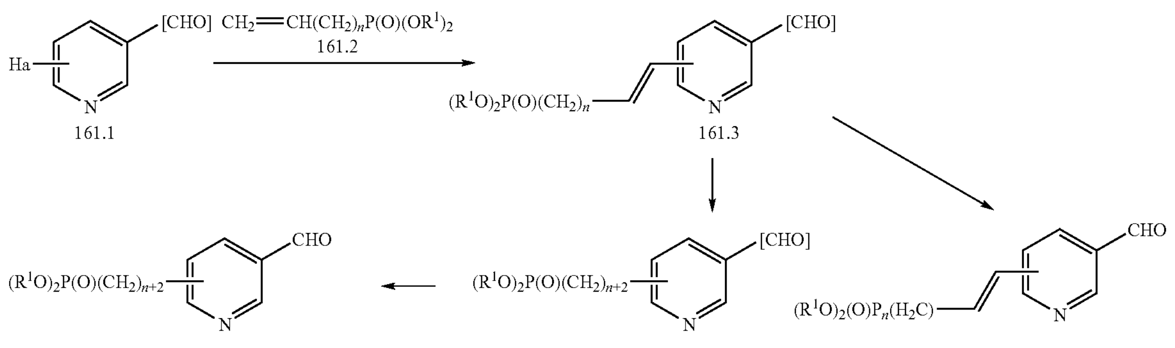
161.1
161.3
161.7
161.5
161.6
Example
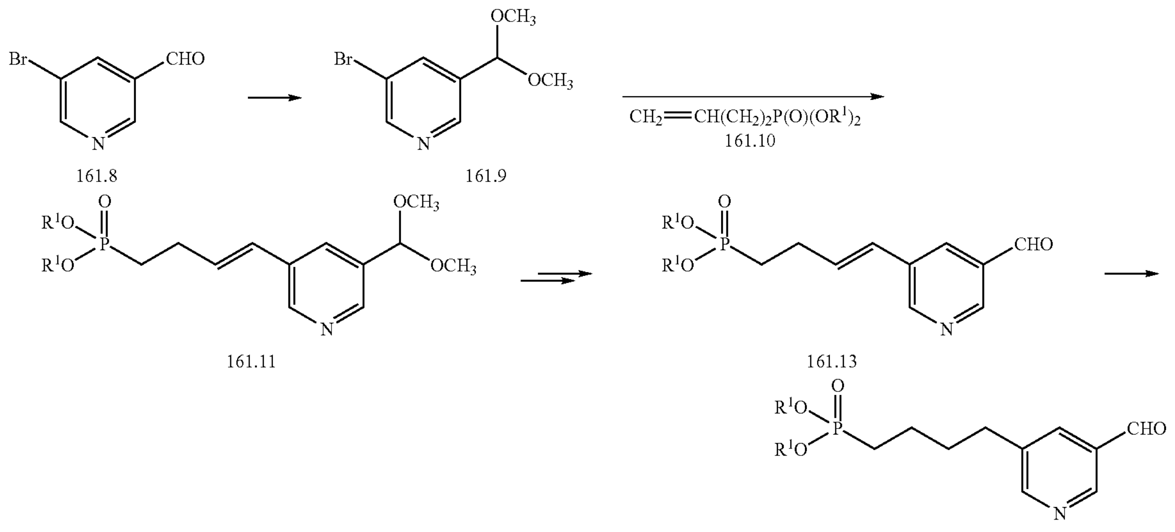
161.8
161.9
161.11
161.13
161.12
Scheme 162
Method
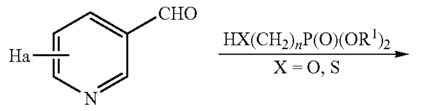
162.1
162.2
-continued
Example
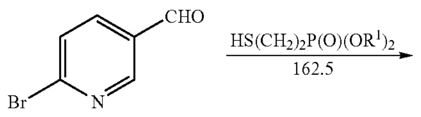
162.4

-continued

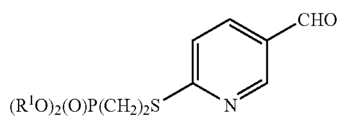

162.6

Scheme 163

Method

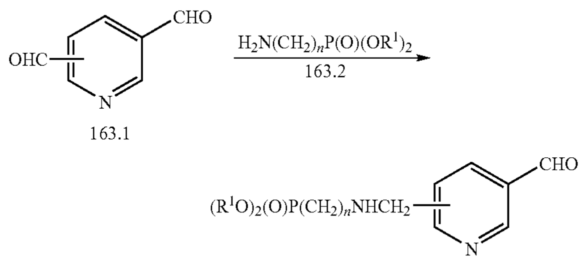

163.1

163.3

Example

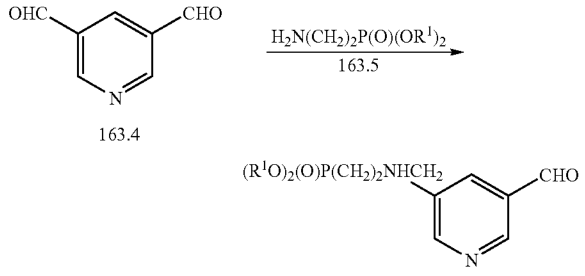

163.4

163.6

Scheme 164

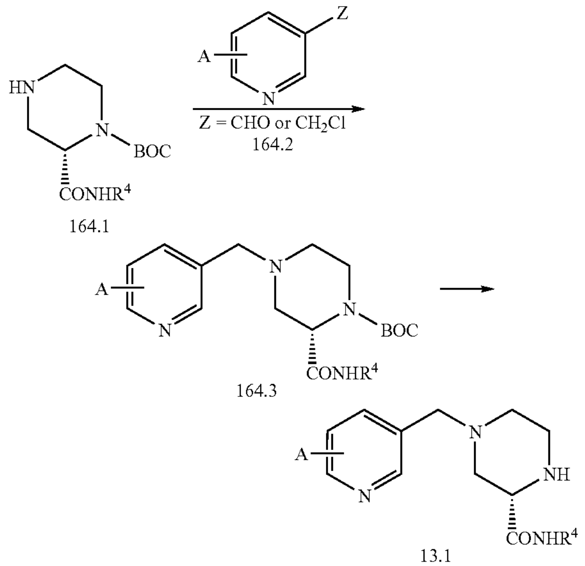

164.1

164.3

13.1

Preparation of Dimethoxybenzyl Halides 49.7 Incorporating Phosphonate Groups.

Schemes 165-169 illustrate the preparation of dimethoxybenzyl halides 49.7 incorporating phosphonate groups, which are employed in the synthesis of the phosphonate esters 6 and 13.

Scheme 165 depicts the preparation of dimethoxybenzyl alcohols in which the phosphonate group is attached either directly to the phenyl ring or by a saturated or unsaturated alkylene chain. In this procedure, a bromo-substituted dimethoxy benzyl alcohol is coupled, in the presence of a palladium catalyst, with a dialkyl alkenyl phosphonate 165.2, to afford the coupled product 165.3. The reaction is conducted under the conditions described in Scheme 150. The product 165.3 is then reduced, for example by treatment with diimide, as described in Scheme 150, to yield the saturated analog 165.4. Alternatively, the bromo compound 165.1 is coupled, in the presence of a palladium catalyst, as described in Scheme 144, with a dialkyl phosphite 165.5, to afford the phosphonate 165.6.

For example, 4-bromo-3,5-dimethoxybenzyl alcohol 165.7, the preparation of which is described in J. Med. Chem., 1977, 20, 299, is coupled with a dialkyl allyl phosphonate 165.8 (Aldrich) in the presence of bis(triphenylphosphine) palladium (II) chloride, as described in J. Med. Chem, 1992, 35, 1371. The reaction is conducted in an aprotic dipolar solvent such as, for example, dimethylformamide, in the presence of triethylamine, at about 100° C. to afford the coupled product 165.9. The product is reduced, for example by treatment with diimide, as described in J. Org. Chem., 52, 4665, 1987, to yield the saturated compound 165.10. Using the above procedures, but employing, in place of the dimethoxy bromobenzyl alcohol 165.7, different benzyl alcohols 165.1, and/or different alkenyl phosphonates 165.2, the corresponding products 165.3 and 165.4 are obtained.

As a further example, 3-bromo-4,5-dimethoxybenzyl alcohol 165.11, the preparation of which is described in J. Org. Chem., 1978, 43, 1580, is coupled, in toluene solution at reflux, with a dialkyl phosphite 165.5, triethylamine and tetrakis(triphenylphosphine)palladium(0), as described in J. Med. Chem., 35, 1371, 1992, to yield the phenyl phosphonate 165.12.

Using the above procedures, but employing, in place of the dimethoxy bromobenzyl alcohol 165.11, different benzyl alcohols 165.1, and/or different dialkyl phosphites 165.5, the corresponding products 165.6 are obtained.

Scheme 166 illustrates the preparation of dimethoxybenzyl alcohols incorporating phosphonate groups attached by means of an amide group. In this procedure, a carboxy-substituted dimethoxybenzyl alcohol 166.1 is coupled, as described in Scheme 1, with a dialkyl aminoalkyl phosphonate 166.2 to prepare the amide 166.3.

For example, 2,6-dimethoxy-4-(hydroxymethyl)benzoic acid 166.4, the preparation of which is described in Chem. Pharm. Bull., 1990, 38, 2118, is coupled in dimethylformamide solution, in the presence of dicyclohexylcarbodiimide, with a dialkyl aminoethyl phosphonate 166.5, the preparation of which is described in J. Org. Chem., 2000, 65, 676, to afford the amide 166.6. Using the above procedures, but employing, in place of the dimethoxybenzoic acid 166.4, different benzoic acids 166.1, and/or different aminoalkyl phosphites 166.2, the corresponding products 166.3 are obtained.

Scheme 167 illustrates the preparation of dimethoxybenzyl alcohols incorporating phosphonate groups attached by means of an aminoalkyl or an amide group. In this procedure, an amino-substituted dimethoxybenzyl alcohol 167.1 is reacted, under reductive amination conditions, as described in Scheme 163, with a dialkyl formylalkylphosphonate 167.2 to yield the aminoalkyl product 167.3. Alternatively, the amino-substituted dimethoxybenzyl alcohol 167.1 is coupled, as described in Scheme 1, with a dialkyl carboxyalkyl phosphonate 167.4, to produce the amide 167.5.

For example, 3-amino-4,5-dimethoxybenzyl alcohol 167.6, the preparation of which is described in Bull. Chem. Soc. Jpn., 1972, 45, 3455, is reacted, in the presence of sodium triacetoxyborohydride, with a dialkyl formylmethyl phosphonate 167.7, as described in Scheme 135, to afford the aminoethyl phosphonate 167.8.

Using the above procedures, but employing, in place of the amine 167.6, different amines 167.1, and/or different formylalkyl phosphites 167.2, the corresponding products 167.3 are obtained.

As a further example, 4-amino-3,5-dimethoxybenzyl alcohol 167.9, the preparation of which is described in Bull. Chem. Soc. Jpn., 1972, 45, 3455, is coupled, in the presence of dicyclohexyl carbodiimide, with a dialkyl phosphonoacetic acid 167.10, (Aldrich) to afford the amide 167.11.

Using the above procedures, but employing, in place of the amine 167.6, different amines 167.1, and/or different carboxyalkyl phosphonates 167.4, the corresponding products 167.5 are obtained.

Scheme 168 illustrates the preparation of dimethoxybenzyl alcohols incorporating phosphonate groups attached by means of an alkoxy group. In this procedure, a dimethoxyhydroxy benzyl alcohol 168.1 is reacted with a dialkyl alkylphosphonate 168.2 with a terminal leaving group to afford the alkoxy product 168.3. The alkylation reaction is effected in a polar organic solvent such as dimethylformamide in the presence of a base such as dimethylaminopyridine or cesium carbonate.

For example, 4-hydroxy-3,5-dimethoxybenzyl alcohol 168.4, the preparation of which is described in J. Med. Chem. 1999, 43, 3657, is reacted in dimethylformamide at 80° C. with an equimolar amount of a dialkyl bromopropyl phosphonate 168.5, prepared as described in J. Am. Chem. Soc., 2000, 122, 1554, and cesium carbonate, to give the alkylated product 168.6. Using the above procedures, but employing, in place of the phenol 168.4, different phenols 168.1, and/or different alkyl phosphonates 168.2, the corresponding products 168.3 are obtained.

As a further example, 4,5-dimethoxy-3-hydroxybenzyl alcohol 168.7, prepared as described in J. Org. Chem., 1989, 54, 4105, is reacted, as described above, with a dialkyl trifluoromethanesulfonyloxymethyl phosphonate 168.8, prepared as described in Tet. Lett., 1986, 27, 1477, to produce the alkylated product 168.9.

Using the above procedures, but employing, in place of the phenol 168.7, different phenols 168.1, and/or different alkyl phosphonates 168.2, the corresponding products 168.3 are obtained.

Scheme 169 illustrates the conversion of the benzyl alcohols 169.1, in which the substituent A is the group link-P(O)$(OR^1)_2$, or a precursor, prepared as described above, into the corresponding halides 169.2. The conversion of alcohols into chlorides, bromides and iodides is described, for example, in Comprehensive Organic Transformations, by R. C. Larock, VCH, 1989, p. 354ff, p. 356ff and p. 358ff. For example, benzyl alcohols are transformed into the chloro compounds, in which Ha is chloro, by reaction with triphenylphosphine and N-chlorosuccinimide, as described in J. Am. Chem. Soc., 106, 3286, 1984. Benzyl alcohols are transformed into bromo compounds by reaction with carbon tetrabromide and triphenylphosphine, as described in J. Am. Chem. Soc., 92, 2139, 1970. Benzyl alcohols are transformed into iodides by reaction with sodium iodide and boron trifluoride etherate, as described in Tet. Lett., 28, 4969, 1987, or by reaction with diphosphorus tetraiodide, as described in Tet. Lett., 1801, 1979. Benzylic chlorides or bromides are transformed into the corresponding iodides by reaction with sodium iodide in acetone or methanol, for example as described in EP 708085.

Preparation of Dimethoxythiophenols 23.1 Incorporating Phosphonate Groups.

Schemes 170-173 illustrate the preparation of the dimethoxythiophenols 23.1 incorporating phosphonate groups, which are used in the synthesis of the phosphonate esters 6 and 13.

Scheme 170 illustrates the preparation of dimethoxythiophenol derivatives incorporating a phosphonate group attached by means of an amide group. In this procedure, a dimethoxyamino-substituted benzoic acid 170.1 is converted into the corresponding thiol 170.2. The conversion of amines into the corresponding thiols is described in Sulfur Lett., 2000, 24, 123. The amine is first converted into the diazonium salt by reaction with nitrous acid. The diazonium salt, preferably the diazonium tetrafluoborate, is reacted in acetonitrile solution with a sulfhydryl ion exchange resin, as described in Sulfur Lett., 2000, 24, 123, to afford the thiol 170.2. The product is then coupled, as described above, with a dialkyl aminoalkyl phosphonate 170.3, to yield the amide 170.4.

For example, 5-amino-2,3-dimethoxybenzoic acid 170.5, the preparation of which is described in JP 02028185, is converted, as described above, into 2,3-dimethoxy-5-mercaptobenzoic acid 170.6. The product is then coupled, as described in Scheme 1, in the presence of dicyclohexyl carbodiimide, with a dialkyl aminopropyl phosphonate 170.7, (Acros) to afford the amide 170.8.

Using the above procedures, but employing, in place of the amine 170.5, different amines 170.1, and/or different aminoalkyl phosphonates 170.3, the corresponding products 170.4 are obtained.

Scheme 171 illustrates the preparation of dimethoxythiophenol derivatives incorporating a phosphonate group attached by means of a saturated or unsaturated alkylene chain. In this procedure, a bromodimethoxyaniline 171.1 is converted, as described in Scheme 170, into the corresponding thiophenol 171.2. The thiol group is then protected to give the derivative 171.3. The protection and deprotection of thiol groups is described in Protective Groups in Organic Synthesis, by T. W. Greene and P. G. M Wuts, Wiley, Second Edition 1990, p. 277. For example, thiol substituents are protected as trialkylsilyloxy groups. Trialkylsilyl groups are introduced by the reaction of the thiophenol with a chlorotrialkylsilane and a base such as imidazole. Alternatively, thiol substituents are protected by conversion to tert-butyl or adamantyl thioethers, or 4-methoxybenzyl thioethers, prepared by the reaction between the thiol and 4-methoxybenzyl chloride in the presence of ammonium hydroxide, as described in Bull. Chem. Soc. Jpn., 37, 433, 1974. The product 171.3 is then coupled, in the presence of a palladium catalyst, as described in Scheme 165, with a dialkyl alkenyl phosphonate 171.4, to give the alkenyl product 171.5. Deprotection then yields the thiol 171.6. Reduction of the double bond, for example by reaction with diimide, as described in J. Org. Chem., 52, 4665, 1987, affords the saturated product 171.7.

For example, 4-bromo-3,5-dimethoxyaniline 171.8, prepared as described in WO9936393, is converted, by diazotization, into 4-bromo-3,5-dimethoxythiophenol 171.9. The product is then transformed into the S-benzoyl derivative 171.10, by reaction with benzoyl chloride in pyridine, and the product is coupled, as described in Scheme 165, with a dialkyl butenyl phosphonate 171.11, the preparation of which is described in J. Med. Chem., 1996, 39, 949, to yield the phosphonate 171.12. Deprotection, for example by treatment with aqueous ammonia at ambient temperature, as described in J. Am. Chem. Soc., 85, 1337, 1963, then afford the thiol 171.13. The double bond is reduced with dllmide to give the saturated analog 171.14.

Using the above procedures, but employing, in place of the amine 171.8, different amines 171.1, and/or different alkenyl phosphonates 171.4, the corresponding products 171.6 and 171.7 are obtained.

Scheme 172 illustrates the preparation of dimethoxythiophenol derivatives incorporating a phosphonate group directly attached to the phenyl ring. In this procedure, a protected bromodimethoxythiophenol 172.1, prepared, for example, from the corresponding aniline, as described above, is coupled, in the presence of a palladium catalyst, as described in Scheme 165, with a dialkyl phosphite 172.2. The product is then deprotected to afford the phosphonate ester 172.4.

For example, 3-bromo-4,5-dimethoxyaniline 172.5, prepared as described in DE 2355394, is converted, as described above in Schemes 165 and 171, into S-benzoyl 3-bromo-4,5-dimethoxythiophenol 172.6. This compound is then coupled, in toluene solution at reflux, with a dialkyl phosphite 172.2, triethylamine and tetrakis(triphenylphosphine)palladium(0), as described in J. Med. Chem., 35, 1371, 1992, to yield the phenyl phosphonate 172.7. Deprotection, as described in Scheme 171, then affords the thiol 172.8.

Using the above procedures, but employing, in place of the protected thiol 172.6, different thiol 172.1, the corresponding products 172.4 are obtained.

Scheme 173 illustrates the preparation of dimethoxythiophenol derivatives incorporating a phosphonate group attached to the phenyl ring by means of an alkoxy group. In this procedure, a dimethoxy aminophenol 173.1 is converted, via the diazo compound, into the corresponding thiophenol 173.2. The thiol group is then protected, and the product 173.3 is alkylated, as described in Scheme 168, with a dialkyl bromoalkyl phosphonate 173.4.

Deprotection of the product 173.5 then affords the thiophenol 173.6.

For example, 5-amino-2,3-dimethoxyphenol 173.7, prepared as described in WO 9841512, is converted by diazotization, as described above, into the thiophenol 173.8, and the product is protected by reaction with one molar equivalent of benzoyl chloride in pyridine, to yield the S-benzoyl product 173.9. The latter compound is then reacted, in dimethylformamide solution at 80° C., with a dialkyl bromoethyl phosphonate 173.10 (Aldrich) and cesium carbonate, to produce the ethoxyphosphonate 173.11. Deprotection, as described in Scheme 171, then yields the thiol 173.12.

Using the above procedures, but employing, in place of the thiol 173.8, different thiol 173.2, and/or different bromoalkyl phosphonates 173.4, the corresponding products 173.6 are obtained.

Scheme 165

Method

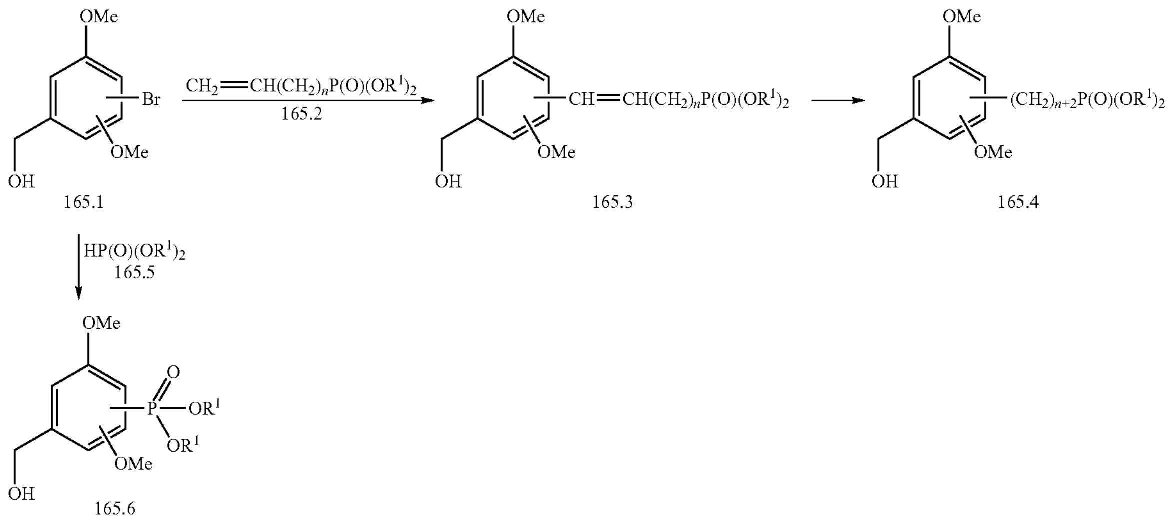

165.1 165.3 165.4 165.6

Example 1

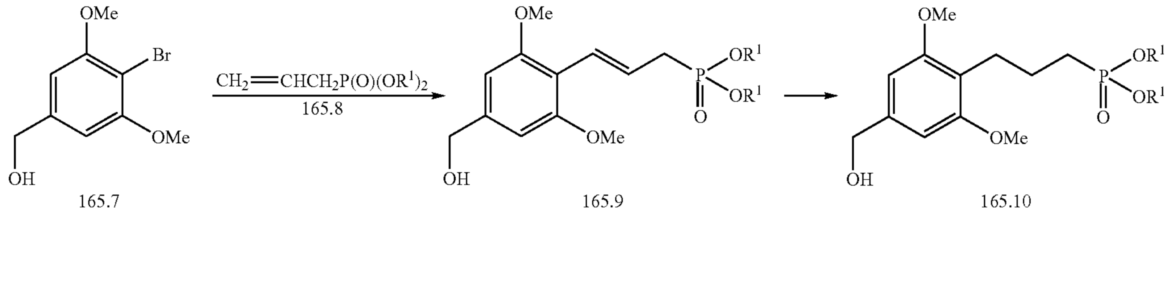

165.7 165.9 165.10

-continued
Example 2
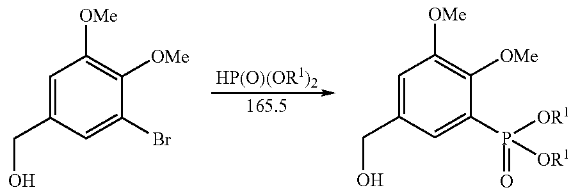
165.11 165.12
Scheme 166
Method
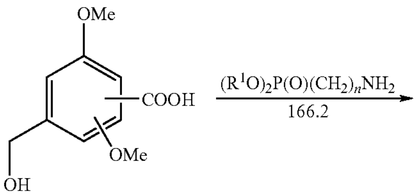
166.1
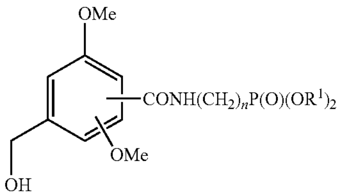
166.3
-continued
Example
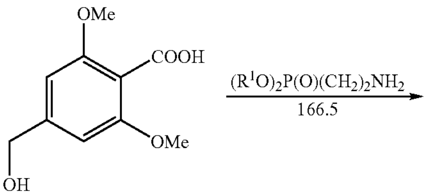
166.4
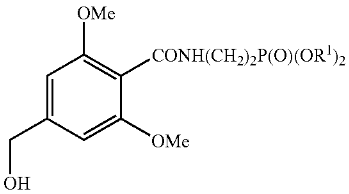
166.6
Scheme 167
Method
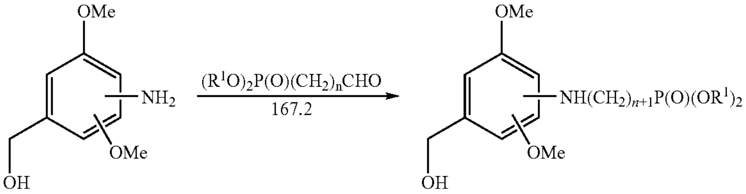
167.1 167.3
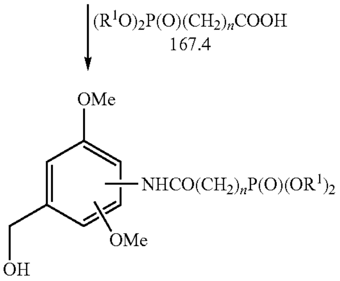
167.5

-continued
Example 1
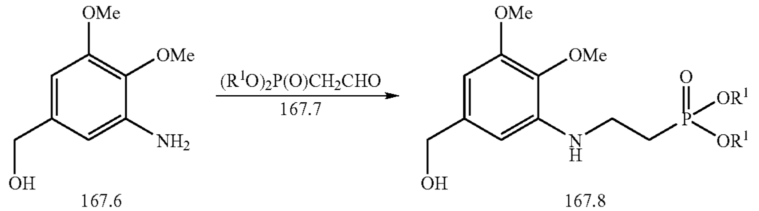
167.6 167.8
Example 2
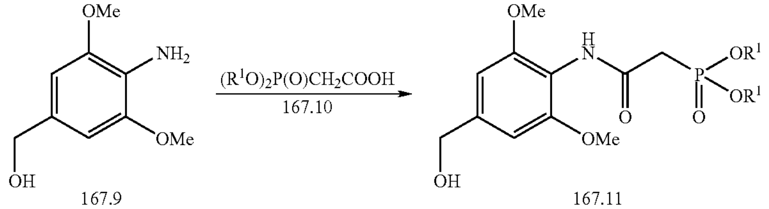
167.9 167.11
Scheme 168
Method
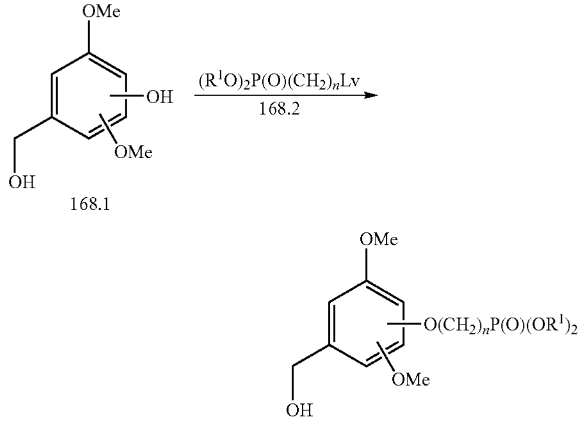
168.1
168.3
Example 1
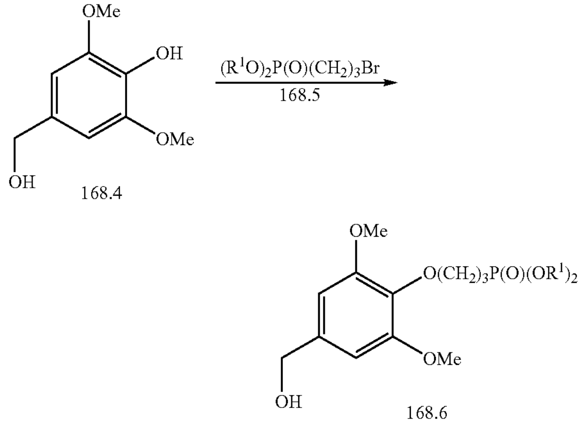
168.4
168.6
-continued
Example 2
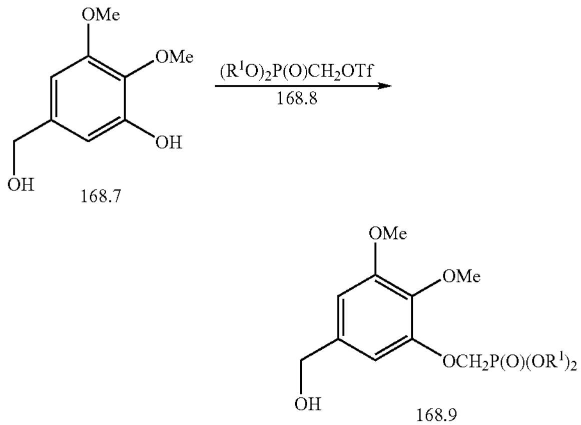
168.7
168.9
Scheme 169
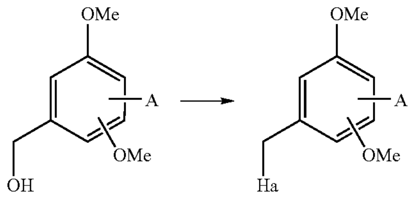
169.1 49.7
Scheme 170
Method -continued
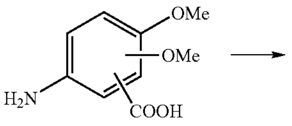
170.1
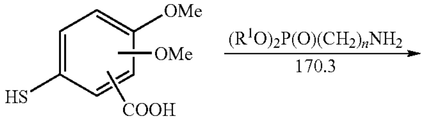
170.2
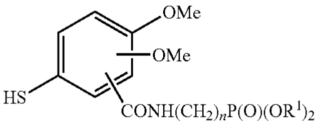
170.4
Example 1
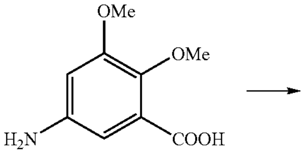
170.5
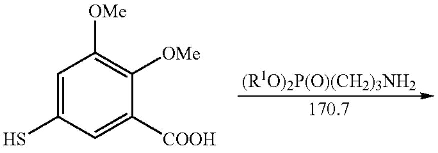
170.6
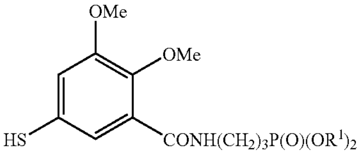
170.8
Scheme 171
Method
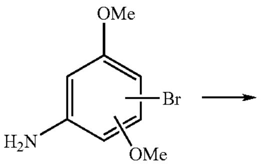
171.1
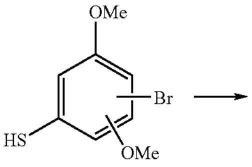
171.2
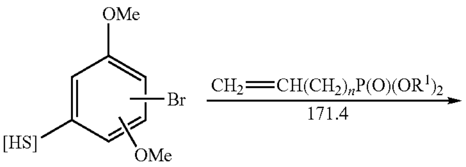
171.3
-continued
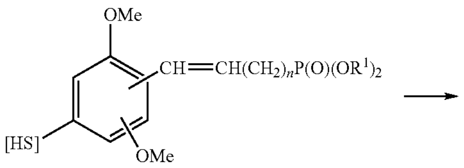
171.5
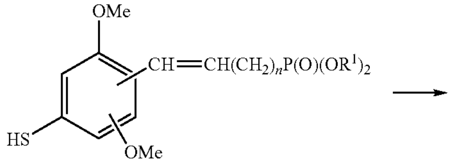
171.6
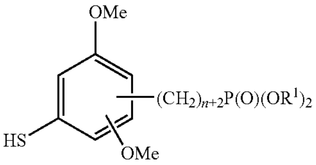
171.7
Example
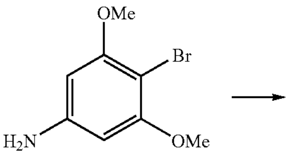
171.8
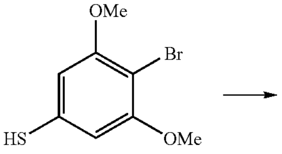
171.9
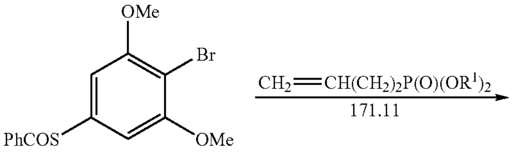
171.10
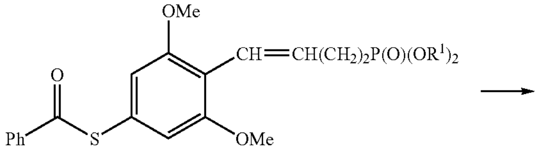
171.12
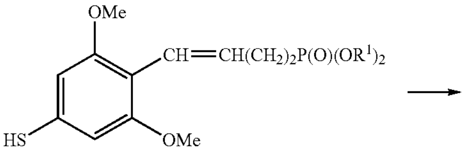
171.13

-continued
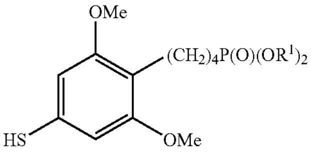
171.14
Scheme 172
Method
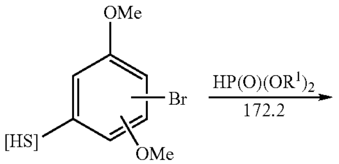
172.1
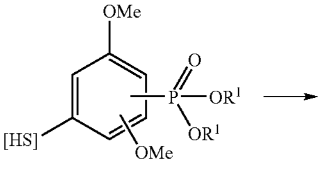
172.3
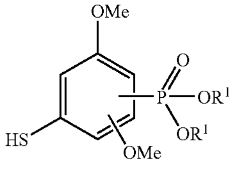
172.4
Example
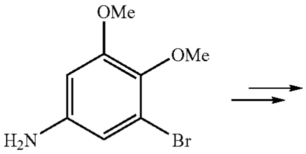
172.5
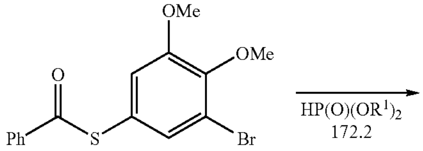
172.6
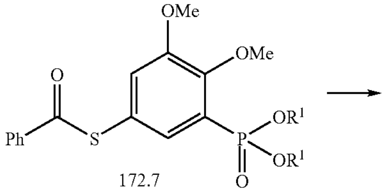
172.7
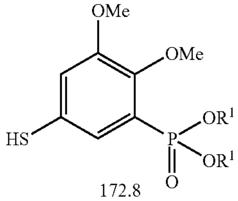
172.8
Scheme 173
Method
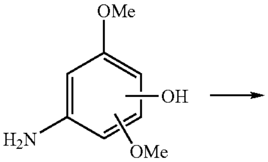
173.1
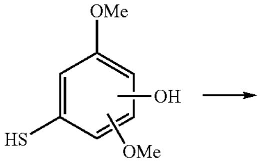
173.2
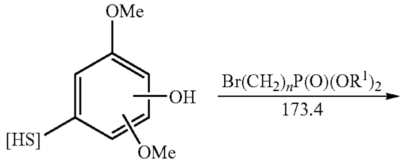
173.3
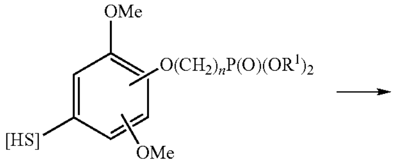
173.5
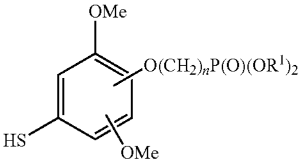
173.6
Example
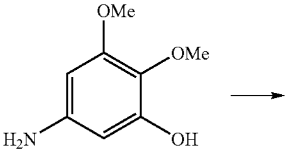
173.7
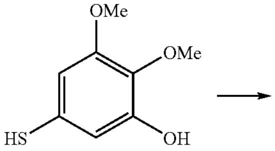
173.8
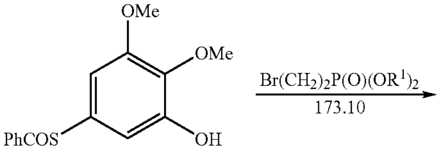
173.9
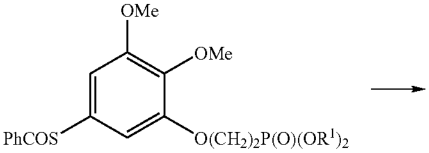
173.11

-continued

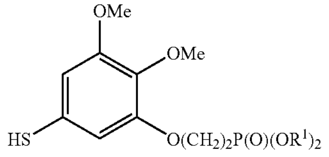

173.12

Preparation of Ethanolaiine Derivatives 29.1 Incorporating Phosphonate Groups.

Schemes 174-178 illustrate the preparation of the ethanolamine derivatives 29.1 which are employed in the preparation of the phosphonate esters 18 and 8.

Scheme 174 illustrates the preparation of ethanolamine derivatives in which the phosphonate group is attached by means of an alkyl chain. In this procedure, ethanolamine 174.1 is protected to give the derivative 174.2. The product is then reacted with a dialkyl alkyl phosphonate 174.3 in which the alkyl group incorporates a leaving group Lv. The alkylation reaction is performed in a polar organic solvent such as acetonitrile or dimethylformamide, in the presence of a strong base such as sodium hydride or lithium hexamethyldisilazide, to afford the ether product 174.4. The protecting group is then removed to yield the amine 174.5. The protection and deprotection of amines is described in Protective Groups in Organic Synthesis, by T. W. Greene and P. G. M Wuts, Wiley, Second Edition 1990, p. 309. The amino compound 174.5 is then coupled, as described in Scheme 1, with the aminoacid 174.6, to give the amide 174.7.

For example, equimolar amounts of phthalimide and ethanolamine are reacted in toluene at 70° C., as described in J. Org. Chem., 43, 2320, 1978, to prepare the phthalimido derivative 174.8, in which Phth is phthalimido. The product is then reacted, in tetrahydrofuran, with sodium hydride and an equimolar amount of a dialkyl trifluoromethylsulfonyloxymethyl phosphonate 174.9, the preparation of which is described in Tet. Lett., 1986, 27, 1497, to afford the ether product 174.10. The phthalimido group is then removed by treatment of the product 174.10 with ethanolic hydrazine at ambient temperature, as described in J. Org. Chem., 43, 2320, 1978, to yield the amine 174.11. The product is then coupled, in the presence of dicyclohexylcarbodiimide, with the aminoacid 174.6, to yield the amide 174.12. Using the above procedures, but employing, in place of the methylphosphonate 174.9, different alkylphosphonates 174.3, the corresponding products 174.7 are obtained.

Scheme 175 illustrates the preparation of ethanolamine derivatives in which the phosphonate group is attached by means of an alkylene chain incorporating a nitrogen. In this procedure, ethanolamine 174.1 and the aminoacid 174.6 are coupled, as described in Scheme 1, to form the amide 175.1. The product is then alkylated with a bromoalkyl aldehyde 175.2 to yield the ether 175.3. The alkylation reaction is performed in a polar organic solvent such as acetonitrile or dioxan, in the presence of a strong base such as potassium tert. butoxide or sodium hydride, at about 60° C. The aldehyde product is then reacted, under reductive amination conditions, as described in Scheme 135, with a dialkyl aminoalkyl phosphonate 175.4, to produce the amine product 175.5.

For example, the amide 175.1 is reacted, as described above, with bromoacetaldehyde 175.6, to afford the ether 175.7. The product is then reacted in ethanol with a dialkyl aminoethyl phosphonate 175.8, (Aurora) and sodium triacetoxyborohydride, to yield the amine 175.9.

Using the above procedures, but employing, in place of the bromoacetaldehyde 175.6, different bromoalkyl aldehydes 175.2, and/or different aminoalkyl phosphonates 175.4, the corresponding products 175.5 are obtained.

Scheme 176 illustrates the preparation of ethanolamine derivatives in which the phosphonate group is attached by means of a phenyl ring. In this procedure, bromoethylamine 176.1 and the aminoacid 174.6 are coupled, as described in Scheme 1, to afford the amide 176.2. The product is then reacted with the dialkyl hydroxyalkyl-substituted phenylphosphonate 176.3 to prepare the ether 176.4. The alkylation reaction is performed in a polar organic solvent such as dimethyl sulfoxide or dioxan, in the presence of a base such as lithium bis(trimethylsilyl)amide, sodium hydride or lithium piperidide.

For example, the amide 176.2 is reacted in dimethylformamide with a dialkyl 4-(2-hydroxyethyl)phenyl phosphonate 176.5, prepared as described in J. Am. Chem. Soc., 1996, 118, 5881, and sodium hydride, to furnish the ether product 176.6.

Using the above procedures, but employing, in place of the hydroxyethyl phenylphosphonate 176.5, different phosphonates 176.3, the corresponding products 176.4 are obtained.

Scheme 177 illustrates the preparation of ethanolamine derivatives in which the phosphonate group is attached by means of an alkylene chain. In this procedure, the aminoacid 174.6 is coupled with a bromoalkoxy-substituted ethylamine 177.1 to give the amide 177.2. The product is then subjected to an Arbuzov reaction with a trialkyl phosphite $P(OR^1)_3$. In this procedure, described in Handb. Organophosphorus Chem., 1992, 115, the reactants are heated together at ca. 100° C. to afford the product 177.4.

For example, the aminoacid 174.6 is coupled, as described in Scheme 1, in acetonitrile solution containing dicyclohexylcarbodiimide, with 2-bromoethoxyethylamine 177.5, prepared as described in Vop. Khim. Tekh., 1974, 34, 6, to produce the amide 177.6. The product is then heated at 120° C. with excess trialkyl phosphite 177.3, to afford the phosphonate 177.7. Using the above procedures, but employing, in place of the bromoethoxyethylamine 177.5, different bromoalkyl ethylamines 177.1, the corresponding products 177.4 are obtained.

Scheme 178 depicts the preparation of the amines 29.1. The BOC-protected ethanolamine derivatives 178.1, in which the group A is either the substituent link-$P(O)(OR^1)_2$, or a precursor thereto, prepared as described in Schemes 174-177, are deprotected to afford the amines 29.1. The removal of BOC protecting groups is described, for example, in Protective Groups in Organic Synthesis, by T. W. Greene and P. G. M Wuts, Wiley, Second Edition 1990, p. 328. The deprotection is effected by treatment of the BOC compound with anhydrous acids, for example, hydrogen chloride in ethyl acetate, or trifluoroacetic acid, or by reaction with trimethylsilyl iodide or aluminum chloride.

Preparation of the Chroman Phosphonate Esters 33.1.

Schemes 179-181a illustrate the preparation of the chroman phosphonate esters 33.1 which are employed in the preparation of the phosphonate esters 17 and 9.

Scheme 179 depicts the preparation of (2-methyl-3a,9b-dihydro-4H-chromeno[4,3-d]oxazol-4-yl)-methanol, 179.6, 2-methyl-3a,9b-dihydro-4H-chromeno[4,3-d]oxazole-4-carbaldehyde, 179.7, and 2-methyl-3a,9b-dihydro-4H-chromeno[4,3-d]oxazole-4-carboxylic acid, 179.8, which are used in the preparation of the phosphonates 33.1. In this procedure, (2H-chromen2-yl)-methanol 179.1, prepared as described in J. Chem. Soc., (D), 344, 1973, is converted, as described above, (Scheme 1) into the tert. butyldimethylsilyl ether 179.2. The product is then reacted, as described in J. Het. Chem., 1975, 12, 1179, with silver cyanate and iodine in ether, so as to afford the addition product 179.3. This compound is then heated on methanol to yield the carbamate derivative 179.4. The latter compound is heated in xylene at reflux, as described in J. Het. Chem., 1975, 12, 1179, to produce the oxazoline derivative 179.5. The silyl group is then removed by reaction with tetrabutylanimonium fluoride in tetrahydrofuran to yield the carbinol 179.6. The carbinol is oxidized to produce the aldehyde 179.7. The conversion of alcohols to aldehydes is described, for example, in Comprehensive Organic Transformations, by R. C. Larock, VCH, 1989, p. 604ff. The alcohol is reacted with an oxidizing agent such as pyridinium chlorochromate, silver carbonate, dimethyl sulfoxide/acetic anhydride or dimethyl sulfoxide-dicyclohexyl carbodiimide. The reaction is conducted in an inert aprotic solvent such as dichloromethane or toluene. The aldehyde 179.7 is oxidized to the carboxylic acid 179.8. The oxidation of aldehydes to carboxylic acids is described in Comprehensive Organic Transformations, by R. C. Larock, VCH, 1989, p. 838ff. The conversion is effected by treatment with oxidizing agents such as potassium permanganate, ruthenium tetroxide, chromium trioxide in acetic acid, or, preferably, by the use of silver oxide, as described in J. Am. Chem. Soc., 73, 2590, 1951.

Scheme 180 illustrates the preparation of chroman derivatives in which the phosphonate group is attached by means of an aminoalkyl chain. In this procedure, the aldehyde 179.7 is reacted, under reductive amination conditions, as described in Scheme 175, with a dialkyl aminoalkyl phosphonate 180.1, to give the amine 180.2. The oxazoline group is then hydrolyzed, for example by reaction with aqueous potassium hydroxide, as described in J. Het. Chem., 1975, 12, 1179, to yield the hydroxyamine 180.3.

For example, the aldehyde 179.7 is reacted in ethanol with a dialkyl aminomethyl phosphonate 180.4, (Interchim) and sodium triacetoxyborohydride, to produce the amine 180.5. The oxazoline is then hydrolyzed, as described above, to afford the hydroxyamine 180.6. Using the above procedures, but employing, in place of the aminomethyl phosphonate 180.4, different phosphonates 180.1, the corresponding products 180.3 are obtained.

Scheme 181 illustrates the preparation of chroman derivatives in which the phosphonate group is attached by means of an amide group. In this procedure, the carboxylic acid 179.8 is coupled, as described in Scheme 1, with a dialkyl aminoalkyl phosphonate 180.1, to produce the amide 181.1. Hydrolysis of the oxazoline group, as described above, then yields the hydroxyamine 181.2.

For example, the carboxylic acid 179.8 is coupled with a dialkyl aminopropyl phosphonate 181.3, (Acros) to afford the amide 181.4, which is then hydrolyzed to give the hydroxyamine 181.5.

Using the above procedures, but employing, in place of the aminopropyl phosphonate 181.3, different phosphonates 180.1, the corresponding products 181.2 are obtained.

Scheme 181a illustrates the preparation of chroman derivatives in which the phosphonate group is attached by means of a thioalkyl group. In this procedure, the carbinol 179.6 is converted into the bromo derivative 181a.1. The conversion of alcohols into bromides is described, for example, in Comprehensive Organic Transformations, by R. C. Larock, VCH, 1989, p. 356ff. For example, the alcohol is reacted with triphenyl phosphine and carbon tetrabromide, trimethylsilyl bromide, thionyl bromide and the like. The bromo compound is then reacted with a dialkyl thioalkyl phosphonate 181a.2 to effect displacement of the bromide and formation of the thioether 181a.3. The reaction is performed in a polar organic solvent such as ethanol in the presence of a base such as potassium carbonate. Removal of the isoxazoline group then produces the hydroxyamine 181a.4.

For example, the bromo compound 181a.1 is reacted in ethanol with a dialkyl thioethyl phosphonate 181a.5, prepared as described in Zh. Obschei. Khim., 1973, 43, 2364, and potassium carbonate, to yield the thioether product 181a.6. Hydrolysis, as described above, then affords the hydroxyamine 181a.7.

Using the above procedures, but employing, in place of the thioethyl phosphonate 181a.5, different phosphonates 181a.2, the corresponding products 181a.4 are obtained.

Scheme 174

Method

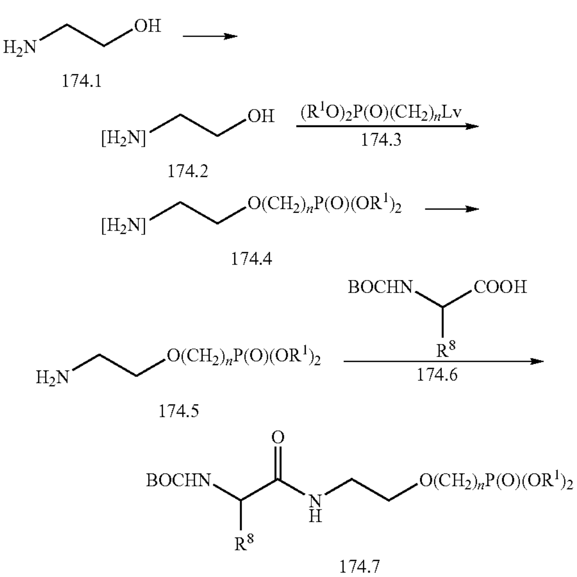

174.1, 174.2, 174.4, 174.5, 174.7

Example

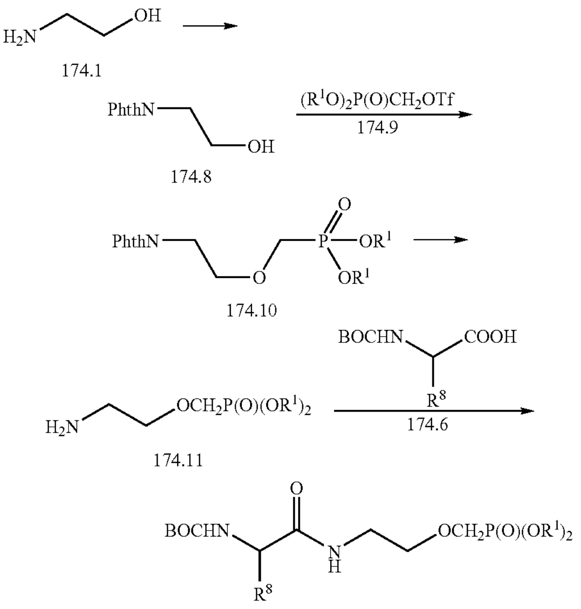

174.1, 174.8, 174.10, 174.11, 174.12

Scheme 175
Method
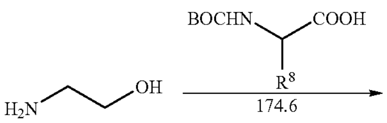
174.1
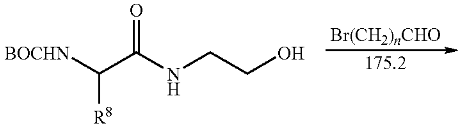
175.1
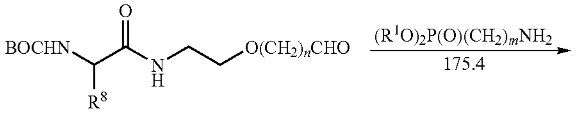
175.3
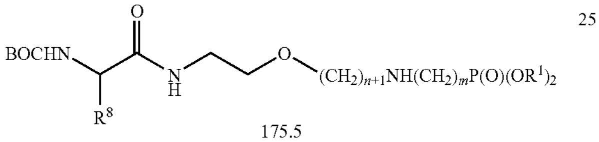
175.5
Example
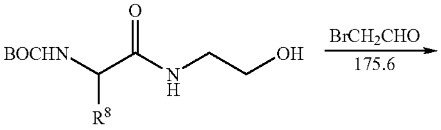
175.1
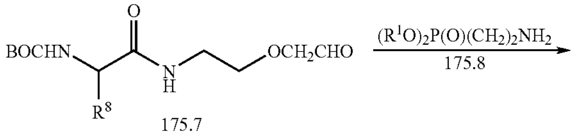
175.7
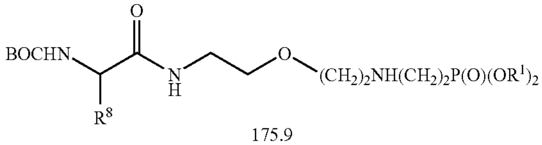
175.9
Scheme 176
Method
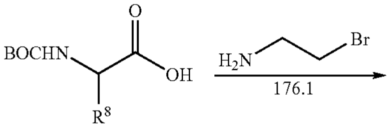
174.6
-continued
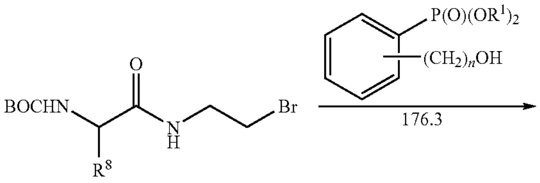
176.2
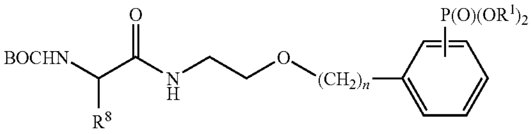
176.4
Example
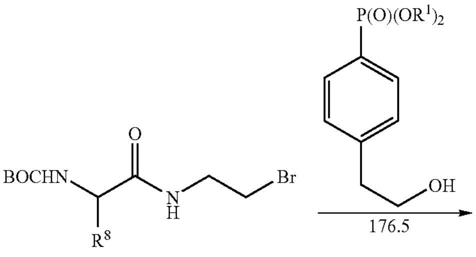
176.2
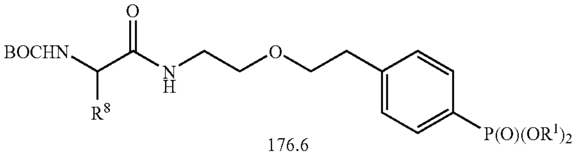
176.6
Scheme 177
Method
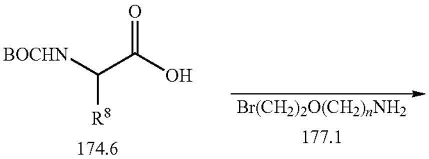
174.6
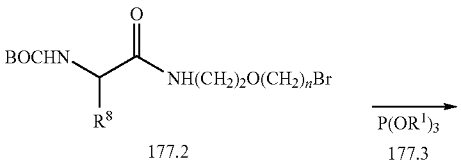
177.2
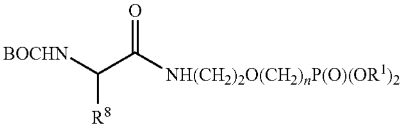
177.4

-continued
Example
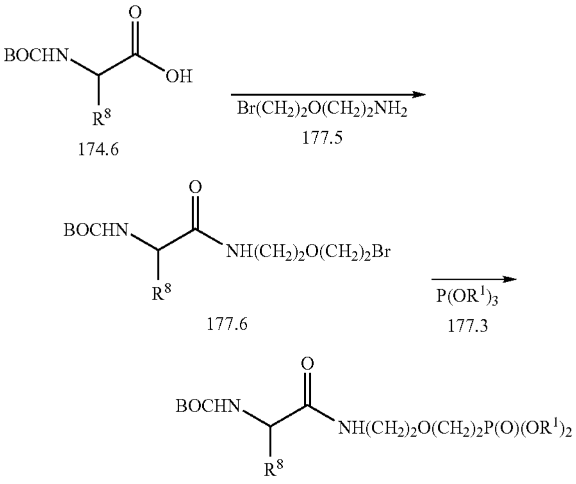
174.6
177.6
177.7
Scheme 178
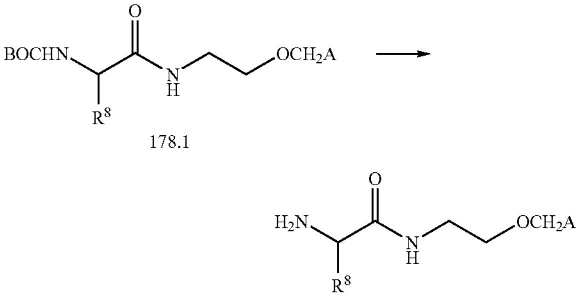
178.1
29.1
Scheme 179
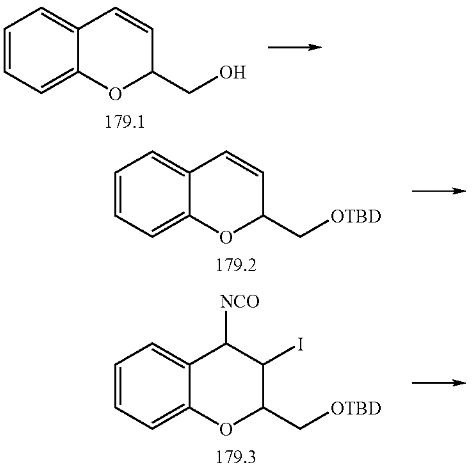
179.1
179.2
179.3
-continued
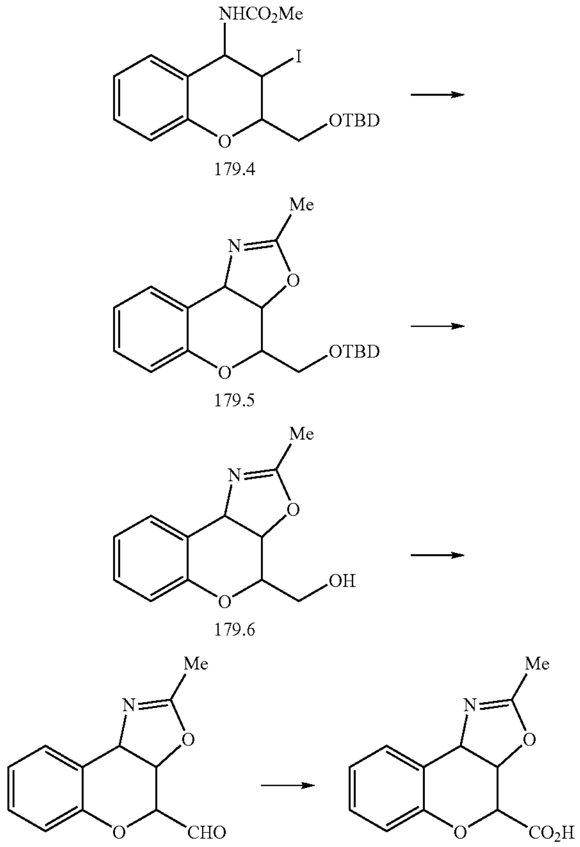
179.4
179.5
179.6
179.7
179.8
Scheme 180
Method
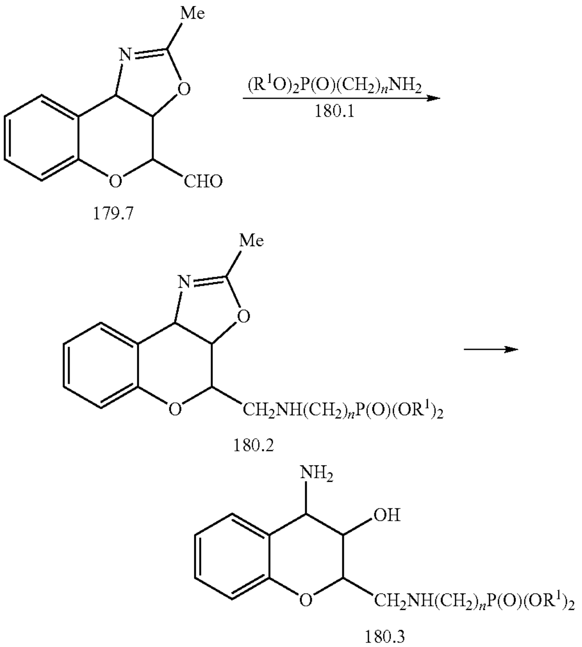
179.7
180.2
180.3

-continued
Example
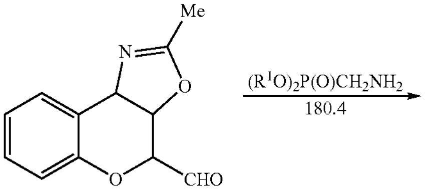
179.7
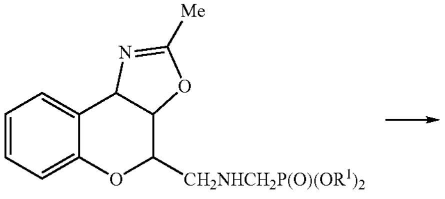
180.5
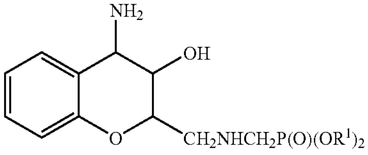
180.6
-continued
Example
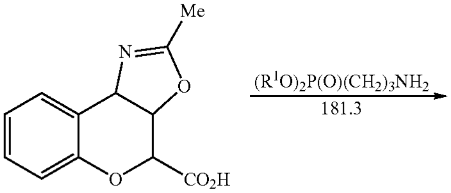
179.8
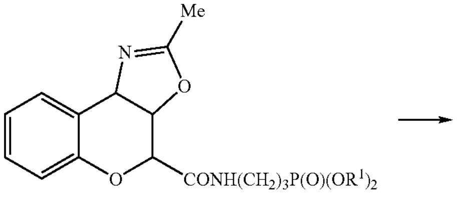
181.4
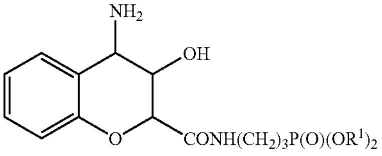
181.5
Scheme 181
Method
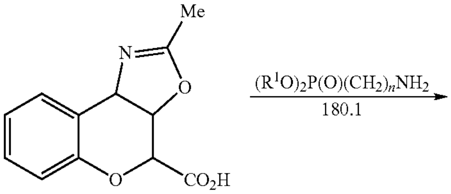
179.8
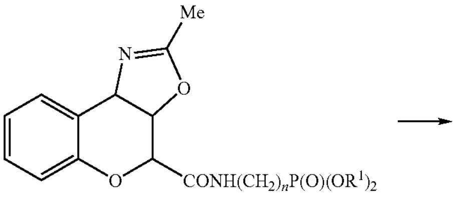
181.1
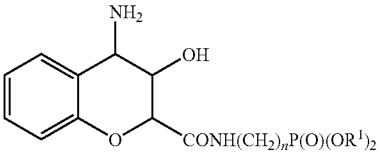
181.2
Scheme 181a
Method
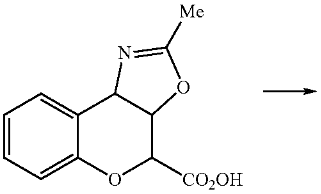
179.6
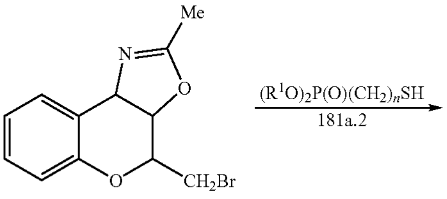
181a.1
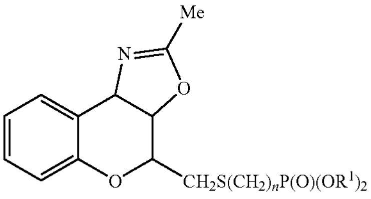
181a.3

-continued

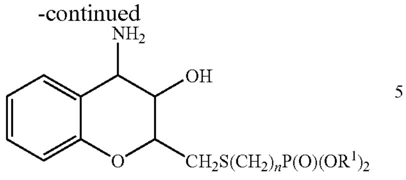

181a.4

Example

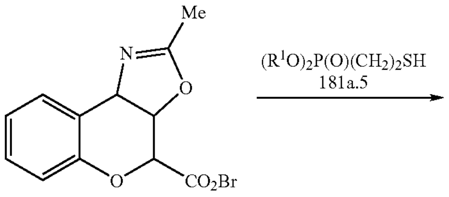

181a.1

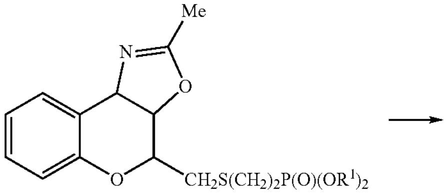

181a.6

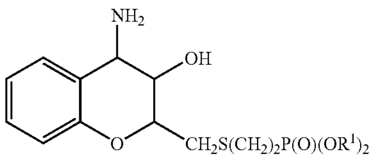

181a.7

Preparation of Phenylalanine Derivatives 37.1 Incorporating Phosphonate Moieties.

Schemes 182-185 illustrate the preparation of phosphonate-containing phenylalanine derivatives 37.1 which are employed in the preparation of the intermediate phosphonate esters 10 and 19.

Scheme 182 illustrates the preparation of phenylalanine derivatives incorporating phosphonate moieties attached to the phenyl ring by means of a heteroatom and an alkylene chain. The compounds are obtained by means of alkylation or condensation reactions of hydroxy or mercapto-substituted phenylalanine derivatives 182.1.

In this procedure, a hydroxy or mercapto-substituted phenylalanine is converted into the benzyl ester 182.2. The conversion of carboxylic acids into esters is described for example, in Comprehensive Organic Transformations, by R. C. Larock, VCH, 1989, p. 966. The conversion is effected by means of an acid-catalyzed reaction between the carboxylic acid and benzyl alcohol, or by means of a base-catalyzed reaction between the carboxylic acid and a benzyl halide, for example benzyl chloride. The hydroxyl or mercapto substituent present in the benzyl ester 182.2 is then protected. Protection methods for phenols and thiols are described respectively, for example, in Protective Groups in Organic Synthesis, by T. W. Greene and P. G. M Wuts, Wiley, Second Edition 1990, p. 10, p. 277. For example, suitable protecting groups for phenols and thiophenols include tert-butyldimethylsilyl or tert-butyldiphenylsilyl. Thiophenols are also protected as S-adamantyl groups, as described in Protective Groups in Organic Synthesis, by T. W. Greene and P. G. M Wuts, Wiley, Second Edition 1990, p. 289. The protected hydroxy- or mercapto ester 182.3 is then converted into the BOC derivative 182.4. The protecting group present on the O or S substituent is then removed. Removal of O or S protecting groups is described in Protective Groups in Organic Synthesis, by T. W. Greene and P. G. M Wuts, Wiley, Second Edition 1990, p. 10, p. 27[7]. For example, silyl protecting groups are removed by treatment with tetrabutylammonium fluoride, in a solvent such as tetrahydrofuran at ambient temperature, as described in J. Am. Chem. Soc., 94, 6190, 1972. S-Adamantyl groups are removed by treatment with mercuric trifluoroacetate in acetic acid, as described in Chem. Pharm. Bull., 26, 1576, 1978. The resultant phenol or thiophenol 182.5 is then reacted under various conditions to provide protected phenylalanine derivatives 182.9, 182.10 or 182.11, incorporating phosphonate moieties attached by means of a heteroatom and an alkylene chain.

In this step, the phenol or thiophenol 182.5 is reacted with a dialkyl bromoalkyl phosphonate 182.6 to afford the ether or thioether product 182.9. The alkylation reaction is effected in the presence of an organic or inorganic base, such as, for example, diazabicyclononene, cesium carbonate or potassium carbonate. The reaction is performed at from ambient temperature to ca. 80° C., in a polar organic solvent such as dimethylformamide or acetonitrile, to afford the ether or thioether product 182.9. Deprotection of the benzyl ester group, for example by means of catalytic hydrogenation over a palladium catalyst, then yields the carboxylic acid 182.12. The benzyl esters 182.10 and 182.11, the preparation of which is described above, are similarly deprotected to produce the corresponding carboxylic acids.

For example, as illustrated in Scheme 182, Example 1, a hydroxy-substituted phenylalanine derivative such as tyrosine, 182.13 is converted, as described above, into the benzyl ester 182.14. The latter compound is then reacted with one molar equivalent of chloro tert-butyldimethylsilane, in the presence of a base such as imidazole, as described in J. Am. Chem. Soc., 94, 6190, 1972, to afford the silyl ether 182.15. This compound is then converted, as described above, into the BOC derivative 182.16. The silyl protecting group is removed by treatment of the silyl ether 182.16 with a tetrahydrofuran solution of tetrabutylammonium fluoride at ambient temperature, as described in J. Am. Chem. Soc., 94, 6190, 1972, to afford the phenol 182.17. The latter compound is then reacted in dimethylformamide at ca. 60° C., with one molar equivalent of a dialkyl 3-bromopropyl phosphonate 182.18 (Aldrich), in the presence of cesium carbonate, to afford the alkylated product 182.19. Debenzylation then produces the carboxylic acid 182.20.

Using the above procedures, but employing, in place of the hydroxy-substituted phenylalanine derivative 182.13, different hydroxy or thio-substituted phenylalanine derivatives 182.1, and/or different bromoalkyl phosphonates 182.6, the corresponding ether or thioether products 182.12 are obtained.

Alternatively, the hydroxy or mercapto-substituted phenylalanine derivative 182.5 is reacted with a dialkyl hydroxymethyl phosphonate 182.7 under the conditions of the Mitsonobu reaction, to afford the ether or thioether compounds 182.10. The preparation of aromatic ethers and thioethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the ether or thioether products 182.10.

For example, as shown in Scheme 182, Example 2,3-mercaptophenylalanine 182.21, prepared as described in WO 0036136, is converted, as described above, into the benzyl ester 182.22. The resultant ester is then reacted in tetrahydrofuran solution with one molar equivalent of 4-methoxybenzyl chloride in the presence of ammonium hydroxide, as described in Bull. Chem. Soc. Jpn., 37, 433, 1974, to afford the 4-methoxybenzyl thioether 182.23. This compound is then converted into the BOC-protected derivative 182.24. The 4-methoxybenzyl group is then removed by the reaction of the thioether 182.24 with mercuric trifluoroacetate and anisole in trifluoroacetic acid, as described in J.Org. Chem., 52, 4420, 1987, to afford the thiol 182.25. The latter compound is reacted, under the conditions of the Mitsonobu reaction, with a dialkyl hydroxymethyl phosphonate 182.7, diethylazodicarboxylate and triphenylphosphine, for example as described in Synthesis, 4, 327, 1998, to yield the thioether product 182.26. The benzyl ester protecting group is then removed to afford the carboxylic acid 182.27.

Using the above procedures, but employing, in place of the mercapto-substituted phenylalanine derivative 182.21, different hydroxy or mercapto-substituted phenylalanines 182.1, and/or different dialkyl hydroxymethyl phosphonates 182.7, the corresponding products 182.10 are obtained.

Alternatively, the hydroxy or mercapto-substituted protected phenylalanine derivative 182.5 is reacted with an activated derivative of a dialkyl hydroxymethylphosphonate 182.8 in which Lv is a leaving group. The components are reacted together in a polar aprotic solvent such as, for example, dimethylformamide or dioxan, in the presence of an organic or inorganic base such as triethylamine or cesium carbonate, to afford the ether or thioether products 182.11. For example, as illustrated in Scheme 182, Example 3,3-hydroxyphenylalanine 182.28 (Fluka) is converted, using the procedures described above, into the protected compound 182.29. The latter compound is reacted, in dimethylformamide at ca. 50° C., in the presence of potassium carbonate, with diethyl trifluoromethanesulfonyloxymethylphosphonate 182.30, prepared as described in Tet. Lett., 1986, 27, 1477, to afford the ether product 182.31. Debenzylation then produces the carboxylic acid 182.32.

Using the above procedures, but employing, in place of the hydroxy-substituted phenylalanine derivative 182.28, different hydroxy or mercapto-substituted phenylalanines 182.1, and/or different dialkyl trifluoromethanesulfonyloxymethylphosphonates 182.8, the corresponding products 182.11 are obtained.

Scheme 183 illustrates the preparation of phenylalanine derivatives incorporating phosphonate moieties attached to the phenyl ring by means of an alkylene chain incorporating a nitrogen atom. The compounds are obtained by means of a reductive alkylation reaction between a formyl-substituted protected phenylalanine derivative 183.3 and a dialkyl aminoalkylphosphonate 183.4.

In this procedure, a hydroxymethyl-substituted phenylalanine 183.1 is converted, as described above, into the BOC protected benzyl ester 183.2. The latter compound is then oxidized to afford the corresponding aldehyde 183.3. The conversion of alcohols to aldehydes is described, for example, in Comprehensive Organic Transformations, by R. C. Larock, VCH, 1989, p. 604ff. Typically, the alcohol is reacted with an oxidizing agent such as pyridinium chlorochromate, silver carbonate, or dimethyl sulfoxide/acetic anhydride, to afford the aldehyde product 183.3. For example, the carbinol 183.2 is reacted with phosgene, dimethyl sulfoxide and triethylamine, as described in J. Org. Chem., 43, 2480, 1978, to yield the aldehyde 183.3. This compound is reacted with a dialkyl aminoalkylphosphonate 183.4 in the presence of a suitable reducing agent to afford the amine product 183.5. The preparation of amines by means of reductive amination procedures is described, for example, in Comprehensive Organic Transformations, by R. C. Larock, VCH, p. 421, and in Advanced Organic Chemistry, Part B, by F. A. Carey and R. J. Sundberg, Plenum, 2001, p. 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The benzyl protecting group is then removed to prepare the carboxylic acid 183.6.

For example, 3-(hydroxymethyl)-phenylalanine 183.7, prepared as described in Acta Chem. Scand. Ser. B, 1977, B31, 109, is converted, as described above, into the formylated derivative 183.8. This compound is then reacted with a dialkyl aminoethylphosphonate 183.9, prepared as described in J. Org. Chem., 200, 65, 676, in the presence of sodium cyanoborohydride, to produce the alkylated product 183.10, which is then deprotected to give the carboxylic acid 183.11.

Using the above procedures, but employing, in place of 3-(hydroxymethyl)-phenylalanine 183.7, different hydroxymethyl phenylalanines 183.1, and/or different aminoalkyl phosphonates 183.4, the corresponding products 183.6 are obtained.

Scheme 184 depicts the preparation of phenylalanine derivatives in which a phosphonate moiety is attached directly to the phenyl ring. In this procedure, a bromo-substituted phenylalanine 184.1 is converted, as described above, (Scheme 182) into the protected derivative 184.2. The product is then coupled, in the presence of a palladium(0) catalyst, with a dialkyl phosphite 184.3 to produce the phosphonate ester 184.4. The preparation of arylphosphonates by means of a coupling reaction between aryl bromides and dialkyl phosphites is described in J. Med. Chem., 35, 1371, 1992. The product is then deprotected to afford the carboxylic acid 184.5.

For example, 3-bromophenylalanine 184.6, prepared as described in Pept. Res., 1990, 3, 176, is converted, as described above, (Scheme 182) into the protected compound 184.7. This compound is then reacted, in toluene solution at reflux, with diethyl phosphite 184.8, triethylamine and tetrakis(triphenylphosphine)palladium(0), as described in J. Med. Chem., 35, 1371, 1992, to afford the phosphonate product 184.9. Debenzylation then yields the carboxylic acid 184.10.

Using the above procedures, but employing, in place of 3-bromophenylalanine 184.6, different bromophenylalanines 184.1, and/or different dialkylphosphites 184.3, the corresponding products 184.5 are obtained.

Scheme 185 depicts the preparation of the aminoacid derivative 37.1 which is employed in the preparation of the phosphonate esters 10 and 19. In this procedure, the BOC-protected phenylalanine derivatives 185.1, in which the substituent A is the group link-$P(O)(OR^1)_2$ or a precursor group, the preparation of which is described in Schemes 182-184, is converted into the esters or amides 185.2 in which $R^9$ is morpholino or alkoxy. The transformation is accomplished by coupling the acid, as described in Scheme 1, with morpholine or an alkanol in the presence of a carbodiimide. The product 185.2 is then deprotected to afford the free amine 185.3, for example as described in Scheme 3. The amine 185.3 is then coupled, as described in Scheme 1, with the aminoacid 174.6, to give the amide 185.4. The BOC group is then removed, as described in Scheme 49, to produce the amine 37.1.

Preparation of the Dimethoxyphenylpropionic Esters 21.1 Incorporating Phosphonate Groups.

Scheme 186 illustrates the preparation of the dimethoxyphenylpropionic acid derivatives 21.1 which are employed in the preparation of the phosphonate esters 6. In this procedure, the dimethoxybenzyl alcohol derivative 186.1, in which the substituent A is the group link-$P(O)(OR^1)_2$ or a precursor group, the preparation of which is described in Schemes 165-168, is converted into the corresponding aldehyde 186.2. The oxidation is effected as described in Scheme 175. The aldehyde is then subjected to a Wittig reaction with methyl triphenylphosphoranylideneacetate 138.2, as described in Scheme 138, to generate the cinnamic ester derivative 186.3. The double bond is then reduced, as described in Scheme 138, to afford the phenylpropionic ester 21.1. Alternatively, the dimethoxybenzyl bromide derivative 186.4, the preparation of which is described in Scheme 169, is reacted, as described in Scheme 138, with dimethyl malonate 186.5 to yield the malonic ester derivative 186.6, which is then transformed, as described in Scheme 138, into the ester 21.1.

Preparation of the Phosphonate-containing Benzyl Iodides 58.1 and Benzylcarbamates 125.3.

Schemes 187-191 illustrate methods for the preparation of the benzyl iodide derivatives 58.1 which are employed in the synthesis of the phosphonate esters 14, and of the benzyl carbamates 125.3 which are employed in the preparation of the phosphonate esters 22.

Scheme 187 illustrates the preparation of benzaldehyde phosphonates 187.3 in which the phosphonate group is attached by means of an alkylene chain incorporation a nitrogen atom. In this procedure, a benzene dialdehyde 187.1 is reacted with one molar equivalent of a dialkyl aminoalkyl phosphonate 187.2, under reductive amination conditions, as describe above in Scheme 135, to yield the phosphonate product 187.3.

For example, benzene-1,3-dialdehyde 187.4 is reacted with a dialkyl aminopropyl phosphonate 187.5, (Acros) and sodium triacetoxyborohydride, to afford the product 187.6.

Using the above procedures, but employing, in place of benzene-1,3-dicarboxaldehyde 187.4, different benzene dialdehydes 187.1, and/or different phosphonates 187.2, the corresponding products 187.3 are obtained.

Scheme 188 illustrates the preparation of benzaldehyde phosphonates either directly attached to the benzene ring or attached by means of a saturated or unsaturated carbon chain. In this procedure, a bromobenzaldehyde 188.1 is coupled, under palladium catalysis as described in Scheme 150, with a dialkyl alkenylphosphonate 188.2, to afford the alkenyl phosphonate 188.3. Optionally, the product is reduced, as described in Scheme 150, to afford the saturated phosphonate ester 188.4. Alternatively, the bromobenzaldehyde is coupled, as described in Scheme 144, with a dialkyl phosphite 188.5 to afford the formylphenylphosphonate 188.6. For example, as shown in Example 1,3-bromobenzaldehyde 188.7 is coupled with a dialkyl propenylphosphonate 188.8 (Aldrich) to afford the propenyl product 188.9. Optionally, the product is reduced, as described in Scheme 150, to yield the propyl phosphonate 188.10.

Using the above procedures, but employing, in place of 3-bromobenzaldehyde 188.7, different bromobenzaldehydes 188.1, and/or different alkenyl phosphonates 188.2, the corresponding products 188.3 and 188.4 are obtained.

Alternatively, as shown in Example 2,4-bromobenzaldehyde 188.11 is coupled, as described in Scheme 144, with a dialkyl phosphite 188.5 to afford the 4-formylphenyl phosphonate product 188.12.

Using the above procedures, but employing, in place of 4-bromobenzaldehyde 188.11, different bromobenzaldehydes 188.1, the corresponding products 188.6 are obtained.

Scheme 189 illustrates the preparation of formylphenyl phosphonates in which the phosphonate moiety is attached by means of alkylene chains incorporating two heteroatoms O, S or N. In this procedure, a formyl phenoxy, phenylthio or phenylamino alkanol, alkanethiol or alkylamine 189.1 is reacted with a an equimolar amount of a dialkyl haloalkyl phosphonate 189.2, to afford the phenoxy, phenylthio or phenylamino phosphonate product 189.3. The alkylation reaction is effected in a polar organic solvent such as dimethylformamide or acetonitrile, in the presence of a base. The base employed depends on the nature of the nucleophile 189.1. In cases in which Y is O, a strong base such as sodium hydride or lithium hexamethyldisilazide is employed. In cases in which Y is S or N, a base such as cesium carbonate or dimethylaminopyridine is employed.

For example, 2-(4-formylphenylthio)ethanol 189.4, prepared as described in Macromolecules, 1991, 24, 1710, is reacted in acetonitrile at 60° C. with one molar equivalent of a dialkyl iodomethyl phosphonate 189.5, (Lancaster) to give the ether product 189.6.

Using the above procedures, but employing, in place of the carbinol 189.4, different carbinols, thiols or amines 189.1, and/or different haloalkyl phosphonates 189.2, the corresponding products 189.3 are obtained.

Scheme 190 illustrates the preparation of formylphenyl phosphonates in which the phosphonate group is linked to the benzene ring by means of an aromatic or heteroaromatic ring. In this procedure, a formylbenzeneboronic acid 190.1 is coupled, in the presence of a palladium catalyst, with one molar equivalent of a dibromoarene, 190.2, in which the group Ar is an aromatic or heteroaromatic group. The coupling of aryl boronates with aryl bromides to afford diaryl compounds is described in Palladium Reagents and Catalysts, by J. Tsuji, Wiley 1995, p. 218. The components are reacted in a polar solvent such as dimethylformamide in the presence of a palladium(0) catalyst and sodium bicarbonate. The product 190.3 is then coupled, as described above (Scheme 144) with a dialkyl phosphite 190.4 to afford the phosphonate 190.5.

For example, 4-formylbenzeneboronic acid 190.6 is coupled with 2,5-dibromothiophene 190.7 to yield the phenylthiophene product 190.8. This compound is then coupled with the dialkyl phosphite 190.4 to afford the thienyl phosphonate 190.9.

Using the above procedures, but employing, in place of dibromothiophene 190.7, different dibromoarenes 190.2, and/or different formylphenyl boronates 190.1, the corresponding products 190.5 are obtained.

Scheme 191 illustrates the preparation of the benzyl carbamates 125.3 and the benzyl iodides 58.1, which are employed respectively in the preparation of the phosphonate esters 22 and 4. In this procedure, the substituted benzaldehydes 191.1, prepared as shown in Schemes 187-190, are converted into the corresponding benzyl alcohols 191.2. The reduction of aldehydes to afford alcohols is described in Comprehensive Organic Transformations, by R. C. Larock, VCH, 1989, p. 527ff. The transformation is effected by the use of reducing agents such as sodium borohydride, lithium aluminum tri-tertiarybutoxy hydride, diisobutyl aluminum hydride and the like. The resultant benzyl alcohol is then reacted with the aminoester 191.3 to afford the carbamate 191.4. The reaction is performed under the conditions described below, Scheme 198. For example, the benzyl alcohol is reacted with carbonyldiimidazole to produce an intermediate benzyloxycarbonyl imidazole, and the intermediate is reacted with the aminoester 191.3 to afford the carbamate 191.4. The methyl ester is then hydrolyzed, as described in Scheme 3, to yield the carboxylic acid 125.3. Alternatively, the benzyl alcohol 191.2 is converted, using the procedures of Scheme 169, into the iodide 58.1.

Scheme 182

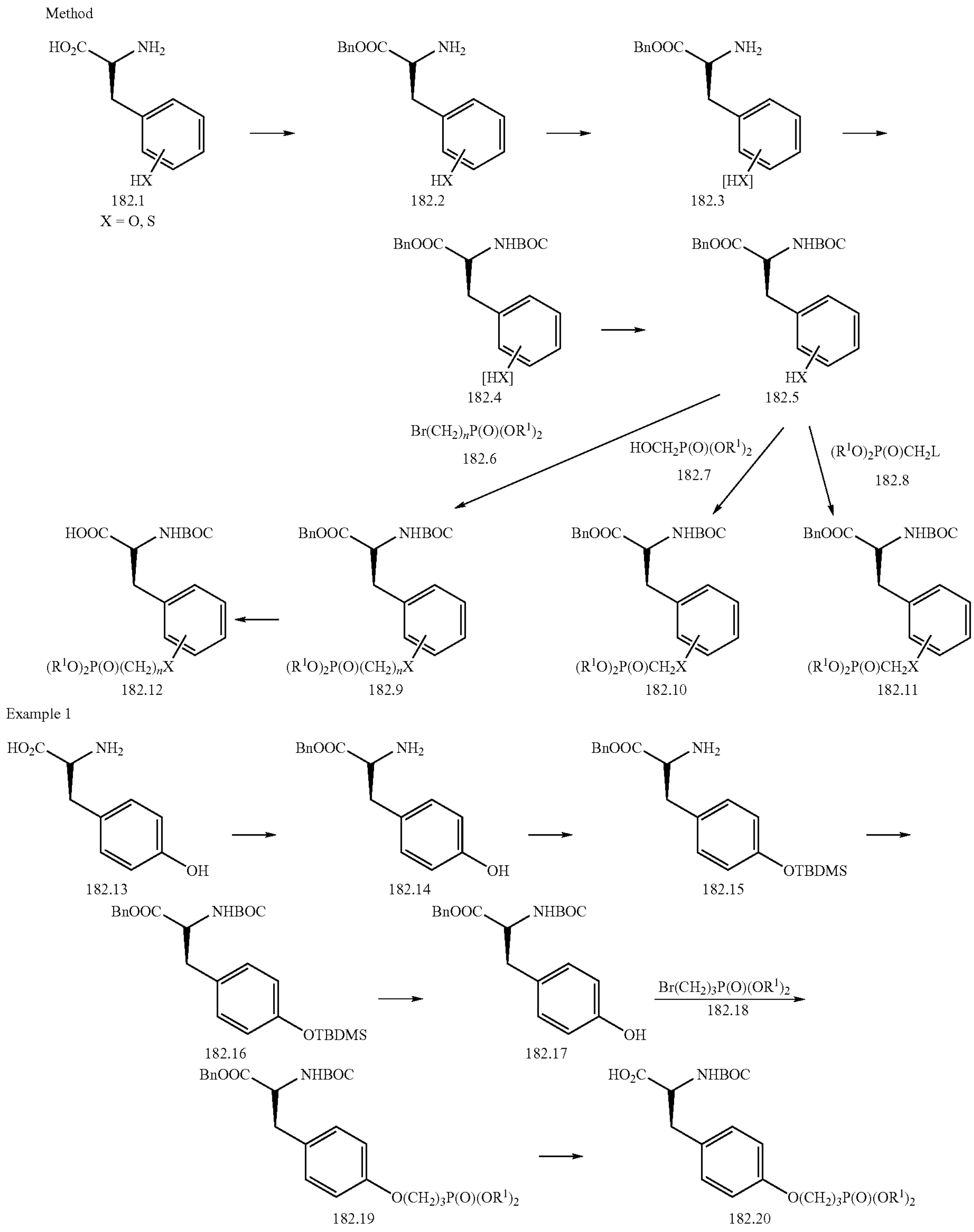

-continued
Example 2
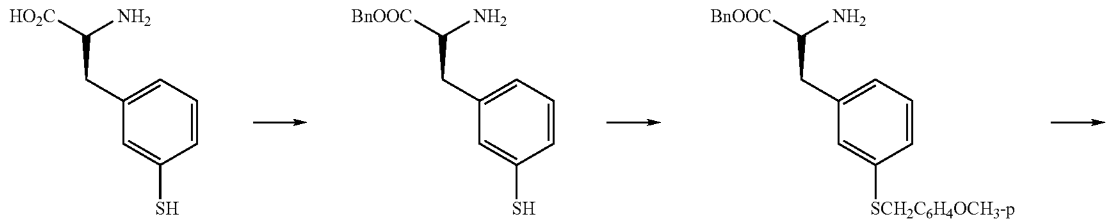
182.21 182.22 182.23
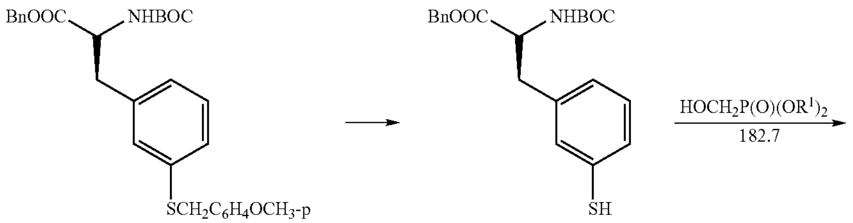
182.24 182.25
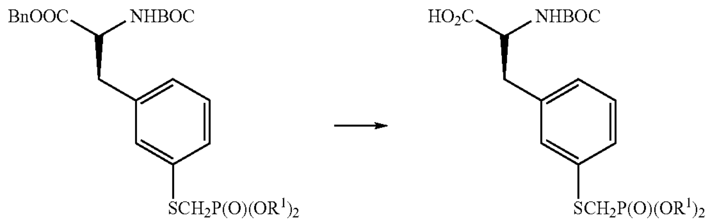
182.26 182.27
Example 3
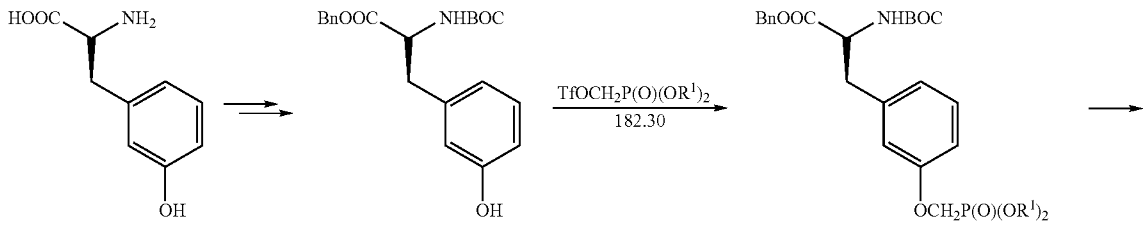
182.28 182.29 182.31
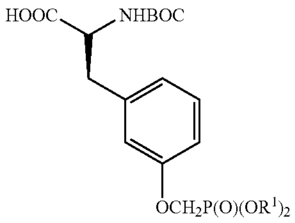
182.32

Scheme 183
Method
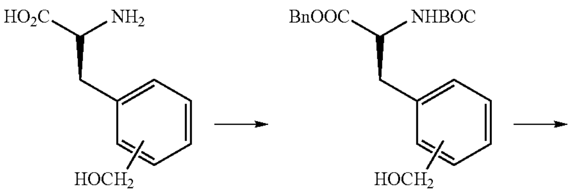
183.1 183.2
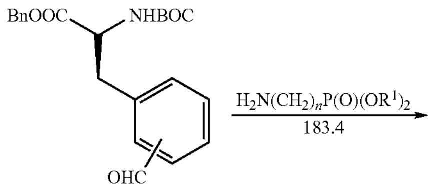
183.3
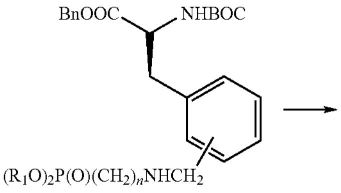
183.5
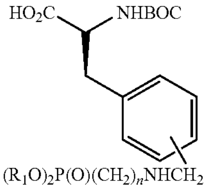
183.6
Example
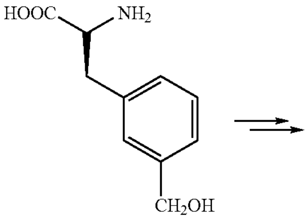
183.7
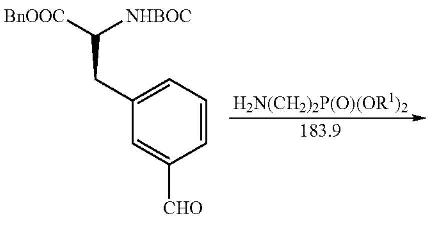
183.8
-continued
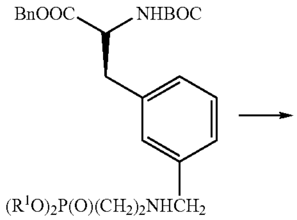
183.10
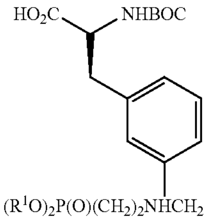
183.11
Scheme 184
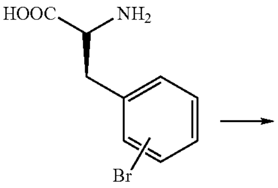
184.1
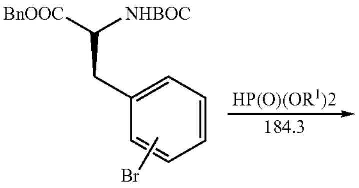
184.2
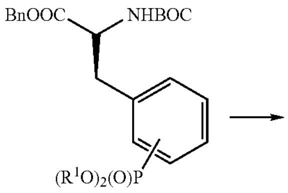
184.4
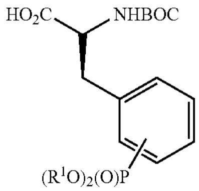
184.5

-continued
Example
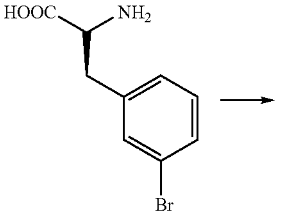
184.6
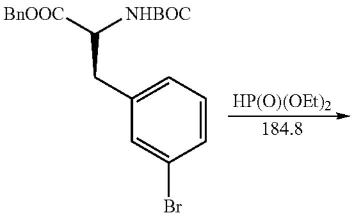
184.7
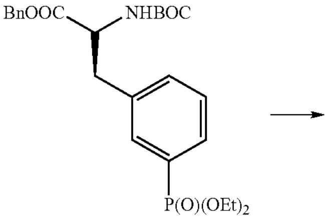
184.9
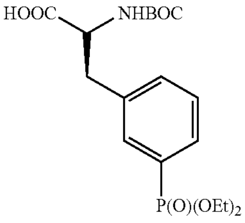
184.10
Scheme 185
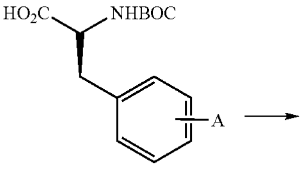
185.1
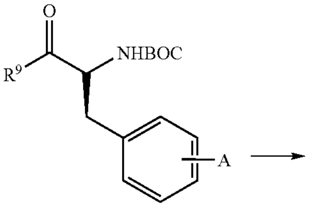
185.2
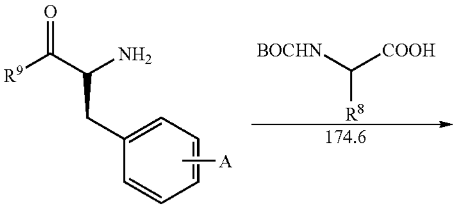
185.3
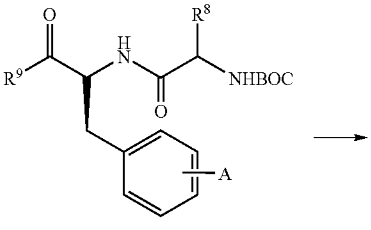
185.4
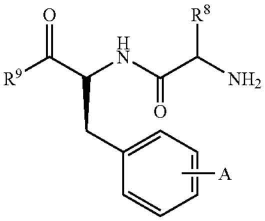
37.1

Scheme 186
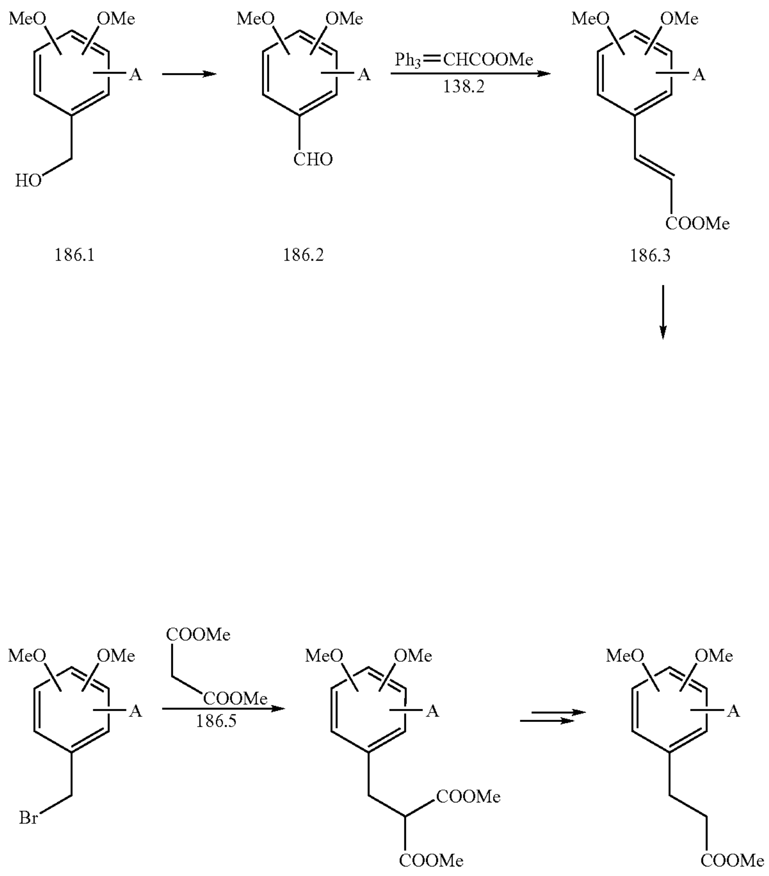
186.1 186.2 186.3
186.4 186.6 21.1
Scheme 187
Method
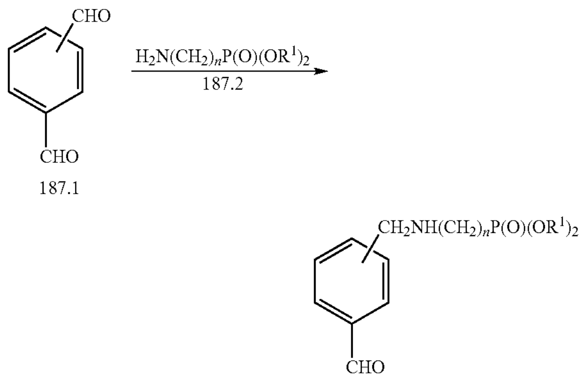
187.1
187.3
-continued
Example
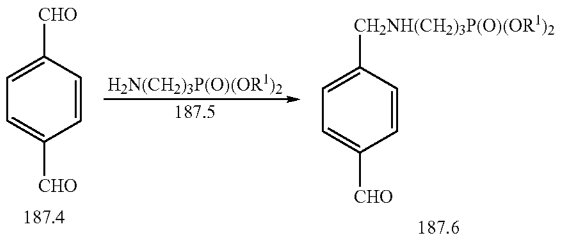
187.4
187.6

Scheme 188
Method
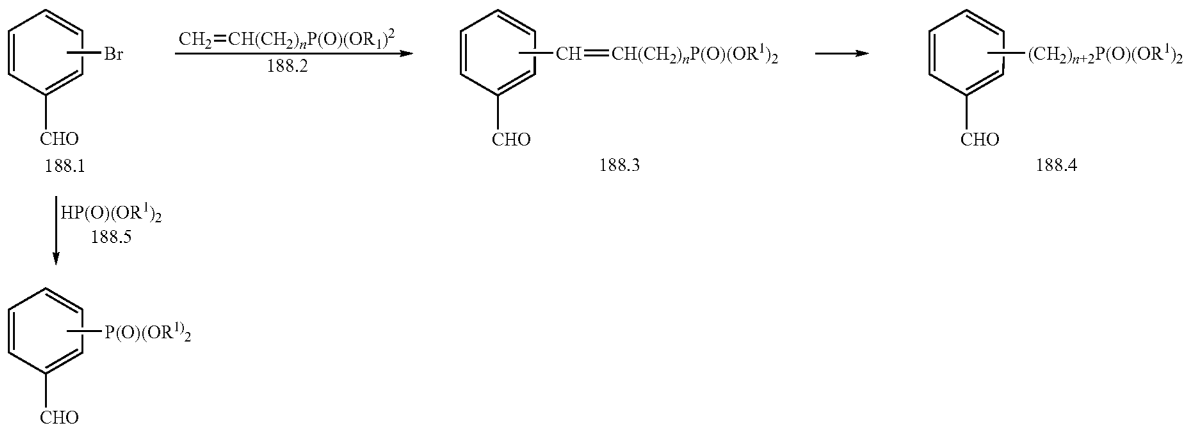
188.1 188.3 188.4
188.6
Example 1
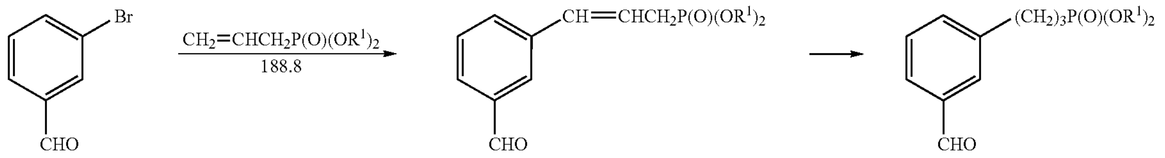
188.7 188.9 188.10
Example 2
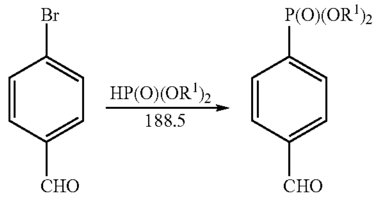
188.11 188.12
Scheme 189
Method
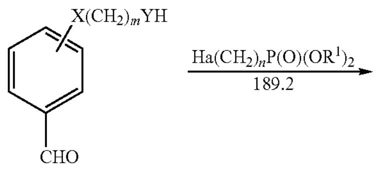
X, Y = O, S, NH
189.1
-continued
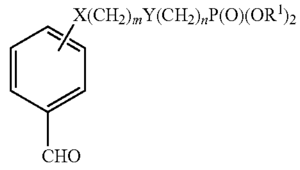
189.3
Example
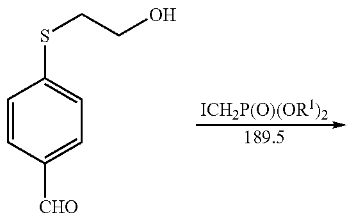
189.4

-continued
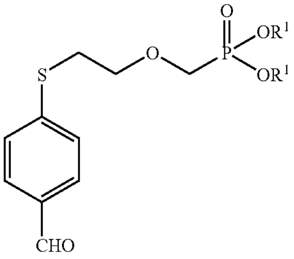
189.6
-continued
Example
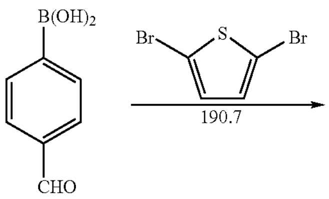
190.6
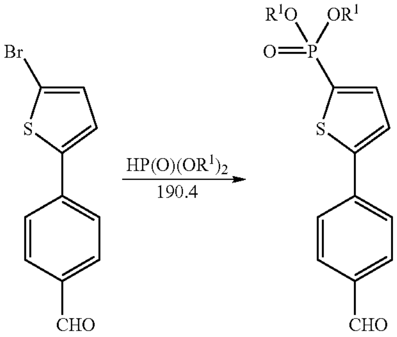
190.8 190.9
Scheme 190
Method
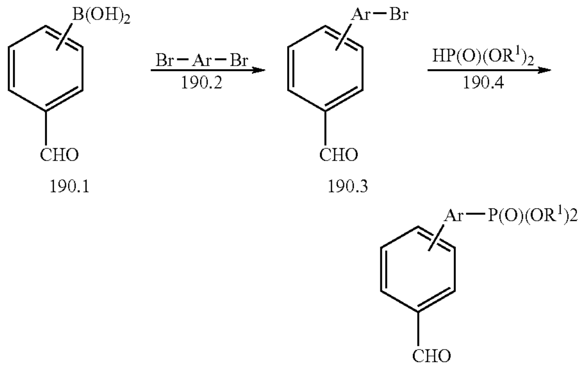
190.1 190.3
190.5
Scheme 191
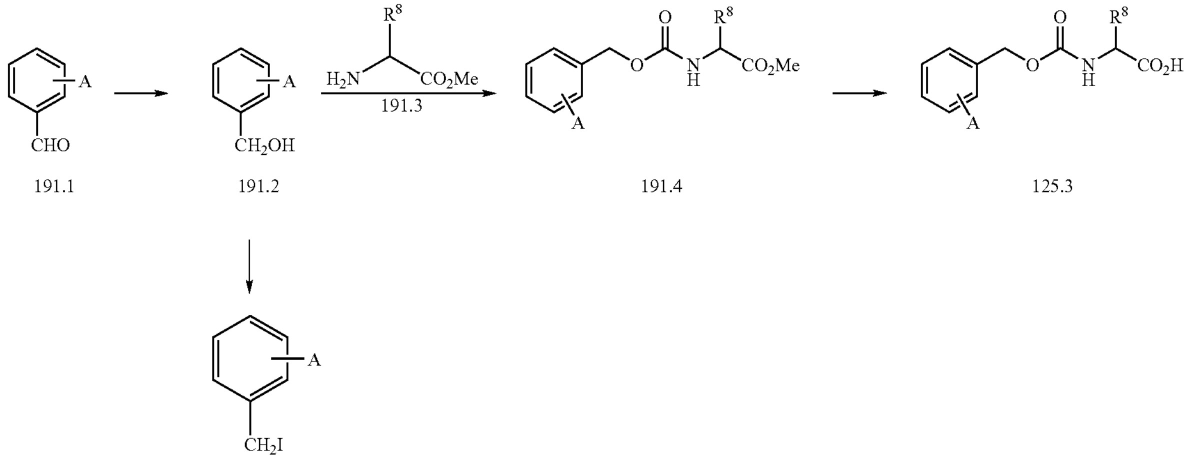
191.1 191.2 191.4 125.3
58.1

Preparation of Phosphonate-substituted Decahydroquinolines 17.1.

Schemes 192-97 illustrate the preparation of decahydroisoquinoline derivatives 17.1 in which the substituent A is either the group link $P(O)(OR^1)_2$ or a precursor, such as [OH], [SH], Br. The compounds are employed in the preparation of the intermediate phosphonate esters 5, 12 and 21.

Scheme 192 illustrates methods for the synthesis of intermediates for the preparation of decahydroquinolines with phosphonate moieties at the 6-position. Two methods for the preparation of the benzenoid intermediate 192.4 are shown.

In the first route, 2-hydroxy-6-methylphenylalanine 192.1, the preparation of which is described in J. Med. Chem., 1969, 12, 1028, is converted into the protected derivative 192.2. For example, the carboxylic acid is first transformed into the benzyl ester, and the product is reacted with acetic anhydride in the presence of an organic base such as, for example, pyridine, to afford the product 192.2, in which R is benzyl. This compound is reacted with a brominating agent, for example N-bromosuccinimide, to effect benzylic bromination and yield the product 192.3. The reaction is conducted in an aprotic solvent such as, for example, ethyl acetate or carbon tetrachloride, at reflux. The brominated compound 192.3 is then treated with acid, for example dilute hydrochloric acid, to effect hydrolysis and cyclization to afford the tetrahydroisoquinoline 192.4, in which R is benzyl.

Alternatively, the tetrahydroisoquinoline 192.4 is obtained from 2-hydroxyphenylalanine 192.5, the preparation of which is described in Can. J. Bioch., 1971, 49, 877. This compound is subjected to the conditions of the Pictet-Spengler reaction, for example as described in Chem. Rev., 1995, 95, 1797.

Typically, the substrate 192.5 is reacted with aqueous formaldehyde, or an equivalent such as paraformaldehyde or dimethoxymethane, in the presence of hydrochloric acid, for example as described in J. Med. Chem., 1986, 29, 784, to afford the tetrahydroisoquinoline product 192.4, in which R is H. Catalytic hydrogenation of the latter compound, using, for example, a platinum catalyst, as described in J. Am. Chem. Soc., 69, 1250, 1947, or using rhodium on alumina as catalyst, as described in J. Med. Chem., 1995, 38, 4446, then gives the hydroxy-substituted decahydroisoquinoline 192.6. The reduction is also performed electrochemically, as described in Trans SAEST 1984, 19, 189.

For example, the tetrahydroisoquinoline 192.4 is subjected to hydrogenation in an alcoholic solvent, in the presence of a dilute mineral acid such as hydrochloric acid, and 5% rhodium on alumina as catalyst. The hydrogenation pressure is ca. 750 psi, and the reaction is conducted at ca 50° C., to afford the decahydroisoquinoline 192.6.

Protection of the carboxyl and NH groups present in 192.6, for example by conversion of the carboxylic acid into the trichloroethyl ester, as described in Protective Groups in Organic Synthesis, by T. W. Greene and P. G. M. Wuts, Wiley, 1991, p. 240, and conversion of the NH into the N-cbz group, as described above, followed by oxidation, using, for example, pyridinium chlorochromate and the like, as described in Reagents for Organic Synthesis, by L. F. Fieser and M. Fieser, Volume 6, p. 498, affords the protected ketone 192.9, in which R is trichloroethyl and $R^1$ is cbz. Reduction of the ketone, for example by the use of sodium borohydride, as described in J. Am. Chem. Soc., 88, 2811, 1966, or lithium tri-tertiary butoxy aluminum hydride, as described in J. Am. Chem. Soc., 80, 5372, 1958, then affords the alcohol 192.10.

For example, the ketone is reduced by treatment with sodium borohydride in an alcoholic solvent such as isopropanol, at ambient temperature, to afford the alcohol 192.10.

The alcohol 192.6 is converted into the thiol 192.13 and the amine 192.14, by means of displacement reactions with suitable nucleophiles, with inversion of stereochemistry. For example, the alcohol 192.6 is converted into an activated ester such as the trifluoromethanesulfonyloxy ester or the methanesulfonate ester 192.7, by treatment with methanesulfonyl chloride and a base. The mesylate 192.7 is then treated with a sulfur nucleophile, for example potassium thioacetate, as described in Tet. Lett., 1992, 4099, or sodium thiophosphate, as described in Acta Chem. Scand., 1960, 1980, to effect displacement of the mesylate, followed by mild basic hydrolysis, for example by treatment with aqueous ammonia, to afford the thiol 192.13.

For example, the mesylate 192.7 is reacted with one molar equivalent of sodium thioacetate in a polar aprotic solvent such as, for example, dimethylformamide, at ambient temperature, to afford the thioacetate 192.12, in which R is $COCH_3$. The product then treated with a mild base such as, for example, aqueous ammonia, in the presence of an organic co-solvent such as ethanol, at ambient temperature, to afford the thiol 192.13.

The mesylate 192.7 is treated with a nitrogen nucleophile, for example sodium phthalimide or sodium bis(trimethylsilyl)amide, as described in Comprehensive Organic Transformations, by R. C. Larock, p. 399, followed by deprotection as described previously, to afford the amine 192.14.

For example, the mesylate 192.7 is reacted, as described in Angew. Chem. Int. Ed., 7, 919, 1968, with one molar equivalent of potassium phthalimide, in a dipolar aprotic solvent, such as, for example, dimethylformamide, at ambient temperature, to afford the displacement product 192.8, in which $NR^aR^b$ is phthalimido. Removal of the phthalimido group, for example by treatment with an alcoholic solution of hydrazine at ambient temperature, as described in J. Org. Chem., 38, 3034, 1973, then yields the amine 192.14.

The application of the procedures described above for the conversion of the β-carbinol 192.6 to the α-thiol 192.13 and the α-amine 192.14 can also be applied to the α-carbinol 192.10, so as to afford the β-thiol and β-amine, 192.11.

Scheme 193 illustrates the preparation of compounds in which the phosphonate moiety is attached to the decahydroisoquinoline by means of a heteroatom and a carbon chain. In this procedure, an alcohol, thiol or amine 193.1 is reacted with a bromoalkyl phosphonate 193.2, under the conditions described above for the preparation of the phosphonate 155.4 (Scheme 155), to afford the displacement product 193.3. Removal of the ester group, followed by conversion of the acid to the $R^4$NH amide and N-deprotection, as described below, (Scheme 197) then yields the amine 193.4.

For example, the thiol 193.5, in which the carboxylic acid group is protected as the trichloroethyl ester, as described in Protective Groups in Organic Synthesis, by T. W. Greene and P. G. M. Wuts, Wiley, 1991, p. 240, and the amine is protected as the cbz group, is reacted with a dialkyl 3-bromopropylphosphonate, 193.6, the preparation of which is described in J. Am. Chem. Soc., 2000, 122, 1554 to afford the displacement product 193.7. Deprotection of the ester group, followed by conversion of the acid to the $R^4$NH amide and N-deprotection, as described below, (Scheme 197) then yields the amine 193.8.

Using the above procedures, but employing, in place of the α-thiol 193.5, the alcohols, thiols or amines 192.6, 192.10, 192.11, 192.13, 192.14, of either α- or β-orientation, there are obtained the corresponding products 193.4, in which the orientation of the side chain is the same as that of the O, N or S precursors.

Scheme 192
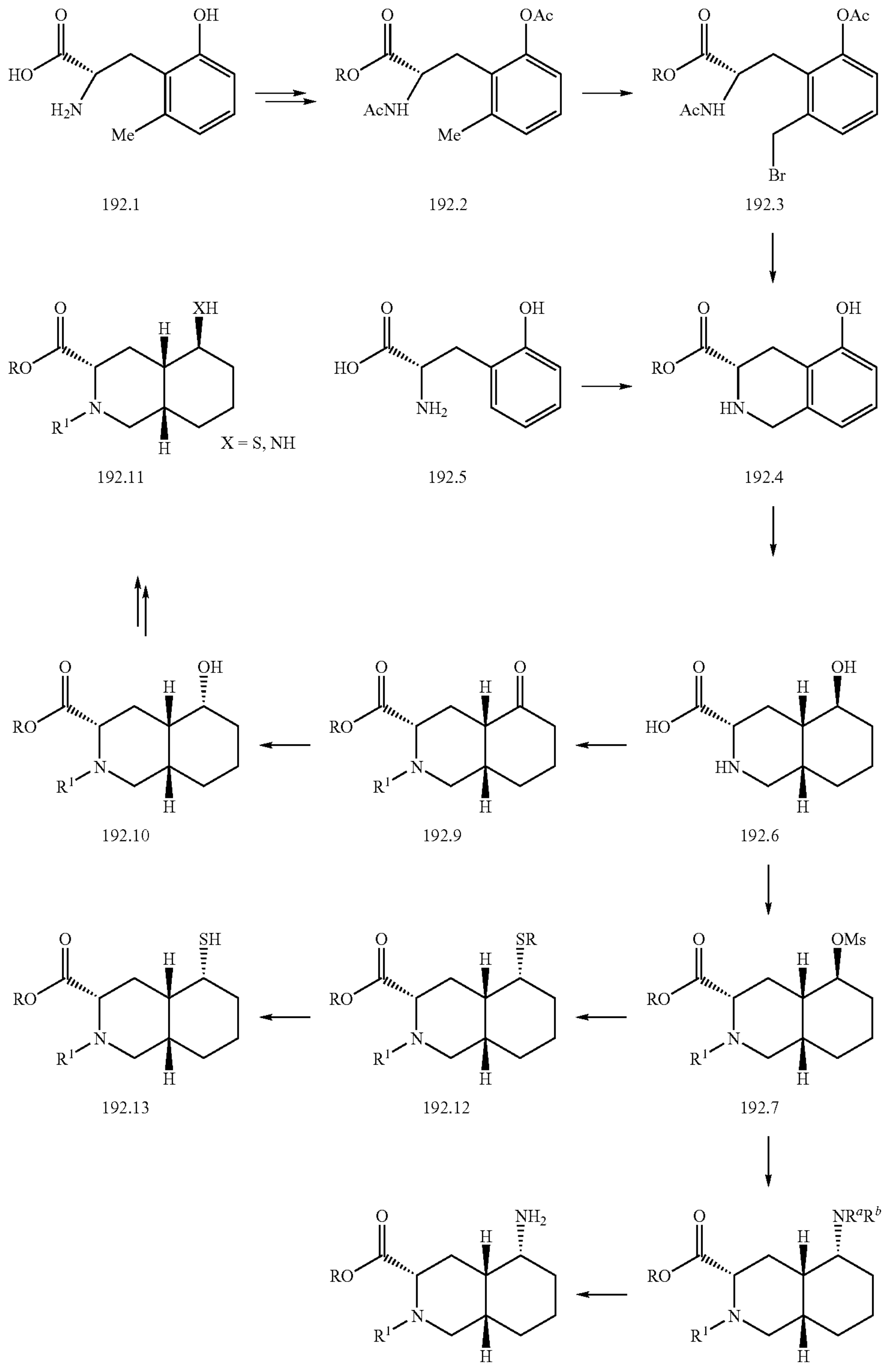
192.1 192.2 192.3
192.11 192.5 192.4
192.10 192.9 192.6
192.13 192.12 192.7
192.14 192.8
$R^1$ = protecting group Scheme 193

Method

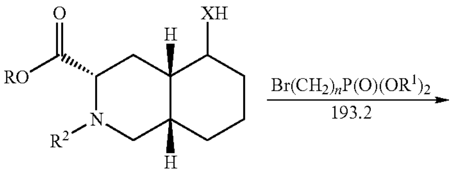

193.1
X = O, S, NH
$R^2$ = protecting group

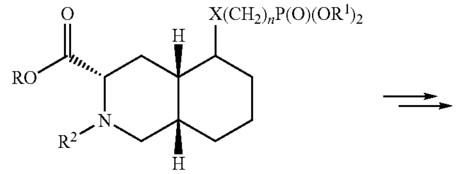

193.3

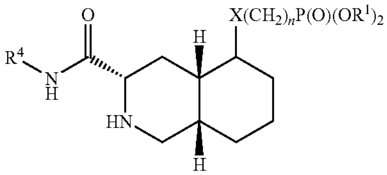

193.4

Example

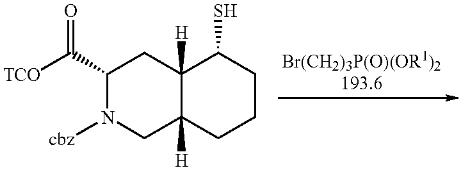

193.5
TC = trichloroethyl

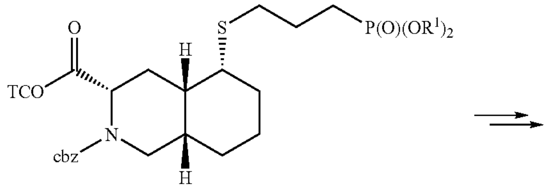

193.7

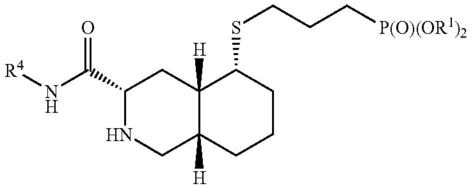

193.8

Scheme 194

Method

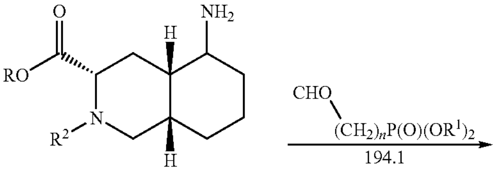

192.11/14
$R^2$ = protecting group

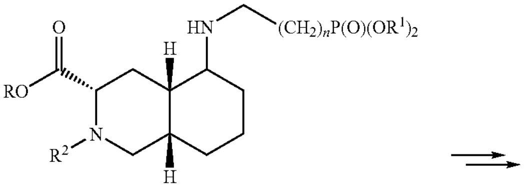

194.2

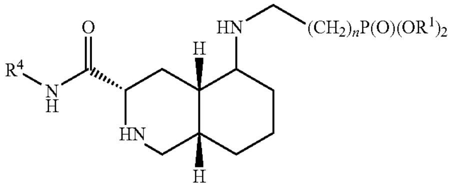

194.3

Example

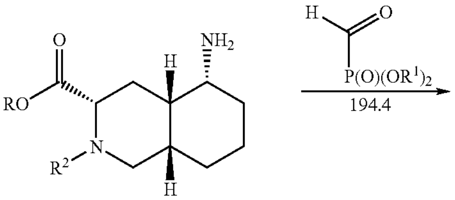

192.14

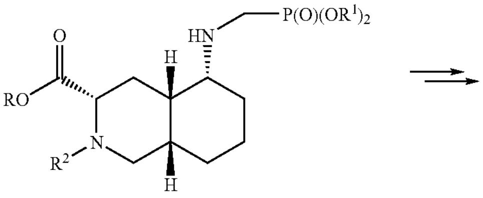

194.5

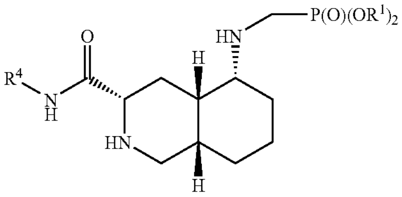

194.6

Scheme 194 illustrates the preparation of phosphonates linked to the decahydroisoquinoline moiety by means of a nitrogen atom and a carbon chain. The compounds are prepared by means of a reductive amination procedure, for example as described in Comprehensive Organic Transformations, by R. C. Larock, p. 421.

In this procedure, the amines 192.14 or 192.11 are reacted with a phosphonate aldehyde 194.1, in the presence of a reducing agent, to afford the alkylated amine 194.2. Deprotection of the ester group, followed by conversion of the acid to the $R^4$NH amide and N-deprotection, as described below, (Scheme 197) then yields the amine 194.3.

For example, the protected amino compound 192.14 is reacted with a dialkyl formylphosphonate 194.4, the preparation of which is described in U.S. Pat. No. 3,784,590, in the presence of sodium cyanoborohydride, and a polar organic solvent such as ethanolic acetic acid, as described in Org. Prep. Proc. Int., 11, 201, 1979, to give the amine phosphonate 194.5. Deprotection of the ester group, followed by conversion of the acid to the $R^4$NH amide and N-deprotection, as described in Scheme 197, then yields the amine 194.6. Using the above procedures, but employing, instead of the α-amine 192.14, the β isomer, 192.11 and/or different aldehydes 194.1, there are obtained the corresponding products 194.3, in which the orientation of the side chain is the same as that of the amine precursor.

Scheme 195 depicts the preparation of a decahydroisoquinoline phosphonate in which the phosphonate moiety is linked by means of a sulfur atom and a carbon chain.

In this procedure, a dialkyl mercaptoalkyl phosphonate 195.2 is reacted with a mesylate 195.1, to effect displacement of the mesylate group with inversion of stereochemistry, to afford the thioether product 195.3. Deprotection of the ester group, followed by conversion of the acid to the $R^4$NH amide and N-deprotection, as described in Scheme 197, then yields the amine 195.4.

For example, the protected mesylate 195.5 is reacted with an equimolar amount of a dialkyl 2-mercaptoethyl phosphonate 195.6, the preparation of which is described in Aust. J. Chem., 43, 1123, 1990. The reaction is conducted in a polar organic solvent such as ethanol, in the presence of a base such as, for example, potassium carbonate, at ambient temperature, to afford the thioether phosphonate 195.7. Deprotection of the ester group, followed by conversion of the acid to the $R^4$NH amide and N-deprotection, as described in Scheme 197, then yields the amine 195.8

Using the above procedures, but employing, instead of the phosphonate 195.6, different phosphonates 195.2, there are obtained the corresponding products 195.4.

Scheme 196 illustrates the preparation of decahydroisoquinoline phosphonates 196.4 in which the phosphonate group is linked by means of an aromatic or heteroaromatic ring. The compounds are prepared by means of a displacement reaction between hydroxy, thio or amino substituted substrates 196.1 and a bromomethyl-substituted arylphosphonate 196.2. The reaction is performed in an aprotic solvent in the presence of a base of suitable strength, depending on the nature of the reactant 196.1. If X is S or NH, a weak organic or inorganic base such as triethylamine or potassium carbonate is employed. If X is O, a strong base such as sodium hydride or lithium hexamethyldisilylazide is employed. The displacement reaction affords the ether, thioether or amine compounds 196.3. Deprotection of the ester group, followed by conversion of the acid to the $R^4$NH amide and N-deprotection, as described in Scheme 197, then yields the amine 196.4.

For example, the alcohol 196.5 is reacted at ambient temperature with a dialkyl 3-bromo-methyl benzylphosphonate 196.6, the preparation of which is described above, (Scheme 143). The reaction is conducted in a dipolar aprotic solvent such as, for example, dioxan or dimethylformamide. The solution of the carbinol is treated with one equivalent of a strong base, such as, for example, lithium hexamethyldisilylazide, and to the resultant mixture is added one molar equivalent of the bromomethyl phosphonate 196.6, to afford the product 196.7. Deprotection of the ester group, followed by conversion of the acid to the $R^4$NH amide and N-deprotection, as described in Scheme 197, then yields the amine 196.8. Using the above procedures, but employing, instead of the β-carbinol 196.5, different carbinols, thiols or amines 196.1, of either α- or β-orientation, and/or different phosphonates 196.2, in place of the phosphonate 196.6, there are obtained the corresponding products 196.4 in which the orientation of the side-chain is the same as that of the starting material 196.1.

Schemes 193-196 illustrate the preparation of decahydroisoquinoline esters incorporating a phosphonate group linked to the decahydroisoquinoline nucleus.

Scheme 197 illustrates the conversion of the latter group of compounds 197.1 (in which the group A is link-$P(O)(OR^1)_2$ or optionally protected precursor substituents, such as, for example, OH, SH, or $NH_2$ to the corresponding $R^4$NH amides 17.1.

As shown in Scheme 197, the ester compounds 197.1 are deprotected to form the corresponding carboxylic acids 197.2. The methods employed for the deprotection are chosen based on the nature of the protecting group R, the nature of the N-protecting group $R^2$, and the nature of the substituent at the 6-position. For example, if R is trichloroethyl, the ester group is removed by treatment with zinc in acetic acid, as described in J. Am. Chem. Soc., 88, 852, 1966. Conversion of the carboxylic acid 197.2 to the $R^4$NH amide 197.4 is then accomplished by reaction, as described in Scheme 1, of the carboxylic acid, or an activated derivative thereof, with the amine $R^4NH_2$ (197.3) to afford the amide 197.4. Deprotection of the $NR^2$ group, as described above, then affords the free amine 17.1.

Preparation of Carbamates.

The phosphonate esters 13-20 in which the $R^{10}$ is alkoxy, and the phosphonate esters 22 contain a carbamate linkage. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 198 illustrates various methods by which the carbamate linkage is synthesized. As shown in Scheme 198, in the general reaction generating carbamates, a carbinol 198.1, is converted into the activated derivative 198.2 in which Lv is a leaving group such as halo, imidazolyl, benztriazolyl and the like, as described below. The activated derivative 198.2 is then reacted with an amine 198.3, to afford the carbamate product 198.4. Examples 1-7 in Scheme 198 depict methods by which the general reaction is effected. Examples 8-10 illustrate alternative methods for the preparation of carbamates.

Scheme 198, Example 1 illustrates the preparation of carbamates employing a chloroformyl derivative of the carbinol 198.1. In this procedure, the carbinol is reacted with phosgene, in an inert solvent such as toluene, at about 0° C., as described in Org. Syn. Conl. Vol. 3, 167, 1965, or with an equivalent reagent such as trichloromethoxy chloroformate, as described in Org. Syn. Coll. Vol. 6, 715, 1988, to afford the chloroformate 198.6. The latter compound is then reacted with the amine component 198.3, in the presence of an organic or inorganic base, to afford the carbamate 198.7. For example, the chloroformyl compound 198.6 is reacted with the amine 198.3 in a water-miscible solvent such as tetrahydrofuran, in the presence of aqueous sodium hydroxide, as described in Org. Syn. Coll. Vol. 3, 167, 1965, to yield the carbamate 198.7. Alternatively, the reaction is performed in dichloromethane in the presence of an organic base such as diisopropylethylamine or dimethylaminopyridine.

Scheme 198, Example 2 depicts the reaction of the chloroformate compound 198.6 with imidazole to produce the imidazolide 198.8. The imidazolide product is then reacted with the amine 198.3 to yield the carbamate 198.7. The preparation of the imidazolide is performed in an aprotic solvent such as dichloromethane at 0° C., and the preparation of the carbamate is conducted in a similar solvent at ambient temperature, optionally in the presence of a base such as dimethylaminopyridine, as described in J. Med. Chem., 1989, 32, 357.

Scheme 198 Example 3, depicts the reaction of the chloroformate 198.6 with an activated hydroxyl compound R"OH, to yield the mixed carbonate ester 198.10. The reaction is conducted in an inert organic solvent such as ether or dichloromethane, in the presence of a base such as dicyclohexylamine or triethylamine. The hydroxyl component R"OH is selected from the group of compounds 198.19-198.24 shown in Scheme 198, and similar compounds. For example, if the component R"OH is hydroxybenztriazole 198.19, N-hydroxysuccinimide 198.20, or pentachlorophenol, 198.21, the mixed carbonate 198.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 198.22 or 2-hydroxypyridine 198.23 is performed in an ethereal solvent in the presence of triethylamine, as described in Syn., 1986, 303, and Chem. Ber. 118, 468, 1985.

Scheme 198 Example 4 illustrates the preparation of carbamates in which an alkyloxycarbonylimidazole 198.8 is employed. In this procedure, a carbinol 198.5 is reacted with an equimolar amount of carbonyl diimidazole 198.11 to prepare the intermediate 198.8. The reaction is conducted in an aprotic organic solvent such as dichloromethane or tetrahydrofuran. The acyloxyimidazole 198.8 is then reacted with an equimolar amount of the amine $R'NH_2$ to afford the carbamate 198.7. The reaction is performed in an aprotic organic solvent such as dichloromethane, as described in Tet. Lett., 42, 2001, 5227, to afford the carbamate 198.7.

Scheme 198, Example 5 illustrates the preparation of carbamates by means of an intermediate alkoxycarbonylbenztriazole 198.13. In this procedure, a carbinol ROH is reacted at ambient temperature with an equimolar amount of benztriazole carbonyl chloride 198.12, to afford the alkoxycarbonyl product 198.13. The reaction is performed in an organic solvent such as benzene or toluene, in the presence of a tertiary organic amine such as triethylamine, as described in Syn., 1977, 704. The product is then reacted with the amine $R'NH_2$ to afford the carbamate 198.7. The reaction is conducted in toluene or ethanol, at from ambient temperature to about 80° C. as described in Syn., 1977, 704.

Scheme 198, Example 6 illustrates the preparation of carbamates in which a carbonate $(R"O)_2CO$, 198.14, is reacted with a carbinol 198.5 to afford the intermediate alkyloxycarbonyl intermediate 198.15. The latter reagent is then reacted with the amine $R'NH_2$ to afford the carbamate 198.7. The procedure in which the reagent 198.15 is derived from hydroxybenztriazole 198.19 is described in Synthesis, 1993, 908; the procedure in which the reagent 198.15 is derived from N-hydroxysuccinimide 198.20 is described in Tet. Lett., 1992, 2781; the procedure in which the reagent 198.15 is derived from 2-hydroxypyridine 198.23 is described in Tet. Lett., 1991, 4251; the procedure in which the reagent 198.15 is derived from 4-nitrophenol 198.24 is described in Syn. 1993, 199. The reaction between equimolar amounts of the carbinol ROH and the carbonate 198.14 is conducted in an inert organic solvent at ambient temperature.

Scheme 198, Example 7 illustrates the preparation of carbamates from alkoxycarbonyl azides 198.16. In this procedure, an alkyl chloroformate 198.6 is reacted with an azide, for example sodium azide, to afford the alkoxycarbonyl azide 198.16. The latter compound is then reacted with an equimolar amount of the amine $R'NH_2$ to afford the carbamate 198.7. The reaction is conducted at ambient temperature in a polar aprotic solvent such as dimethylsulfoxide, for example as described in Syn., 1982, 404.

Scheme 198, Example 8 illustrates the preparation of carbamates by means of the reaction between a carbinol ROH and the chloroformyl derivative of an amine 198.17. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 198.7.

Scheme 198, Example 9 illustrates the preparation of carbamates by means of the reaction between a carbinol ROH and an isocyanate 198.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 198.7.

Scheme 198, Example 10 illustrates the preparation of carbamates by means of the reaction between a carbinol ROH and an amine $R'NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 198.7.

Scheme 195

Method

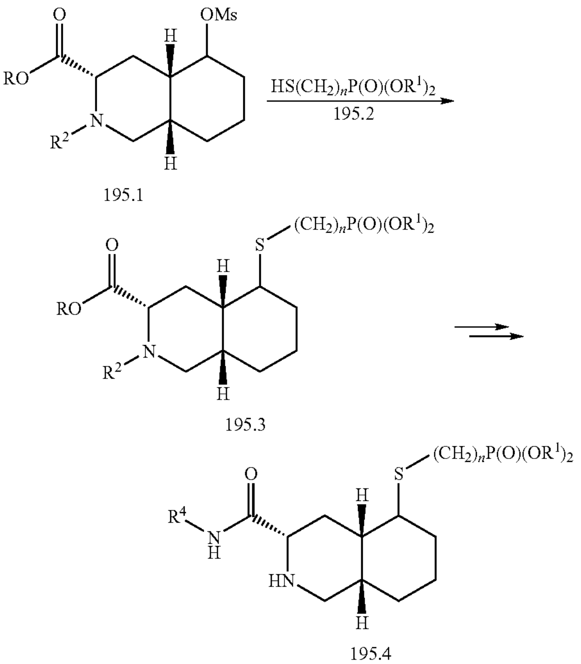

195.1

195.3

195.4

-continued
Example
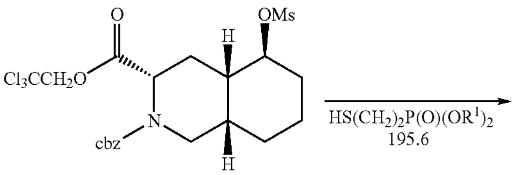
195.5
$R^2$ = protecting group
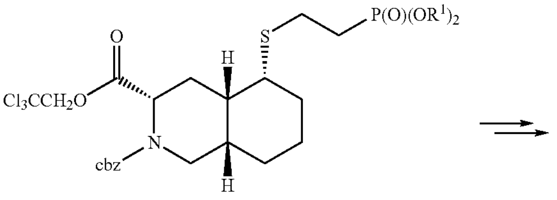
195.7
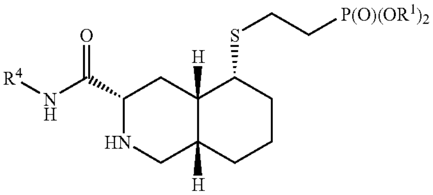
195.8
Scheme 196
Method
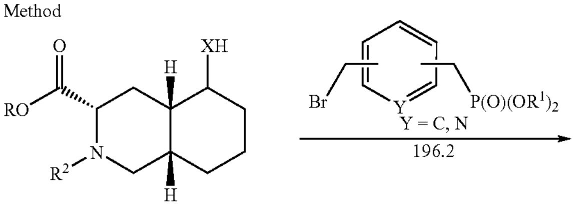
196.1 X = O, S, NH
$R^2$ = protecting group
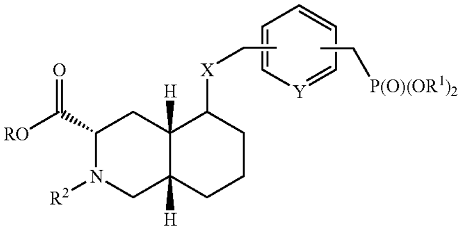
196.3
-continued
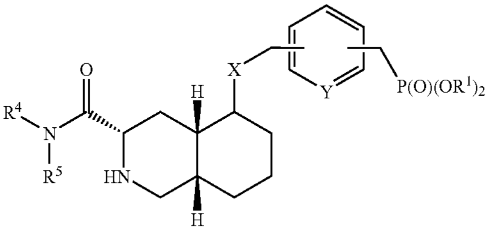
196.4
Example
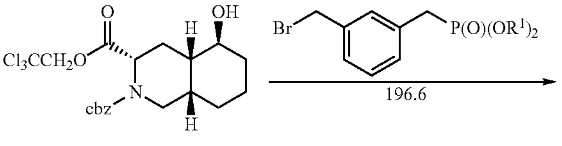
196.5
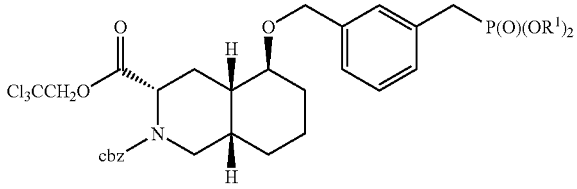
196.7
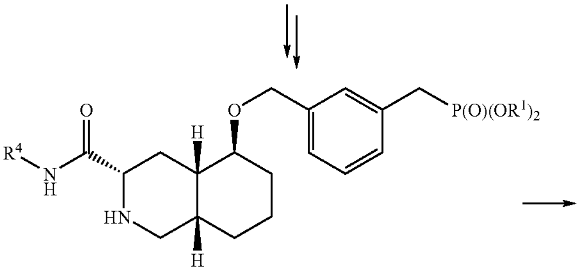
196.8
Scheme 197
Method
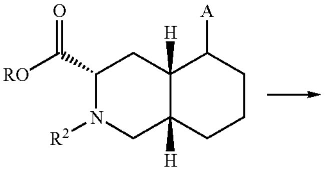
197.1
$R^2$ = protecting group
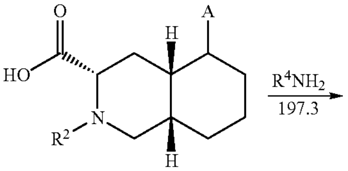
197.2

-continued

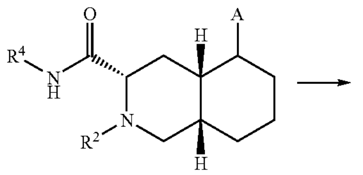

197.4

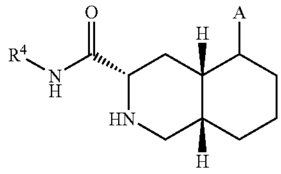

17.1

Scheme 198

General reaction

ROH ROCOLv
R'NH2
198.3
ROCONHR'

198.1 198.2 198.4

Examples (1)

ROH ROCOCl
R'NH2
198.3
ROCONHR'

198.5 198.6 198.7

(2)

ROH ROCOCl

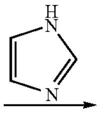

198.5 198.6

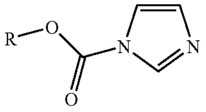

R'NH2
198.3
ROCONHR'

198.8 198.7

(3)

ROH ROCOCl
R"OH
198.9
ROCOOR"
R'NH2
198.3

198.5 198.6 198.10

ROCONHR'

198.7

(4)

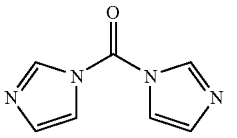

ROH
198.11

198.5

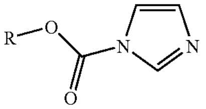

R'NH2
198.3
ROCONHR'

198.8 198.7

-continued (5)

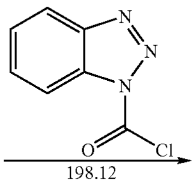

ROH
198.12

198.5

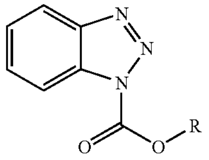

R'NH2
198.3
ROCONHR'

198.13 198.7

(6)

ROH
(R"O2)C=O
198.14
ROCOR"
R'NH2
198.3
ROCONHR'

198.5 198.15 198.7

(7)

ROH ROCOCl ROCON3
R'NH2
198.3

198.5 198.6 198.16

ROCONHR'

198.7

(8)

ROH
R'NHCOCl
198.17
ROCONHR'

198.5 198.7

(9)

ROH
R'NCO
198.18
ROCONHR'

198.5 198.7

(10)

ROH
R'NH2
198.3
ROCONHR'

198.5 198.7

R"OH =

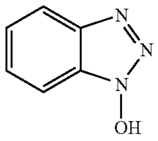

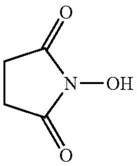

198.19 198.20

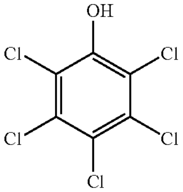

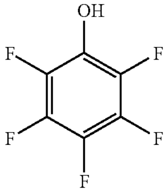

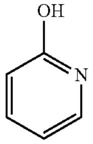

198.21 198.22 198.23

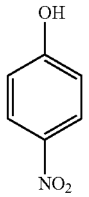

198.24

Interconversions of the Phosphonates R-link-P(O)(OR[1])$_2$, R-link-P(O)(OR[1])(OH) and R-link-P(O)(OH)$_2$.

Schemes 1-197 described the preparations of phosphonate esters of the general structure R-link-P(O)$(OR^1)_2$, in which the groups $R^1$, the structures of which are defined in Chart 1, may be the same or different. The $R^1$ groups attached to the phosphonate esters 1-24, or to precursors thereto, may be changed using established chemical transformations. The interconversions reactions of phosphonates are illustrated in Scheme 199. The group R in Scheme 199 represents the substructure to which the substituent link-P(O)$(OR^1)_2$ is attached, either in the compounds 1-24 or in precursors thereto. The $R^1$ group may be changed, using the procedures described below, either in the precursor compounds, or in the esters 1-24. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 199.1 into the corresponding phosphonate monoester 199.2 (Scheme 199, Reaction 1) is accomplished by a number of methods. For example, the ester 199.1 in which $R^1$ is an aralkyl group such as benzyl, is converted into the monoester compound 199.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110° C. The conversion of the diester 199.1 in which $R^1$ is an aryl group such as phenyl, or an alkenyl group such as allyl, into the monoester 199.2 is effected by treatment of the ester 199.1 with a base such as aqueous sodium hydroxide in acetonitrile or lithium hydroxide in aqueous tetrahydrofuran. Phosphonate diesters 199.1 in which one of the groups $R^1$ is aralkyl, such as benzyl, and the other is alkyl, are converted into the monoesters 199.2 in which $R^1$ is alkyl by hydrogenation, for example using a palladium on carbon catalyst. Phosphonate diesters in which both of the groups $R^1$ are alkenyl, such as allyl, are converted into the monoester 199.2 in which $R^1$ is alkenyl, by treatment with chlorotris(triphenylphosphine) rhodium (Wilkinson's catalyst) in aqueous ethanol at reflux, optionally in the presence of diazabicyclooctane, for example by using the procedure described in J. Org. Chem., 38, 3224, 1973 for the cleavage of allyl carboxylates.

The conversion of a phosphonate diester 199.1 or a phosphonate monoester 199.2 into the corresponding phosphonic acid 199.3 (Scheme 199, Reactions 2 and 3) is effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 199.2 in which $R^1$ is aralkyl such as benzyl, is converted into the corresponding phosphonic acid 199.3 by hydrogenation over a palladium catalyst, or by treatment with hydrogen chloride in an ethereal solvent such as dioxan. A phosphonate monoester 199.2 in which $R^1$ is alkenyl such as, for example, allyl, is converted into the phosphonic acid 199.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 199.1 in which $R^1$ is benzyl is described in J. Org. Chem., 24, 434, 1959. Platinum-catalyzed hydrogenolysis of phosphonate esters 199.1 in which $R^1$ is phenyl is described in J. Am. Chem. Soc., 78, 2336, 1956.

The conversion of a phosphonate monoester 199.2 into a phosphonate diester 199.1 (Scheme 199, Reaction 4) in which the newly introduced $R^1$ group is alkyl, aralkyl, haloalkyl such as chloroethyl, or aralkyl is effected by a number of reactions in which the substrate 199.2 is reacted with a hydroxy compound $R^1$OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 199.2 to the diester 199.1 is effected by the use of the Mitsonobu reaction, as described above (Scheme 142). The substrate is reacted with the hydroxy compound $R^1$OH, in the presence of diethyl azodicarboxylate and a triarylphosphine such as triphenyl phosphine. Alternatively, the phosphonate monoester 199.2 is transformed into the phosphonate diester 199.1, in which the introduced $R^1$ group is alkenyl or aralkyl, by reaction of the monoester with the halide $R^1$Br, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester 199.2 is transformed into the chloro analog RP(O)$(OR^1)$Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product RP(O)$(OR^1)$Cl is then reacted with the hydroxy compound $R^1$OH, in the presence of a base such as triethylamine, to afford the phosphonate diester 199.1.

A phosphonic acid R-link-P(O)$(OH)_2$ is transformed into a phosphonate monoester RP(O)$(OR^1)$(OH) (Scheme 199, Reaction 5) by means of the methods described above of for the preparation of the phosphonate diester R-link-P(O)$(OR^1)_2$ 199.1, except that only one molar proportion of the component $R^1$OH or $R^1$Br is employed.

A phosphonic acid R-link-P(O)$(OH)_2$ 199.3 is transformed into a phosphonate diester R-link-P(O)$(OR^1)_2$ 199.1 (Scheme 199, Reaction 6) by a coupling reaction with the hydroxy compound $R^1$OH, in the presence of a coupling agent such as Aldrithiol-2 (Aldrich) and triphenylphosphine. The reaction is conducted in a basic solvent such as pyridine. Alternatively, phosphonic acids 199.3 are transformed into phosphonic esters 199.1 in which $R^1$ is aryl, by means of a coupling reaction employing, for example, dicyclohexylcarbodiimide in pyridine at ca 70° C. Alternatively, phosphonic acids 199.3 are transformed into phosphonic esters 199.1 in which $R^1$ is alkenyl, by means of an alkylation reaction. The phosphonic acid is reacted with the alkenyl bromide $R^1$Br in a polar organic solvent such as acetonitrile solution at reflux temperature, the presence of a base such as cesium carbonate, to afford the phosphonic ester 199.1.

Scheme 199

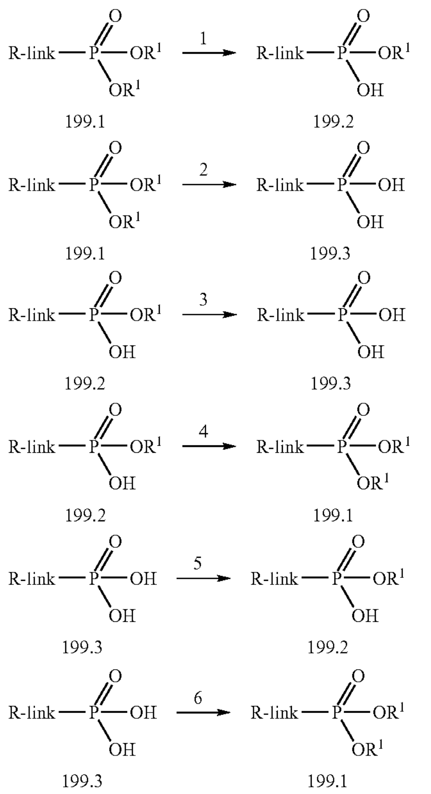

General applicability of methods for introduction of phosphonate substituents.

The procedures described for the introduction of phosphonate moieties (Schemes 133-192) are, with appropriate modifications known to one skilled in the art, transferable to different chemical substrates. Thus, the methods described above for the introduction of phosphonate groups into indanols (Schemes 133-137) are applicable to the introduction of phosphonate moieties into phenylpropionic acids, thiophenols, tert. butylamines, pyridines, benzyl halides, ethanolamines, aminochromans, phenylalanines and benzyl alcohols, and the methods described for the introduction of phosphonate moieties into the above-named substrates (Schemes 138-192) are applicable to the introduction of phosphonate moieties into indanol substrates.

Preparation of Phosphonate Intermediates 23 and 24 with Phosphonate Moieties Incorporated Into the $R^2$, $R^3$, $R^5$, $R^{10}$ or $R^{11}$ groups.

The chemical transformations described in Schemes 1-192 illustrate the preparation of compounds 1-22 in which the phosphonate ester moiety is attached to the indanol moiety, (Schemes 1-4, 76-84), the phenyl group (Schemes 5-8, 21-24, 37-40, 49-52, 58-61, 67-68, 74, 75, 101-108, 125-132) the tert. butylamine group, (Schemes 9-12, 25-28, 41-44, 109-116), the pyridine group (Schemes 13-16), the decahydroisoquinoline group (Schemes 17-20, 45-48, 117-124), the ethanolamine group (Schemes 29-32, 93-100), the aminochroman group (Schemes 33-36, 85-92), and the thiophenyl group (Schemes 53-57, 62-66, 69-73). The various chemical methods employed for the introduction of phosphonate ester groups into the above-named moieties can, with appropriate modifications known to those skilled in the art, be applied to the introduction of a phosphonate ester group into the compounds $R^2R^3NH$, $R^5SH$, $R^5CH_2I$, $R^{10}CO$, $R^{11}SH$, and $R^{11}CH_2CH(NH_2)COOH$. The resultant phosphonate-containing analogs, designated as $R^{2a}R^{3a}NH$, $R^{5a}SH$, $R^{5a}CH_2I$, $R^{10a}CO$, $R^{11a}SH$, and $R^{11a}CH_2CH(NH_2)COOH$ are then, using the procedures described above, employed in the preparation of the compounds 23 and 24. The procedures required for the utilization of the phosphonate-containing analogs are the same as those described above for the utilization of the compounds $R^2R^3NH$, $R^5SH$, $R^5CH_2I$, $R^{10}CO$, $R^{11}SH$, and $R^{11}CH_2CH(NH_2)COOH$.

For example, Schemes 200-204 and Schemes 205-207 depict the introduction of the group link-$P(O)(OR^1)_2$ or a precursor thereto, such as, [OH], [$NH_2$], [SH] onto the $R^2R^3NH$ amines A10a and A10b in Chart 4, to give amines 200.5 and 205.10 respectively. These amine products are then utilized in the generation of compounds 23 where $R^2R^3NH$ is now $R^{2a}R^{3a}NH$ in Chart 3 following the same procedures outlined in Schemes 13 and 15 but replacing the amine 13.1 with 200.5 or 205.10 respectively.

Preparation of Piperazine Furan Compounds 200.5 with Phosphonate Attachments

Schemes 200-204 depict the preparation of the piperazine furan aryl phosphonate compounds 200.5 that are employed in the preparation of the phosphonate esters 23 where $R^2R^3NH$ is now $R^{2a}R^{3a}NH$ as described above.

Scheme 200 depicts the preparation of piperazine biaryl phosphonates in which the terminal aryl ring bears the phosphonate moiety through a linking group. Methods for the preparation of the reagents 200.2 are shown in Schemes 201-204. Furan 200.1 prepared as described in WO02/096359, is treated with the aryl bromide 200.2 in the presence of palladium catalyst by the method of Gronowitz et al. (J. Heterocyclic Chemistry, 1995, 35, p. 771) to give 200.3.

The product 200.3 is then subjected to the sequence of reactions and conditions described in WO02/096359 to prepare the piperazine 200.5. The preparation of reagent 200.6 where $R^4{=}CH_2CF_3$ is also described in WO02/096359. Alternatively, deprotection of amines 164.1 by treatment with trifluoroacetic acid at room temperature as described in Int. J. Pept. Protein Res., 12, 258, 1978, followed by treatment with alloc chloro formate and a base such as pyridine, as described in Protective Groups in Organic Synthesis, by T. W. Greene and P. G. M Wuts, Wiley, Third Edition 1999 p. 526-527 yields 200.6 where $R^4$ is as defined in Chart 1.

Scheme 201 depicts the preparation of phosphonates 200.2 in which the phosphonate moiety is attached to the phenyl ring by means of a heteroatom and an alkyl chain. Many halogenated aromatic compounds are commercially available or can be generated from readily available aromatic compounds through aromatic substitution. Methods for chlorinating or brominating an aryl ring can be found in Comprehensive Organic Transformations, by R. C. Larock, $2^{nd}$ Edition, 1999 p619. The phenol, thiol or amine 201.1 is reacted with a derivative of a hydroxymethyl dialkylphosphonate 140.2, in which Lv is a leaving group such as methanesulfonyloxy and the like. The reaction is conducted in a polar aprotic solvent, in the presence of an organic or inorganic base, to afford the displacement product 201.2. For example, the phenols 201.5 (Aldrich) or 201.9 (Apollo-Chem) are reacted with a dialkyl trifluoromethanesulfonyloxymethyl phosphonate 140.6, prepared as described in Tet. Lett., 1986, 27, 1477, to afford the ether products. Equimolar amounts of the reactants are combined in a polar solvent such as dimethylformamide, in the presence of a base such as potassium carbonate, at about 50°

C., to afford the products 201.6 and 201.10 respectively. Alternatively treatment of amine 201.11 (Apollo) or 201.7 (Aldrich) with the dialkyl trifluoromethylsulfonyloxymethyl phosphonate 140.6 in the presence of a base as described above affords 201.12 and 201.8 respectively.

Using the above procedures, but employing, in place of the phenols and amines, different phenols, thiols or amines 201.1, and/or different dialkyl trifluoromethyl-sulfonyloxymethyl phosphonates 140.2, the corresponding products 201.2 are obtained.

Scheme 202 illustrates the preparation of compounds in which the phosphonate group is attached by means of an aminoalkyl chain. In this procedure, the aldehyde 202.1 is reacted, under reductive amination conditions, as described in Scheme 135, with a dialkyl aminoalkyl phosphonate 202.2, to give the amine 202.3.

For example, the aldehyde 202.4 (Aldrich) is reacted in ethanol with a dialkyl aminoethyl phosphonate 166.5, the preparation of which is described in J. Org. Chem., 2000, 65, 676, and sodium triacetoxyborohydride, to produce the amine 202.5. Using the above procedures, but employing, in place of the aldehyde, 202.4 different aldehydes 202.1 and different phosphonates 202.2, the corresponding products 202.3 are obtained.

Scheme 203 illustrates the preparation of aryl halides incorporating phosphonate groups attached by means of an amide group. In this procedure, a carboxy-substituted aryl halide 203.1 is coupled, as described in Scheme 1, with a dialkyl aminoalkyl phosphonate 202.2 to prepare the amide 203.2.

For example, 2-chloro-4-bromobenzoic acid 203.4, the preparation of which is described in Bioorg. Med. Chem. Lett. 2001, 11, 10, p. 1257, is coupled in dimethylformamide solution, in the presence of dicyclohexylcarbodiimide, with a dialkyl aminoethyl phosphonate 166.5, the preparation of which is described in J. Org. Chem., 2000, 65, 676, to afford the amide 203.5. Using the above procedures, but employing, in place of the benzoic acid 203.4, different benzoic acids 203.1, and/or different aminoalkyl phosphonates 202.2, the corresponding products 203.2 are obtained.

Scheme 204 illustrates the preparation of phosphonate-substituted aryl halides in which the phosphonate group is attached by means of a one-carbon link. In this procedure, a benzoic acid 203.1 is first methylated to give methyl ester 204.1 and then reduced with a reducing agent, as described in J. Org Chem 1987, 52, p. 5419 to give alcohol 204.2. The alcohol 204.2 is then reacted with hexabromoethane in the presence of triphenyl phosphine as described in Syn. 1983, p. 139 to give the bromide 204.3. The bromide 204.3 is reacted with a sodium dialkyl phosphite 204.5 or a trialkyl phosphite, to give the product 204.4 For example, acid 204.6 (Lancaster) is converted to the methyl ester 204.7 by refluxing in methanol and concentrated sulfuric acid and then reduced with lithium aluminum hydride in THF to give 204.8 as described above. The product 204.8 is reacted with hexabromoethane in the presence of triphenyl phosphine as described in Syn. 1983, p. 139 to give the bromide 204.9. This material is reacted with a sodium dialkyl phosphite 204.5, as described in J. Med. Chem., 35, 1371, 1992, to afford the product 204.10. Alternatively, the bromomethyl compound 204.9 is converted into the phosphonate 204.10 by means of the Arbuzov reaction, for example as described in Handb. Organophosphorus Chem., 1992, 115. In this procedure, the bromomethyl compound 204.9 is heated with a trialkyl phosphate $P(OR^1)_3$ at ca. 100° C. to produce the phosphonate 204.10.

Using the above procedures, but employing, in place of the acid 204.6, different acids 203.1, and different phosphites 204.5 there are obtained the corresponding aryl halides 204.4.

The phosphonate-containing bromobenzene derivatives prepared as described in Schemes 201-204 are then transformed, as described in Scheme 200, into the phenylfuran piperazine derivatives 200.5.

Scheme 200

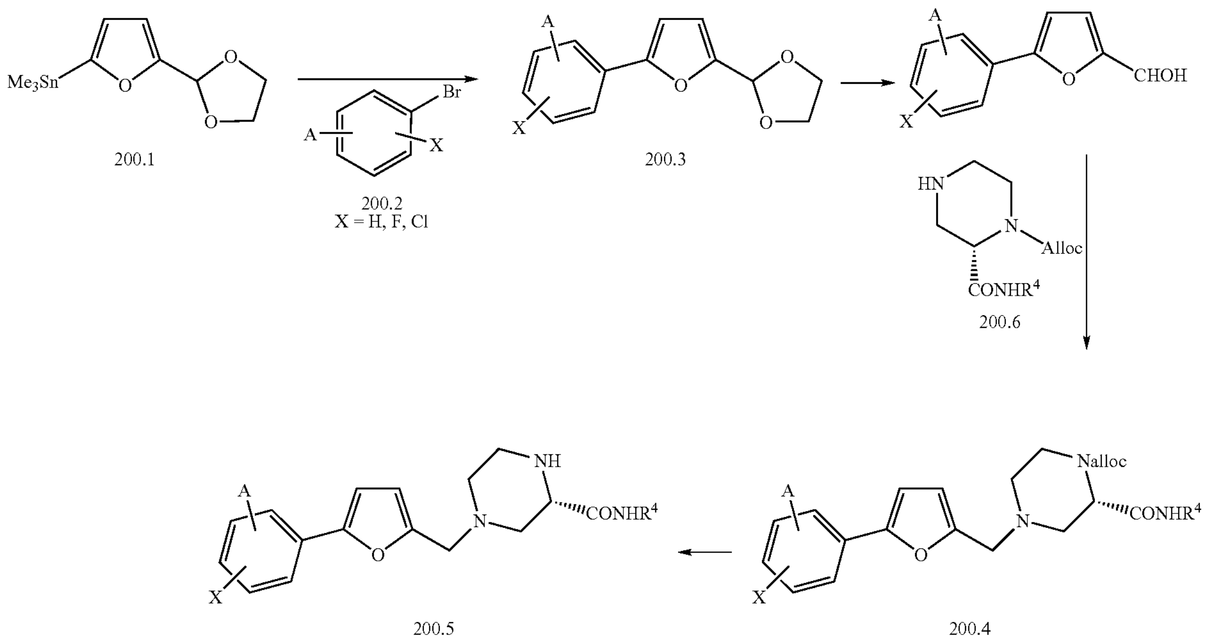
200.1 200.2 X = H, F, Cl 200.3 200.6 200.4 200.5

Scheme 201
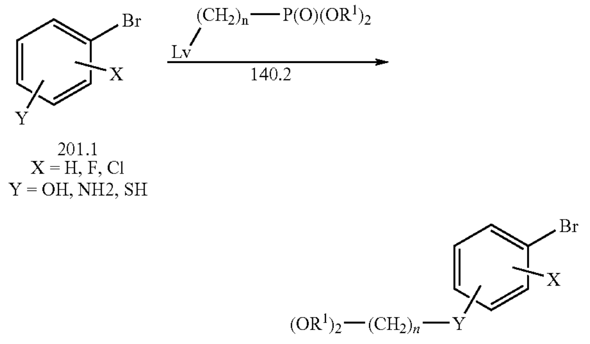
201.1
X = H, F, Cl
Y = OH, NH2, SH
201.2
Example
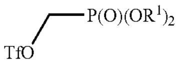
140.6
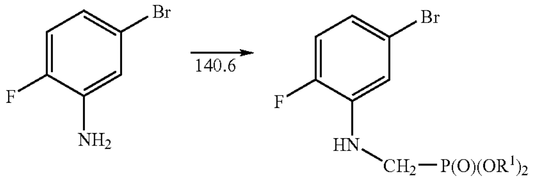
201.11 201.12
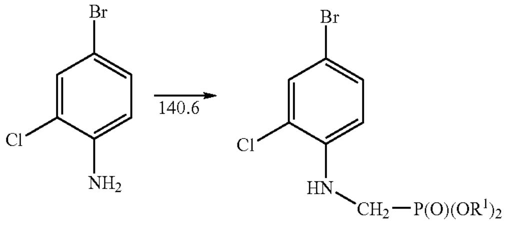
201.7 201.8
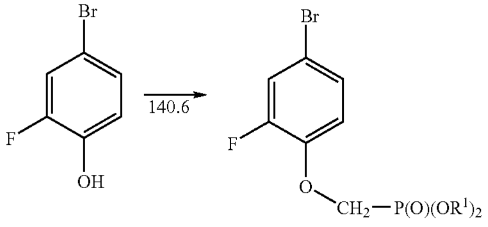
201.5 201.6
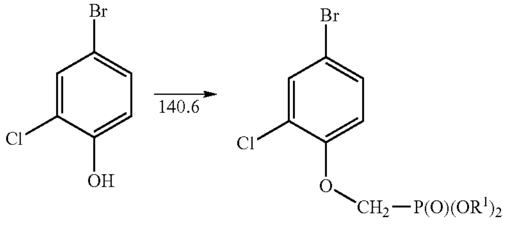
201.9 201.10
Scheme 202
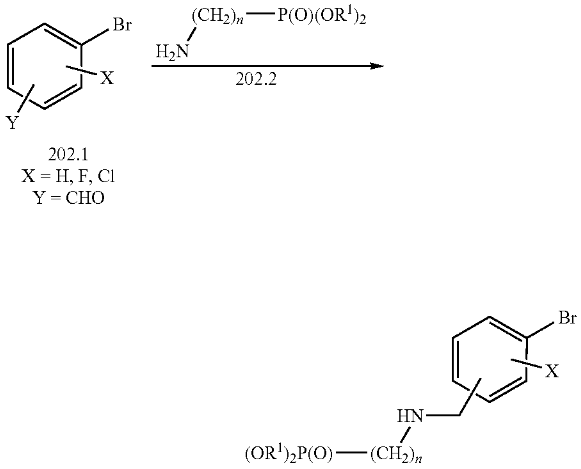
202.1
X = H, F, Cl
Y = CHO
202.3
Example
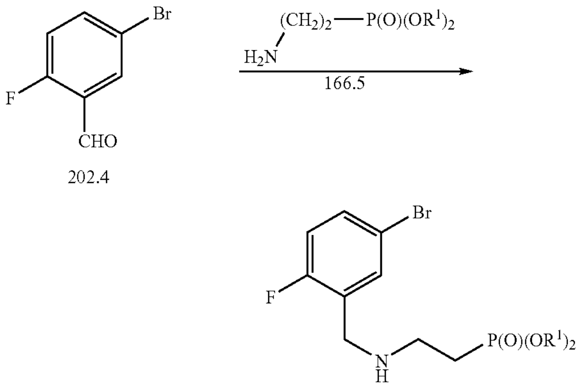
202.4
202.5
Scheme 203
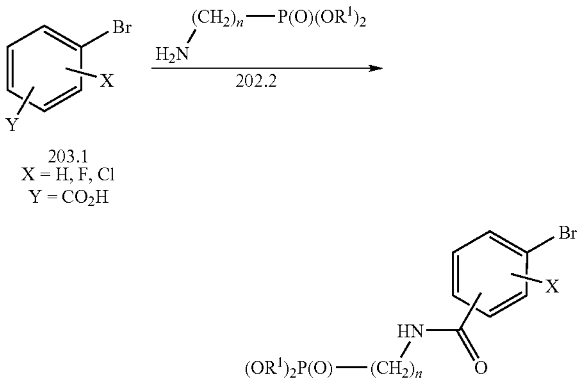
203.1
X = H, F, Cl
Y = $CO_2H$
203.2

-continued

Example

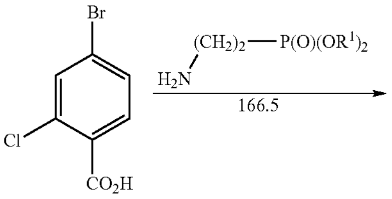

203.4

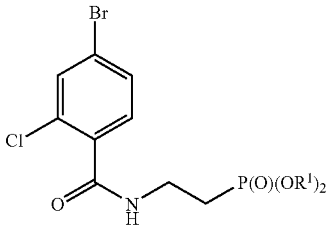

203.5

-continued

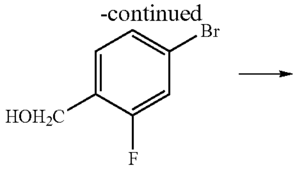

204.8

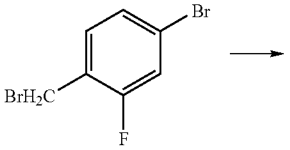

204.9

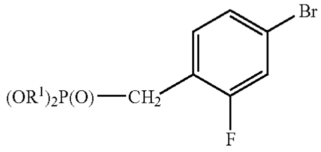

204.10

Scheme 204

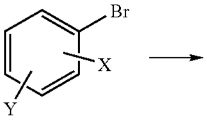

203.1
X = H, F, Cl
Y = $CO_2H$

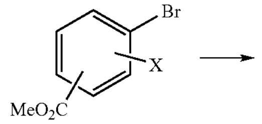

204.1

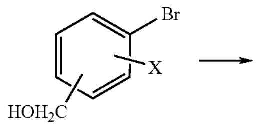

204.2

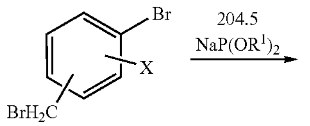

204.3

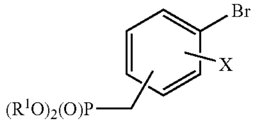

204.4

Example

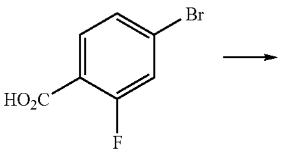

204.6

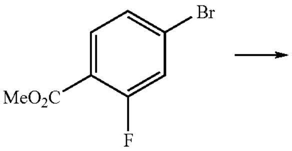

204.7

Preparation of Piperazine Ozaxole Compounds 205.10 Bearing Phosphonate Attachments Schemes 205-207 depict the preparation of the piperazine oxazole phosphonate compounds 205.10 that are employed in the preparation of the phosphonate esters 23 where $R^2R^3NH$ is now $R^{2a}R^{3a}NH$ as described above.

Scheme 205 depicts the preparation of piperazine oxazole phosphonates 205.10 in which the terminal aryl ring bears the phosphonate moiety. The acid 205.1 is converted to the Weinreb amide, for example, as described in J. Med. Chem., 1994, 37, 2918, and then reacted with a methyl Grignard reagent e.g. MeMgBr. Examples of this procedure are reviewed in Org prep Proc Intl 1993, 25, 15. Ketone 205.3 is then brominated using conditions described in Comprehensive Organic Transformations, by R. C. Larock, $2^{nd}$ Edition, 1999, p. 710-711. For example, treatment of 205.3 with bromine in acetic acid yields 205.4. Conversion of the bromomethyl compound 205.4 into the piperazine derivative 205.10, via the intermediates 205.5-205.9, is effected by means of the reactions and procedures described in WO02/096359 for related compounds in which $R^4$ is $CH_2CF_3$ and A is H.

Scheme 206 illustrates the preparation of benzoic acid phosphonates in which the phosphonate moiety is attached by means of alkylene chains and a heteroatom O, S or N. In this procedure, a benzoic acid 206.1 is protected with a suitable protecting group (see Protective Groups in Organic Synthesis, by T. W. Greene and P. G. M Wuts, Wiley, Third Edition 1999 ch5 and then reacted with a an equimolar amount of a dialkyl phosphonate 206.3, in which Ha is a leaving group e.g. halogen, to afford the alkyl phosphonate product 206.4. The alkylation reaction is effected in a polar organic solvent such as dimethylformamide or acetonitrile, in the presence of a base. The base employed depends on the nature of the nucleophile 206.2. In cases in which Y is O, a strong base such as sodium hydride or lithium hexamethyldisilazide is employed. In cases in which Y is S or N, a base such as cesium carbonate or dimethylaminopyridine is employed. Following this reaction the product 206.4 is hydrolyzed by treatment with base to give the acid 206.5

For example, benzoic acid 206.6, (Aldrich) is reacted with diazomethane in ether at 0° C. to give the methyl ester 206.7 or simply refluxed in acidic methanol. The ester in acetonitrile at 60° C. is treated with one molar equivalent of a dialkyl iodomethyl phosphonate 206.8, (Lancaster) to give the ether product 206.9. This product 206.9 is then hydrolyzed by treatment with lithium hydroxide in aqueous THF to give the acid 206.10.

Using the above procedures, but employing, in place of the benzoic acid 206.6, different acids 206.1, and/or different haloalkyl phosphonates 206.3, the corresponding products 206.5 are obtained.

Scheme 207 depicts the preparation of phosphonate esters linked to a benzoic acid nucleus by means of unsaturated and saturated carbon chains. The carbon chain linkage is formed by means of a palladium catalyzed Heck reaction, in which an olefinic phosphonate 207.3 is coupled with an aromatic bromo compound 207.2. The coupling of aryl halides with olefins by means of the Heck reaction is described, for example, in Advanced Organic Chemistry, by F. A. Carey and R. J. Sundberg, Plenum, 2001, p. 503ff and in Ace. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or a palladium(II) catalyst such as palladium(II) acetate, and optionally in the presence of a base such as triethylamine or potassium carbonate, to afford the coupled product 207.4. Deprotection, or hydrogenation of the double bond followed by deprotection, affords respectively the unsaturated phosphonate acid 207.5, or the saturated analog 207.6 respectively.

For example, 4-bromo-3-fluorobenzoic acid 207.7 (Apollo) is converted to the tert butyl ester 207.8 by treatment with t-butanol and DCC in the presence of dimethylaminopyridine. The ester 207.8 is then reacted with a dialkyl 1-propenyl phosphonate 150.8, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 100° C. to afford the coupled product 207.10. Deprotection as described in Protective Groups in Organic Synthesis, by T. W. Greene and P. G. M Wuts, Wiley, Third Edition 1999 p. 406-408, then affords the acid 207.11. Optionally, the acid 207.11 is subjected to catalytic or chemical reduction, for example using diimide, as described in Scheme 138, to yield the saturated product 207.12.

Using the above procedures, but employing, in place of the acid compound 207.7, different acid compounds 207.1, and/or different phosphonates 207.3, there are obtained the corresponding products 207.5 and 207.6.

The phosphonate-containing benzoic acids, prepared as described in Schemes 206 and 207, are then transformed, using the procedures shown in Scheme 205, into the phenyloxazole piperazine derivatives 205.10.

Scheme 205

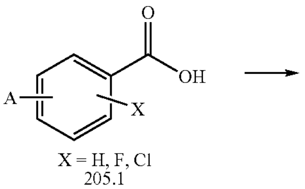

X = H, F, Cl
205.1

-continued

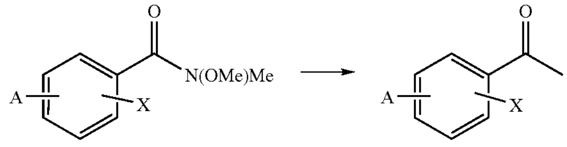

205.2 205.3

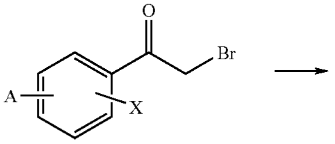

205.4

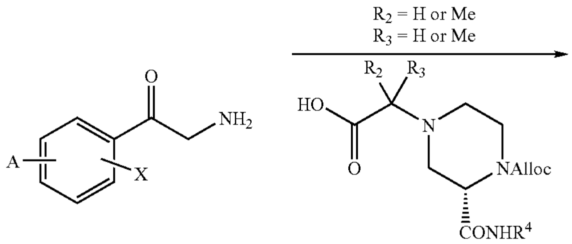

205.6

205.5

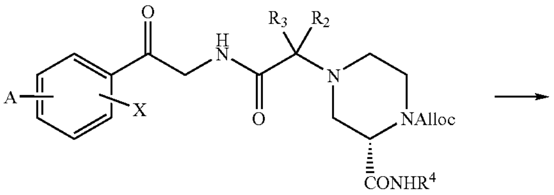

205.7

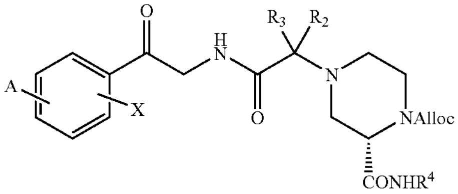

205.8

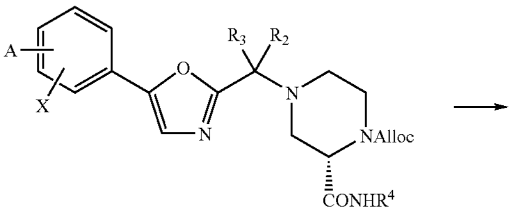

205.9

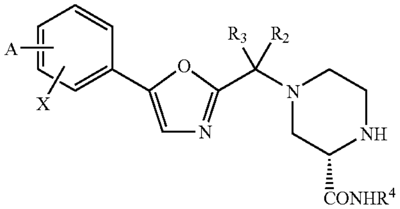

205.10

Scheme 206
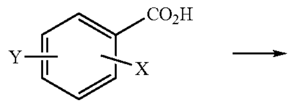
X = H, F, Cl
Y = OH, SH, $NH_2$
206.1
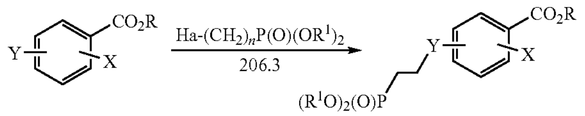
206.2 206.4
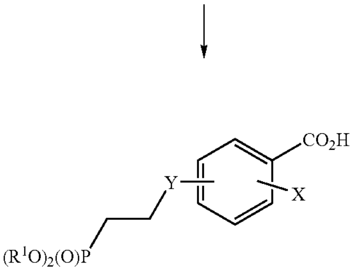
206.5
-continued
Example
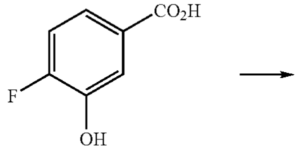
206.6
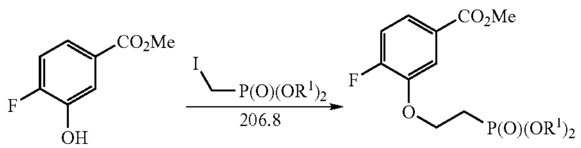
206.7 206.9
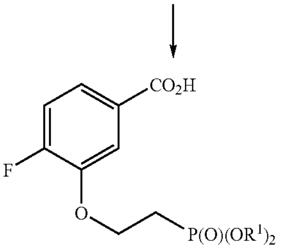
206.10
Scheme 207
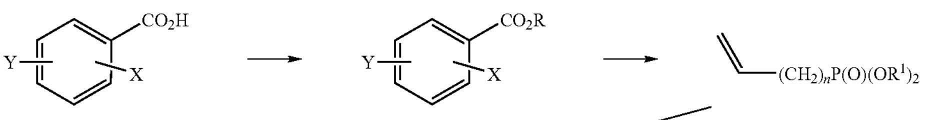
Y = Br, I
X = H, F, Cl
207.1 207.2 207.3
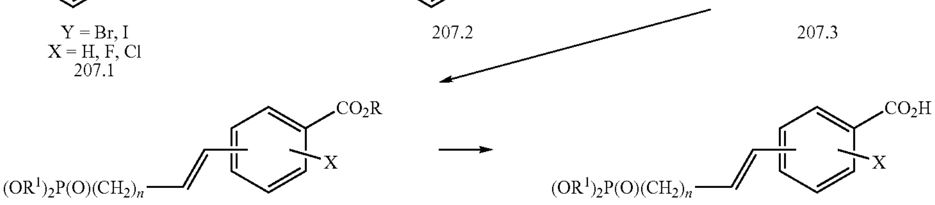
207.4 207.5
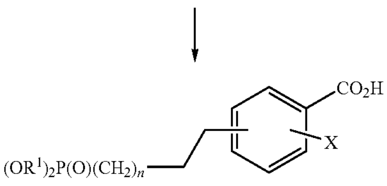
207.6
Example
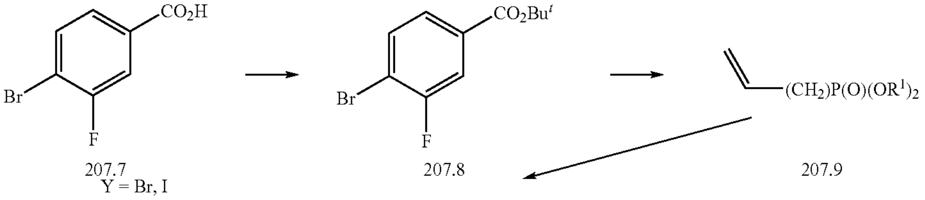
207.7
Y = Br, I
207.8 207.9

-continued

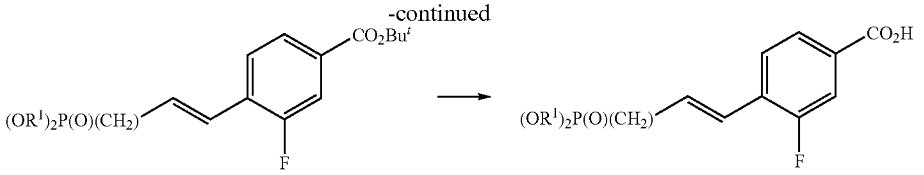

207.10 207.11 207.12

Nelfinavir-like Phosphonate Protease Inhibitors-(NLPPI)

Preparation of the Intermediate Phosphonate Esters.

The intermediate phosphonate esters 1 to 4a of this invention are shown in Chart 1.

Subsequent chemical modifications, as described herein, permit the synthesis of the final compounds of this invention.

The structures of the amine components $R^2NHCH(R^3)CONHBu^t$6-20e are shown in Chart 2. Although specific stereoisomers of some of the amines are shown, all stereoisomers of the amine components are utilized. Chart 2 also illustrates that, in addition to the tert. butyl amines 5, the corresponding 2,2,2-trifluoroethyl and 2-methylbenzyl amides are utilized in the synthesis of the phosphonate intermediate compounds of this invention.

Chart 3 depicts the structures of the $R^4$ components 21-26. Charts 4a-4c illustrate the structures of the carboxylic acid components $R^5COOH$, C1-C49.

The intermediate compounds 1 to 4a incorporate a phosphonate moiety connected to the a nucleus by means of a variable lining group, designated as "link" in the attached structures.

Charts 5 and 5a illustrate examples of the linking groups 38-59 present in the structures 1-4a, and in which "etc" refers to the scaffold, e.g., nelfinavir.

Schemes 1-50 illustrate the syntheses of the intermediate phosphonate compounds of this invention, 1-4a, and of the intermediate compounds necessary for their synthesis.

CHART 1

| Structures of phosphonate ester intermediate compounds |
|---|
| 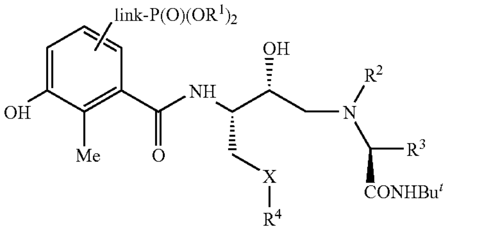 1 |

CHART 1-continued

| Structures of phosphonate ester intermediate compounds |
|---|
| 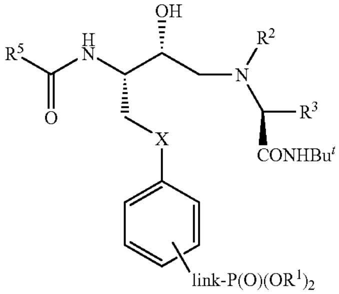 2 |
| 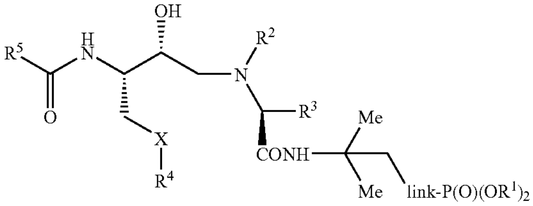 3 |
| 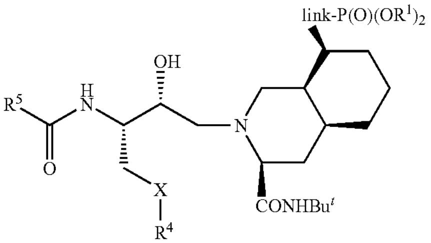 4 |

CHART 1-continued
Structures of phosphonate ester intermediate compounds
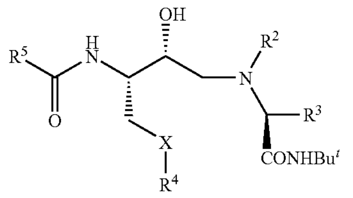
4a
$R^1$ = H, alkyl, alkenyl, aryl, aralkyl
CHART 2
Structures of the amine component $R^2NHCH(R^3)CONHBu^t$
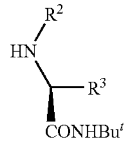
5
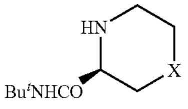
X = N, C
6
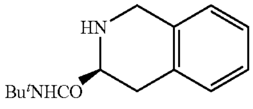
7
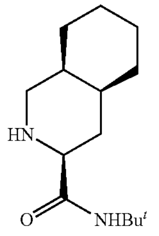
8
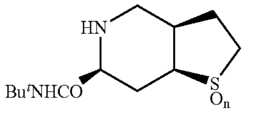
n = 0, 2
9
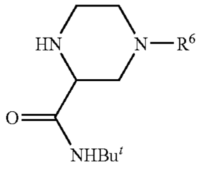
10
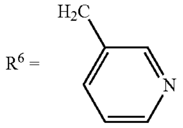
11
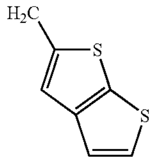
12
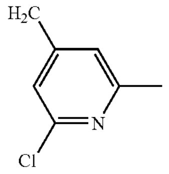
13
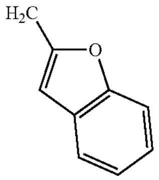
14
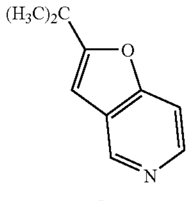
15
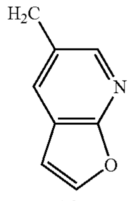
16
CHART 2-continued
Structures of the amine component $R^2NHCH(R^3)CONHBu^t$
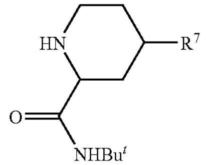
$R^7$ = $OCH_2Ph$
S-3-pyridyl
S-4-pyridyl
$OCH_2$-4-pyridyl
17
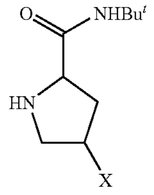
18
X = Cl, OMe
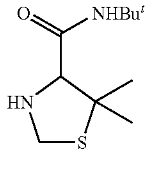
19
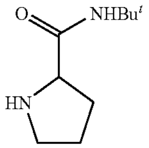
20
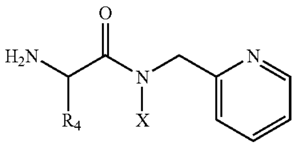
X = H or Me
20a
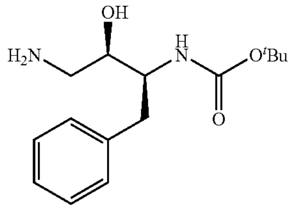
20b
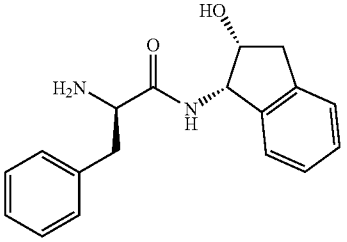
20c
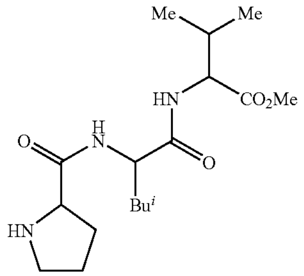
20d CHART 2-continued
Structures of the amine component $R^2NHCH(R^3)CONHBu^t$
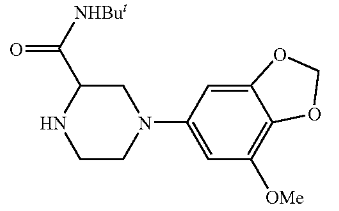
20e
$CONHBu^t$ = $CONHC(CH_3)_3$
$CONHCH_2CF_3$
$CONHCH_2C_6H_4(CH_3)$-2
CHART 3
Structures of the $R^4$ components
$CH_2XR^4$ =
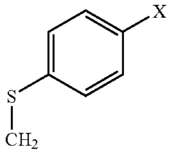
21
X = H, F
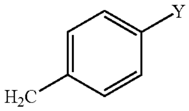
22
Y = H, $OC_2H_5$, $OCH_2C_6H_5$
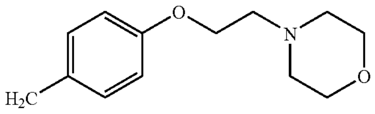
23
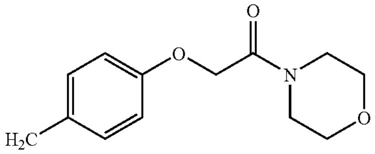
24
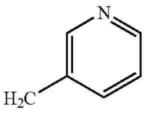
25
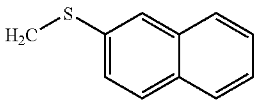
26
CHART 4a
Structures of the $R^5COOH$ components
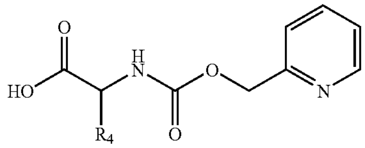
C1
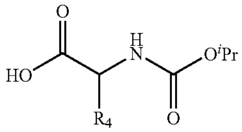
C2
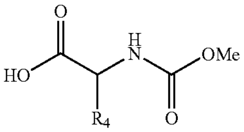
C3
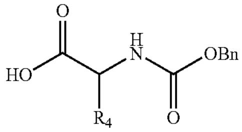
C4
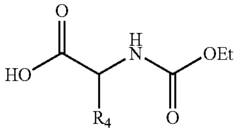
C5
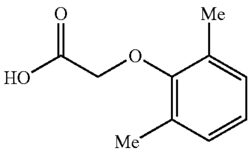
C6
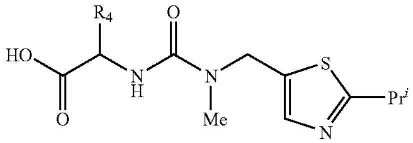
C7
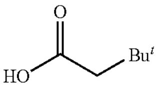
C8
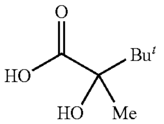
C9
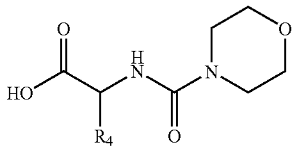
C10
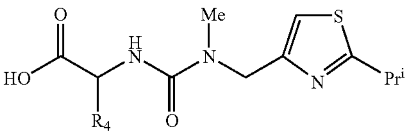
C11
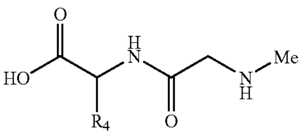
C12

CHART 4a-continued
Structures of the $R^5COOH$ components
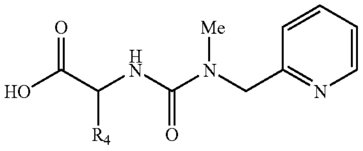
C13
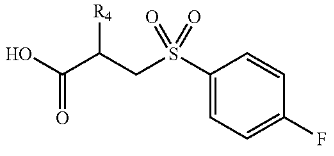
C14
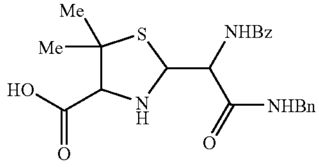
C15
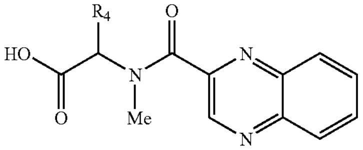
C16
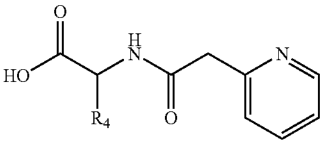
C17
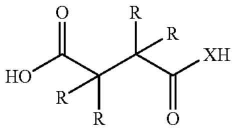
C18
X = O, NH
R = H, alkyl
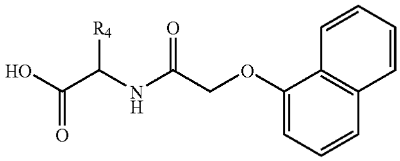
C19
CHART 4a-continued
Structures of the $R^5COOH$ components
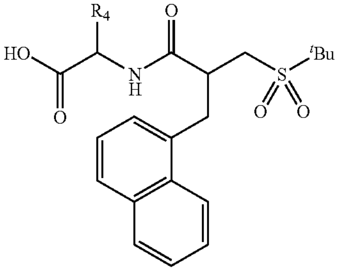
C20
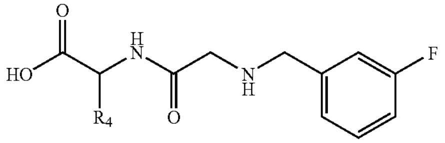
C21
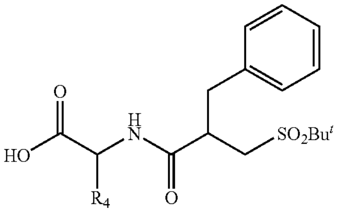
C22
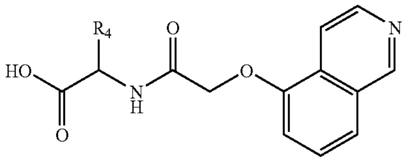
C23
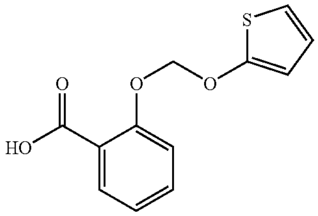
C24
$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 4b
Structures of the $R^5COOH$ components
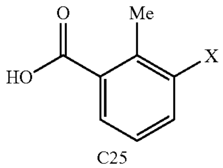
C25
X = OH, $NH_2$
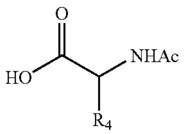
C26

CHART 4b-continued
Structures of the $R^5COOH$ components
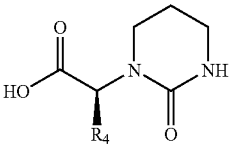
C27
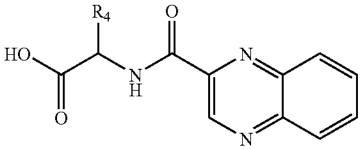
C28
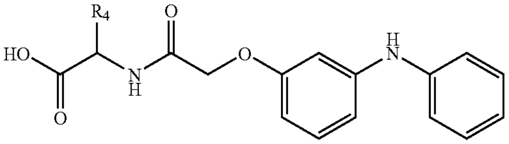
C29
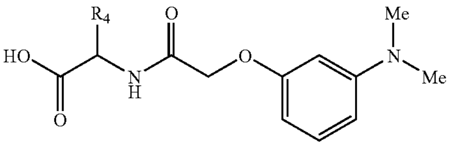
C30
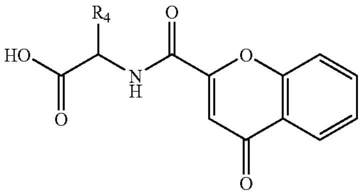
C31
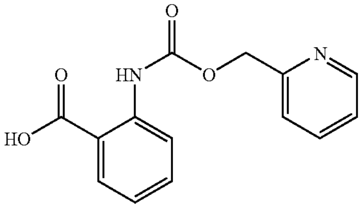
C32
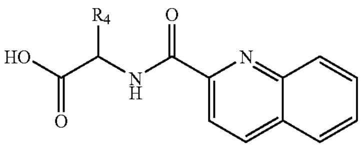
C33
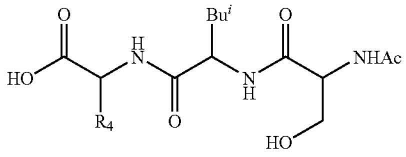
C34
CHART 4b-continued
Structures of the $R^5COOH$ components
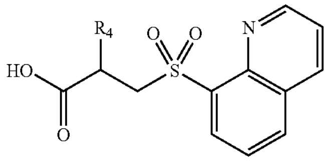
C35
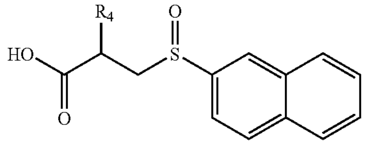
C36
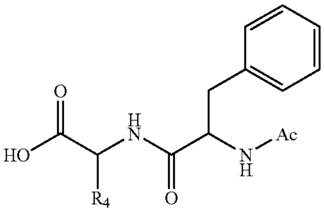
C37
$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 4c
Structures of the $R^5COOH$ components
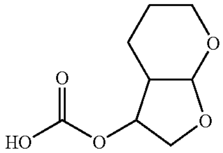
C38
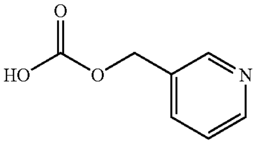
C39
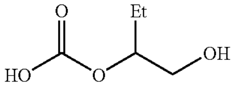
C40
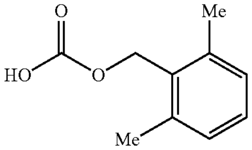
C41
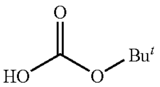
C42
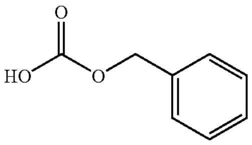
C43
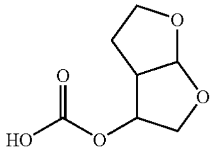
C44
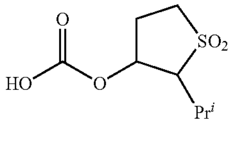
C45

CHART 4c-continued
| Structures of the $R^5COOH$ components | |
|---|---|
| 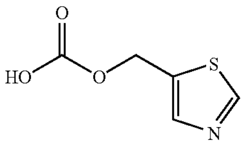 C46 | 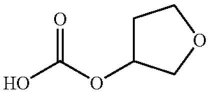 C47 |
| 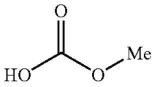 C48 | 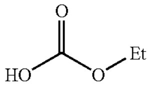 C49 |
CHART 5
Examples of the linking group between the scaffold and the phosphonate moiety.
| link | examples |
|---|---|
| direct bond | 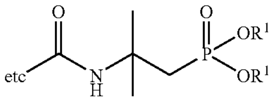 38 |
| | 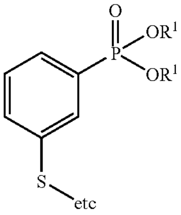 39 |
| | 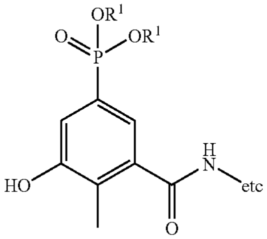 40 |
| single carbon | 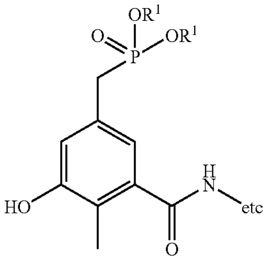 41 |
| | 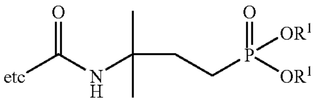 42 |
CHART 5-continued
Examples of the linking group between the scaffold and the phosphonate moiety.
| link | examples |
|---|---|
| | 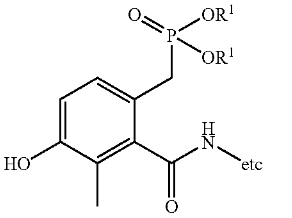 43 |
| multiple carbon | 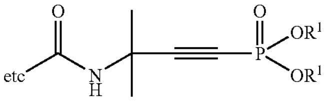 44 |
| | 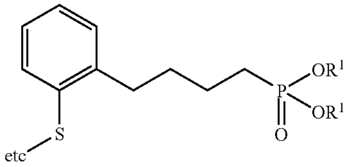 45 |
| | 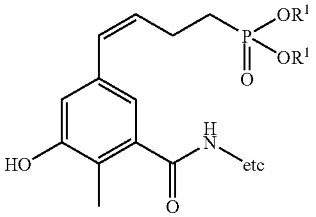 46 |
| hetero atoms | 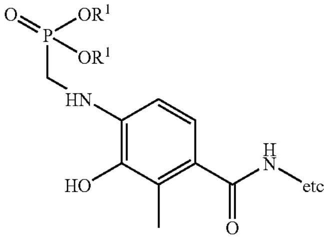 47 |

CHART 5-continued
| Examples of the linking group between the scaffold and the phosphonate moiety. | |
|---|---|
| link | examples |
| | 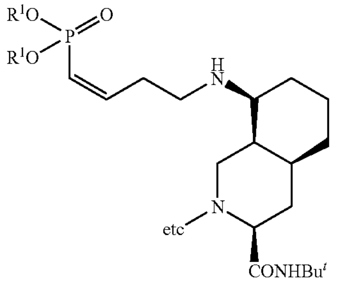 48 |
| | 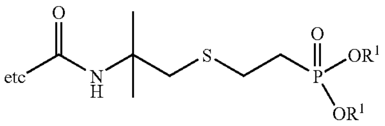 49 |
| | 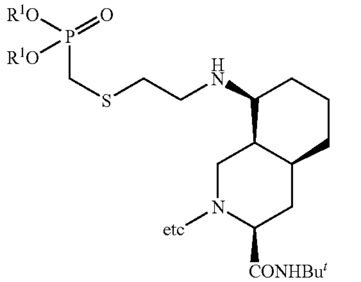 50 |
| | 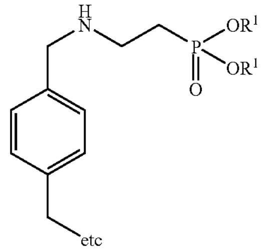 51 |
| | 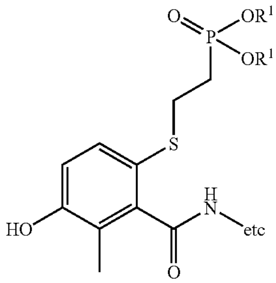 52 |
CHART 5a
| Examples of the linking group between the scaffold and the phosphonate moiety. | |
|---|---|
| link | examples |
| aryl, heteroaryl | 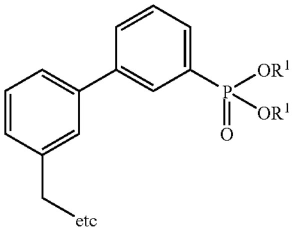 53 |
| | 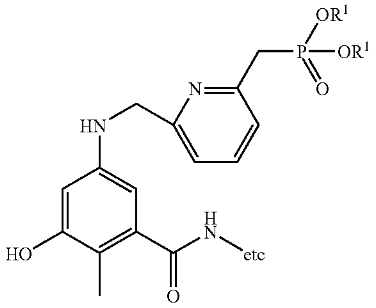 54 |
| | 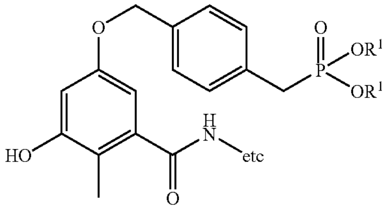 55 |
| cycloalkyl | 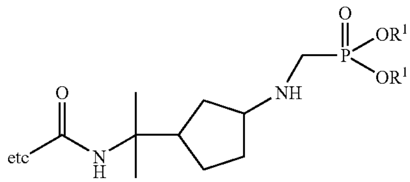 56 |
| | 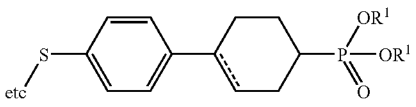 57 |

CHART 5a-continued

Examples of the linking group between the scaffold and the phosphonate moiety.

| link | examples |
| --- | --- |
| cyclized | 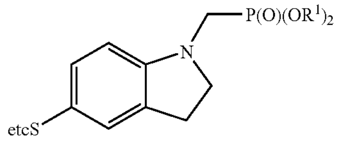 58 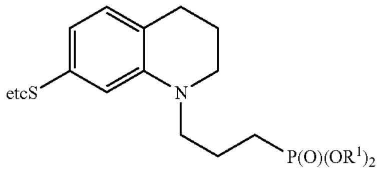 59 |

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Syntheses, by T. W. Greene and P. G. M Wuts, Second Edition 1990. Reactive substituents which may be protected are shown in the accompanying schemes as, for example, [OH], [SH].

Preparation of the Phosphonate Intermediates 1, in which X═S.

The syntheses of the phosphonates 1 in which X═S, and in which the group link-$P(O)(OR^1)_2$ is attached to the benzoic acid moiety, are shown in Schemes 1-3.

Scheme 1 illustrates the preparation of the phosphonate intermediate compounds 1, or precursors thereto. 4-Amino-tetrahydro-furan-3-ol 60, the preparation of which is described in Tet. Lett., 2000, 41, 7017, is reacted with the carboxylic acid 61, or an activated derivative thereof, the preparations of which are described below, to form the amide 62.

The preparation of amides by reaction of carboxylic acids and derivatives is described, for example, in Organic Functional Group Preparations, by S. R. Sandler and W. Karo, Academic Press, 1968, p 274. The carboxylic acid is reacted with the amine in the presence of an activating agent, such as, for example, dicyclohexylcarbodiimide, optionally in the presence of, for example, hydroxybenztriazole, in a non-protic solvent such as, for example, pyridine, DMF or dichloromethane, to afford the amide.

Alternatively, the carboxylic acid may first be converted into an activated derivative such as the acid chloride or anhydride, and then reacted with the amine, in the presence of an organic base such as, for example, pyridine, to afford the amide.

Preferably, the carboxylic acid is first converted into the acid chloride by reaction with, for example, thionyl chloride, oxalyl chloride and the like. The acid chloride 61, in which X is Cl, is then reacted with an equimolar amount of the amine 60, in the presence of a weak inorganic base such as sodium bicarbonate, in an aprotic solvent such as dichloromethane, at ambient temperature, to afford the amide 62.

The hydroxyl group on the tetrahydrofuran moiety so obtained is converted into a leaving group such as p-toluenesulfonyl or the like, by reaction with a sulfonyl chloride in an aprotic solvent such as pyridine or dichloromethane.

Preferably, the hydroxy amide 62 is reacted with an equimolar amount of methanesulfonyl chloride in pyridine, at ambient temperature, to afford the methanesulfonyl ester 63.

The product 63, bearing a suitable sulfonyl ester leaving group, is then subjected to acid-catalyzed rearrangement to afford the isoxazoline 64. The rearrangement reaction is conducted in the presence of an acylating agent such as a carboxylic anhydride, in the presence of a strong acid catalyst.

Preferably, the mesylate 63 is dissolved in an acylating agent such as acetic anhydride at about 0°, in the presence of about 5 mole % of a strong acid such as sulfuric acid, to afford the isoxazoline mesylate 64.

The leaving group, for example a mesylate group, is next subjected to a displacement reaction with an amine.

The compound 64 is reacted with an amine 5, as defined in Chart 2, in a protic solvent such as an alcohol, in the presence of an organic or inorganic base, to yield the displacement product 65.

Preferably, the mesylate compound 64 is reacted with an equimolar amount of the amine 5, in the presence of an excess of an inorganic base such as potassium carbonate, at ambient temperature, to afford the product 65.

The isoxazoline compound 65 is then reacted with a thiol $R^4SH$ 66, in which $R^4$ is phenyl, 4-fluorophenyl or 2-naphthyl, as shown in Chart 3, to afford the thioether 1. The reaction is conducted in a polar solvent such as DMF, pyridine or an alcohol, in the presence of a weak organic or inorganic base, to afford the product 1.

Preferably, the isoxazoline 65 is reacted, in methanol, with an equimolar amount of the thiol $R^4SH$ 66, in the presence of an excess of a base such as potassium bicarbonate, at ambient temperature, to afford the thioether 1.

Alternatively, the compounds 1 can be obtained by means of the reactions shown in Scheme 2. In this sequence, methanesulfonic acid 2-benzoyloxycarbonylamino-2-(2,2-dimethyl-[1,3]dioxolan-4-yl)-ethyl ester, 67, prepared as described in J. Org. Chem, 2000, 65, 1623, is reacted with a thiol $R^4SH$ 66, as defined above, to afford the thioether 68.

The reaction is conducted in a suitable solvent such as, for example, pyridine, DMF and the like, in the presence of an inorganic or organic base, at from 0° to 80°, for from 1-12 hours, to afford 68.

Preferably the mesylate 67 is reacted with an equimolar amount of the thiol $R^4SH$ 66, in a mixture of a water-immiscible organic solvent such as toluene, and water, in the presence of a phase-transfer catalyst such as, for example, tetrabutyl ammonium bromide, and an inorganic base such as sodium hydroxide, at about 50°, to give the product 68.

The 1,3-dioxolane protecting group present in the compound 68 is removed by acid catalyzed hydrolysis or by exchange with a reactive carbonyl compound to afford the diol 69. Methods for conversion of 1,3-dioxolanes to the corresponding diols are described in Protective Groups in Organic Synthesis, by T. W. Greene and P. G. M Wuts, Second Edition 1990, p. 191.

For example, the 1,3-dioxolane compound 68 is hydrolyzed by reaction with a catalytic amount of an acid in an aqueous organic solvent mixture.

Preferably, the 1,3-dioxolane 68 is dissolved in aqueous methanol containing hydrochloric acid, and heated at ca. 50°, to yield the product 69.

The primary hydroxyl group of the diol 69 is then selectively acylated by reaction with an electron-withdrawing acyl halide such as, for example, pentafluorobenzoyl chloride or mono- or di-nitrobenzoyl chlorides. The reaction is conducted in an inert solvent such as dichloromethane and the like, in the presence of an inorganic or organic base.

Preferably, equimolar amounts of the diol 69 and 4-nitrobenzoyl chloride are reacted in a solvent such as ethyl acetate, in the presence of a tertiary organic base such as 2-picoline, at ambient temperature, to afford the ester 70.

The hydroxy ester 70 is next reacted with a sulfonyl chloride such as methanesulfonyl chloride, 4-toluenesulfonyl chloride and the like, in the presence of a base, in an aprotic polar solvent at low temperature, to afford the corresponding sulfonyl ester 71.

Preferably, equimolar amounts of the carbinol 70 and methanesulfonyl chloride are reacted together in ethyl acetate containing triethylamine, at about 10° C., to yield the mesylate 71. The compound 71 is then subjected to a hydrolysis-cyclization reaction to afford the oxirane 72.

The mesylate or analogous leaving group present in 71 is displaced by hydroxide ion, and the carbinol thus produced, without isolation, spontaneously transforms into the oxirane 72 with elimination of 4-nitrobenzoate. To effect this transformation, the sulfonyl ester 71 is reacted with an alkali metal hydroxide or tetraalkylammonium hydroxide in an aqueous organic solvent.

Preferably, the mesylate 71 is reacted with potassium hydroxide in aqueous dioxan at ambient temperature for about 1 hour, to afford the oxirane 72.

The oxirane compound 72 is then subjected to regiospecific ring-opening reaction by treatment with an amine 5, to give the aminoalcohol 73.

The amine and the oxirane are reacted in a protic organic solvent, optionally in the additional presence of water, at 0° to 100°, and in the presence of an inorganic base, for 1 to 12 hours, to give the product 73.

Preferably, equimolar amounts of the reactants 5 and 72 are reacted in aqueous methanol at about 60° in the presence of potassium carbonate, for about 6 hours, to afford 73.

The carbobenzyloxy (cbz) protecting group in the product 73 is removed to afford the free amine 74. Methods for removal of cbz groups are described, for example, in Protective Groups in Organic Synthesis, by T. W. Greene and P. G. M. Wuts, Second Edition, p. 335. The methods include catalytic hydrogenation and acidic or basic hydrolysis.

For example, the cbz-protected amine 73 is reacted with an alkali metal or alkaline earth hydroxide in an aqueous organic or alcoholic solvent, to yield the free amine 74.

Preferably, the cbz group is removed by the reaction of 73 with potassium hydroxide in an alcohol such as isopropanol at ca. 60° to afford the amine 74.

The amine 74 so obtained is next acylated with a carboxylic acid or activated derivative 61, using the conditions described above for the conversion of 60 to 62, to yield the final amide product 75.

The reactions shown in the above-described Schemes 1 and 2 depict the preparation of intermediates 1 in which A is either link-$P(O)(OR^1)_2$ or precursor groups to link-$P(O)(OR^1)_2$ such as OH, SH, NH, as described herein.

Scheme 3 shows the conversion of the compounds 75 in which A is OH, SH, NH, to the compounds 1 in which A is link-$P(O)(OR^1)_2$.

Methods for these transformations are described below, Schemes 20-48, in the descriptions of the preparations of the phosphonate-containing reactants.

Scheme 1

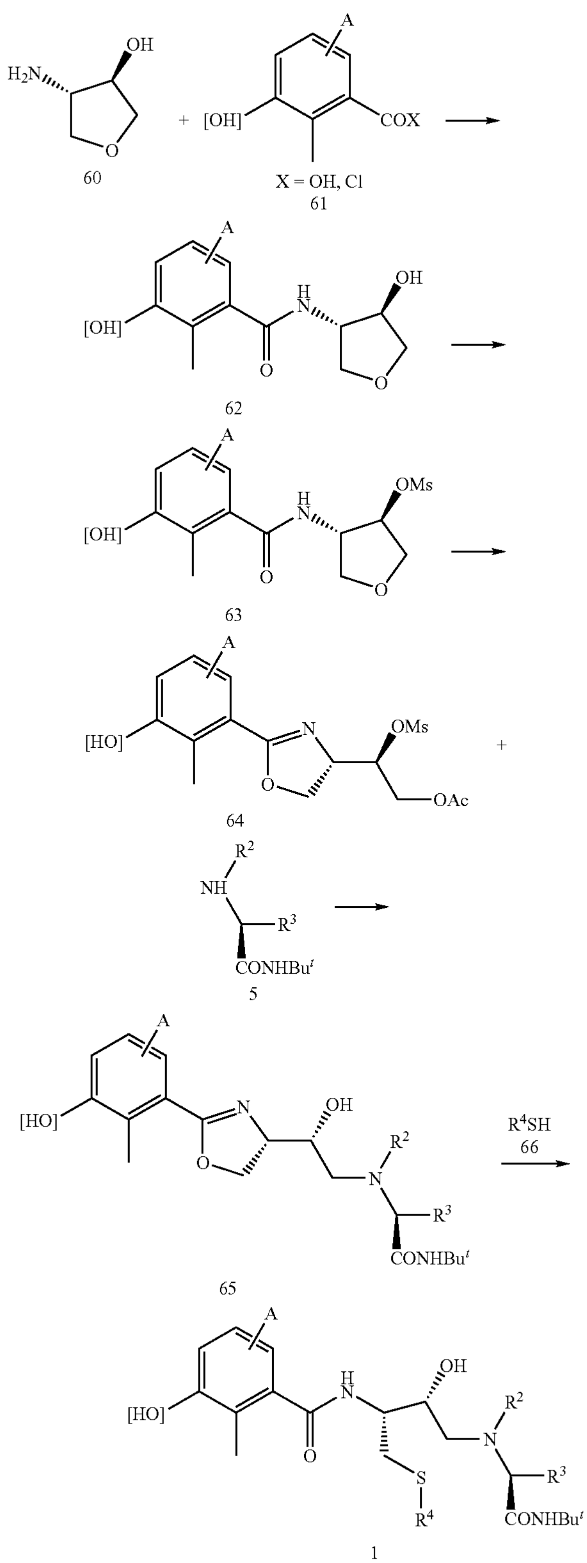

60
61
62
63
64
5
65
1

Scheme 2
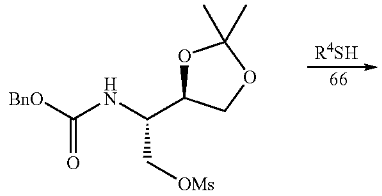
67
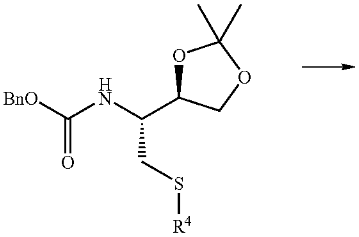
68
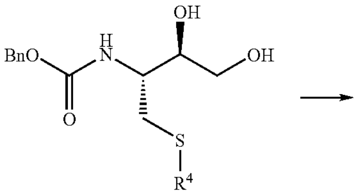
69
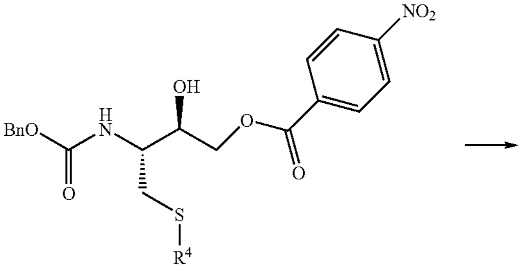
70
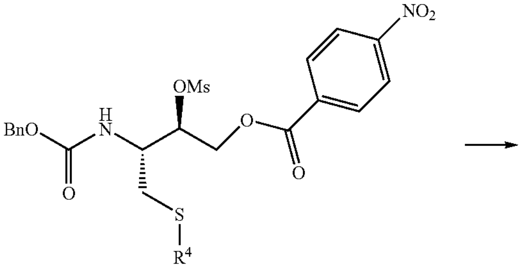
71
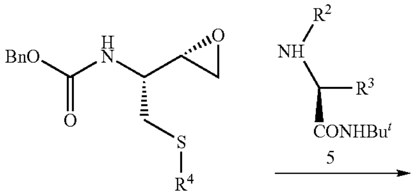
72
-continued
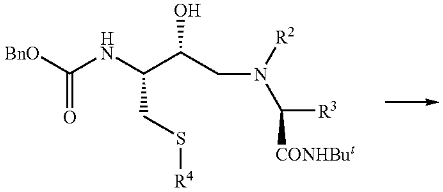
73
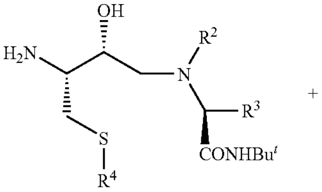
74
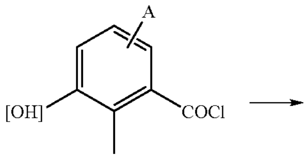
61
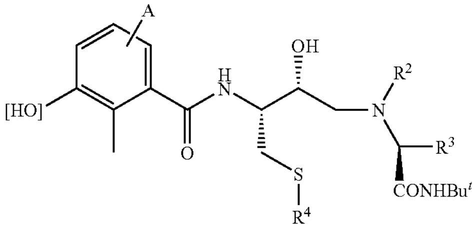
75
Scheme 3
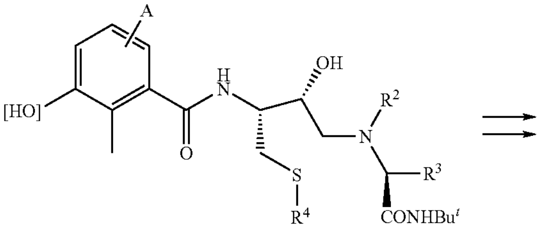
A = OH, SH, $NH_2$ etc
75
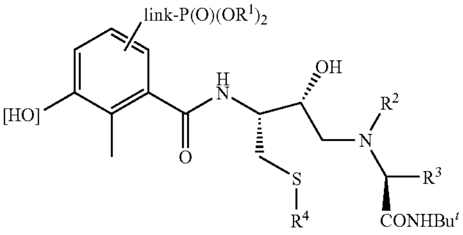
1
Preparation of the Phosphonate Intermediates 2, in which X═S.

The synthesis-of the phosphonate compounds 2 in which the link-$P(O)(OR^1)_2$ group is attached to the phenylthio moiety, is shown in Scheme 4.

In this sequence, 4-amino-tetrahydro-furan-3-ol, 60, the preparation of which is described in Tet. Lett., 2000, 41, 7017, is reacted with a carboxylic acid or activated derivative thereof, $R^5COX$, 76, using the conditions described above for the preparation of the amide 62, Scheme 1, to afford the amide 77. The compounds 77, and analogous acylation products described below, in which the carboxylic acid $R^5COOH$ is one of the carbonic acid derivatives C36-C49, as defined in Chart 4c, are carbamates. Methods for the preparation of carbamates are described below, (Scheme 50).

The amide product 77 is then transformed, using the sequence of reactions shown in Scheme 4, into the isoxazoline compound 80. The conditions for this sequence of transformations are the same as those described for the preparation of the isoxazoline 65 in Scheme 1.

The isoxazoline compound 80 is then reacted with a thiol compound 66, in which the substituent A is either the group link-$P(O)(OR^1)_2$, or a precursor thereto, such as OH, SH, NH, as described herein, to afford the thioether 81.

The conditions for this reaction are the same as those described above for the preparation of the thioether 1, (Scheme 1).

Alternatively, the thioether 81 can be prepared by the sequence of reactions shown in Scheme 5. In this sequence, the previously described 1,3-dioxolane mesylate compound 67 is reacted with a thiol compound 66 in which the substituent A is either the group link-$P(O)(OR^1)_2$, or a precursor thereto, such as OH, SH, NH, as described herein, to afford the thioether 82. The conditions for this reaction are the same as those described above for the preparation of the thiether 68, (Scheme 2).

The thus-obtained thioether 82 is then transformed, using the sequence of reactions shown in Scheme 2 into the compound 81.

The reactions shown in the above-described Schemes 4 and 5 depict the preparation of intermediates 81 in which A is either link-$P(O)(OR^1)_2$ or precursor groups to link-P(O) $(OR^1)_2$ such as OH, SH, NH, as described herein.

Scheme 6 shows the conversion of the compounds 81 in which A is OH, SH, NH, into the compounds 2 in which A is link-$P(O)(OR^1)_2$.

Methods for these transformations are shown in Schemes 20-48 and are discussed in the descriptions of the preparations of the phosphonate-containing reactants.

Scheme 4

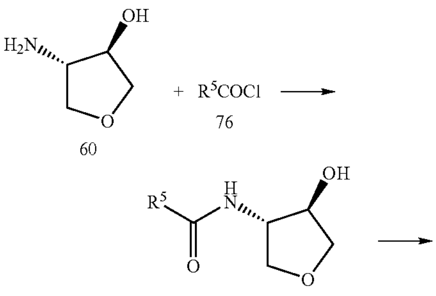

60

76

77

-continued

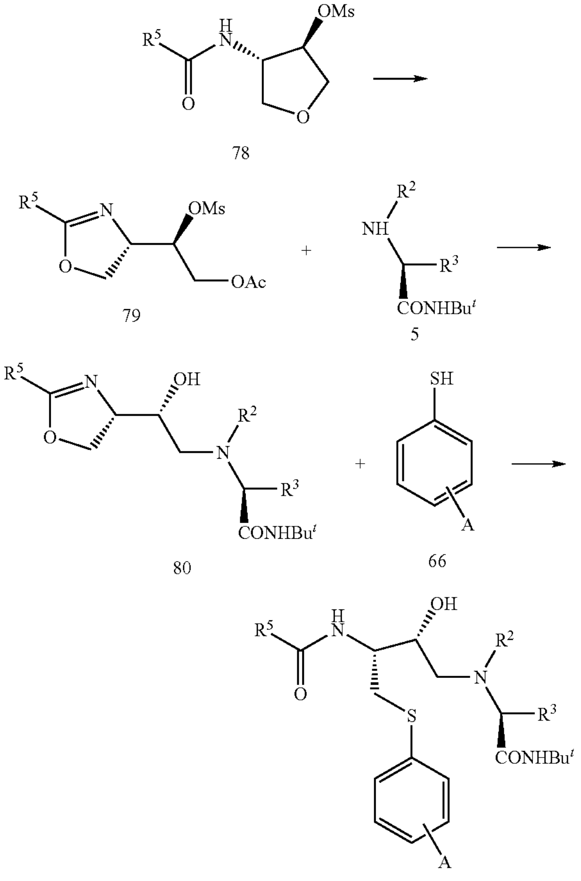

78

79

5

80

66

81

A = link-$(P)(OR^1)_2$ or A = OH, SH, NH, etc.

Scheme 5

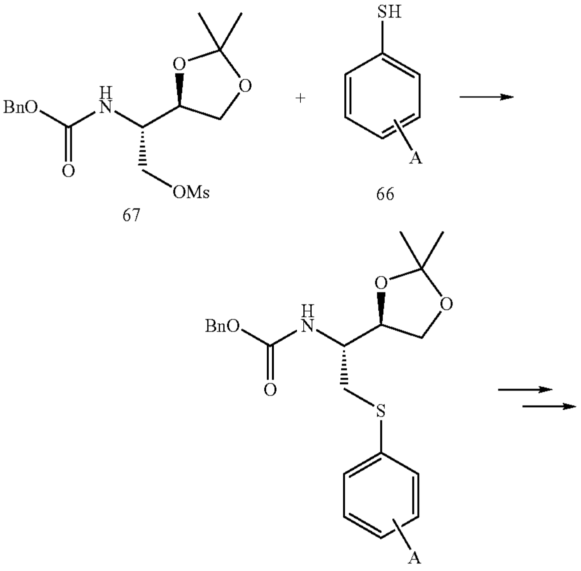

67

66

82

-continued

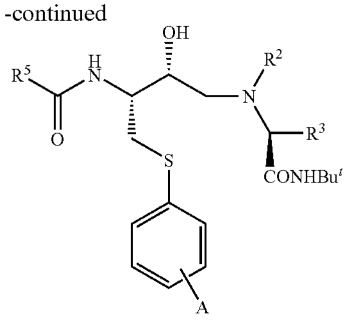

81

A = link-P(O)$(OR^1)_2$ or

A = OH, SH, NH, etc

Scheme 6

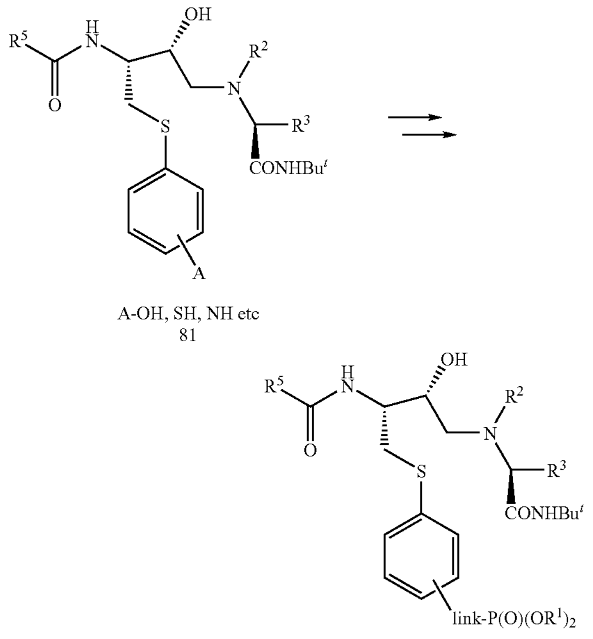

A-OH, SH, NH etc

81

2

Preparation of the Phosphonate Intermediates 3, in which X═S.

The phosphonate intermediates 3 in which X═S, and in which the link-P(O)$(OR^1)_2$ group is attached to the tert. butyl moiety, are prepared as shown in Schemes 7 and 8.

As shown in Scheme 7, the isoxazolines 79, the preparation of which are described above, are reacted with the amines 83, using the conditions described above for the conversion of 64 to 65, (Scheme 1) to afford the product 84.

This compound is then converted, using the methods described above, (Scheme 1) into the compound 85, in which B is either link-P(O)$(OR^1)_2$ or precursor groups to link-P(O)$(OR^1)_2$ such as OH, SH, NH, as described herein.

Alternatively, the compounds 85 can be prepared by the reactions shown in Scheme 8.

In this method, the oxirane 72, the preparation of which is described above, (Scheme 2) is reacted with the amine 83, using the reaction conditions described above for the conversion of 72 to 73 (Scheme 2), to afford the hydroxyamine 86. This compound is then converted, using the procedures described above, into the compound 85, in which B is either link-P(O)$(OR^1)_2$ or precursor groups to link-P(O)$(OR^1)_2$ such as OH, SH, NH, as described herein.

The reactions shown in the above-described Schemes 7 and 8 depict the preparation of intermediates 85 in which A is either link-P(O)$(OR^1)_2$ or precursor groups to link-P(O)$(OR^1)_2$ such as OH, SH, NH, as described herein.

Scheme 9 shows the conversion of the compounds 85 in which A is OH, SH, NH, into the compounds 3 in which A is link-P(O)$(OR^1)_2$.

Methods for these transformations are described below in Schemes 20 to 48 in which the preparations of the phosphonate-containing reactants are depicted.

Preparation of the Phosphonate Intermediates 4 in which X═S.

The preparations of the phosphonate intermediates 4, in which the link-P(O)$(OR^1)_2$ group is attached to the decahydroisoquinoline moiety, are shown in Schemes 10 to 12.

As shown in Scheme 10, the isoxazoline mesylate 79, the preparation of which is described above, (Scheme 4) is reacted with the amine 88, the preparation of which is described below. The reaction is preformed using the procedures described above for the preparation of 65 (Scheme 1).

The reaction product 89 is then transformed, using the procedures described above, (Scheme 1) into the compound 90, in which B is either link-P(O)$(OR^1)_2$ or precursor groups to link-P(O)$(OR^1)_2$ such as OH, SH, NH, as described herein.

Alternatively, the compound 90 can be prepared by the reactions shown in Scheme 11.

In this reaction scheme, the oxirane 72, the preparation of which is described above, (Scheme 2) is reacted with the amine 88, using the conditions described above for the preparation of 73 (Scheme 2) to afford the hydroxyamine 91. This compound is then converted, using the reaction schemes and conditions described above for the preparation of 1, (Scheme 2) into the compound 90, in which B is either link-P(O)$(OR^1)_2$ or precursor groups to link-P(O)$(OR^1)_2$ such as OH, SH, NH, as described herein.

The reactions shown in the above-described Schemes 10 and 11 depict the preparation of intermediates 90 in which B is either link-P(O)$(OR^1)_2$ or precursor groups to link-P(O)$(OR^1)_2$ such as OH, SH, NH, as described herein.

Scheme 12 shows the conversion of the compounds 90 in which B is OH, SH, NH, to the compounds 4 in which A is link-P(O)$(OR^1)_2$.

Methods for these transformations are described below in Schemes 20-48 in which the preparations of the phosphonate-containing reactants are depicted.

Preparation of the Phosphonate Intermediates 1, in which X is a Direct Bond

As shown in Scheme 13, the oxirane 92, in which X is H, the preparation of which is described in J. Med. Chem., 1997, 40, 1995, and in Bioorg. Med. Chem. Lett., 5, 2885, 1995, is reacted with the amine 5. The compounds are reacted together using the conditions described above for the preparation of 73, (Scheme 2) to afford the hydroxyamine 93. This compound is then transformed, using the procedures described above for the preparation of 1, (Scheme 2) into the compound 94, in which A is either link-P(O)$(OR^1)_2$ or precursor groups to link-P(O)$(OR^1)_2$ such as OH, SH, NH, as described herein.

Scheme 14 shows the conversion of the compounds 94 in which A is OH, SH, NH, to the compounds 1 in which A is link-P(O)$(OR^1)_2$.

Methods for these transformations are described below in Schemes 20-43 in which the preparations of the phosphonate-containing reactants are depicted.

Preparation of the Phosphonate Intermediates 2, in which X is a Direct Bond.

The preparation of the compounds 2, in which X is a direct bond, and the group link-P(O)($OR^1$)$_2$ is attached to the phenyl ring, is illustrated in Schemes 14a and 14b.

In the procedure shown in Scheme 14a, the epoxide 14a-1, prepared as described below (Scheme 45) is reacted with an amine 5, using the conditions described above for the preparation of the hydroxyamine 73 (Scheme 2), to afford the hydroxyamine 14a-2. The latter compound, after removal of the BOC protecting group as described in Protective Groups in Organic Synthesis, by T. W. Greene and P. G. M. Wuts, Third Edition 1999, p. 520-522, is then converted, by reaction with the carboxylic acid $R^5$COOH, or an activated derivative thereof, into the amide 14a-3. The conditions for this reaction are the same as those described above for the preparation of the amide 62, (Scheme 1).

The reactions shown in Scheme 14a illustrate the preparation of the compounds 14a-3 in which A is either the group link-P(O)($OR^1$)$_2$ or a precursor thereto such as OH, SH, $NH_2$. Scheme 14b illustrates the conversion of the compounds 14a-3, in which A is OH, SH, $NH_2$, into the compounds 2 in which A is the group link-P(O)($OR^1$)$_2$. The methods for this transformation are described below in Schemes 20-48, in which the preparation of the phosphonate-containing reactants are described.

Scheme 7

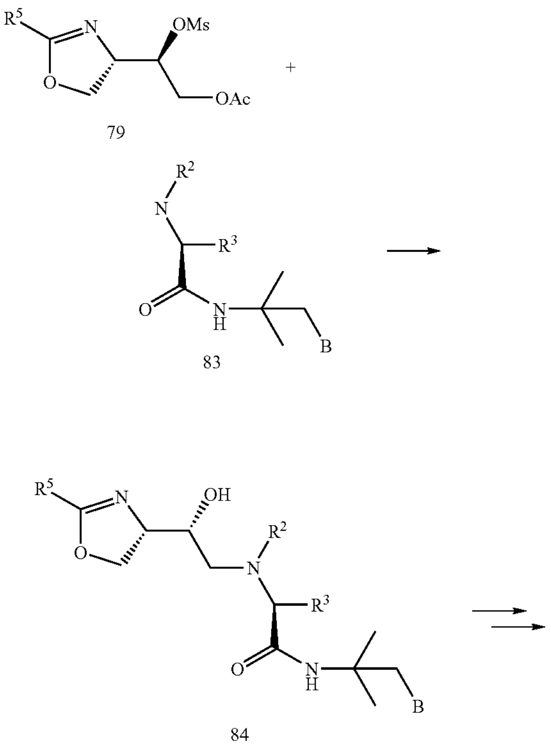

79

83

84

-continued

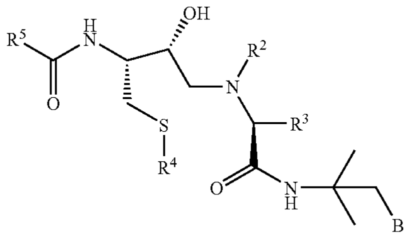

85

B = link-(P)($OR^1$)$_2$ or

B = OH, SH, NH etc.

Scheme 8

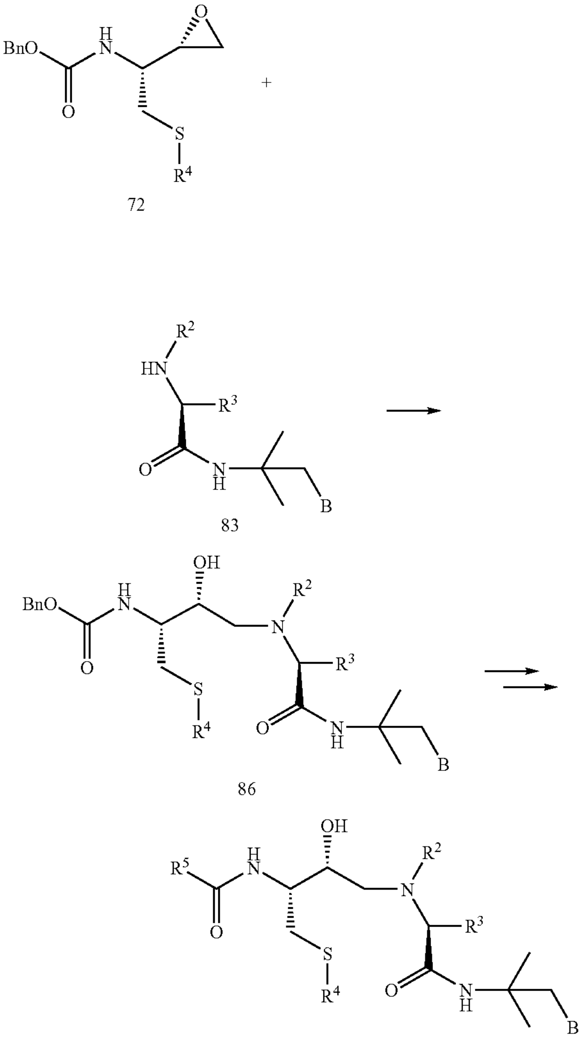

72

83

86

85

B = link-(P)($OR^1$)$_2$ or

B = OH, SH, NH etc.

Scheme 9
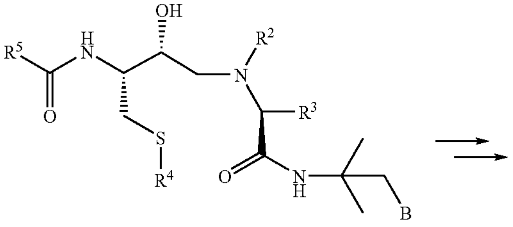
85
B = OH, SH, NH etc.
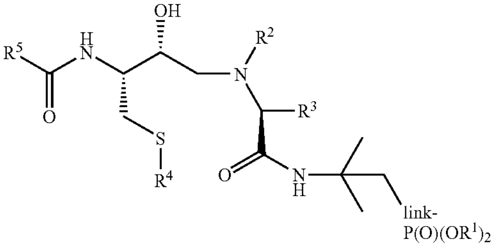
3
Scheme 10
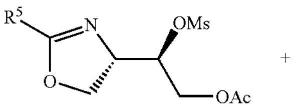
79
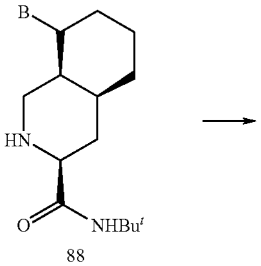
88
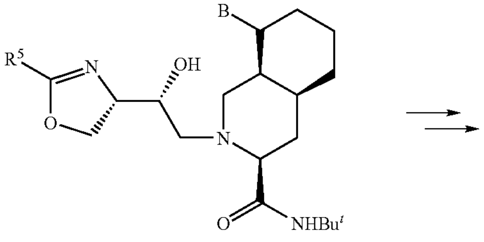
89
-continued
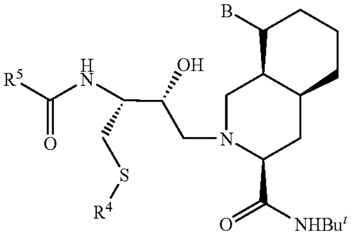
90
B = link-(P)(OR[1])$_2$ or
B = OH, SH, NH etc
Scheme 11
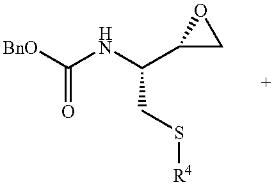
72
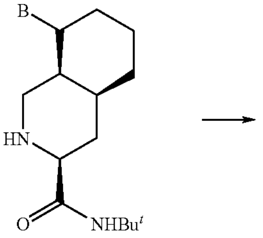
88
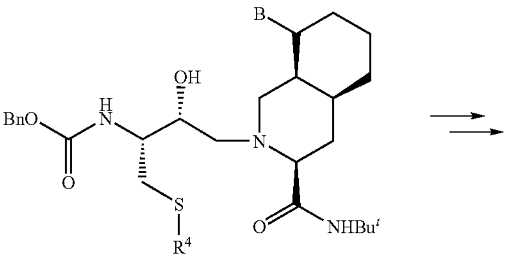
91
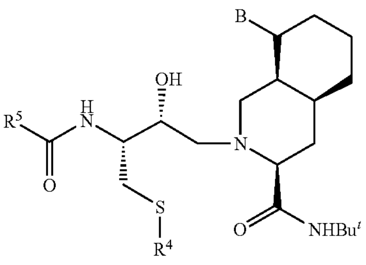
90
B = link-(P)(OR[1])$_2$ or
B = OH, SH, NH etc Scheme 12
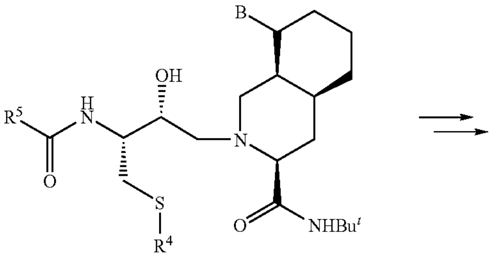
90
B = OH, SH, NH etc
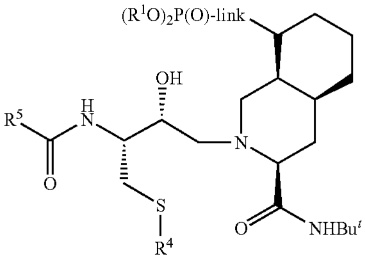
4
Scheme 13
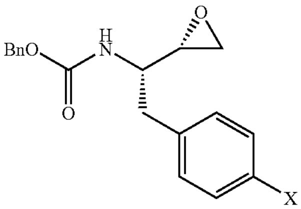
92
X = H, [OH]
+
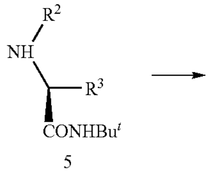
5
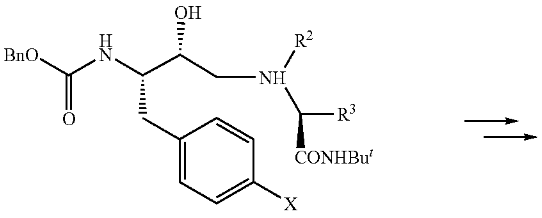
93
-continued
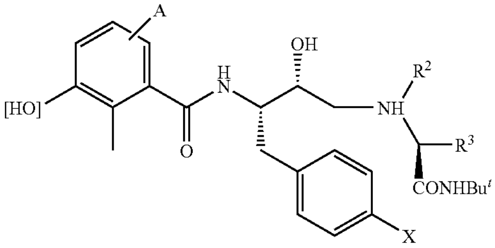
94
A = link-(P)($OR^1$)$_2$ or
A = OH, SH, NH etc
Scheme 14
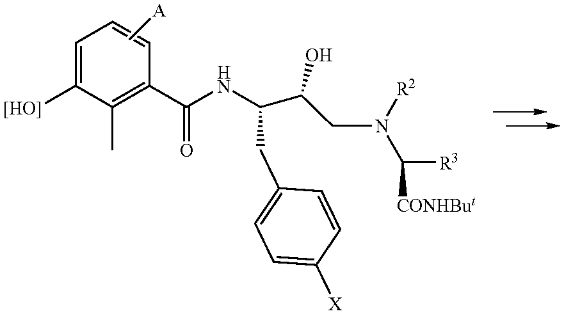
94
X = H, [OH]A = OH, SH, $NH_2$ etc
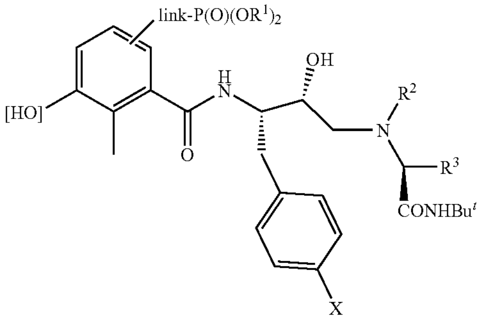
1
Scheme 14a
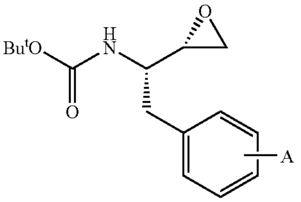
+
A = link-(P)($OR^1$)$_2$ or
A = OH, SH, NH etc
14a-1

-continued

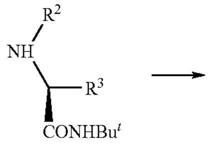

5

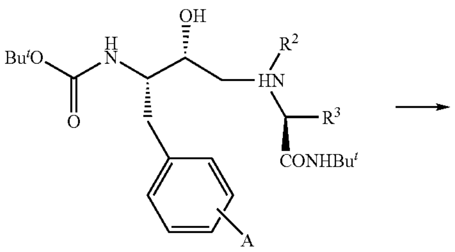

14a-2

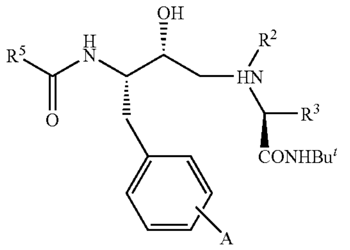

14a-3

Scheme 14b

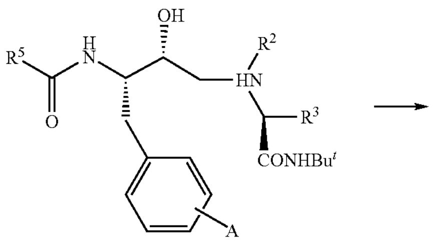

A = OH, SH, NH etc
14a-3

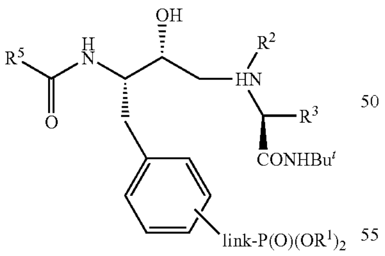

2

Preparation of the Phosphonate Intermediates 3, in which X is a direct Bond.

As shown in Scheme 15, the oxirane 92, in which X is H, is reacted with the amine 83, in which the phosphonate or precursor group is attached to the tert. butyl group, to afford the product 95. The conditions for this reaction are the same as described above for the preparation of 73 (Scheme 2). This compound is then transformed, using the procedures described above for the preparation of 1, (Scheme 2) into the compound 96, in which B is either link-$P(O)(OR^1)_2$ or precursor groups to link-$P(O)(OR^1)_2$ such as OH, SH, NH, as described herein.

Scheme 16 shows the conversion of the compounds 96 in which B is OH, SH, NH, to the compounds 3 in which B is link-$P(O)(OR^1)_2$.

Methods for these transformations are described below in Schemes 20-48 in which the preparations of the phosphonate-containing reactants are depicted.

Preparation of the Phosphonate Intermediates 4, in which X is a Direct Bond.

As shown in Scheme 17, the oxirane 92 is reacted with the amine 88, in which the phosphonate or precursor group is attached to the decahydroisoquinoline moiety, to afford the product 97. The conditions for this reaction are the same as described above for the preparation of 73 (Scheme 2). This compound is then transformed, using the procedures described above for the preparation of 1, (Scheme 2) into the compound 98, in which B is either link-$P(O)(OR^1)_2$ or precursor groups to link-$P(O)(OR^1)_2$ such as OH, SH, NH, as described herein.

Scheme 18 shows the conversion of the compounds 98 in which B is OH, SH, NH, into the compounds 4 in which B is link-$P(O)(OR^1)_2$.

Methods for these transformations are described below in Schemes 20-48 in which the preparations of the phosphonate-containing reactants are depicted.

Schemes 13-18 illustrate the preparations of the compounds 1, 3 and 4, in which X is a direct bond, and in which the phenyl ring is either unsubstituted or incorporates a protected hydroxyl group at the 4-position.

Scheme 19 depicts the synthesis of compounds 1, 3 and 4, in which X is a direct bond, and in which the phenyl ring incorporates different substituents, as described above (Chart 3) in the 4-position.

In this procedure, [2-(4-hydroxy-phenyl)-1-oxiranyl-ethyl]-carbamic acid tert-butyl ester 99, the preparation of which is described in U.S. Pat. No. 5,492,910, is reacted with an appropriate alkylating agent, such as, for example, ethyl iodide, benzyl chloride, bromoethyl morpholine or bromoacetyl morpholine. The reaction is conducted in an aprotic solvent, such as, for example, dichloromethane or dimethylformamide, in the presence of an organic or inorganic base.

Preferably the hydroxy compound 99 is reacted with an equimolar amount of the alkylating agent in dichloromethane, in the presence of diisopropylethylamine, at ambient temperature, so as to afford the ether products 100. The compounds 100 are then transformed, using the conditions described above for the reactions depicted in Schemes 13-18, into the products 1, 3 and 4, in which X is a direct bond, and in which R is as defined in Scheme 19.

Scheme 15

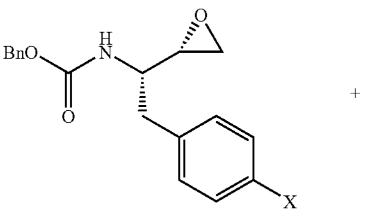

92
X = H, [OH]

-continued
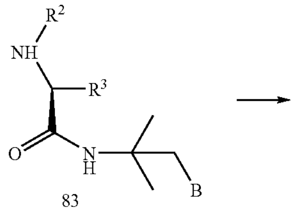
83
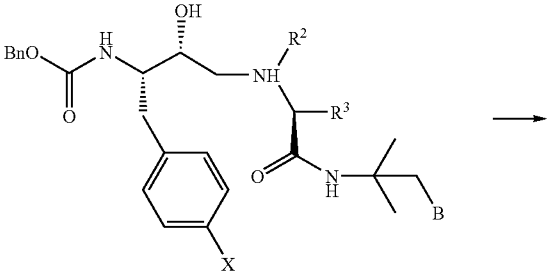
95
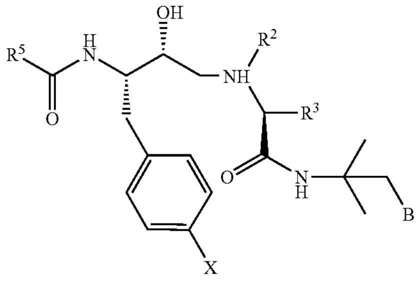
96
B = link-(P)(OR$^1$)$_2$ or
B = OH, SH, NH etc
Scheme 16
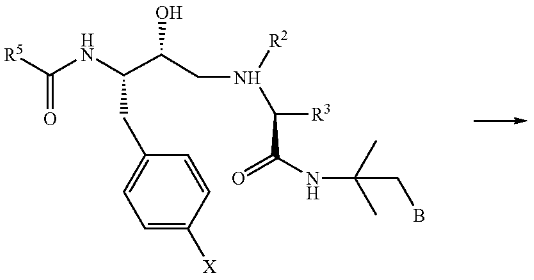
96
X = H, [OH]B = OH, SH, NH etc
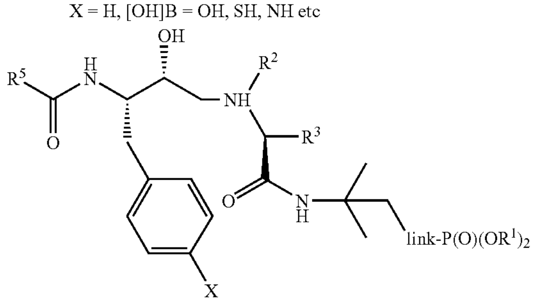
3
Scheme 17
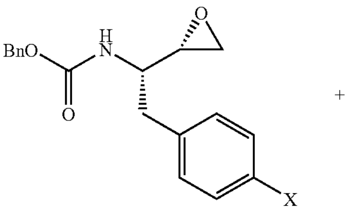
X = H, [OH]
92
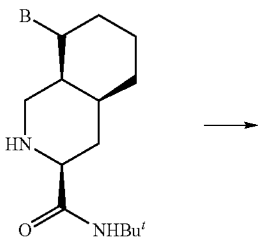
88
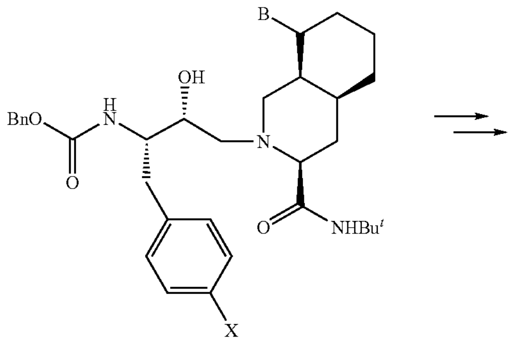
97
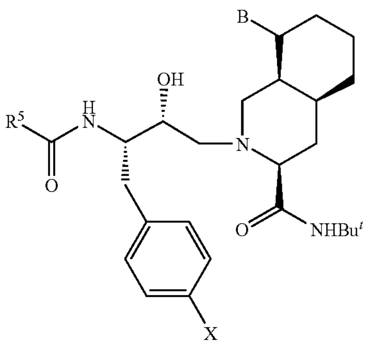
98
B = link-(P)(OR$^1$)$_2$ or
B = OH, SH, NH etc Scheme 18
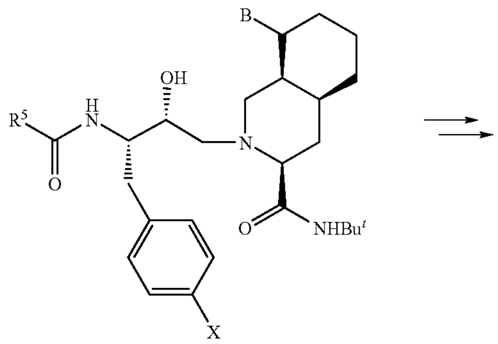
98
B = OH, SH, NH etc
X = H, [OH]
-continued
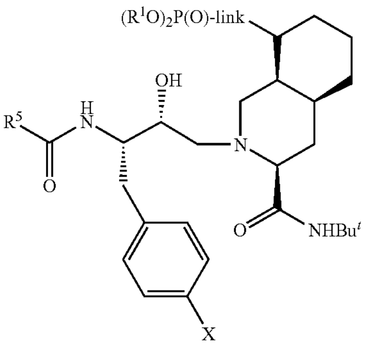
4
Scheme 19
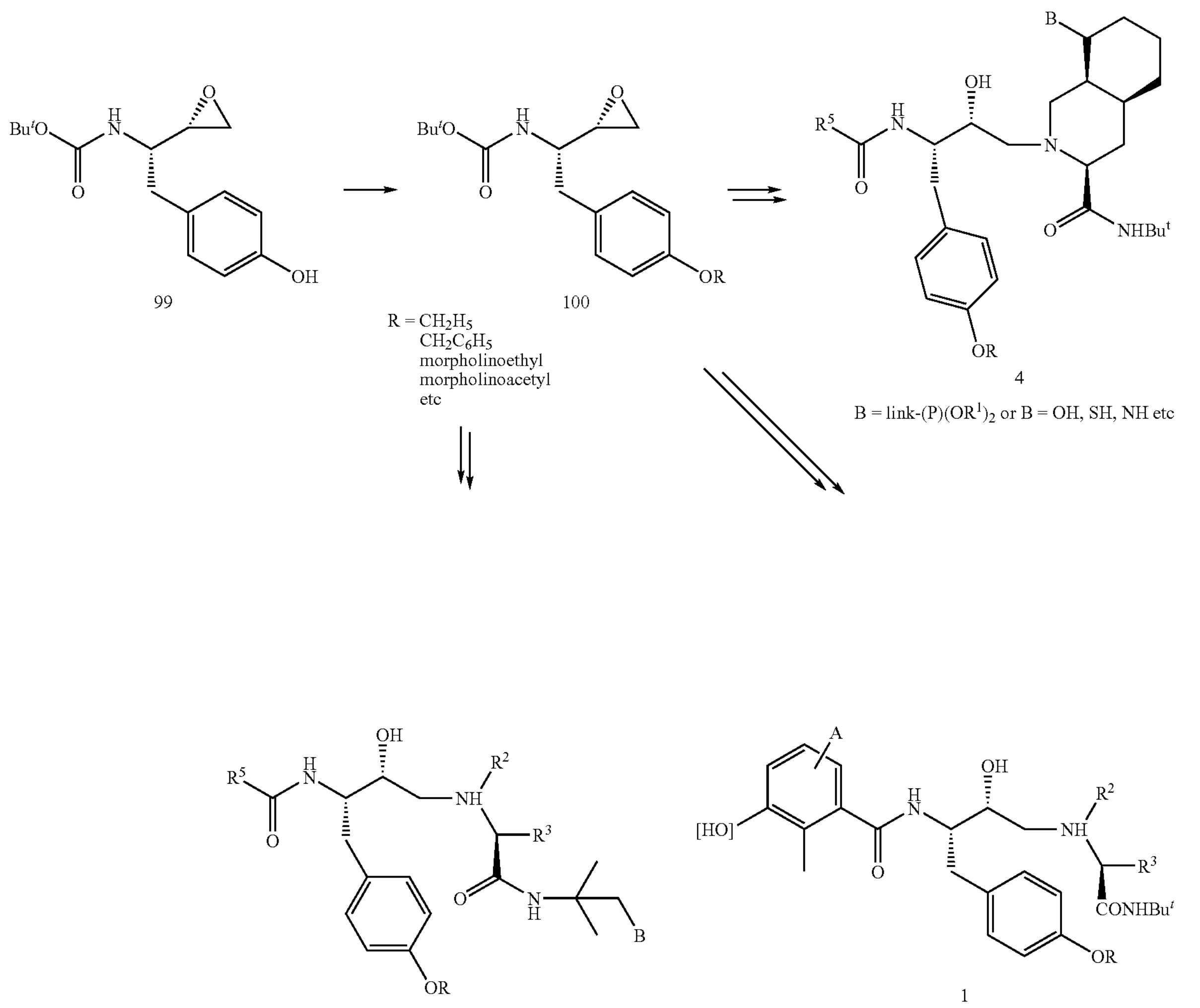
99
100
R = $CH_2H_5$
$CH_2C_6H_5$
morpholinoethyl
morpholinoacetyl
etc
4
B = link-(P)$(OR^1)_2$ or B = OH, SH, NH etc
3
B = link-(P)$(OR^1)_2$ or B = OH, SH, NH etc
1
A = link-(P)$(OR^1)_2$ or A = OH, SH, NH etc Nel10b.cdx Schemes 19a, 19b Preparation of Thiophenol Derivatives $R^4SH$ Incorporating Phosphonate Substituents Various methods for the preparation of thiols are described in The Chemistry of the Thiol Group, S. Patai, Ed., Wiley, 1974, Vol. 14, Part 3, p 42.

Protection/Deprotection of SH Groups.

The preparations of thiophenols incorporating phosphonate moieties are shown in Schemes 20-30. In order to avoid unwanted reactions, it may be necessary to protect the SH group, and to deprotect it after the transformations shown. Protected SH groups are shown in the Schemes as [SH]. The protection and deprotection of SH groups is described in a number of publications. For example, in Protective Groups in Organic Synthesis, by T. W. Greene and P. G. M. Wuts, Wiley, 1991, pp. 277-308, are described the introduction and removal of a number of SH protecting groups. The selection of a SH protecting group for a given series of reactions requires that it be stable to the reaction conditions employed, and that the protecting group can be removed at the end of the reaction sequence without the occurrence of undesired reactions. In the following descriptions, appropriate protection and deprotection methods are indicated.

Scheme 20 illustrates the preparation of thiophenols in which a phosphonate moiety is attached directly to the aromatic ring.

In this procedure, a halo-substituted thiophenol is subjected to a suitable protection procedure.

The protected compound 101 is then coupled, under the influence of a transition metal catalyst, with a dialkyl phosphite 102, to afford the product 103. The product is then deprotected to afford the free thiophenol 104.

Suitable protecting groups for this procedure include alkyl groups such as triphenylmethyl and the like. Palladium (0) catalysts are employed, and the reaction is conducted in an inert solvent such as benzene, toluene and the like, as described in J. Med. Chem., 35, 1371, 1992. Preferably, the 3-bromothiophenol 105 is protected by conversion to the 9-fluorenylmethyl derivative, as described in Protective Groups in Organic Synthesis, by T. W. Greene and P. G. M. Wuts, Wiley, 1991, p. 284, and the product 106 is reacted in toluene with a dialkyl phosphite in the presence of tetrakis (triphenylphosphine)palladium (0) and triethylamine, to yield the product 108. Deprotection, for example by treatment with aqueous ammonia in the presence of an organic co-solvent, as described in J. Chem. Soc. Chem. Comm. 1501, 1986, then gives the thiol 109.

Using the above procedures, but employing, in place of the bromo compound 105, different bromo compounds 101, there are obtained the corresponding thiols 104.

Scheme 21 illustrates an alternative method for obtaining thiophenols with a directly attached phosphonate group. In this procedure, a suitably protected halo-substituted thiophenol 101 is metallated, for example by reaction with magnesium or by transmetallation with an alkyllithium reagent, to afford the metallated derivative 110. The latter compound is reacted with a halodialkyl phosphate 111 to afford the product 103.

Preferably, the 4-bromothiophenol 112 is converted into the S-triphenylmethyl (trityl) derivative 113, as described in Protective Groups in Organic Synthesis, by T. W. Greene and P. G. M. Wuts, Wiley, 1991, pp. 287. The product is converted into the lithium derivative 114 by reaction with butyllithium in an ethereal solvent at low temperature, and the resulting lithio compound is reacted with a dialkyl chlorodiethyl phosphite 115 to afford the phosphonate 116. Removal of the trityl group, for example by treatment with dilute hydrochloric acid in acetic acid, as described in J. Org. Chem., 31, 1118, 1966, then affords the thiol 117.

Using the above procedures, but employing, in place of the halo compound 112, different halo compounds 101, there are obtained the corresponding thiols 104.

Scheme 22 illustrates the preparation of phosphonate-substituted thiophenols in which the phosphonate group is attached by means of a one-carbon link.

In this procedure, a suitably protected methyl-substituted thiophenol is subjected to free-radical bromination to afford a bromomethyl product 118. This compound is reacted with a sodium dialkyl phosphite 119 or a trialkyl phosphite, to give the displacement or rearrangement product 120, which upon deprotection affords the thiophenols 121. Preferably, 2-methylthiophenol 123 is protected by conversion to the benzoyl derivative 124, as described in Protective Groups in Organic Synthesis, by T. W. Greene and P. G. M. Wuts, Wiley, 1991, pp. 298. The product is reacted with N-bromosuccinimide in ethyl acetate to yield the bromomethyl product 125. This material is reacted with a sodium dialkyl phosphite 119, as described in J. Med. Chem., 35, 1371, 1992, to afford the product 126. Alternatively, the bromomethyl compound 125 can be converted into the phosphonate 126 by means of the Arbuzov reaction, for example as described in Handb. Organophosphorus Chem., 1992, 115. In this procedure, the bromomethyl compound 125 is heated with a trialkyl phosphate $P(OR^1)_3$ at ca. 100° to produce the phosphonate 126. Deprotection of 126, for example by treatment with aqueous ammonia, as described in J. Amer. Chem. Soc., 85, 1337, 1963, then affords the thiol 127.

Using the above procedures, but employing, in place of the bromomethyl compound 125, different bromomethyl compounds 118, there are obtained the corresponding thiols 121.

Scheme 23 illustrates the preparation of thiophenols bearing a phosphonate group linked to the phenyl nucleus by oxygen or sulfur. In this procedure, a suitably protected hydroxy or thio-substituted thiophenol 128 is reacted with a dialkyl hydroxyalkylphosphonate 129 under the conditions of the Mitsonobu reaction, for example as described in Org. React., 1992, 42, 335, to afford the coupled product 130. Deprotection then yields the O- or S-linked products 131.

Preferably, the substrate, for example 3-hydroxythiophenol, 132, is converted into the monotrityl ether 133, by reaction with one equivalent of trityl chloride, as described above. This compound is reacted with diethyl azodicarboxylate, triphenyl phosphine and a dialkyl 1-hydroxymethyl phosphonate 134 in benzene, as described in Synthesis, 4, 327, 1998, to afford the ether compound 135. Removal of the trityl protecting group, as described above, then affords the thiophenol 136.

Using the above procedures, but employing, in place of the phenol 132, different phenols or thiophenols 128, there are obtained the corresponding thiols 131.

Scheme 24 illustrates the preparation of thiophenols bearing a phosphonate group linked to the phenyl nucleus by oxygen, sulfur or nitrogen. In this procedure, a suitably protected O, S or N-substituted thiophenol 137 is reacted with an activated ester, for example the trifluoromethanesulfonate, of a dialkyl hydroxyalkyl phosphonate 138, to afford the coupled product 139. Deprotection then affords the thiol 140.

For example, the substrate, 4-methylaminothiophenol 141, is reacted with one equivalent of acetyl chloride, as described in Protective Groups in Organic Synthesis, by T. W. Greene and P. G. M. Wuts, Wiley, 1991, pp. 298, to afford the product 142. This material is then reacted with, for example, diethyl trifluoromethanesulfonylmethyl phosphonate 143, the preparation of which is described in Tet. Lett., 1986, 27, 1477, to afford the displacement product 144.

Preferably, equimolar amounts of the phosphonate 143 and the amine 142 are reacted together in an aprotic solvent such as dichloromethane, in the presence of a base such as 2,6-lutidine, at ambient temperatures, to afford the phosphonate product 144. Deprotection, for example by treatment with dilute aqueous sodium hydroxide for two minutes, as described in J. Amer. Chem. Soc., 85, 1337, 1963, then affords the thiophenol 145.

Using the above procedures, but employing, in place of the thioamine 142, different phenols, thiophenols or amines 137, and/or different phosphonates 138, there are obtained the corresponding products 140.

Scheme 25 illustrates the preparation of phosphonate esters linked to a thiophenol nucleus by means of a heteroatom and a multiple-carbon chain, employing a nucleophilic displacement reaction on a dialkyl bromoalkyl phosphonate 146.

In this procedure, a suitably protected hydroxy, thio or amino substituted thiophenol 137 is reacted with a dialkyl bromoalkyl phosphonate 146 to afford the product 147. Deprotection then affords the free thiophenol 148.

For example, 3-hydroxythiophenol 149 is converted into the S-trityl compound 150, as described above. This compound is then reacted with, for example, a dialkyl 4-bromobutyl phosphonate 151, the synthesis of which is described in Synthesis, 1994, 9, 909. The reaction is conducted in a dipolar aprotic solvent, for example dimethylformamide, in the presence of a base such as potassium carbonate, and optionally in the presence of a catalytic amount of potassium iodide, at about 50°, to yield the ether product 152. Deprotection, as described above, then affords the thiol 153.

Using the above procedures, but employing, in place of the phenol 149, different phenols, thiophenols or amines 137, and/or different phosphonates 146, there are obtained the corresponding products 148.

Scheme 26 depicts the preparation of phosphonate esters linked to a thiophenol nucleus by means of unsaturated and saturated carbon chains. The carbon chain linkage is formed by means of a palladium catalyzed Heck reaction, in which an olefinic phosphonate 155 is coupled with an aromatic bromo compound 154. In this procedure, a suitably protected bromo-substituted thiophenol 154 is reacted with a terminally unsaturated phosphonate 155, to afford the coupled product 156. Deprotection, or hydrogenation of the double bond followed by deprotection, affords respectively the unsaturated phosphonate 157, or the saturated analog 159.

For example, 3-bromothiophenol is converted into the S—Fm derivative 160, as described above, and this compound is reacted with diethyl 1-butenyl phosphonate 161, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 1000 to afford the coupled product 162. Deprotection, as described above, then affords the thiol 163. Optionally, the initially formed unsaturated phosphonate 162 can be subjected to catalytic hydrogenation, using, for example, palladium on carbon as catalyst, to yield the saturated product 164, which upon deprotection affords the thiol 165.

Using the above procedures, but employing, in place of the bromo compound 160, different bromo compounds 154, and/or different phosphonates 155, there are obtained the corresponding products 157 and 159.

Scheme 28 illustrates the preparation of an aryl-linked phosphonate ester 169 by means of a palladium(0) or palladium(II) catalyzed coupling reaction between a bromobenzene and a phenylboronic acid, as described in Comprehensive Organic Transformations, by R. C. Larock; VCH, 1989, p. 57.

The sulfur-substituted phenylboronic acid 166 is obtained by means of a metallation-boronation sequence applied to a protected bromo-substituted thiophenol, for example as described in J. Org. Chem., 49, 5237, 1984. A coupling reaction then affords the diaryl product 168 which is deprotected to yield the thiol 169.

For example, protection of 4-bromothiophenol by reaction with tert-butylchlorodimethylsilane, in the presence of a base such as imidazole, as described in Protective Groups in Organic Synthesis, by T. W. Greene and P. G. M. Wuts, Wiley, 1991, p. 297, followed by metallation with butyllithium and boronation, as described in J. Organomet. Chem., 1999, 581, 82, affords the boronate 170. This material is reacted with diethyl 4-bromophenylphosphonate 171, the preparation of which is described in J. Chem. Soc., Perkin Trans., 1977, 2, 789, in the presence of tetrakis(triphenylphosphine)palladium (0) and an inorganic base such as sodium carbonate, to afford the coupled product 172.

Deprotection, for example by the use of tetrabutyl ammonium fluoride in anhydrous tetrahydrofuran, then yields the thiol 173.

Using the above procedures, but employing, in place of the boronate 170, different boronates 166, and/or different phosphonates 167, there are obtained the corresponding products 169. Scheme 29 depicts the preparation of dialkyl phosphonates in which the phosphonate moiety is linked to the thiophenyl group by means of a chain which incorporates an aromatic or heteroaromatic ring.

In this procedure, a suitably protected O, S or N-substituted thiophenol 137 is reacted with a dialkyl bromomethyl-substituted aryl or heteroarylphosphonate 174, prepared, for example, by means of an Arbuzov reaction between equimolar amounts of a bis(bromo-methyl) substituted aromatic compound and a trialkyl phosphite. The reaction product 175 is then deprotected to afford the thiol 176. For example, 1,4-dimercaptobenzene is converted into the monobenzoyl ester 177 by reaction with one molar equivalent of benzoyl chloride, in the presence of a base such as pyridine. The monoprotected thiol 177 is then reacted with, for example diethyl 4-(bromomethyl)phenylphosphonate, 178, the preparation of which is described in Tetrahedron, 1998, 54, 9341. The reaction is conducted in a solvent such as dimethylformamide, in the presence of a base such as potassium carbonate, at about 50°. The thioether product 179 thus obtained is deprotected, as described above, to afford the thiol 180.

Using the above procedures, but employing, in place of the thiophenol 177, different phenols, thiophenols or amines 137, and/or different phosphonates 174, there are obtained the corresponding products 176.

Scheme 30 illustrates the preparation of phosphonate-containing thiophenols in which the attached phosphonate chain forms a ring with the thiophenol moiety.

In this procedure, a suitably protected thiophenol 181, for example an indoline (in which X—Y is $(CH_2)_2$), an indole (X—Y is CH═CH) or a tetrahydroquinoline (X—Y is $(CH_2)_3$) is reacted with a dialkyl trifluoromethanesulfonyloxymethyl phosphonate 138, in the presence of an organic or inorganic base, in a polar aprotic solvent such as, for example, dimethylformamide, to afford the phosphonate ester 182. Deprotection, as described above, then affords the thiol 183. The preparation of thio-substituted indolines is described in EP 209751. Thio-substituted indoles, indolines and tetrahydroquinolines can also be obtained from the corresponding hydroxy-substituted compounds, for example by thermal rearrangement of the dimethylthiocarbamoyl esters, as described in J. Org. Chem., 31, 3980, 1966. The preparation of hydroxy-substituted indoles is described in Syn., 1994, 10, 1018; preparation of hydroxy-substituted indolines is described in Tet. Lett., 1986, 27, 4565, and the preparation of hydroxy-substituted tetrahydroquinolines is described in J. Het. Chem., 1991, 28, 1517, and in J. Med. Chem., 1979, 22, 599. Thio-substituted indoles, indolines and tetrahydroquinolines can also be obtained from the corresponding amino and bromo compounds, respectively by diazotization, as described in Sulfur Letters, 2000, 24, 123, or by reaction of the derived organolithium or magnesium derivative with sulfur, as described in Comprehensive Organic Functional Group Preparations, A. R. Katritzky et al., eds., Pergamon, 1995, Vol. 2, p. 707. For example, 2,3-dihydro-1H-indole-5-thiol, 184, the preparation of which is described in EP 209751, is converted into the benzoyl ester 185, as described above, and the ester is then reacted with the triflate 143, using the conditions described above for the preparation of 144, (Scheme 24), to yield the phosphonate 186. Deprotection, for example by reaction with dilute aqueous ammonia, as described above, then affords the thiol 187.

Using the above procedures, but employing, in place of the thiol 184, different thiols 181, and/or different triflates 138, there are obtained the corresponding products 183.

Scheme 20

Method

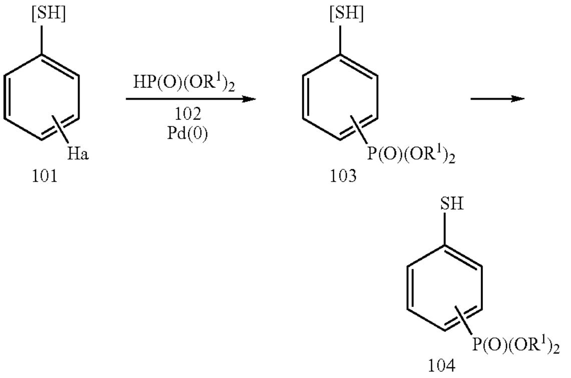

101 103 104

Example

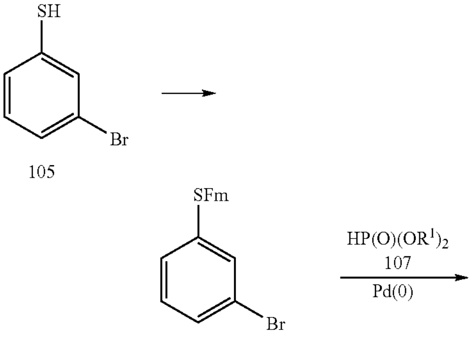

105 106

Fm = 9-fluorenylmethyl

-continued

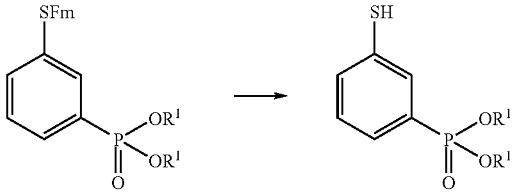

108 109

Scheme 21

Method

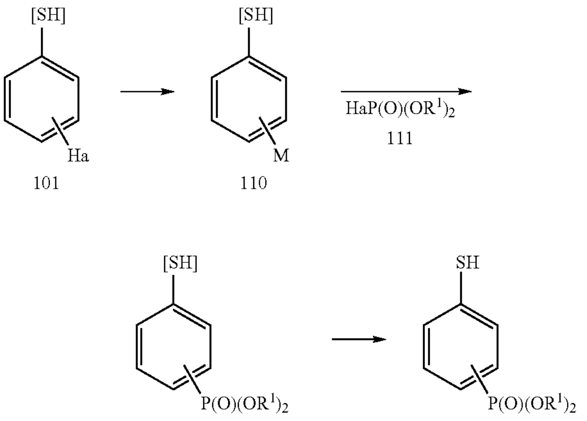

101 110 103 104

Example

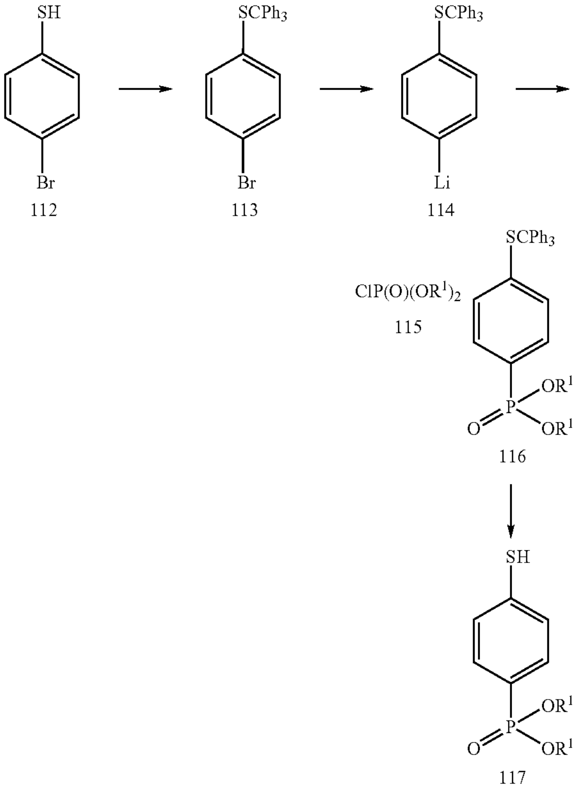

112 113 114 116 117

Scheme 22
Method
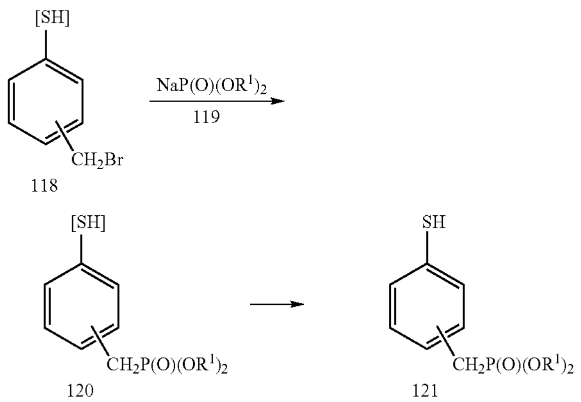
Example
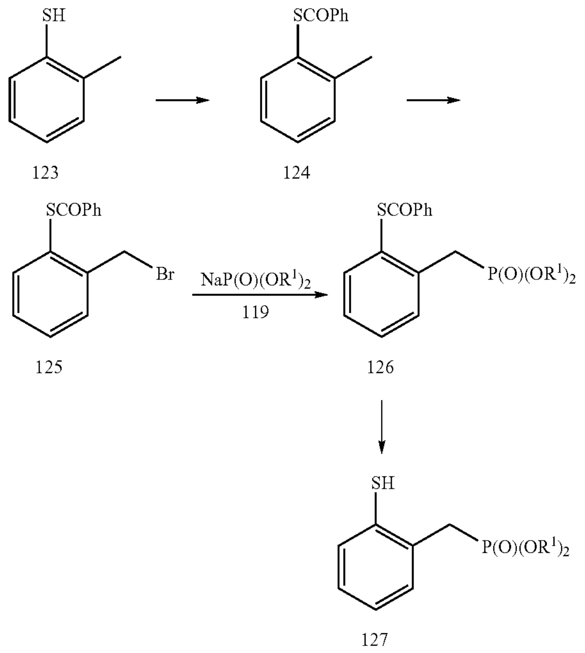
Scheme 23
Method
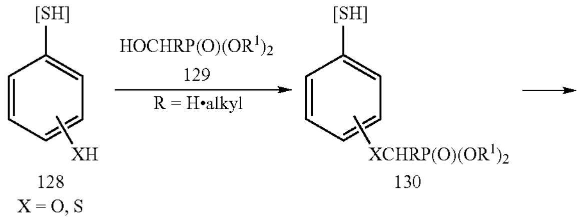
-continued
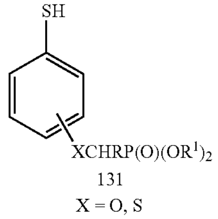
Example
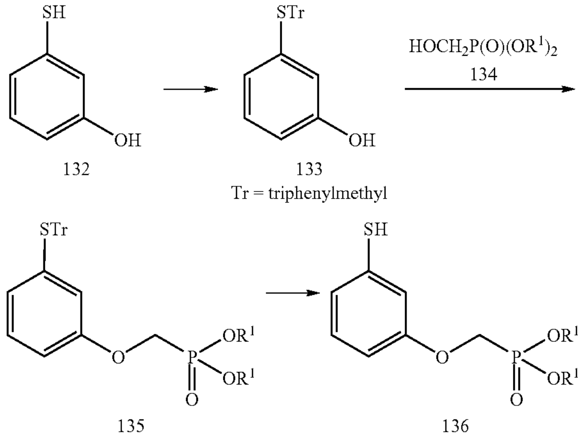
Scheme 24
Method
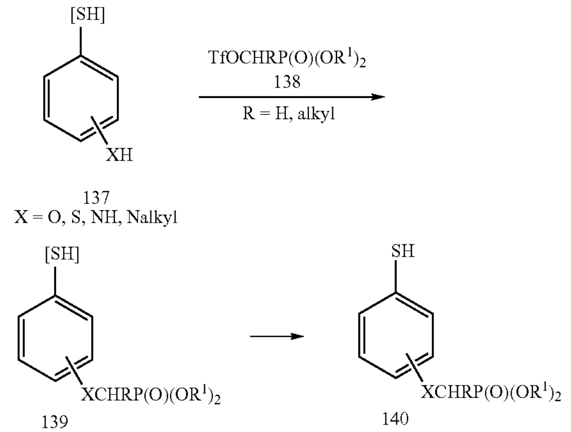
Example
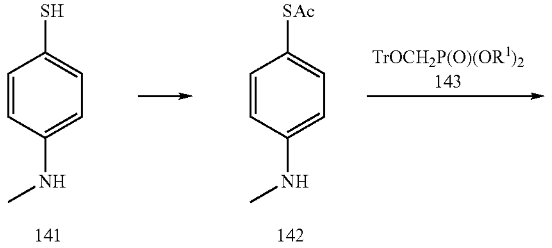

-continued
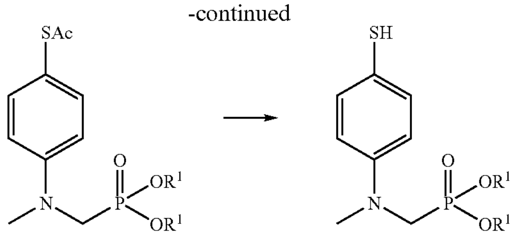
144
145
Scheme 25
Method
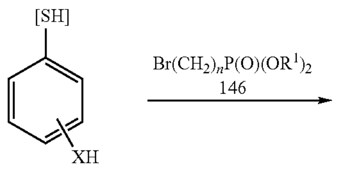
137
X = O, S, NH, Nalkyl
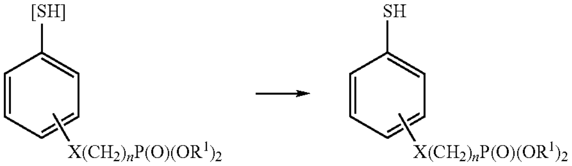
147
148
Example
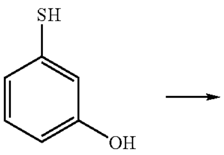
149
-continued
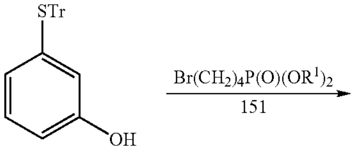
150
Tr = triphenylmethyl
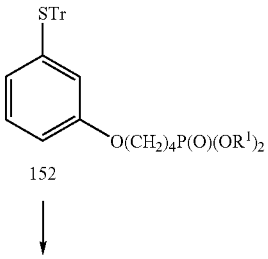
152
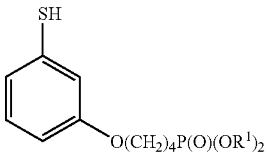
153
Scheme 26
Method
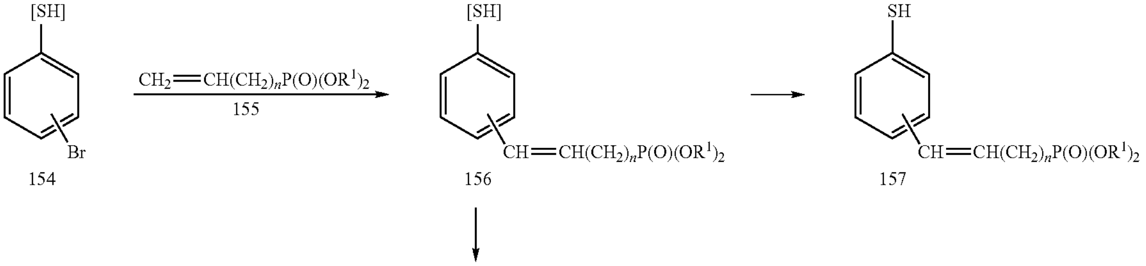
154
156
157

-continued
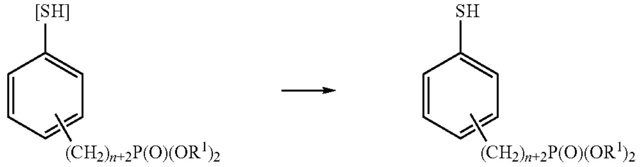
158 159
Example
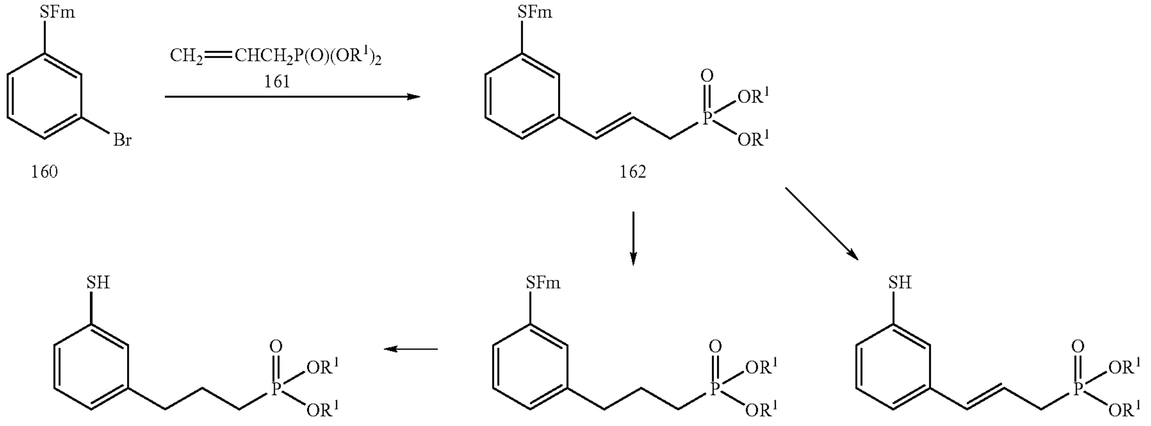
160 162
165 164 163
Scheme 28
Method
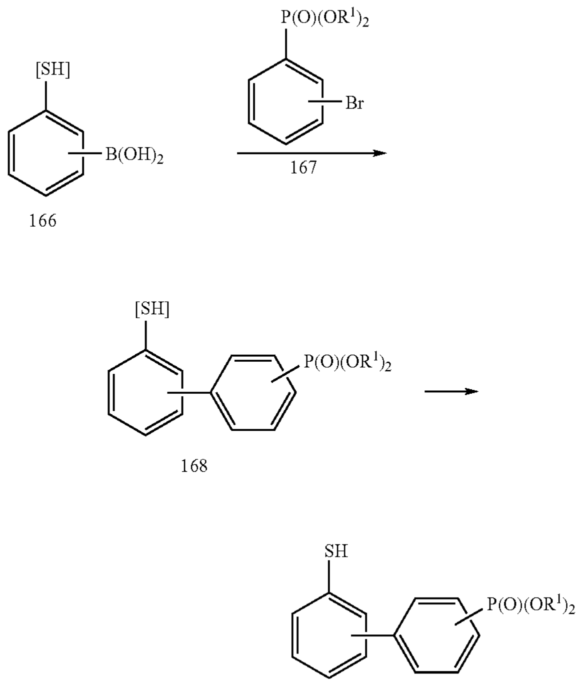
166
168
169
-continued
Example
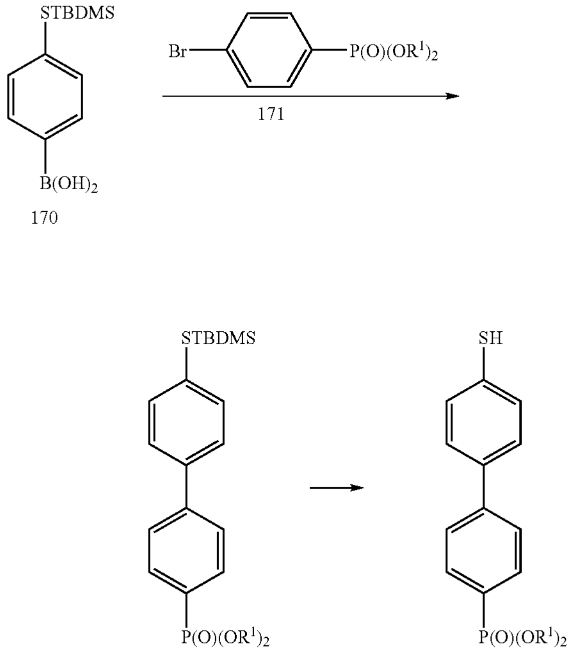
170
172 173

Scheme 29
Method
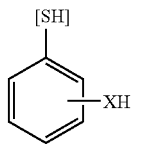
137
X = O, S, NH, Nalkyl
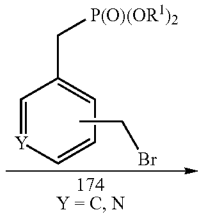
174
Y = C, N
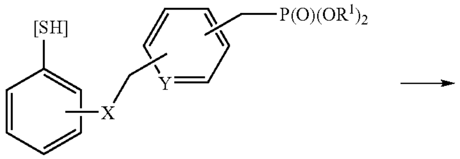
175
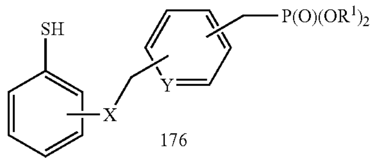
176
Example
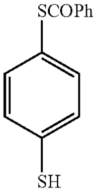
177
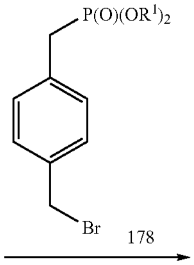
178
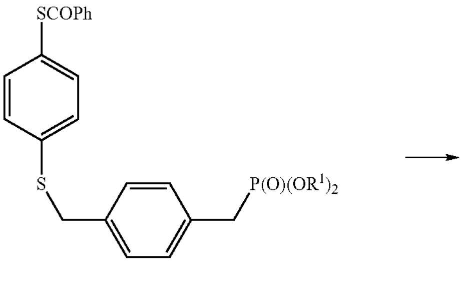
179
-continued
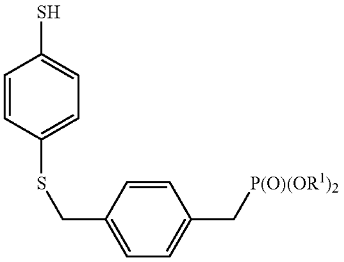
180
Scheme 30
Method
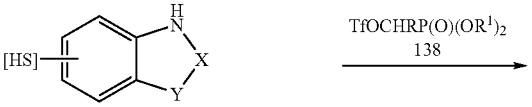
181
X—Y = $(CH_2)_2$, 3; CH═CH
$TfOCHRP(O)(OR^1)_2$
138
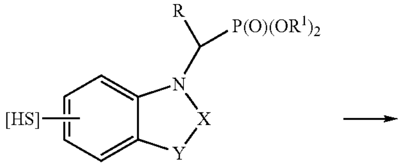
182
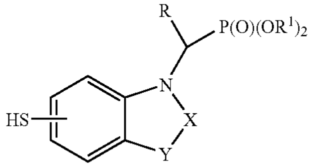
183
Example
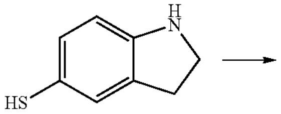
184
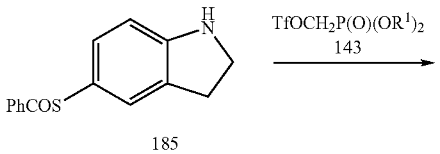
185
$TfOCH_2P(O)(OR^1)_2$
143
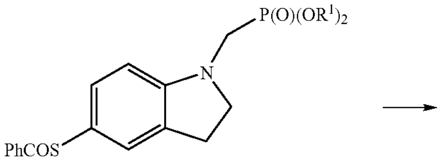
186

-continued

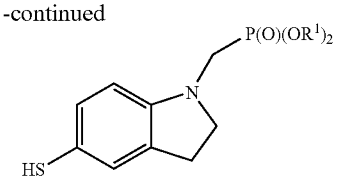

187

Preparation of Benzoic Acid Derivatives Incorporating Phosphonate Moieties.

Scheme 31 illustrates a method for the preparation of hydroxymethylbenzoic acid reactants in which the phosphonate moiety is attached directly to the phenyl ring. In this method, a suitably protected bromo hydroxy methyl benzoic acid 188 is subjected to halogen-methyl exchange to afford the organometallic intermediate 189. This compound is reacted with a chlorodialkyl phosphite 115 to yield the phenylphosphonate ester 190, which upon deprotection affords the carboxylic acid 191.

For example, 4-bromo-3-hydroxy-2-methylbenzoic acid, 192, prepared by bromination of 3-hydroxy-2-methylbenzoic acid, as described, for example, J. Amer. Chem. Soc., 55, 1676, 1933, is converted into the acid chloride, for example by reaction with thionyl chloride. The acid chloride is then reacted with 3-methyl-3-hydroxymethyloxetane 193, as described in Protective Groups in Organic Synthesis, by T. W. Greene and P. G. M. Wuts, Wiley, 1991, pp. 268, to afford the ester 194. This compound is treated with boron trifluoride at 0° to effect rearrangement to the orthoester 195, known as the OBO ester. This material is treated with a silylating reagent, for example tert-butyl chlorodimethylsilane, in the presence of a base such as imidazole, to yield the silyl ether 196. Halogen-metal exchange is performed by the reaction of 196 with butyllithium, and the lithiated intermediate is then coupled with a chlorodialkyl phosphite 115, to produce the phosphonate 197. Deprotection, for example by treatment with 4-toluenesulfonic acid in aqueous pyridine, as described in Can. J. Chem., 61, 712, 1983, removes both the OBO ester and the silyl group, to produce the carboxylic acid 198.

Using the above procedures, but employing, in place of the bromo compound 192, different bromo compounds 188, there are obtained the corresponding products 191.

Scheme 32 illustrates the preparation of hydroxymethylbenzoic acid derivatives in which the phosphonate moiety is attached by means of a one-carbon link.

In this method, a suitably protected dimethyl hydroxybenzoic acid, 199, is reacted with a brominating agent, so as to effect benzylic bromination. The product 200 is reacted with a sodium dialkyl phosphite, 119, to effect displacement of the benzylic bromide to afford the phosphonate 201.

For example, 2,5-dimethyl-3-hydroxybenzoic acid, 203, the preparation of which is described in Can. J. Chem., 1970, 48, 1346, is reacted with excess methoxymethyl chloride, as described in Protective Groups in Organic Synthesis, by T. W. Greene and P. G. M Wuts, Second Edition 1990, p. 17, to afford the ether ester 204. The reaction is performed in an inert solvent such as dichloromethane, in the presence of an organic base such as N-methylmorpholine or diisopropylethylamine. The product 204 is then reacted with a brominating agent, for example N-bromosuccinimide, in an inert solvent such as, for example, ethyl acetate, at reflux, to afford the bromomethyl product 205. This compound is then reacted with a sodium dialkyl phosphite 119, using the conditions described above for the preparation of 120, (Scheme 22) to afford the phosphonate 206. Deprotection, for example by brief treatment with a trace of mineral acid in methanol, as described in J. Chem. Soc. Chem. Comm., 1974, 298, then yields the carboxylic acid 207.

Using the above procedures, but employing, in place of the methyl compound 203, different methyl compounds 199, there are obtained the corresponding products 202.

Scheme 33 illustrates the preparation of phosphonate-containing hydroxymethylbenzoic acids in which the phosphonate group is attached by means of an oxygen or sulfur atom.

In this method, a suitably protected hydroxy- or mercapto-substituted hydroxymethyl benzoic acid 208 is reacted, under the conditions of the Mitsonobu reaction, with a dialkyl hydroxymethyl phosphonate 134, to afford the coupled product 209, which upon deprotection affords the carboxylic acid 210.

For example, 3,6-dihydroxy-2-methylbenzoic acid, 211, the preparation of which is described in Yakugaku Zasshi 1971, 91, 257, is converted into the diphenylmethyl ester 212, by treatment with diphenyldiazomethane, as described in Protective Groups in Organic Synthesis, by T. W. Greene and P. G. M. Wuts, Wiley, 1991, pp. 253. The product is then reacted with one equivalent of a silylating reagent, such as, for example, tert butylchlorodimethylsilane, using the conditions described above for the preparation of 170, to afford the mono-silyl ether 213. This compound is then reacted with a dialkyl hydroxymethylphosphonate 134, under the conditions of the Mitsonobu reaction, as described above for the preparation of 130, (Scheme 23) to afford the coupled product 214. Deprotection, for example by treatment with trifluoroacetic acid at ambient temperature, as described in J. Chem. Soc., C, 1191, 1966, then affords the phenolic carboxylic acid 215.

Using the above procedures, but employing, in place of the phenol 211, different phenols or thiophenols 208, there are obtained the corresponding products 210.

Scheme 34 depicts the preparation of phosphonate esters attached to the hydroxymethylbenzoic acid moiety by means of unsaturated or saturated carbon chains. In this method, a dialkyl alkenylphosphonate 216 is coupled, by means of a palladium catalyzed Heck reaction, with a suitably protected bromo substituted hydroxymethylbenzoic acid 217. The product 218 can be deprotected to afford the phosphonate 219, or subjected to catalytic hydrogenation to afford the saturated compound, which upon deprotection affords the corresponding carboxylic acid 220.

For example, 5-bromo-3-hydroxy-2-methylbenzoic acid 221, prepared as described in WO 9218490, is converted as described above, into the silyl ether OBO ester 222. This compound is coupled with, for example, a dialkyl 4-buten-1-ylphosphonate 223, the preparation of which is described in J. Med. Chem., 1996, 39, 949, using the conditions described above for the preparation of 156, (Scheme 26) to afford the product 224. Deprotection, or hydrogenation/deprotection, of this compound, as described above, then affords respectively the unsaturated and saturated products 225 and 227.

Using the above procedures, but employing, in place of the bromo compound 221, different bromo compounds 217, and/or different phosphonates 216, there are obtained the corresponding products 219 and 220.

Scheme 35 illustrates the preparation of phosphonate esters linked to the hydroxymethylbenzoic acid moiety by means of an aromatic ring.

In this method, a suitably protected bromo-substituted hydroxymethylbenzoic acid 217 is converted to the corresponding boronic acid, as described above, (Scheme 28). The product is subjected to a Suzuki coupling reaction, as described above, with a dialkyl bromophenyl phosphonate 229. The product 230 is then deprotected to afford the diaryl phosphonate product 231.

For example, the silylated OBO ester 232, prepared as described above, (Scheme 31), is converted into the boronic acid 233, as described above. This material is coupled with a dialkyl 4-bromophenyl phosphonate 234, prepared as described in J. Chem. Soc. Perkin Trans., 1977, 2, 789, using tetrakis(triphenylphosphine)palladium(0) as catalyst, as described above for the preparation of 172, (Scheme 28) to afford the diaryl phosphonate 235.

Deprotection, as described above, then affords the benzoic acid 236.

Using the above procedures, but employing, in place of the bromo compound 232, different bromo compounds 217, and/or different phosphonates 229, there are obtained the corresponding carboxylic acid products 231.

Scheme 31

Method

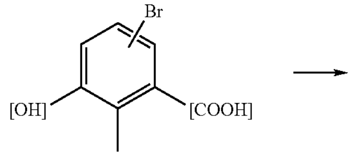

188

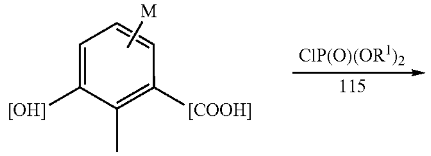

189

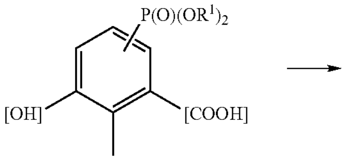

190

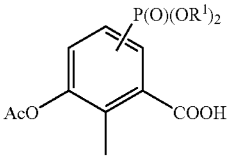

191

Example

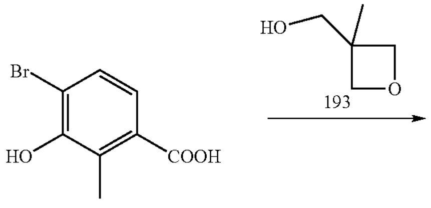

192

193

-continued

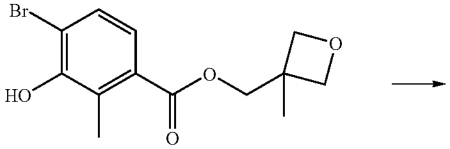

194

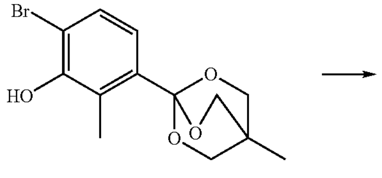

195

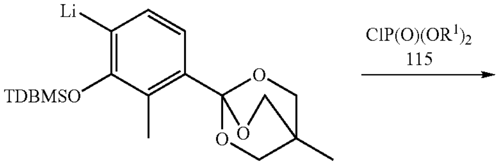

196

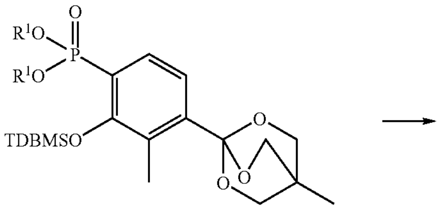

197

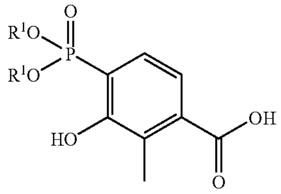

198

Scheme 32

Method

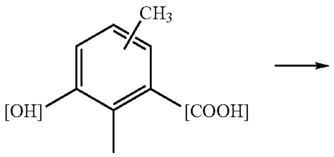

199

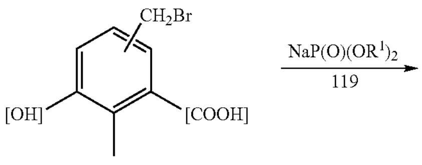

200

-continued
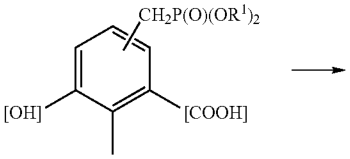
201
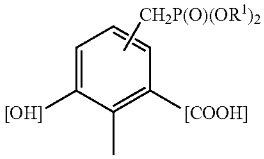
202
Example
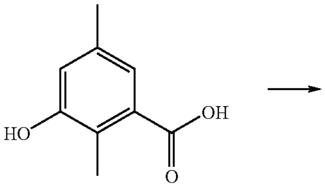
203
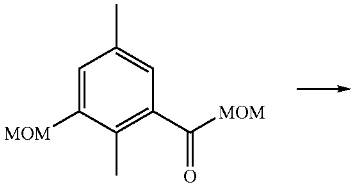
204
MOM = $CH_3OCH_2O$
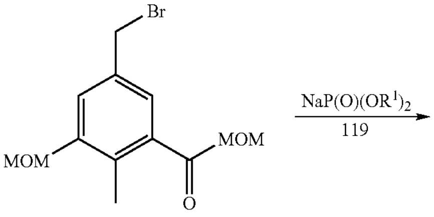
205
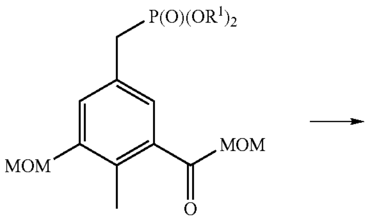
206
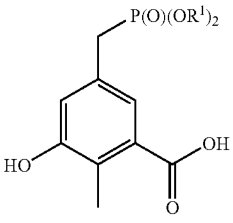
207
Scheme 33
Method
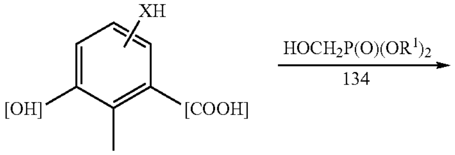
208
X = O, S
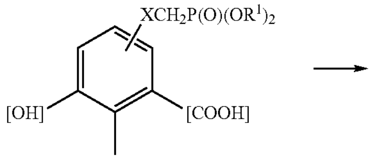
209
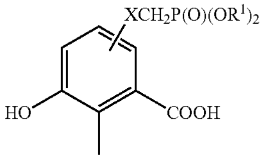
210
Example
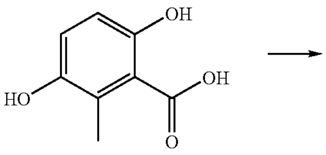
211
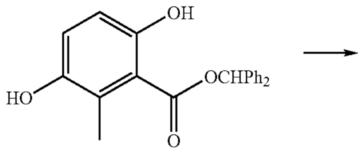
212
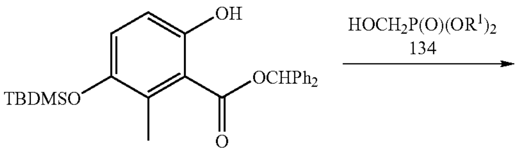
213
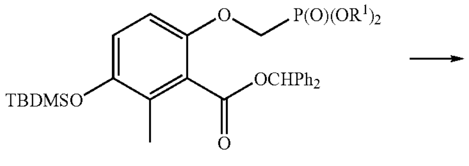
214
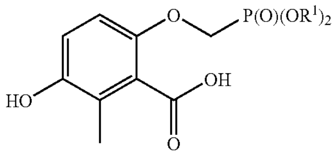
215

Scheme 34
Method
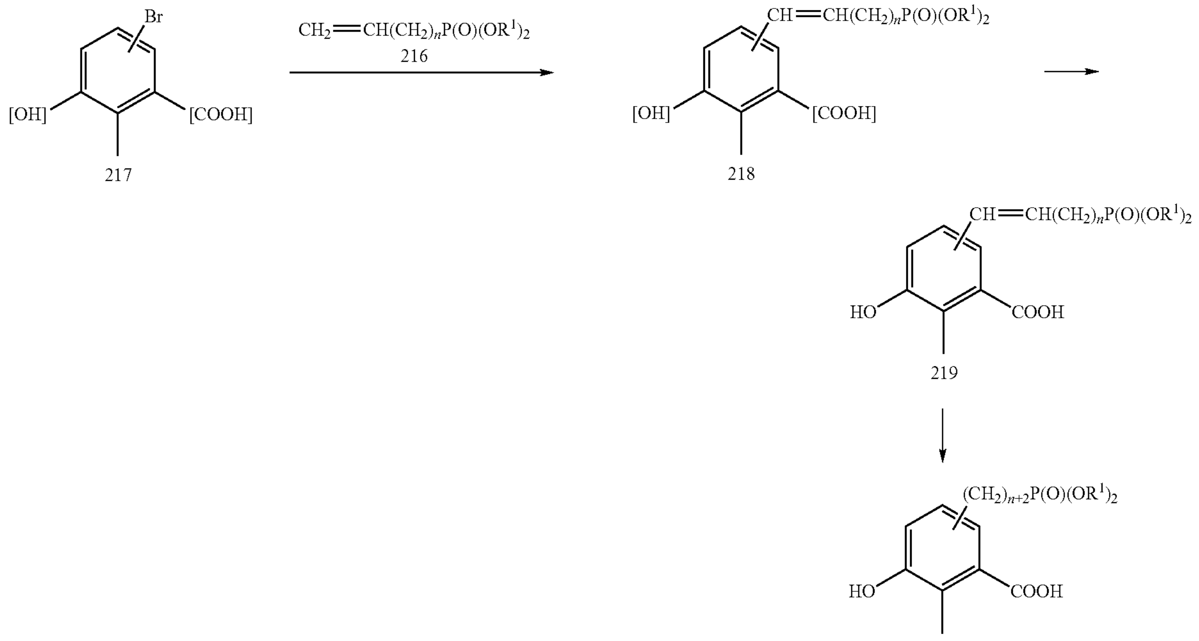
217, 218, 219, 220
Example
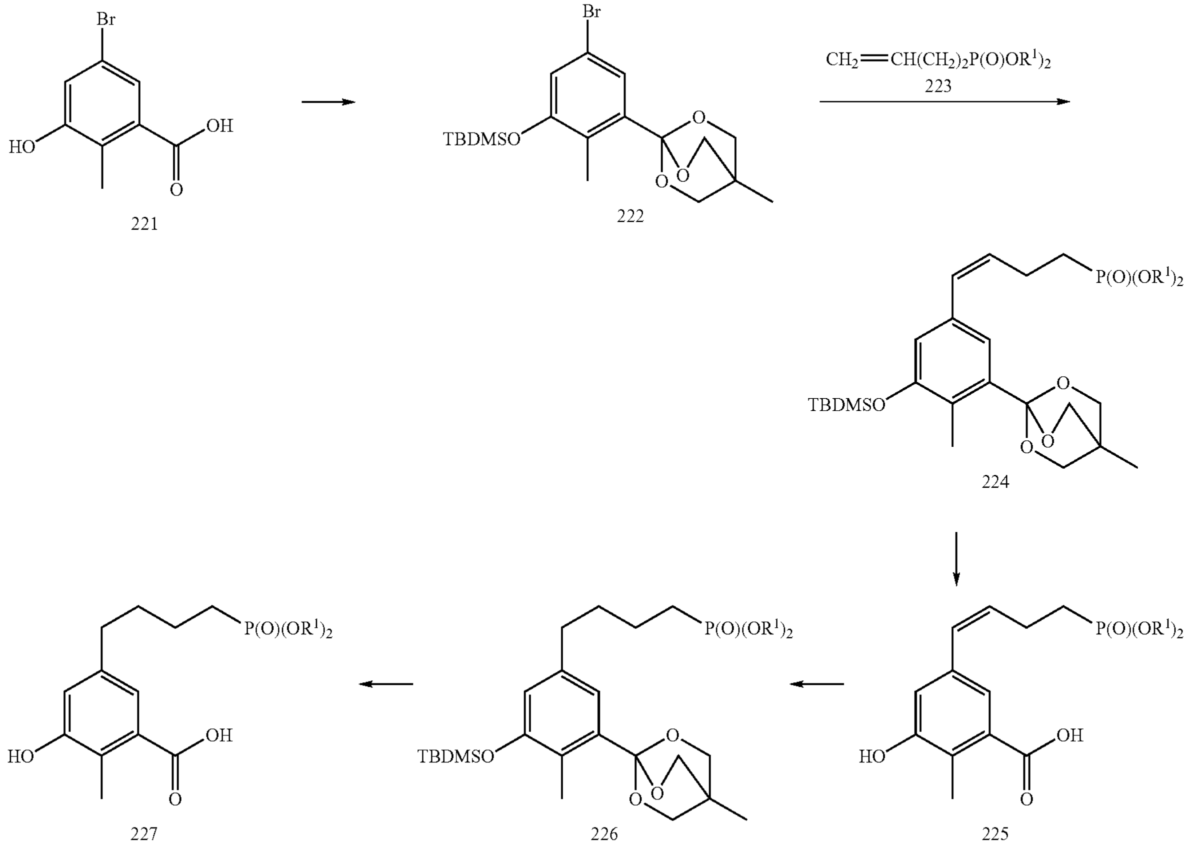
221, 222, 224, 225, 226, 227

Scheme 35

Method

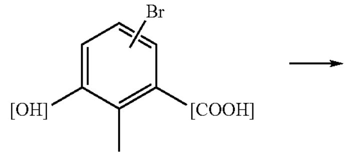

217

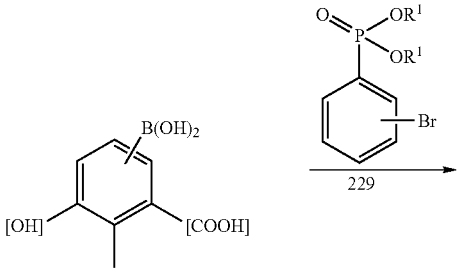

229

228

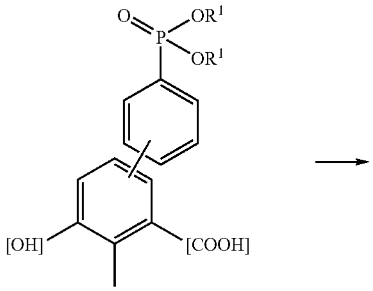

230

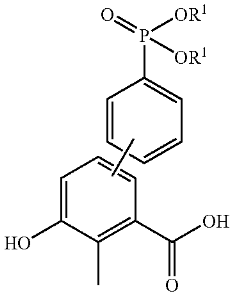

231

Example

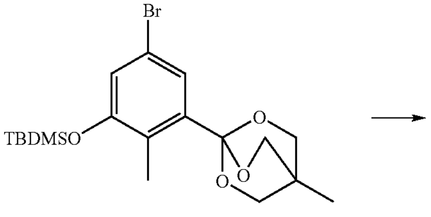

232

-continued

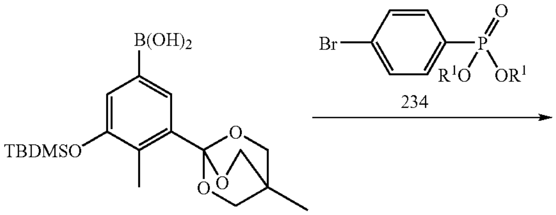

234

233

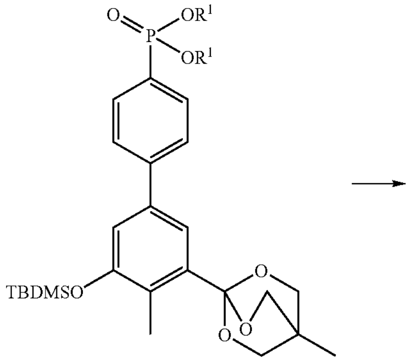

235

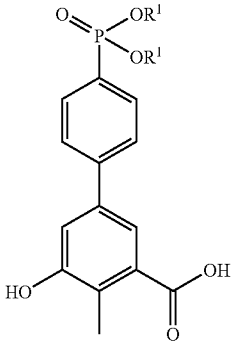

236

Preparation of Tert-butylamine Derivatives Incorporating Phosphonate Moieties.

Scheme 36 describes the preparation of tert-butylamines in which the phosphonate moiety is directly attached to the tert-butyl group. A suitably protected 2.2-dimethyl-2-amino-ethylbromide 237 is reacted with a trialkyl phosphite, under the conditions of the Arbuzov reaction, as described above, to afford the phosphonate 238.

For example, the cbz derivative of 2.2-dimethyl-2-amino-ethylbromide 240, is heated with a trialkyl phosphite at ca 150° to afford the product 241. Deprotection, as previously described, then affords the free amine 242.

Using the above procedures, but employing different trisubstituted phosphites, there are obtained the corresponding amines 239.

Scheme 37 illustrates the preparation of phosphonate esters attached to the tert butylamine by means of a heteroatom and a carbon chain.

An optionally protected alcohol or thiol 243 is reacted with a bromoalkylphosphonate 146, to afford the displacement product 244. Deprotection, if needed, then yields the amine 245.

For example, the cbz derivative of 2-amino-2,2-dimethyl-ethanol 246 is reacted with a dialkyl 4-bromobutyl phosphonate 247, prepared as described in Synthesis, 1994, 9, 909, in dimethylformamide containing potassium carbonate and potassium iodide, at ca 60° to afford the phosphonate 248. Deprotection then affords the free amine 249.

Using the above procedures, but employing different alcohols or thiols 243, and/or different bromoaklylphosphonates 146, there are obtained the corresponding products 245.

Scheme 38 describes the preparation of carbon-linked phosphonate tert butylamine derivatives, in which the carbon chain can be unsaturated or saturated.

In the procedure, a terminal acetylenic derivative of tert-butylamine 250 is reacted, under basic conditions, with a dialkyl chlorophosphite 115, as described above in the preparation of 104, (Scheme 21). The coupled product 251 is deprotected to afford the amine 252. Partial or complete catalytic hydrogenation of this compound affords the olefinic and saturated products 253 and 254 respectively.

For example, 2-amino-2-methylprop-1-yne 255, the preparation of which is described in WO 9320804, is converted into the N-phthalimido derivative 256, by reaction with phthalic anhydride, as described in Protective Groups in Organic Synthesis, by T. W. Greene and P. G. M. Wuts, Wiley, 1991, pp. 358. This compound is reacted with lithium diisopropylamide in tetrahydrofuran at −78°. The resultant anion is then reacted with a dialkyl chlorophosphite 115 to afford the phosphonate 257. Deprotection, for example by treatment with hydrazine, as described in J. Org. Chem., 43, 2320, 1978, then affords the free amine 258. Partial catalytic hydrogenation, for example using Lindlar catalyst, as described in Reagents for Organic Synthesis, by L. F. Fieser and M. Fieser, Volume 1, p. 566, produces the olefinic phosphonate 259, and conventional catalytic hydrogenation, as described in Organic Functional Group Preparations, by S. R. Sandier and W. Karo, Academic Press, 1968, p3. for example using 5% palladium on carbon as catalyst, affords the saturated phosphonate 260. Using the above procedures, but employing different acetylenic amines 250, there are obtained the corresponding products 252, 253 and 254.

Scheme 39 illustrates the preparation of a tert butylamine phosphonate in which the phosphonate moiety is attached by means of a cyclic amine.

In this method, an aminoethyl-substituted cyclic amine 261 is reacted with a limited amount of a bromoalkyl phosphonate 146, using, for example, the conditions described above for the preparation of 147, (Scheme 25) to afford the displacement product 262.

For example, 3-(1-amino-1-methyl)ethylpyrrolidine 263, the preparation of which is described in Chem. Pharm. Bull., 1994, 42, 1442, is reacted with a dialkyl 4-bromobutyl phosphonate 151, prepared as described in Synthesis, 1994, 9, 909, to afford the displacement product 264. Using the above procedures, but employing different cyclic amines 261, and/or different bromoalkylphosphonates 146, there are obtained the corresponding products 262.

Scheme 36

Method

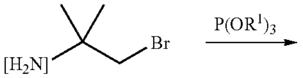

237

-continued

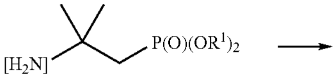

238

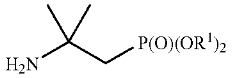

239

Example

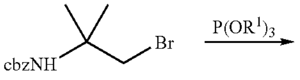

240

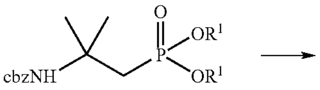

241

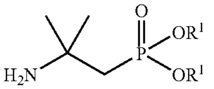

242

Scheme 37

Method

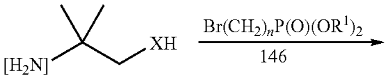

X = O, S
243

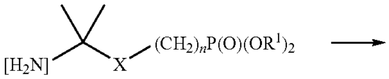

244

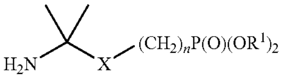

245

Example

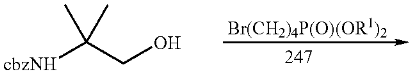

246

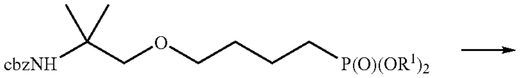

248

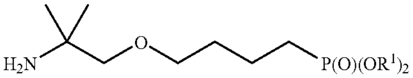

249

Scheme 38
Method
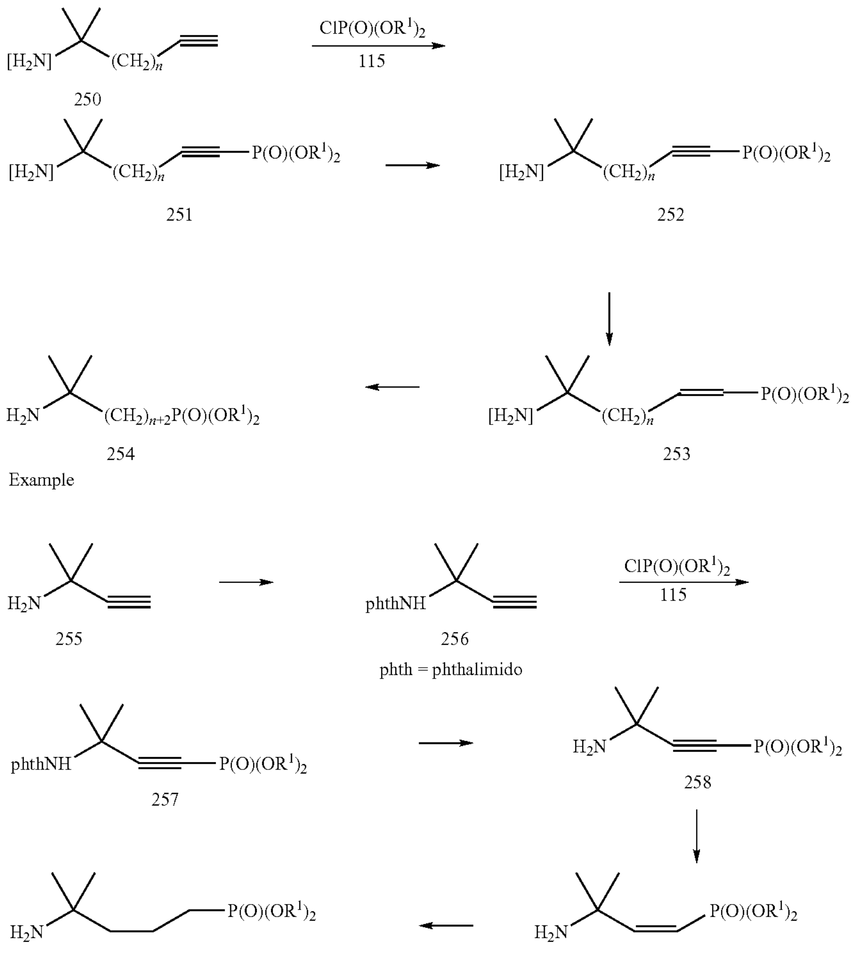
250, 251, 252, 253, 254
Example
255, 256
phth = phthalimido
257, 258, 259, 260
Scheme 39
Method
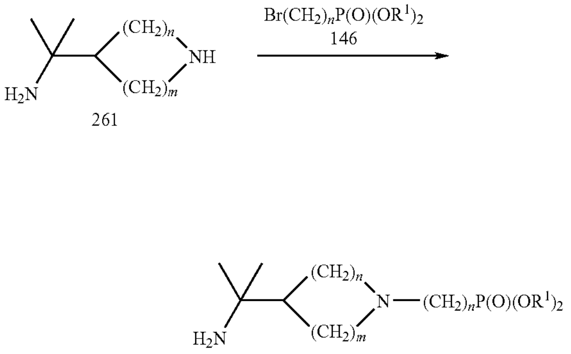
261
262
-continued
Example
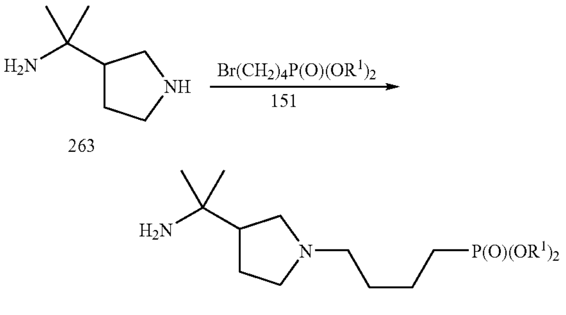
263
264
Preparation of Decahydroquinolines with Phosphonate Moieties at the 6-position.

Chart 6 illustrates methods for the synthesis of intermediates for the preparation of decahydroquinolines with phosphonate moieties at the 6-position. Two methods for the preparation of the intermediate 265 are shown.

In the first route, 2-hydroxy-6-methylphenylalanine 266, the preparation of which is described in J. Med. Chem., 1969, 12, 1028, is converted into the protected derivative 267. For example, the carboxylic acid is first transformed into the benzyl ester, and the product is reacted with acetic anhydride in the presence of an organic base such as, for example, pyridine, to afford the product 267, in which R is benzyl. This compound is reacted with a brominating agent, for example N-bromosuccinimide, to effect benzylic bromination and yield the product 268. The reaction is conducted in an aprotic solvent such as, for example, ethyl acetate or carbon tetrachloride, at reflux. The brominated compound 268 is then treated with acid, for example dilute hydrochloric acid, to effect hydrolysis and cyclization to afford the tetrahydroisoquinoline 265, in which R is benzyl.

Alternatively, the tetrahydroisoquinoline 265 can be obtained from 2-hydroxyphenylalanine 269, the preparation of which is described in Can. J. Bioch., 1971, 49, 877. This compound is subjected to the conditions of the Pictet-Spengler reaction, for example as described in Chem. Rev., 1995, 95, 1797.

Typically, the substrate 269 is reacted with aqueous formaldehyde, or an equivalent such as paraformaldehyde or dimethoxymethane, in the presence of hydrochloric acid, for example as described in J. Med. Chem., 1986, 29, 784, to afford the tetrahydroisoquinoline product 265, in which R is H.

Catalytic hydrogenation of the latter compound, using, for example, platinum as catalyst, as described in J. Amer. Chem. Soc., 69, 1250, 1947, or using rhodium on alumina as catalyst, as described in J. Med. Chem., 1995, 38, 4446, then gives the hydroxy-substituted decahydroisoquinoline 270. The reduction can also be performed electrochemically, as described in Trans SAEST 1984, 19, 189.

For example, the tetrahydroisoquinoline 265 is subjected to hydrogenation in an alcoholic solvent, in the presence of a dilute mineral acid such as hydrochloric acid, and 5% rhodium on alumina as catalyst. The hydrogenation pressure is ca. 750 psi, and the reaction is conducted at ca 50°, to afford the decahydroisoquinoline 270.

Protection of the carboxyl and NH groups present in 270 for example by conversion of the carboxylic acid into the trichloroethyl ester, as described in Protective Groups in Organic Synthesis, by T. W. Greene and P. G. M. Wuts, Wiley, 1991, p. 240, and conversion of the NH into the N-cbz group, as described above, followed by oxidation, using, for example, pyridinium chlorochromate and the like, as described in Reagents for Organic Synthesis, by L. F. Fieser and M. Fieser, Volume 6, p. 498, affords the protected ketone 276, in which R is trichloroethyl and $R_1$ is cbz. Reduction of the ketone, for example by the use of sodium borohydride, as described in J. Amer. Chem. Soc., 88, 2811, 1966, or lithium tri-tertiary butyl aluminum hydride, as described in J. Amer. Chem. Soc., 80, 5372, 1958, then affords the alcohol 277.

For example, the ketone is reduced by treatment with sodium borohydride in an alcoholic solvent such as, for example, isopropanol, at ambient temperature, to afford the alcohol 277. The alcohol 270 carboxyl and NH groups can be protected, for example by conversion of the carboxylic acid into the trichloroethyl ester, as described in Protective Groups in Organic Synthesis, by T. W. Greene and P. G. M. Wuts, Wiley, 1991, p. 240, and by conversion of the NH into the N-cbz group, as described above. The protected alcohol 270 can then be converted into the thiol 271 and the amine 272, by means of displacement reactions with suitable nucleophiles, with inversion of stereochemistry. For example, the alcohol 270 can be converted into an activated ester, for example trifluoromethanesulfonyl ester or the methanesulfonate ester 273, by treatment with methanesulfonyl chloride, as described above for the preparation of 63, (Scheme 1). The mesylate 273 is then treated with a sulfur nucleophile, for example potassium thioacetate, as described in Tet. Lett., 1992, 4099, or sodium thiophosphate, as described in Acta Chem. Scand., 1960, 1980, to effect displacement of the mesylate, followed by mild basic hydrolysis, for example by treatment with aqueous ammonia, to afford the thiol 271.

For example, the mesylate 273 is reacted with one molar equivalent of sodium thioacetate in a polar aprotic solvent such as, for example, dimethylformamide, at ambient temperature, to afford the thioacetate 274, in which R2 is $COCH_3$. The product then treated with, a mild base such as, for example, aqueous ammonia, in the presence of an organic co-solvent such as ethanol, at ambient temperature, to afford the thiol 271.

The mesylate 273 can be treated with a nitrogen nucleophile, for example sodium phthalimide or sodium bis(trimethylsilyl)amide, as described in Comprehensive Organic Transformations, by R. C. Larock, p. 399, to afford the amine 272.

For example, the mesylate 273 is reacted, as described in Angew. Chem. Int. Ed., 7, 919, 1968, with one molar equivalent of potassium phthalimide, in a dipolar aprotic solvent, such as, for example, dimethylformamide, at ambient temperature, to afford the displacement product 275, in which $NR^aR^b$ is phthalimido. Removal of the phthalimido group, for example by treatment with an alcoholic solution of hydrazine at ambient temperature, as described in J. Org. Chem., 38, 3034, 1973, then yields the amine 272.

The application of the procedures described above for the conversion of the β-carbinol 270 to the α-thiol 271 and the α-amine 272 can also be applied to the α-carbinol 277, so as to afford the β-thiol and β-amine, 278.

CHART 6

Intermediates for the preparation of phosphonate-containing decahydroisoquinolines.

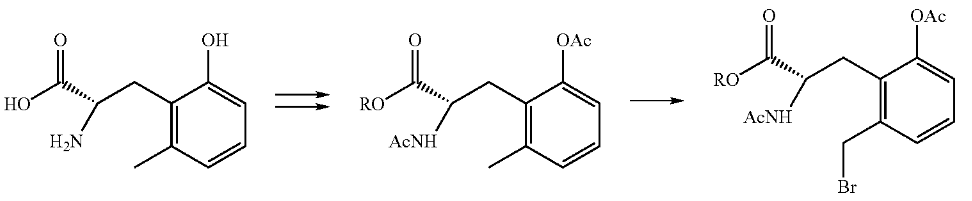

266 267 268

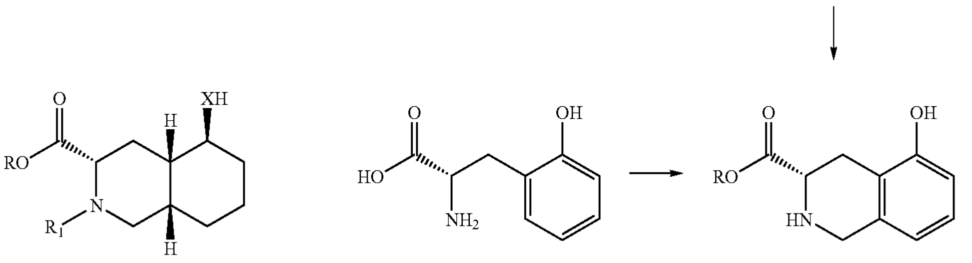

278 269 265

X = S, NH

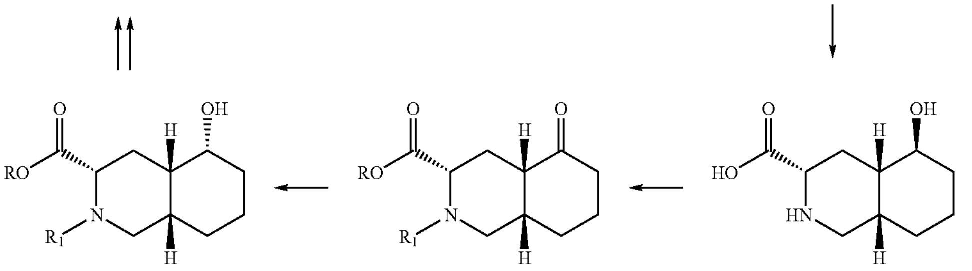

277 276 270

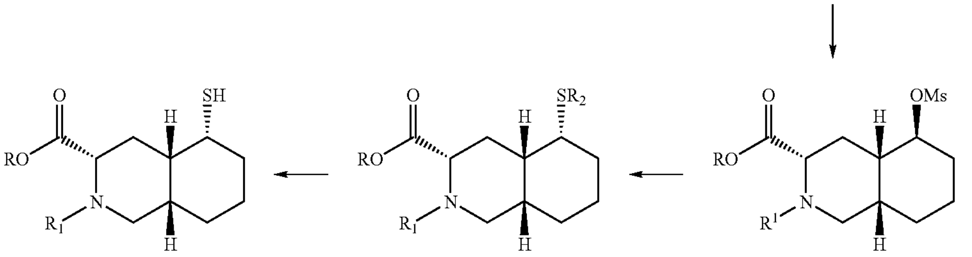

271 274 273

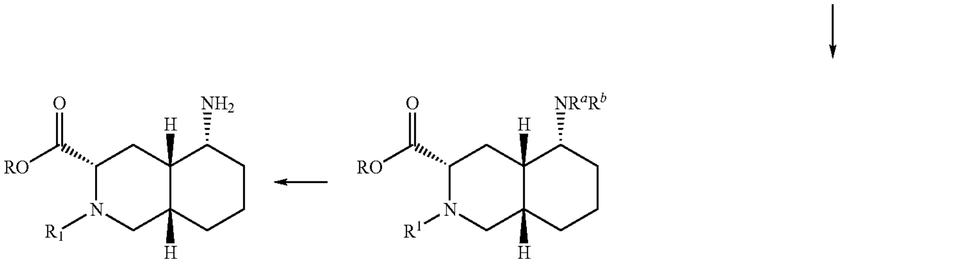

272 275

Scheme 40 illustrates the preparation of compounds in which the phosphonate moiety is attached to the decahydroisoquinoline by means of a heteroatom and a carbon chain. In this procedure, an alcohol, thiol or amine 279 is reacted with a bromoalkyl phosphonate 146, under the conditions described above for the preparation of 147 (Scheme 25), to afford the displacement product 280. Deprotection of the ester group, followed by conversion of the acid to the tert.

butyl amide and N-deprotection, as described below, (Scheme 44) then yields the amine 281.

For example, the compound 282, in which the carboxylic acid group is protected as the trichloroethyl ester, as described in Protective Groups in Organic Synthesis, by T. W. Greene and P. G. M. Wuts, Wiley, 1991, p. 240, and the amine is protected as the cbz group, is reacted with a dialkyl 3-bromopropylphosphonate, 283, the preparation of which is described in J. Amer. Chem. Soc., 2000, 122, 1554 to afford the displacement product 284. Deprotection of the ester group, followed by conversion of the acid to the tert. butyl amide and N-deprotection, as described below, (Scheme 44) then yields the amine 285.

Using the above procedures, but employing, in place of the α-thiol 282, the alcohols, thiols or amines 270, 272, 277, and 278, of either α- or β-orientation, there are obtained the corresponding products 281, in which the orientation of the side chain is the same as that of the O, N or S precursors.

Scheme 41 illustrates the preparation of phosphonates linked to the decahydroisoquinoline moiety by means of a nitrogen atom and a carbon chain. The compounds are prepared by means of a reductive amination procedure, for example as described in Comprehensive Organic Transformations, by R. C. Larock, p. 421.

In this procedure, the amines 272 or 278 are reacted with a phosphonate aldehyde 286, in the presence of a reducing agent, to afford the alkylated amine 287. Deprotection of the ester group, followed by conversion of the acid to the tert. butyl amide and N-deprotection, as described below, (Scheme 44) then yields the amine 288.

For example, the protected amino compound 272 is reacted with a dialkyl formylphosphonate 289, the preparation of which is described in U.S. Pat. No. 3,784,590, in the presence of sodium cyanoborohydride, and a polar organic solvent such as ethanolic acetic acid, as described in Org. Prep. Proc. Int., 11, 201, 1979, to give the amine phosphonate 290. Deprotection of the ester group, followed by conversion of the acid to the tert. butyl amide and N-deprotection, as described below, (Scheme 44) then yields the amine 291.

Using the above procedures, but employing, instead of the α-amine 272, the β isomer, 278 and/or different aldehydes 286, there are obtained the corresponding products 288, in which the orientation of the side chain is the same as that of the amine precursor.

Scheme 42 depicts the preparation of a decahydroisoquinoline phosphonate in which the phosphonate moiety is linked by means of a sulfur atom and a carbon chain.

In this procedure, a thiol phosphonate 292 is reacted with a mesylate 293, to effect displacement of the mesylate group with inversion of stereochemistry, to afford the thioether product 294. Deprotection of the ester group, followed by conversion of the acid to the tert. butyl amide and N-deprotection, as described below, (Scheme 44) then yields the amine 295. For example, the protected mesylate 273 is reacted with an equimolar amount of a dialkyl 2-mercaptoethyl phosphonate 296, the preparation of which is described in Aust. J. Chem., 43, 1123, 1990. The reaction is conducted in a polar organic solvent such as ethanol, in the presence of a base such as, for example, potassium carbonate, at ambient temperature, to afford the thio ether phosphonate 297. Deprotection of the ester group, followed by conversion of the acid to the tert. butyl amide and N-deprotection, as described below, (Scheme 44) then yields the amine 298.

Using the above procedures, but employing, instead of the phosphonate 296, different phosphonates 292, there are obtained the corresponding products 295.

Scheme 43 illustrates the preparation of decahydroisoquinoline phosphonates 299 in which the phosphonate group is linked by means of an aromatic or heteroaromatic ring. The compounds are prepared by means of a displacement reaction between hydroxy, thio or amino substituted substrates 300 and a bromomethyl substituted phosphonate 301. The reaction is performed in an aprotic solvent in the presence of a base of suitable strength, depending on the nature of the reactant 300. If X is S or NH, a weak organic or inorganic base such as triethylamine or potassium carbonate can be employed. If X is O, a strong base such as sodium hydride or lithium hexamethyldisilylazide is required. The displacement reaction affords the ether, thioether or amine compounds 302. Deprotection of the ester group, followed by conversion of the acid to the tert. butyl amide and N-deprotection, as described below, (Scheme 44) then yields the amine 299.

For example, the protected alcohol 303 is reacted at ambient temperature with a dialkyl 3-bromomethyl phenylmethylphosphonate 304, the preparation of which is described above, (Scheme 29). The reaction is conducted in a dipolar aprotic solvent such as, for example, dioxan or dimethylformamide. The solution of the carbinol is treated with one equivalent of a strong base, such as, for example, lithium hexamethyldisylazide, and to the resultant mixture is added one molar equivalent of the bromomethyl phosphonate 304, to afford the product 305. Deprotection of the ester group, followed by conversion of the acid to the tert. butyl amide and N-deprotection, as described below, (Scheme 44) then yields the amine 306.

Using the above procedures, but employing, instead of the β-carbinol 303, different carbinols, thiols or amines 300, of either α- or β-orientation, and/or different phosphonates 301, in place of the phosphonate 304, there are obtained the corresponding products 299, in which the orientation of the side-chain is the same as that of the starting material 300.

Schemes 43-43 illustrate the preparation of decahydroisoquinoline esters incorporating a phosphonate group linked to the decahydroisoquinoline nucleus.

Scheme 44 illustrates the conversion of the latter group of compounds 307 (in which the group B is link-P(O)($OR^1$)$_2$ and precursor compounds thereto (in which B is an optionally protected precursor to the group link-P(O)($OR^1$)$_2$ such as, for example, OH, SH, $NH_2$) to the corresponding tert butyl amides 88.

As shown in Scheme 44, the ester compounds 307 are deprotected to form the corresponding carboxylic acids 308. The methods employed for the deprotection are chosen based on the nature of the protecting group R, the nature of the N-protecting group $R^2$, and the nature of the substituent at the 6-position. For example, if R is trichloroethyl, the ester group is removed by treatment with zinc in acetic acid, as described in J. Amer. Chem. Soc., 88, 852, 1966. Conversion of the carboxylic acid 308 to the tert. butyl amide 309 is then accomplished by reaction of the carboxylic acid, or an activated derivative thereof, with tert. butylamine, as described above for the preparation of 62 (Scheme 1). Deprotection of the $NR^2$ group, as described above, then affords the free amine 88.

Scheme 40
Method
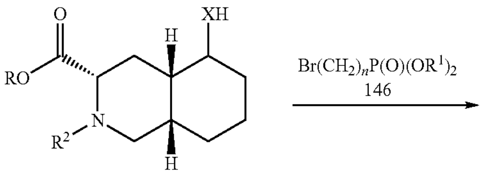
279
X = O, S, NH
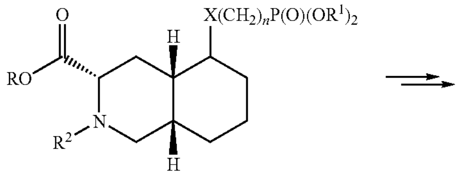
280
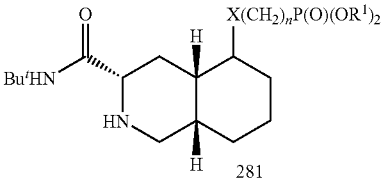
281
Example
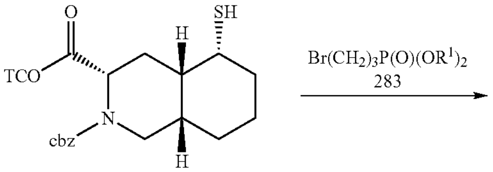
282
TC = trichloroethyl
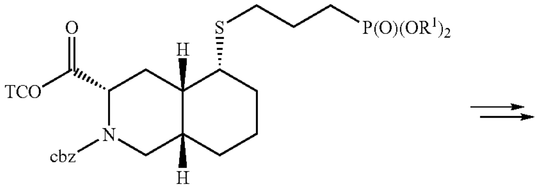
284
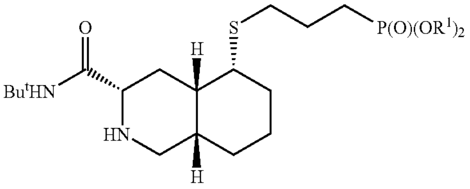
285
Scheme 41
(b) Method
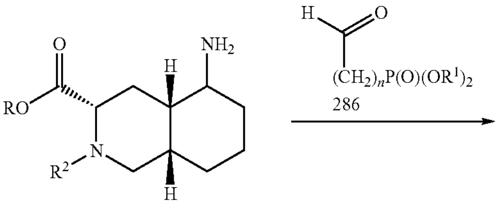
272/8
286
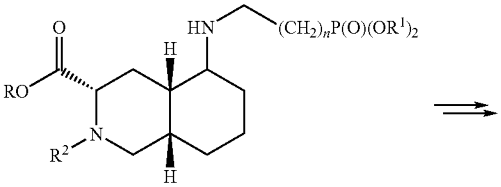
287
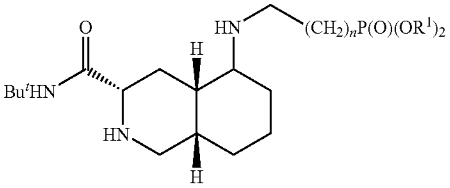
288
Example
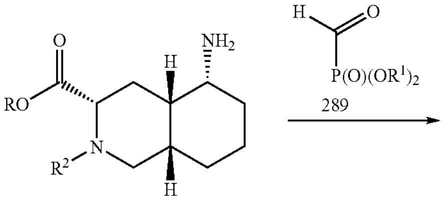
272
289
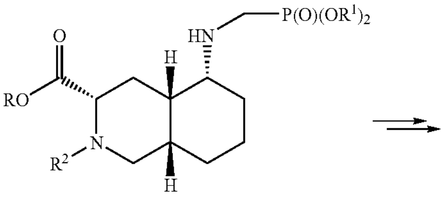
290
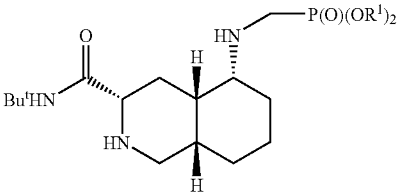
291

Scheme 42
Method
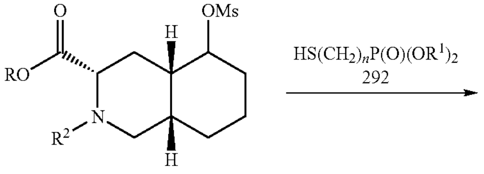
293
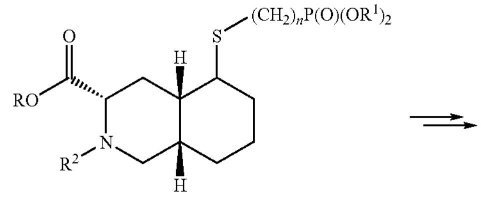
294
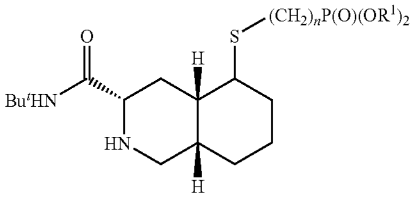
295
Example
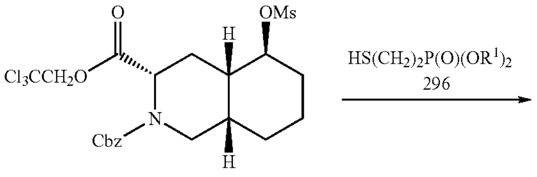
273
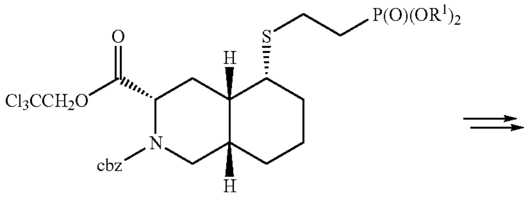
297
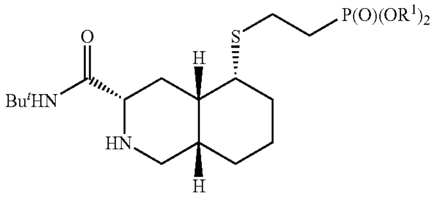
298
Scheme 43
Method
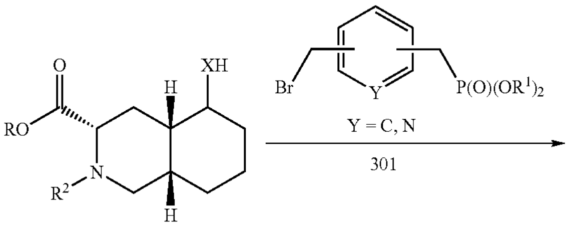
300
X = O, S, NH
$R^2$ = protecting group
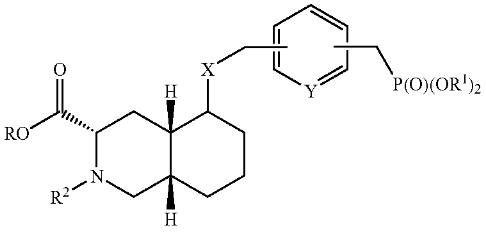
302
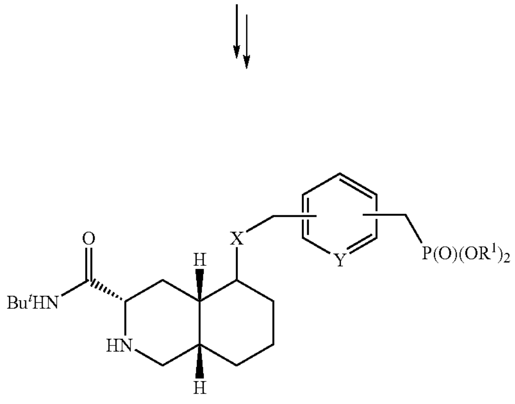
299
Example
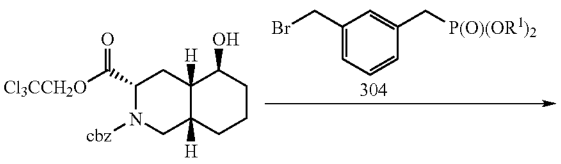
303
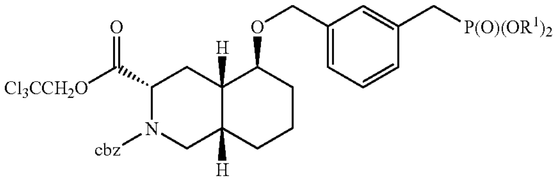
305

-continued

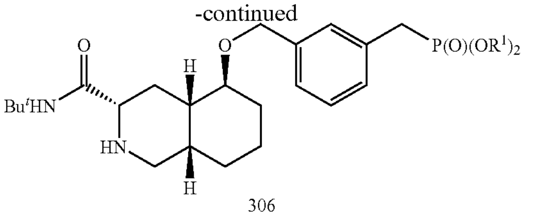

306

Scheme 44

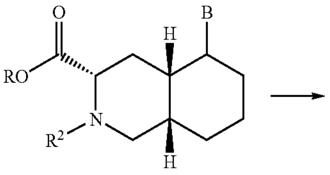

307

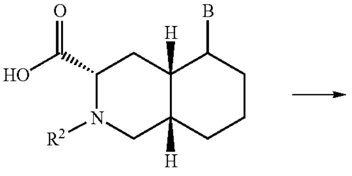

308

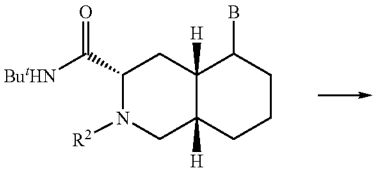

309

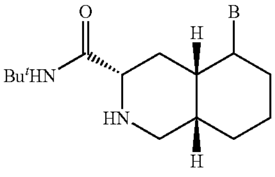

310

Preparation of Phenylalanine Derivatives Incorporating Phosphonate Moieties.

Scheme 45 illustrates the conversion of variously substituted phenylalanine derivatives 311 into epoxides 14a-1, the incorporation of which into the compounds 2 is depicted in Scheme 14a.

A number of compounds 311 or 312, for example those in which X is 2, 3, or 4-OH, or X is 4-$NH_2$ are commercially available. The preparations of different compounds 311 or 312 are described in the literature. For example, the preparation of compounds 311 or 312 in which X is 3-SH, 4-SH, 3-$NH_2$, 3-$CH_2OH$ or 4-$CH_2OH$, are described respectively in WO0036136, J. Amer. Chem. Soc., 1997, 119, 7173, Helv. Chim. Acta, 1978, 58, 1465, Acta Chem. Scand., 1977, B31, 109 and Syn. Com., 1998, 28, 4279. Resolution of compounds 311, if required, can be accomplished by conventional methods, for example as described in Recent Dev. Synth. Org. Chem., 1992, 2, 35.

The variously substituted amino acids 312 are protected, for example by conversion to the BOC derivative 313, by treatment with BOC anhydride, as described in J. Med. Chem., 1998, 41, 1034. The product 313 is then converted into the methyl ester 314, for example by treatment with ethereal diazomethane. The substituent X in 314 is then transformed, using the methods described below, Schemes 46-48, into the group A. The products 315 are then converted, via the intermediates 316-319, into the epoxides 14a-1. The methyl ester 315 is first hydrolyzed, for example by treatment with one molar equivalent of aqueous methanolic lithium hydroxide, or by enzymatic hydrolysis, using, for example, porcine liver esterase, to afford the carboxylic acid 316. The conversion of the carboxylic acid 316 into the epoxide 14a-1, for example using the sequence of reactions which is described in J. Med. Chem., 1994, 37, 1758, is then effected. The carboxylic acid is first converted into the acid chloride, for example by treatment with oxalyl chloride, or into a mixed anhydride, for example by treatment with isobutyl chloroformate, and the activated derivative thus obtained is reacted with ethereal diazomethane, to afford the diazoketone 317. The diazoketone is converted into the chloroketone 318 by reaction with anhydrous hydrogen chloride, in a suitable solvent such as diethyl ether. The latter compound is then reduced, for example by the use of sodium borohydride, to produce a mixture of chlorohydrins from which the desired 2S, 3S diastereomer 319 is separated by chromatography. This material is reacted with ethanolic potassium hydroxide at ambient temperature to afford the epoxide 14a-1. Optionally, the above described series of reactions can be performed on the methyl ester 314, so as to yield the epoxide 14a-1 in which A is OH, SH, NH, Nalkyl or $CH_2OH$.

Methods for the transformation of the compounds 314, in which X is a precursor group to the substituent link-P(O)$(OR^1)_2$, are illustrated in Schemes 46-48.

Scheme 46 depicts the preparation of epoxides 322 incorporating a phosphonate group linked to the phenyl ring by means of a heteroatom O, S or N. In this procedure, the phenol, thiol, amine or carbinol 314 is reacted with a derivative of a dialkyl hydroxymethyl phosphonate 320. The reaction is accomplished in the presence of a base, the nature of which depends on the nature of the substituent X. For example, if X is OH, SH, $NH_2$ or NHalkyl, an inorganic base such as cesium carbonate, or an organic base such as diazabicyclononene, can be employed. If X is $CH_2OH$, a base such as lithium hexamethyldisilylazide or the like can be employed. The condensation reaction affords the phosphonate-substituted ester 321, which, employing the sequence of reactions shown in Scheme 45, is transformed into the epoxide 322.

For example, 2-tert.-butoxycarbonylamino-3-(4-hydroxyphenyl)-propionic acid methyl ester, 323 (Fluka) is reacted with a dialkyl trifluoromethanesulfonyloxy phosphonate 138, prepared as described in Tet. Lett., 1986, 27, 1477, in the presence of cesium carbonate, in dimethylformamide at ca 60°, to afford the ether product 324. The latter compound is then converted, using the sequence of reactions shown in Scheme 45, into the epoxide 325.

Using the above procedures, but employing different phenols, thiols, amines and carbinols 314 in place of 323, and/or different phosphonates 320, the corresponding products 322 are obtained.

Scheme 47 illustrates the preparation of a phosphonate moiety is attached to the phenylalanine scaffold by means of a heteroatom and a multi-carbon chain.

In this procedure, a substituted phenylalanine derivative 314 is reacted with a dialkyl bromoalkyl phosphonate 146 to afford the product 326. The conditions employed for this reaction are the same as those described above for the preparation of 148, (Scheme 25) The product 326 is then transformed, using the sequence of reactions shown in Scheme 45, into the epoxide 327.

For example, the protected aminoacid 328, prepared as described above (Scheme 45) from 3-mercaptophenylalanine, the preparation of which is described in WO 0036136, is reacted with a dialkyl 2-bromoethyl phosphonate 329, prepared as described in Synthesis, 1994, 9, 909, in the presence of cesium carbonate, in dimethylformamide at ca 60°, to afford the thioether product 330. The latter compound is then converted, using the sequence of reactions shown in Scheme 45, into the epoxide 331.

Using the above procedures, but employing different phenols, thiols, and amines 314 in place of 328, and/or different phosphonates 146, the corresponding products 327 are obtained.

Scheme 48 depicts the preparation of phosphonate-substituted phenylalanine derivatives in which the phosphonate moiety is attached by means of an alkylene chain incorporating a heteroatom.

In this procedure, a protected hydroxymethyl-substituted phenylalanine 332 is converted into the halomethyl-substituted compound 333. For example, the carbinol 332 is treated with triphenylphosphine and carbon tetrabromide, as described in J. Amer. Chem. Soc., 108, 1035, 1986 to afford the product 333 in which Z is Br. The bromo compound is then reacted with a dialkyl terminally hetero-substituted alkylphosphonate 334. The reaction is accomplished in the presence of a base, the nature of which depends on the nature of the substituent X. For example, if X is SH, $NH_2$ or NHalkyl, an inorganic base such as cesium carbonate, or an organic base such as diazabicyclononene, can be employed. If X is OH, a strong base such as lithium hexamethyldisilylazide or the like can be employed. The condensation reaction affords the phosphonate-substituted ester 335, which, employing the sequence of reactions shown in Scheme 45, is transformed into the epoxide 336.

For example, the protected 4-hydroxymethyl-substituted phenylalanine derivative 337, obtained from the 4-hydroxymethyl phenylalanine, the preparation of which is described in Syn. Comm., 1998, 28, 4279, is converted into the bromo derivative 338, as described above. The product is then reacted with a dialkyl 2-aminoethyl phosphonate 339, the preparation of which is described in J. Org. Chem., 2000, 65, 676, in the presence of cesium carbonate in dimethylformamide at ambient temperature, to afford the amine product 340. The latter compound is then converted, using the sequence of reactions shown in Scheme 45, into the epoxide 341.

Using the above procedures, but employing different carbinols 332 in place of 337, and/or different phosphonates 334, the corresponding products 336 are obtained.

Scheme 45

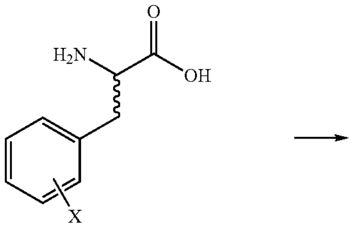

311

X = OH, SH, $NH_2$, NHalkyl, $CH_2OH$

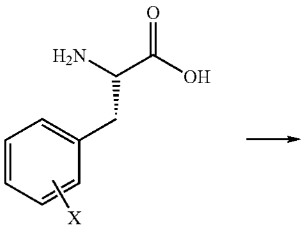

312

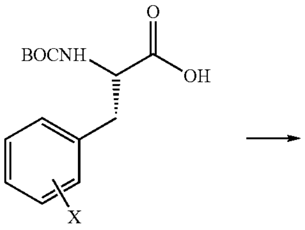

313

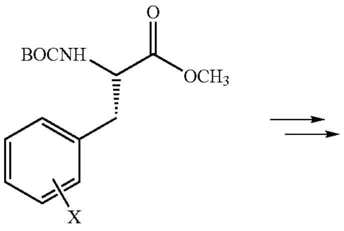

314

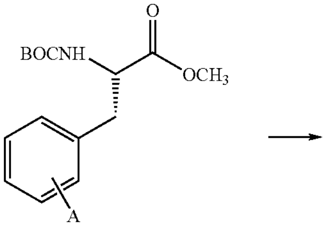

315

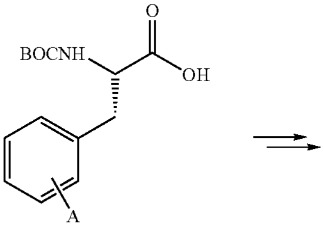

316

-continued
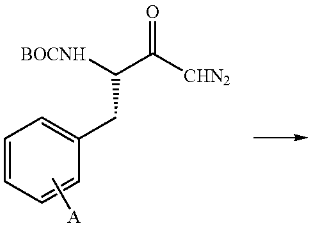
317
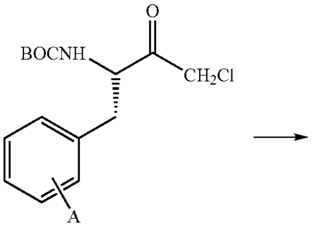
318
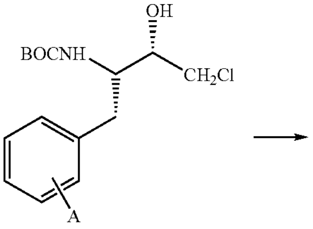
319
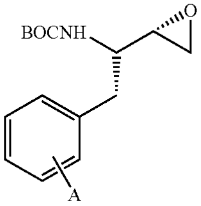
14a-1
-continued
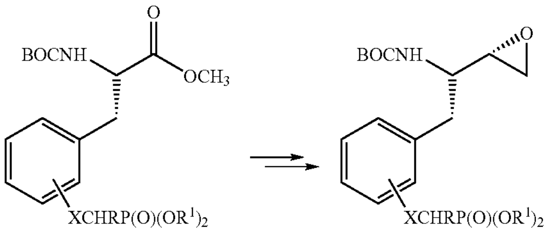
321 322
Example
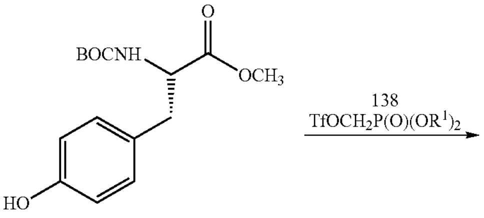
323
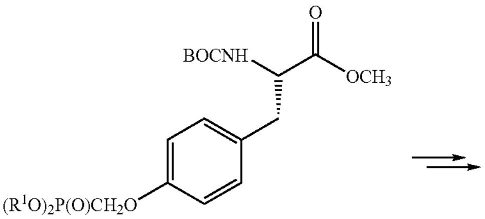
324
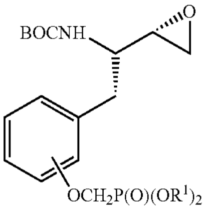
325
Scheme 46
Method
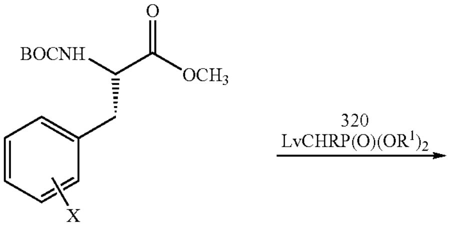
314
X = OH, SH, $NH_2$, NHalkyl, $CH_2OH$
Scheme 47
Method
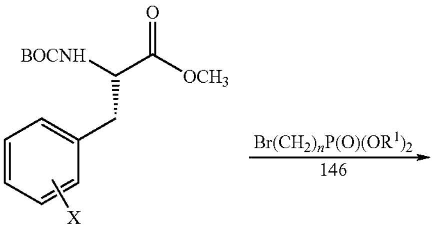
X = OH, SH, $NH_2$, NHalkyl
314

-continued
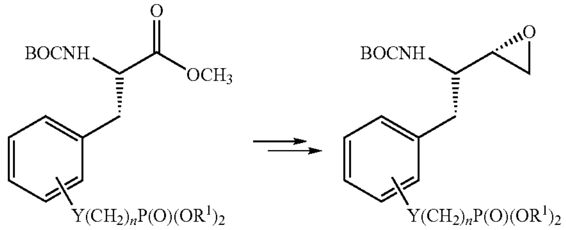
Y = O, S, NH, Nalkyl
326
327
Example
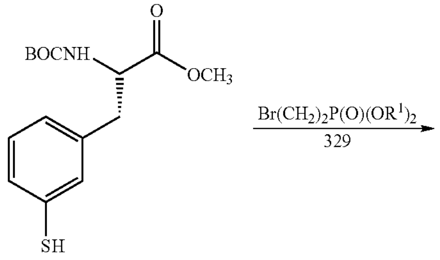
328
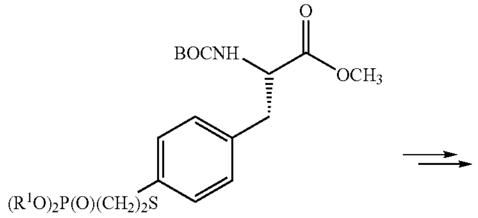
330
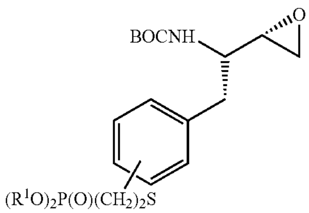
331
Scheme 48
Method
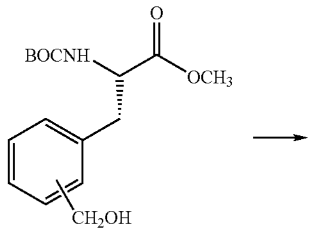
332
-continued
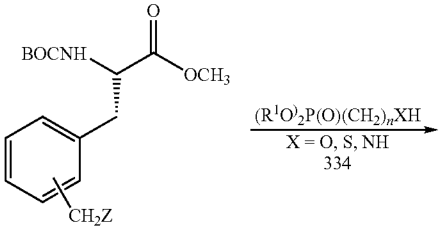
Z = Cl, Br
333
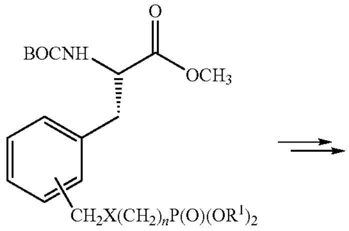
335
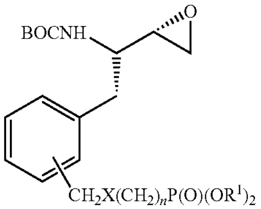
336
Example
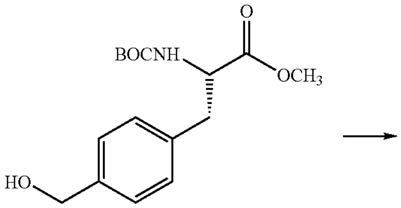
337
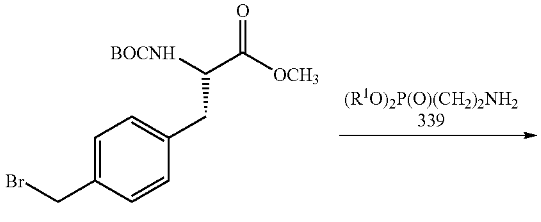
338
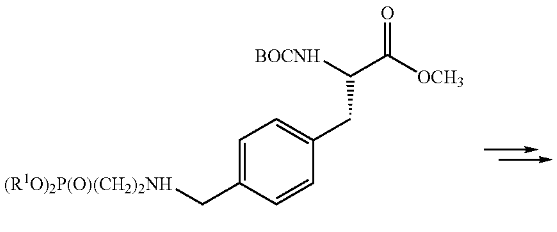
340

-continued

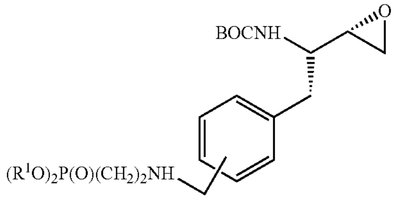

341

Interconversions of the Phosphonates R-link-P(O)($OR^1$)$_2$, R-link-P(O)($OR^1$)(OH) and R-link-P(O)(OH)$_2$.

Schemes 1-48 describe the preparations of phosphonate esters of the general structure R-link-P(O) ($OR^1$)$_2$, in which the groups $R^1$, the structures of which are defined in Chart 1, may be the same or different. The $R^1$ groups attached to phosphonate esters 1-4a, or to precursors thereto, may be changed using established chemical transformations. The interconversions reactions of phosphonates are illustrated in Scheme 49. The group R in Scheme 49 represents the substructure to which the substituent link-P(O)($OR^1$)$_2$ is attached, either in the compounds 1-4a or in precursors thereto. The $R^1$ group may be changed, using the procedures described below, either in the precursor compounds, or in the esters 1-4a. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 342 into the corresponding phosphonate monoester 343 (Scheme 49, Reaction 1) can be accomplished by a number of methods. For example, the ester 342 in which $R^1$ is an aralkyl group such as benzyl, can be converted into the monoester compound 343 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 342 in which $R^1$ is an aryl group such as phenyl, or an alkenyl group such as allyl, into the monoester 343 can be effected by treatment of the ester 342 with a base such as aqueous sodium hydroxide in acetonitrile or lithium hydroxide in aqueous tetrahydrofuran. Phosphonate diesters 343 in which one of the groups $R^1$ is aralkyl, such as benzyl, and the other is alkyl, can be converted into the monoesters 343 in which $R^1$ is alkyl by hydrogenation, for example using a palladium on carbon catalyst. Phosphonate diesters in which both of the groups $R^1$ are alkenyl, such as allyl, can be converted into the monoester 343 in which $R^1$ is alkenyl, by treatment with chlorotris(triphenylphosphine) rhodium (Wilkinson's catalyst) in aqueous ethanol at reflux, optionally in the presence of diazabicyclooctane, for example by using the procedure described in J. Org. Chem., 38 3224 1973 for the cleavage of allyl carboxylates.

The conversion of a phosphonate diester 342 or a phosphonate monoester 343 into the corresponding phosphonic acid 344 (Scheme 49, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 343 in which $R^1$ is aralkyl such as benzyl, can be converted into the corresponding phosphonic acid 344 by hydrogenation over a palladium catalyst, or by treatment with hydrogen chloride in an ethereal solvent such as dioxan. A phosphonate monoester 343 in which $R^1$ is alkenyl such as, for example, allyl, can be converted into the phosphonic acid 344 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 342 in which $R^1$ is benzyl is described in J. Org. Chem., 24, 434, 1959. Platinum-catalyzed hydrogenolysis of phosphonate esters 342 in which $R^1$ is phenyl is described in J. Amer. Chem. Soc., 78, 2336, 1956.

The conversion of a phosphonate monoester 343 into a phosphonate diester 342 (Scheme 49, Reaction 4) in which the newly introduced $R^1$ group is alkyl, aralkyl, haloalkyl such as chloroethyl, or aralkyl can be effected by a number of reactions in which the substrate 343 is reacted with a hydroxy compound $R^1$OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 342 to the diester 342 can be effected by the use of the Mitsonobu reaction, as described above (Scheme 16). The substrate is reacted with the hydroxy compound $R^1$OH, in the presence of diethyl azodicarboxylate and a triarylphosphine such as triphenyl phosphine. Alternatively, the phosphonate monoester 343 can be transformed into the phosphonate diester 342, in which the introduced $R^1$ group is alkenyl or aralkyl, by reaction of the monoester with the halide $R^1$Br, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 343 is transformed into the chloro analog RP(O)($OR^1$)Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product RP(O)($OR^1$)Cl is then reacted with the hydroxy compound $R^1$OH, in the presence of a base such as triethylamine, to afford the phosphonate diester 342.

A phosphonic acid R-link-P(O)(OH)$_2$ can be transformed into a phosphonate monoester RP(O)($OR^1$)(OH) (Scheme 49, Reaction 5) by means of the methods described above of for the preparation of the phosphonate diester R-link-P(O) ($OR^1$)$_2$ 342, except that only one molar proportion of the component $R^1$OH or $R^1$Br is employed.

A phosphonic acid R-link-P(O)(OH)$_2$ 344 can be transformed into a phosphonate diester R-link-P(O) ($OR^1$)$_2$ 342 (Scheme 49, Reaction 6) by a coupling reaction with the hydroxy compound $R^1$OH, in the presence of a coupling agent such as Aldrithiol-2 (Aldrich) and triphenylphosphine. The reaction is conducted in a basic solvent such as pyridine.

Alternatively, phosphonic acids 344 can be transformed into phosphonic esters 342 in which $R^1$ is aryl, by means of a coupling reaction employing, for example, dicyclohexylcarbodiimide in pyridine at ca 70°. Alternatively, phosphonic acids 344 can be transformed into phosphonic esters 342 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 342.

Preparation of Carbamates.

The phosphonate ester compounds 2-4a in which the $R^5CO$ group is derived from the carbonic acid derivatives C38-C49, the structures of which are shown in Chart 4c, are carbamates. The compounds have the general structure ROCONHR', wherein the substructure ROCO represents the group $R^5CO$, as defined in Chart 4c, and the substituent R' represents the substructure to which the amine group is attached. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 50 illustrates various methods by which the carbamate linkage can be synthesized. As shown in Scheme 50, in the general reaction generating carbamates, a carbinol 345 is converted into the activated derivative 346 in which Lv is a leaving group such as halo, imidazolyl, benztriazolyl and the like, as described below. The activated derivative 346 is then reacted with an amine 347, to afford the carbamate product 348. Examples 1-7 in Scheme 50 depict methods by which the general reaction can be effected. Examples 8-10 illustrate alternative methods for the preparation of carbamates.

Scheme 50, Example 1 illustrates the preparation of carbamates employing a chloroformyl derivative of the carbinol 349. In this procedure, the carbinol 349 is reacted with phosgene, in an inert solvent such as toluene, at about 0°, as described in Org. Syn. Coll. Vol. 3, 167, 1965, or with an equivalent reagent such as trichloromethoxy chloroformate, as described in Org. Syn. Coll. Vol. 6, 715, 1988, to afford the chloroformate 350. The latter compound is then reacted with the amine component 347, in the presence of an organic or inorganic base, to afford the carbamate 351. For example, the chloroformyl compound 350 is reacted with the amine 347 in a water-miscible solvent such as tetrahydrofuran, in the presence of aqueous sodium hydroxide, as described in Org. Syn. Coll. Vol. 3, 167, 1965, to yield the carbamate 351. Alternatively, the reaction is preformed in dichloromethane in the presence of an organic base such as diisopropylethylamine or dimethylaminopyridine.

Scheme 50, Example 2 depicts the reaction of the chloroformate compound 350 with imidazole, 351, to produce the imidazolide 352. The imidazolide product is then reacted with the amine 347 to yield the carbamate 351. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in J. Med. Chem., 1989, 32, 357.

Scheme 50 Example 3, depicts the reaction of the chloroformate 350 with an activated hydroxyl compound R"OH, to yield the mixed carbonate ester 354. The reaction is conducted in an inert organic solvent such as ether or dichloromethane, in the presence of a base such as dicyclohexylamine or triethylamine. The hydroxyl component R"OH is selected from the group of compounds 363-368 shown in Scheme 50, and similar compounds. For example, if the component R"OH is hydroxybenztriazole 363, N-hydroxysuccinimide 364, or pentachlorophenol, 365, the mixed carbonate 354 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 366 or 2-hydroxypyridine 367 can be performed in an ethereal solvent in the presence of triethylamine, as described in Syn., 1986, 303, and Chem. Ber. 118, 468, 1985.

Scheme 50 Example 4 illustrates the preparation of carbamates in which an alkyloxycarbonylimidazole 352 is employed. In this procedure, a carbinol 349 is reacted with an equimolar amount of carbonyl diimidazole 355 to prepare the intermediate 352. The reaction is conducted in an aprotic organic solvent such as dichloromethane or tetrahydrofuran. The acyloxyimidazole 352 is then reacted with an equimolar amount of the amine $R'NH_2$ to afford the carbamate 351. The reaction is performed in an aprotic organic solvent such as dichloromethane, as described in Tet. Lett., 42, 2001, 5227, to afford the carbamate 351.

Scheme 50, Example 5 illustrates the preparation of carbamates by means of an intermediate alkoxycarbonylbenztriazole 357. In this procedure, a carbinol ROH is reacted at ambient temperature with an equimolar amount of benztriazole carbonyl chloride 356, to afford the alkoxycarbonyl product 357. The reaction is performed in an organic solvent such as benzene or toluene, in the presence of a tertiary organic amine such as triethylamine, as described in Syn., 1977, 704. This product is then reacted with the amine $R'NH_2$ to afford the carbamate 351. The reaction is conducted in toluene or ethanol, at from ambient temperature to about 80° as described in Syn., 1977, 704.

Scheme 50, Example 6 illustrates the preparation of carbamates in which a carbonate $(R''O)_2CO$, 358, is reacted with a carbinol 349 to afford the intermediate alkyloxycarbonyl intermediate 359. The latter reagent is then reacted with the amine $R'NH_2$ to afford the carbamate 351. The procedure in which the reagent 359 is derived from hydroxybenztriazole 363 is described in Synthesis, 1993, 908; the procedure in which the reagent 359 is derived from N-hydroxysuccinimide 364 is described in Tet. Lett., 1992, 2781; the procedure in which the reagent 359 is derived from 2-hydroxypyridine 367 is described in Tet. Lett., 1991, 4251; the procedure in which the reagent 359 is derived from 4-nitrophenol 368 is described in Syn. 1993, 103. The reaction between equimolar amounts of the carbinol ROH and the carbonate 358 is conducted in an inert organic solvent at ambient temperature.

Scheme 50, Example 7 illustrates the preparation of carbamates from alkoxycarbonyl azides 360. In this procedure, an alkyl chloroformate 350 is reacted with an azide, for example sodium azide, to afford the alkoxycarbonyl azide 360. The latter compound is then reacted with an equimolar amount of the amine $R'NH_2$ to afford the carbamate 351. The reaction is conducted at ambient temperature in a polar aprotic solvent such as dimethylsulfoxide, for example as described in Syn., 1982, 404.

Scheme 50, Example 8 illustrates the preparation of carbamates by means of the reaction between a carbinol ROH and the chloroformyl derivative of an amine. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 351.

Scheme 50, Example 9 illustrates the preparation of carbamates by means of the reaction between a carbinol ROH and an isocyanate 362. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 351.

Scheme 50, Example 10 illustrates the preparation of carbamates by means of the reaction between a carbinol ROH and an amine $R'NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 351.

Scheme 49

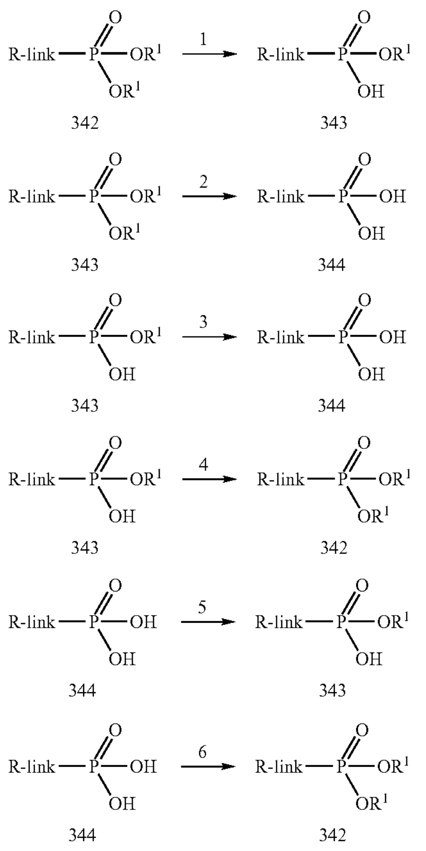

Scheme 50

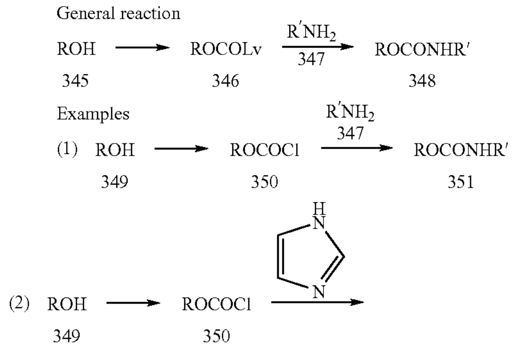

-continued

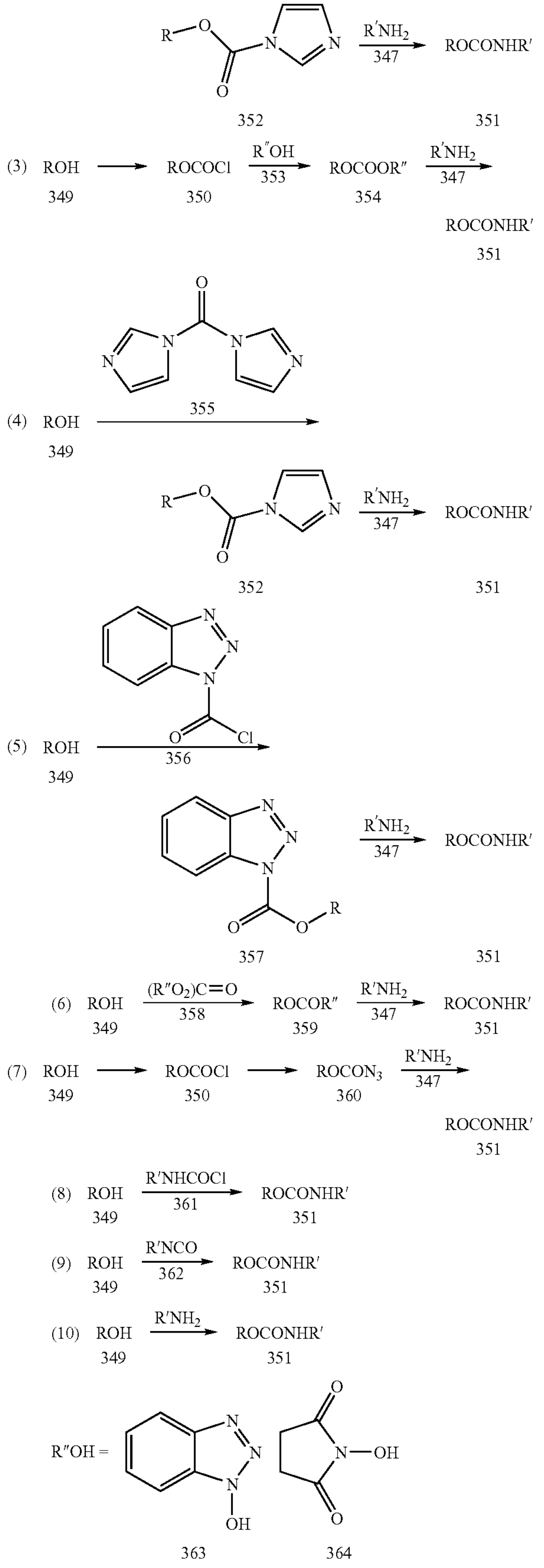

-continued

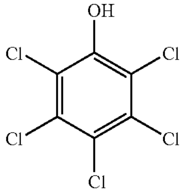

365

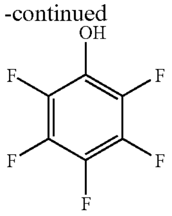

366

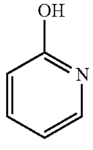

367

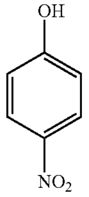

368

General Applicability of Methods for Introduction of Phosphonate Substituents.

The above-described methods for the preparation of phosphonate-substituted thiols, Schemes 20 to 30, can, with appropriate modifications according to the knowledge of one skilled in the art, be applied to the preparation of phosphonate-substituted benzoic acids, tert-butylamines, decahydroisoquinolines and phenylalanines.

Similarly, preparative methods described above for phosphonate-substituted benzoic acids, tert-butylamines, decahydroisoquinolines and phenylalanines, Schemes 31 to 48, can, with appropriate modifications according to the knowledge of one skilled in the art, be applied to the preparation of phosphonate-substituted thiophenols.

Preparation of Compounds 1-4a with Phosphonate Moieties Attached to any Substructural Component.

The chemical transformations described in Schemes 1-50 illustrate the preparation of compounds 1-4 in which the phosphonate ester moiety is attached to the hydroxymethyl benzoic acid group (Schemes 1-3), the phenylthio moiety (Schemes 4-6), the amine moiety (Schemes 7-9), the decahydroisoquinoline moiety (Schemes 10-12) and the phenyl moiety (Schemes 10-14b).

Charts 2-4 illustrate various chemical substructures that may be substituted for the phosphonate-containing moieties. For example, in Chart 2, substructures 6, 7 and 8-20e may be substituted for the decahydroisoquinoline moiety, and in Chart 3, substructures 21-26 may be substituted for the group $CH_2XR^4$ in compounds 1-4. Charts 4a-c illustrate the structures of the compounds $R^5COOH$ which may be incorporated into the phosphonate esters 2-4. By utilization of the methods described herein for the preparation of, and incorporation of phosphonate-containing moieties, and by the application of the knowledge of one skilled in the art, the phosphonate ester moieties described herein may be incorporated into the amines 6, 7, and 8-20, into the $R^4$ groups 21-26, and into the carboxylic acids, or functional equivalents thereof, with the structures C1-C49. Subsequently, the thus-obtained phosphonate-ester containing moieties may, utilizing the procedures described above in Schemes 1-14b, be incorporated into the compounds represented by the formula 4a (Chart 1) in which one of the groups $R^2NHCR^3$, $R^4$, $R^5$ or But contains a phosphonate group of the general formula link-$P(O)(OR^1)_2$.

Lopinavir-like Phosphonate Protease Inhibitors (LLPPI)

Preparation of the Intermediate Phosphonate Esters.

The structures of the intermediate phosphonate esters 1 to 5 and the structures for the component groups R"of this invention are shown in Chart 1.

The structures of the $R^2COOH$ and $R^3OOH$ components C1-C49 are shown in Charts 2a, 2b and 2c. Specific stereoisomers of some of the structures are shown in Charts 1, and 2; however, all stereoisomers are utilized in the syntheses of the compounds 1 to 5. Subsequent chemical modifications to the compounds 1 to 5, as described herein, permit the synthesis of the final compounds of this invention.

The intermediate compounds 1 to 5 incorporate a phosphonate moiety connected to the nucleus by means of a variable linking group, designated as "link" in the attached structures. Charts 4 and 5 illustrate examples of the linking groups present in the structures 1-5, and in which "etc" refers to the scaffold, e.g., lopinavir.

Schemes 1-33 illustrate the syntheses of the intermediate phosphonate compounds of this invention, 1-3, and of the intermediate compounds necessary for their synthesis. The preparation of the phosphonate esters 4 and 5, in which the phosphonate moiety is incorporated into different members of the groups $R^2COOH$ and $R^3COOH$, is also described below.

CHART 1

Intermediate phosphonate esters

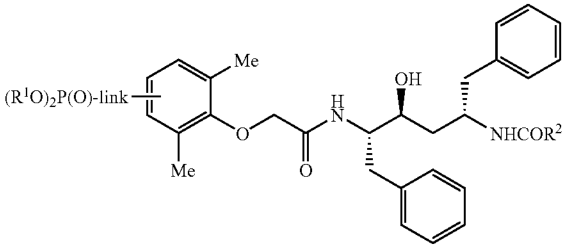

1

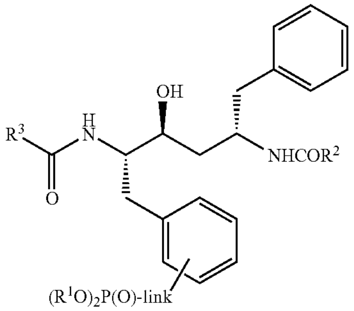

2

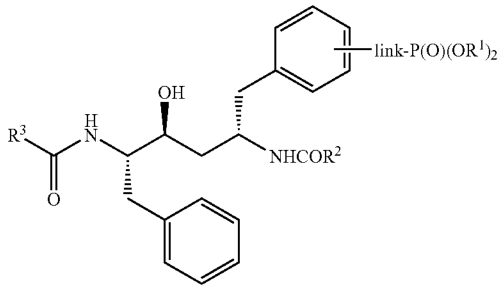

3

CHART 1-continued
Intermediate phosphonate esters
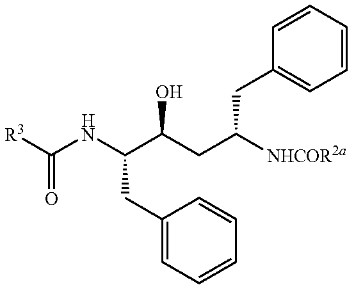
4
$R^{2a}$ = phosphonate-containing $R^2$
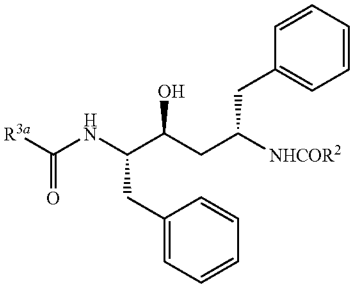
5
$R^{3a}$ = phosphonate-containing $R^3$
$R^1$ = H, alkyl, haloalkyl, alkenyl, aralkyl, aryl
CHART 2a
Structures of the $R^2COOH$ and $R^3COOH$ components
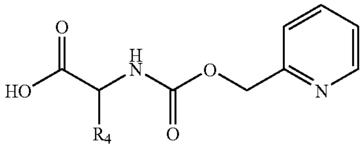
C1
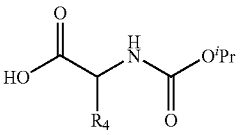
C2
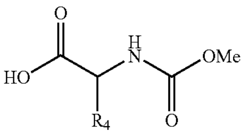
C3
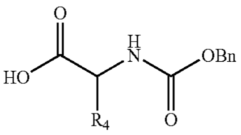
C4
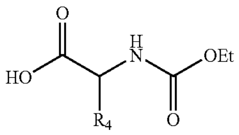
C5
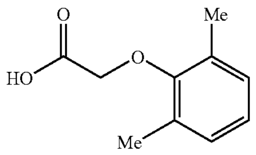
C6
CHART 2a-continued
Structures of the $R^2COOH$ and $R^3COOH$ components
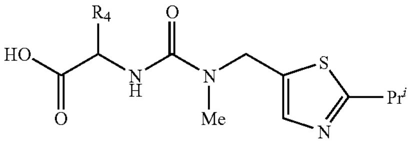
C7
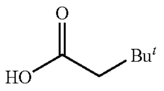
C8
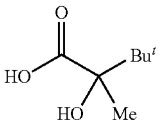
C9
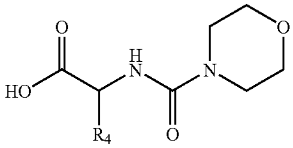
C10
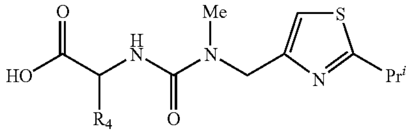
C11
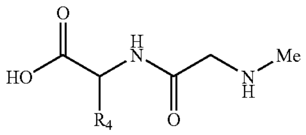
C12
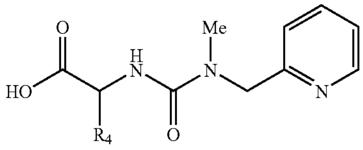
C13
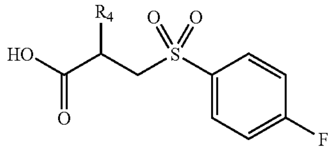
C14
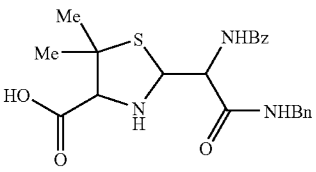
C15

CHART 2a-continued
Structures of the $R^2COOH$ and $R^3COOH$ components
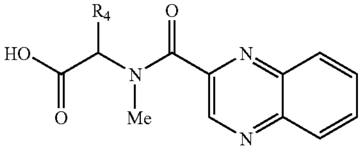
C16
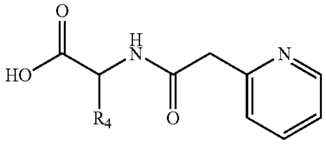
C17
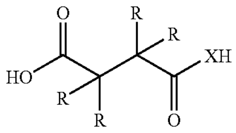
X = O, NH
R = H, alkyl
C18
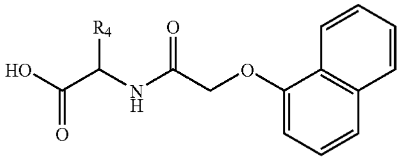
C19
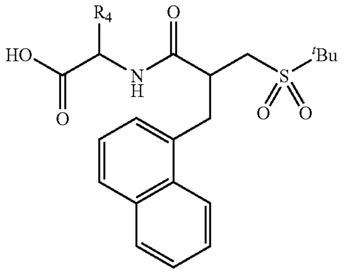
C20
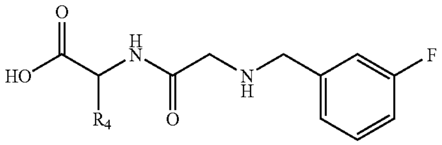
C21
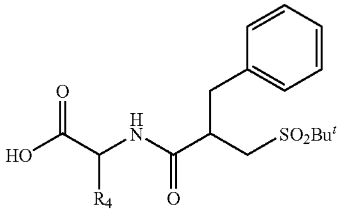
C22
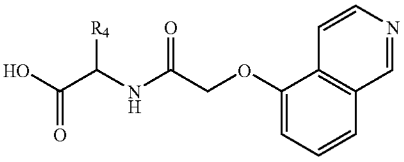
C23
CHART 2a-continued
Structures of the $R^2COOH$ and $R^3COOH$ components
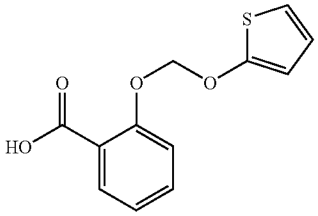
C24
$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 2b
Structures of the $R^2COOH$ and $R^3COOH$ components
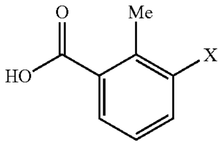
C25
X = OH, $NH_2$
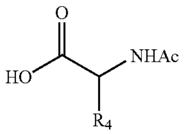
C26
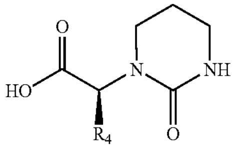
C27
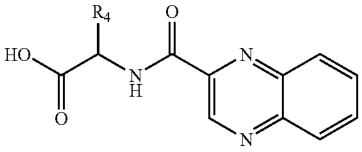
C28
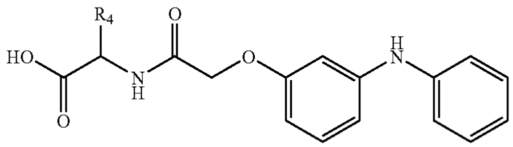
C29
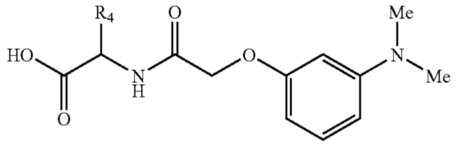
C30
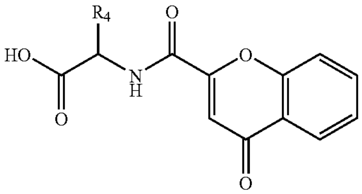
C31

CHART 2b-continued

Structures of the $R^2COOH$ and $R^3COOH$ components

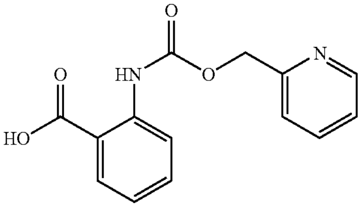

C32

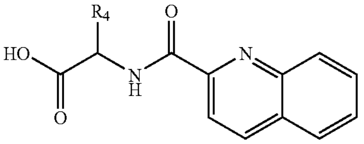

C33

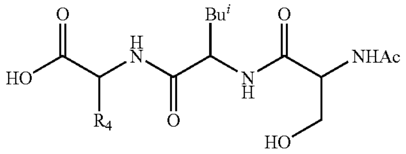

C34

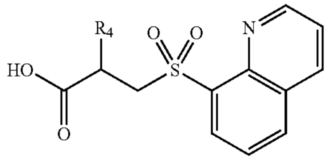

C35

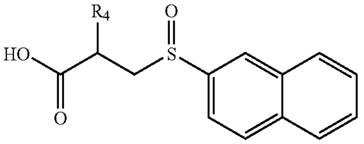

C36

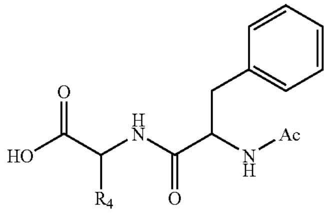

C37

$R^4$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$ CHART 2c Structures of the $R^2COOH$ and $R^3COOH$ components

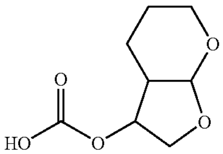

C38

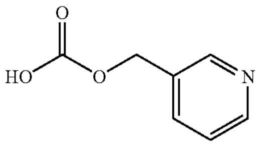

C39

CHART 2c-continued

Structures of the $R^2COOH$ and $R^3COOH$ components

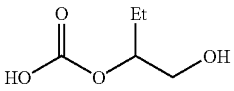

C40

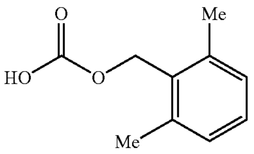

C41

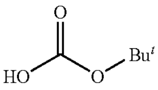

C42

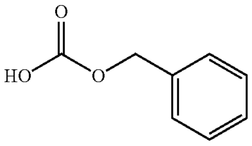

C43

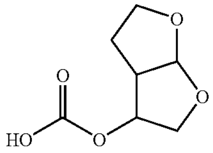

C44

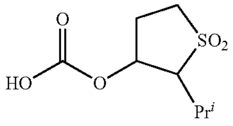

C45

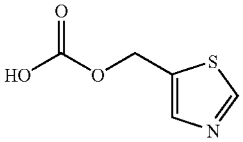

C46

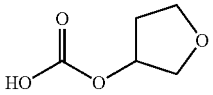

C47

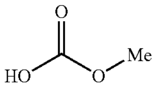

C48

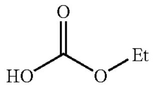

C49

CHART 4

Examples of the linking group between the scaffold and the phosphonate moiety.

| link | examples |
|---|---|
| direct bond | 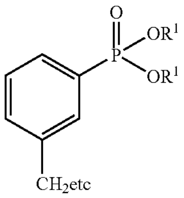 |
| | 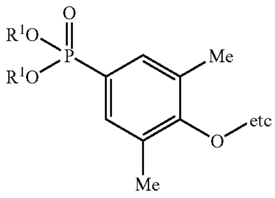 |

CHART 4-continued

| Examples of the linking group between the scaffold and the phosphonate moiety. | |
|---|---|
| link | examples |
| single carbon | 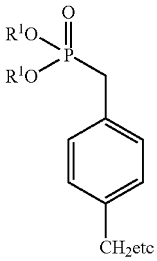 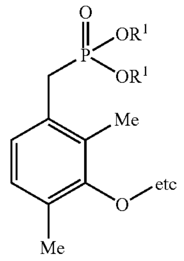 |
| multiple carbon | 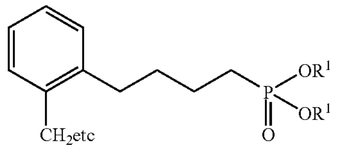 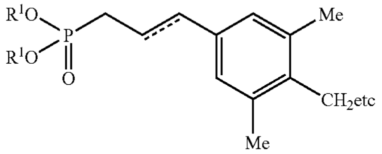 |
| hetero atoms | 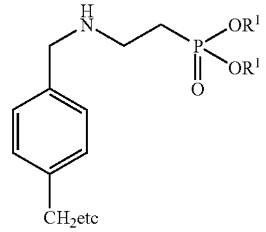 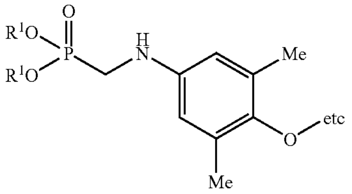 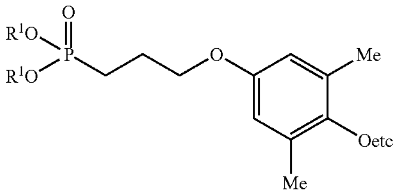 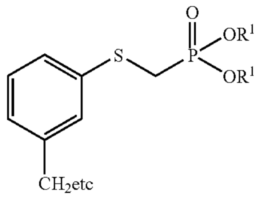 |

CHART 5

| Examples of the linking group between the scaffold and the phosphonate moiety. | |
|---|---|
| link | examples |
| aryl, heteroaryl | 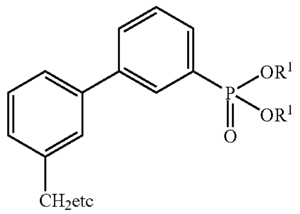 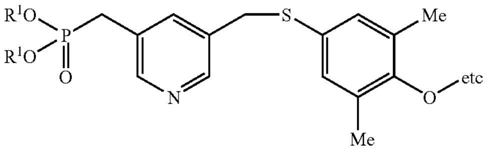 |
| cycloalkyl | 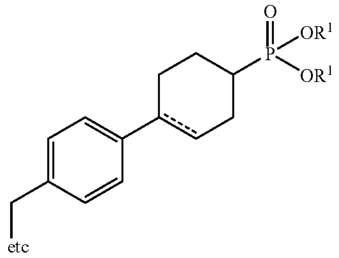 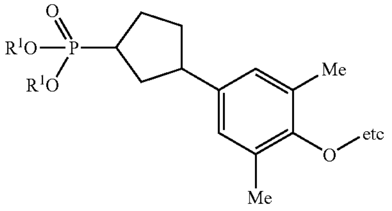 |
| cyclized | 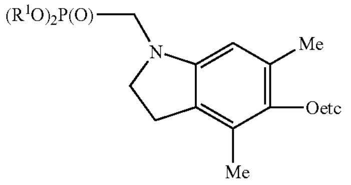 |

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective 10 Groups in Organic Synthesis, by T. W. Greene and P. G. M Wuts, Wiley, Second Edition 1990. Reactive substituents which may be protected are shown in the accompanying schemes as, for example, [OH], [SH].

Preparation of the Phosphonate Intermediates 1.

Two methods for the preparation of the phosphonate intermediate compounds 1 are shown in Schemes 1 and 2. The selection of the route to be employed for a given compound is made after consideration of the substituents which are present, and their stability under the reaction conditions required.

As shown in Scheme 1,5-amino-2-dibenzylamino-1,6-diphenyl-hexan-3-ol, 1.1, the preparation of which is described in Org. Process Res. Dev., 1994, 3, 94, is reacted with a carboxylic acid $R^2COOH$, or an activated derivative 1.2 thereof, to produce the amide 1.3. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of hydroxybenztriazole, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane.

Preferably, the carboxylic acid is converted into the acid chloride 1.2, X═Cl, and the latter compound is reacted with an equimolar amount of the amine 1.1, in an aprotic solvent such as, for example, tetrahydrofuran, at ambient temperature. The reaction is conducted in the presence of an organic base such as triethylamine, so as to afford the amide product 1.3. The N,N-dibenzylamino amide product 1.3 is then transformed into the free amine compound 1.4 by means of a debenzylation procedure. The deprotection of N-benzyl amines is described, for example, in Protective Groups in Organic Synthesis, by T. W. Greene and P. G. M Wuts, Wiley, Second Edition 1990, p. 365. The transformation can be effected under reductive conditions, for example by the use of hydrogen or a hydrogen transfer agent, in the presence of a palladium catalyst, or by treatment of the N-benzyl amine with sodium in liquid ammonia, or under oxidative conditions, for example by treatment with 3-chloroperoxybenzoic acid and ferrous chloride.

Preferably, the N,N-dibenzyl compound 1.3 is converted into the amine 1.4 by means of hydrogen transfer catalytic hydrogenolysis, for example by treatment with methanolic ammonium formate and 5% palladium on carbon catalyst, at ca. 75° for ca. 6 hours, for example as described in U.S. Pat. No. 5,914,332.

The thus-obtained amine 1.4 is then transformed into the amide 1.5 by reaction with the carboxylic acid 1.6, or an activated derivative thereof, in which the substituent A is either the group link-$P(O)(OR^1)_2$ or a precursor thereto, such as [OH], [SH], [NH], [CHO], Br, as described below. Preparations of the carboxylic acids 1.6 are described below, Schemes 9-14. The amide-forming reaction is conducted under similar conditions to those described above for the preparation of the amide 1.3.

Preferably, the carboxylic acid 1.6 is converted into the acid chloride, and the acid chloride is reacted with the amine 1.4 in a solvent mixture composed of an organic solvent such as ethyl acetate, and water, in the presence of a base such as sodium bicarbonate, for example as described in Org. Process Res. Dev., 2000, 4, 264, to afford the amide product 1.5. Alternatively, the amide 1.5 can be obtained by the procedure shown in Scheme 2. In this method, 2-tert-butoxycarbonylamino-5-methyl-1,6-diphenyl-hexan-3-ol, 2.1, the preparation of which is described in U.S. Pat. No. 5,4912,53, is reacted with the carboxylic acid 1.6, or an activated derivative thereof, in which the substituent A is either the group link-P(O)($OR^1$)$_2$ or a precursor thereto. The reaction is conducted under similar conditions to those described above for the preparation of the amides 1.3 and 1.5.

Preferably, equimolar amounts of the amine 2.1 and the carboxylic acid 1.6 are reacted in dimethylformamide in the presence of a carbodiimide, such as, for example, 1-dimethylaminopropyl-3-ethylcarbodiimide, as described, for example, in U.S. Pat. No. 5,914,332, to yield the amide 2.2.

The tert-butoxycarbonyl (BOC) protecting group is then removed from the product 2.2 to afford the free amine 2.3. The removal of BOC protecting groups is described, for example, in Protective Groups in Organic Synthesis, by T. W. Greene and P. G. M Wuts, Wiley, Second Edition 1990, p. 328. The deprotection can be effected by treatment of the BOC compound with anhydrous acids, for example, hydrogen chloride or trifluoroacetic acid, or by reaction with trimethylsilyl iodide or aluminum chloride.

Preferably, the BOC group is removed by treatment of the substrate 2.2 with trifluoroacetic acid in dichloromethane at ambient temperature, for example as described in U.S. Pat. No. 5,9142,32, to afford the free amine product 2.3.

The amine product 2.3 is then reacted with the acid $R^2COOH$ 2.4, or an activated derivative thereof, to produce the amide 2.5. This reaction is conducted under similar conditions to those described above for the preparation of the amides 1.3 and 1.5.

Preferably, equimolar amounts of the amine 2.3 and the carboxylic acid 2.4 are reacted in dimethylformamide in the presence of a carbodiimide, such as, for example, 1-dimethylaminopropyl-3-ethylcarbodiimide, as described, for example, in U.S. Pat. No. 5,914,332, to yield the amide 1.5.

The reactions illustrated in Schemes 1 and 2 illustrate the preparation of the compounds 1.5 in which A is either the group link-$P(O)(OR^1)_2$ or a precursor thereto, such as, for example, optionally protected OH, SH, NH, as described below. Scheme 3 depicts the conversion of the compounds 1.5 in which A is OH, SH, NH, as described below, into the compounds 1 in which A is the group link-$P(O)(OR^1)_2$. In this procedure, the compounds 1.5 are converted, using the procedures described below, Schemes 9-33, into the compounds 1.

Preparation of the Phosphonate Intermediates 2.

Two methods for the preparation of the phosphonate intermediate compounds 2 are shown in Schemes 4 and 5. The selection of the route to be employed for a given compound is made after consideration of the substituents which are present, and their stability under the reaction conditions required.

As depicted in Scheme 4, the tribenzylated phenylalanine derivative 4.1, in which the substituent A is either the group link-$P(O)(OR^1)_2$ or a precursor thereto, as described below, is reacted with the anion 4.2 derived from acetonitrile, to afford the ketonitrile 4.3. Preparations of the tribenzylated phenylalanine derivatives 4.1 are described below, Schemes 15-17.

The anion of acetonitrile is prepared by the treatment of acetonitrile with a strong base, such as, for example, lithium hexamethyldisilylazide or sodium hydride, in an inert organic solvent such as tetrahydrofuran or dimethoxyethane, as described, for example, in U.S. Pat. No. 5,491,253. The solution of the acetonitrile anion 4.2, in an aprotic solvent such as tetrahydrofuran, dimethoxyethane and the like, is then added to a solution of the ester 4.1 at low temperature, to afford the coupled product 4.3.

Preferably, a solution of ca. two molar equivalent of acetonitrile, prepared by the addition of ca. two molar equivalent of sodium amide to a solution of acetonitrile in tetrahydrofuran at −40°, is added to a solution of one molar equivalent of the ester 4.1 in tetrahydrofuran at −40°, as described in J. Org. Chem., 1994, 59, 4040, to produce the ketonitrile 4.3.

The above-described ketonitrile compound 4.3 is then reacted with an organometallic benzyl reagent, such as a benzyl Grignard reagent or benzyllithium, to afford the ketoenamine 4.5. The reaction is conducted in an inert aprotic organic solvent such as diethyl ether, tetrahydrofuran or the like, at from −80° to ambient temperature, to yield the benzylated product 4.5.

Preferably, the ketonitrile 4.3 is reacted with three molar equivalents of benzylmagnesium chloride in tetrahydrofuran at ambient temperature, to produce, after quenching by treatment with an organic carboxylic acid such as citric acid, as described in J. Org. Chem., 1994, 59, 4040, the ketoenamine 4.5.

The ketoenamine 4.5 is then reduced, in two stages, via the ketoamine 4.6, to produce the amino alcohol 4.7. The transformation of the compound 4.5 to the aminoalcohol 4.7 can be effected in one step, or in two steps, with or without isolation of the intermediate ketoamine 4.6, as described in U.S. Pat. No. 5,491,253.

For example, the ketoenamine 4.5 is reduced with a boron-containing reducing agent such as sodium borohydride, sodium cyanoborohydride and the like, in the presence of an acid such as methanesulfonic acid, as described in J. Org. Chem., 1994, 59, 4040, to afford the ketoamine 4.6. The reaction is performed in an ethereal solvent such as, for example, tetrahydrofuran or methyl tert-butyl ether. The product 4.6 is then reduced with sodium borohydride-trifluoroacetic acid, as described in U.S. Pat. No. 5,491,253, to afford the aminoalcohol 4.7. Alternatively, the ketoenamine 4.5 can be reduced to the aminoalcohol 4.7 without isolation of the intermediate ketoamine 4.6. In this procedure, as described in U.S. Pat. No. 5,491,253, the ketoenamine 4.5 is reacted with sodium borohydride-methanesulfonic acid, in an ethereal solvent such as dimethoxyethane and the like. The reaction mixture is then treated with a quenching agent such as triethanolamine, and the procedure is continued by the addition of sodium borohydride and a solvent such as dimethylformamide or dimethylacetamide or the like, to afford the aminoalcohol 4.7.

The aminoalcohol 4.7 is converted into the amide 4.8 by reaction with the acid $R^2COOH$ 2.4 or an activated derivative thereof, to produce the amide 4.8. This reaction is conducted under similar conditions to those described above for the preparation of the amides 1.3 and 1.5. The dibenzylated amide product 4.8 is then deprotected to afford the free amine 4.9. The conditions for the debenzylation reaction are the same as those described above for the deprotection of the dibenzyl amine 1.3 to yield the amine 1.4, (Scheme 1).

The amine 4.9 is then reacted with the carboxylic acid $R^3COOH$ (4.10) as defined in Charts 2a -2c, or an activated derivative thereof, to produce the amide 4.11. This reaction is conducted under similar conditions to those described above for the preparation of the amides 1.3 and 1.5.

Alternatively, the amide 4.11 can be prepared by means of the sequence of reactions illustrated in Scheme 5.

In this sequence, the tribenzylated amino acid derivative 4.1 is converted, by means of the reaction sequence shown in Scheme 4, into the dibenzylated amine 4.7. This compound is then converted into a protected derivative, for example the tert-butoxycarbonyl (BOC) derivative 5.1. Methods for the conversion of amines into the BOC derivative are described in Protective Groups in Organic Synthesis, by T. W. Greene and P. G. M Wuts, Wiley, Second Edition 1990, p. 327. For example, the amine can be reacted with di-tert-butoxycarbonylanhydride (BOC anhydride) and a base, or with 2-(tert-butoxycarbonyloxyimino)-2-phenylacetonitrile (BOC-ON), and the like.

Preferably, the amine 4.7 is reacted with ca. 1.5 molar equivalents of BOC anhydride and excess potassium carbonate, in methyl tert-butyl ether, at ambient temperature, for example as described in U.S. Pat. No. 5,914,3332, to yield the BOC-protected product 5.1.

The N-benzyl protecting groups are then removed from the amide product 5.1 to afford the free amine 5.2. The conditions for this transformation are similar to those described above for the preparation of the amine 1.4, (Scheme 1).

Preferably, the N,N-dibenzyl compound 5.1 is converted into the amine 5.2 by means of hydrogen transfer catalytic hydrogenolysis, for example by treatment with methanolic ammonium formate and 5% palladium on carbon catalyst, at ca. 75° for ca. 6 hours, for example as described in U.S. Pat. No. 5,914,332

The amine compound 5.2 is then reacted with the carboxylic acid $R^3COOH$, or an activated derivative thereof, to produce the amide 5.3. This reaction is conducted under similar conditions to those described above for the preparation of the amides 1.3 and 1.5, (Scheme 1). BOC-protected amide 5.3 is then converted into the amine 5.4 by removal of the BOC protecting group. The conditions for this transformation are similar to those described above for the preparation of the amine 2.3 (Scheme 2). The deprotection can be effected by treatment of the BOC compound with anhydrous acids, for example, hydrogen chloride or trifluoroacetic acid, or by reaction with trimethylsilyl iodide or aluminum chloride.

Preferably, the BOC group is removed by treatment of the substrate 5.3 with trifluoroacetic acid in dichloromethane at ambient temperature, for example as described in U.S. Pat. No. 5,914,232, to afford the free amine product 5.4.

The free amine thus obtained is then reacted with the carboxylic acid $R^2COOH$ 2.4, or an activated derivative thereof, to produce the amide 4.11. This reaction is conducted under similar conditions to those described above for the preparation of the amides 1.3 and 1.5. The reactions shown in Schemes 4 and 5 illustrate the preparation of the compounds 4.11 in which A is either the group link-$P(O)(OR^1)_2$ or a precursor thereto, such as, for example, optionally protected OH, SH, NH, as described below. Scheme 6 depicts the conversion of the compounds 4.11 in which A is OH, SH, NH, as described below, into the compounds 2. In this procedure, the compounds 4.11 are converted, using the procedures described below, Schemes 9-33, into the compounds 2.

Scheme 1

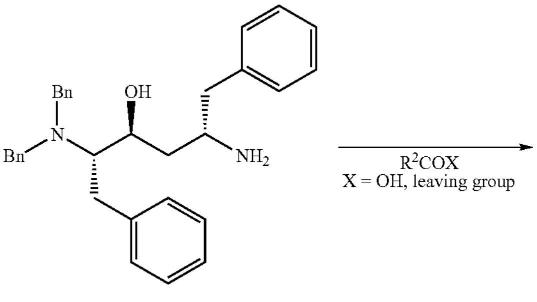

1.1

-continued
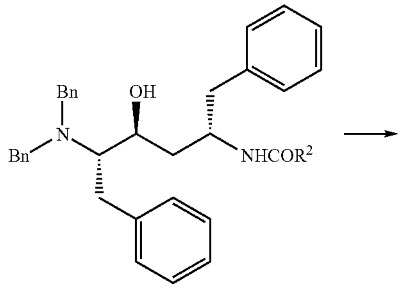
1.3
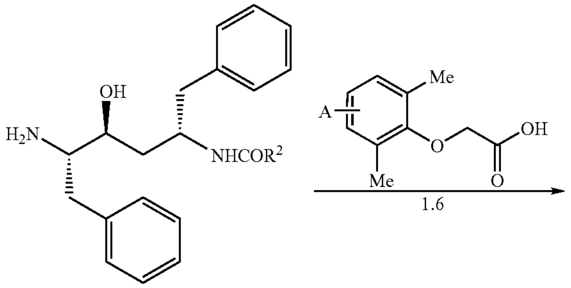
1.4
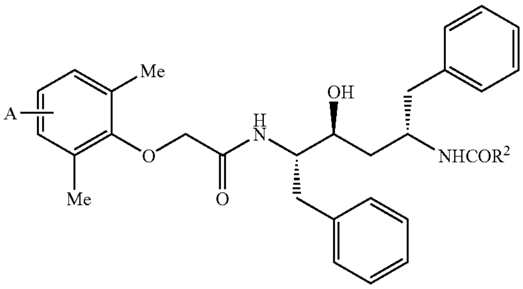
1.5
Scheme 2
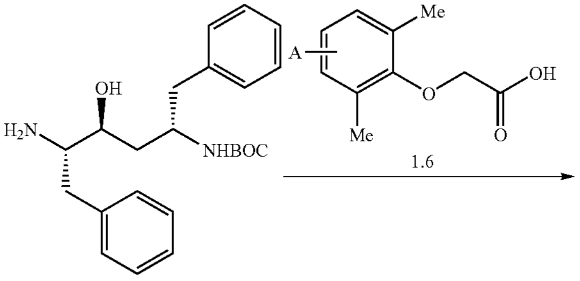
2.1
-continued
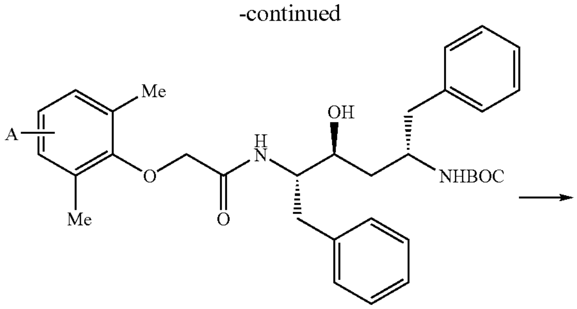
2.2
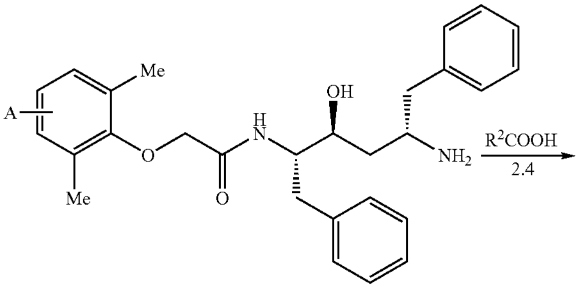
2.3
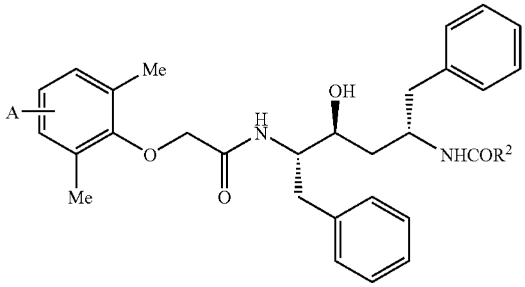
1.5
Scheme 3
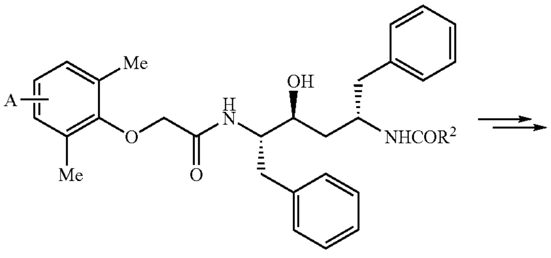
1.5
A = [OH], [SH], [$NH_2$] etc
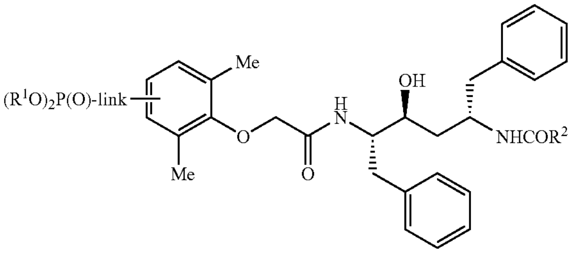
1

Scheme 4
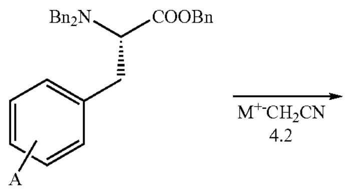
4.1
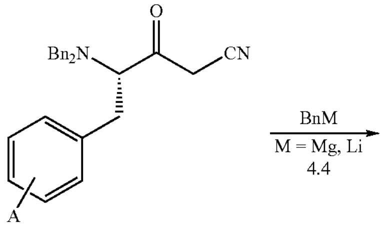
4.3
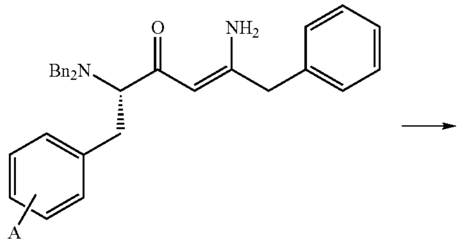
4.5
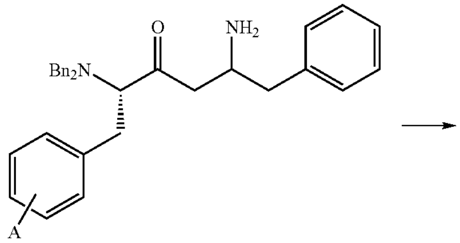
4.6
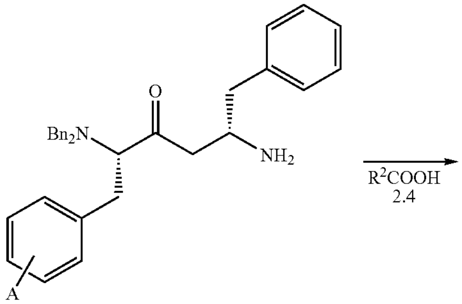
4.7
-continued
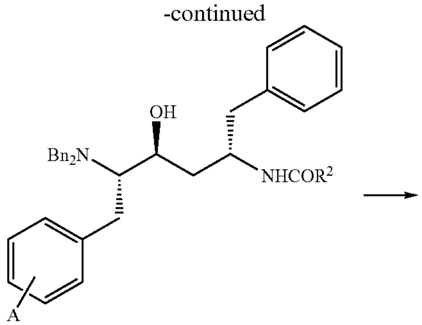
4.8
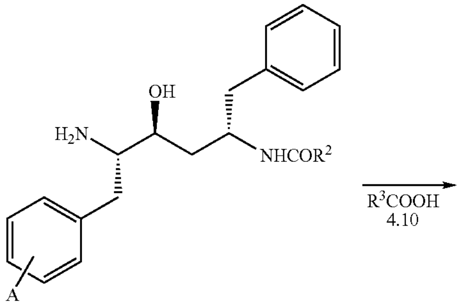
4.9
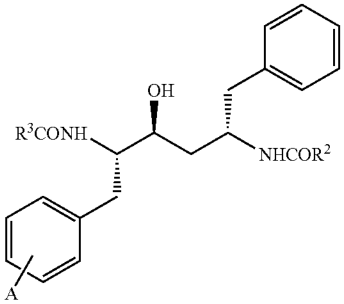
4.11
Scheme 5
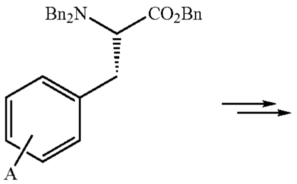
4.1
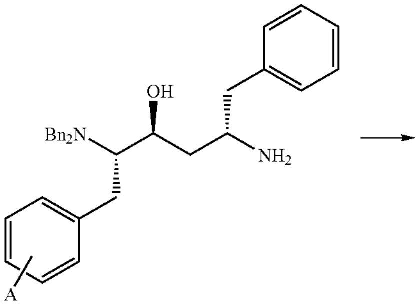
4.7

-continued

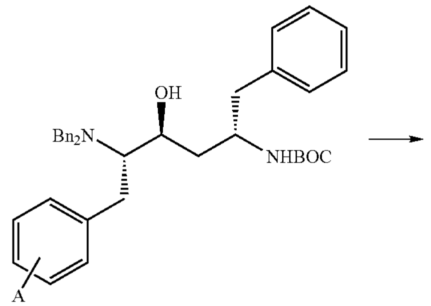

5.1

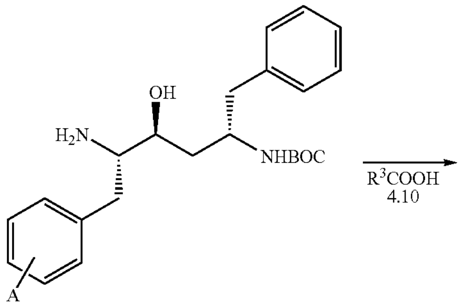

5.2

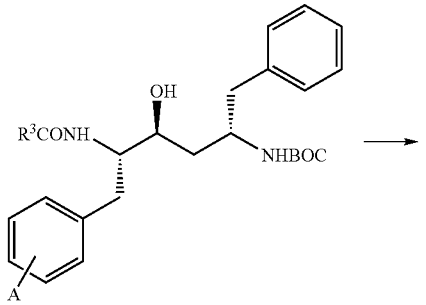

5.3

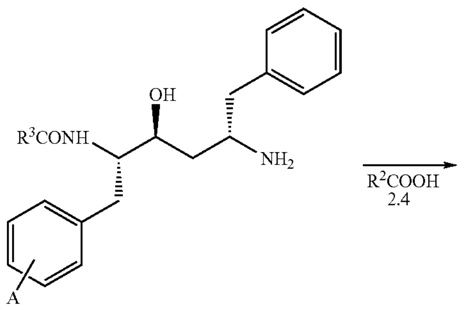

5.4

-continued

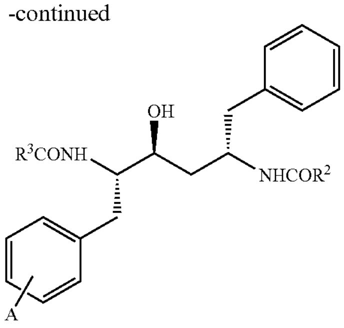

4.11

Scheme 6

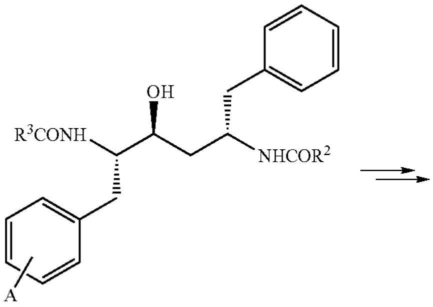

A = [OH], [SH], $[NH_2]$ etc
4.11

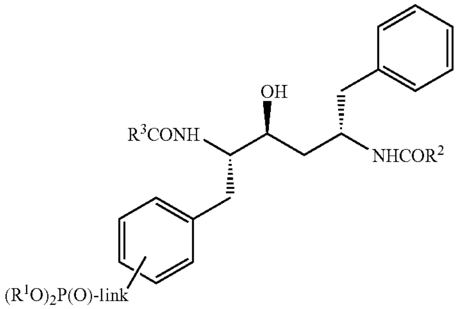

2

Preparation of the Phosphonate Intermediates 3.

The phosphonate ester intermediate compounds 3 can be prepared by two alternative methods, illustrated in Schemes 7 and 8. The selection of the route to be employed for a given compound is made after consideration of the substituents which are present, and their stability under the reaction conditions required.

As shown in Scheme 7,4-dibenzylamino-3-oxo-5-phenylpentanenitrile 7.1, the preparation of which is described in J. Org. Chem., 1994, 59, 4040, is reacted with a substituted benzylmagnesium halide reagent 7.2, in which the group B is a substituent, protected if appropriate, which can be converted, after the sequence of reactions shown in Scheme 7, into the substituent link-$P(O)(OR^1)_2$. Examples of the substituent B are Br, [OH], [SH], $[NH_2]$[CHO] and the like; procedures for the transformation of these groups into the phosphonate moiety are shown below in Schemes 9-33.

The conditions for the reaction between the benzylmagnesium halide 7.2 and the ketonitrile 7.1 are similar to those described above for the preparation of the ketoenamine 4.5 (Scheme 4). Preferably, the ketonitrile 7.1 is reacted with three molar equivalents of the substituted benzylmagnesium chloride 7.2 in tetrahydrofuran at ca. 0°, to produce, after quenching by treatment with an organic carboxylic acid such as citric acid, as described in J. Org. Chem., 1994, 59, 4040, the ketoenamine 7.3.

The thus-obtained ketoenamine 7.3 is then transformed, via the intermediate compounds 7.4, 7.5, 7.6 and 7.7 into the diacylated carbinol 7.8. The conditions for each step in the conversion of the ketoenamine 7.3 to the diacylated carbinol 7.8 are the same as those described above (Scheme 4) for the transformation of the ketoenamine 4.5 into the diacylated carbinol 4.11. The diacylated carbinol 7.8 is then converted into the phosphonate ester 3, using procedures illustrated below in Schemes 9-33.

Alternatively, the phosphonate esters 3 can be obtained by means of the reactions illustrated in Scheme 8. In this procedure, the amine 7.4, the preparation of which is described above, (Scheme 7) is converted into the BOC derivative 8.1. The conditions for the introduction of the BOC group are similar to those described above for the conversion of the amine 4.7 into the BOC-protected product 5.1, (Scheme 5).

Preferably, the amine 7.4 is reacted with ca. 1.5 molar equivalents of BOC anhydride and excess potassium carbonate, in methyl tert-butyl ether, at ambient temperature, for example as described in U.S. Pat. No. 5,914,332, to yield the BOC-protected product 8.1.

The BOC-protected amine 8.1 is then converted, via the intermediates 8.2, 8.3 and 8.4 into the diacylated carbinol 7.8. The reaction conditions for this sequence of reactions are similar to those described above for the transformation of the BOC-protected amine 5.1 into the diacylated carbinol 4.11 (Scheme 5).

The diacylated carbinol 7.8 is then converted into the phosphonate ester 3, using procedures illustrated below in Schemes 18-20.

Preparation of Dimethylphenoxyacetic Acids Incorporating Phosphonate Moieties.

Scheme 9 illustrates two alternative methods by means of which 2,6-dimethylphenoxyacetic acids bearing phosphonate moieties may be prepared. The phosphonate group may be introduced into the 2,6-dimethylphenol moiety, followed by attachment of the acetic acid group, or the phosphonate group may be introduced into a preformed 2,6-dimethylphenoxyacetic acid intermediate. In the first sequence, a substituted 2,6-dimethylphenol 9.1, in which the substituent B is a precursor to the group link-$P(O)(OR^1)_2$, and in which the phenolic hydroxyl may or may not be protected, depending on the reactions to be performed, is converted into a phosphonate-containing compound 9.2. Methods for the conversion of the substituent B into the group link-$P(O)(OR^1)_2$ are described below in Schemes 9-33.

The protected phenolic hydroxyl group present in the phosphonate-containing product 9.2 is then deprotected, using methods described below, to afford the phenol 9.3.

The phenolic product 9.3 is then transformed into the corresponding phenoxyacetic acid 9.4, in a two step procedure. In the first step, the phenol 9.3 is reacted with an ester of bromoacetic acid 9.5, in which R is an alkyl group or a protecting group. Methods for the protection of carboxylic acids are described in Protective Groups in Organic Synthesis, by T. W. Greene and P. G. M Wuts, Wiley, Second Edition 1990, p. 224ff. The alkylation of phenols to afford phenolic ethers is described, for example, in Comprehensive Organic Transformations, by R. C. Larock, VCH, 1989, p. 446ff. Typically, the phenol and the alkylating agent are reacted together in the presence of an organic or inorganic base, such as, for example, diazabicyclononene, (DBN) or potassium carbonate, in a polar organic solvent such as, for example, dimethylformamide or acetonitrile.

Preferably, equimolar amounts of the phenol 9.3 and ethyl bromoacetate are reacted together in the presence of cesium carbonate, in dioxan at reflux temperature, for example as described in U.S. Pat. No. 5,914,332, to afford the ester 9.6.

The thus-obtained ester 9.6 is then hydrolyzed to afford the carboxylic acid 9.4. The methods used for this reaction depend on the nature of the group R. If R is an alkyl group such as methyl, hydrolysis can be effected by treatment of the ester with aqueous or aqueous alcoholic base, or by use of an esterase enzyme such as porcine liver esterase. If R is a protecting group, methods for hydrolysis are described in Protective Groups in Organic Synthesis, by T. W. Greene and P. G. M Wuts, Wiley, Second Edition 1990, p. 224ff.

Preferably, the ester product 9.6 which R is ethyl is hydrolyzed to the carboxylic acid 9.4 by reaction with lithium hydroxide in aqueous methanol at ambient temperature, as described in U.S. Pat. No. 5,914,332.

Alternatively, an appropriately substituted 2,6-dimethylphenol 9.7, in which the substituent B is a precursor to the group link-$P(O)(OR^1)_2$, is transformed into the corresponding phenoxyacetic ester 9.8. The conditions employed for the alkylation reaction are similar to those described above for the conversion of the phenol 9.3 into the ester 9.6.

The phenolic ester 9.8 is then converted, by transformation of the group B into the group link-$P(O)(OR^1)_2$ followed by ester hydrolysis, into the carboxylic acid 9.4. The group B which is present in the ester 9.4 may be transformed into the group link-$P(O)(OR^1)_2$ either before or after hydrolysis of the ester moiety into the carboxylic acid group, depending on the nature of the chemical transformations required.

Schemes 9-14 illustrate the preparation of 2,6-dimethylphenoxyacetic acids incorporating phosphonate ester groups. The procedures shown can also be applied to the preparation of phenoxyacetic esters acids 9.8, with, if appropriate, modifications made according to the knowledge of one skilled in the art.

Scheme 10 illustrates the preparation of 2,6-dimethylphenoxyacetic acids incorporating a phosphonate ester which is attached to the phenolic group by means of a carbon chain incorporating a nitrogen atom. The compounds 10.4 are obtained by means of a reductive alkylation reaction between a 2,6-dimethylphenol aldehyde 10.1 and an aminoalkyl phosphonate ester 10.2. The preparation of amines by means of reductive amination procedures is described, for example, in Comprehensive Organic Transformations, by R. C. Larock, VCH, p. 421. In this procedure, the amine component 10.2 and the aldehyde component 10.1 are reacted together in the presence of a reducing agent such as, for example, borane, sodium cyanoborohydride or diisobutylaluminum hydride, to yield the amine product 10.3. The amination product 10.3 is then converted into the phenoxyacetic acid compound 10.4, using the alkylation and ester hydrolysis procedures described above, (Scheme 9) For example, equimolar amounts of 4-hydroxy-3,5-dimethylbenzaldehyde 10.5 (Aldrich) and a dialkyl aminoethyl phosphonate 10.6, the preparation of which is described in J. Org. Chem., 2000, 65, 676, are reacted together in the presence of sodium cyanoborohydride and acetic acid, as described, for example, in J. Amer. Chem. Soc., 91, 3996, 1969, to afford the amine product 10.3. The product is then converted into the acetic acid 10.8, as described above. Using the above procedures, but employing, in place of the aldehyde 10.5, different aldehydes 10.1, and/or different aminoalkyl phosphonates 10.2, the corresponding products 10.4 are obtained.

In this and succeeding examples, the nature of the phosphonate ester group can be varied, either before or after incorporation into the scaffold, by means of chemical transformations. The transformations, and the methods by which they are accomplished, are described below (Scheme 21)

Scheme 11 depicts the preparation of 2,6-dimethylphenols incorporating a phosphonate group linked to the phenyl ring by means of a saturated or unsaturated alkylene chain. In this procedure, an optionally protected bromo-substituted 2,6-dimethylphenol 11.1 is coupled, by means of a palladium-catalyzed Heck reaction, with a dialkyl alkenyl phosphonate 11.2. The coupling of aryl bromides with olefins by means of the Heck reaction is described, for example, in Advanced Organic Chemistry, by F. A. Carey and R. J. Sundberg, Plenum, 2001, p. 503. The aryl bromide and the olefin are coupled in a polar solvent such as dimethylformamide or dioxan, in the presence of a palladium(0) or palladium (2) catalyst. Following the coupling reaction, the product 11.3 is converted, using the procedures described above, (Scheme 9) into the corresponding phenoxyacetic acid 11.4. Alternatively, the olefinic product 11.3 is reduced to afford the saturated 2,6-dimethylphenol derivative 11.5. Methods for the reduction of carbon-carbon double bonds are described, for example, in Comprehensive Organic Transformations, by R. C. Larock, VCH, 1989, p. 6. The methods include catalytic reduction, or chemical reduction employing, for example, diborane or diimide. Following the reduction reaction, the product 11.5 is converted, as described above, (Scheme 9) into the corresponding phenoxyacetic acid 11.6.

For example, 3-bromo-2,6-dimethylphenol 11.7, prepared as described in Can. J. Chem., 1983, 61, 1045, is converted into the tert-butyldimethylsilyl ether 11.8, by reaction with chloro-tert-butyldimethylsilane, and a base such as imidazole, as described in Protective Groups in Organic Synthesis, by T. W. Greene and P. G. M Wuts, Wiley, Second Edition 1990 p. 77. The product 11.8 is reacted with an equimolar amount of a dialkyl allyl phosphonate 11.9, for example diethyl allylphosphonate (Aldrich) in the presence of ca. 3 mol % of bis(triphenylphosphine)palladium(II) chloride, in dimethylformamide at ca. 60°, to produce the coupled product 11.10. The silyl group is removed, for example by the treatment of the ether 11.10 with a solution of tetrabutylammonium fluoride in tetrahydrofuran, as described in J. Am. Chem., Soc., 94, 6190, 1972, to afford the phenol 11.11. This compound is converted, employing the procedures described above, (Scheme 9) into the corresponding phenoxyacetic acid 11.12. Alternatively, the unsaturated compound 11.11 is reduced, for example by catalytic hydrogenation employing 5% palladium on carbon as catalyst, in an alcoholic solvent such as methanol, as described, for example, in Hydrogenation Methods, by R. N. Rylander, Academic Press, 1985, Ch. 2, to afford the saturated analog 11.13. This compound is converted, employing the procedures described above, (Scheme 9) into the corresponding phenoxyacetic acid 11.14.

Using the above procedures, but employing, in place of 3-bromo-2,6-dimethylphenol 11.7, different bromophenols 11.1, and/or different dialkyl alkenyl phosphonates 11.2, the corresponding products 11.4 and 11.6 are obtained.

Scheme 12 illustrates the preparation of phosphonate-containing 2,6-dimethylphenoxyacetic acids 12.1 in which the phosphonate group is attached to the 2,6-dimethylphenoxy moiety by means of a carbocyclic ring. In this procedure, a bromo-substituted 2,6-dimethylphenol 12.2 is converted, using the procedures illustrated in Scheme 9, into the corresponding 2,6-dimethylphenoxyacetic ester 12.3. The latter compound is then reacted, by means of a palladium-catalyzed Heck reaction, with a cycloalkenone 12.4, in which n is 1 or 2. The coupling reaction is conducted under the same conditions as those described above for the preparation of 11.3. (Scheme 11). The product 12.5 is then reduced catalytically, as described above for the reduction of 11.3, (Scheme 11), to afford the substituted cycloalkanone 12.6. The ketone is then subjected to a reductive amination procedure, by reaction with a dialkyl 2-aminoethylphosphonate 12.7 and sodium triacetoxyborohydride, as described in J. Org. Chem., 61, 3849, 1996, to yield the amine phosphonate 12.8. The reductive amination reaction is conducted under the same conditions as those described above for the preparation of the amine 10.3 (Scheme 10). The resultant ester 12.8 is then hydrolyzed, as described above, to afford the phenoxyacetic acid 12.1.

For example, 4-bromo-2,6-dimethylphenol 12.9 (Aldrich) is converted, as described above, into the phenoxy ester 12.10. The latter compound is then coupled, in dimethylformamide solution at ca. 60°, with cyclohexenone 12.11, in the presence of tetrakis(triphenylphosphine)palladium(0) and triethylamine, to yield the cyclohexenone 12.12. The enone is then reduced to the saturated ketone 12.13, by means of catalytic hydrogenation employing 5% palladium on carbon as catalyst. The saturated ketone is then reacted with an equimolar amount of a dialkyl aminoethylphosphonate 12.14, prepared as described in J. Org. Chem., 2000, 65, 676, in the presence of sodium cyanoborohydride, to yield the amine 12.15. Hydrolysis, employing lithium hydroxide in aqueous methanol at ambient temperature, then yields the acetic acid 12.16.

Using the above procedures, but employing, in place of 4-bromo-2,6-dimethylphenol 12.9, different bromo-substituted 2,6-dimethylphenols 12.2, and/or different cycloalkenones 12.4, and/or different dialkyl aminoalkylphosphonates 12.7, the corresponding products 12.1 are obtained.

Scheme 13 illustrates the preparation of 2,6-dimethylphenoxyacetic acids incorporating a phosphonate group attached to the phenyl ring by means of a heteroatom and an alkylene chain. The compounds are obtained by means of alkylation reactions in which an optionally protected hydroxy, thio or amino-substituted 2,6-dimethylphenol 13.1 is reacted, in the presence of a base such as, for example, potassium carbonate, and optionally in the presence of a catalytic amount of an iodide such as potassium iodide, with a dialkyl bromoalkyl phosphonate 13.2. The reaction is conducted in a polar organic solvent such as dimethylformamide or acetonitrile at from ambient temperature to about 80°. The product of the alkylation reaction, 13.3 is then converted, as described above (Scheme 9) into the phenoxyacetic acid 13.4.

For example, 2,6-dimethyl-4-mercaptophenol 13.5, prepared as described in EP 482342, is reacted in dimethylformamide at ca. 60° with an equimolar amount of a dialkyl bromobutyl phosphonate 13.6, the preparation of which is described in Synthesis, 1994, 9, 909, in the presence of ca. 5 molar equivalents of potassium carbonate, to afford the thioether product 13.7. This compound is converted, employing the procedures described above, (Scheme 9) into the corresponding phenoxyacetic acid 13.8.

Using the above procedures, but employing, in place of 2,6-dimethyl-4-mercaptophenol 13.5, different hydroxy, thio or aminophenols 13.1, and/or different dialkyl bromoalkyl phosphonates 13.2, the corresponding products 13.4 are obtained.

Scheme 14 illustrates the preparation of 2,6-dimethylphenoxyacetic acids incorporating a phosphonate ester group attached by means of an aromatic or heteroaromatic group. In this procedure, an optionally protected hydroxy, mercapto or amino-substituted 2.6-dimethylphenol 14.1 is reacted, under basic conditions, with a bis(halomethyl)aryl or heteroaryl compound 14.2. Equimolar amounts of the phenol and the halomethyl compound are reacted in a polar organic solvent such as dimethylformamide or acetonitrile, in the presence of a base such as potassium or cesium carbonate, or dimethylaminopyridine, to afford the ether, thioether or amino product 14.3. The product 14.3 is then converted, using the procedures described above, (Scheme 9) into the phenoxyacetic ester 14.4. The latter compound is then subjected to an Arbuzov reaction by reaction with a trialkylphosphite 14.5 at ca. 100° to afford the phosphonate ester 14.6. The preparation of phosphonates by means of the Arbuzov reaction is described, for example, in Handb. Organophosphorus Chem., 1992, 115. The resultant product 14.6 is then converted into the acetic acid 14.7 by hydrolysis of the ester moiety, using the procedures described above, (Scheme 9).

For example, 4-hydroxy-2,6-dimethylphenol 14.8 (Aldrich) is reacted with one molar equivalent of 3,5-bis(chloromethyl)pyridine, the preparation of which is described in Eur. J. Inorg. Chem., 1998, 2, 163, to afford the ether 14.10. The reaction is conducted in acetonitrile at ambient temperature in the presence of five molar equivalents of potassium carbonate. The product 14.10 is then reacted with ethyl bromoacetate, using the procedures described above, (Scheme 9) to afford the phenoxyacetic ester 14.11. This product is heated at 100° for 3 hours with three molar equivalents of triethyl phosphite 14.12, to afford the phosphonate ester 14.13. Hydrolysis of the acetic ester moiety, as described above, for example by reaction with lithium hydroxide in aqueous ethanol, then affords the phenoxyacetic acid 14.14.

Using the above procedures, but employing, in place of the bis(chloromethyl) pyridine 14.9, different bis(halomethyl) aromatic or heteroaromatic compounds 14.2, and/or different hydroxy, mercapto or amino-substituted 2,6-dimethylphenols 14.1 and/or different trialkyl phosphites 14.5, the corresponding products 14.7 are obtained.

Scheme 7

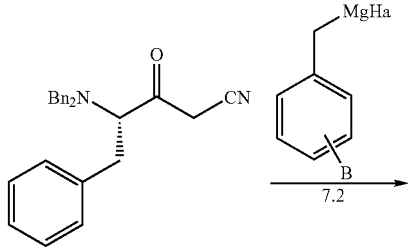

7.1

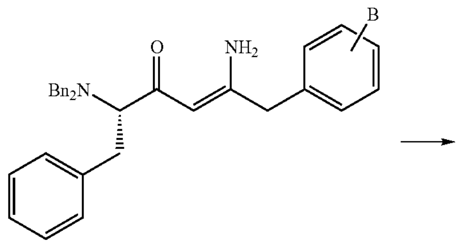

B = Br, [OH], [SH], [$NH_2$] etc 7.3

-continued

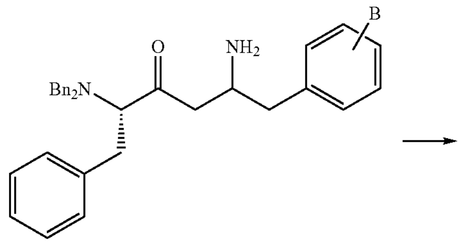

7.4

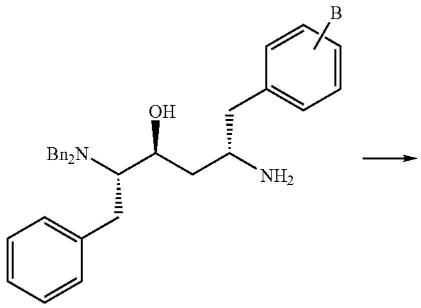

7.5

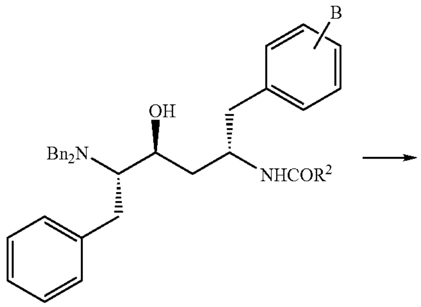

7.6

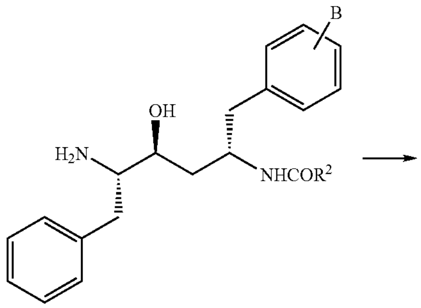

7.7

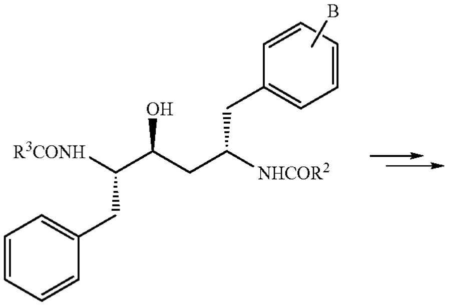

7.8

-continued
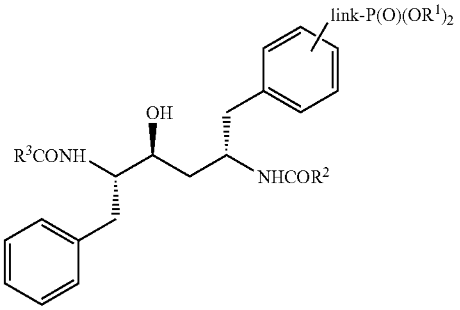
3
Scheme 8
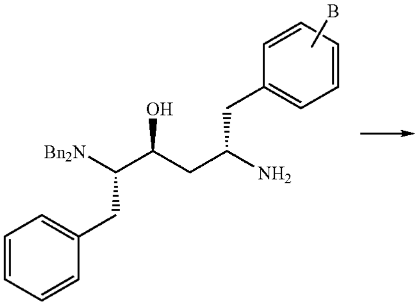
B = [OH], [SH], [$NH_2$] etc
7.4
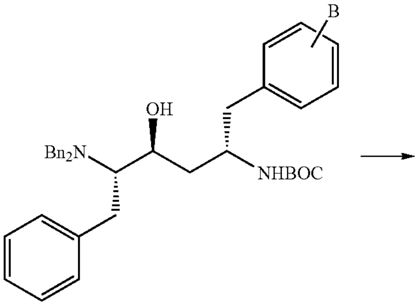
8.1
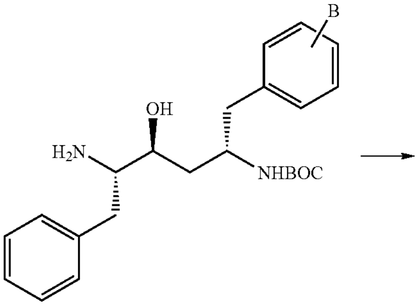
8.2
-continued
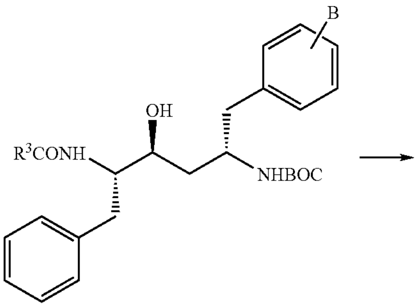
8.3
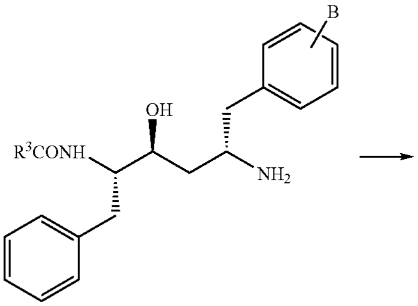
8.4
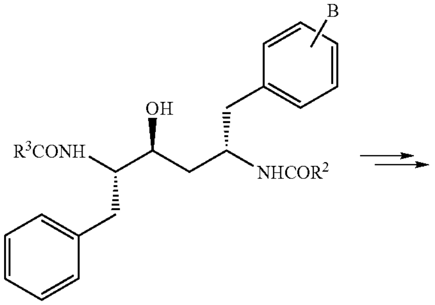
7.8
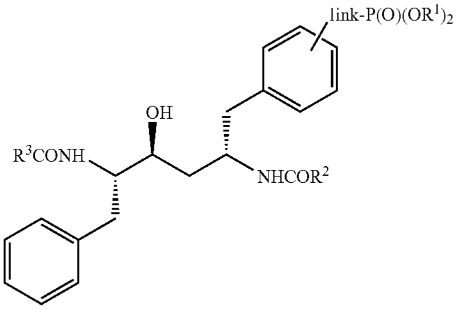
3

Scheme 9
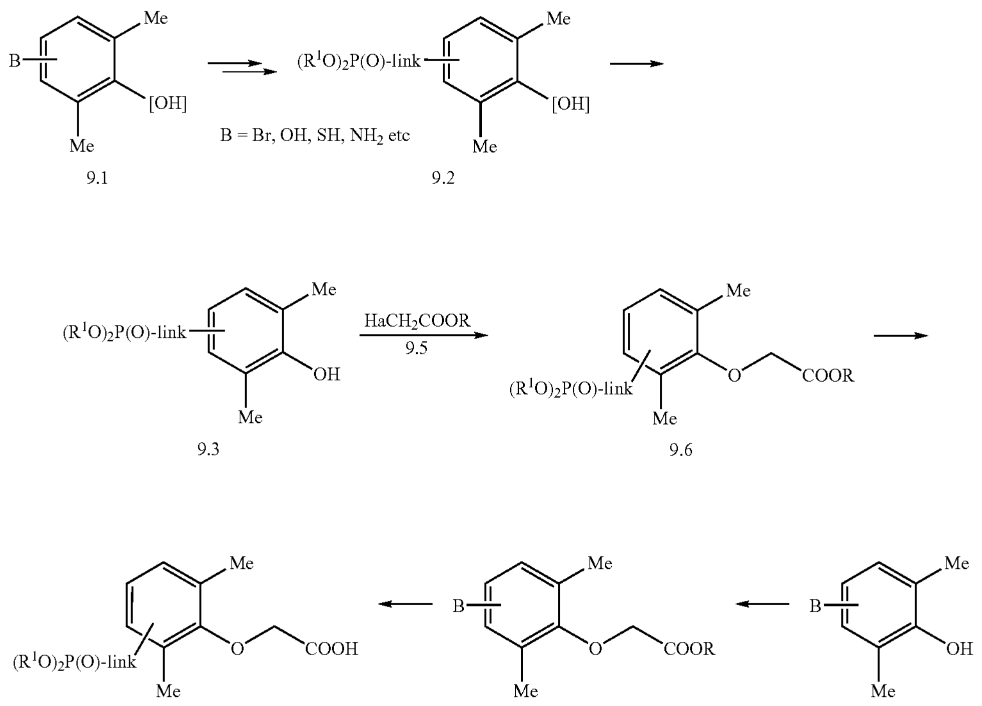
9.1 9.2 9.3 9.6 9.4 9.8 9.7
Scheme 10
Method
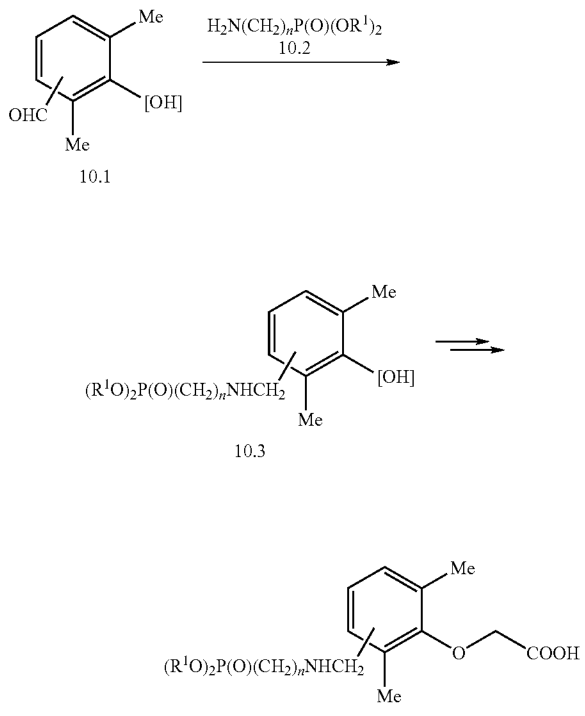
10.1 10.3 10.4
-continued
Example
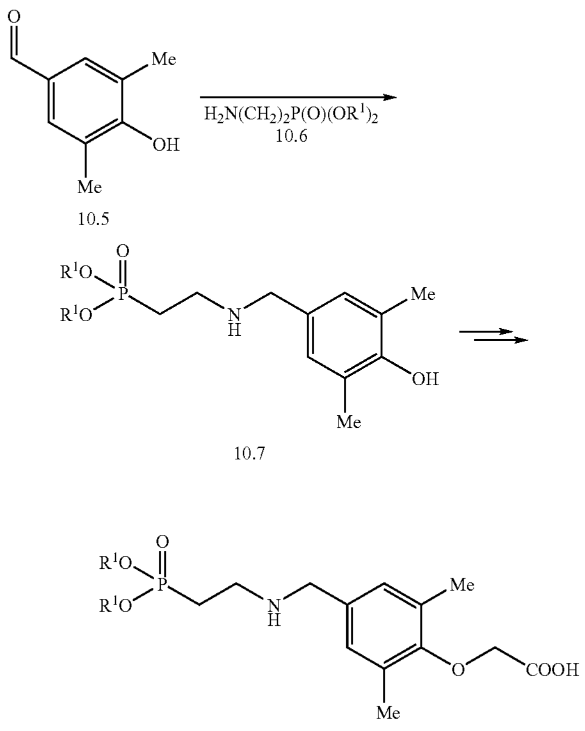
10.5 10.7 10.8

Scheme 11
Method
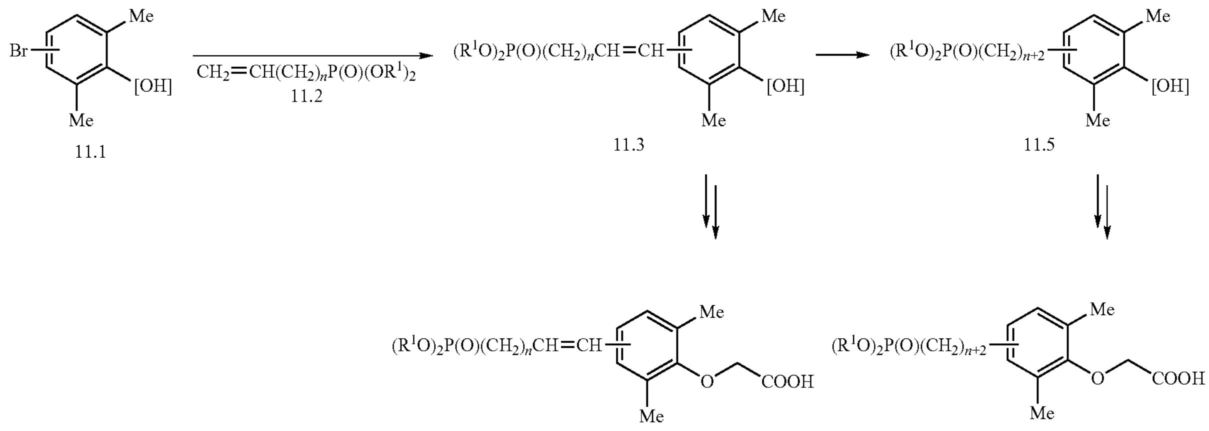
11.1 11.3 11.5 11.4 11.6
Example
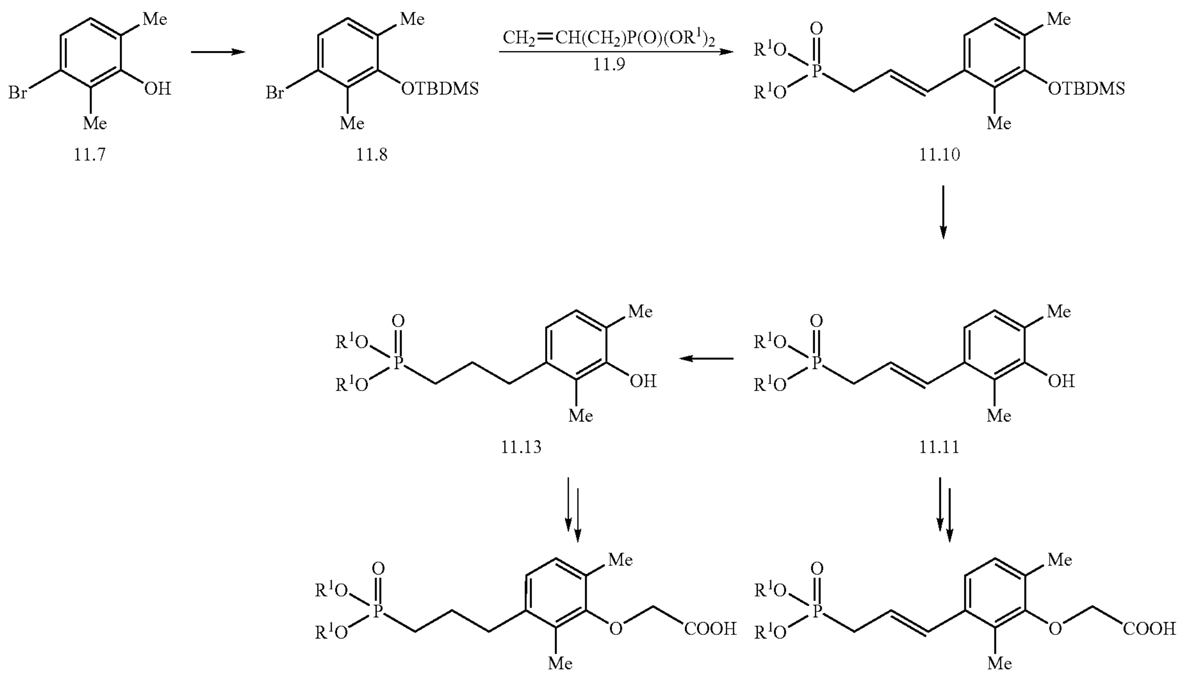
11.7 11.8 11.10 11.13 11.11 11.14 11.12
Scheme 12
Method
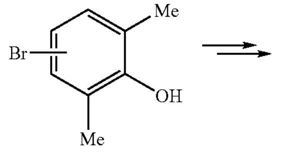
12.2
-continued
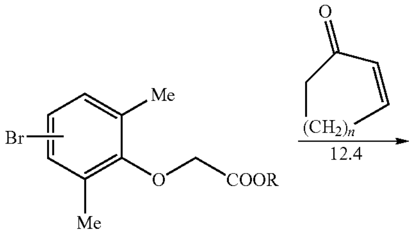
12.3

-continued
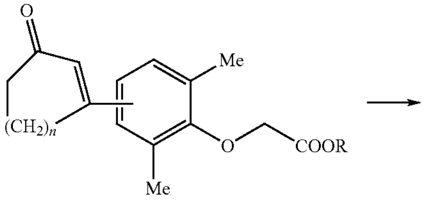
12.5
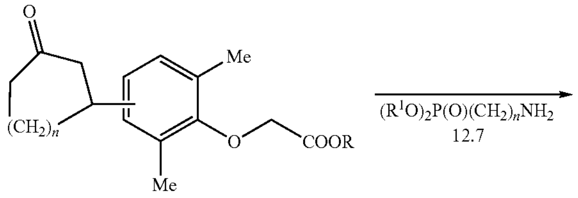
12.6
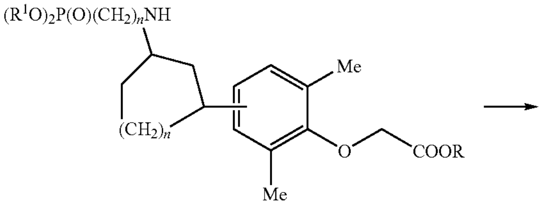
12.8
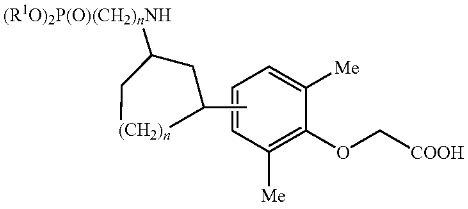
12.1
Example
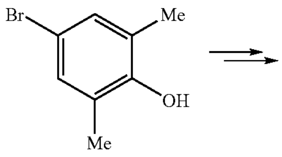
12.9
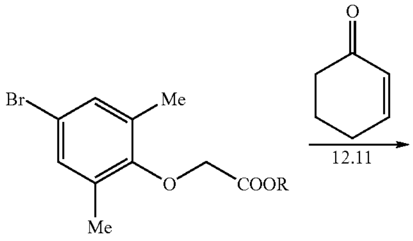
12.10
-continued
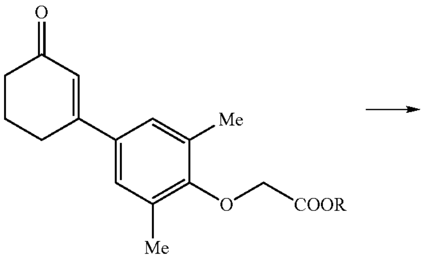
12.12
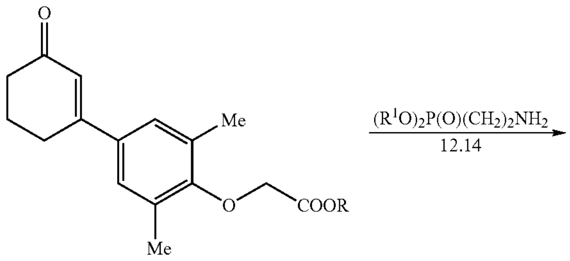
12.13
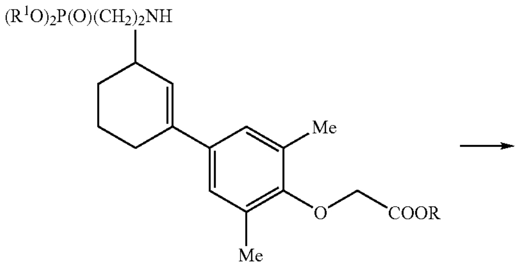
12.15
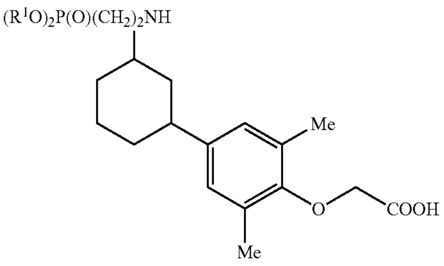
12.16
Scheme 13
Method
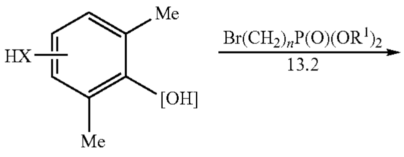
X = O, S, NH, Nalkyl
13.1

-continued
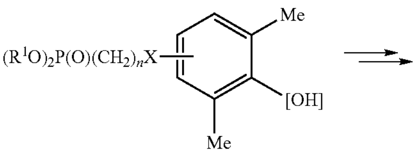
13.3
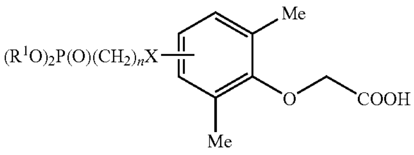
13.4
Example
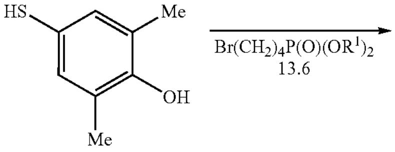
13.5
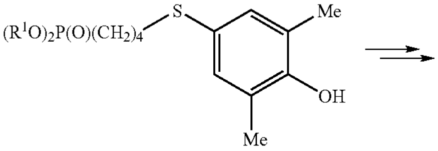
13.7
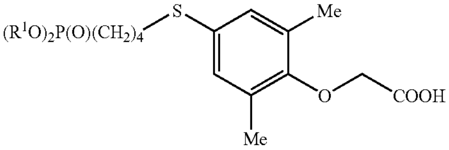
13.8
Scheme 14
Method
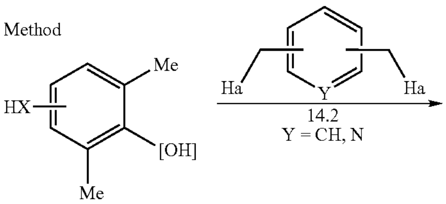
X = O, S, NH, Nalkyl
14.1
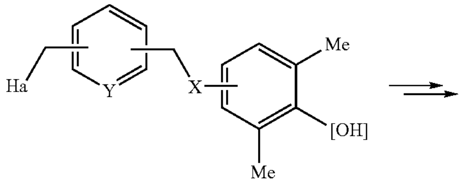
14.3
-continued
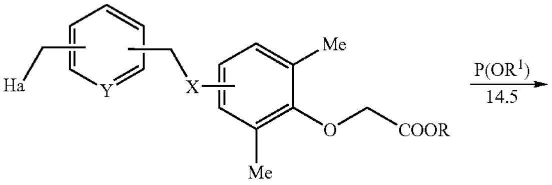
14.4
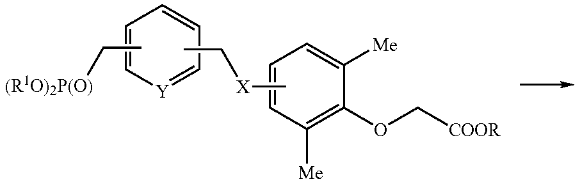
14.6
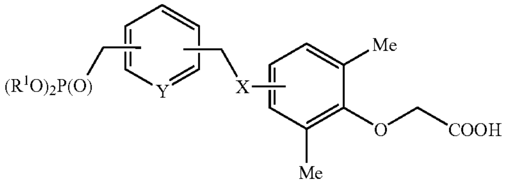
14.7
Example
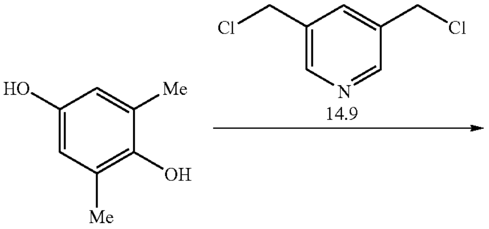
14.8
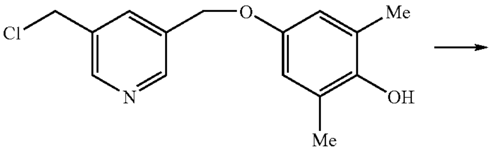
14.10
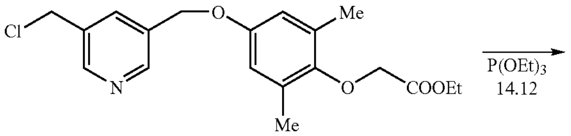
14.11
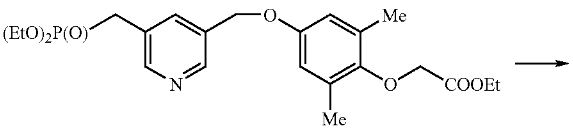
14.13
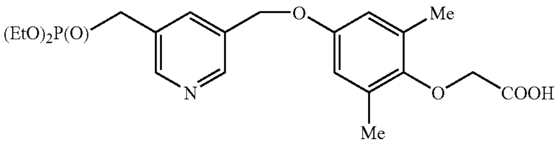
14.14

Preparation of Phenylalanine Derivatives 4.1 Incorporating Phosphonate Moieties, or Precursors Thereto.

Schemes 15-17 describe various methods for the preparation of phosphonate-containing analogs of phenylalanine. The compounds are then employed, as described above, (Schemes 4 and 5) in the preparation of the compounds 2.

Scheme 15 illustrates the preparation of phenylalanine derivatives incorporating phosphonate moieties attached to the phenyl ring by means of a heteroatom and an alkylene chain. The compounds are obtained by means of alkylation or condensation reactions of hydroxy or mercapto-substituted phenylalanine derivatives 15.5.

In this procedure, a hydroxy or mercapto-substituted phenylalanine 15.1 is converted into the benzyl ester 15.2. The conversion of carboxylic acids into esters is described for example, in Comprehensive Organic Transformations, by R. C. Larock, VCH, 1989, p. 966. The conversion can be effected by means of an acid-catalyzed reaction between the carboxylic acid and benzyl alcohol, or by means of a base-catalyzed reaction between the carboxylic acid and a benzyl halide, for example benzyl chloride. The hydroxyl or mercapto substituent present in the benzyl ester 15.2 is then protected. Protection methods for phenols and thiols are described respectively, for example, in Protective Groups in Organic Synthesis, by T. W. Greene and P. G. M Wuts, Wiley, Second Edition 1990, p. 10, p. 277. For example, suitable OH and SH protecting groups include tert-butyldimethylsilyl or tert-butyldiphenylsilyl. Alternative SH protecting groups include 4-methoxybenzyl and S-adamantyl. The protected hydroxy- or mercapto ester 15.3 is then reacted with a benzyl or substituted benzyl halide and a base, for example as described in U.S. Pat. No. 5,491,253, to afford the N,N-dibenzyl product 15.4. For example, the amine 15.3 is reacted at ca. 90° with two molar equivalents of benzyl chloride in aqueous ethanol containing potassium carbonate, to afford the tribenzylated product 15.4, as described in U.S. Pat. No. 5,491,253. The protecting group present on the O or S substituent is then removed. Removal of O or S protecting groups is described in Protective Groups in Organic Synthesis, by T. W. Greene and P. G. M Wuts, Wiley, Second Edition 1990, p10, p. 277. For example, silyl protecting groups are removed by treatment with tetrabutylammonium fluoride and the like, in a solvent such as tetrahydrofuran at ambient temperature, as described in J. Am. Chem. Soc., 94, 6190, 1972. S-Adamantyl protecting groups are removed by treatment with mercuric trifluoroacetate in trifluoroacetic acid, as described in Chem. Pharm. Bull., 26, 1576, 1978.

The resultant phenol or thiophenol 15.5 is then reacted under various conditions to provide protected phenylalanine derivatives 15.6, 15.7 or 15.8, incorporating phosphonate moieties attached by means of a heteroatom and an alkylene chain.

As one option, the phenol or thiophenol 15.5 is reacted with a dialkyl bromoalkyl phosphonate 15.9 to afford the product 15.6. The alkylation reaction between 15.5 and 15.9 is effected in the presence of an organic or inorganic base, such as, for example, diazabicyclononene, cesium carbonate or potassium carbonate. The reaction is performed at from ambient temperature to ca. 80°, in a polar organic solvent such as dimethylformamide or acetonitrile, to afford the ether or thioether product 15.6.

For example, as illustrated in Scheme 15 Example 1, a hydroxy-substituted phenylalanine derivative such as tyrosine, 15.12 is converted, as described above, into the benzyl ester 15.13. The latter compound is then reacted with one molar equivalent of chloro tert-butyldimethylsilane, in the presence of a base such as imidazole, as described in J. Am. Chem. Soc., 94, 6190, 1972, to afford the silyl ether 15.14. This compound is then converted, as described above, into the tribenzylated derivative 15.15. The silyl protecting group is removed by treatment of 15.15 with a tetrahydrofuran solution of tetrabutylammonium fluoride at ambient temperature, as described in J. Am. Chem. Soc., 94, 6190, 1972, to afford the phenol 15.16. The latter compound is then reacted in dimethylformamide at ca. 60°, with one molar equivalent of a dialkyl 3-bromopropyl phosphonate 15.17 (Aldrich), in the presence of cesium carbonate, to afford the alkylated product 15.18.

Using the above procedures, but employing, in place of the 4-hydroxy phenylalanine 15.12, different hydroxy or thio-substituted phenylalanine derivatives 15.1, and/or different bromoalkyl phosphonates 15.9, the corresponding ether or thioether products 15.6 are obtained.

Alternatively, the hydroxy or mercapto-substituted tribenzylated phenylalanine derivative 15.5 is reacted with a dialkyl hydroxymethyl phosphonate 15.10 under the conditions of the Mitsonobu reaction, to afford the ether or thioether compounds 15.7. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine.

For example, as shown in Scheme 15, Example 2,3-mercaptophenylalanine 15.19, prepared as described in WO 0036136, is converted, as described above, into the benzyl ester 15.20. The resultant ester is then reacted in tetrahydrofuran solution with one molar equivalent of 4-methoxybenzyl chloride in the presence of ammonium hydroxide, as described in Bull. Chem. Soc. Jpn., 37, 433, 1974, to afford the 4-methoxybenzyl thioether 15.21. This compound is then converted, as described above for the preparation of the tribenzylated phenylalanine derivative 15.4, into the tribenzyl derivative 15.22. The 4-methoxybenzyl group is then removed by the reaction of the thioether 15.22 with mercuric trifluoroacetate and anisole in trifluoroacetic acid, as described in J. Org. Chem., 52, 4420, 1987, to afford the thiol 15.23. The latter compound is reacted, under the conditions of the Mitsonobu reaction, with a dialkyl hydroxymethyl phosphonate 15.24, diethylazodicarboxylate and triphenylphosphine, for example as described in Synthesis, 4, 327, 1998, to yield the thioether product 15.25.

Using the above procedures, but employing, in place of the mercapto-substituted phenylalanine derivative 15.19, different hydroxy or mercapto-substituted phenylalanines 15.1, and/or different dialkylhydroxymethyl phosphonates 15.10, the corresponding products 15.7 are obtained.

Alternatively, the hydroxy or mercapto-substituted tribenzylated phenylalanine derivative 15.5 is reacted with an activated derivative of a dialkyl hydroxymethylphosphonate 15.11 in which Lv is a leaving group. The components are reacted together in a polar aprotic solvent such as, for example, dimethylformamide or dioxan, in the presence of an organic or inorganic base such as triethylamine or cesium carbonate, to afford the ether or thioether products 15.8.

For example, as illustrated in Scheme 15, Example 3,3-hydroxyphenylalanine 15.26 (Fluka) is converted, using the procedures described above, into the tribenzylated compound 15.27. The latter compound is reacted, in dimethylformamide at ca. 50°, in the presence of potassium carbonate, with diethyl trifluoromethanesulfonyloxymethylphosphonate 15.28, prepared as described in Tet. Lett., 1986, 27, 1477, to afford the ether product 15.29.

Using the above procedures, but employing, in place of the hydroxy-substituted phenylalanine derivative 15.26, different hydroxy or mercapto-substituted phenylalanines 15.1, and/or different dialkyl trifluoromethanesulfonyloxymethylphosphonates 15.11, the corresponding products 15.8 are obtained.

Scheme 16 illustrates the preparation of phenylaianine derivatives incorporating phosphonate moieties attached to the phenyl ring by means of an alkylene chain incorporating a nitrogen atom. The compounds are obtained by means of a reductive alkylation reaction between a formyl-substituted tribenzylated phenylalanine derivative 16.1 and a dialkyl aminoalkylphosphonate 16.2.

In this procedure, a hydroxymethyl-substituted phenylalanine 16.3 is converted into the tribenzylated derivative 16.4 by reaction with three equivalents of a benzyl halide, for example, benzyl chloride, in the presence of an organic or inorganic base such as diazabicyclononene or potassium carbonate. The reaction is conducted in a polar solvent optionally in the additional presence of water. For example, the aminoacid 16.3 is reacted with three equivalents of benzyl chloride in aqueous ethanol containing potassium carbonate, as described in U.S. Pat. No. 5,491,253, to afford the product 16.4. The latter compound is then oxidized to afford the corresponding aldehyde 16.1. The conversion of alcohols to aldehydes is described, for example, in Comprehensive Organic Transformations, by R. C. Larock, VCH, 1989, p. 604ff. Typically, the alcohol is reacted with an oxidizing agent such as pyridinium chlorochromate, silver carbonate, or dimethyl sulfoxide/acetic anhydride, to afford the aldehyde product 16.1. For example, the carbinol 16.4 is reacted with phosgene, dimethyl sulfoxide and triethylamine, as described in J. Org. Chem., 43, 2480, 1978, to yield the aldehyde 16.1. This compound is reacted with a dialkyl aminoalkylphosphonate 16.2 in the presence of a suitable reducing agent to afford the amine product 16.5. The preparation of amines by means of a reductive amination reaction is described above (Scheme 10).

For example, 3-(hydroxymethyl)-phenylalanine 16.6, prepared as described in Acta Chem. Scand. Ser. B, 1977, B31, 109, is converted, as described above, into the formylated derivative 16.8. This compound is then reacted, in ethanol, at ambient temperature, with one molar equivalent of a dialkyl aminoethylphosphonate 16.9, prepared as described in J. Org. Chem., 200, 65, 676, in the presence of sodium cyanoborohydride, to produce the alkylated product 16.10.

Using the above procedures, but employing, in place of 3-(hydroxymethyl)-phenylalanine 16.6, different hydroxymethyl phenylalanines 16.3, and/or different aminoalkyl phosphonates 16.2, the corresponding products 16.5 are obtained.

Scheme 17 depicts the preparation of phenylalanine derivatives in which a phosphonate moiety is attached directly to the phenyl ring. In this procedure, a suitably protected bromo-substituted phenylalanine 17.2 is coupled, in the presence of a palladium(0) catalyst, with a dialkyl phosphite 17.3 to produce the phosphonate ester 17.4. The preparation of arylphosphonates by means of a coupling reaction between aryl bromides and dialkyl phosphites is described in J. Med. Chem., 35, 1371, 1992.

For example, 3-bromophenylalanine 17.5, prepared as described in Pept. Res., 1990, 3, 176, is converted, as described above, (Scheme 15) into the tribenzylated compound 17.6. This compound is then reacted, in toluene solution at reflux, with diethyl phosphite 17.7, triethylamine and tetrakis(triphenylphosphine)palladium(0), as described in J. Med. Chem., 35, 1371, 1992, to afford the phosphonate product 17.8.

Using the above procedures, but employing, in place of 3-bromophenylalanine 17.5, different bromophenylalanines 17.1, and/or different dialkylphosphites 17.3, the corresponding products 17.4 are obtained.

Scheme 15

Method

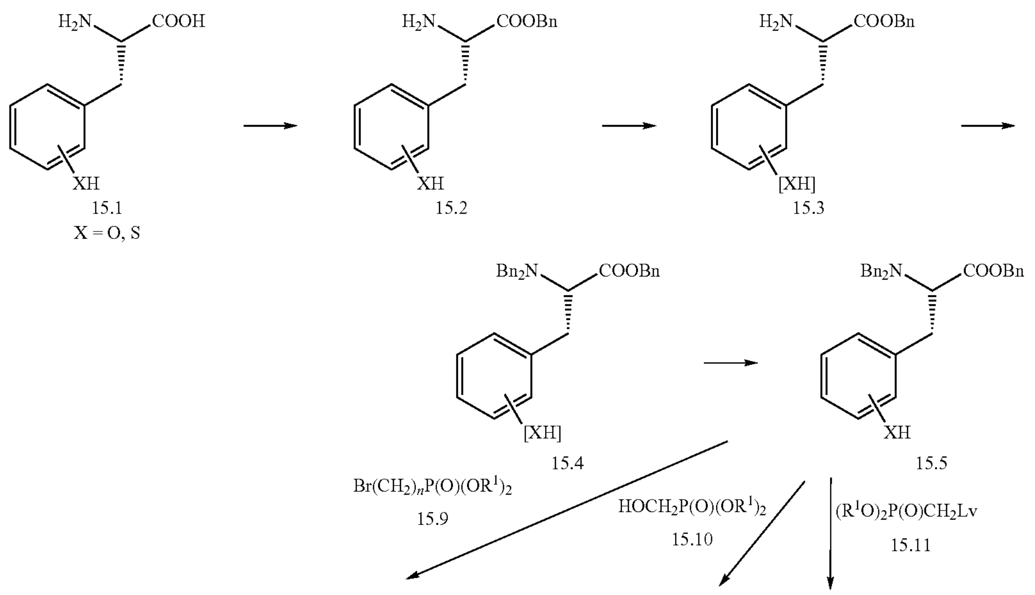

15.1
X = O, S
15.2
15.3
15.4
15.5
15.9
15.10
15.11

-continued
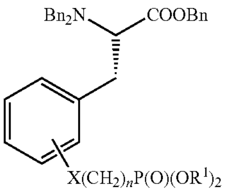
15.6
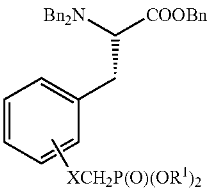
15.7
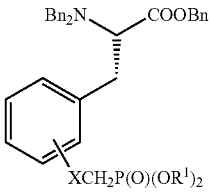
15.8
Example 1
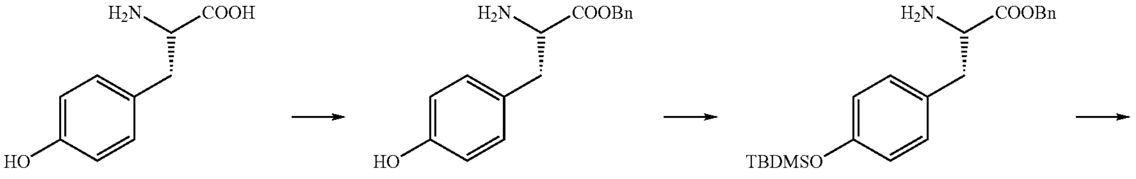
15.12 15.13 15.14
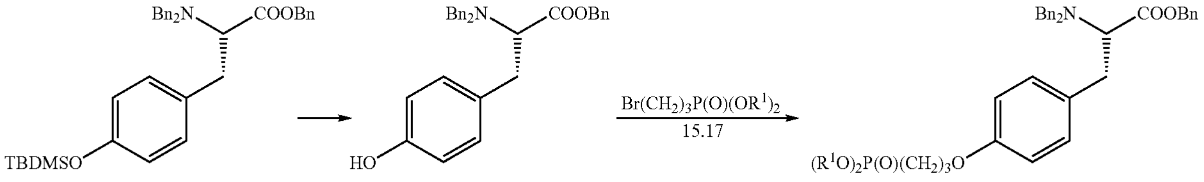
15.15 15.16 15.18
Example 2
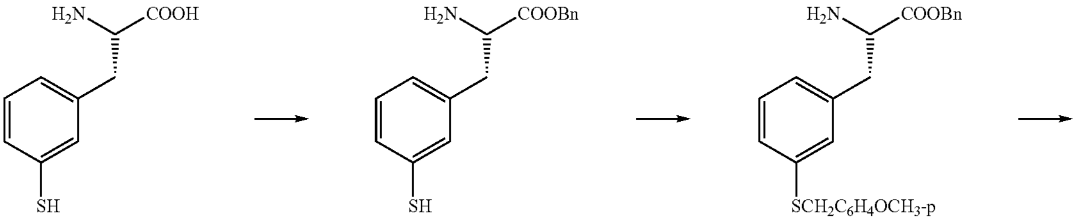
15.19 15.20 15.21
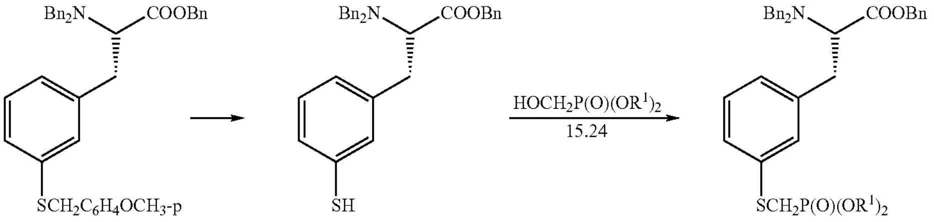
15.22 15.23 15.25
Example 3
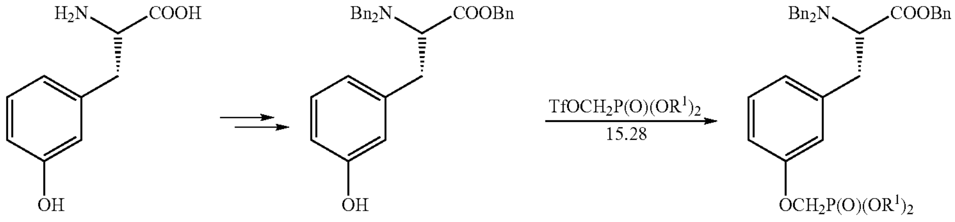
15.26 15.27 15.29

Scheme 16

Method

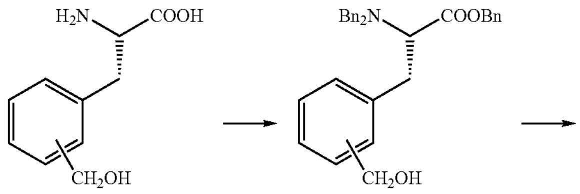

16.3 16.4

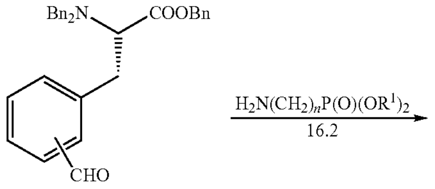

16.1

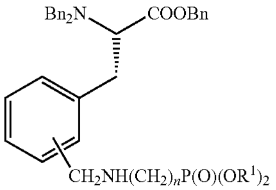

16.5

Example

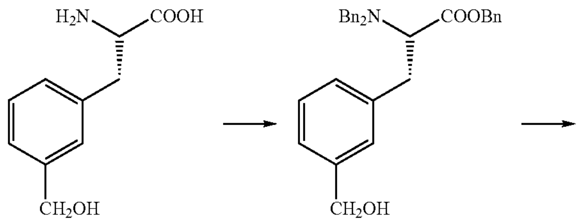

16.6 16.7

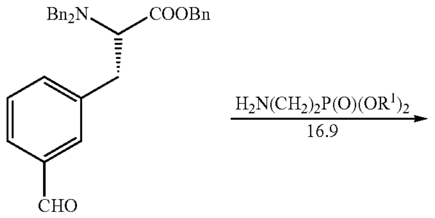

16.8

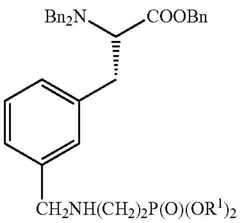

16.10

Scheme 17

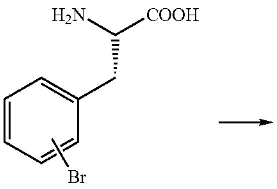

17.1

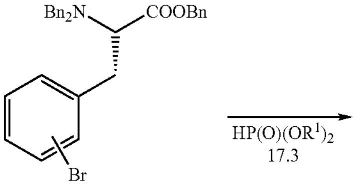

17.2

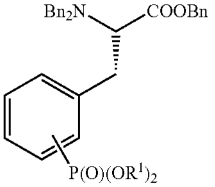

17.4

Example

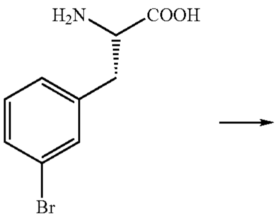

17.5

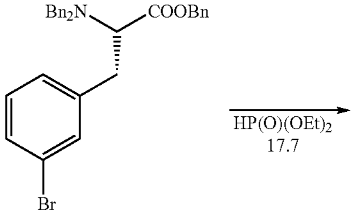

17.6

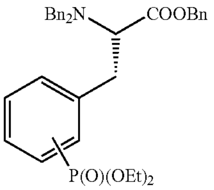

17.8

Preparation of Phosphonate Esters with Structure 3.

Scheme 18 illustrates the preparation of compounds 3 in which the phosphonate ester moiety is attached directly to the phenyl ring. In this procedure, the ketonitrile 7.1, prepared as described in J. Org. Chem., 1994, 59, 4080, is reacted, as described above (Scheme n) with a bromobenzylmagnesium halide reagent 18.1. The resultant ketoenamine 18.2 is then converted into the diacylated bromophenyl carbinol 18.3. The conditions required for the conversion of the ketoenamine 18.2 into the carbinol 18.3 are similar to those described above (Scheme 7), for the conversion of the ketoenamine 7.3 into the carbinol 7.8. The product 18.3 is then reacted with a dialkyl phosphite 17.3, in the presence of a palladium (0) catalyst, to yield the phosphonate ester 3. The conditions for the coupling reaction are the same as those described above (Scheme 17) for the preparation of the phosphonate ester 17.8.

For example, the ketonitrile 7.1 is reacted, in tetrahydrofuran solution at 0°, with three molar equivalents of 4-bromobenzylmagnesium bromide 18.4, the preparation of which is described in Tetrahedron, 2000, 56, 10067, to afford the ketoenamine 18.5. The latter compound is then converted into the diacylated bromophenyl carbinol 18.6, using the sequence of reactions described above (Scheme 7) for the conversion of the ketoenamine 7.3 into the carbinol 7.8. The resultant bromo compound 18.6 is then reacted with diethyl phosphite 18.7 and triethylamine, in toluene solution at reflux, in the presence of tetrakis(triphenylphosphine)palladium(0), as described in J. Med. Chem., 35, 1371, 1992, to afford the phosphonate product 18.8.

Using the above procedures, but employing, in place of 4-bromobenzylmagnesium bromide 18.4, different bromobenzylmagnesium halides 18.1 and/or different dialkyl phosphites 17.3, there are obtained the corresponding phosphonate esters 3.

Scheme 19 illustrates the preparation of compounds 3 in which the phosphonate ester moiety is attached to the nucleus by means of a phenyl ring. In this procedure, a bromophenyl-substituted benzylmagnesium bromide 19.1, prepared from the corresponding bromomethyl compound by reaction with magnesium, is reacted with the ketonitrile 7.1. The conditions for this transformation are the same as those described above (Scheme 7). The product of the Grignard addition reaction is then transformed, using the sequence of reactions described above, (Scheme 7) into the diacylated carbinol 19.2. The latter compound is then coupled, in the presence of a palladium(0) catalyst, with a dialkyl phosphite 17.3, to afford the phenylphosphonate 3. The procedure for the coupling reaction is the same as those described above for the preparation of the phosphonate 17.4.

For example, 4-(4-bromophenyl)benzyl bromide, prepared as described in DE 2262340, is reacted with magnesium to afford 4-(4-bromophenyl)benzylmagnesium bromine 19.3. This product is then reacted with the ketonitrile 7.1, as described above, to yield, after the sequence of reactions shown in Scheme 7, the diacylated carbinol 19.4. The latter compound is then reacted, as described above, (Scheme 17) with a diethyl phosphite 17.3, to afford the phenylphosphonate 19.5.

Using the above procedures, but employing, in place of 4-(4-bromophenyl)benzyl bromide 19.3, different bromophenylbenzyl bromides 19.1, and/or different dialkyl phosphites 17.3, the corresponding products 3 are obtained.

Scheme 20 depicts the preparation of phosphonate esters 3 in which the phosphonate group is attached by means of a heteroatom and a methylene group. In this procedure, a hetero-substituted benzyl alcohol 20.1 is protected, affording the derivative 20.2. The protection of phenyl hydroxyl, thiol and amino groups are described, respectively, in Protective Groups in Organic Synthesis, by T. W. Greene and P. G. M Wuts, Wiley, Second Edition 1990, p. 10, p. 277, 309. For example, hydroxyl and thiol substituents can be protected as trialkylsilyloxy groups. Trialkylsilyl groups are introduced by the reaction of the phenol or thiophenol with a chlorotrialkylsilane, for example as described in Protective Groups in Organic Synthesis, by T. W. Greene and P. G. M Wuts, Wiley, Second Edition 1990, p. 10, p. 68-86. Alternatively, thiol substituents can be protected by conversion to tert-butyl or adamantyl thioethers, as described in Protective Groups in Organic Synthesis, by T. W. Greene and P. G. M Wuts, Wiley, Second Edition 1990, p. 289. Amino groups can be protected, for example by dibenzylation. The conversion of amines into dibenzylamines, for example by treatment with benzyl bromide in a polar solvent such as acetonitrile or aqueous ethanol, in the presence of a base such as triethylamine or sodium carbonate, is described in Protective Groups in Organic Synthesis, by T. W. Greene and P. G. M Wuts, Wiley, Second Edition 1990, p. 364. The resultant protected benzyl alcohol 20.2 is converted into a halo derivative 20.3, in which Ha is chloro or bromo. The conversion of alcohols into chlorides and bromides is described, for example, in Comprehensive Organic Transformations, by R. C. Larock, VCH, 1989, p. 354ff and p. 356ff. For example, benzyl alcohols 20.2 can be transformed into the chloro compounds 20.3, in which Ha is chloro, by reaction with triphenylphosphine and N-chlorosuccinimide, as described in J. Am. Chem. Soc., 106, 3286, 1984. Benzyl alcohols can be transformed into bromo compounds by reaction with carbon tetrabromide and triphenylphosphine, as described in J. Am. Chem. Soc., 92, 2139, 1970. The resultant protected benzyl halide 20.3 is then converted into the corresponding benzylmagnesium halide 20.4 by reaction with magnesium metal in an ethereal solvent, or by a Grignard exchange reaction treatment with an alkyl magnesium halide. The resultant substituted benzylmagnesium halide 20.4 is then converted, using the sequence of reactions described above (Scheme 7) for the preparation of 7.8, into the carbinol 20.5 in which the substituent XH is suitably protected.

The protecting group is then removed to afford the phenol, thiophenol or amine 20.6. Deprotection of phenols, thiophenols and amines is described respectively in Protective Groups in Organic Synthesis, by T. W. Greene and P. G. M Wuts, Wiley, Second Edition 1990. For example, trialkylsilyl ethers or thioethers can be deprotected by treatment with a tetraalkylammonium fluoride in an inert solvent such as tetrahydrofuran, as described in J. Am Chem. Soc., 94, 6190, 1972. Tert-butyl or adamantyl thioethers can be converted into the corresponding thiols by treatment with mercuric trifluoroacetate in aqueous acetic acid at ambient temperature, as described in Chem. Pharm. Bull., 26, 1576, 1978. N,N-dibenzyl amines can be converted into the unprotected amines by catalytic reduction in the presence of a palladium catalyst, as described above (Scheme 1). The resultant phenol, thiophenol or amine 20.6 is then converted into the phosphonate ester 3 by reaction with an activated derivative of a dialkyl hydroxymethyl phosphonate 15.11, in which Lv is a leaving group. The reaction is conducted under the same conditions as described above for the alkylation of the phenol 15.5 to afford the ether or thioether 15.8 (Scheme 15).

For example, 3-hydroxybenzyl alcohol 20.7 (Aldrich) is reacted with chlorotriisopropylsilane and imidazole in dimethylformamide, as described in Tet. Lett., 2865, 1964, to afford the silyl ether 20.8. This compound is reacted with carbon tetrabromide and triphenylphosphine in dichloromethane, as described in J. Am. Chem. Soc., 109, 2738, 1987, to afford the brominated product 20.9. This material is reacted with magnesium in ether to afford the Grignard reagent 20.10, which is then subjected to the series of reaction shown in Scheme 7 to afford the carbinol 20.11. The triisopropylsilyl protecting group is then removed by treatment of the ether 20.11 with tetrabutylammonium fluoride in tetrahydrofuran, as described in J. Org. Chem., 51, 4941, 1986. The resultant phenol 20.12 is then reacted in dimethylformamide solution with a dialkyl trifluoromethanesulfonyloxymethyl phosphonate 15.28, prepared as described in Synthesis, 4, 327, 1998, in the presence of a base such as dimethylaminopyridine, as described above (Scheme 15) to afford the phosphonate product 20.13.

Using the above procedures, but employing, in place of 3-hydroxybenzyl alcohol 20.7, different hydroxy, mercapto or amino-substituted benzyl alcohols 20.1, and/or different dialkyl hydroxymethyl phosphonate derivatives 15.11, the corresponding products 3 are obtained.

Scheme 18

Method

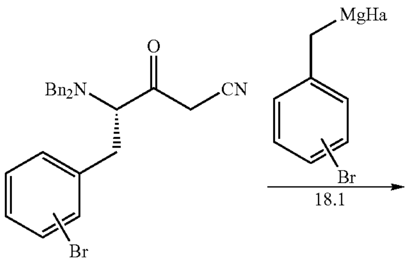

7.1

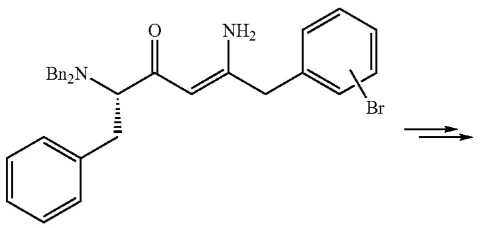

18.2

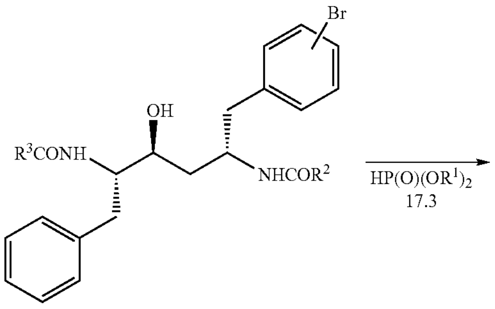

18.3

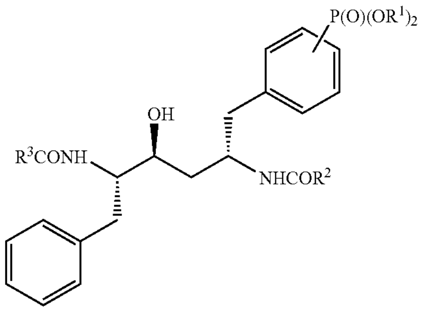

3

-continued

Example

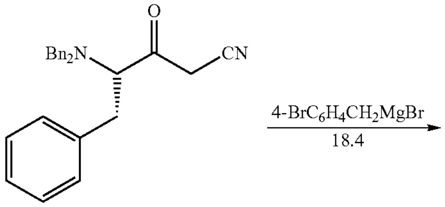

7.1

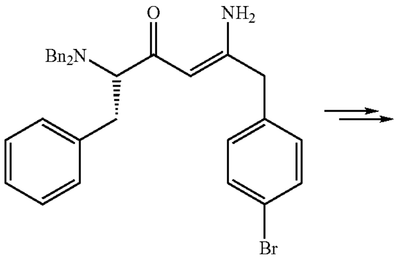

18.5

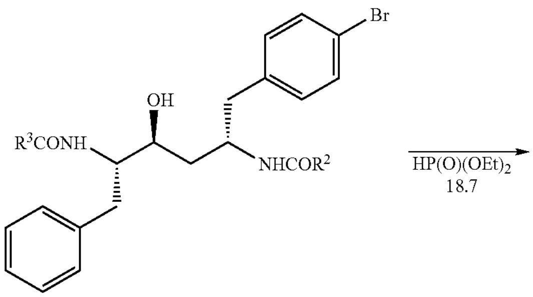

18.6

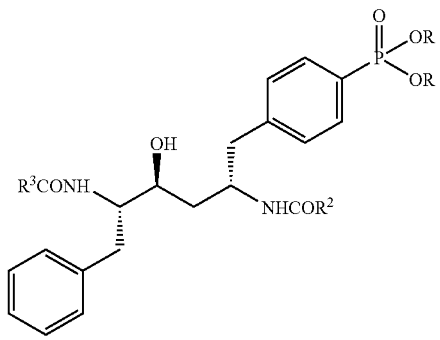

18.8

Scheme 19
Method
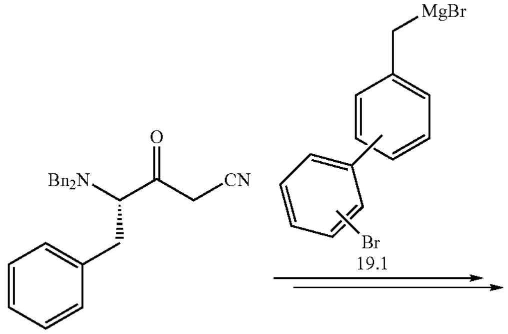
19.1
7.1
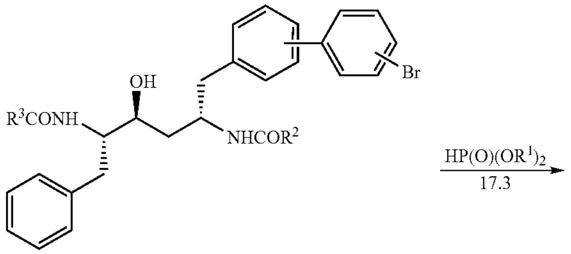
19.2
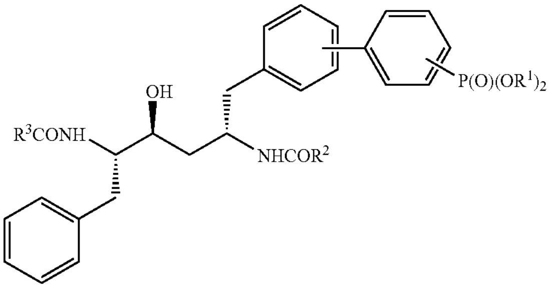
3
Example
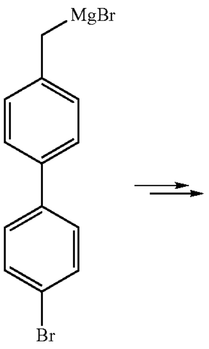
19.3
-continued
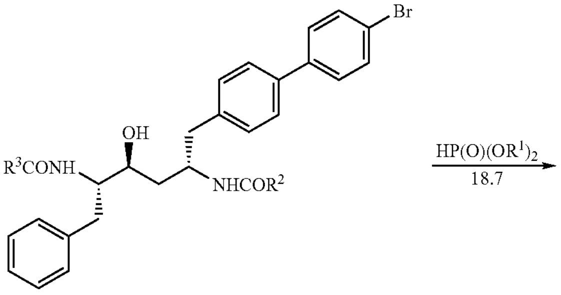
19.4
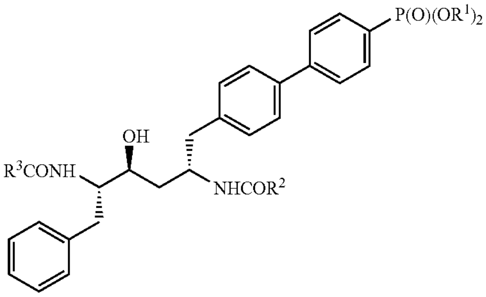
19.5
Scheme 20
Method
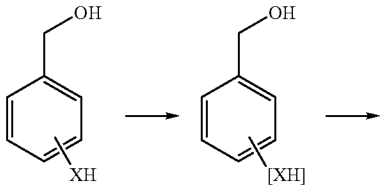
X = O, S, NH
20.1
20.2
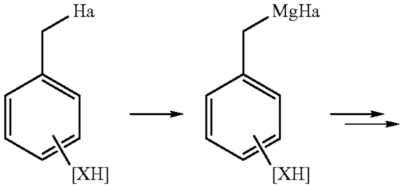
20.3
20.4
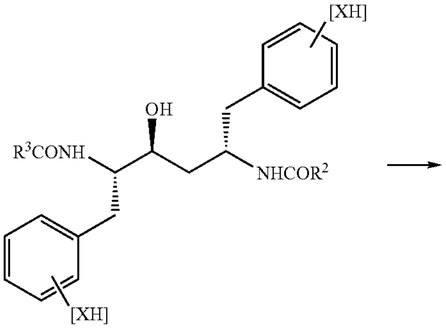
20.5

-continued

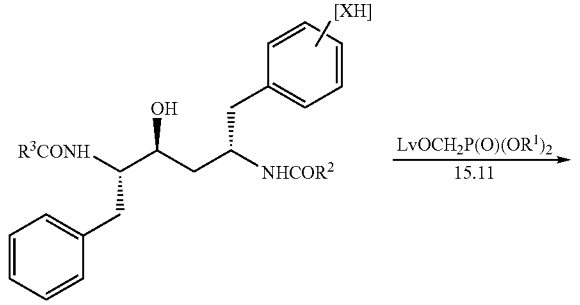

20.6

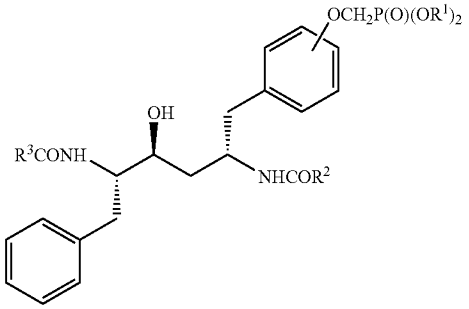

3

Example

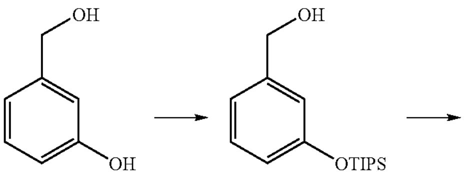

20.7 20.8

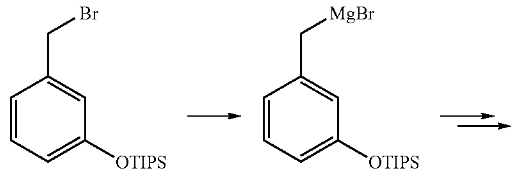

20.9 20.10

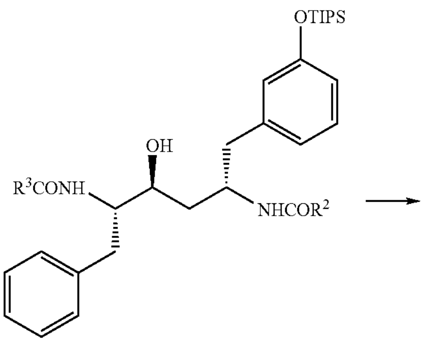

20.11

-continued

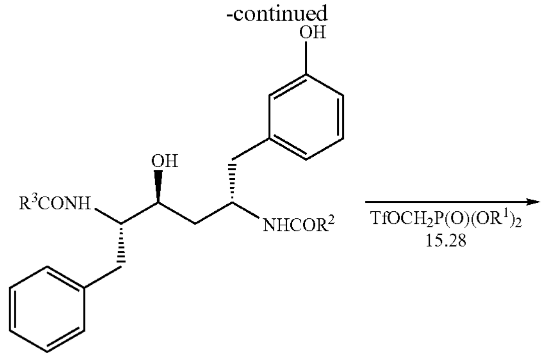

20.12

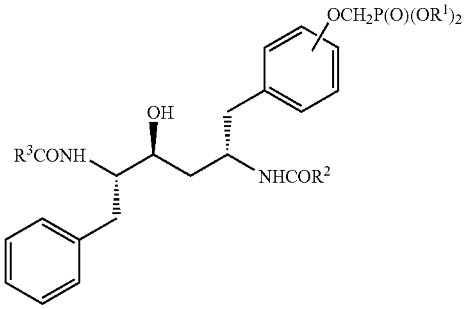

20.13

Interconversions of the Phosphonates R-link-$P(O)(OR^1)_2$, R-link-$P(O)(OR^1)(OH)$ and R-link-$P(O)(OH)_2$.

Schemes 1-33 described the preparations of phosphonate esters of the general structure R-link-$P(O)(OR^1)_2$, in which the groups $R^1$, the structures of which are defined in Chart 1, may be the same or different. The $R^1$ groups attached to a phosphonate esters 1-5, or to precursors thereto, may be changed using established chemical transformations. The interconversions reactions of phosphonates are illustrated in Scheme 21. The group R in Scheme 21 represents the substructure to which the substituent link-$P(O)(OR^1)_2$ is attached, either in the compounds 1-5 or in precursors thereto. The $R^1$ group may be changed, using the procedures described below, either in the precursor compounds, or in the esters 1-5. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 21.1 into the corresponding phosphonate monoester 21.2 (Scheme 21, Reaction 1) can be accomplished by a number of methods. For example, the ester 21.1 in which $R^1$ is an aralkyl group such as benzyl, can be converted into the monoester compound 21.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 21.1 in which $R^1$ is an aryl group such as phenyl, or an alkenyl group such as allyl, into the monoester 21.2 can be effected by treatment of the ester 21.1 with a base such as aqueous sodium hydroxide in acetonitrile or lithium hydroxide in aqueous tetrahydrofuran.

Phosphonate diesters 21.1 in which one of the groups $R^1$ is aralkyl, such as benzyl, and the other is alkyl, can be converted into the monoesters 21.2 in which $R^1$ is alkyl by hydrogenation, for example using a palladium on carbon catalyst. Phosphonate diesters in which both of the groups $R^1$ are alkenyl, such as allyl, can be converted into the monoester 21.2 in which $R^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in J. Org. Chem., 38 3224 1973 for the cleavage of allyl carboxylates.

The conversion of a phosphonate diester 21.1 or a phosphonate monoester 21.2 into the corresponding phosphonic acid 21.3 (Scheme 21, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 21.2 in which $R^1$ is aralkyl such as benzyl, can be converted into the corresponding phosphonic acid 21.3 by hydrogenation over a palladium catalyst, or by treatment with hydrogen chloride in an ethereal solvent such as dioxan. A phosphonate monoester 21.2 in which $R^1$ is alkenyl such as, for example, allyl, can be converted into the phosphonic acid 21.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 21.1 in which $R^1$ is benzyl is described in J. Org. Chem., 24, 434, 1959. Platinum-catalyzed hydrogenolysis of phosphonate esters 21.1 in which $R^1$ is phenyl is described in J. Amer. Chem. Soc., 78, 2336, 1956.

The conversion of a phosphonate monoester 21.2 into a phosphonate diester 21.1 (Scheme 21, Reaction 4) in which the newly introduced $R^1$ group is alkyl, aralkyl, haloalkyl such as chloroethyl, or aralkyl can be effected by a number of reactions in which the substrate 21.2 is reacted with a hydroxy compound $R^1OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 21.2 to the diester 21.1 can be effected by the use of the Mitsonobu reaction, as described above (Scheme 15). The substrate is reacted with the hydroxy compound $R^1OH$, in the presence of diethyl azodicarboxylate and a triarylphosphine such as triphenyl phosphine. Alternatively, the phosphonate monoester 21.2 can be transformed into the phosphonate diester 21.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 21.2 is transformed into the chloro analog RP(O)($OR^1$)Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product RP(O)($OR^1$)Cl is then reacted with the hydroxy compound $R^1OH$, in the presence of a base such as triethylamine, to afford the phosphonate diester 21.1.

A phosphonic acid R-link-P(O)$(OH)_2$ can be transformed into a phosphonate monoester RP(O)($OR^1$)(OH) (Scheme 21, Reaction 5) by means of the methods described above of for the preparation of the phosphonate diester R-link-P(O)$(OR^1)_2$ 21.1, except that only one molar proportion of the component $R^1OH$ or $R^1Br$ is employed.

A phosphonic acid R-link-P(O)$(OH)_2$ 21.3 can be transformed into a phosphonate diester R-link-P(O)$(OR^1)_2$ 21.1 (Scheme 21, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine.

Alternatively, phosphonic acids 21.3 can be transformed into phosphonic esters 21.1 in which $R^1$ is aryl, by means of a coupling reaction employing, for example, dicyclohexylcarbodiimide in pyridine at ca 70°. Alternatively, phosphonic acids 21.3 can be transformed into phosphonic esters 21.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 21.1.

Phosphonate Esters 1-5 Incorporating Carbamate Moieties.

The phosphonate esters 1-5 in which the $R^2CO$ or $R^3CO$ groups are formally derived from the carboxylic acid synthons C38-C49 as shown in Chart 2c, contain a carbamate moiety. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 22 illustrates various methods by which the carbamate linkage can be synthesized. As shown in Scheme 22, in the general reaction generating carbamates, a carbinol 22.1 is converted into the activated derivative 22.2 in which Lv is a leaving group such as halo, imidazolyl, benztriazolyl and the like, as described below. The activated derivative 22.2 is then reacted with an amine 22.3, to afford the carbamate product 22.4. Examples 1-7 in Scheme 22 depict methods by which the general reaction can be effected. Examples 8-10 illustrate alternative methods for the preparation of carbamates.

Scheme 22, Example 1 illustrates the preparation of carbamates employing a chloroformyl derivative of the carbinol 22.5. In this procedure, the carbinol 22.5 is reacted with phosgene, in an inert solvent such as toluene, at about 0°, as described in Org. Syn. Coll. Vol. 3, 167, 1965, or with an equivalent reagent such as trichloromethoxy chloroformate, as described in Org. Syn. Coll. Vol. 6, 715, 1988, to afford the chloroformate 22.6. The latter compound is then reacted with the amine component 22.3, in the presence of an organic or inorganic base, to afford the carbamate 22.7. For example, the chloroformyl compound 22.6 is reacted with the amine 22.3 in a water-miscible solvent such as tetrahydrofuran, in the presence of aqueous sodium hydroxide, as described in Org. Syn. Coll. Vol. 3, 167, 1965, to yield the carbamate 22.7. Alternatively, the reaction is preformed in dichloromethane in the presence of an organic base such as diisopropylethylamine or dimethylaminopyridine.

Scheme 22, Example 2 depicts the reaction of the chloroformate compound 22.6 with imidazole, 22.7, to produce the Imidazolide 22.8. The imidazolide product is then reacted with the amine 22.3 to yield the carbamate 22.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in J. Med. Chem., 1989, 32, 357.

Scheme 22 Example 3, depicts the reaction of the chloroformate 22.6 with an activated hydroxyl compound R"OH, to yield the mixed carbonate ester 22.10. The reaction is conducted in an inert organic solvent such as ether or dichloromethane, in the presence of a base such as dicyclohexylamine or triethylamine. The hydroxyl component R"OH is selected from the group of compounds 22.19-22.24 shown in Scheme 22, and similar compounds. For example, if the component R"OH is hydroxybenztriazole 22.19, N-hydroxysuccinimide 22.20, or pentachlorophenol, 22.21, the mixed carbonate 22.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 22.22 or 2-hydroxypyridine 22.23 can be performed in an ethereal solvent in the presence of triethylamine, as described in Syn., 1986, 303, and Chem. Ber. 118, 468, 1985.

Scheme 22 Example 4 illustrates the preparation of carbamates in which an alkyloxycarbonylimidazole 22.8 is employed. In this procedure, a carbinol 22.5 is reacted with an equimolar amount of carbonyl diimidazole 22.11 to prepare the intermediate 22.8. The reaction is conducted in an aprotic organic solvent such as dichloromethane or tetrahydrofuran. The acyloxyimidazole 22.8 is then reacted with an equimolar amount of the amine R'$NH_2$ to afford the carbamate 22.7. The reaction is performed in an aprotic organic solvent such as dichloromethane, as described in Tet. Lett., 42, 2001, 5227, to afford the carbamate 22.7.

Scheme 22, Example 5 illustrates the preparation of carbamates by means of an intermediate alkoxycarbonylbenztriazole 22.13. In this procedure, a carbinol ROH is reacted at ambient temperature with an equimolar amount of benztriazole carbonyl chloride 22.12, to afford the alkoxycarbonyl product 22.13. The reaction is performed in an organic solvent such as benzene or toluene, in the presence of a tertiary organic amine such as triethylamine, as described in Syn., 1977, 704. This product is then reacted with the amine R'$NH_2$ to afford the carbamate 22.7. The reaction is conducted in toluene or ethanol, at from ambient temperature to about 80° as described in Syn., 1977, 704.

Scheme 22, Example 6 illustrates the preparation of carbamates in which a carbonate $(R''O)_2CO$, 22.14, is reacted with a carbinol 22.5 to afford the intermediate alkyloxycarbonyl intermediate 22.15. The latter reagent is then reacted with the amine R'$NH_2$ to afford the carbamate 22.7. The procedure in which the reagent 22.15 is derived from hydroxybenztriazole 22.19 is described in Synthesis, 1993, 908; the procedure in which the reagent 22.15 is derived from N-hydroxysuccinimide 22.20 is described in Tet. Lett., 1992, 2781; the procedure in which the reagent 22.15 is derived from 2-hydroxypyridine 22.23 is described in Tet. Lett., 1991, 4251; the procedure in which the reagent 22.15 is derived from 4-nitrophenol 22.24 is described in Syn. 1993, 103. The reaction between equimolar amounts of the carbinol ROH and the carbonate 22.14 is conducted in an inert organic solvent at ambient temperature.

Scheme 22, Example 7 illustrates the preparation of carbamates from alkoxycarbonyl azides 22.16. in this procedure, an alkyl chloroformate 22.6 is reacted with an azide, for example sodium azide, to afford the alkoxycarbonyl azide 22.16. The latter compound is then reacted with an equimolar amount of the amine R'$NH_2$ to afford the carbamate 22.7. The reaction is conducted at ambient temperature in a polar aprotic solvent such as dimethylsulfoxide, for example as described in Syn., 1982, 404.

Scheme 22, Example 8 illustrates the preparation of carbamates by means of the reaction between a carbinol ROH and the chloroformyl derivative of an amine. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 22.7.

Scheme 22, Example 9 illustrates the preparation of carbamates by means of the reaction between a carbinol ROH and an isocyanate 22.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 22.7.

Scheme 22, Example 10 illustrates the preparation of carbamates by means of the reaction between a carbinol ROH and an amine R'$NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 22.7.

Scheme 21

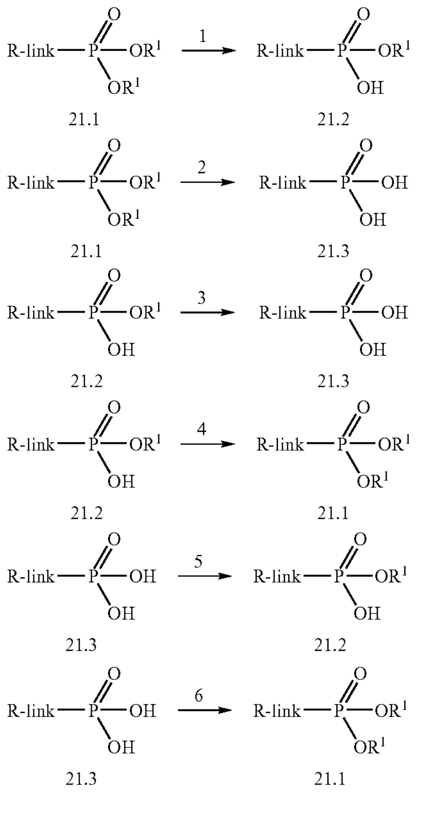

Scheme 22

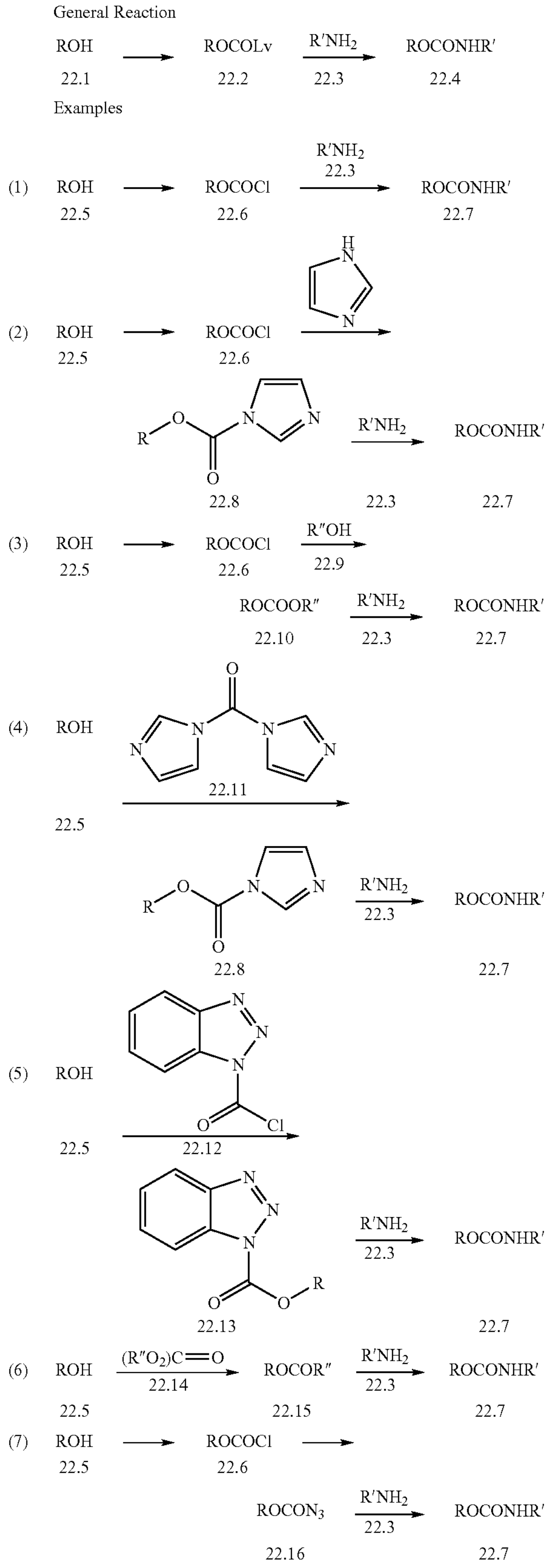

-continued

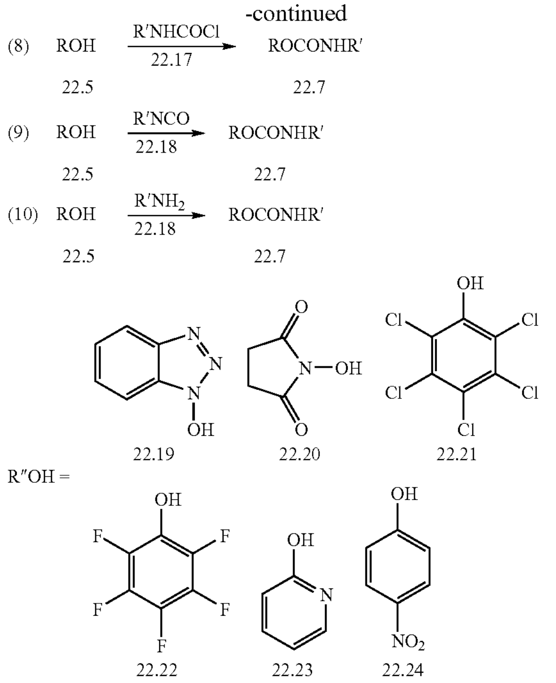

Preparation of Phosphonate Intermediates 4 and 5 with Phosphonate Moieties Incorporated into the Groups $R^2COOH$ and $R^3COOH$.

The chemical transformations described in Schemes 1-22 illustrate the preparation of compounds 1-3 in which the phosphonate ester moiety is attached to the dimethylphenoxyacetyl ($R^3$) substructure, (Schemes 1-3), the phenylalanine moiety (Schemes 4-6), and the benzyl moiety (Schemes 7, 8).

The various chemical methods employed herein (Schemes 9-22) for the preparation of phosphonate groups can, with appropriate modifications known to those skilled in the art, be applied to the introduction of phosphonate ester groups into the compounds $R^2COOH$ and $R^3COOH$, as defined in Charts 2a, 2b, and 2c. The resultant phosphonate-containing analogs $R^{2a}COOH$ and $R^{3a}COOH$ can then, using the procedures described above, be employed in the preparation of the compounds 4 and 5. The procedures required for the introduction of the phosphonate-containing analogs $R^{2a}COOH$ and $R^{3a}COOH$ are the same as those described above (Schemes 4, 5 and 22) for the introduction of the $R^2CO$ and $R^3CO$ moieties.

For example, Schemes 23-27 illustrate methods for the preparation of hydroxymethyl-substituted benzoic acids (structure C25, Chart 2b) incorporating phosphonate moieties; Schemes 28-30 illustrate the preparation of tetrahydropyrimidine aminoacid derivatives (structure C27, Scheme 2b) incorporating phosphonate ester moieties, and Schemes 31-33 show the syntheses of benzyl carbamate aminoacid derivatives (structure C4, Chart 2a) incorporating phosphonate ester moieties. The thus-obtained phosphonate ester synthons are then incorporated into the compounds 4 and 5.

Scheme 23 illustrates a method for the preparation of hydroxymethylbenzoic acid reactants in which the phosphonate moiety is attached directly to the phenyl ring. In this method, a suitably protected bromo hydroxy methyl benzoic acid 23.1 is subjected to halogen-methyl exchange to afford the organometallic intermediate 23.2. This compound is reacted with a chlorodialkyl phosphite 23.3 to yield the phenylphosphonate ester 23.4, which upon deprotection affords the carboxylic acid 23.5.

For example, 4-bromo-3-hydroxy-2-methylbenzoic acid, 23.6, prepared by bromination of 3-hydroxy-2-methylbenzoic acid, as described, for example, J. Amer. Chem. Soc., 55, 1676, 1933, is converted into the acid chloride, for example by reaction with thionyl chloride. The acid chloride is then reacted with 3-methyl-3-hydroxymethyloxetane 23.7, as described in Protective Groups in Organic Synthesis, by T. W. Greene and P. G. M. Wuts, Wiley, 1991, pp. 268, to afford the ester 23.8. This compound is treated with boron trifluoride at 0° to effect rearrangement to the orthoester 23.9, known as the OBO ester. This material is treated with a silylating reagent, for example tert-butyl chlorodimethylsilane, in the presence of a base such as imidazole, to yield the silyl ether 23.10. Halogen-metal exchange is performed by the reaction of 23.10 with butyllithium, and the lithiated intermediate is then coupled with a chlorodialkyl phosphite 23.3, to produce the phosphonate 23.11. Deprotection, for example by treatment with 4-toluenesulfonic acid in aqueous pyridine, as described in Can. J. Chem., 61, 712, 1983, removes both the OBO ester and the silyl group, to produce the carboxylic acid 23.12.

Using the above procedures, but employing, in place of the bromo compound 23.6, different bromo compounds 23.1, there are obtained the corresponding products 23.5.

Scheme 24 illustrates the preparation of hydroxymethylbenzoic acid derivatives in which the phosphonate moiety is attached by means of a one-carbon link.

In this method, a suitably protected dimethyl hydroxybenzoic acid, 24.1, is reacted with a brominating agent, so as to effect benzylic bromination. The product 24.2 is reacted with a sodium dialkyl phosphite, 24.3, as described in J. Med. Chem., 1992, 35, 1371, to effect displacement of the benzylic bromide to afford the phosphonate 24.4. Deprotection of the carboxyl function then yields the carboxylic acid 24.5.

For example, 2,5-dimethyl-3-hydroxybenzoic acid, 24.6, the preparation of which is described in Can. J. Chem., 1970, 48, 1346, is reacted with excess methoxymethyl chloride, as described in Protective Groups in Organic Synthesis, by T. W. Greene and P. G. M Wuts, Second Edition 1990, p17, to afford the ether ester 24.7. The reaction is performed in an inert solvent such as dichloromethane, in the presence of an organic base such as N-methylmorpholine or diisopropylethylamine. The product 24.7 is then reacted with a brominating agent, for example N-bromosuccinimide, in an inert solvent such as, for example, ethyl acetate, at reflux, to afford the bromomethyl product 24.8. This compound is then reacted with a sodium dialkyl phosphite 24.3 in tetrahydrofuran, as described above, to afford the phosphonate 24.9. Deprotection, for example by brief treatment with a trace of mineral acid in methanol, as described in J. Chem. Soc. Chem. Comm., 1974, 298, then yields the carboxylic acid 24.10.

Using the above procedures, but employing, in place of the methyl compound 24.6, different methyl compounds 24.1, there are obtained the corresponding products 24.5.

Scheme 25 illustrates the preparation of phosphonate-containing hydroxymethylbenzoic acids in which the phosphonate group is attached by means of an oxygen or sulfur atom.

In this method, a suitably protected hydroxy- or mercapto-substituted hydroxymethyl benzoic acid 25.1 is reacted, under the conditions of the Mitsonobu reaction, with a dialkyl hydroxymethyl phosphonate 25.2, to afford the coupled product 25.3, which upon deprotection affords the carboxylic acid 25.4.

For example, 3,6-dihydroxy-2-methylbenzoic acid, 25.6, the preparation of which is described in Yakugaku Zasshi 1971, 91, 257, is converted into the diphenylmethyl ester 25.7, by treatment with diphenyldiazomethane, as described in Protective Groups in Organic Synthesis, by T. W. Greene and P. G. M. Wuts, Wiley, 1991, pp. 253. The product is then reacted with one equivalent of a silylating reagent, such as, for example, tert butylchlorodimethylsilane, as described in Protective Groups in Organic Synthesis, by T. W. Greene and P. G. M Wuts, Wiley, Second Edition 1990, p. 77, to afford the mono-silyl ether 25.8. This compound is then reacted with a dialkyl hydroxymethylphosphonate 25.2, under the conditions of the Mitsonobu reaction, as described above (Scheme 15) to afford the coupled product 25.9. Deprotection, for example by treatment with trifluoroacetic acid at ambient temperature, as described in J. Chem. Soc., C, 1191, 1966, then affords the phenolic carboxylic acid 25.10.

Using the above procedures, but employing, in place of the phenol 25.6, different phenols or thiophenols 25.1, there are obtained the corresponding products 25.4.

Scheme 26 depicts the preparation of phosphonate esters attached to the hydroxymethylbenzoic acid moiety by means of unsaturated or saturated carbon chains.

In this method, a dialkyl alkenylphosphonate 26.2 is coupled, by means of a palladium catalyzed Heck reaction, with a suitably protected bromo substituted hydroxymethylbenzoic acid 26.1. The product 26.3 can be deprotected to afford the phosphonate 26.4, or subjected to catalytic hydrogenation to afford the saturated compound, which upon deprotection affords the corresponding carboxylic acid 26.5.

For example, 5-bromo-3-hydroxy-2-methylbenzoic acid 26.6, prepared as described in WO 9218490, is converted as described above, into the silyl ether OBO ester 26.7. This compound is coupled with, for example, a dialkyl 4-buten-1-ylphosphonate 26.8, the preparation of which is described in J. Med. Chem., 1996, 39, 949, using the conditions described above (Scheme 11) to afford the product 26.9. Deprotection, or hydrogenation/deprotection, of this compound, as described above, then affords respectively the unsaturated and saturated products 26.10 and 26.11.

Using the above procedures, but employing, in place of the bromo compound 26.6, different bromo compounds 26.1, and/or different phosphonates 26.2, there are obtained the corresponding products 26.4 and 26.5.

Scheme 27 illustrates the preparation of phosphonate esters linked to the hydroxymethylbenzoic acid moiety by means of an aromatic ring.

In this method, a suitably protected bromo-substituted hydroxymethylbenzoic acid 27.1 is converted to the corresponding boronic acid 27.2, by metallation with butyllithium and boronation, as described in J. Organomet. Chem., 1999, 581, 82. The product is subjected to a Suzuki coupling reaction with a dialkyl bromophenyl phosphonate 27.3. The product 27.4 is then deprotected to afford the diaryl phosphonate product 27.5.

For example, the silylated OBO ester 27.6, prepared as described above, (Scheme 23), is converted into the boronic acid 27.7, as described above. This material is coupled with a dialkyl 4-bromophenyl phosphonate 27.8, prepared as described in J. Chem. Soc. Perkin Trans., 1977, 2, 789, using tetrakis(triphenylphosphine)palladium(0) as catalyst, in the presence of sodium bicarbonate, as described, for example, in Palladium reagents and catalysts J. Tsuji, Wiley 1995, p 218, to afford the diaryl phosphonate 27.9. Deprotection, as described above, then affords the benzoic acid 27.10.

Using the above procedures, but employing, in place of the bromo compound 27.6, different bromo compounds 27.1, and/or different phosphonates 27.3, there are obtained the corresponding carboxylic acid products 27.5.

Scheme 28 illustrates the preparation of analogs of the tetrahydropyrimidine carboxylic acid C27 in which the phosphonate moiety is attached by means of an alkylene chain incorporating a heteroatom O, S, or N. In this procedure, an aminoacid 28.1, in which $R^4$ is as defined in Chart 2b, is converted into the corresponding phenyl carbamate 28.2. The preparation of phenyl carbamates is described in Tet. Lett., 1977, 1936, and in J. Chem. Soc., C, 1967, 2015. The amine substrate is reacted with phenyl chloroformate in the presence of an inorganic or organic base, such as potassium carbonate or triethylamine, in an organic, aqueous or aqueous organic solvent such as dichloromethane, tetrahydrofuran or water or pyridine. Preferably, the aminoacid 28.1 is reacted with phenyl chloroformate, in water containing lithium hydroxide, lithium chloride and alumina, at a pH of about 9.5, as described in Org. Process Res. Dev., 2000, 4, 264, to afford the phenyl carbamate 28.2. This compound is then reacted with di(3-chloropropyl)amine 28.3, prepared as described in Tet. 1995, 51, 1197, to afford the amide product 28.4. The preparation of amides by reaction of an ester with an amide is described, for example, in Comprehensive Organic Transformations, by R. C. Larock, VCH, 1989, p. 987. The displacement reaction is effected by treatment of the substrate with the amine, optionally in the presence of a base such as sodium methoxide and the like, to afford the amide product 28.4. Preferably, the carbamate 28.2 and the amine 28.3 are reacted together in tetrahydrofuran, in the presence of sodium hydroxide or lithium hydroxide, to produce the amide product 28.4. The latter compound is then transformed, optionally without isolation, into the chloropropyl-substituted tetrahydropyrimidine product 28.5, by reaction with a strong base such as potassium tert. butoxide in tetrahydrofuran, as described in Org. Process. Res. Dev., 2000, 4, 264. The compound 28.5 is then reacted with a dialkyl hydroxy, mercapto or alkylamino-substituted alkylphosphonate 28.6 to afford the displacement product 28.7. The reaction is conducted in a polar organic solvent such as dimethylformamide or acetonitrile, in the presence of a base such as sodium hydride, lithium hexamethyldisilazide, potassium carbonate or the like, optionally in the presence of a catalytic amount of potassium iodide, to afford the ether, thioether or amine product 28.7.

Alternatively, the chloropropyl-substituted tetrahydropyrimidine compound 28.5 is transformed into the corresponding propylamine 28.8. The conversion of halo derivatives into amines is described, for example, in Comprehensive Organic Transformations, by R. C. Larock, VCH, 1989, p. 397ff, or Synthetic Organic Chemistry, R. B. Wagner, H. D. Zook, Wiley, 1953 p. 665ff. The chloro compound is reacted with ammonium hydroxide, anhydrous ammonia or hexamethylene tetramine, or with an alkali metal amide such as sodamide to afford the mine product. Preferably, the chloro compound is reacted with potassium phthalimide, and the phthalimido product is then cleaved by treatment with hydrazine, as described in Synthetic Organic Chemistry, R. B. Wagner, H. D. Zook, Wiley, 1953 p. 679, to afford the amine 28.8. The product is then subjected to a reductive amination reaction with a dialkyl formylalkyl phosphonate 28.9, to yield the phosphonate product 28.10.

For example, as shown in Scheme 28, Example 1,3-methyl-2-phenoxycarbonylamino-butyric acid 28.11, prepared as described in Org. Process Res. Dev., 2000, 4, 264, is reacted with di(3-chloropropyl)amine, using the conditions described above, to afford 2-[3,3-bis-(3-chloropropyl)-ureido]-3-methyl-butyric acid 28.4. The product is then reacted sequentially with sodium hydroxide and then potassium tert. butoxide in tetrahydrofuran, as described in Org. Process Res. Dev., 2000, 4, 264, so as to afford the cyclized product 2-[3-(3-chloro-propyl)-2-oxo-tetrahydro-pyrimidin-1-yl]-3-methyl-butyric acid 28.13. The latter compound is then reacted in dimethylformamide solution at about 70°, with a dialkyl 2-mercaptoethyl phosphonate 28.14, prepared as described in Zh. Obschei. Khim., 1973, 43, 2364, potassium carbonate and a catalytic amount of potassium iodide, to yield the phosphonate ester 28.13. Using the above procedures, but employing, in place of the valine carbamate 28.11, different carbamates 28.2, and/or different hetero-substituted alkyl phosphonates 28.6, the corresponding products 28.7 are obtained.

As a further illustration, Scheme 28, Example 2 depicts the reaction of the chloro-propyl tetrahydropyrimidine derivative 28.13 with potassium phthalimide 28.16. Equimolar amounts of the reactants are combined in dimethylformamide at ca 80°, in the presence of a catalytic amount of potassium iodide, to afford 2-{3-[3-(1,3-dioxo-1,3-dihydro-isoindol-2-yl)-propyl]-2-oxo-tetrahydro-pyrimidin-1-yl}-3-methyl-butyric acid 28.17. The product is then reacted under reductive amination conditions, as described above (Scheme 10) with a dialkyl formylphenyl phosphonate 28.19 (Epsilon) to yield the phosphonate ester product 28.20.

Using the above procedures, but employing, in place of the valine carbamate 28.11, different carbamates 28.2, and/or different formyl-substituted alkyl phosphonates 28.9, the corresponding products 28.10 are obtained.

Scheme 29 illustrates the preparation of analogs of the tetrahydropyrimidine carboxylic acid C27 in which the phosphonate moiety is attached by means of an alkylene chain. In this procedure, an aminoacid 29.1 is subjected to an alkylation reaction with a propanol derivative 29.2 in which Lv is a leaving group such as halo or sulfonyl. The reaction is conducted in aqueous or aqueous organic solution in the presence of a base such as sodium hydroxide, potassium carbonate and the like, to afford the product 29.3. This compound is then oxidized to the corresponding aldehyde 29.4. The conversion of alcohols to aldehydes is described, for example, in Comprehensive Organic Transformations, by R. C. Larock, VCH, 1989, p. 604ff.

Typically, the alcohol is reacted with an oxidizing agent such as pyridinium chlorochromate, silver carbonate, or dimethyl sulfoxide/acetic anhydride. The reaction is conducted in an inert aprotic solvent such as pyridine, dichloromethane or toluene. Preferably, the alcohol 29.3 is reacted with an equimolar amount of pyridinium chlorochromate in dichloromethane at ambient temperature, to afford the aldehyde 29.4. This material is then subjected to a reductive amination reaction with a dialkyl aminoalkyl phosphonate 29.5, using the conditions described above (Scheme 10) to produce the phosphonate ester 29.6. The latter compound is then reacted with phosgene, or carbonyldiimidazole or an equivalent reagent, to yield the tetrahydropyrimidine product 29.7. Equimolar amounts of the reagents are combined in an inert polar solvent such as tetrahydrofuran or dimethylformamide at ambient temperature, to effect the cyclization reaction.

For example, 2-(3-hydroxy-propylamino)-3-methyl-butyric acid, the preparation of which is described in Toxicol. Appl. Pharm., 1995, 131, 73, is oxidized, as described above, to afford 3-methyl-2-(3-oxo-propylamino)-butyric acid 29.9. The product is then reacted with a dialkyl aminoethyl phosphonate 29.10, the preparation of which is described in J. Org. Chem., 2000, 65, 676, under reductive amination conditions, to give the product 29.11. This compound is then reacted one molar equivalent of carbonyldiimidazole in dichloromethane, as described in U.S. Pat. No. 5,914,332, to afford the tetrahydropyrimidine product 29.12.

Using the above procedures, but employing, in place of the valine derivative 29.8, different aminoacid derivatives 29.3, and/or different amino-substituted alkyl phosphonates 29.5, the corresponding products 29.7 are obtained.

Scheme 30 illustrates the preparation of analogs of the tetrahydropyrimidine carboxylic acid C27 in which the phosphonate moiety is attached by means of an alkylene chain. In this procedure, a tetrahydropyrimidine aminoacid derivative, prepared as described in U.S. Pat. No. 5,914,332, is converted into the carboxyl-protected compound 30.2. The protection and deprotection of carboxyl groups is described in Protective Groups in Organic Synthesis, by T. W. Greene and P. G. M Wuts, Wiley, Second Edition 1990, p. 224ff. For example, the carboxyl group is protected as a benzyl or substituted benzyl ester, removable by means of hydrogenolysis, or as a tert. butyl ester, removable by treatment with anhydrous acid. The carboxyl-protected derivative 30.2 is then reacted with a dialkyl bromoalkyl phosphonate 30.3, in the presence of a strong base such as sodium hydride, potassium tert. butoxide, lithium hexamethyldisilazide and the like, in a polar solvent such as dimethylformamide, to afford the alkylation product 30.4. The carboxyl group is then deprotected to yield the carboxylic acid 30.5.

For example, 3-methyl-2-(3-methyl-2-oxo-tetrahydro-pyrimidin-1-yl)-butyric acid 30.6, prepared as described in Org. Process Res. Dev., 200, 4, 264, is converted into the benzyl ester 30.7 by reaction with benzyl alcohol, dicyclohexylcarbodiimide and dimethylaminopyridine in dichloromethane, as described in J. Chem. Soc. Chem. Comm., 1982, 1132. The product is then treated with one molar equivalent of lithium hexamethyldisilazide in dimethylformamide, and the resultant anion is reacted with one molar equivalent of a dialkyl 3-bromopropyl phosphonate 30.8 (Aldrich), to prepare the alkylated product 30.9. The benzyl ester is then converted into the carboxylic acid 30.10, by hydrogenolysis over a palladium catalyst, as described in Org. React., VII, 263, 1953.

Using the above procedures, but employing, in place of the valine derivative 30.6, different aminoacid derivatives 30.1, and/or different bromo-substituted alkyl phosphonates 30.3, the corresponding products 30.5 are obtained.

Scheme 31 illustrates the preparation of phosphonate-containing derivatives of the carboxylic acid C4 (Chart 2a) in which the phosphonate group is attached by means of an alkylene chain and a heteroatom O, S or N. In this procedure, a substituted benzyl alcohol 31.1 is reacted with a dialkyl bromoalkyl phosphonate 31.2 to prepare the ether, thioether or amine product 31.3. The alkylation reaction is conducted in a polar organic solvent such as dimethylformamide or acetonitrile, in the presence of a base such as potassium carbonate, optionally in the presence of a catalytic amount of potassium iodide. The benzyl alcohol product 31.3 is then transformed into a formyl derivative 31.4, in which Lv is a leaving group, as described above (Scheme 22). The formate derivative 31.4 is then reacted with a carboxy-protected amino acid 31.5, using the procedures described above for the preparation of carbamates (Scheme 22), to afford the carbamate product 31.6. The carboxy-protecting group is then removed to afford the carboxylic acid 31.7. The carboxyl protecting group present in the aminoacid 31.5 is selected so that the conditions for removal do not cleave the benzyl carbamate moiety in the substrate 31.6.

For example, 3-methylaminobenzyl alcohol 31.8 is reacted in dimethylformamide solution at ca 70° with one molar equivalent of a dialkyl bromoethyl phosphonate 31.9(Aldrich) and potassium carbonate, to afford the amine 31.10. The product is then with reacted one molar equivalent of carbonyldiimidazole in tetrahydrofuran, to give the imidazolide product 31.11. The compound is then reacted with the tert. butyl ester of valine 31.12, in pyridine at ambient temperature, to afford the carbamate product 31.13. The tert. butyl ester is then removed by treatment of the ester 31.13 with trifluoroacetic acid at 0°, as described in J. Am. Chem. Soc., 99, 2353, 1977, to afford the carboxylic acid 31.14.

Using the above procedures, but employing, in place of the benzyl alcohol derivative 31.8, different benzyl alcohols 31.1, and/or different bromo-substituted alkyl phosphonates 31.2, the corresponding products 31.7 are obtained.

Scheme 32 illustrates the preparation of phosphonate-containing derivatives of the carboxylic acid C4 (Chart 2a) in which the phosphonate group is attached by means of a saturated or unsaturated alkylene chain. In this procedure, a bromo-substituted benzyl alcohol 32.1 is coupled, in the presence of a palladium catalyst, with a dialkyl alkenylphosphonate 32.2. The coupling reaction between aryl bromides and olefins is described above (Scheme 11). The coupled product 32.3 is then converted into the carbamate derivative 32.5, by means of the series of reactions illustrated above (Scheme 31) for the conversion of the benzyl alcohol 31.3 into the carbamate derivative 31.7. Alternatively, the unsaturated compound 32.3 is reduced, diimide or diborane, as described in Comprehensive Organic Transformations, by R. C. Larock, VCH, 1989, p.8, to produce the saturated analog 32.4. This material as then transformed, as described above, into the carbamate derivative 32.6.

For example, 4-bromobenzyl alcohol 32.7 is coupled, in the presence of diethyl vinylphosphonate, prepared as described in Synthesis, 1983, 556, in the presence of ca. 3 mol % of palladium(II) acetate, triethylamine and tri(o-tolyl) phosphine in acetonitrile at ca. 100° in a sealed tube, as described in Synthesis, 1983, 556, to produce the coupled product 32.9. The product is then converted, as described above, into the unsaturated and saturated carbamate derivatives 32.10 and 32.11.

Using the above procedures, but employing, in place of 4-bromobenzyl alcohol 32.7, different benzyl alcohols 32.1, and/or different dialkyl alkenyl phosphonates 32.2, the corresponding products 32.5 and 32.6 are obtained.

Scheme 33 illustrates the preparation of phosphonate-containing derivatives of the carboxylic acid C4 (Chart 2a) in which the phosphonate group is attached by means of a phenyl ring. In this procedure, a benzaldehyde boronic acid 33.1 is coupled, using the procedures described above (Scheme 27) with a dialkyl bromophenylphosphonate 33.2, to afford the biphenyl derivative 33.3. The aldehyde group is then reduced to give the corresponding benzyl alcohol 33.4. The reduction of aldehydes to afford alcohols is described, for example, in Organic Functional Group Preparations, by S. R. Sandler and W. Karo, Academic Press, 1968. The conversion can be effected by the use of reducing agents such as sodium borohydride, lithium aluminum tri-tertiarybutoxy hydride, diborane and the like. Preferably, the aldehyde 33.3 is reduced to the carbinol 33.4 by reaction with sodium borohydride in ethanol at ambient temperature. The resulting benzyl alcohol is then transformed, using the procedures described above, (Scheme 31) into the carbamate derivative 33.5.

For example, 3-formylphenylboronic acid 33.6 (Fluka) is coupled with a dialkyl 4-bromophenylphosphonate 33.7, prepared as described in J. Organomet. Chem., 1999, 581, 62, in the presence of tetrakis(triphenylphosphine)palladium and sodium bicarbonate, as described in Palladium Reagents and Catalysts, by J. Tsuji, Wiley 1995, p. 218, to yield the diphenyl compound 33.8. The aldehyde group is reduced to afford the carbinol 33.9, and the latter compound is then transformed, as described above, into the carbamate derivative 33.10.
Using the above procedures, but employing, in place of the benzaldehyde 33.6, different benzaldehydes 33.1, and/or different dialkyl bromophenyl phosphonates 33.2, the corresponding products 33.4 are obtained.
Scheme 23
Method
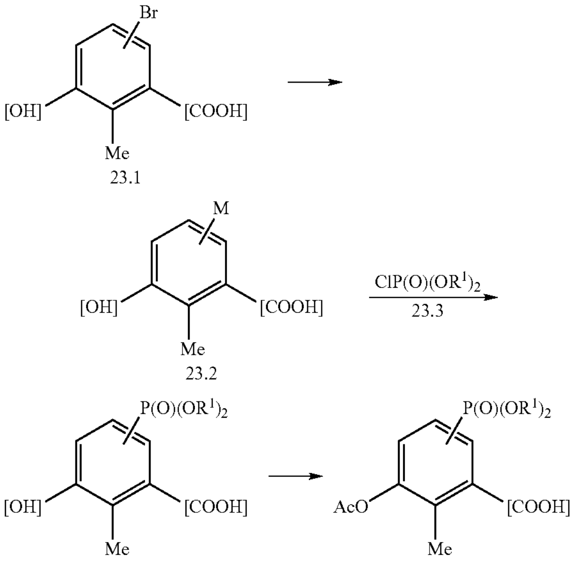
23.1 23.2 23.4 23.5
Example
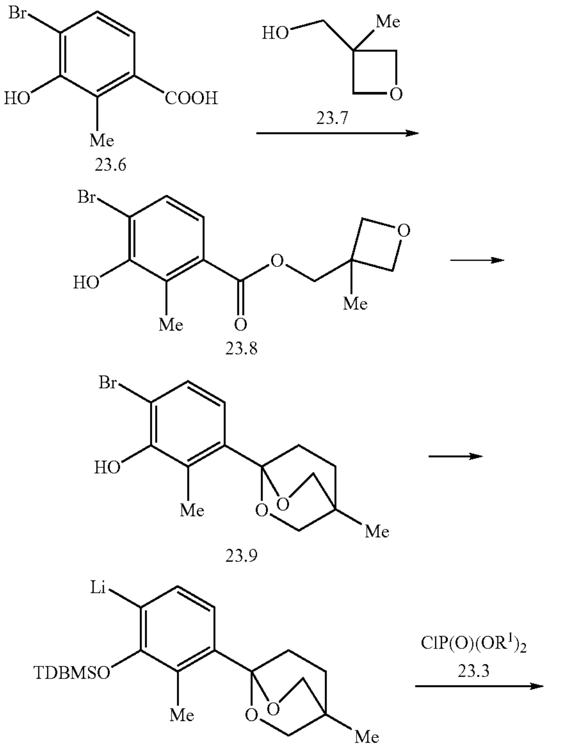
23.6 23.8 23.9 23.10
-continued
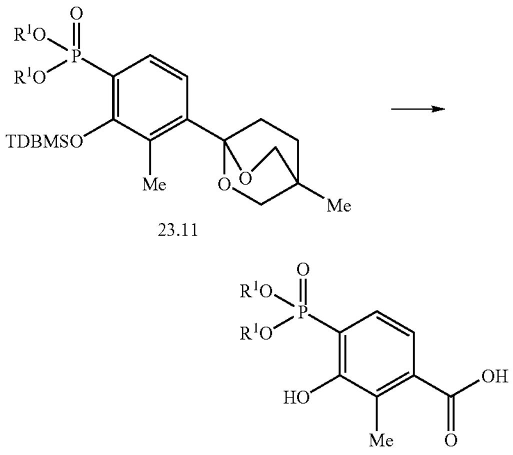
23.11 23.12
Scheme 24
Method
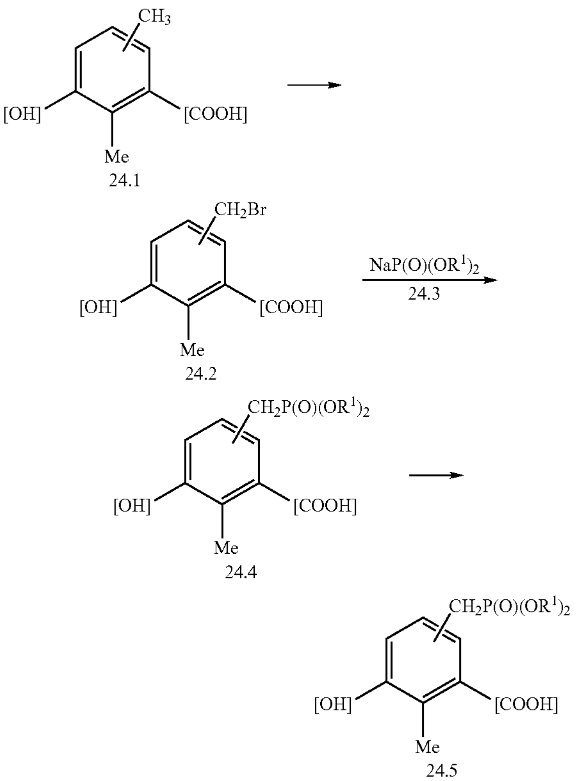
24.1 24.2 24.4 24.5
Example
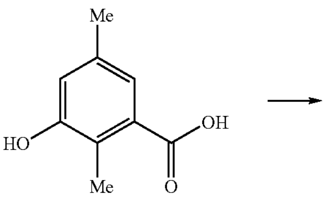
24.6

-continued
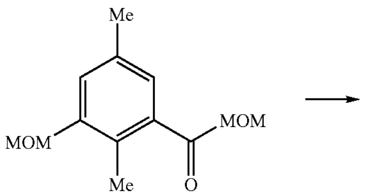
24.7
$MOM = CH_3OCH_2O$
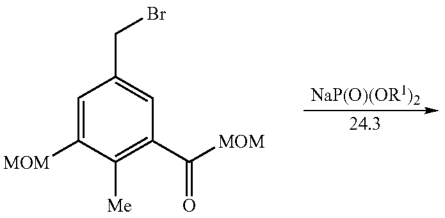
24.8
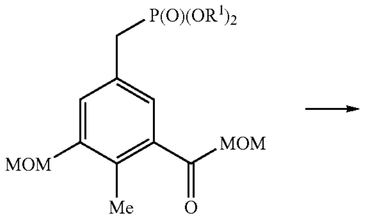
24.9
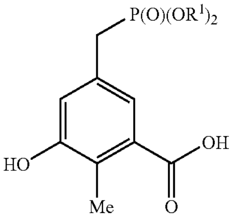
24.10
Scheme 25
Method
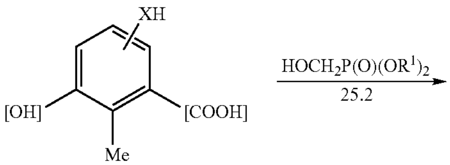
25.1
X = O, S
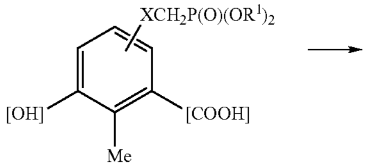
25.3
-continued
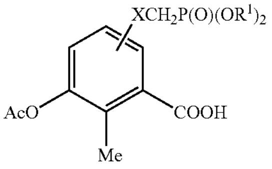
25.4
Example
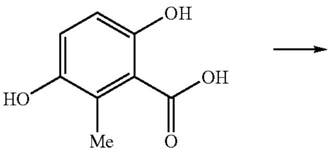
25.6
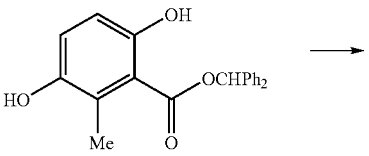
25.7
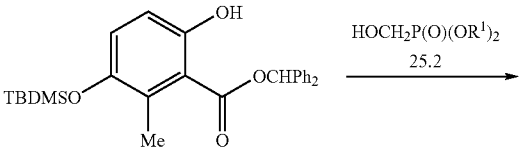
25.8
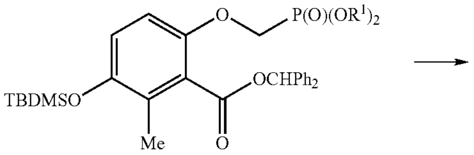
25.9
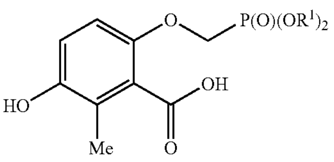
25.10

Scheme 26
Method
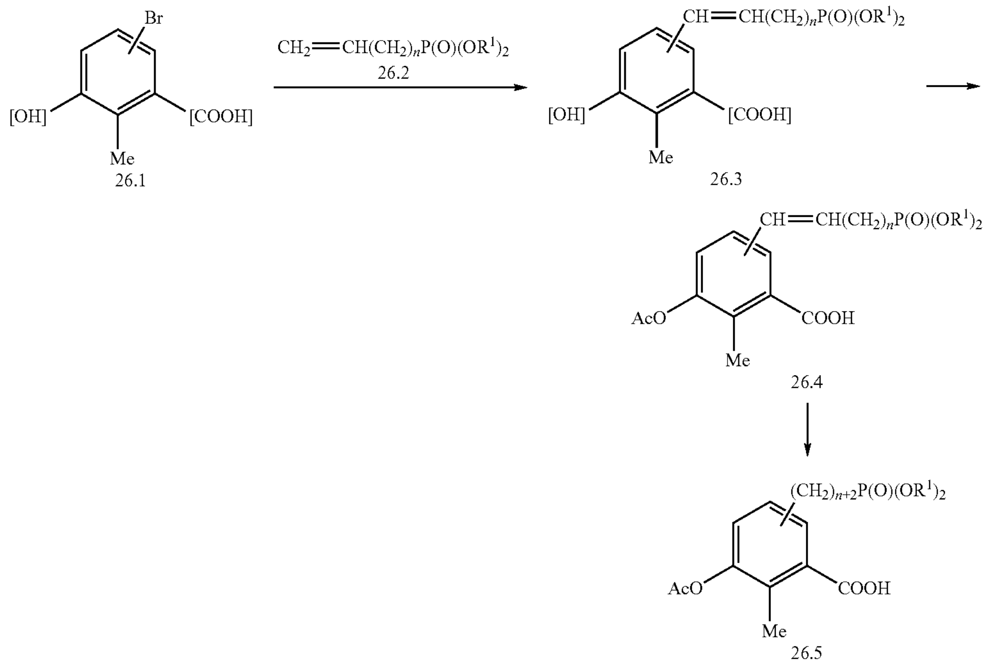
26.1 26.3 26.4 26.5
Example
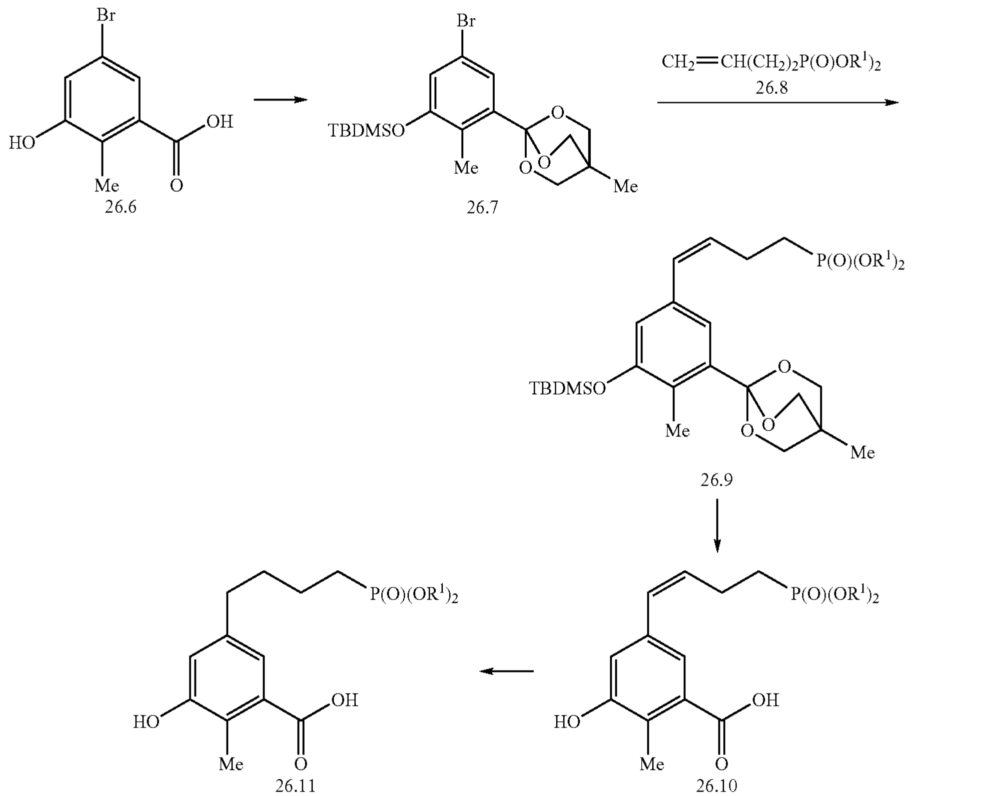
26.6 26.7 26.9 26.10 26.11

Scheme 27
Method
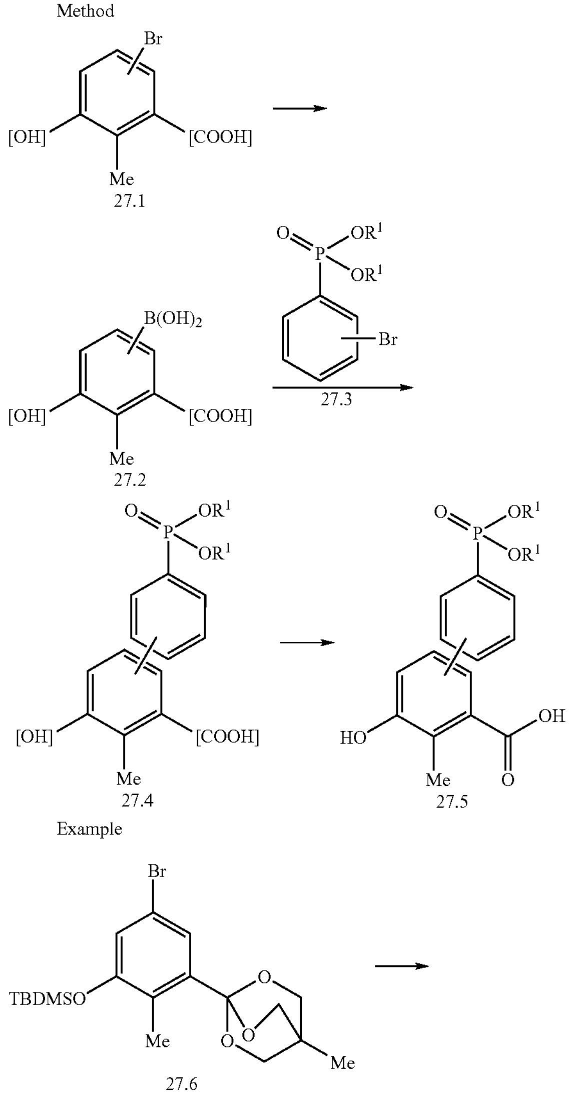
27.1, 27.2, 27.3, 27.4, 27.5
Example
27.6
-continued
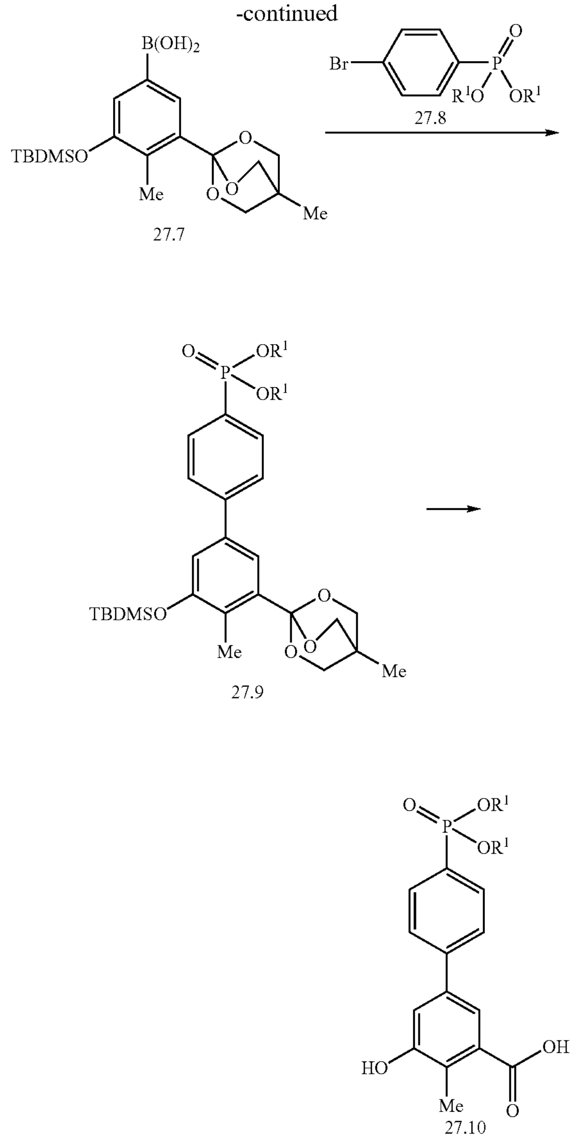
27.7, 27.8, 27.9, 27.10
Scheme 28
Method
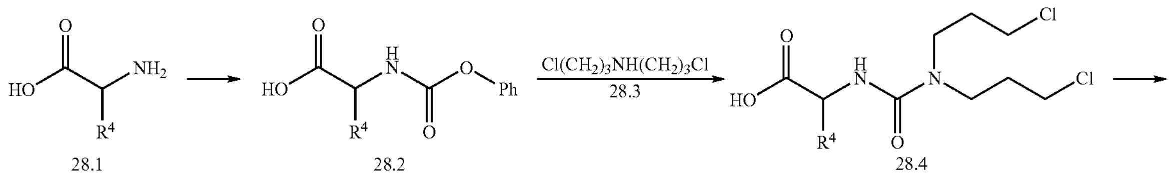
28.1, 28.2, 28.4

-continued
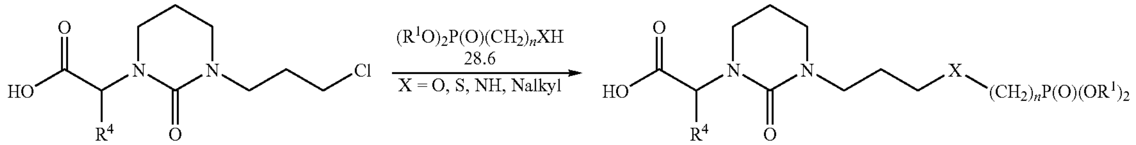
28.5 28.7
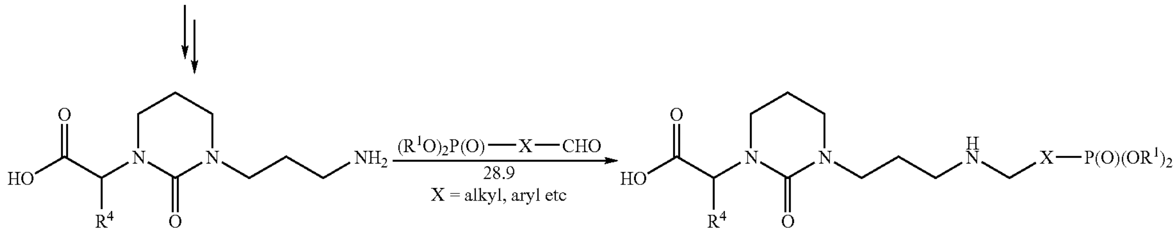
28.8 28.10
Example 1
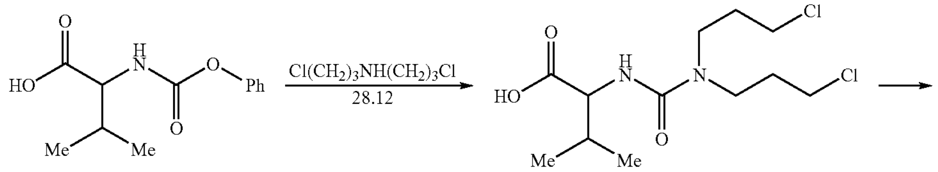
28.11 28.4
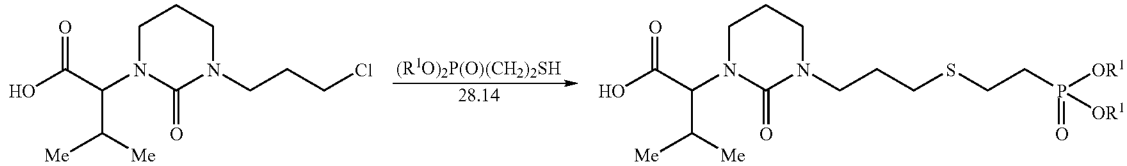
28.13 28.15
Example 2
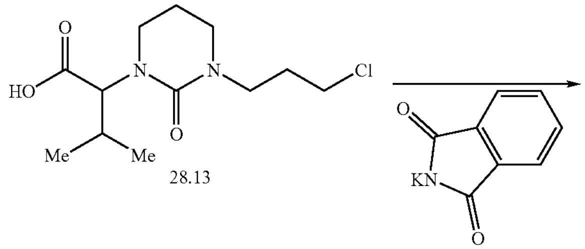
28.13 28.16
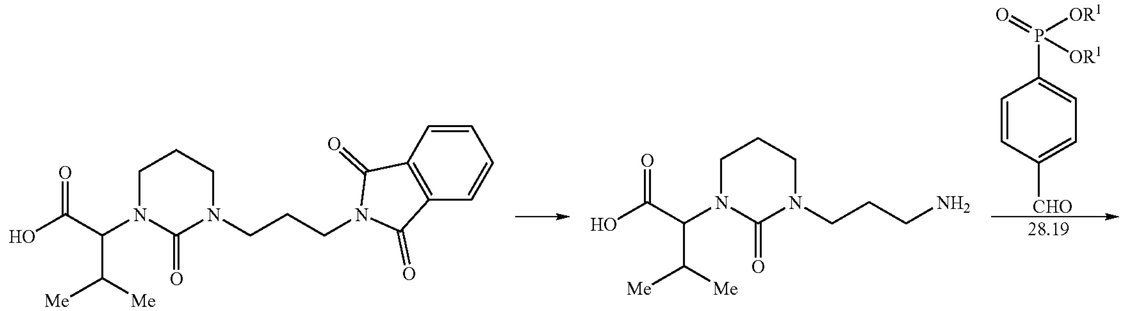
28.17 28.18

-continued
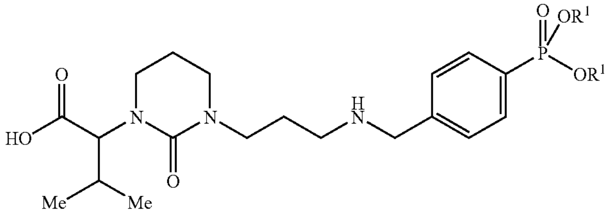
28.20
Scheme 29
Method
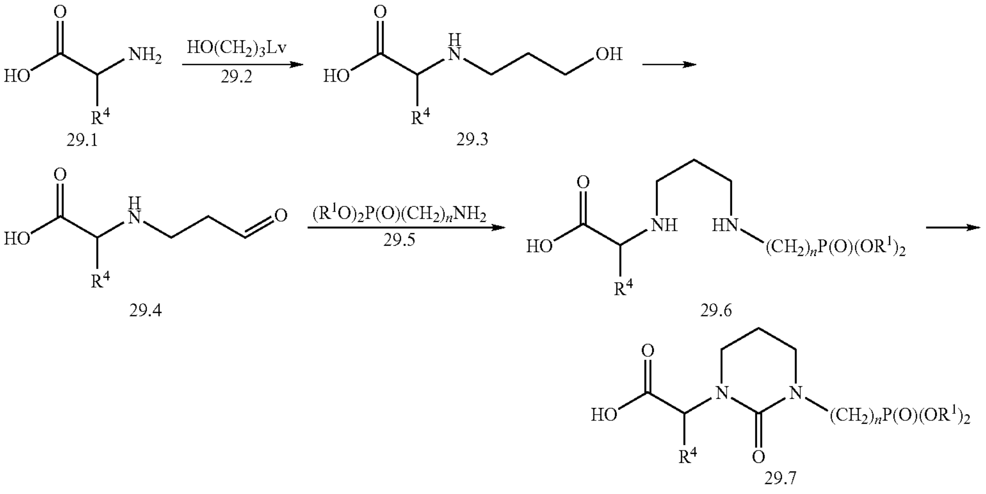
Example
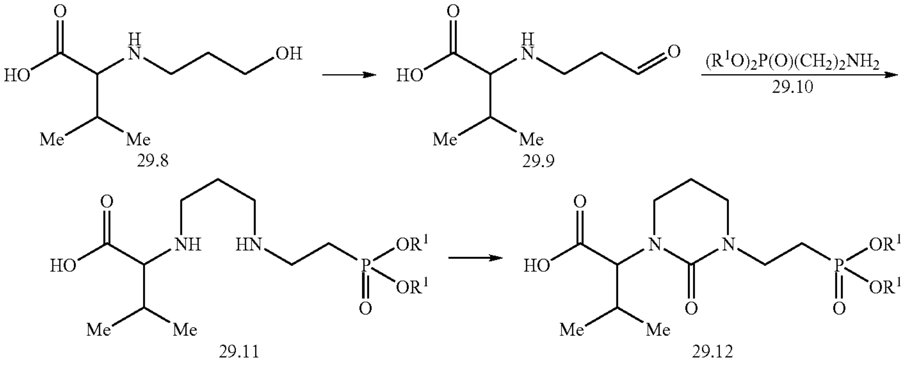
Scheme 30
Method
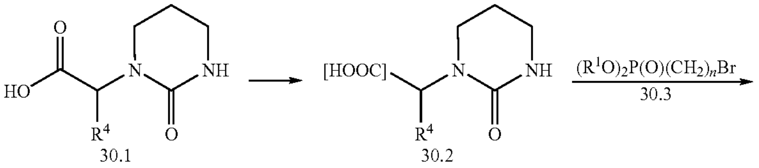

-continued
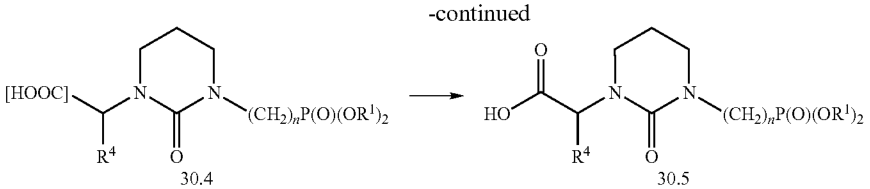
30.4 30.5
Example
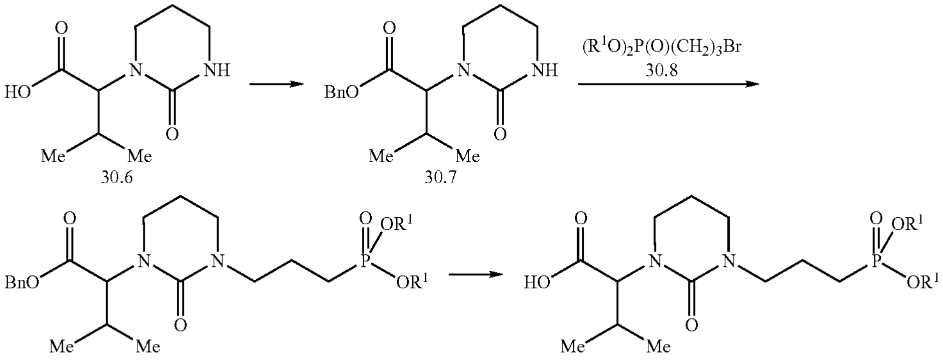
30.6 30.7 30.9 30.10
Scheme 31
Method
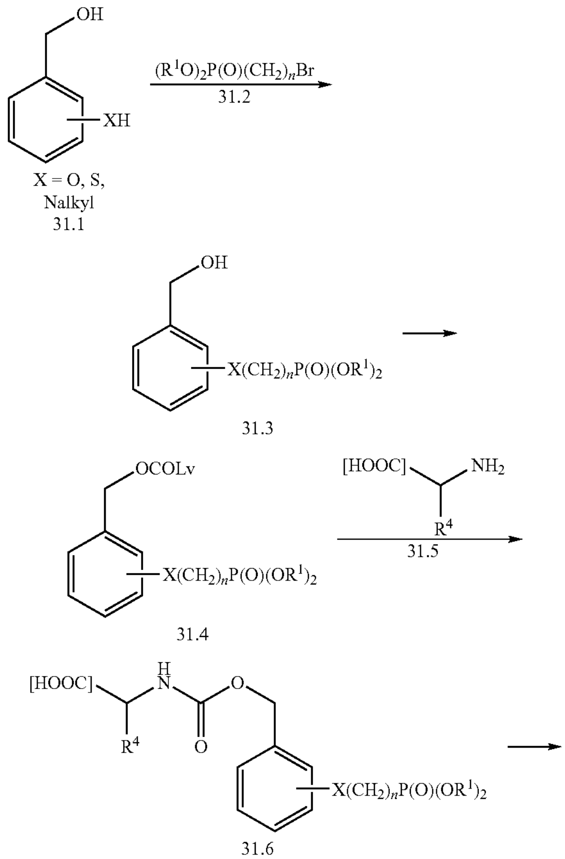
31.1 31.3 31.4 31.6
-continued
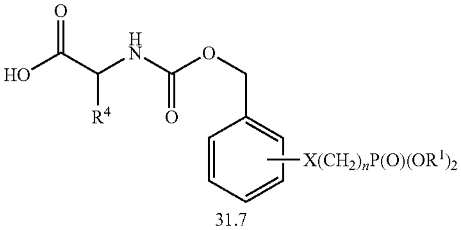
31.7
Example
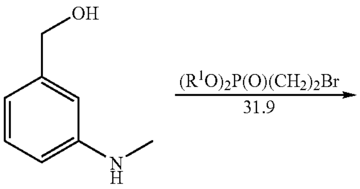
31.8

-continued
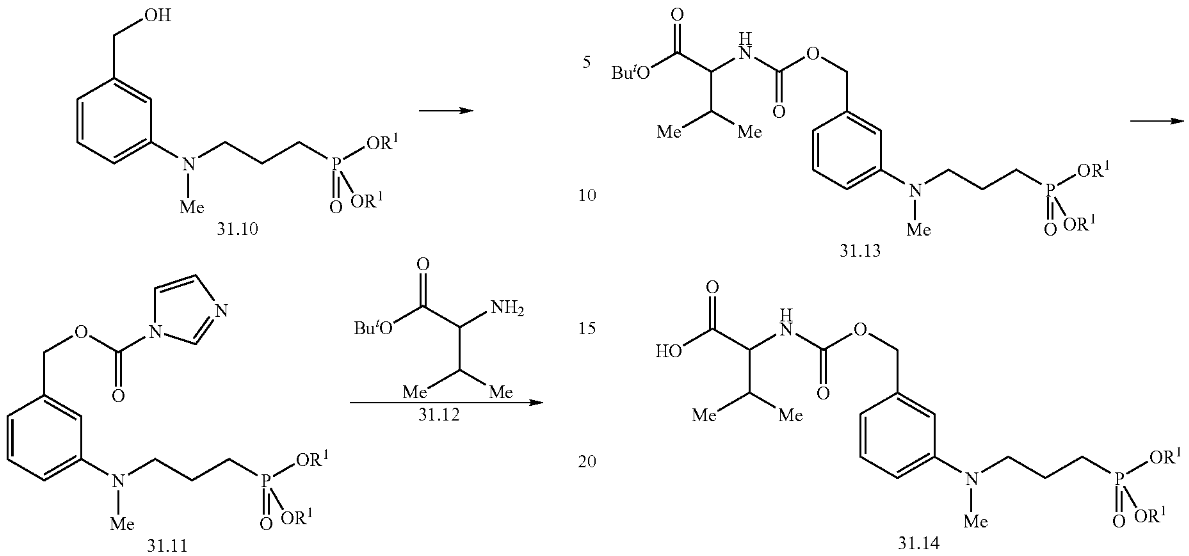
31.10 31.13 31.11 31.12 31.14
Scheme 32
Method
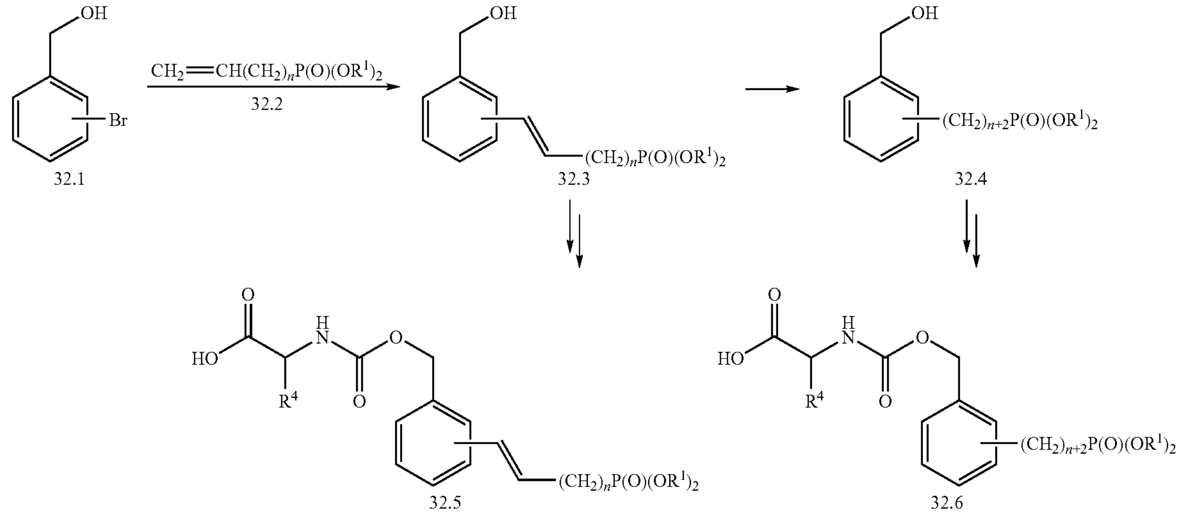
32.1 32.3 32.4 32.5 32.6
Example
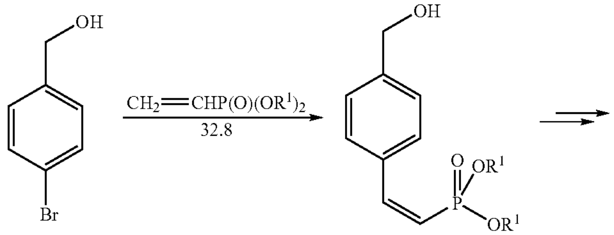
32.7 32.9

-continued
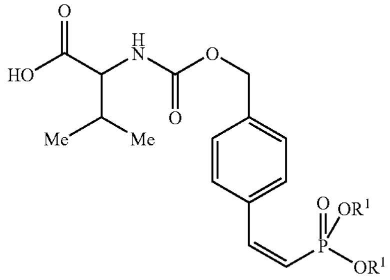
32.10
and
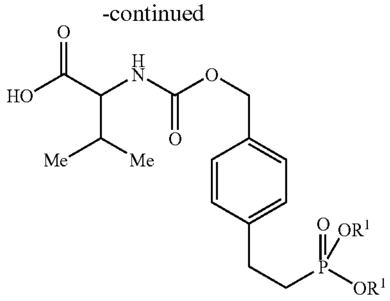
32.11
Scheme 33
Method
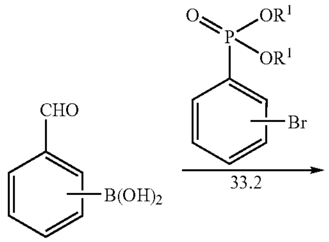
33.2
33.1
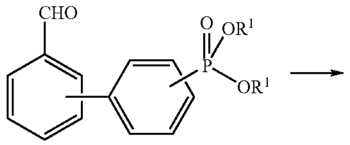
33.3
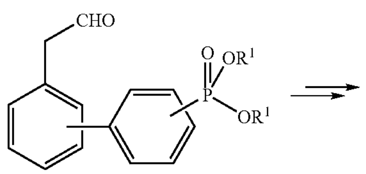
33.4
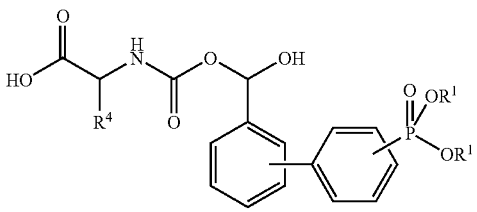
33.5
-continued
Example
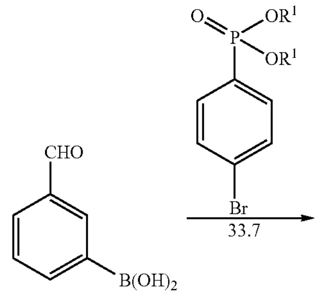
33.7
33.6
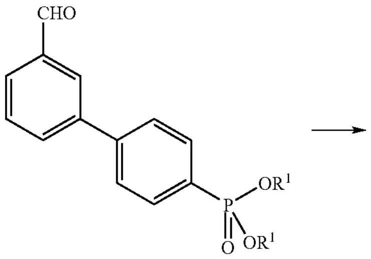
33.8
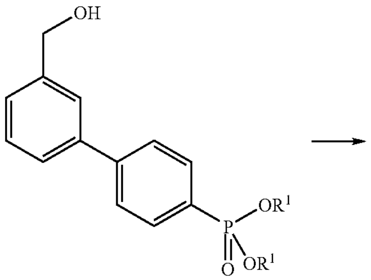
33.9
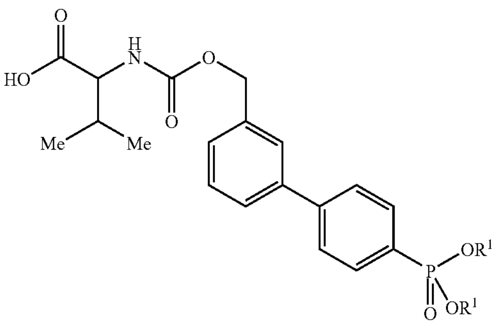
33.10

General Applicability of Methods for Introduction of Phosphonate Substituents.

The methods described herein for the preparation of phosphonate ester intermediate compounds are, with appropriate modifications, generally applicable to different substrates, such as the carboxylic acids depicted in Charts 2a, 2b and 2c. Thus, the methods described above for the introduction of phosphonate groups into the dimethylphenoxyacetic acid moiety (Schemes 9-14), can, with appropriate modifications known to those skilled in the art, be applied to the introduction of phosphonate groups into the phenylalanine synthon for the preparation of the phosphonate esters 3. Similarly, the methods described above for the introduction of phosphonate groups into the phenylalanine moiety (Schemes 15-17), the hydroxy methyl substituted benzoic acids (Schemes 23-27), the tetrahydropyrimidine analogs (Schemes 28-30), and the benzyl carbamates (Schemes 31-33) can, with appropriate modifications known to those skilled in the art, be applied to the introduction of phosphonate groups into the dimethylphenoxyacetic acid component.

Atazanavir-like Phosphonate Protease Inhibitors (ATLPPI)

Preparation of the Intermediate Phosphonate Esters.

The structures of the intermediate phosphonate esters 1 to 7, and the structures for the component groups X, $R^1$, $R^7$ and $R^8$ of this invention are shown in Chart 1. The structures of the $R^2COOH$ and $R^5COOH$ components are shown in Charts 2a, 2b and 2c, and the structures of the $R^3XCH_2$ components are shown in Chart 3. The structures of the $R^4$ components are shown in Chart 4. Specific stereoisomers of some of the structures are shown in Charts 1-4; however, all stereoisomers are utilized in the syntheses of the compounds 1 to 7. Subsequent chemical modifications to the compounds 1 to 7, as described herein, permit the synthesis of the final compounds of this invention.

The intermediate compounds 1 to 7 incorporate a phosphonate moiety $(R^1O)_2P(O)$ connected to the nucleus by means of a variable linking group, designated as "link" in the attached structures. Charts 5 and 6 illustrate examples of the linking groups present in the structures 1-7. The term "etc" in Charts 3, 5 and 6, refers to the scaffold atazanavir.

Schemes 1-56 illustrate the synthses of the intermediate phosphonate compounds of this invention, 1-5, and of the intermediate compounds necessary for their synthesis. The preparation of the phosphonate esters 6 and 7, in which the phosphonate moiety is incorporated into the groups $R^2COOH$ and $R^5COOH$, are also described below.

CHART 1

Structures of the phosphonate esters 1-7.

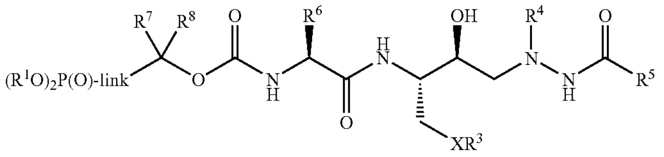

1

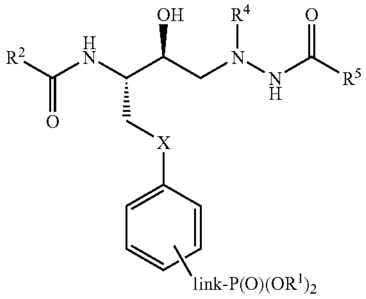

2

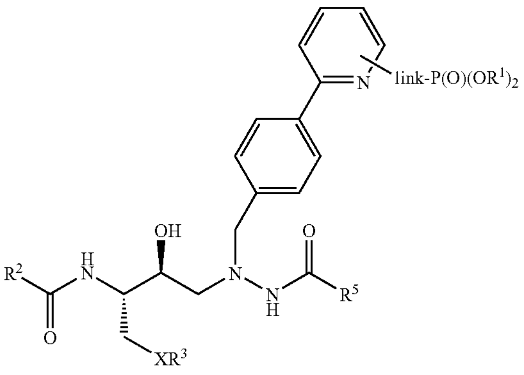

3a

CHART 1-continued
Structures of the phosphonate esters 1-7.
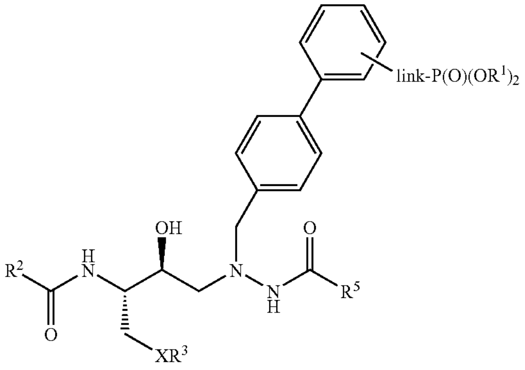
3b
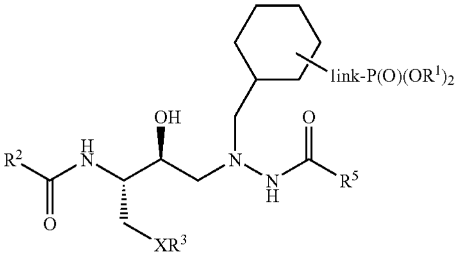
3c
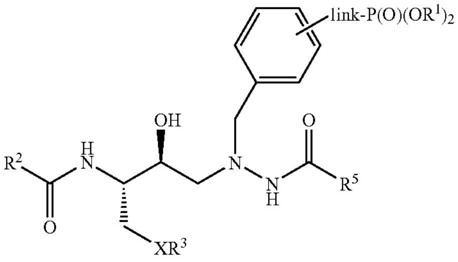
3d
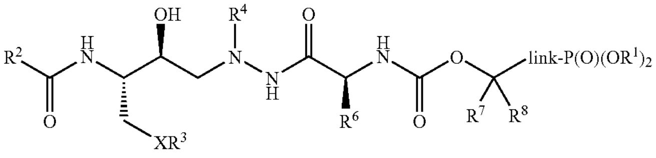
4
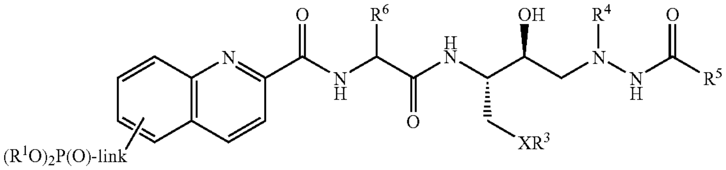
5

CHART 1-continued

Structures of the phosphonate esters 1-7.

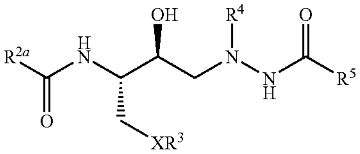
6

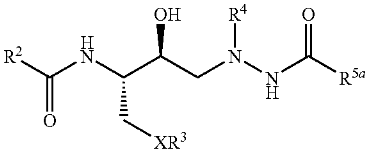
7

$R^{2a}$ = phosphonate-containing $R^2$
$R^1$ = H, alkyl, haloalkyl, alkenyl, aralkyl, aryl
$R^{5a}$ = phosphonate-containing $R^5$
$R^7$, $R^8$ = H, alkyl
X = direct bond; sulfur.

CHART 2a

Structures of the $R^2COOH$ and $R^5COOH$ components

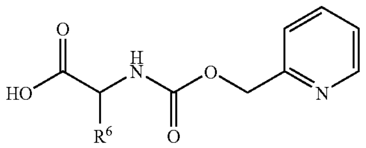
C1

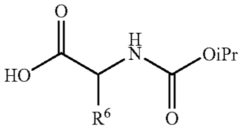
C2

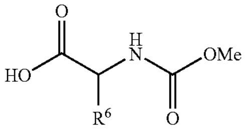
C3

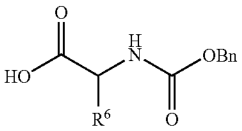
C4

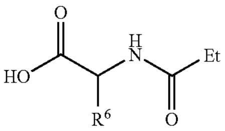
C5

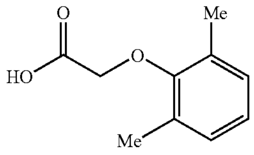
C6

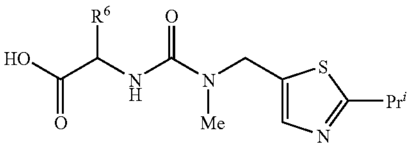
C7

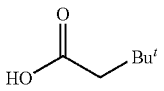
C8

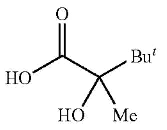
C9

CHART 2a-continued

Structures of the $R^2COOH$ and $R^5COOH$ components

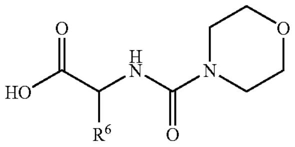
C10

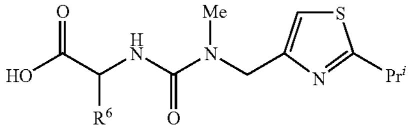
C11

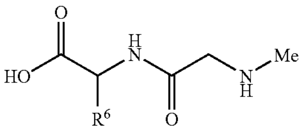
C12

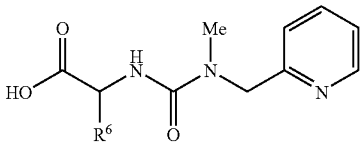
C13

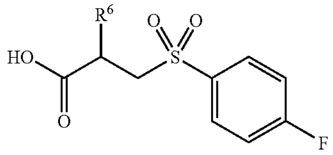
C14

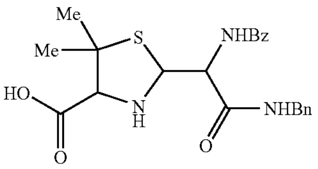
C15

CHART 2a-continued
Structures of the $R^2COOH$ and $R^5COOH$ components
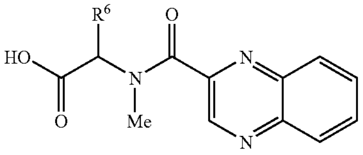
C16
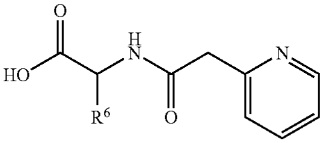
C17
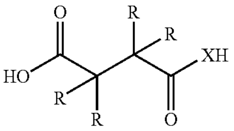
X = O, NH
R = H, alkyl
C18
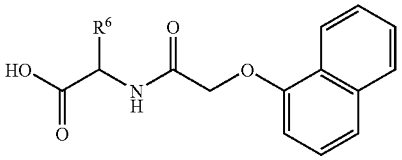
C19
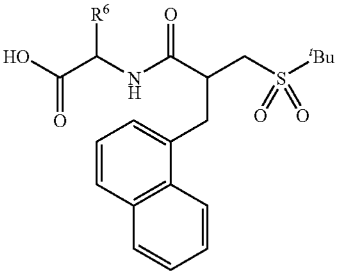
C20
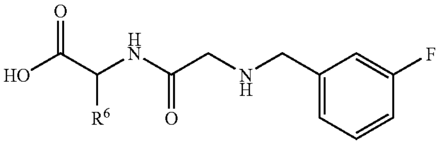
C21
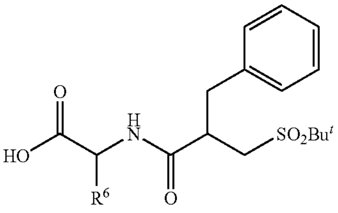
C22
CHART 2a-continued
Structures of the $R^2COOH$ and $R^5COOH$ components
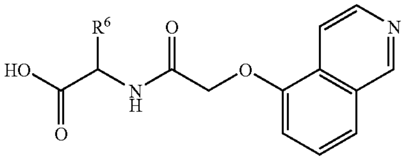
C23
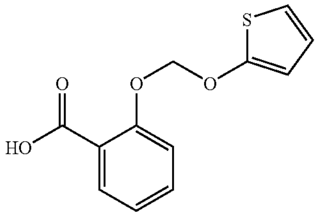
C24
$R^6$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
CHART 2b
Structures of the $R^2COOH$ and $R^5COOH$ components
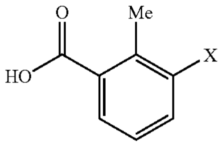
C25
X = OH, $NH_2$
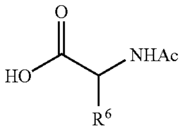
C26
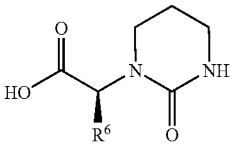
C27
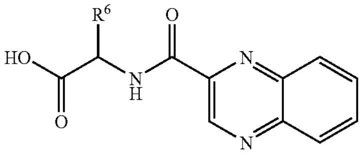
C28
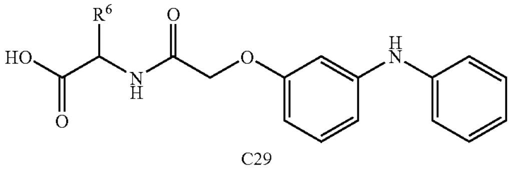
C29
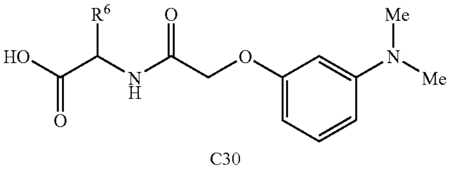
C30

CHART 2b-continued
Structures of the $R^2COOH$ and $R^5COOH$ components
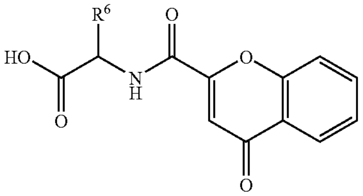
C31
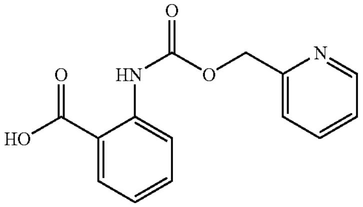
C32
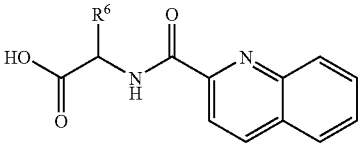
C33
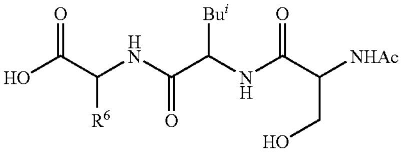
C34
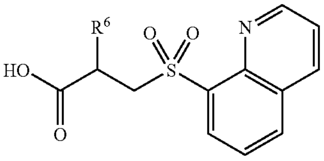
C35
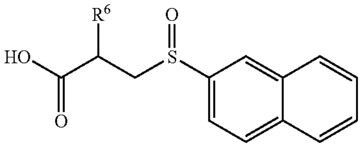
C36
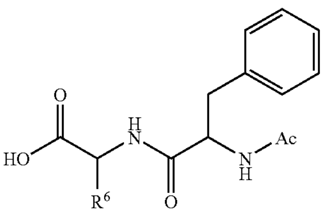
C37
$R^6$ = alkyl, $CH_2SO_2CH_3$, $C(CH_3)_2SO_2CH_3$, $CH_2CONH_2$, $CH_2SCH_3$, imidaz-4-ylmethyl, NHAc, $NHCOCF_3$
CHART 2c
Structures of the $R^2COOH$ and $R^5COOH$ components
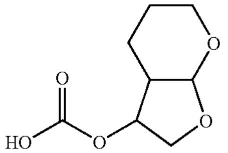
C38
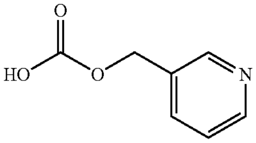
C39
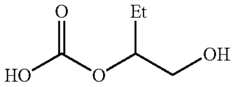
C40
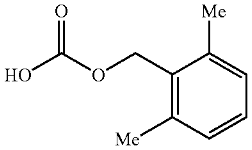
C41
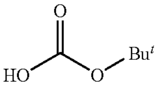
C42
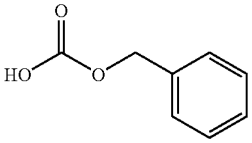
C43
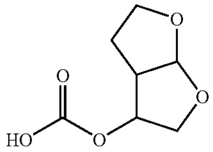
C44
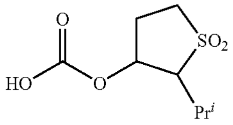
C45
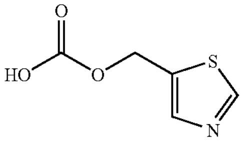
C46
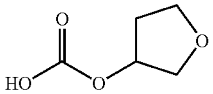
C47
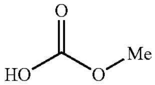
C48
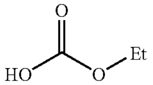
C49
CHART 3
Structures of the $R^3XCH_2$ groups.
$R^3XCH_2$ =
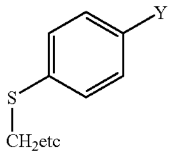
8
Y = H, F
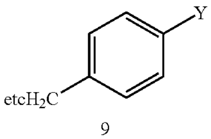
9
Y = H, $OC_2H_5$, $OCH_2C_6H_5$ CHART 3-continued Structures of the $R^3XCH_2$ groups.

$R^3XCH_2$ =

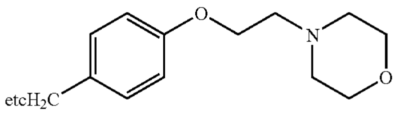

10

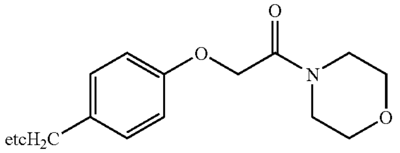

11

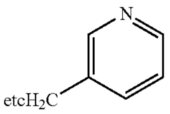

12

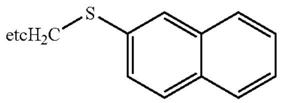

13

CHART 4

Structures of the $R^4$ groups $R^4$ = alkyl, $(CH_2)_n$aryl, $(CH_2)_n$cycloalkyl,

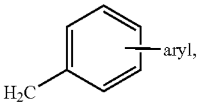

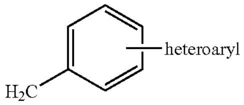

CHART 5

Examples of the linking group between the scaffold and the phosphonate moiety.

| link | examples | |
|---|---|---|
| direct bond | 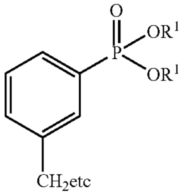 15 | 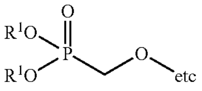 16 |

CHART 5-continued

Examples of the linking group between the scaffold and the phosphonate moiety.

| link | examples | |
|---|---|---|
| | 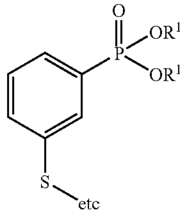 17 | 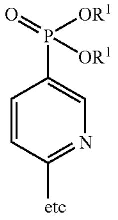 18 |
| single carbon | 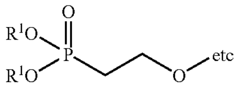 19 | |
| | 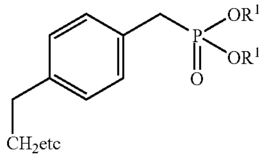 20 | |
| | 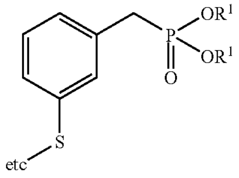 21 | |
| | 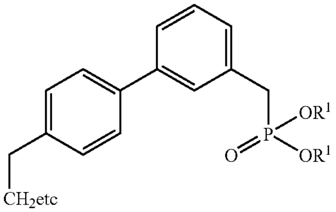 22 | |
| multiple carbon | 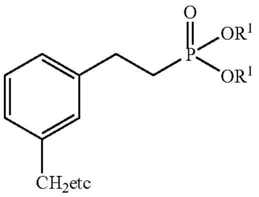 22 | |
| | 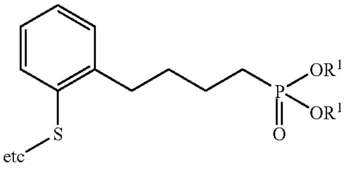 23 | |

CHART 5-continued
| Examples of the linking group between the scaffold and the phosphonate moiety. | |
|---|---|
| link | examples |
| | 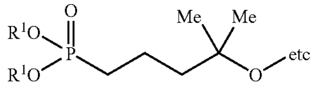 24 |
| | 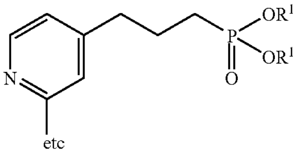 25 |
| hetero atoms | 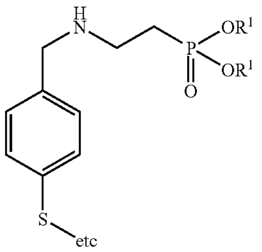 26 |
| | 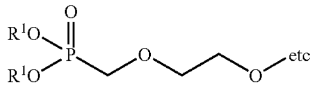 27 |
| | 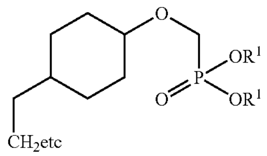 28 |
| | 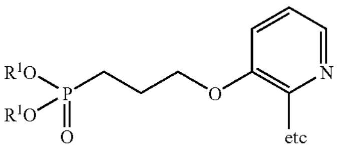 29 |
| | 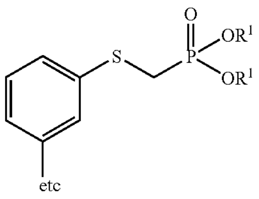 30 |
CHART 5-continued
| Examples of the linking group between the scaffold and the phosphonate moiety. | |
|---|---|
| link | examples |
| | 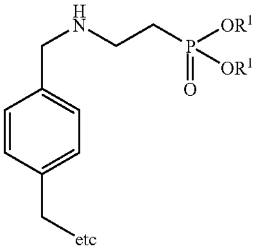 31 |
| | 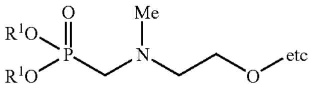 32 |
| | 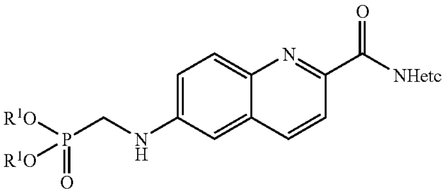 33 |
CHART 6
| Examples of the linking group between the scaffold and the phosphonate moiety. | |
|---|---|
| link | examples |
| aryl, heteroaryl | 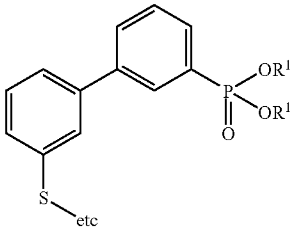 34 |
| | 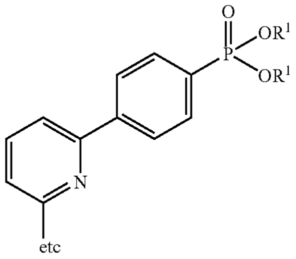 35 |

CHART 6-continued

Examples of the linking group between the scaffold and the phosphonate moiety.

| link | examples |
| --- | --- |
| | 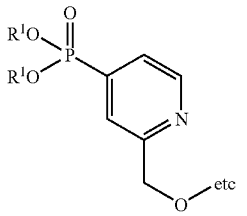 36 |
| | 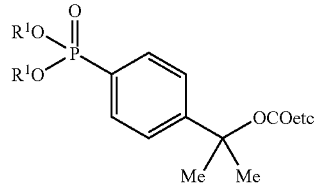 37 |
| cycloalkyl | 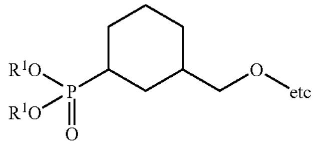 38 |
| | 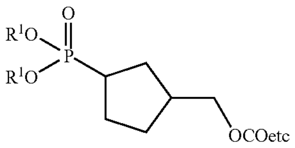 39 |
| | 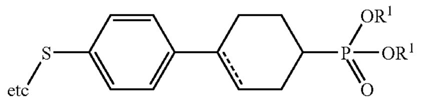 40 |
| cyclized | 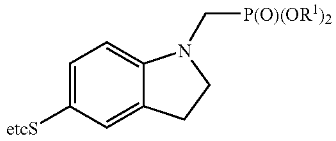 41 |
| | 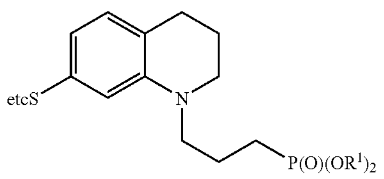 42 |
| amide | 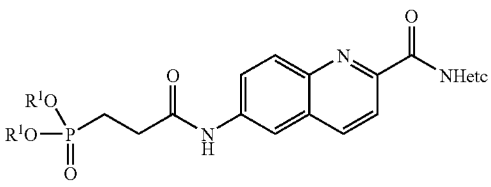 |

CHART 6-continued

Examples of the linking group between the scaffold and the phosphonate moiety.

| link | examples |
| --- | --- |
| | 43 |
| | 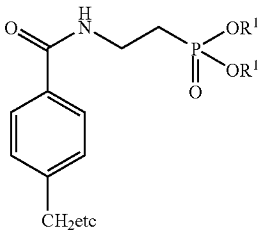 44 |

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990. Reactive substituents which may be protected are shown in the accompanying schemes as, for example, [OH], [SH].

Preparation of the Phosphonate Ester Intermediates 1 in which X is a Direct Bond.

Schemes 1 and 2 illustrate the preparation of the phosphonate esters 1 in which X is a direct bond. As shown in Scheme 1, the oxirane 1.1 is reacted with the BOC-protected hydrazine derivative 1.2 to afford the aminoalcohol 1.3. The preparation of the oxiranes 1.1, in which Y is as defined in Scheme 1, is described below, (Scheme 3). The preparation of the hydrazine derivatives $R^4NHNHBOC$ is described below, (Scheme 4). The reaction between the oxirane 1.1 and the hydrazine 1.2 is conducted in a polar organic solvent such as dimethylformamide, acetonitrile or, preferably, a lower alkanol. For example, equimolar amounts of the reactants are combined in isopropanol and heated to ca. 80° for about 16 hours, as described in WO 9740029, to afford the aminoalcohol 1.3. The cbz protecting group is then removed from the product to yield the free amine 1.4. The removal of carbobenzyloxy substituents to afford the corresponding amines is described in Protective Groups in Organic Synthesis, by T. W. Greene and P. G. M Wuts, Wiley, Second Edition 1990, p. 335. The conversion can be effected by the use of catalytic hydrogenation, in the presence of hydrogen or a hydrogen donor and a palladium catalyst. Alternatively, the cbz group can be removed by treatment of the substrate with triethylsilane, triethylamine and a catalytic amount of palladium (II) chloride, as described in Chem. Ber., 94, 821, 1961, or by the use of trimethylsilyl iodide in acetonitrile at ambient temperature, as described in J. Chem. Soc., Perkin Trans. I, 1277, 1988. The cbz group can also be removed by treatment with a Lewis acid such as boron tribromide, as described in J. Org. Chem., 39, 1247, 1974, or aluminum chloride, as described in Tet. Lett., 2793, 1979.

Preferably, the protected amine 1.3 is converted into the free amine 1.4 by means of hydrogenation over 10% palladium on carbon catalyst in ethanol, as described in U.S. Pat. No. 5,196,438.

The amine product 1.4 is then reacted with a carboxylic acid 1.5 to afford the amide 1.6. The preparation of amides from carboxylic acids and derivatives is described, for example, in Organic Functional Group Preparations, by S. R. Sandler and W. Karo, Academic Press, 1968, p. 274, and in Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane. Preferably, equimolar amounts of the amine and the carboxylic acid are reacted in tetrahydrofuran at ca. −10°, in the presence of dicyclohexylcarbodiimide, as described in U.S. Pat. No. 5,196,438, to afford the aminoamide 1.6. The aminoamide is then reacted with a reagent A-$CR^7R^8OCOX$ (1.7), in which the substituent A is the group $(R^1O)_2P(O)$-link, or a precursor group thereto, such as [OH], [SH], [NH], Br, as described below, and in which the substituent X is a leaving group, to yield the carbamate 1.8. The reagent A-$CR^7R^8OCOX$ is derived from the corresponding alcohol A-$CR^7R^8OH$, using methods described below, (Scheme 20). The preparation of the reactants A-$CR^7R^8OCOX$ is described in Schemes 21-26. The preparation of carbamates by means of reactions between alcohols and amines is described in Scheme 20.

The BOC-protected amine present in the carbamate product 1.8 is then deprotected to produce the free amine 1.9. The removal of BOC protecting groups is described, for example, in Protective Groups in Organic Synthesis, by T. W. Greene and P. G. M Wuts, Wiley, Second Edition 1990, p. 328. The deprotection can be effected by treatment of the BOC compound with anhydrous acids, for example, hydrogen chloride or trifluoroacetic acid or formic acid, or by reaction with trimethylsilyl iodide or aluminum chloride. Preferably, the BOC group is removed by treatment of the substrate 1.8 with hydrogen chloride in tetrahydrofuran, for example as described in Org. Process Res. Dev., 2002, 6, 323. The resulting amine 1.9 is then coupled with a carboxylic acid or an activated derivative thereof 1.10, to afford the amide 1.11, using the conditions described above for the preparation of the amide 1.6.

For example, the amine 1.9 is reacted with the carboxylic acid 1.10, X═OH, in the presence of a water-soluble carbodiimide such as 1-(3-dimethylaminopropyl)-3-ethylcarbodiimide, hydroxybenztriazole and triethylamine, as described in J. Med. Chem., 41, 1988, 3387, to yield the amide 1.11.

The procedures illustrated in Scheme 1 depict the preparation of the compounds 1.11 in which the substituent A is either the group link-$P(O)(OR^1)_2$ or a precursor thereto, such as [OH], [SH], Br, as described below. Scheme 2 illustrates the conversion of compounds 1.11 in which A is a precursor to the group link-$P(O)(OR^1)_2$ into the compounds 1. Procedures for the conversion of the substituent A into the group link-$P(O)(OR^1)_2$ are illustrated below, (Schemes 21-56). In the procedures illustrated above, (Scheme 1) and in the procedures illustrated below (Schemes 3-19) for the preparation of the phosphonate esters 1-7, compounds in which the group A is a precursor to the group link-$P(O)(OR^1)_2$ may be converted into compounds in which A is link-$P(O)(OR^1)_2$ at any appropriate stage in the reaction sequence, or, as shown in Scheme 2, at the end of the sequence. The selection of an appropriate stage to effect the conversion of the group A into the group link-$P(O)(OR^1)_2$ is made after consideration of the nature of the reactions involved in the conversion, and the stability of the various components of the substrate to those reaction conditions.

Scheme 3 illustrates the preparation of the epoxides 1.1 used above in Scheme 1. The preparation of the epoxide 1.1 in which $R^7$ is H is described in J. Org. Chem., 1994, 59, 3656. Analogs in which $R^7$ is one of the substituents defined in Chart 3 are prepared as shown in Scheme 3. A substituted phenylalanine 3.1 is first converted into the benzyloxycarbonyl (cbz) derivative 3.2. The preparation of benzyloxycarbonyl amines is described in Protective Groups in Organic Synthesis, by T. W. Greene and P. G. M Wuts, Wiley, Second Edition 1990, p. 335. The aminoacid 3.1 is reacted with benzyl chloroformate or dibenzyl carbonate in the presence of a suitable base such as sodium carbonate or triethylamine, to afford the protected amine product 3.2. The conversion of the carboxylic acid 3.2 into the epoxide 1.1, for example using the sequence of reactions which is described in J. Med. Chem., 1994, 37, 1758, and in J. Org. Chem., 1994, 59, 3656 is then effected. The carboxylic acid is first converted into an activated derivative such as the acid chloride 3.3, in which X is Cl, for example by treatment with oxalyl chloride, or into a mixed anhydride, for example by treatment with isobutyl chloroformate, and the activated derivative thus obtained is reacted with ethereal diazomethane, to afford the diazoketone 3.4. The reaction is performed by the addition of a solution of the activated carboxylic acid derivative to an ethereal solution of three or more molar equivalents of diazomethane at 0°. The diazoketone 3.4 is converted into the chloroketone 3.5 by reaction with anhydrous hydrogen chloride, in a suitable solvent such as diethyl ether, as described in J. Org. Chem., 1994, 59, 3656. The latter compound is then reduced, for example by the use of an equimolar amount of sodium borohydride in an ethereal solvent such as tetrahydrofuran at 0°, to produce a mixture of chlorohydrins from which the minor diastereomer 3.6 is separated by chromatography. The chlorohydrin 3.6 is then converted into the epoxide 1.1 by treatment with a base such as an alkali metal hydroxide in an alcoholic solvent, for example as described in J. Med. Chem., 1997, 40, 3979. Preferably, the compound 3.6 is reacted with ethanolic potassium hydroxide at ambient temperature to afford the epoxide 1.1. The preparations of analogs of the oxirane 1.1 in which the amino group is protected respectively as the tert-butoxycarbonyl and trifluoroacetyl derivatives are described respectively in J. Med. Chem., 1994, 37, 1758 and J. Med. Chem., 1996, 39, 3203.

Scheme 4 depicts the preparation of the hydrazine derivatives 1.2, in which $R^4$ is $CH_2$-aryl, $CH_2$-alkyl, $CH_2$-cycloalkyl as shown in Chart 4. The general procedure for the preparation of BOC-protected hydrazine derivatives from the corresponding aldehyde RCHO (4.1) is shown in Scheme 4. The aldehyde is reacted with tert. butyl carbazate 4.2, in a solvent such as an alkanol, a hydrocarbon such as toluene, or a polar organic solvent such as dimethylformamide, to afford the substituted hydrazone 4.3. Preferably, equimolar amounts of the reactants are heated in a mixture of toluene and isopropanol, as described in Org. Process Res. Dev., 2002, 6, 323, to prepare the hydrazone 4.3. The product is then reduced to the corresponding hydrazine derivative 4.4. The transformation can be effected by chemical reduction, for example by the use of sodium borohydride, sodium cyanoborohydride, or sodium triacetoxyborohydride or the like, or by palladium-catalyzed reduction in the presence of hydrogen or a hydrogen donor such as ammonium formate. Preferably, the hydrazone 4.3 is reduced to the hydrazine 4.4 by hydrogenation at ambient temperature and pressure, in the presence of palladium hydroxide on carbon, as described in Org. Process Res. Dev., 2002, 6, 323.

The preparation of the hydrazine derivatives 1.2 in which a diaryl moiety is present is shown in Scheme 4, Example 1. In this procedure, a formyl-substituted phenyl boronate 4.5 (Lancaster Synthesis) is transformed, by means of a palladium-catalyzed coupling with an aryl or heteroaryl bromide 4.6, to afford the aldehyde 4.7. The coupling of aryl bromides with aryl boronates is described, for example, in Palladium Reagents and Catalysts, by J. Tsuji, Wiley 1995, p. 218 and in Comprehensive Organic Transformations, by R. C. Larock, VCH, 1989, p 57. Typically, the reactants 4.5 and 4.6 are combined in an aprotic organic solvent such as dimethylformamide in the presence of a palladium (0) catalyst such as tetrakis(triphenylphosphine)palladium and a base such as sodium bicarbonate or potassium acetate, to afford the coupled product 4.7. This material is then reacted with a protected hydrazine derivative such as tert-butoxycarbonylhydrazine (tert-butyl carbazate) 4.2, to yield the hydrazone 4.8. The reaction between equimolar amounts of the aldehyde and the protected hydrazine is conducted in alcoholic solvent such as ethanol, at reflux temperature, for example as described in WO9740029, to produce the hydrazone 4.8. The latter compound is then reduced, for example by the use of hydrogen in the presence of a palladium catalyst, as described in WO 9740029, or by the use of sodium cyanoborohydride and p-toluenesulfonic acid in tetrahydrofuran, as described in J. Med. Chem., 1998, 41, 3387, to afford the substituted hydrazine 1.2. Other reactants 1.2, in which $R^4$ is as defined in Chart 4, are prepared from the appropriate aldehydes, using the procedures of Scheme 4.

Scheme 4, Example 2 illustrates the preparation of phosphonate-containing pyridylphenyl hydrazine derivatives 4.11, which are employed in the preparation of the phosphonate esters 3a. In this procedure, a phosphonate-substituted pyridyl benzaldehyde 4.9, the preparation of which is described below, (Schemes 40 and 41) is reacted, as described above, with tert. butyl carbazate 4.2, to afford the hydrazone 4.10. This compound is then reduced, in the presence of palladium hydroxide as catalyst, as described above, to yield the hydrazine product 4.11.

Scheme 4, Example 3 illustrates the preparation of phosphonate-containing biphenyl hydrazine derivatives 4.13, which are employed in the preparation of the phosphonate esters 3b. In this procedure, a phosphonate-substituted phenyl benzaldehyde 4.12 the preparation of which is described below, (Schemes 42-44) is converted, as described above in Example 2 into hydrazine product 4.13.

Scheme 4, Example 4 illustrates the preparation of phosphonate-containing phenyl hydrazine derivatives 4.15, which are employed in the preparation of the phosphonate esters 3d. In this procedure, a phosphonate-substituted phenyl benzaldehyde 4.14, the preparation of which is described below, (Schemes 45-48) is converted, as described above in Example 2 into hydrazine product 4.15.

Scheme 4, Example 5 illustrates the preparation of phosphonate-containing cyclohexyl hydrazine derivatives 4.17, which are employed in the preparation of the phosphonate esters 3c. In this procedure, a phosphonate-substituted cyclohexane carboxaldehyde 4.16, the preparation of which is described below, (Schemes 49-52) is converted, as described above in Example 2 into hydrazine product 4.17.

Scheme 1

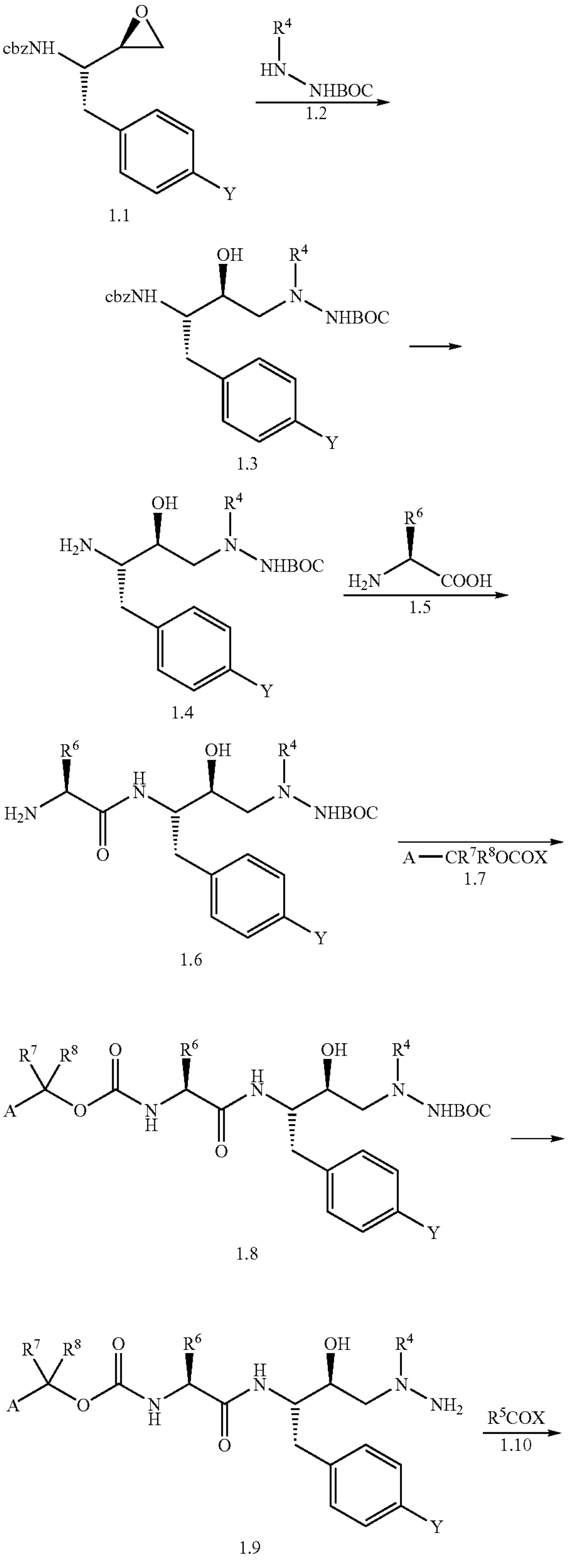

-continued
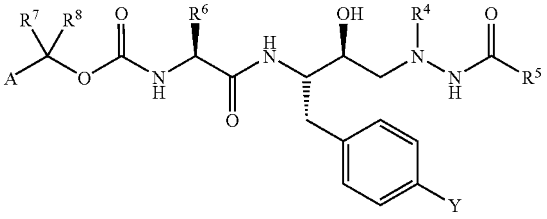
1.11
Y = H, $OC_2H_5$, $OCH_2C_6H_5$, $O(CH_2)_2$morpholino, $OCH_2CO$morpholino
Scheme 2
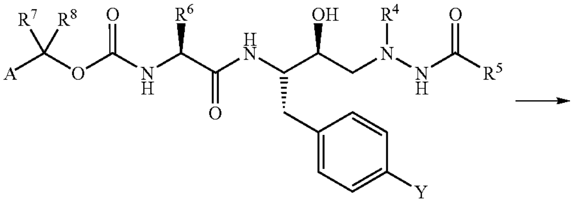
1.11
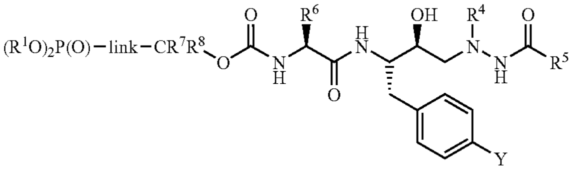
1
Scheme 3
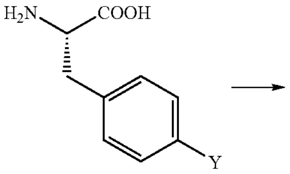
3.1
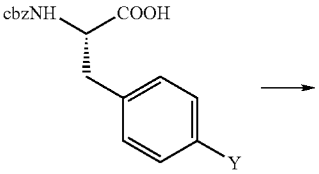
3.2
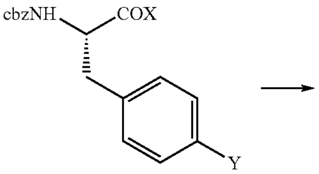
3.3
-continued
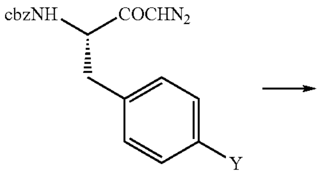
3.4
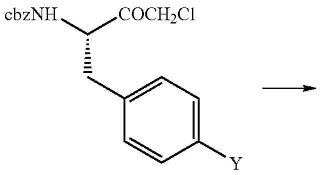
3.6
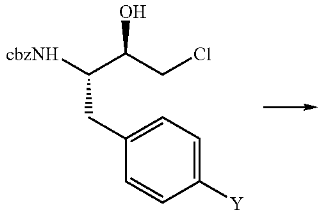
3.6
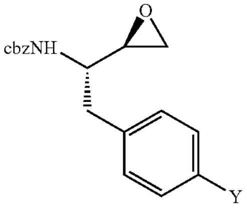
1.1
Scheme 4
General reaction
$RCHO$ 4.1
$BOCNHNH_2$ 4.2
$RCH{=}NNHBOC$ 4.3
$RCH_2NHNHBOC$ 4.4
Example 1
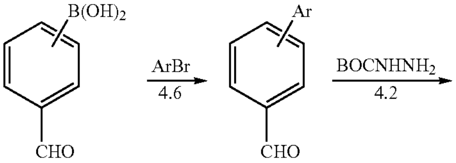
4.5 4.7
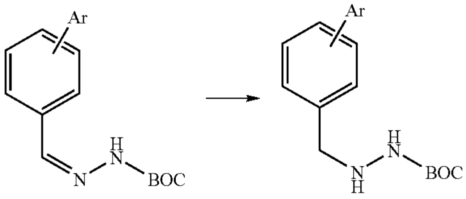
4.8 1.2
Example 2
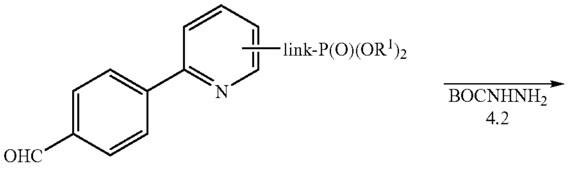
4.9

-continued

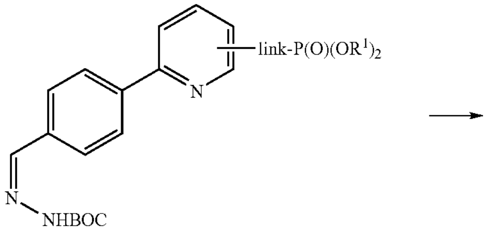

4.10

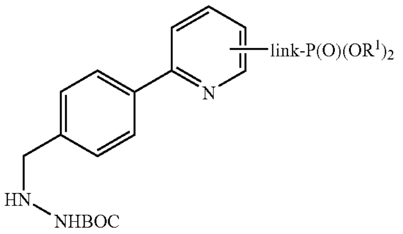

4.11

Example 3

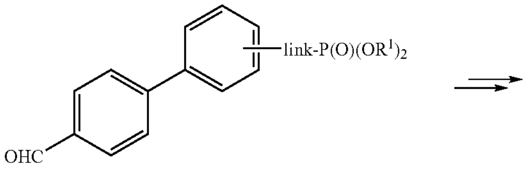

4.12

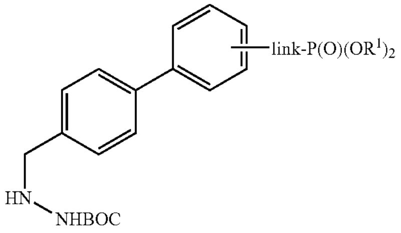

4.13

Example 4

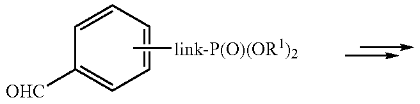

4.14

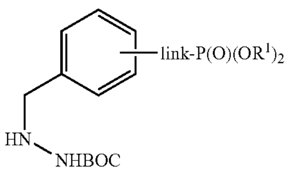

4.15

Example 5

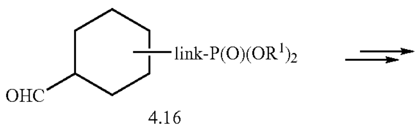

4.16

-continued

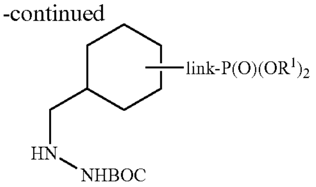

4.17

Preparation of the Phosphonate Ester Intermediates 1 in which X is Sulfur.

Schemes 5 and 6 illustrate the preparation of the compounds 1 in which X is sulfur. In this sequence, methanesulfonic acid 2-benzoyloxycarbonylamino-2-(2,2-dimethyl-[1,3]dioxolan-4-yl)-ethyl ester, 5.1, prepared as described in J. Org. Chem, 2000, 65, 1623, is reacted with a thiol $R^3SH$ 5.2, as defined above, to afford the thioether 5.3.

The reaction is conducted in an organic solvent such as, for example, pyridine, DMF, toluene and the like, optionally in the presence of water, in the presence of an inorganic or organic base, at from 0° to 80°, for from 1-12 hours. Preferably the mesylate 5.1 is reacted with an equimolar amount of the thiol $R^3SH$ 5.2, in a mixture of a water-immiscible organic solvent such as toluene, and water, in the presence of a phase-transfer catalyst such as, for example, tetrabutyl ammonium bromide, and an inorganic base such as sodium hydroxide, at about 50°, as described in J. Org. Chem., 1994, 59, 3656, to give the product 5.3. The 1,3-dioxolane protecting group present in the compound 5.3 is then removed by acid catalyzed hydrolysis or by exchange with a reactive carbonyl compound to afford the diol 5.4. Methods for conversion of 1,3-dioxolanes to the corresponding diols are described in Protective Groups in Organic Synthesis, by T. W. Greene and P. G. M Wuts, Second Edition 1990, p191. For example, the 1,3-dioxolane compound 5.3 is hydrolyzed by reaction with a catalytic amount of an acid in an aqueous organic solvent mixture. Preferably, the 1,3-dioxolane 5.3 is dissolved in aqueous methanol containing hydrochloric acid, and heated at ca. 50°, to yield the diol product 5.4.

The primary hydroxyl group of the diol 5.4 is then selectively activated by reaction with an electron-withdrawing reagent such as, for example, dinitrobenzoyl chloride or p-toluenesulfonyl chloride. The reaction is conducted in an inert solvent such as pyridine, dichloromethane and the like, in the presence of an inorganic or organic base.

Preferably, equimolar amounts of the diol 5.4 and p-toluenesufonyl chloride are reacted in a solvent such as pyridine, in the presence of a tertiary organic base such as 2-picoline, at ambient temperature, as described in J. Org. Chem, 2000, 65, 1623, to afford the p-toluenesulfonate ester 5.5.

The latter compound is then reacted with the hydrazine derivative 1.2 to afford the hydrazine 5.6. The displacement reaction is conducted in a polar aprotic solvent such as dimethylformamide, acetonitrile, dioxan and the like, in the presence of an organic or inorganic base, to afford the product 5.6. Preferably, equimolar amounts of the reactants are combined in dimethylformamide at ca. 80° in the presence of potassium carbonate, to produce the hydrazine product 5.6. The cbz protecting group is then removed to afford the amine 5.7. The removal of carbobenzyloxy substituents to afford the corresponding amines is described in Protective Groups in Organic Synthesis, by T. W. Greene and P. G. M Wuts, Wiley, Second Edition 1990, p. 335. The conversion can be effected by the use of catalytic hydrogenation, in the presence of hydrogen or a hydrogen donor and a palladium catalyst. Alternatively, the cbz group can be removed by treatment of the substrate with triethylsilane, triethylamine and a catalytic amount of palladium (II) chloride, as described in Chem. Ber., 94, 821, 1961, or by the use of trimethylsilyl iodide in acetonitrile at ambient temperature, as described in J. Chem. Soc., Perkin Trans. 1,1277, 1988. The cbz group can also be removed by treatment with Lewis acid such as boron tribromide, as described in J. Org. Chem., 39, 1247, 1974, or aluminum chloride, as described in Tet. Lett., 2793, 1979. Preferably, the cbz protecting group is removed by hydrogenation of the substrate 5.6 in the presence of 5% palladium on carbon catalyst, to yield the amine 5.7. The amine is then coupled with the aminoacid 5.8 to give the amine 5.9. The reaction is effected under the same conditions as described above for the preparation of the amide 1.6.

The amine is then reacted with a reagent A-$CR^7R^8OCOX$ (1.7), in which the substituent A is the group $(R^1O)_2P(O)$-link, or a precursor group thereto, such as [OH], [SH], [NH], Br, as described below, and in which the substituent X is a leaving group, to yield the carbamate 5.10. The reagent A-$CR^7R^8OCOX$ is derived from the corresponding alcohol A-$CR^7R^8OH$, using methods described below, (Scheme 20). The preparation of the reactants A-$CR^7R^8OCOX$ is described in Schemes 21-26. The preparation of carbamates by means of reactions between alcohols and amines is described below, in Scheme 20.

The BOC protecting group is then removed from the product 5.10 to produce the hydrazine 5.11. The conditions for the removal of the BOC group are the same as those described above (Scheme 1). The product is then acylated with the carboxylic acid or activated derivative thereof, 1.10, using the conditions described above, (Scheme 1) to yield the product 5.12.

The procedures illustrated in Scheme 5 depict the preparation of the compounds 5.11 in which the substituent A is either the group link-$P(O)(OR^1)_2$ or a precursor thereto, such as [OH], [SH] Br, as described below. Scheme 6 illustrates the conversion of compounds 5.12 in which A is a precursor to the group link-$P(O)(OR^1)_2$ into the compounds 1. Procedures for the conversion of the substituent A into the group link-P(O)$(OR^1)_2$ are illustrated below, (Schemes 21-56).

Scheme 5

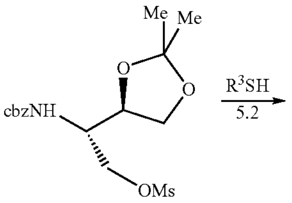

5.1

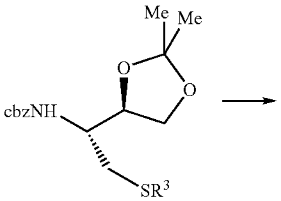

5.3

-continued

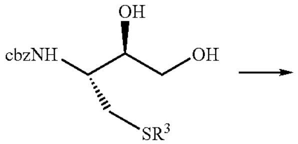

5.4

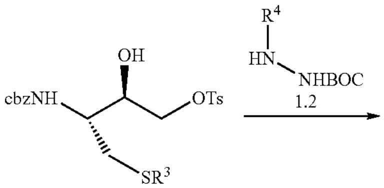

5.5

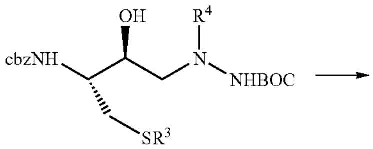

5.6

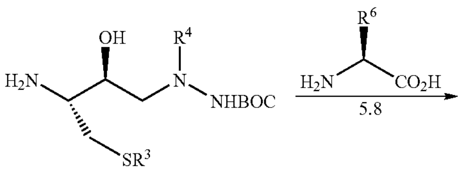

5.7

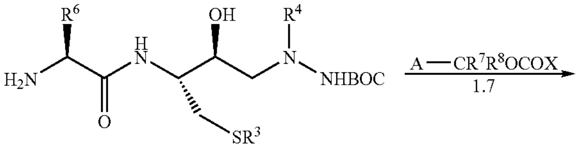

5.9

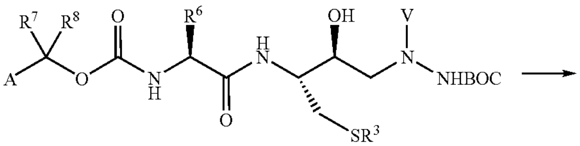

5.10

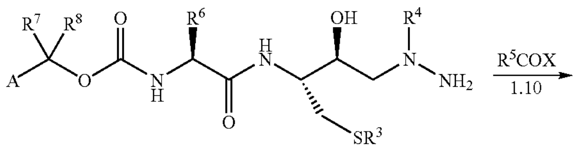

5.11

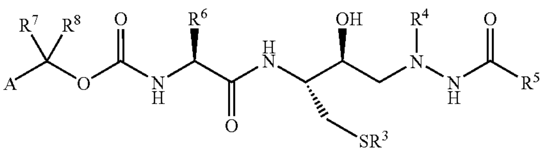

5.12

Scheme 6

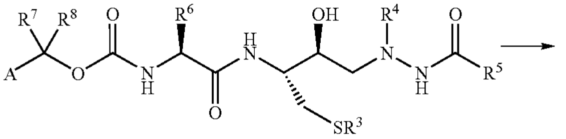

5.12

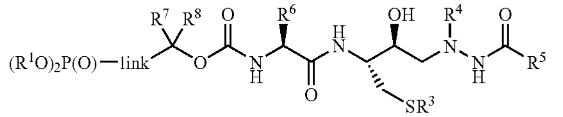

1

Preparation of the Phosphonate Ester Intermediates 2 in which X is a Direct Bond.

Schemes 7 and 8 illustrate the preparation of the phosphonate esters 2 in which X is a direct bond. As shown in Scheme 7, a cbz-protected oxirane 7.1 in which the substituent A is either the group lin-P(O)(OR$^1$)$_2$ or a precursor thereto, such as [OH], [SU] Br, is reacted with a hydrazine derivative 1.2, to afford the ring-opened product 7.3. The conditions for the reaction are the same as those described above for the preparation of the hydrazine derivative 1.3, (Scheme 1). The preparation of the substituted oxiranes 7.1 are described below, in Scheme 9. The product 7.3 is then transformed, using the sequence of reactions illustrated in Scheme 7, into the product 7.8. The conditions employed for the component reactions of this sequence are the same as for the analogous reaction in Scheme 1.

The procedures illustrated in Scheme 7 depict the preparation of the compounds 7.8 in which the substituent A is either the group link-P(O)(OR$^1$)$_2$ or a precursor thereto, such as [OH], [SH] Br, as described below. Scheme 8 illustrates the conversion of compounds 7.8 in which A is a precursor to the group link-P(O)(OR$^1$)$_2$ into the compounds 2. Procedures for the conversion of the substituent A into the group link-P(O)(OR$^1$)$_2$ are illustrated below, (Schemes 21-56).

Scheme 9 illustrates the preparation of the oxiranes 7.1. In this sequence, a substituted phenylalanine 9.1, in which substituent A is either the group link-P(O)(OR$^1$)$_2$ or a precursor thereto, such as [OH], [SH] Br, as described below, is transformed into the cbz-protected derivative 9.2, using the conditions described above for the preparation of the cbz derivative 3.2, (Scheme 3). The latter compound is then transformed, using the using the sequence of reactions illustrated in Scheme 3, into the product 7.1. The conditions for the component reactions of this sequence are the same as for the analogous reactions in Scheme 3.

Preparation of the Phosphonate Ester Intermediates 2 in which X is a Sulfur.

Schemes 10 and 11 illustrate the preparation of the compounds 2 in which X is sulfur. As shown in Scheme 10, the mesylate 5.1 is reacted with the substituted thiophenol 10.1, in which substituent A is either the group link-P(O)(OR$^1$)$_2$ or a precursor thereto, such as [OH], [SH] Br, as described below (scheme 30-39), to afford the thioether 10.2. The conditions employed for this reaction are the same as those described above for the preparation of the thioether 5.3, Scheme 5. The product 10.2 is then transformed, using the series of reactions shown in Scheme 5, into the diacylated thioether 10.3. The conditions for the component reactions of this sequence are the same as for the analogous reactions in Scheme 5.

The procedures illustrated in Scheme 10 depict the preparation of the compounds 10.3 in which the substituent A is either the group link-P(O)(OR$^1$)$_2$ or a precursor thereto, such as [OH], [SH] Br, as described below. Scheme 11 illustrates the conversion of compounds 10.3 in which A is a precursor to the group link-P(O)(OR$^1$)$_2$ into the compounds 2. Procedures for the conversion of the substituent A into the group link-P(O)(OR$^1$)$_2$ are illustrated below, (Schemes 21-56).

Preparation of the Phosphonate Ester Intermediates 3 in which X is a Direct Bond.

Schemes 12 and 13 depict the preparation of the phosphonate esters 3a in which X is a direct bond. As shown in Scheme 12, the oxirane 1.1 is reacted with a BOC protected phenylhydrazine derivative 12.1 in which the substituent A is either the group link-P(O)(OR$^1$)$_2$ or a precursor thereto, such as [OH], [SH] Br, as described below. The preparation of the hydrazine derivatives 12.1 is described in Schemes 4, 40 and 41. The reaction is conducted under the same conditions as described above for the preparation of the hydrazine 7.3, Scheme 7. The product 12.2 is then transformed, using the sequence of reactions shown in Scheme 7 for the transformation of the hydrazine 7.3 into the diacylated compound 7.8, into the diacylated compound 12.3. The conditions for the component reactions of this sequence are the same as for the analogous reactions in Scheme 7.

The procedures illustrated in Scheme 12 depict the preparation of the phosphonate esters 12.3 in which the substituent A is either the group link-P(O)(OR$^1$)$_2$ or a precursor thereto, such as [OH], [SH] Br, as described below. Scheme 13 illustrates the conversion of compounds 12.3 in which A is a precursor to the group link-P(O)(OR$^1$)$_2$ into the compounds 3a in which X is a direct bond. Procedures for the conversion of the substituent A into the group link-P(O)(OR$^1$)$_2$ are illustrated below, (Schemes 21-56).

The phosphonate esters 3b, 3c and 3d, in which X is a direct bond, are prepared using the procedures of Schemes 12 and 13, except that the hydrazine derivatives 4.13, 4.17 and 4.15, prepared as described in Schemes 42-52, are used in place of the hydrazine derivative 12.1.

Preparation of the Phosphonate Ester Intermediates 3 in which X is Sulfur.

Schemes 14 and 15 illustrate the preparation of the phosphonate esters 3a in which X is sulfur. As shown in Scheme 14, the p-toluenesulfonate ester 5.5 is reacted with the phenylhydrazine derivative 12.1, in which the substituent A is either the group link-P(O)(OR$^1$)$_2$ or a precursor thereto, such as [OH], [SH] Br, as described below, to afford the hydrazine derivative 14.1. The reaction is conducted under the same conditions as described above for the preparation of the hydrazine 5.6, Scheme 5. The product 14.1 is then transformed into the diacylated product 14.2, using the sequence of reactions shown in Scheme 5. The conditions for the component reactions of this sequence are the same as for the analogous reactions in Scheme 5. The procedures illustrated in Scheme 14 depict the preparation of the phosphonate esters 14.2 in which the substituent A is either the group link-P(O)(OR$^1$)$_2$ or a precursor thereto, such as [OH], [SH] Br, as described below. Scheme 15 illustrates the conversion of compounds 14.2 in which A is a precursor to the group link-P(O)(OR$^1$)$_2$ into the compounds 3a in which X is S. Procedures for the conversion of the substituent A into the group link-P(O)(OR$^1$)$_2$ are illustrated below, (Schemes 21-56).

The phosphonate esters 3b, 3c and 3d, in which X is S, are prepared using the procedures of Schemes 12 and 13, except that the hydrazine derivatives 4.13, 4.17 and 4.15, prepared as described in Schemes 42-52, are used in place of the hydrazine derivative 12.1.
Scheme 7
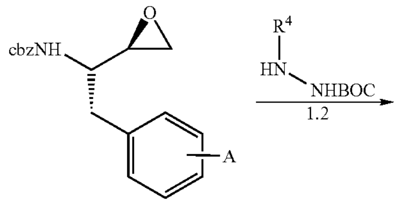
7.1
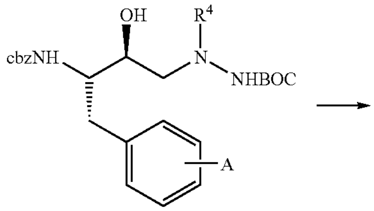
7.3
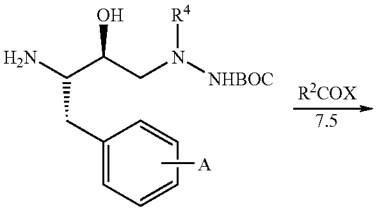
7.4
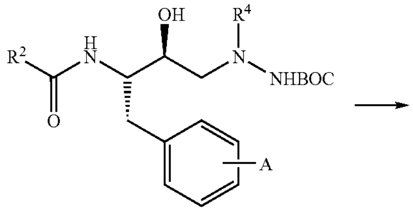
7.6
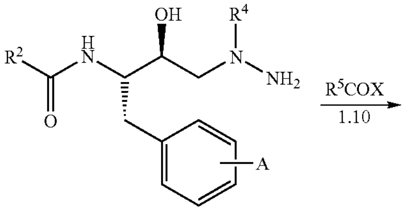
7.7
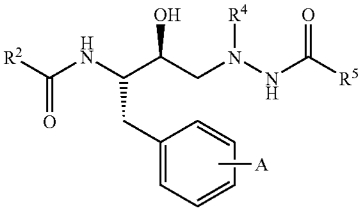
7.8
Scheme 8
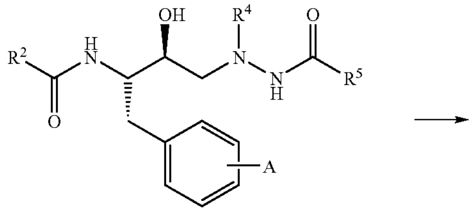
7.8
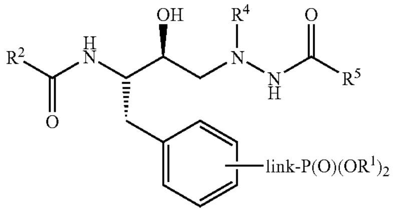
2
Scheme 9
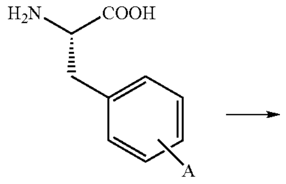
9.1
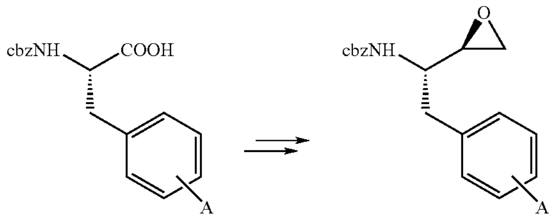
9.2 7.1
Scheme 10
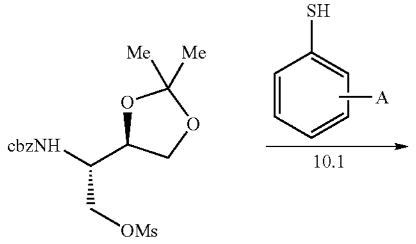
5.1

-continued
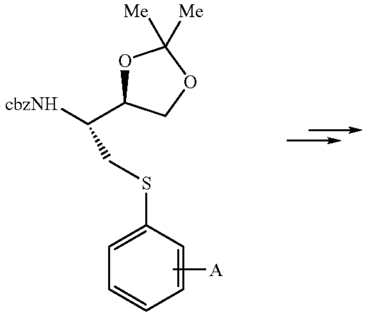
10.2
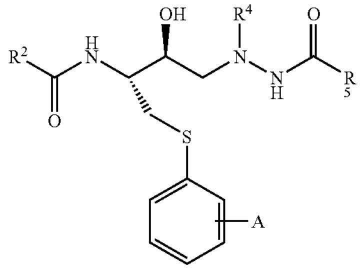
10.3
Scheme 11
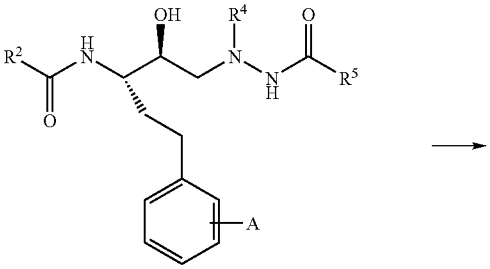
10.3
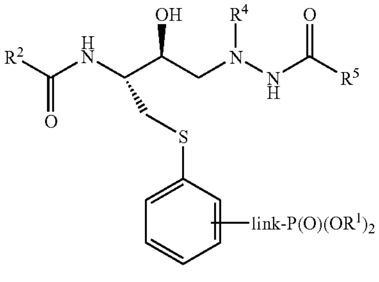
2
Scheme 12
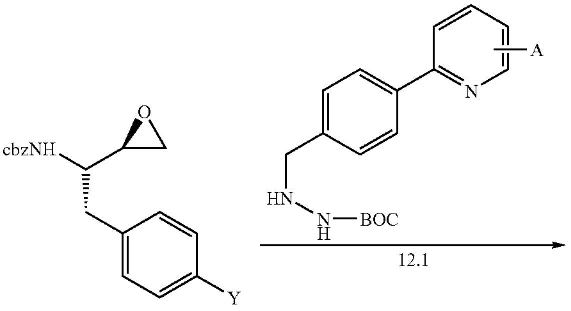
1.1
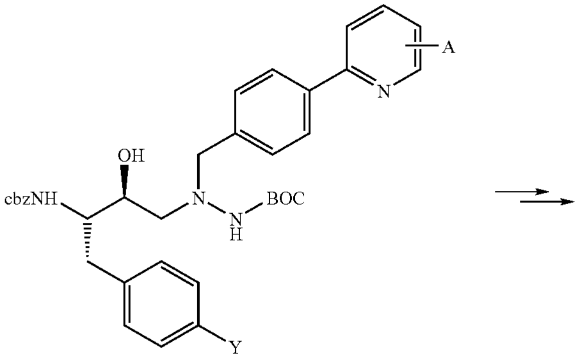
12.2
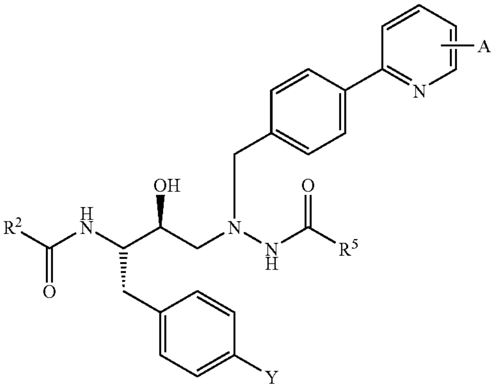
12.3

Scheme 13

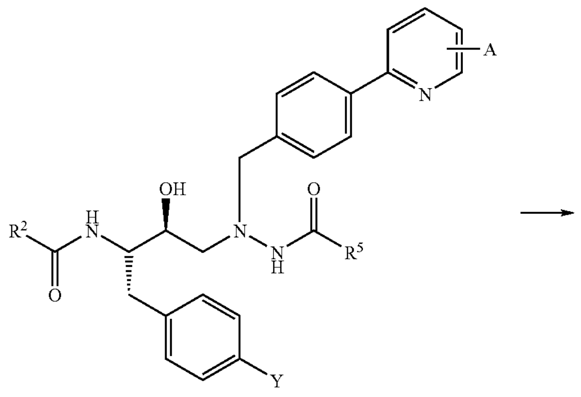

12.3

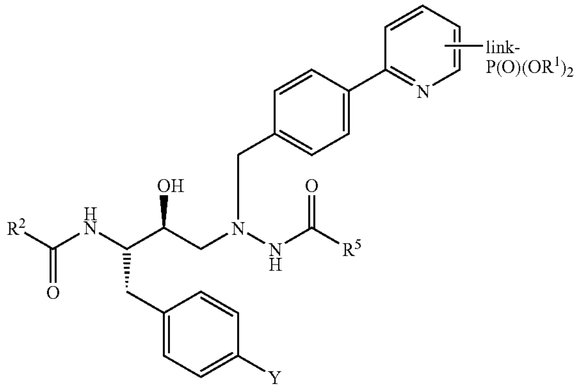

3a

Scheme 14

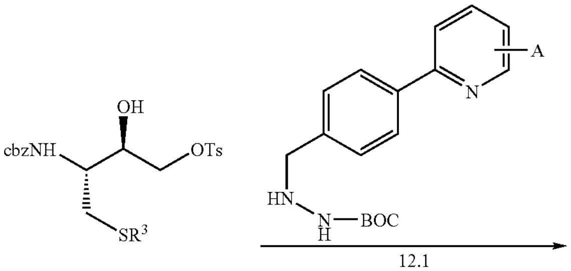

5.5

12.1

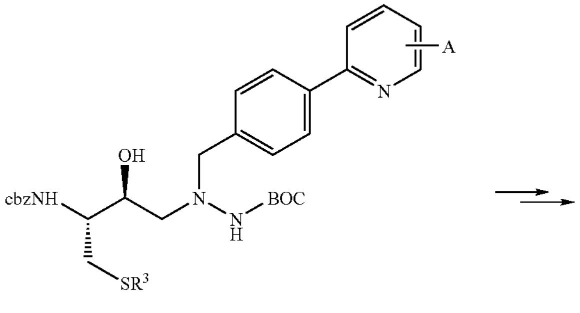

14.1

-continued

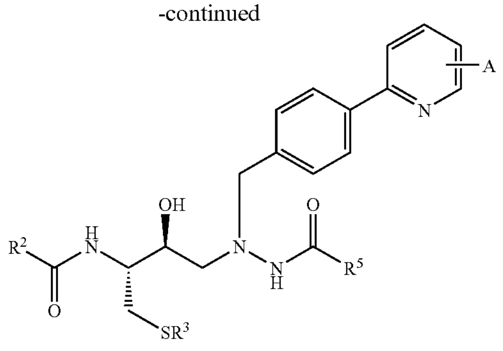

14.2

Scheme 15

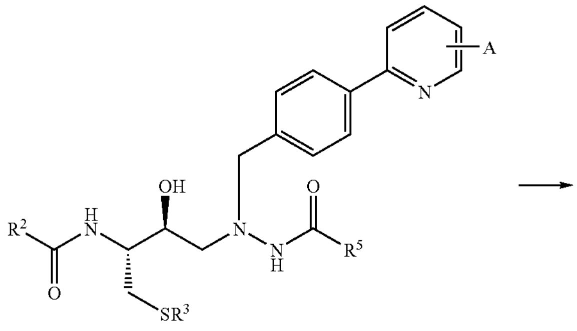

14.3

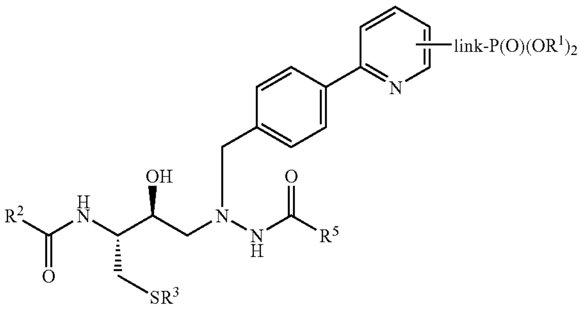

3a

Preparation of the Phosphonate Ester Intermediates 4 in which X is a Direct Bond.

Schemes 16 and 17 illustrate the preparation of the phosphonate esters 4 in which X is a direct bond. As shown in Scheme 16, the amine 1.4, prepared as described in Scheme 1, is reacted with the carboxylic acid or activated derivative thereof $R^2COX$ 7.5, to afford the amide 16.1. The conditions for the amide forming reaction are the same as those described above for the preparation of the amide 1.11, (Scheme 1). The product is then deprotected by removal of the BOC group, using the procedures described above (Scheme 1), to yield the hydrazine 16.2. This material is then coupled with the aminoacid 1.5, using the coupling procedures described above for the preparation of the amide 1.6, to produce the amide 16.3. The product is then reacted with the acylating agent $A\text{-}CR^7R^8OCOX$, 1.7, in which A and X are as described above, Scheme 1, to afford the carbamate product 16.4.

The procedures illustrated in Scheme 16 depict the preparation of the phosphonate esters 16.4 in which the substituent A is either the group link-P(O)($OR^1$)$_2$ or a precursor thereto, such as [OH], [SH] Br, as described below. Scheme 17 illustrates the conversion of compounds 16.4 in which A is a precursor to the group link-P(O)($OR^1$)$_2$ into the compounds 4. Procedures for the conversion of the substituent A into the group link-P(O)($OR^1$)$_2$ are illustrated below, (Schemes 21-56).

Preparation of the Phosphonate Ester Intermediates 4 in which X is Sulfur.

Schemes 18 and 19 illustrate the preparation of the phosphonate esters 4 in which X is sulfur. As shown in Scheme 18, the amine 5.7, prepared as described in Scheme 5, is reacted with the carboxylic acid or activated derivative thereof 7.5, to produce the amide 18.1. The reaction is performed under the conditions described above for the preparation of the amide 1.11. The BOC group present in the amide 18.1 is then removed using the procedures described above, (Scheme 1) to afford the amine 18.2. This material is then coupled with the aminoacid 1.5, using the procedures described above for the preparation of the amide 1.6, to produce the amide 18.3. The latter compound is then reacted with the acylating agent A-$CR^7R^8$OCOX, 1.7, in which A and X are as described above, Scheme 1, to afford the carbamate product 18.4.

The procedures illustrated in Scheme 18 depict the preparation of the phosphonate esters 18.4 in which the substituent A is either the group link-P(O)($OR^1$)$_2$ or a precursor thereto, such as [OH], [SH] Br, as described below. Scheme 19 illustrates the conversion of compounds 18.4 in which A is a precursor to the group link-P(O)($OR^1$)$_2$ into the compounds 4. Procedures for the conversion of the substituent A into the group link-P(O)($OR^1$)$_2$ are illustrated below, (Schemes 21-56).

Preparation of the Phosphonate Ester Intermediates 5 in which X is a Direct Bond.

Schemes 19a and 19b illustrate the preparation of the phosphonate esters 5 in which X is a direct bond. As shown in Scheme 19a, the amine 1.6 is reacted with a quinoline-2-carboxylic acid derivative 19a.1, in which the substituent A is either the group ($R^1O$)$_2$P(O)-link or a precursor group thereto, such as OH, SH, Br to afford the amide 19a.2. The reaction is performed as described above for the preparation of the amide 1.6 (Scheme 1). The BOC protecting group is then removed, using the procedures described in Scheme 1, to yield the amine 19a.3. This compound is then reacted, as described above, with the carboxylic acid $R^5$COOH, or an activated derivative thereof 19a.4, to give the amide 19a.5.

The procedures illustrated in Scheme 19a depict the preparation of the phosphonate esters 19a.5 in which the substituent A is either the group link-P(O)($OR^1$)$_2$ or a precursor thereto, such as [OH], [SH] Br, as described below. Scheme 19b illustrates the conversion of compounds 19a.5 in which A is a precursor to the group link-P(O)($OR^1$)$_2$ into the compounds 5. Procedures for the conversion of the substituent A into the group link-P(O)($OR^1$)$_2$ are illustrated below, (Schemes 21-56). The preparation of the quinoline carboxylic acid reagents 19a.1 is described below, (Schemes 53-56).

Preparation of the Phosphonate Ester Intermediates 5 in which X is Sulfur.

Schemes 19c and 19d illustrate the preparation of the phosphonate esters 5 in which X is sulfur. As shown in Scheme 19c, the amine 5.9 is reacted, as described above, with the quinoline carboxylic acid derivative 19a.1 to yield the amide product 19c.1. The BOC protecting group is then removed, as described above, to give the amine 19c.2. The latter compound is then reacted, as described above, with the carboxylic acid $R^5$COOH, or an activated derivative thereof 19a.4, to give the amide 19c.3.

The procedures illustrated in Scheme 19c depict the preparation of the phosphonate esters 19c.3 in which the substituent A is either the group link-P(O)($OR^1$)$_2$ or a precursor thereto, such as [OH], [SH] Br, as described below. Scheme 19d illustrates the conversion of compounds 19c.3 in which A is a precursor to the group link-P(O)($OR^1$)$_2$ into the compounds 5. Procedures for the conversion of the substituent A into the group link-P(O)($OR^1$)$_2$ are illustrated below, (Schemes 21-56). The preparation of the quinoline carboxylic acid reagents 19a.1 is described below, (Schemes 53-56).

Scheme 16

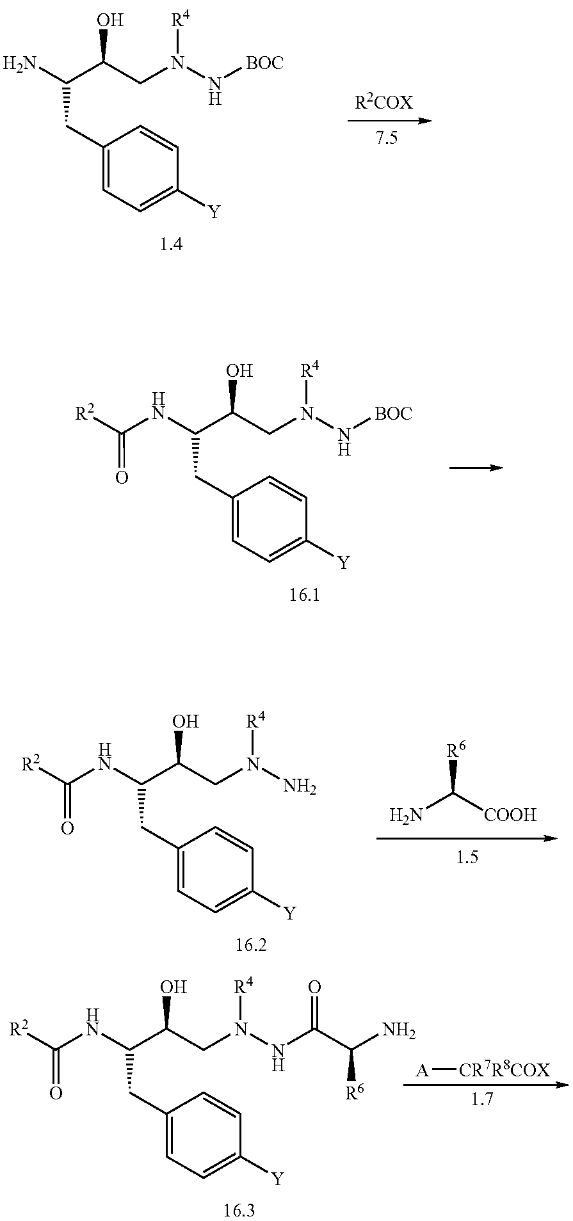

-continued
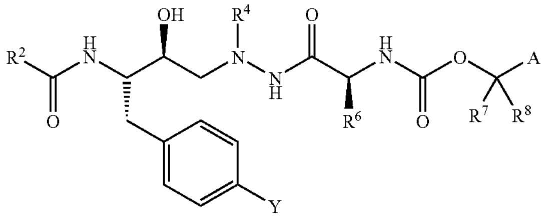
16.4
Scheme 17
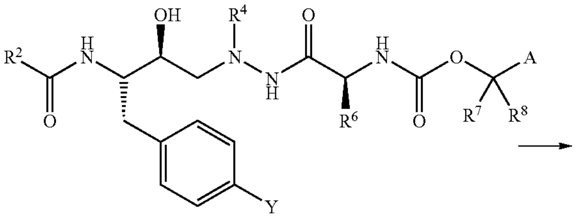
16.4
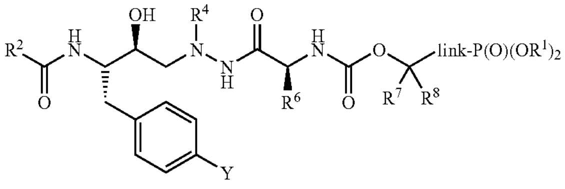
4
Scheme 18
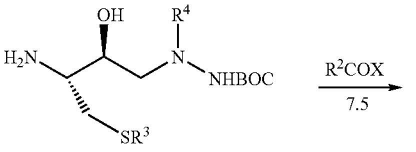
5.7
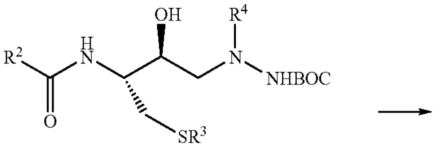
18.1
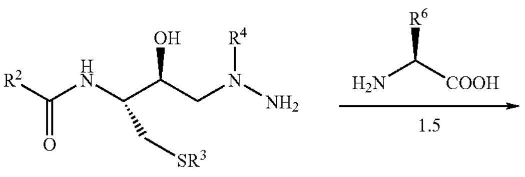
18.2
-continued
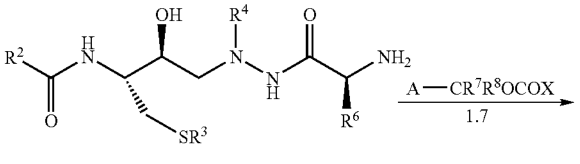
18.3
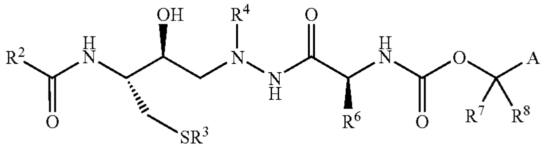
18.4
Scheme 19
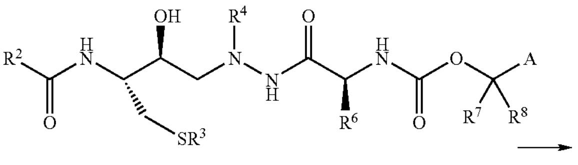
18.4
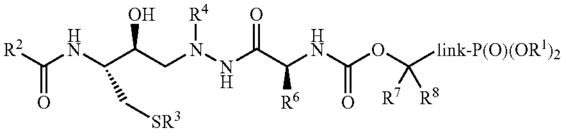
4
Scheme 19a
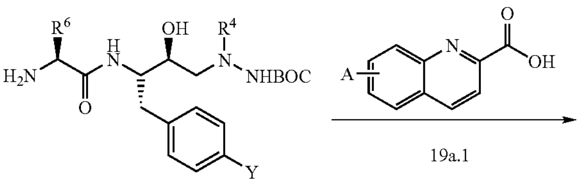
1.6
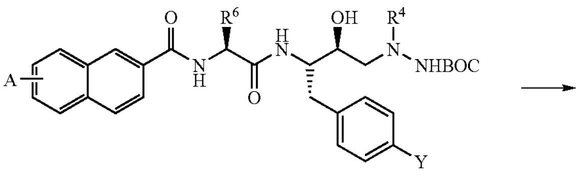
19a.2
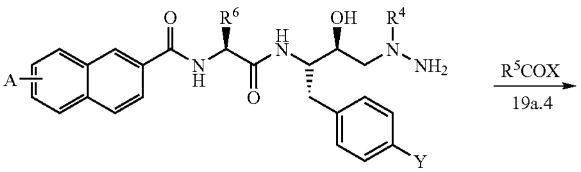
19a.3

-continued
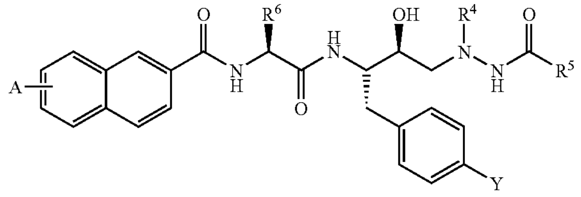
19a.5
Scheme 19b
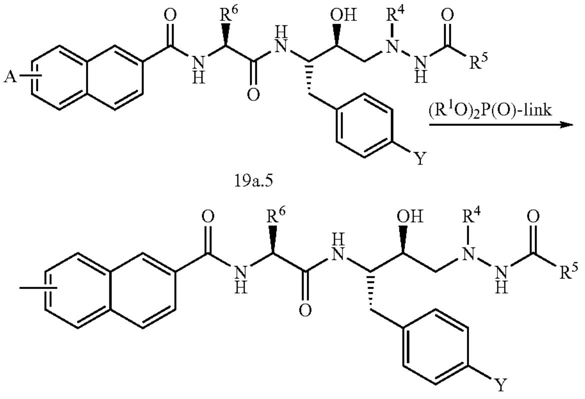
19a.5
5
Scheme 19c
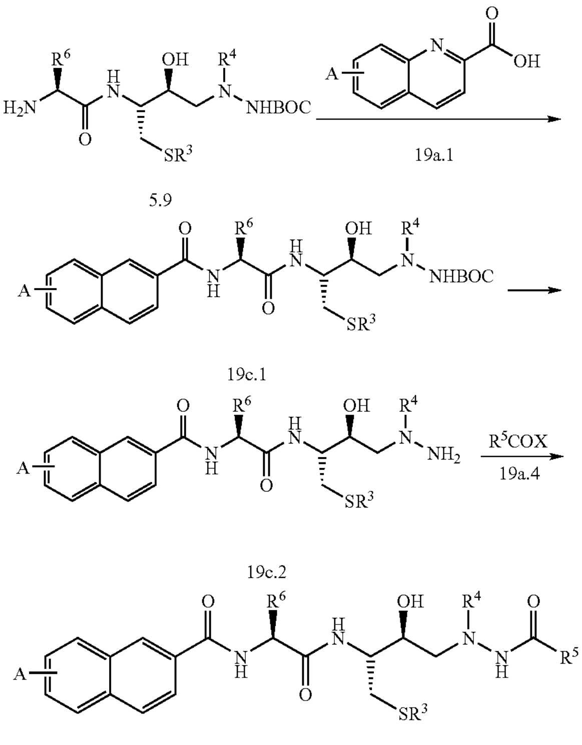
5.9
19c.1
19c.2
19c.3
Scheme 19d
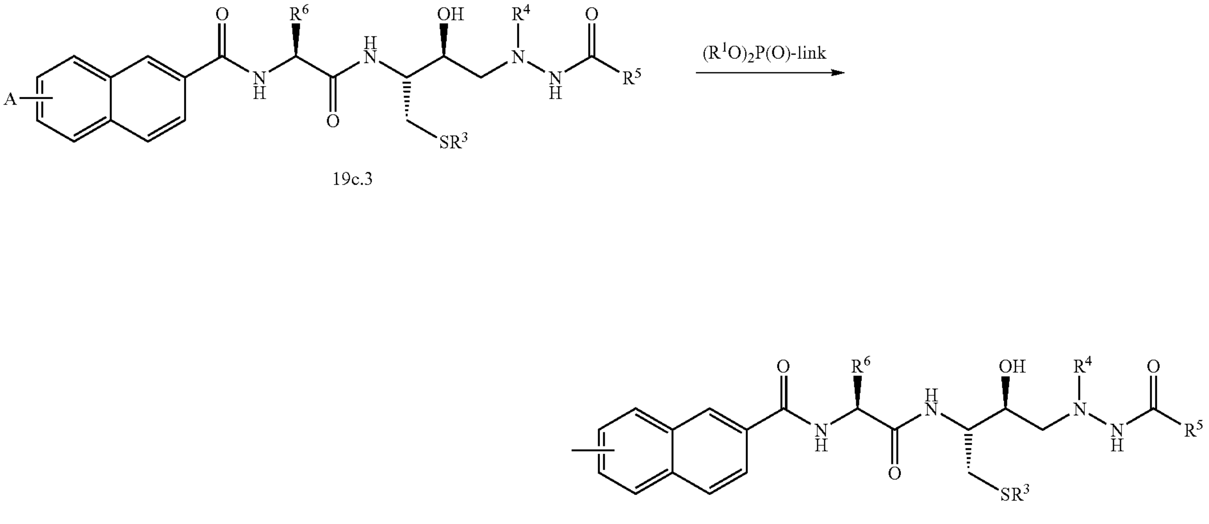
19c.3
5

Preparation of Carbamates.

The phosphonate esters 1 and 4, and the phosphonate ester 1-7 in which the $R^2CO$ or $R^5CO$ groups are formally derived from the carboxylic acids C38-C49 (Chart 2c) contain a carbamate linkage. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 20 illustrates various methods by which the carbamate linkage can be synthesized. As shown in Scheme 20, in the general reaction generating carbamates, a carbinol 20.1, is converted into the activated derivative 20.2 in which Lv is a leaving group such as halo, imidazolyl, benztriazolyl and the like, as described below. The activated derivative 20.2 is then reacted with an amine 20.3, to afford the carbamate product 20.4. Examples 1-7 in Scheme 20 depict methods by which the general reaction can be effected. Examples 8-10 illustrate alternative methods for the preparation of carbamates.

Scheme 20, Example 1 illustrates the preparation of carbamates employing a chloroformyl derivative of the carbinol 20.5. In this procedure, the carbinol 20.5 is reacted with phosgene, in an inert solvent such as toluene, at about 0°, as described in Org. Syn. Coll. Vol. 3, 167, 1965, or with an equivalent reagent such as trichloromethoxy chloroformate, as described in Org. Syn. Coll. Vol. 6, 715, 1988, to afford the chloroformate 20.6. The latter compound is then reacted with the amine component 20.3, in the presence of an organic or inorganic base, to afford the carbamate 20.7. For example, the chloroformyl compound 20.6 is reacted with the amine 20.3 in a water-miscible solvent such as tetrahydrofuran, in the presence of aqueous sodium hydroxide, as described in Org. Syn. Coll. Vol. 3, 167, 1965, to yield the carbamate 20.7. Alternatively, the reaction is performed in dichloromethane in the presence of an organic base such as diisopropylethylamine or dimethylaminopyridine.

Scheme 20, Example 2 depicts the reaction of the chloroformate compound 20.6 with imidazole to produce the imidazolide 20.8. The imidazolide product is then reacted with the amine 20.3 to yield the carbamate 20.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in J. Med. Chem., 1989, 32, 357.

Scheme 20 Example 3, depicts the reaction of the chloroformate 20.6 with an activated hydroxyl compound R"OH, to yield the mixed carbonate ester 20.10. The reaction is conducted in an inert organic solvent such as ether or dichloromethane, in the presence of a base such as dicyclohexylamine or triethylamine. The hydroxyl component R"OH is selected from the group of compounds 20.19-20.24 shown in Scheme 20, and similar compounds. For example, if the component R"OH is hydroxybenztriazole 20.19, N-hydroxysuccinimide 20.20, or pentachlorophenol, 20.21, the mixed carbonate 20.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 20.22 or 2-hydroxypyridine 20.23 can be performed in an ethereal solvent in the presence of triethylamine, as described in Syn., 1986, 303, and Chem. Ber. 118, 468, 1985.

Scheme 20 Example 4 illustrates the preparation of carbamates in which an alkyloxycarbonylimidazole 20.8 is employed. In this procedure, a carbinol 20.5 is reacted with an equimolar amount of carbonyl diimidazole 20.11 to prepare the intermediate 20.8. The reaction is conducted in an aprotic organic solvent such as dichloromethane or tetrahydrofuran. The acyloxyimidazole 20.8 is then reacted with an equimolar amount of the amine $R'NH_2$ to afford the carbamate 20.7. The reaction is performed in an aprotic organic solvent such as dichloromethane, as described in Tet. Lett., 42, 2001, 5227, to afford the carbamate 20.7.

Scheme 20, Example 5 illustrates the preparation of carbamates by means of an intermediate alkoxycarbonylbenztriazole 20.13. In this procedure, a carbinol ROH is reacted at ambient temperature with an equimolar amount of benztriazole carbonyl chloride 20.12, to afford the alkoxycarbonyl product 20.13. The reaction is performed in an organic solvent such as benzene or toluene, in the presence of a tertiary organic amine such as triethylamine, as described in Syn., 1977, 704. The product is then reacted with the amine $R'NH_2$ to afford the carbamate 20.7. The reaction is conducted in toluene or ethanol, at from ambient temperature to about 80° as described in Syn., 1977, 704.

Scheme 20, Example 6 illustrates the preparation of carbamates in which a carbonate $(R''O)_2CO$, 20.14, is reacted with a carbinol 20.5 to afford the intermediate alkyloxycarbonyl intermediate 20.15. The latter reagent is then reacted with the amine $R'NH_2$ to afford the carbamate 20.7. The procedure in which the reagent 20.15 is derived from hydroxybenztriazole 20.19 is described in Synthesis, 1993, 908; the procedure in which the reagent 20.15 is derived from N-hydroxysuccinimide 20.20 is described in Tet. Lett., 1992, 2781; the procedure in which the reagent 20.15 is derived from 2-hydroxypyridine 20.23 is described in Tet. Lett., 1991, 4251; the procedure in which the reagent 20.15 is derived from 4-nitrophenol 20.24 is described in Syn. 1993, 103. The reaction between equimolar amounts of the carbinol ROH and the carbonate 20.14 is conducted in an inert organic solvent at ambient temperature.

Scheme 20, Example 7 illustrates the preparation of carbamates from alkoxycarbonyl azides 20.16. In this procedure, an alkyl chloroformate 20.6 is reacted with an azide, for example sodium azide, to afford the alkoxycarbonyl azide 20.16. The latter compound is then reacted with an equimolar amount of the amine $R'NH_2$ to afford the carbamate 20.7. The reaction is conducted at ambient temperature in a polar aprotic solvent such as dimethylsulfoxide, for example as described in Syn., 1982, 404.

Scheme 20, Example 8 illustrates the preparation of carbamates by means of the reaction between a carbinol ROH and the chloroformyl derivative of an amine 20.17. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 20.7.

Scheme 20, Example 9 illustrates the preparation of carbamates by means of the reaction between a carbinol ROH and an isocyanate 20.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 20.7.

Scheme 20, Example 10 illustrates the preparation of carbamates by means of the reaction between a carbinol ROH and an amine $R'NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 20.7.

Scheme 20

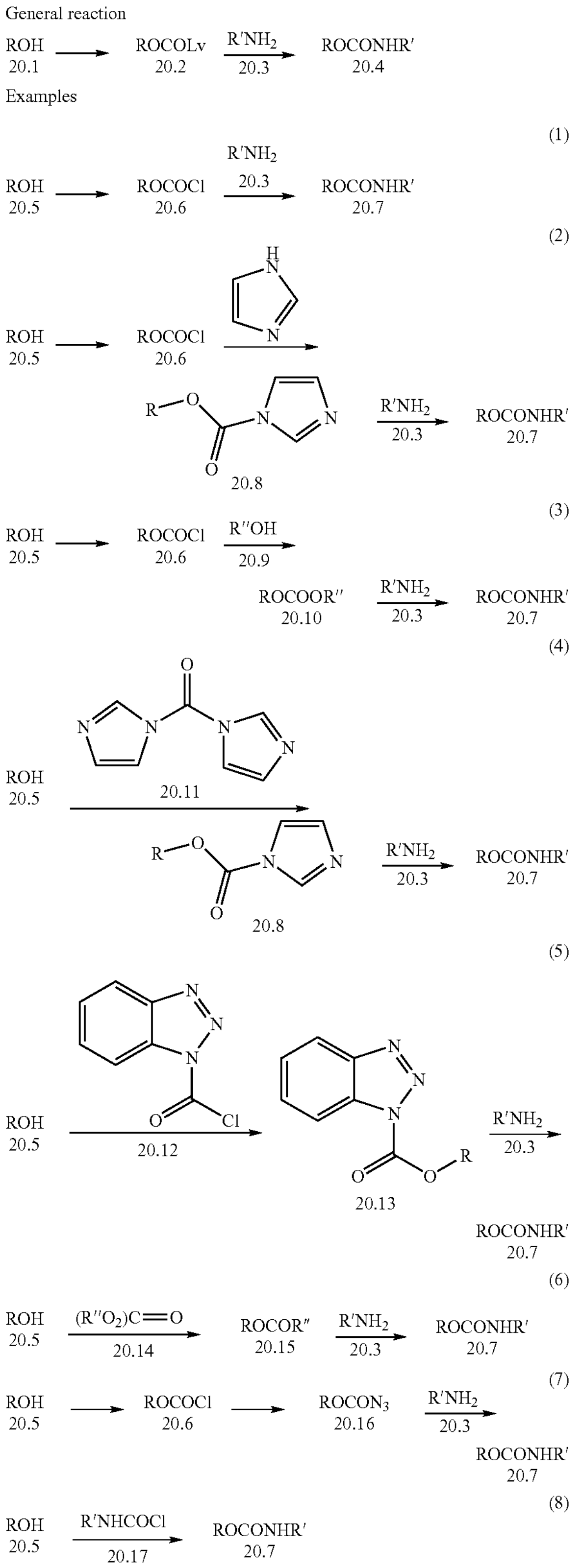

-continued

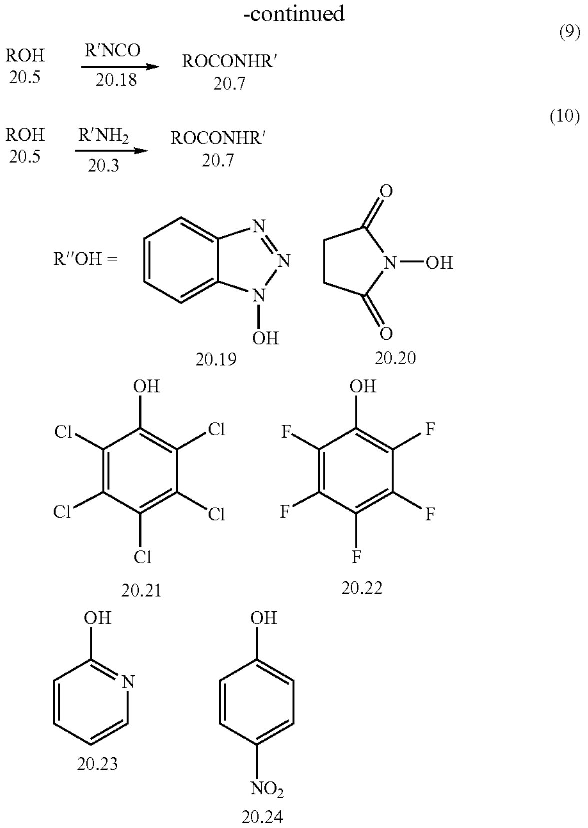

Preparation of the Reagents A-$CR^7R^8$OCOX.

The reagents A-$CR^7R^8$OCOX 1.7 are prepared from the corresponding carbinols A-$CR^7R^8$OH, using procedures such as those described above in Scheme 20. Examples of the preparation of the carbinols A-$CR^7R^8$OH and the derived reagents 1.7 are shown below in Schemes 21-26. The activation methods for the conversion of the carbinols A-$CR^7R^8$OH to the reagents A-$CR^7R^8$OCOX are interchangeable between the different alcohols A-$CR^7R^8$OH.

Scheme 21 depicts the preparation of phosphonate-containing reagents 21.2 in which the phosphonate is linked by means of an alkylene chain. In this procedure, a dialkyl hydroxyalkyl phosphonate 21.1 is reacted with phosgene, or an equivalent reagent, to afford the chloroformate 21.2, as described above in Scheme 20, Example 1. The reaction is conducted in an inert organic solvent such as dichloromethane or toluene, at from about 0° to ambient temperature.

For example, as shown in Scheme 21, Example 1, a dialkyl hydroxymethylphosphonate 21.3 (Aldrich) is reacted with excess phosgene in toluene at 0°, as described in Org. Syn. Coll. Vol. 3, 197, 1965, to afford the chloroformyl product 21.4.

Scheme 21, Example 2 illustrates the analogous conversion of a dialkyl hydroxyethyl phosphonate 21.5 (Aldrich) into the chloroformate derivative 21.6. The reaction is performed as described above for the preparation of the chloroformate 21.4.

Scheme 21, Example 3 illustrates the analogous conversion of a dialkyl phosphono-substituted tert. butanol 21.7, prepared as described in Fr.2462440, into the chloroformate derivative 21.8. The reaction is performed as described above for the preparation of the chloroformate 21.4.

Using the above procedures, but employing, in place of the phosphonates 21.3, 21.5 or 21.7, different dialkyl hydroxyalkyl phosphonates 21.1, the corresponding products 21.2 are obtained.

Scheme 22 depicts the preparation of phosphonate-containing reagents 22.2 in which the phosphonate is linked by means of a phenyl ring. In this procedure, a dialkyl hydroxyalkylphenyl phosphonate 22.1 is converted, as described above, into an activated chloroformyl derivative 22.2, using the procedures described above in Scheme 20.

For example, a dialkyl 4-hydroxymethylphenylphosphonate 22.3 (Aldrich) is reacted in tetrahydrofuran with an equimolar amount of the 2-pyridyl carbonate 22.4, prepared as described in Tet. Let., 1991, 4251, to afford the product 22.5.

Using the above procedure, but employing, in place of a dialkyl hydroxyphenylphosphonate 22.3, different dialkyl hydroxyphenyl phosphonates 22.1, the corresponding products 22.2 are obtained.

Scheme 23 depicts the preparation of phosphonate containing reagents 23.4 in which the phosphonate group is linked by means of an alkylene chain incorporating a heteroatom O, S or N. In this procedure, a dialkyl hydroxy-, thio- or alkylaminoalkylphosphonate 23.1 is alkylated by reaction with a bromoalkanol 23.2. The alkylation reaction is conducted at from ambient temperature to about 70° in a polar organic solvent such as dimethylformamide, dioxan or acetonitrile, in the presence of a base. In cases in which X is oxygen, a strong base such as lithium hexamethyldisilylazide or potassium tert-butoxide is employed. In cases in which X is sulfur or alkylamino, an inorganic base such as potassium carbonate or cesium carbonate is used. The product 23.3 is then converted into an activated derivative 23.4 by means of one of the methods described above in Scheme 20.

For example, as shown in Scheme 23, Example 1, a dialkyl 2-mercaptoethyphosphonate 23.5, prepared as described in Zh. Obschei. Khim., 1973, 43, 2364, is reacted with one molar equivalent of bromoethanol 23.6, in dimethylformamide at 60° in the presence of cesium carbonate, to afford the thioether product 23.7. This compound is then reacted with pentafluorophenyl carbonate 23.8, (Fluorochem) in dimethylformamide solution at ambient temperature in the presence of triethylamine, to afford the pentafluorophenoxycarbonyl product 23.9.

As a further example of the method of Scheme 23, as shown in Example 2, a dialkyl methylaminomethyl phosphonate 23.10, (AsInEx Inc.) is reacted in dimethylformamide at 70° with one molar equivalent of 5-bromo-2-hydroxy-2-methylpentane 23.11, prepared as described in J. Med. Chem., 1994, 37, 2343, and potassium carbonate, to afford the amine product 23.12. The product is then converted, as described above, into the pentafluorophenyl formate derivative 23.13.

Using the above procedures, but employing, in place of a dialkyl 2-mercaptoethyphosphonate 23.5, or a dialkyl methylaminomethyl phosphonate 23.10, different hydroxy, mercapto or aminoalkylphosphonates 23.1, and/or different bromoalkanols 23.2, and/or different activation methods, the corresponding products 23.4 are obtained.

Scheme 24 illustrates the preparation of phosphonate containing reagents 24.4 in which the phosphonate group is linked by means of an alkylene chain incorporating an N-alkyl group. In this procedure, a dialkyl formylalkyl phosphonate 24.1 is reacted with an alkylaminoalkanol 24.2 under reductive amination conditions, so as to afford the product 24.3. The preparation of amines by means of reductive amination procedures is described, for example, in Comprehensive Organic Transformations, by R. C. Larock, VCH, p. 421, and in Advanced Organic Chemistry, Part B, by F. A. Carey and R. J. Sundberg, Plenum, 2001, p. 269. In this reaction, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The reduction reaction can also be performed by hydrogenation in the presence of a palladium catalyst and hydrogen or a hydrogen donor. The reaction product 24.3 is then transformed into the activated derivative 24.4 by means of one of the procedures described above in Scheme 20.

As shown in Scheme 24, Example 1, a dialkyl formylmethylphosphonate 24.5 (Aurora) is reacted with methylaminoethanol 24.6, in the presence of sodium cyanoborohydride, to afford the coupled product 24.7. This compound is then reacted with an equimolar amount of chlorocarbonylbenztriazole 20.13, in toluene at 80°, in the presence of one molar equivalent of triethylamine, as described in Syn., 1977, 704, to yield the product 24.8.

As a further example of the method of Scheme 24, as shown in Example 2, the aldehyde 24.5 is reacted with 2-hydroxy-2-methyl-3-methylaminopropane 24.10, under reductive amination conditions, to afford the amine product 24.11. The latter compound is then reacted with phosgene, or an equivalent thereof, as described above, to afford the chloroformyl product 24.12.

Using the above procedures, but employing, in place of the phosphonates 24.5, different phosphonates 24.1, and/or in place of the aminoalkanols 24.6 or 24.10, different aminoalkylalkanols 24.2, and/or different activation methods described in Scheme 20, the corresponding products 24.4 are obtained.

Scheme 25 illustrates the preparation of phosphonate containing reagents 25.2 in which the phosphonate group is linked by means of an alkylene chain incorporating an acetylenic linkage. In this procedure, a dialkyl hydroxyalkynyl phosphonate 25.1 is converted, by means of one of the procedures described in Scheme 20, into the activated formyl derivative 25.2.

For example, a dialkyl hydroxypropynyl phosphonate 25.3 prepared as described in J. Org. Chem., 1987, 52, 4810, is reacted with one molar equivalent of di(succinimidyloxy) carbonate 25.4, prepared as described in Tet. Lett, 1992, 2781, in dichloromethane at ambient temperature, to afford the product 25.5.

Using the above procedures, but employing, in place of the dialkyl hydroxypropynyl phosphonate 25.3, different dialkyl hydroxyalkynyl phosphonates 25.1, the corresponding products 25.2 are obtained.

Scheme 26 illustrates the preparation of phosphonate containing reagents 26.2 in which the phosphonate group is linked by means of an alkylene chain incorporating an olefinic linkage. In this procedure, a dialkyl hydroxyalkenyl phosphonate 26.1 is converted, by means of one of the procedures described in Scheme 20, into the activated formyl derivative 26.2.

For example, a dialkyl propenylphosphonate 26.3, prepared as described in Zh. Obschei. Khim., 1974, 44, 18343, is reacted with phosgene in toluene at 0°, as described in Org. Syn. Coll. Vol. 3, 167, 1965, to afford the chloroformyl product 26.4.

Using the above procedures, but employing, in place of the dialkyl hydroxypropenyl phosphonate 26.3, different dialkyl hydroxyalkynyl phosphonates 26.1, the corresponding products 26.2 are obtained.

Scheme 21

Method $(R^1O)_2P(O)(CH_2)_nCR^7R^8OH$ 21.1 → $(R^1O)_2P(O)(CH_2)_nCR^7R^8OCOLv$ 21.2

Example 1

$(R^1O)_2P(O)CH_2OH$ 21.3 → $(R^1O)_2P(O)CH_2OCOCl$ 21.4

Example 2

$(R^1O)_2P(O)(CH_2)_2OH$ 21.5 → $(R^1O)_2P(O)(CH_2)_2OCOCl$ 21.6

Example 3

$(R^1O)_2P(O)CH_2C(CH_3)_2OH$ 21.7 → $(R^1O)_2P(O)CH_2C(CH_3)_2OCOCl$ 21.8

Scheme 22

Method

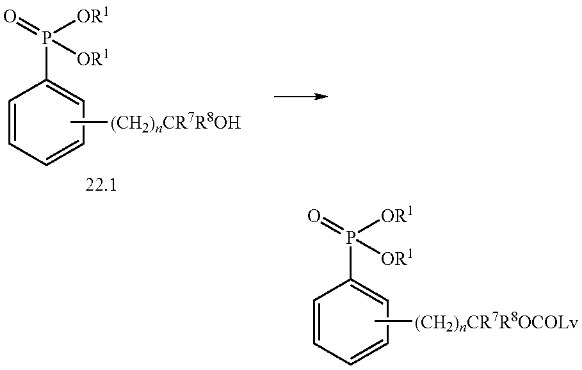

22.1

22.2

Example

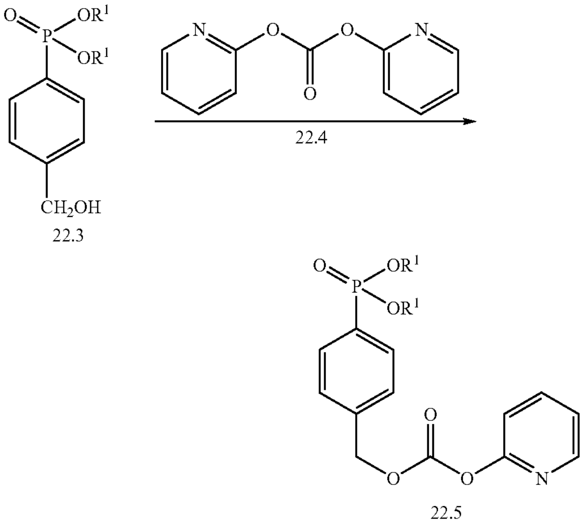

22.3

22.4

22.5

Scheme 23

Method $(R^1O)_2P(O)(CH_2)_nXH$ 23.1

X = O, S, N-alkyl $Br(CH_2)_mCR^7R^8OH$ 23.2

$(R^1O)_2P(O)(CH_2)_nX(CH_2)_mCR^7R^8OH$ 23.3

$(R^1O)_2P(O)(CH_2)_nX(CH_2)_mCR^7R^8OCOLv$ 23.4

Example 1

$(R^1O)_2P(O)CH_2SH$ 23.5

$Br(CH_2)_2OH$ 23.6

$(R^1O)_2P(O)CH_2S(CH_2)_2OH$ 23.7

$(C_6F_5O)_2CO$ 23.8

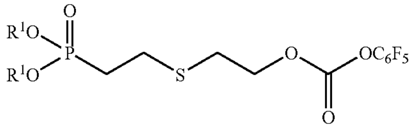

23.9

Example 2

$(R^1O)_2P(O)CH_2NHCH_3$ 23.10

$Br(CH_2)_3C(CH_3)_2OH$ 23.11

$(R^1O)_2P(O)CH_2N(CH_3)(CH_2)_3C(CH_3)_2OH$ 23.12

$(R^1O)_2P(O)CH_2N(CH_3)(CH_2)_3C(CH_3)_2OCOC_6F_5$ 23.13

Scheme 24

Method $(R^1O)_2P(O)(CH_2)_nCHO$ 24.1

$AlkylNH(CH_2)_mCR^7R^8OH$ 24.2

$(R^1O)_2P(O)(CH_2)_nCH_2N(alkyl)(CH_2)_mCR^7R^8OH$ 24.3

$(R^1O)_2P(O)(CH_2)_nCH_2N(alkyl)(CH_2)_mCR^7R^8OCOLv$ 24.4

Example 1

$(R^1O)_2P(O)CH_2CHO$ 24.5

$CH_3NH(CH_2)_2OH$ 24.6

$(R^1O)_2P(O)(CH_2)_2N(CH_3)(CH)_2OH$ 24.7

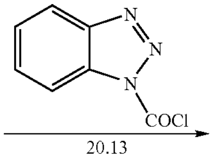

20.13

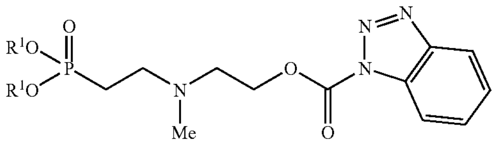

24.8

-continued

Example 2

$(R^1O)_2P(O)CH_2CHO$ 24.5

$CH_3NHCH_2(CH_3)_2OH$ 24.10

$(R^1O)_2P(O)CH_2CH_2N(CH_3)CH_2(CH_3)_2OH$ 24.11

$(R^1O)_2P(O)CH_2CH_2N(CH_3)CH_2(CH_3)_2OCOCl$ 24.12

Scheme 25

Method

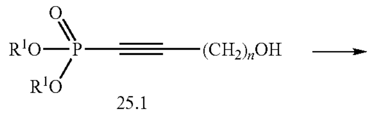

25.1

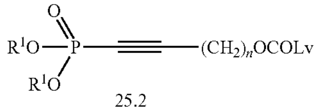

25.2

Example

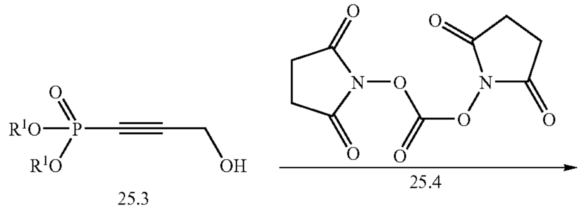

25.3

25.4

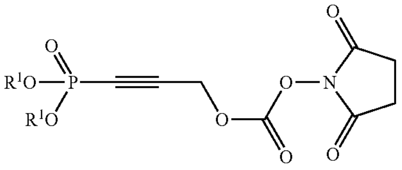

25.5

Scheme 26

Method

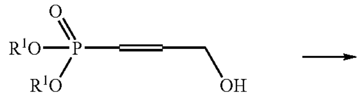

26.1

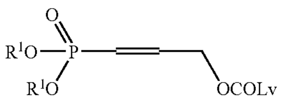

26.2

-continued

Example

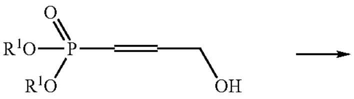

26.3

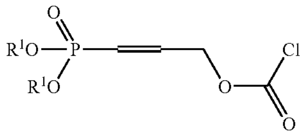

26.4

Preparation of the Oxirane Reactants 7.1.

The oxirane reactants 7.1 are obtained by means of chemical transformations applied to variously substituted phenylalanine derivatives. In the methods described below, the phosphonate moiety can be introduced into the molecule at any appropriate stage in the synthetic sequence, or after the intermediates are incorporated into the phosphonate esters 2.

Scheme 27 depicts the preparation of oxirane reactants 27.5 in which the phosphonate moiety is attached directly to the phenyl ring. In this procedure, a bromo-substituted phenylalanine 27.1 is converted into the cbz-protected derivative, using the procedures described above in Scheme 3. The protected product 27.2 is then converted, by means of the series of reactions shown in Scheme 3, into the oxirane 27.3. The latter compound is then reacted with a dialkyl phosphite 27.4, in the presence of a palladium catalyst, to afford the phosphonate ester 27.5. The preparation of arylphosphonates by means of a coupling reaction between aryl bromides and dialkyl phosphites is described in J. Med. Chem., 35, 1371, 1992.

For example, 4-bromophenylalanine 27.6, prepared as described in Biotech. Lett., 1994, 16, 373, is converted, as described above, (Scheme 3), into the oxirane 27.7. This compound is then reacted, in toluene solution at reflux, with a dialkyl phosphite 27.4, triethylamine and tetrakis(triphenylphosphine)palladium(0), as described in J. Med. Chem., 35, 1371, 1992, to afford the phosphonate product 27.8.

Using the above procedures, but employing, in place of 4-bromophenylalanine 27.6, different bromo-substituted phenylalanines 27.1, and/or different dialkyl phosphites, the corresponding products 27.5 are obtained.

Scheme 28 illustrates the preparation of oxiranes 28.4 in which the phosphonate moiety is attached by means of an alkylene chain. In this procedure, a carbobenzyloxy protected bromo-substituted phenylalanine 27.2, prepared as described above, is coupled, in the presence of a palladium catalyst, with a dialkyl alkenylphosphonate 28.1, to afford the coupled product 28.2. The preparation of aryl alkenyl phosphonates by means of a coupling reaction between aryl bromides and alkenyl phosphonates is described in Syn., 1983, 556. The reaction is performed in a polar organic solvent such as dimethylformamide or acetonitrile, in the presence of a palladium (II) catalyst, a tertiary base such as triethylamine and a phosphine such as triphenylphosphine and the like, to afford the aryl alkenyl phosphonate product 28.2. The latter compound is then reduced, for example by reaction with diimide, as described in Advanced Organic Chemistry, Part B, by F. A. Carey and R. J. Sundberg, Plenum, 2001, p. 262, to afford the saturated product 28.3. The latter compound is then converted, by means of the series of reactions shown in Scheme 3, into the oxirane 28.4.

For example, the cbz-protected 3-bromophenylalanine 28.5, prepared as described in Pept. Res., 1990, 3, 176, is coupled, in acetonitrile solution at 100° in a sealed tube, with a dialkyl vinylphosphonate 28.6, in the presence of palladium (II)acetate, tri-(o-tolyl)phosphine and triethylamine, as described in Syn., 1983, 556, to afford the coupled product 28.7. The product is then reduced with diimide, generated by treatment of disodium azodicarboxylate with acetic acid, as described in J. Am. Chem. Soc., 83, 3725, 1961, to yield the saturated product 28.8. This material is then converted, using the procedures shown in Scheme 3, into the oxirane 28.9.

Using the above procedures, but employing, in place of the 3-bromophenylalanine derivative 28.5, different bromo compounds 27.2, and/or different alkenyl phosphonates 28.1, the corresponding products 28.4 are obtained.

Scheme 29 illustrates the preparation of oxiranes 29.9 in which the phosphonate group is linked by means of an alkylene chain and an oxygen or sulfur atom. In this procedure, a substituted phenylalanine 29.1 is converted into the methyl ester 29.2 by means of a conventional acid-catalyzed esterification reaction. The hydroxy or mercapto substituent is then protected to afford the derivative 29.3. The protection of phenyl hydroxyl and mercapto groups is described respectively, in Protective Groups in Organic Synthesis, by T. W. Greene and P. G. M Wuts, Wiley, Second Edition 1990, p. 10, and p. 277. For example, hydroxyl and thiol substituents can be protected as trialkylsilyloxy groups. Trialkylsilyl groups are introduced by the reaction of the phenol or thiophenol with a chlorotrialkylsilane and a base such as imidazole, for example as described in Protective Groups in Organic Synthesis, by T. W. Greene and P. G. M Wuts, Wiley, Second Edition 1990, p. 10, p. 68-86. Alternatively, thiol substituents can be protected by conversion to tert-butyl, 9-fluorenylmethyl or adamantyl thioethers, or 4-methoxybenzyl thioethers, prepared by the reaction between the thiol and 4-methoxybenzyl chloride in the presence of ammonium hydroxide, as described in Bull. Chem. Soc. Jpn., 37, 433, 1974. The protected compound 29.3 is then transformed into the cbz derivative 29.4, using the procedure described above (Scheme 3). The O or S-protecting group is then removed to produce the phenol or thiol 29.5. Deprotection of phenols and thiophenols is described in Protective Groups in Organic Synthesis, by T. W. Greene and P. G. M Wuts, Wiley, Second Edition 1990. For example, trialkylsilyl ethers or thioethers can be deprotected by treatment with a tetraalkylammonium fluoride in an inert solvent such as tetrahydrofuran, as described in J. Am Chem. Soc., 94, 6190, 1972. Tert-butyl or adamantyl thioethers can be converted into the corresponding thiols by treatment with mercuric trifluoroacetate in aqueous acetic acid at ambient temperatures, as described in Chem. Pharm. Bull., 26, 1576, 1978 or by the use of mercuric acetate in trifluoroacetic acid. The resultant phenol or thiophenol 29.5 is then reacted with a dialkyl halo or alkylsulfonyloxyalkyl phosphonate 29.6, to yield the ether or thioether product 29.7. The alkylation reaction is performed at from ambient temperature to about 80°, in a polar organic solvent such as dimethylformamide or acetonitrile, in the presence of an organic or inorganic base such as dimethylaminopyridine, triethylamine, potassium carbonate or cesium carbonate. The methyl ester is then hydrolyzed, for example by treatment with lithium hydroxide in aqueous tetrahydrofuran, to afford the carboxylic acid 29.8. The latter compound is then transformed, by means of the reactions shown in Scheme 3, into the oxirane 29.9.

For example, as illustrated in Scheme 29, Example 1,4-mercaptophenylalanine 29.10, prepared as described in J. Amer. Chem. Soc., 1997, 119, 7173, is reacted with methanol at reflux temperature in the presence of p-toluenesulfonic acid, to yield the methyl ester 29.11. The thiol substituent is then protected by conversion to the S-adamantyl derivative 29.12, for example by reaction with adamantanol in trifluoroacetic acid, as described in Chem. Pharm. Bull., 26, 1576, 1978. The amino group in the product 29.12 is then protected by conversion to the cbz derivative 29.13, using the procedure described in Scheme 3. Removal of the S-protecting group, for example by treatment of the thioether 29.13 with mercuric trifluoroacetate in acetic acid, as described in Chem. Pharm. Bull., 26, 1576, 1978, then affords the thiophenol 29.14. The latter compound is then reacted in dimethylformamide solution with a dialkyl bromoalkylphosphonate, for example a dialkyl bromoethylphosphonate 29.15, (Aldrich) in the presence of a base such as cesium carbonate, and optionally in the presence of a catalytic amount of potassium iodide, to afford the thioether 29.16. The methyl ester is then hydrolyzed as described above, and the resultant carboxylic acid 29.17 is transformed, by means of the reactions shown in Scheme 3, into the oxirane 29.18.

As a further example of the method of Scheme 29, as shown in Example 2, 3-hydroxyphenylalanine 29.19 (Fluka) is converted into the methyl ester 29.20, and the phenolic hydroxyl group is then protected by reaction with one molar equivalent of tert-butylchlorodimethylsilane and imidazole in dimethylformamide, as described in J. Amer. Chem. Soc., 94, 6190, 1972, to produce the silyl ether 29.21. Conversion to the cbz derivative 29.22, as described above, followed by desilylation, using tetrabutylammonium fluoride in tetrahydrofuran, as described in J. Amer. Chem. Soc., 94, 6190, 1972, then affords the phenol 29.23. The phenolic hydroxyl group is then reacted in dimethylformamide solution with a dialkyl trifluoromethanesulfonyloxymethyl phosphonate, 29.24, prepared as described in Tet. Lett., 1986, 27, 1477, and a base such as triethylamine, to afford the ether 29.25. The methyl ester is then hydrolyzed, as described above, and the resultant carboxylic acid 29.26 is then transformed, by means of the series of reactions shown in Scheme 3, into the oxirane 29.27.

Using the above procedures, but employing, in place of the bromoethyl phosphonate 29.15, or the trifluoromethanesulfonyloxymethyl phosphonate 29.24, different bromoalkyl or trifluoromethanesulfonyloxyalkyl phosphonates 29.6, and/or different phenylalanine derivatives 29.1, the corresponding products 29.9 are obtained.

Scheme 27

Method

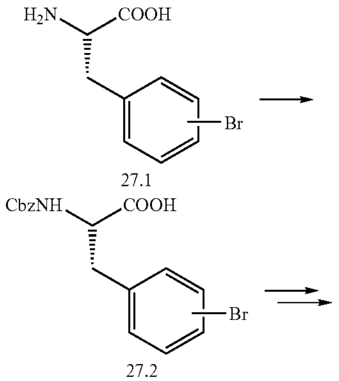

27.1

27.2

-continued
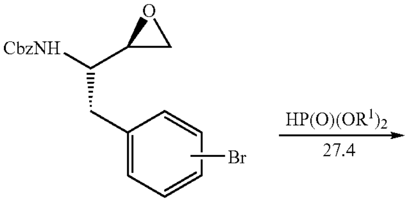
27.3
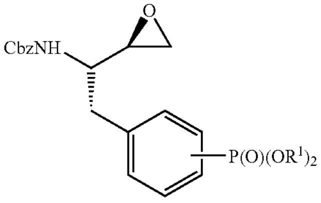
27.5
Example
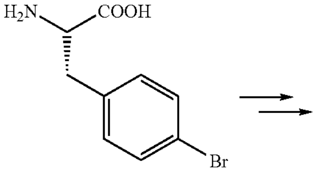
27.6
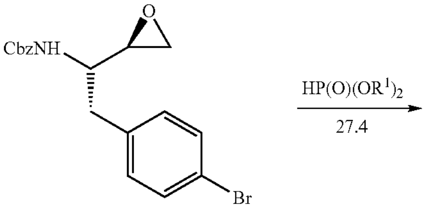
27.7
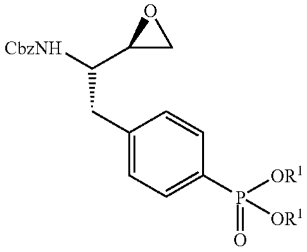
27.8
Scheme 28
Method
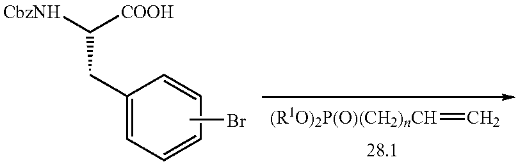
27.2
-continued
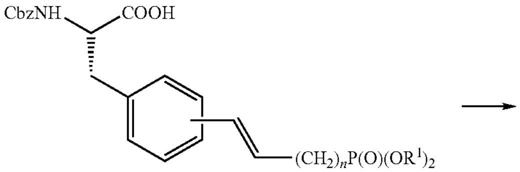
28.2
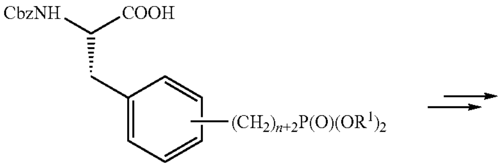
28.3
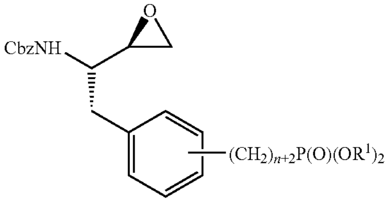
28.4
Example
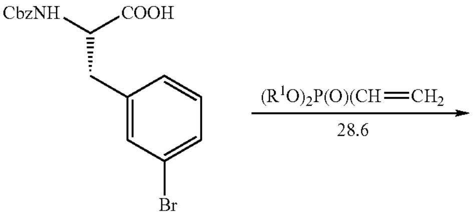
28.5
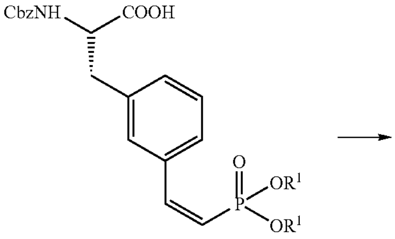
28.7
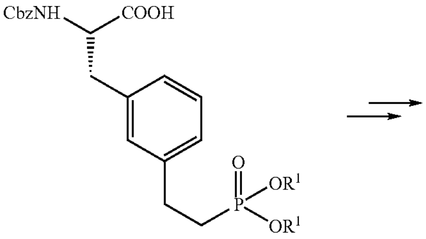
28.8

-continued
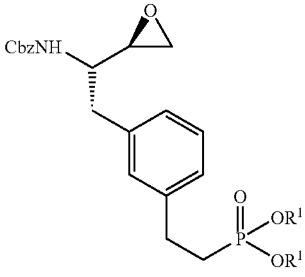
28.9
-continued
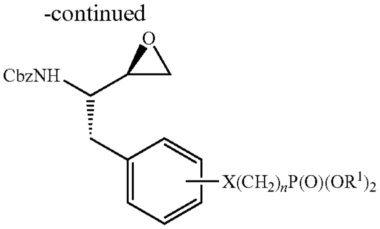
29.9
Scheme 29
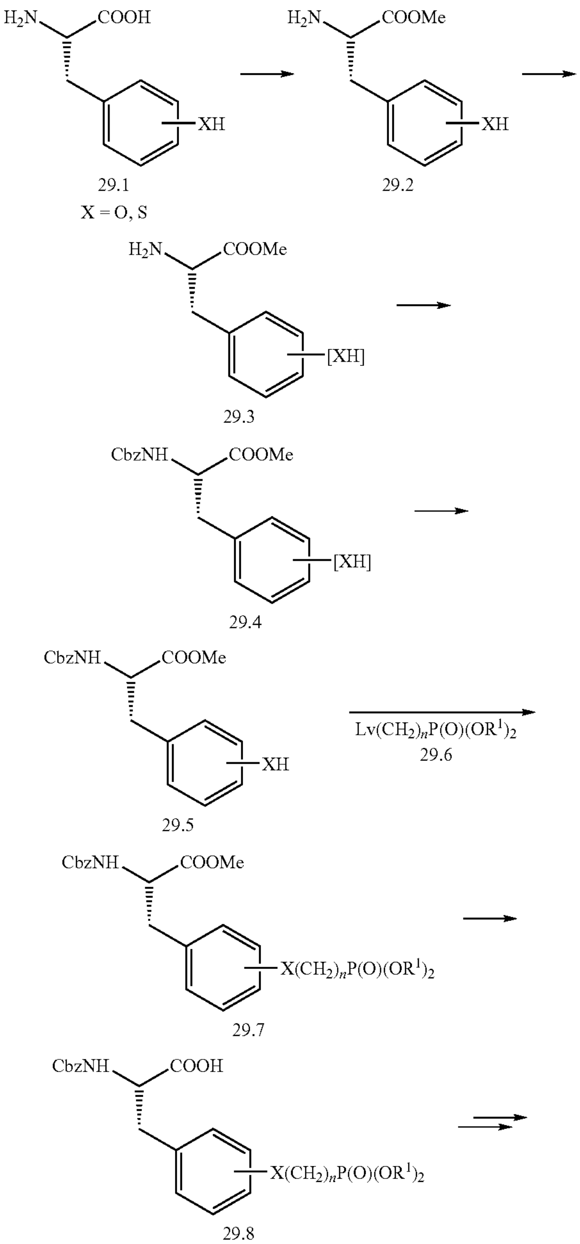
29.1
X = O, S
29.2
29.3
29.4
29.5
29.7
29.8
Example 1
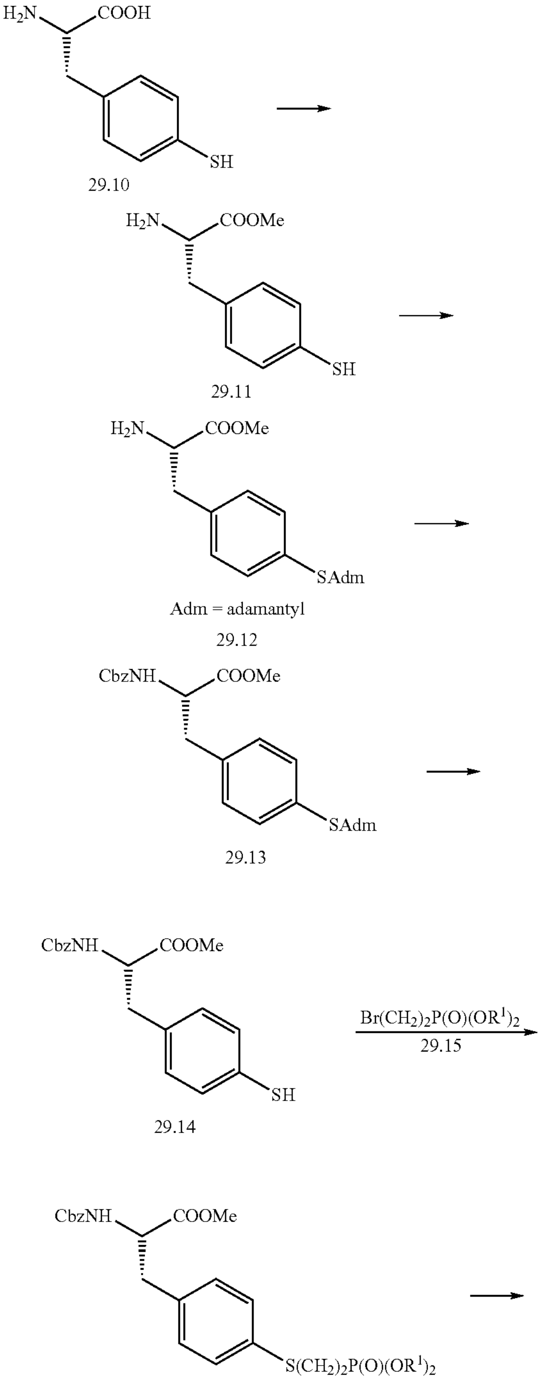
29.10
29.11
Adm = adamantyl
29.12
29.13
29.14
29.16

-continued

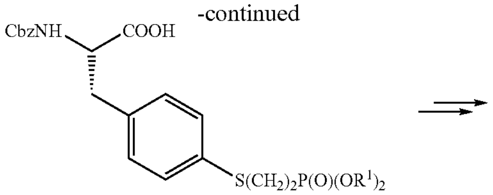

29.17

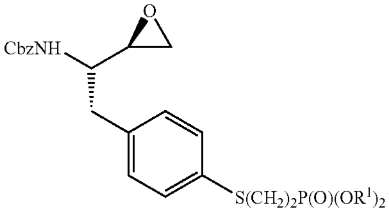

29.18

Example 2

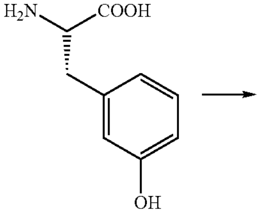

29.19

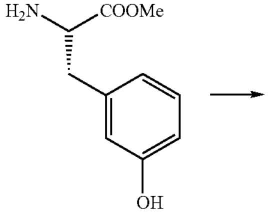

29.20

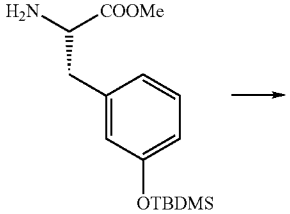

29.21

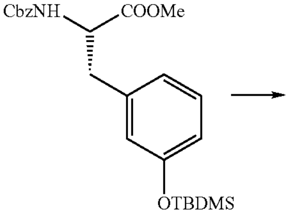

29.22

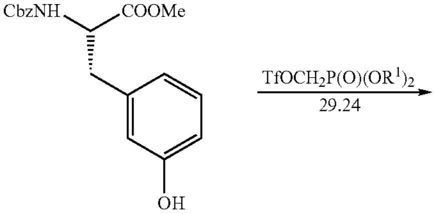

29.23

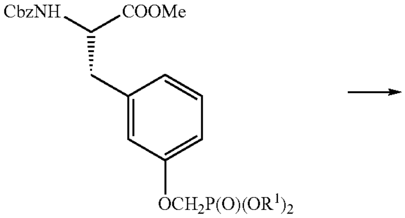

29.25

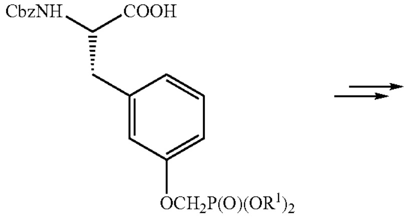

29.26

-continued

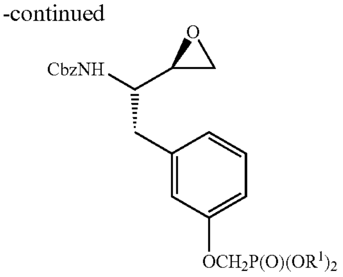

29.27

Preparation of the Phosphonate-containing Thiophenol Derivatives 10.1.

Schemes 30-39 describe the preparation of phosphonate-containing thiophenol derivatives 10.1 which are employed as described above (Schemes 10 and 11) in the preparation of the phosphonate ester intermediates 2.

Scheme 30 depicts the preparation of thiophenol derivatives in which the phosphonate moiety is attached directly to the phenyl ring. In this procedure, a halo-substituted thiophenol 30.1 is protected, as described above (Scheme 29) to afford the protected product 30.2. The product is then coupled, in the presence of a palladium catalyst, with a dialkyl phosphite 30.3. The preparation of arylphosphonates by the coupling of aryl halides with dialkyl phosphites us described above, (Scheme 29). The thiol protecting group is then removed, as described above, to afford the thiol 30.4.

For example, 3-bromothiophenol 30.5 is converted into the 9-fluorenylmethyl (Fm) derivative 30.6 by reaction with 9-fluorenylmethyl chloride and diisopropylamine in dimethylformamide, as described in Int. J. Pept. Protein Res., 20, 434, 1982. The product is then reacted with a dialkyl phosphite 30.3, as described for the preparation of the phosphonate 27.8 (Scheme 27), to afford the phosphonate ester 30.7. The Fm protecting group is then removed by treatment of the product with piperidine in dimethylformamide at ambient temperature, as described in J. Chem. Soc., Chem. Comm., 1501, 1986, to give the thiol 30.8.

Using the above procedures, but employing, in place of 3-bromothiophenol 30.5, different thiophenols 30.1, and/or different dialkyl phosphites 30.3, the corresponding products 30.4 are obtained.

Scheme 31 illustrates an alternative method for obtaining thiophenols with a directly attached phosphonate group. In this procedure, a suitably protected halo-substituted thiophenol 31.2 is metallated, for example by reaction with magnesium or by transmetallation with an alkyllithium reagent, to afford the metallated derivative 31.3. The latter compound is reacted with a halodialkyl phosphite 31.4 to afford the product 31.5; deprotection then affords the thiophenol 31.6

For example, 4-bromothiophenol 31.7 is converted into the S-triphenylmethyl (trityl) derivative 31.8, as described in Protective Groups in Organic Synthesis, by T. W. Greene and P. G. M. Wuts, Wiley, 1991, pp. 287. The product is converted into the lithium derivative 31.9 by reaction with butyllithium in an ethereal solvent at low temperature, and the resulting lithio compound is reacted with a dialkyl chlorodialkyl phosphite 31.10 to afford the phosphonate 31.11. Removal of the trityl group, for example by treatment with dilute hydrochloric acid in acetic acid, as described in J. Org. Chem., 31, 1118, 1966, then affords the thiol 31.12.

Using the above procedures, but employing, in place of the bromo compound 31.7, different halo compounds 31.2, and/or different halo dialkyl phosphites 31.4, there are obtained the corresponding thiols 31.6.

Scheme 32 illustrates the preparation of phosphonate-substituted thiophenols in which the phosphonate group is attached by means of a one-carbon link. In this procedure, a suitably protected methyl-substituted thiophenol is subjected to free-radical bromination to afford a bromomethyl product 32.1. This compound is reacted with a sodium dialkyl phosphite 32.2 or a trialkyl phosphite, to give the displacement or rearrangement product 32.3, which upon deprotection affords the thiophenol 32.4.

For example, 2-methylthiophenol 32.5 is protected by conversion to the benzoyl derivative 32.6, as described in Protective Groups in Organic Synthesis, by T. W. Greene and P. G. M. Wuts, Wiley, 1991, pp. 298. The product is reacted with N-bromosuccinimide in ethyl acetate to yield the bromomethyl product 32.7. This material is reacted with a sodium dialkyl phosphite 32.2, as described in J. Med. Chem., 35, 1371, 1992, to afford the product 32.8. Alternatively, the bromomethyl compound 32.7 can be converted into the phosphonate 32.8 by means of the Arbuzov reaction, for example as described in Handb. Organophosphorus Chem., 1992, 115. In this procedure, the bromomethyl compound 32.7 is heated with a trialkyl phosphate $P(OR^1)_3$ at ca. 100° to produce the phosphonate 32.8. Deprotection of the phosphonate 32.8, for example by treatment with aqueous ammonia, as described in J. Amer. Chem. Soc., 85, 1337, 1963, then affords the thiol 32.9.

Using the above procedures, but employing, in place of the bromomethyl compound 32.7, different bromomethyl compounds 32.1, there are obtained the corresponding thiols 32.4.

Scheme 33 illustrates the preparation of thiophenols bearing a phosphonate group linked to the phenyl nucleus by oxygen or sulfur. In this procedure, a suitably protected hydroxy or thio-substituted thiophenol 33.1 is reacted with a dialkyl hydroxyalkylphosphonate 33.2 under the conditions of the Mitsonobu reaction, for example as described in Org. React., 1992, 42, 335, to afford the coupled product 33.3. Deprotection then yields the O—or S-linked products 33.4.

For example, the substrate 3-hydroxythiophenol, 33.5, is converted into the monotrityl ether 33.6, by reaction with one equivalent of trityl chloride, as described above. This compound is reacted with diethyl azodicarboxylate, triphenyl phosphine and a dialkyl 1-hydroxymethyl phosphonate 33.7 in benzene, as described in Synthesis, 4, 327, 1998, to afford the ether compound 33.8. Removal of the trityl protecting group, as described above, then affords the thiophenol 33.9.

Using the above procedures, but employing, in place of the phenol 33.5, different phenols or thiophenols 33.1, and different dialkylphosphonates 33.2 there are obtained the corresponding thiols 33.4.

Scheme 34 illustrates the preparation of thiophenols 34.4 bearing a phosphonate group linked to the phenyl nucleus by oxygen, sulfur or nitrogen. In this procedure, a suitably protected O, or N-substituted thiophenol 34.1 is reacted with an activated ester, for example the trifluoromethanesulfonate 34.2, of a dialkyl hydroxyalkyl phosphonate, to afford the coupled product 34.3. Deprotection then affords the thiol 34.4.

For example, 4-methylaminothiophenol 34.5 is reacted with one equivalent of acetyl chloride, as described in Protective Groups in Organic Synthesis, by T. W. Greene and P. G. M. Wuts, Wiley, 1991, pp. 298, to afford the product 34.6. This material is then reacted with, for example, a dialkyl trifluoromethanesulfonylmethyl phosphonate 34.7, the preparation of which is described in Tet. Lett., 1986, 27, 1477, to afford the displacement product 34.8. Preferably, equimolar amounts of the phosphonate 34.7 and the amine 34.6 are reacted together in an aprotic solvent such as dichloromethane, in the presence of a base such as 2,6-lutidine, at ambient temperatures, to afford the phosphonate product 34.8. Deprotection, for example by treatment with dilute aqueous sodium hydroxide for two minutes, as described in J. Amer. Chem. Soc., 85, 1337, 1963, then affords the thiophenol 34.9.

Using the above procedures, but employing, in place of the thioamine 34.5, different phenols, thiophenols or amines 34.1, and/or different phosphonates 34.2, there are obtained the corresponding products 34.4.

Scheme 35 illustrates the preparation of phosphonate esters linked to a thiophenol nucleus by means of a heteroatom and a multiple-carbon chain, employing a nucleophilic displacement reaction on a dialkyl bromoalkyl phosphonate 35.2. In this procedure, a suitably protected hydroxy, thio or amino substituted thiophenol 35.1 is reacted with a dialkyl bromoalkyl phosphonate 35.2 to afford the product 35.3. Deprotection then affords the free thiophenol 35.4.

For example, 3-hydroxythiophenol 35.5 is converted into the S-trityl compound 35.6, as described above. This compound is then reacted with, for example, a dialkyl 4-bromobutyl phosphonate 35.7, the synthesis of which is described in Synthesis, 1994, 9, 909. The reaction is conducted in a dipolar aprotic solvent, for example dimethylformamide, in the presence of a base such as potassium carbonate, and optionally in the presence of a catalytic amount of potassium iodide, at about 50°, to yield the ether product 35.8. Deprotection, as described above, then affords the thiol 35.9.

Using the above procedures, but employing, in place of the phenol 35.5, different phenols, thiophenols or amines 35.1, and/or different phosphonates 35.2, there are obtained the corresponding products 35.4.

Scheme 36 depicts the preparation of phosphonate esters linked to a thiophenol nucleus by means of unsaturated and saturated carbon chains. The carbon chain linkage is formed by means of a palladium catalyzed Heck reaction, in which an olefinic phosphonate 36.2 is coupled with an aromatic bromo compound 36.1. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Deprotection, or hydrogenation of the double bond followed by deprotection, affords respectively the unsaturated phosphonate 36.4, or the saturated analog 36.6.

For example, 3-bromothiophenol is converted into the S—Fm derivative 36.7, as described above, and this compound is reacted with a dialkyl 1-butenyl phosphonate 36.8, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 100° to afford the coupled product 36.9. Deprotection, as described above, then affords the thiol 36.10. Optionally, the initially formed unsaturated phosphonate 36.9 is subjected to reduction, for example using diimide, as described above, to yield the saturated product 36.11, which upon deprotection affords the thiol 36.12.

Using the above procedures, but employing, in place of the bromo compound 36.7, different bromo compounds 36.1, and/or different phosphonates 36.2, there are obtained the corresponding products 36.4 and 36.6

Scheme 37 illustrates the preparation of an aryl-linked phosphonate ester 37.4 by means of a palladium(0) or palladium(II) catalyzed coupling reaction between a bromobenzene and a phenylboronic acid, as described in Comprehensive Organic Transformations, by R. C. Larock, VCH, 1989, p. 57. The sulfur-substituted phenylboronic acid 37.1 is obtained by means of a metallation-boronation sequence applied to a protected bromo-substituted thiophenol, for example as described in J. Org. Chem., 49, 5237, 1984. A coupling reaction then affords the diaryl product 37.3 which is deprotected to yield the thiol 37.4.

For example, protection of 4-bromothiophenol by reaction with tert-butylchlorodimethylsilane, in the presence of a base such as imidazole, as described in Protective Groups in Organic Synthesis, by T. W. Greene and P. G. M. Wuts, Wiley, 1991, p. 297, followed by metallation with butyllithium and boronation, as described in J. Organomet. Chem., 1999, 581, 82, affords the boronate 37.5. This material is reacted with diethyl 4-bromophenylphosphonate 37.6, the preparation of which is described in J. Chem. Soc., Perkin Trans., 1977, 2, 789, in the presence of tetrakis(triphenylphosphine)palladium (0) and an inorganic base such as sodium carbonate, to afford the coupled product 37.7. Deprotection, for example by the use of tetrabutylammonium fluoride in anhydrous tetrahydrofuran, then yields the thiol 37.8.

Using the above procedures, but employing, in place of the boronate 37.5, different boronates 37.1, and/or different phosphonates 37.2, there are obtained the corresponding products 37.4.

Scheme 38 depicts the preparation of dialkyl phosphonates in which the phosphonate moiety is linked to the thiophenyl group by means of a chain which incorporates an aromatic or heteroaromatic ring. In this procedure, a suitably protected O, S or N-substituted thiophenol 38.1 is reacted with a dialkyl bromomethyl-substituted aryl or heteroarylphosphonate 38.2, prepared, for example, by means of an Arbuzov reaction between equimolar amounts of a bis(bromo-methyl) substituted aromatic compound and a trialkyl phosphite. The reaction product 38.3 is then deprotected to afford the thiol 38.4. For example, 1,4-dimercaptobenzene is converted into the monobenzoyl ester 38.5 by reaction with one molar equivalent of benzoyl chloride, in the presence of a base such as pyridine. The mono-protected thiol 38.5 is then reacted with, for example diethyl 4-(bromomethyl) phenylphosphonate, 38.6, the preparation of which is described in Tetrahedron, 1998, 54, 9341. The reaction is conducted in a solvent such as dimethylformamide, in the presence of a base such as potassium carbonate, at about 50°. The thioether product 38.7 thus obtained is deprotected, as described above, to afford the thiol 38.8.

Using the above procedures, but employing, in place of the thiophenol 38.5, different phenols, thiophenols or amines 38.1, and/or different phosphonates 38.2, there are obtained the corresponding products 38.4.

Scheme 39 illustrates the preparation of phosphonate-containing thiophenols in which the attached phosphonate chain forms a ring with the thiophenol moiety.

In this procedure, a suitably protected thiophenol 39.1, for example an indoline (in which X—Y is $(CH_2)_2$), an indole (X—Y is CH═CH) or a tetrahydroquinoline (X—Y is $(CH_2)_3$) is reacted with a dialkyl trifluoromethanesulfonyloxymethyl phosphonate 39.2, in the presence of an organic or inorganic base, in a polar aprotic solvent such as, for example, dimethylformamide, to afford the phosphonate ester 39.3. Deprotection, as described above, then affords the thiol 39.4. The preparation of thio-substituted indolines is described in EP 209751. Thio-substituted indoles, indolines and tetrahydroquinolines can also be obtained from the corresponding hydroxy-substituted compounds, for example by thermal rearrangement of the dimethylthiocarbamoyl esters, as described in J. Org. Chem., 31, 3980, 1966. The preparation of hydroxy-substituted indoles is described in Syn., 1994, 10, 1018; preparation of hydroxy-substituted indolines is described in Tet. Lett., 1986, 27, 4565, and the preparation of hydroxy-substituted tetrahydroquinolines is described in J. Het. Chem., 1991, 28, 1517, and in J. Med. Chem., 1979, 22, 599. Thio-substituted indoles, indolines and tetrahydroquinolines can also be obtained from the corresponding amino and bromo compounds, respectively by diazotization, as described in Sulfur Letters, 2000, 24, 123, or by reaction of the derived organolithium or magnesium derivative with sulfur, as described in Comprehensive Organic Functional Group Preparations, A. R. Katritzky et al, eds, Pergamon, 1995, Vol. 2, p. 707. For example, 2,3-dihydro-1H-indole-5-thiol, 39.5, the preparation of which is described in EP 209751, is converted into the benzoyl ester 39.6, as described above, and the ester is then reacted with the trifluoromethanesulfonate 39.7, using the conditions described above for the preparation of the phosphonate 34.8, (Scheme 34), to yield the phosphonate 39.8.

Deprotection, for example by reaction with dilute aqueous ammonia, as described above, then affords the thiol 39.9.

Using the above procedures, but employing, in place of the thiol 39.5, different thiols 39.1, and/or different triflates 39.2, there are obtained the corresponding products 39.4.

Scheme 30

Method

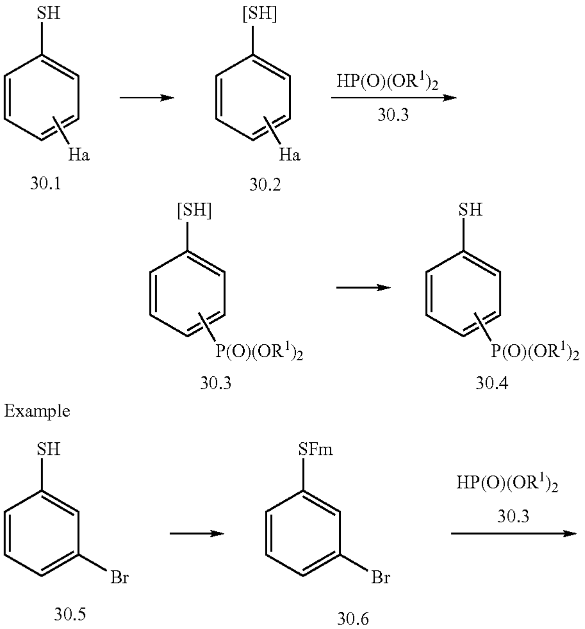

30.1 30.2 30.3 30.4

Example 30.5 30.6

Fm = 9-fluorenylmethyl

-continued
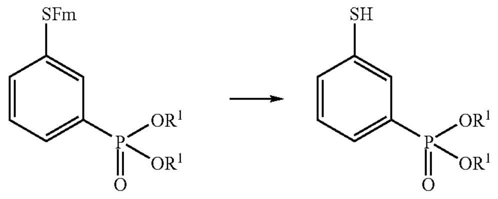
30.7 30.8
Scheme 31
Method
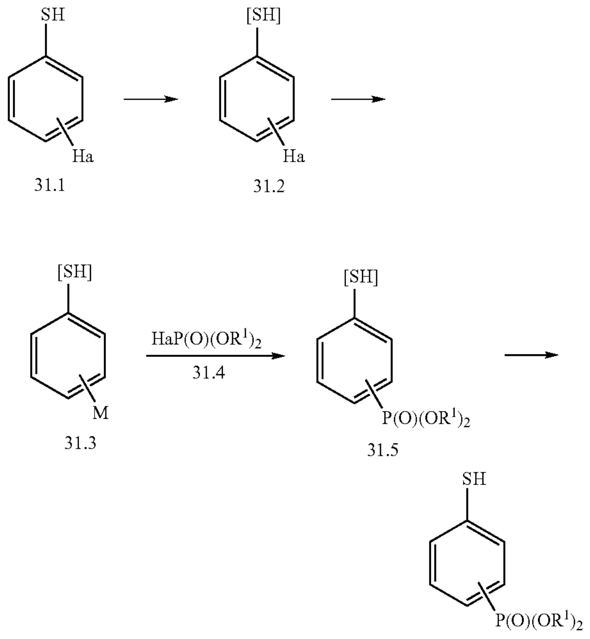
31.1 31.2 31.3 31.5 31.6
Example
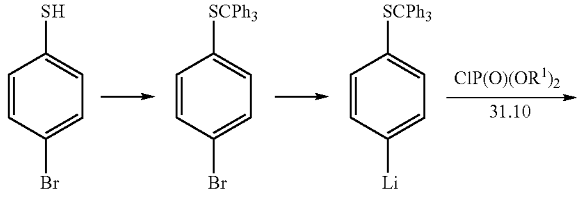
31.7 31.8 31.9
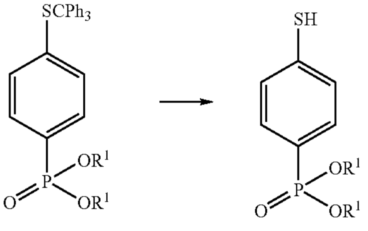
31.11 31.12
Scheme 32
Method
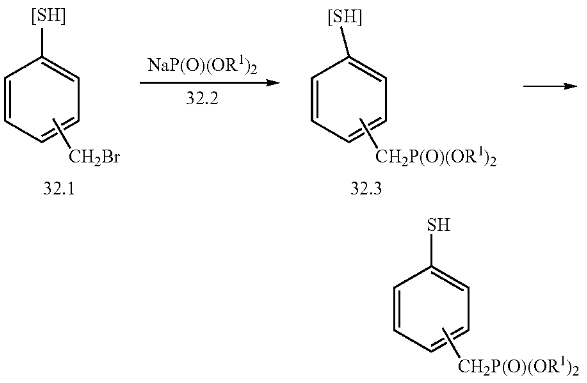
32.1 32.3 32.4
Example
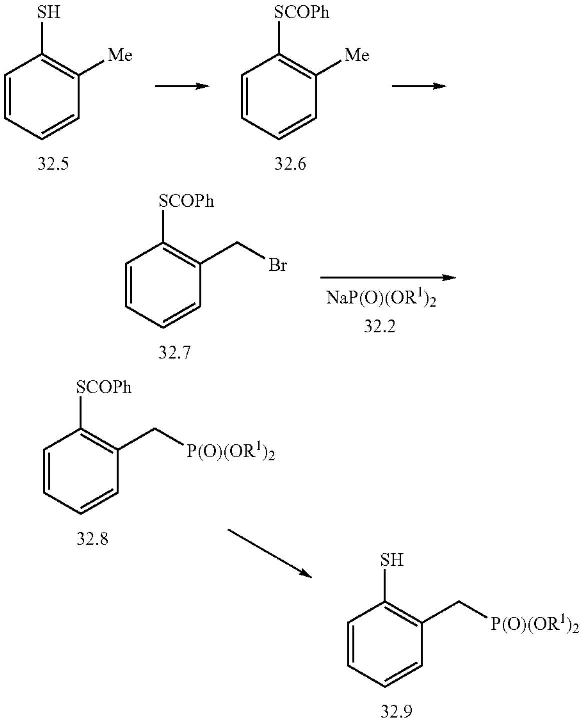
32.5 32.6 32.7 32.8 32.9
Scheme 33
Method
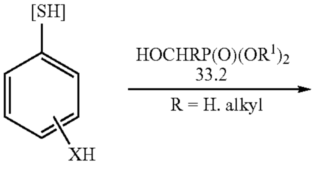
X = O, S
33.1

-continued
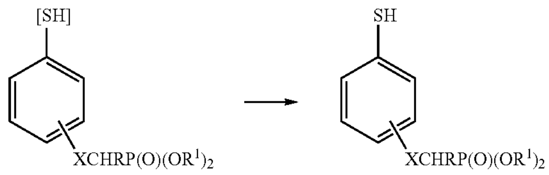
33.3 33.4
Example
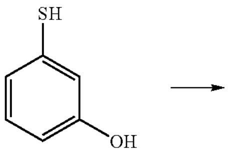
33.5
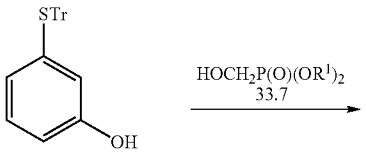
Tr = triphenylmethyl
33.6
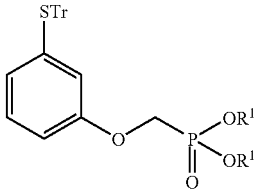
33.8
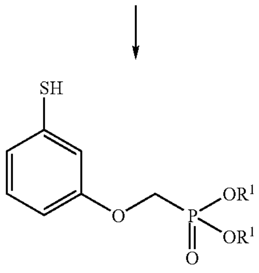
33.9
Scheme 34
Method
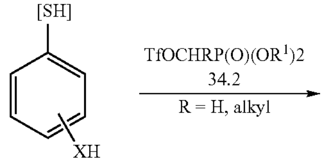
X = O, S, NH, Nalkyl
34.1
-continued
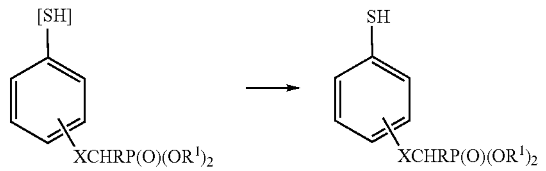
34.3 34.4
Example
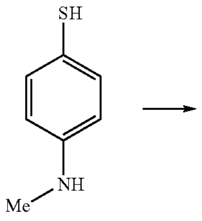
34.5
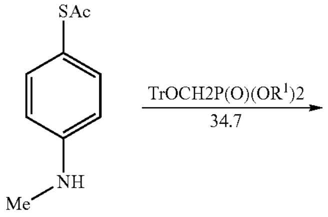
34.6
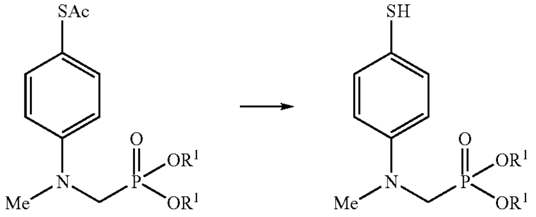
34.8 34.9
Scheme 35
Method
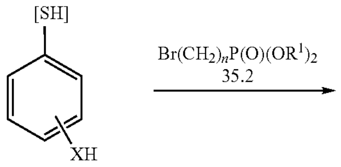
X = O, S, NH, Nalkyl
35.1
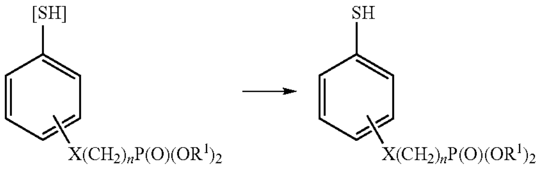
35.3 35.4

-continued
Example
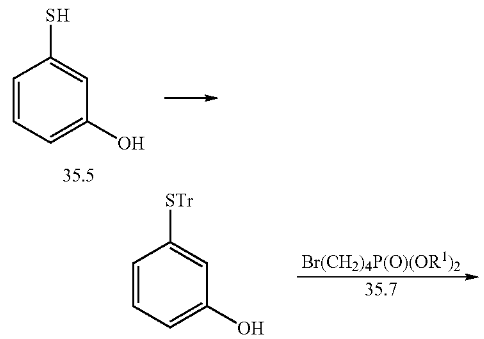
35.5
Tr = triphenylmethyl
35.6
-continued
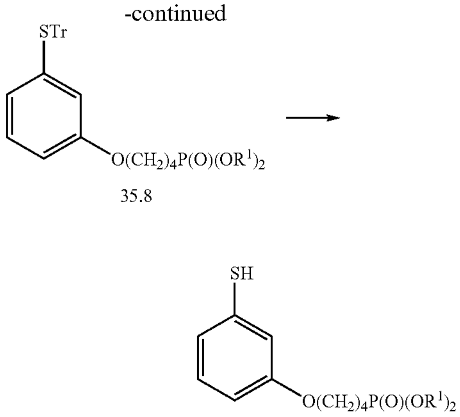
35.8
35.9
Scheme 36
Method
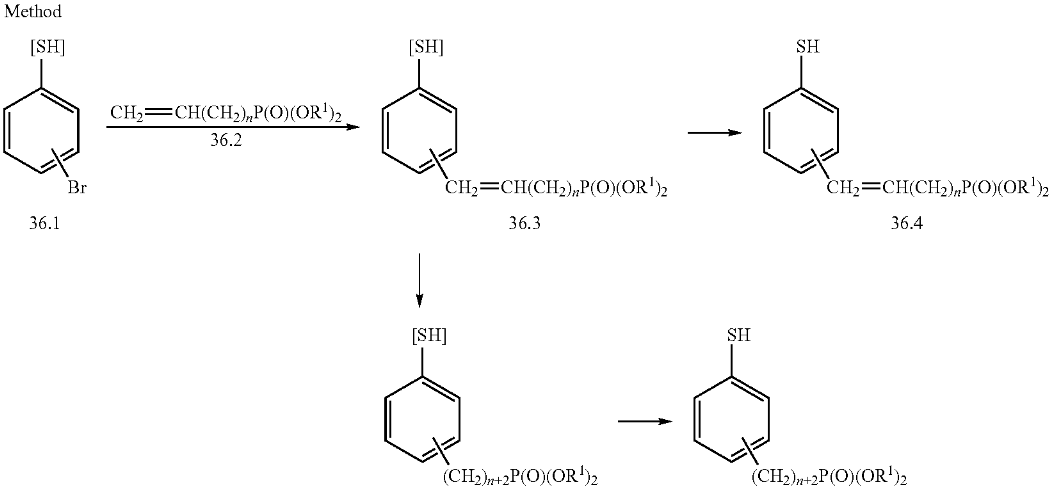
36.1
36.3
36.4
36.5
36.6
Example
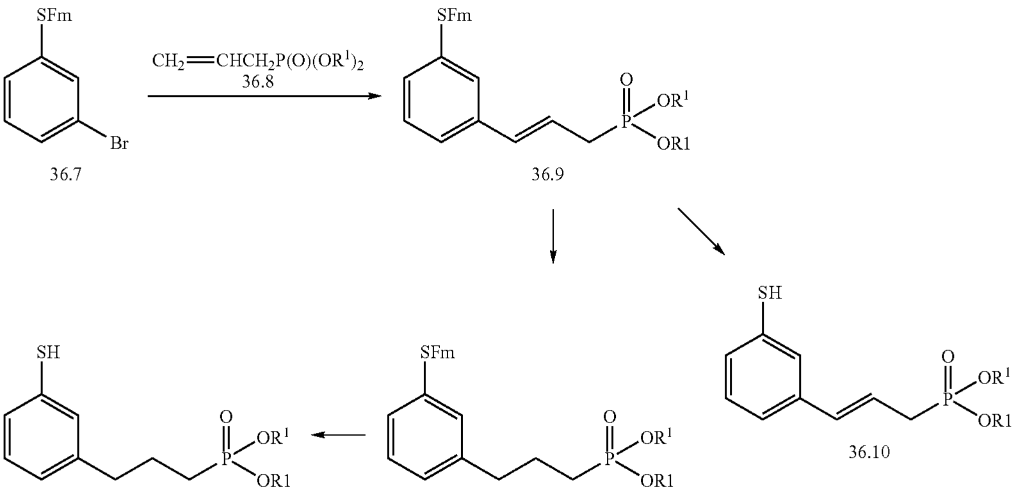
36.7
36.9
36.10
36.11
36.12

Scheme 37
Method
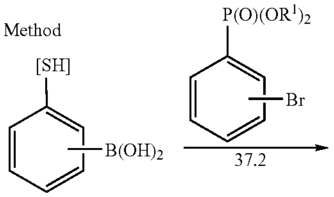
37.1
37.2
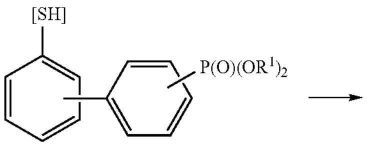
37.3
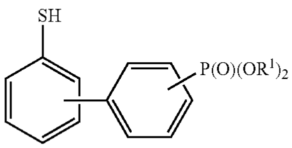
37.4
Example
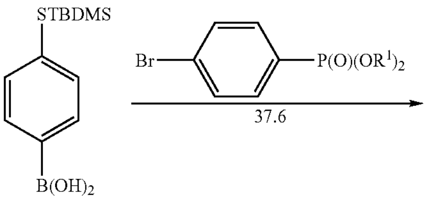
37.5
37.6
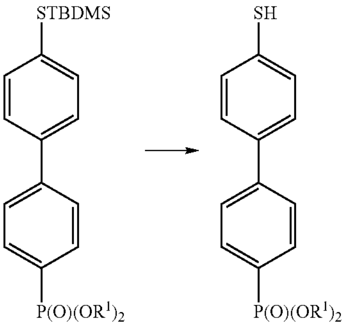
37.7
37.8
Scheme 38
Method
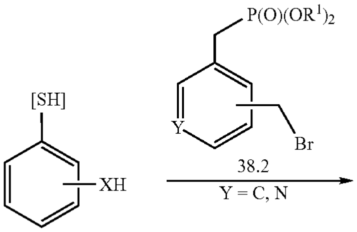
X = O, S, NH, Nalkyl
38.1
38.2
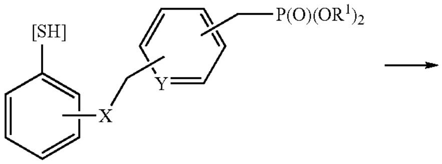
38.3
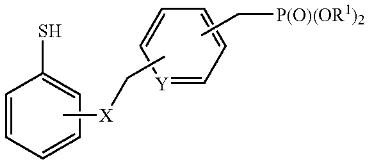
38.4
Example
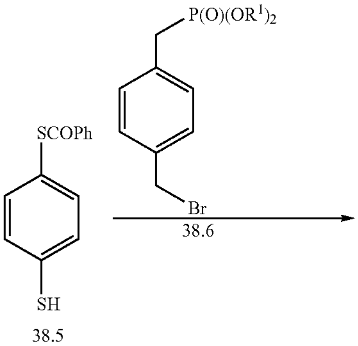
38.5
38.6
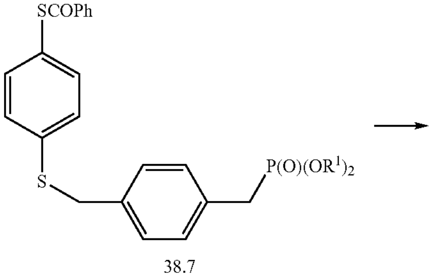
38.7

-continued

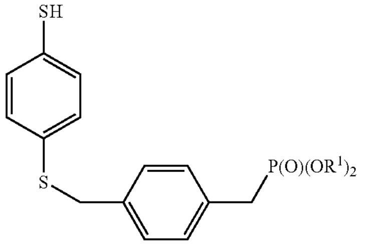

38.8

Scheme 39

Method

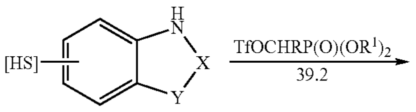

39.1

X—Y═(CH$_2$)$_2$, 3;
CH═CH

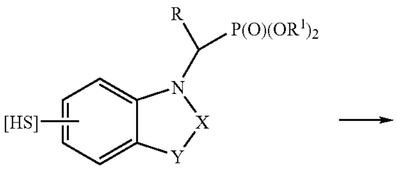

39.3

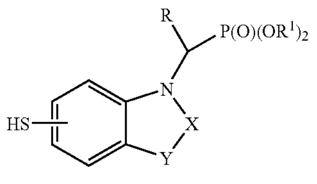

39.4

Example

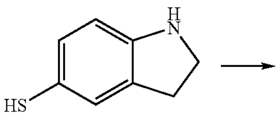

39.5

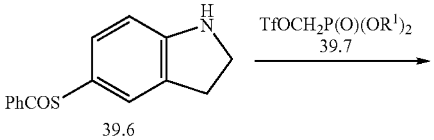

39.6

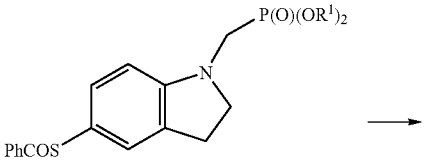

39.8

-continued

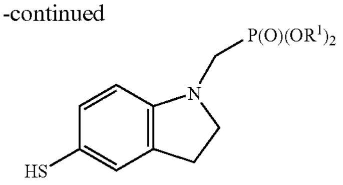

39.9

Preparation of the Phenylpyridylphosphonate Aldehydes 4.9.

Schemes 40 and 41 illustrate methods for the preparation of 4-(2-pyridyl)benzaldehydes 4.9 incorporating phosphonate groups, which are employed in the preparation of the phosphonate ester intermediates 3a.

Scheme 40 illustrates the preparation of benzaldehydes substituted at the 4 position with a bromo-substituted 2-pyridine group, and the conversion of the bromo substituent into various phosphonate substituents, linked to the pyridine ring either directly, or by means of a saturated or unsaturated alkylene chain, or by a heteroatom and an alkylene chain.

In this procedure, a 4-formylphenylboronate 40.1 (Lancaster Synthesis) is coupled with a dibromopyridine 40.2 to afford the bromopyridyl benzaldehyde product 40.3. Equimolar amounts of the reactants are combined in the presence of a palladium catalyst, as described above (Scheme 4). The bromopyridine product 40.3 is then reacted with a dialkyl phosphite 40.4, in the presence of a palladium catalyst, as described above (Scheme 27) to afford the pyridylphosphonate ester 40.5. The preparation of arylphosphonates by means of a coupling reaction between aryl bromides and dialkyl phosphites is described in J. Med. Chem., 35, 1371, 1992.

Alternatively, the bromopyridine compound 40.3 is coupled, in the presence of a palladium catalyst, with a dialkyl alkenylphosphonate 40.6, to yield the alkenyl phosphonate 40.9, using the procedures described above, (Scheme 28). The olefinic bond present in the product is then reduced to afford the saturated analog 40.8. The reduction reaction is performed catalytically, for example by the use of palladium on carbon and hydrogen or a hydrogen donor, or chemically, for example by employing diimide, generated by treatment of disodium azodicarboxylate with acetic acid, as described in J. Am. Chem. Soc., 83, 3725, 1961. Alternatively, the bromopyridine compound 40.3, in which the bromo substituent is in either the 4 or 6 position, is transformed, by reaction with a dialkyl hydroxy, mercapto or aminoalkyl phosphonate 40.7, into the ether, thioether or amine product 40.10. The preparation of pyridine ethers, thioethers and amines by means of displacement reactions of 2- or 4-bromopyridines by alcohols, thiols and amines is described, for example, in Heterocyclic Compounds, Volume 3, R. A. Abramovitch, ed., Wiley, 1975, p. 597, 191, and 41 respectively. Equimolar amounts of the reactants are combined in a polar solvent such as dimethylformamide at ca 100° in the presence of a base such as potassium carbonate, to effect the displacement reaction.

Scheme 40, Example 1, illustrates the coupling reaction of 4-formylphenylboronic acid 40.1 with 2,5-dibromopyridine 40.11, using the procedure described above, to afford 4-(5-bromo-2-pyridyl)benzaldehyde 40.12. This compound is then coupled, as described above, with a dialkyl phosphite 40.4, to afford the pyridyl phosphonate 40.13.

Using the above procedures, but employing, in place of 2,5-dibromopyridine 40.11, different dibromopyridines 40.2, and/or different dialkyl phosphites 40.4, the corresponding products 40.5 are obtained.

Alternatively, as illustrated in Scheme 40, Example 2, the phenylboronic acid 40.1 is coupled, as described above, with 2,4-dibromopyridine 40.14 to afford 4-(4-bromo-2-pyridyl) benzaldehyde 40.15. The product is then reacted with a dialkyl mercaptoethyl phosphonate 40.16, the preparation of which is described in Zh. Obschei. Khim., 1973, 43, 2364, to yield the thioether 40.17. Equimolar amounts of the reactants are combined in dimethylformamide at 80° in the presence of potassium carbonate, to effect the displacement reaction.

Using the above procedures, but employing, in place of the dialkyl mercaptoethyl phosphonate 40.16, different dialkyl hydroxy, mercapto or aminoalkyl phosphonates 40.7, the corresponding products 40.10 are obtained.

Alternatively, as shown in Scheme 40, Example 3,4-(5-bromo-2-pyridyl)benzaldehyde 40.12 is coupled with a dialkyl vinyl phosphonate 40.18, in the presence of a palladium catalyst, as described above, to afford the unsaturated phosphonate 40.19. Optionally, the product can be reduced to the saturated analog 40.20, for example by the use of diimide, as described above.

Using the above procedures, but employing, in place of the bromoaldehyde 40.12, different bromoaldehydes 40.3, and/or, in place of the dialkyl vinylphosphonate 40.18, different dialkyl alkenylphosphonates 40.6, the corresponding products 40.8 and 40.9 are obtained.

Scheme 41 illustrates the preparation of 4-(2-pyridyl)benzaldehydes incorporating phosphonate group linked by means of a alkylene chain incorporating a nitrogen atom. In this procedure, a formyl-substituted 2-bromopyridine 41.2 is coupled, as described above, (Scheme 40) with a 4-(hydroxymethyl)phenylboronic acid 41.1. prepared as described in Macromolecules, 2001, 34, 3130, to afford the 4-(2-pyridyl)benzyl alcohol 41.3. The product is then reacted with a dialkyl aminoalkyl phosphonate 41.4, under reductive amination conditions. The preparation of amines by means of a reductive amination of an aldehyde is described above (Scheme 24). The resultant benzyl alcohol 41.5 is then oxidized to yield the corresponding benzaldehyde 41.6. The conversion of alcohols to aldehydes is described, for example, in Comprehensive Organic Transformations, by R. C. Larock, VCH, 1989, p. 604ff. Typically, the alcohol is reacted with an oxidizing agent such as pyridinium chlorochromate, silver carbonate, or dimethyl sulfoxide/acetic anhydride. The reaction is conducted in an inert aprotic solvent such as dichloromethane or toluene. Preferably, the alcohol 41.5 is oxidized to the aldehyde 41.6 by reaction with pyridinium chlorochromate in dichloromethane.

For example, the phenylboronic acid 41.1 is coupled with 2-bromopyridine-4-carboxaldehyde 41.7, the preparation of which is described in Tet. Lett. 2001, 42, 6815, to afford 4-(4-formyl-2-pyridyl)benzyl alcohol 41.8. The aldehyde is then reductively aminated by reaction with a dialkyl aminoethylphosphonate 41.9, the preparation of which is described in J. Org. Chem., 2000, 65, 676, and a reducing agent, to afford the amine product 41.10. The latter compound is then oxidized, for example by treatment with pyridinium chlorochromate, to afford the aldehyde phosphonate 41.11.

Using the above procedures, but employing, in place of the bromopyridine aldehyde 41.7, different aldehydes 41.2, and/or different dialkyl aminoalkyl phosphonates 41.4, the corresponding products 41.6 are obtained.

Scheme 40

Method

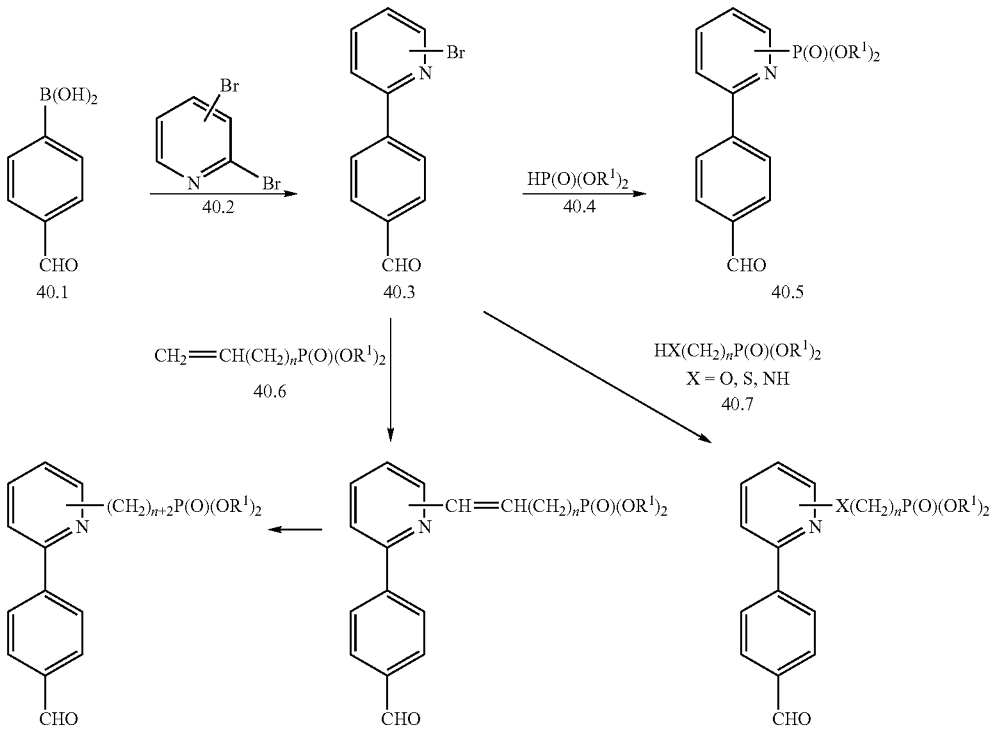

40.1 40.2 40.3 40.5

40.8 40.9 40.10

-continued
Example 1
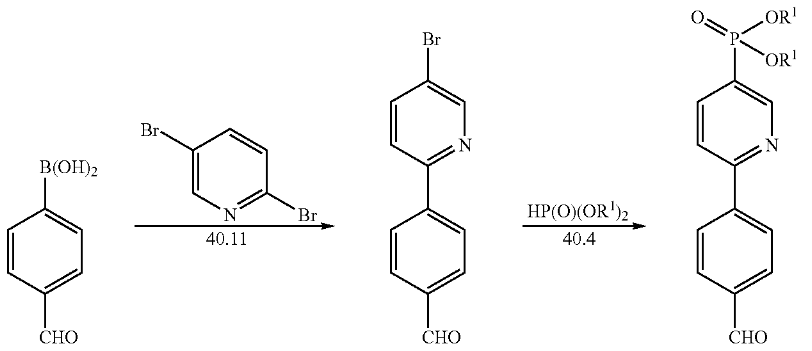
40.1 40.12 40.13
Example 2
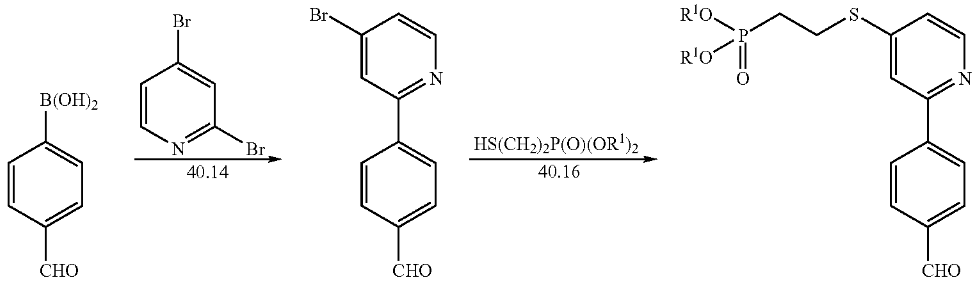
40.1 40.15 40.17
Example 3
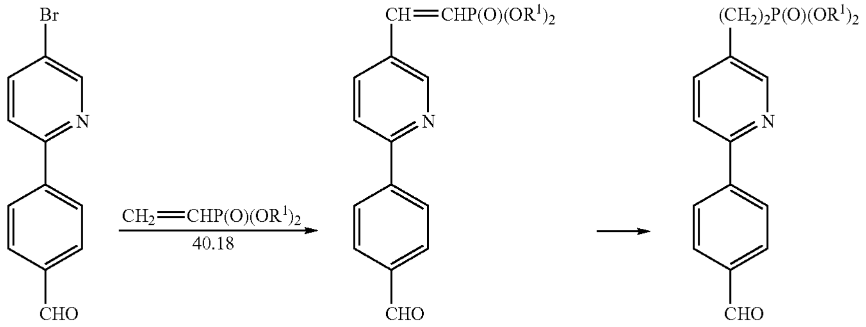
40.12 40.19 40.20
Scheme 41
Method
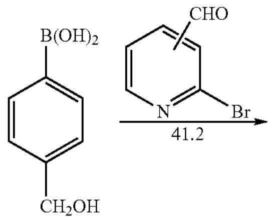
41.1
-continued
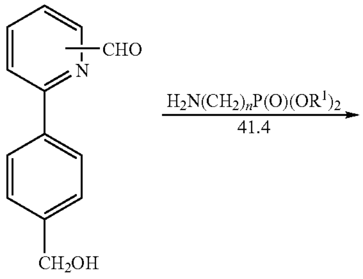
41.3

-continued

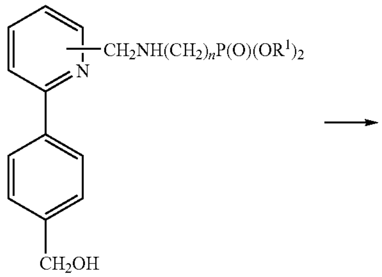

41.5

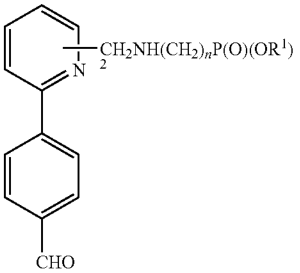

41.6

Example

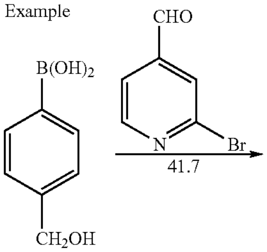

41.7

41.1

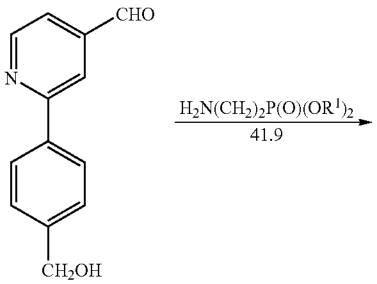

41.9

41.8

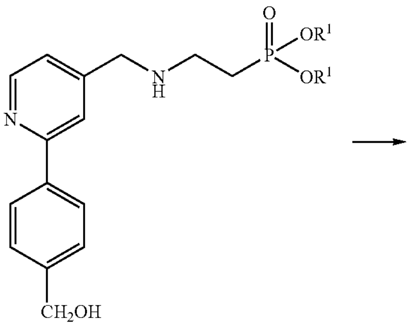

41.10

-continued

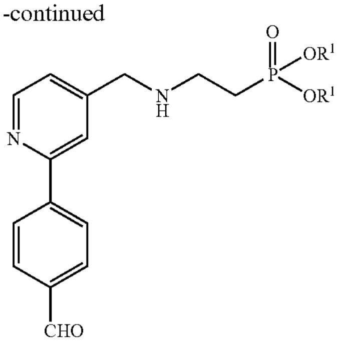

41.11

Preparation of the Biphenyl Phosphonate Aldehydes 4.12.

Schemes 42-44 illustrate methods for the preparation of the biphenylphosphonate aldehydes 4.12 which are employed in the synthesis of the phosphonate esters 3b.

Scheme 42 depicts the preparation of biphenyl aldehyde phosphonates in which the phosphonate moiety is attached to the phenyl ring either directly, or by means of a saturated or unsaturated alkylene chain. In this procedure, 4-formylbenzeneboronic acid 42.1 and a dibromobenzene 42.2 are coupled in the presence of a palladium catalyst, as described above, to produce the bromobiphenyl aldehyde 42.3. The aldehyde is then coupled, as described above, with a dialkyl phosphite 42.4, to afford the phosphonate ester 42.5. Alternatively, the bromoaldehyde 42.3 is coupled with a dialkyl alkenylphosphonate 42.6, using the procedures described above, to afford the alkenyl phosphonate 42.8. Optionally, the latter compound is reduced to yield the saturated analog 42.7.

For example, as shown in Scheme 42, Example 1,4-formylbenzeneboronic acid 42.1 is coupled with 1,3-dibromobenzene 42.9 to give 3'-bromo-4-formylbiphenyl 42.10. The product is then coupled, as described above, with a dialkyl phosphite 42.4 to give the biphenyl phosphonate ester 42.11.

Using the above procedures, but employing, in place of 1,3-dibromobenzene 42.9, different dibromobenzenes 42.2, and/or different dialkyl phosphites 42.4, the corresponding products 42.5 are obtained.

As a further example of the methods of Scheme 42, as shown in Example 2,4'-bromobiphenyl-4-aldehyde 42.12 is coupled with a dialkyl propenylphosphonate 42.13 (Aldrich) in the presence of a palladium catalyst, to produce the propenyl phosphonate 42.15. Optionally, the product is reduced, for example by catalytic hydrogenation over a palladium catalyst, to yield the saturated product 42.16.

Using the above procedures, but employing, in place of the 4-bromobiphenyl aldehyde 42.12, different bromobiphenyl aldehydes, and/or different alkenyl phosphonates 42.6, the corresponding products 42.7 and 42.8 are obtained.

Scheme 43 illustrates the preparation of biphenyl phosphonates in which the phosphonate group is attached by means of a single carbon or by a heteroatom O, S or N and an alkylene chain. In this procedure, a bromotoluene 43.2 is coupled with 4-formylbenzeneboronic acid 43.1 to yield the methyl-substituted biphenyl aldehyde 43.3. The product is then subjected to a free radical bromination to produce the bromomethyl compound 43.4. The conversion of aromatic methyl groups into the corresponding benzylic bromide is described in Comprehensive Organic Transformations, by R. C. Larock, VCH, 1989, p. 313. The transformation is effected, for example, by the use of bromine, N-bromosuccinimide, carbon tetrabromide or bromotrichloromethane. The reaction is performed in an inert organic solvent such as carbon tetrachloride, ethyl acetate and the like, at reflux temperature, optionally in the presence of an initiator such as dibenzoyl peroxide. Preferably, the conversion of the methyl compound 43.3 to the bromomethyl product 43.4 is effected by the use of one molar equivalent of N-bromosuccinimide in refluxing carbon tetrachloride. The bromomethyl compound is then reacted with a sodium dialkyl phosphonate 43.5 to afford the phosphonate product 43.6. The displacement reaction is performed in an inert solvent such as tetrahydrofuran, at from ambient temperature to reflux, as described in J. Med. Chem., 1992, 35, 1371.

Alternatively, the bromomethyl compound 43.4 is reacted with a dialkyl hydroxy, mercapto or aminoalkyl phosphonate 43.7 to prepare the corresponding ether, thioether or aminoalkyl phosphonate products 43.8. The reaction is performed in a polar organic solvent such as dimethylformamide, acetonitrile and the like, at from ambient temperature to about 80°, in the presence of an inorganic or organic base. For the preparation of the ethers 43.8 in which X is O, a strong base such as sodium hydride or potassium tert. butoxide is employed. For the preparation of the thioethers or amines 43.8, a base such as cesium carbonate, dimethylaminopyridine or diisopropylethylamine is employed.

Scheme 43, Example 1 depicts the coupling reaction of 4-formylbenzeneboronic acid 43.1 with 3-bromotoluene 43.9 to afford 3'-methylbiphenyl-4-aldehyde 43.10. The product is then reacted with N-bromosuccinimide, as described above, to afford the bromomethyl product 43.11. This material is reacted with a sodium dialkyl phosphonate 43.5 to afford the phosphonate ester 43.12.

Using the above procedures, but employing, in place of 3-bromotoluene 43.9, different bromotoluenes 43.2, the corresponding products 43.6 are obtained.

Scheme 43, Example 2 shows the free-radical bromination of 4'-methylbiphenyl-4-aldehyde to give the 4'-bromomethylbiphenyl-4-aldehyde 43.14. The product is then reacted in acetonitrile solution at 70° with one molar equivalent of a dialkyl aminoethyl phosphonate 43.15, the preparation of which is described in J. Org. Chem., 2000, 65, 676, and cesium carbonate, to yield the amine product 43.16.

Using the above procedures, but employing, in place of the aminoethyl phosphonate 43.15, different hydroxy, mercapto or aminoalkyl phosphonates 43.7, and/or different biphenyl aldehydes 43.3, the corresponding products 43.8 are obtained.

Scheme 44 illustrates the preparation of the biphenyl phosphonates 44.3 in which the phosphonate group is attached by means of a heteroatom and an alkylene chain. In this procedure, a hydroxy, mercapto or amino-substituted biphenyl aldehyde 44.1 is reacted with a dialkyl bromoalkyl phosphonate 44.2 to afford the alkylation product 44.3. The reaction is conducted between equimolar amounts of the reactants in a polar organic solvent such as dimethylformamide and the like, at from ambient temperature to about 80°, in the presence of a base such as potassium carbonate, and optionally in the presence of a catalytic amount of an inorganic iodide such as potassium iodide.

For example, 3'-hydroxybiphenyl-4-aldehyde 44.4 is reacted with a dialkyl bromoethyl phosphonate 44.5 (Aldrich) and potassium carbonate in dimethylformamide at 80°, to produce the ether 44.6.

Using the above procedures, but employing, in place of 3'-hydroxybiphenyl-4-aldehyde 44.4, different hydroxy, mercapto or aminobiphenyl-4-aldehydes 44.1, and/or different bromoalkyl phosphonates 44.2, the corresponding products 44.3 are obtained.

Preparation of the Benzaldehyde Phosphonates 4.14.

Schemes 45-48 illustrate methods for the preparation of the benzaldehyde phosphonates 4.14 which are employed in the synthesis of the phosphonate esters 3d.

Scheme 45 illustrates the preparation of benzaldehyde phosphonates 45.3 in which the phosphonate group is attached by means of an alkylene chain incorporation a nitrogen atom. In this procedure, a benzene dialdehyde 45.1 is reacted with one molar equivalent of a dialkyl aminoalkyl phosphonate 45.2, under reductive amination conditions, as describe above in Scheme 24, to yield the phosphonate product 45.3.

For example, benzene-1,3-dialdehyde 45.4 is reacted with a dialkyl aminopropyl phosphonate 45.5, (Acros) and sodium triacetoxyborohydride, to afford the product 45.6.

Using the above procedures, but employing, in place of benzene-1,3-dicarboxaldehyde 45.4, different benzene dialdehydes 45.1, and/or different phosphonates 45.2, the corresponding products 45.3 are obtained.

Scheme 46 illustrates the preparation of benzaldehyde phosphonates either directly attached to the benzene ring or attached by means of a saturated or unsaturated carbon chain. In this procedure, a bromobenzaldehyde 46.1 is coupled, under palladium catalysis as described above, with a dialkyl alkenylphosphonate 46.2, to afford the alkenyl phosphonate 46.3. Optionally, the product can be reduced, as described above, to afford the saturated phosphonate ester 46.4. Alternatively, the bromobenzaldehyde can be coupled, as described above, with a dialkyl phosphite 46.5 to afford the formylphenylphosphonate 46.6.

For example, as shown in Example 1,3-bromobenzaldehyde 46.7 is coupled with a dialkyl propenylphosphonate 46.8 to afford the propenyl product 46.9. Optionally, the product is reduced to yield the propyl phosphonate 46.10.

Using the above procedures, but employing, in place of 3-bromobenzaldehyde 46.7, different bromobenzaldehydes 46.1, and/or different alkenyl phosphonates 46.2, the corresponding products 46.3 and 46.4 are obtained.

Alternatively, as shown in Example 2,4-bromobenzaldehyde 46.11 is coupled with a dialkyl phosphite 46.5 to afford the 4-formylphenyl phosphonate product 46.12.

Using the above procedures, but employing, in place of 4-bromobenzaldehyde 46.11, different bromobenzaldehydes 46.1, the corresponding products 46.6 are obtained.

Scheme 47 illustrates the preparation of formylphenyl phosphonates in which the phosphonate moiety is attached by means of alkylene chains incorporating two heteroatorns O, S or N. In this procedure, a formyl phenoxy, phenylthio or phenylamino alkanol, alkanethiol or alkylamine 47.1 is reacted with a an equimolar amount of a dialkyl haloalkyl phosphonate 47.2, to afford the phenoxy, phenylthio or phenylamino phosphonate product 47.3. The alkylation reaction is effected in a polar organic solvent such as dimethylformamide or acetonitrile, in the presence of a base. The base employed depends on the nature of the nucleophile 47.1. In cases in which Y is O, a strong base such as sodium hydride or lithium hexamethyldisilazide is employed. In cases in which Y is O or N, a base such as cesium carbonate or dimethylaminopyridine is employed.

For example, 2-(4-formylphenylthio)ethanol 47.4, prepared as described in Macromolecules, 1991, 24, 1710, is reacted in acetonitrile at 60° with one molar equivalent of a dialkyl iodomethyl phosphonate 47.5, (Lancaster) to give the ether product 47.6.

Using the above procedures, but employing, in place of the carbinol 47.4, different carbinols, thiols or amines 47.1, and/or different haloalkyl phosphonates 47.2, the corresponding products 47.3 are obtained.

Scheme 48 illustrates the preparation of formylphenyl phosphonates in which the phosphonate group is linked to the benzene ring by means of an aromatic or heteroaromatic ring. In this procedure, 4-formylbenzeneboronic acid 43.1 is coupled, as described previously, with one molar equivalent of a dibromoarene, 48.1, in which the group Ar is an aromatic or heteroaromatic group. The product 48.2 is then coupled, as described above (Scheme 46) with a dialkyl phosphite 40.4 to afford the phosphonate 48.3.

For example, 4-formylbenzeneboronic acid 43.1 is coupled with 2,5-dibromothiophene 48.4 to yield the phenylthiophene product 48.5. This compound is then coupled with the dialkyl phosphite 40.4 to afford the thienyl phosphonate 48.6.

Using the above procedures, but employing, in place of dibromothiophene 48.4, different dibromoarenes 48.1, the corresponding products 48.3 are obtained.

Scheme 42

Method

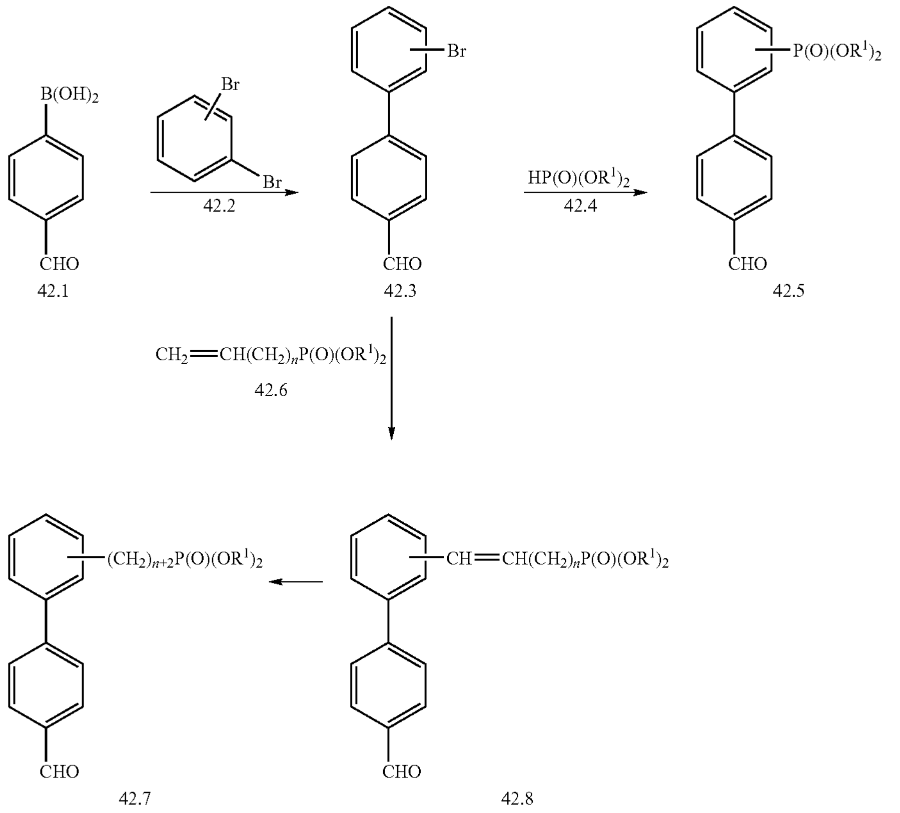

Example 1

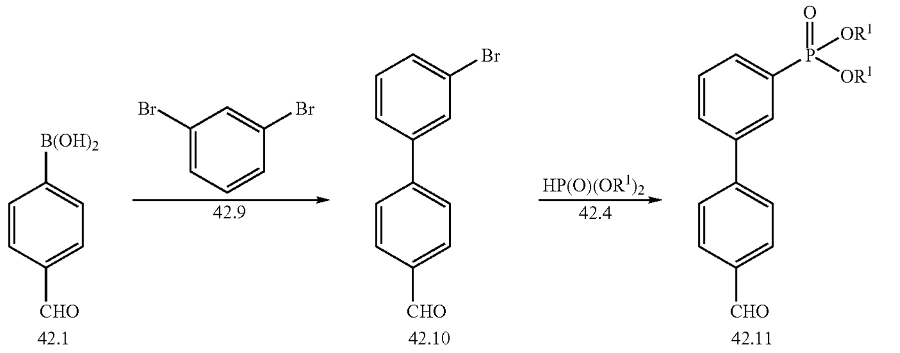

-continued
Example 2
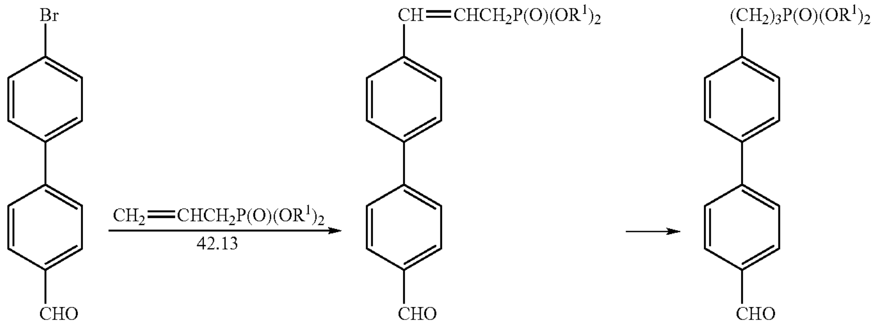
42.12 42.15 42.16
Scheme 43
Method
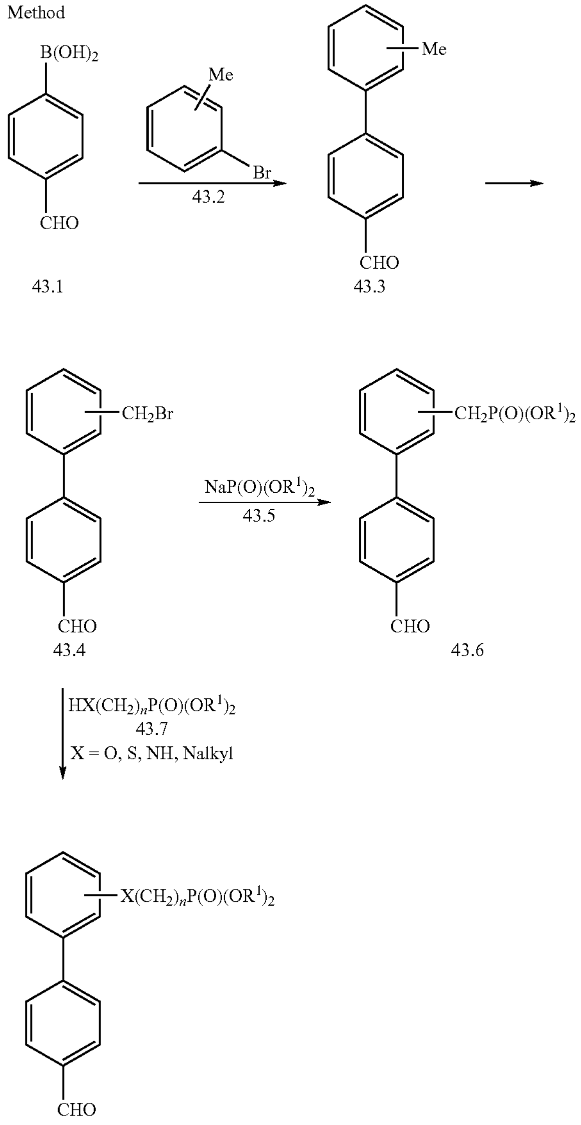
43.1 43.3 43.4 43.6
-continued
Example 1
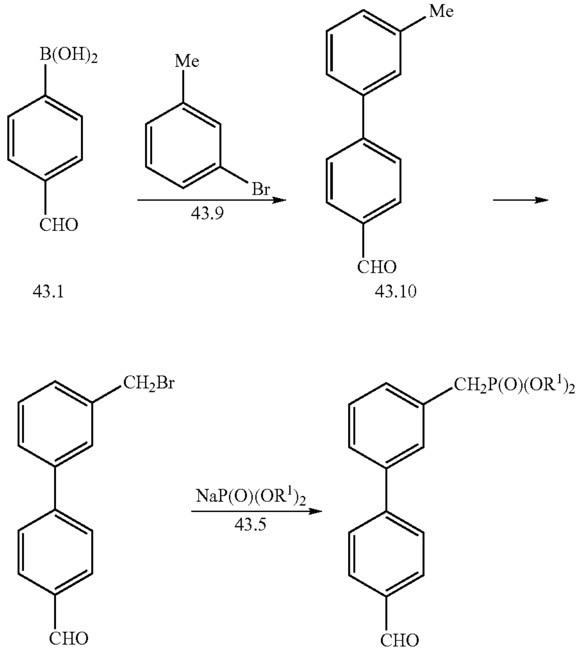
43.1 43.10 43.11 43.12
Example 2
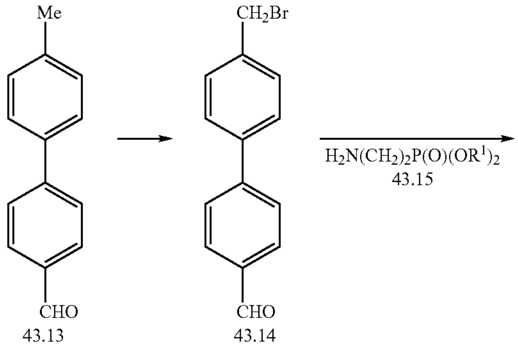
43.13 43.14

-continued
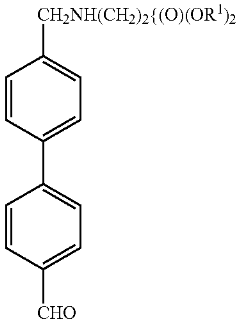
43.16
Scheme 44
Method
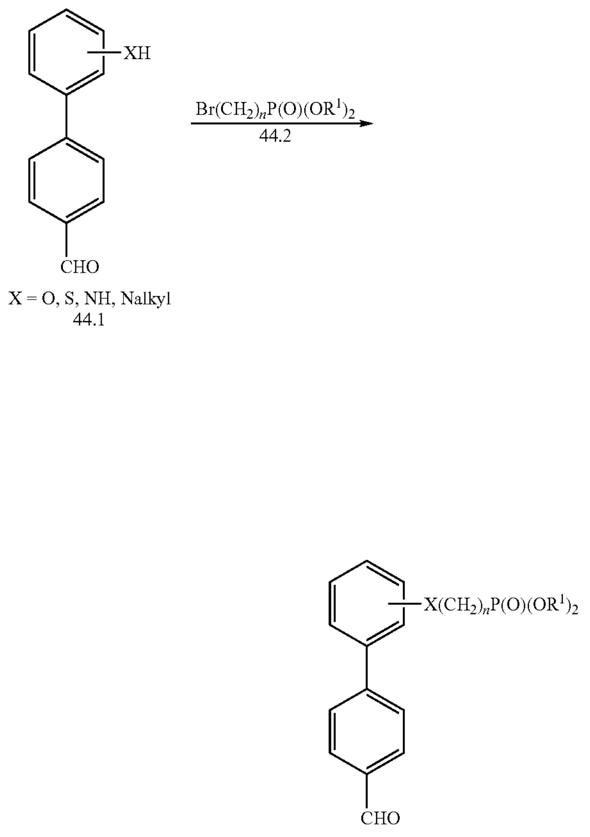
X = O, S, NH, Nalkyl
44.1
44.3
-continued
Example
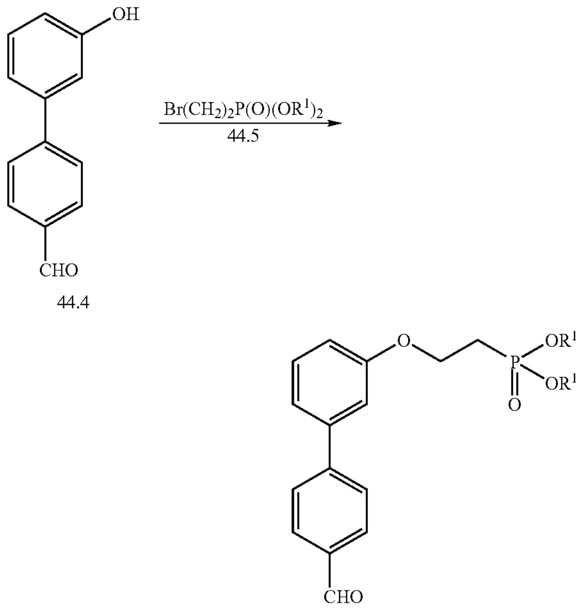
44.4
44.6
Scheme 45
Method
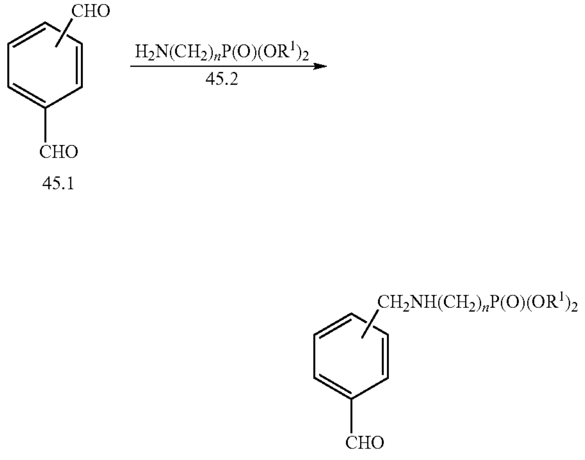
45.1
45.3
Example
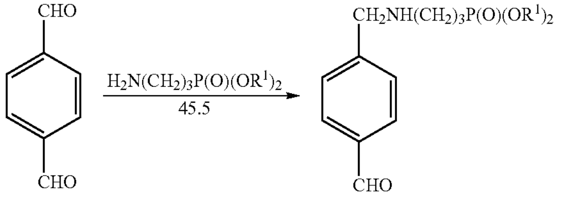
45.4
45.6

Scheme 46
Method
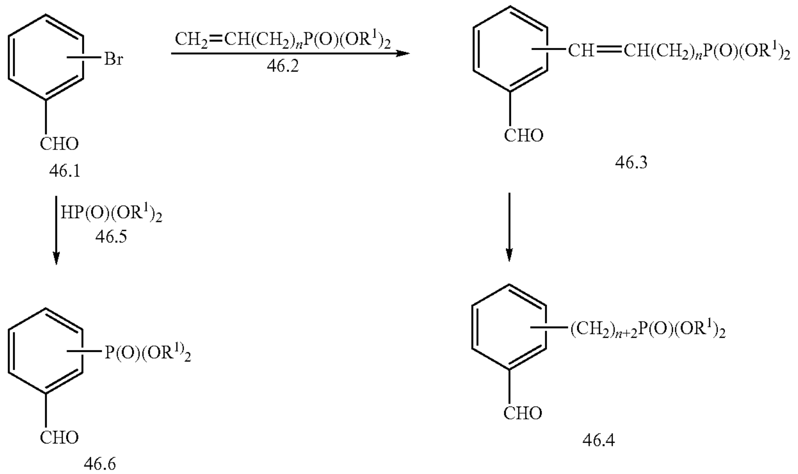
46.1 46.3 46.6 46.4
Example 1
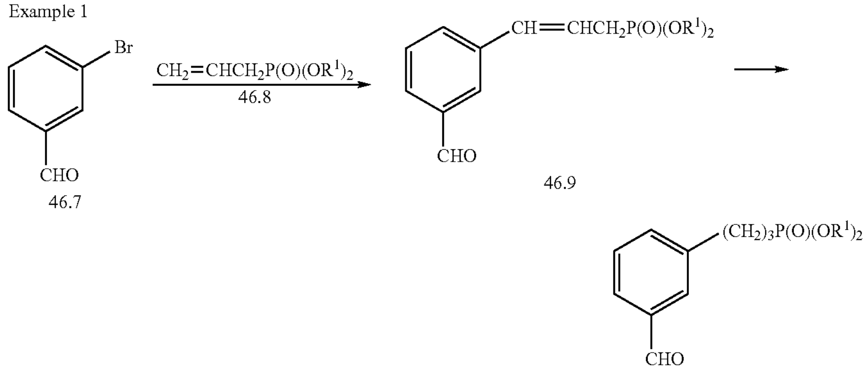
46.7 46.9 46.10
Example 2
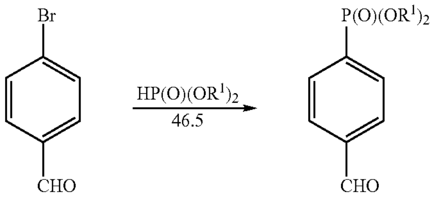
46.11 46.12
Scheme 47
Method
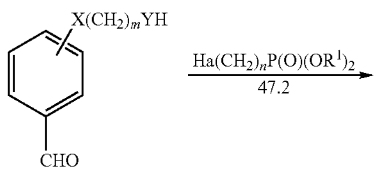
X, Y = O, S, NH
47.1
-continued
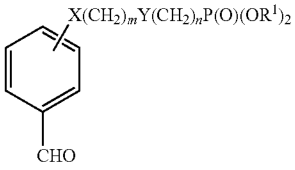
47.3

-continued

Example

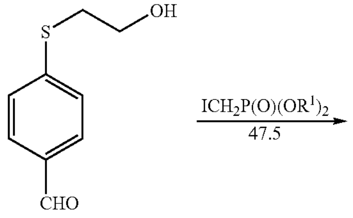

47.4

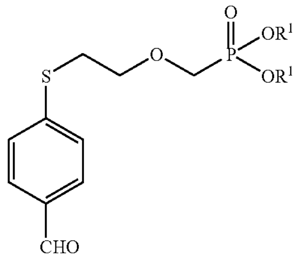

47.6

Scheme 48

Method

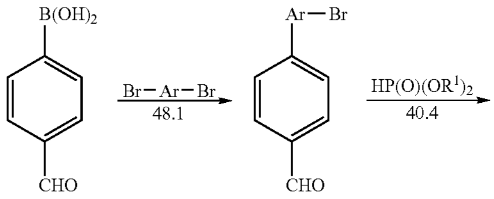

43.1 48.2

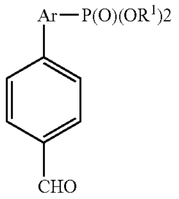

48.3

Example

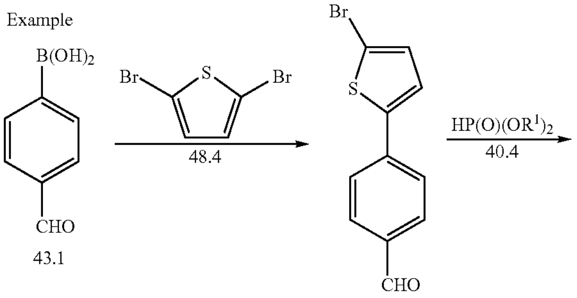

43.1 48.5

-continued

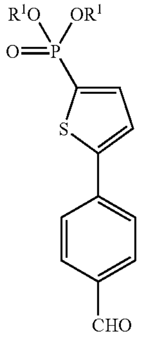

48.6

Preparation of the Cyclohexanecarboxaldehyde Phosphonates 4.16.

Schemes 49-52 illustrate methods for the preparation of the cyclohexanecarboxaldehyde phosphonates 4.16 which are employed in the synthesis of the phosphonate esters 3c. Scheme 49 depicts the preparation of cyclohexyl phosphonates in which the phosphonate group is attached by means of a nitrogen and an alkylene chain. In this procedure, a cyclohexane dicarboxaldehyde 49.1 is reacted with one molar equivalent of a dialkyl aminoalkyl phosphonate 49.2 under reductive amination conditions, as described above, to afford the phosphonate product 49.3.

For example, cyclohexane-1,3-dialdehyde 49.4, the preparation of which is described in J. Macromol. Sci. Chem., 1971, 5, 1873, is reacted with a dialkyl aminopropyl phosphonate 49.5, (Acros) and one molar equivalent of sodium triacetoxyborohydride, to yield the phosphonate product 49.6.

Using the above procedures, but employing, in place of cyclohexane-1,3-dialdehyde 49.4, different cyclohexane dialdehydes 49.1, and/or different aminoalkyl phosphonates 49.2, the corresponding products 49.3 are obtained.

Scheme 50 depicts the preparation of cyclohexyl phosphonates in which the phosphonate group is attached by means of a vinyl or ethylene group and a phenyl ring. In this procedure, a vinyl-substituted cyclohexane carboxaldehyde 50.1 is coupled, in the presence of a palladium catalyst, as described above, (Scheme 36) with a dialkyl bromophenylphosphonate 50.2, to afford the phosphonate product 50.3. Optionally, the product is reduced to afford the ethylene-linked analog 50.4. The reduction reaction is effected catalytically, for example by the use of hydrogen in the presence of a palladium catalyst, or chemically, for example by the use of diimide.

For example, 4-vinylcyclohexanecarboxaldehyde 50.5, the preparation of which is described in WO 9935822, is coupled with a dialkyl 3-bromophenyl phosphonate 50.6, prepared as described in J. Chem. Soc., Perkin Trans., 1977, 2, 789, to give the coupled product 50.7. The product is then reduced with diimide, generated by treatment of disodium azodicarboxylate with acetic acid, as described in J. Am. Chem. Soc., 83, 3725, 1961, to yield the saturated product 50.8.

Using the above procedures, but employing, in place of 4-vinylcyclohexanecarboxaldehyde 50.5, different vinylcyclohexane carboxaldehydes 50.1, and/or different bromophenyl phosphonates 50.2, the corresponding products 50.3 and 50.4 are obtained.

Scheme 51 depicts the preparation of cyclohexyl phosphonates in which the phosphonate group is attached by means of an alkylene chain incorporating an oxygen atom. In this procedure, a hydroxymethyl-substituted cyclohexane carboxaldehyde 51.1 is reacted, in the presence of a strong base such as sodium hydride or potassium tert. butoxide, with one molar equivalent of a dialkyl bromoalkyl phosphonate 51.2, to prepare the phosphonate 51.3. The alkylation reaction is conducted in a polar organic solvent such as dimethylformamide, tetrahydrofuran or acetonitrile, at from ambient temperature to about 60°.

For example, 3-(hydroxymethyl)cyclohexanecarboxaldehyde 51.4, prepared as described in WO 0107382, is treated with one molar equivalent of sodium hydride in tetrahydrofuran at 50°, and one molar equivalent of a dialkyl bromoethyl phosphonate 51.5 (Aldrich) to afford the alkylation product 51.6.

Using the above procedures, but employing, in place of 3-(hydroxymethyl)cyclohexanecarboxaldehyde 51.4 different hydroxymethylcyclohexane carboxaldehydes 51.1, and/or different bromoalkyl phosphonates 51.2, the corresponding products 51.3 are obtained.

Scheme 52 depicts the preparation of cyclohexyl phosphonates in which the phosphonate group is directly attached to the cyclohexane ring. In this procedure, a hydroxy-substituted cyclohexanecarboxaldehyde 52.1 is converted into the corresponding bromo derivative 52.2. The conversion of alcohols into the corresponding bromides is described, for example, in Comprehensive Organic Transformations, by R. C. Larock, VCH, 1989, p. 354ff and p. 356ff. The transformation is effected by treatment of the alcohol with hydrobromic acid, or by reaction with hexabromoethane and triphenylphosphine, as described in Synthesis, 139, 1983. The resulting bromo compound 52.2 is then subjected to an Arbuzov reaction, by treatment with a trialkyl phosphite 52.3 at ca 100°. The preparation of phosphonates by mean of the Arbuzov reaction is described in Handb. Organophosphorus Chem., 1992, 115.

For example, 4-hydroxycyclohexanecarboxaldehyde 52.5 is reacted with one molar equivalent of hexabromoethane and triphenyl phosphine in dichloromethane, to yield 4-bromocyclohexanecarboxaldehyde 52.6. The product is heated at 100° with a trialkyl phosphite 52.3 to afford the cyclohexyl phosphonate 52.7.

Using the above procedures, but employing, in place of 4-(hydroxymethyl)cyclohexanecarboxaldehyde 52.5, different hydroxy-substituted cyclohexanecarboxaldehydes 52.1, the corresponding products 52.4 are obtained.

Preparation of Quinoline 2-carboxylic Acids 19a.1 Incorporating Phosphonate Moieties or Precursors Thereto.

The reaction sequence depicted in Schemes 19a-19d require the use of a quinoline-2-carboxylic acid reactant 19a.1 in which the substituent A is either the group link-P(O)$(OR^1)_2$ or a precursor thereto, such as [OH], [SH] Br.

A number of suitably substituted quinoline-2-carboxylic acids are available commercially or are described in the chemical literature. For example, the preparations of 6-hydroxy, 6-amino and 6-bromoquinoline-2-carboxylic acids are described respectively in DE 3004370, J. Het. Chem., 1989, 26, 929 and J. Labelled Comp. Radiopharm., 1998, 41, 1103, and the preparation of 7-aminoquinoline-2-carboxylic acid is described in J. Am. Chem. Soc., 1987, 109, 620. Suitably substituted quinoline-2-carboxylic acids can also be prepared by procedures known to those skilled in the art. The synthesis of variously substituted quinolines is described, for example, in Chemistry of Heterocyclic Compounds, Vol. 32, G. Jones, ed., Wiley, 1977, p 93ff. Quinoline-2-carboxylic acids can be prepared by means of the Friedlander reaction, which is described in Chemistry of Heterocyclic Compounds, Vol. 4, R. C. Elderfield, ed., Wiley, 1952, p. 204.

Scheme 53 illustrates the preparation of quinoline-2-carboxylic acids by means of the Friedlander reaction, and further transformations of the products obtained. In this reaction sequence, a substituted 2-aminobenzaldehyde 53.1 is reacted with an alkyl pyruvate ester 53.2, in the presence of an organic or inorganic base, to afford the substituted quinoline-2-carboxylic ester 53.3. Hydrolysis of the ester, for example by the use of aqueous base, then afford the corresponding carboxylic acid 53.4. The carboxylic acid product 53.4 in which X is $NH_2$ can be further transformed into the corresponding compounds 53.6 in which Z is OH, SH or Br. The latter transformations are effected by means of a diazotization reaction. The conversion of aromatic amines into the corresponding phenols and bromides by means of a diazotization reaction is described respectively in Synthetic Organic Chemistry, R. B. Wagner, H. D. Zook, Wiley, 1953, pages 167 and 94; the conversion of amines into the corresponding thiols is described in Sulfur Lett., 2000, 24, 123. The amine is first converted into the diazonium salt by reaction with nitrous acid. The diazonium salt, preferably the diazonium tetrafluoborate, is then heated in aqueous solution, for example as described in Organic Functional Group Preparations, by S. R. Sandler and W. Karo, Academic Press, 1968, p. 83, to afford the corresponding phenol 53.6, X═OH. Alternatively, the diazonium salt is reacted in aqueous solution with cuprous bromide and lithium bromide, as described in Organic Functional Group Preparations, by S. R. Sandler and W. Karo, Academic Press, 1968, p. 138, to yield the corresponding bromo compound, 53.6, Y=Br. Alternatively, the diazonium tetrafluoborate is reacted in acetonitrile solution with a sulfhydryl ion exchange resin, as described in Sulfur Lett., 200, 24, 123, to afford the thiol 53.6, Y=SH. Optionally, the diazotization reactions described above can be performed on the carboxylic esters 53.3 instead of the carboxylic acids 53.5.

For example, 2,4-diaminobenzaldehyde 53.7 (Apin Chemicals) is reacted with one molar equivalent of methyl pyruvate 53.2 in methanol, in the presence if a base such as piperidine, to afford methyl-7-aminoquinoline-2-carboxylate 53.8. Basic hydrolysis of the product, employing one molar equivalent of lithium hydroxide in aqueous methanol, then yields the carboxylic acid 53.9. The amino-substituted carboxylic acid is then converted into the diazonium tetrafluoborate 53.10 by reaction with sodium nitrite and tetrafluoboric acid. The diazonium salt is heated in aqueous solution to afford the 7-hydroxyquinoline-2-carboxylic acid, 53.11, Z=OH. Alternatively, the diazonium tetrafluoborate is heated in aqueous organic solution with one molar equivalent of cuprous bromide and lithium bromide, to afford 7-bromoquinoline-2-carboxylic acid 53.11, X═Br. Alternatively, the diazonium tetrafluoborate 53.10 is reacted in acetonitrile solution with the sulfhydryl form of an ion exchange resin, as described in Sulfur Lett., 2000, 24, 123, to prepare 7-mercaptoquinoline-2-carboxylic acid 53.11, Z=SH.

Using the above procedures, but employing, in place of 2,4-diaminobenzaldehyde 53.7, different aminobenzaldehydes 53.1, the corresponding amino, hydroxy, bromo or mercapto-substituted quinoline-2-carboxylic acids 53.6 are obtained. The variously substituted quinoline carboxylic acids and esters can then be transformed, as described below, (Schemes 54-56) into phosphonate-containing derivatives.

Scheme 49
Method
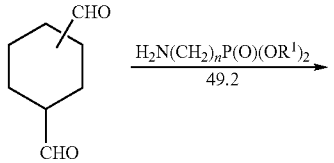
49.1
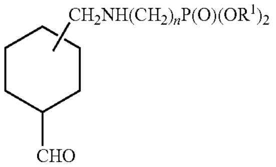
49.3
Example
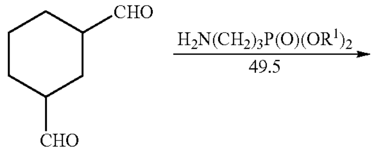
49.4
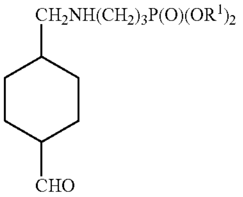
49.6
Scheme 50
Method
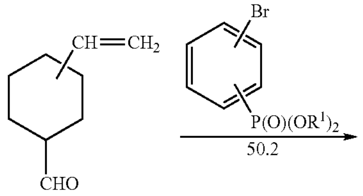
50.1
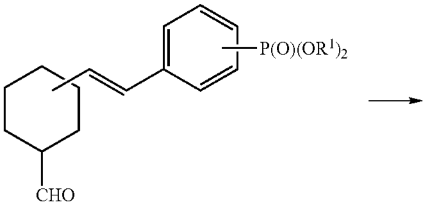
50.3
-continued
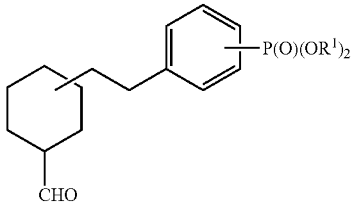
50.4
Example
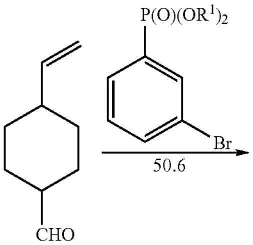
50.5
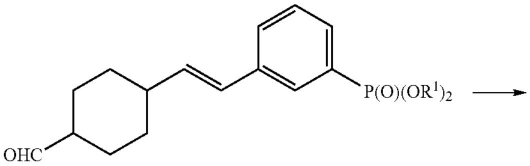
50.7
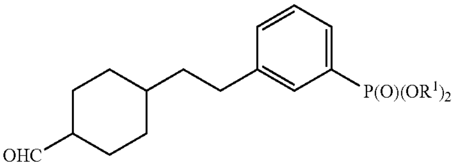
50.8
Scheme 51
Method
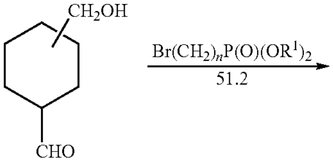
51.1
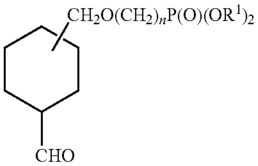
51.3

-continued

Example

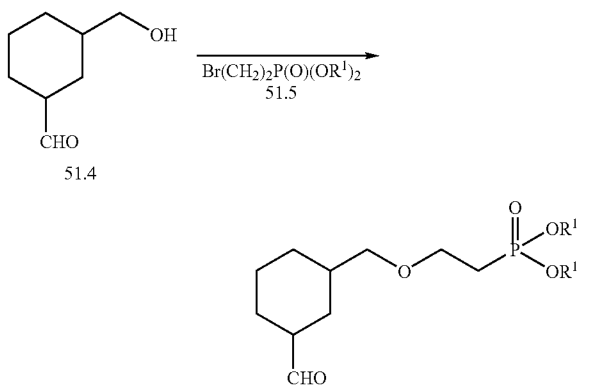

51.4

51.6

Scheme 52

Method

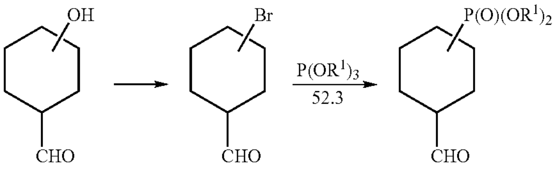

52.1 52.2 52.4

Example

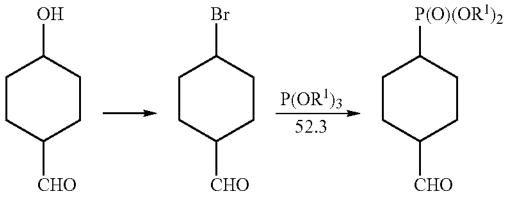

52.5 52.6 52.7

Scheme 53

Method

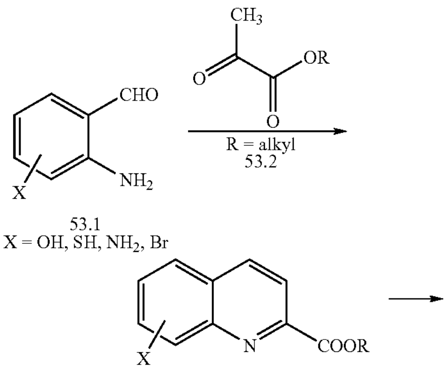

53.1

X = OH, SH, $NH_2$, Br 53.3

-continued

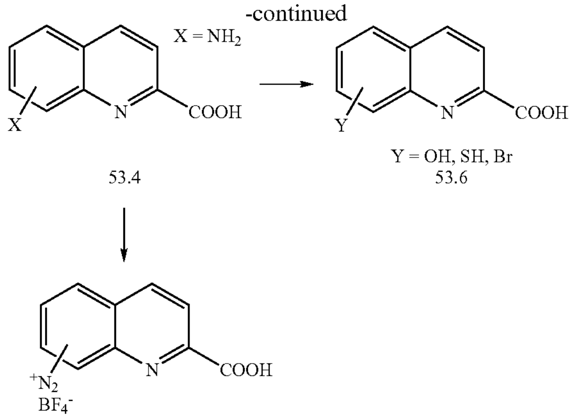

Y = OH, SH, Br 53.4 53.6

53.5

Example

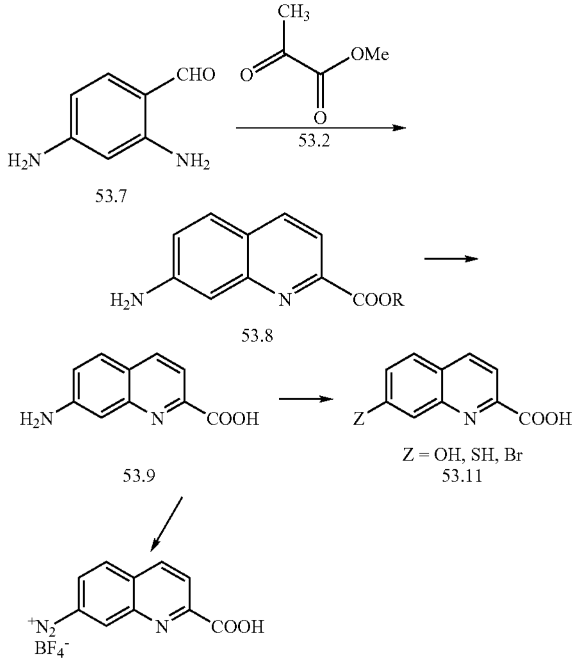

53.7

53.8

53.9

Z = OH, SH, Br 53.11

53.10

Scheme 54 depicts the preparation of quinoline-2-carboxylic acids incorporating a phosphonate moiety attached to the quinoline ring by means of an oxygen or a sulfur atom. In this procedure, an amino-substituted quinoline-2-carboxylate ester 54.1 is transformed, via a diazotization procedure as described above (Scheme 53) into the corresponding phenol or thiol 54.2. The latter compound is then reacted with a dialkyl hydroxymethylphosphonate 54.3, under the conditions of the Mitsonobu reaction, to afford the phosphonate ester 54.4. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the thioether products 54.5. Basic hydrolysis of the ester group, for example employing one molar equivalent of lithium hydroxide in aqueous methanol, then yields the carboxylic acid 54.6.

For example, methyl 6-amino-2-quinoline carboxylate 54.7, prepared as described in J. Het. Chem., 1989, 26, 929, is converted, by means of the diazotization procedure described above, into methyl 6-mercaptoquinoline-2-carboxylate 54.8. This material is reacted with a dialkyl hydroxymethylphosphonate 54.9 (Aldrich) in the presence of diethyl azodicarboxylate and triphenylphosphine in tetrahydrofuran solution, to afford the thioether 54.10. Basic hydrolysis then afford the carboxylic acid 54.11.

Using the above procedures, but employing, in place of methyl 6-amino-2-quinoline carboxylate 54.7, different aminoquinoline carboxylic esters 54.1, and/or different dialkyl hydroxymethylphosphonates 54.3 the corresponding phosphonate ester products 54.6 are obtained.

Scheme 55 illustrates the preparation of quinoline-2-carboxylic acids incorporating phosphonate esters attached to the quinoline ring by means of a saturated or unsaturated carbon chain. In this reaction sequence, a bromo-substituted quinoline carboxylic ester 55.1 is coupled, by means of a palladium-catalyzed Heck reaction, with a dialkyl alkenylphosphonate 55.2. The coupling of aryl halides with olefins by means of the Heck reaction is described, for example, in Advanced Organic Chemistry, by F. A. Carey and R. J. Sundberg, Plenum, 2001, p. 503ff. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Thus, Heck coupling of the bromo compound 55.1 and the olefin 55.2 affords the olefinic ester 55.3. Hydrolysis, for example by reaction with lithium hydroxide in aqueous methanol, or by treatment with porcine liver esterase, then yields the carboxylic acid 55.4. Optionally, the unsaturated carboxylic acid 55.4 can be reduced to afford the saturated analog 55.5. The reduction reaction can be effected chemically, for example by the use of diimide, as described in Comprehensive Organic Transformations, by R. C. Larock, VCH, 1989, p. 5.

For example, methyl 7-bromoquinoline-2-carboxylate, 55.6, prepared as described in J. Labelled Comp. Radiopharm., 1998, 41, 1103, is reacted in dimethylformamide at 60° with a dialkyl vinylphosphonate 55.7 (Aldrich) in the presence of 2 mol % of tetrakis(triphenylphosphine)palladium and triethylamine, to afford the coupled product 55.8. The product is then reacted with lithium hydroxide in aqueous tetrahydrofuran to produce the carboxylic acid 55.9. The latter compound is reacted with dumide, prepared by basic hydrolysis of diethyl azodicarboxylate, as described in Angew. Chem. Int. Ed., 4, 271, 1965, to yield the saturated product 55.10.

Using the above procedures, but employing, in place of methyl 6-bromo-2-quinolinecarboxylate 55.6, different bromoquinoline carboxylic esters 55.1, and/or different dialkyl alkenylphosphonates 55.2, the corresponding phosphonate ester products 55.4 and 55.5 are obtained.

Scheme 56 depicts the preparation of quinoline-2-carboxylic acids 56.5 in which the phosphonate group is attached by means of a nitrogen atom and an alkylene chain. In this reaction sequence, a methyl aminoquinoline-2-carboxylate 56.1 is reacted with a phosphonate aldehyde 56.2 under reductive amination conditions, to afford the aminoalkyl product 56.3. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The ester product 56.4 is then hydrolyzed to yield the free carboxylic acid 56.5.

For example, methyl 7-aminoquinoline-2-carboxylate 56.6, prepared as described in J. Amer. Chem. Soc., 1987, 109, 620, is reacted with a dialkyl formylmethylphosphonate 56.7 (Aurora) in methanol solution in the presence of sodium borohydride, to afford the alkylated product 56.8. The ester is then hydrolyzed, as described above, to yield the carboxylic acid 56.9.

Using the above procedures, but employing, in place of the formylmethyl phosphonate 56.2, different formylalkyl phosphonates, and/or different aminoquinolines 56.1, the corresponding products 56.5 are obtained.

Interconversions of the Phosphonates R-link-P(O)($OR^1$)$_2$, R-link-P(O)($OR^1$)(OH) and R-link-P(O)(OH)$_2$.

Schemes 1-56 described the preparations of phosphonate esters of the general structure R-link-P(O)($OR^1$)$_2$, in which the groups $R^1$, the structures of which are defined in Chart 1, may be the same or different. The $R^1$ groups attached to a phosphonate esters 1-7, or to precursors thereto, may be changed using established chemical transformations. The interconversions reactions of phosphonates are illustrated in Scheme 57. The group R in Scheme 57 represents the substructure to which the substituent link-P(O)($OR^1$)$_2$ is attached, either in the compounds 1-7 or in precursors thereto. The $R^1$ group may be changed, using the procedures described below, either in the precursor compounds, or in the esters 1-7. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 57.1 into the corresponding phosphonate monoester 57.2 (Scheme 57, Reaction 1) can be accomplished by a number of methods. For example, the ester 57.1 in which $R^1$ is an aralkyl group such as benzyl, can be converted into the monoester compound 57.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 57.1 in which $R^1$ is an aryl group such as phenyl, or an alkenyl group such as allyl, into the monoester 57.2 can be effected by treatment of the ester 57.1 with a base such as aqueous sodium hydroxide in acetonitrile or lithium hydroxide in aqueous tetrahydrofuran.

Phosphonate diesters 57.1 in which one of the groups $R^1$ is aralkyl, such as benzyl, and the other is alkyl, can be converted into the monoesters 57.2 in which $R^1$ is alkyl by hydrogenation, for example using a palladium on carbon catalyst. Phosphonate diesters in which both of the groups $R^1$ are alkenyl, such as allyl, can be converted into the monoester 57.2 in which $R^1$ is alkenyl, by treatment with chlorotris (triphenylphosphine)rhodium (Wlikinson's catalyst) in aqueous ethanol at reflux, optionally in the presence of diazabicyclooctane, for example by using the procedure described in J. Org. Chem., 38, 3224, 1973 for the cleavage of allyl carboxylates.

The conversion of a phosphonate diester 57.1 or a phosphonate monoester 57.2 into the corresponding phosphonic acid 57.3 (Scheme 57, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 57.2 in which $R^1$ is aralkyl such as benzyl, can be converted into the corresponding phosphonic acid 57.3 by hydrogenation over a palladium catalyst, or by treatment with hydrogen chloride in an ethereal solvent such as dioxan. A phosphonate monoester 57.2 in which $R^1$ is alkenyl such as, for example, allyl, can be converted into the phosphonic acid 57.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 57.1 in which $R^1$ is benzyl is described in J. Org. Chem., 24, 434, 1959. Platinum-catalyzed hydrogenolysis of phosphonate esters 57.1 in which $R^1$ is phenyl is described in J. Amer. Chem. Soc., 78, 2336, 1956.

The conversion of a phosphonate monoester 57.2 into a phosphonate diester 57.1 (Scheme 57, Reaction 4) in which the newly introduced $R^1$ group is alkyl, aralkyl, haloalkyl such as chloroethyl, or aralkyl can be effected by a number of reactions in which the substrate 57.2 is reacted with a hydroxy compound $R^1OH$, in the presence of a coupling agent. Suitable coupling agents are those employed for the preparation of carboxylate esters, and include a carbodirimde such as dicyclohexylcarbodiimide, in which case the reaction is preferably conducted in a basic organic solvent such as pyridine, or (benzotriazol-1 yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 57.2 to the diester 57.1 can be effected by the use of the Mitsonobu reaction, as described above (Scheme 54). The substrate is reacted with the hydroxy compound $R^1OH$, in the presence of diethyl azodicarboxylate and a triarylphosphine such as triphenyl phosphine. Alternatively, the phosphonate monoester 57.2 can be transformed into the phosphonate diester 57.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 57.2 is transformed into the chloro analog RP(O)$(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product RP(O)$(OR^1)Cl$ is then reacted with the hydroxy compound $R^1OH$, in the presence of a base such as triethylamine, to afford the phosphonate diester 57.1.

A phosphonic acid R-link-P(O)$(OH)_2$ can be transformed into a phosphonate monoester RP(O)$(OR^1)(OH)$ (Scheme 57, Reaction 5) by means of the methods described above of for the preparation of the phosphonate diester R-link-P(O)$(OR^1)_2$ 57.1, except that only one molar proportion of the component $R^1OH$ or $R^1Br$ is employed.

A phosphonic acid R-link-P(O)$(OH)_2$ 57.3 can be transformed into a phosphonate diester R-link-P(O)$(OR^1)_2$ 57.1 (Scheme 57, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine.

Alternatively, phosphonic acids 57.3 can be transformed into phosphonic esters 57.1 in which $R^1$ is aryl, by means of a coupling reaction employing, for example, dicyclohexylcarbodiimide in pyridine at ca 70°. Alternatively, phosphonic acids 57.3 can be transformed into phosphonic esters 57.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 57.1.

General Applicability of Methods for Introduction of Phosphonate Substituents.

The procedures described herein for the introduction of phosphonate moieties (Schemes 21-56) are, with appropriate modifications known to one skilled in the art, transferable to different chemical substrates. Thus, the methods described above for the introduction of phosphonate groups into carbinols (Schemes 21-26) are applicable to the introduction of phosphonate moieties into the oxirane, thiophenol, aldehyde and quinoline substrates, and the methods described herein for the introduction of phosphonate moieties into the oxirane, thiophenol, aldehyde and quinoline substrates, (Schemes 27-56) are applicable to the introduction of phosphonate moieties into carbinol substrates.

Scheme 54

Method

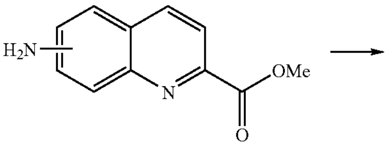

54.1

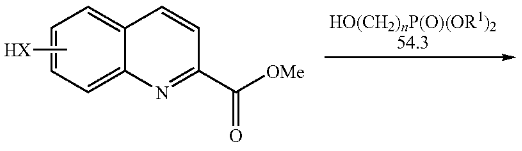

X = O, S 54.2

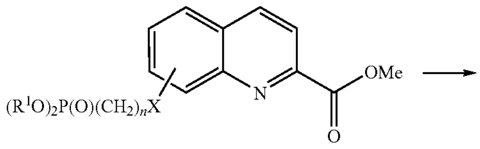

54.4

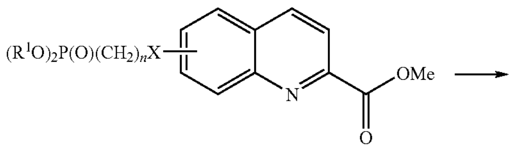

54.5

-continued
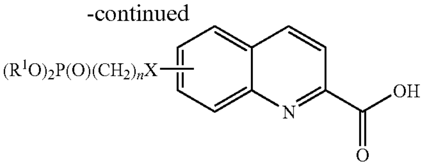
54.6
Example
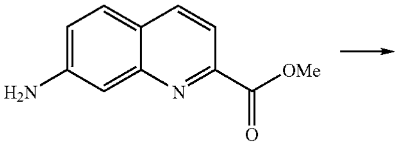
54.7
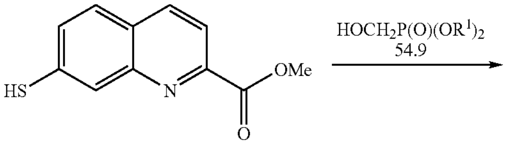
54.8
-continued
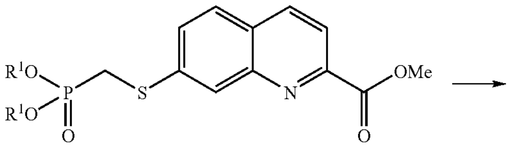
54.10
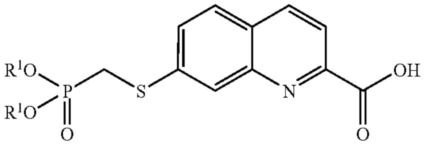
54.11
Scheme 55
Method
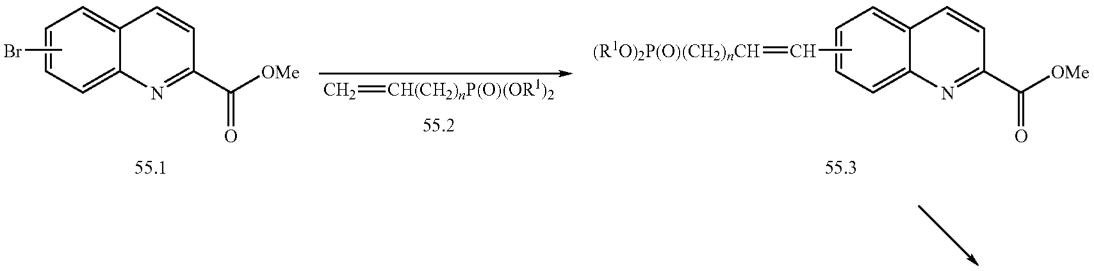
55.1
55.3
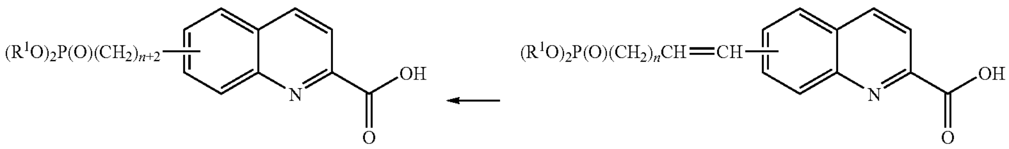
55.5
55.4
Example
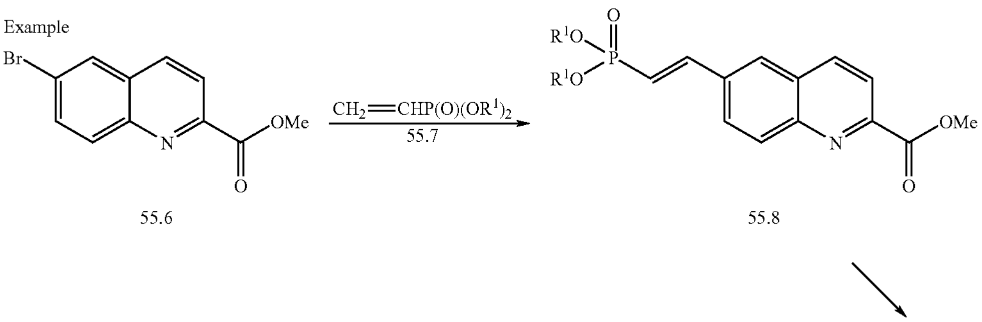
55.6
55.8

-continued
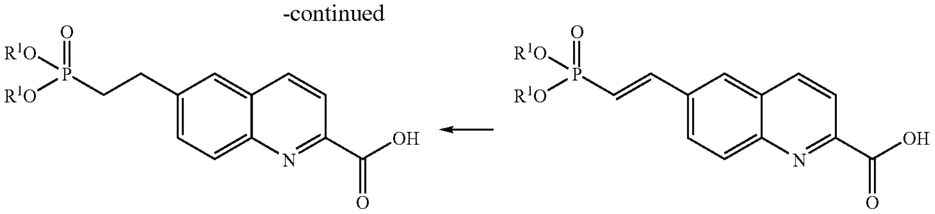
55.10 55.9
Scheme 56
Method
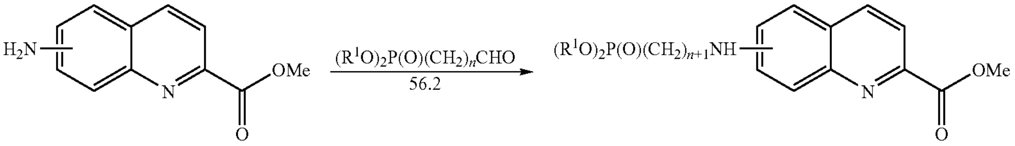
56.1 56.3
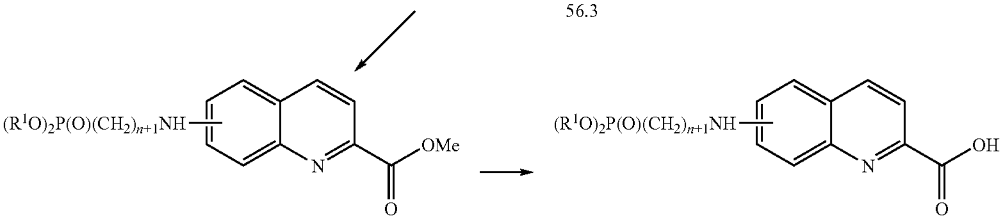
56.4 56.5
Example
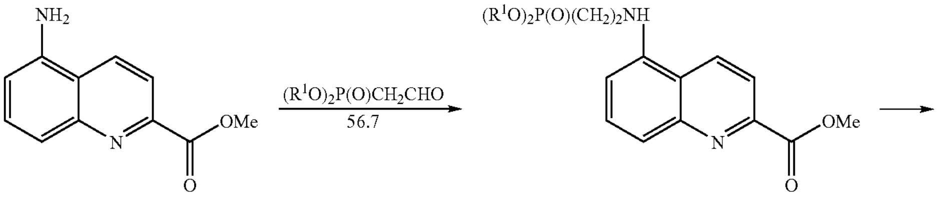
56.6 56.8
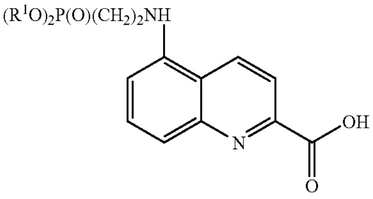
56.9
Scheme 57
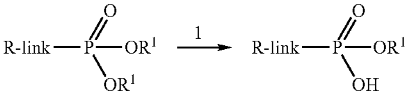
57.1 57.2
-continued
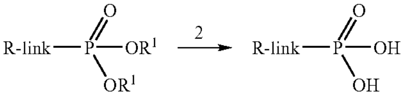
57.1 57.3
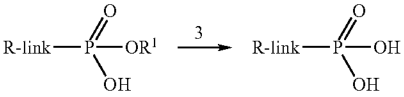
57.2 57.3

-continued

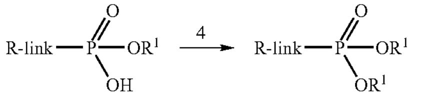

57.2 57.1

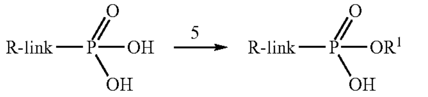

57.3 57.2

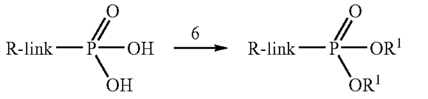

57.3 57.1

Preparation of Phosphonate Intermediates 6 and 7 with Phosphonate Moieties Incorporated into the Group $R^2COOH$ and $R^5COOH$.

The chemical transformations described in Schemes 1-56 illustrate the preparation of compounds 1-5 in which the phosphonate ester moiety is attached to the carbinol moiety, (Schemes 21-26), the oxirane moiety (Schemes 27-29), the thiophenol moiety (Schemes 30-39), the aldehyde moiety (Schemes 40-52) or the quinoline moiety (Schemes 53-56). The various chemical methods employed for the preparation of phosphonate groups can, with appropriate modifications known to those skilled in the art, be applied to the introduction of phosphonate ester groups into the compounds $R^2COOH$ and $R^5COOH$, as defined in Charts 2a, 2b and 2c. The resultant phosphonate-containing analogs, designated as $R^{2a}COOH$ and $R^{5a}COOH$ can then, using the procedures described above, be employed in the preparation of the compounds 6 and 7. The procedures required for the introduction of the phosphonate-containing analogs $R^{2a}COOH$ and $R^{5a}COOH$ are the same as those described above (Schemes 1, 5, 7 and 10) for the introduction of the $R^2CO$ and $R^5CO$ moieties.

Tipranavir-like Phosphonate Protease Inhibitors (TLPPI)

Chart 1 illustrates the target compounds of the invention. A linkage group (link) is a portion of the structure that links two substructures, one of which is the scaffold having the structures shown above, the other a phosphonate moiety bearing the appropriate R and $R^0$ groups, as defined below. The link has at least one uninterrupted chain of atoms, other than hydrogen, typically ranging in up to 25 atoms, more preferably less than 10 atoms (hydrogen excluded). The link can be formed using a variety of functional groups such as heteroatom, carbon, alkenyl, aryl etc. Chart 2 illustrates the intermediate phosphonate compounds of this invention that are used in the preparation of the targets, Chart 1. Chart 3 shows some examples illustrated below of linking groups present in the structures in Chart 1 and 2. The R and $R^0$ groups can be both natural and un-natural amino acid esters linked through the amine nitrogen, or alternatively, one of the groups can be substituted for an oxygen linked aryl, alkyl, aralkyl group etc. Alternatively one of the groups may be an oxygen linked aryl, alkyl, aralkyl group etc and the other a lactate ester.

CHART 1

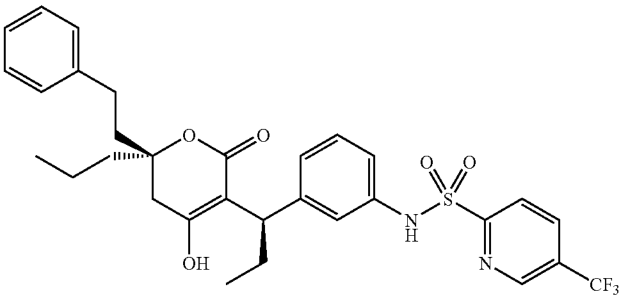

Tipranavir

U.S. Pat. No. 5852195

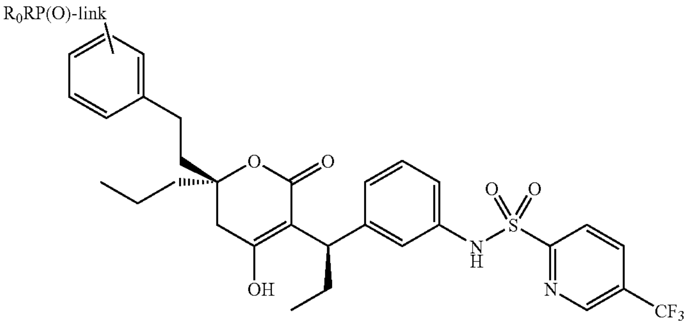

1a

CHART 1-continued
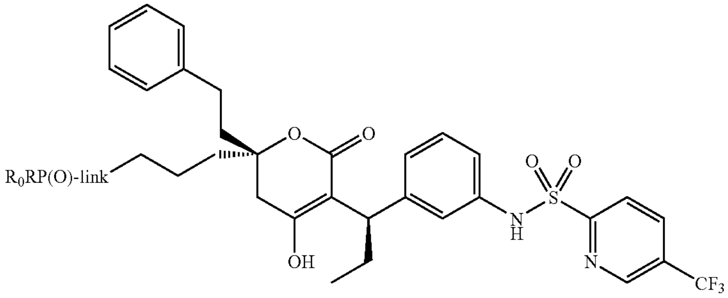
2a
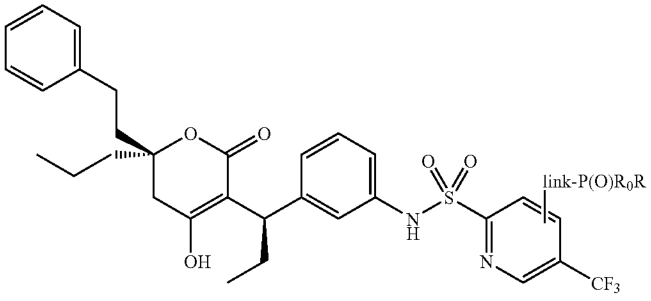
3a
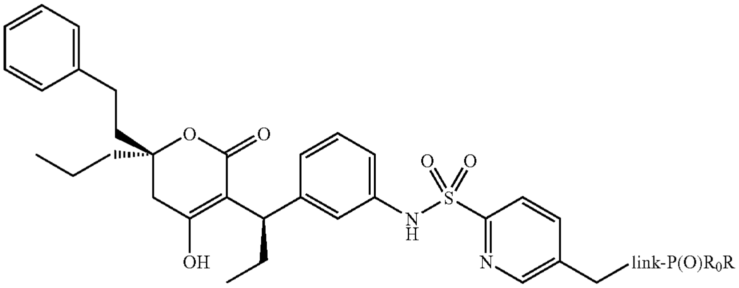
4a
CHART 2
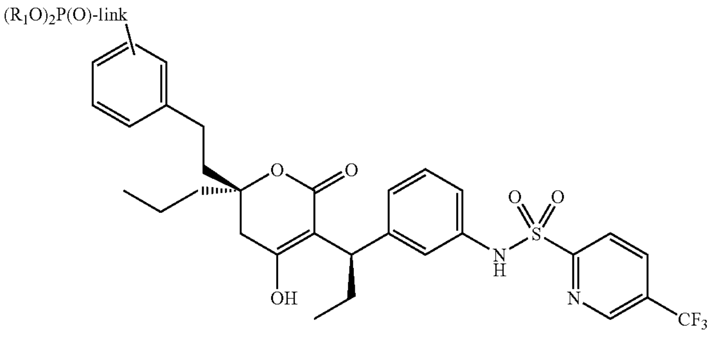
1

CHART 2-continued
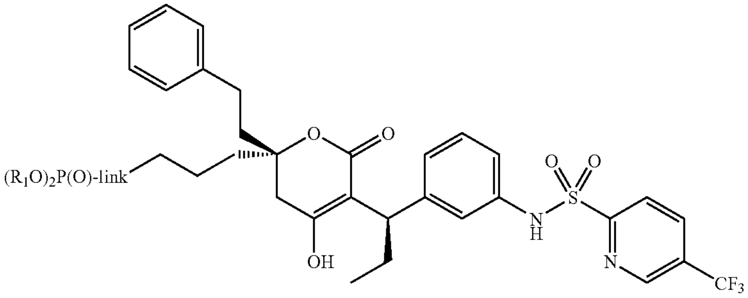
2
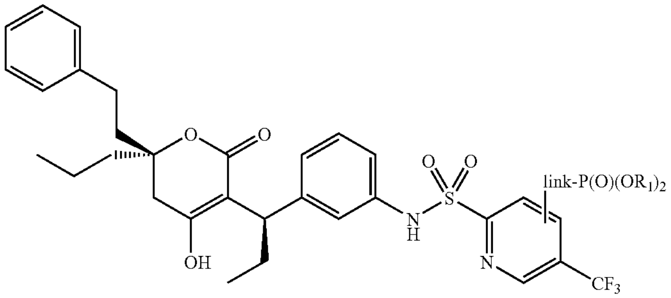
3
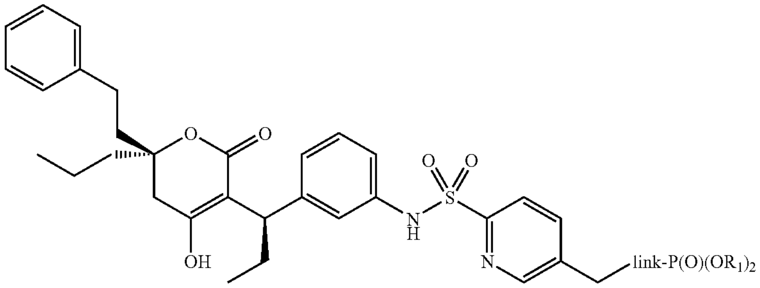
4
$R_1$ = H, alkyl, haloalkyl, alkenyl, aralkyl, aryl
CHART 3
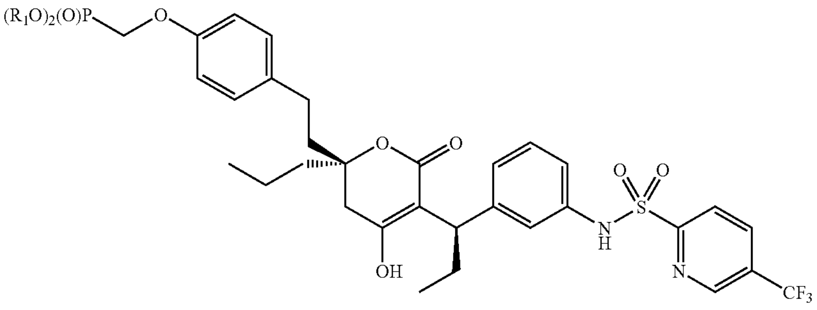

CHART 3-continued

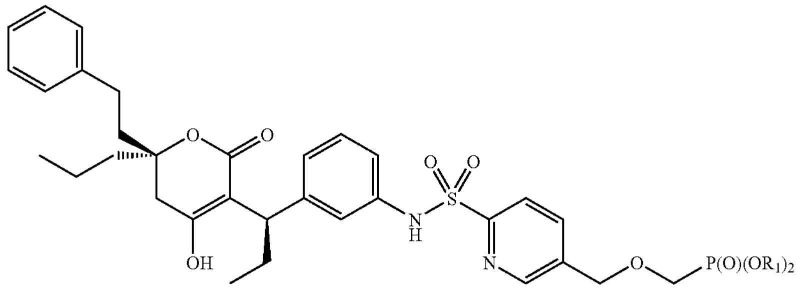

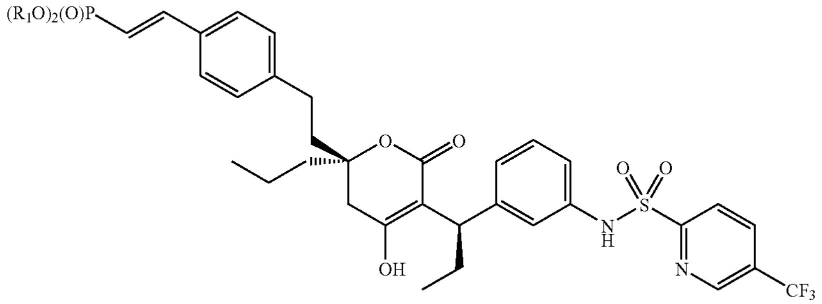

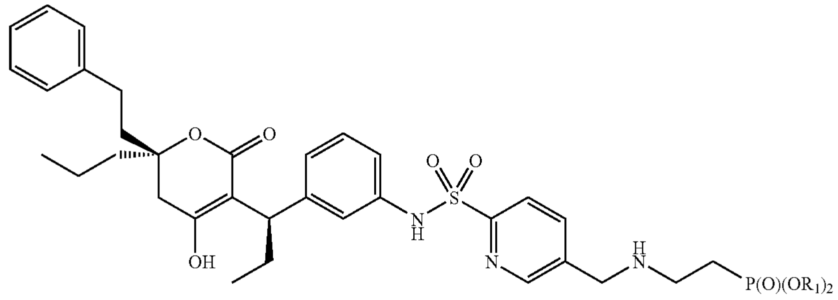

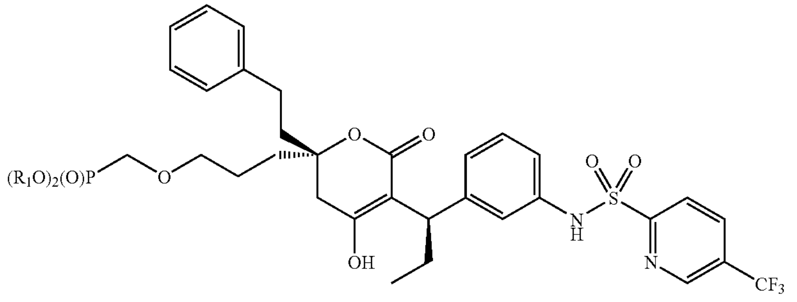

Phosphonate Interconversions

The final compounds described above are synthesized according to the methods described in the following Schemes 1-16. The intermediate phosphonate esters are shown in Chart 2 and these compounds can be used to prepare the final compounds illustrated above in Chart 1, by one skilled in the art, using known methods for synthesis of substituted phosphonates. These methods are similar to those described for the synthesis of amides. The preparation of amides from carboxylic acids and derivatives is described, for example, in Organic Functional Group Preparations, by S. R. Sandler and W. Karo, Academic Press, 1968, p. 274. Further methods are described in Scheme 16 below for the synthesis of the phosphonate diesters and can in some cases be applied to the synthesis of phosphor-amides.

In the following schemes, the conversion of various substituents into the group link-$P(O)(OR^1)_2$, where $R^1$ is defined in Chart 2, or indeed the final stage of $P(O)RR^0$, as defined above, can be effected at any convenient stage of the synthetic sequence, or in the final step. The selection of an appropriate step for the introduction of the phosphonate substituent is made after consideration of the chemical procedures required, and the stability of the substrates to those procedures. It may be necessary to protect reactive groups, for example hydroxyl, amino, during the introduction of the group link-$P(O)(OR^1)_2$ or $P(O)RR^0$ In the succeeding examples, the nature of the phosphonate ester group $P(O)(OR^1)_2$ can be varied, either before or after incorporation into the scaffold, by means of chemical transformations. The transformations, and the methods by which they are accomplished, are described below (Scheme 16). Examples shown in charts 1-3 indicate a specific stereochemistry. However, the methods are applicable to the synthesis all of the possible stereoisomers and the separation of possible isomers can be effected at any stage of the sequence after introduction of the stereocenter. The point in the synthetic sequence would be determined by the resolution that could be achieved in the separation by one skilled in the art.

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Third Edition 1999. Reactive substituents which may be protected are shown in the accompanying schemes as, for example, [OH], [SH], etc.

Preparation of Intermediate Phosphonates Shown in Chart 2

Scheme 1-3 illustrates the synthesis of target molecules of type 1, chart 2, in which A is Br, Cl, [OH], [NH], or the group link-P(O)$(OR^1)_2$. The procedures described in J. Med. Chem. 1998, 41, p3467 are used to generate compounds of the type 1 from 1.2 in which A is Hydrogen. The conversion of 1.1 into 1.2 follows procedures described in Bioorg Med. Chem 1999, 7, p2775 for the preparation of a similar compound. The preparation of 1.1 is described in Scheme 13-14. For example, acid 1.1 is converted via the Weinreb amide to the ketone 1.2. The ketone 1.2 is then treated with 3-oxo-butyric acid methyl ester, as described in J. Med Chem. 1998, 41, 3467, to give the pyrone 1.3. A mixture of R and S isomers can be carried forward or alternatively separated by chiral chromatography at this stage. Aluminium chloride catalysed condensation of 3-nitrobenzaldehyde onto the pyrone 1.3, as described in J. Med Chem. 1998, 41, 3467-3476, affords nitro pyrone 1.4. Nitro pyrone 1.4 upon treatment with triethylaluminum in the presence of copper(1) bromide-dimethylsulfide as described in J. Med Chem. 1998, 41, 3467-3476 affords the dihydropyrone 1.5. Protection of the dihydropyran hydroxyl in 1.5 with a suitable protecting group as described in Protective Groups in Organic Synthesis, by T. W. Greene and P. G. M Wuts, Wiley, Third Edition 1999 p.249ff gives the hydroxylprotected compound 1.6. For example, treatment with SEMCl in the presence of base e.g. potassium carbonate, generates the SEM ether protected 1.6. Catalytic hydrogenolysis of the nitro group, as described in J. Med Chem. 1998, 41, 3467-3476, affords the aryl amine 1.7 which is then coupled with the 5-trifluoromethyl-pyridine-2-sulfonyl chloride in the presence of pyridine, as described in J. Med Chem. 1998, 41, 3467-3476 to afford the sulfonamide 1.8. Finally, removal of the protecting group as described in Protective Groups in Organic Synthesis, by T. W. Greene and P. G. M Wuts, Wiley, Third Edition 1999 p.249ff affords the product 1.9. For example, treatment of the SEM protected product indicated above with TBAF produces the de-silylated (6R, 3R/S) product 1.9. The diastereoisomers are then separated through silica gel chromatography.

Scheme 2 also illustrates the synthesis of target molecules of type 1, chart 2, in which A is Br, Cl, [OH], [NH], or the group link-P(O)$(OR^1)_2$ but the products in this example have the absolute stereochemistry (6R, 3R). The ketone 1.2, prepared in Scheme 1, is transformed into the dihydropyrone 2.2 as described in Drugs of the Future, 1998, 23(2), p146. This 2 step reaction involves reaction of the ketone with dioxalone 2.1, prepared as described in Drugs of the Future, 1998, 23(2), p146 in the presence of $Ti(OBu)Cl_3$, followed by treatment with a base such as potassium tert-butoxide. Treatment of the dihydropyrone 2.2 with the same procedures reported in Scheme 1 for the conversion of 1.5 into 1.9 then affords the final product 1.9 in chiral form (6R, 3R). For example, the pyrone hydroxyl 2.2 is first protected as described in Protective Groups in Organic Synthesis, by T. W. Greene and P. G. M Wuts, Wiley, Third Edition 1999 p.249ff, to afford 2.3 and then the dibenzyl groups are removed from 2.3 by catalytic hydrogenolysis as described in Protective Groups in Organic Synthesis, by T. W. Greene and P. G. M Wuts, Wiley, Third Edition 1999 p.579 to afford the amine product 1.7. Amine 1.7 is then converted into 1.9 as described in Scheme 1.

The reactions shown in Scheme 1-2 illustrate the preparation of the compounds 1.9 in which the substituent A is either the group link-P(O)$(OR^1)_2$ or a precursor such as [OH], [SH], [NH], Br etc. Scheme 3 depicts the conversion of the compounds 1.9 in which A is [OH], [SH], [NH], Br etc, into the phosphonate esters 1. In this procedure, the compounds 1.9 are converted, using the procedures described below, Schemes 10-15, into the compounds 1.

Scheme 1

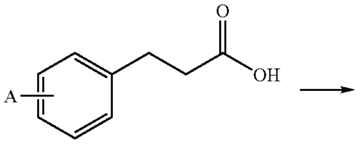

1.1

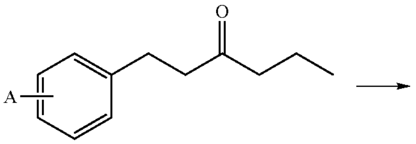

1.2

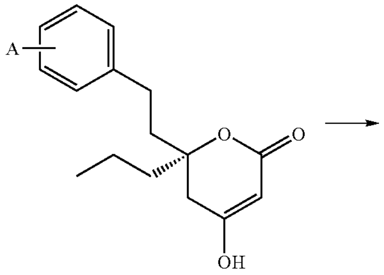

1.3

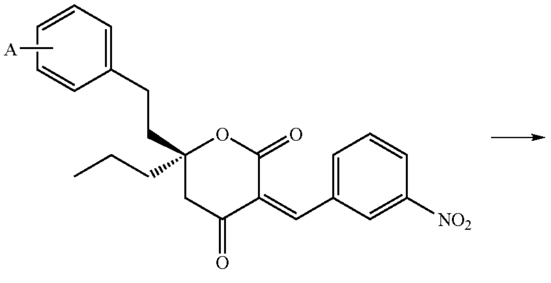

1.4

-continued
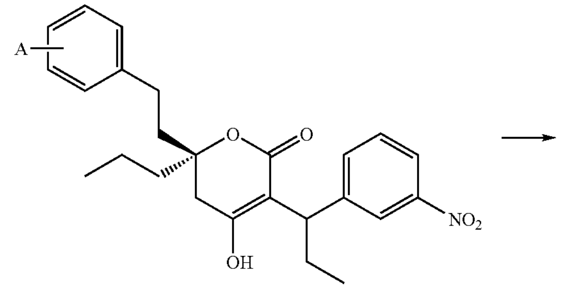
1.5
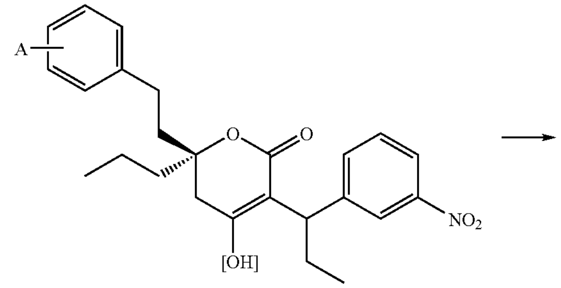
1.6
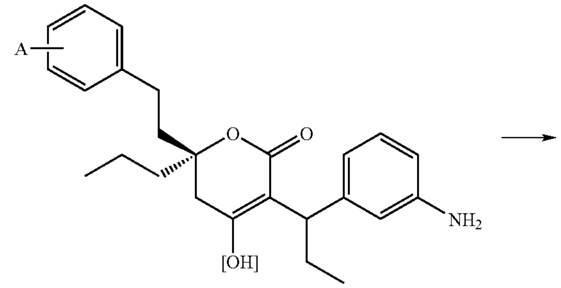
1.7
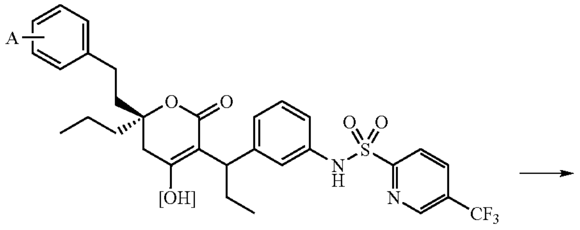
1.8
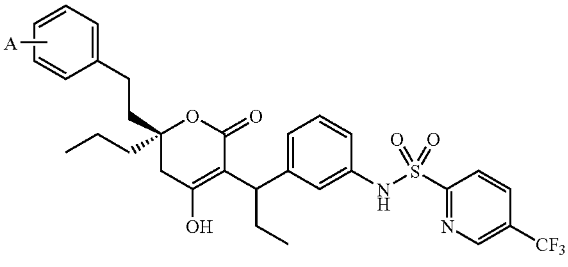
1.9
Scheme 2
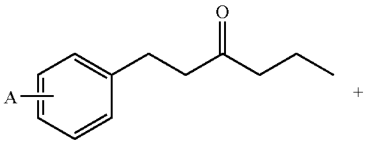
1.2
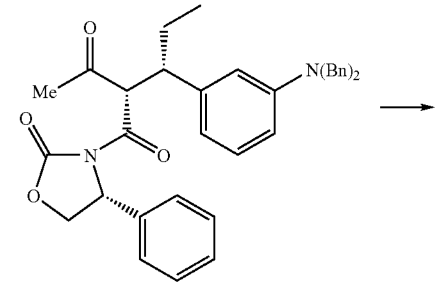
2.1
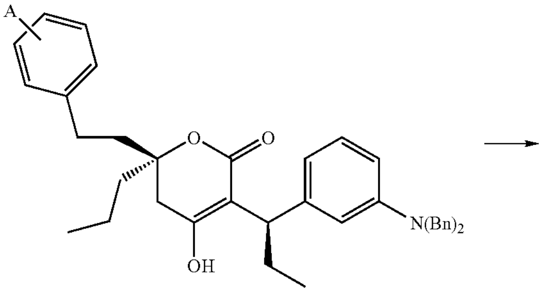
2.2
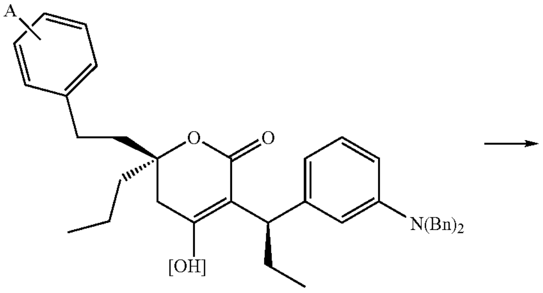
2.3
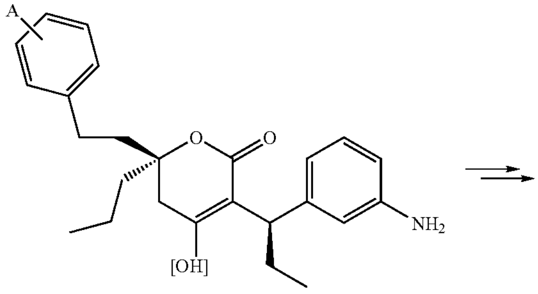
2.3

-continued

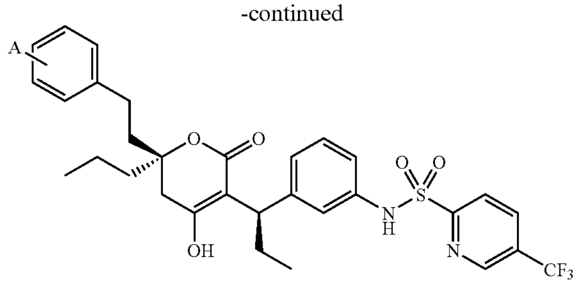

1.9

Scheme 4

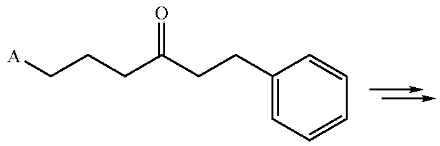

4.1

Scheme 3

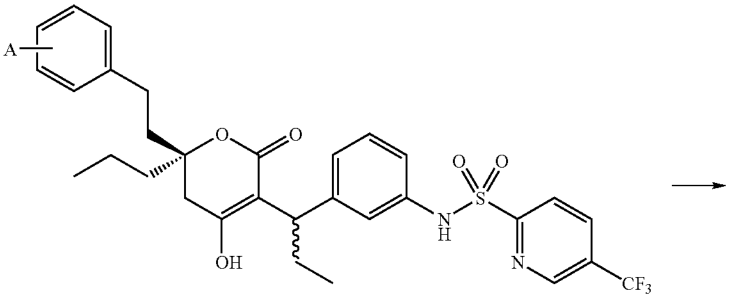

1.9

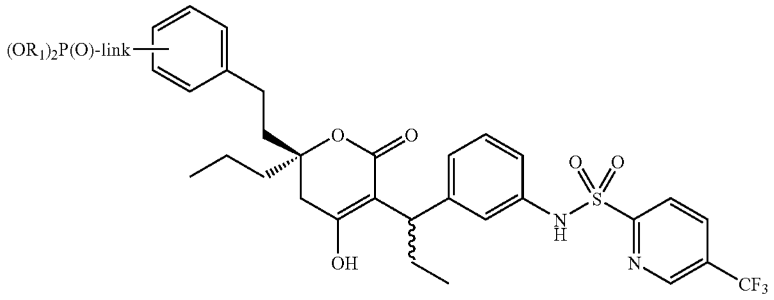

1

Scheme 4 illustrates the synthesis of target molecules of type 2, chart 2, in which A is Br, Cl, [OH], [NH], or the group link-$P(O)(OR^1)_2$. The acid 4.1 prepared as described below (Scheme 15), is converted into 4.2 using the procedures described in Scheme 1 or Scheme 2.

The reactions shown in Scheme 4 illustrate the preparation of the compounds 4.2 in which the substituent A is either the group link-$P(O)(OR^1)_2$ or a precursor such as [OH], [SH], [NH], Br etc. Scheme 5 depicts the conversion of the compounds 4.2 in which A is [OH], [SH], [NH], Br etc, into the phosphonate esters 2. In this procedure, the compounds 4.2 are converted, using the procedures described below, Schemes 10-15, into the compounds 2.

-continued

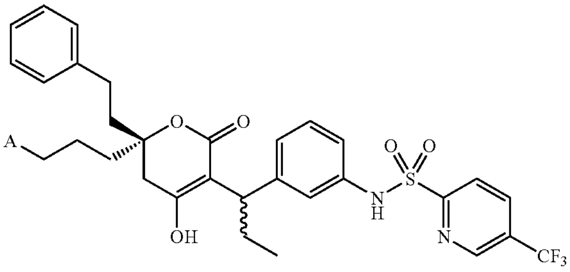

4.2

Scheme 5

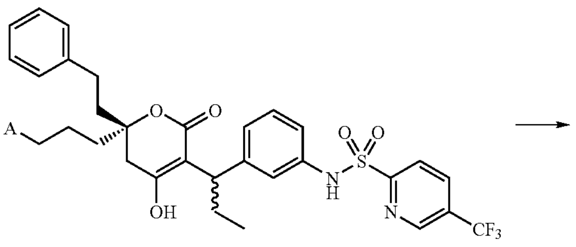

4.2

-continued

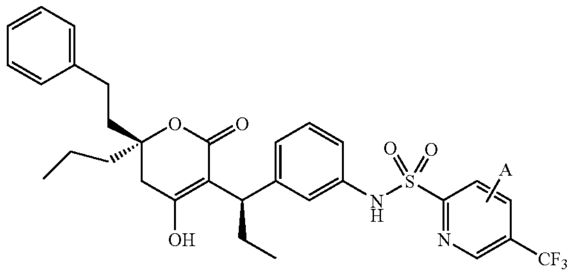

6.2

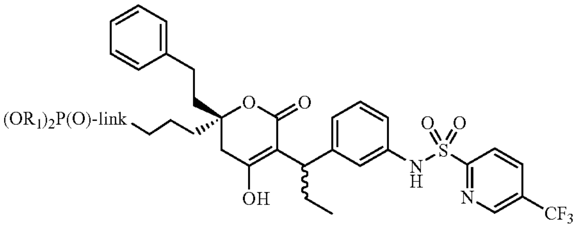

2

Scheme 7

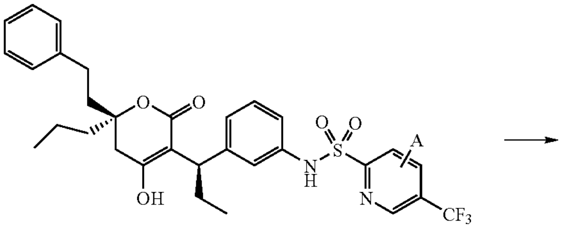

6.2

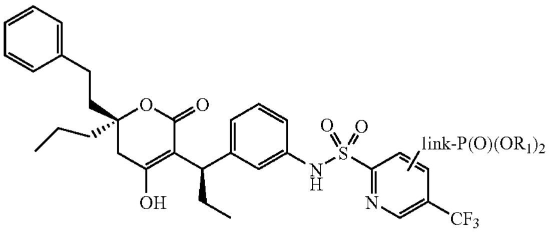

3

Scheme 6-7 illustrates the synthesis of target molecules of type 3, chart 2, in which A is Br, Cl, [OH], [NH], or the group link-P(O)(OR$^1$)$_2$. The amine 6.1 prepared as described in Drugs of the Future, 1998, 23(2), p146 or U.S. Pat. No. 5,852,195, is converted into the sulfonamide 6.2 using the procedures described in Scheme 1 or Scheme 2 for the preparation of 1.8 from 1.7. The synthesis of the sulfonyl chlorides 6.3 is shown below in Schemes 11-12.

The reactions shown in Scheme 6 illustrate the preparation of the compounds 6.2 in which the substituent A is either the group link-P(O)(OR$^1$)$_2$ or a precursor such as [OH], [SH], [NH], Br etc. Scheme 7 depicts the conversion of the compounds 6.2 in which A is [OH], [SH], [NH], Br etc, into the phosphonate esters 3. In this procedure, the compounds 6.2 are converted, using the procedures described below, Schemes 10-15, into the compounds 3.

Scheme 6

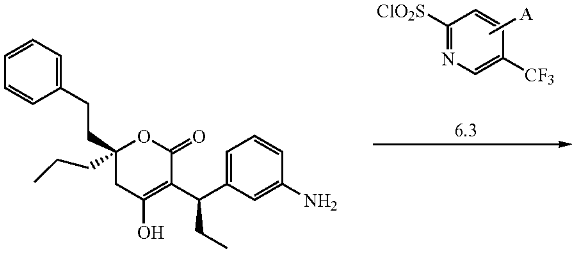

6.3

6.1

Scheme 8 illustrates the synthesis of target molecules of type 4, chart 2, in which A is Br, Cl, [OH], [NH], or the group link-P(O)(OR$^1$)$_2$. The amine 6.1 prepared as described in Drugs of the Future, 1998, 23(2), p146 or U.S. Pat. No. 5,852,195, is converted into the sulfonamide 8.1 by treatment with 8.2 using the procedures described in Scheme 1 or Scheme 2. The synthesis of the sulfonyl chlorides 8.2 is shown below in Scheme 10.

The reactions shown in Scheme 8 illustrate the preparation of the compounds 8.1 in which the substituent A is either the group link-P(O)(OR$^1$)$_2$ or a precursor such as [OH], [SH], [NH], Br etc. Scheme 9 depicts the conversion of the compounds 8.1 in which A is [OH], [SH], [NH], Br etc, into the phosphonate esters 4. In this procedure, the compounds 8.1 are converted, using the procedures described below, Schemes 10-15, into the compounds 4.

Scheme 8

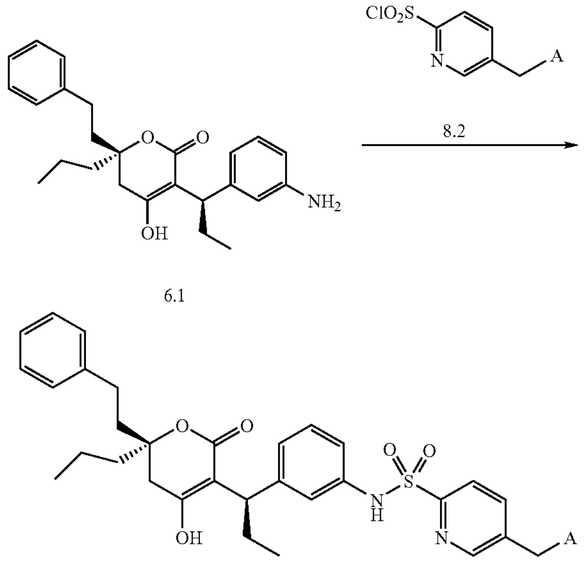

6.1

8.1

Scheme 9

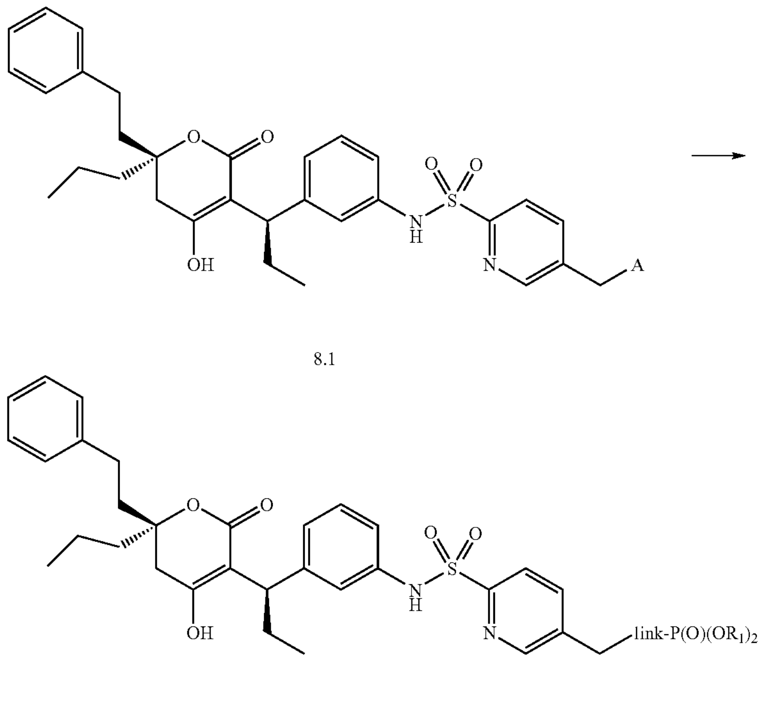

8.1

4

Preparation of Phosphonate Reagents Used in the Synthesis of Compounds 1-4

Schemes 10 describes the preparation of phosphonate-containing derivatives 8.2, in which the phosphonate is linked through a heteroatom, which are employed in the preparation of the phosphonate ester intermediates 4. The pyridyl ester 10.1 (Acros) is first reduced to the alcohol 10.2. This transformation involves reducing the ester with lithium aluminium hydride, or other reducing agent, in an inert solvent such as THF or dioxane. Alcohol 10.2 is then converted to the bromide 10.3 through typical hydroxyl to bromide conversion conditions described in Comprehensive Organic Transformations, R. C. Larock, $2^{nd}$ edition, p693-697. For instance, treatment of 10.2 with carbon tetrabromide and triphenylphosphine in THF or dioxane affords the bromide 10.3. Treatment of the bromide 10.3 with a thiol, amino, or hydroxyl alkyl phosphonate 10.6 then affords the phosphonate product 10.4. The reaction is performed in the presence of a base, in a polar aprotic solvent such as dioxane or N-methylpyrrolidinone. The base employed in the reaction depends on the nature of the reactant 10.6. For example, if X is O, a strong base such as, for example, lithium hexamethyldisilylazide or potassium tert. butoxide is employed. If X is S, NH or N-alkyl, an inorganic base such as cesium carbonate and the like is employed. The chloride 10.4 is then treated KHS in methanol, as described in Justus Liebigs Annalen Chemie, 1931, p105 or thiourea followed by potassium hydroxide treatment, as described in Heterocycles 1984, p117, to give the α-sulfide 10.5. If appropriate, reactive groups e.g. amines in the phosphonate chain, are protected using methods known to one skilled in the art. The α-sulfide 10.5 is then converted to the sulfonyl chloride 8.2 by treatment with chlorine in HCl, as described in Synthesis 1987, 4, p409, or J. Med. Chem 1980, 12, p1376.

For example, the pyridyl bromide 10.3, described above, is treated with amino phosphonate 10.7, prepared as described in J. Org. Chem. 2000, 65, p676, in the presence of potassium carbonate and DMF to afford the phosphonate product 10.8. Protection of the amine by conversion to the CBZ carbamate 10.9 is performed by treatment of 10.8 with benzyl chloroformate in the presence of triethylamine. Further treatment of 10.9 with thiourea in ethanol at reflux followed by treatment with potassium hydroxide in water then affords the thiol 10.10. Thiol 10.10 is then treated with chlorine in HCl (aqueous) to afford the sulfonyl chloride 10.11. Using the above procedures, but employing, in place of the amino alkyl phosphonate 10.7, different alkyl phosphonates 10.6, the corresponding products 8.2 are obtained.

Alternatively (Example 2), illustrates the preparation of phosphonates in which the link is through an oxygen atom. The pyridyl bromide 10.3 described above, is treated with hydroxyl phosphonate 10.12, prepared as described in Synthesis 1998, 4, p327, in the presence of potassium carbonate and DMF to afford the phosphonate product 10.13. Further treatment of 10.13, as described above, for the conversion of 10.8 into 10.11 affords the sulfonyl chloride 10.16. Using the above procedures, but employing, in place of the hydroxy alkyl phosphonate 10.12, different alkyl phosphonates 10.6 the corresponding products 8.2 are obtained.

Scheme 10

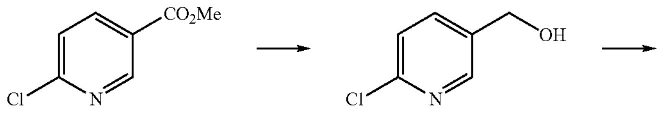

10.1 10.2

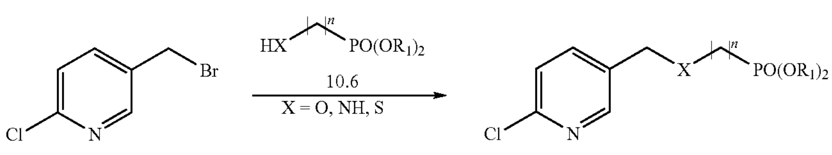

10.3 10.4

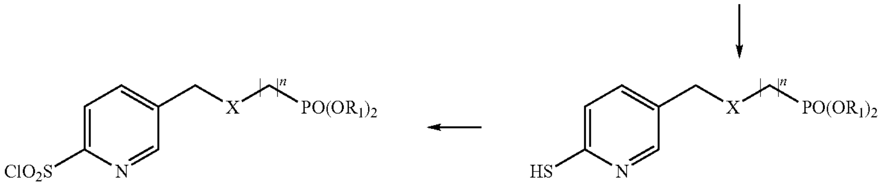

8.2 10.5

Example 1

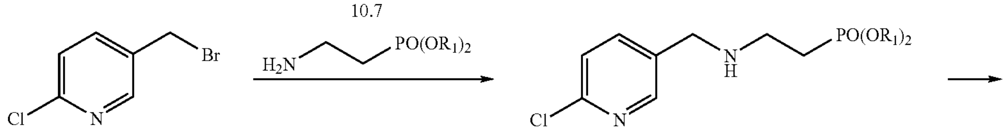

10.3 10.8

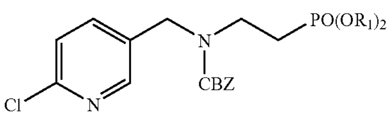

10.9

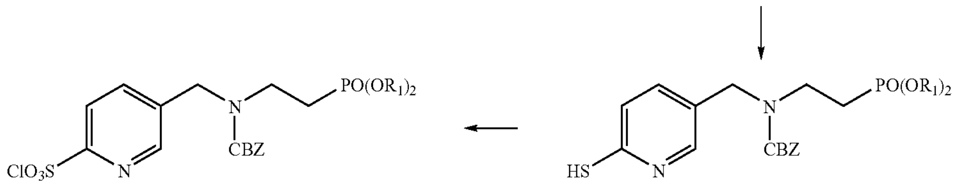

10.11 10.10

-continued

Example 2

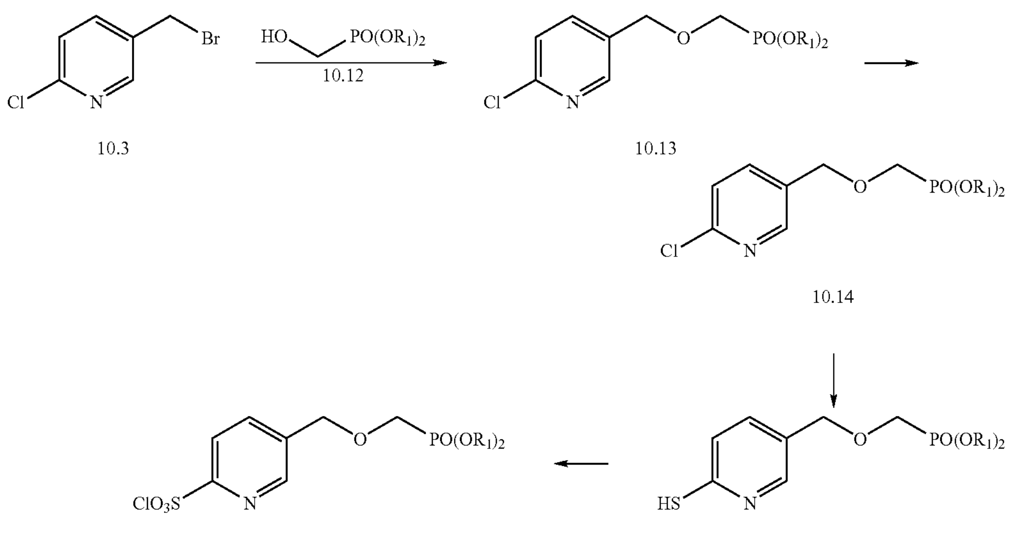

10.12

10.3 10.13 10.14 10.16 10.15

Schemes 11-12 describe the preparation of phosphonate-containing derivatives 6.3, which are employed in the preparation of the phosphonate ester intermediates 3. Scheme 11 illustrates compounds of type 6.3 in which the link is through a oxygen, sulfur or nitrogen heteroatom.

Pyridyl halide 11.1 is treated with the dialkyl hydroxy, thio or amino-substituted alkylphosphonate 10.6 to give the product 11.3. The reaction is performed in the presence of a base, in a polar aprotic solvent such as dioxan or N-methylpyrrolidinone. The base employed in the reaction depends on the nature of the reactant 10.6. For example, if X is O, a strong base such as, for example, lithium hexamethyldisilylazide or potassium tert. butoxide is employed. If X is S, NH or N-alkyl, an inorganic base such as cesium carbonate and the like is employed. Upon formation of 11.3 the pyridine is converted to the α-chloro pyridine 11.4 by treatment with chlorine at high temperature in a sealed vessel as described in Recl. Trav. Chim Pays-Bas 1939, 58, p709 or, preferably, the α-chloro compound is generated by treatment of 11.3 with butyl lithium in hexane and $Me_2N(CH_2)_2OLi$ followed by addition of a chloride source such as hexachloroethane, as described in Chem Commun. 2000, 11, p951. Chloride 11.4 is then converted to the thiol 11.4 as described above (Scheme 10). Thiol 11.5 is then converted to the sulfonyl chloride 6.3 as described in Scheme 10.

For example, bromo pyridine (Apollo) 11.6 is treated with amine 10.7 in the presence of cesium carbonate in THF or alternative solvent at reflux to give the amine 11.7. The amine is then converted to the sulfonyl chloride 11.9 through the intermediate chloride 11.8 as described in Scheme 10. Using the above procedures, but employing, in place of the amino alkyl phosphonate 10.7, different alkyl phosphonates 10.6, and in place of the pyridine 11.6 different halo pyridines 11.1, the corresponding products 6.3 are obtained.

Alternatively the bromo pyridine 11.6 (Apollo) is treated with thiol 11.10, prepared as described in Zh. Obschei. Khim 1973, 43. p2364, in the presence of cesium carbonate in THF or alternative solvent at reflux to give the thiol 11.11. The thiol is then converted to the sulfonyl chloride 11.12 as described above for the conversion of 11.7 into 11.9. Using the above procedures, but employing, in place of the thiol alkyl phosphonate 11.10, different alkyl phosphonates 10.6, and in place of the pyridine 11.6 different halo pyridines 11.1, the corresponding products 6.3 are obtained.

Scheme 12 illustrates compounds of type 6.3 in which the phosphonate is attached through an unsaturated or saturated carbon linker. In this procedure, pyridyl bromo compound 11.1 is treated under a palladium catalyzed Heck coupling conditions with the alkene 12.1 to give the coupled alkene 12.2. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxane, in the presence of a palladium(0) catalyst such as tetrakis(triphenylphosphine) palladium(0) or a palladium(II) catalyst such as palladium(II) acetate, and optionally in the presence of a base such as triethylamine or potassium carbonate, to afford the coupled product 12.2. Optionally, the product 12.2 can be reduced to afford the saturated phosphonate 12.4. Methods for the reduction of carbon-carbon double bonds are described, for example, in Comprehensive Organic Transformations, by R. C. Larock, VCH, 1989, p. 6. The methods include catalytic reduction, and chemical reduction, the latter for example employing diborane or dlimide. Following the Heck reaction or reduction the pyridyl compounds 12.2 and 12.4 are converted to the sulfonyl chlorides 12.3 and 12.5 respectively, using the same procedures described in Scheme 11 for the conversion of 11.3 into 6.3

For example, pyridine 11.6 (Aldrich) is reacted with a dialkyl propenyl phosphonate 12.6, the preparation of which is described in J. Med. Chem., 1996, 39, 949, in the presence of bis(triphenylphosphine)palladium(II) chloride, as described in J. Med. Chem., 1992, 35, 1371, to-afford the coupled product 12.7. The product 12.7 is then reduced, for example by reaction with dlimide, as described in J. Org. Chem., 30, 3965, 1965, to afford the saturated product 12.9. Conversion of the products 12.7 and 12.9 into the sulfonyl chlorides 12.8 and 12.10 respectively follows the same procedures described above for the conversion of pyridine 11.7 into 11.9. Using the above procedures, but employing, in place of the halo pyridine compound 11.6, different pyridines 11.1, and/or different phosphonates 12.1 in place of 12.6, the corresponding products 12.3 and 12.5 are obtained.

Scheme 11
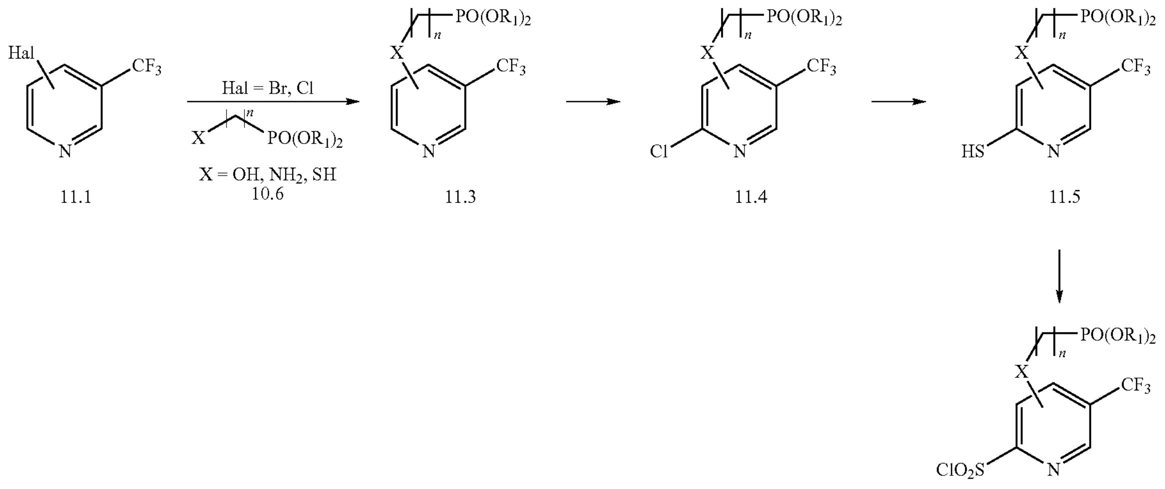
11.1 10.6 11.3 11.4 11.5
6.3
Example 1
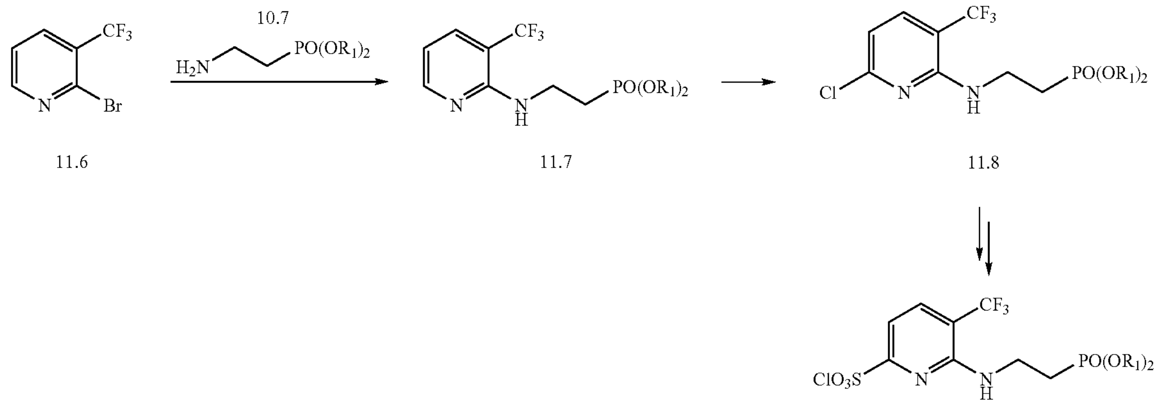
11.6 11.7 11.8
11.9
Example 2
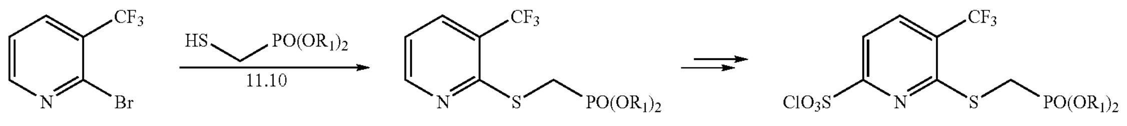
11.6 11.11 11.12
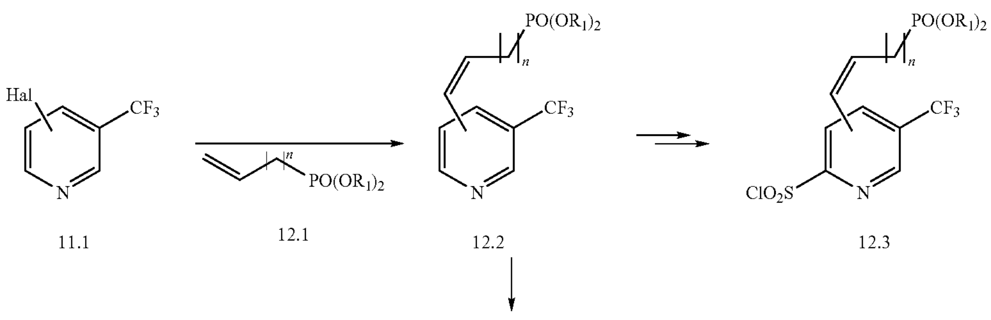
11.1 12.1 12.2 12.3

-continued

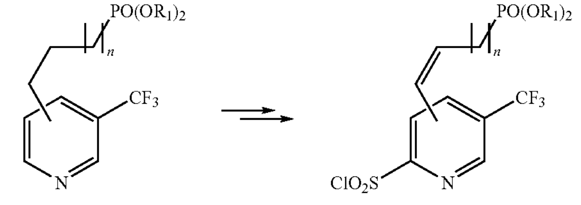

12.4 12.5

Example 1

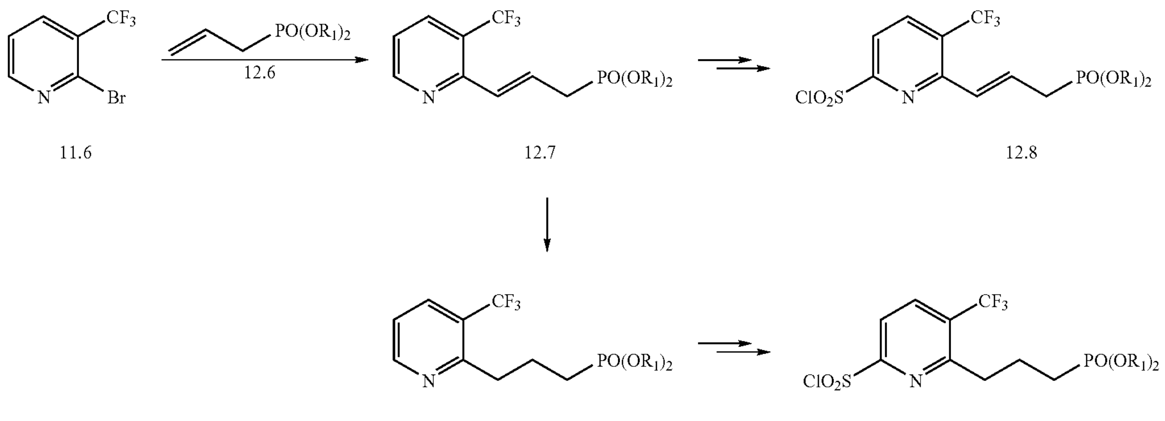

11.6 12.7 12.8

12.9 12.10

Schemes 13-14 illustrate the preparation of phosphonate containing compounds 1.1 that are used in the preparation of the compounds of type 1, chart 2. Scheme 13 illustrates the preparation of phosphonates 1.1 in which the phosphonate is attached through a heteroatom such as S, O or N. The aryl halide 13.1 bearing a hydroxyl, amino or thiol group, is treated with one equivalent of the phosphonate alkylating agent 13.2, in which Lv is a group such as mesyl, trifluoromethanesulfonyl, Br, I, Cl, tosyl etc, in the presence of base e.g. potassium or cesium carbonate in DMF, to give the compound 13.3. The product 13.3 is then converted to the alkene 13.4 using a palladium mediated Heck coupling with Methyl acrylate as described above, Scheme 12. The acrylate is reduced as described in Scheme 12 and then the ester is hydrolyzed by treatment with base such as lithium or sodium hydroxide to afford the acid 1.1.

For example, the halide 13.6 (Aldrich) is treated with triflate phosphonate 13.7, prepared as described in Tet. Lett. 1986, 27, p1497, and potassium carbonate in DMF, to give the ether 13.8. The ether is then treated with methyl acrylate under Heck coupling conditions as described in J. Med. Chem. 1992, 35, p1371, to give the alkene 13.9. 13.9 is reduced by treatment with dlimide, as described analogously in Bioorg Med. Chem. 1999, 7, p2775 to give the saturated aryl ester 13.10. Treatment of 13.10 with lithium hydroxide in THF and water then affords the acid 13.11. Using the above procedures, but employing, in place of the aryl halide 13.6, different aryl halides 13.1, and/or different phosphonates 13.2 in place of 13.7, the corresponding products 1.1 are obtained.

Scheme 14 illustrates the preparation of phosphonates 1.1 in which the link is through a carbon bond and a nitrogen heteroatom. The aryl halide bearing an carbonyl group is treated with one equivalent of the amino alkyl phosphonate 14.2 under reductive amination conditions to give the amine 14.3. The preparation of amines by means of reductive amination procedures is described, for example, in Comprehensive Organic Transformations, by R. C. Larock, $2^{nd}$ edition, p. 835. In this procedure, the amine component and the aldehyde component are reacted together in the presence of a reducing agent such as, for example, borane, sodium cyanoborohydride or diisobutylaluminum hydride, to yield the amine product 14.3. The amine product 14.3 is then converted to the alkene 14.4 using a palladium mediated Heck coupling with Methyl acrylate as described above, Scheme 13. The acrylate is then reduced as described in Scheme 13 to give 14.5, and then the ester is hydrolyzed by treatment with base such as lithium or sodium hydroxide to afford the acid 1.1.

For example, the halide 14.6 (Aldrich) is treated with amino phosphonate 10.7, prepared as described above, in methanol for 30 min. After 30 min sodium borohydride is added to give the amine 14.7. The amine 14.7 is then treated with methyl acrylate under Heck coupling conditions as described above, to give the alkene 14.8. Alkene 14.8 is reduced as described in Scheme 13 to give the saturated ester 14.9. Treatment of 14.9 with lithium hydroxide in THF and water then affords the acid 14.10. Using the above procedures, but employing, in place of the aryl halide 14.6, different aryl halides 14.1, and/or different amino phosphonates 14.2 in place of 10.7, the corresponding products 1.1 are obtained.

Scheme 13
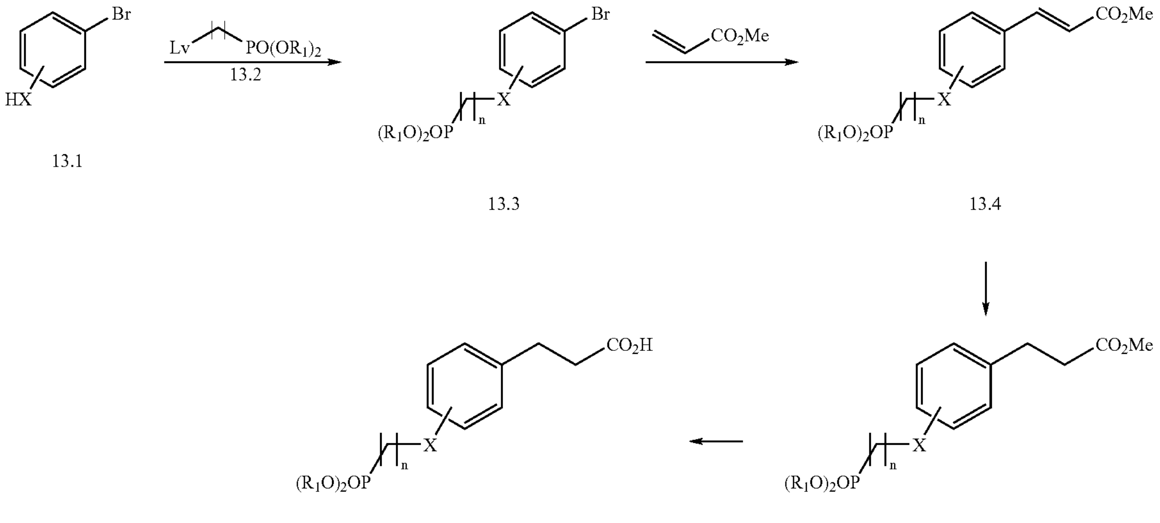
13.1 13.3 13.4 13.5 1.1
Example 1
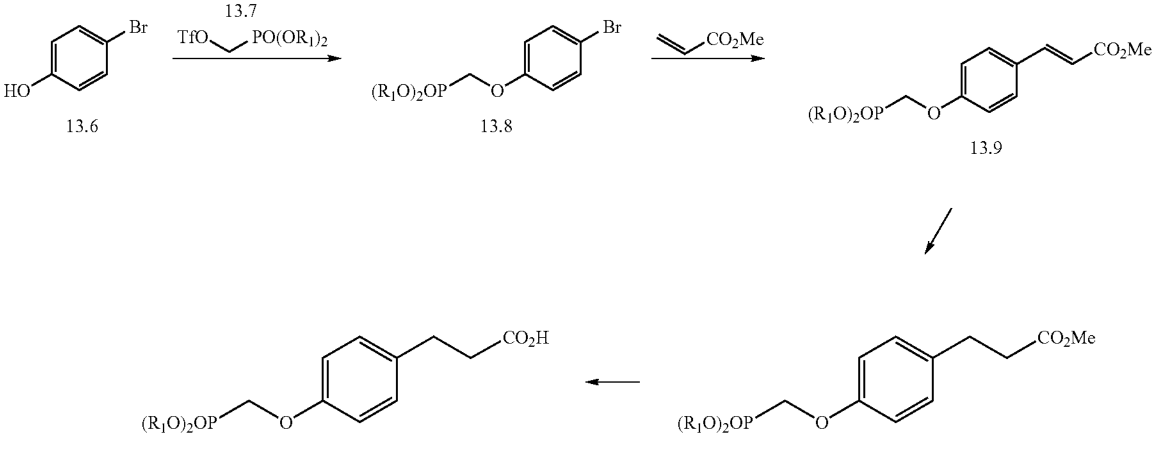
13.6 13.8 13.9 13.10 13.11
Scheme 14
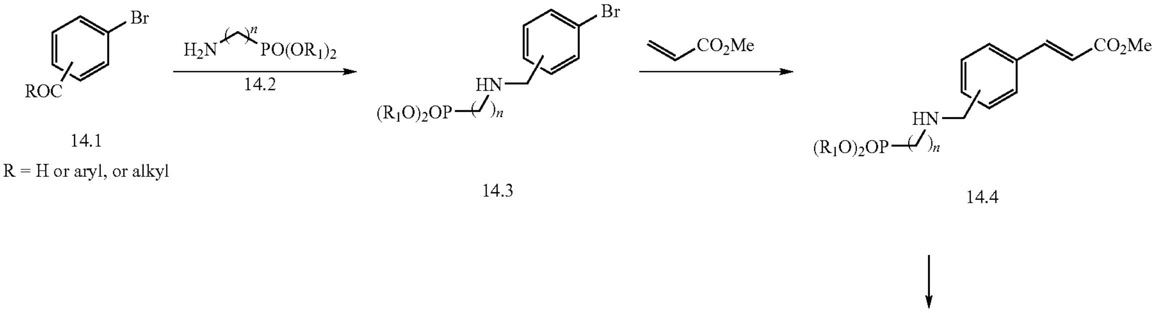
14.1 14.3 14.4
R = H or aryl, or alkyl -continued

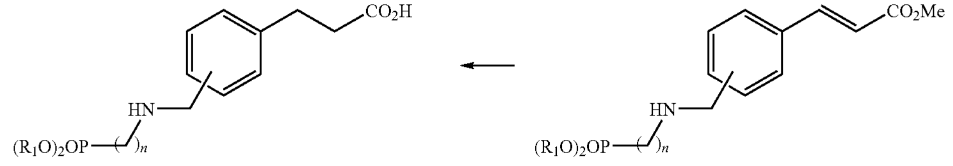

1.1 14.5

Example 1

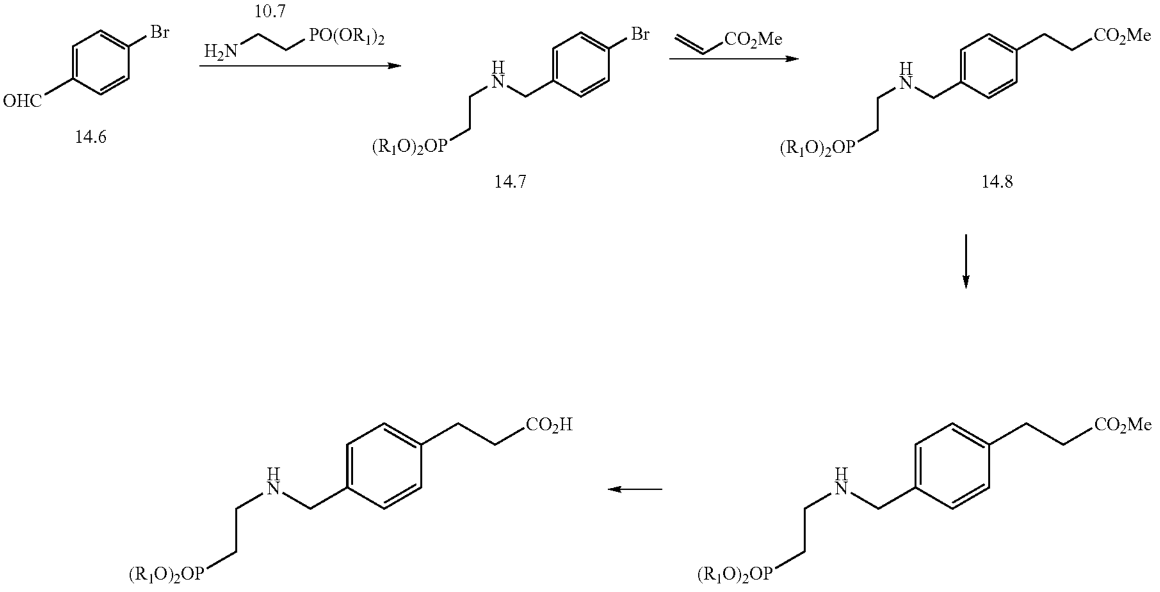

14.6 14.7 14.8

14.10 14.9

Scheme 15 describes the preparation of phosphonate-containing derivatives 4.1 which are employed in the preparation of the phosphonate ester intermediates 2, chart 2. The alcohol 15.1 prepared as described in J. Org Chem. 1994, 59, p3445, is treated with ethylene glycol and a catalytic amount of toxic acid in benzene at reflux to give the 1,3-dioxalone 15.2. The dioxalone is then treated with carbon tetrabromide and triphenyl phosphine in acetonitrile, or alternate conditions as described in Comprehensive Organic Transformations, R. C. Larock, $2^{nd}$ editions, p693-697, to generate the bromide 15.3. Bromide 15.3 is then treated with the dialkyl hydroxy, thio or amino-substituted alkylphosphonate 10.6 to give the product 15.4. The reaction is performed in the presence of a base, in a polar aprotic solvent such as dioxan or N-methylpyrrolidinone. The base employed in the reaction depends on the nature of the reactant 10.6. For example, if X is O, a strong base such as, for example, lithium hexamethyldisilylazide or potassium tert. butoxide is employed. If X is S, NH or N-alkyl, an inorganic base such as cesium carbonate and the like is employed. Following preparation of 15.4 the dioxalone is removed as described in Protective Groups in Organic Synthesis, by T. W. Greene and P. G. M Wuts, Wiley, Third Edition 1999 p.317.

For example, 15.5 described above, is treated with alcohol 10.12, prepared as described in Scheme 10, in DMF and potassium carbonate at ca 80° C. to give the phosphonate 15.7. Alternatively bromide 15.5 is then heated at reflux with an equimolar amount of a dialkyl 2-mercaptoethylphosphonate 11.10, the preparation of which is described in Aust. J. Chem., 43, 1123, 1990, in the presence of sodium carbonate, to afford the thioether product 15.9.

Treatment of 15.7 and 15.9 with aqueous HCl in THF then affords the ketones 15.8 and 15.10 respectively. Using the above procedures, but employing, in place of 10.12 and 11.10, different alkyl phosphonates 10.6 the corresponding products, 4.1 are obtained.

Scheme 15

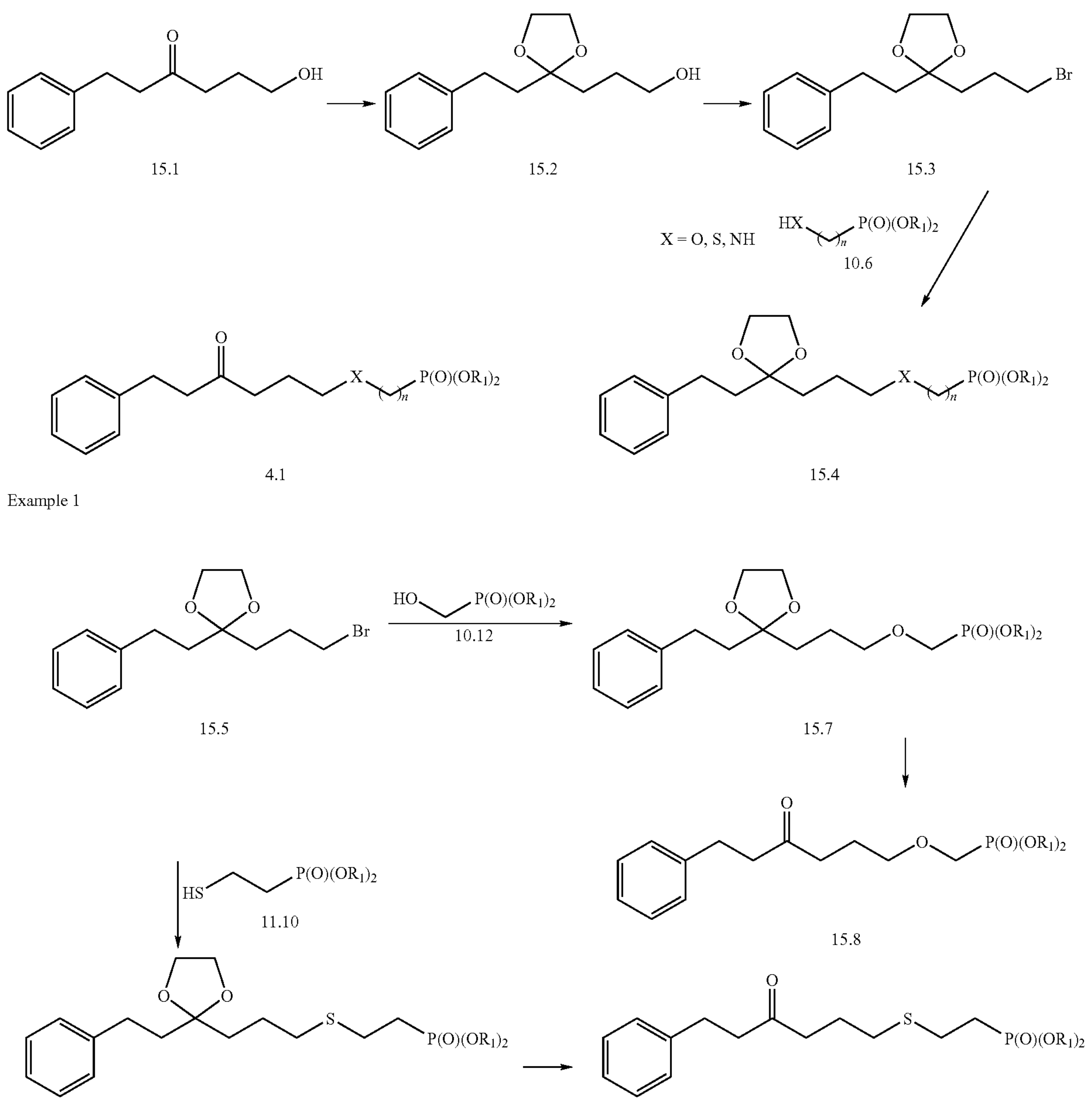

15.1 15.2 15.3 4.1 15.4 15.5 15.7 15.8 15.9 15.10

General Applicability of Methods for Introduction of Phosphonate Substituents.

The procedures described for the introduction of phosphonate moieties (Schemes 10-15) are, with appropriate modifications known to one skilled in the art, transferable to different chemical substrates. Thus, for example, the methods described above for the introduction of phosphonate groups onto the pyridyl ring of 11.1, are also applicable to the introduction of phosphonate moieties onto the aryl rings of 13.1 and 14.1, and the reverse is also true.

Interconversions of the Phosphonates Between R-link-P(O)$(OR^1)_2$, R-link-P(O)$(OR^1)(OH)_2$ and R-link-P(O)$(OH)_2$.

The schemes above describe the preparation of phosphonates of general structure R-link-P(O)$(OR^1)_2$ in which the $R^1$ groups are defined as indicated in Chart 2, and the R group refers to the scaffold. The $R^1$ groups attached to the phosphonate esters in Chart 2 may be changed using established chemical transformations. The interconversion reactions of the phosphonates attached through the link group to the scaffold (R) are illustrated in Scheme 16.

The interconversions may be carried out in the precursor compounds or the final products using the methods described below. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 16.1 into the corresponding phosphonate monoester 16.2 (Scheme 16, Reaction 1) can be accomplished by a number of methods. For example, the ester 16.1 in which $R^1$ is an aralkyl group such as benzyl, can be converted into the monoester compound 16.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 16.1 in which $R^1$ is an aryl group such as phenyl, or an alkenyl group such as allyl, into the monoester 16.2 can be effected by treatment of the ester 16.1 with a base such as aqueous sodium hydroxide in acetonitrile or lithium hydroxide in aqueous tetrahydrofuran.

Phosphonate diesters 16.2 in which one of the groups $R^1$ is aralkyl, such as benzyl, and the other is alkyl, can be converted into the monoesters 16.2 in which $R^1$ is alkyl by hydrogenation, for example using a palladium on carbon catalyst. Phosphonate diesters in which both of the groups $R^1$ are alkenyl, such as allyl, can be converted into the monoester 16.2 in which $R^1$ is alkenyl, by treatment with chlorotris(triphenylphosphine)rhodium (Wilkinson's catalyst) in aqueous ethanol at reflux, optionally in the presence of diazabicyclooctane, for example by using the procedure described in J. Org. Chem., 38 3224 1973 for the cleavage of allyl carboxylates.

The conversion of a phosphonate diester 16.1 or a phosphonate monoester 16.2 into the corresponding phosphonic acid 16.3 (Scheme 16, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 16.2 in which $R^1$ is aralkyl such as benzyl, can be converted into the corresponding phosphonic acid 16.3 by hydrogenation over a palladium catalyst, or by treatment with hydrogen chloride in an ethereal solvent such as dioxan. A phosphonate monoester 16.2 in which $R^1$ is alkenyl such as, for example, allyl, can be converted into the phosphonic acid 16.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 16.1 in which $R^1$ is benzyl is described in J. Org. Chem., 24, 434, 1959. Platinum-catalyzed hydrogenolysis of phosphonate esters 16.1 in which $R^1$ is phenyl is described in J. Amer. Chem. Soc., 78, 2336, 1956.

The conversion of a phosphonate monoester 16.2 into a phosphonate diester 16.1 (Scheme 16, Reaction 4) in which the newly introduced $R^1$ group is alkyl, aralkyl, haloalkyl such as chloroethyl, or aralkyl can be effected by a number of reactions in which the substrate 16.2 is reacted with a hydroxy compound $R^1OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 16.1 to the diester 16.1 can be effected by the use of the Mitsonobu reaction. The substrate is reacted with the hydroxy compound $R^1OH$, in the presence of diethyl azodicarboxylate and a triarylphosphine such as triphenyl phosphine. Alternatively, the phosphonate monoester 16.2 can be transformed into the phosphonate diester 16.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate.

Alternatively, the phosphonate monoester can be transformed into the phosphonate diester in a two step procedure. In the first step, the phosphonate monoester 16.2 is transformed into the chloro analog $RP(O)(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester 16.1.

A phosphonic acid R-link-$P(O)(OH)_2$ can be transformed into a phosphonate monoester $RP(O)(OR^1)(OH)$ (Scheme 16, Reaction 5) by means of the methods described above of for the preparation of the phosphonate diester R-link-$P(O)(OR^1)_2$ 16.1, except that only one molar proportion of the component $R^1OH$ or $R^1Br$ is employed. A phosphonic acid R-link-$P(O)(OH)_2$ 16.3 can be transformed into a phosphonate diester R-link-$P(O)(OR^1)_2$ 16.1 (Scheme 16, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids 16.3 can be transformed into phosphonic esters 16.1 in which $R^1$ is aryl, by means of a coupling reaction employing, for example, dicyclohexylcarbodiimide in pyridine at ca 70°. Alternatively, phosphonic acids 16.3 can be transformed into phosphonic esters 16.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 16.1.

Scheme 16

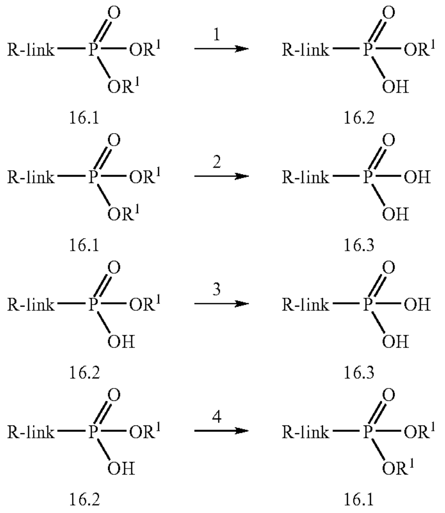

16.1 16.2
16.1 16.3
16.2 16.3
16.2 16.1

-continued

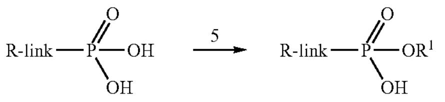

16.3 16.2

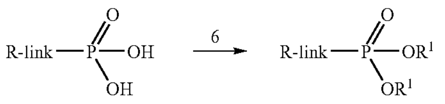

16.3 16.1

Amprenavir-like Phosphonate Protease Inhibitors (AMLPPI)

Preparation of the Intermediate Phosphonate Esters 1-13.

The structures of the intermediate phosphonate esters 1 to 13 and the structures of the component groups $R^1$, $R^5$, X of this invention are shown in Charts 1-2. The structures of the $R^2NH_2$ components are shown in Chart 3; the structures of the $R^3$—Cl components are shown in Chart 4; the structures of the $R_4COOH$ groups are shown in Chart 5a-c; and the structures of the $R^9CH_2NH_2$ amine components are illustrated in Chart 6.

Specific stereoisomers of some of the structures are shown in Charts 1-6; however, all stereoisomers are utilized in the syntheses of the compounds 1 to 13. Subsequent chemical modifications to the compounds 1 to 10, as described herein, permit the synthesis of the final compounds of this invention.

The intermediate compounds 1 to 10 incorporate a phosphonate moiety $(R^1O)_2P(O)$ connected to the nucleus by means of a variable linking group, designated as "link" in the attached structures. Charts 7, and 8 illustrate examples of the linking groups present in the structures 1-10.

Schemes 1-99 illustrate the syntheses of the intermediate phosphonate compounds of this invention, 1-10, and of the intermediate compounds necessary for their synthesis. The preparation of the phosphonate esters 11, 12 and 13, in which a phosphonate moiety is incorporated into one of the groups $R^4$, $R^3$, $R^2$, respectively, is also described below.

CHART 1

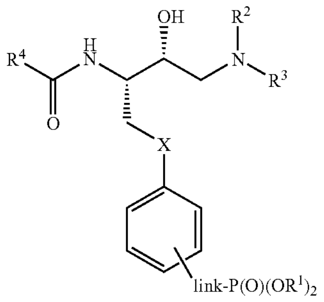

1

CHART 1-continued

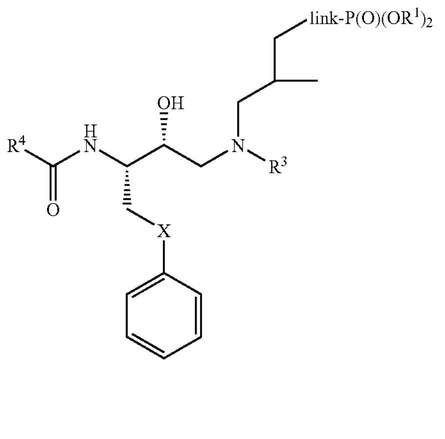

2

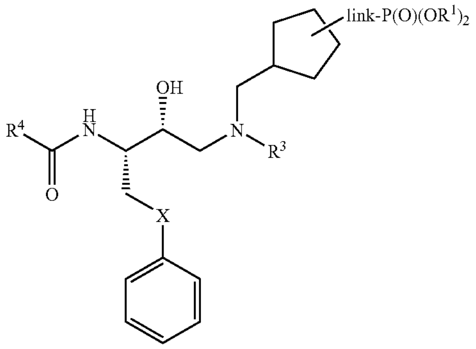

3

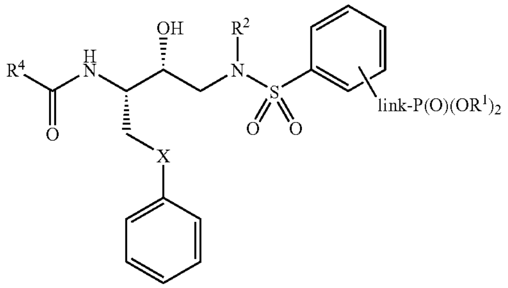

4

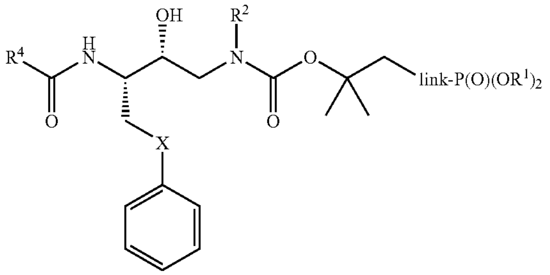

5

CHART 1-continued

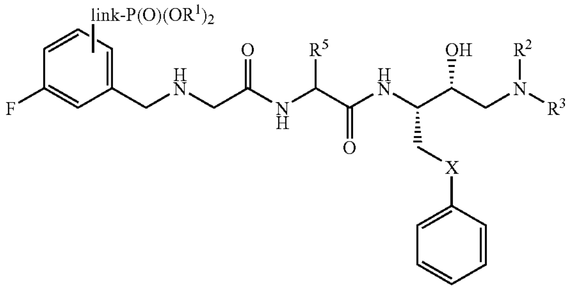

6

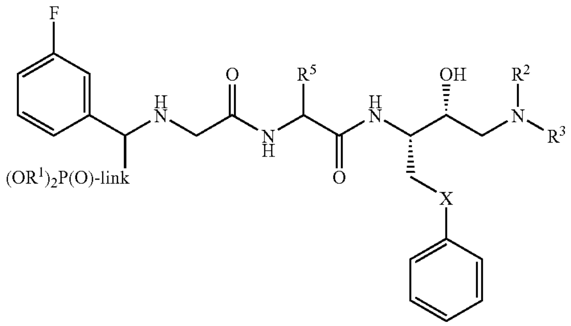

7

$R^1$ = H, alkyl, haloalkyl, alkenyl, aralkyl, aryl

X = S or direct bond $R^5$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$, tert-butyl

CHART 2

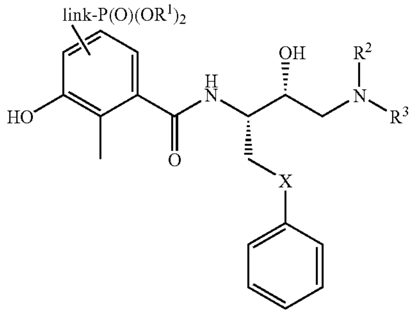

8

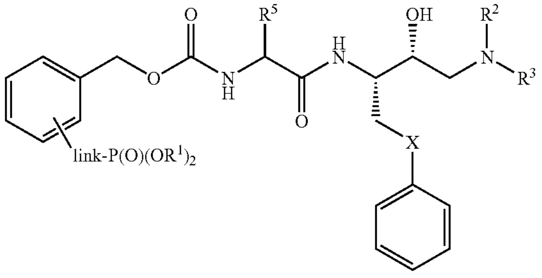

9

CHART 2-continued

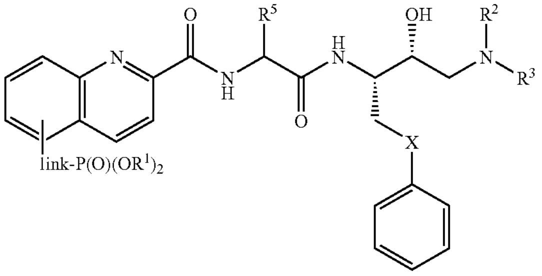

10

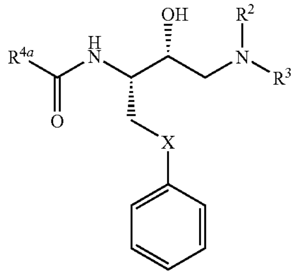

$R^{4a}$ = phosphonate containing $R^4$

11

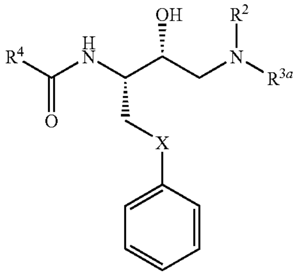

$R^{3a}$ = phosphonate containing $R^3$

12

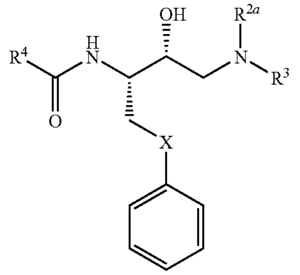

$R^{2a}$ = phosphonate containing $R^2$

13

$R^1$ = H, alkyl, haloalkyl, alkenyl, aralkyl, aryl

X = S or direct bond $R^5$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$, tert-butyl CHART 3
Structures containing the $R^2$—$NH_2$ components
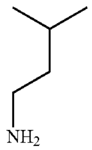
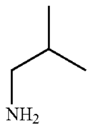
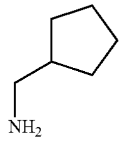
CHART 4
Structures containing the $R^3$—Cl components
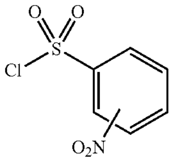
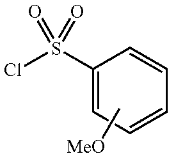
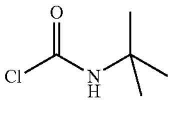
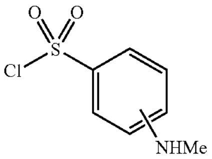
CHART 5a
Structures of the $R^4$COOH components
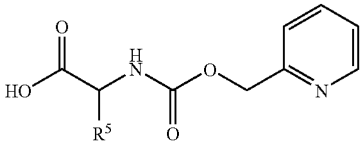
C1
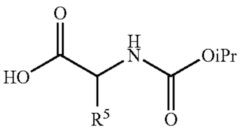
C2
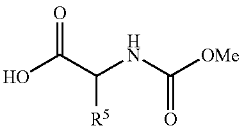
C3
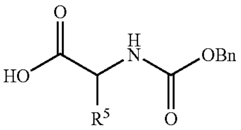
C4
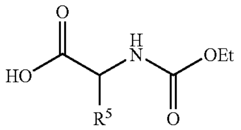
C5
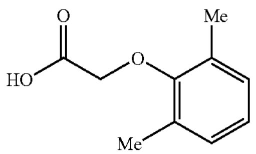
C6
CHART 5a-continued
Structures of the $R^4$COOH components
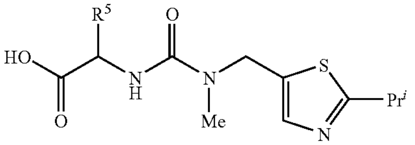
C7
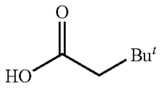
C8
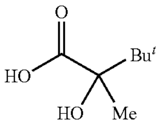
C9
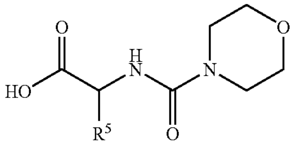
C10
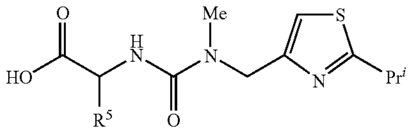
C11
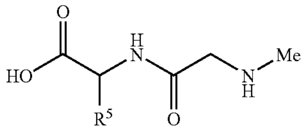
C12
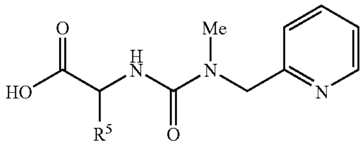
C13
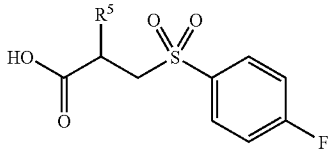
C14
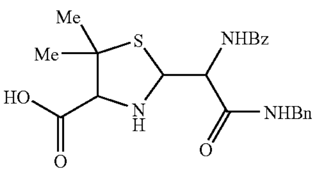
C15
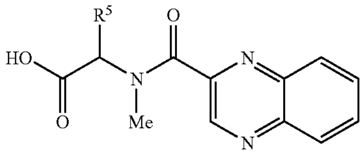

CHART 5a-continued
Structures of the $R^4COOH$ components
C16
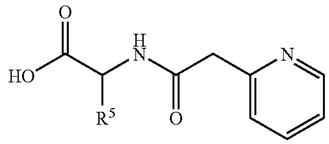
C17
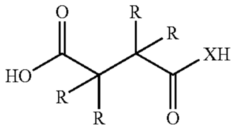
X = O, NH
R = H, alkyl
C18
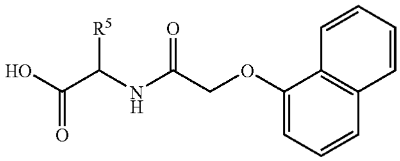
C19
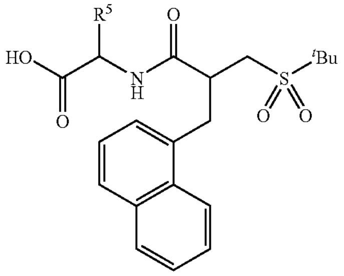
C20
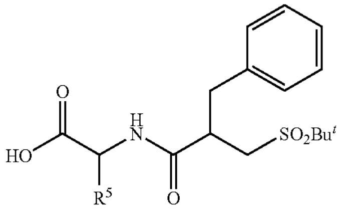
C21
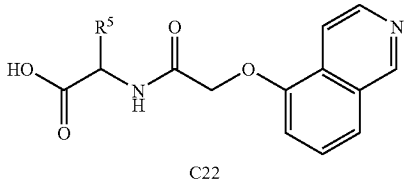
C22
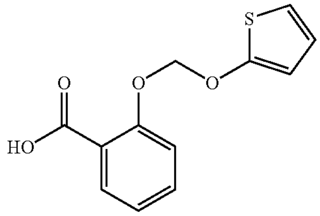
CHART 5a-continued
Structures of the $R^4COOH$ components
C23
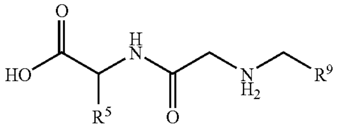
C24
$R^5$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$, tert-butyl
CHART 5b
Structures of the $R^4COOH$ components
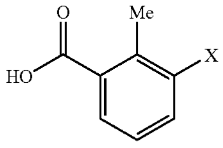
C25
X = OH, $NH_2$
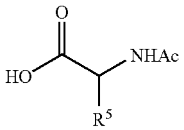
C26
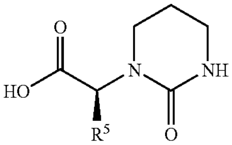
C27
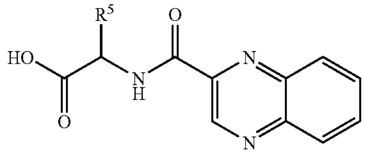
C28
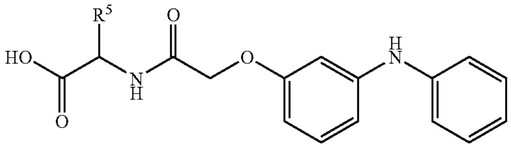
C29
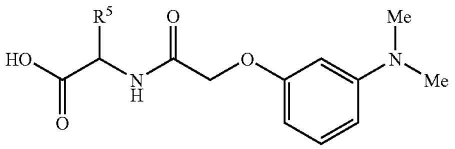
C30
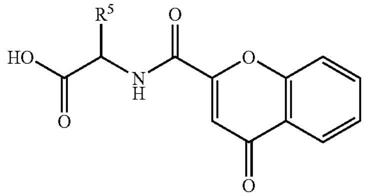
C31

CHART 5b-continued
Structures of the $R^4COOH$ components
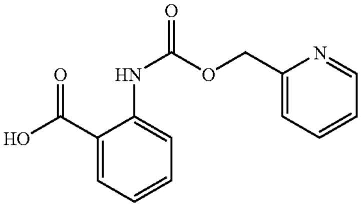
C32
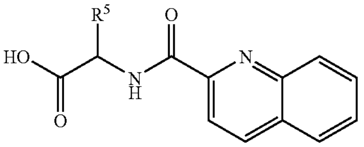
C33
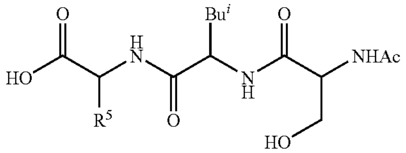
C34
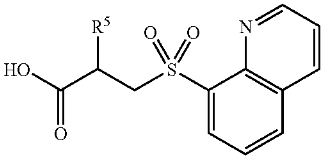
C35
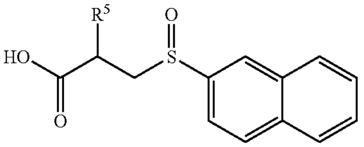
C36
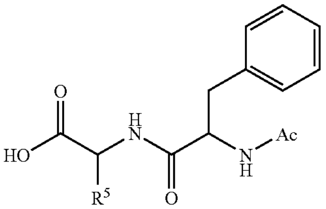
C37
$R^5$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$, tert-butyl
CHART 5c
Structures of the $R^4COOH$ components
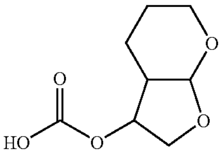
C38
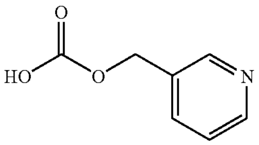
C39
CHART 5c-continued
Structures of the $R^4COOH$ components
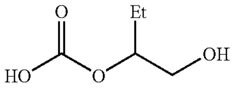
C40
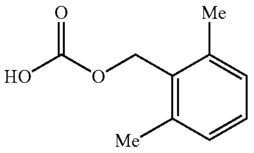
C41
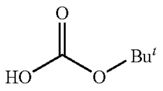
C42
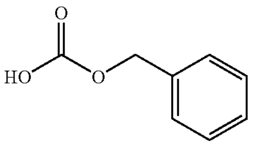
C43
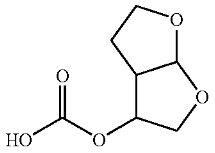
C44
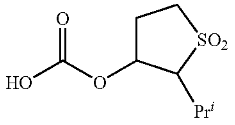
C45
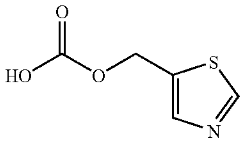
C46
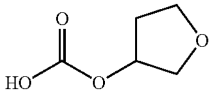
C47
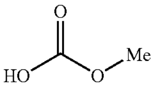
C48
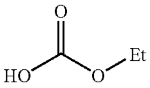
C49
CHART 6
Structures of the $R^9CH_2NH_2$ components
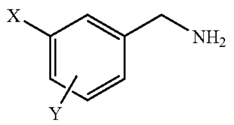
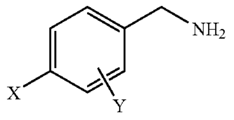
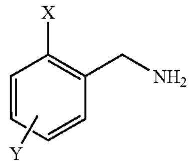
X = F, Br, Cl; Y = H, F, Br, Cl CHART 7
direct bond
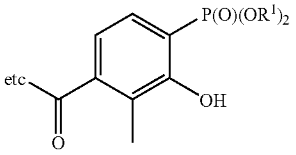
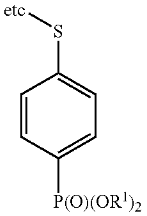
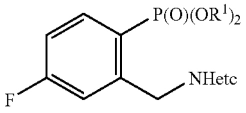
single carbon
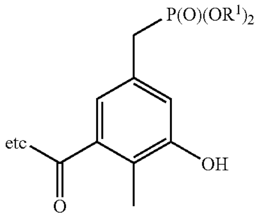
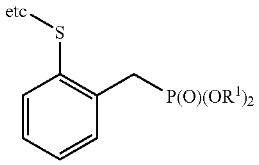
multiple carbon
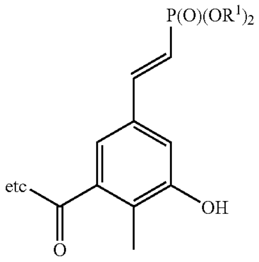
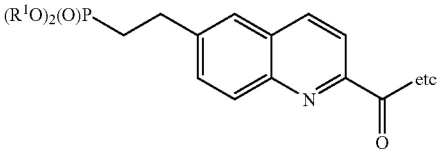
heteroatom
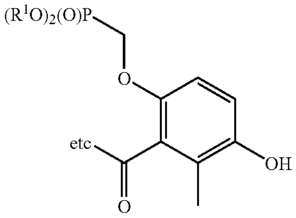
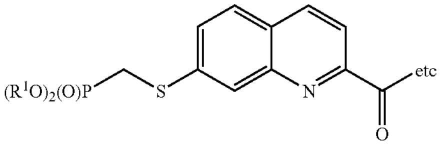
CHART 7-continued
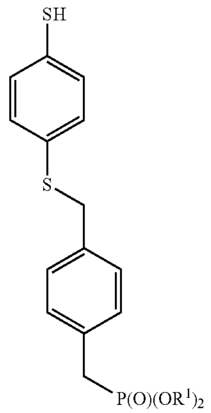
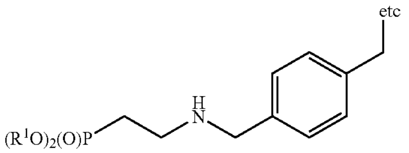
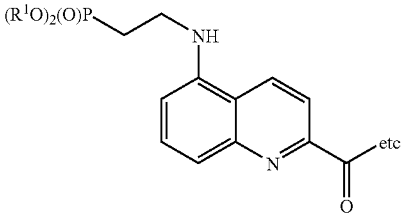
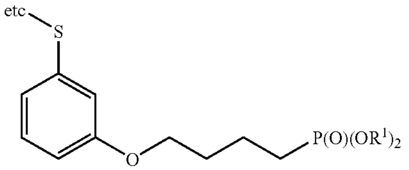
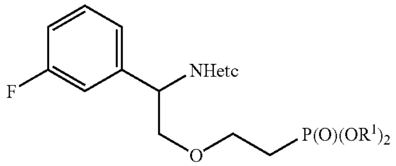
CHART 8
aryl
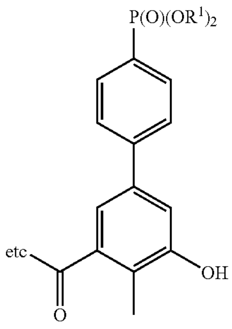
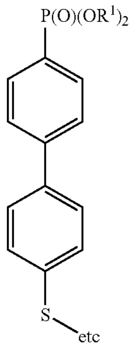

CHART 8-continued

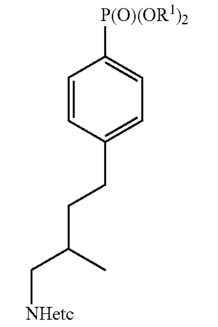

cyclized

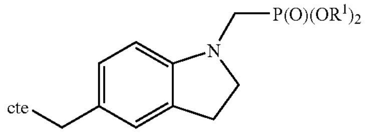

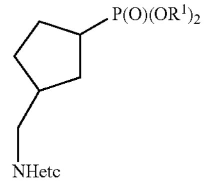

amide

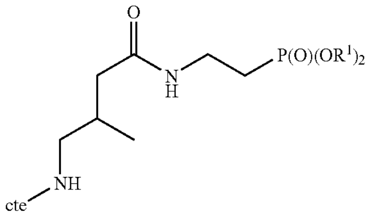

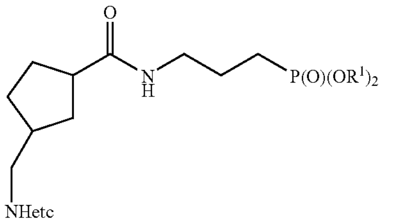

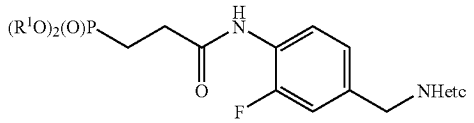

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990 or Third Edition 1999. Reactive substituents which may be protected are shown in the accompanying schemes as, for example, [OH], [SH], etc.

Preparation of the Phosphonate Ester Intermediates 1 in which X is a Direct Bond.

The intermediate phosphonate esters 1, in which the group A is attached to the aryl moiety, the $R_4COOH$ group does not contain an secondary amine, and in which the substituent A is either the group link-$P(O)(OR^1)_2$ or a precursor such as [OH], [SH], [NH], Br etc are prepared as shown in Schemes 1-2. The epoxide 1.1 in which the substituent A is either the group link-$P(O)(OR^1)_2$ or a precursor such as [OH], [SH], [NH], Br is prepared as described in Schemes 56-59 below. Treatment of the epoxide 1.1 with the amine 1.2 affords the aminoalcohol 1.3. The preparation of aminoalcohols by reaction between an amine and an epoxide is described, for example, in Advanced Organic Chemistry, by J. March, McGraw Hill, 1968, p 334. In a typical procedure, equimolar amounts of the reactants are combined in a polar solvent such as an alcohol or dimethylformamide and the like, at from ambient to about 100°, for from 1 to 24 hours, to afford the product 1.3. The amino alcohol 1.3 is then treated with an acylating agent 1.4 to afford the product 1.5. The acylating agent is typically a chloroformate or a sulfonyl chloride as shown in chart 4. Coupling conditions for amines with sulfonyl chlorides is described in Protective Groups in Organic Synthesis, by T. W. Greene and P. G. M Wuts, Wiley, Third Edition 1999 p. 603-615 or for chloroformates, p494ff. Preferably, the amine 1.3 is treated with the sulfonyl chloride 1.4 in the presence of a base such as pyridine, potassium carbonate etc and THF/water to give the product 1.5. Product 1.5 is deprotected using conditions described in Protective Groups in Organic Synthesis, by T. W. Greene and P. G. M Wuts, Wiley, Third Edition 1999 p. 503ff. Preferably, the BOC amine is treated with TFA in an aprotic solvent such as THF. Conversion to the amide 1.8 is performed using standard coupling conditions between an acid 1.7 and the amine. The preparation of amides from carboxylic acids and derivatives is described, for example, in Organic Functional Group Preparations, by S. R. Sandler and W. Karo, Academic Press, 1968, p. 274. The carboxylic acid is reacted with the amine in the presence of an activating agent, such as, for example, dicyclohexylcarbodiimide or diisopropylcarbodiimide, optionally in the presence of, for example, hydroxybenztriazole, in a non-protic solvent such as, for example, pyridine, DMF or dichloromethane, to afford the amide.

Alternatively, the carboxylic acid may first be converted into an activated derivative such as the acid chloride or anhydride, and then reacted with the amine, in the presence of an organic base such as, for example, pyridine, to afford the amide.

The conversion of a carboxylic acid into the corresponding acid chloride is effected by treatment of the carboxylic acid with a reagent such as, for example, thionyl chloride or oxalyl chloride in an inert organic solvent such as dichloromethane.

Preferably, the carboxylic acid 1.7 is reacted with an equimolar amount of the amine 1.6 in the presence of dicyclohexylcarbodiimide and hydroxybenztriazole, in an aprotic solvent such as, for example, tetrahydrofuran, at about ambient temperature, so as to afford the amide product 1.8. The compound 1.8, and analogous acylation products described below, in which the carboxylic acid $R^4COOH$ is one of the carbonic acid derivatives C38-C49, as defined in Chart 5c, are carbamates. Methods for the preparation of carbamates are described below, Scheme 98.

Scheme 2 illustrates an alternative method for the preparation of intermediate phosphonate esters 1, in which the group A is attached to the aryl moiety, the $R_4COOH$ group does not contain an secondary amine, and in which the substituent A is either the group link-$P(O)(OR^1)_2$ or a precursor such as [OH], [SH], [NH], Br etc. The oxazolidinone 2.1, prepared as described in Schemes 60-62, is first activated as shown in 2.2 and then treated with amine 1.2 to afford the secondary amine 2.3. The hydroxyl group can be activated by converting into a bromo derivative, for example by reaction with triphenylphosphine and carbon tetrabromide, as described in J. Am. Chem. Soc., 92, 2139, 1970, or a methanesulfonyloxy derivative, by reaction with methanesulfonyl chloride and a base, or, preferably, into the 4-nitrobenzenesulfonyloxy derivative 2.2, by reaction in a solvent such as ethyl acetate or tetrahydrofuran, with 4-nitrobenzenesulfonyl chloride and a base such as triethylamine or N-methylmorpholine, as described in WO 9607642. The nosylate product 2.2 is then reacted with the amine component 1.2 to afford the displacement product 2.3.

Equimolar amounts of the reactants are combined in an inert solvent such as dimethylformamide, acetonitrile or acetone, optionally in the presence of an organic or inorganic base such as triethylamine or sodium carbonate, at from about 0° C. to 100° C. to afford the amine product 2.3. Preferably, the reaction is performed in methyl isobutyl ketone at 80° C., in the presence of sodium carbonate, as described in WO 9607642. Treatment of the amine product 2.3 with the R3 chloride 1.4 as described in Scheme 1 then affords the product 2.4. The oxazolidinone group present in the product 2.4 is then hydrolyzed to afford the hydroxyamine 2.5. The hydrolysis reaction is effected in the presence of aqueous solution of a base such as an alkali metal hydroxide, optionally in the presence of an organic co-solvent. Preferably, the oxazolidinone compound 2.4 is reacted with aqueous ethanolic sodium hydroxide at reflux temperature, as described in WO 9607642, to afford the amine 2.5. This product is then reacted with the $R^4COOH$ carboxylic acid or activated derivative thereof, 1.7, to afford the product 1.8. The amide-forming reaction is conducted under the same conditions as described above, (Scheme 1).

Scheme 2

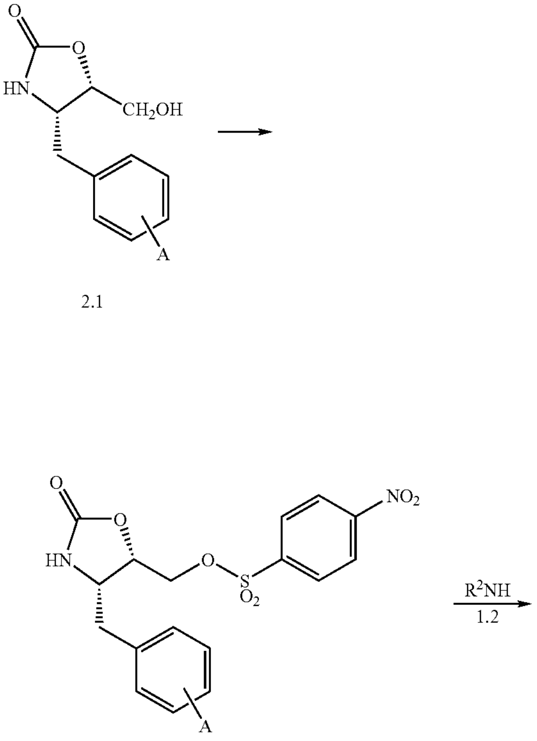

2.1

2.2

Scheme 1

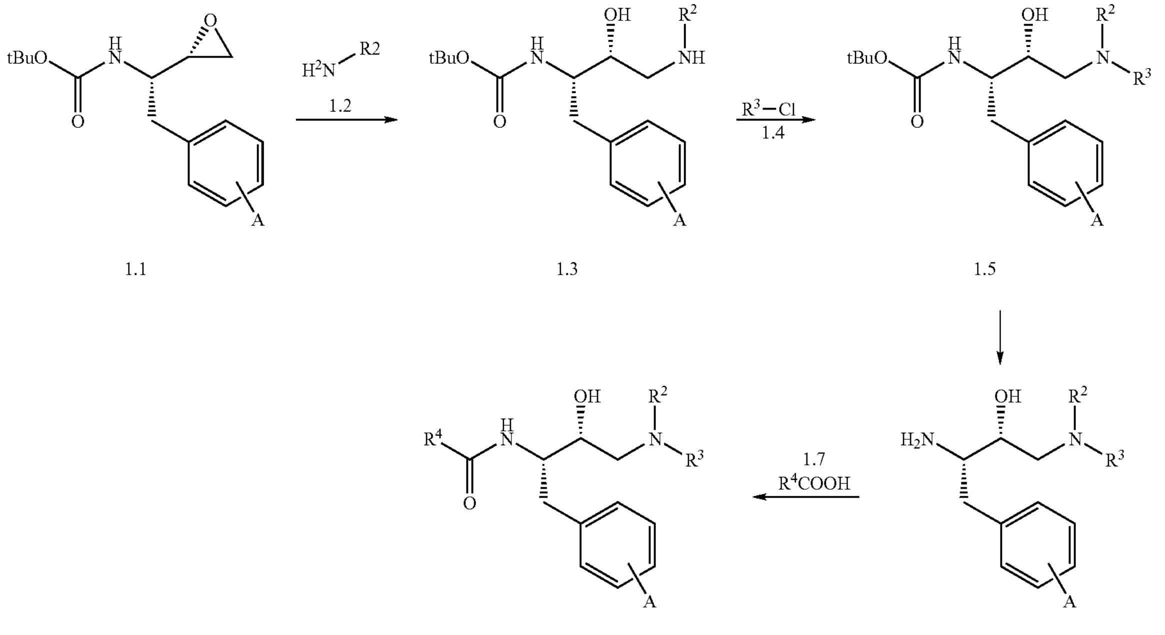

1.1

1.3

1.5

1.8

1.6

-continued

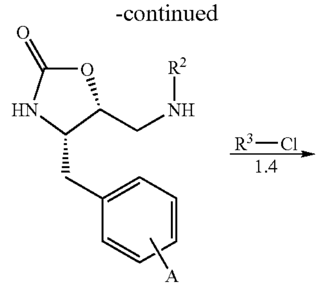

2.3

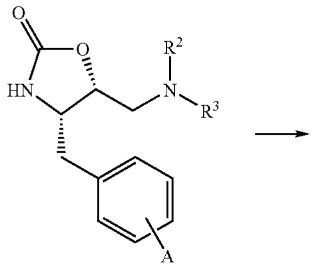

2.4

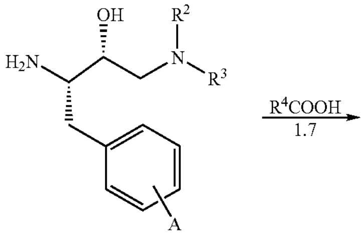

2.5

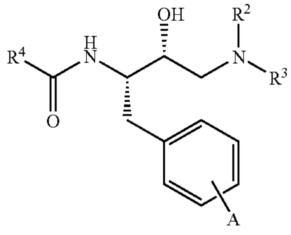

1.8

Scheme 3 illustrates the preparation of intermediate phosphonate esters 1, in which the group A is attached to the aryl moiety, the $R_4$COOH group contains an secondary amine, and in which the substituent A is either the group link-P(O)$(OR^1)_2$ or a precursor such as [OH], [SH], [NH], Br etc. The dibenzyl amine 3.2 is prepared from epoxide 3.1 and amine 1.2, following the same procedures described in Scheme 1 for the preparation of 1.3. Epoxide 3.1 is prepared as described below in Schemes 56a. The amine 3.2 is then converted to the amine 3.4 as described in U.S. Pat. No. 6,391,919. Preferably, the amine is first protected as the BOC carbamate and then treated with palladium hydroxide on carbon (20%) in methanol under hydrogen at high pressure to give the amine 3.4. Treatment of 3.4 with the $R_4$COOH acid 1.7 which contains a secondary or primary amine, under standard amide bond forming conditions as described above, Scheme 1, then affords the amide 3.5. Preferably, the acid 1.7, EDC and n-hydroxybenzotriazole in DMF is treated with the amine 3.4 to give the amide 3.5. Removal of the BOC group as described in Protective Groups in Organic Synthesis, by T. W. Greene and P. G. M Wuts, Wiley, Third Edition 1999 p. 520-525 then affords the amine 3.6. Preferably the BOC amine 3.5 is treated with HCl in dioxane and water to give the free amine 3.6. The amine 3.6 is then treated with an acylating agent such as an acid, chloroformate or sulfonyl chloride to give the final product 1.8. Standard coupling conditions for amines with acids or sulfonyl chlorides is indicated above Scheme 1. Preferably, the amine 3.6 is treated with nitro-sulfonyl chloride in THF and water in the presence of a base such as potassium carbonate to give the sulfonamide 1.8.

The reactions shown in Scheme 1-3 illustrate the preparation of the compound 1.8 in which the substituent A is either the group link-P(O)$(OR^1)_2$ or a precursor such as [OH], [SH], [NH], Br etc. Scheme 4 depicts the conversion of 1.8 in which A is [OH], [SH], [NH], Br etc, into the phosphonate ester 1 in which X is a direct bond. In this procedure 1.8 is converted, using the procedures described below, Schemes 47-99, into the compound 1. Also, in the preceding and following Schemes, the amino substituted sulfonamide reagents are typically introduced as a nitro-sulfonamide reagents. Therefore, where appropriate, an additonal step of nitro group reduction as described in Comprehensive Organic Transformations, by R. C. Larock, $2^{nd}$ Edition, 1999, p.821ff, is performed to give the final amino products.

Scheme 3

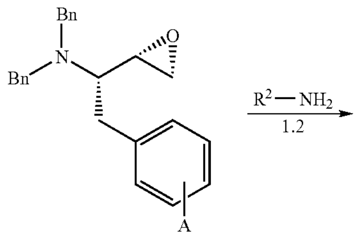

3.1

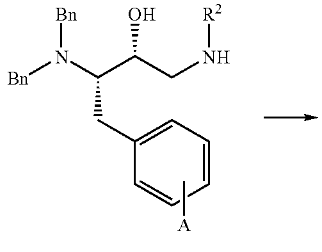

3.2

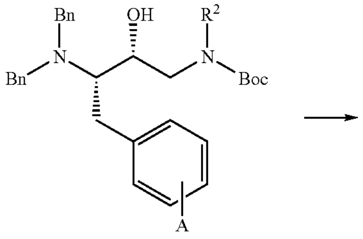

3.3

-continued

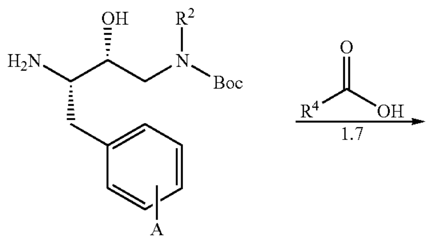

3.4

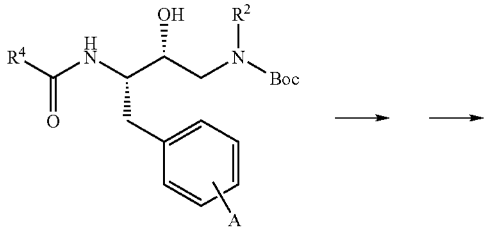

3.5

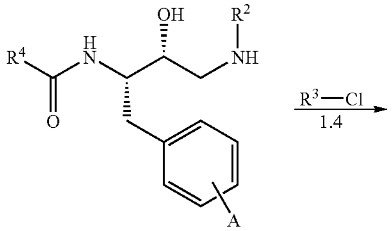

3.6

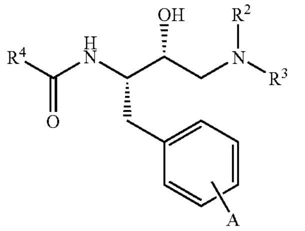

1.8

Scheme 4

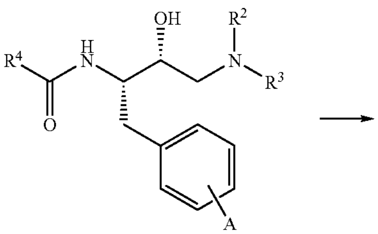

1.8

-continued

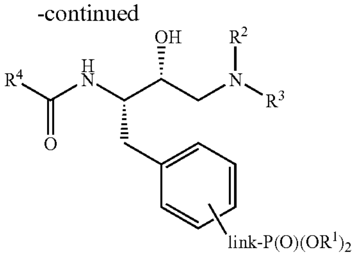

1

Scheme 5 illustrates an alternative method for the preparation of the compound 1 in which the group A is attached to the aryl moiety, the $R_4COOH$ group contains a primary or secondary amine and in which the substituent A is either the group link-P(O)($OR^1$)$_2$ or a precursor such as [OH], [SH], [NH], Br etc. The amine 3.4, (Scheme 3) is treated with an amino acid 5.1 under typical amide bond forming conditions to give the amide 5.2 as described above, Scheme 1. Preferably the acid 5.1 is first treated with EDC and n-hydroxybenzotriazole in DMF and then the amine 3.4 is added in DMF followed by N-methyl morpholine to give the amide 5.2. Reduction of the amide under the same catalytic hydrogenation conditions as described above in Scheme 3 gives the free amine 5.3. The amine is further treated with chloroacetyl chloride to provide the chloro compound 5.4. Preferably treatment with the chloroacetyl chloride is performed in ethyl acetate and water mixture in the presence of a base such as potassium hydrogen carbonate. The chloro compound 5.4 is treated with hydrochloric acid in dioxane and ethyl acetate to give the salt of the free amine 5.5. The salt 5.5 is then treated with a nitro-sulfonyl chloride 1.4 in THF and water in the presence of a base such as potassium carbonate to give the sulfonamide 5.6. Alternatively the free amine 5.5 is treated with a chloroformate 1.4 in the presence of a base such as triethylamine to afford the carbamate. Methods for the preparation of carbamates are also described below, Scheme 98. Compound 5.6 is then treated with the amine 5.7 to give the secondary amine 5.8. Preferably the chloride is refluxed in the presence of the amine 5.7 in THF.

The reactions shown in Scheme 5 illustrate the preparation of the compound 5.8 in which the substituent A is either the group link-P(O)($OR^1$)$_2$ or a precursor such as [OH], [SH], [NH], Br etc. Scheme 6 depicts the conversion of 5.8 in which A is [OH], [SH], [NH], Br etc, into the phosphonate ester 1 in which X is a direct bond. In this procedure 5.8 is converted, using the procedures described below, Schemes 47-99, into the compound 1.

In the preceding and following schemes, the conversion of various substituents into the group link-P(O)($OR^1$)$_2$ can be effected at any convenient stage of the synthetic sequence, or in the final step. The selection of an appropriate step for the introduction of the phosphonate substituent is made after consideration of the chemical procedures required, and the stability of the substrates to those procedures. It may be necessary to protect reactive groups, for example hydroxyl, during the introduction of the group link-P(O)($OR^1$)$_2$.

In the preceding and succeeding examples, the nature of the phosphonate ester group can be varied, either before or after incorporation into the scaffold, by means of chemical transformations. The transformations, and the methods by which they are accomplished, are described below (Scheme 99).

Scheme 5

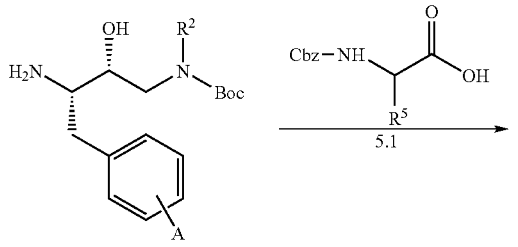

3.4

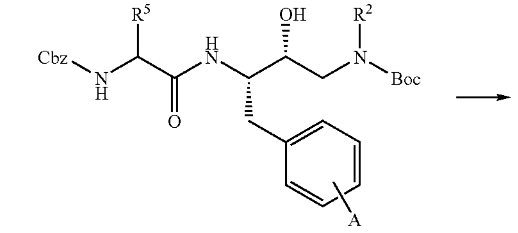

5.2

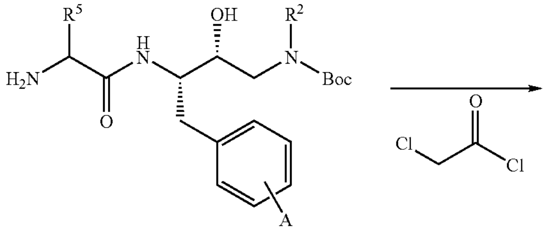

5.3

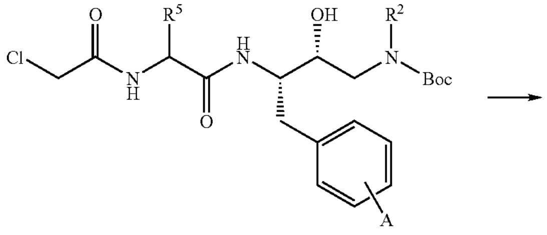

5.4

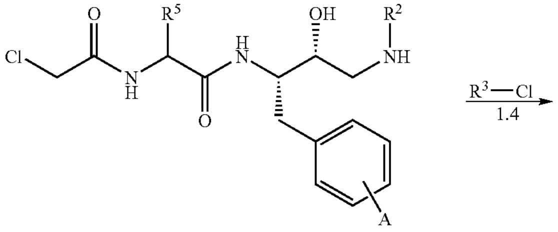

5.5

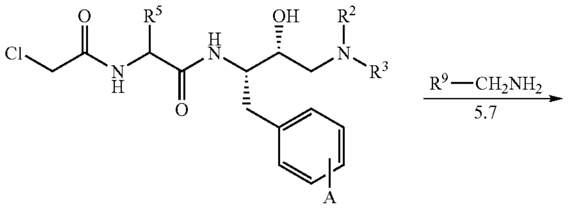

5.6

-continued

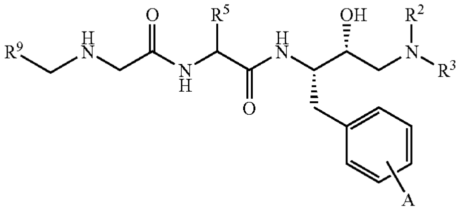

5.8

Scheme 6

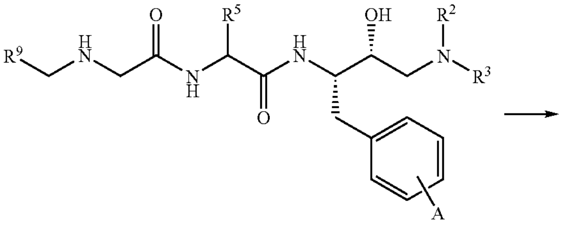

5.8

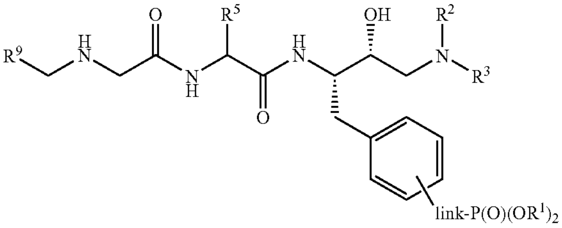

1

Preparation of the Phosphonate Ester Intermediates 1 in which X is a Sulfur.

The intermediate phosphonate esters 1, in which X is sulfur, the $R_4COOH$ group does not contain a amine group, and in which substituent A is either the group link-$P(O)(OR^1)_2$ or a precursor such as [OH], [SH], [NH], Br etc, are prepared as shown in Schemes 7-9.

Scheme 7 illustrates one method for the preparation of the compounds 1 in which the substituent X is S, and in which the group A is either the group link-$P(O)(OR^1)_2$ or a precursor thereto, such as [OH], [SH] Br etc. In this sequence, methanesulfonic acid 2-benzoyloxycarbonylamino-2-(2,2-dimethyl-[1,3]dioxolan-4-yl)-ethyl ester, 7.1, prepared as described in J. Org. Chem, 2000, 65, 1623, is reacted with a thiol 7.2 to afford the thioether 7.3. The preparation of thiol 7.2 is described in Schemes 63-72. The reaction is conducted in a suitable solvent such as, for example, pyridine, DMF and the like, in the presence of an inorganic or organic base, at from 0° C. to 80° C., for from 1-12 hours, to afford the thioether 7.3. Preferably the mesylate 7.1 is reacted with an equimolar amount of the thiol, in a mixture of a water-immiscible organic solvent such as toluene, and water, in the presence of a phase-transfer catalyst such as, for example, tetrabutyl ammonium bromide, and an inorganic base such as sodium hydroxide, at about 50° C., to give the product 7.3. The 1,3-dioxolane protecting group present in the compound 7.3 is then removed by acid catalyzed hydrolysis or by exchange with a reactive carbonyl compound to afford the diol 7.4. Methods for conversion of 1,3-dioxolanes to the corresponding diols are described in Protective Groups in Organic Synthesis, by T. W. Greene and P. G. M Wuts, Second Edition 1990, p191. For example, the 1,3-dioxolane compound 7.3 is hydrolyzed by reaction with a catalytic amount of an acid in an aqueous organic solvent mixture. Preferably, the 1,3-dioxolane 7.3 is dissolved in aqueous methanol containing hydrochloric acid, and heated at ca. 50° C., to yield the product 7.4.

The primary hydroxyl group of the diol 7.4 is then selectively acylated by reaction with an electron-withdrawing acyl halide such as, for example, pentafluorobenzoyl chloride or mono- or di-nitrobenzoyl chlorides. The reaction is conducted in an inert solvent such as dichloromethane and the like, in the presence of an inorganic or organic base.

Preferably, equimolar amounts of the diol 7.4 and 4-nitrobenzoyl chloride are reacted in a solvent such as ethyl acetate, in the presence of a tertiary organic base such as 2-picoline, at ambient temperature, to afford the hydroxy ester 7.5. The hydroxy ester is next reacted with a sulfonyl chloride such as methanesulfonyl chloride, 4-toluenesulfonyl chloride and the like, in the presence of a base, in an aprotic polar solvent at low temperature, to afford the corresponding sulfonyl ester 7.6. Preferably, equimolar amounts of the carbinol 7.5 and methanesulfonyl chloride are reacted together in ethyl acetate containing triethylamine, at about 10° C., to yield the mesylate 7.6. The compound 7.6 is then subjected to a hydrolysis-cyclization reaction to afford the oxirane 7.7. The mesylate or analogous leaving group present in 7.6 is displaced by hydroxide ion, and the carbinol thus produced, without isolation, spontaneously transforms into the oxirane 7.7 with elimination of 4-nitrobenzoate. To effect this transformation, the sulfonyl ester 7.6 is reacted with an alkali metal hydroxide or tetraalkylammonium hydroxide in an aqueous organic solvent. Preferably, the mesylate 7.6 is reacted with potassium hydroxide in aqueous dioxan at ambient temperature for about 1 hour, to afford the oxirane 7.7.

The oxirane compound 7.7 is then subjected to regiospecific ring-opening reaction by treatment with a secondary amine 1.2, to give the aminoalcohol 7.8. The amine and the oxirane are reacted in a protic organic solvent, optionally in the additional presence of water, at 0° C. to 100° C., and in the presence of an inorganic base, for 1 to 12 hours, to give the product 7.8. Preferably, equimolar amounts of the reactants 7.7 and 1.2 are reacted in aqueous methanol at about 60° C. in the presence of potassium carbonate, for about 6 hours, to afford the aminoalcohol 7.8. The free amine is then substituted by treatment with an acid, chloroformate or sulfonyl chloride as described above in Scheme 1 to give the amine 7.9. The carbobenzyloxy (cbz) protecting group in the product 7.9 is removed to afford the free amine 7.10. Methods for removal of cbz groups are described, for example, in Protective Groups in Organic Synthesis, by T. W. Greene and P. G. M Wuts, Second Edition, p. 335. The methods include catalytic hydrogenation and acidic or basic hydrolysis. For example, the cbz-protected amine 7.9 is reacted with an alkali metal or alkaline earth hydroxide in an aqueous organic or alcoholic solvent, to yield the free amine 7.10. Preferably, the cbz group is removed by the reaction of 7.9 with potassium hydroxide in an alcohol such as isopropanol at ca. 60° C. to afford the amine 7.10. The amine 7.10 so obtained is next acylated with a carboxylic acid or activated derivative 1.7, using the conditions described above in Scheme 1 to afford the product 7.11

Scheme 7

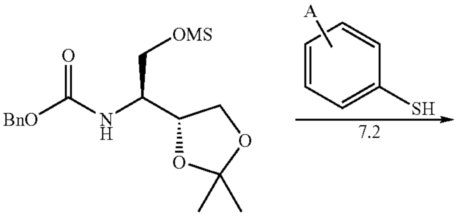

7.1

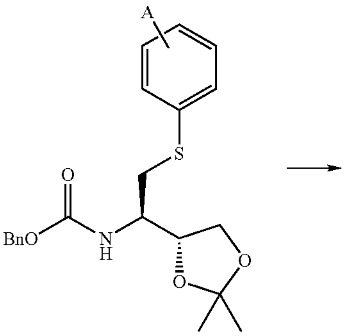

7.3

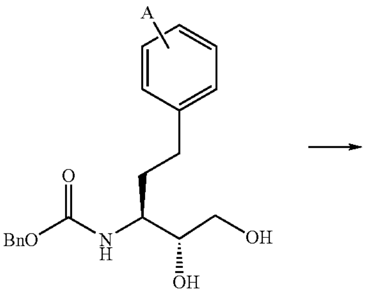

7.4

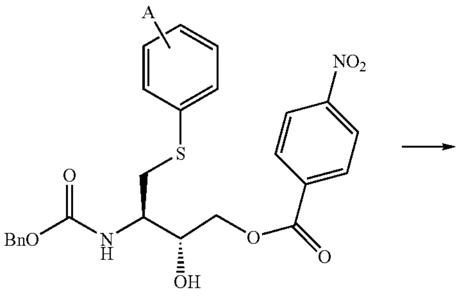

7.5

-continued

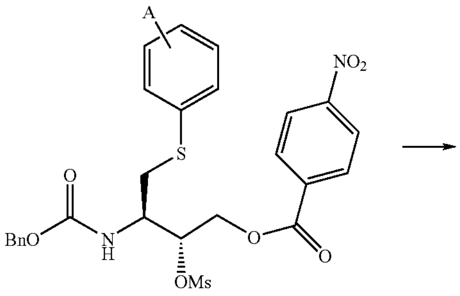

7.6

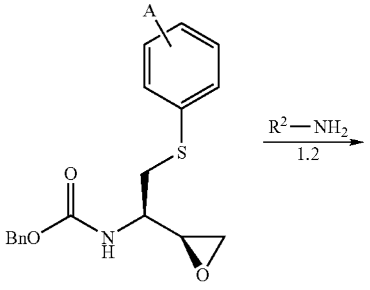

7.7

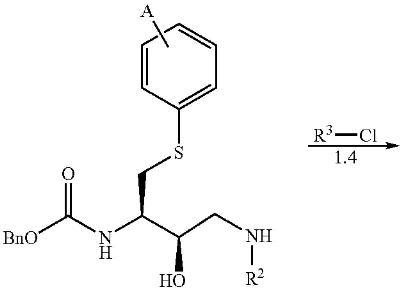

7.8

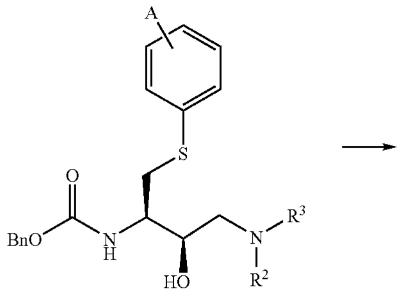

7.9

-continued

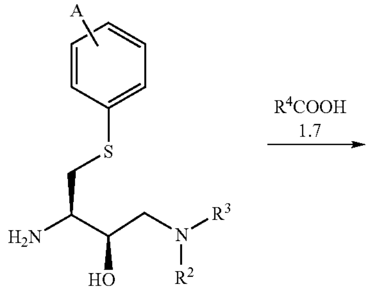

7.10

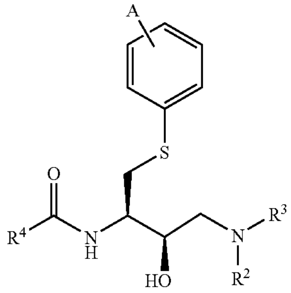

7.11

Scheme 8 illustrates an alternative preparation of the compounds 1 in which the substituent X is S, and in which the group A is either the group link-P(O)(OR$^1$)$_2$ or a precursor thereto, such as [OH], [SH] Br etc. In this sequence, 4-amino-tetrahydro-furan-3-ol, 8.1, the preparation of which is described in Tet. Lett., 2000, 41, 7017, is reacted with a carboxylic acid or activated derivative thereof, $R^4$COOH, 1.7, using the conditions described above for in Scheme 1 for the preparation of amides, to afford the amide 8.2. The amide product 8.2 is then transformed, using the sequence of reactions shown in Scheme 8, into the isoxazoline compound 8.5. The hydroxyl group on the tetrahydrofuran moiety in 8.2 is converted into a leaving group such as p-toluenesulfonyl or the like, by reaction with a sulfonyl chloride in an aprotic solvent such as pyridine or dichloromethane. Preferably, the hydroxy amide 8.2 is reacted with an equimolar amount of methanesulfonyl chloride in pyridine, at ambient temperature, to afford the methanesulfonyl ester 8.3. The product 8.3, bearing a suitable sulfonyl ester leaving group, is then subjected to acid-catalyzed rearrangement to afford the isoxazoline 8.4. The rearrangement reaction is conducted in the presence of an acylating agent such as a carboxylic anhydride, in the presence of a strong acid catalyst. Preferably, the mesylate 8.3 is dissolved in an acylating agent such as acetic anhydride at about 0° C., in the presence of about 5 mole % of a strong acid such as sulfuric acid, to afford the isoxazoline mesylate 8.4. The leaving group, for example a mesylate group, is next subjected to a displacement reaction with an amine. The compound 8.4 is reacted-with an amine 1.2, as defined in Chart 3, in a protic solvent such as an alcohol, in the presence of an organic or inorganic base, to yield the displacement product 8.5. Preferably, the mesylate compound 8.4 is reacted with an equimolar amount of the amine 1.2, in the presence of an excess of an inorganic base such as potassium carbonate, at ambient temperature, to afford the product 8.5. The product 8.5 is then treated with $R^3$Cl, chart 6 as described above in Scheme 1 to afford the amine 8.6. The compound 8.6 is then reacted with a thiol 7.2 to afford the thioether 7.11. The reaction is conducted in a polar solvent such as DMF, pyridine or an alcohol, in the presence of a weak organic or inorganic base, to afford the product 7.11. Preferably, the isoxazoline 8.6 is reacted, in methanol, with an equimolar amount of the thiol 7.2, in the presence of an excess of a base such as potassium bicarbonate, at ambient temperature, to afford the thioether 7.11.

The procedures illustrated in Scheme 7-8 depict the preparation of the compounds 7.11 in which X is S, and in which the substituent A is either the group link-P(O)(OR$^1$)$_2$ or a precursor thereto, such as [OH], [SH] Br etc, as described below. Scheme 9 illustrates the conversion of compounds 7.11 in which A is a precursor to the group link-P(O)(OR$^1$)$_2$ into the compounds 1 in which X═S. Procedures for the conversion of the substituent A into the group link-P(O)(OR$^1$)$_2$ are illustrated below, (Schemes 47-99).

Scheme 9a-9b depicts the preparation of phosphonate esters 1, in which X is sulfur, the R$_4$COOH group does contain a amine group, and in which substituent A is either the group link-P(O)(OR$^1$)$_2$ or a precursor such as [OH], [SH], [NH], Br etc. The amine 7.10 prepared in Scheme 7 is treated with the CBZ protected amine 5.1 using the same conditions described in Scheme 5 for the preparation of 5.2 to give CBZ amine 9a.1. Removal of the CBZ group as described in Scheme 5 to give 9a.2 followed by treatment with chloroacetyl chloride as described in Scheme 5 gives chloride 9a.3. The chloride 9a.3 is then treated with the amine 5.7 to give the amine 9a.4 as described in Scheme 5.

The reactions shown in Scheme 9a illustrate the preparation of the compound 9a.4 in which the substituent A is either the group link-P(O)(OR$^1$)$_2$ or a precursor such as [OH], [SH], [NH], Br etc. Scheme 9b depicts the conversion of 9a.4 in which A is [OH], [SH], [NH], Br etc, into the phosphonate ester 1 in which X is sulfur. In this procedure 9a.4 is converted, using the procedures described below, Schemes 47-99, into the compound 1.

Scheme 8

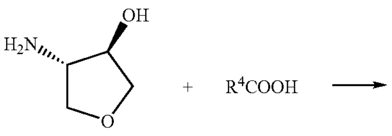

8.1 1.7

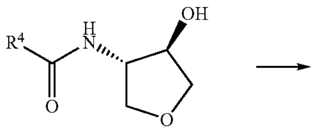

8.2

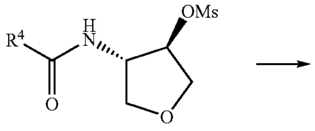

8.3

-continued

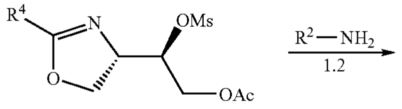

8.4

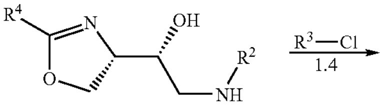

8.5

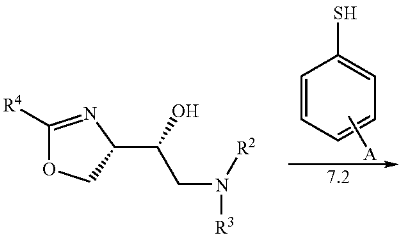

8.6

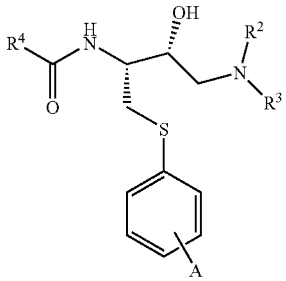

7.11

Scheme 9

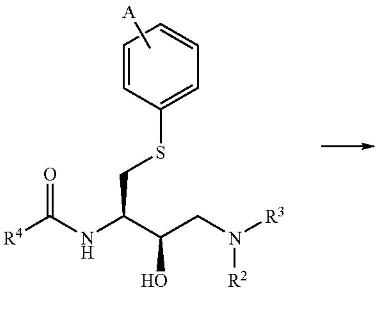

7.11

-continued

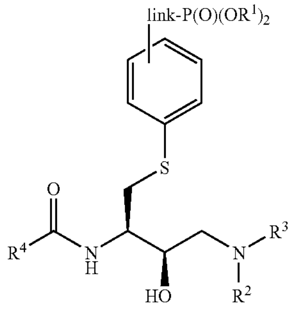

1

Scheme 9a

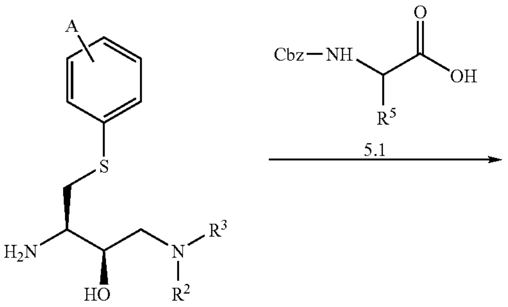

7.10

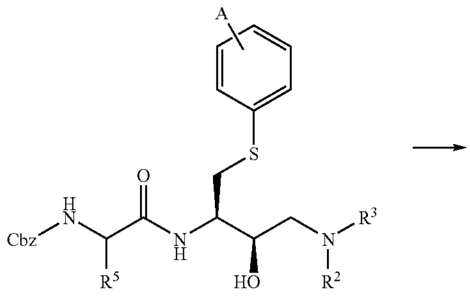

9a.1

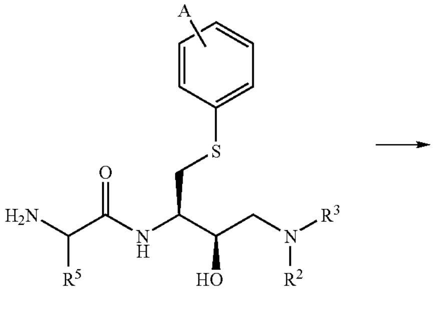

9a.2

-continued

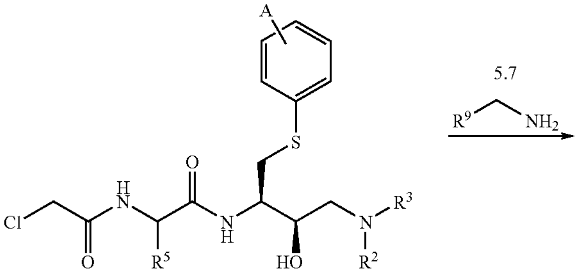

9a.3

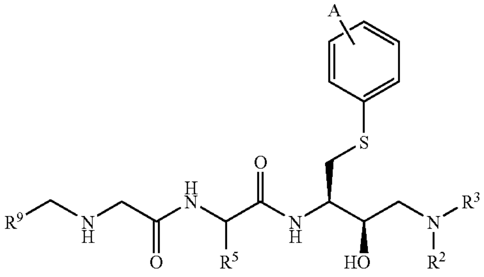

9a.4

Scheme 9b

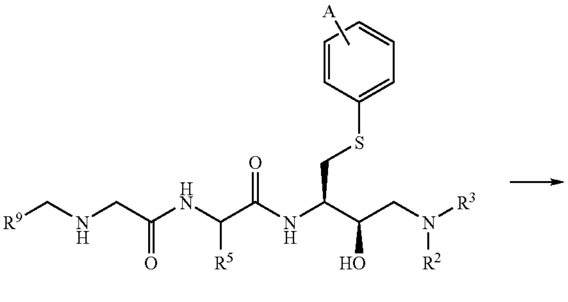

9a.4

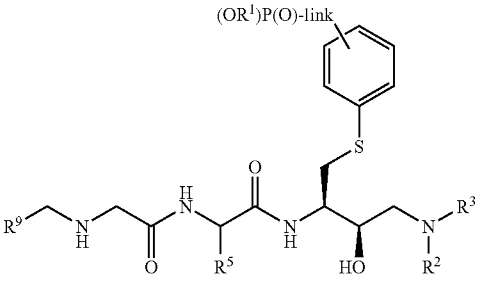

1

Preparation of the Phosphonate Ester Intermediates 2 and 3 in which X is a Direct Bond Schemes 10-12 illustrate the preparation of the phosphonate esters 2 and 3 in which X is a direct bond and the $R_4COOH$ group does not contain a primary or secondary amine group. As shown in Scheme 10, the epoxide 10.1, prepared as described in J. Med. Chem 1994, 37, 1758 is reacted with the amine 10.2 or 10.5, in which the substituent A is either the group link-$P(O)(OR^1)_2$ or a precursor such as

[OH], [SH], [NH], Br etc, to afford the amine 10.3 and 10.6 respectively. The reaction is performed under the same conditions as described above, Scheme 1 for the preparation of the amine 1.3. The preparation of the amines 10.2 is described in Schemes 73-75 and amines 10.5 in schemes 76-78. The products 10.3 and 10.6 are then transformed, using the sequence of reactions described above, Scheme 1, for the conversion of the amine 1.3 into the amide 1.8, into the amino amide 10.4 and 10.7 respectively.

An alternative route to the amines 10.4 and 10.7 is shown in Scheme 11 in which sulfonyl ester 11.1 prepared according to Chimia 1996, 50, 532 is treated under conditions described in Scheme 2 with the amines 10.2 or 10.5 to give the amines 11.2 or 11.3 respectively. These amine products are then converted as described above, Scheme 2, into the amides 10.4 and 10.7 respectively.

The reactions shown in Scheme 10 and 11 illustrate the preparation of the compounds 10.4 and 10.7 in which the substituent A is either the group link-$P(O)(OR^1)_2$ or a precursor such as [OH], [SH], [NH], Br etc. Scheme 12 depicts the conversion of these compounds 10.4 and 10.7 in which A is [OH], [SH], [NH], Br etc, into the phosphonate esters 2 and 3 respectively, in which X is a direct bond. In this procedure, the amines 10.4 and 10.7 are converted, using the procedures described below, Schemes 47-99, into the compounds 2 and 3 respectively.

Scheme 10

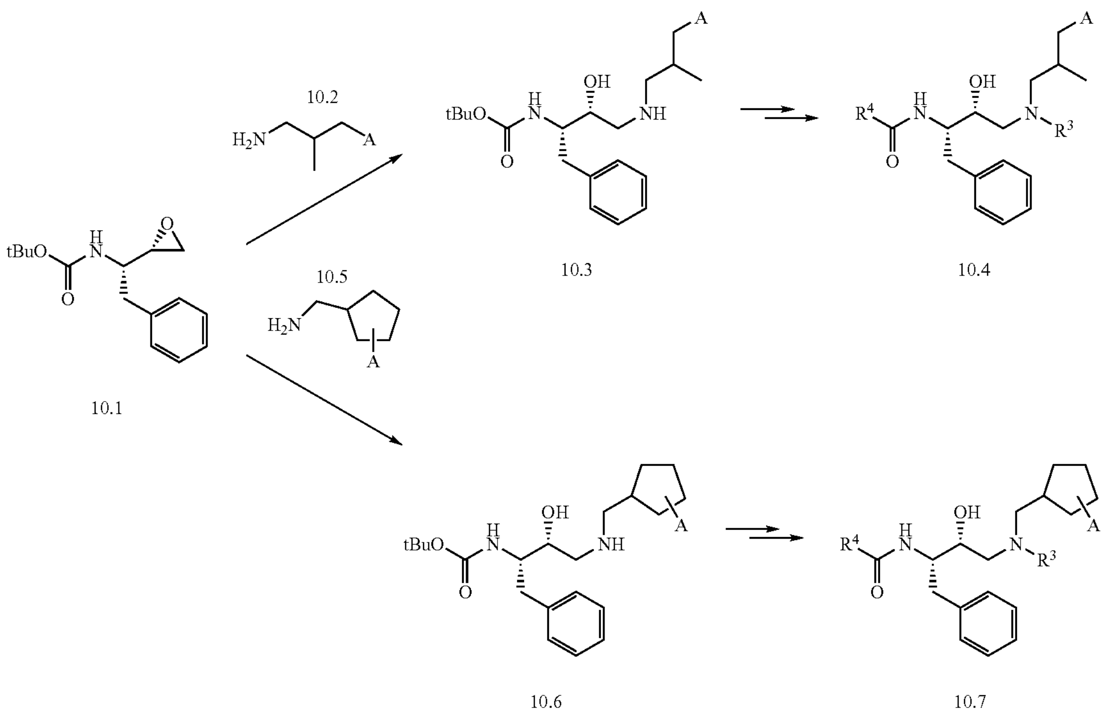

Scheme 11

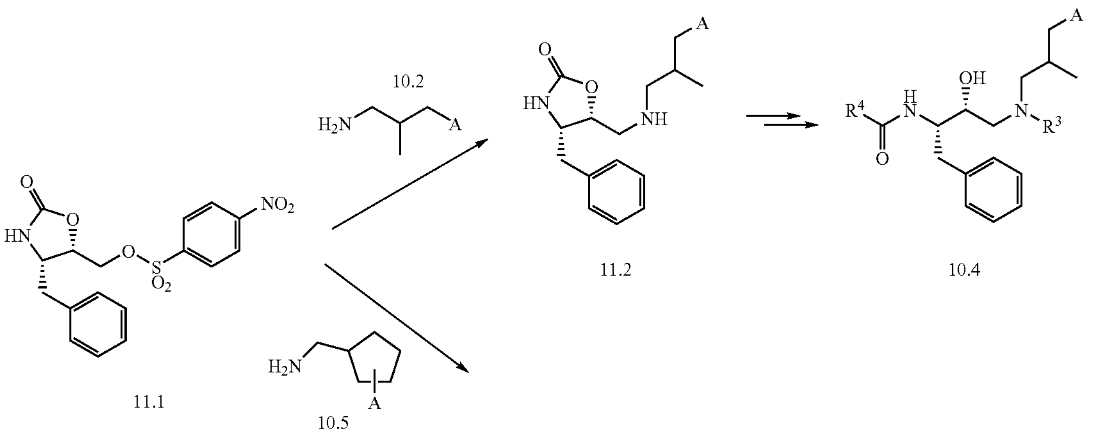

-continued

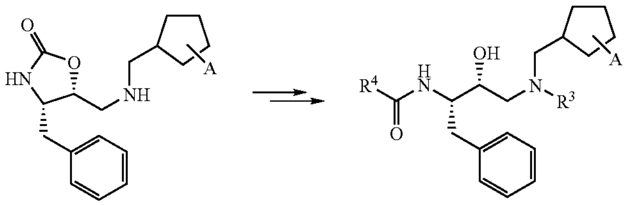

11.3 10.7

Scheme 12

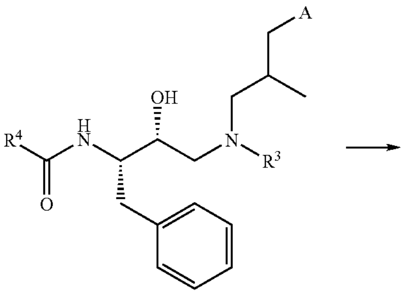

10.4

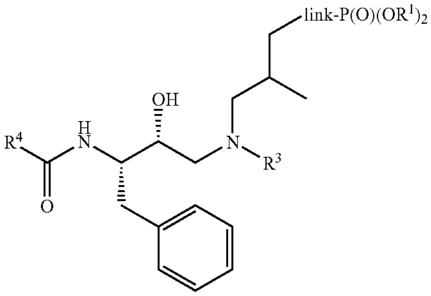

2

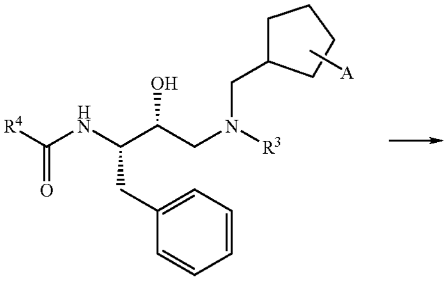

10.7

-continued

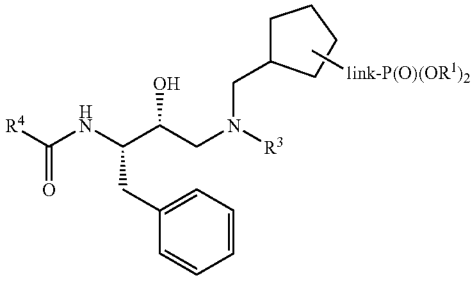

3

Schemes 13-14 illustrates the preparation of the phosphonate esters 2 and 3 in which X is a direct bond and the $R_4COOH$ group contains an amine. The epoxide 13.1, prepared as described in U.S. Pat. No. 6,391,919B1, or J. Org. Chem. 1996, 61, 3635 is reacted, as described above, (Scheme 1) with the amine 10.2 or 10.5, in which substituent A is either the group link-$P(O)(OR^1)_2$ or a precursor such as [OH], [SH], [NH], Br etc, to give the amino alcohols 13.2 and 13.4, respectively. These amines are then converted as described in Scheme 3 for the conversion of 3.2 into 3.4 and Scheme 5 for the conversion of 3.4 into 5.8, into the amine products 13.3 and 13.5 respectively.

The reactions shown in Scheme 13 illustrate the preparation of the compounds 13.3 and 13.5 in which the substituent A is either the group link-$P(O)(OR^1)_2$ or a precursor such as [OH], [SH], [NH], Br etc. Scheme 14 depicts the conversion of the compounds 13.3 and 13.5 in which A is [OH], [SH], [NH], Br etc, into the phosphonate esters 2 and 3 in which X is a direct bond. In this procedure, the compounds 13.3 and 13.5 are converted, using the procedures described below, Schemes 47-99, into the compounds 2 and 3 respectively.

Scheme 13
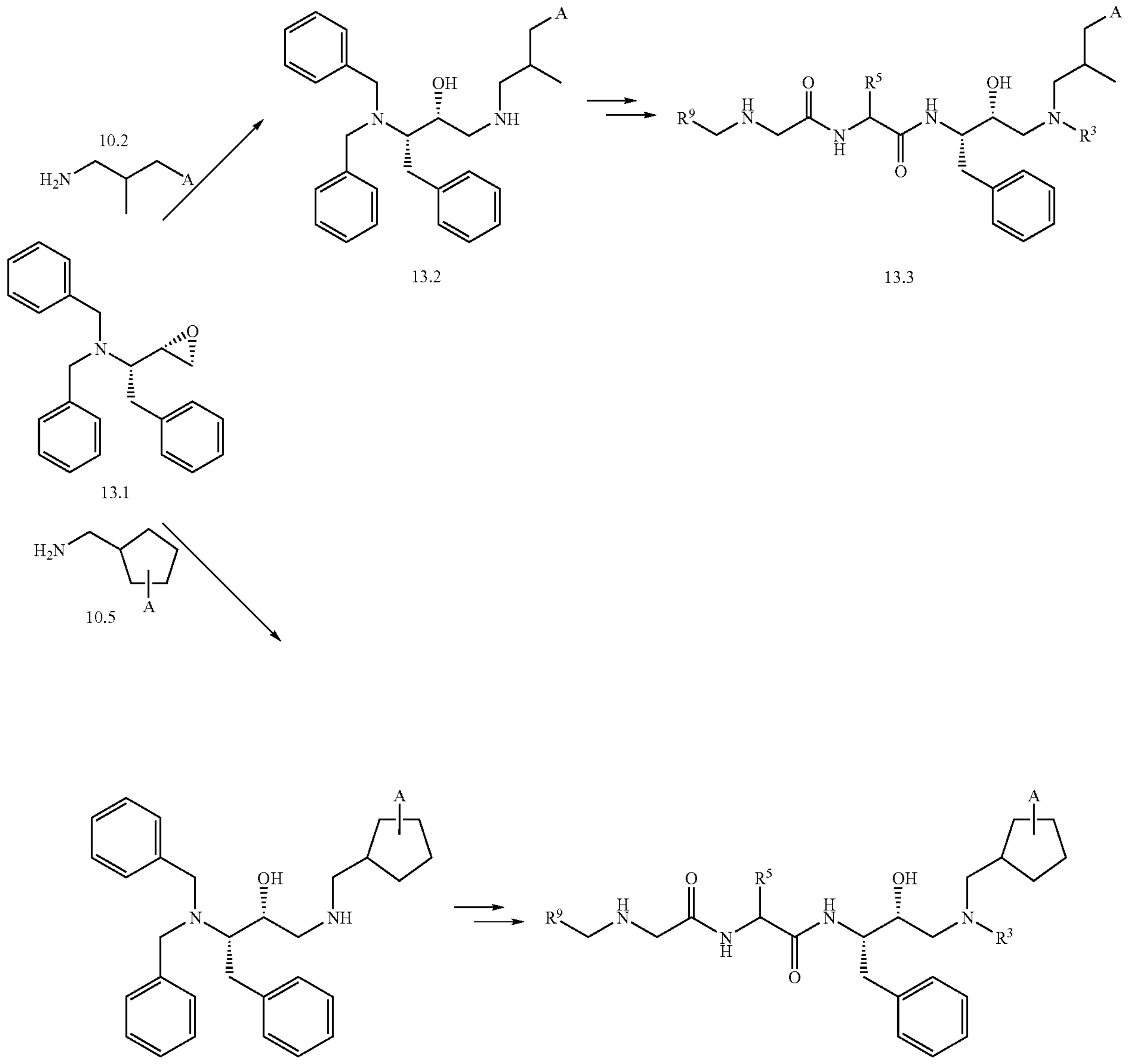
10.2
13.1
10.5
13.2
13.3
13.4
13.5
-continued
Scheme 14
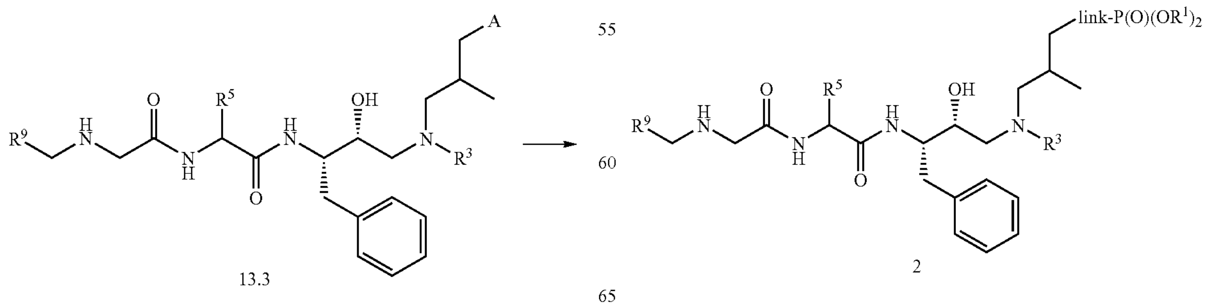
13.3
2

-continued

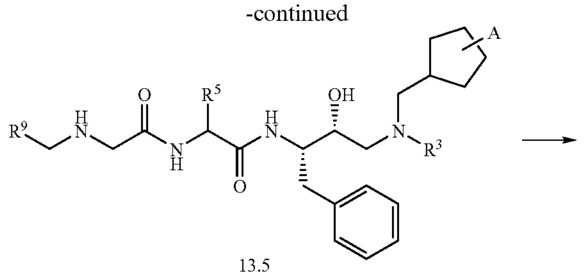

13.5

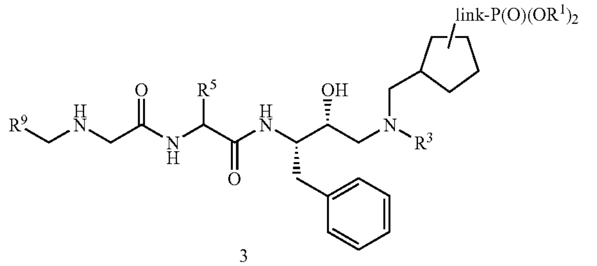

3

Preparation of the Phosphonate Ester Intermediates 2 and 3 in which X is a Sulfur The intermediate phosphonate esters 2 and 3, in which the group A is attached to a sulfur linked aryl moiety, and the $R_4COOH$ group does not contain an amine group, are prepared as shown in Schemes 15-17. In Scheme 15, epoxide 15.1 is prepared from mesylate 7.1 using the conditions described in Scheme 7 for the preparation of 7.7 from 7.1, except incorporating thiophenol for thiol 7.2. The epoxide 15.1 is then treated with amine 10.2 or amine 10.5, in which substituent A is either the group link-$P(O)(OR^1)_2$ or a precursor such as [OH], [SH], [NH], Br etc, as described in Scheme 7, to give the amines 15.2 and 15.4. Further application of Scheme 7 on the amines 15.2 and 15.4 yields the alcohols 15.3 and 15.5 respectively.

Alternatively, Scheme 16 depicts the preparation of 15.3 and 15.5 using the mesylate 8.4. The amines 10.2 and 10.5 are reacted with mesylate 8.4 under conditions described in Scheme 8 to give amines 16.1 and 16.2 respectively. Further modification of 16.1 and 16.2 according to the conditions described in Scheme 8 then affords alcohols 15.3 and 15.5 respectively.

The reactions shown in Scheme 15-16 illustrate the preparation of the compounds 15.3 and 15.5 in which the substituent A is either the group link-$P(O)(OR^1)_2$ or a precursor such as [OH], [SH], [NH], Br etc. Scheme 17 depicts the conversion of 15.3 and 15.5 in which A is [OH], [SH], [NH], Br etc, into the phosphonate ester 2 and 3 in which X is sulfur. In this procedure 15.3 or 15.5 is converted, using the procedures described below, Schemes 47-99, into the compound 2 and 3.

Scheme 15

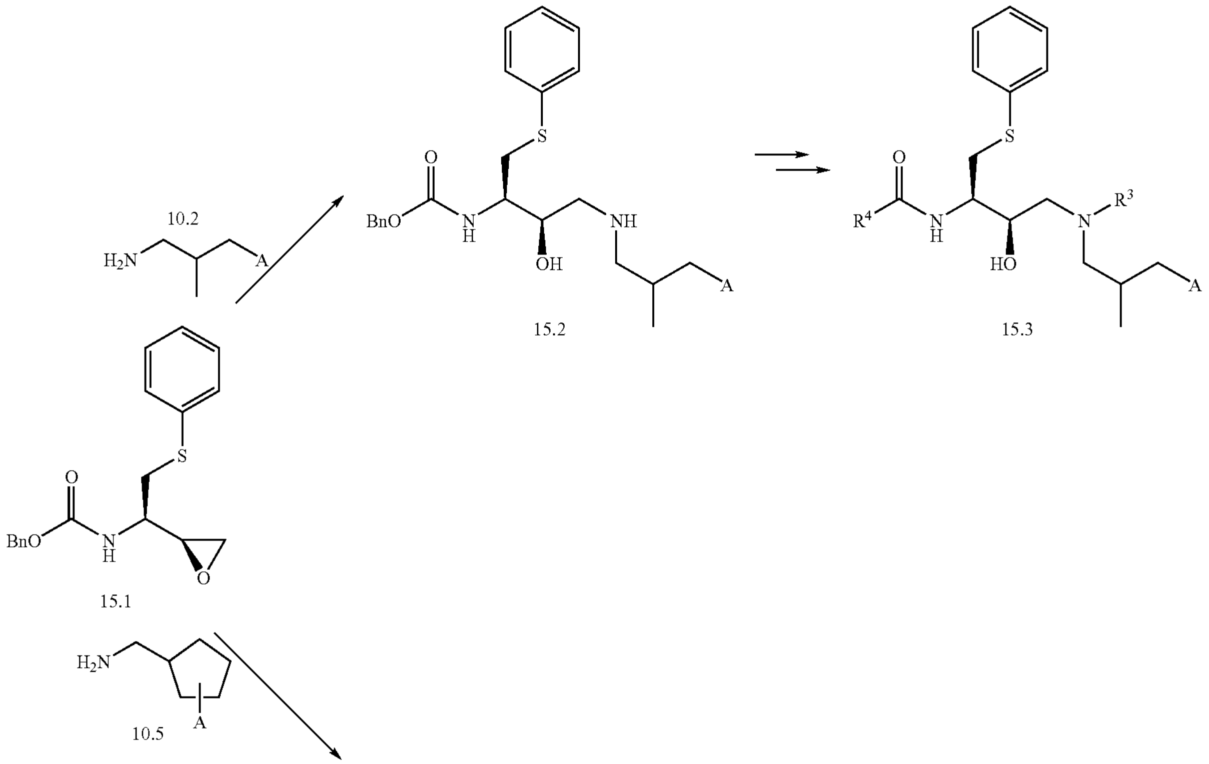

10.2

15.1

10.5

15.2

15.3

-continued
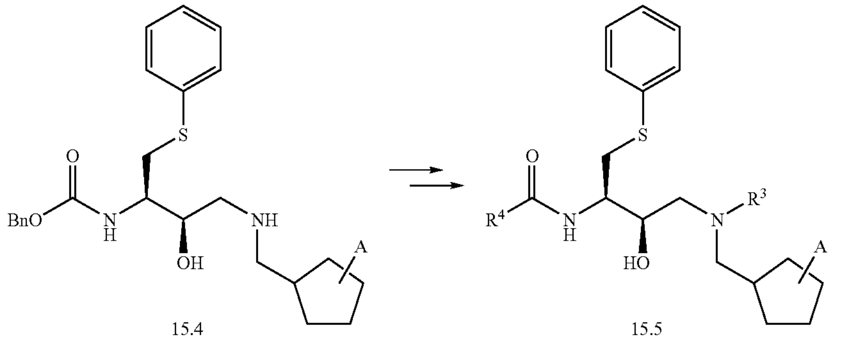
15.4 15.5
Scheme 16
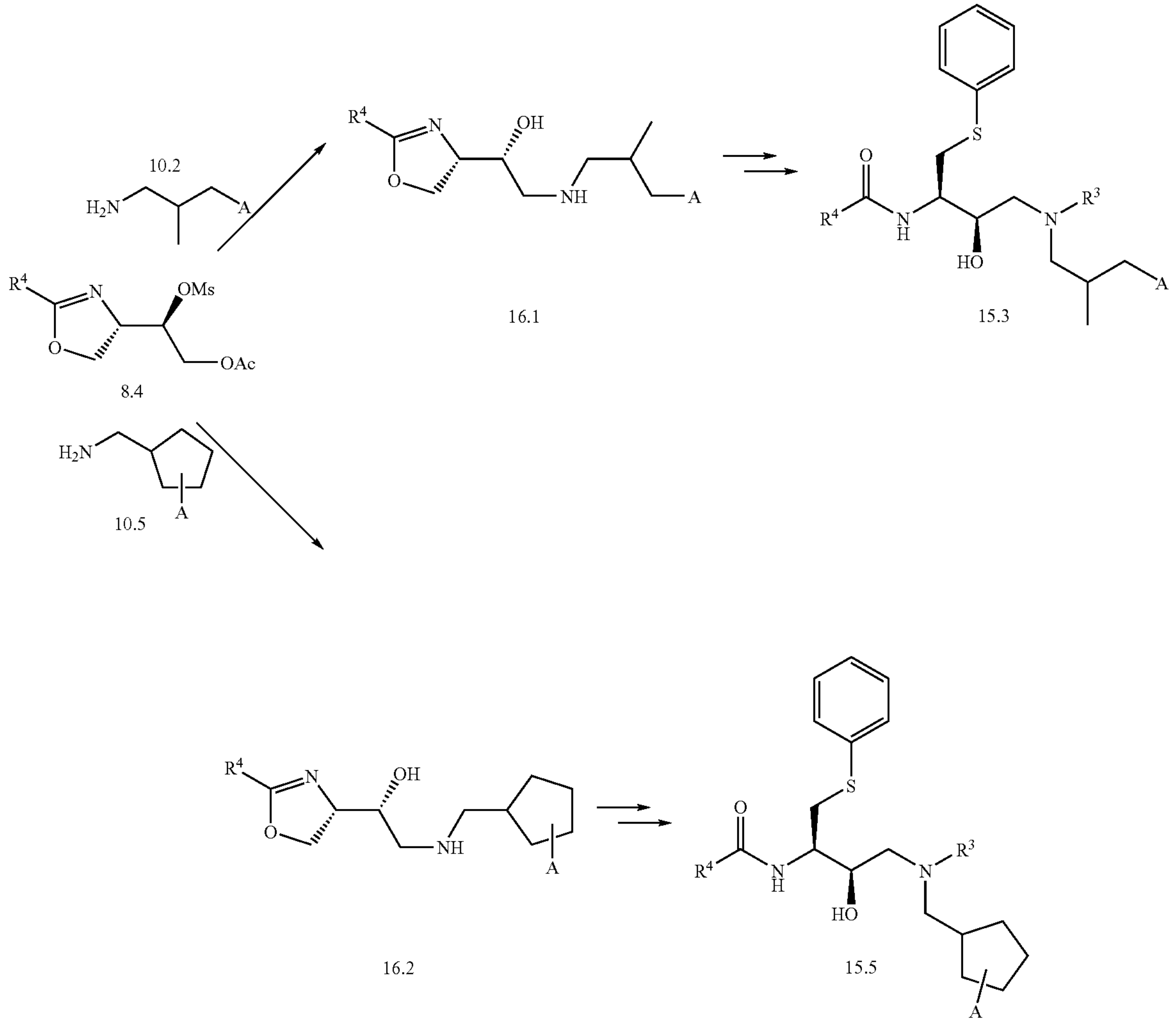
10.2
8.4
10.5
16.1
15.3
16.2
15.5

Scheme 17

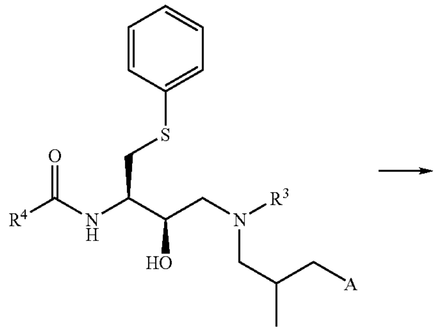

15.3

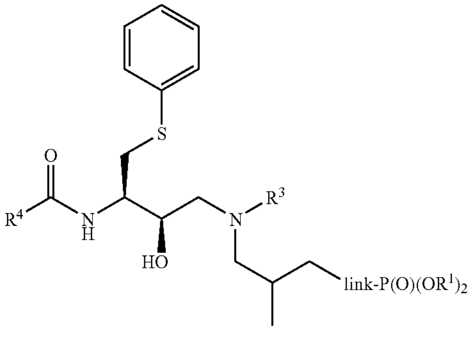

2

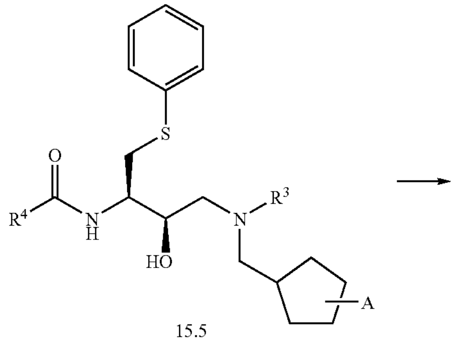

15.5

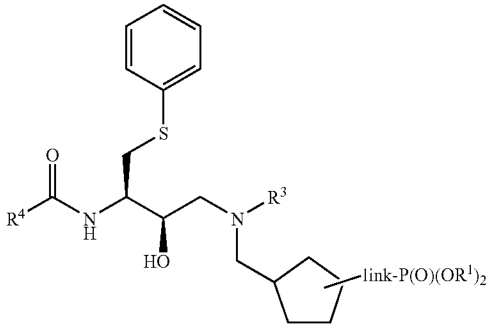

3

Scheme 18-19 depict the preparation of phosphonate esters 2 and 3, in which the group A is attached to a sulfur linked aryl moiety, and the $R_4COOH$ group contains a amine group. The amines 15.2 and 15.4, in which substituent A is either the group link-$P(O)(OR^1)_2$ or a precursor such as [OH], [SH], [NH], Br etc, prepared in Scheme 15, are converted using the same conditions described in Scheme 7 for the preparation of the amine 7.10 from 7.8 and Scheme 9a for the preparation of 9a.4 from 7.10 to give 18.1 and 18.2 respectively.

The reactions shown in Scheme 18 illustrate the preparation of the compound 18.1 and 18.2 in which the substituent A is either the group link-$P(O)(OR^1)_2$ or a precursor such as [OH], [SH], [NH], Br etc. Scheme 19 depicts the conversion of 18.1 and 18.2 in which A is [OH], [SH], [NH], Br etc. into the phosphonate ester 2 and 3 respectively in which X is sulfur. In this procedure 18.1 and 18.2 are converted, using the procedures described below, Schemes 47-99, into the compounds 2 and 3

Scheme 18

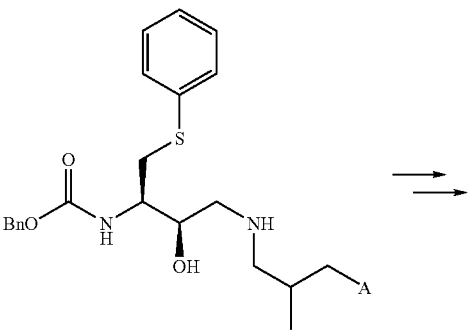

15.2

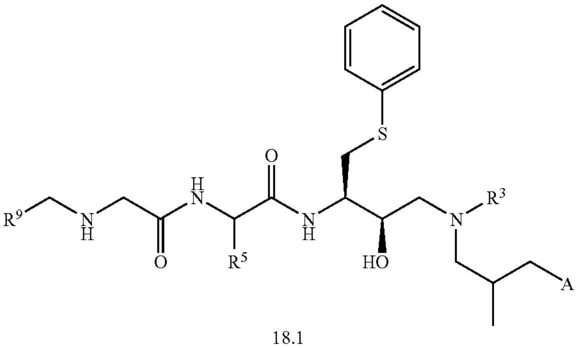

18.1

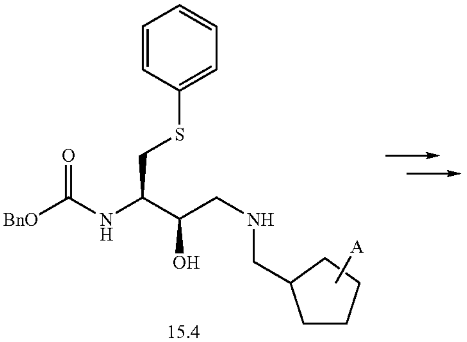

15.4

-continued

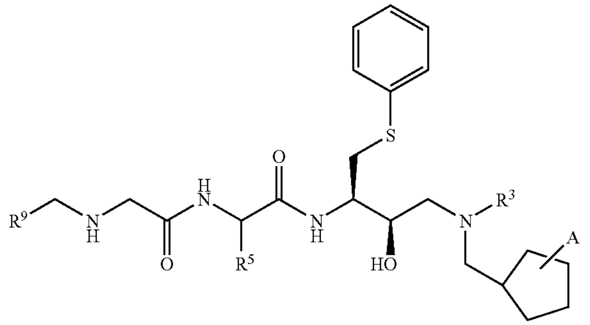

18.2

Scheme 19

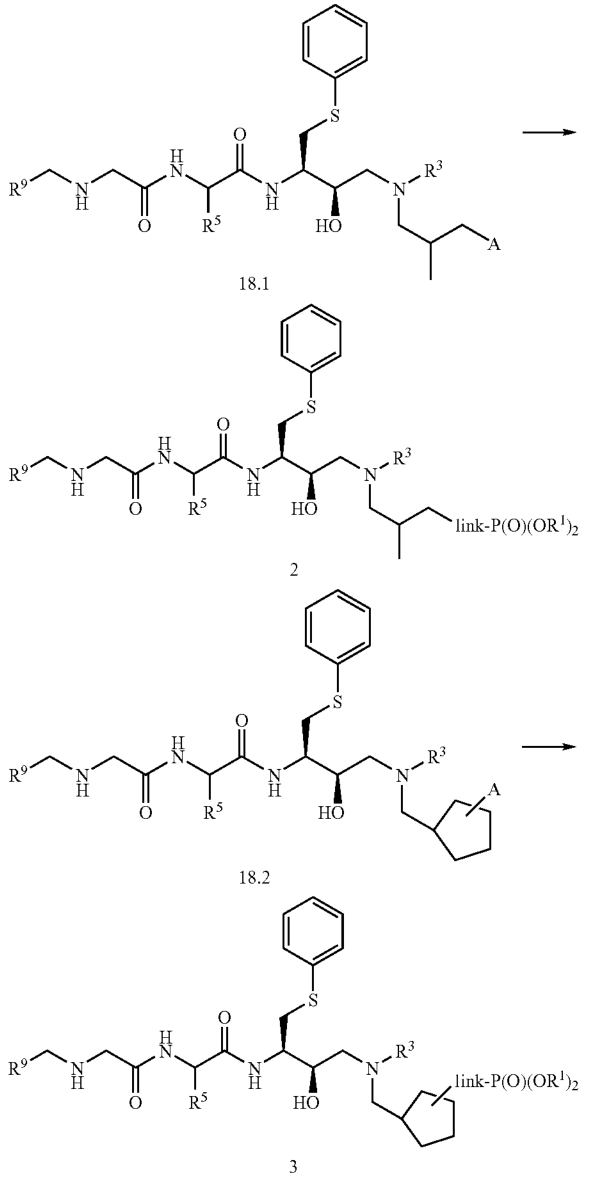

18.1

2

18.2

3

Preparation of the Phosphonate Ester Intermediates 4 in which X is a Direct Bond Schemes 20-22 illustrate the preparation of the phosphonate esters 4 in which X is a direct bond and the R group does not contain a primary or secondary amine group. As shown in Scheme 20, the amine 20.1 is reacted with the sulfonyl chloride 20.2 in which the substituent A is either the group link-$P(O)(OR^1)_2$ or a precursor such as [OH], [SH], [NH], Br etc, to afford the product 20.3. The reaction is performed under the same conditions as described above, Scheme 1 for the preparation of the sulfonamide 1.5. Amine 20.1 is prepared by treatment of epoxide 10.1 with the amine 1.2 as described in Scheme 1 for the preparation of 1.3. The preparation of sulfonyl chloride 20.2 is described in Schemes 92-97. The product 20.3 is then transformed, using the sequence of reactions described above, Scheme 1, for the conversion of the amide 1.5 into the amide 1.8, into the product 20.4.

An alternative route to the product 20.4 is shown in Scheme 21 in which amine 11.1 is treated under conditions described in Scheme 2 with the amine 1.2 to give the amine 21.1. The amine 21.1 is then sulfonylated with 20.2 in which the substituent A is either the group link-$P(O)(OR^1)_2$ or a precursor such as [OH], [SH], [NH], Br etc, as described in Scheme 2, to afford the product 21.2. The product 21.2 is then converted as described above, Scheme 2, into the sulfonamide 20.4.

The reactions shown in Scheme 20 and 21 illustrate the preparation of the compound 20.4 in which the substituent A is either the group Ank-$P(O)(OR^1)_2$ or a precursor such as [OH], [SH], [NH], Br etc. Scheme 22 depicts the conversion of this compounds 20.4 in which A is [OH], [SH], [NH], Br etc, into the phosphonate esters 4 respectively, in which X is a direct bond. In this procedure, the amines 20.4 is converted, using the procedures described below, Schemes 47-99, into the compounds 4.

Scheme 20

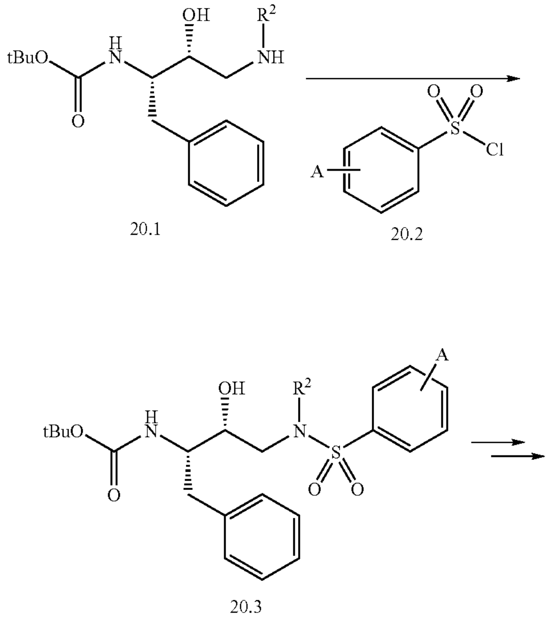

20.1

20.2

20.3

-continued

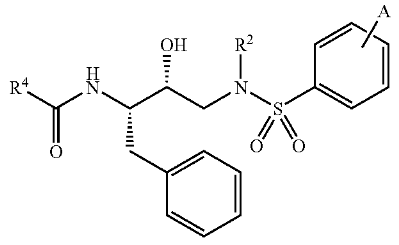

20.4

-continued

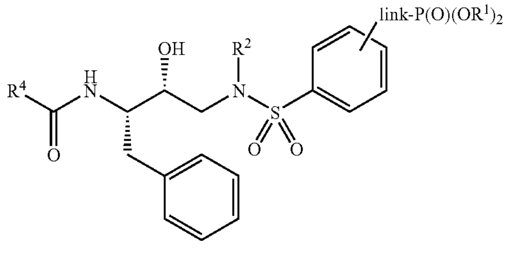

4

Schemes 23 illustrate the preparation of the phosphonate esters 4 in which X is a direct bond and the $R_4COOH$ group contains an amine group. The amine 23.1, prepared from the epoxide 13.1 and an amine 1.2 as decsribed in Sheme 13 for the synthesis of 13.2 from 13.1, is reacted with the sulfonyl chloride 20.2 in which the substituent A is either the group link-$P(O)(OR^1)_2$ or a precursor such as [OH], [SH], [NH], Br etc, as described in Schemes 1 for the synthesis of 1.5, to give the product 23.2. The product 23.2 is then reduced to amine 23.3 according to the conditions described in Scheme 3 for the preparation of 3.4 from 3.3. The amine product is then converted as described in Scheme 5 into the chloride 23.4. The chloride is treated with the amine 5.7 to afford the amine 23.5, as described in Scheme 5 for the preparation of 5.8 from 5.7.

The reactions shown in Scheme 23 illustrate the preparation of the compound 23.5 in which the substituent A is either the group link-$P(O)(OR^1)_2$ or a precursor such as [OH], [SH], [NH], Br etc. Scheme 24 depicts the conversion of the compound 23.5 in which A is [OH], [SH], [NH], Br etc, into the phosphonate esters 4 in which X is a direct bond. In this procedure, the compound 23.5 is converted, using the procedures described below, Schemes 47-99, into the compound 4.

Scheme 21

11.1

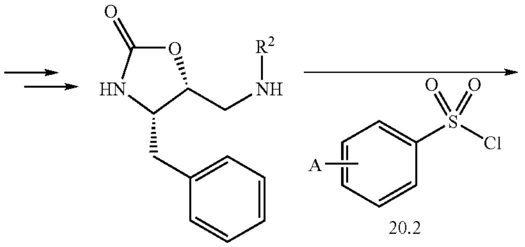

20.2

21.1

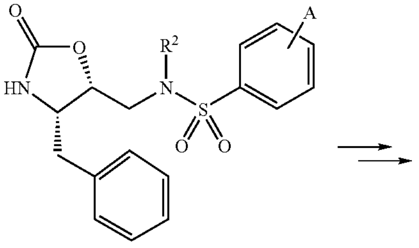

21.2

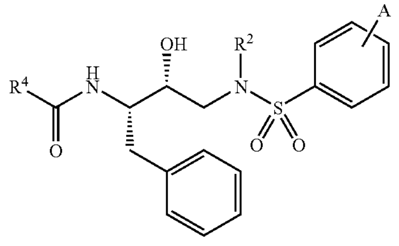

20.4

Scheme 22

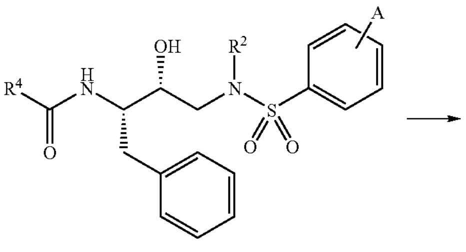

20.4

Scheme 23

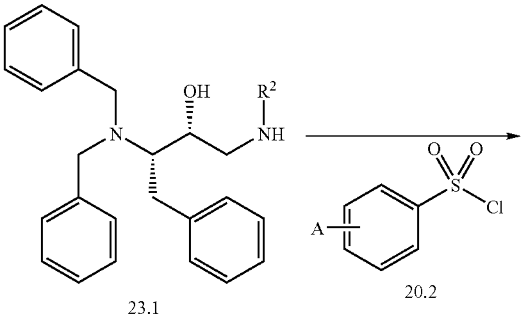

20.2

23.1

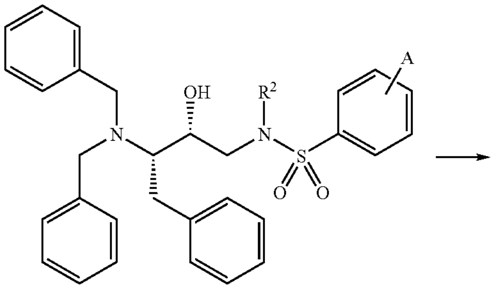

23.2

-continued

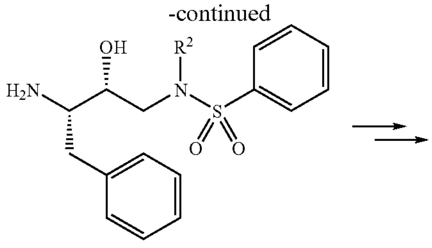

23.3

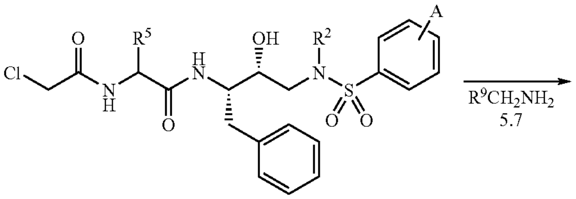

23.4

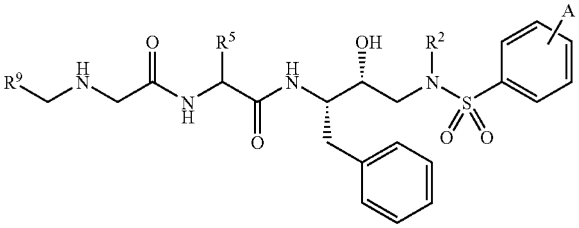

23.5

Scheme 24

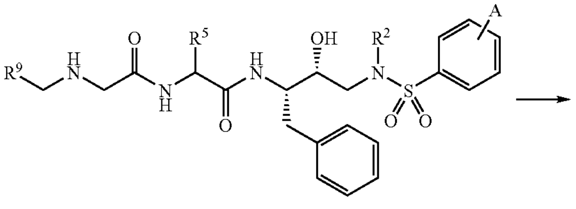

23.5

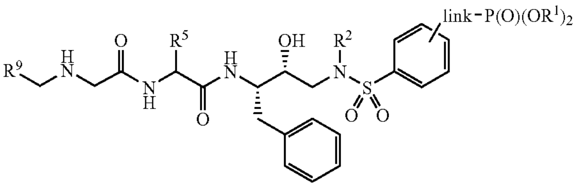

4

Preparation of the Phosphonate Ester Intermediates 4 in which X is a sulfur

The intermediate phosphonate ester 4, in which the group A is attached to a sulfur linked aryl moiety, and the $R_4COOH$ group does not contain an amine is prepared as shown in Schemes 25-27. Amine 25.1 prepared from epoxide 15.1 and amine 1.2 as described in Scheme 15 is treated with sulfonamide 20.2 in which the substituent A is either the group link-$P(O)(OR^1)_2$ or a precursor such as [OH], [SH], [NH], Br etc, using the conditions described in Scheme 7, to give the sulfonamide 25.2. The sulfonamide 25.2 is then converted as described in Scheme 7 for the conversion of 7.9 to 7.10, and Scheme 9a for the conversion of 7.10 into 9a.4, to the product 25.3. Alternatively, Scheme 26, illustrates how the amine 8.5 prepared according to Scheme 8 is reacted with 20.2 under conditions described in Scheme 8 for the preparation of 8.6 from 8.5, to give the sulfonamide 26.1. Further modification according to the conditions described in Scheme 8 for the preparation of 7.11, affords sulfonamide 25.3.

The reactions shown in Scheme 25-26 illustrate the preparation of the compounds sulfonamide 25.3 in which the substituent A is either the group link-$P(O)(OR^1)_2$ or a precursor such as [OH], [SH], [NH], Br etc. Scheme 27 depicts the conversion of 25.3 in which A is [OH], [SH], [NH], Br etc, into the phosphonate 4 in which X is sulfur. In this procedure 25.3 is converted, using the procedures described below, Schemes 47-99, into the compound 4.

Preparation of the intermediate phosphonate ester 4, in which the group A is attached to a sulfur linked aryl moiety, and the $R_4COOH$ group contains an amine are prepared as shown in Schemes 28-29. Amine 25.2 (Scheme 25) in which the substituent A is either the group link-$P(O)(OR^1)_2$ or a precursor such as [OH], [SH], [NH], Br etc, is converted to 28.1 as described in Scheme 7 for the preparation of the amine 7.10 from 7.9 and Scheme 9a for the preparation of 9a.4 from 7.10.

The reactions shown in Scheme 28 illustrate the preparation of the compounds sulfonamide 28.1 in which the substituent A is either the group link-$P(O)(OR^1)_2$ or a precursor such as [OH], [SH], [NH], Br etc. Scheme 29 depicts the conversion of 28.1 in which A is [OH], [SH], [NH], Br etc, into the phosphonate 4 in which X is sulfur. In this procedure 28.1 is converted, using the procedures described below, Schemes 47-99, into the compound 4.

Scheme 25

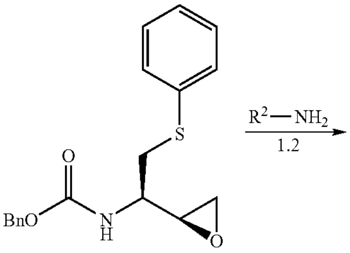

15.1

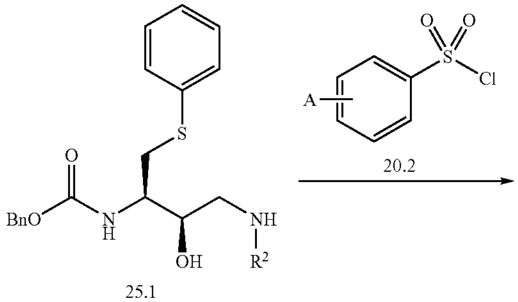

25.1

-continued
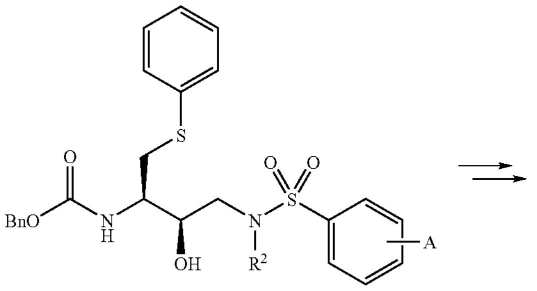
25.2
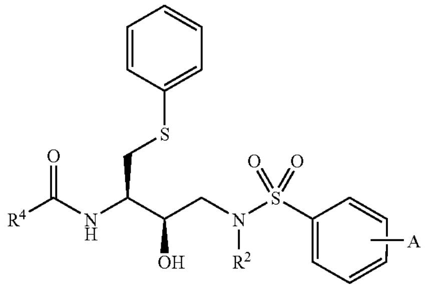
25.3
Scheme 26
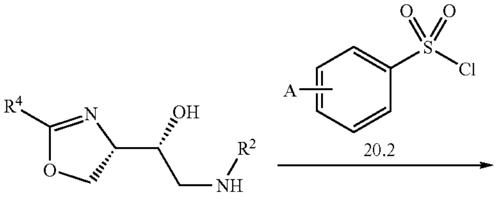
20.2
8.5
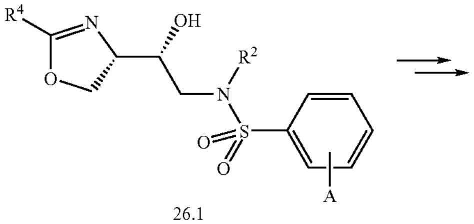
26.1
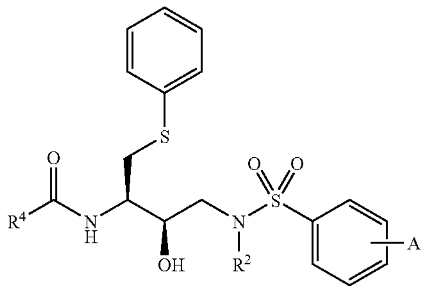
25.3
Scheme 27
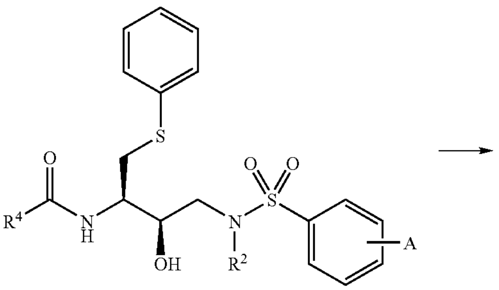
25.3
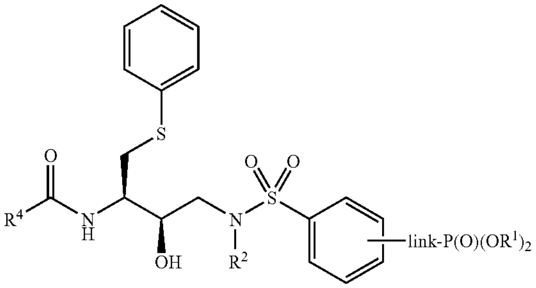
4
Scheme 28
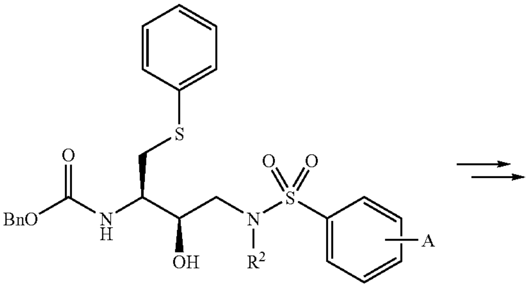
25.2
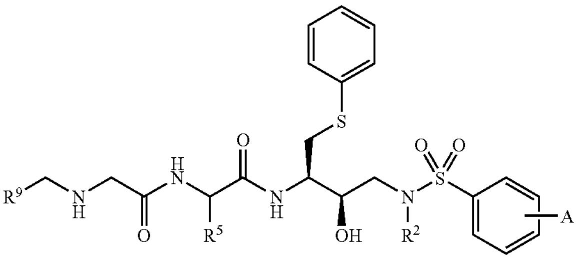
28.1

Scheme 29

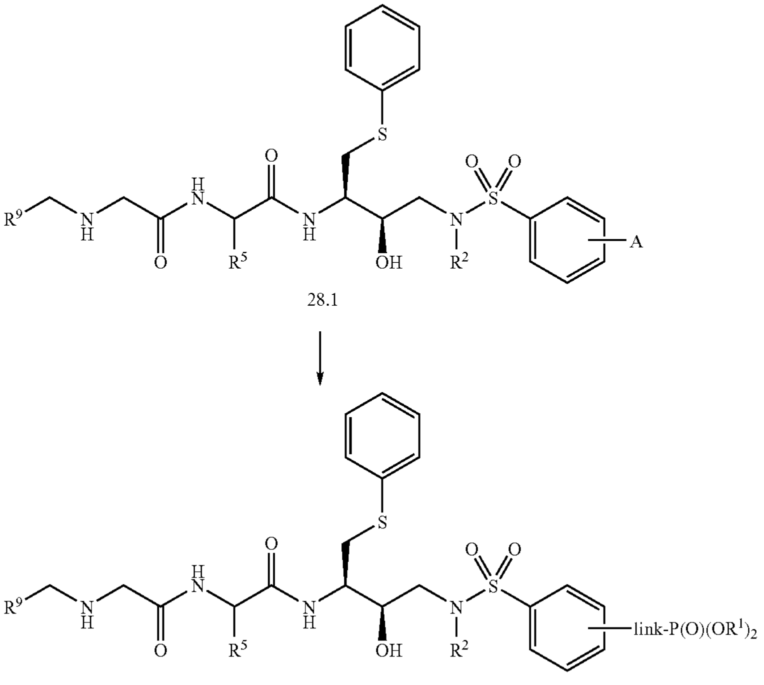

28.1

4

Preparation of the Phosphonate Ester Intermediates 5 in which X is a Direct Bond Schemes 30 illustrates the preparation of the phosphonate esters 5 in which X is a direct bond and the R group does not contain a primary or secondary amine group. As shown in Scheme 30, the amine 23.1 (Scheme 23) is reacted with the alcohol 30.1 in which the substituent A is either the group link-P(O)$(OR^1)_2$ or a precursor such as [OH], [SH], [NH], Br etc, to afford the carbamate 30.2. The reaction is performed under conditions described below, Scheme 98, for making carbamates from amines and alcohols. The preparation of the 30.1 is described in Schemes 83-86. The carbamate 30.2 is then deprotected using conditions described in Scheme 3 for removal of the benzyl groups to give 30.3. Treatment of 30.3 with the $R^4$COOH acid 1.7 using the conditions described in Scheme 1 then afford the amide 30.4

The reactions shown in Scheme 30 illustrate the preparation of the compound 30.4 in which the substituent A is either the group link-P(O)$(OR^1)_2$ or a precursor such as [OH], [SH], [NH], Br etc. Scheme 31 depicts the conversion of this compounds 30.4 in which A is [OH], [SH], [NH], Br etc, into the phosphonate esters 5 respectively, in which X is a direct bond. In this procedure, the amines 30.4 is converted, using the procedures described below, Schemes 47-99, into the compounds 5.

Schemes 32 illustrates the preparation of the phosphonate esters 5 in which X is a direct bond and the $R_4$COOH group contains an amine. The carbamate 30.2 in which the substituent A is either the group link-P(O)$(OR^1)_2$ or a precursor such as [OH], [SH], [NH], Br etc, is converted into the chloride 32.1 using conditions as described in Scheme 9a. Chloride 32.1 is then treated with amine 5.7 to give the amine 32.2, as described in Scheme 9a for the conversion of 7.10 into 9a.3.

The reactions shown in Scheme 32 illustrate the preparation of the compound 32.2 in which the substituent A is either the group link-P(O)$(OR^1)_2$ or a precursor such as [OH], [SH], [NH], Br etc. Scheme 33 depicts the conversion of the compound 32.2 in which A is [OH], [SH], [NH], Br etc, into the phosphonate esters 5 in which X is a direct bond. In this procedure, the compound 32.2 is converted, using the procedures described below, Schemes 47-99, into the compound 5.

Scheme 30

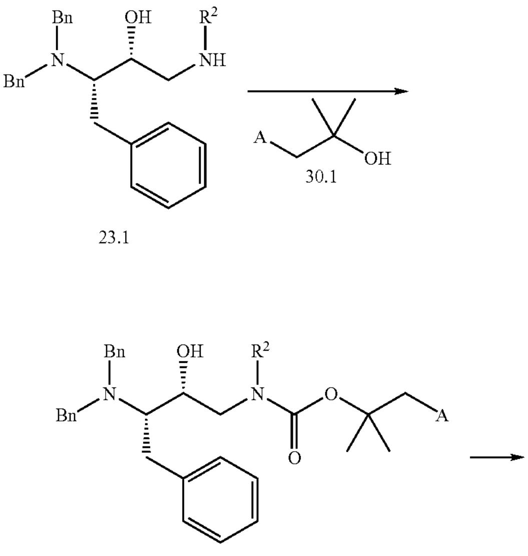

23.1

30.1

30.2

-continued
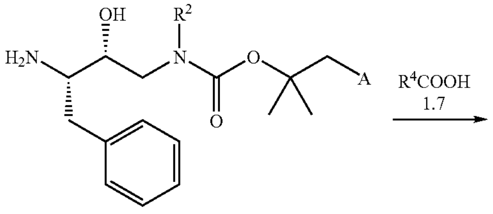
30.3
Scheme 31
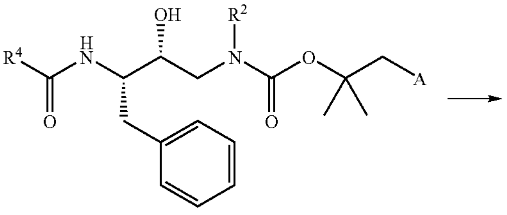
30.4
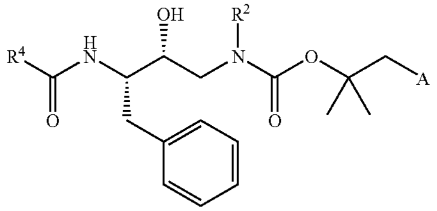
30.4
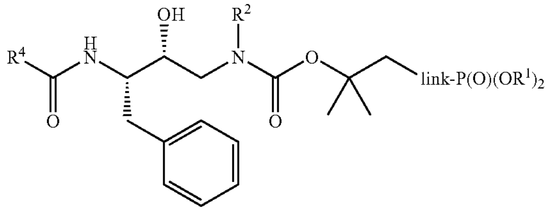
5
Scheme 32
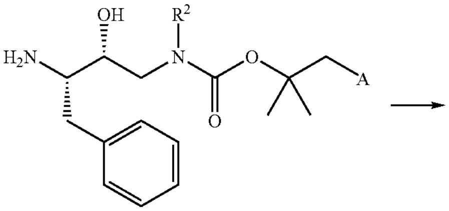
30.2
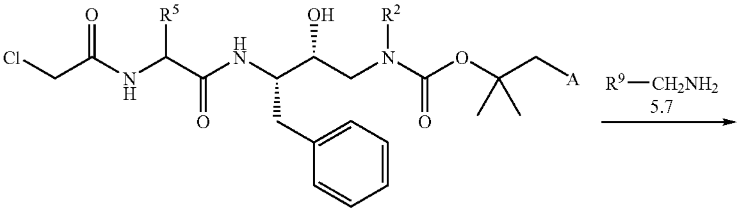
32.1

-continued

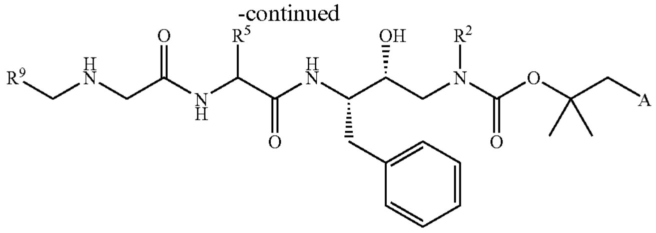

32.2

Scheme 33

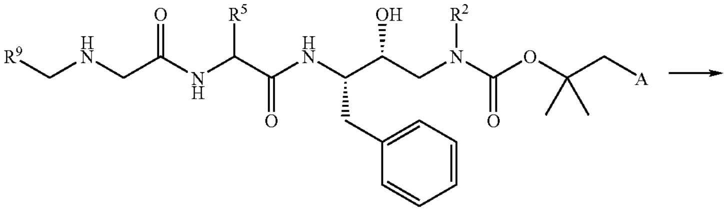

32.2

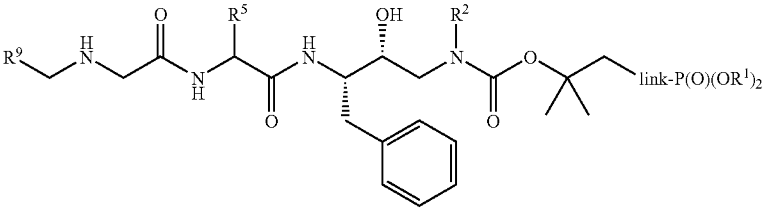

5

Preparation of the Phosphonate Ester Intermediates 5 in which X is a Sulfur

The intermediate phosphonate ester 5, in which the group A is attached to a sulfur linked aryl moiety, is prepared as shown in Schemes 34-36. Amine 25.1 prepared according to Scheme 25, is treated with alcohol 30.1 in which the substituent A is either the group link-P(O)(OR$^1$)$_2$ or a precursor such as [OH], [SH], [NH], Br etc, using the conditions described below, Scheme 98, to give the carbamate 34.1. The carbamate 34.1 is then converted as described in Scheme 7, for the conversion of 7.9 to 7.11, to the product 34.2. Alternatively the amine 8.5 prepared according to Scheme 8 can be reacted with alcohol 30.1 under conditions described in Scheme 98 to give the carbamate 35.1. Further modification according to the conditions described in Scheme 8, except incorporating thiophenol, then affords sulfonamide 34.2.

The reactions shown in Scheme 34-35 illustrate the preparation of the compounds sulfonamide 34.2 in which the substituent A is either the group link-P(O)(OR$^1$)$_2$ or a precursor such as [OH], [SH], [NH], Br etc. Scheme 36 depicts the conversion of 34.2 in which A is [OH], [SH], [NH], Br etc, into the phosphonate 5 in which X is sulfur. In this procedure 34.2 is converted, using the procedures described below, Schemes 47-99, into the compound 5.

Preparation of the intermediate phosphonate ester 5, in which the group A is attached to a sulfur linked aryl moiety, and the R$_4$COOH group contains an amine are prepared as shown in Schemes 37-38. Carbamate 34.1 (Scheme 35) in which the substituent A is either the group link-P(O)(OR$^1$)$_2$ or a precursor such as [OH], [SH], [NH], Br etc, is converted to 37.1, as described in Scheme 7 for the preparation of the amine 7.10 from 7.9 and Scheme 9a for the preparation of 9a.4 from 7.10.

The reactions shown in Scheme 37 illustrate the preparation of the compounds sulfonamide 37.1 in which the substituent A is either the group link-P(O)(OR$^1$)$_2$ or a precursor such as [OH], [SH], [NH], Br etc. Scheme 38 depicts the conversion of 37.1 in which A is [OH], [SH], [NH], Br etc, into the phosphonate 5 in which X is sulfur. In this procedure 37.1 is converted, using the procedures described below, Schemes 47-99, into the compound 5.

Scheme 34

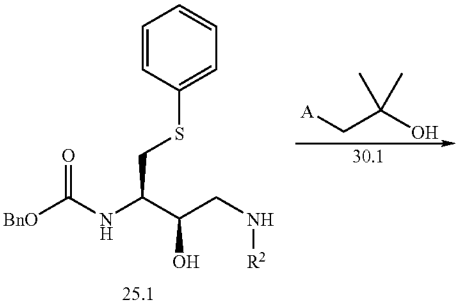

30.1

25.1

-continued
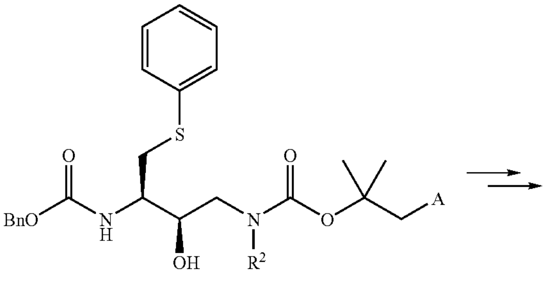
34.1
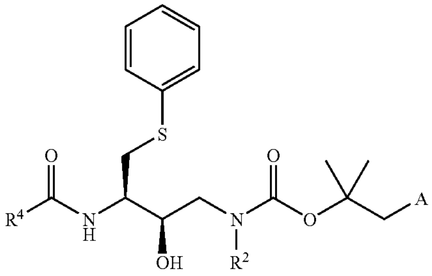
34.2
Scheme 35
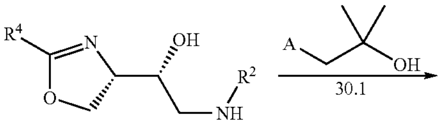
8.5
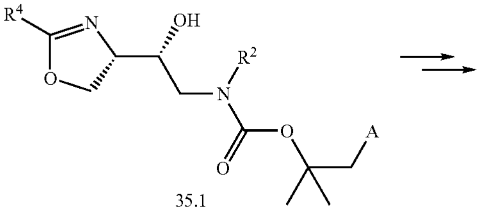
35.1
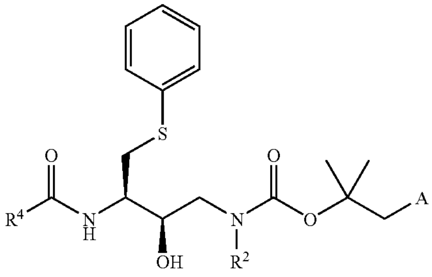
34.2
Scheme 36
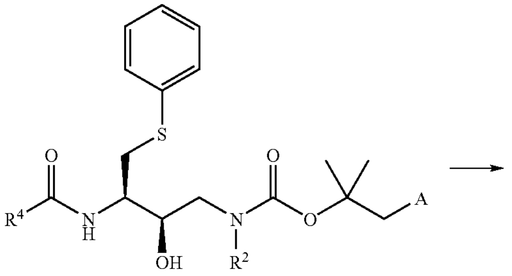
34.2
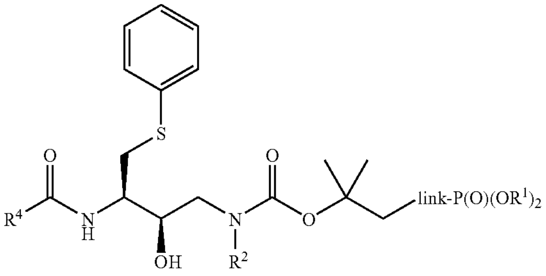
5
Scheme 37
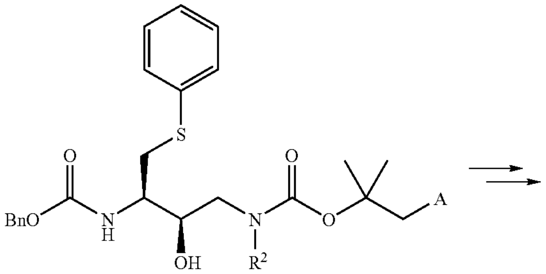
34.1
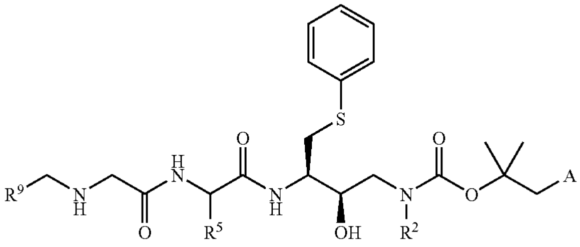
37.1

Scheme 38

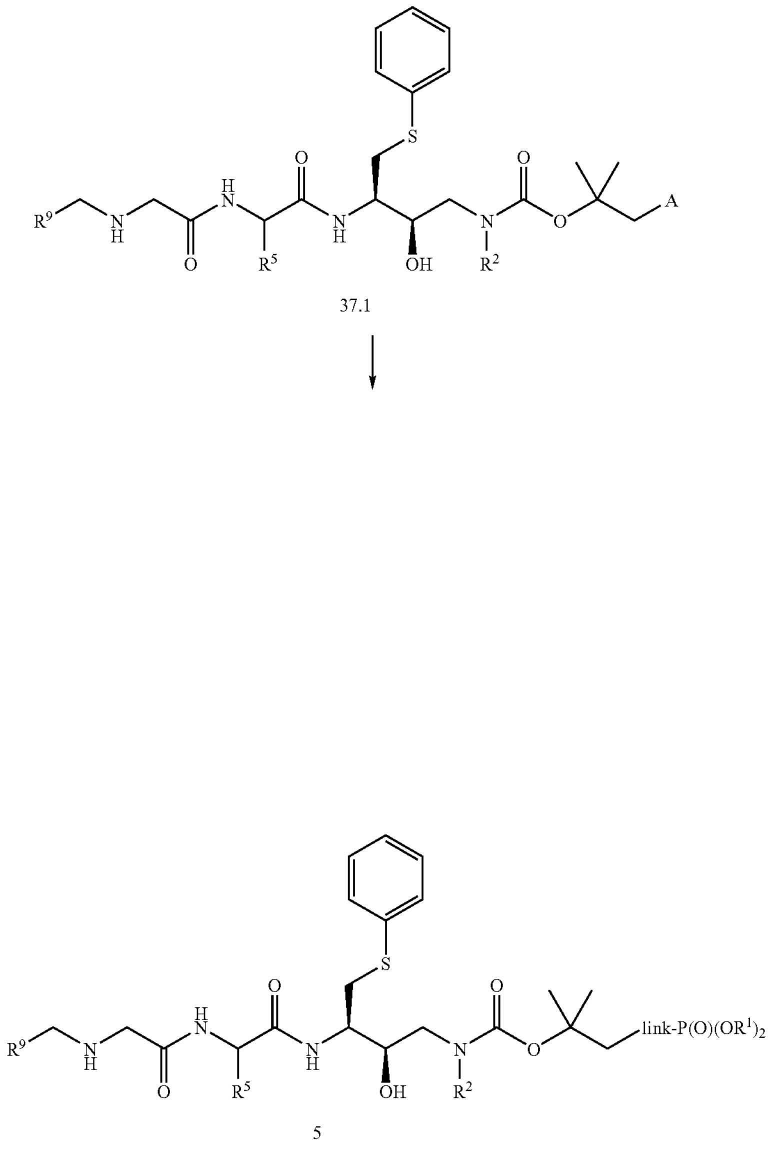

37.1

5

Preparation of the Phosphonate Ester Intermediates 6 and 7 in which X is a Direct Bond Schemes 39-40 illustrate the preparation of the phosphonate esters 6 and 7 in which X is a direct bond. As shown in Scheme 39, the epoxide 13.1, prepared as described in Scheme 13 is converted to the chloride 39.1, as described in Scheme 3, for the preparation of 3.4, and Scheme 5, for the conversion of 3.4 into 5.6. The chloride 39.1 is then reacted with the amine 39.2 or 39.4, in which the substituent A is either the group link-P(O)(OR$^1$)$_2$ or a precursor such as [OH], [SH], [NH], Br etc, to afford the amine 39.3 and 39.5 respectively. The reaction is performed under the same conditions as described above, Scheme 5 for the preparation of the amine 5.8 from 5.6. The prepartion of 39.2 and 39.4, amines in which A is link-P(O)(OR$^1$)$_2$, are shown in Schemes 79-80 and Schemes 81-82 respectively.

The reactions shown in Scheme 39 illustrate the preparation of the compounds 39.3 and 39.5 in which the substituent A is either the group link-P(O)(OR$^1$)$_2$ or a precursor such as [OH], [SH], [NH], Br etc. Scheme 40 depicts the conversion of these compounds 39.3 and 39.5 in which A is [OH], [SH], [NH], Br etc, into the phosphonate esters 6 and 7 respectively, in which X is a direct bond. In this procedure, the amines 39.3 and 39.5 are converted, using the procedures described below, Schemes 47-99, into the compounds 6 and 7 respectively.

Scheme 39

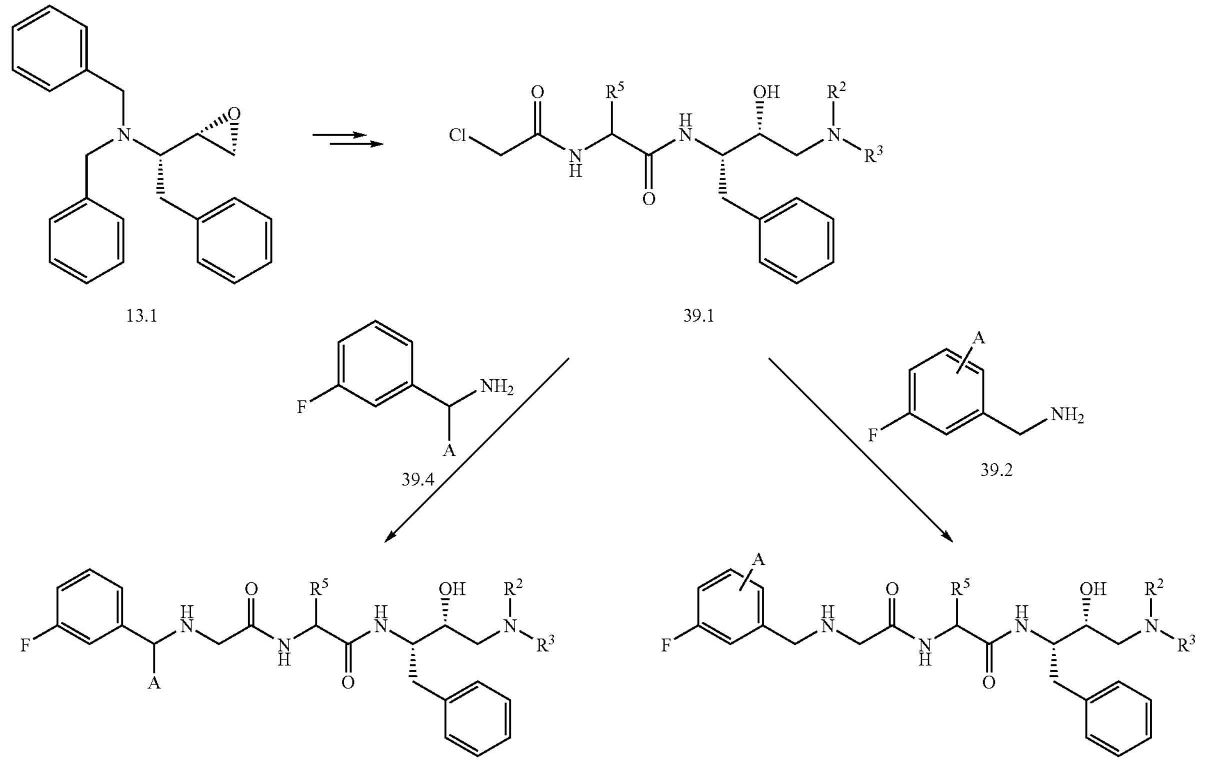

13.1 39.1 39.4 39.2 39.5 39.3

Scheme 40

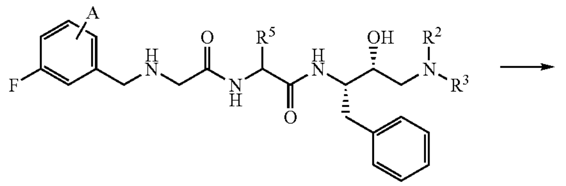

39.3

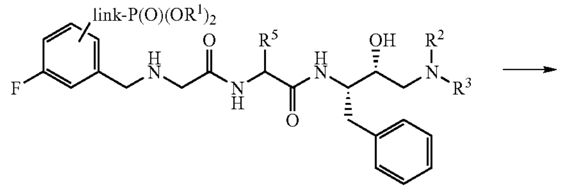

6

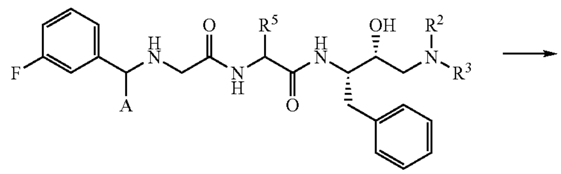

39.5

-continued

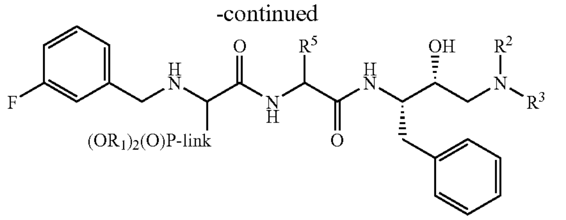

7

Preparation of the Phosphonate Ester Intermediates 6 and 7 in which X is a Sulfur The intermediate phosphonate esters 6 and 7, in which the group A is attached to a sulfur linked aryl moiety, are prepared as shown in Scheme 41-42. The amine 25.1 (Scheme 25) is converted to the chloride 41.1 as described in Scheme 7 for the preparation of 7.10 from 7.8, and Scheme 9a for conversion of 7.10 to 9a3. The chloride 41.1 is then treated with amine 39.2 or amine 39.4, in which substituent A is either the group link-$P(O)(OR^1)_2$ or a precursor such as [OH], [SH], [NH], Br etc, as described in Scheme 5, to give the amines 41.2 and 41.3 respectively.

The reactions shown in Scheme 41 illustrate the preparation of the compounds 41.2 and 41.3 in which the substituent A is either the group link-$P(O)(OR^1)_2$ or a precursor such as [OH], [SH], [NH], Br etc. Scheme 42 depicts the conversion of 41.2 and 41.3 in which A is [OH], [SH], [NH], Br etc, into the phosphonate ester 6 and 7 in which X is sulfur. In this procedure 41.2 or 41.3 is converted, using the procedures described below, Schemes 47-99, into the compound 6 and 7.

Scheme 41
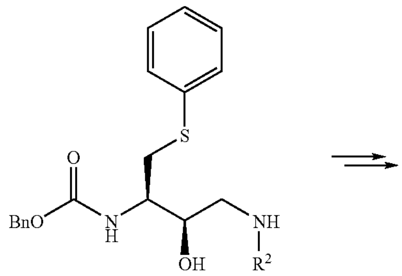
25.1
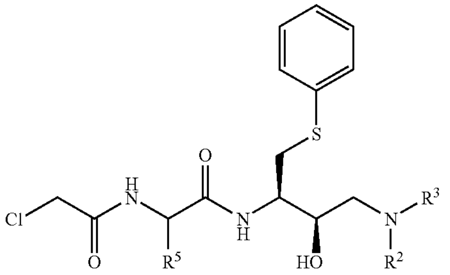
41.1
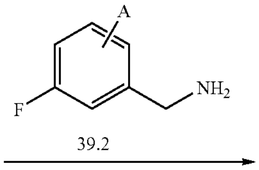
39.2
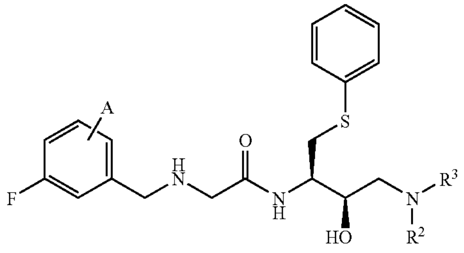
41.2
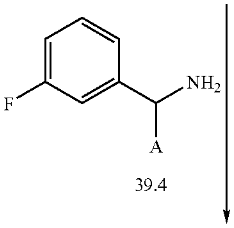
39.4
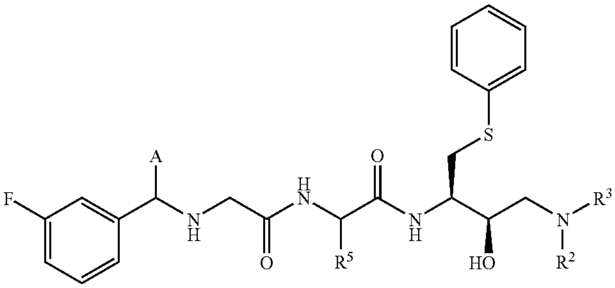
41.3

Scheme 42

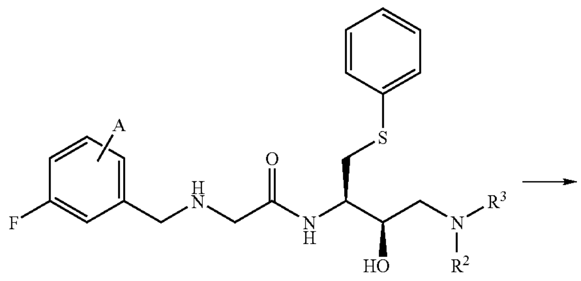

41.2

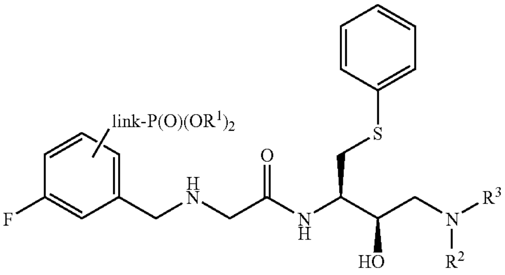

6

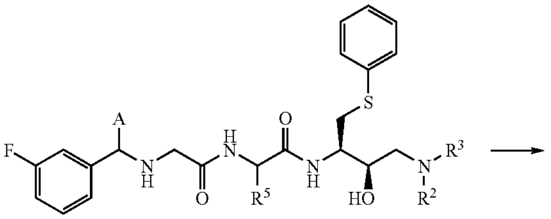

41.3

-continued

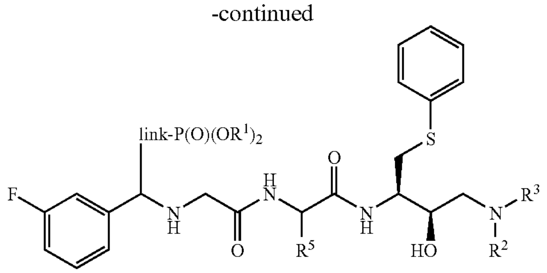

7

Preparation of the Phosphonate Ester Intermediates 8-10 in which X is a Direct Bond Schemes 43-44 illustrate the preparation of the phosphonate esters 8-10 in which X is a direct bond. As shown in Scheme 43, the amine 43.1 prepared from 10.1 or 21.2 is reacted with the acid 43.2, 43.4 or 43.6, in which the substituent A is either the group link-P(O)$(OR^1)_2$ or a precursor such as [OH], [SH], [NH], Br etc, to afford the amide 43.3, 43.5 and 43.7 respectively. The reaction is performed under the same conditions as described above, Scheme 1 for the preparation of the amide 1.8. Amine 43.1 is prepared from epoxide 10.1 using the conditions described in Scheme 1 except utilising 10.1 in place of 1.1. Amine 43.1 is prepared from 21.2 according to the conditions described in Scheme 2 except utilizing 21.2 in place of 2.1. The preparation of the acid 43.2 is described in Schemes 47-51, acid 43.4 is described in Schemes 87-91, and acid 43.6 is described in Schemes 52-55.

The reactions shown in Scheme 43 illustrate the preparation of the compounds 43.3, 43.5 and 43.7 in which the substituent A is either the group link-P(O)$(OR^1)_2$ or a precursor such as [OH], [SH], [NH], Br etc. Scheme 44 depicts the conversion of these compounds 43.3, 43.5, and 43.7 in which A is [OH], [SH], [NH], Br etc, into the phosphonate esters 8, 9 and 10 respectively, in which X is a direct bond. In this procedure, the amines 43.3, 43.5 and 43.7 are converted, using the procedures described below, Schemes 47-99, into the compounds 8, 9, and 10 respectively.

Scheme 43

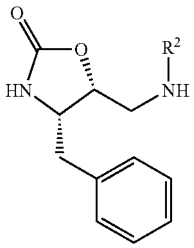

21.2

-continued
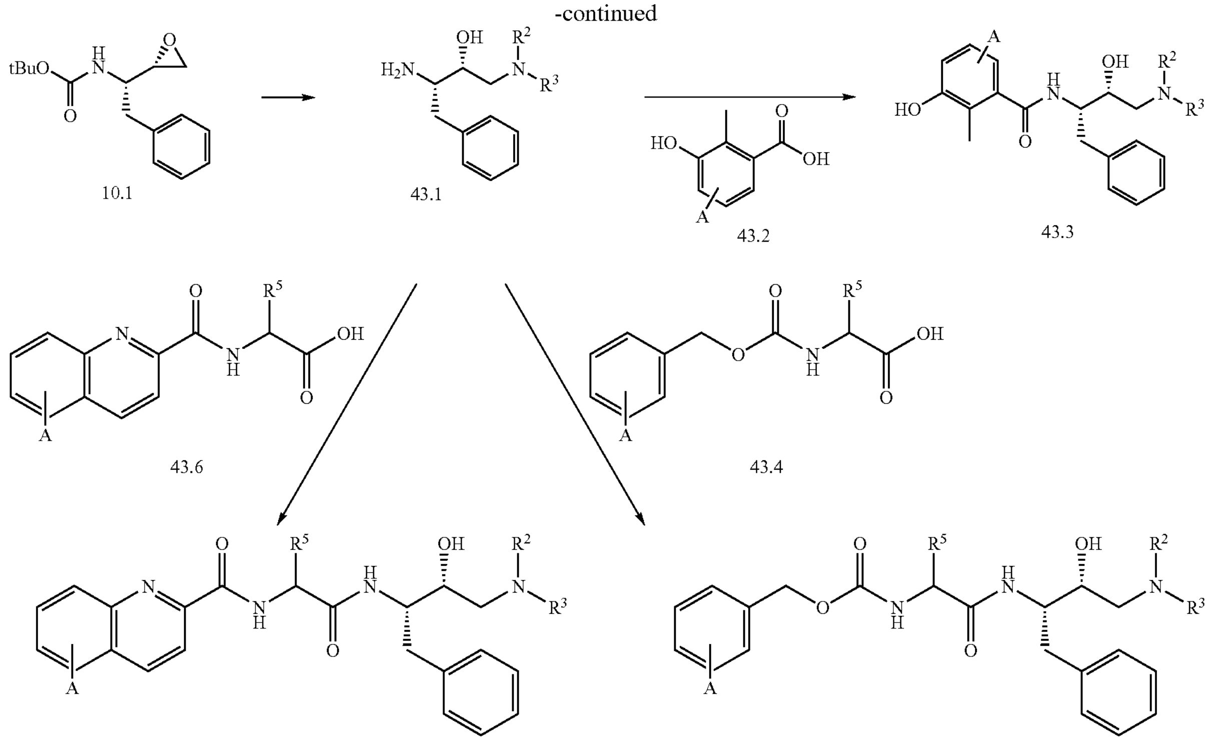
10.1 43.1 43.2 43.3 43.6 43.4 43.7 43.5
Scheme 44
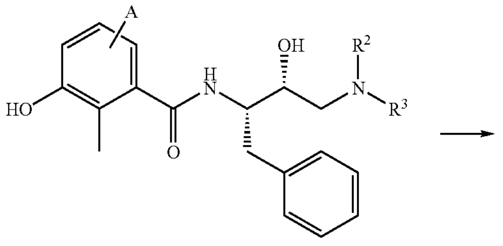
43.3
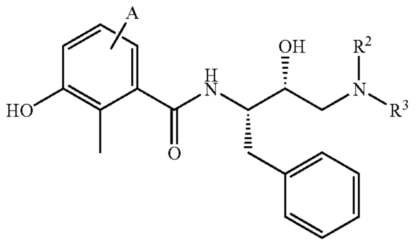
8
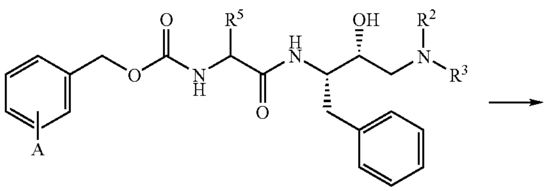
43.5
-continued
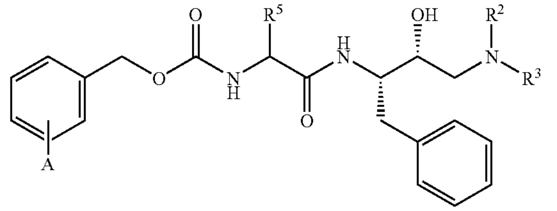
9
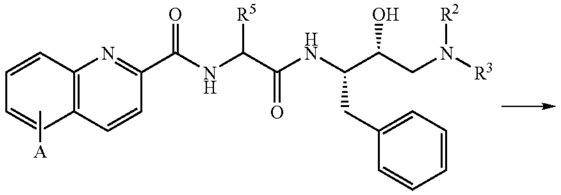
43.7
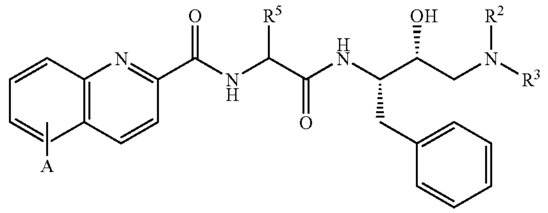
10
Preparation of the Phosphonate Ester Intermediates 8-10 in which X is a Sulfur The intermediate phosphonate esters 8-10, in which the group A is attached to a sulfur linked aryl moiety, are prepared as shown in Schemes 45-46. In Scheme 45, epoxide 15.1 is prepared from mesylate 7.1 using the conditions described in Scheme 7 except incorporating thiophenol for thiol 7.2. The epoxide 15.1 is then converted to amine 45.1 according to the conditions described in Scheme 7 for the preparation of 7.10 from 7.7. Amine 45.1 is then treated with acids 43.2, 43.4 or 43.6, in which substituent A is either the group link-P(O)$(OR^1)_2$ or a precursor such as [OH], [SH], [NH], Br etc, as described in Scheme 7, to give the amides 45.2, 45.3, and 45.4 respectively.

The reactions shown in Scheme 45 illustrate the preparation of the compounds 45.2, 45.3, and 45.4 in which the substituent A is either the group link-P(O)$(OR^1)_2$ or a precursor such as [OH], [SH], [NH], Br etc. Scheme 46 depicts the conversion 45.2, 45.3, and 45.4 in which A is [OH], [SH], [NH], Br etc, into the phosphonate ester 8, 9 and 10 respectively in which X is sulfur. In this procedure 45.2, 45.3, and 45.4 is converted, using the procedures described below, Schemes 47-99, into the compounds 8, 9 and 10 respectively.

Scheme 45

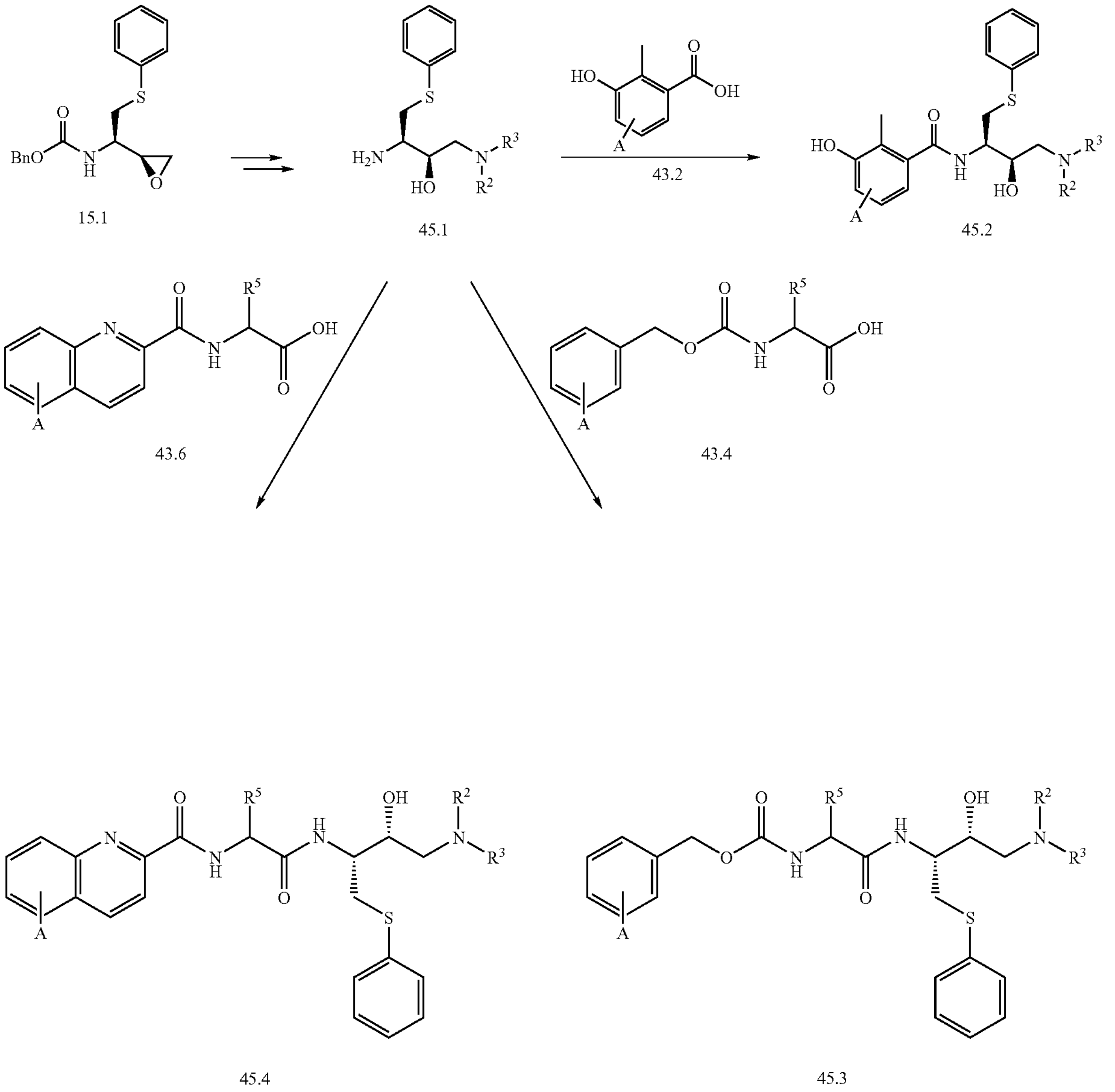

Scheme 46

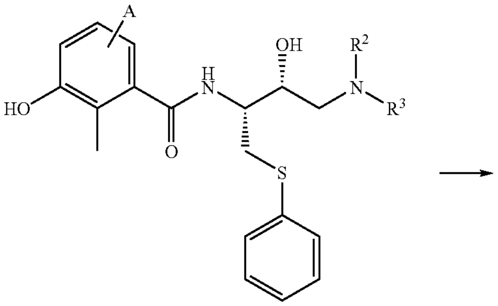

45.2

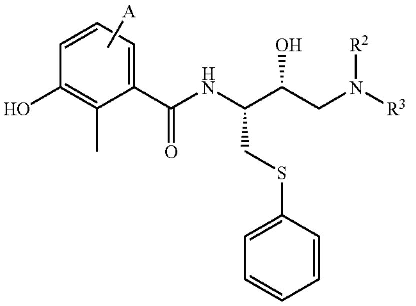

8

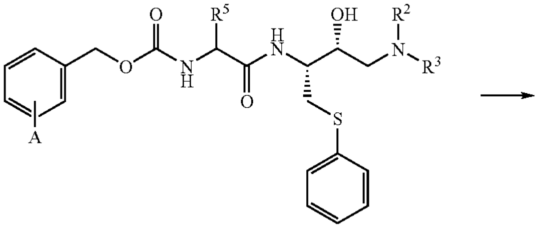

45.3

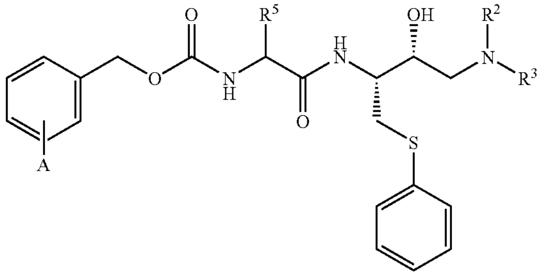

9

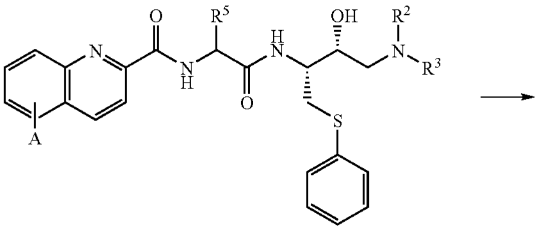

45.4

-continued

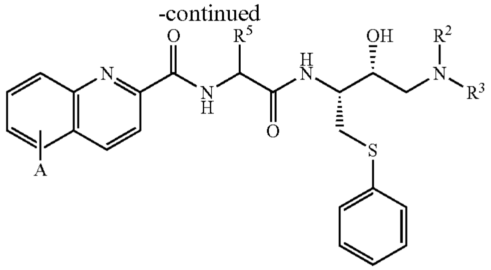

10

Preparation of Phosphonate-containing Hydroxymethyl Benzoic Acids 43.2.

Schemes 47-51 illustrate methods for the preparation of phosphonate-containing hydroxymethyl benzoic acids 43.2 which are employed in the preparation of the phosphonate esters 8.

Scheme 47 illustrates a method for the preparation of hydroxymethylbenzoic acid reactants in which the phosphonate moiety is attached directly to the phenyl ring. In this method, a suitably protected bromo hydroxy methyl benzoic acid 47.1 is subjected to halogen-methyl exchange to afford the organometallic intermediate 47.2. This compound is reacted with a chlorodialkyl phosphite 47.3 to yield the phenylphosphonate ester 47.4, which upon deprotection affords the carboxylic acid 47.5.

For example, 4-bromo-3-hydroxy-2-methylbenzoic acid, 47.6, prepared by bromination of 3-hydroxy-2-methylbenzoic acid, as described, for example, J. Am. Chem. Soc., 55, 1676, 1933, is converted into the acid chloride, for example by reaction with thionyl chloride. The acid chloride is then reacted with 3-methyl-3-hydroxymethyloxetane 47.7, as described in Protective Groups in Organic Synthesis, by T. W. Greene and P. G. M. Wuts, Wiley, 1991, pp. 268, to afford the ester 47.8. This compound is treated with boron trifluoride at 0° to effect rearrangement to the orthoester 47.9, known as the OBO ester. This material is treated with a silylating reagent, for example tert-butyl chlorodimethylsilane, in the presence of a base such as imidazole, to yield the silyl ether 47.10. Halogen-metal exchange is performed by the reaction of the substrate 47.10 with butyllithium, and the lithiated intermediate is then coupled with a chlorodialkyl phosphite 47.3, to produce the phosphonate 47.11. Deprotection, for example by treatment with 4-toluenesulfonic acid in aqueous pyridine, as described in Can. J. Chem., 61, 712, 1983, removes both the OBO ester and the silyl group, to produce the carboxylic acid 47.12.

Using the above procedures, but employing, in place of the bromo compound 47.6, different bromo compounds 47.1, there are obtained the corresponding products 47.5.

Scheme 48 illustrates the preparation of hydroxymethylbenzoic acid derivatives in which the phosphonate moiety is attached by means of a one-carbon link.

In this method, a suitably protected dimethyl hydroxybenzoic acid, 48.1, is reacted with a brominating agent, so as to effect benzylic bromination. The product 48.2 is reacted with a sodium dialkyl phosphite, 48.3, as described in J. Med. Chem., 1992, 35, 1371, to effect displacement of the benzylic bromide to afford the phosphonate 48.4. Deprotection of the carboxyl function then yields the carboxylic acid 48.5.

For example, 2,5-dimethyl-3-hydroxybenzoic acid, 48.6, the preparation of which is described in Can. J. Chem., 1970, 48, 1346, is reacted with excess methoxymethyl chloride, as described in Protective Groups in Organic Synthesis, by T. W. Greene and P. G. M Wuts, Second Edition 1990, p.17, to afford the ether ester 48.7. The reaction is performed in an inert solvent such as dichloromethane, in the presence of an organic base such as N-methylmorpholine or diisopropylethylamine. The product 48.7 is then reacted with a brominating agent, for example N-bromosuccinimide, in an inert solvent such as, for example, ethyl acetate, at reflux, to afford the bromomethyl product 48.8. This compound is then reacted with a sodium dialkyl phosphite 48.3 in tetrahydrofuran, as described above, to afford the phosphonate 48.9. Deprotection, for example by brief treatment with a trace of mineral acid in methanol, as described in J. Chem. Soc. Chem. Comm., 1974, 298, then yields the carboxylic acid 48.10. Using the above procedures, but employing, in place of the methyl compound 48.6, different methyl compounds 48.1, there are obtained the corresponding products 48.5.

Scheme 49 illustrates the preparation of phosphonate-containing hydroxymethylbenzoic acids in which the phosphonate group is attached by means of an oxygen or sulfur atom.

In this method, a suitably protected hydroxy- or mercapto-substituted hydroxy methyl benzoic acid 49.1 is reacted, under the conditions of the Mitsonobu reaction, with a dialkyl hydroxymethyl phosphonate 49.2, to afford the coupled product 49.3, which upon deprotection affords the carboxylic acid 49.4.

For example, 3,6-dihydroxy-2-methylbenzoic acid, 49.5, the preparation of which is described in Yakugaku Zasshi 1971, 91, 257, is converted into the diphenylmethyl ester 49.6, by treatment with diphenyldiazomethane, as described in Protective Groups in Organic Synthesis, by T. W. Greene and P. G. M. Wuts, Wiley, 1991, pp. 253. The product is then reacted with one equivalent of a silylating reagent, such as, for example, tert butylchlorodimethylsilane, as described in Protective Groups in Organic Synthesis, by T. W. Greene and P. G. M Wuts, Wiley, Second Edition 1990, p 77, to afford the mono-silyl ether 49.7. This compound is then reacted with a dialkyl hydroxymethylphosphonate 49.2, under the conditions of the Mitsonobu reaction. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The reaction affords the coupled product 49.8. Deprotection, for example by treatment with trifluoroacetic acid at ambient temperature, as described in J. Chem. Soc., C, 1191, 1966, then affords the phenolic carboxylic acid 49.9.

Using the above procedures, but employing, in place of the phenol 49.5, different phenols or thiophenols 49.1, there are obtained the corresponding products 49.4.

Scheme 50 depicts the preparation of phosphonate esters attached to the hydroxymethylbenzoic acid moiety by means of unsaturated or saturated carbon chains.

In this method, a dialkyl alkenylphosphonate 50.2 is coupled, by means of a palladium catalyzed Heck reaction, with a suitably protected bromo substituted hydroxymethylbenzoic acid 50.1. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or a palladium(II) catalyst such as palladium(II) acetate, and optionally in the presence of a base such as triethylamine or potassium carbonate. The product 50.3 is deprotected to afford the phosphonate 50.4; the latter compound is subjected to catalytic hydrogenation to afford the saturated carboxylic acid 50.5.

For example, 5-bromo-3-hydroxy-2-methylbenzoic acid 50.6, prepared as described in WO 9218490, is converted as described above, into the silyl ether OBO ester 50.7 as described above. This compound is coupled with, for example, a dialkyl 4-buten-1-ylphosphonate 50.8, the preparation of which is described in J. Med. Chem., 1996, 39, 949, using the conditions described above to afford the product 50.9. Deprotection, or hydrogenation/deprotection, of this compound, as described above, then affords respectively the unsaturated and saturated products 50.10 and 50.11.

Using the above procedures, but employing, in place of the bromo compound 50.6, different bromo compounds 50.1, and/or different phosphonates 50.2, there are obtained the corresponding products 50.4 and 50.5.

Scheme 51 illustrates the preparation of phosphonate esters linked to the hydroxymethylbenzoic acid moiety by means of an aromatic ring.

In this method, a suitably protected bromo-substituted hydroxymethylbenzoic acid 51.1 is converted to the corresponding boronic acid 51.2, by metallation with butyllithium and boronation, as described in J. Organomet. Chem., 1999, 581, 82. The product is subjected to a Suzuki coupling reaction with a dialkyl bromophenyl phosphonate 51.3. The product 51.4 is then deprotected to afford the diaryl phosphonate product 51.5.

For example, the silylated OBO ester 51.6, prepared as described above, (Scheme 47), from 5-bromo-3-hydroxybenzoic acid, the preparation of which is described in J. Labelled. Comp. Radiopharm., 1992, 31, 175, is converted into the boronic acid 51.7, as described above. This material is coupled with a dialkyl 4-bromophenyl phosphonate 51.8, prepared as described in J. Chem. Soc. Perkin Trans., 1977, 2, 789, using tetrakis(triphenylphosphine)palladium(0) as catalyst, in the presence of sodium bicarbonate, as described, for example, in Palladium reagents and catalysts J. Tsuji, Wiley 1995, p 218, to afford the diaryl phosphonate 51.9. Deprotection, as described above, then affords the benzoic acid 51.10.

Using the above procedures, but employing, in place of the bromo compound 51.6, different bromo compounds 51.1, and/or different phosphonates 51.3, there are obtained the corresponding carboxylic acid products 51.5.

Scheme 47

Method

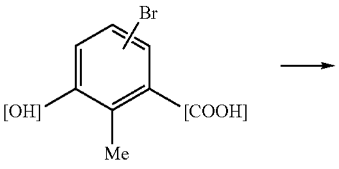

47.1

-continued
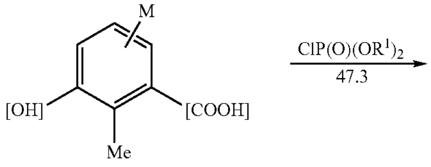
47.2
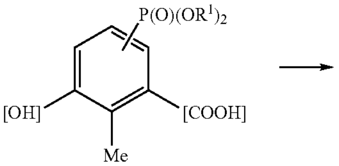
47.4
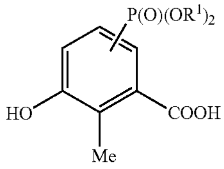
47.5
Example
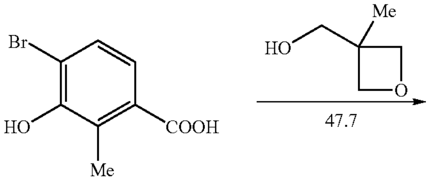
47.6
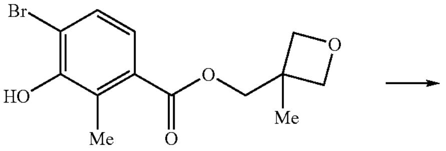
47.8
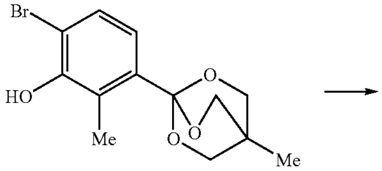
47.9
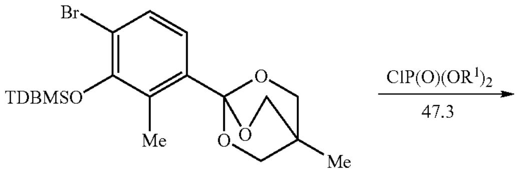
47.10
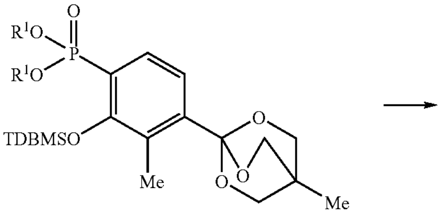
47.11
-continued
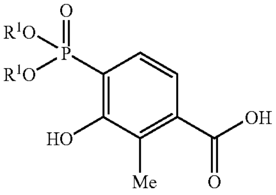
47.12
Scheme 48
Method
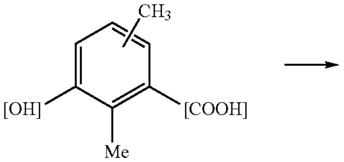
48.1
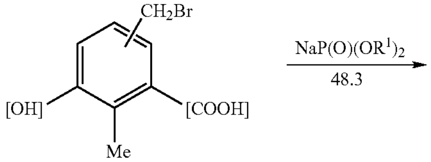
48.2
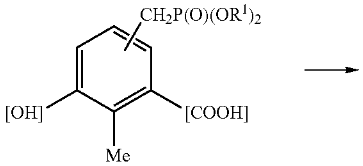
48.4
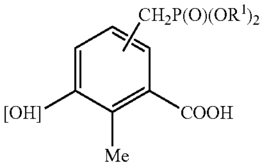
48.5
Example
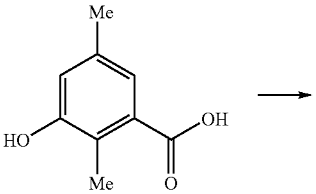
48.6

-continued
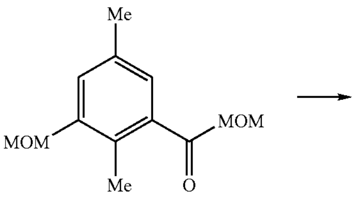
48.7
MOM = $CH_3OCH_2O$
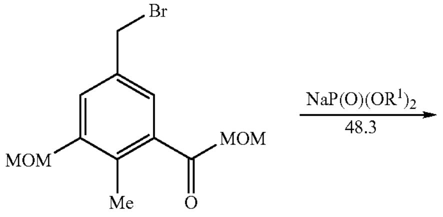
48.8
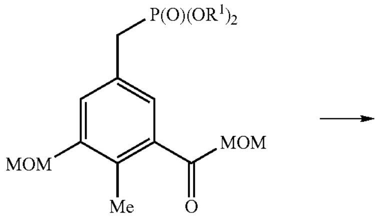
48.9
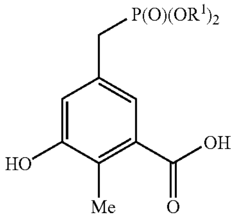
48.10
Scheme 49
Method
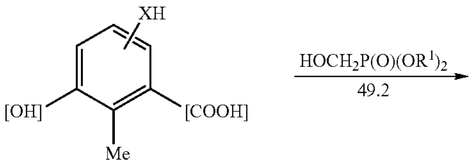
49.1
X = O, S
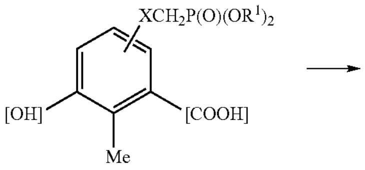
49.3
-continued
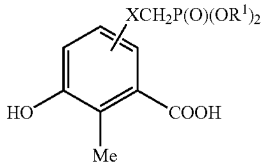
49.4
Example
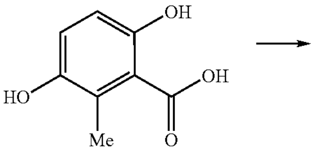
49.5
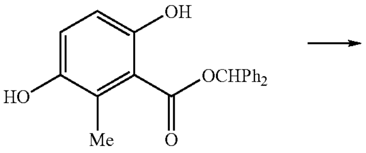
49.6
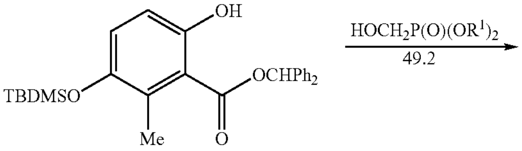
49.7
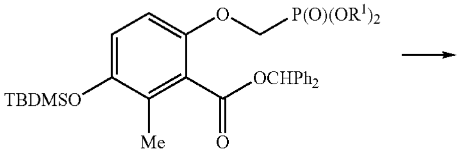
49.8
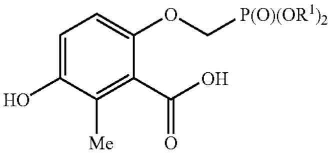
49.9
Scheme 50
Method
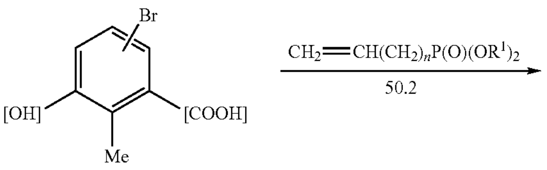
50.1

-continued
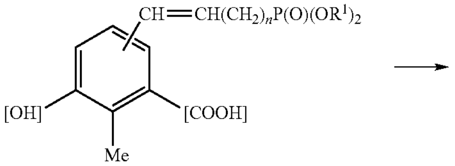
50.3
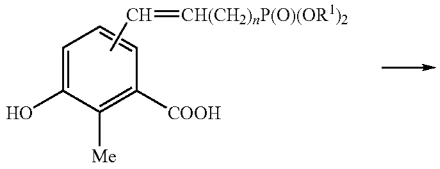
50.4
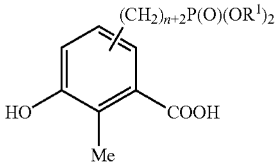
50.5
Example
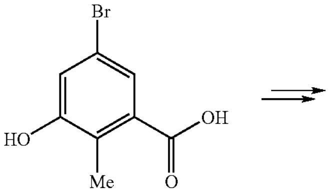
50.6
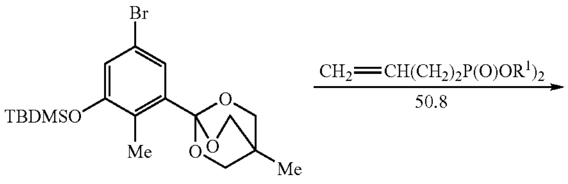
50.7
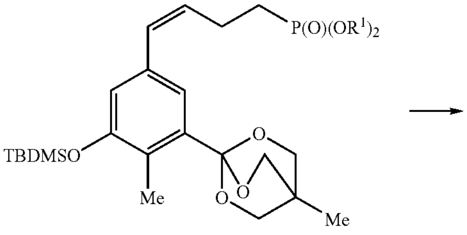
50.9
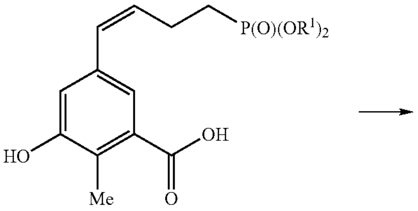
50.10
-continued
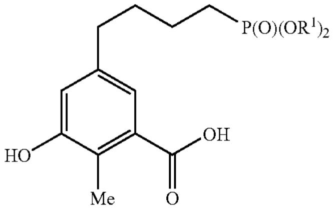
50.11
Scheme 51
Method
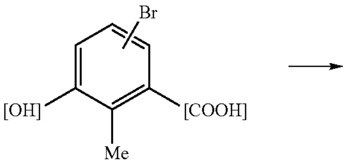
51.1
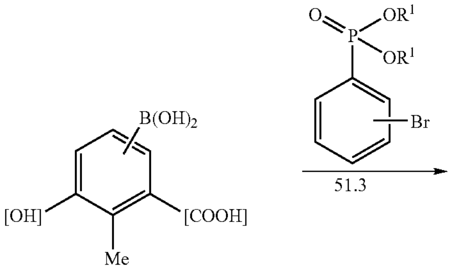
51.2
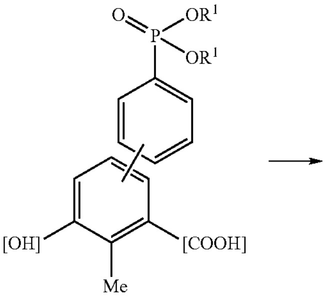
51.4
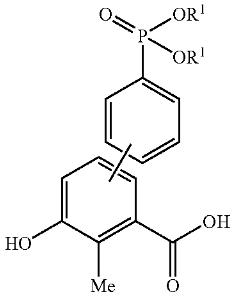
51.5

-continued

Example

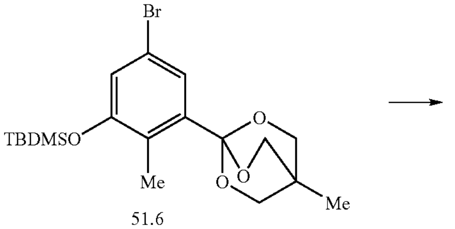

51.6

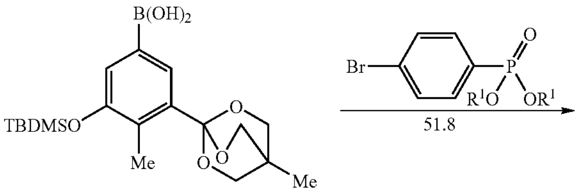

51.7

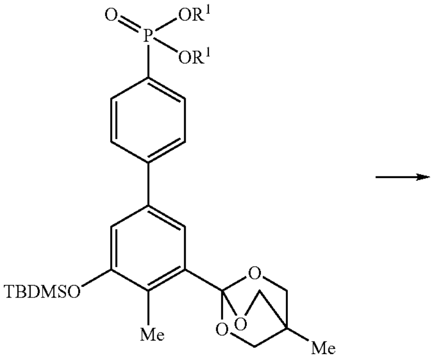

51.9

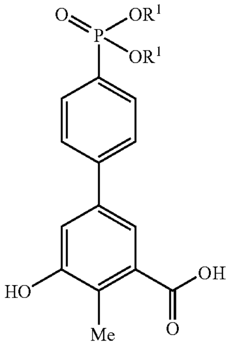

51.10

Preparation of Quinoline 2-Carboxylic Acids 43.6 Incorporating Phosphonate Moieties.

The reaction sequences depicted in Schemes 43-46 for the preparation of the phosphonate esters 10 employ a quinoline-2-carboxylic acid reactant 43.6 in which the substituent A is either the group link-P(O)($OR^1$)$_2$ or a precursor thereto, such as [OH], [SH] Br etc.

A number of suitably substituted quinoline-2-carboxylic acids are available commercially or are described in the chemical literature. For example, the preparations of 6-hydroxy, 6-amino and 6-bromoquinoline-2-carboxylic acids are described respectively in DE 3004370, J. Het. Chem., 1989, 26, 929 and J. Labelled Comp. Radiopharm., 1998, 41, 1103, and the preparation of 7-aminoquinoline-2-carboxylic acid is described in J. Am. Chem. Soc., 1987, 109, 620. Suitably substituted quinoline-2-carboxylic acids can also be prepared by procedures known to those skilled in the art. The synthesis of variously substituted quinolines is described, for example, in Chemistry of Heterocyclic Compounds, Vol. 32, G. Jones, ed., Wiley, 1977, p 93ff. Quinoline-2-carboxylic acids can be prepared by means of the Friedlander reaction, which is described in Chemistry of Heterocyclic Compounds, Vol. 4, R. C. Elderfield, ed., Wiley, 1952, p. 204.

Scheme 52 illustrates the preparation of quinoline-2-carboxylic acids by means of the Friedlander reaction, and further transformations of the products obtained. In this reaction sequence, a substituted 2-aminobenzaldehyde 52.1 is reacted with an alkyl pyruvate ester 52.2, in the presence of an organic or inorganic base, to afford the substituted quinoline-2-carboxylic ester 52.3. Hydrolysis of the ester, for example by the use of aqueous base, then afford the corresponding carboxylic acid 52.4. The carboxylic acid product 52.4 in which X is $NH_2$ can be further transformed into the corresponding compounds 52.6 in which Z is OH, SH or Br. The latter transformations are effected by means of a diazotization reaction. The conversion of aromatic amines into the corresponding phenols and bromides by means of a diazotization reaction is described respectively in Synthetic Organic Chemistry, R. B. Wagner, H. D. Zook, Wiley, 1953, pages 167 and 94; the conversion of amines into the corresponding thiols is described in Sulfur Lett., 2000, 24, 123. The amine is first converted into the diazonium salt by reaction with nitrous acid. The diazonium salt, preferably the diazonium tetrafluoborate, is then heated in aqueous solution, for example as described in Organic Functional Group Preparations, by S. R. Sandler and W. Karo, Academic Press, 1968, p. 83, to afford the corresponding phenol 52.6, Y=OH. Alternatively, the diazonium salt is reacted in aqueous solution with cuprous bromide and lithium bromide, as described in Organic Functional Group Preparations, by S. R. Sandler and W. Karo, Academic Press, 1968, p. 138, to yield the corresponding bromo compound, 52.6, Y=Br. Alternatively, the diazonium tetrafluoborate is reacted in acetonitrile solution with a sulfhydryl ion exchange resin, as described in Sulfur Lett., 2000, 24, 123, to afford the thiol 52.6, Y=SH. Optionally, the diazotization reactions described above can be performed on the carboxylic esters 52.3 instead of the carboxylic acids 52.5.

For example, 2,4-diaminobenzaldehyde 52.7 (Apin Chemicals) is reacted with one molar equivalent of methyl pyruvate 52.2 in methanol, in the presence of a base such as piperidine, to afford methyl-7-aminoquinoline-2-carboxylate 52.8. Basic hydrolysis of the product, employing one molar equivalent of lithium hydroxide in aqueous methanol, then yields the carboxylic acid 52.9. The amino-substituted carboxylic acid is then converted into the diazonium tetrafluoborate 52.10 by reaction with sodium nitrite and tetrafluoboric acid. The diazonium salt is heated in aqueous solution to afford the 7-hydroxyquinoline-2-carboxylic acid, 52.11, Z=OH. Alternatively, the diazonium tetrafluoborate is heated in aqueous organic solution with one molar equivalent of cuprous bromide and lithium bromide, to afford 7-bromoquinoline-2-carboxylic acid 52.11, Z=Br. Alternatively, the diazonium tetrafluoborate 52.10 is reacted in acetonitrile solution with the sulfhydryl form of an ion exchange resin, as described in Sulfur Lett., 2000, 24, 123, to prepare 7-mercaptoquinoline-2-carboxylic acid 52.11, Z=SH.

Using the above procedures, but employing, in place of 2,4-diaminobenzaldehyde 52.7, different aminobenzaldehydes 52.1, the corresponding amino, hydroxy, bromo or mercapto-substituted quinoline-2-carboxylic acids 52.6 are obtained. The variously substituted quinoline carboxylic acids and esters can then be transformed, as described herein, (Schemes 53-55) into phosphonate-containing derivatives.

Scheme 53 depicts the preparation of quinoline-2-carboxylic acids incorporating a phosphonate moiety attached to the quinoline ring by means of an oxygen or a sulfur atom. In this procedure, an amino-substituted quinoline-2-carboxylate ester 53.1 is transformed, via a diazotization procedure as described above (Scheme 52) into the corresponding phenol or thiol 53.2. The latter compound is then reacted with a dialkyl hydroxymethylphosphonate 53.3, under the conditions of the Mitsonobu reaction, to afford the phosphonate ester 53.4. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the ether or thioether products 53.4. Basic hydrolysis of the ester group, for example employing one molar equivalent of lithium hydroxide in aqueous methanol, then yields the carboxylic acid 53.5. The product is then coupled with a suitably protected aminoacid derivative 53.6 to afford the amide 53.7. The reaction is performed under similar conditions to those described above, Scheme 1. The ester protecting group is then removed to yield the carboxylic acid 53.8.

For example, methyl 6-amino-2-quinoline carboxylate 53.9, prepared as described in J. Het. Chem., 1989, 26, 929, is converted, by means of the diazotization procedure described above, into methyl 6-mercaptoquinoline-2-carboxylate 53.10. This material is reacted with a dialkyl hydroxymethylphosphonate 53.11 (Aldrich) in the presence of diethyl azodicarboxylate and triphenylphosphine in tetrahydrofuran solution, to afford the thioether 53.12. Basic hydrolysis then afford the carboxylic acid 53.13. The latter compound is then converted, as described above, into the aminoacid derivative 53.16.

Using the above procedures, but employing, in place of methyl 6-amino-2-quinoline carboxylate 53.9, different aminoquinoline carboxylic esters 53.1, and/or different dialkyl hydroxymethylphosphonates 53.3 the corresponding phosphonate ester products 53.8 are obtained.

Scheme 54 illustrates the preparation of quinoline-2-carboxylic acids incorporating phosphonate esters attached to the quinoline ring by means of a saturated or unsaturated carbon chain. In this reaction sequence, a bromo-substituted quinoline carboxylic ester 54.1 is coupled, by means of a palladium-catalyzed Heck reaction, with a dialkyl alkenylphosphonate 54.2. The coupling of aryl halides with olefins by means of the Heck reaction is described, for example, in Advanced Organic Chemistry, by F. A. Carey and R. J. Sundberg, Plenum, 2001, p. 503ff. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Thus, Heck coupling of the bromo compound 54.1 and the olefin 54.2 affords the olefinic ester 54.3. Hydrolysis, for example by reaction with lithium hydroxide in aqueous methanol, or by treatment with porcine liver esterase, then yields the carboxylic acid 54.4. The latter compound is then transformed, as described above, into the homolog 54.5. Optionally, the unsaturated carboxylic acid 54.4 can be reduced to afford the saturated analog 54.6. The reduction reaction can be effected chemically, for example by the use of diimide or diborane, as described in Comprehensive Organic Transformations, by R. C. Larock, VCH, 1989, p. 5, or catalytically. The product 54.6 is then converted, as described above (Scheme 53) into the aminoacid derivative 54.7.

For example, methyl 7-bromoquinoline-2-carboxylate, 54.8, prepared as described in J. Labelled Comp. Radiopharm., 1998, 41, 1103, is reacted in dimethylformamide at 60° with a dialkyl vinylphosphonate 54.9 (Aldrich) in the presence of 2 mol % of tetrakis(triphenylphosphine)palladium and triethylamine, to afford the coupled product 54.10 The product is then reacted with lithium hydroxide in aqueous tetrahydrofuran to produce the carboxylic acid 54.11. The latter compound is reacted with diimide, prepared by basic hydrolysis of diethyl azodicarboxylate, as described in Angew. Chem. Int. Ed., 4, 271, 1965, to yield the saturated product 54.12. The latter compound is then converted, as described above, into the aminoacid derivative 54.13. The unsaturated product 54.11 is similarly converted into the analog 54.14.

Using the above procedures, but employing, in place of methyl 6-bromo-2-quinolinecarboxylate 54.8, different bromoquinoline carboxylic esters 54.1, and/or different dialkyl alkenylphosphonates 54.2, the corresponding phosphonate ester products 54.5 and 54.7 are obtained.

Scheme 52

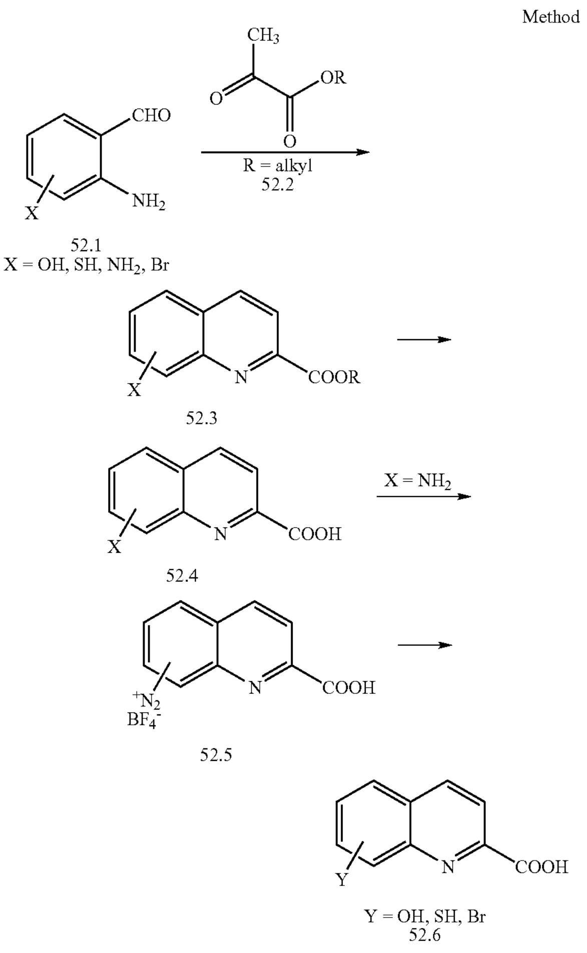

-continued
Example
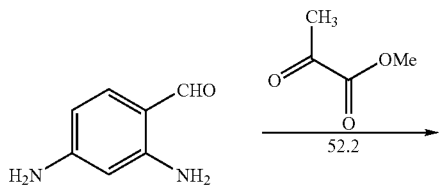
52.7
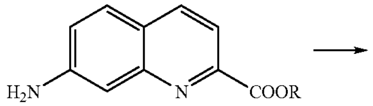
52.8
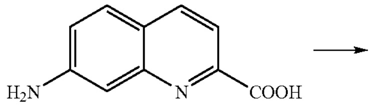
52.9
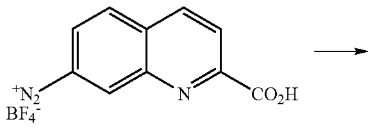
52.10
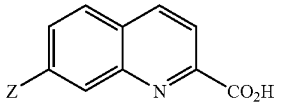
Z = OH, SH, Br
52.11
Scheme 53
Method
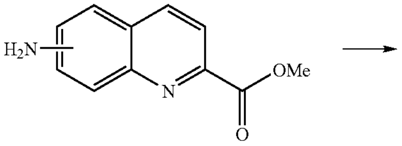
53.1
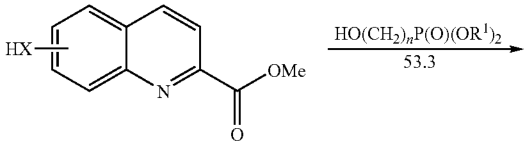
X = O, S
53.2
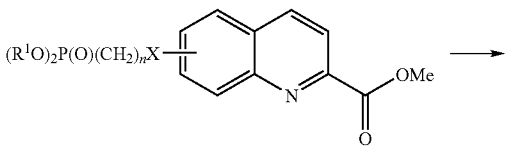
53.4
-continued
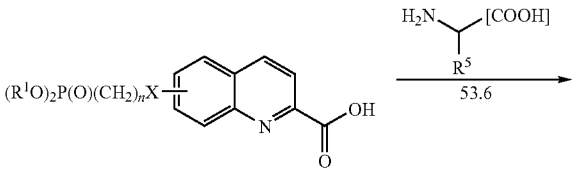
53.5
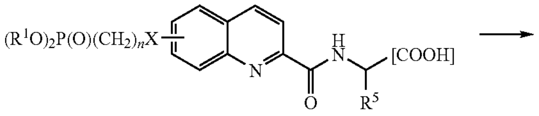
53.7
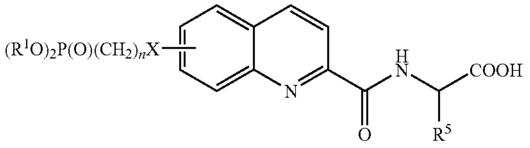
53.8
Example
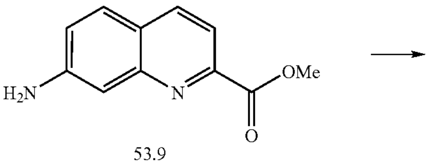
53.9
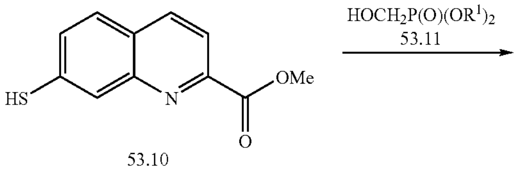
53.10
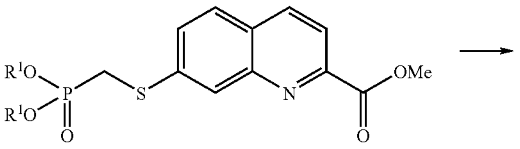
53.12
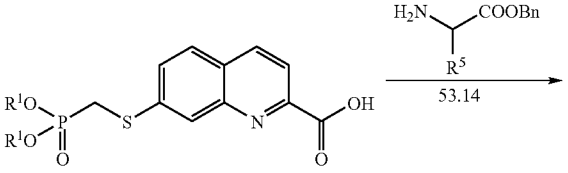
53.13
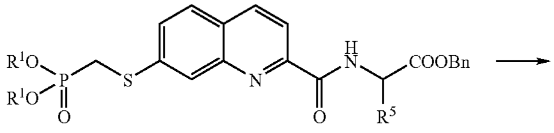
53.15
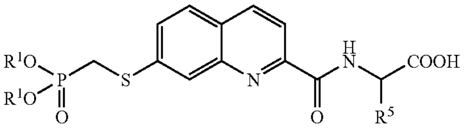
53.16

Scheme 54
Method
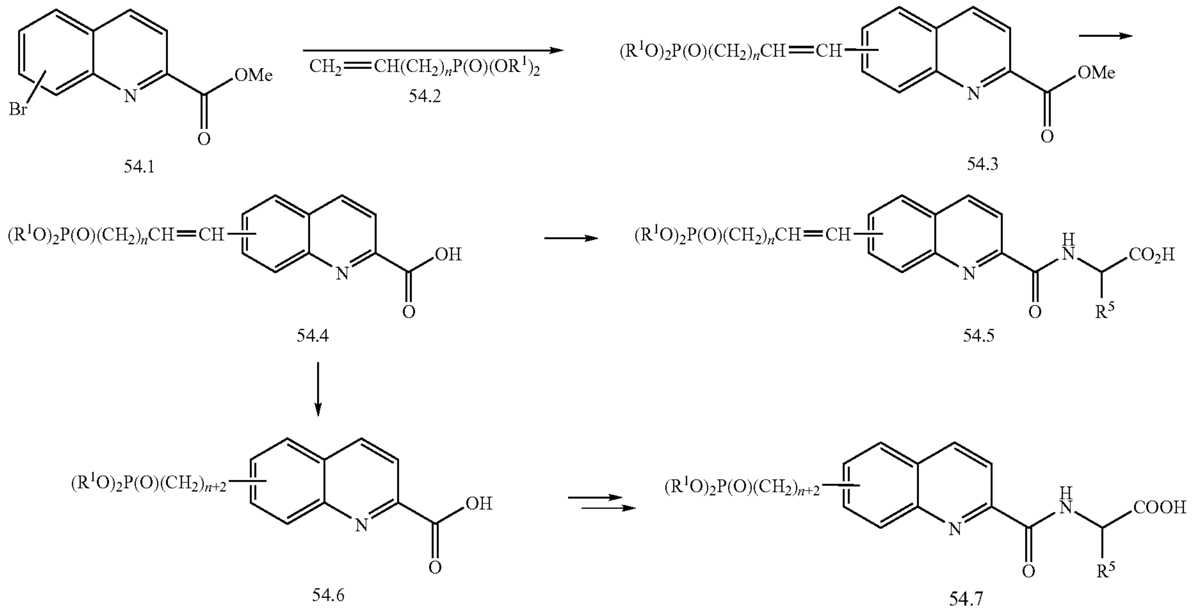
Example
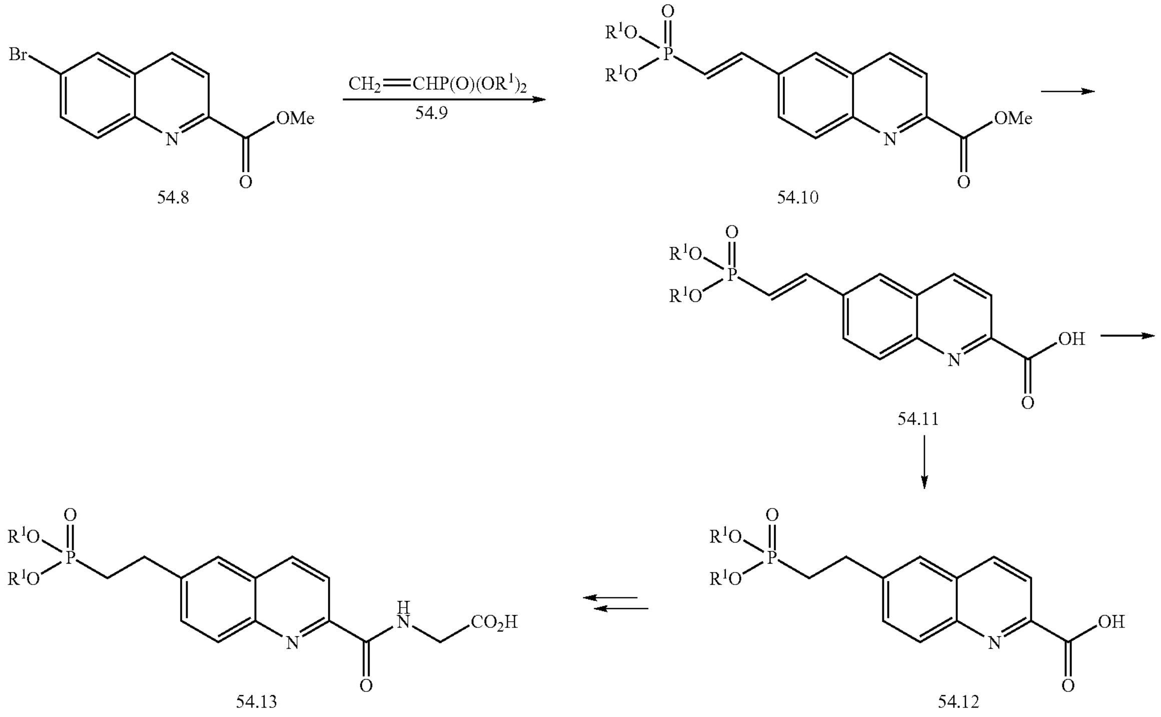

-continued

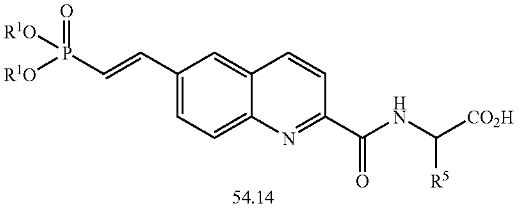

54.14

Scheme 55 depicts the preparation of quinoline-2-carboxylic acid derivatives 55.5 in which the phosphonate group is attached by means of a nitrogen atom and an alkylene chain. In this reaction sequence, a methyl aminoquinoline-2-carboxylate 55.1 is reacted with a phosphonate aldehyde 55.2 under reductive amination conditions, to afford the aminoalkyl product 55.3. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The ester product 55.3 is then hydrolyzed to yield the free carboxylic acid 55.4. The latter compound is then converted, as described above, into the aminoacid derivative 55.5.

For example, methyl 7-aminoquinoline-2-carboxylate 55.6, prepared as described in J. Am. Chem. Soc., 1987, 109, 620, is reacted with a dialkyl formylmethylphosphonate 55.7 (Aurora) in methanol solution in the presence of sodium borohydride, to afford the alkylated product 55.8. The ester is then hydrolyzed, as described above, to yield the carboxylic acid 55.9. The latter compound is then converted, as described above, into the aminoacid derivative 55.10. Using the above procedures, but employing, in place of the formylmethyl phosphonate 55.7, different formylalkyl phosphonates 55.2, and/or different aminoquinolines 55.1, the corresponding products 55.5 are obtained.

Scheme 55

Method

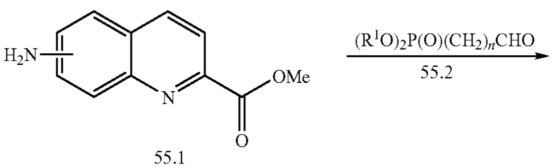

55.1

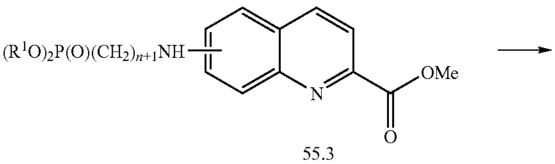

55.3

-continued

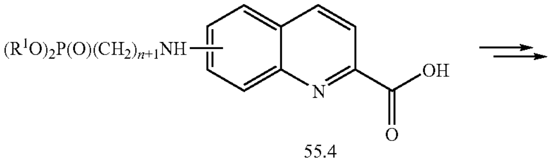

55.4

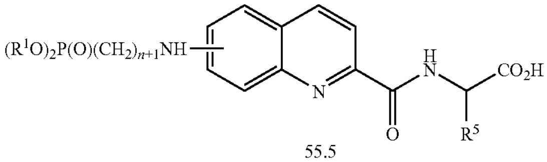

55.5

Example

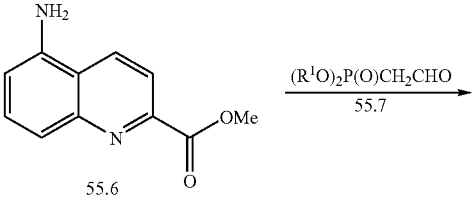

55.6

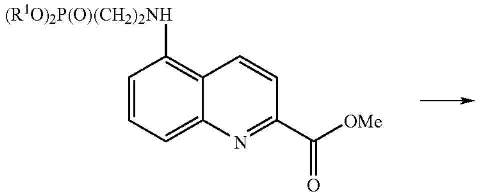

55.8

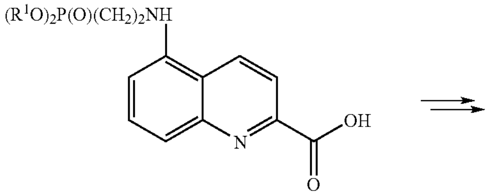

55.9

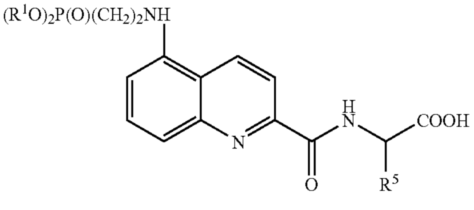

55.10

Preparation of Phenylalanine Derivatives 1.1 Incorporating Phosphonate Moieties.

Scheme 56 illustrates the conversion of variously substituted phenylalanine derivatives 56.1 into epoxides 1.1, the incorporation of which into the compounds 1 is depicted in Schemes 1 and 3.

A number of compounds 56.1 or 56.2, for example those in which X is 2, 3, or 4-OH, or X is 4-$NH_2$ are commercially available. The preparations of different compounds 56.1 or 56.2 are described in the literature. For example, the preparation of compounds 56.1 or 56.2 in which X is 3-SH, 4-SH, 3-$NH_2$, 3-$CH_2OH$ or 4-$CH_2OH$, are described respectively in WO0036136, J. Am. Chem. Soc., 1997, 119, 7173, Helv. Chim. Acta, 1978, 58, 1465, Acta Chem. Scand., 1977, B31, 109 and Syn. Corn., 1998, 28, 4279. Resolution of compounds 56.1, if required, can be accomplished by conventional methods, for example as described in Recent Dev. Synth. Org. Chem., 1992, 2, 35.

The variously substituted aminoacids 56.2 are protected, for example by conversion to the BOC derivative 56.3, by treatment with BOC anhydride, as described in J. Med. Chem., 1998, 41, 1034. The product 56.3 is then converted into the methyl ester 56.4, for example by treatment with ethereal diazomethane. The substituent X in 56.4 is then transformed, using the methods described below, Schemes 57-59, into the group A. The products 56.5 are then converted, via the intermediates 56.6-56.9, into the epoxides 1.1. The methyl ester 56.5 is first hydrolyzed, for example by treatment with one molar equivalent of aqueous methanolic lithium hydroxide, or by enzymatic hydrolysis, using, for example, porcine liver esterase, to afford the carboxylic acid 56.6. The conversion of the carboxylic acid 56.6 into the epoxide 1.1, for example using the sequence of reactions which is described in J. Med. Chem., 1994, 37, 1758, is then effected. The carboxylic acid is first converted into the acid chloride, for example by treatment with oxalyl chloride, or into a mixed anhydride, for example by treatment with isobutyl chloroformate, and the activated derivative thus obtained is reacted with ethereal diazomethane, to afford the diazoketone 56.7. The diazoketone is converted into the chloroketone 56.8 by reaction with anhydrous hydrogen chloride, in a suitable solvent such as diethyl ether. The latter compound is then reduced, for example by the use of sodium borohydride, to produce a mixture of chlorohydrins from which the desired 2S, 3S diastereomer 56.9 is separated by chromatography. This material is reacted with ethanolic potassium hydroxide at ambient temperature to afford the epoxide 1.1. Optionally, the above described series of reactions can be performed on the methyl ester 56.4, so as to yield the epoxide 1.1 in which A is OH, SH, NH, Nalkyl or $CH_2OH$.

Methods for the transformation of the compounds 56.4, in which X is a precursor group to the substituent link-P(O)$(OR^1)_2$, are illustrated in Schemes 57-59.

Scheme 56a illustrates the conversion of variously substituted phenylalanine derivatives 56a.1 into epoxides 3.1, the incorporation of which into the compounds 1 is depicted in Schemes 3. Starting from the same reagents described above, Scheme 56, the compound 56.2 is converted into the epoxide 56a.6 as described in J. Org. Chem 1996,61, 3635. The amino acid 56.2 is converted to the tribenzyl ester 56a.3 by treatment with benzyl bromide in ethanol in the presence of potassium carbonate. The substituent X in 56a.3 is then transformed, using the methods described below, Schemes 57-59, into the group A, compound 56a.4. These methods describe procedures in which the amine is BOC protected. However the same procedures are applicable to other amine protecting groups such as dibenzyl. The products 56a.4 are then converted, via the intermediates 56a.5 into the epoxides 3.1. The ester 56a.4 is reduced with lithium aluminum hydride to the alcohol which is then oxidized to the aldehyde 56a.4 by treatment with pyridine sulfur trioxide in DMSO and triethylamine. The aldehyde 56a.4 is then converted to the epoxide 3.1 by treatment with chloromethylbromide and excess lithium in THF at −65° C. A mixture of isomers are produced which are separated by chromatography.

Scheme 57 depicts the preparation of epoxides 57.4 incorporating a phosphonate group linked to the phenyl ring by means of a heteroatom O, S or N. In this procedure, the phenol, thiol, amine or carbinol 57.1 is reacted with a derivative of a dialkyl hydroxymethyl phosphonate 57.2. The reaction is accomplished in the presence of a base, the nature of which depends on the nature of the substituent X. For example, if X is OH, SH, $NH_2$ or NHalkyl, an inorganic base such as cesium carbonate, or an organic base such as diazabicyclononene, can be employed. If X is $CH_2OH$, a base such as lithium hexamethyldisilylazide or the like can be employed. The condensation reaction affords the phosphonate-substituted ester 57.3, which, employing the sequence of reactions shown in Scheme 56 or 56a, is transformed into the epoxide 57.4.

For example, 2-tert.-butoxycarbonylamino-3-(4-hydroxy-phenyl)-propionic acid methyl ester, 57.5 (Fluka) is reacted with a dialkyl trifluoromethanesulfonyloxy phosphonate 57.6, prepared as described in Tet. Lett., 1986, 27, 1477, in the presence of cesium carbonate, in dimethylformamide at ca 60°, to afford the ether product 57.5. The latter compound is then converted, using the sequence of reactions shown in Scheme 56, into the epoxide 57.8.

Using the above procedures, but employing different phenols, thiols, amines and carbinols 57.1 in place of 57.5, and/or different phosphonates 57.2, the corresponding products 57.4 are obtained.

Scheme 58 illustrates the preparation of a phosphonate moiety is attached to the phenylalanine scaffold by means of a heteroatom and a multi-carbon chain.

In this procedure, a substituted phenylalanine derivative 58.1 is reacted with a dialkyl bromoalkyl phosphonate 58.2 to afford the product 58.3. The reaction is conducted in a polar organic solvent such as dimethylformamide or acetonitrile, in the presence of a suitable base such as sodium hydride or cesium carbonate. The product is then transformed, using the sequence of reactions shown in Scheme 56, into the epoxide 58.4.

For example, the protected aminoacid 58.5, prepared as described above (Scheme 56) from 3-mercaptophenylalanine, the preparation of which is described in WO 0036136, is reacted with a dialkyl 2-bromoethyl phosphonate 58.6, prepared as described in Synthesis, 1994, 9, 909, in the presence of cesium carbonate, in dimethylformamide at ca 60°, to afford the thioether product 58.7. The latter compound is then converted, using the sequence of reactions shown in Scheme 56, into the epoxide 58.8.

Using the above procedures, but employing different phenols, thiols, and amines 58.1 in place of 58.5, and/or different phosphonates 58.2, the corresponding products 58.4 are obtained.

Scheme 59 depicts the preparation of phosphonate-substituted phenylalanine derivatives in which the phosphonate moiety is attached by means of an alkylene chain incorporating a heteroatom.

In this procedure, a protected hydroxymethyl-substituted phenylalanine 59.1 is converted into the halomethyl-substituted compound 59.2. For example, the carbinol 59.1 is treated with triphenylphosphine and carbon tetrabromide, as described in J. Am. Chem. Soc., 108, 1035, 1986 to afford the product 59.2 in which Z is Br. The bromo compound is then reacted with a dialkyl terminally hetero-substituted alkylphosphonate 59.3. The reaction is accomplished in the presence of a base, the nature of which depends on the nature of the substituent X. For example, if X is SH, $NH_2$ or NHalkyl, an inorganic base such as cesium carbonate, or an organic base such as diazabicyclononene, can be employed. If X is OH, a strong base such as lithium hexamethyldisilylazide or the like can be employed. The condensation reaction affords the phosphonate-substituted ester 59.4, which, employing the sequence of reactions shown in Scheme 56, is transformed into the epoxide 59.5.

For example, the protected 4-hydroxymethyl-substituted phenylalanine derivative 59.6, obtained from the 4-hydroxymethyl phenylalanine, the preparation of which is described in Syn. Comm., 1998, 28, 4279, is converted into the bromo derivative 59.7, as described above. The product is then reacted with a dialkyl 2-aminoethyl phosphonate 59.8, the preparation of which is described in J. Org. Chem., 2000, 65, 676, in the presence of cesium carbonate in dimethylformamide at ambient temperature, to afford the amine product 59.9. The latter compound is then converted, using the sequence of reactions shown in Scheme 56, into the epoxide 59.10.

Using the above procedures, but employing different carbinols 59.1 in place of 59.6, and/or different phosphonates 59.3, the corresponding products 59.5 are obtained.

Scheme 56

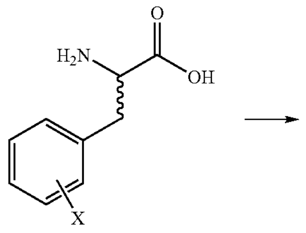

56.1

X = OH, SH, $NH_2$, NHalkyl, $CH_2OH$

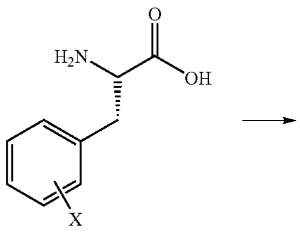

56.2

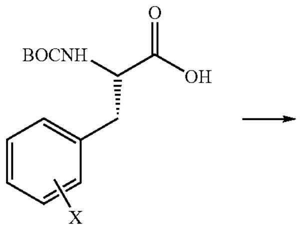

56.3

-continued

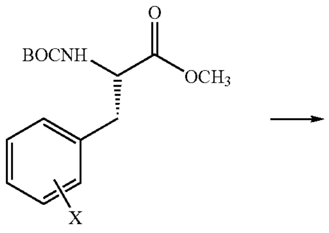

56.4

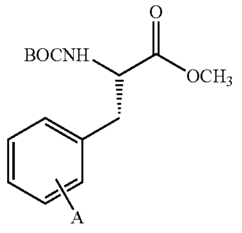

56.5

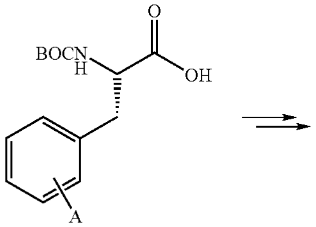

56.6

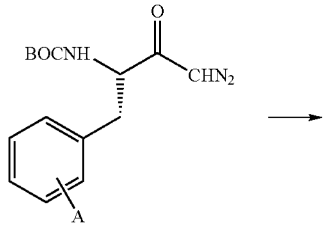

56.7

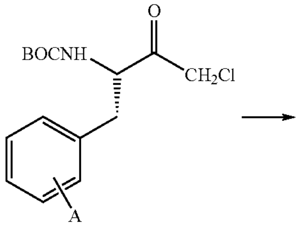

56.8

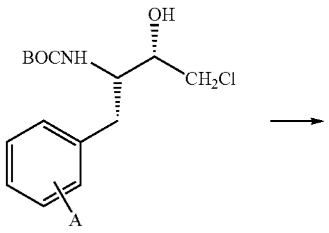

56.9

-continued
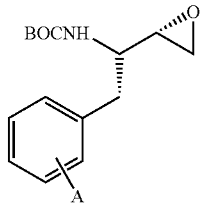
1.1
Scheme 57
Method
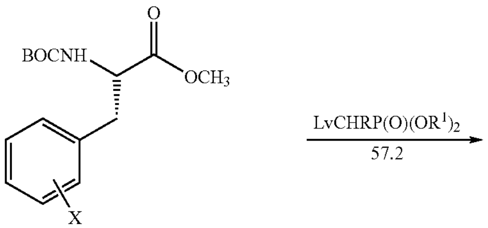
57.1
X = OH, SH, $NH_2$, NHalkyl, $CH_2OH$
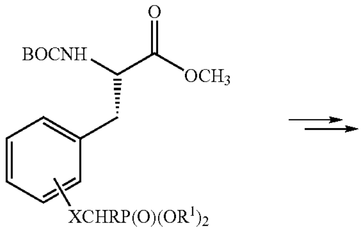
57.3
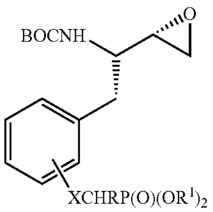
57.4
Example
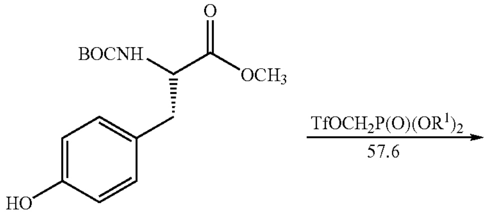
57.5
-continued
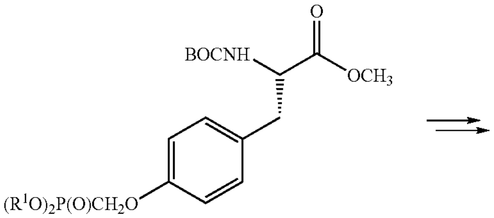
57.7
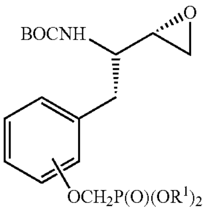
57.8
Scheme 56a
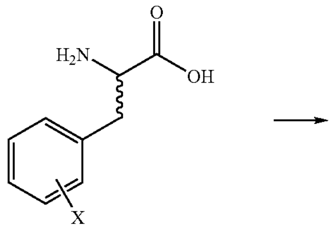
56.1
X = OH, SH, $NH_2$, NHalkyl, $CH_2OH$
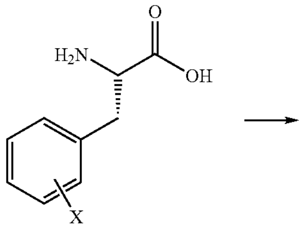
56.2
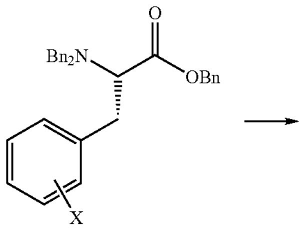
56a.3

-continued
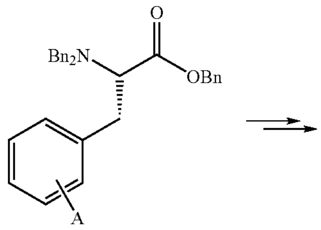
56a.4
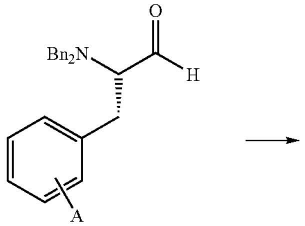
56a.5
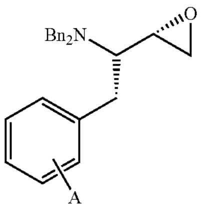
3.1
Scheme 58
Method
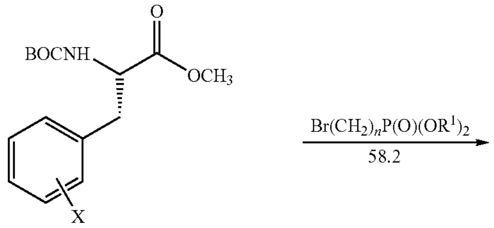
X = OH, SH, $NH_2$, NHalkyl
58.1
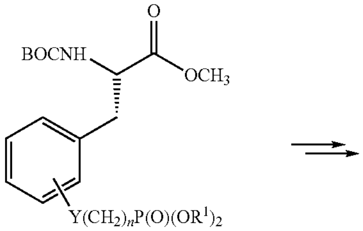
Y = O, S, NH, Nalkyl
58.3
-continued
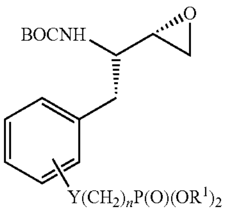
58.4
Example
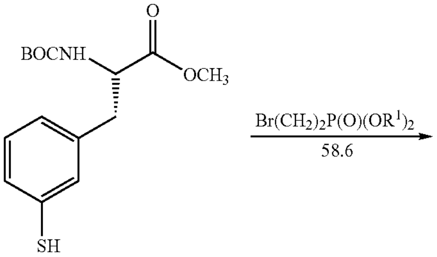
58.5
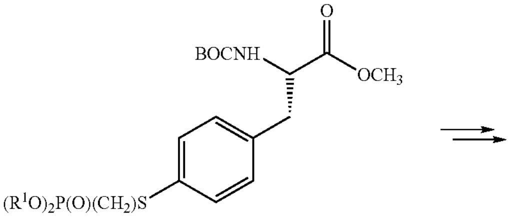
58.7
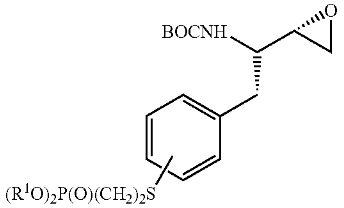
58.8
Scheme 59
Method
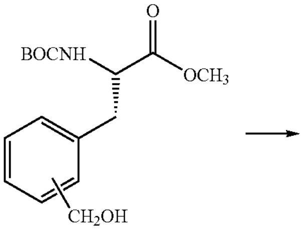
59.1

-continued

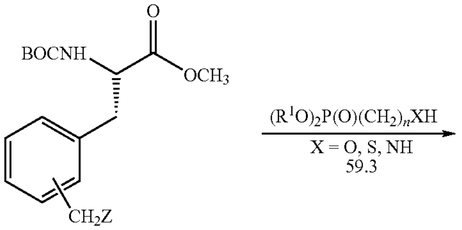

Z = Cl, Br
59.2

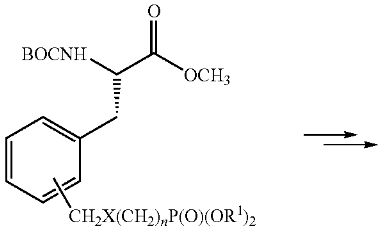

59.4

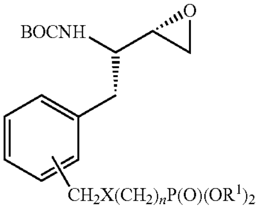

59.5

Example

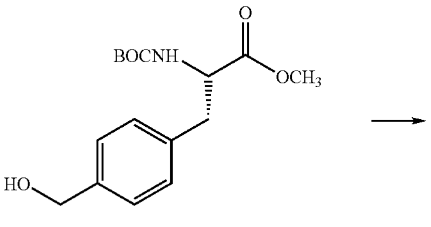

59.6

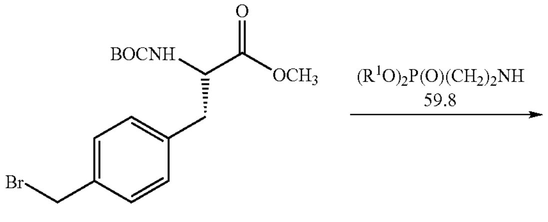

59.7

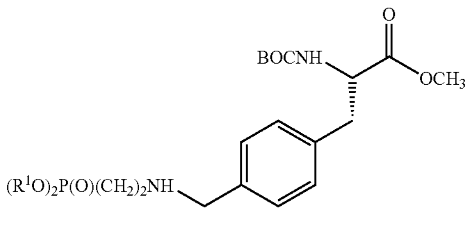

59.9

-continued

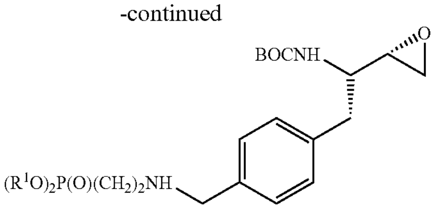

59.10

Preparation of Phenylalanine Derivatives 2.1 Incorporating Phosphonate Moieties or Precursors Thereto.

Scheme 60 illustrates the preparation of the hydroxymethyl oxazolidine derivative 2.1, in which the substituent A is either the group link-$P(O)(OR^1)_2$ or a precursor thereto, such as [OH], [SH] Br etc. In this reaction sequence, the substituted phenylalanine 60.1, in which A is as defined above, is transformed, via the intermediates 60.2-60.9, into the hydroxymethyl product 2.1. In this procedure, phenylalanine, or a substituted derivative thereof, 60.1, is converted into the phthalimido derivative 60.2. The conversion of amines into phthalimido derivatives is described, for example, in Protective Groups in Organic Synthesis, by T. W. Greene and P. G. M Wuts, Wiley, Second Edition 1990, p. 358. The amine is reacted with phthalic anhydride, 2-carboethoxybenzoyl chloride or N-carboethoxyphthalimide, optionally in the presence of a base such as triethylamine or sodium carbonate, to afford the protected amine 60.2. Preferably, the aminoacid is reacted with phthalic anhydride in toluene at reflux, to yield the phthalimido product. The carboxylic acid is then transformed into an activated derivative such as the acid chloride 60.3, in which X is Cl. The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of a tertiary amide such as dimethylformamide. Preferably, the carboxylic acid is transformed into the acid chloride by reaction with oxalyl chloride and a catalytic amount of dimethylformamide, in toluene solution at ambient temperature, as described in WO 9607642. The acid chloride 60.3, X═Cl, is then converted into the aldehyde 60.4 by means of a reduction reaction. This procedure is described, for example, in Comprehensive Organic Transformations, by R. C. Larock, VCH, 1989, p. 620. The transformation can be effected by means of catalytic hydrogenation, a procedure which is referred to as the Rosenmund reaction, or by chemical reduction employing, for example, sodium borohydride, lithium aluminum tri-tertiarybutoxy hydride or triethylsilane. Preferably, the acid chloride 60.3 X═Cl, is hydrogenated in toluene solution over a 5% palladium on carbon catalyst, in the presence of butylene oxide, as described in WO 9607642, to afford the aldehyde 60.4. The aldehyde 60.4 is then transformed into the cyanohydrin derivative 60.5. The conversion of aldehydes into cyanohydrins is described in Protective Groups in Organic Synthesis, by T. W. Greene and P. G. M Wuts, Wiley, Second Edition 1990, p. 211. For example, the aldehyde 60.4 is converted into the cyanohydrin 60.5 by reaction with trimethylsilyl cyanide in an inert solvent such as dichloromethane, followed by treatment with an organic acid such as citric acid, as described in WO 9607642, or by alternative methods described therein. The cyanohydrin is then subjected to acidic hydrolysis, to effect conversion of the cyano group into the corresponding carboxy group, with concomitant hydrolysis of the phthalimido substituent to afford the aminoacid 60.6 The hydrolysis reactions are effected by the use of aqueous mineral acid. For example, the substrate 60.5 is reacted with aqueous hydrochloric acid at reflux, as described in WO 9607642, to afford the carboxylic acid product 60.6. The aminoacid is then converted into a carbamate, for example the ethyl carbamate 60.7. The conversion of amines into carbamates is described in Protective Groups in Organic Synthesis, by T. W. Greene and P. G. M Wuts, Wiley, Second Edition 1990, p. 317. The amine is reacted with a chloroformate, for example ethyl chloroformate, in the presence of a base such as potassium carbonate, to afford the carbamate 60.7. For example, the aminoacid 60.6 is reacted, in aqueous solution, with ethyl chloroformate and sufficient aqueous sodium hydroxide to maintain a neutral pH, as described in WO 9607642, to afford the carbamate 60.7. The latter compound is then transformed into the oxazolidinone 60.8, for example by treatment with aqueous sodium hydroxide at ambient temperature, as described in WO 9607642. The resultant carboxylic acid is transformed into the methyl ester 60.9 by means of a conventional esterification reaction. The conversion of carboxylic acids into esters is described for example, in Comprehensive Organic Transformations, by R. C. Larock, VCH, 1989, p. 966. The conversion can be effected by means of an acid-catalyzed reaction between the carboxylic acid and an alcohol, or by means of a base-catalyzed reaction between the carboxylic acid and an alkyl halide, for example an alkyl bromide. For example, the carboxylic acid 60.8 is converted into the methyl ester 60.9 by treatment with methanol at reflux temperature, in the presence of a catalytic amount of sulfuric acid, as described in WO 9607642. The carbomethoxyl group present in the compound 60.9 is then reduced to yield the corresponding carbinol 2.1. The reduction of carboxylic esters to the carbinols is described in Comprehensive Organic Transformations, by R. C. Larock, VCH, 1989, p. 550. The transformation can be effected by the use of reducing agents such as borane-dimethylsulfide, lithium borohydride, diisobutyl aluminum hydride, lithium aluminum hydride and the like. For example, the ester 60.9 is reduced to the carbinol 2.1 by reaction with sodium borohydride in ethanol at ambient temperature, as described in WO 9607642.

The conversion of the substituent A into the group link-P(O)($OR^1$)$_2$ may be effected at any convenient step in the reaction sequence, or after the reactant 2.1 has been incorporated into the intermediates 1. Specific examples of the preparation of the hydroxymethyl oxazolidinone reactant 2.1 are shown below, (Schemes 61-62)

Scheme 61 depicts the preparation of hydroxymethyloxazolidinones 61.9 in which the phosphonate ester moiety is attached directly to the phenyl ring. In this procedure, a bromo-substituted phenylalanine 61.1 is converted, using the series of reactions illustrated in Scheme 60, into the bromophenyloxazolidinone 61.2. The bromophenyl compound is then coupled, in the presence of a palladium (0) catalyst, with a dialkyl phosphite 61.3, to afford the phosphonate product 61.4. The reaction between aryl bromide and dialkyl phosphites to yield aryl phosphonates is described in Synthesis, 56, 1981, and in J. Med. Chem., 1992, 35, 1371. The reaction is conducted in an inert solvent such as toluene or xylene, at about 100°, in the presence of a palladium(0) catalyst such as tetrakis(triphenylphosphine)palladium and a tertiary organic base such as triethylamine. The carbomethoxy substituent in the resultant phosphonate ester 61.4 is then reduced with sodium borohydride to the corresponding hydroxymethyl derivative 61.5, using the procedure described above (Scheme 60) For example, 3-bromophenylalanine 61.6, prepared as described in Pept. Res., 1990, 3, 176, is converted, using the sequence of reactions shown in Scheme 60, into 4-(3-bromo-benzyl)-2-oxo-oxazolidine-5-carboxylic acid methyl ester 61.7. This compound is then coupled with a dialkyl phosphite 61.3, in toluene solution at reflux, in the presence of a catalytic amount of tetrakis(triphenylphosphine)palladium(0) and triethylamine, to afford the phosphonate ester 61.8. The carbomethoxy substituent is then reduced with sodium borohydride, as described above, to afford the hydroxymethyl product 61.9.

Using the above procedures, but employing, in place of 3-bromophenylalanine 61.6 different bromophenylalanines 61.1 and/or different dialkyl phosphites 61.3, the corresponding products 61.5 are obtained.

Scheme 62 illustrates the preparation of phosphonate-containing hydroxymethyl oxazolidinones 62.9 and 62.12 in which the phosphonate group is attached by means of a heteroatom and a carbon chain. In this sequence of reactions, a hydroxy or thio-substituted phenylalanine 62.1 is converted into the benzyl ester 62.2 by means of a conventional acid catalyzed esterification reaction. The hydroxyl or mercapto group is then protected. The protection of phenyl hydroxyl and thiol groups are described, respectively, in Protective Groups in Organic Synthesis, by T. W. Greene and P. G. M Wuts, Wiley, Second Edition 1990, p. 10, and p. 277. For example, hydroxyl and thiol substituents can be protected as trialkylsilyloxy groups. Trialkylsilyl groups are introduced by the reaction of the phenol or thiophenol with a chlorotrialkylsilane and a base such as imidazole, for example as described in Protective Groups in Organic Synthesis, by T. W. Greene and P. G. M Wuts, Wiley, Second Edition 1990, p. 10, p. 68-86. Alternatively, thiol substituents can be protected by conversion to tert-butyl or adamantyl thioethers, or 4-methoxybenzyl thioethers, prepared by the reaction between the thiol and 4-methoxybenzyl chloride in the presence of ammonium hydroxide, as described in Bull. Chem. Soc. Jpn., 37, 433, 1974. The protected ester 62.3 is then reacted with phthalic anhydride, as described above (Scheme 60) to afford the phthalimide 62.4. The benzyl ester is then removed, for example by catalytic hydrogenation or by treatment with aqueous base, to afford the carboxylic acid 62.5. This compound is transformed, by means of the series of reactions shown in Scheme 60, into the carbomethoxy oxazolidinone 62.6, using in each step the same conditions as are described above (Scheme 60). The protected OH or SH group is then deprotected. Deprotection of phenols and thiophenols is described in Protective Groups in Organic Synthesis, by T. W. Greene and P. G. M Wuts, Wiley, Second Edition 1990, p. For example, trialkylsilyl ethers or thioethers can be deprotected by treatment with a tetraalkylammonium fluoride in an inert solvent such as tetrahydrofuran, as described in J. Am Chem. Soc., 94, 6190, 1972. Tert-butyl or adamantyl thioethers can be converted into the corresponding thiols by treatment with mercuric trifluoroacetate in aqueous acetic acid at ambient temperatures, as described in Chem. Pharm. Bull., 26, 1576, 1978. The resultant phenol or thiol 62.7 is then reacted with a hydroxyalkyl phosphonate 62.20 under the conditions of the Mitsonobu reaction, as described above (Scheme 49), to afford the ether or thioether 62.8. The latter compound is then reduced with sodium borohydride, as described above (Scheme 60) to afford the hydroxymethyl analog 62.9.

Alternatively, the phenol or thiophenol 62.7 is reacted with a dialkyl bromoalkyl phosphonate 62.10 to afford the alkylation product 62.11. The alkylation reaction is performed in a polar organic solvent such as dimethylformamide, acetonitrile and the like, optionally in the presence of potassium iodide, and in the presence of an inorganic base such as potassium or cesium carbonate, or an organic base such as diazabicyclononene or dimethylaminopyridine. The ether or thioether product is then reduced with sodium borohydride to afford the hydroxymethyl compound 62.12.

For example, 3-hydroxyphenylalanine 62.13 (Fluka) is converted in to the benzyl ester 62.14 by means of a conventional acid-catalyzed esterification reaction. The ester is then reacted with tert-butylchlorodimethylsilane and imidazole in dimethylformamide, to afford the silyl ether 62.15. The protected ether is then reacted with phthalic anhydride, as described above (Scheme 60) to yield the phthalimido-protected compound 62.16. Basic hydrolysis, for example by reaction with lithium hydroxide in aqueous methanol, then affords the carboxylic acid 62.17. This compound is then transformed, by means of the series of reactions shown in Scheme 60, into the carbomethoxy-substituted oxazolidinone 62.18. The silyl protecting group is then removed by treatment with tetrabutylammonium fluoride in tetrahydrofuran at ambient temperature, to produce the phenol 62.19. The latter compound is reacted with a dialkyl hydroxymethyl phosphonate 62.20 diethylazodicarboxylate and triphenylphosphine, by means of the Mitsonobu reaction. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol or thiophenol and the alcohol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The reaction yields the phenolic ether 62.21. The carbomethoxy group is then reduced by reaction with sodium borohydride, as described above, to afford the carbinol 62.22.

Using the above procedures, but employing, in place of 3-hydroxyphenylalanine 62.13, different hydroxy or mercapto-substituted phenylalanines 62.1, and/or different dialkyl hydroxyalkyl phosphonates 62.20, the corresponding products 62.9 are obtained.

As a further example of the methods illustrated in Scheme 62, 4-mercaptophenylalanine 62.23, prepared as described in J. Am. Chem. Soc., 1997, 119, 7173, is converted into the benzyl ester 62.24 by means of a conventional acid-catalyzed esterification reaction. The mercapto group is then protected by conversion to the S-adamantyl group, by reaction with 1-adamantanol and trifluoroacetic acid at ambient temperature as described in Chem. Pharm. Bull., 26, 1576, 1978. The amino group is then converted into the phthalimido group as described above, and the ester moiety is hydrolyzed with aqueous base to afford the carboxylic acid 62.27. The latter compound is then transformed, by means of the series of reactions shown in Scheme 60, into the carbomethoxy oxazolidinone 62.28. The adamantyl protecting group is then removed by treatment of the thioether 62.28 with mercuric acetate in trifluoroacetic acid at 0°, as described in Chem. Pharm. Bull., 26, 1576, 1978, to produce the thiol 62.29. The thiol is then reacted with one molar equivalent of a dialkyl bromoethylphosphonate 62.30, (Aldrich) and cesium carbonate in dimethylformamide at 70°, to afford the thioether product 62.31. The carbomethoxy group is then reduced with sodium borohydride, as described above, to prepare the carbinol 62.32.

Using the above procedures, but employing, in place of 4-mercaptophenylalanine 62.23, different hydroxy or mercapto-substituted phenylalanines 62.1, and/or different dialkyl bromoalkyl phosphonates 62.10, the corresponding products 62.12 are obtained.

Scheme 60

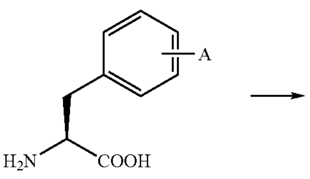

60.1

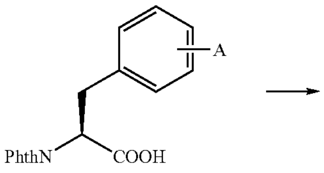

60.2

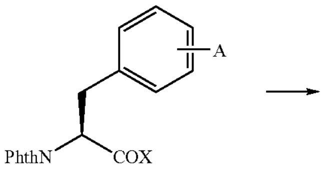

60.3

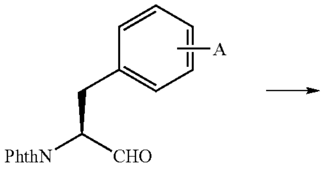

60.4

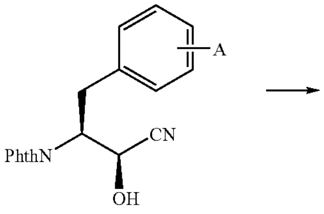

60.5

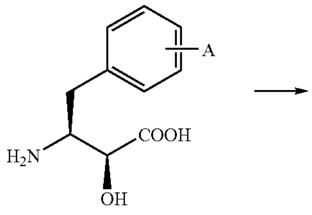

60.6

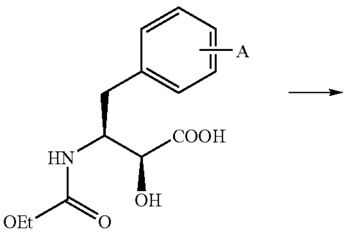

60.7

-continued
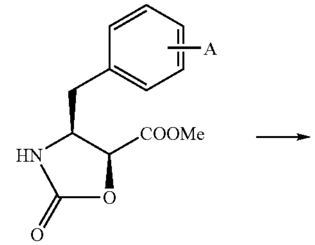
60.8
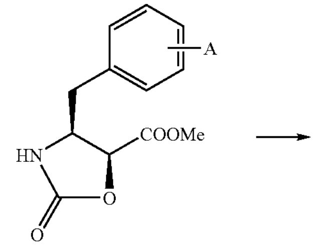
60.9
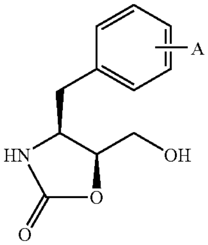
2.1
Scheme 61
Method
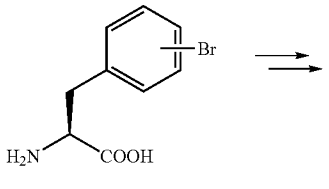
61.1
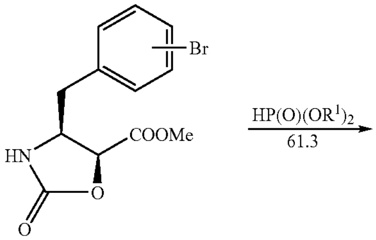
61.2
-continued
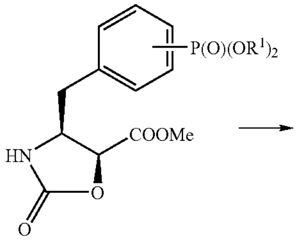
61.4
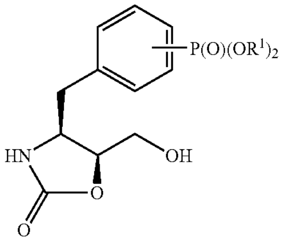
61.5
Example
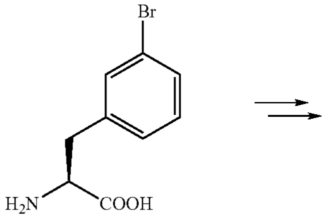
61.6
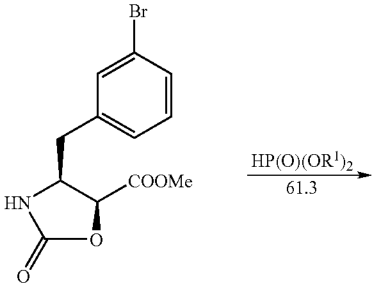
61.7
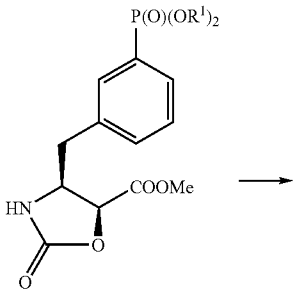
61.8

-continued
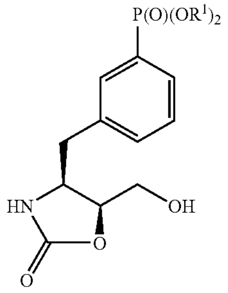
61.9
Scheme 62
Method
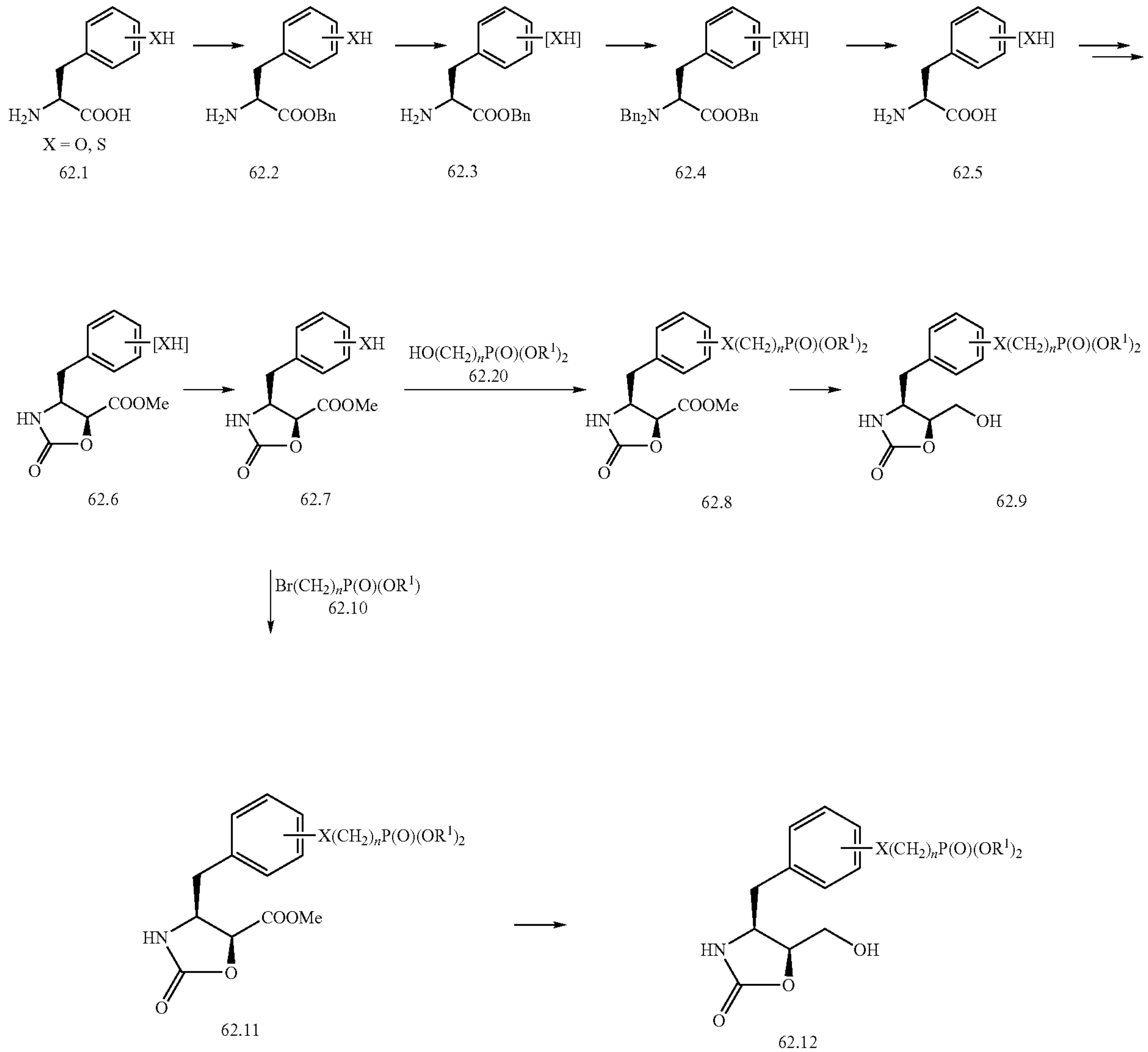
62.1 62.2 62.3 62.4 62.5
62.6 62.7 62.8 62.9
62.11 62.12

Scheme 62
Example 1
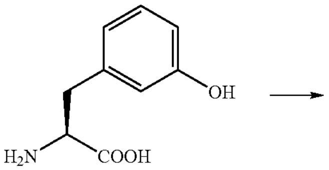
62.13
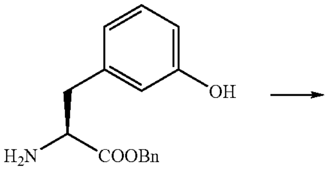
62.14
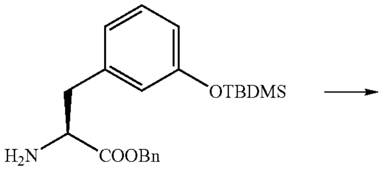
62.15
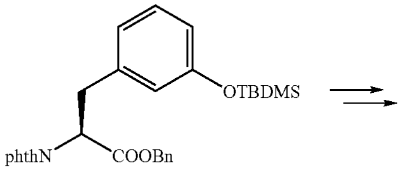
phth = phthalimido
62.16
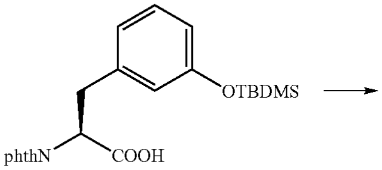
62.17
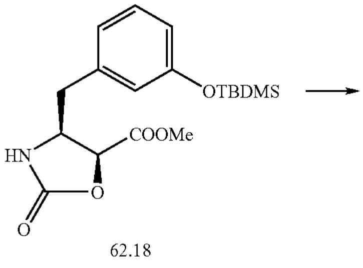
62.18
-continued
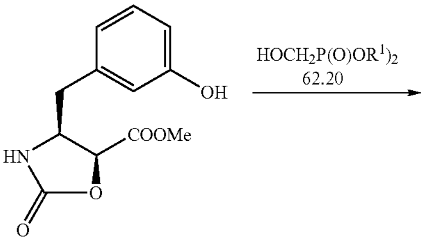
62.19
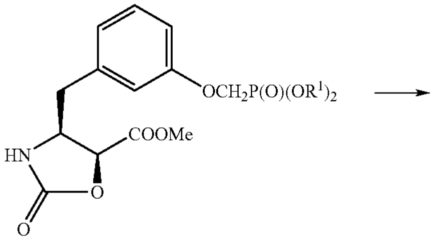
62.21
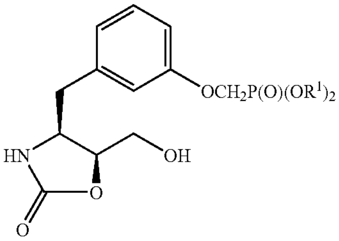
62.22
Scheme 62
Example 2
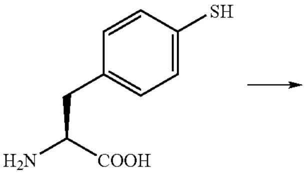
62.23
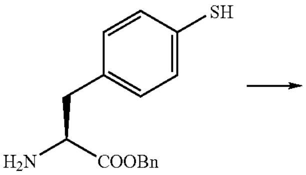
62.24
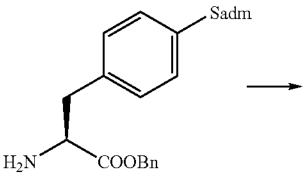
62.25

-continued

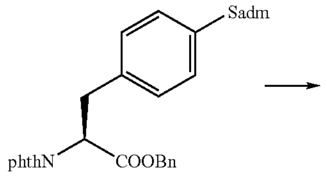

62.26 adm = adamantyl

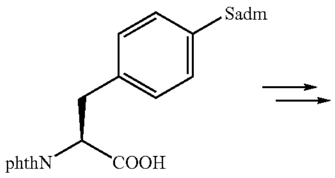

62.27

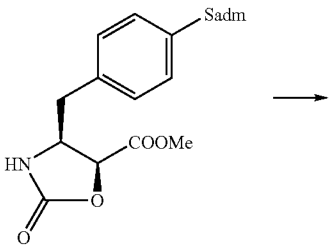

62.28

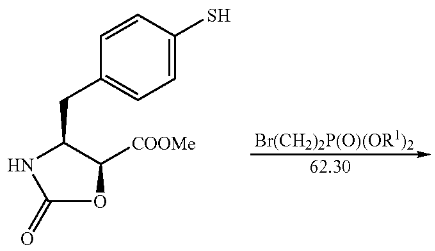

62.29

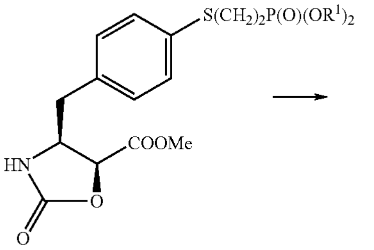

62.31

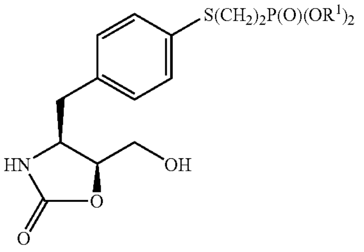

62.32

Preparation of the Phosphonate-containing Thiophenol Derivatives 7.2.

Schemes 63-83 describe the preparation of phosphonate-contarning thiophenol derivatives 7.2 which are employed as described above (Schemes 7-9) in the preparation of the phosphonate ester intermediates 1 in which X is sulfur.

Scheme 63 depicts the preparation of thiophenol derivatives in which the phosphonate moiety is attached directly to the phenyl ring. In this procedure, a halo-substituted thiophenol 63.1 is protected to afford the product 63.2. The protection of phenyl thiol groups is described in Protective Groups in Organic Synthesis, by T. W. Greene and P. G. M Wuts, Wiley, Second Edition 1990, p. 277. For example, thiol substituents can be protected as trialkylsilyloxy groups. Trialkylsilyl groups are introduced by the reaction of the thiophenol with a chlorotrialkylsilane and a base such as imidazole, for example as described in Protective Groups in Organic Synthesis, by T. W. Greene and P. G. M Wuts, Wiley, Second Edition 1990, p. 10, p. 68-86. Alternatively, thiol substituents can be protected by conversion to tert-butyl or adamantyl thioethers, or 4-methoxybenzyl thioethers, prepared by the reaction between the thiol and 4-methoxybenzyl chloride in the presence of ammonium hydroxide, as described in Bull. Chem. Soc. Jpn., 37, 433, 1974. The product is then coupled, in the presence of triethylamine and tetrakis(triphenylphosphine)palladium(0), as described in J. Med. Chem., 35, 1371, 1992, with a dialkyl phosphite 63.3, to afford the phosphonate ester 63.4. The thiol protecting group is then removed, as described above, to afford the thiol 63.5.

For example, 3-bromothiophenol 63.6 is converted into the 9-fluorenylmethyl (Fm) derivative 63.7 by reaction with 9-fluorenylmethyl chloride and diisopropylethylamine in dimethylformamide, as described in Int. J. Pept. Protein Res., 20, 434, 1982. The product is then reacted with a dialkyl phosphite 63.3, as described above, to afford the phosphonate ester 63.8. The Fm protecting group is then removed by treatment of the product with piperidine in dimethylformamide at ambient temperature, as described in J. Chem. Soc., Chem. Comm., 1501, 1986, to give the thiol 63.9.

Using the above procedures, but employing, in place of 3-bromothiophenol 63.6, different thiophenols 63.1, and/or different dialkyl phosphites 63.3, the corresponding products 63.5 are obtained.

Scheme 64 illustrates an alternative method for obtaining thiophenols with a directly attached phosphonate group. In this procedure, a suitably protected halo-substituted thiophenol 64.2 is metallated, for example by reaction with magnesium or by transmetallation with an alkyllithium reagent, to afford the metallated derivative 64.3. The latter compound is reacted with a halodialkyl phosphite 64.4 to afford the product 64.5; deprotection then affords the thiophenol 64.6

For example, 4-bromothiophenol 64.7 is converted into the S-triphenylmethyl (trityl) derivative 64.8, as described in Protective Groups in Organic Synthesis, by T. W. Greene and P. G. M. Wuts, Wiley, 1991, pp. 287. The product is converted into the lithium derivative 64.9 by reaction with butyllithium in an ethereal solvent at low temperature, and the resulting lithio compound is reacted with a dialkyl chlorophosphite 64.10 to afford the phosphonate 64.11. Removal of the trityl group, for example by treatment with dilute hydrochloric acid in acetic acid, as described in J. Org. Chem., 31, 1118, 1966, then affords the thiol 64.12.

Using the above procedures, but employing, in place of the bromo compound 64.7, different halo compounds 64.1, and/or different halo dialkyl phosphites 64.4, there are obtained the corresponding thiols 64.6.

Scheme 65 illustrates the preparation of phosphonate-substituted thiophenols in which the phosphonate group is attached by means of a one-carbon link. In this procedure, a suitably protected methyl-substituted thiophenol 65.1 is subjected to free-radical bromination to afford a bromomethyl product 65.2. This compound is reacted with a sodium dialkyl phosphite 65.3 or a trialkyl phosphite, to give the displacement or rearrangement product 65.4, which upon deprotection affords the thiophenol 65.5.

For example, 2-methylthiophenol 65.6 is protected by conversion to the benzoyl derivative 65.7, as described in Protective Groups in Organic Synthesis, by T. W. Greene and P. G. M. Wuts, Wiley, 1991, pp. 298. The product is reacted with N-bromosuccinimide in ethyl acetate to yield the bromomethyl product 65.8. This material is reacted with a sodium dialkyl phosphite 65.3, as described in J. Med. Chem., 35, 1371, 1992, to afford the product 65.9. Alternatively, the bromomethyl compound 65.8 is converted into the phosphonate 65.9 by means of the Arbuzov reaction, for example as described in Handb. Organophosphorus Chem., 1992, 115. In this procedure, the bromomethyl compound 65.8 is heated with a trialkyl phosphate $P(OR^1)_3$ at ca. 100° to produce the phosphonate 65.9. Deprotection of the phosphonate 65.9, for example by treatment with aqueous ammonia, as described in J. Am. Chem. Soc., 85, 1337, 1963, then affords the thiol 65.10.

Using the above procedures, but employing, in place of the bromomethyl compound 65.8, different bromomethyl compounds 65.2, there are obtained the corresponding thiols 65.5.

Scheme 66 illustrates the preparation of thiophenols bearing a phosphonate group linked to the phenyl nucleus by oxygen or sulfur. In this procedure, a suitably protected hydroxy or thio-substituted thiophenol 66.1 is reacted with a dialkyl hydroxyalkylphosphonate 66.2 under the conditions of the Mitsonobu reaction, for example as described in Org. React., 1992, 42, 335, to afford the coupled product 66.3. Deprotection then yields the O- or S-linked products 66.4.

For example, the substrate 3-hydroxythiophenol, 66.5, is converted into the monotrityl ether 66.6, by reaction with one equivalent of trityl chloride, as described above. This compound is reacted with diethyl azodicarboxylate, triphenyl phosphine and a dialkyl 1-hydroxymethyl phosphonate 66.7 in benzene, as described in Synthesis, 4, 327, 1998, to afford the ether compound 66.8. Removal of the trityl protecting group, as described above, then affords the thiophenol 66.9.

Using the above procedures, but employing, in place of the phenol 66.5, different phenols or thiophenols 66.1, there are obtained the corresponding thiols 66.4.

Scheme 63

Method

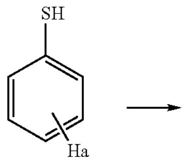

63.1

Ha = halogen

-continued

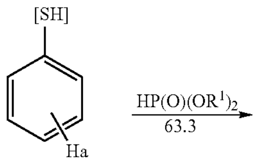

63.2

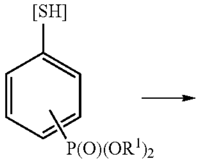

63.4

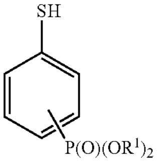

63.5

Example

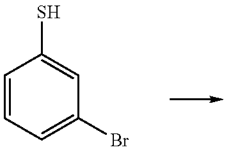

63.6

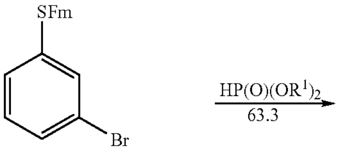

63.7

Fm = 9-fluorenylmethyl

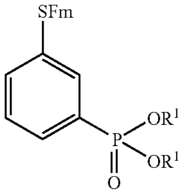

63.8

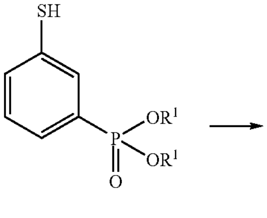

63.9

Scheme 64
Method
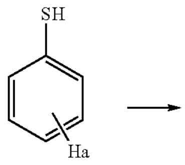
64.1
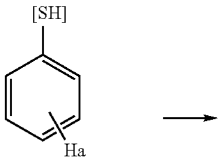
64.2
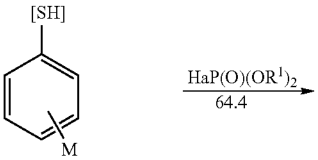
64.3
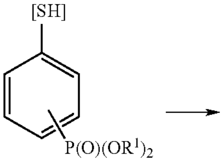
64.5
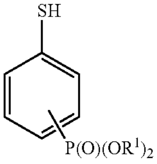
64.6
Example
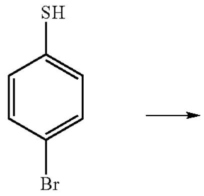
64.7
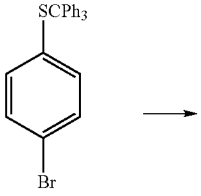
64.8
-continued
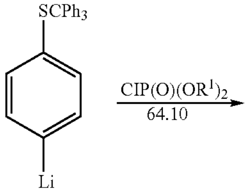
64.9
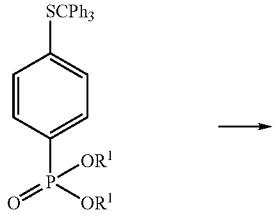
64.11
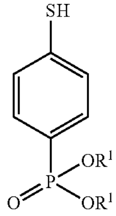
64.12
Scheme 65
Method
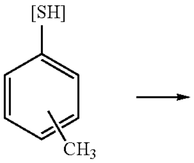
65.1
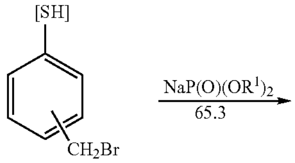
65.2
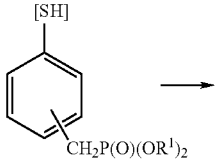
65.4
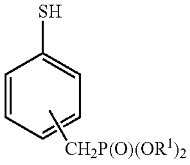
65.5

-continued

Example

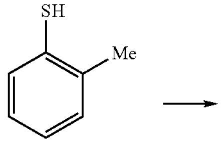

65.6

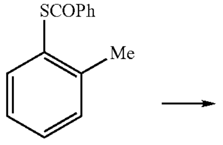

65.7

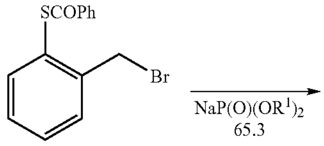

65.8

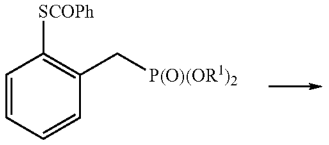

65.9

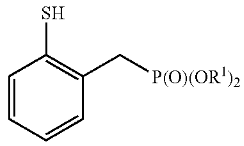

65.10

Scheme 66

Method

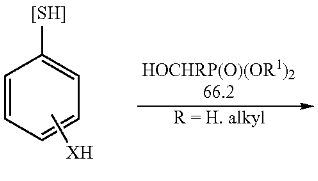

X = O, S
66.1

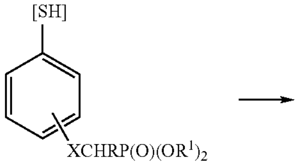

66.3

-continued

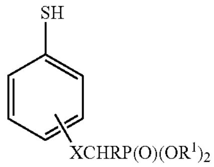

66.4

Example

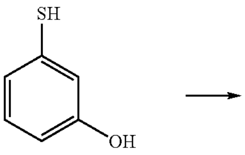

66.5

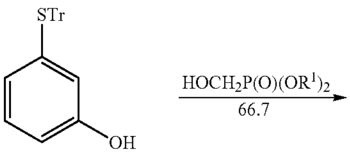

Tr = triphenylmethyl
66.6

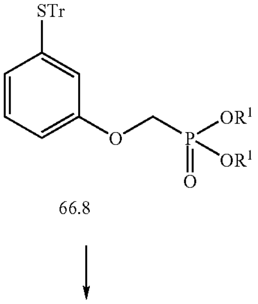

66.8

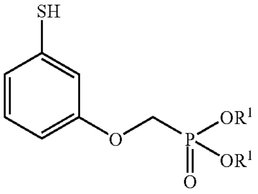

66.9

Scheme 67 illustrates the preparation of thiophenols 67.4 bearing a phosphonate group linked to the phenyl nucleus by oxygen, sulfur or nitrogen. In this procedure, a suitably protected O, S or N-substituted thiophenol 67.1 is reacted with an activated ester, for example the trifluoromethanesulfonate 67.2, of a dialkyl hydroxyalkyl phosphonate, to afford the coupled product 67.3. Deprotection then affords the thiol 67.4.

For example, 4-methylaminothiophenol 67.5 is reacted in dichloromethane solution with one equivalent of acetyl chloride and a base such as pyridine, as described in Protective Groups in Organic Synthesis, by T. W. Greene and P. G. M. Wuts, Wiley, 1991, pp. 298, to afford the S-acetyl product 67.6. This material is then reacted with a dialkyl trifluoromethanesulfonylmethyl phosphonate 67.7, the preparation of which is described in Tet. Lett., 1986, 27, 1477, to afford the displacement product 67.8. Preferably, equimolar amounts of the phosphonate 67.7 and the amine 67.6 are reacted together in an aprotic solvent such as dichloromethane, in the presence of a base such as 2,6-lutidine, at ambient temperatures, to afford the phosphonate product 67.8. Deprotection, for example by treatment with dilute aqueous sodium hydroxide for two minutes, as described in J. Am. Chem. Soc., 85, 1337, 1963, then affords the thiophenol 67.9.

Using the above procedures, but employing, in place of the thioamine 67.5, different phenols, thiophenols or amines 67.1, and/or different phosphonates 67.2, there are obtained the corresponding products 67.4.

Scheme 68 illustrates the preparation of phosphonate esters linked to a thiophenol nucleus by means of a heteroatom and a multiple-carbon chain, employing a nucleophilic displacement reaction on a dialkyl bromoalkyl phosphonate 68.2. In this procedure, a suitably protected hydroxy, thio or amino substituted thiophenol 68.1 is reacted with a dialkyl bromoalkyl phosphonate 68.2 to afford the product 68.3. Deprotection then affords the free thiophenol 68.4.

For example, 3-hydroxythiophenol 68.5 is converted into the S-trityl compound 68.6, as described above. This compound is then reacted with, for example, a dialkyl 4-bromobutyl phosphonate 68.7, the synthesis of which is described in Synthesis, 1994, 9, 909. The reaction is conducted in a dipolar aprotic solvent, for example dimethylformamide, in the presence of a base such as potassium carbonate, and optionally in the presence of a catalytic amount of potassium iodide, at about 50°, to yield the ether product 68.8. Deprotection, as described above, then affords the thiol 68.9.

Using the above procedures, but employing, in place of the phenol 68.5, different phenols, thiophenols or amines 68.1, and/or different phosphonates 68.2, there are obtained the corresponding products 68.4.

Scheme 69 depicts the preparation of phosphonate esters linked to a thiophenol nucleus by means of unsaturated and saturated carbon chains. The carbon chain linkage is formed by means of a palladium catalyzed Heck reaction, in which an olefinic phosphonate 69.2 is coupled with an aromatic bromo compound 69.1. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate, to afford the coupled product 69.3. Deprotection, or hydrogenation of the double bond followed by deprotection, affords respectively the unsaturated phosphonate 69.4, or the saturated analog 69.6.

For example, 3-bromothiophenol is converted into the S—Fm derivative 69.7, as described above, and this compound is reacted with a dialkyl 1-butenyl phosphonate 69.8, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 100° to afford the coupled product 69.9. Deprotection, as described above, then affords the thiol 69.10. Optionally, the initially formed unsaturated phosphonate 69.9 is subjected to reduction, for example using diimide, as described above, to yield the saturated product 69.11, which upon deprotection affords the thiol 69.12.

Using the above procedures, but employing, in place of the bromo compound 69.7, different bromo compounds 69.1, and/or different phosphonates 69.2, there are obtained the corresponding products 69.4 and 69.6

Scheme 67

Method

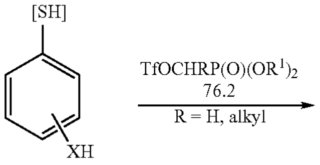

X = O, S, NH, Nalkyl
67.1

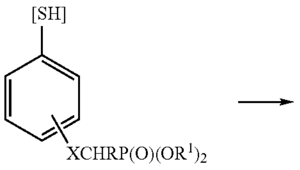

67.3

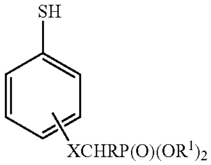

67.4

Example

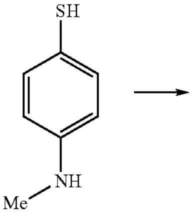

67.5

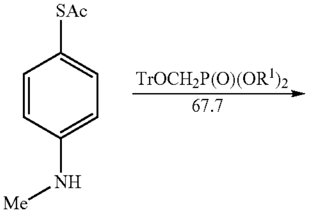

67.6

-continued
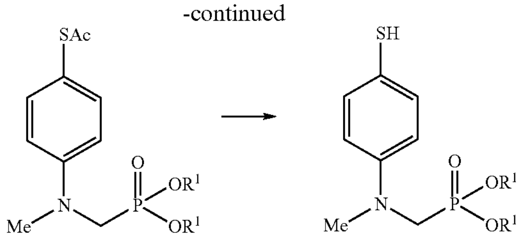
67.8 67.9
Scheme 68
Method
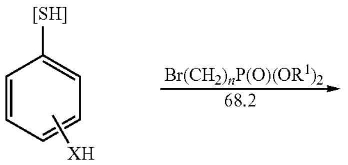
X = O, S, NH, Nalkyl
68.1
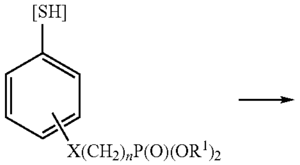
68.3
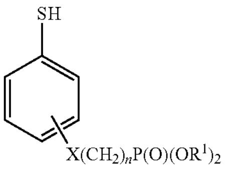
68.4
-continued
Example
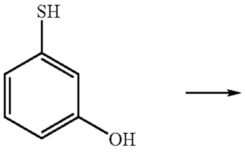
68.5
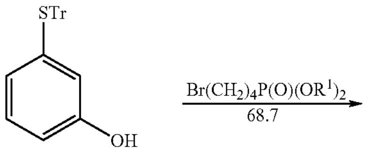
Tr = triphenylmethyl
68.6
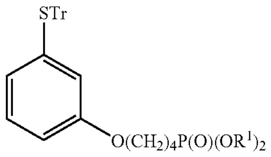
68.8
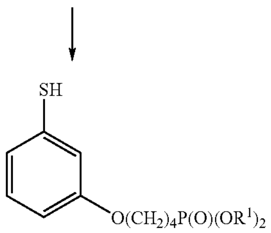
68.9
Scheme 69
Method
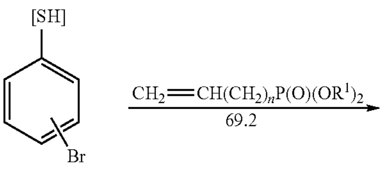
69.1
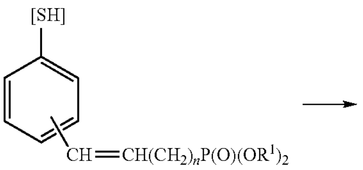
69.3
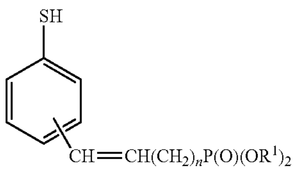
69.4

-continued

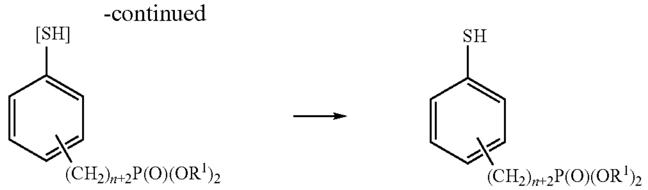

69.5 69.6

Example

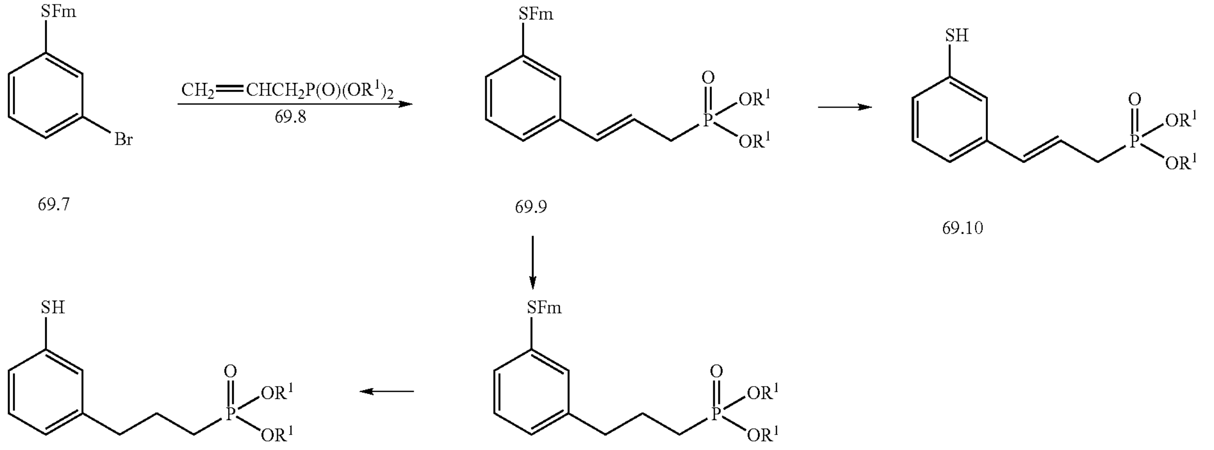

69.7 69.9 69.10

69.12 69.11

Scheme 70 illustrates the preparation of an aryl-linked phosphonate ester 70.4 by means of a palladium(0) or palladium(II) catalyzed coupling reaction between a bromobenzene and a phenylboronic acid, as described in Comprehensive Organic Transformations, by R. C. Larock, VCH, 1989, p. 57. The sulfur-substituted phenylboronic acid 70.1 is obtained by means of a metallation-boronation sequence applied to a protected bromo-substituted thiophenol, for example as described in J. Org. Chem., 49, 5237, 1984. A coupling reaction then affords the diaryl product 70.3 which is deprotected to yield the thiol 70.4.

For example, protection of 4-bromothiophenol by reaction with tert-butylchlorodimethylsilane, in the presence of a base such as imidazole, as described in Protective Groups in Organic Synthesis, by T. W. Greene and P. G. M. Wuts, Wiley, 1991, p. 297, followed by metallation with butyllithium and boronation, as described in J. Organomet. Chem., 1999, 581, 82, affords the boronate 70.5. This material is reacted with a dialkyl 4-bromophenylphosphonate 70.6, the preparation of which is described in J. Chem. Soc., Perkin Trans., 1977, 2, 789, in the presence of tetrakis(triphenylphosphine)palladium (0) and an inorganic base such as sodium carbonate, to afford the coupled product 70.7. Deprotection, for example by the use of tetrabutylammonium fluoride in anhydrous tetrahydrofuran, then yields the thiol 70.8.

Using the above procedures, but employing, in place of the boronate 70.5, different boronates 70.1, and/or different phosphonates 70.2, there are obtained the corresponding products 70.4.

Scheme 71 depicts the preparation of dialkyl phosphonates in which the phosphonate moiety is linked to the thiophenyl group by means of a chain which incorporates an aromatic or heteroaromatic ring. In this procedure, a suitably protected O, S or N-substituted thiophenol 71.1 is reacted with a dialkyl bromomethyl-substituted aryl or heteroarylphosphonate 71.2, prepared, for example, by means of an Arbuzov reaction between equimolar amounts of a bis(bromo-methyl) substituted aromatic compound and a trialkyl phosphite. The reaction product 71.3 is then deprotected to afford the thiol 71.4. For example, 1,4-dimercaptobenzene is converted into the monobenzoyl ester 71.5 by reaction with one molar equivalent of benzoyl chloride, in the presence of a base such as pyridine. The monoprotected thiol 71.5 is then reacted with a dialkyl 4-(bromomethyl)phenylphosphonate, 71.6, the preparation of which is described in Tetrahedron, 1998, 54, 9341. The reaction is conducted in a solvent such as dimethylformamide, in the presence of a base such as potassium carbonate, at about 50°. The thioether product 71.7 thus obtained is deprotected, as described above, to afford the thiol 71.8.

Using the above procedures, but employing, in place of the thiophenol 71.5, different phenols, thiophenols or amines 71.1, and/or different phosphonates 71.2, there are obtained the corresponding products 71.4.

Scheme 72 illustrates the preparation of phosphonate-containing thiophenols in which the attached phosphonate chain forms a ring with the thiophenol moiety.

In this procedure, a suitably protected thiophenol 72.1, for example an indoline (in which X—Y is $(CH_2)_2$), an indole (X—Y is CH═CH) or a tetrahydroquinoline (X—Y is $(CH_2)_3$) is reacted with a dialkyl trifluoromethanesulfonyloxymethyl phosphonate 72.2, in the presence of an organic or inorganic base, in a polar aprotic solvent such as, for example, dimethylformamide, to afford the phosphonate ester 72.3. Deprotection, as described above, then affords the thiol 72.4. The preparation of thio-substituted indolines is described in EP 209751. Thio-substituted indoles, indolines and tetrahydroquinolines can also be obtained from the corresponding hydroxy-substituted compounds, for example by thermal rearrangement of the dimethylthiocarbamoyl esters, as described in J. Org. Chem., 31, 3980, 1966. The preparation of hydroxy-substituted indoles is described in Syn., 1994, 10, 1018; preparation of hydroxy-substituted indolines is described in Tet. Lett., 1986, 27, 4565, and the preparation of hydroxy-substituted tetrahydroquinolines is described in J. Het. Chem., 1991, 28, 1517, and in J. Med. Chem., 1979, 22, 599. Thio-substituted indoles, indolines and tetrahydroquinolines can also be obtained from the corresponding amino and bromo compounds, respectively by diazotization, as described in Sulfur Letters, 2000, 24, 123, or by reaction of the derived organolithium or magnesium derivative with sulfur, as described in Comprehensive Organic Functional Group Preparations, A. R. Katritzky et al, eds, Pergamon, 1995, Vol. 2, p 707. For example, 2,3-dihydro-1H-indole-5-thiol, 72.5, the preparation of which is described in EP 209751, is converted into the benzoyl ester 72.6, as described above, and the ester is then reacted with the trifluoromethanesulfonate 72.7, in a polar organic solvent such as dimethylformamide, in the presence of a base such as potassium carbonate, to yield the phosphonate 72.8. Deprotection, for example by reaction with dilute aqueous ammonia, as described above, then affords the thiol 72.9.

Using the above procedures, but employing, in place of the thiol 72.5, different thiols 72.1, and/or different triflates 72.2, there are obtained the corresponding products 72.4.

Scheme 70

Method

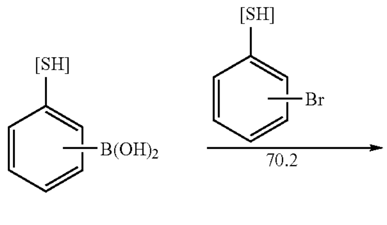

70.2

70.1

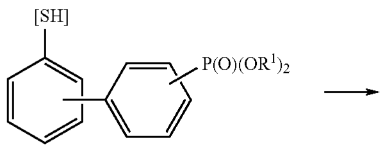

70.3

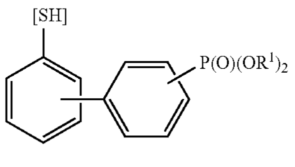

70.4

-continued

Example

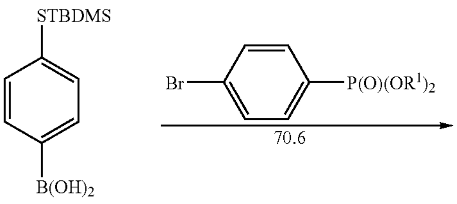

70.6

70.5

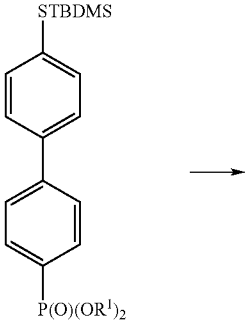

70.7

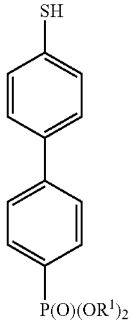

70.8

Scheme 71

Method

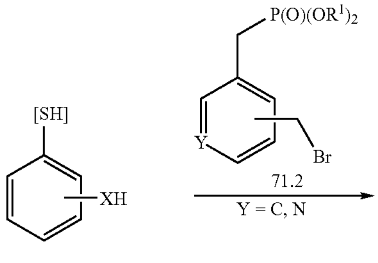

71.2

X = O, S, NH, Nalkyl 71.1

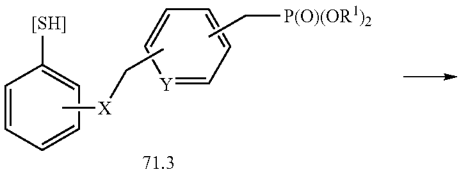

71.3

-continued

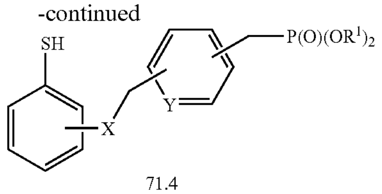

71.4

Example

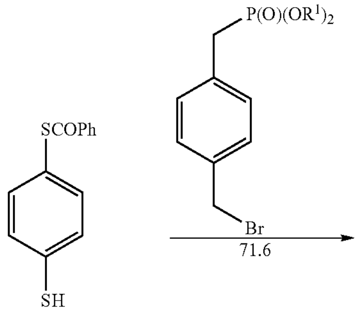

71.6

71.5

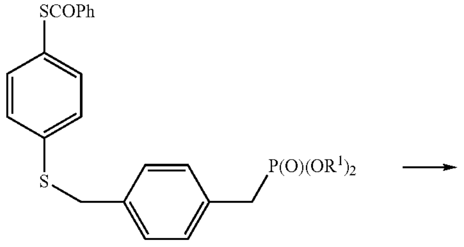

71.7

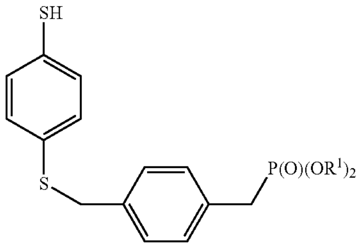

71.8

Preparation of Phosphonate-containing Analogs of Isobutylamine 10.2.

Schemes 73-75 illustrate the preparation of the phosphonate-containing analogs of isobutylamine which are employed in the preparation of the phosphonate esters 2.

Scheme 73 depicts the preparation of phosphonates which are attached to the isobutylamine by means of an amide linkage. In this procedure, an aminoacid 73.1 is protected to afford the product 73.2. The protection of amino groups is described in Protective Groups in Organic Synthesis, by T. W. Greene and P. G. M Wuts, Wiley, Second Edition 1990, 309. Amino groups are protected, for example, by conversion into carbamates such as the tert. butoxycarbamate (BOC) derivative, or by reaction with phthalic anhydride to afford the phthalimido (phth) derivative. The amine-protected aminoacid 73.2 is then coupled with a dialkyl aminoalkyl phosphonate 73.3, to yield the amide 73.4. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide. The protecting group is then removed to afford the amine 73.5. Deprotection of amines is described in Protective Groups in Organic Synthesis, by T. W. Greene and P. G. M Wuts, Wiley, Second Edition 1990, p 309ff. For example, BOC groups are removed by treatment with acids such as trifluoroacetic acid, and phthalimido groups are removed by reaction with hydrazine hydrate.

For example, 2-methyl-4-aminobutyric acid 73.6 (Acros) is reacted with phthalic anhydride in refluxing toluene, as described in Protective Groups in Organic Synthesis, by T. W. Greene and P. G. M Wuts, Wiley, Second Edition 1990, p 358, to give the phthalimido derivative 73.7. The product is coupled with a dialkyl aminoethyl phosphonate 73.8, the preparation of which is described in J. Org. Chem., 2000, 65, 676, in the presence of dicyclohexyl carbodiimide, to give the amide 73.9 The protecting group is removed by reaction of the product with ethanolic hydrazine at ambient temperature, as described in Protective Groups in Organic Synthesis, by T. W. Greene and P. G. M Wuts, Wiley, Second Edition 1990, p 358, to afford the amine 73.10.

Using the above procedures, but employing, in place of the acid 73.6, different acids 73.1, and/or different amines 73.3, the corresponding amides 73.5 are obtained.

Scheme 74 depicts the preparation of isobutylamine phosphonates in which the phosphonate is attached by means of an aromatic ring. In this procedure, 2-methyl-but-3-enylamine 74.1, prepared as described in Org. Prep. Proc. Int. 1976, 8, 75, is coupled, in the presence of a palladium catalyst, as described above (Scheme 50) with a dialkyl bromophenyl phosphonate 74.2 to afford the olefinic product 74.3. Optionally, the product is reduced to afford the saturated analog 74.4. The reduction is effected catalytically, for example by the use of a palladium catalyst, or chemically, for example by the use of diimide.

For example, the amine 74.1 is coupled with a dialkyl 4-bromophenyl phosphonate 74.5, prepared as described in J. Organomet. Chem., 1999, 581, 62, to yield the product 74.6. Catalytic hydrogenation in ethanol, using a 5% palladium catalyst, then affords the saturated compound 74.7.

Using the above procedures, but employing, in place of the phosphonate 74.5, different phosphonates 74.2 the corresponding products 74.3 and 74.4 are obtained.

Scheme 75 illustrates the preparation of isobutylamine phosphonates in which the phosphonate group is attached by means of an alkylene chain. In this procedure, a bromoamine 75.1 is protected, as described in Scheme 73, to afford the derivative 75.2. The product is then reacted with a trialkyl phosphite 75.3, in an Arbuzov reaction, as described in Scheme 65, to give the phosphonate 75.4. Deprotection then affords the amine 75.5.

For example, 4-bromo-2-methyl-butylamine 75.6, prepared as described in Tet., 1998, 54, 2365, is converted, as described above, into the phthalimido derivative 75.7. The product is then heated at 110° with a trialkyl phosphite 75.3 to yield the phosphonate 75.8, which upon reaction with ethanolic hydrazine affords the amine 75.9.
Using the above procedures, but employing, in place of the bromide 75.6, different bromides 75.1, and/or different phosphites 75.3, the corresponding products 75.5 are obtained.
Scheme 72
Method
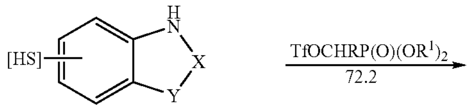
72.1
X—Y = $(CH_2)_{2,3}$; CH=CH
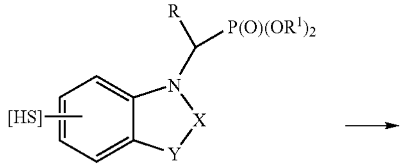
72.3
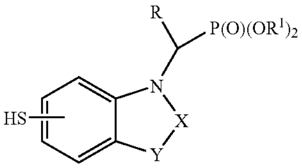
72.4
Example
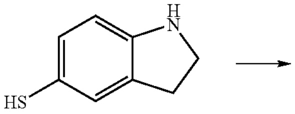
72.5
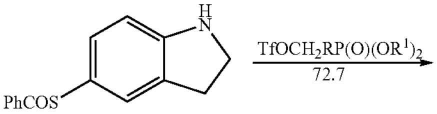
72.6
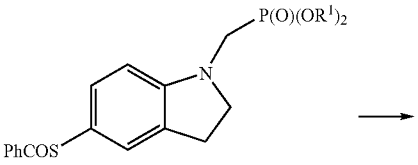
72.8
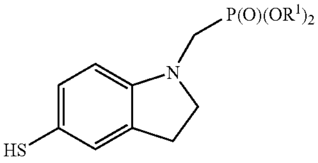
72.9
Scheme 73
Method
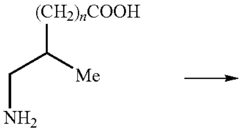
73.1
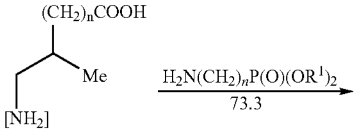
73.2
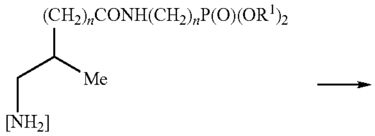
73.4
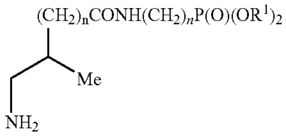
73.5
Example
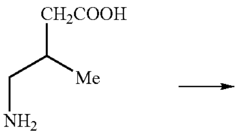
73.6
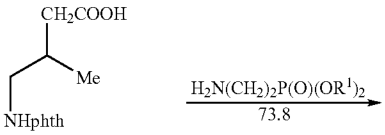
73.7
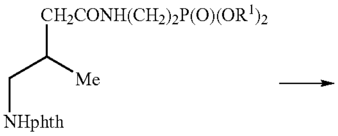
73.9
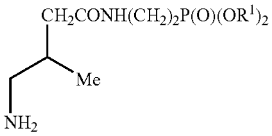
73.10

Scheme 74

Method

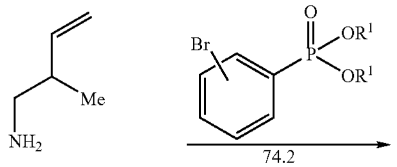

74.2

74.1

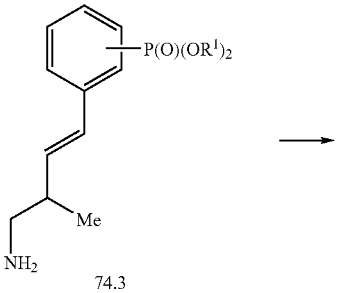

74.3

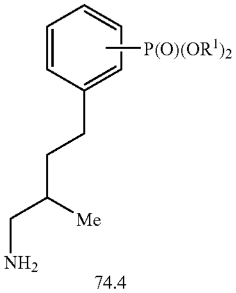

74.4

Example

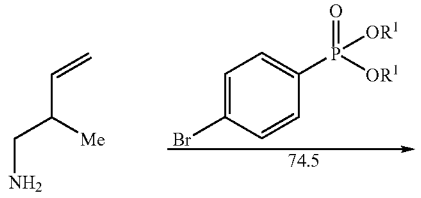

74.5

74.1

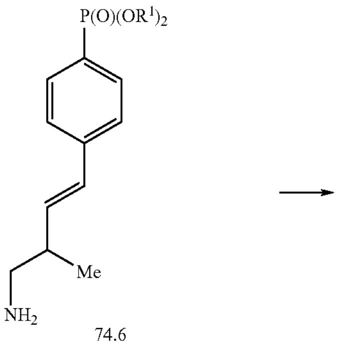

74.6

-continued

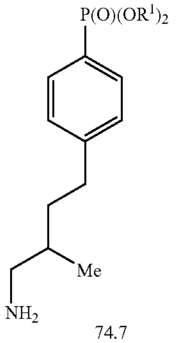

74.7

Scheme 75

Method

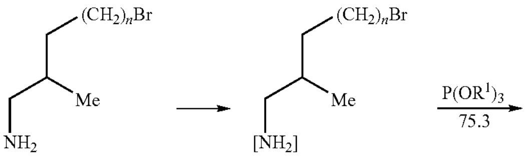

75.1 75.2

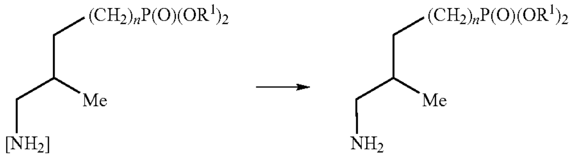

75.4 75.5

Example

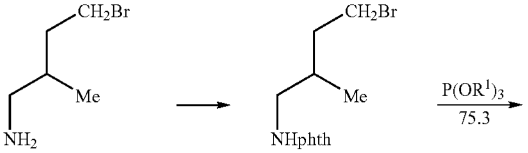

75.6 75.7

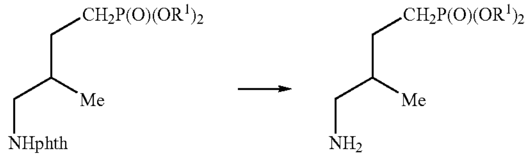

75.8 75.9

Preparation of Cyclopentylmethylamine Phosphonates.

Schemes 76-78 illustrate the preparation of cyclopentylmethylamine phosphonates which are employed, as shown in Schemes 10-12, in the preparation of the phosphonate esters 3.

Scheme 76 depicts the preparation of phosphonates attached to the cyclopentyl ring either directly or by means of an alkoxy link. In this procedure, a hydroxy-substituted cyclopentylmethylamine 76.1 is protected, and the protected derivative 76.2 is converted into the corresponding bromide 76.3, for example by treatment with carbon tetrabromide and triphenyl phosphine as described in Scheme 59. The bromo compound is then reacted with a trialkyl phosphite 76.4 in an Arbuzov reaction, as described above, to afford the phosphonate 76.5 which is then deprotected to give the amine 76.6. Alternatively, the protected amine 76.2 is reacted with a dialkyl bromoalkyl phosphonate 76.7 to give the ether 76.8. The alkylation reaction is conducted at ca 100° in a polar organic solvent such as dimethylformamide in the presence of a base such as sodium hydride or lithium hexamethyl disilylazide. The product is then deprotected to give the amine 76.9.

For example, 3-aminomethyl-cyclopentanol 76.10, prepared as described in Tet., 1999, 55, 10815, is converted, as described above, into the phthalimido derivative 76.11. The product is then converted, as described above, into the bromo analog 76.12. The latter compound is reacted at ca 120° with a trialkyl phosphite 76.4 to afford the phosphonate 76.13, which upon deprotection by reaction with hydrazine yields the amine 76.14.

Using the above procedures, but employing, in place of the bromide 76.12, different bromides 76.3, and/or different phosphites 76.4, the corresponding products 76.6 are obtained.

Alternatively, 2-aminomethyl-cyclopentanol 76.15, prepared as described in Tet., 1999, 55, 10815, is converted into the phthalimido derivative 76.16. The product is then reacted in dimethylformamide solution with an equimolar amount of a dialkyl bromopropyl phosphonate 76.17, prepared as described in J. Am. Chem. Soc., 2000, 122, 1554, and sodium hydride, to give the ether 76.18. Deprotection, as described above, then affords the amine 76.19.

Using the above procedures, but employing, in place of the carbinol 76.15, different carbinols 76.1, and/or different phosphonates 76.7, the corresponding products 76.9 are obtained.

Scheme 77 illustrates the preparation of cyclopentylmethylamines in which the phosphonate group is attached by means of an amide group. In this procedure, a carboxyalkyl-substituted cyclopentylmethylamine 77.1 is protected to afford the derivative 77.2. The product is then coupled, as described above, (Scheme 1) with a dialkyl aminoalkyl phosphonate 77.3 to yield the amide 77.4. Deprotection then affords the amine 77.5.

For example, 3-aminomethyl-cyclopentanecarboxylic acid 77.6 prepared as described in J. Chem. Soc. Perkin 2, 1995, 1381, is converted into the BOC derivative 77.7, by reaction with BOC anhydride in aqueous sodium hydroxide, as described in Proc. Nat. Acad. Sci., 69, 730, 1972. The product is then coupled, in the presence of dicyclohexyl carbodiimide, with a dialkyl aminopropyl phosphonate 77.8 to produce the amide 77.9. Removal of the BOC group, for example by treatment with hydrogen chloride in ethyl acetate, then affords the amine 77.10. Using the above procedures, but employing, in place of the carboxylic acid 77.6, different carboxylic acids 77.1, and/or different phosphonates 77.3, the corresponding products 77.5 are obtained.

Scheme 78 illustrates the preparation of cyclopentylmethylamines in which the phosphonate group is attached by means of an aminoalkyl group. In this procedure, the more reactive amino group of an amino-substituted cyclopentylmethylamine 78.1 is protected, to give the derivative 78.2. The product is then coupled, by means of a reductive amination reaction, as described in Scheme 55, with a dialkyl formylalkyl phosphonate 78.3 to give the amine product 78.4, which upon deprotection affords the amine 78.5.

For example, 2-aminomethyl-cyclopentylamine 78.6 prepared as described in WO 9811052, is reacted with one molar equivalent of phthalic anhydride in refluxing tetrahydrofuran, to yield the phthalimido derivative 78.7. The latter compound is reacted, in the presence of sodium cyanoborohydride, with a dialkyl formylmethyl phosphonate 78.8, prepared as described in Zh. Obschei. Khim., 1987, 57, 2793, to afford the product 78.9. Deprotection, as described above, then yields the amine 78.10.

Using the above procedures, but employing, in place of the diamine 78.6, different diamines 78.1, and/or different phosphonates 78.3, the corresponding products 78.5 are obtained.

Scheme 76

Method

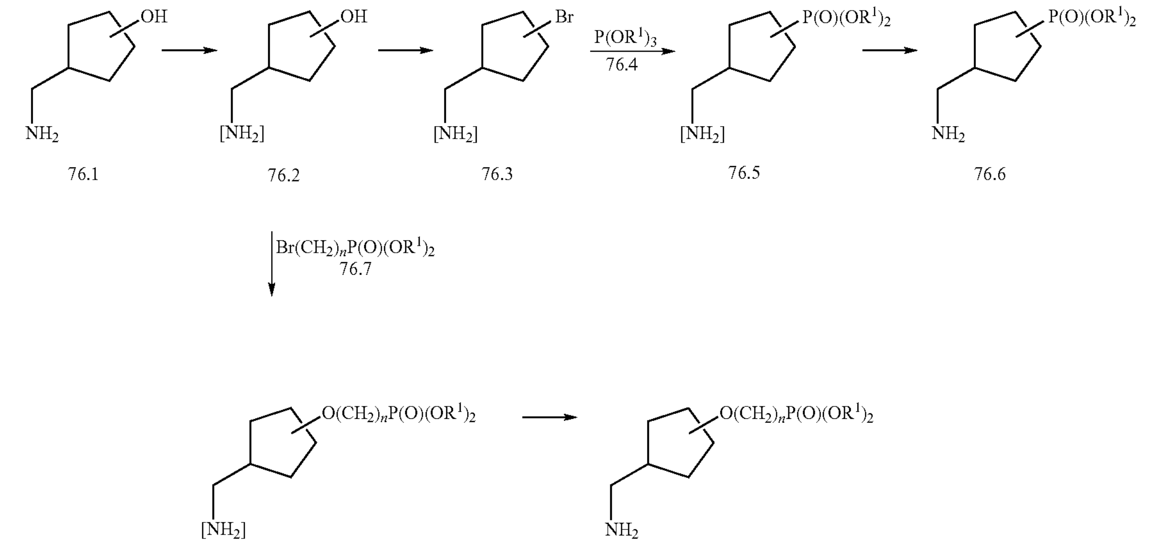

76.1 76.2 76.3 76.5 76.6

76.8 76.9

-continued
Example 1
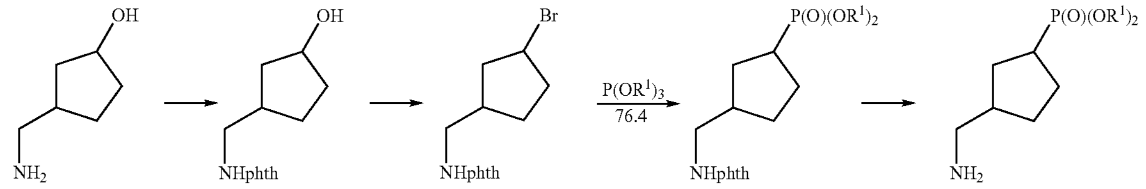
76.10 76.11 76.12 76.13 76.14
Example 2
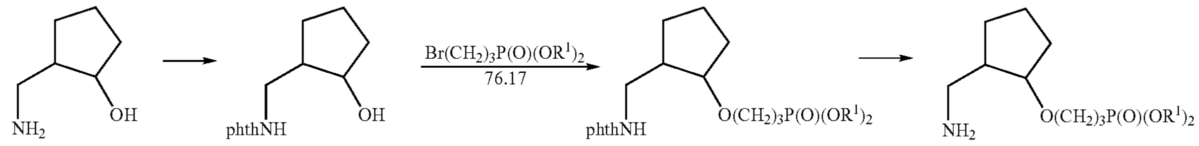
76.15 76.16 76.18 76.19
Scheme 77
Method
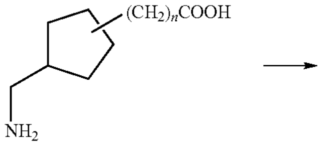
77.1
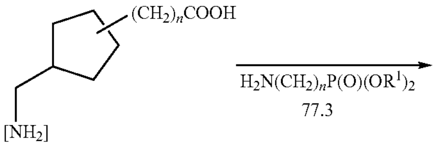
77.2
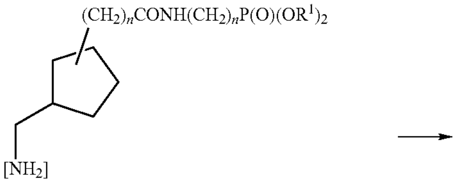
77.4
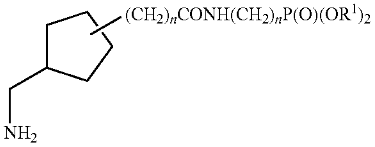
77.5
-continued
Example
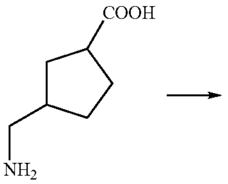
77.6
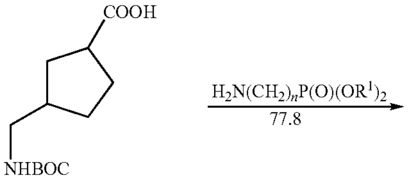
77.7
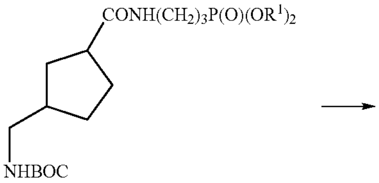
77.9
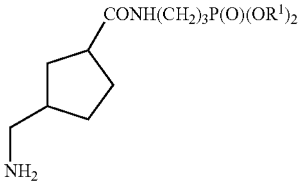
77.10

Scheme 78

Method

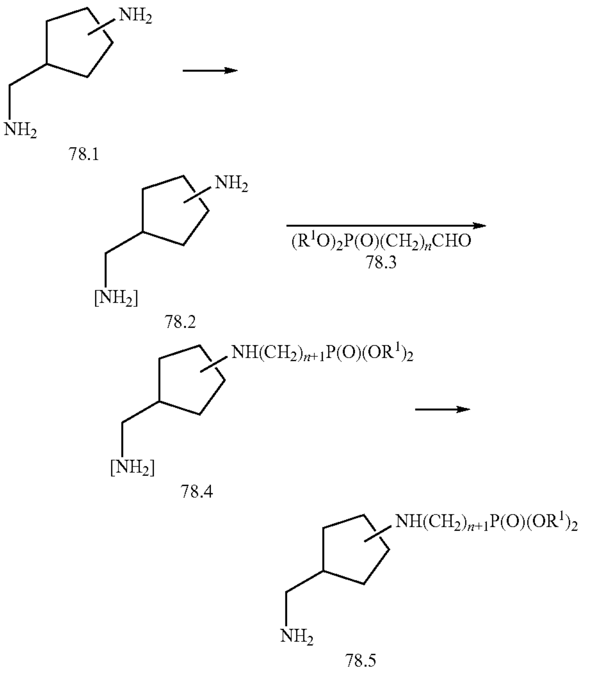

78.1 78.2 78.4 78.5

Example

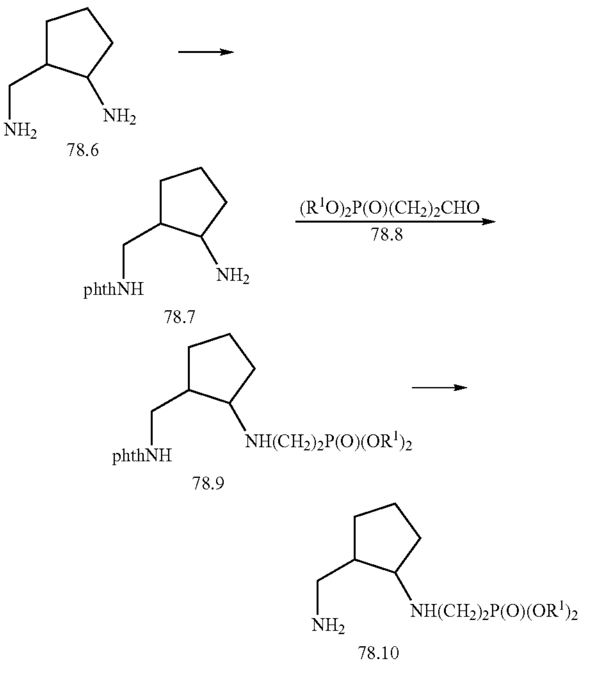

78.6 78.7 78.9 78.10

Preparation of Phosphonate-substituted Fluorobenzylamines 39.2.

Schemes 79 and 80 illustrate the preparation of phosphonate-substituted 3-fluorobenzylamines 39.2 which are used in the preparation of the phosphonate esters 6.

Scheme 79 depicts the preparation of fluorobenzylamines in which the phosphonate is attached by means of an amide or aminoalkyl linkage. In this procedure, the more reactive amino group in an amino-substituted 3-fluorobenzylamine 79.1 is protected. The product 79.2 is then coupled with a dialkyl carboxyalkyl phosphonate 79.3 to give the amide 79.4, which upon deprotection yields the free amine 79.5. Alternatively, the mono-protected diamine 79.2 is coupled, under reductive amination conditions, with a dialkyl formylalkyl phosphonate 79.6, to produce the amine 79.7, which upon deprotection affords the benzylamine 79.8.

For example, 4-amino-3-fluorobenzylamine 79.9, prepared as described in WO 9417035, is reacted in pyridine solution with one molar equivalent of acetic anhydride, to give the acetylamino product 79.10. The product is reacted with a dialkyl carboxyethyl phosphonate 79.11, (Epsilon) and dicyclohexyl carbodiimide, to afford the amide 79.12. Deprotection, for example by reaction with 85% hydrazine, as described in J. Org. Chem., 43, 4593, 1978, then gives the amine 79.13.

Using the above procedures, but employing, in place of the diamine 79.9, different diamines 79.1, and/or different phosphonates 79.3, the corresponding products 79.5 are obtained.

As a further example, the mono-protected diamine 79.10 is reacted, as described above, with a dialkyl formyl phosphonate 79.13, (Aurora) and sodium cyanoborohydride, to give the amination product 79.14. Deprotection then affords the amine 79.15.

Using the above procedures, but employing, in place of the diamine 79.10 different diamines 79.2, and/or different phosphonates 79.6, the corresponding products 79.8 are obtained.

Scheme 80 depicts the preparation of fluorobenzylamines in which the phosphonate is attached either directly or by means of a saturated or unsaturated alkylene linkage. In this procedure, a bromo-substituted 3-fluorobenzylamine 80.1 is protected. The product 80.2 is coupled, by means of a palladium-catalyzed Heck reaction, as described in Scheme 50, with a dialkyl alkenyl phosphonate 80.3, to give the olefinic product 80.4 which upon deprotection affords the amine 80.5. Optionally, the double bond is reduced, for example by catalytic hydrogenation over a palladium catalyst, to yield the saturated analog 80.9. Alternatively, the protected bromobenzylamine 80.6 is coupled, as described in Scheme 61, in the presence of a palladium catalyst, with a dialkyl phosphite 80.6 to produce the phosphonate 80.7.

Deprotection then affords the amine 80.8.

For example, 2-bromo-5-fluorobenzylamine 80.10, (Esprix Fine Chemicals) is converted, as described above, into the N-acetyl derivative 80.11. The product is the coupled in dimethylformamide solution with a dialkyl vinyl phosphonate 80.12, (Fluka) in the presence of palladium (II) acetate and triethylamine, to give the coupled product 80.13. Deprotection then affords the amine 80.14 and hydrogenation of the latter compound yields the saturated analog 80.15.

Using the above procedures, but employing, in place of the bromo compound 80.10 different bromo compounds 80.1, and/or different phosphonates 80.3, the corresponding products 80.5 and 80.9 are obtained.

As a further example, the protected amine 80.11 is coupled, in toluene at 100°, with a dialkyl phosphite 80.6, in the presence of tetrakis(triphenylphosphine)palladium and a tertiary organic base such as triethylamine, to give the phosphonate 80.16. Deprotection then affords the amine 80.17.

Using the above procedures, but employing, in place of the bromo compound 80.11 different bromo compounds 80.2, and/or different phosphites 80.6, the corresponding products 80.8 are obtained.

Scheme 79
Method
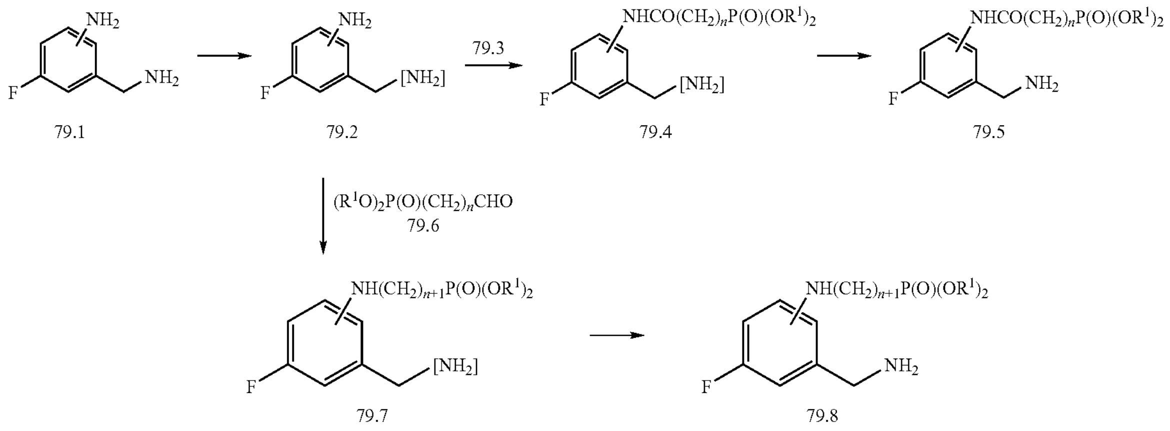
Example 1
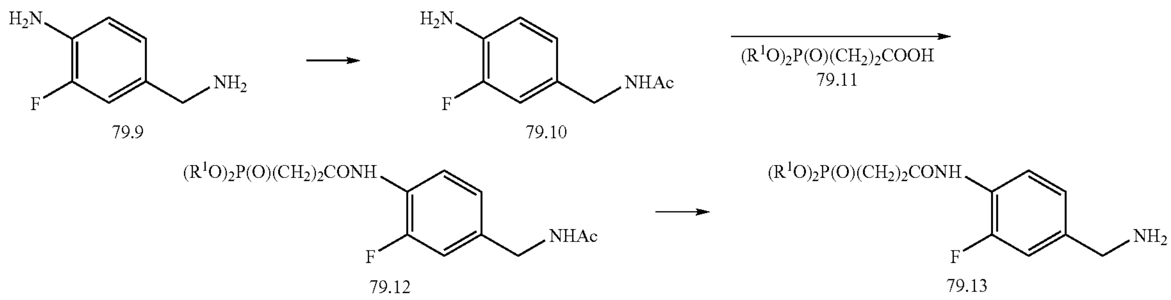
Example 2
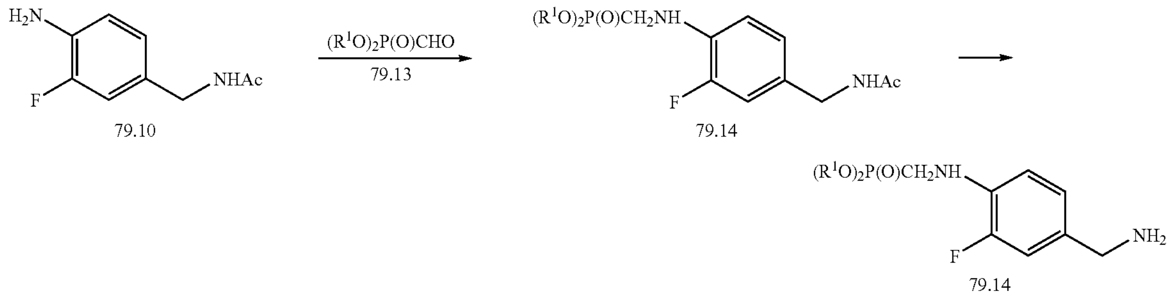
Scheme 80
Method
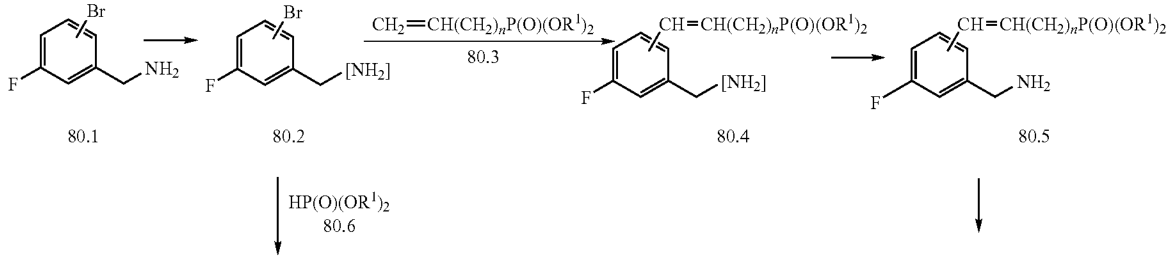

-continued

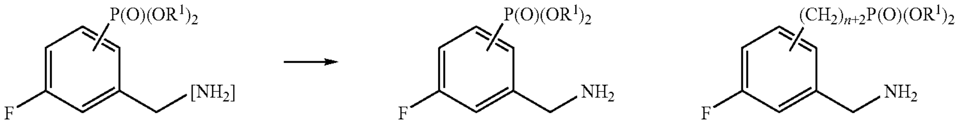

80.7 80.8 80.9

Example 1

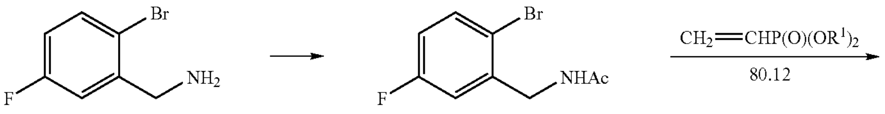

80.10 80.11

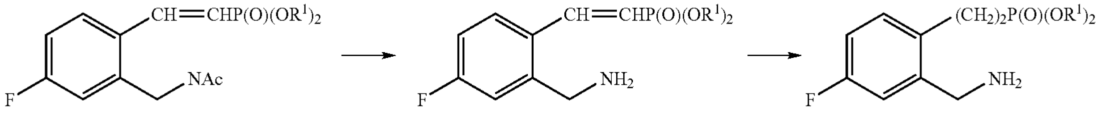

80.13 80.14 80.15

Example 2

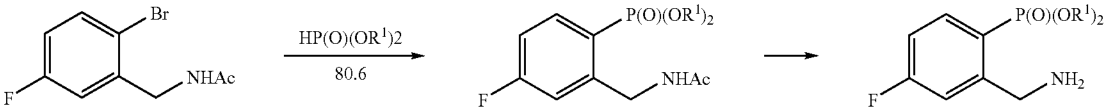

80.11 80.16 80.17

Preparation of Phosphonate-substituted Fluorobenzylamines 39.4.

Schemes 81 and 82 illustrate the preparation of phosphonate-substituted 3-fluorobenzylamines 39.4 which are used in the preparation of the phosphonate esters 7.

Scheme 81 depicts the preparation of 3-fluorobenzylamines in which the phosphonate group is attached by means of an amide linkage. In this procedure, 3-fluorophenylalanine 81.1, (Alfa Aesar) is converted into the BOC derivative 81.2. The product is then coupled with a dialkyl aminoalkyl phosphonate 81.3 to afford the amide 81.4, which upon deprotection gives the amine 81.5.

For example, the BOC-protected aminoacid 81.2 is coupled, in the presence of dicyclohexyl carbodiimide, with a dialkyl aminomethyl phosphonate 81.6 (Interchim), to prepare the amide 81.7. Deprotection then affords the amine 81.8.

Using the above procedures, but employing, in place of the amine 81.6 different amines 81.3, the corresponding products 81.5 are obtained.

Scheme 82 illustrates the preparation of fluorobenzylamine derivatives in which the phosphonate group is attached by means of an alkyl or alkoxy chain. In this procedure, a hydroxyalkyl-substituted 3-fluorobenzylamine 82.1 is converted into the BOC derivative 82.2. This compound is then reacted with a dialkyl bromoalkyl phosphonate 82.3 to give the ether 82.4. The alkylation reaction is conducted in a polar organic solvent such as N-methylpyrrolidinone in the presence of a strong base such as sodium bis(trimethylsilyl) amide. Deprotection of the product then affords the amine 82.5. Alternatively, the N-protected carbinol 82.2 is converted into the corresponding bromide 82.6, for example by reaction with N-bromoacetamide and triphenyl phosphine. The bromo compound is then reacted with a trialkyl phosphite in an Arbuzov reaction, as described above, to give the phosphonate 82.8, which upon deprotection affords the amine 82.9.

For example, 2-amino-2-(3-fluoro-phenyl)-ethanol 82.10, prepared as described in DE 4443892, is converted into the BOC derivative 82.11. The latter compound is then reacted in dimethylformamide at 100° with a dialkyl bromoethyl phosphonate 82.12 (Aldrich) and sodium hydride, to give the ether product 82.13. Removal of the BOC group then yields the amine 82.14.

Using the above procedures, but employing, in place of the carbinol 82.10 different carbinols 82.1, and/or different phosphonates 82.3 the corresponding products 82.5 are obtained.

As a further example, the BOC-protected carbinol 82.11 is reacted with carbon tetrabromide and triphenylphosphine to produce the bromo compound 82.15. This material is heated at 120° with an excess of a trialkyl phosphite 82.7 to give the phosphonate 82.16. Deprotection then yields the amine 82.17.

Using the above procedures, but employing, in place of the carbinol 82.11 different carbinols 82.2, and/or different phosphonates 82.7 the corresponding products 82.9 are obtained.

Scheme 81

Method

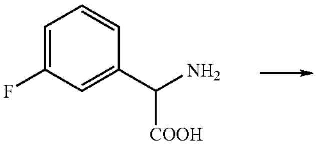

81.1

-continued
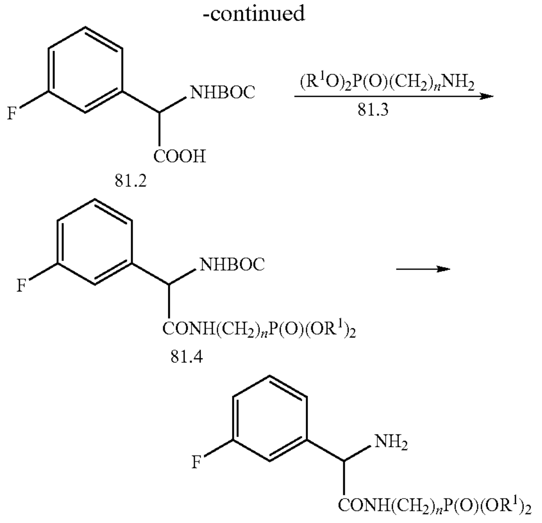
81.2, 81.4, 81.5
Example
-continued
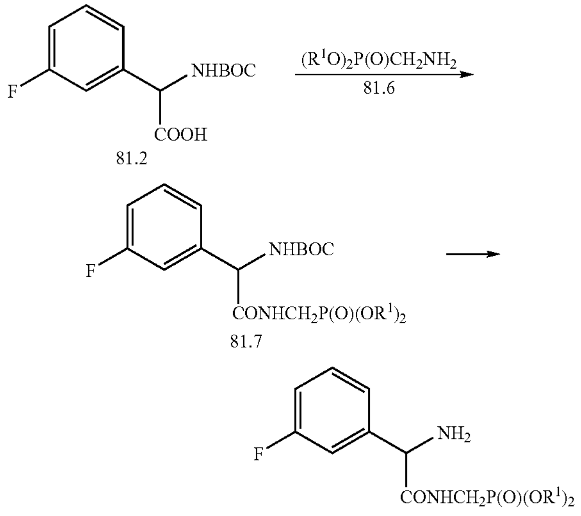
81.2, 81.7, 81.8
Scheme 82
Method
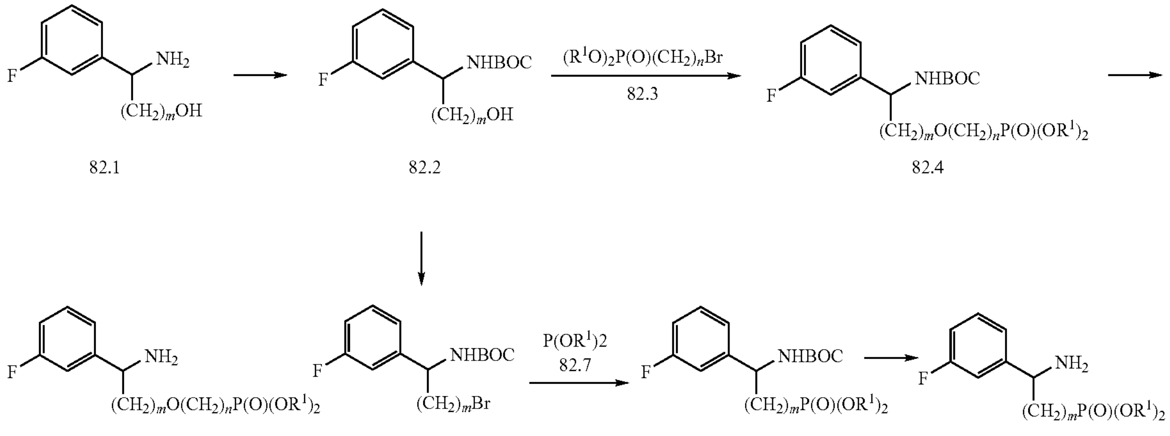
82.1, 82.2, 82.4, 82.5, 82.6, 82.8, 82.9
Example 1
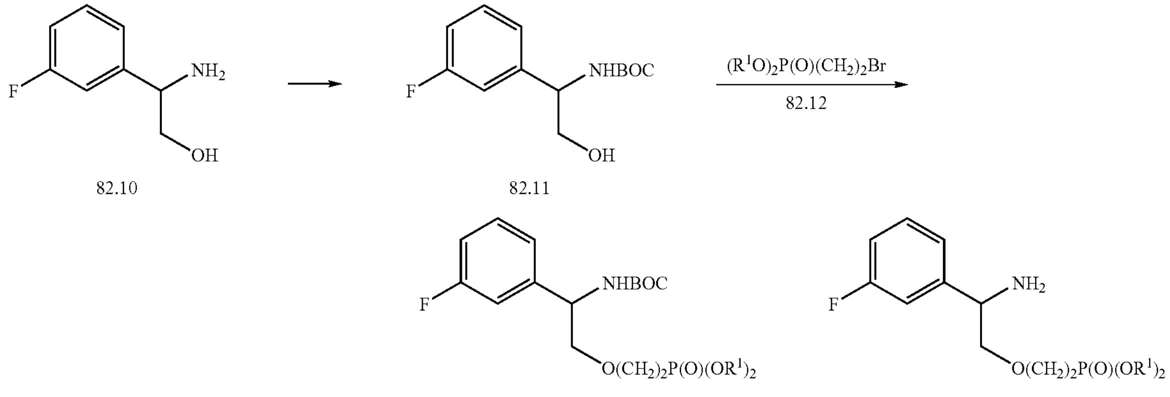
82.10, 82.11, 82.13, 82.14

Preparation of the Phosphonate-containing Tert. Butanol Derivatives 30.1.

Schemes 83-86 illustrate the preparation of the tert. butanol derivatives 30.1 which are employed in the preparation of the phosphonate esters 5.

Scheme 83 depicts the preparation of tert. butanol derivatives in which the phosphonate is attached by means of an alkylene chain. In this procedure, a bromoalkyl carbinol 83.1 is reacted with a trialkyl phosphite 83.2 in an Arbuzov reaction, to afford the phosphonate 83.3. For example, 4-bromo-2-methyl-butan-2-ol 83.4 prepared as described in Bioorg. Med. Chem. Lett., 2001, 9, 525, and a trialkyl phosphite 83.2 are heated at ca. 120° to produce the phosphonate 83.5.

Using the above procedures, but employing, in place of the bromo compound 83.4 different bromo compounds 83.1, and/or different phosphites 83.2 the corresponding products 83.3 are obtained.

Scheme 84 depicts the preparation of tert. butanol derivatives in which the phosphonate is attached by means of an amide linkage. In this procedure, a carboxylic acid 84.1 is coupled with a dialkyl aminoalkyl phosphonate 84.2 to afford the amide 84.3. The reaction is conducted under the conditions previously described (Scheme 1) for the preparation of amides.

For example, equimolar amounts of 3-hydroxy-3-methyl-butyric acid 84.4, (Fluka) and a dialkyl aminoethyl phosphonate 84.5, the preparation of which is described in J. Org. Chem., 2000, 65, 676 are reacted in tetrahydrofuran in the presence of dicyclohexylcarbodiimide to yield the amide 84.6.

Using the above procedures, but employing, in place of the carboxylic acid 84.4 different acids 84.1, and/or different amines 84.2 the corresponding products 84.3 are obtained.

Scheme 85 depicts the preparation of tert. butanol derivatives in which the phosphonate is attached by means of a heteroatom and an alkylene chain. In this procedure, a hydroxy, mercapto or amino-substituted carbinol 85.1 is reacted with a dialkyl bromoalkyl phosphonate 85.2 to afford the ether, thioether or amine products 85.3. The reaction is conducted in a polar organic solvent in the presence of suitable base such as sodium hydride or cesium carbonate. For example, 4-mercapto-2-methyl-butan-2-ol 85.4 prepared as described in Bioorg. Med. Chem. Lett., 1999, 9, 1715, is reacted in tetrahydrofuran containing cesium carbonate with a dialkyl bromobutyl phosphonate 85.5, the preparation of which is described in Synthesis, 1994, 9, 909, to yield the thioether 85.6.

Using the above procedures, but employing, in place of the thiol 85.4 different alcohols, thiol or amines 85.1, and/or different bromides 85.2 the corresponding products 85.3 are obtained.

Scheme 86 depicts the preparation of tert. butanol derivatives in which the phosphonate is attached by means of a nitrogen and an alkylene chain. In this procedure, a hydroxyaldehyde 86.1 is reacted with a dialkyl aminoalkyl phosphonate 86.2 under reductive amination conditions, as described above, (Scheme 55) to afford the amine 86.3.

For example, 3-hydroxy-3-methyl-butyraldehyde 86.4 and a dialkyl aminoethyl phosphonate 86.5 the preparation of which is described in J. Org. Chem., 2000, 65, 676 are reacted together in the presence of sodium triacetoxyborohydride, to yield the amine 86.6.

Using the above procedures, but employing, in place of the aldehyde 86.4 different aldehydes 86.1, and/or different amines 86.2 the corresponding products 86.3 are obtained.

Scheme 82

Example 2

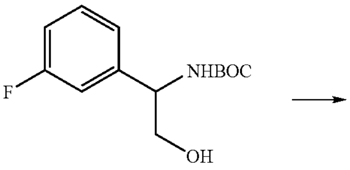

82.11

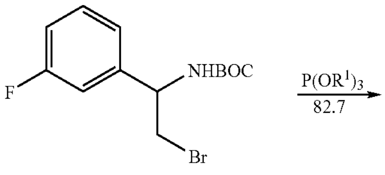

82.15

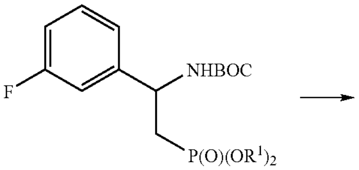

82.16

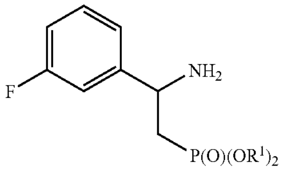

82.17

Scheme 83

Method

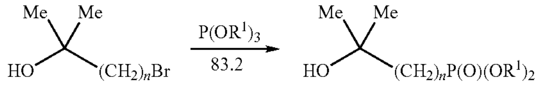

83.1 83.3

Example

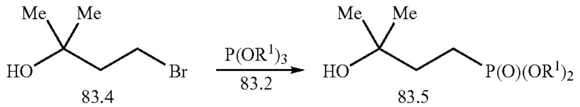

83.4 83.5

Scheme 84

Method

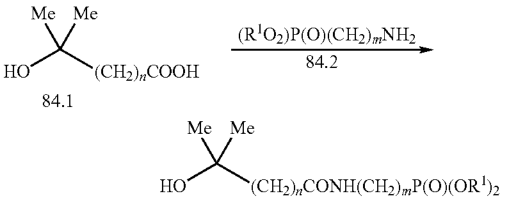

84.1

84.2

84.3

Example

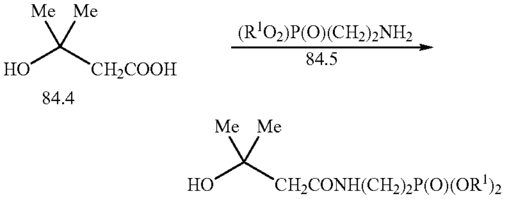

84.4

84.5

84.6

Scheme 85

Method

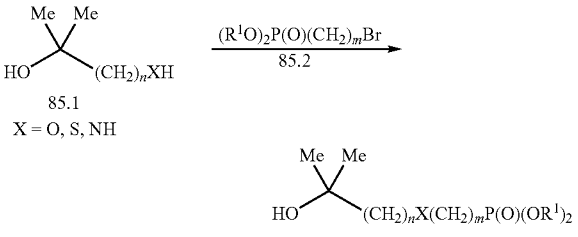

85.1

X = O, S, NH 85.2

85.3

Example

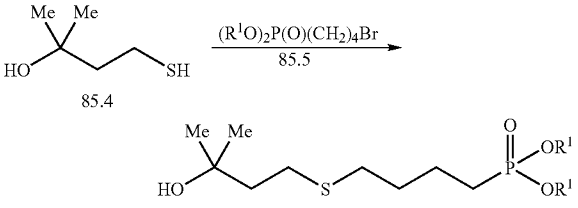

85.4

85.5

85.6

Scheme 86

Method

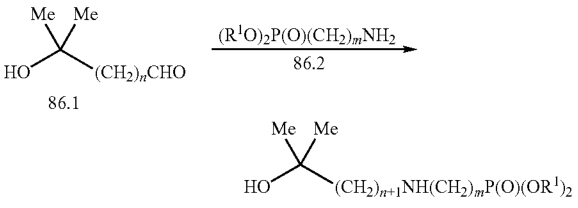

86.1

86.2

86.3

-continued

Example

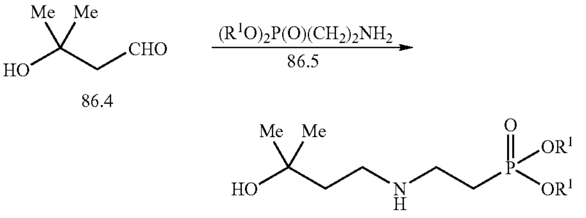

86.4

86.5

86.6

Preparation of the Phosphonate-containing Benzyl Carbamates 43.4.

Schemes 87-91 illustrate methods for the preparation of the benzyl carbamates 43.4 which are employed in the preparation of the phosphonate esters 9. The benzyl alcohols are obtained by reduction of the corresponding benzaldehydes, the preparation of which is described in Schemes 87-90.

Scheme 87 illustrates the preparation of benzaldehyde phosphonates 87.3 in which the phosphonate group is attached by means of an alkylene chain incorporation a nitrogen atom. In this procedure, a benzene dialdehyde 87.1 is reacted with one molar equivalent of a dialkyl aminoalkyl phosphonate 87.2, under reductive amination conditions, as described above in Scheme 55, to yield the phosphonate product 87.3.

For example, benzene-1,3-dialdehyde 87.4 is reacted with a dialkyl aminopropyl phosphonate 87.5, (Acros) and sodium triacetoxyborohydride, to afford the product 87.6.

Using the above procedures, but employing, in place of benzene-1,3-dicarboxaldehyde 87.4, different benzene dialdehydes 87.1, and/or different phosphonates 87.2, the corresponding products 87.3 are obtained.

Scheme 88 illustrates the preparation of benzaldehyde phosphonates either directly attached to the benzene ring or attached by means of a saturated or unsaturated carbon chain. In this procedure, a bromobenzaldehyde 88.1 is coupled, as described above, with a dialkyl alkenylphosphonate 88.2, to afford the alkenyl phosphonate 88.3. Optionally, the product is reduced to afford the saturated phosphonate ester 88.4. Alternatively, the bromobenzaldehyde is coupled, as described above, with a dialkyl phosphite 88.5 to afford the formylphenylphosphonate 88.6.

For example, as shown in Example 1, 3-bromobenzaldehyde 88.7 is coupled with a dialkyl propenylphosphonate 88.8 (Aldrich) to afford the propenyl product 88.9. Optionally, the product is reduced, for example by the use of diimide, to yield the propyl phosphonate 88.10. Using the above procedures, but employing, in place of 3-bromobenzaldehyde 88.7, different bromobenzaldehydes 88.1, and/or different alkenyl phosphonates 88.2, the corresponding products 88.3 and 88.4 are obtained.

Alternatively, as shown in Example 2,4-bromobenzaldehyde is coupled, in the presence of a palladium catalyst, with a dialkyl phosphite 88.5 to afford the 4-formylphenyl phosphonate product 88.12.

Using the above procedures, but employing, in place of 4-bromobenzaldehyde 88.11, different bromobenzaldehydes 88.1, the corresponding products 88.6 are obtained.

Scheme 89 illustrates the preparation of formylphenyl phosphonates in which the phosphonate moiety is attached by means of alkylene chains incorporating two heteroatoms O, S or N. In this procedure, a formyl phenoxy, phenylthio or phenylamino alkanol, alkanethiol or alkylamine 89.1 is reacted with a an equimolar amount of a dialkyl haloalkyl phosphonate 89.2, to afford the phenoxy, phenylthio or phenylamino phosphonate product 89.3. The alkylation reaction is effected in a polar organic solvent such as dimethylformamide or acetonitrile, in the presence of a base. The base employed depends on the nature of the nucleophile 89.1. In cases in which Y is O, a strong base such as sodium hydride or lithium hexamethyldisilazide is employed. In cases in which Y is S or N, a base such as cesium carbonate or dimethylaminopyridine is employed.

For example, 2-(4-formylphenylthio)ethanol 89.4, prepared as described in Macromolecules, 1991, 24, 1710, is reacted in acetonitrile at 60° with one molar equivalent of a dialkyl iodomethyl phosphonate 89.5, (Lancaster) to give the ether product 89.6.

Using the above procedures, but employing, in place of the carbinol 89.4, different carbinols, thiols or amines 89.1, and/or different haloalkyl phosphonates 89.2, the corresponding products 89.3 are obtained.

Scheme 90 illustrates the preparation of formylphenyl phosphonates in which the phosphonate group is linked to the benzene ring by means of an aromatic or heteroaromatic ring. In this procedure, a formylbenzeneboronic acid 90.1 is coupled, in the presence of a palladium catalyst, with one molar equivalent of a dibromoarene, 90.2, in which the group Ar is an aromatic or heteroaromatic group. The coupling of aryl boronates with aryl bromides to afford diaryl compounds is described in Palladium Reagents and Catalysts, by J. Tsuji, Wiley 1995, p. 218. The components are reacted in a polar solvent such as dimethylformamide in the presence of a palladium(0) catalyst and sodium bicarbonate. The product 90.3 is then coupled, as described above (Scheme 50) with a dialkyl phosphite 90.4 to afford the phosphonate 90.5. For example, 4-formylbenzeneboronic acid 90.6 is coupled with 2,5-dibromothiophene 90.7 to yield the phenylthiophene product 90.8. This compound is then coupled with the dialkyl phosphite 90.4 to afford the thienyl phosphonate 90.9.

Using the above procedures, but employing, in place of dibromothiophene 90.7, different dibromoarenes 90.2, and/or different formylphenyl boronates 90.1, the corresponding products 90.5 are obtained.

Scheme 91 illustrates the preparation of the benzyl carbamates 43.4 which are employed in the preparation of the phosphonate esters 9. In this procedure, the substituted benzaldehydes 91.1, prepared as shown in Schemes 87-90, are converted into the corresponding benzyl alcohols 91.2. The reduction of aldehydes to afford alcohols is described in Comprehensive Organic Transformations, by R. C. Larock, VCH, 1989, p. 527ff. The transformation is effected by the use of reducing agents such as sodium borohydride, lithium aluminum tri-tertiarybutoxy hydride, diisobutyl aluminum hydride and the like. The resultant benzyl alcohol is then reacted with the aminoester 91.3 to afford the carbamate 91.4. The reaction is performed under the conditions described below, Scheme 98. For example, the benzyl alcohol is reacted with carbonyldiimidazole to produce an intermediate benzyloxycarbonyl imidazole, and the intermediate is reacted with the aminoester 91.3 to afford the carbamate 91.4. The methyl ester is then hydrolyzed to yield the carboxylic acid 43.4.

Scheme 87

Method

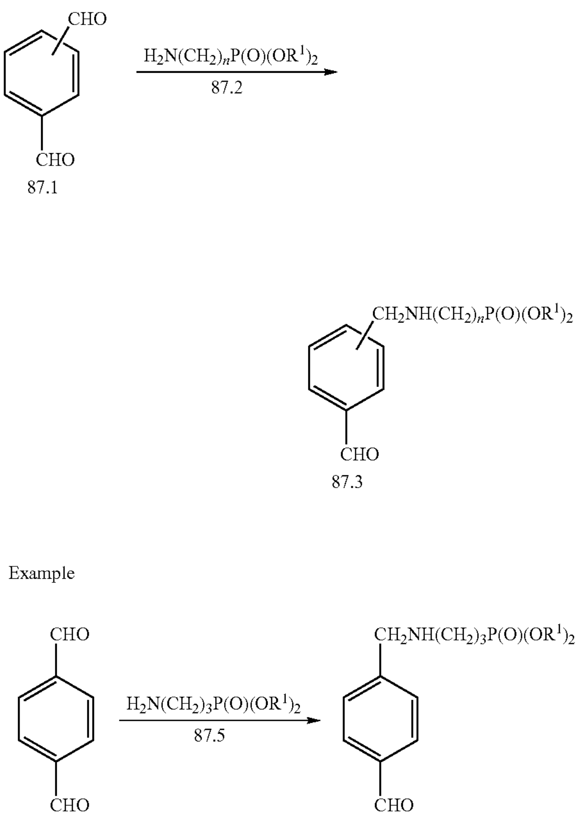

87.1 87.3

Example 87.4 87.6

Scheme 88

Method

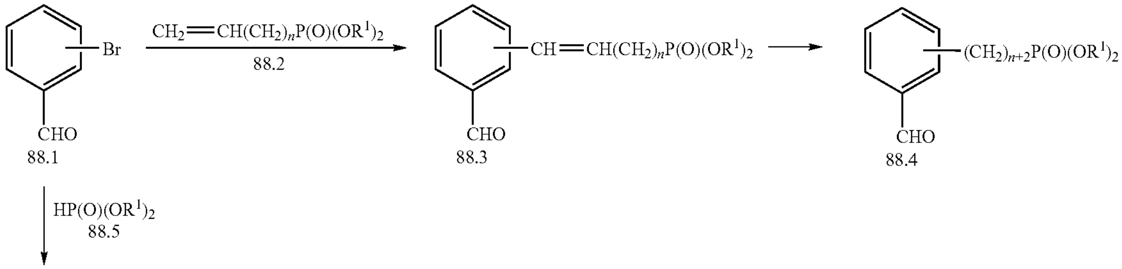

88.1 88.3 88.4

-continued
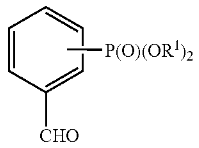
88.6
Example 1
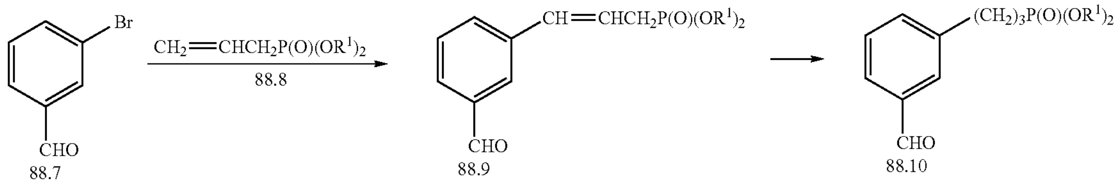
88.7 88.9 88.10
Example 2
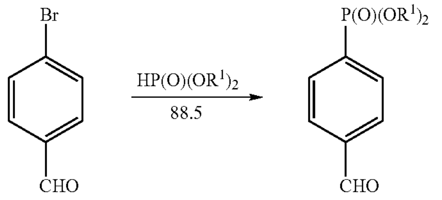
88.11 88.12
Scheme 89
Method
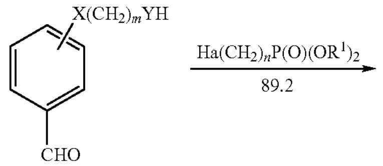
X, Y = O, S, NH
89.1
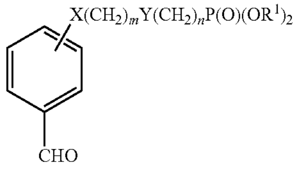
89.3
Example
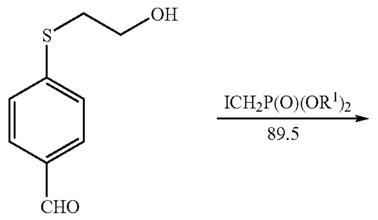
89.4
-continued
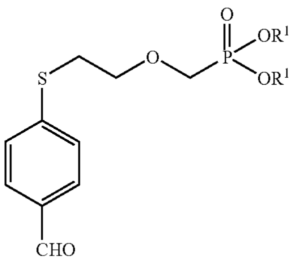
89.6
Scheme 90
Method
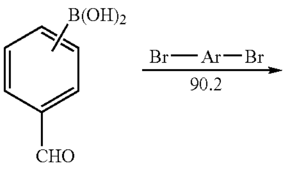
90.1
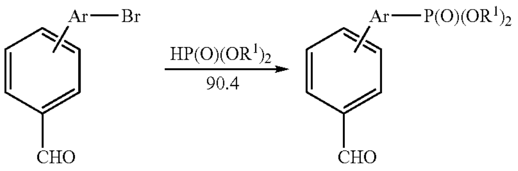
90.3 90.5

-continued

Example

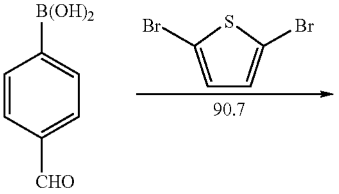
90.7

90.6

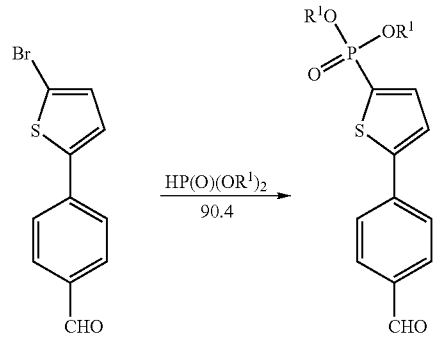

90.8 90.9

Scheme 91

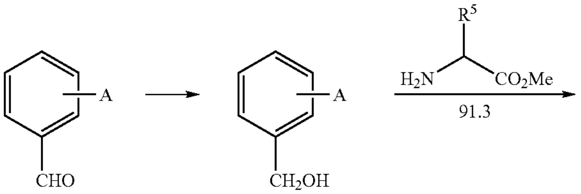

91.1 91.2

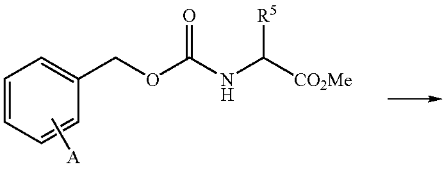
91.4

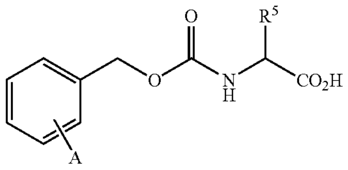
43.4

Preparation of Phosphonate-containing Benzenesulfonyl Chlorides 20.2.

Schemes 92-97 illustrate methods for the preparation of the sulfonyl chlorides 20.2 which are employed in the preparation of the phosphonate esters 4. Sulfonic acids and/or sulfonyl halides are obtained by oxidation of the corresponding thiols, as described in Synthetic Organic Chemistry, R. B. Wagner, H. D. Zook, Wiley, 1953, p. 813, and in Tet. 1965, 21, 2271. For example, the phosphonate-containing thiols which are prepared according to Schemes 63-72 are transformed into the corresponding sulfonic acids by oxidation with bromine in aqueous organic solution, as described in J. Am. Chem. Soc., 59, 811, 1937, or by oxidation with hydrogen peroxide, as described in Rec. Trav. Chim., 54, 205, 1935, or by reaction with oxygen in alkaline solution, as described in Tet. Let., 1963, 1131, or by the use of potassium superoxide, as described in Aust. J. Chem., 1984, 37, 2231. Schemes 92-96 describe the preparation of phosphonate-substituted benzenesulfonic acids; Scheme 97 describes the conversion of the sulfonic acids into the corresponding sulfonyl chlorides. Alternatively, the intermediate thiols, when propduced, can be directly converted to the sulfonyl chloride as described in Scheme 97a Scheme 92 depicts the preparation of variously substituted benzenesulfonic acids in which the phosphonate group is directly attached to the benzene ring. In this procedure, a bromo-substituted benzenethiol 92.1 is protected, as previously described. The protected product 92.2 is then reacted, in the presence of a palladium catalyst, with a dialkyl phosphite 92.3, to give the corresponding phosphonate 92.4. The thiol group is then deprotected to afford the thiol 92.5, and this compound is oxidized to afford the sulfonic acid 92.6.

For example, 4-bromobenzenethiol 92.7 is converted into the S-adamantyl derivative 92.8, by reaction with 1-adamantanol in trifluoroacetic acid, as described in Chem. Pharm. Bull., 26, 1576, 1978. The product is then reacted with a dialkyl phosphite and a palladium catalyst, as described previously, to yield the phosphonate 92.9. The adamantyl group is then removed by reaction with mercuric acetate in trifluoroacetic acid, as described in Chem. Pharm. Bull., 26, 1576, 1978, to give the thiol 92.10. The product is then reacted with bromine in aqueous solution to prepare the sulfonic acid 92.11.

Using the above procedures, but employing, in place of the thiol 92.7, different thiols 92.1, and/or different dialkyl phosphites 92.3, the corresponding products 92.6 are obtained.

Scheme 93 illustrates the preparation of amino-substituted benzenesulfonic acids in which the phosphonate group is attached by means of an alkoxy group. In this procedure, a hydroxy amino-substituted benzenesulfonic acid 93.1 is reacted with a dialkyl bromoalkyl phosphonate 93.2 to afford the ether 93.3. The reaction is performed in a polar solvent such as dimethylformamide in the presence of a base such as potassium carbonate. The yield of the product 93.3 is increased by treatment of the crude reaction product with dilute aqueous base, so as to hydrolyze any sulfonic esters which are produced.

For example, 3-amino-4-hydroxybenzenesulfonic acid 93.4 (Fluka) is reacted with a dialkyl bromopropyl phosphonate 93.5 prepared as described in J. Am. Chem. Soc., 2000, 122, 1554, in dimethylformamide containing potassium carbonate, followed by the addition of water, to produce the ether 93.6.

Using the above procedures, but employing, in place of the phenol 93.4, different phenols 93.1, and/or different phosphonates 93.2, the corresponding products 93.3 are obtained.

Scheme 94 illustrates the preparation of methoxyl-substituted benzenesulfonic acids in which the phosphonate group is attached by means of an amide group. In this procedure, a methoxy amino-substituted benzenesulfonic acid 94.1 is reacted, as described previously for the preparation of amides, with a dialkyl carboxyalkyl phosphonate 94.2 to produce the amide 94.3.

For example, 3-amino-4-methoxybenzenesulfonic acid 94.4, (Acros) is reacted in dimethylformamide solution with a dialkyl phosphonoacetic acid 94.2 (Aldrich) and dicyclohexyl carbodiimide, to produce the amide 94.6.

Using the above procedures, but employing, in place of the amine 94.4, different amines 94.1, and/or different phosphonates 94.2, the corresponding products 94.3 are obtained.

Scheme 95 illustrates the preparation of substituted benzenesulfonic acids in which the phosphonate group is attached by means of a saturated or unsaturated alkylene group. In this procedure, a halo-substituted benzenesulfonic acid 95.1 is coupled, in a palladium catalyzed Heck reaction with a dialkyl alkenyl phosphonate 95.2 to afford the phosphonate 95.3. Optionally, the product is reduced, for example by catalytic hydrogenation over a palladium catalyst, to give the saturated analog 95.4.

For example, 4-amino-3-chlorobenzenesulfonic aid 95.5 (Acros) is reacted in N-methylpyrrolidinone solution at 80° with a dialkyl vinylphosphonate 95.6 (Aldrich), palladium (II) chloride bis(acetonitrile), sodium acetate and tetraphenylphosphonium chloride, as described in Ang. Chem. Int. Ed. Engl., 37, 481, 1998, to produce the olefinic product 95.7. Catalytic hydrogenation using a 5% palladium on carbon catalyst then affords the saturated analog 95.8.

Using the above procedures, but employing, in place of the chloro compound 95.5, different chlorides 95.1, and/or different phosphonates 95.2, the corresponding products 95.3 and 95.4 are obtained.

Scheme 96 depicts the preparation of benzenesulfonic acids in which the phosphonate group is attached by means of an amide linkage. In this procedure, an amino carboxy substituted benzene thiol 96.1 is coupled with a dialkyl aminoalkyl phosphonate 96.2 to produce the amide 96.3. The product is then oxidized, as described above, to afford the corresponding sulfonic acid 96.4.

For example, 2-amino-5-mercaptobenzoic acid 96.5, prepared as described in Pharmazie, 1973, 28, 433, is reacted with a dialkyl aminoethyl phosphonate 96.6 and dicyclohexyl carbodiimide, to prepare the amide 96.7. The product is then oxidized with aqueous hydrogen peroxide to yield the sulfonic acid 96.8.

Using the above procedures, but employing, in place of the carboxylic acid 96.5, different acids 96.1, and/or different phosphonates 96.2, the corresponding products 96.4 are obtained.

Scheme 97 illustrates the conversion of benzenesulfonic acids into the corresponding sulfonyl chlorides. The conversion of sulfonic acids into sulfonyl chlorides is described in Synthetic Organic Chemistry, R. B. Wagner, H. D. Zook, Wiley, 1953, p. 821. The transformation is effected by the use, of reagents such as thionyl chloride or phosphorus pentachloride.

For example, as shown in Scheme 97, the variously substituted phosphonate-containing benzenesulfonic acids 97.1, prepared as described above, are treated with thionyl chloride, oxalyl chloride, phosphorus pentachloride, phosphorus oxychloride and the like to prepare the corresponding sulfonyl chlorides 97.2.

Scheme 97a illustrates the conversion of thiols into the corresponding sulfonyl chlorides which can be applied to any of the thiol intermediates in Schemes 92-96. The thiol is oxidized as described in Synthesis 1987, 4, 409 or J. Med. Chem. 1980, 12, 1376 to afford the sulfonyl chloride directly. For example, treatment of protected thiol 97a.1, prepared from 96.7 using standard protecting groups for amines as described in Greene and Wuts, third edition, ch 7, with HCl and chlorine affords the sulfonyl chloride 97a.2. Alternatively treatment of 92.10 with the same conditions gives the sulfonyl chloride 97a.3.

Scheme 92

Method

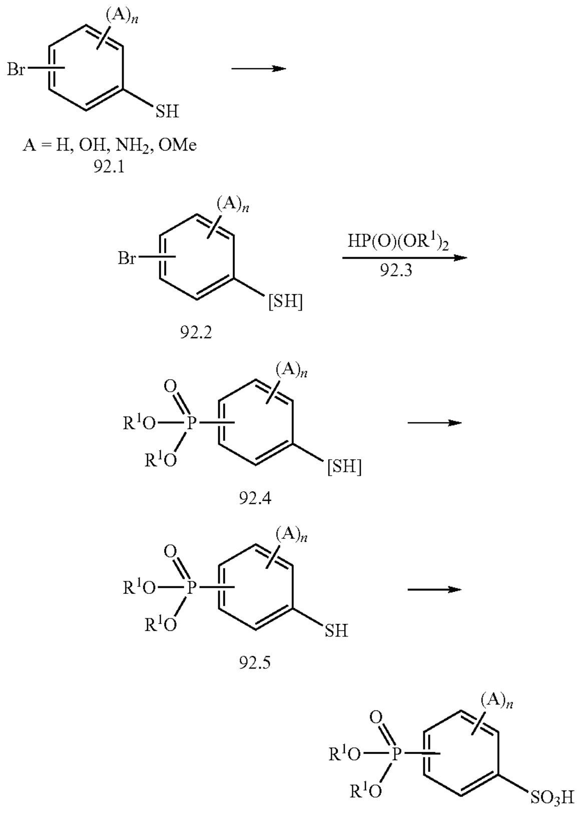

A = H, OH, $NH_2$, OMe 92.1 92.2 92.4 92.5 92.6

Example

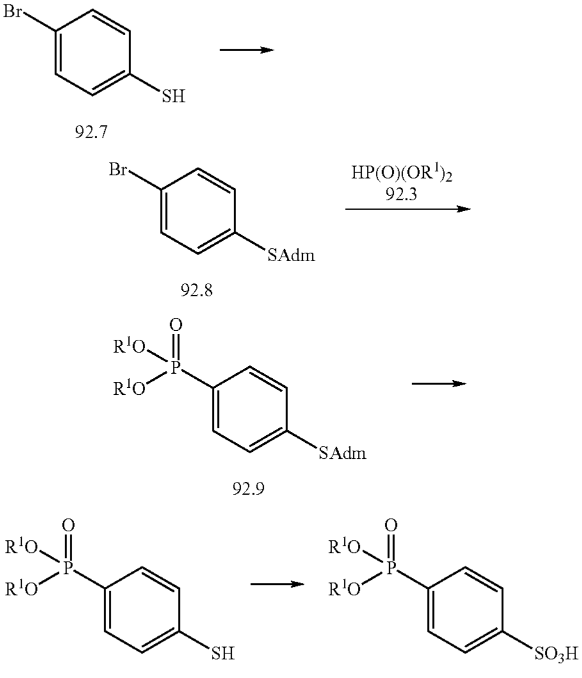

92.7 92.8 92.9 92.10 92.11

Scheme 93
Method
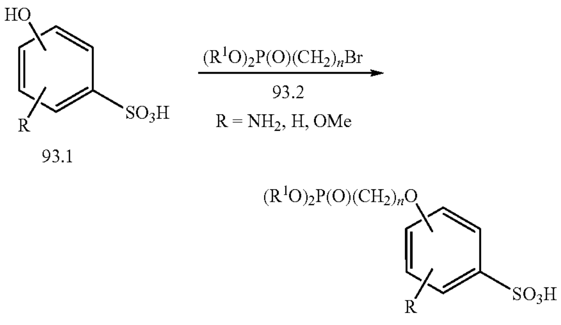
93.1
93.3
Example
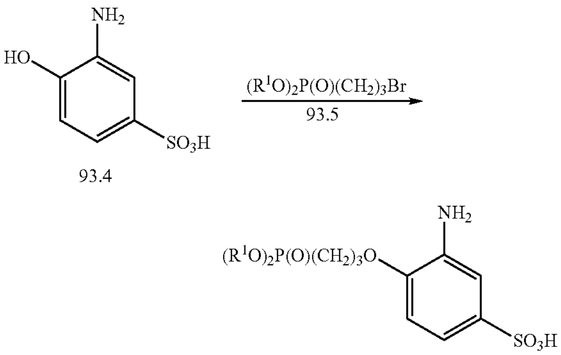
93.4
93.6
Scheme 94
Method
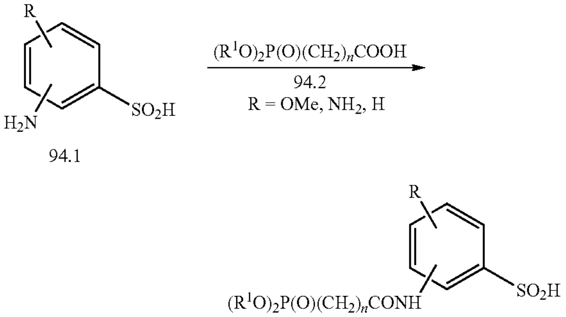
94.1
94.3
Example
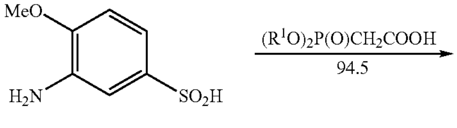
94.4
-continued
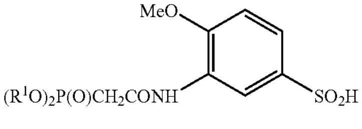
94.6
Scheme 95
Method
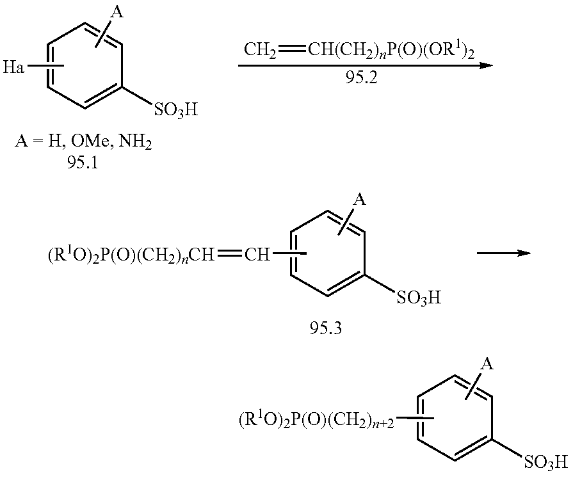
95.1
95.3
95.4
Example
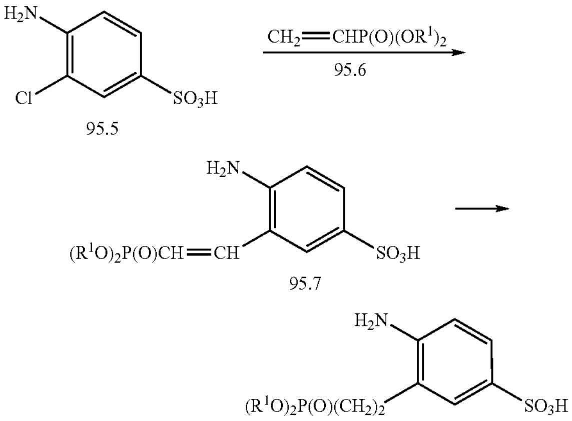
95.5
95.7
95.8
Scheme 96
Method
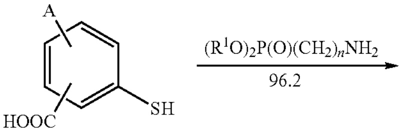
96.1

-continued

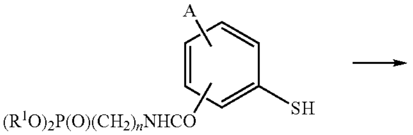

96.3

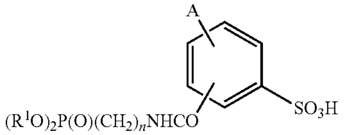

96.4

Example

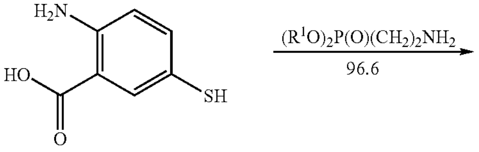

96.5

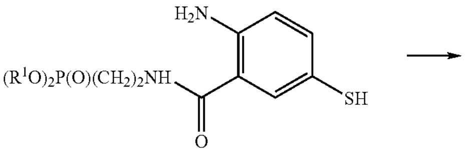

96.7

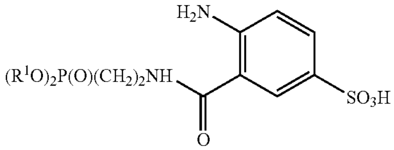

96.8

Scheme 97

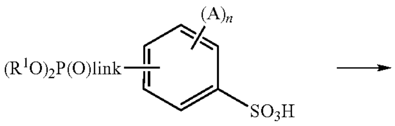

A = H, Ha, MeO, $NH_2$ etc
97.1

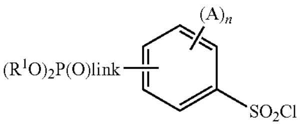

97.2

Scheme 97a

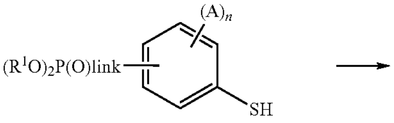

A = H, Ha, MeO, $NH_2$ etc
97a.1

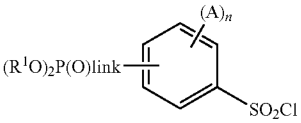

97.2

Example

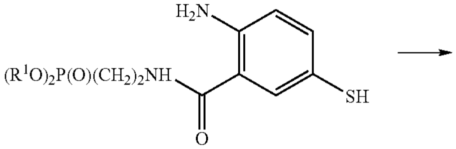

97a.1

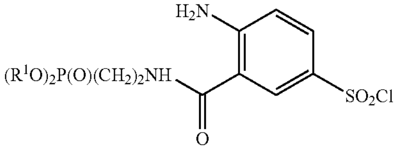

97a.2

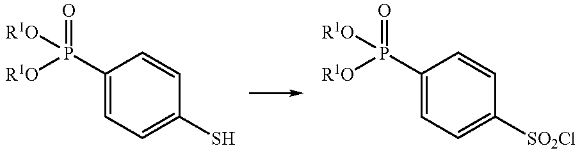

92.10

97a.3

Preparation of Carbamates.

The phosphonate esters 1-4 in which $R^4$ is formally derived from the carboxylic acids shown in Chart 5c, and the phosphonate esters 5 and 9 contain a carbamate linkage. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 98 illustrates various methods by which the carbamate linkage is synthesized. As shown in Scheme 98, in the general reaction generating carbamates, a carbinol 98.1, is converted into the activated derivative 98.2 in which Lv is a leaving group such as halo, imidazolyl, benztriazolyl and the like, as described below. The activated derivative 98.2 is then reacted with an amine 98.3, to afford the carbamate product 98.4. Examples 1-7 in Scheme 98 depict methods by which the general reaction is effected. Examples 8-10 illustrate alternative methods for the preparation of carbamates.

Scheme 98, Example 1 illustrates the preparation of carbamates employing a chloroformyl derivative of the carbinol 98.1. In this procedure, the carbinol is reacted with phosgene, in an inert solvent such as toluene, at about 0°, as described in Org. Syn. Coll. Vol. 3, 167, 1965, or with an equivalent reagent such as trichloromethoxy chloroformate, as described in Org. Syn. Coll. Vol. 6, 715, 1988, to afford the chloroformate 98.6. The latter compound is then reacted with the amine component 98.3, in the presence of an organic or inorganic base, to afford the carbamate 98.7. For example, the chloroformyl compound 98.6 is reacted with the amine 98.3 in a water-miscible solvent such as tetrahydrofuran, in the presence of aqueous sodium hydroxide, as described in Org. Syn. Coll. Vol. 3, 167, 1965, to yield the carbamate 98.7. Alternatively, the reaction is performed in dichloromethane in the presence of an organic base such as diisopropylethylamine or dimethylaminopyridine.

Scheme 98, Example 2 depicts the reaction of the chloroformate compound 98.6 with imidazole to produce the imidazolide 98.8. The imidazolide product is then reacted with the amine 98.3 to yield the carbamate 98.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in J. Med. Chem., 1989, 32, 357.

Scheme 98 Example 3, depicts the reaction of the chloroformate 98.6 with an activated hydroxyl compound R"OH, to yield the mixed carbonate ester 98.10. The reaction is conducted in an inert organic solvent such as ether or dichloromethane, in the presence of a base such as dicyclohexylamine or triethylamine. The hydroxyl component R"OH is selected from the group of compounds 98.19-98.24 shown in Scheme 98, and similar compounds. For example, if the component R"OH is hydroxybenztriazole 98.19, N-hydroxysuccinimide 98.20, or pentachlorophenol, 98.21, the mixed carbonate 98.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 98.22 or 2-hydroxypyridine 98.23 is performed in an ethereal solvent in the presence of triethylamine, as described in Syn., 1986, 303, and Chem. Ber. 118, 468, 1985.

Scheme 98 Example 4 illustrates the preparation of carbamates in which an alkyloxycarbonylimidazole 98.8 is employed. In this procedure, a carbinol 98.5 is reacted with an equimolar amount of carbonyl diimidazole 98.11 to prepare the intermediate 98.8. The reaction is conducted in an aprotic organic solvent such as dichloromethane or tetrahydrofuran. The acyloxyimidazole 98.8 is then reacted with an equimolar amount of the amine $R'NH_2$ to afford the carbamate 98.7. The reaction is performed in an aprotic organic solvent such as dichloromethane, as described in Tet. Lett., 42, 2001, 5227, to afford the carbamate 98.7.

Scheme 98, Example 5 illustrates the preparation of carbamates by means of an intermediate alkoxycarbonylbenztriazole 98.13. In this procedure, a carbinol ROH is reacted at ambient temperature with an equimolar amount of benztriazole carbonyl chloride 98.12, to afford the alkoxycarbonyl product 98.13. The reaction is performed in an organic solvent such as benzene or toluene, in the presence of a tertiary organic amine such as triethylamine, as described in Syn., 1977, 704. The product is then reacted with the amine $R'NH_2$ to afford the carbamate 98.7. The reaction is conducted in toluene or ethanol, at from ambient temperature to about 80° as described in Syn., 1977, 704.

Scheme 98, Example 6 illustrates the preparation of carbamates in which a carbonate $(R''O)_2CO$, 98.14, is reacted with a carbinol 98.5 to afford the intermediate alkyloxycarbonyl intermediate 98.15. The latter reagent is then reacted with the amine $R'NH_2$ to afford the carbamate 98.7. The procedure in which the reagent 98.15 is derived from hydroxybenztriazole 98.19 is described in Synthesis, 1993, 908; the procedure in which the reagent 98.15 is derived from N-hydroxysuccinimide 98.20 is described in Tet. Lett., 1992, 2781; the procedure in which the reagent 98.15 is derived from 2-hydroxypyridine 98.23 is described in Tet. Lett., 1991, 4251; the procedure in which the reagent 98.15 is derived from 4-nitrophenol 98.24 is described in Syn. 1993, 199. The reaction between equimolar amounts of the carbinol ROH and the carbonate 98.14 is conducted in an inert organic solvent at ambient temperature.

Scheme 98, Example 7 illustrates the preparation of carbamates from alkoxycarbonyl azides 98.16. In this procedure, an alkyl chloroformate 98.6 is reacted with an azide, for example sodium azide, to afford the alkoxycarbonyl azide 98.16. The latter compound is then reacted with an equimolar amount of the amine $R'NH_2$ to afford the carbamate 98.7. The reaction is conducted at ambient temperature in a polar aprotic solvent such as dimethylsulfoxide, for example as described in Syn., 1982, 404.

Scheme 98, Example 8 illustrates the preparation of carbamates by means of the reaction between a carbinol ROH and the chloroformyl derivative of an amine 98.17. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 98.7.

Scheme 98, Example 9 illustrates the preparation of carbamates by means of the reaction between a carbinol ROH and an isocyanate 98.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 98.7.

Scheme 98, Example 10 illustrates the preparation of carbamates by means of the reaction between a carbinol ROH and an amine $R'NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 98.7.

Scheme 98

General reaction

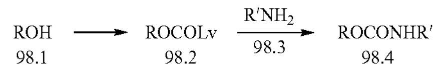

Examples (1)

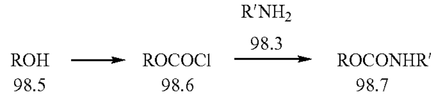

(2)

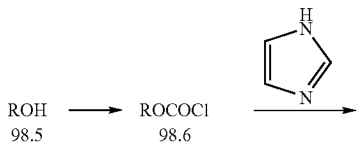

-continued

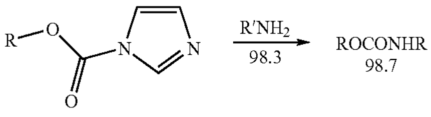

98.8

(3)

ROH 98.5 ROCOCl 98.6 R"OH 98.9 ROCOOR" 98.10 R'NH2 98.3 ROCONHR' 98.7

(4)

ROH
98.5

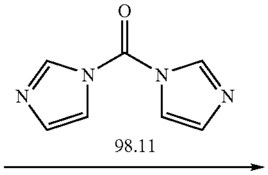

98.11

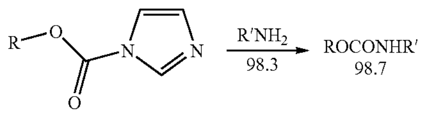

98.8

(5)

ROH
98.5

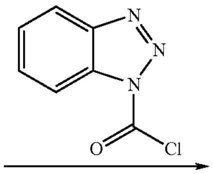

98.12

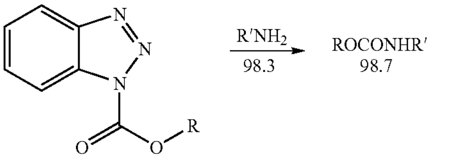

98.13

(6)

ROH 98.5 $(R''O_2)C{=}O$ 98.14 ROCOR" 98.5 R'NH2 98.3 ROCONHR' 98.7

(7)

ROH 98.5 ROCOCl 98.6 $ROCON_3$ 98.16 R'NH2 98.3 ROCONHR' 98.7

(8)

ROH 98.5 R'NHCOCl 98.17 ROCONHR' 98.7

(9)

ROH 98.5 R'NCO 98.18 ROCONHR' 98.7

(10)

ROH 98.5 $R'NH_2$ 98.3 ROCONHR' 98.7

-continued

R"OH =

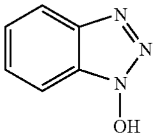

98.19

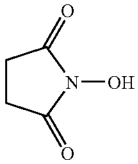

98.20

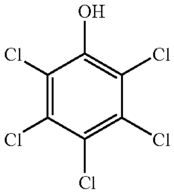

98.21

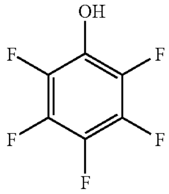

98.22

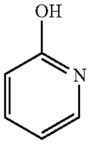

98.23

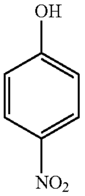

98.24

Interconversions of the Phosphonates R-link-P(O)$(OR^1)_2$, R-link-P(O)$(OR^1)$(OH) and R-link-P(O)$(OH)_2$.

Schemes 1-97 described the preparations of phosphonate esters of the general structure R-link-P(O)$(OR^1)_2$, in which the groups $R^1$, the structures of which are defined in Charts 1 and 2, may be the same or different. The $R^1$ groups attached to the phosphonate esters 1-13, or to precursors thereto, may be changed using established chemical transformations. The interconversions reactions of phosphonates are illustrated in Scheme 99. The group R in Scheme 99 represents the substructure to which the substituent link-P(O)$(OR^1)_2$ is attached, either in the compounds 1-13 or in precursors thereto. The $R^1$ group may be changed, using the procedures described below, either in the precursor compounds, or in the esters 1-13. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 99.1 into the corresponding phosphonate monoester 99.2 (Scheme 99, Reaction 1) is accomplished by a number of methods. For example, the ester 99.1 in which $R^1$ is an aralkyl group such as benzyl, is converted into the monoester compound 99.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 99.1 in which $R^1$ is an aryl group such as phenyl, or an alkenyl group such as allyl, into the monoester 99.2 is effected by treatment of the ester 99.1 with a base such as aqueous sodium hydroxide in acetonitrile or lithium hydroxide in aqueous tetrahydrofuran.

Phosphonate diesters 99.1 in which one of the groups $R^1$ is aralkyl, such as benzyl, and the other is alkyl, are converted into the monoesters 99.2 in which $R^1$ is alkyl by hydrogenation, for example using a palladium on carbon catalyst. Phosphonate diesters in which both of the groups $R^1$ are alkenyl, such as allyl, are converted into the monoester 99.2 in which $R^1$ is alkenyl, by treatment with chlorotris(triphenylphosphine)rhodium (Wilkinson's catalyst) in aqueous ethanol at reflux, optionally in the presence of diazabicyclooctane, for example by using the procedure described in J. Org. Chem., 38, 3224, 1973 for the cleavage of allyl carboxylates.

The conversion of a phosphonate diester 99.1 or a phosphonate monoester 99.2 into the corresponding phosphonic acid 99.3 (Scheme 99, Reactions 2 and 3) is effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 99.2 in which $R^1$ is aralkyl such as benzyl, is converted into the corresponding phosphonic acid 99.3 by hydrogenation over a palladium catalyst, or by treatment with hydrogen chloride in an ethereal solvent such as dioxan. A phosphonate monoester 99.2 in which $R^1$ is alkenyl such as, for example, allyl, is converted into the phosphonic acid 99.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 99.1 in which $R^1$ is benzyl is described in J. Org. Chem., 24, 434, 1959. Platinum-catalyzed hydrogenolysis of phosphonate esters 99.1 in which $R^1$ is phenyl is described in J. Am. Chem. Soc., 78, 2336, 1956.

The conversion of a phosphonate monoester 99.2 into a phosphonate diester 99.1 (Scheme 99, Reaction 4) in which the newly introduced $R^1$ group is alkyl, aralkyl, haloalkyl such as chloroethyl, or aralkyl is effected by a number of reactions in which the substrate 99.2 is reacted with a hydroxy compound $R^1OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 99.2 to the diester 99.1 is effected by the use of the Mitsonobu reaction, as described above, Scheme 49. The substrate is reacted with the hydroxy compound $R^1OH$, in the presence of diethyl azodicarboxylate and a triarylphosphine such as triphenyl phosphine. Alternatively, the phosphonate monoester 99.2 is transformed into the phosphonate diester 99.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester 99.2 is transformed into the chloro analog $RP(O)(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester 99.1.

A phosphonic acid R-link-$P(O)(OH)_2$ is transformed into a phosphonate monoester $RP(O)(OR^1)(OH)$ (Scheme 99, Reaction 5) by means of the methods described above of for the preparation of the phosphonate diester R-link-$P(O)(OR^1)_2$ 99.1, except that only one molar proportion of the component $R^1OH$ or $R^1Br$ is employed.

A phosphonic acid R-link-$P(O)(OH)_2$ 99.3 is transformed into a phosphonate diester R-link-$P(O)(OR^1)_2$ 99.1 (Scheme 99, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine.

Alternatively, phosphonic acids 99.3 are transformed into phosphonic esters 99.1 in which $R^1$ is aryl, by means of a coupling reaction employing, for example, dicyclohexylcarbodiimide in pyridine at ca 70°. Alternatively, phosphonic acids 99.3 are transformed into phosphonic esters 99.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 99.1.

Scheme 99

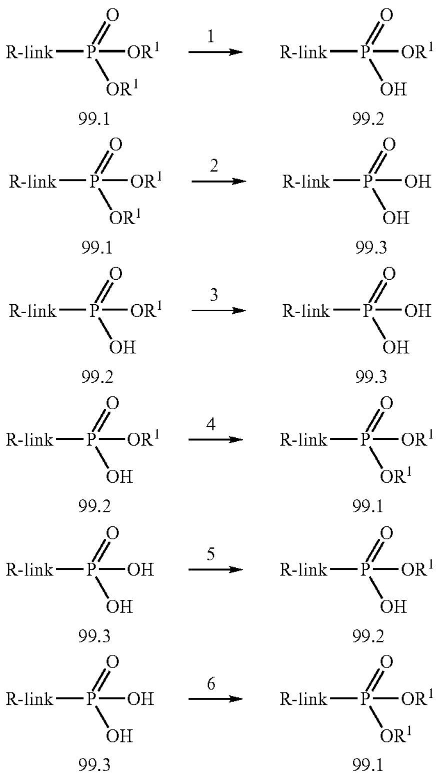

99.1 → 99.2; 99.1 → 99.3; 99.2 → 99.3; 99.2 → 99.1; 99.3 → 99.2; 99.3 → 99.1

General applicability of methods for introduction of phosphonate substituents.

The procedures described for the introduction of phosphonate moieties (Schemes 47-97) are, with appropriate modifications known to one skilled in the art, transferable to different chemical substrates. Thus, the methods described above for the introduction of phosphonate groups into hydroxymethyl benzoic acids, (Schemes 47-51) are applicable to the introduction of phosphonate moieties into quinolines, thiophenols, isobutylamines, cyclopentylamines, tert. butanols, benzyl alcohols, phenylalanines, benzylamines and benzenesulfonic acids, and the methods described for the introduction of phosphonate moieties into the above-named substrates (Schemes 52-97) are applicable to the introduction of phosphonate moieties into hydroxymethyl benzoic acid substrates.

Preparation of Phosphonate Intermediates 11-13 with Phosphonate Moieties Incorporated Into the $R^2$, $R^3$ or $R^4$ Groups.

The chemical transformations described in Schemes 1-99 illustrate the preparation of compounds 1-10 in which the phosphonate ester moiety is attached to the substructures listed above. The various chemical methods employed for the introduction of phosphonate ester groups into the above-named moieties can, with appropriate modifications known to those skilled in the art, be applied to the introduction of a phosphonate ester group into the compounds $R^4COOH$, $R^3Cl$, $R^2NH_2$. The resultant phosphonate-containing analogs, designated as $R^{4a}COOH$, $R^{3a}Cl$ and $NH_2R^{2a}$ are then, using the procedures described above, employed in the preparation of the compounds 11, 12 and 13. The procedures required for the utilization of the phosphonate-containing analogs are the same as those described above for the utilization of the compounds $R^2NH_2$, $R^3Cl$ and $R^4COOH$.

KNI-like Phosphonate Protease Inhibitors (KNILPPI)

Preparation of the Intermediate Phosphonate Esters 1-12.

The structures of the intermediate phosphonate esters 1 to 12 and the structures for the component groups $R^1$, $R^2$, $R^1$, $R^7$, $R^9$, X and Y of this invention are shown in Charts 1 and 2. The structures of the $R^8COOH$ components are shown in Charts 3a, 3b and 3c.

The structures of the $R^{10}R^{11}NH$ and $R^4R^5NH$ components are shown in Charts 4a, and 4b respectively. The structures of the $R^6XCH_2$ groups are shown in Chart 5. Specific stereoisomers of some of the structures are shown in Charts 1-5; however, all stereoisomers are utilized in the syntheses of the compounds 1 to 12. Subsequent chemical modifications to the compounds 1 to 12, as described herein, permit the synthesis of the final compounds of this invention.

The intermediate compounds 1 to 12 incorporate a phosphonate moiety $(R^1O)_2P(O)$ connected to the nucleus by means of a variable linking group, designated as "link" in the attached structures. Charts 6 and 7 illustrate examples of the linking groups present in the structures 1-12.

Schemes 1-103 illustrate the syntheses of the intermediate phosphonate compounds of this invention, 1-10, and of the intermediate compounds necessary for their synthesis. The preparation of the phosphonate esters 11 and 12, in which the phosphonate moiety is incorporated into the groups $R^8COOH$ and $R^{10}R^{11}NH$, is also described below.

CHART 1

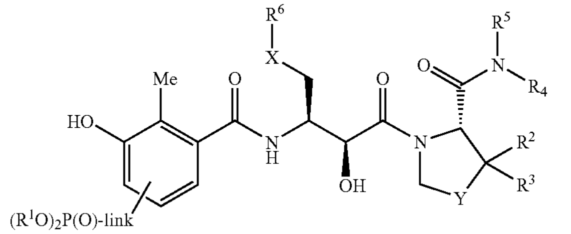

1

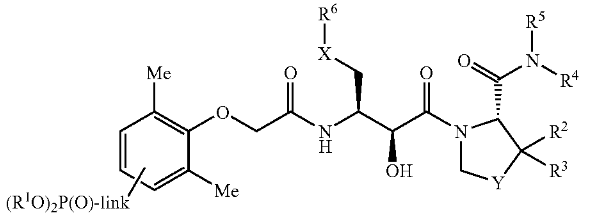

2

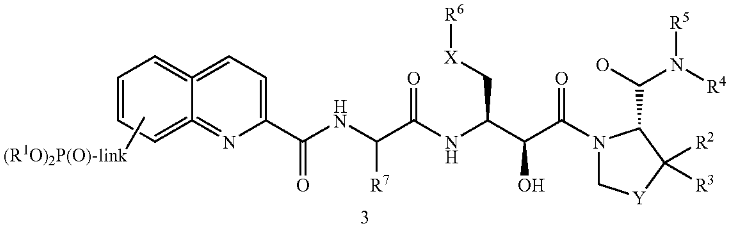

3

CHART 1-continued
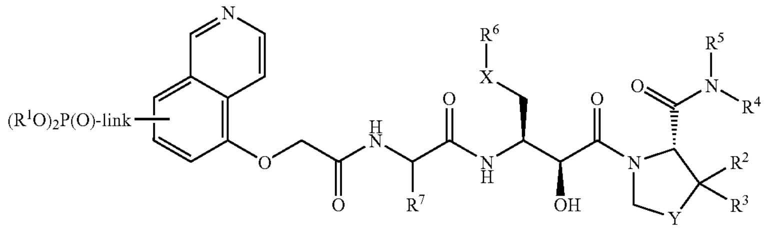
4
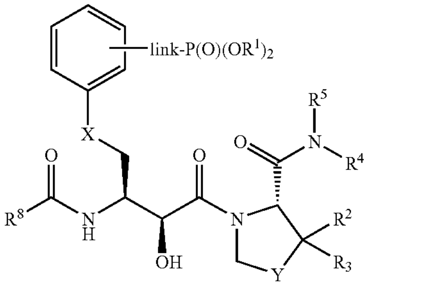
5
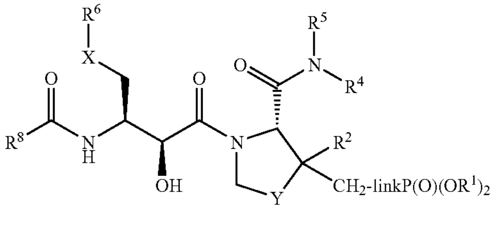
6
$R^1$ = H, alkyl, haloalkyl, alkenyl, aralkyl, aryl
$R^2$, $R^3$ = H, H; H, methyl; methyl, methyl; H, Cl
$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$
X = S or direct bond
Y = S, $CH_2$
CHART 2
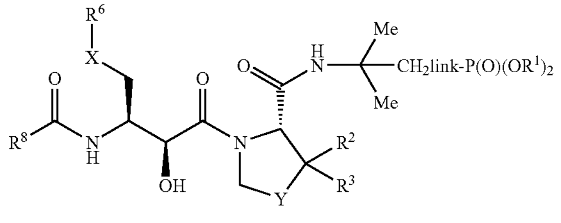
7
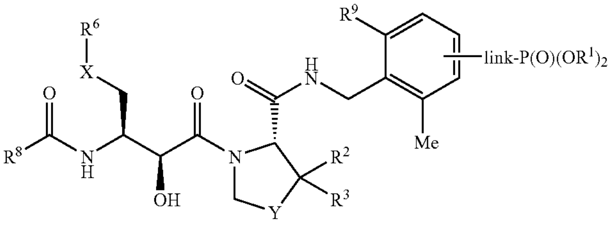
8

CHART 2-continued
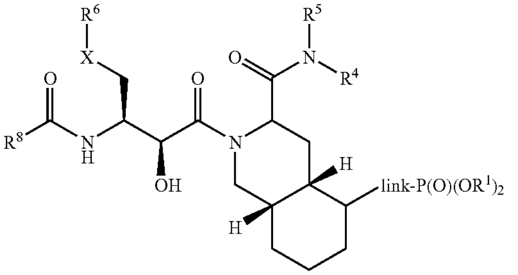
9
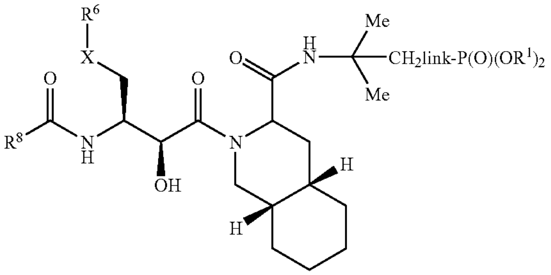
10
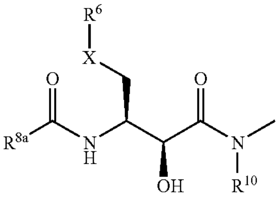
11
$R^{8a}$ = phosphonate-containing $R^8$
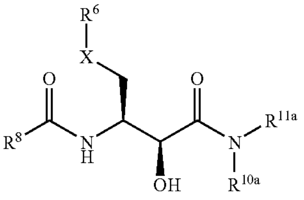
12
$R^{10a}$, $R^{11a}$ = phosphonate-containing $R^{10}$ or $R^{11}$
$R^1$ = H, alkyl, haloalkyl, alkenyl, aralkyl, aryl
$R^2$, $R^3$ = H, H; H, methyl; methyl, methyl; H, Cl.
$R^9$ = H, methyl
X = S or direct bond
Y = S, $CH_2$
CHART 3a
Structures of the $R^8COOH$ components
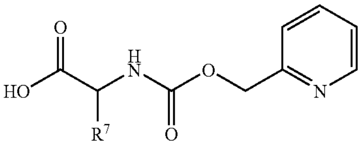
C1
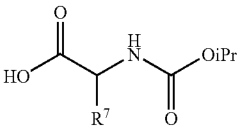
C2
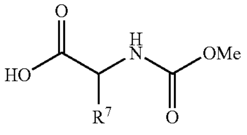
C3
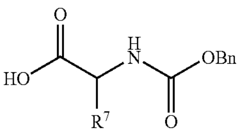
C4
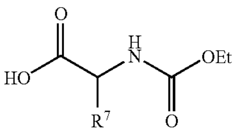
C5
CHART 3a-continued
Structures of the $R^8COOH$ components
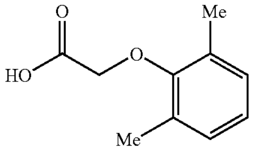
C6
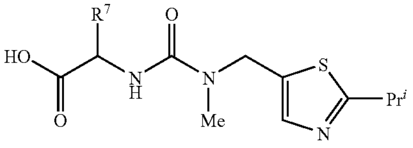
C7
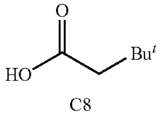
C8
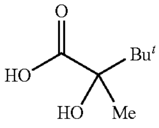
C9
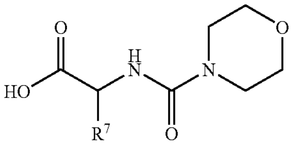
C10

CHART 3a-continued
Structures of the $R^8COOH$ components
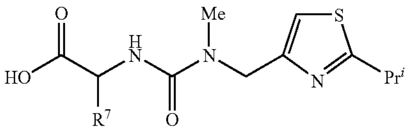
C11
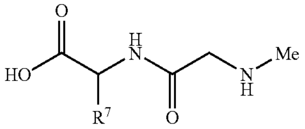
C12
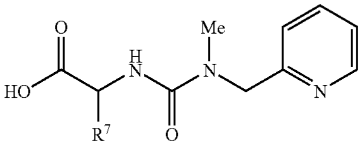
C13
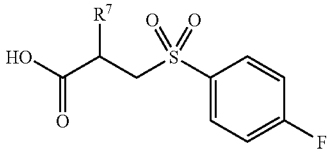
C14
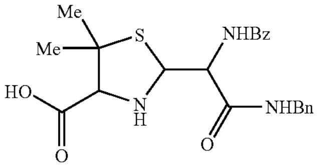
C15
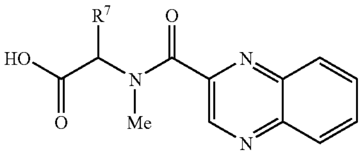
C16
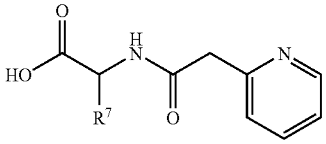
C17
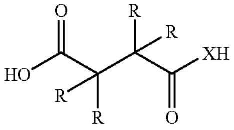
X = O, NH
R = H, alkyl
C18
CHART 3a-continued
Structures of the $R^8COOH$ components
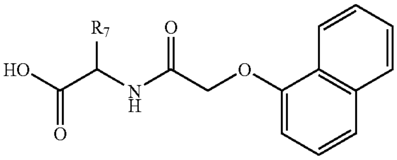
C19
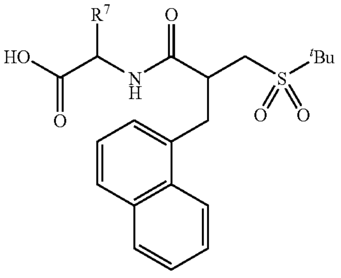
C20
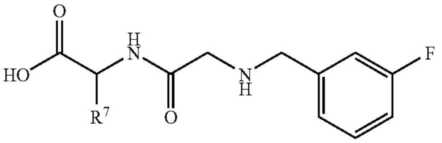
C21
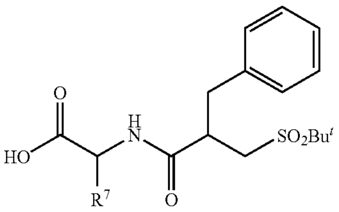
C22
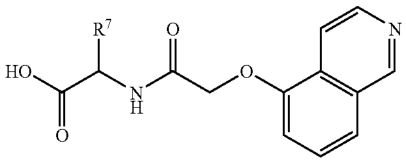
C23
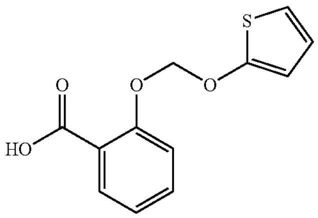
C24
$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$ CHART 3b
| Structures of the $R^8COOH$ components |
| --- |
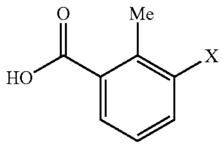
C25
X = OH, $NH_2$
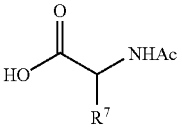
C26
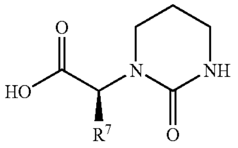
C27
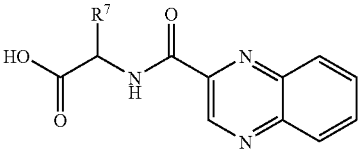
C28
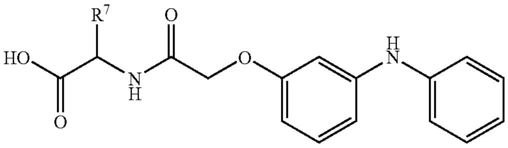
C29
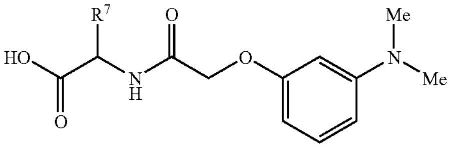
C30
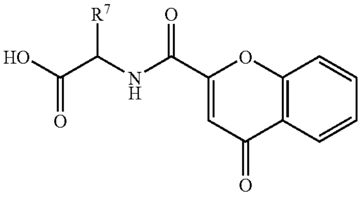
C31
CHART 3b-continued
| Structures of the $R^8COOH$ components |
| --- |
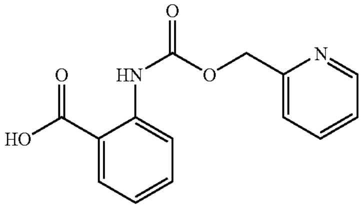
C32
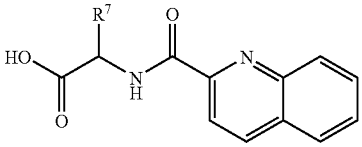
C33
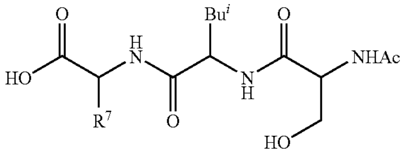
C34
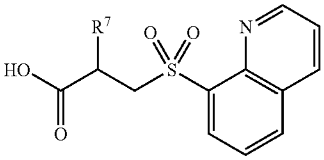
C35
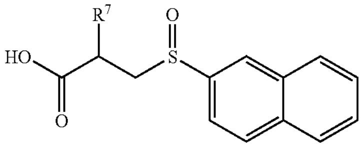
C36
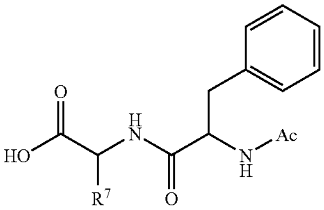
C37
$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$ CHART 3c
| Structures of the $R^8COOH$ components |
|---|
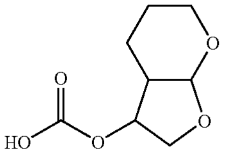
C38
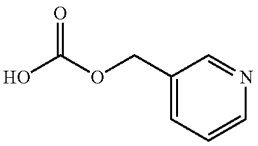
C39
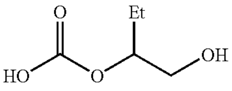
C40
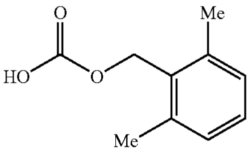
C41
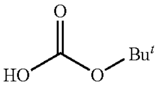
C42
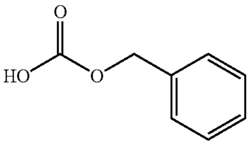
C43
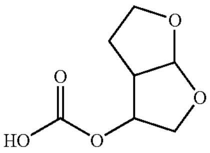
C44
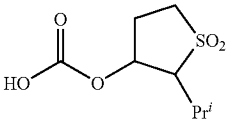
C45
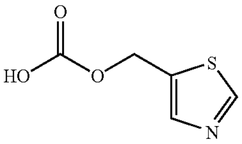
C46
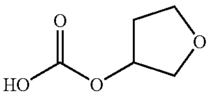
C47
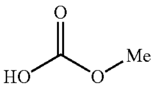
C48
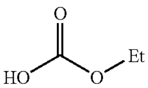
C49
CHART 4a
| Structures of the $R^{10}R^{11}NH$ components |
|---|
$R^{10}R^{11}NH$ =
1.2
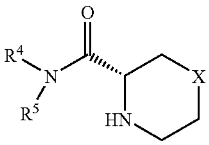
X = N, C
A1
CHART 4a-continued
| Structures of the $R^{10}R^{11}NH$ components |
|---|
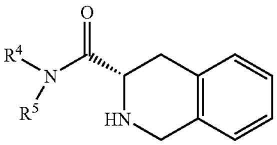
A2
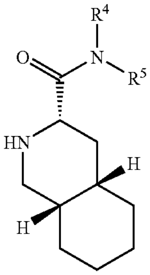
A3
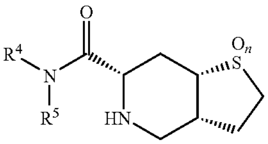
n = 0, 2
A4
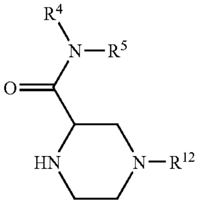
A-5
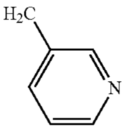
A6
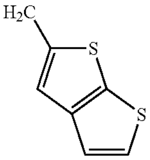
A7
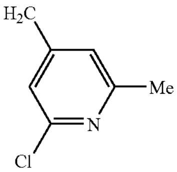
A8

CHART 4a-continued
Structures of the $R^{10}R^{11}NH$ components
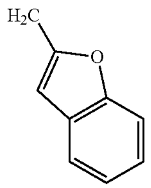
A9
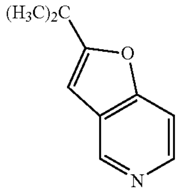
A10
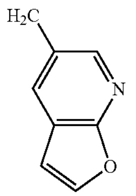
A11
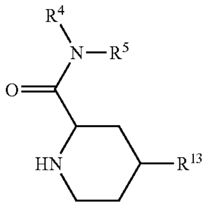
A12
$R^{13}$ = $OCH_2Ph$
S-3-pyridyl
S-4-pyridyl
$OCH_2$-4-pyridyl
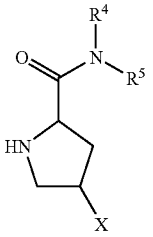
A13
X = Cl, OMe
CHART 4a-continued
Structures of the $R^{10}R^{11}NH$ components
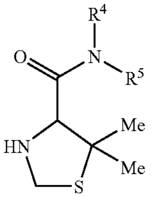
A14
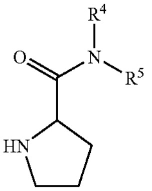
A15
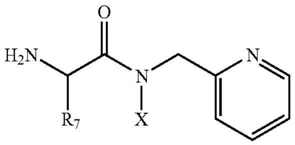
X = H or Me
A16
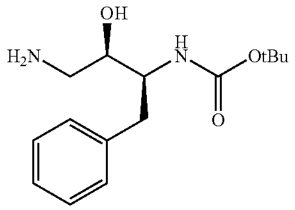
A17
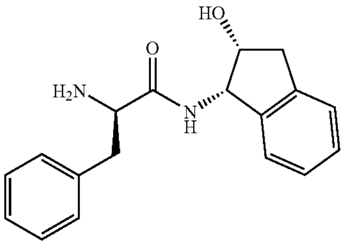
A18
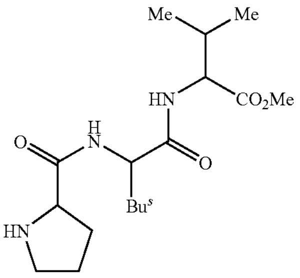
A19

CHART 4a-continued

Structures of the $R^{10}R^{11}NH$ components

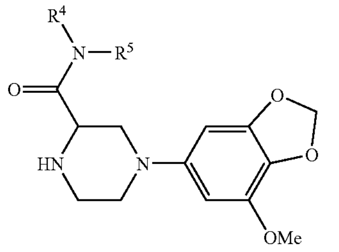

A20

$R^7$ = alkyl, $CH_2SO_2CH_3$, $C(CH_3)_2SO_2CH_3$, $CH_2CONH_2$, $CH_2SCH_3$, imidaz-4-ylmethyl, $CH_2NHAc$, $CH_2NHCOCF_3$

CHART 5

Structures of the $R^6XCH_2$ groups.

$R^6SCH_2$ =

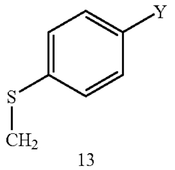

13

Y = H, F

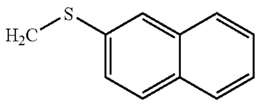

14

$R^6CH_2$ =

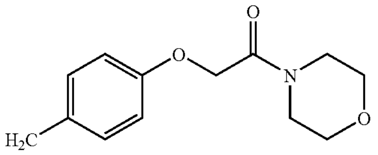

15

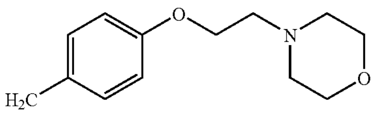

16

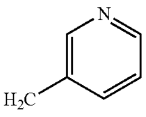

17

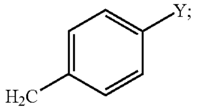

18

Y = H, $OC_2H_5$, $OCH_2C_6H$

CHART 6

Examples of the linking groups between the scaffold and the phosphonate moiety.

| link | examples |
|---|---|
| direct bond | 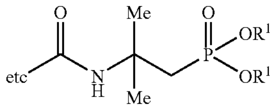 L1 |
| | 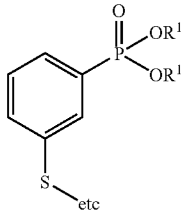 L2 |
| | 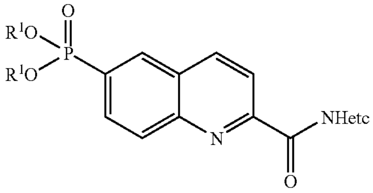 L3 |
| | 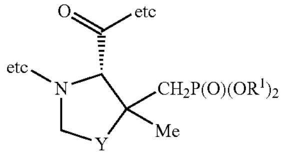 L4 |
| | 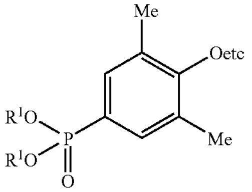 L5 |
| | 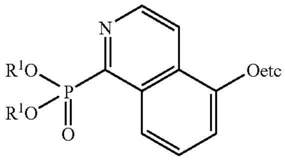 L6 |
| single carbon | 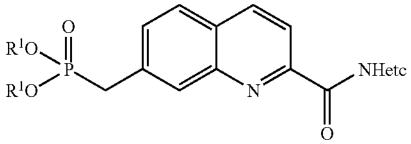 L7 |

CHART 6-continued
Examples of the linking groups between the scaffold and the phosphonate moiety.
| link | examples |
|---|---|
| | 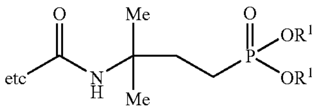<br>L8 |
| | 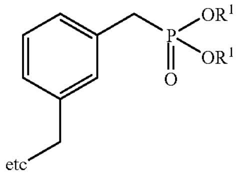<br>L9 |
| | 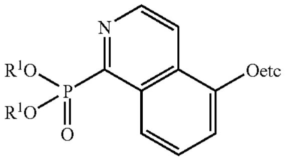<br>L10 |
| | 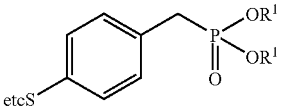<br>L11 |
| | 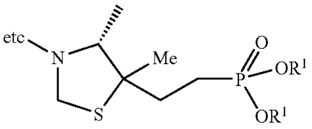<br>L12 |
| multiple carbon | 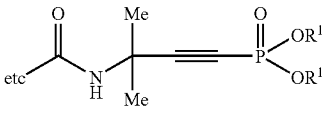<br>L13 |
| | 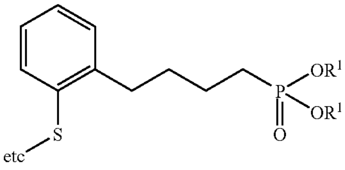<br>L14 |
CHART 6-continued
Examples of the linking groups between the scaffold and the phosphonate moiety.
| link | examples |
|---|---|
| | 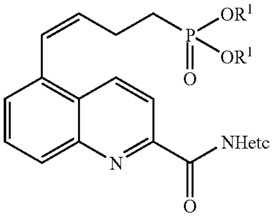<br>L15 |
| hetero atoms | 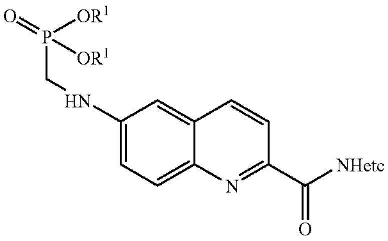<br>L16 |
| | 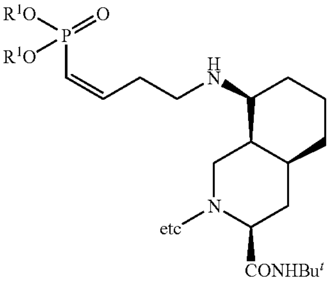<br>L17 |
| | 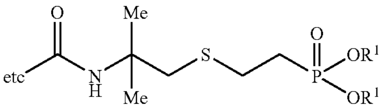<br>L18 |
| | 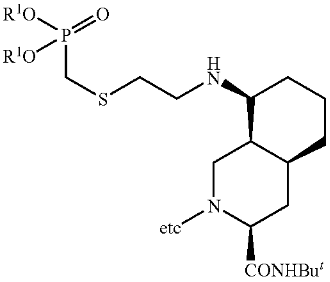<br>L19 |

CHART 6-continued

| Examples of the linking groups between the scaffold and the phosphonate moiety. | |
|---|---|
| link | examples |
| | 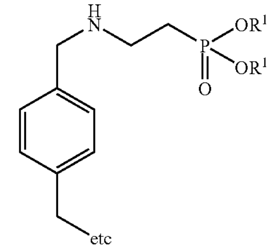<br>L20 |
| | 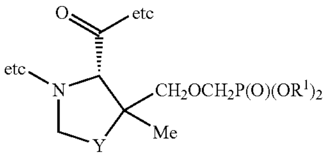<br>L21 |

CHART 7

| Examples of the linking groups between the scaffold and the phosphonate moiety. | |
|---|---|
| link | examples |
| aryl, heteroaryl | 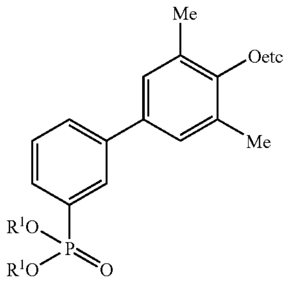<br>L22 |
| | 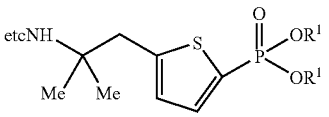<br>L23 |
| | 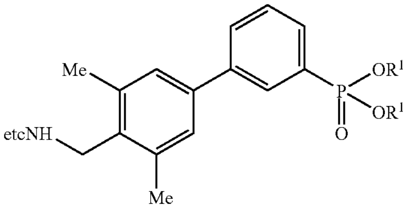<br>L24 |

CHART 7-continued

| Examples of the linking groups between the scaffold and the phosphonate moiety. | |
|---|---|
| link | examples |
| cycloalkyl | 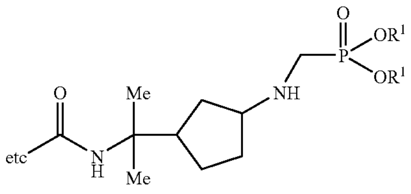<br>L25 |
| | 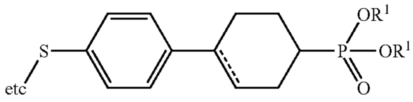<br>L26 |
| cyclized | 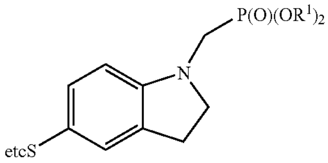<br>L27 |
| | 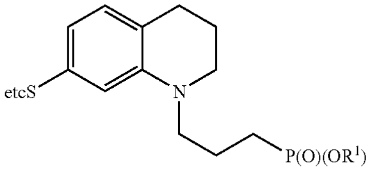<br>L28 |
| amide | 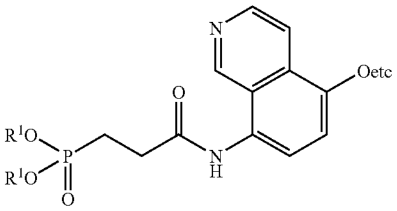<br>L29 |
| | 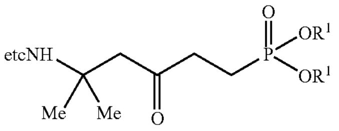<br>L30 |

CHART 7-continued

Examples of the linking groups between the scaffold and the phosphonate moiety.

| link | examples |
| --- | --- |
| | 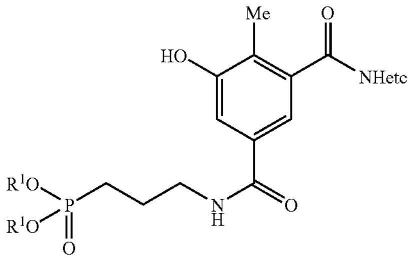 |
| | L31 |

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990. Reactive substituents which may be protected are shown in the accompanying schemes as, for example, [OH], [SH], etc.

Preparation of the Phosphonate Ester Intermediates 1 in which X is a Direct Bond.

Schemes 1 and 2 illustrate the preparation of the phosphonate esters 1 in which X is a direct bond. As shown in Scheme 1, a BOC-protected cyclic aminoacid 1.1 is reacted with an amine 1.2 to afford the amide 1.3. The carboxylic acid 1.1 in which Y is $CH_2$ and $R^2$ and $R^3$ are H is commercially available (Bachem). The preparation of the carboxylic acid 1.1 in which Y is S and $R^2$ and $R^3$ are $CH_3$ is described in Tet. Asym., 13, 2002, 1201; the preparation of the carboxylic acid 1.1 in which Y is S and $R^2$ is H and $R^3$ is $CH_3$ is described in JP 60190795; the preparation of the carboxylic acid 1.1 in which Y is S and $R^2$ and $R^3$ are H is described in EP 0574135; the preparation of the carboxylic acid 1.1 in which Y is $CH_2$, $R^2$ is H and $R^3$ is Cl is described in EP 587311.

The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide. Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide. Preferably, equimolar amounts of the carboxylic acid 1.1 and the amine 1.2 are reacted together in tetrahydrofuran solution in the presence of dicyclohexylcarbodiimide and N-hydroxysuccinimide, for example as described in EP 574135, to yield the amide product 1.3. The BOC protecting group is then removed to give the free amine 1.4. The removal of BOC protecting groups is described, for example, in Protective Groups in Organic Synthesis, by T. W. Greene and P. G. M Wuts, Wiley, Second Edition 1990, p. 328. The deprotection can be effected by treatment of the BOC compound with anhydrous acids, for example, hydrogen chloride or trifluoroacetic acid, or by reaction with trimethylsilyl iodide or aluminum chloride. Preferably, the BOC protecting group is removed by treatment of the compound 1.3 with 8M methanesulfonic acid in acetonitrile, as described in Tet. Asym., 13, 2000, 1201, to afford the amine 1.4. The latter compound is then reacted with a carboxylic acid 1.5, to afford the amide 1.6. The preparation of the carboxylic acid reactants 1.5 is described below, (Schemes 41, 42). The reaction is performed under similar conditions to those described above for the preparation of the amide 1.3. Preferably, equimolar amounts of the amine 1.4 and the carboxylic acid 1.6 are reacted in tetrahydrofuran solution at ambient temperature in the presence of dicyclohexylcarbodiimide and hydroxybenztriazole, for example as described in EP 574135, to yield the amide 1.6. The BOC protecting group is then removed from the product 1.6 to afford the amine 1.7, using similar conditions to those described above for the removal of BOC protecting group from the compound 1.3. Preferably, the BOC group is removed by treatment of the substrate 1.6 with a 4M solution of hydrogen chloride in dioxan at 00, for example as described in EP 574135, to give the amine product 1.7.

The amine is then reacted with a carboxylic acid 1.8, or an activated derivative thereof, in which the substituent A is the group link-$P(O)(OR^1)_2$, or a precursor group thereto, such as [OH], [SH], $NH_2$, Br, etc, as described herein, to afford the amide 1.9. The preparation of the carboxylic acids 1.8 is described below in Schemes 45-49. The reaction between the amine 1.7 and the carboxylic acid 1.8 is conducted under similar conditions to those described above for the preparation of the amides 1.3 and 1.6.

The procedures illustrated in Scheme 1 describe the preparation of the compounds 1.9 in which the substituent A is either the group fink-$P(O)(OR^1)_2$, or a precursor group thereto, such as [OH], [SH], [$NH_2$], Br, etc, as described herein.

Scheme 2 depicts the conversion of the compounds 1.9 in which the A is a precursor to the substituent link-$P(O)(OR^1)_2$ into the compounds 1. Procedures for the conversion of the substituents [OH], [SH], [$NH_2$], Br etc into the substituent link-$P(O)(OR^1)_2$ are described below in Schemes 45-101.

In the preceding and following schemes, the conversion of various substituents into the group link-$P(O)(OR^1)_2$ can be effected at any convenient stage of the synthetic sequence, as well as at the end. The selection of an appropriate step for the introduction of the phosphonate substituent is made after consideration of the chemical procedures required, and the stability of the substrates to those procedures.

The phosphonate esters 5-12 in which the substituent $R^8CO$ is derived from one of the carboxylic acids C38-C49, as shown in Chart 3c, incorporate a carbamate linkage. Various methods for the preparation of carbamate groups are described below in Scheme 102.

In the above and succeeding examples, the nature of the phosphonate ester group can be varied, either before or after incorporation into the scaffold, by means of chemical transformations. The transformations, and the methods by which they are accomplished, are described below (Scheme 103)

Preparation of the Phosphonate Ester Intermediates 1 in which X is Sulfur.

Schemes 3 and 4 illustrate the preparation of the phosphonate ester intermediates 1 in which X is sulfur. Scheme 3 illustrates the reaction of the amine 1.3, prepared as described in Scheme 1, with a carboxylic acid reagent 3.1, to give the amide product 3.2. The preparation of the carboxylic acid reagents 3.1 is described below in Schemes 43 and 44. The reaction between the carboxylic acid 3.1 and the amine 1.3 is performed under similar conditions to those described above for the preparation of the amide 1.6. The amide product 3.2 is then subjected to a deprotection reaction to remove the BOC substituent and afford the amine 3.3. The reaction is performed under similar conditions to those described in Scheme 1 for the removal of BOC protecting groups. The amine product 3.3 is then reacted with a carboxylic acid 1.8, or an activated derivative thereof, in which the substituent A is the group link-P(O)(OR$^1$)$_2$, or a precursor group thereto, such as [OH], [SH], NH$_2$, Br, etc, as described herein, to afford the amide product 3.4. The amide forming reaction is performed under similar conditions to those described above for the preparation of the amide 1.9.

The procedures illustrated in Scheme 3 describe the preparation of the compounds 3.4 in which the substituent A is either the group link-P(O)(OR$^1$)$_2$, or a precursor group thereto, such as [OH], [SH], [NH$_2$], Br, etc, as described herein.

Scheme 4 depicts the conversion of the compounds 3.4 in which the A is a precursor to the substituent link-P(O)(OR$^1$)$_2$ into the compounds 1. Procedures for the conversion of the substituents [OH], [SH], [NH$_2$], Br etc into the substituent link-P(O)(OR$^1$)$_2$ are described below in Schemes 45-101.

Scheme 1

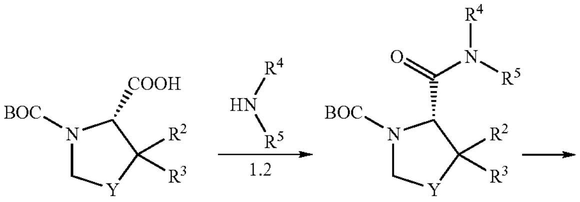

1.1 1.2 1.3

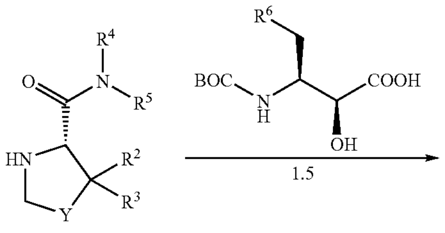

1.4 1.5

-continued

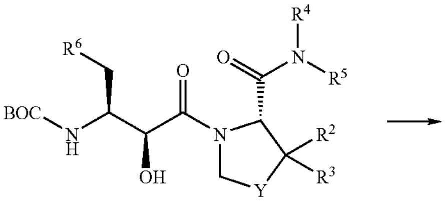

1.6

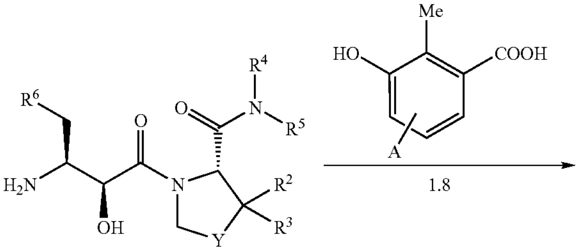

1.7 1.8

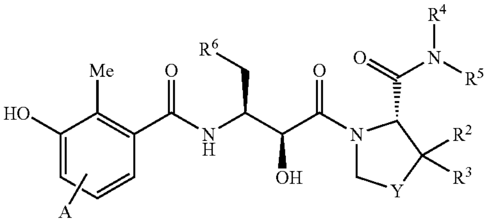

1.9

Scheme 2

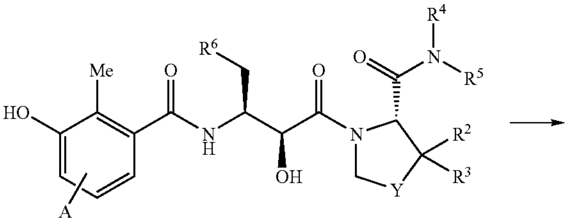

1.9

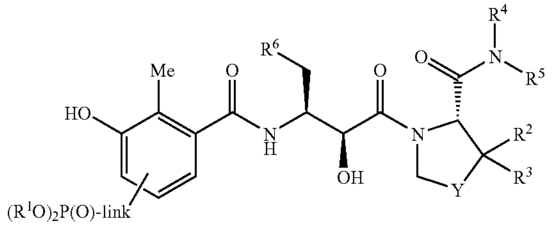

1

Scheme 3

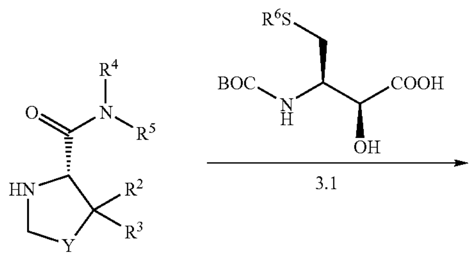

1.3

3.1

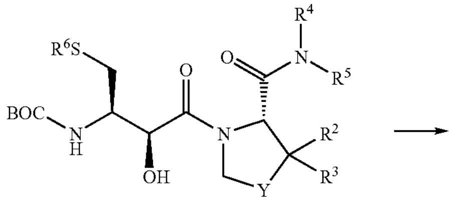

3.2

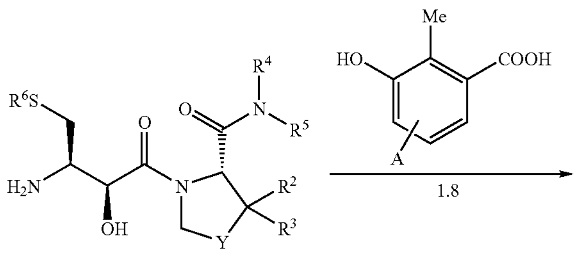

3.3

1.8

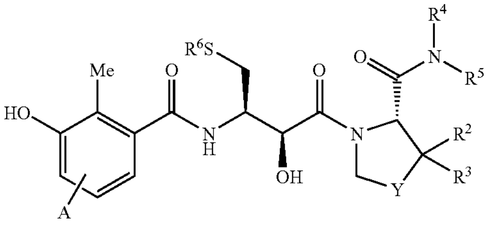

3.4

Scheme 4

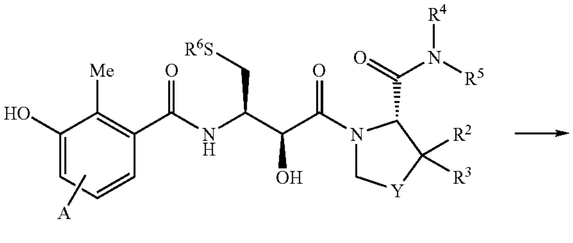

3.4

-continued

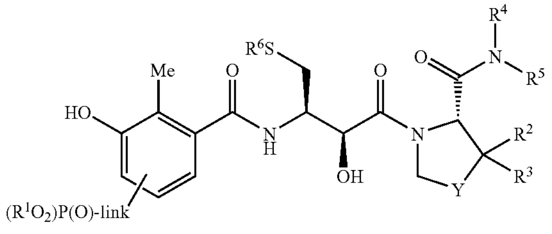

1

Preparation of the Phosphonate Ester Intermediates 2 in which X is a Direct Bond.

Schemes 5 and 6 depict the preparation of the intermediate phosphonate esters 2 in which X is direct bond. As shown in Scheme 5, the amine 1.7, prepared as described in Scheme 1, is reacted with a carboxylic acid 5.1, or an activated derivative thereof, in which the substituent A is the group link-P(O)$(OR^1)_2$, or a precursor group thereto, such as [OH], [SH], $NH_2$, Br, etc, as described herein, to afford the amide product 5.2. The preparation of the carboxylic acids 5.1 is described below in Schemes 50-56. The amide forming reaction is performed under similar conditions to those described above for the preparation of the amide 1.9.

The procedures illustrated in Scheme 5 describe the preparation of the compounds 5.2 in which the substituent A is either the group link-P(O)$(OR^1)_2$, or a precursor group thereto, such as [OH], [SH], [$NH_2$], Br, etc, as described herein.

Scheme 6 depicts the conversion of the compounds 5.2 in which the A is a precursor to the substituent Link-P(O)$(OR^1)_2$ into the compounds 2. Procedures for the conversion of the substituents [OH], [SH], [$NH_2$], Br etc into the substituent link-P(O)$(OR^1)_2$ are described below in Schemes 45-101.

Preparation of the Phosphonate Ester Intermediates 2 in which X is Sulfur.

Schemes 7 and 8 depict the preparation of the intermediate phosphonate esters 2 in which X is sulfur. As shown in Scheme 7, the amine 3.3, prepared as described in Scheme 3, is reacted with a carboxylic acid 5.1, or an activated derivative thereof, in which the substituent A is the group link-P(O)$(OR^1)_2$, or a precursor group thereto, such as [OH], [SH], $NH_2$, Br, etc, as described herein, to afford the amide product 7.1. The preparation of the carboxylic acids 5.1 is described below in Schemes 50-56. The amide forming reaction is performed under similar conditions to those described above for the preparation of the amide 1.9.

The procedures illustrated in Scheme 7 describe the preparation of the compounds 7.1 in which the substituent A is either the group link-P(O)$(OR^1)_2$, or a precursor group thereto, such as [OH], [SH], [$NH_2$], Br, etc, as described herein.

Scheme 8 depicts the conversion of the compounds 7.1 in which the A is a precursor to the substituent link-P(O)$(OR^1)_2$ into the compounds 2. Procedures for the conversion of the substituents [OH], [SH], [$NH_2$], Br etc into the substituent link-P(O)$(OR^1)_2$ are described below in Schemes 45-101.

Scheme 5

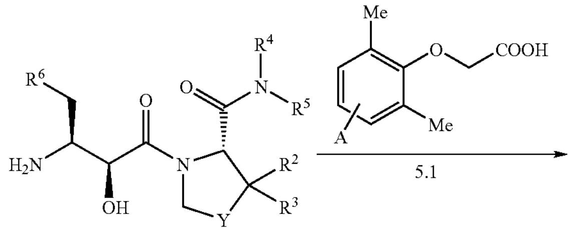

1.7

5.1

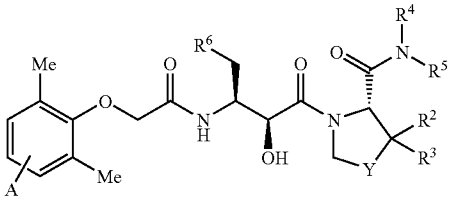

5.2

Scheme 6

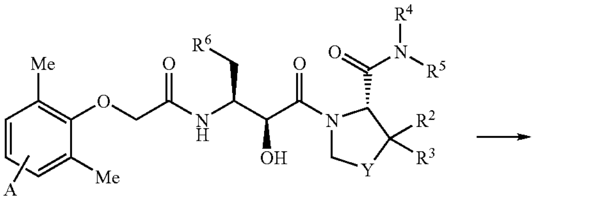

5.2

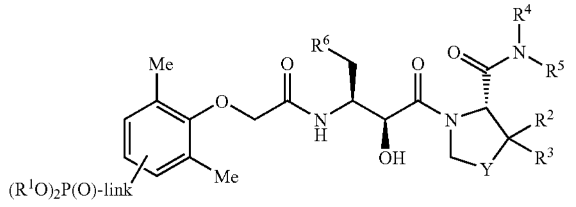

2

Scheme 7

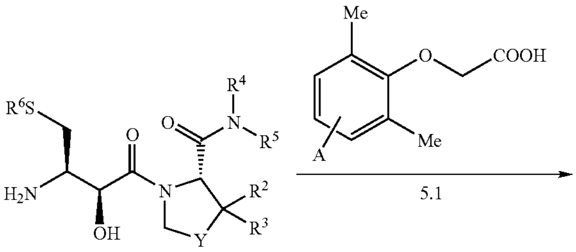

3.3

5.1

-continued

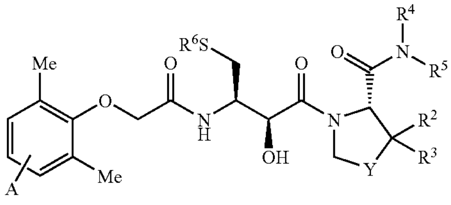

7.1

Scheme 8

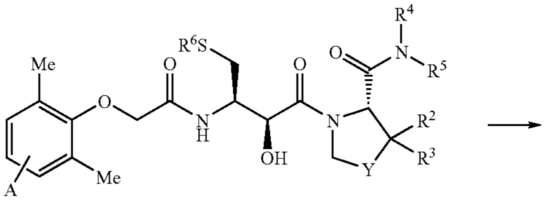

7.1

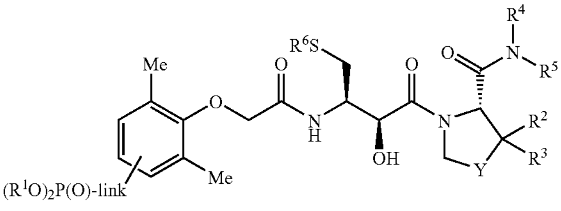

2

Preparation of the Phosphonate Ester Intermediates 3 in which X is a Direct Bond.

Schemes 9 and 10 depict the preparation of the intermediate phosphonate esters 3 in which X is direct bond. As shown in Scheme 9, the amine 1.7, prepared as described in Scheme 1, is reacted with a carboxylic acid 9.1, or an activated derivative thereof, in which the substituent A is the group link-P(O)$(OR^1)_2$, or a precursor group thereto, such as [OH], [SH], $NH_2$, Br, etc, as described herein, to afford the amide product 9.2. The preparation of the carboxylic acids 9.1 is described below in Schemes 57-60. The amide forming reaction is performed under similar conditions to those described above for the preparation of the amide 1.9.

The procedures illustrated in Scheme 9 describe the preparation of the compounds 9.2 in which the substituent A is either the group link-P(O)$(OR^1)_2$, or a precursor group thereto, such as [OH], [SH], $[NH_2]$, Br, etc, as described herein.

Scheme 10 depicts the conversion of the compounds 9.2 in which the group A is a precursor to the substituent link-P(O)$(OR^1)_2$ into the compounds 3. Procedures for the conversion of the substituents [OH], [SH], $[NH_2]$, Br etc into the substituent link-P(O)$(OR^1)_2$ are described below in Schemes 45-101.

Preparation of the Phosphonate Ester Intermediates 3 in which X is Sulfur.

Schemes 11 and 12 depict the preparation of the intermediate phosphonate esters 3 in which X is sulfur. As shown in Scheme 11, the amine 3.3, prepared as described in Scheme 3, is reacted with a carboxylic acid 9.1, or an activated derivative thereof, in which the substituent A is the group link-P(O)$(OR^1)_2$, or a precursor group thereto, such as [OH], [SH], $NH_2$, Br, etc, as described herein, to afford the amide product 11.1. The preparation of the carboxylic acids 9.1 is described below in Schemes 57-60. The amide forming reaction is performed under similar conditions to those described above for the preparation of the amide 1.9.

The procedures illustrated in Scheme 11 describe the preparation of the compounds 11.1 in which the substituent A is either the group link-P(O)$(OR^1)_2$, or a precursor group thereto, such as [OH], [SH], $[NH_2]$, Br, etc, as described herein.

Scheme 12 depicts the conversion of the compounds 11.1 in which the A is a precursor to the substituent link-P(O)$(OR^1)_2$ into the compounds 3. Procedures for the conversion of the substituents [OH], [SH], $[NH_2]$, Br etc into the substituent link-P(O)$(OR^1)_2$ are described below in Schemes 45-101.

Scheme 9

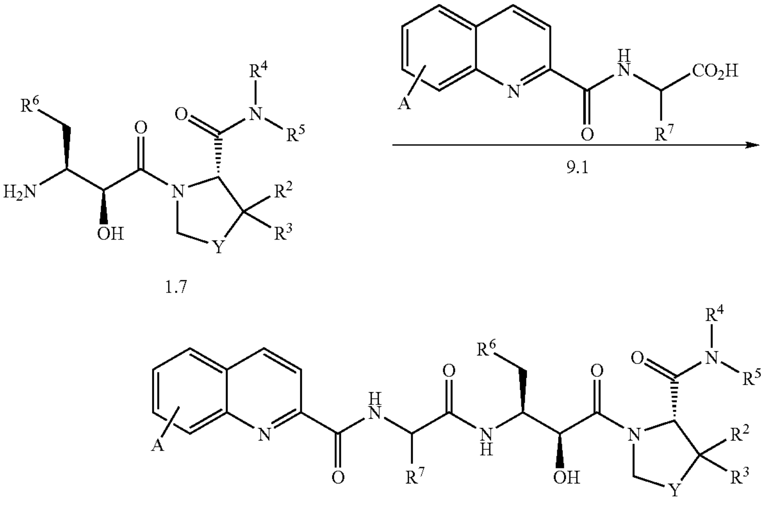

1.7

9.1

9.2

Scheme 10

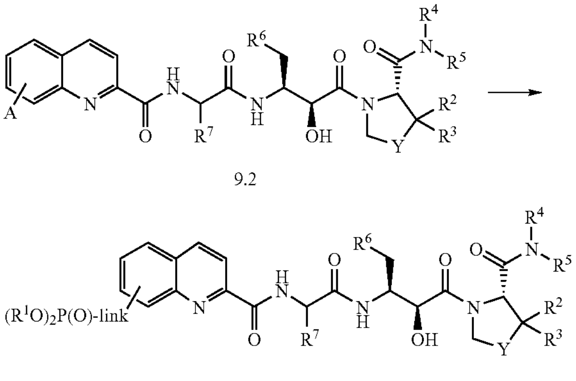

9.2

3

Scheme 11

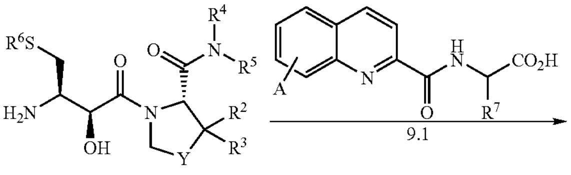

9.1

3.3

-continued

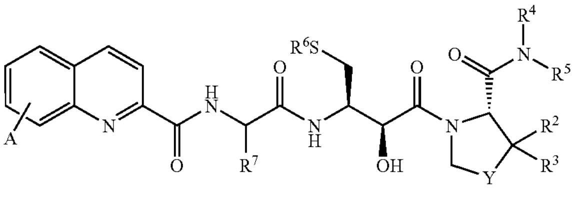

11.1

Scheme 12

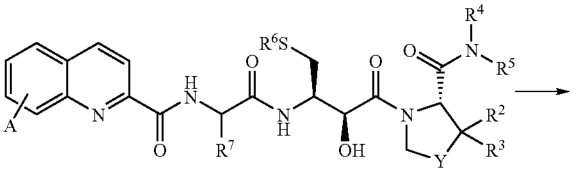

11.1

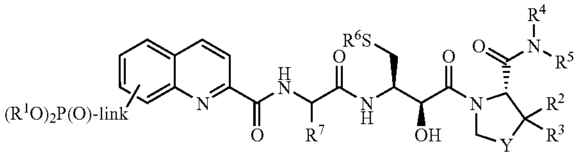

3

Preparation of the Phosphonate Ester Intermediates 4 in which X is a Direct Bond.

Schemes 13 and 14 depict the preparation of the intermediate phosphonate esters 4 in which X is direct bond. As shown in Scheme 13, the amine 1.7, prepared as described in Scheme 1, is reacted with a carboxylic acid 13.1, or an activated derivative thereof, in which the substituent A is the group link-$P(O)(OR^1)_2$, or a precursor group thereto, such as [OH], [SH], $NH_2$, Br, etc, as described herein, to afford the amide product 13.2. The preparation of the carboxylic acids 13.1 is described below in Schemes 61-66. The amide forming reaction is performed under simliar conditions to those described above for the preparation of the amide 1.9.

The procedures illustrated in Scheme 13 describe the preparation of the compounds 13.2 in which the substituent A is either the group link-$P(O)(OR^1)_2$, or a precursor group thereto, such as [OH], [SH], [$NH_2$], Br, etc, as described herein.

Scheme 14 depicts the conversion of the compounds 13.2 in which the A is a precursor to the substituent link-P(O)$(OR^1)_2$ into the compounds 4. Procedures for the conversion of the substituents [OH], [SH], [$NH_2$], Br etc into the substituent link-$P(O)(OR^1)_2$ are described below in Schemes 45-101.

Preparation of the Phosphonate Ester Intermediates 4 in which X is Sulfur.

Schemes 15 and 16 depict the preparation of the intermediate phosphonate esters 4 in which X is sulfur. As shown in Scheme 15, the amine 3.3, prepared as described in Scheme 3, is reacted with a carboxylic acid 13.1, or an activated derivative thereof, in which the substituent A is the group link-P(O)$(OR^1)_2$, or a precursor group thereto, such as [OH], [SH], $NH_2$, Br, etc, as described herein, to afford the amide product 15.1. The preparation of the carboxylic acids 13.1 is described below in Schemes 61-66. The amide forming reaction is performed under similar conditions to those described above for the preparation of the amide 1.9.

The procedures illustrated in Scheme 15 describe the preparation of the compounds 15.1 in which the substituent A is either the group link-$P(O)(OR^1)_2$, or a precursor group thereto, such as [OH], [SH], [$NH_2$], Br, etc, as described herein.

Scheme 16 depicts the conversion of the compounds 15.1 in which the A is a precursor to the substituent link-P(O)$(OR^1)_2$ into the compounds 4. Procedures for the conversion of the substituents [OH], [SH], [$NH_2$], Br etc into the substituent link-$P(O)(OR^1)_2$ are described below in Schemes 45-101.

Preparation of the Phosphonate Ester Intermediates 5 in which X is a Direct Bond.

Schemes 17 and 18 show the preparation of the intermediate phosphonate esters 5 in which X is a direct bond. As depicted in Scheme 17, the amine 1.4, prepared as described in Scheme 1, is reacted with the carboxylic acid 17.1, or an activated derivative thereof, to yield the amide product 17.2. The preparation of the carboxylic acids 17.1 in which the group A is either the group link-$P(O)(OR^1)_2$, or a precursor group thereto, such as [OH], [SH], [$NH_2$], Br, etc, is described in Schemes 67-71. The amide forming reaction is performed under similar conditions to those described above for the preparation of the amide 1.6. The BOC protecting group is then removed from the product 17.2 to afford the amine 17.3. The deprotection reaction is performed using similar conditions to those described above in Scheme 1. The resultant amine 17.3 is then reacted with a carboxylic acid $R^8COOH$ or activated derivative thereof, 17.4 to give the amide 17.5. For those carboxylic acids $R^8COOH$ listed in Charts 3a and 3b, the reaction is performed using similar conditions to those described above for the preparation of the amide 1.9, (Scheme 1); for those carboxylic acids $R^8COOH$ listed in Chart 3c, the reaction is performed using conditions described below (Scheme 102) for the preparation of carbamates.

The procedures illustrated in Scheme 17 describe the preparation of the compounds 17.5 in which the substituent A is either the group link-$P(O)(OR^1)_2$, or a precursor group thereto, such as [OH], [SH], [$NH_2$], Br, etc, as described herein.

Scheme 18 depicts the conversion of the compounds 17.5 in which the A is a precursor to the substituent link-P(O)$(OR^1)_2$ into the compounds 5. Procedures for the conversion of the substituents [OH], [SH], [$NH_2$], Br etc into the substituent link-$P(O)(OR^1)_2$ are described below in Schemes 45-101.

Preparation of the Phosphonate Ester Intermediates 5 in which X is Sulfur.

Schemes 19 and 20 show the preparation of the intermediate phosphonate esters 5 in which X is sulfur. As depicted in Scheme 19, the amine 1.4, prepared as described in Scheme 1, is reacted with the carboxylic acid 19.1, or an activated derivative thereof, to yield the amide product 19.2. The preparation of the carboxylic acids 19.1 in which the group A is either the group link-$P(O)(OR^1)_2$, or a precursor group thereto, such as [OH], [SH], [$NH_2$], Br, etc, is described in Schemes 72-83. The amide forming reaction is performed under similar conditions to those described above for the preparation of the amide 1.6. The BOC protecting group is then removed from the product 19.2 to afford the amine 19.3. The deprotection reaction is performed using similar conditions to those described above in Scheme 1. The resultant amine 19.3 is then reacted with a carboxylic acid $R^8COOH$ or activated derivative thereof, 19.4 to give the amide 19.4. For those carboxylic acids $R^8COOH$ listed in Charts 3a and 3b, the reaction is performed using similar conditions to those described above for the preparation of the amide 1.9, (Scheme 1); for those carboxylic acids $R^8COOH$ listed in Chart 3c, the reaction is performed using conditions described below (Scheme 102) for the preparation of carbamates.

The procedures illustrated in Scheme 19 describe the preparation of the compounds 19.4 in which the substituent A is either the group link-$P(O)(OR^1)_2$, or a precursor group thereto, such as [OH], [SH], [$NH_2$], Br, etc, as described herein.

Scheme 20 depicts the conversion of the compounds 19.4 in which the A is a precursor to the substituent link-$P(O)(OR^1)_2$ into the compounds 5. Procedures for the conversion of the substituents [OH], [SH], [$NH_2$], Br etc into the substituent link-$P(O)(OR^1)_2$ are described below in Schemes 45-101.

Scheme 13

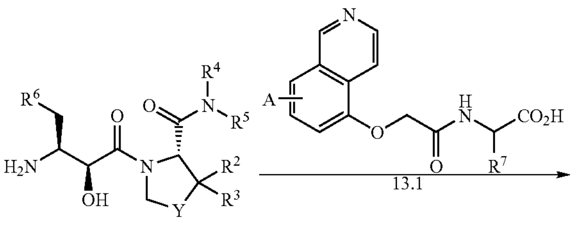

1.7

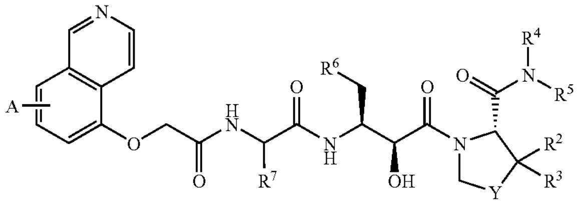

13.2

Scheme 14

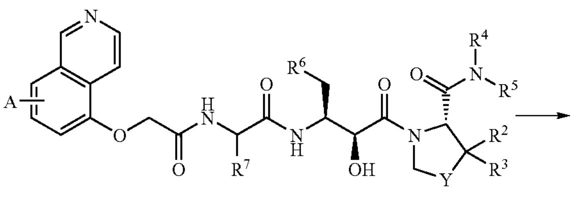

13.2

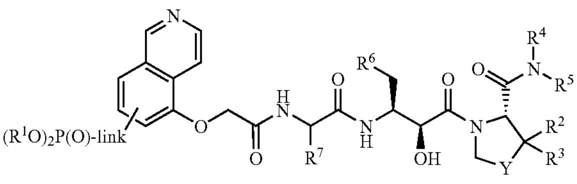

4

Scheme 15

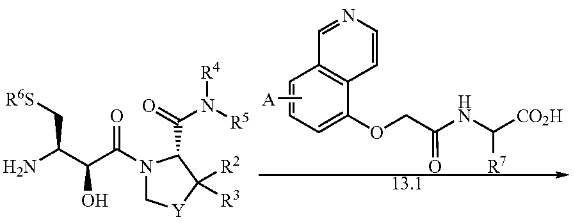

3.3

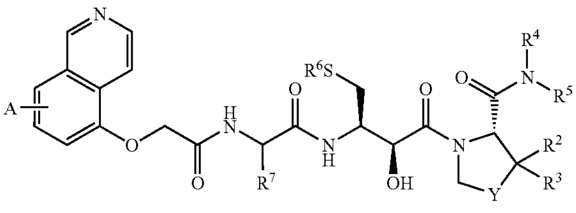

15.1

Scheme 16

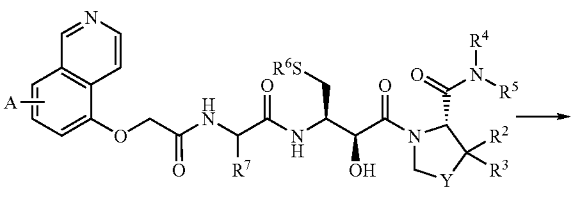

15.1

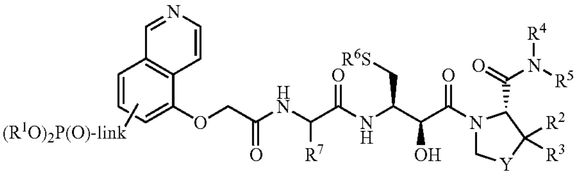

4

Scheme 17

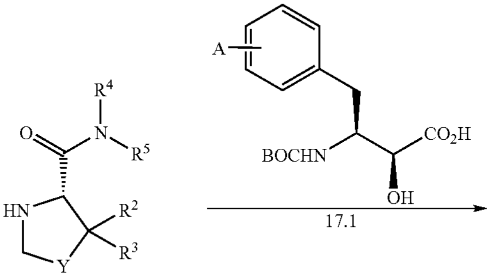

1.4

-continued
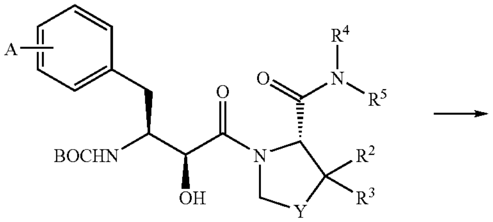
17.2
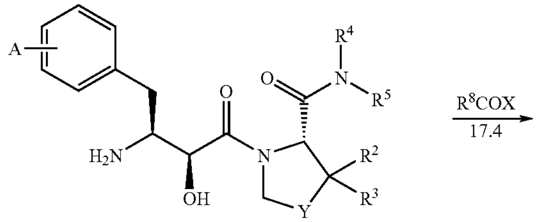
17.3
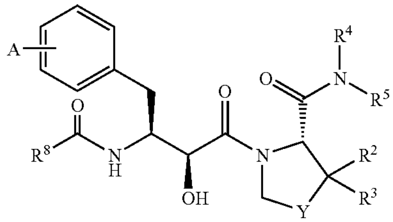
17.5
Scheme 18
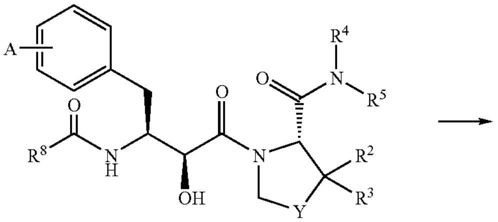
17.5
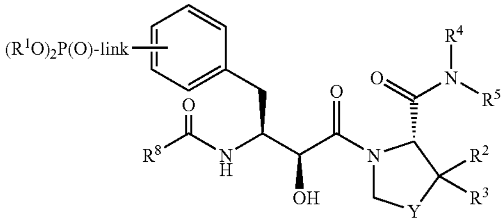
5
Scheme 19
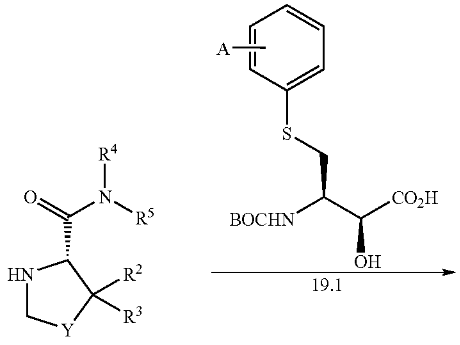
1.4
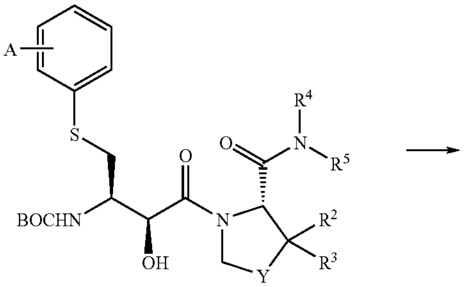
19.2
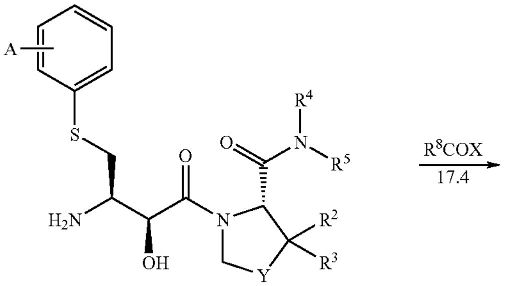
19.3
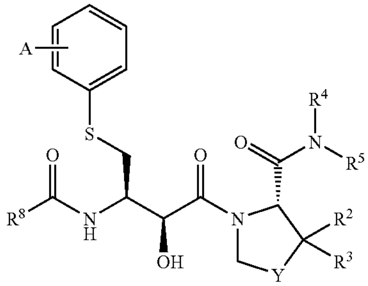
19.4

Scheme 20

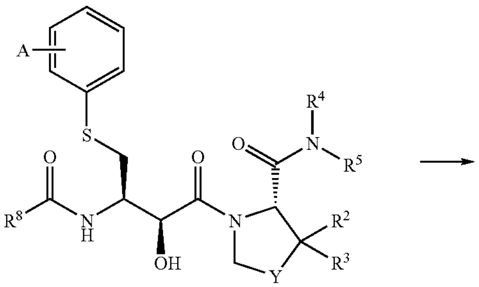

19.4

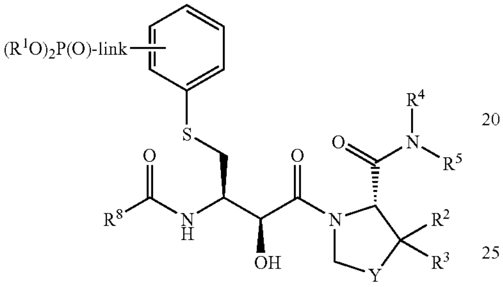

5

Preparation of the Phosphonate Ester Intermediates 6 in which X is a Direct Bond.

Schemes 21 and 22 illustrate the preparation of the phosphonate esters 6 in which X is a direct bond. In this procedure, the carboxylic acid 21.1, in which the group A is the substituent link-P(O)(OR$^1$)$_2$, or a precursor group thereto, such as [OH], [SH], [NH$_2$], Br, etc, as described herein, is reacted with the amine 1.2 to afford the amide 21.2. The preparation of the carboxylic acids 21.1 is described below in Schemes 98-101. The reaction is performed under similar conditions to those described in Scheme 1 for the preparation of the amide 1.3. The product 21.2 is then deprotected to yield the free amine 21.3, using the procedures described above for the removal of BOC groups. The amine 21.3 is then converted, by reaction with the carboxylic acid 1.5, into the amide 21.4, using the conditions described above for the preparation of the amide 1.6. The amide 21.4 is then deprotected to afford the amine 21.5, and the latter compound is acylated with the carboxylic acid 17.4 to give the amide 21.6.

The procedures illustrated in Scheme 21 describe the preparation of the compounds 21.6 in which the substituent A is either the group link-P(O)(OR$^1$)$_2$, or a precursor group thereto, such as [OH], [SH], [NH$_2$], Br, etc, as described herein.

Scheme 22 depicts the conversion of the compounds 21.6 in which the A is a precursor to the substituent link-P(O)(OR$^1$)$_2$ into the compounds 6. Procedures for the conversion of the substituents [OH], [SH], [NH$_2$], Br etc into the substituent link-P(O)(OR$^1$)$_2$ are described below in Schemes 45-101.

Preparation of the Phosphonate Ester Intermediates 6 in which X is Sulfur.

Schemes 23 and 24 illustrate the preparation of the phosphonate esters 6 in which X is Sulfur. In the procedure shown in Scheme 23, the amine 21.3, prepared as described in Scheme 21, is reacted with the carboxylic acid 3.1 to afford the amide 23.1. The reaction is performed under similar conditions to those described in Scheme 1 for the preparation of the amide 1.3. The product 23.1 is then converted, by means of deprotection and acylation, as shown in Scheme 21 for the conversion of the compound 21.4 into the compound 21.6, into the amide product 23.2.

The procedures illustrated in Scheme 23 describe the preparation of the compounds 23.2 in which the substituent A is either the group link-P(O)(OR$^1$)$_2$, or a precursor group thereto, such as [OH], [SH], [NH$_2$], Br, etc, as described herein.

Scheme 24 depicts the conversion of the compounds 23.2 in which the A is a precursor to the substituent link-P(O)(OR$^1$)$_2$ into the compounds 6. Procedures for the conversion of the substituents [OH], [SH], [NH$_2$], Br etc into the substituent link-P(O)(OR$^1$)$_2$ are described below in Schemes 45-101.

Preparation of the Phosphonate Ester Intermediates 7 in which X is a Direct Bond.

Schemes 25 and 26 illustrate the preparation of the phosphonate esters 7 in which X is a direct bond. As shown in Scheme 25, the carboxylic acid 1.1 is reacted with the amine 25.1, in which the substituent A is either the group link-P(O)(OR$^1$)$_2$, or a precursor group thereto, such as [OH], [SH], [NH$_2$], Br, etc, as described herein, to produce the amide 25.2. The reaction is performed using similar conditions to those described above for the preparation of the amide 1.3. The preparation of the amines 25.1 is described below, in Schemes 84-87. The amide product 25.2 is then transformed, using the sequence of reactions shown in Scheme 21 for the conversion of the amide 21.2 into the compound 21.6, into the compound 25.3.

The procedures illustrated in Scheme 25 describe the preparation of the compounds 25.3 in which the substituent A is either the group link-P(O)(OR$^1$)$_2$, or a precursor group thereto, such as [OH], [SH], [NH$_2$], Br, etc, as described herein.

Scheme 25 depicts the conversion of the compounds 25.3 in which the A is a precursor to the substituent link-P(O)(OR$^1$)$_2$ into the compounds 7. Procedures for the conversion of the substituents [OH], [SH], [NH$_2$], Br etc into the substituent link-P(O)(OR$^1$)$_2$ are described below in Schemes 45-101.

Preparation of the Phosphonate Ester Intermediates 7 in which X is Sulfur.

Schemes 27 and 28 illustrate the preparation of the phosphonate esters 7 in which X is Sulfur. As shown in Scheme 27, the BOC-protected amine 25.2 is deprotected to yield the free amine 27.1, using the conditions previously described. The amine 27.1 is then reacted, as described above, with the carboxylic acid 3.1 to afford the amide 27.2. The latter compound is then transformed, as described above, (Scheme 23) into the product 27.3.

The procedures illustrated in Scheme 27 describe the preparation of the compounds 27.3 in which the substituent A is either the group link-P(O)(OR$^1$)$_2$, or a precursor group thereto, such as [OH], [SH], [NH$_2$], Br, etc, as described herein.

Scheme 28 depicts the conversion of the compounds 27.3 in which the A is a precursor to the substituent link-P(O)(OR$^1$)$_2$ into the compounds 7. Procedures for the conversion of the substituents [OH], [SH], [NH$_2$], Br etc into the substituent link-P(O)(OR$^1$)$_2$ are described below in Schemes 45-101.

Scheme 21
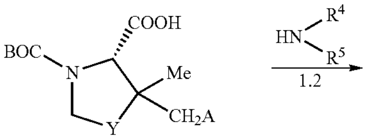
21.1
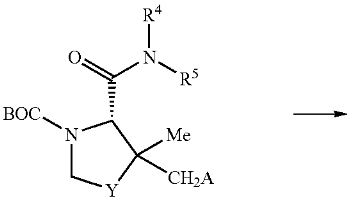
21.2
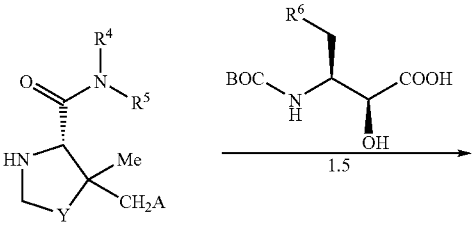
21.3
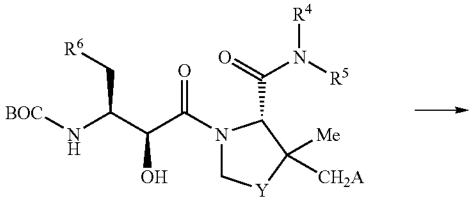
21.4
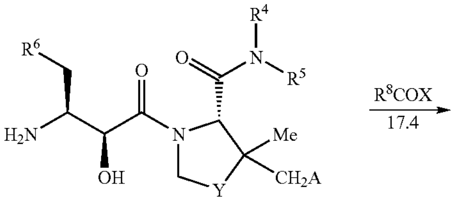
21.5
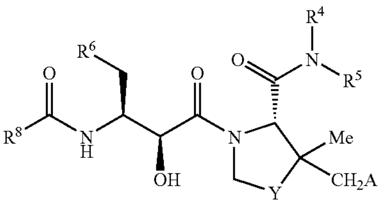
21.6
Scheme 22
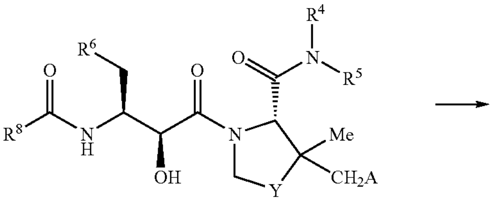
21.6
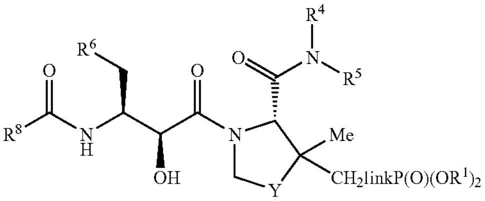
6
Scheme 23
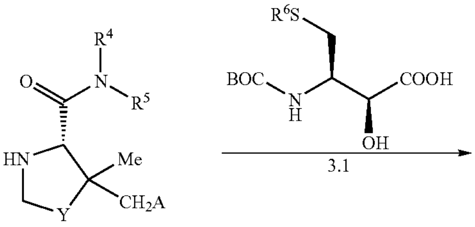
21.3
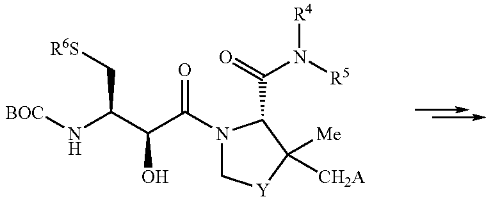
23.1
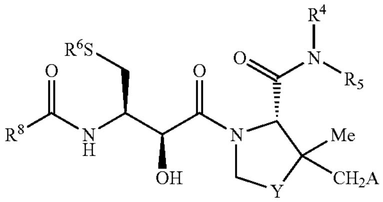
23.2
Scheme 24
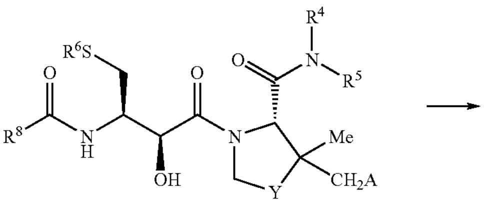
23.2

-continued
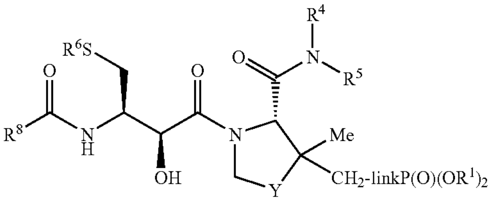
6
Scheme 25
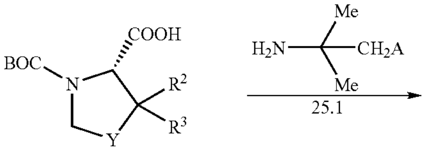
25.1
1.1
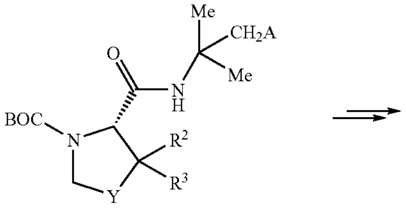
25.2
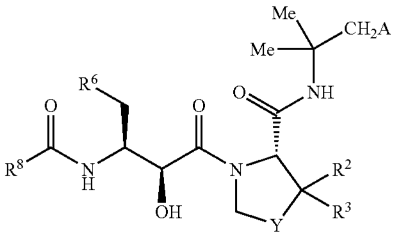
25.3
Scheme 26
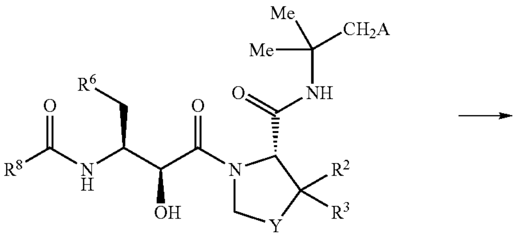
25.3
-continued
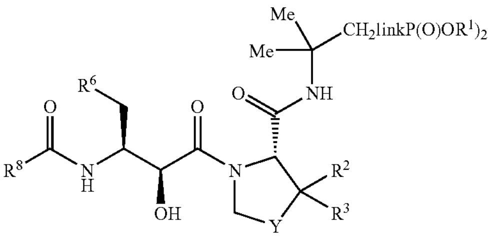
7
Scheme 27
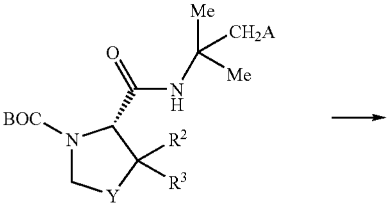
25.2
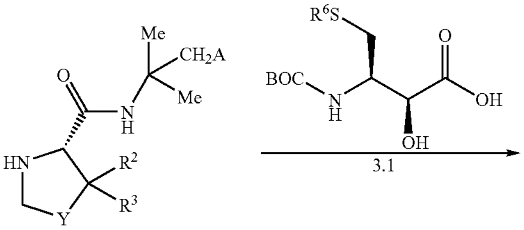
3.1
27.1
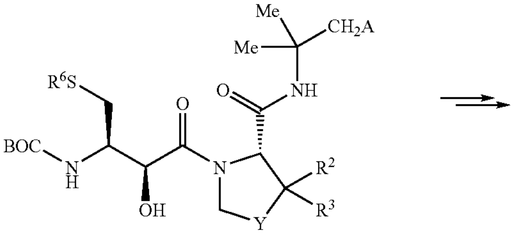
27.2
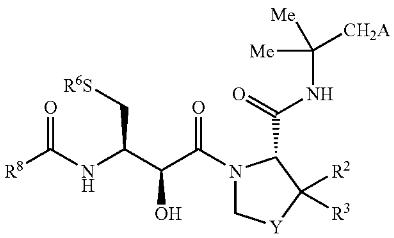
27.3

Scheme 28

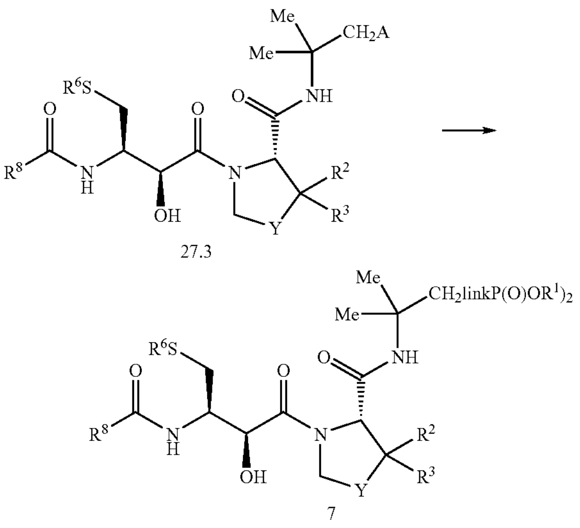

Preparation of the Phosphonate Ester Intermediates 8 in which X is a Direct Bond.

Schemes 29 and 30 illustrate the preparation of the phosphonate esters 8 in which X is a direct bond. As shown in Scheme 29, the carboxylic acid 1.1 is reacted with the amine 29.1, in which the substituent A is either the group link-P(O)$(OR^1)_2$, or a precursor group thereto, such as [OH], [SH], $[NH_2]$, Br, etc, as described herein, to produce the amide 29.2. The reaction is performed using similar conditions to those described above for the preparation of the amide 1.3. The preparation of the amines 29.1 is described below, in Schemes 86-88. The amide product 29.2 is then transformed, using the sequence of reactions shown in Scheme 21 for the conversion of the amide 21.2 into the compound 21.6, into the compound 29.3.

The procedures illustrated in Scheme 29 describe the preparation of the compounds 29.3 in which the substituent A is either the group link-P(O)$(OR^1)_2$, or a precursor group thereto, such as [OH], [SH], $[NH_2]$, Br, etc, as described herein.

Scheme 30 depicts the conversion of the compounds 29.3 in which the A is a precursor to the substituent link-P(O)$(OR^1)_2$ into the compounds 8. Procedures for the conversion of the substituents [OH], [SH], $[NH_2]$, Br etc into the substituent link-P(O)$(OR^1)_2$ are described below in Schemes 45-101.

Preparation of the Phosphonate Ester Intermediates 8 in which X is Sulfur.

Schemes 31 and 32 illustrate the preparation of the phosphonate esters 8 in which X is Sulfur. As shown in Scheme 31, the BOC-protected amine 29.2 is deprotected to yield the free amine 31.1, using the conditions previously described. The amine 31.1 is then reacted, as described above, with the carboxylic acid 3.1 to afford the amide 31.2. The latter compound is then transformed, as described above, (Scheme 23) into the product 31.3.

The procedures illustrated in Scheme 31 describe the preparation of the compounds 31.3 in which the substituent A is either the group link-P(O)$(OR^1)_2$, or a precursor group thereto, such as [OH], [SH], $[NH_2]$, Br, etc, as described herein.

Scheme 32 depicts the conversion of the compounds 31.3 in which the A is a precursor to the substituent link-P(O)$(OR^1)_2$ into the compounds 8. Procedures for the conversion of the substituents [OH], [SH], $[NH_2]$, Br etc into the substituent link-P(O)$(OR^1)_2$ are described below in Schemes 45-101.

Preparation of the Phosphonate Ester Intermediates 9 in which X is a Direct Bond.

Schemes 33 and 34 illustrate the preparation of the phosphonate esters 9 in which X is a direct bond. As shown in Scheme 33, the carboxylic acid 1.5 is reacted with the amine 33.1, in which the substituent A is either the group link-P(O)$(OR^1)_2$, or a precursor group thereto, such as [OH], [SH], $[NH_2]$, Br, etc, as described herein, to produce the amide 33.2. The reaction is performed using similar conditions to those described above for the preparation of the amide 1.6 in Scheme 1. The preparation of the amines 33.1 is described below, in Schemes 91-97. The amide product 33.2 is then transformed into the compound 33.3, using the sequence of reactions shown in Scheme 21 for the conversion of the amide 21.4 into the compound 21.6.

The procedures illustrated in Scheme 33 describe the preparation of the compounds 33.3 in which the substituent A is either the group link-P(O)$(OR^1)_2$, or a precursor group thereto, such as [OH], [SH], $[NH_2]$, Br, etc, as described herein.

Scheme 34 depicts the conversion of the compounds 33.3 in which the A is a precursor to the substituent link-P(O)$(OR^1)_2$ into the compounds 9. Procedures for the conversion of the substituents [OH], [SH], $[NH_2]$, Br etc into the substituent link-P(O)$(OR^1)_2$ are described below in Schemes 45-101.

Preparation of the Phosphonate Ester Intermediates 9 in which X is Sulfur.

Schemes 35 and 36 illustrate the preparation of the phosphonate esters 9 in which X is Sulfur. As shown in Scheme 35 the amine 33.2 is transformed into 35.1 by similar means described above (Scheme 23) for converting 21.3 into 23.2.

The procedures illustrated in Scheme 35 describe the preparation of the compounds 35.1 in which the substituent A is either the group link-P(O)$(OR^1)_2$, or a precursor group thereto, such as [OH], [SH], $[NH_2]$, Br, etc, as described herein.

Scheme 36 depicts the conversion of the compounds 35.1 in which the A is a precursor to the substituent link-P(O)$(OR^1)_2$ into the compounds 9. Procedures for the conversion of the substituents [OH], [SH], $[NH_2]$, Br etc into the substituent link-P(O)$(OR^1)_2$ are described below in Schemes 45-101.

Preparation of the Phosphonate Ester Intermediates 10 in which X is a Direct Bond.

Schemes 37 and 38 illustrate the preparation of the phosphonate esters 10 in which X is a direct bond. As shown in Scheme 37, the carboxylic acid 1.5 is reacted with the amine 37.1, in which the substituent A is either the group link-P(O)$(OR^1)_2$, or a precursor group thereto, such as [OH], [SH], $[NH_2]$, Br, etc, as described herein, to produce the amide 37.2. The reaction is performed using similar conditions to those described above for the preparation of the amide 1.6. The preparation of the amines 37.1 is described below, in Scheme 91-97. The amide product 37.2 is then transformed into the compound 37.3, using the sequence of reactions shown in Scheme 21 for the conversion of the amide 21.4 into the compound 21.6.

The procedures illustrated in Scheme 37 describe the preparation of the compounds 37.3 in which the substituent A is either the group link-$P(O)(OR^1)_2$, or a precursor group thereto, such as [OH], [SH], $[NH_2]$, Br, etc, as described herein.

Scheme 38 depicts the conversion of the compounds 37.3 in which the A is a precursor to the substituent link-P(O) $(OR^1)_2$ into the compounds 10. Procedures for the conversion of the substituents [OH], [SH], $[NH_2]$, Br etc into the substituent link-$P(O)(OR^1)_2$ are described below in Schemes 45-101.

Preparation of the Phosphonate Ester Intermediates 10 in which X is Sulfur.

Schemes 39 and 40 illustrate the preparation of the phosphonate esters 10 in which X is Sulfur.

As shown in Scheme 39 the amine 37.1 is transformed into the product 39.1, as described above, (Scheme 23) for the conversion of 21.3 into 23.2.

The procedures illustrated in Scheme 39 describe the preparation of the compounds 39.1 in which the substituent A is either the group link-$P(O)(OR^1)_2$, or a precursor group thereto, such as [OH], [SH], $[NH_2]$, Br, etc, as described herein.

Scheme 40 depicts the conversion of the compounds 39.1 in which the A is a precursor to the substituent link-P(O) $(OR^1)_2$ into the compounds 10. Procedures for the conversion of the substituents [OH], [SH], $[NH_2]$, Br etc into the substituent link-$P(O)(OR^1)_2$ are described below in Schemes 45-101.

Scheme 29

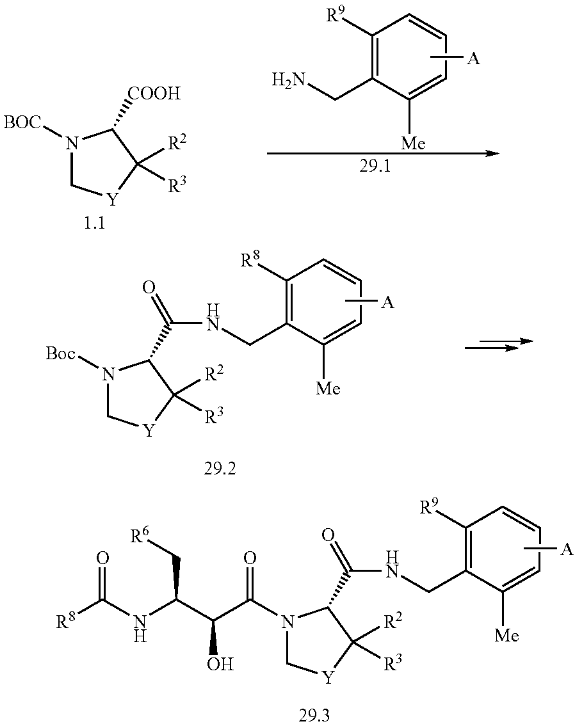

1.1

29.1

29.2

29.3

Scheme 30

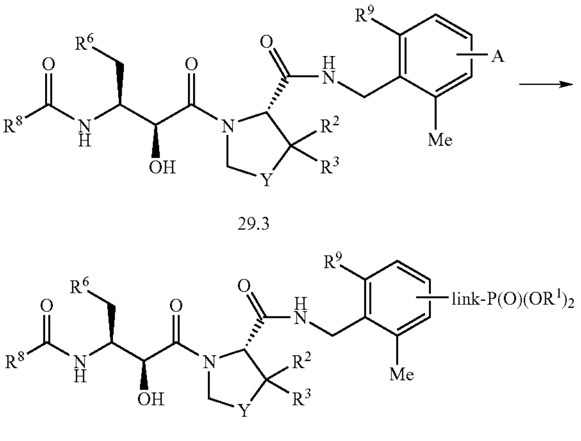

29.3

8

Scheme 31

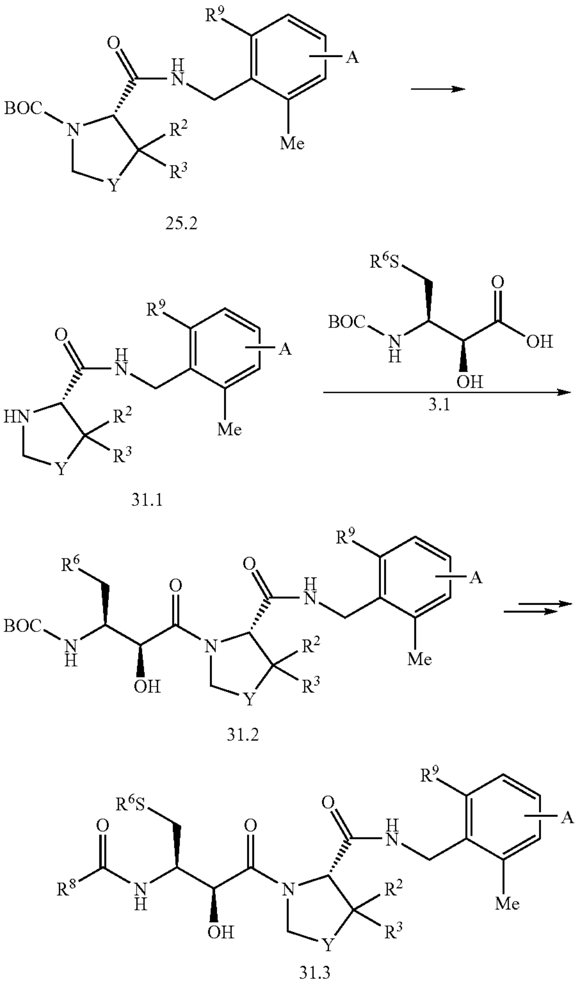

25.2

31.1

3.1

31.2

31.3

Scheme 32
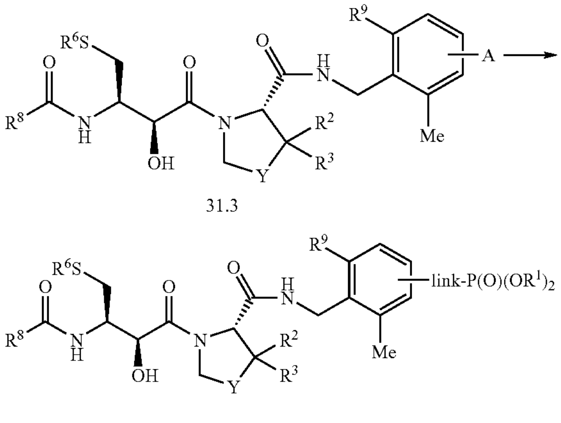
31.3
8
Scheme 33
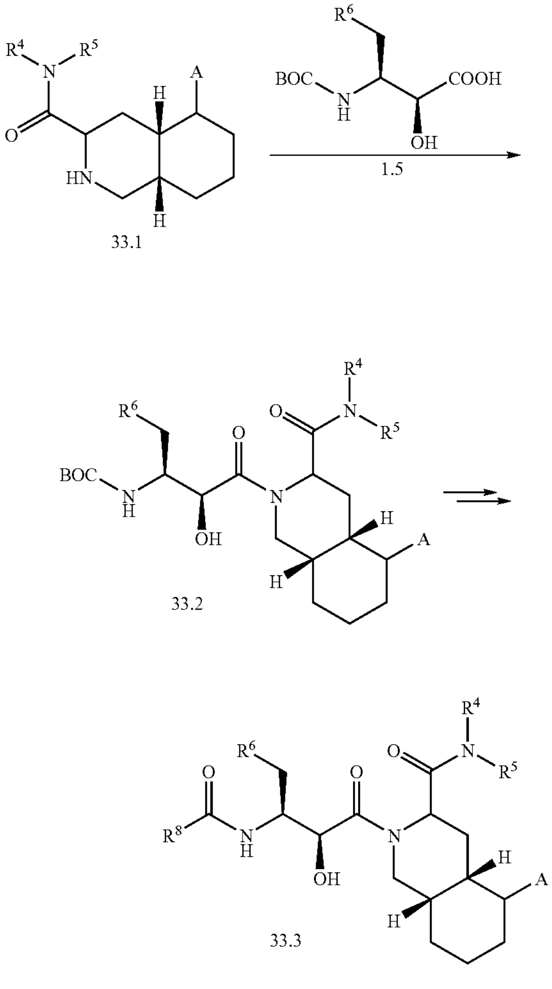
33.1
1.5
33.2
33.3
Scheme 34
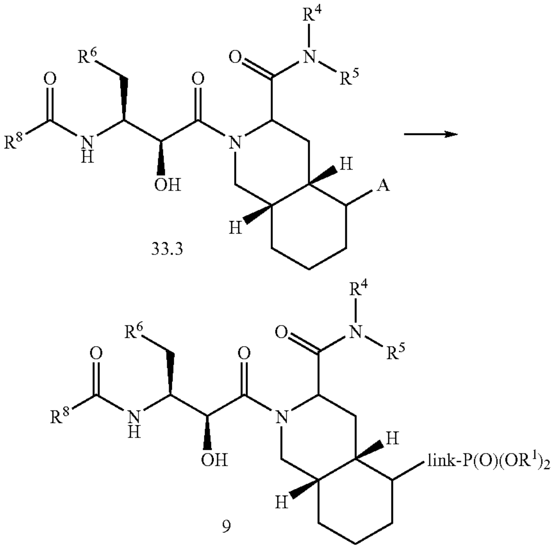
33.3
9
Scheme 35
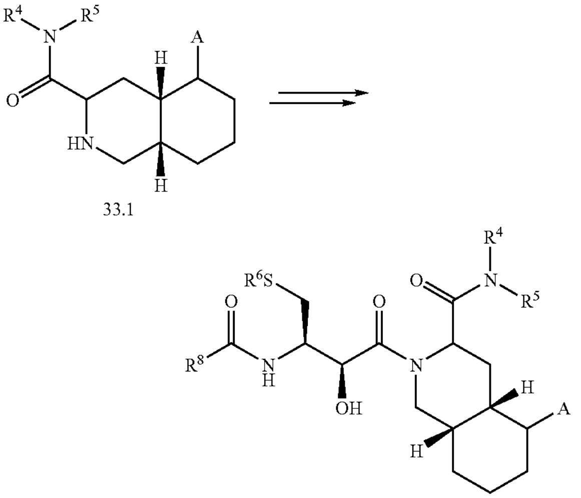
33.1
35.1
Scheme 36
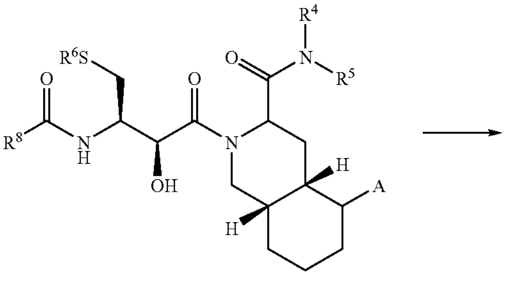
35.1

-continued

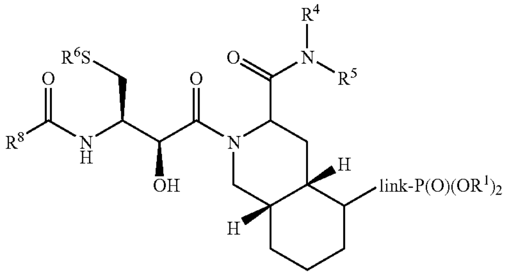

9

Scheme 37

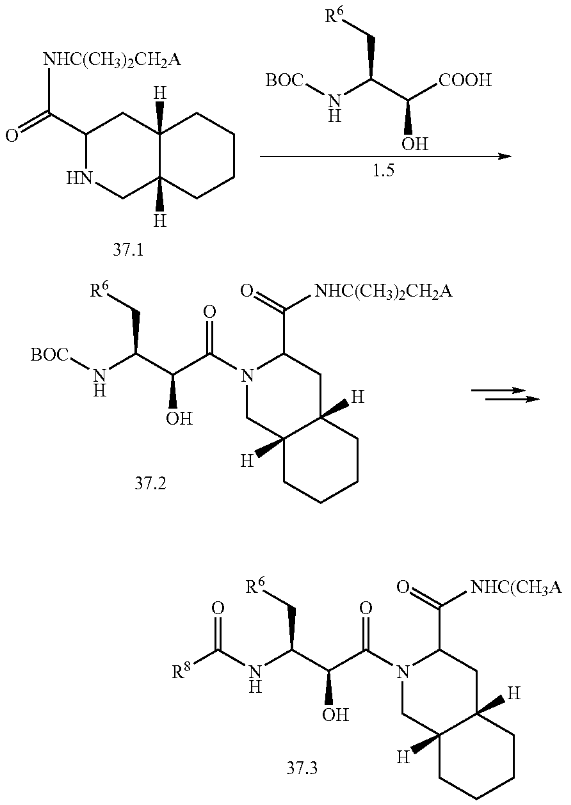

37.1

37.2

37.3

Scheme 38

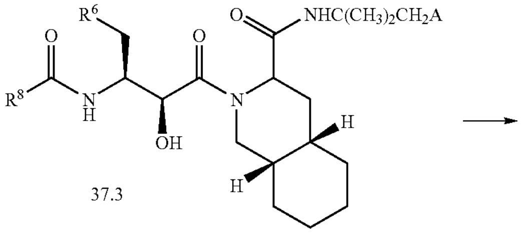

37.3

-continued

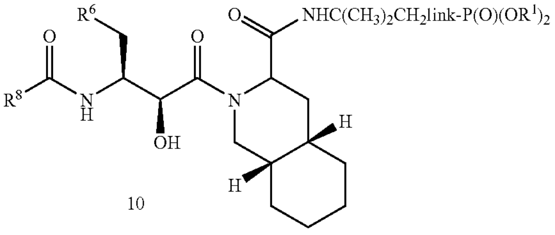

10

Scheme 39

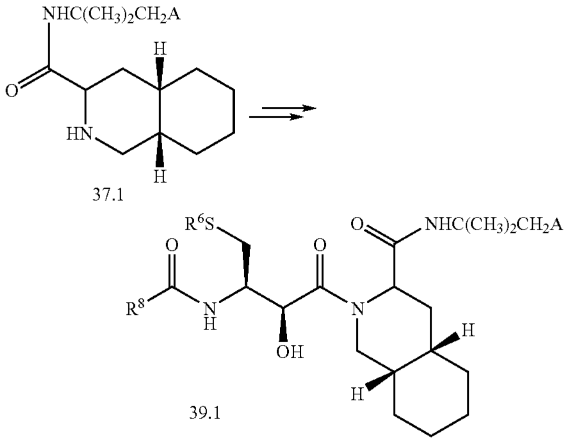

37.1

39.1

Scheme 40

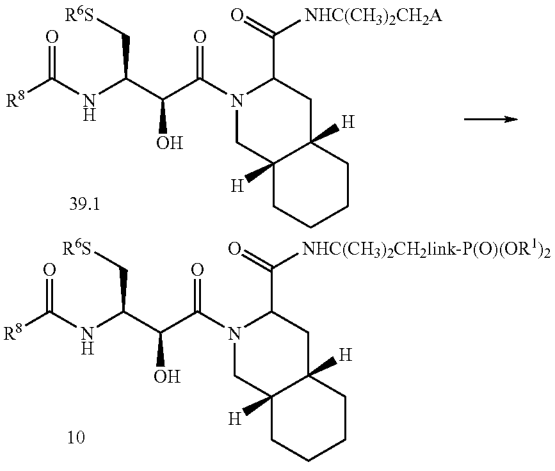

39.1

10

Preparation of the BOC-protected Aminohydroxy Phenylbutanoic Acids 1.5.

The preparation of the butanoic acid derivatives 1.5 in which $R^6$ is phenyl is described, for example, in Tet. Asym., 2002, 13, 1201, Eur. J. Med. Chem., 2000, 35, 887, Chem. Pharm. Bull., 2000, 48, 1310, J. Med. Chem., 1994, 37, 2918, J. Chem. Res., 1999, 282 and J. Med. Chem., 1993, 36, 211. The analogs 1.5 in which the substituent $R^6$ is as described in Chart 5 are prepared by analogous reaction sequences.

Schemes 41 and 42 illustrate two alternative procedures for the preparation of the reactants 1.5. As shown in Scheme 41, the BOC-protected aminoacid 41.1 is converted into the corresponding aldehyde 41.3. Numerous methods are known for the conversion of carboxylic acids and derivatives into the corresponding aldehydes, for example as described in Comprehensive Organic Transformations, by R. C. Larock, VCH, 1989, p. 619-627. The conversion is effected by direct reduction of the carboxylic acid, for example employing diisobutyl aluminum hydride, as described in J. Gen. Chem. USSR., 34, 1021, 1964, or alkyl borane reagents, for example as described in J. Org. Chem., 37, 2942, 1972. Alternatively, the carboxylic acid is converted into an amide, such as the N-methoxy N-methyl amide, and the latter compound is reduced with lithium aluminum hydride, for example as described in J. Med. Chem., 1994, 37, 2918, to afford the aldehyde 41.3. Alternatively, the carboxylic acid is reduced to the corresponding carbinol 41.2. The reduction of carboxylic acids to carbinols is described, for example, in Comprehensive Organic Transformations, by R. C. Larock, VCH, 1989, p. 548ff. The reduction reaction is performed by the use of reducing agents such as borane, as described in J. Am. Chem. Soc., 92, 1637, 1970, or by lithium aluminum hydride, as described in Org. Reac., 6, 649, 1951. The resultant carbinol 41.2 is then converted into the aldehyde 41.3 by means of an oxidation reaction. The oxidation of a carbinol to the corresponding aldehyde is described, for example, in Comprehensive Organic Transformations, by R. C. Larock, VCH, 1989, p. 604ff. The conversion is effected by the use of oxidizing agents such as pyridinium chlorochromate, as described in J. Org. Chem., 50, 262, 1985, or silver carbonate, as described in Compt. Rend. Ser. C., 267, 900, 1968, or dimethyl sulfoxide/acetic anhydride, as described in J. Am. Chem. Soc., 87, 4214, 1965. Preferably, the carbinol 41.2 is converted into the aldehyde 41.3 by oxidation with pyridine-sulfur trioxide in dimethyl sulfoxide, as described in Eur. J. Med. Chem., 35, 2000, 887. The aldehyde 41.3 is then transformed into the cyanohydrin 1.4. The transformation of an aldehyde into the corresponding cyanohydrin is effected by reaction with an alkali metal cyanide such as potassium cyanide, in an aqueous organic solvent mixture. Preferably, a solution of the aldehyde in ethyl acetate is reacted with an aqueous solution of potassium cyanide, as described in Eur. J. Med. Chem., 35, 2000, 887, to yield the cyanohydrin 41.4. Optionally, a methanolic solution of the aldehyde is first treated with an aqueous solution of sodium bisulfite, and the bisulfite adduct which is formed in situ is then reacted with an aqueous solution of sodium cyanide, as described in J. Med. Chem., 37, 1994, 2918, to give the cyanohydrin 41.4. The latter compound is then hydrolyzed to afford the hydroxyacid product 41.5. The hydrolysis is effected under acidic conditions; for example, the cyanohydrin 41.4 is heated in a mixture of concentrated hydrochloric acid and dioxan, as described in Eur. J. Med. Chem., 35, 2000, 887, optionally in the presence of anisole, as described in J. Med. Chem., 37, 1994, 2918, to afford the hydroxyacid product, from which the (2S), (3S) isomer 41.5 is isolated. The BOC protecting group is then attached, for example by reaction of the aminoacid 41.5 with BOC anhydride in aqueous tetrahydrofuran containing triethylamine, as described in Eur. J. Med. Chem., 35, 2000, 887.

Alternatively, the BOC-protected aminohydroxy phenylbutanoic acids 1.5 are obtained by means of the reaction sequence shown in Scheme 42. In this sequence, the N,N-dibenzyl aminoacid ester 42.1, prepared as described in Tet., 1995, 51, 6397, is converted, using the procedures described above in Scheme 41, into the corresponding aldehyde 42.2. The latter compound is then reacted with a silylmethyl Grignard reagent, for example isopropoxydimethylsilylmethylmagnesium chloride 42.3, to give the carbinol product 42.4. Preferably, the aldehyde and ca. two molar equivalents of the Grignard reagent are reacted in tetrahydrofuran solution at 0°, as described in Tet. Asym., 2002, 13, 1201. The silyl carbinol 42.4 is then reacted with aqueous ammonium chloride, as described in Tet. Asym., 2002, 13, 1201, to give the diol 42.5. The N-benzyl groups are then removed to afford the free amine 42.6. The removal of N-benzyl groups is described, for example, in Protective Groups in Organic Synthesis, by T. W. Greene and P. G. M Wuts, Wiley, Second Edition 1990, p. 365. Benzyl groups are removed by catalytic hydrogenation in the presence of hydrogen or a hydrogen donor, by reduction with sodium in ammonia, by treatment with trichloroethyl chloroformate, or by oxidation, for example by the use of ruthenium tetroxide or 3chloroperoxybenzoic acid and ferrous chloride. Preferably, the debenzylation is effected by hydrogenation of the substrate 42.5 in ethanol at ca 50° in the presence of 5% palladium on carbon catalyst, as described in Tet. Asym., 2002, 13, 1201, to produce the amine 42.6. The BOC protecting group is then attached using the procedures described above, and the resultant product 42.7 is oxidized to give the carboxylic acid 1.5. The oxidation of carbinols to afford the corresponding carboxylic acid is described in Comprehensive Organic Transformations, by R. C. Larock, VCH, 1989, p. 835. The conversion can be effected by the sue of oxidizing agents such as chromium trioxide in acetic acid, potassium permanganate, ruthenium tetroxide or silver oxide. Preferably, the transformation is effected by the use of sodium chlorite and sodium hypochlorite in aqueous acetonitrile in the presence of a pH 6.7 phosphate buffer and a catalytic amount of 2,2,6,6,-tetramethylpiperidin-1-oxyl, as described in Tet. Asym., 2002, 13, 1201, to afford the carboxylic acid 1.5.

Preparation of the BOC-protected Aminohydroxy Arylthiobutanoic Acids 3.1.

Schemes 43 and 44 illustrate two alternative methods for the preparation of the BOC-protected aminohydroxy arylthiobutanoic acids 3.1. As shown in Scheme 43, N,N-dibenzyl serine methyl ester 43.1, prepared as described in J. Org. Chem., 1986, 63, 1709, is converted into the methanesulfonate ester 43.2. The carbinol is reacted with methanesulfonyl chloride and triethylamine in toluene, as described in J. Org. Chem., 65, 2000, 1623, to produce the mesylate 43.2. The latter compound is then reacted with a thiophenol $R^6SH$, in the presence of a base, to give the thioether 43.4. The displacement reaction is performed in an organic solvent such as dimethylformamide, or in an aqueous organic solvent mixture, in the presence of an organic base such as triethylamine or dimethylaminopyridine, or an inorganic base such as potassium carbonate and the like. Preferably, the reactants are combined in toluene solution in the presence of aqueous sodium hydroxide and a phase transfer catalyst such as tetrabutyl ammonium bromide, as described in J. Org. Chem., 65, 2000, 1623, to afford the product 43.4. The ester product is then transformed into the corresponding aldehyde 43.5, using the procedures described above (Scheme 41). The aldehyde is then converted, using the sequence of reactions shown in Scheme 41, into the BOC-protected aminohydroxy arylthiobutanoic acids 3.1.

Alternatively, as shown in Scheme 44, the aldehyde 43.5 is converted, using the sequence of reactions shown in Scheme 42, into the product 3.1. The component reactions of this sequence are performed under similar conditions to those described for the analogous reactions in Scheme 42.

Preparation of Phosphonate-containing Hydroxymethyl Benzoic Acids 1.8.

Schemes 45-49 illustrate methods for the preparation of phosphonate-containing hydroxymethyl benzoic acids 1.8 which are employed in the preparation of the phosphonate esters 1.

Scheme 45 illustrates a method for the preparation of hydroxymethylbenzoic acid reactants in which the phosphonate moiety is attached directly to the phenyl ring. In this method, a suitably protected bromo hydroxy methyl benzoic acid 45.1 is subjected to halogen-methyl exchange to afford the organometallic intermediate 45.2. This compound is reacted with a chlorodialkyl phosphite 45.3 to yield the phenylphosphonate ester 45.4, which upon deprotection affords the carboxylic acid 45.5.

For example, 4-bromo-3-hydroxy-2-methylbenzoic acid, 45.6, prepared by bromination of 3-hydroxy-2-methylbenzoic acid, as described, for example, J. Am. Chem. Soc., 55, 1676, 1933, is converted into the acid chloride, for example by reaction with thionyl chloride. The acid chloride is then reacted with 3-methyl-3-hydroxymethyloxetane 45.7, as described in Protective Groups in Organic Synthesis, by T. W. Greene and P. G. M. Wuts, Wiley, 1991, pp. 268, to afford the ester 45.8. This compound is treated with boron trifluoride at 0° to effect rearrangement to the orthoester 45.9, known as the OBO ester. This material is treated with a silylating reagent, for example tert-butyl chlorodimethylsilane, in the presence of a base such as imidazole, to yield the silyl ether 45.10. Halogen-metal exchange is performed by the reaction of the substrate 45.10 with butyllithium, and the lithiated intermediate is then coupled with a chlorodialkyl phosphite 45.3, to produce the phosphonate 45.11. Deprotection, for example by treatment with 4-toluenesulfonic acid in aqueous pyridine, as described in Can. J. Chem., 61, 712, 1983, removes both the OBO ester and the silyl group, to produce the carboxylic acid 45.12.

Using the above procedures, but employing, in place of the bromo compound 45.6, different bromo compounds 45.1, there are obtained the corresponding products 45.5.

Scheme 46 illustrates the preparation of hydroxymethylbenzoic acid derivatives in which the phosphonate moiety is attached by means of a one-carbon link.

In this method, a suitably protected dimethyl hydroxybenzoic acid, 46.1, is reacted with a brominating agent, so as to effect benzylic bromination. The product 46.2 is reacted with a sodium dialkyl phosphite, 46.3, as described in J. Med. Chem., 1992, 35, 1371, to effect displacement of the benzylic bromide to afford the phosphonate 46.4. Deprotection of the carboxyl function then yields the carboxylic acid 46.5.

For example, 2,5-dimethyl-3-hydroxybenzoic acid, 46.6, the preparation of which is described in Can. J. Chem., 1970, 48, 1346, is reacted with excess methoxymethyl chloride, as described in Protective Groups in Organic Synthesis, by T. W. Greene and P. G. M Wuts, Second Edition 1990, p.17, to afford the ether ester 46.7. The reaction is performed in an inert solvent such as dichloromethane, in the presence of an organic base such as N-methylmorpholine or diisopropylethylamine. The product 46.7 is then reacted with a brominating agent, for example N-bromosuccinimide, in an inert solvent such as, for example, ethyl acetate, at reflux, to afford the bromomethyl product 46.8. This compound is then reacted with a sodium dialkyl phosphite 46.3 in tetrahydrofuran, as described above, to afford the phosphonate 46.9. Deprotection, for example by brief treatment with a trace of mineral acid in methanol, as described in J. Chem. Soc. Chem. Comm., 1974, 298, then yields the carboxylic acid 46.10. Using the above procedures, but employing, in place of the methyl compound 46.6, different methyl compounds 46.1, there are obtained the corresponding products 46.5.

Scheme 47 illustrates the preparation of phosphonate-containing hydroxymethylbenzoic acids in which the phosphonate group is attached by means of an oxygen or sulfur atom.

In this method, a suitably protected hydroxy- or mercapto-substituted hydroxy methyl benzoic acid 47.1 is reacted, under the conditions of the Mitsonobu reaction, with a dialkyl hydroxymethyl phosphonate 47.2, to afford the coupled product 47.3, which upon deprotection affords the carboxylic acid 47.4.

For example, 3,6-dihydroxy-2-methylbenzoic acid, 47.5, the preparation of which is described in Yakugaku Zasshi 1971, 91, 257, is converted into the diphenylmethyl ester 47.6, by treatment with diphenyldiazomethane, as described in Protective Groups in Organic Synthesis, by T. W. Greene and P. G. M. Wuts, Wiley, 1991, pp. 253. The product is then reacted with one equivalent of a silylating reagent, such as, for example, tert butylchlorodimethylsilane, as described in Protective Groups in Organic Synthesis, by T. W. Greene and P. G. M Wuts, Wiley, Second Edition 1990, p 77, to afford the mono-silyl ether 47.7. This compound is then reacted with a dialkyl hydroxymethylphosphonate 47.2, under the conditions of the Mitsonobu reaction. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol or thiophenol and the alcohol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The reaction affords the coupled product 47.9. Deprotection, for example by treatment with trifluoroacetic acid at ambient temperature, as described in J. Chem. Soc., C, 1191, 1966, then affords the phenolic carboxylic acid 47.9.

Using the above procedures, but employing, in place of the phenol 47.5, different phenols or thiophenols 47.1, there are obtained the corresponding products 47.4.

Scheme 48 depicts the preparation of phosphonate esters attached to the hydroxymethylbenzoic acid moiety by means of unsaturated or saturated carbon chains. In this method, a dialkyl alkenylphosphonate 48.2 is coupled, by means of a palladium catalyzed Heck reaction, with a suitably protected bromo substituted hydroxymethylbenzoic acid 48.1. The coupling of aryl halides with olefins by means of the Heck reaction is described, for example, in Advanced Organic Chemistry, by F. A. Carey and R. J. Sundberg, Plenum, 2001, p. 503ff and in Ace. Chem. Res., 12, 146, 1979. The aryl bromide and the olefin are coupled in a polar solvent such as dimethylformamide or dioxan, in the presence of a palladium (0) catalyst such as tetrakis(triphenylphosphine)palladium(0) or palladium(II) catalyst such as palladium(II) acetate, and optionally in the presence of a base such as triethylamine or potassium carbonate. The product 48.3 is deprotected to afford the phosphonate 48.4; the latter compound is subjected to catalytic hydrogenation to afford the saturated carboxylic acid 48.5.

For example, 5-bromo-3-hydroxy-2-methylbenzoic acid 48.6, prepared as described in WO 9218490, is converted as described above, into the silyl ether OBO ester 48.7. This compound is coupled with, for example, a dialkyl 4-buten-1-ylphosphonate 48.8, the preparation of which is described in J. Med. Chem., 1996, 39, 949, using the conditions described above to afford the product 48.9. Deprotection, or hydrogenation/deprotection, of this compound, as described above, then affords respectively the unsaturated and saturated products 48.10 and 48.11.

Using the above procedures, but employing, in place of the bromo compound 48.6, different bromo compounds 48.1, and/or different phosphonates 48.2, there are obtained the corresponding products 48.4 and 48.5.

Scheme 49 illustrates the preparation of phosphonate esters linked to the hydroxymethylbenzoic acid moiety by means of an aromatic ring.

In this method, a suitably protected bromo-substituted hydroxymethylbenzoic acid 49.1 is converted to the corresponding boronic acid 49.2, by metallation with butyllithium and boronation, as described in J. Organomet. Chem., 1999, 581, 82. The product is subjected to a Suzuki coupling reaction with a dialkyl bromophenyl phosphonate 49.3. The product 49.4 is then deprotected to afford the diaryl phosphonate product 49.5.

For example, the silylated OBO ester 49.6, prepared as described above, (Scheme 45), from 5-bromo-3-hydroxybenzoic acid, the preparation of which is described in J. Labelled. Comp. Radiopharm., 1992, 31, 175, is converted into the boronic acid 49.7, as described above. This material is coupled with a dialkyl 4-bromophenyl phosphonate 49.8, prepared as described in J. Chem. Soc. Perkin Trans., 1977, 2, 789, using tetrakis(triphenylphosphine)palladium(0) as catalyst, in the presence of sodium bicarbonate, as described, for example, in Palladium reagents and catalysts J. Tsuji, Wiley 1995, p 218, to afford the diaryl phosphonate 49.9. Deprotection, as described above, then affords the benzoic acid 49.10.

Using the above procedures, but employing, in place of the bromo compound 49.6, different bromo compounds 49.1, and/or different phosphonates 49.3, there are obtained the corresponding carboxylic acid products 49.5.

Scheme 41

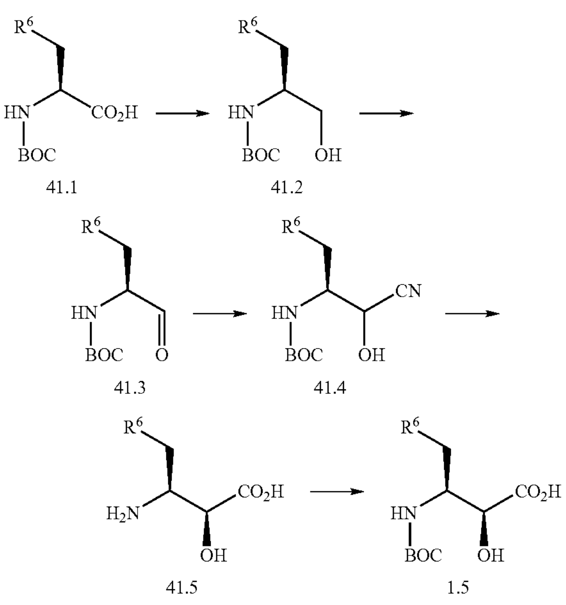

41.1 41.2 41.3 41.4 41.5 1.5

Scheme 42

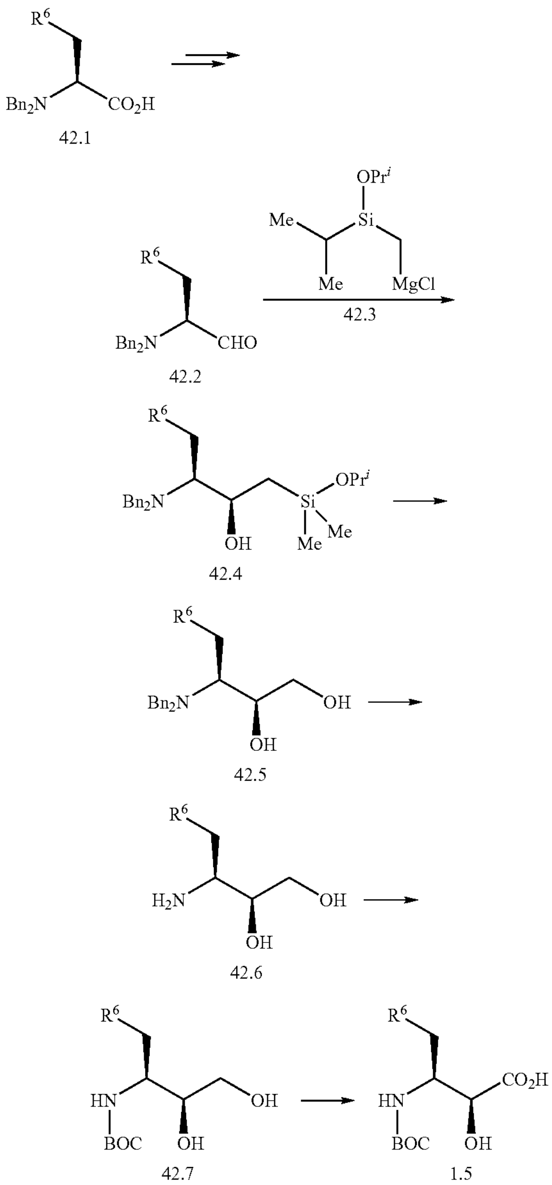

42.1 42.2 42.4 42.5 42.6 42.7 1.5

Scheme 43

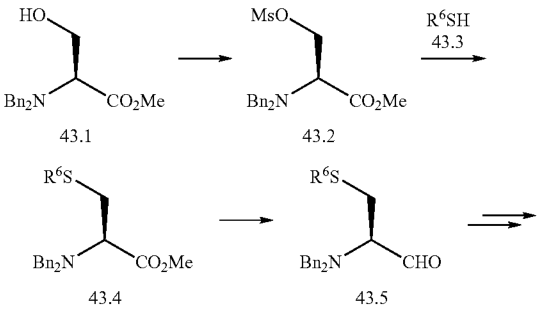

43.1 43.2 43.4 43.5

-continued
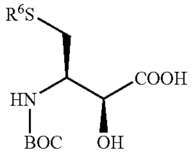
3.1
Scheme 44
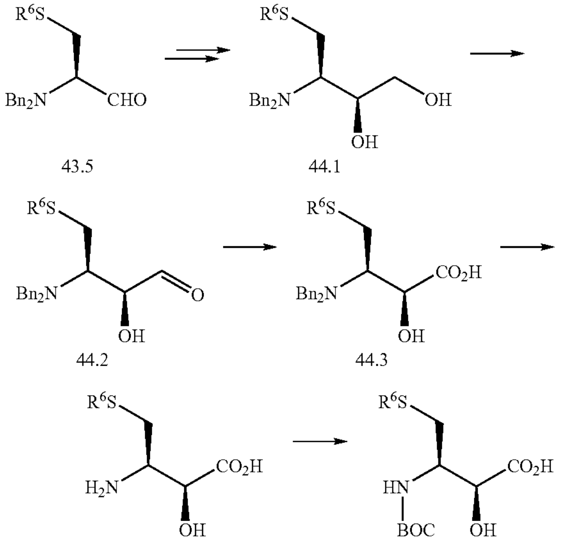
43.5 44.1 44.2 44.3 44.4 3.1
Scheme 49
Method
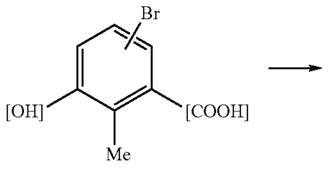
49.1
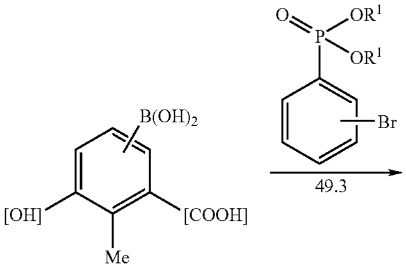
49.2 49.3
-continued
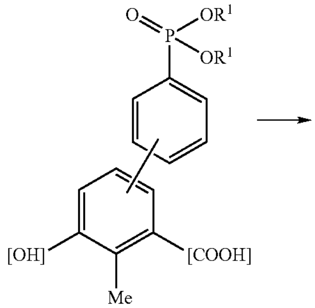
49.4
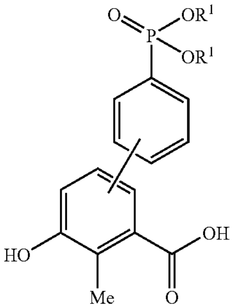
49.5
Example
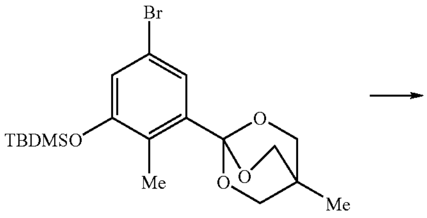
49.6
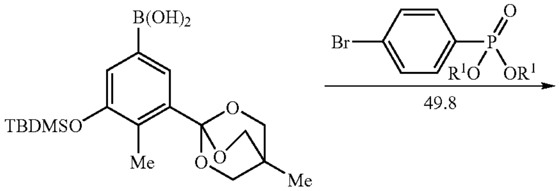
49.7 49.8
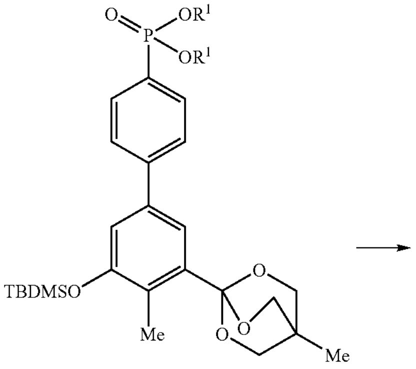
49.9

-continued

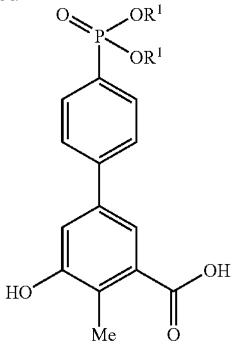

49.10

Preparation of Dimethylphenoxyacetic Acids 5.1 Incorporating Phosphonate Moieties.

The preparation of the dimethylphenoxyacetic acids 5.1 incorporating phosphonate moieties which are used in the preparation of the phosphonate esters 2 is described in Schemes 50-56.

Scheme 50 illustrates two alternative methods by means of which 2,6-dimethylphenoxyacetic acids bearing phosphonate moieties may be prepared. The phosphonate group may be introduced into the 2,6-dimethylphenol moiety, followed by attachment of the acetic acid group, or the phosphonate group may be introduced into a preformed 2,6-dimethylphenoxyacetic acid intermediate. In the first sequence, a substituted 2,6-dimethylphenol 50.1, in which the substituent B is a precursor to the group link-$P(O)(OR^1)_2$, and in which the phenolic hydroxyl may or may not be protected, depending on the reactions to be performed, is converted into a phosphonate-containing compound 50.2. Methods for the conversion of the substituent B into the group link-$P(O)(OR^1)_2$ are described in Schemes 46-101.

The protected phenolic hydroxyl group present in the phosphonate-containing product 50.2 is then deprotected, using methods described below, to afford the phenol 50.3.

The phenolic product 50.3 is then transformed into the corresponding phenoxyacetic acid 50.4, in a two step procedure. In the first step, the phenol 50.3 is reacted with an ester of bromoacetic acid 50.4, in which R is an alkyl group or a protecting group. Methods for the protection of carboxylic acids are described in Protective Groups in Organic Synthesis, by T. W. Greene and P. G. M Wuts, Wiley, Second Edition 1990, p. 224ff. The alkylation of phenols to afford phenolic ethers is described, for example, in Comprehensive Organic Transformations, by R. C. Larock, VCH, 1989, p. 446ff. Typically, the phenol and the alkylating agent are reacted together in the presence of an organic or inorganic base, such as, for example, diazabicyclononene, (DBN) or potassium carbonate, in a polar organic solvent such as, for example, dimethylformamide or acetonitrile.

Preferably, equimolar amounts of the phenol 50.3 and ethyl bromoacetate are reacted together in the presence of cesium carbonate, in dioxan at reflux temperature, for example as described in U.S. Pat. No. 5,914,332, to afford the ester 50.5.

The thus-obtained ester 50.5 is then hydrolyzed to afford the carboxylic acid 50.6. The methods used for this reaction depend on the nature of the group R. If R is an alkyl group such as methyl, hydrolysis can be effected by treatment of the ester with aqueous or aqueous alcoholic base, or by use of an esterase enzyme such as porcine liver esterase. If R is a protecting group, methods for hydrolysis are described in Protective Groups in Organic Synthesis, by T. W. Greene and P. G. M Wuts, Wiley, Second Edition 1990, p. 224ff.

Preferably, the ester product 50.5 which R is ethyl is hydrolyzed to the carboxylic acid 50.6 by reaction with lithium hydroxide in aqueous methanol at ambient temperature, as described in U.S. Pat. No. 5,914,332.

Alternatively, an appropriately substituted 2,6-dimethylphenol 50.8, in which the substituent B is a precursor to the group link-$P(O)(OR^1)_2$, is transformed into the corresponding phenoxyacetic ester 50.7. The conditions employed for the alkylation reaction are similar to those described above for the conversion of the phenol 50.3 into the ester 50.5.

The phenolic ester 50.7 is then converted, by transformation of the group B into the group link-$P(O)(OR^1)_2$ followed by ester hydrolysis, into the carboxylic acid 50.6. The group B which is present in the ester 50.6 may be transformed into the group link-$P(O)(OR^1)_2$ either before or after hydrolysis of the ester moiety into the carboxylic acid group, depending on the nature of the chemical transformations required.

Schemes 51-56 illustrate the preparation of 2,6-dimethylphenoxyacetic acids incorporating phosphonate ester groups. The procedures shown can also be applied to the preparation of phenoxyacetic esters acids 50.7, with, if appropriate, modifications made according to the knowledge of one skilled in the art.

Scheme 51 illustrates the preparation of 2,6-dimethylphenoxyacetic acids incorporating a phosphonate ester which is attached to the phenolic group by means of a carbon chain incorporating a nitrogen atom. The compounds 51.4 are obtained by means of a reductive alkylation reaction between a 2,6-dimethylphenol aldehyde 51.1 and an aminoalkyl phosphonate ester 51.2. The preparation of amines by means of reductive amination procedures is described, for example, in Comprehensive Organic Transformations, by R. C. Larock, VCH, p. 421. In this procedure, the amine component 51.2 and the aldehyde component 51.1 are reacted together in the presence of a reducing agent such as, for example, borane, sodium cyanoborohydride or diisobutylaluminum hydride, to yield the amine product 51.3. The amination product 51.3 is then converted into the phenoxyacetic acid compound 51.4, using the alkylation and ester hydrolysis procedures described above, (Scheme 50) For example, equimolar amounts of 4-hydroxy-3,5-dimethylbenzaldehyde 51.5 (Aldrich) and a dialkyl aminoethyl phosphonate 51.6, the preparation of which is described in J. Org. Chem., 2000, 65, 676, are reacted together in the presence of sodium cyanoborohydride and acetic acid, as described, for example, in J. Am. Chem. Soc., 91, 3996, 1969, to afford the amine product 51.7. The product is then converted into the acetic acid 51.8, as described above. Using the above procedures, but employing, in place of the aldehyde 51.5, different aldehydes 51.1, and/or different aminoalkyl phosphonates 51.2, the corresponding products 51.4 are obtained.

Scheme 52 depicts the preparation of 2,6-dimethylphenols incorporating a phosphonate group linked to the phenyl ring by means of a saturated or unsaturated alkylene chain. In this procedure, an optionally protected bromo-substituted 2,6-dimethylphenol 52.1 is coupled, by means of a palladium-catalyzed Heck reaction, with a dialkyl alkenyl phosphonate 52.2. The coupling of aryl bromides with olefins by means of the Heck reaction is described, for example, in Advanced Organic Chemistry, by F. A. Carey and R. J. Sundberg, Plenum, 2001, p. 503. The aryl bromide and the olefin are coupled in a polar solvent such as dimethylformamide or dioxan, in the presence of a palladium(0) or palladium (2) catalyst. Following the coupling reaction, the product 52.3 is converted, using the procedures described above, (Scheme 50) into the corresponding phenoxyacetic acid 52.4. Alternatively, the olefinic product 52.3 is reduced to afford the saturated 2,6-dimethylphenol derivative 52.5. Methods for the reduction of carbon-carbon double bonds are described, for example, in Comprehensive Organic Transformations, by R. C. Larock, VCH, 1989, p. 6. The methods include catalytic reduction, or chemical reduction employing, for example, diborane or diimide. Following the reduction reaction, the product 52.5 is converted, as described above, (Scheme 50) into the corresponding phenoxyacetic acid 52.6.

For example, 3-bromo-2,6-dimethylphenol 52.7, prepared as described in Can. J. Chem., 1983, 61, 1045, is converted into the tert-butyldimethylsilyl ether 52.8, by reaction with chloro-tert-butyldimethylsilane, and a base such as imidazole, as described in Protective Groups in Organic Synthesis, by T. W. Greene and P. G. M Wuts, Wiley, Second Edition 1990 p. 77. The product 52.8 is reacted with an equimolar amount of a dialkyl allyl phosphonate 52.9, for example diethyl allylphosphonate (Aldrich) in the presence of ca. 3 mol % of bis(triphenylphosphine)palladium(II) chloride, in dimethylformamide at ca. 60°, to produce the coupled product 52.10. The silyl group is removed, for example by the treatment of the ether 52.10 with a solution of tetrabutylammonium fluoride in tetrahydrofuran, as described in J. Am. Chem., Soc., 94, 6190, 1972, to afford the phenol 52.11. This compound is converted, employing the procedures described above, (Scheme 50) into the corresponding phenoxyacetic acid 52.12. Alternatively, the unsaturated compound 52.11 is reduced, for example by catalytic hydrogenation employing 5% palladium on carbon as catalyst, in an alcoholic solvent such as methanol, as described, for example, in Hydrogenation Methods, by R. N. Rylander, Academic Press, 1985, Ch. 2, to afford the saturated analog 52.13. This compound is converted, employing the procedures described above, (Scheme 50) into the corresponding phenoxyacetic acid 52.14.

Using the above procedures, but employing, in place of 3-bromo-2,6-dimethylphenol 52.7, different bromophenols 52.1, and/or different dialkyl alkenyl phosphonates 52.2, the corresponding products 52.4 and 52.6 are obtained.

Scheme 53 illustrates the preparation of phosphonate-containing 2,6-dimethylphenoxyacetic acids 53.1 in which the phosphonate group is attached to the 2,6-dimethylphenoxy moiety by means of a carbocyclic ring. In this procedure, a bromo-substituted 2,6-dimethylphenol 53.2 is converted, using the procedures illustrated in Scheme 50, into the corresponding 2,6-dimethylphenoxyacetic ester 53.3. The latter compound is then reacted, by means of a palladium-catalyzed Heck reaction, with a cycloalkenone 53.4, in which n is 1 or 2. The coupling reaction is conducted under the same conditions as those described above for the preparation of the unsaturated phosphonate 52.3. (Scheme 52). The product 53.5 is then reduced catalytically, as described above for the reduction of the phosphonate 52.3, (Scheme 52), to afford the substituted cycloalkanone 53.6. The ketone is then subjected to a reductive amination procedure, by reaction with a dialkyl 2-aminoalkylphosphonate 53.7 and sodium triacetoxyborohydride, as described in J. Org. Chem., 61, 3849, 1996, to yield the amine phosphonate 53.8. The reductive amination reaction is conducted under the same conditions as those described above for the preparation of the amine 51.3 (Scheme 51). The resultant ester 53.8 is then hydrolyzed, as described above, to afford the phenoxyacetic acid 53.1.

For example, 4-bromo-2,6-dimethylphenol 53.9 (Aldrich) is converted, as described above, into the phenoxy ester 53.10. The latter compound is then coupled, in dimethylformamide solution at ca. 60°, with cyclohexenone 53.11, in the presence of tetrakis(triphenylphosphine)palladium(0) and triethylamine, to yield the cyclohexenone 53.12.

The enone is then reduced to the saturated ketone 53.13, by means of catalytic hydrogenation employing 5% palladium on carbon as catalyst. The saturated ketone is then reacted with an equimolar amount of a dialkyl aminoethylphosphonate 53.14, prepared as described in J. Org. Chem., 2000, 65, 676, in the presence of sodium cyanoborohydride, to yield the amine 53.15. Hydrolysis, employing lithium hydroxide in aqueous methanol at ambient temperature, then yields the acetic acid 53.16.

Using the above procedures, but employing, in place of 4-bromo-2,6-dimethylphenol 53.9, different bromo-substituted 2,6-dimethylphenols 53.2, and/or different cycloalkenones 53.4, and/or different dialkyl aminoalkylphosphonates 53.7, the corresponding products 53.1 are obtained.

Scheme 54 illustrates the preparation of 2,6-dimethylphenoxyacetic acids incorporating a phosphonate group attached to the phenyl ring by means of a heteroatom and an alkylene chain. The compounds are obtained by means of alkylation reactions in which an optionally protected hydroxy, thio or amino-substituted 2,6-dimethylphenol 54.1 is reacted, in the presence of a base such as, for example, potassium carbonate, and optionally in the presence of a catalytic amount of an iodide such as potassium iodide, with a dialkyl bromoalkyl phosphonate 54.2. The reaction is conducted in a polar organic solvent such as dimethylformamide or acetonitrile at from ambient temperature to about 80°. The product of the alkylation reaction, 54.3 is then converted, as described above (Scheme 50) into the phenoxyacetic acid 54.4.

For example, 2,6-dimethyl-4-mercaptophenol 54.5, prepared as described in EP 482342, is reacted in dimethylformamide at ca. 60° with an equimolar amount of a dialkyl bromobutyl phosphonate 54.6, the preparation of which is described in Synthesis, 1994, 9, 909, in the presence of ca. 5 molar equivalents of potassium carbonate, to afford the thioether product 54.7. This compound is converted, employing the procedures described above, (Scheme 50) into the corresponding phenoxyacetic acid 54.8.

Using the above procedures, but employing, in place of 2,6-dimethyl-4-mercaptophenol 54.5, different hydroxy, thio or aminophenols 54.1, and/or different dialkyl bromoalkyl phosphonates 54.2, the corresponding products 54.4 are obtained.

Scheme 55 illustrates the preparation of 2,6-dimethylphenoxyacetic acids incorporating a phosphonate ester group attached by means of an aromatic or heteroaromatic group. In this procedure, an optionally protected hydroxy, mercapto or amino-substituted 2.6-dimethylphenol 55.1 is reacted, under basic conditions, with a bis(halomethyl)aryl or heteroaryl compound 55.2. Equimolar amounts of the phenol and the halomethyl compound are reacted in a polar organic solvent such as dimethylformamide or acetonitrile, in the presence of a base such as potassium or cesium carbonate, or dimethylaminopyridine, to afford the ether, thioether or amino product 55.3. The product 55.3 is then converted, using the procedures described above, (Scheme 50) into the phenoxyacetic ester 55.4. The latter compound is then subjected to an Arbuzov reaction by reaction with a trialkylphosphite 55.5 at ca. 100° to afford the phosphonate ester 55.6. The preparation of phosphonates by means of the Arbuzov reaction is described, for example, in Handb. Organophosphorus Chem., 1992, 115. The resultant product 55.6 is then converted into the acetic acid 55.7 by hydrolysis of the ester moiety, using the procedures described above, (Scheme 50).

For example, 4-hydroxy-2,6-dimethylphenol 55.8 (Aldrich) is reacted with one molar equivalent of 3,5-bis(chloromethyl)pyridine, the preparation of which is described in Eur. J. Inorg. Chem., 1998, 2, 163, to afford the ether 55.10. The reaction is conducted in acetonitrile at ambient temperature in the presence of five molar equivalents of potassium carbonate. The product 55.10 is then reacted with ethyl bromoacetate, using the procedures described above, (Scheme 50) to afford the phenoxyacetic ester 55.11. This product is heated at 100° for 3 hours with three molar equivalents of triethyl phosphite 55.12, to afford the phosphonate ester 55.13. Hydrolysis of the acetic ester moiety, as described above, for example by reaction with lithium hydroxide in aqueous ethanol, then affords the phenoxyacetic acid 55.14.

Using the above procedures, but employing, in place of the bis(chloromethyl) pyridine 55.9, different bis(halomethyl) aromatic or heteroaromatic compounds 55.2, and/or different hydroxy, mercapto or amino-substituted 2,6-dimethylphenols 55.1 and/or different trialkyl phosphites 55.5, the corresponding products 55.7 are obtained.

Scheme 56 illustrates the preparation of dimethylphenoxyacetic acids incorporating a phosphonate group attached by mans of an amide group. In this procedure, a carboxy-substituted 2,6-dimethylphenol 56.1 is reacted with a dialkyl aminoalkyl phosphonate 56.2 to afford the amide product 56.3. The amide-forming reaction is performed under similar conditions to those described above for the preparation of the amides 1.3 and 1.6. The product 56.3 is then transformed, as described above (Scheme 50) into the phenoxyacetic acid 56.4. For example, 3,5-dimethyl-4-hydroxybenzoic acid 56.5 (Aldrich) is reacted with a dialkyl aminoethylphosphonate 56.6, the preparation of which is described in J. Org. Chem., 2000, 65, 676, in tetrahydrofuran solution in the presence of dicyclohexylcarbodiimide to produce the amide 56.7. The product is then transformed, as described above, (Scheme 50) into the corresponding phenoxyacetic acid 56.8.

Using the above procedures, but employing, in place of 3,5-dimethyl-4-hydroxybenzoic acid 56.5, different carboxy-substituted 2,6-dimethylphenols 56.1, and/or different dialkyl aminoalkyl phosphonates 56.2, the corresponding PRODUCTS 56.4 are obtained.

Scheme 56

Method

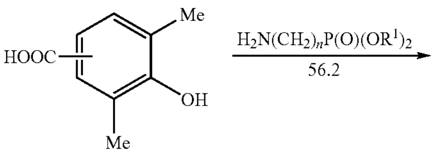

56.1

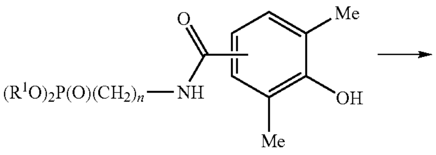

56.3

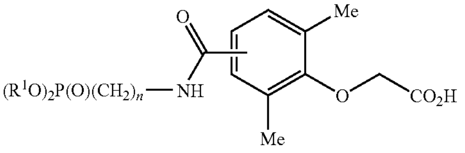

56.4

-continued

Example

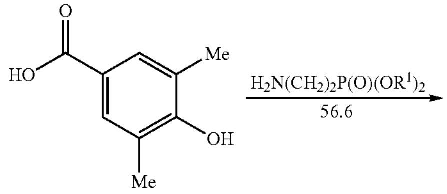

56.5

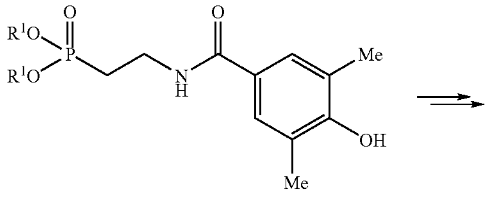

56.7

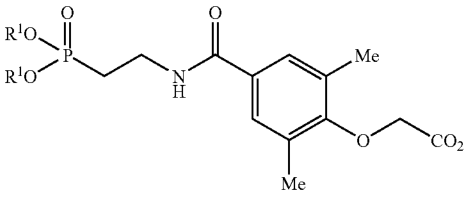

56.8

Preparation of Quinoline 2-Carboxylic Acids 9.1 Incorporating Phosphonate Moieties.

The reaction sequences depicted in Schemes 9-12 for the preparation of the phosphonate esters 3 employ a quinoline-2-carboxylic acid reactant 9.1 in which the substituent A is either the group link-$P(O)(OR^1)_2$ or a precursor thereto, such as [OH], [SH] Br etc.

A number of suitably substituted quinoline-2-carboxylic acids are available commercially or are described in the chemical literature. For example, the preparations of 6-hydroxy, 6-amino and 6-bromoquinoline-2-carboxylic acids are described respectively in DE 3004370, J. Het. Chem., 1989, 26, 929 and J. Labelled Comp. Radiopharm., 1998, 41, 1103, and the preparation of 7-aminoquinoline-2-carboxylic acid is described in J. Am. Chem. Soc., 1987, 109, 620. Suitably substituted quinoline-2-carboxylic acids can also be prepared by procedures known to those skilled in the art. The synthesis of variously substituted quinolines is described, for example, in Chemistry of Heterocyclic Compounds, Vol. 32, G. Jones, ed., Wiley, 1977, p 93ff. Quinoline-2-carboxylic acids can be prepared by means of the Friedlander reaction, which is described in Chemistry of Heterocyclic Compounds, Vol. 4, R. C. Elderfield, ed., Wiley, 1952, p. 204.

Scheme 57 illustrates the preparation of quinoline-2-carboxylic acids by means of the Friedlander reaction, and further transformations of the products obtained. In this reaction sequence, a substituted 2-aminobenzaldehyde 57.1 is reacted with an alkyl pyruvate ester 57.2, in the presence of an organic or inorganic base, to afford the substituted quinoline-2-carboxylic ester 57.3. Hydrolysis of the ester, for example by the use of aqueous base, then afford the corresponding carboxylic acid 57.4. The carboxylic acid product 57.4 in which X is $NH_2$ can be further transformed into the corresponding compounds 57.6 in which Z is OH, SH or Br. The latter transformations are effected by means of a diazotization reaction. The conversion of aromatic amines into the corresponding phenols and bromides by means of a diazotization reaction is described respectively in Synthetic Organic Chemistry, R. B. Wagner, H. D. Zook, Wiley, 1953, pages 167 and 94; the conversion of amines into the corresponding thiols is described in Sulfur Lett., 2000, 24, 123. The amine is first converted into the diazonium salt by reaction with nitrous acid. The diazonium salt, preferably the diazonium tetrafluoborate, is then heated in aqueous solution, for example as described in Organic Functional Group Preparations, by S. R. Sandler and W. Karo, Academic Press, 1968, p. 83, to afford the corresponding phenol 57.6, Y=OH. Alternatively, the diazonium salt is reacted in aqueous solution with cuprous bromide and lithium bromide, as described in Organic Functional Group Preparations, by S. R. Sandler and W. Karo, Academic Press, 1968, p. 138, to yield the corresponding bromo compound, 57.6, Y=Br. Alternatively, the diazonium tetrafluoborate is reacted in acetonitrile solution with a sulfhydryl ion exchange resin, as described in Sulfur Lett., 2000, 24, 123, to afford the thiol 57.6, Y=SH. Optionally, the diazotization reactions described above can be performed on the carboxylic esters 57.3 instead of the carboxylic acids 57.5.

For example, 2,4-diaminobenzaldehyde 57.7 (Apin Chemicals) is reacted with one molar equivalent of methyl pyruvate 57.2 in methanol, in the presence of a base such as piperidine, to afford methyl-7-aminoquinoline-2-carboxylate 57.8. Basic hydrolysis of the product, employing one molar equivalent of lithium hydroxide in aqueous methanol, then yields the carboxylic acid 57.9. The amino-substituted carboxylic acid is then converted into the diazonium tetrafluoborate 57.10 by reaction with sodium nitrite and tetrafluoboric acid. The diazonium salt is heated in aqueous solution to afford the 7-hydroxyquinoline-2-carboxylic acid, 57.11, Z=OH. Alternatively, the diazonium tetrafluoborate is heated in aqueous organic solution with one molar equivalent of cuprous bromide and lithium bromide, to afford 7-bromoquinoline-2-carboxylic acid 57.11, Z=Br. Alternatively, the diazonium tetrafluoborate 57.10 is reacted in acetonitrile solution with the sulfhydryl form of an ion exchange resin, as described in Sulfur Lett., 2000, 24, 123, to prepare 7-mercaptoquinoline-2-carboxylic acid 57.11, Z=SH.

Using the above procedures, but employing, in place of 2,4-diaminobenzaldehyde 57.7, different aminobenzaldehydes 57.1, the corresponding amino, hydroxy, bromo or mercapto-substituted quinoline-2-carboxylic acids 57.6 are obtained. The variously substituted quinoline carboxylic acids and esters can then be transformed, as described herein, (Schemes 58-60) into phosphonate-containing derivatives.

Scheme 58 depicts the preparation of quinoline-2-carboxylic acids incorporating a phosphonate moiety attached to the quinoline ring by means of an oxygen or a sulfur atom. In this procedure, an amino-substituted quinoline-2-carboxylate ester 58.1 is transformed, via a diazotization procedure as described above (Scheme 57) into the corresponding phenol or thiol 58.2. The latter compound is then reacted with a dialkyl hydroxymethylphosphonate 58.3, under the conditions of the Mitsonobu reaction, to afford the phosphonate ester 58.4. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4. The phenol or thiophenol and the alcohol component are reacted together in an aprotic solvent such as, for example, tetrahydrofuran, in the presence of a dialkyl azodicarboxylate and a triarylphosphine, to afford the ether or thioether products 58.4. Basic hydrolysis of the ester group, for example employing one molar equivalent of lithium hydroxide in aqueous methanol, then yields the carboxylic acid 58.5. The product is then coupled with a suitably protected aminoacid derivative 58.6 to afford the amide 58.7. The reaction is performed under similar conditions t those described above for the preparation of the amide 1.6 (Scheme 1). The ester protecting group is the removed to yield the carboxylic acid 58.8.

For example, methyl 6-amino-2-quinoline carboxylate 58.9, prepared as described in J. Het. Chem., 1989, 26, 929, is converted, by means of the diazotization procedure described above, into methyl 6-mercaptoquinoline-2-carboxylate 58.10. This material is reacted with a dialkyl hydroxymethylphosphonate 58.11 (Aldrich) in the presence of diethyl azodicarboxylate and triphenylphosphine in tetrahydrofuran solution, to afford the thioether 58.12. Basic hydrolysis then afford the carboxylic acid 58.13. The latter compound is then converted, as described above, into the aminoacid derivative 58.16.

Using the above procedures, but employing, in place of methyl 6-amino-2-quinoline carboxylate 58.9, different aminoquinoline carboxylic esters 58.1 and/or different dialkyl hydroxymethylphosphonates 58.3 the corresponding phosphonate ester products 58.8 are obtained.

Scheme 59 illustrates the preparation of quinoline-2-carboxylic acids incorporating phosphonate esters attached to the quinoline ring by means of a saturated or unsaturated carbon chain. In this reaction sequence, a bromo-substituted quinoline carboxylic ester 59.1 is coupled, by means of a palladium-catalyzed Heck reaction, with a dialkyl alkenylphosphonate 59.2. The coupling of aryl halides with olefins by means of the Heck reaction is described, for example, in Advanced Organic Chemistry, by F. A. Carey and R. J. Sundberg, Plenum, 2001, p. 503ff. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Thus, Heck coupling of the bromo compound 59.1 and the olefin 59.2 affords the olefinic ester 59.3. Hydrolysis, for example by reaction with lithium hydroxide in aqueous methanol, or by treatment with porcine liver esterase, then yields the carboxylic acid 59.4. The latter compound is then transformed, as described above, into the homolog 59.5. Optionally, the unsaturated carboxylic acid 59.4 can be reduced to afford the saturated analog 59.6. The reduction reaction can be effected chemically, for example by the use of diimide or diborane, as described in Comprehensive Organic Transformations, by R. C. Larock, VCH, 1989, p. 5, or catalytically. The product 59.6 is then converted, as described above (Scheme 58) into the aminoacid derivative 59.7.

For example, methyl 7-bromoquinoline-2-carboxylate, 59.8, prepared as described in J. Labelled Comp. Radiopharm., 1998, 41, 1103, is reacted in dimethylformamide at 60° with a dialkyl vinylphosphonate 59.9 (Aldrich) in the presence of 2 mol % of tetrakis(triphenylphosphine)palladium and triethylamine, to afford the coupled product 59.10 The product is then reacted with lithium hydroxide in aqueous tetrahydrofuran to produce the carboxylic acid 59.11. The latter compound is reacted with diimide, prepared by basic hydrolysis of diethyl azodicarboxylate, as described in Angew. Chem. Int. Ed., 4, 271, 1965, to yield the saturated product 59.12. The latter compound is then converted, as described above, into the aminoacid derivative 59.13. The unsaturated product 59.11 is similarly converted into the analog 59.14.

Using the above procedures, but employing, in place of methyl 6-bromo-2-quinolinecarboxylate 59.8, different bromoquinoline carboxylic esters 59.1 and/or different dialkyl alkenylphosphonates 59.2, the corresponding phosphonate ester products 59.5 and 59.7 are obtained.

Scheme 60 depicts the preparation of quinoline-2-carboxylic acid derivatives 60.5 in which the phosphonate group is attached by means of a nitrogen atom and an alkylene chain. In this reaction sequence, a methyl aminoquinoline-2-carboxylate 60.1 is reacted with a phosphonate aldehyde 60.2 under reductive amination conditions, to afford the aminoalkyl product 60.3. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The ester product 60.3 is then hydrolyzed to yield the free carboxylic acid 60.4. The latter compound is then converted, as described above, into the aminoacid derivative 60.5.

For example, methyl 7-aminoquinoline-2-carboxylate 60.6, prepared as described in J. Am. Chem. Soc., 1987, 109, 620, is reacted with a dialkyl formylmethylphosphonate 60.7 (Aurora) in methanol solution in the presence of sodium borohydride, to afford the alkylated product 60.8. The ester is then hydrolyzed, as described above, to yield the carboxylic acid 60.9. The latter compound is then converted, as described above, into the aminoacid derivative 60.10. Using the above procedures, but employing, in place of the formylmethyl phosphonate 60.7, different formylalkyl phosphonates 60.2, and/or different aminoquinolines 60.1, the corresponding products 60.5 are obtained.

Preparation of 5-hydroxyisoquinoline Derivatives 13.1 Incorporating Phosphonate Moieties.

Schemes 61-65 illustrate methods for the preparation of the 5-hydroxyisoquinoline derivatives 13.1 which are employed in the preparation of the intermediate phosphonate esters 4.

A number of substituted 5-hydroxyisoquinolines are commercially available, or have syntheses described in the literature. The synthesis of substituted 5-hydroxyisoquinolines is described, for example, in Heterocyclic Compounds, Vol. 38, Part 3, E. M. Coppola, H. F. Schuster, eds., Wiley, 1995, p. 229ff, and in Heterocyclic Chemistry, by T. L. Gilchrist, Longman, 1992, p. 162ff.

Scheme 61 illustrates methods for the preparation of substituted 5-hydroxyisoquinolines. As shown in Method 1, variously substituted 3-hydroxybenzaldehydes or 3-hydroxyphenyl ketones 61.1 are reacted with substituted or unsubstituted 2,2-dialkoxyethylamines 61.2 in a procedure known as the Pomeranz-Fritsch reaction. The reactants are combined in a hydrocarbon solvent such as toluene at reflux temperature with azeotropic removal of water, to yield the imine product 61.3. The latter compound is then subjected to acid-catalyzed cyclization, for example as described in Heterocyclic Chemistry, by T. L. Gilchrist, Longman, 1992, p. 164, to yield the substituted 5-hydroxyisoquinoline 61.4.

Scheme 61, Method 2 illustrates the preparation of variously substituted 5-hydroxyisoquinolines from the corresponding amino-substituted compounds. In this procedure, a suitably protected amino-substituted 5-hydroxyisoquinoline 61.5 is subjected to a diazotization reaction to afford the diazonium tetrafluoborate, using the conditions described above in Scheme 57. The diazonium salt is then converted, as described above, into the corresponding hydroxy, mercapto or halo derivative 61.7.

Scheme 62 illustrates the preparation of the isoquinolinyl-5-oxyacetic acids 62.2 and the conversion of these compounds into the corresponding aminoacid derivatives 13.1. In this procedure, the 5-hydroxyisoquinoline substrate 62.1, in which the substituent A is either the group link-$P(O)(OR^1)_2$, or a precursor group thereto, such as [OH], [SH], [$NH_2$], Br, etc, as described herein, is converted into the corresponding aryloxyacetic acid 62.2. The procedures employed for this transformation are the same as those described above, (Scheme 50) for the conversion of 2,6-dimethoxyphenol derivatives into the corresponding phenoxyacetic acids. The product 62.2 is then transformed, as described above, (Scheme 57) into the aminoacid derivative 13.1.

Schemes 63-65 illustrate the preparation of 5-hydroxyisoquinoline derivatives incorporating phosphonate substituents. The quinolinol products are then converted, as described above, into analogs of the aminoacid derivative 13.1.

Scheme 63 illustrates the preparation of 5-hydroxyisoquinoline derivatives in which a phosphonate substituent is attached by means of an amide bond. In this procedure, an amino-substituted 5-hydroxyisoquinoline 63.1 is reacted with a dialkyl carboxyalkyl phosphonate 63.2 to afford the amide 63.3. The reaction is effected as described above for the preparation of the amides 1.3 and 1.6.

For example, 8-amino-5-hydroxyisoquinoline 63.4, the preparation of which is described in Syn. Comm., 1986, 16, 1557, is reacted in tetrahydrofuran solution with one molar equivalent of a dialkyl 2-carboxyethyl phosphonate 63.5 (Epsilon) and dicyclohexyl carbodiimide, to produce the amide 63.6.

Using the same procedures, but employing, in place of the 8-amino quinolinol 63.4, different aminoquinolinols 63.1, and/or different dialkyl carboxyalkyl phosphonates 63.2, the corresponding products 63.3 are obtained.

Scheme 64 illustrates the preparation of 5-hydroxyisoquinoline derivatives in which a phosphonate substituent is attached by means of a carbon link or a carbon and a heteroatom link. In this procedure, a methyl-substituted 5-hydroxyisoquinoline 64.1 is protected, and the product 64.2 is reacted with a free radical brominating agent, for example N-bromosuccinimide, as described in Chem. Rev., 63, 21, 1963, to afford the bromomethyl derivative 64.3. The latter compound is reacted with a trialkyl phosphite $(R^1O)_3P$ under the conditions of the Arbuzov reaction, as described in Scheme 55, to yield the phosphonate 64.4; deprotection then affords the phenol 64.5.

Alternatively, the protected bromomethyl derivative 64.3 is reacted with a dialkyl hydroxy, mercapto or amino-substituted alkyl phosphonate 64.6, to afford the alkylation product 64.7. The displacement reaction is conducted in a polar organic solvent such as dimethyl formamide, acetonitrile and the like, in the presence of a base such as sodium hydride or lithium hexamethyldisilazide, for substrates in which X is O, or potassium carbonate for substrates in which X is S or N. The protecting group is then removed from the product 64.7 to yield the phenolic product 64.8.

For example, 5-hydroxy-1-methylisoquinoline 64.9, prepared as described in J. Med. Chem., 1968, 11, 700, is reacted with acetic anhydride in pyridine to afford 5-acetoxy-1-methylisoquinoline 64.10. The latter compound is reacted with N-bromosuccinimide in refluxing ethyl acetate to yield 5-acetoxy-1-bromomethylisoquinoline 64.11. The product is then reacted with five molar equivalents of a trialkyl phosphite at 120° to give the phosphonate product 64.12. The acetoxy group is hydrolyzed by reaction with sodium bicarbonate in aqueous methanol as described in J. Am. Chem. Soc., 93, 746, 1971, to produce the phenol 64.13.

Using the above procedures, but employing, in place of 5-hydroxy-1-methylisoquinoline 64.9, different hydroxymethylisoquinolines 64.1, the corresponding products 64.5 are obtained. As a further illustration of the method of Scheme 64, as shown in Example 2,5-hydroxy-3-methylisoquinoline 64.14, prepared as described in J. Med. Chem., 1998, 41, 4062, is reacted with one molar equivalent of tert. butyl chlorodimethylsilane and imidazole in dichloromethane to yield the silyl ether 64.15. The product is brominated, as described above, to afford 3-bromomethyl-5-tert. butyldimethylsilyloxyisoquinoline 64.16. The bromomethyl compound is then reacted in dimethylformamide at 60° with one molar equivalent of a dialkyl mercaptoethyl phosphonate 64.17, prepared as described in Zh. Obschei. Khim., 1973, 43, 2364, and potassium carbonate, to give the thioether product 64.18; deprotection, for example by treatment with 1M tetrabutylammonium fluoride in tetrahydrofuran, then yields the phenol 64.19.

Using the above procedures, but employing, in place of 5-hydroxy-3-methylisoquinoline 64.11, different hydroxymethylisoquinolines 64.1, and/or different hetero-substituted alkyl phosphonates 64.6, the corresponding products 64.8 are obtained.

Scheme 65 illustrates the preparation of 5-hydroxyisoquinoline derivatives incorporating a phosphonate moiety attached by means of a heteroatom and an alkylene chain. In this procedure, the phenolic hydroxyl group of 5-hydroxyisoquinolin-1-one 65.1 (Acros) is protected. The protection of phenolic hydroxyl groups is described, for example, in Protective Groups in Organic Synthesis, by T. W. Greene and P. G. M Wuts, Wiley, Second Edition 1990, p. 143ff. The product 65.2 is then converted into the bromo analog 65.3, for example by reaction with phosphorus oxybromide, as described in Heterocyclic Compounds, Vol. 38, Part 2, E. M. Coppola, H. F. Schuster, eds., Wiley, 1995, p. 13ff. The bromo compound is then reacted with a dialkyl hydroxy, mercapto or amino-substituted alkyl phosphonate 65.4, to afford the displacement product 65.5. The displacement reaction of 2-haloisoquinolines with nucleophiles to produce ethers, thioethers and amines is described in Heterocyclic Chemistry, by T. L. Gilchrist, Longman, 1992, p. 165. The reaction is conducted in an organic solvent such as dimethylformamide, toluene and the like, in the presence of a base such as sodium hydride or potassium carbonate. The phenolic hydroxyl group is then deprotected to yield the phenol 65.6.

For example, 5-hydroxyisoquinolin-1-one 65.1 is reacted with one molar equivalent of benzoyl chloride in pyridine to afford the ester 65.7. The latter compound is treated with phosphorus oxybromide in refluxing toluene to produce the 5-benzoyloxy-1-bromoisoquinoline 65.8. This material is reacted with a dialkyl 3-hydroxypropyl phosphonate 65.9, prepared as described in Zh. Obschei. Khim., 1974, 44, 1834, and sodium hydride in tetrahydrofuran to prepare the ether product 65.10. Deprotection, for example by reaction with aqueous alcoholic sodium bicarbonate, then yields the phenol 65.11.

Using the above procedures, but employing, in place of a dialkyl 3-hydroxypropyl phosphonate 65.9, different dialkyl hydroxy, mercapto or amino-substituted alkyl phosphonates 65.4, the corresponding products 65.6 are obtained.

Scheme 66 described the preparation of 5-hydroxyisoquinolines in which a phosphonate substituent is attached by means of a saturated or unsaturated alkylene chain. In this procedure, a bromo-substituted 5-hydroxyisoquinoline 66.1 is protected, as described above. The product 66.2 is coupled, in the presence of a palladium catalyst, with a dialkyl alkenyl phosphonate 66.3. The coupling of aryl bromides and alkenes is described above (Scheme 52). The product 66.4 is then deprotected to yield the phenol 66.5. Optionally, the compound 66.5 is reduced, for example by treatment with diimide or diborane, to afford the saturated analog 66.6.

For example, 5-hydroxyisoquinoline 66.7 is reacted with bromine in carbon tetrachloride to afford 8-bromo-5-hydroxyisoquinoline 66.8. The product is reacted with acetic anhydride in pyridine to give 5-acetoxy-8-bromoisoquinoline 66.9. The latter compound is coupled with a dialkyl propenyl phosphonate 66.10 (Aldrich) in the presence of ca. 3 mol % of bis(triphenylphosphine)palladium(II) chloride and triethylamine, in dimethylformamide at ca. 60°, to produce the coupled product 66.11. The acetyl protecting group is then removed by reaction with dilute aqueous methanolic ammonia, as described in J. Chem. Soc., 2137, 1964, to afford the phenol 66.12. The product is optionally reduced to yield the saturated analog 66.13. The reduction reaction is effected chemically, for example by the use of diimide or diborane, as described in Comprehensive Organic Transformations, by R. C. Larock, VCH, 1989, p. 5, or catalytically.

Using the above procedures, but employing, in place of 8-bromo-5-hydroxyisoquinoline 66.8, different bromo-substituted 5-hydroxyisoquinolines 66.1, and/or different dialkyl alkenyl phosphonates 66.3, the corresponding products 66.5 and 66.6 are obtained.

Scheme 65

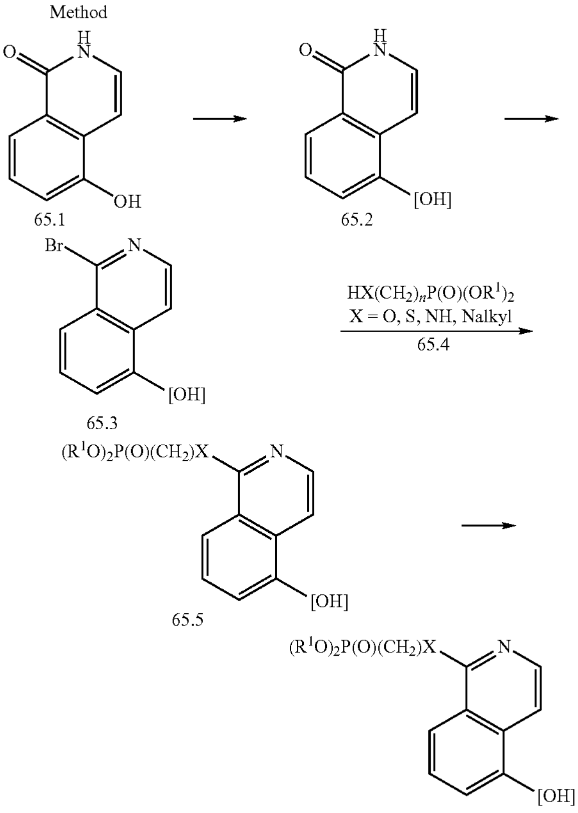

65.1

65.2

65.3

65.5

65.6

-continued

Example

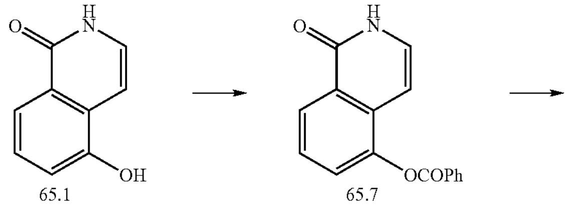

65.1 65.7

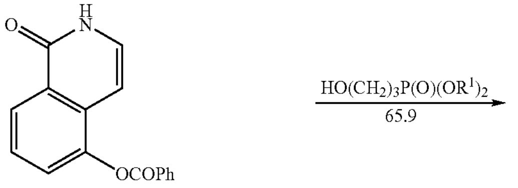

65.8

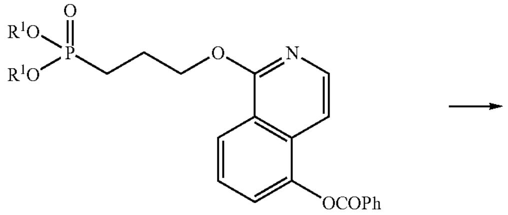

65.10

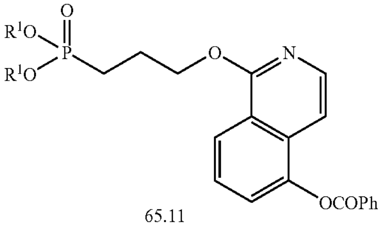

65.11

Scheme 66

Method

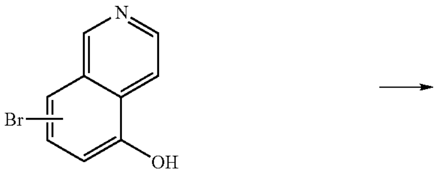

66.1

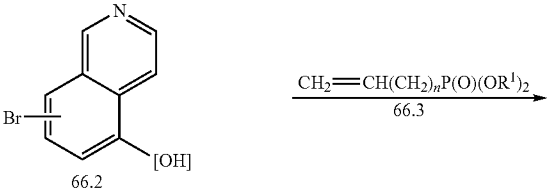

66.2

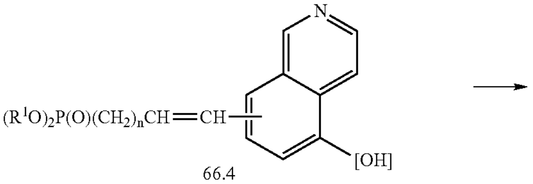

66.4

-continued

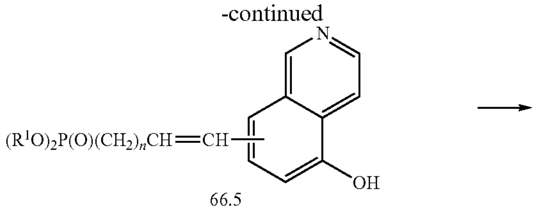

66.5

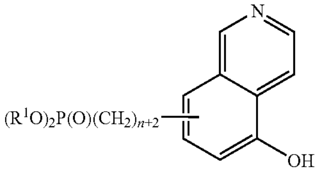

66.6

Example

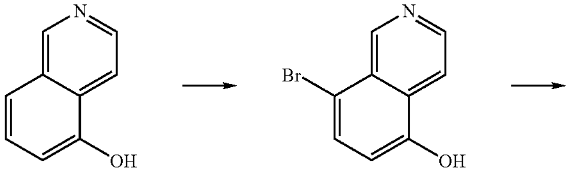

66.7 66.8

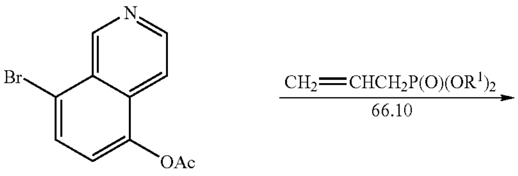

66.9

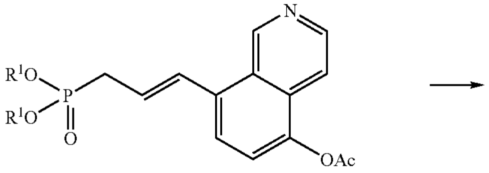

66.11

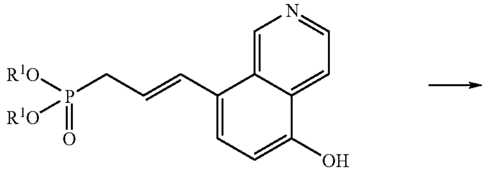

66.12

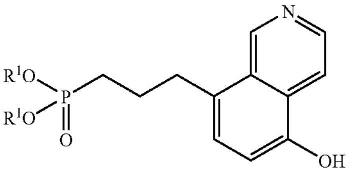

66.13

Preparation of Phenylalanine Derivatives 17.1 Incorporating Phosphonate Moieties.

Schemes 67-71 illustrate the preparation of phosphonate-containing phenylalanine derivatives 17.1 which are employed in the preparation of the intermediate phosphonate esters 5.

Scheme 67 illustrates the preparation of phenylalanine derivatives incorporating phosphonate moieties attached to the phenyl ring by means of a heteroatom and an alkylene chain. The compounds are obtained by means of alkylation or condensation reactions of hydroxy or mercapto-substituted phenylalanine derivatives 67.1.

In this procedure, a hydroxy or mercapto-substituted phenylalanine is converted into the benzyl ester 67.2. The conversion of carboxylic acids into esters is described for example, in Comprehensive Organic Transformations, by R. C. Larock, VCH, 1989, p 966. The conversion can be effected by means of an acid-catalyzed reaction between the carboxylic acid and benzyl alcohol, or by means of a base-catalyzed reaction between the carboxylic acid and a benzyl halide, for example benzyl chloride. The hydroxyl or mercapto substituent present in the benzyl ester 67.2 is then protected. Protection methods for phenols and thiols are described respectively, for example, in Protective Groups in Organic Synthesis, by T. W. Greene and P. G. M Wuts, Wiley, Second Edition 1990, p 10, p 277. For example, suitable protecting groups for phenols and thiophenols include tert-butyldimethylsilyl or tert-butyldiphenylsilyl. Thiophenols may also be protected as S-adamantyl groups, as described in Protective Groups in Organic Synthesis, by T. W. Greene and P. G. M Wuts, Wiley, Second Edition 1990, p. 289 The protected hydroxy- or mercapto ester 67.3 is then converted into the BOC derivative 67.4. The protecting group present on the O or S substituent is then removed. Removal of O or S protecting groups is described in Protective Groups in Organic Synthesis, by T. W. Greene and P. G. M Wuts, Wiley, Second Edition 1990, p10, p 277. For example, silyl protecting groups are removed by treatment with tetrabutylammonium fluoride and the like, in a solvent such as tetrahydrofuran at ambient temperature, as described in J. Am. Chem. Soc., 94, 6190, 1972. S-Adamantyl groups can be removed by treatment with mercuric trifluoroacetate in acetic acid, as described in Chem. Pharm. Bull., 26, 1576, 1978.

The resultant phenol or thiophenol 67.5 is then reacted under various conditions to provide protected phenylalanine derivatives 67.9, 67.10 or 67.11, incorporating phosphonate moieties attached by means of a heteroatom and an alkylene chain.

In this step, the phenol or thiophenol 67.5 is reacted with a dialkyl bromoalkyl phosphonate 67.6 to afford the ether or thioether product 67.9. The alkylation reaction is effected in the presence of an organic or inorganic base, such as, for example, diazabicyclononene, cesium carbonate or potassium carbonate, The reaction is performed at from ambient temperature to ca. 80°, in a polar organic solvent such as dimethylformamide or acetonitrile, to afford the ether or thioether product 67.9. Deprotection of the benzyl ester group, for example by means of catalytic hydrogenation over a palladium catalyst, then yields the carboxylic acid 67.12. The benzyl esters 67.10 and 67.11, the preparation of which is described above, are similarly deprotected to produce the corresponding carboxylic acids.

For example, as illustrated in Scheme 67, Example 1, a hydroxy-substituted phenylalanine derivative such as tyrosine, 67.13 is converted, as described above, into the benzyl ester 67.14. The latter compound is then reacted with one molar equivalent of chloro tert-butyldimethylsilane, in the presence of a base such as imidazole, as described in J. Am. Chem. Soc., 94, 6190, 1972, to afford the silyl ether 67.15. This compound is then converted, as described above, into the BOC derivative 67.16. The silyl protecting group is removed by treatment of the silyl ether 67.16 with a tetrahydrofuran solution of tetrabutyl ammonium fluoride at ambient temperature, as described in J. Am. Chem. Soc., 94, 6190, 1972, to afford the phenol 67.17. The latter compound is then reacted in dimethylformamide at ca. 60°, with one molar equivalent of a dialkyl 3-bromopropyl phosphonate 67.18 (Aldrich), in the presence of cesium carbonate, to afford the alkylated product 67.19. Debenzylation then produces the carboxylic acid 67.20.

Using the above procedures, but employing, in place of the hydroxy-substituted phenylalanine derivative 67.13, different hydroxy or thio-substituted phenylalanine derivatives 67.1, and/or different bromoalkyl phosphonates 67.6, the corresponding ether or thioether products 67.12 are obtained.

Alternatively, the hydroxy or mercapto-substituted tribenzylated phenylalanine derivative 67.5 is reacted with a dialkyl hydroxymethyl phosphonate 67.7 under the conditions of the Mitsonobu reaction, to afford the ether or thioether compounds 67.10. The preparation of aromatic ethers by means of the Mitsonobu reaction is described, for example, in Comprehensive Organic Transformations, by R. C. Larock, VCH, 1989, p 448, and in Advanced Organic Chemistry, Part B, by F. A. Carey and R. J. Sundberg, Plenum, 2001, p 153-4. The phenol or thiophenol and the alcohol component are reacted together in an aprotic solvent such as, for example, tetrahydrofuran, in the presence of a dialkyl azodicarboxylate and a triarylphosphine, to afford the ether or thioether products 67.10.

For example, as shown in Scheme 67, Example 2,3-mercaptophenylalanine 67.21, prepared as described in WO 0036136, is converted, as described above, into the benzyl ester 67.22. The resultant ester is then reacted in tetrahydrofuran solution with one molar equivalent of 4-methoxybenzyl chloride in the presence of ammonium hydroxide, as described in Bull. Chem. Soc. Jpn., 37, 433, 1974, to afford the 4-methoxybenzyl thioether 67.23. This compound is then converted, as described above for the preparation of the compound 67.4, into the BOC-protected derivative 67.24. The 4-methoxybenzyl group is then removed by the reaction of the thioether 67.24 with mercuric trifluoroacetate and anisole in trifluoroacetic acid, as described in J. Org. Chem., 52, 4420, 1987, to afford the thiol 67.25. The latter compound is reacted, under the conditions of the Mitsonobu reaction, with a dialkyl hydroxymethyl phosphonate 67.7, diethylazodicarboxylate and triphenylphosphine, for example as described in Synthesis, 4, 327, 1998, to yield the thioether product 67.26. The benzyl ester protecting group is then removed to afford the carboxylic acid 67.27.

Using the above procedures, but employing, in place of the mercapto-substituted phenylalanine derivative 67.21, different hydroxy or mercapto-substituted phenylalanines 67.1, and/or different dialkyl hydroxymethyl phosphonates 67.7, the corresponding products 67.10 are obtained.

Alternatively, the hydroxy or mercapto-substituted tribenzylated phenylalanine derivative 67.5 is reacted with an activated derivative of a dialkyl hydroxymethylphosphonate 67.8 in which Lv is a leaving group. The components are reacted together in a polar aprotic solvent such as, for example, dimethylformamide or dioxan, in the presence of an organic or inorganic base such as triethylamine or cesium carbonate, to afford the ether or thioether products 67.11. For example, as illustrated in Scheme 67, Example 3,3-hydroxyphenylalanine 67.28 (Fluka) is converted, using the procedures described above, into the protected compound 67.29. The latter compound is reacted, in dimethylformamide at ca. 50°, in the presence of potassium carbonate, with diethyl trifluoromethanesulfonyloxymethylphosphonate 67.30, prepared as described in Tet. Lett., 1986, 27, 1477, to afford the ether product 67.31. Debenzylation then produces the carboxylic acid 67.32.

Using the above procedures, but employing, in place of the hydroxy-substituted phenylalanine derivative 67.28, different hydroxy or mercapto-substituted phenylalanines 67.1, and/or different dialkyl trifluoromethanesulfonyloxymethylphosphonates 67.8, the corresponding products 67.11 are obtained.

Scheme 68 illustrates the preparation of phenylalanine derivatives incorporating phosphonate moieties attached to the phenyl ring by means of an alkylene chain incorporating a nitrogen atom. The compounds are obtained by means of a reductive alkylation reaction between a formyl-substituted tribenzylated phenylalanine derivative 68.3 and a dialkyl aminoalkylphosphonate 68.4.

In this procedure, a hydroxymethyl-substituted phenylalanine 68.1 is converted, as described above, into the BOC protected benzyl ester 68.2. The latter compound is then oxidized to afford the corresponding aldehyde 68.3. The conversion of alcohols to aldehydes is described, for example, in Comprehensive Organic Transformations, by R. C. Larock, VCH, 1989, p 604ff. Typically, the alcohol is reacted with an oxidizing agent such as pyridinium chlorochromate, silver carbonate, or dimethyl sulfoxide/acetic anhydride, to afford the aldehyde product 68.3. For example, the carbinol 68.2 is reacted with phosgene, dimethyl sulfoxide and triethylamine, as described in J. Org. Chem., 43, 2480, 1978, to yield the aldehyde 68.3. This compound is reacted with a dialkyl aminoalkylphosphonate 68.4 in the presence of a suitable reducing agent to afford the amine product 68.5. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem., 55, 2552, 1990. The benzyl protecting group is then removed to prepare the carboxylic acid 68.6.

For example, 3-(hydroxymethyl)-phenylalanine 68.7, prepared as described in Acta Chem. Scand. Ser. B, 1977, B31, 109, is converted, as described above, into the formylated derivative 68.8. This compound is then reacted with a dialkyl aminoethylphosphonate 68.9, prepared as described in J. Org. Chem., 200, 65, 676, in the presence of sodium cyanoborohydride, to produce the alkylated product 68.10, which is then deprotected to give the carboxylic acid 68.11.

Using the above procedures, but employing, in place of 3-(hydroxymethyl)-phenylalanine 68.7, different hydroxymethyl phenylalanines 68.1, and/or different aminoalkyl phosphonates 68.4, the corresponding products 68.6 are obtained.

Scheme 69 depicts the preparation of phenylalanine derivatives in which a phosphonate moiety is attached directly to the phenyl ring. In this procedure, a bromo-substituted phenylalanine 69.1 is converted, as described above, (Scheme 68) into the protected derivative 69.2. The product is then coupled, in the presence of a palladium(0) catalyst, with a dialkyl phosphite 69.3 to produce the phosphonate ester 69.4. The preparation of arylphosphonates by means of a coupling reaction between aryl bromides and dialkyl phosphites is described in J. Med. Chem., 35, 1371, 1992. The product is then deprotected to afford the carboxylic acid 69.5. For example, 3-bromophenylalanine 69.6, prepared as described in Pept. Res., 1990, 3, 176, is converted, as described above, (Scheme 68) into the protected compound 69.7. This compound is then reacted, in toluene solution at reflux, with diethyl phosphite 69.8, triethylamine and tetrakis (triphenylphosphine)palladium(0), as described in J. Med. Chem., 35, 1371, 1992, to afford the phosphonate product 69.9. Debenzylation then yields the carboxylic acid 69.10.

Using the above procedures, but employing, in place of 3-bromophenylalanine 69.6, different bromophenylalanines 69.1, and/or different dialkylphosphites 69.3, the corresponding products 69.5 are obtained.

Schemes 70 and 71 illustrate two methods for the conversion of the compounds 70.1, in which the substituent A is either the group link $P(O)(OR^1)_2$ or a precursor thereto, such as [OH], [SH], Br etc, into the homologated derivatives 17.1 which are employed in the preparation of the intermediate phosphonate esters 5.

As shown in Scheme 70, the BOC-protected phenylalanine derivative 70.1 is converted, using the procedures described above in Scheme 41, into the aldehyde 70.2. The aldehyde is then converted, via the cyanohydrin 70.3, into the homologated derivative 17.1. The reaction sequence and conditions employed are the same as shown in Scheme 41 for the conversion of the BOC-protected aminoacid 41.1 into the homologated derivative 1.5.

Alternatively, as illustrated in Scheme 71, the BOC-protected aminoacid 70.1 is deprotected to afford the amine 71.1. The product is then converted, as described in Scheme 42, into the dibenzylated product 71.2. The latter compound is then transformed, using the sequence of reactions and conditions shown in Scheme 42 for the conversion of the dibenzylated aminoacid 42.1 into the hydroxyacid 1.5, into the homologated derivative 17.1.

Scheme 70

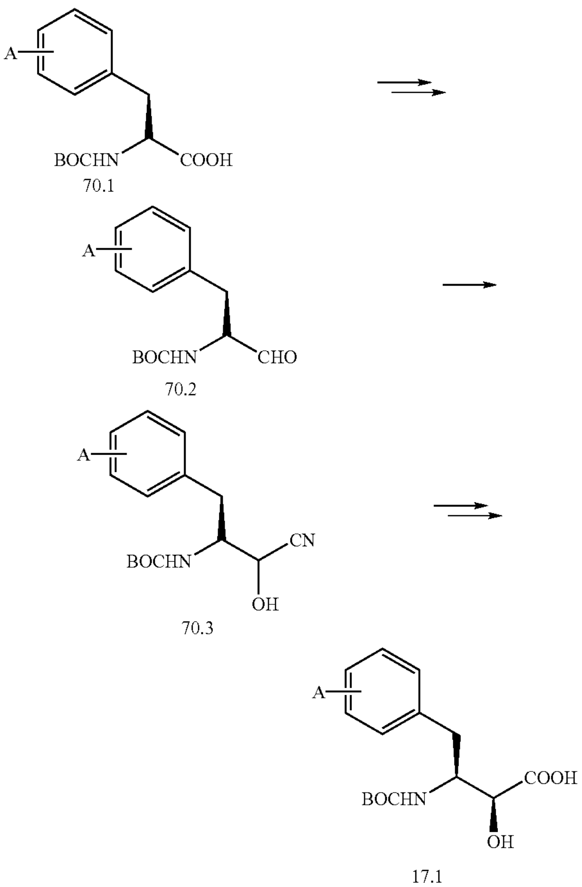

70.1

70.2

70.3

17.1

Scheme 71

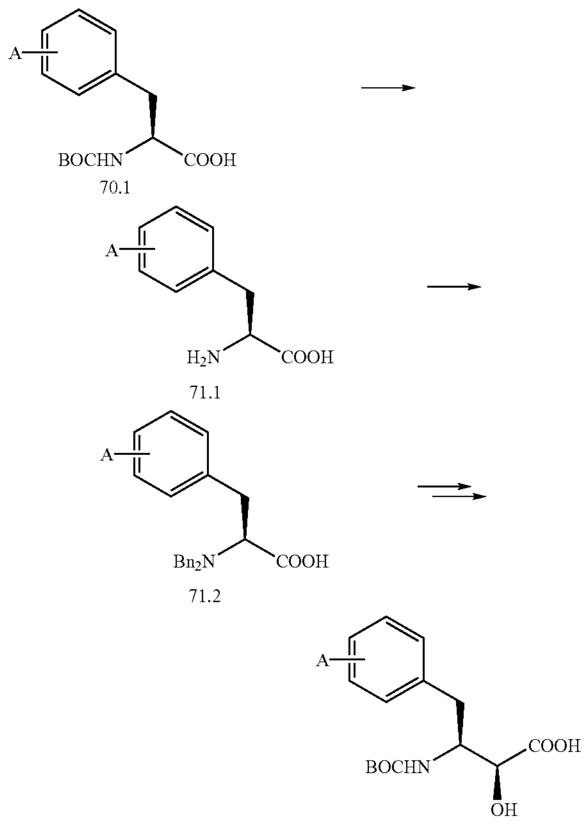

70.1

71.1

71.2

17.1

Preparation of the Phosphonate-containing Thiophenol Derivatives 19.1.

Schemes 72-83 describe the preparation of phosphonate-containing thiophenol derivatives 19.1 which are employed as described above (Schemes 19 and 20) in the preparation of the phosphonate ester intermediates 5 in which X is sulfur. Schemes 72-81 described the syntheses of the thiophenol components; Schemes 82 and 83 described methods for the incorporation of the thiophenols into the reactants 19.1.

Scheme 72 depicts the preparation of thiophenol derivatives in which the phosphonate moiety is attached directly to the phenyl ring. In this procedure, a halo-substituted thiophenol 72.1 is protected, as described above (Scheme 67) to afford the protected product 72.2. The product is then coupled, in the presence of a palladium catalyst, with a dialkyl phosphite 72.3, to afford the phosphonate ester 72.4. The preparation of arylphosphonates by the coupling of aryl halides with dialkyl phosphites is described above, (Scheme 69). The thiol protecting group is then removed, as described above, to afford the thiol 72.5.

For example, 3-bromothiophenol 72.6 is converted into the 9-fluorenylmethyl (Fm) derivative 72.7 by reaction with 9-fluorenylmethyl chloride and diisopropylethylamine in dimethylformamide, as described in Int. J. Pept. Protein Res., 20, 434, 1982. The product is then reacted with a dialkyl phosphite 72.3, as described for the preparation of the phosphonate 69.4 (Scheme 69), to afford the phosphonate ester 72.8. The Fm protecting group is then removed by treatment of the product with piperidine in dimethylformamide at ambient temperature, as described in J. Chem. Soc., Chem. Comm., 1501, 1986, to give the thiol 72.9. Using the above procedures, but employing, in place of 3-bromothiophenol 72.6, different thiophenols 72.1, and/or different dialkyl phosphites 72.3, the corresponding products 72.5 are obtained.

Scheme 73 illustrates an alternative method for obtaining thiophenols with a directly attached phosphonate group. In this procedure, a suitably protected halo-substituted thiophenol 73.2 is metallated, for example by reaction with magnesium or by transmetallation with an alkyllithium reagent, to afford the metallated derivative 73.3. The latter compound is reacted with a halodialkyl phosphite 73.4 to afford the product 73.5; deprotection then affords the thiophenol 73.6

For example, 4-bromothiophenol 73.7 is converted into the S-triphenylmethyl (trityl) derivative 73.8, as described in Protective Groups in Organic Synthesis, by T. W. Greene and P. G. M. Wuts, Wiley, 1991, pp. 287. The product is converted into the lithium derivative 73.9 by reaction with butyllithium in an ethereal solvent at low temperature, and the resulting lithio compound is reacted with a dialkyl chlorophosphite 73.10 to afford the phosphonate 73.11. Removal of the trityl group, for example by treatment with dilute hydrochloric acid in acetic acid, as described in J. Org. Chem., 31, 1118, 1966, then affords the thiol 73.12.

Using the above procedures, but employing, in place of the bromo compound 73.7, different halo compounds 73.1, and/or different halo dialkyl phosphites 73.4, there are obtained the corresponding thiols 73.6.

Scheme 74 illustrates the preparation of phosphonate-substituted thiophenols in which the phosphonate group is attached by means of a one-carbon link. In this procedure, a suitably protected methyl-substituted thiophenol 74.1 is subjected to free-radical bromination to afford a bromomethyl product 74.2. This compound is reacted with a sodium dialkyl phosphite 74.3 or a trialkyl phosphite, to give the displacement or rearrangement product 74.4, which upon deprotection affords the thiophenol 74.5.

For example, 2-methylthiophenol 74.6 is protected by conversion to the benzoyl derivative 74.7, as described in Protective Groups in Organic Synthesis, by T. W. Greene and P. G. M. Wuts, Wiley, 1991, pp. 298. The product is reacted with N-bromosuccinimide in ethyl acetate to yield the bromomethyl product 74.8. This material is reacted with a sodium dialkyl phosphite 74.3, as described in J. Med. Chem., 35, 1371, 1992, to afford the product 74.9. Alternatively, the bromomethyl compound 74.8 is converted into the phosphonate 74.9 by means of the Arbuzov reaction, for example as described in Handb. Organophosphorus Chem., 1992, 115. In this procedure, the bromomethyl compound 74.8 is heated with a trialkyl phosphate $P(OR^1)_3$ at ca. 100° to produce the phosphonate 74.9. Deprotection of the phosphonate 74.9, for example by treatment with aqueous ammonia, as described in J. Am. Chem. Soc., 85, 1337, 1963, then affords the thiol 74.10.

Using the above procedures, but employing, in place of the bromomethyl compound 74.8, different bromomethyl compounds 74.2, there are obtained the corresponding thiols 74.5.

Scheme 75 illustrates the preparation of thiophenols bearing a phosphonate group linked to the phenyl nucleus by oxygen or sulfur. In this procedure, a suitably protected hydroxy or thio-substituted thiophenol 75.1 is reacted with a dialkyl hydroxyalkylphosphonate 75.2 under the conditions of the Mitsonobu reaction, for example as described in Org. React., 1992, 42, 335, to afford the coupled product 75.3. Deprotection then yields the O- or S-linked products 75.4.

For example, the substrate 3-hydroxythiophenol, 75.5, is converted into the monotrityl ether 75.6, by reaction with one equivalent of trityl chloride, as described above. This compound is reacted with diethyl azodicarboxylate, triphenyl phosphine and a dialkyl 1-hydroxymethyl phosphonate 75.7 in benzene, as described in Synthesis, 4, 327, 1998, to afford the ether compound 75.8. Removal of the trityl protecting group, as described above, then affords the thiophenol 75.9.

Using the above procedures, but employing, in place of the phenol 75.5, different phenols or thiophenols 75.1, there are obtained the corresponding thiols 75.4.

Scheme 76 illustrates the preparation of thiophenols 76.4 bearing a phosphonate group linked to the phenyl nucleus by oxygen, sulfur or nitrogen. In this procedure, a suitably protected O, S or N-substituted thiophenol 76.1 is reacted with an activated ester, for example the trifluoromethanesulfonate 76.2, of a dialkyl hydroxyalkyl phosphonate, to afford the coupled product 76.3. Deprotection then affords the thiol 76.4.

For example, 4-methylaminothiophenol 76.5 is reacted in dichloromethane solution with one equivalent of acetyl chloride and a base such as pyridine, as described in Protective Groups in Organic Synthesis, by T. W. Greene and P. G. M. Wuts, Wiley, 1991, pp. 298, to afford the S-acetyl product 76.6. This material is then reacted with a dialkyl trifluoromethanesulfonylmethyl phosphonate 76.7, the preparation of which is described in Tet. Lett., 1986, 27, 1477, to afford the displacement product 76.8. Preferably, equimolar amounts of the phosphonate 76.7 and the amine 76.6 are reacted together in an aprotic solvent such as dichloromethane, in the presence of a base such as 2,6-lutidine, at ambient temperatures, to afford the phosphonate product 76.8. Deprotection, for example by treatment with dilute aqueous sodium hydroxide for two minutes, as described in J. Am. Chem. Soc., 85, 1337, 1963, then affords the thiophenol 76.9.

Using the above procedures, but employing, in place of the thioamine 76.5, different phenols, thiophenols or amines 76.1, and/or different phosphonates 76.2, there are obtained the corresponding products 76.4.

Scheme 77 illustrates the preparation of phosphonate esters linked to a thiophenol nucleus by means of a heteroatom and a multiple-carbon chain, employing a nucleophilic displacement reaction on a dialkyl bromoalkyl phosphonate 77.2. In this procedure, a suitably protected hydroxy, thio or amino substituted thiophenol 77.1 is reacted with a dialkyl bromoalkyl phosphonate 77.2 to afford the product 77.3. Deprotection then affords the free thiophenol 77.4.

For example, 3-hydroxythiophenol 77.5 is converted into the S-trityl compound 77.6, as described above. This compound is then reacted with, for example, a dialkyl 4-bromobutyl phosphonate 77.7, the synthesis of which is described in Synthesis, 1994, 9, 909. The reaction is conducted in a dipolar aprotic solvent, for example dimethylformamide, in the presence of a base such as potassium carbonate, and optionally in the presence of a catalytic amount of potassium iodide, at about 50°, to yield the ether product 77.8. Deprotection, as described above, then affords the thiol 77.9.

Using the above procedures, but employing, in place of the phenol 77.5, different phenols, thiophenols or amines 77.1, and/or different phosphonates 77.2, there are obtained the corresponding products 77.4.

Scheme 78 depicts the preparation of phosphonate esters linked to a thiophenol nucleus by means of unsaturated and saturated carbon chains. The carbon chain linkage is formed by means of a palladium catalyzed Heck reaction, in which an olefinic phosphonate 78.2 is coupled with an aromatic bromo compound 78.1. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate, to afford the coupled product 78.3. Deprotection, or hydrogenation of the double bond followed by deprotection, affords respectively the unsaturated phosphonate 78.4, or the saturated analog 78.6.

For example, 3-bromothiophenol is converted into the S—Fm derivative 78.7, as described above, and this compound is reacted with a dialkyl 1-butenyl phosphonate 78.8, the preparation of which is described in J. Med. Chem., 1996, 39, 949, in the presence of a palladium (II) catalyst, for example, bis(triphenylphosphine)palladium (II) chloride, as described in J. Med. Chem, 1992, 35, 1371. The reaction is conducted in an aprotic dipolar solvent such as, for example, dimethylformamide, in the presence of triethylamine, at about 100° to afford the coupled product 78.9. Deprotection, as described above, then affords the thiol 78.10. Optionally, the initially formed unsaturated phosphonate 78.9 is subjected to reduction, for example using diimide, as described above, to yield the saturated product 78.11, which upon deprotection affords the thiol 78.12.

Using the above procedures, but employing, in place of the bromo compound 78.7, different bromo compounds 78.1, and/or different phosphonates 78.2, there are obtained the corresponding products 78.4 and 78.6

Scheme 79 illustrates the preparation of an aryl-linked phosphonate ester 79.4 by means of a palladium(0) or palladium(II) catalyzed coupling reaction between a bromobenzene and a phenylboronic acid, as described in Comprehensive Organic Transformations, by R. C. Larock, VCH, 1989, p. 57. The sulfur-substituted phenylboronic acid 79.1 is obtained by means of a metallation-boronation sequence applied to a protected bromo-substituted thiophenol, for example as described in J. Org. Chem., 49, 5237, 1984. A coupling reaction then affords the diaryl product 79.3 which is deprotected to yield the thiol 79.4.

For example, protection of 4-bromothiophenol by reaction with tert-butylchlorodimethylsilane, in the presence of a base such as imidazole, as described in Protective Groups in Organic Synthesis, by T. W. Greene and P. G. M. Wuts, Wiley, 1991, p. 297, followed by metallation with butyllithium and boronation, as described in J. Organomet. Chem., 1999, 581, 82, affords the boronate 79.5. This material is reacted with a dialkyl 4-bromophenylphosphonate 79.6, the preparation of which is described in J. Chem. Soc., Perkin Trans., 1977, 2, 789, in the presence of tetrakis(triphenylphosphine)palladium (0) and an inorganic base such as sodium carbonate, to afford the coupled product 79.7. Deprotection, for example by the use of tetrabutylammonium fluoride in anhydrous tetrahydrofuran, then yields the thiol 79.8.

Using the above procedures, but employing, in place of the boronate 79.5, different boronates 79.1, and/or different phosphonates 79.2, there are obtained the corresponding products 79.4.

Scheme 80 depicts the preparation of dialkyl phosphonates in which the phosphonate moiety is linked to the thiophenyl group by means of a chain which incorporates an aromatic or heteroaromatic ring. In this procedure, a suitably protected O, S or N-substituted thiophenol 80.1 is reacted with a dialkyl bromomethyl-substituted aryl or heteroarylphosphonate 80.2, prepared, for example, by means of an Arbuzov reaction between equimolar amounts of a bis(bromo-methyl) substituted aromatic compound and a trialkyl phosphite. The reaction product 80.3 is then deprotected to afford the thiol 80.4. For example, 1,4-dimercaptobenzene is converted into the monobenzoyl ester 80.5 by reaction with one molar equivalent of benzoyl chloride, in the presence of a base such as pyridine. The monoprotected thiol 80.5 is then reacted with a dialkyl 4-(bromomethyl)phenylphosphonate, 80.6, the preparation of which is described in Tetrahedron, 1998, 54, 9341. The reaction is conducted in a solvent such as dimethylformamide, in the presence of a base such as potassium carbonate, at about 50°. The thioether product 80.7 thus obtained is deprotected, as described above, to afford the thiol 80.8.

Using the above procedures, but employing, in place of the thiophenol 80.5, different phenols, thiophenols or amines 80.1, and/or different phosphonates 80.2, there are obtained the corresponding products 80.4.

Scheme 81 illustrates the preparation of phosphonate-containing thiophenols in which the attached phosphonate chain forms a ring with the thiophenol moiety.

In this procedure, a suitably protected thiophenol 81.1, for example an indoline (in which X—Y is $(CH_2)_2$), an indole (X—Y is CH═CH) or a tetrahydroquinoline (X—Y is $(CH_2)_3$) is reacted with a dialkyl trifluoromethanesulfonyloxymethyl phosphonate 81.2, in the presence of an organic or inorganic base, in a polar aprotic solvent such as, for example, dimethylformamide, to afford the phosphonate ester 81.3. Deprotection, as described above, then affords the thiol 81.4. The preparation of thio-substituted indolines is described in EP 209751. Thio-substituted indoles, indolines and tetrahydroquinolines can also be obtained from the corresponding hydroxy-substituted compounds, for example by thermal rearrangement of the dimethylthiocarbamoyl esters, as described in J. Org. Chem., 31, 3980, 1966. The preparation of hydroxy-substituted indoles is described in Syn., 1994, 10, 1018; preparation of hydroxy-substituted indolines is described in Tet. Lett., 1986, 27, 4565, and the preparation of hydroxy-substituted tetrahydroquinolines is described in J. Het. Chem., 1991, 28, 1517, and in J. Med. Chem., 1979, 22, 599. Thio-substituted indoles, indolines and tetrahydroquinolines can also be obtained from the corresponding amino and bromo compounds, respectively by diazotization, as described in Sulfur Letters, 2000, 24, 123, or by reaction of the derived organolithium or magnesium derivative with sulfur, as described in Comprehensive Organic Functional Group Preparations, A. R. Katritzky et al, eds, Pergamon, 1995, Vol. 2, p 707. For example, 2,3-dihydro-1H-indole-5-thiol, 81.5, the preparation of which is described in EP 209751, is converted into the benzoyl ester 81.6, as described above, and the ester is then reacted with the trifluoromethanesulfonate 81.7, using the conditions described above for the preparation of the phosphonate 76.8, (Scheme 76), to yield the phosphonate 81.8.

Deprotection, for example by reaction with dilute aqueous ammonia, as described above, then affords the thiol 81.9.

Using the above procedures, but employing, in place of the thiol 81.5, different thiols 81.1, and/or different triflates 81.2, there are obtained the corresponding products 81.4.

Schemes 82 and 83 illustrate alternative methods for the conversion of the thiophenols 82.1, in which the substituent A is either the group link $P(O)(OR^1)_2$ or a precursor thereto, such as [OH], [SH], Br etc, prepared as described above, (Schemes 72-81) in which the substituent A is either the group link $P(O)(OR^1)_2$ or a precursor thereto, such as [OH], [SH], Br etc, into the homologated derivatives 19.1 which are employed in the preparation of the intermediate phosphonate esters 5 in which X is sulfur.

As shown in Scheme 82, the thiophenol 82.1 is reacted with the mesylate ester 43.2, using the conditions described above for the preparation of the thioether 43.4, to afford the corresponding thioether 82.2. The latter compound is then transformed, using the same sequence of reactions and reaction conditions described above (Scheme 43) for the conversion of the thioether 43.4 into the hydroxyacid 3.1, into the hydroxyacid 19.1.

Alternatively, as shown in Scheme 83, the aldehyde 82.3 is converted, as shown in Scheme 44, into the diol 83.1. The latter compound is then converted, as shown in Scheme 44 into the hydroxyacid 19.1.

Scheme 81

Method

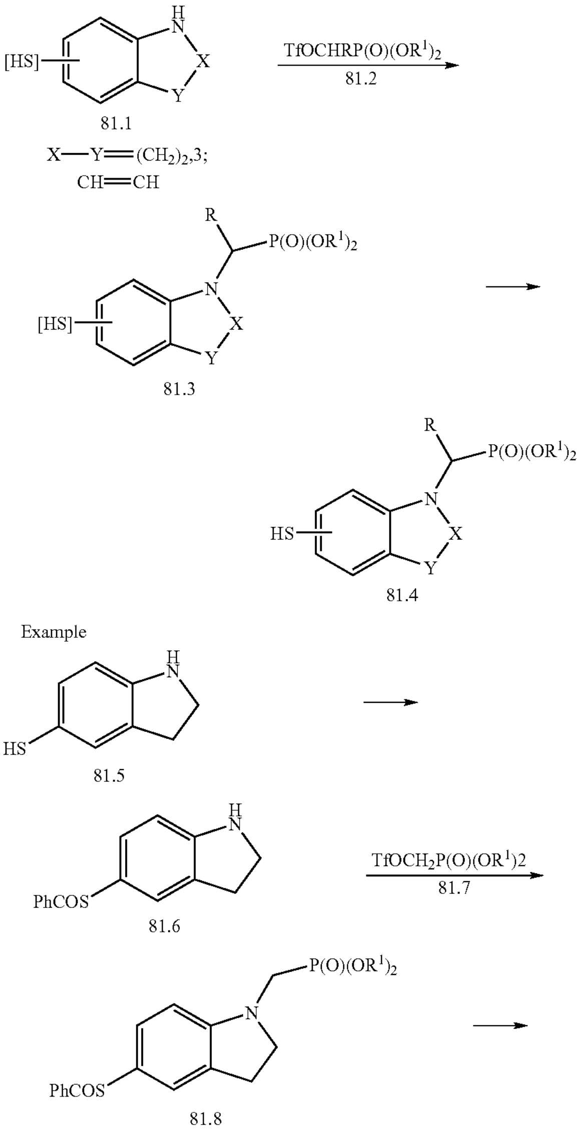

81.1

X—Y═$(CH_2)_{2,3}$; CH═CH 81.3

81.4

Example 81.5

81.6

81.8

-continued

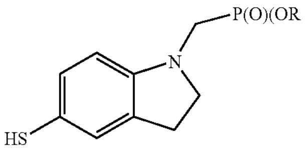

81.9

Scheme 82

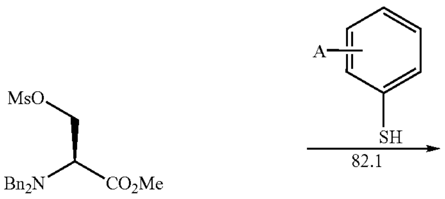

82.1

43.2

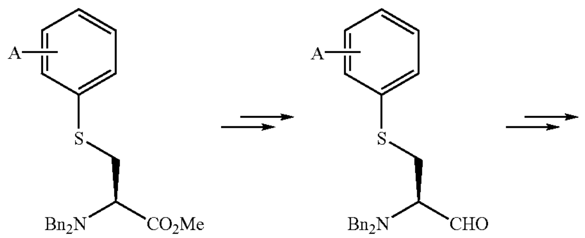

82.2

82.3

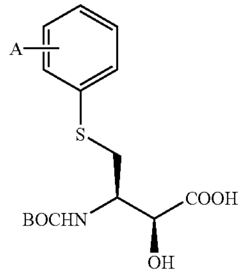

19.1

Scheme 83

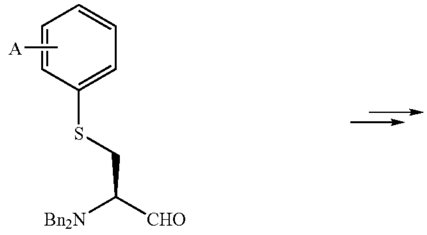

82.3

-continued

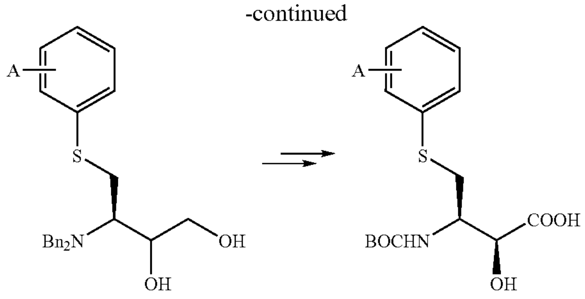

83.1

19.1

Preparation of Tert-butylamine Derivatives 25.1 Incorporating Phosphonate Groups.

Schemes 84-87 illustrate the preparation of the tert. butylamine derivatives 25.1 in which the substituent A is either the group link $P(O)(OR^1)_2$ or a precursor thereto, such as [OH], [SH], Br etc, which are employed in the preparation of the intermediate phosphonate esters 7.

Scheme 84 describes the preparation of tert-butylamines in which the phosphonate moiety is directly attached to the tert-butyl group. A suitably protected 2.2-dimethyl-2-aminoethyl bromide 84.1 is reacted with a trialkyl phosphite 84.2, under the conditions of the Arbuzov reaction, as described above, to afford the phosphonate 84.3, which is then deprotected as described previously to give 84.4

For example, the cbz derivative of 2,2-dimethyl-2-aminoethyl bromide 84.6, is heated with a trialkyl phosphite at ca 150° to afford the product 84.7. Deprotection, as previously described, then affords the free amine 84.8.

Using the above procedures, but employing different trisubstituted phosphites, there are obtained the corresponding amines 84.4.

Scheme 85 illustrates the preparation of phosphonate esters attached to the tert butylamine by means of a heteroatom and a carbon chain. An optionally protected alcohol or thiol 85.1 is reacted with a bromoalkylphosphonate 85.2, to afford the displacement product 85.3. Deprotection, if needed, then yields the amine 85.4.

For example, the cbz derivative of 2-amino-2,2-dimethylethanol 85.5 is reacted with a dialkyl 4-bromobutyl phosphonate 85.6, prepared as described in Synthesis, 1994, 9, 909, in dimethylformamide containing potassium carbonate and a catalytic amount of potassium iodide, at ca 60° to afford the phosphonate 85.7 Deprotection, by hydrogenation over a palladium catalyst, then affords the free amine 85.8.

Using the above procedures, but employing different alcohols or thiols 85.1, and/or different bromoalkylphosphonates 85.2, there are obtained the corresponding ether and thioether products 85.4.

Scheme 86 describes the preparation of carbon-linked tert. butylamine phosphonate derivatives, in which the carbon chain can be unsaturated or saturated.

In the procedure, a terminal acetylenic derivative of tert-butylamine 86.1 is reacted, under basic conditions, with a dialkyl chlorophosphite 86.2, to afford the acetylenic phosphonate 86.3. The coupled product 86.3 is deprotected to afford the amine 86.4. Partial or complete catalytic hydrogenation of this compound affords the olefinic and saturated products 86.5 and 86.6 respectively.

For example, 2-amino-2-methylprop-1-yne 86.7, the preparation of which is described in WO 9320804, is converted into the N-phthalimido derivative 86.8, by reaction with phthalic anhydride, as described in Protective Groups in Organic Synthesis, by T. W. Greene and P. G. M. Wuts, Wiley, 1991, pp. 358. This compound is reacted with lithium diisopropylamide in tetrahydrofuran at −78°. The resultant anion is then reacted with a dialkyl chlorophosphite 86.2 to afford the phosphonate 86.9. Deprotection, for example by treatment with hydrazine, as described in J. Org. Chem., 43, 2320, 1978, then affords the free amine 86.10. Partial catalytic hydrogenation, for example using Lindlar catalyst, as described in Reagents for Organic Synthesis, by L. F. Fieser and M. Fieser, Volume 1, p 566, produces the olefinic phosphonate 86.11, and conventional catalytic hydrogenation, as described in Organic Functional Group Preparations, by S. R. Sandler and W. Karo, Academic Press, 1968, p. 3. for example using 5% palladium on carbon as catalyst, affords the saturated phosphonate 86.12. Using the above procedures, but employing different acetylenic amines 86.1, and/or different dialkyl halophosphites, there are obtained the corresponding products 86.4, 86.5 and 86.6.

Scheme 87 illustrates the preparation of a tert butylamine phosphonate in which the phosphonate moiety is attached by means of a cyclic amine.

In this method, an aminoethyl-substituted cyclic amine 87.1 is reacted with a limited amount of a bromoalkyl phosphonate 87.2, using, for example, the conditions described above (Scheme 78) to afford the displacement product 87.3.

For example, 3-(1-amino-1-methyl)ethylpyrrolidine 87.4, the preparation of which is described in Chem. Pharm. Bull., 1994, 42, 1442, is reacted with one molar equivalent of a dialkyl 4-bromobutyl phosphonate 87.5, prepared as described in Synthesis, 1994, 9, 909, to afford the displacement product 87.6.

Using the above procedures, but employing, in place of 3-(1-amino-1-methyl)ethylpyrrolidine 87.4, different cyclic amines 87.1, and/or different bromoalkylphosphonates 87.2, there are obtained the corresponding products 87.3.

Scheme 86

Method

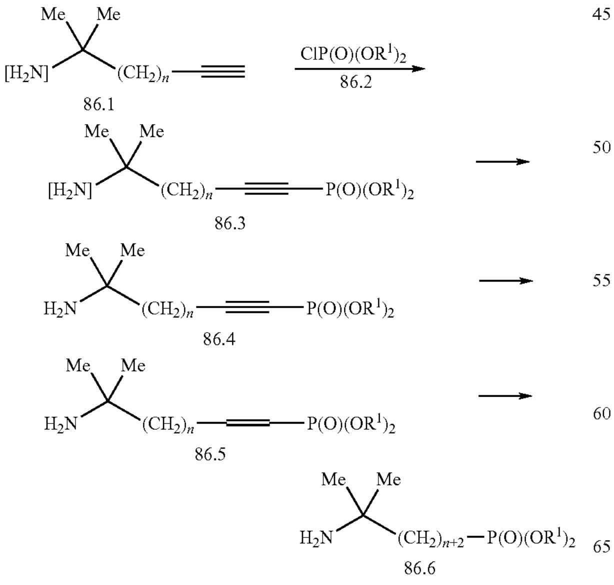

86.1 86.3 86.4 86.5 86.6

-continued

Example

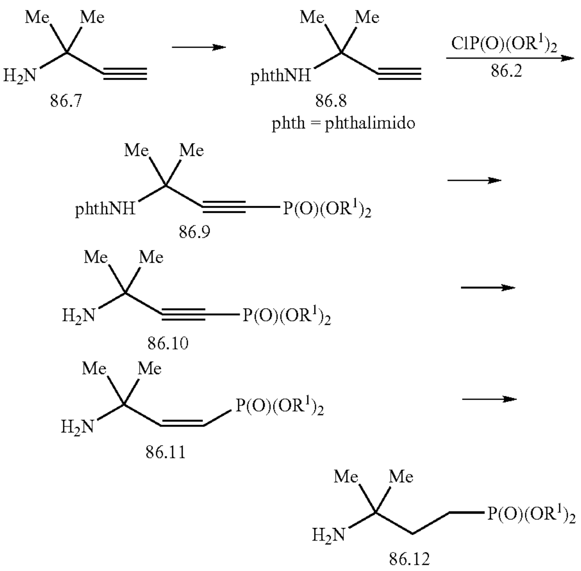

86.7 86.8 86.9 86.10 86.11 86.12

Scheme 87

Method

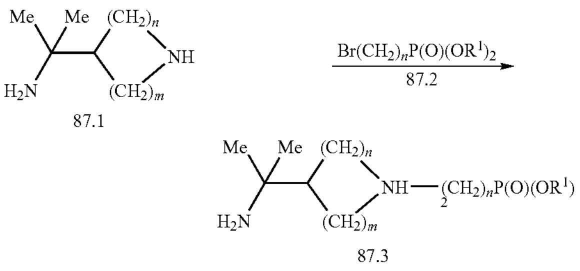

87.1 87.3

Example

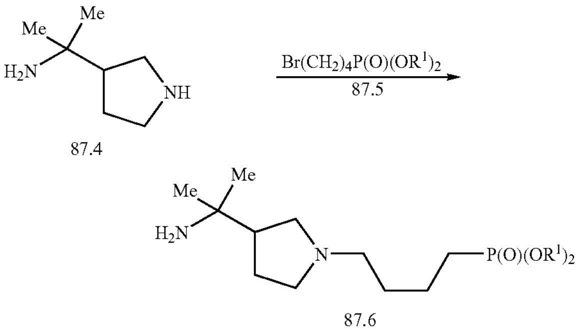

87.4 87.6

Preparation of Phosphonate-containing Methyl-substituted Benzylamines 29.1.

Schemes 88-90 illustrate the preparation of phosphonate-containing 2-methyl and 2,6-dimethylbenzylamines 29.1 in which the substituent A is either the group link $P(O)(OR^1)_2$ or a precursor thereto, such as [OH], [SH], Br etc, which are employed in the preparation of the phosphonate ester intermediates 8, as described in Schemes 29-32. A number of variously substituted 2-methyl and 2,6-dimethylbenzylamies are commercially available or have published syntheses. In addition, substituted benzylamines are prepared by various methods known to those skilled in the art. For example, substituted benzylamines are obtained by reduction of the correspondingly substituted benzamides, for example by the use of diborane or lithium aluminum hydride, as described, for example, in Comprehensive Organic Transformations, by R. C. Larock, VCH, 1989, p. 432ff.

Scheme 88 depicts the preparation of 2-methyl or 2,6-dimethylbenzyamines incorporating a phosphonate moiety directly attached to the benzene ring, or attached by means of a saturated or unsaturated alkylene chain. In this procedure, a bromo-substituted 2-methyl or 2,6-dimethylbenzylamine 88.1 is protected to produce the analog 88.2. The protection of amines is described, for example, in Protective Groups in Organic Synthesis, by T. W. Greene and P. G. M Wuts, Wiley, Second Edition 1990, p. 309ff. For example, the amine 88.1 is protected as an amide or carbamate derivative. The protected amine is then reacted with a dialkyl phosphite 88.3, in the presence of a palladium catalyst, as described above (Scheme 69) to afford the phosphonate product 88.4. Deprotection then affords the free amine 88.5. Alternatively, the protected bromo-substituted benzylamine 88.2 is coupled with a dialkyl alkenyl phosphonate 88.6, using the conditions of the Heck reaction, as described above, (Scheme 59) to afford the alkenyl product 88.7. The amino protecting group is then removed to yield the free amine 88.8. Optionally, the olefinic double bond is reduced, for example by the use of diborane or diimide, or by means of catalytic hydrogenation, as described above (Scheme 59) to produce the saturated analog 88.9.

For example, 4-bromo-2,6-dimethylbenzylamine 88.10, (Trans World Chemicals) is converted into the BOC derivative 88.11, as described above, and the product is coupled with a dialkyl phosphite 88.3, in the presence of triethylamine and tetrakis(triphenylphosphine)palladium(0), as described in J. Med. Chem., 35, 1371, 1992, to yield the phosphonate ester 88.12.

Deprotection, for example by treatment with trifluoroacetic acid, then produces the free amine 88.13.

Using the above procedures, but employing, in place of 4-bromo-2,6-dimethylbenzylamine 88.10, different bromobenzylamines 88.1, the corresponding products 88.5 are obtained.

As an additional example of the methods of Scheme 88, 4-bromo-2-methylbenzylamine 88.14 (Trans World Chemicals) is converted into the BOC derivative 88.15. The latter compound is then reacted with a dialkyl vinylphosphonate 88.16, (Aldrich) in the presence of 2 mol % of tetrakis(triphenylphosphine)palladium and triethylamine, to afford the coupled product 88.17. Deprotection then affords the amine 88.18, and reduction of the latter compound with diimide gives the saturated analog 88.19.

Using the above procedures, but employing, in place of 4-bromo-2-methylbenzylamine 88.14, different bromobenzylamines 88.1, and/or different alkenyl phosphonates 88.6, the corresponding products 88.8 and 88.9 are obtained.

Scheme 89 depicts the preparation of 2-methyl or 2,6-dimethylbenzyamines incorporating a phosphonate moiety attached to the benzene ring by means of an amide linkage. In this procedure, the amino group of a carboxy-substituted 2-methyl or 2,6-dimethylbenzylamine 89.1 is protected to yield the product 89.2. The latter compound is then reacted with a dialkyl aminoalkyl phosphonate 89.3 to afford the amide 89.4. The reaction is performed as described above for the preparation of the amides 1.3 and 1.6. The amine protecting group is then removed to give the free amine 89.5.

For example, 4-carboxy-2-methylbenzylamine 89.6, prepared as described in Chem. Pharm. Bull., 1979, 21, 3039, is converted into the BOC derivative 89.7. This material is then reacted in tetrahydrofuran solution with one molar equivalent of a dialkyl aminoethyl phosphonate 89.8, in the presence of dicyclohexylcarbodiimide and hydroxybenztriazole, to produce the amide 89.9. Deprotection, for example by reaction with methanesulfonic acid in acetonitrile, then yields the amine 89.10.

Using the above procedures, but employing, in place of 4-carboxy-2-methylbenzylamine 89.6, different carboxy-substituted benzylamines 89.1, and/or different aminoalkyl phosphonates 89.3, the corresponding products 89.5 are obtained.

Scheme 90 depicts the preparation of 2-methyl or 2,6-dimethylbenzyamines incorporating a phosphonate moiety attached to the benzene ring by means of a heteroatom and an alkylene chain. In this procedure, the amino group of a hydroxy or mercapto-substituted methylbenzylamine 90.1 is protected to afford the derivative 90.2. This material is then reacted with a dialkyl bromoalkyl phosphonate 90.3 to yield the ether or thioether product 90.4. The reaction is conducted in a polar organic solvent such as dimethylformamide or N-methylpyrrolidinone, in the presence of a base such as diazabicyclononene or cesium carbonate. The amino protecting group is then removed to afford the product 90.5.

For example, 2,6-dimethyl-4-hydroxybenzylamine 90.6, prepared, as described above, from 2,6-dimethyl-4-hydroxybenzoic acid, the preparation of which is described in J. Org. Chem., 1985, 50, 2867, is protected to afford the BOC derivative 90.7. The latter compound is then reacted with one molar equivalent of a dialkyl bromoethyl phosphonate 90.8, (Aldrich) and cesium carbonate in dimethylformamide solution at 80° to give the ether 90.9. Deprotection then afford the amine 90.10.

Using the above procedures, but employing, in place of 4-hydroxy-2,6-dimethylbenzylamine 90.6, different hydroxy or mercapto-substituted benzylamines 90.1, and/or different bromoalkyl phosphonates 90.3, the corresponding products 90.5 are obtained.

Scheme 89

Method

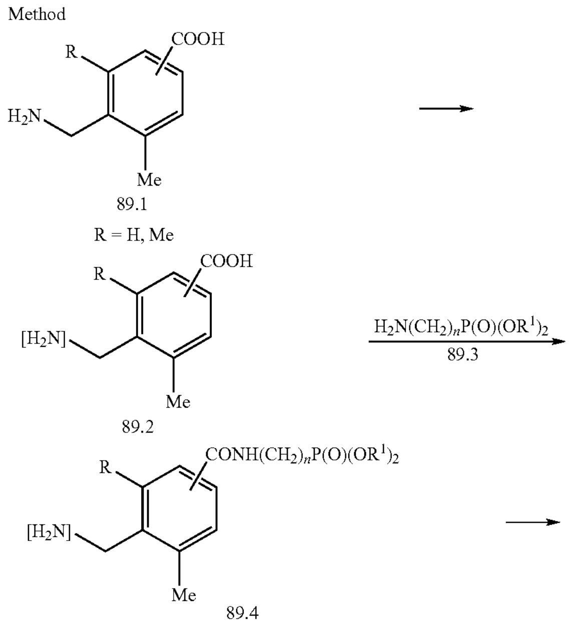

89.1

R = H, Me 89.2

89.4

-continued

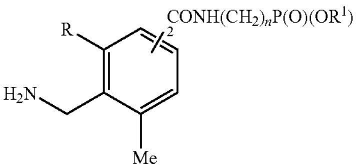

89.5

Example

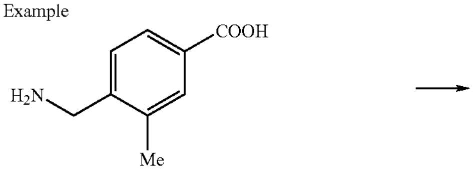

89.6

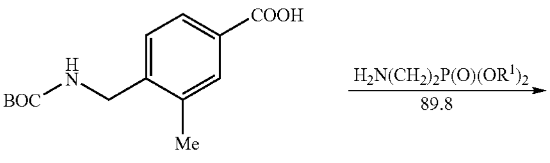

89.7

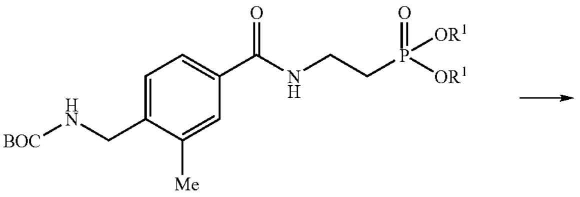

89.9

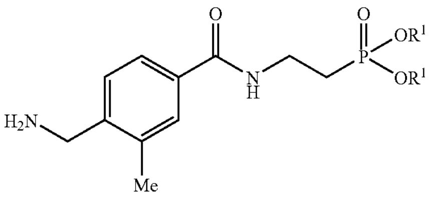

89.10

Scheme 90

Method

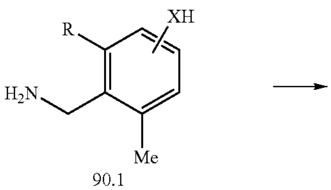

90.1

R = H, Me X = O,S

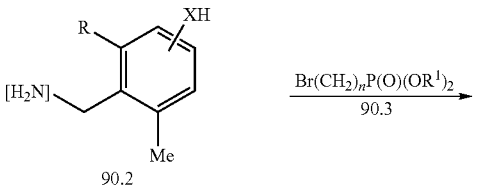

90.2

-continued

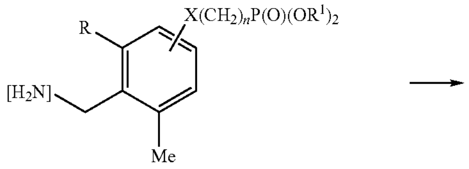

90.4

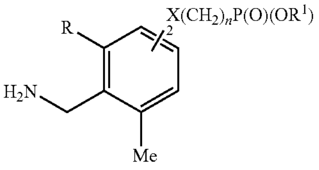

90.5

Example

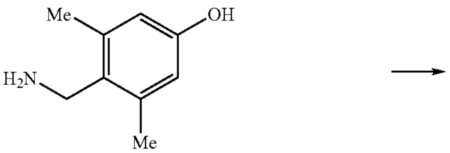

90.6

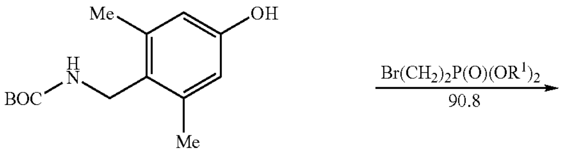

90.7

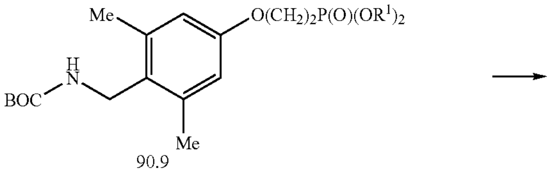

90.9

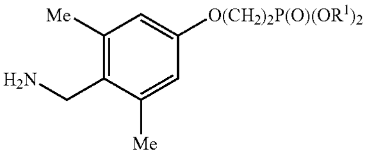

90.10

Preparation of Phosphonate-substituted Decahydroquinolines 33.1.

Schemes 91-97 illustrate the preparation of decahydroisoquinoline derivatives 33.1 in which the substituent A is either the group link $P(O)(OR^1)_2$ or a precursor thereto, such as [OH], [SH], Br etc. The compounds are employed in the preparation of the intermediate phosphonate esters 9, (Schemes 33-36)

Scheme 91 illustrates methods for the synthesis of intermediates for the preparation of decahydroquinolines with phosphonate moieties at the 6-position. Two methods for the preparation of the benzenoid intermediate 91.4 are shown.

In the first route, 2-hydroxy-6-methylphenylalanine 91.1, the preparation of which is described in J. Med. Chem., 1969, 12, 1028, is converted into the protected derivative 91.2. For example, the carboxylic acid is first transformed into the benzyl ester, and the product is reacted with acetic anhydride in the presence of an organic base such as, for example, pyridine, to afford the product 91.2, in which R is benzyl. This compound is reacted with a brominating agent, for example N-bromosuccinimide, to effect benzylic bromination and yield the product 91.3. The reaction is conducted in an aprotic solvent such as, for example, ethyl acetate or carbon tetrachloride, at reflux. The brominated compound 91.3 is then treated with acid, for example dilute hydrochloric acid, to effect hydrolysis and cyclization to afford the tetrahydroisoquinoline 91.4, in which R is benzyl.

Alternatively, the tetrahydroisoquinoline 91.4 can be obtained from 2-hydroxyphenylalanine 91.5, the preparation of which is described in Can. J. Bioch., 1971, 49, 877. This compound is subjected to the conditions of the Pictet-Spengler reaction, for example as described in Chem. Rev., 1995, 95, 1797.

Typically, the substrate 91.5 is reacted with aqueous formaldehyde, or an equivalent such as paraformaldehyde or dimethoxymethane, in the presence of hydrochloric acid, for example as described in J. Med. Chem., 1986, 29, 784, to afford the tetrahydroisoquinoline product 91.4, in which R is H. Catalytic hydrogenation of the latter compound, using, for example, a platinum catalyst, as described in J. Am. Chem. Soc., 69, 1250, 1947, or using rhodium on alumina as catalyst, as described in J. Med. Chem., 1995, 38, 4446, then gives the hydroxy-substituted decahydroisoquinoline 91.6. The reduction can also be performed electrochemically, as described in Trans SAEST 1984, 19, 189.

For example, the tetrahydroisoquinoline 91.4 is subjected to hydrogenation in an alcoholic solvent, in the presence of a dilute mineral acid such as hydrochloric acid, and 5% rhodium on alumina as catalyst. The hydrogenation pressure is ca. 750 psi, and the reaction is conducted at ca 50°, to afford the decahydroisoquinoline 91.6.

Protection of the carboxyl and NH groups present in 91.6 for example by conversion of the carboxylic acid into the trichloroethyl ester, as described in Protective Groups in Organic Synthesis, by T. W. Greene and P. G. M. Wuts, Wiley, 1991, p. 240, and conversion of the NH into the N-cbz group, as described above, followed by oxidation, using, for example, pyridinium chlorochromate and the like, as described in Reagents for Organic Synthesis, by L. F. Fieser and M. Fieser, Volume 6, p. 498, affords the protected ketone 91.9, in which R is trichloroethyl and $R_1$ is cbz. Reduction of the ketone, for example by the use of sodium borohydride, as described in J. Am. Chem. Soc., 88, 2811, 1966, or lithium tri-tertiary butyl aluminum hydride, as described in J. Am. Chem. Soc., 80, 5372, 1958, then affords the alcohol 91.10.

For example, the ketone is reduced by treatment with sodium borohydride in an alcoholic solvent such as isopropanol, at ambient temperature, to afford the alcohol 91.10.

The alcohol 91.6 can be converted into the thiol 91.13 and the amine 91.14, by means of displacement reactions with suitable nucleophiles, with inversion of stereochemistry. For example, the alcohol 91.6 can be converted into an activated ester such as the trifluoromethanesulfonyl ester or the methanesulfonate ester 91.7, by treatment with methanesulfonyl chloride and a base. The mesylate 91.7 is then treated with a sulfur nucleophile, for example potassium thioacetate, as described in Tet. Lett., 1992, 4099, or sodium thiophosphate, as described in Acta Chem. Scand., 1960, 1980, to effect displacement of the mesylate, followed by mild basic hydrolysis, for example by treatment with aqueous ammonia, to afford the thiol 91.13.

For example, the mesylate 91.7 is reacted with one molar equivalent of sodium thioacetate in a polar aprotic solvent such as, for example, dimethylformamide, at ambient temperature, to afford the thioacetate 91.12, in which R is $COCH_3$. The product then treated with, a mild base such as, for example, aqueous ammonia, in the presence of an organic co-solvent such as ethanol, at ambient temperature, to afford the thiol 91.13.

The mesylate 91.7 can be treated with a nitrogen nucleophile, for example sodium phthallmide or sodium bis(trimethylsilyl)amide, as described in Comprehensive Organic Transformations, by R. C. Larock, p399, followed by deprotection as described previously, to afford the amine 91.14.

For example, the mesylate 91.7 is reacted, as described in Angew. Chem. Int. Ed., 7, 919, 1968, with one molar equivalent of potassium phthalimide, in a dipolar aprotic solvent, such as, for example, dimethylformamide, at ambient temperature, to afford the displacement product 91.8, in which $NR^aR^b$ is phthalimido. Removal of the phthalimido group, for example by treatment with an alcoholic solution of hydrazine at ambient temperature, as described in J. Org. Chem., 38, 3034, 1973, then yields the amine 91.14.

The application of the procedures described above for the conversion of the β-carbinol 91.6 to the α-thiol 91.13 and the α-amine 91.14 can also be applied to the α-carbinol 91.10, so as to afford the β-thiol and β-amine, 91.11.

Scheme 92 illustrates the preparation of compounds in which the phosphonate moiety is attached to the decahydroisoquinoline by means of a heteroatom and a carbon chain.

In this procedure, an alcohol, thiol or amine 92.1 is reacted with a bromoalkyl phosphonate 92.2, under the conditions described above for the preparation of the phosphonate 90.4 (Scheme 90), to afford the displacement product 92.3. Removal of the ester group, followed by conversion of the acid to the $R^4R^5N$ amide and N-deprotection, as described herein, (Scheme 96) then yields the amine 92.8.

For example, the compound 92.5, in which the carboxylic acid group is protected as the trichloroethyl ester, as described in Protective Groups in Organic Synthesis, by T. W. Greene and P. G. M. Wuts, Wiley, 1991, p. 240, and the amine is protected as the cbz group, is reacted with a dialkyl 3-bromopropylphosphonate, 92.6, the preparation of which is described in J. Am. Chem. Soc., 2000, 122, 1554 to afford the displacement product 92.7. Deprotection of the ester group, followed by conversion of the acid to the $R^4R^5N$ amide and N-deprotection, as described herein, (Scheme 96) then yields the amine 92.8.

Using the above procedures, but employing, in place of the α-thiol 92.5, the alcohols, thiols or amines 91.6, 91.10, 91.11, 91.13, 91.14, of either α- or β-orientation, there are obtained the corresponding products 92.4, in which the orientation of the side chain is the same as that of the O, N or S precursors.

Scheme 93 illustrates the preparation of phosphonates linked to the decahydroisoquinoline moiety by means of a nitrogen atom and a carbon chain. The compounds are prepared by means of a reductive amination procedure, for example as described in Comprehensive. Organic Transformations, by R. C. Larock, p421.

In this procedure, the amines 91.14 or 91.11 are reacted with a phosphonate aldehyde 93.1, in the presence of a reducing agent, to afford the alkylated amine 93.2. Deprotection of the ester group, followed by conversion of the acid to the $R^4NH$ amide and N-deprotection, as described herein, (Scheme 96) then yields the amine 93.3.

For example, the protected amino compound 91.14 is reacted with a dialkyl formylphosphonate 93.4, the preparation of which is described in U.S. Pat. No. 3,784,590, in the presence of sodium cyanoborohydride, and a polar organic solvent such as ethanolic acetic acid, as described in Org. Prep. Proc. Int., 11, 201, 1979, to give the amine phosphonate 93.5. Deprotection of the ester group, followed by conversion of the acid to the $R^4R^5N$ amide and N-deprotection, as described herein, (Scheme 96) then yields the amine 93.6.

Using the above procedures, but employing, instead of the α-amine 91.14, the β isomer, 91.11 and/or different aldehydes 93.1, there are obtained the corresponding products 93.3, in which the orientation of the side chain is the same as that of the amine precursor.

Scheme 94 depicts the preparation of a decahydroisoquinoline phosphonate in which the phosphonate moiety is linked by means of a sulfur atom and a carbon chain.

In this procedure, a thiol phosphonate 94.2 is reacted with a mesylate 94.1, to effect displacement of the mesylate group with inversion of stereochemistry, to afford the thioether product 94.3. Deprotection of the ester group, followed by conversion of the acid to the $R^4R^5N$ amide and N-deprotection, as described herein, (Scheme 96) then yields the amine 94.4.

For example, the protected mesylate 94.5 is reacted with an equimolar amount of a dialkyl 2-mercaptoethyl phosphonate 94.6, the preparation of which is described in Aust. J. Chem., 43, 1123, 1990. The reaction is conducted in a polar organic solvent such as ethanol, in the presence of a base such as, for example, potassium carbonate, at ambient temperature, to afford the thio ether phosphonate 94.7. Deprotection of the ester group, followed by conversion of the acid to the $R^4R^5N$ amide and N-deprotection, as described herein, (Scheme 96) then yields the amine 94.8

Using the above procedures, but employing, instead of the phosphonate 94.6, different phosphonates 94.2, there are obtained the corresponding products 94.4.

Scheme 95 illustrates the preparation of decahydroisoquinoline phosphonates 95.4 in which the phosphonate group is linked by means of an aromatic or heteroaromatic ring. The compounds are prepared by means of a displacement reaction between hydroxy, thio or amino substituted substrates 95.1 and a bromomethyl substituted phosphonate 95.2. The reaction is performed in an aprotic solvent in the presence of a base of suitable strength, depending on the nature of the reactant 95.1. If X is S or NH, a weak organic or inorganic base such as triethylamine or potassium carbonate can be employed. If X is O, a strong base such as sodium hydride or lithium hexamethyldisilylazide is required. The displacement reaction affords the ether, thioether or amine compounds 95.3. Deprotection of the ester group, followed by conversion of the acid to the $R^4R^5N$ amide and N-deprotection, as described herein, (Scheme 96) then yields the amine 95.4.

For example, the protected alcohol 95.5 is reacted at ambient temperature with a dialkyl 3-bromomethyl phenylmethylphosphonate 95.6, the preparation of which is described above, (Scheme 80). The reaction is conducted in a dipolar aprotic solvent such as, for example, dioxan or dimethylformamide. The solution of the carbinol is treated with one equivalent of a strong base, such as, for example, lithium hexamethyldisilylazide, and to the resultant mixture is added one molar equivalent of the bromomethyl phosphonate 95.6, to afford the product 95.7. Deprotection of the ester group, followed by conversion of the acid to the $R^4R^5N$ amide and N-deprotection, as described herein, (Scheme 96) then yields the amine 95.8.

Using the above procedures, but employing, instead of the β-carbinol 95.5, different carbinols, thiols or amines 95.1, of either α- or β-orientation, and/or different phosphonates 95.2, in place of the phosphonate 95.6, there are obtained the corresponding products 95.4 in which the orientation of the side-chain is the same as that of the starting material 95.1.

Schemes 92-95 illustrate the preparation of decahydroisoquinoline esters incorporating a phosphonate group linked to the decahydroisoquinoline nucleus.

Scheme 96 illustrates the conversion of the latter group of compounds 96.1 (in which the group B is link-$P(O)(OR^1)_2$ or optionally protected precursor substituents thereto, such as, for example, OH, SH, $NH_2$) to the corresponding $R^4R^5N$ amides 96.5.

As shown in Scheme 96, the ester compounds 96.1 are deprotected to form the corresponding carboxylic acids 96.2. The methods employed for the deprotection are chosen based on the nature of the protecting group R, the nature of the N-protecting group $R^2$, and the nature of the substituent at the 6-position. For example, if R is trichloroethyl, the ester group is removed by treatment with zinc in acetic acid, as described in J. Am. Chem. Soc., 88, 852, 1966.

Conversion of the carboxylic acid 96.2 to the $R^4R^5N$ amide 96.4 is then accomplished by reaction of the carboxylic acid, or an activated derivative thereof, with the amine $R^4R^5NH$ 96.3 to afford the amide 96.4, using the conditions described above for the preparation of the amide 1.6. Deprotection of the $NR^2$ group, as described above, then affords the free amine 96.5.

Scheme 95

Method

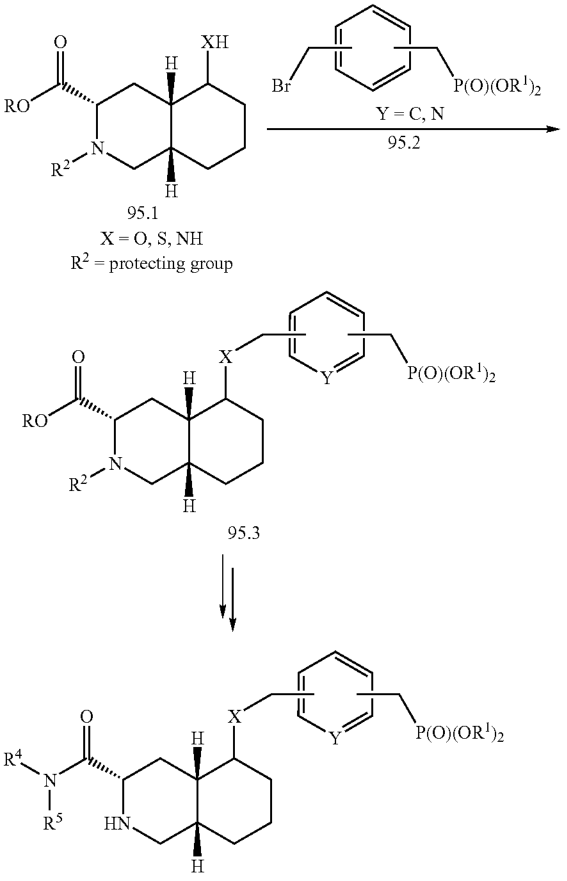

95.1

X = O, S, NH $R^2$ = protecting group 95.3

95.4

-continued

Example

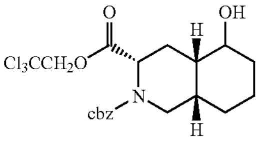

95.5

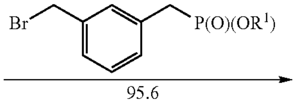

95.6

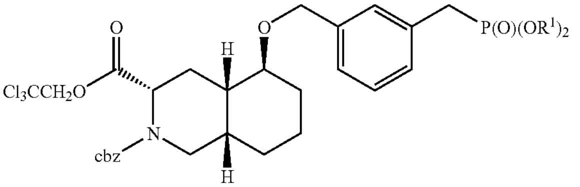

95.7

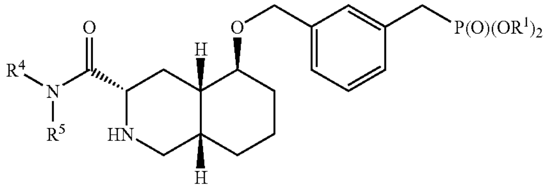

95.8

Scheme 96

Method

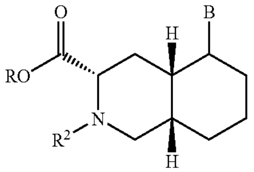

96.1

$R^2$ = protecting group

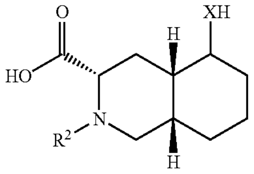

96.2

$R^4R^5NH$ 96.3

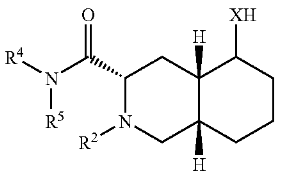

96.4

-continued

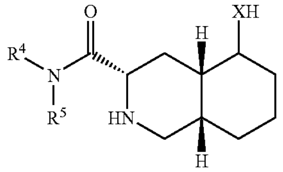

96.5

Preparation of the Phosphonate-containing Tert. Butylamides 37.1.

Scheme 97 illustrates the preparation of the amides 37.1 in which the substituent A is either the group link $P(O)(OR^1)_2$ or a precursor thereto, such as [OH], [SH], Br etc, which are employed in the preparation of the intermediate phosphonate esters 10 (Schemes 37-40). In this procedure, the BOC-protected decahydroisoquinoline carboxylic acid 97.1 is reacted with the tert. butylamine derivative 25.1, in which the substituent A is the group link-$P(O)(OR^1)_2$, or a precursor group thereto, such as [OH], [SH], Br, etc, to afford the amide 97.2. The reaction is conducted as described above for the preparation of the amides 1.3 and 1.6. The BOC protecting group is then removed to yield the amine 37.1.

Preparation of the Phosphonate-containing Thiazolidines 21.1.

Schemes 98-101 illustrate the preparation of the thiazolidine derivatives 37.1, in which the substituent A is either the group link $P(O)(OR^1)_2$ or a precursor thereto, such as [OH], [SH], Br etc, which are employed in the preparation of the intermediate phosphonate esters 6. The preparation of the penicillamine analogs 98.5 in which R is alkyl is described in J. Org. Chem., 1986, 51, 5153 and in J. Labelled. Comp. Radiochem., 1987, 24, 1265. The conversion of the penicillamine analogs 98.5 into the corresponding thiazolidines 98.7 is described in J. Med. Chem., 1999, 42, 1789 and in J. Med. Chem., 1989, 32, 466. The above-cited procedures, and their use to afford analogs of the thiazolidines 98.7 are shown in Scheme 98.

In this procedure, a methyl ketone 98.2 is reacted with methyl isocyanoacetate 98.1 to afford the aminoacrylate product 98.3. The condensation reaction is conducted in the presence of a base such as butyllithium or sodium hydride, in a solvent such as tetrahydrofuran at from −80° to 0°, to afford after treatment with aqueous ammonium chloride the N-formyl acrylate ester 98.3. The latter compound is then reacted with phosphorus pentasulfide or Lawessons reagent and the like to yield the thiazoline derivative 98.4. The reaction is performed in an aprotic solvent such as benzene, for example as described in J. Org. Chem., 1986, 51, 5153. The thiazoline product 98.4 is then treated with dilute acid, for example dilute hydrochloric acid, to produce the aminothiol 98.5. This compound is reacted with aqueous formaldehyde at pH 5, for example as described in J. Med. Chem., 1999, 42, 1789, to prepare the thiazolidine 98.6. The product is then converted, as described previously, into the BOC-protected analog 98.7. Some examples of the use of the reactions of Scheme 98 for the preparation of functionally substituted thiazolidines 98.7 are shown below.

Scheme 98, Example 1 illustrates the preparation of the BOC-protected hydroxymethyl thiazolidine 98.11. In this procedure, methyl isocyanoacetate 98.1 is reacted with hydroxyacetone 98.8 in the presence of a base such as sodium hydride, to yield the aminoacrylate derivative 98.9. The product is then reacted with phosphorus pentasulfide, as described above, to prepare the thiazoline 98.10. The latter compound is then converted, as described above, into the thiazolidine derivative 98.11.

Scheme 98, Example 2, depicts the preparation of bromophenyl-substituted thiazolidines 98.14. In this reaction sequence, methyl isocyanoacetate 98.1 is condensed, as described above, with a bromoacetophenone 98.12 to give the aminocinnamate derivative 98.13. The latter compound is then transformed, as described above, into the thiazolidine derivative 98.14.

Scheme 98, Example 3 depicts the preparation of the BOC-protected thiazolidine-5-carboxylic acid 98.18. In this procedure, methyl isocyanoacetate 98.1 is reacted, as described above, with trichloroethyl pyruvate 98.15 to afford the aminoacrylate derivative 98.16. This compound is then transformed, as described above, into the thiazolidine diester 98.17. The trichloroethyl ester is then cleaved, for example by treatment with zinc in aqueous tetrahydrofuran at pH 4.2, as described in J. Am. Chem. Soc., 88, 852, 1966, to afford the 5-carboxylic acid 98.18.

Scheme 98, Example 4, depicts the preparation of the BOC-protected thiazolidine-4-carboxylic acid incorporating a phosphonate moiety. In this procedure, methyl isocyanoacetate 98.1 is condensed, as described above, with a dialkyl 2-oxopropyl phosphonate 98.19, (Aldrich); the product 98.20 is then transformed, as described above, into the corresponding 4-carbomethoxythiazolidine. Hydrolysis of the methyl ester, for example by the use of one equivalent of lithium hydroxide in aqueous tetrahydrofuran, then yields the carboxylic acid 98.21.

Scheme 99 illustrates the preparation of BOC-protected thiazolidine-4-carboxylic acids incorporating a phosphonate group attached by means of an oxygen atom and an alkylene chain. In this procedure, the hydroxymethyl thiazolidine 98.11 is reacted with a dialkyl bromoalkyl phosphonate 99.1 to afford the ether product 99.2. The hydroxymethyl substrate 98.11 is treated in dimethylformamide solution with a strong base such as sodium hydride or lithium hexamethyldisilylazide, and an equimolar amount of the bromo compound 99.1 is added. The product 99.2 is then treated with aqueous base, as described above, to effect hydrolysis of the methyl ester to yield the carboxylic acid 99.3.

For example, the hydroxymethyl thiazolidine 98.11 is reacted with sodium hydride and a dialkyl bromoethyl phosphonate 99.4 (Aldrich) in dimethylformamide at 70°, to produce the phosphonate product 99.5. Hydrolysis of the methyl ester then affords the carboxylic acid 99.6.

Using the above procedures, but employing, in place of the dialkyl bromoethyl phosphonate 99.4, different bromoalkyl phosphonates 99.1, the corresponding products 99.3 are obtained.

Scheme 100 illustrates the preparation of BOC-protected thiazolidine-4-carboxylic acids incorporating a phosphonate group attached by means of a phenyl group. In this procedure, a bromophenyl-substituted thiazolidine 98.14 is coupled, as described above (Scheme 46) in the presence of a palladium catalyst, with a dialkyl phosphite 100.1, to produce the phenylphosphonate derivative 100.2. The methyl ester is then hydrolyzed to afford the carboxylic acid 100.3.

For example, the BOC-protected 5-(4-bromophenyl)thiazolidine 100.4 is coupled with a dialkyl phosphite 100.1 to yield the product 100.5, which upon hydrolysis affords the carboxylic acid 100.6.

Using the above procedures, but employing, in place of the 4-bromophenyl thiazolidine 100.4, different bromophenyl thiazolidines 98.14, the corresponding products 100.3 are obtained. Scheme 101 illustrates the preparation of BOC-protected thiazolidine-4-carboxylic acids incorporating a phosphonate group attached by means of an amide linkage. In this procedure, a thiazolidine-5-carboxylic acid 98.18 is reacted with a dialkyl aminoalkyl phosphonate 101.1 to produce the amide 101.2. The reaction is conducted as described above for the preparation of the amides 1.3 and 1.6. The methyl ester is then hydrolyzed to afford the carboxylic acid 101.3.

For example, the carboxylic acid 98.18 is reacted in tetrahydrofuran solution with an equimnolar amount of a dialkyl aminopropyl phosphonate 101.4 (Acros) and dicyclohexylcarbodiimide, to afford the amide 101.5. The methyl ester is then hydrolyzed to afford the carboxylic acid 101.6.

Using the above procedures, but employing, in place of the dialkyl aminopropyl phosphonate 101.4, different aminoalkyl phosphonates 101.1, the corresponding products 101.3 are obtained.

Scheme 99

Method

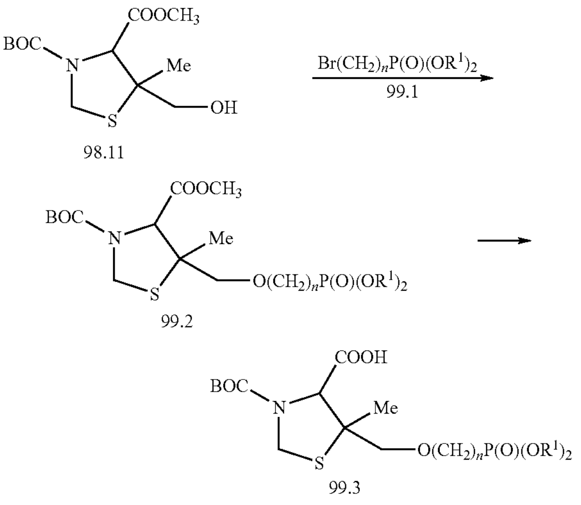

Example

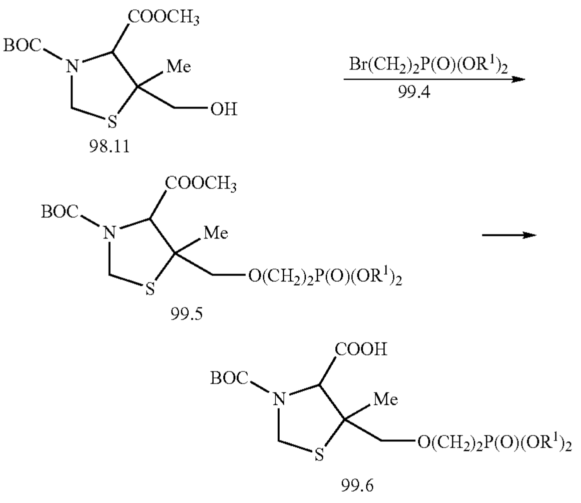

Scheme 100

Method

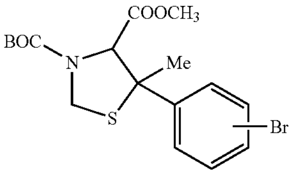

98.14

$HP(O)(OR^1)_2$ 100.1

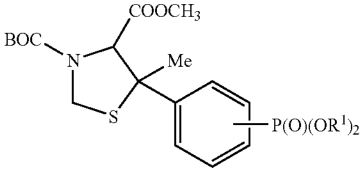

100.2

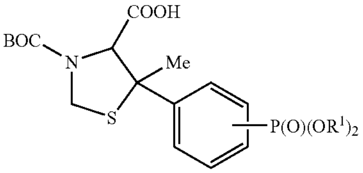

100.3

Example

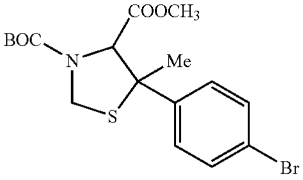

100.4

$HP(O)(OR^1)_2$ 100.1

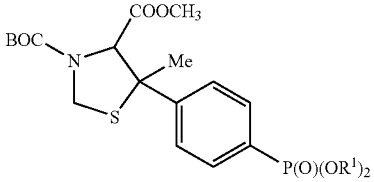

100.5

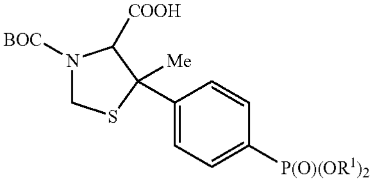

100.6

Scheme 101

Method

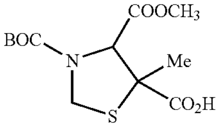

98.18

$H_2N(CH_2)_nP(O)(OR^1)_2$ 101.1

-continued

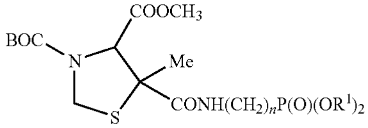

101.2

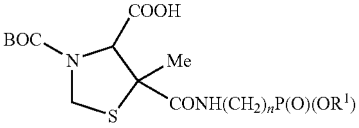

101.3

Example

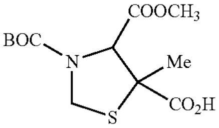

98.18

$H_2N(CH_2)_3P(O)(OR^1)_2$ 101.1

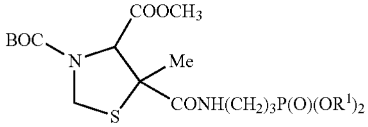

101.5

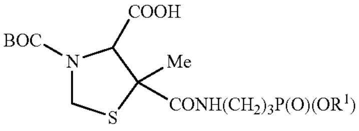

101.6

Preparation of Carbamates.

The phosphonate esters 5-12 in which the $R^8CO$ groups are formally derived from the carboxylic acids C38-C49 (Chart 2c) contain a carbamate linkage. The preparation of carbamates is described in Comprehensive Organic Functional Group Transformations, A. R. Katritzky, ed., Pergamon, 1995, Vol. 6, p. 416ff, and in Organic Functional Group Preparations, by S. R. Sandler and W. Karo, Academic Press, 1986, p. 260ff.

Scheme 102 illustrates various methods by which the carbamate linkage can be synthesized. As shown in Scheme 102, in the general reaction generating carbamates, a carbinol 102.1, is converted into the activated derivative 102.2 in which Lv is a leaving group such as halo, imidazolyl, benztriazolyl and the like, as described herein. The activated derivative 102.2 is then reacted with an amine 102.3, to afford the carbamate product 102.4. Examples 1-7 in Scheme 102 depict methods by which the general reaction can be effected. Examples 8-10 illustrate alternative methods for the preparation of carbamates.

Scheme 102, Example 1 illustrates the preparation of carbamates employing a chloroformyl derivative of the carbinol 102.5. In this procedure, the carbinol 102.5 is reacted with phosgene, in an inert solvent such as toluene, at about 0°, as described in Org. Syn. Coll. Vol. 3, 167, 1965, or with an equivalent reagent such as trichloromethoxy chloroformate, as described in Org. Syn. Coll. Vol. 6, 715, 1988, to afford the chloroformate 102.6. The latter compound is then reacted with the amine component 102.3, in the presence of an organic or inorganic base, to afford the carbamate 102.7. For example, the chloroformyl compound 102.6 is reacted with the amine 102.3 in a water-miscible solvent such as tetrahydrofuran, in the presence of aqueous sodium hydroxide, as described in Org. Syn. Coll. Vol. 3, 167, 1965, to yield the carbamate 102.7. Alternatively, the reaction is performed in dichloromethane in the presence of an organic base such as diisopropylethylamine or dimethylaminopyridine.

Scheme 102, Example 2 depicts the reaction of the chloroformate compound 102.6 with imidazole to produce the imidazolide 102.8. The imidazolide product is then reacted with the amine 102.3 to yield the carbamate 102.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in J. Med. Chem., 1989, 32, 357.

Scheme 102 Example 3, depicts the reaction of the chloroformate 102.6 with an activated hydroxyl compound R"OH, to yield the mixed carbonate ester 102.10. The reaction is conducted in an inert organic solvent such as ether or dichloromethane, in the presence of a base such as dicyclohexylamine or triethylamine. The hydroxyl component R"OH is selected from the group of compounds 102.19-102.24 shown in Scheme 102, and similar compounds. For example, if the component R"OH is hydroxybenztriazole 102.19, N-hydroxysuccinimide 102.20, or pentachlorophenol, 102.21, the mixed carbonate 102.10 is obtained by the reaction of the chloroformate with the hydroxyl compound in an ethereal solvent in the presence of dicyclohexylamine, as described in Can. J. Chem., 1982, 60, 976. A similar reaction in which the component R"OH is pentafluorophenol 102.22 or 2-hydroxypyridine 102.23 can be performed in an ethereal solvent in the presence of triethylamine, as described in Syn., 1986, 303, and Chem. Ber. 118, 468, 1985.

Scheme 102 Example 4 illustrates the preparation of carbamates in which an alkyloxycarbonylimidazole 102.8 is employed. In this procedure, a carbinol 102.5 is reacted with an equimolar amount of carbonyl diimidazole 102.11 to prepare the intermediate 102.8. The reaction is conducted in an aprotic organic solvent such as dichloromethane or tetrahydrofuran. The acyloxyimidazole 102.8 is then reacted with an equimolar amount of the amine $R'NH_2$ to afford the carbamate 102.7. The reaction is performed in an aprotic organic solvent such as dichloromethane, as described in Tet. Lett., 42, 2001, 5227, to afford the carbamate 102.7.

Scheme 102, Example 5 illustrates the preparation of carbamates by means of an intermediate alkoxycarbonylbenztriazole 102.13. In this procedure, a carbinol ROH is reacted at ambient temperature with an equimolar amount of benztriazole carbonyl chloride 102.12, to afford the alkoxycarbonyl product 102.13. The reaction is performed in an organic solvent such as benzene or toluene, in the presence of a tertiary organic amine such as triethylamine, as described in Syn., 1977, 704. The product is then reacted with the amine $R'NH_2$ to afford the carbamate 102.7. The reaction is conducted in toluene or ethanol, at from ambient temperature to about 80° as described in Syn., 1977, 704.

Scheme 102, Example 6 illustrates the preparation of carbamates in which a carbonate $(R''O)_2CO$, 102.14, is reacted with a carbinol 102.5 to afford the intermediate alkyloxycarbonyl intermediate 102.15. The latter reagent is then reacted with the amine $R'NH_2$ to afford the carbamate 102.7. The procedure in which the reagent 102.15 is derived from hydroxybenztriazole 102.19 is described in Synthesis, 1993, 908; the procedure in which the reagent 102.15 is derived from N-hydroxysuccinimide 102.20 is described in Tet. Lett., 1992, 2781; the procedure in which the reagent 102.15 is derived from 2-hydroxypyridine 102.23 is described in Tet. Lett., 1991, 4251; the procedure in which the reagent 102.15 is derived from 4-nitrophenol 102.24 is described in Syn. 1993, 103. The reaction between equimolar amounts of the carbinol ROH and the carbonate 102.14 is conducted in an inert organic solvent at ambient temperature.

Scheme 102, Example 7 illustrates the preparation of carbamates from alkoxycarbonyl azides 102.16. In this procedure, an alkyl chloroformate 102.6 is reacted with an azide, for example sodium azide, to afford the alkoxycarbonyl azide 102.16. The latter compound is then reacted with an equimolar amount of the amine $R'NH_2$ to afford the carbamate 102.7. The reaction is conducted at ambient temperature in a polar aprotic solvent such as dimethylsulfoxide, for example as described in Syn., 1982, 404.

Scheme 102, Example 8 illustrates the preparation of carbamates by means of the reaction between a carbinol ROH and the chloroformyl derivative of an amine 102.17. In this procedure, which is described in Synthetic Organic Chemistry, R. B. Wagner, H. D. Zook, Wiley, 1953, p. 647, the reactants are combined at ambient temperature in an aprotic solvent such as acetonitrile, in the presence of a base such as triethylamine, to afford the carbamate 102.7.

Scheme 102, Example 9 illustrates the preparation of carbamates by means of the reaction between a carbinol ROH and an isocyanate 102.18. In this procedure, which is described in Synthetic Organic Chemistry, R. B. Wagner, H. D. Zook, Wiley, 1953, p. 645, the reactants are combined at ambient temperature in an aprotic solvent such as ether or dichloromethane and the like, to afford the carbamate 102.7.

Scheme 102, Example 10 illustrates the preparation of carbamates by means of the reaction between a carbinol ROH and an amine $R'NH_2$. In this procedure, which is described in Chem. Lett. 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate 102.7.

Interconversions of the Phosphonates R-link-$P(O)(OR^1)_2$, R-link-$P(O)(OR^1)(OH)$ and R-link-$P(O)(OH)_2$.

Schemes 1-102 described the preparations of phosphonate esters of the general structure R-link-$P(O)(OR^1)_2$, in which the groups $R^1$, the structures of which are defined in Chart 1, may be the same or different. The $R^1$ groups attached to a phosphonate esters 1-12, or to precursors thereto, may be changed using established chemical transformations. The interconversions reactions of phosphonates are illustrated in Scheme 103. The group R in Scheme 103 represents the substructure to which the substituent link-$P(O)(OR^1)_2$ is attached, either in the compounds 1-12 or in precursors thereto. The $R^1$ group may be changed, using the procedures described below, either in the precursor compounds, or in the esters 1-12. The methods employed for a given phosphonate transformation depend on the nature of the substituent $R^1$. The preparation and hydrolysis of phosphonate esters is described in Organic Phosphorus Compounds, G. M. Kosolapoff, L. Maeir, eds, Wiley, 1976, p. 9ff.

The conversion of a phosphonate diester 103.1 into the corresponding phosphonate monoester 103.2 (Scheme 103, Reaction 1) can be accomplished by a number of methods. For example, the ester 103.1 in which $R^1$ is an aralkyl group such as benzyl, can be converted into the monoester compound 103.2 by reaction with a tertiary organic base such as diazabicyclooctane (DABCO) or quinuclidine, as described in J. Org. Chem., 1995, 60, 2946. The reaction is performed in an inert hydrocarbon solvent such as toluene or xylene, at about 110°. The conversion of the diester 103.1 in which $R^1$ is an aryl group such as phenyl, or an alkenyl group such as allyl, into the monoester 103.2 can be effected by treatment of the ester 103.1 with a base such as aqueous sodium hydroxide in acetonitrile or lithium hydroxide in aqueous tetrahydrofuran. Phosphonate diesters 103.1 in which one of the groups $R^1$ is aralkyl, such as benzyl, and the other is alkyl, can be converted into the monoesters 103.2 in which $R^1$ is alkyl by hydrogenation, for example using a palladium on carbon catalyst. Phosphonate diesters in which both of the groups $R^1$ are alkenyl, such as allyl, can be converted into the monoester 103.2 in which $R^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in J. Org. Chem., 38, 3224, 1973 for the cleavage of allyl carboxylates.

The conversion of a phosphonate diester 103.1 or a phosphonate monoester 103.2 into the corresponding phosphonic acid 103.3 (Scheme 103, Reactions 2 and 3) can effected by reaction of the diester or the monoester with trimethylsilyl bromide, as described in J. Chem. Soc., Chem. Comm., 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 103.2 in which $R^1$ is aralkyl such as benzyl, can be converted into the corresponding phosphonic acid 103.3 by hydrogenation over a palladium catalyst, or by treatment with hydrogen chloride in an ethereal solvent such as dioxan. A phosphonate monoester 103.2 in which $R^1$ is alkenyl such as, for example, allyl, can be converted into the phosphonic acid 103.3 by reaction with Wilkinson's catalyst in an aqueous organic solvent, for example in 15% aqueous acetonitrile, or in aqueous ethanol, for example using the procedure described in Helv. Chim. Acta., 68, 618, 1985. Palladium catalyzed hydrogenolysis of phosphonate esters 103.1 in which $R^1$ is benzyl is described in J. Org. Chem., 24, 434, 1959. Platinum-catalyzed hydrogenolysis of phosphonate esters 103.1 in which $R^1$ is phenyl is described in J. Am. Chem. Soc., 78, 2336, 1956.

The conversion of a phosphonate monoester 103.2 into a phosphonate diester 103.1 (Scheme 103, Reaction 4) in which the newly introduced $R^1$ group is alkyl, aralkyl, haloalkyl such as chloroethyl, or aralkyl can be effected by a number of reactions in which the substrate 103.2 is reacted with a hydroxy compound $R^1OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 103.2 to the diester 103.1 can be effected by the use of the Mitsonobu reaction, as described above (Scheme 47). The substrate is reacted with the hydroxy compound $R^1OH$, in the presence of diethyl azodicarboxylate and a triarylphosphine such as triphenyl phosphine. Alternatively, the phosphonate monoester 103.2 can be transformed into the phosphonate diester 103.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 103.2 is transformed into the chloro analog RP(O)$(OR^1)$Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product RP(O)$(OR^1)$Cl is then reacted with the hydroxy compound $R^1$ OH, in the presence of a base such as triethylamine, to afford the phosphonate diester 103.1.

A phosphonic acid R-link-P(O)$(OH)_2$ can be transformed into a phosphonate monoester RP(O)$(OR^1)$(OH) (Scheme 103, Reaction 5) by means of the methods described above of for the preparation of the phosphonate diester R-link-P(O)$(OR^1)_2$ 103.1, except that only one molar proportion of the component $R^1OH$ or $R^1Br$ is employed.

A phosphonic acid R-link-P(O)$(OH)_2$ 103.3 can be transformed into a phosphonate diester R-link-P(O)$(OR^1)_2$ 103.1 (Scheme 103, Reaction 6) by a coupling reaction with the hydroxy compound $R^1$ OH, in the presence of a coupling agent such as Aldrithiol-2 (Aldrich) and triphenylphosphine. The reaction is conducted in a basic solvent such as pyridine.

Alternatively, phosphonic acids 103.3 can be transformed into phosphonic esters 103.1 in which $R^1$ is aryl, by means of a coupling reaction employing, for example, dicyclohexylcarbodiimide in pyridine at ca 70°. Alternatively, phosphonic acids 103.3 can be transformed into phosphonic esters 103.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester 103.1.

Scheme 102

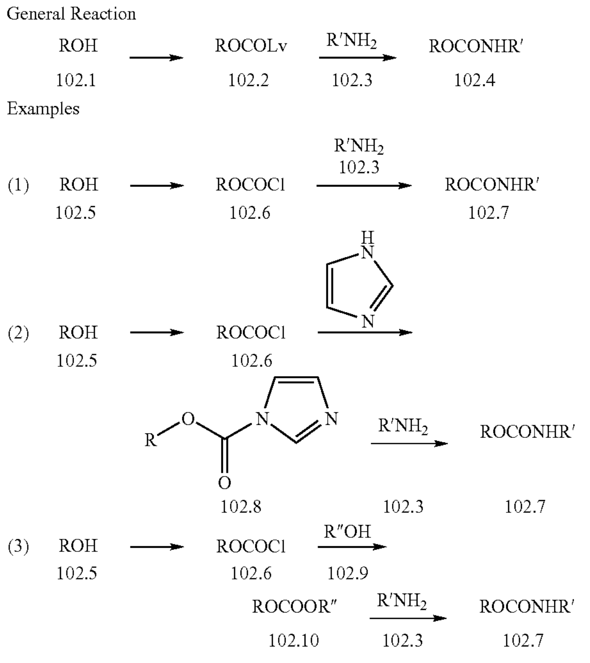

-continued

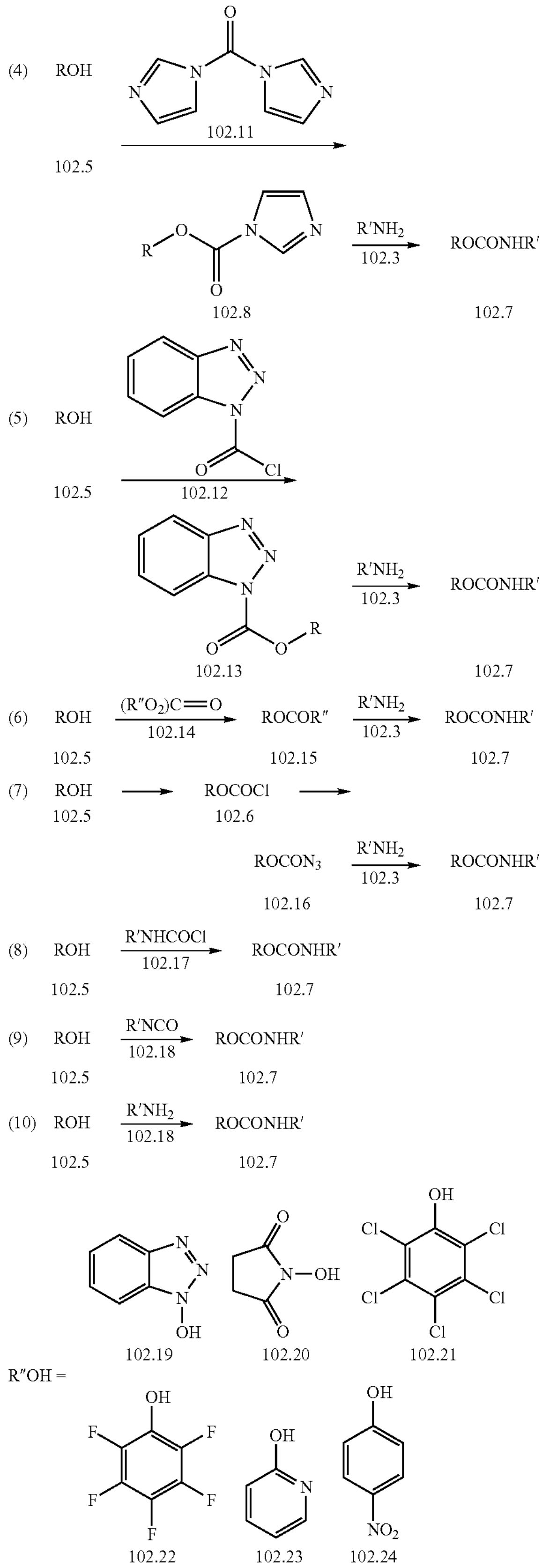

Scheme 103

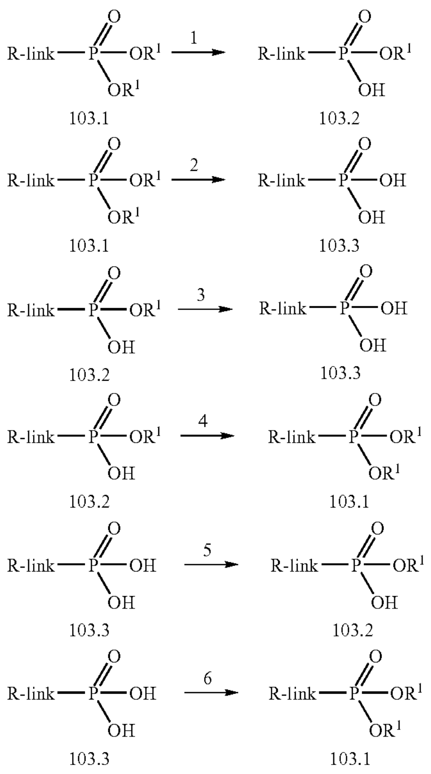

General Applicability of Methods for Introduction of Phosphonate Substituents.

The procedures described herein for the introduction of phosphonate moieties (Schemes 45-101) are, with appropriate modifications known to one skilled in the art, transferable to different chemical substrates. Thus, the methods described above for the introduction of phosphonate groups into hydroxymethyl benzoic acids (Schemes 45-52) are applicable to the introduction of phosphonate moieties into the dimethoxyphenol, quinoline, phenylalanine, thiophenol, tert. butylamine, benzylamine, decahydroisoquinoline or thiazolidine substrates, and the methods described herein for the introduction of phosphonate moieties into the dimethoxyphenol, quinoline, phenylalanine, thiophenol, tert. butylamine, benzylamine, decahydroisoquinoline or thiazolidine substrates, (Schemes 53-101) are applicable to the introduction of phosphonate moieties into carbinol substrates.

Preparation of Phosphonate Intermediates 11 and 12 with Phosphonate Moieties Incorporated into the Groups $R^8CO$ and $R^{10}R^{11}N$.

The chemical transformations described in Schemes 1-103 illustrate the preparation of compounds 1-10 in which the phosphonate ester moiety is attached to the benzoic acid moiety, (Schemes 46-52), the dimethylphenol moiety (Schemes 53-56), the quinoline carboxamide moiety (Schemes 57-61), the 5-hydroxyisoquinoline moiety (Schemes 62-66), the phenylalanine moiety (Schemes 67-71), the thiophenol moiety, (Schemes 72-83), the tert. butylamine moiety, (Schemes 84-87), the benzylamine moiety, (Schemes 88-90), the decahydroisoquinoline moiety, (Schemes 91-97) or the thiazolidine moiety, (Schemes 98-101). The various chemical methods employed for the preparation of phosphonate groups can, with appropriate modifications known to those skilled in the art, be applied to the introduction of a phosphonate ester group into the compounds $R^8COOH$ and $R^{10}R^{11}NH$, as defined in Charts 3a, 3b, 3c and 4. The resultant phosphonate-containing analogs, designated as $R^{8a}COOH$ and $R^{10a}R^{11a}NH$ can then, using the procedures described above, be employed in the preparation of the compounds 11 and 12. The procedures required for the utilization of the phosphonate-containing analogs $R^{8a}COOH$ and $R^{10a}R^{11a}NH$ are the same as those described above for the utilization of the $R^8COOH$ and $R^{10}R^{11}NH$ reactants.

Cyclic Carbonyl Phosphonate Protease Inhibitors (CCPPI)

Scheme Section B

Schemes 1 and 2 are described below in the Examples.

Scheme 1

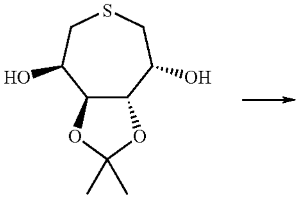

1

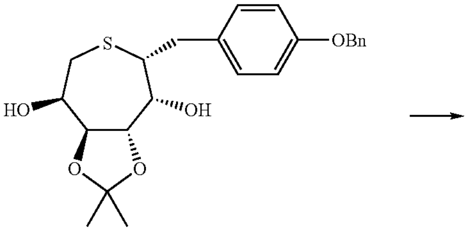

2

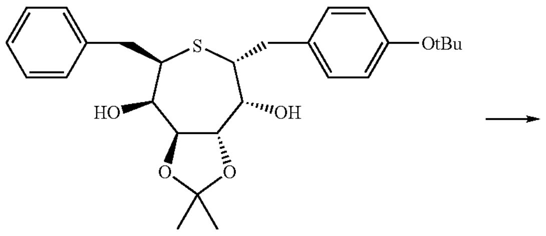

3

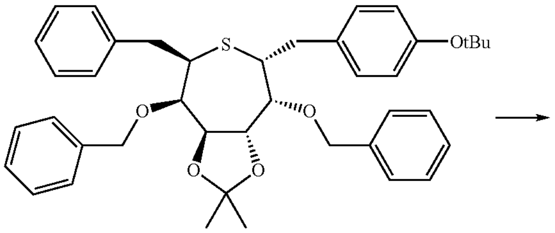

4

-continued

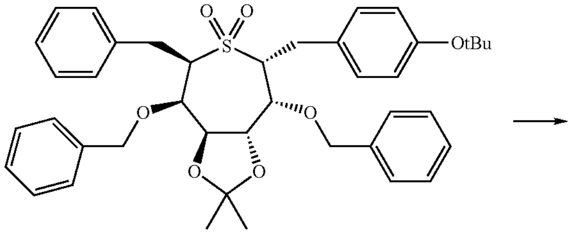

5

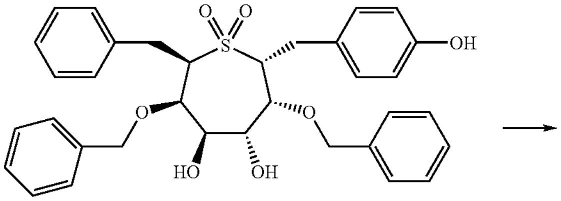

6

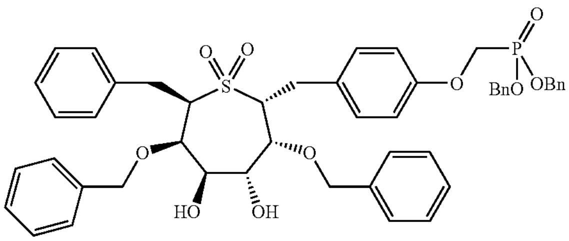

7

Scheme 2

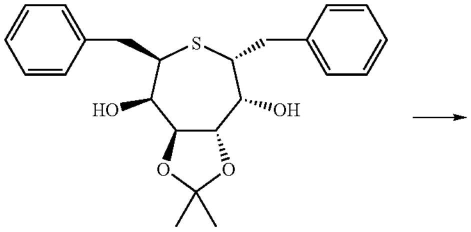

8

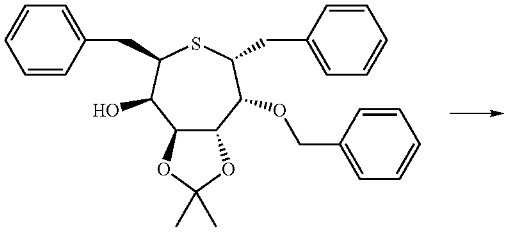

9

-continued

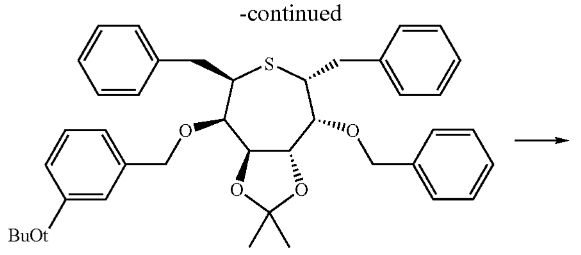

10

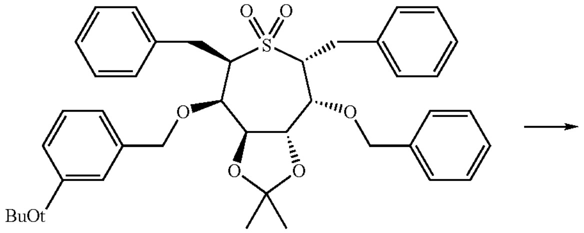

11

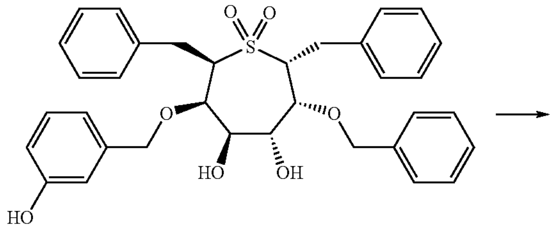

12

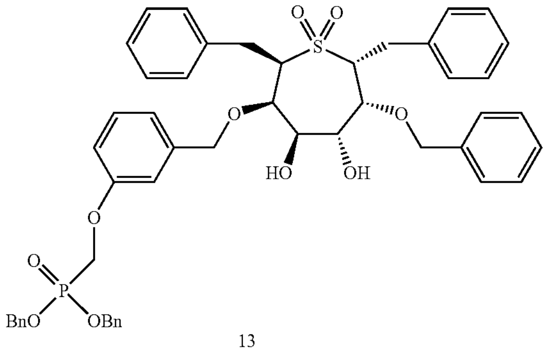

13

Example Section B

Example 1

Scheme 1: Example, [4-(7-Benzyl-3,6-bis-benzyloxy-4,5-dihydroxy-1,1-dioxo-116-thiepan-2-ylmethyl)-phenoxymethyl]-phosphonic acid dibenzyl ester (7)

The cyclic sulfide 1 is prepared according to the procedures reported by Kim et al. (J. Med. Chem. 1996, 39, 3431-3434) and Bischofberger (WO96/14314, Gilead Sciences). Treatment of the sulfide 1 with 4-benzyloxybenzaldehyde affords the benzyl ether 2 (J. Med. Chem. 1996, 39, 3431-3434). A second alkylation with benzaldehyde gives 3 which is subsequently treated with excess benzylbromide to afford the full substituted product 4. Ozone is used to covert the sulfide to the sulfone 5 (J. Med. Chem. 1996, 39, 3431-3434). Sulfone 5 is treated with TFA to give the phenol 6 which upon alkyaltion with trifluoro-methanesulfonic acid bis-benzyloxy-phosphorylmethyl ester in the presence of base (e.g. cesium carbonate) gives the dibenzyl phosphonate 7.

The meta analog, [3-(7-Benzyl-3,6-bis-benzyloxy-4,5-dihydroxy-1,1-dioxo-116-thiepan-2-ylmethyl)-phenoxymethyl]-phosphonic acid dibenzyl ester and ortho analog, [2-(7-Benzyl-3,6-bis-benzyloxy-4,5-dihydroxy-1,1-dioxo-116-thiepan-2-ylmethyl)-phenoxymethyl]-phosphonic acid dibenzyl ester are prepared using Scheme 1 except 4-benzyloxybenzaldehyde is replaced with 3-benzyloxybenzaldehyde and 2-benzyloxybenzaldehyde respectively.

Example 2

Scheme 2: Example, [3-(2,7-Dibenzyl-6-benzyloxy-4,5-dihydroxy-1,1-dioxo-116-thiepan-3-yloxymethyl)-phenoxymethyl]-phosphonic acid dibenzyl ester (13).

The sulfide 8 is prepared according to the procedure of Kim et al. (J. Med. Chem. 1996, 39, 3431-3434) and is then treated with benzyl bromide in the presence of sodium hydride to give the benzyl ether 9. A second treatment with 3-t-butyloxybenzylchloride in the presence of sodium hydride affords the benzyl ether 10. Ozone treatment of the benzyl ether 10 gives the sulfone 11. (J. Med. Chem. 1996, 39, 3431-3434) which is then treated with TFA to give the phenol 12 (Green). Phenol 12 is treated with trifluoro-methanesulfonic acid bis-benzyloxy-phosphorylmethyl benzyloxy-phosphorylmethyl ester in the presence of base (e.g. cesium carbonate) to give the dibenzyl phosphonate 13.

The para analog, [3-(2,7-Dibenzyl-6-benzyloxy-4,5-dihydroxy-1,1-dioxo-116-thiepan-3-yloxymethyl)-phenoxymethyl]-phosphonic acid dibenzyl ester, and ortho analog, [3-(2,7-Dibenzyl-6-benzyloxy-4,5-dihydroxy-1,1-dioxo-116-thiepan-3-yloxymethyl)-phenoxymethyl]-phosphonic acid dibenzyl ester, are prepared using the same procedures found in Scheme 2 except utilizing the 4-t-butyloxybenzylchloride and 2-t-butyloxybenzylchloride instead of 3-t-butyloxybenzylchloride. The benzylchlorides are prepared from the corresponding commercially available benzylalcohols by treatment with thionyl chloride (*Jour. Chem. Soc.* (1956), 2455-2461).

Scheme Section C

Schemes 1-4 are described in the Examples.

Scheme 1

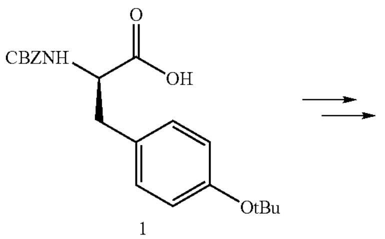

1

-continued
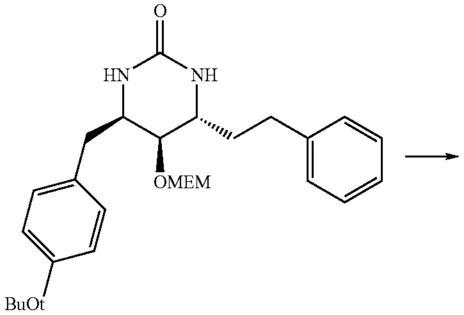
2
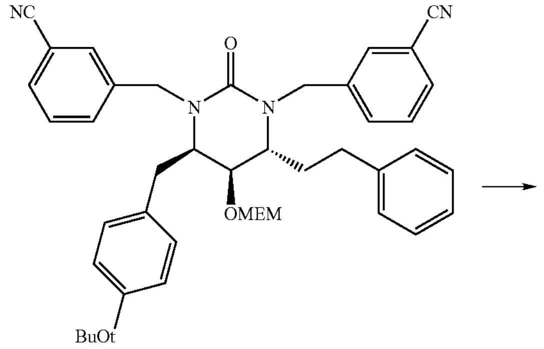
3
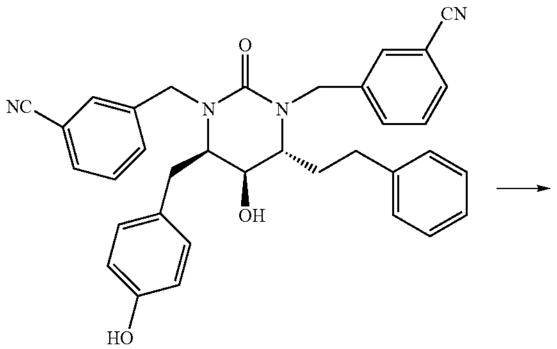
4
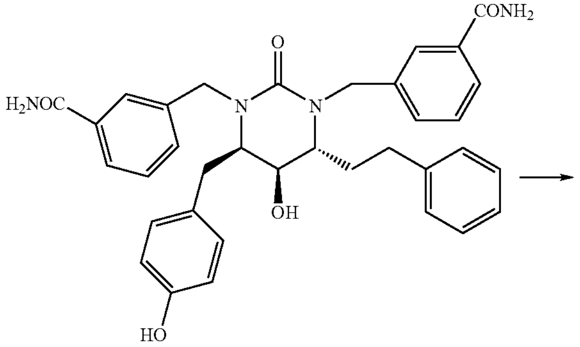
5
-continued
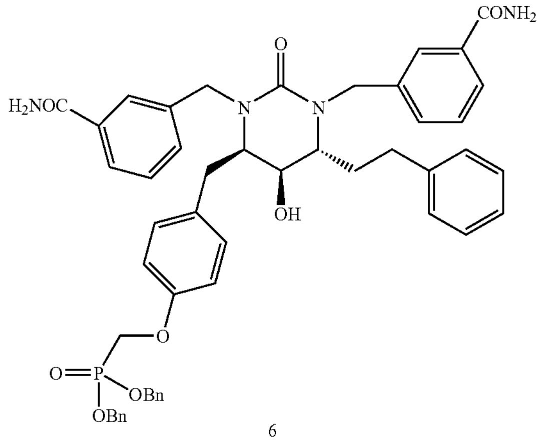
6
Scheme 2
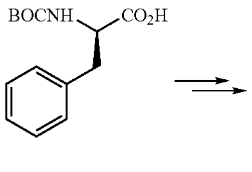
7
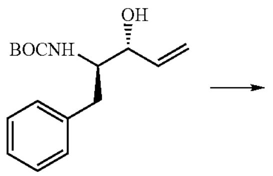
8
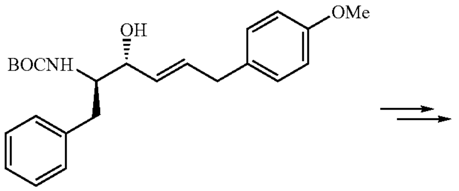
9
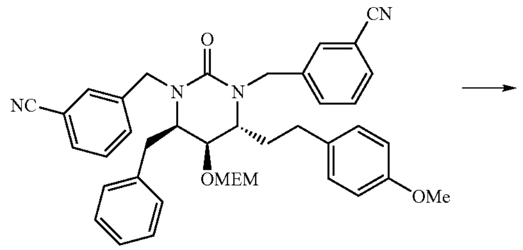
10
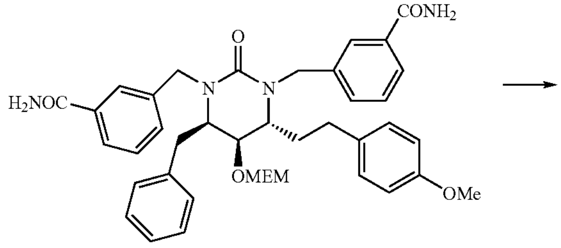
11

-continued
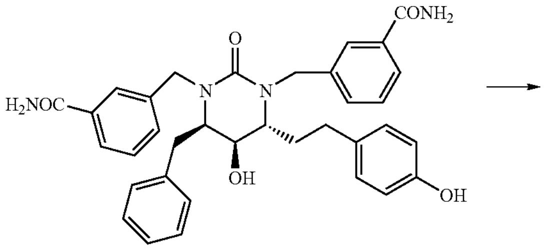
12
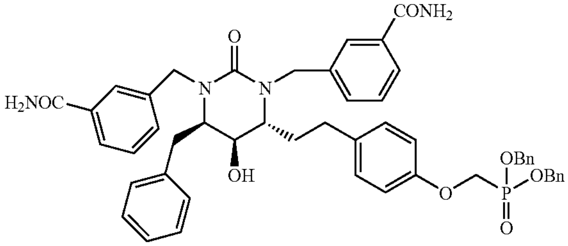
13
Scheme 3
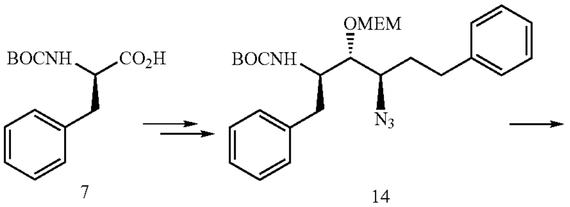
7
14
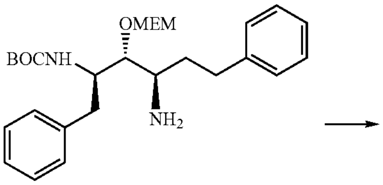
15
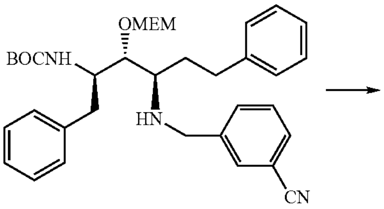
16
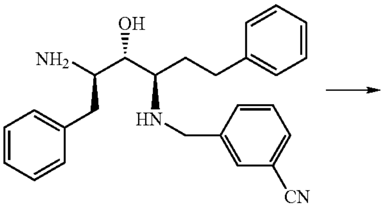
17
-continued
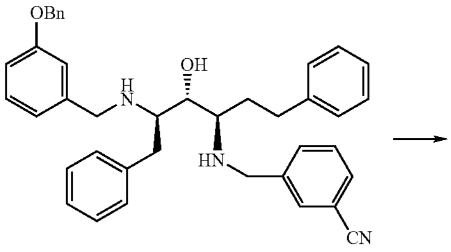
18
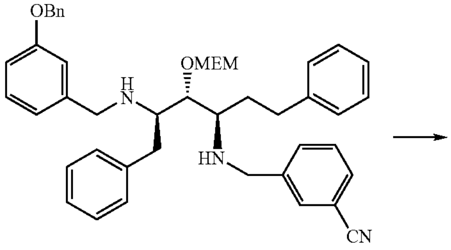
19
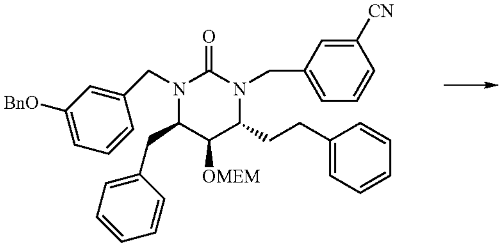
20
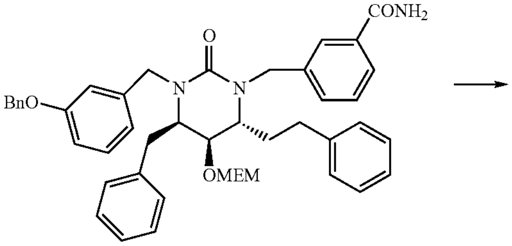
21
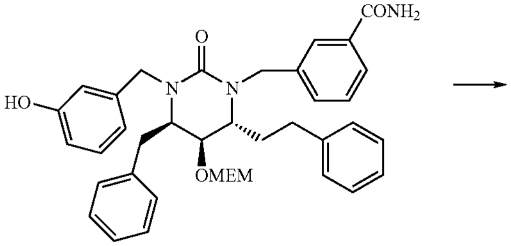
22

-continued
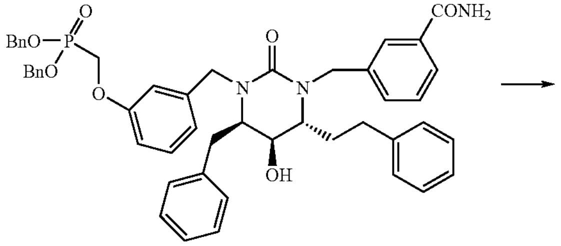
23
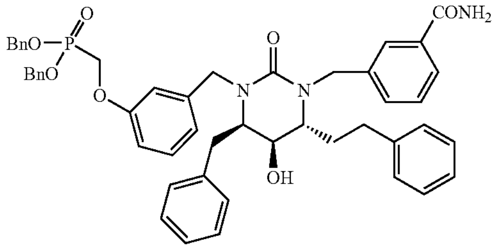
24
Scheme 4
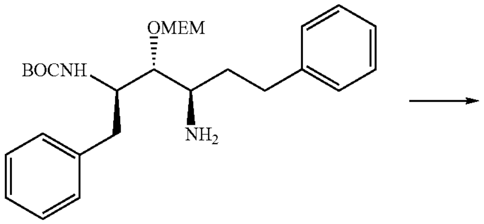
15
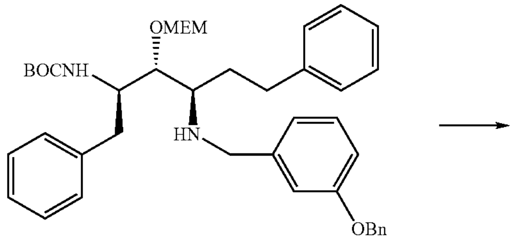
25
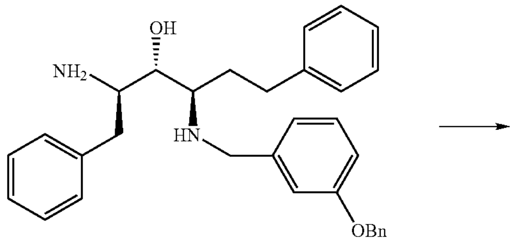
26
-continued
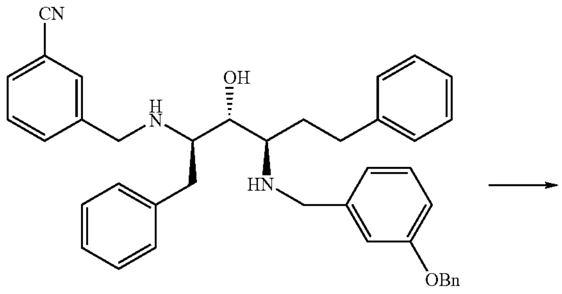
27
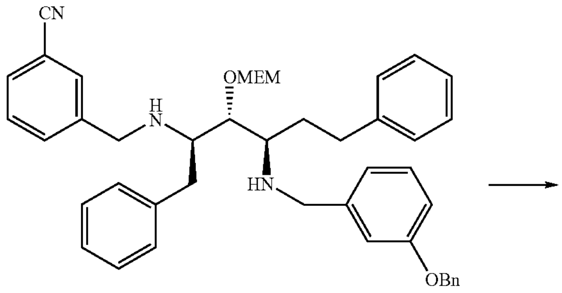
28
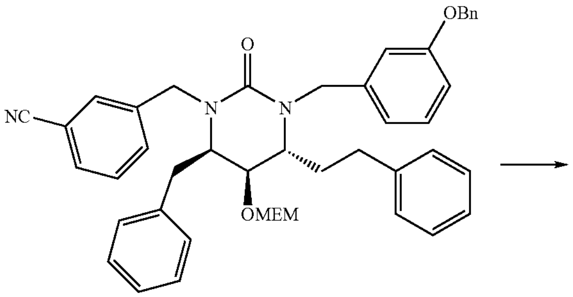
29
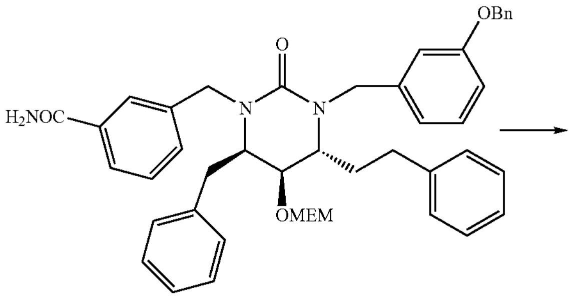
30

-continued

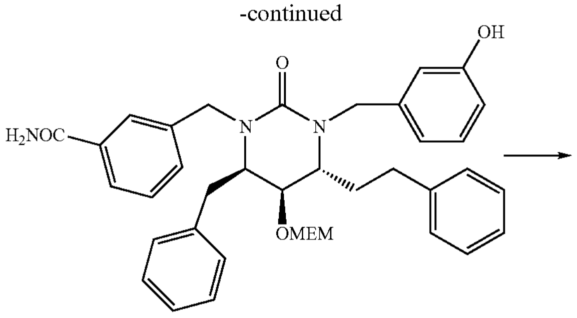

31

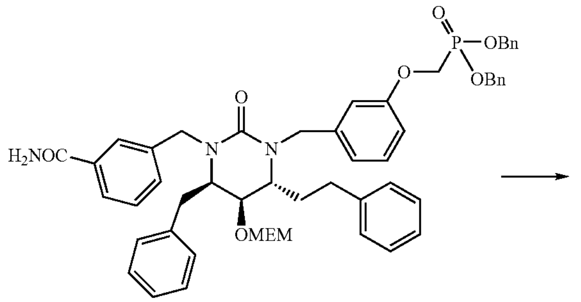

32

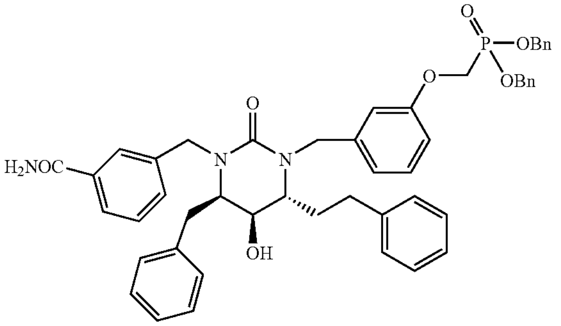

33

Example Section C

Example 1

Scheme 1: Example, {4-[1,3-Bis-(3-carbamoyl-benzyl)-5-hydroxy-2-oxo-6-phenethyl-hexahydro-pyrimidin-4-ylmethyl]-phenoxymethyl}-phosphonic acid dibenzyl ester (6)

Commercially available Z-D-Tyr(TBU)-OH 1 is converted to the tetrahydropyrimidine 2 using the same procedures reported by De Lucca for conversion of Z-Phe into the analogous tetrahydropyrimidinone (J. Med. Chem. 1997, 40, 1707-1719). Bis-alkylation by treatment with excess m-cyanobenzylbromide affords the disubstituted urea 3 (J. Med. Chem. 1997, 40, 1707-1719). Removal of the MEM group and the t-butyl ether using standard conditions e.g. TFA (Green) affords the diol 4. Treatment of the diol 4 with hydrogen peroxide in DMSO affords the carboxamide 5. Alkyation of 5 with trifluoro-methanesulfonic acid bis-benzyloxy-phosphorylmethyl ester in the presence of base (e.g. cesium carbonate) affords the dibenzyl phosphonate 6.

The meta analog, {3-[1,3-Bis-(3-carbamoyl-benzyl)-5-hydroxy-2-oxo-6-phenethyl-hexahydro-pyrimidin-4-ylmethyl]-phenoxymethyl}-phosphonic acid dibenzyl ester and para analog, {2-[1,3-Bis-(3-carbamoyl-benzyl)-5-hydroxy-2-oxo-6-phenethyl-hexahydro-pyrimidin-4-ylmethyl]-phenoxymethyl}-phosphonic acid dibenzyl ester are prepared using Scheme 1 except substituting Z-D-m-Tyr(TBU)-OH and Z-D-o-Tyr(TBU)-OH for Z-D-Tyr(TBU)-OH respectively. The Z-D-m-Tyr(TBU)-OH and Z-D-o-Tyr(TBU)-OH amino acids are prepared from the unprotecetd amino acids. Thus, D-m-Tyr-OH and D-o-Tyr-OH (see Abbott scheme 1) are treated with dibenzyl dicarbonate in the presence of base e.g. triethylamine to afford the Z-D-m-Tyr-OH and Z-D-o-Tyr-OH protected amino acids respectively. Further treatment of Z-D-m-Tyr-OH and Z-D-o-Tyr-OH with t-butyl chloride in the presence of base e.g. pyridine affords the Z-D-m-Tyr(TBU)-OH and Z-D-o-Tyr(TBU)-OH amino acids respectively (Green).

Example 2

Scheme 2: Example, (4-{2-[6-Benzyl-1,3-bis-(3-carbamoyl-benzyl)-5-(2-methoxyethoxy-methoxy)-2-oxo-hexahydro-pyrimidin-4-yl]-ethyl}-phenoxymethyl)-phosphonic Acid Dibenzyl Ester (13)

Boc-Phe 7 is converted to the allylic alcohol 8 using the same procedures reported by De Lucca et al. for the conversion of Z-Phe to the corresponding Z-allylic alcohol (J. Med. Chem. 1997, 40, 1707-1719). The allylic alcohol 8 is reacted with 4-methoxybenzylmagnesium chloride to afford the alkene 9 (J. Med. Chem. 1997, 40, 1707-1719). The 4-methoxybenzylmagnesium chloride is prepared from 4-methoxybenzylchloride according to the procedure of Van Campen et al. (J. Amer. Chem. Soc. 1948, 70 p2296). The alkene 9 is converted to the tetrahydropyrimidinone 10 using the same series of procedures reported by De Lucca et al. (J. Med. Chem. 1997, 40, 1707-1719). Treatment of the nitrile 10 with hydrogen peroxide in DMSO affords the carboxamide 11 (Synthesis, 1989, 949-950). The carboxamide 11 is treated with trimethylsilylbromide to form the phenol 12 (Green) which is then alkylated with trifluoro-methanesulfonic acid bis-benzyloxy-phosphorylmethyl ester in the presence of base (e.g. cesium carbonate) to yield the dibenzyl phosphonate 13.

The ortho, (2-{2-[6-Benzyl-1,3-bis-(3-carbamoyl-benzyl)-5-(2-methoxy-ethoxymethoxy)-2-oxo-hexahydro-pyrimidin-4-yl]-ethyl}-phenoxymethyl)-phosphonic acid dibenzyl ester and meta, (3-{2-[6-Benzyl-1,3-bis-(3-carbamoyl-benzyl)-5-(2-methoxy-ethoxymethoxy)-2-oxo-hexahydro-pyrimidin-4-yl]-ethyl}-phenoxymethyl)-phosphonic acid dibenzyl ester analogs, are prepared using the same procedures reported in Scheme 2 except 4-methoxybenzylmagnesium chloride is replaced with 2-methoxybenzylmagnesium chloride and 3-methoxybenzylmagnesium chloride respectively. The grignard reagents are prepared from commercially available benzyl chlorides using the procedure of Van Campen et al. (J. Amer. Chem. Soc. 1948, 70 p2296).

Example 3

Scheme 3: Example, {3-[6-Benzyl-3-(3-carbamoyl-benzyl)-5-hydroxy-2-oxo-4-phenethyl-tetrahydro-pyrimidin-1-ylmethyl]-phenoxymethyl}-phosphonic acid dibenzyl ester (24).

Boc-Phe 7 is converted into the azide 14 using the same procedures reported by De Lucca et al. for the conversion of CBZ-Phe into the analogous CBZ azide (J. Med. Chem. 1997, 40, 1707-1719). Catalytic hydrogenolysis of the azide affords the amine 15 (J. Med. Chem. 1997, 40, 1707-1719). Reductive amination of the amine with 3-cyanobenzaldehyde (U.S. Pat. No. 6,313,110) affords the secondary amine 16. Treatment with 4N HCl affords the primary amine 17 (Green). Reductive amination with 3-benzyloxybenzadehyde affords the benzyl ether 18 (U.S. Pat. No. 6,313,110). Treatment of the benzyl ether 18 with MEM-chloride in the presence of base (e.g. DIEA) forms the MEM protected product 19 (J. Med. Chem. 1997, 40, 1707-1719). Treatment of diamine 19 with CDI affords the tetrahydropyrimldinone 20. Treatment of the nitrile 20 with DMSO and hydrogen peroxide (Synthesis 1989, 949-950) affords the carboxamide 21. Catalytic hydrogenolysis affords the phenol 22 (Green) which is then alkylated with trifluoro-methanesulfonic acid bis-benzyloxy-phosphorylmethyl ester in the presence of base (e.g. cesium carbonate) to yield the dibenzyl phosphonate 23. Removal of the MEM group using trifluoroacetic acid affords the product 24 (Green).

The ortho {2-[6-Benzyl-3-(3-carbamoyl-benzyl)-5-hydroxy-2-oxo-4-phenethyl-tetrahydro-pyrimidin-1-ylmethyl]-phenoxymethyl}-phosphonic acid dibenzyl ester. and para, {4-[6-Benzyl-3-(3-carbamoyl-benzyl)-5-hydroxy-2-oxo-4-phenethyl-tetrahydro-pyrimidin-1-ylmethyl]-phenoxymethyl}-phosphonic acid dibenzyl ester are prepared using the same procedures reported in Scheme 3 except substituting 3-benzyloxybenzaldehyde with 2-benzyloxybenzaldehyde and 4-benzyloxybenzaldehyde respectively.

Example 4

Scheme 4: Example, {3-[4-Benzyl-3-(3-carbamoyl-benzyl)-5-hydroxy-2-oxo-6-phenethyl-tetrahydro-pyrimidin-1-ylmethyl]-phenoxymethyl}-phosphonic acid dibenzyl ester (33) The amine 15 (Scheme 3) is transformed to the secondary amine 25 through reductive amination with 3-benzyloxybenzadehyde. (U.S. Pat. No. 6,313,110). Treatment of BOC-amine 25 with trifluoroacetic acid releases the primary amine 26 (Green) which is then subjected to a second reductive amination with 3-cyanobenzaldehyde to afford the bis-substituted amine 27 (U.S. Pat. No. 6,313,110). Treatment of the benzyl ether 27 with MEM-chloride in the presence of base (e.g. DIEA) forms the MEM protected product 28 (J. Med. Chem. 1997, 40, 1707-1719). Treatment of diamine 28 with CDI affords the tetrahydropyrimidinone 29. Treatment of the nitrile 29 with DMSO and hydrogen peroxide (Synthesis 1989, 949-950) affords the carboxamide 30. Catalytic hydrogenolysis affords the phenol 31 (Green) which is then alkylated with trifluoro-methanesulfonic acid bis-benzyloxy-phosphorylmethyl ester in the presence of base (e.g. cesium carbonate) to yield the dibenzyl phosphonate 32. Removal of the MEM group using trifluoroacetic acid affords the product 33 (Green).

Example 5

Ortho analog, {2-[4-Benzyl-3-(3-carbamoyl-benzyl)-5-hydroxy-2-oxo-6-phenethyl-tetrahydro-pyri -Benzyl-3-(3-carbamoyl-benzyl)-5-hydroxy-2-oxo-6-phenethyl-tetrahydro-pyrimidin-1-ylmethyl]-phenoxymethyl}-phosphonic acid dibenzyl ester are prepared using Scheme 4 except replacing 3-benzyloxybenzadehyde with 2-benzyloxybenzadehyde and 4-benzyloxybenzadehydes respectively.

Scheme Section D

Schemes 1-6 are described in the examples.

Scheme 1

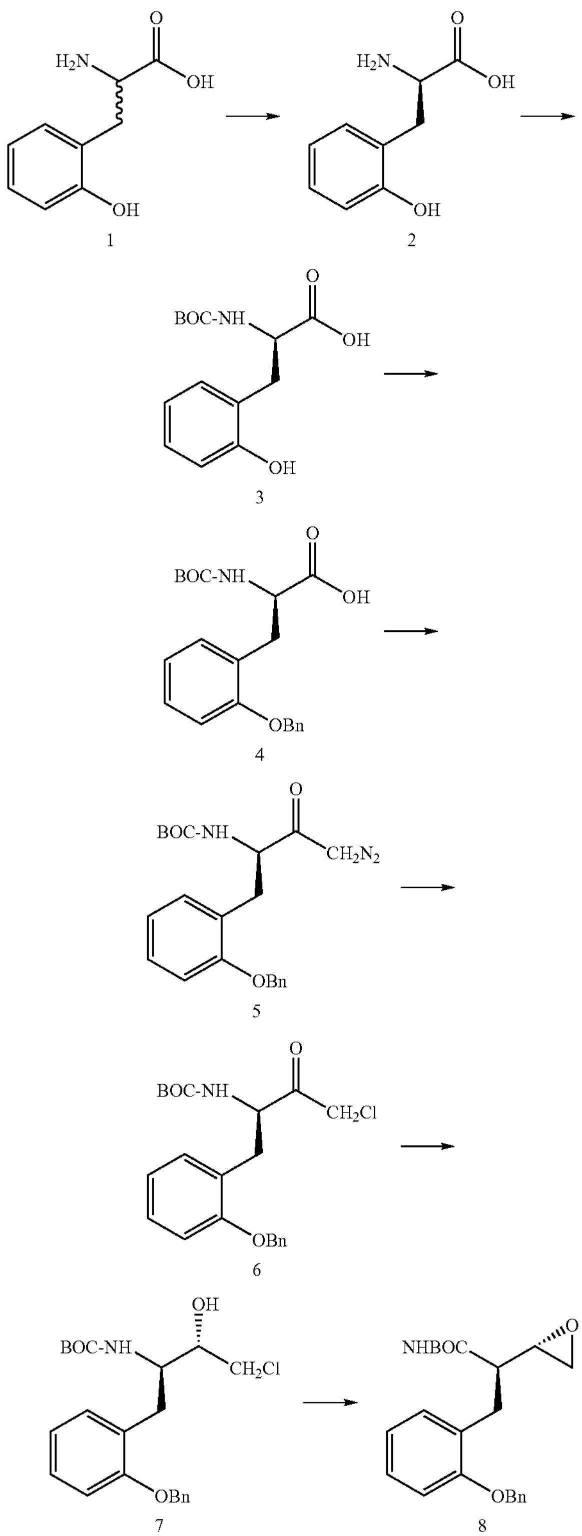

1, 2, 3, 4, 5, 6, 7, 8

Scheme 2
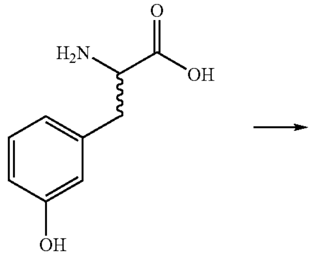
9
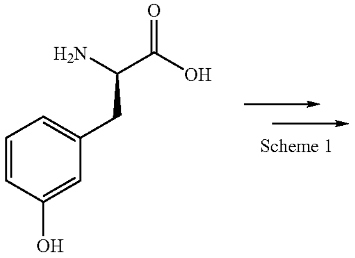
10
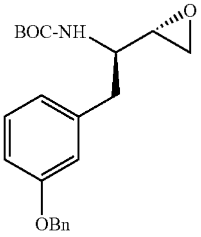
11
Scheme 3
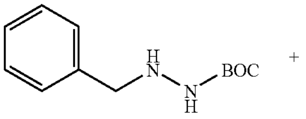
12
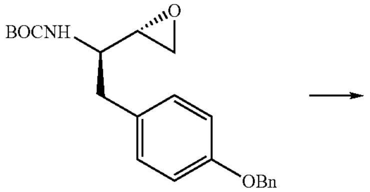
13
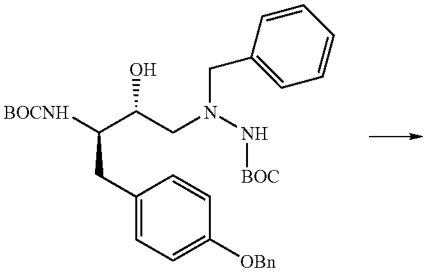
14
-continued
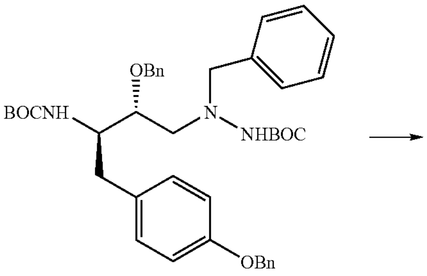
15
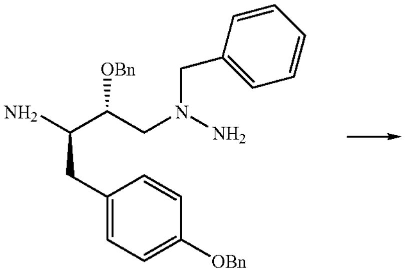
16
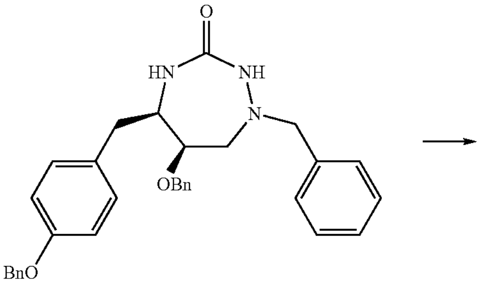
17
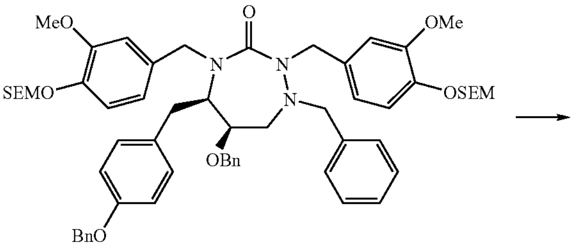
18
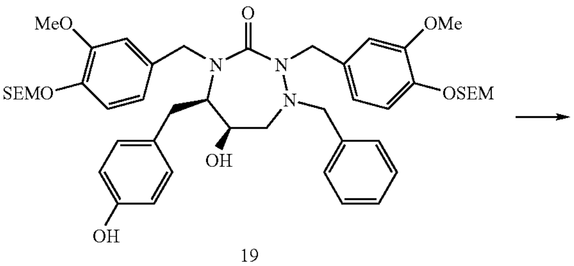
19

-continued
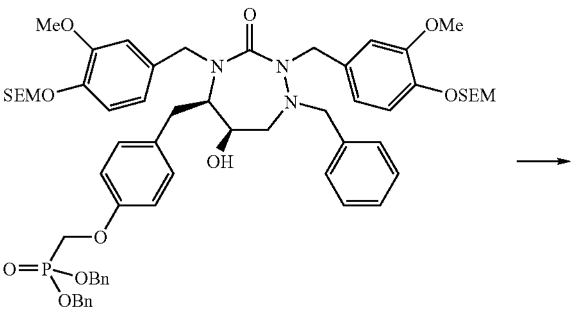
20
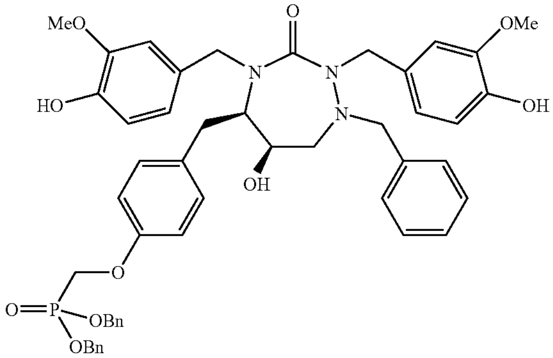
21
Scheme 4
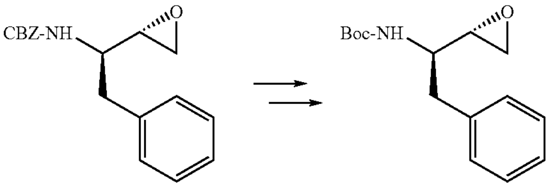
24 25
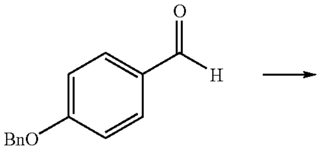
22
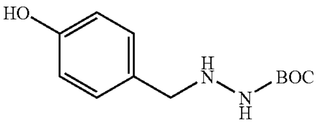
+ 25
23
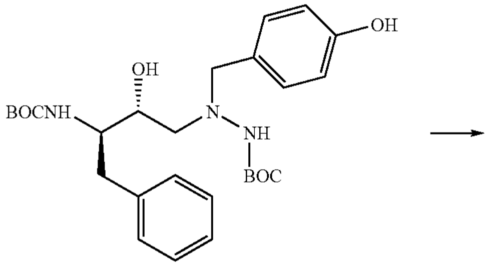
26
-continued
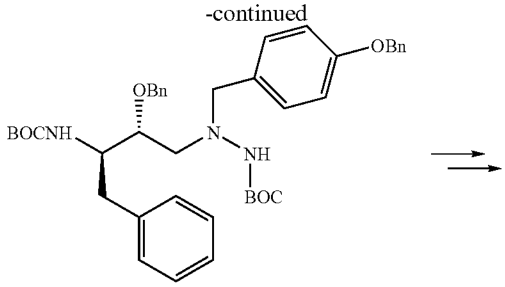
27
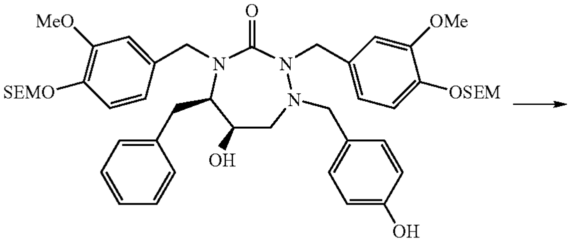
28
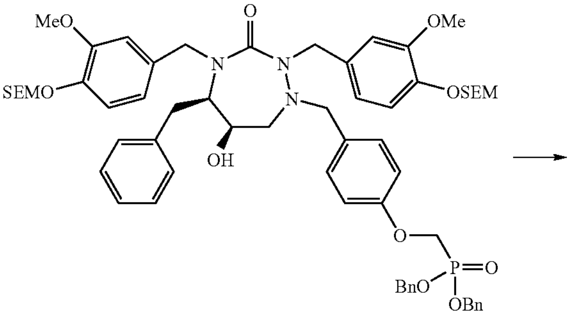
29
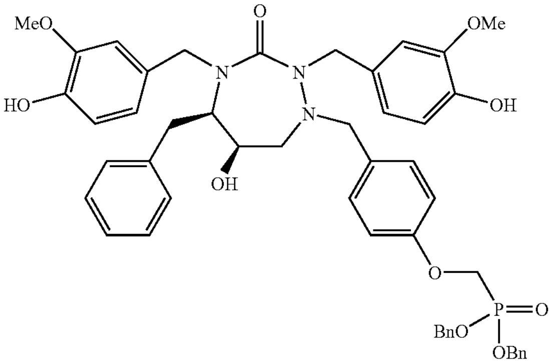
30
Scheme 5
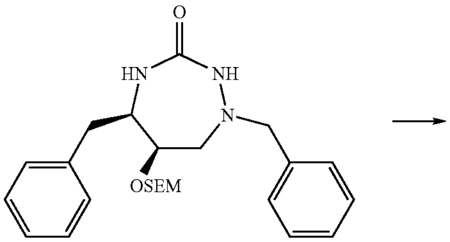
31

-continued
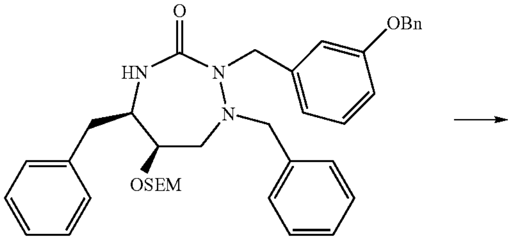
32
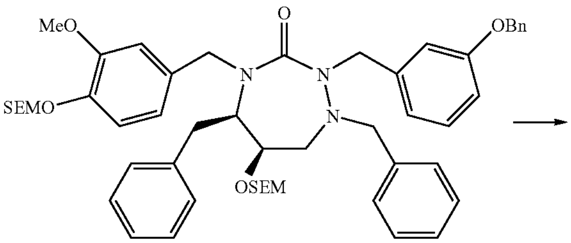
33
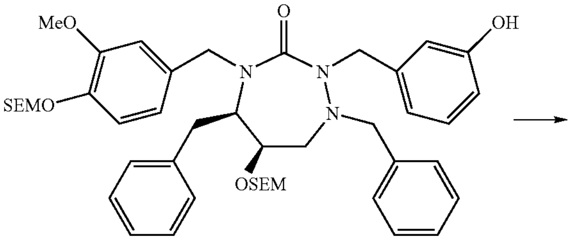
34
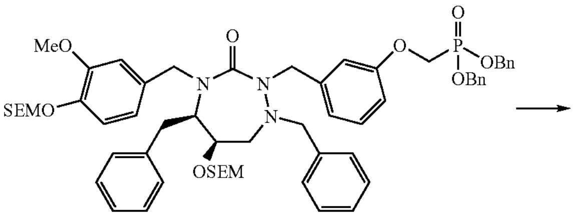
35
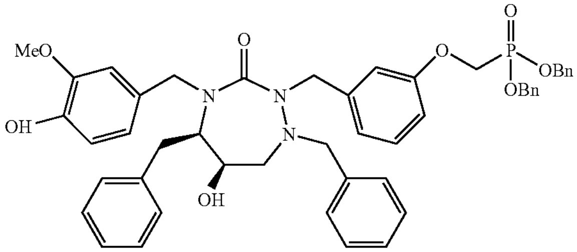
36
Scheme 6
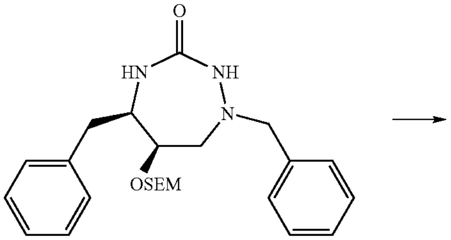
31
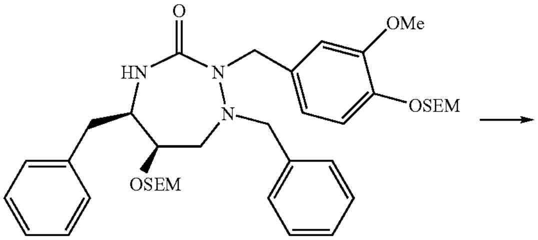
37
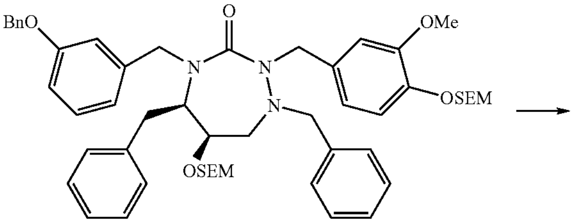
38
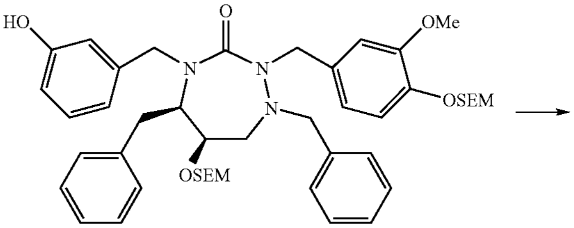
39
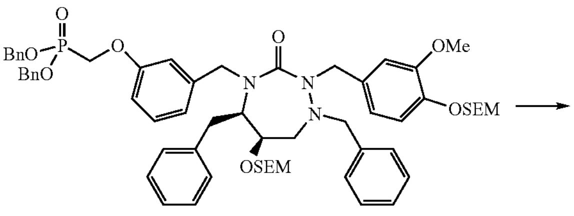
40
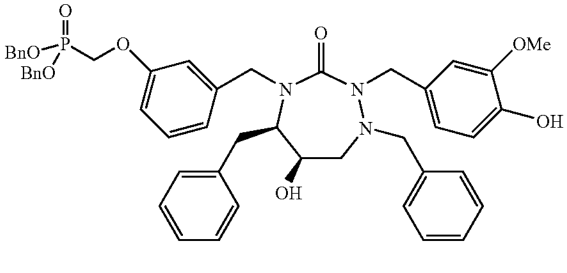
41

Example Section D

Example 1

Scheme 1: Example; [2-(2-Benzyloxy-phenyl)-1-oxiranyl-ethyl]-carbamic acid tert-butyl ester (8)

Commercially available DL-o-tyrosine 1 (Fluka) is treated with L-aminoacid oxidase and oxygen according to the procedure of Sun et al. (J. Med. Chem. 1998, 41, 1034-1041) to afford the D-o-tyrosine 2. Reaction with di-t-butyl-dicarbonate in the presence of base affords the boc protected amino acid 3 (J. Med. Chem. 1998, 41, 1034-1041). The boc protected acid 3 is then treated with benzyl bromide in the presence of potassium carbonate to afford the benzyl ether 4 (J. Med. Chem. 1998, 41, 1034-1041). The four step sequence reported for the preparation of the corresponding epoxide of phenylalanine (see J. Med. Chem. 1994, 37, 1758-1768) is used to prepare the desired epoxides. Thus, the acid 4 is treated with isobutylchloroformate in the presence of N-methylmorpholine to afford the mixed anhydride which is then treated with diazomethane to afford the α-diazoketone 5 (see scheme 1). The ketone 5 is treated with HCl to form the α-chloroketone 6 which is then reduced with sodium borohydride to form the chloro alcohol 7. The 2S, 3R diastereoisomer is separated by chromatography and treated with base (e.g. potassium hydroxide) to afford the epoxide 8.

Commercially available DL-m-tyrosine 9 (Aldrich) is resolved by treatment with α-chymotrypsin to afford D-m-tyrosine 10 (Recl.: J. R. Neth. Chem. Soc. 1984, 103, 4, p110-111.) (Scheme 2). The tyrosine 10 is then treated in the same manner as the D-o-tyrosine (Scheme 1) to form the m-benzyloxy epoxide 11.

The Boc-D-Tyr(Bzl)-OH acid is commerically available (Bachem) and is treated according to the four step procedure in Scheme 1 to generate the p-benzyloxy epoxide 13 shown in Scheme 3.

Example 2

Scheme 3: Example, {4-[1-Benzyl-6-hydroxy-2,4-bis-(4-hydroxy-3-methoxy-benzyl)-3-oxo-[1,2,4]triazepan-5-ylmethyl]-phenoxymethyl}-phosphonic acid dibenzyl ester The boc protected benzylhydrazine 12 is prepared by condensation of boc-carbazate with benzaldehyde followed by catalytic hydrogenolysis (J. Chem. Soc. Perkin Trans. I 1975, 1712-1720). Treatment of the epoxide 13 with the boc protected benzylhydrazine 12 affords the alcohol 14 (J. Med. Chem. 1996, 39, 392-397). Benzylation of the secondary alcohol with benzylchloride in the presence of base (Green) affords the benzylether 15. Deprotection of the BOC groups with trifluoroacetic acid yields the diamine 16 (Green). CDI mediated cyclization affords the cyclic triazacycloheptanone 17 (J. Med. Chem. 1996, 39, 392-397). Alkyation of the nitrogens with [2-(4-chloromethyl-2-methoxy-phenoxymethoxy)-ethyl]-trimethyl-silane (prepared according to the reference J. Med. Chem. 1996, 39, 392-397) affords the bis-substituted triazacycloheptanone 18 (J. Med. Chem. 1996, 39, 392-397). Catalytic hydrogenolysis affords the unprotected phenol 19 (Green) which upon alkylation with trifluoro-methanesulfonic acid bis-benzyloxy-phosphorylmethyl ester in the presence of base (e.g. cesium carbonate) yields the dibenzyl phosphonate 20. Removal of the silyl protecting groups using trimethylsilyl chloride or anhydrous HCl in methanol affords the dibenzyl phosphonate ester product 21 (J. Med. Chem. 1996, 39, 392-397).

The meta substituted analog {3-[1-Benzyl-6-hydroxy-2,4-bis-(4-hydroxy-3-methoxy-benzyl)-3-oxo-[1,2,4]triazepan-5-ylmethyl]-phenoxymethyl}-phosphonic acid dibenzyl ester or the ortho analog, {2-[1-Benzyl-6-hydroxy-2,4-bis-(4-hydroxy-3-methoxy-benzyl)-3-oxo-[1,2,4]triazepan-5-ylmethyl]-phenoxymethyl}-phosphonic acid dibenzyl ester, are prepared using the same methods except replacing the p-benzyloxyepoxide 13 with the meta- and ortho-substituted benzyloxy epoxides, 11 and 8, respectively.

Example 3

Scheme 4: Example, {4-[5-Benzyl-6-hydroxy-2,4-bis-(4-hydroxy-3-methoxy-benzyl)-3-oxo-[1,2,4]triazepan-1-ylmethyl]-phenoxymethyl}-phosphonic acid dibenzyl ester (30)

p-Benzyloxybenzaldehyde 22 is treated with boc-carbazate and then reduced by catalytic hydrogenolysis to afford the hydrazine 23 (J. Chem. Soc. Perkin Trans. I 1975, 1712-1720). The Boc epoxide 25 is prepared from the corresponding CBZ epoxide 24 by catalytic hydrogenolysis followed by treatment with BOC anhydride (Green). The CBZ-epoxide 24 is prepared according to the procedure of Sham et al. (J. Med. Chem. 1996, 39, 392-397).

Treatment of the epoxide 25 with the hydrazine 23 affords the alcohol 26. The alcohol 26 is treated with benzyl bromide in the presence of base (e.g. cesium carbonate) to afford the dibenzyl compound 27 (Green). The Boc groups are then removed using trifluoroacetic acid to yield diamine 28 (Green). Subjecting the diamine 28 to the same procedures shown in Scheme 1 then affords the dibenzyl phosphonate ester 29. Removal of the silyl protecting groups using trimethylsilyl chloride or anhydrous HCl in methanol affords the dibenzyl phosphonate ester product 30 (J. Med. Chem. 1996, 39, 392-397).

The corresponding meta- and ortho-analogs are prepared using the same procedures as in Scheme 4 except substituting p-benzyloxybenzaldehyde with m- or o-benzyloxybenzaldehyde respectively.

Example 4

Scheme 5: {3-[1,5-Dibenzyl-4-(4-hydroxy-3-methoxy-benzyl)-3-oxo-6-(2-trimethylsilanyl-ethoxymethoxy)-[1,2,4]triazepan-2-ylmethyl]-phenoxymethyl}-phosphonic acid dibenzyl ester (36)

The SEM protected triazacycloheptanone 31 is prepared according to the reported procedure of Sham et al. (J. Med. Chem. 1996, 39, 392-397). Regioselective alkylation by treatment of the triazacycloheptanone with m-benzyloxybenzylchloride and sodium hydride in DMF affords 32 which is then alkylated a second time under similar conditions to afford the bis-substituted compound 33 (J. Med. Chem. 1996, 39, 392-397). Catalytic hydrogenolysis affords the phenol 34 (Green). Alkylation with trifluoro-methanesulfonic acid bis-benzyloxy-phosphorylmethyl ester using the standard conditions affords the dibenzyl ester 35. Removal of the silyl protecting groups using trimethylsilyl chloride or anhydrous HCl in methanol affords the dibenzyl phosphonate ester product 36 (J. Med. Chem. 1996, 39, 392-397).

Ortho analog {2-[1,5-Dibenzyl-4-(4-hydroxy-3-methoxy-benzyl)-3-oxo-6-(2-trimethylsilanyl-ethoxymethoxy)-[1,2,4]triazepan-2-ylmethyl]-phenoxymethyl}-phosphonic acid dibenzyl ester and para analog {4-[1,5-Dibenzyl-4-(4-hydroxy-3-methoxy-benzyl)-3-oxo-6-(2-trimethylsilanyl-ethoxymethoxy)-[1,2,4]triazepan-2-ylmethyl]-phenoxymethyl}phosphonic acid dibenzyl ester are prepared using the same procedures except substituting o-benzyloxy-benzylchloride and p-benzyloxybenzylchloride respectively, for the m-benzyloxybenzylchloride. O-benzyloxybenzyl-chloride is prepared from o-benzyloxybenzaldehyde by reduction with sodium borohydride and then treatment with methanesulfonylchloride (J. Med. Chem. 1996, 39, 392-397).

Example 5

Scheme 6: {3-[1,5-Dibenzyl-6-hydroxy-2-(4-hydroxy-3-methoxy-benzyl)-3-oxo-[1,2,4]triazepan-4-ylmethyl]-phenoxymethyl}-phosphonic acid dibenzyl ester (41)

The SEM protected triazacycloheptanone 31 is prepared according to the reported procedure of Sham et al. (J. Med. Chem. 1996, 39, 392-397). Regioselective alkylation by treatment of the triazacycloheptanone with SEM protected benzylchloride and sodium hydride in DMF affords 37 which is then alkylated with m-benzyloxybenzylchloride under similar conditions to afford the bis-substituted compound 38 (J. Med. Chem. 1996, 39, 392-397). Catalytic hydrogenolysis affords the phenol 39 (Green). Alkylation with trifluoro-methanesulfonic acid bis-benzyloxy-phosphorylmethyl ester using the standard conditions affords the dibenzyl ester 40. Removal of the silyl protecting groups using trimethylsilyl chloride or anhydrous HCl in methanol affords the dibenzyl phosphonate ester product 41 (J. Med. Chem. 1996, 39, 392-397).

Ortho analog, {2-[1,5-Dibenzyl-6-hydroxy-2-(4-hydroxy-3-methoxy-benzyl)-3-oxo-[1,2,4]triazepan-4-ylmethyl]-phenoxymethyl}-phosphonic acid dibenzyl ester and para analog, {4-[1,5-Dibenzyl-6-hydroxy-2-(4-hydroxy-3-methoxy-benzyl)-3-oxo-[1,2,4]triazepan-4-ylmethyl]-phenoxymethyl}-phosphonic acid dibenzyl ester are prepared using the same procedures except substituting o-benzyloxy-benzylchloride and p-benzyloxybenzylchloride respectively, for the m-benzyloxybenzylchloride.

Scheme General Section

General aspects of these exemplary methods are described below and in the Example. Each of the products of the following processes is optionally separated, isolated, and/or purified prior to its use in subsequent processes.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes above and in the examples (hereafter "exemplary schemes") leads to various analogs of the specific exemplary materials produce. The above cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

Scheme 1001

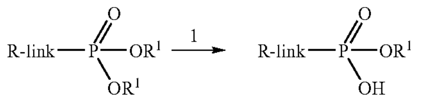

27.1 27.2

-continued

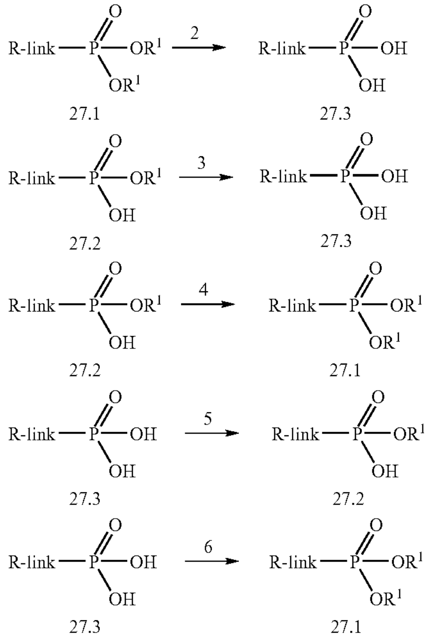

27.1 27.3
27.2 27.3
27.2 27.1
27.3 27.2
27.3 27.1

Scheme 1001 shows the interconversions of certain phosphonate compounds: acids —$P(O)(OH)_2$; mono-esters —$P(O)(OR_1)(OH)$; and diesters —$P(O)(OR_1)_2$ in which the $R^1$ groups are independently selected, and defined herein before, and the phosphorus is attached through a carbon moiety (link, i.e. linker), which is attached to the rest of the molecule, e.g. drug or drug intermediate (R). The $R^1$ groups attached to the phosphonate esters in Scheme 1001 may be changed using established chemical transformations. The interconversions may be carried out in the precursor compounds or the final products using the methods described below. The methods employed for a given phosphonate transformation depend on the nature of the substituent $R^1$. The preparation and hydrolysis of phosphonate esters is described in *Organic Phosphorus Compounds*, G. M. Kosolapoff, L. Maeir, eds, Wiley, 1976, p. 9ff.

The conversion of a phosphonate diester 27.1 into the corresponding phosphonate monoester 27.2 (Scheme 1001, Reaction 1) can be accomplished by a number of methods. For example, the ester 27.1 in which $R^1$ is an arylalkyl group such as benzyl, can be converted into the monoester compound 27.2 by reaction with a tertiary organic base such as diazabicyclooctane (DABCO) or quinuclidine, as described in *J. Org. Chem.,* 1995, 60:2946. The reaction is performed in an inert hydrocarbon solvent such as toluene or xylene, at about 110° C. The conversion of the diester 27.1 in which $R^1$ is an aryl group such as phenyl, or an alkenyl group such as allyl, into the monoester 27.2 can be effected by treatment of the ester 27.1 with a base such as aqueous sodium hydroxide in acetonitrile or lithium hydroxide in aqueous tetrahydrofuran. Phosphonate diesters 27.2 in which one of the groups $R^1$ is arylalkyl, such as benzyl, and the other is alkyl, can be converted into the monoesters 27.2 in which $R^1$ is alkyl, by hydrogenation, for example using a palladium on carbon catalyst. Phosphonate diesters in which both of the groups $R^1$ are alkenyl, such as allyl, can be converted into the monoester 27.2 in which $R^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in *J. Org. Chem.,* 38:3224 1973 for the cleavage of allyl carboxylates.

The conversion of a phosphonate diester 27.1 or a phosphonate monoester 27.2 into the corresponding phosphonic acid 27.3 (Scheme 1001, Reactions 2 and 3) can be effected by reaction of the diester or the monoester with trimethylsilyl bromide, as described in *J. Chem. Soc., Chem. Comm.,* 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 27.2 in which $R^1$ is arylalkyl such as benzyl, can be converted into the corresponding phosphonic acid 27.3 by hydrogenation over a palladium catalyst, or by treatment with hydrogen chloride in an ethereal solvent such as dioxane. A phosphonate monoester 27.2 in which $R^1$ is alkenyl such as, for example, allyl, can be converted into the phosphonic acid 27.3 by reaction with Wilkinson's catalyst in an aqueous organic solvent, for example in 15% aqueous acetonitrile, or in aqueous ethanol, for example using the procedure described in *Helv. Chim. Acta.,* 68:618, 1985. Palladium catalyzed hydrogenolysis of phosphonate esters 27.1 in which $R^1$ is benzyl is described in *J. Org. Chem.,* 24:434, 1959. Platinum-catalyzed hydrogenolysis of phosphonate esters 27.1 in which $R^1$ is phenyl is described in *J. Amer. Chem. Soc.,* 78:2336, 1956.

The conversion of a phosphonate monoester 27.2 into a phosphonate diester 27.1 (Scheme 1001, Reaction 4) in which the newly introduced $R^1$ group is alkyl, arylalkyl, or haloalkyl such as chloroethyl, can be effected by a number of reactions in which the substrate 27.2 is reacted with a hydroxy compound $R^1OH$, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 27.1 to the diester 27.1 can be effected by the use of the Mitsunobu reaction. The substrate is reacted with the hydroxy compound $R^1OH$, in the presence of diethyl azodicarboxylate and a triarylphosphine such as triphenyl phosphine. Alternatively, the phosphonate monoester 27.2 can be transformed into the phosphonate diester 27.1, in which the introduced $R^1$ group is alkenyl or arylalkyl, by reaction of the monoester with the halide $R^1Br$, in which $R^1$ is as alkenyl or arylalkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 27.2 is transformed into the chloro analog —$P(O)(OR^1)Cl$ by reaction with thionyl chloride or oxalyl chloride and the like, as described in Organic Phosphorus Compounds, G. M. Kosolapoff, L. Maeir, eds, Wiley, 1976, p. 17, and the thus-obtained product —$P(O)(OR^1)Cl$ is then reacted with the hydroxy compound $R^1OH$, in the presence of a base such as triethylamine, to afford the phosphonate diester 27.1.

A phosphonic acid —$P(O)(OH)_2$ can be transformed into a phosphonate monoester —$P(O)(OR^1)(OH)$ (Scheme 1001, Reaction 5) by means of the methods described above of for the preparation of the phosphonate diester —$P(O)(OR^1)_2$ 27.1, except that only one molar proportion of the component $R^1OH$ or $R^1Br$ is employed.

A phosphonic acid —$P(O)(OH)_2$ 27.3 can be transformed into a phosphonate diester —$P(O)(OR^1)_2$ 27.1 (Scheme 1, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids 27.3 can be transformed into phosphonic esters 27.1 in which $R^1$ is aryl, such as phenyl, by means of a coupling reaction employing, for example, phenol and dicyclohexylcarbodiimide in pyridine at about 70° C. Alternatively, phosphonic acids 27.3 can be transformed into phosphonic esters 27.1 in which $R^1$ is alkenyl, by means of an alkylation reaction. The phosphonic acid is reacted with the alkenyl bromide $R^1Br$ in a polar organic solvent such as acetonitrile solution at reflux temperature, in the presence of a base such as cesium carbonate, to afford the phosphonic ester 27.1.

Amino alkyl phosphonate compounds 809:

809

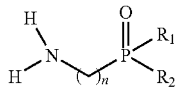

are a generic representative of compounds 811, 813, 814, 816 and 818. Some methods to prepare embodiments of 809 are shown in Scheme 1002. Commercial amino phosphonic acid 810 was protected as carbamate 811. The phosphonic acid 811 was converted to phosphonate 812 upon treatment with ROH in the presence of DCC or other conventional coupling reagents. Coupling of phosphonic acid 811 with esters of amino acid 820 provided bisamidate 817. Conversion of acid 811 to bisphenyl phosphonate followed by hydrolysis gave mono-phosphonic acid 814 (Cbz=$C_6H_5CH_2C(O)$—), which was then transformed to mono-phosphonic amidate 815. Carbamates 813, 816 and 818 were converted to their corresponding amines upon hydrogenation. Compounds 811, 813, 814, 816 and 818 are useful intermediates to form the phosphonate compounds of the invention.

Preparation of Carboalkoxy-substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116, 3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters. Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980, 23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2, -dioxaphosphinane as described in Nucleosides Nucleotides 1995, 14, 871, and diphenyl chlorophosphate, as described in J. Med. Chem., 1988, 31, 1305.

Phosphonic acids are converted into amidates and esters by means of the Mitsonobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., 1,1993, 19, 2303, or J. Med. Chem., 1995, 38, 1372, or Tet. Lett., 2002, 43, 1161.

Schemes 1-4 illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4).

Scheme 1 illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an aminoester 1.9, in which the group $R^2$ is H or alkyl, the group $R^4$ is an alkylene moiety such as, for example, $CHCH_3$, $CHPr^1$, $CH(CH_2Ph)$, $CH_2CH(CH_3)$ and the like, or a group present in natural or modified aminoacids, and the group $R^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsonobu reaction. The preparation of amidates by means of the Mitsonobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsonobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing, in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different.

An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid 1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl duimidazole to produce the activated intermediate 1.35, and the product is then reacted, under the same conditions, with ethyl N-methylalaninate 1.33a to give the bisamidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above. The product 1.8 is then reacted with an aminoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethyl acetate over a 5% palladium on carbon catalyst to produce the monoacid product 1.29. The product is subjected to a Mitsonobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5. An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150° C., in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 illustrates methods for the preparation of phosphonate monoamidates.

In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1. The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10.

Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsonobu reaction etc) described in Scheme 1 for the coupling of amines and phosphonic acids.

Scheme 1

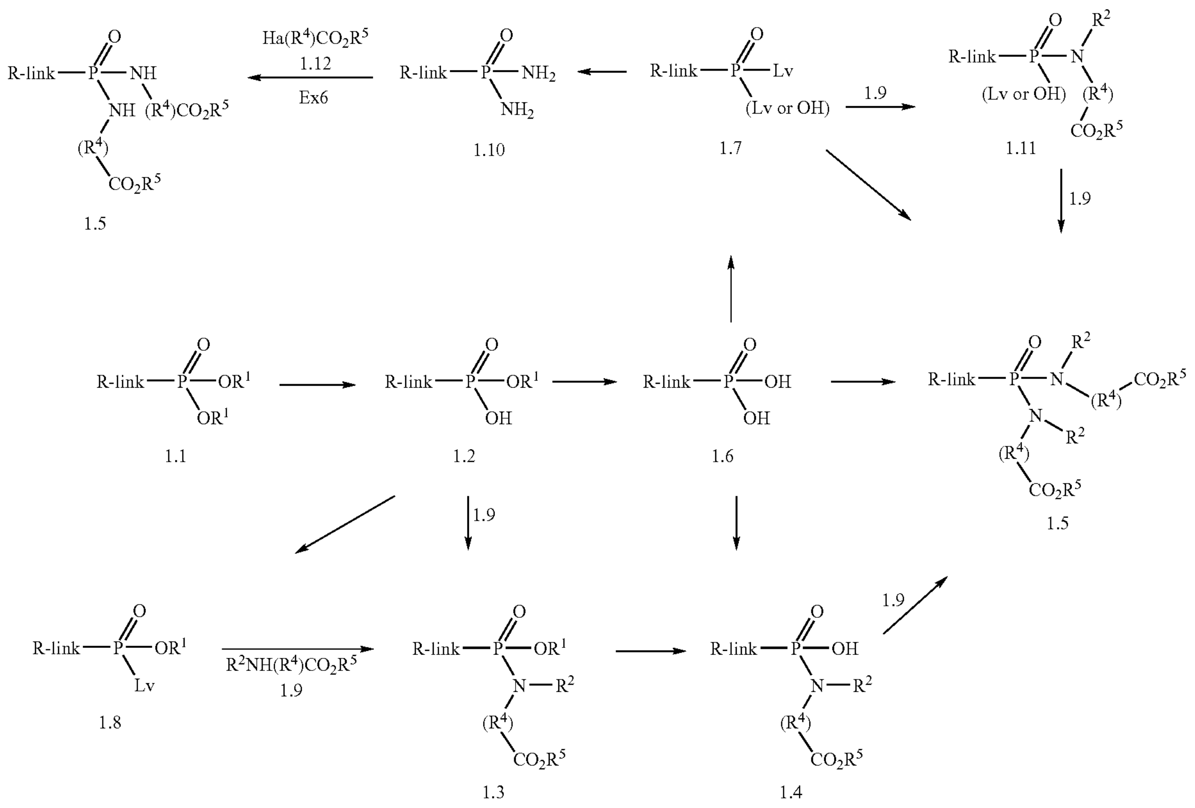

1.5 1.10 1.7 1.11 1.1 1.2 1.6 1.5 1.8 1.3 1.4

-continued
Scheme 1 Example 1
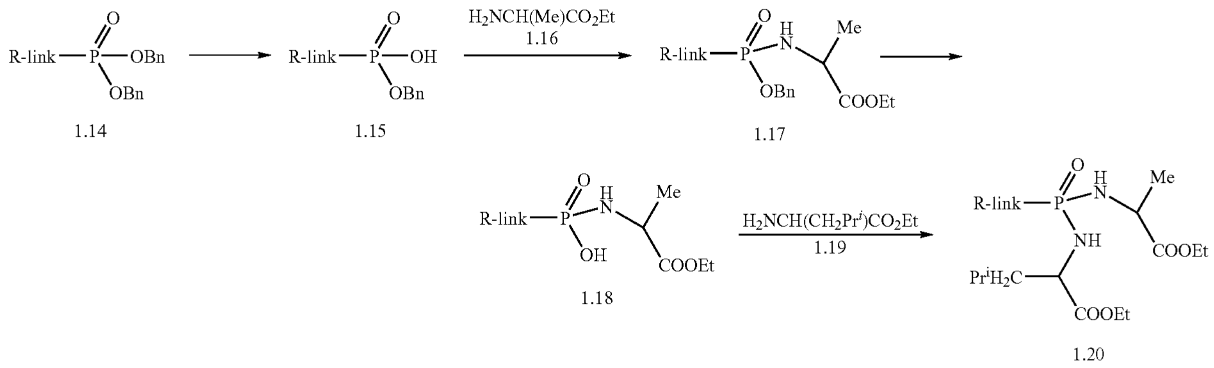
1.14 1.15 1.17
1.18 1.20
Scheme 1 Example 2
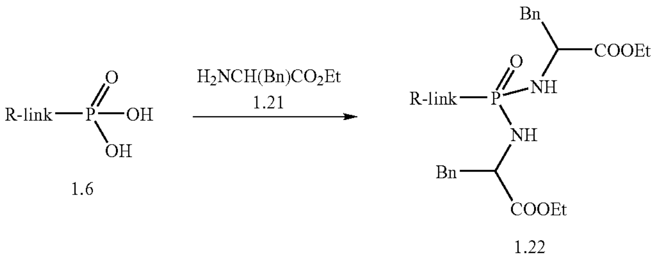
1.6 1.22
Scheme 1 Example 3
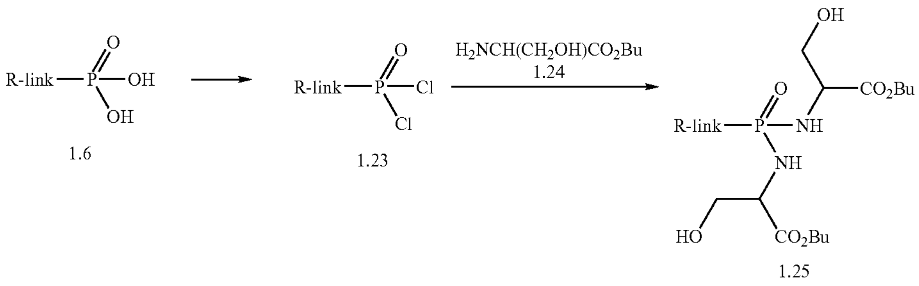
1.6 1.23 1.25
Scheme 1 Example 4
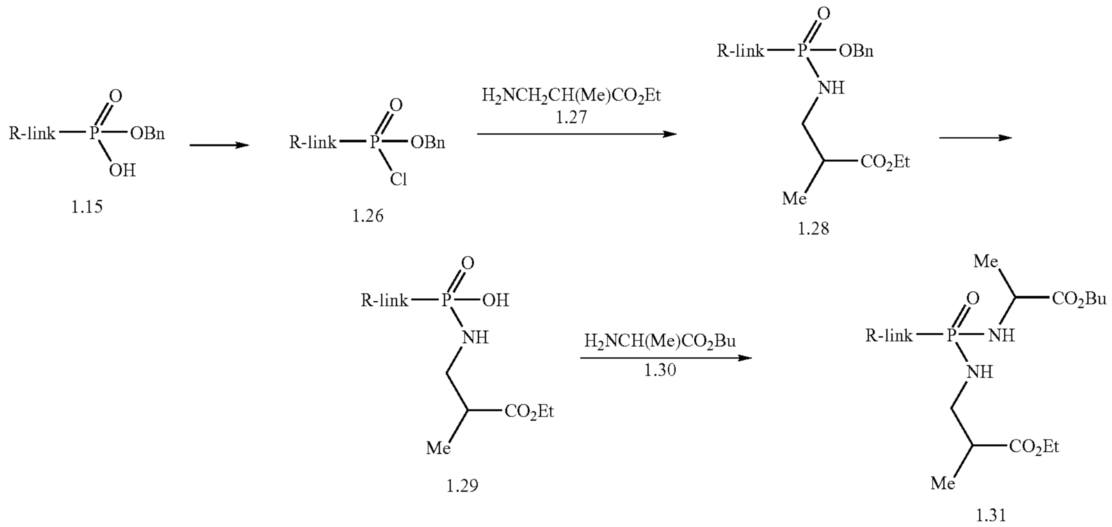
1.15 1.26 1.28
1.29 1.31

-continued
Scheme 1 Example 5
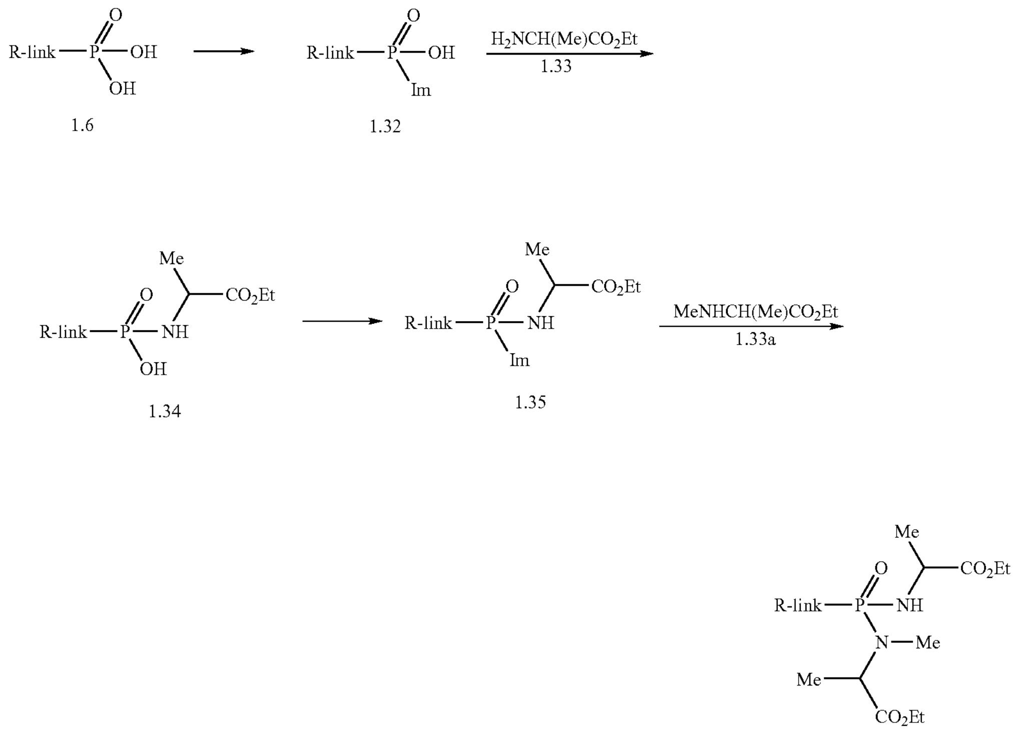
1.6 1.32 1.34 1.35
1.36
Scheme 1 Example 6
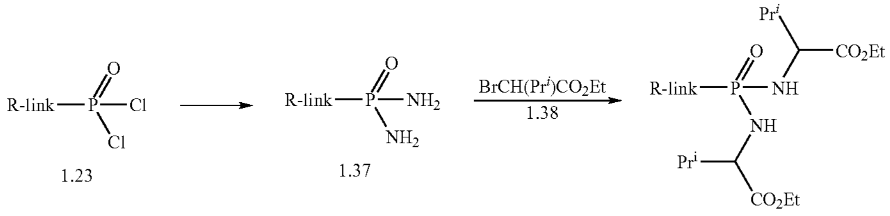
1.23 1.37
1.39
Scheme 1 Example 7
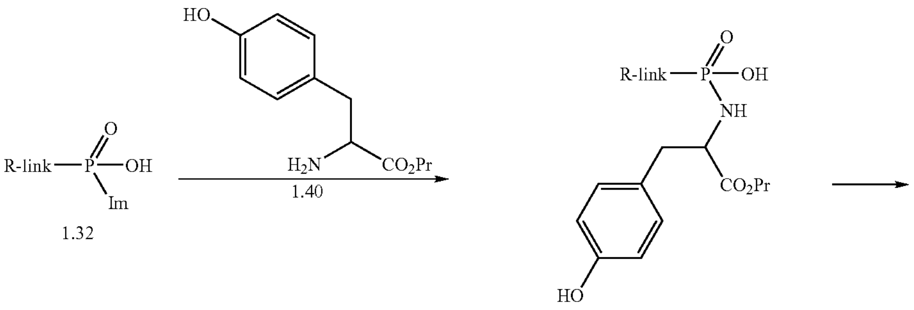
1.32
1.41

-continued

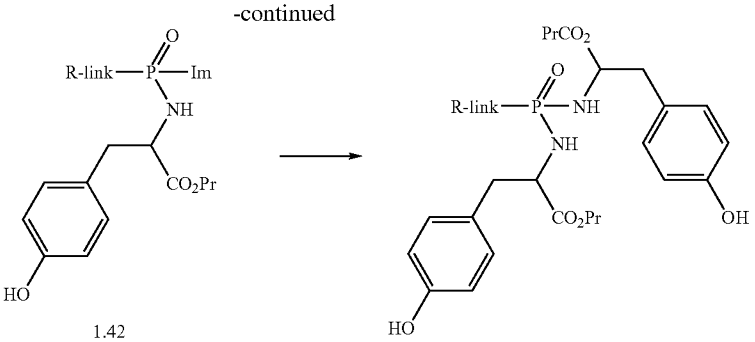

1.42 1.43

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethyl acetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds $R^3OH$, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the $R^1$ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° C. with butyl 2-bromo-3-phenylpropionate 2.20 and potassium carbonate, to afford the amidate product 2.21. Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the monodisplacement product 1.11. The latter compound is then reacted with the hydroxy compound $R^3OH$ in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds $R^3OH$, the corresponding products 2.3 are obtained.

Scheme 2

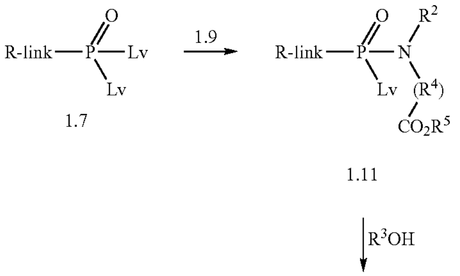

1.7 1.11

-continued
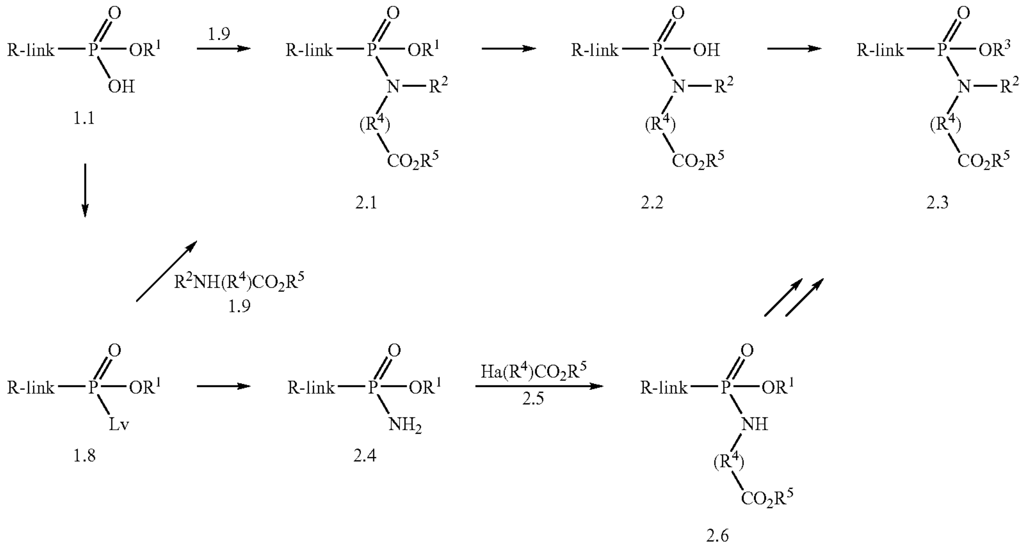
Scheme 2 Example 1
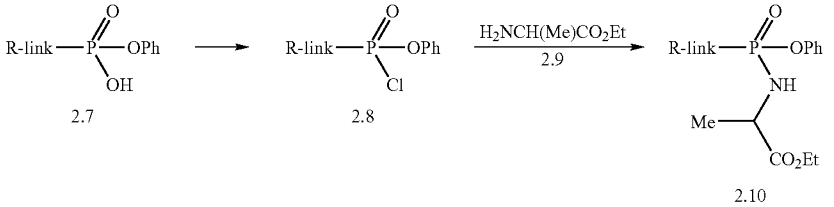
Scheme 2 Example 2
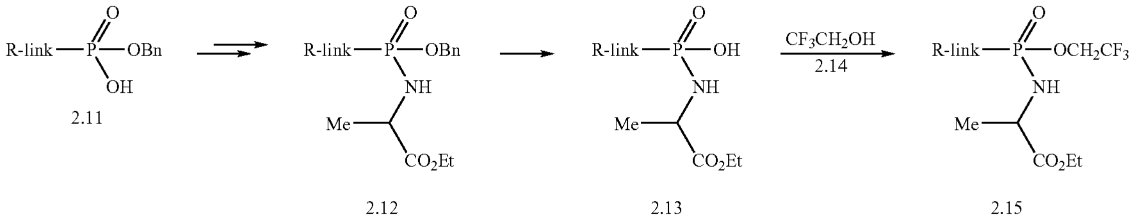
Scheme 2 Example 2
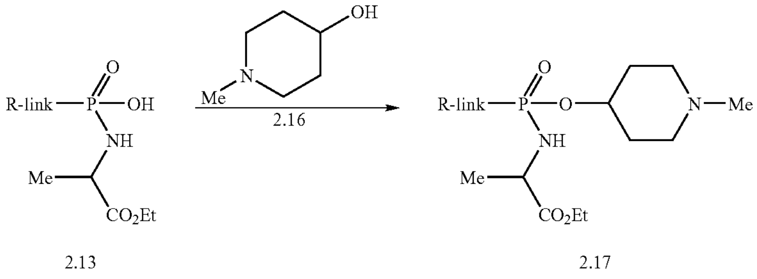
Scheme 2 Example 4
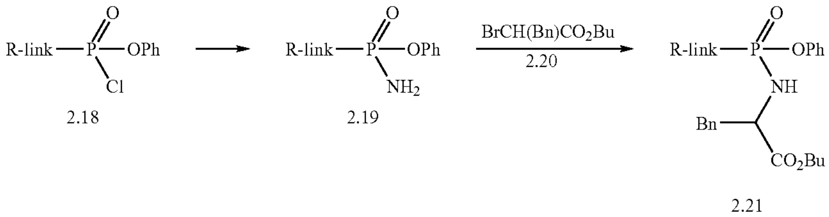

-continued

Scheme 2 Example 5

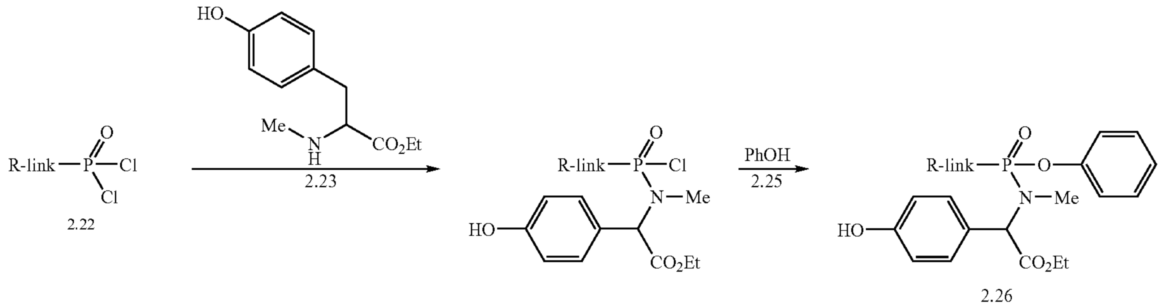

2.22 2.23 2.24 2.26

Scheme 3 illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carboduimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsonobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine) rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70° C., with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^3O$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl)phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 3

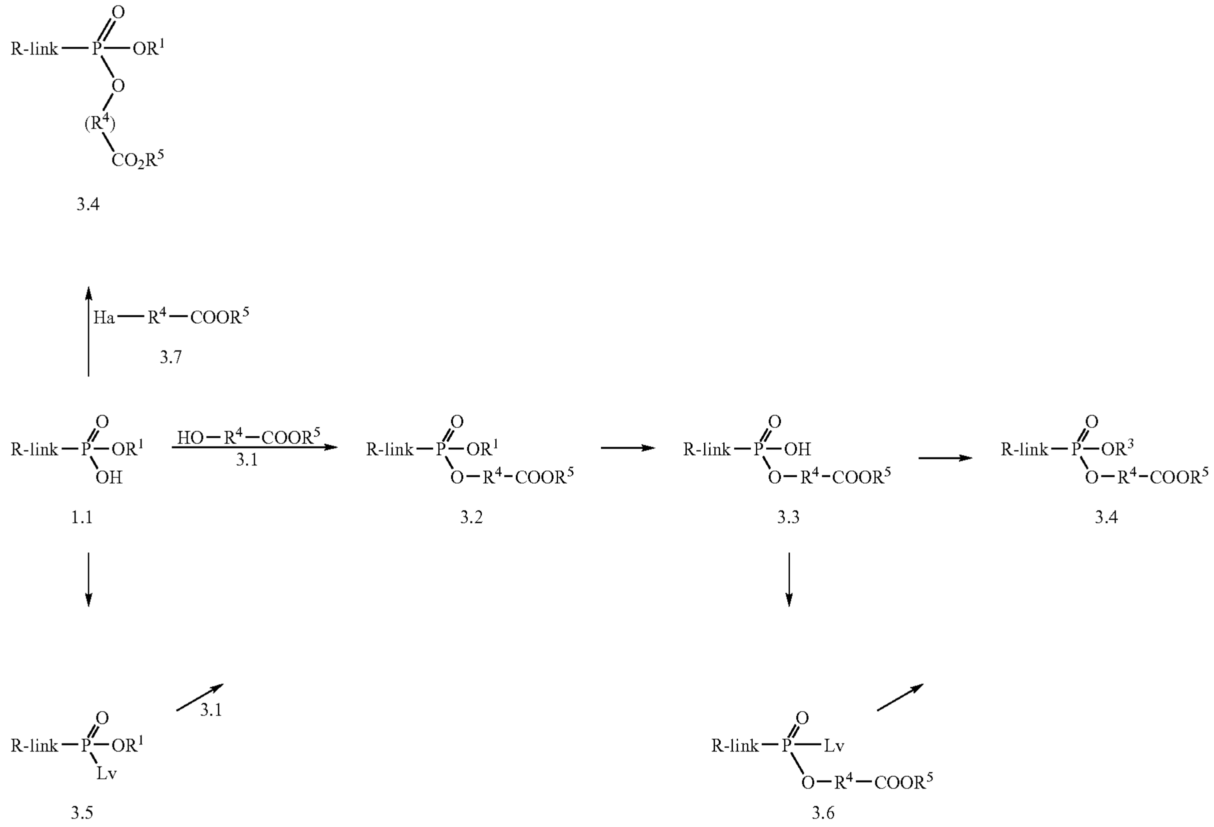

3.4, 1.1, 3.2, 3.3, 3.4, 3.5, 3.6

Scheme 3 Example 1

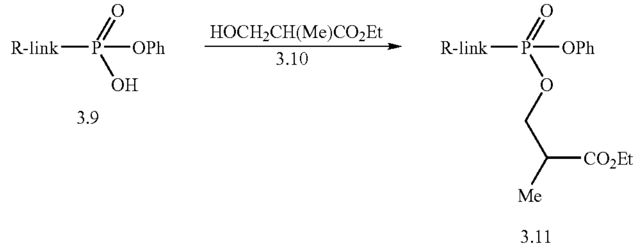

3.9, 3.11

Scheme 3 Example 2

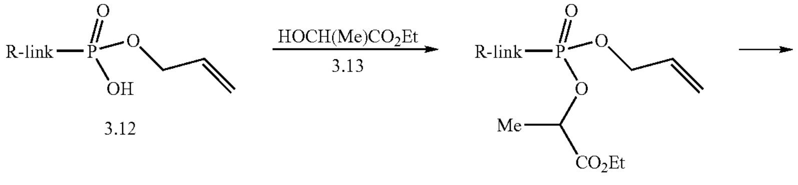

3.12, 3.14

-continued

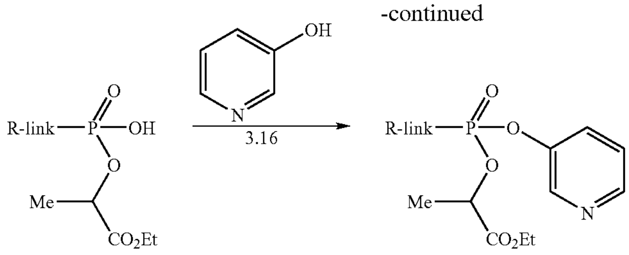

3.15 3.17

Scheme 3 Example 3

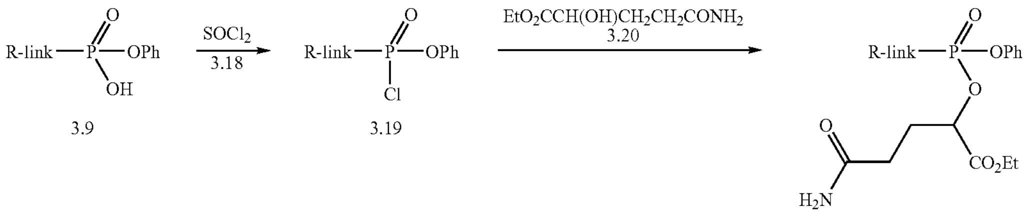

3.9 3.19 3.21

Scheme 3 Example 4

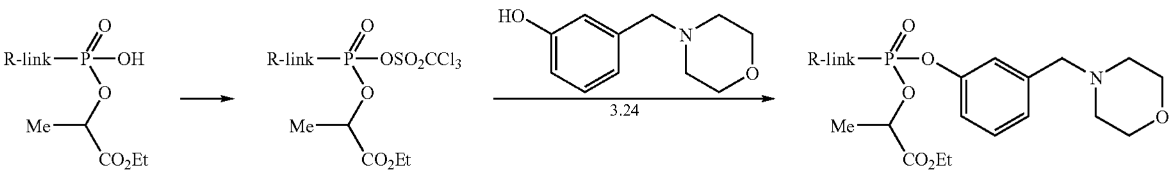

3.22 3.23 3.25

Scheme 3 Example 5

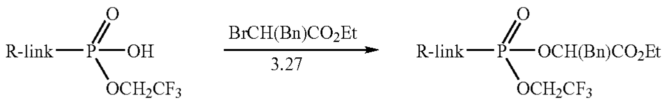

3.26 3.28

Scheme 4 illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsonobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70° C., to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80° C., as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different. The methods are illustrated in Scheme 4, Examples 3 and 4. As shown in Example 3, the phosphoryl dichloride 2.22 is reacted with three molar equivalents of ethyl 3-hydroxy-2(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° C. in the presence of diisopropylethylamine. The product 4.12 is then reacted, under the same conditions, with one molar equivalent of ethyl lactate 4.13, to give the diester product 4.14.

Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

Scheme 4

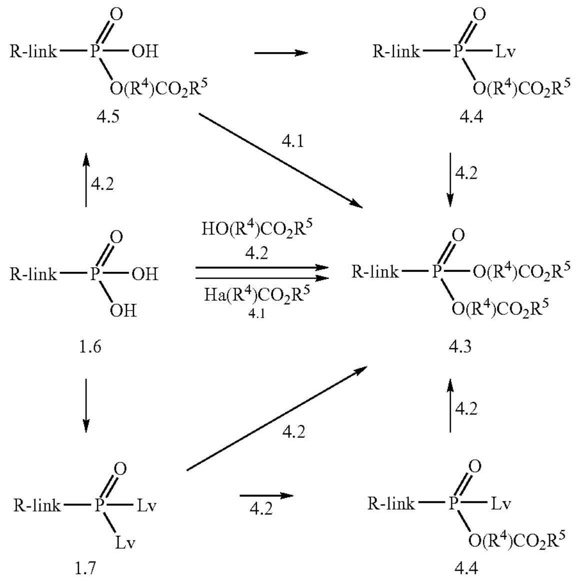

Scheme 4 Example 1

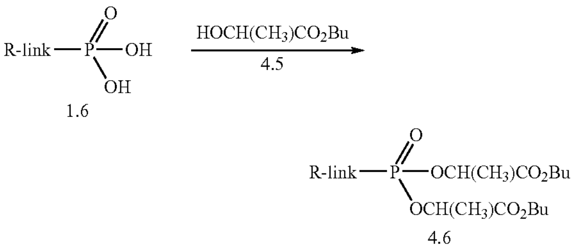

Scheme 4 Example 2

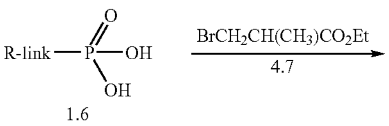

-continued

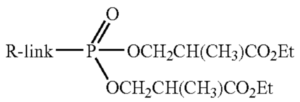

4.8

Scheme 4 Example 3

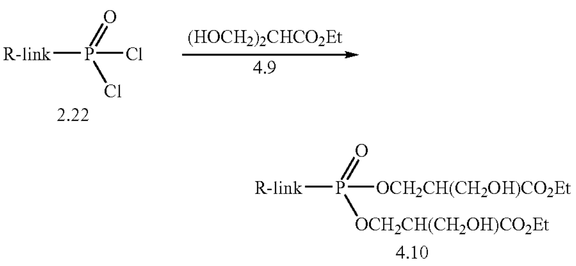

Scheme 4 Example 4

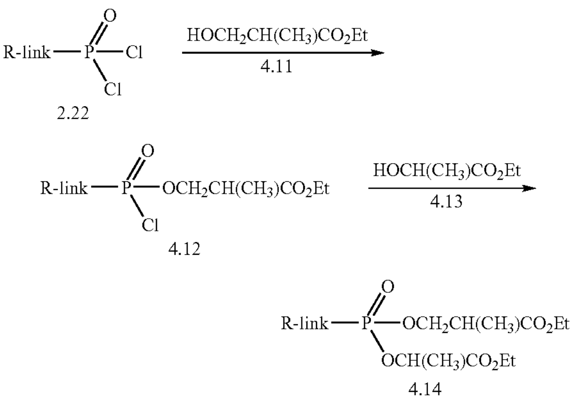

Scheme 1002

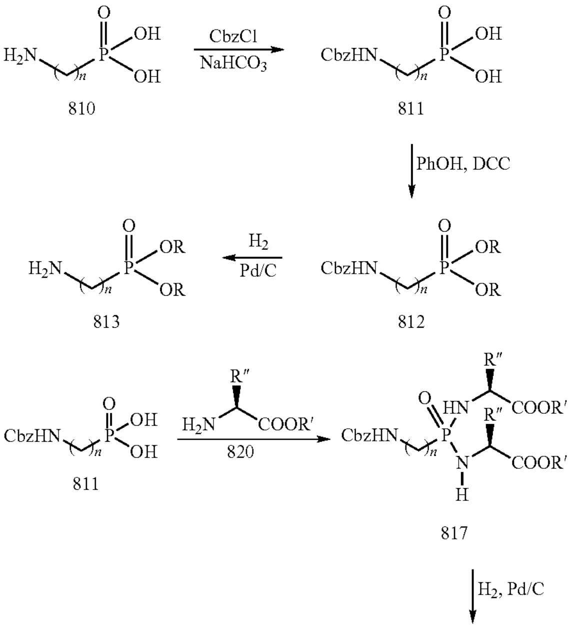

-continued

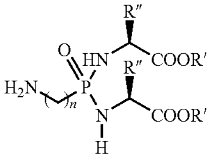

818

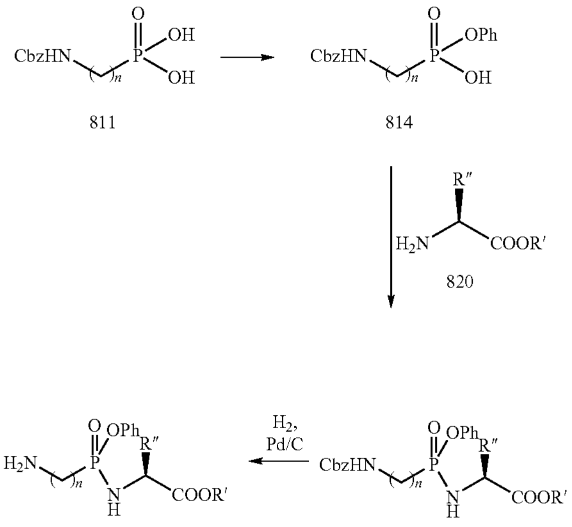

811 814 820 815 816

Following the similar procedures, replacement of amino acid esters 820 with lactates 821 (Scheme 1003) provides mono-phosphonic lactates 823. Lactates 823 are useful intermediates to form the phosphonate compounds of the invention.

Scheme 1003

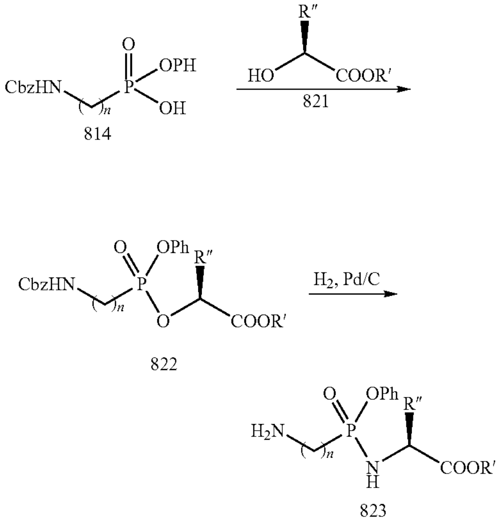

814 821 822 823

Scheme 1004

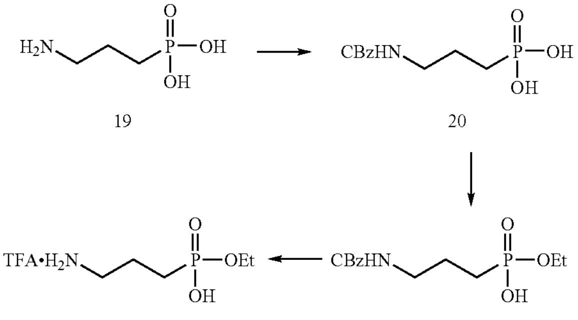

19 20 21 22

Scheme 1005

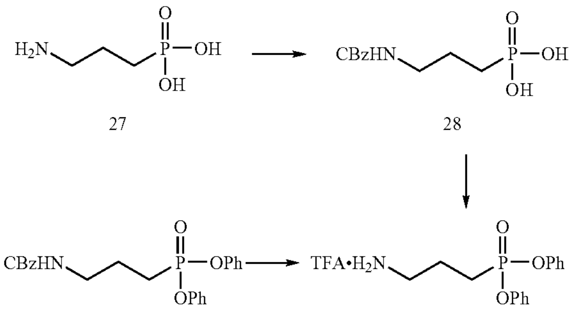

27 28 29 30

Example 1

To a solution of 2-aminoethylphosphonic acid (1.26 g, 10.1 mmol) in 2N NaOH (10.1 mL, 20.2 mmol) was added benzyl chloroformate (1.7 mL, 12.1 mmol). After the reaction mixture was stirred for 2 d at room temperature, the mixture was partitioned between $Et_2O$ and water. The aqueous phase was acidified with 6N HCl until pH=2. The resulting colorless solid was dissolved in MeOH (75 mL) and treated with Dowex 50W×8-200 (7 g). After the mixture was stirred for 30 minutes, it was filtered and evaporated under reduced pressure to give carbamate 28 (2.37 g, 91%) as a colorless solid (Scheme 1005).

To a solution of carbamate 28 (2.35 g, 9.1 mmol) in pyridine (40 mL) was added phenol (8.53 g, 90.6 mmol) and 1,3-dicyclohexylcarbodiimide (7.47 g, 36.2 mmol). After the reaction mixture was warmed to 70° C. and stirred for 5 h, the mixture was diluted with $CH_3CN$ and filtered. The filtrate was concentrated under reduced pressure and diluted with EtOAc. The organic phase was washed with sat. $NH_4Cl$, sat. $NaHCO_3$, and brine, then dried over $Na_2SO_4$, filtered, and evaporated under reduced pressure. The crude product was chromatographed on silica gel twice (eluting 40-60% EtOAc/hexane) to give phosphonate 29 (2.13 g, 57%) as a colorless solid.

To a solution of phosphonate 29 (262 mg, 0.637 mmol) in iPrOH (5 mL) was added TFA (0.05 mL, 0.637 mmol) and 10% Pd/C (26 mg). After the reaction mixture was stirred under $H_2$ atmosphere (balloon) for 1 h, the mixture was filtered through Celite. The filtrate was evaporated under reduced pressure to give amine 30 (249 mg, 100%) as a colorless oil (Scheme 1005).
Scheme Section A
Exemplary methods of preparing the compounds of the invention are shown in Schemes 1-7 below. A detailed description of the methods is found in the Experimental section below.
Scheme1
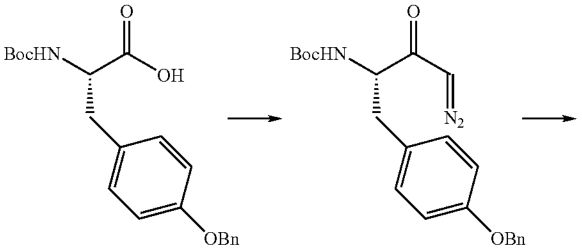
1
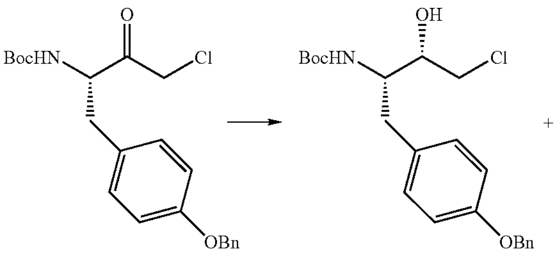
2
3
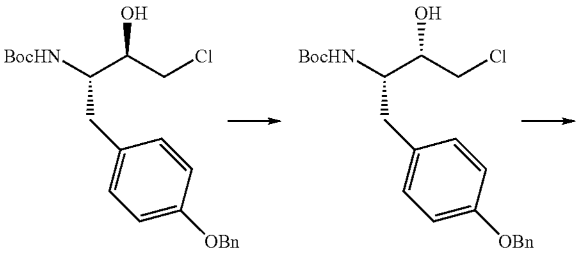
4
3
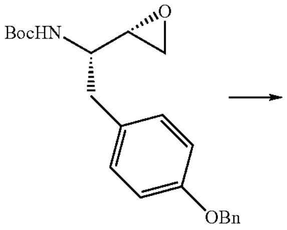
5
-continued
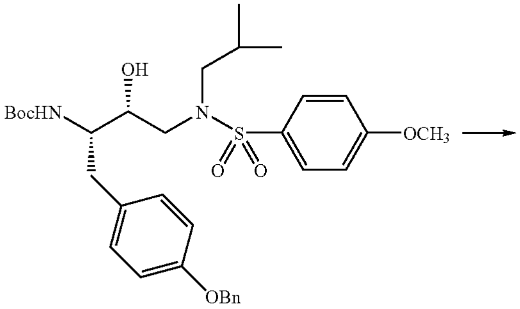
6
Scheme 2
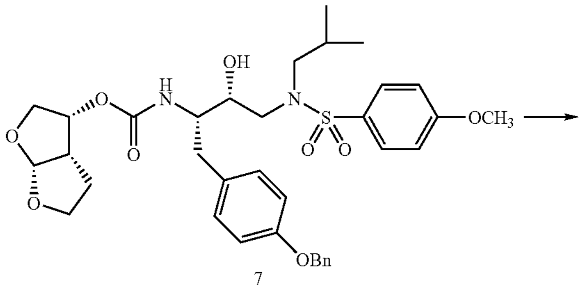
7
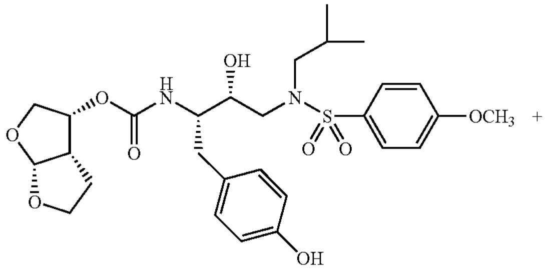
8
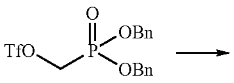
9
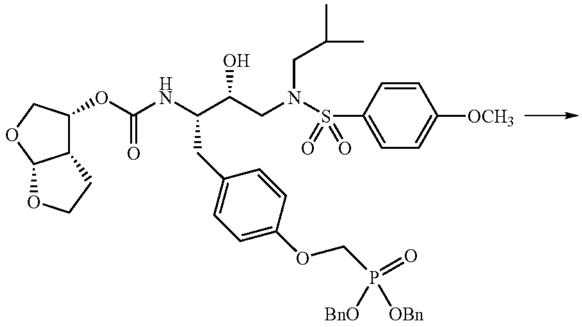
10

-continued
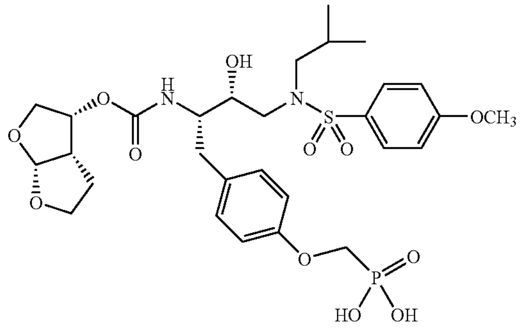
11
Scheme 3
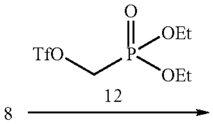
12
8
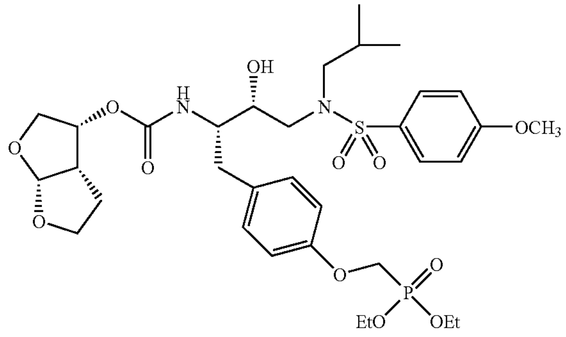
13
11
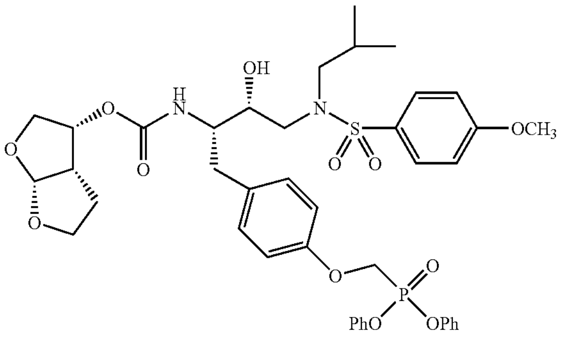
14
11
-continued
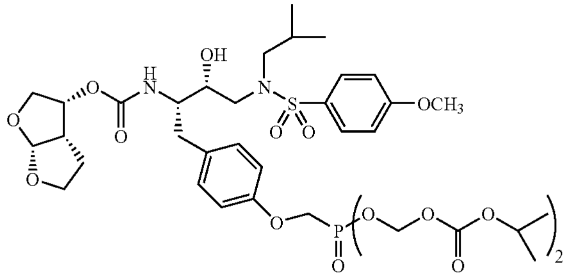
15
Scheme 4
11
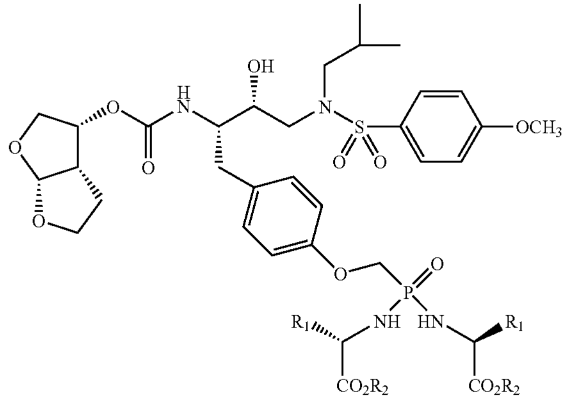
16a-f
Scheme 5
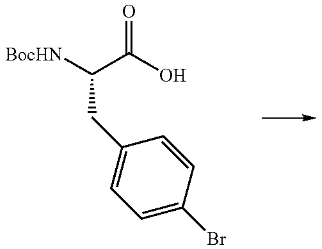
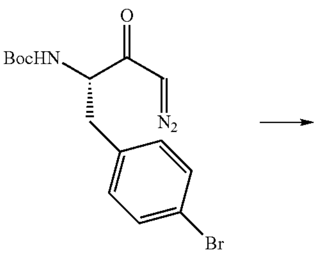
17

-continued
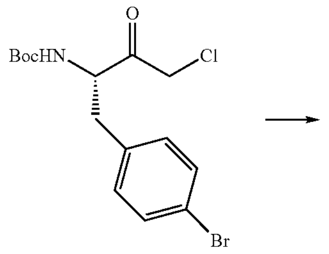
18
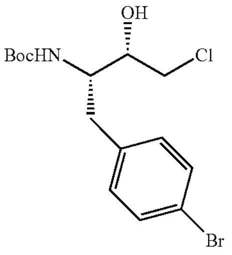
19
+
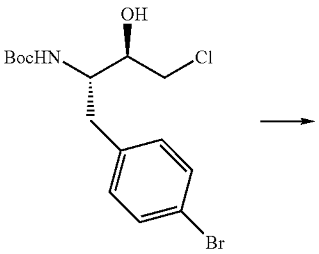
20
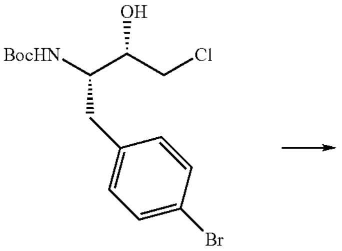
19
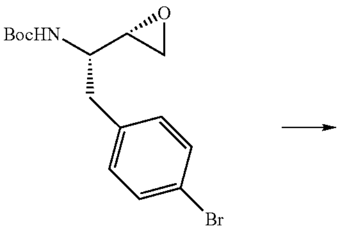
21
-continued
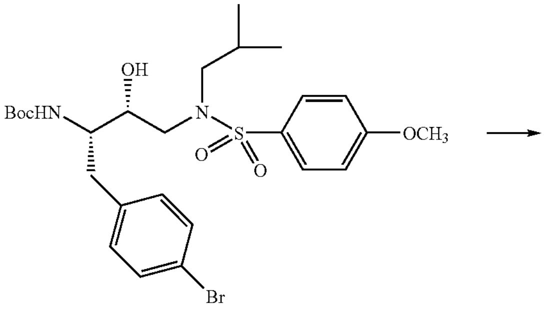
22
Scheme 6
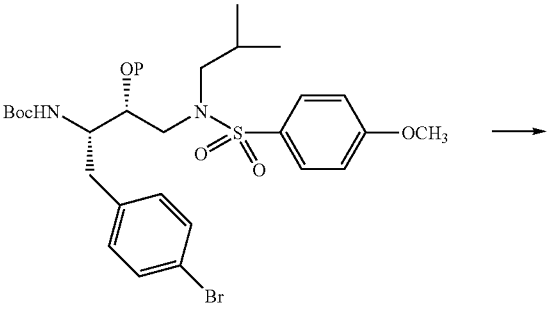
23
P = tert-butyldimethylsilyl
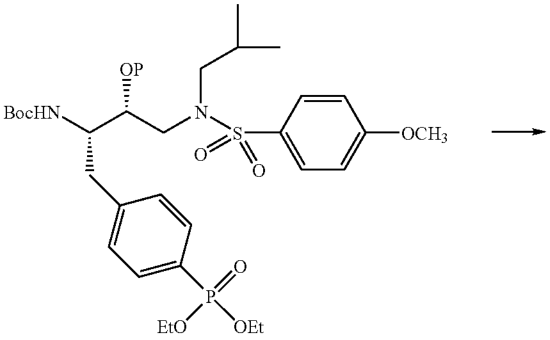
24
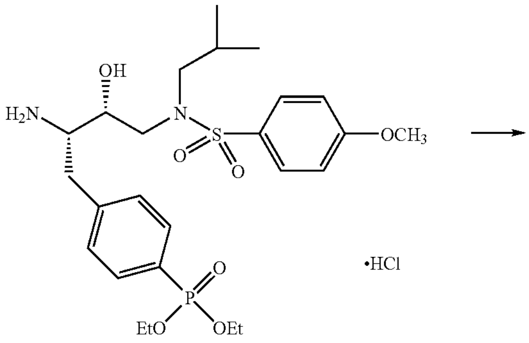
25

-continued
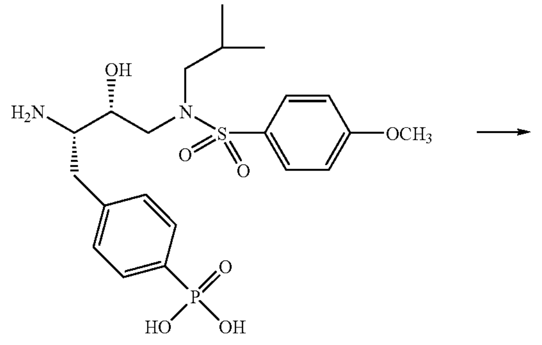
26
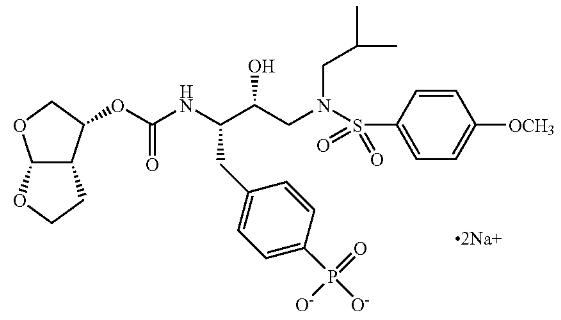
27
25
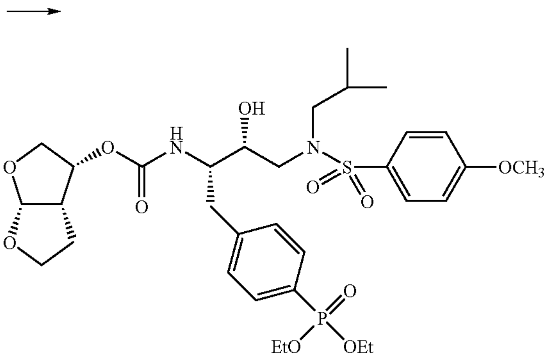
28
Scheme 7
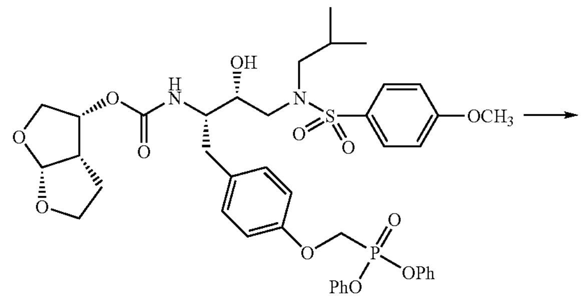
14
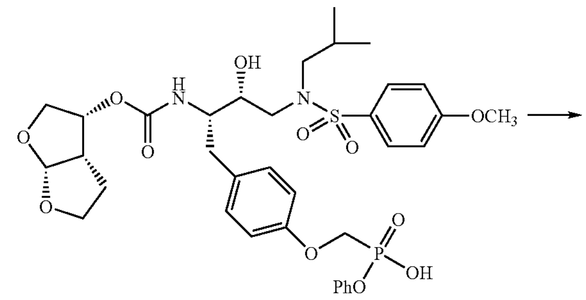
29
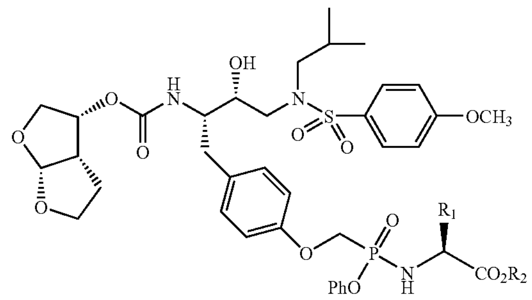
30
Scheme Section B
Alternative exemplary methods of preparing the compounds of the invention are shown in Schemes 101-113 below.
Scheme 101
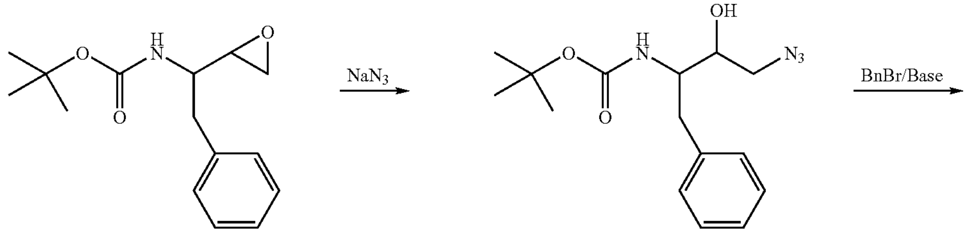
1
2

-continued

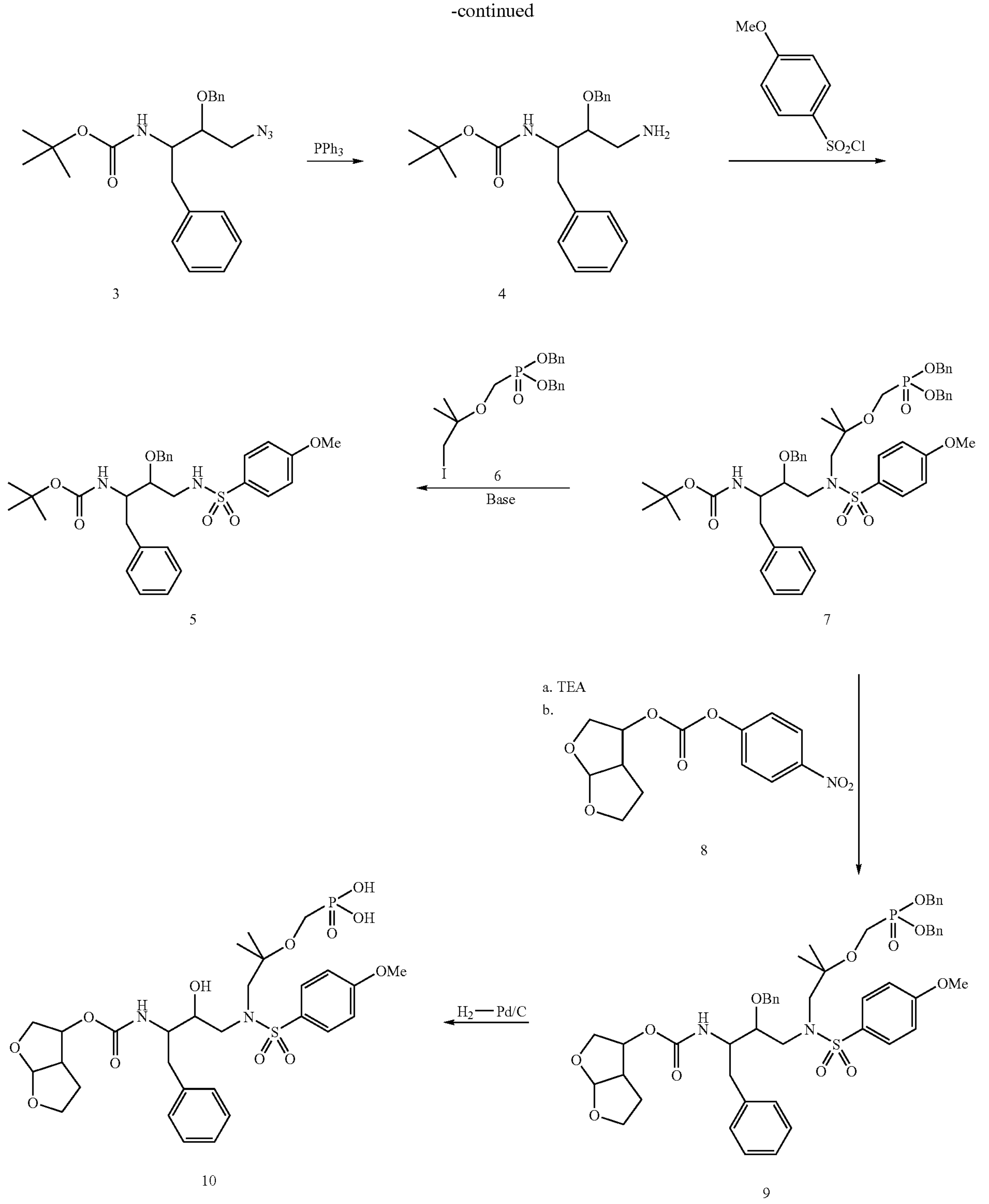

Treatment of commercially available epoxide 1 with sodum azide (Bioorg. & Med. Chem. Lett., 5, 459, 1995) furnishes the azide intermediate 2. The free hydroxyl is converted to benzyl ether 3 by treating it with benzyl bromide in the presence of base such as potassium carbonate. Compound 4 is achieved by the reduction of the azide group with triphenyl phosphine, as described in the publication Bioorg. & Med. Chem. Lett., 7, 1847, 1997. Conversion of the amino group to its sulfonamide derivative 5 is achieved by treating the amine with stoichiometric amounts of sulfonyl chloride. Regioselective alkylation is performed (as shown in the article J. Med. Chem., 40, 2525, 1997) on the sulfonamide nitrogen using the iodide 6 (J. Med. Chem., 35, 2958, 1992) to get the compound 7. Upon TFA catalyzed deprotection of BOC group followed by the reaction with bisfuranyl carbonate 8 (for a similar coupling see, J. Med. Chem., 39, 3278, 1996) furnishes the compound 9. Final deprotection of the protecting groups by catalytic hydrogenolysis result the compound 10.

Scheme 102

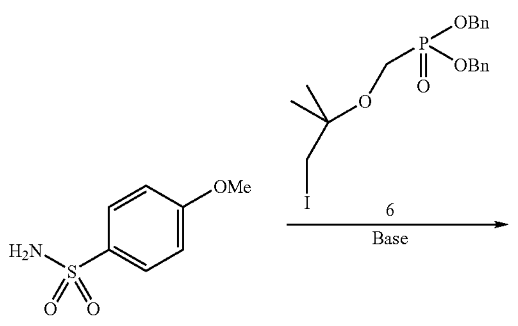

11

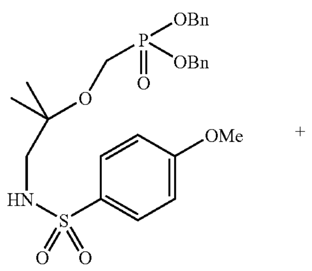

12

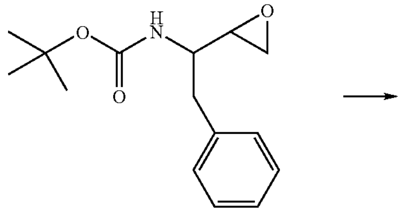

1

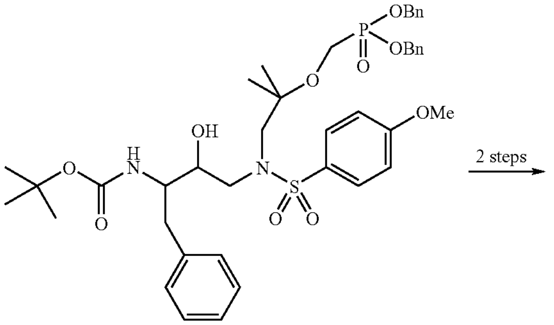

13

-continued

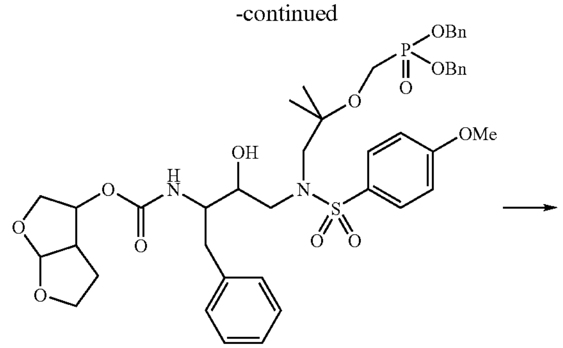

14

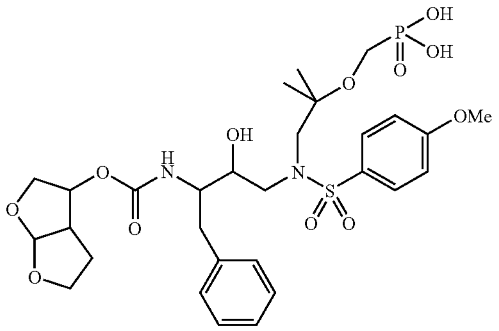

10

The sulfonamide 11 is readily alkylated with the iodide 6 (J. Med. Chem., 35, 2958, 1992) to get the intermediate 12. Regioselective epoxide opening (JP-9124630) of the epoxide 1 with 12 furnishes the intermediate 13. Deprotection of the BOC group followed by the treatment of bisfuranyl carbonate 8 yields the intermediate 14 which is subjected to hydrogenation to furnish the compound 10.

Scheme 103

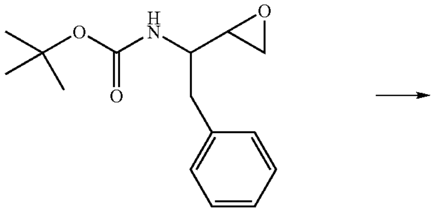

1

-continued

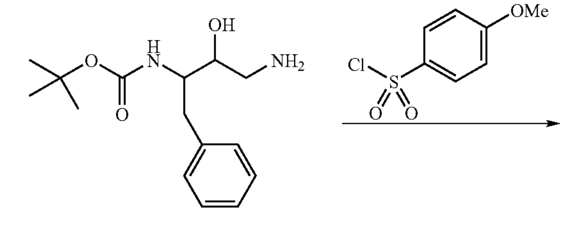

15

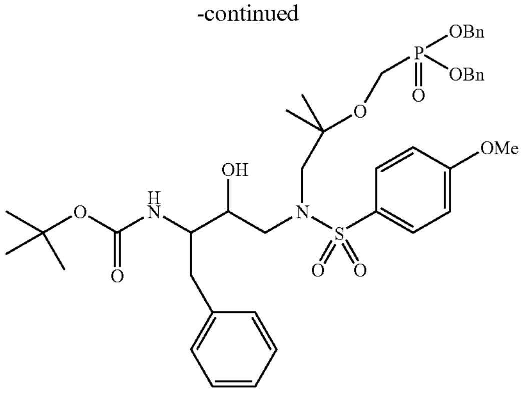

13

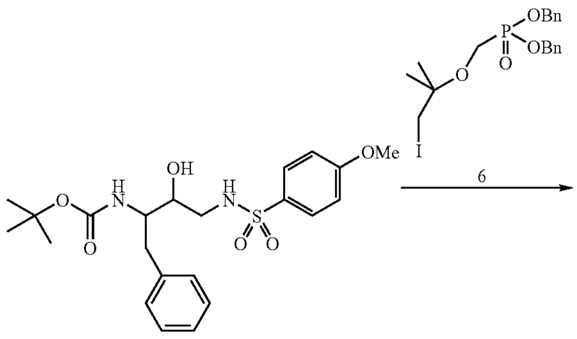

16

The epoxide 1 is converted to the aminohydroxyl derivative 15 using the known procedure (J. Med. Chem., 37, 1758, 1994). Sulfonylation of 15 using benzene sulfonylchloride affords the compound 16. Installation of the side chain to get the intermediate 13 is achieved by alkylation of sulfonamide nitrogen with iodide 6. The intermediate 13 is converted to the compound 10 using the same sequence as shown in scheme 102.

Scheme 104

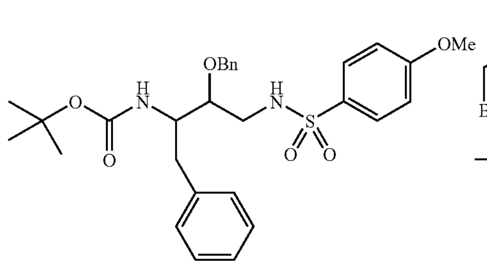

5

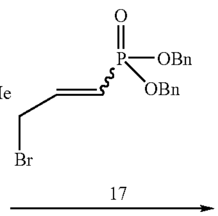

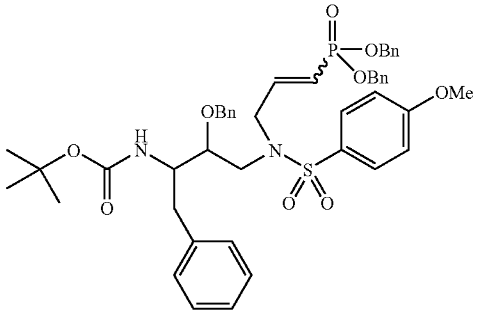

18

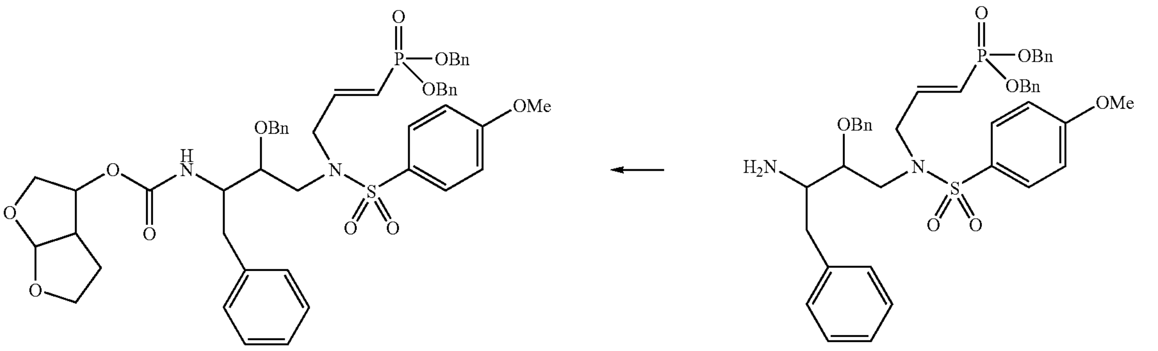

20

19

-continued

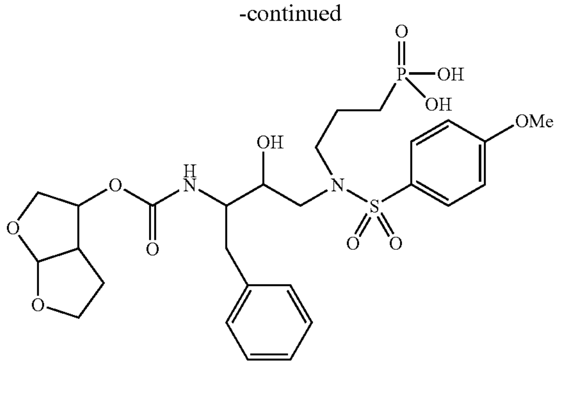

21

Sulfonamide 5 is alkylated under basic conditions using the allyl bromide 17 (Chem. Pharm. Bull., 30, 111, 1982) to get the intermediate 18. Similar transformation is reported in literature (J. Med. Chem., 40, 2525, 1997). Hydrolysis of BOC group with TFA and acylation of the resulting amine 19 with bisfuranyl carbonate 8 yields the compound 20. Hydrogenation using Pd/C catalysis under $H_2$ atmosphere affords the phosphonic acid 21.

Scheme 105

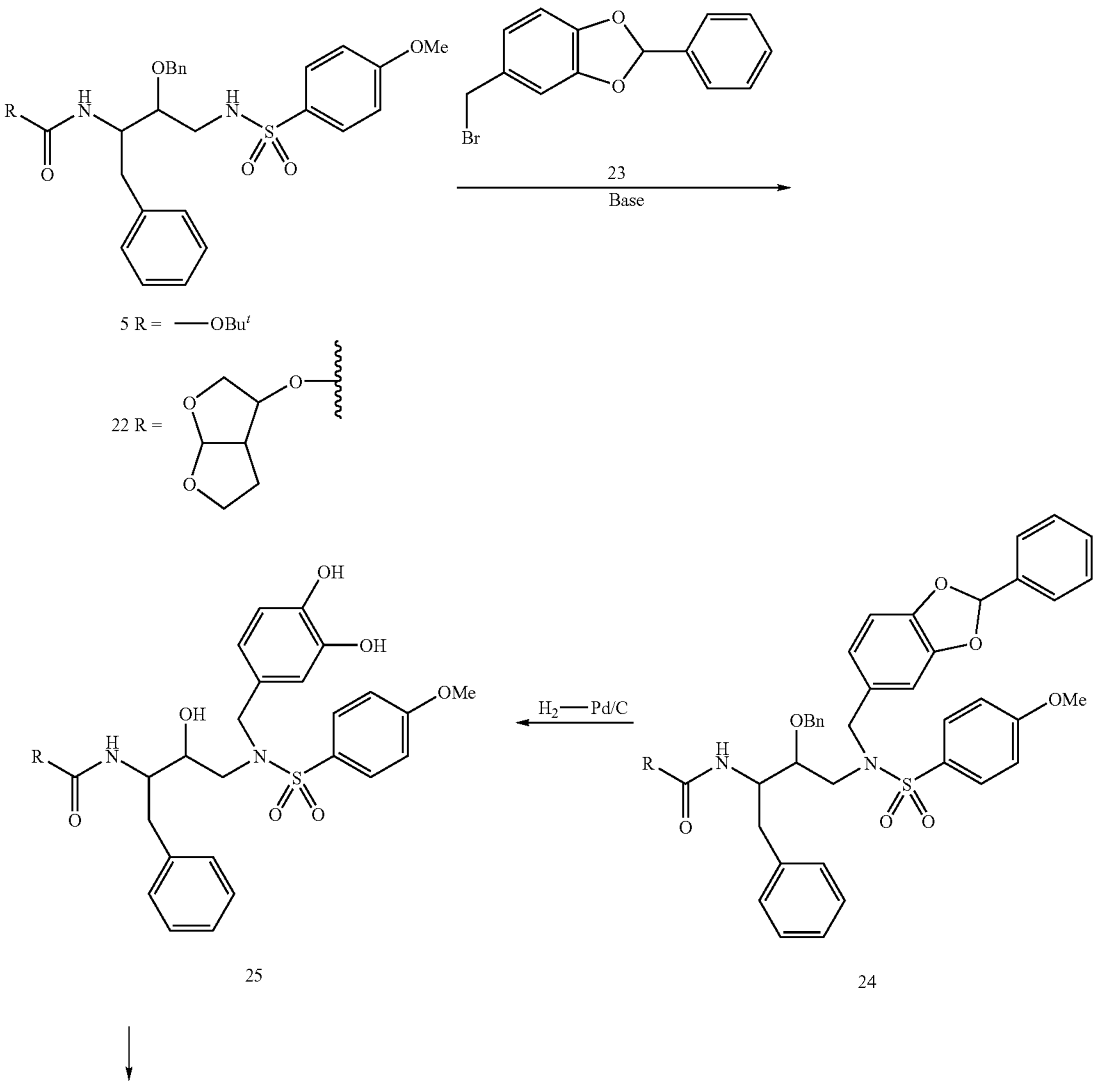

5 R = —$OBu^t$

22 R =

25

24

-continued
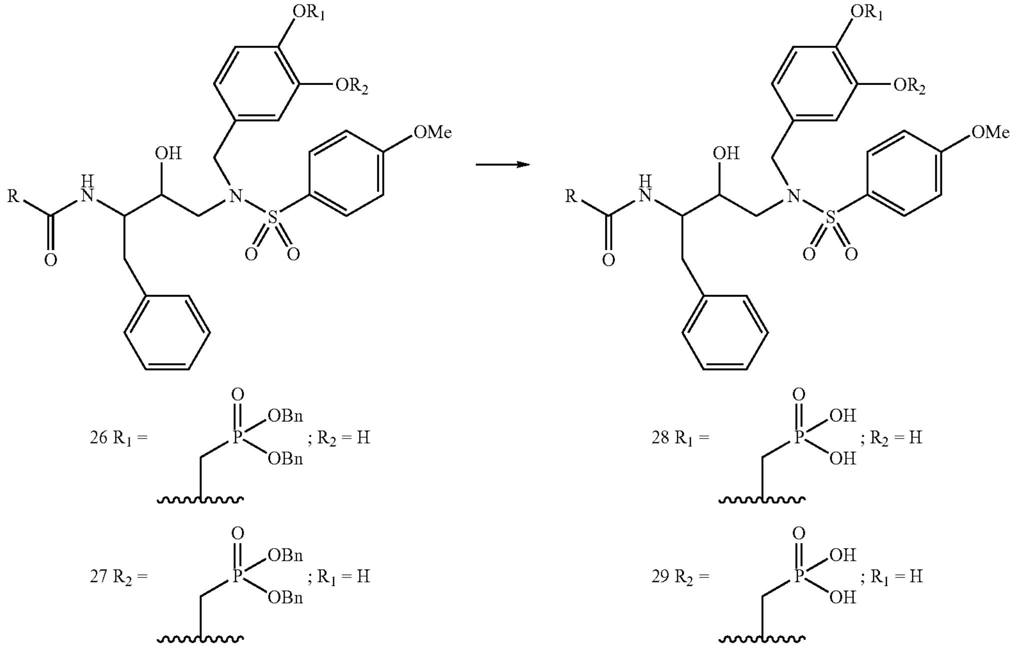
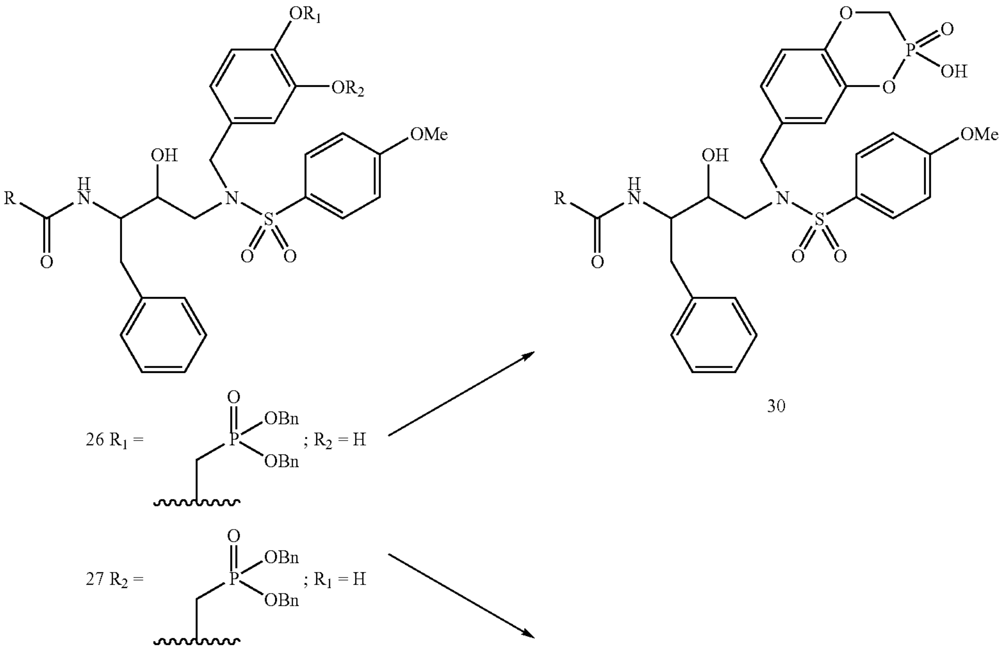
30

-continued

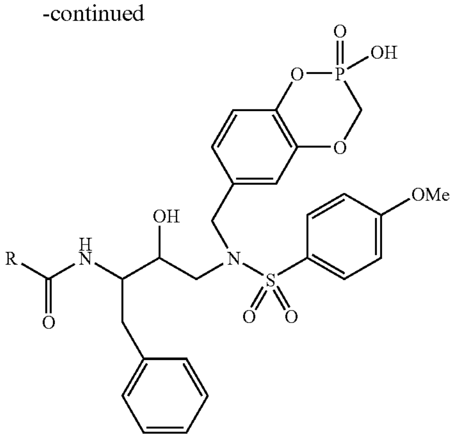

31

Sulfonamide 5 is converted to 22 via hydrolysis of BOC group with TFA and acylation with bisfuranyl carbonate 8. The sulfonamide 22 is alkylated with the bromide 23 (J. Med. Chem., 40, 2525, 1997) to get the compound 24, which upon hydrogenolysis gives the catechol 25. Alkylation of the phenolic groups using dibenzylhydroxymethyl phosphonate (J. Org. Chem., 53, 3457, 1988) affords regioisomeric compounds 26 and 27. These compounds 26 and 27 are hydrogenated to get the phophonic acids 28 and 29, respectively. Individual cyclic phosphonic acids 30 and 31 are obtained under basic (like NaH) conditions (U.S. Pat. No. 5,886,179) followed by hydrogenolysis of the dibenzyl ester derivatives 26 and 27.

Scheme 106

In this route, compound 25 is obtained by conducting a reaction between the epoxide 32 and the sulfonamide 33 using the conditions described in the Japanese Patent No. 9124630.

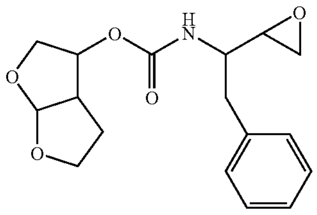

32

+

-continued

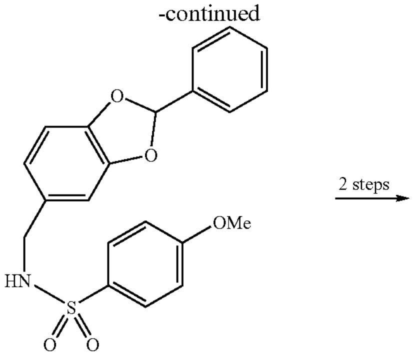

33

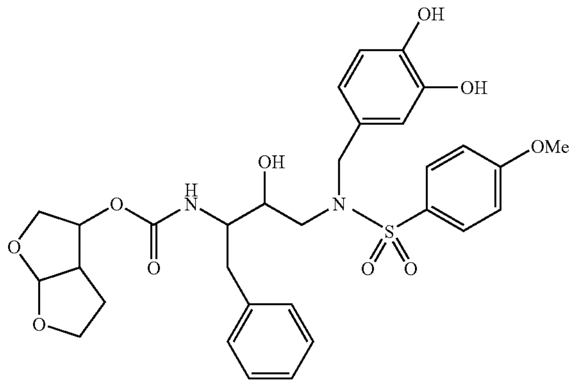

25

Epoxide 32 and sulfonamide 33 are synthesized utilizing similar methodology delineated in the same patent.

Scheme 107
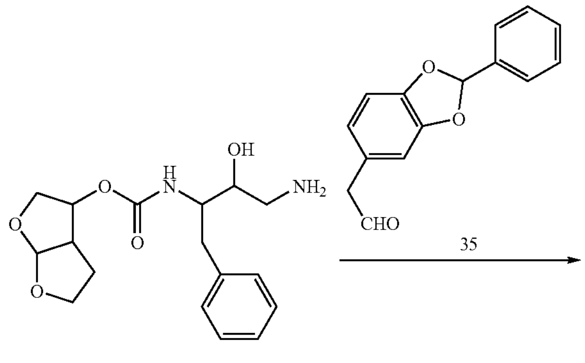
35
34
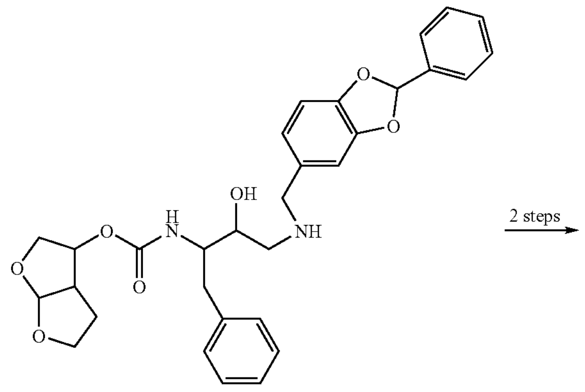
36
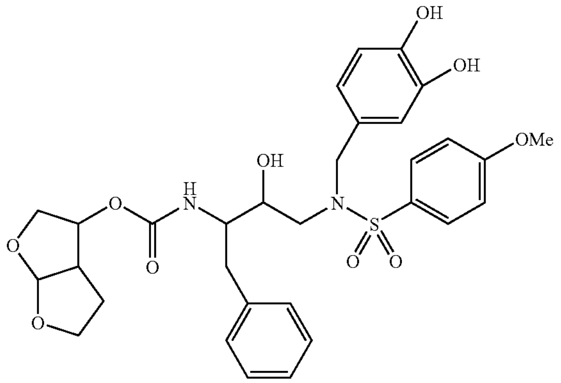
25
Compound 34 is obtained from 32 using similar sequence depicted in J. Med. Chem., 37, 1758, 1994. Reductive amination (for similar transformation see WO 00/47551) of compound 34 with aldehyde 35 furnishes the intermediate 36 which is converted to the compound 25 by sulfonylation followed by hydrogenation.
Scheme 108
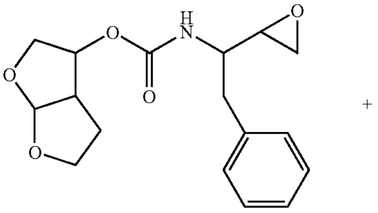
32
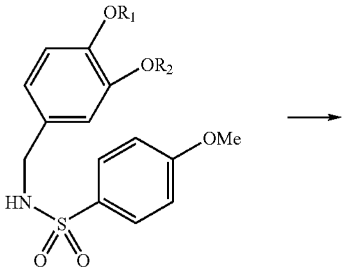
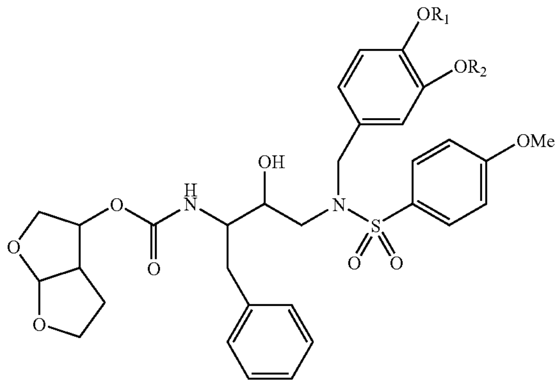
26
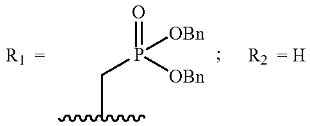
27
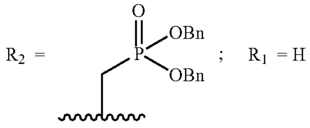
37
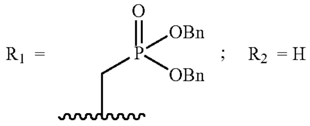
38
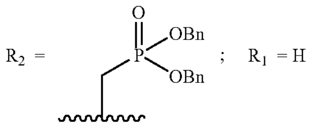

Treatment of epoxide 32 with sulfonamides 37 and/or 38 under conditions described in Japanese Patent No. 9124630 furnishes 26 and 27.

Scheme 109

Reductive amination of aminohydroxyl intermediate 34 with the aldehydes 39 and 40 as described in patent WO 00/47551, furnish 41 and 42 which undergoes smooth sulfonylation to give 26 and 27.

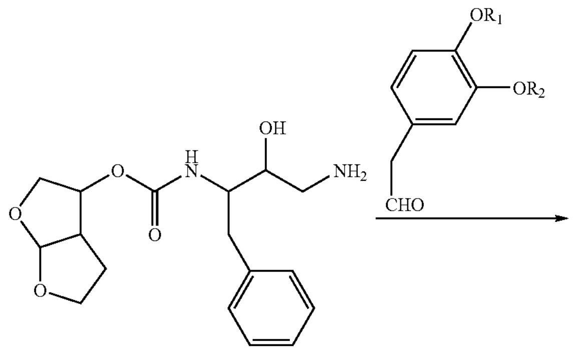

34

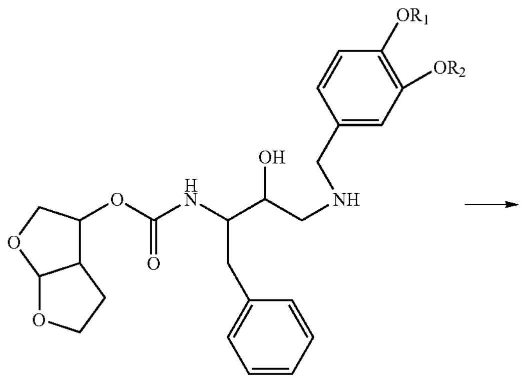

39 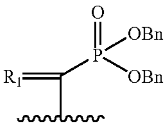 ; $R_2$ = H 41 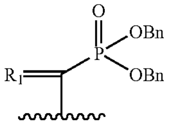 ; $R_2$ = H

40 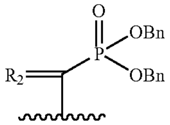 ; $R_1$ = H 42 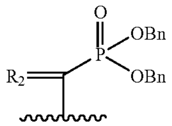 ; $R_1$ = H

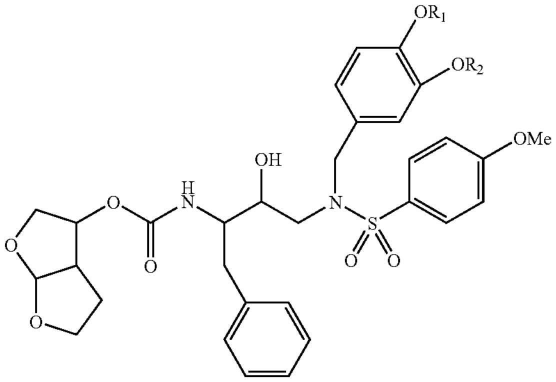

-continued

26 $R_1$ = 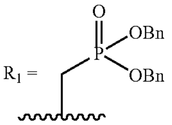 ; $R_2$ = H 27 $R_2$ = 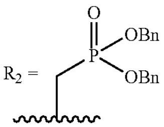 ; $R_1$ = H

Scheme 110

In an alternate approach, where epoxide 32 is opened with benzyl amines 43 and 44 under Condition described above furnishes 41 and 42, respectively. Similar transformations were documented in the Japanese Patent No. 9124630.

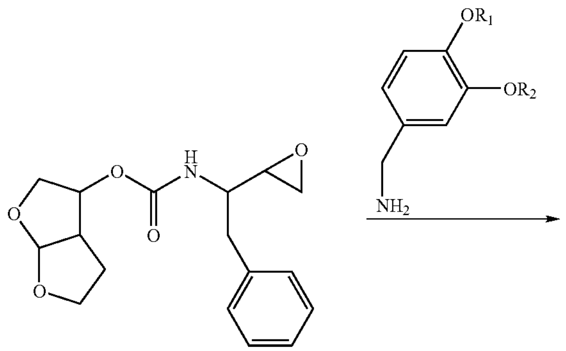

32

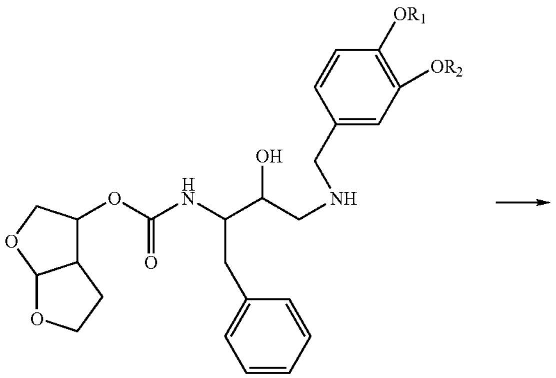

43 $R_1$ = 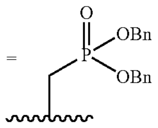 ; $R_2$ = H 41 $R_1$ = 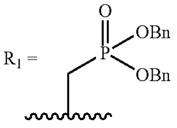 ; $R_2$ = H

44 $R_2$ = 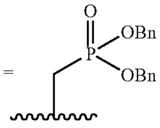 ; $R_1$ = H 42 $R_2$ = 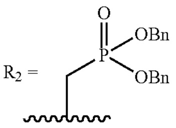 ; $R_1$ = H

Scheme 111
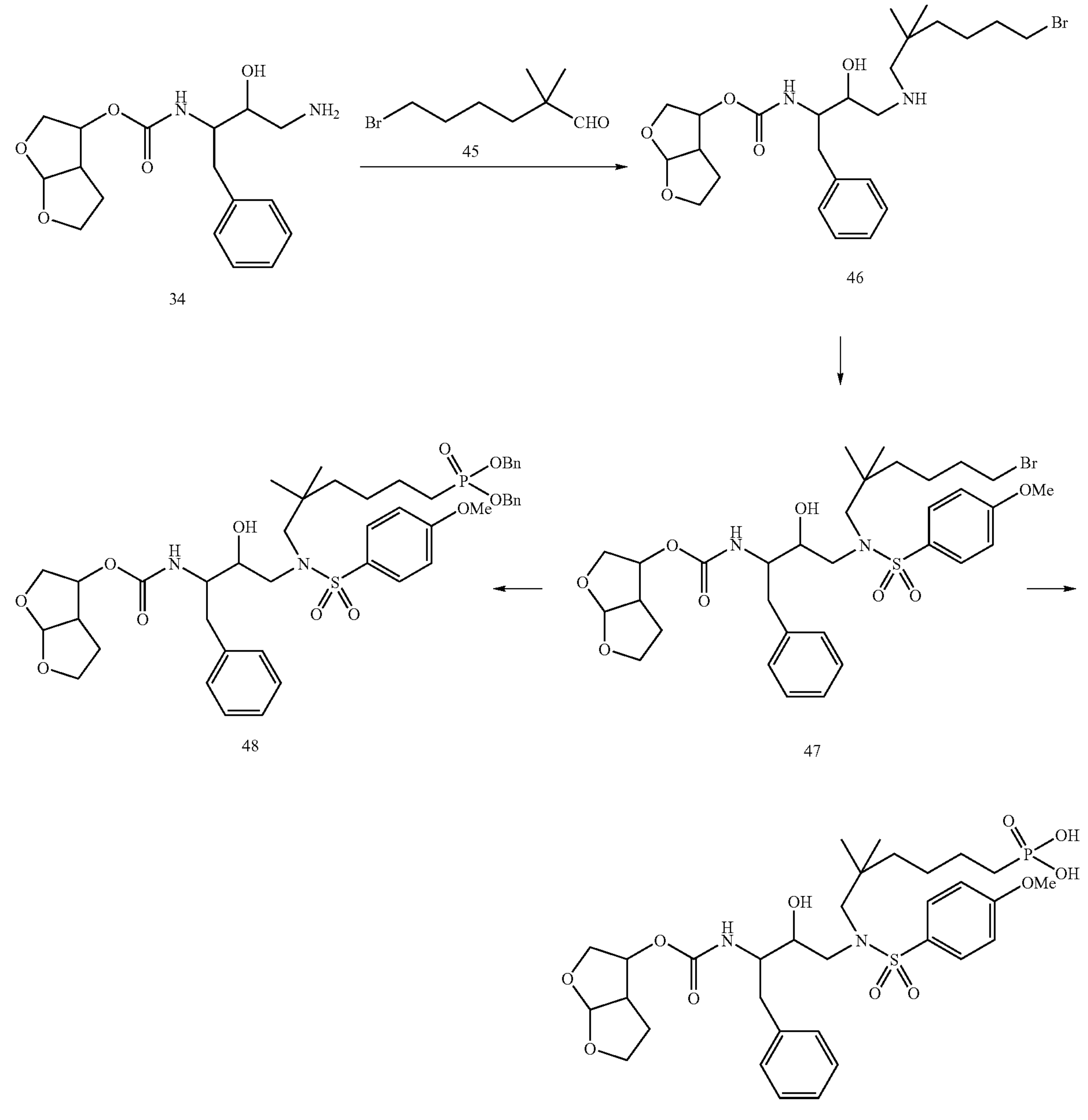
34
45
46
47
48
49
Reductive amination of the bromoaldehyde 45 (J. Organomet. Chem., FR; 122, 123, 1976) with the amine 34 gives 46 which then undergoes sulfonylation to furnish 47. The bromoderivative 47 is converted to the phosphonate 48 under Michaelis-Arbuzov reaction conditions (Bioorg. Med. Chem. Lett., 9, 3069, 1999). Final hydrogenation of 48 delivers the phosphonic acid 49.
Scheme 112
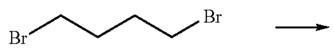
-continued
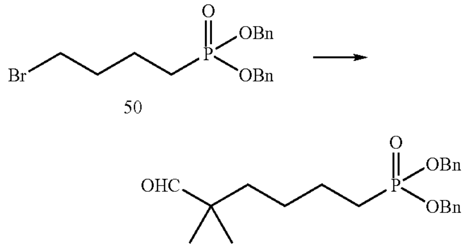
50
51

-continued

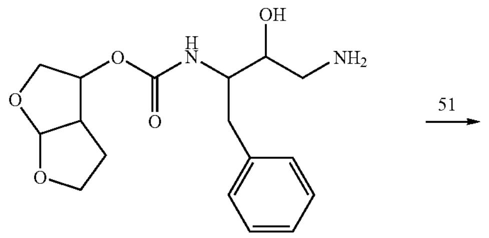

34

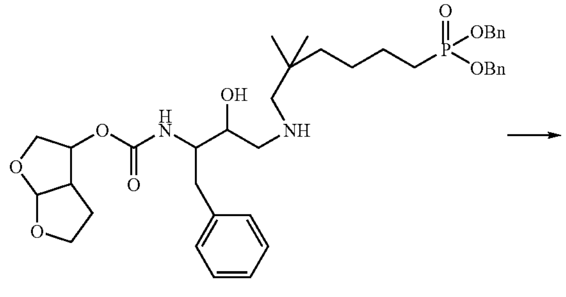

52

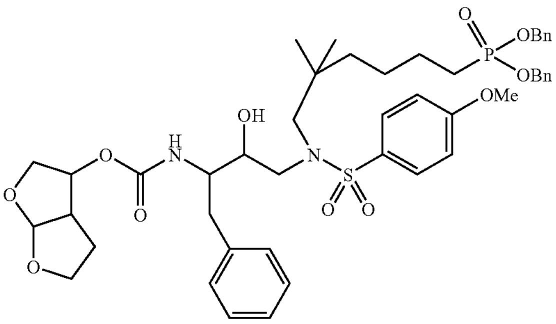

48

The intermediate 48 is also obtained as shown in scheme 112. Reductive amination of the aldehyde 52 with the amine 34 offers the phosphonate 52 and sulfonylation of this intermediate furnishes 48.

Scheme 113

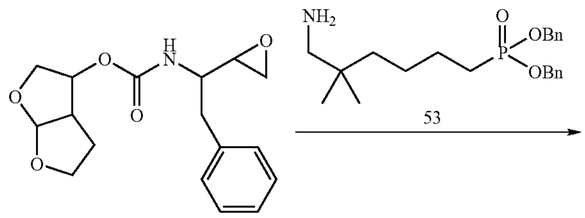

32

-continued

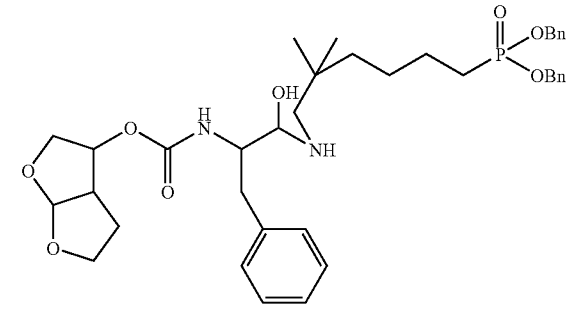

52

Alternatively, compound 52 is obtained from the epoxide 32 by a ring opening reaction with the aminophosphonate 53 (Scheme 113).

Scheme Section C

Scheme 9 is described in the Examples.

Scheme 9

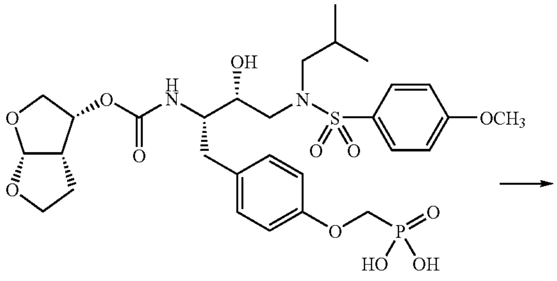

30

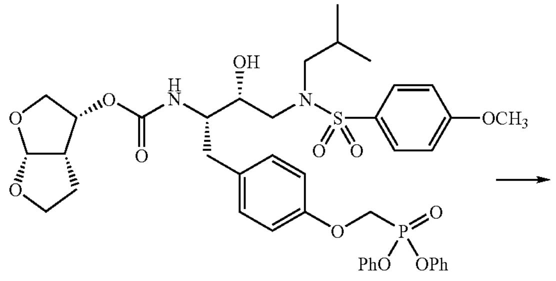

31

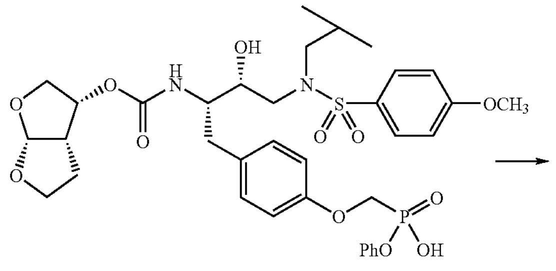

32

-continued
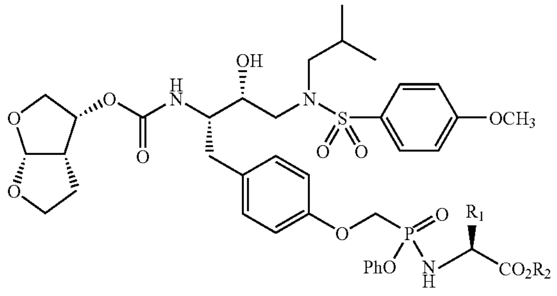
33
Scheme Section D
The following schemes are described in the Examples.
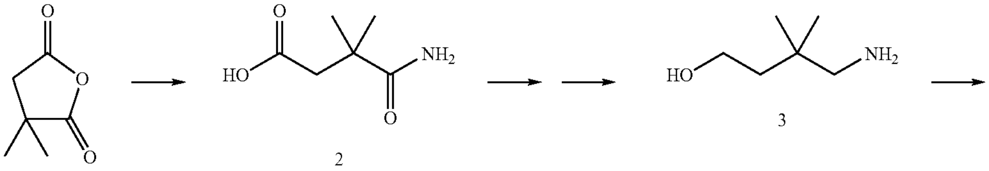
1 2 3
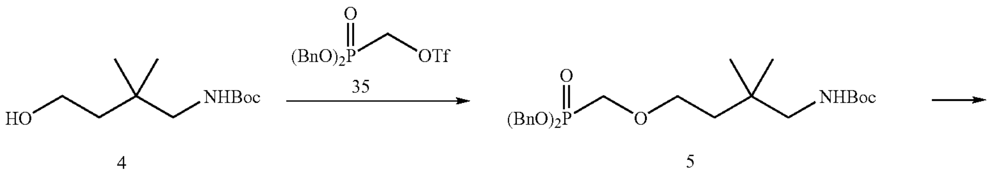
4 5
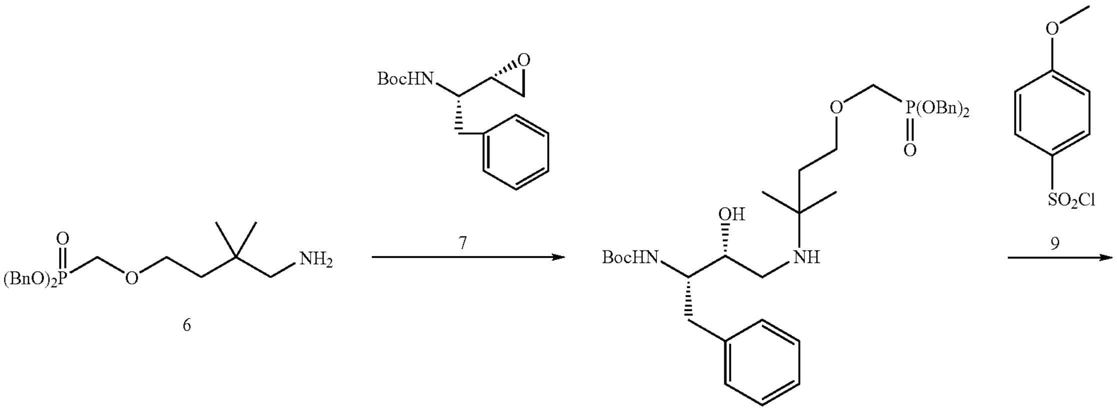
6 8

-continued
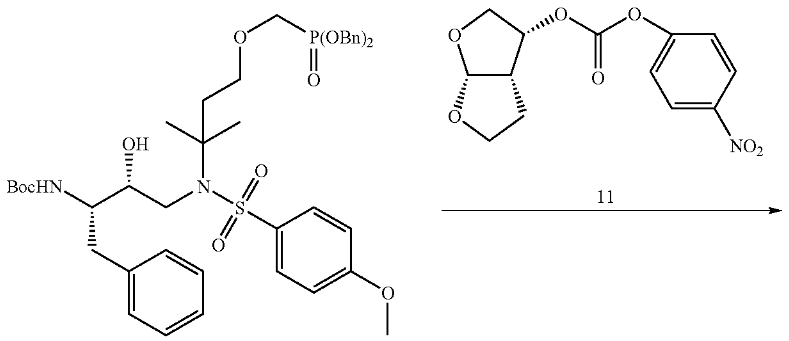
10
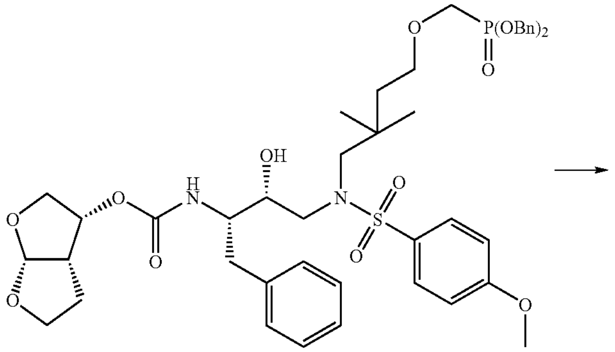
12
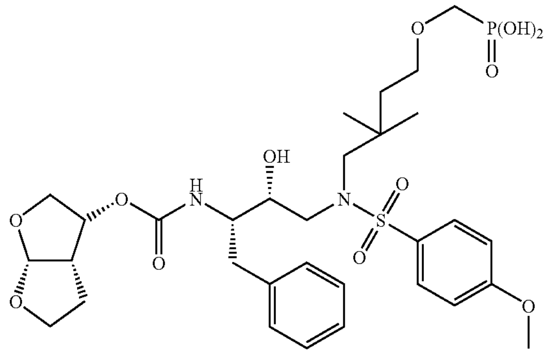
13
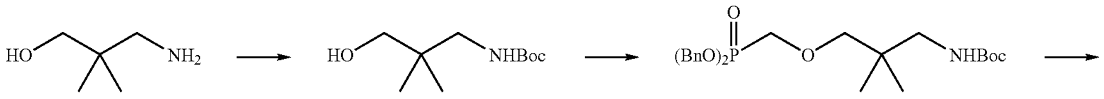
14 15 16
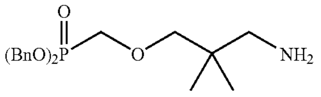
17

-continued
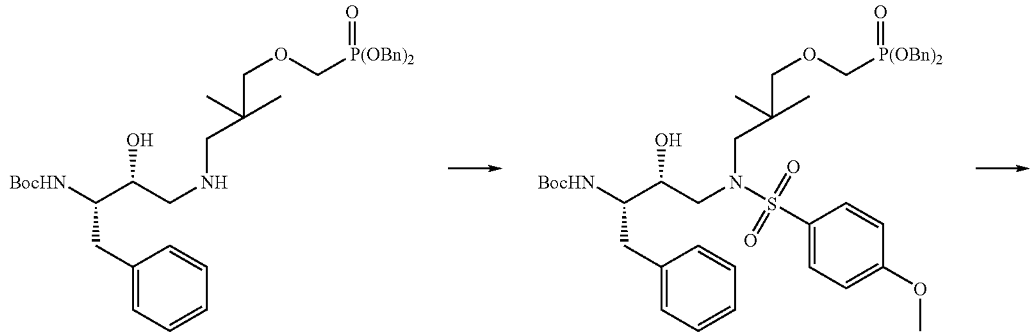
18
19
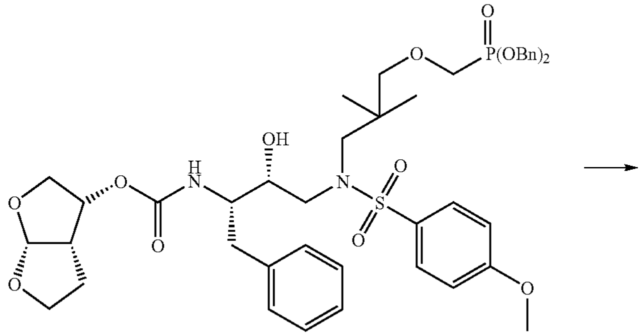
20
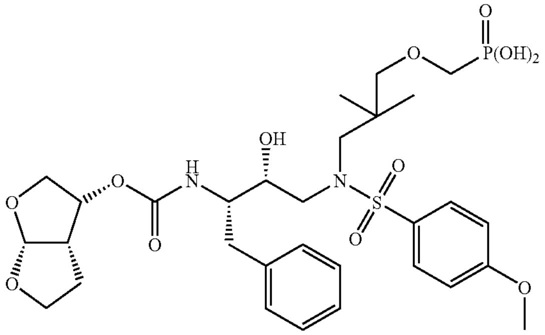
21
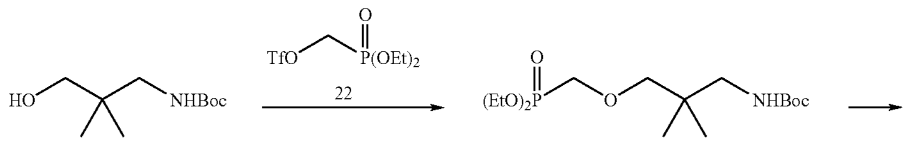
15
23
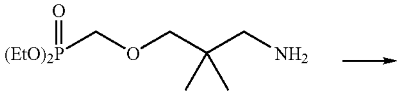
24
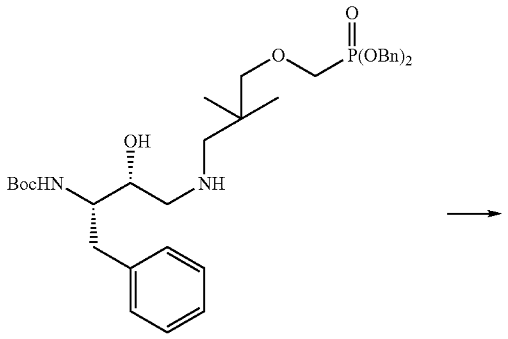
25

-continued
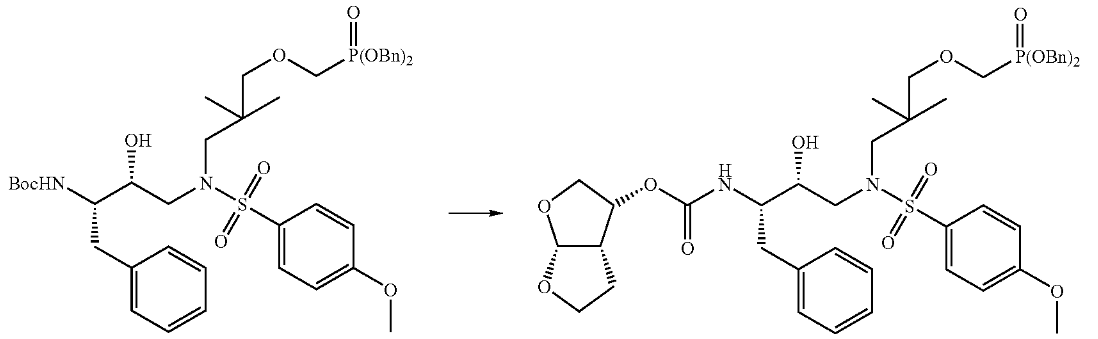
26 27
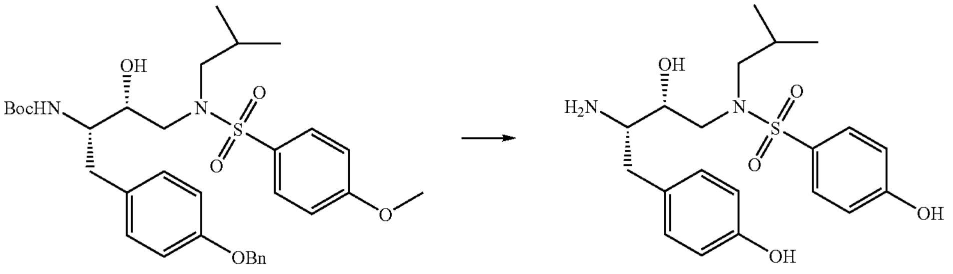
28 29
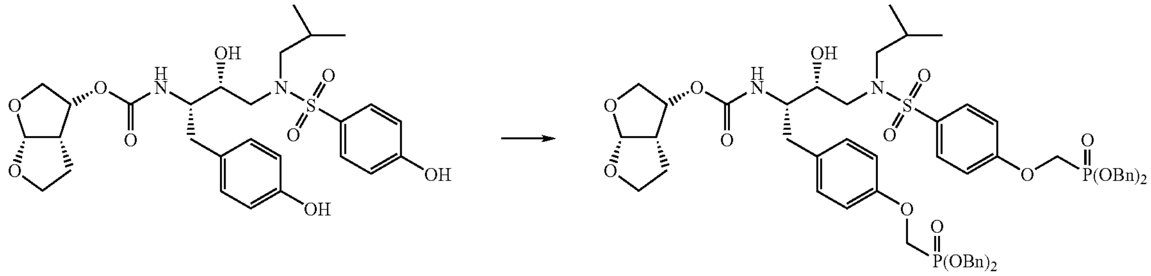
30 31
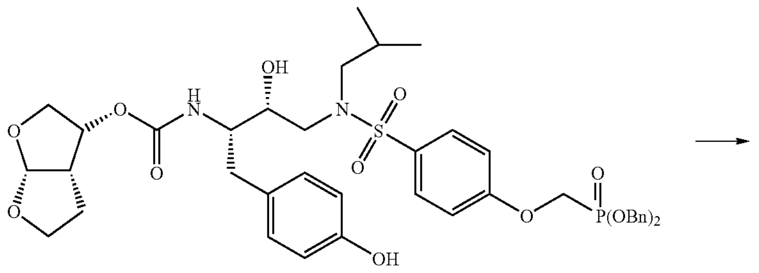
32

-continued
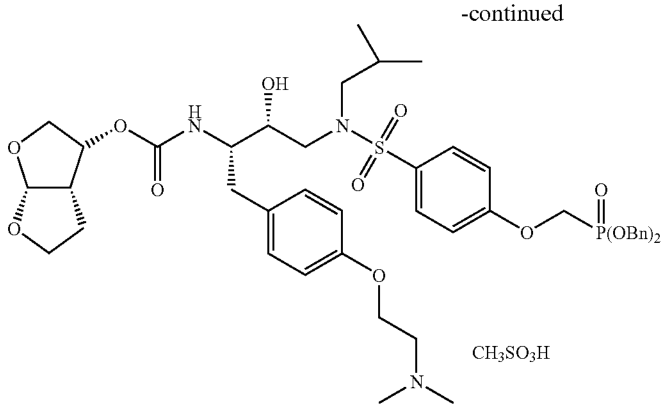
34
Scheme Section E
Schemes 1-3 are described in the examples.
Scheme 1
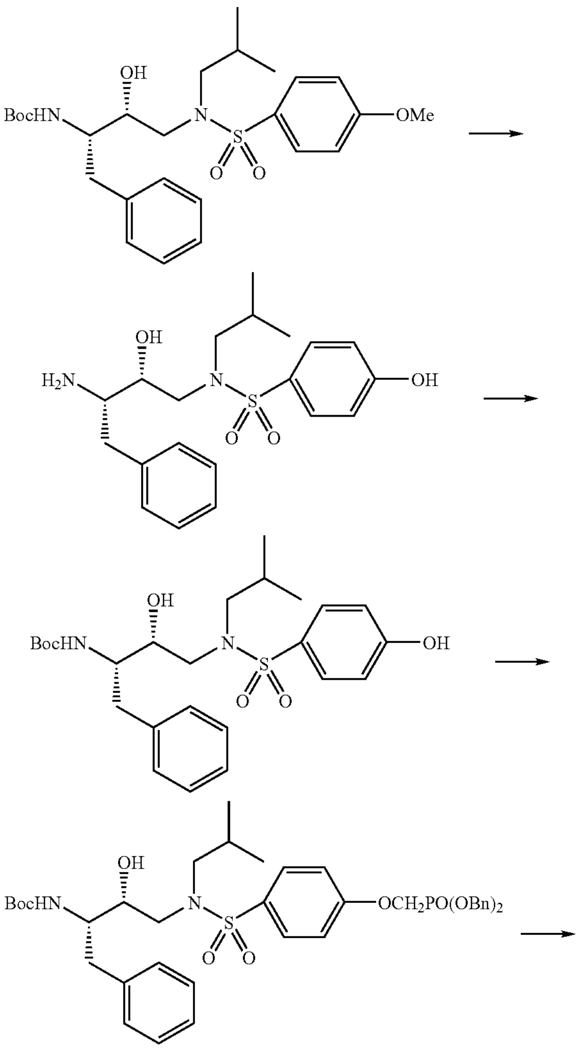
-continued
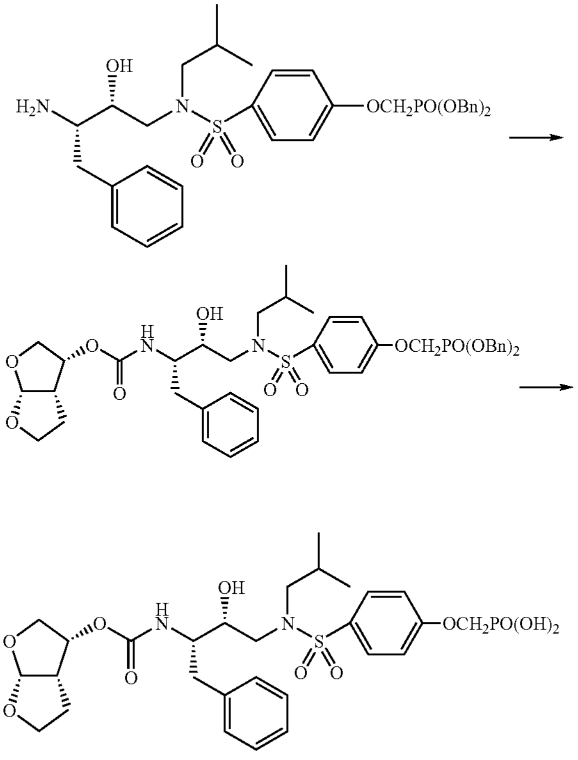
Scheme 2
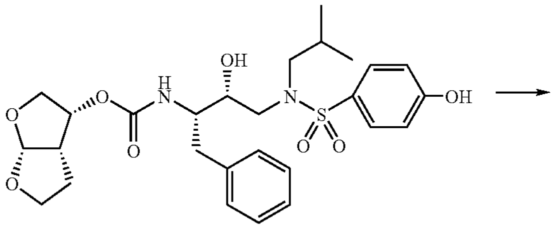

-continued
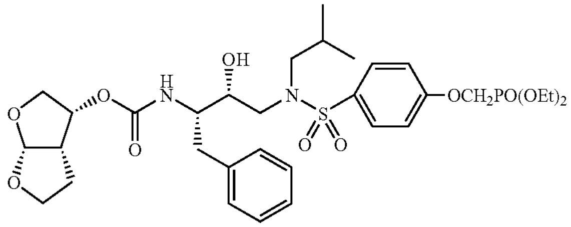
Scheme 3
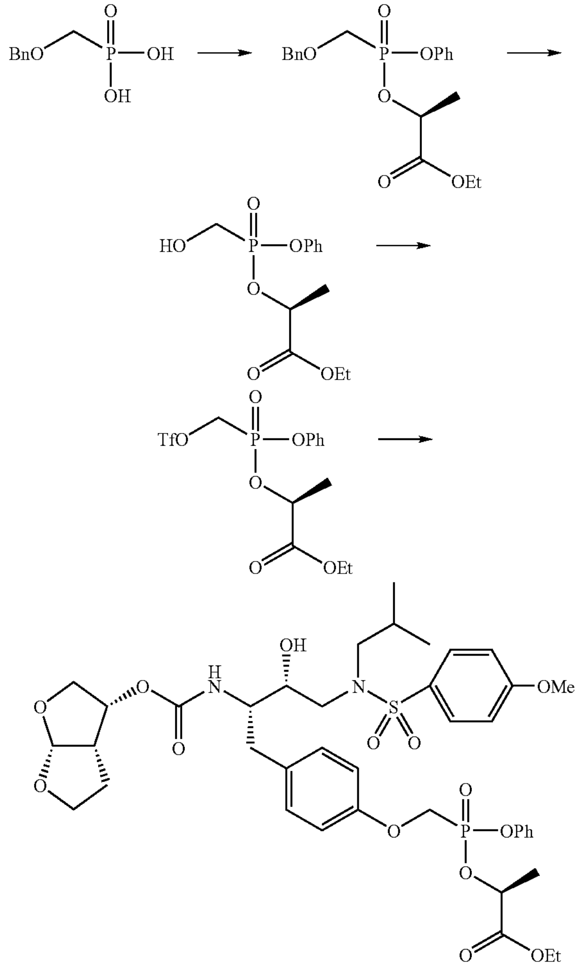
Scheme Section F
Schemes 1-5 are described in the examples.
Scheme 1
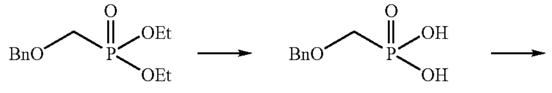
1 2
-continued
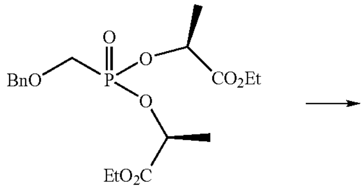
3
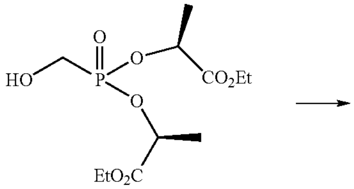
4
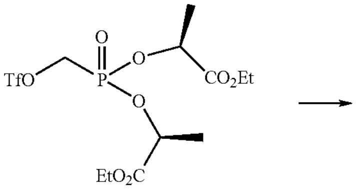
5
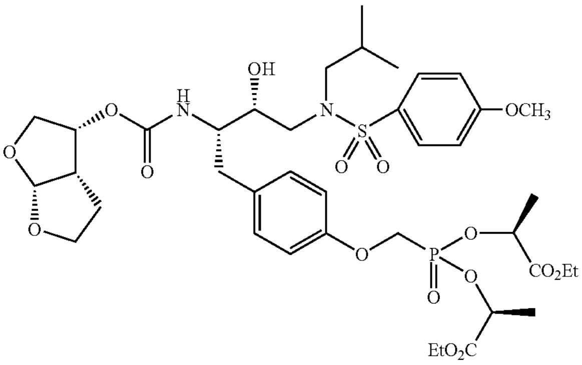
6
Scheme 2
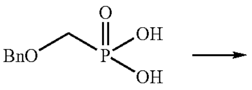
2
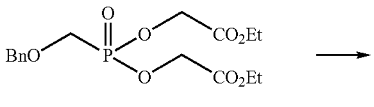
7
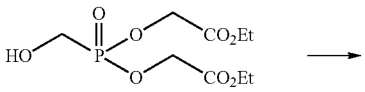
8

-continued
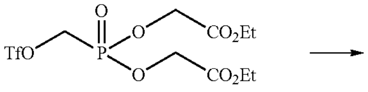
9
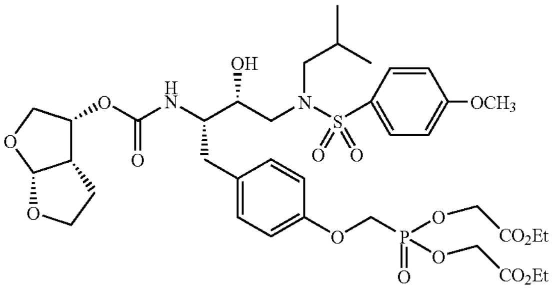
10
Scheme 3
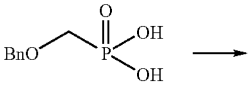
2
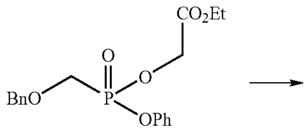
11
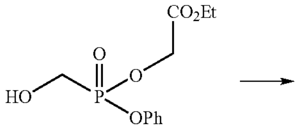
12
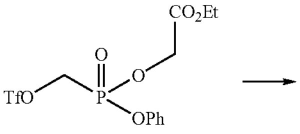
13
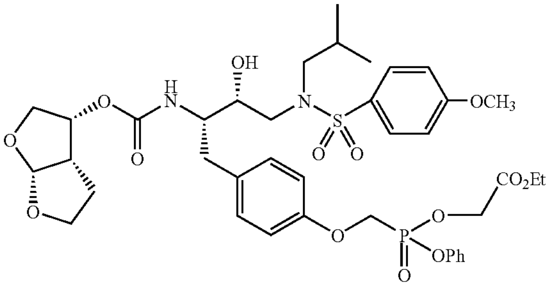
14
Scheme 4
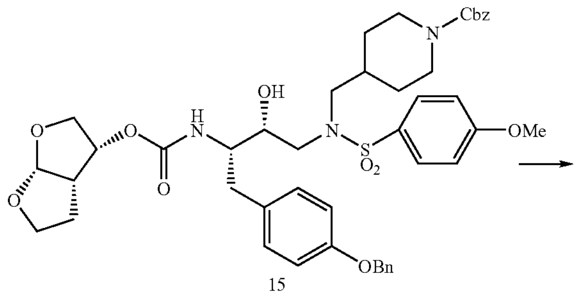
15
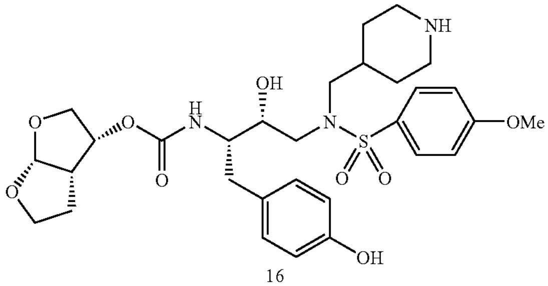
16
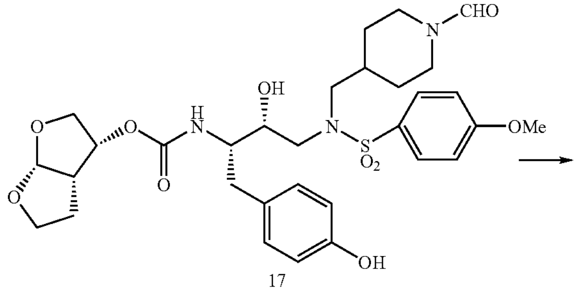
17
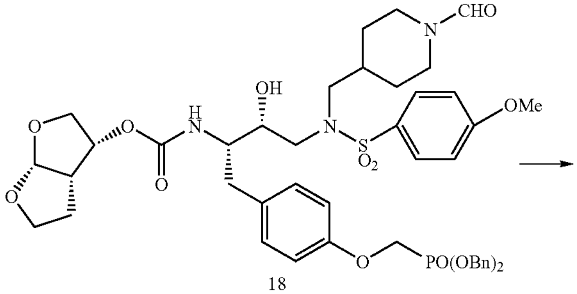
18
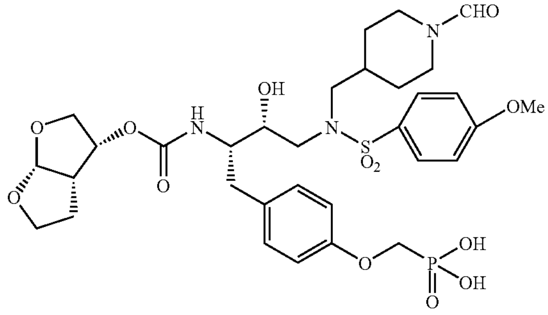
19

Scheme 5
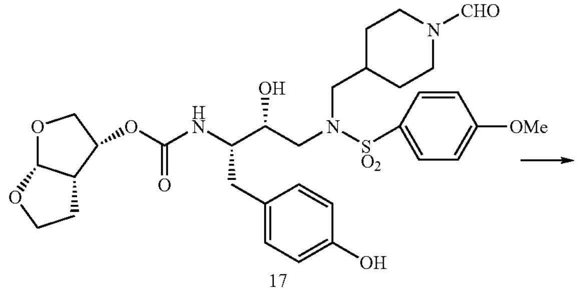
17
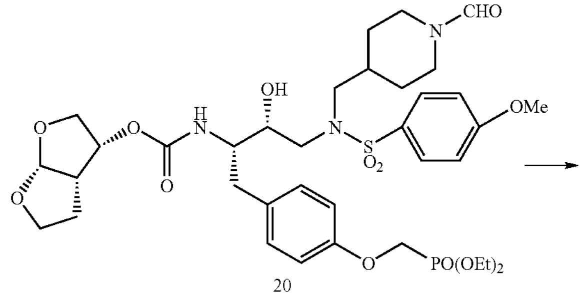
20
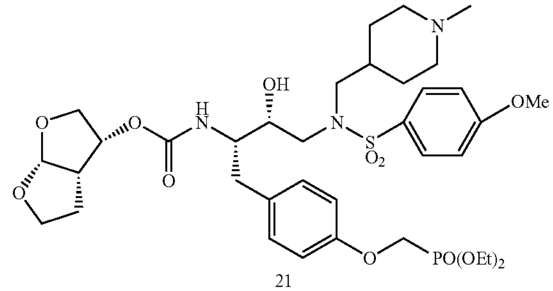
21
Scheme Section G
Schemes 1 to 9 are described in the examples.
Scheme 1
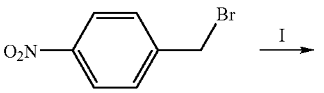
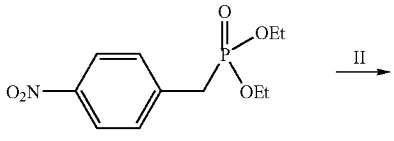
1
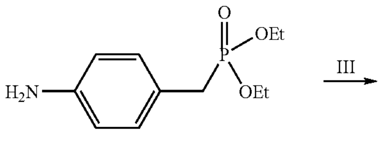
2
-continued
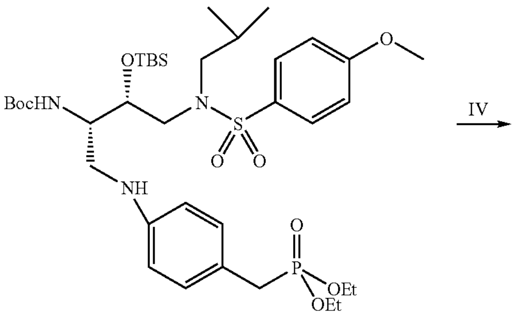
3
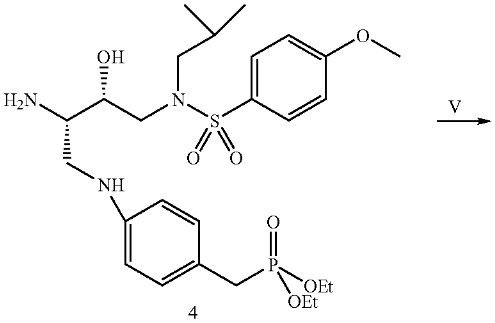
4
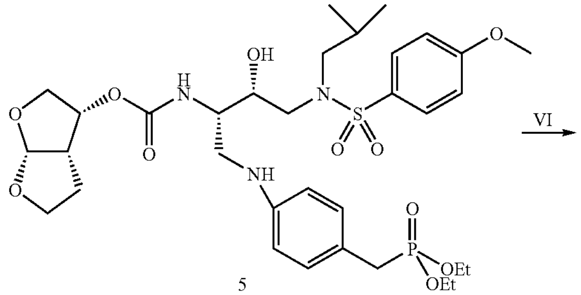
5
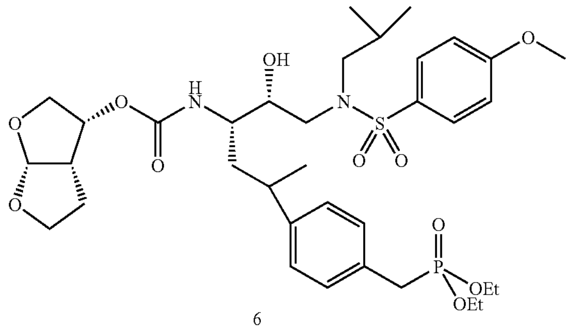
6
I. $P(OEt)_3$/120 C.;
II. $H_2$/10% PD-C.;
III. See Scheme Section H, Scheme 13, Compound 48/$NaBH_3CN$/HOAc/MeOH;
IV. a. TFA; b. n-$Bu_4NF$;
V. bisfuracarbonate/DMAP;
VI. HCHO/$NaBH_3CN$/HOAc/MeOH Scheme 2
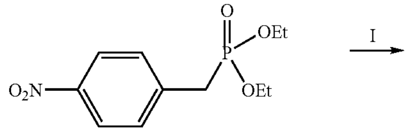
1
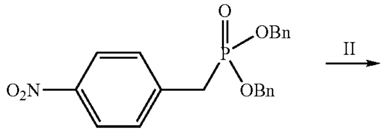
7
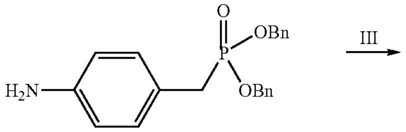
8
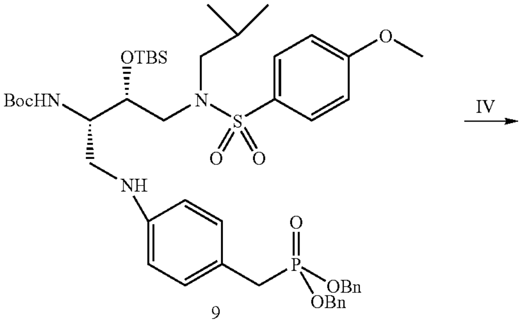
9
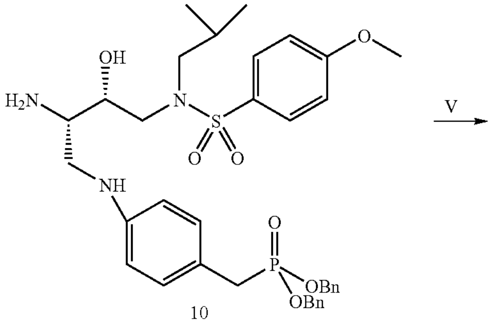
10
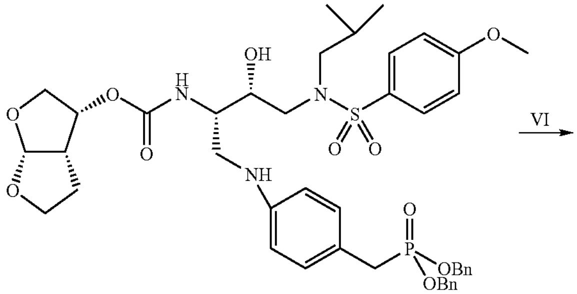
11
-continued
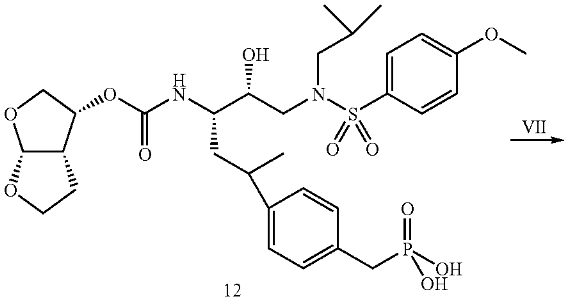
12
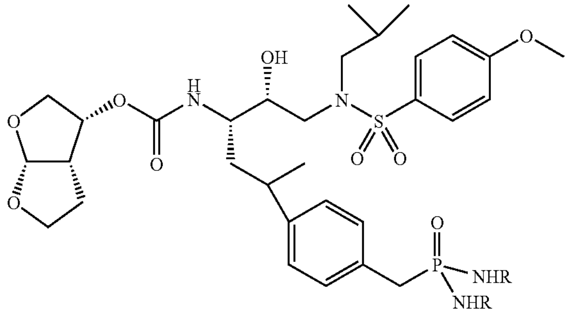
13
R =
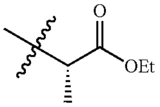
I. a.TMSBr; b. $SOCl_2$/60 C.; c. BnOH/$Et_3N$;
II. Zn/HOAc;
III. See Scheme Section H, Scheme 13, Compound 48/$NaBH_3CN$/HOAc/MeOH;
IV. a. TFA; b. n-$Bu_4NF$;
V. bisfurancarbonate/DMAP;
VI. $H_2$/10%Pd-C;
VIII. $RNH_2PPh_3$/aldrithiol
Scheme 3
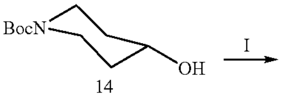
14
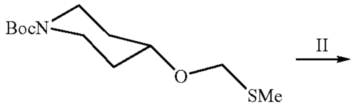
15
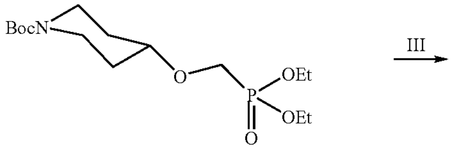
16
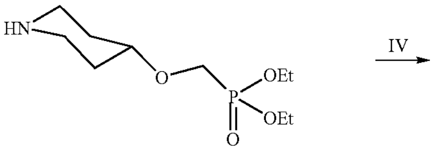
17

-continued
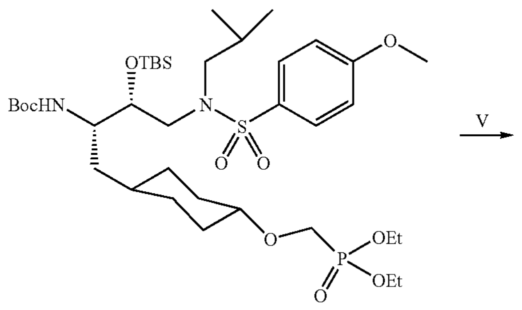
18
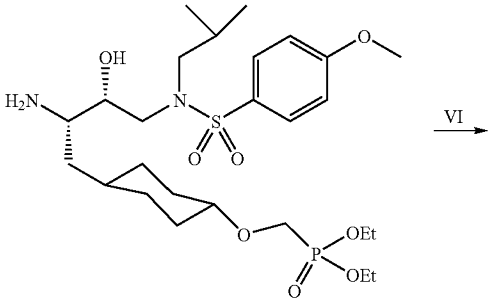
19
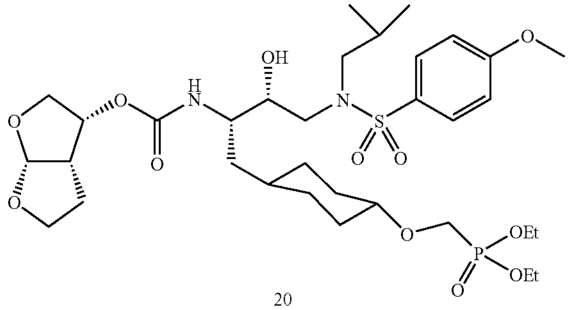
20
I. a. NaH; b. MTMCl;
II. a. $SOCl_2$; b. $P(OEt)_3$/120 C.;
III. TFA;
IV. See Scheme Section H, Scheme 13, Compound 48/$NaBH_3CN$/HOAc/MeOH;
V. a. TFA; b. n-$Bu_4NF$
VI. bisfurancarbonate/DMAP
Scheme 4
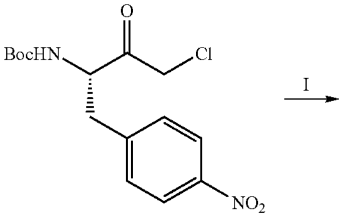
21
-continued
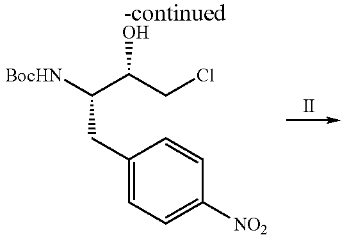
22
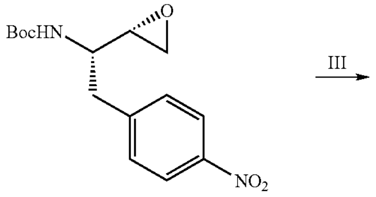
23
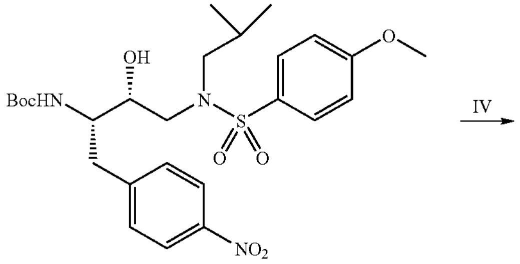
24
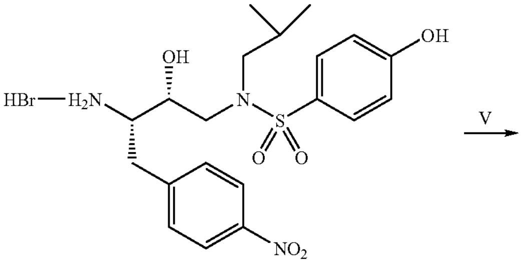
25
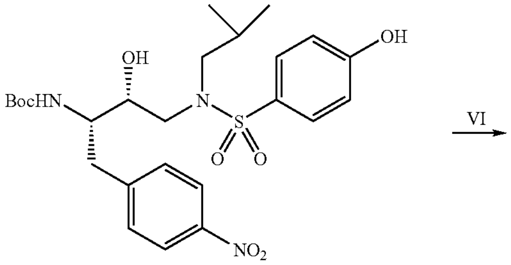
26

-continued

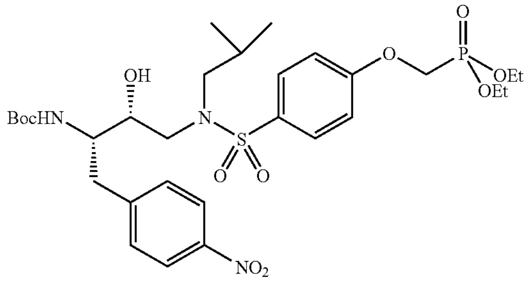

27

I. $NaBH_4/THF/H_2O$;
II. KOH/EtOH;
III. a. isobutylamine/iropropanol/80 C.; b.4-methoxybenzenexulfonyl chloride/$Et_3N$;
IV. $BBr_3/CH_2CL_2$;
V. $Boc_2O/NaHCO_3$;
VI. $TfOCH_2PO(OEt)_2/Cs_2CO_3$ Scheme 5

27

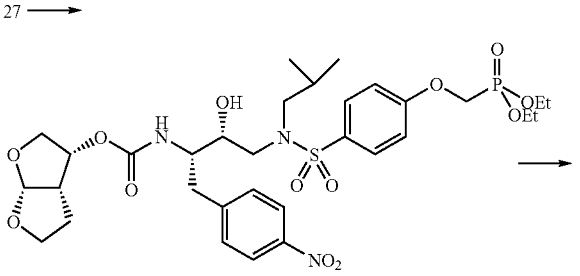

28

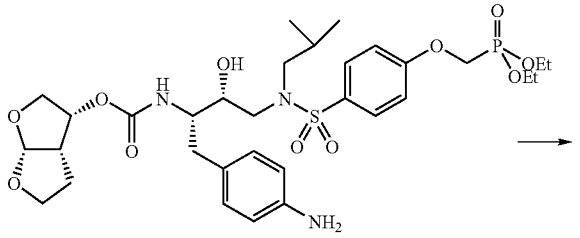

29

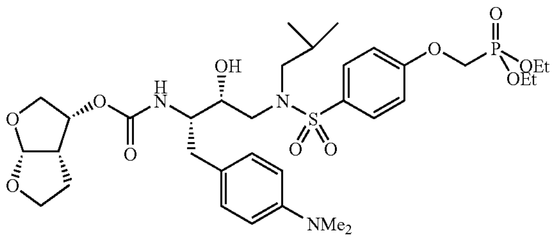

30

I. $TFA/CH_2Cl_2$; b. bisfurancarbonate/DMAP;
II. $H_2$/10%Pd-C/EtOH;
III. $HCHO/NaBH_3CN/HOAc/MeOH$ Scheme 6

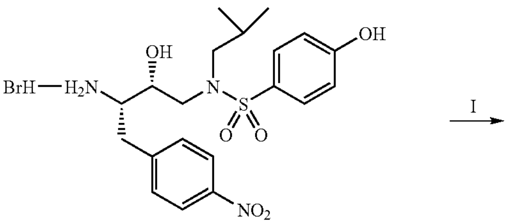

25

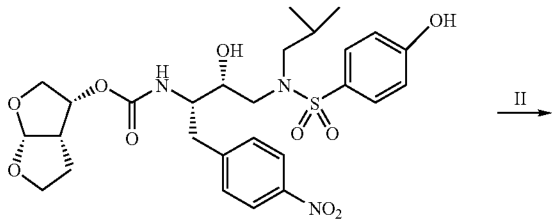

31

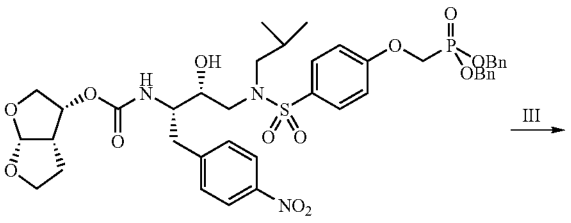

32

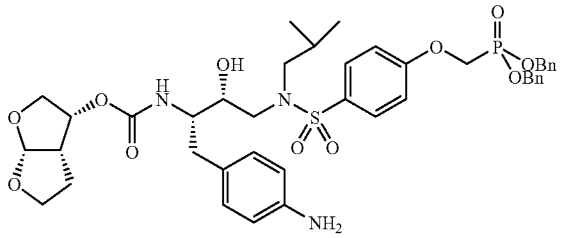

33

I.a. $TMSCl/Et_3N$; b. bisfurancarbonate/DMAP; c.n-$Bu_4NF/HOAc$;
II. $TfOCH_2PO(OBn)_2/Cs_2CO_3$;
III. Zn/HOAc Scheme 7

32

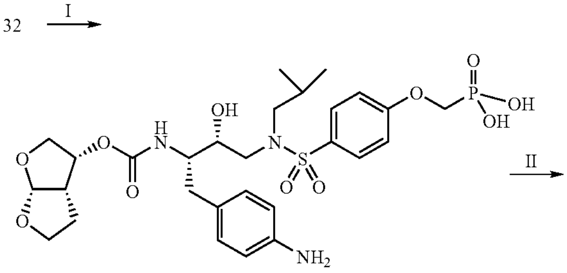

34

-continued
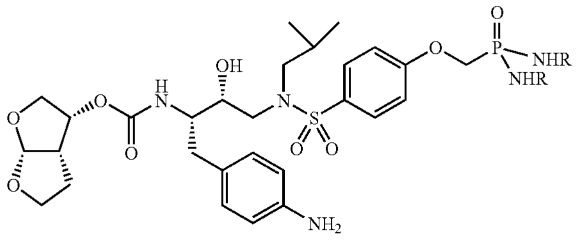
35
R = 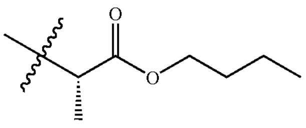
I. $H_2$/10% Pd-C; II. $RNH_2PPH_3$/Aldrithiol/diisopropylethylamine/pyridine
Scheme 8
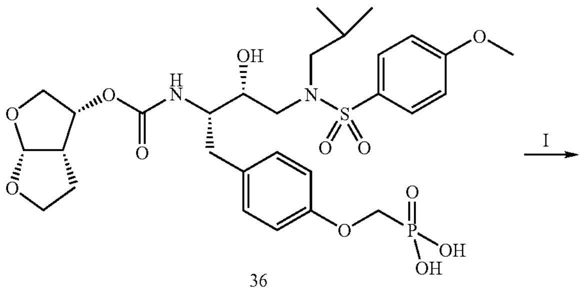
36
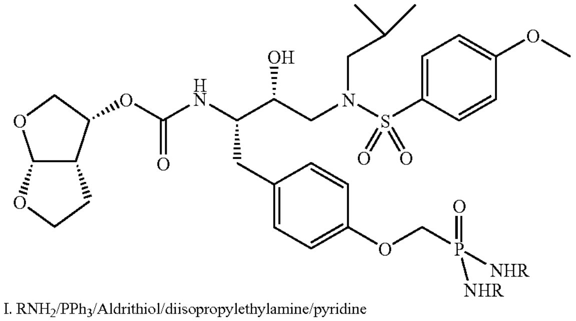
I. $RNH_2/PPh_3$/Aldrithiol/diisopropylethylamine/pyridine
37 R = 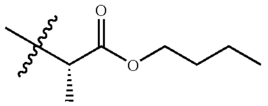
38 R = 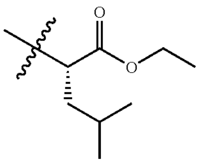
39 R = 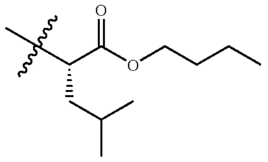
Scheme 9
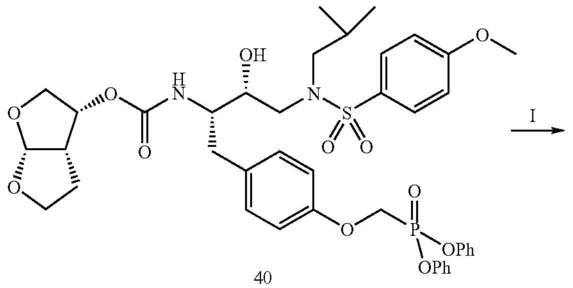
40
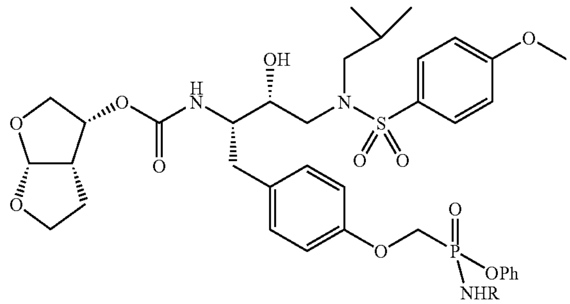
I. $RNH_2/PPh_3$Aldrithiol/diisopropylethylamine/pyridine
41 R = 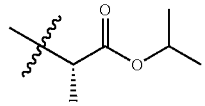
42 R = 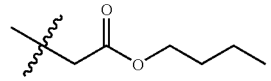
Scheme Section H
Schemes 1-14 are described in the examples.
Scheme 1
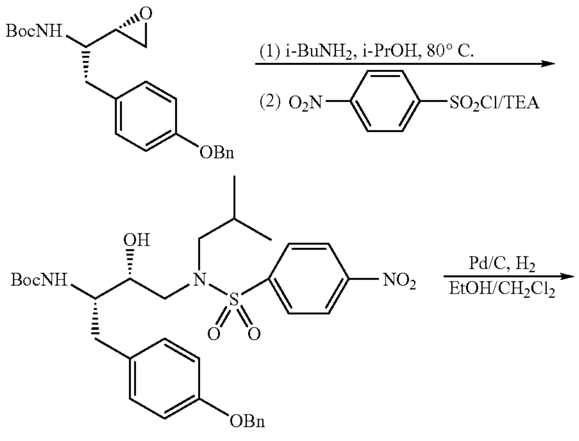
1

-continued
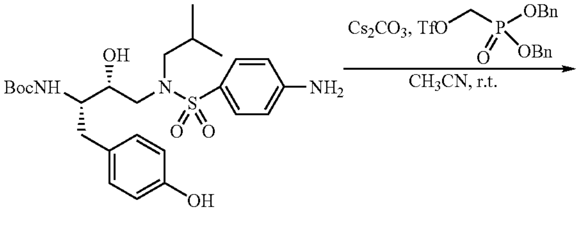
2
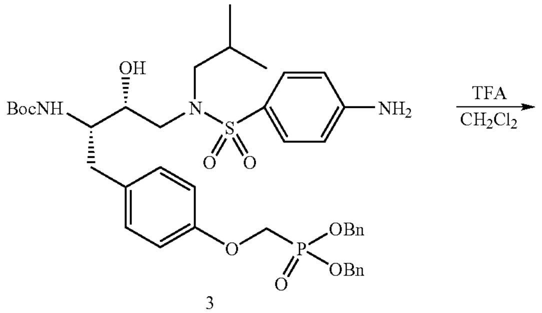
3
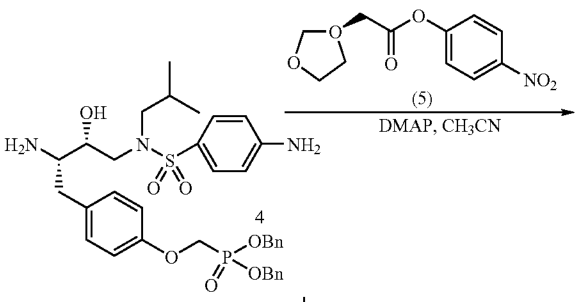
4
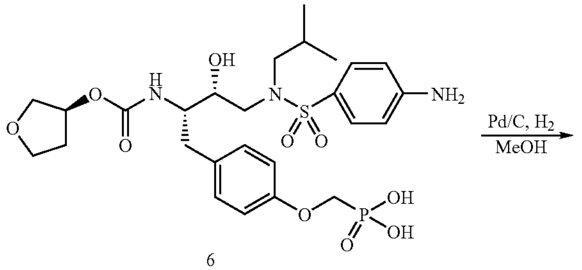
6
Scheme 2
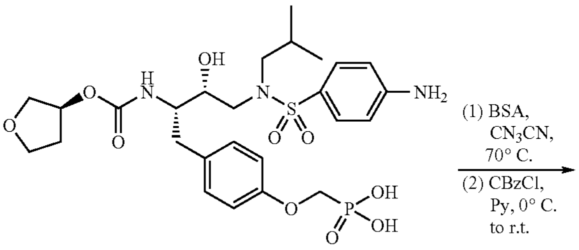
7
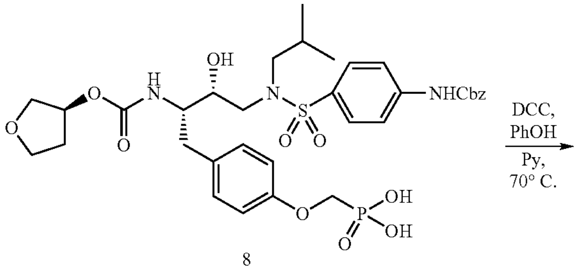
8
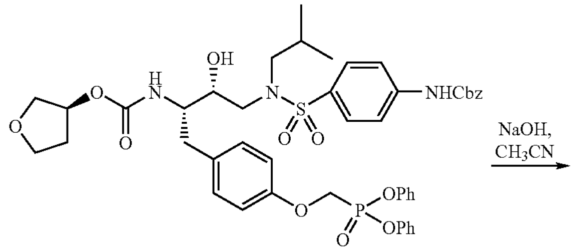
9
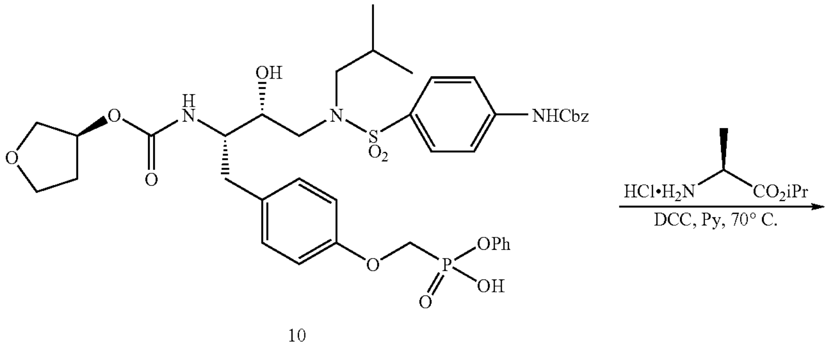
10

-continued
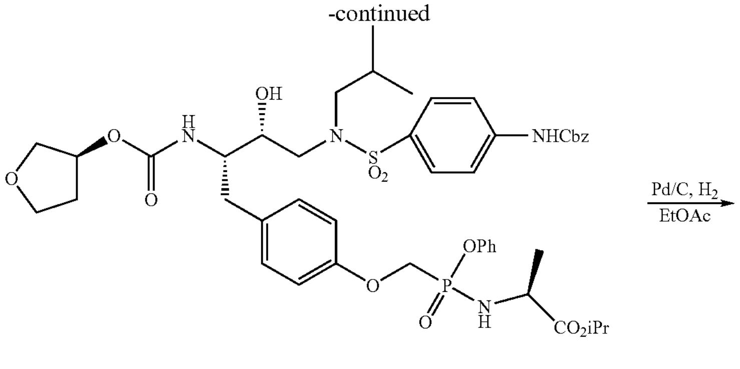
11
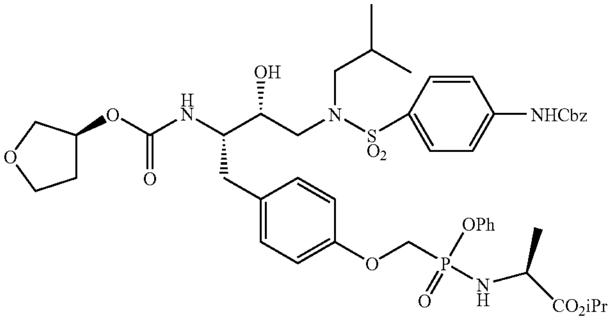
12a-c
12a, GS 108577 (isomer A/B = 1:1)
12b, GS 108578 (isomer A)
12c, GS 108579 (isomer B)
Scheme 4
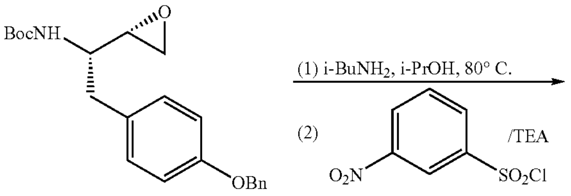
-continued
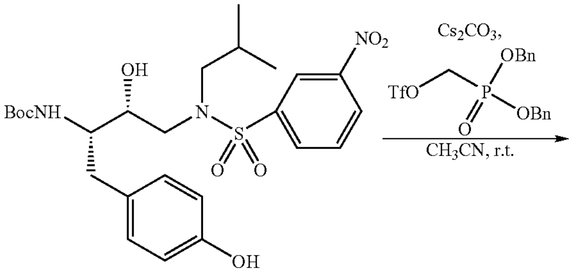
14
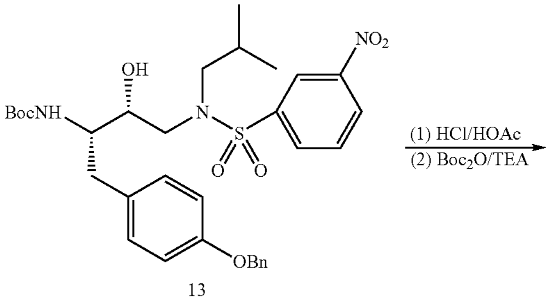
13
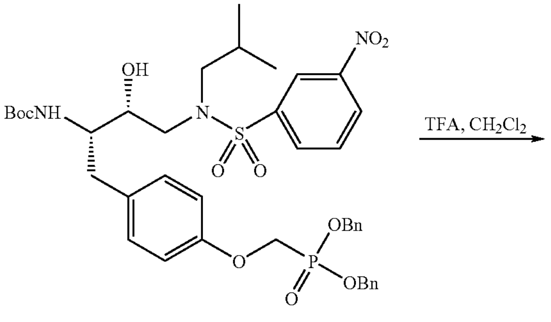
15

Scheme 5
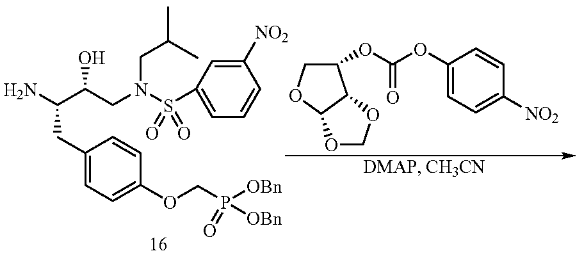
16
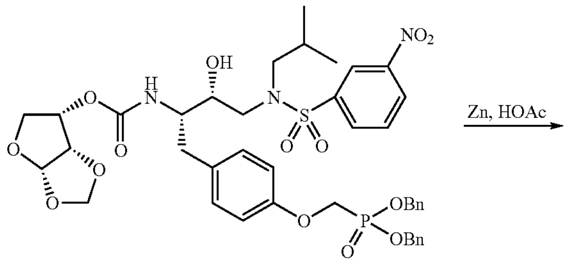
17
-continued
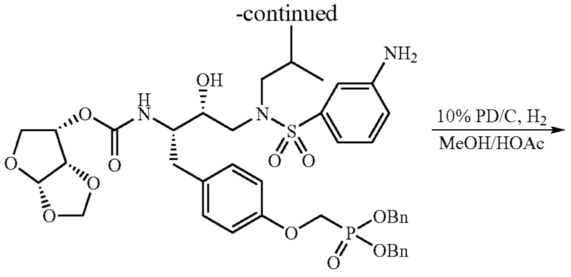
18
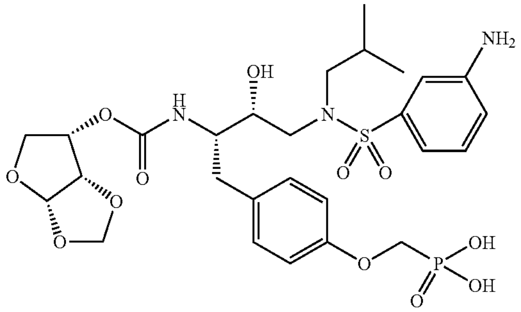
19
GS 17424
Scheme 6
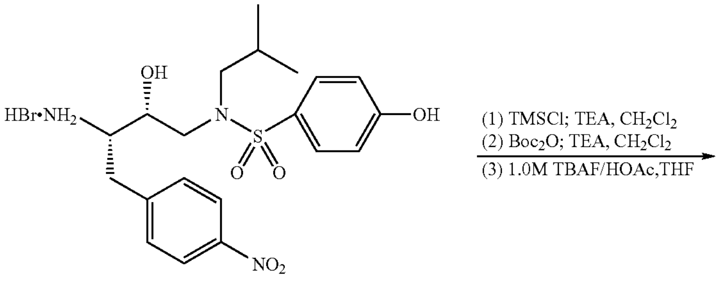
20
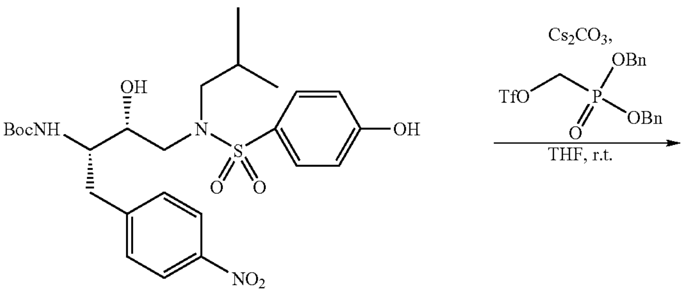
21

-continued
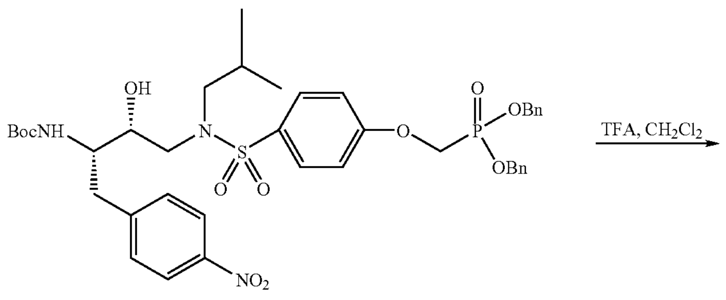
22
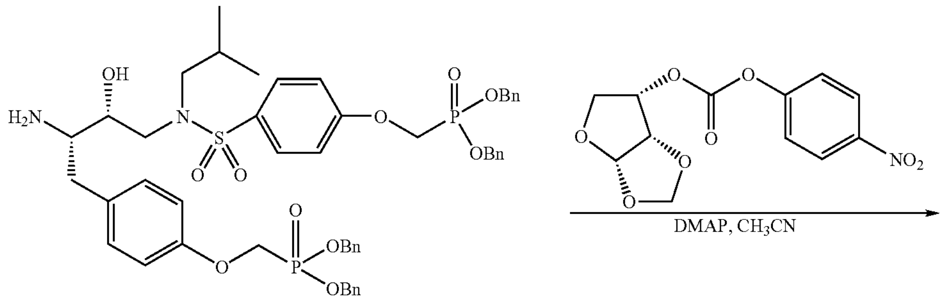
23
Scheme 7
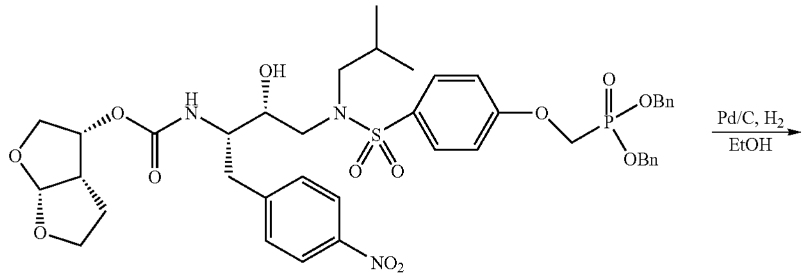
24
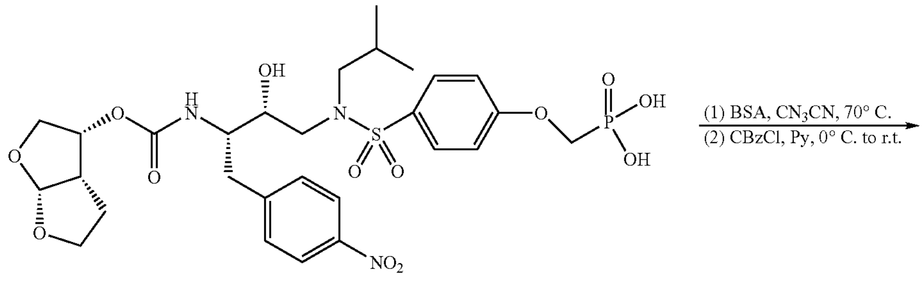
25

-continued
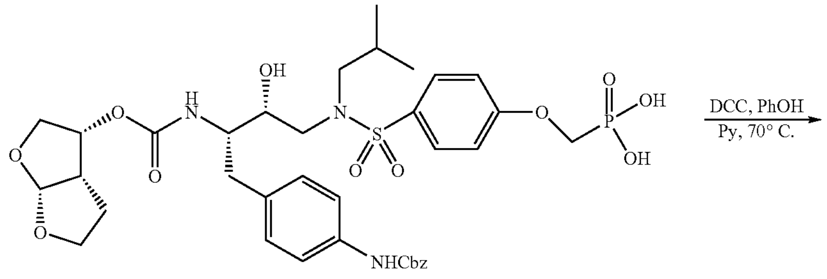
26
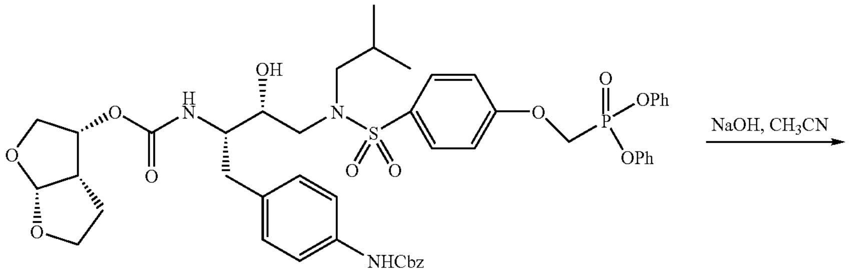
27
Scheme 8
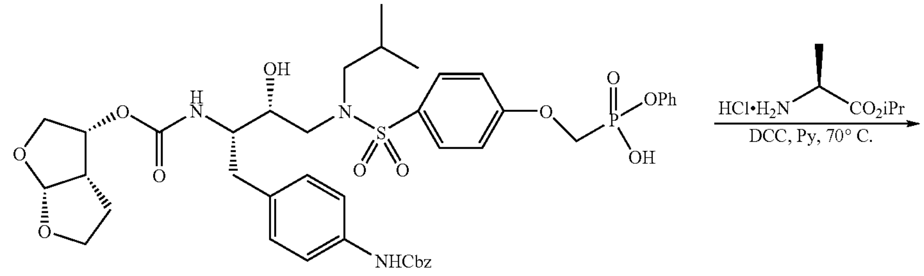
28
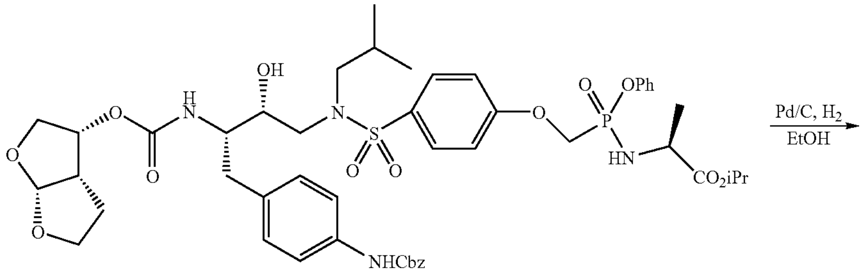
29

-continued
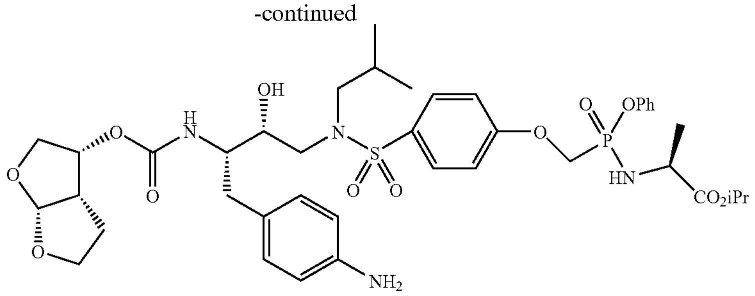
30 a-b
30a R = H, GS 77369
30b R = Et, GS 77425
Scheme 9
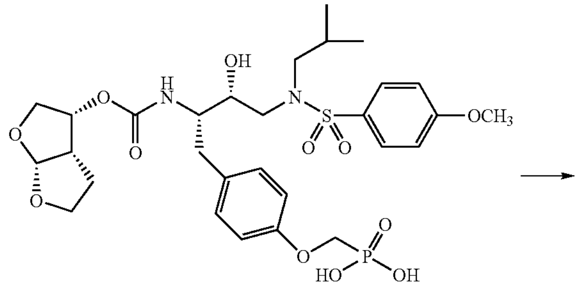
31
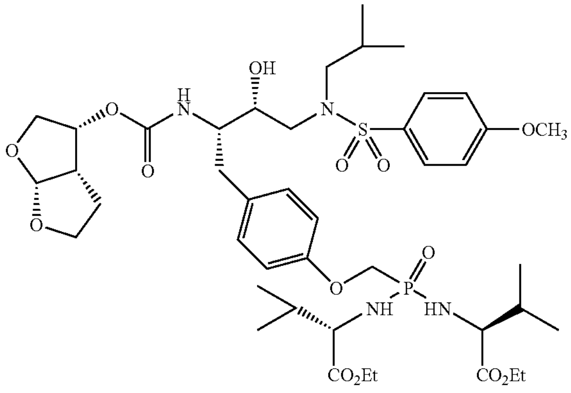
32
GS 17389

Scheme 10
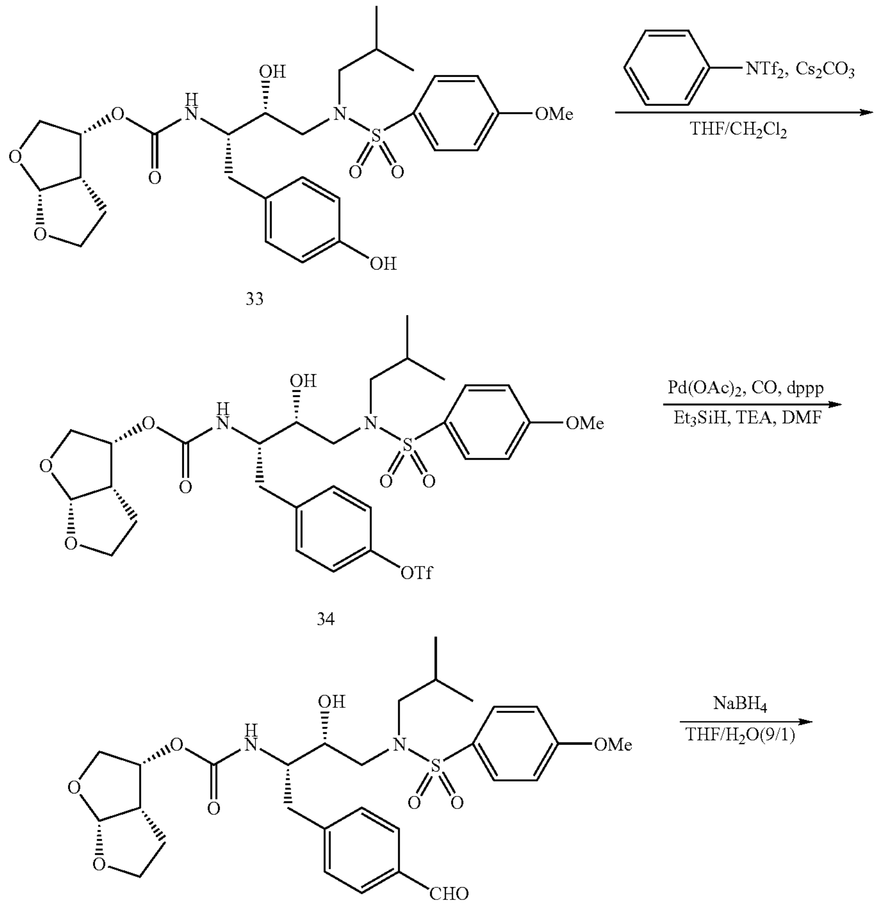
33
34
35
Scheme 11
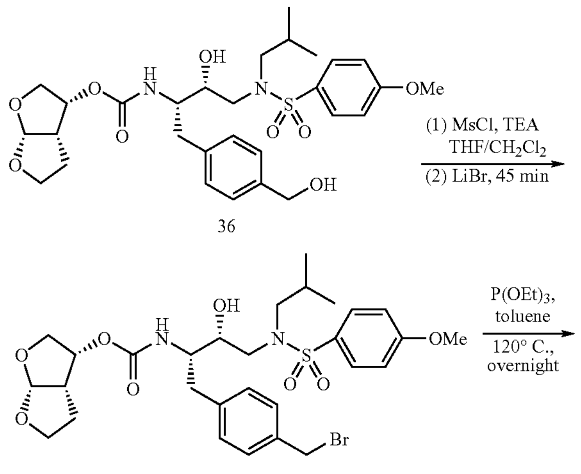
36
37
-continued
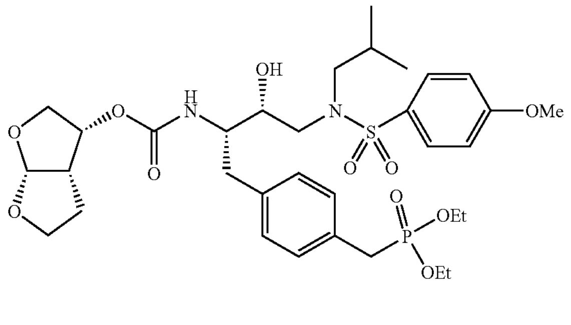
38
GS 191338

Scheme 12
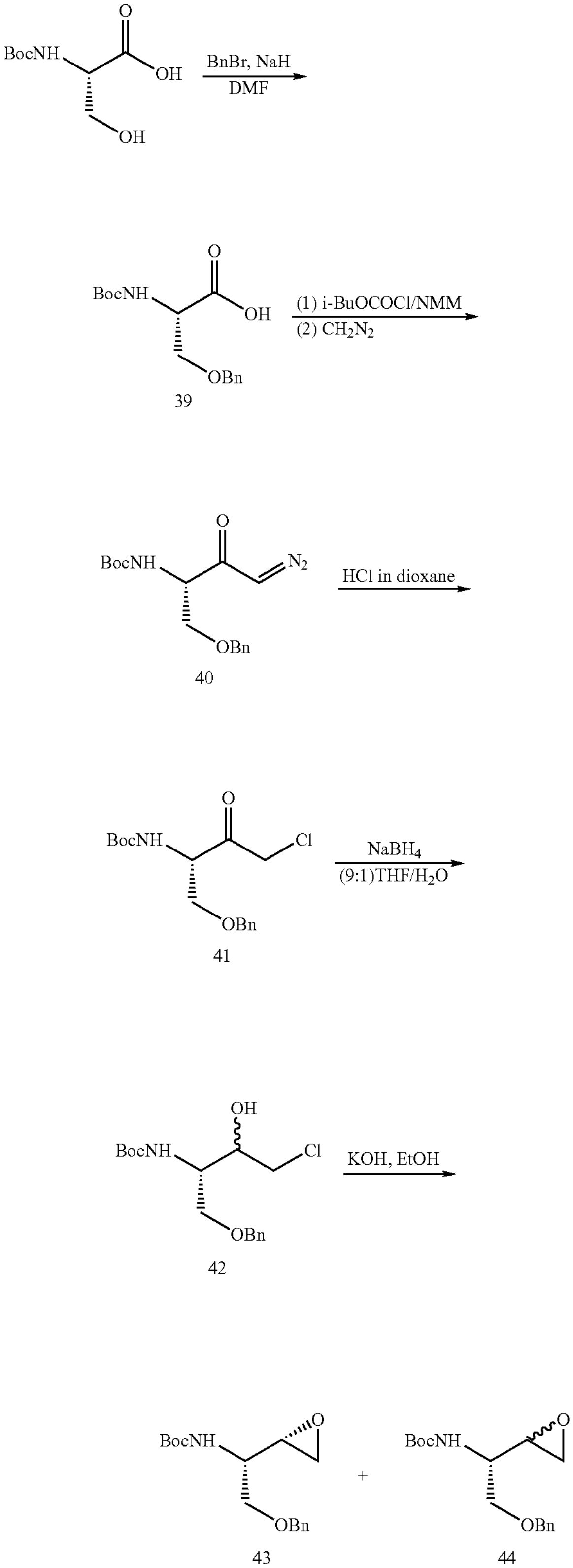
39
40
41
42
43 + 44
Scheme 13
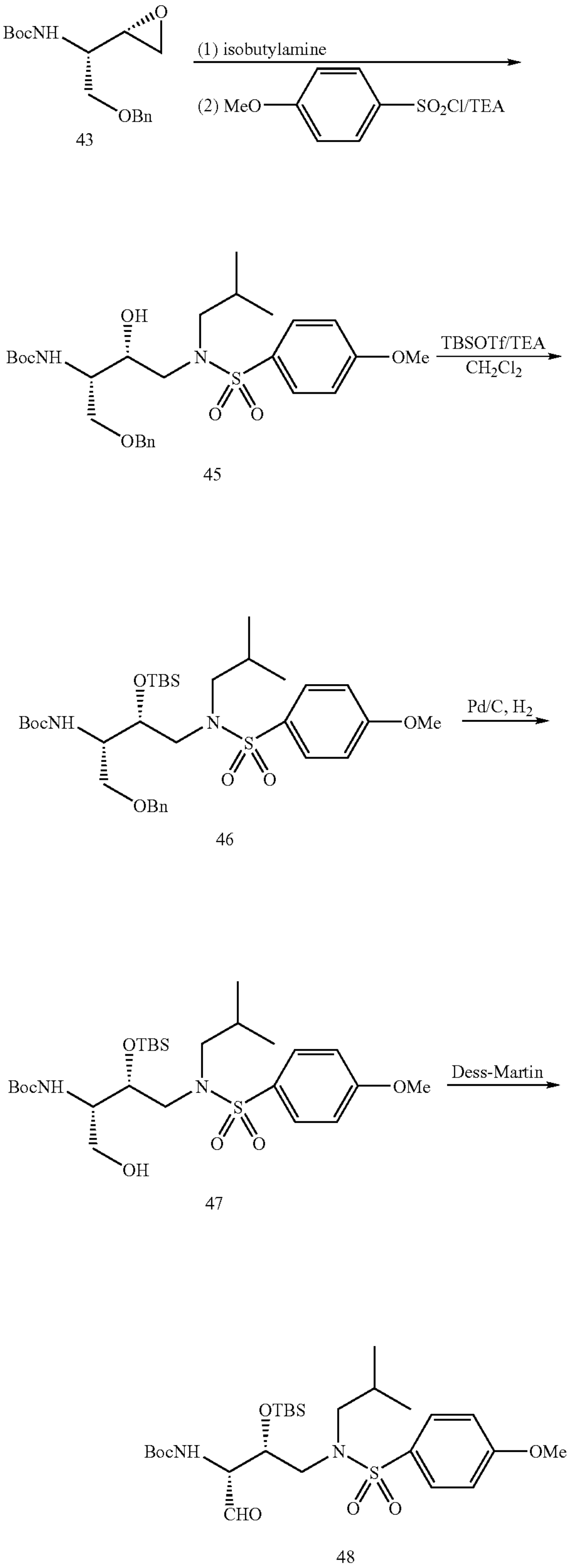
43
45
46
47
48

Scheme 14
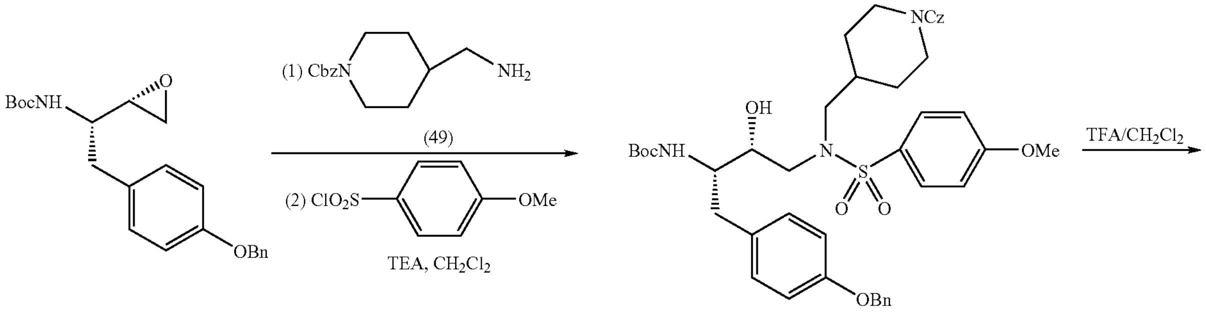
50
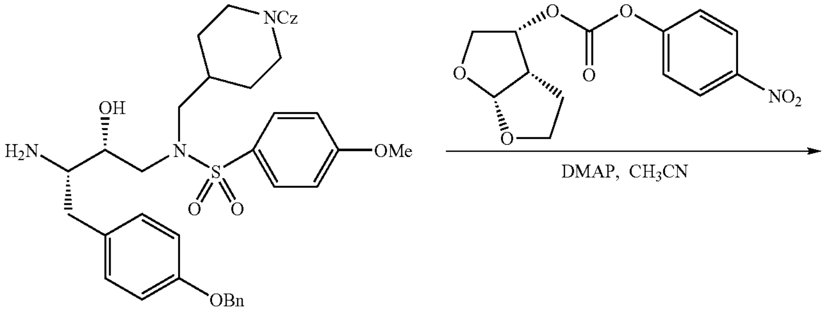
51
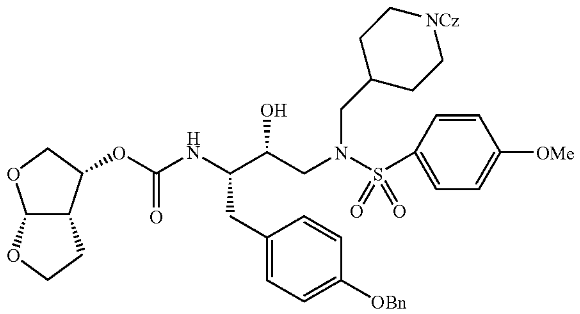
52

Scheme Section I
Schemes 1 to 3 are described in the examples.
Scheme 1
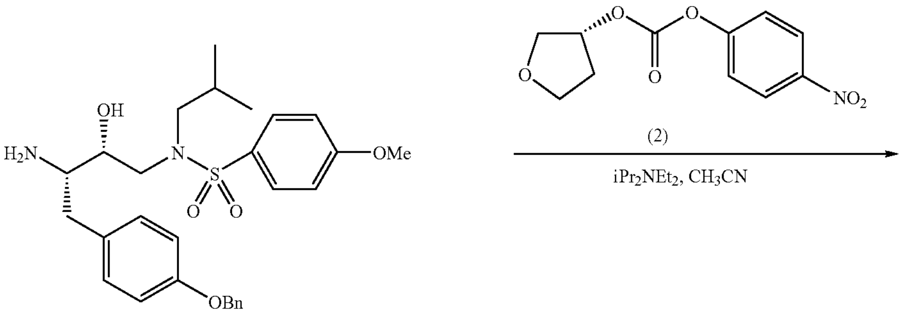
1
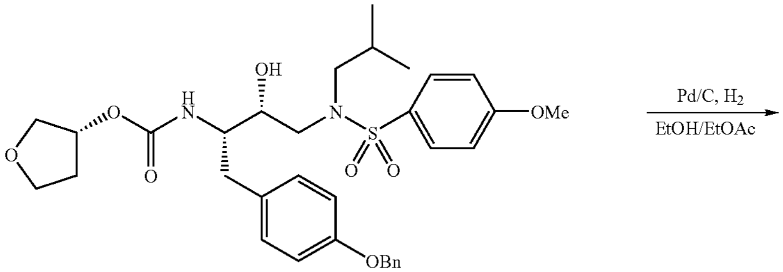
3
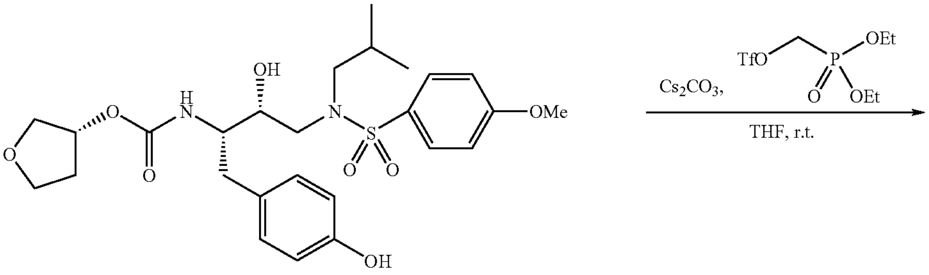
4
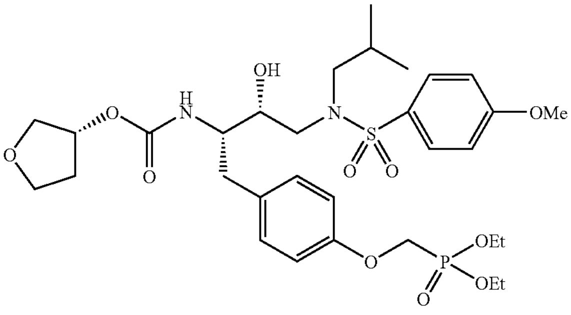
5
GS16573

Scheme 2
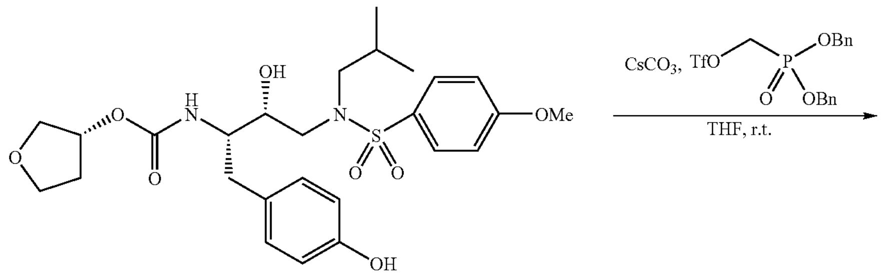
4
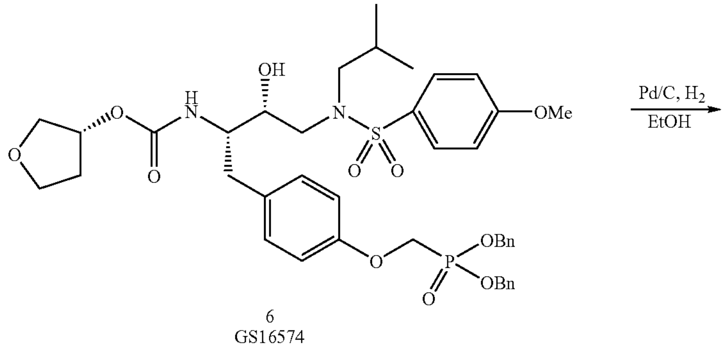
6
GS16574
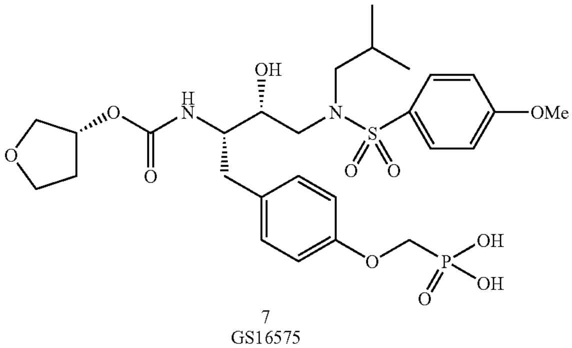
7
GS16575
Scheme 3
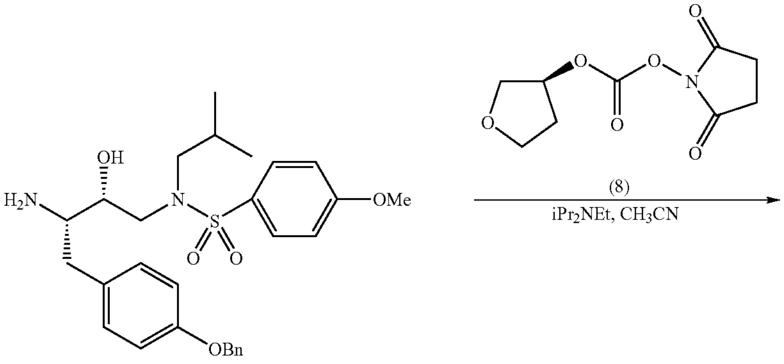
1

-continued
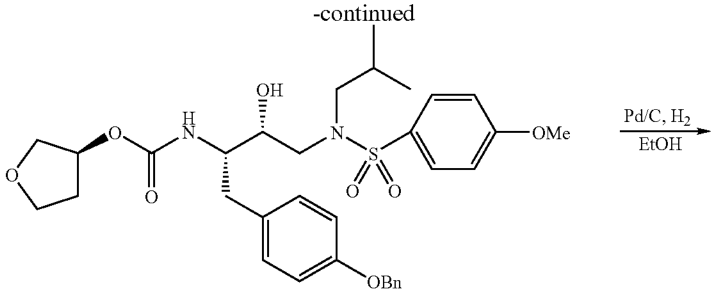
9
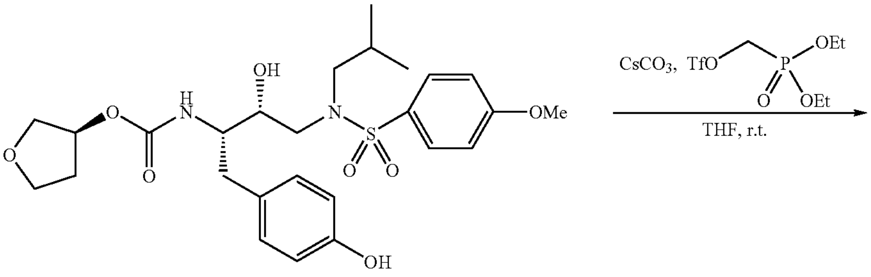
10
GS17089
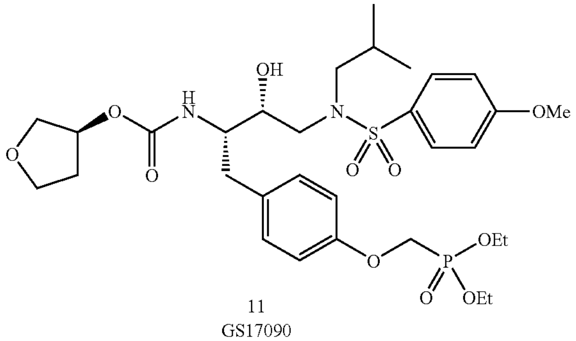
11
GS17090
Scheme Section I
Schemes 1-4 are described in the examples.
Scheme 1
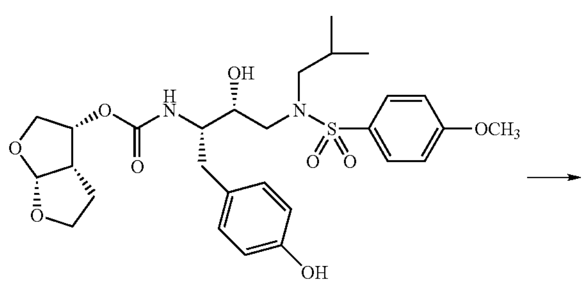
A
-continued
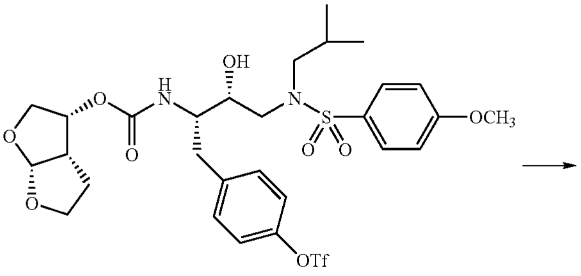
1

-continued
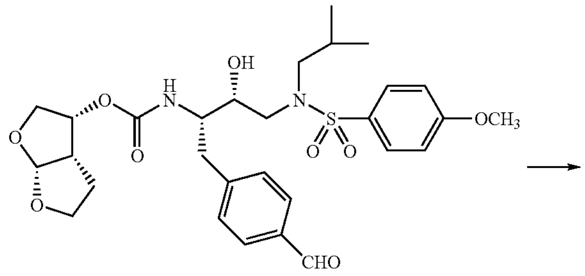
2
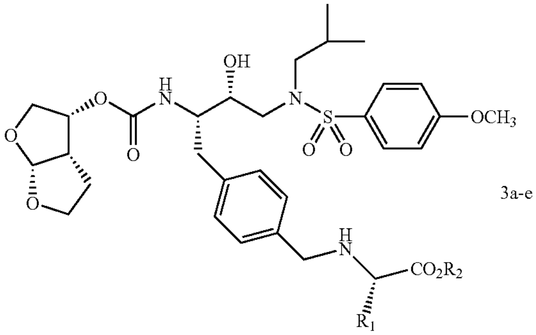
3a-e
3
Scheme 2
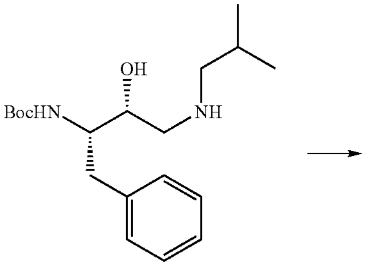
A
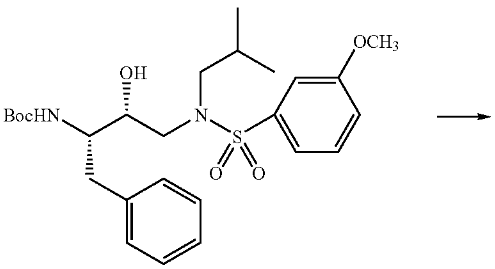
1
-continued
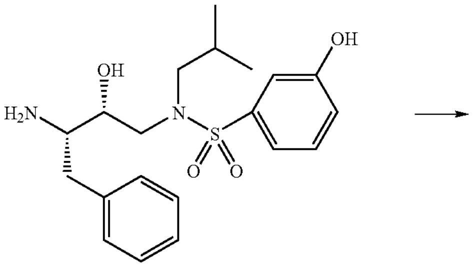
2
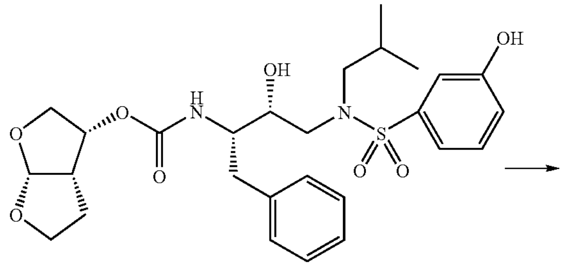
3
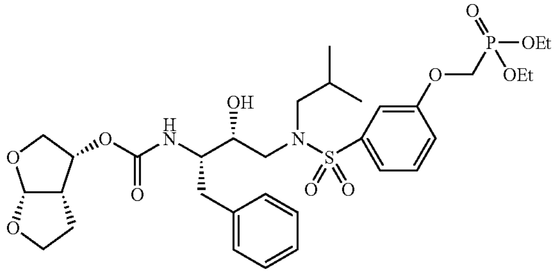
4
3 
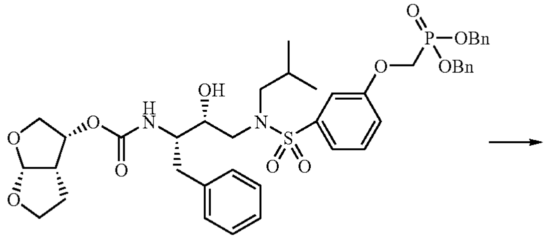
5
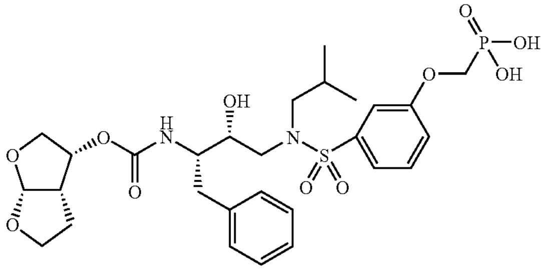
6

Scheme 3
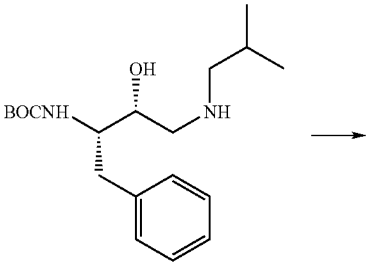
A
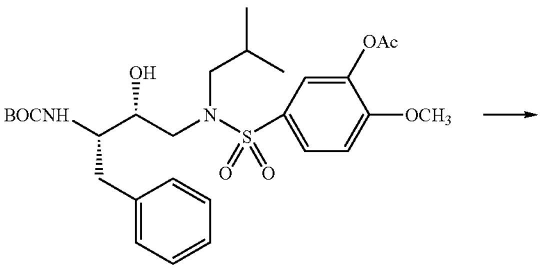
1
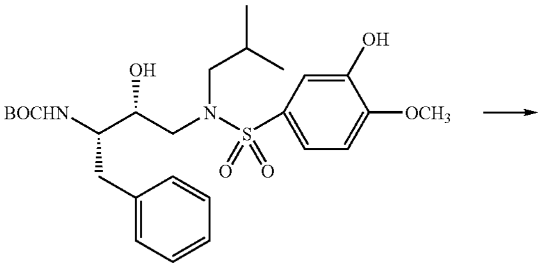
2
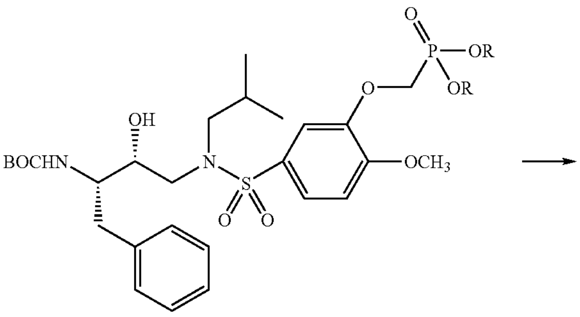
3a:R = -Bn
3b:R = -Et
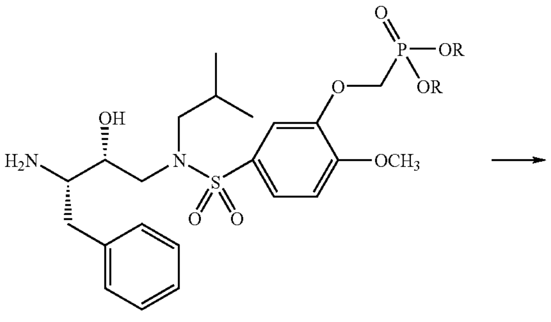
4a:R = -Bn
4b:R = -Et
-continued
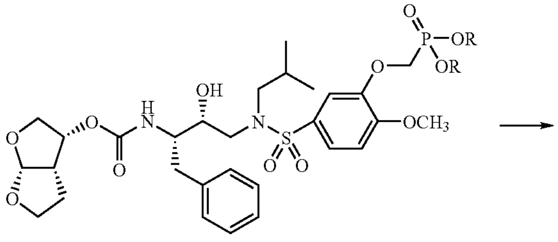
5a:R = -Bn
5b:R = -Et
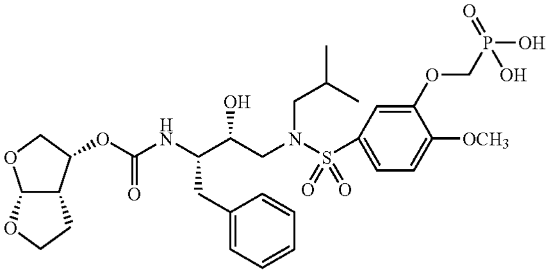
6
Scheme 4
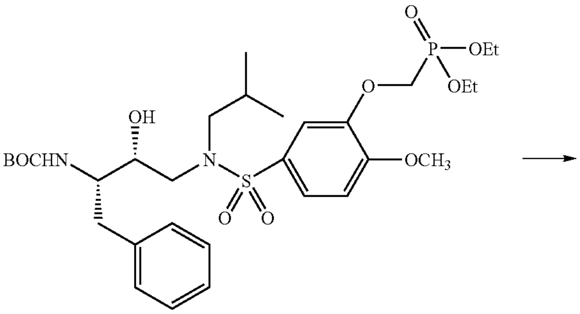
3b
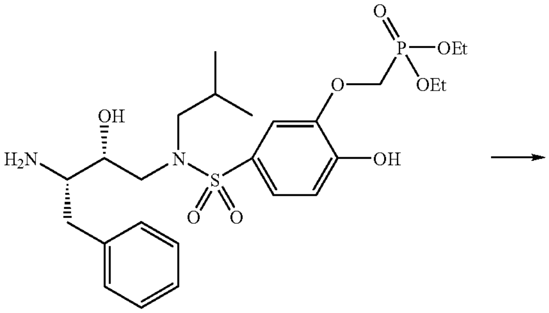
7

-continued
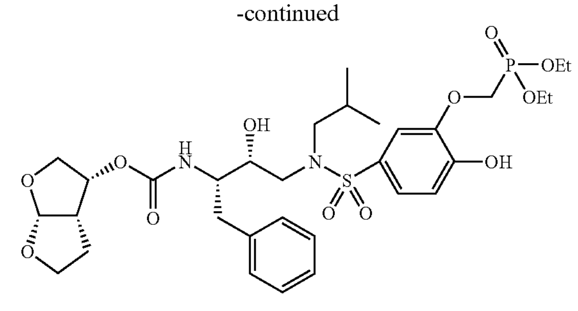
8
Scheme Section K
Schemes 1-9 are described in the examples.
Scheme 1
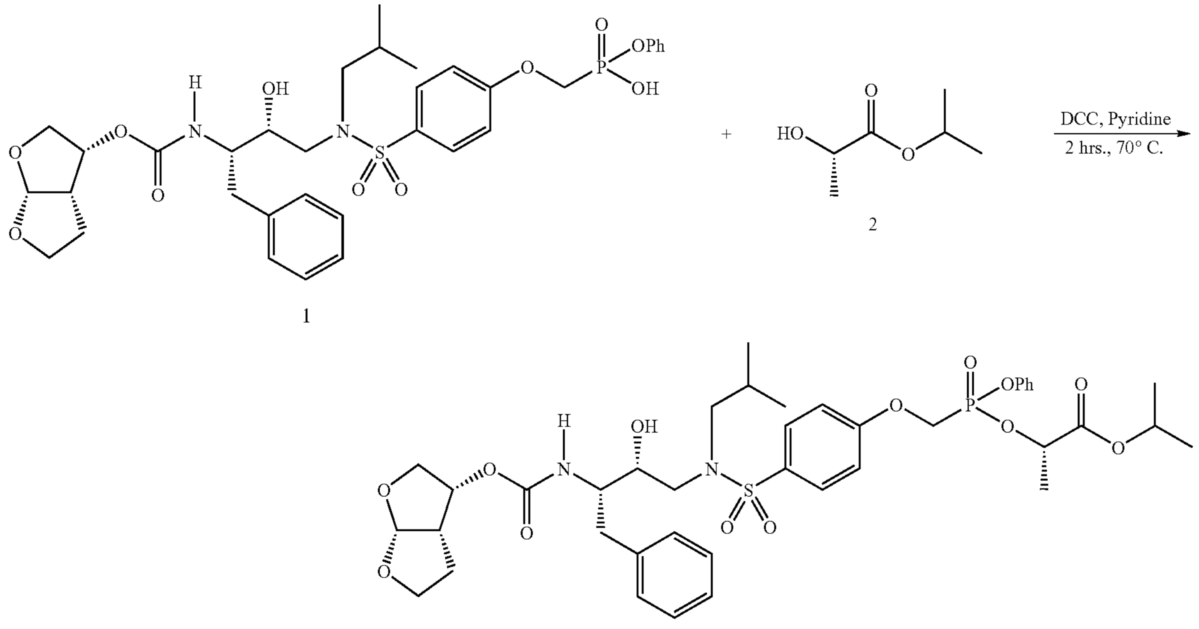
1
2
3
Scheme 2
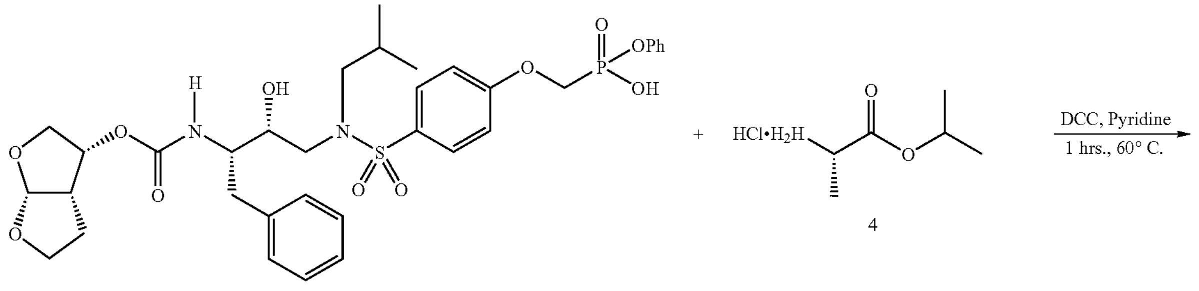
1
4

-continued
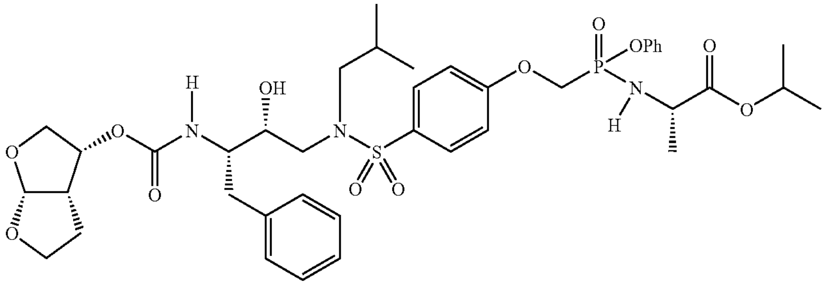
5
Scheme 3
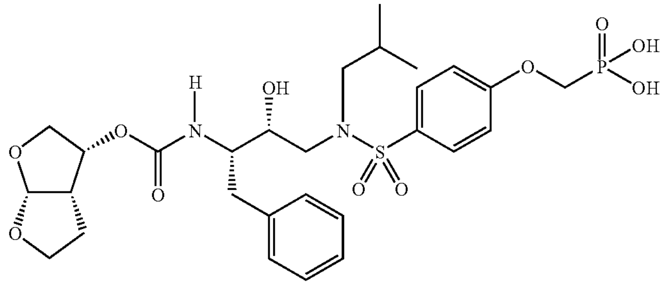
6
+
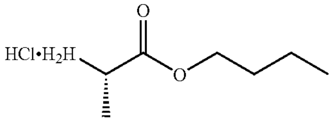
7
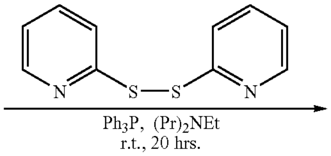
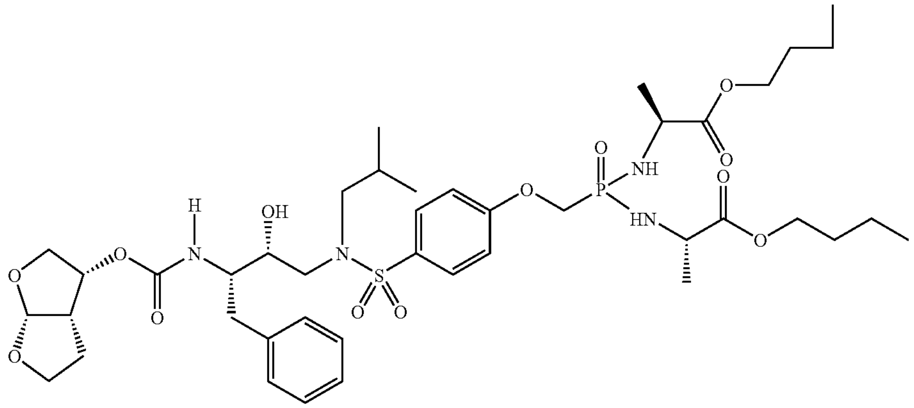
8

Scheme 4
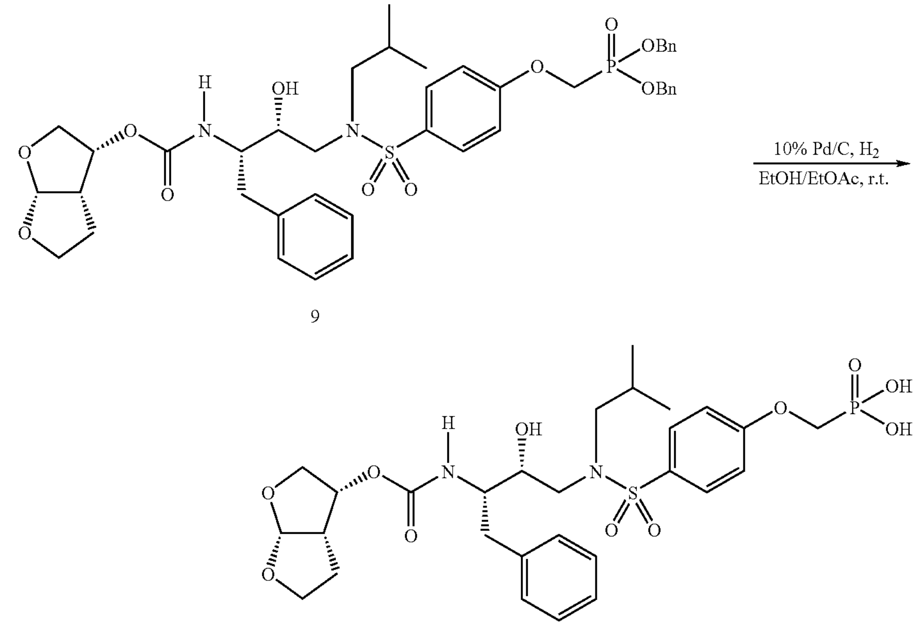
9
6
Scheme 5
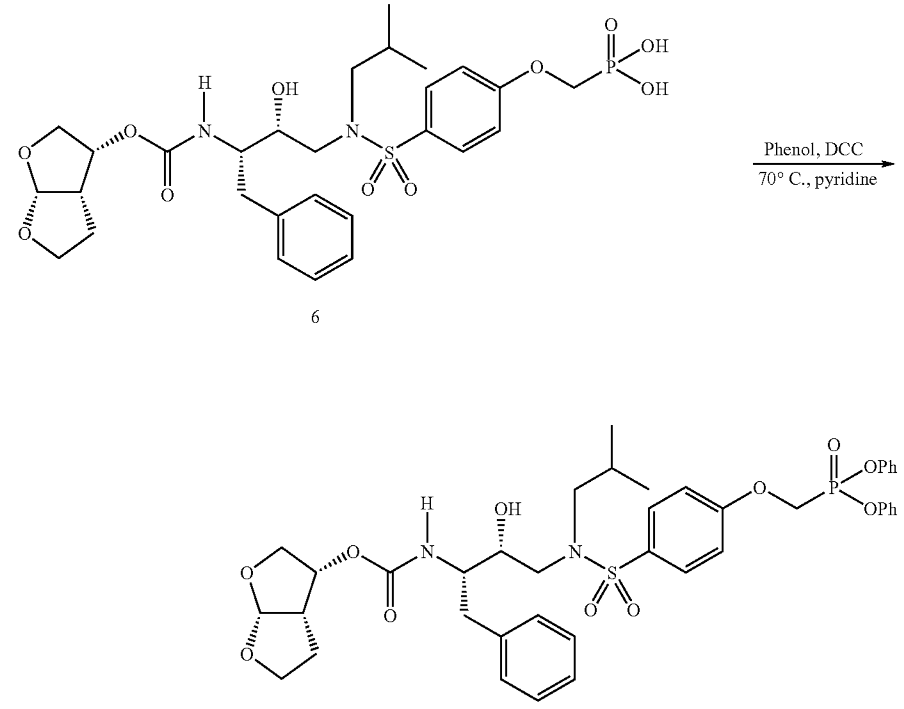
6
10

Scheme 6
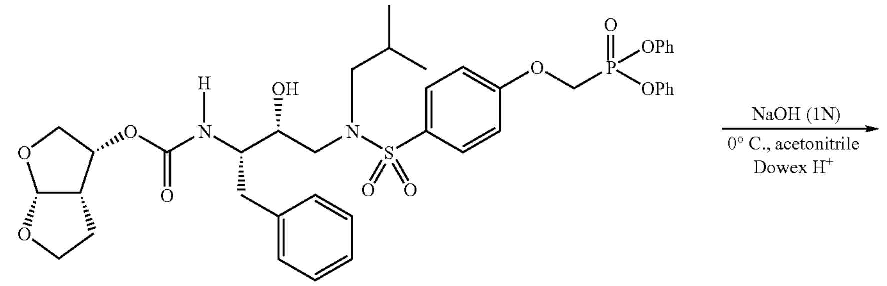
10
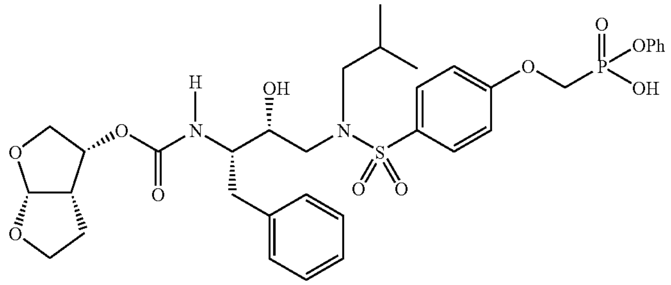
1
Scheme 7
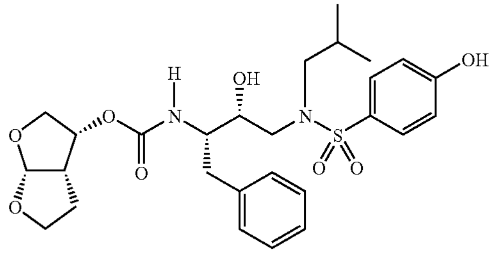
11
+
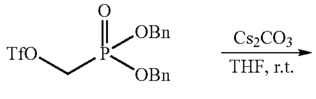
12
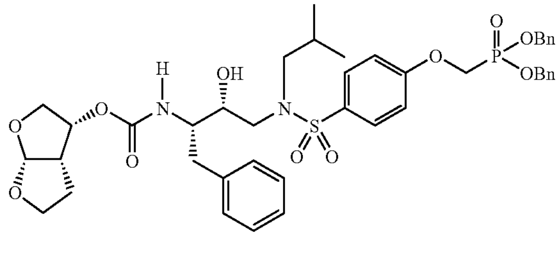
9
Scheme 8
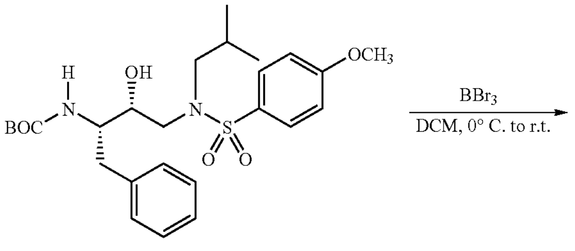
13
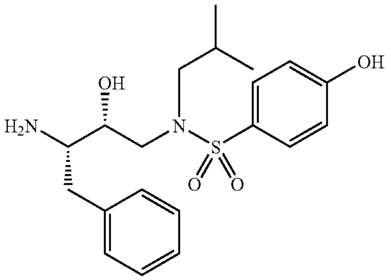
14

Scheme 9
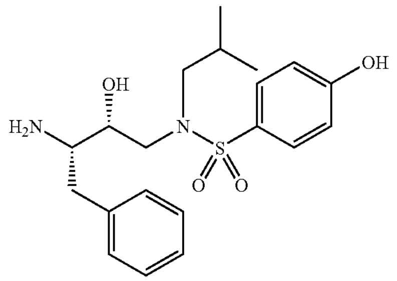
14
+
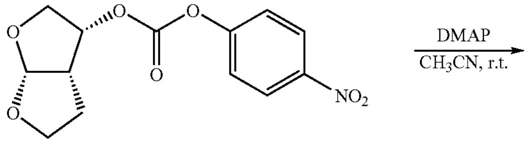
15
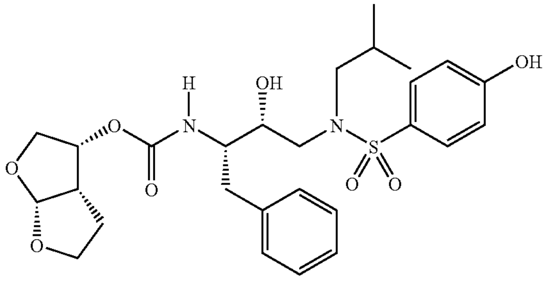
16
Scheme Section L
Schemes 1-9 are described in the examples.
Scheme 1
Synthesis of P1-Phosphonic ester
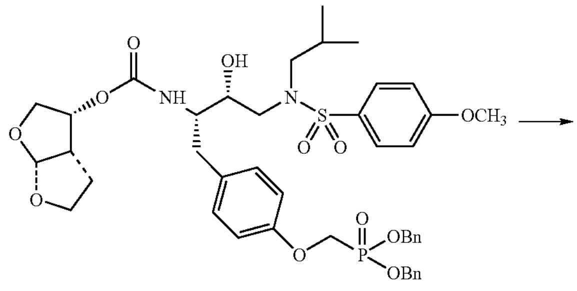
1
-continued
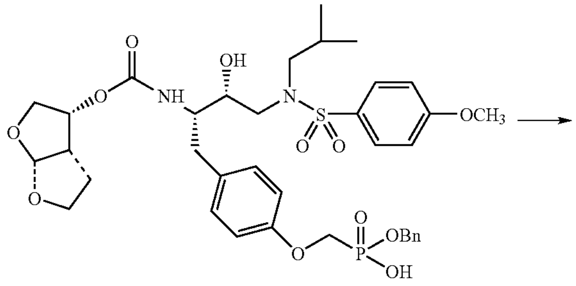
2
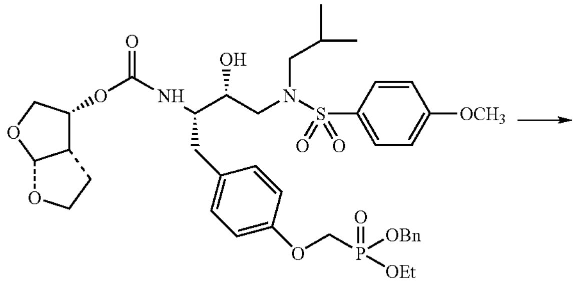
3
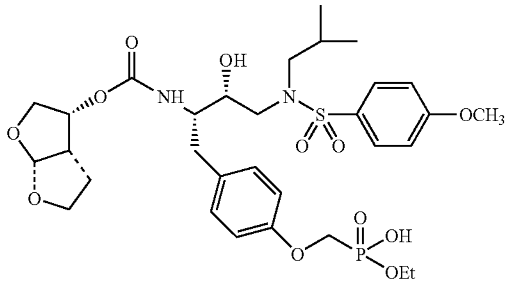
4
Scheme 2
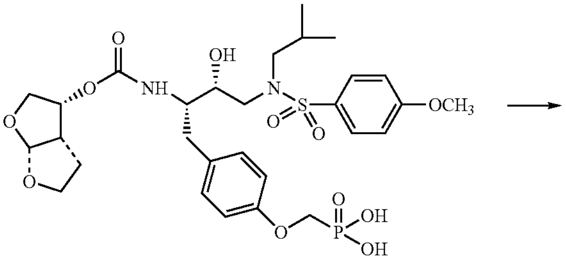
11

-continued
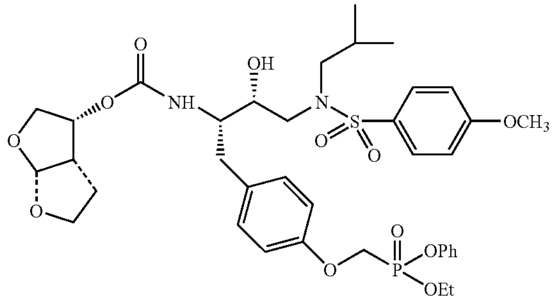
5
Scheme 3
Synthesis of P2′-Amino-P1-Phosphonic ester
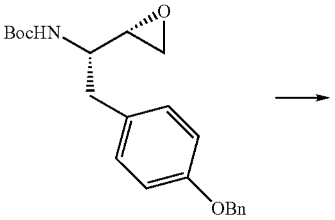
5
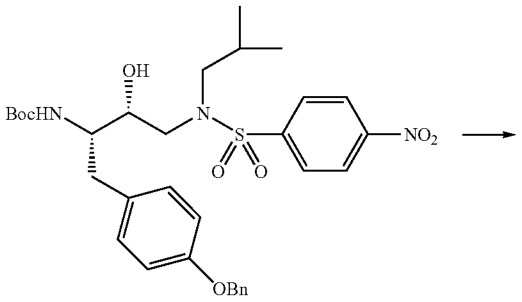
6
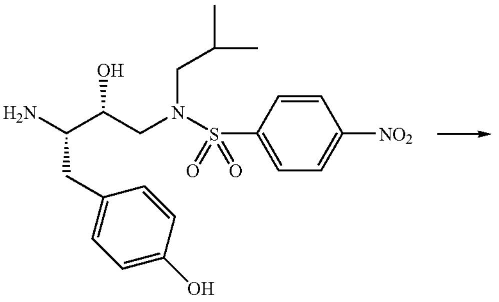
7
-continued
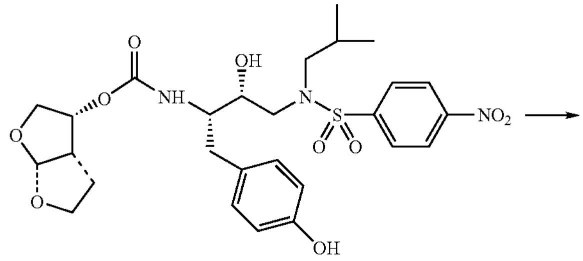
8
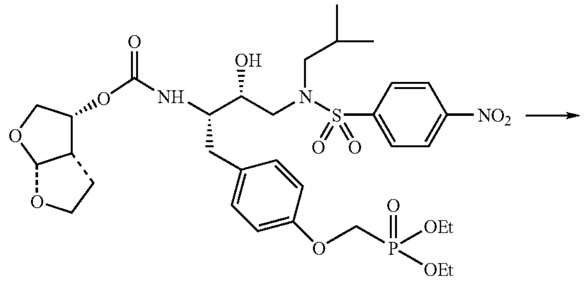
9
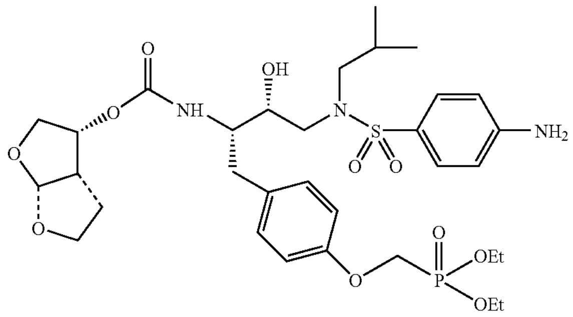
10

Scheme 4
Synthesis of Bisamidates
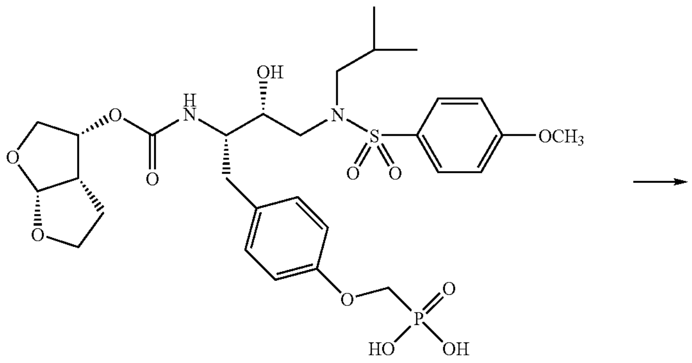
11
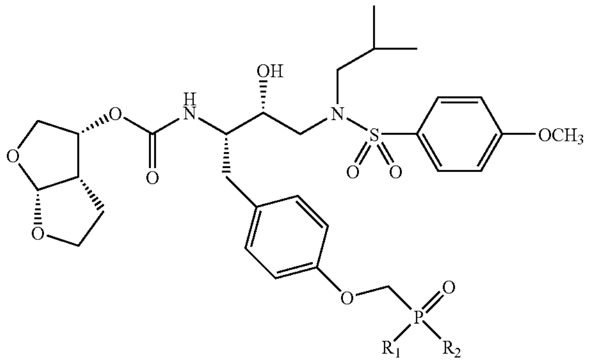
16 a, b, j and k
| Compound | $R_1$ | $R_2$ |
|---|---|---|
| 16a | Gly-Et | Gly-Et |
| 16b | Gly-Bu | Gly-Bu |
| 16j | Phe-Bu | Phe-Bu |
| 16k | NHEt | NHEt |

Scheme 5
Synthesis of Monoamidates
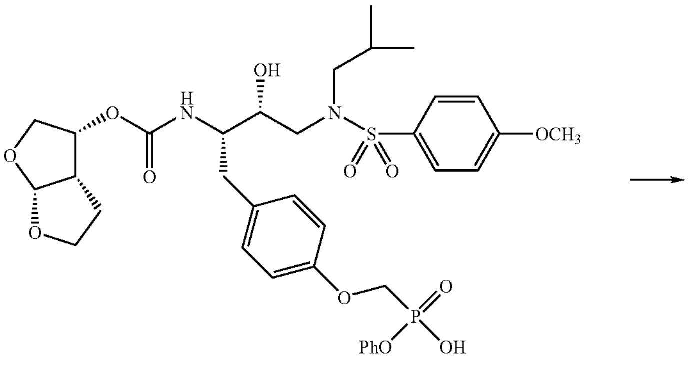
29
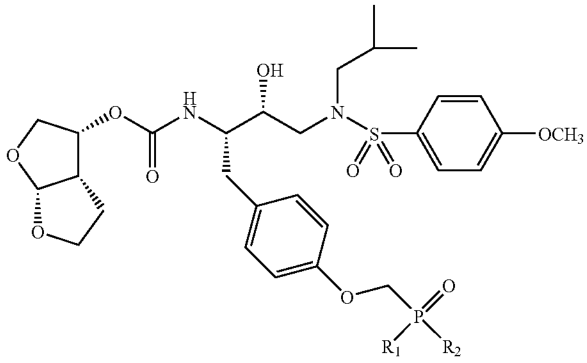
30
| Compound | $R_1$ | $R_2$ |
|---|---|---|
| 30a | OPh | Ala-Me |
| 30b | OPh | Ala-Et |
| 30c | OPh | (D)-Ala-iPr |
| 30d | OPh | Ala-Bu |
| 30e | OBn | Ala-Et |
Scheme 6
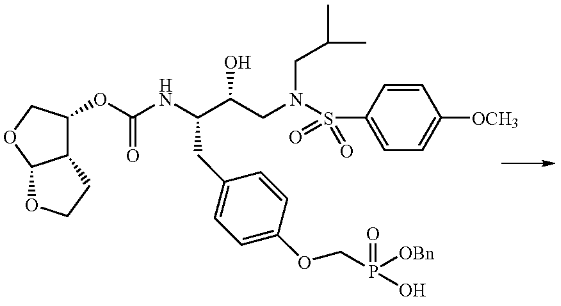
2
-continued
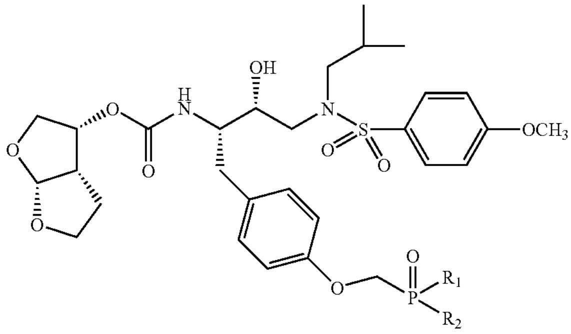
30e Scheme 7
Synthesis of Lactates
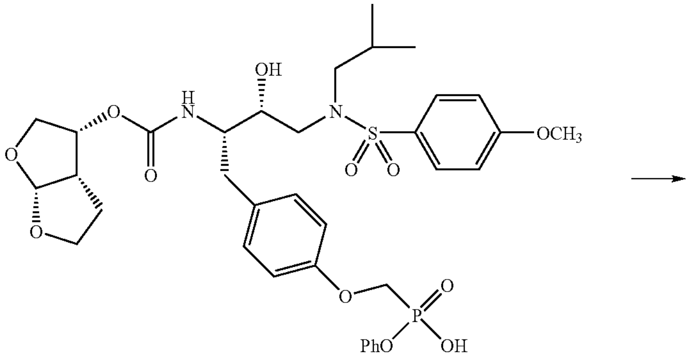
29
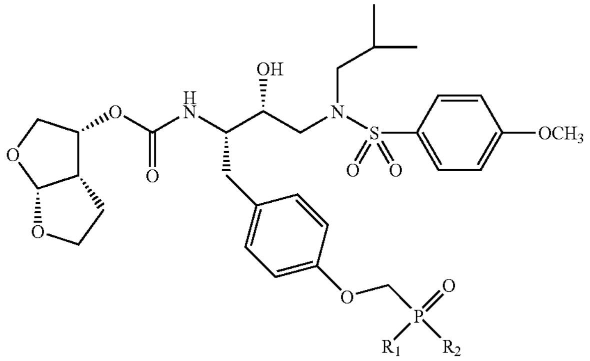
31
| Compound | $R_1$ | $R_2$ |
|---|---|---|
| 31a | OPh | Lac-iPr |
| 31b | OPh | Lac-Et |
| 31c | OPh | Lac-Bu |
| 31d | OPh | (R)-Lac-Me |
| 31e | OPh | (R)-Lac-Et |
Scheme 8
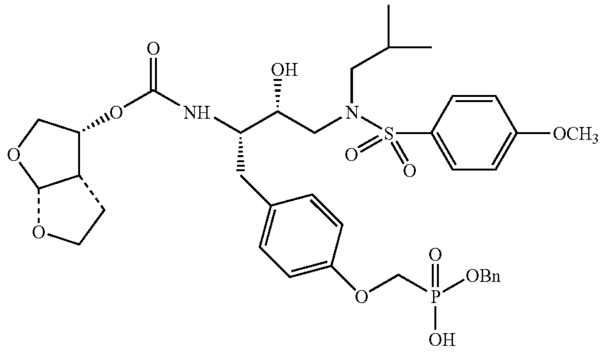
2
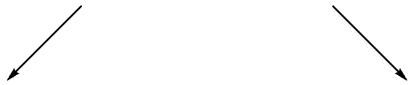

-continued
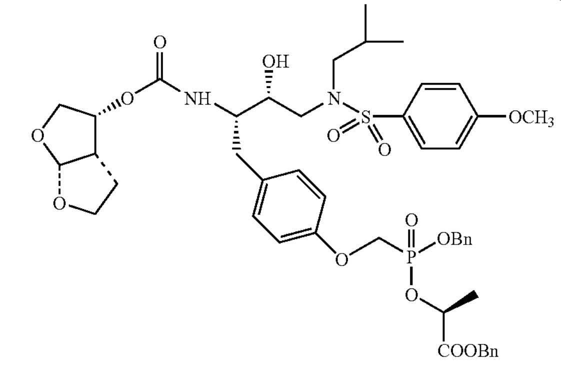
32
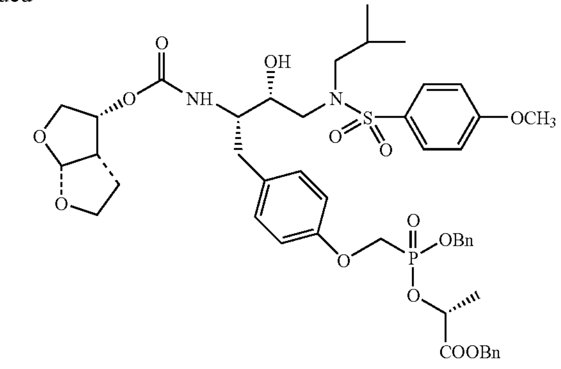
33
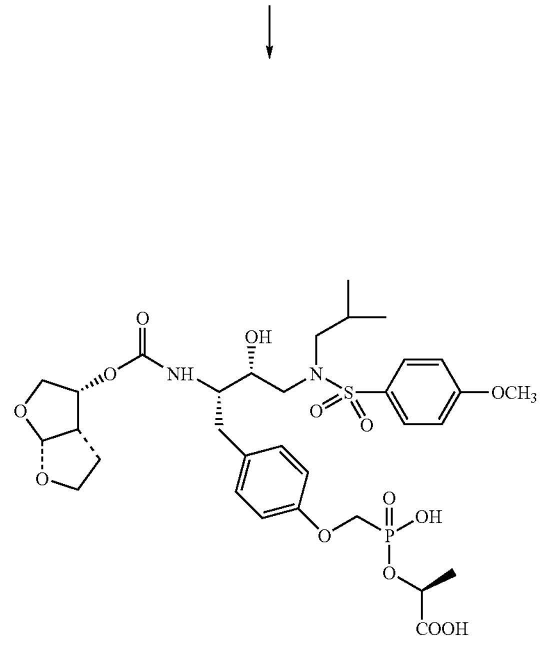
34
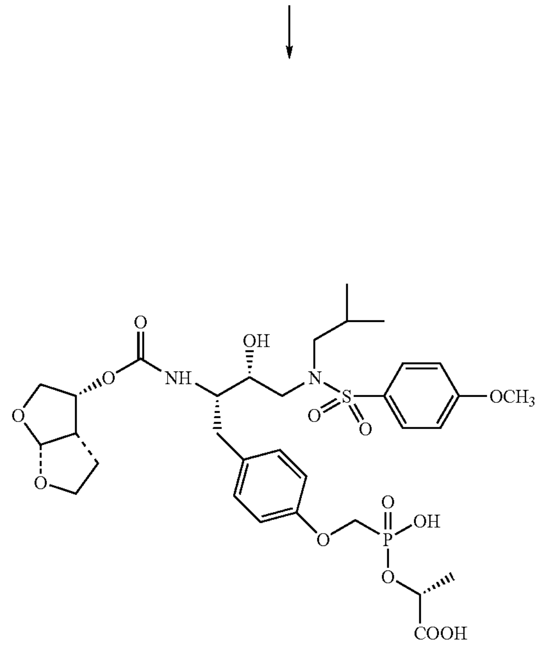
35
Scheme 9
Synthesis of Bislactate
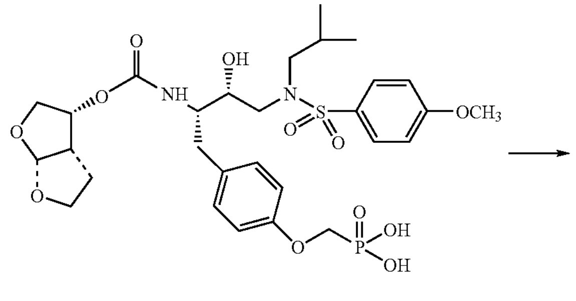
11
-continued
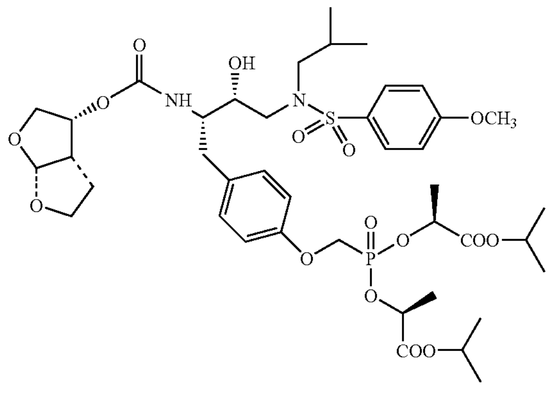
36

EXAMPLES

The following Examples refer to the Schemes.

Some Examples have been performed multiple times. In repeated Examples, reaction conditions such as time, temperature, concentration and the like, and yields were within normal experimental ranges. In repeated Examples where significant modifications were made, these have been noted where the results varied significantly from those described. In Examples where different starting materials were used, these are noted. When the repeated Examples refer to a "corresponding" analog of a compound, such as a "corresponding ethyl ester", this intends that an otherwise present group, in this case typically a methyl ester, is taken to be the same group modified as indicated.

Example Section A

Example 1

Diazo ketone 1: To a solution of N-tert-Butoxycarbonyl-O-benzyl-L-tyrosine (11 g, 30 mmol, Fluka) in dry THF (55 mL) at −25-30° C. (external bath temperature) was added isobutylchloroformate (3.9 mL, 30 mmol) followed by the slow addition of N.methylmorpholine (3.3 mL, 30 mmol). The mixture was stirred for 25 min, filtered while cold, and the filter cake was rinsed with cold (0° C.) THF (50 mL). The filtrate was cooled to −25° C. and diazomethane (~50 mmol, generated from 15 g Diazald according to Aldrichimica Acta 1983, 16, 3) in ether (~150 mL) was poured into the mixed anhydride solution. The reaction was stirred for 15 min and was then placed in an icebath at 0° C., allowing the bath to warm to room temperature while stirring overnight for 15 h. The solvent was evaporated under reduced pressure and the residue was dissolved in EtOAc, washed with water, saturated $NaHCO_3$, saturated NaCl, dried ($MgSO_4$), filtered and evaporated to a pale yellow solid. The crude solid was slurried in hexane, filtered, and dried to afford the diazo ketone (10.9 g, 92%) which was used directly in the next step.

Example 2

Chloroketone 2: To a suspension of diazoketone 1 (10.8 g, 27 mmol) in ether (600 mL) at 0° C. was added 4M HCl in dioxane (7.5 mL, 30 mmol). The solution was removed from the cooling bath, and allowed to warm to room temperature at which time the reaction was stirred 1 h. The reaction solvent was evaporated under reduced pressure to give a solid residue that was dissolved in ether and passed through a short column of silica gel. The solvent was evaporated to afford the chloroketone (10.7 g, 97%) as a solid.

Example 3

Chloroalcohol 3: To a solution of chloroketone 2 (10.6 g, 26 mmol) in THF (90 mL) was added water (10 mL) and the solution was cooled to 3-4° C. (internal temperature). A solution of $NaBH_4$ (1.5 g, 39 mmol) in water (5 mL) was added dropwise over a period of 10 min. The mixture was stirred for 1 h at 0° C. and saturated $KHSO_4$ was slowly added until the pH<4 followed by saturated NaCl. The organic phase was washed with saturated NaCl, dried ($MgSO_4$) filtered and evaporated under reduced pressure. The crude product consisted of a 70:30 mixture of diastereomers by HPLC analysis (mobile phase, 77:25-$CH_3CN$:$H_2O$; flow rate: 1 mL/min; detection: 254 nm; sample volume: 20 µL; column: 5µ C18, 4.6×250 mm, Varian; retention times: major diastereomer 3, 5.4 min, minor diastereomer 4, 6.1 min). The residue was recrystallized from EtOAc/hexane twice to afford the chloro alcohol 3 (4.86 g, >99% diastereomeric purity by HPLC analysis) as a white solid.

Example 4

Epoxide 5: A solution of chloroalcohol 3 (4.32 g, 10.6 mmol) in EtOH (250 mL) and THF (100 mL) was treated with $K_2CO_3$ (4.4 g, 325 mesh, 31.9 mmol) and the mixture was stirred for at room temperature for 20 h. The reaction mixture was filtered and was evaporated under reduced pressure. The residue was partitioned between EtOAc and water and the organic phase was washed with saturated NaCl, dried ($MgSO_4$), filtered, and evaporated under reduced pressure. The crude product was chromatographed on silica gel to afford the epoxide (3.68 g, 94%) as a white solid.

Example 5

Sulfonamide 6: To a suspension of epoxide 5 (2.08 g, 5.6 mmol) in 2-propanol (20 mL) was added isobutylamine (10.7 mL, 108 mmol) and the solution was refluxed for 30 min. The solution was evaporated under reduced pressure and the crude solid was dissolved in $CH_2Cl_2$ (20 mL) and cooled to 0° C. N,N'-diisopropylethylamine (1.96 mL, 11.3 mmol) was added followed by the addition of 4-methoxybenzenesulfonyl chloride (1.45 g, 7 mmol) in $CH_2Cl_2$ (5 mL) and the solution was stirred for 40 min at 0° C., warmed to room temperature and evaporated under reduced pressure. The residue was partitioned between EtOAc and saturated $NaHCO_3$. The organic phase was washed with saturated NaCl, dried ($MgSO_4$), filtered and evaporated under reduced pressure. The crude product was recrystallized from EtOAc/hexane to give the sulfonamide (2.79 g, 81%) as a small white needles: mp 122-124° C. (uncorrected).

Example 6

Carbamate 7: A solution of sulfonamide 6 (500 mg, 0.82 mmol) in $CH_2Cl_2$ (5 mL) at 0° C. was treated with trifluoroacetic acid (5 mL). The solution was stirred at 0° C. for 30 min and was removed from the cold bath stirring for an additional 30 min. Volatiles were evaporated under reduced pressure and the residue was partitioned between $CH_2Cl_2$ and saturated $NaHCO_3$. The aqueous phase was extracted twice with $CH_2Cl_2$ and the combined organic extracts were washed with saturated NaCl, dried ($MgSO_4$), filtered, and evaporated under reduced pressure. The residue was dissolved in $CH_3CN$ (5 mL) and was treated with (3R,3aR,6aS)-hexahydrofuro[2,3-b]furan-2-yl 4-nitrophenyl carbonate (263 mg, 0.89 mmol, prepared according to Ghosh et al., J. Med. Chem. 1996, 39, 3278.) and N,N-dimethylaminopyridine (197 mg, 1.62 mmol). After stirring for 1.5 h at room temperature, the reaction solvent was evaporated under reduced pressure and the residue was partitioned between EtOAc and 5% citric acid. The organic phase was washed twice with 1% $K_2CO_3$, and then was washed with saturated NaCl, dried ($MgSO_4$), filtered, and evaporated under reduced pressure. The crude product was purified by chromatography on silica gel (1/1-EtOAc/hexane) affording the carbamate (454 mg, 83%) as a solid: mp 128-129° C. (MeOH, uncorrected).

Example 7

Phenol 8: A solution of carbamate 7 (1.15 g, 1.7 mmol) in EtOH (50 mL) and EtOAc (20 mL) was treated with 10%

Pd/C (115 mg) and was stirred under $H_2$ atmosphere (balloon) for 18 h. The reaction solution was purged with $N_2$, filtered through a 0.45 μM filter and was evaporated under reduced pressure to afford the phenol as a solid that contained residual solvent: mp 131-134° C. (EtOAc/hexane, uncorrected).

Example 8

Dibenzylphosphonate 10: To a solution of dibenzylhydroxymethyl phosphonate (527 mg, 1.8 mmol) in $CH_2Cl_2$ (5 mL) was treated with 2,6-lutidine (300 μL, 2.6 mmol) and the reaction flask was cooled to −50° C. (external temperature). Trifluoromethanesulfonic anhydride (360 μL, 2.1 mmol) was added and the reaction mixture was stirred for 15 min and then the cooling bath was allowed to warm to 0° C. over 45 min. The reaction mixture was partitioned between ether and ice-cold water. The organic phase was washed with cold 1M $H_3PO_4$, saturated NaCl, dried ($MgSO_4$), filtered and evaporated under reduced pressure to afford triflate 9 (697 mg, 91%) as an oil which was used directly without any further purification. To a solution of phenol 8 (775 mg, 1.3 mmol) in THF (5 mL) was added $Cs_2CO_3$ (423 mg, 1.3 mmol) and triflate 9 (710 mg, 1.7 mmol) in THF (2 mL). After stirring the reaction mixture for 30 min at room temperature additional $Cs_2CO_3$ (423 mg, 1.3 mmol) and triflate (178 mg, 0.33 mmol) were added and the mixture was stirred for 3.5 h. The reaction mixture was evaporated under reduced pressure and the residue was partitioned between EtOAc and saturated NaCl. The organic phase was dried ($MgSO_4$), filtered and evaporated under reduced pressure. The crude product was chromatographed on silica gel eluting (5% 2-propanol/$CH_2Cl_2$) to give the dibenzylphosphonate as an oil that solidified upon standing. The solid was dissolved in EtOAc, ether was added, and the solid was precipitated at room temperature overnight. After cooling to 0° C., the solid was filtered and washed with cold ether to afford the dibenzylphosphonate (836 mg, 76%) as a white solid:

$^1$H NMR ($CDCl_3$) δ 7.66 (d, 2H), 7.31 (s, 10H), 7.08 (d, 2H), 6.94 (d, 2H), 6.76 (d, 2H), 5.59 (d, 1H), 5.15-4.89 (m, 6H), 4.15 (d, 2H), 3.94-3.62 (m, 10H), 3.13-2.69 (m, 7H), 1.78 (m, 1H), 1.70-1.44 (m, 2H), 0.89-0.82 (2d, 6H); $^{31}$P NMR ($CDCl_3$) δ 18.7; MS (ESI) 853 (M+H).

Example 9

Phosphonic acid 11: A solution of dibenzylphosphonate 10 (0.81 g) was dissolved in EtOH/EtOAc (30 mL/10 mL), treated with 10% Pd/C (80 mg) and was stirred under $H_2$ atmosphere (balloon) for 1.5 h. The reaction was purged with $N_2$, and the catalyst was removed by filtration through celite. The filtrate was evaporated under reduced pressure and the residue was dissolved in MeOH and filtered with a 0.45 μM filter. After evaporation of the filtrate, the residue was triturated with ether and the solid was collected by filtration to afford the phosphonic acid (634 mg, 99%) as a white solid: $^1$H NMR ($CDCl_3$) δ 7.77 (d, 2H), 7.19 (d, 2H), 7.09 (d, 2H), 6.92 (d, 2H), 5.60 (d, 1H), 4.95 (m, 1H), 4.17 (d, 2H), 3.94 (m, 1H), 3.89 (s, 3H), 3.85-3.68 (m, 5H), 3.42 (dd, 1H), 3.16-3.06 (m, 2H), 2.96-2.84 (m, 3H), 2.50 (m, 1H), 2.02 (m, 1H), 1.58 (m, 1H), 1.40 (dd, 1H), 0.94 (d, 3H), 0.89 (d, 3H); $^{31}$P NMR ($CDCl_3$) δ 16.2; MS (ESI) 671 (M−H).

Example 10

Diethylphosphonate 13: Triflate 12 was prepared from diethyl hydroxymethylphosphonate (2 g, 11.9 mmol), 2,6-lutidine (2.1 mL, 17.9 mmol), and trifluoromethanesulfonic anhydride (2.5 mL; 14.9 mmol) as described for compound 9. To a solution of phenol 8 (60 mg, 0.10 mmol) in THF (2 mL) was added $Cs_2CO_3$ (65 mg, 0.20 mmol) and triflate 12 (45 mg, 0.15 mmol) in THF (0.25 mL). The mixture was stirred at room temperature for 2 h and additional triflate (0.15 mmol) in THF (0.25 mL) was added. After 2 h the reaction mixture was partitioned between EtOAc and saturated NaCl. The organic phase was dried ($MgSO_4$), filtered, and evaporated under reduced pressure. The crude product was chromatographed on silica gel (EtOAc) to give a residue that was purified by chromatography on silica gel (5% 2-propanol/$CH_2Cl_2$) to afford the diethylphosphonate as a foam: $^1$H NMR ($CDCl_3$) δ 7.66 (d, 2H), 7.10 (d, 2H), 6.94 (d, 2H), 6.82 (d, 2H), 5.60 (d, 1H), 4.97 (d, 2H), 4.23-4.13 (m, 6H), 3.93-3.62 (m, 10H), 3.12-2.68 (m, 7H), 1.84-1.44 (m, 3H), 1.31 (t, 6H), 0.88-0.82 (2d, 6H); $^{31}$P NMR ($CDCl_3$) δ 17.7; MS (ESI) 729 (M+H).

Example 11

Diphenylphosphonate 14: To a solution of 11 (100 mg, 0.15 mmol) and phenol (141 mg, 1.5 mmol) in pyridine (1.5 mL) was added N,N-diisopropylcarbodiimide (50 μL, 0.38 mmol). The solution was stirred for 31 h at room temperature and for 20 h at 50° C. The solvent was evaporated under reduced pressure and the residue was purified by chromatography on silica gel eluting (EtOAc) to provide diphenylphosphonate 14 (16 mg) as a foam: $^{31}$P NMR ($CDCl_3$) δ 10.9; MS (ESI) 847 (M+Na).

Example 12

Bis-Poc-phosphonate 15: To a solution of 11 (50 mg, 0.74 mmol) and isopropylchloromethyl carbonate (29 mg, 0.19 mmol) in DMF (0.5 mL) was added triethylamine (26 μL, 0.19 mmol) and the solution was heated at 70° C. (bath temperature) for 4.5 h. The reaction was concentrated under reduced pressure and the residue was purified by preparative layer chromatography (2% 2-propanol/$CH_2Cl_2$) to afford 15 (7 mg): $^1$H NMR ($CDCl_3$) δ 7.71 (d, 2H), 7.15 (d, 2H); 7.01 (d, 2H), 6.93 (d, 2H), 5.80-5.71 (m, 4H), 5.67 (d, 1H), 5.07-4.87 (m, 4H), 4.35 (d, 2H), 4.04-3.68 (m, 10H), 3.13 (dd, 1H), 3.04-2.90 (m, 5H), 2.79 (dd, 1H), 1.881.50 (m, 3H+$H_2O$ peak), 1.30 (m, 12H), 0.93 (d, 3H), 0.88 (d, 3H); $^{31}$P NMR ($CDCl_3$) δ 19.6.

Example 13

Synthesis of Bisamidates 16a-j. Representative Procedure, Bisamidate 16f: A solution of phosphonic acid 11 (100 mg, 0.15 mmol) and (S)-2-aminobutyric acid butyl ester hydrochloride (116 mg, 0.59 mmol) was dissolved in pyridine (5 mL) and the solvent was distilled under reduced pressure at 40-60° C. The residue was treated with a solution of $Ph_3P$ (117 mg, 0.45 mmol) and 2,2'-dipyridyl disulfide (98 mg, 0.45 mmol) in pyridine (1 mL) stirring for 20 h at room temperature. The solvent was evaporated under reduced pressure and the residue was chromatographed on silica gel (1% to 5% 2-propanol/$CH_2Cl_2$). The purified product was suspended in ether and was evaporated under reduced pressure to afford bisamidate 16f (106 mg, 75%) as a white solid: $^1$H NMR ($CDCl_3$) δ 7.72 (d, 2H), 7.15 (d, 2H), 7.01 (d, 2H), 6.87 (d, 2H), 5.67 (d, 1H), 5.05 (m, 1H), 4.96 (d, 1H), 4.19-3.71 (m overlapping s, 18H,), 3.42 (t, 1H), 3.30 (t, 1H), 3.20 (dd, 1H), 3.20-2.97 (m, 4H), 2.80 (dd, 2H), 1.87-1.54 (m, 19H), 1.42-1.35 (4H), 0.97-0.88 (m, 18H); $^{31}$P NMR ($CDCl_3$) δ 20.3; MS (ESI) 955 (M+H).

| Compound | $R_1$ | $R_2$ | Amino Acid |
|---|---|---|---|
| 16a | H | Et | Gly |
| 16b | H | Bu | Gly |
| 16c | Me | Et | Ala |
| 16d | Me | Bu | Ala |
| 16e | Et | Et | Aba[1] |
| 16f | Et | Bu | Aba[1] |
| 16g | iBu | Et | Leu |
| 16h | iBu | Bu | Leu |
| 16i | Bn | Et | Phe |
| 16j | Bn | Bu | Phe |

[1]Aba, 2-aminobutyric acid

Example 14

Diazo ketone 17: To a solution of N-tert-Butoxycarbonyl-p-bromo-L-phenylalanine (9.9 g, 28.8 mmol, Synthetech) in dry THF (55 mL) at −25-30° C. (external bath temperature) was added isobutylchloroformate (3.74 mL, 28.8 mmol) followed by the slow addition of N-methylmorpholine (3.16 mL, 28.8 mmol). The mixture was stirred for 25 min, filtered while cold, and the filter cake was rinsed with cold (0° C.) THF (50 mL). The filtrate was cooled to −25° C. and diazomethane (~50 mmol, generated from 15 g diazald according to Aldrichimica Acta 1983, 16, 3) in ether (~150 mL) was poured into the mixed anhydride solution. The reaction was stirred for 15 min and was then placed in an icebath at 0° C., allowing the bath to warm to room temperature while stirring overnight for 15 h. The solvent was evaporated under reduced pressure and the residue was suspended in ether, washed with water, saturated $NaHCO_3$, saturated NaCl, dried ($MgSO_4$), filtered and evaporated to a pale yellow solid. The crude solid was slurried in hexane, filtered, and dried to afford diazo ketone 17 (9.73 g, 90%) which was used directly in the next step.

Example 15

Chloroketone 18: To a solution of diazoketone 17 (9.73 g, 26 mmol) in ether (500 mL) at 0° C. was added 4M HCl in dioxane (6.6 mL, 26 mmol). The solution was stirred for 1 h at 0° C. and 4M HCl in dioxane (1 mL) was added. After 1 h, the reaction solvent was evaporated under reduced pressure to afford the chloroketone 18 (9.79 g, 98%) as a white solid.

Example 16

Chloroalcohol 19: A solution of chloroketone 18 (9.79 g, 26 mmol) in THF (180 mL) and water (16 mL) was cooled to 0° C. (internal temperature). Solid $NaBH_4$ (2.5 g, 66 mmol) was added in several portions over a period of 15 min while maintaining the internal temperature below 5° C. The mixture was stirred for 45 min and saturated $KHSO_4$ was slowly added until the pH<3. The mixture was partitioned between EtOAc and water. The aqueous phase was extracted with EtOAc and the combined organic extracts were washed with brine, dried ($MgSO_4$) filtered and evaporated under reduced pressure. The residue was dissolved in EtOAc, and was passed through a short column of silica gel, and the solvent was evaporated. The solid residue was recrystallized from EtOAc/hexane to afford the chloroalcohol 19 (3.84 g) as a white solid.

Example 17

Epoxide 21: A partial suspension of chloroalcohol 19 (1.16 g, 3.1 mmol) in EtOH (50 mL) was treated with $K_2CO_3$ (2 g, 14.5 mmol) and the mixture was stirred for 4 h at room temperature. The reaction mixture was diluted with EtOAc, filtered, and the solvents were evaporated under reduced pressure. The residue was partitioned between EtOAc and saturated NaCl, and the organic phase was dried ($MgSO_4$), filtered, and evaporated under reduced pressure to afford epoxide 21 (1.05 g; 92%) as a white crystalline solid.

Example 18

Sulfonamide 22: To a solution of epoxide 21 (1.05 g, 3.1 mmol) in 2-propanol (40 mL) was added isobutylamine (6 mL, 61 mmol) and the solution was refluxed for 30 min. The solution was evaporated under reduced pressure and the crude solid was dissolved in $CH_2Cl_2$ (20 mL) and cooled to 0° C. Triethylamine (642 μL, 4.6 mmol) was added followed by the addition of (634 mg, 3.4 mmol) in $CH_2Cl_2$ (5 mL) and the solution was stirred for 2 h at 0° C. at which time the reaction solution was treated with additional triethylamine (1.5 mmol) and 4-methoxybenzenesulfonyl chloride (0.31 mmol). After 1.5 h, the reaction solution was evaporated under reduced pressure. The residue was partitioned between EtOAc and cold 1M $H_3PO_4$. The organic phase was washed with saturated $NaHCO_3$, saturated NaCl, dried ($MgSO_4$), filtered and the solvent was evaporated under reduced pressure. The crude product was purified on silica gel (15/1-$CH_2Cl_2$/EtOAc) to afford 1.67 g of a solid which was recrystallized from EtOAc/hexane to give sulfonamide 22 (1.54 g, 86%) as a white crystalline solid.

Example 19

Silyl ether 23: To a solution of the sulfonamide 22 (1.53 g, 2.6 mmol) in $CH_2Cl_2$ (12 mL) at 0° C. was added N,N-diisopropylethylamine (0.68 mL, 3.9 mmol) followed by tert-butyldimethylsilyl trifluoromethanesulfonate (0.75 mL, 3.3 mmol). The reaction solution was stirred for 1 h at 0° C. and was warmed to room temperature, stirring for 17 h. Additional N,N-diisopropylethylamine (3.9 mmol) and tert-butyldimethylsilyl trifluoromethanesulfonate (1.6 mmol) was added, stirred for 2.5 h, then heated to reflux for 3 h and stirred at room temperature for 12 h. The reaction mixture was partitioned between EtOAc and cold 1M $H_3PO_4$. The organic phase was washed with saturated $NaHCO_3$, saturated NaCl, and was dried ($MgSO_4$), filtered and evaporated under reduced pressure. The crude product was purified on silica gel (2/1-hexane/ether) to afford silyl ether 23 (780 mg, 43%) as an oil.

Example 20

Phosphonate 24: A solution of 23 (260 mg, 0.37 mmol), triethylamine (0.52 mL, 3.7 mmol), and diethylphosphite (0.24 mmol, 1.85 mmol) in toluene (2 mL) was purged with argon and to the solution was added $(Ph_3P)_4Pd$ (43 mg, 10 mol %). The reaction mixture was heated at 110° C. (bath temperature) for 6 h, and was then allowed to stir at room temperature for 12 h. The solvent was evaporated under reduced pressure and the residue was partitioned between ether and water. The aqueous phase was extracted with ether and the combined organic extracts were washed with saturated NaCl, dried ($MgSO_4$), filtered, and the solvent was evaporated under reduced pressure. The residue was purified by chromatography on silica gel (2/1-ethyl acetate/hexane) to afford diethylphosphonate 24 (153 mg, 55%).

Example 21

Phosphonic acid 26: To a solution of 24 (143 mg) in MeOH (5 mL) was added 4N HCl (2 nL). The solution was stirred at room temperature for 9 h and was evaporated under reduced pressure. The residue was triturated with ether and the solid was collected by filtration to provide hydrochloride salt 25 (100 mg, 92%) as a white powder. To a solution of X (47 mg, 0.87 mmol) in $CH_3CN$ (1 mL) at 0° C. was added TMSBr (130 μL, 0.97 mmol). The reaction was warmed to room temperature and stirred for 6.5 h at which time TMSBr (0.87 mmol) was added and stirring was continued for 16 h. The solution was cooled to 0° C. and was quenched with several drops of ice-cold water. The solvents were evaporated under reduced pressure and the residue was dissolved in several milliters of MeOH and treated with propylene oxide (2 mL). The mixture was heated to gentle boiling and evaporated. The residue was triturated with acetone and the solid was collected by filtration to give phosphonic acid 26 (32 mg, 76%) as a white solid.

Example 22

Phosphonate 27: To a suspension of 26 (32 mg, 0.66 mmol) in $CH_3CN$ (1 mL) was added bis(trimethylsilyl)acetamide (100 μL, 0.40 mmol) and the solution was stirred for 30 min at room temperature. The solvent was evaporated under reduced pressure and the residue was dissolved in $CH_3CN$ (1 mL). To this solution was added (3R,3aR,6aS)-hexahydro-furo[2,3-b]furan-2-yl 4-nitrophenyl carbonate (20 mg, 0.069 mmol, prepared according to Ghosh et al. J. Med. Chem. 1996, 39, 3278.), N,N-diisopropylethylamine (35 μL, 0.20 mmol), and N,N-dimethylaminopyridine (catalytic amount). The solution was stirred for 22 h at room temperature, diluted with water (0.5 mL) and was stirred with IR 120 ion exchange resin (325 mg, $H^+$ form) until the pH was <2. The resin was removed by filtration, washed with methanol and the filtrate was concentrated under reduced pressure. The residue was dissolved water, treated with solid $NaHCO_3$ until pH=8 and was evaporated to dryness. The residue was dissolved in water and was purified on C18 reverse phase chromatography eluting with water followed by 5%, 10% and 20% MeOH in water to give the disodium salt 27 (24 mg) as a pale yellow solid: $^1$H NMR ($D_2O$) δ 7.72 (d, 2H), 7.52 (dd, 2H), 7.13 (dd, 2H), 7.05 (d, 2H), 5.58 (d, 1H), 4.87 (m, 1H), 3.86-3.53 (m overlapping s, 10H), 3.22 (dd, 1H), 3.12-2.85 (6H), 2.44 (m, 1H), 1.83 (m, 1H), 1.61 (m, 1H) 1.12 (dd, 1H), 0.77 (m, 6H); $^{31}$P NMR ($D_2O$) δ 11.23; MS (ESI) 641 (M−H).

Example 23

Diethylphosphonate 28: To a solution of 25 (16 mg, 0.028 mmol) in $CH_3CN$ (0.5 mL) was added (3R,3aR,6aS)-hexahydrofuro[2,3-b]furan-2-yl 4-nitrophenyl carbonate (9 mg, 0.031 mmol), N,N-diisopropylethylamine (20 μL, 0.11 mmol), and N,N-dimethylaminopyridine (catalytic amount). The solution was stirred at room temperature for 48 h and was then concentrated under reduced pressure. The residue was partitioned between EtOAc and saturated $NaHCO_3$. The organic phase was washed with saturated $NaHCO_3$, saturated NaCl, and was dried ($MgSO_4$), filtered, and concentrated under reduced pressure. The residue was purified by silica gel chromatography (2.5-5% 2-propanol/$CH_2Cl_2$). The residue obtained was further purified by preparative layer chromatography (5% MeOH/$CH_2Cl_2$) followed by column chromatography on silica gel (10% 2-propanol/$CH_2Cl_2$) to afford diethylphosphonate 28 (7 mg) as a foam: $^1$H NMR ($CDCl_3$) δ 7.72-7.66 (m, 4H), 7.32-7.28 (2H), 6.96 (d, 2H), 5.60 (d, 1H), 4.97 (m, 2H), 4.18-4.01 (m, 4H), 3.94-3.60 (m overlapping s, 10H), 3.15-2.72 (m, 7H), 1.78 (m, 1H), 1.61 (m+$H_2O$, ~3H), 1.28 (t; 6H), 0.86 (m, 6H); $^{31}$P NMR ($CDCl_3$) δ 18.6; MS (ESI) 699 (M+H).

Prospective Example 24

Diphenyl phosphonate 14 is treated with aqueous sodium hydroxide to provide monophenyl phosphonate 29 according to the method found in J. Med. Chem. 1994, 37, 1857. Monophenyl phosphonate 29 is then converted to the monoamidate 30 by reaction with an amino acid ester in the presence of $Ph_3$ and 2,2'-dipyridyl disulfide as described in the synthesis of bisamidate 16f. Alteratively, monoamidate 30 is prepared by treating 29 with an amino acid ester and DCC. Coupling conditions of this type are found in Bull. Chem. Soc. Jpn. 1988, 61, 4491.

Example 25

Diazo ketone 1: To a solution of N-tert-Butoxycarbonyl-O-benzyl-L-tyrosine (25 g, 67 mmol, Fluka) in dry THF (150 mL) at −25-30° C. (external bath temperature) was added isobutylchloroformate (8.9 mL, 69 mmol) followed by the slow addition of N.methylmorpholine (37.5 mL, 69 mmol). The mixture was stirred for 40 min, and diazomethane (170 mmol, generated from 25 g 1-methyl-3-nitro-1-nitroso-guanidine according to Aldrichimica Acta 1983, 16, 3) in ether (400 mL) was poured into the mixed anhydride solution. The reaction was stirred for 15 min allowing the bath to warm to room temperature while stirring overnight for 4 h. The mixture was bubbled with $N_2$ for 30 min., washed with water, saturated $NaHCO_3$, saturated NaCl, dried ($MgSO_4$), filtered and evaporated to a pale yellow solid. The crude solid was slurried in hexane, filtered, and dried to afford the diazo ketone (26.8 g, 99%) which was used directly in the next step.

Example 26

Chloroketone 2: To a suspension of diazoketone 1 (26.8 g, 67 mmol) in ether/THF (750 mL, 3/2) at 0° C. was added 4M HCl in dioxane (16.9 mL, 67 mmol). The solution was stirred at 0° C. for 2 hr. The reaction solvent was evaporated under reduced pressure to give the chloroketone (27.7 g, 97%) as a solid.

Example 27

Chloroalcohol 3: To a solution of chloroketone 2 (127.1 g, 67 mmol) in THF (350 mL) was added water (40 mL) and the solution was cooled to 3-4° C. (internal temperature). $NaBH_4$ (6.3 g, 168 mmol) was added in portions. The mixture was stirred for 1 h at 0° C. and the solvents were removed. The mixture was diluted with ethyl acetate and saturated $KHSO_4$ was slowly added until the pH<4 followed by saturated NaCl. The organic phase was washed with saturated NaCl, dried ($MgSO_4$) filtered and evaporated under reduced pressure. The crude product consisted of a 70:30 mixture of diastereomers by HPLC analysis (mobile phase, 77:25-$CH_3CN$:$H_2O$; flow rate: 1 mL/min; detection: 254 nm; sample volume: 20 μL; column: 5μ C18, 4.6×250 mm, Varian; retention times: major diastereomer 3, 5.4 min, minor diastereomer 4, 6.1 min). The residue was recrystallized from EtOAc/hexane twice to afford the chloro alcohol 3 (12.2 g, >96% diastereomeric purity by HPLC analysis) as a white solid.

Example 28

Epoxide 5: To a solution of chloroalcohol 3 (12.17 g, 130 mmol) in EtOH (300 mL) was added KOH/EtOH solution (0.71N, 51 mL, 36 mmol). The mixture was stirred for at room temperature for 1.5 h. The reaction mixture was evaporated under reduced pressure. The residue was partitioned between EtOAc and water and the organic phase was washed with saturated $NH_4Cl$, dried ($MgSO_4$), filtered, and evaporated under reduced pressure to afford the epoxide (10.8 g, 97%) as a white solid.

Example 29

Sulfonamide 6: To a suspension of epoxide 5 (10.8 g, 30 mmol) in 2-propanol (100 mL) was added isobutylamine (129.8 mL, 300 mmol) and the solution was refluxed for 1 hr. The solution was evaporated under reduced pressure to give a crude solid. The solid (42 mmol) was dissolved in $CH_2Cl_2$ (200 mL) and cooled to 0° C. Triethylamine (11.7 mL, 84 mmol) was added followed by the addition of 4-methoxybenzenesulfonyl chloride (8.68 g, 42 mmol) and the solution was stirred for 40 min at 0° C., warmed to room temperature and evaporated under reduced pressure. The residue was partitioned between EtOAc and saturated $NaHCO_3$. The organic phase was washed with saturated NaCl, dried ($MgSO_4$), filtered and evaporated under reduced pressure. The crude product was recrystallized from EtOAc/hexane to give the sulfonamide (23.4 g, 91%) as a small white needles: mp 122-124° C. (uncorrected).

Example 30

Carbamate 7: A solution of sulfonamide 6 (6.29 mg, 10.1 mmol) in $CH_2Cl_2$ (20 mL) was treated with trifluoroacetic acid (10 mL). The solution was stirred for 3 hr. Volatiles were evaporated under reduced pressure and the residue was partitioned between EtOAc and 0.5 N NaOH. The organic phase were washed with 0.5 N NaOH (2×), water (2×) and saturated NaCl, dried ($MgSO_4$), filtered, and evaporated under reduced pressure. The residue was dissolved in $CH_3CN$ (60 mL), cooled to 0° C. and was treated with (3R,3aR,6aS)hexahydrofuro[2, 3-b]furan-2-yl 4-nitrophenyl carbonate (298.5 g, 10 mmol, prepared according to Ghosh et al. J. Med. Chem. 1996, 39, 3278.) and N,N-dimethylaminopyridine (2.4 g, 20 mmol). After stirring for 1 h at 0° C., the reaction solvent was evaporated under reduced pressure and the residue was partitioned between EtOAc and 5% citric acid. The organic phase was washed twice with 1% $K_2CO_3$, and then was washed with saturated NaCl, dried ($MgSO_4$), filtered, and evaporated under reduced pressure. The crude product was purified by chromatography on silica gel (1/1-EtOAc/hexane) affording the carbamate (5.4 g, 83%) as a solid: mp 128-129° C. (MeOH, uncorrected).

Example 31

Phenol 8: A solution of carbamate 7 (5.4 g, 8.0 mmol) in EtOH (260 mL) and EtOAc (130 mL) was treated with 10% Pd/C (540 mg) and was stirred under $H_2$ atmosphere (balloon) for 3 h. The reaction solution stirred with celite for 10 min, and passed through a pad of celite. The filtrate was evaporated under reduced pressure to afford the phenol as a solid (4.9 g) that contained residual solvent: mp 131-134° C. (EtOAc/hexane, uncorrected).

Example 32

Dibenzylphosphonate 10: To a solution of dibenzylhydroxymethyl phosphonate (3.1 g, 10.6 mmol) in $CH_2Cl_2$ (30 mL) was treated with 2,6-lutidine (1.8 mL, 15.6 mmol) and the reaction flask was cooled to −50° C. (external temperature). Trifluoromethanesulfonic anhydride (2.11 mL, 12.6 mmol) was added and the reaction mixture was stirred for 15 min and then the cooling bath was allowed to warm to 0° C. over 45 min. The reaction mixture was partitioned between ether and ice-cold water. The organic phase was washed with cold 1M $H_3PO_4$, saturated NaCl, dried ($MgSO_4$), filtered and evaporated under reduced pressure to afford triflate 9 (3.6 g, 80%) as an oil which was used directly without any further purification. To a solution of phenol 8 (3.61 g, 6.3 mmol) in THF (90 mL) was added $Cs_2CO_3$ (4.1 g, 12.6 mmol) and triflate 9 (4.1 g, 9.5 mmol) in THF (10 mL). After stirring the reaction mixture for 30 min at room temperature additional $Cs_2CO_3$ (6.96 g, 3 mmol) and triflate (1.26 g, 3 mmol) were added and the mixture was stirred for 3.5 h. The reaction mixture was evaporated under reduced pressure and the residue was partitioned between EtOAc and saturated NaCl. The organic phase was dried ($MgSO_4$), filtered and evaporated under reduced pressure. The crude product was chromatographed on silica gel eluting (5% 2-propanol/$CH_2Cl_2$) to give the dibenzylphosphonate as an oil that solidified upon standing. The solid was dissolved in EtOAc, ether was added, and the solid was precipitated at room temperature overnight. After cooling to 0° C. the solid was filtered and washed with cold ether to afford the dibenzylphosphonate (3.43 g, 64%) as a white solid: $^1$H NMR ($CDCl_3$) δ 7.66 (d, 2H), 7.31 (s, 10H), 7.08 (d, 2H), 6.94 (d, 2H), 6.76 (d, 2H), 5.59 (d, 1H), 5.15-4.89 (m, 6H), 4.15 (d, 2H), 3.94-3.62 (m, 10H), 3.13-2.69 (m, 7H), 1.78 (m, 1H), 1.70-1.44 (m, 2H), 0.89-0.82 (2d, 6H); $^{31}$P NMR ($CDCl_3$) δ 18.7; MS (ESI) 853 (M+H).

Example 33

Phosphonic acid 11: A solution of dibenzylphosphonate 10 (3.43 g) was dissolved in EtOH/EtOAc (150 mL/50 mL), treated with 10% Pd/C (350 mg) and was stirred under $H_2$ atmosphere (balloon) for 3 h. The reaction mixture was stirred with celite, and the catalyst was removed by filtration through celite. The filtrate was evaporated under reduced pressure and the residue was dissolved in MeOH and filtered with a 0.45 μM filter. After evaporation of the filtrate, the residue was triturated with ether and the solid was collected by filtration to afford the phosphonic acid (2.6 g, 94%) as a white solid: $^1$H NMR ($CDCl_3$) δ 7.77 (d, 2H), 7.19 (d, 2H), 7.09 (d, 2H), 6.92 (d, 2H), 5.60 (d, 1H), 4.95 (m, 1H), 4.17 (d, 2H), 3.94 (i, 1H), 3.89 (s, 3H), 3.85-3.68 (m, 5H), 3.42 (dd, 1H), 3.16-3.06 (m, 2H), 2.96-2.84 (m, 3H), 2.50 (m, 1H), 2.02 (m, 1H), 1.58 (m, 1H), 1.40 (dd, 1H), 0.94 (d, 3H), 0.89 (d, 3H); $^{31}$P NMR ($CDCl_3$) δ 16.2; MS (ESI) 671 (M−H).

Example Section B

There is no Section B in this application.

Example Section C

Example 1

Diphenyl phosphonate 31: To a solution of phosphonic acid 30 (11 g, 16.4 mmol) and phenol (11 g, 117 mmol) in pyridine (100 mL) was added 1,3-dicyclohexylcarbodiimide (13.5 g, 65.5 mmol). The solution was stirred at room temperature for 5 min and then at 70° C. for 2 h. The reaction mixture was cooled to room temperature, diluted with ethyl acetate (100 mL) and filtered. The filtrate was evaporated under reduced pressure to remove pyridine. The residue was dissolved in ethyl acetate (250 mL) and acidified to pH=4 by addition of HCl (0.5 N) at 0° C. The mixture was stirred at 0° C. for 0.5 h, filtered and the organic phase was separated and washed with brine, dried over $MgSO_4$, filtered and concentrated under reduced pressure. The residue was purified on silica gel to give diphenyl phosphonate 31 (9 g, 67%) as a solid. $^{31}P$ NMR ($CDCl_3$) d 12.5.

Example 2

Monophenyl phosphonate 32: To a solution of diphenylphosphonate 31 (9.0 g, 10.9 mmol) in acetonitrile (400 mL) was added NaOH (1N, 27 mL) at 0° C. The reaction mixture was stirred at 0° C. for 1 h, and then treated with Dowex (50W×8-200, 12 g). The mixture was stirred for 0.5 h at 0° C., and then filtered. The filtrate was concentrated under reduced pressure and co-evaporated with toluene. The residue was dissolved in ethyl acetate and hexane was added to precipitate out the monophenyl phosphonate 32 (8.1 g, 100%). $^{31}P$ NMR ($CDCl_3$) d 18.3.

Example 3

Monoamidate 33a ($R_1$=Me, $R_2$=n-Bu): To a flask charged with monophenyl phosphonate 32 (4.0 g, 5.35 mmol), was added L-alanine n-butyl ester hydrochloride (4.0 g, 22 mmol), 1,3-dicyclohexylcarbodiimide (6.6 g, 32 mmol), and finally pyridine (30 mL) under nitrogen. The resultant mixture was stirred at 60-70° C. for 1 h, then cooled to room temperature and diluted with ethyl acetate. The mixture was filtered and the filtrate was concentrated under reduced pressure. The residue was partitioned between ethyl acetate and HCl (0.2 N) and the organic layer was separated. The ethyl acetate phase was washed with water, saturated $NaHCO_3$, dried over MgSO4, filtered and concentrated under reduced pressure. The residue was purified on silica gel (pre-treated with 10% $MeOH/CH_3CO_2Et$, eluting with 40% $CH_2Cl_2/CH_3CO_2Et$ and $CH_3CO_2Et$) to give two isomers of 33a in a total yield of 51%. Isomer A (1.1 g): $^1H$ NMR ($CDCl_3$) d 0.88 (m, 9H), 1.3 (m, 2H), 1.35 (d, J=7 Hz, 3H), 1.55 (m, 2H), 1.55-1.7 (m, 2H), 1.8 (m, 1H), 2.7-3.2 (m, 7H), 3.65-4.1 (m, 9H), 3.85 (s, 3H), 4.2 (m, 1H), 4.3 (d, J=9.6 Hz, 2H), 5.0 (m, 2H), 5.65 (d, J=5.4 Hz, 1H), 6.85 (d, J=8.7 Hz, 2H), 7.0 (d, J=8.7 Hz, 2H), 7.1-7.3 (m, 7H), 7.7 (d, J=8.7 Hz, 2H); $^{31}P$ NMR ($CDCl_3$) d 20.5. Isomer B (1.3 g) $^1H$ NMR ($CDCl_3$) d 0.88 (m, 9H), 1.3 (m, 2H), 1.35 (d, J=7 Hz, 3H), 1.55 (m, 2H), 1.55-1.7 (m, 2H), 1.8 (m, 1H), 2.7-3.2 (m, 7H), 3.65-4.1 (m, 9H), 3.85 (s, 3H), 4.2-4.35 (m, 3H), 5.0 (m, 2H), 5.65 (d, J=5.4 Hz, H), 6.85 (d, J=8.7 Hz, 2H), 7.0 (d, J=8.7 Hz, 2H), 7.1-7.3 (m, 7H), 7.7 (d, J=8.7 Hz, 2H); $^{31}P$ NMR ($CDCl_3$) d 19.4.

Example 4

Monoamidate 33b ($R_1$=Me, $R_2$=i-Pr) was synthesized in the same manner as 33a in 77% yield. Isomer A: $^1H$ NMR ($CDCl_3$) d 0.9 (2d, J=6.3 Hz, 6H), 1.2 (d, J=7 Hz, 6H), 1.38 (d, J=7 Hz, 3H), 1.55-1.9 (m, 3H), 2.7-3.2 (m, 7H), 3.65-4.1 (m, 8H), 3.85 (s, 3H), 4.2 (m, 1H), 4.3 (d, J=9.6 Hz, 2H), 5.0 (m, 2H), 5.65 (d, J=5.4 Hz, 1H), 6.85 (d, J=8.7 Hz, 2H), 7.0 (d, J=8.7 Hz, 2H), 7.1-7.3 (m, 7H), 7.7 (d, J=8.7 Hz, 2H); $^{31}P$ NMR ($CDCl_3$) d 20.4. Isomer B: $^1H$ NMR ($CDCl_3$) d 0.9 (2d, J=6.3 Hz, 6H), 1.2 (d, J=7 Hz, 6H), 1.38 (d, J=7 Hz, 3H), 1.55-1.9 (m, 3H), 2.7-3.2 (m, 7H), 3.65-4.1 (m, 8H), 3.85 (s, 3H), 4.2 (m, 1H), 4.3 (d, J=9.6 Hz, 2H), 5.0 (m, 2H), 5.65 (d, J=5.4 Hz, 1H), 6.85 (d, J=8.7 Hz, 2H), 7.0 (d, J=8.7 Hz, 2H), 7.1-7.3 (m, 7H), 7.7 (d, J=8.7 Hz, 2H); $^{31}P$ NMR ($CDCl_3$) d 19.5.

Example Section D

Example 1

Cyclic Anhydride 1 (6.57 g, 51.3 mmol) was treated according to the procedure of Brown et al., J. Amer. Chem. Soc. 1955, 77, 1089-1091 to afford amino alcohol 3 (2.00 g, 33%), for intermediate 2: $^1H$ NMR ($CD_3OD$) δ 2.40 (S, 2H), 1.20 (s, 6H).

Example 2

Amino alcohol 3 (2.0 g, 17 mmol) was stirred in 30 mL 1:1 THF: water. Sodium Bicarbonate (7.2 g, 86 mmol) was added, followed by Boc Anhydride (4.1 g, 19 mmol). The reaction was stirred for 1 hour, at which time TLC in 5% methanol/DCM with ninhydrin stain showed completion. The reaction was partitioned between water and ethyl acetate. The organic layer was dried and concentrated, and the resulting mixture was chromatographed on silica in 1:1 hexane: ethyl acetate to afford two fractions, "upper" and "lower" each having the correct mass. By NMR the correct product 4 was "lower" (0.56 g, 14%) $^1H$ NMR ($CDCl_3$) δ 3.7 (t, 2H), 3.0 (d, 2H), 1.45 (t, 2H) 1.4 (s, 9H), 0.85 (s, 6H), MS (ESI): 240 (M+23).

Example 3

Sodium Hydride (60% emulsion in oil) was added to a solution of the alcohol 4 (1.1 g, 5.2 mmol) in dry DMF in a 3-neck flask under dry nitrogen. Shortly afterward triflate 35 (2.4 g, 5.7 mmol) was added with stirring for 1.5 hrs. Mass spectrometry showed the presence of the starting material (240, M+23), thus 100 mg more 60% sodium hydride emulsion as well as ~1 g more triflate were added with an additional hour of stirring. The reaction was quenched by the addition of saturated $NaHCO_3$ then partitioned between ethyl acetate and water. The organic layer was dried with brine and $MgSO_4$ and eluted on silica with 1:1 hexane:ethyl acetate to afford 5 (0.445 g, 15%). NMR showed some contamination with alcohol 4 starting material. $^1H$ NMR ($CDCl_3$): δ 7.28 (s, 10H), 5.00 (m, 4H), 3.70 (t, 2H), 2.94, (d, 2H), 1.44 (t, 2H), 1.40 (s, 9H), 0.83 (s, 6H) MS (ESI): 514 (M+23).

Example 4

Phosphonate ester 5 (0.445 g, 0.906 mmol) was stirred with with 20% TFA in DCM. (5 mL) TLC showed completion in 1 hr time. The reaction was azeotroped with toluene then run on a silica gel column with 10% methanol in DCM. Subsequently, the product was dissolved in ethyl acetate and shaken with saturated sodium bicarbonate: water (1:1), dried with brine and magnesium sulfate to afford the free amine 6 (30 mg, 8.5%). $^1H$ NMR ($CDCl_3$): δ 7.30 (s, 10H), 5.00 (m, 4H), 3.67 (d, 2H), 3.47, (t, 2H), 2.4-2.6 (brs) 1.45 (t, 2H), 0.82 (s, 6H), MS (ESI): 393 (M+1).

Example 5

Amine 6 (30 mg, 0.08 mmol) and epoxide 7 (21 mg, 0.08 mmol) were dissolved in 2 mL IprOH and heated to reflux for 1 hr then monitored by TLC in 10% MeOH/DCM. Added ~20 mg more epoxide 7 and continued reflux for 1 hr. Cool to room temperature, dilute with ethyl acetate, shake with water and brine, dry with magnesium sulfate. Silica gel chromatography using first 5% then 10% MeOH in EtOAc yielded amine 8 (18 mg, 36%). $^1H$ NMR ($CDCl_3$): δ 7.30 (s, 10H), 7.20-7-14 (m, 5H), 5.25-4.91 (m, 4H), 3.83, (m, 1H), 3.71 (d, 2H) 3.64 (m, 1H), 3.54 (t, 2H), 3.02-2.61 (m, 5H), 2.65-2.36 (dd, 2H) (t, 2H), 1.30 (s, 9H) 0.93 (s, 9H) 0.83 (t, 2H) MS (ESI) 655 (M+1).

Example 6

Amine 8 (18 mg, 0.027 mmol) was dissolved in 1 mL DCM then acid chloride 9 (6 mg, 0.2 mmol) followed by triethylamine (0.004 mL, 0.029 mmol). The reaction was monitored by TLC. Upon completion the reaction was diluted with DCM shaken with 5% citric acid, saturated sodium bicarbonate, brine, and dried with $MgSO_4$. Purification on silica (1:1 Hexane:EtOAc) afforded sulfonamide 10 (10.5 mg, 46%). $^1H$ NMR ($CDCl_3$): δ 7.69 (d, 2H), 7.30 (s, 10H), 7.24-7-18 (m, 5H), 5.00 (m, 4H), 4.73, (d, 1H), 4.19 (s, 1H) 3.81 (m, 1H), 3.80 (s, 3H), 3.71 (d, 2H), 3.57 (t, 2H), 3.11-2.95 (m, 5H) 2.75 (m, 1H) 1.25 (s, 1H), 0.90 (s, 6H) MS (ESI) 847 ($M+Na^+$).

Example 7

Sulfonamide 10 (10.5 mg, 0.013 mmol) was stirred at room temperature in 20% TFA/DCM. Once Boc deprotection was complete by TLC (1:1 Hexane:EtOAc) and MS, the reaction was azeotroped with toluene. The TFA salt of the amine was dissolved in acetonitrile (0.5 mg) and to this were added carbonate 11 (4.3 mg, 0.014 mmol) followed by DMAP (4.6 mg, 0.038 mg). Stir at room temp until TLC (1:1 Hexane:EtOAc) shows completion. Solvent was evaporated and the residue was redissolved in EtOAc then shaken with saturated $NaHCO_3$. The organic layer was washed with water and brine, then dried with $MgSO_4$ Purification on silica with Hexane:EtOAc afforded compound 12 (7.1 mg, 50%). $^1H$ NMR ($CDCl_3$): δ 7.75 (d, 2H) 7.24-7.35 (15H) 6.98 (d, 2H), 5.62 (d, 1H) 5.04 (m, 4H) 4.98 (m, 1H) 4.03 (m, 1H), 3.85 (s, 3H), 3.61-3.91 (9H), 3.23-3.04 (5H) 2.85 (m, 1H), 2.74 (m, 1H) 1.61 (d, 2H), 1.55 (m, 1H) 1.36 (m, 1H) 0.96 (d, 6H) MS (ESI): 903 (M+23).

Example 8

Compound 12 (6.1 mg, 0.007 mmol) was dissolved in 1 mL 3:1 EtOH:EtoAc. Palladium catalyst (10% on C, 1 mg) was added and the mixture was purged three times to vacuum with 1 atmosphere hydrogen gas using a balloon. The reaction was stirred for 2 hrs, when MS and TLC showed completion. The reaction was filtered through Celite with EtOH washing and all solvent to was evaporated to afford final compound 13 (5 mg, 100%). $^1H$ NMR ($CD_3OD$): δ 7.79 (d, 2H) 7.16-7.24 (5H) 7.09 (d, 2H) 5.58 (d, 1H) 4.92 (m, 1H) 3.97 (m, 1H), 3.92 (dd, 1H) 3.89 (s, 3H) 3.66-3.78 (8H) 3.40 (d, 1H), 3.37 (dd, 1H), 3.15 (m, 1H) 3.12 (dd, 1H) 2.96 (d, 1H), 2.87 (m, 1H), 2.74 (m, 1H) 2.53 (m, 1H) 1.70 (m, 2H), 1.53 (m, 1H) 1.32 (m, 1H) 1.04 (d, 6H) MS (ESI): 723 (M+23).

Example 9

Amino Alcohol 14 (2.67 g, 25.9 mmol) was dissolved in THF with stirring and Boc Anhydride (6.78 g, 31.1 mmol) was added. Heat and gas evolution ensued. TEA (3.97 mL, 28.5 mmol) was added and the reaction was stirred overnight. In the morning, the reaction was quenched by the addition of saturated $NaHCO_3$. The organic layer was separated out and shaken with water, dried with brine and $MgSO_4$ to afford 15 which was used without further purification. (100% yield) (some contamination): $^1H$ NMR ($CDCl_3$): δ 3.76 (t, 1H) 3.20, (d, 2H), 2.97 (d, 2H), 1.44 (s, 9H), 0.85 (s, 6H).

Example 10

A solution of the alcohol 15 (500 mg, 2.45 mmol) in dry THF was cooled under dry $N_2$ with stirring. To this was added n-butyl lithium (1.29 mL, 2.71 mmol) as a solution in hexane in a manner similar to that described in Tetrahedron. 1995, 51 #35, 9737-9746. Triflate 35 (1.15 g, 2.71 mmol) was added neat with a tared syringe. The reaction was stirred for four hours, then quenched with saturated $NaHCO_3$. The mixture was then partitioned between water and EtOAc. The organic layer was dried with brine and $MgSO_4$, then chromatographed on silica in 1:1 Hexane:EtOAc to afford phosphonate 16 (445 mg, 38%) $^1H$ NMR ($CDCl_3$): δ 7.37 (m, 10H), 5.09 (m, 4H), 3.73-3.75 (m, 2H), 3.24 (s, 2H), 3.02 (d, 2H), 1.43 (s, 9H), 0.86 (s, 6H).

Example 11

Phosphonate 16 (249 mg, 0.522 mmol) was stirred in 20% TFA/DCM for 1 hr. The reaction was then azeotroped with toluene. The residue was re-dissolved in EtOAc, then shaken with water:saturated $NaHCO_3$ (1:1). The organic layer was dried with brine and $MgSO_4$ and solvent was removed to afford amine 17 (143 mg, 73%) $^1H$ NMR ($CDCl_3$): δ 7.30 (s, 10H), 5.05-4.99 (m, 4H), 3.73 (d, 2H), 3.23 (s, 2H), 2.46 (brs, 2H), 0.80 (s, 6H) $^{31}P$ NMR ($CDCl_3$): δ 23.77 (s).

Example 12

Amine 17 (143 mg, 0.379 mmol) and epoxide 7 (95 mg, 0.360 mmol) were dissolved in 3 mL IprOH and heated to 85° C. for 1 hr. The reaction was cooled to room temperature overnight then heated to 85° C. for 1 hr more in the morning. The reaction was then diluted with EtOAc, shaken with water, dried with brine $MgSO_4$ and concentrated. The residue was eluted on silica in a gradient from 5% to 10% MeOH in DCM to afford compound 18 (33 mg, 14%).

Example 13

Mix compound 18 (33 mg, 0.051 mmol) and chlorosulfonyl compound 9 (11 mg, 0.054 mmol) in 2 mL DCM then add TEA (0.0075 mL, 0.054 mmol), stir for 5 hrs. TLC in 1:1 EtOAc:hexane shows reaction not complete. Place in freezer overnight. In the morning, take out of freezer, stir for 2 hrs, TLC shows completion. Workup done with 5% citric acid, saturated $NaHCO_3$, then dry with brine and $MgSO_4$. The reaction mixture was concentrated and chromatographed on a Monster Pipette column in 1:1 hexane:EtOAc then 7:3 hexane:EtOAc to avail compound 19 (28 mg, 67%) $^1H$ NMR ($CDCl_3$): δ 7.37 (d, 2H), 7.20 (m, 15H), 6.90 (d, 2H), 5.07-4.93 (m, 4H), 4.16 (brs, 1H), 3.80 (s, 3H), 3.75-3.37 (m, 4H), 3.36 (d, 1H), 3.20-2.93 (m, 6H), 2.80-2.75 (dd, 1H).

Example 14

Compound 19 (28 mg, 0.35 mmol) was stirred in 4 mL DCM with addition of 1 mL TFA. Stir for 45 minutes, at which time complete deprotection was noted by TLC as well as MS. Azeotrope with toluene. The residue was dissolved in 1 mL $CH_3CN$, cooled to 0° C. Bis-Furan para-Nitro phenol carbonate 11 (12 mg, 0.038 mmol), dimethyl amino pyridine (~1 mg, 0.008 mmol) and diisopropylethylamine (0.018 mL, 0.103 mmol) were added. The mixture was stirred and allowed to come to room temperature and stirred until TLC in 1:1 hexane:EtOAc showed completion. The reaction mixture was concentrated and the residue was partitioned between saturated $NaHCO_3$ and EtOAc. The organic layer was dried with brine and $MgSO_4$, then chromatographed on silica with hexane:EtOAc to afford compound 20 (20 mg, 67%). $^1$NMR ($CDCl_3$): δ 7.76 (d, 2H), 7.34-7.16 (m, 15H), 7.07 (d, 2H), 5.56 (d, 1H), 5.09 (m, 4H), 4.87 (m, 1H), 4.01 (m, 1H), 3.91 (m, 2H), 3.87 (s, 3H), 3.86 (m, 1H), 3.69 (m, 1H), 3.67 (m, 1H) 3.60 (d, 2H) 3.28 (m, 1H) 3.25 (d, 2H), 3.32 (d, 1H), 3.13 (m, 1H), 3.02 (m, 1H) 2.85 (d, 1H), 2.83 (m, 1H) 2.52 (m, 1H) 1.47 (m, 1H), 1.31 (m, 1H) 0.98 (s, 3H), 0.95 (s, 3H).

Example 15

Compound 20 (7 mg, 0.008 mmol) was treated in a manner identical to example 8 to afford compound 21 (5 mg, 90%) $^1$H NMR ($CDCl_3$): δ 7.80 (d, 2H), 7.25-7.16 (m, 5H), 7.09 (d, 2H), 5.58 (d, 1H), 4.92 (m, 1H), 3.99 (m, 1H), 3.92 (m, 1H), 3.88 (s, 3H), 3.86 (m, 1H), 3.77 (m, 1H), 3.75 (m, 1H), 3.73 (m, 1H), 3.71 (m, 1H) 3.71 (m, 1H), 3.68 (m, 1H), 3.57 (d, 1H), 3.41 (d, 1H), 3.36 (m, 1H), 3.29 (d, 1H), 3.25 (d, 2H), 3.18 (m, 1H), 3.12 (m, 1H), 3.01 (d, 1H) 2.86 (m, 1H), 2.53 (m, 1H) 1.50 (m, 1H), 1.33 (m, 1H), 1.02 (s, 3H), 0.99 (s, 3H).

Example 16

Compound 15 (1.86 g, 9.20 mmol) was treated with triflate 22 in a manner identical to example 10 to afford compound 23 (0.71 g, 21.8%) $^1$H NMR ($CDCl_3$): δ 5.21 (brs, 1H) 4.164.07 (m, 4H), 3.71-3.69 (d, 2H), 3.24 (s, 2H), 1.43 (s, 9H), 1.34-1.28 (m, 6H) 0.86 (s, 6H).

Example 17

Compound 23 (151 mg, 0.427 mmol) was dissolved in 10 mL DCM and 1.0 mL TFA was added. The reaction was stirred until completion. The reaction was azeotroped with toluene and the residue was then dissolved in THF and treated with basic Dowex resin beads. Afterwards, the beads were filtered away and solvent was removed to avail compound 24 (100 mg, 92%) $^1$H NMR ($CDCl_3$): δ 4.15-4.05 (m, 4H), 3.72-3.69 (d, 2H), 3.27 (s, 2H), 1.30-1.26 (m, 6H) 0.81 (s, 6H).

Example 18

Compound 24 (100 mg, 0.395 mmol) was treated in a manner identical to example 12 to avail compound 25 (123 mg, 60%). $^1$H NMR ($CDCl_3$): δ 7.26-7.13 (m, 5H), 4.48-4.83 (d, 1H) 4.17-4.06 (m, 4H), 3.75 (d, 2H) 3.56 (brs, 1H), 3.33 (s, 2H), 2.93-2.69 (m, 4H), 2.44-2.55 (dd, 2H) 1.32 (m, 6H), 0.916 (s, 6H).

Example 19

Compound 25 (88 mg, 0.171 mmol) was treated in a manner identical to example 13 to afford compound 26 (65 mg, 55%) $^1$H NMR ($CDCl_3$): δ 7.26-7.13 (m, 5H), 4.48-4.83 (d, 1H) 4.17-4.06 (m, 4H), 3.75 (d, 2H) 3.56 (brs, 1H), 3.33 (s, 2H), 2.93-2.69 (m, 4H), 2.44-2.55 (dd, 2H) 1.32 (m, 6H), 0.916 (s, 6H).

Example 20

Compound 26 (65 mg, 0.171 mmol) was treated in a manner identical to example 14 to afford compound 27 (49 mg, 70%) $^1$H NMR:

($CDCl_3$): δ 7.75 (d, 2H), 7.25-7.24 (m, 4H), 7.18 (m, 1H) 6.99 (d, 2H), 5.63 (d, 1H), 5.01 (m, 1H), 4.16 (m, 4H), 3.94 (m, 1H), 3.88 (m, 1H), 3.88 (s, 3H), 3.84 (m, 1H), 3.81 (m, 1H), 3.74 (m, 2H),), 3.70 (m, 1H), 3.69 (m, 1H) 3.43 (m, 1H), 3.24 (m, 1H), 3.22 (m, 2H) 3.21 (m, 2H) 3.12 (m, 1H), 3.02 (m, 1H) 2.86 (m, 1H), 2.72 (m, 1H), 1.54 (m, 1H), 1.38 (m, 1H) 1.35 (m, 6H) 1.00 (s, 3H), 0.96 (s, 3H).

Example 21

Boc protected amine 28 (103 mg, 0.153 mmol) was dissolved in DCM (5 mL). The stirred solution was cooled to 0° C. $BBr_3$ as a 1.0 M solution in DCM (0.92 mL, 0.92 mmol) was added dropwise over 10 min, and the reaction was allowed to continue stirring at 0° C. for 20 min. The reaction was warmed to room temperature and stirring was continued for 2 hours. The reaction was then cooled to 0° C. and quenched by dropwise addition of MeOH (1 mL). The reaction mixture was evaporated and the residue suspended in methanol which was removed under reduced pressure. The procedure was repeated for EtOAc and finally toluene to afford free amine HBr salt 29 (107 mg, >100%) which was used without further purification.

Example 22

Amine HBr salt 29 (50 mg, 0.102 mmol) was suspended in 2 mL $CH_3CN$ with stirring then cooled to 0° C. DMAP (25 mg, 0.205 mmol) was added, followed by Carbonate 11. The reaction was stirred at 0° C. for 1.5 hrs then allowed to warm to room temperature. The reaction was stirred overnight. A few drops Acetic acid were added to the reaction mixture, which was concentrated and re-diluted with ethyl acetate, shaken with 10% citric acid then saturated $NaHCO_3$. The organic layer was dried with brine and $MgSO_4$ and eluted on silica to afford di-phenol 30 (16 mg, 28%) $^1$H NMR ($CD_3OD$): δ 7.61, (d, 2H), 7.01 (d, 2H), 6.87 (d, 2H), 6.62 (d, 2H), 5.55 (d, 1H), 4.93 (m, 1H), 3.92 (m, 2H), 3.79 (m, 5H), 3.35 (m, 1H), 3.07 (m, 2H), 2.88 (m, 3H), 2.41 (m, 1H), 2.00 (m, 1H), 1.54 (m, 1H), 1.31 (dd, 1H) 0.89-0.82 (dd, 6H).

Example 23

A solution of di-phenol 30 (100 mg, 0.177 mmol) was made in $CH_3CN$ that had been dried over $K_2CO_3$. To this, the triflate (0.084 mL, 0.23 mmol) was added, followed by $Cs_2CO_3$ (173 mg, 0.531 mmol). The reaction was stirred for 1 hr. TLC (5% IprOH/DCM) showed 2 spots with no starting materials left. Solvent was evaporated and the residue was partitioned between EtOAc and water. The organic layer was washed with saturated $NaHCO_3$, then dried with brine and $MgSO_4$. The mixture was separated by column chromatography on silica with 3% IprOH in DCM. The upper spot 31 (90 mg, 46%) was confirmed to be the bis alkylation product. The lower spot required further purification on silica gel plates to afford a single mono alkylation product 32 (37 mg, 26%). The other possible alkylation product was not observed. NMR: $^1$H NMR ($CDCl_3$): for 31: δ 7.57 (d, 2H), 7.37 (m, 10H) 7.03 (d, 2H), 6.99 (d, 2H), 6.73 (d, 2H), 5.69 (d, 1H), 5.15-5.09 (m, 4H), 5.10 (m, 1H), 4.32 (d, 2H), 4.02 (d, 1H), 3.82 (m, 1H) 3.81 (m, 1H), 3.93-3.81 (m, 2H), 3.74 (d, 1H), 3.06 (m, 1H), 3.00 (m, 1H), 2.96 (m, 1H), 2.91 (m, 1H)

2.77 (m, 1H) 2.64 (m, 1H) 2.47 (m, 1H) 1.82 (m, 2H) 1.79 (m, 1H), 0.94-0.86 (dd, 6H) for 32: δ 7.68 (d, 2H), 7.33-7.35 (m, 20H), 7.11 (d, 2H), 6.96 (d, 2H), 6.80 (d, 2H), 5.26 (d, 1H), 5.11 (m, 8H), 5.00 (m, 1H) 4.23 (d, 2H), 4.19 (d, 2H), 3.93 (m, 1H), 3.82-3.83 (m, 3H), 3.68-3.69 (m, 2H) 3.12-2.75 (m, 7H), 1.82 (m, 1H), 1.62-1.52 (d, 2H), 0.89-0.86 (dd, 6H).

Example 24

Ref: J. Med. Chem. 1992, 35 10, 1681-1701

To a solution of phosphonate 32 (100 mg, 0.119 mmol) in dry dioxane was added $Cs_2CO_3$ (233 mg, 0.715 mmol), followed by 2-(dimethylamino)ethyl chloride hydrochloride salt (69 mg, 0.48 mmol). The reaction was stirred at room temperature and monitored by TLC. When it was determined that starting material remained, additional $Cs_2CO_3$ (233 mg, 0.715 mmol) as well as amine salt (69 mg, 0.48 mmol) were added and the reaction was stirred overnight at 60° C. In the morning when TLC showed completion the reaction was cooled to room temperature, filtered, and concentrated. The product amine 33 (40 mg, 37%) was purified on silica. Decomposition was noted as lower spots were seen to emerge with time using 15% MeOH in DCM on silica.

Example 25:

Amine 33 (19 mg, 0.021 mmol) was dissolved in 1.5 mL DCM. This solution was stirred in an icebath. Methane sulfonic acid (0.0015 mL, 0.023 mmol) was added and the reaction was stirred for 20 minutes. The reaction was warmed to room temperature and stirred for 1 hour. The product, amine mesylate salt 34 (20 mg, 95%) was precipitated out by addition of hexane. $^1$H NMR ($CD_3OD$): δ 7.69 (d, 2H), 7.35 (m, 10H), 7.15 (m, 4H) 6.85 (m, 2H), 5.49 (d, 1H), 5.10 (m, 4H), 4.83 (m, 1H), 4.62 (d, 2H), 4.22 (m, 2H), 3.82 (m, 1H), 3.56 (m, 1H), 3.48 (m, 2H), 3.35 (m, 1H), 2.99 (m, 1H), 2.95 (m, 1H), 2.84 (s, 6H), 2.78 (m, 1H), 2.75 (m, 1H), 2.70 (m, 1H), 2.40 (m, 1H) 1.94 (m, 1H), 1.43 (m, 1H), 1.27 (m, 1H), 0.77 (dd, 6H).

Example Section E

Scheme 1

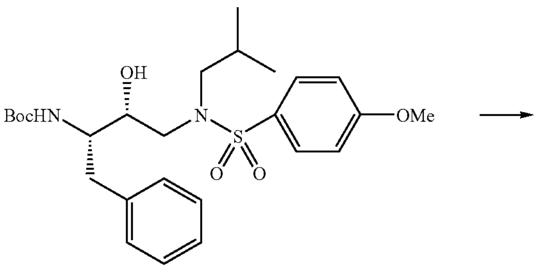

1

-continued

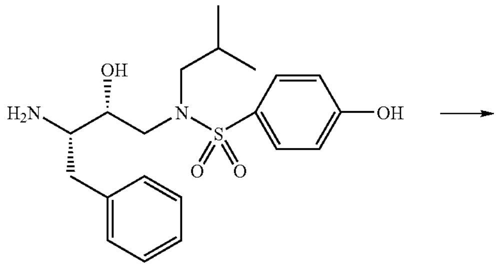

2

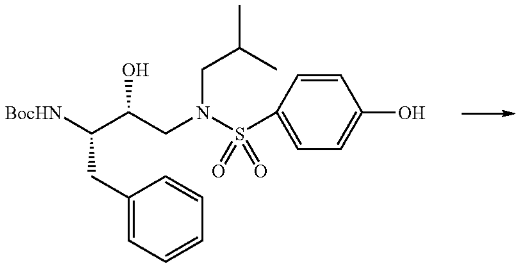

3

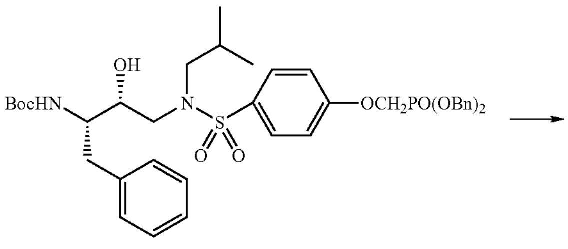

4

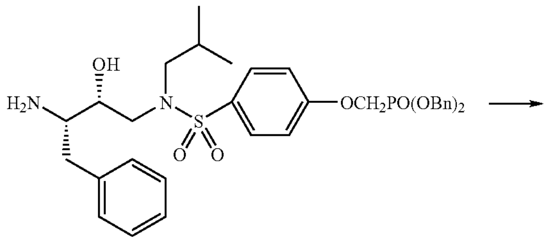

5

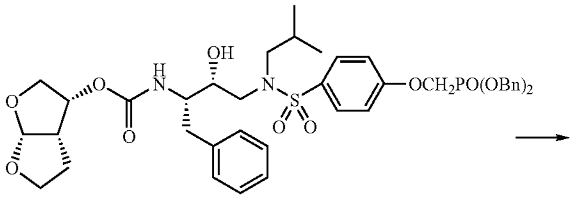

6

-continued

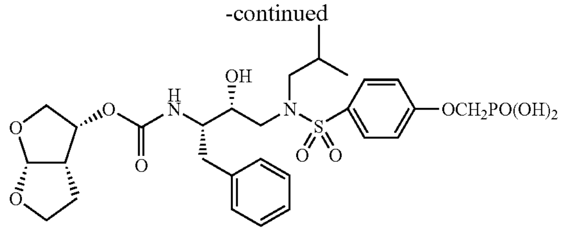

7

Example 1

To a solution of phenol 3 (336 mg, 0.68 mmol) in THF (10 mL) was added $Cs_2CO_3$ (717 mg, 2.2 mmol) and triflate (636 mg, 1.5 mmol) in THF (3 mL). After the reaction mixture was stirred for 30 min at room temperature, the mixture was partitioned between EtOAc and water. The organic phase was dried over $Na_2SO_4$, filtered, and evaporated under reduced pressure. The crude product was chromatographed on silica gel (eluting 40-50% EtOAc/hexane) to give dibenzylphosphonate 4 (420 mg, 80%) as a colorless oil.

Example 2

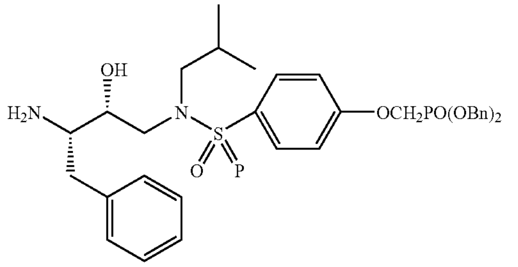

To a solution of dibenzylphosphonate 4 (420 mg, 0.548 mmol) in $CH_2Cl_2$ (10 mL) was added TFA (0.21 mL, 2.74 mmol). After the reaction mixture was stirred for 2 h at room temperature, additional TFA (0.84 mL, 11 mmol) was added and the mixture was stirred for 3 h. The reaction mixture was evaporated under reduced pressure and the residue was partitioned between EtOAc and 1M $NaHCO_3$. The organic phase was dried over $Na_2SO_4$, filtered, and evaporated under reduced pressure to give amine 5 (325 mg, 89%).

Example 3

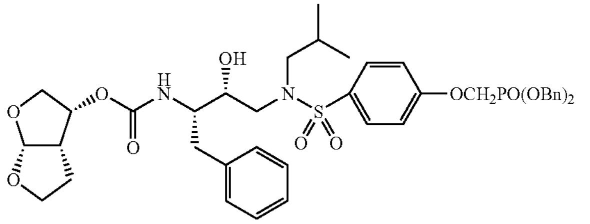

To a solution of carbonate (79 mg, 0.27 mmol), amine 5 (178 mg, 0.27 mmol), and $CH_3CN$ (10 mL) was added DMAP (66 mg, 0.54 mmol) at 0° C. After the reaction mixture was warmed to room temperature and stirred for 16 hours, the mixture was concentrated under reduced pressure. The residue was chromatographed on silica gel (eluting 60-90% EtOAc/hexane) to give a mixture of carbamate 6 and starting carbonate. The mixture was further purified by HPLC on C18 reverse phase chromatography (eluting 60% $CH_3CN$/water) to give carbamate 6 (49 mg, 22%) as a colorless oil. $^1H$ NMR (300 MHz, $CDCl_3$) δ 7.68 (d, 2H), 7.22 (m, 15H), 6.95 (d, 2H), 5.62 (d, 1H), 5.15 (dt, 4H), 5.00 (m, 2H), 4.21 (d, 2H), 3.88 (m, 4H), 3.67 (m, 3H), 3.15 (m, 2H), 2.98 (m, 3H), 2.80 (m, 2H), 1.82 (m, 1H), 1.61 (m, 1H), 0.93 (d, 3H), 0.88 (d, 3H).

Example 4

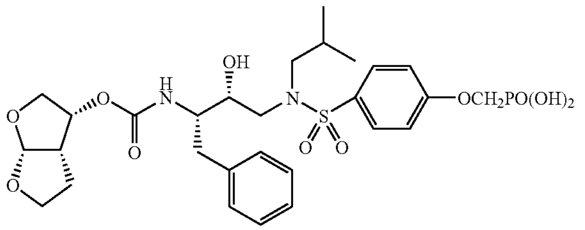

To a solution of carbamate 6 (21 mg, 0.026 mmol) in EtOH/EtOAc (2 mL/1 mL) was added 10% Pd/C (11 mg). After the reaction mixture was stirred under $H_2$ atmosphere (balloon) for 2 hours, the mixture was filtered through Celite. The filtrate was evaporated under reduced pressure to give phosphonic acid 7 (17 mg, 100%) as a colorless solid. $^1H$ NMR (300 MHz, $CD_3OD$) δ 7.73 (d, 2H), 7.19 (m, 5H), 7.13 (d, 2H), 5.53 (d, 1H), 4.26 (d, 2H), 3.86 (m, 1H), 3.64 (m, 5H), 3.38 (d, 1H), 3.13 (d, 1H), 3.03 (dd, 1H), 2.86 (m, 3H), 2.48 (m, 1H), 1.97 (m, 1H), 1.47 (m, 1H), 1.28 (m, 2H), 1.13 (t, 1H), 0.88 (d, 3H), 0.83 (d, 3H).

Scheme 2

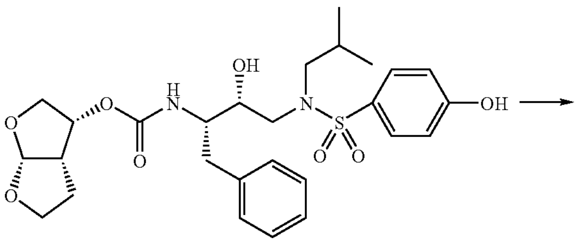

8

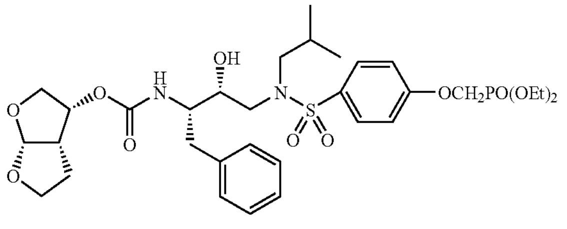

9

-continued

Example 5

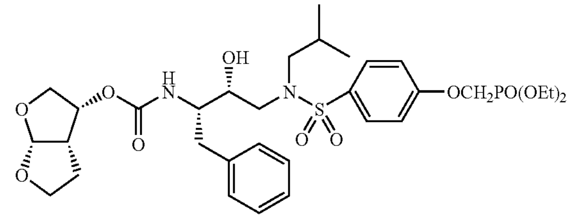

Example 5

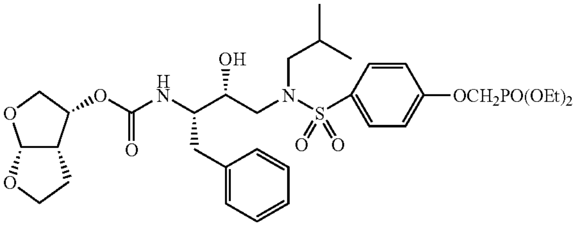

To a solution of phenol 8 (20 mg, 0.036 mmol) and triflate (22 mg, 0.073 mmol) in THF (2 mL) was added $Cs_2CO_3$ (29 mg, 0.090 mmol). After the reaction mixture was stirred for 30 min at room temperature, the mixture was partitioned between EtOAc and water. The organic phase was dried over $Na_2SO_4$, filtered, and evaporated under reduced pressure. The crude product was purified by preparative thin layer chromatography (eluting 80% EtOAc/hexane) to give diethylphosphonate 9 (21 mg, 83%) as a colorless oil. $^1H$ NMR (300 MHz, $CDCl_3$) δ 7.73 (d, 2H), 7.25 (m, 5H), 7.07 (d, 2H), 5.64 (d, 1H), 5.01 (m, 2H), 4.25 (m, 6H), 3.88 (m, 4H), 3.70 (m, 3H), 2.97 (m, 6H), 1.70 (m, 4H), 1.38 (t, 6H), 0.92 (d, 3H), 0.88 (d, 3H). $^{31}P$ NMR (300 MHz, $CDCl_3$) δ 18.1.

Scheme 3

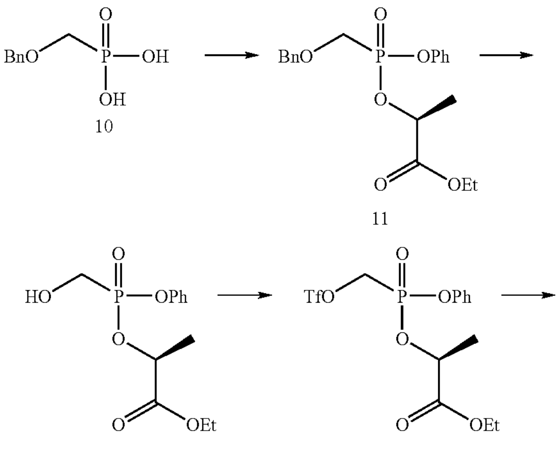

10 11 12 13

-continued

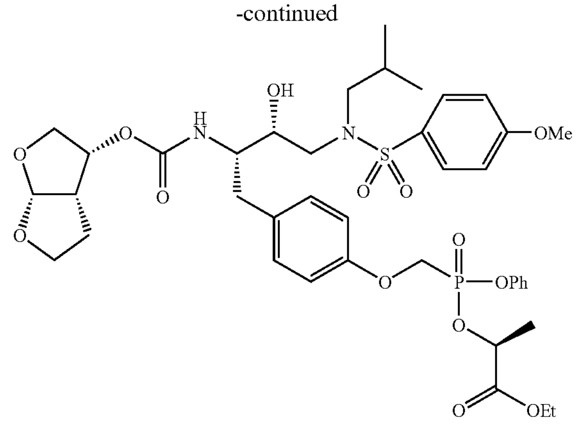

14

Example 6

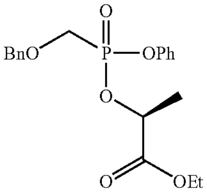

Example 6

To a solution of phosphonic acid 10 (520 mg, 2.57 mmol) in $CH_3CN$ (5 mL) was added thionyl chloride (0.75 mL, 10.3 mmol) and heated to 70° C. in an oil bath. After the reaction mixture was stirred for 2 h at 70° C., the mixture was concentrated and azeotroped with toluene. To a solution of the crude chloridate in toluene (5 mL) was added tetrazole (18 mg, 0.26 mmol) at 0° C. To this mixture was added phenol (121 mg, 1.28 mmol) and triethylamine (0.18 mL, 1.28 mmol) in toluene (3 mL) at 0° C. After the reaction mixture was warmed to room temperature and stirred for 2 h, ethyl lactate (0.29 mL, 2.57 mmol) and triethylamine (0.36 mL, 2.57 mmol) in toluene (2.5 mL) were added. The reaction mixture was stirred for 16 hours at room temperature, at which time the mixture was partitioned between EtOAc and sat. $NH_4Cl$. The organic phase was washed with sat. $NH_4Cl$, 1M $NaHCO_3$, and brine, then dried over $Na_2SO_4$, filtered, and evaporated under reduced pressure. The crude product was chromatographed on silica gel (eluting 20-40% EtOAc/hexane) to give two diastereomers of phosphonate 11 (66 mg, 109 mg, 18% total) as colorless oils.

Example 7A

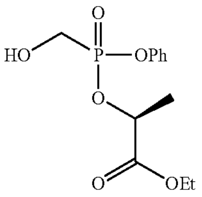

To a solution of phosphonate 11 isomer A (66 mg, 0.174 mmol) in EtOH (2 mL) was added 10% Pd/C (13 mg). After the reaction mixture was stirred under $H_2$ atmosphere (balloon) for 6 h, the mixture was filtered through Celite. The filtrate was evaporated under reduced pressure to give alcohol 12 isomer A (49 mg, 98%) as a colorless oil.

Example 7B

To a solution of phosphonate 11 isomer B (110 mg, 0.291 mmol) in EtOH (3 mL) was added 10% Pd/C (22 mg). After the reaction mixture was stirred under $H_2$ atmosphere (balloon) for 6 h, it was filtered through Celite. The filtrate was evaporated under reduced pressure to give alcohol 12 isomer B (80 mg, 95%) as a colorless oil.

Example 8A

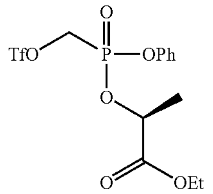

To a solution of alcohol 12 isomer A (48 mg, 0.167 mmol) in $CH_2Cl_2$ (2 mL) was added 2,6-lutidine (0.03 mL, 0.250 mmol) and trifluoromethanesulfonic anhydride (0.04 mL, 0.217 mmol) at −40° C. (dry ice-$CH_3CN$ bath). After the reaction mixture was stirred for 15 min at −40° C., the mixture was warmed to 0° C. and partitioned between $Et_2O$ and 1M $H_3PO_4$. The organic phase was washed with 1M $H_3PO_4$ (3 times), dried over $Na_2SO_4$, filtered, and evaporated under reduced pressure to give triflate 13 isomer A (70 mg, 100%) as a pale yellow oil.

Example 8B

To a solution of alcohol 12 isomer B (80 mg, 0.278 mmol) in $CH_2Cl_2$ (3 mL) was added 2,6-lutidine (0.05 mL, 0.417 mmol) and trifluoromethanesulfonic anhydride (0.06 mL, 0.361 mmol) at −40° C. (dry ice-$CH_3CN$ bath). After the reaction mixture was stirred for 15 min at −40° C., the mixture was warmed to 0° C. and partitioned between $Et_2O$ and 1M $H_3PO_4$. The organic phase was washed with 1M $H_3PO_4$ (3 times), dried over $Na_2SO_4$, filtered, and evaporated under reduced pressure to give triflate 13 isomer B (115 mg, 98%) as a pale yellow oil.

Example 9A

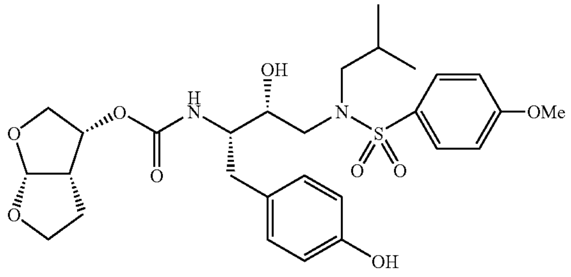

To a solution of phenol (64 mg, 0.111 mmol):

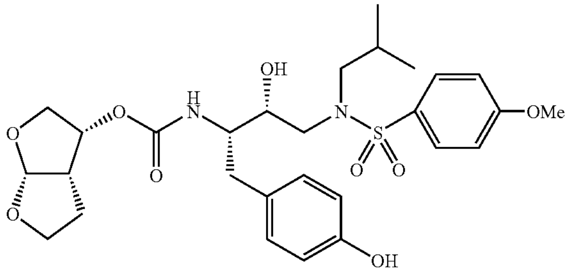

and triflate 13 isomer A (70 mg, 0.167 mmol) in THF (2 mL) was added $Cs_2CO_3$ (72 mg, 0.222 mmol). After the reaction mixture was stirred for 30 min at room temperature, the mixture was partitioned between EtOAc and water. The organic phase was dried over $Na_2SO_4$, filtered, and evaporated under reduced pressure. The crude product was chromatographed on silica gel (eluting 60-80% EtOAc/hexane) to give a mixture. The mixture was further purified by HPLC on C18 reverse phase chromatography (eluting 55% $CH_3CN$/water) to give phosphonate 14 isomer A (30 mg, 32%) as a colorless solid. $^1H$ NMR (300 MHz, $CDCl_3$) δ 7.71 (d, 2H), 7.26 (m, 6H), 7.00 (m, 5H), 5.65 (d, 1H), 5.14 (m, 1H), 5.00 (m, 2H), 4.54 (dd, 1H), 4.44 (dd, 1H), 4.17 (m, 2H), 3.96 (dd, 1H), 3.86 (m, 5H), 3.72 (m, 3H), 3.14 (m, 1H), 2.97 (m, 4H), 2.79 (m, 2H), 1.83 (m, 1H), 1.62 (m, 3H), 1.50 (d, 3H), 1.25 (m, 3H), 0.93 (d, 3H), 0.88 (d, 3H). $^{31}P$ NMR (300 MHz, $CDCl_3$) δ 17.4.

Example 9B

To a solution of phenol (106 mg, 0.183 mmol):

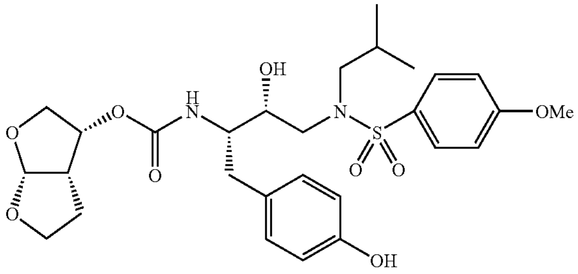

and triflate 13 isomer B (115 mg, 0.274 mmol) in THF (2 mL) was added $Cs_2CO_3$ (119 mg, 0.366 mmol). After the reaction mixture was stirred for 30 min at room temperature, the mixture was partitioned between EtOAc and water. The organic phase was dried over $Na_2SO_4$, filtered, and evaporated under reduced pressure. The crude product was chromatographed on silica gel (eluting 60-80% EtOAc/hexane) to give a mixture. The mixture was further purified by HPLC on C18 reverse phase chromatography (eluting 55% $CH_3CN$/water) to give phosphonate 14 isomer B (28 mg, 18%) as a colorless solid. $^1H$ NMR (300 MHz, $CDCl_3$) δ 7.71 (d, 2H), 7.26 (m, 6H), 6.94 (m, 5H), 5.66 (d, 1H), 5.17 (m, 1H), 4.99 (m, 2H), 4.55 (m, 1H), 4.42 (m, 1H), 4.16 (m, 2H), 3.97 (m, 1H), 3.85 (m, 5H), 3.72 (m, 3H), 3.13 (m, 1H), 2.97 (m, 4H), 2.80 (m, 2H), 1.83 (m, 1H), 1.60 (m, 6H), 1.22 (m, 3H), 0.93 (d, 3H), 0.88 (d, 3H). $^{31}P$ NMR (300 MHz, $CDCl_3$) δ 15.3.

Resolution of Compound 14 Diastereomers

Figure 2:
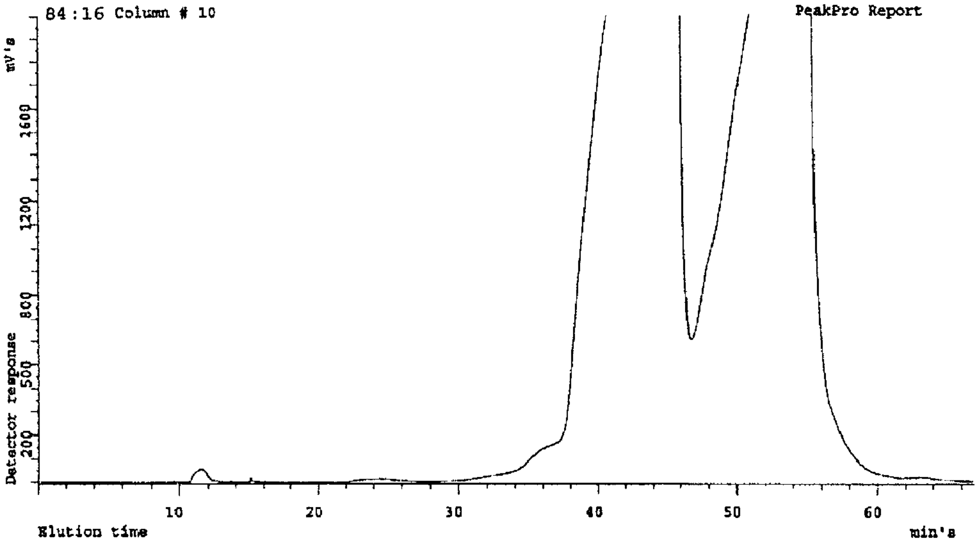
FIG. 2 shows resolution of compound 14 diastereomers by HPLC on an Ailtech Econocil semi-preparative column.

Analysis was performed on an analytical Alltech Econosil column, conditions are described below, with a total of about 0.5 mg 14 injected onto the column. See also FIG. 1 for separation of compound 14 diastereomers. This lot was a mixture of Major and minor diastereomers where the lactate ester carbon is a mix of R and S configurations. Up to 2 mg could be resolved on the analytical column. Larger scale injections (up to 50 mg 14) were performed on an Alltech Econosil semi-preparative column, conditions are described below. See also FIG. 2 for separation of compound 14 diastereomers.

The isolated diastereomer fractions were stripped to dryness on a rotary evaporator under house vacuum, followed by a final high vacuum strip on a vacuum pump. The chromatographic solvents were displaced by two portions of dichloromethane before the final high vacuum strip to aid in removal of trace solvents, and to yield a friable foam.

The bulk of the diastereomer resolution was performed with n-heptane substituted for hexanes for safety considerations.

Sample Dissolution: While a fairly polar solvent mixture is described below, the sample may be dissolved in mobile phase with a minimal quantity of ethyl alcohol added to dissolve the sample.

HPLC CONDITIONS FOR FIG. 1

| | |
|---|---|
| Column | Alltech Econosil, 5 μm, 4.6 × 250 mm |
| Mobile Phase | Hexanes - Isopropyl Alcohol (90:10) |
| Flow Rate | 1.5 mL/min |
| Run Time | 50 min |
| Detection | UV at 242 nm |
| Temperature | Ambient |
| Injection Size | 100 μL |
| Sample Prep. | ~5 mg/mL, dissolved in hexanes - ethyl alcohol (75:25) |
| Retention Times | 14~22 min |
| | 14~29 min |
| | Less Polar Impurity ~19 min |

HPLC CONDITIONS FOR FIG. 2

| | |
|---|---|
| Column | Alltech Econosil, 10 μm, 22 × 250 mm |
| Mobile Phase | n-Heptane - Isopropyl Alcohol (84:16) |
| Flow Rate | 10 mL/min |
| Run Time | 65 min |
| Detection | UV at 257 nm |
| Temperature | Ambient |
| Injection Size | ~50 mg |
| Dissolution | 2 mL mobile phase plus ~0.75 mL ethyl alcohol |
| Retention Times | 14~41 min |
| | 14~54 min |
| | Less Polar Impurity ~Not resolved |

Example Section F

Example 1

Phosphonic acid 2: To a solution of compound 1 (A. Flohr et al, J. Med. Chem., 42, 12, 1999; 2633-2640) (4.45 g, 17 mmol) in $CH_2Cl_2$ (50 mL) at room temperature was added bromotrimethylsilane (1.16 mL, 98.6 mmol). The solution was stirred for 19 h. The volatiles were evaporated under reduced pressure to give the oily phosphonic acid 2 (3.44 g, 100%). $^1H$ NMR ($CDCl_3$) δ 7.30 (m, 5H), 4.61 (s, 2H), 3.69 (d, 2H).

Example 2

Compound 3: To a solution of phosphonic acid 2 (0.67 g, 3.3 mmol) in $CH_3CN$ (5 mL) was added thionyl chloride (1 mL, 13.7 mmol) and the solution was heated at 70° C. for 2.5 h. The volatiles were evaporated under reduced pressure and dried in vacuo to afford an oily phophonyl dichloride. The crude chloride intermediate was dissolved in $CH_2Cl_2$ (20 mL) and cooled in an ice/water bath. Ethyl lactate (1.5 mL, 13.2 mmol) and triethyl amine (1.8 mL, 13.2 mmol) were added dropwise. The mixture was stirred for 4 h at room temperature and dilluted with more $CH_2Cl_2$ (100 mL). The organic solution was washed with 0.1N HCl, saturated aqueous $NaHCO_3$, and brine, dried ($MgSO_4$) filtered and evaporated under reduced pressure. The crude product was chromatographed on silica gel to afford oily compound 3 (0.548 g, 41%). $^1H$ NMR ($CDCl_3$) δ 7.30 (m, 5H), 5.00-5.20 (m, 2H), 4.65 (m, 2H), 4.20 (m, 4H), 3.90 (d, 2H), 1.52 (t, 6H), 1.20 (t, 6H).

Example 3

Alcohol 4: A solution of compound 3 (0.54 g, 1.34 mmol) in EtOH (15 mL) was treated with 10% Pd/C (0.1 g) under $H_2$ (100 psi) for 4 h. The mixture was filtered and the filtrate was treated with fresh 10% PD/C (0.1 g) under $H_2$ (1 atmosphere) for 18 h. The mixture was filtered and the filtrate was evaporated to afford alcohol 4 (0.395 g, 94%) as an oil. $^1H$ NMR ($CDCl_3$) δ 4.90-5.17 (m, 2H), 4.65 (q, 2H), 4.22 (m, 4H), 4.01 (m, 2H), 1.55 (t, 6H), 1.21 (t, 6H); $^{31}P$ NMR ($CDCl_3$) δ 22.8.

Example 4

Triflate 5: To a solution of alcohol 4 (122.8 mg, 0.393 mmol) in $CH_2Cl_2$ (5 mL) at −40° C. were added 2,6-lutidine (0.069 mL, 0.59 mmol) and trifluoromethansulfonic anhydride (0.086 mL, 0.51 mmol). Stirring was continued at 0° C. for 2 h. and the mixture partitioned in $CH_2Cl_2$ and saturated $NaHCO_3$. The organic layer was washed with 0.1N HCl, saturated NaCl, dried ($MgSO_4$), filtered and evaporated under reduced pressure. The crude product 5 (150 mg, 87%) was used for the next step without further purification. $^1H$ NMR ($CDCl_3$) δ 5.0-5.20 (m, 2H), 4.93 (d, 2H), 4.22 (m, 4H), 1.59 (m, 6H), 1.29 (t, 6H).

Example 5

Phosphonate 6: A solution of phenol 8 (see Scheme Section A, Scheme 1 and 2) (32 mg, 0.055 mmol) and triflate 5 (50 mg, 0.11 mmol) in THF (1.5 mL) at room temperature was treated with $Cs_2CO_3$ (45.6 mg, 0.14 mmol). The mixture was stirred for 2.5 h and partitioned in EtOAc and saturated $NaHCO_3$. The organic layer was washed with 0.1N HCl, saturated NaCl, dried ($MgSO_4$), filtered and evaporated under reduced pressure. The crude product was purified by chromatography on silica gel (30-70% EtOAc/hexane) affording the phosphonate 6 (41 mg, 84%) as a solid. $^1H$ NMR ($CDCl_3$) δ 7.71 (d, 2H), 7.13 (d, 2H), 7.00 (d, 2H), 6.90 (d, 2H), 5.65 (d, 1H), 4.90-5.22 (m, 3H), 4.40 (m, 2H), 4.20 (m, 4H), 3.90 (s, 3H), 3.65-4.00 (m, 5H), 2.70-3.20 (m, 6H), 1.52-1.87 (m, 12H), 1.25 (m, 6H), 0.85-0.90 (m, 6H); $^{31}P$ NMR ($CDCl_3$) δ 20.0.

Example 6

Compound 7: To a solution of phosphonic acid 2 (0.48 g, 2.37 mmol) in $CH_3CN$ (4 mL) was added thionyl chloride (0.65 mL, 9.48 mmol) and the solution was heated at 70° C. for 2.5 h. The volatiles were evaporated under reduced pressure and dried in vacuo to afford an oily phophonyl dichloride. The crude chloride intermediate was dissolved in $CH_2Cl_2$ (5 mL) and cooled in an ice/water bath. Ethyl glycolate (0.9 mL, 9.5 mmol) and triethyl amine (1.3 mL, 9.5 mmol) were added dropwise. The mixture was stirred for 2 h at room temperature and diluted with more $CH_2Cl_2$ (100 mL). The organic solution was washed with 0.1N HCl, saturated aqueous $NaHCO_3$, and saturated NaCl, dried ($MgSO_4$) filtered and concentrated under reduced pressure. The crude product was chromatographed on silica gel to afford oily compound 7 (0.223 g, 27%). $^1H$ NMR ($CDCl_3$) δ 7.30 (m, 5H), 4.65 (m, 6H), 4.25 (q, 4H), 3.96 (d, 2H), 1.27 (t, 6H); $^{31}P$ NMR ($CDCl_3$) δ 24.0.

Example 7

Alcohol 8: A solution of compound 7 (0.22 g, 0.65 mmol) in EtOH (8 mL) was treated with 10% Pd/C (0.04 g) under $H_2$ (1 atmosphere) for 4 h. The mixture was filtered and the filtrate was evaporated to afford alcohol 8 (0.156 g, 96%) as an oil. $^1H$ NMR ($CDCl_3$) δ 4.66 (m, 4H), 4.23 (q, 4H), 4.06 (d, 2H), 1.55 (t, 6H), 1.26 (t, 6H); $^{31}P$ NMR ($CDCl_3$) δ 26.8.

Example 8

Triflate 9: To a solution of alcohol 8 (156 mg, 0.62 mmol) in $CH_2Cl_2$ (5 mL) at −40° C. were added 2,6-lutidine (0.11 mL, 0.93 mmol) and trifluoromethansulfonic anhydride (0.136 mL, 0.8 mmol). Stirring was continued at 0° C. for 2 h. and the mixture partitioned in $CH_2Cl_2$ and saturated $NaHCO_3$. The organic layer was washed with 0.1N HCl, saturated NaCl, dried ($MgSO_4$), filtered and evaporated under reduced pressure. The crude product 9 (210 mg, 88%) was used for the next step without further purification. $^1H$ NMR ($CDCl_3$) δ 4.90 (d, 2H), 4.76 (d, 4H), 4.27 (q, 4H), 1.30 (t, 6H).

Example 9

Phosphonate 10: A solution of phenol 8 (30 mg, 0.052 mmol) and triflate 9 (30 mg, 0.078 mmol) in THF (1.5 mL) at room temperature was treated with $Cs_2CO_3$ (34 mg, 0.1 mmol). The mixture was stirred for 2.5 h and partitioned in EtOAc and saturated $NaHCO_3$. The organic layer was washed with 0.1N HCl, saturated NaCl, dried ($MgSO_4$), filtered and evaporated under reduced pressure. The crude product was purified by chromatography on silica gel (30-70% EtOAc/hexane) affording the unreacted phenol (xx) (12 mg, 40%) and the phosphonate 10 (16.6 mg, 38%) as a solid. $^1H$ NMR ($CDCl_3$) δ 7.71 (d, 2H), 7.13 (d, 2H), 7.00 (d, 2H), 6.90 (d, 2H), 5.65 (d, 1H), 5.00 (m, 2H), 4.75 (m, 4H), 4.48 (d, 2H), 4.23 (q, 4H), 3.90 (s, 3H), 3.65-4.00 (m, 5H), 2.70-3.20 (m, 6H), 2.23 (b.s., 2H), 1.52-1.87 (m, 4H), 1.25 (t, 6H), 0.85-0.90 (m, 6H); $^{31}P$ NMR ($CDCl_3$) δ 22.0.

Example 10

Compound 11: To a solution of phosphonic acid 2 (0.512 g, 2.533 mmol) in $CH_3CN$ (5 mL) was added thionyl chloride (0.74 mL, 10 mmol) and the solution was heated at 70° C. for 2.5 h. The volatiles were evaporated under reduced pressure and dried in vacuo to afford an oily phophonyl dichloride. The crude chloride intermediate was dissolved in toluene (8 mL) and cooled in an ice/water bath. A catalytic amount of tetrazol (16 mg, 0.21 mmol) was added followed by the addition of a solution of triethylamine (0.35 mL, 2.53 mmol) and phenol (238 mg, 2.53 mmol) in toluene (5 mL). The mixture was stirred at room temperature for 3 h. A solution of ethyl glycolate (0.36 mL, 3.8 mmol) and triethyl amine (0.53 mL, 3.8 mmol) in toluent (3 mL) was added dropwise. The mixture was stirred for 18 h at room temperature and partitioned in EtOAc and 0.1N HCl. The organic solution was washed with saturated aqueous $NaHCO_3$, and saturated NaCl, dried ($MgSO_4$) filtered and concentrated under reduced pressure. The crude product was chromatographed on silica gel to afford diphenyl phophonate as a byproduct (130 mg) and compound 11 (0.16 g, 18%). $^1H$ NMR ($CDCl_3$) δ 7.15-7.40 (m, 10H), 4.58-4.83 (m, 4H), 4.22 (q, 2H), 4.04 (dd, 2H), 1.24 (t, 3H).

Example 11

Alcohol 12: A solution of compound 11 (0.16 g, 0.44 mmol) in EtOH (5 mL) was treated with 10% Pd/C (0.036 g) under $H_2$ (1 atmosphere) for 22 h. The mixture was filtered and the filtrate was evaporated to afford alcohol 12 (0.112 g, 93%) as an oil. $^1H$ NMR ($CDCl_3$) δ 7.15-7.36 (m, 5H), 4.81 (dd, 1H), 4.55 (dd, 1H), 4.22 (q, 2H), 4.12 (m, 2H), 3.78 (b.s., 1H), 1.26 (t, 6H); $^{31}P$ NMR ($CDCl_3$) δ 22.9

Example 12

Triflate 13: To a solution of alcohol 12 (112 mg, 0.41 mmol) in $CH_2Cl_2$ (5 mL) at −40° C. were added 2,6-lutidine (0.072 mL, 0.62 mmol) and trifluoromethansulfonic anhydride (0.09 mL, 0.53 mmol). Stirring was continued at 0° C. for 3 h. and the mixture partitioned in $CH_2Cl_2$ and saturated $NaHCO_3$. The organic layer was washed with 0.1N HCl, saturated NaCl, dried ($MgSO_4$), filtered and evaporated under reduced pressure. The crude product was purified by chromatography on silica gel (30% EtOAc/hexane) affording triflate 13 (106 mg, 64%). $^1H$ NMR ($CDCl_3$) δ 7.36 (m, 2H), 7.25 (m, 3H), 4.80-5.10 (m, 3H), 4.60 (dd, 1H), 4.27 (q, 2H), 1.28 (t, 3H); $^{31}P$ NMR ($CDCl_3$) δ 11.1

Example 13

Phosphonate 14: A solution of phenol 8 (32 mg, 0.052 mmol) and triflate 13 (32 mg, 0.079 mmol) in $CH_3CN$ (1.5 mL) at room temperature was treated with $Cs_2CO_3$ (34 mg, 0.1 mmol). The mixture was stirred for 1 h and partitioned in EtOAc and saturated $NaHCO_3$. The organic layer was washed with saturated NaCl, dried ($MgSO_4$), filtered and evaporated under reduced pressure. The crude product was purified by chromatography on silica gel (70% EtOAc/hexane) affording phosphonate 14 (18 mg, 40%). $^1H$ NMR ($CDCl_3$) δ 7.71 (d, 2H), 6.75-7.35 (m, 1H, 5.65 (d, 1H), 5.00 (m, 2H), 4.50-4.88 (m, 3H), 4.20 (q, 2H), 3.84 (s, 3H), 3.65-4.00 (m, 5H), 2.70-3.20 (m, 6H), 1.52-1.87 (m, 6H), 1.25 (t, 3H), 0.85-0.90 (m, 6H); $^{31}P$ NMR ($CDCl_3$) δ 17.9, 17.7.

Example 14

Piperidine 16: A solution of compound 15 (3.1 g, 3.673 mmol) in MeOH (100 mL) was treated with 10% Pd/C (0.35 g) under $H_2$ (1 atmosphere) for 18 h. The mixture was filtered and the filtrate was evaporated to afford phenol 16 (2 g, 88%). $^{1}H$ NMR ($CD_3OD$) δ 7.76 (d, 2H), 7.08 (d, 2H), 7.04 (d, 2H), 6.65 (d, 2H), 5.59 (d, 1H), 4.95 (m, 1H), 3.98 (s, 3H), 3.65-4.00 (m, 5H), 3.30-3.50 (m, 3H), 2.80-3.26 (m, 5H), 2.40-2.70 (m, 3H), 1.35-2.00 (m, 7H), 1.16 (m, 2H); MS (ESI) 620 (M+H).

Example 15

Formamide 17: Piperidine 16 obtained above (193 mg, 0.3118 mmol) in DMF (4 mL) was treated with formic acid (0.035 mL, 0.936 mmol), triethylamine (0.173 mL, 1.25 mmol) and EDCI (179 mg, 0.936 mmol) at room temperature. The mixture was stirred for 18 h and partitioned in EtOAc and saturated $NaHCO_3$. The organic layer was washed with saturated NaCl, dried ($MgSO_4$), filtered and evaporated under reduced pressure. The crude product was purified by chromatography on silica gel (EtOAC/hexane) affording formamide 17 (162 mg, 80%). $^{1}H$ NMR ($CDCl_3$) δ 7.96 (s, 1H), 7.68 (d, 2H), 7.04 (d, 2H), 6.97 (d, 2H), 6.76 (d, 2H), 5.63 (d, 1H), 5.37 (bs, 1H), 5.04 (m, 1H), 4.36 (m, 1H), 3.93 (s, 3H), 3.52-3.95 (m, 7H), 2.70-3.20 (m, 8H), 1.48-2.00 (m, 7H), 1.02 (m, 2H).

Example 16

Dibenzyl phosphonate 18: A solution of phenol 17 (123 mg, 0.19 mmol) and dibenzyl trifluoromethansulfonyloxymethanphosphonate YY (120 mg, 0.28 mmol) in $CH_3CN$ (1.5 mL) at room temperature was treated $Cs_2CO_3$ (124 mg, 0.38 mmol). The mixture was stirred for 3 h and partitioned in $CH_2Cl_2$ and saturated $NaHCO_3$. The organic layer was washed with 0.1N HCl, saturated NaCl, dried ($MgSO_4$), filtered and evaporated under reduced pressure. The crude product was purified by chromatography on silica gel (10% $MeOH/CH_2Cl_2$) affording phosphonate 18 (154 mg, 88%). $^{1}H$ NMR ($CDCl_3$) δ 7.96 (s, 1H), 7.68 (d, 2H), 7.35 (m, 10H), 7.10 (d, 2H), 6.97 (d, 2H), 6.80 (d, 2H), 5.63 (d, 1H), 4.96-5.24 (m, 6H), 4.37 (m, 1H), 4.20 (d, 2H), 3.84 (s, 3H), 3.52-3.95 (m, 7H), 2.55-3.20 (m, 8H), 1.48-2.00 (m, 7H), 1.02 (m, 2H). $^{31}P$ NMR ($CDCl_3$) δ 20.3.

Example 17

Phosphonic acid 19: A solution of phosphonate 18 (24 mg, 0.026 mmol) in MeOH (3 mL) was treated with 10% Pd/C (5 mg) under $H_2$ (1 atmosphere) for 4 h. The mixture was filtered and the filtrate was evaporated to afford phosphonic acid 19 as a solid (18 mg, 93%). $^{1}H$ NMR ($CD_3OD$) δ 8.00 (s, 1H), 7.67 (d, 2H), 7.18 (d, 2H), 7.09 (d, 2H), 6.90 (d, 2H), 5.60 (d, 1H), 4.30 (m, 1H), 4.16 (d, 2H), 3.88 (s, 3H), 3.60-4.00 (m, 7H), 3.04-3.58 (m 5H), 2.44-2.92 (m, 5H), 1.28-2.15 (m, 5H), 1.08 (m, 2H). $^{31}P$ NMR ($CDCl_3$) δ 16.3.

Example 18

Diethyl phosphonate 20: A solution of phenol 17 (66 mg, 0.1 mmol) and diethyl trifluoromethansulfonyloxymethanphosphonate XY (46 mg, 0.15 mmol) in $CH_3CN$ (1.5 mL) at room temperature was treated $Cs_2CO_3$ (66 mg, 0.2 mmol). The mixture was stirred for 3 h and partitioned in $CH_2Cl_2$ and saturated $NaHCO_3$. The organic layer was washed with 0.1N HCl, saturated NaCl, dried ($MgSO_4$), filtered and evaporated under reduced pressure. The crude product was purified by chromatography on silica gel (10% $MeOH/CH_2Cl_2$) affording the unreacted 17 (17 mg, 26%) and diethyl phosphonate 20 (24.5 mg, 41%). $^{1}H$ NMR ($CDCl_3$) δ 8.00 (s, 1H), 7.70 (d, 2H), 7.16 (d, 2H), 7.00 (d, 2H), 6.88 (d, 2H), 5.66 (d, 1H), 4.98-5.10 (m, 2H), 4.39 (m 1H), 4.24 (m, 5H), 3.89 (s, 3H), 3.602-3.98 (m, 7H), 2.55-3.16 (m, 8H), 1.50-2.00 (m, 7H), 1.36 (t, 6H), 1.08 (m, 2H). $^{31}P$ NMR ($CDCl_3$) δ 19.2

Example 19

N-methyl pepiridine diethyl phosphonate 21: A solution of compound 20 (22.2 mg, 0.0278 mmol) in THF (1.5 mL) at 0° C. was treated with a solution of borane in THF (1M, 0.083 mL). The mixture was stirred for 2 h at room temperature and the starting material was consumed completely as monitored by TLC. The reaction mixture was cooled in an ice/water bath and excess methanol (1 mL) was added to quench the reaction. The solution was concentrated in vacuo and the crude product was chromatographed on silica gel with MeOH/EtOAc to afford compound 21 (7 mg, 32%). $^{1}H$ NMR ($CDCl_3$) δ 7.70 (d, 2H), 7.16 (d, 2H), 7.00 (d, 2H), 6.88 (d, 2H), 5.66 (d, 1H), 4.98-5.10 (m, 2H), 4.24 (m, 4H), 3.89 (s, 3H), 3.602-3.98 (m, 7H), 2.62-3.15 (m, 9H), 2.26 (s, 3H), 1.52-2.15 (m, 10H), 1.36 (t, 6H). $^{31}P$ NMR ($CDCl_3$) δ 19.3

Example Section G

Example 1

Compound 1: To a solution of 4-nitrobenzyl bromide (21.6 g, 100 mmol) in toluene (100 mL) was added triethyl phosphite (17.15 mL, 100 mL). The mixture was heated at 120° C. for 14 hrs. The evaporation under reduced pressure gave a brown oil, which was purified by flash column chromatography (hexane/EtOAc=2/1 to 100% EtOAc) to afford compound 1.

Example 2

Compound 2: To a solution of compound 1 (1.0 g) in ethanol (60 mL) was added 10% Pd—C (300 mg). The mixture was hydrogenated for 14 hrs. Celite was added and the mixture was stirred for 5 mins. The mixture was filtered through a pad of celite, and washed with ethanol. Concentration gave compound 2.

Example 3

Compound 3: To a solution of compound 3 (292 mg, 1.2 mmol) and aldehyde (111 mg, 0.2 mmol) in methanol (3 mL) was added acetic acid (48 μL, 0.8 mmol). The mixture was stirred for 5 mins, and sodium cyanoborohydride (25 mg, 0.4 mmol) was added. The mixture was stirred for 14 hrs, and methanol was removed under reduced pressure. Water was added, and was extracted with EtOAc. The organic phase was washed 0.5 N NaOH solution (1×), water (2×), and brine (1×), and was dried over $MgSO_4$. Purification by flash column chromatography ($CH_2Cl_2$/MeOH=100/3) gave compound 3.

Example 4

Compound 4: To a solution of compound 3 (79 mg, 0.1 mmol) in $CH_2Cl_2$ (5 mL) was added trifluoroacetic acid (1 mL). The mixture was stirred for 2 hrs, and solvents were evaporated under reduced pressure. Coevaporation with EtOAc and $CH_2Cl_2$ gave an oil. The oil was dissolved in THF (1 mL) and tetrabutylamonium fluoride (0.9 mL, 0.9 mmol) was added. The mixture was stirred for 1 hr, and solvent was removed. Purification by flash column chromotogaphy ($CH_2Cl_2$/MeOH=100/7) gave compound 4.

Example 5

Compound 5: To a solution of compound 4 (0.1 mmol) in acetonitrile (1 mL) at 0° C. was added DMAP (22 mg, 0.18 mmol), followed by bisfurancarbonate (27 mg, 0.09 mmol). The mixture was stirred for 3 hrs at 0° C., and diluted with EtOAc. The organic phase was washed with 0.5 N NaOH solution (2×), water (2×), and brine (1×), and dried over $MgSO_4$. Purification by flash column chromotography ($CH_2Cl_2$/MeOH=100/3 to 100/5) afford compound 5 (50 mg): $^1$H NMR ($CDCl_3$) δ 7.70 (2H, d, J=8.9 Hz), 7.11 (2H, d, J=8.5 Hz), 6.98 (2H, d, J=8.9 Hz), 6.61 (2H, d, J=8.5 Hz), 5.71 (1H, d, J=5.2 Hz), 5.45 (1H, m), 5.13 (1H, m), 4.0 (6H, m), 3.98-3.70 (4H, m), 3.86 (3H, s), 3.38 (2H, m), 3.22 (1H, m), 3.02 (5H, m), 2.8 (1H, m), 2.0-1.8 (3H, m), 1.26 (6H, t, J=7.0 Hz), 0.95 (3H, d, J=6.7 Hz), 0.89 (3H, d, J=6.7 Hz).

Example 6

Compound 6: To a solution of compound 5 (30 mg, 0.04 mmol) in MeOH (0.8 mL) was added 37% fomaldehyde (30 μL, 0.4 mmol), followed by acetic acid (23 μL, 0.4 mmol). The mixture was stirred for 5 mins, and sodium cyanoborohydride (25 mg, 0.4 mmol) was added. The reaction mixture was stirred for 14 hrs, and diluted with EtOAc. The organic phase was washed 0.5 N NaOH solution (2×), water (2×), and brine, and dried over $MgSO_4$. Purification by flash column chromatography ($CH_2Cl_2$/MeOH=100/3) gave compound 6 (11 mg): $^1$H NMR ($CDCl_3$) δ 7.60 (2H, d, J=8.9 Hz), 7.17 (2H, m), 6.95 (2H, d, J=8.9 Hz), 6.77 (2H, d, J=8.5 Hz), 5.68 (1H, d, J=5.2 Hz), 5.21 (1H, m), 5.09 (1H, m), 4.01 (6H, m), 3.87 (3H, s), 3.8-3.3 (4H, m), 3.1-2.6 (7H, m), 2.90 (3H, s), 1.8 (3H, m), 1.25 (6H, m), 0.91 (6H, m).

Example 7

Compound 7: To a solution of compound 1 (24.6 g, 89.8 mmol) in acetonitrile (500 mL) was added TMSBr (36 mL, 269 mmol). The reaction mixture was stirred for 14 hrs, and evaporated under reduced pressure. The mixture was coevaporated with MeOH (2×), toluene (2×), EtOAc (2×), and $CH_2Cl_2$ to give a yellow solid (20 g). To the suspension of above yellow solid (15.8 g, 72.5 mmol) in toluene (140 mL) was added DMF (1.9 mL), followed by thionyl chloride (53 mL, 725 mmol). The reaction mixture was heated at 60° C. for 5 hrs, and evaporated under reduced pressure. The mixture was coevaporated with toluene (2×), EtOAc, and $CH_2Cl_2$ (2×) to afford a brown solid. To the solution of the brown solid in $CH_2Cl_2$ at 0° C. was added benzyl alcohol (29 mL, 290 mmol), followed by slow addition of pyridine (35 mL, 435 mmol). The reaction mixture was allowed to warm to 25° C. and stirred for 14 hrs. Solvents were removed under reduced pressure. The mixture was diluted with EtOAc, and washed with water (3×) and brine (1×), and dried over $MgSO_4$. Concentration gave a dark oil, which was purified by flash column chromatography (hexanes/EtOAc=2/1 to 1/1) to afford compound 7.

Example 8

Compound 8: To a solution of compound 7 (15.3 g) in acetic acid (190 mL) was added Zinc dust (20 g). The mixture was stirred for 14 hrs, and celite was added. The suspension was filtered through a pad of celite, and washed with EtOAc. The solution was concentrated under reduced pressure to dryness. The mixture was diluted with EtOAc, and was washed with 2N NaOH (2×), water (2×), and brine (1×), and dried over $MgSO_4$. Concentration under reduced pressure gave compound 8 as an oil (15 g).

Example 9

Compound 9: To a solution of compound 8 (13.5 g, 36.8 mmol) and aldehyde (3.9 g, 7.0 mmol) in methanol (105 mL) was added acetic acid (1.68 mL, 28 mmol). The mixture was stirred for 5 mins, and sodium cyanoborohydride (882 mg, 14 mmol) was added. The mixture was stirred for 14 hrs, and methanol was removed under reduced pressure. Water was added, and was extracted with EtOAc. The organic phase was washed 0.5 N NaOH solution (1×), water (2×), and brine (1×), and was dried over $MgSO_4$. Purification by flash column chromatography ($CH_2Cl_2$/MeOH=100/3) gave compound 9 (6.0 g).

Example 10

Compound 10: To a solution of compound 9 (6.2 g, 6.8 mmol) in $CH_2Cl_2$ (100 mL) was added trifluoroacetic acid (20 mL). The mixture was stirred for 2 hrs, and solvents were evaporated under reduced pressure. Coevaporation with EtOAc and $CH_2Cl_2$ gave an oil. The oil was dissolved in THF (1 mL) and tetrabutylamonium fluoride (0.9 mL, 0.9 mmol) was added. The mixture was stirred for 1 hr, and solvent was removed. Purification by flash column chromotogaphy ($CH_2Cl_2$/MeOH=100/7) gave compound 10.

Example 11

Compound 11: To a solution of compound 10 (5.6 mmol) in acetonitrile (60 mL) at 0° C. was added DMAP (1.36 g, 11.1 mmol), followed by bisfurancarbonate (1.65 g, 5.6 mmol). The mixture was stirred for 3 hrs at 0° C., and diluted with EtOAc. The organic phase was washed with 0.5 N NaOH solution (2×), water (2×), and brine (1×), and dried over $MgSO_4$. Purification by flash column chromotography ($CH_2Cl_2$/MeOH=100/3 to 100/5) afford compound 11 (3.6 g): $^1$H NMR ($CDCl_3$) δ 7.70 (2H, d, J=8.9 Hz), 7.30 (10H, m), 7.07 (2H, m), 6.97 (2H, d, J=8.9 Hz), 6.58 (2H, d, J=8.2 Hz), 5.70 (1H, d, J=5.2 Hz), 5.42 (1H, m), 5.12 (1H, m), 4.91 (4H, m), 4.0-3.7 (6H, m), 3.85 (3H, s), 3.4 (2H, m), 3.25 (1H, m), 3.06 (2H, d, J=21 Hz), 3.0 (3H, m), 2.8 (1H, m), 1.95 (1H, m), 1.82 (2H, m), 0.91 (6H, m).

Example 12

Compound 12: To a solution of compound 11 (3.6 g) in ethanol (175 mL) was added 10% Pd—C (1.5 g). The reaction mixture was hydrogenated for 14 hrs. The mixture was stirred with celite for 5 mins, and filtered through a pad of celite. Concentration under reduced pressure gave compound 12 as a white solid (2.8 g): $^1$H NMR (DMSO-$d_6$) δ 7.68 (2H, m), 7.08 (2H, m), 6.93 (2H, m), 6.48 (2H, m), 5.95 (1H, m), 5.0 (2H, m), 3.9-3.6 (6H, m), 3.82 (3H, s), 3.25 (3H, m), 3.05 (4H, m), 2.72 (2H, d, J=20.1 Hz), 2.0-1.6 (3H, m), 0.81 (6H, m).

Example 13

Compound 13: Compound 12 (2.6 g, 3.9 mmol) and L-alanine ethyl ester hydrochloride (3.575 g, 23 mmol) were coevaporated with pyridine (2×). The mixture was dissolved in pyridine (20 mL) and diisopropylethylamine (4.1 mL, 23 mmol) was added. To above mixture was added a solution of Aldrithiol (3.46 g, 15.6 mmol) and triphenylphosphine (4.08 g, 15.6 g) in pyridine (20 mL). The reaction mixture was stirred for 20 hrs, and solvents were evaporated under reduced pressure. The mixture was diluted with ethyl acetate, and was washed with 0.5 N NaOH solution (2×), water (2×), and brine, and dried over $MgSO_4$. Concentration under reduced pressure gave a yellow oil, which was purified by flash column chromatography ($CH_2Cl_2$/MeOH=100/5 to 100/10) to afford compound 13 (750 mg): $^1$H NMR ($CDCl_3$) δ 7.71 (2H, d, J=8.8 Hz), 7.13 (2H, m), 6.98 (2H, d, J=8.8 Hz), 6.61 (2H, d, J=8.0 Hz), 5.71 (1H, d, J=5.2 Hz), 5.54 (1H, m), 5.16 (1H, m), 4.15 (6H, m), 4.1-3.6 (6H, m), 3.86 (3H, s), 3.4-3.2 (3H, m), 3.1-2.8 (8H, m), 2.0 (1H, m), 1.82 (2H, m), 1.3 (12H, m), 0.92 (6H, m).

Example 14

Compound 14: To a solution of 4-hydroxypiperidine (19.5 g, 193 mmol) in THF at 0° C. was added sodium hydroxide solution (160 mL, 8.10 g, 203 mmol), followed by di-tert-butyl dicarbonate (42.1 g, 193 mmol). The mixture was warmed to 25° C., and stirred for 12 hours. THF was removed under reduced pressure, and the aqueous phase was extracted with EtOAc (2×). The combined organic layer was washed with water (2×) and brine, and dried over MgSO4. Concentration gave a compound 14 as a white solid (35 g).

Example 15

Compound 15: To a solution of alcohol 14 (5.25 g, 25 mmol) in THF (100 mL) was added sodium hydride (1.2 g, 30 mmol, 60%). The suspension was stirred for 30 mins, and chloromethyl methyl sulfide (2.3 mL, 27.5 mmol) was added. Starting material alcohol 14 still existed after 12 hrs. Dimethy sulfoxide (50 mL) and additional chloromethyl methyl sulfide (2.3 mL, 27.5 mmol) were added. The mixture was stirred for additional 3 hrs, and THF was removed under reduced pressure. The reaction was quenched with water, and extracted with ethyl acetate. The organic phase was washed with water and brine, and was dried over $MgSO_4$. Purification by flash column chromatography (hexanes/EtOAc=8/1) gave compound 15 (1.24 g).

Example 16

Compound 16: To a solution of compound 15 (693 mg, 2.7 mmol) in $CH_2Cl_2$ (50 mL) at −78° C. was added a solution of sulfuryl chloride (214 μL, 2.7 mmol) in $CH_2Cl_2$ (5 mL). The reaction mixture was kept at −78° C. for 3 hrs, and solvents were removed to give a white solid. The white solid was dissolved in toluene (7 mL), and triethyl phosphite (4.5 mL, 26.6 mmol) was added. The reaction mixture was heated at 120° C. for 12 hrs. Solvent and excess reagent was removed under reduced pressure to give compound 16.

Example 17

Compound 17: To a solution of compound 17 (600 mg) in $CH_2Cl_2$ (10 mL) was added trifluoroacetic acid (2 mL). The mixture was stirred for 2 hrs, and was concentrated under reduced pressure to give an oil. The oil was diluted with methylene chloride and base resin was added. The suspension was filtered and the organic phase was concentrated to give compound 17.

Example 18

Compound 18: To a solution of compound 17 (350 mg, 1.4 mmol) and aldehyde (100 mg, 0.2 mmol) in methanol (4 mL) was added acetic acid (156 μL, 2.6 mmol). The mixture was stirred for 5 mins, and sodium cyanoborohydride (164 mg, 2.6 mmol) was added. The mixture was stirred for 14 hrs, and methanol was removed under reduced pressure. Water was added, and was extracted with EtOAc. The organic phase was washed 0.5 N NaOH solution (1×), water (2×), and brine (1×), and was dried over $MgSO_4$. Purification by flash column chromatography ($CH_2Cl_2$/MeOH=100/3) gave compound 18 (62 mg).

Example 19

Compound 19: To a solution of compound 18 (62 mg, 0.08 mmol) in THF (3 mL) were added acetic acid (9 μL, 0.15 mmol) and tetrabutylamonium fluoride (0.45 mL, 1.0 N, 0.45 mmol). The mixture was stirred for 3 hr, and solvent was removed. Purification by flash column chromotogaphy ($CH_2Cl_2$/MeOH=100/5) gave an oil. To a solution of above oil in d$CH_2Cl_2$ (2 mL) was added trifluoroacetic acid (2 mL). The mixture was stirred for 1 hrs, and was concentrated under reduced pressure. Coevaporation with EtOAc and $CH_2Cl_2$ gave compound 19.

Example 20

Compound 20: To a solution of compound 19 (55 mg 0.08 mmol) in acetonitrile (1 mL) at 0° C. was added DMAP (20 mg, 0.16 mmol), followed by bisfurancarbonate (24 mg, 0.08 mmol). The mixture was stirred for 3 hrs at 0° C., and diluted with EtOAc. The organic phase was washed with 0.5 N NaOH solution (2×), water (2×), and brine (1×), and dried over $MgSO_4$. Purification by flash column chromotography ($CH_2Cl_2$/MeOH=100/3 to 100/5) afford compound 20 (46 mg): $^1$H NMR ($CDCl_3$) δ 7.70 (2H, d, J=8.9 Hz), 7.01 (2H, d, J=8.9 Hz), 5.73 (1H, d, J=5.1 Hz), 5.51 (1H, m), 5.14 (1H, m), 4.16 (1H, m), 4.06 (1H, m), 3.94 (3H, m), 3.86 (3H, s), 3.80 (1H, m), 3.75 (2H, d, J=9.1 Hz), 3.58 (1H, m), 3.47 (1H, m), 3.30 (1H, m), 3.1-2.6 (8H, m), 2.3 (2H, m), 2.1-1.8 (5H, m), 1.40 (2H, m), 1.36 (6H, t, J=7.0 Hz), 0.93 (3H, d, J=6.7 Hz), 0.86 (3h, d, J=6.7 Hz).

Example 21

Compound 21: Compound 21 was made from Boc-4-Nitro-L-Phenylalanine (Fluka) following the procedure for Compound 2 in Scheme Section A, Scheme 1.

Example 22

Compound 22: To a solution of chloroketone 21 (2.76 g, 8 mmol) in THF (50 mL) and water (6 mL) at 0° C. (internal temperature) was added solid $NaBH_4$ (766 mg, 20 mmol) in several portions over a period of 15 min while maintaining the internal temperature below 5° C. The mixture was stirred for 1.5 hrs at 0° C. and solvent was removed under reduced pressure. The mixture was quenched with saturated $KHSO_3$ and extracted with EtOAc. The organic phase was washed with waster and brine, and dried over $MgSO_4$. Concentration gave a solid, which was recrystalized from EtOAc/hexane (1/1) to afford the chloroalcohol 22 (1.72 g).

Example 23

Compound 23: To a suspension of chloroalcohol 22 (1.8 g, 5.2 mmol) in EtOH (50 mL) was added a solution of KOH in ethanol (8.8 mL, 0.71 N, 6.2 mmol). The mixture was stirred for 2 h at room temperature and ethanol was removed under reduced pressure. The reaction mixture was diluted with EtOAc, and washed with water (2×), saturated $NH_4Cl$ (2×), water, and brine, and dried over $MgSO_4$. Concentration under reduced pressure afforded epoxide 23 (1.57 g) as a white crystalline solid.

Example 24

Compound 24: To a solution of epoxide 23 (20 g, 65 mmol) in 2-propanol (250 mL) was added isobutylamine (65 mL) and the solution was refluxed for 90 min. The reaction mixture was concentrated under reduced pressure and was coevaporated with MeOH, $CH_3CN$, and $CH_2Cl_2$ to give a white solid. To a solution of the white solid in $CH_2Cl_2$ (300 mL) at 0° C. was added triethylamine (19 mL, 136 mmol), followed by the addition of 4-methoxybenzenesulfonyl chloride (14.1 g, 65 mmol) in $CH_2Cl_2$ (50 mL). The reaction mixture was stirred at 0° C. for 30 min, and warmed to room temperature and stirred for additional 2 hrs. The reaction solution was concentrated under reduced pressure and was diluted with EtOAc. The organic phase was washed with saturated $NaHCO_3$, water and brine, and dried over $MgSO_4$. Concentration under reduced pressure gave compound 24 as a white solid (37.5 g).

Example 25

Compound 25: To a solution of compound 24 (37.5 g, 68 mmol) in $CH_2Cl_2$ (100 mL) at 0° C. was added a solution of tribromoborane in $CH_2Cl_2$ (340 mL, 1.0 N, 340 mmol). The reaction mixture was kept at 0° C. for 1 hr, and warmed to room temperature and stirred for additional 3 hrs. The mixture was cooled to 0° C., and methanol (200 mL) was added slowly. The mixture was stirred for 1 hr and solvents were removed under reduced pressure to give a brown oil. The brown oil was coevaporated with EtOAc and toluene to afford compound 25 as a brown solid, which was dried under vacuum for 48 hrs.

Example 26

Compound 26: To a solution of compound 25 in THF (80 mL) was added a saturated sodium bicarbonate solution (25 mL), followed by a solution of Boc2O (982 mg, 4.5 mmol) in THF (20 mL). The reaction mixture was stirred for 5 hrs. THF was removed under reduced pressure, and aqueous phase was extracted with EtOAc. The organic phase was washed with water (2×) and Brine (1×), and dried over $MgSO_4$. Purification by flash column chromatography (hexanes/EtOAc=1/1) gave compound 26 (467 mg).

Example 27

Compound 27: To a solution of compound 26 (300 mg, 0.56 mmol) in THF (6 mL) was added $Cs_2CO_3$ (546 mg, 1.68 mmol), followed by a solution of triflate (420 mg, 1.39 mmol) in THF (2 mL). The reaction mixture was stirred for 1.5 hrs. The mixture was diluted with EtOAc, and washed with water (3×) and brine (1×), and dried over $MgSO_4$. Purification by flash column chromatography (hexanes/EtOAc=1/1 to 1/3) gave compound 27 (300 mg).

Example 28

Compound 28: To a solution of compound 27 (300 mg, 0.38 mmol) in $CH_2Cl_2$ (2 mL) was added trifluoroacetic acid (2 mL). The mixture was stirred for 2.5 hrs, and was concentrated under reduced pressure. The mixture was diluted with EtOAc and was washed with 0.5 N NaOH solution (3×), water (2×), and brine (1×), and dried over $MgSO_4$. Concentration gave a white solid. To the solution of above white solid in acetonitrile (3 mL) at 0° C. was added DMAP (93 mg, 0.76 mmol), followed by bisfurancarbonate (112 mg, 0.38 mmol). The mixture was stirred for 3 hrs at 0° C., and diluted with EtOAc. The organic phase was washed with 0.5 N NaOH solution (2×), water (2×), and brine (1×), and dried over $MgSO_4$. Purification by flash column chromotography ($CH_2Cl_2$/MeOH=100/3 to 100/5) afford compound 28 (230 mg): $^1$H NMR ($CDCl_3$) δ 8.16 (2H, d, J=8.5 Hz), 7.73 (2H, d, J=9.2 Hz), 7.42 (2H, d, J=8.5 Hz), 7.10 (2H, d, J=9.2 Hz), 5.65 (1H, d, J=4.8 Hz), 5.0 (2H, m), 4.34 (2H, d, J=10 Hz), 4.25 (4H, m), 4.0-3.6 (6H, m), 3.2-2.8 (7H, m), 1.82 (1H, m), 1.6 (2H, m), 1.39 (6H, t, J=7.0 Hz), 0.95 (6H, m).

Example 29

Compound 29: To a solution of compound 28 (50 mg) in ethanol (5 mL) was added 10% Pd—C (20 mg). The mixture was hydrogenated for 5 hrs. Celite was added, and the mixture was stirred for 5 mins. The reaction mixture was filtered through a pad of celite. Concentration under reduced pressure gave compound 29 (50 mg): $^1$H NMR ($CDCl_3$) δ 7.72 (2H, d, J=8.8 Hz), 7.07 (2H, 2H, d, J=8.8 Hz), 7.00 (2H, d, J=8.5 Hz), 6.61 (2H, d, J=8.5 Hz), 5.67 (1H, d, J=5.2 Hz), 5.05 (1H, m), 4.90 (1H, m), 4.34 (2H, d, J=10.3 Hz), 4.26 (2H, m), 4.0-3.7 (6H, m), 3.17 (1H, m), 2.95 (4H, m), 2.75 (2H, m), 1.82 (1H, m), 1.65 (2H, m), 1.39 (6H, t, J=7.0 Hz), 0.93 (3h, d, J=6.4 Hz), 0.87 (3h, d, J=6.4 Hz).

Example 30

Compound 30: To a solution of compound 29 (50 mg, 0.07 mmol) and formaldehyde (52 μL, 37%, 0.7 mmol) in methanol (1 mL) was added acetic acid (40 μL, 0.7 mmol). The mixture was stirred for 5 mins, and sodium cyanoborohydride (44 mg, 0.7 mmol) was added. The mixture was stirred for 14 hrs, and methanol was removed under reduced pressure. Water was added, and was extracted with EtOAc. The organic phase was washed 0.5 N NaOH solution (1×), water (2×), and brine (1×), and was dried over $MgSO_4$. Purification by flash column chromatography ($CH_2Cl_2$/MeOH=100/3) gave compound 30 (40 mg): $^1$H NMR ($CDCl_3$) δ 7.73 (2H, d, J=8.9 Hz), 7.10 (4H, m), 6.66 (2H, d, J=8.2 Hz), 5.66 (1H, d, J=5.2 Hz), 5.02 (1H, m), 4.88 (1H, m), 4.32 (2H, d, J=10.1 Hz), 4.26 (4H, m), 3.98 (1H, m), 3.85 (3H, m), 3.75 (2H, m), 3.19 (1H, m), 2.98 (4H, m), 2.93 (6H, s), 2.80 (2H, m), 1.82 (1H, m), 1.62 (2H, m), 1.39 (6H, t, J=7.0 Hz), 0.90 (6H, m).

Example 31

Compound 31: To a suspension of compound 25 (2.55 g, 5 mmol) in $CH_2Cl_2$ (20 mL) at 0° C. was added triehtylamine (2.8 mL, 20 mmol), followed by TMSCl (1.26 mL, 10 mmol). The mixture was stirred at 0° C. for 30 mins, and warmed to 25° C. and stirred for additional 1 hr. Concentration gave a yellow solid. The yellow solid was dissolved in acetonitrile (30 mL) and cooled to 0° C. To this solution was added DMAP (1.22 g, 10 mmol) and Bisfurancarbonate (1.48 g, 5 mmol). The reaction mixture was stirred at 0° C. for 2 hrs and for additional 1 hr at 25° C. Acetonitrile was removed under reduced pressure. The mixture was diluted with EtOAc, and washed with 5% citric acid (2×), water (2×), and brine (1×), and dried over $MgSO_4$. Concentration gave a yellow solid. The yellow solid was dissolved in THF (40 mL), and acetic acid (1.3 mL, 20 mmol) and tetrabutylammonium fluoride (8 mL, 1.0 N, 8 mmol) were added. The mixture was stirred for 20 mins, and THF was removed under reduced pressure. Purification by flash column chromatography (hexenes/EtOAc=1/1) gave compound 31 (1.5 g).

Example 32

Compound 32: To a solution of compound 31 (3.04 g, 5.1 mmol) in THF (75 mL) was added $Cs_2CO_3$ (3.31 g, 10.2 mmol), followed by a solution of triflate (3.24 g, 7.65 mmol) in THF (2 nL). The reaction mixture was stirred for 1.5 hrs, and THF was removed under reduced pressure. The mixture was diluted with EtOAc, and washed with water (3×) and brine (1×), and dried over $MgSO_4$. Purification by flash column chromatography (hexanes/EtOAc=1/1 to 1/3) gave compound 32 (2.4 g): $^1$H NMR ($CDCl_3$) δ 8.17 (2H, d, J=8.5 Hz), 7.70 (2H, J=9.2 Hz), 7.43 (2H, d, J=8.5 Hz), 7.37 (10H, m), 6.99 (2H, d, J=9.2 Hz), 5.66 (1H, d, J=5.2 Hz), 5.15 (4H, m), 5.05 (2H, m), 4.26 (2H, d, J=10.2 Hz), 3.9-3.8 (4H, m), 3.75 (2H, m), 3.2-2.8 (7H, m), 1.82 (1H, m), 1.62 (2H, m), 0.92 (6H, m).

Example 33

Compound 33: To a solution of compound 32 (45 mg) in acetic acid (3 mL) was added zinc (200 mg). The mixture was stirred for 5 hrs. Celite was added, and the mixture was filtered and washed with EtOAc. The solution was concentrated to dryness and diluted with EtOAc. The organic phase was washed with 0.5 N NaOH solution, water, and brine, and dried over $MgSO_4$. Purification by flash column chromatography ($CH_2Cl_2$/isoproanol=100/5) gave compound 33 (25 mg): $^1$H NMR ($CDCl_3$) δ 7.67 (2H, d, J=8.8 Hz), 7.36 (10H, m), 6.98 (4H, m), 6.60 (2H, d, J=8.0 Hz), 5.67 (1H, d, J=4.9 Hz), 5.12 (4H, m), 5.05 (1H, m), 4.90 (1H, m), 4.24 (2H, d, J=10.4 Hz), 4.0-3.6 (6H, m), 3.12 (1H, m), 3.95 (4H, m), 2.75 (2H, m), 1.80 (1H, m), 1.2 (2H, m), 0.9 (6H, m).

Example 34

Compound 34: To a solution of compound 32 (2.4 g) in ethanol (140 mL) was added 10% Pd—C (1.0 g). The mixture was hydrogenated for 14 hrs. Celite was added, and the mixture was stirred for 5 mins. The slurry was filtered through a pad of celite, and washed with pyridine. Concentration under reduced pressure gave compound 34: $^1$H NMR (DMSO-$d_6$) δ 7.67 (2H, d, J=8.9 Hz), 7.14 (2H, d, J=8.9 Hz), 6.83 (2H, d, J=8.0 Hz), 6.41 (2H, d, J=8.0 Hz), 5.51 (H, d, J=5.2 Hz), 5.0-4.8 (2H, m), 4.15 (2H, d, =10.0 Hz), 3.9-3.2 (8H, m), 3.0 (2H, m), 2.8 (4H, m), 2.25 (1H, m), 1.4 (2H, m), 0.8 (6H, m).

Example 35

Compound 35: Compound 34 (1.62 g, 2.47 mmol) and L-alanine butyl ester hydrochloride (2.69 g, 14.8 mmol) were coevaporated with pyridine (2×). The mixture was dissolved in pyridine (12 mL) and diisopropylethylamine (2.6 mL, 14.8 mmol) was added. To above mixture was added a solution of Aldrithiol (3.29 g, 14.8 mmol) and triphenylphosphine (3.88 g, 14.8 g) in pyridine (12 mL). The reaction mixture was stirred for 20 hrs, and solvents were evaporated under reduced pressure. The mixture was diluted with ethyl acetate, and was washed with 0.5 N NaOH solution (2×), water (2×), and brine, and dried over $MgSO_4$. Concentration under reduced pressure gave a yellow oil, which was purified by flash column chromatography ($CH_2Cl_2$/MeOH=100/5 to 100/15) to afford compound 35 (1.17 g): $^1$H NMR ($CDCl_3$) δ 7.70 (2H, d, J=8.6 Hz), 7.05 (2H, d, J=8.6 Hz), 6.99 (2H, d, J=8.0 Hz), 6.61 (2H, d, J=8.0 Hz), 5.67 (1H, d, J=5.2 Hz), 5.05 (1H, m), 4.96 (1H, m), 4.28 (2H, m), 4.10 (6H, m), 4.0-3.6 (6H, m), 3.12 (2H, m), 2.92 (3H, m), 2.72 (2H, m), 1.82 (1H, m), 1.75-1.65 (2H, m), 1.60 (4H, m), 1.43 (6H, m), 1.35 (4H, m), 0.91 (12H, m).

Example 36

Compound 37: Compound 36 (100 mg, 0.15 mmol) and L-alanine butyl ester hydrochloride (109 mg, 0.60 mmol) were coevaporated with pyridine (2×). The mixture was dissolved in pyridine (1 mL) and diisopropylethylamine (105 µL, 0.6 mmol) was added. To above mixture was added a solution of Aldrithiol (100 mg, 0.45 mmol) and triphenylphosphine (118 mg, 0.45 mmol) in pyridine (1 mL). The reaction mixture was stirred for 20 hrs, and solvents were evaporated under reduced pressure. The mixture was diluted with ethyl acetate, and was washed with water (2×), and brine, and dried over $MgSO_4$. Concentration under reduced pressure gave an oil, which was purified by flash column chromatography ($CH_2Cl_2$/MeOH=100/5 to 100/15) to afford compound 37 (21 mg): $^1$H NMR ($CDCl_3$) δ 7.71 (2H, d, J=8.8 Hz), 7.15 (2H, d, J=8.2 Hz), 7.01 (2H, d, J=8.8 Hz), 6.87 (2H, d, J=8.2 Hz), 5.66 (1H, d, J=5.2 Hz), 5.03 (1H, m), 4.95 (1H, m), 4.2-4.0 (8H, m), 3.98 (1H, m), 3.89 (3H, s), 3.88-3.65 (5H, m), 3.15 (1H, m), 2.98 (4H, m), 2.82 (2H, m), 1.83 (1H, m), 1.63 (4H, m), 1.42 (6H, m), 1.35 (4H, m), 0.95 (12H, m).

Example 37

Compound 38: Compound 36 (100 mg, 0.15 mmol) and L-leucine ethyl ester hydrochloride (117 mg, 0.60 mmol) were coevaporated with pyridine (2×). The mixture was dissolved in pyridine (1 mL) and diisopropylethylamine (105 µL, 0.6 mmol) was added. To above mixture was added a solution of Aldrithiol (100 mg, 0.45 mmol) and triphenylphosphine (118 mg, 0.45 mmol) in pyridine (1 mL). The reaction mixture was stirred for 20 hrs, and solvents were evaporated under reduced pressure. The mixture was diluted with ethyl acetate, and was washed with water (2×), and brine, and dried over $MgSO_4$. Concentration under reduced pressure gave an oil, which was purified by flash column chromatography ($CH_2Cl_2$/MeOH=100/5 to 100/15) to afford compound 38 (12 mg): $^1$H NMR ($CDCl_3$) δ 7.72 (2H, d, J=8.5 Hz), 7.14 (2H, d, J=8.0 Hz), 7.00 (2H, d, J=8.5 Hz), 6.86 (2H, d, J=8.0 Hz), 5.66 (1H, d, J=5.2 Hz), 5.05 (1H, m), 4.95 (1H, m), 4.2-4.0 (8H, m), 4.0-3.68 (6H, m), 3.88 (3H, s), 3.2-2.9 (5H, m), 2.80 (2H, m), 1.80 (1H, m), 1.65 (4H, m), 1.65-1.50 (4H, m), 1.24 (6H, m), 0.94 (18H, m).

Example 38

Compound 39: Compound 36 (100 mg, 0.15 mmol) and L-leucine butyl ester hydrochloride (117 mg, 0.60 mmol) were coevaporated with pyridine (2×). The mixture was dissolved in pyridine (1 mL) and diisopropylethylamine (105 µL, 0.6 mmol) was added. To above mixture was added a solution of Aldrithiol (100 mg, 0.45 mmol) and triphenylphosphine (118 mg, 0.45 mmol) in pyridine (1 mL). The reaction mixture was stirred for 20 hrs, and solvents were evaporated under reduced pressure. The mixture was diluted with ethyl acetate, and was washed with water (2×), and brine, and dried over $MgSO_4$. Concentration under reduced pressure gave an oil, which was purified by flash column chromatography ($CH_2Cl_2$/MeOH=100/5 to 100/15) to afford compound 39 (32 mg): $^1$H NMR ($CDCl_3$) δ 7.72 (2H, d, J=8.8 Hz), 7.15 (2H, d, J=8.0 Hz), 7.0 (2H, d, J=8.8 Hz), 6.89 (2H, d, J=8.0 Hz), 5.66 (1H, d, J=4.3 Hz), 5.07 (1H, m), 4.94 (1H, m), 4.2-4.0 (8H, m), 3.89 (3H, s), 4.0-3.6 (6H, m), 3.2-2.9 (5H, m), 2.8 (2H, m), 1.81 (1H, m), 1.78-1.44 (10H, m), 1.35 (4H, m), 0.95 (24H, m).

Example 39

Compound 41: Compound 40 (82 mg, 0.1 mmol) and L-alanine isopropyl ester hydrochloride (92 mg, 0.53 mmol) were coevaporated with pyridine (2×). The mixture was dissolved in pyridine (1 mL) and diisopropylethylamine (136 μL, 0.78 mmol) was added. To above mixture was added a solution of Aldrithiol (72 mg, 0.33 mmol) and triphenylphosphine (87 mg, 0.33 mmol) in pyridine (1 mL). The reaction mixture was stirred at 75° C. for 20 hrs, and solvents were evaporated under reduced pressure. The mixture was diluted with ethyl acetate, and was washed with water (2×), and brine, and dried over $MgSO_4$. Concentration under reduced pressure gave an oil, which was purified by flash column chromatography ($CH_2Cl_2$/MeOH=100/1 to 100/3) to afford compound 41 (19 mg): $^1$H NMR ($CDCl_3$) δ 7.71 (2H, d, J=8.9 Hz), 7.2-7.35 (5H, m), 7.15 (2H, m), 7.01 (2H, d, J=8.9 Hz), 6.87 (2H, m), 5.65 (1H, d, J=5.4 Hz), 5.05-4.93 (2H, m), 4.3 (2H, m), 4.19 (1H, m), 3.98 (1H, m), 3.88 (3H, s), 3.80 (2H, m), 3.70 (3H, m), 3.18 (1H, m), 2.95 (4H, m), 2.78 (2H, m), 1.82 (1H, m), 1.62 (2H, m), 1.35 (3H, m), 1.25-1.17 (6H, m), 0.93 (3H, d, J=6.4 Hz), 0.88 (3H, d, J=6.4 Hz).

Example 40

Compound 42: Compound 40 (100 mg, 0.13 mmol) and L-glycine butyl ester hydrochloride (88 mg, 0.53 mmol) were coevaporated with pyridine (2×). The mixture was dissolved in pyridine (1 mL) and diisopropylethylamine (136 μL, 0.78 mmol) was added. To above mixture was added a solution of Aldrithiol (72 mg, 0.33 mmol) and triphenylphosphine (87 mg, 0.33 mmol) in pyridine (1 mL). The reaction mixture was stirred at 75° C. for 20 hrs, and solvents were evaporated under reduced pressure. The mixture was diluted with ethyl acetate, and was washed with water (2×), and brine, and dried over $MgSO_4$. Concentration under reduced pressure gave an oil, which was purified by flash column chromatography ($CH_2Cl_2$/MeOH=100/1 to 100/3) to afford compound 42 (18 mg): $^1$H NMR ($CDCl_3$) δ 7.71 (2H, d, J=9.2 Hz), 7.35-7.24 (5H, m), 7.14 (2H, m), 7.00 (2H, d, J=8.8 Hz), 6.87 (2H, m), 5.65 (1H, d, J=5.2 Hz), 5.04 (1H, m), 4.92 (1H, m), 4.36 (2H, m), 4.08 (2H, m), 3.95 (3H, m), 3.88 (3H, s), 3.80 (2H, m), 3.76 (3H, m), 3.54 (1H, m), 3.15 (1H, m), 2.97 (4H, m), 2.80 (2H, m), 1.82 (1H, m), 1.62 (4H, m), 1.35 (2H, m), 0.9 (9H, m).

Example Section H

Example 1

Sulfonamide 1: To a suspension of epoxide (20 g, 54.13 mmol) in 2-propanol (250 mL) was added isobutylamine (54 mL, 541 mmol) and the solution was refluxed for 30 min. The solution was evaporated under reduced pressure and the crude solid was dissolved in $CH_2Cl_2$ (250 mL) and cooled to 0° C. Triethylamine (15.1 mL, 108.26 mmol) was added followed by the addition of 4-nitrobenzenesulfonyl chloride (12 g, 54.13 mmol) and the solution was stirred for 40 min at 0° C., warmed to room temperature for 2 h, and evaporated under reduced pressure. The residue was partitioned between EtOAc and saturated $NaHCO_3$. The organic phase was washed with saturated NaCl, dried with $Na_2SO_4$, filtered, and evaporated under reduced pressure. The crude product was recrystallized from EtOAc/hexane to give the sulfonamide (30.59 g, 90%) as an off-white solid.

Example 2

Phenol 2: A solution of sulfonamide 1 (15.58 g, 24.82 mmol) in EtOH (450 mL) and $CH_2Cl_2$ (60 mL) was treated with 10% Pd/C (6 g). The suspension was stirred under $H_2$ atmosphere (balloon) at room temperature for 24 h. The reaction mixture was filtered through a plug of celite and concentrated under reduced pressure. The crude product was purified by column chromatography on silica gel (6% MeOH/$CH_2Cl_2$) to give the phenol (11.34 g, 90%) as a white solid.

Example 3

Dibenzylphosphonate 3: To a solution of phenol 2 (18.25 g, 35.95 mmol) in $CH_3CN$ (200 mL) was added $Cs_2CO_3$ (23.43 g, 71.90 mmol) and triflate (19.83 g, 46.74 mmol). The reaction mixture was stirred at room temperature for 1 h and the solvent was evaporated under reduced pressure. The residue was partitioned between EtOAc and saturated NaCl. The organic phase was dried with $Na_2SO_4$, filtered, and evaporated under reduced pressure. The crude product was purified by column chromatography on silica gel (2/1-EtOAc/hexane) to give the dibenzylphosphonate (16.87 g, 60%) as a white solid.

Example 4

Amine 4: A solution of dibenzylphosphonate (16.87 g, 21.56 mmol) in $CH_2Cl_2$ (60 mL) at 0° C. was treated with trifluoroacetic acid (30 mL). The solution was stirred for 30 min at 0° C. and then warmed to room temperature for an additional 30 min. Volatiles were evaporated under reduced pressure and the residue was partitioned between EtOAc and 0.5 N NaOH. The organic phase was washed with 0.5 N NaOH (2×), water (2×), saturated NaCl, dried with $Na_2SO_4$, filtered, and evaporated under reduced pressure to give the amine (12.94 g, 88%) as a white solid.

Example 5

Carbonate 5: To a solution of (S)-(+)-3-hydroxytetrahydrofuran (5.00 g, 56.75 mmol) in $CH_2Cl_2$ (80 mL) was added triethylamine (11.86 mL, 85.12 mmol) and bis(4-nitrophenyl)carbonate (25.90 g, 85.12 mmol). The reaction mixture was stirred at room temperature for 24 h and partitioned between $CH_2Cl_2$ and saturated $NaHCO_3$. The $CH_2Cl_2$ layer was dried with $Na_2SO_4$, filtered, and concentrated. The crude product was purified by column chromatography on silica gel (2/1-EtOAc/hexane) to give the carbonate (8.62 g, 60%) as a pale yellow oil which solidified upon refrigerating.

Example 6

Carbamate 6: Two methods have been used.

Method 1: To a solution of 4 (6.8 g, 9.97 mmol) and 5 (2.65 g, 10.47 mmol) in $CH_3CN$ (70 mL) at 0° C. was added 4-(dimethylamino)pyridine (2.44 g, 19.95 mmol). The reaction mixture was stirred at 0° C. for 3 h and concentrated. The residue was dissolved in EtOAc and washed with 0.5 N NaOH, saturated $NaHCO_3$, $H_2O$, dried with $Na_2SO_4$, filtered, and concentrated. The crude product was purified by column chromatography on silica gel (3% 2-propanol/$CH_2Cl_2$) to give the carbamate (3.97 g, 50%) as a pale yellow solid.

Method 2: To a solution of 4 (6.0 g, 8.80 mmol) and 5 (2.34 g, 9.24 mmol) in $CH_3CN$ (60 mL) at 0° C. was added 4-(dimethylamino)pyridine (0.22 g, 1.76 mmol) and N, N-diisopropylethylamine (3.07 mL, 17.60 mmol). The reaction mixture was stirred at 0° C. for 1 h and warmed to room temperature overnight. The solvent was evaporated under reduced pressure. The crude product was dissolved in EtOAc and washed with 0.5 N NaOH, saturated $NaHCO_3$, $H_2O$, dried with $Na_2SO_4$, filtered, and concentrated. The crude product was purified by column chromatography on silica gel (3% 2-propanol/$CH_2Cl_2$) to give the carbamate (3.85 g, 55%) as a pale yellow solid.

Example 7

Phosphonic Acid 7: To a solution of 6 (7.52 g, 9.45 mmol) in MeOH (350 mL) was added 10% Pd/C (3 g). The suspension was stirred under $H_2$ atmosphere (balloon) at room temperature for 48 h. The reaction mixture was filtered through a plug of celite. The filtrate was concentrated and dried under vacuum to give the phosphonic acid (5.24 g, 90%) as a white solid.

Example 8

Cbz Amide 8: To a solution of 7 (5.23 g, 8.50 mmol) in $CH_3CN$ (50 mL) was added N, O-bis(trimethylsilyl)acetamide (16.54 mL, 68 mmol) and then heated to 70° C. for 3 h. The reaction mixture was cooled to room temperature and concentrated. The residue was co-evaporated with toluene and dried under vacuum to afford the silylated intermediate which was used directly without any further purification. To a solution of the silylated intermediate in $CH_2Cl_2$ (40 mL) at 0° C. was added pyridine (1.72 mL, 21.25 mmol) and benzyl chloroformate (1.33 mL, 9.35 mmol). The reaction mixture was stirred at 0° C. for 1 h and warmed to room temperature overnight. A solution of MeOH (50 mL) and 1% aqueous HCl (150 mL) was added at 0° C. and stirred for 30 min. $CH_2Cl_2$ was added and two layers were separated. The organic layer was dried with $Na_2SO_4$, filtered, concentrated, co-evaporated with toluene, and dried under vacuum to give the Cbz amide (4.46 g, 70%) as an off-white solid.

Example 9

Diphenylphosphonate 9: A solution of 8 (4.454 g, 5.94 mmol) and phenol (5.591 g, 59.4 mmol) in pyridine (40 mL) was heated to 70° C. and 1,3-dicyclohexylcarbodiimide (4.903 g, 23.76 mmol) was added. The reaction mixture was stirred at 70° C. for 4 h and cooled to room temperature. EtOAc was added and the side product 1,3-dicyclohexyl urea was filtered off. The filtrate was concentrated and dissolved in $CH_3CN$ (20 mL) at 0° C. The mixture was treated with DOWEX 50W×8-400 ion-exchange resin and stirred for 30 min at 0° C. The resin was filtered off and the filtrate was concentrated. The crude product was purified by column chromatography on silica gel (4% 2-propanol/$CH_2Cl_2$) to give the diphenylphosphonate (2.947 g, 55%) as a white solid.

Example 10

Monophosphonic Acid 10: To a solution of 9 (2.945 g, 3.27 mmol) in $CH_3CN$ (25 mL) at 0° C. was added 1N NaOH (8.2 mL, 8.2 mmol). The reaction mixture was stirred at 0° C. for 1 h. DOWEX 50W×8-400 ion-exchange resin was added and the reaction mixture was stirred for 30 min at 0° C. The resin was filtered off and the filtrate was concentrated and co-evaporated with toluene. The crude product was triturated with EtOAc/hexane (1/2) to give the monophosphonic acid (2.427 g, 90%) as a white solid.

Example 11

Cbz Protected Monophosphoamidate 11: A solution of 10 (2.421 g, 2.93 mmol) and L-alanine isopropyl ester hydrochloride (1.969 g, 11.73 mmol) in pyridine (20 mL) was heated to 70° C. and 1,3-dicyclohexylcarbodiimide (3.629 g, 17.58 mmol) was added. The reaction mixture was stirred at 70° C. for 2 h and cooled to room temperature. The solvent was evaporated under reduced pressure and the residue was partitioned between EtOAc and 0.2 N HCl. The EtOAc layer was washed with 0.2 N HCl, $H_2O$, saturated $NaHCO_3$, dried with $Na_2SO_4$, filtered, and concentrated. The crude product was purified by column chromatography on silica gel (4% 2-propanol/$CH_2Cl_2$) to give the monoamidate (1.569 g, 57%) as a white solid.

Example 12

Monophosphoamidate 12: To a solution of 11 (1.569 g, 1.67 mmol) in EtOAc (80 mL) was added 10% Pd/C (0.47 g). The suspension was stirred under $H_2$ atmosphere (balloon) at room temperature overnight. The reaction mixture was filtered through a plug of celite. The filtrate was concentrated and the crude product was purified by column chromatography on silica gel ($CH_2Cl_2$ to 1-8% 2-propanol/$CH_2Cl_2$) to give the monophosphoamidate 12a (1.12 g, 83%, GS 108577, 1:1 diastereomeric mixture A/B) as a white solid: $^1$H NMR ($CDCl_3$) δ 7.45 (dd, 2H), 7.41-7.17 (m, 7H), 6.88 (dd, 2H), 6.67 (d, J=8.4 Hz, 2H), 5.16 (broad s, 1H), 4.95 (m, 1H), 4.37-4.22 (m, 5H), 3.82-3.67 (m, 7H), 2.99-2.70 (m, 6H), 2.11-1.69 (m, 3H), 1.38 (m, 3H), 1.19 (m, 6H), 0.92 (d, J=6.3 Hz, 3H), 0.86 (d, J=6.3 Hz, 3H); $^{31}$P NMR ($CDCl_3$) δ 20.5, 19.6. 12b (29 mg, 2%, GS108578, diastereomer A) as a white solid: $^1$H NMR ($CDCl_3$) δ 7.43 (d, J=7.8 Hz, 2H), 7.35-7.17 (m, 7H), 6.89 (d, J=8.4 Hz, 2H), 6.67 (d, J=8.4 Hz, 2H), 5.16 (broad s, 1H), 4.96 (m, 1H), 4.38-4.32 (m, 4H), 4.20 (m, 1H), 3.82-3.69 (m, 7H), 2.99-2.61 (m, 6H), 2.10 (m, 1H), 1.98 (m, 1H), 1.80 (m, 1H), 1.38 (d, J=7.2 Hz, 3H), 1.20 (d, J=6.3 Hz, 6H), 0.92 (d, J=6.3 Hz, 3H), 0.86 (d, J=6.3 Hz, 3H); $^{31}$P NMR ($CDCl_3$) δ 20.5. 12c (22 mg, 1.6%, GS 108579, diastereomer B) as a white solid: $^1$H NMR ($CDCl_3$) δ 7.45 (d, J=8.1 Hz, 2H), 7.36-7.20 (m, 7H), 6.87 (d, J=8.7 Hz, 2H), 6.67 (d, J=8.4 Hz, 2H), 5.15 (broad s, 1H), 4.95 (m, 1H), 4.34-4.22 (m, 5H), 3.83-3.67 (m, 7H), 2.99-2.64 (m, 6H), 2.11-1.68 (m, 3H), 1.33 (d, J=6.9 Hz, 3H), 1.20 (d, J=6.0 Hz, 6H), 0.92 (d, J=6.3 Hz, 3H), 0.86 (d, J=6.3 Hz, 3H); $^{31}$P NMR ($CDCl_3$) δ 19.6.

Example 13

Sulfonamide 13: To a suspension of epoxide (1.67 g, 4.52 mmol) in 2-propanol (25 mL) was added isobutylamine (4.5 mL, 45.2 mmol) and the solution was refluxed for 30 min. The solution was evaporated under reduced pressure and the crude solid was dissolved in $CH_2Cl_2$ (20 mL) and cooled to 0° C. Triethylamine (1.26 mL, 9.04 mmol) was added followed by the treatment of 3-nitrobenzenesulfonyl chloride (1.00 g, 4.52 mmol). The solution was stirred for 40 min at 0° C., warmed to room temperature for 2 h, and evaporated under reduced pressure. The residue was partitioned between EtOAc and saturated $NaHCO_3$. The organic phase was washed with saturated NaCl, dried with $Na_2SO_4$, filtered, and evaporated under reduced pressure. The crude product was purified by column chromatography on silica gel (1/1-EtOAc/hexane) to give the sulfonamide (1.99 g, 70%) as a white solid.

Example 14

Phenol 14: Sulfonamide 13 (1.50 g, 2.39 mmol) was suspended in HOAc (40 mL) and concentrated HCl (20 mL) and heated to reflux for 3 h. The reaction mixture was cooled to room temperature and concentrated under reduced pressure. The crude product was partitioned between 10% MeOH/$CH_2Cl_2$ and saturated $NaHCO_3$. The organic layers were washed with $NaHCO_3$, $H_2O$, dried with $Na_2SO_4$, filtered, and concentrated to give a yellow solid. The crude product was dissolved in $CHCl_3$ (20 mL) and treated with triethylamine (0.9 mL, 6.45 mmol) followed by the addition of $Boc_2O$ (0.61 g, 2.79 mmol). The reaction mixture was stirred at room temperature for 6 h. The product was partitioned between $CHCl_3$ and $H_2O$. The $CHCl_3$ layer was washed with $NaHCO_3$, $H_2O$, dried with $Na_2SO_4$, filtered, and concentrated. The crude product was purified by column chromatography on silica gel (1-5% MeOH/$CH_2Cl_2$) to give the phenol (0.52 g, 45%) as a pale yellow solid.

Example 15

Dibenzylphosphonate 15: To a solution of phenol 14 (0.51 g, 0.95 mmol) in $CH_3CN$ (8 mL) was added $Cs_2CO_3$ (0.77 g, 2.37 mmol) and triflate (0.8 g, 1.90 mmol). The reaction mixture was stirred at room temperature for 1.5 h and the solvent was evaporated under reduced pressure. The residue was partitioned between EtOAc and saturated NaCl. The organic phase was dried $Na_2SO_4$, filtered, and evaporated under reduced pressure. The crude product was purified by column chromatography on silica gel (3% MeOH/$CH_2Cl_2$) to give the dibenzylphosphonate (0.62 g, 80%) as a white solid.

Example 16

Amine 16: A solution of dibenzylphosphonate 15 (0.61 g, 0.75 mmol) in $CH_2Cl_2$ (8 mL) at 0° C. was treated with trifluoroacetic acid (2 mL). The solution was stirred for 30 min at 0° C. and then warmed to room temperature for an additional 30 min. Volatiles were evaporated under reduced pressure and the residue was partitioned between EtOAc and 0.5 N NaOH. The organic phase was washed with 0.5 N NaOH (2×), water (2×), saturated NaCl, dried ($Na_2SO_4$), filtered, and evaporated under reduced pressure to give the amine (0.48 g, 90%) which was used directly without any further purification.

Example 17

Carbamate 17: To a solution of amine 16 (0.48 g, 0.67 mmol) in $CH_3CN$ (8 mL) at 0° C. was treated with (3R,3aR,6aS)-hexahydrofuro[2,3-b]furan-2-yl 4-nitrophenyl carbonate (0.2 g, 0.67 mmol, prepared according to Ghosh et al. J. Med. Chem. 1996, 39, 3278.) and 4-(dimethylamino)pyridine (0.17 g, 1.34 mmol). After stirring for 2 h at 0° C., the reaction solvent was evaporated under reduced pressure and the residue was partitioned between EtOAc and 0.5 N NaOH. The organic phase was washed with 0.5N NaOH (2×), 5%-citric acid (2×), saturated $NaHCO_3$, dried with $Na_2SO_4$, filtered, and evaporated under reduced pressure. The crude product was purified by column chromatography on silica gel (3% 2-propanol/$CH_2Cl_2$) to give the carbamate (0.234 g, 40%) as a white solid.

Example 18

Analine 18: To a solution of carbamate 17 (78 mg, 0.09 mmol) in 2 mL HOAc was added zinc powder. The reaction mixture was stirred at room temperature for 1.5 h and filtered through a small plug of celite. The filtrate was concentrated and co-evaporated with toluene. The crude product was purified by column chromatography on silica gel (5% 2-propanaol/$CH_2Cl_2$) to give the analine (50 mg, 66%) as a white solid.

Example 19

Phosphonic Acid 19: To a solution of analine (28 mg, 0.033 mmol) in MeOH (1 mL) and HOAc (0.5 mL) was added 10% Pd/C (14 mg). The suspension was stirred under $H_2$ atmosphere (balloon) at room temperature for 6 h. The reaction mixture was filtered through a small plug of celite. The filtrate was concentrated, co-evaporated with toluene, and dried under vacuum to give the phosphonic acid (15 mg, 68%, GS 17424) as a white solid: $^1H$ NMR (DMSO-$d_6$) δ 7.16-6.82 (m, 8H), 5.50 (d, 1H), 4.84 (m, 1H), 3.86-3.37 (m, 9H), 2.95-2.40 (m, 6H), 1.98 (m, 1H), 1.42-1.23 (m, 2H), 0.84 (d, J=6.3 Hz, 3H), 0.79 (d, J=6.3 Hz, 3H). MS (ESI) 657 (M−H).

Example 20

Phenol 21: A suspension of aminohydrobromide salt 20 (22.75 g, 44 mmol) in $CH_2Cl_2$ (200 mL) at 0° C. was treated with triethylamine (24.6 mL, 176 mmol) followed by slow addition of chlorotrimethylsilane (11.1 mL, 88 mmol). The reaction mixture was stirred at 0° C. for 30 min and warmed to room temperature for 1 h. The solvent was removed under reduced pressure to give a yellow solid. The crude product was dissolved in $CH_2Cl_2$ (300 mL) and treated with triethylamine (18.4 mL, 132 mmol) and $Boc_2O$ (12 g, 55 mmol). The reaction mixture was stirred at room temperature overnight. The product was partitioned between $CH_2Cl_2$ and $H_2O$. The $CH_2Cl_2$ layer was washed with $NaHCO_3$, $H_2O$, dried with $Na_2SO_4$, filtered, and concentrated. The crude product was dissolved in THF (200 mL) and treated with 1.0 M TBAF (102 mL, 102 mmol) and HOAc (13 mL). The reaction mixture was stirred at room temperature for 1 h and concentrated under reduced pressure. The residue was partitioned between $CH_2Cl_2$ and $H_2O$, dried with $Na_2SO_4$, filtered, and concentrated. The crude product was purified by column chromatography on silica gel (1-3% 2-propanol/$CH_2Cl_2$) to give the phenol (13.75 g, 58%) as a white solid.

Example 21

Dibenzylphosphonate 22: To a solution of phenol 21 (13.70 g, 25.48 mmol) in THF (200 mL) was added $Cs_2CO_3$ (16.61 g, 56.96 mmol) and triflate (16.22 g, 38.22 mmol). The reaction mixture was stirred at room temperature for 1 h and the solvent was evaporated under reduced pressure. The residue was partitioned between EtOAc and saturated NaCl. The organic phase was dried with $Na_2SO_4$, filtered, and evaporated under reduced pressure. The crude product was purified by column chromatography on silica gel (3% MeOH/$CH_2Cl_2$) to give the dibenzylphosphonate (17.59 g, 85%) as a white solid.

Example 22

Amine 23: A solution of dibenzylphosphonate 22 (17.58 g, 21.65 mmol) in $CH_2Cl_2$ (60 mL) at 0° C. was treated with trifluoroacetic acid (30 mL). The solution was stirred for 30 min at 0° C. and then warmed to room temperature for an additional 1.5 h. Volatiles were evaporated under reduced pressure and the residue was partitioned between EtOAc and 0.5 N NaOH. The organic phase was washed with 0.5 N NaOH (2×), water (2×), saturated NaCl, dried with $Na_2SO_4$, filtered, and evaporated under reduced pressure to give the amine (14.64 g, 95%) which was used directly without any further purification.

Example 23

Carbamate 24: To a solution of amine 23 (14.64 g, 20.57 mmol) in $CH_3CN$ (200 mL) at 0° C. was treated with (3R, 3aR,6aS)-hexahydrofuro[2,3-b]furan-2-yl 4-nitrophenyl carbonate (6.07 g, 20.57 mmol, prepared according to Ghosh et al., J. Med. Chem. 1996, 39, 3278.) and 4-(dimethylamino) pyridine (5.03 g, 41.14 mmol). After stirring for 2 h at 0° C., the reaction solvent was evaporated under reduced pressure and the residue was partitioned between EtOAc and 0.5 N NaOH. The organic phase was washed with 0.5N NaOH (2×), 5% citric acid (2×), saturated $NaHCO_3$, dried with $Na_2SO_4$, filtered, and evaporated under reduced pressure. The crude product was purified by column chromatography on silica gel (3% 2-propanol/$CH_2Cl_2$) to give the carbamate (10 g, 56%) as a white solid.

Example 24

Phosphonic Acid 25: To a solution of carbamate 24 (8 g, 9.22 mmol) in EtOH (500 mL was added 10% Pd/C (4 g). The suspension was stirred under $H_2$ atmosphere (balloon) at room temperature for 30 h. The reaction mixture was filtered through a plug of celite. The celite paste was suspended in pyridine and stirred for 30 min and filtered. This process was repeated twice. The combined solution was concentrated under reduced pressure to give the phosphonic acid (5.46 g, 90%) as an off-white solid.

Example 25

Cbz Amide 26: To a solution of 25 (5.26 g, 7.99 mmol) in $CH_3CN$ (50 mL) was added N, Obis(trimethylsilyl)acetamide (15.6 mL, 63.92 mmol) and then heated to 70° C. for 3 h. The reaction mixture was cooled to room temperature and concentrated. The residue was co-evaporated with toluene and dried under vacuum to afford the silylated intermediate which was used directly without any further purification. To a solution of the silylated intermediate in $CH_2Cl_2$ (40 mL) at 0° C. was added pyridine (1.49 mL, 18.38 mmol) and benzyl chloroformate (1.25 mL, 8.79 mmol). The reaction mixture was stirred at 0° C. for 1 h and warmed to room temperature overnight. A solution of MeOH (50 mL) and 1% aqueous HCl (150 mL) was added at 0° C. and stirred for 30 min. $CH_2Cl_2$ was added and two layers were separated. The organic layer was dried with $Na_2SO_4$, filtered, concentrated, co-evaporated with toluene, and dried under vacuum to give the Cbz amide (4.43 g, 70%) as an off-white solid.

Example 26

Diphenylphosphonate 27: A solution of 26 (4.43 g, 5.59 mmol) and phenol (4.21 g, 44.72 mmol) in pyridine (40 mL) was heated to 70° C. and 1,3-dicyclohexylcarbodiimide (4.62 g, 22.36 mmol) was added. The reaction mixture was stirred at 70° C. for 36 h and cooled to room temperature. EtOAc was added and the side product 1,3-dicyclohexyl urea was filtered off. The filtrate was concentrated and dissolved in $CH_3CN$ (20 mL) at 0° C. The mixture was treated with DOWEX 50W×8-400 ion-exchange resin and stirred for 30 min at 0° C. The resin was filtered off and the filtrate was concentrated. The crude product was purified by column chromatography on silica gel (2/1-EtOAc/hexane to EtOAc) to give the diphenylphosphonate (2.11 g, 40%) as a pale yellow solid.

Example 27

Monophosphonic Acid 28: To a solution of 27 (2.11 g, 2.24 mmol) in $CH_3CN$ (15 mL) at 0° C. was added 1N NaOH (5.59 mL, 5.59 mmol). The reaction mixture was stirred at 0° C. for 1 h. DOWEX 50W×8-400 ion-exchange resin was added and the reaction mixture was stirred for 30 min at 0° C. The resin was filtered off and the filtrate was concentrated and co-evaporated with toluene. The crude product was triturated with EtOAc/hexane (1/2) to give the monophosphonic acid (1.75 g, 90%) as a white solid.

Example 28

Cbz Protected Monophosphoamidate 29: A solution of 28 (1.54 g, 1.77 mmol) and L-alanine isopropyl ester hydrochloride (2.38 g, 14.16 mmol) in pyridine (15 mL) was heated to 70° C. and 1,3-dicyclohexylcarbodiimide (2.20 g, 10.62 mmol) was added. The reaction mixture was stirred at 70° C. overnight and cooled to room temperature. The solvent was removed under reduced pressure and the residue was partitioned between EtOAc and 0.2 N HCl. The EtOAc layer was washed with 0.2 N HCl, $H_2O$, saturated $NaHCO_3$, dried with $Na_2SO_4$, filtered, and concentrated. The crude product was purified by column chromatography on silica gel (3% MeOH/$CH_2Cl_2$) to give the monophosphoamidate (0.70 g, 40%) as an off-white solid.

Example 29

Monophosphoamidate 30a-b: To a solution of 29 (0.70 g, 0.71 mmol) in EtOH (10 mL) was added 10% Pd/C (0.3 g). The suspension was stirred under $H_2$ atmosphere (balloon) at room temperature for 6 h. The reaction mixture was filtered through a small plug of celite. The filtrate was concentrated and the crude products were purified by column chromatography on silica gel (7-10% MeOH/$CH_2Cl_2$) to give the monoamidates 30a (0.106 g, 18%, GS 77369, 1/1 diastereomeric mixture) as a white solid: $^1$H NMR ($CDCl_3$) δ 7.71 (d, J=8.7 Hz, 2H), 7.73-7.16 (m, 5H), 7.10-6.98 9 m, 4H), 6.61 (d, J=8.1 Hz, 2H), 5.67 (d, J=4.8 Hz, 1H), 5.31-4.91 (m, 2H), 4.44 (m, 2H), 4.20 (m, 1H), 4.00-3.61 (m, 6H), 3.18-2.74 (m, 7H), 1.86-1.64 (m, 3H), 1.38 (m, 3H), 1.20 (m, 6H), 0.93 (d, J=6.6 Hz, 3H), 0.87 (d, J=6.6 Hz, 3H); $^{31}$P NMR ($CDCl_3$) □ 19.1, 18; MS (ESI) 869 (M+Na). 30b (0.200 g, 33%, GS 77425, 1/1 diastereomeric mixture) as a white solid: $^1$H NMR ($CDCl_3$) δ 7.73 (dd, J=8.7 Hz, J=1.5 Hz, 2H), 7.36-7.16 (m, 5H), 7.09-7.00 (m, 4H), 6.53 (d, J=8.7 Hz, 2H), 5.66 (d, J=5.4

Hz, 1H), 5.06-4.91 (m, 2H), 4.40 (m, 2H), 4.20 (m, 1H), 4.00-3.60 (m, 6H), 3.14 (m, 3H), 3.002.65 (m, 6H), 1.86-1.60 (m, 3H), 1.35 (m, 3H), 1.20 (m, 9H), 0.92 (d, J=6.6 Hz, 3H), 0.87 (d, J=6.6 Hz, 3H); 3' P NMR ($CDCl_3$) □ 19.0, 17.9. MS (ESI) 897 (M+Na).

Example 30

Synthesis of Bisamidates 32: A solution of phosphonic acid 31 (100 mg, 0.15 mmol) and L-valine ethyl ester hydrochloride (108 mg, 0.60 mmol) was dissolved in pyridine (5 mL) and the solvent was distilled under reduced pressure at 40-60° C. The residue was treated with a solution of $Ph_3P$ (117 mg, 0.45 mmol) and 2,2'-dipyridyl disulfide (98 mg, 0.45 mmol) in pyridine (1 mL) followed by addition of N,N-diisopropylethylamine (0.1 mL, 0.60 mmol). The reaction mixture was stirred at room temperature for two days. The solvent was evaporated under reduced pressure and the residue was purified by column chromatography on silica gel to give the bisamidate (73 mg, 53%, GS 17389) as a white solid: $^1$H NMR ($CDCl_3$) δ 7.72 (d, J=8.7 Hz, 2H), 7.15 (d, J=8.1 Hz, 2H), 7.00 (d, J=8.7 Hz, 2H), 6.86 (d, J=8.1 Hz, 2H), 5.66 (d, J=4.8 Hz, 1H), 5.05 (m, 1H), 4.95 (d, J=8.7 Hz, 1H), 4.23-4.00 (m, 4H,), 3.97-3.68 (m, 11H), 3.39-2.77 (m, 9H), 2.16 (m, 2H), 1.82-1.60 (m, 3H), 1.31-1.18 (m, 6H), 1.01-0.87 (m, 18H); $^{31}$P NMR ($CDCl_3$) δ 21.3; MS (ESI) 950 (M+Na).

Example 31

Triflate 34: To a solution of phenol 33 (2.00 g, 3.46 mmol) in THF (15 mL) and $CH_2Cl_2$ (5 mL) was added N-phenyltrifluoromethanesulfonimide (1.40 g, 3.92 mmol) and cesium carbonate (1.40 g, 3.92 mmol). The reaction mixture was stirred at room temperature overnight and concentrated. The crude product was partitioned between $CH_2Cl_2$ and saturated NaCl, dried with $Na_2SO_4$, filtered, and concentrated. The crude product was purified by column chromatography on silica gel (3% MeOH/$CH_2Cl_2$) to give the triflate (2.09 g, 85%) as a white solid.

Example 32

Aldehyde 35: To a suspension of triflate 34 (1.45 g, 2.05 mmol), palladium (II) acetate (46 mg, 0.20 mmol) and 1,3-bis(diphenylphosphino)propane (84 mg, 0.2 mmol) in DMF (8 mL) under CO atmosphere (balloon) was slowly added triethylamine (1.65 mL, 11.87 mmol) and triethylsilane (1.90 mL, 11.87 mmol). The reaction mixture was heated to 70° C. under CO atmosphere (balloon) and stirred overnight. The solvent was concentrated under reduced pressure and partitioned between $CH_2Cl_2$ and $H_2O$. The organic phase was dried with $Na_2SO_4$, filtered, and concentrated. The crude product was purified by column chromatography on silica gel (4% 2-propanol/$CH_2Cl_2$) to give the aldehyde (0.80 g, 66%) as a white solid.

Example 33

Substituted Benzyl Alcohol 36: To a solution of aldehyde 35 (0.80 g, 1.35 mmol) in THF (9 mL) and $H_2O$ (1 mL) at −10° C. was added $NaBH_4$ (0.13 g, 3.39 mmol). The reaction mixture was stirred for 1 h at −10° C. and the solvent was evaporated under reduced pressure. The residue was dissolved in $CH_2Cl_2$ and washed with $NaHSO_4$, $H_2O$, dried with $Na_2SO_4$, filtered, and concentrated. The crude product was purified by column chromatography on silica gel (6% 2-propanol/$CH_2Cl_2$) to give the alcohol (0.56 g, 70%) as a white solid.

Example 34

Substituted Benzyl Bromide 37: To a solution of alcohol 36 (77 mg, 0.13 mmol) in THF (1 mL) and $CH_2Cl_2$ (1 mL) at 0° C. was added triethylamine (0.027 mL, 0.20 mmol) and methanesulfonyl chloride (0.011 mL, 0.14 mmol). The reaction mixture was stirred at 0° C. for 30 min and warmed to room temperature for 3 h. Lithium bromide (60 mg, 0.69 mmol) was added and stirred for 45 min. The reaction mixture was concentrated and the residue was partitioned between $CH_2Cl_2$ and $H_2O$, dried with $Na_2SO_4$, filtered, and concentrated. The crude product was purified by column chromatography on silica gel (2% MeOH/$CH_2Cl_2$) to give the bromide (60 mg, 70%).

Example 35

Diethylphosphonate 38: A solution of bromide 37 (49 mg, 0.075 mmol) and triethylphosphite (0.13 mL, 0.75 mmol) in toluene (1.5 mL) was heated to 120° C. and stirred overnight. The reaction mixture was cooled to room temperature and concentrated under reduced pressure. The crude product was purified by column chromatography on silica gel (6% MeOH/$CH_2Cl_2$) to give the diethylphosphonate (35 mg, 66%, GS 191338) as a white solid: $^1$H NMR ($CDCl_3$) δ 7.72 (d, J=8.7 Hz, 2H), 7.27-7.16 (m, 4H), 7.00 (d, J=8.7 Hz, 2H), 5.66 (d, J=5.1 Hz, 1H), 5.00 (m, 2H), 4.04-3.73 (m, 13H), 3.13-2.80 (m, 9H), 1.82-1.64 (m, 3H), 1.25 (t, J=6.9 Hz, 611), 0.92 (d, J=6.3 Hz, 3H), 0.88 (d, J=6.3 Hz, 3H); $^{31}$P NMR ($CDCl_3$) □ 26.4; MS (ESI) 735 (M+Na).

Example 36

N-tert-Butoxycarbonyl-O-benzyl-L-serine 39: To a solution of Boc-L-serine (15 g, 73.09 mmol) in DMF (300 mL) at 0° C. was added NaH (6.43 g, 160.80 mmol, 60% in mineral oil) and stirred for 1.5 h at 0° C. After the addition of benzyl bromide (13.75 g, 80.40 mmol), the reaction mixture was warmed to room temperature and stirred overnight. The solvent was evaporated under reduced pressure and the residue was dissolved in $H_2O$. The crude product was partitioned between $H_2O$ and $Et_2O$. The aqueous phase was acidified to pH<4 with 3 N HCl and extracted with EtOAc three times. The combined EtOAc solution was washed with $H_2O$, dried with $Na_2SO_4$, filtered, and concentrated to give the N-tert-butoxycarbonyl-Obenzyl-L-serine (17.27 g, 80%).

Example 37

Diazo Ketone 40: To a solution of N-tert-Butoxycarbonyl-O-benzyl-L-serine 39 (10 g, 33.86 mmol) in dry THF (120 mL) at −15° C. was added 4-methylmorpholine (3.8 mL, 34.54 mmol) followed by the slow addition of isobutylchloroformate (4.40 mL, 33.86 mmol). The reaction mixture was stirred for 30 min and diazomethane (~50 mmol, generated from 15 g Diazald according to Aldrichimica Acta 1983, 16, 3) in ether (~150 mL) was poured into the mixed anhydride solution. The reaction was stirred for 15 min and was then placed in an ice bath at 0° C. and stirred for 1 h. The reaction was allowed to warm to room temperature and stirred overnight. The solvent was evaporated under reduced pressure and the residue was dissolved in EtOAc, washed with water, saturated $NaHCO_3$, saturated NaCl, dried with $Na_2SO_4$, filtered and evaporated. The crude product was purified by column chromatography (EtOAc/hexane) to afford the diazo ketone (7.50 g, 69%) as a yellow oil.

Example 38

Chloroketone 41: To a suspension of diazoketone 40 (7.50 g, 23.48 mmol) in ether (160 mL) at 0° C. was added 4N HCl in dioxane (5.87 mL, 23.48 mmol). The reaction mixture was stirred at 0° C. for 1 h. The reaction solvent was evaporated under reduced pressure to give the chloroketone which was used directly without any further purification.

Example 39

Chloroalcohol 42: To a solution of chloroketone 41 (7.70 g, 23.48 mmol) in THF (90 mL) was added water (10 mL) and the solution was cooled to 0° C. A solution of $NaBH_4$ (2.67 g, 70.45 mmol) in water (4 mL) was added dropwise over a period of 0.10 min. The mixture was stirred for 1 h at 0° C. and saturated $KHSO_4$ was slowly added until the pH<4 followed by saturated NaCl. The organic phase was washed with saturated NaCl, dried with $Na_2SO_4$, filtered, and evaporated under reduced pressure. The crude product was purified by column chromatography on silica gel (1/4 EtOAc/hexane) to give the chloroalcohol (6.20 g, 80%) as a diastereomeric mixture.

Example 40

Epoxide 43: A solution of chloroalcohol 42 (6.20 g, 18.79 mmol) in EtOH (150 mL) was treated with 0.71 M KOH (1.27 g, 22.55 mmol) and the mixture was stirred at room temperature for 1 h. The reaction mixture was evaporated under reduced pressure and the residue was partitioned between EtOAc and water. The organic phase was washed with saturated NaCl, dried with $Na_2SO_4$, filtered, and evaporated under reduced pressure. The crude product was purified by column chromatography on silica gel (1/6 EtOAc/hexane) to afford the desired epoxide 43 (2.79 g, 45%) and a mixture of diastereomers 44 (1.43 g, 23%).

Example 41

Sulfonamide 45: To a suspension of epoxide 43 (2.79 g, 8.46 mmol) in 2-propanol (30 mL) was added isobutylamine (8.40 mL, 84.60 mmol) and the solution was refluxed for 1 h. The solution was evaporated under reduced pressure and the crude solid was dissolved in $CH_2Cl_2$ (40 mL) and cooled to 0° C. Triethylamine (2.36 mL, 16.92 mmol) was added followed by the addition of 4-methoxybenzenesulfonyl chloride (1.75 g, 8.46 mmol). The solution was stirred for 40 min at 0° C., warmed to room temperature, and evaporated under reduced pressure. The residue was partitioned between EtOAc and saturated $NaHCO_3$. The organic phase was washed with saturated NaCl, dried with $Na_2SO_4$, filtered, and evaporated under reduced pressure. The crude product was directly used without any further purification.

Example 42

Silyl Ether 46: A solution of sulfonamide 45 (5.10 g, 8.46 mmol) in $CH_2Cl_2$ (50 mL) was treated with triethylamine (4.7 mL, 33.82 mmol) and TMSOTf (3.88 mL, 16.91 mmol). The reaction mixture was stirred at room temperature for 1 h and partitioned between $CH_2Cl_2$ and saturated $NaHCO_3$. The aqueous phase was extracted twice with $CH_2Cl_2$ and the combined organic extracts were washed with saturated NaCl, dried with $Na_2SO_4$, filtered, and evaporated under reduced pressure. The crude product was purified by column chromatography on silica gel (1/6 EtOAc/hexane) to give the silyl ether (4.50 g, 84%) as a thick oil.

Example 43

Alcohol 47: To a solution of silyl ether 46 (4.5 g, 7.14 mmol) in MeOH (50 mL) was added 10% Pd/C (0.5 g). The suspension was stirred under $H_2$ atmosphere (balloon) at room temperature for 2 h. The reaction mixture was filtered through a plug of celite and concentrated under reduced pressure. The crude product was purified by column chromatography on silica gel (3% $MeOH/CH_2Cl_2$) to give the alcohol (3.40 g, 85%) as a white solid.

Example 44

Aldehyde 48: To a solution of alcohol 47 (0.60 g, 1.07 mmol) in $CH_2Cl_2$ (6 mL) at 0° C. was added Dess Martin reagent (0.77 g, 1.82 mmol). The reaction mixture was stirred at 0° C. for 3 h and partitioned between $CH_2Cl_2$ and $NaHCO_3$. The organic phase was washed with $H_2O$, dried with $Na_2SO_4$, filtered, and concentrated. The crude product was purified by column chromatography on silica gel (1/4 EtOAc/hexane) to give the aldehyde (0.45 g, 75%) as a pale yellow solid.

Example 45

Sulfonamide 50: To a suspension of epoxide (2.00 g, 5.41 mmol) in 2-propanol (20 mL) was added amine 49 (4.03 g, 16.23 mmol) (prepared in 3 steps starting from 4-(aminomethyl)piperidine according to Bioorg. Med. Chem. Lett., 2001, 11, 1261.). The reaction mixture was heated to 80° C. and stirred for 1 h. The solution was evaporated under reduced pressure and the crude solid was dissolved in $CH_2Cl_2$ (20 mL) and cooled to 0° C. Triethylamine (4.53 mL, 32.46 mmol) was added followed by the addition of 4-methoxybenzenesulfonyl chloride (3.36 g, 16.23 mmol). The solution was stirred for 40 min at 0° C., warmed to room temperature for 1.5 h, and evaporated under reduced pressure. The residue was partitioned between EtOAc and saturated $NaHCO_3$. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the sulfonamide (2.50 g, 59%).

Example 46

Amine 51: A solution of sulfonamide 50 (2.50 g, 3.17 mmol) in $CH_2Cl_2$ (6 mL) at 0° C. was treated with trifluoroacetic acid (3 mL). The solution was stirred for 30 min at 0° C. and then warmed to room temperature for an additional 1.5 h. Volatiles were evaporated under reduced pressure and the residue was partitioned between EtOAc and 0.5 N NaOH. The organic phase was washed with 0.5 N NaOH (2×), water (2×) and saturated NaCl, dried with $Na_2SO_4$, filtered, and evaporated under reduced pressure to give the amine (1.96 g, 90%) which was used directly without any further purification.

Example 47

Carbamate 52: To a solution of amine 51 (1.96 g, 2.85 mmol) in $CH_3CN$ (15 mL) at 0° C. was treated with (3R,3aR,6aS)-hexahydrofuro[2,3-b]furan-2-yl 4-nitrophenyl carbonate (0.84 g, 2.85 mmol, prepared according to Ghosh et al., J. Med. Chem. 1996, 39, 3278.) and 4-(dimethylamino)pyridine (0.70 g, 5.70 mmol). After stirring for 2 h at 0° C., the reaction solvent was evaporated under reduced pressure and the residue was partitioned between EtOAc and 0.5 N NaOH. The organic phase was washed with 0.5N NaOH (2×), 5% citric acid (2×), saturated $NaHCO_3$, dried with $Na_2SO_4$, filtered, and evaporated under reduced pressure. The crude product was purified by column chromatography on silica gel (3% 2-propanol/$CH_2Cl_2$) to give the carbamate (1.44 g, 60%) as a white solid.

Example Section I

Example 1

Carbonate 2: To a solution of (R)-(+)-3-hydroxytetrahydrofuran (1.23 g, 14 mmol) in $CH_2Cl_2$ (50 mL) was added triethylamine (2.9 mL, 21 mmol) and bis(4-nitrophenyl)carbonate (4.7 g, 15.4 mmol). The reaction mixture was stirred at room temperature for 24 h and partitioned between $CH_2Cl_2$ and saturated $NaHCO_3$. The $CH_2Cl_2$ layer was dried with $Na_2SO_4$, filtered, and concentrated. The crude product was purified by column chromatography on silica gel (2/1-EtOAc/hexane) to give the carbonate (2.3 g, 65%) as a pale yellow oil which solidified upon standing.

Example 2

Carbamate 3: To a solution of 1 (0.385 g, 0.75 mmol) and 2 (0.210 g, 0.83 mmol) in $CH_3CN$ (7 mL) at room temperature was added N,N-diisopropylethylamine (0.16 mL, 0.90 mmol). The reaction mixture was stirred at room temperature for 44 h. The solvent was evaporated under reduced pressure. The crude product was dissolved in EtOAc and washed with saturated $NaHCO_3$, brine, dried with $Na_2SO_4$, filtered, and concentrated. The crude product was purified by column chromatography on silica gel (1/1-EtOAc/hexane) to give the carbamate (0.322 g, 69%) as a white solid: mp 98-100° C. (uncorrected).

Example 3

Phenol 4: To a solution of 3 (0.31 g, 0.49 mmol) in EtOH (10 mL) and EtOAc (5 mL) was added 10% Pd/C (30 mg). The suspension was stirred under $H_2$ atmosphere (balloon) at room temperature for 15 h. The reaction mixture was filtered through a plug of celite. The filtrate was concentrated and dried under vacuum to give the phenol (0.265 g) in quantitative yield.

Example 4

Diethylphosphonate 5: To a solution of phenol 4 (100 mg, 0.19 mmol) in THF (3 mL) was added $Cs_2CO_3$ (124 mg, 0.38 mmol) and triflate (85 mg, 0.29 mmol). The reaction mixture was stirred at room temperature for 4 h and the solvent was evaporated under reduced pressure. The residue was partitioned between EtOAc and saturated NaCl. The organic phase was dried with $Na_2SO_4$, filtered, and evaporated under reduced pressure. The crude product was purified by column chromatography on silica gel (5% 2-propanol/$CH_2Cl_2$) to give the diethylphosphonate (63 mg, 49%, GS 16573) as a white solid: $^1H$ NMR ($CDCl_3$) δ 7.65 (d, J=8.7 Hz, 2H), 7.21 (d, J=8.7 Hz, 2H), 6.95 (d, J=9 Hz, 2H), 6.84 (d, J=8.4 Hz, 2H), 5.06 (broad, s, 1H), 4.80 (d, J=7.5 Hz, 1H), 4.19 (m, 6H), 3.83 (s, 3H), 3.80-3.70 (m, 6H), 3.09-2.72 (m, 6H), 2.00 (m, 1H), 1.79 (m, 2H), 1.32 (t, J=7.5 Hz, 6H), 0.86 (d, J=6.6 Hz, 3H), 0.83 (d, J=6.6 Hz, 3H); $^{31}P$ NMR δ 17.8.

Example 5

Dibenzylphosphonate 6: To a solution of phenol 4 (100 mg, 0.19 mmol) in THF (3 mL) was added $Cs_2CO_3$ (137 mg, 0.42 mmol) and triflate (165 mg, 0.39 mmol). The reaction mixture was stirred at room temperature for 6 h and the solvent was evaporated under reduced pressure. The residue was partitioned between EtOAc and saturated NaCl. The organic phase was dried with $Na_2SO_4$, filtered, and evaporated under reduced pressure. The crude product was purified by column chromatography on silica gel (5% 2-propanol/$CH_2Cl_2$) to give the dibenzylphosphonate (130 mg, 84%, GS 16574) as a white solid: $^1H$ NMR ($CDCl_3$) δ 7.65 (d, J=9 Hz, 2H), 7.30 (m, 10H), 7.08 (d, J=8.4 Hz, 2H), 6.94 (d, J=9 Hz, 2H), 6.77 (d, J=8.7 Hz, 2H), 5.16-5.04 (m, 5H), 4.80 (d, J=8.1 Hz, 1H), 4.16 (d, J=10.2 Hz, 2H), 3.82 (s, 3H), 3.75-3.71 (m, 6H), 3.10-2.72 (m, 6H), 2.00 (m, 1H), 1.79 (m, 2H), 0.86 (d, J=6.6 Hz, 3H), 0.83 (d, J=6.6 Hz, 3H); $^{31}P$ NMR ($CDCl_3$) δ 18.8.

Example 6

Phosphonic Acid 7: To a solution of 6 (66 mg, 0.08 mmol) in EtOH (3 mL) was added 10% Pd/C (12 mg). The suspension was stirred under $H_2$ atmosphere (balloon) at room temperature for 15 h. The reaction mixture was filtered through a plug of celite. The filtrate was concentrated under reduced pressure and triturated with EtOAc to give the phosphonic acid (40 mg, 78%, GS 16575) as a white solid.

Example 7

Carbonate 8: To a solution of (S)-(+)-3-hydroxytetrahydrofuran (2 g, 22.7 mmol) in $CH_3CN$ (50 mL) was added triethylamine (6.75 mL, 48.4 mmol) and N,N'-disuccinimidyl carbonate (6.4 g, 25 mmol). The reaction mixture was stirred at room temperature for 5 h and concentrated under reduced pressure. The residue was partitioned between EtOAc and $H_2O$. The organic phase was dried with $Na_2SO_4$, filtered, and concentrated under reduced pressure. The crude product was purified by column chromatography on silica gel (EtOAc as eluant) followed by recrystallization (EtOAc/hexane) to give the carbonate (2.3 g, 44%) as a white solid.

Example 8

Carbamate 9: To a solution of 1 (0.218 g, 0.42 mmol) and 8 (0.12 g, 0.53 mmol) in $CH_3CN$ (3 mL) at room temperature was added N,N-diisopropylethylamine (0.11 mL, 0.63 mmol). The reaction mixture was stirred at room temperature for 2 h. The solvent was evaporated and the residue was partitioned between EtOAc and saturated $NaHCO_3$. The organic phase was washed with brine, dried with $Na_2SO_4$, filtered, and concentrated. The crude product was purified by column chromatography on silica gel (1/1-EtOAc/hexane) to give the carbamate (0.176 g, 66%) as a white solid.

Example 9

Phenol 10: To a solution of 9 (0.176 g, 0.28 mmol) in EtOH (10 mL) was added 10% Pd/C (20 mg). The suspension was stirred under $H_2$ atmosphere (balloon) at room temperature for 4 h. The reaction mixture was filtered through a plug of celite. The filtrate was concentrated and dried under vacuum to give the phenol (0.151 g, GS 10) in quantitative yield.

Example 10

Diethylphosphonate 11: To a solution of phenol 10 (60 mg, 0.11 mmol) in THF (3 mL) was added $Cs_2CO_3$ (72 mg, 0.22 mmol) and triflate (66 mg, 0.22 mmol). The reaction mixture was stirred at room temperature for 4 h and the solvent was evaporated under reduced pressure. The residue was partitioned between EtOAc and saturated NaCl. The organic phase was dried with $Na_2SO_4$, filtered, and evaporated under reduced pressure. The crude product was purified by column chromatography on silica gel (5% 2-propanol/$CH_2Cl_2$) to give the diethylphosphonate (38 mg, 49%, GS 11) as a white solid.

Example Section J

Example 1

Triflate 1: To a solution of A (4 g, 6.9 mmol) in THF (30 mL) and $CH_2Cl_2$ (10 mL) was added $Cs_2CO_3$ (2.7 g, 8 mmol) and N-phenyltrifluoromethanesulfonimide (2.8 g, 8.0 mmol) and stirred at room temperature for 16 h. The reaction mixture was concentrated under reduced pressure. The residue wsa partitioned between $CH_2Cl_2$ and saturated brine twice. The organic phase was dried over sodium sulfate and used for next reaction without further purification.

Example 2

Aldehyde 2: A solution of crude above triflate 1 (~6.9 mmol) in DMF (20 mL) was degassed (high vacumn for 5 min, argon purge, repeat 3 times). To this solution were quickly added $Pd(OAc)_2$ (120 mg, 266 μmol) and bis(diphenylphosphino-propane (dppp, 220 mg, 266 μmol), and heated to 70° C. To this reaction mixture was rapidly introduced carbon monoxide, and stirred at room temperature under an atmopheric pressure of carbon monoxide, followed by slow addition of TEA (5.4 mL, 38 mmol) and triethylsilane (3 mL, 18 mmol). The resultant mixture was stirred at 70° C. for 16 h, then cooled to room temperature, concentrated under reduced pressure, partitioned between $CH_2Cl_2$ and saturated brine. The organic phase was concentrated under reduced pressure and purified on silica gel column to afford aldehyde 2 (2.1 g, 51%) as white solid.

Example 3

Compounds 3a-3e: Respresentative Procedure, 3c: A solution of aldehyde 2 (0.35 g, 0.59 mmol), L-alanine isopropyl ester hydrochloride (0.2 g, 1.18 mmol), glacial acetic acid (0.21 g, 3.5 mmol) in 1,2-dichloroethane (10 mL) was stirred at room temperature for 16 h, followed by addition of sodium cyanoborohydride (0.22 g, 3.5 mmol) and methanol (0.5 mL). The resulting solution was stirred at room temperature for one h. The reaction mixture was washed with sodium bicarbonate solution, saturated brine, and chromatographed on silica gel to afford 3c (0.17 g, 40%). $^1H$ NMR ($CDCl_3$): δ 7.72 (d, 2H), 7.26 (d, 2H), 7.20 (d, 2H), 7.0 (d, 2H), 5.65 (d, 1H), 4.90-5.30 (m, 3H), 3.53-4.0 (m overlapping s, 13H), 3.31 (q, 1H), 2.70-3.20 (m, 7H), 1.50-1.85 (m, 3H), 1.25-1.31 (m, 9H), 0.92 (d, 3H), 0.88 (d, 3H). MS: 706 (M+1).

| Compound | $R_1$ | $R_2$ | Amino Acid |
|---|---|---|---|
| 3a | Me | Me | Ala |
| 3b | Me | Et | Ala |
| 3c | Me | iPr | Ala |
| 3d | Me | Bn | Ala |
| 3e | iPr | Et | Val |

Example 4

Sulfonamide 1: To a solution of crude amine A (1 g, 3 mmol) in $CH_2Cl_2$ was added TEA (0.6 g, 5.9 mmol) and 3-methoxybenzenesulfonyl chloride (0.6 g, 3 mmol). The resulting solution was stirred at room temperature for 5 h, and evaporated under reduced pressure. The residue was chromatographed on silica gel to afford sulfonamide 1 (1.0 g, 67%).

Example 5

Amine 2: To a 0° C. cold solution of sulfonamide 1 (0.85 g, 1.6 mmol) in $CH_2Cl_2$ (40 mL) was treated with $BBr_3$ in $CH_2Cl_2$ (10 mL of 1 M solution, 10 mmol). The solution was stirred at 0° C. 10 min and then warmed to room temperature and stirred for 1.5 h. The reaction mixture was quenched with $CH_3OH$, concentrated under reduced pressure, azeotroped with $CH_3CN$ three times. The crude amine 2 was used for next reaction without further purification.

Example 6

Carbamate 3: A solution of crude amine 2 (0.83 mmol) in $CH_3CN$ (20 mL) and was treated with (3R,3aR,6aS)-hexahydrofuro[2,3-b]furan-2-yl 4-nitrophenyl carbonate (245 mg, 0.83 mmol, prepared according to Ghosh et al., J. Med. Chem. 1996, 39, 3278.) and N,N-dimethylaminopyridine (202 mg, 1.7 mmol). After stirring for 16 h at room temperature, the reaction solvent was evaporated under reduced pressure and the residue was partitioned between $CH_2Cl_2$ and saturated $NaHCO_3$ three times. The organic phase was evaporated under reduced pressure. The residue was purified by chromatography on silica gel affording the carbamate 3 (150 mg, 33%) as a solid.

Example 7

Diethylphosphonate 4: To a solution of carbamate 3(30 mg, 54 μmol) in THF (5 mL) was added $Cs_2CO_3$ (54 mg, 164 μmol) and triflate # (33 mg, 109 μmol). After stirring the reaction mixture for 30 min at room temperature, additional $Cs_2CO_3$ (20 mg, 61 μmol) and triflate (15 mg, 50 μmol) were added and the mixture was stirred for 1 more hour. The reaction mixture was evaporated under reduced pressure and the residue was partitioned between $CH_2Cl_2$ and water. The organic phase was dried ($Na_2SO_4$), filtered and evaporated under reduced pressure. The crude product was chromatographed on silica gel and repurified by HPLC (50% $CH_3CN$-50% $H_2O$ on C18 column) to give the diethylphosphonate 4 (15 mg, 39%). $^1H$ NMR ($CDCl_3$): δ 7.45 (m, 3H), 7.17-7.30 (m, 6H), 5.64 (d, 1H), 5.10 (d, 1H), 5.02 (q, 1H), 4.36 (d, 2H), 4.18-4.29 (2 q overlap, 4H), 3.60-3.98 (m, 7H), 2.70-3.10 (m, 7H), 1.80-1.90 (m, 1H), 1.44-1.70 (m, 2H+H2O), 1.38 (t, 6H), 0.94 (d, 3H), 0.90 (d, 3H). $^{31}P$ NMR ($CDCl_3$): 18.7 ppm; MS (ESI) 699 (M+H).

Example 8

Dibenzylphosphonate 5: To a solution of carbamate 3 (100 mg, 182 μmol) in THF (10 mL) was added $Cs_2CO_3$ (180 mg, 550 μmol) and dibenzylhydroxymethyl phosphonate triflate, Section A, Scheme 2, Compound 9, (150 mg, 360 μmol). After stirring the reaction mixture for 1 h at room temperature, the reaction mixture was evaporated under reduced pressure and the residue was partitioned between $CH_2Cl_2$ and water. The organic phase was dried ($Na_2SO_4$), filtered and evaporated under reduced pressure. The residue was purified by HPLC (50% $CH_3CN$-50% $H_2O$ on C18 column) to give the dibenzylphosphonate 5 (110 mg, 72%). $^1H$ NMR ($CDCl_3$): δ 7.41 (d, 2H), 7.35 (s, 10H), 7.17-7.30 (m, 6H), 7.09-7.11 (m, 1H), 5.64 (d, 1H), 4.90-5.15 (m, 6H), 4.26 (d, 2H), 3.81-3.95 (m, 4H), 3.64-3.70 (m, 2H), 2.85-3.25 (m, 7H), 1.80-1.95 (m, 1H), 1.35-1.50 (m, 1H), 0.94 (d, 3H), 0.91 (d, 3H). $^{31}P$ NMR ($CDCl_3$) δ 19.4 ppm; MS (ESI): 845 (M+Na), 1666 (2M+Na).

Example 9

Phosphonic acid 6: A solution of dibenzylphosphonate 5 (85 mg, 0.1 mmol) was dissolved in MeOH (10 mL) treated with 10% Pd/C (40 mg) and stirred under $H_2$ atmosphere (balloon) overnight. The reaction was purged with $N_2$, and the catalyst was removed by filtration through celite. The filtrate was evaporated under reduced pressure to afford phosphonic acid 6 (67 mg, quantitatively). $^1H$ NMR ($CD_3OD$): δ 7.40-7.55 (m, 3H), 7.10-7.35 (m, 6H), 5.57 (d, 1H), 4.32 (d, 2H), 3.90-3.95 (m, 1H), 3.64-3.78 (m, 5H), 3.47 (m, 1H), 2.85-3.31 (m, 5H), 2.50-2.60 (m, 1H), 2.00-2.06 (m, 1H), 1.46-1.60 (m, 1H), 1.30-1.34 (m, 1H), 0.9 (d, 3H), 0.90 (d, 3H). $^{31}P$ NMR ($CD_3OD$): 16.60 ppm; MS (ESI): 641 (M−H).

Example 10

Sulfonamide 1: To a solution of crude amine A (0.67 g, 2 mmol) in $CH_2Cl_2$ (50 mL) was added TEA (0.24 g, 24 mmol) and crude 3-acetoxy-4-methoxybenzenesulfonyl chloride (0.58 g, 2.1 mmol, was prepared according to Kratzl et al., Monatsh. Chem. 1952, 83, 1042-1043), and the solution was stirred at room temperature for 4 h, and evaporated under reduced pressure. The residue was chromatographed on silica gel to afford sulfonamide 1 (0.64 g, 54%). MS: 587 (M+Na), 1150 (2M+Na)

Phenol 2: Sulfonamide 1 (0.64 g, 1.1 mmol) was treated with saturated $NH_3$ in MeOH (15 mL) at room temperature for 15 min., then evaporated under reduced pressure. The residue was purified on silica gel column to afford phenol 2 (0.57 g, 96%).

Example 11

Dibenzylphosphonate 3a: To a solution of phenol 2 (0.3 g, 0.57 mmol) in THF (8 mL) was added $Cs_2CO_3$ (0.55 g, 1.7 mmol)) and dibenzylhydroxymethyl phosphonate triflate (0.5 g, 1.1 mmol). After stirring the reaction mixture for 1 h at room temperature, the reaction mixture was quenched with water and partitioned between $CH_2Cl_2$ and saturated ammonium chloride aqueous solution. The organic phase was dried ($Na_2SO_4$), filtered and evaporated under reduced pressure. The residue was chromatographed on silica gel (40% EtOAc/60% hexane) to give the dibenzylphosphonate 3a (0.36 g, 82%). $^1H$ NMR ($CDCl_3$): δ 7.20-7.40 (m, 17H), 6.91 (d, 1H), 5.10-5.25 (2 q(ab) overlap, 4H), 4.58-4.70 (m, 1H), 4.34 (d, 2H), 3.66-3.87 (m+s, 5H), 2.85-3.25 (m, 6H), 1.80-1.95 (m, 1H), 1.58 (s, 9H), 0.86-0.92 (2d, 6H).

Example 12

Diethylphosphonate 3b: To a solution of phenol 2 (0.15 g, 0.28 mmol) in THF (4 mL) was added $Cs_2CO_3$ (0.3 g, 0.92 mmol)) and diethylhydroxymethyl phosphonate triflate (0.4 g, 1.3 mmol). After stirring the reaction mixture for 1 h at room temperature, the reaction mixture was quenched with water and partitioned between $CH_2Cl_2$ and saturated $NaHCO_3$ aqueous solution. The organic phase was dried ($Na_2SO_4$), filtered and evaporated under reduced pressure. The residue was chromatographed on silica gel (1% $CH_3OH$—$CH_2Cl_2$) to give the diethylphosphonate 3b (0.14 g, 73%).

Example 13

Amine 4a: To a solution of 3a (0.35 g, 0.44 mmol) in $CH_2Cl_2$ (10 mL) was treated with TFA (0.75 g, 6.6 mmol) at room temperature for 2 h. The reaction was evaporated under reduced pressure, azeotroped with $CH_3CN$ twice, dried to afford crude amine 4a. This crude 4a was used for next reaction without further purification.

Example 14

Amine 4b: To a solution of 3b (60 mg, 89 μmol) in $CH_2Cl_2$ (1 mL) was treated with TFA (0.1 mL, 1.2 mmol) at room temperature for 2 h. The reaction was evaporated under reduced pressure, azeotroped with $CH_3CN$ twice, dried to afford crude amine 4b (68 mg). This crude 4b was used for next reaction without further purification.

Example 15

Carbamate 5a: An ice-cold solution of crude amine 4a (0.44 mmol) in $CH_3CN$ (10 mL) and was treated with (3R,3aR,6aS)-hexahydrofuro[2,3-b]furan-2-yl 4-nitrophenyl carbonate (120 mg, 0.4 mmol) and N,N-dimethylaminopyridine (DMAP, 110 mg, 0.88 mmol). After 4 h, more DMAP (0.55 g, 4.4 mmol) was added to the reaction mixture. After stirring for 1.5 h at room temperature, the reaction solvent was evaporated under reduced pressure and the residue was partitioned between $CH_2Cl_2$ and saturated $NaHCO_3$. The organic phase was evaporated under reduced pressure. The residue was purified by chromatography on silica gel affording the crude carbamate 5a (220 mg) containing some p-nitrophenol. The crude 5a was repurified by HPLC (50% $CH_3CN$/50% $H_2O$) to afford pure carbamate 5a (176 mg, 46%, 2 steps). $^1H$ NMR ($CDCl_3$): δ 7.20-7.36 (m, 1H), 6.94 (d, 1H), 5.64 (d, 1H), 5.10-5.25 (2 q(ab) overlap, 4H), 4.90-5.10 (m, 1H), 4.90 (d, 1H), 4.34 (d, 2H), 3.82-3.91 (m+s, 6H), 3.63-3.70 (m, 3H), 2.79-3.30 (m, 7H), 1.80-1.90 (m, 1H), 1.40-1.50 (m, 1H), 0.94 (d, 3H), 0.89 (d, 3H). $^{31}P$ NMR ($CDCl_3$): 17.2 ppm.

Example 16

Carbamate 5b: An ice-cold solution of crude amine 4b (89 μmol)) in $CH_3CN$ (5 mL) and was treated with (3R,3aR,6aS)-hexahydrofuro[2,3-b]furan-2-yl 4-nitrophenyl carbonate (26 mg, 89 μmol) and N,N-dimethylaminopyridine (DMAP, 22 mg, 0.17 mmol). After 1 h at 0° C., more DMAP (10 mg. 82 μmol) was added to the reaction mixture. After stirring for 2 h at room temperature, the reaction solvent was evaporated under reduced pressure and the residue was partitioned between $CH_2Cl_2$ and saturated $NaHCO_3$. The organic phase was evaporated under reduced pressure. The residue was purified by HPLC (C18 column, 45% $CH_3CN$/55% $H_2O$) to afford pure carbamate 5b (18.8 mg, 29%, 3 steps). $^1H$ NMR ($CDCl_3$): δ 7.38 (d, 2H), 7.20-7.36 (m, 6H), 7.0 (d, 1H), 5.64 (d, 1H), 4.96-5.03 (m, 2H), 4.39 (d, 2H), 4.20-4.31 (2q overlap, 4H) 3.80-4.00 ((s overlap with m, 7H), 3.60-3.73 (m, 2H), 3.64-3.70 (m, 2H), 2.85-3.30 (m, 7H), 1.80-1.95 (m, 1H), 1.55-1.75 (m, 1H), 1.35-1.50 (s overlap with m, 7H), 0.94 (d, 3H), 0.88 (d, 3H). $^{31}P$ NMR ($CDCl_3$): 18.1 ppm.

Example 17

Phosphonic acid 6: A solution of dibenzylphosphonate 5a (50 mg, 58 μmol) was dissolved in MeOH (5 mL) and EtOAc (3 mL) and treated with 10% Pd/C (25 mg) and was stirred at room temperature under $H_2$ atmosphere (balloon) for 8 h. The catalyst was filtered off. The filtrate was concentrated and redissolved in MeOH (5 mL), treated with 10% Pd/C (25 mg) and was stirred at room temperature under $H_2$ atmosphere (balloon) overnight. The catalyst was filtered off. The filtrate was evaporated under reduced pressure to afford phosphonic acid 6 (38 mg, quantitatively). $^1$H NMR ($CD_3OD$): δ 7.42 (m, 1H), 7.36 (s, 1H), 7.10-7.25 (m, 6H), 5.58 7 (d, 1H), 4.32 (d, 2H), 3.90 (s, 3H), 3.60-3.80 (m, 6H), 3.38 (d, 1H), 2.85-3.25 (m, 5H), 2.50-2.60 (m, 1H), 1.95-2.06 (m, 1H), 1.46-1.60 (m, 1H), 1.30-1.40 (m, 1H), 0.93 (d, 3H), 0.89 (d, 3H). $^{31}$P NMR ($CD_3OD$): 14.8 ppm; MS (ESI): 671 (M−H).

Example 18

Amine 7: To a 0° C. cold solution of diethylphosphonate 3b (80 mg, 0.118 mmol) in $CH_2Cl_2$ was treated with $BBr_3$ in $CH_2Cl_2$ (0.1 mL of 1 M solution, 1 mmol). The solution was stirred at 0° C. 10 min and then warmed to room temperature and stirred for 3 h. The reaction mixture was concentrated under reduced pressure. The residue was redissolved in $CH_2Cl_2$ (containing some $CH_3OH$, concentrated, azeotroped with $CH_3CN$ three times. The crude amine 7 was used for next reaction without further purification.

Example 19

Carbamate 8: An ice-cold solution of crude amine 7 (0.118 mmol) in $CH_3CN$ (5 mL) and was treated with (3R,3aR,6aS)-hexahydrofuro[2,3-b]furan-2-yl 4-nitrophenyl carbonate (35 mg, 0.118 mmol) and N,N-dimethylaminopyridine (29 mg, 0.24 mmol), warmed to room temperature. After stirring for 1 h at room temperature, more DMAP (20 mg, 0.16 mmol) was added to reaction mixture. After 2 h stirred at room temperature, the reaction solvent was evaporated under reduced pressure and the residue was partitioned between $CH_2Cl_2$ and saturated $NaHCO_3$. The organic phase was evaporated under reduced pressure. The residue was purified by HPLC on C18 ($CH_3CN$-55% $H_2O$) to afford the desired carbamate 8 (11.4 mg, 13.4%) as an off-white solid. $^1$H NMR ($CDCl_3$): δ 7.20-7.40 (m, 7H), 7.00 (d, 1H), 5.64 (d, 1H), 5.00-5.31 (m, 2H), 4.35 (d, 2H), 4.19-4.30 (2q overlap, 4H), 3.80-4.00 (m, 4H), 3.68-3.74 (m, 2H), 3.08-3.20 (m, 3H), 2.75-3.00 (m, 4H), 1.80-1.90 (m, 1H), 1.55-1.75 (m, 1H), 1.38 (t, 6H), 0.91 (2d overlap, 6H). $^{31}$P NMR ($CD_3OD$): 619.5 ppm.

Example Section K

Example 1

Monophenyl-monolactate 3: A mixture of monoacid 1 (0.500 g, 0.7 mmol), alcohol 2 (0.276 g, 2.09 mmol) and dicyclohexylcarbodiimide (0.431 g, 2.09 mmol) in dry pyridine (4 mL) was placed into a 70° C. oil bath and heated for two hours. The reaction was monitored by TLC assay ($SiO_2$, 70% ethyl acetate in hexanes as eluent, product $R_f$=0.68, visualization by UV). The reaction contents were cooled to ambient temperature with the aid of a cool bath and diluted with dichloromethane (25 mL). TLC assay may show presence of starting material. The diluted reaction mixture was filtered to remove solids. The filtrate was then cooled to 0° C. and charged with 0.1 N HCl (10 mL). The pH 4 mixture was stirred for 10 minutes and poured into separatory funnel to allow the layers to separate. The lower organic layer was collected and dried over sodium sulfate. The drying agent was filtered off and the filtrate concentrated to an oil via rotary evaporator (<30° C. warm bath). The crude product oil was purified on pretreated silica gel (deactivated using 10% methanol in dichlorormethane followed by rinse with 60% ethyl acetate in dichloromethane). The product was eluted with 60% ethyl acetate in dichloromethane to afford the product monophenyl-monolactate 3 as a white foam (0.497 g, 86% yield). $^1$H NMR ($CDCl_3$) δ 7.75 (d, 2H), 7.40-7.00 (m, 14H), 5.65 (d, 1H), 5.20-4.90 (m, 4H), 4.70 (d, 1H), 4.55-4.50 (m, 1H), 4.00-3.80 (m, 4H), 3.80-3.60 (m, 3H), 3.25-2.75 (m, 7H), 1.50 (d, 3H), 1.30-1.20 (m, 7H), 0.95 (d, 3H), 0.85 (d, 3H). $^{31}$P NMR ($CDCl_3$) δ 16.2, 13.9.

Example 2

Monophenyl-monoamidate 5: A mixture of monoacid 1 (0.500 g, 0.70 mmol), amine hydrochloride 4 (0.467 g, 2.78 mmol) and dicyclohexylcarbodiimide (0.862 g, 4.18 mmol) in dry pyridine (8 mL) was placed into a 60° C. oil bath, and heated for one hour (at this temperature, product degrades if heating continues beyond this point). The reaction was monitored by TLC assay ($SiO_2$, 70% ethyl acetate in hexanes as eluent, product $R_f$=0.39, visualization by UV). The contents were cooled to ambient temperature and diluted with ethyl acetate (15 mL) to precipitate a white solid. The mixture was filtered to remove solids and the filtrate was concentrated via rotary evaporator to an oil. The oil was diluted with dichloromethane (20 mL) and washed with 0.1 N HCl (2×20 mL), water (1×20 mL) and dilute sodium bicarbonate (1×20 mL). The organic layer was dried over sodium sulfate, filtered, and concentrated to an oil via rotary evaporator. The crude product oil was dissolved in dichloromethane (10 mL). Hexane was slowly charged to the stirring solution until cloudiness persisted. The cloudy mixture was stirred for a few mintues until TLC assay showed that the dichloromethane/hexane layer contained no product. The dichloromethane/hexanes layer was decanted and the solid was further purified on silica gel first pretreated with 10% methanol in ethyl acetate and rinsed with 50% ethyl acetate in hexanes. The product 5 was eluted with 50% ethyl acetate in hexanes to afford a white foam (0.255 g, 44% yield) upon removal of solvents. $^1$H NMR ($CDCl_3$) δ 7.75 (d, 2H), 7.40-7.15 (m, 10H), 7.15-7.00 (t, 2H), 5.65 (d, 1H), 5.10-4.90 (m, 3H), 4.50-4.35 (m, 2H), 4.25-4.10 (m, 1H), 4.00-3.60 (m, 8H), 3.20-2.75 (m, 7H), 1.40-1.20 (m, 11H), 0.95 (d, 3H), 0.85 (d, 3H). $^{31}$P NMR ($CDCl_3$) δ 19.1, 18.0.

Example 3

Bisamidate 8: A solution of triphenylphosphine (1.71 g, 6.54 mmol) and aldrithiol (1.44 g, 6.54 mmol) in dry pyridine (5 mL), stirred for at least 20 minutes at room temperature, was charged into a solution of diacid 6 (1.20 g, 1.87 mmol) and amine hydrochloride 7 (1.30 g, 7.47 mmol) in dry pyridine (10 mL). Diisopropylethylamine (0.97 g, 7.48 mmol) was then added to this combined solution and the contents were stirred at room temperature for 20 hours. The reaction was monitored by TLC assay ($SiO_2$, 5:5:1 ethyl acetate/hexanes/methanol as eluent, product $R_f$=0.29, visualization by UV). The reaction mixture was concentrated via rotary evaporator and dissolved in dichloromethane (50 mL). Brine (25 mL) was charged to wash the organic layer. The aqueous layer was back extracted with dichloromethane (1×50 mL). The combined organic layers were dried over sodium sulfate, filtered, and concentrated via rotary evaporator to afford an oil. The crude product oil was purified on silica gel using 4% isopropanol in dichloromethane as eluent. The combined fractions containing the product may have residual amine contamination. If so, the fractions were concentrated via rotary evaporator and further purified by silica gel chromatography using a gradient of 1:1 ethyl acetate/hexanes to 5:5:1 ethyl acetate/hexanes/methanol solution as eluent to afford the product 8 as a foam (0.500 g, 30% yield).

Example 4

Diacid 6: A solution of dibenzylphosphonate 9 (8.0 g, 9.72 mmol) in ethanol (160 mL) and ethyl acetate (65 mL) under a nitrogen atmosphere and at room temperature was charged 10% Pd/C (1.60 g, 20 wt %). The mixture was stirred and evacuated by vacuum and purged with hydrogen several times. The contents were then placed under atmospheric pressure of hydrogen via a balloon. The reaction was monitored by TLC assay ($SiO_2$, 7:2.5:0.5 dichloromethane/methanol/ammonium hydroxide as eluent, product $R_f$=0.05, visualization by UV) and was judged complete in 4 to 5 hours. The reaction mixture was filtered through a pad of celite to remove Pd/C and the filter cake rinsed with ethanol/ethyl acetate mixture (50 mL). The filtrate was concentrated via rotary evaporation followed by several co-evaporations using ethyl acetate (3×50 mL) to remove ethanol. The semi-solid diacid 6, free of ethanol, was carried forward to the next step without purification.

Example 5

Diphenylphosphonate 10: To a solution of diacid 6 (5.6 g, 8.71 mmol) in pyridine (58 mL) at room temperature was charged phenol (5.95 g, 63.1 mmol). To this mixture, while stirring, was charged dicyclohexylcarbodiimide (7.45 g, 36.0 mmol). The resulting cloudy, yellow mixture was placed in a 70-80° C. oil bath. The reaction was monitored by TLC assay ($SiO_2$, 7:2.5:0.5 dichloromethane/methanol/ammonium hydroxide as eluent, diacid $R_f$=0.05, visualization by UV for the disappearance of starting material. $SiO_2$, 60% ethyl acetate in hexanes as eluent, diphenyl $R_f$=0.40, visualization by UV) and was judged complete in 2 hours. To the reaction mixture was charged isopropyl acetate (60 mL) to produce a white precipitation. The slurry was filtered through a pad of celite to remove the white precipitate and the filter cake rinsed with isopropyl acetate (25 mL). The filtrate was concentrated via rotary evaporator. To the resulting yellow oil was charged a premixed solution of water (58 mL) and 1N HCl (55 mL) followed by isopropyl acetate (145 mL). The mixture was stirred for one hour in an ice bath. After separating the layers, the aqueous layer was back extracted with ethyl acetate (2×50 mL). The combined organic layers were dried over sodium sulfate, filtered, and concentrated via rotary evaporator. The crude product oil was purified by silica gel column chromatography using 50% ethyl acetate in hexanes as eluent to afford the product 10 as a white foam (3.52 g, 51% yield). $^1H$ NMR ($CDCl_3$) δ 7.75 (d, 2H), 7.40-7.20 (m, 15H), 7.10 (d, 2H), 5.65 (d, 1H), 5.10-4.90 (m, 2H), 4.65 (d, 2H), 4.00-3.80 (m, 4H), 3.75-3.65 (m, 3H), 3.25-2.75 (m, 7H), 1.90-1.75 (m, 1H), 1.70-1.60 (m, 1H), 1.50-1.40 (m, 1H), 0.90 (d, 3H), 0.85 (d, 3H). $^{31}P$ NMR ($CDCl_3$) δ 10.9.

Example 6

Monophenyl 1: To a solution of diphenyl 10 (3.40 g, 4.28 mmol) in acetonitrile (170 mL) at 0° C. was charged 1N sodium hydroxide (4.28 mL). The reaction was monitored by TLC assay ($SiO_2$, 7:2.5:0.5 dichloromethane/methanol/ammonium hydroxide as eluent, diphenyl $R_f$=0.65, visualization by UV for the disappearance of starting material. Product monophenyl $R_f$=0.80, visualization by UV). Additional 1N NaOH was added (if necessary) until the reaction was judged complete. To the reaction contents at 0° C. was charged Dowex $H^+$ (Dowex 50W×8-200) (4.42 g) and stirred for 30 minutes at which time the pH of the mixture reached pH 1 (monitored by pH paper). The mixture was filtered to remove the Dowex resin and the filtrate was concentrated via rotary evaporation (water bath<40° C.). The resulting solution was co-evaporated with toluene to remove water (3×50 mL). The white foam was dissolved in ethyl acetate (8 mL) followed by slow addition of hexanes (16 mL) over 30 minutes to induce precipitation. A premixed solution of 2:1 hexnaes/ethyl acetate solution (39 mL) was charged to the precipitated material and stirred. The product 1 was filtered and rinsed with premixed solution of 2:1 hexanes/ethyl acetate solution (75 mL) and dried under vacuum to afford a white powder (2.84 g, 92% yield). $^1H$ NMR ($CD_3OD$) δ 7.80 (d, 2H), 7.40-7.30 (m, 2H), 7.20-7.15 (m, 11H), 5.55 (d, 1H), 4.50 (d, 2H), 3.95-3.85 (m, 1H), 3.80-3.60 (m, 5H), 3.45 (bd, 1H), 3.25-3.15 (m, 2H), 3.00-2.80 (m, 3H), 2.60-2.45 (m, 1H), 2.10-1.95 (m, 2H), 1.85-1.60 (m, 2H), 1.50-1.40 (m, 1H), 1.40-1.30 (m, 1H), 0.95 (d, 3H), 0.85 (d, 3H). $^{31}P$ NMR ($CDCl_3$) δ 13.8. The monophenyl product 1 is sensitive to silica gel. On contact with silica gel 1 converts to an unknown compound possessing $^{31}P$ NMR chemical shift of 8 ppm. However, the desired monophenyl product 1 can be regenerated by treatment of the unknown compound with 2.5 M NaOH in acetonitrile at 0° C. for one hour followed by Dowex $H^+$ treatment as described above.

Example 7

Dibenzylphosphonate 9: To a solution of phenol 11 (6.45 g, 11.8 mmol) in tetrahydrofuran (161 mL) at room temperature was charged triflate reagent 12 (6.48 g, 15.3 mmol). Cesium carbonate (11.5 g, 35.3 mmol) was added and the mixture was stirred and monitored by TLC assay ($SiO_2$, 5% methanol in dichloromethane as eluent, dibenzyl product $R_f$=0.26, visualization by UV or ninhydrin stain and heat). Additional $Cs_2CO_3$ was added until the reaction was judged complete. To the reaction contents was charged water (160 mL) and the mixture extracted with ethyl acetate (2×160 mL). The combined organic layer was dried over sodium sulfate, filtered, and concentrated via rotary evaporator to afford a viscous oil. The crude oil was purified by silica gel column chromatography using a gradient of 100% dichloromethane to 1% methanol in dichloromethane to afford product 9 as a white foam (8.68 g, 90% yield). $^1H$ NMR ($CDCl_3$) δ 7.75 (d, 2H), 7.40-7.20 (m, 16H), 6.95 (d, 2H), 5.65 (d, 1H), 5.20-4.90 (m, 6H), 4.25 (d, 2H), 4.00-3.80 (m, 4H), 3.75-3.65 (m, 3H), 3.20-2.75 (m, 7H), 1.90-1.75 (m, 1H), 1.30-1.20 (m, 1H), 0.90 (d, 3H), 0.85 (d, 3H). $^{31}P$ NMR ($CDCl_3$) δ 19.1.

Example 7a

Hydroxyphenylsulfonamide 14: To a solution of methoxyphenylsulfonamide 13 (35.9 g, 70.8 mmol) in dichloromethane (3.5 L) at 0° C. was charged boron tribromide (1M in DCM, 40.1 mL, 425 mmol). The reaction content was allowed to warm to room temperature, stirred over two hours, and monitored by TLC assay ($SiO_2$, 10% methanol in dichloromethane as eluent, dibenzyl product $R_f$=0.16, visualization by UV). To the contents at 0° C. was slowly charged propylene oxide (82 g, 1.42 mmol). Methanol (200 mL) was added and the reaction mixture was concentrated via rotary evaporator to afford a viscous oil. The crude product mixture was purified by silica gel column chromatography using 10% methanol in dichloromethane to afford the product 14 as a foam (22 g, 80% yield). $^1$H NMR (DMSO) δ 7.60 (d, 2H), 7.30-7.20 (m, 5H), 6.95 (d, 2H), 3.90-3.75 (m, 1H), 3.45-3.20 (m, 5H), 3.00-2.55 (m, 5H), 2.50-2.40 (m, 1H), 1.95-1.85 (m, 1H), 0.85 (d, 3H), 0.80 (d, 3H).

Example 8

Cisfuran carbamate 16: To a solution of amine 14 (20.4 g, 52.0 mmol) in acetonitrile (600 mL) at room temperature was charged dimethylaminopyridine (13.4 g, 109 mmol) followed by cisfuran p-nitrophenylcarbonate reagent 15 (14.6 g, 49.5 mmol). The resulting solution was stirred at room temperature for at least 48 hours and monitored by TLC assay ($SiO_2$, 10% methanol in dichloromethane as eluent, cisfuran product $R_f$=0.34, visualization by UV). The reaction mixture was concentrated via rotary evaporator. The crude product mixture was purified by silica gel column chromatography using a gradient of 60% ethyl acetate in hexanes to 70% ethyl acetate in hexanes to afford the product 16 as a solid (18.2 g, 64% yield). $^1$H NMR (DMSO) δ 10.4 (bs, 1H), 7.60 (d, 2H), 7.30-7.10 (m, 6H), 6.95 (d, 2H), 5.50 (d, 1H), 4.85 (m, 1H), 3.85 (m, 1H), 3.70 (m, 1H), 3.65-3.50 (m, 4H), 3.30 (d, 1H), 3.05-2.95 (m, 2H), 2.80-2.65 (m, 3H), 2.50-2.40 (m, 1H), 2.00-1.90 (m, 1H), 1.45-1.20 (m, 2H), 0.85 (d, 3H), 0.80 (d, 3H).

Example Section L

Example 1

Monobenzyl phosphonate 2 A solution of dibenzylphosphonate 1 (150 mg, 0.175 mmol) was dissolved in toluene (1 mL), treated with DABCO (20 mg, 0.178 mmol) and was refluxed under N2 atmosphere (balloon) for 3 h. The solvent was removed and the residual was dissolved in aqueous HCl (5%). The aqueous layer was extracted with ethyl acetate and the organic layer was dried over sodium sulfate. After evaporation to yield the monobenzyl phosphonate 2 (107 mg, 80%) as a white powder. $^1$H NMR ($CD_3OD$) δ 7.75 (d, J=5.4 Hz, 2H), 7.42-7.31 (m, 5H) 7.16 (d, J=5.4 Hz, 2H), 7.01 (d, J=5.4 Hz, 2H), 6.86 (d, J=5.4 Hz, 2H), 5.55 (d, J=3.3 Hz, 1H), 5.14 (d, J=5.1 Hz, 2H), 4.91 (m, 1H), 4.24-3.66 (m overlapping s, 111H), 3.45 (m, 2H), 3.14-2.82 (m, 6H), 2.49 (m, 1H), 2.01 (m, 1H), 1.51-1.34 (m, 2H), 0.92 (d, J=3.9 Hz, 3H), 0.87 (d, J=3.9 Hz, 3H); $^{31}$P NMR ($CD_3OD$) δ 20.5; MS (ESI) 761 (M−H).

Example 2

Monobenzyl, ethyl phosphonate 3 To a solution of monobenzyl phosphonate 2 (100 mg, 0.13 mmol) in dry THF (5 mL) at room temperature under $N_2$ was added $Ph_3P$ (136 mg, 0.52 mmol) and ethanol (30 μL, 0.52 mmol). After cooled to 0° C., DEAD (78 μL, 0.52 mmol) was added. The mixture was stirred for 20 h at room temperature. The solvent was evaporated under reduced pressure and the residue was purified by using chromatograph on silica gel (10% to 30% ethyl acetate/hexane) to afford the monobenzyl, ethyl phosphonate 3 (66 mg, 64%) as white solid. $^1$H NMR ($CDCl_3$) 7.70 (d, J=8.7 Hz, 2H), 7.43-7.34 (m, 5H) 7.14 (d, J=8.4 Hz, 2H), 7.01 (d, J=8.7 Hz, 2H), 6.84 (d, J=8.4 Hz, 2H), 5.56 (d, J=5.4 Hz, 1H), 5.19 (d, J=8.7 Hz, 2H), 5.00 (m, 2H), 4.22-3.67 (m overlapping s, 13H), 3.18-2.76 (m, 7H), 1.82-1.54 (m, 3H), 1.33 (t, J=7.0 Hz, 3H), 0.92 (d, J=6.6 Hz, 3H), 0.88 (d, J=6.6 Hz, 3H); $^{31}$P NMR ($CDCl_3$) δ 19.8; MS (ESI) 813 (M+Na).

Example 3

Monoethyl phosphonate 4 A solution of monobenzyl, ethyl phosphonate 3 (60 mg) was dissolved in EtOAc (2 mL), treated with 10% Pd/C (6 mg) and was stirred under $H_2$ atmosphere (balloon) for 2 h. The catalyst was removed by filtration through celite. The filtered was evaporated under reduced pressure, the residue was triturated with ether and the solid was collected by filtration to afford the monoethyl phosphonate 4 (50 mg, 94%) as white solid. $^1$H NMR ($CD_3OD$) 7.76 (d, J=8.7 Hz, 2H), 7.18 (d, J=8.4 Hz, 2H), 7.01 (d, J=8.7 Hz, 2H), 6.89 (d, J=8.4 Hz, 2H), 5.58 (d, J=5.4 Hz, 1H), 5.90 (m, 1H), 4.22-3.67 (m overlapping s, 13H), 3.18-2.50 (m, 7H), 1.98 (m, 1H), 1.56 (m, 2H), 1.33 (t, J=6.9 Hz, 3H), 0.92 (d, J=6.6 Hz, 3H), 0.87 (d, J=6.6 Hz, 3H); $^{31}$P NMR ($CD_3OD$) δ 18.7; MS (ESI) 700 (M−H).

Example 4

Monophenyl, ethyl phosphonate 5 To a solution of phosphonic acid 11 (800 mg, 1.19 mmol) and phenol (1.12 g, 11.9 mmol) in pyridine (8 mL) was added ethanol (69 μL, 1.19 mmol) and 1,3-dicyclohexylcarbodiimide (1 g, 4.8 mmol). The solution was stirred at 70° C. for 2 h. The reaction mixture was cooled to room temperature, then diluted with ethyl acetate (10 mL) and filtered. The filtrate was evaporated under reduced pressure to remove pyridine. The residue was dissolved in ethyl acetate and the organic phase was separated and washed with brine, dried over MgSO4, filtered and concentrated. The residue was purified by chromatography on silica gel to give monophenyl, ethyl phosphonate 5 (600 mg, 65%) as white solid. $^1$H NMR ($CDCl_3$) 7.72 (d, J=9 Hz, 2H), 7.36-7.18 (m, 5H), 7.15 (d, J=8.7 Hz, 2H), 6.98 (d, J=9 Hz, 2H), 6.87 (d, J=8.7 Hz, 2H), 5.64 (d, J=5.4 Hz, 1H), 5.00 (m, 2H), 4.34 (m, 4H), 3.94-3.67 (m overlapping s, 9H), 3.18-2.77 (m, 7H), 1.82-1.54 (m, 3H), 1.36 (t, J=7.2 Hz, 3H), 0.92 (d, J=6.6 Hz, 3H), 0.87 (d, J=6.6 Hz, 3H); $^{31}$P NMR ($CDCl_3$) δ 16.1; MS (ESI) 799 (M+Na).

Example 5

Sulfonamide 6 To a suspension of epoxide 5 (3 g, 8.12 mmol) in 2-propanol (30 mL) was added isobutylamine (8 mL, 81.2 mmol) and the solution was stirred at 80° C. for 1 h. The solution was evaporated under reduced pressure and the crude solid was dissolved in $CH_2Cl_2$ (40 mL) and cooled to 0° C. TEA (2.3 mL, 16.3 mmol) was added followed by the addition of 4-nitrobenzenesulfonyl chloride (1.8 g, 8.13 mmol) in $CH_2Cl_2$ (5 mL) and the solution was stirred for 30 min at 0° C., warmed to room temperature and evaporated under reduced pressure. The residue was partitioned between EtOAc and saturated $NaHCO_3$. The organic phase was washed with saturated NaCl, dried over $Na_2SO_4$, filtered and evaporated under reduced pressure. The crude product was recrystallized from EtOAc/hexane to give the sulfonamide 6 (4.6 g, 91%) as an off-white solid. MS (ESI) 650 (M+Na).

Example 6

Phenol 7 A solution of sulfonamide 6 (4.5 g, 7.1 mmol) in $CH_2Cl_2$ (50 mL) at 0° C. was treated with $BBr_3$ (1M in $CH_2Cl_2$, 50 mL). The solution was stirred at 0° C. to room temperature for 48 h. $CH_3OH$ (10 mL) was carefully added.

The solvent was evaporated under reduced pressure and the residue was partitioned between EtOAc and saturated $NaHCO_3$. The organic phase washed with saturated NaCl, dried over $Na_2SO_4$, filtered, and evaporated under reduced pressure. The crude product was purified by chromatography on silica gel (10%-MeOH/$CH_2Cl_2$) to give the phenol 7 (2.5 g, 80%) as an off-white solid. MS (ESI) 528 (M+H).

Example 7

Carbamate 8 A solution of sulfonamide 7 (2.5 g, 5.7 mmol) in $CH_3CN$ (100 mL) and was treated with proton-sponge (3 g, 14 mmol) and followed by (3R,3aR,6aS)-hexahydrofuro[2,3-b]furan-2-yl 4-nitrophenyl carbonate (1.7 g, 5.7 mmol) at 0° C. After stirring for 48 h at room temperature, the reaction solvent was evaporated under reduced pressure and the residue was partitioned between EtOAc and 10% HCl. The organic phase was washed with saturated NaCl, dried over $Na_2SO_4$, filtered, and evaporated under reduced pressure. The crude product was purified by chromatography on silica gel (10% MeOH/$CH_2Cl_2$) affording the carbamate 8 (2.1 g, 62%) as a white solid. MS (ESI) 616 (M+Na).

Example 8

Diethylphosphonate 9 To a solution of carbamate 8 (2.1 g, 3.5 mmol) in $CH_3CN$ (50 mL) was added $Cs_2CO_3$ (3.2 g, 9.8 mmol) and diethyltriflate (1.6 g, 5.3 mmol). The mixture was stirred at room temperature for 1 h. After removed the solvent, the residue was partitioned between EtOAc and saturated NaCl. The organic phase was dried over $Na_2SO_4$, filtered, and evaporated under reduced pressure. The crude product was chromatographed on silica gel (1% to 5% MeOH/$CH_2Cl_2$) to afford the diethylphosphonate 9 as a white solid: $^1$H NMR ($CDCl_3$) δ 8.35 (d, J=9 Hz, 2H), 7.96 (d, J=9 Hz, 2H), 7.13 (d, J=8.4 Hz, 2H), 6.85 (d, J=8.4 Hz, 2H), 5.63 (d, J=5.1 Hz, 1H), 5.18-5.01 (m, 2H), 4.27-4.17 (m, 6H), 3.94-3.67 (m, 7H), 3.20-2.73 (m, 7H), 1.92-1.51 (m, 3H), 1.35 (t, J=7.2 Hz, 6H), 0.88-0.85 (m, 6H); $^{31}$P NMR ($CDCl_3$) δ 19.2; MS (ESI) 756 (M+Na).

Example 9

Amine 10 A solution of diethylphosphonate 9 (1 g) was dissolved in EtOH (100 mL), treated with 10% Pd/C (300 mg) and was stirred under $H_2$ atmosphere (balloon) for 3 h. The reaction was purged with $N_2$, and the catalyst was removed by filtration through celite. After evaporation of the filtrate, the residue was triturated with ether and the solid was collected by filtration to afford the amine 10 (920 mg, 96%) as a white solid. $^1$H NMR ($CDCl_3$) $^1$H NMR ($CDCl_3$) δ 7.41 (d, J=8.4 Hz, 2H), 7.17 (d, J=8.4 Hz, 2H), 6.88 (d, J=8.4 Hz, 2H), 6.68 (d, J=8.4 Hz, 2H), 5.67 (d, J=5.1 Hz, 1H), 5.13-5.05 (m, 2H), 4.42 (s, 2H), 4.29-4.20 (m, 6H), 4.00-3.69 (m, 7H), 3.00-2.66 (m, 7H), 1.80-1.69 (m, 3H), 1.38 (m, 6H), 0.94 (d, J=6.4 Hz, 3H), 0.86 (d, J=6.4 Hz, 6H); $^{31}$P NMR ($CDCl_3$) δ 19.4; MS (ESI) 736 (M+Na).

| Compound | $R_1$ | $R_2$ |
|---|---|---|
| 16a | Gly-Et | Gly-Et |
| 16b | Gly-Bu | Gly-Bu |
| 16j | Phe-Bu | Phe-Bu |
| 16k | NHEt | NHEt |

Example 10

Synthesis of Bisamidates 16a. A solution of phosphonic acid 11 (100 mg, 0.15 mmol) L-alanine ethyl ester hydrochloride (84 mg, 0.6 mmol) was dissolved in pyridine (5 mL) and the solvent was distilled under reduced pressure at 40-60° C. The residue was treated with a solution of $Ph_3P$ (118 mg, 0.45 mmol) and 2,2'-dipyridyl disulfide (99 mg, 0.45 mmol) in pyridine (1 mL) stirring for 20 h at room temperature. The solvent was evaporated under reduced pressure and the residue was chromatographed on silica gel (1% to 5% 2-propanol/$CH_2Cl_2$). The purified product was suspended in ether and was evaporated under reduced pressure to afford bisamidate 16a (90 mg, 72%) as a white solid: $^1$H NMR ($CDCl_3$) δ 7.72 (d, J=8.7 Hz, 2H), 7.15 (d, J=8.7 Hz, 2H), 7.01 (d, J=8.7 Hz, 2H), 6.87 (d, J=8.7 Hz, 2H), 5.68 (d, J=5.1 Hz, 1H), 5.05 (m, 1H), 4.25 (d, J=9.9 Hz, 2H), 4.19 (q, 4H), 3.99-3.65 (m overlapping s, 13H,), 3.41 (m, 1H), 3.20-2.81 (m, 7H), 1.85-1.60 (m, 3H), 1.27 (t, J=7.2 Hz, 6H), 0.93 (d, J=6.3 Hz, 3H), 0.89 (d, J=6.3 Hz, 3H); $^{31}$P NMR ($CDCl_3$) δ 21.8; MS (ESI) 843 (M+H).

Example 11

Synthesis of Bisamidates 16b. A solution of phosphonic acid 11 (100 mg, 0.15 mmol) L-alanine n-butyl ester hydrochloride (101 mg, 0.6 mmol) was dissolved in pyridine (5 mL) and the solvent was distilled under reduced pressure at 40-60° C. The residue was treated with a solution of $Ph_3P$ (118 mg, 0.45 mmol) and 2,2'-dipyridyl disulfide (99 mg, 0.45 mmol) in pyridine (1 mL) stirring for 20 h at room temperature. The solvent was evaporated under reduced pressure and the residue was chromatographed on silica gel (1% to 5% 2-propanol/$CH_2Cl_2$). The purified product was suspended in ether and was evaporated under reduced pressure to afford bisamidate 16b (100 mg, 74%) as a white solid: $^1$H NMR ($CDCl_3$) δ 7.72 (d, J=9 Hz, 2H), 7.15 (d, J=9 Hz, 2H), 7.01 (d, J=9 Hz, 2H), 6.87 (d, J=9 Hz, 2H), 5.67 (d, J=5.4 Hz, 1H), 5.05 (m, 1H), 4.96 (m, 1H), 4.25 (d, J=9.9 Hz, 2H), 4.11 (t, J=6.9 Hz, 4H), 3.99-3.71 (m overlapping s, 13H,), 3.41 (m, 1H), 3.20-2.80 (m, 7H), 1.87-1.60 (m, 7H), 1.42 (m, 4H), 0.96-0.88 (m, 12H); $^{31}$P NMR ($CDCl_3$) δ 21.8; MS (ESI) 890 (M+H).

Example 12

Synthesis of Bisamidates 16j. A solution of phosphonic acid 11 (100 mg, 0.15 mmol) L-phenylalanine n-butyl ester hydrochloride (155 mg, 0.6 mmol) was dissolved in pyridine (5 mL) and the solvent was distilled under reduced pressure at 40-60° C. The residue was treated with a solution of $Ph_3P$ (118 mg, 0.45 mmol) and 2,2'-dipyridyl disulfide (99 mg, 0.45 mmol) in pyridine (1 mL) stirring for 36 h at room temperature. The solvent was evaporated under reduced pressure and the residue was chromatographed on silica gel (1% to 5% 2-propanol/$CH_2Cl_2$). The purified product was suspended in ether and was evaporated under reduced pressure to afford bisamidate 16j (106 mg, 66%) as a white solid. $^1$H NMR ($CDCl_3$) δ 7.72 (d, J=8.7 Hz, 2H), 7.31-7.10 (m, 12H), 7.01 (d, J=9 Hz, 2H), 6.72 (d, J=8.7 Hz, 2H), 5.67 (d, J=5.1 Hz, 1H), 5.05 (m, 1H), 4.96 (m, 1H), 4.35-3.98 (m, 7H), 3.90-3.61 (m overlapping s, 10H,), 3.19-2.78 (m, 11H), 1.87-1.25 (m, 11H), 0.96-0.88 (m, 12H); $^{31}$P NMR ($CDCl_3$) δ 19.3; MS (ESI) 1080 (M+H).

Example 13

Synthesis of Bisamidates 16k. A solution of phosphonic acid 11 (80 mg, 0.12 mmol), ethylamine (0.3 mL, 2M in THF, 0.6 mmol) was dissolved in pyridine (5 mL) and the solvent was distilled under reduced pressure at 40-60° C. The residue was treated with a solution of $Ph_3P$ (109 mg, 0.42 mmol) and 2,2'-dipyridyl disulfide (93 mg, 0.42 mmol) in pyridine (1 mL) stirring for 48 h at room temperature. The solvent was evaporated under reduced pressure and the residue was chromatographed on silica gel (1% to 5% 2-propanol/$CH_2Cl_2$). The purified product was suspended in ether and was evaporated under reduced pressure to afford bisamidate 16k (60 mg, 70%) as a white solid: $^1$H NMR ($CDCl_3$) δ 7.72 (d, J=8.7 Hz, 2H), 7.15 (d, J=8.7 Hz, 2H), 7.01 (d, J=8.7 Hz, 2H), 6.87 (d, J=8.7 Hz, 2H), 5.67 (d, J=5.1 Hz, 1H), 5.05-4.95 (m, 2H), 4.15 (d, J=9.6 Hz, 2H), 3.99-3.72 (m overlapping s, 9H,), 3.18-2.81 (m, 11H), 2.55 (br, 1H), 1.85-1.65 (m, 3H), 1.18 (t, J=7.2 Hz, 6H), 0.93 (d, J=6.3 Hz, 3H), 0.89 (d, J=6.3 Hz, 3H); $^{31}$P NMR ($CDCl_3$) δ 21.6; MS (ESI) 749 (M+Na).

| Compound | $R_1$ | $R_2$ |
|---|---|---|
| 30a | OPh | Ala-Me |
| 30b | OPh | Ala-Et |
| 30c | OPh | (D)-Ala-iPr |
| 30d | OPh | Ala-Bu |
| 30e | OBn | Ala-Et |

Example 14

Monoamidate 30a (R1=OPh, R2=Ala-Me) To a flask was charged with monophenyl phosphonate 29 (75 mg, 0.1 mmol), L-alanine methyl ester hydrochloride (4.0 g, 22 mmol) and 1,3-dicyclohexylcarbodiimide (84 mg, 0.6 mmol), then pyridine (1 mL) was added under N2. The resulted mixture was stirred at 60-70° C. for 2 h, then cooled to room temperature and diluted with ethyl acetate. The mixture was filtered and the filtrate was evaporated. The residue was partitioned between ethyl acetate and HCl (0.2 N), the ethyl acetate phase was washed with water and $NaHCO_3$, dried over $Na_2SO_4$ filtered and concentrated. The residue was purified by chromatography on silica gel (ethyl acetate/hexane 1:5) to give 30a (25 mg, 30%) as a white solid. $^1$H NMR ($CDCl_3$) δ 7.72 (d, J=8.7 Hz, 2H), 7.73-7.24 (m, 5H) 7.19-7.15 (m, 2H), 7.01 (d, J=8.7 Hz, 2H), 6.90-6.83 (m, 2H), 5.65 (d, J=5.1 Hz, 1H), 5.01 (m, 2H), 4.30 (m, 2H), 3.97-3.51 (m overlapping s, 12H), 3.20-2.77 (m, 7H), 1.81 (m, 1H), 1.58 (m, 3H), 0.92 (d, J=6.3 Hz, 3H), 0.88 (d, J=6.3 Hz, 3H); $^{31}$P NMR ($CDCl_3$) δ 20.4 and 19.3; MS (ESI) 856 (M+Na).

Example 15

Monoamidate 30b (R1=OPh, R2=Ala-Et) was synthesized in the same manner in 35% yield. $^1$H NMR ($CDCl_3$) δ 7.72 (d, J=8.7 Hz, 2H), 7.73-7.24 (m, 5H) 7.19-7.15 (m, 2H), 7.01 (d, J=8.7 Hz, 2H), 6.90-6.83 (m, 2H), 5.65 (d, J=5.4 Hz, 1H), 5.01 (m, 3H), 4.30-3.67 (m overlapping s, 14H), 3.18-2.77 (m, 7H), 1.81-1.35 (m, 6H), 1.22 (m, 3H), 0.92 (d, J=6.3 Hz, 3H), 0.88 (d, J=6.3 Hz, 3H); $^{31}$P NMR ($CDCl_3$) δ 20.4 and 19.3; MS (ESI) 870 (M+Na).

Example 16

Monoamidate 30c (R1=OPh, R2=(D)-Ala-iPr) was synthesized in the same manner in 52% yield. Isomer A $^1$H NMR ($CDCl_3$) δ 7.72 (d, J=8.7 Hz, 2H), 7.73-7.24 (m, 5H) 7.19-7.15 (m, 2H), 7.01 (d, J=8.7 Hz, 2H), 6.90-6.83 (m, 2H), 5.66 (m 1H), 5.01 (m, 3H), 4.30-3.67 (m overlapping s, 14H), 3.18-2.77 (m, 7H), 1.81-1.35 (m, 6H), 1.23 (m, 6H), 0.92 (d, J=6.3 Hz, 3H), 0.88 (d, J=6.3 Hz, 3H); $^{31}$P NMR ($CDCl_3$) δ 20.4; MS (ESI) 884 (M+Na). Isomer B $^1$H NMR ($CDCl_3$) δ 7.72 (d, J=8.7 Hz, 2H), 7.73-7.24 (m, 5H) 7.19-7.15 (m, 2H), 7.01 (d, J=8.7 Hz, 2H), 6.90-6.83 (m, 2H), 5.66 (m 1H), 5.01 (m, 3H), 4.30-3.67 (m overlapping s, 14H), 3.18-2.77 (m, 7H), 1.81-1.35 (m, 6H), 1.23 (m, 6H), 0.92 (d, J=6.3 Hz, 3H), 0.88 (d, J=6.3 Hz, 3H); $^{31}$P NMR ($CDCl_3$) δ 19.3; MS (ESI) 884 (M+Na).

Example 17

Monoamidate 30d (R1=OPh, R2=Ala-Bu) was synthesized in the same manner in 25% yield. $^1$H NMR ($CDCl_3$) δ 7.72 (d, J=8.7 Hz, 2H), 7.73-7.24 (m, 5H) 7.19-7.15 (m, 2H), 7.01 (d, J=8.7 Hz, 2H), 6.90-6.83 (m, 2H), 5.65 (d, J=5.4 Hz, 1H), 5.01 (m, 3H), 4.30-3.67 (m overlapping s, 16H), 3.18-2.77 (m, 7H), 1.81-1.35 (m, 8H), 1.22 (m, 3H), 0.92 (d, J=6.3 Hz, 3H), 0.88 (d, J=6.3 Hz, 3H); $^{31}$P NMR ($CDCl_3$) δ 20.4 and 19.4; MS (ESI) 898 (M+Na).

Example 18

Monoamidate 30e (R1=OBn, R2=Ala-Et) To a flask was charged with monobenzyl phosphonate 2 (76 mg, 0.1 mmol), L-alanine methyl ester hydrochloride (4.0 g, 22 mmol) and 1,3-dicyclohexylcarbodiimide (84 mg, 0.6 mmol), then pyridine (1 mL) was added under N2. The resulted mixture was stirred at 60-70° C. for 2 h, then cooled to room temperature and diluted with ethyl acetate. The mixture was filtered and the filtrate was evaporated. The residue was partitioned between ethyl acetate and HCl (0.2 N), the ethyl acetate phase was washed with water and $NaHCO_3$, dried over $Na_2SO_4$ filtered and concentrated. The residue was purified by chromatography on silica gel (ethyl acetate/hexane 1:5) to give 30a (25 mg, 30%) as a white solid. $^1$H NMR ($CDCl_3$) δ 7.72 (d, J=8.7 Hz, 2H), 7.38-7.34 (m, 5H), 7.13 (d, J=8.7 Hz, 2H), 7.00 (d, J=8.7 Hz, 2H), 6.86-6.80 (m, 2H), 5.65 (d, J=5.4 Hz, 1H), 5.15-5.01 (m, 5H), 4.30-3.67 (m overlapping s, 14H), 3.18-2.77 (m, 7H), 1.81-1.35 (m, 6H), 1.22 (m, 3H), 0.92 (d, J=6.3 Hz, 3H), 0.88 (d, J=6.3 Hz, 3H); $^{31}$P NMR ($CDCl_3$) δ 23.3 and 22.4; MS (ESI) 884 (M+Na).

| Compound | $R_1$ | $R_2$ |
|---|---|---|
| 31a | OPh | Lac-iPr |
| 31b | OPh | Lac-Et |
| 31c | OPh | Lac-Bu |
| 31d | OPh | (R)-Lac-Me |
| 31e | OPh | (R)-Lac-Et |

Example 19

Monolactate 31a (R1=OPh, R2=Lac-iPr): To a flask was charged with monophenyl phosphonate 29 (1.5 g, 2 mmol), isopropyl-(s)-lactate (0.88 nL, 6.6 mmol) and 1,3-dicyclohexylcarbodiimide (1.36 g, 6.6 mmol), then pyridine (15 mL) was added under $N_2$. The resulted mixture was stirred at 60-70° C. for 2 h, then cooled to room temperature and diluted with ethyl acetate. The mixture was filtered and the filtrate was evaporated. The residue was washed with ethyl acetate and the combined organic phase was washed with $NH_4Cl$, brine and water, dried over $Na_2SO_4$, filtered and concentrated. The residue was purified by chromatography on silica gel (ethyl acetate/$CH_2Cl_2$ 1:5) to give 31a (1.39 g, 81%) as a white solid. Isomer A $^1$H NMR ($CDCl_3$) δ 7.72 (d, J=8.7 Hz, 2H), 7.73-7.19 (m, 5H), 7.15 (d, J=8.4 Hz, 2H), 7.00 (d, J=8.7 Hz, 2H), 6.92 (d, J=8.4 Hz, 2H), 5.65 (d, J=5.4 Hz, 1H), 5.15-5.00 (m, 4H), 4.56-4.44 (m, 2H), 3.96-3.68 (m overlapping s, 9H), 3.13-2.78 (m, 7H), 1.81-1.23 (m, 6H), 1.22 (m, 6H), 0.92 (d, J=6.6 Hz, 3H), 0.88 (d, J=6.6 Hz, 3H); $^{31}$P NMR ($CDCl_3$) δ 17.4; MS (ESI) 885 (M+Na). Isomer B $^1$H NMR ($CDCl_3$) δ 7.72 (d, J=8.7 Hz, 2H), 7.73-7.19 (m, 5H), 7.14 (d, J=8.4 Hz, 2H), 7.00 (d, J=8.7 Hz, 2H), 6.88 (d, J=8.4 Hz, 2H), 5.64 (d, J=5.4 Hz, 1H), 5.15-5.00 (m, 4H), 4.53-4.41 (m, 2H), 3.96-3.68 (m overlapping s, 9H), 3.13-2.78 (m, 7H), 1.81-1.23 (m, 6H), 1.22 (m, 6H), 0.92 (d, J=6.6 Hz, 3H), 0.88 (d, J=6.6 Hz, 3H); $^{31}$P NMR ($CDCl_3$) δ 15.3; MS (ESI) 885 (M+Na).

Example 20

Monolactate 31b (R1=OPh, R2=Lac-Et) was synthesized in the same manner in 75% yield. $^1$H NMR ($CDCl_3$) δ 7.72 (d, J=8.7 Hz, 2H), 7.73-7.14 (m, 7H), 6.99 (d, J=8.7 Hz, 2H), 6.88 (d, J=8.7 Hz, 2H), 5.63 (m, 1H), 5.19-4.95 (m, 3H), 4.44-4.40 (m, 2H), 4.17-4.12 (m, 2H), 3.95-3.67 (m overlapping s, 9H), 3.15-2.77 (m, 7H), 1.81-1.58 (m, 6H), 1.23 (m, 3H), 0.91 (d, J=6.6 Hz, 3H), 0.87 (d, J=6.6 Hz, 3H); $^{31}$P NMR ($CDCl_3$) δ 17.5 and 15.4; MS (ESI) 872 (M+Na).

Example 21

Monolactate 31c (R1=OPh, R2=Lac-Bu) was synthesized in the same manner in 58% yield. Isomer A $^1$H NMR ($CDCl_3$) δ 7.72 (d, J=8.7 Hz, 2H), 7.73-7.19 (m, 5H), 7.14 (d, J=8.4 Hz, 2H), 7.00 (d, J=8.7 Hz, 2H), 6.90 (d, J=8.4 Hz, 2H), 5.63 (d, J=5.4 Hz, 1H), 5.15-5.00 (m, 3H), 4.56-4.51 (m, 2H), 4.17-4.10 (m, 2H), 3.95-3.67 (m overlapping s, 9H), 3.10-2.77 (m, 7H), 1.81-1.23 (m, 10H), 1.23 (m, 6H), 0.91 (d, J=6.6 Hz, 3H), 0.87 (d, J=6.6 Hz, 3H); $^{31}$P NMR ($CDCl_3$) δ 17.3; MS (ESI) 899 (M+Na). Isomer B $^1$H NMR ($CDCl_3$) δ 7.72 (d, J=8.7 Hz, 2H), 7.73-7.19 (m, 5H), 7.14 (d, J=8.4 Hz, 2H), 7.00 (d, J=8.7 Hz, 2H), 6.90 (d, J=8.4 Hz, 2H), 5.64 (d, J=5.4 Hz, 1H), 5.15-5.00 (m, 3H), 4.44-4.39 (m, 2H), 4.17-4.10 (m, 2H), 3.95-3.67 (m overlapping s, 9H), 3.10-2.77 (m, 7H), 1.81-1.23 (m, 10H), 1.23 (m, 6H), 0.91 (d, J=6.6 Hz, 3H), 0.87 (d, J=6.6 Hz, 3H); $^{31}$P NMR ($CDCl_3$) δ 15.3; MS (ESI) 899 (M+Na).

Example 22

Monolactate 31d (R1=OPh, R2=(R)-Lac-Me): To a stirred solution of monophenyl phosphonate 29 (100 mg, 0.13 mmol) in 10 mL of THF at room temperature under $N_2$ was added methyl-(S)-lactate (54 mg, 0.52 mmol) and $Ph_3P$ (136 mg g 0.52 mmol), followed by DEAD (82 μL, 0.52 mmol). After 2 h, the solvent was removed under reduced pressure, and the resulting crude mixture was purified by chromatography on silica gel (ethyl acetate/hexane 1:1) to give 31d (33 mg, 30%) as a white solid. $^1$H NMR ($CDCl_3$) δ 7.72 (d, J=8.7 Hz, 2H), 7.73-7.14 (m, 7H), 6.99 (d, J=8.7 Hz, 2H), 6.88 (d, J=8.7 Hz, 2H), 5.63 (m, 1H), 5.19-4.95 (m, 3H), 4.44-4.40 (m, 2H), 3.95-3.64 (m overlapping s, 12H), 3.15-2.77 (m, 7H), 1.81-1.55 (m, 4H), 0.91 (d, J=6.6 Hz, 3H), 0.87 (d, J=6.6 Hz, 3H); $^{31}$P NMR ($CDCl_3$) δ 17.4 and 15.3; MS (ESI) 857 (M+Na).

Example 23

Monolactate 31 e (R1=OPh, R2=(R)-Lac-Et): To a stirred solution of monophenyl phosphonate 29 (50 mg, 0.065 mmol) in 2.5 mL of THF at room temperature under $N_2$ was added ethyl-(s)-lactate (31 mg, 0.52 mmol) and $Ph_3P$ (68 mg g, 0.26 mmol), followed by DEAD (41 μL, 0.52 mmol). After 2 h, the solvent was removed under reduced pressure, and the resulting crude mixture was purified by chromatography on silica gel (ethyl acetate/hexane 1:1) to give 31e (28 mg, 50%) as a white solid. $^1$H NMR ($CDCl_3$) δ 7.72 (d, J=8.7 Hz, 2H), 7.73-7.14 (m, 7H), 6.99 (d, J=8.7 Hz, 2H), 6.85 (m, 2H), 5.63 (m, 1H), 5.19-4.95 (m, 3H), 4.44-4.40 (m, 2H), 4.17-4.12 (m, 2H), 3.95-3.67 (m overlapping s, 9H), 3.15-2.77 (m, 7H), 1.81-1.58 (m, 6H), 1.23 (m, 3H), 0.91 (d, J=6.6 Hz, 3H), 0.87 (d, J=6.6 Hz, 3H); $^{31}$P NMR ($CDCl_3$) δ 17.5 and 15.4; MS (ESI) 872 (M+Na).

Example 24

Monolactate 32 (R1=OBn, R2=(S)-Lac-Bn): To a stirred solution of monobenzyl phosphonate 2 (76 mg, 0.1 mmol) in 0.5 mL of DMF at room temperature under $N_2$ was added benzyl-(s)-lactate (27 mg, 0.15 mmol) and PyBOP (78 mg, 0.15 mmol), followed by DIEA (70 μL, 0.4 mmol). After 3 h, the solvent was removed under reduced pressure, and the resulting crude mixture was purified by chromatography on silica gel (ethyl acetate/hexane 1:1) to give 32 (46 mg, 50%) as a white solid. $^1$H NMR ($CDCl_3$) δ 7.72 (d, J=8.7 Hz, 2H), 7.38-7.44 (m, 10H), 7.13 (d, J=8.4 Hz, 2H), 6.99 (d, J=8.7 Hz, 2H), 6.81 (m, 2H), 5.63 (d, J=5.1 Hz, 1H), 5.23-4.92 (m, 7H), 4.44-22 (m, 2H), 3.96-3.67 (m overlapping s, 9H), 3.15-2.77 (m, 7H), 1.81-1.58 (m, 6H), 0.93 (d, J=6.3 Hz, 3H), 0.88 (d, J=6.3 Hz, 3H); $^{31}$P NMR ($CDCl_3$) δ 20.8 and 19.6; MS (ESI) 947 (M+Na).

Example 25

Monolactate 33 (R1=OBn, R2=(R)-Lac-Bn): To a stirred solution of monobenzyl phosphonate 2 (76 mg, 0.1 mmol) in 5 mL of THF at room temperature under $N_2$ was added benzyl-(s)-lactate (72 mg, 0.4 mmol) and $Ph_3P$ (105 mg g, 0.4 mmol), followed by DEAD (60 μL, 0.4 mmol). After 20 h, the solvent was removed under reduced pressure, and the resulting crude mixture was purified by chromatography on silica gel (ethyl acetate/hexane 1:1) to give 33 (44 mg, 45%) as a white solid. $^1$H NMR ($CDCl_3$) δ 7.72 (d, J=8.7 Hz, 2H), 7.38-7.44 (m, 10H), 7.13 (m, 2H), 6.99 (d, J=8.7 Hz, 2H), 6.81 (m, 2H), 5.63 (m, 1H), 5.23-4.92 (m, 7H), 4.44-22 (m, 2H), 3.96-3.67 (m overlapping s, 9H), 3.15-2.77 (m, 7H), 1.81-1.58 (m, 6H), 0.93 (d, J=6.3 Hz, 3H), 0.88 (d, J=6.3 Hz, 3H); $^{31}$P NMR ($CDCl_3$) δ 20.8 and 19.6; MS (ESI) 947 (M+Na).

Example 26

Monophosphonic acid 34: A solution of monobenzyllactate 32 (20 mg) was dissolved in EtOH/EtOAc (3 mL/1 mL), treated with 10% Pd/C (4 mg) and was stirred under H2 atmosphere (balloon) for 1.5 h. The catalyst was removed by filtration through celite. The filtered was evaporated under reduced pressure, the residue was triturated with ether and the solid was collected by filtration to afford the monophosphonic acid 33 (15 mg, 94%) as a white solid. $^1$H NMR ($CD_3OD$) δ 7.76 (d, J=8.7 Hz, 2H), 7.18 (d, J=8.7 Hz, 2H), 7.08 (d, J=8.7 Hz, 2H), 6.90 (d, J=8.7 Hz, 2H), 5.69 (d, J=5.7 Hz, 1H), 5.03-4.95 (m, 2H), 4.20 (m, 2H), 3.90-3.65 (m overlapping s, 9H), 3.41 (m, 2H), 3.18-2.78 (m, 5H), 2.44 (m, 1H), 2.00 (m, 1H), 1.61-1.38 (m, 5H), 0.93 (d, J=6.3 Hz, 3H), 0.88 (d, J=6.3 Hz, 3H); 31P NMR ($CD_3OD$) δ 18.0; MS (ESI) 767 (M+Na).

Example 27

Monophosphonic acid 35: A solution of monobenzyllactate 33 (20 mg) was dissolved in EtOH (3 mL), treated with 10% Pd/C (4 mg) and was stirred under H2 atmosphere (balloon) for 1 h. The catalyst was removed by filtration through celite. The filtered was evaporated under reduced pressure, the residue was triturated with ether and the solid was collected by filtration to afford the monophosphonic acid 35 (15 mg, 94%) as a white solid. $^1$H NMR ($CD_3OD$) δ 7.76 (d, J=8.7 Hz, 2H), 7.18 (d, J=8.7 Hz, 2H), 7.08 (d, J=8.7 Hz, 2H), 6.90 (d, J=8.7 Hz, 2H), 5.69 (d, J=5.7 Hz, 1H), 5.03-4.95 (m, 2H), 4.20 (m, 2H), 3.90-3.65 (m overlapping s, 9H), 3.41 (m, 2H), 3.18-2.78 (m, 5H), 2.44 (m, 1H), 2.00 (m, 1H), 1.61-1.38 (m, 5H), 0.93 (d, J=6.3 Hz, 3H), 0.88 (d, J=6.3 Hz, 3H); $^{31}$P NMR ($CD_3OD$) δ 18.0; MS (ESI) 767 (M+Na).

Example 28

Synthesis of Bislactate 36: A solution of phosphonic acid 11 (100 mg, 0.15 mmol) isopropyl-(S)-lactate (79 mg, 0.66 mmol) was dissolved in pyridine (1 mL) and the solvent was distilled under reduced pressure at 40-60° C. The residue was treated with a solution of $Ph_3P$ (137 mg, 0.53 mmol) and 2,2'-dipyridyl disulfide (116 mg, 0.53 mmol) in pyridine (1 mL) stirring for 20 h at room temperature. The solvent was evaporated under reduced pressure and the residue was chromatographed on silica gel (1% to 5% 2-propanol/$CH_2Cl_2$).

The purified product was suspended in ether and was evaporated under reduced pressure to afford bislactate 36 (42 mg, 32%) as a white solid: $^1$H NMR ($CDCl_3$) δ 7.72 (d, J=8.7 Hz, 2H), 7.14 (d, J=8.7 Hz, 2H), 7.01 (d, J=8.7 Hz, 2H), 6.89 (d, J=8.7 Hz, 2H), 5.66 (d, J=5.1 Hz, 1H), 5.05 (m, 3H), 4.25 (d, J=9.9 Hz, 2H), 4.19 (q, 4H), 3.99-3.65 (m overlapping s, 9H,), 3.41 (m, 1H), 3.20-2.81 (m, 7H), 1.85-1.60 (m, 3H), 1.58 (m, 6H), 1.26 (m, 12H), 0.93 (d, J=6.3 Hz, 3H), 0.89 (d, J=6.3 Hz, 3H); $^{31}$P NMR ($CDCl_3$) δ 21.1; MS (ESI) 923 (M+Na).

Example 29

Triflate derivative 1: A THF—$CH_2Cl_2$ solution (30 mL-10 mL) of 8 (4 g, 6.9 mmol), cesium carbonate (2.7 g, 8 mmol), and N-phenyltrifluoromethane sulfonimide (2.8 g, 8 mmol) was reacted overnight. The reaction mixture was worked up, and concentrated to dryness to give crude triflate derivative 1.

Aldehyde 2: Crude triflate 1 (4.5 g, 6.9 mmole) was dissolved in DMF (20 mL), and the solution was degassed (high vacuum for 2 min, Ar purge, repeat 3 times). $Pd(OAc)_2$ (0.12 g, 0.27 mmol), and bis(diphenylphosphino)propane (dppp, 0.22 g, 0.27 mmol) were added and the solution was heated to 70° C. Carbon monoxide was rapidly bubbled through the solution, then under 1 atmosphere of carbon monoxide. To this solution were slowly added TEA (5.4 mL, 38 mmol), and triethylsilane (3 mL, 18 mmol). The resulting solution was stirred overnight at room temperature. The reaction mixture was worked up, and purified on silica gel column chromatograph to afford aldehyde 2 (2.1 g, 51%). (Hostetler, et al. J. Org. Chem., 1999. 64, 178-185).

Lactate prodrug 4: Compound 4 is prepared as described above procedure for 3a-e by the reductive amination between 2 and 3 with $NaBH_3CN$ in 1,2-dichloroethane in the presence of HOAc.

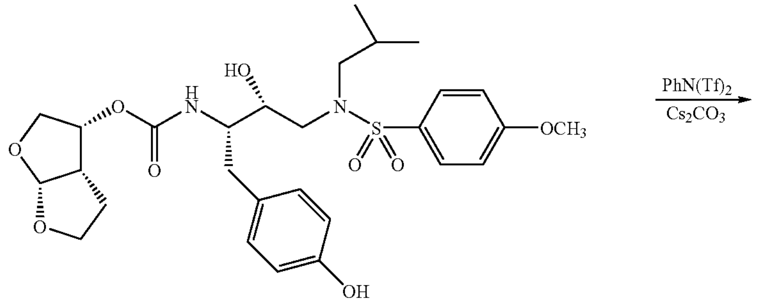

8

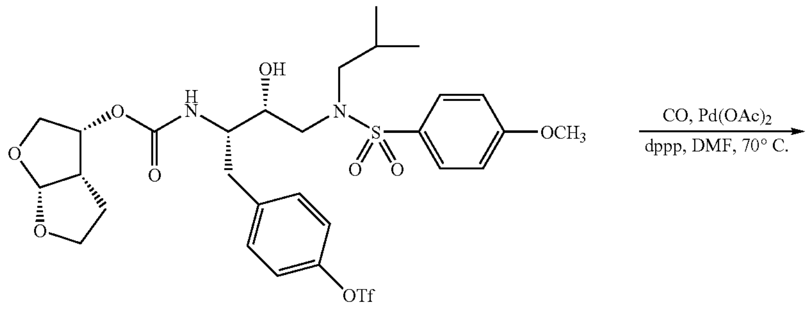

1

-continued

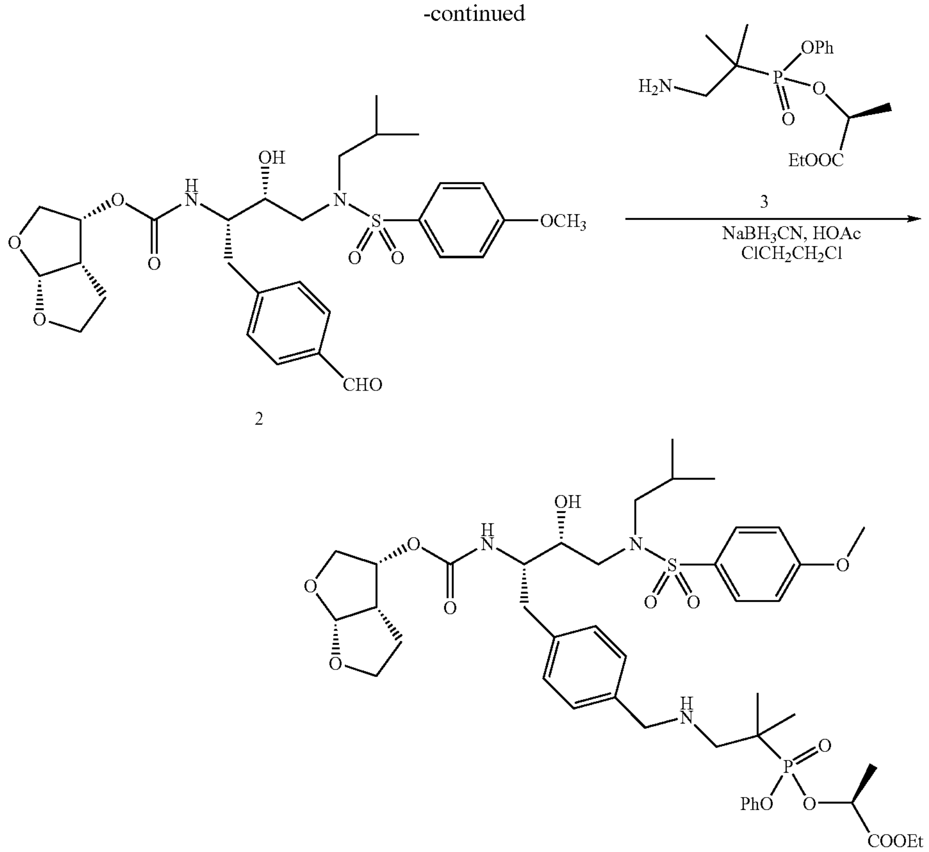

2 3 4

Example 30

Preparation of compound 3 Diethyl(cyano(dimethyl)methyl)phosphonate 5: A THF solution (30 mL) of NaH (3.4 g of 60% oil dispersion, 85 mmole) was cooled to −10° C., followed by the addition of diethyl(cyanomethyl)phosphonate (5 g, 28.2 mmol) and iodomethane (17 g, 112 mmol). The resulting solution was stirred at −10° C. for 2 hr, then 0° C. for 1 hr, was worked up, and purified to give dimethyl derivative 5 (5 g, 86%). Dietyl(2-amino-1,1-diemthyl-ethyl)phosphonate 6: Compound 5 was reduced to amine derivative 6 by the described procedure (J. Med. Chem. 1999, 42, 5010-5019). A ethanol (150 mL) and 1N HCl aqueous solution (22 mL) of 5 (2.2 g, 10.7 mmol) was hydrogenated at 1 atmosphere in the presence of $PtO_2$ (1.25 g) at room temperature overnight. The catalyst was filtered through a celite pad. The filtrate was concentrated to dryness, to give crude 6 (2.5 g, as HCl salt).

2-Amino-1,1-dimethyl-ethyl phosphonic acid 7: A $CH_3CN$ (30 mL) of crude 6 (2.5 g) was cooled to 0° C., and treated with TMSBr (8 g, 52 mmol) for 5 hr. The reaction mixture was stirred with methanol for 1.5 hr at room temperature, concentrated, recharged with methanol, concentrated to dryness to give crude 7 which was used for next reaction without further purification.

Lactate phenyl(2-amino-1,1-diemthyl-ethyl)phosphonate 3: Compound 3 is synthesized according to the procedures described in a previous scheme for the preparation of a lactate phenyl 2-aminoethyl phosponate. Compound 7 is protected with CBZ, followed by the reaction with thionyl chloride at 70° C. The CBZ protected dichlorodate is reacted phenol in the presence of DIPEA. Removal of one phenol, follow by coupling with ethyl L-lactate leads N-CBZ-2-amino-1,1-dimethyl-ethyl phosphonated derivative. Hydrogenation of N-CBZ derivative at 1 atmosphere in the presence of 10% Pd/C and 1 equivalent of TFA affords compound 3 as TFA salt.

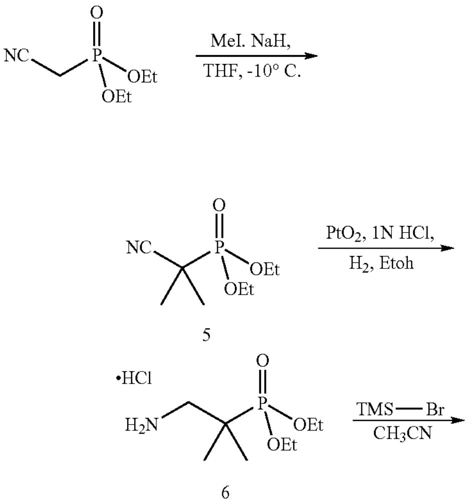

5 6

-continued
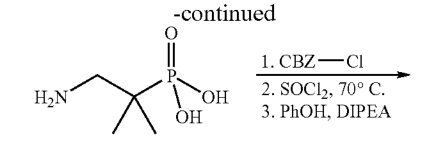
7
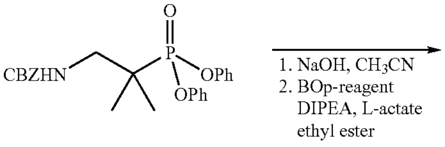
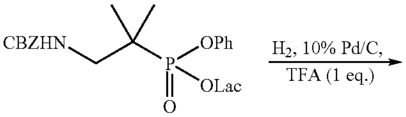
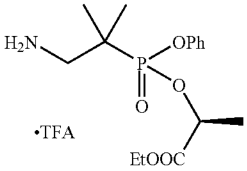
3
Example Section M
Scheme 1
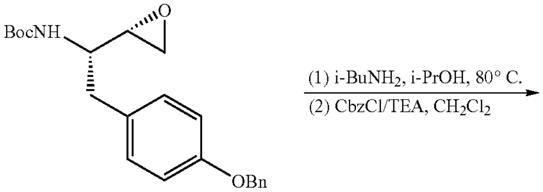
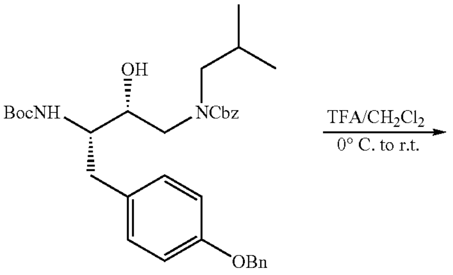
1
-continued
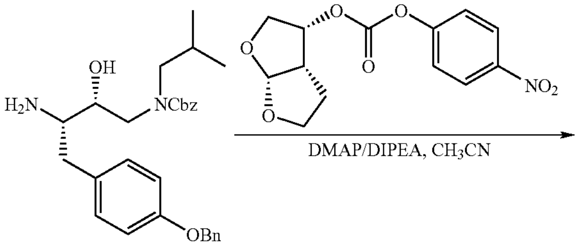
2
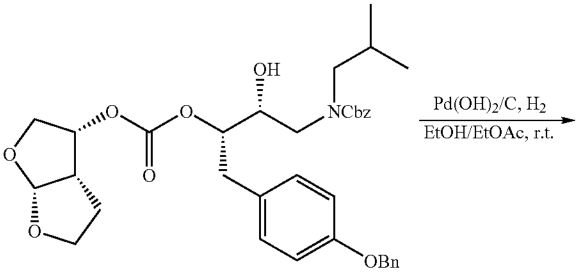
3
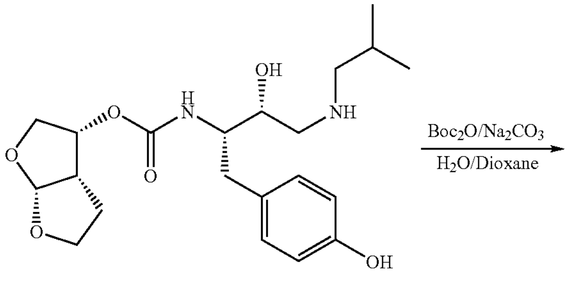
4
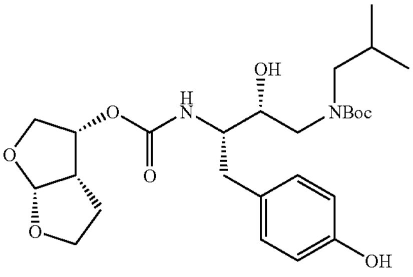
5

Scheme 2
5
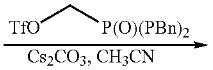
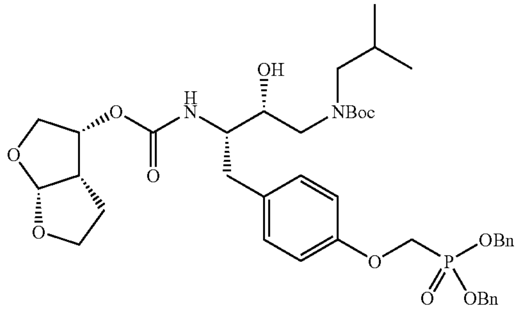
6
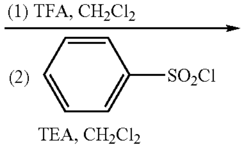
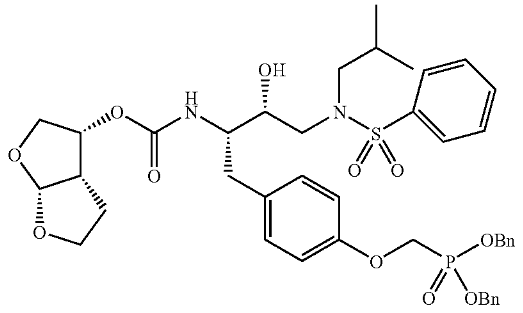
7
GS 191477
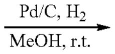
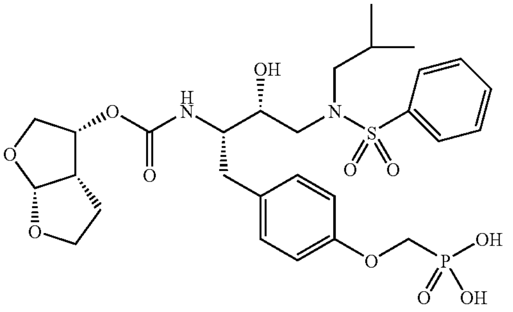
8
GS 191478
6
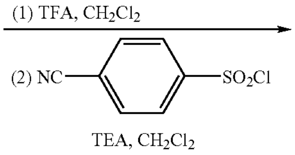
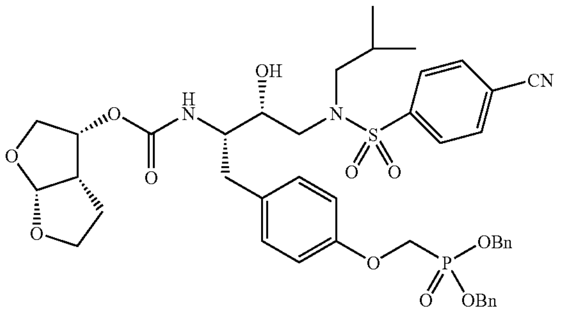
9
GS 191717

Scheme 3
6
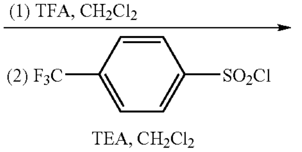
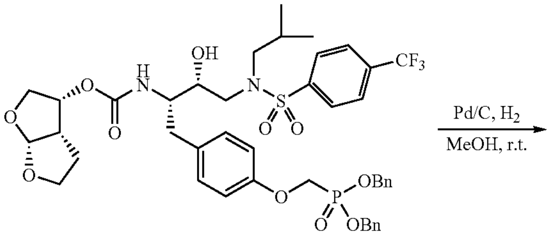
10
GS 191479
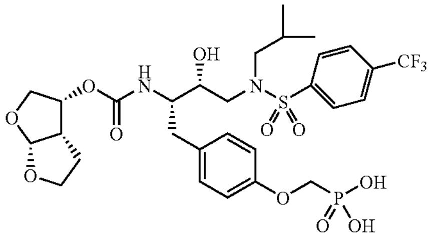
11
GS 191480
6
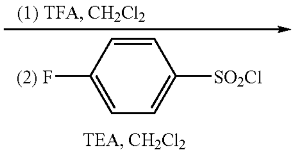
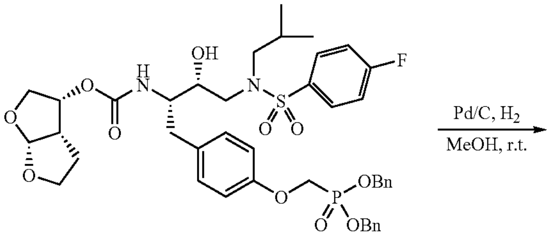
12
GS 191482
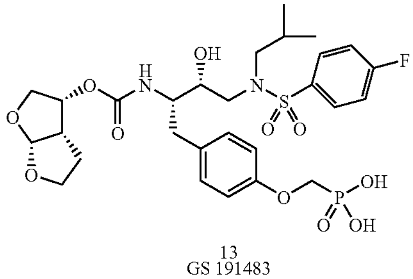
13
GS 191483
Scheme 4
6
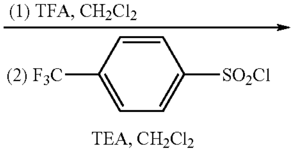
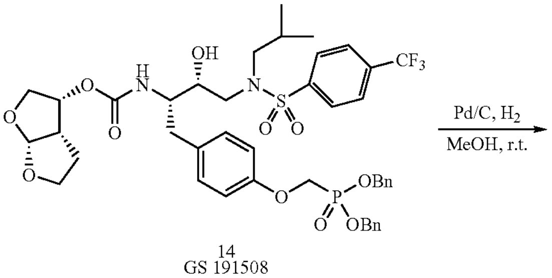
14
GS 191508
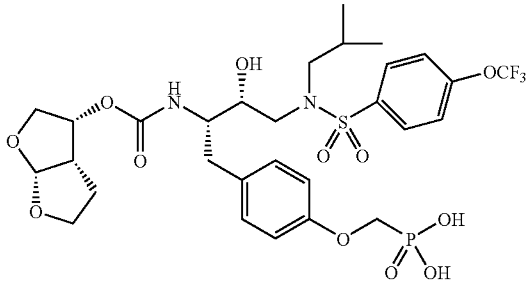
15
GS 192041
6
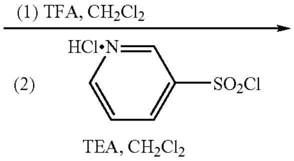
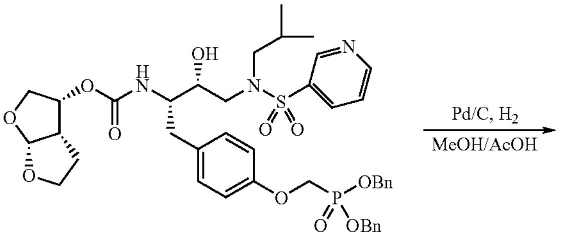
16
GS 273805
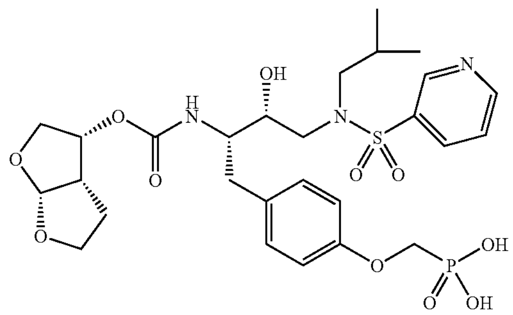
17
GS 273845

Scheme 5

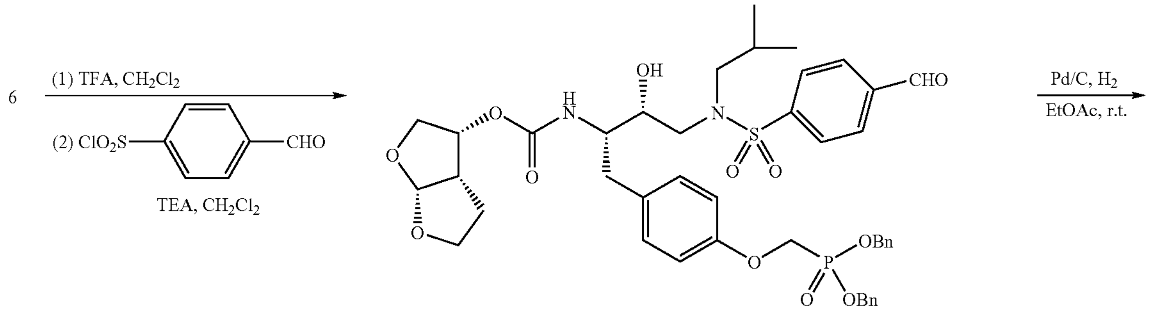

18
GS 278114

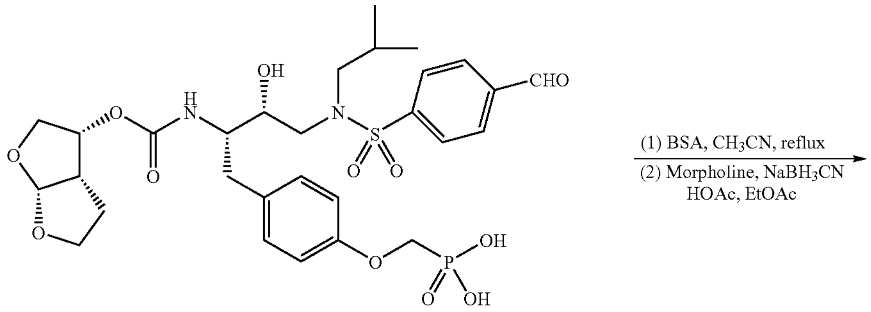

19

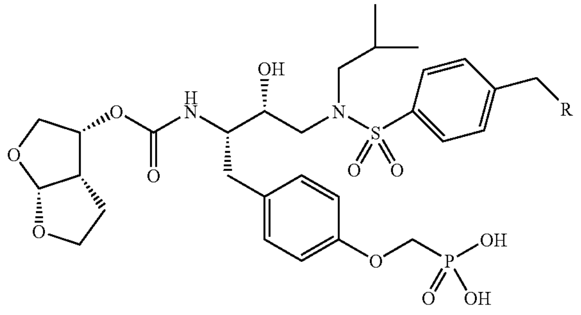

20 (GS 278118) R = OH 21 (GS 278117) R = 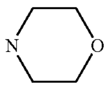

Example 1

Cbz Amide 1: To a suspension of epoxide (34 g, 92.03 mmol) in 2-propanol (300 mL) was added isobutylamine (91.5 mL, 920 mmol) and the solution was refluxed for 1 h. The solution was evaporated under reduced pressure and the crude solid was dried under vacuum to give the amine (38.7 g, 95%) which was dissolved in $CH_2Cl_2$ (300 mL) and cooled to 0° C. Triethylamine (18.3 mL, 131 mmol) was added followed by the addition of benzyl chloroformate (13.7 mL, 96.14 mmol) and the solution was stirred for 30 min at 0° C., warmed to room temperature overnight, and evaporated under reduced pressure. The residue was partitioned between EtOAc and 0.5 M $H_3PO_4$. The organic phase was washed with saturated $NaHCO_3$, brine, dried with $Na_2SO_4$, filtered, and evaporated under reduced pressure. The crude product was purified by column chromatography on silica gel (1/2-EtOAc/hexane) to give the Cbz amide (45.37 g, 90%) as a white solid.

Example 2

Amine 2: A solution of Cbz amide 1 (45.37 g, 78.67 mmol) in $CH_2Cl_2$ (160 mL) at 0° C. was treated with trifluoroacetic acid (80 mL). The solution was stirred for 30 min at 0° C. and then warmed to room temperature for an additional 30 min. Volatiles were evaporated under reduced pressure and the residue was partitioned between EtOAc and 0.5 N NaOH. The organic phase was washed with 0.5 N NaOH (2×), water (2×), saturated NaCl, dried with $Na_2SO_4$, filtered, and evaporated under reduced pressure to give the amine (35.62 g, 95%) as a white solid.

Example 3

Carbamate 3: To a solution of amine 2 (20.99 g, 44.03 mmol) in $CH_3CN$ (250 mL) at 0° C. was treated with (3R,3aR,6aS)-hexahydrofuro[2,3-b]furan-2-yl 4-nitrophenyl carbonate (13.00 g, 44.03 mmol, prepared according to Ghosh et al. J. Med. Chem. 1996, 39, 3278.), N,N-diisopropylethylamine (15.50 mL, 88.06 mmol) and 4-dimethylaminopyridine (1.08 g, 8.81 mmol). The reaction mixture was stirred at 0° C. for 30 min and then warmed to room temperature overnight. The reaction solvent was evaporated under reduced pressure and the residue was partitioned between EtOAc and 0.5 N NaOH. The organic phase was washed with 0.5 N NaOH (2×), 5% citric acid (2×), saturated $NaHCO_3$, dried with $Na_2SO_4$, filtered, and evaporated under reduced pressure. The crude product was purified by column chromatography on silica gel (3% 2-propanol/$CH_2Cl_2$) to give the carbamate (23.00 g, 83%) as a white solid.

Example 4

Amine 4: To a solution of 3 (23.00 g, 36.35 mmol) in EtOH (200 mL) and EtOAc (50 mL) was added 20% $Pd(OH)_2/C$ (2.30 g). The suspension was stirred under $H_2$ atmosphere (balloon) at room temperature for 3 h. The reaction mixture was filtered through a plug of celite. The filtrate was concentrated and dried under vacuum to give the amine (14.00 g, 94%) as a white solid.

Example 5

Phenol 5: To a solution of amine 4 (14.00 g, 34.27 mmol) in $H_2O$ (80 mL) and 1,4-dioxane (80 mL) at 0° C. was added $Na_2CO_3$ (5.09 g, 47.98 mmol) and di-tert-butyl dicarbonate (8.98 g, 41.13 mmol). The reaction mixture was stirred at 0° C. for 2 h and then warmed to room temperature for 30 min. The residue was partitioned between EtOAc and $H_2O$. The organic layer was dried with $Na_2SO_4$, filtered, and concentrated. The crude product was purified by column chromatography on silica gel (3% MeOH/$CH_2Cl_2$) to give the phenol (15.69 g, 90%) as a white solid.

Example 6

Dibenzylphosphonate 6: To a solution of phenol 5 (15.68 g, 30.83 mmol) in $CH_3CN$ (200 mL) was added $Cs_2CO_3$ (15.07 g, 46.24 mmol) and triflate (17.00 g, 40.08 mmol). The reaction mixture was stirred at room temperature for 1 h, the salt was filtered off, and the solvent was evaporated under reduced pressure. The residue was partitioned between EtOAc and saturated NaCl. The organic phase was dried with $Na_2SO_4$, filtered, and evaporated under reduced pressure. The crude product was purified by column chromatography on silica gel (3% 2-propanol/$CH_2Cl_2$) to give the dibenzylphosphonate (15.37 g, 73%) as a white solid.

Example 7

Sulfonamide 7: A solution of dibenzylphosphonate 6 (0.21 g, 0.26 mmol) in $CH_2Cl_2$ (0.5 mL) at 0° C. was treated with trifluoroacetic acid (0.25 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.15 mL, 1.04 mmol) was added followed by the treatment of benzenesulfonyl chloride (47 mg, 0.26 mmol). The solution was stirred for 1 h at 0° C. and the product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the sulfonamide 7 (0.12 g, 55%, GS 191477) as a white solid: $^1$HNMR ($CDCl_3$) δ 7.79 (dd, 2H), 7.61-7.56 (m, 3H), 7.38-7.36 (m, 10H), 7.13 (d, J=8.4 Hz, 2H), 6.81 (d, J=8.4 Hz, 2H), 5.65 (d, J=5.4 Hz, 1H), 5.18 (m, 4H), 5.05 (m, 1H), 4.93 (d, J=8.7 Hz, 1H), 4.20 (d, J=10.2 Hz, 2H), 4.0-3.67 (m, 7H), 3.15-2.8 (m, 7H), 1.84 (m, 1H), 1.65-1.59 (m, 2H), 0.93 (d, J=6.6 Hz, 3H), 0.88 (d, J=6.3 Hz, 3H); $^{31}$P NMR ($CDCl_3$) δ 20.36.

Example 8

Phosphonic Acid 8: To a solution of 7 (70 mg, 0.09 mmol) in MeOH (4 mL) was added 10% Pd/C (20 mg). The suspension was stirred under $H_2$ atmosphere (balloon) at room temperature overnight. The reaction mixture was filtered through a plug of celite. The filtrate was concentrated and dried under vacuum to give the phosphonic acid (49 mg, 90% GS 191478) as a white solid: $^1$HNMR ($CD_3OD$) δ 7.83 (dd, 2H), 7.65-7.56 (m, 3H), 7.18 (d, J=8.4 Hz, 2H), 6.91 (d, J=7.8 Hz, 2H), 5.59 (d, J=5.4 Hz, 1H), 4.96 (m, 1H), 4.15 (d, J=9.9 Hz, 2H), 3.95-3.68 (m, 6H), 3.44 (dd, 2H), 3.16 (m, 2H), 2.99-2.84 (m, 4H), 2.48 (m, 1H), 2.02 (m, 1H), 1.6 (m, 1H), 1.37 (m, 1H), 0.93 (d, J=6.3 Hz, 3H), 0.87 (d, J=6.3 Hz, 3H); $^{31}$P NMR ($CD_3OD$) δ 17.45.

Example 9

Sulfonamide 9: A solution of dibenzylphosphonate 6 (0.24 g, 0.31 mmol) in $CH_2Cl_2$ (0.5 mL) at 0° C. was treated with trifluoroacetic acid (0.25 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.17 mL, 1.20 mmol) was added followed by the treatment of 4-cyanobenzenesulfonyl chloride (61.4 mg, 0.30 mmol). The solution was stirred for 1 h at 0° C. and the product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the sulfonamide 9 (0.20 g, 77%, GS 191717) as a white solid: $^1$H NMR ($CDCl_3$) δ 7.90 (d, J=8.4 Hz, 2H), 7.83 (d, J=7.8 Hz, 2H), 7.36 (m, 10H), 7.11 (d, J=8.4 Hz, 2H), 6.82 (d, J=8.7 Hz, 2H), 5.65 (d, J=5.4 Hz, 1H), 5.2-4.9 (m, 5H), 4.8 (d, 1H), 4.2 (d, J=9.9 Hz, 2H), 3.99 (m 1H), 3.94 (m, 3H), 3.7 (m, 2H), 3.48 (broad, s, 1H), 3.18-2.78 (m, 7H), 1.87 (m, 1H), 1.66-1.47 (m, 2H), 0.91 (d, J=6.3 Hz, 3H), 0.87 (d, J=6.3 Hz, 3H); $^{31}$P NMR ($CDCl_3$) δ 20.3.

Example 10

Sulfonamide 10: A solution of dibenzylphosphonate 6 (0.23 g, 0.29 mmol) in $CH_2Cl_2$ (0.5 mL) at 0° C. was treated with trifluoroacetic acid (0.25 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.16 mL, 1.17 mmol) was added followed by the treatment of 4-trifluoromethyl benzenesulfonyl chloride (72 mg, 0.29 mmol). The solution was stirred for 1 h at 0° C. and the product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the sulfonamide (0.13 g, 50%, GS 191479) as a white solid: $^1$H NMR ($CDCl_3$) δ 7.92 (d, J=8.1 Hz, 2H), 7.81 (d, J=8.1 Hz, 2H), 7.36 (m, 10H), 7.12 (d, J=8.4 Hz, 2H), 6.81 (d, J=8.4 Hz, 2H), 5.65 (d, J=5.1 Hz, 1H), 5.20-4.89 (m, 6H), 4.20 (d, J=9.9 Hz, 2H), 3.95 (m, 1H), 3.86 (m, 3H), 3.71 (m, 2H), 3.19-2.78 (m, 7H), 1.86 (m, 1H), 1.65 (m, 2H), 0.93 (d, J=6.3 Hz, 3H), 0.88 (d, J=6.3 Hz, 3H); $^{31}$P NMR ($CDCl_3$) δ 20.3.

Example 11

Phosphonic Acid 11: To a solution of 10 (70 mg, 0.079 mmol) in MeOH (4 mL) was added 10% Pd/C (20 mg). The suspension was stirred under $H_2$ atmosphere (balloon) at room temperature overnight. The reaction mixture was filtered through a plug of celite. The filtrate was concentrated and dried under vacuum to give the phosphonic acid (50 mg, 90%, GS 191480) as a white solid: $^1$H NMR ($CD_3OD$) δ 8.03 (dd, 2H), 7.90 (dd, 2H), 7.17 (d, J=8.1 Hz, 2H), 6.91 (d, J=7.8 Hz, 2H), 5.59 (d, J=5.7 Hz, 1H), 4.94 (m, 1H), 4.15 (d, J=10.2 Hz, 2H), 3.94-3.72 (m, 6H), 3.48 (m, 1H), 3.2-3.1 (m, 3H), 3.0-2.9 (m, 2H), 2.47 (m, 1H), 2.06 (m, 1H), 1.56 (m, 1H), 1.37 (m, 1H), 0.93 (d, J=6.3 Hz, 3H), 0.88 (d, J=6.3 Hz, 3H); $^{31}$P NMR ($CD_3OD$) δ 17.5.

Example 12

Sulfonamide 12: A solution of dibenzylphosphonate 6 (0.23 g, 0.29 mmol) in $CH_2Cl_2$ (0.5 mL) at 0° C. was treated with trifluoroacetic acid (0.25 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.16 mL, 1.17 mmol) was added followed by the treatment of 4-fluorobenzenesulfonyl chloride (57 mg, 0.29 mmol). The solution was stirred for 1 h at 0° C. and the product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the sulfonamide (0.13 g, 55%, GS 191482) as a white solid: $^1$H NMR ($CDCl_3$) δ 7.81 (m, 2H), 7.38 (m, 10H), 7.24 (m, 2H), 7.12 (d, J=8.1 Hz, 2H), 6.82 (d, J=8.4 Hz, 2H), 5.65 (d, J=5.4 Hz, 1H), 5.17 (m, 4H), 5.0 (m, 1H), 4.90 (d, 1H), 4.20 (d, J=9.9 Hz, 2H), 3.97 (m, 1H), 3.86 (m, 3H), 3.73 (m, 2H), 3.6 (broad, s, 1H), 3.13 (m, 1H), 3.03-2.79 (m, 6H), 1.86 (m, 1H), 1.66-1.58 (m, 2H), 0.92 (d, J=6.6 Hz, 3H), 0.88 (d, J=6.6 Hz, 3H); $^{31}$P NMR ($CDCl_3$) δ 20.3.

Example 13

Phosphonic Acid 13: To a solution of 12 (70 mg, 0.083 mmol) in MeOH (4 mL) was added 10% Pd/C (20 mg). The suspension was stirred under $H_2$ atmosphere (balloon) at room temperature overnight. The reaction mixture was filtered through a plug of celite. The filtrate was concentrated and dried under vacuum to give the phosphonic acid (49 mg, 90%, GS 191483) as a white solid: $^1$H NMR ($CD_3OD$) δ 7.89 (m, 2H), 7.32 (m, 2H), 7.18 (d, J=8.4 Hz, 2H), 6.9 (d, J=8.1 Hz, 2H), 5.59 (d, J=5.1 Hz, 1H), 4.94 (m, 1H), 4.16 (d, J=9.9 Hz, 2H), 3.94 (m, 1H), 3.85-3.7 (m, 5H), 3.43 (dd, 1H), 3.15-2.87 (m, 5H), 2.48 (m, 1H), 2.03 (m, 1H), 1.59-1.36 (m, 2H), 0.93 (d, J=6.3 Hz, 3H), 0.87 (d, J=6.3 Hz, 3H); $^{31}$P NMR ($CD_3OD$) δ 17.5.

Example 14

Sulfonamide 14: A solution of dibenzylphosphonate 6 (0.21 g, 0.26 mmol) in $CH_2Cl_2$ (0.5 mL) at 0° C. was treated with trifluoroacetic acid (0.25 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.15 mL, 1.04 mmol) was added followed by the treatment of 4-trifluoromethoxybenzenesulfonyl chloride (69 mg, 0.26 mmol). The solution was stirred for 1 h at 0° C. and the product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the sulfonamide (0.17 g, 70%, GS 191508) as a white solid: $^1$H NMR ($CDCl_3$) δ 7.84 (d, J=9 Hz, 2H), 7.36 (m, 12H), 7.12 (d, J=8.7 Hz, 2H), 6.81 (d, J=8.7 Hz, 2H), 5.65 (d, J=5.4 Hz, 1H), 5.16 (m, 4H), 5.03 (m, 1H), 4.89 (d, 1H), 4.2 (d, J=9.9 Hz, 2H), 3.97 (m, 1H), 3.85 (m, 3H), 3.7 (m, 2H), 3.59 (broad, s, 1H), 3.18 (m, 1H), 3.1-3.0 (m, 3H), 2.96-2.78 (m, 3H), 1.86 (m, 1H), 1.66-1.5 (m, 2H), 0.93 (d, J=6.6 Hz, 3H), 0.88 (d, J=6.6 Hz, 3H); $^-$P NMR ($CDCl_3$) δ 20.3.

Example 15

Phosphonic Acid 15: To a solution of 14 (70 mg, 0.083 mmol) in MeOH (4 mL) was added 10% Pd/C (20 mg). The suspension was stirred under $H_2$ atmosphere (balloon) at room temperature overnight. The reaction mixture was filtered through a plug of celite. The filtrate was concentrated and dried under vacuum to give the phosphonic acid (50 mg, 90%, GS 192041) as a white solid: $^1$H NMR ($CD_3OD$) δ 7.95 (dd, 2H), 7.49 (dd, 2H), 7.17 (dd, 2H), 6.92 (dd, 2H), 5.58 (d, J=5.4 Hz, 1H), 4.89 (m, 1H), 4.17 (d, J=9 Hz, 2H), 3.9 (m, 1H), 3.82-3.7 (m, 5H), 3.44 (m, 1H), 3.19-2.9 (m, 5H), 2.48 (m, 1H), 2.0 (m, 1H), 1.6 (m, 1H), 1.35 (m, 1H), 0.93 (d, J=6.0 Hz, 3H), 0.88 (d, J=6.0 Hz, 3H); $^{31}$P NMR ($CD_3OD$) δ 17.4.

Example 16

Sulfonamide 16: A solution of dibenzylphosphonate 6 (0.59 g, 0.76 mmol) in $CH_2Cl_2$ (2.0 mL) at 0° C. was treated with trifluoroacetic acid (1.0 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.53 mL, 3.80 mmol) was added followed by the treatment of hydrogen chloride salt of 3-pyridinylsulfonyl chloride (0.17 g, 0.80 mmol, prepared according to Karaman, R. et al. J. Am. Chem. Soc. 1992, 114, 4889). The solution was stirred for 30 min at 0° C. and warmed to room temperature for 30 min. The product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (4% 2-propanol/$CH_2Cl_2$) to give the sulfonamide (0.50 g, 80%, GS 273805) as a white solid: $^1$H NMR ($CDCl_3$) δ 9.0 (d, J=1.5 Hz, 1H), 8.8 (dd, 1H), 8.05 (d, J=8.7 Hz, 1H), 7.48 (m, 1H), 7.36 (m, 10H), 7.12 (d, J=8.4 Hz, 2H), 6.82 (d, J=9.0 Hz, 2H), 5.65 (d, J=5.1 Hz, 1H), 5.18 (m, 4H), 5.06 (m, 1H), 4.93 (d, 1H), 4.21 (d, J=8.4 Hz, 2H), 3.97 (m, 1H), 3.86 (m, 3H), 3.74 (m, 2H), 3.2 (m, 1H), 3.1-2.83 (m, 5H), 2.76 (m, 1H), 1.88 (m, 1H), 1.62 (m, 2H), 0.92 (d, J=6.3 Hz, 3H), 0.88 (d, J=6.3 Hz, 3H); $^{31}$P NMR ($CDCl_3$) δ 20.3.

Example 17

Phosphonic Acid 17: To a solution of 16 (40 mg, 0.049 mmol) in MeOH (3 mL) and AcOH (1 mL) was added 10% Pd/C (10 mg). The suspension was stirred under $H_2$ atmosphere (balloon) at room temperature overnight. The reaction mixture was filtered through a plug of celite. The filtrate was concentrated and dried under vacuum to give the phosphonic acid (28 mg, 90%, GS 273845) as a white solid: $^1$H NMR ($CD_3OD$) δ 8.98 (s, 1H), 8.77 (broad, s, 1H), 8.25 (dd, 1H), 7.6 (m, 1H), 7.15 (m, 2H), 6.90 (m, 2H), 5.6 (d, J=5.4 Hz, 1H), 4.98 (m, 1H), 4.15 (d, 2H), 3.97-3.7 (m, 6H), 3.45-2.89 (m, 6H), 2.50 (m, 1H), 2.0 (m, 1H), 1.6-1.35 (m, 2H), 0.9 (m, 6H).

Example 18

Sulfonamide 18: A solution of dibenzylphosphonate 6 (0.15 g, 0.19 mmol) in $CH_2Cl_2$ (0.60 mL) at 0° C. was treated with trifluoroacetic acid (0.30 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (2 mL) and cooled to 0° C. Triethylamine (0.11 mL, 0.76 mmol) was added followed by the treatment of 4-formylbenzenesulfonyl chloride (43 mg, 0.21 mmol). The solution was stirred for 30 min at 0° C. and warmed to room temperature for 30 min. The product was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (3% 2-propanoyl/$CH_2Cl_2$) to give the sulfonamide (0.13 g, 80%, GS 278114) as a white solid: $^1$H NMR ($CDCl_3$) δ 10.1 (s, 1H), 8.04 (d, J=8.1 Hz, 2H), 7.94 (d, J=8.1 Hz, 2H), 7.35 (m, 10H), 7.13 (m, J=8.1 Hz, 2H), 6.82 (d, J=8.1 Hz, 2H), 5.65 (d, J=5.4 Hz, 1H), 5.17 (m, 4H), 5.06 (m, 1H), 4.93 (m, 1H), 4.2 (d, J=9.9 Hz, 2H), 3.94 (m, 1H), 3.85 (m, 3H), 3.7 (m, 2H), 3.18-2.87 (m, 5H), 2.78 (m, 1H), 1.86 (m, 1H), 1.67-1.58 (m, 2H), 0.93 (d, J=6.6 Hz, 3H), 0.88 (d, J=6.6 Hz, 3H); $^{31}$P NMR ($CDCl_3$) δ 20.3.

Example 19

Phosphonic Acid 19: To a solution of 18 (0.12 g, 0.15 mmol) in EtOAc (4 mL) was added 10% Pd/C (20 mg). The suspension was stirred under $H_2$ atmosphere (balloon) at room temperature for 6 h. The reaction mixture was filtered through a plug of celite. The filtrate was concentrated and dried under vacuum to give the phosphonic acid (93 mg, 95%) as a white solid.

Example 20

Phosphonic Acids 20 and 21: Compound 19 (93 mg, 0.14 mmol) was dissolved in $CH_3CN$ (2 mL). N. O-Bis(trimethylsilyl)acetamide (BSA, 0.28 g, 1.4 mmol) was added. The reaction mixture was heated to reflux for 1 h, cooled to room temperature and concentrated. The residue was co-evaporated with toluene and chloroform and dried under vacuum to give a semi-solid which was dissolved in EtOAc (2 mL). Morpholine (60 μL, 0.9 mmol), AcOH (32 μL, 0.56 mmol), and $NaBH_3CN$ (17 mg, 0.28 mmol) were added and the reaction mixture was stirred at room temperature overnight. The reaction was quenched with $H_2O$, stirred for 2 h, filtered, and concentrated. The crude product was purified by HPLC to give the phosphonic acid 20 (10 mg, GS 278118) as a white solid: $^1$H NMR ($CD_3OD$) δ 7.80 (d, J=7.8 Hz, 2H), 7.56 (d, J=7.5 Hz, 2H), 7.17 (d, J=7.8 Hz, 2H), 6.91 (d, J=7.5 Hz, 2H), 5.59 (d, J=5.1 Hz, 1H), 5.06 (m, 1H), 4.7 (s, 2H), 4.15 (d, J=10.2 Hz, 2H), 3.92 (m, 1H), 3.82-3.7 (m, 5H), 3.43 (dd, 1H), 3.11-2.89 (m, 6H), 2.50 (m, 1H), 2.0 (m, 1H), 1.6-1.35 (m, 2H), 0.93 (d, J=6.3 Hz, 3H), 0.88 (d, J=6.3 Hz, 3H); $^{31}$P NMR ($CD_3OD$) δ 17.3. Phosphonic acid 21 (15 mg, GS 278117) as a white solid: $^1$H NMR ($CD_3OD$) δ 7.8-7.7 (m, 4H), 7.20 (d, J=8.4 Hz, 2H), 6.95 (d, J=8.4 Hz, 2H), 5.62 (d, J=5.1 Hz, 1H), 5.00 (m, 1H), 4.42 (s, 2H), 4.20 (dd, 2H), 3.98-3.68 (in 9H), 3.3-2.92 (m, 1H), 2.6 (m, 1H), 2.0 (m, 1H), 1.6 (m, 2H), 0.92 (d, J=6.6 Hz, 3H), 0.88 (d, J=6.6 Hz, 3H); $^{31}$P NMR ($CD_3OD$) δ 16.2.

Scheme 6

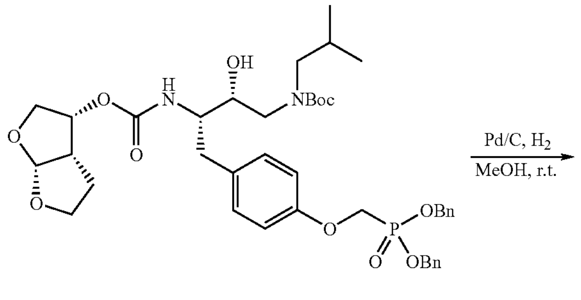

6

-continued
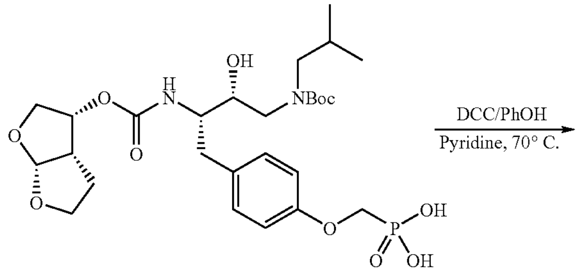
22
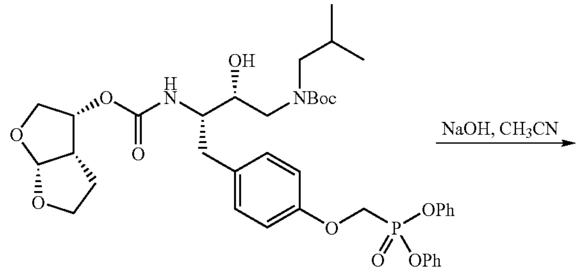
23
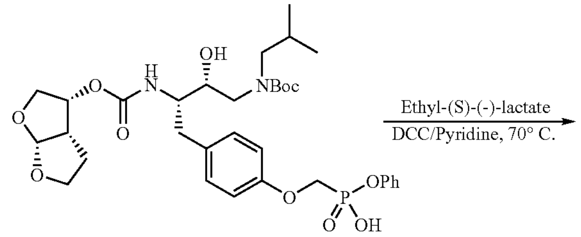
24
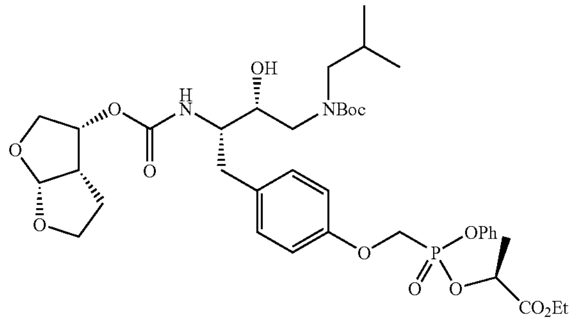
25
Scheme 7
25 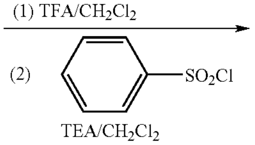
-continued
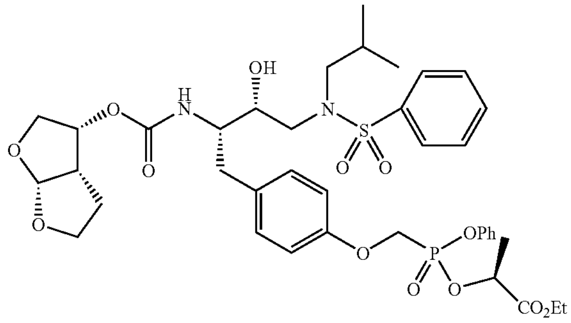
26
GS 192779
25 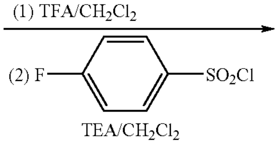
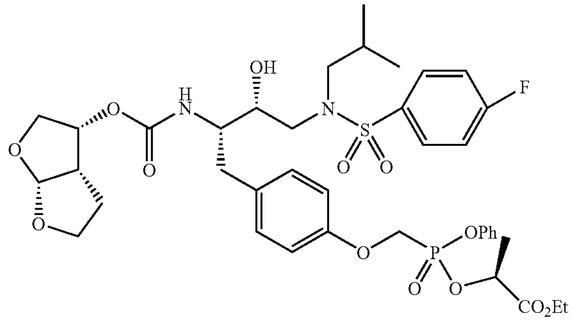
27
GS 192776
25 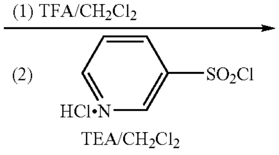
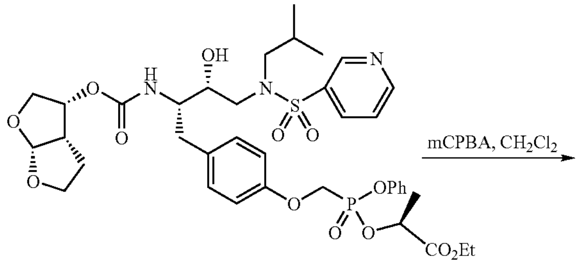
28
GS 273806

-continued
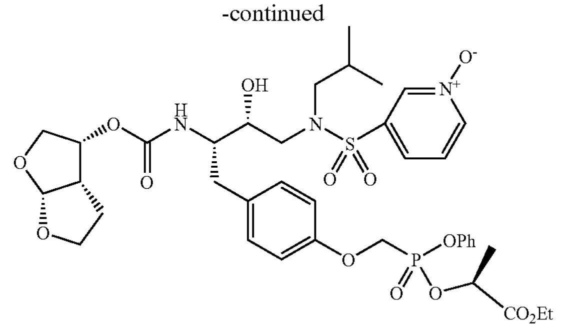
29
GS 273851
Scheme 8
28
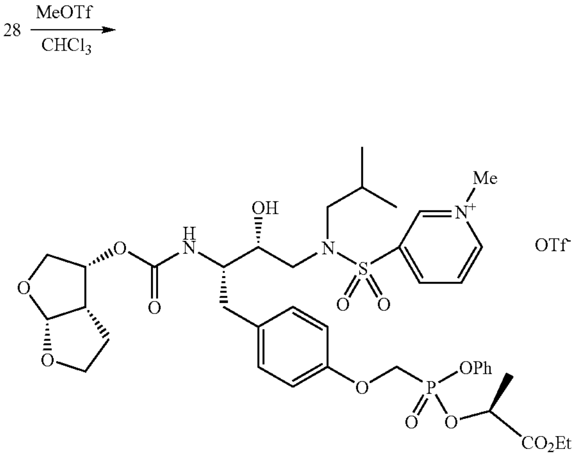
30
GS 273813
16
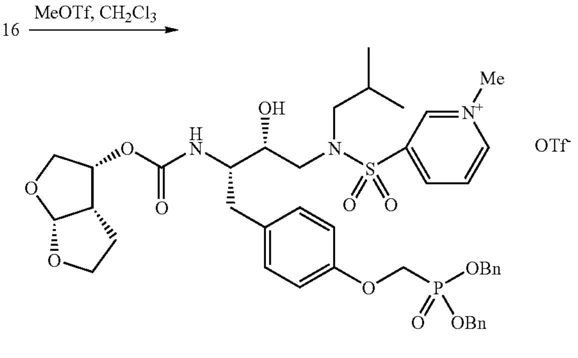
31
GS 273812
-continued
16
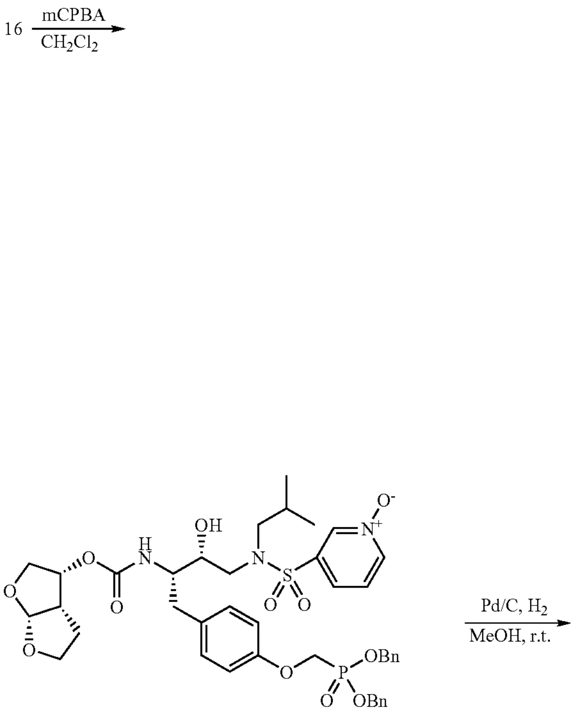
32
GS 277774
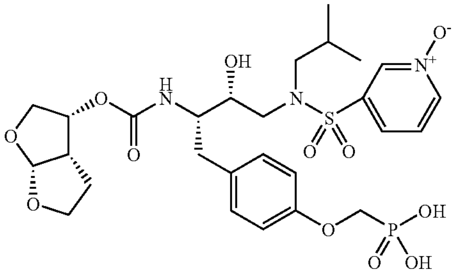
33
GS 277775

Scheme 9
25
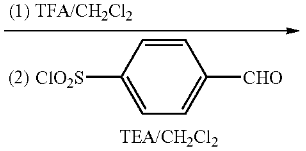
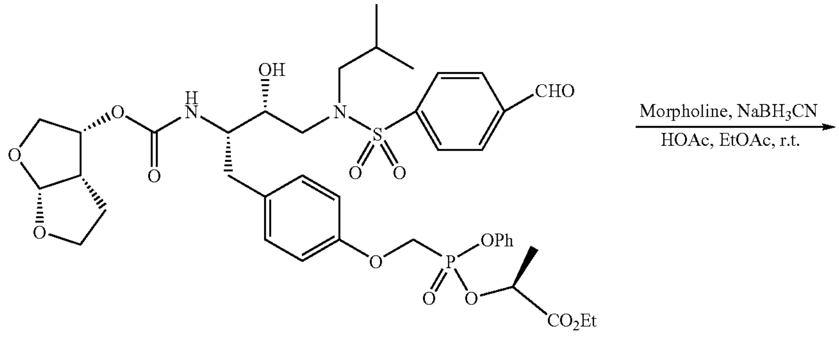
34
GS 278052
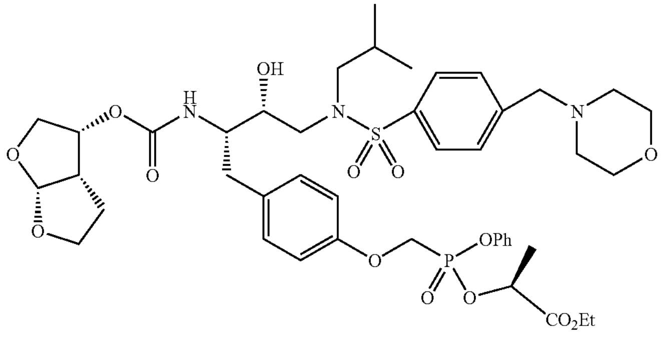
35
GS 278115
25
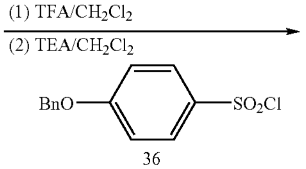
36
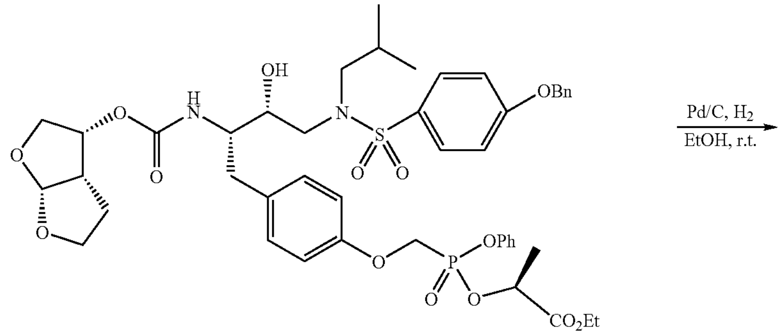
37

-continued
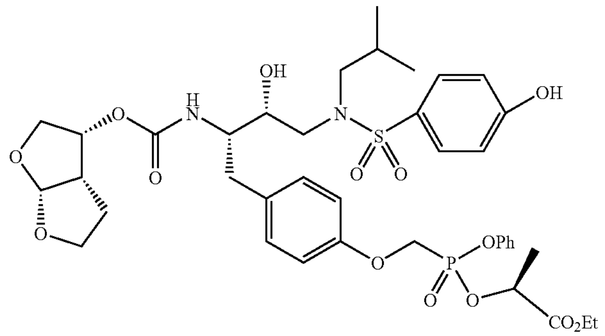
38
GS 273838
Scheme 10
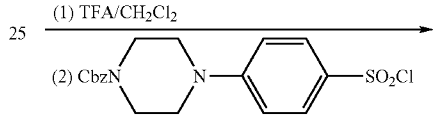
39
TEA/$CH_2Cl_2$
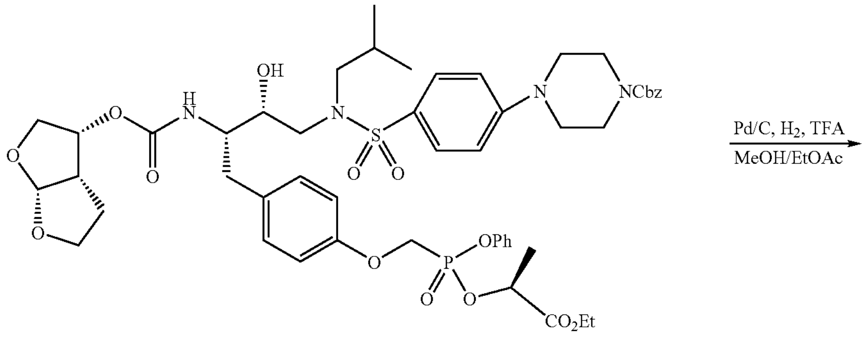
40
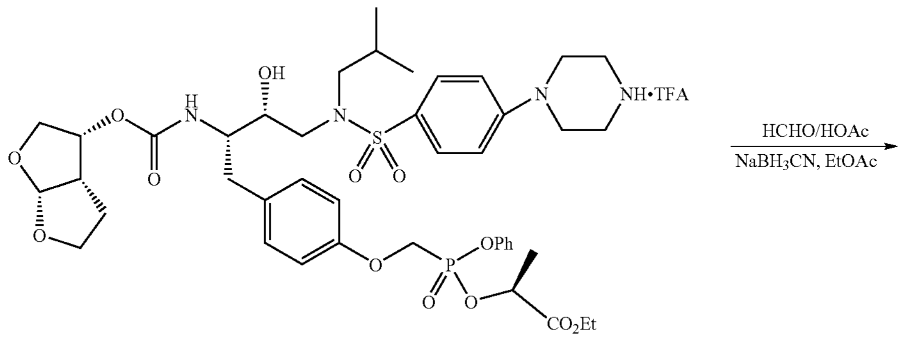
41

-continued
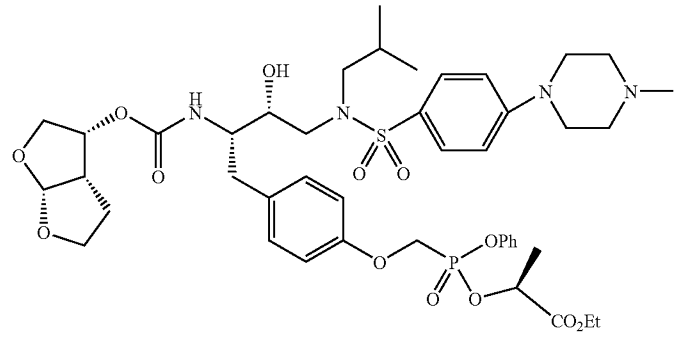
42
GS 277937
Scheme 11
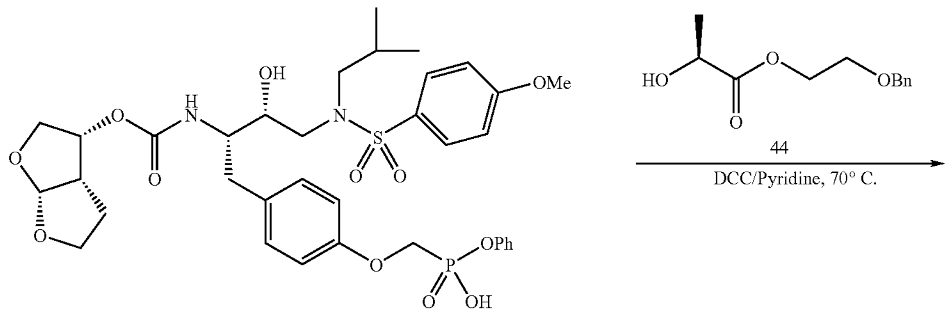
43
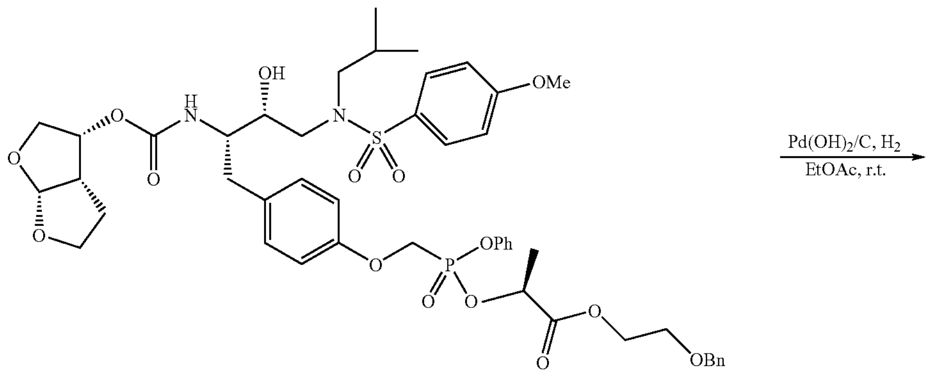
45

-continued

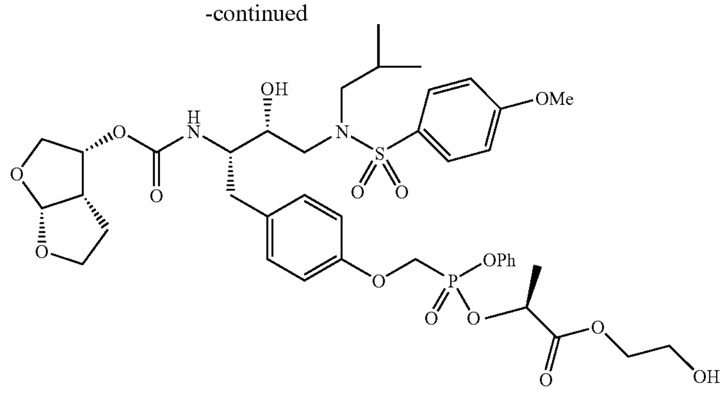

46
GS 278809

Example 21

Phosphonic Acid 22: To a solution of dibenzylphosphonate 6 (5.00 g, 6.39 mmol) in EtOH (100 mL) was added 10% Pd/C (1.4 g). The suspension was stirred under $H_2$ atmosphere (balloon) at room temperature overnight. The reaction mixture was filtered through a plug of celite. The filtrate was concentrated and dried under vacuum to give the phosphonic acid (3.66 g, 95%) as a white solid.

Example 22

Diphenylphosphonate 23: A solution of 22 (3.65 g, 6.06 mmol) and phenol (5.70 g, 60.6 mmol) in pyridine (30 mL) was heated to 70° C. and 1,3-dicyclohexylcarbodiimide (5.00 g, 24.24 mmol) was added. The reaction mixture was stirred at 70° C. for 2 h and cooled to room temperature. EtOAc was added and the side product 1,3-dicyclohexyl urea was filtered off. The filtrate was concentrated and dissolved in $CH_3CN$ (20 mL) at 0° C. The mixture was treated with DOWEX 50W×8-400 ion-exchange resin and stirred for 30 min at 0° C. The resin was filtered off and the filtrate was concentrated. The crude product was purified by column chromatography on silica gel (3% 2-propanol/$CH_2Cl_2$) to give the diphenylphosphonate (2.74 g, 60%) as a white solid.

Example 23

Monophosphonic Acid 24: To a solution of 23 (2.74 g, 3.63 mmol) in $CH_3CN$ (40 mL) at 0° C. was added 1 N NaOH (9.07 mL, 9.07 mmol). The reaction mixture was stirred at 0° C. for 1 h. DOWEX 50W×8-400 ion-exchange resin was added and the reaction mixture was stirred for 30 min at 0° C. The resin was filtered off and the filtrate was concentrated and co-evaporated with toluene. The crude product was triturated with EtOAc/hexane (1/2) to give the monophosphonic acid (2.34 g, 95%) as a white solid.

Example 24

Monophospholactate 25: A solution of 24 (2.00 g, 2.95 mmol) and ethyl-(S)-(−)-lactate (1.34 mL, 11.80 mmol) in pyridine (20 mL) was heated to 70° C. and 1,3-dicyclohexylcarbodiimide (2.43 g, 11.80 mmol) was added. The reaction mixture was stirred at 70° C. for 2 h and cooled to room temperature. The solvent was removed under reduced pressure. The residue was suspended in EtOAc and 1,3-dicyclohexyl urea was filtered off. The product was partitioned between EtOAc and 0.2 N HCl. The EtOAc layer was washed with 0.2 N HCl, $H_2O$, saturated NaCl, dried with $Na_2SO_4$, filtered, and concentrated. The crude product was purified by column chromatography on silica gel (3% 2-propanol/$CH_2Cl_2$) to give the monophospholactate (1.38 g, 60%) as a white solid.

Example 25

Monophospholactate 26: A solution of 25 (0.37 g, 0.48 mmol) in $CH_2Cl_2$ (0.80 mL) at 0° C. was treated with trifluoroacetic acid (0.40 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.27 mL, 1.92 mmol) was added followed by the treatment of benzenesulfonyl chloride (84 mg, 0.48 mmol). The solution was stirred for 30 min at 0° C. and then warmed to room temperature for 30 min. The product was partitioned between $CH_2Cl_2$ and 0.2 N HCl. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the monophospholactate (0.33 g, 85%, GS 192779, 1:1 diastereomeric mixture) as a white solid: $^1H$ NMR ($CDCl_3$) δ 7.78 (dd, 2H), 7.59 (m, 3H), 7.38-7.18 (m, 7H), 6.93 (dd, 2H), 5.66 (m, 1H), 5.18-4.93 (m, 3H), 4.56-4.4 (m, 2H), 4.2 (m, 2H), 4.1-3.7 (m, 6H), 3.17 (m, 1H), 3.02-2.8 (m, 6H), 1.84 (m, 1H), 1.82-1.5 (m, 5H), 1.27 (m, 3H), 0.93 (d, J=6.3 Hz, 3H), 0.88 (d, J=6.3 Hz, 3H); $^{31}P$ NMR ($CDCl_3$) δ 17.4, 15.3.

Example 26

Monophospholactate 27: A solution of 25 (0.50 g, 0.64 mmol) in $CH_2Cl_2$ (1.0 mL) at 0° C. was treated with trifluoroacetic acid (0.5 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (4 mL) and cooled to 0° C. Triethylamine (0.36 mL, 2.56 mmol) was added followed by the treatment of 4-fluorobenzenesulfonyl chloride (0.13 g, 0.64 mmol). The solution was stirred for 30 min at 0° C. and then warmed to room temperature for 30 min. The product was partitioned between $CH_2Cl_2$ and 0.2 N HCl. The organic phase was washed with saturated NaCl, dried with $Na_2SO_4$, filtered, and evaporated under reduced pressure. The crude product was purified by column chromatography on silica gel (3% 2-propanol/$CH_2Cl_2$) to give the monophospholactate (0.44 g, 81%, GS 192776, 3/2 diastereomeric mixture) as a white solid: $^1$H NMR ($CDCl_3$) δ 7.80 (m, 2H), 7.38-7.15 (m, 9H), 6.92 (m, 2H), 5.66 (m, 1H), 5.2-4.9 (m, 3H), 4.57-4.4 (m, 2H), 4.2 (m, 2H), 4.1-3.7 (m, 6H), 3.6 (broad, s, 1H), 3.17 (m, 1H), 3.02-2.75 (m, 6H), 1.85 (m, 1H), 1.7-1.5 (m, 5H), 1.26 (m, 3H), 0.93 (d, J=6.3 Hz, 3H), 0.88 (d, J=6.3 Hz, 3H); $^{31}$P NMR ($CDCl_3$) δ 17.3, 15.2.

Example 27

Monophospholactate 28: A solution of 25 (0.50 g, 0.64 mmol) in $CH_2Cl_2$ (1.0 mL) at 0° C. was treated with trifluoroacetic acid (0.5 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.45 mL, 3.20 mmol) was added followed by the treatment of hydrogen chloride salt of 3-pyridinylsulfonyl chloride (0.14 g, 0.65 mmol). The solution was stirred for 30 min at 0° C. and then warmed to room temperature for 30 min. The product was partitioned between $CH_2Cl_2$ and $H_2O$. The organic phase was washed with saturated NaCl, dried with $Na_2SO_4$, filtered, and evaporated under reduced pressure. The crude product was purified by column chromatography on silica gel (4% 2-propanol/$CH_2Cl_2$) to give the monophospholactate (0.41 g, 79%, GS 273806, 1:1 diastereomeric mixture) as a white solid: $^1$H NMR ($CDCl_3$) δ 9.0 (s, 1H), 8.83 (dd, 1H), 8.06 (d, J=7.8 Hz, 1H), 7.5 (m, 1H), 7.38-7.15 (m, 7H), 6.92 (m, 2H), 5.66 (m, 1H), 5.18-4.95 (m, 3H), 4.6-4.41 (m, 2H), 4.2 (m, 2H), 4.0 (m, 1H), 3.95-3.76 (m, 6H), 3.23-2.8 (m, 7H), 1.88 (m, 1H), 1.7-1.5 (m, 5H), 1.26 (m, 3H), 0.93 (d, J=6.6 Hz, 3H), 0.83 (d, J=6.6 Hz, 3H); $^{31}$P NMR ($CDCl_3$) δ 17.3, 15.3.

Example 28

Monophospholactate 29: A solution of compound 28 (0.82 g, 1.00 mmol) in $CH_2Cl_2$ (8 mL) at 0° C. was treated with mCPBA (1.25 eq). The solution was stirred for 1 h at 0° C. and then warmed to room temperature for an additional 6 h. The reaction mixture was partitioned between $CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (10% 2-propanol/$CH_2Cl_2$) to give the monophospholactate (0.59 g, 70%, GS 273851, 1:1 diastereomeric mixture) as a white solid: $^1$H NMR ($CDCl_3$) δ 8.63 (dd, 1H), 8.3 (dd, 1H), 7.57 (m, 1H), 7.44 (m, 1H), 7.38-7.13 (m, 7H), 6.92 (m, 2H), 5.66 (m, 1H), 5.2-5.05 (m, 2H), 4.57-4.4 (m, 2H), 4.2 (m, 2H), 4.0-3.73 (m, 6H), 3.2 (m, 2H), 3.0 (m, 4H), 2.77 (m, 1H), 1.92 (m, 1H), 1.7-1.49 (m, 5H), 1.26 (m, 3H), 0.91 (m, 6H); $^{31}$P NMR ($CDCl_3$) δ 17.3, 15.3.

Example 29

Monophospholactate 30: A solution of compound 28 (71 mg, 0.087 mmol) in $CHCl_3$ (1 mL) was treated with MeOTf (18 mg, 0.11 mmol). The solution was stirred at room temperature for 1 h. The reaction mixture was concentrated and co-evaporated with toluene (2×), $CHCl_3$ (2×) and dried under vacuum to give the monophospholactate (81 mg, 95%, GS 273813, 1:1 diastereomeric mixture) as a white solid: $^1$H NMR ($CDCl_3$) δ 9.0 (dd, 1H), 8.76 (m, 2H), 8.1 (m, 1H), 7.35-7.1 (m, 7H), 6.89 (m, 2H), 5.64 (m, 1H), 5.25-5.0 (m, 3H), 4.6-4.41 (m, 5H), 4.2 (m, 2H), 3.92-3.72 (m, 6H), 3.28 (m, 2H), 3.04-2.85 (m, 3H), 2.62 (m, 1H), 1.97 (m, 1H), 1.62-1.5 (m, 5H), 1.25 (m, 3H), 0.97 (m, 6H); $^{31}$P NMR ($CDCl_3$) δ 17.4, 15.4.

Example 30

Dibenzylphosphonate 31: A solution of compound 16 (0.15 g, 0.18 mmol) in $CHCl_3$ (2 mL) was treated with MeOTf (37 mg, 0.23 mmol). The solution was stirred at room temperature for 2 h. The reaction mixture was concentrated and co-evaporated with toluene (2×), $CHCl_3$ (2×) and dried under vacuum to give the dibenzylphosphonate (0.17 g, 95%, GS 273812) as a white solid: $^1$H NMR ($CDCl_3$) δ 9.0 (dd, 1H), 8.73 (m, 2H), 8.09 (m, 1H), 7.35 (m, 10H), 7.09 (d, J=8.4 Hz, 2H), 6.79 (d, J=8.1 Hz, 2H), 5.61 (d, J=4.2 Hz, 1H), 5.2-4.96 (m, 6H), 4.54 (s, 3H), 4.2 (dd, 2H), 3.92-3.69 (m, 6H), 3.3 (m, 2H), 3.04-2.6 (m, 5H), 1.97 (m, 1H), 1.6 (m, 2H), 0.98 (m, 6H); $^{31}$P NMR ($CDCl_3$) δ 20.4.

Example 31

Dibenzylphosphonate 32: A solution of compound 16 (0.15 g, 0.18 mmol) in $CH_2Cl_2$ (3 mL) at 0° C. was treated with mCPBA (1.25 eq). The solution was stirred for 1 h at 0° C. and then warmed to room temperature overnight. The reaction mixture was partitioned between 10% 2-propanol/$CH_2Cl_2$ and saturated $NaHCO_3$. The organic phase was washed with saturated NaCl, dried with $Na_2SO_4$, filtered, and evaporated under reduced pressure. The crude product was purified by column chromatography on silica gel (10% 2-propanol/$CH_2Cl_2$) to give the dibenzylphosphonate (0.11 g, 70%, GS 277774) as a white solid: $^1$H NMR ($CDCl_3$) δ 8.64 (m, 1H), 8.27 (d, J=6.9 Hz, 1H), 7.57 (d, J=8.4 Hz, 1H), 7.36 (m, 111H), 7.10 (d, J=8.4 Hz, 2H), 6.81 (d, J=8.7 Hz, 2H), 5.65 (d, J=5.4 Hz, 1H), 5.22-5.02 (m, 6H), 4.21 (dd, 2H), 3.99-3.65 (m, 6H), 3.2 (m, 2H), 3.03-2.73 (m, 5H), 1.90 (m, 1H), 1.66-1.56 (m, 2H), 0.91 (m, 6H); $^{31}$P NMR ($CDCl_3$) δ 20.3.

Example 32

Phosphonic Acid 33: To a solution of dibenzylphosphonate 32 (0.1 g, 0.12 mmol) in MeOH (4 mL) was added 10% Pd/C (20 mg). The suspension was stirred under $H_2$ atmosphere (balloon) at room temperature for 1 h. The reaction mixture was filtered through a plug of celite. The filtrate was concentrated and purified by HPLC to give the phosphonic acid (17 mg, GS 277775) as a white solid: $^1$H NMR ($CD_3OD$) δ 8.68 (s, 1H), 8.47 (d, J=6.0 Hz, 1H), 7.92 (d, J=7.8 Hz, 1H), 7.68 (m, 1H), 7.14 (m, 2H), 6.90 (d, J=7.8 Hz, 2H), 5.58 (d, J=5.4 Hz, 1H), 5.00 (m, 1H), 4.08 (d, J=9.9 Hz, 2H), 3.93-3.69 (m, 6H), 3.4-2.9 (m, 7H), 2.5 (m, 1H), 2.04 (m, 1H), 1.6-1.35 (m, 2H), 0.92 (m, 6H); $^{31}$P NMR ($CD_3OD$) δ 15.8.

Example 33

Monophospholactate 34: A solution of 25 (2.50 g, 3.21 mmol) in $CH_2Cl_2$ (5.0 mL) at 0° C. was treated with trifluoroacetic acid (2.5 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (30 mL) and cooled to 0° C. Triethylamine (1.79 mL, 12.84 mmol) was added followed by the treatment of 4-formylbenzenesulfonyl chloride (0.72 g, 3.53 mmol) and the solution was stirred at 0° C. for 1 h. The product was partitioned between $CH_2Cl_2$ and 5% HCl. The organic phase was washed with $H_2O$, saturated NaCl, dried with $Na_2SO_4$, filtered, and evaporated under reduced pressure. The crude product was purified by column chromatography on silica gel (3% 2-propanol/$CH_2Cl_2$) to give the monophospholactate (2.11 g, 77%, GS 278052, 1:1 diastereomeric mixture) as a white solid: $^1$H NMR ($CDCl_3$) δ 10.12 (s, 1H), 8.05 (d, J=8.7 Hz, 2H), 7.95 (d, J=7.5 Hz, 2H), 7.38-7.15 (m, 7H), 6.94 (m, 2H), 5.67 (m, 1H), 5.18-4.91 (m, 3H), 4.57-4.4 (m, 2H), 4.2 (m, 2H), 4.0-3.69 (m, 6H), 3.57 (broad, s, 1H), 3.19-2.8 (m, 7H), 1.87 (m, 1H), 1.69-1.48 (m, 5H), 1.25 (m, 3H), 0.93 (d, J=6.3 Hz, 3H), 0.88 (d, J=6.3 Hz, 3H); $^{31}$P NMR ($CDCl_3$) δ 17.3, 15.2.

Example 34

Monophospholactate 35: A solution of 34 (0.60 g, 0.71 mmol) and morpholine (0.31 mL, 3.54 mmol) in EtOAc (8 mL) was treated with HOAc (0.16 mL, 2.83 mmol) and $NaBH_3CN$ (89 mg, 1.42 mmol). The reaction mixture was stirred at room temperature for 4 h. The product was partitioned between EtOAc and $H_2O$. The organic phase was washed with brine, dried with $Na_2SO_4$, filtered, and concentrated. The crude product was purified by column chromatography on silica gel (6% 2-propanol/$CH_2Cl_2$) to give the monophospholactate (0.46 g, 70%, GS 278115, 1:1 diastereomeric mixture) as a white solid: $^1$H NMR ($CDCl_3$) δ 7.74 (d, J=8.4 Hz, 2H), 7.52 (d, J=8.4 Hz, 2H), 7.38-7.15 (m, 7H), 6.92 (m, 2H), 5.66 (mA 1H), 5.2-5.0 (m, 2H), 4.57-4.4 (m, 2H), 4.2 (m, 2H), 3.97-3.57 (m, 12H), 3.2-2.78 (m, 7H), 2.46 (broad, s, 4H), 1.87 (m, 1H), 1.64-1.5 (m, 5H), 1.25 (m, 3H), 0.93 (d, J=6.3 Hz, 3H), 0.88 (d, J=6.3 Hz, 3H); $^{31}$P NMR ($CDCl_3$) δ 17.3, 15.3.

Example 35

Monophospholactate 37: A solution of 25 (0.50 g, 0.64 mmol) in $CH_2Cl_2$ (2.0 mL) at 0° C. was treated with trifluoroacetic acid (1 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (3 mL) and cooled to 0° C. Triethylamine (0.45 mL, 3.20 mmol) was added followed by the treatment of 4-benzyloxybenzenesulfonyl chloride (0.18 g, 0.64 mmol, prepared according to Toja, E. et al. Eur. J. Med. Chem. 1991, 26, 403). The solution was stirred for 30 min at 0° C. and then warmed to room temperature for 30 min. The product was partitioned between $CH_2Cl_2$ and 0.1 N HCl. The organic phase was washed with saturated NaCl, dried with $Na_2SO_4$, filtered, and concentrated. The crude product was purified by column chromatography on silica gel (4% 2-propanol/$CH_2Cl_2$) to give the monophospholactate (0.51 g, 85%) as a white solid.

Example 36

Monophospholactate 38: To a solution of 37 (0.48 g, 0.52 mmol) in EtOH (15 mL) was added 10% Pd/C (0.10 g). The suspension was stirred under $H_2$ atmosphere (balloon) at room temperature overnight. The reaction mixture was filtered through a plug of celite. The filtrate was concentrated and the crude product was purified by column chromatography on silica gel (5% 2-propanol/$CH_2Cl_2$) to give the monophospholactate (0.38 g, 88%, GS 273838, 1:1 diastereomeric mixture) as a white solid: $^1$H NMR ($CDCl_3$) δ 8.86 (dd, 1H), 7.42-7.25 (m, 9H), 6.91 (m., 4H), 5.73 (d, J=5.1 Hz, 1H), 5.42 (m, 1H), 5.18 (m, 2H), 4.76-4.31 (m, 2H), 4.22 (m, 2H), 4.12-3.75 (m, 6H), 3.63 (broad, s, 1H), 3.13 (m, 3H), 2.87 (m, 1H), 2.63 (m, 1H), 2.4 (m, 1H), 2.05 (m, 2H), 1.9 (m, 1H), 1.8 (m, 1H), 1.6 (m, 3H), 1.25 (m, 3H), 0.95 (d, J=6.6 Hz, 3H), 0.85 (d, J=6.6 Hz, 3H); $^{31}$P NMR ($CDCl_3$) δ 17.1, 15.7.

Example 37

Monophospholactate 40: A solution of 25 (0.75 g, 0.96 mmol) in $CH_2Cl_2$ (2.0 mL) at 0° C. was treated with trifluoroacetic acid (1 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (4 mL) and cooled to 0° C. Triethylamine (0.67 mL, 4.80 mmol) was added followed by the treatment of 4-(4'-benzyloxycarbonyl piperazinyl)benzenesulfonyl chloride (0.48 g, 1.22 mmol, prepared according to Toja, E. et al. Arzneim. Forsch. 1994, 44, 501). The solution was stirred at 0° C. for 1 h and then warmed to room temperature for 30 min. The product was partitioned between 10% 2-propanol/$CH_2Cl_2$ and 0.1 N HCl. The organic phase was washed with saturated NaCl, dried with $Na_2SO_4$, filtered, and concentrated. The crude product was purified by column chromatography on silica gel (3% 2-propanol/$CH_2Cl_2$) to give the monophospholactate (0.63 g, 60%) as a white solid.

Example 38

Monophospholactate 41: To a solution of 40 (0.62 g, 0.60 mmol) in MeOH (8 mL) and EtOAc (2 mL) was added 10% Pd/C (0.20 g). The suspension was stirred under $H_2$ atmosphere (balloon) at room temperature overnight. The reaction mixture was filtered through a plug of celite. The filtrate was treated with 1.2 equivalent of TFA, co-evaporated with $CHCl_3$ and dried under vacuum to give the monophospholactate (0.55 g, 90%) as a white solid.

Example 39

Monophospholactate 42: A solution of 41 (0.54 g, 0.53 mmol) and formaldehyde (0.16 mL, 5.30 mmol) in EtOAc (10 mL) was treated with HOAc (0.30 mL, 5.30 mmol) and $NaBH_3CN$ (0.33 g, 5.30 mmol). The reaction mixture was stirred at room temperature overnight. The product was partitioned between EtOAc and $H_2O$. The organic phase was washed with brine, dried with $Na_2SO_4$, filtered, and concentrated. The crude product was purified by column chromatography on silica gel (6% 2-propanol/$CH_2Cl_2$) to give the monophospholactate (97.2 mg, 20%, GS 277937, 1:1 diastereomeric mixture) as a white solid: $^1$H NMR ($CDCl_3$) δ 7.64 (d, J=9.0 Hz, 2H), 7.38-7.17 (m, 7H), 6.95-6.88 (m, 4H), 5.67 (m, 1H), 5.2-4.96 (m, 2H), 4.57-4.4 (m, 2H), 4.2 (m, 2H), 3.97-3.64 (m, 8H), 3.49-3.37 (m, 4H), 3.05-2.78 (m, 12H), 1.88-1.62 (m, 3H), 1.58 (m, 3H), 1.25 (m, 3H), 0.93 (d, J=6.3 Hz, 3H), 0.88 (d, J=6.3 Hz, 3H); $^{31}$P NMR ($CDCl_3$) δ 17.3, 15.3.

Example 40

Monophospholactate 45: A solution of 43 (0.12 g, 0.16 mmol) and lactate 44 (0.22 g, 1.02 mmol) in pyridine (1 mL) was heated to 70° C. and 1,3-dicyclohexylcarbodiimide (0.17 g, 0.83 mmol) was added. The reaction mixture was stirred at 70° C. for 4 h and cooled to room temperature. The solvent was removed under reduced pressure. The residue was suspended in EtOAc and 1,3-dicyclohexyl urea was filtered off. The product was partitioned between EtOAc and 0.2 N HCl. The EtOAc layer was washed with 0.2 N HCl, $H_2O$, saturated NaCl, dried with $Na_2SO_4$, filtered, and concentrated. The crude product was purified by column chromatography on silica gel (3% 2-propanol/$CH_2Cl_2$) to give the monophospholactate (45 mg, 26%) as a white solid.

Example 41

Alcohol 46: To a solution of 45 (40 mg, 0.042 mmol) in EtOAc (2 mL) was added 20% $Pd(OH)_2/C$ (10 mg). The suspension was stirred under $H_2$ atmosphere (balloon) at room temperature for 3 h. The reaction mixture was filtered through a plug of celite. The filtrate was concentrated and the product was dried under vacuum to give the alcohol (33 mg, 90%, GS 278809, 3/2 diastereomeric mixture) as a white solid: $^1$H NMR ($CDCl_3$) δ 7.72 (d, J=8.7 Hz, 2H), 7.39-7.15 (m, 7H), 7.02-6.88 (m, 4H), 5.66 (d, J=4.5 Hz, 1H), 5.13-5.02 (m, 2H), 4.54-4.10 (m, 4H), 4.00-3.69 (m, 11H), 3.14 (m, 1H), 3.02-2.77 (m, 6H), 1.85-1.6 (m, 6H), 0.94 (d, J=6.3 Hz, 3H), 0.89 (d, J=6.3 Hz, 3H); $^{31}$P NMR ($CDCl_3$) δ 17.4, 15.9.

Scheme 12

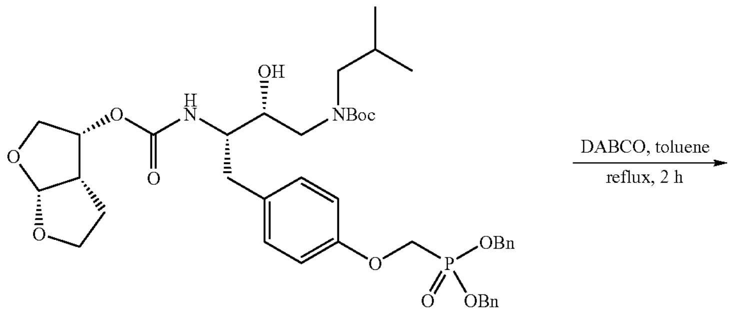

6

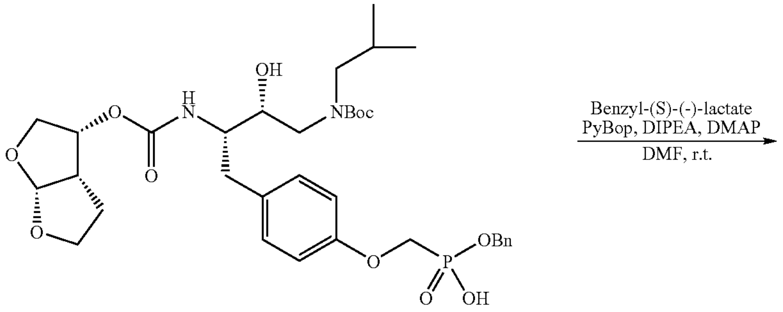

47

-continued
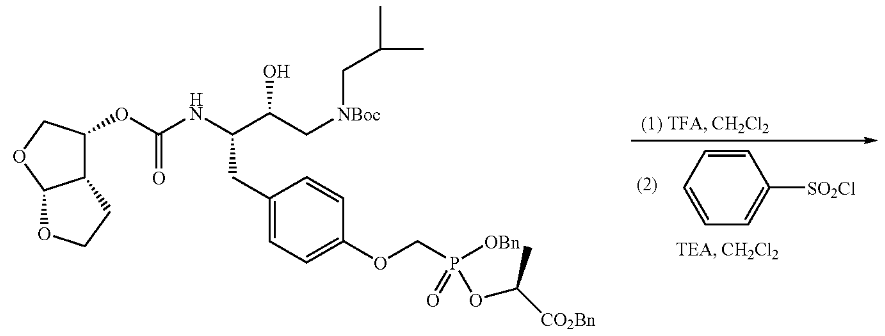
48
Scheme 13
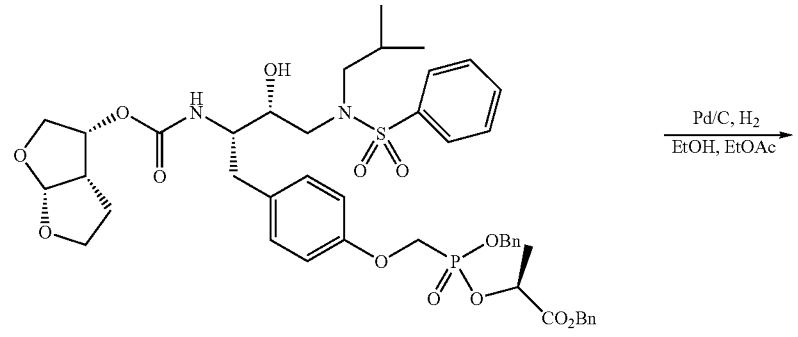
49
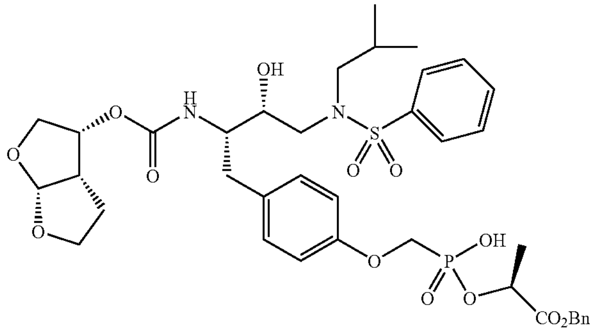
50
GS 224342
48
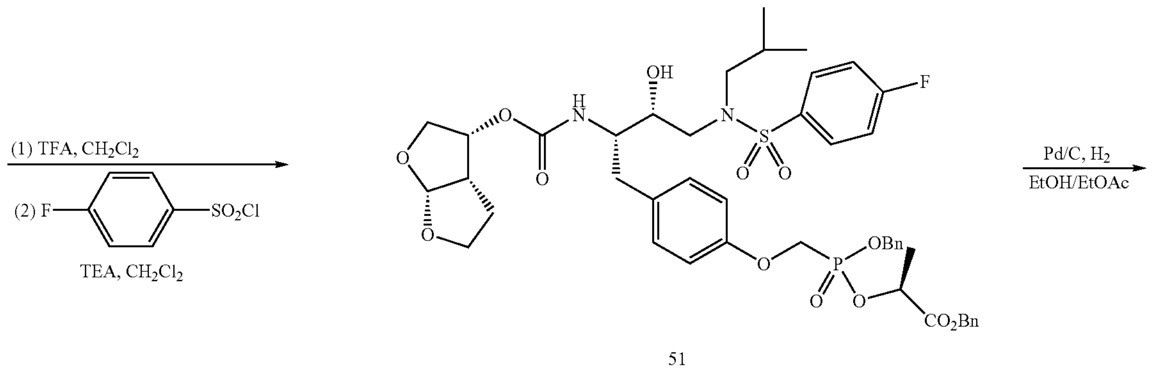
51

-continued
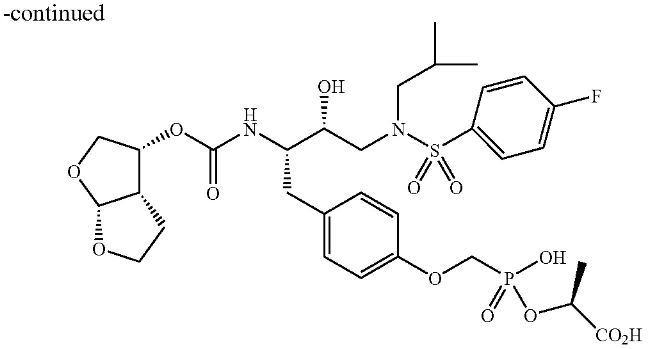
52
GS 224343
Scheme 14
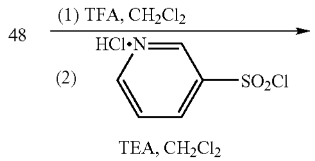
-continued
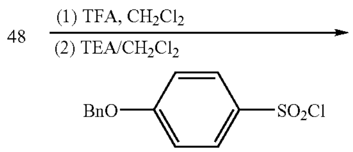
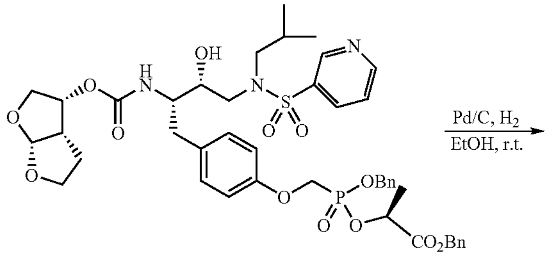
53
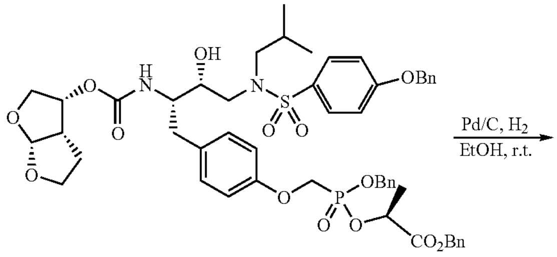
55
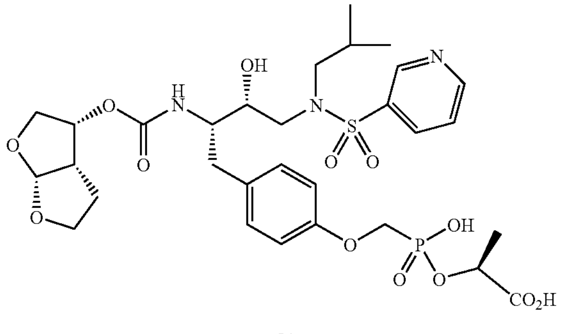
54
GS 273834
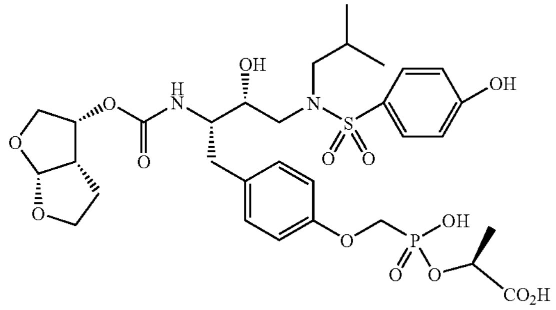
56
GS 273847

Scheme 15
29
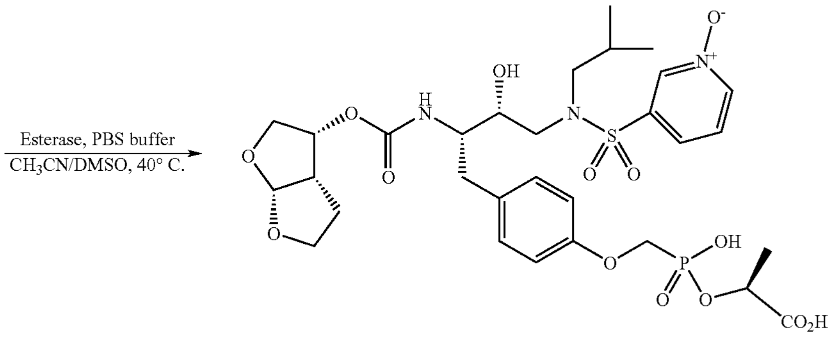
57
GS 277777
35
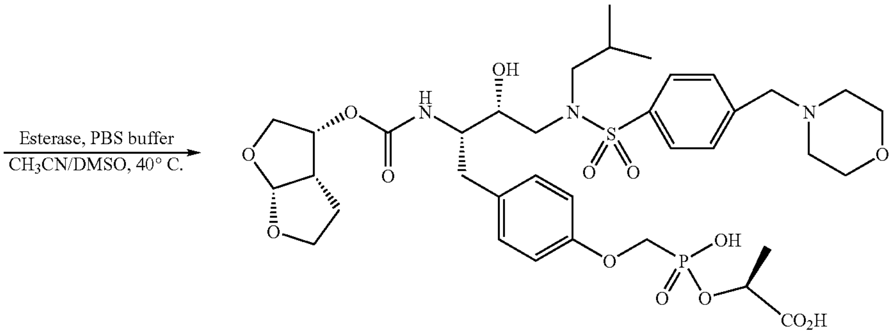
58
GS 278116
34
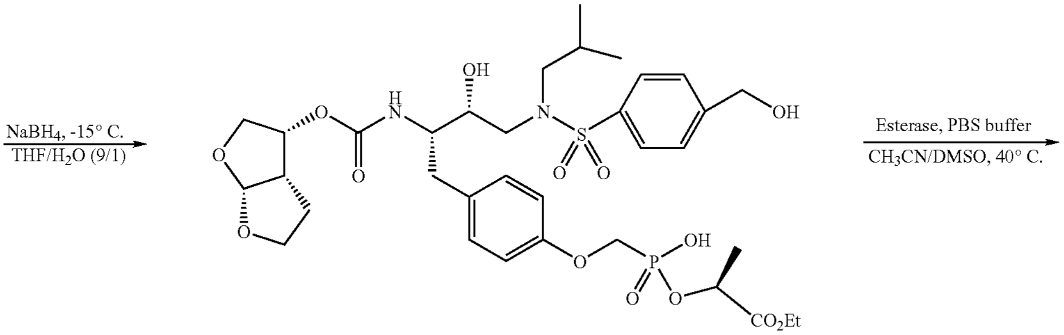
59
GS 278503
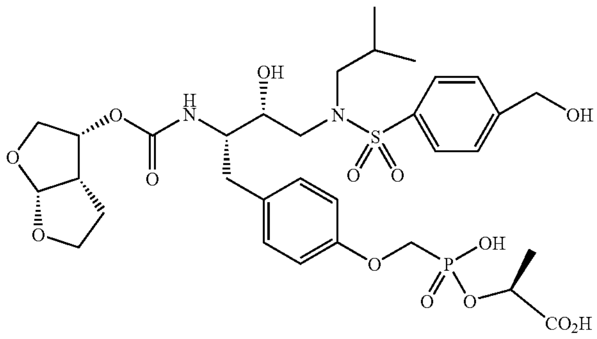
60
GS 278764

Example 42

Monobenzylphosphonate 47: A solution of 6 (2.00 g, 2.55 mmol) and DABCO (0.29 g, 2.55 mmol) in toluene (10 mL) was heated to reflux for 2 h. The solvent was evaporated under reduced pressure. The residue was partitioned between EtOAc and 0.2 N HCl. The EtOAc layer was washed with $H_2O$, saturated NaCl, dried with $Na_2SO_4$, filtered, and concentrated. The crude product was dried under vacuum to give the monobenzylphosphonate (1.68 g, 95%) as a white solid.

Example 43

Monophospholactate 48: To a solution of 47 (2.5 g, 3.61 mmol) and benzyl-(S)-(−)-lactate (0.87 mL, 5.42 mmol) in DMF (12 mL) was added PyBop (2.82 g, 5.42 mmol) and N,N-diisopropylethylamine (2.51 mL, 14.44 mmol). The reaction mixture was stirred at room temperature for 3 h and concentrated. The residue was partitioned between EtOAc and 0.2 N HCl. The EtOAc layer was washed with $H_2O$, saturated NaCl, dried with $Na_2SO_4$, filtered, and concentrated. The crude product was purified by column chromatography on silica gel (3% 2-propanol/$CH_2Cl_2$) to give the monophospholactate (1.58 g, 51%) as a white solid.

Example 44

Monophospholactate 49: A solution of 48 (0.30 g, 0.35 mmol) in $CH_2Cl_2$ (0.6 mL) at 0° C. was treated with trifluoroacetic acid (0.3 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (2 mL) and cooled to 0° C. Triethylamine (0.20 mL, 1.40 mmol) was added followed by the treatment of benzenesulfonyl chloride (62 mg, 0.35 mmol). The solution was stirred at 0° C. for 30 min and then warmed to room temperature for 30 min. The product was partitioned between $CH_2Cl_2$ and 0.1 N HCl. The organic phase was washed with saturated NaCl, dried with $Na_2SO_4$, filtered, and concentrated. The crude product was purified by column chromatography on silica gel (3% 2-propanol/$CH_2Cl_2$) to give the monophospholactate (0.17 g, 53%) as a white solid.

Example 45

Metabolite X 50: To a solution of 49 (80 mg, 0.09 mmol) in EtOH (6 mL) and EtOAc (2 mL) was added 10% Pd/C (20 mg). The suspension was stirred under $H_2$ atmosphere (balloon) at room temperature for 8 h. The reaction mixture was filtered through a plug of celite. The filtrate was concentrated, co-evaporated with $CHCl_3$ and dried under vacuum to give the metabolite X (61 mg, 95%, GS 224342) as a white solid: $^1H$ NMR ($CD_3OD$) δ 7.83 (d, J=6.9 Hz, 2H), 7.65-7.58 (m, 3H), 7.18 (d, J=7.8 Hz, 2H), 6.90 (d, J=7.8 Hz, 2H), 5.59 (d, J=4.8 Hz, 1H), 5.0 (m, 1H), 4.27 (d, J=10.2 Hz, 2H), 3.95-3.68 (m, 6H), 3.45 (dd, 1H), 3.18-2.84 (m, 6H), 2.50 (m, 1H), 2.02 (m, 1H), 1.6-1.38 (m, 5H), 0.93 (d, J=6.3 Hz, 3H), 0.88 (d, J=6.3 Hz, 3H); $^{31}P$ NMR ($CD_3OD$), δ 18.0.

Example 46

Monophospholactate 51: A solution of 48 (0.28 g, 0.33 mmol) in $CH_2Cl_2$ (0.6 mL) at 0° C. was treated with trifluoroacetic acid (0.3 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (2 mL) and cooled to 0° C. Triethylamine (0.18 mL, 1.32 mmol) was added followed by the treatment of 4-fluorobenzenesulfonyl chloride (64 mg, 0.33 mmol). The solution was stirred at 0° C. for 30 min and then warmed to room temperature for 30 min. The product was partitioned between $CH_2Cl_2$ and 0.1 N HCl. The organic phase was washed with saturated NaCl, dried with $Na_2SO_4$, filtered, and concentrated. The crude product was purified by column chromatography on silica gel (3% 2-propanol/$CH_2Cl_2$) to give the monophospholactate (0.16 g, 52%) as a white solid.

Example 47

Metabolite X 52: To a solution of 51 (80 mg, 0.09 mmol) in EtOH (6 mL) and EtOAc (2 mL) was added 10% Pd/C (20 mg). The suspension was stirred under $H_2$ atmosphere (balloon) at room temperature for 8 h. The reaction mixture was filtered through a plug of celite. The filtrate was concentrated, co-evaporated with $CHCl_3$ and dried under vacuum to give the metabolite X (61 mg, 95%, GS 224343) as a white solid: $^1H$ NMR ($CD_3OD$) δ 7.9 (dd, 2H), 7.32 (m, 2H), 7.18 (dd, 2H), 6.90 (dd, 2H), 5.59 (d, J=5.4 Hz, 1H), 5.0 (m, 1H), 4.28 (d, J=10.2 Hz, 2H), 3.95-3.72 (m, 6H), 3.44 (dd, 1H), 3.15-2.85 (m, 6H), 2.5 (m, 1H), 2.02 (m, 1H), 1.55-1.38 (m, 5H), 0.93 (d, J=6.3 Hz, 3H), 0.88 (d, J=6.3 Hz, 3H). $^{31}P$ NMR ($CD_3OD$) δ 18.2.

Example 48

Monophospholactate 53: A solution of 48 (0.20 g, 0.24 mmol) in $CH_2Cl_2$ (0.6 mL) at 0° C. was treated with trifluoroacetic acid (0.3 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (2 mL) and cooled to 0° C. Triethylamine (0.16 mL, 1.20 mmol) was added followed by the treatment of hydrogen chloride salt of 3-pyridinysulfonyl chloride (50 mg, 0.24 mmol). The solution was stirred at 0° C. for 30 min and then warmed to room temperature for 30 min. The product was partitioned between $CH_2Cl_2$ and $H_2O$. The organic phase was washed with saturated NaCl, dried with $Na_2SO_4$, filtered, and concentrated. The crude product was purified by column chromatography on silica gel (4% 2-propanol/$CH_2Cl_2$) to give the monophospholactate (0.11 g, 53%) as a white solid.

Example 49

Metabolite X 54: To a solution of 53 (70 mg, 0.09 mmol) in EtOH (5 mL) was added 10% Pd/C (20 mg). The suspension was stirred under $H_2$ atmosphere (balloon) at room temperature for 5 h. The reaction mixture was filtered through a plug of celite. The filtrate was concentrated, co-evaporated with $CHCl_3$ and dried under vacuum to give the metabolite X (53 mg, 95%, GS 273834) as a white solid: $^1H$ NMR ($CD_3OD$) δ 8.99 (s, 1H), 8.79 (d, J=4.2 Hz, 1H), 8.29 (d, J=7.5 Hz, 1H), 7.7 (m, H), 7.15 (d, J=8.4 Hz, 2H), 6.9 (d, J=7.8 Hz, 2H), 5.59 (d, J=5.4 Hz, 1H), 5.0 (m, 1H), 4.28 (d, J=9.9 Hz, 2H), 3.97-3.70 (m, 6H), 3.44 (dd, 1H), 3.17-2.85 (m, 6H), 2.5 (m, 1H), 2.03 (m, 1H), 1.65-1.38 (m, 5H), 0.93 (d, J=6.3 Hz, 3H), 0.88 (d, J=6.3 Hz, 3H). $^{31}P$ NMR ($CD_3OD$) δ 17.8.

Example 50

Monophospholactate 55: A solution of 48 (0.15 g, 0.18 mmol) in $CH_2Cl_2$ (1 mL) at 0° C. was treated with trifluoroacetic acid (0.5 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (2 mL) and cooled to 0° C. Triethylamine (0.12 mL, 0.88 mmol) was added followed by the treatment of 4-benzyloxybenzenesulfonyl chloride (50 mg, 0.18 mmol). The solution was stirred at 0° C. for 30 min and then warmed to room temperature for 30 min. The product was partitioned between $CH_2Cl_2$ and 0.1 N HCl. The organic phase was washed with saturated NaCl, dried with $Na_2SO_4$, filtered, and concentrated. The crude product was purified by column chromatography on silica gel (3% 2-propanol/$CH_2Cl_2$) to give the monophospholactate (0.11 g, 63%) as a white solid.

Example 51

Metabolite X 56: To a solution of 55 (70 mg, 0.07 mmol) in EtOH (4 mL) was added 10% Pd/C (20 mg). The suspension was stirred under $H_2$ atmosphere (balloon) at room temperature for 4 h. The reaction mixture was filtered through a plug of celite. The filtrate was concentrated, co-evaporated with $CHCl_3$ and dried under vacuum to give the metabolite X (46 mg, 90%, GS 273847) as a white solid: $^1$H NMR ($CD_3OD$), δ 7.91 (s, 1H), 7.65 (d, J=8.4 Hz, 2H), 7.17 (d, J=8.1 Hz, 2H), 6.91 (m, 4H), 5.59 (d, J=5.1 Hz, 1H), 5.0 (m, 1H), 4.27 (d, J=10.2 Hz, 2H), 3.97-3.74 (m, 6H), 3.4 (dd, 1H), 3.17-2.8 (m, 6H), 2.5 (m, 1H), 2.0 (m, 1H), 1.6-1.38 (m, 5H), 0.93 (d, J=6.3 Hz, 3H), 0.88 (d, J=6.3 Hz, 3H); $^{31}$P NMR ($CD_3OD$) δ 17.9.

Example 52

Metabolite X 57: To a suspension of 29 (40 mg, 0.05 mmol) in $CH_3CN$ (1 mL), DMSO (0.5 mL), and 1.0 M PBS buffer (5 mL) was added esterase (200 μL). The suspension was heated to 40° C. for 48 h. The reaction mixture was concentrated, suspended in MeOH and filtered. The filtrate was concentrated and purified by HPLC to give the metabolite X (20 mg, 57%, GS 277777) as a white solid: $^1$H NMR ($CD_3OD$) δ 8.68 (s, 1H), 8.47 (d, J=6.0 Hz, 1H), 7.93 (d, J=7.8 Hz, 1H), 7.68 (m, 1H), 7.15 (d, J=8.4 Hz, 2H), 6.9 (d, J=8.4 Hz, 2H), 5.59 (d, J=5.4 Hz, 1H), 5.0 (m, 1H), 4.23 (d, J=10.5 Hz, 2H), 3.97-3.68 (m, 6H), 3.45 (dd, 1H), 3.15-2.87 (m, 6H), 2.46 (m, 1H), 2.0 (m, 1H), 1.6-1.38 (m, 5H), 0.95 (d, J=6.6 Hz, 3H), 0.92 (d, J=6.6 Hz, 3H); $^{31}$P NMR ($CD_3OD$) δ 17.2.

Example 53

Metabolite X 58: To a suspension of 35 (60 mg, 0.07 mmol) in $CH_3CN$ (1 mL), DMSO (0.5 mL), and 1.0 M PBS buffer (5 mL) was added esterase (400 μL). The suspension was heated to 40° C. for 3 days. The reaction mixture was concentrated, suspended in MeOH and filtered. The filtrate was concentrated and purified by HPLC to give the metabolite X (20 mg, 38%, GS 278116) as a white solid: $^1$H NMR ($CD_3OD$) δ 7.74 (d, J=6.9 Hz, 2H), 7.63 (d, J=7.5 Hz, 2H), 7.21 (d, J=8.4 Hz, 2H), 6.95 (d, J=8.1 Hz, 2H), 5.64 (d, J=5.1 Hz, 1H), 5.0 (m, 2H), 4.41 (m, 2H), 4.22 (m, 2H), 3.97-3.65 (m, 12H), 3.15-2.9 (m, 8H), 2.75 (m, 1H), 2.0 (m, 1H), 1.8 (m, 2H), 1.53 (d, J=6.9 Hz, 3H), 0.88 (m, 6H).

Example 54

Monophospholactate 59: A solution of 34 (2.10 g, 2.48 mmol) in THF (72 mL) and $H_2O$ (8 mL) at −15° C. was treated with $NaBH_4$ (0.24 g, 6.20 mmol). The reaction mixture was stirred for 10 min at −15° C. The reaction was quenched with 5% aqueous $NaHSO_3$ and extracted with $CH_2Cl_2$ (3×). The combined organic layers were washed with $H_2O$, dried with $Na_2SO_4$, filtered, and concentrated. The crude product was purified by column chromatography on silica gel (5% 2-propanol/$CH_2Cl_2$) to give monophospholactate (1.89 g, 90%, GS 278053, 1:1 diastereomeric mixture) as a white solid: $^1$H NMR ($CDCl_3$) δ 7.64 (m, 2H), 7.51 (m, 2H), 7.38-7.19 (m, 7H), 6.92 (m, 2H), 5.69 (d, J=4.8 Hz, 1H), 5.15 (m, 2H), 4.76 (s, 2H), 4.54 (d, J=10.5 Hz, 1H), 4.44 (m, 1H), 4.2 (m, 2H), 4.04-3.68 (m, 6H), 3.06-2.62 (m, 7H), 1.8 (m, 3H), 1.62-1.5 (dd, 3H), 1.25 (m, 3H), 0.94 (d, J=6.3 Hz, 3H), 0.87 (d, J=6.3 Hz, 3H); $^{31}$P NMR ($CDCl_3$) δ 17.4, 15.4.

Example 55

Metabolite X 60: To a suspension of 59 (70 mg, 0.08 mmol) in $CH_3CN$ (1 mL), DMSO (0.5 mL), and 1.0 M PBS buffer (5 mL) was added esterase (600 μL). The suspension was heated to 40° C. for 36 h. The reaction mixture was concentrated, suspended in MeOH and filtered. The filtrate was concentrated and purified by HPLC to give the metabolite X (22 mg, 36%, GS 278764) as a white solid: $^1$H NMR ($CD_3OD$) δ 7.78 (dd, 2H), 7.54 (dd, 2H), 7.15 (m, 2H), 6.9 (m, 2H), 5.57 (d, 1H), 5.0 (m, 2H), 4.65 (m, 4H), 4.2 (m, 2H), 3.9-3.53 (m, 6H), 3.06-2.82 (m, 6H), 2.5 (m, 1H), 2.0 (m, 2H), 1.62-1.35 (m, 3H), 0.94 (m, 6H).

Scheme 16

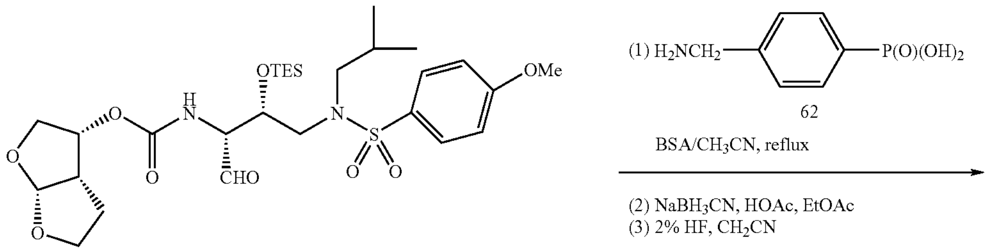

61

-continued
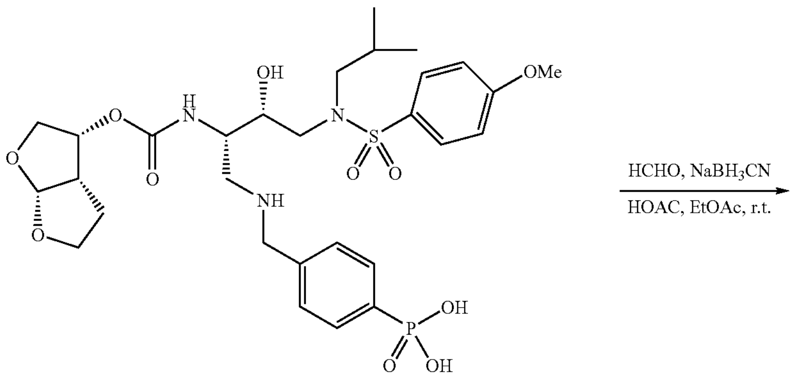
63
GS 277929
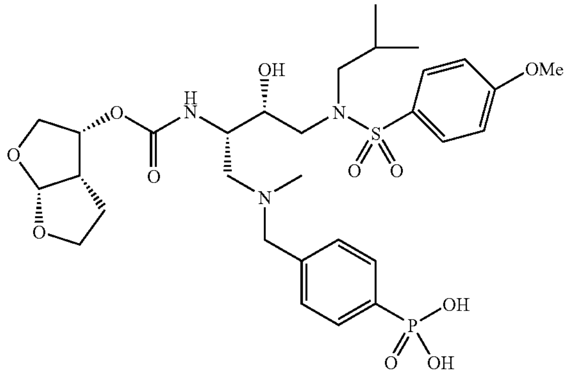
64
GS 277935
Scheme 17
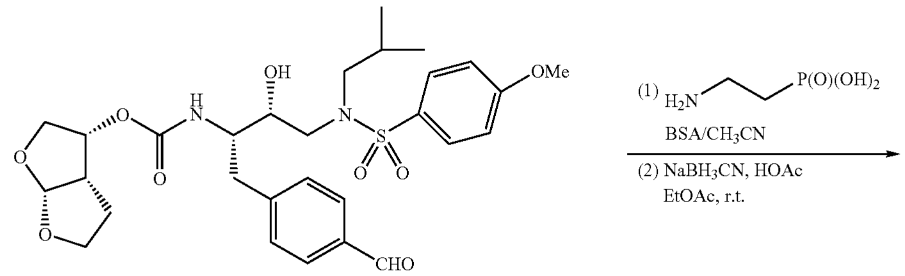
65
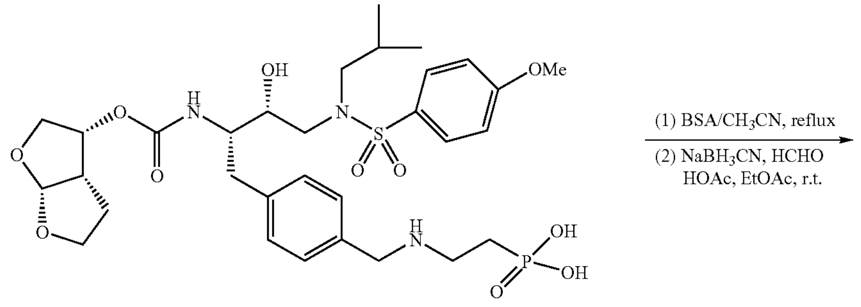
66

-continued

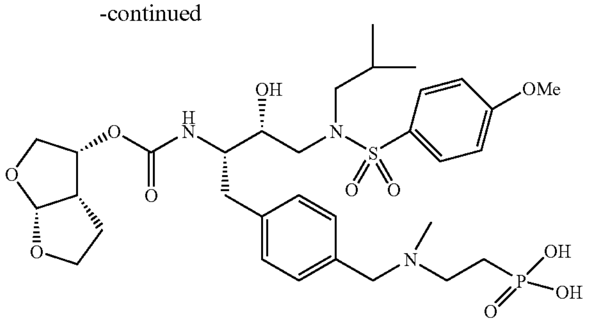

67
GS 277957

Scheme 18

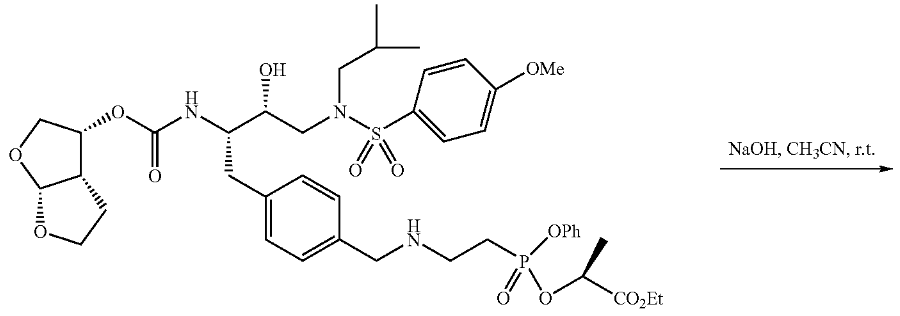

68

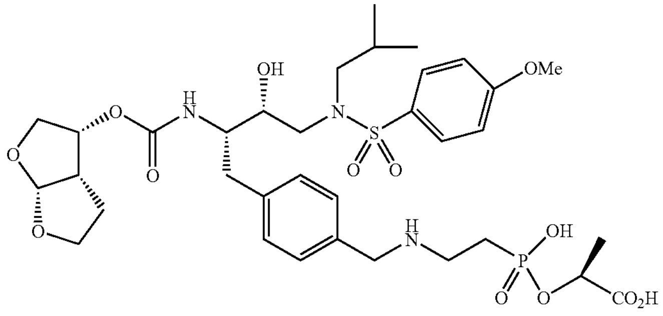

69
GS 273842

Example 56

Phosphonic Acid 63: Compound 62 (0.30 g, 1.12 mmol) was dissolved in $CH_3CN$ (5 mL). N,O-Bis(trimethylsilyl) acetamide (BSA, 2.2 mL, 8.96 mmol) was added. The reaction mixture was heated to reflux for 2 h, cooled to room temperature, and concentrated. The residue was co-evaporated with toluene and chloroform and dried under vacuum to give a thick oil which was dissolved in EtOAc (4 mL) and cooled to 0° C. Aldehyde 61 (0.20 g, 0.33 mmol), AcOH (0.18 mL, 3.30 mmol), and $NaBH_3CN$ (0.20 g, 3.30 mmol) were added. The reaction mixture was warmed to room temperature and stirred overnight. The reaction was quenched with $H_2O$, stirred for 30 min, filtered, and concentrated. The crude product was dissolved in $CH_3CN$ (13 mL) and 48% aqueous HF (0.5 mL) was added. The reaction mixture was stirred at room temperature for 2 h and concentrated. The crude product was purified by HPLC to give the phosphonic acid (70 mg, 32%, GS 277929) as a white solid: $^1$H NMR ($CD_3OD$) δ 7.92 (dd, 2H), 7.73 (d, J=8.7 Hz, 2H), 7.63 (dd, 2H), 7.12 (d, J=8.7 Hz, 2H), 5.68 (d, J=5.1 Hz, 1H), 5.13 (m, 1H), 4.4 (m, 2H), 4.05-3.89 (m, 8H), 3.75 (m, 1H), 3.5 (m, 1H), 3.37 (m, 1H), 3.23-3.0 (m, 3H), 2.88-2.7 (m, 2H), 2.2 (m, 1H), 1.8 (m, 2H), 0.92 (d, J=6.3 Hz, 3H), 0.85 (d, J=6.3 Hz, 3H); $^{31}$P NMR ($CD_3OD$) δ 14.5.

Example 57

Phosphonic Acid 64: A solution of 63 (50 mg, 0.07 mmol) and formaldehyde (60 mg, 0.70 mmol) in EtOAc (2 mL) was treated with HOAc (43 μL, 0.70 mmol) and $NaBH_3CN$ (47 mg, 0.7 mmol). The reaction mixture was stirred at room temperature for 26 h. The reaction was quenched with $H_2O$, stirred for 20 min, and concentrated. The crude product was purified by HPLC to give the phosphonic acid (15 mg, 29%, GS 277935) as a white solid: $^1$H NMR ($CD_3OD$) δ 7.93 (m, 2H), 7.75 (m, 2H), 7.62 (m, 2H), 7.11 (m, 2H), 5.66 (m, 1H), 5.13 (m, 1H), 4.4 (m, 2H), 4.05-3.89 (m, 8H), 3.75 (m, 2H), 3.09-2.71 (m, 6H), 2.2 (m, 1H), 1.9 (m, 5H), 0.92 (d, J=6.3 Hz, 3H), 0.85 (d, J=6.3 Hz, 3H); $^{31}$P NMR ($CD_3OD$) δ 14.0.

Example 58

Phosphonic Acid 66: 2-Aminoethylphosphonic acid (2.60 g, 21.66 mmol) was dissolved in $CH_3CN$ (40 mL). N. O-Bis (trimethylsilyl)acetamide (BSA, 40 mL) was added. The reaction mixture was heated to reflux for 2 h and cooled to room temperature and concentrated. The residue was co-evaporated with toluene and chloroform and dried under vacuum to give a thick oil which was dissolved in EtOAc (40 mL). Aldehyde 65 (1.33 g, 2.25 mmol), AcOH (1.30 mL, 22.5 mmol) and $NaBH_3CN$ (1.42 g, 22.5 mmol) were added. The reaction mixture was stirred at room temperature overnight. The reaction was quenched with $H_2O$, stirred for 1 h, filtered, and concentrated. The residue was dissolved in MeOH and filtered. The crude product was purified by HPLC to give the phosphonic acid (1.00 g, 63%) as a white solid.

Example 59

Phosphonic Acid 67: Phosphonic acid 66 (0.13 g, 0.19 mmol) was dissolved in $CH_3CN$ (4 mL). N,O-Bis(trimethylsilyl)acetamide (BSA, 0.45 mL, 1.90 mmol) was added. The reaction mixture was heated to reflux for 2 h, cooled to room temperature, and concentrated. The residue was co-evaporated with toluene and chloroform and dried under vacuum to give a thick oil which was dissolved in EtOAc (3 mL). Formaldehyde (0.15 mL, 1.90 mmol), AcOH (0.11 mL, 1.90 mmol) and $NaBH_3CN$ (63 mg, 1.90 mmol) were added. The reaction mixture was stirred at room temperature overnight. The reaction was quenched with $H_2O$, stirred for 6 h, filtered, and concentrated. The residue was dissolved in MeOH and filtered. The crude product was purified by HPLC to give the phosphonic acid (40 mg, 30%, GS 277957) as a white solid: $^{1}$H NMR ($CD_3OD$) δ 7.78 (d, J=8.4 Hz, 2H), 7.4 (m, 4H), 7.09 (d, J=8.4 Hz, 2H), 5.6 (d, J=5.1 Hz, 1H), 4.33 (m, 2H), 3.95-3.65 (m, 9H), 3.5-3.05 (m, 6H), 2.91-2.6 (m, 7H), 2.0 (m, 3H), 1.5 (m, 2H), 0.93 (d, J=6.3 Hz, 3H), 0.87 (d, J=6.3 Hz, 3H); $^{31}$P NMR ($CD_3OD$) δ 19.7.

Example 60

Metabolite X 69: Monophospholactate 68 (1.4 g, 1.60 mmol) was dissolved in $CH_3CN$ (20 mL) and $H_2O$ (20 mL). 1.0 N NaOH (3.20 mL, 3.20 mmol) was added. The reaction mixture was stirred at room temperature for 1.5 h and cooled to 0° C. The reaction mixture was acidified to pH=1-2 with 2 N HCl (1.6 mL, 3.20 mmoL). The solvent was evaporated under reduced pressure. The crude product was purified by HPLC to give the metabolite X (0.60 g, 49%, GS 273842) as a white solid: $^{1}$H NMR (DMSO-$d_6$) δ 7.72 (d, J=8.7 Hz, 2H), 7.33 (m, 4H), 7.09 (d, J=9.0 Hz, 2H), 5.52 (d, J=5.7 Hz, 1H), 5.1 (broad, s, 1H), 4.85 (m, 1H), 4.63 (m, 1H), 4.13 (m, 2H), 3.8 (m, 5H), 3.6 (m, 4H), 3.36 (m, 1H), 3.03 (m, 4H), 2.79 (m, 3H), 2.5 (m, 1H), 2.0 (m, 3H), 1.5-1.3 (m, 5H), 0.85 (d, J=6.6 Hz, 3H), 0.79 (d, J=6.6 Hz, 3H); $^{31}$P NMR (DMSO-$d_6$) δ 21.9.

Scheme 19

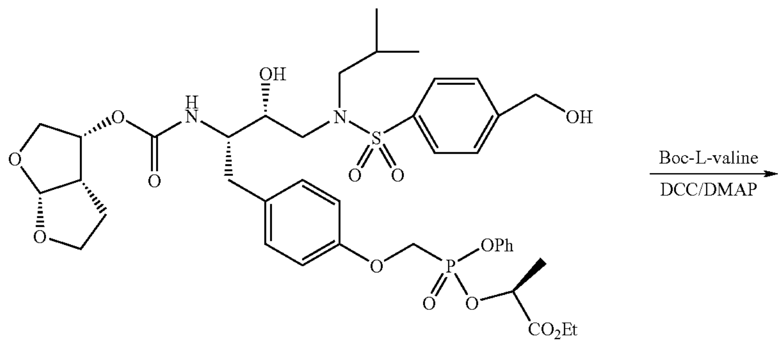

59

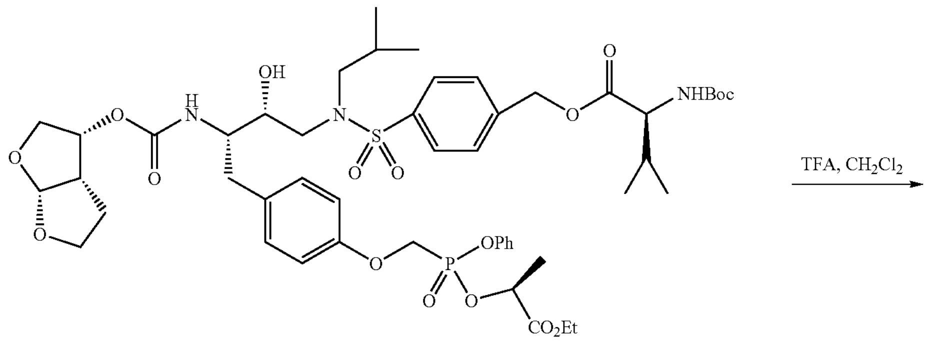

70

-continued
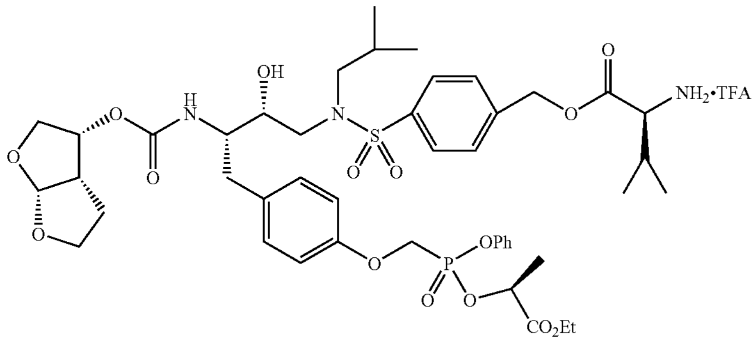
71
GS 278635
Scheme 20
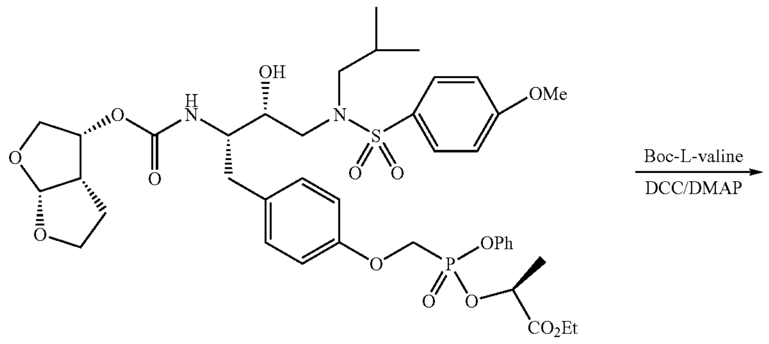
72
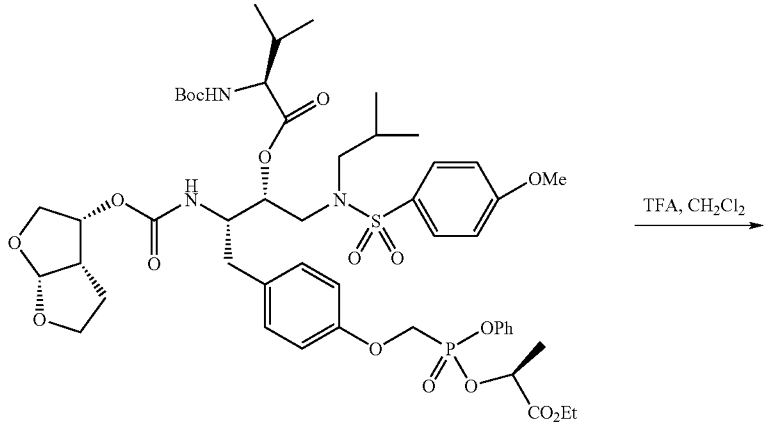
73

-continued
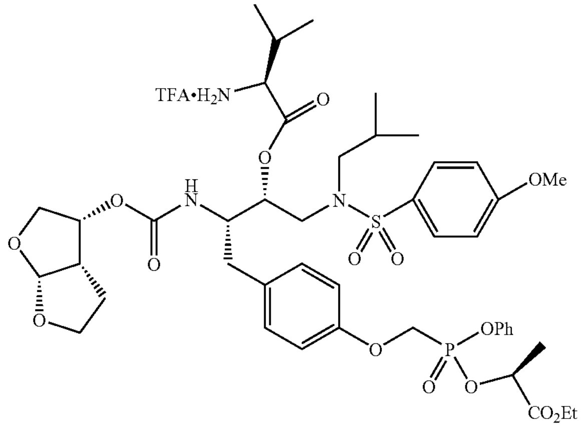
74
GS 278785
Scheme 21
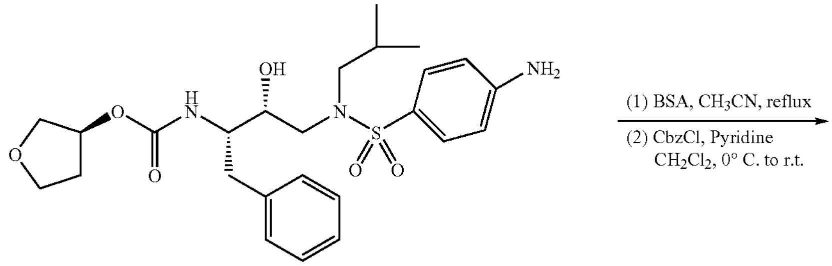
75
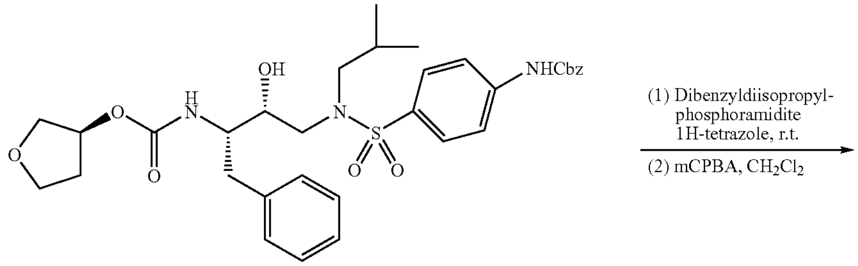
76
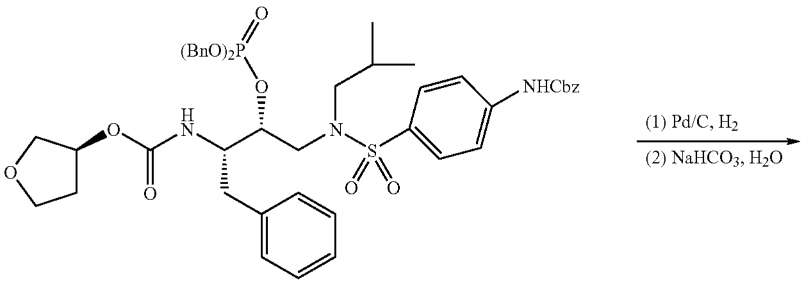
77

-continued

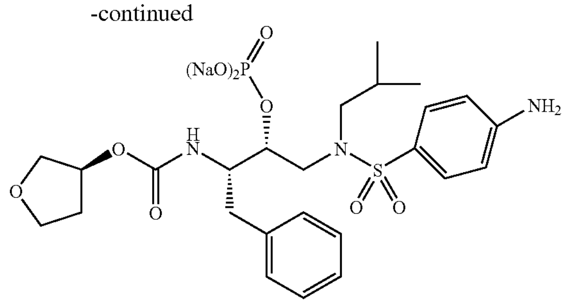

78
GS 277962

Example 61

Monophospholactate 70: A solution of 59 (1.48 g, 1.74 mmol) and Boc-L-valine (0.38 g, 1.74 mmol) in $CH_2Cl_2$ (30 mL) at 0° C. was treated with 1,3-dicyclohexylcarbodiimide (0.45 g, 2.18 mmol) and 4-dimethylaminopyridine (26 mg, 0.21 mmol). The reaction mixture was stirred at 0° C. for 1 h and then warmed to room temperature for 2 h. The product was partitioned between $CH_2Cl_2$ and 0.2 N HCl. The organic layer was washed with $H_2O$, dried with $Na_2SO_4$, filtered, and concentrated. The crude product was purified by column chromatography on silica gel (4% 2-propanol/$CH_2Cl_2$) to give the monophospholactate (1.65 g, 90%) as a white solid.

Example 62

Monophospholactate 71: A solution of 70 (1.65 g, 1.57 mmol) in $CH_2Cl_2$ (8 mL) at 0° C. was treated with trifluoroacetic acid (4 mL). The solution was stirred for 30 min at 0° C. and then warmed to room temperature for an additional 30 min. The reaction mixture was diluted with toluene and concentrated under reduced pressure. The crude product was purified by column chromatography on silica gel (10% 2-propanol/$CH_2Cl_2$) to give the monophospholactate (1.42 g, 85%, GS 278635, 2/3 diastereomeric mixture) as a white solid: $^1$H NMR ($CDCl_3$) δ 7.73 (m, 2H), 7.49 (d, J=7.2 Hz, 2H), 7.4-7.1 (m, 7H), 6.89 (m, 2H), 5.64 (m, 1H), 5.47 (m, 1H), 5.33-5.06 (m, 4H), 4.57-4.41 (m, 2H), 4.2 (m, 2H), 3.96-3.7 (m, 7H), 3.15-2.73 (m, 7H), 2.38 (m, 1H), 1.9 (m, 1H), 1.7 (m, 1H), 1.63-1.5 (m, 4H), 1.24 (m, 3H), 1.19 (m, 6H), 0.91 (d, 3H), 0.88 (d, 3H); $^{31}$P NMR ($CDCl_3$) δ 17.3, 15.4.

Example 63

Monophospholactate 73: A solution of 72 (0.43 g, 0.50 mmol) and Boc-L-valine (0.11 g, 0.50 mmol) in $CH_2Cl_2$ (6 mL) was treated with 1,3-dicyclohexylcarbodiimide (0.13 g, 0.63 mmol) and 4-dimethylaminopyridine (62 mg, 0.5 mmol). The reaction mixture was stirred at room temperature overnight. The product was partitioned between $CH_2Cl_2$ and 0.2 N HCl. The organic layer was washed with $H_2O$, dried with $Na_2SO_4$, filtered, and concentrated. The crude product was purified by column chromatography on silica gel (2% 2-propanol/$CH_2Cl_2$) to give the monophospholactate (0.45 g, 85%) as a white solid.

Example 64

Monophospholactate 74: A solution of 73 (0.44 g, 0.42 mmol) in $CH_2Cl_2$ (1 mL) at 0° C. was treated with trifluoroacetic acid (0.5 mL). The solution was stirred for 30 min at 0° C. and then warmed to room temperature for an additional 30 min. The reaction mixture was diluted with toluene and concentrated under reduced pressure. The crude product was purified by column chromatography on silica gel (10% 2-propanol/$CH_2Cl_2$) to give the monophospholactate (0.40 g, 90%, GS 278785, 1:1 diastereomeric mixture) as a white solid: $^1$H NMR ($CDCl_3$) δ 7.69 (d, J=8.4 Hz, 2H), 7.34-7.2 (m, 7H), 6.98 (d, J=8.4 Hz, 2H), 6.88 (m, 2H), 6.16 (m, 1H), 5.64 (m, 1H), 5.46 (m, 1H), 5.2-5.0 (m, 2H), 4.5 (m, 2H), 4.2 (m, 3H), 4.0-3.4 (m, 9H), 3.3 (m, 1H), 3.0-2.8 (m, 5H), 2.5 (m, 1H), 1.83 (m, 1H), 1.6-1.5 (m, 5H), 125 (m, 3H), 1.15 (m, 6H), 0.82 (d, J=6.0 Hz, 3H), 0.76 (d, J=6.0 Hz, 3H); $^{31}$P NMR ($CDCl_3$) δ 17.3, 15.5.

Example 65

Cbz Amide 76: Compound 75 (0.35 g, 0.69 mmol) was dissolved in $CH_3CN$ (6 mL). N,O-Bis(trimethylsilyl)acetamide (BSA, 0.67 mL, 2.76 mmol) was added. The reaction mixture was heated to reflux for 1 h, cooled to room temperature, and concentrated. The residue was co-evaporated with toluene and chloroform and dried under vacuum to give a thick oil which was dissolved in $CH_2Cl_2$ (3 mL) and cooled to 0° C. Pyridine (0.17 mL, 2.07 mmol) and benzyl chloroformate (0.12 mL, 0.83 mmol) were added. The reaction mixture was stirred at 0° C. for 1 h and then warmed to room temperature overnight. The reaction was quenched with MeOH (5 mL) and 10% HCl (20 mL) at 0° C. and stirred for 1 h. The product was extracted with $CH_2Cl_2$, washed with brine, dried with $Na_2SO_4$, filtered, and concentrated. The crude product was purified by column chromatography on silica gel (3% 2-propanol/$CH_2Cl_2$) to give the CBz amide (0.40 g, 90%) as a white solid.

Example 66

Dibenzylphosphonate 77: A solution of 76 (0.39 g, 0.61 mmol) and 1H-tetrazole (54 mg, 0.92 mmol) in $CH_2Cl_2$ (8 mL) was treated with dibenzyldiisopropylphosphoramidite (0.32 g, 0.92 mmol) and stirred at room temperature overnight. The solution was cooled to 0° C., treated with mCPBA, stirred for 1 h at 0° C. and then warmed to room temperature for 1 h. The reaction mixture was poured into a mixture of aqueous $Na_2SO_3$ and $NaHCO_3$ and extracted with $CH_2Cl_2$. The organic layer was washed with $H_2O$, dried with $Na_2SO_4$, filtered, and concentrated. The crude product was purified by column chromatography on silica gel (3% 2-propanol/$CH_2Cl_2$) to give the dibenzylphosphonate (0.42 g, 76%) as a white solid.

Example 67

Disodium Salt of Phosphonic Acid 78: To a solution of 77 (0.18 g, 0.20 mmol) in EtOH (20 mL) and EtOAc (4 mL) was added 10% Pd/C (40 mg). The suspension was stirred under $H_2$ atmosphere (balloon) at room temperature for 4 h. The reaction mixture was filtered through a plug of celite. The filtrate was concentrated and dried under vacuum to give the phosphonic acid (0.11 g, 95%) which was dissolved in $H_2O$ (4 mL) and treated with $NaHCO_3$ (32 mg, 0.38 mmol). The reaction mixture was stirred at room temperature for 1 h and lyopholyzed overnight to give the disodium salt of phosphonic acid (0.12 g, 99%, GS 277962) as a white solid: $^1H$ NMR ($D_2O$) δ 7.55 (dd, 2H), 7.2 (m, 5H), 7.77 (dd, 2H), 4.65 (m, 1H), 4.24 (m, 1H), 4.07 (m, 1H), 3.78-2.6 (m, 12H), 1.88-1.6 (m, 3H), 0.75 (m, 6H).

Scheme 1

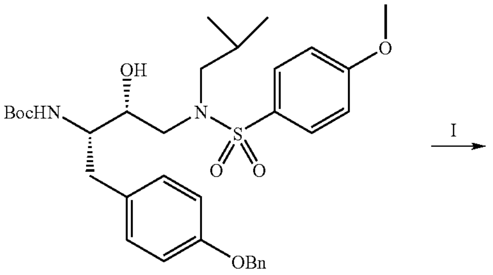

1

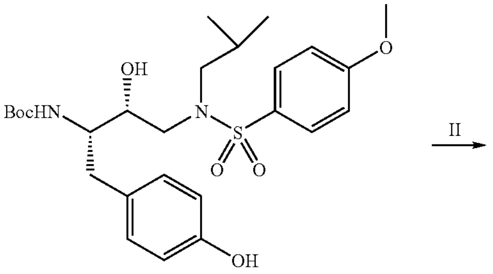

2

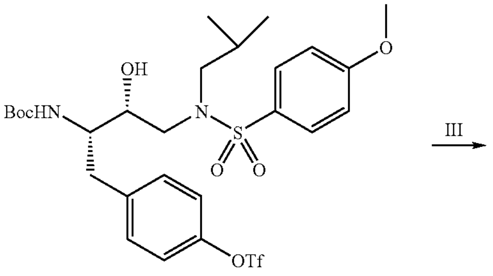

3

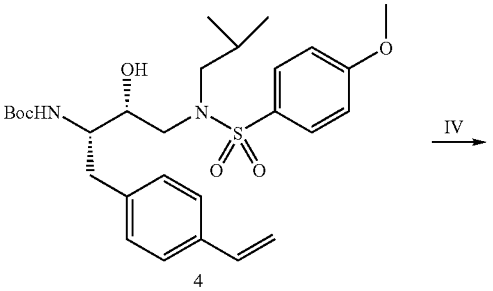

4

-continued

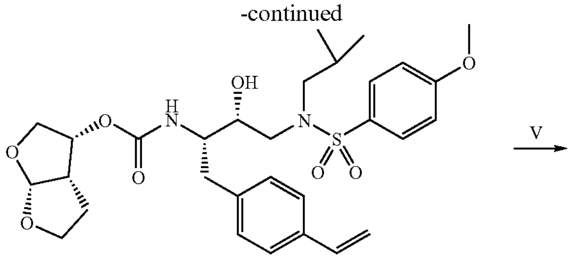

5

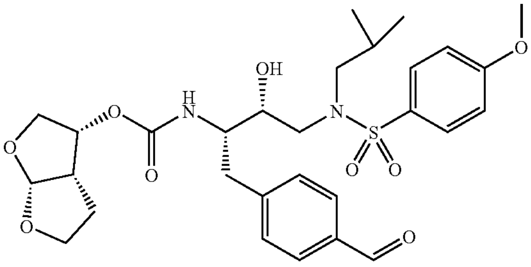

6

I. $H_2$/10% Pd-C/EtOAc-EtOH;
II. $Tf_2NPh/Cs_2CO_3$;
III. $Bu_3SnCH{=}CH_2/PdCl_2(PPh_3)_2$/LiCl/DMF/90 C.;
IV.a. $TFA/CH_2Cl_2$; b. Bisfurancarbonate/i-$Pr_2NEt$/DMAP;
V. $NaIO_4/OsO_4$/EtOAc-$H_2O$ Example 1

Compound 1 was prepared by methods from Examples herein.

Example 2

Compound 2: To a solution of compound 1 (47.3 g) in EtOH/EtOAc (1000 mL/500 mL) was added 10% Pd—C (5 g). The mixture was hydrogenated for 19 hours. Celite was added and the mixture was stirred for 10 minutes. The mixture was filtered through a pad of celite and was washed with ethyl acetate. Concentration gave compound 2 (42.1 g).

Example 3

Compound 3: To a solution of compound 2 (42.3 g, 81 mmol) in $CH_2Cl_2$ (833 mL) was added N-phenyltrifluoromethanesulfonimide (31.8 g, 89 mmol), followed by cesium carbonate (28.9 g, 89 mmol). The mixture was stirred for 24 hours. The solvent was removed under reduced pressure, and ethyl acetate was added. The reaction mixture was washed with water (3×) and brine (1×), and was dried over $MgSO_4$. Purification by flash column chromatography ($CH_2Cl_2$/EtOAc=13/1) gave compound 3 (49.5 g) as a white powder.

Example 4

Compound 4: To a solution of compound 3 (25.2, 38.5 mmol) in DMF (240 mL) was added lithium chloride (11.45 g, 270 mmol), followed by dichlorobis(triphenylphosphine) palladium(II) (540 mg, 0.77 mmol). The mixture was stirred for 3 minutes under high vacuum and recharged with nitrogen. To the above solution was added tributylvinyltin (11.25 mL). The reaction mixture was heated at 90° C. for 6 hours and cooled to 25° C. Water was added to the reaction, and the mixture was extracted with ethyl acetate (3×). The combined organic layer was washed with water (6×) and brine, and dried over $MgSO_4$. Concentration gave an oil. The oil was diluted with dichloromethane (40 mL), water (0.693 mL, 38.5 mmol) and DBU (5.76 mL, 38.5 mmol) were added. The mixture was stirred for 5 minutes, and subjected to flash column chromatography (hexanes/EtOAc=2.5/1). Compound 4 was obtained as white solid (18.4 g).

Example 5

Compound 5: To a solution of compound 4 (18.4 g, 34.5 mmol) in $CH_2Cl_2$ (70 mL) at 0° C. was added trifluoroacetic acid (35 mL). The mixture was stirred at 0° C. for 2 hrs, and solvents were evaporated under reduced pressure. The reaction mixture was quenched with saturated sodium carbonate solution, and was extracted with ethyl acetate (3×). The combined organic layer was washed with saturated sodium carbonate solution (1×), water (2×), and brine (1×), and dried over $MgSO_4$. Concentration gave a solid. To a solution of the above solid in acetonitrile (220 mL) at 0° C. was added bisfurancarbonate (10.09 g, 34.2 mmol), followed by di-isopropylethylamine (12.0 mL, 69.1 mmol) and DMAP (843 mg, 6.9 mmol). The mixture was warmed to 25° C. and stirred for 12 hours. Solvents were removed under reduced pressure. The mixture was diluted with ethyl acetate, and was washed with water (2×), 5% hydrochloric acid (2×), water (2×), 1N sodium hydroxide (2×), water (2×), and brine (1×), and dried over $MgSO_4$. Purification by flash column chromatography (hexanes/EtOAc=1/1)) gave compound 5 (13.5 g).

Example 6

Compound 6: To a solution of compound 5 (13.5 g, 23 mmol) in ethyl acetate (135 mL) was added water (135 mL), followed by 2.5% osmium tetraoxide/tert-butanol (17 mL). Sodium periodate (11.5 g) was added in portions over 2 minutes period. The mixture was stirred for 90 minutes, and was diluted with ethyl acetate. The organic layer was separated and washed with water (3×) and brine (1×), and dried over $MgSO_4$. Purification by flash column chromatography (hexanes/EtOAc=½) gave compound 6 as white powder (12 g): $^1H$ NMR ($CDCl_3$) δ 9.98 (1H, s), 7.82 (2H, m), 7.75 (2H, m), 7.43 (2H, m), 6.99 (2H, m), 5.64 (1H, m), 5.02 (2H, m), 4.0-3.8 (9H, m), 3.2-2.7 (7H, m), 1.9-1.4 (3H, m), 0.94 (6H, m).

Scheme 2

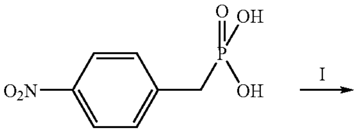

7

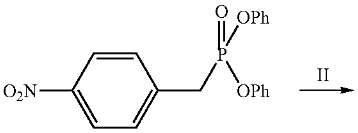

8

-continued

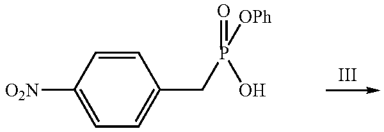

9

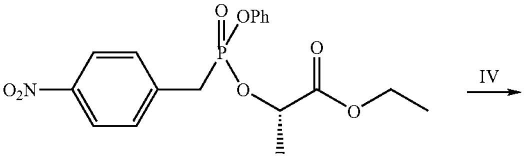

10

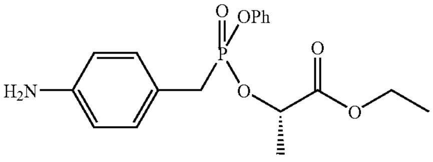

11

I. a.. $SOCl_2$/toluene/60 C.; b. PhOH/pyridine;
II. a. NaOH/THF/$H_2O$; b. HCl;
III. b. $SOCl_2$/toluene/60 C.; c. ethyl lactate/pyridine;
IV. $H_2$/10% Pd-C/EtOAc Scheme 3

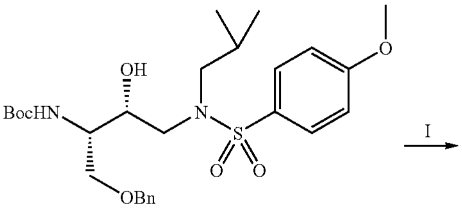

12

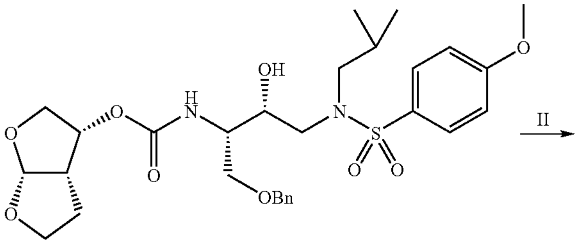

13

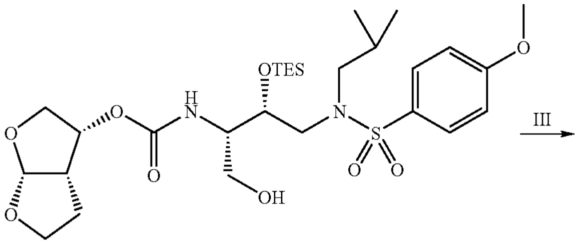

14

-continued

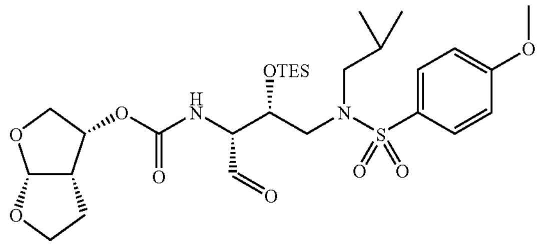

15

I. a. TFA/$CH_2Cl_2$; b. bisfurancarbonate/i-$Pr_2NEt$/DMAP;
II. a.$Et_3SiCl$/Imidazole/DMF; b. $H_2$/20% $Pd(OH)_2$—C/PrOH;
III. Des-Martin reagent/$CH_2Cl_2$ Scheme 4

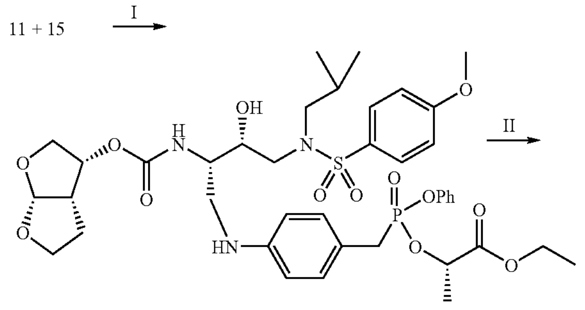

16

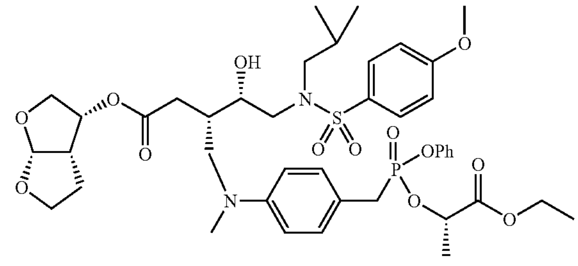

17

I. a. $NaBH_3CN$/HOAc/EtOAc; b. 2% HF/$CH_3CN$;
II. HCHO/$NaBH_3CN$/HOAc/EtOAc

Example 8

Compound 8: To the suspension of compound 7 (15.8 g, 72.5 mmol) in toluene (140 mL) was added DMF (1.9 mL), followed by thionyl chloride (53 mL, 725 mmol). The reaction mixture was heated at 60° C. for 5 hrs, and evaporated under reduced pressure. The mixture was coevaporated with toluene (2×), EtOAc, and $CH_2Cl_2$ (2×) to afford a brown solid. To the solution of the brown solid in $CH_2Cl_2$ at 0° C. was added phenol (27.2 g, 290 mmol), followed by slow addition of pyridine (35 mL, 435 mmol). The reaction mixture was allowed to warm to 25° C. and stirred for 14 hrs. Solvents were removed under reduced pressure. The mixture was diluted with EtOAc, and washed with water (3×) and brine (1×), and dried over $MgSO_4$. Concentration gave a dark oil, which was purified by flash column chromatography (hexanes/EtOAc=4/1 to 1/1) to afford compound 8 (12.5 g).

Example 9

Compound 9: To a solution of compound 8 (2.21 g, 6 mmol) in THF (30 mL) was added 12 mL of 1.0 N NaOH solution. The mixture was stirred at 25° C. for 2 hours, and THF was removed under reduced pressure. The mixture was diluted with water, and acetic acid (343 mL, 6 mmol) was added. The aqueous phase was washed with EtOAc (3×), and then acidified with concentrated HCl until pH=1. The aqueous was extracted with EtOAc (3×). The combined organic layer was washed with water (1×) and brine (1×), and dried over $MgSO_4$. Concentration under reduced pressure gave compound 9 as a solid (1.1 g).

Example 10

Compound 10: To a suspension of compound 9 (380 mg, 1.3 mmol) in toluene (2.5 mL) was added thionyl chloride (1 mL, 13 mmol), followed by DMF (1 drop). The mixture was heated at 60° C. for 2 hours. The solvent and reagent were removed under reduced pressure. The mixture was coevaporated with toluene (2×) and $CH_2Cl_2$ to give a white solid. To the solution of the above solid in $CH_2Cl_2$ (5 ml) at −20° C. was added ethyl lactate (294 μL, 2.6 mmol), followed by pyridine (420 μL, 5.2 mmol). The mixture was warmed to 25° C. and stirred for 12 hours. The reaction mixture was concentrated under reduced pressure to give a yellow solid, which was purified by flash column chromatography to generate compound 10 (427 mg).

Example 11

Compound 11: To a solution of compound 10 (480 mg) in EtOAc (20 mL) was added 10% Pd—C (80 mg). The reaction mixture was hydrogenated for 6 hrs. The mixture was stirred with celite for 5 mins, and filtered through a pad of celite. Concentration under reduced pressure gave compound 11 (460 mg).

Example 12

Compound 12 was prepared by the methods of the Examples herein

Example 13

Compound 13: To a solution of compound 12 (536 mg, 1.0 mmol) in $CH_2Cl_2$ (10 mL) was added trifluoroacetic acid (2 mL). The mixture was stirred for 2 hrs, and was concentrated under reduced pressure. The liquid was coevaporated with $CH_2Cl_2$ (3×) and EtOAc (3×) to give a brown solid. To the solution of above brown solid in acetonitrile (6.5 mL) at 0° C. was added bisfurancarbonate (295 mg, 1.0 mmol), followed by diisopropylethylamine (350 μL, 2.0 mmol) and DMAP (24 mg). The mixture was warmed to 25° C., and was stirred for 12 hrs. The mixture was diluted with EtOAc, and was washed sequentially with water (2×), 0.5 N HCl (2×), water (2×), 0.5 N NaOH solution (2×), water (2×), and brine (1×), and dried over $MgSO_4$. Purification by flash column chromatography (hexanes/EtOAc=1/1) afford compound 13 (540 mg).

Example 14

Compound 14: To a solution of compound 13 (400 mg, 0.67 mmol) in DMF (3 mL) was added imidazole (143 mg, 2.10 mmol), followed by triethylchlorosilane (224 μL, 1.34 mmol). The mixture was stirred for 12 hours. The mixture was diluted with EtOAc, and was washed with water (5×) and brine, and dried over $MgSO_4$. Purification by flash column chromatography (hexanes/EtOAc=2/1) gave a white solid (427 mg). To the solution of above solid in isopropanol (18 mL) was added 20% palladium(II) hydroxide on carbon (120 mg). The mixture was hydrogenated for 12 hours. The mixture was stirred with celite for 5 mins, and filtered through a pad of celite. Concentration under reduced pressure gave compound 14(360 mg).

Example 15

Compound 15: To a solution of compound 14 (101 mg, 0.18 mmol) in $CH_2Cl_2$ (5 mL) was added Dess-Martin periodiane (136 mg, 0.36 mmol). The mixture was stirred for 1 hour. Purification by flash column chromatography (hexanes/EtOAc=2/1) gave compound 15 (98 mg).

Example 16

Compound 16: To a solution of compound 15 (50 mg, 0.08 mmol) in EtOAc (0.5 mL) was added compound 11 (150 mg, 0.41 mmol). The mixture was cooled to 0° C., acetic acid (19 μL, 0.32 mmol) was added, followed by sodium cyanoborohydride (10 mg, 0.16 mmol). The mixture was warmed to 25° C., and was stirred for 14 hrs. The mixture was diluted with EtOAc, and was washed with water (3×) and brine, and was dried over $MgSO_4$. Concentration gave a oil. To the solution of above oil in acetonitrile (2.5 mL) was added 48% $HF/CH_3CN$ (0.1 mL). The mixture was stirred for 30 minutes, and was diluted with EtOAc. The organic phase was washed with water (3×) and brine (1×), and was dried over $MgSO_4$. Purification by flash column chromatography ($CH_2Cl_2$/iP-rOH=100/3) gave compound 16 (50 mg): $^1H$ NMR ($CDCl_3$) δ 7.72 (2H, d, J=8.9 Hz), 7.15-7.05 (7H, m), 7.30 (2H, d, J=8.9 Hz), 6.64 (2H, m), 5.73 (1H, m), 5.45 (1H, m), 5.13 (1H, m), 4.93 (1H, m), 4.22-3.75 (11H, m), 3.4 (4H, m), 3.35-2.80 (5H, m), 2.1-1.8 (3H, m), 1.40-1.25 (6H, m), 0.94 (6H, m).

Example 17

Compound 17: To a solution of compound 16 (30 mg, 0.04 mmol) in EtOAc (0.8 mL) was added 37% formaldehyde (26 μL, 0.4 mmol). The mixture was cooled to 0° C., acetic acid (20 μL, 0.4 mmol) was added, followed by sodium cyanoborohydride (22 mg, 0.4 mmol). The mixture was warmed to 25° C., and was stirred for 14 hrs. The mixture was diluted with EtOAc, and was washed with water (3×) and brine, and was dried over $MgSO_4$. Purification by flash column chromatography ($CH_2Cl_2$/iPrOH=100/3) gave compound 17 (22 mg): $^1H$ NMR ($CDCl_3$) δ 7.63 (2H, m), 7.3-6.9 (9H, m), 6.79 (2H, m), 5.68 (1H, m), 5.2 (1H, m), 5.10 (1H, m), 4.95 (1H, m), 4.22 (2H, m), 4.2-3.7 (21H, m), 2.0-1.7 (3H, m), 1.4-1.2 (6H, m), 0.93 (6H, m).

Scheme 5

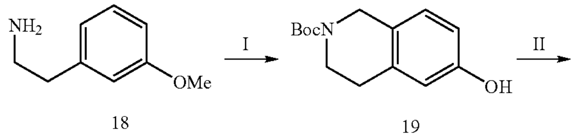

18 19

-continued

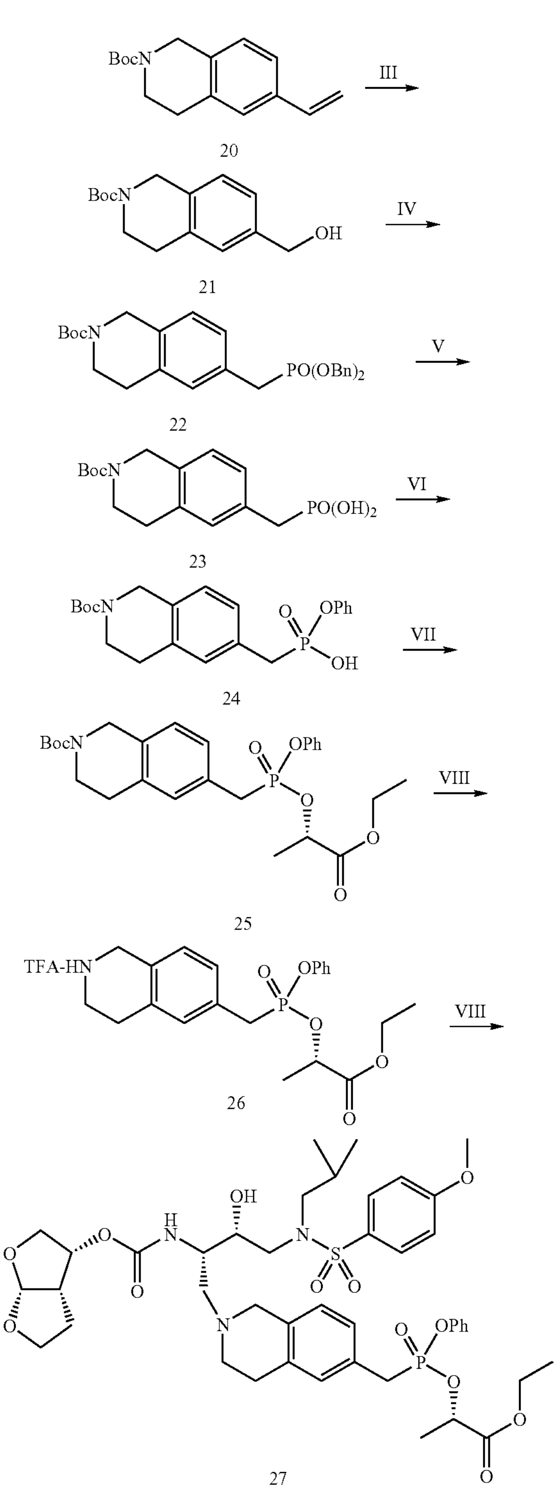

20 21 22 23 24 25 26 27

I. a. HCHO/100 C.; b. HCl/100 C.; c. HBr/120 C.; d. $Boc_2O/Na_2CO_3$
II. a.$Tf_2NPh/Cs_2CO_3$; b. $Bu_3Sn$ CH═$CH_2$/LiCl/$PdCl_2(PPh_3)_2$/90 C.;
III. a. $NaIO4/OsO_4$; b. $NaBH_4$;
IV. a. $CBr_4/PPh_3$; b. $(BnO)_2POH/Cs_2CO_3$;
V. $H_2$/10% Pd-C;
VI. a. PhOH/DCC; b. NaOH; C. HCl;
VII. Ethyl lactate/BOP; VIII.TFA/$CH_2Cl_2$;
VIII. compound 15/$NaBH_3CN$/HOAc.

Example 18

Compound 18: Compound 18 was purchased from Aldrich.

Example 19

Compound 19: To compound 18 (12.25 g, 81.1 mmol) was added 37% formaldehyde (6.15 mL, 82.7 mmol) slowly. The mixture was heated at 100° C. for 1 hour. The mixture was cooled to 25° C., and was diluted with benzene, and was washed with water (2×). Concentration under reduced pressure gave a yellow oil. To above oil was added 20% HCl (16 mL), and the mixture was heated at 100° C. for 12 hours. The mixture was basified with 40% KOH solution at 0° C., and was extracted with EtOAc (3×). The combined organic layer was washed with water and brine, and was dried over $MgSO_4$. Concentration gave a oil. To the oil was added 48% HBr (320 mL), and the mixture was heated at 120° C. for 3 hours. Water was removed at 100° C. under reduced pressure to give a brown solid. To the solution of above solid in water/dioxane (200 mL/200 mL) at 0° C. was added sodium carbonate (25.7 g, 243 mmol) slowly, followed by di-tert-butyl dicarbonate (19.4 g, 89 mmol). The mixture was warmed to 25° C. and stirred for 12 hours. Dioxane was removed under reduced pressure, and the remaining was extracted with EtOAc (3×). The combined organic phase was washed with water (3×) and brine, and was dried over $MgSO_4$. Purification by flash column chromatography (hexanes/EtOAc=4/1 to 3/1) gave compound 19 as white solid (13.6 g).

Example 20

Compound 20: To a solution of compound 19 (2.49 g, 10 mmol) in $CH_2Cl_2$ (100 mL) was added N-phenyltrifluoromethanesulfonimide (3.93 g, 11 mmol), followed by cesium carbonate (3.58 g, 11 mmol). The mixture was stirred for 48 hours. The solvent was removed under reduced pressure, and ethyl acetate was added. The reaction mixture was washed with water (3×) and brine (1×), and was dried over $MgSO_4$. Purification by flash column chromatography (hexanes/EtOAc=6/1) gave a white solid (3.3 g). To the solution of above solid (2.7 g, 7.1 mmol) in DMF (40 mL) was added lithium chloride (2.11 g, 49.7 mmol), followed by dichlorobis(triphenylphosphine)palladium(II) (100 mg, 0.14 mmol). The mixture was stirred for 3 minutes under high vacuum and recharged with nitrogen. To the above solution was added tributylvinyltin (2.07 mL, 7.1 mmol). The reaction mixture was heated at 90° C. for 3 hours and cooled to 25° C. Water was added to the reaction, and the mixture was extracted with ethyl acetate (3×). The combined organic layer was washed with water (6×) and brine, and dried over $MgSO_4$. Concentration gave an oil. The oil was diluted with $CH_2Cl_2$ (5 mL), water (128 μL, 7.1 mmol) and DBU (1 mL, 7.1 mmol) were added. The mixture was stirred for 5 minutes, and was subjected to flash column chromatography (hexanes/EtOAc=9/1). Compound 20 was obtained as white solid (1.43 g).

Example 21

Compound 21: To a solution of compound 20 (1.36 g, 5.25 mmol) in ethyl acetate (16 mL) was added water (16 mL), followed by 2.5% osmium tetraoxide/tert-butanol (2.63 mL). Sodium periodate (2.44 g) was added in portions over 2 minutes period. The mixture was stirred for 45 minutes, and was diluted with ethyl acetate. The organic layer was separated and washed with water (3×) and brine (1×), and dried over $MgSO_4$. Concentration gave a brown solid. To the solution of above solid in methanol (100 mL) at 0° C. was added sodium borohydride. The mixture was stirred for 1 hour at 0° C., and was quenched with saturated $NH_4Cl$ (40 mL). Methanol was removed under reduced pressure, and the remaining was extracted with EtOAc (3×). The combined organic layer was washed with water and brine, and was dried over $MgSO_4$. Purification by flash column chromatography (hexanes/EtOAc=2/1) gave compound 21 (1.0 g).

Example 22

Compound 22: To a solution of compound 21 (657 mg, 2.57 mmol) in $CH_2Cl_2$ (2 mL) was added a solution of tetrabromocarbon (1.276 g, 3.86 mmol) in $CH_2Cl_2$ (2 mL). To the above mixture was added a solution of triphenylphsophine (673 mg, 2.57 mmol) in $CH_2Cl_2$ (2 mL) over 30 minutes period. The mixture was stirred for 2 hours, and was concentrated under reduced pressure. Purification by flash column chromatography (hexanes/EtOAc=9/1) gave the bromide intermediate (549 mg). To the solution of above bromide (548 mg, 1.69 mmol) in acetonitrile (4.8 mL) was added dibenzyl phosphite (0.48 mL, 2.19 mmol), followed by cesium carbonate (828 mg, 2.54 mmol). The mixture was stirred for 48 hours, and was diluted with EtOAc.

The mixture was washed with water (3×) and brine, and was dried over $MgSO_4$. Purification by flash column chromatography (hexanes/EtOAc=3/1 to 100% EtOAc) gave compound 22 (863 mg).

Example 23

Compound 23: To a solution of compound 22 (840 mg) in ethanol (80 mL) was added 10% palladium on carbon (200 mg). The mixture was hydrogenated for 2 hours. The mixture was stirred with celite for 5 mins, and was filtered through a pad of celite. Concentration under reduced pressure gave compound 23 (504 mg).

Example 24

Compound 24: To a solution of compound 23 (504 mg, 1.54 mmol) in pyridine (10.5 mL) was added phenol (1.45 g, 15.4 mmol), followed by DCC (1.28 g, 6.2 mmol). The mixture was heated at 65° C. for 3 hours, and pyridine was removed under reduced pressure. The mixture was diluted with EtOAc (5 ml), and was filtered and washed with EtOAc (2×5 mL). Concentration gave a oil, which was purified by flash column chromatography ($CH_2Cl_2$/isopropanol=100/3) to give diphenylphosphonate intermediate (340 mg). To a solution of above compound (341 mg, 0.71 mmol) in THF (1 mL) was added 0.85 mL of 1.0 N NaOH solution. The mixture was stirred at 25° C. for 3 hours, and THF was removed under reduced pressure. The mixture was diluted with water, and was washed with EtOAc (3×), and then acidified with concentrated HCl until pH=1. The aqueous was extracted with EtOAc (3×). The combined organic layer was washed with water (1×) and brine (1×), and dried over $MgSO_4$. Concentration under reduced pressure gave compound 24 as a solid (270 mg).

Example 25

Compound 25: To a solution of compound 24 (230 mg, 0.57 mmol) in DMF (2 mL) was added ethyl(s)-lactate (130 μL, 1.14 mmol), followed by diisopropylethylamine (400 μL, 2.28 mmol) and benzotriazol-1-yloxytris(dimethylamino)

phosphonium hexafluorophosphate (504 mg, 1.14 mmol). The mixture was stirred for 14 hours, was diluted with EtOAc. The organic phase was washed with water (5×) and brine (1×), and was dried over $MgSO_4$. Purification by flash column chromatography ($CH_2Cl_2$/isopropanol=100/3) gave compound 25 (220 mg).

Example 26

Compound 26: To a solution of compound 25 (220 mg) in $CH_2Cl_2$ (2 mL) was added trifluoroacetic acid (1 mL). The mixture was stirred for 2 hrs, and was concentrated under reduced pressure. The mixture was diluted with EtOAc, and was washed with saturated sodium carbonate solution, water, and brine, and was dried over $MgSO_4$. Concentration gave compound 26 (170 mg).

Example 27

Compound 27: To a solution of compound 15 (258 mg, 0.42 mmol) in EtOAc (2.6 mL) was added compound 26 (170 mg, 0.42 mmol), followed by acetic acid (75 μL, 1.26 mmol). The mixture was stirred for 5 minutes, and sodium cyanoborohydride (53 mg, 0.84 mmol) was added. The mixture was stirred for 14 hrs. The mixture was diluted with EtOAc, and was washed with saturated sodium bicarbonate solution, water (3×) and brine, and was dried over $MgSO_4$. Purification by flash column chromatography ($CH_2Cl_2$/iPrOH=100/4 to 100/6) gave the intermediate (440 mg). To the solution of above compound (440 mg) in acetonitrile (10 mL) was added 48% HF/$CH_3CN$ (0.4 mL). The mixture was stirred for 2 hours, and acetonitrile was removed under reduced pressure. The remaining was diluted with EtOAc, and was washed with water (3×) and brine (1×), and was dried over $MgSO_4$. Purification by flash column chromatography ($CH_2Cl_2$/iPrOH=100/5) gave compound 27 (120 mg): $^1H$ NMR ($CDCl_3$) δ 7.70 (2H, m), 7.27 (2H, m), 7.15 (5H, m), 6.95 (3H, m), 5.73 (1H, m), 5.6-5.4 (1H, m), 5.16 (1H, m), 4.96 (1H, m), 4.22-3.60 (13H, m), 3.42 (2H, m), 3.4-2.6 (11H, m), 2.1-3.8 (3H, m), 1.39 (3H, m), 1.24 (3H, m), 0.84 (6H, m).

Scheme 6

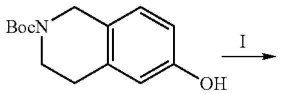

19

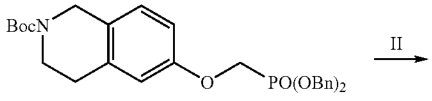

28

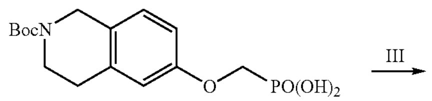

29

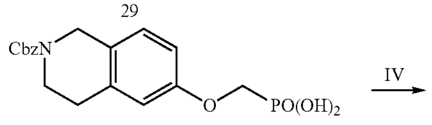

30

-continued

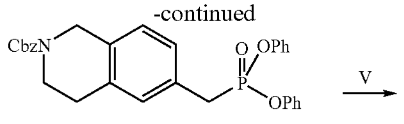

31

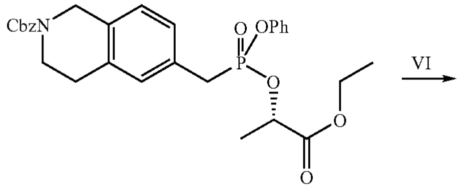

32

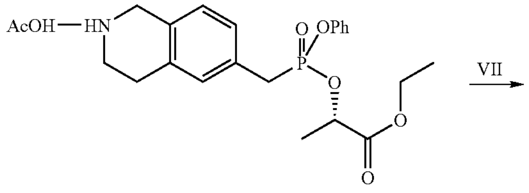

33

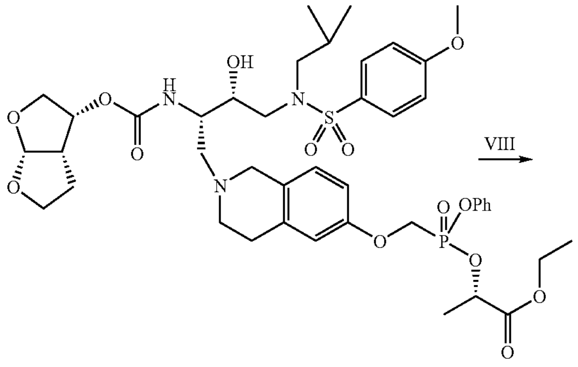

34

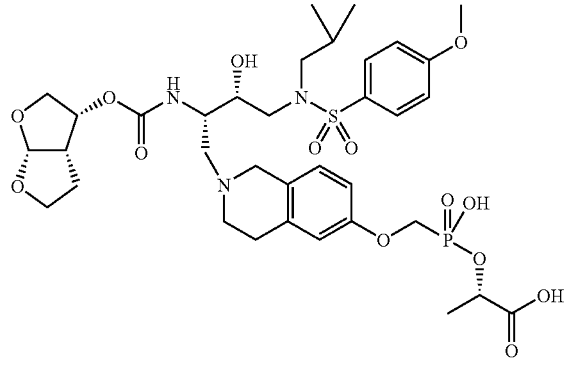

35

I. $TfOCH_2PO(OBn)_2/CsCO_3$
II. $H_2$/10% Pd-C;
III. a. TFA/$CH_2Cl_2$; b. CbzCl/NaOH;
IV. a.$SOCl_2$/60 C;b. PhOH/pyridine;V. a. NaOH/THF; b. HCl; c. $SOCl_2$/60 C.; d. Ethyl (s) Lactate/pyridine; VI. $H_2$/10% Pd-C/HOAc;
VII. a. compound 15/$NaBH_3CN$/HOAc; b. 2% HF/$CH_3CN$;
VIII. esterase/1.0 PBS buffer/$CH_3CN$/DMSO

Example 28

Compound 28: To a solution of compound 19 (7.5 g, 30 mmol) in acetonitrile (420 mL) was added dibenzyl triflate (17.8 g, 42 mmol), followed by cesium carbonate (29.4 g, 90 mmol). The mixture was stirred for 2.5 hours, and was filtered. Acetonitrile was removed under reduced pressure, and the remaining was diluted with EtOAc. The mixture was washed with water (3×) and brine, and was dried over $MgSO_4$. Purification by flash column chromatography (hexanes/EtOAc=2/1 to 1/1) gave compound 28 (14.3 g).

Example 29

Compound 29: To a solution of compound 28 (14.3 g) in ethanol (500 mL) was added 10% palladium on carbon (1.45 g). The mixture was hydrogenated for 2 hours. The mixture was stirred with celite for 5 mins, and was filtered through a pad of celite. Concentration under reduced pressure gave compound 29 (9.1 g).

Example 30

Compound 30: To a solution of compound 29 (9.1 g) in $CH_2Cl_2$ (60 mL) was added trifluoroacetic acid (30 mL). The mixture was stirred for 4 hrs, and was concentrated under reduced pressure. The mixture was coevaporated with $CH_2Cl_2$ (3×) and toluene, and was dried under high vacuum to give a white solid. The white solid was dissolved in 2.0 N NaOH solution (45 mL, 90 mmol), and was cooled to 0° C. To the above solution was added slowly a solution of benzyl chloroformate (6.4 mL, 45 mmol) in toluene (7 mL). The mixture was warmed to 25° C., and was stirred for 6 hours. 2.0 N sodium hydroxide was added to above solution until pH=11. The aqueous was extracted with ethyl ether (3×), and was cooled to 0° C. To the above aqueous phase at 0° C. was added concentrated HCl until pH=1. The aqueous was extracted with EtOAc (3×). The combine organic layers were washed with brine, and were dried over $MgSO_4$. Concentration gave compound 30 (11.3 g) as a white solid.

Example 31

Compound 31: To the suspension of compound 30 (11.3 g, 30 mmol) in toluene (150 mL) was added thionyl chloride (13 mL, 180 mmol), followed by DMF (a few drops). The reaction mixture was heated at 65° C. for 4.5 hrs, and evaporated under reduced pressure. The mixture was coevaporated with toluene (2×) to afford a brown solid. To the solution of the brown solid in $CH_2Cl_2$ (120 ml) at 0° C. was added phenol (11.28 g, 120 mmol), followed by slow addition of pyridine (14.6 mL, 180 mmol). The reaction mixture was allowed to warm to 25° C. and stirred for 14 hrs. Solvents were removed under reduced pressure. The mixture was diluted with EtOAc, and washed with water (3×) and brine (1×), and dried over $MgSO_4$. Concentration gave a dark oil, which was purified by flash column chromatography (hexanes/EtOAc=3/1 to 1/1) to afford compound 31 (9.8 g).

Example 32

Compound 32: To a solution of compound 31 (9.8 g, 18.5 mmol) in THF (26 mL) was added 20.3 mL of 1.0 N NaOH solution. The mixture was stirred at 25° C. for 2.5 hours, and THF was removed under reduced pressure. The mixture was diluted with water, and was washed with EtOAc (3×). The aqueous phase was cooled to 0° C., and was acidified with concentrated HCl until pH=1. The aqueous was extracted with EtOAc (3×). The combined organic layer was washed with water (1×) and brine (1×), and dried over $MgSO_4$. Concentration under reduced pressure gave a solid (8.2 g). To a suspension of above solid (4.5 g, 10 mmol) in toluene (50 mL) was added thionyl chloride (4.4 mL, 60 mmol), followed by DMF (0.2 mL). The mixture was heated at 70° C. for 3.5 hours. The solvent and reagent were removed under reduced pressure. The mixture was coevaporated with toluene (2×) to give a white solid. To the solution of the above solid in $CH_2Cl_2$ (40 mL) at 0° C. was added ethyl(s)-lactate (2.3 mL, 20 mmol), followed by pyridine (3.2 mL, 40 mmol). The mixture was warmed to 25° C. and stirred for 12 hours. The reaction mixture was concentrated under reduced pressure, and was diluted with EtOAc. The organic phase was washed with 1 N HCl, water, and brine, and was dried over $MgSO_4$. Purification by flash column chromatography (hexanes/EtOAc=2/1 to 1/1) gave compound 32 (4.1 g).

Example 33

Compound 33: To a solution of compound 32 (3.8 g, 6.9 mmol) in EtOAc/EtOH (30 mL/30 mL) was added 10% palladium on carbon (380 mg), followed by acetic acid (400 μL, 6.9 mmol). The mixture was hydrogenated for 3 hours. The mixture was stirred with celite for 5 mins, and was filtered through a pad of celite. Concentration under reduced pressure gave compound 33 (3.5 g).

Example 34

Compound 34: To a solution of compound 15 (1.70 g, 2.76 mmol) in EtOAc (17 mL) was added compound 33 (3.50 g, 6.9 mmol). The mixture was stirred for 5 minutes, and was cooled to 0° C., and sodium cyanoborohydride (347 mg, 5.52 mmol) was added. The mixture was stirred for 6 hrs. The mixture was diluted with EtOAc, and was washed with saturated sodium bicarbonate solution, water (3×) and brine, and was dried over $MgSO_4$. Purification by flash column chromatography ($CH_2Cl_2$/iPrOH=100/6) gave the intermediate (3.4 g). To the solution of above compound (3.4 g) in acetonitrile (100 mL) was added 48% HF/$CH_3CN$ (4 mL). The mixture was stirred for 2 hours, and acetonitrile was removed under reduced pressure. The remaining was diluted with EtOAc, and was washed with saturated sodium carbonate, water (3×), and brine (1×), and was dried over $MgSO_4$. Purification by flash column chromatography ($CH_2Cl_2$/iPrOH=100/5) gave compound 34 (920 mg): $^1H$ NMR ($CDCl_3$) δ 7.71 (2H, m), 7.38-7.19 (5H, m), 6.92 (3H, m), 6.75 (2H, m), 5.73 (1H, m), 5.57-5.35 (1H, m), 5.16 (2H, m), 4.5 (2H, m), 4.2-3.6 (13H, m), 3.25-2.50 (11H, m), 2.0-1.8 (3H, m), 1.5 (3H, m), 1.23 (3H, m), 0.89 (6H, m).

Example 35

Compound 35: To a solution of compound 34 (40 mg) in $CH_3CN$/DMSO (1 mL/0.5 mL) was added 1.0 M PBS buffer (5 mL), followed by esterase (200 μL). The mixture was heated at 40° C. for 48 hours. The mixture was purified by reverse phase HPLC to give compound 35 (11 mg).

Scheme 7

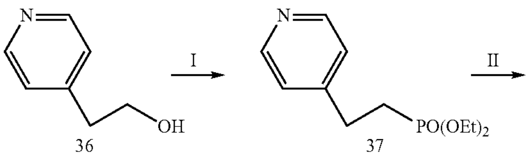

36 37

-continued

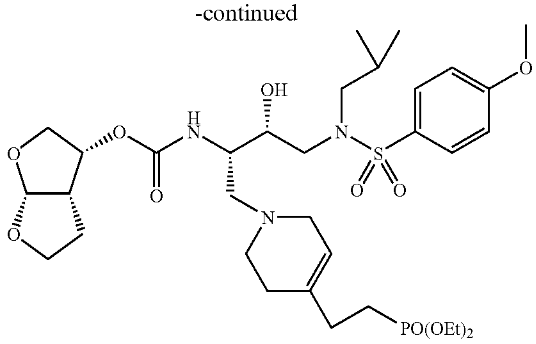

38

I. a. $SOCl_2$/toluene/60 C.; b. $P(OEt)_3$/toluene/120 C.;
II. a.compound 14/$Tf_2O$; b. $NaBH_4$/EtOH/HOAc; c. 2% HF/$CH_3CN$

Example 36

Compound 36: Compound 36 was purchased from Aldrich.

Example 37

Compound 37: To a solution of compound 36 (5.0 g, 40 mmol) in chloroform (50 mL) was added thionyl chloride (12 mL) slowly. The mixture was heated at 60° C. for 2.5 hours. The mixture was concentrated under reduced pressure to give a yellow solid. To the suspension of above solid (5.2 g, 37 mmol) in toluene (250 mL) was added triethyl phosphite (19 mL, 370 mmol). The mixture was heated at 120° C. for 4 hours, and was concentrated under reduced pressure to give a brown solid. The solid was dissolved in EtOAc, and was basified with 1.0 N NaOH. The organic phase was separated and was washed with water (2×) and brine, and was dried over $MgSO_4$. Purification by flash column chromatography ($CH_2Cl_2$/iPrOH=9/1) gave compound 37 (4.8 g).

Example 38

Compound 38: To a solution of compound 14 (100 mg, 0.16 mmol) and compound 37 (232 mg, 0.74 mmol) in $CH_2Cl_2$ (1 mL) at −40° C. was added triflic anhydride (40 μL, 0.24 mmol) slowly. The mixture was warmed to 25° C. slowly, and was stirred for 12 hours. The mixture was concentrated, and was diluted with EtOH/EtOAc (2 mL/0.4 mL). To the above solution at 0° C. was added sodium borohydride (91 mg) in portions. The mixture was stirred at 0° C. for 3 hours, and was diluted with EtOAc. The mixture was washed with saturated sodium bicarbonate, water, and brine, and was dried over $MgSO_4$. Purification by flash column chromatograph ($CH_2Cl_2$/iPrOH=100/5 to 100/10) gave the intermediate (33 mg). To the solution of above intermediate in acetonitrile (2.5 mL) was added 48% HF/$CH_3CN$ (0.1 mL). The mixture was stirred for 30 minutes, and was diluted with EtOAc. The organic solution was washed with 0.5 N sodium hydroxide, water, and brine, was dried over $MgSO_4$. Purification by reverse HPLC gave compound 38 (12 mg): $^1H$ NMR ($CDCl_3$) δ 7.72 (2H, d, J=8.9 Hz), 7.02 (2H, d, J=8.9 Hz), 5.70 (1H, m), 5.45 (1H, m), 5.05 (1H, m), 4.2-3.4 (19H, m), 3.4-2.8 (5H, m), 2.45-2.20 (4H, m), 2.15-1.81 (5H, m), 1.33 (6H, m), 0.89 (6H, m).

Scheme 8

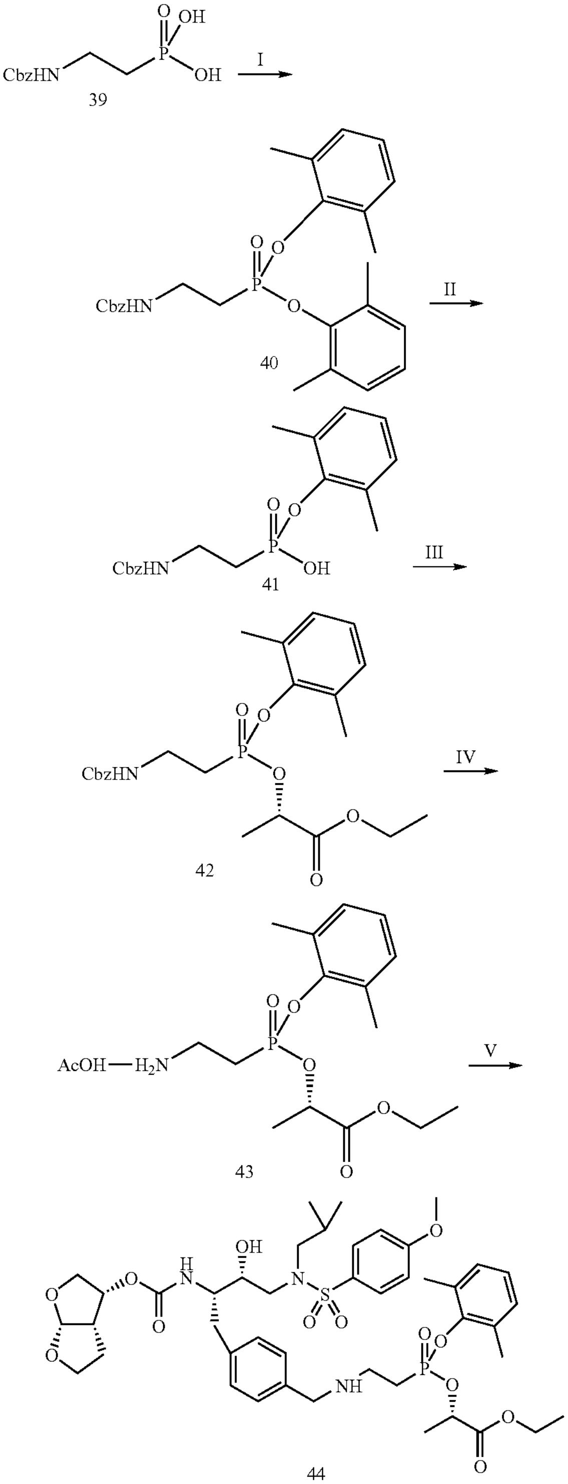

39, 40, 41, 42, 43, 44

I. a.. $SOCl_2$/toluene/60 C.; b. ArOH/pyridine;
II. a. NaOH/THF/$H_2O$; b. HCl;
III. b. $SOCl_2$/toluene/60 C.; c. ethyl lactate/pyridine;
IV. $H_2$/10% Pd-C/EtOAc/HOAc;
V. a. compound 6/$MgSO_4$; b. HOAc/$NaCNBH_3$ Example 39

Compound 39 was prepared by the methods of the previous Examples.

Example 40

Compound 40: To the suspension of compound 39 (4.25 g, 16.4 mmol) in toluene (60 mL) was added thionyl chloride (7.2 mL, 99 mmol), followed by DMF (a few drops). The reaction mixture was heated at 65° C. for 5 hrs, and evaporated under reduced pressure. The mixture was coevaporated with toluene (2×) to afford a brown solid. To the solution of the brown solid in $CH_2Cl_2$ (60 ml) at 0° C. was added 2,6-dimethylphenol (8.1 g, 66 mmol), followed by slow addition of pyridine (8 mL, 99 mmol). The reaction mixture was allowed to warm to 25° C. and stirred for 14 hrs. Solvents were removed under reduced pressure. The mixture was diluted with EtOAc, and washed with water (3×) and brine (1×), and dried over $MgSO_4$. Purification by flash column chromatography (hexanes/EtOAc=3/1 to 1/1) afforded compound 40 (1.38 g).

Example 41

Compound 41: To a solution of compound 40 (1.38 g, 1.96 mmol) in THF (6 mL) was added 3.55 mL of 1.0 N NaOH solution. The mixture was stirred at 25° C. for 24 hours, and THF was removed under reduced pressure. The mixture was diluted with water, and was washed with EtOAc (3×). The aqueous phase was cooled to 0° C., and was acidified with concentrated HCl until pH=1. The aqueous was extracted with EtOAc (3×). The combined organic layer was washed with water (1×) and brine (1×), and dried over $MgSO_4$. Concentration under reduced pressure gave compound 41 as a white solid (860 mg).

Example 42

Compound 42: To a suspension of compound 41 (1.00 g, 2.75 mmol) in toluene (15 mL) was added thionyl chloride (1.20 mL, 16.5 mmol), followed by DMF (3 drops). The mixture was heated at 65° C. for 5 hours. The solvent and reagent were removed under reduced pressure. The mixture was coevaporated with toluene (2×) to give a brown solid. To the solution of the above solid in $CH_2Cl_2$ (11 mL) at 0° C. was added ethyl(s)-lactate (1.25, 11 mmol), followed by pyridine (1.33 mL, 16.6 mmol). The mixture was warmed to 25° C. and stirred for 12 hours. The reaction mixture was concentrated under reduced pressure, and was diluted with EtOAc. The organic phase was washed with 1 N HCl, water, and brine, and was dried over $MgSO_4$. Purification by flash column chromatography (hexanes/EtOAc=1.5/1 to 1/1) gave compound 42 (470 mg).

Example 43

Compound 43: To a solution of compound 42 (470 mg) in EtOH (10 mL) was added 10% palladium on carbon (90 mg), followed by acetic acid (150 μL). The mixture was hydrogenated for 6 hours. The mixture was stirred with celite for 5 mins, and was filtered through a pad of celite. Concentration under reduced pressure gave compound 43 (400 mg).

Example 44

Compound 44: To a solution of compound 6 (551 mg, 0.93 mmol) in 1,2-dichloroethane (4 mL) was added compound 43 (400 mg, 1.0 mmol), followed by $MgSO_4$ (1 g). The mixture was stirred for 3 hours, and acetic acid (148 μL) and sodium cyanoborohydride (117 mg, 1.86 mmol) were added sequentially. The mixture was stirred for 1 hour. The mixture was diluted with EtOAc, and was washed with saturated sodium bicarbonate solution, water (3×) and brine, and was dried over $MgSO_4$. Purification by flash column chromatography (EtOAc to EtOAc/EtOH=9/1) gave compound 44. Compound 44 was dissolved in $CH_2Cl_2$ (25 mL), and trifluoroacetic acid (100 μL) was added. The mixture was concentrated to give compound 44 as a TFA salt (560 mg): $^1$H NMR ($CDCl_3$) δ 7.74 (2H, m), 7.39 (2H, m), 7.20 (2H, m), 7.03 (5H, m), 5.68 (1H, m), 5.43 (1H, m), 5.01 (1H, m), 4.79 (1H, m), 4.35-4.20 (4H, m), 4.18-3.4 (11H, m), 3.2-2.6 (9H, m), 2.30 (6H, m), 1.82 (1H, m), 1.70 (2H, m), 1.40-1.18 (6H, m), 0.91 (6H, m).

Scheme 9

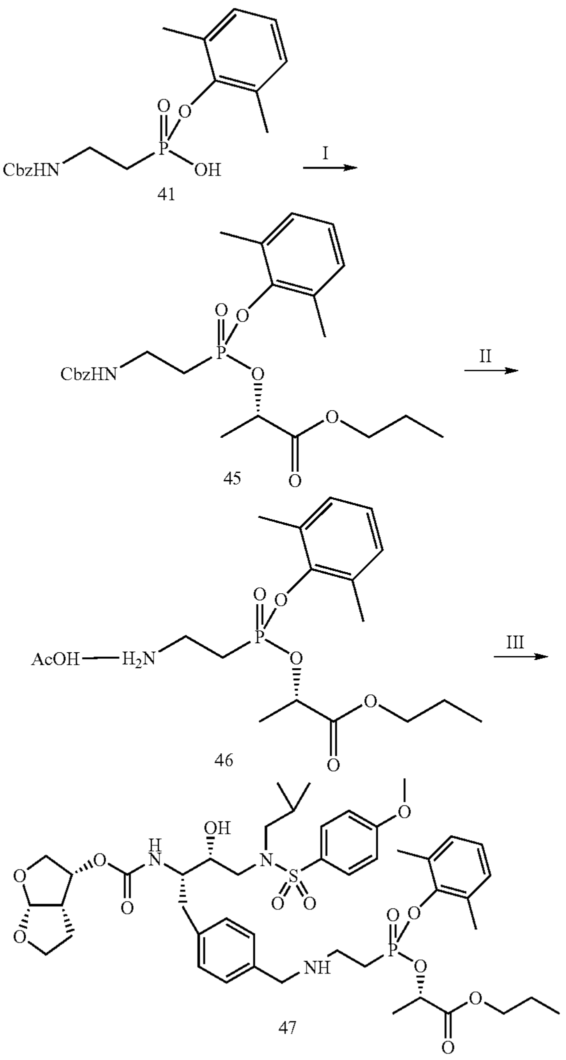

41

45

46

47

I. a. $SOCl_2$/toluene/60 C.; c. propyl (s)-lactate/pyridine;
II. $H_2$/10% Pd-C/EtOAc/HOAc;
III. a. compound 6/$MgSO_4$; b. HOAc/$NaCNBH_3$ Example 45

Compound 45: To a suspension of compound 41 (863 mg, 2.4 mmol) in toluene (13 mL) was added thionyl chloride (1.0 mL, 14.3 mmol), followed by DMF (3 drops). The mixture was heated at 65° C. for 5 hours. The solvent and reagent were removed under reduced pressure. The mixture was coevaporated with toluene (2×) to give a brown solid. To the solution of the above solid in $CH_2Cl_2$ (10 mL) at 0° C. was added propyl(s)-lactate (1.2 mL, 9.6 mmol), followed by triethylamine (2.0 mL, 14.4 mmol). The mixture was warmed to 25° C. and stirred for 12 hours. The reaction mixture was concentrated under reduced pressure, and was diluted with EtOAc. The organic phase was washed with water and brine, and was dried over $MgSO_4$. Purification by flash column chromatography (hexanes/EtOAc=1.5/1 to 1/1) gave compound 45 (800 mg).

Example 46

Compound 46: To a solution of compound 45 (785 mg) in EtOH (17 mL) was added 10% palladium on carbon (150 mg), followed by acetic acid (250 μL). The mixture was hydrogenated for 16 hours. The mixture was stirred with celite for 5 mins, and was filtered through a pad of celite. Concentration under reduced pressure gave compound 46 (700 mg).

Example 47

Compound 47: To a solution of compound 6 (550 mg, 0.93 mmol) in 1,2-dichloroethane (4 mL) was added compound 43 (404 mg, 1.0 mmol), followed by $MgSO_4$ (1 g). The mixture was stirred for 3 hours, and acetic acid (148 AL) and sodium cyanoborohydride (117 mg, 1.86 mmol) were added sequentially. The mixture was stirred for 1 hour. The mixture was diluted with EtOAc, and was washed with saturated sodium bicarbonate solution, water (3×) and brine, and was dried over $MgSO_4$. Purification by flash column chromatography (EtOAc to EtOAc/EtOH=9/1) gave compound 47. Compound 47 was dissolved in $CH_2Cl_2$ (25 mL), and trifluoroacetic acid (100 AL) was added. The mixture was concentrated to give compound 47 as a TFA salt (650 mg): $^1H$ NMR ($CDCl_3$) δ 7.74 (2H, m), 7.41 (2H, m), 7.25-7.1 (2H, m), 7.02 (5H, m), 5.65 (1H, m), 5.50 (1H, m), 5.0-4.75 (2H, m), 4.25-4.05 (4H, m), 4.0-3.4 (11H, m), 3.2-2.6 (9H, m), 2.31 (6H, m), 1.82-1.51 (3H, m), 1.45-1.2 (5H, m), 0.93 (9H, m).

Scheme 10

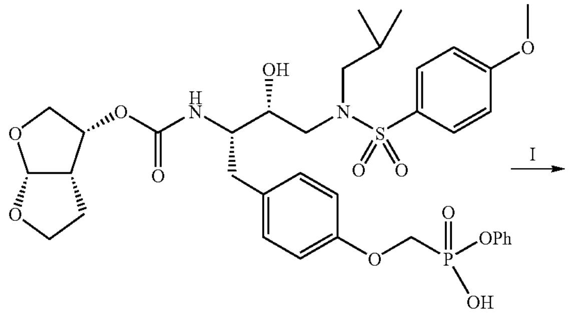

48

I. DCC/pyridine/60 C.

-continued

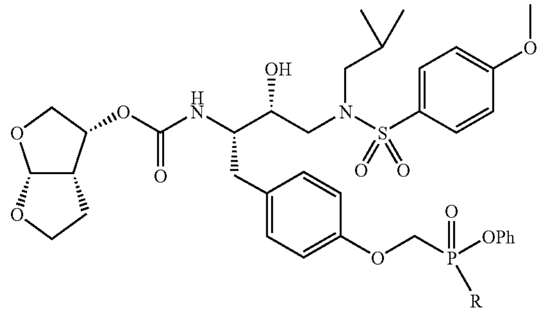

49 R = 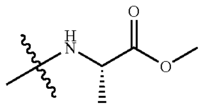

50 R = 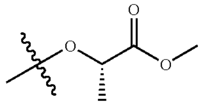

Example 48

Compound 48 was made by the methods of the previous Examples.

Example 49

Compound 49: To a solution of compound 48 (100 mg, 0.13 mmol) in pyridine (0.75 mL) was added L-alanine methyl ester hydrochloride (73 mg, 0.52 mmol), followed by DCC (161 mg, 0.78 mmol). The mixture was heated at 60° C. for 1 hour. The mixture was diluted with EtOAc, and was washed with 0.2 N HCl, water, 5% sodium bicarbonate, and brine, and was dried over $MgSO_4$. Purification by flash column chromatography ($CH_2Cl_2$/iPrOH=100/5) gave compound 49 (46 mg): $^1H$ NMR ($CDCl_3$) δ 7.73 (2H, m), 7.38-7.18 (7H, m), 7.03 (2H, m), 6.89 (2H, m), 5.68 (1H, m), 5.05 (1H, m), 4.95 (1H, m), 4.30 (3H, m), 4.0-3.6 (12H, m), 3.2-2.8 (7H, m), 1.84-1.60 (3H, m), 1.38 (3H, m), 0.93 (6H, m).

Example 50

Compound 50: To a solution of compound 48 (100 mg, 0.13 mmol) in pyridine (0.75 mL) was added methyl(s)-lactate (41 mg, 0.39 mmol), followed by DCC (81 mg, 0.39 mmol). The mixture was heated at 60° C. for 2 hours, and pyridine was removed under reduced pressure. The mixture was diluted with EtOAc (5 mL), and was filtered. Purification by flash column chromatography ($CH_2Cl_2$/iPrOH=100/5) gave compound 50 (83 mg): $^1H$ NMR ($CDCl_3$) δ 7.74 (2H, m), 7.38-7.14 (7H, m), 7.02 (2H, m), 6.93 (2H, m), 5.67 (1H, m), 5.18 (1H, m), 5.04 (1H, m), 4.92 (1H, m), 4.5 (2H, m), 4.0-3.68 (12H, m), 3.2-2.75 (7H, m), 1.82 (1H, m), 1.75-1.50 (5H, m), 0.93 (6H, m).

Scheme 11

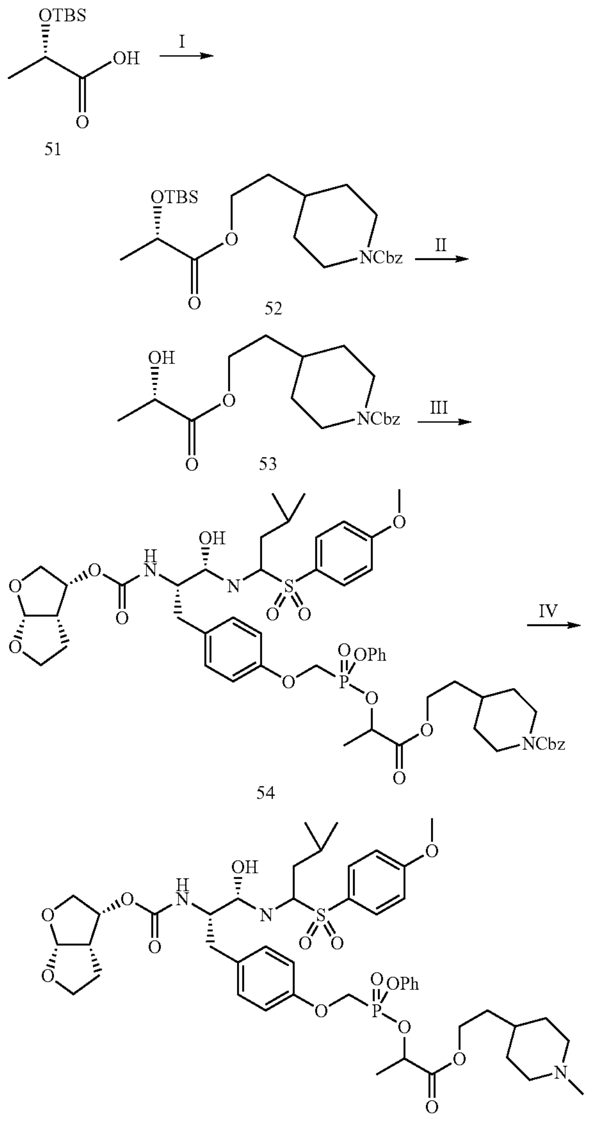

51

52

53

54

55

I. Benzotriazol-1-yloxytripyrrolidinophosphonium hexafluorophosphate/ROH/$i$Pr$_2$NEt;
II. 15% HF/$CF_3CH$;
III. Compound 48/DCC/pyridine/60 C.;
IV. a. $H_2$/10% Pd-C; b. $NaBH_3CN$/HCHO/HOAc

Example 51

Compound 51: To a solution of benzyl(s)-lactate (4.0 g, 20 mmol) in DMF (40 mL) was added imidazole (2.7 g, 20 mmol), followed by tert-butyldimethylsilyl chloride (3.3 g, 22 mmol). The mixture was stirred for 14 hours, and diluted with EtOAc. The organic phase was washed with 1.0 N HCl solution (2×), water (2×), and brine (1×), and dried over $MgSO_4$. Concentration gave the lactate intermediate (6.0 g). To the solution of the above intermediate in EtOAc (200 mL) was added 10% Palladium on carbon (700 mg). The mixture was hydrogenated for 2 hours. The mixture was stirred with celite for 5 minutes, and was filtered through a pad of celite. Concentration gave compound 51 (3.8 g).

Example 52

Compound 52: To a solution of compound 51 (1.55 g, 7.6 mmol) in $CH_2Cl_2$ (20 mL) was added 4-benzyloxycarbonylpiperidineethanol (2.00 g, 7.6 mmol), followed by benzotriazol-1-yloxytripyrrolidinophosphonium hexafluorophosphate (4.74 g, 9.1 mmol) and diisopropylethylamine (1.58 mL, 9.1 mmol). The mixture was stirred for 14 hours, and dichloromethane was removed. The mixture was diluted with EtOAc, and was washed with brine, and dried with $MgSO_4$. Purification by flash column chromatography (hexanes/EtOAc=10/1) gave compound 52 (1.50 g).

Example 53

Compound 53: To a solution of compound 52 (1.50 g) in $CH_3CN$ was added 58% HF/$CH_3CN$ (5 mL). The mixture was stirred for 30 minutes, and acetonitrile was removed under reduced pressure. The mixture was diluted with EtOAc, and was washed with water and brine, and was dried over $MgSO_4$. Purification by flash column chromatography (hexanes/EtOAc=1/1) gave compound 53 (1.00 g).

Example 54

Compound 54: To a solution of compound 48 (769 mg, 1.0 mmol) in pyridine (6.0 mL) was added compound 53 (1.0 g, 3.0 mmol), followed by DCC (618 mg, 3.0 mmol). The mixture was heated at 60° C. for 2 hours, and pyridine was removed under reduced pressure. The mixture was diluted with EtOAc (5 mL), and was filtered. Purification by flash column chromatography ($CH_2Cl_2$/iPrOH=100/4) gave compound 54 (630 mg).

Example 55

Compound 55: To a solution of compound 54 (630 mg, 0.58 mmol) in EtOAc (30 mL) was added 10% Palladium on carbon (63 mg), followed by acetic acid (80 μL). The mixture was hydrogenated for 2 hours. The mixture was stirred with celite for 5 minutes, and was filtered through a pad of celite. Concentration gave the intermediate. To the solution of the above intermediate in EtOAc (10 mL) was added 37% formaldehyde (88 μL, 1.18 mmol), followed by acetic acid (10 μL, 1.77 mmol). The mixture was cooled to 0° C., and sodium cyanoborohydride (74 mg, 1.18 mmol) was added. The mixture was stirred at 25° C. for 80 minutes, and was diluted with EtOAc. The mixture was washed with water and brine, and was dried over $MgSO_4$. Concentration gave compound 55 as a white solid (530 mg): $^1H$ NMR ($CDCl_3$) δ 7.74 (2H, m), 7.40-7.15 (7H, m), 7.03 (2H, m), 6.92 (2H, m), 5.66 (1H, m), 5.20-5.00 (3H, m), 4.58-4.41 (2H, m), 4.16 (2H, m), 4.0-3.7 (9H, m), 3.4-2.6 (14H, m), 1.90-1.50 (13H, m), 0.92 (6H, m).

Scheme 12

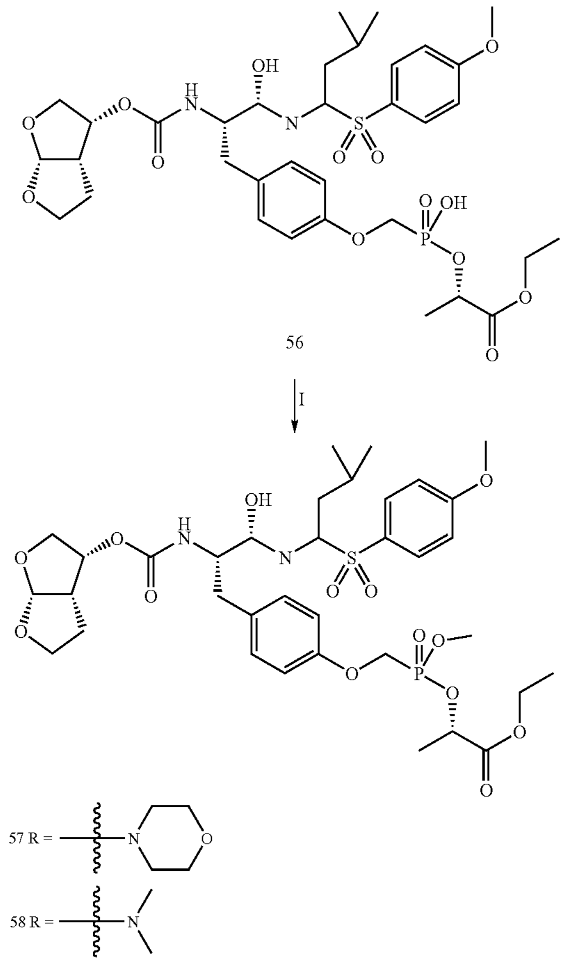

56

57 R =

58 R =

I. $R_2NOH$/DCC/pyridine

Example 56

Compound 56 was made by the methods of the previous Examples.

Example 57

Compound 57: To a solution of compound 56 (100 mg, 0.12 mmol) in pyridine (0.6 mL) was added N-hydroxymorpholine (50 mg, 0.48 mmol), followed by DCC (99 mg, 0.48 mmol). The mixture was stirred for 14 hours, and pyridine was removed under reduced pressure. The mixture was diluted with EtOAc, and was filtered. Purification by flash column chromatography ($CH_2Cl_2$/iPrOH=100/5) gave compound 57 (53 mg): $^1$H NMR ($CDCl_3$) δ 7.71 (2H, d, J=8.6 Hz), 7.15 (2H, d, J=7.6 Hz), 6.99 (2H, d, J=8.8 Hz), 6.90 (2H, m), 5.67 (1H, m), 5.18 (1H, m), 5.05 (1H, m), 4.95 (1H, m), 4.58-4.38 (2H, m), 4.21 (2H, m), 4.02-3.80 (13H, m), 3.55-3.38 (2H, m), 3.2-2.78 (9H, m), 1.9-1.8 (1H, m), 1.8-0.95 (5H, m), 1.29 (3H, m), 0.93 (6H, m).

Example 58

Compound 58: To a solution of compound 56 (100 mg, 0.12 mmol) in pyridine (0.6 mL) was added N,N-dimethylhydroxylamine hydrochloride (47 mg, 0.48 mmol), followed by DCC (99 mg, 0.48 mmol). The mixture was stirred for 6 hours, and pyridine was removed under reduced pressure. The mixture was diluted with EtOAc, and was filtered. Purification by flash column chromatography ($CH_2Cl_2$/iPrOH=100/5) gave compound 58 (35 mg). $^1$H NMR ($CDCl_3$) δ 7.71 (2H, d, J=8.9 Hz), 7.15 (2H, d, J=8.2 Hz), 6.99 (2H, d, J=8.4 Hz), 6.89 (2H, m), 5.65 (1H, d, J=5.2 Hz), 5.15 (1H, m), 4.98 (2H, m), 4.42 (2H, m), 4.18 (2H, m), 4.0-3.6 (9H, m), 3.2-2.7 (13H, m), 1.92-1.45 (6H, m), 1.25 (3H, m), 0.90 (6H, m).

Scheme 13

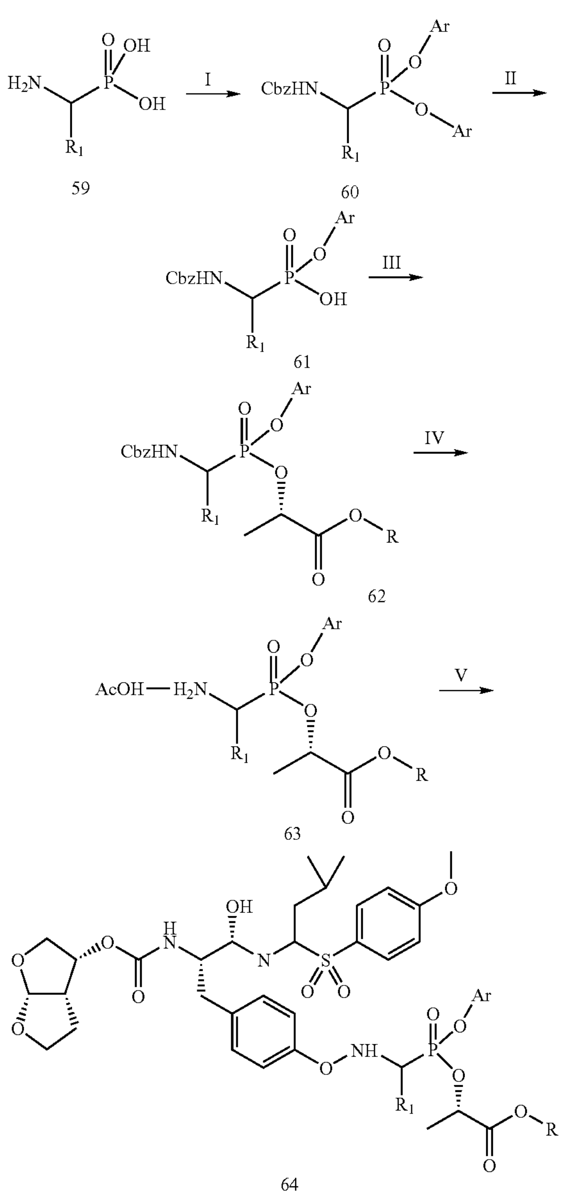

59

60

61

62

63

64

R = Me, Et, Pr, i-Pr; $R_1$ = H, Me, Et, i-Pr; Ar = phenyl, 2, 6-dimethylphenyl

I. a. CbzCl/NaOH; b..$SOCl_2$/toluene/60 C.; c. ArOH/pyridine;

II. a. NaOH/THF/$H_2O$; b. HCl;

III. a. $SOCl_2$/toluene/60 C.; b. alkyll lactate/pyridine;

IV. $H_2$/10% Pd-C/EtOAc/HOAc;

V. a. compound 6/$MgSO_4$; b. HOAc/$NaCNBH_3$

Aminomethylphosphonic acid 59 is protected as benzyl carbamate. The phosphonic acid is treated with thionyl chloride to generate dichloridate, which reacts with phenol or 2,6-dimethylphenol to give compound 60. Compound 60 is hydrolyzed with sodium hydroxide, followed by acidification to afford monoacid 61. Monoacid 61 is treated with thionyl chloride to generate monochloridate, which reacts with different alkyl(s)-lactates to form compound 62. Compound 62 is hydrogenated with 10% Pd—C in the presence of acetic acid to give compound 63. Compound 63 reacts with aldehyde 6 in the presence of $MgSO_4$ to form imine, which is reduced with sodium cyanoborohydride to generate compound 64.

Scheme 14

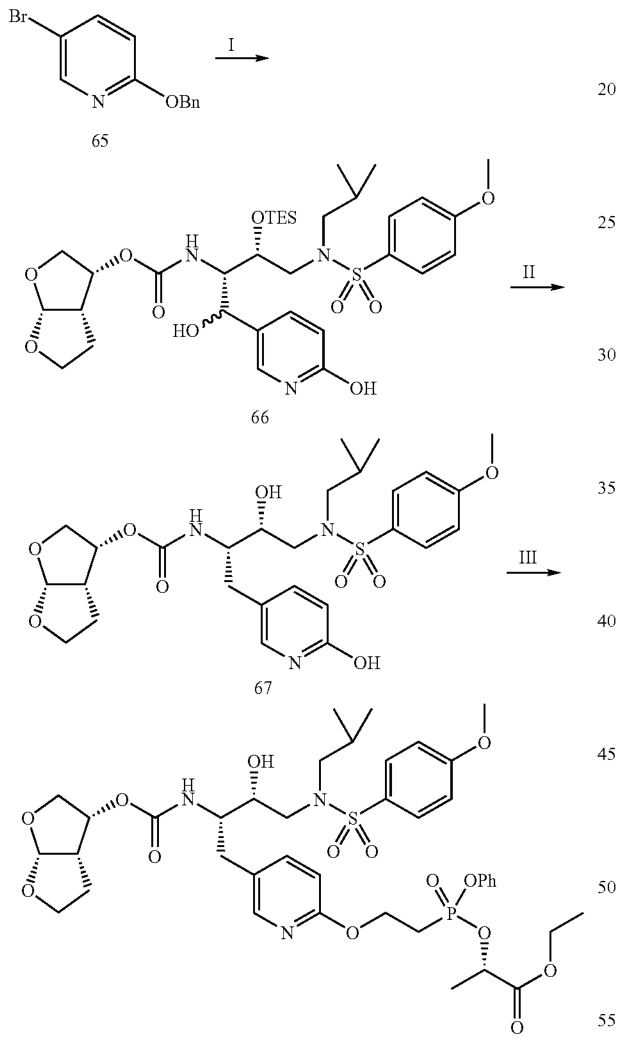

65

66

67

68

I.a. n-BuLi; b compound 15; II. $H_2$/10% Pd—C/HOAc; IV. $PPh_3$/DEAD

Compound 65 is prepared from 2-hydroxy-5-bromopyridine by alkylation. J. Med. Chem. 1992, 35, 3525. Compound 65 is treated with n-Butyl lithium to generate aryl lithium, which reacts with aldehyde 15 to form compound 66. J. Med. Chem. 1994, 37, 3492. Compound 66 is hydrogenated with 10% Pd—C in the presence of acetic acid to give compound 67. J. Med. Chem. 2000, 43, 721. Compound 68 is prepared from compound 67 with corresponding alcohol under Mitsunobu reaction conditions. Bioorg. Med. Chem. Lett. 1999, 9, 2747.

Scheme 1

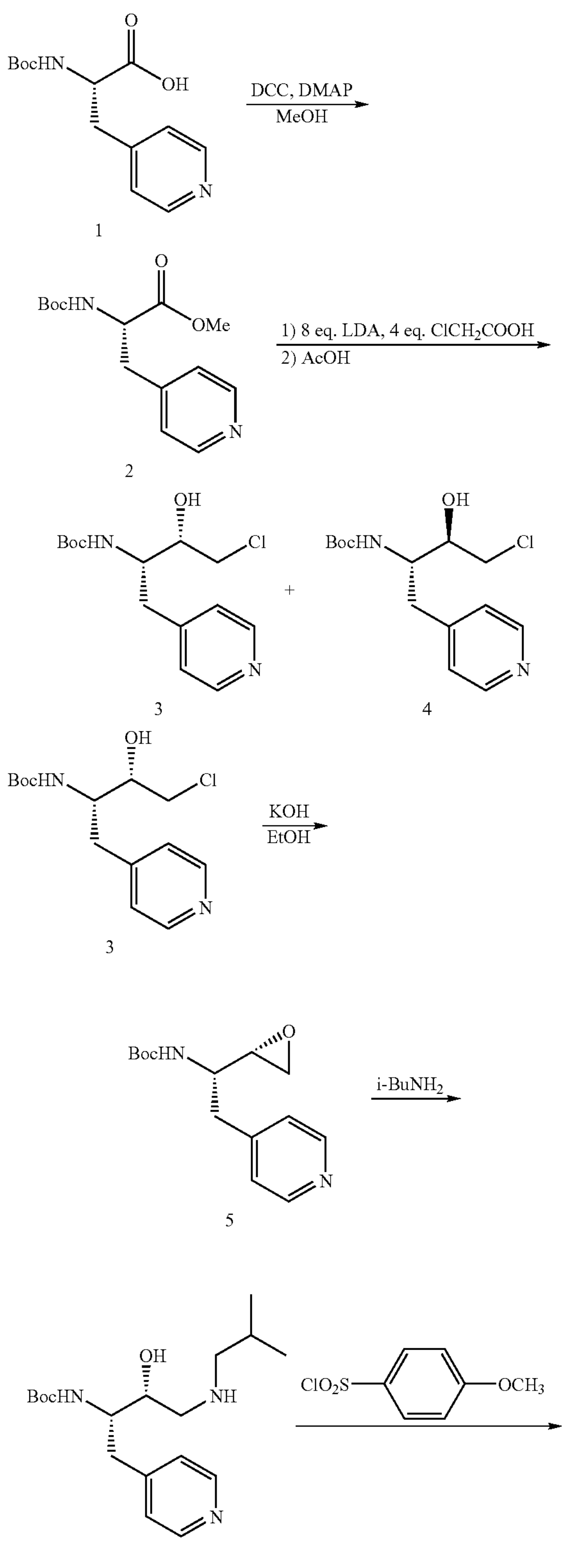

1

2

3

4

3

5

6

-continued

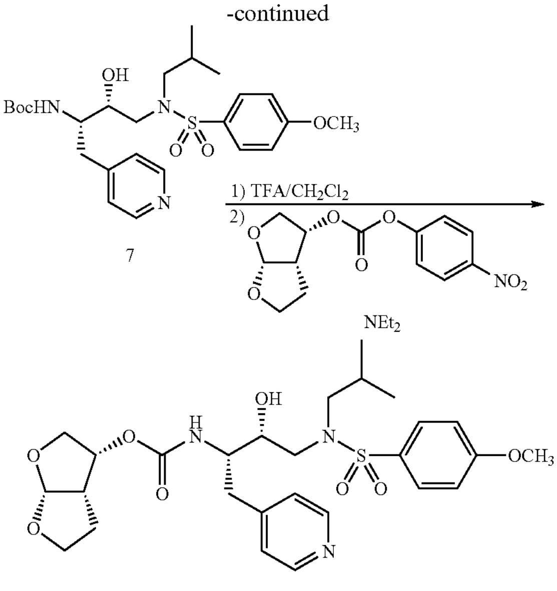

7

9
GS7921

Example 1

Methyl 2-(S)-(dimethylethoxycarbonylamino)-3-(4-pyridyl)propanoate (2): A solution of N-tert-Butoxycarbonyl-4-pyridylalanine (1, 9.854 g, 37 mmol, Peptech), 4-dimethylaminopyridine (4.52 g, 37 mmol, Aldrich), and dicyclohexylcarbodiimide (15.30 g, 74.2 mmol, Aldrich) in methanol (300 mL) was stirred at 0° C. for 2 h and at room temperature for 12 h. After the solids were removed by filtration, the filtrate was concentrated under reduced pressure. More dicyclohexylurea was removed by repeated trituration of the concentrated residue in EtOAc followed by filtration. The residue was chromatographed on silica gel to afford the methyl ester 2 (9.088 g, 88%): $^1H$ NMR ($CDCl_3$) δ 8.53 (d, 2H, J=5.7 Hz), 7.09 (d, 2H, J=5.7 Hz), 5.04 (br, 1H), 4.64 (br, 1H), 3.74 (s, 3H), 3.16 (dd, 1H, J=13.5 and 5.7 Hz), 3.02 (dd, 1H, J=13.5 and 6.3 Hz), 1.42 (s, 9H); MS (ESI) 281 (M+H).

Example 2

1-Chloro-3-(S)-(dimethylethoxycarbonylamino)-4-(4-pyridyl)-2-(S)-butanol (3): A solution of diisopropylamine (37.3 mL, 266 mmol, Aldrich) in THF (135 mL) was stirred at −78° C. as a solution of n-butyllithium (102 mL of 2.3 M solution and 18 mL of 1.4 M solution 260 mmol, Aldrich) in hexane was added. After 10 min, the cold bath was removed and stirred the solution for 10 min at the ambient temperature. The solution was cooled at −78° C. again and stirred as a solution of chloroacetic acid (12.255 g, 130 mmol, Aldrich) in THF (50 mL) was added over 20 min. After the solution was stirred for 15 min, this dianion solution was transferred to a stirred solution of the methyl ester 2 (9.087 g, 32.4 mmol) in THF (100 mL) at 0° C. over 15 min. The resulting yellow slurry was stirred at 0° C. for 10 min and cooled at −78° C. A solution of acetic acid (29 mL, 507 mmol, Aldrich) in THF (29 mL) was added quickly to the slurry and the resulting slurry was stirred at −78° C. for 30 min, at 0° C. for 30 min, and at room temperature for 15 min. The resulting slurry was dissolved in saturated $NaHCO_3$ solution (750 mL) and EtOAc (500 mL). The separated aqueous layer was extracted with EtOAc (300 mL×2) and the combined organic fractions were washed with water (750 mL×2) and saturated NaCl solution (250 mL). The resulting solution was dried ($MgSO_4$) and evaporated under reduced pressure.

A solution of the residue in THF (170 mL) and water (19 mL) was stirred at 0° C. as $NaBH_4$ (3.375 g, 89.2 mmol, Aldrich) was added. After 30 min, the solution was evaporated under reduced pressure and the residue was dissolved in EtOAc, acidified with aqueous $NaHSO_4$, and then neutralized by adding saturated aqueous $NaHCO_3$ solution. The separated aqueous fraction was extracted with EtOAc (100 mL) and the combined organic fractions were washed with water (500 mL) and saturated NaCl solution (100 mL). The solution was dried ($MgSO_4$) and evaporated under reduced pressure. The residue was chromatographed on silica gel to afford the chlorohydrin 3 and 4 (4.587 g, 47%) as a mixture of two diastereomers (34:1). The obtained mixture was recrystallized from EtOAc-hexane twice to obtain pure desired diastereomer 3 (2.444 g, 25%) as yellow crystals: $^1H$ NMR ($CDCl_3$) δ 8.53 (d, 2H, J=5.7 Hz), 7.18 (d, 2H, J=5.7 Hz), 4.58 (br, 1H), 3.94 (m, 1H), 3.87 (br, 1H), 3.75-3.54 (m, 2H), 3.05 (dd, 1H, J=13.8 and 3.9 Hz), 2.90 (dd, 1H, J=13.8 and 8.4 Hz), 1.36 (s, 9H); MS (ESI) 301 (M+H).

Example 3

The epoxide 5: A solution of the chlorohydrin 3 (1.171 g, 3.89 mmol) in ethanol (39 mL) was stirred at room temperature as 0.71 M KOH in ethanol (6.6 mL) was added. After 1.5 h, the mixture was concentrated under reduced pressure and the residue was dissolved in EtOAc (60 mL) and water (60 mL). The separated aqueous fraction was extracted with EtOAc (60 mL) and the combined organic fractions were washed with saturated NaCl solution, dried ($MgSO_4$), and concentrated under reduced pressure to obtain the epoxide (1.058 g, quantitative): $^1H$ NMR ($CDCl_3$) δ 8.52 (d, 2H, J=6.0 Hz), 7.16 (d, 2H, J=6.0 Hz), 4.57 (d, 1H, J=7.8 Hz), 3.76 (br, 1H), 3.02-2.92 (m, 2H), 2.85-2.79 (m, 2H), 2.78-2.73 (m, 1H), 1.37 (s, 9H); MS (ESI) 265 (M+H).

Example 4

The hydroxy-amine 6: A solution of the epoxide 5 obtained above and i-$BuNH_2$ (3.9 mL, 39.2 mmol, Aldrich) in 58 mL of i-PrOH was stirred at 65° C. for 2 h and the solution was concentrated under reduced pressure. The residual i-PrOH was removed by dissolving the residue in toluene and concentration of the solution twice: $^1H$ NMR ($CDCl_3$) δ 8.51 (d, 2H, J=6.0 Hz), 7.18 (d, 2H, J=6.0 Hz), 4.70 (d, 1H, J=9.6 Hz), 3.86 (br, 1H), 3.46 (q, 1H, J=5.8 Hz), 3.06 (dd, 1H, J=14.1 and 3.9 Hz), 2.79 (dd, 1H, J=14.1 and 9.0 Hz), 2.76-2.63 (m, 3H), 2.43 (m, 2H, J=6.9 Hz), 1.73 (m, 1H, J=6.6 Hz), 1.36 (s, 9H), 0.93 (d, 3H, J=6.6 Hz), 0.92 (d, 3H, J=6.6 Hz); MS (ESI) 338 (M+H).

Example 5

The sulfoamide 7: A solution of the crude 6 and p-methoxybenzene sulfonyl chloride (890 mg, 4.31 mmol, Aldrich) in $CH_2Cl_2$ (24 mL) was stirred at 0° C. for 2 h and at room temperature for 13 h. The solution was washed with saturated $NaHCO_3$ solution and the aqueous washing was extracted with $CH_2Cl_2$ (60 mL). After the combined organic fractions were dried ($MgSO_4$) and concentrated under reduced pressure, the residue was purified by chromatography on silica gel to obtain the sulfoamide 7 (1.484 g, 75%): $^1H$ NMR ($CDCl_3$)

δ 8.51 (d, 2H, J=5.7 Hz), 7.73 (d, 2H, J=8.7 Hz), 7.21 (d, 2H, J=5.7 Hz), 7.00 (d, 2H, J=8.7 Hz), 4.68 (d, 1H, J=8.1 Hz), 4.08 (br, 1H), 3.88 (s, 3H), 3.83 (br, 2H), 3.09 (d, 2H, J=5.1 Hz), 3.06-2.80 (m, 4H), 1.85 (m, 1H, J=7.0 Hz), 1.34 (s, 9H), 0.92 (d, 3H, J=6.3 Hz), 0.89 (d, 3H, J=6.6 Hz); MS (ESI) 508 (M+H).

Example 6

The bisfurancarbamate 9: A solution of the sulfoamide 7 (1.484 g, 2.92 mmol) and trifluoroacetic acid (6.8 mL, 88.3 mmol, Aldrich) in $CH_2Cl_2$ (18 mL) was stirred at room temperature for 2 h. After the solution was evaporated under reduced pressure, the residue was dissolved in acetonitrile (10 mL) and toluene (10 mL), and evaporated to dryness twice to result crude amine as TFA salt. A solution of the crude amine, dimethylaminopyridine (72 mg, 0.59 mmol, Aldrich), diisopropylethylamine (2.55 mL, 14.6 mmol, Aldrich) in acetonitrile was stirred at 0° C. as the bisfurancarbonate 8 (907 mg, 3.07 mmol, obtained from Azar) was added in portion. The solution was stirred at 0° C. for 1 h and at room temperature for 19 h, and concentrated under reduced pressure. The residue was dissolved in EtOAc (60 mL) and washed with saturated $NaHCO_3$ solution (60 mL). After the aqueous washing was extracted with EtOAc (60 mL), the combined organic fractions were washed with saturated $NaHCO_3$ (60 mL) and saturated NaCl solution (60 mL), dried ($MgSO_4$), and concentrated under reduced pressure. The residue was purified by chromatography on silica gel to obtain the carbamate 9 (1.452 g, 88%): $^1$H NMR ($CDCl_3$) δ 8.50 (d, 2H, J=5.7 Hz), 7.72 (d, 2H, J=8.7 Hz), 7.19 (d, 2H, J=5.7 Hz), 7.01 (d, 2H, J=8.7 Hz), 5.65 (d, 1H, J=5.1 Hz), 5.12 (d, 1H, J=9.3 Hz), 5.02 (q, 1H, J=6.7 Hz), 4.01-3.77 (m, 4H), 3.88 (s, 3H), 3.76-3.63 (m, 2H), 3.18-2.76 (m, 7H), 1.95-1.77 (m, 1H), 1.77-1.56 (m, 2H), 1.56-1.41 (m, 1H), 0.94 (d, 3H, J=6.6 Hz), 0.90 (d, 3H, J=6.9 Hz); MS (ESI) 564 (M+H).

Scheme 2

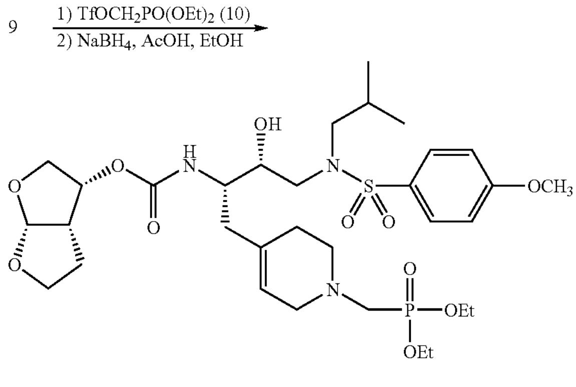

11
GS192710

Example 7

The tetrahydropyridine-diethyl phosphonate 11: A solution of the pyridine 9 (10.4 mg, 0.018 mmol) and the triflate 10 (8.1 mg, 0.027 mmol, in acetone-$d_6$ (0.75 mL) was stored at room temperature for 9 h and the solution was concentrated under reduced pressure: $^{31}$P NMR (acetone-$d_3$) δ 14.7; MS (ESI) 714 ($M^+$). The concentrated crude pyridinium salt was dissolved in ethanol (2 mL) and stirred at room temperature as $NaBH_4$ (~10 mg, Aldrich) was added occasionally over 4 h. To the mixture was added a solution of acetic acid (0.6 mL, Aldrich) in ethanol (3 mL) until the pH of the mixture became 3~4. More $NaBH_4$ and acetic acid were added until the reaction was completed. The mixture was carefully concentrated under reduced pressure and the residue was dissolved in saturated NaHCO3 solution (10 mL). The product was extracted using EtOAc (10 mL×3) and washed with saturated NaCl solution, dried ($MgSO_4$), and concentrated under reduced pressure. The residue was purified by chromatography on silica gel to obtain the product 11 (8.5 mg, 64%): $^1$H NMR ($CDCl_3$) δ 7.73 (d, 2H, J=8.7 Hz), 7.00 (d, 2H, J=8.7 Hz), 5.71 (d, 1H, J=5.1 Hz), 5.41 (br, 1H), 5.15-5.08 (m, 1H), 5.00 (br, 1H), 4.14 (dq, 4H, J=7.2 Hz), 4.06-3.94 (m, 2H), 3.88 (s, 3H), 3.92-3.80 (m, 2H), 3.75 (dd, 1H, J=9.6 and 6.6 Hz), 3.79-3.61 (m, 1H), 3.24-2.94 (m, 6H), 2.85 (d, 2H, J=11.7 Hz), 2.88-2.76 (m, 2H), 2.75-2.63 (m, 1H), 2.38-2.29 (n, 1H), 2.24-2.2.12 (m, 2H), 2.12-1.78 (m, 4H), 1.30 (t, 6H, J=7.1 Hz), 0.94 (d, 3H, J=6.6 Hz), 0.91 (d, 3H, J=6.3 Hz); $^{31}$P NMR ($CDCl_3$) δ 24.6; MS (ESI) 740 (M+Na).

Scheme 3

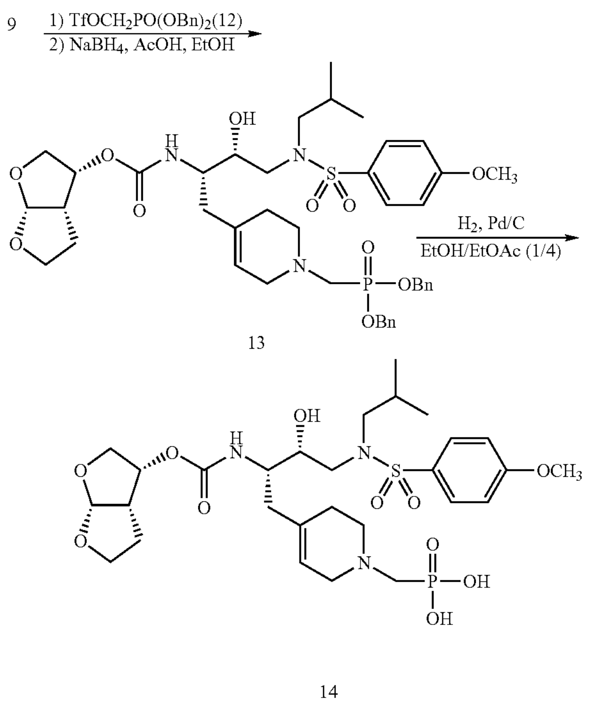

13

14
GS192711

Example 8

The tetrahydropyridine-dibenzyl phosphonate 13: The compound 13 was obtained by the same procedure as described for compound 11 using the pyridine 9 (10.0 mg, 0.018 mmol) and the triflate 12 (9.4 mg, 0.022 mmol). The product 13 was purified by preparative TLC to afford the dibenzyl phosphonate 13 (8.8 mg, 59%): $^1$H NMR ($CDCl_3$) δ 7.73 (d, 2H, J=8.7 Hz), 7.35 (s, 10H), 7.00 (d, 2H, J=8.7 Hz), 5.65 (d, 1H2H, J=5.1 Hz), 5.39 (br, 1H), 5.15-4.92 (m, 6H), 4.03-3.77 (m, 6H), 3.77-3.62 (m, 2H), 3.56 (br, 1H), 3.24-2.62 (m, 9H), 2.32 (d, 1H, J=13.5 Hz), 2.24-1.75 (m, 6H), 0.94 (d, 3H, J=6.6 Hz), 0.89 (d, 3H, J=6.3 Hz); $^{31}P$ NMR ($CDCl_3$) δ 25.5; MS (ESI) 842 (M+H).

Example 9

The phosphonic acid 14: A mixture of the dibenzyl phosphonate 13 (8.8 mg, 0.011 mmol) and 10% Pd/C in EtOAc (2 mL) and EtOH (0.5 mL) was stirred under $H_2$ atmosphere for 10 h at room temperature. After the mixture was filtered through celite, the filtrate was concentrated to dryness to afford the product 14 (6.7 mg, quantitative): $^{1}H$ NMR ($CD_3OD$) δ 7.76 (d, 2H, J=9.0 Hz), 7.10 (d, 2H, J=9.0 Hz), 5.68 (d, 1H, J=5.1 Hz), 5.49 (br, 1H), 5.11 (m, 1H), 3.90 (s, 3H), 4.04-3.38 (m, 10H), 3.22 (d, 2H, J=12.9 Hz), 3.18-3.00 (m, 2H), 2.89-2.75 (m, 2H), 2.68-2.30 (m, 3H), 2.21-1.80 (m, 4H), 0.92 (d, 3H, J=6.3 Hz), 0.85 (d, 3H, J=6.3 Hz); $^{31}P$ NMR ($CD_3OD$) δ 6.29; MS (ESI) 662 (M+H).

Scheme 4

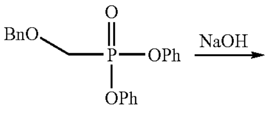

15

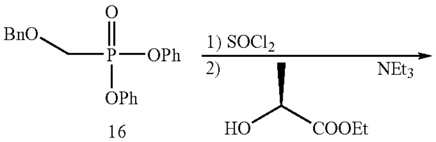

16

17

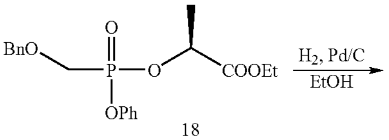

18

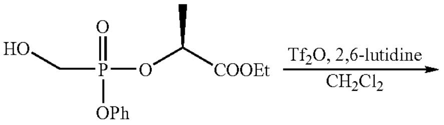

19

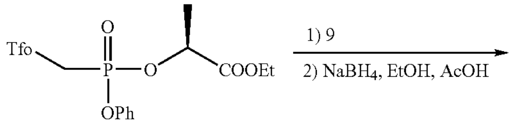

20

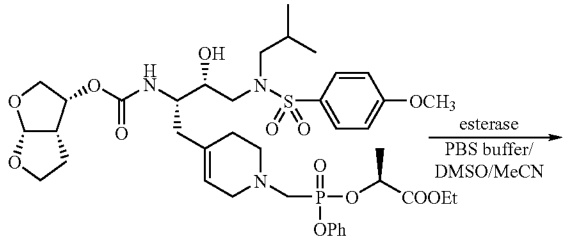

21
GS193786

-continued

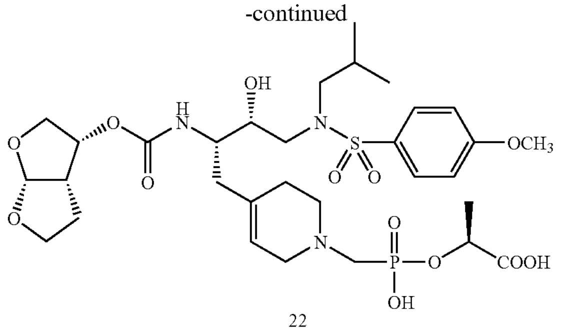

22
GS193816

Example 10

Diphenyl benzyloxymethylphosphonate 15: To a solution of diphenylphosphite (46.8 g, 200 mmol, Aldrich) in acetonitrile (400 mL) (at ambient temperature) was added potassium carbonate (55.2 g, 400 mmol) followed by the slow addition of benzyl chloromethyl ether (42 mL, 300 mmol, about 60%, Fluka). The mixture was stirred overnight, and was concentrated under reduced pressure. The residue was dissolved in EtOAc, washed with water, saturated NaCl, dried ($Na_2SO_4$), filtered and evaporated. The crude product was chromatographed on silica gel to afford the benzylether (6.8 g, 9.6%) as a colorless liquid.

Example 11

Monoacid 16: To a solution of diphenyl benzyloxymethylphosphonate 15 (6.8 g, 19.1 mmol) in THF (100 mL) at room temperature was added 1N NaOH in water (21 mL, 21 mmol). The solution was stirred 3 h. The THF was evaporated under reduced pressure and water (100 mL) was added. The aqueous solution was cooled to 0° C., neutralized to pH 7 with 3N HCl and washed with EtOAc. The aqueous solution was again cooled to 0° C., acidified with 3N HCl to pH 1, saturated with sodium chloride, and extracted with EtOAc. The organic layer was washed with brine and dried ($Na_2SO_4$), filtered and evaporated, then co-evaporated with toluene to yield the monoacid (4.0 g, 75%) as a colorless liquid. $^{1}H$ NMR ($CDCl_3$) δ 7.287.09 (m, 10H), 4.61 (s, 2H), 3.81 (d, 2H); $^{31}P$ NMR ($CDCl_3$) δ 20.8.

Example 12

Ethyl lactate phosphonate 18: To a solution of monoacid 16 (2.18 g, 7.86 mmol) in anhydrous acetonitrile (50 mL) under a nitrogen atmosphere was slowly added thionyl chloride (5.7 mL, 78 mmol). The solution was stirred in a 70° C. oil bath for three hours, cooled to room temperature and concentrated. The residue was dissolved in anhydrous dichloromethane (50 mL), and this solution cooled to 0° C. and stirred under a nitrogen atmosphere. To the stirring solution was added ethyl (S)-(−)-lactate (2.66 mL, 23.5 mmol) and triethylamine (4.28 mL, 31.4 mmol). The solution was warmed to room temperature and allowed to stir for one hour. The solution was diluted with ethyl acetate, washed with water, brine, citric acid and brine again, dried ($MgSO_4$), filtered through Celite, concentrated under reduced pressure and chromatographed on silica gel using 30% ethylacetate in hexane. The two diastereomers were pooled together. $^{1}H$ NMR ($CDCl_3$) δ 7.40-7.16 (m, 20H), 5.18-5.13 (m, 2H), 4.73 (s, 2H), 4.66 (d, 2H), 4.28-4.11

(m, 5H), 4.05 (d, 2H), 3.95 (d, 2H), 1.62 (d, 3H), 1.46 (d, 3H), 1.30-1.18 (m, 6H); $^{31}$P NMR ($CDCl_3$) δ 19.6, 17.7.

Example 13

Ethyl lactate phosphonate with free alcohol 19: Ethyl lactate phosphonate 18 was dissolved in EtOH (50 mL) and under a nitrogen atmosphere 10% Pd—C (approximately 20 wt %) was added. The nitrogen atmosphere was replaced with hydrogen (1 atm) and the suspension stirred for two hours. 10% Pd—C was again added (20 wt %) and the suspension stirred five hours longer. Celite was added, the reaction mixture was filtered through Celite and the filtrate was concentrated to afford 1.61 g (71% from monoacid 16) of the alcohol as a colorless liquid. $^1$H NMR ($CDCl_3$) δ 7.40-7.16 (m, 10H), 5.16-5.03 (m, 2H), 4.36-4.00 (m, 8H), 1.62 (d, 3H), 1.46 (d, 3H), 1.30-1.22 (m, 6H); $^{31}$P NMR ($CDCl_3$) δ 22.3, 20.0.

Example 14

Triflate 20: To a solution of ethyl lactate phosphonate with free alcohol 19 (800 mg, 2.79 mmol) in anhydrous dichloromethane (45 mL) chilled to −40° C. under a nitrogen atmosphere was added triflic anhydride (0.516 mL, 3.07 mmol) and 2-6 lutidine (0.390 mL, 3.34 mmol). The solution was stirred for 3 hr, then warmed to −20° C. and stirred one hour longer. 0.1 equivalents of triflic anhydride and 2-6 lutidine were then added and stirring was resumed for 90 minutes more. The reaction mixture was diluted with ice-cold dichloromethane, washed with ice-cold water, washed with ice-cold brine and the organic layer was dried ($MgSO_4$) and filtered. The filtrate was concentrated and chromatographed on silica gel using 30% EtOAc in hexane as eluent to afford 602 mg (51%) of the triflate diastereomers as a slightly pink, transparent liquid. $^1$H NMR ($CDCl_3$) δ 7.45-7.31 (m, 4H), 7.31-7.19 (m, 6H), 5.15-4.75 (m, 6H), 4.32-4.10 (4H), 1.62 (d, 3H), 1.50 (d, 3H), 1.30-1.22 (m, 6H); $^{31}$P NMR ($CDCl_3$) δ 10.3, 8.3.

Example 15

The tetrahydropyridine-prodrug 21: A solution of the pyridine 9 (11.1 mg, 0.020 mmol) and the triflate 20 (11.4 mg, 0.027 mmol) in acetone-$d_6$ (0.67 mL, Aldrich) was stored at room temperature for 7 h and the solution was concentrated under reduced pressure: $^{31}$P NMR (acetone-$d_6$) δ 11.7, 10.9; MS (ESI) 838 (M+H). The concentrated crude pyridinium salt was dissolved in ethanol (1 mL) and added 23 drops of a solution of acetic acid (0.6 mL, Aldrich) in ethanol (3 mL). The solution was stirred at 0° C. as $NaBH_4$ (7~8 mg, Aldrich) was added. More acetic acid solution was added to adjust pH 3~4 of the reaction mixture. Additions of $NaBH_4$ and the acetic acid solution were repeated until the reaction was completed. The mixture was carefully concentrated under reduced pressure and the residue was purified by chromatography on C18 reverse phase column material followed by preparative TLC using C18 reverse phase plate to obtain the prodrug 21 (13.6 mg, 70%) as a 2:3 mixture of two diastereomers: $^1$H NMR ($CD_3CN$) δ 7.78 (d, 2H, J=9.0 Hz), 7.48-7.42 (m, 2H), 7.35-7.27 (m, 3H), 7.10 (d, 2H, J=9.0 Hz), 5.86 (m, 1H), 5.60 (m, 1H), 5.48 (br, 1H), 5.14-5.03 (m, 2H), 4.29-4.13 (m, 2H), 3.89 (s, 3H), 3.97-3.32 (m, 12H), 3.29 (br, 0.4H), 3.24 (br, 0.6H), 3.02-2.82 (m, 4H), 2.64-2.26 (m, 3H), 2.26-2.08 (m, 1H), 1.94-1.76 (m, 3H), 1.57 (d, 1.8H, J=6.9 Hz), 1.46 (d, 1.2H, J=6.9 Hz), 1.28 (d, 1.2H, J=6.9 Hz), 1.21 (d, 1.8H, J=7.2 Hz), 0.92-0.88 (m, 6H); $^{31}$P NMR ($CD_3CN$) δ 14.4 (0.4P), 13.7 (0.6P); MS (ESI) 838 (M+H).

Example 16

Metabolite 22: To a solution of the prodrug 21 (10.3 mg, 0.011 mmol) in DMSO (0.1 mL) and acetonitrile (0.2 mL) was added 0.1 M PBS buffer (3 mL) mixed thoroughly to result a suspension. To the suspension was added porcine liver esterase suspension (0.05 mL, EC3.1.1.1, Sigma). After the suspension was stored in 37° C. for 1.5 h, the mixture was centrifuged and the supernatant was taken. The product was purified by HPLC and the collected fraction was lyophilized to result the product 22 as trifluoroacetic acid salt (7.9 mg, 86%): $^1$H NMR ($D_2O$) δ 7.70 (d, 1H), 7.05 (d, 2H), 5.66 (d, 1H), 5.40 (br, 1H), 5.02 (br, 1H), 4.70 (br, 1H), 3.99-3.89 (m, 2H), 3.81 (s, 3H), 3.83-3.50 (m, 8H), 3.34-2.80 (m, 7H), 2.50-2.18 (m, 3H), 2.03 (m, 1H), 1.92-1.70 (m, 3H), 1.39 (d, 3H), 0.94 (d, 3H), 0.93 (d, 3H); $^{31}$P NMR ($D_2O$) δ 9.0, 8.8; MS (ESI) 734 (M+H).

Scheme 5

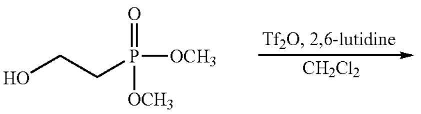

23

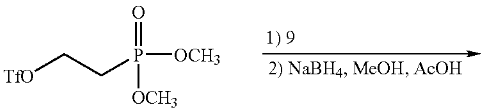

24

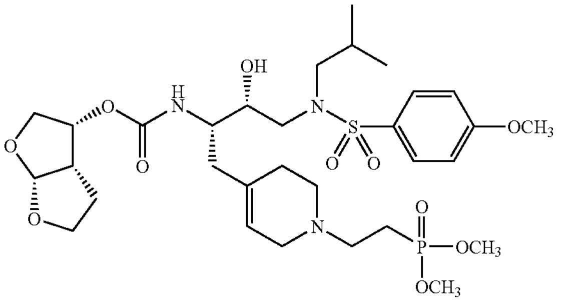

25
GS273819

Example 17

Triflate 24: Triflate 24 was prepared analogously to triflate 20, except that dimethylhydroxyethylphosphonate 23 (Aldrich) was substituted for ethyl lactate phosphonate with free alcohol 19.

Example 18

Tetrahydropyridine 25: Tetrahydropyridine 25 was prepared analogously to tetrahydropyridine 30, except that triflate 24 was substituted for triflate 29. $^1$H NMR ($CDCl_3$) δ 7.71 (d, 2H), 7.01 (d, 2H), 5.71 (d, 2H), 5.43 (bs, 1H), 5.07-4.87 (m, 1H), 4.16-3.46 (m, 13H), 3.34-3.18 (m, 3H), 3.16-2.80 (m, 5H), 2.52-1.80 (m, 12H), 1.28-1.04 (m, 3H+$H_2O$ peak), 0.98-0.68 (m, 6H).

Scheme 6

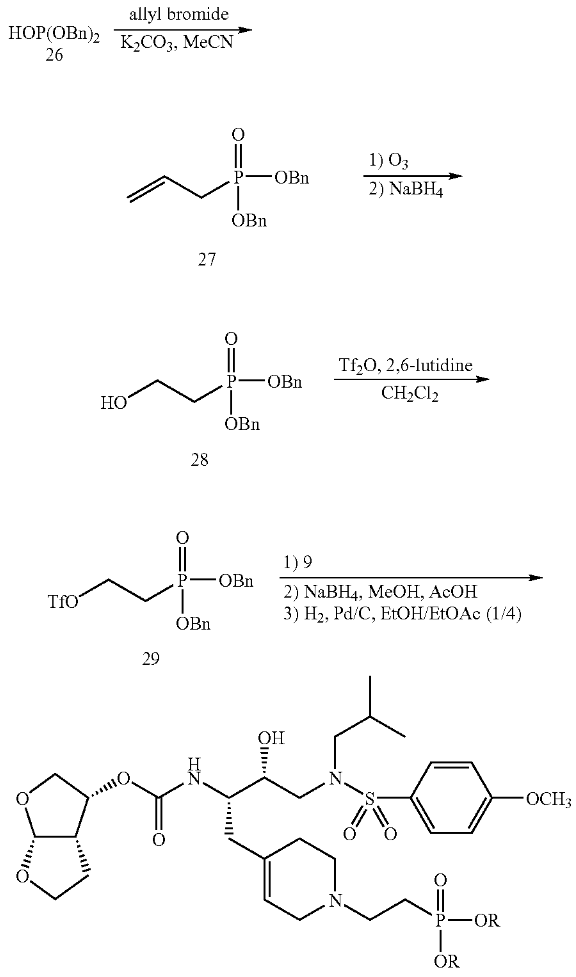

26

27

28

29

30:R = Bn (GS173848)
31:R = H (GS173850)

Example 19

Dibenzyl phosphonate with double bond 27: To a stirring solution of allyl bromide (4.15 g, 34 mmol, Aldrich) and dibenzylphosphite (6 g, 23 mmol, Aldrich) in acetonitrile (25 mL) was added potassium carbonate (6.3 g, 46 mmol, powder 325 mesh Aldrich) to create a suspension, which was heated to 65° C. and stirred for 72 hours. The suspension was cooled to room temperature, diluted with ethyl acetate, filtered, and the filtrate was washed with water, then brine, dried ($MgSO_4$), concentrated and used directly in the next step.

Example 20

Dibenzylhydroxyethylphosphonate 28: Dibenzyl phosphonate with double bond 27 was dissolved in methanol (50 mL), chilled to −78° C., stirred, and subjected to ozone by bubbling ozone into the solution for three hours until the solution turned pale blue. The ozone flow was stopped and oxygen bubbling was done for 15 minutes until the solution became colorless. Sodium borohydride (5 g, excess) was added slowly portionwise. After the evolution of gas subsided the solution was allowed to warm to room temperature, concentrated, diluted with ethyl acetate, made acidic with acetic acid and water and partitioned. The ethyl acetate layer was washed with water, then brine and dried ($MgSO_4$), filtered, concentrated and chromatographed on silica gel eluting with a gradient of eluent from 50% ethyl acetate in hexane to 100% ethyl acetate, affording 2.76 g of the desired product. $^1H$ NMR ($CDCl_3$) δ 7.36 (m, 10H), 5.16-4.95 (m, 4H), 3.94-3.80 (dt, 2H), 2.13-2.01 (dt, 2H); $^{31}P$ NMR ($CDCl_3$) δ 31.6.

Example 21

Dibenzyl phosphonate 30: A solution of the alcohol 28 (53.3 mg, 0.174 mmol) and 2,6-lutidine (0.025 mL, 0.215 mmol, Aldrich) in $CH_2Cl_2$ (1 mL) was stirred at −45° C. as trifluoromethanesulfonic anhydride (0.029 mL, 0.172 mmol, Aldrich) was added. The solution was stirred for 1 h at −45° C. and evaporated under reduced pressure to obtain the crude triflate 29.

A solution of the crude triflate 29, 2,6-lutidine (0.025 mL, 0.215 mmol, Aldrich), and the pyridine 9 in acetone-$d_6$ (1.5 mL, Aldrich) was stored at room temperature for 2 h. The solution was concentrated under reduced pressure to obtain crude pyridinium product: $^{31}P$ NMR (acetone-$d_6$) δ 25.8; MS (ESI) 852 ($M^+$).

To a solution of the crude pyridinium salt in ethanol (2 mL) was added 78 drops of a solution of acetic acid (0.4 mL, Aldrich) in ethanol (2 mL). The solution was stirred at 0° C. as $NaBH_4$ (7~8 mg) was added. The solution was maintained to be pH 3-4 by adding the acetic acid solution. More $NaBH_4$ and the acetic acid were added until the reduction was completed. After 4 h, the mixture was concentrated and the remaining residue was dissolved in saturated $NaHCO_3$ (10 mL). The product was extracted with EtOAc (10 mL×3), dried ($MgSO_4$), and concentrated under reduced pressure. The residue was purified by repeated chromatography on silica gel followed by HPLC purification. Lyophilization of the collected fraction resulted the product 30 (13.5 mg, 26%) as trifluoroacetic acid salt: $^1H$ NMR ($CDCl_3$) δ 7.72 (d, 2H, J=8.7 Hz), 7.36 (br, 10H), 7.00 (d, 2H, J=8.7 Hz), 5.69 (d, 1H, J=5.1 Hz), 5.41 (br, 1H), 5.13-4.93 (m, 6H), 4.05-2.5 (m, 19H), 3.88 (s, 3H), 2.5-1.9 (m, 5H), 1.90-1.74 (m, 2H), 0.88 (d, 6H, J=6.1 Hz); $^{31}P$ NMR ($CDCl_3$) δ 25.8; MS (ESI) 856 (M+H).

Example 22

Phosphonic acid 31: A mixture of the dibenzyl phosphonate 30 (9.0 mg, 0.009 mmol) and 10% Pd/C (5.2 mg, Aldrich) in EtOAc (2 mL) and ethanol (0.5 mL) was stirred under $H_2$ atmosphere for 3 h at room temperature. After the mixture was filtered through celite, a drop of trifluoroacetic acid (Aldrich) was added to the filtrate and the filtrate was concentrated to dryness to afford the product 31 (6.3 mg, 86%): $^1H$ NMR ($CD_3OD$) δ 7.76 (d, 2H, J=9.0 Hz), 7.11 (d, 2H, J=9.0 Hz), 5.69 (d, 1H, J=5.1 Hz), 5.54 (br, 1H), 5.09 (br, 1H), 4.05-3.84 (m, 4H), 3.89 (s, 3H), 3.84-3.38 (m, 9H), 3.07 (dd, 2H, J=13.5 and 8.4 Hz), 2.9-2.31 (m, 5H), 2.31-1.83 (m, 6H), 0.92 (d, 3H, J=6.3 Hz), 0.85 (d, 3H, J=6.9 Hz); $^{31}P$ NMR ($CD_3OD$) δ 21.6; MS (ESI) 676 (M+H).

Scheme 7
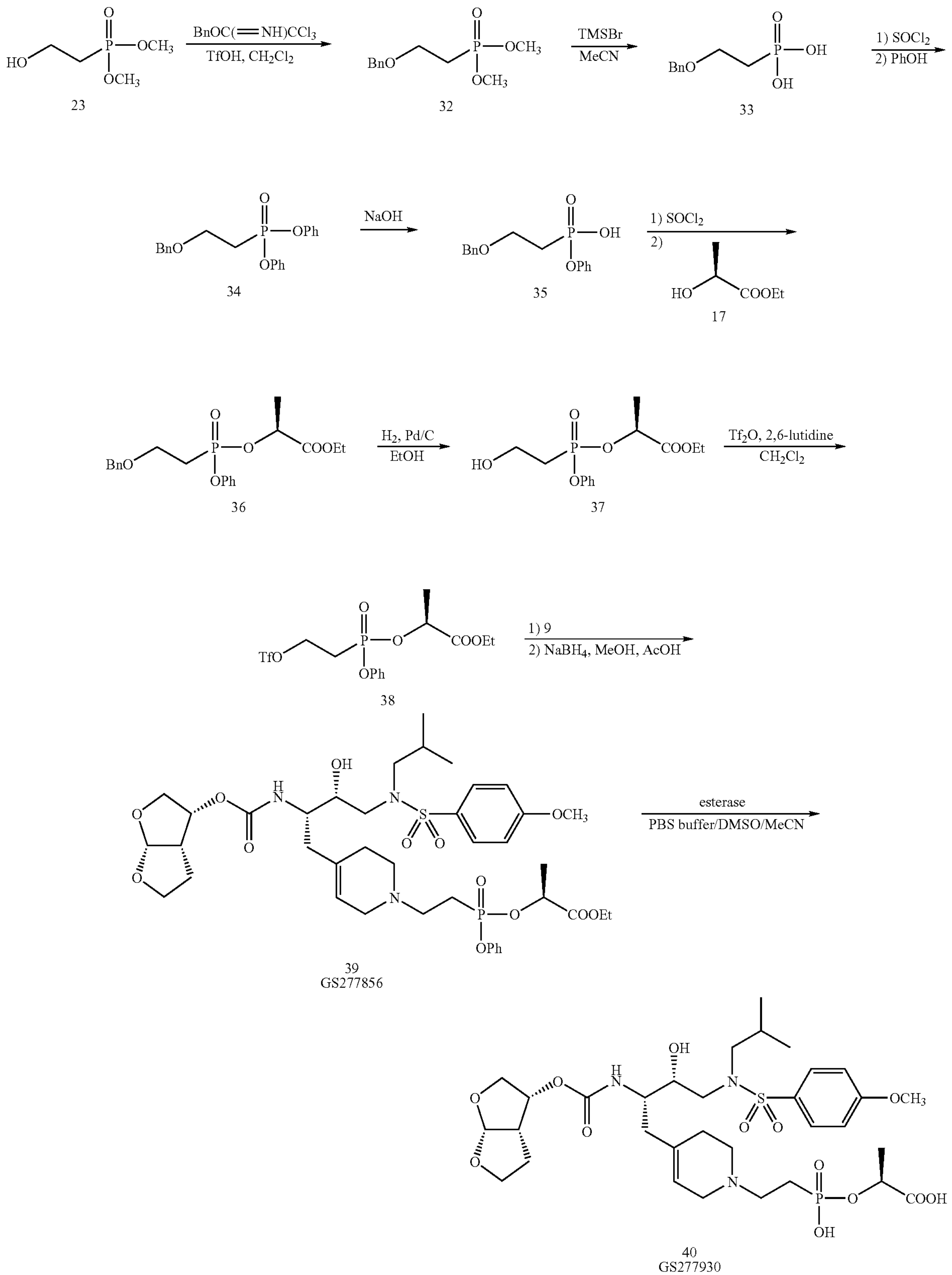
23 32 33 34 35 17 36 37 38
39
GS277856
40
GS277930

Example 23

Benzylether 32: A solution of dimethyl hydroxyethylphosphonate (5.0 g, 32.5 mmol, Across) and benzyl 2,2,2-trichloroacetimidate (97.24 mL, 39.0 mmol, Aldrich) in $CH_2Cl_2$ (100 mL) at 0° C. under a nitrogen atmosphere was treated with trifluoromethanesulfonic acid (0.40 mL). Stirring was performed for three hours at 0° C. and the reaction was then allowed to warm to room temperature while stirring continued. The reaction continued for 15 hours, and the reaction mixture was then diluted with dichloromethane, washed with saturated sodium bicarbonate, washed with brine, dried ($MgSO_4$), concentrated under reduced pressure and chromatographed on silica gel eluting with a gradient of eluent from 60% EtOAc in hexane to 100% EtOAc to afford 4.5 g, (57%) of the benzyl ether as a colorless liquid. $^{31}$P NMR ($CDCl_3$) δ 31.5.

Example 24

Diacid 33: A solution of benzylether 32 (4.5 g, 18.4 mmol) was dissolved in anhydrous acetonitrile (100 mL), chilled to 0° C. under a nitrogen atmosphere and treated with TMS bromide (9.73 mL, 74 mmol). The reaction mixture was warmed to room temperature and after 15 hours of stirring was concentrated repeatedly with MeOH/water to afford the diacid, which was used directly in the next step. $^{31}$P NMR ($CDCl_3$) δ 31.9.

Example 25

Diphenylphosphonate 34: Diacid 33 (6.0 g, 27 mmol) was dissolved in toluene and concentrated under reduced pressure three times, dissolved in anhydrous acetonitrile, stirred under a nitrogen atmosphere, and treated with thionyl chloride (20 mL, 270 mmol) by slow addition. The solution was heated to 70° C. for two hours, then cooled to room temperature, concentrated and dissolved in anhydrous dichloromethane, chilled to −78° C. and treated with phenol (15 g, 162 mmol) and triethylamine (37 mL, 270 mmol). The reaction mixture was warmed to room temperature and stirred for 15 hours, and was then diluted with ice cold dichloromethane, washed with ice cold 1 N. NaOH, washed with ice cold water, dried ($MgSO_4$), and concentrated under reduced pressure. The resulting residue was used directly in the next step. $^1$H NMR ($CDCl_3$) δ 7.40-7.16 (d, 15H), 4.55 (s, 2H), 3.98-3.84 (m, 2H), 2.55-2.41 (m, 2H); $^{31}$P NMR ($CDCl_3$) δ 22.1.

Example 26

Mono acid 35: Monoacid 35 was prepared using conditions analogous to those used to prepare monoacid 16, except that diphenylphosphonate 34 was substituted for benzylether 15. $^1$H NMR ($CDCl_3$) δ 7.38-7.16 (d, 10H), 4.55 (s, 2H), 3.82-3.60 (m, 3H), 2.33-2.21 (m, 2H); $^{31}$P NMR ($CDCl_3$) δ 29.0.

Example 27

Ethyl lactate phosphonate 36: Ethyl lactate phosphonate 36 was prepared analogously to ethyl lactate phosphonate 18 except monoacid 35 was substituted for monoacid 16. $^{31}$P NMR ($CDCl_3$) δ 27.0, 25.6.

Example 28

Ethyl lactate phosphonate with free alcohol 37: Ethyl lactate phosphonate with free alcohol 37 was prepared analogously to ethyl lactate phosphonate with free alcohol 19 except that ethyl lactate phosphonate 36 was substituted for ethyl lactate phosphonate 18. $^{31}$P NMR ($CDCl_3$) δ 28.9, 26.8.

Example 29

Triflate 38: A solution of the alcohol 37 (663 mg, 2.19 mmol) and 2,6-lutidine (0.385 mL, 3.31 mmol, Aldrich) in $CH_2Cl_2$ (5 mL) was stirred at −45° C. as trifluoromethanesulfonic anhydride (0.48 mL, 2.85 mmol, Aldrich) was added. The solution was stirred for 1.5 h at −45° C., diluted with ice-cold water (50 mL), and extracted with EtOAc (30 mL×2). The combined extracts were washed with ice cold water (50 mL), dried ($MgSO_4$), and concentrated under reduced pressure to obtain a crude mixture of two diastereomers (910 mg, 96%, 1:3 ratio): $^1$H NMR (acetone-$d_6$) δ 7.48-7.37 (m, 2H), 7.37-7.18 (m, 3H), 5.2-4.95 (m, 3H), 4.3-4.02 (m, 2H), 3.38-3.0 (m, 1H), 3.0-2.7 (m, 2H), 2.1-1.9 (m, 1H), 1.52 (d, 1H), 1.4 (d, 2H), 1.4-1.1)m, 3H); $^{31}$P NMR (acetone-$d_6$) δ 21.8 (0.75P), 20.5 (0.25P).

Example 30

The prodrug 39: A solution of the crude triflate 38 (499 mg, 1.15 mmol) and the pyridine 9 (494 mg, 0.877 mmol) in acetone (5 mL) was stirred at room temperature for 16.5 h. The solution was concentrated under reduced pressure to obtain the crude pyridinium salt. To a solution of the crude pyridinium salt in ethanol (10 mL) was added 5 drops of a solution of acetic acid (1 mL) in ethanol (5 mL). The solution was stirred at 0° C. as $NaBH_4$ (~10 mg, Aldrich) was added. The solution was maintained to be pH 3-4 by adding the acetic acid solution. More $NaBH_4$ and the acetic acid were added until the reduction was completed. After 5.5 h, the mixture was concentrated under reduced pressure and the remaining residue was dissolved in ice-cold saturated $NaHCO_3$ (50 mL). The product was extracted with ice-cold EtOAc (30 mL×2) and the combined extracts were washed with 50% saturated $NaHCO_3$ (50 mL), dried ($MgSO_4$), and concentrated under reduced pressure. The residue was purified by a chromatography on silica gel followed by a chromatography on C18 reverse phase column material. Lyophilization of the collected fraction resulted the product 39 mixture (376 mg, 50%, ~2.5:1 ratio) as trifluoroacetic acid salt: $^1$H NMR ($CD_3CN$+TFA) δ 7.78 (d, 2H, J=8.7 Hz), 7.52-7.42 (m, 2H); 7.37-7.22 (m 3H), 7.10 (d, 2H, J=8.7 Hz), 5.78 (d, 1H, J=9.0 Hz), 5.64 (m; 1H), 5.50 (br, 1H), 5.08 (m, 2H), 4.31-4.12 (m, 2H), 4.04-3.42 (m, 11H), 3.90 (s, 3H), 3.29 (m, 2H), 3.23-3.16 (m, 1H), 3.08-2.78 (m, 6H), 2.76-2.27 (m, 5H), 2.23-2.11 (m, 1H), 2.08-1.77 (m, 3H), 1.58 (d, 0.9H, J=7.2 Hz), 1.45 (d, 2.1H, J=6.6 Hz), 1.32-1.20 (m, 3H), 0.95-0.84 (m, 6H); $^{31}$P NMR ($CD_3CN$+TFA) δ 24.1 and 23.8, 22.2 and 22.1; MS (ESI) 852 (M+H).

Example 31

Metabolite 40: To a solution of the prodrug 39 (35.4 mg, 0.037 mmol) in DMSO (0.35 mL) and acetonitrile (0.70 mL) was added 0.1 M PBS buffer (10.5 mL) mixed thoroughly to result a suspension. To the suspension was added porcine liver esterase suspension (0.175 mL, EC3.1.1.1, Sigma). After the suspension was stored in 37° C. for 6.5 h, the mixture was filtered through 0.45 um membrane filter and the filtrate was purified by HPLC. The collected fraction was lyophilized to result the product 40 as trifluoroacetic acid salt (28.8 mg, 90%): $^1$H NMR ($D_2O$) δ 7.96 (d, 2H, J=8.7 Hz), 7.32 (d, 2H, J=8.7 Hz), 5.89 (d, 1H, J=5.1 Hz), 5.66 (br, 1H), 5.27 (m, 1H), 4.97 (m, 1H), 4.23-4.12 (m, 2H), 4.08 (s, 3H), 4.06-3.10 (m, 14H), 3.03 (dd, 1H, J=14.1 and 6.6 Hz), 2.78-1.97 (m, 9H), 1.66 (d, 3H, J=6.9 Hz), 1.03 (d, 3H, J=7.5 Hz), 1.01 (d, 3H, J=6.9 Hz); $^{31}$P NMR ($CD_3CN$+TFA) δ 20.0, 19.8; MS (ESI) 748 (M+H).

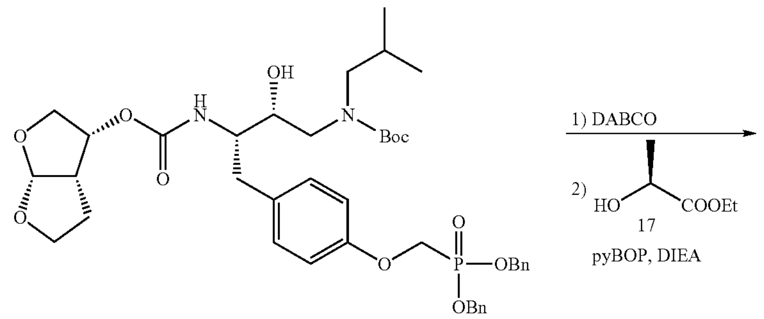
41
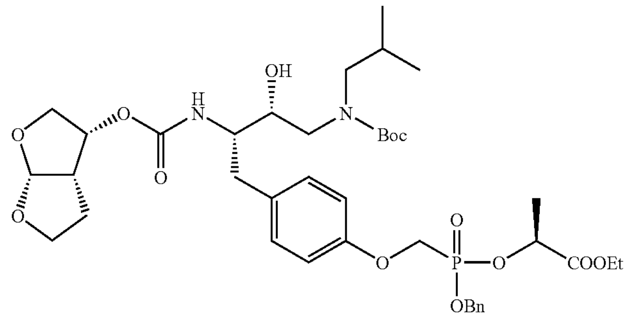
42
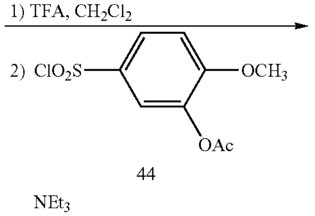
44
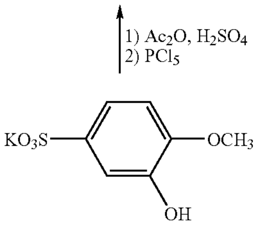
43
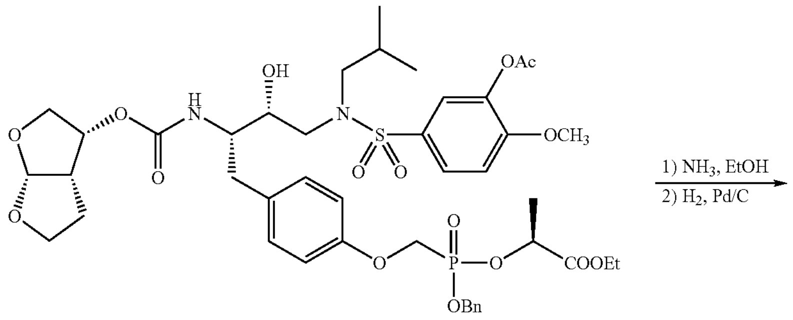
45
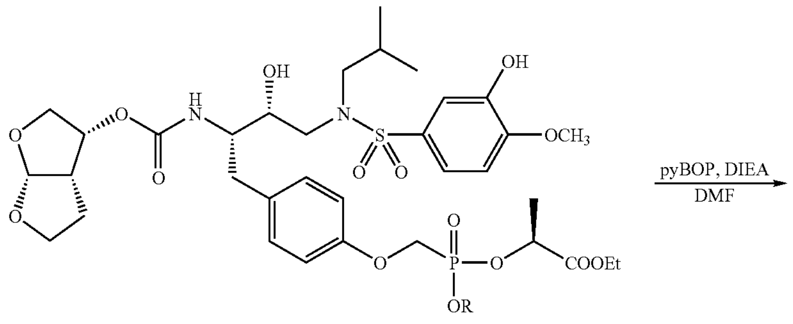
46: R = Bn
47: R = H -continued

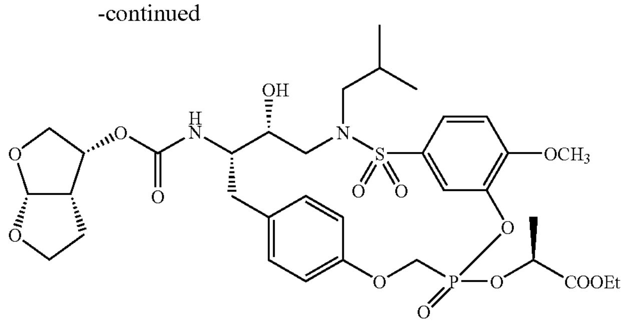

48A: a minor diastereomer (GS277932)
48B: a major diastereomer (GS277933)

Example 32

Compound 42: The dibenzyl phosphonate 41 (947 mg, 1.21 mmol) was treated with DABCO (140.9 mg, 1.26 mmol, Aldrich) in 4.5 mL toluene to obtain the monoacid (890 mg, 106%). The crude monoacid (890 mg) was dried by evaporation with toluene twice and dissolved in DMF (5.3 mL) with ethyl(S)-lactate (0.3 mL, 2.65 mmol, Aldrich) and pyBOP (945 mg, 1.82 mmol, Aldrich) at room temperature. After diisopropylethylamine (0.85 mL, 4.88 mmol, Aldrich) was added, the solution was stirred at room temperature for 4 h and concentrated under reduced pressure to a half volume. The resulting solution was diluted with 5% aqueous HCl (30 mL) and the product was extracted with EtOAc (30 mL×3). After the combined extracts were dried ($MgSO_4$) and concentrated, the residue was chromatographed on silica gel to afford the compound 42 (686 mg, 72%) as a mixture of two diastereomers (2:3 ratio): $^1$H NMR ($CDCl_3$) δ 7.46-7.32 (m, 5H), 7.13 (d, 2H, J=8.1 Hz), 6.85 (t, 2H, J=8.1 Hz), 5.65 (m, 1H), 5.35-4.98 (m, 4H), 4.39 (d, 0.8H, J=10.2H), 4.30-4.14 (m, 3.2H), 3.98 (dd, 1H, J=9.3 and 6.0 Hz), 3.92-3.78 (m, 3H), 3.78-3.55 (m, 3H), 3.16-2.68 (m, 6H), 1.85 (m, 1H), 1.74-1.55 (m, 2H), 1.56 (d, 1.8H, J=7.2 Hz), 1.49 (d, 1.2H), 1.48 (s, 9H), 1.30-1.23 (m, 3H), 0.88 (d, 3H, J=6.3 Hz), 0.87 (d, 3H, J=6.3 Hz); 31P NMR ($CDCl_3$) δ 20.8 (0.4P), 19.5 (0.6P); MS (ESI) 793 (M+H).

Example 33

Compound 45: A solution of compound 42 (101 mg, 0.127 mmol) and trifluoroacetic acid (0.27 mL, 3.5 mmol, Aldrich) in $CH_2Cl_2$ (0.6 mL) was stirred at 0° C. for 3.5 h and concentrated under reduced pressure. The resulting residue was dried in vacuum to result the crude amine as TFA salt.

A solution of the crude amine salt and triethylamine (0.072 mL, 0.52 mmol, Aldrich) in $CH_2Cl_2$ (1 mL) was stirred at 0° C. as the sulfonyl chloride 42 (37 mg, 0.14 mmol) was added. After the solution was stirred at 0° C. for 4 h and 0.5 h at room temperature, the reaction mixture was diluted with saturated $NaHCO_3$ (20 mL) and extracted with EtOAc (20 mL×1; 15 mL×2). The combined organic fractions were washed with saturated NaCl solution, dried ($MgSO_4$), and concentrated under reduced pressure. Purification by chromatography on silica gel provided the sulfonamide 45 (85 mg, 72%) as a mixture of two diastereomers (~1:2 ratio): $^1$H NMR ($CDCl_3$) δ 7.45-7.31 (m, 7H), 7.19 (d, 1H, J=8.4 Hz), 7.12 (d, 2H, J=7.8 Hz), 6.85 (m, 2H), 5.65 (d, 1H, J=5.4 Hz), 5.34-5.16 (m, 2H), 5.13-4.97 (m, 2H), 4.97-4.86 (m, 1H), 4.38 (d, 0.7H, J=10.8 Hz), 4.29-4.12 (m, 3.3H), 3.96 (dd, 1H, J=9.3 and 6.3 Hz), 3.89 (s, 3H), 3.92-3.76 (m, 3H), 3.76-3.64 (m, 2H), 3.64-3.56 (br, 1H), 3.34-3.13 (m, 1H), 3.11-2.70 (m, 6H), 2.34 (s, 3H), 1.86 (m, 1H, J=7.0 Hz), 1.75-1.58 (m, 2H), 1.56 (d, 2H, J=7.2 Hz), 1.49 (d, 1H, J=7.2 Hz), 1.29-1.22 (m, 3H), 0.94 (d, 3H, J=6.6 Hz), 0.90 (d, 3H, J=6.9 Hz); $^{31}$P NMR ($CDCl_3$) δ 20.7 (0.3P), 19.5 (0.7P); MS (ESI) 921 (M+H).

Example 34

Compound 46: Compound 45 (257 mg, 0.279 mmol) was stirred in a saturated solution of ammonia in ethanol (5 mL) at 0° C. for 15 min and the solution was concentrated under reduced pressure. Purification of the residue by chromatography on silica gel provided compound 46 (2.6 mg, 84%): $^1$H NMR ($CDCl_3$) δ 7.48-7.34 (m, 4H), 7.22-7.05 (m, 5H), 7.01 (d, 1H, J=8.1 Hz), 6.87-6.80 (m, 2H), 5.68 (d, 1H, J=4.8 Hz), 5.32 (dd, 1.3H, J=8.7 and 1.8 Hz), 5.22 (d, 0.7H, J=9.0 Hz), 5.11-5.00 (m, 3H), 4.47-4.14 (m, 4H), 4.00 (dd, 1H, J=9.9 and 6.6 Hz), 3.93 (s, 3H), 3.95-3.63 (m, 5H), 3.07-2.90 (m, 4H), 2.85-2.75 (m, 1H), 2.75-2.63 (m, 2H), 1.88-1.67 (m, 3H), 1.65-1.55 (m, 2H), 1.57 (d, 2H, J=6.9 Hz), 1.50 (d, 1H, J=7.2 Hz), 1.31-1.20 (m, 3H), 0.95 (d, 3H, J=6.6 Hz), 0.88 (d, 3H, J=6.3 Hz); $^{31}$P NMR ($CDCl_3$) δ 20.7 (0.3P), 19.6 (0.7P); MS (ESI) 879 (M+H).

Example 35

Compound 47: A mixture of compound 46 (176 mg, 0.200 mmol) and 10% Pd/C (9.8 mg, Aldrich) in EtOAc (4 mL) and ethanol (1 mL) was stirred under $H_2$ atmosphere for 3 h at room temperature. After the mixture was filtered through celite, the filtrate was concentrated to dryness to afford compound 47 (158 mg, 100%) as white powder: $^1$H NMR ($CDCl_3$) δ 7.30-7.16 (m, 2H), 7.12 (d, 2H, J=7.5 Hz), 7.01 (d, 1H, J=7.8 Hz), 6.84 (d, 2H, J=7.5 Hz), 5.66 (d, 1H, J=4.5 Hz), 5.13-4.97 (m, 2H), 4.38-4.10 (m, 4H), 3.93 (s, 3H), 4.02-3.66 (m, 6H), 3.13-2.69 (m, 7H), 1.96-1.50 (m, 3H), 1.57 (d, 3H, J=6.6 Hz), 1.26 (t, 3H, J=7.2 Hz), 0.93 (d, 3H, J=6.0 Hz), 0.88 (d, 3H, J=6.0 Hz); $^{31}$P NMR ($CDCl_3$) δ 20.1; MS (ESI) 789 (M+H).

Example 36

Compound 48A and 48B: A solution of pyBOP (191 mg, 0.368 mmol, Aldrich) and diisopropylethylamine (0.1 mL, 0.574 mmol, Aldrich) in DMF (35 mL) was stirred at room temperature as a solution of compound 47 (29 mg, 0.036 mmol) in DMF (5.5 mL) was added over 16 h. After addition, the solution was stirred at room temperature for 3 h and concentrated under reduced pressure. The residue was dissolved in ice-cold water and extracted with EtOAc (20 mL×1; 10 mL×2). The combined extracts were dried ($MgSO_4$) and concentrated under reduced pressure. The residue was purified by chromatography on silica gel followed by preparative TLC gave two isomers of structure 48 (1.0 mg, 3.6% and 3.6 mg, 13%). Isomer 48A: $^1H$ NMR ($CDCl_3$) δ 7.39 (m, 1H), 7.12 (br, 1H), 7.01 (d, 2H, J=8.1 Hz), 6.98 (br, 1H), 6.60 (d, 2H, J=8.1 Hz), 5.75 (d, 1H, J=5.1 Hz), 5.37-5.28 (m, 2H), 5.18 (q, 1H, J=8.7 Hz), 4.71 (dd, 1H, J=14.1 and 7.5 Hz), 4.29 (m, 3H), 4.15-4.06 (m, 1H), 3.99 (s, 3H), 4.05-3.6 (m, 5H), 3.35 (m, 1H), 3.09 (br, 1H), 2.90-2.78 (m, 3H), 2.2-2.0 (m, 3H), 1.71 (d, 3H, J=6.6 Hz), 1.34 (t, 3H, J=6.9 Hz), 1.01 (d, 3H, J=6.3 Hz), 0.95 (d, 3H, J=6.3 Hz); $^{31}P$ NMR ($CDCl_3$) δ 17.8; MS (ESI) 793 (M+Na); isomer 48B: $^1H$ NMR ($CDCl_3$) δ 7.46 (d, 1H, J=9.3 Hz), 7.24 (br, 1H), 7.00 (d, 2H, J=8.7 Hz), 6.91 (d, 1H, J=8.7 Hz), 6.53 (d, 2H, J=8.7 Hz), 5.74 (d, 1H, J=5.1 Hz), 5.44 (m, 1H), 5.35 (d, 1H, J=9.0 Hz), 5.18 (q, 1H, J=7.2 Hz), 4.68 (dd, 1H, J=14.4 and 6.3 Hz), 4.23 (m, 3H), 4.10 (m, 1H), 4.04 (s, 3H), 3.77-4.04 (m, 6H), 3.46 (dd, 1H, J=12.9 and 11.4 Hz), 3.08 (br, 1H), 2.85 (m, 2H), 2.76 (dd, 1H, J=12.9 and 4.8 Hz), 1.79-2.11 (m, 3H), 1.75 (d, 3H, J=6.6 Hz), 1.70 (m, 2H), 1.27 (t, 3H, J=6.9 Hz), 1.01 (d, 3H, J=6.6 Hz), 0.93 (d, 3H, J=6.6 Hz); $^{31}P$ NMR ($CDCl_3$) δ 15.4; MS (ESI) 793 (M+Na).

Example 1

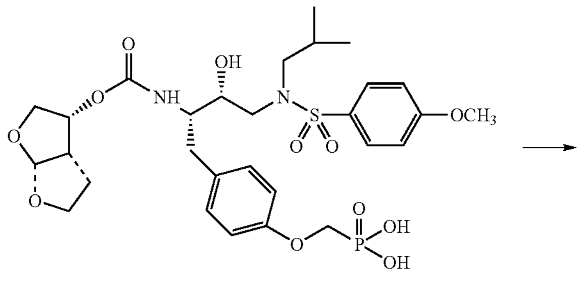

1

-continued

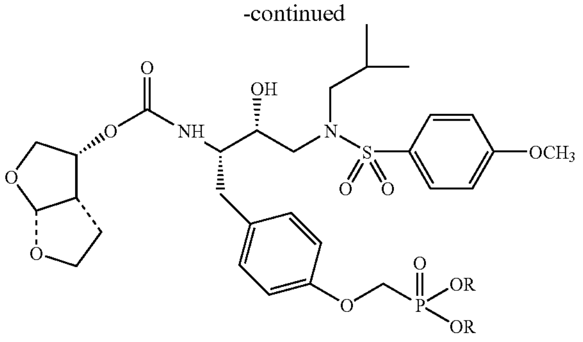

2 R = $CH_3$
3 R = $CH(CH_3)_2$

Example 1A

Dimethylphosphonic ester 2 (R=$CH_3$): To a flask was charged with phosphonic acid 1 (67 mg, 0.1 mmol), methanol (0.1 mL, 2.5 mmol) and 1,3-dicyclohexylcarbodiimide (83 mg, 0.4 mmol), then pyridine (1 mL) was added under $N_2$. The resulted mixture was stirred at 60-70° C. for 2 h, then cooled to room temperature and diluted with ethyl acetate. The mixture was filtered and the filtrate was evaporated. The residue was diluted with ethyl acetate and the combined organic phase was washed with $NH_4Cl$, brine and water, dried over $Na_2SO_4$, filtered and concentrated. The residue was purified by chromatography on silica gel (isopropanol/$CH_2Cl_2$, 1% to 7%) to give 2 (39 mg, 56%) as a white solid. $^1H$ NMR ($CDCl_3$) δ 7.71 (d, J=8.7 Hz, 2H), 7.15 (d, J=8.7 Hz, 2H), 7.00 (d, J=8.7 Hz, 2H), 6.87 (d, J=8.7 Hz, 2H), 5.65 (d, J=5.1 Hz, 1H), 5.10-4.92 (m, 4H), 4.26 (d, J=9.9 Hz, 2H), 3.96-3.65 (m overlapping s, 15H), 3.14-2.76 (r, 7H), 1.81-1.55 (m, 3H), 0.91 (d, J=6.6 Hz, 3H), 0.88 (d, J=6.6 Hz, 3H); $^{31}P$ NMR ($CDCl_3$) δ 21.7; MS (ESI) 723 (M+Na).

Example 1B

Diisopropylphosphonic ester 3 (R=$CH(CH_3)_2$) was synthesized in the same manner in 60% yield. $^1H$ NMR ($CDCl_3$) δ 7.71 (d, J=8.7 Hz, 2H), 7.15 (d, J=8.7 Hz, 2H), 7.15 (d, J=8.7 Hz, 2H), 6.99 (d, J=8.7 Hz, 2H), 6.87 (d, J=8.7 Hz, 2H), 5.66 (d, J=5.1 Hz, 1H), 5.08-4.92 (m, 3H), 4.16 (d, J=10.5 Hz, 2H), 3.98-3.68 (m overlapping s, 9H), 3.16-2.78 (m, 7H), 1.82-1.56 (m, 3H), 1.37 (t, J=6.3 Hz, 6H), 0.93 (d, J=6.6 Hz, 3H), 0.88 (d, J=6.6 Hz, 3H); $^{31}P$ NMR ($CDCl_3$) δ 17.3; MS (ESI) 779 (M+Na).

Example 2

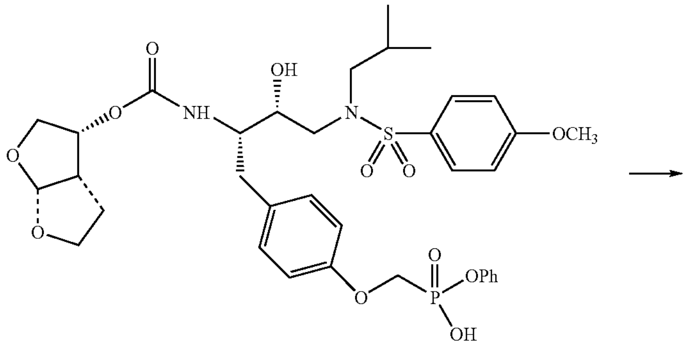

4

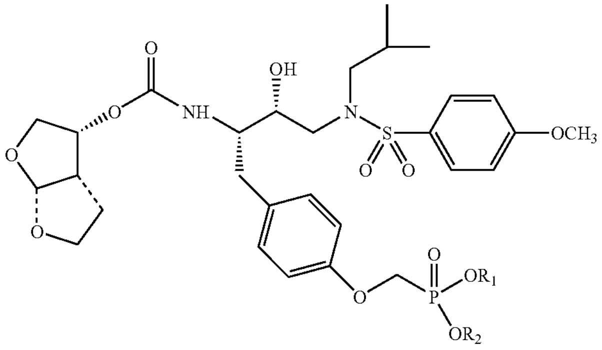

5

| Compound | $R_1$ | $R_2$ |
|---|---|---|
| 5a | OPh | mix-Hba-Et |
| 5b | OPh | (S)-Hba-Et |
| 5c | OPh | (S)-Hba-tBu |
| 5d | OPh | (S)-Hba-EtMor |
| 5e | OPh | (R)-Hba-Et |

Example 2A

Monolactate 5a (R1=OPh, R2=Hba-Et): To a flask was charged with monophenyl phosphonate 4 (250 mg, 0.33 mmol), 2-hydroxy-n-butyric acid ethyl ester (145 mg, 1.1 mmol) and 1,3-dicyclohexylcarbodiimide (226 mg, 1.1 mmol), then pyridine (2.5 mL) was added under $N_2$. The resulted mixture was stirred at 60-70° C. for 2 h, then cooled to room temperature and diluted with ethyl acetate. The mixture was filtered and the filtrate was evaporated. The residue was diluted with ethyl acetate and the combined organic phase was washed with $NH_4Cl$, brine and water, dried over $Na_2SO_4$, filtered and concentrated. The residue was purified by chromatography on silica gel ($EtOAc/CH_2Cl_2$, 1:1) to give 5a (150 mg, 52%) as a white solid. $^1H$ NMR ($CDCl_3$) δ 7.70 (d, J=8.7 Hz, 2H), 7.37-7.19 (m, 5H), 7.14 (d, J=8.7 Hz, 2H), 7.00 (d, J=8.7 Hz, 2H), 6.91 (d, J=8.7 Hz, 1H), 6.86 (d, J=8.7 Hz, 1H), 5.65 (m, 1H), 5.10-4.95 (m, 3H), 4.57-4.39 (m, 2H), 4.26 (m, 2H), 3.96-3.68 (m overlapping s, 9H), 3.15-2.77 (m, 7H), 1.81-1.55 (m, 5H), 1.21 (m, 3H), 1.04-0.86 (m, 6H); $^{31}P$ NMR ($CDCl_3$) δ 17.5 and 15.1; MS (ESI) 885 (M+Na).

Example 2B

Monolactate 5b (R1=OPh, R2=(S)-Hba-Et): To a flask was charged with monophenyl phosphonate 4 (600 mg, 0.8 mmol), (S)-2-hydroxy-n-butyric acid ethyl ester (317 mg, 2.4 mmol) and 1,3-dicyclohexylcarbodiimide (495 mg, 2.4 mmol), then pyridine (6 mL) was added under $N_2$. The resulted mixture was stirred at 60-70° C. for 2 h, then cooled to room temperature and diluted with ethyl acetate. The mixture was filtered and the filtrate was evaporated. The residue was diluted with ethyl acetate and the combined organic phase was washed with $NH_4Cl$, brine and water, dried over $Na_2SO_4$, filtered and concentrated. The residue was purified by chromatography on silica gel ($EtOAc/CH_2Cl_2$, 1:1) to give 5b (360 mg, 52%) as a white solid. $^1H$ NMR ($CDCl_3$) δ 7.71 (d, J=8.7 Hz, 2H), 7.37-7.19 (m, 5H), 7.15 (d, J=8.7 Hz, 2H), 7.00 (d, J=8.7 Hz, 2H), 6.92 (d, J=8.7 Hz, 1H), 6.86 (d, J=8.7 Hz, 1H), 5.65 (m, 1H), 5.10-4.95 (m, 3H), 4.57-4.39 (m, 2H), 4.26 (m, 2H), 3.96-3.68 (m overlapping s, 9H), 3.15-2.77 (m, 7H), 1.81-1.55 (m, 5H), 1.23 (m, 3H), 1.04-0.86 (m, 6H); $^{31}P$ NMR ($CDCl_3$) δ 17.5 and 15.2; MS (ESI) 885 (M+Na).

Example 2C

Monolactate 5c (R1=OPh, R2=(S)-Hba-tBu): To a flask was charged with monophenyl phosphonate 4 (120 mg, 0.16 mmol), tert-butyl(S)-2-hydroxybutyrate (77 mg, 0.48 mmol) and 1,3-dicyclohexylcarbodiimide (99 mg, 0.48 mmol), then pyridine (1 nL) was added under $N_2$. The resulted mixture was stirred at 60-70° C. for 2 h, then cooled to room temperature and diluted with ethyl acetate. The mixture was filtered and the filtrate was evaporated. The residue was diluted with ethyl acetate and the combined organic phase was washed with $NH_4Cl$, brine and water, dried over $Na_2SO_4$, filtered and concentrated. The residue was purified by chromatography on silica gel ($EtOAc/CH_2Cl_2$, 1:1) to give 5c (68 mg, 48%) as a white solid. $^1H$ NMR ($CDCl_3$) δ 7.71 (d, J=8.7 Hz, 2H), 7.37-7.19 (m, 5H), 7.14 (d, J=8.7 Hz, 2H), 7.00 (d, J=8.7 Hz, 2H), 6.93 (d, J=8.7 Hz, 1H), 6.86 (d, J=8.7 Hz, 1H), 5.64 (m, 1H), 5.10-4.95 (m, 3H), 4.57-4.39 (m, 2H), 4.26 (m, 2H), 3.96-3.68 (m overlapping s, 9H), 3.15-2.77 (m, 7H), 1.81-1.55 (m, 5H), 1.44 (d, J=11 Hz, 9H), 1.04-0.86 (m, 9H); $^{31}P$ NMR ($CDCl_3$) δ 17.5 and 15.2; MS (ESI) 913 (M+Na).

Example 2D

Monolactate 5d (R1=OPh, R2=(S)-Lac-EtMor): To a flask was charged with monophenyl phosphonate 4 (188 mg, 0.25 mmol), (S)-lactate ethylmorpholine ester (152 mg, 0.75 mmol) and 1,3-dicyclohexylcarbodiimide (155 mg, 0.75 mmol), then pyridine (2 mL) was added under $N_2$. The resulted mixture was stirred at 60-70° C. for 2 h, then cooled to room temperature and diluted with ethyl acetate. The mixture was filtered and the filtrate was evaporated. The residue was washed with ethyl acetate and the combined organic phase was washed with $NH_4Cl$, brine and water, dried over $Na_2SO_4$, filtered and concentrated. The residue was purified by chromatography on silica gel (isopropanol/$CH_2Cl_2$, 1:9) to give 5d (98 mg, 42%) as a white solid. $^1H$ NMR ($CDCl_3$) δ 7.72 (d, J=8.7 Hz, 2H), 7.34-7.20 (m, 5H), 7.15 (d, J=8.7 Hz, 2H), 7.00 (d, J=8.7 Hz, 2H), 6.92 (d, J=8.7 Hz, 1H), 6.87 (d, J=8.7 Hz, 1H), 5.65 (m, 1H), 5.21-4.99 (m, 3H), 4.57-4.20 (m, 4H), 3.97-3.63 (m overlapping s, 13H), 3.01-2.44 (m, 13H), 1.85-1.50 (m, 6H), 0.92 (d, J=6.5 Hz, 3H), 0.88 (d, J=6.5, 3H); $^{31}P$ NMR ($CDCl_3$) δ 17.4 and 15.3; MS (ESI) 934 (M).

Example 2E

Monolactate 5e (R1=OPh, R2=(R)-Hba-Et): To a flask was charged with monophenyl phosphonate 4 (600 mg, 0.8 mmol), (R)-2-hydroxy-n-butyric acid ethyl ester (317 mg, 2.4 mmol) and 1,3-dicyclohexylcarbodiimide (495 mg, 2.4 mmol), then pyridine (6 mL) was added under $N_2$. The resulted mixture was stirred at 60-70° C. for 2 h, then cooled to room temperature and diluted with ethyl acetate. The mixture was filtered and the filtrate was evaporated. The residue was diluted with ethyl acetate and the combined organic phase was washed with $NH_4Cl$, brine and water, dried over $Na_2SO_4$, filtered and concentrated. The residue was purified by chromatography on silica gel ($EtOAc/CH_2Cl_2$, 1:1) to give 5e (345 mg, 50%) as a white solid. $^1H$ NMR ($CDCl_3$) δ 7.70 (d, J=8.7 Hz, 2H), 7.37-7.19 (m, 5H), 7.15 (d, J=8.7 Hz, 2H), 7.00 (d, J=8.7 Hz, 2H), 6.92 (d, =8.7 Hz, 1H), 6.86 (d, J=8.7 Hz, 1H), 5.65 (m, 1H), 5.10-4.95 (m, 3H), 4.57-4.39 (m, 2H), 4.26 (m, 2H), 3.96-3.68 (m overlapping s, 9H), 3.15-2.77 (m, 7H), 1.81-1.55 (m, 5H), 1.23 (m, 3H), 1.04-0.86 (m, 6H); $^{31}P$ NMR ($CDCl_3$) δ 17.5 and 15.1; MS (ESI) 885 (M+Na).

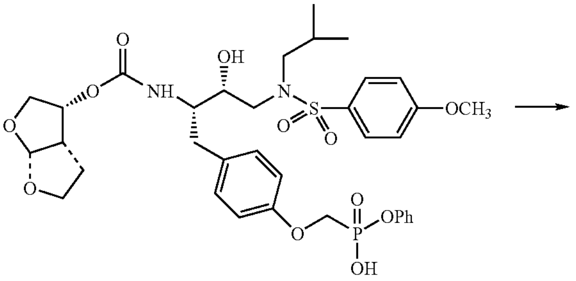

4

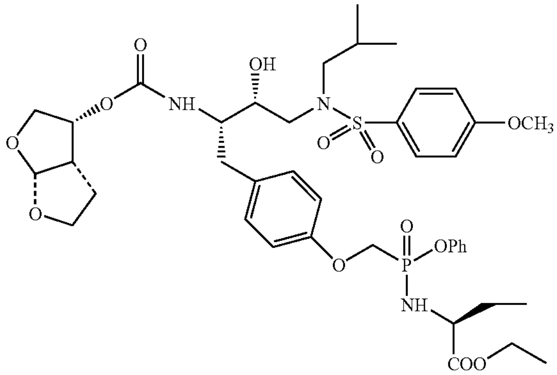

6

Example 3

Monoamidate 6: To a flask was charged with monophenyl phosphonate 4 (120 mg, 0.16 mmol), L-alanine butyric acid ethyl ester hydrochloride (160 mg, 0.94 mmol) and 1,3-dicyclohexylcarbodiimide (132 mg, 0.64 mmol), then pyridine (1 mL) was added under $N_2$. The resulted mixture was stirred at 60-70° C. for 2 h, then cooled to room temperature and diluted with ethyl acetate. The mixture was filtered and the filtrate was evaporated. The residue was diluted with ethyl acetate and the combined organic phase was washed with $NH_4Cl$, brine and water, dried over $Na_2SO_4$, filtered and concentrated. The residue was purified by chromatography on silica gel (isopropanol/$CH_2Cl_2$, 1:9) to give 6 (55 mg, 40%) as a white solid. $^1H$ NMR ($CDCl_3$) δ 7.72 (d, J=8.7 Hz, 2H), 7.37-7.23 (m, 5H), 7.16 (d, J=8.7 Hz, 2H), 7.00 (d, J=8.7 Hz, 2H), 6.90-6.83 (m, 2H), 5.65 (d, J=5.1 Hz, 1H), 5.10-4.92 (m, 3H), 4.28 (m, 2H), 3.96-3.68 (m overlapping s, 9H), 3.15-2.77 (m, 7H), 1.81-1.55 (m, 5H), 1.23 (m, 3H), 1.04-0.86 (m, 6H); $^{31}P$ NMR ($CDCl_3$) δ 20.7 and 19.6; MS (ESI) 884(M+Na).

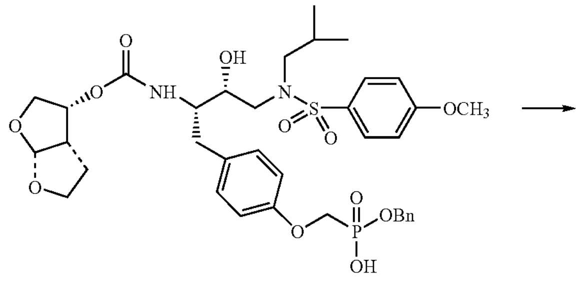

7

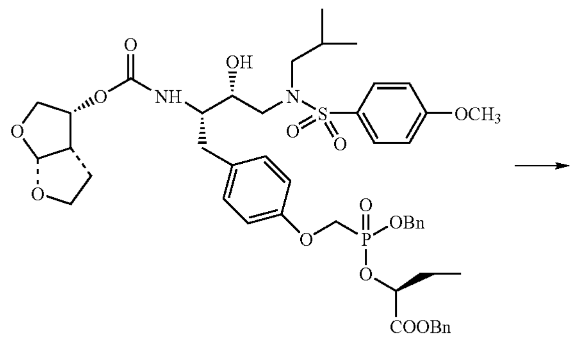

8

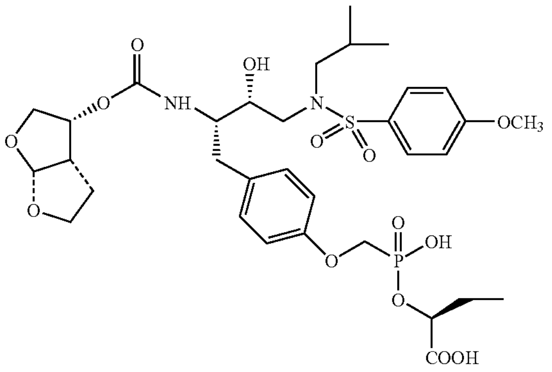

9

Example 4A

Compound 8: To a stirred solution of monobenzyl phosphonate 7 (195 mg, 0.26 mmol) in 1 mL of DMF at room temperature under $N_2$ was added benzyl-(s)-lactate (76 mg, 0.39 mmol) and PyBOP (203 mg, 0.39 mmol), followed by DIEA (181 μL, 1 mmol). After 3 h, the solvent was removed under reduced pressure, and the resulting crude mixture was purified by chromatography on silica gel (ethyl acetate/hexane 1:1) to give 8 (120 mg, 50%) as a white solid. $^1$H NMR ($CDCl_3$) δ 7.71 (d, J=8.7 Hz, 2H), 7.38-7.34 (m, 5H), 7.12 (d, J=8.7 Hz, 2H), 6.99 (d, J=8.7 Hz, 2H), 6.81 (d, J=8.7 Hz, 2H), 5.64 (d, J=5.4 Hz, 1H), 5.24-4.92 (m, 7H), 4.28 (m, 2H), 3.96-3.67 (m overlapping s, 9H), 3.16-2.76 (m, 7H), 1.95-1.62 (m, 5H), 0.99-0.87 (m, 9H); $^{31}$P NMR ($CDCl_3$) δ 21.0 and 19.7; MS (ESI) 962 (M+Na).

Example 4B

Compound 9: A solution of compound 8 (100 mg) was dissolved in EtOH/EtOAc (9 mL/3 mL), treated with 10% Pd/C (10 mg) and was stirred under $H_2$ atmosphere (balloon) for 1.5 h. The catalyst was removed by filtration through celite. The filtered was evaporated under reduced pressure, the residue was triturated with ether and the solid was collected by filtration to afford the compound 9 (76 mg, 94%) as a white solid. $^1$H NMR ($CD_3OD$) δ 7.76 (d, J=8.7 Hz, 2H), 7.18 (d, J=8.7 Hz, 2H), 7.08 (d, J=8.7 Hz, 2H), 6.90 (d, J=8.7 Hz, 2H), 5.59 (d, J=5.4 Hz, 1H), 5.03-4.95 (m, 2H), 4.28 (m, 2H), 3.90-3.65 (m overlapping s, 9H), 3.41 (m, 2H), 3.18-2.78 (m, 5H), 2.44 (m, 1H), 1.96 (m, 3H), 1.61 (m, 2H), 1.18 (m, 3H), 0.93 (d, J=6.3 Hz, 3H), 0.87 (d, J=6.3 Hz, 3H); $^{31}$P NMR ($CD_3OD$) δ 18.3; MS (ESI) 782 (M+Na).

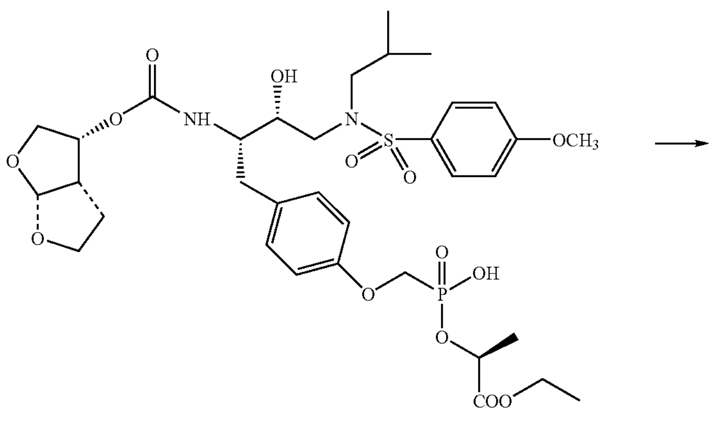

10

-continued

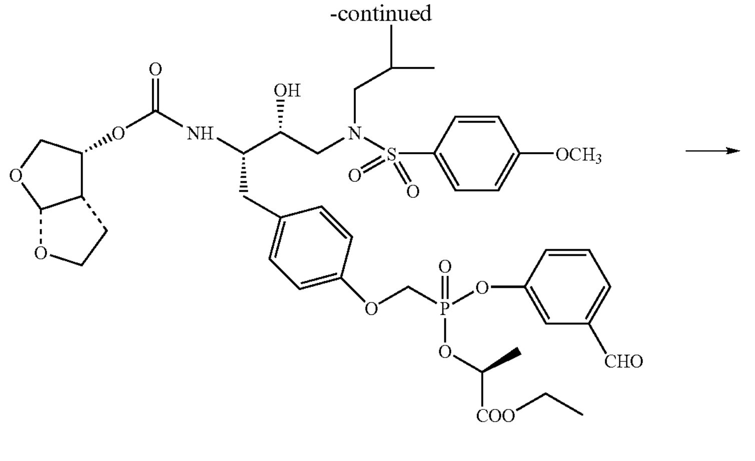

11

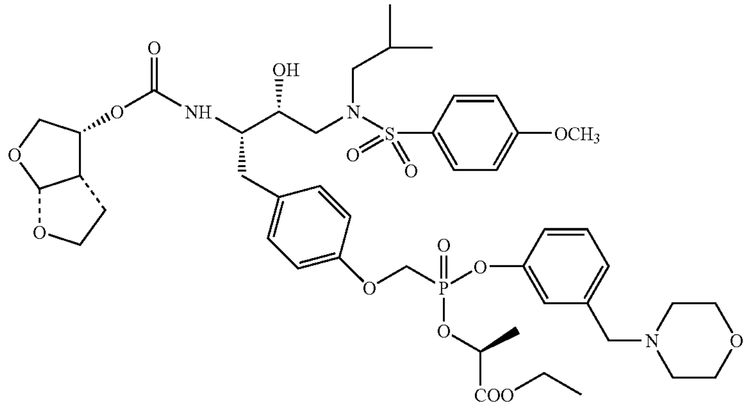

12

Example 5A

Compound 11: To a stirred solution of compound 10 (1 g, 1.3 mmol) in 6 mL of DMF at room temperature under $N_2$ was added 3-hydroxybenzaldehyde (292 mg, 2.6 mmol) and PyBOP (1 g, 1.95 mmol), followed by DIEA (0.9 mL, 5.2 mmol). After 5 h, the solvent was removed under reduced pressure, and the resulting crude mixture was purified by chromatography on silica gel (ethyl acetate/hexane 1:1) to give 11 (800 mg, 70%) as a white solid. $^1$H NMR ($CDCl_3$) δ 9.98 (s, 1H), 7.79-6.88 (m, 12H), 5.65 (m, 1H), 5.21-4.99 (m, 3H), 4.62-4.16 (m, 4H), 3.99-3.61 (m overlapping s, 9H), 3.11-2.79 (m, 5H), 1.85-1.53 (m, 6H), 1.25 (m, 3H), 0.90 (m, 6H); $^{31}$P NMR ($CDCl_3$) δ 17.9 and 15.9; MS (ESI) 899 (M+Na).

Example 5B

Compound 12: To a stirred solution of compound 11 (920 mg, 1.05 mmol) in 10 mL of ethyl acetate at room temperature under $N_2$ was added morpholine (460 mg, 5.25 mmol) and acedic acid (0.25 mL, 4.2 mmol), followed by sodium cyanoborohydride (132 mg, 2.1 mmol). After 20 h, the solvent was removed under reduced pressure, and the residue was diluted with ethyl acetate and the combined organic phase was washed with $NH_4Cl$, brine and water, dried over $Na_2SO_4$, filtered and concentrated. The residue was purified by chromatography on silica gel (isopropanol/$CH_2Cl_2$, 6%) to give 12 (600 mg, 60%) as a white solid. $^1$H NMR ($CDCl_3$) δ 7.71 (d, J=8.7 Hz, 2H), 7.27 (m, 4H), 7.15 (d, J=8.7 Hz, 2H), 6.95 (d, J=8.7 Hz, 2H), 6.89 (m, 2H), 5.65 (m, 1H), 5.21-5.02 (m, 3H), 4.58-4.38 (m, 2H), 4.21-4.16 (m, 2H), 3.99-3.63 (m overlapping s, 15H), 3.47 (s, 2H), 3.18-2.77 (m, 7H), 2.41 (s, 4H), 1.85-1.53 (m, 6H), 1.25 (m, 3H), 0.90 (m, 6H); $^{31}$P NMR ($CDCl_3$) δ 17.4 and 15.2; MS (ESI) 971 (M+Na).

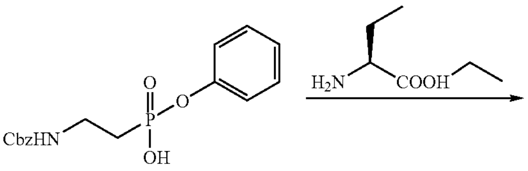

13

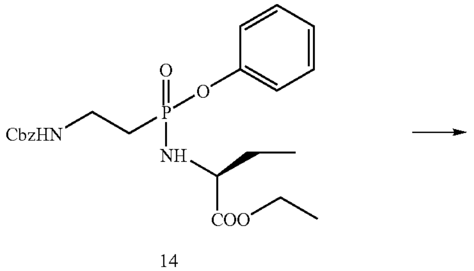

14

-continued

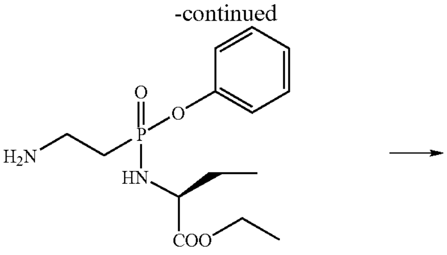

15

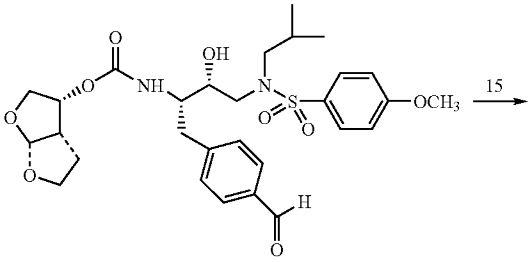

16

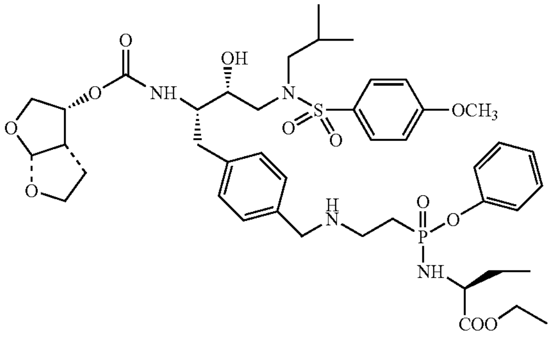

17

Example 6A

Compound 14: To a stirred solution of compound 13 (1 g, 3 mmol) in 30 mL of acetonitrile at room temperature under $N_2$ was added thionyl chloride (0.67 mL, 9 mmol). The resulted mixture was stirred at 60-70° C. for 0.5 h. After cooled to room temperature, the solvent was removed under reduced pressure, and the residue was added 30 mL of DCM, followed by DIEA (1.7 mL, 10 mmol), L-alanine butyric acid ethyl ester hydrochloride (1.7 g, 10 mmol) and TEA (1.7 mL, 12 mmol). After 4 h at room temperature, the solvent was removed under reduced pressure, and the residue was diluted with DCM and washed with brine and water, dried over $Na_2SO_4$, filtered and concentrated. The residue was purified by chromatography on silica gel (Hexane/EtOAc 1:1) to give 14 (670 mg, 50%) as a yellow oil. $^1$H NMR ($CDCl_3$) δ 7.33-7.11 (m, 10H), 5.70 (m, 1H), 5.10 (s, 2H), 4.13-3.53 (m, 5H), 2.20-2.10 (m, 2H), 1.76-1.55 (m, 2H), 1.25-1.19 (m, 3H), 0.85-0.71 (m, 3H); $^{31}$P NMR ($CDCl_3$) δ 30.2 and 29.9; MS (ESI) 471 (M+Na).

Example 6B

Compound 15: A solution of compound 14 (450 mg) was dissolved in 9 mL of EtOH, then 0.15 mL of acetic acid and 10% Pd/C (90 mg) was added. The resulted mixture was stirred under H2 atmosphere (balloon) for 4 h. After filtration through celite, the filtered was evaporated under reduced pressure to afford the compound 15 (300 mg, 95%) as a colorless oil. $^1$H NMR ($CDCl_3$) δ 7.29-7.12 (m, 5H), 4.13-3.53 (m, 5H), 2.20-2.10 (m, 2H), 1.70-1.55 (m, 2H), 1.24-1.19 (m, 3H), 0.84-0.73(m, 3H); $^{31}$P NMR ($CDCl_3$) δ 29.1 and 28.5; MS (ESI) 315 (M+1).

Example 6C

Monoamdidate 17: To a stirred solution of compound 16 (532 mg, 0.9 mmol) in 4 mL of 1,2-dichloroethane was added compound 15 (300 mg, 0.96 mmol) and $MgSO_4$ (50 mg), the resulted mixture was stirred at room temperature under argon for 3 h, then acetic acid (1.3 mL, 23 mmol) and sodium cyanoborohydride (1.13 g, 18 mmol) were added. The reaction mixture was stirred at room temperature for 1 h under argon. Then aqueous $NaHCO_3$ (50 mL) was added, and the mixture was extracted with ethyl acetate, and the combined organic layers were washed with brine and water, dried over $Na_2SO_4$, filtered and concentrated. The residue was purified by chromatography on silica gel (EtOH/EtOAc, 1/9) to give 17 (600 mg, 60%) as a white solid. $^1$H NMR ($CDCl_3$) δ 7.73 (d, J=8.7 Hz, 2H), 7.33-7.13 (m, 9H), 7.00 (d, J=8.7 Hz, 2H), 5.65 (d, J=5.4 Hz, 1H), 5.11-4.98 (m, 2H), 4.22-3.68 (m overlapping s, 15H), 3.20-2.75 (m, 9H), 2.21-2.10 (m, 2H), 1.88-1.55 (m, 5H), 1.29-1.19 (m, 3H), 0.94-0.70 (m, 9H); $^{31}$P NMR ($CDCl_3$) δ 31.8 and 31.0; MS (ESI) 889 (M).

Example 7

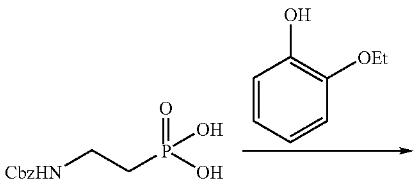

18

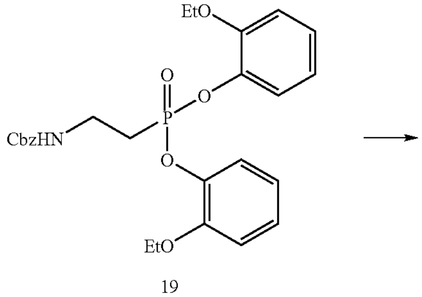

19

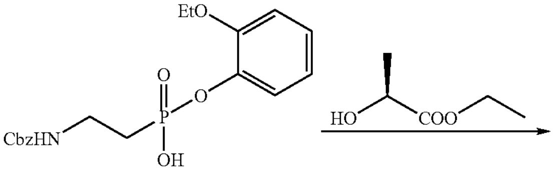

20

-continued

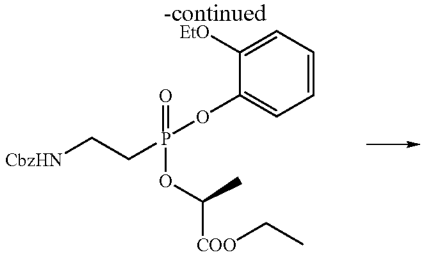

21

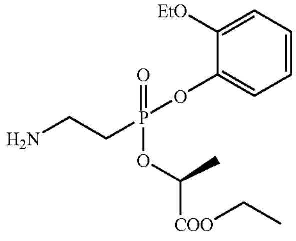

22

Example 7A

Compound 19: To a stirred solution of compound 18 (3.7 g, 14.3 mmol) in 70 mL of acetonitrile at room temperature under $N_2$ was added thionyl chloride (6.3 mL, 86 mmol). The resulted mixture was stirred at 60-70° C. for 2 h. After cooled to room temperature, the solvent was removed under reduced pressure, and the residue was added 150 mL of DCM, followed by TEA (12 mL, 86 mmol) and 2-ethoxyphenol (7.2 mL, 57.2 mmol). After 20 h at room temperature, the solvent was removed under reduced pressure, and the residue was diluted with ethyl acetate and washed with brine and water, dried over $Na_2SO_4$, filtered and concentrated. The residue was purified by chromatography on silica gel (DCM/EtOAc 9:1) to give 19 (4.2 g, 60%) as a yellow oil. $^1$H NMR ($CDCl_3$) δ 7.32-6.83 (m, 13H), 5.22 (m, 1H), 5.12 (s, 2H), 4.12-3.73 (m, 6H), 2.52-2.42 (m, 2H), 1.41-1.37 (m, 6H); $^{31}$P NMR ($CDCl_3$) δ 25.4; MS (ESI) 522 (M+Na).

Example 7B

Compound 20: A solution of compound 19(3 g, 6 mmol) was dissolved in 70 mL of acetonitrile at 0° C., then 2N NaOH (12 mL, 24 mmol) was added dropwisely. The reaction mixture was stirred at room temperature for 1.5 h. Then the solvent was removed under reduced pressure, and the residue diluted with water and extracted with ethyl acetate. The aqueous layer was acidified with conc. HCl to PH=1, then extracted with ethyl acetate, combined the organic layer and dried over $Na_2SO_4$, filtered and concentrated to give compound 20 (2 g, 88%) as a off-white solid. $^1$H NMR ($CDCl_3$) δ 7.33-6.79 (m, 9H), 5.10 (s, 2H), 4.12-3.51 (m, 6H), 2.15-2.05 (m, 2H), 1.47-1.33 (m, 3H); $^{31}$P NMR($CDCl_3$) δ 30.5; MS (ESI) 380 (M+1).

Example 7C

Compound 21: To a stirred solution of compound 20 (1 g, 2.6 mmol) in 20 mL of acetonitrile at room temperature under $N_2$ was added thionyl chloride (1.1 mL, 15.6 mmol). The resulted mixture was stirred at 60-70° C. for 45 min. After cooled to room temperature, the solvent was removed under reduced pressure, and the residue was added 25 mL of DCM, followed by TEA (1.5 mL, 10.4 mmol) and (S) lactate ethyl ester (0.9 mL, 7.8 mmol). After 20 h at room temperature, the solvent was removed under reduced pressure, and the residue was diluted with DCM and washed with brine and water, dried over $Na_2SO_4$, filtered and concentrated. The residue was purified by chromatography on silica gel (DCM/EtOAc 3:1) to give 21 (370 mg, 30%) as a yellow oil. $^1$H NMR ($CDCl_3$) δ 7.33-6.84 (m, 9H), 6.17-6.01 (m, 1H), 5.70 (m, 1H), 5.18-5.01 (m, 3H), 4.25-4.04 (m, 4H), 3.78-3.57 (m, 2H), 2.38-2.27 (m, 2H), 1.5-1.23 (m, 9H); $^{31}$P NMR ($CDCl_3$) δ 29.2 and 27.3; MS (ESI) 502 (M+Na).

Example 7D

Compound 22: A solution of compound 21 (370 mg) was dissolved in 8 mL of EtOH, then 0.12 mL of acetic acid and 10% Pd/C (72 mg) was added. The resulted mixture was stirred under $H_2$ atmosphere (balloon) for 4 h. After filtration through celite, the filtered was evaporated under reduced pressure to afford the compound 22 (320 mg, 96%) as a colorless oil. $^1$H NMR ($CDCl_3$) 7.27-6.86 (m, 4H), 5.98 (s, 2H), 5.18-5.02 (m, 1H), 4.25-4.06 (m, 4H), 3.34-3.24 (m, 2H), 2.44-2.30 (m, 2H), 1.62-1.24 (m, 9H); $^{31}$P NMR ($CDCl_3$) δ 28.3 and 26.8; MS (ESI) 346 (M+1).

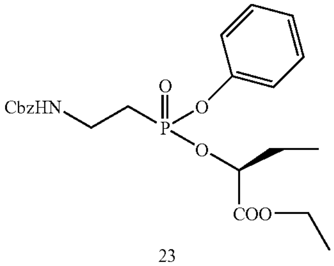

23

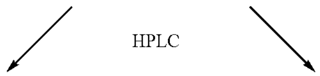

-continued

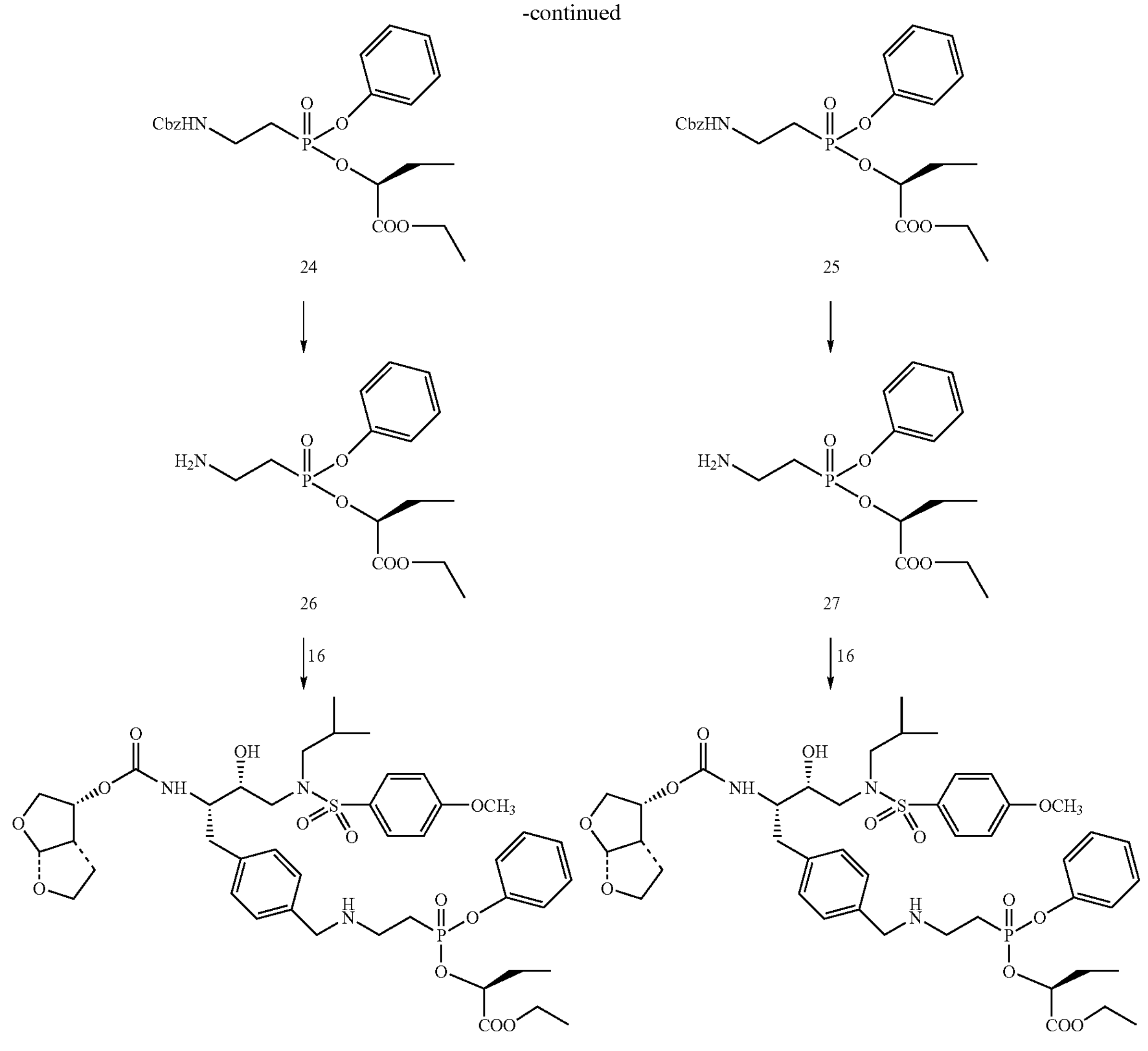

24 25

26 27

28 29

Example 8A

Compound 24: Compound 23 was purified using a Dynamax SD-200 HPLC system. The mobile phase consisted of acetonitrile: water (65:35, v/v) at a flow rate of 70 mL/min. The injection volume was 4 mL. The detection was by fluorescence at 245 nm and peak area ratios were used for quantitations. Retention time was 8.2 min for compound 24 as yellow oil. $^{1}$H NMR ($CDCl_3$) δ 7.36-7.19 (m, 10H), 5.88 (m, 1H), 5.12 (s, 2H), 4.90-4.86 (m, 1H), 4.26-4.12 (m, 2H), 3.72-3.61 (m, 2H), 2.36-2.29 (m, 2H), 1.79-1.74 (m, 2H); 1.27 (t, J=7.2 Hz, 3H), 0.82 (t, J=7.2 Hz, 3H); $^{3}$P NMR ($CDCl_3$) δ 28.3; MS (ESI) 472 (M+Na).

Example 8B

Compound 25 was purified in the same manner and retention time was 7.9 min for compound 25 as yellow oil. $^{1}$H NMR ($CDCl_3$) δ 7.34-7.14 (m, 10H), 5.75 (m, 1H), 5.10 (s, 2H), 4.964.91 (m, 1H), 4.18-4.12 (m, 2H), 3.66-3.55 (m, 2H), 2.29-2.19 (m, 2H), 1.97-1.89 (m, 2H); 1.21 (t, J=7.2 Hz, 3H), 0.97 (t, J=7.2 Hz, 3H); $^{31}$P NMR ($CDCl_3$) δ 26.2; MS (ESI) 472 (M+Na).

Example 8C

Compound 26: A solution of compound 24 (1 g) was dissolved in 20 mL of EtOH, then 0.3 mL of acetic acid and 10% Pd/C (200 mg) was added. The resulted mixture was stirred under H2 atmosphere (balloon) for 4 h. After filtration through celite, the filtered was evaporated under reduced pressure to afford the compound 26 (830 mg, 99%) as a colorless oil. $^{1}$H NMR ($CDCl_3$) δ 7.46-7.19 (m, 5H), 4.92-4.81 (m, 1H), 4.24-4.21 (m, 2H), 3.41-3.28 (m, 2H), 2.54-2.38 (m, 2H), 1.79-1.74 (m, 2H), 1.27 (t, J=7.2 Hz, 3H), 0.80 (t, J=7.2 Hz, 3H); $^{31}$P NMR ($CDCl_3$) δ 26.9; MS (ESI) 316 (M+1).

Example 8D

Compound 27: A solution of compound 25 (700 g) was dissolved in 14 mL of EtOH, then 0.21 mL of acetic acid and 10% Pd/C (140 mg) was added. The resulted mixture was stirred under H2 atmosphere (balloon) for 4 h. After filtration through celite, the filtered was evaporated under reduced pressure to afford the compound 27 (510 mg, 98%) as a colorless oil. $^{1}$H NMR ($CDCl_3$) δ 7.39-7.18 (m, 5H), 4.98-4.85 (m, 1H), 4.25-4.22 (m, 2H), 3.43-3.28 (m, 2H), 2.59-2.41 (m, 2H), 1.99-1.85 (m, 2H), 1.28 (t, J=7.2 Hz, 3H), 1.02 (t, J=7.2 Hz, 3H); $^{31}$P NMR ($CDCl_3$) δ 24.2; MS (ESI) 316 (M+1).

Example 8E

Compound 28: To a stirred solution of compound 16 (1.18 g, 2 mmol) in 9 mL of 1,2-dichloroethane was added compound 26 (830 mg, 2.2 mmol) and $MgSO_4$ (80 mg), the resulted mixture was stirred at room temperature under argon for 3 h, then acetic acid (0.34 mL, 6 mmol) and sodium cyanoborohydride (251 mg, 4 mmol) were added. The reaction mixture was stirred at room temperature for 2 h under argon. Then aqueous $NaHCO_3$ (50 mL) was added, and the mixture was extracted with ethyl acetate, and the combined organic layers were washed with brine and water, dried over $Na_2SO_4$, filtered and concentrated. The residue was purified by chromatography on silica gel (EtOH/EtOAc, 1/9) to give 28 (880 mg, 50%) as a white solid. $^{1}$H NMR ($CDCl_3$) δ 7.71 (d, J=8.7 Hz, 2H), 7.35-7.16 (m, 9H), 6.99 (d, J=8.7 Hz, 2H), 5.64 (d, J=5.4 Hz, 1H), 5.03-4.85 (m, 3H), 4.24-3.67 (m overlapping s, 15H), 3.14-2.70 (m, 9H), 2.39-2.28 (m, 2H), 1.85-1.51 (m, 5H), 1.29-1.25 (m, 3H), 0.93-0.78 (m, 9H); $^{31}$P NMR ($CDCl_3$) δ 29.2; MS (ESI) 912 (M+Na).

Example 8F

Compound 29: To a stirred solution of compound 16 (857 g, 1.45 mmol) in 7 mL of 1,2-dichloroethane was added compound 27 (600 mg, 1.6 mmol) and $MgSO_4$ (60 mg), the resulted mixture was stirred at room temperature under argon for 3 h, then acetic acid (0.23 mL, 3 mmol) and sodium cyanoborohydride (183 mg, 2.9 mmol) were added. The reaction mixture was stirred at room temperature for 2 h under argon. Then aqueous $NaHCO_3$ (50 mL) was added, and the mixture was extracted with ethyl acetate, and the combined organic layers were washed with brine and water, dried over $Na_2SO_4$, filtered and concentrated. The residue was purified by chromatography on silica gel (EtOH/EtOAc, 1/9) to give 29 (650 mg, 50%) as a white solid. $^{1}$H NMR ($CDCl_3$) δ 7.72 (d, J=8.7 Hz, 2H), 7.35-7.16 (m, 9H), 7.00 (d, J=8.7 Hz, 2H), 5.64 (d, J=5.4 Hz, 1H), 5.03-4.90 (m, 3H), 4.17-3.67 (m overlapping s, 15H), 3.16-2.77 (m, 9H), 2.26-2.19 (m, 2H), 1.94-1.53 (m, 5H), 1.26-1.18 (m, 3H), 1.00-0.87 (m, 9H); $^{31}$P NMR ($CDCl_3$) 627.4; MS (ESI) 912 (M+Na).

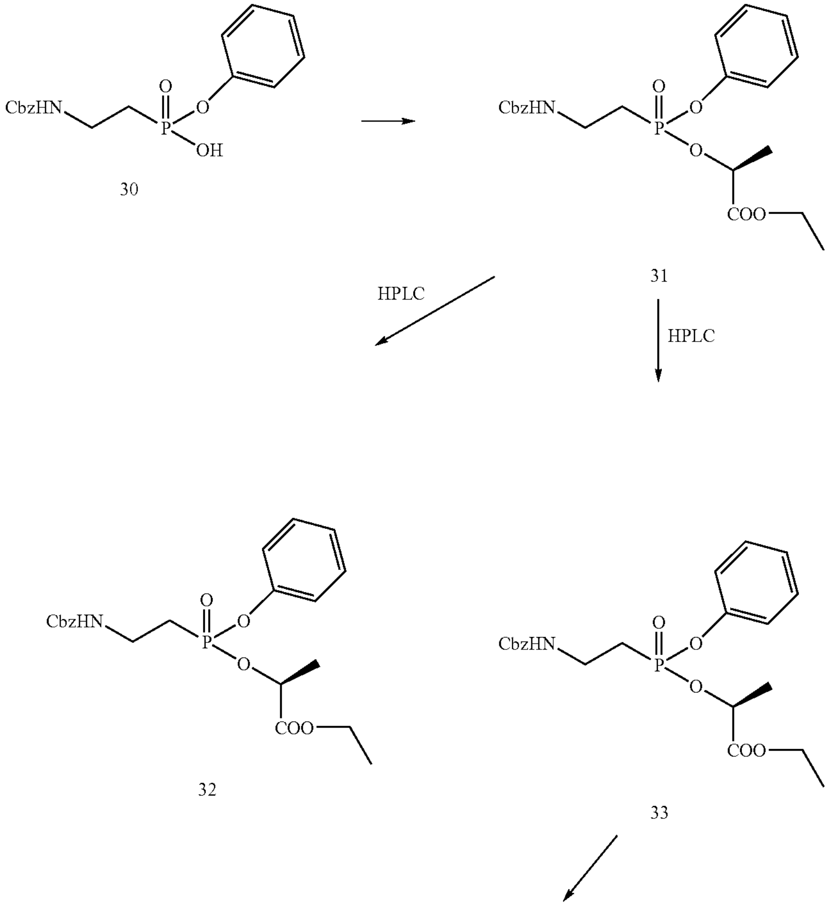

30
31
32
33

-continued

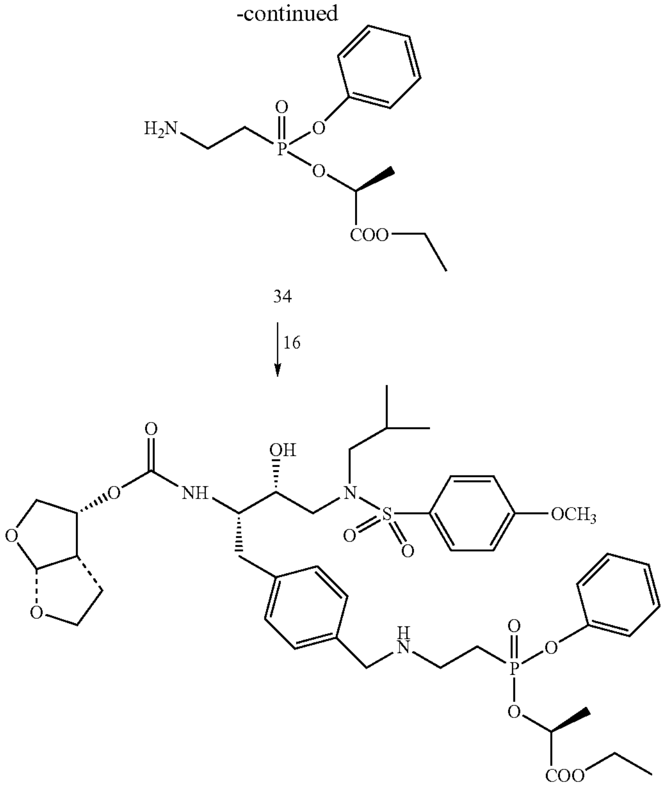

34

35

Example 9A

Compound 31: To a stirred solution of compound 30 (20 g, 60 mmol) in 320 mL of toluene at room temperature under $N_2$ was added thionyl chloride (17.5 mL, 240 mmol) and a few drops of DMF. The resulted mixture was stirred at 60-70° C. for 3 h. After cooled to room temperature, the solvent was removed under reduced pressure, and the residue was added 280 mL of DCM, followed by TEA (50 mL, 360 mmol) and (S) lactate ethyl ester (17 mL, 150 mmol). After 20 h at room temperature, the solvent was removed under reduced pressure, and the residue was diluted with DCM and washed with brine and water, dried over $Na_2SO_4$, filtered and concentrated. The residue was purified by chromatography on silica gel (DCM/EtOAc, 1:1) to give 31 (24 g, 92%) as a yellow oil. $^1$H NMR ($CDCl_3$) δ 7.33-7.18 (m, 10H), 5.94-6.63 (m, 1H), 5.70 (m, 1H), 5.12-4.95 (m, 3H), 4.24-4.14 (m, 2H), 3.72-3.59 (m, 2H), 2.35-2.20 (m, 2H), 1.58-1.19 (m, 6H); $^{31}$P NMR ($CDCl_3$) δ 28.2 and 26.2; MS (ESI) 458 (M+Na).

Example 9B

Compound 32: Compound 31 was purified using a Dynamax SD-200 HPLC system. The mobile phase consisted of acetonitrile: water (60:40, v/v) at a flow rate of 70 mL/min. The injection volume was 3 mL. The detection was by fluorescence at 245 nm and peak area ratios were used for quantitations. Retention time was 8.1 min for compound 32 as yellow oil. $^1$H NMR ($CDCl_3$) δ 7.33-7.18 (m, 10H), 5.94-6.63 (m, 1H), 5.70 (m, 1H), 5.12-4.95 (m, 3H), 4.24-4.14 (m, 2H), 3.72-3.59 (m, 2H), 2.35-2.20 (m, 2H), 1.58-1.19 (m, 6H); $^{31}$P NMR ($CDCl_3$) 628.2; MS (ESI) 458 (M+Na).

Example 9C

Compound 33 was purified in the same manner and retention time was 7.9 min for compound 33 as yellow oil. $^1$H NMR ($CDCl_3$) δ 7.33-7.18 (m, 10H), 5.94-6.63 (m, 1H), 5.70 (m, 1H), 5.12-4.95 (m, 3H), 4.24-4.14 (m, 2H), 3.72-3.59 (m, 2H), 2.35-2.20 (m, 2H), 1.58-1.19 (m, 6H); $^{31}$P NMR ($CDCl_3$) δ 26.2; MS (ESI) 458 (M+Na).

Example 9D

Compound 34: A solution of compound 33 (3.2 g) was dissolved in 60 mL of EtOH, then 0.9 mL of acetic acid and 10% Pd/C (640 mg) was added. The resulted mixture was stirred under $H_2$ atmosphere (balloon) for 4 h. After filtration through celite, the filtered was evaporated under reduced pressure to afford the compound 34 (2.7 g, 99%) as a colorless oil. $^1$H NMR ($CDCl_3$) δ 7.42-7.18 (m, 5H), 6.10 (s, 1H), 5.15-5.02 (m, 1H), 4.24-4.05 (m, 2H), 3.25-3.16 (m, 2H), 2.36-2.21 (m, 2H), 1.61-1.58 (m, 3H), 1.35-1.18, m, 3H); $^{31}$P NMR ($CDCl_3$) δ 26.1; MS (ESI) 302 (M+1).

Example 9E

Compound 35: To a stirred solution of compound 16 (8.9 g, 15 mmol) in 70 mL of 1,2-dichloroethane was added compound 34 (8.3 g, 23 mmol) and $MgSO_4$ (80 mg), the resulted mixture was stirred at room temperature under argon for 2.5 h, then acetic acid (3 mL, 52.5 mmol) and sodium cyanoborohydride (1.9 g, 30 mmol) were added. The reaction mixture was stirred at room temperature for 1.5 h under argon. Then aqueous $NaHCO_3$ (100 mL) was added, and the mixture was extracted with ethyl acetate, and the combined organic layers were washed with brine and water, dried over $Na_2SO_4$, filtered and concentrated. The residue was purified by chromatography on silica gel (EtOH/EtOAc, 1/9) to give 35 (8.4 g, 64%) as a white solid. $^1H$ NMR ($CDCl_3$) δ 7.73 (d, J=8.7 Hz, 2H), 7.36-7.17 (m, 9H), 7.00 (d, J=8.7 Hz, 2H), 5.64 (d, J=5.1 Hz, 1H), 5.07-4.97 (m, 3H), 4.19-3.67 (m overlapping s, 13H), 3.15-2.78 (m, 9H), 2.25-2.19 (m, 2H), 1.91-1.54 (m, 6H), 1.24-1.20 (m, 3H), 0.94-0.87 (m, 6H); $^{31}P$ NMR ($CDCl_3$) δ 27.4; MS (ESI) 876 (M+1).

Resolution of Compound 35 Diastereomers

Analysis was performed on an analytical Daicel Chiralcel OD column, conditions are described below, with a total of about 3.5 mg compound 35 free base injected onto the column. See also FIGS. 3 and 4 for separation of compound 35 diastereomer. This lot was about a 3:1 mixture of major to minor diastereomers where the lactate ester carbon is a 3:1 mix of R and S configurations.

Two injections of 3.8 and 3.5 mg each were made using the conditions described below. The isolated major diastereomer fractions were evaporated to dryness on a rotary evaporator under house vacuum. The chromatographic solvents were displaced by two portions of ethyl acetate followed by a single portion of ethyl acetate-trifluoroacetic acid (about 95:5) and a final high vacuum strip to aid in removal of trace solvents. This yielded the major diastereomer trifluoroacetate salt as a gummy solid.

The resolved minor diastereomer was isolated for biological evaluation by an 11 mg injection, performed on an analytical Daicel Chiralcel OD column, using the conditions described in below. The minor diastereomer of 35 was isolated as the trifluoroacetate salt by the conditions described above.

Larger scale injections (~300 mg 35 per injection) were later performed on a Daicel Chiralcel OD column semi-preparative column with a guard column, conditions are described below. See also FIG. 5 for separation of compound 35 diastereomers. A minimal quantity of isopropyl alcohol was added to heptane to dissolve the 3:1 diastereomeric mix of 35 and the resolved diastereomers sample, and the isolated fractions were refrigerated until the eluted mobile phase was stripped.

Figure 3:
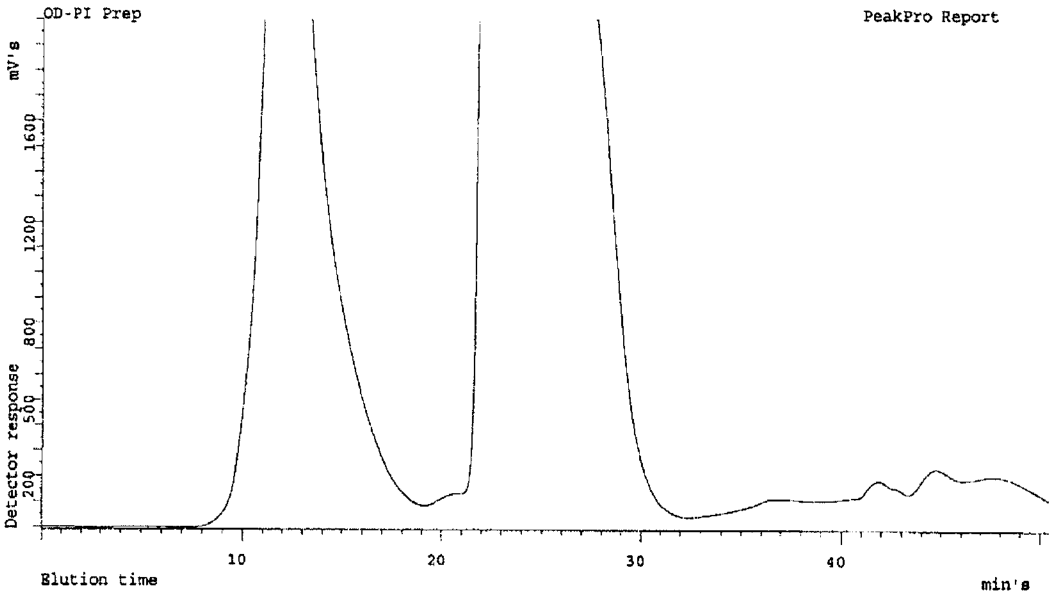
FIGS. 3 and 4 show resolution of compound 35 diastereomers by HPLC on an analytical Daicel Chiralcel OD column.

| HPLC CONDITIONS FOR FIG. 3 | |
|---|---|
| Column: | Chiralcel OD, 10 μm, 4.6 × 250 mm |
| Mobile Phase | Heptane - Ethyl Alcohol (20:80 initial) |
| | 100% Ethyl Alcohol (final) |
| | Note: Final began after first peak eluted |
| Flow Rate | 1.0 mL/min |
| Run Time | As needed |
| Detection | UV at 250 nm |
| Temperature | Ambient |
| Injection | ~4 mg on Column |
| Sample Prep. | Dissolved in ~1 mL |
| | heptane - ethyl alcohol (50:50) |
| Retention Times | 35 Minor ~14 min |
| | 35 Major ~25 min |

Figure 4:
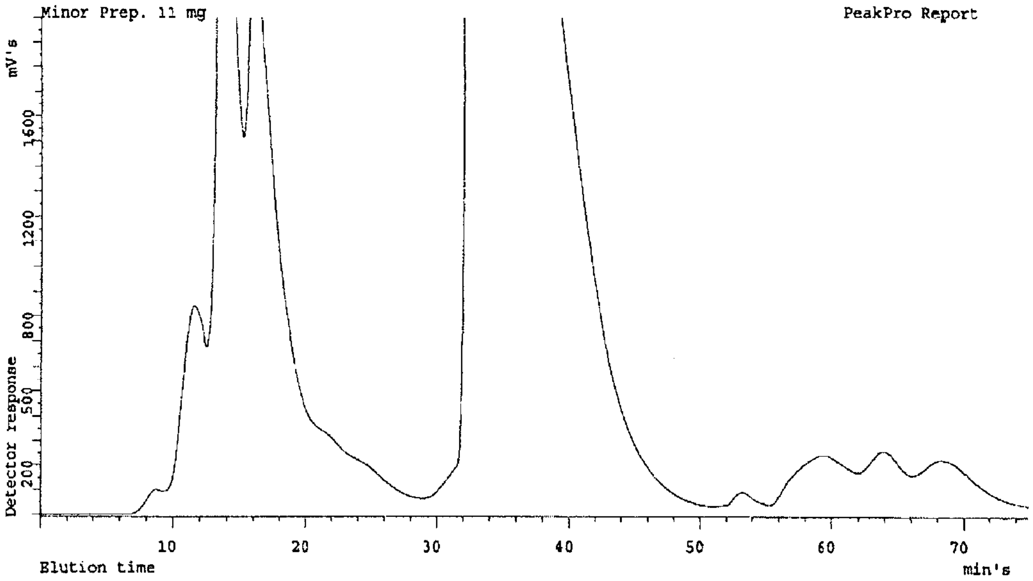

| HPLC CONDITIONS FOR FIG. 4 | |
|---|---|
| Column | Chiralcel OD, 10 μm, 4.6 × 250 mm |
| Mobile Phase | Heptane - Ethyl Alcohol (65:35 initial) |
| | Heptane - Ethyl Alcohol (57.5:42.5 intermediate) |
| | Note: Intermediate began after impurity peaks eluted |
| | Heptane - Ethyl Alcohol (20:80 final) |
| | Note: Final mobile phase began after minor diastereomer eluted |
| Flow Rate | 1.0 mL/min |
| Run Time | As needed |
| Detection | UV at 250 nm |
| Temperature | Ambient |
| Injection | ~4 mg on Column |
| Sample Prep. | Dissolved in ~1 mL |
| | heptane - ethyl alcohol (50:50) |
| Retention Times | 35 Minor ~14 min |
| | 35 Major ~40 min |

Figure 5:
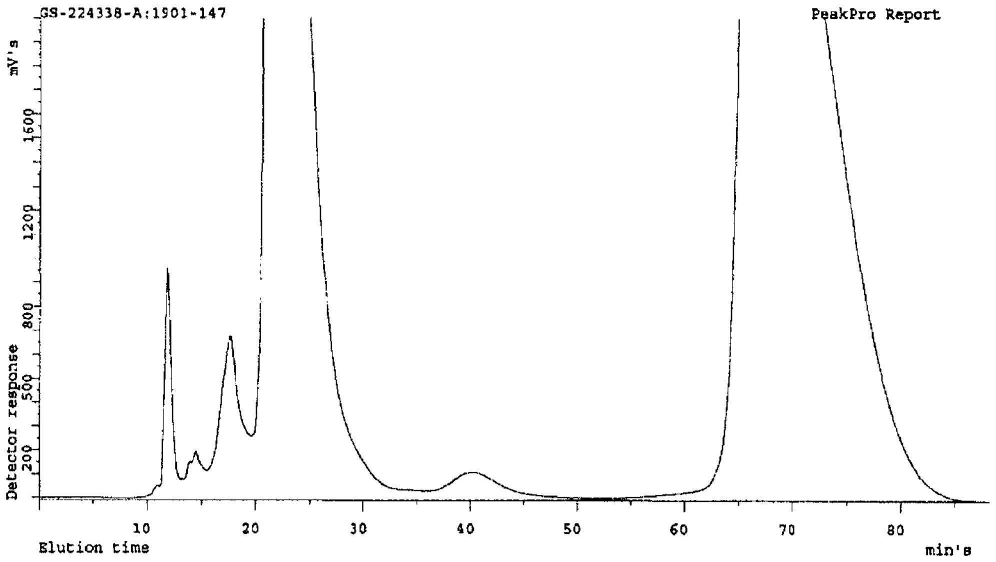
FIG. 5 shows resolution of compound 35 diastereomers by HPLC on a Daicel Chiralcel OD column semi-preparative column.

| HPLC CONDITIONS FOR FIG. 5 | |
|---|---|
| Columns | Chiralcel OD, 20 μm, 21 × 50 mm (guard) |
| | Chiralcel OD, 20 μm, 21 × 250 mm |
| Mobile Phase | Heptane - Ethyl Alcohol (65:35 initial) |
| | Heptane - Ethyl Alcohol (50:50 intermediate) |
| | Note: Intermediate began after minor diastereomer peak eluted |
| | Heptane - Ethyl Alcohol (20:80 final) |
| | Note: Final mobile phase began after major diastereomer began to elute |
| Flow Rate | 10.0 mL/min |
| Run Time | As needed |
| Detection | UV at 260 nm |
| Temperature | Ambient |
| Injection | ~300 mg on Column |
| Sample Prep. | Dissolved in ~3.5 mL |
| | hetpane - ethyl alcohol (70:30) |
| Retention Times | 35 Minor ~14 min |
| | 35 Major ~40 min |

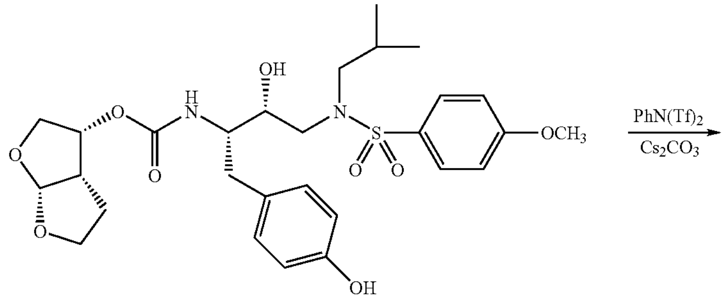
8
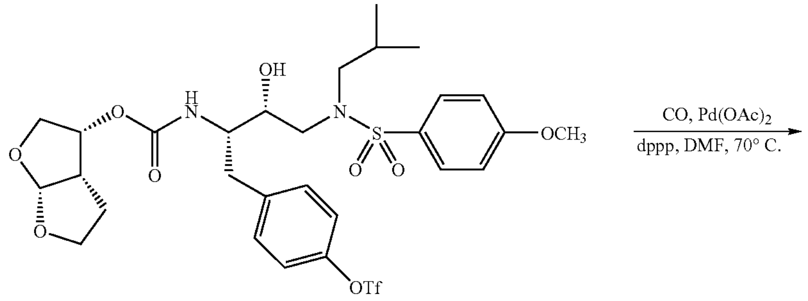
1
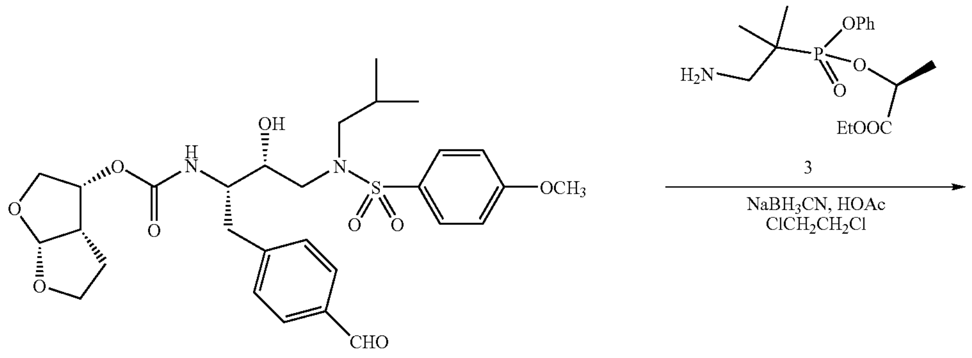
2
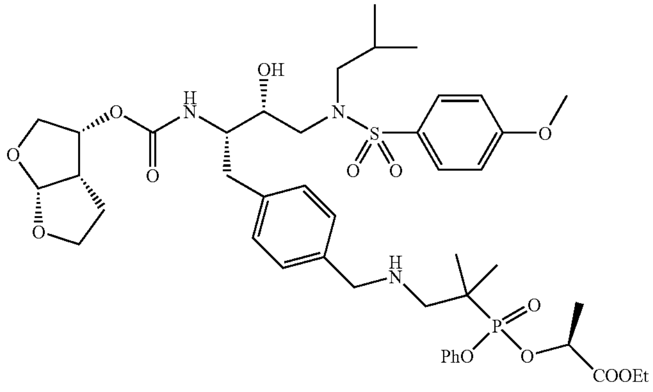
4

-continued

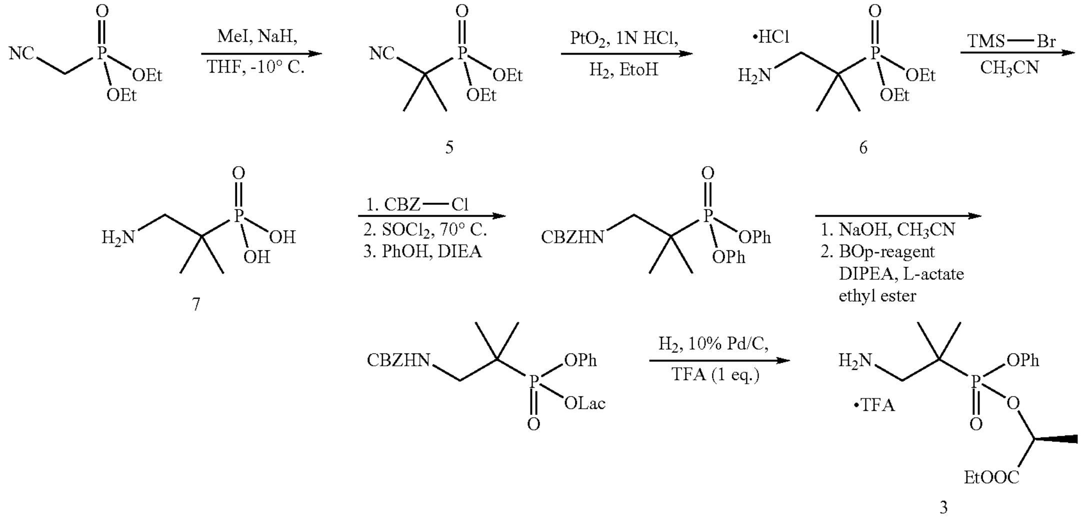

Example 29

Triflate derivative 1: A THF-$CH_2Cl_2$ solution (30 mL-10 mL) of 8 (4 g, 6.9 mmol), cesium carbonate (2.7 g, 8 mmol), and N-phenyltrifluoromethane sulfonimide (2.8 g, 8 mmol) was reacted overnight. The reaction mixture was worked up, and concentrated to dryness to give crude triflate derivative 1.

Aldehyde 2: Crude triflate 1 (4.5 g, 6.9 mmol) was dissolved in DMF (20 mL), and the solution was degassed (high vacuum for 2 min, Ar purge, repeat 3 times). $Pd(OAc)_2$ (0.12 g, 0.27 mmol), and bis(diphenylphosphino)propane (dppp, 0.22 g, 0.27 mmol) were added, the solution was heated to 70° C. Carbon monoxide was rapidly bubbled through the solution, then under 1 atmosphere of carbon monoxide. To this solution were slowly added TEA (5.4 mL, 38 mmol), and triethylsilane (3 ml), 18 mmol). The resulting solution was stirred overnight at room temperature. The reaction mixture was worked up, and purified on silica gel column chromatograph to afford aldehyde 2 (2.1 g, 51%). (Hostetler, et al J. Org. Chem., 1999. 64, 178-185).

Lactate prodrug 4: Compound 4 is prepared as described above procedure for Example 9E, Compound 35 by the reductive amination between 2 and 3 with $NaBH_3CN$ in 1,2-dichloroethane in the presence of HOAc.

Example 30

Preparation of Compound 3

Diethyl(cyano(dimethyl)methyl)phosphonate 5: A THF solution (30 mL) of NaH (3.4 g of 60% oil dispersion, 85 mmol) was cooled to −10° C., followed by the addition of diethyl (cyanomethyl)phosphonate (5 g, 28.2 mmol) and iodomethane (17 g, 112 mmol). The resulting solution was stirred at −10° C. for 2 hr, then 0° C. for 1 hr, was worked up, and purified to give dimethyl derivative 5 (5 g, 86%).

Dietyl(2-amino-1,1-dimethyl-ethyl)phosphonate 6: Compound 5 was reduced to amine derivative 6 by the described procedure (J. Med. Chem. 1999, 42, 5010-5019).

A solution of ethanol (150 mL) and 1N HCl aqueous solution (22 mL) of 5 (2.2 g, 10.7 mmol) was hydrogenated at 1 atmosphere in the presence of $PtO_2$ (1.25 g) at room temperature overnight. The catalyst was filtered through a celite pad. The filtrate was concentrated to dryness, to give crude 6 (2.5 g, as HCl salt).

2-Amino-1,1-dimethyl-ethyl phosphonic acid 7: A solution of $CH_3CN$ (30 mL) of crude 6 (2.5 g) was cooled to 0° C., and treated with TMSBr (8 g, 52 mmol) for 5 hr. The reaction mixture was stirred with methanol for 1.5 hr at room temperature, concentrated, recharged with methanol, concentrated to dryness to give crude 7 which was used for next reaction without further purification.

Lactate phenyl(2-amino-1,1-dimethyl-ethyl)phosphonate 3: Compound 3 is synthesized according to the procedures described in Example 9D, Compound 34 for the preparation of lactate phenyl 2-aminoethyl phosphonate 34. Compound 7 is protected with CBZ, followed by the reaction with thionyl chloride at 70° C. The CBZ protected dichlorodate is reacted phenol in the presence of DIPEA. Removal of one phenol, follow by coupling with ethyl L-lactate leads N-CBZ-2-amino-1,1-dimethyl-ethyl phosphonate derivative. Hydrogenation of N-CBZ derivative at 1 atmosphere in the presence of 10% Pd/C and 1 eq. of TFA affords compound 3 as TFA salt.

Scheme 1

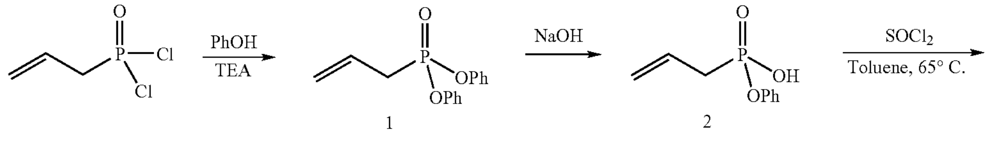

-continued

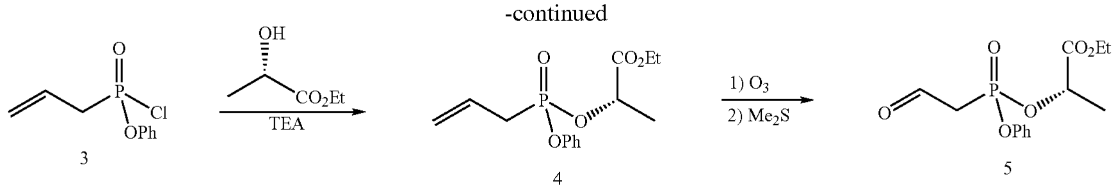

3 4 5

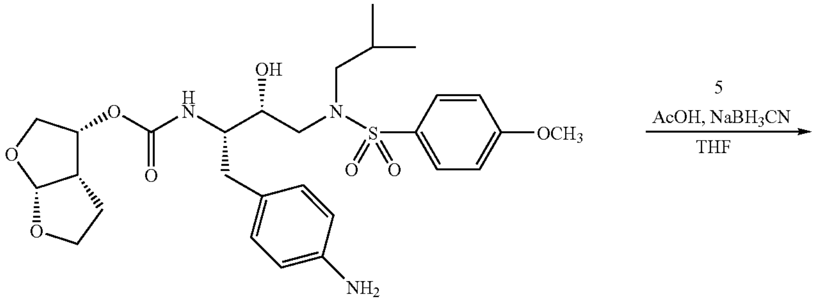

6

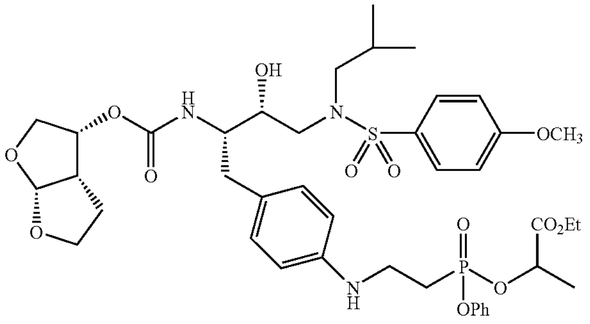

7

Example 1

Monophenol Allylphosphonate 2: To a solution of allylphosphonic dichloride (4 g, 25.4 mmol) and phenol (5.2 g, 55.3 mmol) in $CH_2Cl_2$ (40 mL) at 0° C. was added TEA (8.4 mL, 60 mmol). After stirred at room temperature for 1.5 h, the mixture was diluted with hexane-ethyl acetate and washed with HCl (0.3 N) and water. The organic phase was dried over $MgSO_4$, filtered and concentrated under reduced pressure. The residue was filtered through a pad of silica gel (eluted with 2:1 hexane-ethyl acetate) to afford crude product diphenol allylphosphonate 1 (7.8 g, containing the excessive phenol) as an oil which was used directly without any further purification. The crude material was dissolved in $CH_3CN$ (60 mL), and NaOH (4.4N, 15 mL) was added at 0° C. The resulted mixture was stirred at room temperature for 3 h, then neutralized with acetic acid to pH=8 and concentrated under reduced pressure to remove most of the acetonitrile. The residue was dissolved in water (50 mL) and washed with $CH_2Cl_2$ (3x25 mL). The aqueous phase was acidified with concentrated HCl at 0° C. and extracted with ethyl acetate. The organic phase was dried over $MgSO_4$, filtered, evaporated and co-evaporated with toluene under reduced pressure to yield desired monophenol allylphosphonate 2 (4.75 g. 95%) as an oil.

Example 2

Monolactate Allylphosphonate 4: To a solution of monophenol allylphosphonate 2 (4.75 g, 24 mmol) in toluene (30 mL) was added $SOCl_2$ (5 mL, 68 mmol) and DMF (0.05 mL). After stirred at 65° C. for 4 h, the reaction was completed as shown by $^{31}P$ NMR. The reaction mixture was evaporated and co-evaporated with toluene under reduced pressure to give mono chloride 3 (5.5 g) as an oil. To a solution of chloride 3 in $CH_2Cl_2$ (25 mL) at 0° C. was added ethyl(s)-lactate (3.3 mL, 28.8 mmol), followed by TEA. The mixture was stirred at 0° C. for 5 min then at room temperature for 1 h, and concentrated under reduced pressure. The residue was partitioned between ethyl acetate and HCl (0.2N), the organic phase was washed with water, dried over $MgSO_4$, filtered and concentrated under reduced pressure. The residue was purified by chromatography on silica gel to afford desired monolactate 4 (5.75 g, 80%) as an oil (2:1 mixture of two isomers): $^1H$ NMR ($CDCl_3$) δ 7.1-7.4 (m, 5H), 5.9 (m, 1H), 5.3 (m, 2H), 5.0 (m, 1H), 4.2 (m, 2H), 2.9 (m, 2H), 1.6; 1.4 (d, 3H), 1.25 (m, 3H); $^{31}P$ NMR ($CDCl_3$) δ 25.4, 23.9.

Example 3

Aldehyde 5: A solution of allylphosphonate 4 (2.5 g, 8.38 mmol) in $CH_2Cl_2$ (30 mL) was bubbled with ozone air at −78°

C. until the solution became blue, then bubbled with nitrogen until the blue color disappeared. Methyl sulfide (3 mL) was added at −78° C. The mixture was warmed up to room temperature, stirred for 16 h and concentrated under reduced pressure to give desired aldehyde 5 (3.2 g, as a 1:1 mixture of DMSO): $^1$H NMR ($CDCl_3$) δ 9.8 (m, 1H), 7.1-7.4 (m, 5H), 5.0 (m, 1H), 4.2 (m, 2H), 3.4 (m, 2H), 1.6; 1.4 (d, 3H), 1.25 (m, 3H); $^{31}$P NMR ($CDCl_3$) δ 17.7, 15.4.

Example 4

Compound 7: To a solution of aniline 6 (reported before) (1.62 g, 2.81 mmol) in THF (40 mL) was added acetic acid (0.8 mL, 14 mmol), followed by aldehyde 5 (1.3 g, 80%, 3.46 mmol) and $MgSO_4$ (3 g). The mixture was stirred at room temperature for 0.5 h, then $NaBH_3CN$ (0.4 g, 6.37 mmol) was added. After stirred for 1 h, the reaction mixture was filtered. The filtrate was diluted with ethyl acetate and washed with $NaHCO_3$, dried over $MgSO_4$, filtered and concentrated under reduced pressure. The residue was purified by chromatography on silica gel to give compound 6 (1.1 g, 45%) as a 3:2 mixture of two isomers, which were separated by HPLC (mobile phase, 70% $CH_3CN/H_2O$; flow rate: 70 mL/min; detection: 254 nm; column: 8 μL C18, 41×250 mm, Varian). Isomer A (0.39 g): $^1$H NMR ($CDCl_3$) δ 7.75 (d, 2H), 7.1-7.4 (m, 5H), 7.0 (m, 4H), 6.6 (d, 2H), 5.65 (d, 1H), 5.05 (m, 2H), 4.9 (d, 1H), 4.3 (brs, 1H), 4.2 (q, 2H), 3.5-4.0 (m, 6H), 3.9 (s, 3H), 2.6-3.2 (m, 9H), 2.3 (m, 2), 1.6-1.9 (m, 5H), 1.25 (t, 3H), 0.9 (2d, 6H); $^{31}$P NMR ($CDCl_3$) δ 26.5; MS (ESI): 862 (M+H). Isomer B (0.59 g): $^1$H NMR ($CDCl_3$) δ 7.75 (d, 2H), 7.1-7.4 (m, 5H), 7.0 (m, 4H), 6.6 (d, 2H), 5.65 (d, 1H), 5.05 (m, 2H), 4.9 (d, 1H), 4.5 (brs, 1H), 4.2 (q, 2H), 3.5-4.0 (m, 6H), 3.9 (s, 3H), 2.7-3.2 (m, 9H), 2.4 (m, 2), 1.6-1.9 (m, 2H), 1.4 (d, 3H), 1.25 (t, 3H), 0.9 (2d, 6H); $^{31}$P NMR ($CDCl_3$) δ 28.4; MS (ESI): 862 (M+H).

Scheme 2

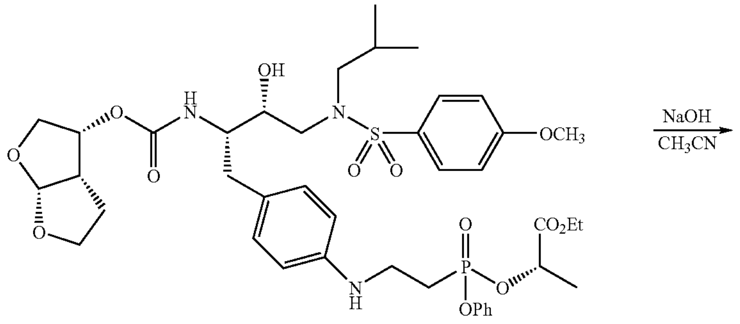

7

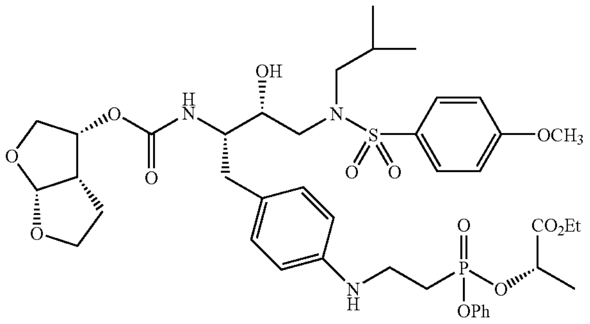

8

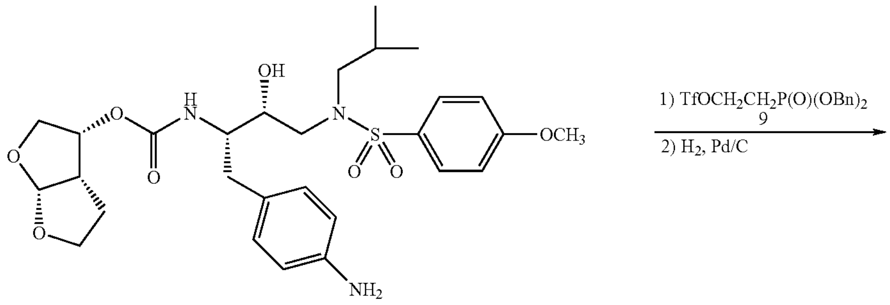

6

-continued

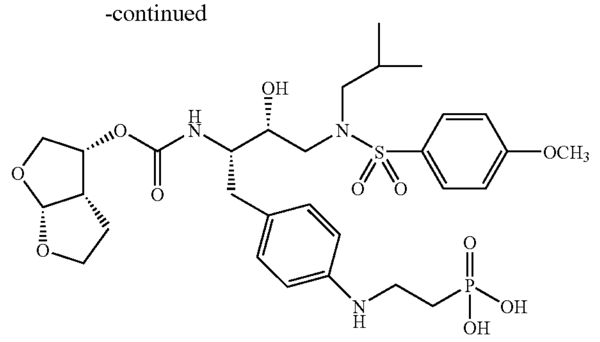

10

Example 5

Acid 8: To a solution of compound 7 (25 mg, 0.029 mmol) in acetonitrile (1 mL) at 0° C. was added NaOH (1N, 0.125 mL). The mixture was stirred at 0° C. for 0.5 h and at room temperature for 1 h. The reaction was quenched with acetic acid and purified by HPLC to give acid 8 (10 mg, 45%). $^1$H NMR ($CD_3OD$) δ 7.8 (d, 2H), 7.5 (d, 2H), 7.4 (d, 2H), 7.1 (d, 2H), 5.6 (d, 1H), 4.9 (m, 3H), 3.2-4.0 (m, 6H), 3.9 (s, 3H), 2.6-3.2 (m, 9H), 2.05 (m, 2), 1.4-1.7 (m, 2H), 1.5 (d, 3H), 0.9 (2d, 6H); $^{31}$P NMR ($CD_3OD$) δ 20.6; MS (ESI): 758 (M+H).

Example 6

Diacid 10: To a solution of triflate 9 (94 mg, 0.214 mmol) in $CH_2Cl_2$ (2 mL) was added a solution of aniline 6 (100 mg, 0.173 mmol) in $CH_2Cl_2$ (2 mL) at −40° C., followed by 2,6-lutidine (0.026 mL). The mixture was warmed up to room temperature and stirred for 1 h. Cesium carbonate (60 mg) was added and the reaction mixture was stirred for additional 1 h. The mixture was diluted with ethyl acetate, washed with HCl (0.2N), dried over $MgSO_4$, filtered and concentrated under reduced pressure. The residue was purified by HPLC to afford dibenzyl phosphonate (40 mg). To a solution of this dibenzyl phosphonate in ethanol (3 mL) and ethyl acetate (1 mL) was added 10% Pd/C (40 mg). The mixture was stirred under hydrogen atmosphere (balloon) for 4 h. The reaction mixture was diluted with methanol, filtered and concentrated under reduced pressure. The residue was washed with ethyl acetate and dried to give desired product diacid 10 (20 mg). $^1$H NMR ($CD_3OD$) δ 7.8 (d, 2H), 7.3 (d, 2H), 7.1 (2d, 4H), 5.6 (d, 1H), 4.9 (m, 2H), 3.4-4.0 (m, 6H), 3.9 (s, 3H), 2.53.2 (m, 9H), 2.0 (m, 2), 1.4-1.7 (m, 2H), 0.9 (2d, 6H); $^{31}$P NMR ($CD_3OD$) δ 22.1; MS (ESI): 686 (M+H).

Scheme 3

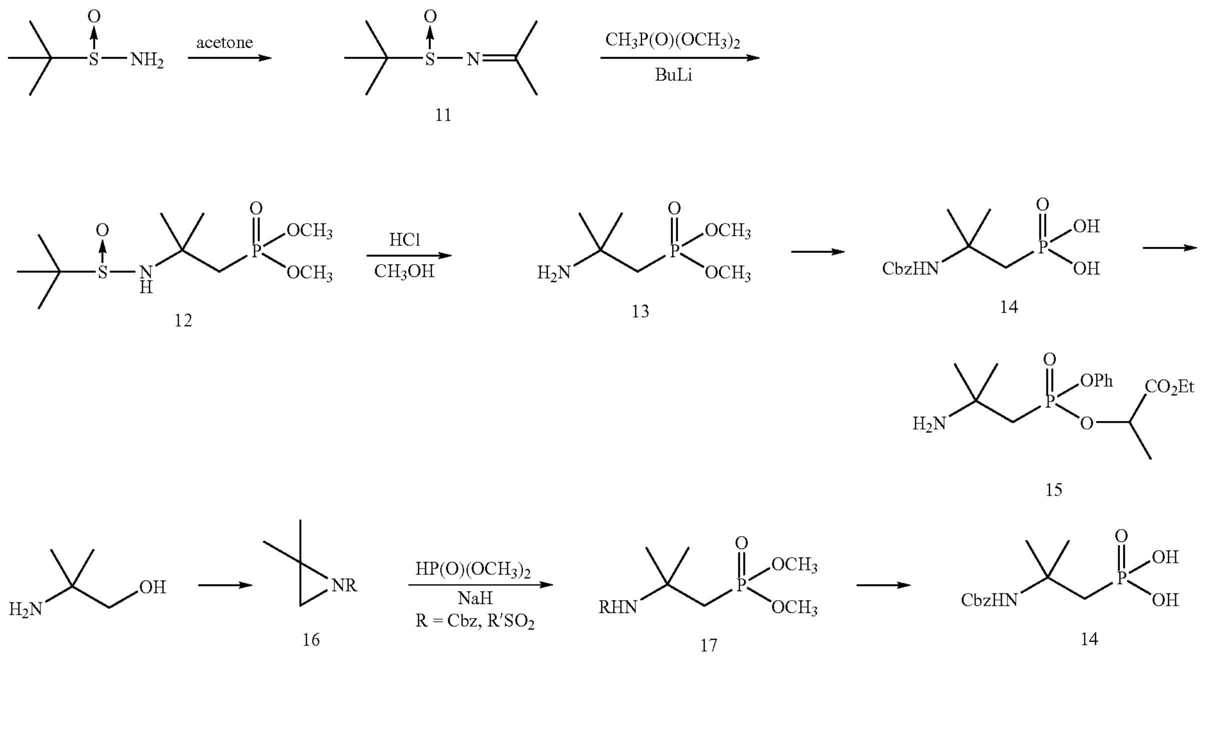

-continued

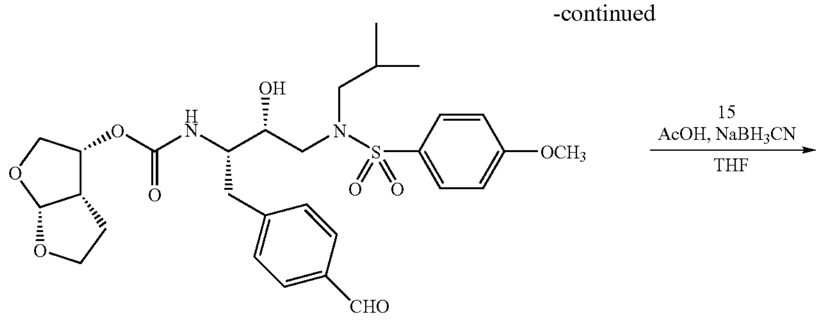

18

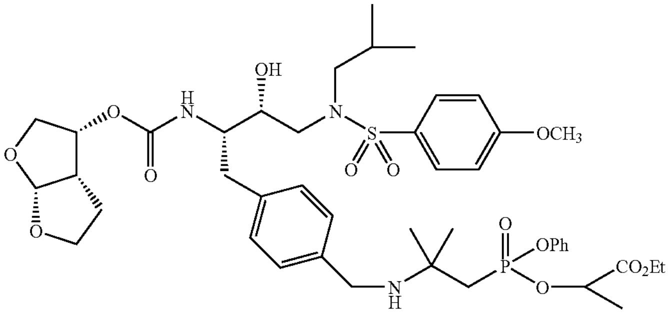

19

The synthesis of compound 19 is outlined in Scheme 3. Condensation of 2-methyl-25 propanesulfinamide with acetone give sulfinyl imine 11 (J. Org. Chem. 1999, 64, 12). Addition of dimethyl methylphosphonate lithium to 11 afford 12. Acidic methanolysis of 12 provide amine 13. Protection of amine with Cbz group and removal of methyl groups yield phosphonic acid 14, which can be converted to desired 15 using methods reported earlier on. An alternative synthesis of compound 14 is also shown in Scheme 3. Commercially available 2-amino-2-methyl-1-propanol is converted to aziridines 16 according to literature methods (J. Org. Chem. 1992, 57, 5813; and Syn. Lett. 1997, 8, 893). Aziridine opening with phosphite give 17 (Tetrahedron Lett. 1980, 21, 1623). Deprotection (and, if necessary, reprotection) of 17 afford 14. Reductive amination of amine 15 and aldehyde 18 provides compound 19.

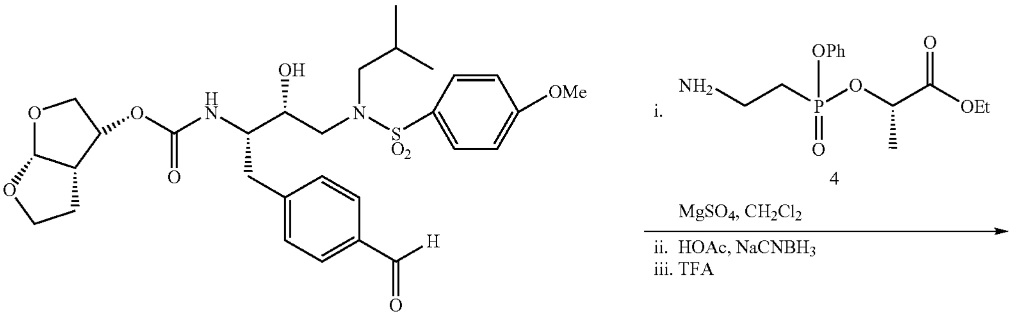

1

-continued

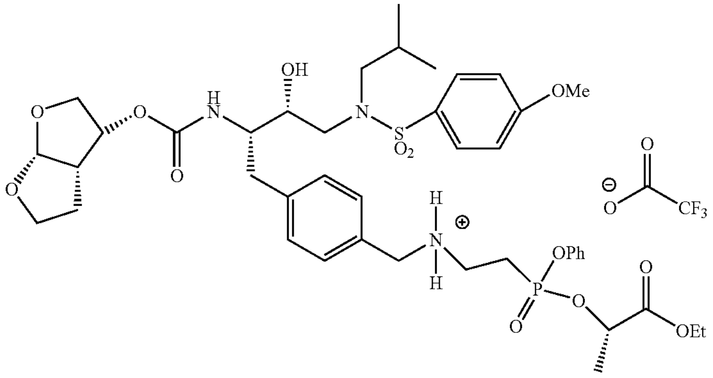

2

+

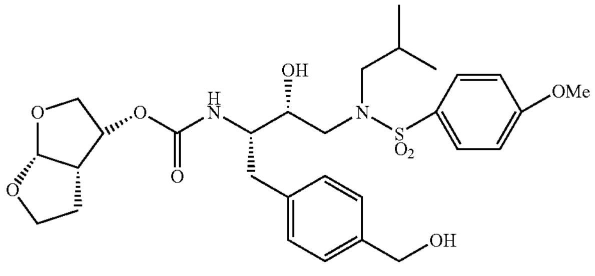

3

Example 1

2-{[2-(4-{2-(Hexahydro-furo[2,3-b]furan-3-yloxycarbonylamino)-3-hydroxy-4-[isobutyl-(4-methoxy-benzene-sulfonyl)-amino]-butyl}-benzylamino)-ethyl]-phenoxy-phosphinoyloxy}-propionic acid ethyl ester 2 (Compound 35, previous Example 9E).

A solution of 1 (2.07 g, 3.51 mmol) and 4 (1.33 g, 3.68 mmol of a 4:1 mixture of two diastereomers at the phosphorous center) were dissolved in 14 mL of $(CH_2Cl_2)_2$ to provide a clear solution. Addition of $MgSO_4$ (100 mg) to the solution resulted in a white cloudy mixture. The solution was stirred at ambient temperature for 3 hours when acetic acid (0.80 mL, 14.0 mmol) and sodium cyanoborohydride (441 mg, 7.01 mmol) were added. Following the reaction progress by TLC showed complete consumption of the aldehyde starting materials in 1 hour. The reaction mixture was worked up by addition of 200 mL of saturated aqueous $NaHCO_3$ and 400 mL of $CH_2Cl_2$. The aqueous layer was extracted with $CH_2Cl_2$ two more times (2×300 mL). The combined organic extracts were dried in vacuo and purified by column chromatography (EtOAc-10% MeOH: EtOAc) to provide the desired product as a foam. The early eluting compound from the column was collected and characterized as alcohol 3 (810 mg, 39%). Addition of TFA (3×1 mL) generated the TFA salt which was lyopholized from 50 mL of a 1:1 $CH_3CN$: $H_2O$ to provide 1.63 g (47%) of the product 2 as a white powder. $^1H$ NMR ($CD_3CN$) δ 8.23 (br s, 2H), 7.79 (d, J=8.4 Hz, 2H), 7.45-7.13 (m, 9H), 7.09 (d, J=8.4 Hz, 2H), 5.86 (d, J=9.0 Hz, 1H), 5.55 (d, J=4.8 Hz, 1H), 5.05-4.96 (m, 1H), 4.96-4.88 (m, 1H), 4.30-4.15 (m, 4H), 3.89 (s, 3H), 3.86-3.76 (m, 4H), 3.70-3.59 (m, 4H), 3.56-3.40 (m, 2H), 3.34 (d, J=15 Hz, 1H), 3.13 (d, J=13.5 Hz, 1H), 3.06-2.93 (m, 2H), 2.92-2.80 (m, 2H), 2.69-2.43 (m, 3H), 2.03-1.86 (m, 1H), 1.64-1.48 (m, 1H), 1.53 and 1.40 (d, J=6.3 Hz, J=6.6 Hz, 3H), 1.45-1.35 (m, 1H), 1.27 and 1.23 (t, J=6.9 Hz, J=7.2 Hz, 3H), 0.90 (t, J=6.9 Hz, 6H). $^{31}P$ NMR ($CD_3CN$) δ 24.47, 22.86. ESI $(M+H)^+$ 876.4.

Example 2

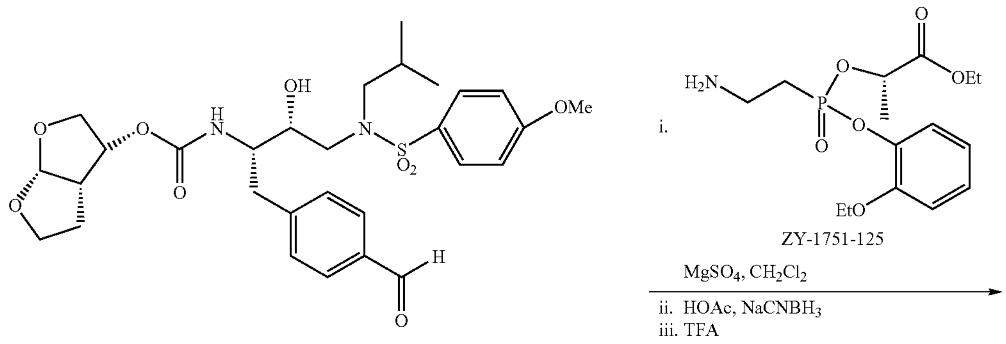

MF-1912-67

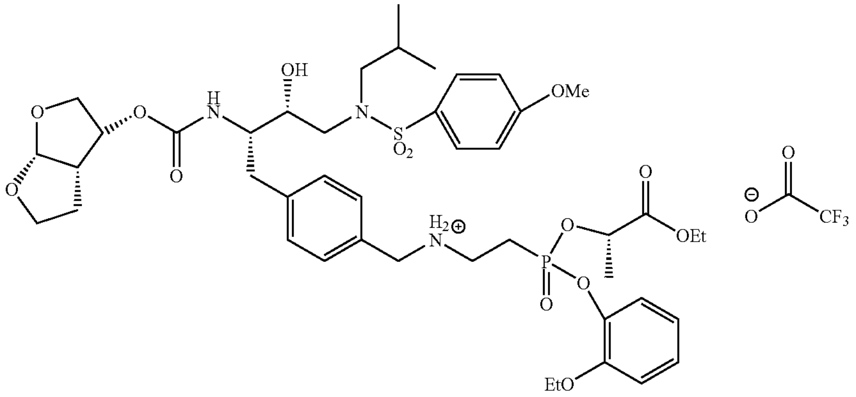

MF-1912-68

2-{[2-(4-{2-(Hexahydro-furo[2,3-b]furan-3-yloxy-carbonylamino)-3-hydroxy-4-[isobutyl-(4-methoxy-benzenesulfonyl)-amino]-butyl}-benzylamino)-ethyl]-phenoxy-phosphinoyloxy}-propionic acid ethyl ester (MF-1912-68)

A solution of MF-1912-67 (0.466 g, 0.789 mmol) and ZY-1751-125 (0.320 g, 0.789 mmol of a 1:1 mixture of two diastereomers at the phosphorous center) were dissolved in 3.1 mL of $(CH_2Cl_2)_2$ to provide a clear solution. Addition of $MgSO_4$ (20 mg) to the solution resulted in a white cloudy mixture. The solution was stirred at ambient temperature for 3 hours when acetic acid (0.181 mL, 3.16 mmol) and sodium cyanoborohydride (99 mg, 1.58 mmol) were added. Following the reaction progress by TLC showed complete consumption of the aldehyde starting materials in 1.5 hour. The reaction mixture was worked up by addition of 50 mL of saturated aqueous $NaHCO_3$ and 200 mL of $CH_2Cl_2$. The aqueous layer was extracted with $CH_2Cl_2$ two more times (2×200 mL). The combined organic extracts were dried in vacuo and purified by column chromatography (EtOAc-10% MeOH: EtOAc) to provide the desired product as a foam. The early eluting compound from the column was collected and characterized to be MF-1912-48b alcohol (190 mg, 41%). Addition of TFA (3×1 mL) generated the TFA salt which was lyopholized from 50 mL of a 1:1 $CH_3CN$: $H_2O$ to provide 0.389 g (48%) of the product as a white powder. $^1H$ NMR (CD3CN) δ 8.39 (br s, 2H), 7.79 (d, J=8.7 Hz, 2H), 7.40 (d, J=7.5 Hz, 2H), 7.34 (d, J=8.1 Hz, 2H), 7.26-7.16 (m, 2H), 7.10 (d, J=9 Hz, 3H), 7.01-6.92 (m, 1H), 5.78 (d, J=9.0 Hz, 1H), 5.55 (d, J=5.1 Hz, 1H), 5.25-5.03 (m, 1H), 4.95-4.88 (m, 1H), 4.30-4.17 (m, 4H), 4.16-4.07 (m, 2H), 3.90 (s, 3H), 3.88-3.73 (m, 4H), 3.72-3.60 (m, 2H), 3.57-3.38 (m, 2H), 3.32 (br d, J=15.3 Hz, 1H), 3.13 (br d, J=14.7 Hz, 1H), 3.05-2.92 (m, 2H), 2.92-2.78 (m, 2H), 2.68-2.48 (m, 3H), 2.03-1.90 (m, 1H), 1.62-1.51 (m, 1H), 1.57 and 1.46 (d, J=6.9 Hz, J=6.9 Hz, 3H), 1.36-1.50 (m, 1H), 1.43-1.35 (m, 4H), 1.33-1.22 (m, 3H), 0.91 (t, J=6.6 Hz, 6H). $^{31}P$ NMR ($CD_3CN$) δ 25.27, 23.56. ESI $(M+H)^+$ 920.5.

Scheme 1
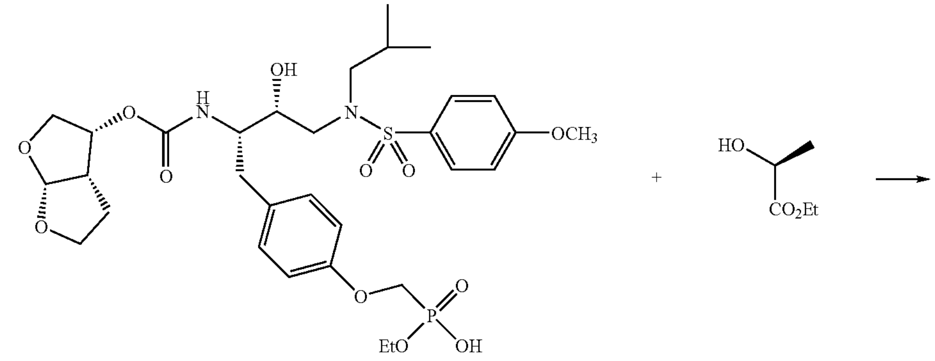
1 2
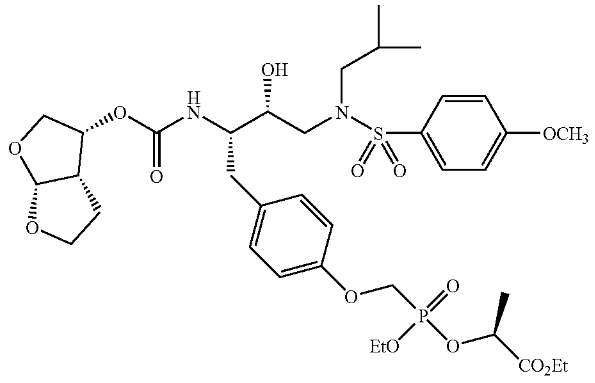
3
Scheme 2
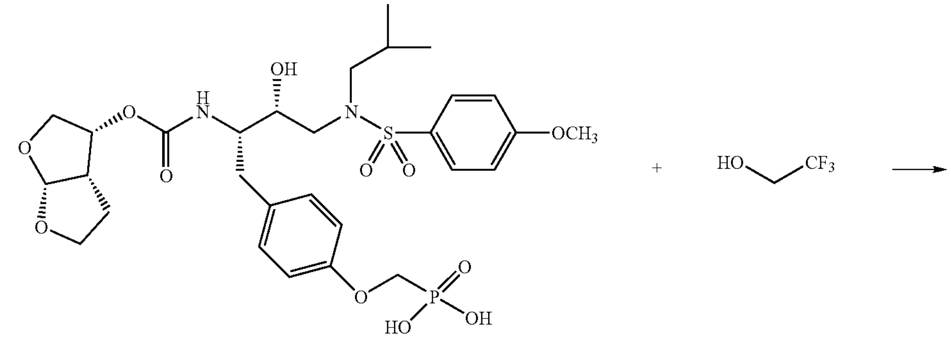
4 5

-continued

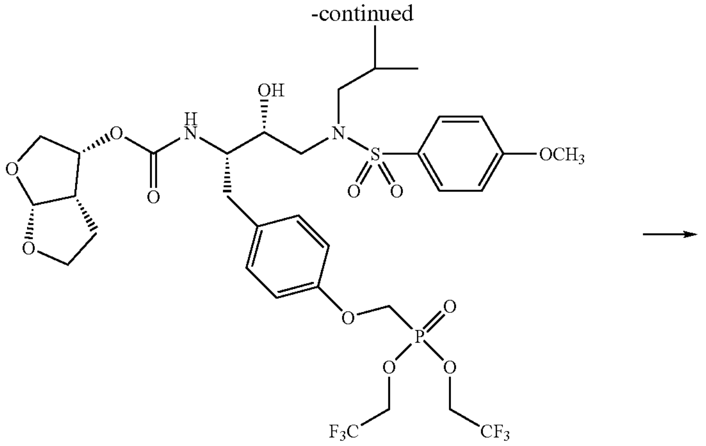

6

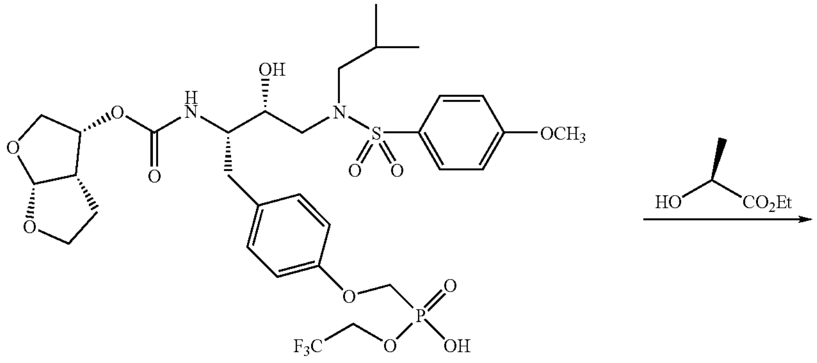

7

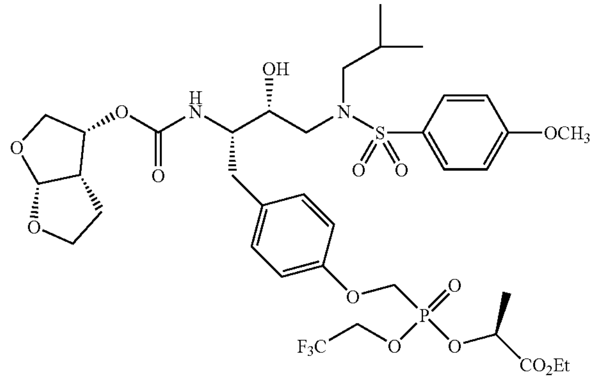

8

Example 1

Mono-Ethyl mono-lactate 3: To a solution of 1 (96 mg, 0.137 mmol) and ethyl lactate 2 (0.31 mL, 2.7 mmol) in pyridine (2 mL) was added N,N-dicyclohexylcarbodiimide (170 mg, 0.822 mmol). The solution was stirred for 18 h at 70° C. The mixture was cooled to room temperature and diluted with dichloromethane. The solid was removed by filtration and the filtrate was concentrated. The residue was suspended in diethyl ether/dichloromethane and filtered again. The filtrate was concentrated and mixture was chromatographed on silica gel eluting with EtOAc/hexane to provide compound 3 (43 mg, 40%) as a foam: $^{1}H$ NMR ($CDCl_3$) δ 7.71 (d, 2H), 7.00 (d, 2H); 7.00 (d, 2H), 6.88 (d, 2H), 5.67 (d, 1H), 4.93-5.07 (m, 2H), 4.15-4.39 (m, 6H), 3.70-3.99 (m, 10H), 2.76-3.13 (m, 7H), 1.55-1.85 (m, 9H), 1.23-1.41 (m, 6H), 0.90 (dd, 6H); $^{31}P$ NMR ($CDCl_3$) δ 19.1, 20.2; MS (ESI) 823 (M+Na).

Example 2

Bis-2,2,2-trifluoroethyl phosphonate 6: To a solution of 4 (154 mg, 0.228 mmol) and 222,-trifluoroethanol 5 (1 mL, 13.7 mmol) in pyridine (3 mL) was added N, N-dicyclohexylcarbodiimide (283 mg, 1.37 mmol). The solution was stirred for 6.5 h at 70° C. The mixture was cooled to room temperature and diluted with dichloromethane. The solid was removed by filtration and the filtrate was concentrated. The residue was suspended in dichloromethane and filtered again. The filtrate was concentrated and mixture was chromatographed on silica gel eluting with EtOAc/hexane to provide compound 6 (133 mg, 70%) as a foam: $^1$H NMR ($CDCl_3$) δ 7.71 (d, 2H), 7.21 (d, 2H); 7.00 (d, 2H), 6.88 (dd, 2H), 5.66 (d, 1H), 4.94-5.10 (m, 3H), 4.39-4.56 (m, 6H), 3.71-4.00 (m, 10H), 2.77-3.18 (m, 7H), 1.67-1.83(m, 2H), 0.91 (dd, 4H); $^{31}$P NMR ($CDCl_3$) δ 22.2; MS (ESI) 859 (M+Na).

Example 3

Mono-2,2,2-trifluoroethyl phosphonate 7: To a solution of 6 (930 mg, 1.11 mmol) in THF (14 mL) and water (10 mL) was added an aqueous solution of NaOH in water (1N, 2.2 mL). The solution was stirred for 1 h at 0° C. An excess amount of Dowex resin ($H^+$) was added to until pH=1. The mixture was filtered and the filtrate was concentrated under reduced pressure. The concentrated solution was azeotroped with EtOAc/toluene three times and the white powder was dried in vacuo provide compound 7 (830 mg, 100%). $^1$H NMR ($CDCl_3$) δ 7.71 (d, 2H), 7.11 (d, 2H); 6.99 (d, 2H), 6.85 (d, 2H), 5.63 (d, 1H), 5.26 (m, 1H), 5.02 (m, 1H), 4.40 (m, 1H), 4.14 (m, 4H), 3.60-3.95 (m, 12H), 2.62-3.15 (m, 15H), 1.45-1.84 (m, 3H), 1.29 (m, 4H), 0.89 (d, 6H); $^{31}$P NMR ($CDCl_3$) δ 19.9; MS (ESI) 723 (M+Na).

Example 4

Mono-2,2,2-trifluoroethyl mono-lactate 8: To a solution of 7 (754 mg, 1 mmol) and N,N-dicyclohexylcarbodiimide (1.237 g, 6 mmol) in pyridine (10 mL) was added ethyl lactate (2.26 mL, 20 mmol). The solution was stirred for 4.5 h at 70° C. The mixture was concentrated and the residue was suspended in diethyl ether (5 mL) and dichloromethane (5 mL) and filtered. The solid was washed a few times with diethyl ether. The combined filtrate was concentrated and the crude product was chromatographed on silica gel, eluting with EtOAc and hexane to provide compound 8 (610 mg, 71%) as a foam. $^1$H NMR ($CDCl_3$) δ 7.71 (d, 2H), 7.16 (d, 2H); 6.99 (d, 2H), 6.88 (dd, 2H), 5.66 (d, 1H), 4.95-5.09 (m, 2H), 4.19-4.65 (m, 6H), 3.71-4.00 (m, 9H), 2.76-3.13 (m, 6H), 1.57-1.85 (m, 7H), 1.24-1.34 (m, 4H), 0.91 (dd, 6H); $^{31}$P NMR ($CDCl_3$) δ 20.29, 21.58; MS (ESI) 855 (M+1).

Example 1

Boc-protected hydroxylamine 1: A solution of diethyl hydroxymethyl phosphonate triflate (0.582 g, 1.94 mmol) in dichloromethane (19.4 mL) was treated with triethylamine (0.541 mL, 3.88 mmol). Tert-butyl N-hydroxy-carbamate (0.284 g, 2.13 mmol) was added and the reaction mixture was stirred at room temperature overnight. The mixture was partitioned between dichloromethane and water. The organic phase was washed with saturated NaCl, dried ($MgSO_4$) and evaporated under reduced pressure. The crude product was purified by chromatography on silica gel (1/1-ethyl acetate/hexane) affording the BOC-protected hydroxylamine 1 (0.41 g, 75%) as an oil: $^1$H NMR ($CDCl_3$) δ 7.83 (s, 1H), 4.21 (d, 2H), 4.18 (q, 4H), 1.47 (s, 9H), 1.36 (t, 6H); $^{31}$P NMR ($CDCl_3$) δ 19.3.

Example 2

Hydroxylamine 2: A solution of BOC-protected hydroxylamine 1 (0.305 g, 1.08 mmol) in dichloromethane (2.40 mL) was treated with trifluoroacetic acid (0.829 mL, 10.8 mmol). The reaction was stirred for 1.5 hours at room temperature and then the volatiles were evaporated under reduced pressure with toluene to afford the hydroxylamine 2 (0.318 g, 100%) as the TFA salt which was used directly without any further purification: $^1$H NMR ($CDCl_3$) δ 10.87 (s, 2H), 4.45 (d, 2H), 4.24 (q, 4H), 1.38 (t, 6H); $^{31}$P NMR ($CDCl_3$) δ 16.9; MS (ESI) 184 (M+H).

Example 3

Oxime 4: To a solution of aldehyde 3 (96 mg, 0.163 mmol) in 1,2-dichloroethane (0.65 mL) was added hydroxylamine 2 (72.5 mg, 0.244 mmol), triethylamine (22.7 μL, 0.163 mmol) and $MgSO_4$ (10 mg). The reaction mixture was stirred at room temperature for 2 hours then the mixture was partitioned between dichloromethane and water. The organic phase was washed with saturated NaCl, dried ($MgSO_4$) and evaporated under reduced pressure. The crude product was purified by chromatography on silica gel (90/10-ethyl acetate/hexane) affording, GS-277771, oxime 4 (0.104 g, 85%) as a solid: $^1$H NMR ($CDCl_3$) δ 8.13 (s, 1H), 7.72 (d, 2H), 7.51 (d, 2H), 7.27 (d, 2H), 7.00 (d, 2H), 5.67 (d, 1H), 5.02 (m, 2H), 4.54 (d, 2H), 4.21 (m, 4H), 3.92 (m, 1H), 3.89 (s, 3H), 3.88 (m, 1H), 3.97-3.71 (m, 2H), 3.85-3.70 (m, 2H), 3.16-2.99 (m, 2H), 3.16-2.81 (m, 7H), 1.84 (m, 1H), 1.64-1.48 (m, 2H), 1.37 (t, 6H), 0.94-0.90 (dd, 6H); $^{31}$P NMR ($CDCl_3$) δ 20.0; MS (ESI) 756 (M+H).

Scheme 1

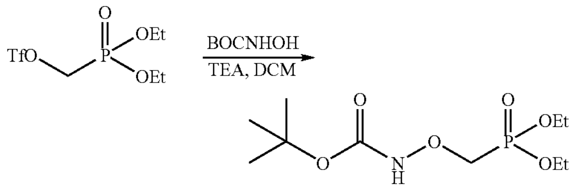

1

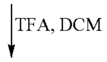

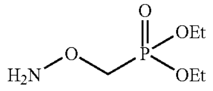

2

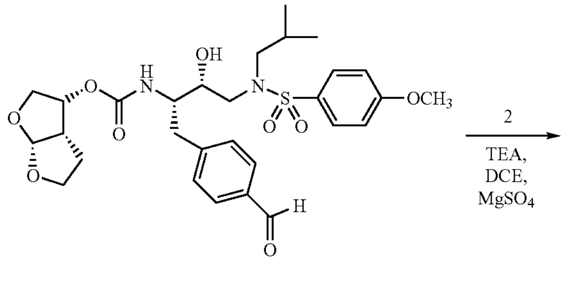

3

-continued

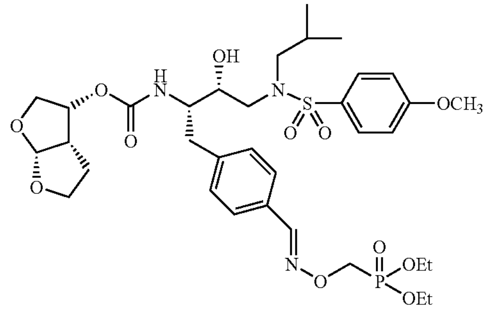

4

Scheme 1

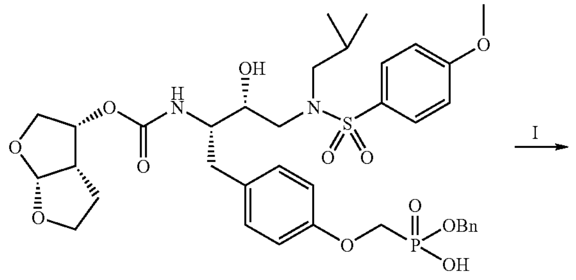

1

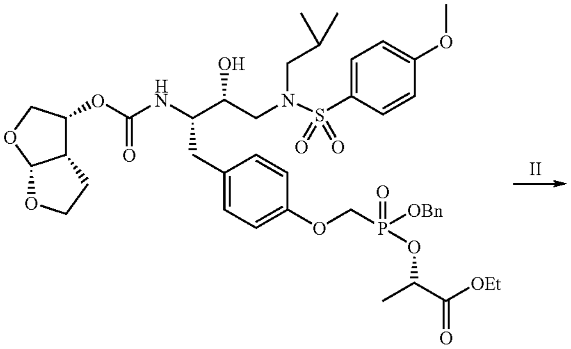

2

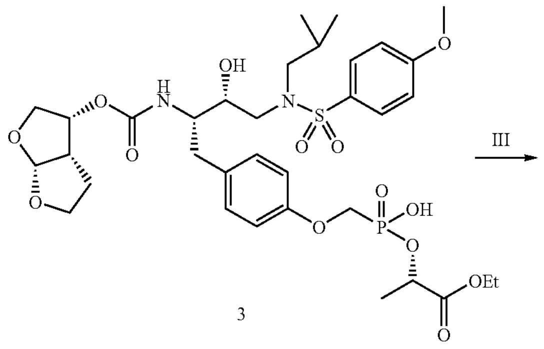

3

-continued

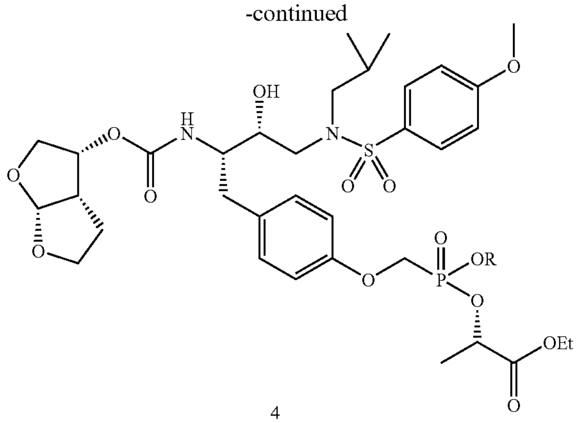

4

I. Ethyl(S)-(-)lactate/Benzotriazol-1-yloxytripyrrolidinophosphonium hexafluorophosphate/DIPEA/EtOAc;
II. $H_2$/20% Pd-C/EtOAc-EtOH;
III. ROH/Benzotriazol-1-yloxytripyrrolidinophosphonium hexafluorophosphate/DIPEA/EtOAc

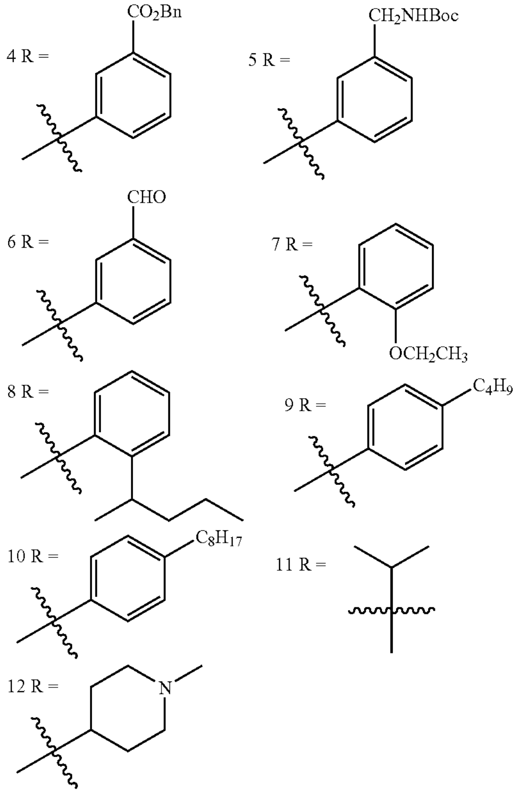

4 R =, 5 R =, 6 R =, 7 R =, 8 R =, 9 R =, 10 R =, 11 R =, 12 R =

Example 1

Compound 1 was prepared according to methods from previous Schemes

Example 2

Compound 2: To a solution of compound 1 (5.50 g, 7.30 mmol), Benzotriazol-1-yloxytripyrrolidinophosphonium hexafluorophosphate (5.70 g, 10.95 mmol), and Ethyl(S)-(−)

lactate (1.30 g, 10.95 mmol) in DMF (50 mL) was added Diisopropylethylamine (5.08 mL, 29.2 mmol). The mixture was stirred for 7 hours after which was diluted in EtOAc. The organic phase was washed with $H_2O$ (5×), brine, dried over $MgSO_4$ and concentrated in vacuo. The residue was purified by silica gel chromatography ($CH_2Cl_2$/Isopropanol=100/4) to give 3.45 g of compound 2.

Example 3

Compound 3: To the mixture of compound 2 (3.45 g) in EtOH/EtOAc (300 mL/100 mL) was added 20% Pd/C (0.700 g). The mixture was hydrogenated for 1 hour. Celite was added and the mixture was stirred for 10 minutes. The mixture was filtered through a pad of celite and washed with ethanol. Concentration gave 2.61 g of compound 3.

Example 4

Compound 4: To a solution of compound 3 (1.00 g, 1.29 mmol) in dry dimethylformamide (5 mL) was added 3-Hydroxy-benzoic acid benzyl ester (0.589 g, 2.58 mmol), Benzotriazol-1-yloxytripyrrolidinophosphonium hexafluorophosphate (1.34 g, 2.58 mmol), followed by addition of Diisopropylethylamine (900 μL, 5.16 mmol). The mixture was stirred for 14 hours, the resulting residue was diluted in EtOAc, washed with brine (3×) and dried over sodium sulfate, filtered, and concentrated under reduced pressure. The residue was purified by silica gel chromatography ($CH_2Cl_2$/Isopropanol=100/3) to provide 67.3 mg of compound 4: $^1$H NMR ($CDCl_3$) δ 7.91 (2H, d, J=8.9 Hz), 7.75 (2H, m), 7.73-7.3 (13H, m), 7.25 (2H, m), 7.21-6.7 (6H, m), 5.87 (1H, m), 5.4-4.8 (6H, m), 4.78-4.21 (4H, m), 3.98 (3H, s), 2.1-1.75 (8H, m), 1.55 (3H, m), 1.28 (3H, m), 0.99(6H, m).

Example 5

Compound 5: To a solution of compound 3 (1.40 g, 1.81 mmol) in dry dimethylformamide (5 mL) was added (4-Hydroxy-benzyl)-carbamic acid tert-butyl ester (0.80 g, 3.62 mmol), Benzotriazol-1-yloxytripyrrolidinophosphonium hexafluorophosphate (1.74 g, 3.62 mmol), followed by addition of Diisopropylethylamine (1.17 ml, 7.24 mmol). The mixture was stirred for 14 hours, the resulting residue was diluted in EtOAc, washed with brine (3×) and dried over sodium sulfate, filtered, and concentrated under reduced pressure. The residue was purified by silica gel chromatography ($CH_2Cl_2$/Isopropanol=100/3.5) to provide 770 mg of compound 5: $^1$H NMR ($CDCl_3$) δ 7.8(2H, d, J=8.9 Hz), 7.4 (2H, m), 7.3-6.8 (8H, m), 5.75 (1H, m), 5.3-5.1 (2H, m), 4.6-4.23 (4H, m), 3.98 (3H, s), 3.7-2.6 (15H, m), 2.2-1.8 (12H, m), 1.72 (3H, s), 1.58 (3H, m), 1.25 (3H, m), 0.95 (6H, m).

Example 6

Compound 6: To a solution of compound 3 (1.00 g, 1.29 mmol) in dry dimethylformamide (6 mL) was added 3-Hydroxybenzaldehyde (0.320 g, 2.60 mmol), Benzotriazol-1-lyloxytripyrrolidinophosphonium hexafluorophosphate (1.35 g, 2.60 mmol), followed by addition of Diisopropylethylamine (901 μL, 5.16 mmol). The mixture was stirred for 14 hours, the resulting residue was diluted in EtOAc, washed with brine (3×) and dried over sodium sulfate, filtered, and concentrated under reduced pressure. The residue was purified by silica gel chromatography ($CH_2Cl_2$/Isopropanol=100/5) to provide 880 mg of compound 6.

Example 7

Compound 7: To a solution of compound 3 (150 mg, 0.190 mmol) in dry dimethylformamide (1 mL) was added 2-Ethoxy-phenol (48.0 μL, 0.380 mmol), Benzotriazol-1-yloxytripyrrolidinophosphonium hexafluorophosphate (198 mg, 0.380 mmol), followed by addition of Diisopropylethylamine (132 mL, 0.760 mmol). The mixture was stirred for 14 hours, the resulting residue was diluted in EtOAc, washed with brine (3×) and dried over sodium sulfate, filtered, and concentrated under reduced pressure. The residue was purified by silica gel chromatography ($CH_2Cl_2$/Isopropanol=100/4) to provide 84.7 mg of compound 7: $^1$H NMR ($CDCl_3$) δ 7.73 (2H, d, J=8.9 Hz), 7.15 (2H, m), 7.01-6.9 (8H, m), 5.66 (1H, m), 5.22-5.04 (2H, m), 4.56-4.2 (6H, m), 4.08 (2H, m), 3.89 (3H, m), 3.85-3.69 (6H, m), 3.17-2.98 (7H, m), 2.80 (3H, m) 1.86 (1H, m), 1.65 (2H, m) 1.62-1.22 (6H, m), 0.92 (6H, m).

Example 8

Compound 8: To a solution of compound 3 (50.0 mg, 0.0650 mmol) in dry dimethylformamide (1 mL) was added 2-(1-methylbutyl)phenol (21.2 mg, 0.130 mmol), Benzotriazol-1-yloxytripyrrolidinophosphonium hexafluorophosphate (67.1 mg, 0.130 mmol), followed by addition of Diisopropylethylamine (45.0 μL, 0.260 mmol). The mixture was stirred for 14 hours, the resulting residue was diluted in EtOAc, washed with brine (3×) and dried over sodium sulfate, filtered, and concentrated under reduced pressure. The residue was purified by reversed phase HPLC to provide 8.20 mg of compound 8: $^1$H NMR ($CDCl_3$) δ 7.73 (2H, d, J=8.9 Hz), 7.25 (2H, m), 7.21-6.89 (8H, m), 5.7 (1H, m), 5.29-4.9 (2H, m), 4.56-4.2 (6H, m), 3.89 (3H, m), 3.85-3.69 (6H, m), 3.17-2.89 (8H, m), 2.85 (3H, m), 2.3-1.65 (4H, m), 1.55-1.35 (6H, m), 0.92 (6H, m).

Example 9

Compound 9: To a solution of compound 3 (50.0 mg, 0.0650 mmol) in dry dimethylformamide (1 mL) was added) 4-N-Butylphenol (19.4 mg, 0.130 mmol), Benzotriazol-1-yloxytripyrrolidinophosphonium hexafluorophosphate (67.1 mg, 0.130 mmol), followed by addition (45.0 μL, 0.260 mmol) of Diisopropylethylamine. The mixture was stirred for 14 hours, the resulting residue was diluted in EtOAc, washed with brine (3×) and dried over sodium sulfate, filtered, and concentrated under reduced pressure. The residue was purified by reversed phase HPLC to provide 9.61 mg of compound 9: $^1$H NMR ($CDCl_3$) δ 7.8 (2H, d, J=8.9 Hz), 7.4 (2H, m), 7.3-6.8 (8H, m), 5.75 (1H, m), 5.3-4.5 (4H, m), 4.3-3.4.1 (4H, m), 3.9 (3H, m), 3.3-2.59 (11H, m), 2.25 (2H, m), 1.85-1.5 (5H, m), 1.4-1.1 (10H, m), 0.95 (9H, m).

Example 10

Compound 10: To a solution of compound 3 (50.0 mg, 0.0650 mmol) in dry dimethylformamide (1 mL) was added 4-Octylphenol (26.6 mg, 0.130 mmol), Benzotriazol-1-yloxytripyrrolidinophosphonium hexafluorophosphate (67.1 mg, 0.130 mmol), followed by addition of Diisopropylethylamine (45.0 μL, 0.260 mmol). The mixture was stirred for 14 hours, the resulting residue was diluted in EtOAc, washed with brine (3×) and dried over sodium sulfate, filtered, and concentrated under reduced pressure. The residue was purified by reversed phase HPLC to provide 7.70 mg of compound 10: $^1$H NMR ($CDCl_3$) δ 7.75 (2H, d, J=8.9 Hz), 7.3 (2H, m), 7.2-6.8 (8H, m), 5.70 (1H, m), 5.3-4.9 (4H, m), 4.6-3.9 (4H, m), 3.89 (3H, m), 3.85-2.59 (12H, m), 2.18-1.75 (10H, m), 1.69-1.50 (8H, m), 1.4-1.27 (6H, m), 0.95 (9H, m).

Example 11

Compound 11: To a solution of compound 3 (100 mg, 0.120 mmol) in dry dimethylformamide (1 mL) was added Isopropanol (20.0 μL, 0.240 mmol), Benzotriazol-1-yloxytripyrrolidinophosphonium hexafluorophosphate (135 mg, 0.240 mmol), followed by addition of Diisopropylethylamine (83.0 μL, 0.480 mmol). The mixture was stirred for 14 hours, the resulting residue was diluted in EtOAc, washed with brine (3×) and dried over sodium sulfate, filtered, and concentrated under reduced pressure. The residue was purified by silica gel chromatography ($CH_2Cl_2$/Isopropanol=100/4) to provide 12.2 mg of compound 11: $^1H$ NMR ($CDCl_3$) δ 7.71 (2H, d, J=8.9 Hz), 7.15 (2H, m), 7.0 (2H, m), 6.89 (2H, m), 5.65 (1H, m), 5.03-4.86 (4H, m), 4.34-4.19 (3H, m), 3.89 (3H, s), 3.88 (1H, m), 3.82 (2H, m), 3.65 (4H, m), 3.2-2.9 (11H, m), 2.80 (3H, m) 1.65 (2H, m), 1.86 (1H, m), 1.6 (3H, m), 1.30 (3H, m), 0.92 (6H, m).

Example 12

Compound 12: To a solution of compound 3 (100 mg, 0.120 mmol) in dry dimethylformamide (1 mL) was added 4-Hyrdroxy-1-methylpiperidine (30.0 mg, 0.240 mmol), Benzotriazol-1-yloxytripyrrolidinophosphonium hexafluorophosphate (135 mg, 0.240 mmol), followed by addition of Diisopropylethylamine (83.0 μL, 0.480 mmol). The mixture was stirred for 14 hours, the resulting residue was diluted in EtOAc, washed with brine (3×) and dried over sodium sulfate, filtered, and concentrated under reduced pressure. The residue was purified by reversed phase HPLC to provide 50.1 mg of compound 12: $^1H$ NMR ($CDCl_3$) δ 7.73 (2H, d, J=8.9 Hz), 7.18 (2H, m), 7.0 (2H, m), 6.9 (2H, m), 5.67 (1H, m), 5.2-4.9 (4H, m), 4.30-4.11 (4H, m), 3.98 (1H, m), 3.89 (3H, s), 3.87 (1H, m), 3.75 (2H, m), 3.5-3.3 (4H, m), 3.2-2.9 (14H, m), 2.80 (3H, m) 1.65 (2H, m), 1.86 (1H, m), 1.6 (3H, m), 1.30 (3H, m), 0.92 (6H, m).

Scheme 2

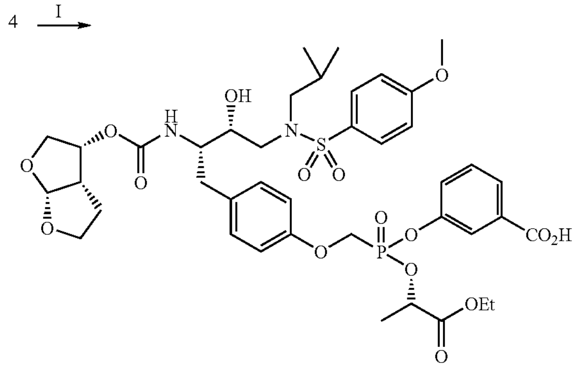

13

I. $H_2$/10% Pd-C/EtOAc

Scheme 3

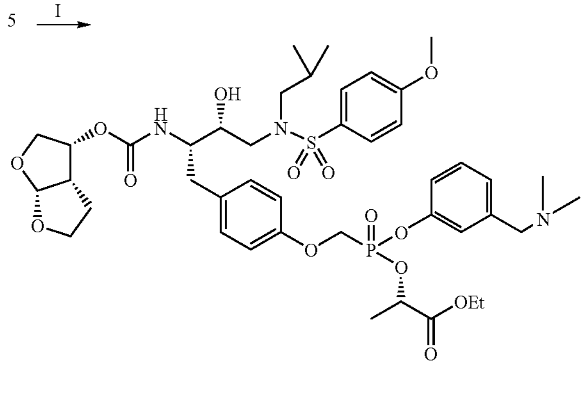

14

I. a: TFA/$CH_2Cl_2$/0° C.; b: HCHO/HOAc/$NaBH_3CN$/EtOAc/0° C.

Scheme 4

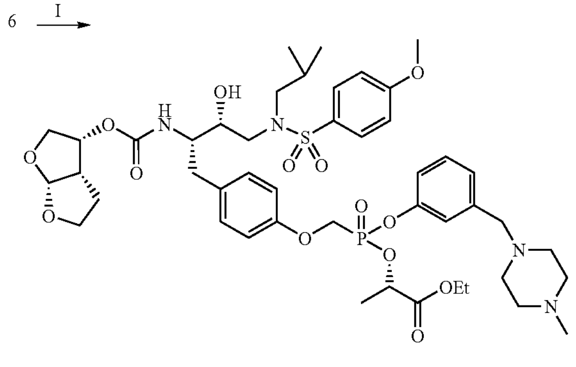

15

I. $R_2NH$/HoAC/$NaBH_3CN$/EtOAc

Example 13

Compound 13: To a solution of compound 4 (4.9 g)) in EtOAc (150 ml) was added 20% Pd/C (0.90 g), the reaction mixture was hydrogenated for 1 hour. Celite was added and the mixture was stirred for 10 minutes. The mixture was filtered through a pad of celite and washed with ethanol. Concentration gave 4.1 g of compound 13: $^1H$ NMR ($CDCl_3$) δ 7.91 (2H, d, J=8.9 Hz), 7.75 (2H, m), 7.73-7.3 (8H, m), 7.25 (2H, m), 7.21-6.7 (6H, m), 5.4-4.8 (6H, m), 4.78-4.21 (4H, m), 3.98 (3H, s), 2.1-1.75 (8H, m), 1.55 (3H, m), 1.28 (3H, m), 0.99 (6H, m).

Example 14

Compound 14: To a solution of compound 5 (0.770 g, 0.790 mmol) in dichloromethane (10 mL), under ice-cooling, was added triflouroacetic acid (5 mL), the resulting mixture was stirred at 25° C. for two hours. The reaction mixture was concentrated under reduced pressure and the residue was co-evaporated with EtOAc to provide an yellow oil. To a solution of the above oil in (10 mL) of EtOAc, under ice-cooling and stirring was added formaldehyde (210 mL, 2.86 mmol), acetic acid (252 μL, 4.30 mmol), followed by sodium cyanoborohydride (178 mg, 2.86 mmol). The mixture was further stirred at 25° C. for 2 hours. The above mixture was concentrated and diluted with EtOAc and washed with $H_2O$ (3×), brine, dried over sodium sulfate, filtered, and concentrated under reduced pressure. The residue was purified using reversed-phase HPLC to provide 420 mg of compound 14: $^1H$ NMR ($CDCl_3$) δ 7.8 (2H, d, J=8.9 Hz), 7.4 (2H, m), 7.3-6.8 (8H, m), 5.75 (1H, m), 5.3-5.1 (2H, m), 4.6-4.23 (4H, m), 3.98 (3H, s), 3.7-2.6 (15H, m), 2.2-1.8 (8H, m), 1.72 (3H, s), 1.58 (3H, m), 1.25 (3H, m), 0.95 (6H, m).

Example 15

Compound 15: To a solution of compound 6 (100 mg, 0.114 mmol) in EtOAc (1 mL) was added 1-Methyl-piperazine (63.2 mg, 0.570 mmol), acetic acid (34.0 μl, 0.570 mmol) followed by Sodium Cyanoborohydride (14.3 mg, 0.228 mmol). The mixture was stirred at 25° C. for 14 hours. The reaction mixture was concentrated and diluted with EtOAc and washed with $H_2O$ (5×), brine (2×), dried over sodium sulfate, filtered, and concentrated under reduced pressure. The residue was purified using silica gel chromatography ($CH_2Cl_2$/Isopropanol=100/6.5) to give 5.22 mg of compound 15: $^1H$ NMR ($CDCl_3$) δ 7.73 (2H, d, J=8.9 Hz), 7.4-7.18 (8H, m), 7.1-6.89 (2H, m), 5.67 (1H, m), 5.2-4.9 (4H, m), 4.30-4.11 (4H, m), 3.98 (1H, m), 3.89 (3H, s), 3.87 (1H, m), 3.75 (2H, m), 3.5-3.3 (4H, m), 3.2-2.9 (10H, m), 2.80-2.25 (8H, m) 1.65 (2H, m), 1.86 (1H, m), 1.6 (3H, m), 1.30 (3H, m), 0.92 (6H, m).

Scheme 5

3

I

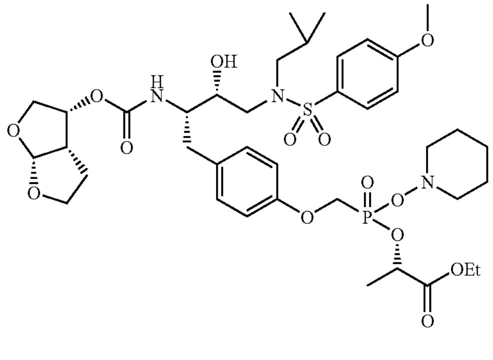

16

I. Piperidin-1-ol/DCC/Pyridine

Scheme 6

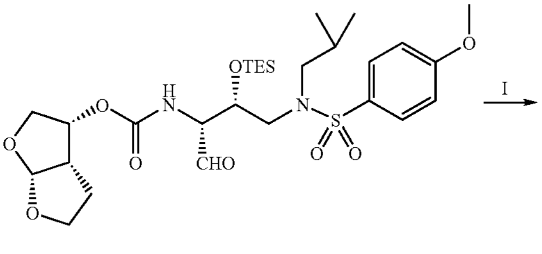

17

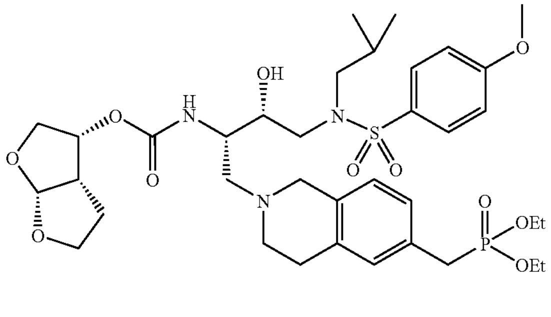

18

I. a: $R_2NH$/HOAc/$NaBH_3CN$/EtOAc b. 2% HF/$CH_3CN$

Example 16

Compound 16: To a solution of compound 3 (100 mg, 0.120 mmol) in Pyridine (600 μL) was added Piperidin-1-ol (48.5 mg, 0.480 mmol), followed by N,N-Dicyclohexylcarbodiimide (99.0 mg, 0.480 mmol). The mixture was stirred for 6 hours, the solvent was concentrated under reduced pressure. The resulting residue was purified by silica gel chromatography ($CH_2Cl_2$/Methanol=100/5) to provide 17 mg of compound 16: $^1H$ NMR ($CDCl_3$) δ 7.73 (2H, d, J=8.9 Hz), 7.16 (2H, m), 7.0 (2H, m), 6.9 (2H, m), 5.68 (1H, m), 5.17 (1H, m), 5.04 (1H, m), 4.5-4.2 (4H, m), 3.90 (3H, s), 3.75 (2H, m), 3.5-3.3 (4H, m), 3.2-2.9 (10H, m), 2.80 (3H, m) 1.65 (2H, m), 1.86 (1H, m), 1.6 (3H, m), 1.5-1.27 (9H, m), 0.92 (6H, m).

Example 17

Compound 18: To a solution of compound 17 (148 mg, 0.240 mmol) in 4 mL of Methanol was added (1,2,3,4-Tetrahydro-isoquinolin-6-ylmethyl)-phosphonic acid diethyl ester (70.0 mg, 0.240 mmol), acetic acid (43.0 μL, 0.720 mmol). The reaction mixture was stirred for 3 minutes, followed by addition of Sodium Cyanoborohydride (75.3 mg, 1.20 mmol). The reaction mixture was stirred at 25° C. for 14 hours. The reaction mixture was diluted with EtOAc and washed with $H_2O$ (3×), brine, dried over sodium sulfate, filtered, and concentrated under reduced pressure. The residue was purified using silica gel chromatography ($CH_2Cl_2$/Isopropanol=100/5) to give 59 mg of TES protected intermediate. 83 μL of 48% HF solution was added to acetonitrile (4 mL) to prepare the 2% HF solution. The above 2% HF solution was added to TES protected intermediate (47 mg, 0.053 mmol) and the reaction mixture was stirred for 2 hours. The solvent was concentrated and the residue was diluted with EtOAc, dried over sodium sulfate, filtered, and concentrated under reduced pressure. The residue was purified using silica gel chromatography ($CH_2Cl_2$/Methanol=100/10) to give 35.2 mg of compound 18: $^1H$ NMR ($CDCl_3$) δ 7.73 (2H, d, J=8.9 Hz), 7.05 (2H, m), 6.89 (2H, m), 6.76 (1H, m), 5.75 (1H, m), 5.67 (1H, m), 5.3 (2H, m), 4.2-3.6 (12H, m), 3.4-2.4 (11H, m), 2.1-1.8 (6H, m), 1.4-1.28 (8H, m), 0.92 (6H, m).

Scheme 7

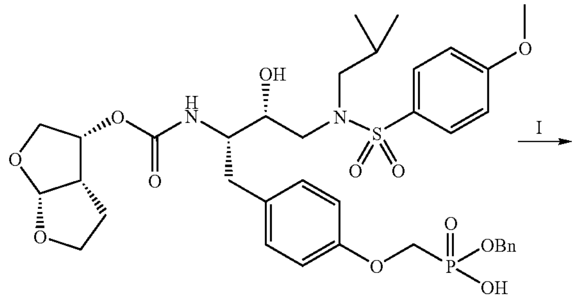

1

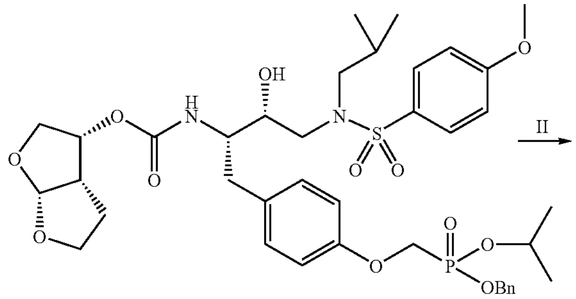

19

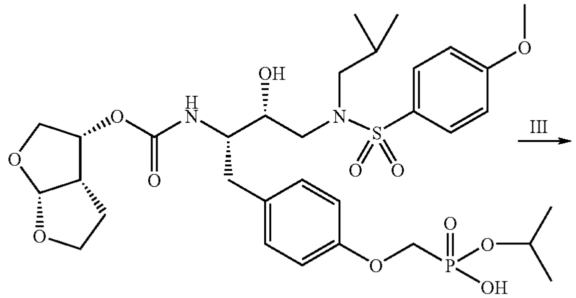

20

-continued

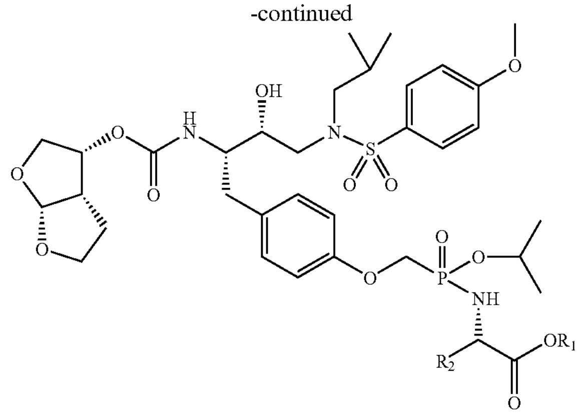

21

$R_1$ = Me, Et, i-Pr
$R_2$ = Me, Et, i-Pr

I. Isopropanol/Benzotriazol-1-yloxytripyrrolidinophosphonium hexafluorophosphate/DIPEA/DMF;
II. $H_2$/10% Pd-C/EtOAc-EtOH
III. $RNH_2$/Aldrithiol-2/$PPh_3$/$iPr_2NET$/pyridine Compound 19 is prepared following the procedure for compound 2 by using monoacid 1. Compound 20 is made following a hydrogenation of compound 19. Mono acid 20 reacts with corresponding amino esters in the presence of Aldrithiol-2 and triphenylphosphine to form compound 21.

Scheme 8

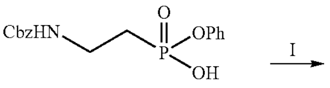

22

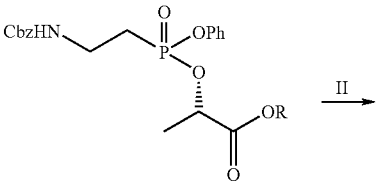

23

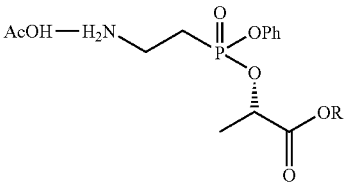

24

-continued

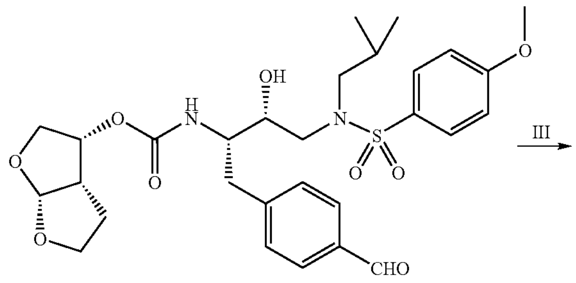

25

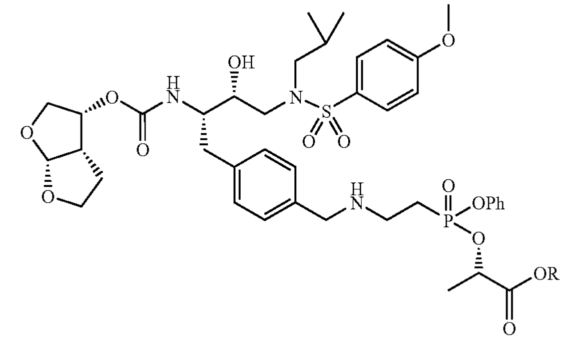

26 R = Me, Pr, i-Pr

I. a. $SOCl_2$/60 C.; b. Alkyl (s)-lactate/$Et_3N$;
II. $H_2$/10% Pd-C/EtOAc-HOAc;
III. a. compound 25/$MgSO_4$; b. HOAc/$NaBH_3CN$ Monoacid 22 is treated with thionyl chloride at 60° C. to form monochloridate, which reacts with corresponding alkyl (s)lactate to generate monolactate 23. Monolactate 23 is hydrogenated with 10% Pd—C in the presence of acetic acid to form amine 24. Aldehyde 25 reacts with amine 24 in the presence of $MgSO_4$ to form the intermediate imine, which is reduced with sodium cyanoborohydride to afford compound 26.

Scheme 1

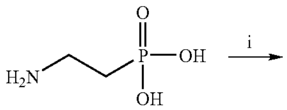

1

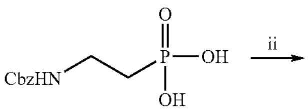

2

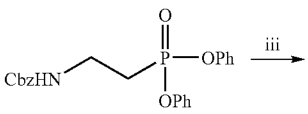

3

-continued

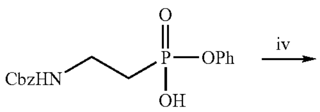

4

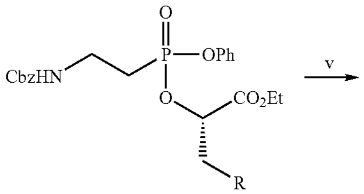

5 R = H
6 R = H

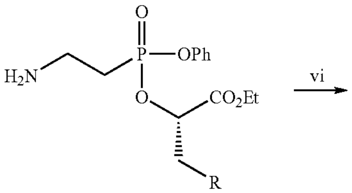

7 R = Me

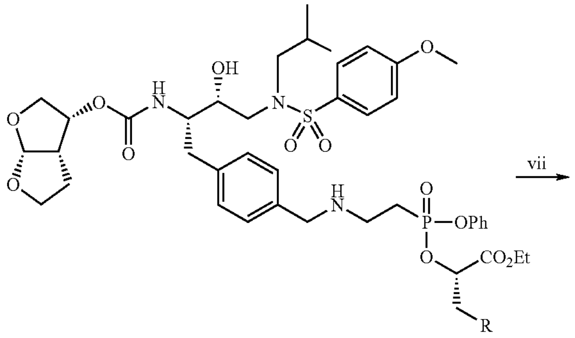

9 R = Me

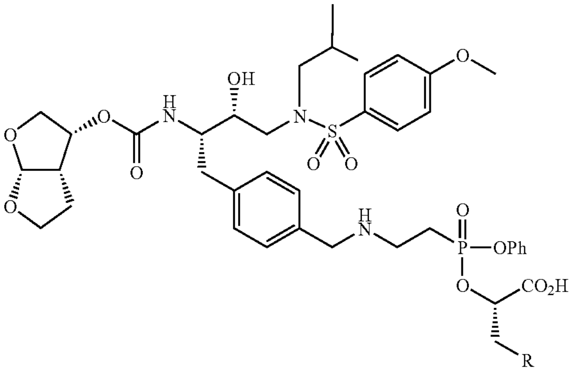

10 R = Me

-continued

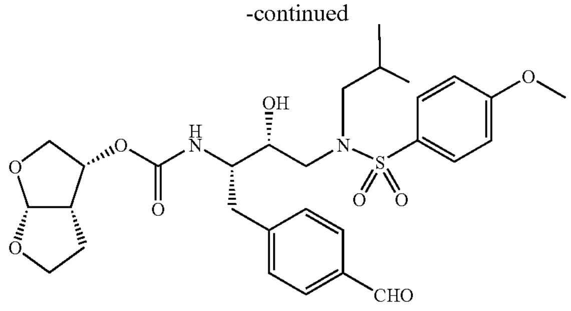

8

Reagents and conditions:
i. CbzCl, NaOH, tol/$H_2O$, 100%;
ii. a. $SOCl_2$, DMF, tol, 65° C.; b. PhOH, $Et_3N$, $CH_2Cl_2$, 71%;
iii. aq. NaOH, $CH_3CN$, 79%
iv. a. $SOCl_2$, DMF, tol, 65° C.; b. ethyl lactate, $Et_3N$, $CH_2Cl_2$, (5) 85%; 2-hydroxy butyric acid ethyl ester, $Et_3N$, $CH_2Cl_2$, (6) 75%;
v. $H_2$, AcOH, 10% Pd/C, EtOH, 94%;
vi. a. 7 + 8, 1,2-DCE, $MgSO_4$; b. $NaBH_3CN$, AcOH, 50%;
vii. pig liver esterase, 20% DMSO/PBS, 40° C., 25%

Example 1

Compound 2: A 3L, 3-neck flask was equipped with a mechanical stirrer and addition funnel and charged with 2-aminoethyl phosphonic acid (60.0 g, 480 mmol). 2N Sodium hydroxide (480 mL, 960 mmol) was added and flask cooled to 0° C. Benzyl chloroformate (102.4 g, 600 mmol) in toluene (160 mL) was added dropwise with vigorous stirring. The reaction mixture was stirred at 0° C. for 30 minutes, then at room temperature for 4 h. 2N sodium hydroxide (240 mL, 480 mmol) was added, followed by benzyl chloroformate (20.5 g, 120 mmol) and the reaction mixture was vigorously stirred for 12 h. The reaction mixture was washed with diethyl ether (3×). The aqueous layer was acidified to pH 2 with concentrated HCl to give a white precipitate. Ethyl acetate was added to the mixture and concentrated HCl (80 mL, 960 mmol) was added. The aqueous layer was extracted with ethyl acetate and combined organic layer was dried ($MgSO_4$) and concentrated to give a waxy, white solid (124 g, 479 mmol, 100%). $^1H$ NMR (300 MHz, $CD_3OD$): δ 7.45-7.30 (m, 5H, Ar), 5.06 (d, J=14.7 Hz, 2H, $CH_2Ph$), 3.44-3.31 (m, 2H, $NCH_2CH_2$), 2.03-1.91 (m, 2H, $CH_2CH_2P$); $^{31}P$ NMR (121 MHz, $CD_3OD$): δ 26.3.

Example 2

Compound 3: To a mixture of compound 2 (50.0 g, 193 mmol) in toluene (1.0 L) was added DMF (1.0 mL) followed by thionyl chloride (56 mL, 768 mmol). The reaction mixture was heated at 65° C. for 3-4 h under a stream of argon. The reaction mixture was cooled to room temperature and concentrated. Residual solvent was removed under high vacuum for 1 h. The residue was dissolved in $CH_2Cl_2$ (1.0 L) and cooled to 0° C. Triethylamine (161 mL, 1158 mmol) was added, followed by phenol (54.5 g, 579 mmol). The reaction mixture was warmed to room temperature overnight, then washed with 1.0N HCl, saturated $NaHCO_3$ solution, brine and dried ($MgSO_4$). Concentrated and purified (silica gel, 1:1 EtOAc/Hex) to give a pale yellow solid (56 g, 136 mmol, 71%). $^1H$ NMR (300 MHz, $CDCl_3$): δ 7.40-7.10 (m, 15H, Ar), 5.53 (br s, 1H, NH), 5.11 (br s, 2H, $CH_2Ph$), 3.72-3.60 (m, 2H, $NCH_2CH_2$), 2.49-2.30 (m, 2H, $CH_2CH_2P$); $^{31}P$ NMR (121 MHz, $CDCl_3$): δ 22.9.

Example 3

Compound 4: To a solution of compound 3 (64 g, 155.6 mmol) in acetonitrile (500 mL) at 0° C. was added 2.0M sodium hydroxide. The reaction mixture was stirred at 0° C. for 30 min, then at room temperature for 2.5 h. The reaction mixture was concentrated to 100 mL and diluted with $H_2O$ (500 mL). The aqueous solution was washed with EtOAc (3×300 mL). The aqueous layer was acidified to pH 1 with concentrated HCl, producing a white precipitated. The mixture was extracted with EtOAc (4×300 mL) and combined organic layer was washed with brine and dried ($MgSO_4$). Concentration gave a solid, which was recrystallized from hot EtOAc (450 mL) to give a white solid (41.04 g, 122 mmol, 79%). $^1H$ NMR (300 MHz, $CD_3OD$): δ 7.45-7.10 (m, 10H, Ar), 5.09 (s, 2H, $CH_2Ph$), 3.53-3.30 (m, 2H, $NCH_2CH_2$), 2.25-2.10 (m, 2H, $CH_2CH_2P$); $^{31}P$ NMR (121 MHz, $CD_3OD$): δ 24.5.

Example 4

Compound 5: To a mixture of compound 4 (28 g, 83 mmol) in toluene (500 mL) was added DMF (1.0 mL), followed by thionyl chloride (36.4 mL, 499 mmol). The mixture was heated at 65° C. for 2 h providing a pale yellow solution. The reaction mixture was concentrated and dried for 45 min under high vacuum. The residue was dissolved in anhydrous $CH_2Cl_2$ (350 mL) and cooled to 0° C. Triethylamine (45.3 mL, 332 mmol) was added slowly, followed by the dropwise addition of ethyl lactate (18.8 mL, 166 mmol). The reaction mixture was stirred at 0° C. for 30 min, then warmed to room temperature overnight. The reaction mixture was diluted with $CH_2Cl_2$ and washed with 1 N HCl, saturated $NaHCO_3$ solution, brine and dried ($MgSO_4$). Concentration and purification (silica gel, 1:5 to 1:0 EtOAc/Hex) gave a pale yellow oil (30.7 g, 71 mmol, 85%) as a mixture of diastereomers which were separated by HPLC (Dynamax reverse phase C-18 column, 60% acetonitrile/$H_2O$). More polar diastereomer: $^1H$ NMR (300 MHz, $CDCl_3$): δ 7.40-7.10 (m, 10H, Ar), 5.65 (s, 1H, NH), 5.12 (s, 2H, $CH_2Ph$), 5.10-5.00 (m, 1H, OCHC) 4.17 (q, J=6.9 Hz, 2H, $OCH_2CH_3$), 3.62 (dt, $J_1$=20.4 Hz, $J_2$=6.0 Hz, 2H, $NCH_2CH_2$), 2.25 (dt, $J_1$=18.0 Hz, $J_2$=6.0 Hz, 2H, $CH_2CH_2P$), 1.60 (dd, J=$J_2$=6.9 Hz, 3H, $CHCH_3$), 1.23 (t, J=6.9 Hz, 3H, $OCH_2CH_3$); $^{31}P$ NMR (121 MHz, $CDCl_3$): δ 26.2. Less polar diastereomer: $^1H$ NMR (300 MHz, $CDCl_3$): δ 7.40-7.10 (m, 10H, Ar), 5.87 (s, 1H, NH), 5.13 (s, 2H, $CH_2Ph$), 5.10-5.00 (dq, $J_1$=$J_2$=6.9 Hz, 1H, OCHC) 4.22 (q, J=7.2 Hz, 2H, $OCH_2CH_3$), 3.68 (dt, $J_1$=21.6 Hz, $J_2$=6.9 Hz, 2H, $NCH_2CH_2$), 2.40-2.20 (m, 2H, $CH_2CH_2P$), 1.49 (dd, J. =70.2 Hz, $J_2$=6.9 Hz, 3H, $CHCH_3$), 1.28 (t, J=6.9 Hz, 3H, $OCH_2CH_3$); $^{31}P$ NMR (121 MHz, $CDCl_3$): δ 28.3.

Example 5

Compound 6:2-Hydroxy-butyric acid ethyl ester was prepared as follows: To a solution of L-2-aminobutyric acid (100 g, 970 mmol) in 1.0 N $H_2SO_4$ (2 L) at 0° C. was added $NaNO_2$ (111 g, 1610 mmol) in $H_2O$ (400 mL) over 2 h. The reaction mixture was stirred at room temperature for 18 h. Reaction mixture was extracted with EtOAc (4×) and combined organic layer was dried ($MgSO_4$) and concentrated to give a yellow solid (41.5 g). This solid was dissolved in absolute ethanol (500 mL) and concentrated HCl (3.27 mL, 39.9 mmol) was added. Reaction mixture was heated to 80° C. After 24 h, concentrated HCl (3 mL) was added and reaction continued for 24 h. Reaction mixture was concentrated and product was distilled to give a colorless oil (31 g, 235 mmol, 59%).

To a mixture of compound 4 (0.22 g, 0.63 mmol) in anhydrous acetonitrile (3.0 mL) was added thionyl chloride (0.184 mL, 2.52 mmol). The mixture was heated at 65° C. for 1.5 h providing a pale yellow solution. The reaction mixture was concentrated and dried for 45 min under high vacuum. The residue was dissolved in anhydrous $CH_2Cl_2$ (3.3 mL) and cooled to 0° C. Triethylamine (0.26 mL, 1.89 mmol) was added slowly, followed by the dropwise addition of 2-hydroxy-butyric acid ethyl ester (0.167 mL, 1.26 mmol). The reaction mixture was stirred at 0° C. for 5 min, then warmed to room temperature overnight. The reaction mixture was concentrated, dissolved in EtOAc and washed with 1.0 N HCl, saturated $NaHCO_3$ solution, brine and dried ($MgSO_4$). Concentration and purification (silica gel, 3:2 EtOAc/Hex) gave a pale yellow oil (0.21 g, 0.47 mmol, 75%). For major diastereomer, $^1H$ NMR (300 MHz, $CDCl_3$): δ 7.35-7.10 (m, 10H, Ar), 5.91 (s, 1H, NH)), 5.12 (s, 2H, $CH_2Ph$), 4.94-4.83 (m, 1H, OCHC), 4.27-4.12 (m, 2H, $OCH_2CH_3$), 3.80-3.50 (m, 2H, $NCH_2CH_2$), 2.39-2.19 (m, 2H, $CH_2CH_2P$), 1.82-1.71 (m, 2H, $CHCH_2CH_3$), 1.30-1.195 (m, 3H. $OCH_2CH_3$), 0.81 (t, J=7.5 Hz, 3H, $CHCH_2CH_3$); $^{31}P$ NMR (120 MHz, $CDCl_3$): δ 28.3. For minor diastereomer, $^1H$ NMR (300 MHz, $CDCl_3$): δ 7.35-7.10 (m, 10H, Ar), 5.74 (s, 1H, NH)), 5.11 (s, 2H, $CH_2Ph$), 4.98-4.94 (m, 1H, OCHC), 4.27-4.12 (m, 2H, $OCH_2CH_3$), 3.803.50 (m, 2H, $NCH_2CH_2$), 2.39-2.19 (m, 2H, $CH_2CH_2P$), 1.98-1.82 (m, 2H, $CHCH_2CH_3$), 1.30-1.195 (m, 3H, $OCH_2CH_3$), 1.00 (t, J=7.5 Hz, 3H, $CHCH_2CH_3$); $^{31}P$ NMR (121 MHz, $CDCl_3$): δ 26.2.

Example 6

Compound 7: A mixture of compound 6, (0.53 g, 1.18 mmol) acetic acid (0.135 mL, 2.36 mmol) and 10% palladium on activated carbon (0.08 g) in absolute ethanol (12 mL) was stirred under a hydrogen atmosphere (1 atm) for 3 h. Reaction mixture was filtered through Celite, concentrated, and resubjected to identical reaction conditions. After 2 h, Celite was added to the reaction mixture and mixture was stirred for 2 min, then filtered through a pad of Celite and concentrated. Dried under high vacuum to give the diasteromeric acetate salt as a oil (0.42 g, 1.11 mmol, 94%). $^1H$ NMR (300 MHz, $CDCl_3$): δ 7.40-7.10 (m, 5H, Ar), 5.004.80 (m, 1H, OCHC), 4.28-4.10 (m, 2H, $OCH_2CH_2$), 3.32-3.14 (m, 2H, $NCH_2CH_2$), 2.452.22 (m, 2H, $CH_2CH_2P$), 1.97 (s, 3H, Ac), 1.97-1.70 (m, 2H, $CHCH_2CH_3$), 1.30-1.18 (m, 3H, $OCH_2CH_3$), 1.00 (t, J=7.5 Hz, 1H, $CHCH_2CH_3$), 0.80 (t, J=7.5 Hz, 2H, $CHCH_2CH_3$); $^{31}P$ NMR (121 MHz, $CDCl_3$): δ 27.6 (major, 1.85), 26.0 (minor, 1.01).

Example 7

Compound 9: A solution of aldehyde 8 (0.596 g, 1.01 mmol) and compound 7 (0.42 g, 1.11 mmol) were stirred together in 1,2-dichloroethane (4.0 mL) in the presence of $MgSO_4$ for 3 h. Acetic acid (0.231 mL, 4.04 mmol) and sodium cyanoborohydride (0.127 g, 2.02 mmol) were added and reaction mixture was stirred for 50 min at room temperature. Reaction mixture was quenched with saturated $NaHCO_3$ solution, diluted with EtOAc, and vigorously stirred for 5 min. Brine was added and extracted with EtOAc (2×). Combined organic layer was dried ($MgSO_4$) concentrated and purified (silica gel, EtOAc, then 10% EtOH/EtOAc) to give a colorless foam. Acetonitrile (4 mL) and trifluoroacetic acid (0.06 mL) were added and concentrated to a volume of 1 mL. $H_2O$ (10 mL) was added and lyophilized to give the TFA salt as a white powder (0.51 g, 0.508 mmol, 50%). $^1H$ NMR (300 MHz, $CD_3CN$): δ 7.79 (d, J=8.4 Hz, 2H, $(SO_2C(CH)_2)$, 7.43-7.20 (m, 9H, Ar), 7.10 (d, J=8.4 Hz, 2H, $(CH)_2COCH_3$), 5.85 (d, J=8.4 Hz, 1H, NH), 5.55 (d, J=4.5 Hz, 1H, OCHO), 5.00-4.75 (m, 2H, $CH_2CHOC(O)$, POCHC), 4.39-4.05 (m, 2H, $PhCH_2N$, $OCH_2CH_3$), 3.89 (s, 3H, $OCH_3$), 3.88-3.30 (m, 9H), 3.15-2.84 (m, 5H), 2.65-2.42 (m, 3H), 2.10-1.68 (m, 5H), 1.65-1.15 (m, 5H), 1.05-0.79 (m, 9H); $^{31}P$ NMR (121 MHz, $CD_3CN$): δ 24.8 (major, 1.85), 23.1 (minor, 1.01).

Example 8

Compound 10: Compound 9 (0.041 g, 0.041 mmol) was dissolved in DMSO (1.9 mL) and to this solution was added phosphate buffered saline, pH 7.4 (10 mL) and pig liver esterase (Sigma, 0.2 mL). Reaction mixture was stirred for 24 h at 40° C. After 24 h, additional esterase (0.2 mL) was added and reaction was continued for 24 h. Reaction mixture was concentrated, resuspended in methanol and filtered. Filtrate was concentrated and purified by reverse phase chromatography to give a white powder after lyophilization (8 mg, 0.010 mmol, 25%). $^1H$ NMR (500 MHz, $CD_3OD$): δ 7.78 (d, J=8.9 Hz, 2H, $(SO_2C(CH)_2)$, 7.437.35 (m, 4H, Ar), 7.11 (d, J=8.9 Hz, 2H, $(CH)_2COCH_3$), 5.62 (d, J=5.2 Hz, 1H, OCHO), 4.96-4.77 (m, 2H, $CH_2CHOC(O)$, POCHC), 4.21 (br s, 2H, $PhCH_2N$), 3.97-3.70 (m, 6H), 3.90 (s, 3H, $OCH_3$), 3.50-3.30 (m, 3H), 3.26-3.02 (m, 2H), 2.94-2.58 (m, 4H), 2.09-1.78 (m, 5H), 1.63-1.52 (m, 2H), 1.05-0.97 (m, 3H); 0.94 (d, J=6.7 Hz, 3H), 0.88 (d, J=6.7 Hz, 3H); $^{31}P$ NMR (121 MHz, $CD_3OD$): δ 20.8.

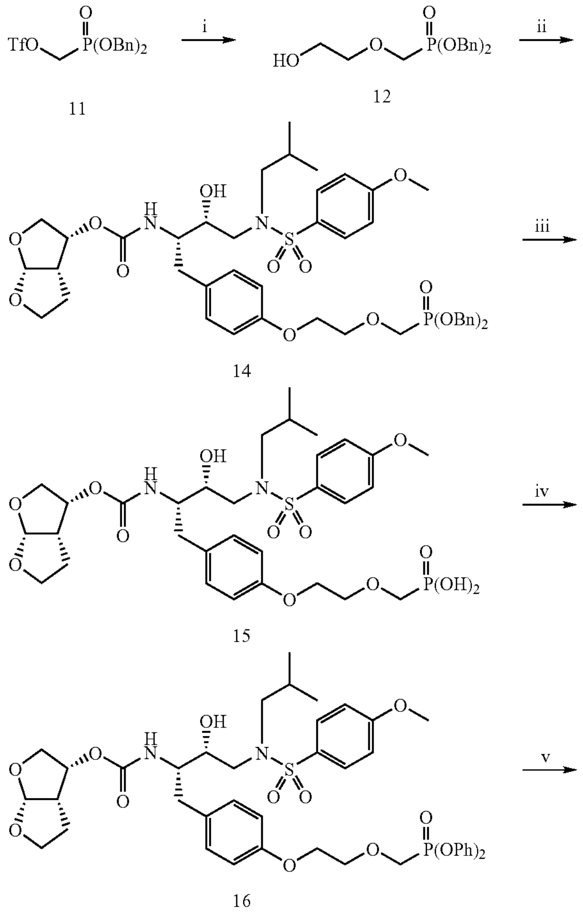

11

12

14

15

16

-continued

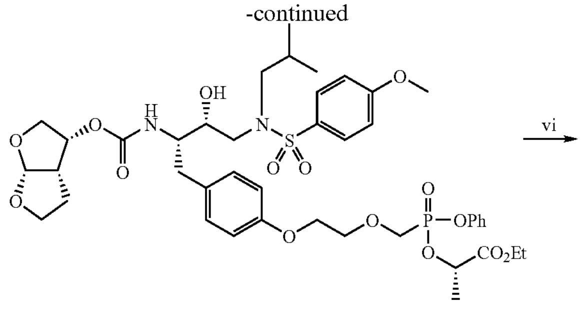

17

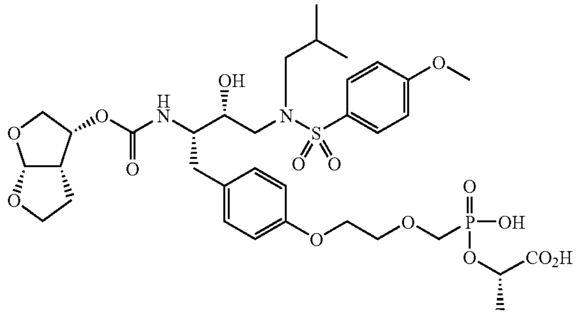

18

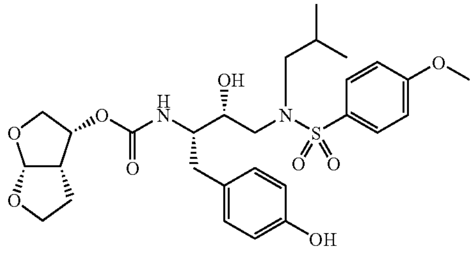

13

Reagents and conditions:
i. ehtylene glycol, $Mg(OtBu)_2$, DMF, 48%;
ii. a. $Tf_2O$, 2,6-lutidine, $CH_2Cl_2$, -78° C.; b. $CsCO_3$, $CH_3CN$, 0° C. to room temperature, 65%;
iii. $H_2$, Pd/C, EtOH, 107%;
iv. DCC, PhOH, pyr, 70° C., 31%;
v. a. NaOH, $CH_3CN$, 0° C.; b. DCC, ethyl lactate, pyr, 70° C., 52%;
vi. $CH_3CN$, DMSO, PBS, porcine liver esterase, 38° C., 69%.

Example 9

Compound 12: To a solution of compound 11 (4.10 g, 9.66 mmol) and anhydrous ethylene glycol (5.39 mL, 96.6 mmol) in anhydrous DMF (30 mL) at 0° C. was added powdered magnesium tert-butoxide (2.05 g, 12.02 mmol). The reaction mixture was stirred at 0° C. for 1.5 h, then concentrated. The residue was partitioned between EtOAc and $H_2O$ and washed with 1 N HCl, saturated $NaHCO_3$ solution, and brine. Organic layer dried ($MgSO_4$), concentrated and purified (silica gel, 4% MeOH/$CH_2Cl_2$) to give a colorless oil (1.55 g, 48%). $^1$H NMR (300 MHz, $CDCl_3$): δ 7.37 (s, 10H, Ar), 5.40-5.05 (m, 4H, $CH_2Ph$), 3.84 (d, J=8.1 Hz, 2H, $PCH_2O$), 3.70-3.60 (m, 4H, $OCH_2CH_2O$, $OCH_2CH_2O$); $^{31}$P NMR (121 MHz, $CDCl_3$): δ 22.7.

Example 10

Compound 14: To a solution of compound 12 (0.75 g, 2.23 mmol) and 2,6-lutidine (0.78 mL, 6.69 mmol) in $CH_2Cl_2$ (20 mL) at −78° C. was added trifluoromethanesulfonic anhydride (0.45 mL, 2.68 mmol). The reaction mixture was stirred at −78° C. for 40 min, then diluted with $CH_2Cl_2$ and washed with 1 N HCl, saturated $NaHCO_3$ and dried ($MgSO_4$). Concentration gave a yellow oil that was dissolved in anhydrous acetonitrile (20 mL). Phenol 13 (1.00 g, 1.73 mmol) was added to the solution, which was cooled to 0° C. Cesium carbonate (0.619 g, 1.90 mmol) was added and reaction mixture was stirred at 0° C. for 2 h, then at room temperature for 1.5 h. Additional cesium carbonate (0.200 g, 0.61 mmol) was added and reaction was continued for 1.5 h, then filtered. Concentration of the filtrate and purification (silica gel, 3% MeOH/$CH_2Cl_2$) gave a yellow gum (1.005 g, 65%). $^1$H NMR (300 MHz, $CDCl_3$): δ 7.71 (d, J=8.7 Hz, 2H, $SO_2C(CH)_2$), 7.34 (s, 10H, $PhCH_2O$), 7.11 (d, J=8.1 Hz, 2H, $CH_2C(CH)_2(CH)_2$), 6.98 (d, J=8.7 Hz, 2H, $(CH)_2COCH_3$), 6.78 (d, J=8.7 Hz, 2H, $(CH)_2COCH_2$), 5.62 (d, J=5.4 Hz, 1H, OCHO), 5.16-4.97 (m, 6H), 4.05-3.65 (m, 12H), 3.86 (s, 3H, $OCH_3$), 3.19-2.66 (m, 7H), 1.95-1.46 (m, 3H), 0.92 (d, J=6.6 Hz, 3H, $CH(CH_3)_2$), 0.88 (d, J=6.6 Hz, 3H, $CH(CH_3)_2$); $^{31}$P NMR (121 MHz, $CDCl_3$): δ 21.9.

Example 11

Compound 15: A mixture of compound 14 (0.410 g, 0.457 mmol) and 10% palladium on carbon (0.066 g) in ethanol (5.0 mL) was stirred under a hydrogen atmosphere (1 atm) for 16 h. Celite was added and the mixture was stirred for 5 min, then filtered through Celite and concentrated to give a foam (0.350 g, 107%). $^1$H NMR (300 MHz, $CD_3OD$): δ 7.76 (d, J=8.7 Hz, 2H, $SO_2C(CH)_2$), 7.15 (d, J=8.4 Hz, 2H, $CH_2C(CH)_2(CH)_2$), 7.08 (d, J=8.4 Hz, 2H, $(CH)_2COCH_3$), 6.82 (d, J=8.4 Hz, 2H, $(CH)_2COCH_2$), 5.59 (d, J=5.4 Hz, 1H, OCHO), 5.16-4.97 (masked by $CD_3OH$, 1H), 4.09-4.02 (m, 2H), 3.99-3.82 (m, 10H), 3.88 (s, 3H, $OCH_3$), 3.52-3.32 (m, 1H), 3.21-2.75 (m, 5H), 2.55-2.40 (m, 1H), 2.10-1.95 (m, 1H), 1.75-1.25 (m, 2H), 0.93 (d, J=6.3 Hz, 3H, $CH(CH_3)_2$), 0.88 (d, J=6.6 Hz, 3H, $CH(CH_3)_2$); $^{31}$P NMR (121 MHz, $CD_3OD$): δ 19.5.

Example 12

Compound 16: Compound 15 (0.350 g, 0.488 mmol) was coevaporated with anhydrous pyridine (3×10 mL), each time filling with $N_2$. Residue was dissolved in anhydrous pyridine (2.5 mL) and phenol (0.459 g, 4.88 mmol) was added. This solution was heated to 70° C., then 1,3-dicyclohexylcarbodiimide (0.403 g, 1.93 mmol) was added and reaction mixture was heated at 70° C. for 7 h. Reaction mixture was concentrated, coevaporated with toluene and residue obtained was diluted with EtOAc, precipitating 1,3-dicyclohexylurea. The mixture was filtered and filtrate concentrated and residue obtained was purified (silica gel, 2% MeOH/$CH_2Cl_2$, then another column 75% EtOAc/Hex) to give a clear oil (0.1324 g, 31%). $^1$H NMR (300 MHz, $CDCl_3$): δ 7.71 (d, J=8.7 Hz, 2H, $SO_2C(CH)_2$), 7.41-7.18 (m, 10H, Ar), 7.14 (d, J=8.4 Hz, 2H, $CH_2C(CH)_2(CH)_2$), 6.99 (d, J=9.0 Hz, 2H, $(CH)_2COCH_3$), 6.83 (d, J=8.4 Hz, 2H, $(CH)_2COCH_2$), 5.64 (d, J=5.1 Hz, 1H, OCHO), 5.16-4.92 (m, 2H), 4.32-3.62 (m, 12H), 3.87 (s, 3H, $OCH_3$), 3.22-2.73 (m, 7H), 1.95-1.75 (m, 3H), 0.93 (d, J=6.6 Hz, 3H, $CH(CH_3)_2$), 0.88 (d, J=6.6 Hz, 3H, $CH(CH_3)_2$); $^{31}$P NMR (121 MHz, $CDCl_3$): δ 14.3.

Example 13

Compound 17: To a solution of compound 16 (0.132 g, 0.152 mmol) in acetonitrile (1.5 mL) at 0° C. was added 1.0 M NaOH (0.38 mL, 0.381 mmol). Reaction mixture was stirred for 2 h at 0° C., then Dowex 50 (H+) resin was added until pH=1. The resin was removed by filtration and the filtrate was concentrated and washed with EtOAc/Hex (1:2, 25 mL), then dried under high vacuum to give a clear film (0.103 g, 85%). This film was co-evaporated with anhydrous pyridine (3×5 mL), filling with $N_2$. The residue was dissolved in anhydrous pyridine (1 mL) and ethyl lactate (0.15 mL, 1.30 mmol) was added and reaction mixture was heated at 70° C. After 5 min, 1,3-dicyclohexylcarbodiimide (0.107 g, 0.520 mmol) was added and reaction mixture was stirred at 70° C. for 2.5 h. Additional 1,3-dicyclohexylcarbodiimide (0.055 g, 0.270 mmol) was added and reaction continued for another 1.5 h. Reaction mixture was concentrated and coevaporated with toluene and diluted with EtOAc, precipitating 1,3-dicyclohexylurea. The mixture was filtered and filtrate concentrated and residue obtained was purified (silica gel, 80 to 100% EtOAc/Hex) to give a white foam (0.0607 g, 52%). $^1$H NMR (300 MHz, $CDCl_3$): δ 7.71 (d, J=8.7 Hz, 2H, $SO_2C(CH)_2$), 7.39-7.16 (m, 5H. Ar), 7.13 (d, J=8.1 Hz, 2H, $CH_2C(CH)_2(CH)_2$), 6.99 (d, J=9.0 Hz, 2H, $(CH)_2COCH_3$), 6.82 (d, J=8.4 Hz, 2H, $(CH)_2COCH_2$), 5.64 (d, J=5.1 Hz, 1H, OCHO), 5.16-4.92 (m, 3H), 4.353.65 (m, 14H), 3.87 (s, 3H, $OCH_3$), 3.22-2.73 (m, 7H), 1.95-1.80 (m, 3H), 1.59 (d, J=6.9 Hz, 1.5H, $CCHCH_3$), 1.47 (d, J=7.2 Hz, 1.5H, $CCHCH_3$), 1.37-1.18 (m, 3H), 0.92 (d, J=6.6 Hz, 3H, $CH(CH_3)_2$), 0.88 (d, J=6.6 Hz, 3H, $CH(CH_3)_2$); $^{31}$P NMR (121 MHz, $CDCl_3$): δ 19.2, 17.2.

Example 14

Compound 18: Compound 17 (11.5 mg, 0.013 mmol) was dissolved in DMSO (0.14 mL) and acetonitrile (0.29 mL). PBS (pH 7.4, 1.43 mL) was added slowly with stirring. Porcine liver esterase (Sigma, 0.1 mL) was added and reaction mixture was gently stirred at 38° C. After 24 h, additional porcine liver esterase (0.1 mL) and DMSO (0.14 mL) were added and reaction mixture stirred for 48 h at 38° C. Reaction mixture concentrated and methanol was added to precipitate the enzyme. The mixture was filtered, concentrated and purified by reverse phase chromatography to give a white powder after lyophilization (7.1 mg, 69%). $^1$H NMR (300 MHz, $CD_3OD$): δ 7.76 (d, J=8.7 Hz, 2H, $SO_2C(CH)_2$), 7.15 (d, J=8.4 Hz, 2H, $CH_2C(CH)_2(CH)_2$), 7.08 (d, J=9.0 Hz, 2H, $(CH)_2COCH_3$), 6.83 (d, J=8.7 Hz, 2H, $(CH)_2COCH_2$), 5.59 (d, J=5.1 Hz, 1H, OCHO), 5.16-4.90 (masked by $CD_3OH$, 2H), 4.193.65 (m, 12H), 3.88 (s, 3H, $OCH_3$), 3.50-3.27 (m, 1H), 3.20-2.78 (m, 5H), 2.55-2.40 (m, 1H), 2.05-1.90 (m, 1H), 1.75-1.30 (m, 2H), 1.53 (d, J=6.6 Hz, 3H, $CCHCH_3$), 0.93 (d, J=6.6 Hz, 3H, $CH(CH_3)_2$), 0.88 (d, J=6.6 Hz, 3H, $CH(CH_3)_2$); $^{31}$P NMR (121 MHz, $CD_3OD$): δ 16.7.

Alternatively, compound 17 was prepared as described below (Scheme 3).

Scheme 3

14

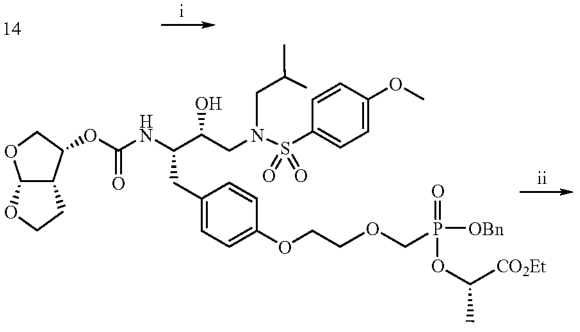

19

17

Reagents and conditions:
i. a. 14, DABCO, tol, reflux, b. ethyl lactate, PyBOP, DIPEA, DMF, 59%;
ii. a. $H_2$, Pd/C, EtOH; b. PhOH, PyBOP, DIPEA, DMF, 35%.

Example 15

Compound 19: To a solution of compound 14 (0.945 g, 1.05 mmol) in anhydrous toluene (10.0 mL) was added 1,4-diazobicyclo[2.2.2]octane (0.130 g, 1.16 mmol) and reaction mixture was refluxed for 2 h. After cooling to room temperature, reaction mixture was diluted with EtOAc and washed with 1.0 N HCl and dried ($MgSO_4$). Concentration gave a white foam (0.785 g, 93%). Residue was dissolved in anhydrous DMF (10.0 mL) and to this solution was added ethyl (S)-lactate (0.23 mL, 2.00 mmol) and diisopropylethylamine (0.70 mL, 4.00 mmol), followed by benzotriazol-1-yloxytripyrroldinophosphonium hexafluorophosphate (1.041 g, 2.00 mmol). Reaction mixture was stirred for 20 h, then concentrated and residue was dissolved in EtOAc and washed with 1.0 N HCl, saturated $NaHCO_3$, brine and dried ($MgSO_4$). Concentration and purification (silica gel, 2% $MeOH/CH_2Cl_2$) gave an off-white foam (0.520 g, 59%). $^1$H NMR (300 MHz, $CDCl_3$): δ 7.72 (d, J=7.5 Hz, 2H, $SO_2C(CH)_2$), 7.50-7.27 (m, 4H, Ar), 7.12 (d, J=8.1 Hz, 2H, $CH_2C(CH)_2(CH)_2$), 7.00 (d, J=6.6 Hz, 2H, $(CH)_2COCH_3$), 6.81 (d, J=8.4 Hz, 2H, $(CH)_2COCH_2$), 5.64 (d, J=5.1 Hz, 1H, OCHO), 5.37-4.90 (m, 5H), 4.35-3.65 (m, 14H), 3.88 (s, 3H, $OCH_3$), 3.24-2.70 (m, 7H), 1.90-1.70 (m, 3H), 1.54 (d, J=6.9 Hz, 1.5H, $CCHCH_3$), 1.47 (d, J=6.9 Hz, 1.5H, $CCHCH_3$), 1.37-1.22 (m, 3H), 0.93 (d, J=6.3 Hz, 3H, $CH(CH_3)_2$), 0.89 (d, J=6.0 Hz, 3H, $CH(CH_3)_2$); $^{31}$P NMR (121 MHz, $CDCl_3$): δ 22.3, 21.2.

Example 16

Compound 17: A mixture of compound 19 (0.520 g, 0.573 mmol) and 10% palladium on carbon (0.055 g) in ethanol (10 mL) was stirred under a hydrogen atmosphere (1 atm) for 2 h. Celite was added to the reaction mixture and stirred for 5 min, then mixture was filtered through Celite and concentrated to give a white foam (0.4649 g, 99%). Residue was dissolved in anhydrous DMF (5.0 mL) and to this solution was added phenol (0.097 g, 1.03 mmol), diisopropylethylamine (0.36 mL, 2.06 mmol) followed by benzotriazol-1-yloxytripyrroldinophosphonium hexafluorophosphate (0.536 g, 1.03 mmol). Reaction mixture was stirred for 20 h, then concentrated and residue was dissolved in EtOAc and washed with 1 N HCl, $H_2O$, sat. $NaHCO_3$, brine and dried ($MgSO_4$). Concentration and purification (silica gel, 2% $MeOH/CH_2Cl_2$) gave a white foam (0.180 g, 35%).

Scheme 4

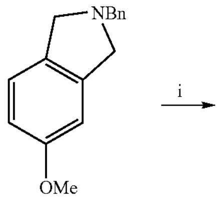

20

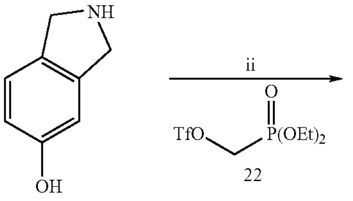

22

21

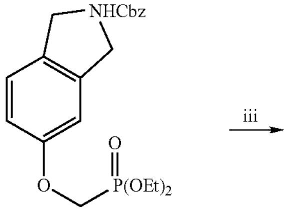

23

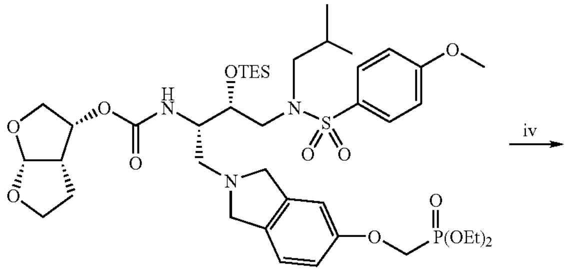

25

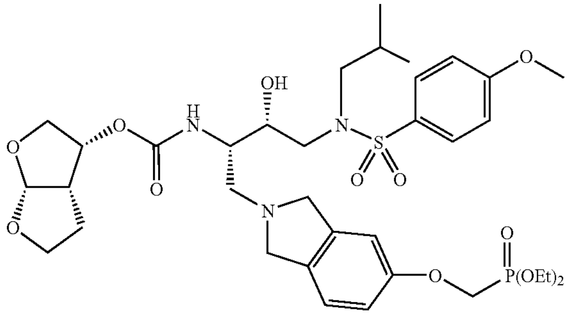

26

-continued

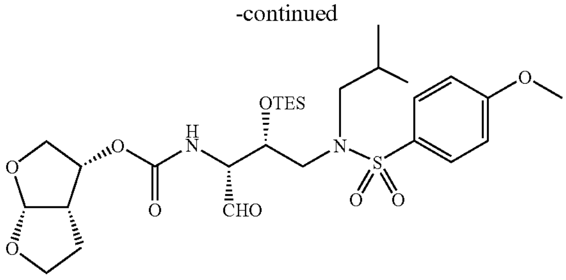

24

Reagents and conditions:
i. a. 48% HBr, 120° C., 65%; b. $H_2$, $Pd(OH)_2$, EtOH, 100%;
ii. CbzCl, NaOH, tol/$H_2O$, 0° C. to rt, 43%; b. 22, $CsCO_3$, $CH_3CN$, 99%;
iii. a. $H_2$, Pd/C, AcOH, EtOAc/EtOH, 95%; b. 24, $NaBH(OAc)_3$, 1,2-DCE, 21%;
iv, 4% $HF/CH_3CN$, 62%.

Example 17

Compound 21: Compound 20 (11.5 g, 48.1 mmol) in 48% HBr (150 mL) was heated at 120° C. for 4 h, then cooled to room temperature and diluted with EtOAc. Mixture was neutralized with saturated $NaHCO_3$ solution and solid $NaHCO_3$ and extracted with EtOAc containing MeOH. Organic layer dried ($MgSO_4$), concentrated, and purified (silica gel, 1:2 EtOAc/Hex with 1% MeOH) to give a brown solid (7.0 g, 65%). The resulting compound (7.0 g, 31.1 mmol) and 10% palladium hydroxide (2.1 g) in EtOH (310 mL) was stirred under a hydrogen atmosphere for 1 d, then filtered through Celite and concentrated to give an off-white solid (4.42 g, 100%). $^1H$ NMR (300 MHz, $CDCl_3$): δ 7.01 (d, J=7.8 Hz, 1H, Ar), 6.64 (s, 1H, Ar), 6.61 (d, J=8.1 Hz, 2H, Ar), 4.07 (s, 2H, $ArCH_2N$), 4.05 (s, 2H, $ArCH_2N$).

Example 18

Compound 22: To a solution of compound 21 (4.42 g, 32.7 mmol) in 1.0 M NaOH (98 mL, 98.25 mmol) at 0° C. was added dropwise benzyl chloroformate (7.00 mL, 49.13 mmol) in toluene (7 mL). After addition was complete, reaction mixture was stirred overnight at room temperature. Reaction mixture was diluted with EtOAc and extracted with EtOAc (3×). Combined organic layer was dried ($MgSO_4$), concentrated and purified (silica gel, 2% $MeOH/CH_2Cl_2$) to give a white solid (3.786 g, 43%). The resulting compound (0.6546 g, 2.43 mmol) was dissolved in anhydrous acetonitrile (10 mL), and compound 23 (0.782 g, 2.92 mmol) was added, followed by cesium carbonate (1.583 g, 4.86 mmol). Reaction mixture was stirred for 2 h at room temperature, then filtered, concentrated, and purified (3% $MeOH/CH_2Cl_2$) to give a brownish oil (1.01 g, 99%).

Example 19

Compound 25: To a solution of compound 22 (0.100 g, 0.238 mmol) in EtOAc/EtOH (2 mL, 1:1) was added acetic acid (14 μL, 0.238 mmol) and 10% palladium on carbon (0.020 g) and the mixture was stirred under a hydrogen atmosphere for 2 h. Celite was added to the reaction mixture and stirred for 5 min, then filtered through Celite. Concentration and drying under high vacuum gave a reddish film (0.0777 g, 95%). The resulting amine (0.0777 g, 0.225 mmol) and aldehyde 24 (0.126 g, 0.205 mmol) in 1,2-dichloroethane (1.2 mL) were stirred for 5 min at 0° C., then sodium triacetoxyborohydride (0.0608 g, 0.287 mmol) was added. Reaction mixture was stirred for 1 h at 0° C., then quenched with saturated $NaHCO_3$ solution and brine. Extracted with EtOAc, the organic layer was dried ($MgSO_4$), concentrated and purified (silica gel, 2% $MeOH/CH_2Cl_2$) to give a brown foam (38.7 mg, 21%). $^1H$ NMR (300 MHz, $CDCl_3$): δ 7.74 (d, J=8.7 Hz, 2H, Ar), 7.09 (d, J=8.7 Hz, 1H, Ar), 7.05-6.72 (m, 4H, Ar), 5.71 (d, J=5.1 Hz, 1H), 5.22-5.07 (m, 2H), 4.22-4.17 (m, 7H), 4.16-3.69 (m, 9H), 3.82 (s, 3H), 3.25-2.51 (m, 7H), 2.22-1.70 (m, 3H), 1.37 (t, J=6.9 Hz, 6H), 1.10-0.58 (m, 21H); $^{31}P$ NMR (121 MHz, $CDCl_3$): δ 19.5.

Example 20

Compound 26: To a solution of compound 25 (38.7 mg, 0.0438 mmol) in acetonitrile (0.5 mL) at 0° C. was added 48% HF (0.02 mL). The reaction mixture was stirred at room temperature for 2 h, then quenched with saturated $NaHCO_3$ solution and extracted with EtOAc. Organic layer was separated, dried ($MgSO_4$), concentrated and purified (silica gel, 3 to 5% $MeOH/CH_2Cl_2$) to give a red film (21.2 mg, 62%). $^1H$ NMR (300 MHz, $CDCl_3$): δ 7.73 (d, J=8.7 Hz, 2H, Ar), 7.10 (d, J=8.7 Hz, 1H, Ar), 6.97 (d, J=8.70 Hz, 2H), 6.90-6.76 (m, 2H), 5.72 (d, J=5.1 Hz, 1H), 5.41 (d, J=9.0 Hz, 1H), 5.15 (q, J=6.6 Hz, 1H), 4.38-4.17 (m, 7H), 4.16-3.65 (m, 9H), 3.87 (s, 3H), 3.20-2.82 (m, 7H), 2.75-1.79 (m, 3H), 1.37 (t, J=6.9 Hz, 6H), 0.90 (d, J=6.6 Hz, 3H), 0.88 (d, J=6.6 Hz, 3H); $^{31}P$ NMR (121 MHz, $CDCl_3$): 819.3.

Scheme 5

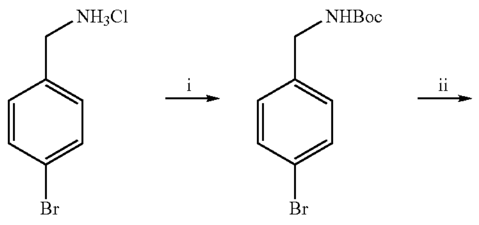

27 28

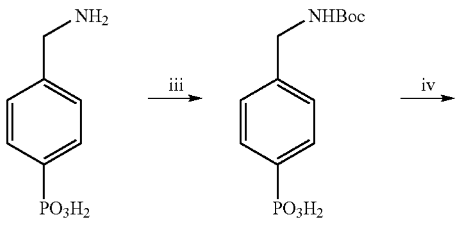

29 30

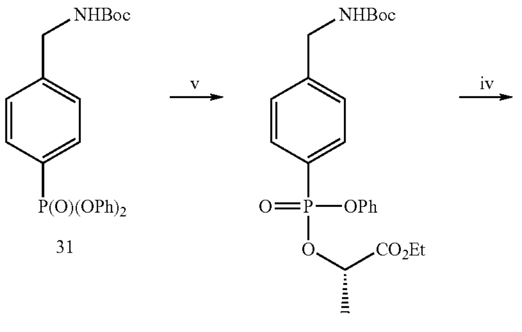

31 32

-continued

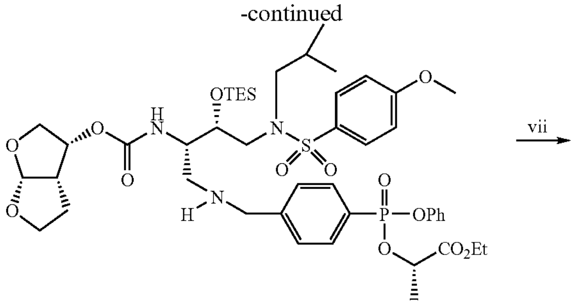

33

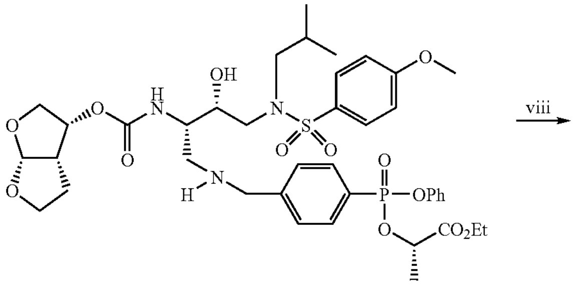

34

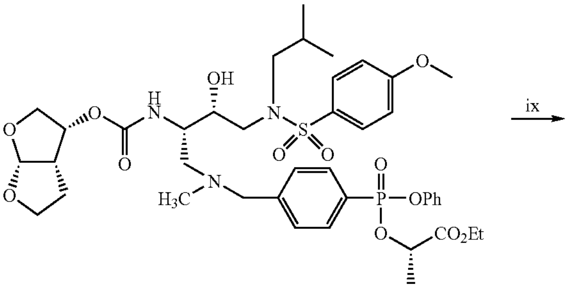

35

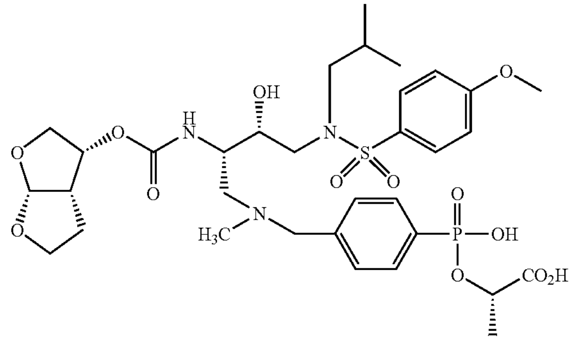

36

Reagents and conditions:
i. $Boc_2O$, NaOH, $H_2O$, 96%;
ii. a. $HP(OEt)_2$, $Et_3N$, $(PPh_3)_4Pd$, 90° C., b. TMSBr, $CH_3CN$, 65%;
iii. $Boc_2O$, NaOH, $THF/H_2O$, 89%; iv. PhOH, DCC, pyr. 70° C., 71%;
v. a. NaOH, $CH_3CN$, 94%; b. Et lactate, DCC, pyr, 70°C., 80%;
vi. a. TFA, $CH_2Cl_2$; b. 24, AcOH, $NaBH_3CN$, EtOH, 33%;
vii. 4% $HF/CH_3CN$, 88%;
viii. HCHO, AcOH, $NaBH_3CN$, EtOH, 67%;
ix. $CH_3CN$, DMSO, PBS, porcine liver esterase, 38° C., 21%.

Example 21

Compound 28: To a mixture of 4-bromobenzylamine hydrochloride (15.23 g, 68.4 mmol) in $H_2O$ (300 mL) was added sodium hydroxide (8.21 g, 205.2 mmol), followed by di-tert-butyl dicarbonate (16.45 g, 75.3 mmol). Reaction mixture was vigorously stirred for 18 h, then diluted with EtOAc (500 mL). Organic layer separated and aqueous layer extracted with EtOAc (200 mL). Combined organic layer was dried (MgSO$_4$), concentrated and dried under high vacuum to give a white solid (18.7 g, 96%). $^1$H NMR (300 MHz, CDCl$_3$): δ 7.41 (d, J=8.4 Hz, 2H), 7.12 (d, J=8.3 Hz, 2H), 4.82 (s, 1H, NH), 4.22 (d, J=6.1 Hz, 2H), 1.41 (s, 9H).

Example 22

Compound 29: Compound 28 (5.00 g, 17.47 mmol) was coevaporated with toluene. Diethyl phosphite (11.3 mL, 87.36 mmol) was added and mixture was coevaporated with toluene (2×). Triethylamine (24.0 mL, 174.7 mmol) was added and mixture was purged with argon for 10 min, then tetrakis(triphenylphosphine)palladium(0) (4.00 g, 3.49 mmol) was added. Reaction mixture was refluxed for 18 h, cooled, concentrated and diluted with EtOAc. Washed with 0.5 N HCl, 0.5 M NaOH, H$_2$O, brine and dried (MgSO$_4$). Concentrated and purification (silica gel, 70% EtOAc/Hex) gave an impure reaction product as a yellow oil (6.0 g). This material (6.0 g) was dissolved in anhydrous acetonitrile (30 mL) and cooled to 0° C. Bromotrimethylsilane (11.5 mL, 87.4 mmol) was added and reaction mixture was warmed to room temperature over 15 h. Reaction mixture was concentrated, dissolved in MeOH (50 mL) and stirred for 1.5 h. H$_2$O (1 mL) was added and mixture stirred for 2 h. Concentrated to dryness and dried under high vacuum, then triturated with Et$_2$O containing 2% MeOH to give a white solid (3.06 g, 65%). $^1$H NMR (300 MHz, D$_2$O): δ 7.67 (dd, J=12.9, 7.6 Hz, 2H), 7.45-7.35 (m, 2H), 4.10 (s, 2H); $^{31}$P NMR (121 MHz, D$_2$O): δ 12.1.

Example 23

Compound 30: Compound 29 (4.78 g, 17.84 mmol) was dissolved in H$_2$O (95 mL) containing sodium hydroxide (3.57 g, 89.20 mmol). Di-tert-butyl dicarbonate (7.63 g, 34.94 mmol) was added, followed by THF (25 mL). The clear reaction mixture was stirred overnight at room temperature then concentrated to ~100 mL. Washed with EtOAc and acidified to pH 1 with 1 N HCl and extracted with EtOAc (7×). Combined organic layer was dried (MgSO$_4$), concentrated and dried under high vacuum. Trituration with Et$_2$O gave a white powder (4.56 g, 89%). $^1$H NMR (300 MHz, CD$_3$OD): δ 7.85-7.71 (m, 2H), 7.39-7.30 (m, 2H), 4.26 (s, 2H), 1.46 (s, 9H); $^{31}$P NMR (121 MHz, CD$_3$OD): δ 16.3.

Example 24

Compound 31: Compound 30 (2.96 g, 10.32 mmol) was coevaporated with anhydrous pyridine (3×10 mL). To this residue was added phenol (9.71 g, 103.2 mmol) and mixture was coevaporated with anhydrous pyridine (2×10 mL). Pyridine (50 mL) was added and solution heated to 70° C. After 5 min, 1,3-dicyclohexylcarbodiimide (8.51 g, 41.26 mmol) was added and resulting mixture was stirred for 8 h at 70° C. Reaction mixture was cooled and concentrated and coevaporated with toluene. Residue obtained was diluted with EtOAc and the resulting precipitate was removed by filtration. The filtrate was concentrated and purified (silica gel, 20 to 40% EtOAc/Hex, another column 30 to 40% EtOAc/Hex) to give a white solid (3.20 g, 71%). $^1$H NMR (300 MHz, CDCl$_3$): δ 7.90 (dd, J=13.8, 8.2 Hz, 2H), 7.41-7.10 (m, 14H), 5.17 (brs, 1H, NH), 4.35 (d, J=5.2 Hz, 2H), 1.46(s, 9H); $^{31}$P NMR (121 MHz, CDCl$_3$): δ 11.8.

Example 25

Compound 32: To a solution of compound 31 (3.73 g, 8.49 mmol) in acetonitrile (85 mL) at 0° C. was added 1 M NaOH (21.2 mL, 21.21 mmol). Reaction mixture was stirred at 0° C. for 30 min, then warmed to room temperature over 4 h. Reaction mixture cooled to 0° C. and Dowex (H+) residue was added to pH 2. Mixture was filtered, concentrated and residue obtained was triturated with EtOAc/Hex (1:2) to give a white powder (2.889 g, 94%). This compound (2.00 g, 5.50 mmol) was coevaporated with anhydrous pyridine (3×10 mL). The residue was dissolved in anhydrous pyridine (30 mL) and ethyl(S)-lactate (6.24 mL, 55 mmol) and reaction mixture was heated to 70° C. After 5 min, 1,3-dicyclocarbodiiimide (4.54 g, 22.0 mmol) was added. Reaction mixture was stirred at 70° C. for 5 h, then cooled and concentrated. Residue was dissolved in EtOAc and precipitate was removed by filtration. The filtrate was concentrated and purified (25 to 35% EtOAc/Hex, another column 40% EtOAc/Hex) to give a colorless oil (2.02 g, 80%). $^1$H NMR (300 MHz, CDCl$_3$): δ 7.96-7.85 (m, 2H), 7.42-7.35 (m, 2H), 7.35-7.08 (m, 4H), 5.16-5.00 (m, 1H), 4.93 (s, 1H, NH), 4.37 (d, J=5.5 Hz, 1H), 4.21 (q, J=7.3 Hz, 1H), 4.11 (dq, J=5.7, 2.2 Hz, 1H), 1.62-1.47 (m, 3H), 1.47 (s, 9H), 1.27 (t, J=7.3 Hz, 1.5H), 1.17 (t, J=7.3 Hz, 1.5H); $^{31}$P NMR (121 MHz, CDCl$_3$): δ 16.1, 15.0.

Example 26

Compound 33: Compound 32 (2.02 g, 4.36 mmol) was dissolved in CH$_2$Cl$_2$ (41 mL) and cooled to 0° C. To this solution was added trifluoroacetic acid (3.5 mL) and reaction mixture was stirred at 0° C. for 1 h, then at room temperature for 3 h. Reaction mixture was concentrated, coevaporated with EtOAc and diluted with H$_2$O (400 mL). Mixture was neutralized with Amberlite IRA-67 weakly basic resin, then filtered and concentrated. Coevaporation with MeOH and dried under high vacuum to give the TFA amine salt as a semi-solid (1.48 g, 94%). To a solution of the amine (1.48 g, 4.07 mmol) in absolute ethanol (20 mL) at 0° C. was added aldehyde 24 (1.39 g, 2.26 mmol), followed by acetic acid (0.14 mL, 2.49 mmol). After stirring for 5 min, sodium cyanoborohydride (0.284 g, 4.52 mmol) was added and reaction mixture stirred for 30 min at 0° C. Reaction was quenched with saturated NaHCO$_3$ solution and diluted with EtOAc and H$_2$O. Aqueous layer was extracted with EtOAc (3×) and combined organic layer was dried (MgSO$_4$), concentrated and purified (silica gel, 2 to 4% MeOH/CH$_2$Cl$_2$) to give white foam (0.727 g, 33%). $^1$H NMR (300 MHz, CDCl$_3$): δ 7.98-7.86 (m, 2H), 7.71 (d, J=8.6 Hz, 2H), 7.49 (br s, 2H), 7.38-7.05 (m, 5H), 6.98 (d, J=8.8 Hz, 2H), 5.72 (d, J=5.1 Hz, 1H), 5.28-5.00 (m, 2H), 4.30-3.72 (m, 12H), 3.42-3.58 (m, 1H), 3.20-2.68 (m, 7H), 2.25-1.42 (m, 6H), 1.26 (t, J=7.2 Hz, 1.5H), 1.17 (t, J=7.2 Hz, 1.5H), 1.08-0.50 (m, 21H); $^{31}$P NMR (121 MHz, CDCl$_3$): δ 16.1, 15.1.

Example 27

Compound 34: To a solution of compound 33 (0.727 g, 0.756 mmol) in acetonitrile (7.6 mL) at 0° C. was added 48% hydrofluoric acid (0.152 mL) and reaction mixture was stirred for 40 min at 0° C., then diluted with EtOAc and H$_2$O. Saturated NaHCO$_3$ was added and aqueous layer was extracted with EtOAc (2×). Combined organic layer was dried ($MgSO_4$), concentrated and purified (silica gel, 4 to 5% $MeOH/CH_2Cl_2$) to give a colorless foam (0.5655 g, 88%). $^1$H NMR (300 MHz, $CDCl_3$): δ 7.95-7.82 (m, 2H), 7.67 (d, J=8.1 Hz, 2H), 7.41 (br s, 2H), 7.38-7.05 (m, 5H), 6.95 (d, J=7.2 Hz, 2H), 5.76 (d, J=7.9 Hz, 1H), 5.67 (d, J=5.0 Hz, 1H), 5.32-4.98 (m, 2H), 4.25-3.75 (m, 13H), 3.25-2.70 (m, 7H), 2.15-1.76 (m, 3H), 1.53-1.41 (m, 3H), 1.25-1.08 (m, 3H), 0.87 (d, J=4.2 Hz, 6H); $^{31}$P NMR (121 MHz, $CDCl_3$): δ 16.1, 15.0.

Example 28

Compound 35: To a solution of compound 33 (0.560 g, 0.660 mmol) in absolute ethanol (13 mL) at 0° C. was added 37% formaldehyde (0.54 mL, 6.60 mmol), followed by acetic acid (0.378 mL, 6.60 mmol). The reaction mixture was stirred at 0° C. for 5 min, then sodium cyanoborohydride (0.415 g, 6.60 mmol) was added. Reaction mixture was warmed to room temperature over 2 h, then quenched with saturated $NaHCO_3$ solution. EtOAc was added and mixture was washed with brine. Aqueous layer was extracted with EtOAc (2×) and combined organic layer was dried ($MgSO_4$), concentrated and purified (silica gel, 3% $MeOH/CH_2Cl_2$) to give a white foam (0.384 g, 67%). $^1$H NMR (300 MHz, $CDCl_3$): δ 7.95-7.82 (m, 2H), 7.71 (d, J=8.4 Hz, 2H), 7.38 (br s, 2H), 7.34-7.10 (m, 5H), 6.98 (d, J=8.8 Hz, 2H), 5.72 (d, J=5.0 Hz, 1H), 5.50 (br s, 1H), 5.19-5.01 (m, 2H), 4.29-3.75 (m, 10H), 3.85 (s, 3H), 3.35-2.70 (m, 7H), 2.23 (s, 3H), 2.17-1.79 (m, 3H), 1.54 (d, J=6.9 Hz, 1.5H), 1.48 (d, J=6.8 Hz, 1.5H), 1.25 (t, J=7.2 Hz, 1.5H), 1.16 (t, J=7.2 Hz, 1.5H), 0.92 (d, J=6.6 Hz, 3H), 0.87 (d, J=6.6 Hz, 3H). $^{31}$P NMR (121 MHz, $CDCl_3$): δ 16.0, 14.8.

Example 29

Compound 36: To a solution of compound 35 (44 mg, 0.045 mmol) in acetonitrile (1.0 mL) and DMSO (0.5 mL) was added phosphate buffered saline (pH 7.4, 5.0 mL) to give a cloudy white suspension. Porcine liver esterase (200 μL) was added and reaction mixture was stirred for 48 h at 38° C. Additional esterase (600 μL) was added and reaction was continued for 4 d. Reaction mixture was concentrated, diluted with MeOH and the resulting precipitate removed by filtration. Filtrate was concentrated and purified by reverse phase HPLC to give a white powder after lyophilization (7.2 mg, 21%). $^1$H NMR (300 MHz, $CD_3OD$): δ 7.95 (br s, 2H), 7.76 (d, J=8.4 Hz, 2H), 7.64 (br s, 2H), 7.13 (d, J=8.7 Hz, 2H), 5.68 (d, J=5.1 Hz, 1H), 5.14 (br s, 1H), 4.77 (br s, 1H), 4.35-3.59 (m, 8H), 3.89 (s, 3H), 3.45-2.62 (m, 10H), 2.36-1.86 (m, 3H), 1.44 (d, J=6.3 Hz, 3H), 0.92 (d, J=6.6 Hz, 3H), 0.84 (d, J=6.6 Hz, 3H); $^{31}$P NMR (121 MHz, $CD_3OD$): δ 13.8.

Scheme 1

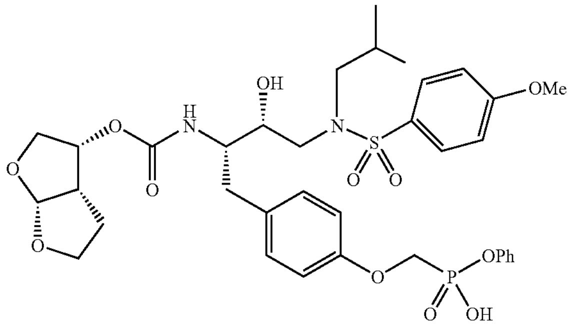

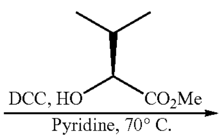

1

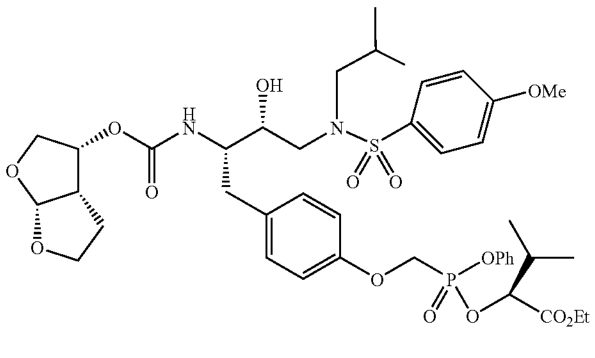

2
GS 192771

1

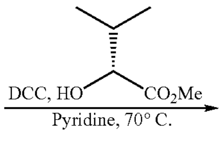

-continued
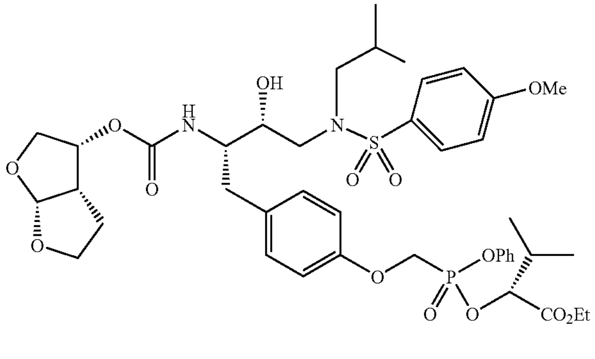
3
GS 192772
Scheme 2
1
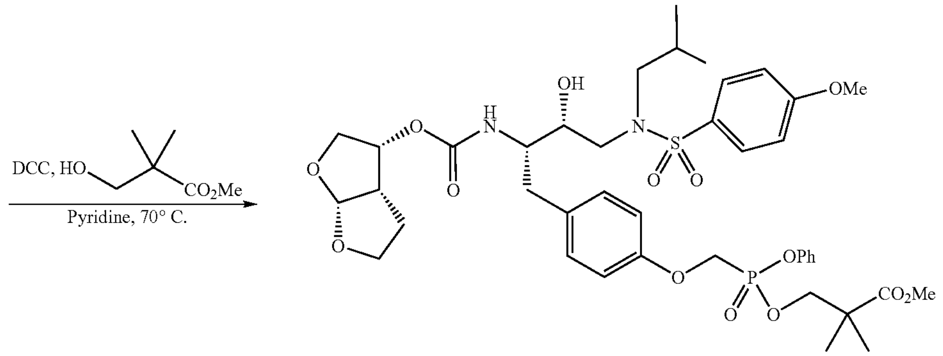
4
GS 191484
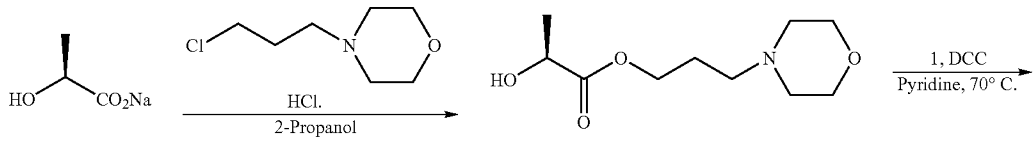
5
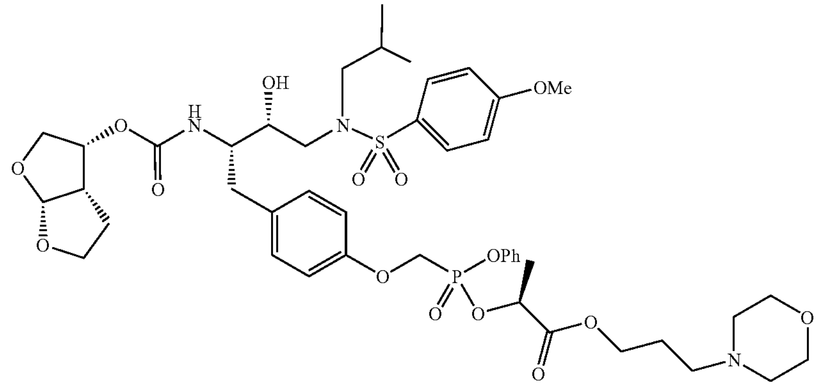
6
GS 192781

Scheme 3
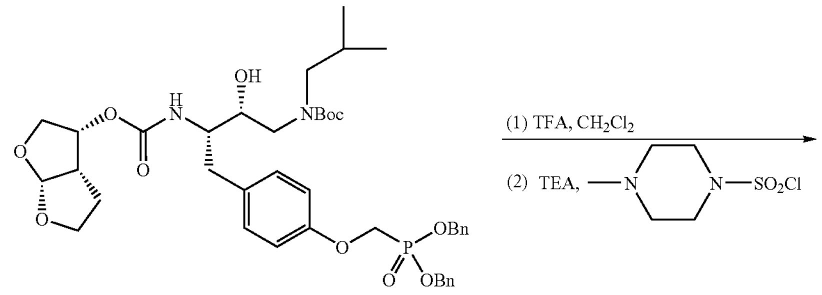
7
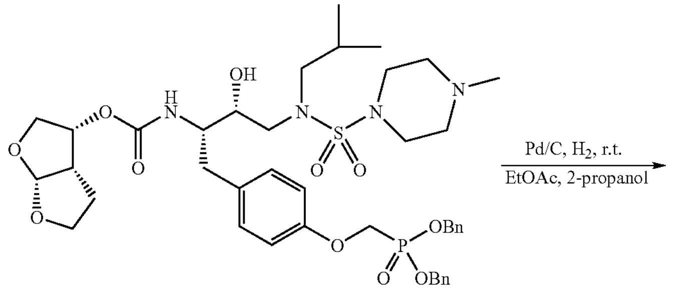
8
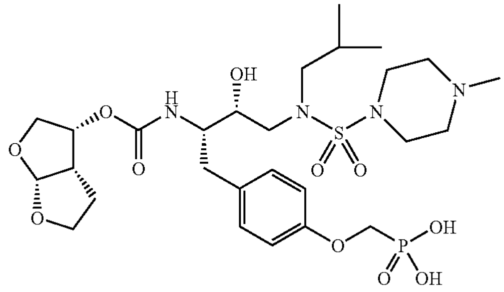
9
Scheme 4
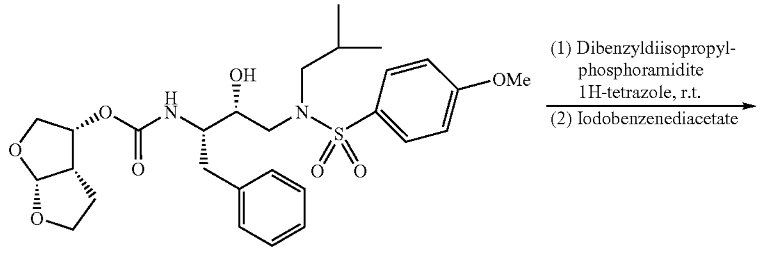
10

-continued
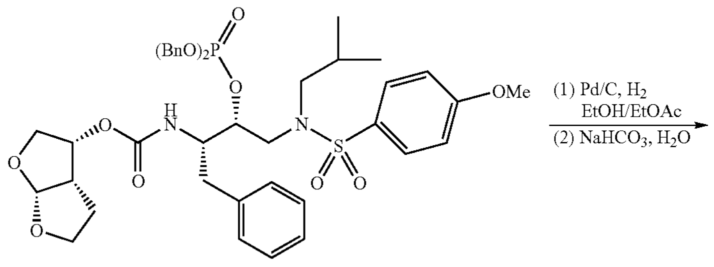
11
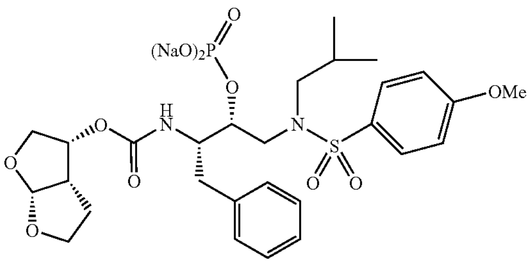
12
Scheme 5
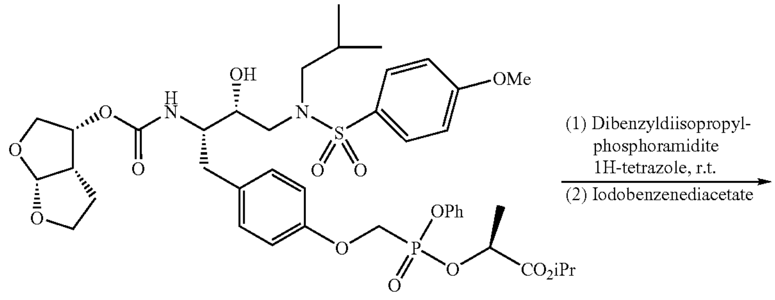
13
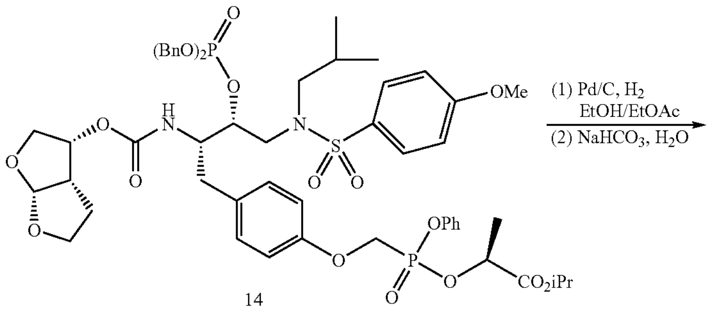
14

-continued

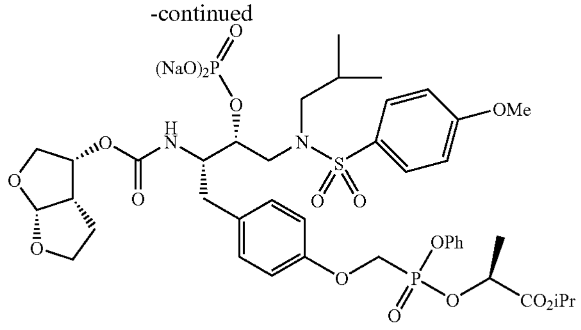

15
GS 273811

Example 1

Monophospholactate 2: A solution of 1 (0.11 g, 0.15 mmol) and α-hydroxyisovaleric acid ethyl-(S)-ester (71 mg, 0.49 mmol) in pyridine (2 mL) was heated to 70° C. and 1,3-dicyclohexylcarbodiimide (0.10 g, 0.49 mmol) was added. The reaction mixture was stirred at 70° C. for 2 h and cooled to room temperature. The solvent was removed under reduced pressure. The residue was suspended in EtOAc and 1,3-dicyclohexyl urea was filtered off. The product was partitioned between EtOAc and 0.2 N HCl. The EtOAc layer was washed with 0.2 N HCl, $H_2O$, saturated NaCl, dried with $Na_2SO_4$, filtered, and concentrated. The crude product was purified by column chromatography on silica gel (3% 2-propanol/$CH_2Cl_2$) to give the monophospholactate (35 mg, 28%, GS 192771, 1/1 diastereomeric mixture) as a white solid: $^1H$ NMR ($CDCl_3$) δ 7.71 (d, J=8.7 Hz, 2H), 7.36-7.14 (m, 7H), 6.99 (d, J=8.7 Hz, 2H), 6.94-6.84 (dd, 2H), 5.65 (d, J=5.4 Hz, 1H), 5.00-4.85 (m, 3H), 4.55 (dd, 1H), 4.41 (dd, 1H), 4.22-4.07 (m, 2H), 3.96-3.68 (m, 9H), 3.12-2.74 (m, 7H), 2.29 (m, 1H), 1.85-1.57 (m, 3H), 1.24 (m, 3H), 1.05 (d, J=6.6 Hz, 3H), 0.98 (d, J=6.6 Hz, 3H), 0.9 (m, 6H); $^{31}P$ NMR ($CDCl_3$) δ 17.7, 15.1.

Example 2

Monophospholactate 3: A solution of 1 (0.11 g, 0.15 mmol) and (X-hydroxyisovaleric acid ethyl-(R)-ester (71 mg, 0.49 mmol) in pyridine (2 mL) was heated to 70° C. and 1,3-dicyclohexylcarbodiimide (0.10 g, 0.49 mmol) was added. The reaction mixture was stirred at 70° C. for 2 h and cooled to room temperature. The solvent was removed under reduced pressure. The residue was suspended in EtOAc and 1,3-dicyclohexyl urea was filtered off. The product was partitioned between EtOAc and 0.2 N HCl. The EtOAc layer was washed with 0.2 N HCl, $H_2O$, saturated NaCl, dried with $Na_2SO_4$, filtered, and concentrated. The crude product was purified by column chromatography on silica gel (3% 2-propanol/$CH_2Cl_2$) to give the monophospholactate (35 mg, 28%, GS 192772, 1/1 diastereomeric mixture) as a white solid: $^1H$ NMR ($CDCl_3$) δ 7.71 (d, J=8.7 Hz, 2H), 7.35-7.13 (m, 7H), 6.98 (d, J=8.7 Hz, 2H), 6.93-6.83 (dd, 2H), 5.64 (d, J=5.4 Hz, 1H), 5.04-4.85 (m, 3H), 4.54 (dd, 1H), 4.39 (dd, 1H), 4.21-4.06 (m, 2H), 3.97-3.67 (m, 9H), 3.12-2.75 (m, 7H), 2.27 (m, 1H), 1.83-1.57 (m, 3H), 1.26 (m, 3H), 1.05 (d, J=6.6 Hz, 3H), 0.98 (d, J=6.6 Hz, 3H), 0.9 (m, 6H); $^{31}P$ NMR ($CDCl_3$) δ 17.7, 15.1.

Example 3

Monophospholactate 4: A solution of 1 (0.10 g, 0.13 mmol) and methyl-2,2-dimethyl-3-hydroxypropionate (56 μL, 0.44 mmol) in pyridine (1 mL) was heated to 70° C. and 1,3-dicyclohexylcarbodiimide (91 mg, 0.44 mmol) was added. The reaction mixture was stirred at 70° C. for 2 h and cooled to room temperature. The solvent was removed under reduced pressure. The residue was suspended in EtOAc and 1,3-dicyclohexyl urea was filtered off. The product was partitioned between EtOAc and 0.2 N HCl. The EtOAc layer was washed with 0.2 N HCl, $H_2O$, saturated NaCl, dried with $Na_2SO_4$, filtered, and concentrated. The crude product was purified by column chromatography on silica gel (3% 2-propanol/$CH_2Cl_2$) to give the monophospholactate (72 mg, 62%, GS 191484) as a white solid: $^1H$ NMR ($CDCl_3$) δ 7.71 (d, J=8.7 Hz, 2H), 7.34 (m, 2H), 7.25-7.14 (m, 5H), 7.00 (d, J=9.0 Hz, 2H), 6.87 (d, J=8.7 Hz, 2H), 5.65 (d, J=5.4 Hz, 1H), 5.05 (m, 2H), 4.38 (d, J=9.6 Hz, 2H), 4.32-4.20 (m, 2H), 4.00 (m, 2H), 3.87-3.63 (m, 12H), 3.12-2.78 (m, 7H), 1.85-1.67 (m, 3H), 1.20 (m, 6H), 0.91 (d, J=6.6 Hz, 3H), 0.88 (d, J=6.6 Hz, 3H); $^{31}P$ NMR ($CDCl_3$) δ 16.0.

Example 4

Lactate 5: To a suspension of lactic acid sodium salt (5 g, 44.6 mmol) in 2-propanol (60 mL) was added 4-(3-chloropropyl)morpholine hydrochloride (8.30 g, 44.6 mmol). The reaction mixture was heated to reflux for 18 h and cooled to room temperature. The solid was filtered and the filtrate was recrystallized from EtOAc/hexane to give the lactate (1.2 g, 12%).

Example 5

Monophospholactate 6: A solution of 1 (0.10 g, 0.13 mmol) and lactate 5 (0.10 g, 0.48 mmol) in pyridine (2 mL) was heated to 70° C. and 1,3-dicyclohexylcarbodiimide (0.10 g, 0.49 mmol) was added. The reaction mixture was stirred at 70° C. for 2 h and cooled to room temperature. The solvent was removed under reduced pressure. The residue was suspended in EtOAc and 1,3-dicyclohexyl urea was filtered off. The product was partitioned between EtOAc and $H_2O$. The EtOAc layer was washed with saturated NaCl, dried with $Na_2SO_4$, filtered, and concentrated. The crude product was purified by column chromatography on silica gel (4% 2-propanol/$CH_2Cl_2$) to give the monophospholactate (30 mg, 24%, GS 192781, 1/1 diastereomeric mixture) as a white solid: $^1H$ NMR ($CDCl_3$) δ 7.71 (d, J=8.7 Hz, 2H), 7.38-7.15 (m, 7H), 7.00 (d, J=8.7 Hz, 2H), 6.91 (m, 2H), 5.65 (d, J=3.3 Hz, 1H), 5.18-4.98 (m, 3H), 4.54 (dd, 1H), 4.42 (dd, 1H), 4.2 (m, 2H), 4.00-3.67 (m, 16H), 3.13-2.77 (m, 7H), 2.4 (m, 5H), 1.85-1.5 (m, 5H), 1.25 (m, 2H), 0.93 (d, J=6.6 Hz, 3H), 0.88 (d, J=6.6 Hz, 3H); $^{31}P$ NMR ($CDCl_3$) δ 17.4, 15.4.

Example 6

Sulfonamide 8: A solution of dibenzylphosphonate 7 (0.1 g, 0.13 mmol) in $CH_2Cl_2$ (0.5 mL) at 0° C. was treated with trifluoroacetic acid (0.25 mL). The solution was stirred for 30 min at 0° C. and then warmed to room temperature for an additional 30 min. The reaction mixture was diluted with toluene and concentrated under reduced pressure. The residue was co-evaporated with toluene (2×), chloroform (2×), and dried under vacuum to give the ammonium triflate salt which was dissolved in $CH_2Cl_2$ (1 mL) and cooled to 0° C. Triethylamine (72 μL, 0.52 mmol) was added followed by the treatment of 4-methylpiperazinylsulfonyl chloride (25 mg, 0.13 mmol). The solution was stirred for 1 h at 0° C. and the product was partitioned between $CH_2Cl_2$ and $H_2O$. The organic phase was washed with saturated NaCl, dried with $Na_2SO_4$, filtered, and evaporated under reduced pressure. The crude product was purified by column chromatography on silica gel (5% 2-propanol/$CH_2Cl_2$) to give the sulfonamide 8 (32 mg, 30%, GS 273835) as a white solid: $^1H$NMR ($CDCl_3$) δ 7.35 (m, 10H), 7.11 (d, J=8.7 Hz, 2H), 6.81 (d, J=8.7 Hz, 2H), 5.65 (d, J=5.4 Hz, 1H), 5.2-4.91 (m, 4H), 4.2 (d, J=10.2 Hz, 2H), 4.0-3.69 (m, 6H), 3.4-3.19 (m, 5H), 3.07-2.75 (m, 5H), 2.45 (m, 4H), 2.3 (s, 3H), 1.89-1.44 (m, 7H), 0.93 (m, 6H); $^{31}P$ NMR ($CDCl_3$) δ 20.3.

Example 7

Phosphonic Acid 9: To a solution of 8 (20 mg, 0.02 mmol) in EtOAc (2 mL) and 2-propanol (0.2 mL) was added 10% Pd/C (5 mg). The suspension was stirred under $H_2$ atmosphere (balloon) at room temperature overnight. The reaction mixture was filtered through a plug of celite. The filtrate was concentrated and dried under vacuum to give the phosphonic acid (10 mg, 64%) as a white solid.

Example 8

Dibenzylphosphonate 11: A solution of 10 (85 mg, 0.15 mmol) and 1H-tetrazole (14 mg, 0.20 mmol) in $CH_2Cl_2$ (2 mL) was treated with Dibenzyldiisopropylphosphoramidite (60 μL, 0.20 mmol) and stirred at room temperature overnight. The product was partitioned between $CH_2Cl_2$ and $H_2O$, dried with $Na_2SO_4$, filtered and concentrated. The crude product was purified by column chromatography to give the intermediate dibenzylphosphite (85 mg, 0.11 mmol) which was dissolved in $CH_3CN$ (2 mL) and treated with iodobenzenediacetate (51 mg, 0.16 mmol). The reaction mixture was stirred at room temperature for 3 h and concentrated. The residue was partitioned between EtOAc and $NaHCO_3$. The organic layer was washed with $H_2O$, dried with $Na_2SO_4$, filtered, and concentrated. The crude product was purified by column chromatography on silica gel (3% 2-propanol/$CH_2Cl_2$) to give the dibenzylphosphonate (45 mg, 52%) as a white solid.

Example 9

Disodium Salt of Phosphonic Acid 12: To a solution of 11 (25 mg, 0.03 mmol) in EtOAc (2 mL) was added 10% Pd/C (10 mg). The suspension was stirred under $H_2$ atmosphere (balloon) at room temperature for 4 h. The reaction mixture was filtered through a plug of celite. The filtrate was concentrated and dried under vacuum to give the phosphonic acid which was dissolved in $H_2O$ (1 mL) and treated with $NaHCO_3$ (2.53 mg, 0.06 mmol). The reaction mixture was stirred at room temperature for 1 h and lyophilized overnight to give the disodium salt of phosphonic acid (19.77 mg, 95%, GS 273777) as a white solid: $^1H$ NMR ($CD_3OD$) δ 7.81 (d, J=9.0 Hz, 2H), 7.35 (d, J=8.1 Hz, 2H), 7.27-7.09 (m, 5H), 5.57 (d, J=5.1 Hz, 1H), 5.07 (m, 1H), 4.87-4.40 (m, 3H), 3.93-3.62 (m, 6H), 3.45-2.6 (m, 6H), 2.0 (m, 2H), 1.55 (m, 1H), 0.95-0.84 (m, 6H).

Example 10

Dibenzylphosphonate 14: A solution of 13 (0.80 g, 0.93 mmol) and 1H-tetrazole (98 mg, 1.39 mmol) in $CH_2Cl_2$ (15 mL) was treated with dibenzyldiisopropylphosphoramidite (0.43 mL, 1.39 mmol) and stirred at room temperature overnight. The product was partitioned between $CH_2Cl_2$ and $H_2O$, dried with $Na_2SO_4$, filtered and concentrated. The crude product was purified by column chromatography to give the intermediate dibenzylphosphite (0.68 g, 67%). To a solution of the dibenzylphosphite (0.39 g, 0.35 mmol) in $CH_3CN$ (5 mL) was added iodobenzenediacetate (0.17 g, 0.53 mmol). The reaction mixture was stirred at room temperature for 2 h and concentrated. The residue was partitioned between EtOAc and $NaHCO_3$. The organic layer was washed with $H_2O$, dried with $Na_2SO_4$, filtered, and concentrated. The crude product was purified by column chromatography on silica gel (3% 2-propanol/$CH_2Cl_2$) to give the dibenzylphosphonate (0.35 g, 88%) as a white solid.

Example 11

Disodium Salt of Phosphonic Acid 15: To a solution of 14 (0.39 g, 0.35 mmol) in EtOAc (30 mL) was added 10% Pd/C (0.10 g). The suspension was stirred under $H_2$ atmosphere (balloon) at room temperature for 4 h. The reaction mixture was filtered through a plug of celite. The filtrate was concentrated and dried under vacuum to give the phosphonic acid, which was dissolved in $H_2O$ (3 mL) and treated with $NaHCO_3$ (58 mg, 0.70 mmol). The reaction mixture was stirred at room temperature for 1 h and lyophilized overnight to give the disodium salt of phosphonic acid (0.31 g, 90%, GS 273811) as a white solid: $^1H$ NMR ($CD_3OD$) δ 7.81 (d, J=9.0 Hz, 2H), 7.43-7.2 (m, 7H), 7.13 (d, J=9.0 Hz, 2H), 6.9 (m, 2H), 5.55 (d, J=4.8 Hz, 1H), 5.07 (m, 2H), 4.87 (m, 1H), 4.64-4.4 (m, 4H), 3.93-3.62 (m, 9H), 3.33-2.63 (m, 5H), 2.11 (m, 1H), 1.6-1.42 (m, 4H), 1.38-1.25 (m, 7H), 0.95 (d, J=6.3 Hz, 3H), 0.84 (d, J=6.3 Hz, 3H).

Examples for the Preparation of Cyclic Carbonyl-like Phosphonate Protease Inhibitors (CCPPI)

Phosphonamidate Prodrugs

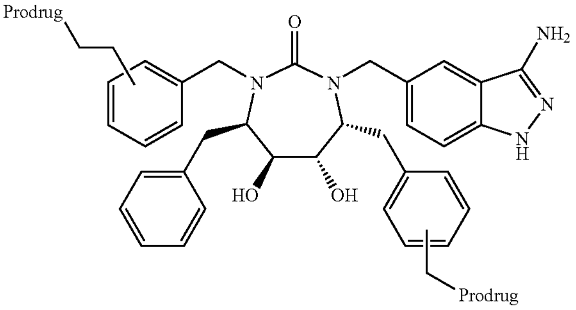

| | |
|---|---|
| Scheme 1-2 | Scaffold Synthesis |
| Scheme 3-10 | P2'-Benzyl ether phosphonates |
| Scheme 11-13 | P2'-Alkyl ether phosphonates |
| Scheme 14-17 | P2'-Benzyl Amide phosphonates |
| Scheme 18-25 | P1-Phosphonates |
| Scheme 50 | Reagents |

Scheme 1

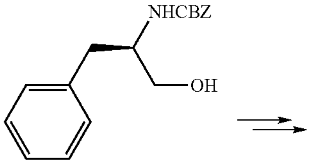

1

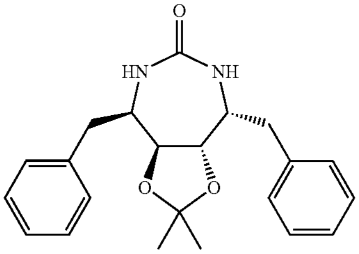

1.1

The conversion of 1 to 1.1 is described in J. Org Chem 1996, 61, p444-450

Scheme 2

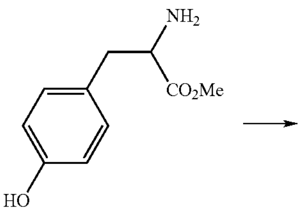

2.1

-continued

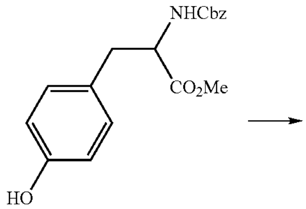

2.2

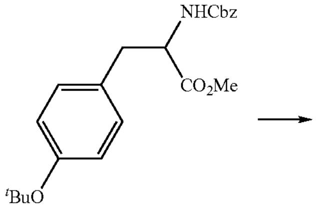

2.3

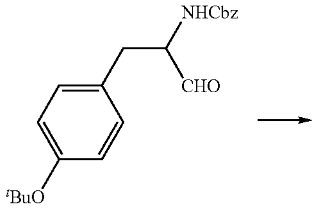

2.4

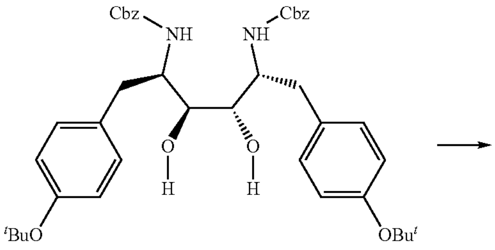

2.5

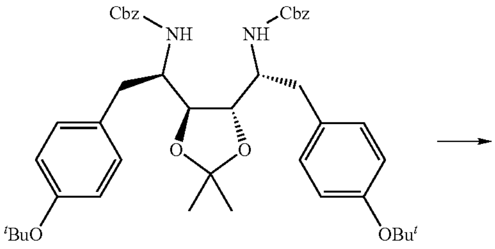

2.6

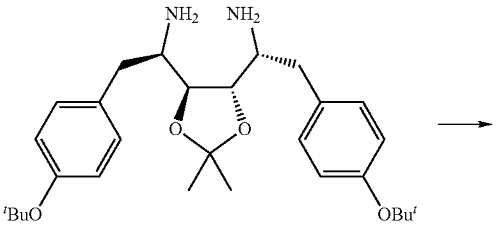

2.7

-continued

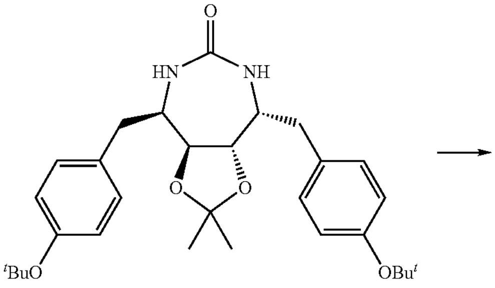

2.8

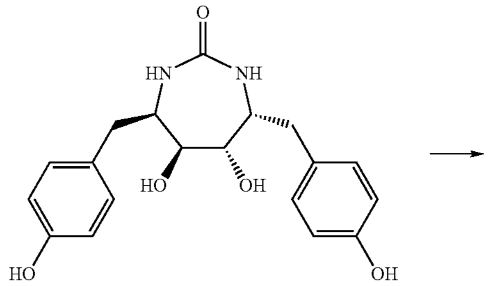

2.9

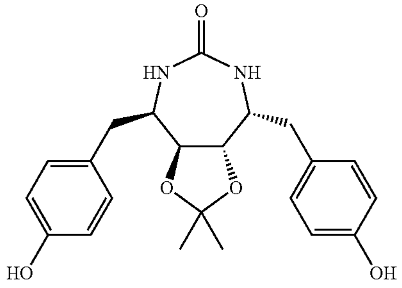

2.10

2-Benzyloxycarbonylamino-3-(4-tert-butoxy-phenyl)-propionic Acid Methyl Ester (2.3)

H-D-Tyr-O-me hydrochloride 2.1 (25 g, 107.7 mmol) is dissolved in methylene chloride (150 mL) and aqueous sodium bicarbonate (22 g in 150 mL water), and then cooled to 0° C. To this resulting solution benzyl chloroformate (20 g, 118 mmol) is slowly added. After complete addition, the resulting solution is warmed to room temperature, and is then stirred for 2 h. The organic phase is separated, dried over $Na_2SO_4$, and concentrated under reduced pressure, to give the crude carbamate 2.2 (35 g). The crude CBZ-Tyr-OMe product is dissolved in methylene chloride (300 mL) containing concentrated $H_2SO_4$. Isobutene is bubbled though the solution for 6 h. The reaction is then cooled to 0° C., and neutralized with saturated $NaHCO_3$ aqueous solution. The organic phase is separated, dried, concentrated under reduced pressure, and purified by silica gel column chromatography to afford the tert-butyl ether 2.3 (25.7 g, 62%).

[2-(4-tert-Butoxy-phenyl)-1-formyl-ethyl]-carbamic Acid Benzyl Ester (2.4) (Reference J. O. C. 1997, 62, 3884).

To a stirred −78° C. methylene chloride solution (60 mL) of 2.3, DIBAL (82 mL of 1.5 M in toluene, 123 mmol) was added over 15 min. The resultant solution was stirred at −78° C. for 30 min. Subsequently, a solution of EtOH/36% HCl (9/1; 15 mL) is added slowly. The solution is added to a vigorously stirred aqueous HCl solution (600 mL, 1N) at 0° C. The layers are then separated, and the aqueous phase is extracted with cold methylene chloride. The combined organic phases are washed with cold 1N HCl aqueous solution, water, dried over $Na_2SO_4$, and then concentrated under reduced pressure to give the crude aldehyde 2.4 (20 g, 91%).

[4-Benzyloxycarbonylamino-1-(4-tert-butoxy-benzyl)-5-(4-tert-butoxy-phenyl)-2,3-dihydroxy-pentyl]-carbamic Acid Benzyl Ester (2.5)

To a slurry of $VCl_3(THF)_3$ in methylene chloride (150 mL) at room temperature is added Zinc powder (2.9 g, 44 mmol), and the resulting solution is then stirred at room temperature for 1 hour. A solution of aldehyde 2.4 (20 g, 56 mmol) in methylene chloride (100 mL) is then added over 10 min. The resulting solution is then stirred at room temperature overnight, poured into an ice-cold $H_2SO_4$ aqueous solution (8 mL in 200 mL), and stirred at 0° C. for 30 min. The methylene chloride solution is separated, washed with 1N HCl until the washing solution is light blue. The organic solution is then concentrated under reduced pressure (solids are formed during concentration), and diluted with hexane. The precipitate is collected and washed thoroughly with a hexane/methylene chloride mixture to give the diol product 2.5. The filtrate is concentrated under reduced pressure and subjected to silica gel chomatography to afford a further 1.5 g of 2.5. (Total=13 g, 65%).

[1-{5-[1-Benzyloxycarbonylamino-2-(4-tert-butoxy-phenyl)-ethyl]-2,2-dimethyl-[1,3]dioxolan-4-yl}-2-(4-tert-butoxy-phenyl)-ethyl]-carbamic Acid Benzyl Ester (2.6)

Diol 2.5 (5 g, 7 mmol) is dissolved in acetone (120 mL), 2,2-dimethoxypropane (20 mL), and pyridinium p-toluenesulfonate (120 mg, 0.5 mmol). The resulting solution is refluxed for 30 min., and then concentrated under reduced pressure to almost dryness. The resulting mixture is partitioned between methylene chloride and saturated $NaHCO_3$ aqueous solution, dried, concentrated under reduced pressure, and purified by silica gel column chomatography to afford isopropylidene protected diol 2.6 (4.8 g, 92%).

4,8-Bis-(4-tert-butoxy-benzyl)-2,2-dimethyl-hexahydro-1,3-dioxa-5,7-diaza-azulen-6-one (2.8)

The diol 2.6 is dissolved in EtOAc/EtOH (10 mL/2 mL) in the presence of 10% Pd/C and hydrogenated at atmospheric pressure to afford the diamino compound 2.7. To a solution of crude 2.7 in 1,1,2,2-tetrachloroethane is added 1,1-carboxydiimidazole (1.05 g, 6.5 mmol) at room temperature. The mixture is stirred for 10 min, and the resulting solution is then added dropwise to a refluxing 1,1',2,2'-tetrachloroethane solution (150 mL). After 30 min., the reaction mixture is cooled to room temperature, and washed with 5% citric acid aqueous solution, dried over $Na_2SO4$, concentrated under reduced pressure, and purified by silica gel column chomatography to afford the cyclourea derivative 2.8 (1.92 g, 60% over 2 steps).

5,6-Dihydroxy-4,7-bis-(4-hydroxy-benzyl)-[1,3]diazepan-2-one (2.9)

Cyclic Urea 2.8 (0.4 g, 0.78 mmol) was dissolved in dichloromethane (3 mL) and treated with TFA (1 mL). The mixture was stirred at room temperature for 2 h upon which time a white solid precipitated. 2 drops of water and methanol (2 mL) were added and the homogeneous solution was stirred for 1 h and concentrated under reduced pressure. The crude solid, 2.9, was dried overnight and then used without further purification.

4,8-Bis-(4-hydroxy-benzyl)-2,2-dimethyl-hexahydro-1,3-dioxa-5,7-diaza-azulen-6-one (2.10)

Diol 2.9 (1.8 g, 5.03 mmol) was dissolved in DMF (6 mL) and 2,2-dimethoxypropane (12 mL). P-TsOH (95 mg) was added and the mixture stirred at 65° C. for 3 h. A vacuum was applied to remove water and then the mixture was stirred at 65° C. for a further 1 h. The excess dimethoxypropane was then distilled and the remaining DMF solution was then allowed to cool. The solution of acetonide 2.10 can then used without further purification in future reactions.

Scheme 3

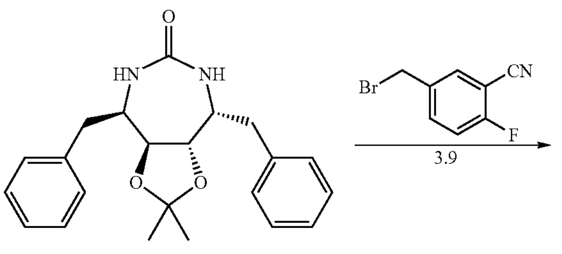

1.1

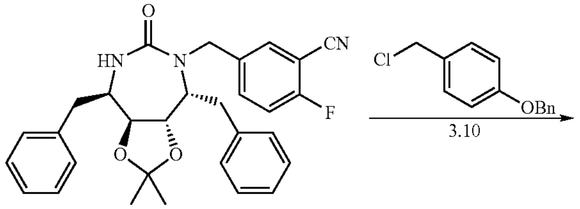

3.1

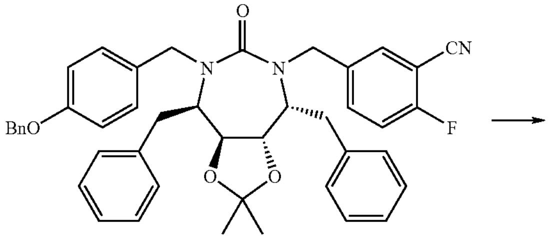

3.2

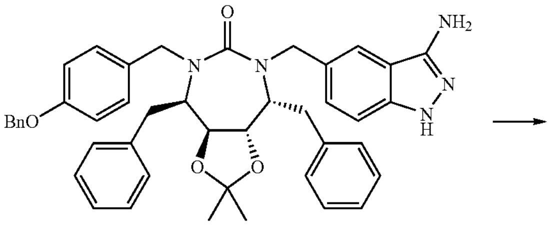

3.3

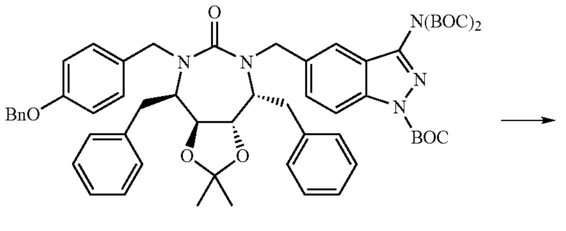

3.4

-continued

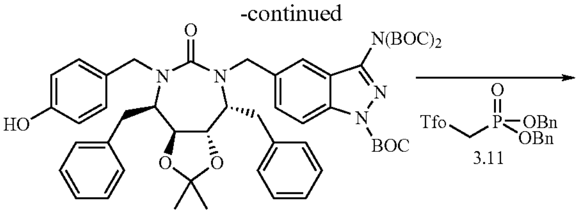

3.5

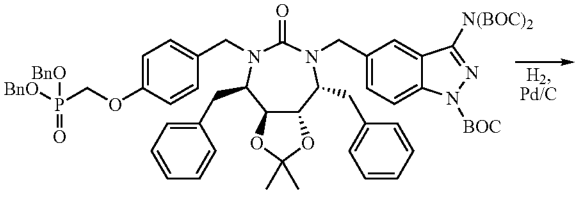

3.6

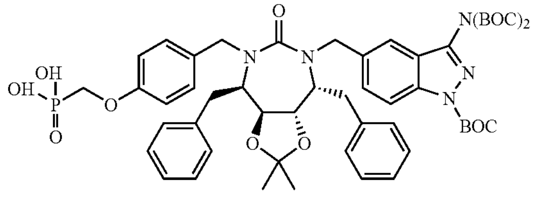

3.7

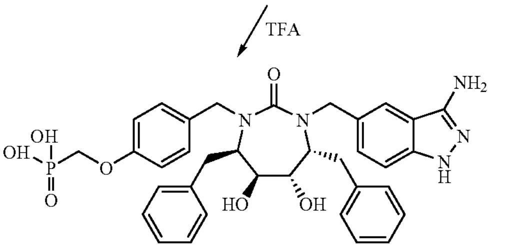

3.8

3-Cyano-4-fluorobenzyl urea 3.1: A solution of urea 1.1 (1.6 g, 4.3 mmol) in THF was treated with sodium hydride (0.5 g of 60% oil dispersion, 13 mmol). The mixture was stirred at room temperature for 30 min and then treated with 3-cyano-4-fluorobenzyl bromide 3.9 (1.0 g, 4.8 mmol). The resultant solution was stirred at room temperature for 3 h, concentrated under reduced pressure, and then partitioned between $CH_2Cl_2$ and saturated brine solution containing 1% citric acid. The organic phase was separated, dried over sodium sulfate, filtered and concentrated under reduced pressure. The residue was purified by silica gel eluting with 15-25% ethyl acetate in hexanes to yield urea 3.1 (1.5 g, 69%) as a white form.

Benzyl ether 3.2: A solution of 3.1 (0.56 g, 1.1 mmol) in DMF (5 mL) was treated with sodium hydride (90 mg of 60% oil dispersion, 2.2 mmol) and the resultant mixture stirred at room temperature for 30 min. 4-Benzyloxy benzyl chloride 3.10 (0.31 g, 1.3 mmol) was added and the resultant solution stirred at room temperature for 3 h. The mixture was concentrated under reduced pressure and then partitioned between $CH_2Cl_2$ and saturated brine solution. The organic phase was separated, dried over sodium sulfate, filtered, and concentrated under reduced pressure. The residue was purified by silica gel eluting with 110% ethyl acetate in hexanes to yield compound 3.2 (0.52 g, 67%) as white form.

Indazole 3.3: Benzyl ether 3.2 (0.51 g, 0.73 mmol) was dissolved in n-butanol (10 mL) and treated with hydrazine hydrate (1 g, 20 mmol). The mixture was refluxed for 4 h and then allowed to cool to room temperature. The mixture was concentrated under reduced pressure and the residue was then partitioned between $CH_2Cl_2$ and 10% citric acid solution. The organic phase was separated, concentrated under reduced pressure, and then purified by silica gel column eluting with 5% methanol in $CH_2Cl_2$ to afford indazole 3.3 (0.42 g, 82%) as white solid.

Boc-indazole 3.4: A solution of indazole 3.3 (0.4 g, 0.59 mmol) in $CH_2Cl_2$ (10 mL) was treated with diisopropylethylamine (0.19 g, 1.5 mmol), DMAP (0.18 g, 1.4 mmol), and di-tert-butyl dicarbonate (0.4 g, 2 mmol). The mixture was stirred at room temperature for 3 h and then partitioned between $CH_2Cl_2$ and 5% citric acid solution. The organic phase was separated, dried over sodium sulfate, filtered and concentrated under reduced pressure. The residue was purified by silica gel eluting with 2% methanol in $CH_2Cl_2$ to afford 3.4 (0.42 g, 71%).

Phenol 3.5: A solution of 3.4 (300 mg, 0.3 mmol) in ethyl acetate (10 mL) and methanol (10 mL) was treated with 10% Pd/C (40 mg) and stirred under a hydrogen atmosphere (balloon) for 16 h. The catalyst was removed by filtration and the filtrate was concentrated under reduced pressure to yield 3.5 as a white powder. This was used without further purification.

Dibenzyl ester 3.6: A solution of 3.5 (0.1 mmol) in THF (5 mL) was treated with dibenzyl triflate 3.11 (90 mg, 0.2 mmol), and cesium carbonate (0.19 g, 0.3 mmol). The mixture was stirred at room temperature for 4 h and then concentrated under reduced pressure. The residue was partitioned between $CH_2Cl_2$ and saturated brine. The organic phase was separated, dried over sodium sulfate, filtered and concentrated under reduced pressure. The residue was purified by silica gel eluting with 20-40% ethyl acetate in hexanes to afford 3.6 (70 mg, 59%). $^1H$ NMR ($CDCl_3$): δ 8.07 (d, 1H), 7.20-7.43 (m, 16H), 7.02-7.15 (m, 8H), 6.80 (d, 2H), 5.07-5.18 (m, 4H), 5.03 (d, 1H), 4.90 (d, 1H), 4.20 (d, 2H), 3.74-3.78 (m, 4H), 3.20 (d, 1H), 3.05 (d, 1H) 2.80-2.97 (m, 4H), 1.79 (s, 9H), 1.40 (s, 18H), 1.26 (s, 6H); $^{31}P$ NMR ($CDCl_3$): 20.5 ppm.

Phosphonic acid 3.7: A solution of dibenzylphosphonate 3.6 (30 mg) in EtOAc (10 mL) was treated with 10% Pd/C (10 mg) and the mixture was stirred under a hydrogen atmosphere (balloon) for 3 h. The catalyst was removed by filtration and the filtrate was concentrated under reduced pressure to afford phosphonic acid 3.7. This was used without further purification.

Phosphonic acid 3.8: The crude phosphonic acid 3.7 was dissolved in $CH_2Cl_2$ (2 mL) and treated with trifluoroacetic acid (0.4 mL). The resultant mixture was stirred at room temperature for 4 h. The mixture was concentrated under reduced pressure and then purified by preparative HPLC (35% $CH_3CN$/65% $H_2O$) to afford the phosphonic acid 3.8 (9.4 mg, 55%). $^1H$ NMR ($CD_3OD$): δ 7.71 (s, 1H), 7.60 (d, 1H), 6.95-7.40 (m, 15H), 4.65 (d, 2H), 4.17 (d, 2H), 3.50-3.70 (m, 3H), 3.42 (d, 1H), 2.03-3.14 (m, 6H); $^{31}P$ NMR ($CDCl_3$): 17.30

Scheme 4

3.6

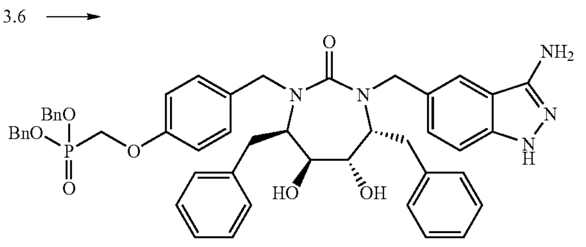

4.1

Dibenzylphosphonate 4.1: A solution of 3.6 (30 mg, 25 μmol) in $CH_2Cl_2$ (2 mL) was treated with TFA (0.4 mL) and the resultant mixture was stirred at room temperature for 4 h. The mixture was concentrated under reduced pressure and the residue was purified by silica gel eluting with 50% ethyl acetate in hexanes to afford 4.1 (5 mg, 24%). $^1H$ NMR ($CDCl_3$): δ 6.96-7.32 (m, 25H), 6.95 (d, 2H), 5.07-5.18 (m, 4H), 4.86 (d, 1H), 4.75 (d, 1H), 4.18 (d, 2H), 3.40-3.62 (m, 4H), 3.25 (d, 1H), 2.80-3.15 (m, 6H); $^{31}P$ NMR ($CDCl_3$) 20.5 ppm; MS: 852 (M+H), 874 (M+Na).

Scheme 5

3.5

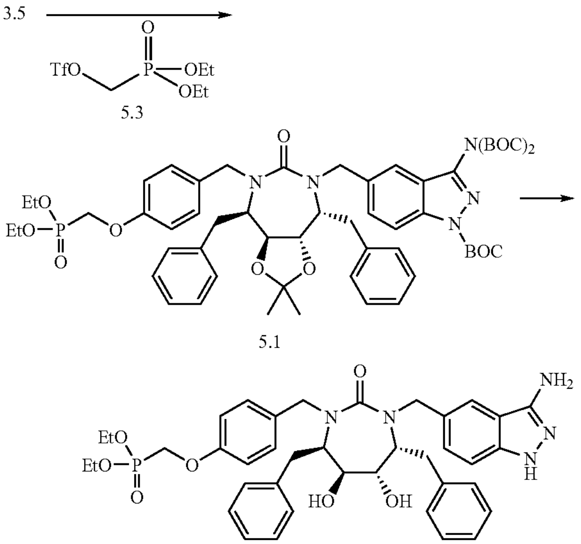

5.3

5.1

5.2

Diethylphosphonate 5.1: A solution of phenol 3.5 (48 mg, 52 μmol) in THF (5 mL) was treated with triflate 5.3 (50 mg, 165 μmol), and cesium carbonate (22 mg, 0.2 mmol). The resultant mixture was stirred at room temperature for 5 h and then concentrated under reduced pressure. The residue was partitioned between $CH_2Cl_2$ and saturated brine. The organic phase was separated, dried over sodium sulfate, filtered and concentrated under reduced pressure. The residue was purified by silica gel eluting with 7% methanol in $CH_2Cl_2$ to afford 5.1 (28 mg, 50%). $^1H$ NMR ($CDCl_3$): δ 8.06 (d, 1H), 7.30-7.43 (m, 7H), 7.02-7.30 (m, 7H), 6.88 (d, 2H), 5.03 (d, 1H), 4.90 (d, 1H), 4.10-4.25 (m, 6H), 3.64-3.80 (m, 4H), 3.20

(d, 1H), 3.05 (d, 1H) 2.80-2.97 (m, 4H), 1.79 (s, 9H), 1.20-1.50 (m, 30H); $^{31}$P NMR ($CDCl_3$): 18.5 ppm; MS: 1068 (M+H), 1090 (M+Na).

Diethylphosphonate 5.2: A solution of 5.1 (28 mg, 26 μmol) in $CH_2Cl_2$ (2 mL) was treated with TFA (0.4 mL) and the resultant mixture was stirred at room temperature for 4 hrs. The mixture was concentrated under reduced pressure and the residue was purified by silica gel to afford 5.2 (11 mg, 55%). $^{1}$H NMR ($CDCl_3$+10% $CD_3OD$): δ 6.96-7.35 (m, 15H), 6.82 (d, 2H), 4.86 (d, 1H), 4.75 (d, 1H), 4.10-4.23 (M, 6H), 3.40-3.62 (m, 4H), 2.80-3.20 (m), 1.31 (t, 6H); $^{31}$P NMR ($CDCl_3$+10% $CD_3OD$): 19.80 ppm; MS: 728 (M+H).

3.1

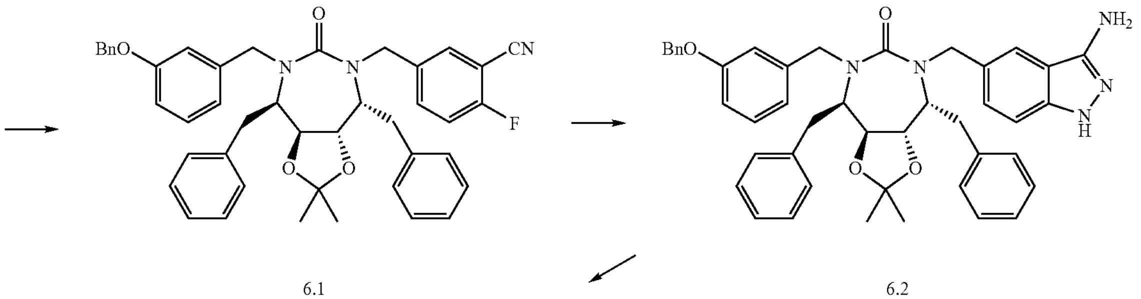

6.1

6.2

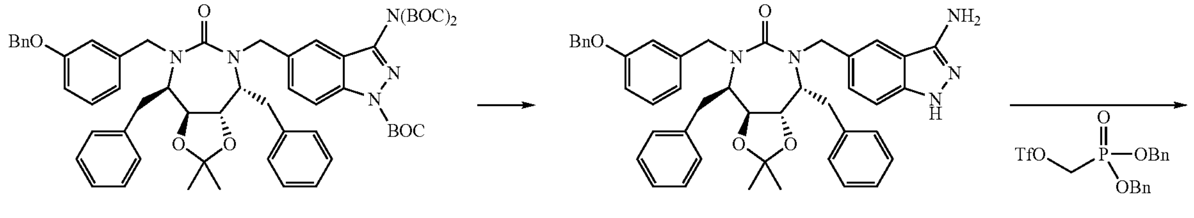

6.3

6.4

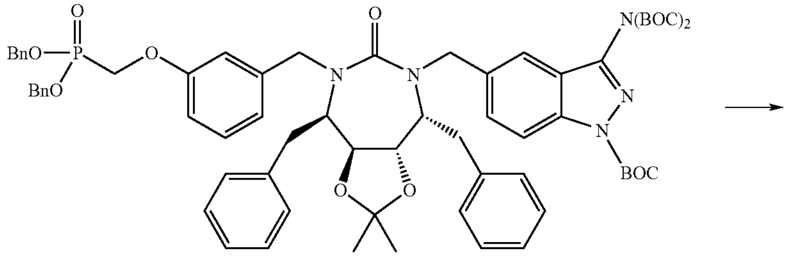

6.5

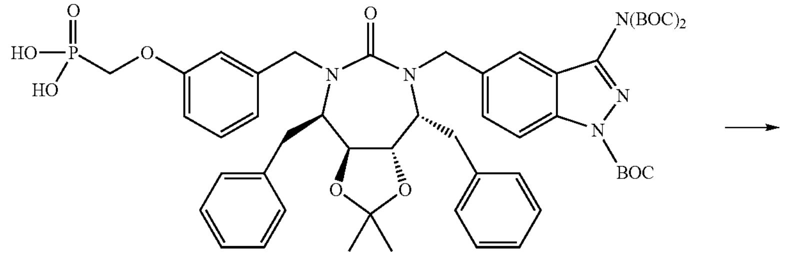

6.6

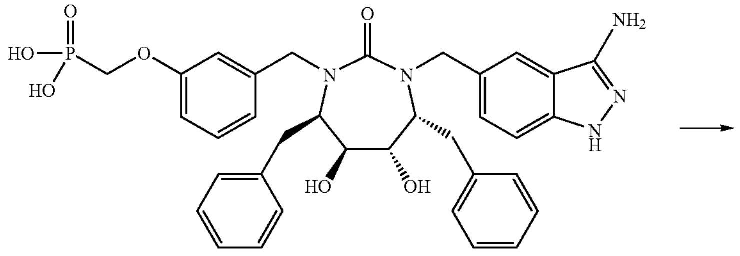

6.7

-continued

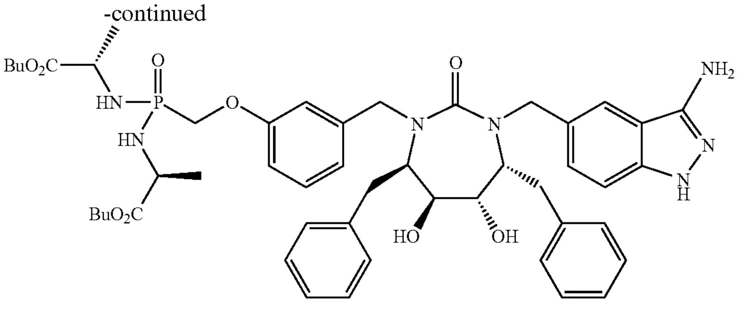

6.8

3-Benzyloxybenzyl urea 6.1: The urea 3.1 (0.87 g, 1.7 mmol) was dissolved in DMF and treated with sodium hydride (60% dispersion, 239 mg, 6.0 mmol) followed by m-benzyloxybenzylbromide 6.9 (0.60 g, 2.15 mmol). The mixture was stirred for 5 h and then diluted with ethyl acetate. The solution was washed with water, brine, dried over magnesium sulfate, filtered and concentrated under reduced pressure. The residue was purified by silica gel eluting with 25% ethyl acetate in hexanes to afford urea 6.1 (0.9 g, 75%).

Indazole 6.2: The urea 6.1 (41 mg, 59 μmol) was dissolved in n-butanol (1.5 mL) and treated with hydrazine hydrate (100 μL, 100 mmol). The mixture was refluxed for 2 h and then allowed to cool. The mixture was diluted with ethyl acetate, washed with 10% citric acid solution, brine, saturated $NaHCO_3$, and finally brine again. The organic phase was dried over sodium sulfate, filtered and concentrated under reduced pressure to give the crude product 6.2 (35 mg, 83%). (Chem. Biol. 1998, 5, 597-608).

Boc-indazole 6.3: The indazole 6.2 (1.04 g, 1.47 mmol) was dissolved in $CH_2Cl_2$ (20 mL) and treated with di-t-butyl dicarbonate (1.28 g, 5.9 mmol), DMAP (0.18 g, 1.9 mmol) and DIPEA (1.02 ml, 9.9 mmol). The mixture was stirred for 3 h and then diluted with ethyl acetate. The solution was washed with 5% citric acid solution, $NaHCO_3$, brine, dried over magnesium sulfate, filtered and concentrated under reduced pressure. The residue was purified by silica gel eluting with 50% ethyl acetate in hexanes to give 6.3 (0.71 g, 49%).

Phenol 6.4: Compound 6.3 (20 mg, 0.021 mmol) was dissolved in MeOH (1 mL) and EtOAc (1 mL) and treated with 10% Pd/C catalyst (5 mg). The mixture was stirred under a hydrogen atmosphere (balloon) until completion. The catalyst was removed by filtration and the filtrate concentrated under reduced pressure to afford compound 6.4 (19 mg, 100%).

Dibenzyl phosphonate 6.5: A solution of compound 6.4 (0.34 g, 0.37 mmol) in acetonitrile (5 mL) was treated with $Cs_2CO_3$ (0.36 g, 1.1 mmol) and triflate 3.11 (0.18 mL, 0.52 mmol). The reaction mixture was stirred for 1 h. The reaction mixture was filtered and the filtrate was then concentrated under reduced pressure. The residue was re-dissolved in EtOAc, washed with water, saturated $NaHCO_3$, and finally brine, dried over $MgSO_4$, filtered and concentrated under reduced pressure. The residue was purified by silica gel eluting with hexane:EtOAc (1:1) to afford compound 6.5 (0.32 g, 73%).

Phosphonic acid 6.6: Compound 6.5 (208 mg, 0.174 mmol) was treated in the same manner as benzyl phosphonate 3.6 in the preparation of phosphonate diacid 3.7, except MeOH was used as the solvent, to afford compound 6.6 (166 mg, 94%).

Phosphonic acid 6.7: Compound 6.6 (89 mg, 0.088 mmol) was treated according to the conditions described in Scheme 3 for the conversion of 3.7 into 3.8. The residue was purified by preparative HPLC eluting with a gradient of 90% methanol in 100 mM TEA bicarbonate buffer and 100% TEA bicarbonate buffer to afford phosphonic acid 6.7 (16 mg, 27%)

Bisamidate 6.8: Triphenylphosphine (112 mg, 0.43 mmol) and aldrithiol-2 (95 mg, 0.43 mmol) were mixed in dry pyridine (0.5 mL). In an adjacent flask the diacid 6.7 (48 mg, 0.71 mmol) was suspended in dry pyridine (0.5 mL) and treated with DIPEA (0.075 mL 0.43 mmol) and L-AlaButyl ester hydrochloride (78 mg, 0.43 mmol) and finally the triphenylphosphine, aldrithiol-2 mixture. The reaction mixture was stirred under nitrogen for 24 h then concentrated under reduced pressure. The residue was purified by preparative HPLC eluting with a gradient of 5% to 95% acetonitrile in water. The product obtained was then further purified by silica gel eluting with $CH_2Cl_2$: MeOH (9:1) to give compound 6.8 (9 mg, 14%).

Scheme 7

6.4 → 5.3

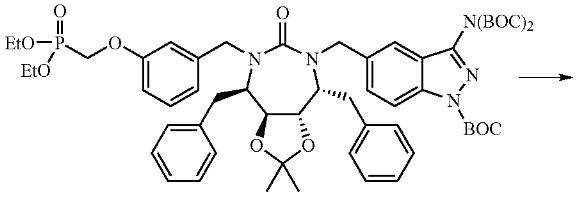

7.1

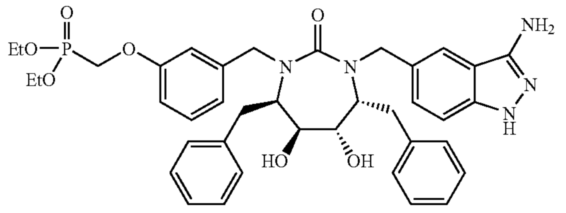

7.2

Diethyl phosphonate 7.1: Compound 6.4 (164 mg, 0.179 mmol) was treated according to the procedure used to generate compound 6.5 except triflate 5.3 was used in place of triflate 3.11 to afford compound 7.1 (142 mg, 74%).

Diethylphosphonate 7.2: Compound 7.1 (57 mg, 0.053 mmol) was treated according to the conditions used to form 6.7 from 6.6. The residue formed was purified by silica gel eluting with $CH_2Cl_2$: MeOH (9:1) to afford compound 7.2 (13 mg, 33%).

Scheme 8

6.6

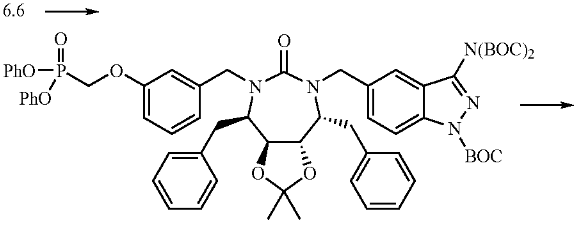

8.1

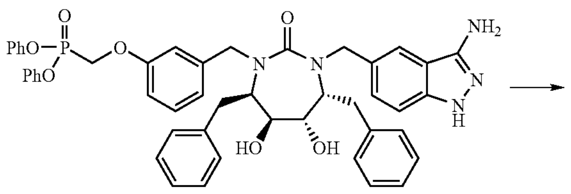

8.2

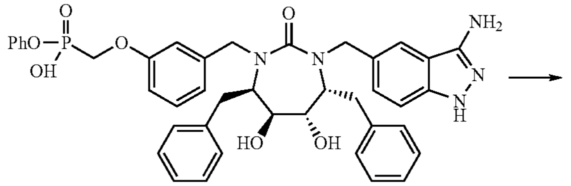

8.3

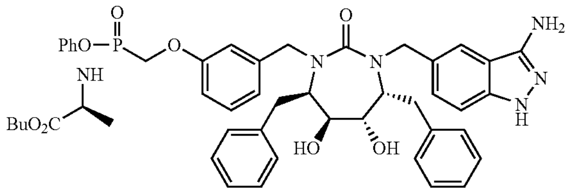

8.4

Diphenylphosphonate 8.1: A solution of 6.6 (0.67 g, 0.66 mmol) in pyridine (10 mL) was treated with phenol (0.62 g, 6.6 mmol) and DCC (0.82 mg, 3.9 mmol). The resultant mixture was stirred at room temperature for 5 min and then the solution was heated at 70° C. for 3 h. The mixture was allowed to cool to room temperature and then diluted with EtOAc and water (2 mL). The resultant mixture was stirred at room temperature for 30 min and then concentrated under reduced pressure. The residue was triturated with $CH_2Cl_2$, and the white solid that formed was removed by filtration. The filtrate was concentrated under reduced pressure and the resultant residue was purified by silica gel eluting with 30% ethyl acetate in hexanes to yield 8.1 (0.5 g, 65%). $^1$H NMR ($CDCl_3$): δ 8.08 (d, 1H), 7.41 (d, 1H), 7.05-7.35 (m, 22H), 6.85 (d, 2H), 6.70 (s, 1H). 5.19 (d, 1H), 5.10 (d, 1H), 4.70 (d, 2H), 3.70-3.90 (m, 4H), 3.20 (d, 1H), 3.11 (d, 1H), 2.80-2.97 (m, 4H), 1.79 (s, 9H), 1.40 (s, 18H), 1.30 (s, 6H); $^{31}$P NMR ($CDCl_3$): 12.43 ppm Diphenylphosphonate 8.2: A solution of 8.1 (0.5 g, 0.42 mmol) in $CH_2Cl_2$ (4 mL) was treated with TFA (1 mL) and the resultant mixture was stirred at room temperature for 4 h. The reaction mixture was concentrated under reduced pressure and azeotroped twice with $CH_3CN$. The residue was purified by silica gel eluting with 5% methanol in $CH_2Cl_2$ to afford diphenylphosphonate 8.2 (0.25 g, 71%). $^1$H NMR ($CDCl_3$): δ 7.03-7.40 (m, 21H), 6.81-6.90 (m, 3H), 4.96 (d, 1H), 4.90 (d, 1H) 4.60-4.70 (m, 2H), 3.43-3.57 (m, 4H), 3.20 (d, 1H), 2.80-2.97 (m, 5H); $^{31}$P NMR ($CDCl_3$): 12.13 ppm; MS: 824 (M+H).

Monophenol 8.3: The monophenol 8.3 (124 mg, 68%) was prepared from the diphenol 8.2 by treating with 1N NaOH in acetonitrile at 0° C.

Monoamidate 8.4: To a pyridine solution (0.5 mL) of 8.3 (40 mg, 53 mmol), n-butyl amidate HCl salt (116 mg, 640 mmol), and DIPEA (83 mg, 640 μmol) was added a pyridine solution (0.5 mL) of triphenyl phosphine (140 mg, 640 μmol), and aldrithiol-2 (120 mg, 640 μmol). The resulting solution was stirred at 65° C. overnight, worked up, and purified by preparative TLC twice to give 8.4 (1.8 mg). δ 4.96 (d, 1H), 4.90 (d, 1H) 4.30-4.6 (m, 2H), 3.9-4.2 (m, 2H), 3.6-3.70 (m, 4H), 3.2-3.3 (d, 1H), 2.80-3.1 (m, 4H); MS: 875 (M+H) & 897 (M+Na)

Scheme 9

8.3

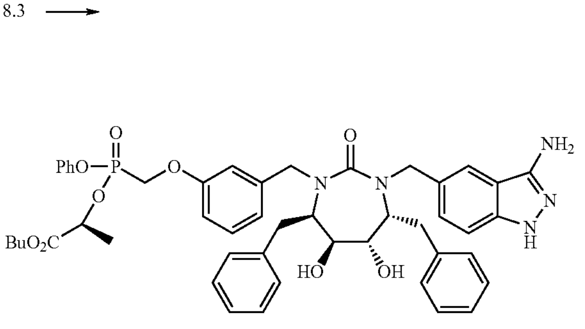

9.1

Monolactate 9.1: The monolactate 9.1 is prepared from 8.3 using the conditions described above for the preparation of the monoamidate 8.4 except n-butyl lactate was used in place of n-butyl amidate HCl salt.

Scheme 10

6.5

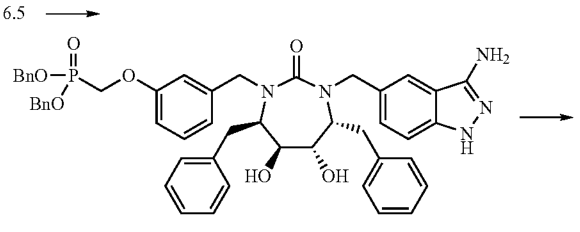

10.1

-continued

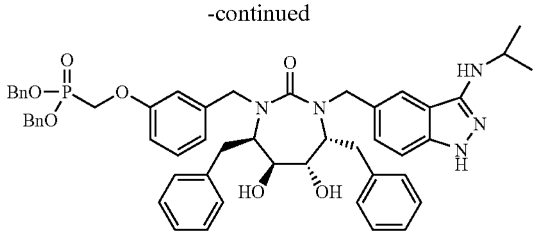

10.2

Dibenzylphosphonate 10.1: Compound 6.5 (16 mg, 0.014 mmol) was dissolved in $CH_2Cl_2$ (2 mL) and cooled to 0° C. TFA (1 mL) was added and the reaction mixture was stirred for 0.5 h. The mixture was then allowed to warm to room temperature for 2 h. The reaction mixture was concentrated under reduced pressure and azeotroped with toluene. The residue was purified by silica gel eluting with $CH_2Cl_2$: MeOH (9:1) to afford compound 10.1 (4 mg, 32%).

Isopropylamino indazole 10.2: Compound 10.1 (30 mg, 0.35 mmol) was treated with acetone according to the method of Henke et al. (J. Med Chem. 40 17 (1997) 2706-2725) to yield 10.2 as a crude residue. The residue was purified by silica gel eluting with $CH_2Cl_2$: MeOH (93:7) to afford compound 10.2 (3.4 mg, 10%).

Scheme 11

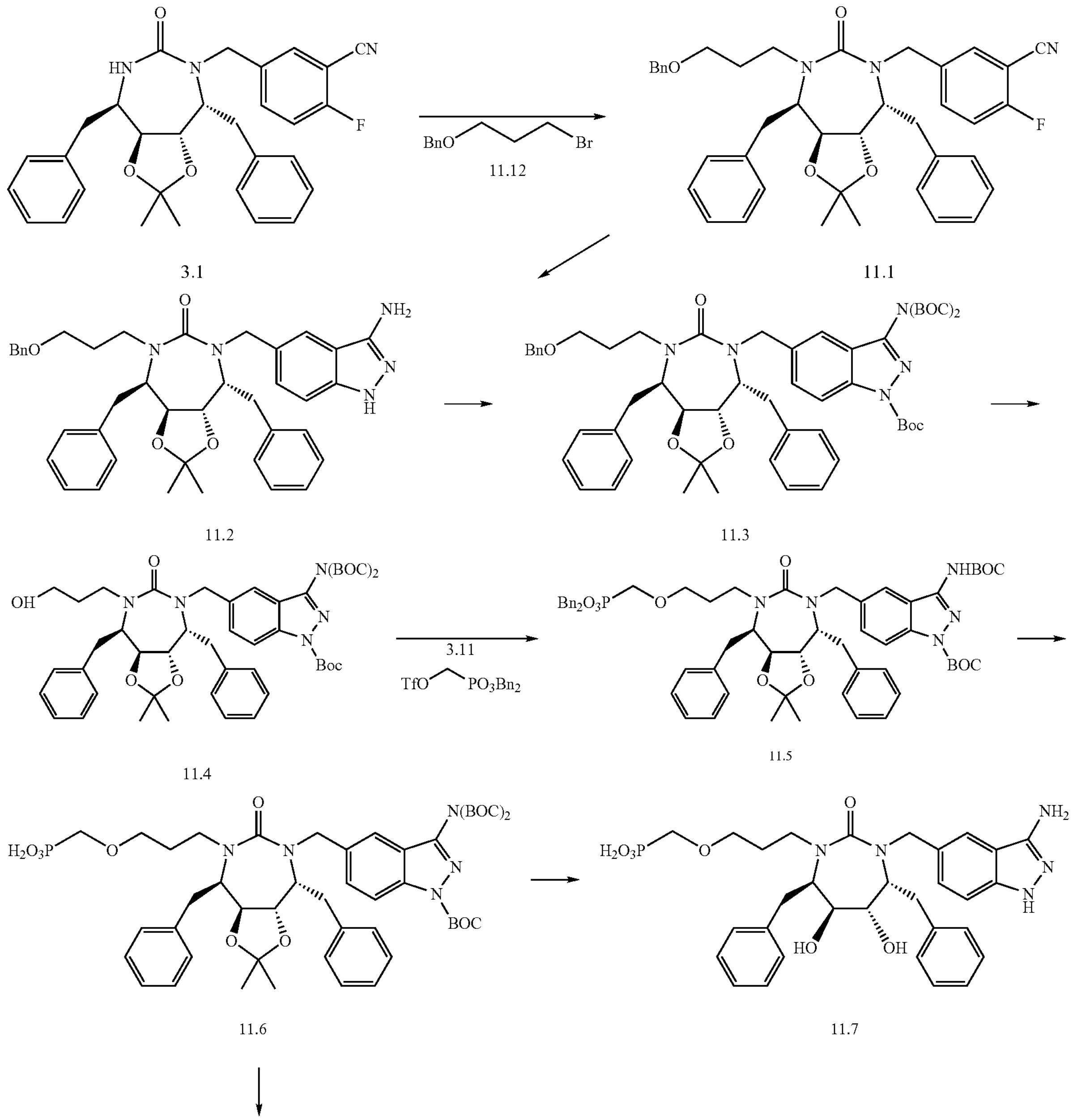

3.1 11.1 11.2 11.3 11.4 11.5 11.6 11.7

-continued
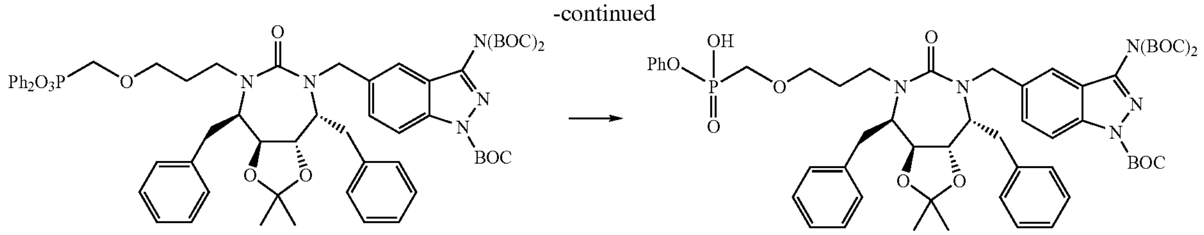
11.8 11.9
11.9
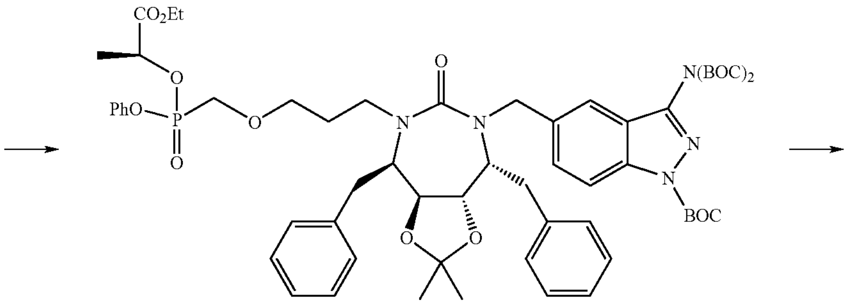
11.10
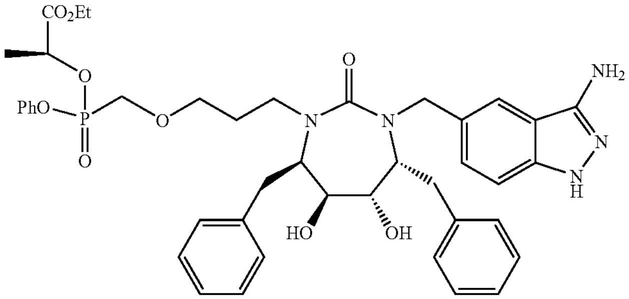
11.11
11.4
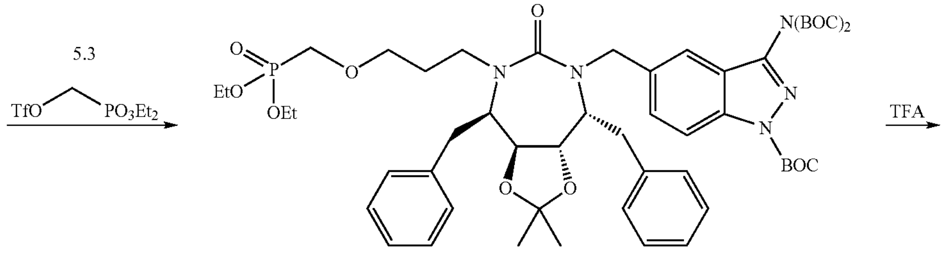
11.12
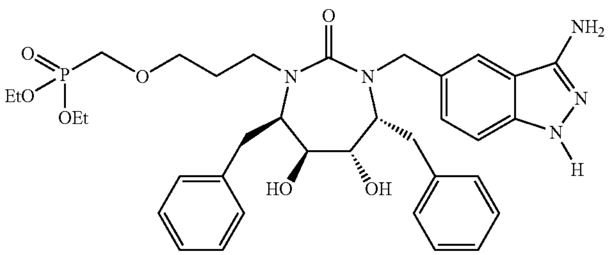
11.13
Benzyl ether 11.1: A DMF solution (5 mL) of 3.1 (0.98 g, 1.96 mmol) was treated with NaH (0.24 g of 60% oil dispersion, 6 mmol) for 30 min, followed by the addition of sodium iodide (0.3 g, 2 mmol), and benzoxypropyl bromide (0.55 g, 2.4 mmol). After the reaction for 3 h at room temperature, the reaction mixture was partitioned between methylene chloride and saturated NaCl, dried, and purified to give 11.1 (0.62 g, 49%).

Aminoindazole 11.2: A n-butanol solution (10 mL) of 11.1 (0.6 g, 0.92 mmol) and hydrazine hydrate (0.93 g, 15.5 mmol) was heated at reflux for 4 h. The reaction mixture was concentrated under reduced pressure to give crude 11.2 (0.6 g).

Tri-BOC-Aminoindazole 11.3: A methylene chloride solution (10 mL) of crude 11.2, DIPEA (0.36 g, 2.8 mmol), $(BOC)_2O$ (0.73 g, 3.3 mmol), and DMAP (0.34 g, 2.8 mmol) was stirred for 5 h at room temperature, partitioned between methylene chloride and 5% citric acid solution, dried, purified by silica gel column chomatography to give 11.3 (0.51 g, 58%, 2 steps).

3-Hydroxypropyl cyclic urea 11.4: An ethyl acetate/ethanol solution (30 mL/5 mL) of 11.3 (0.5 g, 0.52 mmol) was hydrogenated at 1 atm in the presence of 10% Pd/C (0.2 g) for 4 h. The catalyst was removed by filtration. The filtrate was then concentrated under reduced pressure to afford crude 11.4 (0.44 g, 98%).

Dibenzyl phosphonate 11.5: A THF solution (3 mL) of 11.4 (0.5 g, 0.57 mmol) and triflate dibenzyl phosphonate 3.11 (0.37 g, 0.86 mmol) was cooled to −3° C., followed by addition of n-BuLi (0.7 mL of 2.5 M hexane solution, 1.7 mmol). After 2 h reaction, the reaction mixture was partitioned between methylene chloride and saturated NaCl solution, concentrated under reduced pressure. The residue was redissolved in methylene chloride (10 mL), and reacted with $(BOC)_2O$ (0.15 g, 0.7 mmol) in the presence of DMAP (0.18 g, 0.57 mmol), DIPEA (0.18 g, 1.38 mmol) for 2 h at room temperature. The reaction mixture was worked up, and purified by silica gel chromatography to give 11.5 (0.25 g, 43%).

Phosphonic diacid 11.7: An ethyl acetate solution (2 mL) of 11.5A (11 mg, 10.5 μmol) was hydrogenated at 1 atm in the presence of 10% Pd/C (10 mg) for 6 h. The catalyst was removed by filtration, and the filtrate was concentrated under reduced pressure to give crude 11.6. The crude 11.6 was redissolved in methylene chloride (1 mL) and treated with TFA (0.2 mL) for 4 h at room temperature. The reaction mixture was concentrated under reduced pressure and purified by HPLC to give 11.7 (2 mg, 30%).

NMR ($CD_3OD$): δ 7.1-7.3 (m, 11H), 7.0-7.1 (d, 2H), 4.95 (d, 1H), 3.95-4.1 (d, 1H), 2.9-3.3 (m, 4H), 2.3-2.45 (m, 1H), 1.6-1.8 (m, 2H). P NMR ($CD_3OD$): 15.5 ppm. MS: 624 (M+1).

Diphenyl phosphonate 11.8: A pyridine solution (1 mL) of 11.6 (0.23 g, 0.23 mmol), phenol (0.27 g, 2.8 mmol), and DCC (0.3 g, 1.4 mmol) was stirred for 5 min. at room temperature, then reacted at 70° C. for 3 h. The reaction mixture was cooled to room temperature, concentrated under reduced pressure, and purified by silica gel column chromatograph to afford 11.8 (0.11 g, 41%).

Monophenyl phosphonate 11.9: An acetonitrile solution (2 mL) of 11.8 (0.12 g, 0.107 mmol) at 0° C. was treated with 1N sodium hydroxide aqueous solution (0.2 mL) for 1.5 h., then acidified with Dowex (50w×8-200, 120 mg). The Dowex was removed by filtration, and the filtrate was concentrated under reduced pressure. The residue was triturated with 10% EtOAc/90% hexane twice to afford 11.9 (90 mg, 76%) as a white solid.

Mono-ethyl lactate phosphonate 11.10: A pyridine solution (0.3 mL) of 11.9 (33 mg, 30 μmol), ethyl lactate (41 mg, 340 μmol), and DCC (31 mg, 146 μmol) was stirred at room temperature for 5 min, then reacted at 70° C. for 1.5 h. The reaction mixture was concentrated under reduced pressure, partitioned between methylene chloride and saturated NaCl solution, and purified by silica gel chromatography to give 11.10 (18 mg, 50%).

Ethyl lactate phosphonate 11.11: A methylene chloride solution (0.8 mL) of 11.10 (18 mg, 15.8 μmol) was treated with TFA (0.2 mL) for 4 h, and then concentrated under reduced pressure. The residue was purified by preparative TLC to give 11.11 (6 mg, 50%). NMR ($CDCl_3$+~10% $CD_3OD$): δ 7.0-7.3 (m, 16H), 6.8-7.0 (m, 2H), 4.9-5.0 (m, 1H), 4.75 (d, 1H), 4.1-4.2 (m, 2H), 3.5-4.0 (m, 10H), 2.18-2.3, (m, 1H), 1.6-1.7 (m, 1), 1.47 & 1.41 (2d, 3H), 1.22 (t, 3H). P NMR ($CDCl_3$+~10% $CD_3OD$): 19.72 & 17.86 ppm.

Diethyl phosphonate 11.13: Compound 11.13 (6 mg) was prepared as described above in Scheme 5 from 11.4 (30 mg, 34 μmol) and triflate phosphonate 5.3 (52 mg, 172 μmol), followed by TFA treatment. NMR ($CDCl_3$+~10% $CD_3OD$): δ 7.1-7.32 (m, 11H), 6.9-7.0 (d, 2H), 4.75 (d, 1H), 4.1-4.2 (2q, 4H), 3.84-3.9 (m, 1H), 3.4-3.8 (m, 8H), 2.7-3.1 (m, 4H), 2.1-2.5 (m, 1H), 1.5-1.7 (m, 2H), 1.25-1.35 (2t, 6H). P NMR ($CDCl_3$+~10% $CD_3OD$): 21.63 ppm. MS: 680 (M+1).

Scheme 12

11.9

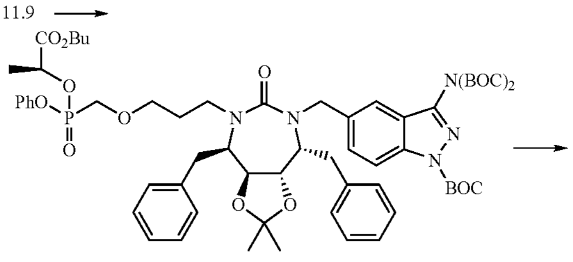

12.1

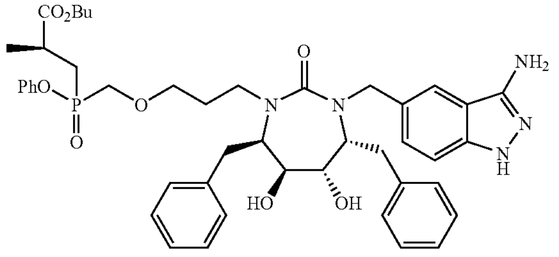

12.2

Butyl lactate phosphonate 12.2: A pyridine solution (0.3 mL) of 11.9 (27 mg, 22 μmol), butyl lactate (31 mg, 265 mmol), and DCC (28 mg, 132 μmol) was stirred at room temperature for 5 min, then reacted at 70° C. for 1.5 h. The reaction mixture was concentrated under reduced pressure, partitioned between methylene chloride and saturated NaCl solution, and purified by preparative TLC to give 12.1 (12 mg). A methylene chloride solution (0.8 mL) of 12.1 (12 mg) was treated with TFA (0.2 mL) for 4 h, concentrate. The residue was purified by preparative TLC to give 12.2 (3 mg, 16%). NMR ($CDCl_3$+~10% $CD_3OD$): δ 6.8-7.4 (m, 18H), 6.4-6.6 (m), 4.9-5.05 (m, 1H), 4.75 (d, 1H), 4.1-4.2 (m, 2H). 3.5-4.0 (m, 10H), 3.1-3.25 (m, 2H), 2.2-2.35 (m, 1H), 1.8-1.9 (m, 1H), 1.4 & 1.8 (m, 7H), 1.22 (t, 3H). P NMR ($CDCl_3$+~10% $CD_3OD$): 19.69 & 17.86 ppm.

Scheme 13

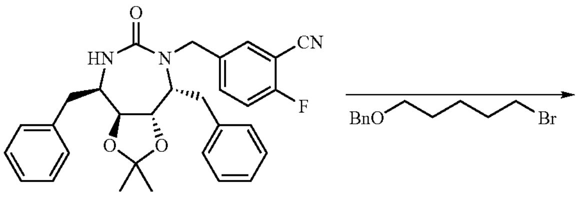

3.1

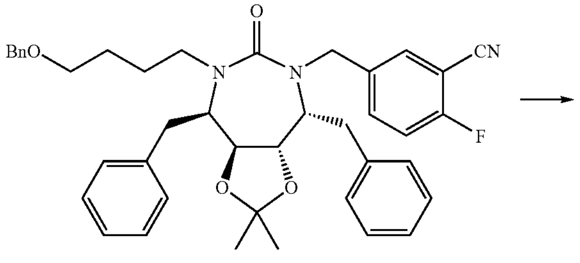

13.1

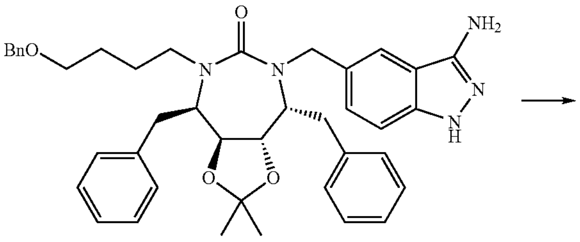

13.2

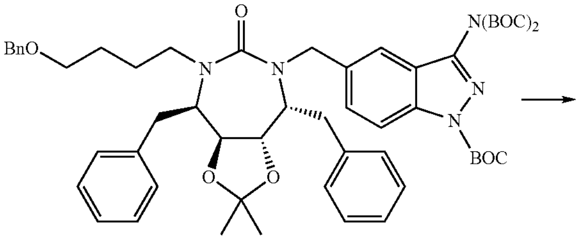

13.3

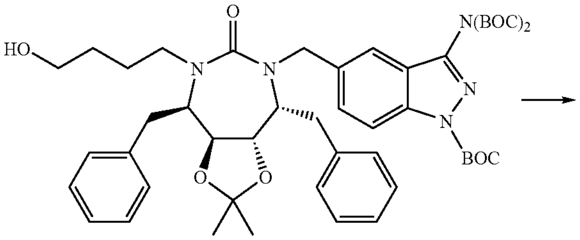

13.4

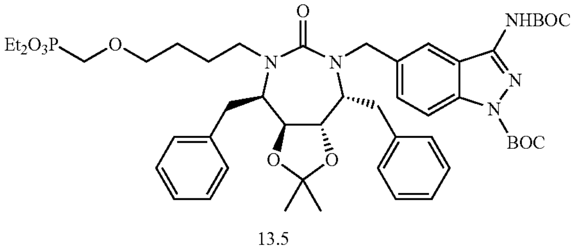

13.5

-continued

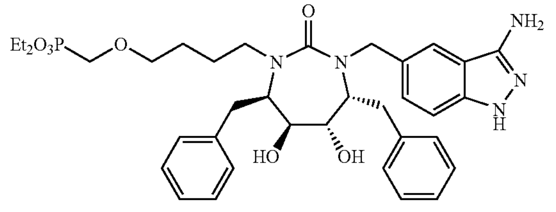

13.6

Benzyl ether 13.1: A DMF solution (5 mL) of 3.1 (1 g, 2 mmol) was treated with NaH (0.24 g of 60% oil dispersion, 6 mmol) for 30 min, followed by the addition of sodium iodide (0.3 g, 2 mmol), and benzoxybutyl bromide (0.58 g, 2.4 mmol). After the reaction for 5 h at room temperature, the reaction mixture was partitioned between methylene chloride and saturated NaCl, dried, and purified to give 13.1 (0.58 g, 44%).

Aminoindazole 13.2: A n-butanol solution (10 mL) of 11.1 (0.58 g, 0.87 mmol) and hydrazine hydrate (0.88 g, 17.5 mmol) was heated at reflux for 4 h. The reaction mixture was concentrated under reduced pressure to give crude 13.2 (0.56 g).

Tri-BOC-aminoindazole 13.3: A methylene chloride solution (10 mL) of 13.2 (0.55 g, 0.82 mmol), DIPEA (0.42 g, 3.2 mmol), $(BOC)_2O$ (0.71 g, 3.2 mmol), and DMAP (0.3 g, 2.4 mmol) was stirred for 4 h at room temperature, partitioned between methylene chloride and 5% citric acid solution, dried, purified by silica gel chromatography to give 13.3 (0.56 g, 71%, 2 steps).

3-Hydroxybutyl cyclic urea 13.4: An ethyl acetate/methanol solution (30 mL/5 mL) of 11.3 (0.55 g, 0.56 mmol) was hydrogenated at 1 atm in the presence of 10% Pd/C (0.2 g) for 3 h. The catalyst was removed by filtration. The filtrate was concentrated under reduced pressure to afford crude 13.4 (0.5 g, 98%).

Diethyl phosphonate 13.6: A THF solution (1 mL) of 13.4 (5 mg, 56 μmol) and triflate diethyl phosphonate 5.3 (30 mg, 100 μmol) was cooled to −3° C., followed by addition of n-BuLi (80 μl of 2.5 M hexane solution, 200 μmol). After 2 h reaction, the reaction mixture was partitioned between methylene chloride and saturated NaCl solution, concentrated under reduced pressure to give crude 13.5. The residue was dissolved in methylene chloride (0.8 mL) and treated with TFA (0.2 mL) for 4 h. concentrated under reduced pressure, and purified by HPLC to give 13.6 (8 mg, 21%). NMR ($CDCl_3$): δ 7.1-7.4 (m, 11H), 7.0-7.1 (m, 2H) 4.81 (d, 1H), 4.1-4.25 (m, 4H). 3.85-3.95 (m, 1H), 3.4-3.8 (m, 7H), 3.3-3.4 (m, 1H), 2.8-3.25 (m, 5H), 2.0-2.15 (m, 1H), 1.3-1.85 (m, 10H). P NMR ($CDCl_3$): 21.45 ppm.

Scheme 13a
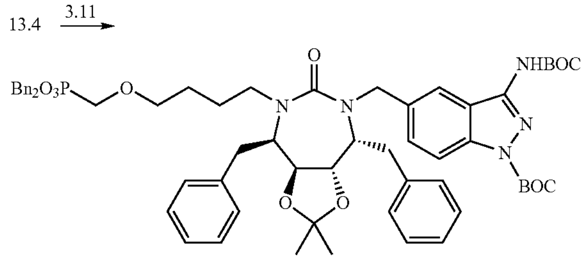
13.7
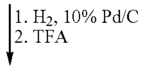
-continued
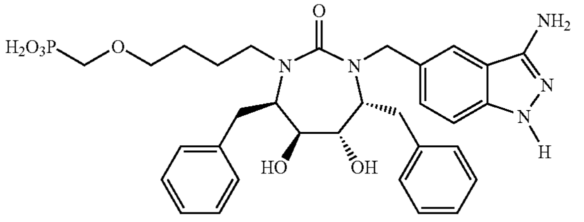
13.8
Phosphonic diacid 13.8: Compound 13.8 (4.5 mg) was prepared from 13.4 as described above for the preparation of 11.7 from 11.4 (Scheme 11). NMR ($CD_3OD$): δ 7.41 (s, 1H), 7.1-7.4 (m, 10H), 6.9-7.0 (m, 2H) 4.75 (d, 1H), 3.8-4.0 (m, 1H). 3.4-3.8 (m, 8H), 2.8-3.25 (m, 5H), 2.1-2.25 (m, 1H), 1.6-1.85 (m, 4H). MS: 638 (M+1).
Scheme 14
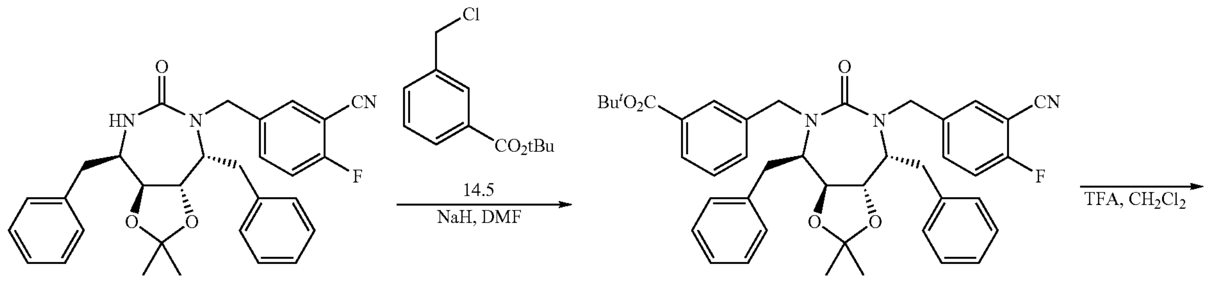
3.1 14.1
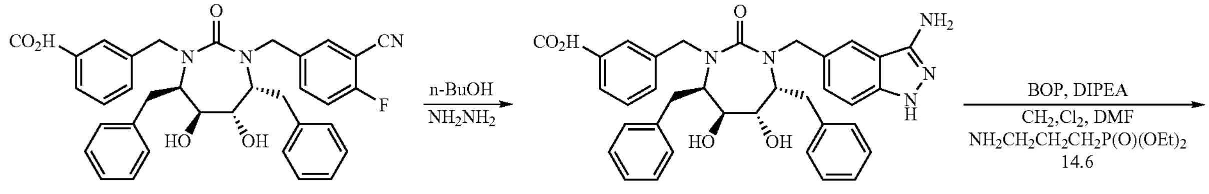
14.2 14.3
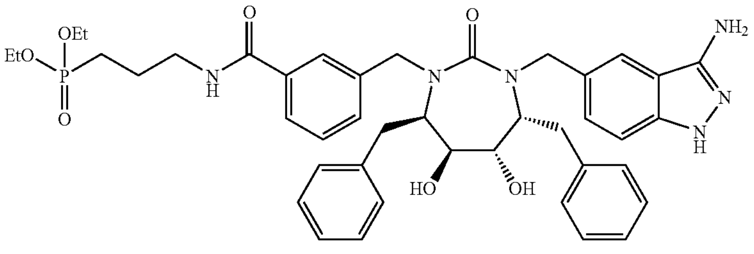
14.4
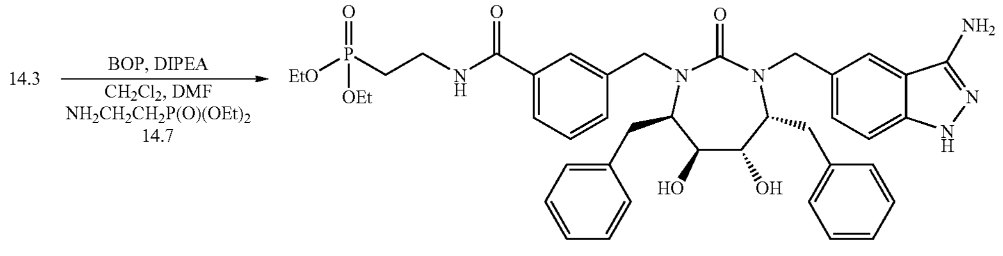
14.5 t-Butyl ester 14.1: A DMF solution (3 mL) of 3.1 (0.5 g, 1 mmol) was treated with NaH (80 mg of 60% oil dispersion, 2 mmol) for 10 min, followed by the addition of 14.5 (0.25 g, 1.1 mmol). After the reaction for 1 h at room temperature, the reaction mixture was partitioned between methylene chloride and saturated NaCl, dried, and purified to give 14.1 (0.4 g, 59%).

Aminoindazole derivative 14.3: A methylene chloride solution (5 mL) of 14.1 (0.4 g, 0.58 mmol) was treated with TFA (1 mL) at room temperature for 1.5 h, and then concentrated under reduced pressure to give crude 14.2. The crude 14.2 was dissolved in n-BuOH (5 mL) and reacted with hydrazine hydrate (0.58 g, 11.6 mmol) at reflux for 5 h. The reaction mixture was concentrated under reduced pressure and purified by silica gel chromatography to give the desired product 14.3 (0.37 g, quantitative yield).

Diethylphosphonate ester 14.4: A methylene chloride solution (3 mL) of 14.3 (23 mg, 38 μmol) was reacted with aminopropyl-diethylphosphonate 14.6 (58 mg, 190 μmol), DIPEA (50 mg, 380 μmol), and ByBOP (21 mg, 48 μmol) at room temperature for 2 h, and then concentrated under reduced pressure. The residue was triturated with methylene chloride/hexane. The solid was purified by preparative TLC to give 14.4 (9 mg, 34%). NMR ($CDCl_3$+~10% $CD_3O$): δ 7.87 (t, 1H), 7.61 (b, 1H), 7.51 (s, 1H), 7.14-7.2 (m, 10H), 6.937.0 (m, 4H), 4.79 (d, 2H), 3.99-4.04 (m, 4H), 3.38-3.65 (m, 6H), 2.60-3.2 (m, 6H), 1.70-1.87 (m, 4H), 1.25 (t, 6H). P NMR ($CDCl_3$+~10% $CD_3OD$): 32.7 ppm.

Diethylphosphonate ester 14.5: A methylene chloride solution (2 mL) of 14.3 (13 mg, 21 μmol) was reacted with aminoethyl-diethylphosphonate oxalate 14.7 (23 mg, 85 μmol), DIPEA (22 mg, 170 μmol), and ByBOP (12 mg, 25 μmol) at room temperature for 2 h, and then concentrated under reduced pressure. The residue was triturated with methylene chloride/hexane. The solid was purified by preparative TLC to give 14.5 (5 mg, 30%). Ms: 783 (M+1). NMR ($CDCl_3$+~10% $CD_3O$): δ 7.88 (b, 1H), 7.58 (b, 1H), 7.49 (s, 1H), 7.14-7.2 (m, 10H), 6.90-7.0 (m, 4H), 4.75 (d, 2H), 3.90-4.04 (m, 4H), 2.50-3.3 (m, 6H), 1.97-2.08 (m, 2H). P NMR ($CDCl_3$+~10% $CD_3OD$): 30.12 ppm.

Scheme 15

14.3

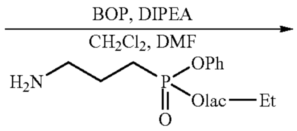

15.5

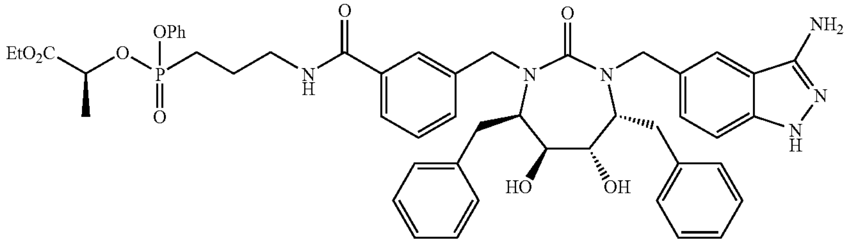

15.1

14.3

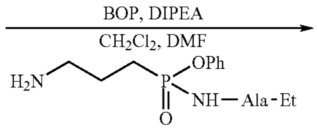

15.6

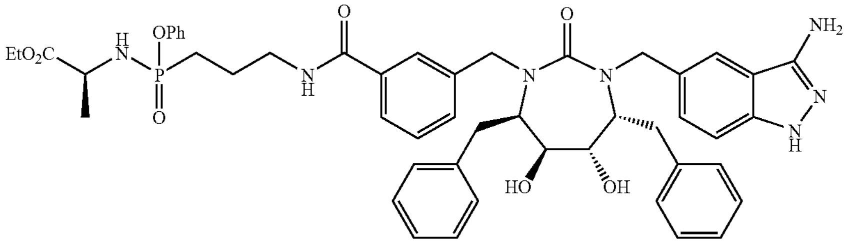

15.2

14.3

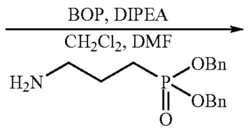

15.7

-continued

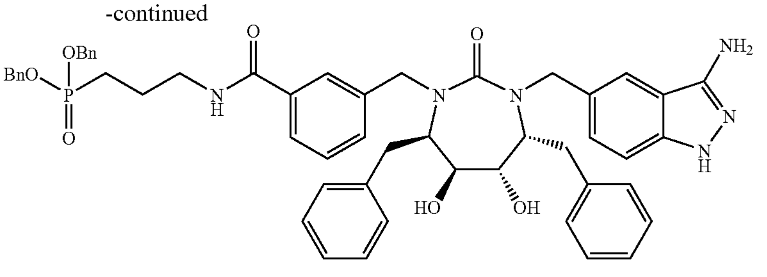

15.3

$H_2$, Pd/C

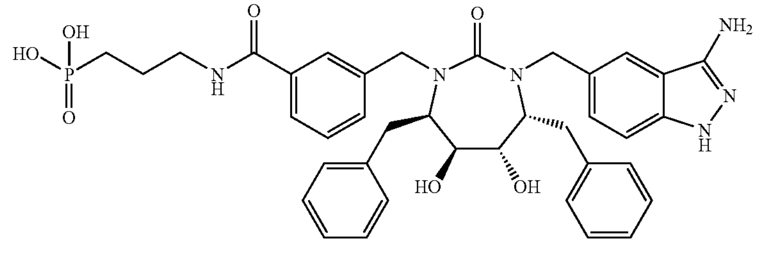

15.4

Monophenol-ethyl lactate phosphonate prodrug 15.1: A methylene chloride/DMF 5 mg, 49 μmmol) was reacted with aminopropyl-phenol-ethyl lactate phosphonate 15.5 (100 mg, 233 μmol), DIPEA (64 mg, 495 μmol), and BOP reagent (45 mg, 100 μmol) at room temperature for 2 h, and then concentrated under reduced pressure. The residue was triturated with methylene chloride/hexane. The solid was purified by silica gel chromatography to give 15.1 (28 mg, 64%). NMR ($CDCl_3$+~10% $CD_3O$): δ 7.83 (b, 1H), 7.59 (b, 1H), 7.51 (s, 1H), 7.14-7.2 (m, 11H), 6.90-7.0 (m, 4H), 4.75-4.87 (d+q, 3H), 4.10 (q, 2H), 3.3-3.61 (m, 6H), 2.60-3.2 (m, 6H), 1.92-2.12 (m, 4H), 1.30 (d, 3H), 1.18 (t, 3H). P NMR ($CDCl_3$+~10% $CD_3OD$): 30.71 ppm. MS: 903 (M+1).

Phenol-ethyl alanine phosphonate prodrug 15.2: A methylene chloride/DMF solution (2 mL/0.5 mL) of 14.3 (30 mg, 49 μmol) was reacted with aminopropyl-phenol-ethyl alanine phosphonate 15.6 (80 mg TFA salt, 186 μmol), DIPEA (64 mg, 500 μmol), and BOP reagent (45 mg, 100 μmol) at room temperature for 2 h, and then concentrated under reduced pressure. The residue was triturated with methylene chloride/hexane. The solid was purified by preparative TLC to give 15.2 (12 mg, 27%). NMR ($CDCl_3$+~10% $CD_3O$): δ 7.91 (b, 1H), 7.61 (b, 1H), 7.52 (s, 1H), 7.14-7.2 (m, 11H), 6.90-7.0 (m, 4H), 4.75 (d, 2H), 3.82-4.1 (2q, 3H), 3.4-3.65 (m, 6H), 2.60-3.15 (m, 6H), 1.8-2.0 (m, 4H), 1.3 (d, 3H). P NMR ($CDCl_3$+~10% $CD_3OD$): 32.98 & 33.38 ppm. MS: 902 (M+1).

Dibenzyl phosphonate 15.3: A methylene chloride/DMF solution (2 mL/0.5 mL) of 14.3 (30 mg, 49 μmol) was reacted with aminopropyl dibenzyl phosphonate 15.7 (86 mg TFA salt, 200 μmol), DIPEA (64 mg, 500 μmol), and BOP reagent (45 mg, 100 μmol) at room temperature for 2 h, and then concentrated under reduced pressure. The residue was triturated with methylene chloride/hexane. The solid was purified by preparative TLC to give 15.3 (20 mg, 44%). NMR ($CDCl_3$+5% $CD_3O$): δ 7.50-7.58 (m, 2H), 7.14-7.3 (m, 21H), 6.90-7.0 (m, 4H), 4.7-5.1 (m, 6H), 3.6-3.8 (m, 4H), 3.3-3.55 (m, 2H), 2.60-3.15 (m, 6H), 1.82.0 (m, 4H). P NMR ($CDCl_3$+5% $CD_3OD$): 33.7 ppm. MS: 907 (M+1).

Phosphonic diacid 15.4: An ethanol solution (5 mL) of 15.3 (17 mg, 18.7 μmol) was hydrogenated at 1 atm in the presence of 10% Pd/C for 4 h. The catalyst was removed by filtration, and the filtrate was concentrated under reduced pressure to give the desired product 15.4 (12 mg, 85%). NMR ($CD_3O$+20% $CDCl_3$): δ 7.88 (b, 1H), 7.59 (b, 1H), 7.6 (s, 1H), 7.1-7.25 (m, 10H), 6.90-7.1 (m, 4H), 4.8 (d, 2H+water peak), 3.6-3.8 (m, 4H), 3.4-3.5 (m, 2H), 1.85-2.0 (m, 4H).

Scheme 16

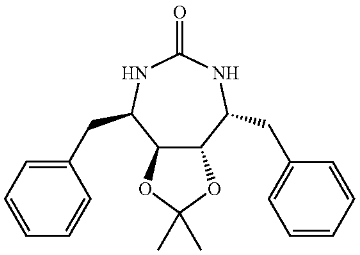

1.1

NaH, DMF

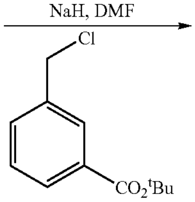

14.5

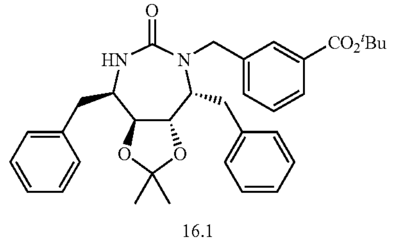

16.1

NaH, DMF

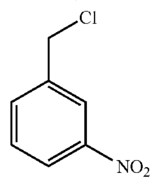

16.6

-continued

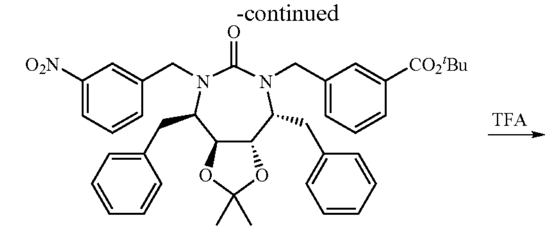

16.2

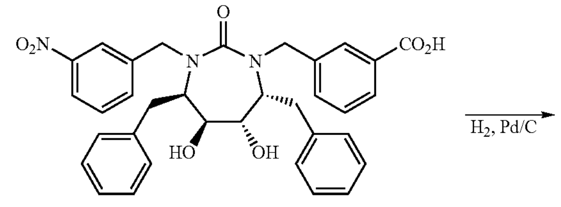

16.3

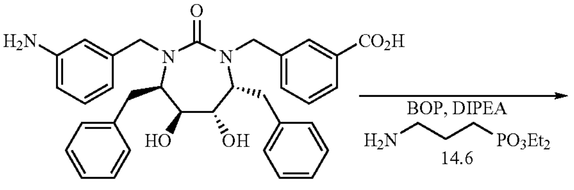

16.4

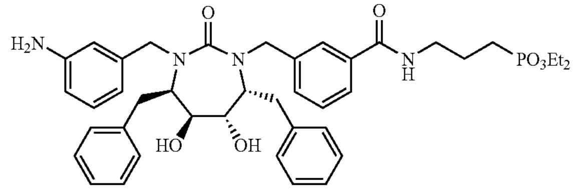

16.5

Monobenzyl derivative 16.1: A DMF solution (4 mL) of 1.1 (0.8 g, 2.2 mmol) was treated with NaH (0.18 g of 60% oil dispersion, 4.4 mmol) for 10 min at room temperature followed by the addition of 14.5 (0.5 g, 2.2 mmol). The resulting solution was reacted at room temperature for 2 h, worked up, and then purified to afford 16.1 (0.48 g, 40%).

3-Nitrobenzyl cyclic urea derivative 16.2: A DMF solution (0.5 mL) of 16.1 (65 mg, 117 μmol) was treated with NaH (15 mg of 60% oil dispersion, 375 μmol) for 10 min at room temperature, followed by the addition of 3-nitrobenzyl bromide (33 mg, 152 μmol). The resulting solution was reacted at room temperature for 1 h, worked up, and purified by preparative TLC to afford 16.2 (66 mg, 82%).

Diol 16.3: A methylene chloride solution (2 mL) of 16.2 (46 mg, 61 μmol) was treated with TFA (0.4 mL) for 2 h at room temperature, and then concentrated under reduced pressure to afford 16.3. This material was used without further purification.

3-Aminobenzyl cyclic urea 16.4: An ethyl acetate/ethanol (5 mL/1 mL) solution of 16.3 (crude) was hydrogenated at 1 atm in the presence of 10% Pd/C for 2 h. The catalyst was removed by filtration. The filtrate was concentrated under reduced pressure, and purified by preparative TLC to afford 16.4 (26 mg, 70%, 2 steps).

Diethyl phosphonate 16.5: A methylene chloride/DMF solution (2 mL/0.5 mL) of 16.4 (24 mg, 42 μmol) was reacted with aminopropyl-diethylphosphonate ester TFA salt 14.6 (39 mg, 127 μmol), DIPEA (27 mg, 210 μmol), and BOP reagent (28 mg, 63 μmol) at room temperature for 2 h, and then concentrated under reduced pressure. The residue was purified by preparative TLC to give 16.5 (20.7 mg, 63%). NMR ($CDCl_3$+~10% $CD_3O$): δ 7.62 (b, 1H), 7.51 (s, 1H), 7.0-7.35 (m, 12H), 6.95 (d, 2H), 6.85 (d, 2H), 4.6-4.71 (2d, 2H), 3.95-4.1 (m, 4H). 3.3-3.55 (m, 3H), 2.60-2.8 (m, 2H), 2.95-3.15 (m, 4H), 1.85-2.0 (m, 4H), 1.25 (t, 6H). P NMR ($CDCl_3$+~10% $CD_3OD$): 32.65 ppm.

Scheme 17

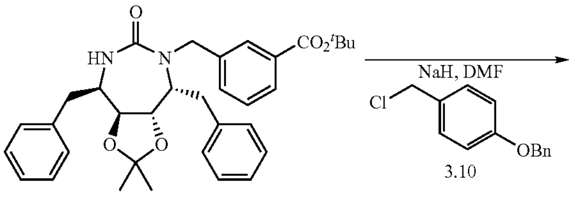

16.1

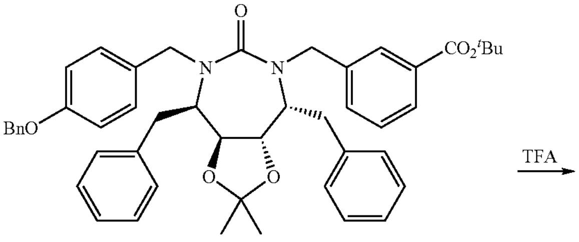

17.1

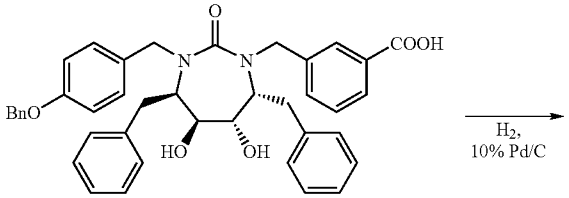

17.2

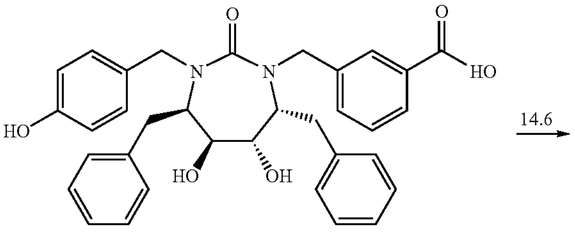

17.3

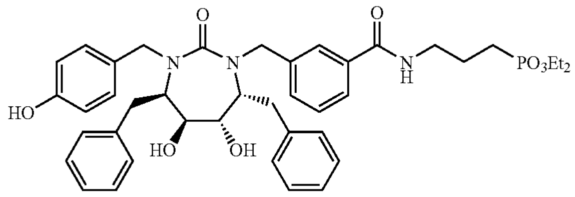

17.4 p-Benzoxybenzyl cyclic urea derivative 17.1: A DMF solution (0.5 mL) of 16.1 (65 mg, 117 μmol) was treated with NaH (15 mg of 60% oil dispersion, 375 μmol) for 10 min at room temperature, followed by the addition of 4-benzoxy benzyl chloride 3.10 (35 mg, μmol). The resulting solution was stirred for 2 h at room temperature. The reaction mixture was concentrated under reduced pressure, purified by preparative TLC to generate 17.1 (62 mg, 70%).

Diethyl phosphonate 17.3: A methylene chloride solution (2 mL) of 17.1 (46 mg, 61 μmol) was treated with TFA (0.4 mL) for 2 h at room temperature, and then concentrated under reduced pressure to give crude 17.2. An ethyl acetate/ethanol solution (3 mL/2 mL) of the crude 17.2 was then hydrogenated at 1 atm in the presence of 10% Pd/C (10 mg) for 5 h at room temperature. The catalyst was removed by filtration. The filtrate was concentrated under reduced pressure to afford 17.3 (crude).

Diethyl phosphonate cyclic urea 17.4: A methylene chloride/DMF solution (2 mL/0.5 mL) of 17.3 (25 mg, 42 μmol) was reacted with aminopropyl-diethylphosphonate ester TFA salt 14.6 (40 mg, 127 mmol), DIPEA (27 mg, 210 μmol), and BOP reagent (28 mg, 63 μmol) at room temperature for 2 h, and then concentrated under reduced pressure. The residue was purified by preparative TLC to give 17.4 (14.6 mg, 44%). NMR ($CDCl_3$+~10% $CD_3O$): δ 7.82 (t), 7.62 (d, 1H), 7.51 (s, 1H), 7.05-7.35 (m, 10H), 6.8-6.95 (2d, 4H), 6.85 (d, 2H), 4.8 (d, 1H), 4.65 (d, 1H), 3.95-4.1 (m, 4H). 3.4-3.75 (m, 6H), 2.60-3.2 (m), 1.85-2.0 (m, 4H), 1.25 (t, 6H). P NMR ($CDCl_3$+~10% $CD_3OD$): 32.72 ppm.

Scheme 18

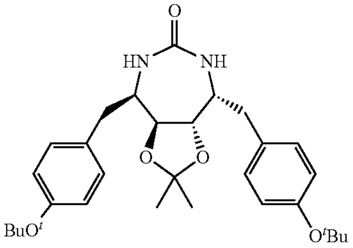

2.8

NaH, DMF

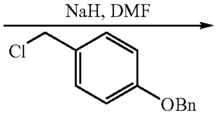

3.10

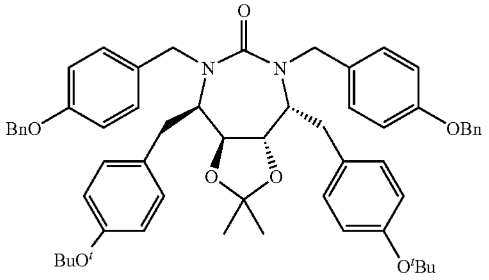

18.1

TFA

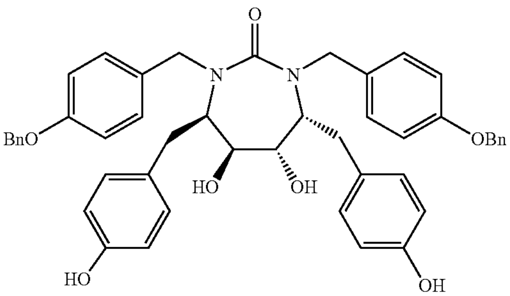

18.2

+

-continued

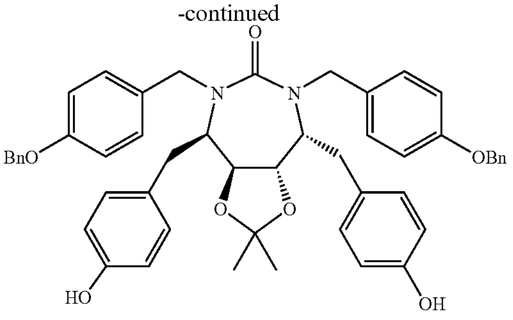

20.1

18.2

$Cs_2CO_3$, THF

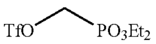

5.3

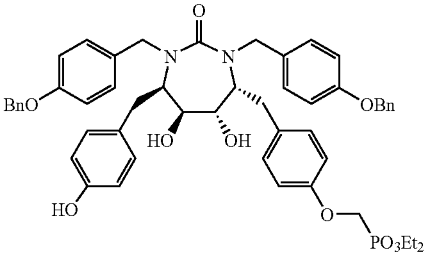

18.3

MeI, $Cs_2CO_3$

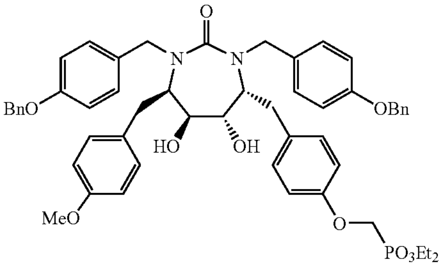

18.4

$H_2$, Pd/C

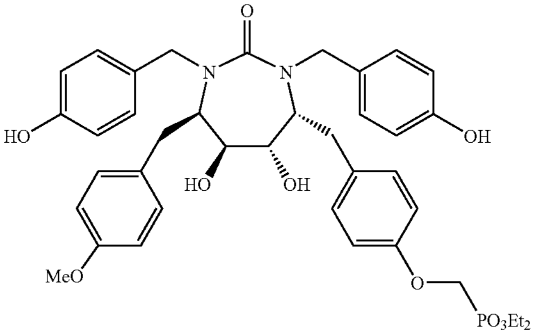

18.5

Dibenzyl derivative 18.1: A DMF solution (3 mL) of compound 2.8 (0.4 g, 0.78 mmol) was reacted with 60% NaH (0.13 g, 1.96 mmol), 4-benzoxy benzylchloride 3.10 (0.46 g, 1.96 mmol) and sodium iodide (60 mg, 0.39 mmol) at room temperature for 4 h. The reaction mixture was partitioned between methylene chloride and saturated $NaHCO_3$ solution. The organic phase was isolated, dried over $Na_2SO_4$, concentrated under reduced pressure, and purified by silica gel chromatography to give the desired product 18.1 (0.57 g, 81%).

Diol derivative 18.2 and diphenol derivative 20.1: A methylene chloride solution (4 mL) of 18.1 (0.57 g, 0.63 mmol) was treated with TFA (1 mL) at room temperature for 20 min, concentrated under reduced pressure, and purified by silica gel chromatography to give diol derivative 18.2 (133 mg, 28%) and diphenol derivative 20.1 (288 mg. 57.6%).

Monophosphonate derivative 18.3: A THF solution (10 mL) of 18.2 (130 mg, 0.17 mmol) was stirred with cesium carbonate (70 mg, 0.21 mmol) and diethylphosphonate triflate 5.3 (52 mg, 0.17 mmol) at room temperature for 4 h. The reaction mixture was concentrated under reduced pressure and purified to give 18.3 (64 mg, 41%), and recovered 18.2 (25 mg, 19%).

Methoxy derivative 18.4: A THF solution (2 mL) of 18.3 (28 mg, 25 μmol) was treated with cesium carbonate (25 mg, 76 μmol) and iodomethane (10 eq. Excess) at room temperature for 5 h. The reaction mixture was concentrated under reduced pressure and partitioned between methylene chloride and saturated $NaHCO_3$. The organic phase was separated, concentrated under reduced pressure and the residue purified by preparative TLC to afford 18.4 (22 mg, 78%).

Diethylphosphonate 18.5: An ethyl acetate/ethanol (2 mL/2 mL) solution of 18.4 (22 mg, 24 μmol) was hydrogenated at 1 atm in the presence of 10% Pd/C for 3 h. The catalyst was removed by filtration, the filtrate was concentrated under reduced pressure to give the desired product 18.5 (18 mg, quantitative). NMR ($CDCl_3$+~10% $CD_3O$): δ 6.7-7.0 (m, 12H), 6.62-6.69 (m, 4H), 4.65 (d, 1H), 4.50 (d, 1H), 4.18-4.3 (m, 6H). 3.75 (s, 3H), 3.3-3.4 (m, 4H), 2.8-3.0 (m, 6H), 1.30 (t, 6H). P NMR ($CDCl_3$+~10% $CD_3OD$): 20.16 ppm.

Scheme 19

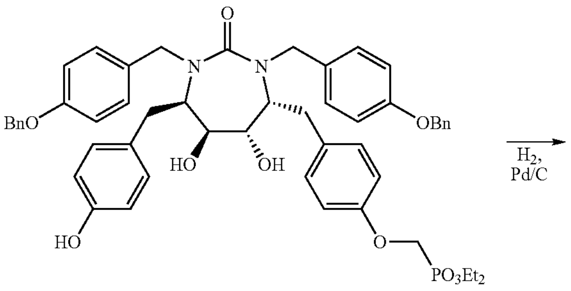

18.3

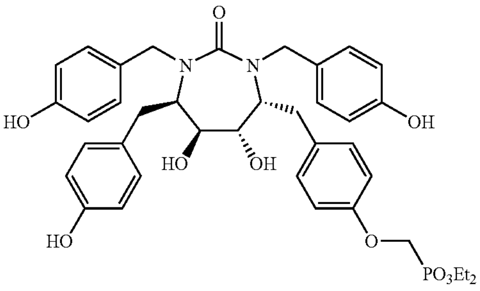

19.1

Diethyl phosphonate 19.1: An ethyl acetate/ethanol (2 mL/1 mL) solution of 18.3 (14 mg, 15.5 μmol) was hydrogenated at 1 atm in the presence of 10% Pd/C (5 mg) for 3 h. The catalyst was then removed by filtration, and the filtrate was concentrated under reduced pressure to give the desired product 19.1 (10 mg, 90%). NMR ($CDCl_3$+~15% $CD_3O$): δ 6.6-7.0 (m, 16H), 4.5-4.65 (2d, 2H), 4.1-4.3 (m, 6H). 2.7-3.0 (m, 6H), 1.29 (t, 6H). P NMR ($CDCl_3$+~15% $CD_3OD$): 20.12 ppm.

Scheme 20

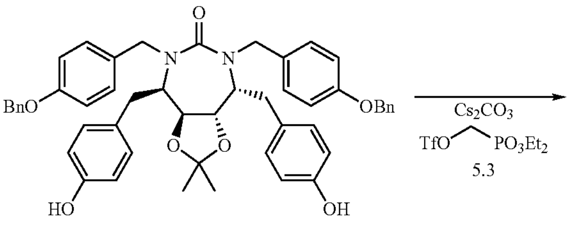

20.1

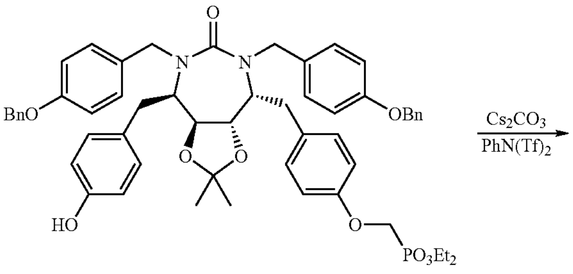

20.2

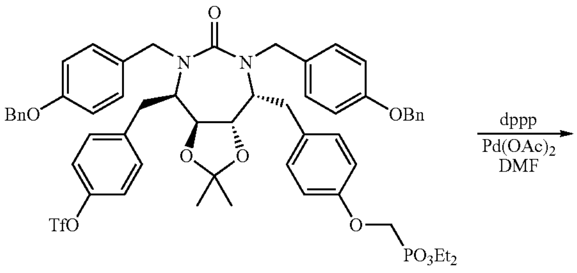

20.3

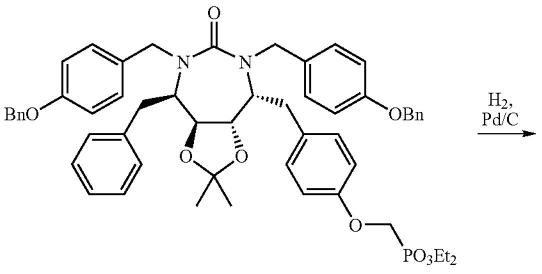

20.4

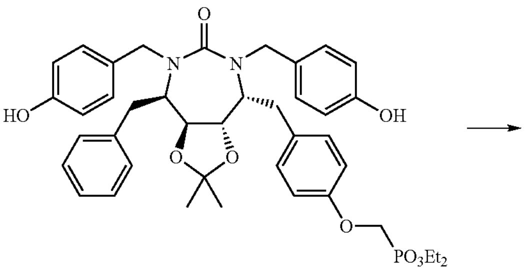

20.5

-continued

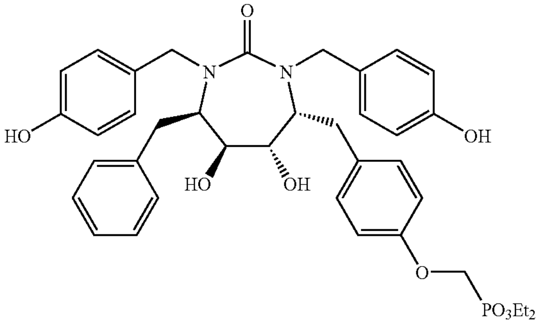

20.6

Monophosphonate 20.2: A THF solution (8 mL) of 20.1 (280 mg, 0.36 mmol) was stirred with cesium carbonate (140 mg, 0.43 mmol) and diethylphosphonate triflate 5.3 (110 mg, 0.36 mmol) at room temperature for 4 h. The reaction mixture was concentrated under reduced pressure and purified to give 20.2 (130 mg, 39%), and recovered 20.1 (76 mg, 27%).

Triflate derivative 20.3: A THF solution (6 mL) of 20.2 (130 mg, 0.13 mmol) was stirred with cesium carbonate (67 mg, 0.21 mmol) and N-phenyltrifluoromethane-sulfonimide (60 mg, 0.17 mmol) at room temperature for 4 h. The reaction mixture was concentrated under reduced pressure and purified to give 20.3 (125 mg, 84%).

Benzyl ether 20.4: To a DMF solution (2 mL) of $Pd(OAc)_2$ (60 mg, 267 μmol), and dppp (105 mg. 254 μmol) was added 20.3 (120 mg, 111 μmol) under nitrogen, followed by the addition of triethylsilane (0.3 mL). The resulting solution was stirred at room temperature for 4 h, then concentrated under reduced pressure. The residue was purified by silica gel chromatography to afford 20.4 (94 mg, 92%).

Diethyl phosphonate 20.6: An ethyl acetate/ethanol (2 mL/2 mL) solution of 20.4 (28 mg, 30 μmol) was hydrogenated at 1 atm in the presence of 10% Pd/C (5 mg) for 3 h. The catalyst was removed by filtration, and the filtrate was concentrated under reduced pressure to give the desired product 20.5. The crude product 20.5 was redissolved in methylene chloride (2 mL) and treated with TFA (0.4 mL) and a drop of water. After 1 h stirring at room temperature, the reaction mixture was concentrated under reduced pressure, and purified by preparative TLC plate to give 20.6 (18 mg, 85%, 2 steps). δ 6.6-7.3 (m, 17H), 4.65 (d, 1H), 4.58 (d, 1H), 4.18-4.3 (m, 6H), 3.3-3.5 (m, 4H), 2.8-3.1 (m), 1.34 (t, 6H). P NMR ($CDCl_3$+~10% $CD_3OD$): 20.16 ppm. MS: 705 (M+1).

Scheme 21

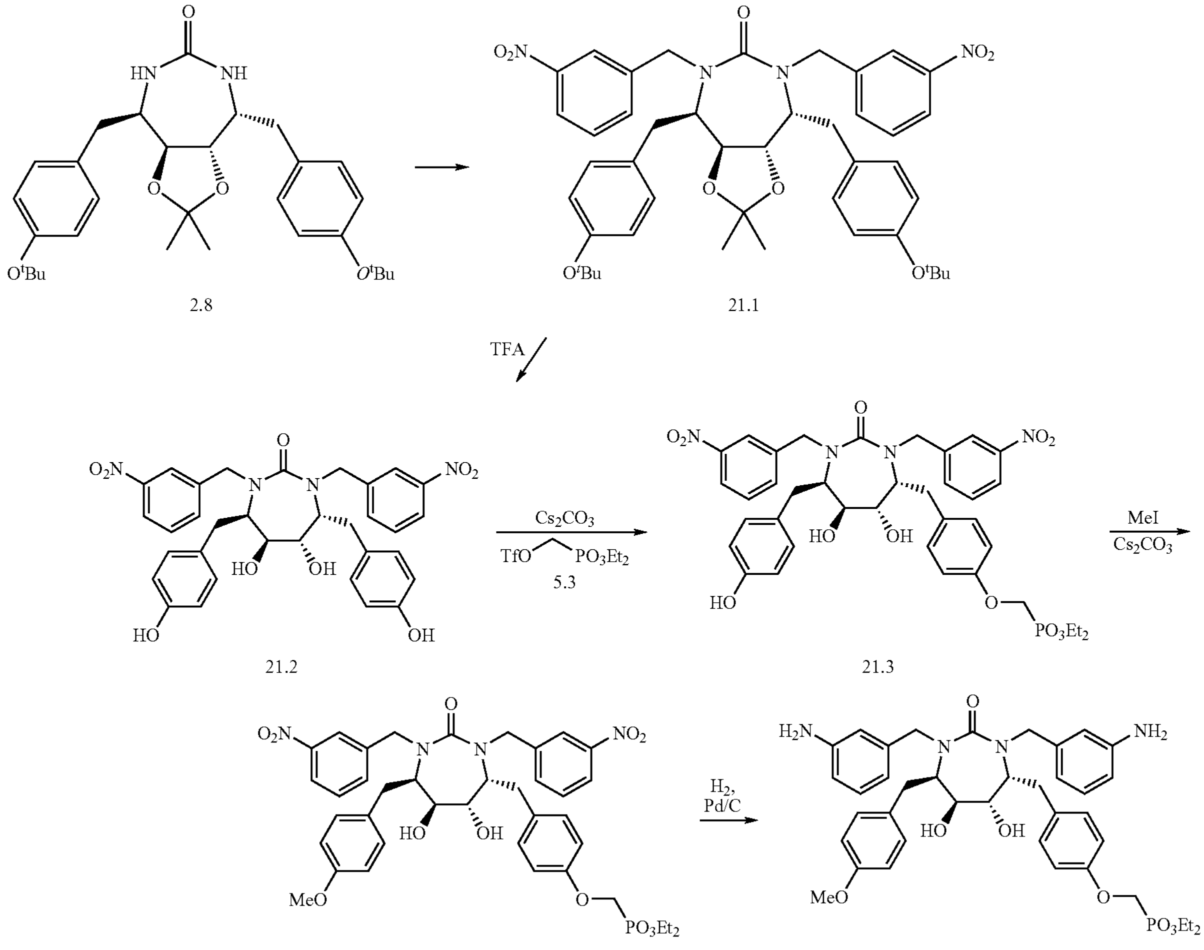

-continued 21.3

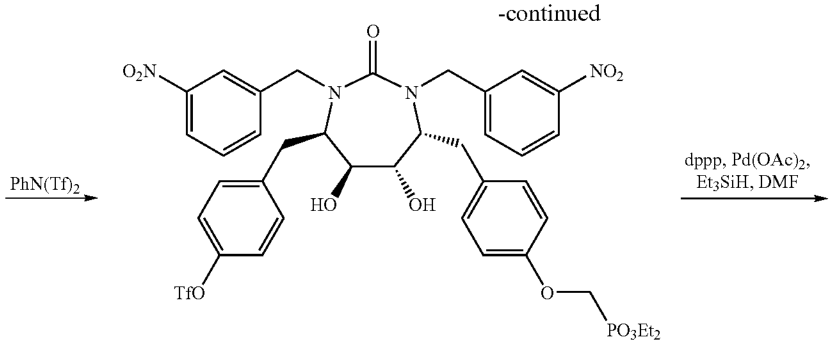

21.6

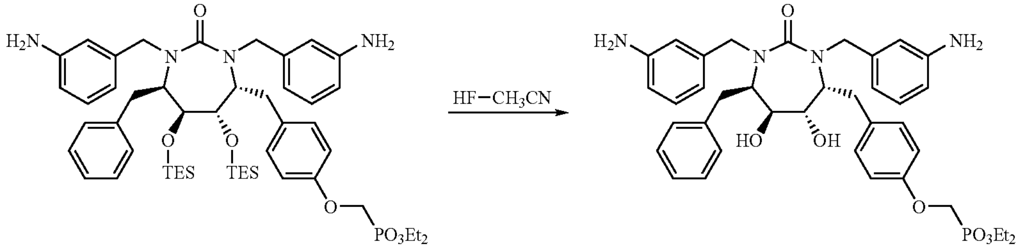

21.7

21.8

Bis-(3-nitrobenzyl) derivative 21.1: A DMF solution (2 mL) of compound 2.8 (0.3 g, 0.59 mmol) was reacted with 60% NaH (0.07 g, 1.76 mmol), 3-nitrobenzyl bromide (0.38 g, 1.76 mmol) and sodium iodide (60 mg, 0.39 mmol) at room temperature for 3 h. The reaction mixture was partitioned between methylene chloride and saturated $NaHCO_3$ solution. The organic phase was isolated, dried over $Na_2SO_4$, concentrated under reduced pressure, and purified by silica gel chromatography to give the desired product 21.1 (0.37 g, 82%).

Diphenol derivative 21.2: A methylene chloride solution (4 mL) of 21.1 (0.37 g, 0.47 mmol) was treated with TFA (1 mL) at room temperature for 3 h, and then concentrated under reduced pressure, and azeotroped with $CH_3CN$ twice to give diphenol derivative 21.2 (0.3 g, quantitative).

Monophosphonate derivative 21.3: A THF solution (8 mL) of 18.2 (0.28 g, 0.44 mmol) was stirred with cesium carbonate (0.17 g, 0.53 mmol) and diethylphosphonate triflate 5.3 (0.14 g, 0.44 mmol) at room temperature for 4 h. The reaction mixture was concentrated under reduced pressure and purified to give 21.3 (120 mg, 35%), and recovered 21.2 (150 mg, 53%).

Methoxy derivative 21.4: A THF solution (2 mL) of 21.3 (9 mg, 11 μmol) was treated with cesium carbonate (15 mg, 46 μmol) and iodomethane (10 eq. Excess) at room temperature for 6 h. The reaction mixture was concentrated under reduced pressure and partitioned between methylene chloride and saturated $NaHCO_3$. The organic phase was separated, dried over sodium sulfate, filtered and concentrated under reduced pressure. The residue was purified by preparative TLC to afford 21.4 (9 mg)

Diethylphosphonate 21.5: A ethyl acetate/ethanol (2 mL/0.5 mL) solution of 21.4 (9 mg, 11 μmol) was hydrogenated at 1 atm in the presence of 10% Pd/C for 4 h. The catalyst was removed by filtration, and the filtrate was concentrated under reduced pressure to give the desired product 21.5 (4.3 mg, 49%, 2 steps). NMR ($CDCl_3$+~10% $CD_3O$): δ 7.0-7.10 (m, 6H), 6.8-6.95 (m, 4H), 6.5-6.6 (m, 4H), 6.4-6.45 (m, 2H), 4.72 (d, 2H), 4.18-4.3 (m, 6H). 3.72 (s, 3H), 3.4-3.5 (m, 4H), 2.8-3.0 (m, 6H), 1.34 (t, 6H). P NMR ($CDCl_3$+~10% $CD_3OD$): 19.93 ppm.

Triflate 21.6: A THF solution (6 mL) of 21.3 (0.1 g, 0.14 mmol), cesium carbonate (0.07 g, 0.21 mmol), and N-phenyltrifluoromethane-sulfonimide (60 mg, 0.17 mmol) was stirred at room temperature for 4 h, and then concentrated under reduced pressure, and worked up. The residue was purified by silica gel chromatography to give 21.6 (116 mg, 90%).

Diamine 21.7: A DMF solution (2 mL) of 21.6 (116 mg, 127 μmol), dppp (60 mg, 145 μmol), and $Pd(OAc)_2$ (30 mg, 134 μmol) was stirred under nitrogen, followed by addition of triethylsilane (0.3 mL), and reacted for 4 h at room temperature. The reaction mixture was worked up and purified to give 21.7 (50 mg).

Diethyl phosphonate 21.8: An acetonitrile solution (1 mL) of crude 21.7 (50 mg) was treated with 48% HF (0.1 mL) for 4 h. The reaction mixture was concentrated under reduced pressure, and purified to give 21.8 (10 mg, 11% (2 steps). NMR ($CDCl_3$+~10% $CD_3O$): δ 7.05-7.30 (m, 9H), 6.8-6.95 (d, 2H), 6.4-6.6 (m, 6H), 4.72 (d, 2H), 4.18-4.3 (m, 6H). 3.4-3.5 (m, 4H), 2.8-3.0 (m, 6H), 1.34 (t, 6H). P NMR ($CDCl_3$+~10% $CD_3OD$): 19.83 ppm.

Scheme 22
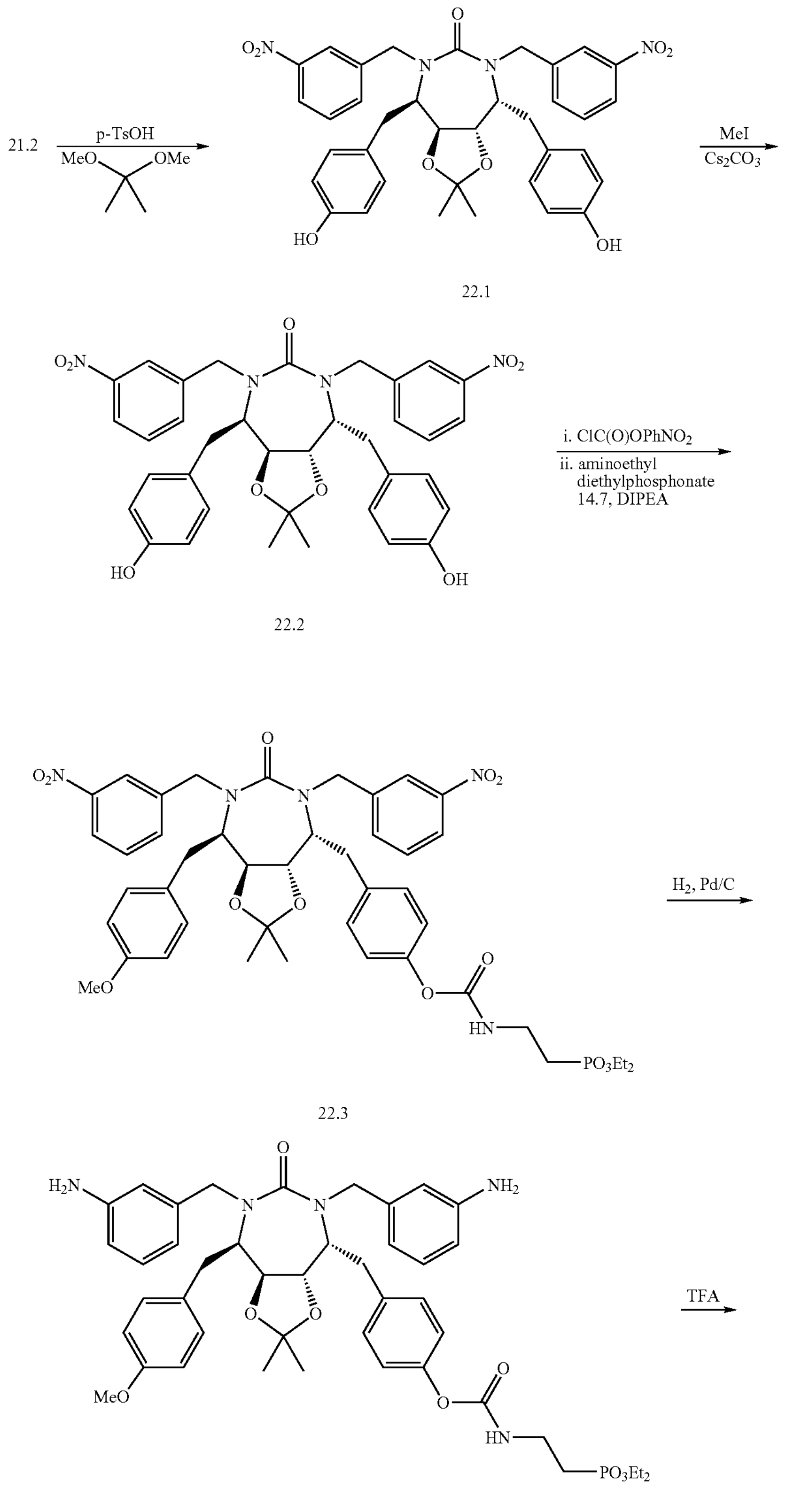
22.1
22.2
22.3
22.4

-continued

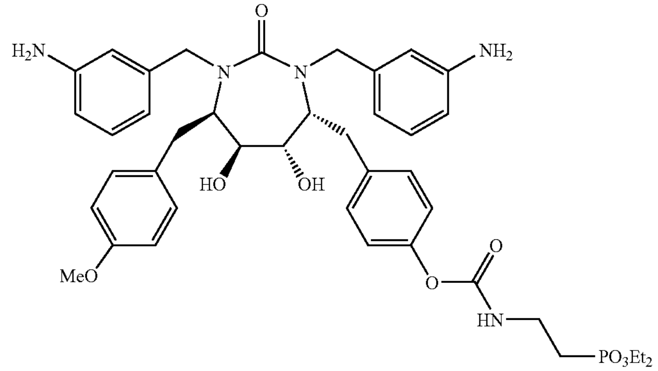

22.5

22.2

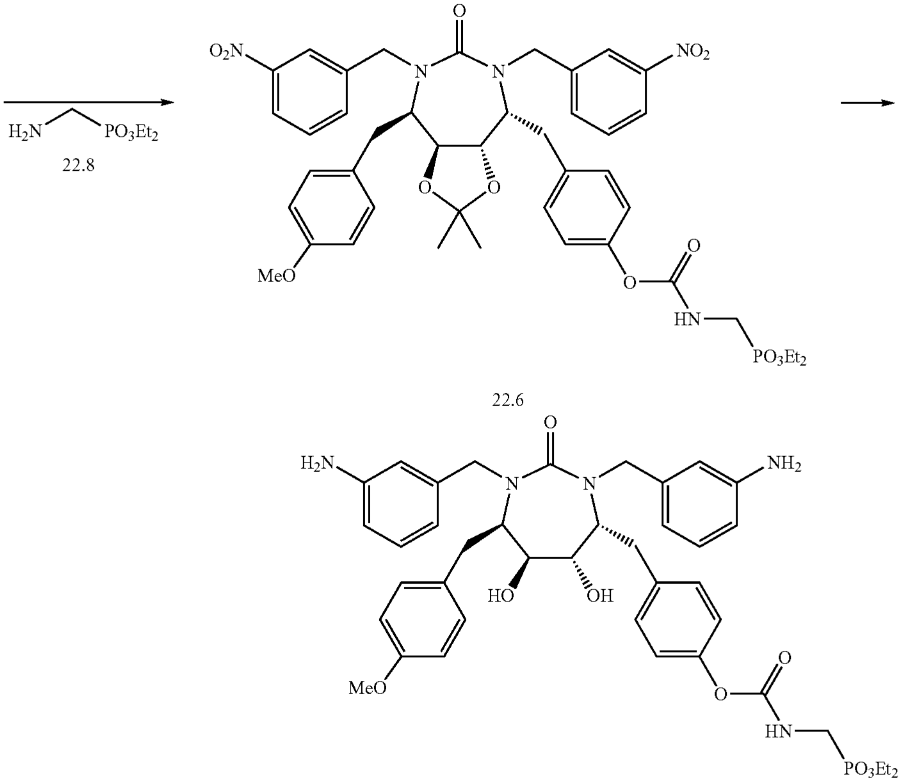

22.8

22.6

22.7

Acetonide 22.1: An acetone/2,2-diemethoxypropane solution (15 mL/5 mL) of compound 21.2 (240 mg, 0.38 mmol) and pyridinium toluenesulfonate (10 mg) was heated at reflux for 30 min. After cooled to room temperature, the reaction mixture was concentrated under reduced pressure. The residue was partitioned between methylene chloride and saturated $NaHCO_3$ aqueous solution, dried, concentrated under reduced pressure and purified to afford 22.1 (225 mg, 88%).

Monomethoxy derivative 22.2: A THF solution (10 mL) of 22.1 (225 mg, 0.33 mmol) was treated with cesium carbonate (160 mg, 0.5 mmol) and iodomethane (52 mg. 0.37 mmol) at room temperature overnight. The reaction mixture was concentrated under reduced pressure, and purified by preparative silica gel column chomatography to afford 22.2 (66 mg, 29%) and recovered starting material 22.1 (25 mg, 11%).

Diethyl phosphonate 22.3: A methylene chloride solution (2 mL) of 22.2 (22 mg, 32 μmol), DIPEA (9 mg, 66 μmol), and p-nitrophenyl chloroformate (8 mg, 40 μmol) was stirred at room temperature for 30 min. The resulting reaction mixture was reacted with DIPEA (10 mg, 77 μmol), and aminoethyl diethylphosphonate 14.7 (12 mg. 45 μmol) at room temperature overnight. The reaction mixture was washed with 5% citric acid solution, saturated $NaHCO_3$, dried, and purified by preparative TLC to afford 22.3 (12 mg, 43%).

Bis(3-aminobenzyl)-diethylphosphonate ester 22.5: An ethyl acetate/t-BuOH (4 mL/2 mL) solution of 22.3 (12 mg, 13 μmol) was hydrogenated at 1 atm in the presence of 10% Pd/C 95 mg) at room temperature for 5 h. The catalyst was removed by filtration. The filtrate was concentrated under reduced pressure, and purified by preparative TLC to give 22.4 (8 mg, 72%). A methylene chloride solution (0.5 mL) of 22.4 (8 mg) was treated with TFA (0.1 mL) at room temperature for 1 h., concentrated under reduced pressure, and then azeotroped with $CH_3CN$ twice to afford 22.5 (8.1 mg, 81%). NMR ($CDCl_3$+~10% $CD_3OD$): δ 7.2 (d, 1H), 6.95-7.15 (m, 6H), 6.75-6.9 (m, 5H), 4.66 (d, 1H), 4.46 (d, 1H), 4.06-4.15 (m, 4H). 3.75 (s, 3H), 3.6-3.7 (m, 4H), 2.6-3.1 (m, 6H), 2.0-2.1 (m, 2H), 1.30 (t, 6H). P NMR ($CDCl_3$+~10% $CD_3OD$): 29.53 ppm. MS: 790 (M+1).

Bis(3-aminobenzyl)diethylphosphonate ester 22.7: Compound 22.7 was prepared from 22.2 (22 mg, 32 μmol) and aminomethyl diethylphosphonate 22.8 as shown above for the preparation of 22.5 from 22.2. NMR ($CDCl_3$+~10% $CD_3OD$): δ 7.24 (d, 1H), 6.8-7.12 (m, 11H), 4.66 (d, 1H), 4.45 (d, 1H), 4.06-4.15 (m, 4H). 3.75 (s, 3H), 2.6-3.1 (m, 6H), 1.30 (t, 6H). P NMR ($CDCl_3$+~10% $CD_3OD$): 22.75 ppm. MS: 776 (M+1).

Scheme 23

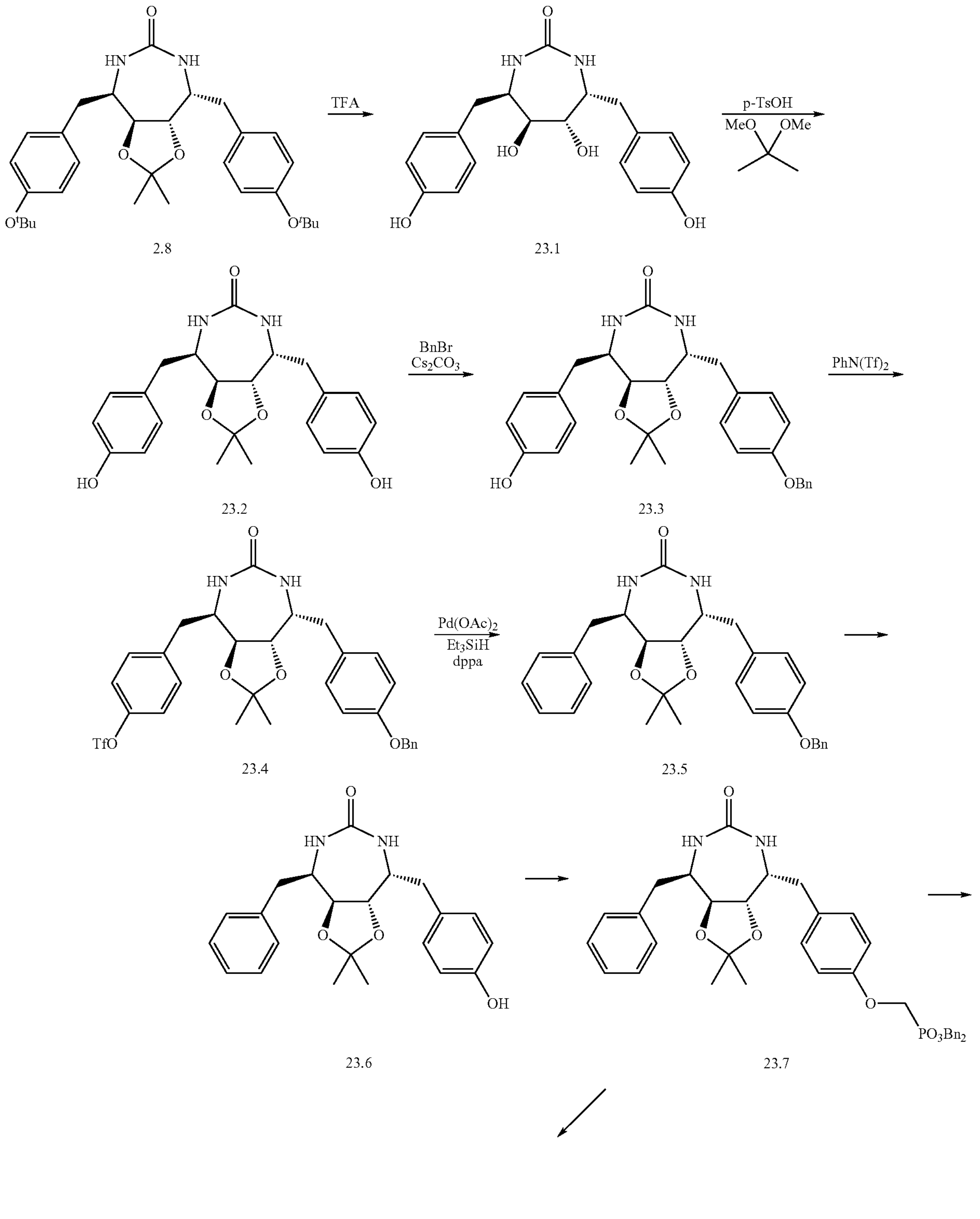

2.8

23.1

23.2

23.3

23.4

23.5

23.6

23.7

-continued

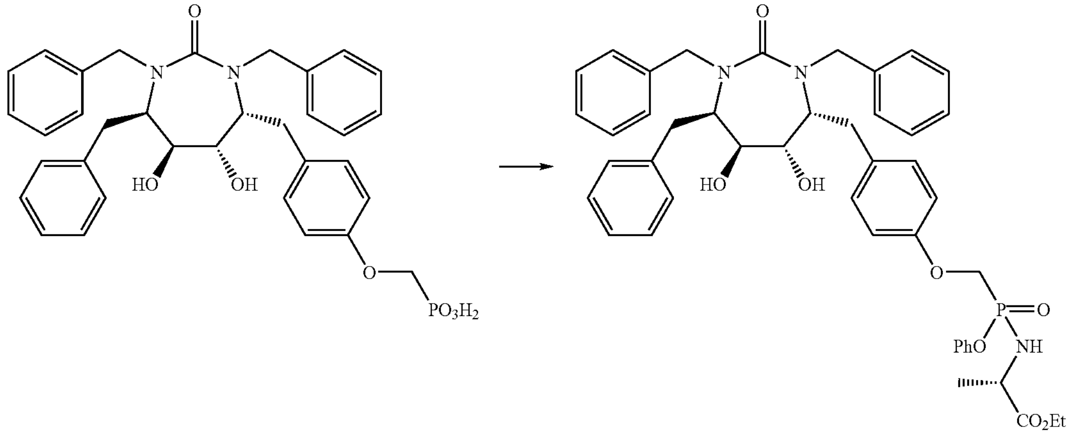

23.8 23.9

Diol 23.1: To a solution of compound 2.8 (2.98 g, 5.84 mmol) in methylene chloride (14 mL) was added TFA (6 mL). The resulted mixture was stirred at room temperature for 2 h. Methanol (5 mL) and additional TFA (5 mL) were added. The reaction mixture was stirred for additional 4 h and then concentrated under reduced pressure. The residue was washed with hexane/ethyl acetate (1:1) and dried to afford compound 23.1 (1.8 g, 86%) as an off-white solid.

Benzyl ether 23.3: To a solution of compound 23.1 (1.8 g, 5.03 mmol) in DMF (6 mL) and 2,2-dimethoxyl propane (12 mL) was added p-toluenesulfonic acid monohydrate (0.095 g, 0.5 mmol). The resultant mixture was stirred at 65° C. for 3 h. The excess 2,2-dimethoxyl propane was slowly distilled. The reaction mixture was cooled to room temperature and charged with THF (50 mL), benzyl bromide (0.8 mL, 6.73 mmol) and cesium carbonate (2.0 g, 6.13 mmol). The resulted mixture was stirred at 65° C. for 16 h. The reaction was quenched with acetic acid aqueous solution (4%, 100 mL) at 0° C., and extracted with ethyl acetate. The organic phase was dried over magnesium sulfate and concentrated under reduced pressure. The residue was purified by chromatography on silica gel to afford desired mono protected compound 23.3 (1.21 g, 49%).

Benzyl ether 23.5: To a solution of compound 23.3 (0.65 g, 1.33 mmol) and N-phenyltrifluoromethanesulfonimide (0.715 g, 2 mmol) in THF (12 mL) was added cesium carbonate (0.65 g, 2 mmol). The mixture was stirred at room temperature for 3 h. The reaction mixture was filtered through a pad of silica gel and concentrated under reduced pressure. The residue was purified on silica gel chromatography to give triflate 23.4 (0.85 g). To a solution of 1,3-bis(diphenylphosphino)propane (0.275 g, 0.66 mmol) in DMF (10 mL) was added palladium(II) acetate (0.15 g, 0.66 mmol) under argon. This mixture was stirred for 2 min. and then added to triflate 23.4. After stirring for 2 min., triethylsilane was added and the resulted mixture was stirred for 1.5 h. The solvent was removed under reduced pressure and the residue was purified by chromatography on silica gel to afford compound 23.5 (0.56 g, 89%).

Phenol 23.6: A solution of 23.5 (0.28 g, 0.593 mmol) in ethyl acetate (5 mL) and isopropyl alcohol (5 mL) was treated with 10% Pd/C (0.05 g) and stirred under a hydrogen atmosphere (balloon) for 16 h. The catalyst was removed by filtration and the filtrate was concentrated under reduced pressure to yield 23.6 (0.22 g, 97%) as a white solid.

Dibenzyl phosphonate 23.7: To a solution of compound 23.6 (0.215 g, 0.563 mmol) in THF (10 mL) was added dibenzyl triflate 3.11 (0.315 g, 0.74 mmol) and cesium carbonate (0.325 g, 1 mmol). The mixture was stirred at room temperature for 2 h, then diluted with ethyl acetate and washed with water. The organic phase was dried over magnesium sulfate, filtered and concentrated under reduced pressure. The residue was purified by chromatography on silica gel to afford compound 23.7 (0.31 g, 84%).

Diphenyl ester 23.8: A solution of compound 23.7 (0.3 g, 0.457 mmol) and benzyl bromide (0.165 mL, 1.39 mmol) in THF (10 mL) was treated with potassium tert-butoxide (1M/THF, 1.2 mL) for 0.5 h. The mixture was diluted with ethylacetate and washed with HCl (0.2N). The organic phase was dried over magnesium sulfate, filtered and concentrated under reduced pressure. The residue was dissolved in ethyl acetate and treated with 10% Pd/C (0.05 g) under hydrogen atmosphere (balloon) for 16 h. The catalyst was removed by filtration and the filtrate was concentrated under reduced pressure. The residue was treated with TFA (1 mL) in methanol (5 mL) for 1 h, and then concentrated under reduced pressure. The residue was dissolved in pyridine (1 mL) and mixed with phenol (0.45 g, 4.8 mmol) and 1,3-dicyclohexylcarbodiimide (0.38 g, 1.85 mmol). The mixture was stirred at 70° C. for 2 h, and then concentrated under reduced pressure. The residue was partitioned between ethyl acetate and HCl (0.2N). The organic phase was dried over magnesium sulfate, filtered and concentrated. The residue was purified by chromatography on silica gel to afford compound 23.8 (0.085 g, 24%).

Mono amidate 23.9: To a solution of 23.8 (0.085 g, 0.11 mmol) in acetonitrile (1 mL) was added sodium hydroxide (1N, 0.25 mL) at 0° C. After stirred at 0° C. for 1 h, the mixture was acidified with Dowex resin to pH=3, and filtered. The filtrate was concentrated under reduced pressure. The residue was dissolved in pyridine (0.5 mL) and mixed with L-alanine ethyl ester hydrochloride (0.062 g, 0.4 mmol) and 1,3-dicyclohexyl-carbodiimide (0.125 g, 0.6 mmol). The mixture was stirred at 60° C. for 0.5 h, and then concentrated under reduced pressure. The residue was partitioned between ethyl acetate and HCl (0.2N). The organic phase was dried over magnesium sulfate, filtered and concentrated. The residue was purified by HPLC (C-18, 65% acetonitrile/water) to afford compound 23.9 (0.02 g, 23%). $^{1}$H NMR ($CDCl_3$): δ 1.2 (m, 3H), 1.4 (m, 3H), 1.8 (brs, 2H), 2.8-3.1 (m, 6H), 3.5-3.7 (m, 4H), 3.78 (m, 1H), 4.0-4.18 (m, 2H), 4.2-4.4 (m, 3H), 4.9 (m, 2H), 6.8-7.4 (m, 24H). $^{31}$P NMR ($CDCl_3$): d 20.9, 19.8. MS: 792 (M+1).

Scheme 24
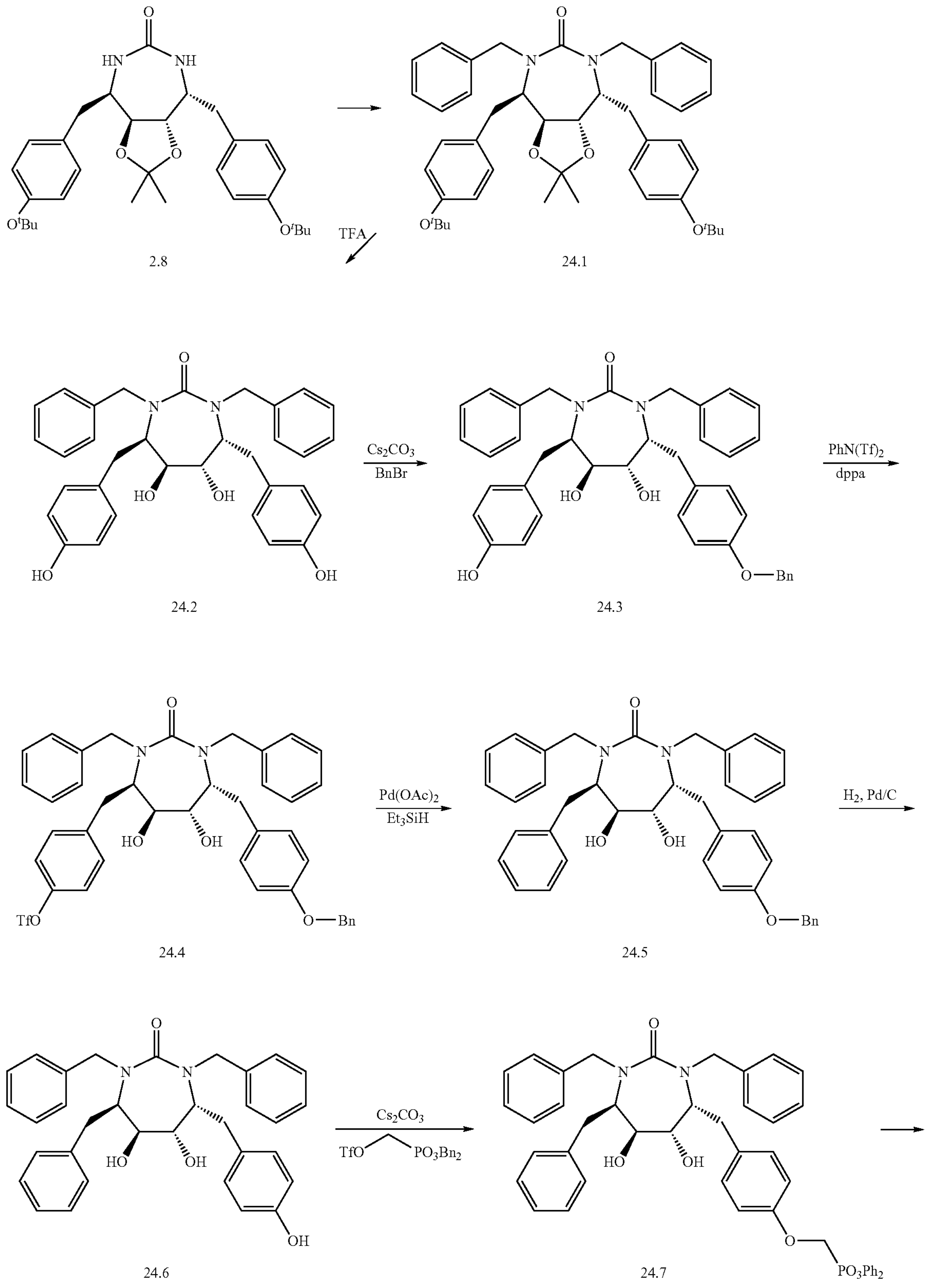
2.8
24.1
24.2
24.3
24.4
24.5
24.6
24.7

-continued

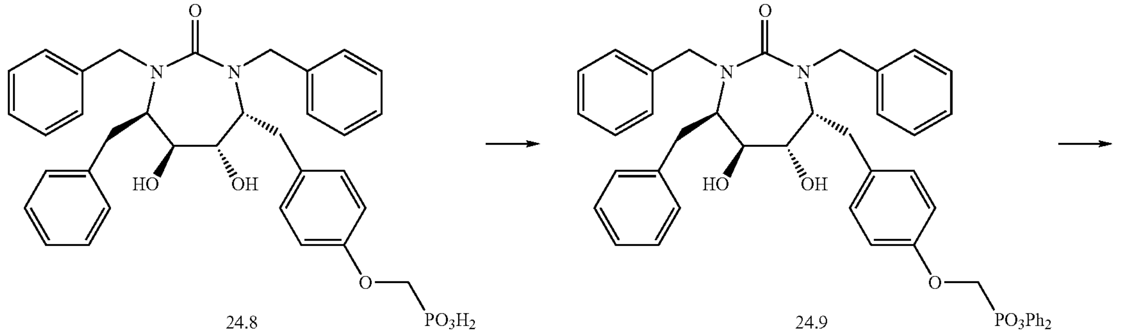

24.8 24.9

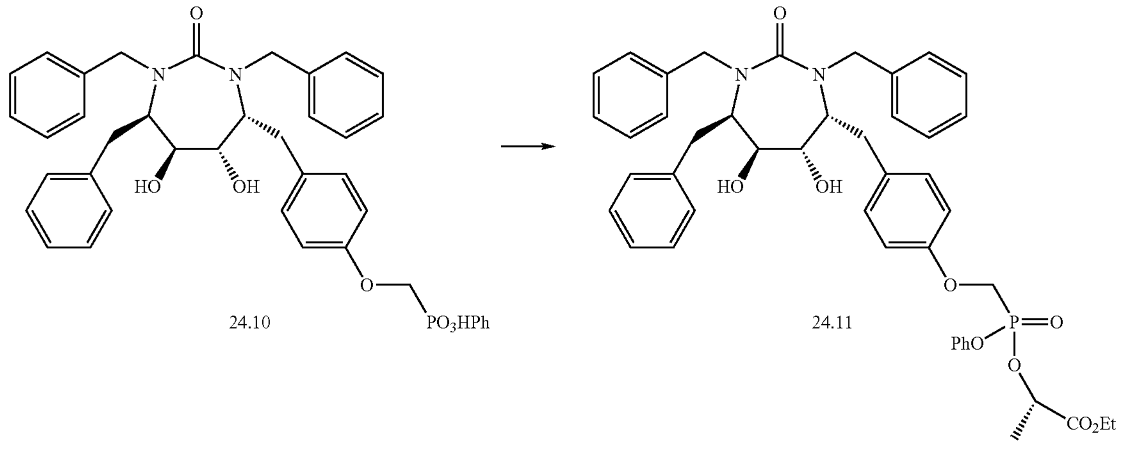

24.10 24.11

Di-tert butyl ether 24.1: To a solution of compound 2.8 (0.51 g, 1 mmol) and benzyl bromide (0.43 g, 2.5 mmol) in THF (6 mL) was added potassium tert-butoxide (1M/THF, 2.5 mL). The mixture was stirred at room temperature for 0.5 h, then diluted with ethyl acetate and washed with water. The organic phase was dried over magnesium sulfate, filtered and concentrated under reduced pressure. The residue was purified by chromatography on silica gel to afford compound 24.1 (0.62 g, 90%).

Diol 24.2: To a solution of compound 24.1 (0.62 g, 0.9 mmol) in methylene chloride (4 mL) was added TFA (1 mL) and water (0.1 mL). The mixture was stirred for 2 h, and then concentrated under reduced pressure. The residue was purified by chromatography on silica gel to afford compound 24.2 (0.443 g, 92%).

Benzyl ether 24.3: Compound 24.3 was prepared in 46% yield according to the procedure described in Scheme 23 for the preparation of 23.3.

Triflate 24.4: Compound 24.4 was prepared in 95% yield according to the procedure described in Scheme 23 for the preparation of 23.4.

Benzyl ether 24.5: Compound 24.5 was prepared in 93% yield according to the procedure described in Scheme 23 for the preparation of 23.5.

Phenol 24.6: Compound 24.6 was prepared in 96% yield according to the procedure described in Scheme 23 for the preparation of 23.6 from 23.5.

Dibenzyl phosphonate 24.7: Compound 24.7 was prepared in 82% yield according to the procedure described in Scheme 23 for the preparation of 23.7.

Diacid 24.8: A solution of 24.7 (0.16 g, 0.207 mmol) in ethyl acetate (4 mL) and isopropyl alcohol (4 mL) was treated with 10% Pd/C (0.05 g) and stirred under a hydrogen atmosphere (balloon) for 4 h. The catalyst was removed by filtration and the filtrate was concentrated under reduced pressure to yield 24.8 (0.125 g, 98%) as a white solid.

Diphenyl ester 24.9: To a solution of compound 24.8 (0.12 g, 0.195 mmol) in pyridine (1 mL) was added phenol (0.19 g, 2 mmol) and 1,3-dicyclohexylcarbodiimide (0.206 g, 1 mmol). The mixture was stirred at 70° C. for 2 h, and then concentrated under reduced pressure. The residue was partitioned between ethyl acetate and HCl (0.2N). The organic phase was dried over magnesium sulfate, filtered and concentrated. The residue was purified by chromatography on silica gel to afford compound 24.9 (0.038 g, 25%).

Mono lactate 24.11: Compound 24.9 was converted, via compound 24.10, into compound 24.11 in 36% yield according to the procedure described in Scheme 23 for the preparation of 23.9 except utilizing the ethyl lactate ester in place of L-alanine ethyl ester. $^1H$ NMR (CDCl3): δ 1.05 (t, J=8 Hz, 1.5H), 1.1 (t, J=8 Hz, 1.5H), 1.45 (d, J=8 Hz, 1.5H), 1.55 (d, J=8 Hz, 1.5H), 2.6 (brs, 2H), 2.9-3.1 (m, 6H), 3.5-3.65 (m, 4H), 4.15-4.25 (m, 2H), 4.4-4.62 (m, 2H), 4.9 (m, 2H), 5.2 (m, 1H), 6.9-7.4 (m, 24H). 31P NMR ($CDCl_3$): d 17.6, 15.5. MS: 793 (M+1).

Scheme 25

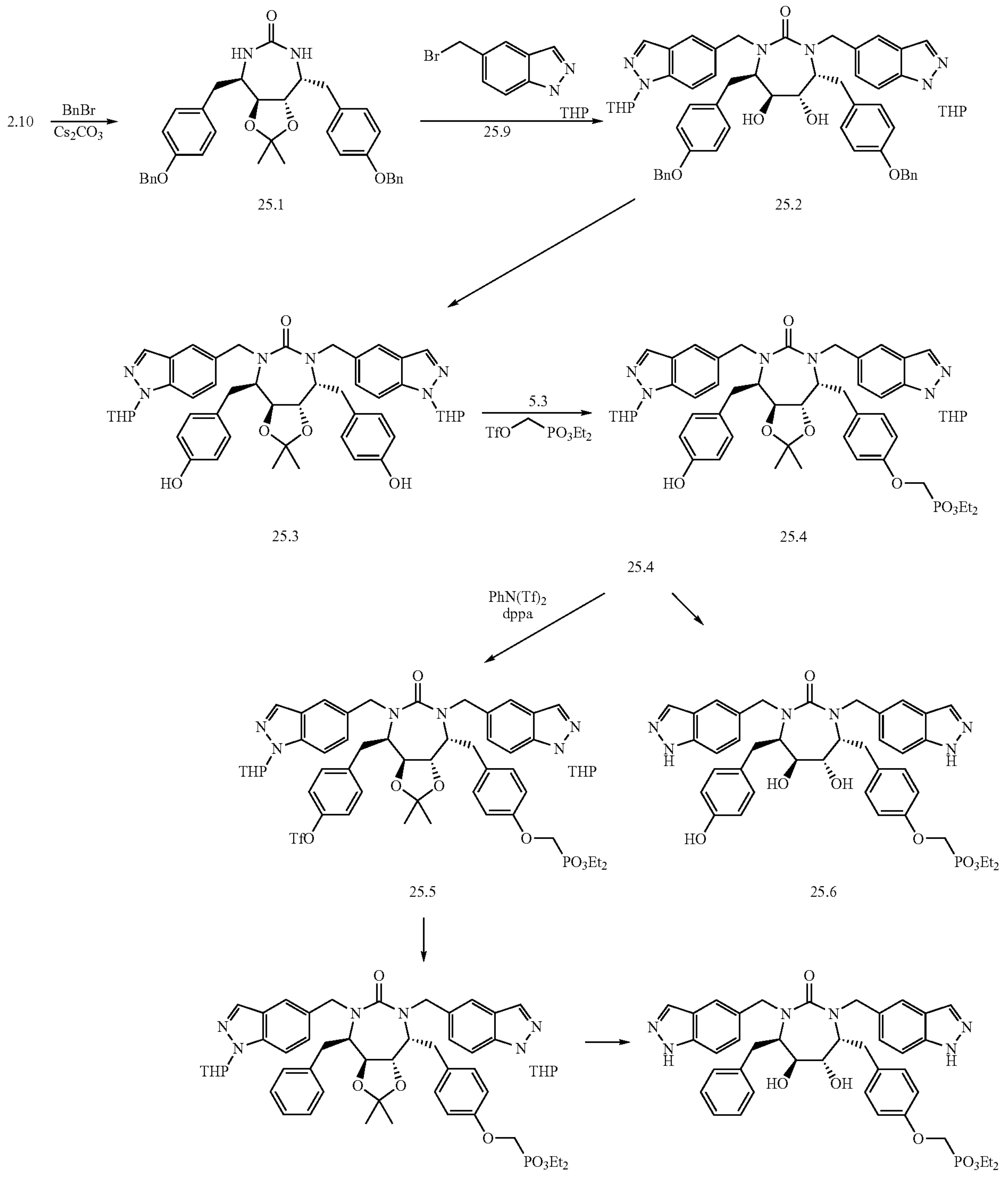

25.1 25.2 25.3 25.4 25.5 25.6 25.7 25.8

Dibenzyl ether 25.1: The protection reaction of compound 2.10 with benzyl bromide was carried out in the same manner as described in Scheme 23 to afford compound 25.1.

Bis indazole 25.2: The alkylation of compound 25.1 with bromide 25.9 was carried out in the same manner as described in Scheme 23 to afford compound 25.2 in 96% yield.

Diol 25.3: A solution of 25.2 (0.18 g, 0.178 mmol) in ethyl acetate (5 mL)) and isopropyl alcohol (5 mL) was treated with 20% $Pd(OH)_2/C$ (0.09 g) and stirred under a hydrogen atmosphere (balloon) for 24 h. The catalyst was removed by filtration and the filtrate was concentrated under reduced pressure to afford 25.3 in quantitative yield.

Diethyl phosphonate 25.4: To a solution of compound 25.3 (0.124 g, 0.15 mmol) in acetonitrile (8 mL) and DMF (1 mL) was added potassium tert-butoxide (0.15 mL, 1M/THF). The mixture was stirred for 10 min. to form a clear solution. Diethyl triflate 5.3 (0.045 g, 0.15 mmol) was added to the reaction mixture. After stirred for 0.5 h, the reaction mixture was diluted with ethyl acetate and washed with HCl (0.1N). The organic phase was dried over magnesium sulfate, filtered and concentrated under reduced pressure. The residue was purified by chromatography on silica gel to afford compound 25.4 (0.039 g, 55% (based on recovered starting material: 0.064 g, 52%).

Bisindazole 25.6: A mixture of compound 25.4 (0.027 g), ethanol (1.5 mL), TFA (0.6 mL) and water (0.5 mL) was stirred at 60° C. for 18 h. The mixture was concentrated under reduced pressure, and the residue was purified by HPLC to afford compound 25.6 as a TFA salt (0.014 g, 51%). $^{1}$H NMR (CD3OD): δ 1.4 (t, J=8 Hz, 6H), 2.9 (M, 4H), 3.2 (m, 2H), 3.58 (brs, 2H), 3.65 (m, 2H), 4.25 (m, 4H), 4.42 (d, J=10 Hz, 2H), 4.85 (m, 2H), 6.75 (d, J=9 Hz, 2H), 6.9 (m, 4H), 7.0 (d, J=9 Hz, 2H), 7.4-7.6 (m, 6H), 8.1 (brs, 2H). $^{31}$P NMR (CD3OD): δ 20.8. MS: 769 (M+1).

Diethyl phosphonate 25.7: Compound 25.4 was converted into compound 25.7 in 76% yield according to the procedures described in Scheme 23 for the conversion of 23.3 into 23.5.

Bis indazole 25.8: Compound 25.7 (0.029 g) was treated in the same manner as compound 25.4 in the preparation of 25.6 to afford compound 25.8 as a TFA salt (0.0175 g, 59%). $^{1}$H NMR (CD3OD): δ 1.4 (t, J=8 Hz, 6H), 3.0 (M, 4H), 3.15 (d, J=14 Hz, 1H), 3.25 (d, J=14 Hz, 1H), 3.58 (brs, 2H), 3.65 (m, 2H), 4.25 (m, 4H), 4.42 (d, J=10 Hz, 2H), 4.85 (m, 2H), 6.9 (d, J=9 Hz, 2H), 7.0 (d, J=9 Hz, 2H), 7.1 (d, J=7 Hz, 2H), 7.2-7.6 (m, 9H), 8.1 (brs, 2H). $^{31}$P NMR (CD3OD): δ 20.8. MS: 753 (M+1).

Preparation of Alkylating and Phosphonate Reagents

Scheme 50

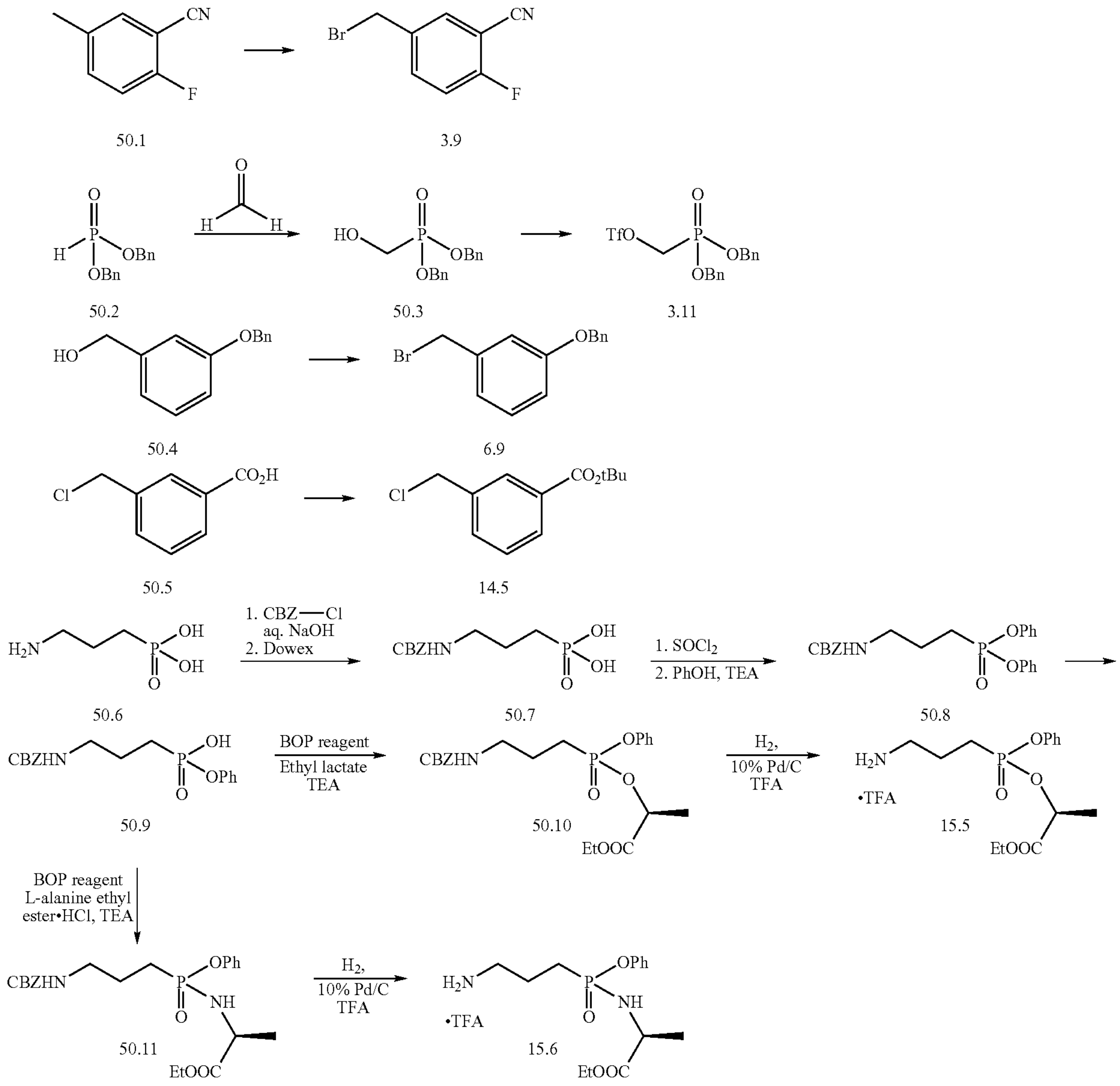

3-cyano-4-fluoro-benzylbromide 3.9: The commercially available 2-fluoro-4-methylbenzonitrile 50.1 (10 g, 74 mmol) was dissolved in carbon tetrachloride (50 mL) and then treated with NBS (16 g, 90 mmol) followed by AIBN (0.6 g, 3.7 mmol). The mixture was stirred at 85° C. for 30 min and then allowed to cool to room temperature. The mixture was filtered and the filtrate concentrated under reduced pressure. The residue was purified by silica gel eluting with 5-20% ethyl acetate in hexanes to give 3.9 (8.8 g, 56%).

4-benzyloxy benzyl chloride 3.10 is purchased from Aldrich

Dibenzyl triflate 3.11: To a solution of dibenzyl phosphite 50.2 (100 g, 381 mmol) and formaldehyde (37% in water, 65 mL, 860 mmol) in THF (200 mL) was added TEA (5 mL, 36 mmol). The resulted mixture was stirred for 1 h, and then concentrated under reduced pressure. The residue was dissolved in methylene chloride and hexane (1:1, 300 mL), dried over sodium sulfate, filtered through a pad of silica gel (600 g) and eluted with ethyl acetate and hexane (1:1). The filtrate was concentrated under reduced pressure. The residue 50.3 (95 g) was dissolved in methylene chloride (800 mL), cooled to −78° C. and then charged with pyridine (53 mL, 650 mmol). To this cooled solution was slowly added trifluoromethanesulfonic anhydride (120 g, 423 mmol). The resulted reaction mixture was stirred and gradually warmed up to −15° C. over 1.5 h period of time. The reaction mixture was cooled down to about −50° C., diluted with hexane-ethyl acetate (2:1, 500 mL) and quenched with aqueous phosphoric acid (1M, 100 mL) at −10° C. to 0° C. The mixture diluted with hexane-ethyl acetate (2:1, 1000 mL). The organic phase was washed with water, dried over magnesium sulfate, filtered and concentrated under reduced pressure. The residue was purified by chromatography on silica gel to afford dibenzyl triflate 3.11 (66 g, 41%) as a colorless oil.

Diethyl triflate 5.3 is prepared as described in Tet Lett. 1986, 27, p1477-1480

3-Benzyloxybenzylbromide 6.9: To a solution of triphenyl phosphine (15.7 g, 60 mmol) in THF (150 mL) was added a solution of carbon tetrabromide (20 g, 60 mmol) in THF (50 mL). A precipitation was formed and stirred for 10 min. A solution of 3-benzyloxybenzyl alcohol 50.4 (10 g, 46.7 mmol) was added. After stirred for 1.5 h, the reaction mixture was filtered and concentrated under reduced pressure. The majority of triphenyl phosphine oxide was removed by precipitation from ethyl acetate-hexane. The crude product was purified by chromatography on silica gel and precipitation from hexane to give the desired product 3-Benzyloxybenzylbromide 6.9 (10 g, 77%) as a white solid.

t-Butyl-3-chloromethyl benzoate 14.5: A benzene solution (15 ml) of 3-chloromethylbenzoic acid 50.5 (1 g, 5.8 mmol) was heated at reflux, followed by the slow addition of N,N-dimethylforamide-di-t-butylacetal (5 m). The resulting solution was refluxed for 4 h, concentrated under reduced pressure and purified by silica gel column to afford 14.5 (0.8 g, 60%).

Aminopropyl-diethylphosphonate 14.6 is purchased from Acros

Aminoethyl-diethylphosphonate oxalate 14.7 is purchased from Acros

Aminopropyl-phenol-ethyl lactate phosphonate 15.5

N-CBZ-aminopropyl diphenylphosphonate 50.8: An aqueous sodium hydroxide solution (50 mL of 1 N solution, 50 mmol) of 3-aminopropyl phosphonic acid 50.6 (3 g, 1.5 mmol) was reacted with CBZ-Cl (4.1 g, 24 mmol) at room temperature overnight. The reaction mixture was washed with methylene chloride, acidified with Dowex 50w×8-200. The resin was filtered off. The filtrate was concentrated to dryness. The crude N-CBZ-aminopropyl phosphonic acid 50.7 (5.8 mmol) was suspended in $CH_3CN$ (40 mL), and reacted with thionyl chloride (5.2 g, 44 mmol) at reflux for 4 hr, concentrated, and azeotroped with $CH_3CN$ twice. The reaction mixture was redissolved in methylene chloride (20 mL), followed by the addition of phenol (3.2 g, 23 mmol), was cooled to 0° C. To this 0° C. cold solution was added TEA (2.3 g, 23 mmol), and stirred at room temperature overnight. The reaction mixture was concentrated and purified on silica gel column chromatograph to afford 50.8 (1.5 g, 62%).

Monophenol derivative 50.9: A $CH_3CN$ solution (5 mL) of 50.8 (0.8 g, 1.88 mmol) was cooled to 0° C., and treated with 1N NaOH aqueous solution (4 mL, 4 mmol) for 2 h. The reaction was diluted with water, extracted with ethyl acetate, acidified with Dowex 50w×8-200. The aqueous solution was concentrated to dryness to afford 50.9 (0.56 g, 86%).

Monolactate derivative 50.10: A DMF solution (1 mL) of crude 50.9 (0.17 g, 0.48 mmol), BOP reagent (0.43 g, 0.97 mmol), ethyl lactate (0.12 g, 1 mmol), and DIPEA (0.31 g, 2.4 mmol) was reacted for 4 hr at room temperature. The reaction mixture was partitioned between methylene chloride and 5% citric acid aqueous solution. The organic solution was separated, concentrated, and purified on preparative TLC to give 50.10 (0.14 g, 66%).

3-Aminopropyl lactate phosphonate 15.5: An ethyl acetate/ethanol solution (10 mL/2 mL) of 50.10 (0.14 g, 0.31 mmol) was hydrogenated at 1 atm in the presence of 10% Pd/C (40 mg) for 3 hr. The catalyst was filtered off. The filtrate was concentrated to dryness to afford 15.5 (0.14 g, quantitative). NMR ($CDCl_3$): δ 8.0-8.2 (b, 3H), 7.1-7.4 (m, 5H), 4.9-5.0 (m, 1H), 4.15-4.3 (m, 2H), 3.1-3.35 (m, 2H), 2.1-2.4 (n, 4H), 1.4 (d, 3H), 1.3 (t, 3H).

Aminopropyl-phenol-ethyl alanine phosphonate 15.6: Compound 15.6 (80 mg) was prepared from the reaction of 50.9 (160 mg, 0.45 mmol) and L-alanine ethyl ester hydrochloride salt (0.11 g, 0.68 mmol) in the presence of DIPEA and BOP reagent to give 50.11, followed by the hydrogenation in the presence of 10% Pd/C and TFA to yield 15.6. NMR ($CDCl_3$+~10% $CD_3OD$): δ 8.0-8.2 (b), 7.25-7.35 (t, 2H), 7.1-7.2 (m, 3H), 4.0-4.15 (m, 2H), 3.8-4.0 (m, 1H), 3.0-3.1 (m, 2H), 1.15-1.25 (m, 6H). P NMR ($CDCl_3$+~10% $CD_3OD$): 32.1 & 32.4 ppm.

Aminopropyl dibenzyl phosphonate 15.7:

N-BOC-3-aminopropyl phosphonic acid 50.13: A THF-1N aqueous solution (16 mL-16 mL) of 3-aminopropyl phosphonic acid 50.12 (1 g, 7.2 mmol) was reacted with $(BOC)_2O$ (1.7 g, 7.9 mmol) overnight at room temperature. The reaction mixture was concentrated, and partitioned between methylene chloride and water. The aqueous solution was acidified with Dowex 50w×8-200. The resin was filtered off. The filtrate was concentrated to give 50.13 (2.2 g, 92%).

N-BOC-3-aminopropyl dibenzyl phosphonate 50.14: A $CH_3CN$ solution (10 mL) of 50.13 (0.15 g, 0.63 mmol), cesium carbonate (0.61 g, 1.88 mmol), and benzyl bromide (0.24 g, 1.57 mmol) was heated at reflux overnight. The reaction mixture was cooled to room temperature, and diluted with methylene chloride. The white solid was filtered off, washed thoroughly with methylene chloride. The organic phase was concentrated, and purified on preparative TLC to give 50.14 (0.18 g, 70%). MS: 442 (M+Na).

Aminopropyl dibenzyl phosphonate 15.7: A methylene chloride solution (1.6 mL) of 50.14 (0.18 g) was treated with TFA (0.4 mL) for 1 hr. The reaction mixture was concentrated to dryness, and azeotroped with $CH_3CN$ twice to afford 15.7 (0.2 g, as TFA salt). NMR ($CDCl_3$): δ 8.6 (b, 2H), 7.9 (b, 2H), 7.2-7.4 (m, 10H), 4.71-5.0 (2 abq, 4H), 3.0 (b, 2H), 1.8-2 (m, 4H). 31P NMR ($CDCl_3$): 32.0 ppm. F NMR ($CDCl_3$): -76.5 ppm.

Aminomethyl diethylphosphonate 22.8 is purchased from Acros

Bromomethyl, tetrahydropyran indazole 25.9 is prepared according to J. Org. Chem. 1997, 62, p5627

Activity of the CCPPI Compounds

The enzyme inhibitory potency (Ki), antiviral activity (EC50), and cytotoxicity (CC50) of the tested compounds were measured and demonstrated.

Biological Assays used for the Characterization of PI Prodrugs

HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, Int. J. Peptide Protein Res. 36, 544 (1990)

Substrate: (2-aminobenzoyl)Thr-Ile-Nle-(p-nitro)Phe-Gln-Arg

Substrate supplied by Bachem California, Inc. (Torrance, Calif.; Cat. no. H-2992)

Enzyme: recombinant HIV-1 protease expressed in *E. Coli*

Enzyme supplied by Bachem California, Inc. (Torrance, Calif.; Cat. no. H-9040)

Reaction buffer:

100 mM ammonium acetate, pH 5.3

1 M sodium chloride 1 mM ethylendiaminetetraacetic acid 1 mM dithiothreitol

10% dimethylsulfoxide

Assay Protocol for the Determination of Inhibition Constant Ki:

1. Prepare series of solutions containing identical amount of the enzyme (1 to 2.5 nM) and a tested inhibitor at different concentrations in the reaction buffer
2. Transfer the solutions (190 uL each) into a white 96-well plate
3. Preincubate for 15 min at 37° C.
4. Solubilize the substrate in 100% dimethylsulfoxide at a concentration of 800 μM. Start the reaction by adding 10 μL of 800 μM substrate into each well (final substrate concentration of 40 μM)
5. Measure the real-time reaction kinetics at 37° C. by using Gemini 96-well plate fluorimeter (Molecular Devices, Sunnyvale, Calif.) at λ(Ex)=330 nm and λ(Em)=420 nm
6. Determine initial velocities of the reactions with different inhibitor concentrations and calculate Ki (in picomolar concentration units) value by using EnzFitter program (Biosoft, Cambridge, U.K.) according to an algorithm for tight-binding competitive inhibition described by Ermolieff J., Lin X., and Tang J., Biochemistry 36, 12364 (1997)

Anti-HIV-1 Cell Culture Assay ($EC_{50}$)

The assay is based on quantification of the HIV-1-associated cytopathic effect by a colorimetric detection of the viability of virus-infected cells in the presence or absence of tested inhibitors. The HIV-1-induced cell death is determined using a metabolic substrate 2,3-bis(2-methoxy-4-nitro-5-sulfophenyl)-2H-tetrazolium-5-carboxanilide (XTT) which is converted only by intact cells into a product with specific absorption characteristics as described by Weislow O S, Kiser R, Fine D L, Bader J, Shoemaker R H and Boyd M R, J. Natl. Cancer Inst. 81, 577 (1989).

Assay Protocol for Determination of $EC_{50}$:

1. Maintain MT2 cells in RPMI-1640 medium supplemented with 5% fetal bovine serum and antibiotics.
2. Infect the cells with the wild-type HIV-1 strain IIIB (Advanced Biotechnologies, Columbia, Md.) for 3 hours at 37° C. using the virus inoculum corresponding to a multiplicity of infection equal to 0.01.
3. Prepare a set of solutions containing various concentrations of the tested inhibitor by making 5-fold serial dilutions in 96-well plate (100 μL/well). Distribute the infected cells into the 96-well plate (20,000 cells in 100 mL/well). Include samples with untreated infected and untreated mock-infected control cells.
4. Incubate the cells for 5 days at 37° C.
5. Prepare XTT solution (6 mL per assay plate) at a concentration of 2 mg/mL in a phosphate-buffered saline pH 7.4. Heat the solution in water-bath for 5 min at 55° C. Add 50 μL of N-methylphenazonium methasulfate (5 μg/mL) per 6 mL of XTT solution.
6. Remove 100 μL media from each well on the assay plate.
7. Add 100 μL of the XTT substrate solution per well and incubate at 37° C. for 45 to 60 min in a $CO_2$ incubator.
8. Add 20 μL of 2% Triton X-100 per well to inactivate the virus.
9. Read the absorbance at 450 nm with subtracting off the background absorbance at 650 nm.
10. Plot the percentage absorbance relative to untreated control and estimate the $EC_{50}$ value as drug concentration resulting in a 50% protection of the infected cells.

Cytotoxicity Cell Culture Assay ($CC_{50}$):

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, J. Natl. Cancer Inst. 81, 577 (1989).

Assay Protocol for Determination of $CC_{50}$:

1. Maintain MT-2 cells in RPMI-1640 medium supplemented with 5% fetal bovine serum and antibiotics.
2. Prepare a set of solutions containing various concentrations of the tested inhibitor by making 5-fold serial dilutions in 96-well plate (100 μL/well). Distribute cells into the 96-well plate (20,000 cells in 100 μL/well). Include samples with untreated cells as a control.
3. Incubate the cells for 5 days at 37° C.
4. Prepare XTT solution (6 mL per assay plate) in dark at a concentration of 2 mg/mL in a phosphate-buffered saline pH 7.4. Heat the solution in a water-bath at 55° C. for 5 min. Add 50 μL of N-methylphenazonium methasulfate (5 μg/mL) per 6 mL of XTT solution.
5. Remove 100 μL media from each well on the assay plate and add 100 μL of the XTT substrate solution per well. Incubate at 37° C. for 45 to 60 min in a $CO_2$ incubator.
6. Add 20 μL of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

Resistance Evaluation (150V and 184V/L90M Fold Change)

The assay is based on the determination of a difference in the susceptibility to a particular HIV protease inhibitor between the wild-type HIV-1 strain and a mutant HIV-1 strain containing specific drug resistance-associated mutation(s) in the viral protease gene. The absolute susceptibility of each virus ($EC_{50}$) to a particular tested compound is measured by using the XTT-based cytopathic assay as described above. The degree of resistance to a tested compound is calculated as fold difference in $EC_{50}$ between the wild type and a specific mutant virus. This represents a standard approach for HIV drug resistance evaluation as documented in various publications (e.g. Maguire et al., Antimicrob. Agents Chemother. 46: 731, 2002; Gong et al., Antimicrob. Agents Chemother. 44: 2319, 2000; Vandamme and De Clercq, in Antiviral Therapy (Ed. E. De Clercq), pp. 243, ASM Press, Washington, D.C., 2001).

HIV-1 Strains Used for the Resistance Evaluation:

Two strains of mutant viruses containing 150V mutation in the protease gene have been used in the resistance assays: one with M46I/I47V/I50V mutations (designated I50V #1) and the other with L10I/M46I/I50V (designated I50V #2) mutations in the viral protease gene. A third virus with I84V/L90M mutations was also employed in the resistance assays. Mutants I50V #1 and I84V/L90M were constructed by a homologous recombination between three overlapping DNA fragments: 1. linearized plasmid containing wild-type HIV-1 proviral DNA (strain HXB2D) with the protease and reverse transcriptase genes deleted, 2. DNA fragment generated by PCR amplification containing reverse transcriptase gene from HXB2D strain (wild-type), 3. DNA fragment of mutated viral protease gene that has been generated by PCR amplification. An approach similar to that described by Shi and Mellors in Antimicrob. Agents Chemother. 41: 2781-85, 1997 was used for the construction of mutant viruses from the generated DNA fragments. Mixture of DNA fragments was delivered into Sup-T1 cells by using a standard electroporation technique. The cells were cultured in RPMI-1640 medium supplemented with 10% fetal bovine serum and antibiotics until the recombinant virus emerged (usually 10 to 15 days following the electroporation). Cell culture supernatant containing the recombinant virus was harvested and stored in aliquots. After verification of protease gene sequence and determination of the infectious virus titer, the viral stock was used for drug resistance studies. Mutant I50V #2 is an amprenavir-resistant HIV-1 strain selected in vitro from the wild-type IIIB strain in the presence of increasing concentration of amprenavir over a period of >9 months using an approach similar to that described by Partaledis et al., J. Virol. 69: 5228-5235, 1995. Virus capable of growing in the presence of 5 μM amprenavir was harvested from the supernatant of infected cells and used for resistance assays following the titration and protease gene sequencing.

Example 37

Activity of the Tested Compounds

The enzyme inhibitory potency (Ki), antiviral activity (EC50), and cytotoxicity (CC50) of the tested compounds are summarized in Table 1.

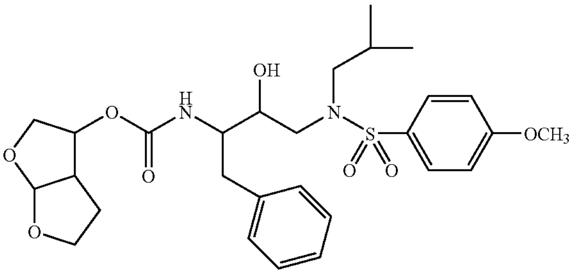

TABLE 1

Enzyme inhibition activity (Ki), antiviral cell culture activity (EC50), and cytotoxicity (CC50) of the tested compounds.

| Substitution of (P1)phenyl | Compound | Phosphonate substitution | HIV-1 protease inhibition Ki [pM] | Anti-HIV-1 Cell Culture Activity EC50 [nM] | Cytotoxicity CC50 [μM] |
|---|---|---|---|---|---|
| none | Amprenavir | none | 45.6 ± 18.2 | 16 ± 2.2 | |
| none | 94-003 | none | 1.46 ± 0.58 | 1.4 ± 0.3 | |
| phosphonyl | 27 | diacid | 11.8 ± 6.0 | >100,000 | >100 |
| | 28 | diethyl | 1.2 ± 0.8 | 5.0 ± 2.8 | 70 |
| phosphonyl methoxy | 11 | diacid | 2.1 ± 0.2 | 4,800 ± 1,800 | >100 |
| | 13 | diethyl | 2.6 ± 1.5 | 3.0 ± 0 | 50 |
| | 14 | dibenzyl | 12.7 ± 1.9 | 2.3 ± 0.4 | 35 |
| | 16c | bis(Ala-ethylester) | 15.4 ± 0.85 | 105 ± 43 | 60 |
| | 16d | bis(Ala-butylester) | 18.75 ± 3.04 | 6.0 ± 1.4 | |
| | 16e | bis(ABA-ethylester) | 8.8 ± 1.7 | 12.5 ± 3.5 | |
| | 16f | bis(ABA-butylester) | 3.5 ± 1.4 | 4.8 ± 1.8 | |
| | 16a | bis(Gly-ethylester) | 29 ± 8.2 | 330 ± 230 | |
| | 16b | bis(Gly-butylester) | 4.9 ± 1.8 | 17.5 ± 10.5 | |
| | 16g | bis(Leu-ethylester) | 29 ± 9 | 6.8 ± 0.4 | |
| | 16h | bis(Leu-butylester) | 31.7 ± 19.3 | 120 ± 42 | |

TABLE 1-continued

| Enzyme inhibition activity (Ki), antiviral cell culture activity (EC50), and cytotoxicity (CC50) of the tested compounds. | | | | | |
|---|---|---|---|---|---|
| Substitution of (P1)phenyl | Compound | Phosphonate substitution | HIV-1 protease inhibition Ki [pM] | Anti-HIV-1 Cell Culture Activity EC50 [nM] | Cytotoxicity CC50 [μM] |
| | 16i | bis(Phe-ethylester) | | 17 ± 12 | |
| | 16j | bis(Phe-butylester) | | 35 ± 7 | |
| | 15 | bis(POC) | 36 | 825 ± 106 | |
| | 11 | Monoethyl, monoacid | 0.45 ± 0.15 | 700 ± 0 | |

Cross-Resistance Profile Assay

The assay is based on the determination of a difference in the susceptibility to a particular HIV protease inhibitor between the wild-type HIV-1 strain and a recombinant HIV-1 strain expressing specific drug resistance-associated mutation(s) in the viral protease gene. The absolute susceptibility of each virus to a particular tested compound is measured by using the XTT-based cytopathic assay as described in Example B. The degree of resistance to a tested compound is calculated as fold difference in EC50 between the wild type and a specific mutant virus.

Recombinant HIV-1 Strains with Resistance Mutations in the Protease Gene:

One mutant virus (82T/84V) was obtained from NIH AIDS Research and Reference Reagent Program (Rockville, Md.). Majority of the mutant HIV-1 strains were constructed by a homologous recombination between three overlapping DNA fragments: 1. linearized plasmid containing wild-type HIV-1 proviral DNA (strain HXB2D) with the protease and reverse transcriptase genes deleted, 2. DNA fragment generated by PCR amplification containing reverse transcriptase gene from HXB2D strain (wild-type), 3. DNA fragment generated by RT-PCR amplification from patients plasma samples containing viral protease gene with specific mutations selected during antiretroviral therapy with various protease inhibitors. Additional mutant HIV-1 strains were constructed by a modified procedure relying on a homologous recombination of only two overlapping DNA fragments: 1. linearized plasmid containing wild-type HIV-1 proviral DNA (strain HXB2D) with only the protease gene deleted, and 2. DNA fragment generated by RT-PCR amplification from patients plasma samples containing viral protease gene with specific mutations. In both cases, mixture of DNA fragments was delivered into Sup-T1 cells by using a standard electroporation technique. The cells were cultured in RPMI-1640 medium supplemented with 10% fetal bovine serum and antibiotics until the recombinant virus emerged (usually 10 to 15 days following the electroporation). Cell culture supernatant containing the recombinant virus was harvested and stored in aliquots. After determination of the virus titer the virus stock was used for drug resistance studies.

Example 39

Cross-Resistance Profile of the Tested Compounds

Cross-resistance profile of currently used HIV-1 protease inhibitors was compared with that of the newly invented compounds (Table 2).

TABLE 2

| Cross-resistance profile of HIV-1 protease inhibitors | | | | | | | | | | | | | |
|---|---|---|---|---|---|---|---|---|---|---|---|---|---|
| | | Fold Change in $EC_{50}$ Relative to WT HIV-1 | | | | | | | | | | | |
| Compound | EC 50 [nM] WT HIV-1 | 8K[a] 46I **90M** | 46I **84A** | 10I **48V** 54V **82A** | 46I 47V **50V** | 10R 46I **82T** **84V** | **30N** 50S **82I** 88D | 54V 71V **82S** | 10F 46I 71V **82T** **90M** | 10I **48V** 71V **82A** **90M** | **48V** 54V 71V **82S** | 10I **84V** 71V **73S** **90M** | Total No. of Resistant Viruses[b] |
| Amprenavir | 20 | 1.25 | **14** | 2 | **38** | 4 | 0.8 | 4 | **13** | 2.5 | 2 | **10** | 4 |
| Nelfinavir | 14 | **13** | **11** | **11.5** | 2 | 3 | **43** | **12** | **33** | **27** | **12** | **65** | 9 |
| Indinavir | 15 | 4 | **10** | **15** | nd | **7** | 1 | **10** | **13** | **28** | **23** | **43** | 8 |
| Ritonavir | 15 | **34** | **18** | **20** | **13** | **47** | 2 | **20** | **32** | **22** | **>50** | **42** | 10 |
| Saquinavir | 4 | 1 | 2.5 | **11** | 1 | 2.5 | 1 | 3 | 2.5 | **12** | **45** | **40** | 4 |
| Lopinavir | 8 | nd | **9** | nd | **19** | **11** | nd | nd | **7.5** | 4.5 | **60** | **11** | 6 |
| Tipranavir | 80 | nd | 1 | 0.4 | 0.5 | **5** | 0.5 | 3.5 | 3 | 0.3 | 2 | **nd** | 1 |
| 94-003 | 0.5 | nd | **8** | 0.5 | **29** | nd | 0.4 | 3.5 | nd | nd | nd | **8** | 3 |
| **GS 16503** | **16** | 1.2 | 1 | 0.4 | 3.3 | 1 | 0.6 | 0.9 | 1 | 0.4 | 0.5 | 2 | 0 |
| GS 16571 | 22 | 1.8 | 1 | 0.3 | 0.8 | 0.6 | 0.7 | 0.6 | 0.8 | 0.2 | 0.2 | 0.9 | 0 |
| GS 16587 | 15 | 1.5 | 1 | 0.5 | 2 | 1 | 1 | 0.9 | 1 | 0.4 | 0.4 | 1 | 0 |

[a]Resistance-associated mutations present in the viral protease. The highlighted changes represent primary resistance mutations.
[b]Resistance is considered as a 5-fold and higher change in the EC50 value of the mutant virus relative to the wild-type virus.

Example Section N

Plasma and PBMC Exposure Following Intravenous and Oral Administration of Prodrug to Beagle Dogs The pharmacokinetics of a phosphonate prodrug GS77366 (P1-monoLac-ipr), its active metabolite (metabolite X, or GS77568), and GS8373 were studied in dogs following intravenous and oral administration of the prodrug.

Dose Administration and Sample Collection. The in-life phase of this study was conducted in accordance with the USDA Animal Welfare Act and the Public Health Service Policy on Humane Care and Use of Laboratory Animals, and followed the standards for animal husbandry and care found in the Guide for the Care and Use of Laboratory Animals, 7$^{th}$ Edition, Revised 1996. All animal housing and study procedures involving live animals were carried out at a facility which had been accredited by the Association for Assessment and Accreditation of Laboratory Animal Care—International (AAALAC).

Each animal in a group of 4 female beagle dogs was given a bolus dose of GS77366 (P1-monoLac-iPr) intravenously at 1 mg/kg in a formulation containing 40% PEG 300, 20% propylene glycol and 40% of 5% dextrose. Another group of 4 female beagle dogs was dosed with GS77366 via oral gavage at 20 mg/kg in a formulation containing 60% Vitamin-E TPGS, 30% PEG 400 and 10% propylene glycol.

Blood samples were collected pre-dose, and at 5 min, 15 min, 30 min, 1 hr, 2 hr, 4 hr, 8 hr, 12 hr and 24 hr post-dose. Plasma (0.5 to 1 mL) was prepared from each sample and kept at 70° C. until analysis. Blood samples (8 mL) were also collected from each dog at 2, 8 and 24 hr post dose in Becton-Dickinson CPT vacutainer tubes. PBMCs were isolated from the blood by centrifugation for 15 minutes at 1500 to 1800 G. After centrifugation, the fraction containing PBMCs was transferred to a 15 mL conical centrifuge tube and the PBMCs were washed twice with phosphate buffered saline (PBS) without $Ca^{2+}$ and $Mg^{2+}$. The final wash of the cell pellet was kept at −70° C. until analysis.

Measurement of the prodrug, metabolite X and GS8373 in plasma and PBMCs. For plasma sample analysis, the samples were processed by a solid phase extraction (SPE) procedure outlined below. Speedisk C18 solid phase extraction cartridges (1 mL, 20 mg, 10 μM, from J. T. Baker) were conditioned with 200 μL of methanol followed by 200 μL of water. An aliquot of 200 μL of plasma sample was applied to each cartridge, followed by two washing steps each with 200 μL of deionized water. The compounds were eluted from the cartridges with a two-step process each with 125 μL of methanol. Each well was added 50 μL of water and mixed. An aliquot of 25 μL of the mixture was injected onto a ThermoFinnigan TSQ Quantum LC/MS/MS system.

The column used in liquid chromatography was HyPURITY® C18 (50×2.1 mm, 3.5 um) from Thermo-Hypersil. Mobile phase A contained 10% acetonitrile in 10 mM ammonium formate, pH 3.0. Mobile phase B contained 90% acetonitrile in 10 mM ammonium formate, pH 4.6. The chromatography was carried out at a flow rate of 250 μL/min under an isocratic condition of 40% mobile phase A and 60% mobile phase B. Selected reaction monitoring (SRM) were used to measure GS77366, GS8373 and Metabolite X with the positive ionization mode on the electrospray probe. The limit of quantitation (LOQ) was 1 nM for GS77366, GS8373 and GS77568 (Metabolite X) in plasma.

For PBMC sample analysis, phosphate buffered saline (PBS) was added to each PBMC pellet to bring the total sample volume to 500 μL in each sample. An aliquot of 150 μL from each PBMC sample was mixed with an equal volume of methanol, followed by the addition of 700 μL of 1% formic acid in water. The resulting mixture was applied to a Speedisk C18 solid phase extraction cartridge (1 mL, 20 mg, 10 um, from J. T. Baker) which had been conditioned as described above. The compounds were eluted with methanol after washing the cartridge 3 times with 10% methanol. The solvent was evaporated under a stream of $N_2$, and the sample was reconstituted in 150 μL of 30% methanol. An aliquot of 75 μL of the solution was injected for LC/MS/MS analysis. The limit of quantitation was 0.1 ng/mL in the PBMC suspension.

Pharmacokinetic Calculations. The pharmacokinetic parameters were calculated using WinNonlin. Noncompartmental analysis was used for all pharmacokinetic calculation. The intracellular concentrations in PBMCs were calculated from the measured concentrations in PBMC suspension on the basis of a reported volume of 0.2 picoliter/cell (B. L. Robins, R. V. Srinivas, C. Kim, N. Bischofberger, and A. Fridland, (1998) Antimicrob. Agents Chemother. 42, 612).

Plasma and PBMC Concentration-time Profiles.

The concentration-time profiles of GS77366, GS77568 and GS8373 in plasma and PBMCs following intravenous dosing of GS77366 were compared at 1 mg/kg in dogs. The data demonstrate that the prodrug can effectively deliver the active components (metabolite X and GS8373) into cells that are primarily responsible for HIV replication, and that the active components in these cells had much longer half-life than in plasma.

The pharmacokinetic properties of GS77568 in PBMCs following oral administration of GS77366 in dogs are compared with that of nelfinavir and amprenavir, two marketed HIV protease inhibitors (Table 3). These data show that the active component (GS77568) from the phosphonate prodrug had sustained levels in PBMCs compared to nelfinavir and amprenavir.

TABLE 3

Comparison of GS77568 with nelfinavir and amprenavir in PBMCs following oral administration in beagle dogs.

| Compound | Dose | $t_{1/2}$ (hr) | $AUC_{(2\text{-}24\ hr)}$ |
|---|---|---|---|
| Nelfinavir | 17.5 mg/kg | 3.0 hr | 33,000 nM · hr |
| Amprenavir | 20 mg/kg | 1.7 hr | 102,000 nM · hr |
| GS77568 | 20 mg/kg of GS77366 | >20 hr | 42,200 nM · hr |

Example Section O

Intracellular Metabolism/In Vitro Stability

1. Uptake and Persistence in MT2 Cells, Quiescent and Stimulated PBMC

The protease inhibitor (PI) phosphonate prodrugs undergo rapid cell uptake and metabolism to produce acid metabolites including the parent phosphonic acid. Due to the presence of charges, the acid metabolites are significantly more persistent in the cells than non-charged PI's. In order to estimate the relative intracellular levels of the different PI prodrugs, three compounds representative of three classes of phosphonate PI prodrugs—bisamidate phosphonate, monoamidate phenoxy phosphonate and monolactate phenoxy phosphonate (FIG. 1) were incubated at 10 μM for 1 hr with MT-2 cells, stimulated and quiescent peripheral blood mononuclear cells (PBMC) (pulse phase). After incubation, the cells were washed, resuspended in the cell culture media and incubated for 24 hr (chase phase). At specific time points, the cells were washed, lysed and the lysates were analyzed by HPLC with UV detection. Typically, the cell lysates were centrifuged and 100 uL of the supernatant were mixed with 200 μL of 7.5 uM amprenavir (Internal Standard) in 80% acetonitrile/20% water and injected into an HPLC system (70 μL).

HPLC Conditions:

Analytical Column: Prodigy ODS-3, 75×4.6, 3u+C18 guard at 40° C.

Gradient:

Mobile Phase A: 20 mM ammonium acetate in 10% ACN/90% $H_2O$

Mobile Phase B: 20 mM ammonium acetate in 70% ACN/30% $H_2O$ 30-100% B in 4 min, 100% B for 2 min, 30% B for 2 min at 2.5 mL/min.

Run Time: 8 min

UV Detection at 245 nm

Concentrations of Intracellular metabolites were calculated based on cell volume 0.2 μL/mLn cells for PBMC and 0.338 μL/mLn (0.676 uL/mL) for MT-2 cells.

Chemical Structures of Selected Protease Inhibitor Phosphonate Prodrugs and Intracellular Metabolites:

TABLE 4

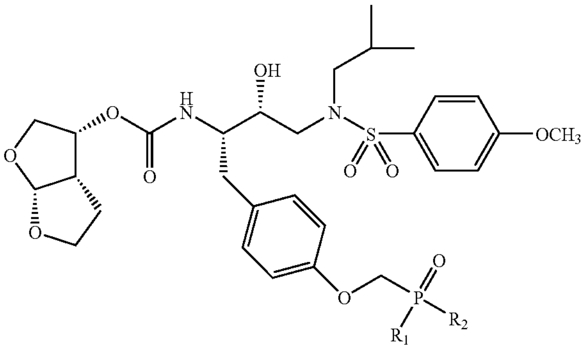

| GS No. | R1 | R2 | $EC_{50}$ (nM) |
|---|---|---|---|
| 8373 | OH | OH | 4,800 ± 1,800 |
| 16503 | $HNCH(CH_3)COOBu$ | $HNCH(CH_3)COOBu$ | 6.0 ± 1.4 |
| 16571 | OPh | $HNCH(CH_3)COOEt$ | 15 ± 5 |
| 17394 | OPh | $OCH(CH_3)COOEt$ | 20 ± 7 |
| 16576 | OPh | $HNCH(CH_2CH_3)COOEt$ | 12.6 ± 4.8 |
| Met X | OH | $HNCH(CH_3)COOH$ | >10,000 |
| Met LX | OH | $OCH(CH_3)COOEt$ | 1750 ± 354 |

A significant uptake and conversion of all 3 compounds in all cell types was observed (Table 4). The uptake in the quiescent PBMC was 2-3-fold greater than in the stimulated cells. GS-16503 and GS-16571 were metabolized to Metabolite X and GS-8373. GS-17394 metabolized to the Metabolite LX. Apparent intracellular half-lives were similar for all metabolites in all cell types (7-12 hr). A persistence of Total Acid Metabolites of Protease Inhibitor Prodrugs in Stimulated (A), Quiescent PBMC (B) and MT-2 Cells (C) (1 hr, 10 uM Pulse, 24 hr Chase) was observed.

2. Uptake and Persistence in Stimulated and Quiescent T-cells

Since HIV mainly targets T-lymphocytes, it is important to establish the uptake, metabolism and persistence of the metabolites in the human T-cells. In order to estimate the relative intracellular levels of the different PI prodrugs, GS-16503, 16571 and 17394 were incubated at 10 μM for 1 hr with quiescent and stimulated T-cells (pulse phase). The prodrugs were compared with a non-prodrug PI, nelfinavir. After incubation, the cells were washed, resuspended in the cell culture media and incubated for 4 hr (chase phase). At specific time points, the cells were washed, lysed and the lysates were analyzed by HPLC with UV detection. The sample preparation and analysis were similar to the ones described for MT-2 cells, quiescent and stimulated PBMC.

Table 5 demonstrate the levels of total acid metabolites and corresponding prodrugs in T-cells following pulse/chase and continuous incubation. There was significant cell uptake/metabolism in T-lymphocytes. There was no apparent difference in uptake between stimulated and quiescent T-lymphocytes. There was significantly higher uptake of phosphonate PI's than nelfinavir. GS 17394 demonstrates higher intracellular levels than GS16571 and GS16503. The degree of conversion to acid metabolites varied between different prodrugs. GS-17394 demonstrated the highest degree of conversion, followed by GS-16503 and GS-16571. The metabolites, generally, were an equal mixture of the mono-phosphonic acid metabolite and GS-8373 except for GS-17394, where Metabolite LX was stable, with no GS-8373 formed.

TABLE 5

Intracellular Levels of Metabolites and Intact Prodrug Following Continuous and 1 hr Pulse/4 hr Chase Incubation (10 μM/0.7 mLn cells/1 mL) of 10 μM PI Prodrugs and Nelfinavir with Quiescent and Stimulated T-cell

| | | Continuous Incubation | | | | 1 hr Pulse/4 hr Chase | | | |
|---|---|---|---|---|---|---|---|---|---|
| | | Quiescent T-cells | | Stimulated T-cells | | Quiescent T-cells | | Stimulated T-cells | |
| Compound | Time (h) | Acid Met (μM) | Prodrug (μM) | Acid Met (μM) | Prodrug (μM) | Acid Met (μM) | Prodrug (μM) | Acid Met (μM) | Prodrug (μM) |
| 16503 | 0 | 1180 | 42 | 2278 | 0 | 2989 | 40 | 1323 | 139 |
| | 2 | 3170 | 88 | 1083 | 116 | 1867 | 4 | 1137 | 31 |
| | 4 | 5262 | 0 | 3198 | 31 | 1054 | 119 | 1008 | 0 |
| 16571 | 0 | 388 | 1392 | 187 | 1417 | 1042 | 181 | 858 | 218 |
| | 2 | 947 | 841 | 1895 | 807 | 1170 | 82 | 1006 | 35 |
| | 4 | 3518 | 464 | 6147 | 474 | 1176 | 37 | 616 | 25 |

TABLE 5-continued

Intracellular Levels of Metabolites and Intact Prodrug Following Continuous and 1 hr Pulse/4 hr Chase Incubation (10 μM/0.7 mLn cells/1 mL) of 10 μM PI Prodrugs and Nelfinavir with Quiescent and Stimulated T-cell

| | | Continuous Incubation | | | | 1 hr Pulse/4 hr Chase | | | |
|---|---|---|---|---|---|---|---|---|---|
| | | Quiescent T-cells | | Stimulated T-cells | | Quiescent T-cells | | Stimulated T-cells | |
| Compound | Time (h) | Acid Met (μM) | Prodrug (μM) | Acid Met (μM) | Prodrug (μM) | Acid Met (μM) | Prodrug (μM) | Acid Met (μM) | Prodrug (μM) |
| 17394 | 0 | 948 | 1155 | 186 | 1194 | 4480 | 14 | 2818 | 10 |
| | 2 | 7231 | 413 | 3748 | 471 | 2898 | 33 | 1083 | 51 |
| | 4 | 10153 | 167 | 3867 | 228 | 1548 | 39 | 943 | 104 |
| Nelfinavir | 0 | | 101 | | 86 | | 886 | | 1239 |
| | 2 | | 856 | | 846 | | 725 | | 770 |
| | 4 | | 992 | | 1526 | | 171 | | 544 |

3. PBMC Uptake and Metabolism of Selected PI Prodrugs Following 1-hr Incubation in MT-2 Cells at 10, 5 and 1 μM.

To were similar to the determine if the cell uptake/metabolism is concentration dependent, selected PI's were incubated with the 1 mL of MT-2 cell suspension (2.74 mLn cells/mL) for 1 hr at 37° C. at 3 different concentrations: 10, 5 and 1 μM. Following incubation, cells were washed twice with the cell culture medium, lysed and assayed using HPLC with UV detection. The sample preparation and analysis ones described for MT-2 cells, quiescent and stimulated PBMC. Intracellular concentrations were calculated based on cell count, a published single cell volume of 0.338 pl for MT-2 cells, and concentrations of analytes in cell lysates. Data are shown in Table 6.

Uptake of all three selected PI's in MT-2 cells appears to be concentration-independent in the 1-10 μM range. Metabolism (conversion to acid metabolites) appeared to be concentration-dependent for GS-16503 and GS-16577 (3-fold increase at 1 μM vs. 10 μM) but independent for GS-17394 (monolactate). Conversion from a respective metabolite X to GS-8373 was concentration-independent for both GS-16503 and GS-16577 (no conversion was observed for metabolite LX of GS-17394).

4. PBMC Uptake and Metabolism of Selected PI Prodrugs Following 1-hr Incubation in Human Whole Blood at 10 μM.

In order to estimate the relative intracellular levels of the different PI prodrugs under conditions simulating the in vivo environment, compounds representative of three classes of phosphonate PI prodrugs—bisamidate phosphonate (GS-16503), monoamidate phenoxy phosphonate (GS-16571) and monolactate phenoxy phosphonate (GS-17394) were incubated at 10 μM for 1 hr with intact human whole blood at 37° C. After incubation, PBMC were isolated, then lysed and the lysates were analyzed by HPLC with UV detection. The results of analysis are shown in Table 7. There was significant cell uptake/metabolism following incubation in whole blood. There was no apparent difference in uptake between GS-16503 and GS-16571. GS-17394 demonstrated significantly higher intracellular levels than GS16571 and GS-16503.

The degree of conversion to acid metabolites varies between different prodrugs after 1 hr incubation. GS-17394 demonstrated the highest degree of conversion, followed by GS-16503 and GS-16571 (Table 7). The metabolites, generally, were an equimolar mixture of the mono-phosphonic acid

TABLE 6

Uptake and Metabolism of Selected PI Prodrugs Following 1-hr Incubation in MT-2 Cells at 10, 5 and 1 μM.

| | Extracellular | Cell-Assosiated Prodrug and Metabolites Concentration, μM | | | | % Conversion to acid |
|---|---|---|---|---|---|---|
| Compound | Concentration, μM | Metabolite X | GS8373 | Prodrug | Total | metabolites |
| GS-17394 | 10 | 1358 | 0 | 635 | 1993 | 68 |
| | 5 | 916 | 0 | 449 | 1365 | 67 |
| | 1 | 196 | 0 | 63 | 260 | 76 |
| GS-16576 | 10 | 478 | 238 | 2519 | 3235 | 22 |
| | 5 | 250 | 148 | 621 | 1043 | 40 |
| | 1 | 65 | 36 | 61 | 168 | 64 |
| GS-16503 | 10 | 120 | 86 | 1506 | 1712 | 12 |
| | 5 | 58 | 60 | 579 | 697 | 17 |
| | 1 | 12 | 18 | 74 | 104 | 29 |

*For GS16576, Metabolite X is mono-aminobutyric acid metabolite and GS-8373 (parent acid) except for GS-17394, where Metabolite LX was stable with no GS-8373 formed.

TABLE 7

PBMC Uptake and Metabolism of Selected PI Prodrugs Following 1-hr Incubation in Human Whole Blood at 10 μM (Mean ± SD, N = 3).

| | Intracellular Prodrug and Metabolites Concentration, μM | | | Major Intracellular |
|---|---|---|---|---|
| GS# | Acid Metabolite | Prodrug, μM | Total, μM | Metabolites |
| 16503 | 279 ± 47 | 61 ± 40 | 340 ± 35 | X, GS-8373 |
| 16571 | 319 ± 112 | 137 ± 62 | 432 ± 208 | X, GS-8373 |
| 17394 | 629 ± 303 | 69 ± 85 | 698 ± 301 | LX |

*PBMC Intracellular Volume = 0.2 μL/mln

5. Distribution of PI Prodrugs in PBMC

In order to compare distribution and persistence of PI phosphonate prodrugs with those of non-prodrug PI's, GS-16503, GS-17394 and nelfinavir, were incubated at 10 μM for 1 hr with PBMC (pulse phase). After incubation, the cells were washed, resuspended in the cell culture media and incubated for 20 more hr (chase phase). At specific time points, the cells were washed and lysed. The cell cytosol was separated from membranes by centrifugation at 9000×g. Both cytosol and membranes were extracted with acetonitrile and analyzed by HPLC with UV detection.

Table 8 shows the levels of total acid metabolites and corresponding prodrugs in the cytosol and membranes before and after the 22 hr chase. Both prodrugs exhibited complete conversion to the acid metabolites (GS-8373 and X for GS-16503 and LX for GS-17394, respectively). The levels of the acid metabolites of the PI phosphonate prodrugs in the cytosol fraction were 2-3-fold greater than those in the membrane fraction after the 1 hr pulse and 10-fold greater after the 22 hr chase. Nelfinavir was present only in the membrane fractions. The uptake of GS-17394 was about 3-fold greater than that of GS-16503 and 30-fold greater than nelfinavir. The metabolites were an equimolar mixture of metabolite X and GS-8373 (parent acid) for GS-16503 and only metabolite LX for GS-17394.

6. PBMC Extract/Dog Plasma/Human Serum Stability of Selected PI Prodrugs

The in vitro metabolism and stability of the PI phosphonate prodrugs were determined in PBMC extract, dog plasma and human serum (Table 9). Biological samples listed below (120 μL) were transferred into an 8-tube strip placed in the aluminum 37° C. heating block/holder and incubated at 37° C. for 5 min. Aliquots (2.5 μL) of solution containing 1 mM of test compounds in DMSO, were transferred to a clean 8-tube strip, placed in the aluminum 37° C. heating block/holder. 60 μL aliquots of 80% acetonitrile/20% water containing 7.5 μM of amprenavir as an internal standard for HPLC analysis were placed into five 8-tube strips and kept on ice/refrigerated prior to use. An enzymatic reaction was started by adding 120 μL aliquots of a biological sample to the strip with the test compounds using a multichannel pipet. The strip was immediately vortex-mixed and the reaction mixture (20 μL) was sampled and transferred to the Internal Standard/ACN strip. The sample was considered the time-zero sample (actual time was 1-2 min). Then, at specific time points, the reaction mixture (20 μL) was sampled and transferred to the corresponding IS/ACN strip. Typical sampling times were 6, 20, 60 and 120 min. When all time points were sampled, an 80 μL aliquot of water was added to each tube and strips were centrifuged for 30 min at 3000×G. The supernatants were analyzed with HPLC under the following conditions:

Column: Inertsil ODS-3, 75×4.6 mm, 3 μm at 40° C.

Mobile Phase A: 20 mM ammonium acetate in 10% ACN/90% water

Mobile Phase B 20 mM ammonium acetate in 70% ACN/30% water

Gradient: 20% B to 100% B in 4 min, 2 min 100% B, 2 min 20% B

Flow Rate: 2 mL/min

Detection: UV at 243 nm

Run Time: 8 min

The biological samples evaluated were as follows:

PBMC cell extract was prepared from fresh cells using a modified published procedure (A. Pompon, I. Lefebvre, J-L. Imbach, S. Kahn, and D. Farquhar, Antiviral Chemistry & Chemotherapy, 5, 91-98 (1994)). Briefly, the extract was prepared as following: The cells were separated from their cul-

TABLE 8

Uptake and Cell Distribution of Metabolites and Intact Prodrugs Following Continuous and 1 hr Pulse/22 hr Chase Incubation of 10 μM PI Prodrugs and Nelfinavir with Quiescent PBMC.

| | | | Cell-Associated PI, pmol/mln cells | | | |
|---|---|---|---|---|---|---|
| | | | 1 hr Pulse/ 0 hr Chase | | 1 hr Pulse/22 hr Chase | |
| GS# | Cell Type | Fraction | Acid Metabolites | Prodrug | Acid Metabolites | Prodrug |
| GS-16503 | PBMC | Membrane | 228 | 0 | 9 | 0 |
| GS-16503 | PBMC | Cytosol | 390 | 0 | 130 | 0 |
| GS-17394 | PBMC | Membrane | 335 | 0 | 26 | 0 |
| GS-17394 | PBMC | Cytosol | 894 | 0 | 249 | 0 |
| Nelfinavir | PBMC | Membrane | | 42 | | 25 |
| Nelfinavir | PBMC | Cytosol | | 0 | | 0 |

Uptake and cell distribution of metabolites and intact prodrugs following 1 hr pulse/22 hr chase incubation of 10 μM PI prodrugs and Nelfinavir with quiescent PBMC were measured.

ture medium by centrifugation (1000 g, 15 min, ambient temperature). The residue (about 100 μL, $3.5\times10^8$ cells) was resuspended in 4 mL of a buffer (0.010 M HEPES, pH 7.4, 50 mM potassium chloride, 5 mM magnesium chloride and 5 mM dl-dithiothreitol) and sonicated. The lysate was centrifuged (9000 g, 10 min, 4° C.) to remove membranes. The upper layer (0.5 mg protein/mL) was stored at −70° C. The reaction mixture contained the cell extract at about 0.5 mg protein/mL.

Human serum (pooled normal human serum from George King Biomedical Systems, Inc.). Protein concentration in the reaction mixture was about 60 mg protein/mL.

Dog Plasma (pooled normal dog plasma (EDTA) from Pel Freez, Inc.). Protein concentration in the reaction mixture was about 60 mg protein/mL.

TABLE 9

PBMC Extract/Dog Plasma/Human Serum Stability of Selected PI Prodrugs

| GS# | PBMC Extract[1] $T_{1/2}$, min | Dog Plasma $T_{1/2}$, min | Human Serum $T_{1/2}$, min | HIV $EC_{50}$ (nM) |
|---|---|---|---|---|
| 16503 | 2 | 368 | >>400 | 6.0 ± 1.4 |

TABLE 9-continued

PBMC Extract/Dog Plasma/Human Serum Stability of Selected PI Prodrugs

| GS# | PBMC Extract[1] $T_{1/2}$, min | Dog Plasma $T_{1/2}$, min | Human Serum $T_{1/2}$, min | HIV $EC_{50}$ (nM) |
|---|---|---|---|---|
| 16571 | 49 | 126 | 110 | 15 ± 5 |
| 17394 | 15 | 144 | 49 | 20 ± 7 |

Example Section P

TABLE 10

Enzymatic and Cellular data
Formula II ALPPI activity

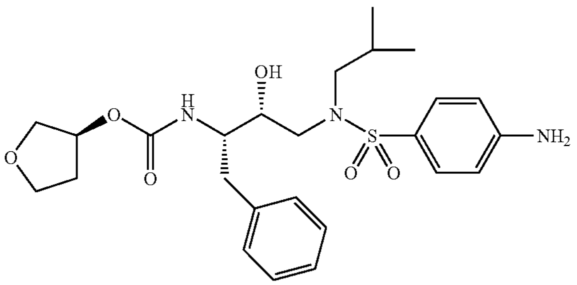

Amprenavir

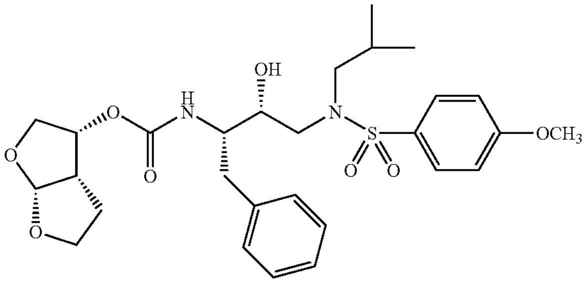

94-0003

| Ki [pM] | |
|---|---|
| ≦10 | +++ |
| >10 to ≦100 | ++ |
| >100 to ≦1,000 | + |
| >1,000 | − |

| $EC_{50}$ [mM] | |
|---|---|
| ≦50 | +++ |
| >50 to ≦500 | ++ |
| >500 to ≦5,000 | + |
| >5,000 | − |

| I50V and I84V/L90M fold change | |
|---|---|
| >30 | +++ |
| >10 to ≦30 | ++ |
| >3 to ≦10 | + |
| ≦3 | − |

TABLE 10-continued

| CC$_{50}$ [μM] | |
|---|---|
| ≦5 | ++ |
| >5 to ≦50 | + |
| >50 | − |

| Compound | Ki (pM) | EC$_{50}$ (nM) | I50V (#1) fold change | I50V (#2) fold change | I84V/L90M fold change | CC$_{50}$ (μM) |
|---|---|---|---|---|---|---|
| Saquinavir | ++ | +++ | − | − | +++ | |
| Nelfinavir | + | +++ | − | + | +++ | |
| Indinavir | + | +++ | − | + | +++ | |
| Ritonavir | ++ | +++ | ++ | ++ | +++ | |
| Lopinavir | ++ | +++ | ++ | +++ | ++ | |
| Amprenavir | + | +++ | +++ | +++ | ++ | − |
| Atazanavir | ++ | +++ | − | − | +++ | |
| Tipranavir | ++ | ++ | − | − | + | |
| 94-003 | +++ | +++ | +++ | +++ | ++ | + |
| TMC114 | +++ | +++ | ++ | ++ | − | |

P1-Phosphonic acid and esters

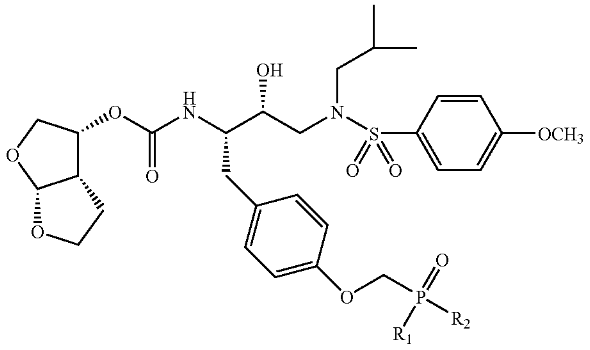

| R1 | R2 | Ki (pM) | EC$_{50}$ (nM) | I50V (#1) fold change | I84V/L90M fold change | CC$_{50}$ (μM) |
|---|---|---|---|---|---|---|
| OH | OH | +++ | + | − | − | − |
| OMe | OMe | ++ | +++ | | | |
| OEt | OEt | +++ | +++ | − | − | + |
| OCH$_2$CF$_3$ | OCH$_2$CF$_3$ | ++ | − | | | |
| OiPr | OiPr | ++ | +++ | − | − | |
| OPh | OPh | | +++ | | | |
| OMe | OPh | ++ | +++ | | | |
| OEt | OPh | +++ | +++ | | | |
| OBn | OBn | ++ | +++ | − | − | + |
| OEt | OBn | ++ | +++ | | | ++ |
| OPoc | OPoc | | + | | | |
| OH | OEt | | ++ | | | |
| OH | OPh | +++ | − | | | |
| OH | OBn | | + | − | − | |

P1-Phosphonic acid and esters
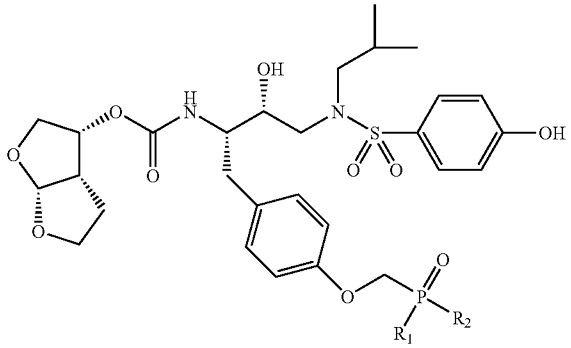
| R1 | R2 | Ki (pM) | $EC_{50}$ (nM) | I50V (#1) fold change | I84V/L90M fold change | $CC_{50}$ (μM) |
|---|---|---|---|---|---|---|
| OH | OH | +++ | + | | | |
| Et | Et | +++ | +++ | | | |
P1-Direct phosphonic acid and esters
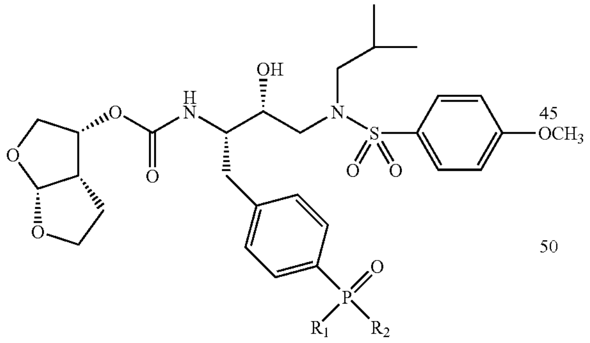
| R1 | R2 | Ki (pM) | $EC_{50}$ (nM) | I50V (#1) fold change | I84V/L90M fold change | $CC_{50}$ μM |
|---|---|---|---|---|---|---|
| OH | OH | ++ | – | | | |
| OEt | OEt | +++ | +++ | + | – | |

P1-$CH_2$-phosphonic acid and esters

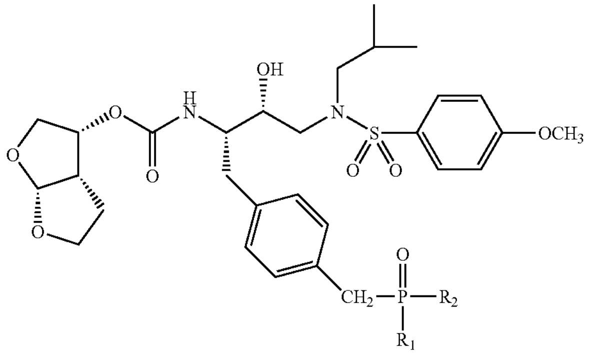

| R1 | R2 | Ki (pM) | $EC_{50}$ (nM) | I50V (#1) fold change | I84V/L90M fold change | $CC_{50}$ μM |
|---|---|---|---|---|---|---|
| OE | OE | +++ | +++ | + | + | |

P1-P-Bisamidates

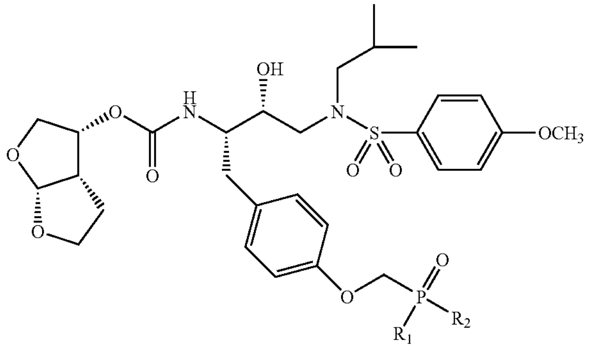

| R1 | R2 | Ki (pM) | $EC_{50}$ (nM) | I50V (#1) fold change | I84V/L90M fold change | $CC_{50}$ μM |
|---|---|---|---|---|---|---|
| NHEt | NHEt | +++ | ++ | − | − | |
| Gly-Et | Gly-Et | ++ | ++ | | | |
| Gly-Bu | Gly-Bu | +++ | +++ | | | |
| Ala-Et | Ala-Et | ++ | ++ | | − | − |
| Ala-Bu | Ala-Bu | ++ | +++ | + | − | |
| Aba-Et | Aba-Et | +++ | +++ | | | |
| Aba-Bu | Aba-Bu | +++ | +++ | ++ | + | |
| Val-Et | Val-Et | + | +++ | − | − | |
| Leu-Et | Leu-Et | ++ | +++ | | | |
| Leu-Bu | Leu-Bu | ++ | ++ | + | + | |
| Phe-Et | Phe-Et | | +++ | | | |
| Phe-Bu | Phe-Bu | | +++ | | | |

P1-P-Bislactates

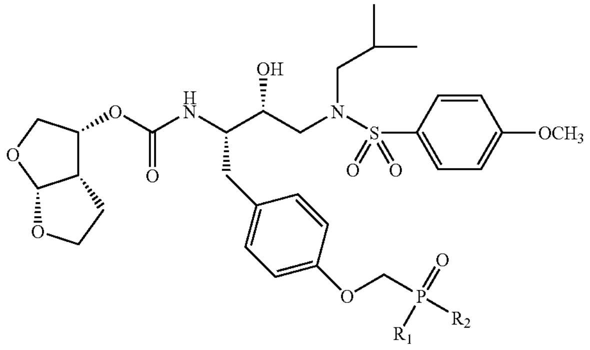

| R1 | R2 | Ki (pM) | $EC_{50}$ (nM) | I50V (#1) fold change | I84V/L90M fold change | $CC_{50}$ μM |
|---|---|---|---|---|---|---|
| Glc-Et | Glc-Et | +++ | + | – | – | |
| Lac-Et | Lac-Et | ++ | ++ | – | – | |
| Lac-iPr | Lac-iPr | ++ | +++ | | – | |

P1-P-Monoamidates

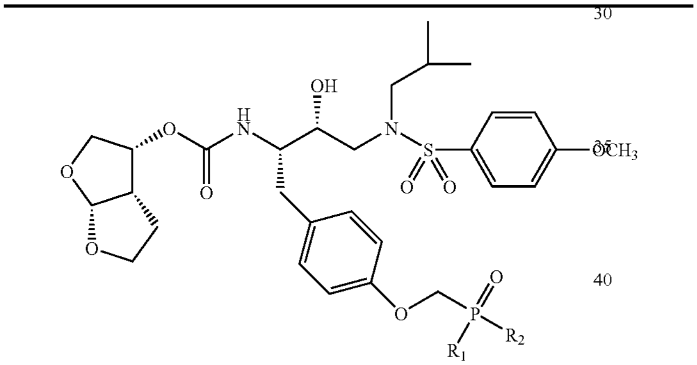

| R1 | R2 | Ki (pM) | $EC_{50}$ (nM) | I50V (#1) fold change | I84V/L90M fold change | $CC_{50}$ μM |
|---|---|---|---|---|---|---|
| OPh | Gly-Bu | ++ | ++ | – | – | |
| OPh | Ala-Me | ++ | +++ | | – | |
| OPh | Ala-Et | +++ | +++ | – | – | |
| OPh | Ala-iPr | ++ | +++ | – | – | |
| OPh | Ala-iPr | +++ | +++ | | | |
| OPh | Ala-iPr | ++ | +++ | | | |
| OPh | (D)Ala-iPr | ++ | +++ | | – | |
| OPh | (D)Ala-iPr | +++ | +++ | | | |
| OPh | (D)Ala-iPr | +++ | +++ | | | |
| OPh | Ala-Bu | ++ | +++ | – | – | |
| OPh | Ala-Bu | ++ | +++ | – | | |
| OPh | Ala-Bu | ++ | +++ | – | | |
| OPh | Aba-Et | | +++ | | | |
| OPh | Aba-Et | | +++ | – | – | |
| OPh | Aba-Et | | ++ | | | |
| OPh | Aba-Bu | | +++ | + | – | |
| OPh | Aba-Bu | | ++ | – | – | |
| OBn | Ala-Et | +++ | +++ | – | – | |
| OH | Ala-OH | +++ | – | | | |
| OH | Ala-Bu | | – | | | |

P1-P-Monolactates (1)

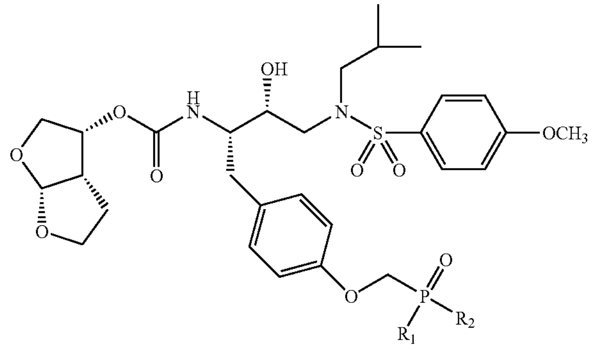

| R1 | R2 | Ki (pM) | $EC_{50}$ (nM) | I50V (#1) fold change | I50V (#2) fold change | I84V/L90M fold change | $CC_{50}$ μM |
|---|---|---|---|---|---|---|---|
| OPh | Glc-Et | +++ | +++ | − | | − | |
| OPh | Lac-Me | | ++ | − | | | |
| OPh | Lac-Et | | +++ | − | + | − | + |
| OPh | Lac-Et | +++ | +++ | − | | − | |
| OPh | Lac-Et | ++ | +++ | − | | − | |
| OPh | Lac-iPr | ++ | +++ | − | | − | |
| OPh | Lac-iPr | +++ | +++ | | | | |
| OPh | Lac-iPr | ++ | +++ | | | | |
| OPh | Lac-Bu | ++ | ++ | | | − | |
| OPh | Lac-Bu | ++ | ++ | | | | |
| OPh | Lac-Bu | ++ | ++ | | | | |
| OPh | Lac-EtMor | | − | | | | |
| OPh | Lac-PrMor | | − | | | | |
| OPh | (R)Lac-Me | +++ | +++ | | | | |
| OPh | (R)Lac-Et | +++ | +++ | − | | − | |
| OEt | Lac-Et | | ++ | | | | |
| $OCH_2CF_3$ | Lac-Et | | ++ | | | | |
| OBn | Lac-Bn | ++ | ++ | | | | |
| OBn | (R)Lac-Bn | | | | | | |
| OH | Lac-OH | +++ | + | | | − | |
| OH | (R)Lac-OH | ++ | + | | | − | |

P1-P-Monolactates (2)

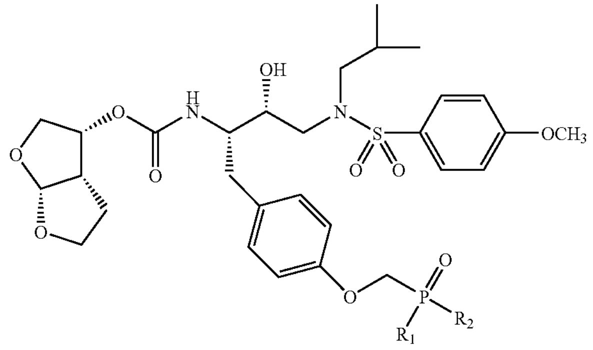

| R1 | R2 | Ki (pM) | $EC_{50}$ (nM) | I50V (#1) fold change | I84V/L90M fold change | $CC_{50}$ μM |
|---|---|---|---|---|---|---|
| OPh | mix-Hba-Et | ++ | +++ | + | − | |
| OPh | (S)Hba-Et | + | +++ | | | |
| OPh | (S)Hba-tBu | | +++ | | | |
| OH | (S)Hba-OH | ++ | | | | |
| OPh | (R)Hba-Et | | +++ | | | |
| OPh | (S)MeBut-Et | | +++ | | | |
| OPh | (R)MeBut-Et | | +++ | | | |

-continued

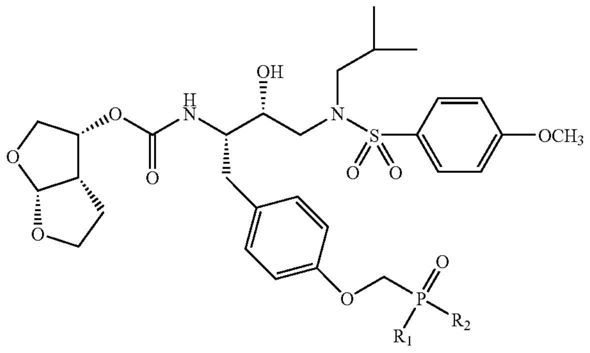

| R1 | R2 | Ki (pM) | $EC_{50}$ (nM) | I50V (#1) fold change | I84V/L90M fold change | $CC_{50}$ μM |
|---|---|---|---|---|---|---|
| OPh | DiMePro-Me | ++ | | | | |
| OPh | (S)Lac-EtMor | | – | | | |
| OPh | (S)Lac-PrMor | | – | | | |
| OPh | (S)Lac-EtPip | | – | – | | |

P1-P-Monolactates (3)

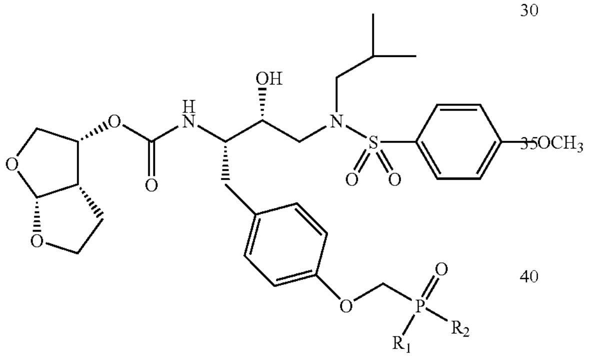

| R1 | R2 | Ki (pM) | $EC_{50}$ (nM) | I50V (#1) fold change | I84V/L90M fold change | $CC_{50}$ μM |
|---|---|---|---|---|---|---|
| OPh-o-i-But | (S)Lac-Et | | +++ | | | |
| OPh-p-n-Oct | (S)Lac-Et | | ++ | | | |
| OPh-p-n-But | (S)Lac-Et | | +++ | | | |
| OPh-m-COOBn | (S)Lac-Et | | ++ | | | |
| OPh-m-COOH | (S)Lac-Et | | ++ | | | |
| OPh-m-$CH_2$OH | (S)Lac-Et | | ++ | – | – | |
| OPh-m-$CH_2NH_2$ | (S)Lac-Et | ++ | ++ | | | |
| OPh-m-$CH_2NMe_2$ | (S)Lac-Et | | + | | | |
| OPh-m-$CH_2$Mor | (S)Lac-Et | | ++ | – | – | |
| OPh-m-$CH_2$Pip | (S)Lac-Et | | ++ | | | |
| OPh-m-$CH_2$NMeC2OM | (S)Lac-Et | | ++ | | | |
| OPh-o-OEt | (S)Lac-Et | | +++ | | | |
| $ONMe_2$ | (S)Lac-Et | | ++ | | | |
| OPip | (S)Lac-Et | | + | | | |
| OMor | (S)Lac-Et | | – | | | |

P1-$C_2H_4$-P-Monolactates

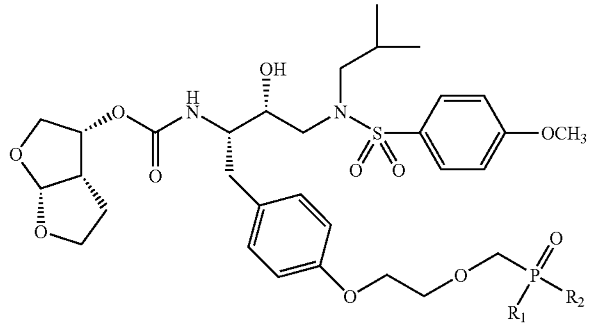

| R1 | R2 | Ki (pM) | $EC_{50}$ (nM) | I50V (#1) fold change | I84V/L90M fold change | $CC_{50}$ μM |
|---|---|---|---|---|---|---|
| —$OC_2H_4OBn$ | | | +++ | | | |
| OEt | OEt | | +++ | – | – | |
| OPh | Lac-Et | | ++ | – | – | |
| OH | OH | ++ | | | | |
| OH | Lac | ++ | | | | |

P1-$CH_2N$—P-diester and monolactate (1)

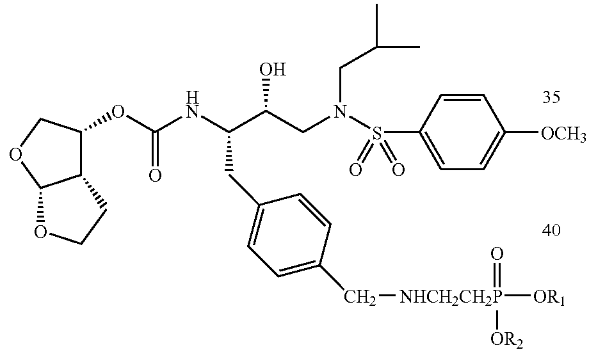

| $R_1$ | $R_2$ | Ki (pM) | $EC_{50}$ (nM) | I50V (#1) fold change | I50V (#2) fold change | I84V/L9M fold change | $CC_{50}$ μM |
|---|---|---|---|---|---|---|---|
| Et | Et | ++ | +++ | | – | | |
| H | H | ++ | – | | + | | |
| Ph | Lac-Et | | ++ | – | ++ | – | |
| Ph | Lac-Et | | + | | + | – | – |
| Ph | Lac-Et | | + | | ++ | – | |
| Ph | Aba-Et | | + | | + | – | |
| Ph-oEt | Lac-Et | ++ | ++ | – | ++ | – | |
| Ph-dM | Lac-Et | | +++ | | + | + | |
| Ph-dM | Lac-Pr | | +++ | | | | |
| H | Lac | ++ | | | | | |
| Ph | Hba-Et | | ++ | | ++ | – | |
| Ph | Hba-Et | | ++ | | ++ | – | + |
| Ph | Hba-Et | | ++ | | ++ | – | |
| H | Hba | + | | | | | |

P1-$CH_2N$—P-diester and monolactate (2)
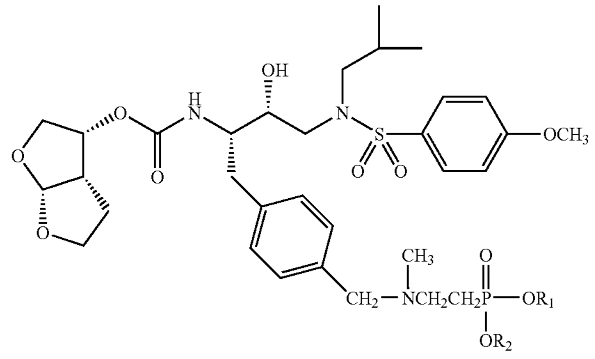
| $R_1$ | $R_2$ | Ki (pM) | $EC_{50}$ (nM) | I50V (#1) fold change | I84V/L90M fold change | $CC_{50}$ μM |
|---|---|---|---|---|---|---|
| Ph | Lac-Et | + | ++ | + | + | |
| H | H | ++ | | | | |
P1-$CH_2N$—P-diester and monolactate (3)
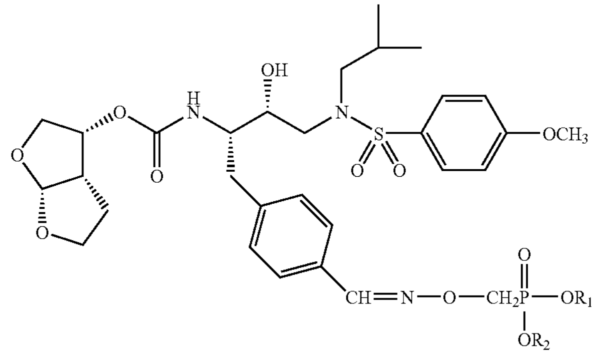
| $R_1$ | $R_2$ | Ki (pM) | $EC_{50}$ (nM) | I50V (#1) fold change | I84V/L90M fold change | $CC_{50}$ μM |
|---|---|---|---|---|---|---|
| Et | Et | ++ | +++ | | – | |

P1-N—P1-Phosphonic acid and esters (1)
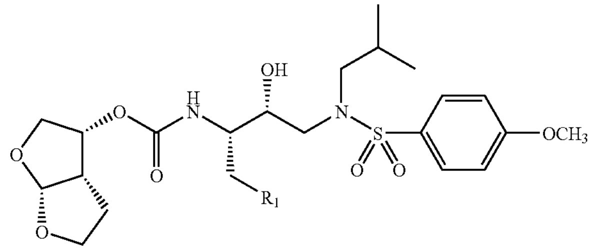
| R1 | Ki (pM) | $EC_{50}$ (nM) | I50V (#1) fold change | I84V/L90M fold change | $CC_{50}$ µM |
|---|---|---|---|---|---|
| 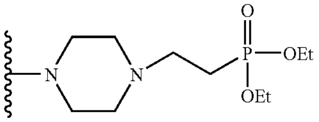 | – | ++ | | | |
| 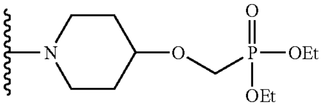 | – | ++ | | | |
| 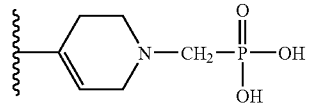 | – | | | | |
| 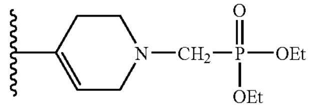 | ++ | +++ | | + | |
| 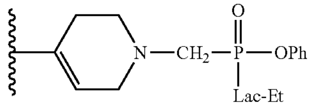 | | – | | | |
| 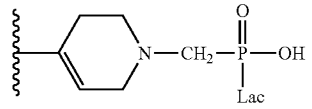 | – | | | | |
| 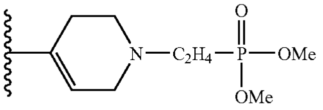 | + | ++ | | | |
| 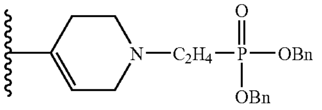 | ++ | +++ | | + | |
| 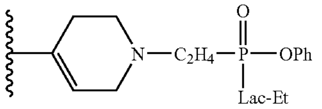 | | – | | | |
| 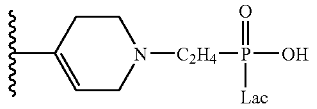 | | – | | | |

-continued
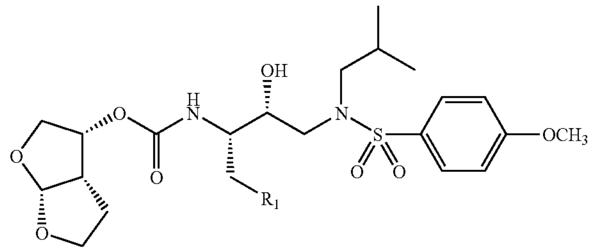
| R1 | Ki (pM) | $EC_{50}$ (nM) | I50V (#1) fold change | I84V/L90M fold change | $CC_{50}$ μM |
|---|---|---|---|---|---|
| 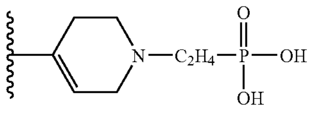 | – | | | | |
| 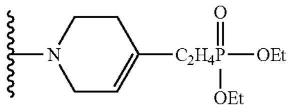 | + | +++ | | + | |
P1-N—P1-Phosphonic acid and esters (2)
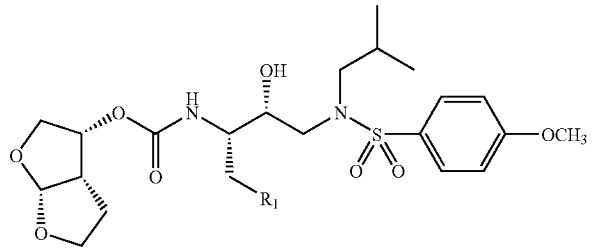
| R1 | Ki (pM) | $EC_{50}$ (nM) | I50V (#1) fold change | I84V/L90M fold change | $CC_{50}$ μM |
|---|---|---|---|---|---|
| 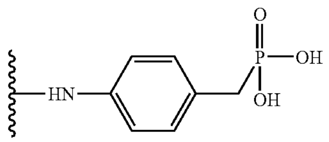 | + | + | | + | |
| 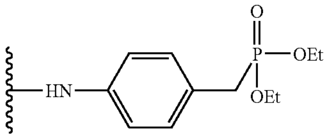 | ++ | +++ | | + | |
| 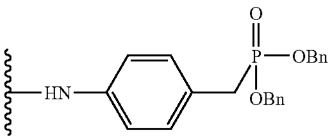 | ++ | +++ | | | |

-continued
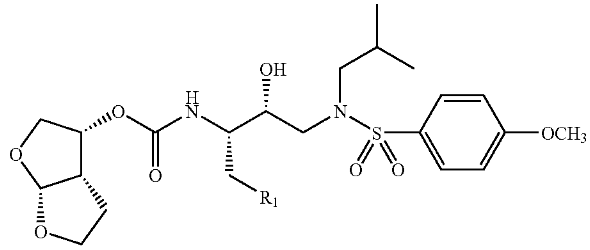
| R1 | Ki (pM) | $EC_{50}$ (nM) | I50V (#1) fold change | I84V/L90M fold change | $CC_{50}$ μM |
|---|---|---|---|---|---|
| 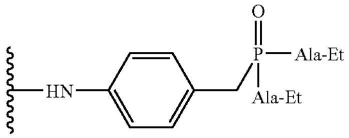 | ++ | ++ | | – | |
| 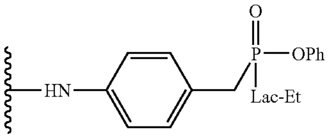 | | +++ | | | |
| 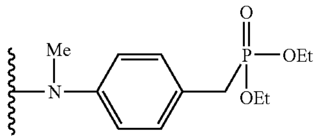 | ++ | +++ | | + | |
| 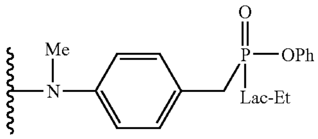 | | +++ | | – | |
| 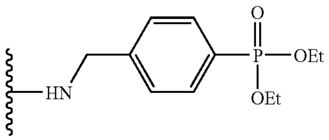 | – | +++ | | ++ | |
| 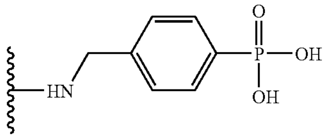 | – | | | | |
| 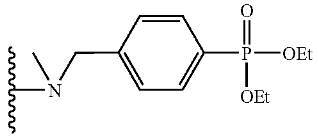 | + | +++ | +++ | – | |
| 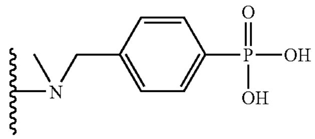 | – | | | | |

-continued
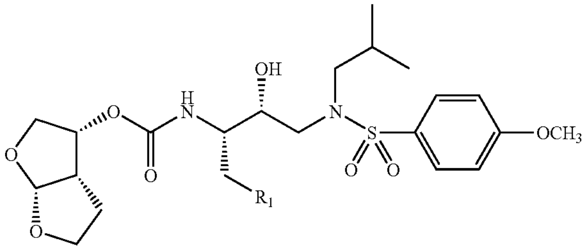
| R1 | Ki (pM) | $EC_{50}$ (nM) | I50V (#1) fold change | I84V/L90M fold change | $CC_{50}$ μM |
|---|---|---|---|---|---|
| 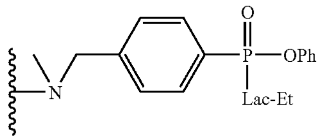 | | +++ | ++ | + | |
| 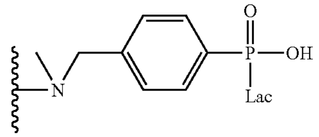 | – | | | | |
P1-N—P1-Phosphonic acid and esters (3)
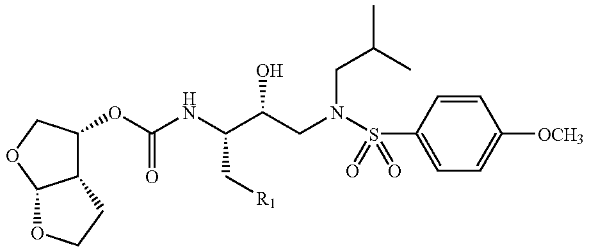
| R1 | Ki (pM) | $EC_{50}$ (nM) | I50V (#1) fold change | I84V/L90M fold change | $CC_{50}$ μM |
|---|---|---|---|---|---|
| 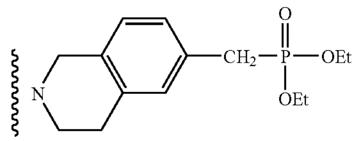 | ++ | +++ | + | + | |
| 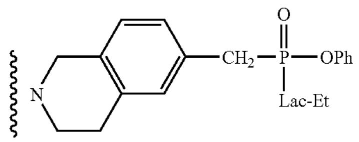 | + | ++ | + | + | |
| 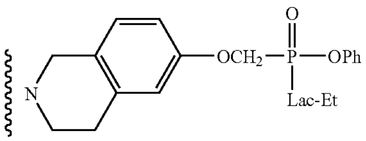 | + | ++ | + | + | |

-continued
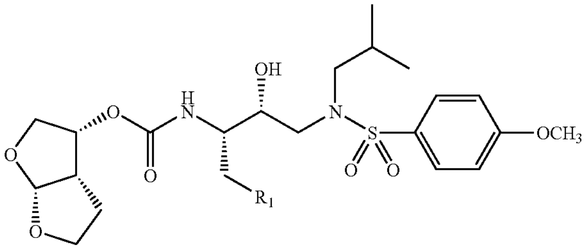
| R1 | Ki (pM) | $EC_{50}$ (nM) | I50V (#1) fold change | I84V/L90M fold change | $CC_{50}$ μM |
|---|---|---|---|---|---|
| 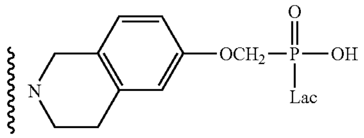 | + | | | | |
| 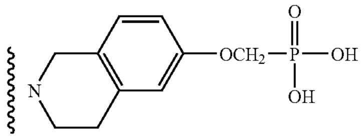 | | | | | |
| 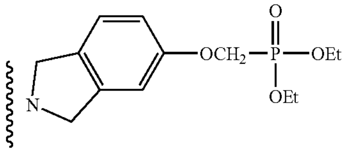 | – | – | | | |
P1-N—P1-Phosphonic acid and esters (4)
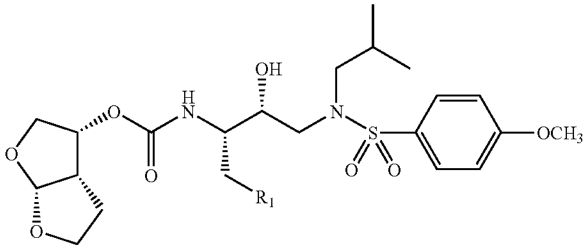
| R1 | Ki (pM) | $EC_{50}$ (nM) | I50V (#1) fold change | I84V/L90M fold change | $CC_{50}$ μM |
|---|---|---|---|---|---|
| 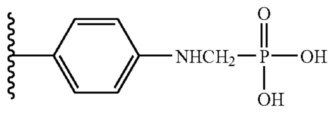 | +++ | | | | |
| 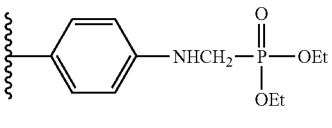 | +++ | +++ | – | – | |
| 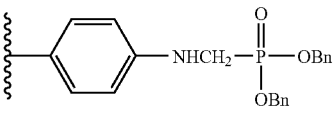 | ++ | +++ | + | – | |

-continued
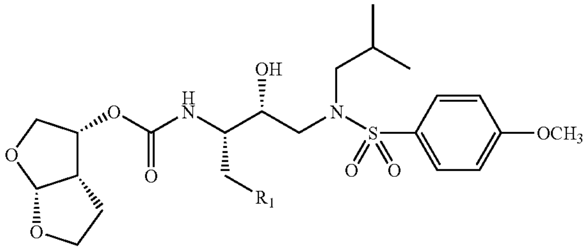
| R1 | Ki (pM) | $EC_{50}$ (nM) | I50V (#1) fold change | I84V/L90M fold change | $CC_{50}$ μM |
|---|---|---|---|---|---|
| 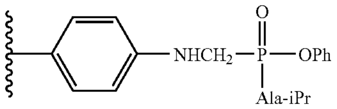 | ++ | +++ | | | |
| 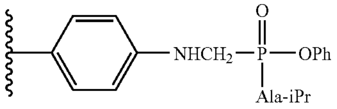 | ++ | ++ | | | |
| 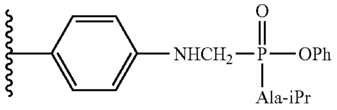 | +++ | +++ | | | |
| 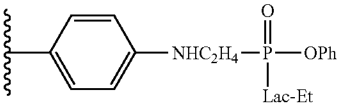 | | +++ | ++ | – | |
| 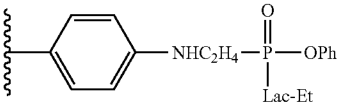 | | +++ | ++ | – | |
| 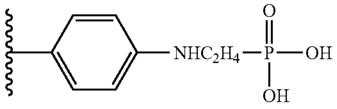 | ++ | | | | |
| 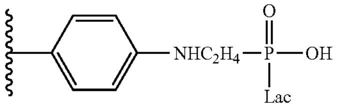 | ++ | | | | |

P1P-cyclic monolactate
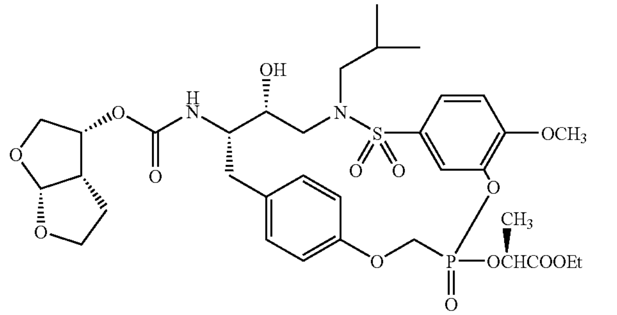
| $R_1$ | $R_2$ | Ki (pM) | $EC_{50}$ (nM) | I50V (#1) fold change | I84V/L90M fold change | $CC_{50}$ μM |
|---|---|---|---|---|---|---|
| | | nd | nd | | | |
| | | nd | nd | | | |
P1'-N—P1-Phosphonic acid and esters
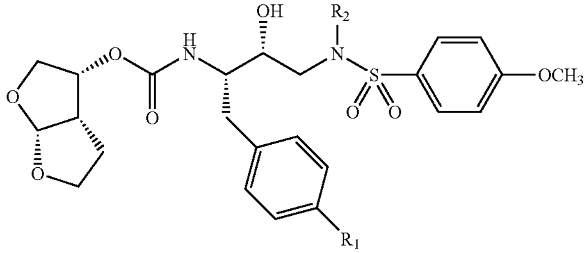
| R1 | R2 | Ki (pM) | $EC_{50}$ (nM) | I50V (#1) fold change | I84V/L90M fold change | $CC_{50}$ μM |
|---|---|---|---|---|---|---|
| $CH_3$ | 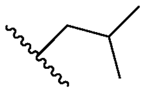 | ++ | +++ | ++ | + | |
| OH | 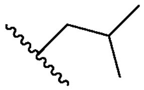 | | +++ | – | – | |
| $CH_2OH$ | 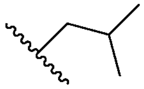 | +++ | +++ | – | – | |
| OBn | 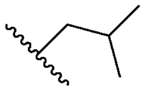 | +++ | +++ | – | – | |
| OH | 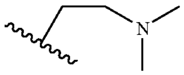 | – | ++ | – | – | |
| OBn | 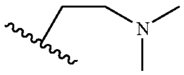 | – | +++ | | – | |

-continued
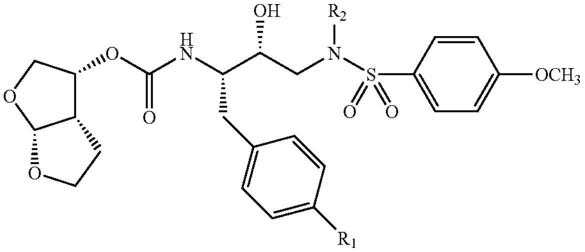
| R1 | R2 | Ki (pM) | $EC_{50}$ (nM) | I50V (#1) fold change | I84V/L90M fold change | $CC_{50}$ μM |
|---|---|---|---|---|---|---|
| 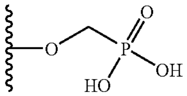 | 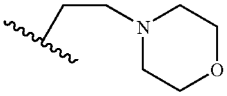 | – | – | + | + | |
| 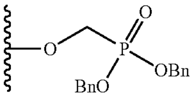 | 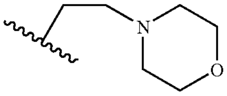 | + | ++ | + | + | |
| OH | 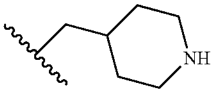 | – | – | | | |
| 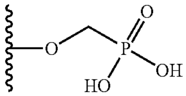 | 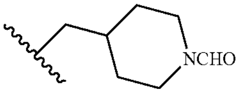 | ++ | – | | | |
| 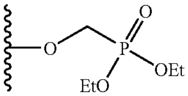 | 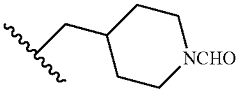 | ++ | – | | | |
| 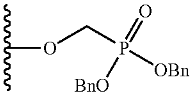 | 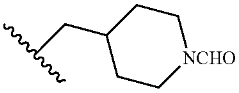 | ++ | ++ | | | |
| 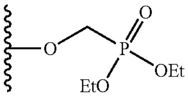 | 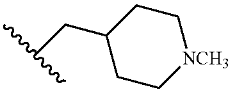 | + | – | | | |

P1'-Phosphonic acid and esters
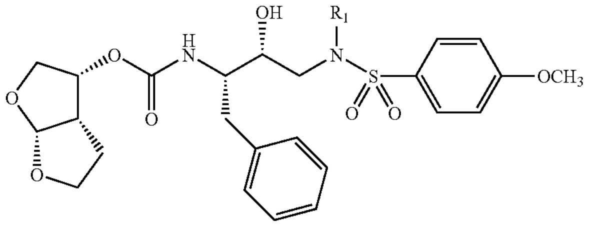
| R1 | Ki (pM) | $EC_{50}$ (nM) | I50V (#1) fold change | I84V/L90M fold change | $CC_{50}$ μM |
|---|---|---|---|---|---|
| 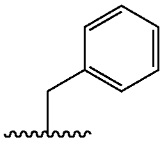 | ++ | +++ | +++ | +++ | |
| 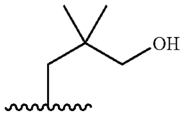 | +++ | +++ | +++ | +++ | |
| 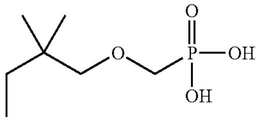 | ++ | + | | +++ | |
| 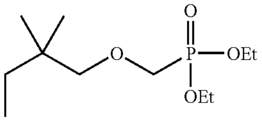 | +++ | +++ | | +++ | |
| 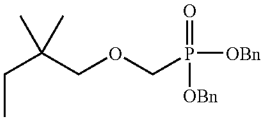 | +++ | +++ | | ++ | |
| 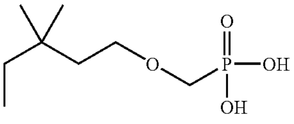 | ++ | ++ | ++ | ++ | |
| 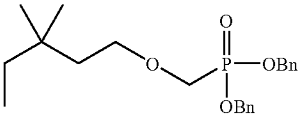 | ++ | +++ | +++ | +++ | |

P2-Monofuran-P1-phosphonic acid and esters

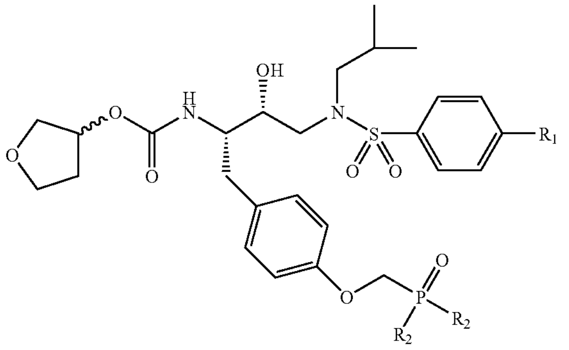

| R1 | R2 | Ki (pM) | $EC_{50}$ (nM) | I50V (#1) fold change | I84V/L90M fold change | $CC_{50}$ μM |
|---|---|---|---|---|---|---|
| OMe | OH | | – | +++ | +++ | |
| OMe | OEt | +++ | +++ | +++ | ++ | |
| OMe | OBn | | +++ | ++ | ++ | |
| OMe | phenol | +++ | +++ | +++ | + | |
| OMe | OEt | ++ | +++ | +++ | ++ | |
| $NH_2$ | phenol | + | ++ | + | – | |
| $NH_2$ | OH | | – | | + | |
| $NH_2$ | OBn | ++ | ++ | | + | |

P2-Monofuran-P1-P-monoamidates

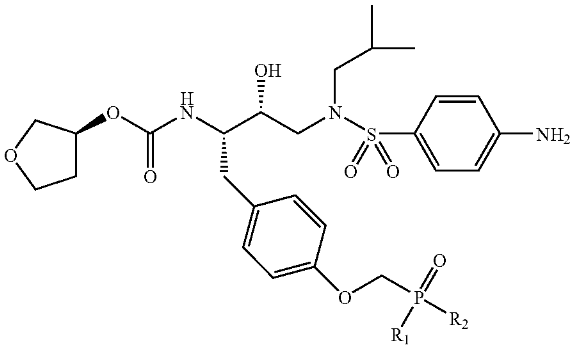

| R1 | R2 | Ki (pM) | $EC_{50}$ (nM) | I50V (#1) fold change | I84V/L90M fold change | $CC_{50}$ μM |
|---|---|---|---|---|---|---|
| OPh | Ala-iPr | ++ | ++ | | + | |
| OPh | Ala-iPr | ++ | ++ | | | |
| OPh | Ala-iPr | + | ++ | | | |

P2-Other Modifications-P1-phosphonic acid and esters

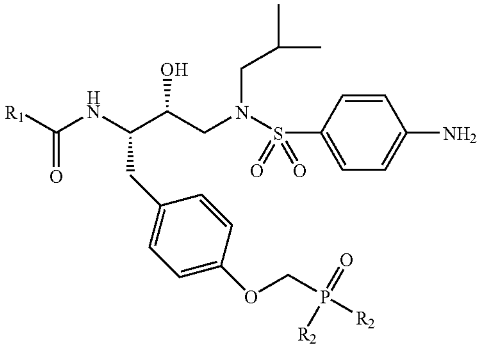

| R1 | R2 | Ki (pM) | $EC_{50}$ (nM) | I50V (#1) fold change | I84V/L90M fold change | $CC_{50}$ μM |
|---|---|---|---|---|---|---|
| 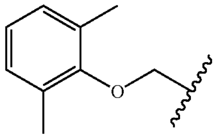 | phenyl | + | +++ | +++ | ++ | |
| 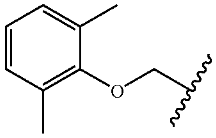 | phenol | + | ++ | ++ | + | |
| 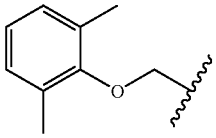 | OH | – | – | ++ | – | |

-continued
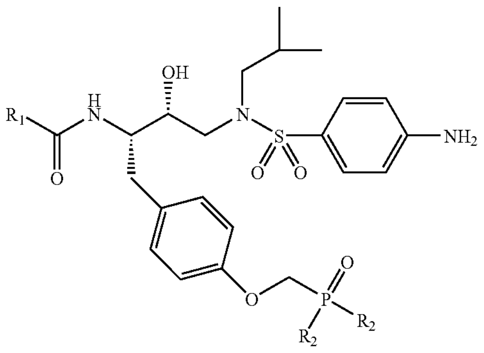
| R1 | R2 | Ki (pM) | $EC_{50}$ (nM) | I50V (#1) fold change | I84V/L90M fold change | $CC_{50}$ μM |
|---|---|---|---|---|---|---|
| 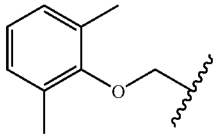 | OBn | + | ++ | + | − | |
| 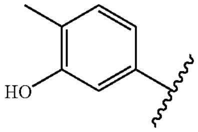 | phenyl | + | ++ | +++ | + | |
| 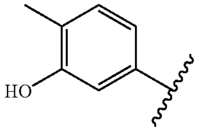 | OH | + | − | ++ | + | |
| 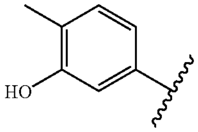 | OBn | + | ++ | +++ | + | |
| 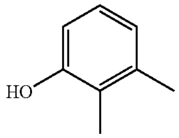 | phenyl | − | ++ | | ++ | |
| 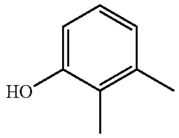 | phenol | + | + | | − | |
| 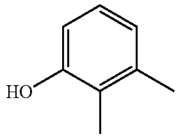 | OH | + | − | − | − | |
| 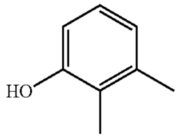 | OBn | ++ | ++ | + | − | |

P2'-Amino-P1-phosphonic acid and esters
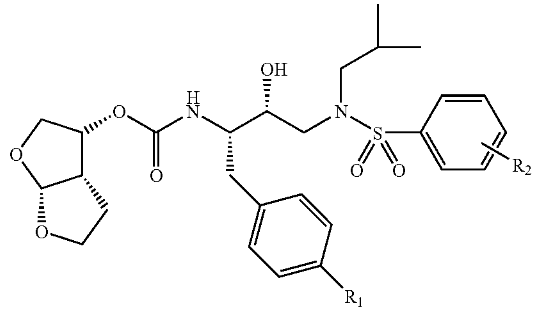
| R1 | R2 | Ki (pM) | $EC_{50}$ (nM) | I50V (#1) fold change | I84V/L90M fold change | $CC_{50}$ μM |
|---|---|---|---|---|---|---|
| OH | p-$NH_2$ | ++ | ++ | – | – | |
| 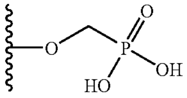 | p-$NH_2$ | ++ | – | + | – | |
| 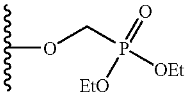 | p-$NH_2$ | ++ | +++ | | – | |
| 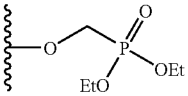 | p-$NO_2$ | ++ | +++ | | – | |
| 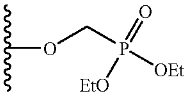 | p-NHEt | ++ | +++ | | – | |
| 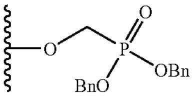 | p-$NH_2$ | ++ | +++ | – | – | |
| OH | m-$NH_2$ | ++ | ++ | | – | |
| 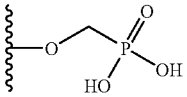 | m-$NH_2$ | ++ | + | | – | |
| 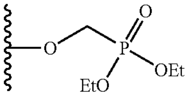 | m-$NH_2$ | ++ | ++ | | – | |
| 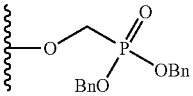 | m-$NH_2$ | ++ | +++ | – | – | |
| 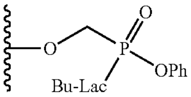 | m-$NH_2$ | + | ++ | – | – | |
| 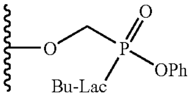 | m-$NH_2$ | ++ | ++ | | | |

-continued
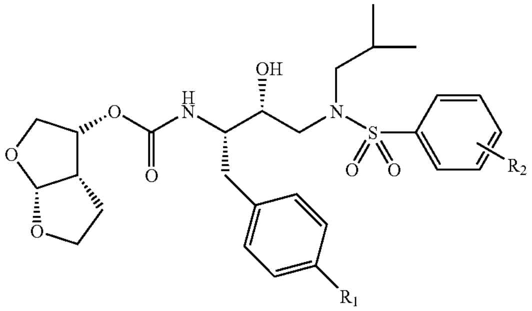
| R1 | R2 | Ki (pM) | $EC_{50}$ (nM) | I50V (#1) fold change | I84V/L90M fold change | $CC_{50}$ μM |
|---|---|---|---|---|---|---|
| 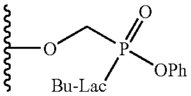 | m-$NH_2$ | + | ++ | | | |
P2'-Substituted-P1-phosphonic acid and esters (1)
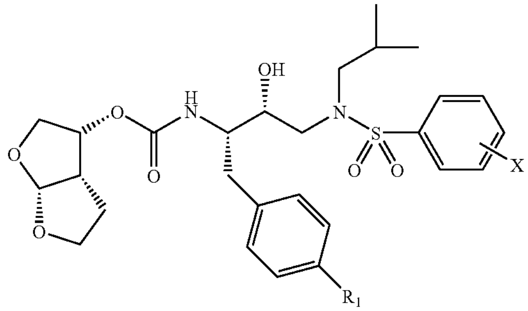
| R1 | X | Ki (pM) | $EC_{50}$ (nM) | I50V (#1) fold change | I84V/L90M fold change | $CC_{50}$ μM |
|---|---|---|---|---|---|---|
| 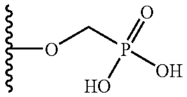 | p-OH | +++ | + | | | |
| 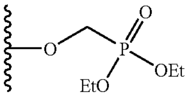 | p-OH | +++ | +++ | | | |
| 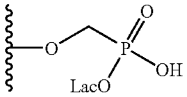 | p-OH | ++ | | | | |
| 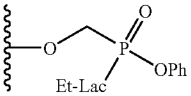 | p-OH | | +++ | | – | |
| 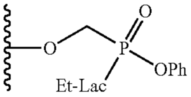 | p-OBn | | ++ | | | |

-continued
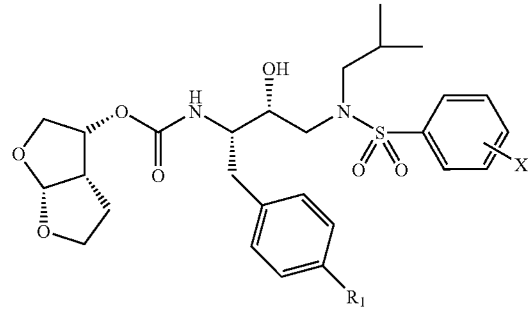
| R1 | X | Ki (pM) | $EC_{50}$ (nM) | I50V (#1) fold change | I84V/L90M fold change | $CC_{50}$ μM |
|---|---|---|---|---|---|---|
| 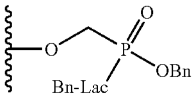 | p-OBn | | – | | | |
| 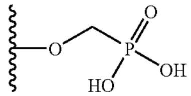 | p-H | ++ | – | | | |
| 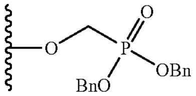 | p-H | ++ | +++ | | + | |
| 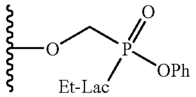 | p-H | | +++ | + | + | |
| 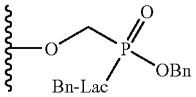 | p-H | | ++ | | | |
| 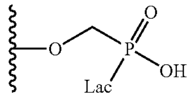 | p-H | ++ | | | | |
| 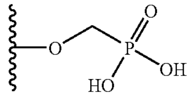 | p-F | ++ | + | | | |
| 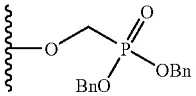 | p-F | ++ | +++ | | + | |
| 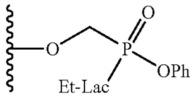 | p-F | | +++ | + | + | |
| 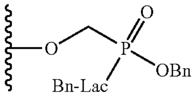 | p-F | | ++ | + | + | |
| 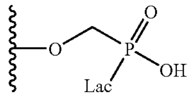 | p-F | ++ | | | | |

-continued
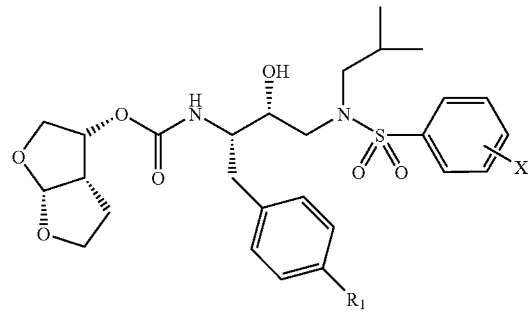
| R1 | X | Ki (pM) | $EC_{50}$ (nM) | I50V (#1) fold change | I84V/L90M fold change | $CC_{50}$ μM |
|---|---|---|---|---|---|---|
| 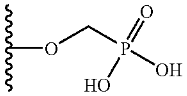 | p-$CF_3$ | +++ | + | | | |
| 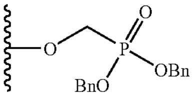 | p-$CF_3$ | ++ | +++ | | − | |
| 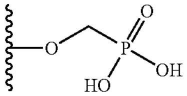 | p-$OCF_3$ | ++ | + | | | |
| 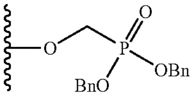 | p-$OCF_3$ | ++ | +++ | | + | |
| 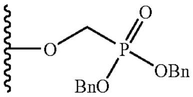 | p-CN | ++ | +++ | | − | |
| 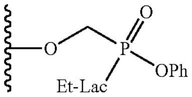 | p-Pip | − | − | | | |
| 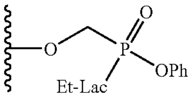 | p-Pip-Me | − | − | | | |

P2'-Substituted-P1-phosphonic acid and esters (2)
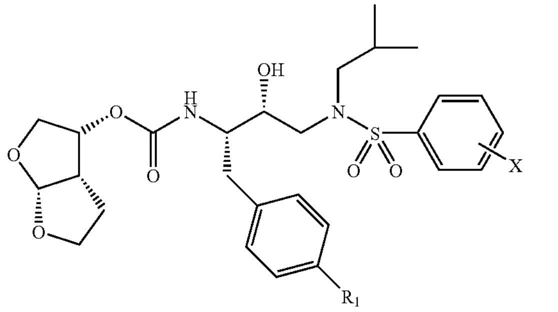
| R1 | X | Ki (pM) | $EC_{50}$ (nM) | I50V (#1) fold change | I84V/L90M fold change | $CC_{50}$ μM |
|---|---|---|---|---|---|---|
| 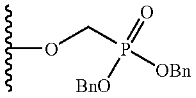 | m-Py | ++ | +++ | | | |
| 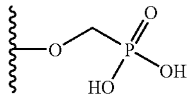 | m-Py | ++ | | | | |
| 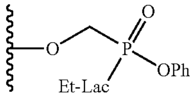 | m-Py | ++ | ++ | + | – | |
| 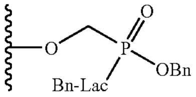 | m-Py | ++ | ++ | | | |
| 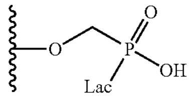 | m-Py | ++ | | | | |
| 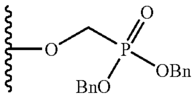 | m-Py-Me$^{+}$ | | + | | | |
| 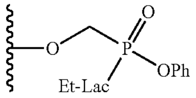 | m-Py-Me$^{+}$ | | ++ | | | |
| 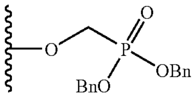 | m-Py-oxide | | ++ | | | |
| 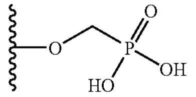 | m-Py-oxide | ++ | | | | |
| 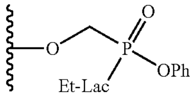 | m-Py-oxide | ++ | ++ | | – | |

-continued
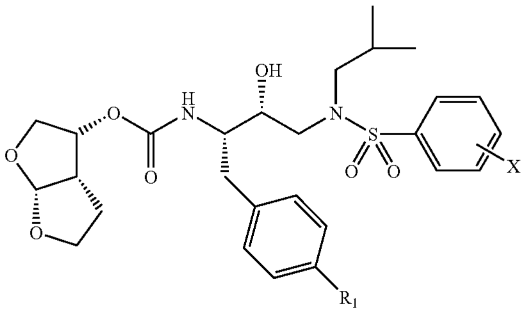
| R1 | X | Ki (pM) | $EC_{50}$ (nM) | I50V (#1) fold change | I84V/L90M fold change | $CC_{50}$ μM |
|---|---|---|---|---|---|---|
| 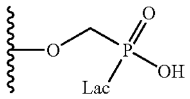 | m-Py-oxide | + | | | | |
| 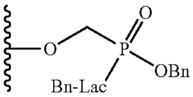 | m-Py-oxide | | – | | | |
| p-Py-oxide | p-OMe | ++ | – | | | |
| 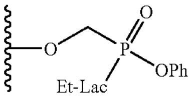 | p-CHO | | +++ | | | |
| 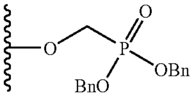 | p-CHO | | +++ | | | |
| 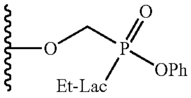 | p-CH2 OH | | +++ | – | – | |
| 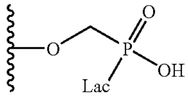 | p-CH2 OH | ++ | | | | |
| 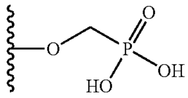 | p-CH2 OH | ++ | | | | |
| 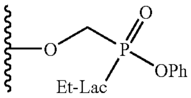 | p-CH2 Mor | | ++ | – | – | |
| 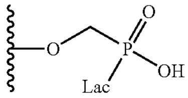 | p-CH2 Mor | – | | | | |
| 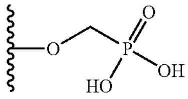 | p-CH2 Mor | – | | | | |

P2'-Alkylsulfonyl-P1-phosphonic acid and esters
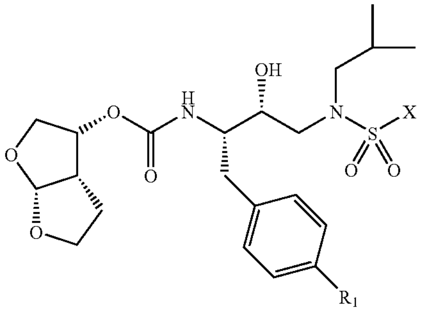
| R1 | X | Ki (pM) | $EC_{50}$ (nM) | I50V (#1) fold change | I84V/L90M fold change | $CC_{50}$ μM |
|---|---|---|---|---|---|---|
| 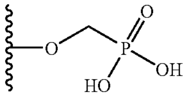 | 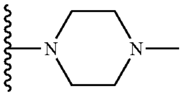 | – | – | | | |
| 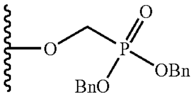 | 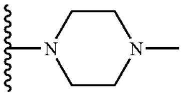 | + | ++ | | | |
P2'-Carbonyl-substituted-P1-phosphonic acid and esters
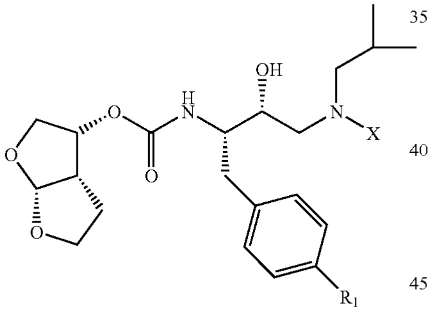
| R1 | X | Ki (pM) | $EC_{50}$ (nM) | I50V (#1) fold change | I84V/L90M fold change | $CC_{50}$ μM |
|---|---|---|---|---|---|---|
| 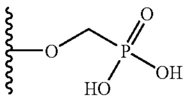 | 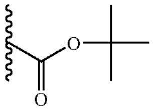 | – | | | | |
| 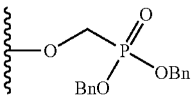 | 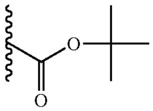 | – | ++ | | | |
| 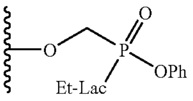 | 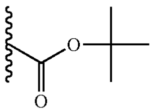 | | + | | | |

P2'-Phosphonic acid and esters
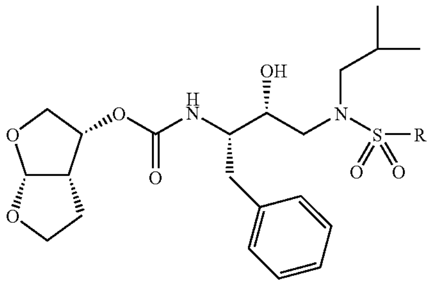
| R | Ki (pM) | $EC_{50}$ (nM) | I50V (#1) fold change | I84V/L90M fold change | $CC_{50}$ μM |
|---|---|---|---|---|---|
| 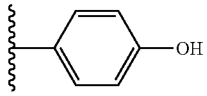 | +++ | +++ | – | – | |
| 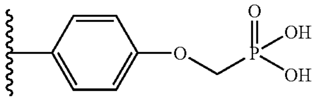 | +++ | + | – | – | |
| 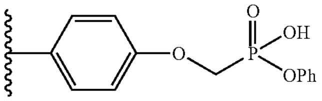 | ++ | – | | | |
| 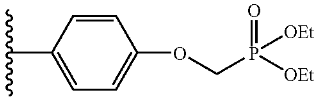 | ++ | +++ | ++ | ++ | |
| 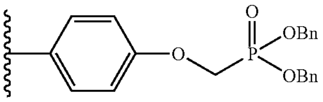 | + | ++ | +++ | +++ | |
| 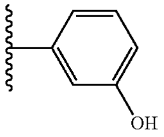 | +++ | +++ | + | + | |
| 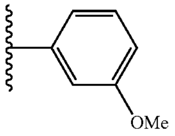 | +++ | +++ | +++ | ++ | |
| 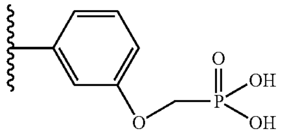 | ++ | ++ | ++ | + | |
| 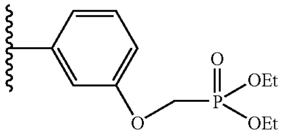 | +++ | +++ | +++ | ++ | |

-continued
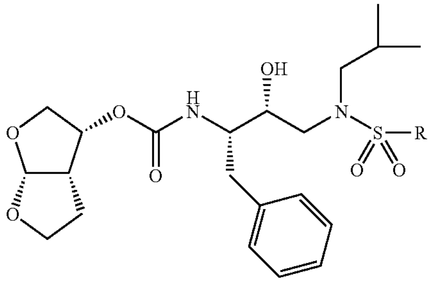
| R | Ki (pM) | $EC_{50}$ (nM) | I50V (#1) fold change | I84V/L90M fold change | $CC_{50}$ μM |
|---|---|---|---|---|---|
| 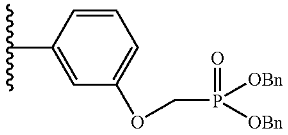 | ++ | +++ | ++ | ++ | |
| 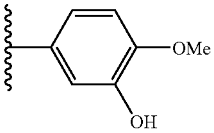 | +++ | +++ | − | − | |
| 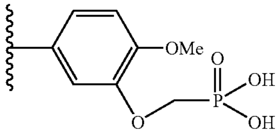 | +++ | ++ | + | − | |
| 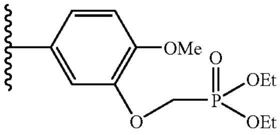 | + | ++ | + | + | |
| 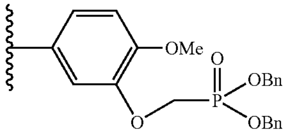 | − | + | +++ | ++ | |
| 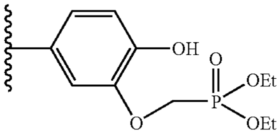 | + | ++ | + | − | |

P2'-P-Bisamidate, monoamidate, and monolactate

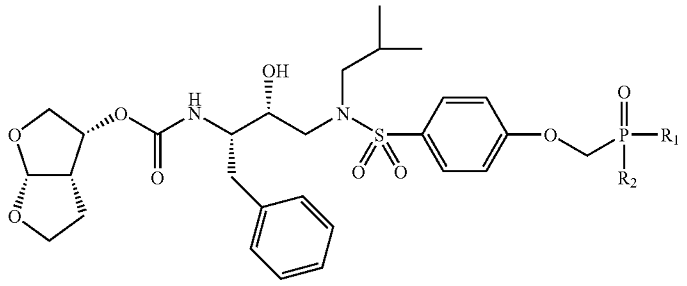

| $R_1$ | $R_2$ | Ki (pM) | $EC_{50}$ (nM) | I50V (#1) fold change | I84V/L90M fold change | $CC_{50}$ μM |
|---|---|---|---|---|---|---|
| Ala-Bu | Ala-Bu | + | ++ | + | + | |
| OPh | Ala-iPr | ++ | ++ | | | |
| OPh | Lac-iPr | + | + | | | |
| OH | Ala-OH | ++ | | | | |

P1-N—P2'-Phosphonic acid and esters

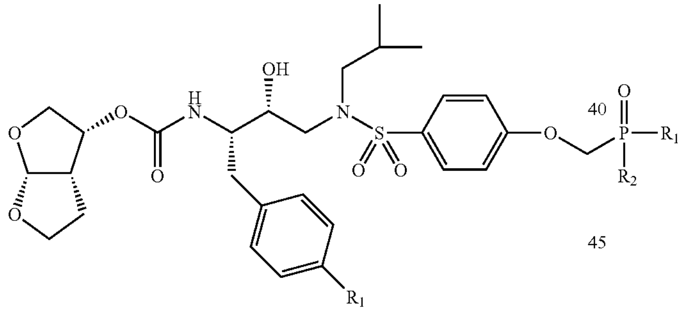

| $R_1$ | $R_2$ | Ki (pM) | $EC_{50}$ (nM) | I50V (#1) fold change | I84V/L90M fold change | $CC_{50}$ μM |
|---|---|---|---|---|---|---|
| $NO_2$ | phenol | | +++ | – | | |
| $NH_2$ | OH | ++ | – | | | |
| $NH_2$ | OEt | + | ++ | | ++ | |
| $NH_2$ | OBn | + | + | | + | |
| $NMe_2$ | OEt | ++ | +++ | | ++ | |
| OH | OH | ++ | – | | | |
| OH | OBn | ++ | ++ | | | |
| $OC_2H_4NMe_2$ | OH | +++ | + | | | |
| $OC_2H_4$—$NMe_2$ | OBn | ++ | ++ | | | |

P1-N—P2'-P-Bisamidate and monoamidate
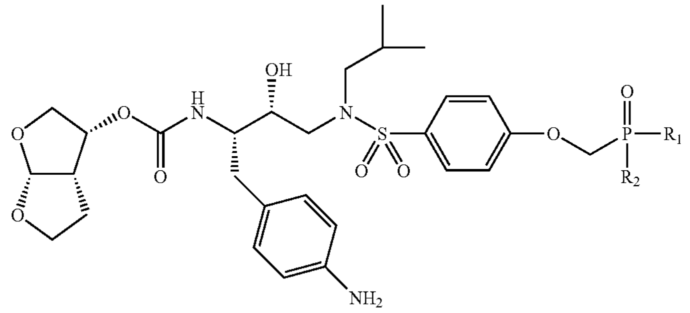
| $R_1$ | $R_2$ | Ki (pM) | $EC_{50}$ (nM) | I50V (#1) fold change | I84V/L90M fold change | $CC_{50}$ μM |
|---|---|---|---|---|---|---|
| Ala-Bu | Ala-Bu | + | + | | | |
| OPh | Ala-iPr | + | − | | | |
| OPh | Ala-iPr | ++ | − | | | |
P1-NEt-P2'-P-Bisamidate and monoamidate
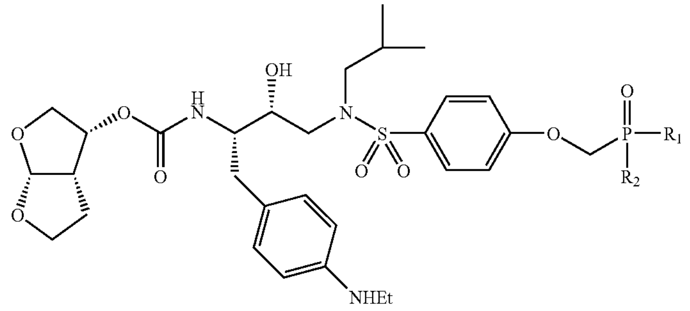
| $R_1$ | $R_2$ | Ki (pM) | $EC_{50}$ (nM) | I50V (#1) fold change | I84V/L90M fold change | $CC_{50}$ μM |
|---|---|---|---|---|---|---|
| OPh | Ala-iPr | + | + | | | |
| OPh | Ala-iPr | + | + | − | − | |
Phosphate Prodrug of Ampenavir
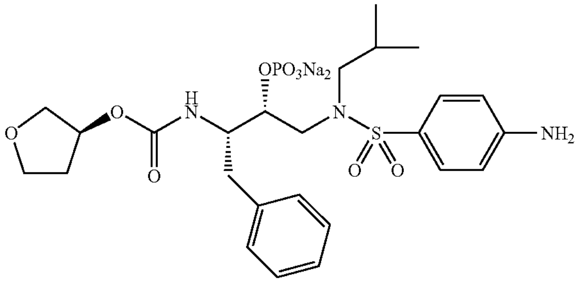
| $R_1$ | $R_2$ | Ki (pM) | $EC_{50}$ (nM) | I50V (#1) fold change | I84V/L90M fold change | $CC_{50}$ μM |
|---|---|---|---|---|---|---|
| | | | ++ | | | |

Phosphate Prodrug of 94-003

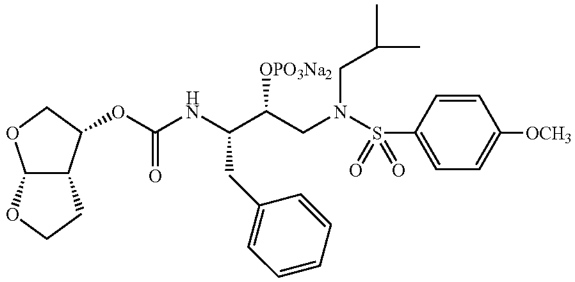

| $R_1$ | $R_2$ | Ki (pM) | $EC_{50}$ (nM) | I50V (#1) fold change | I84V/L90M fold change | $CC_{50}$ μM |
|---|---|---|---|---|---|---|
| | | | +++ | | | |

Phosphate Prodrug of GS77366 (P1-mono(S)Lac-iPr)

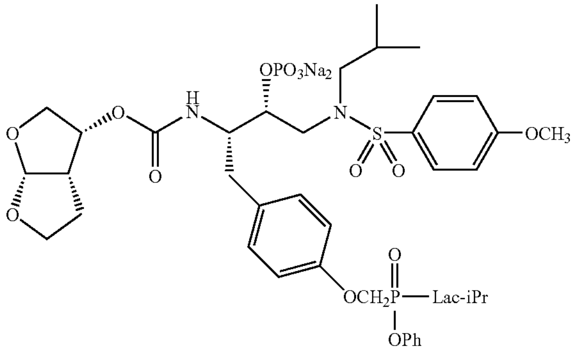

| $R_1$ | $R_2$ | Ki (pM) | $EC_{50}$ (nM) | I50V (#1) fold change | I84V/L90M fold change | $CC_{50}$ μM |
|---|---|---|---|---|---|---|
| | | | +++ | | | |

Valine Prodrug of (P1-mono(S)Lac-Et)

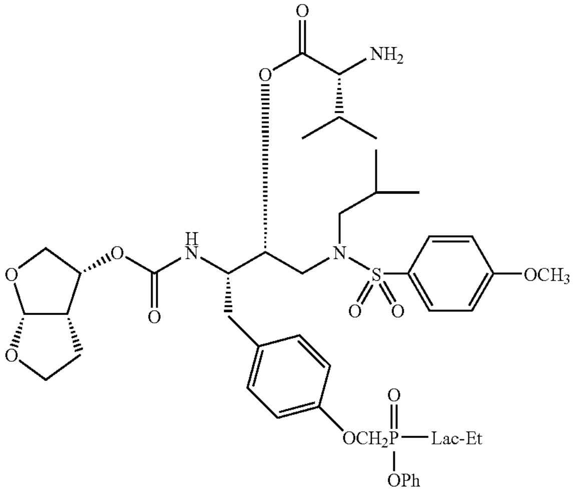

| $R_1$ | $R_2$ | Ki (pM) | $EC_{50}$ (nM) | I50V (#1) fold change | I84V/L90M fold change | $CC_{50}$ μM |
|---|---|---|---|---|---|---|
| | | | ++ | | | |

Valine Prodrug of GS278053 (P1-mono(S)Lac-Et, P2'-$CH_2OH$)

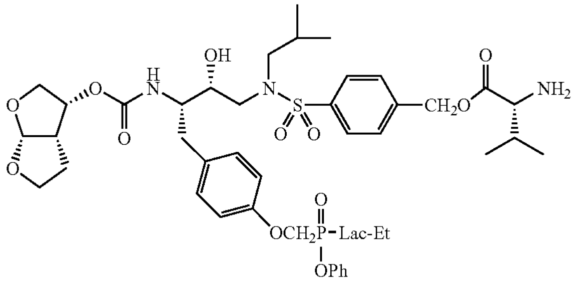

| $R_1$ | $R_2$ | Ki (pM) | $EC_{50}$ (nM) | I50V (#1) fold change | I84V/L90M fold change | $CC_{50}$ μM |
|---|---|---|---|---|---|---|
| | | | ++ | | | |

TABLE 11

Enzymatic and Cellular Activity Data
Formula VIIIa CCLPPI activity

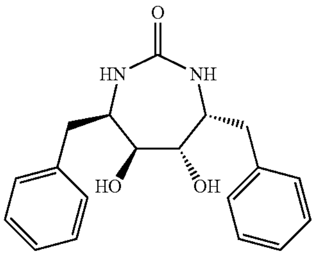

DMP-850

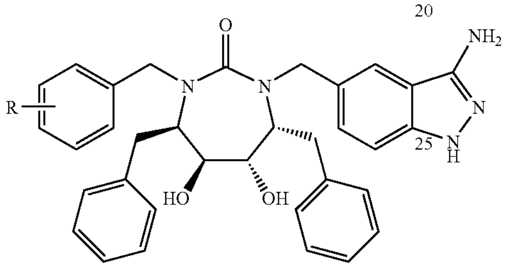

| | Enzymatic assay | | | Cell-based assay (MT-4) $EC_{50}$/nM | | | | | | |
|---|---|---|---|---|---|---|---|---|---|---|
| Structure, R | $K_i$ (nM) | WT $IC_{50}$/nM | 84V90M $IC_{50}$/nM | WT | 84V90M | 30N82I88D | 48V54V82A | 48V54V82S | 48V82A90M | 46I50V |
| H (DMP-850) | 0.033 | 3.0 | 9.1 | 165 | 819 | 82 | 82 | 73 | 45 | 88 |
| p-OH | 0.029 | 3.0 | 12 | 149 | 143 | 79 | 32 | 39 | 19 | 55 |
| p-OBn | >5 | 353 | 781 | 2123 | 5312 | 1548 | ND | ND | ND | ND |
| p-$OCH_2PO_3Bn_2$ | >5 | 276 | 2042 | 2697 | 4963 | 2119 | ND | ND | ND | ND |
| p-$OCH_2PO_3Et_2$ | >5 | 627 | 1474 | 2480 | >6000 | 1340 | ND | ND | ND | ND |
| p-$OCH_2PO_3H_2$ | >5 | 551 | 1657 | >12000 | ND | ND | ND | ND | ND | ND |
| m-OH | 0.128 | 1.6 | 1.2 | 151 | 475 | 249 | 84 | | | 104 |
| m-OBn | 0.253 | 6.9 | 27 | 218 | 2422 | 82 | 709 | ND | ND | 601 |
| m-$OCH_2PO_3Bn_2$ (N-iPr indazole) | 1.54[a] | 31 | 72 | 489 | 514 | 237 | 159 | 171 | 168 | 708 |
| m-$OCH_2PO_3Bn_2$ | 0.177 | 18 | 43 | 898 | >6000 | 705 | 2597 | ND | ND | 3121 |
| m-$OCH_2PO_3Et_2$ | 1.93[a] | 70 | 169 | 665 | 3005 | 93 | 513 | ND | ND | 857 |
| m-$OCH_2PO_3H_2$ | 0.254 | 8.3 | 33 | >12000 | ND | ND | ND | ND | ND | ND |
| m-$OCH_2PO_3Ph_2$ | 0.543[a] | 10 | 42 | 1349 | >6000 | 1541 | 2183 | ND | ND | 3380 |
| m-$OCH_2PO_3HPh$ | 0.644 | 17 | 65 | 1745 | >6000 | ND | ND | ND | ND | ND |
| m-mono-Ala-Bu | 0.858[a] | 6.6 | 39 | 1042 | >6000 | 425 | 790 | ND | ND | 797 |
| m-mono-Ala-Et¶ | | 35 | 68 | 1436 | >6000 | 219 | 734 | ND | ND | 1350 |
| m-mono-Lac-Bu | | 15 | 34 | 2663 | >6000 | 1089 | ND | ND | ND | ND |
| m-mono-Lac-Et | | 23 | 80 | 2609 | >6000 | 516 | 5923 | ND | ND | >6000 |
| m-bis-Ala-Bu | 1.279[a] | 18 | 103 | 1079 | >6000 | 2362 | 1854 | ND | ND | 1536 |
| m-bis-Ala-Et | 1.987[a] | 31 | 202 | 5620 | >6000 | 1852 | ND | ND | ND | ND |

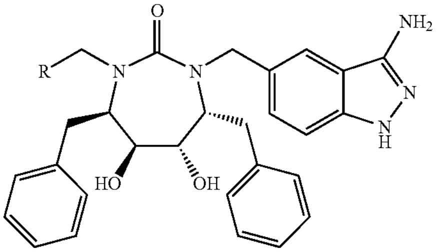
| Structure, R | $K_i$ (nM) | Enzymatic assay: WT $IC_{50}$/nM | Enzymatic assay: 84V90M $IC_{50}$/nM | Cell-based assay (MT-4) $EC_{50}$/nM: WT | 84V90M | 30N82I88D | 48V54V82A | 48V54V82S | 48V82A90M | 46I50V |
|---|---|---|---|---|---|---|---|---|---|---|
| H (DMP-850) | 0.033 | 3.0 | 9.1 | 165 | 819 | 82 | 82 | 73 | 45 | 88 |
| 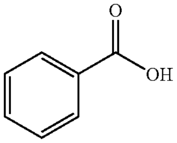 | 0.091 | 3.4 | 27 | 1548 | >6000 | >6000 | ND | ND | ND | ND |
| 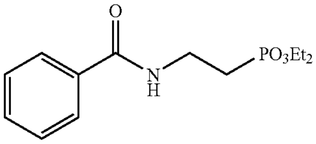 | 0.354 | 3.3 | 25 | 168 | 909 | 750 | 277 | | | 489 |
| 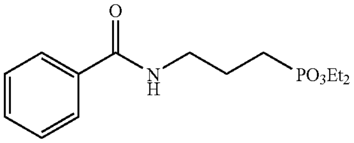 | 0.157 | 1.6 | 10 | 188 | 476 | 666 | 240 | | | 319 |
| 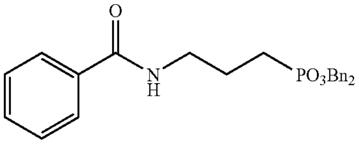 | 0.044 | 5.0 | 27 | 491 | 387 | 234 | 238 | | | 192 |
| 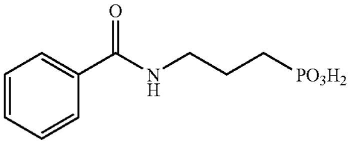 | 0.362 | 7.3 | 70 | 5141 | >6000 | 4480 | ND | ND | ND | ND |
| 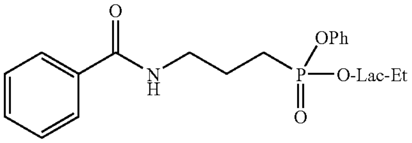 | 0.112 | 1.4 | 6.4 | 603 | 1276 | 678 | 208 | | | 209 |
| 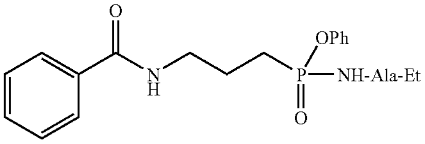 | <0.03 | 1.3 | 7.5 | 625 | 708 | 899 | 301 | | | 398 |

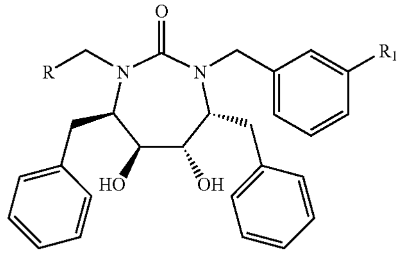
| | | Enzymatic assay | | | Cell-based assay (MT-4) $EC_{50}$/nM | | | | | | |
|---|---|---|---|---|---|---|---|---|---|---|---|
| Structure, R1 | Structure, R | $K_i$ (nM) | WT $IC_{50}$/nM | 84V90M $IC_{50}$/nM | WT | 84V90M | 30N82I8 8D | 48V54V 82A | 48V54V82 S | 48V82A90 M | 46I50V |
| $CO_2H$ | 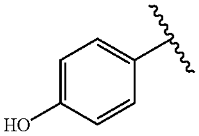 | | 15 | 174 | 3055 | >6000 | 887 | ND | ND | ND | ND |
| $CONH(CH_2)_3PO_3Et_2$ | 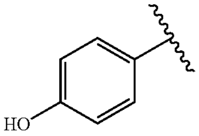 | 0.009 | 1.1 | 12 | 65 | 311 | 74 | 80 | 75 | 74 | 85 |
| $CO_2H$ | 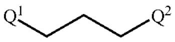 | | 18 | 299 | 2344 | >6000 | 3360 | ND | ND | ND | ND |
| $CONH(CH_2)_3PO_3Et_2$ | 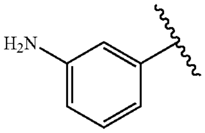 | <0.004 | 2.3 | 29 | 176 | 824 | 171 | 233 | ND | ND | 195 |
| $CO_2H$ | 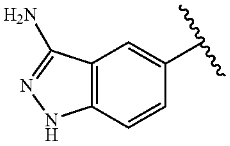 | 0.091 | 3.4 | 27 | 1548 | >6000 | >6000 | ND | ND | ND | ND |
| $CONH(CH_2)_2PO_3Et_2$ | 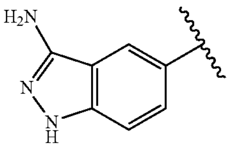 | 0.157 | 1.6 | 10 | 188 | 476 | 666 | 240 | | | 319 |

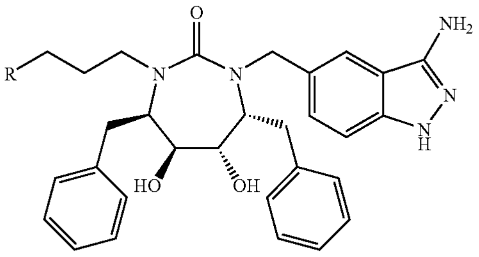
| Structure, R | Enzymatic assay $K_i$ (nM) | WT $IC_{50}$/nM | 84V90 M $IC_{50}$/nM | Cell-based assay (MT-4) $EC_{50}$/nM WT | 84V90 M | 30N 82I88D | 48V5 4V82 A | 48V5 4V82 S | 48V82 A90M | 46I50 V |
|---|---|---|---|---|---|---|---|---|---|---|
| $CH_3$ (DMP-851) | 0.033 | 3.8 | 9.4 | 54 | 918 | 69 | 33 | 30 | 22 | 17 |
| OH | 0.65[a] | 6.1 | 77 | 356 | 2791 | 669 | 294 | ND | ND | 683 |
| $OCH_2PO_3Et_2$ | 1.230[a] | 23 | 157 | 356 | >6000 | 145 | 175 | ND | ND | 138 |
| $OCH_2PO_3H_2$ | 0.809 | 59 | 137 | 1074 | >6000 | ND | ND | ND | ND | ND |
| O-mono-Lac-Et | >2.0 | 93 | 553 | >6000 | >6000 | ND | ND | ND | ND | ND |
| O-mono-Lac-Bu | >2.0 | 25 | 249 | >6000 | >6000 | ND | ND | ND | ND | ND |
| $CH_2OH$ | 0.017 | 2.8 | 31 | 253 | 1106 | 486 | 413 | ND | ND | 524 |
| $CH_2OCH_2PO_3Et_2$ | 2.8 | 13 | 123 | 119 | 3295 | 267 | 430 | ND | ND | 789 |
| $CH_2OCH_2PO_3H$ | | 42 | 205 | 1757 | >4243 | ND | ND | ND | ND | ND |
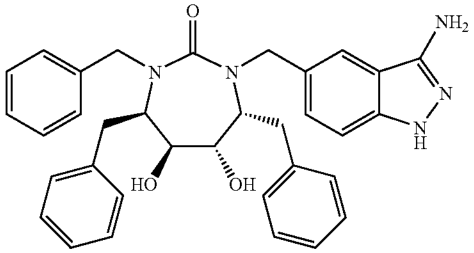
77546
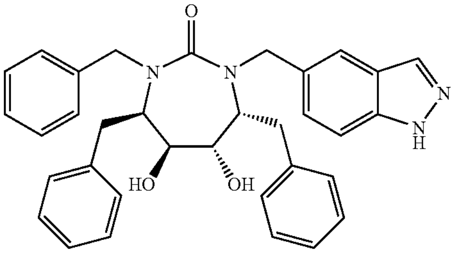
277735

-continued

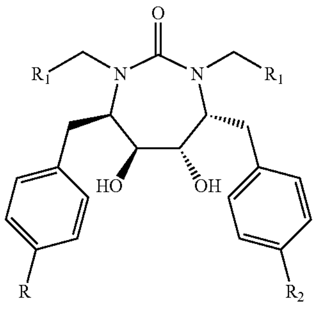

| R | R1 | R2 | $K_i$ (nM) | Enzymatic assay WT $IC_{50}$/nM | 84V9 0M $IC_{50}$/nM | Cell-based assay (MT-4) $EC_{50}$/nM WT | 84V9 0M | 30N 82I88 D | 48V5 4V82 A | 48V5 4V82 S | 48V8 2A90 M | 46I50 V |
|---|---|---|---|---|---|---|---|---|---|---|---|---|
| — | — | — | 0.033 | 3.0 | 9.1 | 165 | 819 | 82 | 82 | 73 | 45 | 88 |
| — | — | — | 0.374 | 5.8 | 43.3 | 193 | 2312 | 281 | 705 | ND | ND | 772 |
| H | Ph | H | | 34 | 631 | 2492 | >600 | 3360 | ND | ND | ND | ND |
| OH | Ph | OH | | 31 | 397 | 117 | 5609 | 756 | 2266 | ND | ND | 928 |
| OH | Ph | $OCH_2PO_3$ | | 9 | 40 | 33 | 791 | 92 | 807 | 1103 | 1429 | 53 |
| H | Ph | $OCH_2PO_3$ | 0.656 | 3.9 | 48 | 107 | 2456 | 293 | 1438 | 1899 | 3292 | 589 |
| H | Indazol | H | <0.01 | 2.5 | 13 | 11 | 22 | <8 | 5.5 | 8 | 4 | 4.0 |
| OH | Indazol | OH | 0.012 | 0.6 | 3.5 | >600 | 2728 | 7224 | ND | ND | ND | ND |
| OH | Indazol | $OCH_2PO_3$ | 0.137 | 1.1 | 5.5 | 1698 | 1753 | 1998 | ND | ND | ND | ND |
| H | Indazol | $OCH_2PO_3$ | 0.028 | 1.4 | 6.2 | 57 | 40 | 68 | 28 | 26 | 32 | 27 |

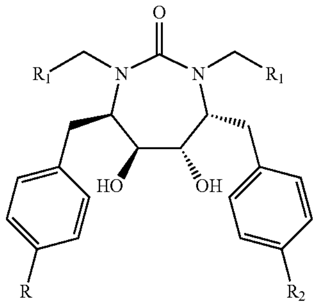

| R | R1 | R2 | $K_i$ (nM) | Enzymatic assay WT $IC_{50}$/nM | 84V9 0M $IC_{50}$/nM | Cell-based assay (MT-4) $EC_{50}$/nM WT | 84V9 0M | 30N 82I8 8D | 48V5 4V82 A | 48V5 4V82 S | 48V 82A 90M | 46I50 V |
|---|---|---|---|---|---|---|---|---|---|---|---|---|
| — | — | — | 0.033 | 3.0 | 9.1 | 165 | 819 | 82 | 82 | 73 | 45 | 88 |
| OH | Ph | $OCH_2PO_3Et_2$ | | 9 | 40 | 33 | 791 | 92 | 807 | 1103 | 1429 | 53 |
| H | Ph | $OCH_2PO_3Et_2$ | 0.656 | 3.9 | 48 | 107 | 2456 | 293 | 1438 | 1899 | 3292 | 589 |
| $OCH_3$ | Ph | $OCH_2PO_3Et_2$ | | | | | | | | | | |
| OH | Ph-pOH | $OCH_2PO_3Et_2$ | <0.01 | 2.6 | 18 | 285 | 1912 | 211 | 986 | ND | ND | 1107 |
| H | Ph-pOH | $OCH_2PO_3Et_2$ | 0.319 | 2.1 | 33 | 65 | 272 | 90 | 128 | 198 | 126 | 144 |
| $OCH_3$ | Ph-pOH | $OCH_2PO_3Et_2$ | 0.045 | 1.8 | 17 | 29 | 146 | 23 | 67 | 106 | 48 | 68 |
| OH | Ph-$mNH_2$/NHEt | $OCH_2PO_3Et_2$ | | 8.7 | 67 | 286 | 1902 | 562 | 789 | 1781 | 684 | 239 |
| H | Ph-$mNH_2$ | $OCH_2PO_3Et_2$ | 0.126 | 3.4 | 39 | 65 | 328 | 16 | 168 | 146 | 74 | 46 |
| $OCH_3$ | Ph-$mNH_2$ | $OCH_2PO_3Et_2$ | <0.01 | 3.6 | 56 | 63 | 535 | 18 | 202 | 117 | 102 | 36 |
| $OCH_3$ | m-pyridine | $OCH_2PO_3Et_2$ | | | | 115 | 765 | 106 | 1019 | 970 | 480 | 352 |

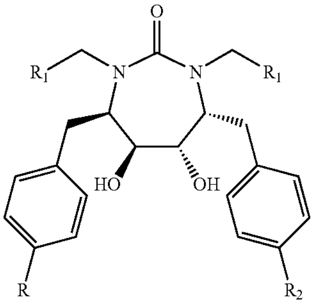

| | | | Enzymatic assay | | | Cell-based assay (MT-4) $EC_{50}$/nM | | | | | | |
|---|---|---|---|---|---|---|---|---|---|---|---|---|
| R | R1 | R2 | $K_i$ (nM) | WT $IC_{50}$/ nM | 84V90M $IC_{50}$/ nM | WT | 84V90M | 30N82I88D | 48V54V82A | 48V54V82S | 48V82A90M | 46I50V |
| — | — | — | 0.033 | 3.0 | 9.1 | 165 | 819 | 82 | 82 | 73 | 45 | 88 |
| H | Ph-m$NH_2$ | $OCH_2PO_3Et_2$ | 0.126 | 3.4 | 39 | 65 | 328 | 16 | 168 | 146 | 74 | 46 |
| $OCH_3$ | Ph-m$NH_2$ | $OCH_2PO_3Et_2$ | <0.01 | 3.6 | 56 | 63 | 535 | 18 | 202 | 117 | 102 | 36 |
| $OCH_3$ | Ph-m$NH_2$ | $O(CH_2)_2PO_3Et_2$ | | | | | | | | | | |
| $OCH_3$ | Ph-m$NH_2$ | OCONH $(CH_2)_2PO_3Et_2$ | | 11.3 | 116 | 74 | 2265 | 77 | 262 | 214 | 215 | 184 |
| $OCH_3$ | Ph-m$NH_2$ | OCONH $(CH_2)PO_3Et_2$ | | 9.9 | 85 | 58 | 2151 | 68 | 223 | 203 | 185 | 104 |
| H | Ph-pOH | $OCH_2PO_3Et_2$ | 0.319 | 2.1 | 33 | 65 | 272 | 90 | 128 | 222 | 146 | 144 |
| $OCH_3$ | Ph-pOH | $OCH_2PO_3Et_2$ | 0.045 | 1.8 | 17 | 30 | 148 | 25 | 70 | 129 | 54 | 90 |
| $OCH_3$ | Ph-pOH | OCONH $(CH_2)_2PO_3Et_2$ | | 6.6 | 49 | 33 | 495 | 31 | 74 | 51 | 55 | 223 |
| — | — | — | 0.033 | 3.0 | 9.1 | 165 | 819 | 82 | 82 | 73 | 45 | 88 |
| H | Ph | $OCH_2PO_3Et_2$ | 0.656 | 3.9 | 48 | 107 | 2456 | 293 | 1438 | 1899 | 3292 | 589 |
| H | Ph | OH | 0.330 | 15 | 162 | 1261 | >6000 | 2952 | >6000 | | | |
| H | Ph | $OCH_2PO_3Bn_2$ | 0.125 | 7.4 | 158 | 1769 | >6000 | 3135 | >6000 | | | |
| H | Ph | $OCH_2PO_3H_2$ | 0.386 | 9.7 | 210 | >6000 | >6000 | ND | ND | | | |
| H | Ph | Mono-lac-Et | 0.120 | 6.6 | 56 | 1726 | >6000 | 2793 | >6000 | | | |
| H | Ph | Mono-Ala-Et | | 5 | 50 | 310 | 2943 | 238 | 2851 | 1948 | 2450 | 1250 |

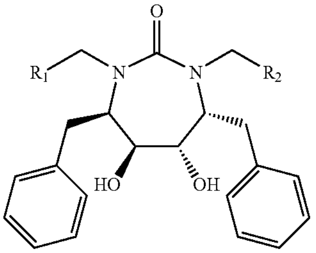

| | | Enzymatic assay | | | Cell-based assay (MT-4) $EC_{50}$/nM | | | | | | |
|---|---|---|---|---|---|---|---|---|---|---|---|
| R1 | R2 | $K_i$ (nM) | WT $IC_{50}$/ nM | 84V90M $IC_{50}$/ nM | WT | 84V90M | 30N82I88D | 48V54V82A | 48V54V82S | 48V82A90M | 46I50V |
| Phenyl | 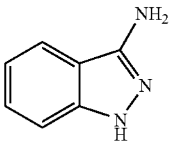 | 0.03 | 3.0 | 9.1 | 165 | 819 | 82 | 82 | 73 | 45 | 88 |

-continued
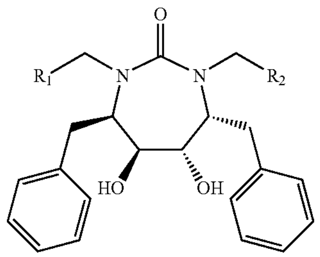
| R1 | R2 | $K_i$ (nM) | Enzymatic assay: WT $IC_{50}$/nM | Enzymatic assay: 84V 90 M $IC_{50}$/nM | Cell-based assay (MT-4) $EC_{50}$/nM: WT | 84V 90M | 30N 82I88 D | 48V 54V 82A | 48V54 V82S | 48V82 A90M | 46I5 0V |
|---|---|---|---|---|---|---|---|---|---|---|---|
| Phenyl | 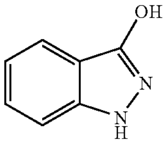 | 0.42 | 6.6 | 85 | 1226 | >600 | 869 | 774 | ND | ND | 937 |
| Phenyl | 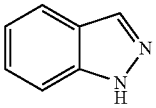 | 0.37 | 5.8 | 43.3 | 193 | 2312 | 281 | 705 | ND | ND | 772 |
| Phenyl | 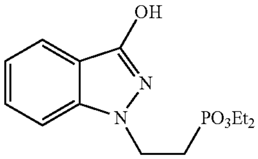 | | 109 | >25 | >6000 | ND | ND | ND | ND | ND | ND |
| Phenyl | 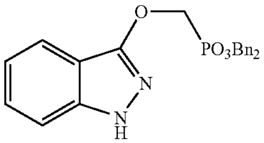 | | | | | | | | | | |
| Phenyl | 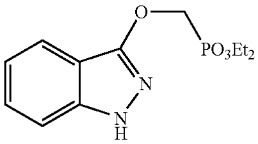 | | | | | | | | | | |
| Phenyl | 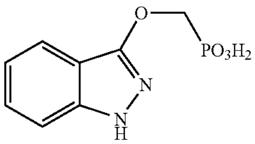 | | | | | | | | | | |
| 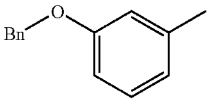 | 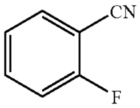 | 1.43 | 302 | 114 | >6000 | >600 | ND | ND | ND | ND | ND |
| 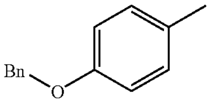 | 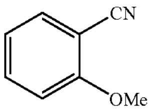 | >5 | >25 | ND | 5949 | ND | ND | ND | ND | ND | ND |

-continued

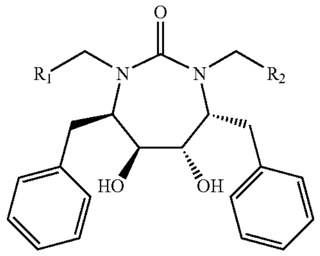

| R1 | R2 | $K_i$ (nM) | Enzymatic assay WT $IC_{50}$/nM | 84V90M $IC_{50}$/nM | Cell-based assay (MT-4) $EC_{50}$/nM WT | 84V90M | 30N82I88D | 48V54V82A | 48V54V82S | 48V82A90M | 46I50V |
|---|---|---|---|---|---|---|---|---|---|---|---|
| 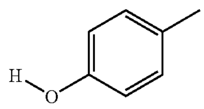 | 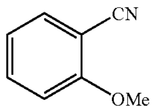 | >5 | 130 | 348 | 2006 | 3121 | ND | ND | ND | ND | ND |

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

The invention claimed is:

1. A compound having the following structural formula:

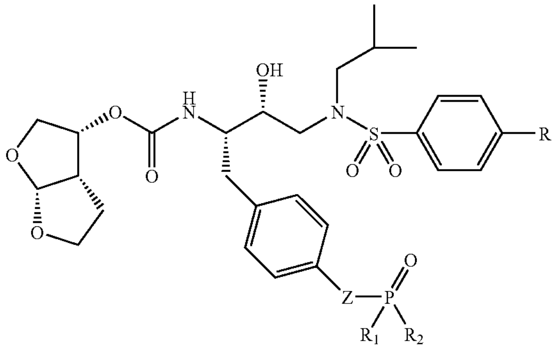

wherein R is ($C_1$-$C_4$) alkyl or hydroxy; Z is —O—$CH_2$—, or —$CH_2$—, or a bond; $R_1$ and $R_2$ are independently selected from hydroxy, methoxy, ethoxy, trifluoroethoxy, isopropoxy, phenoxy, benzyloxy, O-pivaloyloxymethyl, or a lactate ester; or $R_1$ and $R_2$ are independently selected from —NR' where R' is $C_1$-$C_6$ alkyl or an amino acid ester.

2. The compound of claim 1, Z is —O—CH2-.

3. The compound of claim 1, R is hydroxy or methoxy.

4. A compound having the following structural formula:

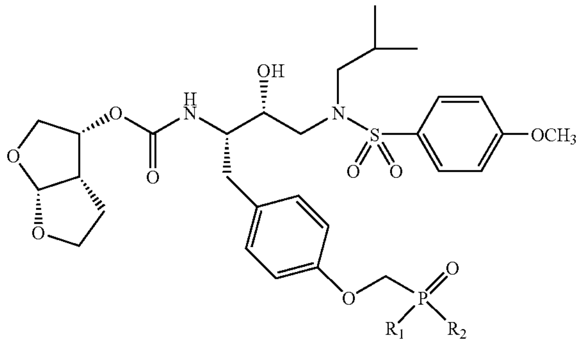

wherein $R_1$ and $R_2$ are independently selected from hydroxy, methoxy, ethoxy, trifluoroethoxy, isopropoxy, phenoxy, benzyloxy, or O-pivaloyloxymethyl.

5. The compound of claim 4, wherein $R_1$ and $R_2$ are ethoxy.

6. A compound having the following structural formula:

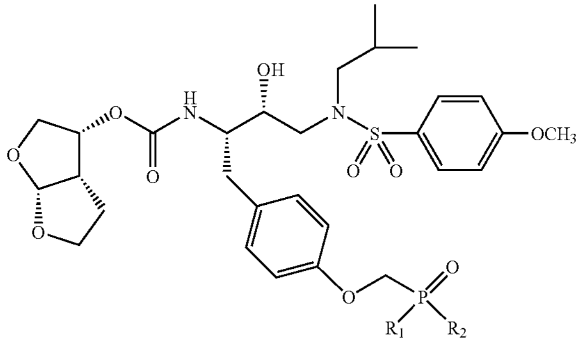

wherein $R_1$ and $R_2$ are independently selected from -NMe, -NEt, Gly-Et, Ala-Et, Aba-Et, Val-Et, Leu-Et, Phe-Bu, and Phe-Et.

7. A compound having the following structural formula:

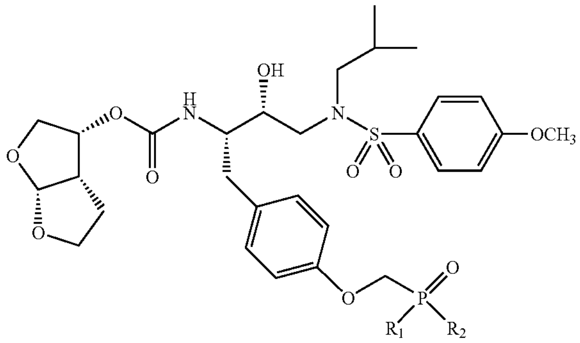

wherein $R_1$ is hydroxy, methoxy, ethoxy, trifluoroethoxy, isopropoxy, phenoxy, substituted phenoxy or benzyloxy; and $R_2$ is (1). a lactate ester selected from Glc-Et, Lac-Me, Lac-Et, Lac-iPr, Lac-Bu, Lac-EtMor, Lac-Me, Lac-Et, Lac-Bn, Lac-Bn, Lac-OH, Lac-OH, Hba-Et, Hba-tBu, Hba-OH, MeBut-Et, and DiMePro-Me; or (2). an amino acid ester is selected from Gly-Bu, Ala-Me, Ala-Et, Ala-iPr, (D)Ala-iPr, Ala-Bu, Aba-Et, Aba-Bu, and Ala-OH.

8. A compound having the following structure:

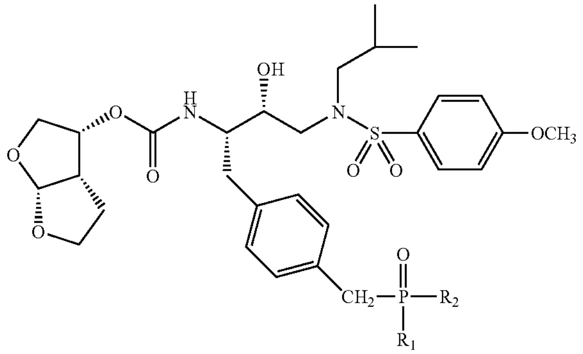

wherein $R_1$ and $R_2$ are independently selected from hydroxy, methoxy, ethoxy, trifluoroethoxy, isopropoxy, phenoxy, benzyloxy, or O-pivaloyloxymethyl.

9. A pharmaceutical composition comprising a compound of claim 1 and a pharmaceutically acceptable carrier.

10. A pharmaceutical composition comprising a compound of claim 4 and a pharmaceutically acceptable carrier.

11. A pharmaceutical composition comprising a compound of claim 5 and a pharmaceutically acceptable carrier.

* * * * *

UNITED STATES PATENT AND TRADEMARK OFFICE

CERTIFICATE OF CORRECTION

PATENT NO. : 7,649,015 B2
APPLICATION NO. : 10/423496
DATED : January 19, 2010
INVENTOR(S) : Arimilli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1254 days.

Signed and Sealed this

Twenty-sixth Day of October, 2010

David J. Kappos
*Director of the United States Patent and Trademark Office*